United States Patent [19]
Feder et al.

[11] Patent Number: 5,872,237
[45] Date of Patent: Feb. 16, 1999

[54] MEGABASE TRANSCRIPT MAP: NOVEL SEQUENCES AND ANTIBODIES THERETO

[75] Inventors: John Nathan Feder, San Carlos; Gregory Scott Kronmal, Pacifica; Peter M. Lauer, San Francisco; David A. Ruddy, San Francisco; Winston Thomas, San Mateo; Zenta Tsuchihashi, Menlo Park; Roger K. Wolff, Mill Valley, all of Calif.

[73] Assignee: Mercator Genetics, Inc., Menlo Park, Calif.

[21] Appl. No.: 724,394

[22] Filed: Oct. 1, 1996

Related U.S. Application Data

[63] Continuation-in-part of Ser. No. 630,912, Apr. 4, 1996, abandoned, and Ser. No. 652,265, May 23, 1996.

[51] Int. Cl.$^6$ ................................................. C07H 21/04
[52] U.S. Cl. ................................................... 536/23.5
[58] Field of Search ........................................ 536/23.5

[56] References Cited

PUBLICATIONS

Amadou, C. et al., "Localization of New Genes and Markers to the Distal Part of the Human Major Histocompatibility Complex (MHC) Region and Comparison with the Mouse: New Insights into the Evolution of Mammalian Genomes," *Genomics* 26:9–20 (1995).
Anderson, J.R. et al., "Precipitating Autoantibodies in Sjogren's Disease," *Lancet* 2:456–460 (1961).
Chong, S.S. et al., "Molecular Cloning of the cDNA Encoding a Human Renal Sodium Phosphate Transport Protein and its Assignment ot Chromosome 6p21.3–p23," *Genomics* 18:355–359 (1993).
Church, D.M. et al., "Isolation of genes from complex sources of mammalian genomic DNA using exon amplification," *Nature Genetics* 6:98–105 (1994).
Clark, G. et al., "Characterization of a Soluble Cytoplasmic Antigen REactive with SEra from Patients with Systemic Lupus Erythmatosus," *J. Immunology* 102(1):117–122 (1969).
Feder, J.N. et al., "A novel MHC class I–like gene is mutated in patients with hereditary haemochromatosis," *Nature Genetics* 13:399–408 (1996).
Freemont, P.S. et al., "A Novel Cysteine–Rich Sequence Motif," *Cell* 64:483–484 (1991).
Jack, L.J. et al., "Cloning and Analysis of cDNA Encoding Bovine Butyrophilin, an Apical Glycoprotein Expressed in Mammary Tissue and Secreted in Association with Milk–fat Globule Membrane During Lactation," *J. Biol. Chem.* 265(24):14481–14486 (1990).
Levy–Lahad, E. et al., "Candidate Gene for the Chromosome 1 Familial Alzeimer's Disease Locus," *Science* 269:973–977 (1995).
Lovett, M. et al., "Direct selection: A method for the isolation of cDNAs encoded by large genomic regions," *Proc. Natl. Acad. Sci. U.S.A.* 88:9628–9632 (1991).
Miller, M.M et al., "Immunoglobulin variable–region–like domains of diverse sequence within the major histocompatibility complex of the chicken," *Proc. Natl. Acad. Sci. U.S.A.* 88:4377–4381 (1991).
Simon, M. et al., "Association of HLA–A3 and HLA–B14 antigens with idiopathic haemochromatosis," *Gut* 17:332–334 (1976).
Taylor, M.R. et al., "Cloning and sequence analysis of human butyrophilin reveals a potential receptor function," *Biochem. Biophy. Acta* 1306:1–4 (1996).
Vernet, C. et al., "Evolutionary Study of Moltigenic Families Mapping Close to the Human MHC Class 1 Region," *J. Molecular Evolution* 37:600–612 (1993).
Yu, C.E. et al., "Positional Cloning of the Werner's Syndrome Gene," *Science* 272:258–262 (1996).
Vogel, F and Motulsky, AG. Human chromosomes. in Human Genetics. Springer–Verlag, Berlin. pp. 18–81, 1982.

*Primary Examiner*—David Saunders
*Assistant Examiner*—F. Pierre VanderVegt
*Attorney, Agent, or Firm*—Pennie & Edmonds LLP

[57] ABSTRACT

A fine structure map of the 1 megabase region surrounding the candidate HH gene is provided, along with 250 KB of DNA sequence and 8 loci corresponding to candidate genes within the 1 megabase region. These loci are useful as genetic markers for further mapping studies. Additionally, the eight cDNA sequences corresponding to those loci are useful, for example, for the isolation of other genes in putative gene families, and as probes for diagnostic assays. Additionally, the proteins encoded by those cDNAs are useful in the generation of antibodies for analysis of gene expression and in diagnostic assays, and in the purification of related proteins.

1 Claim, 334 Drawing Sheets

FIG. 3-1

```
BT      --MAVFPSSGLPRCL---LTLILLQLPKLDSAPFD VIGPPEPILAVVGEDAELPCRLSPN
BTF1    MESAAALHFSRPAS----LLLLLLSLCALVSAQFT  VVGPTDPILATVGENTTLRCHLSPE
BTF2    MEPAAALHFSLPASLLLLLLLLLLSLCALVSAQFT  VVGPANPILAMVGENTTLRCHLSPE
BTF5    MKMASFLAFLLLNFR---VCLLLLQLLMPHSAQFS  VLGPSGPILAMVGEDADLPCHLFPT
BTF3    MKMASSLAFLLLNFH---VSLFLVQLLTPCSAQFS  VLGPSGPILAMVGEDADLPCHLFPT
BTF4    MKMASSLAFLLLNFH---VSLLLVQLLTPCSAQFS  VLGPSGPILAMVGEDADLPCHLFPT
            *            ** *       * **  **** ***   * * *
```

```
BT      ASAEHLELRWFRKKVSPAVLVHRDGREQEAEQMPEYRGRATLVQDGIAKGRVALRIRGVR
BTF1    KNAEDMEVRWFRSQFSPAVFVYKGGRERTEEQMEEYRGRTTFVSKDISRGSVALVIHNIT   B-G
BTF2    KNAEDMEVRWFRSQFSPAVFVYKGGRERTEEQMEEYRGRITFVSKDINRGSVALVIHNVT   DOMAIN
BTF5    MSAETMELKWVSSSLRQVVNVYADGKEVEDRQSAPYRGRTSILRDGITAGKAALRIHNVT
BTF3    MSAETMELRWVSSSLRQVVNVYADGKEVEDRQSAPYRGRTSILRDGITAGKAALRIHNVT
BTF4    MSAETMELKWVSSSLRQVVNVYADGKEVEDRQSAPYRGRTSILRDGITAGKAALRIHNVT
         **  *  *      *  *  *        *  ****    *  *  ** *
```

```
BT      VSDDGEYTCFFREDGSYEEALVHLKVA ALGSDPHISMQVQENGEICLECTSVGWYPEPQV
BTF1    AQENGTYRCYFQEGRSYDEAILHLVVA GLGSKPLISMRGHEDGGIRLECISRGWYPKPLT
BTF2    AQENGIYRCYFQEGRSYDEAILRLVVA GLGSKPLIEIKAQEDGSIWLECISGGWYPEPLT
BTF5    ASDSGKYLCYFQDGDFYEKALVELKVA ALGSDLHVDVKGYKDGGIHLECRSTGWYPQPQI
BTF3    ASDSGKYLCYFQDGDFYEKALVELKVA ALGSDLHIEVKGYEDGGIHLECRSTGWYPQPQI
BTF4    ASDSGKYLCYFQDGDFYEKALVELKVA ALGSNLHVEVKGYEDGGIHLECRSTGWYPQPQI
         *  *   * *    *  *    **  ***          * *** * **** *
```

```
BT      QWRTSKGEKFPSTSESRNPDEEGLFTVAASVIIRDTSTKNVSCYIQNLLLGQEKKVEISI
BTF1    VWRDPYGGVAPALKEVSMPDADGLFMVTTAVIIRDKSVRNMSCSINNTLLGQKKESVIFI
BTF2    VWRDPYGEVVPALKEVSIADADGLFMVTTAVIIRDKYVRNVSCSVNNTLLGQEKETVIFI
BTF5    QWSNNKGENIPTVEAPVVADGVGLYAVAASVIMRGSSGEGVSCTIRSSLLGLEKTASISI
BTF3    KWSDTKGENIPAVEAPVVADGVGLYAVAASVIMRGSSGGGVSCIIRNSLLGLEKTASISI
BTF4    QWSNAKGENIPAVEAPVVADGVGLYEVASSVIMRGGSGEGVSCIIRNSLLGLEKTASISI
         *    *     *      ** *  ** *     **   ***  *** *  *  *
```

```
BT      PASSLPRLTPWIVAVAV--------------ILMVLGLLTIGSIFFTW RLYNER-------
BTF1    PESFMPSVSPCAVALP--------------IIVVILMIPIAVCIYWIN KLQKEKKILSGEK
BTF2    PESFMPSASPWMVALAVILTASPWMVSMTVILAVFIIFMAVSICCIK  KLQREKKILSGEK   TM
BTF5    ADPFFRSAQRWIAAALAR-------------TLPVLLLLLGGAGYFLW QQQEEKKTQFRKK   DOMAIN
BTF3    ADPFFRSAQPWIAAALAG-------------TLPISLLLLAGASYFLW RQQKEKIALSRET
BTF4    ADPFFRSAQPWIAAALAG-------------TLPILLLLLAGASYFLW RQQKEITALSSEI
                         *                                            *
```

```
BT      PRER----------RNEFS-------SKERLLEELKWKKATLHA----------------
BTF1    EFERETREIALKELEKERVQKEEELQVKEKLQEELRWRRTFLHA----------------
BTF2    KVEQE---------EKE---------LAQQLQEELRWRRTFLHA----------------
BTF5    KREQELREMAWSTMKQEQS-------TRVKLLEELRWRSIQYASRGERHSAYNEWKKALF
BTF3    ERERENMKEMGYAATEQEIS------LRKKLQEELKWRKIQYMARGEKSLAYHEWLMALF
BTF4    ESEQEMKEMGYAATEREIS-------LRESLQEELKRKKSST------------------
           *          *       * ***
```

FIG. 3-2

```
BT     --VDV TLDPDTAHPHLFLYEDSKSVRLEDSRQK---LPEKTERFDSWPCVLGRETFTSGR
BTF1   --VDV VLDPDTAHPDLFLSEDRRSVRRCPFRHLGESVPDNPERFDSQPCVLGRESFASGK
BTF2   --ADV VLDPDTAHPELFLSEDRRSVRRGPYRQR---VPDNPERFDSQPCVLGWESFASGK
BTF5   KPADV ILDPKTANPILLVSEDQRSVQRAKEPQD---LPDNPERFNWHYCVLGCESFISGR
BTF3   KPADV ILDPDTANAILLVSEDQRSVQRAEEPRD---LPDNPERFEWRYCVLGCENFTSGR
BTF4   -----
```

```
BT     HYWEVEVGDRTDWAIGVCRENVMKK-GFDPMTPENGFWAVELY-GNGYWALTPLRTPLPL
BTF1   HYWEVEVENVIEWTVGVCRDSVERK-GEVLLIPQNGFWTLEMH-KGQYRAVSSPDRILPL
BTF2   HYWEVEVENVMVWTVGVCRHSVERK-GEVLLIPQNGFWTLEMF-GNQYRALSSPERILPL    B30-2
BTF5   HYWEVEVGDRKEWHIGVCSKNVQRK-GWVKMTPENGFWTMGLTDGNKYRTLTEPRTNLKL    DOMAIN
BTF3   HYWEVEVGDRKEWHIGVCSKNVERKKGWVKMTPENGYWTMGLTDGNKYRALTEPRTNLKL
BTF4   -----
```

```
BT     AGPPRRVGIFLDYESGDISFYNMNDGSDIYTFSNVTFSGPLRK FFCLWSSGKKPLTICPI
BTF1   KESLCRVGVFLDYEAGDVSFYNMRDRSHIYTCPRSAFSVPVRK FFRLGC-EDSPIFICPA
BTF2   KESLCRVGVFLDYEAGDVSFYNMRDRSHIYTCPRSAFTVPVRK FFRLGS-DDSPIFICPA
BTF5   PKPPKKVGVFLDYETGDISFYNAVDGSHIHTFLDVSFSEALYK VFRILTLEPTALSICPA
BTF3   PEPPRKVGIFLDYETGEISFYNATDGSHIYTFPHASFSEPLYK VFRILTLEPTALTICPI
BTF4   -----
```

```
BT     ADGPERVTVIANAQDLSKEIPLSPMGEESAPRDADTLHSKLIPTQPSQGAP---------
BTF1   LTGANGVTVP---------------EEGLTLHRVGTHQSL------------------
BTF2   LTGASGVMVP---------------EEGLKLHRVGTHQSL------------------
BTF5   ----------
BTF3   PKEVESSPDPDLVPDHSLETPLTPGLANESGEPQAEVTSLLLPAHPGAEVSPSATTNQNH
BTF4   ----------
```

```
BT     ----------
BTF1   ----------
BTF2   ----------
BTF5   ----------
BTF3   KLQARTEALY
BTF4   ----------
```

FIG. 5A

```
                   ─────────────────────────CYSTEINE-RICH DOMAIN─────────────────────────
52 kD Ro  MASAARLTMMWEEVTCPICLDPFVEPVSIECGHSFCQECISQVGKGGGS------VCPVCRQRFLLKNLRPNRQLAMMVN
RoRet     MASTTSTKKMMEEATCSICLSLMTNPVSINCGHSYCHLCITDFFKNPSQKQLRQETFCCPQCRAPFHMDSLRPNKQLGSLIE
          ***  *    ** *****  **  **  ** * *  *  *****  ** *     ***   *       ** **

52 kD Ro  NLKKISQEAREGTQGERCAVHGERLHLFCEKDGKALCWWCAQSKKHRDHAMVPLEEAAQEYQEKLQVALGELRRKQELAEKL
RoRet     ALKKTDQEM------SCEEHGEQFHLFCEDEGQLICWRCERAPQHKGHITALVEDVCQGYKEKLQKAVTKLKQLEDRCTEQ
          *** * * *        ** ** ***** *   ***  * *  ** * *** ** ****  *      **  **

52 kD Ro  EVEIAIKRADWKKTVETQKSRIHAEFVQQKNFLVEEEQRQLQELEKDEREQLRILGEKEAKLAQQSQALQELISELDRRCHS
RoRet     KLSTAMRITKWKEKVQIQRQKIRSDFKNLQCFLHEEEKSYLWRLEKEEQQTLSRLRDYEAGLGLKSNELKSHILELEKKCQG
          ***     *  **     ** *   *  *  *  **       ** ** * ** *    ***  ***        *

─────────B 30-2 DOMAIN─────────
52 kD Ro  SALELLQEVIVLERSESWNLKDLDITSPELRSVCHVP-----GLKKMLRTCAVHIT DPDTANPWLILSEDRRQVRLGDTQQ
RoRet     SAQKLLQNVNDTLSRSWAVKLETSEAVSLELHTMCNVSKLYFDVKKMLRSHQVSVT DPDTAHHELILSEDRRQVTRGYTQE
          ** ***      ****   *    *         *      ****        ** ****    ***********

52 kD Ro  SIPGNEERFDSYPMVLGAQHFHSGKHYWEVDVTGKEAWDLGVCRDSVRRKGHFLLSSKSGFWTIWLWNKQKYEAGTYPQTPL
RoRet     NQDTSSRRFTAFPCVLGCEGFTSGRRYFEVDVGEGTGWDLGVCMENVQRGTGMKQEPQSGFWTLRLCKKKGYVALTSPPTSL
            *   ***    * ** *  ****  * **** *   *******      * *        ****  *        *

52 kD Ro  HLQVPPCQVGIFLDYEAGMVSFYNITDHGSLIYSFSECAFTGPLRPFFSPGFNDGGKNTAPLILCPLNIGSQGSTDY
RoRet     HLHEQPLLVGIFLDYEAGWVSFSFYNG-NTGCHIFTFPKASFSDTLRPYFQVYQYS------PLFLPPP--G----D--
          **      *********  **      * *      * *   ** ***        *
```

```
NPT1  MQMDNRLPPKKVPGFCSFRYGLSFLVHCCNVIITAQRACLNLTMVWMVNSTDPHGLPNTSTKKLLDNIKN------
NPT3  ---MDGKPATRKGPDFCSLRYGLALIMHFSNFTMITQRVSLSIAIIAMVNTTQQQGLSNASTEGPVADAFNNSSISIKEFDTK
NPT4  MQVDETLIPRKGPSLCSARYGIALVLHFCNFTTIAQNVIMNITMVAMVNSTSPQSQLNDSSE----------------
                  *           *        *         ****        *

NPT1  -PMYNWSPDIQFIILSSTSYGVIIIQVPVGYFSGIYSTKKMIGFALCLSSVLSLLIPPAAGIGVAWWVCRAVQGAAQGIVA
NPT3  ASVYQWSPETQGIIFSSINYGILTLLIPSGYLAGIFGAKKMLGAGLLISSLLILFTPLAADFGVILVIMVRTVQGMAQGMAW
NPT4  ------------------VLPVDSFGGLSKAPKSLP---------------------------------AKSSIL
                      *                    *

NPT1  TAQFEIYVKWAPPLERGRLTSMSTSGFLLGPFIVLLVTGVICESLGWPMVFYIFGACGCAVCLLWFVLFYDDPKDHPCISIS
NPT3  IGQFTIWAKWAPPLERSKLTTIAGSGSAFGSFIILCVGGLISQALSWPFIFYIFGSTGCCVCCLLWFTVIYDDPMHHPCISVR
NPT4  GGQFAIWEKWGPPQERSRLCSIALSGMLLGCFTAILIGGFISETLGWPFVFYFYFGGVGCVCCLLWFVIYDPFSYPWISTS
         ** *   ** *    *                 *    ***       * ****       ****

NPT1  EKEYITSSLVQQVSSSRQSLPIKAILKSLPWAISIGSFTFFWSHNIMILYTPMFINSMLHVNIKENGFLSSLPYLFAWICG
NPT3  EKEHILSSLAQQPSSPGRAVPIKAMVTCLPLWAIFLGFFSHFWLCTIILYLPTYISTLLHVNIRDSGVLSSLPFIAAASCT
NPT4  EKEYIISSLKQQVGSSKQPLPIKAMLRSLPIWSICLGCFSHQWLVSTMVVYIPTYISSVYHVNIRDNGLLSALPFIVAWVIG
      *** **** **      **  ***  * * **  *        **  *    * **** **     ******

NPT1  NLAGQLSDFFLTRNILSVIAVRKLFTAAGFLLPAIFGVCLPYLSSTFYSIVIFLILAGATGSFCLGGVFINGLDIAPRYGF
NPT3  ILGGQLADFLLSRNLLRLLIVRKLFSSLDMQVSSWE---------------SQGDLGSSQES-SLPLPLDSSS-------
NPT4  MVGGYLADFLLLK-KFRLITVRKIATILGSLPSSALIVSLPYLNSGYITATALLTLSCGLSTLCQSGIYNVLDIAPRYSSF
         *   *      *   *    **                                                    **

NPT1  IKACSTLTGMIGGLIASTLTGLILKQDPESAWFKTFILMAAINVTGLIFYLIVATAEIQDWAKEKQHTRL
NPT3  ---VRILSLVGGMSFSCLL-----QSTCLAWSFTSRLDKQNFKTGPKRGPLPASEDIKLQT---------
NPT4  LMGASRGFSSIAPVIVPTVSGFLLSQDPEFGWRNVFFLLFAVNLLGLLFYLIFGEADVQEWAKERKLITRL
                     *
```

>CDNA21
cgacccacgcgtccgaacatggcgacctaggagaaagggaagaacaattttttctcctct
tttgggaaggtttgcgtctagtagtgcctgtgcccctgggcagattggagagaagaggga
cgactggagaatcgtcgagaaccagcggagaaaagaaaaagcaacgtttaattctagaag
gcctcctgtccctgcctgctctgggtgctcatggaatcagctgctgccctgcacttctcc
cggccagcctccctcctcctcctcctcagcctgtgtgcactggtctcagcccagttt
attgtcgtggggcccactgatcccatcttggccacggttggagaaaacactacgttacgc
tgccatctgtcacccgagaaaaatgctgaggacatggaggtgcggtggttccggtctcag
ttctcccccgcagtgtttgtgtataaaggtggcagagagagaacagaggagcagatggag
gagtaccgaggaagaaccacctttgtgagcaaagacatcagcaggggcagcgtggccctg
gtcatacacaacatcacagcccaggaaaacggcacctaccgctgttacttccaagaaggc
aggtcctacgatgaggccatcctgcacctcgtagtggcaggactaggctctaagcccctc
atttcaatgaggggccatgaagacgggggcatccggctggagtgcatatctagagggtgg
tacccaaagcccctcacagtgtggagggaccctacggtggggttgcgcctgccctgaaa
gaggtctccatgcctgatgcagacggcctcttcatggtcaccacggctgtgatcatcaga
gacaagtctgtgaggaacatgtcctgctctatcaacaacaccctgctcggccagaagaaa
gaaagtgtcatttttattccagaatcctttatgcccagtgtgtctccctgtgcagtggcc
ctgcctatcattgtggttattctgatgatacccattgccgtatgcatctattggatcaac
aaactccaaaaggaaaaaaagattctgtcaggggaaaaggagtttgaacgggaaacaaga
gaaattgctctaaaggaactggagaaagaacgtgtgcaaaaagaggaagaacttcaagta
aaagagaaacttcaagaagaattgcgatggagaagaacattcttacatgctgttgatgtg
gtcctggatccagacaccgctcatcccgatctcttcctgtcagaggaccggagaagtgtg
agaaggtgccccttcaggcacctaggggagagcgtgcctgacaacccagagagattcgac
agtcagccttgtgtcctaggccgggagagcttcgcttcagggaaacattactgggaggtg
gaggtggaaaacgtgattgagtggactgtggggtctgtagagacagtgttgagaggaaa
ggggaggtcctgctgattcctcagaatggcttctggaccttggagatgcataaagggcaa
taccgggccgtgtcctcccctgataggattctccctttgaaggagtcccttttgccgggtg
ggcgtcttcctggactatgaagctggagatgtctccttctacaacatgagggacagatcg
cacatctacacatgtccccgttcagccttttccgtgcctgtgaggcccttcttcaggttg
gggtgtgaggacagccccatcttcatctgccctgcactcacaggagccaatggggtcacg
gtgcctgaagagggcctgacacttcacagagtggggacccaccagagcctatagaatcaa
ttccttggtctcacagccatgtagacaagccctggtcatctcagcagccaccgcacaaca
cccctggtggaagacacgccctcctcccctctggtcacacaagagaacatcttccagctg
cctctttcacacccactacagacctcagccccagttttctcctcctcactaggctgtgtt
tttagtagttcctttgcttgtaactatgggatgggatccaggcatagggaactagttgtt
acacagctcccagccaagaagaaagtgtgagaagttgatgggcagcaaacctgctgttta
acatcagggtgaccacattaagcccagtattccagttggcaccagaagatatggacttgg
aatgaggcctacagggttcaccaggatgtaagaggagagaggaatccacaggaccaccag
agaggagagggaaccagatatgcagatcagagatagaggaagtggaaccagagagctggg
agggaccaaggttgtaagggtggctaagtcccaccataacagctaaggggacctgggaga

FIG. 7-2 tgatggctcatttccacccagccccaggatttccagagcgcacatccacaggcctggacc
tgggatgaagatgaatgaagaacatggatgcacgtggatgtagtttggctcaggtgtccc
tgcagttggcaaggagtcagtactcagtccctgagtgtggctgaaatttgaggtcctggc
tgagccaaggagtaatggaccagatctacctcagtattcaagttcagtggggacaccagt
ggcttcaaacttcctggtttcatgatatcttgagacgccttacaaatgatggaggattcc
aaagagttttgtttatttgggttaatatttgttggtatttatggcatttgagattgaaa
ctaagaaatgttttaatttattacctttacaacatttatttacattacatacatacattt
acaacatttattaatttatattaaaatagcatgaataagccaattataggttaatataag
tagaatgtttgtgaaaaataagtatggtatccaaagcaaaataaattttattgtgaagtg
tg >CDNA29
acgcgtccgcttcggaatgagagactcaaccataatagaaagaatggagaactattaacc
accattcttcagtgggctgtgattttcagaggggaatactaagaaatggttttccatact
ggaacccaaaggtaaagacactcaaggacagacattttggcagagcatagatgaaaatg
gcaagttccctggctttccttctgctcaactttcatgtctccctcttcttggtccagctg
ctcactccttgctcagctcagttttctgtgcttggaccctctgggcccatcctggccatg
gtgggtgaagacgctgatctgccctgtcacctgttcccgaccatgagtgcagagaccatg
gagctgaggtgggtgagttccagcctaaggcaggtggtgaacgtgtatgcagatggaaag
gaagtggaagacaggcagagtgcaccatatcgagggagaacttcgattctgcgggatggc
atcactgcagggaaggctgctctccgaatacacaacgtcacagcctctgacagtggaaag
tacttgtgttatttccaagatggtgacttctacgaaaaagccctggtggagctgaaggtt
gcagcattgggttctgatcttcacattgaagtgaagggttatgaggatggagggatccat
ctggagtgcaggtccactggctggtaccccaaccccaaataaagtggagcgacaccaag
ggagagaacatcccggctgtggaagcacctgtggttgcagatggagtgggcctgtatgca
gtagcagcatctgtgatcatgagaggcagctctggtgggggtgtatcctgcatcatcaga
aattccctcctcggcctggaaaagacagccagcatatccatcgcagaccccttcttcagg
agcgcccagccctggatcgcggccctggcagggaccctgcctatctcgttgctgcttctc
gcaggagccagttacttcttgtggagacaacagaaggaaaaaattgctctgtccagggag
acagaaagagagcgagagatgaaagaaatgggatacgctgcaacagagcaagaaataagc
ctaagagagaagctccaggaggaactcaagtggaggaaaatccagtacatggctcgtgga
gagaagtctttggcctatcatgaatggaaaatggccctcttcaaacctgcggatgtgatt
ctggatccagacacggcaaacgccatcctccttgtttctgaggaccagaggagtgtgcag
cgtgctgaagagccgcgggatctgccagacaaccctgagagatttgaatggcgttactgt
gtccttggctgtgaaaacttcacatcagggagacattactgggaggtggaagtgggggac
agaaaagagtggcatattggggtatgtagtaagaacgtggagaggaaaaaaggttgggtc
aaaatgacaccggagaacggatactggactatgggcctgactgatgggaataagtatcgg
gctctcactgagcccagaaccaacctgaaacttcctgagcctcctaggaaagtggggatc
ttcctggactatgagactggagagatctcgttctataatgccacagatggatctcatatc

FIG. 7-3

```
tacacctttccgcacgcctctttctctgagcctctatatcctgttttcagaattttgacc
ttggagcccactgccctgaccatttgcccaataccaaaagaagtagagagttcccccgat
cctgacctagtgcctgatcattccctggagacaccactgaccccgggcttagctaatgaa
agtggggagcctcaggctgaagtaacatctctgcttctccctgcccaccctggagctgag
gtctccccttctgcaacaaccaatcagaaccataagctacaggcacgcactgaagcactt
tactgatattcattccattattccatatgacagttgttttgagtttcgtaccaccttatt
gtcccttatacagataaggaaactggggtgcagaaggtgaattaactttacaaagtag
acatgacaagtgaacagcagagctgggatctaaacagcaataactaacattaacagagaa
tttaaaatgttcttagtgctgtgttataagctttggtggatgtcactcctttaatcctca
caacaccctgtcgggtagtcatattttgcaagtatggaagctgaggcagggcaacatgaa
gtaacttacataattcatacagtaatttgtgcagttgggagatgttcagccttagtccct
ggctaattgcctgttcttttccagcctgatttttttcccacaggaagagcccacatgta
gccctgaggtttccttcccaggacagctgcagggtagagatcattttaagtgcttgtgga
gttgacatccctattgactctttcccagctgatatcagagacttagacccagcactcctt
ggattagctctgcagagtgtcttggttgagagaataacctcatagtaccaacatgacatg
tgacttggaaagagactagaggccacacttgataaatcatggggcacagatatgttccca
cccaacaaatgtgataagtgattgtgcagccagagccagccttccttcaatcaaggtttc
caggcagagcaaatacctagagattctctgtgatataggaaatttggatcaaggaagct
aaaagaattacagggatgttttaatcccactatggactcagtctcctggaaataggtct
gtccactcctggtcattggtggatgttaaacccatattcctttcaactgctgcctgctag
ggaaaactgctcctcattatcatcactattattgctcaccactgtatcccctctacttgg
caagtggttgtcaagttctagttgttcaataaatgtgttaataatg
```

```
>CDNA23
atttgctttctcttttccttcttccggatgagaggctaagccataatagaaagaatgg
agaattattgattgaccgtctttattctgtgggctctgattctccaatgggaataccaag
ggatggttttccatactggaacccaaaggtaaagacactcaaggacagacattttggca
gagcatagatgaaaatggcaagttccctggcttccttctgctcaactttcatgtctccc
tcctcttggtccagctgctcactccttgctcagctcagttttctgtgcttggaccctctg
ggcccatcctggccatggtgggtgaagacgctgatctgccctgtcacctgttcccgacca
tgagtgcagagaccatggagctgaagtgggtaagttccagcctaaggcaggtggtgaacg
tgtatgcagatggaaaggaagtggaagacaggcagagtgcaccgtatcgagggagaactt
cgattctgcgggatggcatcactgcagggaaggctgctctccgaatacacaacgtcacag
cctctgacagtggaaagtacttgtgttatttccaagatggtgacttctatgaaaaagccc
tggtggagctgaaggttgcagcactgggttctaatcttcacgtcgaagtgaagggttatg
aggatggagggatccatctggagtgcaggtccaccggctggtaccccaaccccaaatac
agtggagcaacgccaagggagagaacatcccagctgtggaagcacctgtggttgcagatg
gagtgggcctatatgaagtagcagcatctgtgatcatgagaggcggctccggggagggtg
tatcctgcatcatcagaaattccctcctcggcctggaaaagacagccagcatttccatcg
cagacccctcttcaggagcgcccagccctggatcgcagccctggcagggaccctgccta
```

FIG. 7-4 tcttgctgctgcttctcgccggagccagttacttcttgtggagacaacagaaggaaataa
ctgctctgtccagtgagatagaaagtgagcaagagatgaaagaaatgggatatgctgcaa
cagagcgggaaataagcctaagagagagcctccaggaggaactcaagaggaaaaaatcca
gtacttgactcgtggagaggagtcttcgtccgataccaataagtcagcctgatgctctaa
tggaaaaatggccctcttcaagcctggtgaggaaatgcttcagatgaggctccaccttgt
taaataaattggatgtatggaaaaatagactgcagaaaaggggaactcatttagctcacg
agtggtcgagtgaagattgaaaattaacctctgagggccagcacagcagctcatgcctgt
aatcctagcactttggaaggctgaggagggcggatcacaaggtcaggagatcaagaccat
cctggctaacacggtgaaaccccgtctctactaaaaatacaaaaaataaaaaattagccg
ggcatggtgacgggcacctgtagtcccagctactcgggaggctgaggcaggagaatggca
tgaacccggaaggcagagcttgcagtgagccgagatcacgccactgcactccagcctggg
agacagagcgagactctgtctcaag >CDNA44
ctgaagcttgcatgcctgcaggtcgacccacgcgtccgcggacgcgtgggcggacgcgtg
ggttttccttcttccagaaggagatttaaccatagtagaaagaatggagaactattaa
ctgccttccttctgtgggctgtgattttcagaggggaatgctaagaggtgattttcaatg
ttgggactcaaaggtgaagacactgaaggacagaattttggcagaggaaagatcttctt
cggtcaccatacttgagttagctctagggaagtggaggtttccatttggaattctatagc
ttcttccaggtcatagtgtctgccccccaccttccagtatctcctgatatgcagcatgaa
tgaaaatggcaagtttcctggccttccttctgctcaactttcgtgtctgcctccttttgc
ttcagctgctcatgcctcactcagctcagttttctgtgcttggaccctctgggcccatcc
tggccatggtgggtgaagacgctgatctgccctgtcacctgttcccgaccatgagtgcag
agaccatggagctgaagtgggtgagttccagcctaaggcaggtggtgaacgtgtatgcag
atggaaaggaagtggaagacaggcagagtgcaccgtatcgagggagaacttcgattctgc
gggatggcatcactgcagggaaggctgctctccgaatacacaacgtcacagcctctgaca
gtggaaagtacttgtgttatttccaagatggtgacttctatgaaaaagccctggtggagc
tgaaggttgcagcactgggttctgatcttcacgttgatgtgaagggttacaaggatggag
ggatccatctggagtgcaggtccactggctggtaccccaaccccaaatacagtggagca
acaacaagggagagaacatcccgactgtggaagcacctgtggttgcagacggagtgggcc
tgtatgcagtagcagcatctgtgatcatgagaggcagctctggggagggtgtatcctgta
ccatcagaagttccctcctcggcctggaaaagacagccagcatttccatcgcagaccct
tcttcaggagcgcccagaggtggatcgccgccctggcacggaccctgcctgtcttgctgc
tgcttcttgggggagccggttacttcctgtggcaacagcaggaggaaaaaaagactcagt
tcagaaagaaaagagagagcaagagttgagagaaatggcatggagcacaatgaagcaag
aacaaagcacaagagtgaagctcctggaggaactcagatggagaagtatccagtatgcat
ctcggggagagagacattcagcctataatgaatggaaaaaggccctcttcaagcctgcgg
atgtgattctggatccaaaaacagcaaaccccatcctccttgtttctgaggaccagagga
gtgtgcagcgtgccaaggagccccaggatctgccagacaaccctgagagatttaattggc
attattgtgttctcggctgtgagagcttcatatcagggagacattactgggaggtggagg

FIG. 7-5 taggggacaggaaagagtggcatataggggtgtgcagtaagaatgtgcagagaaaaggct
gggtcaaaatgacacctgagaatggattctggactatggggctgactgatgggaataagt
atcggactctaactgagcccagaaccaacctgaaacttcctaagccccctaagaaagtgg
gggtcttcctggactatgagactggagatatctcattctacaatgctgtggatggatcgc
atattcatactttcctggacgtctccttctctgaggctctatatcctgttttcagaattt
tgaccttggagcccacggccctgagtatttgtccagcgtgaaaagaagaagagagttcct
ccaattctgaccgagtgctgatcattccctagagacaccagtaaccccgggcttagctaa
cgaaagtggggagcctcaggctgaagtaacttttctctgcttctccctgcccagctcaga
gctgagggcctcccccctccacagcaaccaatcacaaccataaagctacaagcacgcactg
aagcactttactgatactcattcaattattcatatgacagttgtttgagtttggtaccat
cttattttccccttatacagataaggaaactgggggtgcagaaaagtgaattgactacaaa
gtagacatgactagttaacaacacagctgggatctaaacagcaataactaacattaatgg
agaacttaaaatgctctgagtgctgtgttatgagctttggtggatgtcactcctttaatc
ctcgcaacaccctgtcgggtagtctcatttagcaagtatggaagttgaggcagggcaaca
ttaagcaacttacataactcatgcagtaatttctgcagttggggagatgttcagcttcagt
ccccggccctatggccgttctttctttccaccctgtttcttcccccataggaagaacccacct
gtagccctgaggttctttctttcccaggatggctccaggataaggatcactgtaggtggttgt
ggagttgacaccccctgttgactccttcccagctgattgtcagagccttagacccagcacg
ccttggattagctttgcagagtgtcttggttgagagaataacctcaccgtacccacatga
cacgtgatttggaaagagactagaggccacacttgataaatcatggggaacagatgtgtt
ccacccaacaaatgtgataagtgatcatgcagccagagccagccttccttcaatcaaggt
ttccaggcagagcaaatacccctagagattttctgtgatataggaaatttggatgaaggga
gctagaagaaatacagggatttttttttttttttaagatggagtcttactctgttgctag
gctggagtgcagtggtgcgatctcagctccctgcaacctccacctcctgggttcaaacaa
ttctcctgcctcagcctcccgagtactgggaatataggtgcacgccaccacacccaacaa
attttgtacttttagtacagatgagggttcactatgttggccaggatggtctcgatctc
ttgacctcatgatccacccacctcggtctcccaaagtgctgggattacaggcttgagcca
ccgggtgaccggcttacagggatattttaatcccgttatggactctgtctccaggagag
gggtctatccacccctgctcattggtggatgttaaaccaatattcctttcaactgctgcc
tgctagggaaaaactactcctcattatcatcattattattgctctccactgtatcccctc
tacctggcatgtgcttgtcaagttctagttgttcaataaatttgttataatgctg >CDNA32
agagaacaggtcccagataccgagtccgcaaccccaaacatcgcgattaataggaggcct
ctggtctctgcctgccctgggtgctcatggaaccagctgctgctctgcacttctccctgc
cagcctccctcctcctcctgctcctcctccttctcagcctgtgtgcactggtctcag
cccagtttactgtcgtggggccagctaatcccatcctggccatggtgggagaaaacacta
cattacgctgccatctgtcacccgagaaaaatgctgaggacatggaggtgcggtggttcc
ggtctcagttctcccccgcagtgtttgtgtataagggtgggagagagagaacagaggagc
agatggaggagtaccggggaagaatcacctttgtgagcaaagacatcaacaggggcagcg
tggccctggtcatacataacgtcacagcccaggagaatgggatctaccgctgttacttcc

FIG. 7-6 aagaaggcaggtcctacgatgaggccatcctacgcctcgtggtggcaggccttgggtcta
agcccctcattgaaatcaaggcccaagaggatgggagcatctggctggagtgcatatctg
gagggtggtacccagagcccctcacagtgtggagggaccccctacggtgaggttgtgcccg
ccctgaaggaggtttccatcgctgatgctgacggcctcttcatggtcaccacagctgtga
tcatcagagacaagtatgtgaggaatgtgtcctgctctgtcaacaacaccctgctcggcc
aggagaaggaaactgtcattttattccagaatcctttatgcccagcgcatctccctgga
tggtggccctagctgtcatcctgaccgcatctccctggatggtgtccatgactgtcatcc
tggctgttttcatcatcttcatggctgtcagcatctgttgcatcaagaaacttcaaggg
aaaaaaagattctgtcagggaaaagaaagttgaacaagaggaaaaagaaattgcacagc
aacttcaagaagaattgcgatggagaagaacattcttacatgctgctgatgtggtcctgg
atccagacaccgctcatcccgagctcttcctgtcagaggaccggagaagtgtgaggcggg
gcccctacaggcagagagtgcctgacaacccagagagattcgacagtcagccttgtgtcc
tgggatgggagagcttcgcctcagggaaacattactgggaggtggaggtggaaaacgtga
tggtgtggactgtggggtctgcagacacagtgttgagaggaaaggggaggtcctgctga
ttcctcagaatggcttctggaccctggagatgtttggaaaccaataccgggccctgtcct
ccctgagaggattctccctttgaaggagtccctttgccgggtgggcgtcttcctggact
atgaagctggagatgtctccttctacaacatgagggacagatcacacatctacacatgtc
cccgttcagcctttactgtgcctgtgaggcccttcttcaggttagggtctgatgacagcc
ccatcttcatctgccctgcactcacaggagccagtggggtcatggtgcctgaagagggcc
tgaaacttcacagagtggggacccaccagagcctatagaatcaattccttggactcacag
ccatgcagataagccctggccatctcagcagccaccgcacaacccccctaatgaaagaca
cgccctcctccctctggtcacgtaagagaacatcttccagctgccttttcacacccac
tccagccctctgccccagttttctcctcctcactagtctgtggctttagtagttcctttg
cttgtaattatgggatgggatccaggcatagggaactagttgtttcatagctcccagtca
aaaagaaagtgagagaagctgttgggcagtgaacctactgtttaaaatcaggataaccac
attaagcccaatatgccagttggcaccagatgctgtggacttggaatgaggccaacaggg
ttcaccaggatgagagaggagagaggaatccacaggaccaccagaagggagagggaacca
gatatgcagatcagagatagaggaagtggaaccagagagctgggagggaccaaggttgta
aggatggctaagtcccaccataagagctaaagggtcctgggagatgatggctcatttcca
cccaaccccaggatttccacagcacacacccacaggcctggacctgggatgaagatgaat
gaagaacatggactcatgtggatgtggtttggctcagatgtccctgcaataaacaagggg
tcagtacttagtccctgagtgtggttgaggtttgaggtcctggtcgagcagggcagtact
ggaccaggtctacgtcagcattcaggttcaatggggacaccagtggcttcaaacttcctg
atctaattatgttttagacacttagaagttattgaggactttaaagagcttttgtttat
ttgggttaatatttatgacatttgacattgaaacaaaaatttaaaatgttatcttttaat
ttatgttaaaatagcattaataaatcagttataggttaatgtagataggatgttttgtga
aaaagcaatctattgtgtccaaataaaaaaacaaaaagtgtgacactggttaacttttt
ccagatctcatgtctggcttaataagagatatttgtattatcatatctgcctttgtatta
aacctattggtatatcataggtcatgttagctcaaaaaaactttactgcacactactgag
agaatgagatgaaaaacgattaatgtttcattattattattgtgaaaatattattaacac
tggggactccttaagagtacatcagagttctctctaggaatcccaaaaccacattttgaa

FIG. 7-7 actagaatagtggatcctggaagttaatccatgtgctggttaattttagatgtcaacctg
gtgtttccagaagagattggcaagtgagtcagtgggaaattctctccttctgttggctgg
gtgcccaatacaacaaaaaggcagaggaaaggcaaattcttctctcctctggagctgaga
cactcttcttcttctgcccttggacatcagaactcctggctctccggcctttgaacttca
ggacttgtaccaggaggccctgggttctcaggcctttggctttggactgagagttacaca
atcagcttccctggttctgaggcttttcagacttaaactgagccatgctaccagcatccca
gggtctccagcctacagatgagctgttgtgcgatttcttagcctccataatcacatgagc
caatctccttaataaatgcctgctcatagatctgtatctacatctatatctgtatgtgca
tctatatctatgcctatatctatatctatatcatattgattttgtctctctggagaaccc
tgactaataaaatgaggcatct >CDNA27
gacccacgcgtccgaaaagctatggcctcaaccaccagcaccaagaagatgatggaggaa
gccacctgctccatctgcctgagcctgatgacgaacccagtaagcatcaactgtggacac
agctactgccacttgtgtataacagacttctttaaaaacccaagccaaaagcaactgagg
caggagacattctgctgtccccagtgtcgggctccatttcatatggatagcctccgaccc
aacaagcagctgggaagcctcattgaagccctcaaagagacggatcaagaaatgtcatgt
gaggaacacggagagcagttccacctgttctgcgaagacgaggggcagctcatctgctgg
cgctgtgagcgggcaccacagcacaaagggcacaccacagctcttgttgaagacgtatgc
cagggctacaaggaaaagctccagaaagctgtgacaaaactgaagcaacttgaagacaga
tgtacggagcagaagctgtccacagcaatgcgaataactaaatggaaagagaaggtacag
attcagagacaaaaaatccggtctgactttaagaatctccagtgtttcctacatgaggaa
gagaagtcttatctctggaggctggagaagaagaacaacagactctgagtagactgagg
gactatgaggctggtctggggctgaagagcaatgaactcaagagccacatcctggaactg
gaggaaaaatgtcagggctcagcccagaaattgctgcagaatgtgaatgacactttgagc
aggagttgggctgtgaagctggaaacatcagaggctgtctccttggaacttcatactatg
tgcaatgtttccaagctttacttcgatgtgaagaaaatgttaaggagtcatcaagttagt
gtgactctggatccagatacagctcatcacgaactaattctctctgaggatcggagacaa
gtgactcgtggatacacccaggagaatcaggacacatcttccaggagatttactgccttc
ccctgtgtcttgggttgtgaaggcttcacctcaggaagacgttactttgaagtggatgtt
ggcgaaggaaccggatgggatttaggagtttgtatggaaaatgtgcagaggggcactggc
atgaagcaagagcctcagtctggattctggaccctcaggctgtgcaaaaagaaaggctat
gtagcacttacttctcccccaacttcccttcatctgcatgagcagcccctgcttgtggga
attttctggactatgaggccggagttgtatccttttataacgggaatactggctgccac
atctttactttcccgaaggcttccttctctgatactctccggccctatttccaggtttat
caatattctcctttgtttctgcctcccccaggtgactaaggaaaagagcagaagctcctt
ggtttaaccagcacagagaaataatataaatcccataagggcagacgtttggtctgttt
tcttcgctgtcatttccttagtagttagactagtgctgagattttagtggatatataatt
gatttatgttgaatatatggacttagcaactaaaaataccacagatggttaacctggact
ggggcaaagcaagataatagtgatgatcgtatgttgctgtctccatccgtctttaatggg
tcagggctttgatttccaagggtcttcaggtgatgagtaggggtacccacaagtcagaag

FIG. 7-8 gtctgcgttctcctagtttgtttgctgccatttgaactcatgtagggaatgaaagaaagc
tgcaattatccgccaactgcatttaaaacaaaacaaaacagaaaaatcaaaataacattg
actcttccaaccactgacatgttgtttaataatctaagcggcagtcctggaggctaccag
acttactgagttctacctgagaaacagccaagcaaagtgtgagagaagggttaagactgg
cttacaatgagatgcttcaaatgaaaagggaattatgagtaaaattgaactttgatgggg
gattcagttctggaaaagaatttggtattttccagtctgctaggaccaattaccttgaaa
tattttaaaatctcagtaaatagttattgctgaaatggctgttggcagttcttattatga
ttcagagaagagcaaatagaccttaacttcattttgaaaaagaccaaattaccatacccg
agtgagtaatgacaggactacaactaaaacataaacaacattaatgatgaccataaaaag
tcacaaaattgctaaatgttataatttagagttgacataaaaattgatggccaggcatgg
tggctcacgcctgtaatcccagaactatgtgaggctgaggcaggtggatcacttgaggtc
aggagttcaacaccagcctggccaacatggtgaaaccctgtctctactaaaaatacaaaa
attagccgggcatggtggtaggggcctgtaacccagctactcgtgaggccaaggcaggag
aattgcttgagcctgcagcagctgcagtaagccaagatcatgctgtgcctcaaggaaaaa
aaaaattaatgtttactgatatttgttgaagtcctacaacatcacctctgagaataggag
aaatgaagcaacagttgtgtctagatgtcagaggcatggctgggcctccatctctgccta
agggagatataaaagagttcaaactattgcccatgttccccagggtcagaagttctaatt
atgatgatagaggctggttgtaagtagtaagtgaagggtagcagaatatgccatctttg
gcataagaagtattttgagttgaagacaattgag >CDNA22B
ggacagaaaactccctcctttttccaagttagccttatagtctagggcttaaaatactggt
ttaatggtgaaggtaagtgcttttcttcttttgggtagaaggattattactaacttacc
aaaggtccattaaggggagggaacagttttaggagaagtcagagaaaagacattaacagc
aacataaggatctccatctggtaatattgcctaattccaaaatgaagagactctctgaaa
aagataactgattcaatgaagaccctagggcaaggcttgagaagccactggtaccaatgg
acactgtggacaatggtcatttctccaaggacgctataaaagactgtcgtagtaaaagag
attcagggcacagggaaactccaccacaaagcgtggtaccatttcccacagaagctaaat
ggacgggaagcctgccaccaggaaaggtccagatttctgttcattacgctatgggctggc
tcttatcatgcacttctcaaacttcaccatgataacgcagcgtgtgagtctgagcattgc
gatcatcgccatggtgaacaccactcagcagcaaggtctatctaatgcctccactgaggg
gcctgttgcagatgccttcaataactccagcatatccatcaaggaatttgatacaaaggc
ctctgtgtatcaatggagcccagaaactcagggtatcatctttagctccatcaactatgg
gataatactgactctgatcccaagtggatatttagcagggatatttggagcaaaaaaaat
gcttggtgctggtttgctgatctcttcccttctcaccctctttacaccactggctgctga
cttcggagtgattttggtcatcatggttcggacagtccagggcatggcccagggaatggc
atggacaggtcagtttactatttgggcaaagtgggctcctccacttgaacgaagcaagct
caccaccattgcaggatcagggtcagcatttggatccttcatcatcctctgtgtgggggg
actaatctcacaggccttgagctggccttttatcttctacatctttggtagcactggctg
tgtctgctgtctcctatggttcacagtgatttatgatgaccccatgcatcacccgtgcat
aagtgttagggaaaaggagcacatcctgtcctcactggctcaacagcccagttctcctgg

FIG. 7-9 acgagctgtccccataaaggcgatggtcacatgcctaccactttgggccattttcctggg
tttttcagccatttctggttatgcaccatcatcctaacatacctaccaacgtatatcag
tactctgctccatgttaacatcagagatagtggagttctgtcctccctgccttttattgc
tgctgcaagctgtacaatttttaggaggtcagctggcagatttccttttgtccaggaatct
tctcagattgatcactgtgcgaaagctcttttcatctcttgatatgcaagtttcctcatg
ggaatctcaaggggatttgggctcatcgcaggaatcatctcttccactgccactggattc
ctcatcagtcaggatttgagtctggttggaggaatgtcttttcctgtctgctgcagtc
aacatgtttggcctggtcttttacctcacgtttggacaagcagaacttcaagactgggcc
aaagagaggacccttacccgcctctgaggacataaagttacaaacttaaatgtggtactg
agcatgaacttttaaacatttttacttctctccatattcctgaccatagactcagcag
ttcttaactctggctgtgtgttagtcttccctggggagcctttataagacactgatactt
gggacccactccagagattctgaatgaattggtctggggtggaacccagatactactaat
ttttagatactccttagaggtttctagcatgcgcccggggttgacaacagctggacaaac
ttgaaaagtcaattcatgtggcctttgaattttcctcattggaaagtactaaataaataa
aaattcatgtgaaaatgatcactgataaatatcttcatggtggggcaggttattggatgc
agagaagatctgctcggaattgtagccatatgttacagatctcagcaccgatcagaactg
taaagctataatccccagaattaaagttttattattttttatacattgtaaaacataga
cgtttatttatgtgattaaattctattaaaatttacatgctaaaat >CDNA22E
acgcgtccgcccacgcgtccgcccacgcgtccggtcggggccagagcgcaggtgtacctg
gcggccgtgctggagcacctgaccgccgagatcctggagctggctggcaacccggcccgc
gacaagaagacccgcatcatcctgcgccacctgtagctggccattcgcaacggcgaggag
cttaacaagctgctgggcgaagtcaccatcgcgcagggcggtgtcctgcccaacattcag
ggcgtgcttctgccccagaagaccaagagccaccacaaggccaagggtgaaaaccattca
ctaggagaggagaaacacaatggccaccaagacagagttgagtcccacagcaagggagag
caagaacgcacaagatatgcaagtggatgagacactgatccccaggaaaggtccaagttt
atgttctgctcgctatggaatagccctcgtcttacatttctgcaatttcacaacgatagc
acaaaatgtcatcatgaacatcaccatggtagccatggtcaacagcacaagccctcaatc
ccagctcaatgattcctctgaggtgctgcctgttgactcatttggtggcctaagtaaagc
cccaaagagtcttcctgcaaagtcctcaatacttggggtcagtttgcaatttgggaaaa
gtggggccctccacaagaacgaagcagactctgcagcattgctttatcaggaatgttact
gggatgctttactgccatcctcataggtggcttcattagtgaaacccttgggtggccctt
tgtcttctatatctttggaggtgttggctgtgtctgctgccttctctggtttgttgtgat
ttatgatgaccccttttcctatccatggataagcacctcagaaaagaatacatcatatc
ctccttgaaacaacaggtcgggtcttctaagcagcctcttcccatcaaagctatgctcag
atctctacccatttggtccatatgtttaggctgtttcagccatcaatggttagttagcac
aatggttgtatacataccaacttacatcagctctgtgtaccatgttaacatcagagacaa
tggacttctatctgcccttccttttattgttgcctgggtcataggcatggtgggaggcta
tctggcagatttccttctaaccaaaaagtttagactcatcactgtgaggaaaattgccac
aatttttaggaagtctcccctcttcagcactcattgtgtctctgccttacctcaattccgg

FIG. 7-10

```
ctatatcacagcaactgccttgctgacgctctcttgcggattaagcacattgtgtcagtc
agggatttatatcaatgtcttagatattgctccaaggtattccagttttctcatgggagc
atcaagaggattttcgagcatagcacctgtcattgtacccactgtcagcggatttcttct
tagtcaggaccctgagtttgggtggaggaatgtcttcttcttgctgtttgccgttaacct
gttaggactactcttctacctcatatttggagaagcagatgtccaagaatgggctaaaga
gagaaaactcactcgtttatgaagttatcccaccttggatggaaaagtcattaggcaccg
tattgcataaaatagaaggcttccgtgatgaaaataccagtgaaaagatttttttttcct
gtggctcttttcaattatgagatcagttcattatttattcagacttttttttgagagaa
atgtaagatgaataaaaattcaaataaaatgataactaag
```

FIG. 8-1

>HLA-H.CONTIG
TTTGTAAGTATTCTATTTTATTTATATGTGTTTGTGTTTCTGAGTATGTCC
TGAGTTGCACGATAATACTATATTTCTTATTGGGTAACATTGTCAGAAAAG
TTTCTAAAAACTTTCTCTGCTGCACTTATTTTATACATTTTATTTATGTTA
ATAATCTCACATTTAACACACTTATGATTTATTCTCAACAGAAAAAGGTGG
TATTTCTTTCATTTAGTCTTTTAAAAAGCTCACATTATCAAATGATTGCTC
AATCATTTAATCTCTTTGCTTCTCTTATATGCATTGATTTAATAAATATGT
ATACTAGTTTCTCCATCGATTCTTTAGATTTGAAACTTATTTTCCTTTTAT
TCTTACAAAACTGACTTGTCTATAGGCCCACTTCTACTTCCTTTATTCTAT
CATCTTCCTCAACTTATTCTGTGGTCAAAGAATGGAGAAATAATATTAATA
ATATGTTTTTCTCATCAATGACTTCCACCTGTTCTCTGAGAAATTCAGCTT
CAAGAACTTTAGTTTGATATGACTGCAAAGATAATACACAGTCTAAATCAT
AAAAATGTCTCAAAGGTTTTTTTTTTATTTGTTTCTTTGAAATATCCATGA
ACAGGCATGTTTCTCCCCCTGTAGTGCAATTTGTGTGAAATTCTGGCATGC
ACTTAAGAGGATGTCCTAAAATACCAATATTTAATTGATTCTAAGTCATGT
ATTGTATCACATTTTTGCCCATGGATTGTTGAAATCCATGGACAAAACTGA
TAGCATTTTAGAACTTCCTTTGTCTAGTGGCAGTCTTGATATATTCACACT
ATCTATTGACAAAAAATCTAAAGCACCAGGCTCAAAGCTTGTAGAGTAGGT
GTCAGTGATTTGGAGGACATCTCTAGGGCAATAGTAGAGGCATTTTTAACC
CCTAACAACTAAATGATCATCAGAAGTGAGTGATATCCTCACTCATGACCC
CAACTGCTCTAATTTCTATTGTTTTCTTGCAGAAATGAGAGCAGGTGGGGT
CATGGGTGAGGAATGAGGTGTTGAAAGTGAATGGGGTGTTGAAAGCAAGGT
GTTTAGCAGTGTTCTGAAAGCATACATTTAAGTAGGCTATCCGGGCACTGT
CAATAGCTAAGTGTCAAGCTAAGTACTCTATTTTATTCTAAGAACTATTTT
TAGAAATGCTGAATCAACAAATCTCAGATGGCACAGAGGTTGTCATTTTTG
AATAATATGAATATCAGTAATTTTAGTTGGAAAAGAAGATTTTCAAAGAGC
CATCTAAGTTTCCAAAATAAGTGTTGCAGTCATATTAACTATTATATTTTC
CTGCCTGTTGATCTACTGCCTGTGAATTGCTTATCAAACCAACAACCAACT
GGAATACATAGACTGCATGTCTTGTTCATTTCCTGCATTCTCAAGTAATGG
TTTAACAAACTCATGAGCTTACTCTTTAATCTGAACCATGCTTAACTTCAA
TTATGTTGATTTAGTCTAAGGATGCAGAATTTATTTTATAGTTATGTAGGA
ACTGGAATCCAAAATGTAATATGCCTCCAAGCTTTTCTTTGTTGGCCTCTG
AAGGAGCATCACCTCTACAACTTCAACGTTGTTATGAATACCTCTGGGGAG
GTGTTCACCTCAGGACCCAAATTTGGAAAAAGGGAAGTGCCACTTTGGAGG
AGTGCTCTGAGCAGCTGATCCATTAAATGTCCCGATCACATGCACGTGGAA
GTGTCATTGCAATATCTGCACTAACAGAAGCTCAGTGACTTGAGAAGTGAG
TCTGGAATTCTAAGAAAAAGGCAAGGCATCTCTCTTGCCACTTGTTATTTT
TCCAGTCAAGCAACTGTGATAAGAGGGCATGGAGAGCAGGAAGAAGTGAAA
AATCCCAGGAAAGTCTGGAGTGGAATCATTAAACCAATTCTGCTCCCTCTC
TAGGCCAACTTGGGCCTATTATGAATAAGGAGGTCTCTTATAATCCATCTA
ACTCCACTCAGGAACAATTTGGGGATCTGAGACTGTGAACTCAGTGGGCAA
AAAAATATTTCTTGGCCTATCATTATTCTCTGTAGGATGTTAAGGACAGGT
TTCTGTATGTGGAGTCCTCAGTTTTTGCCTTCTCTCCTTGAGATATTTTTA
TGCTATTTAGTAATTGATGGCCACAGTTGATCGACCACATTTCTGGGCAAC
TCTAATAATCCTTGTTATATTAATCATTGGACCAATCTTGATTGTGTATGA
CCATCATCTTGTAGCTACCACCTCTATGTGGATGCTCTCCTCACCCTGCTT
AAGTGCCAATGTCTGTGCTATGGGCCTACCTGTCACATGGATAATCTCTTC

FIG. 8-2

```
ACTCCAGTCAGGCTCCAACATTAACACAGGGCTGTTCTCTTGTCCCCCTTT
GAAGACAGCTTCATCACCCTATTCAAGTTGCAGTACTCTCACTGGGCCTCC
ACTGTTGCCTCTCTCTCACTCTGCTTAGGTTTCTTCACTCCACTCCAGGCA
ACTGTCACTAAACATCCTTTCCCCCATATATAACACAGACATCTACCTTGC
TTGGCCAAACCCACTGGATTTCAGACTCACTCATTCAGAGAGTAAGACAGA
GAGGGGTTCATTTTTTATTTTATTTTATTTTTTATTTTTTGAGACGTTGTC
TCACCCTGTCGCCCAGGCTGGAGTGCAGTGGTGCAGTCTTGGCTCACTGCA
ATCCCCACGTCCCAGGTTCAAACGATTCTCCTGCCTCAGTCTCCCAAGCAG
CTGGGATTACAGGTGCCTGCCACCATGCCCAGCTAATTTTTGTATTTTTAG
TAGAGACAGGGTTTCGCCGTGTTGGCCAGGCTGGTCTCGAACTCCTGACCT
CAAGTGATCTACCCGCCTCGGCCTCCCAAAGTGCTGGGATTACAGGTGTGA
GCCACTGCGCCCAGCCGGGGTTCATCCTTAATACATACATTAGAGATATAG
ATTCTGTTTTTATCTAAAAAGTCTTTATAAGGCCGGGCGCGGTGGCTCACG
CCTGTAATCCCAGCACTTTGGGAGGCCGAGGCGGGCGGATCACGAGGTCAG
GAGATCGAGACCATCCCGGCTAAAACGGTGAAACCCCGTCTCTACTAAAAA
TACAAAAAATTAGCCGGGCGTAGTGGCGGGCGCCTGTAGTCCCAGCTACTT
GGGAGGCTGAGGCAGGAGAATGGCGTGAACCCGGGAGGCGGAGCTTGCAGT
GAGCCGAGATCCCGCCACTGCACTCCAGCCTGGGCGACAGAGCAAGACTCC
GTCTCAAAAAAAAAAAAAAAAAAAAAAAAAAAAAGTCTTTATAAAAATCTG
ATTGAATGGTTGAATGCTGTGCTAAAATCTGCATAATATCTTACAACACTT
CTGTGAATCACGAGACAGTTTTGAATGCTAAATGTCAGTTAACAGATCTAA
AGGGACCAACATCTGCTTTCCCAAATTATATGAAAGAAGATCCTGATCCCT
CATCAGGTGAAACTCACATCAGACAACAGTGTCTGCATTTCTCCAAAACCC
GCCTCAGCCCCATGGCCACTTTCCAGGGTTATCCTGCCTACCAAGCACTCT
CTTTCCTCAGAAAAACTTGGGGGAAAATGTAGAATAATAATTTTTTGAAGT
TCTGACCAACTTCTTGAATCACTCAGCATGTTTTTGACTGCAGGTACAGAA
AACGCTGACTCAACAAATTTAAACACTATATAAATTTCTTATCTCCCCAAA
CAGGACATCAAAGGCAGAAAGGTTCCAGAGCAGGGTGATCAGAGCTCTGGC
TCCACTGCCCTCAGTCTTCTTGCCTCTGCTCTCCTTCACAGCAGGCTTTAC
CCCCCATGCTGGTCACAGTTTCAAGTGTCCATGCAGACACAAGTTAAAGGC
AGGAAGAAACAGTGCGTTTCTCTTGGAGATCAAGGAATGCCTTTCCAGAAA
ACTCCCCCTTATGTCTCATTTGCCAAAACTTGGCCTAGTCTCAGGTGCTGC
CTGAGCTAATCAGCTACAGAAGAAGGGACCACATGACTGGTGTGGACCAGT
CAGAATTCACCACATGAAGCTAGTAATGTGGCTCACACTTCCCAGGGGGAT
ATGGCCAGGTAGCAGACAGTGGATCGCTGAACAGAATACTGATAGATTTCA
GCACCAAGGTTAGAATGGCTACCACACCTAATCCCACCCTATCCCCGTTTC
CTTCTTTAATTTTTTCCATAGCACTTATCAGTAGCTGACAAACTGTATATG
TTTTTACTTTTTTATTGTCTGTAGCTCCCAAGTAGAATACAAACATCTGAA
ACTCACTGTATCCATCCTGAGTAATGTTCTTTTCAGCTCAGTCACAATCAT
TTTTTGATAGCCTATCCTATAAGCTTAACTTATAGTGTTAATCAGTATTAA
TACATCTTAGTGGGAAAGAAGGAAAAAATAAACGATCACACACACACACAC
ACACACACACACACATACATTTACGTAACAGAGCAAGTGTGAAAATACC
TAAAGGCTTTATAGCTCCTTTTGTCAATGGATACATGACAGCATTTTTGGC
ATTCTTTACTACTCTTATTCTATGCTCCATTTGTCTTCAGTCAGCACCTCA
GCTGCCCTTATGTTTTACTTGGTAAGGCAAATTCCTAAATGAGCCTGGTAA
TTAGTCATCCAGCTTATAGGAAGGTACTATAGTTTTTCATTAACTTTTTCA
```

FIG. 8-3

```
CTGGGCTTGAGAGTAGTAAGGACTCCCAGAGAATTCCTTGTGTTCCAAAAG
TACTTCTCCTTGACATCTTGGTATAGGATTAATAACTGTTTACCTTTGATA
ATCAGGAAGAATGACTCCAGCTAGTACAGTTACGTGATGCCTATACATTCC
TTTTTTTCTGGGAAAAATGTAATGTGAAATTAAGTGCAAAAACCATGCCTT
GTTTATGTATGTATCAAACACTTCTAGAGCTTTCCCAATACAGTTCTCTTC
TCAGCAAACAAGAGGACTATACCCTCATCCCCACCCCTGCACTTAGGTGTA
GCCAATGTGTTGTAACTTAAAGAGGAGAGGGCACTGGATGAAGGGAAATCT
GTCTAACAAGCTTCTTTATTTCACCTAGTGGAAAAAAGCCTTAATCTGCAG
TGGGGCAGTTTTCAAGGACATAGACTGAATTGGCTCATGCATTTATGGAAG
ATGAGGAGTCCCATGATCTGTAATCTGCAAGCTGGAGACCCAGGAAAGCTG
GTGGTATGATTCAGTCTGAATCTGAAGGCCTGAGAACCAGAGGAACTGATG
ATGTAAATCCCAGTTCAAGAGCAGGAGACCAGATGAGATGTCCCAGCTCAA
GCAGTGAGGCAGAAAAAAGGCCCAAATTCCCCCTTCCTCTGCCTTTTCTT
CTATTCAGACCCTGAATATCAGGTGGCATAATGCCATCCACACTGGGAAAG
ACAGTTACTTTACTAGGATCACCTATTCAAAGGCTAATCTCATCCAGAAA
CACGCTCACAAACACAGCCAGAAATAATGTTTAACCAGATAGCTGGTTATC
CCCTGACTCAGTCAAGTTGACACAAAAAATGAACTATTTCAAAGCTTACTG
TAATCAACAGTTTTGTCAAAAAGATAGACACAAATCAGTGGAATGAGATAA
ACAGTCTAGAAATAAACCAACAAAAATATTGCCAACTAAGGCAAAGGTAAT
CAATGGAAAAAAGATAGTCTTAGCAACAAATAGTACTGGAACACCACAATG
TGTTAATAAAGTGAAACTGGAGACATCTCTCACACCTTATACAAAAGTAAC
TAAAAATAAATCAAAGGACTAGATGTAATGTATCAAACATTACATCTTTTA
GAATGTATCAAACATTACAAGCTTTTAGAATAAAATATAGAAGAAAATTTA
CATGATCTAAGATTTGGCCCCAATGAAGTTTTAGCTATAATAACAAAAGTA
TTAGTCATGGAAGAAAACAAAATTGATAAGTTCAGGTGGGCTAAATTAAGG
GAAAAAAATCACTTTGCAGTAGAGAAACCTGAAACATTACCTAAACCACAT
GATGAAGGTTAATATCAGTGATGTCATGTGGATATCATGTTCTCCCTAAAA
TGATGTGACAAGAAGGGCCCTTTGCCCTTGTGGTATTATTTCAAAAAATCT
ATAACTCCGGTGTAATTATGAAAAAAAAGCAAATGATCTTCAGGACTGTTA
AGGTCATGAAAAGCAAGAAAAGACTGAGACATTGTCACAGACAAAAAAAGA
CTAGGGAGATATGACAAGAAAATGCAGTGTGGTATTCCAGATTGGACCTTG
GAACAGAAAGAAAACATTAGTGGAAACAGTGGTGAAATCCACATAAAGTCT
AGGGTTTGGTTAATAGAGTTTCATGTATCAATGTGAGTTGCTTATATTTGA
CAAATGTATCATAATAATGTAAAATCCTAACAATGGGGGAAAGCTAGGTGA
AAGATATATGGGAACTCTCCTGTACTGTCTTTGTACTATCTTTGCAACTTT
CCTGAAAATCCAAATTATTCTAAAACAGAAAAGTTCATGCTATTAGAAGTG
AGGATAGAGGTTACCTTGAAGAAGCTGAGGTCTAGAAGAGACCATGAAGGG
TCTAATTAGCTAACACACGTTGAGTATCCCTTATGCTTAGAACCAGAAGTA
TTTCAGATTTTTTCAGATTTGGAATGTTTGCATTATACTGAGTATCTCAAA
TCCAAAAATCCAAATCTGAAATATTCCATGAGCACTCCTTTGAGAATCAT
GTTAGCATTCAAAAAGTTGCCGATTTTGGAGCATTTTGAATTTCCAATTTT
TAGATTAGGAATACTCAACCTGAGTAGAGGCTGCCTGCTAATTACCTGGGA
GCTAATTACATGGATATGTCATTTTGAGAAAGTTTAGCTTGCTGATATGGA
TGATTTTCTGGATAAAAATTATACTTTGATAACAATTCTTTTAAAGGAGAC
AATAATTATTAACTTTAAGTACTTTTTAGCTCTACAATTCAGAATTCTTT
AGTGCTAAATATTACATATTTTGAAACAAAAGTTTTGTTTATATTTATTTA
```

FIG. 8-4

```
TTTGTTTCCCCCCCCCTTTTTTTTTTTTGAGACAAGTTCTCACCTTATTG
CCCATGCTATAGTGCAGTGGGTGATTATAGCTCACTGCAGCCTCAAACTCC
TGGACTCAAAGGATCCTCCTGCCTCAACCTCCCAAGTAGCTAGGAGTACAA
GCATGCACCACCATATCCAGCTAATTTTTGTTTATTTCTACAGAGGCAGGG
TCTCACTATGTTGCCCAGGCTGATCTCAAATTCCTGGCCTCAAGTATCCTC
CCACCTCTGCTTCCCAAAGCGCTGGGATTACAGGTGTAAGTCATTGCACCC
AGCCAAAAGTTTTATTTTAAACTTATTATTATGAGCATGTAACAGATTTAT
GTGGTTTGAAATTCAAACCTACAAAAGAAAATAATAAAAAGCTAACAGATA
GACAAACAAAAACAAAAGCAAAACCCCACTTGGCCATGCTCTCTAGTTCCT
CATTTCTCTCTTGGAAGAAACCAGAGCAATGTTCCCTGTGTATCCTTCCAG
AGATAATTTTTTAAAATACTTTTTTCTTTTTAACAGAAGAGATGGTAGACT
ACTTCTTTTAAATTAAATTAATATACATTTACTTGTTTCTTTTTATTGCTA
TAGAAAATGAAGTTGGGGAAACAGGAAAAATGACCTAGTATTATCATACTA
ACATACCAAAATTTTTCAGTTATATGTATTTCCTGTTTCAGTTTTTACCCC
ACCTGTTTTTTATTTGGTTTGAAATCATAGTACAGATAAAAACTTGAGGCA
GGTATTTTAGACTTGTTTTTCTTTTGTAACATAAAACTTTGAGAGCACCAG
GAAATCTGGAAATATTCATTTAGTTATTCATAATTCAAAATATTGTTATAT
CCACTTTGTGTCAGACTATTTGTTAAGAACTAAACTAAAAGAAAAAGATGG
GGCTGGACATGGTGGCTCACACCTGTAATCCCAGCACTTTGGGAGGCTGAG
GCGGGTGGATCACCTGAGTTTGGGAGTTCGAGGAAAGCCTTGCCAACACGG
TGAAACCCTGTCTCTACTAAAAATACAAAAATTAGCCAGGTGTGGTGACAC
ACGTCTGTAATCCCAGCTACTCAGGAGGCTGAGGCAGGAGAATCACTTGAA
CCCAGGAGGTGGAGGTTGCTGTGAGCCGAGATCATGCCACTGCACTCCAGC
CTGGGCAGCAAAGCAAGATTCCATCTCAAAAAAAAAGATGATAACACCCTC
TGGGAGATTACATTCAGATAGAACAAATAAAGGTGTAGAACCTAAGATGTG
ACAAGGACACTGTTGGGTGACTGATTCTTCCTGGGAACATTTATAAAGGCT
TCCTAGGGGAGGGCGTGTTTGTGTAAGAGCTTTCCAGGTCAGAAAGTATGT
ACAGTGGAAAATGTATATGAAAAGACCGTGTTTGGGAATCAGGGATTATAT
ATTGTGATTAGAGGAAAGAGTCCTAGGGTTTGATACCTACAAAGAATTAGA
GTTTCTAGGTGCTTCTGGACATGTGGATTGATGACAGCAATACTAAAAATA
CAAAAATTAGTGGGGCATAGTGGTGAGCGCCTGTAGTCCCAGCTACTTGGG
AGGCTGAGGCAGGAGAATAGCTTGAACCCGGGAGGCGGAGGTTGCAGTGAG
CCGAGATTGTGCCACTGCACTCCAGCCTGGGTGACAGAACGAGACTCCGTC
TCAAAAAAAAAAAAAGAAAAAAAGCAGGAGTTAGCAGAAAACCAACAAGAC
ATGGGAAGGAGAGAGAGAGCTGCAACACCCAAGAGAAAAAATAGCAATGCT
GAAATCAAAGTATAATGAAGGAGAGAGGATGCTGGAAGCTATGAAATTCTT
TCTGTGAGGCAATGGGGCAATGACCCTAGAACTGCTGAGTTAGCAGCAGTG
ACAGACTCAGTGCCAAATCATATATTAGAAAAAAAAATCAGATAGAGGTAA
AGTCCAGATCCAAAGAAGAGGGTTTTTAGCAGTAAAGCAGACAGTAGAACC
CACCCAGCTTTCTAGGGTGCAGGGGGCCTCCCTTTCAGGCATCATGAACAG
TGGGGGACCATAACTAGGCATGATGGCTTCAGATACAGGGCTTGTTCATCT
CTTGTTGTGGTCAGGCACTGCCTAATGAGAGCAACCCCTTCCAAATGCTAC
TGCTGTGTTTAACTAGGGCTCTTGATAATCTGACCAGCTTCTGTCTTACTG
ATTTTAGGAGAAAAATGGAGCAACCTGCAAGATGAGTGGGATTAGCTTCGT
GCTGTCTCCCATGCACACCACTCATGCACACTTGGCGAGCATGGCAGTTCC
ATTTATTTTGCACCCAGTTGTGATTTAAAAACTTTTAATTAATTAGTCTTA
```

FIG. 8-5

```
TTAGTCTTCAGTTGGATTTAAATGCCAAATAATAACCTTCTACCTTGTAAG
AGGAGCCCTTTTACCTAAAGCAAGGCTTAAGTTTGGATAAATTTTGTCCTA
TTTATTATTCATCCACAAGCTCTCTTAAAACACTGAATACACACTAAGAAG
GCTCTCAGCACTCCGAATAGTGTGATAAATCAAAAGCCAGTAACTTCTCAA
AGTCATTGTGTATTAGTCAGGGCTCTCCAGAAAAATAAAACCAATAGAACA
TATATACATGGGCTTTTACCCAAATGTCATCTTTTCAATGAGTCCTCTTGC
CTGCTTAATTTTTCTTTTTAGCATTTGCCACCTCCATATAACATGCACTTT
ACTTATTTATTGTCTTATTCTCTTTCACATGGGCAGGGGTTGCATTTGTCT
GTTTACTGCTGTATCCCTAGCACCTAGAGTGGTGCCTGGCATACGGCTGGT
GTGTGATACATATATTTGGAGTGGAGGTAAAAGTCACCACTTAGGCTATCC
ACTTTTGTGACAGGGACAACACACGTATCACTTGTCATTGTACCTATAGCA
TCTCACCCAGAGCCACAAAAAAAGTGGCTCAAAGTATATATTAACAAAGAA
CAAAATGGAATAATCCCATCTGAAGGCGAGGATATAATAAAAGCAACATAC
CTTTTTTTGGAAGGACATGGAGAGCATCAACCTTAAGACTAAAGACTAAAC
TTGAGAAGCAATTATTACATTTCTATTAAAAATTACCAAATACAAATAGTT
AACTTTGAAGAAATATATGAATAATGATGGTATCTGCAAAAGAGGAAAAGA
CTTACTCAATTTCATTGTACCTTAGTTGTAAATAGTATTCAGGCCACCATT
TGGAACCTATGTGACACAGTTTAGTTCCTGTCTATGTTCATAAGAGAGGGC
AAAGGCCCGTTTACATCCAACCTCTGTATGCCAGCAGCCACGTATGCCACA
CTCTAAAATGGCTAAACAGTCATTCATCAGAATCGGTTCCAAGAACTCCAA
CAAAAATTAGAGCTCATGGTGCCAGATTGGCCTGGATTTTCATGCTCCTGG
GTGATTACAAAGTTGTAAATAATGATGCTGTCCACTGATTTTCATCATGCG
GGGCTCTCTGCTTCACTGTGCCTTCCTCTTATGTCCATGGCACCAATTTCT
CTGATAGTTCCCCCAGGGGATAGGGTTAGATGTGGGTTCATAAGCGCTGGA
CCACTGAGGGTAATTCACTCTTAAGACTAGCGAGCACTTTCTGAATCTGAG
GAGTCACATATTAAAAGAGGCAGAATCATCTTCTGATTTCAAAAAAGCAAC
TACATGACCACCCTGAAAGTGATTTCAAAACAGTTGAAAGCTAGCTGTTCA
AGTTGATAAAAGCCACTGCAGTTCCCTGCAGGGAATGCTGATGGGCTCCGT
TCCCTCTGCACATTAGAGCCATTTAAATGAAATAATTGATCATATTAACTG
AAATCACCTGGCTTATAGCTCAGGTCCTAAGAATTGTTAGTGGCACTTGGA
GCTACAAAGAGGAGTCCCCAAAAGAAACGATTCTCACTTTATTTTGGCAAA
TGGGTGGCTTAAGTAGAACTGGTCCTATTCCATAACAATAAAAAAGGAAAA
AATAAATTTTATATAAACTTATTTCCAAGATTTCTTACCCCTTCTTGTCAG
CATTTCAACTTTATTTGGTGGAACTATCTTTTCTCAATTATGTGTGATGTA
TTGTGGTCGTGAATCATGGTGTCCTGAACTCCCTTTGGAAGCTAAAACGGT
CTGTTGAGGCTCTGCCTACCAGCTCTCTAGGGTTTGTTAAAGCAAAAGAGT
GAGCACTTTACTTAAATTTCACCAATTATATTATCTTCTGAGACCTTAAAT
GTTGAGTAGAGGGAAAATACAAGTTCAAGCCTATTTATTTCAACAATGGAG
CAAGTTGCTACAGCTAAGACCTTTGAGGCTGCCTGTTTCTTCAGGTTTTC
CTTTGATTCTCAGAGTAACCCCACCTCAATTTATTTGAATACATGTACTTA
TGGCTTAACCAACACACAGGTGGTTTCTTTAACTACAGTGCAAAAATCTTC
ACACATACAAACTTTTTAAAAAACAATTCTCAATATGAAAAAGAGAAATCA
ATATAATTGGCTACAAATTATTGGCATCTTTTCAGAGATTTTCTCAAGAAA
GTAACTGAATTCCTAAAATTCTTATGACTTTGTTAAAGGACTCAAAATGAA
CATATATTCTGGCTGGGCAGGTGGCTCATGCTTGTAATCATAGCACTTTGG
GAGGCCAAGGATTGTGGATCACTTGAGGTCAGGAGTTCGAGACCAGCCTGG
```

FIG. 8-6

```
CCAACATGGTGAAACCCCGTCTCTACCAGAAATACAAAAATTAGCCAGGCG
TGGTAGTGGGTGCCTGTAATCCCAGCTACTTGGAAGGCTGAGGCAGGAGAA
TTGCTTGAACCCAGGAGGCAGAGGTTGCAGTGAGCCAAGATTGCGCCATTG
CACTCCAGCACGGGCAACAGAGGGAGACTGCATCTCCAAAAAAAAAAAAAA
ACAAAAACCTCATATGTCCTACAAAGCAAGTGATAAAAATCAAAATATGAC
AATGGGCTGAGAGGAAAGGGAAACTAGTAGTATTAAAGAAAGTTTTTAATG
AACAAATAATGTTAAGGCGGATTTTTTTGTTTGTTTATTTGTTTTTGGCCT
TTTTTTTTTTTTTTTTTTTTTTTTGAGACAGAGTCTCACTCTGTCGCC
GAGGCTGGAGGGCAGTGGCACTGTGTTGGCTCACTGCAACCTCCGTCTCCT
GGGTTCAAGCAATTCTCCTGTGCTAAGGCAAATTTTTAAGGATTATAAATA
GTAAATATTAGAAGGGATACTGCTTAAAAATAAACAATTTGGATAGCTAAA
TGGTCTTCAGACTCTTTTGATTGTACAACATGTAAAAGAATTTTGAAAACT
TTAGGCATTCCTTTGAATATTTTTAACTTGATTTCTAAAACTTTTCATCAA
AAAATAAATTGTTTTGTAAATAAAAGAAAACATTAAACATGTTATAAGATG
AAATAAGATGAAGAGTGACTATAATTAGAATAAGTATTTCATGACATAAGT
TTATTTTAATAAAAGTTCTAACCACTTTATTGTATCATTCATATCAAGTTT
TTTAAATATATATTGAAATTTGGTGCTCTGGGAAAATATGCCAGCTTCATT
TGAAAGAATGAGTTCCTATCCTGTACTGCTTCAGTTATTCTGAATTCAGAA
CATTCCCACTCTGGCCAGTCCTCTCTTATAATAAAACATACAATACTGTGC
ATATTCTCAGTGATTAAAAAAAATACACACAGCAGATAAAAGAAGAGGGAG
CAGGCAAACCAAGAGCCAAGGTGAATGTGTTAATCATTAGCAGGTTATCCC
CAAACCAATATTTGGAAGTACTCCTTTGTTGACAACCAGGAAGTGTTTACA
CTTCAGGCATTGCACCTAAATAAAGTGTGGATGCCTTTCCTTTCTAAAGTG
GAAGGAGGGATATTGTGGACATAGGCACATTCTGAGGCAATTTTAGGAAAT
AAGTTGAAATTGATGGAAATTGAGAAAGACTTTGGAAAGTGTTTGCCTGCC
TCCACTACCAAAAAGTCCATGGAGAAAGCAAAGTAAAAGGTCCAAAAATGA
AAGTCAGCAGAAACCAGAAAGATGGGCAACAAGGTTTTACCATACAGATAA
ATAGAAGAGAGATTCTTAGTAAAGAAAACAAATTGAGGACAATCACTAAAT
AAAACAAAATCGAAGGAAACTCTAAGACCACCAGCCAAAAAGCAAGAGAAA
ATGATTAACACCTTGGCACATCTTGGTGAAGGAATTCCAGGATAAAGAGAA
TCCTATAGCACCTAGCCTAAACATAGCTCTCCTACAAAAAGTAGCTGGCTA
ACTAGACTTCCTCATATTGGACATCAGAAGAGACTAGCAGGAAGTCAATAC
TGTTTTGAATAAGACAAATTGTGGAACAAAATTTCTGTTCCCAGCTAAGTT
AATATTACAATGTTTTAAGGCTCCACAGTGATCATAAAGAGTACTATGAAA
TAAATTCTCAGCTACTGTGGGACTCAGAGGCTCATCCAAGTACTGCTCCAA
AAAAATACTCCATTGAAATGTTTTGAGATGAAGAAGGATAAAGGATGGACA
TGAAAAAACAAAACAAAAAACACTTCATTGTCCAGGGGTATGCTAAGTGAG
CAAGAAGTGTCCAGCACTCAAAATTAAGGAGGCACTCACTCTCATGTGCCA
ATTCTGTTCTTGCATGAGCCTAAGAAAGGATGCCTCCTTAAATATTGCTTC
TTGGGCACCTCACTTGCCTCATCTTGGTTTCAGCCCTCAAATTATGTTCAA
ATAACAGTGAAAAGTATAATACCCAACAGAATGCAAATGGTATAATTCTTC
TATGGAAACTACTCAATGCAAAATTAATACATTAACTGCAAAAGGTCAGAG
CAAAACTTCCAGAGAACAGTAGTGAAACCAAGAGTGAGATGATAGGATGCC
TCAGTGTGTCTGTTTTCTTATTATATATAAGGAGAGAGACATGGCTAGGCA
TGGTGTCTCATGTCTGTCATCCCAGCATTTTGTGAGACCAAGGCAGGAGGA
TCCCTTGAAGCCAGCAGTTTCAGACCAGCCTGAGCAACACAGCAAGATCCC
```

FIG. 8-7

```
TGTATCTACAAAAAAAAAAAAAAAAAAAAAAAGCTGAGAGTCAACAGCCAC
TTTTTTACTATATAGGTTATTAACTTGAGAAATAAAGCATTAAAAGAACAA
TGAATTTGGGAGCACAACACAGCAAAATGTAATCTGCCCACAAAATTGGAC
TTAGAGGAGCAATTTTCCTCTAAGCTTTAACCTGTTTCATAATTAAATGAA
AAATAAATAAACTATCCAAAACAAAATTTATATGAAGTAAAGCAAAGGGAA
ATAGGACATAAGCTTGATAAAAGATAAAGCTAATCAAATATAAAATAAAAA
GACAAGCAGGGCTGGGCGCAGTGGCTCATGCCTGTAATCCCAGCACTTTGG
GAGGCCAAGGTGGGTAGATCATCTAAGGTCAGGAGTTTGAGACCAGCTTGG
CCAACATAGCAAAACCCCATCTCTATTAAAAATACAGAAATTAGCCAGACA
TGGTGGTGCATGACTGTAATCCCAGCTACTCGGGAGTCTGAGGCAGGAGAA
TCACTTGAACCCGGGAGGCGGAGGTTGCAGTGAGCCGAGATCGCGCCACTG
CACTCCAGCCTGGGTGACAGAGTGAGACTCCGTCTCAAAAATAAATAAGTA
AATAAATAAAAGACAAGCTATTCTTAAAATTAGTAAATGACTAAGTAGTCT
AATGAAGGAGAAAGAAAGCACACATGCAATTGGGTCAGAAGTACAAAGAAG
CTAAAACCTCAGATATAGATAAAATGATATATTATTAAAAAGATAGCCTGA
TAAAACAGTTGAATTTTTGCAAATATACTTTAAATAGTGTGTAAAATAGAT
GATCCTCCAGATAACATAAATGGTCCAAATTGATCAAAGAAAAATATAAAA
CCCCTTAAAAGACCAGTAACTGAAGGAAATTGAGAAAGTTATCAAAGTCTC
CTCAAAATGGCTTTCAGCCTGCATGATTTTTACAAACCAATGCTTTCAAGC
TTTCAAATAACAACAGCAATTATAAAAATTCCATTCTAGTCAATCTTTTTC
AGAGTAATGGGGAAAAAGGAAAGTTCTCCTTTCTTGTTTTTGAAATCAGCA
TAAGCTCCATATCCAGACACAAAAAAGATACACAAAACACATGTATGCATA
CAGAGCCAATCTCATATATCAGTACATCAGCCAAAGTCCTAAATAAACTAT
TAGTGAATCAAATTCTGTCGTACATCAAAAGAATATTCAAGGGAAAGCTCA
ACATTAAGAAATACATTAATATAATTCATAATATTTAACAGTCAAGGAGAA
AAAGTAAGTCATCTCATCATTAGGTAGATGACAATAAACTATTTGAGAAAA
GTGAATTAATTTTCATGACTATTGTTAGAAACAATCCTTTAGGGATGGGGA
GGGGAGATGAATTAGAAATGTTTCCTATCAGTTCACAATTGCATCTATTCT
GAAGCCATTAGGAATGTGAATGGTAACTCTTCCTCAAACCATCACATAAGG
AAAGATACCCTGAAAGTCTGACACACCGAAGTCATCTGTCAGGAATCAATC
AGAGAAGCTGCTGGGAAAACCTCAGAGAAGCTGCTGGGAAAACCTAGGCAT
TCTGAGTCATCATTGTTCTTATCACCCGTGGCAACTGATGCAATTGGAAGC
AACTGATGCTTTCAGGGTCATGGTTTCTTCAAAGCCTGAGCTCATTAATTT
TGCTGTTTGAGAACTTGCAGTTTGATCCAAAAGCTGACAGCATCGATTGAC
CCATTGCCTTCCTTCCTGCTCTGATACTGGAAGTTCCAACAAAAGAGGAGG
AGGAACAGGACCAAGAAGAACATGAAAGCAGAGGACCAGGGGCCGGGCGCG
GTGGCTCACACCTGTAATCCCAGCACTTTGGGAGGCTCAGGTGGGCGGATC
ACGAGGTCAGGAGATCGAGACCATCCTGGCTAACATGGTGAAACCCCGTCT
CTACTAAAAATACAAAAAATTAGCCGGGCATGGTGGCAGGTGCCTGTAGT
CCCAGCTACTGGGGAGGCTGAGGCAGGAGAATGGCATGAACCCGGGAGGCA
AAGCTTTCAGTGAGCTAAGATCGAGCCACTGCACTCCAGCCCGGGCGACAG
AGTAAGACTCTGTCTAAAAAAAAAAAAAAAAAAAAAAAGCAAAGGACCG
AAGGACCAAGACCCCTTCCCAACTGCTCCATTGGTCAAAACGAAGTCAGAG
CAGAAGCTCTCAAAAGGATGATACTTTGAATTTGCTTTCTGTTTTATTTTC
TACATTCATAAACGTGCACAAATCATAAATGTACAATATTCACAAAGTAAA
CACACATCCAAGTCAAGAAATAAAATATTTCTAGTACCCCAGGAGCACTTC
```

FIG. 8-8

```
TTAAGTACCATCCATCCAGCCACAACCCCCATCCCTGCACAAGGGAAATCG
CTCACTGATTTTTAACAGGACAGATTGGTTGTAGCTGTTTTTAAAAAGTAT
TTTATAAACCTTTAAAAGAATGTGCGTTTTGTCTTCCTTTAATCAATATTG
TGCTTATGAGACCCATTCATCTATTATATATTGGGGTCTGTTAATTCTCAT
TGCTATACAAATAGACCGTGGTTTATTTACTCATTCTTTTTTTAACAGACA
ACTTCCTGTTCAGGCTATTACAGATAGTGCTCCTATGAACATTGTTGTACA
TGTTTTATGGATGTATATGTGCATTTCTAAGTAAAATGTTTGAGTCACTGG
AATTGTACATTTAGCTTTAGGAGATATTGCCGAGCAGCTTTCCAAAGTTCA
CATTCGTAACGTATGAAAGTTCCAGTTGCTCCACATGTCTGGCAACATTTT
GTTTTCCATCTCCTTTCATTTTATCCATTAGTTAATTTTATAGTGGTATTT
CATTGTAGTTTTGATTTTCATTTCTGTAATGACTAATGAAGTTGAACATCT
TTTTATATGTTAAGGAGCCACTTACATTTTCTCTTTTATGAAGTCCCTGTT
CAAGTCATTGGCCCATTTTTTAGTTGGGTTGTCTGTCCCCCACCCTTTTTT
GTTTTTTTTTCTCTTTTTTCTGTACATAATTTGACTACCTATTATACTAT
GTCTTTCTTTTTTCTTCTACTTCTTCTTTTAGTTTTCTGCAAACCCCCTTT
CCTCTTTGTGTTGTCAATATCATGAAGGCAAAATCAATGTTCTCATCTTAG
TACCACCCTCAGGGCCTGACACTCTGTTTTTCTGAAAAACTTGCTCAAAAA
TACCCATTGATTTGCATTAGGAGATTCTCTTCATCTGCTGAATTAACCCAA
GGTTCTTGTCCAAGCAGTTTTTTAATAGGATTTAAAATATGGTGGGAACTT
CTTCTCTAGACATGTTGTGGCAAAACCAGAATCAGTTCTGTGTGAGGAGAC
AAACTAAAGGATATGTCTTAAGTGTTAGGAGCCAAATTAATTCCTGTTAGA
GTTGACGCTGCCTATCTGAGTATCTTGGGAAAGTAAGAAAAATATGAAGAA
GGTTAAATTATCTTTTTCTACGCTCAAAAGGAACTTCTCTTGTATGTGATA
CACTTCTATGCCTTGTATGTGATACATTTCTATGCCTTTTCTCATCTTGTT
ATGTCTTCAATATTTTTCTCCCCCATATAAATTGTCATTTCACTTGAAAGT
GTCTCTGTCATCTCTCTCCAATTTTCATTATATGGTCTAAACTATATTGCT
ATCCCTTCTGGAAGTGTCTACATTGCCTTCCTTCACATTCATTCTTCTCAC
AATACAAGCCTTCCAGTTCTATCTTCTCTGTCCTTGATTTCTAAGTTAACC
TCATTTATTTAATCTTGTATTGGTCATTTTCTCATCATTAATCTCTTGCAA
TTGGGCTAGGATAAATAAATATCTGTTTAATCTGATGGAAATATCTGGATC
TAAATAATTTGAAAATGGTCTATTTTATTTTAGCATGTAAATTTTAATAGA
ATTTAATCACATAAATAAACGTCTATGTTTACAATGTATAAAAAATAATA
AAAACTTTAATTCTGGGGATTATAGCTTTACAGTTCCGATCGGTGCTGAGA
TCTGTAACATATGGCTACAATTCCGAGCAGATCTTCTCTGCATCCAATAAC
CTGCCCCACCATGAAGATATTTATCAGTGATCATTTTCACATGAATTTTTA
TTTATTTAGTACTTTCCAATGAGGAAAATTCAAAGGCCACATGAATTGACT
TTTCAAGTTTGTCCAGCTGTTGTCAACCCCGGGCGCATGCTAGAAACCTCT
AAGGAGTATCTAAAAATTAGTAGTATCTGGGTTCCACCCCAGACCAATTCA
TTCAGAATCTCTGGAGTGGGTCCCAAGTATCAGTGTCTTATAAAGGCTCCC
CAGGGAAGACTAACACACAGCCAGAGTTAAGAACTGCTGAGTCTATGGTCA
GGAATATGGAGAGAAGTAAAAAATGTTTAAAAAGTTCATGCTCAGTACCAC
ATTTAAGTTTGTAACTTTATGTCCTCAGAGGCGGGTAAGGGTCCTCTCTTT
GGCCCAGTCTTGAAGTTCTGCTTGTCCAAACGTGAGGTAAAAGACCAGGCC
AAACATGTTGACTGCAGCAGACAGGAAAAAGACATTCCTCCAACCAGACTC
AAAATCCTAGATGTAAAAAACAGAGAAAATGATCAATCTCACAAGTTCCTT
CTACACCAGTTCTAGTAGCCCTCCCAGTTGTGTATTGCAATGTTGATCACA
```

FIG. 8-9

```
AGGAATATAAGGAACAATGTGCAGTAGTTACTTAAGAAAGTTTATGAAACT
ATTGGAAACAAAATGGCCAAAATGCACATGGGGTTCTGAGTTGAGATGGTT
ATTTCTTTAAACAAAAATAAAATACACTAATGTTTTTCTGAAAATTTGGAT
TTCAACATATAATATTACTCATTTAAAATTATGCCTAAAATGGCATTGTGG
CATTGTGTTTGTGTCTTCTCTGTTTTTTTTTGTTGTTGTTGTTGCTGTTTG
TTTTGTTTTTTTTGTTTCTGTATTGGCTGTTGACAACTATCACTACAACC
CATCTCAATTCAACATGAGTTCTCTTTGGTCTTCTGTGTGACCCTCCTCAG
AAAGCCCTACTAAGTCATTTCCAGCATTATAGTCACAGTGGATTCCTAGCA
GTTTAGTCAAATATTAACCTGGGAACTTGATCACATAGAAATGTAGTAAAA
ACAAAACTTCTCTTTGTAAGTTGGTTCTCGTCAGTCCTTCCATCCCTGCCT
GGGTCTGTCTTTTCATCTTCCTCATGAGCCTGCATTTCCAAACACCGAGCA
AGCCTCCTTGCAATGTCTCACAGCCGATCTGTTTCCAGACATTAAATTATC
TTTAAACTGGCCTAGGACACTTTGTTTCCCTTTTGTGATTTTTTAAAAATT
GGATTAGTCTGAACATATTCTTCATGATCTTCTTTTGCCCCTCTGTCTTCG
TCTCTTGCTATTCCTTGACATGTGTCTTTCATTCTGGTCATAACTAAGAAC
TGTTTCATGCTCATGTACCTCTAGGAAGTCACACGTGCTGTCTTCTGCACC
GGAACAGCTCATTTTAATCAATCTAACATCTATTCATCTTGAGAAAATAAG
CTTATATTTTCTTCCTCTGGGAAATCTGACCTACCAGAGTCTGATTTAGA
GGCTCATGTAAATAGAGTAATTGTGTTGCCATCCAGATCTTTAGAGCACCG
TGTGTATCTCCAACACCTAAAACAATACCTGCCACTTGAAGATGTTCAATA
AACTGGCCCAACCTGACTGATGAGGAATCCAGTGGCAGTGGAAGAGATGAT
TCCTGCGATGAGCCCAAATCCCCTTGAGATTCCCATGAGGAAACTTGCATA
TCTGTGGGAAGATGATTTTATAAATGATTTTATATAGAAAGCCACCTACAG
CTTCTGCAGCAACTCAACTTTAATGCAATTCAGCTCTAATGGCAAAGTCAT
TTTGCTTAATGCAGTTTTTCATTCACCTAAAGACATTCAGGGCAATGTCTA
TTTGCCAAACCTGAAATTACCAATCTACCAAGTCAATAACCAGGGAGCAAT
GCAGTCTCTCTGGGAACCACGTTTCTTTACCCCGGCTGCTCAGTGGAGAAG
CCAGTTTGTGCAACGGGCAGGACACAGACTCCAAAGCCAGACTCCCCCAGT
CCAAATCCTGGCTCTGCCTTTATGTGACCATAGTCACACCATTTAACCTCC
TTGTGCCTCAGCCTTCTCCCTTATAAAATGGGGATAACAATAGGGCCTACC
TAATATAACTGTGAGGATTAGATGTGTTGATATATGGCAAGTCTTGGCACA
GGAGCTGGCTTATTGTGACTGTATATATATATATATATATATATATATATA
TATGGTAGCTAATATGAACAACACCATGGAAACTTTTCCAAATCACCTGTG
TGTGGGCCTTTTCCCAGCATACACAGTTCAATCTCTGTTAGGGAAGCTTGG
GAAGGTTTTTGTCAAAATGATTACTGGCCAAGATTGGAAATTGTTGTTCTA
AAAATGCCACATTTGTTGTTCTAAAAATGGCCACAGACAGATATTTGTAGT
TATTTGTCATTCTGCCATTAGTGCAATGTCAGTAACATTAAAGAGTTTCAC
GGCGACCACTGAGGTCTAACACCTCTGGAGGGGTCTGGAGGAGGGGAAAAA
ACAGGTAGAGCTCTTACCTGGGGGCGATATCTAAGGTGTTGATGATAAACC
CTGAGTCACATAGGTTACTGGTCCCAGGAATAAGTATCAGCAAAATAATGG
TTATCACGTAACTGGAGGCCACAAAGGGCAGGGCCACAGCACATATTGATG
GAAGGAGGAGCCCTGGGCAATGAGGACATGCTGTCAGGGAACCCTCTGAGA
CCATGTGCAGAAAAGGGATTGGTTAAATGGGCCCACACGCTTATCCTTACC
AAGAGATGAAAAGAGCTTTCGCACAGTGATCAATCTGAGAAGATTCCTGGA
CAAAAGGAAATCTGCCAGCTGACCTCCTAAAATTGTACAGCTTGCAGCAGC
AATAAAAGGCAGGGAGGACAGAACTCCACTCTGAAGGAAGGAAGTTTATAC
```

FIG. 8-10

```
AGAGTAGTTATAGAGATACGTTAGCACCAAAATTTGTCAGTTACACAGACC
AGCCATTAACTTACCCCCATGATACTGTGGGTTGTTTGGGGGAAAATTAGC
ATCCTTTTTCACACTAAAAGAACACTGTCTCAGATAAGAGGGCCAGAAGCT
GCATCACTCTGGGCTCCAGATAAAAGCAATATTAATTTCTTGGGTTTTTTG
TTTTTGAAACGGAGTCTTACTCTGTCGCCCAGGCTGGAGTGCAGTGGCATG
ATCTTGGCTCAATGCAACCTCCACCTCCTGGGTTCAAGCGATTCTCCTGTC
TCAGCCTCCTGAATAGCTGGGATTACAGGTGCCTGCCACCACACCTGGCTA
ATTTTTGTATTTTTAGTAGATGATATTTAGTAAACCATATTGGTCAGGCTG
GTCTTGCATTCCTGACCTCATGATCTGCCTGCCTCGGCCTCCCAAAGTGCT
GGAATTACAGGCATGACCACCATGCCTGGCCCAGCAATATTATTTCTAAAA
GAAGCTTTGGAATCAGCTGGTGTGGTAGTATAGCATAGTGGTTAAGAATAT
GGATGCTGCAGCAGCTCTATCACTTAGTATTGTGCAACCTGGGGCAAGTTA
TCTCACCTCTAAGTGTCCTGTTTCCACATCTGTGAAAAGGGAATTATAACA
ATGCCTCTCAAGGTCATTGTGAAGGTTAAATTAATGGTTATATGTAAAG
CCAGAATGTAATAGGTAACACAGAACTGTTTCTCCTTATTACCATTATCAT
TTTCGTAGAAGTATAGGAAGTAAACTCACATCTCTGATGTTAACATGGAGC
AGAGTACTGATATACGTTGGTAGGTATGTTAGGATGATGGTGCACAACCAG
AAATGGCTGAAAAAACCCAGGAAAATGGCCCAAAGTGGTAGGCATGTGACC
ATCGCCTTTATGGGGACAGCTCGTCCAGGAGAACTGGGCTGAAAAGAAAGA
TCTAATCAGCATGAGTATTAGAGCAGCCAAGATGGTGCCTCTCAGAGGAGA
TCCACACCCTGCCCTAGAGACCTCTGCATGGGCCACAGGTACAAGGTGTGC
ACTGTACCTGTTGAGCCAGTGAGGACAGGATGTGCTCCTTTTCCCTAACAC
TTATGCACGGGTGATGCATGGGGTCATCATAAATCACTGTGAACCATAGGA
GACAGCAGACACAGCCAGTGCTACCTGGGAAGAAGGGATAAAATTAGTTTT
TAGGTAGATTTGTTTACTGGGGGAAGGAAGTTTCCTCTGAAGTGGCATGCC
TCTCCCTTCTACACACTAATCAATTAATGCTTATTCTACCATAAGGACCTA
AATGTTCCCATTCTTTCTTTCAATCCTTCTACAAACCTGTTAAAGCTTTTT
AGATATTACGTCTCAAATAGAAAGCCACCATTTGTCAATGTCAGAGCCCTC
TGGAGATAACAGGAGCGTGGCATTGCATAGCTGATTAATTACTTTAAAGTC
TCCAATGATTACAGTGTTATGTATTTTAGGCAGCAACTTCTTAATGCACAC
ATAAGTTGTCTTGTTGCGGAAGATCTGAATAGTCAGGTTTGCAGTCATACA
TACACGAAACAACCTTCCATGAAATCATGTGGCAGGGAAAAATTTCCAATG
CACTTACAAGAGACAGTATTATTTGTATTCAAGCCATACATCCATTATGGA
TTCCCAAAAGAAATATTTTTGTACAATACCTGGTTAACATGTACAAACCAA
AATAATTAGCATCATTAATGAGAAAGCCATTCAGGCCAGGACTATATTTAA
TGACACCATTTGGCTATAAAAACAAATCAAGTGTAGAAAATTGTCTTATTA
TTGGAATTCCTTATTTGAAGAACATTCTATGTTAAAAGATTCTGAGGACTA
GTTTTCTTTAAATCCCCTCTAATTACTGGATTCACTGATTCTTTTATTTTA
AAGCTAAAAATCAGGCACCATGATGACACCCAAGTGATGAAAACATAGAAT
GGATTCCTTGCCTCAAGCATTTCACAGTCTAGTGGAAAGAAAAGGAGAAAT
AAATAATTACACACCAACATAACCTAGAGAGGAAATATCATAAAGGAGAGA
ATGCCAGAATCTGATAGGGTAAGCCCTGGAAGGGCCCATGGGGAAGGGAAC
ATTTGAATTGAACTTTGCAAGATTAACTTGGTAGAGAACAGGTGAAAGGCA
TCTTGGACAGAAATAATAATTATAATGAAATATGAAGACACATTGAAAATG
TACTTCACTATCTTTGACATCTTAACTGCATATAGCAGGCACTTCAGATGT
GGTGGTAGAGATTCTGCAGAAGGTGCTTGATATGGAAGGACAAGACTGCAT
```

FIG. 8-11
```
CACAAGTCGGTGGGTGCCATGTGAATAGTCAACTCCTCTACCTTGTGCGTG
TGGCTTCCCAGAACCACCAGGAAGGTGTTAATCAGGTTGTGTGACTAGATT
AAAAATGATACCAACCGTTGACATTTTTTATCATCTTCCATTTGATAAAGG
ACATTTTCTTTCATATAGGAAGAATGTGGGTGGTGTAGGTGCCAAAATGGA
TGCTCAGGAAATGGAGGCGTTAGGATTTAAGAGAAAGTGACTCACCAAAGA
TGTACAAGATAAAAGGCCAGCTCAAGGCCTGTGAGATTAGTCCCCCCACAC
AGAGGATGATGAAGGATCCAAATGCTGACCCTAAAGGAAAAAGGGAGAAAA
ACACTTATGAAAATATCAAAGGCTGAGACTTCGTGGCCTCCCTAAACAATG
TCCCAACAGTGAGGTGGCAGACTTAGAATTATTGGGCAATGAGAGTATTTA
TTTCTAAAATAGCTCACAGATTTTCCCCAGTAAAGTAATATGATATAATTA
AAATTAACAAATAATAGTAACACACTCTCTGATTCTTCAATGGCTCCTCAA
CACCAATGTGACCAAATCTAAATCCCTTAGTTTGTCACAGTAACTCTCTGC
TATCACAGCCCATTAGCATTTTCTTGTGATTACAGTTGCATTCTTGCATGA
TCTAATATGAGGCTAGGGGCAGGAAATGAAAGACTTACAAAAATCGGTAAG
ATACAGCCCCTGCCCTCAAAGAGCTTCTGGTCCAATTGGAGAGAAAATGT
GAATAAAATTGATTGTCACTAGTGAAATGCCATGTAGGCTTTGGAAGTCTA
CATTAAAAAACAACAAGACACATATTTCACAGAGACCTATAGTAAGAAATG
CATTTTACAGGGTAACATAACACACACACCAATATGCATAAACACTTGTAC
ATACAACCACACATATGCCTCAAACGATGGTTTCATGAATCGATATTTA
ACTTTACCATGTCCAATGCACTCCAACAATTTCTATTCTATTCTATTCATT
TTTTAAAATAATGATTTTAACCCGCTCAATGGATTTTATGACTCACTAATG
GGTCCCAAACTGAAATTTGAAAAAAAAGATGTAAAATATAAATATAATAAA
ACTACAATGTACGTGGAAGTATATCTGAGGATAAATTGATAATAATTATAA
GATTTAGGAAGTTTTGGCCGGGCGCGGTGGCTCACGCCTGTAATCCCAGCA
CTTTGGGAGGCCGAGGCGGGCGGATCACGAGGTCAGGAGATTGAGACCATC
CTGGCTTGAAACCCGTCTCTACTAAAAATACAAAAAATTAGCCGGTCATG
GTGGCAGGCGCCTGTAGTCCCAGCTACTCGGGAGGCTGAGGCAGGAAAATG
GCGTGAACCCGGGAGGCGGAGCTTGCAGTGAGCCGAGATAGCGCTACTGCA
GTCCGGCCTGGGCGAAAGAGTGAGACACCGTCTCAAAAAAAAAAAAAAAAA
AAAAAAAAAAAGGTTTAGGAAGTTTTTACATAAGCTATGCAATAGGATAGA
TGGAATTTTGGCACAAGGAACAGGGGCAAAGAACTTTCCAGGCATATAAAC
TAACGGGAGCAGAGCCAGAGGGAAGTGCAGTGCAGATCTATGTGGAGAGCA
GCCAATGTCCAGTGCCACTGGAGCCATGCTTGCACAGGGGAGTTGAGTGGA
ACAAGGTTGGGGCCAGATGGCTAAGAACTTTTGTATTCATGCAATAAAGAG
GTCAGGCTTTACTCTGTAAGCATGAAGGAACACATTGAAAATTCTCAAGCG
GGTGAGTAAAAATGTGCCATCTTTATTTTAGCAAGCTAACTTGGTTTTGGT
GGGAAGAAGGTTGAAAGAAACCAGTCTAGAAGAGAGAGATCAGCAGATAGT
ATTTGCAAATAGAGGAGATGGTTACAACTATGATGGAAGGAAGCAAGAACG
CAGGAGGGTTGCTTGAGGTAAAAGTCTGCAGGATGCAGCTGTGTAGTGGAC
CTAGGAGTGAGAAGCTGGATGGAATTTTAGTTCTGCTCTTCGAGTATATAC
TCTCAGCACGACAGGCTGGGGAGAACAGCAATGATAAAGCTGTAGAGGCCT
GAGTAGGATCACATACCATGGAAAGGCAGTCTAGCATAGTGATTGAGAATG
TCTGCTCTGGGGCTAAAATCTGCATGGGCTTAAATCTCAGACCTACCACCT
GCTGGCTATTTGTATTTGGGCAATTTTCTTAATCTCCACCTTCCTTAACTC
CCTTCTCTGTAAAATAAGAATTTAAAATGGTACTTATATGAGAGGGTTGTT
GTGAGAATTAATGAGCTCATAATAGAATAGTAAAGAGCTTAGAATAATACA
```

FIG. 8-12

```
GAAACTTCAAACTCTTCCAGCCTGATTTCTCTCCTTACCACCTGGAGCTGT
GGTAGCCTTAATTCTCACTTCAAAATCATTGCTAAGATGGTGTATATATAG
CTTACTTGATCTTTTTCCATGTGTGCAATTCTTAAAGGTTTAAACTTTTTC
CGACAAGGCTTTTCTGACTACTAAGGCTTTTCTGACTACTAAGGCTTTTCT
GAGCTGAAACCTAGCTCACAATGGTTTTTTCTACTTCTAAGCTTCAATGTC
TTTACTGCACAGATGCATCTTTCCTATTTGTGATGCAAGTGTCTTATATTG
TTGAATTTTTCAGCAGTACTTTTTCTCTCTCTTCCCCAAACCATTTGATTC
ATAGAAGATAAGACACAGTGGGATGGAACAGATGACAAAGCTATGACCCAT
CTGTGCACACTTACCTGATCCTGCAATGGTGGTGAGCTTGCTTCGTTCAAG
TGGAGGAGCCCACTTTGCCCAAATAGTAAACTGACCTGTCCATGCCATTCC
CTGAAATGAAAATCATTAAGACCTTTGATATTTTGTAGAATTCAGAAATCT
GGATCCCACCAAGAATGAGAAAGTATCTGGATACCTGGGCCAAGCCCTGGA
CTGTCCGAACCATGATGACCAAAATCACTCCGAAGTCAGCAGCCAGTGGTG
TAAAGAGGGTGAGAAGGGAAGAGATCAGCAAACCAGCACCAAGCATTTTTT
TTGCTCCAAATATCCCTGCTAAATATCCACTTGGGATCAGAGTCAGTATTA
TCCCATAGTTGATGGAGCTAAAGATGATACCCTGAGTTTCTGGGCTCCATT
GATACACAGAGGCCTGGGGGAAAAATAGGAAAACTCTTTGTCAAGAAGTCC
TATTATGAAAATCTACTTTACAGTCAGAGTTGCTTGAGGTTAGTGAGACCC
TAGTATAAAATATTGATTTTTGTTTCTCTCTATATTCTTCCTACCTTCCCA
AATAACCAATTATACCCCTAATTTGCTTGTCTTAGTAGAAGGAGAGAAAAA
CAGAAGAAATGAAGAAAAGAGGTAAAGAAAATGATTATATAGATGAATAAT
AGGAAGAAGTAAATGGAAGAAAACATTGAGAGATATTTCATCTGTGAAAGC
ACTTCCTCTATTTTGCTTCTAGTAAAAGTTGAGTAACATCTTGACTCTTAT
ATCAAAGAATTTTTTAAAACACACACACAAAACTTTACTGAACTCTTAACC
AAAATCAGTGCCTAATTAAAAAGAAAAGTCAAGTTTGGGAATCATGGTCTG
CCCTGGCTGAACTGAGTTCCTAAAACACATATTACAAATGAATAAGATCAC
ATTCTTCTGATATAACTCAATAAATAATTTGAATTATTTTAAAATAACTAC
CTAAAATTCCTAAATAATTACATAAATTATATTACCTGAATATTTACCTAA
AAATAAATAGATTTTAAAATAAATAAATAAAAAATAAAATAGATTTTAAAA
TAAAATAAAAAATAAATGCAATAAGGCCCCTAAATATCTGGCATCATGCTA
TAAAGTAGAGAGCCAAAGAATATAAAATATGAAATATTTTACCCACTCAAA
AAAACTATAAATAATACAAGGTATATGATTCATGTGAGAATCAAGATTTGA
GGATGAACATAAATAAAACAGAGACTTTGAGAGGAGAAAATAATAATTTGG
GAAGGTCCCAGAAAGGAAGCAATACTTGAACTATCCCTTGAAAAATGACTA
TGATTTGTAGAAAGTCAAAAAGGAAAATTTTATCTCATCGGAAAAAATAGC
AAAAGTGAACTTGTAGCATTTGGAAGAAACTAACAGGGACTCTGGCTTGCT
CAGGGCAAAAACTTTCCATGGGTCATTGATAGCAGATGTGAGTGTGCTGAG
AAGCAGGCCCAAATTCTGAAGGAACACAGCATGTCCAGTGAACACTGCATG
TTTGGCAACTTGAAGGTGTCCAAGATTCCTGAGTAGTGAATCTACTCAGTG
TGGATATGTAGACGGGATAATGGAGGAAAGACTGGAGACAATAAATTTATG
TACTCATTGTAAATAAGCTAGGTCCAATGTAATAAAATCATTAATCATGAA
TTATAGGGATGACATGGGAAATGTACAGTACAAGATAATTTAAAGGATAAT
TTTTTAATTGGGTAAATTCATGGTTTTCATATAAATGTAAAATAAACATA
CAACAAAGATTTTATTTAACTCATTGATTAATGGAGGAAGTAAGTAAGATG
TTATAACTGGTTCAAAGGAAAACTCAAAGAATCACGCATAACACAAGCAGG
AAGCAATGCTGAAATAGACTTTAAATATACAGCAGAGCCTGGCACAGTGGC
```

FIG. 8-13

```
TCACACCTGTAATCCCAACACTTTGGGAGGCCGAGGCGGGTGGATCACCTG
AGGTCAGGAGTTCGAGACCAGCCTAGTGAAACCCTGTCTTTACTAAAAATA
CAAAAATTAGCCAGCCGCGGTGGCATGCCCCCTTACTCCCAGCTACTTGGG
AGGCCGAGACAGGAAAATCTCTTGAACCCGGGAGGCGGAGGCTGCAGTGAG
CTGAGATCATGCCACTGCACTCCAGCCTGAATGACAGAGGAAGACTCTATC
TCAAAAAACAAACAAACAAACAAACAGCAAAATTGGCTAATTCAACTGGGA
GGTGAGTGGAGAAAAGTTTTAACTGATTTTTCTCTTGGCAAAATTTATTTG
CAAAGCTATGGACAAGAATCGTTTGCATTTCTATTGGTTATATAGAATTTA
CAGGGATATAAAATTGCTCAGAAACAATAAAACAGGCAGAGAACTGAATAG
GATTGAGTAACCTATAAGAATGTGCCCAGGTAATACCTAGTTTTTCATTGA
AGACATCACATAAACTGTTCCATTTTTAAATTTTTCACATTTAACTCTACA
GTTCCCCCACCTTATAATCATAATAACCTCAATGAAATCTTATTTTTATTA
TTGAAGTAAGCAATGTCTCAAAGAAAAATAGTTCCAGTCAGTTTTAATTTG
TCATTGGAAATGTATACTTCCATACTCCACAGAATCAAGATCTATGCCTTC
CTTTCAAAGTTTTTTCTCTCAACAAAGAGCCCTATTTTCCATCATACTTAC
CTTTGTATCAAATTCCTTGATGGATATGCTGGAGTTATTGAAGGCATCTGC
AACAGGCCCCTCAGTGGAGGCATTAGATAGACCTTGCTGCTGAGTGGTGTT
CACCATGGCGATGATCGCAATGCTCAGACTCACACGCTGCGTTATCATGGT
GAAGTTTGAGAAGTGCATGATAAGAGCCAGCCCATAGCGTAATGAACAGAA
ATCTGGACCTAGACAACAACACAGATGTATGTAGTGAGCATCCTGACTGAG
ACCCCTTTCTTTTCCTTTCTCTCACAGCTCGATCTGATAGAACTTTGGATG
ACACATGAAGTCTCATTGTCTTTTTTTCACCAAAATAGCCAGCACTACAAA
CCCACTTTGTCAAATTATTTGGTTGGCTTCAAGACAGCGAATATGGGATCT
TATAACCAAGTAAAGCAAATATGGCCATCTTTCAAGGGGATAGGAAACACA
TGATAAATAGAGAAAACCCACATGTAAGGCATTTATGTCATATTGCTCCAA
AATGAAGTGAATGGGGATGACAGTGGCAGAGCCAGTCACATAACCTTCTCA
GCGTCAATAAAATTCCCTGGGCTGTAAGTGAATAGTCCCATCTGTTATGCA
CATTTGTTTATCACAAAGCTTGAGAGTTTATACATAACGAGCTGCCTTTGA
ATTAAGGTATTGCACATCCAAGGATTCTCTTTTAATACATTTGAGAGATGG
TACTTTAAATGAGCACTTCGACTAATTCCCTAGTGTAATGTCTACTTGGAA
ATGTTATTGCTATGTGTCACTAGGTCCTGCCTTCACATATGTTCAACTTAA
AAAAAAAAAAAAACTACGTGGGGTGCAGTGGCTCACGCCTGTAGTCCCAGC
ATTTGGGAGGCTAAGGCAGGTGGATCACTTGAGGTCAGGAGTTTGAGACC
AGCCTGGTCAACATGGTGAAACCCCATCTCTACTAAAAATACAAAAATTAC
CCAGGCATGGTGATGCATGCCTGTAATCCCAGCTACTCGGGAGGCTGAGTC
AGGAGAATCACTTGAACCCAGGAGGCAGAGGTTGCAATGAGCCAAGATCAT
GTCACTGTACTCCAGCCTGGGTGACAGAATGAGACTCAATCTCAAAAAAAA
AAAAAAATTAATATGTAGAACTATTTTTACAAAGCTTGCAGGTGATGTGG
TGCTGGAAGATATTCAATATATTGAAAGGACAAATTTTTTCTTTAAAAGCA
TCCCCATAAAATGGAACAACCACAGACCAATATTGAAAGGGTTCCCATGTG
CATGATAGATTGGATTTTTCCTGCTTATTTGAAGAAAAGCACTAAAGTGAA
AGAAAGAGAAAACCTGTGAAGACACAGATAAAAATATAATGGAAGAAATAA
TTTTTAATGGCCAAAAAAGCTCACAGATAAGAGTGGTGGTCTGGGAAATAA
TTATTTCCATTTTACTGGAGGTTTCCAAGCTCAGGAGAAAGAGCCAGCCGC
TTGGTGAGAATATTATAGTAGGGATTCATACATAGGTTGGTTTAAAATGAC
TTTCCCGGGCCAGGCGTGGTGGCCCATGCCTGTAATCCCAGCACTTTGGGA
```

FIG. 8-14

```
GGCCGAGGCCGGTGGATCACGAGGTCAGGAGATCGAGACCATCCTGGCTAA
CACGGCGAAACTCCATCTCTACTAAAAATACAAAAATTCATCTGGGCATGG
TGGTGTGTGCCTGTAGTCCAAGCTACTCGGGAGGCTGAGGCAGGAGAATCA
CTTGAACCCGGGAGGCAGAGGTTGCAGTGAGCCGAGATCGCACCACTGCAC
TCCAGCCTGTGAGACAGAGCAAGACTCAGTCAAAAAAAAAAAAAAAAAAGA
CTTTCCCAAAACTTATTCCACTCCCTAGATCCCAGGATTTATTGCTTATTT
GGCTTAATTTCTCACAGATGATTTCATGGGGCTAAGGAAAAAGCAACAGGA
TCAGGGGCTGGAGCTGGCTCCAATGTTACACTGGGAGTATCTTTACGAAGG
GTCAGTGTGATGCAGAGATGTGTAAATGTGTCGGAATAAGCTTCAGCTTAT
TAACATAGCCTGCAAACAAGAGCAGTGGCTTTACCTTTCCTGGTGGCAGGC
TTCCCGTCCATTTAGCTTCTGTGGGAAATGGTACCACGCTTTGTGGTGGAG
TTTCCCTGTGCCCTGAATCTCTTTTACTACGACAGTCTTTTATCTATGGAG
AGAACATAATCCAAAACATAATACACAAATAATTTCCCCTTGTTAATGTTG
CCTCCTCTTAGCATCAGTAAAAGTTTTGACCCAACACAGCTCTATAACTTA
CATTTTATGGGGCACTACTGGTATGCTTTTGGTTACAGGATTGTTAAAAGG
AAATCTGGCTGTAAGTTCCAGCTGTGTGACCTAGAGCTAGTCATTTAAATT
CTCTAATCATTCATTTCCTCATCTGTTCAATAAAGATAAGGCTCCTTTCTT
AGTGCAGCTGGAAGAATTAAATGAAAAATTGCATGTACTTTATCAAACCAC
AGAGAAGCATGCGAAGGTGAAGAGTGGTATTGCTTGTAGCAGACCATAAGA
CAGGACAATTAAACTAAGCTCAAGAGCTAAGGAGGAAGGTTCCAGAGCGGT
CTTTCCTTTCATTCTGATGGTGTTTCTCTCCCTCTGTACCACCAGAACAA
TGTTCCATGTGCCTTCGAACATGAAGGATGACATTACATAACACTAATATG
TATTACATTTAAAAGTTTAAAATGTTTATTCTCATGTTTGCTACACACAAT
GTGGACACTTGCTTGGACTGACAAAGTCTTCATATCACCTAGAAAATTATA
ATGAACAGGGACTAATTACTACAATTGTGAATAAATCCAGCTATTGTGACA
GGCAAAGAGAATTCATGGCTCTAAATATGGACATGTTTAATTTAATATTTG
TATACTAATCAAATTATCTTTGGGGATGCATACATTTGTTTCTTTTAGGAA
AAATCCATATCCTAAGAATATCATCAATTTTCCATTCATTCCTAAATTGAA
GCTTCTATGACTTTATTTTTAAATTGCTTAAAATCCTTCAAGACATCTGA
AATTTCTGTGACTTTAAAAACACATGTATCGGCCGGGTGCAGTGGCTCACA
CCTGTAATCCCAGCACTTTGGGAGACTGAGGTGGGTGGATCACTTGAGGTC
AGGTGTTCGAGATCATCCTGGCCAACATGGTGAAACCCCATCTCTACTAAA
AATACAAAAACAGCCGGGTGTGGTGGCACATGCCTGTAGACCCTGCTACTA
AGGAGGCTGAGGCAGGATAATTGCTTGAACCCAAGAGGCAAAGGTTGCAGT
GAGCCAAGATCGTGCCACTGCACTACAGCTTGGGGGACAGAGCAGGAATCC
GTCTCAAAACAAACAAACAAAAAAACACATATATCAAACCTCTATTTTATC
ATTCAAGGCTTTGCACTGTTTTTGCACACAAAATTTAAAAGACTTGTCCGT
ACTTTAAAGATATTCATAATCTGTGACCTTAGGATGAAGGATTATAAAGAA
AGGCATAGATGAAAAATTGTGTCCAAAAATATCCTTTGTAGTATTACTCAT
GACTGCATAATGTTAGAGATAAATTAACCTAATAATGAGAGTCTGGCAAGT
CAATTTGATAGATTATTGTGATGGAAGCTATTTTAAAATGTTTTCGACAAT
ATTGAATTACATTAGAAAAATGCTAGTACTCTAGTGTACAAAGCAGGATAC
GCTGTGCACATCCACATACAGGAATAGAAACTGATTCACACAAGTGCCAGT
AATGACTATTTCTGGGTTACAAAACAGGATGATCACTTCATTCTTTGTGAC
TTTCTATATTTACCAAGTGATTTTGTAAATAATTAGTAGATACTCATTTTA
TATTCAGAAGTAGCTAAATGTATTTAAAAGAGCAATAATTGGACTTCATCA
```

FIG. 8-15

```
GCATGGCAAGTATAGTTTTCTGCTTTCCAAATATCTCTAGAATTCTGGGAA
TAGTATCTCTCCATCTAAATTTTGAATTTTGGGTGTTTGGAGATTTTATTG
TTGTTGTTGTTGTTTTGTACAATGGACCCAAATGGAGGCCCAATTGCT
AGTAAGATCAGGTCAGCACCAGGACAGATACTGGTTGTTGCTCTGCCTTAG
AAGGCCTCCAAGTCTTGCTAACATCTGGATATCAGGAGTTCAGCTCATTGC
TCTACACTCAGATCCTAGCTGAAGTCATCTGTGGTCAAACCCAGAGTTTGG
ACCATTTTCTATTTGATTTCACTTTTTATGCAAGATCCCGTGGCTTGGCTG
AAGGCAACTCTTTAACTGTACATGCAGCTGCAATTACTTACACTCCACTTA
AAGCTTTCCCACCAACTTCTCCAATCTTATAAACACTGAAAGCTGAAAGAG
ACTCAGAGATCCTCTGGCCCAACTGTTTATTTTATTGATAAGAAAATTTGC
GTAGAAAATTTGAAAAGTTGCCTGAAACCACATGATGCACAGAGCCAGCAC
CAGATCCCCTAATGCCTAGACTACTGCTTGTTCTACCTATTACAACTTCCC
CTTTGTTTTCGTAATATTTTAATCACAAGCTTAAAACTCAATGGGGTAGCT
CCATTTTGAGGTATTATAAAGGAGAATTTGTATATTTTAAATCAAGTTTTA
ATCATTTATTCTAGAAGGAAGTTTGATAATGAAAAATACTTTTAGGTTGAG
CTTTGAATATTAAACATAAACACAACAAAACTACTTCTCCTTGCTCTTTAT
GTTACTGGAATTGTATCACAAACCCATCACTTTAGTTTTTCTTCCCATTCT
CTGTTGCTGTCTAACGAGAAAGGATGAAAAGCCCTACTTAAGTTTTATGGT
TTCAAATGCTACTTTGATTTTGTATCAATAGGTAATTTCAGTTCTTCGTTT
CCTATTTTCCTTTGCATGAGACGAATGCAGAAATCAGGCTAACATACCAAA
CCATCCTAAACTGAGGTCTTTCATGGTAATGGGAAATGTTTTTCCAAAATA
AGCACAGAAGCTAATAAAATTATGGAGGCTGAACACTGGCATGGTTGATAT
GTACTTAGAGACACTGGAATAATTATTAACCTATTTGCAAACAATTGAGAA
CATGTAACAGTGTCAGAACCCTTCCCTTTAAGGAGATATACCTCTAAAAAA
AAATTGTGAATTCTAGTGCCAAAGTTGTAAGTAGACACAGAAAAATGAATT
GAAATTAAGTTAAAGGAAAATGTTATATTAAAAAAAATTACTTGACACAGT
ATAGGTTGAATTTGAGAAAAAAATAAATAATGTAAATATTATGGTATACGC
ATAAGCAAAAAAACAGGTTTTTCCCTTTTTTAAGTCTAGAACTCATGATT
TTATTATAATGGTCGTTAGATTGCTCTTAGATTCTCCTAATATCCAGCCTG
TCTTGCTTCATCTCTGTTAGCCCAGAGTCCTAGTTTACTCAGAGTAAATGT
TACACCTAGATCAAAGAGCATGAACCTGCAGTGGGAGGATATTCAAGGACT
GAATTCTGCTCTGCCATTCCCAAATTGAGTAAACCAGGTAAAGTTTCAAAA
ACTCTTAGGGCTTTCACTGTTTCATAGGAAGAATTGGGATAATGTTACTTC
ACTGGGCAGTTTGGAGTGAAAACAAAAGTATGAGACATGCCTCGTAAATTG
CAAAGTGTTATATGTTGTATAATATTCTAGATACTAGCAACAGCAATAATA
ATAAACAGTCACAATATTGGCAGTCTAGCCCTCTCAGATCCATAAATACAG
GCCTACAGCAAATGAAATGTATTTCTATAAAAGTGCCTTTGATTGGTTGTT
AAATTGGTTTTAAATGTTTCTTTTTTAAAGTGGATTCTTCTGGCCTGGAAT
CCTCAAGATGAGTGGGGAGGAGTTCACCAGAAAACATAGAAGCAATTCCTT
CAGTGTTAGAAAAACTGAGGGCCCTCTCATCATCTGCCTATCTTTCTGAGA
AATTGGTGCTGACCACAATGTCCCTGGGTGCCTTTTCTTAGCTGTACAATG
AGGGCAACAAGCTAGGTGATCTCTACAAGCGTACAATTTTCTTGCCTTCAG
TCTTATTCATAACTTTGGTCATGTTCTCCTTTTCTTTTATTATTATTATTT
TTTTGAGACAGAGTCTTACTCTGTCACCTAGGCTGGAGTGCAGTGGTATGA
TCTCAACTACTGCAACCTCTACGTCCTGGGTTCAAGCAATTCTCCTGCCTC
AGCCTTCTGAATAGCTGGCACGCGCACTATGCATGCGCATAGGTGCACGCG
```

FIG. 8-16

```
CCGCTACGCCCTGCTAATTTTTGTATTTTTAGTGGAGACAGGGTTTCACCA
TGTTGGCCAGGCTGGTCTCAAACTCCTGACCTCAAGTGATCTGCCCGCCTC
AGCCTGCCAAAGTGCTGGGATTACAGGCGTGAGCCACCAGGCCCGGCCATG
TTCTCCTTTTCCTGAGAGACCATTTCAAATTCATATAGAAGTCTGAAAAGA
CTCGTTAGCCACAGTCCCAAACACAAATCTTGTCAGTTCTGATCAGTATTT
CATTCCACAGCCAATCCCAGTCTGACTAATCACAGCATCACAGTTAATACT
CACAGCGTCCTTGGAGAAATGACCATTGTCCACAGTGTCCATTGGTACCAG
TGGCTTCTCAAGCCTTGCCCTAGGGTCTTCATTGAATCAGTTATCTTTTTC
AGAGAGTCTCTTCATTTTGGAATTAGGCAATATTACCAGATGGAGATCCTT
ATGTTGCTGTTAATGTCTTTTCTCTGACTTCTCCTAAAACTGTTCCCTCCC
CTTAATGGACCTTTGGTAAGTTAGTAATAATCCTTCTACCCAAAAAGAAGA
AAAGCACTTACCTTCACCATTAAACCAGTATTTTAAGCCCTAGACTATAAG
CTAACTTGGAAAAGGAGGGAGTTTTCTGTCCCTTCTTCCCTTTCAAATAC
TTTTGCAGATTTTTACAGGGATAAATAGTGAGCCACGTGGCAGTCAGACGG
CAACAGGTTTGGCCCCACTTTCTCAGAAAGCCTCGGCTTGGTTTTGCCGCT
TAATTTTTAACTTCATTTTCAAGTTCTCACTGTTAGAGTATCTCAAAAGAT
GTCATCGTGTGTTTCTGCTTTGAACTGTGCATACAACCATTCAGTCAACAA
GCCTTTTTTTCTGAAAGCAAGGGGGCATGGTGTGGAGGAAAGGGCAGGGCT
CCTGAAATCAGTGATGGAGTCAGACCCATATTCACTTCCTAGTGTTTTCCC
TGAGCTTGGACAAGTCACTGAACCTCTTTGAATTGGCTTCCGCTTTAGTAA
AGCAAGGATTGTGTTACTGTACTCATGGGGTTATTGAACAAATGAAATACA
TATTCTAATTGGTAGTAGCTCCTCAATAAATGAGGTGTTCATTCCTCTTCA
GGAGTTCAGTTAAGTCAGCTAGATTTTCCATATGCATTTGGTGCCCACAGC
CTAATGAATGTGAACTGTGACTGCCCTGGCAACTTCCCAGGAAGCTGCCTT
GTACCCCTCCTTCCTGTTTCATATCATCCATGTCTTCCCTAATCCATTTTC
TGCTTGGCTCCCGACTCTTGGAATTGTGTCCTATTTGTAATCATTAATTTT
GAGACTGTGGTTGCTATTGGATCTTCCTAGTGTGACGCAACCCTTATAAAA
TGAAATGAGAGCCTTCCCTCTCTGGCTTATCAGCTTCAGACTTCCTTAATT
GAGTTCCGCCATCCTAGTGAGTCTCACCATACTCCCGAAATAACCTGCTGG
AGTAGGCTTATCCTACTCAACTCCTCAGATCTCTGTATTTAATTCTATTTT
ATTGCTGTTGTAGTAAATTACCACAACTGTGATGGCTTGAAACAACACAAA
ATTATTTATTTATTTACAATTCTAAAGGTCAGAAGTCCAAAATGGGTTTCA
CTGAGCCAAAATCAAGGTATTGGCAAGGTTGTGCCCCCTCCAGAGGCTTTA
GGGGAAAATCCATTTCTTTTTCTTTTCAGCTTGTAGTGACCACTGCATTTT
TTGGCTCTTGGCCTTTCCTCCACCTTAAAGCCAGCAGTGTAACATCTTGAA
GTATTTTCTCTTATTCTGACTCTTCTGCCTGTCTCTTATAAGGACCCTTG
TGATTACACTAGGGCCCATCTGCAAAATTCAGGAAAATCTGCCCATCTCAA
AATTCTTAACTTATTAAACATGTAAAGTCCCTTTTGTCATATAAGGTAATA
TATTTACAGGTTCTGGGGATTAGGACATGGATATCTTTGGAGGACAACATT
CAGCCTACCCTTTTGAGGGATAGAGGGGTAGCAGGAAGAGTTGAAACAATT
CCTTCCTTTCTTTATTTAAAAATTCTGGTTATTGATTTATTATAGTTATCA
TGTGCCTGATAAGCCAATGAAAATAGTTATAATGGCCAGGGGCAGTGGCTC
ATGCCTGTAATCCCAGGACTTTGGGAGGCTGAGGCAGGAGAATCGCATAAG
CCCAGGAATCCAAGACCAGCCTTAGCAACATAGGGAGATCCCGTCTCCACA
AAAAAATGCAAAAATTAGCTTGATGTTGTGGCACATGCCTATAGTCCCAGC
TACTCAGGAGGATTGCTTGAGCCCTGGAGTTCAAGGCTGCAGTGAGCTGAG
```

FIG. 8-17

```
ATTGCACCACTGCACTCCAGCCTAGGCAATAGAGCAAGACCCTGTCAGAAA
GAAAAAGAAAGAAAGAAAGAAAGAAAGAAAGAAAGAAAGAAAGAAAGAGAG
AGAGAGAAAGAAAGAAAGAGAAAGAGAGAAAGAAAGAAAGAGAGAAAGAGA
AGAAAGGAGAACTTTCTTGGCTTAATTTACCCAAAAGGTATGATATTTTCT
TAATTTGCATAAGGCAGAGCATGAGCTGATACCAGTTCTGGTAGAAAAAGT
AGGTGAGACTGGATCCCCCAAACAAGAGTAAATATTTAATATAATAAGGAA
AGAGTGGCCGAAAGTATTCAATGCCACAAGTAAGATTCAGAGTAGATTTTT
CAAACTGCATAATTTGTTTAAAAAGCATAATTTTATAGCTGGATTTTGCAA
GCTCTCTGAGGGGATCTTGTTCATTTTGAGAATCACTATATCCACAATTCT
TGGCACAGTGTCTGTCCTATGGTGTGTGCTATGATCCAAATGTCTGTATCC
TCTCAAAACTCATGTTGAAATCCTAACCCACAAAGTGATAATATTAGAAGG
AGGGGTCTTTGGGCAGTAGTTATACCATGAGGGCAGAAACCTCATCACTAG
GATTAGTGTCCTTATAAAAGAAACCCAAGGAAGTTTATTCAACCCTTCTGC
CATGTTAGGACTCAGCAAAAAGATGGCTACCTGTCCTCACCAGACACTAAA
TTTGCCAGGGCCTTAATCTTAGACTTCCCACCTCCAGAACTGTAAGAAATA
AATTTTTTGTTGTTTATAAGTCACCCAGTTTATGATATTTTGTTACAGCAG
TCTGAACAGACTAAGACAGTACACGCTTAATAAACATTAGTTTACTGAATG
AATGAATTCTTGCATTGCTTCACCACCAACAATCAAGATCTCTGTAGCTGG
TTTAACCCCCTCACTCCCAATCATGATTTTCATATAACAAAGTTAACTCAG
TTAAATCAACTCAATAAGGTATACATTAAATGAAATTAAAGAAGTTGTAAC
ATTTATAAACATCAAGAGTAATGTAGAAGAAAAGTCCAGAGATCCTTAAAA
ATTTAAGCCTCTCTGGCCTGACATTAACAGCTAAGGCAGGAACAGAAAACC
AAACACCTCATGTTCTCACTTATGAGTGGGAGCTGAACAATGAGAACATGT
GGACACAGGGAGGGGAACAACACTCACTGGGGCCTGTTGGGGGAGGATGGG
GTGGGGGTGTGGGAGAACATTAGGTAAAAGAGCTAATGCATGCTGTACTTA
ATACCTAGGTGATGGGTTGATAGGTGCAGCAAATCACCATGGCACACGTTT
ACCTATGTAACAAACCTGCACATCCTGTACTTGTACCCAGGAACTTAAAAA
ATAATAATTTTTTAAAAAACAGCTATTTCCAATCAGAGCAGTTCAATTCCA
TACAATTATTATTATTATTATTATTATTATTATTATTATTTTGAGATG
GAGTCTCACTGTCGCCCAGGCTGGAGTGCAGTGGCATGATCTCAGCTCATT
GCAATCTCTGCCTCCCAGGTTCAAGTGATCCTCCCGCTTCAGCCTCCTGAG
TAGCTGGGATTACAGGTGGGCACCACCACGCCTGGCTACTTTTTGTATTTT
TAGTAGAGATGAGGTTTCACCATTTTGGCCAGGCTGGTCTTGAATTTCTGA
CCTCATGTGATCCTCCTGCCTCGGCCTCCCAAAGTGCTGGGATTACGGGCT
TGATCCACTGCGCCCAGCCAACATACTATATTTTTTTTGATAAATTTTCT
GTATTCTAGACATGACATTAGCTTCCGACAATATTAATTTATTAAGATCTG
ACCCATGACATGACTTCATAAGAGTTCAGAGTCCACTGAATGAGACCACAC
ACAGAGACAGACAACTAGAATGAAGGATGATAAACATGAACAATACAAACT
TGCACAGGTGACTAGAAAAGAACAAATGAAGACTCCTGCCAACTGGGGGTA
TCAGGGGAAGGCTTCCCAGGCAGAACAGGGCTGCGCCAGTCTCCATGTGTG
GTATGAATAAGTCAGTAATACAGGGGAAGCACCTTCCAGAAAGAGCAAACC
CGTTGAGGCTTGGTGTGAGGAATAAGAAGTGTCCAACATGACTGGGGATTA
AAGTACAAAGGTATAAAGGAAATGTGGTGAACTGACTGGAAAGATAAGAAT
TTTTTTTAACAGTTACTTTTCCCAATAGTAGAATTAACTAGACAGGAATAG
AAATGGAAGAAGTTTTTATGTTCCCTTAGAATGAAAACTATACATTTTTA
AGAATTATATGAACAAGGAAAATGTGACTCAAAGGCAGAAAATGATAGAAT
```

FIG. 8-18

```
TTTATTATAGGGCAGAAAACAGGATCTGGCTAAATTAAACTAAGTACTCTA
CTATACTATACCATATGCTATATTCTTGAATGGGAGAAGTAATACCATAAA
AACTATTGATTCTTCCTAAATTAGTAAACACATTGAGTGAAAATCCAAGAG
GAAGAAAGAAAAATGGAAGACAAACTGGAAATAGCCCAAATTTTCATCAGT
GGAAGACTGAGTACTTTGTGATACATAGTCATTGCAGAAAAATAACACAGT
TAAAAAGAATGAATCACATCTATAACATTTGACCTGAATACTTTCATATAA
TGTAATACATTTTTAAATGAGTAAAGCAGATACTAAGGACGTATAAAGGGA
CTCCATTTTTTTCTGAATATTAATCAAGAAAATTCTATATATCTGTATCTT
TGTTTACATAAGATTGTGTGAGCCATAATAGCTGTTGACTTGGGTTATCAG
GTTTGGGTAAACAGTTTAGTGGTAAAAAAAAGATGTGTAAGACTTGGCCGG
GTGCAGTGGCTCACATCTGTAATCCCAGAACTTTGGGAATCTGAGGCAGGC
AGATCACTTGAGGTCAGGAGTTCCAGACCAGCTTGGCCAACATGGTGAAAC
CTCGTCTCTATAAAAAAACTACAAAAATTAGCCAGGCATGGTGGCGCACAC
CTGTAGTACCAGCTACTCAGGAGGCTAAGGCAGGAGAACCGCTTGAACCCG
GGAGGTCGAGGTTGCAGTGAGGTGAGATCGCGCTACTGCACTAAGCCTGGG
CAATGACAACAAAACTCCGTCTCAAAAAAAAAAAAAAAAAGTGTAAGACTT
AGCAAAAAGGTGACCAAAAAAAAGCAACATTTATAAACTATGGATGTAAAA
CTCTATGTATGTGTGAGTGTGTATACATGTGTGAATATACATAGGATACAT
TTTTGTCTGTATGTGTATATGTACATACATGCATGTATGTGTATGTGTGTG
TATATATACAAGCTTTTTTAAAATGTTTTCAACAATATTGAATTACATTAG
AAAAATGCTAGTACTGTAGTGTACAAAGCAGGATGCGTTGTGCACATCCAC
ATACAGGAATAGAAACAGATATATACATACACACACACTACACACACCCCT
ATACCTACACCAAATATACATTGAGAGAGAGAGATAGAGAAAATAGTAACT
AAGGTAGTTAATTCTGGCCACAAGGATTTTTAGATGAATCTGACTTTCTTC
CTTAGGTTTTTTTGTATTGTTTAAAGTTTCACACAAATAGCATTTATTTA
CTGTATAATCATAAAAGGCAAAAACCTATTTTGATTTTAGGAAAACACAAA
GCATCCAAACCAAAAATCTCAACTTAGGAAATAGCGGGAAATCTAGGGAAG
TCAACAGGACCAGGTCATGACGGTCTTTTATGCAATGTCCAGGAGCTTGAA
CTTTATCTTGTCGTTCCTATATTTCCTCAAAACAAATGTGTGTGGACGCAG
AAATGGAAATGCACAGCAGTGCACTGAGGTCACAGGAAAAATACAAAACAG
TTTTTCTGAAGTACTAACTTCACTCAAAACTTCGGGAAACATTTTAAAAAT
GGTTTTAAACAAATTTGACTAAATTTGACAAATTTAGTCAAATGCAAAATT
TTCATTTTTAAAAGGAAATAAATTTTAGAGGAAAAAACAGATGTGAAAAAG
AATACATGAAATAGTACATGAAGGAATACATGCACGTGGCATACACTTGAA
TCCATGTATATGCCAGGTTTTCTTGTGTTGCACACAAGACCAACTCTGAAG
TTAAAGATAACCCAGTAGAAAAAATTAAATGATGGGGAGTAATTAAAATGT
TTTCAGCAGGAGTAGGACATGATTTTTATATTTAGACTGTTTAGTCGGCTA
GTTATGTCTGACGGATAGAAGTGAGGACACTCCTAATTGAAAAGTAAGTGC
TACTAAGAAACTCAACGTGGGGGTCATAGAATGAAGCCAGACTTTTGTTCC
CAAGCAGGAGACAGATGCAGATAAGAGGGAATGAAGATGAAGTAAGGGCTG
AACCACAGAAGCTTCGCATCATAAGTCATTGTATTTCTCTGAGTGAACATC
ATAGAACTTATTTACTATCTGGTCACAAAATGCCACTGACATGAAAAGAAA
TCGGGTTGAAATGGCTCTAGACCAAGATTCCCAAGACATCAAGAAATCACC
AAAAGTTGCCTCAGGTTCACAAAAAAAGATATTCCAAGGGAGTTCTCCAAG
TAAGTAAACACTCATTATTTCTATAAGGCTTAGGCCACAAGACCTTGGCTG
AGACCCCTGTCTCTGTGATCTGGTCTGTACCACATTGGAAGGGCCATGACT
```

FIG. 8-19

```
GATTTCTACCTAGACATTTAAGGCTGAACGGAGGCTGAAGAACCTCTTGCT
TGCTTTCCCATAGACTCACATCTGATAACAGCCCTCATCTTAGGCCCCAGA
GGGCAAGAAGAGGTTAAGAAGGATCAACCAAAGGTAAAGTACACCAAGAAA
AGAGCAGCTCTTTGGTTAGAATTTTAAGATAAAGAGAGACACATAAAAGCT
ACTGTTGAAAAATAACAGAAGGAACAACGTTTTATCTAATCAATAGATGGA
ACAAGACAATAGAGGACCATCTCAACAATAACCTAGAATACCATGGAAGAC
AGACATAAATCATCTGTATTTGTCCTGCTCAAGACTTGCCATATGCCAGGT
ATGGTGGCTTATACCTATAATCCCAGAACTTTTAGGCTAAGGCAGGAGAAT
TGCTTGAGCGCAGGAGTTCCAGACCAGCTTGTCTCTACAAAGTTCTCTGGG
GGTTTTTTTTCGTTTGTTTGTTTTTAGGCAGGTGTGATGGCACACACTTG
TGGTCCCAGCTACTCAGGATGCTGAGGTGGGAGAACAGATTGATTCTGGGA
GGTCAAGGCTGCAGTGAGCTATGATTGCTCCACTGCACTCCACCCTGGGTG
ACAGGAACTGCAGACAGCCTCTAGAAGTTGAATCAGCCTCTACCAAGAAGC
TTCTACCGGTGCAAAGAACTGAATTTTTCAACAAACCTGAGGGAGCTTGGA
AGTGGAAATTTCCACAATCAAGCCTCTGATGAGAATTCAGACTCAGCCAAC
ACCTGGATTGCAGCCACATGAGGCTTGAAGCAGGGAACCCAGTTAAGCCAT
GTCAGAACTTCTATCCACAGACCTTAGGTAATAATAAATGTGTGTTGCTTT
AAGCCACTAAGTTTTTGCTAATTTGTTTTGTAACAATTATATATAACTAGT
ACACATGAATAGTAGAATCTAATATCAGCCATTGACTTCAATGAAGGAAAA
AACAGATGTGAAAAAGAATACATGAAATAGTACATGAAAGAATACCTGCAC
ATGGCATACACTTGAATCCATGTATATGCCAGGCTTTCTTGTGTTGCACAC
CCAGACCAACCCTGTAGTTAAAGATAACACAGTAGAAAAACTGAAGAGTTA
CTGAGAGTAATTAAAATGTCTTAAGCAGGAGTGGGGCATGATTTTTATTTT
TAGACCGTTTAGTCTGCTAGTTATATCTGATGGTTAGAAGTGAGCCTATCT
CTGGTCCCATGTTCTTAGAGAGTACTTTTATCTCTTTATCCATCTAACA
TCTCTAATTTATGTAACATCCCAAGTCCTCATTAATCCTGTGTTATTGCTG
TTGGAAGTCCATCTATCCCCTCAAGAACAGAGCCTGAAATTCCTCTTTGAA
AAATTTCCATTCATCATAATCTCAAATTTCTCCAATGTCATTTTCCACCTA
AATTTCATGTGTGACTTGAATCTCAAGACTATTCATCTGCCCCAGGTATCT
GTTTGATGCCTGGATATGTCTGAATTATTATTATTGTTATTATTATTATTT
TTTTTTTAAATGGAGTCTTGCTCTGTCACCCAGGCTGGAGTGCAGTGGTGC
GATCTCAGCTCACTACAACCTCTGCCTCCTGAGTTCAAGTGATTGTCCTCC
CTCAGCCTCCCCAGTAGCTGGGATTACAGGTGCCTGGCACCTCGCCCAGCT
AATTTTTTTGTATTCTTAGTAGAGATGGGTTTTCACCATGTTGGCCAGGCT
GGTTTTGAACTCCTGACCTCAAGTGATCCACCCACCTCAGTCTCCCAAAGT
GCTGGGATTACAGGTATGAGCCGCCACACCCAACCTTAGACCTCATCCTAC
CCAGCTCACGTGTCTTTTAATCCTTTAGCTGAGGTTGTAGTTTTAACTTAT
TGCTGCTTGAACCTATTTCAATGCAAAAGTTCTAAAAGAACTCAGCCACCA
AAATTCCCTTGATTTGCTGCACTGTACCAAATATTAGTCTTAATGAAATAC
AAGATTTGTTTCAGGATCTCAAGCCCAATATTTTCAACTGTAGGCTTCCCA
GTATCCAAGGTTTACGCAGGAGATTGGCAGTGGGTACATTCCCAGGGTCAG
TGGTTTTTATCCAGGAAGGAACCTCAGAATCACCTGGGGAATTTTAGCAAC
ATACACACCAGTGTTCTCAGGAGTGAGGCTCAGGTATGTGGATGGCAACAA
TACTTCCCTTATCAAAAGCTGCCACCACACCAGACAAATGAAAACTGCTC
TTTAATTATACAGCTTGGCCTTACCTAATGGTTCTCAATTTTGGATGGACA
TTCAAATCACAAGGGTAGTTGGTTTTTTTTGTTTTGTTTTGTTGAGACAGA
```

FIG. 8-20

```
CTCTCACTCTGTCGCCCAGGTTGGAGTGCAGTGGCGCCATCTCGGCTCACT
GCAACCTCCACCTCATGAACGTAGTTTTAAACAGCACTAGTGCCTAAACCA
GACTCCAGAGATCATGATCCCTAATCCTATCCCTACCCTGCGGTACTCATT
CTGAGATATGCCCTGGGTAATAAGAATTTTAGAAGGTACTCAGGTGATTCT
AATGTTCAACCAGTCTGAGAACCATTCGCAGACTTCATATAGATACTTTAT
TCCAAACAGCTGAGCTGGACCATAGCTAGAAGAAGGAATAGAGATGAATGA
GAGTTCATATTTTCCATAGAAAGCCGCTGCCCTCTTCTAAATGTGAATGGA
AGTTCTGGAGACCCCTATCCTAAGGTAGACAGATGACAGATACACTGGAGA
ATGCTGAAGGAAGCAGATAGGAGTCTAGGCTTTAGACCACACCTTCCAAGA
CGTACTACTCATGCCTGATGAAGTATTACCAAACATACCCCTGGGCCAATA
AACAAAGCAGGAGCAAATGTGTTTGTGTGTGTATAACTTTCTACACAAAAT
ACAGAAAAAGTGATTCAATGTTCAGCATAAATAAAATTTTGTGTTTTAGT
ATTGTTTTATTTCAAAGTACATCTTGGTGAGAATGCATTATTTTGAACTGG
ATAAAAGCCCCCCACTACTGAATCCCAGGTCTCTCTATGAAGCCTGAATAG
AGGCACTGTAACTCTAATGGCCAAAGGGCTGGCCTGGAAATTCTCCCTTCA
GCTGCAAAAAGAGAAAAAGAATAATCCAAGCAAACAAACAAAACAAAGAAA
TGAGCAAACCACTACAACACAAAACCCTTGGGATGAGATGAGTACTAGACT
GGGAAAGTGATAGCTCTGGTATTCATGTGTGTGTGTGTGTGTGTGTGTGTG
TGTGTGAGAGAGAGAGAGAGAGAGAGCACATGAGAGCACACACAAGACC
CTATAGAGGAACCAAGTAGCTTATCTTCTTCCTTGGATTCCTCTATCTCAT
AGCCTAGAAGACATGGGGTGATCCTAGCCCCTGGTAGTGTAGGACAAGGTA
GAGTGGGACTGTGGTTTTAAAATACTTTTTAGACCGGGTGTGGTGGCTCAT
CAACACTTTCGGAGGCGGAGGTGGGTGGATCACCTGAGGTCAGGAGTTTGA
GACAAGCTTGACCAACATGCTGAAACCCCGTCTCTACTAAAAATATAAAAA
TTAGCTGGGCATGGTGGCAGGCACCTGTAATCTCAGCTACTCAGGAGTCTG
AGGCAAGAGAATCGCTTAAACACAGGAGGCAGAGTTTGCAGTGAGCCAACA
TCATGCCATTGCACTCCAGCCTGGGTGACAAGGGTGAAACTCTGACTCAAA
GTTAATTAGTTAATTAAAATAAAATACTTTTTTATTTGGGGCTGGGTGCAG
TGGCTCATGCCTATAATTCTAGCACTTTGGGAGGCCAAAGTGGGAGGATCA
CTTGGGGGCAGGAGTTTGAGACTAGCCTGGGTGACATAGCAACATGCCATC
TCTACAAAAATTTAAAAAATAAAAATTAGCTGAGTGCAGTGGTGCACACCT
GAAGTACCAGCTACTCATGAGCCTGAGGTAGGGGGAATTACTGGAGCCCAG
GAAGTTGAGGCTGCAGTGAGCAATGATTGGGCCACTGAGCTACAGCCTGGT
GACAGAATAAGATGCTGTCTCTAAAAACAAAAAACAAACAAAAAAAACCCA
AAAACCTTCTTATTTTAAAATGATTTCAAACATATAGAAAAATCAGAAAAA
CAGTACAAAGAACACTCATATACTTTTTACCTAGATTGTTAATATTATACA
TTTGCTTTTTCTCTACCTATCCATTTATTTATATGTCTTTATATCTCTTTA
TATATATATATACTTACTGAAACATTTGAAAGTTGCAGATAATCATCTTCC
TATATTACTCAATACTTTATCTTTAAATTCAAATTCAAATTTTACCAGCTG
TCCCAATCATGTCTCTGACAACACTTTTTCCCCTCAATCCAGGATCACAAA
TTGCATTTGGTTGCTATCTCTTTAGTCTCTATTAACCTGGAACAGTTTCCT
GGCCTTTCTTTATCTTTCATGATATGAAATGACAATGAATTTTTAAAGGTT
AGGTGTTTTGTAGATTAGTTCAGTTTTAAAACTTCACAACAAAGTGCCAAA
GATGTCTTGGCAGCAGTGCTCAAAACAGGTTGGAGATGCATAGGAGCCACA
GAGAAGGGTCTGGTTCAAAGGCCAGTGGTCGTCTCATTACAGCACTGCTCC
ATCAGGTCTAGGTCTGGAGACTTGGTAGCACGTCTATGGCCCCAAAGTGTG
```

FIG. 8-21

```
TAGAGAATGTTGAGAATTGCCTAGGGTGGCAGACTTAGAGGAAGAAAGGTT
GGTATGAGGCCTGTCTAAAATTGAATTTGGCTATAGAGTTATGGAAGGGTT
TTAGGCCATGTCTGGGTGGAATCAGATTCAGTCAGCAAGTAAGGGGTCTTT
GGGAGGTGAGCTTAGGCTGTCTGGGCCCCTTCGAGGAGGGCAGATTTTATG
GGGAAGGGCTCTCCTAGAAGAACCTAGTTTAGGATGAGCAAATCACGCAGG
TTCATTCTCCACTTTACCCTAGCACTTCCTAGGCTCAGTGGTGGTTTTGAA
CTTTTCCCATCCCTGCAATTACTCCATAAAGGGAATGTGCAAGGAAGAGGG
GAGGAAAGAGATGTGAGTTCTGCCAGAGGCTTCACTGTTTCATTCCCAGAT
TTATTTGAAACCAACCCTCCTCCTGTACTTCATGCTCTCCAAGCTCATGGT
CCTGGAACTTCACATTTACATAATACGGAATTTTTTTTATTACCCTTGATC
TTTATGCATGCAATCTTTCTGAACACCCTGGACCCCCTCCTTCTCTTGGTG
ACCTTTTCCTTCTCCAAAACATGGTTCACCAGTTATTACCTCTGCAGCAGT
GGTCCTTCCAGGAGTTGCTTGCTGCTTTGTTCTTCTCAGCCTCAACACT
TTTTCTTATCTTGTTACAGCATTTAGAATGTAATGTTTTGTTTTGTTTTTA
AAACACATCTTGGCTTTCTGGAAACTTATATAGAAAATAATTTTTTTTCCC
TCAATAGATATATGGCTAGGGTCCAGCCTAATGTCTGCCATAGAGAAGCCT
AATGTCCAGCCTAATGTCAATAAATGTTTATTGTGGGCATAAAGGAATACA
TTTTAAAATAATGGAGTGTTTAGGTAAAATTAGGATTATTAGCTTGAGTCA
TTTAAAATCATCCACAAGAACCAGATCAAATGTACATGTCTTTAATACTGG
TGAAAGAAGTAGTTACGCTGTCTTAAAGGCAAAACGATATGGACATAGCCA
CCAGAAATACAAGAGTGCCATCTCTTGGTAAACCTGTTAGCAGACAGAGAA
GACACTGAGAAGCCATGTAAAATATACTTGATAATGTGTCTCTTATGTAGG
TTATGTAAAATGTGGAAGAAAGATGGAAACAAAATTGAGAGACGTGGTTAT
GGCATTTTCCAGGAAAATTGGAAAATATTTTCTCCTAATAATTCATGCAAA
ATGTAATGATATTTTTTAATGCAGAAGAAAACAGTGTAACAAAAGCATTA
TAATTATGGCAAATTGTTGAATGCTTTCTCCACCCCTGCCCTTTCCACTCA
GAGTAGGAATGAAATAAGGATGTCAGTTATCACACTTTATGTTCAATATTA
TATGGGAGATGCTAGCCAGTGTACTGTGGAAAGAAAATAAATGTTAATGT
TAGATGTTAATGGTGTAAATATTTCAATTGAAAGGCAAAGATTGTTAGAAT
CGACTTAAAAATGCAAGAACCAAACACGTTGGCTAGAAGAGAAACATCTTA
AATATAAAAACACAGATAACTTGAGAATAAACATATTAAAATATATACACT
ATGCAAACAGAAAGCATAAAAAGACTAAAATGGCTATAATAATAACAGCTA
AAATAGAGTTTAAGACAGAGAGTGTTACCAGAGACAGAGTGATATTTTGTA
TTGTTAAAGGAGTCAGTTGCCAGCCTGGCCAACATAGAAAAACCCCATCTC
TACTAAAAATACAAAAATTAGCCAGTCATGGTGGTATGTGCCTGTAATCCC
AGCTACTCGGGAGGCTGAGGCATGGGAATTGCTTGAACCCAGGAGGCGGAG
GTTGCAGTGAGCCAAGATCACACCACCGCATTCTACCCTGGGTGACAGAGT
GAGACTCTGTCTCAAAAAAATAAAATAAAATAAAAATGCCGAGGTGGGCGG
ATCACCTGAGGTCAGAGGTTCGAGACCAGCCTGGCCAACGTGGTGAAACTC
TGTCTCTAATAAAAATACAAAATTAGTTTGGCATGCTGGCACATGCCTGTA
ATCCCAGCTACTTGGAGGCTGAGTCAGGAGACTCGCTTGAACCCAGGAGGT
GGAGGTTGCAGTGAACCAAGATTGTGCCACTGTACTCCAGCCTGGGCAACA
GAGTGAGACTCCATTTCAGAAAAAACAAAAACAATGACAATAGAAAAGTGT
CATTTCATCAAGAAAACATAATAATCATAAATGTATGATTCTAACAACAGA
GTTTCAAAATACATAACGAAGTTTTAAAATACATAGCAAAATGTCATAACA
GAGTTTCAAAATACATAAAGTAAAAATGGAAAAGAAAAGACAAAATAGACA
```

FIG. 8-22

```
ATTCTACAATCACATTTGGAGAGTTTAACACCCTTTTTTTGGTAATGATGC
AATAACTAGACAAAATATCAGTAAAGACACAGAAGATCTGAACAATCCTAT
CTATTATCTTGAGCTAATTGATTTATAGAACATTATACACAATATCTGCAT
GCACATTTTGCTCAAGTACACATGATATATACATCATGATAGATCATATTC
TTTTTTTCTTTTATTTTTAGTTGACATATAATAACTGTACATATATACGGG
ATAAAGAGTGATATTTTTATATGTGTACACAATGTGTAATAATCAAATCAG
AGTAATTAGTATATCCATCACCTTAAACATTTATCATTTATTTTGTTGTGA
GTATTCAAAATTCTTTTCTAGCTTTTTGAAAATATACAATAAATGAGAGTT
AACCATATGCACCCTACAATGGTGCAGAACACCGGAACTCATTTCTACAAT
CTAGCTGTAATTTTGTCACCATTAACCAACCTCTCCCTATCCTCCCCTCCT
TGCTACCCTTCCCAGCTTCCGGTACCCACAGTTCTGTTCTCTAAATCCATG
AGCTAAAAATTTTTCTCTACTTTCACATATGAGTGATAACATGTAGTATTT
ATCTTTCCAATCCTAGCTTATCTTACTTAACATAATGTTCTCCAGTTTCAT
CTACGTTGCCACAAATGACAAGATTGCATTCTTCTCATGGCCAAATAGTAT
TTCATTGTGTATATATGCCACATTTTCTATCCATTTGTCTGTTAATGAACA
TTTAGGGTTGACTCTATATATCAGCTCTTGTGAAGAGTGACGCAATAAACA
TGGGGATGTAGGTGTCTCTTTGTATACTGATTTCCTTCCCTTTGGATAAAT
AGCCAGTAGCAGATTTTCAGCCTCATCTGGTAGATCTATTTTTAGGTTTCT
GAGAAACCTCTGTTGTCAGTAGGCTGGTTCAGATTCTTGAATTCCCTGCAC
AAAAGAATTTGAAAGCCAGTCCAAAGTAAAAGTAGGCAAAGGAGTTTATTG
CAAGGTGAAAGTACACGCTGATAGCAGAGTCAGGGTCGGCTACTTCAGCAC
CAATTGACACTGAAGAAACTCCCGTTATGGGAGTCCTACGTGATTATCCAT
GAGGGGGTGGGAATGGGCATTGTTGTTAAATATGTTTTGGGTGGTCTCTTG
AATGTGCATGCAATATTGCCATACACGCTAGTACATACATCACATGTATTA
TTAGCATTTTAATTCTCTACCCAAGGGTGTGTTTCTTACTATTAAAATGAG
TATATGTCAACCTGAGAACACAGCTTGTGGGTTTCTGCACTTGCACGAACT
TAGGGATTTTCCCTCCTGCTCTTCTACCTCCTTGACTGAGGATATTCTAAC
CACTAGCCCCAGATGCAGTTTGTGTAATGTCAAGAGATTTGTTCTCTCCAT
CAATTTGACAAGTTTCTTGTTTCCTTTCAAGGGAGGCTGTGACCACCCTAT
GTAACCTACCTCACTTCCATACTATTTTGCATAATGGCTATGCTAATTGAC
ATTTCCACCAGTGGGACATAAGAGTCCCCTCTTCTGTACATCCTCACCAGC
ATTTGTTATTTTTGTTTTTTTGACAATAGCCATTCTAACTGGGGTGAGAT
GATACCTTATTGTGGTTTTGATTTGCATTTCCCTGATGATTAGTTATTTAT
ATGGTTTGGCTGTGTCCCTACCCAAATCTCATCTTGAATTGTAACTCCCAC
AATTCCCATGTGTCCTGGGAGGAACCCAGTGGGAGGTGACTGAATTATGGG
CCGGGTCTTTCCTATGCTGTTCTTATGATAGTGAATGAGTCTCACGAGATC
TGATGGTTTTAAAAACGGGAGTTTCCCTGCACAAGCTCTCTCTTTGCCTGC
TGCCATCCATGTAAGATGTGACTTGCTCCTCCTTGCCTTCCACCATGATTG
TGAGATCTCTCCAGCCATGTGGAACTGTAAGTCCATTAAACCTCTTTCTCT
TGTAAATTCCCCAGTCTCAGGTTAAGTCTTTATTAGCAGCATGAAAACAGA
CTAATACAGTGATGTTGAGCATTCTTTCATATATTTGTTGGCCAATTGTAT
GCCTTCTTTTGAGAAATGTCTGTTCAGTTCACTTGCCCACTTTTTAAATGA
ATTGTTGGTTGTGCACGGGTGGCTCGTGCCTATAATCCCAGCACTTTGGGT
GGCTGAGGCAGGAGAACTGCTTGGGACTAGGAGTTTGGGACAAACCTGGGC
AACACAGAAAGGCCCTGTCTCTAAAAAAATGAAAATAATAAAAATAAATGA
ATTATTAAATCTGACTACAGTAGAAATAAATTTGAAATCAATAAAAATAAG
```

FIG. 8-23

```
AAATGTAGAAAAAAACACACATATTTGGAAATTAAACATCATTCTAATTAA
TCAATCTCTCCAAACAAATCACAAAAAATTACAAAATACATTGTACTATAT
AATAATGACAATAAAGCACATCAAAATTCATGGGATGCAACTTAAACAGTG
TGTAGAGAGATCTGTAACTTAAATTGCTTATAGTAGAAAACAAATAAAGTC
TAAAATGAAAGTCCAGATTCTACAAAGGTGGTATGTCTAATAAGAGATACT
TGTGTTCTCCCAGTAATACTGCGATCCCAAAGGATGATAAAAGTAAACTAG
AAGTAATCCCATCCTACTCTCTGGAAACTGCTAGAATGTTTGCTCTGCTTC
TCAGCAGAGCAAGGGATGTGAGAGAGGTGGGGAGAGACAGAGAGAGAGAGA
GAGAGAGAGAGATCATCAATCCTGATAAGTTGTAACCACAAGCCAACTT
TTATACACATTTAGGCTAAAAAATAAAAAGTCTTGGCTAGCCACAGAGGCT
CATGCCTGTAACCCCAGCACTTTGGGAGACCAAGGTGGGAGGATCACTTGA
GCCCAGGAGCTCGAGACTGGCCTGGGCAACAAAGTGAGCCCCATCTCTAAA
AAAAATATTTAAAAAATTAGTCAGGCATGGTGGCACACACCTGTAGTCCTA
GCTATACAGAATGGTGAGGCAGAAGGATTGCTTGAGCTCAGTAGGTTGAGG
CTGCAGTGAGCCATGTTCACACCGCTGCACTCCAGCCTGGGTGACAGAGTA
GGACTCTGCGTAAAAAAAAAAAAAAAAAAAAAAGTCTCAATTCATGAATTG
AGTTTAAAGTAATACTTGACTGGTGGTACCCCAGCTTCCTGGCAAAAGCAG
ACACAAACCCCCTCTAGAAGAAAGAACATCCCAGTCCTCAGTGACCCATAA
GTAATTTTACCAGAAAAATAAAGAAGTTACTGGCAAAATCATCAAATGCAC
AAAATGGATTGGAGGAAGCGTAGCAAGAATAAATGAAGAGGAGCTGGGTGC
TGTGGCTCACGCCTGTAATCCCAGCACTTTGGGAGGCTGAGGTCAGGCGTT
TGAGACCAACCTGGCCAACATGGCAAAACCCCGTCTCTACTAAAAATATAA
TAATTAGCTGGGCATGGTGGCATGTGCCTATAGTCCCAGCTACTTGGGAGG
CCTGAGGCAGGAGAATCGCTTGAACCCGAGAGGTAGAGGCTGCAGTGAGCC
TAGATGGTGCCACTGCACTCCAGCCTGGGCAACAGAGTCAGACTCTGTCTC
AAAAATAAATAAATAAATAAATAAATAAATAAATAAATAAATAAATAAATA
GGGATCAGGAGGTTTGAGTAAATAAGGTTAAAAGTGATGGTGTTCTAGACT
ATTTGTGTCTTTATATTAAAGTGAATTTTTTGTAGGCAGCATGTTGTGGCT
CTTTTTTTGCTTTTTTTTGTTGTTGTCTGTTTTTTTAATTCAATCTGACAA
CCTCTGCTTTTGTATTAGAGTATTTAGATCATTTACCTTAAGTGTGATAAT
CTATATGGGTAGAGTTAAGTCTATCATCTTGCTATTACTTTCCCATTTGTC
CCATCTGTTCTTTGTTCTCTTTTTCCTCTTTTTTTTCCCATCTGTTGAACA
ACTTAAATATTTTTTCTCATTCTATTTTATTTCTTTTTGTGGCTTGTTAGC
CATAATTCTTCGTTTCATTATTTCAGTGGTTGCCTTAGAGTTTATAGTATA
CATCATTAATTTATCGTAGTTCATCTAAAAGTATACCACTTATATAAAATA
ACATTATTTTCATTTCCACTTCTTTTGCACTGTTGTTGTCATACACTTTTC
TTTTGTGTGTGTGTGTGTGTGACAGAGTCTAGCTCTGTTGCCTAGGCTG
GAGCACAGTGGTATAATTTTGCCTCACTGCAACTTCCACCTCCTGGATTCA
AGTGATTCTTGTGCCTCAGCCTCCAGAGTAGCTGGGATTACAGGCGTGCAC
CACCACGCCTGGTTAATTTTTGTATTTTTAGTAGAGATGGGGTTTTGCCAT
GTTAGCCAGGCTGGTCTTGAACTCCTGTCCTCAAGTGATCTGCACGCCTCG
GCCTCCAAAAGTGCTGGGATTACAGGCACGAACCTTTGTGCCCGGCCTGTT
TTACTTTTAAATGCTATAAATCACACATTACATTGTTAACTATTTTGTGA
AAATAGTCAACCACATTTTATGGAGAAAAAATATTATCTGTTTACTCACAT
AGTTACAATTTTCTAGTACTGTTTATTCCTTTGTATAAATAGGAATTTCAA
TATGCCTAAGGGACTTTTATCATTCTGCCTAAAGGACTTTTAAAAAATATT
```

FIG. 8-24

```
TTTTATTGTTCTAGTCTGCTGATTAGATGTTTATTGCCTTTAGGCAGGGAG
ATAAAAAAATACTACAATATTTTAGTTAATGACTGTGTCAATCAAAAAGAA
GCAAGACAATCTACCATTTAATTGCACGGTTGATTTTTTAAATGAAATAGA
AAACATCCACATATACAGTACAAAATGTATCATAAAACTCTCACATATGAC
TAGATAAATTCCTTCCTCTTTTCTCTGTATTAAATTGTCTTATTTCACCCT
CATTTGGGGGGAGTTTTTTTGCTTGGTACAGAATTGTAGGTCTTTCATTAA
TCTAAAAAATTTTGCTCCACTGTCTTTTTGCTTATATTGTGTCTATGAGAA
ATATGTGATCTATACACTTGTTCTTCTGTACATAATGTGCCTTTTGTTCTT
GGCTGCTTTGAAATTTTTCATTTTCCTCTTGCTTGCTTTGGGTTTGATTTG
TTCTTATTTTTCTAGTTTCTTTTTTTTTTAATTTTGAGACGGAGTCTCG
CTCTGTCTCCCAGGCTGGAATGCAGTGGCGCGATCTCAGCTCACTGCAATC
TCTGCCTCCTGGGTTCAAGTGATTCTCCTGCCTCAGTGTCCCGAGTAGCTG
GGACTACAGGCAGATGCCACCAGGCCTGGCTAATTTTTGTATTTTGTTAGT
AGAGACAGGGTTTCACCATGTTGGTCAGGCTGGTCTCAAACTCCTGACCTC
GTGATCTGTCCGCCTTGGCCTCCCAAAGTGCTGGGATTACAGGCGTGAGCC
ATCACGCCCAGCCTAGTTATTGATTTCTATCTTCATTCCACTTTGGTCAGA
GAATATATACTCTATTATTATAGTCCTTTTACATTTATTGAGACTTATTTC
ATGAAGTAATATACAGTCTATCCTGAAAAATGTTTCATGTGAGCTTCAGAA
GGATGTTTATTCTGCTGTTTTGGGGTGTAGTGACCTATAGATTTATGTTAG
GGTCAGGTTAGGTGTTTTCAAGTGTTAAGTCTTCTATTTTTTGTTGATCT
TGTCTAACTAGTGAGGTATTGATGTCTCCAACTATTATTGTCGAATTTTCT
ATTTCTCCCTTCAATTCTGTCAGTTTTGTTTCATGAATATTAGGGCTCTGT
TGTTAGGTGCATGTATGTTTATAATGTTATGTTTTCTTGATGAATTGACAC
TTTTATCATTACAAAATACCTTTCTTTATTTATTATAACAATGCTTATCTT
AAAGTTTATTTTGTCTGATATTAGTATACCTACTCCAGACATCTTTTGAGT
ACTATTTGTATGTGATGAATTGTTCCTTTCTTTCTGCTCTCAAGATTCATC
TTCTTCATCTTTTGATAATCTGATTATGATGTGTCTAGGTATGGATCTCTT
TGAGTGTATCCTACTTGGAATTCATTGAGCTCCTAAAATATGTATGCAAGT
TAATGCTTTTTTGCCAAACATGGGAAGCTTTGAGAAATTATTTCTCCAAAC
ATTCTCTCTCCCTGTCCTCTCACTTTTCTCCTTCTAGGAGTCCCATTATGC
ATATATTAGTATGCTTGATGGTATCCCCTGTCTCTAAGGCTCTATTTCTTT
TTCTTCATTCTGTCTTCTTTCTGTTTTTCAGAGTAGATCATTTCAATTGAC
CTATCTTTGAGTTCACTGATTACTTCTTTTTGCTGCTCAAATTTGCTGTTA
AAGCCCTCTAGTAATTTTTTTTTCTTACAGATGAGATATCATGCTGTCGTT
CAGGCTGGAGTGACCATGATCCTCTTACTGGGATCACAGATCACGCATGCT
CCAGTCTGAGCAGCAGCATGAGCTCCAGCTTGCTCCAGCCTGAACAGCAGC
AATACATTCTTTCACACACAAAAGGGTTATTGGATCTCACACAAGAAGGAA
TTTGGGGCTAGTCCATACAGTAAAGTGAAAACAAGTTTATTAAGAAAGTAA
AGAAGGGCCGAGCGCAGTGATTTATGCCTGTAATCACAGCACTTTGGGAGG
CTGAGGCAGGCAGACCACTTGAGGTTAGGAGTTCGAGACAAGCCTGACAAA
CATGGCAAGACACTGTCTCTACTAAAAATACAAAATTAGCTGGGTGTAGTG
GCACATGTCTGTAGTCCCAGCTCCTCAGGAGACTGAGGCAGAAGAATCGCT
TGAACCCAGGAGGCAGAGGTTGCAGTGAACCAAGATCGCACCACTGCACTC
CAGCCTCTAGCCTGGGTGACAGAGTGAGACTCTGTCTCAAAAAAACAAAAA
AAAGTTAAGAAATAAAAGAATGGGTCATGCATAGTGGGTAATGCCTGTAAT
CCTAGCACTTTGGGAGGCCAAGGCAAGTGGATCGCTTGAGGCCAGGAGTTC
```

FIG. 8-25

```
GAGACCAGCCTGGCCAACATGGCGAAACCCCATCTCTACTAATAATACAAA
AATTAGCCAGGCATGGTGGCACCCACCTGTGGTCCCAGCTAGTTGGGAGGC
TGAGGCAGGAGAATTGCTTGAACCCGGGAGGTGAAGGTTGCAGTGAGCCAA
AACACGTCACTGCACTCCAGACTCCAGCCTGAGTGACAGAGCGAGTCTTTA
TCTAAAAAATAAAAATAAAAGAAAAGAATGGCTACTCCATAGGCAGAGCAG
CAGTATGGACTGCTCAAATAAGCAGACGTATAGTTATTTCTGGATTATGTG
CTAAACTAATGGATTATTCAAGAATTTTTCAGGAAAGAGGTGGACAATTCC
CAGAACTAAGGGTTCTTCCCCGTTTTAGACCATATAAGGTAACGTCCAGAT
GTTGTCATGGTATTTGTAAACTGTCGTGGCACTGGTGGGAGTGTCTTGTAG
CATGCTAATGCAGTATAATTAGTGTATATGAGCAGTGAGGATGACAAGAGG
TCACTTTTGTGGCCATGTTGGTTTTGGTGGGCTTTAGCTGGCTTCTTTACC
GTTACCTATTTTATCAGCAAGGTCTTTGTGACGGGTACCTTGTGCAACCTT
CTATCTCATCCTGTGACTAAACTCCTGGTTAGAATGCCTAACCTAACCCAG
CAGGCCTCAGCCTTATTTTACCCAGCCCCTATTCAAGATGGAGTCACTCTG
ATTCAAATGCCTCTGACATATTTTCCCACTCCCTTTTACCAGGGAACCCTT
AATCCTAAGGATTGCAGTGGGATAAAGATCCGTCTTCTATAACTTCTTCAG
ACTAAATAGGGGCAATGATATTCCTGTCTAATTATTAGGGTCTCTTGTGTC
CAGGGTAGAGAGGAGCTCAGTCACAAAGTGTCAGTATGGTGAGACATTCAT
AACTCTGAGGCTTCCCAAAGTGTTGAGATTACAGGCGTGAGCCACTGTGCC
TGGCCAGGGTCCCATTTTTATACCAGATCCTGGATCCCAAAAGAGGGAATC
AGCCCTCTTTTGGGGGATCAGCCATCTCCCCTGGGAATCTTATCTCTCGGT
GGGGATGGAGACATTTCCATACCTTCTAGGTAGTCAAGAGAATGCTTCTTG
TGATCCAAAAGTGCAAATAGCCAAGTATTCACCTATATTTGCCTTTAGCTA
TCCCCAGAAGTATATTTCCTACCTGGTTATTACACACCAGATCTCCCTCAT
AATGCAAAGTAATTTCTGATACCCCCAAAAGTCAAAAACATCAGATAACAT
AATGCAAAGCCAAACAGAGCCTTAGATTTTGCGAAGGATCTATCCACTTCC
AGTTCCTGGGGTTTCATGAGGAAAACAGAGGTTTTCCCAAAATGGGGTCTG
TGGTGCCTCCTCTGCTTTTCCCAAGGAGTCCCAGGCTTTTAGAGATTGAAT
ATCCACTTTTAATTAAGCTTTTAACCATAAACCATAGCACTCTAAAGCAAA
AAAAAAAGGAGTCCTTTTAAGTTTCTTATTACTCAACTTTAGCCATCCCAC
ACGGCCATTATTTCTGGCTTTTGAACTTTACCAAAGATAATCTCCCAGGTT
CTCAGAGAGAGGAAAACTCAAGACAGTGTGTGGAGGGGAAGAGAACAGAAT
CAACAAATGGTAAAGGTCACACAGATATCAATCAGAAAGTACTCATTCCCT
AAGCCAGGATTGAACCTTGGCCGCCATTATAAAATGACAAATCCTTAGCTG
CTGAGCTACAACACTGGTTAGTTTCCATTGCCCTTCCCAGAAGGGGTCCAG
AGCAGCCAATTTTGAGCTTGCAATGGCTTGAGATAATTTTTAGAGTTAACT
ATTACATAAACCCCAAAATTCCTGTTCCCTGGATGGCAGAGACCAAGAGAA
AGTACCGCCACGTGGTTACAAGGTGAAGCTCCAAAGGACATAAAACAAGAT
GAGAAGGAAACTTCATCCAGTTTTTATTTTTTTTTTTTCCAGGGACCTGT
AATAAACTTTGCAACGGACCAGTTTACTGGGCTGGCTTGAACAGCAGGCTT
ATGGAGTCCTGAGCCCATGTTCTATCCTACCATATTCCTCTTTATGACAGA
GTAATACAGAAAGACAAATTGATATCACAAAGTATACCAGATTCATTACAG
CTTAAGACTAGCCCCACAAATCCTTGTTCCCATTAATCAAAACTTTACAGA
GGTGATAAACAGTGATTTTTACCATTCATTCAGTTTTCACTAAGAGAGAGA
GGCCAGAAGCCTGACTGGTAAGAAATCTTTACCCTTTTGCTGGCATGCCAG
GTTTCTGGGTTCTCTTTCACTGAGCAGCACTAGCAACCTTGCTCACTGCAA
```

FIG. 8-26

```
AGCCCTTGGGTCCAAGCTACGACACAAAAGAAAACCAACTTTTTTCTGTTT
CATGGAACCACAGGCAAATAAATGTCTCTCACTTTTGTAAGATGCTGCCCA
ATGGCCACATAAAGTAACCAAATTAACGTTTTCCATTTCAGCCAGAGCAAT
ATACATGTGACAAAACATAGACATTGGCCACTCCACTTAGCACCCAATATC
TAACTGGGAAGGCTCAAACTTGCCCCCAGATAGGCCCTTTCATCTTTAATC
AAACTTCTGACCAGGAGTTTCAACATATGGTCTCTGGGCAAGATGGTTGTC
TCAAGTAACAGAAAAGACAGAAAAGAGAAAAGAGAGAAAGGGAGAAAAGCA
TTGCCTGTGGTGAGATGGGGAAGGTGAGGAGTTCACAGAGGCCAGAGAAAG
ACCCACCCATTGCAGCAACACTGAATCAAAAGTTCAGGCGGCTGCTTGTCA
TAGCAAAGGGATCTTTTCCAACAGTCCTATCAGCTGTCAAGCTTCCCCTTT
TGGAGAGAAGAAAAGTTCCCAATGTCCCGTGATCCTGTACATGCCTAATCC
TGTCACCCATAGCTGTCAGCAAAGAGCACAGGGAAGATTAATACAAACAGA
ATAGCAGTTAACATCCCCTAATGCTAAATCCGTTTTTAACCAAGAGAGACT
TTACTGAGAGGGGCCTCTAACCCCTTAAATCTTAAGGACTGTAGCCTTCCT
AAGTTGGGTCTCAAACCCAAGTTCGGTCAAGCATTCTTGCCCTTTATTAAG
AGCGGACTGAAACCCTCTCTGTCTTAGGAGAGACCCTATCTCCCCTAAGTT
GCACCTCTAACCCAATCCTATCCTTTACCCGGGGACTCCACCACTTACCCA
AAGTCAGCCAGTTGGTGCTGTAGTCTGTTTCCTTTGGCTTCAGAGTCTCCT
CAGTATTGTCCCTTCGTGGTCACAGAAAGATTTACCAGAAANGGGTCTTGA
TCCAGACCCCAAGAGAGGGTTCTTGGATCTCACACAAGAAAGAATTTAGGG
CAAGTCCATACAGTAAAGTGAAAGCAGGTTTATTAAGAAAGTAAGGAAATA
AAAGAATGGCTACTCTGTAGGCAGAACAGCAGCGTGGTCTGCTCAAATAAG
CATACTTATAGTTATTTCTGGATTATGTGCTAAACAAGGGGTGGATTATTC
ATGAGCATTCCAAAAAAGGGGTGGACAATTCCCAAAATTGAGGGTTCCTCC
ACCTTTTAGACCATATAAGGTAAAGTCCAGATATTGCCGCAGTATTTGTAA
GCTGTCATGATGCTGGTAGGAGTGTCTTTTAGCATGTTAATACATTATAAT
TAACATATAATGAGCAGTGAAGACAACCAGAGGTCCCTTTGGTGGCCATGT
TGGTTTTGATGGGTTTTGGCCAACTTCTTTACCACAACCTATTTTATCAGC
AAGGTCTTTGTGATGTGTACCTTGTGCTGACTTCCTATCTCATCCTGTGAC
TAAGAATGCCTAACATACTGGAAATGCAGCCTAGCAGGTGTCAGCCTTATT
TTATCCAGCGCCTATTCAAGATAGAGTCATTCTGGTTCAAATGCCTCTGAC
AATGCAGCCTTGAATTCCTGGGCTGAAGCCATCTTCCCACTTCAGCCTCCT
GAGTAGCAGGGACTACAGGCACACACCATCATGCCTGGCTAATTTTTTTGT
ATTTTTTTTTTAGAGATGGGGTCTCACTGTGTTGCCCAGGCTGGTCTTGA
GCTCCTAGGCTAAAGCAATCCTCCTGTGTCATCCTCCCAAAGTGTTGGGCT
TGTCAGAGGTATTTGAACAAGAAAGACTCCATCTTGAATAGGAGCTGGGTG
AAATAAGGCTGAGTCCTGCTGGGCTGCATTCCCTGTAAGTTAGGCATTGTA
AGCCACAGGATGAGGCAGGCAGTGGGCACAAAATACAGGTCATAAAGACCT
TGCTGATAAAACAGGTTGCAGTAAAGAAGCCGGCTAGGCCAGGTGGGGTGG
CTCACACCTATAAGCCCAGCACTTTGGGAGGCTAAGGTGGCTGGATGGCTT
GAGCGCAGGAGTTGGAGATCAGCGTAGGCAACATGGCGAAACCCGGTCTCT
ATTAAAAATATAAAAAATTAGCTGGGTGTGGTGGCACATGCCTGTAATCCC
AGCTACTTGGGAGGCTGAGGCACGAGAATCGCTTGAACTCAGAAATTGGAG
GTTTCAGTGAGCTGAGATCGTGCCACTGCACTCCAGCCTGGGCAAAAAAAA
AAAAGAAAAAAGTAAAGAAGCTGGCTAAACCCCACCAAATCCAAGATGGCG
ATGAGAGTGACCTCTGGTCATCCTCACTGCTCCCCACCAAATCCAAGATGG
```

FIG. 8-27

```
CGATGAGAGTGACCTCTGGTCGTCCTCACTGCTATGCTCATACCAGCGCCA
CGACAGTTTACGAATGCCATGGCAACGTCAGGAAGTTACTTTATATGGTCT
AAAAAATGGAGGCATGAATTATCCACCCCTTGTTTAGCACATAATCAAGAA
ATAACCATAAAAATGAGCGACCAGCAGCCCTCAGAGCTGCTCTGCCTATGG
AGTAGCCGTTCTTTTATTCCTCTACTTTCTTAATAAACTTGCTTTCACTTT
ACAGACTCGCCCGAATTCTTTCTTGTGTGAGATCCAAGAACCCTCTCTTGG
GGTCTGGATCTGGACGGACCCCTTTCCGGTAACAGGATTACAGGTGTGAGT
GAGCCACCATCCCCAGCCTTAGTAAATTTTTATTTCAGTTATTATATATTT
TTATTTATTTTCTGTTTTTCAGTTATTATATTTGAAACTCCAGAATTTTTA
TTTAGAATGTATTAACAAATCAGGAGTACTGGCATAAGCCTGGCACAAAGC
AAATGTTGACATAGGTCTGGCACAAAACAAGTGTTCAATGCATTTTAGCTA
CCTTTAAGTGTATTATTACTAGCTGCTTCTGGGGCTATCCGGGGAAAATTA
TCCTTGCAAAACCCCCACTCACTTCCAGAGCAGGCTTCAGTGAAGCAGTCA
TCTGTGTCATGACAAGAGCCAAACTCTGTAAAACATTTGAAGAGATTTATT
CTGAGCCAAATTTGAGTGACCATGGCCCATGACACAGCCCTCAGGAGGTCC
TGAGAACAAGCGCTCAAGGTGGTTGGGATGCACCTTGGCTTTATACATTTT
AGGGAGGCATGGGACATCAATCAAATACGTTTAAGAAATGTACACTGGTTT
GGTCCAGAGAGGCGGGACAACTGGAAGCAGCGGAGGAGTGGGGTGGAGGTG
ATGACAATTGGTTGAGTTTGTATAAAGATTTGGGATTAATAGAAAGGAGCA
CTAGGTTGTGATAACAGGTTGTGAAGACCAAAGTTGTACTATGGGATGAAG
TTTTTAGCTAGCAGGCTTCAGAGAGAATAGGTTGTAAAATGTTCTTATCAG
ACTTAAAAGCTGTGTTGATGTTAATGCCAGAGAGGAATAATGAGGCATGTT
CAACCCCCACTTCCCTTAATGGCCTGAGCCAGTCTTTCAGGTTACATTTTA
AGAAGCCTGACTGAAGAGAAAGTCTATTCAGATGGTTGGGGGCTTTAGAAT
TTTATTTTTGTTTTATACCTTTGCCCTTGGAAGTTTTGCTGAAAAATGAAC
ACAAAAAAAGGCAGATTCATAAGATAAAAGGCTTTACAATTTAATTACTCT
GTGGTTCTCCTCATGCACATAGTACCAATATCCCAGTGGAATTTAGAAGCT
TATATGCCACCTTGAAGTTGAAGAAATAACAGGGGCTTGATCCTTGCAAAA
TAGGTTATGGGAAACAGAAGAAGAGGAATTCTGTTGAGGGGCAATATGTAA
CTACCAGGAGAGACTAATTGGATCAAAGAACAGATAAATTTGTAAATAGTT
CTCCTTGGAATTTAAATGATGCTTAGAGACTGATTATCTTATAAAAGGGTC
TGTTCAGGTGTGGTTACATTCTTGGTCTTTCCTATAATGCACAATGAGATA
ACAGAGAGGGAGAAAAGAACAATTGTTCTCGCTGGTGGGGCCATCCTATTT
TTATGTACCTAGGGAAAAGTCTCTTTAGTGTCTGTTGATCTCTAAGAGTTT
TTCATTCAAAATACTCATTATATCAGGAAGCCACATTTTGGGGTGAAATTC
ACTACTCCCTTTTAGAGATACGGGTACAAACTGTTTGTAAAGAATGCTAAG
ACTTTGCCGGGTGCAGTGACTCACGCCTGTAATCCCAGCACTATGGAGGGG
CCAAGGTGGGCAGATCACTTGAGGTCAGGAGTTCAAGACCTGCCTGGTTAA
CATGGCAAAACCCCATCTCTATTAAAAAAAACAAAAATTAGCCAGGCGTGG
TGGTGGGCATCTGTAATCCCAGCTACTTGGGAGGCTGAAGGCAGGGAGAAT
TGCTTGAGCCTGGGAGGCAGCTGTTGCAGTGAGCCGAGATCACGCCACTGA
ACTTCAGCCTGGGCAACACAGCGAGACTGTCTCAAAAAAAAAAAAAAAATG
CTAAGACTTACTTTGGGACATCCTTTGTCAGGGTCCATGATTCTGATTAGC
TCAAGGCAGGTATTTTTTTTTTAATAGAGACAGCATCTTGCTATGTTGG
CCAGGCTCGTCTCGAACTCCTGGCCTCCAGTGACTCCCCCCACCTCAGCCT
CCCCAAGTGCTGTGATTACAGGTGTGAGCCACCACACCGGTCTGGTTTTTT
```

FIG. 8-28

```
TTGGTGGTTGTTGTTTTAATCCTATAATCCTGTGTCCTTTCTTCCTACCTC
TGAGTAGTGCTTACTCTCTCCCCTTTAGTCATTTGAAAAGTTTATCAGAAA
GTGGGTGCAGTTTCAGGCTGGGTACCGTGGCTCATGCCTGTAATCCCAACA
CTTTGAAATGCTTAGATGGGAGGATCATTTGAACCCAGTTCAAGATTACAG
TGAGCTGTGATCGTACCATTGTACTTCAGCCAGGGTGACAGTGCAAGAGCC
TGTCTCTAAAAACAAACAAAAAATTGCTTTCACACTGTGATGCTATCACAT
CTCTCCTAAGCTCTTGTTGGGGCTCAGAAATTGATACCCTAATATATGGCC
CTTGGTCATATTGAACTGAAGAAGCCTCAAAGTCTCTCTGACATCCCTGCC
ACCAACTATCCCTACCAAAACACATCGTGGAATTAAAGTTTCTTTATCTAC
CTAAGATCCAGACCCACCAAAAAGAGCAATTATTTTTATTTACCCTTCCTG
TAAGACCAAGAATGTAACCATGCCCGAACGGACTTTCACAAGATAATGTTC
AAGTTAATCTCTGTTCCCTGATCTACTTACTCTCCCTAGTAATGAAAGGAG
TTGGCCAGCTTGCTTTAGGCAGACAGTAAGGGAATGGTACCCAGAGAACCT
CTGACCTGCCCCACAAGTGCTTACACCGGATGTTTTGTGCAGATAAGGGAA
CTTGCACAGGGGGCTTGCCTAAACATGCCTGCAGTGGATGATTCCTTTCCT
TAACACATGCACAGTTCAGGAAATTAATCAATATGGAGTAGCTCAGTCTAA
AGGCCTGCATGCACTGGTAGGACAGGGTGGAGTTGTCAGGAATTTGAGTCT
TAAGCCCTAGTATTCAACTGTGAAGAGCAAACCAGAAATCTGCTTTCAGGA
CCCTTGTCTTTGCTGAGAGCTTTCCTTTCACTTAATAAATTCTACTCCACT
CATTCTTTGATGGCTGCATGCCTAATTCTTCCTGGCTGTGAGACAAAAACC
CGGACCTAGCTGAGCGAAGGAGCAAAAATCCGCAACAGTAATCCCATCAAC
AGAGTTTCTCTTCTTCCCCTCCCATAATCTGTTTTGCCAGGATAATATATA
AGCTTTTAAGCCCTCTTGGGAAGTGGATAATCATTCTATGGTTCTCCCTGT
GTACATGTTAATAAATTTGTGAGTTGATTTTTCAGCAAAGTTTCCCCAGAA
GCCAAAGGGGAAATTTCCCTTGGCCCCTCCACTCTCTTTTCCCAGCTCTTC
TTTTACTTTCGTTTTTATTTCCTCAGCCCAGTAGGTCACAGCCTTCTTTTT
ATTTCTTCTCTGTCCAAACCATCAGTATATCCTACAGGTGGGAGAGAAGCA
GCTCTCTGGGAAACCAGTAAGCACCATGAGTTCTGATACTTTCTAGTACCA
TTTGACATATTAACATCCCCGCCACCCCTAATATGTATGGACACGCACACA
CATACCACATCACATGCATCACACTAACACAAACTATGTATCACATACCAC
ACACAGCACACACAGTACCACATACCCCACACAACACCCACACCACACTAC
GTGCATCATGCACATATGTGCACACACCTCTTGTGATGTGTGTTTAGTGCA
ATTCAGAAAGTTACTCTTTGATTTAATGCACATCACTATGCTTAGAAATAT
TCTAGTTACTGGGATTCATCAGTGAACAATATTGAAAAAAATCCATCCCTT
TGCATTCTCATGAGGGAAGCAAACACTAAACAAAATAAATTAGTAAAATAT
TCAGTGATAAGTGCCATGGGAACAAAATAGATTTGAAAATGTTTGGGAGGG
AGAGAGGGGTACACTTGCTAACAAGTGGTCAGGATAGGGTTAGTTGAGAGG
CAAAATCTGAAGGAGTTGAGGAAAGGCATTCTAGGAATAGCTGAGTGCTGA
CTCTTGCCCACAGTGGGAACACACAGTACAGAGCTTCTGAAGGAGACTCTA
GTGACCTACTTCCCATTGTGAGTCTTTGGACTCCTATATCCCATAATCACA
GGATCAAGCCTAACTTTACATATTAGAGATAATGCATTCCTCCTTGGGGAT
AGTTCAGGTTGATTTCTCCCTAGGCCTGCCTTTGTCAACATATTCCTGAAG
TCTCATCTGCACCCCATCTCTGCTTCTAATATTGGCCACTCTGTGCATGAA
CCAGCCCCTCCTTCCTGCAATGGGAAACAGGTGTGAGATGGGACAGCTGTC
ACAATCCGTTTTGCTTTTGTCTTGCTGTTATTATTGGTAATGGTAGTTTGT
TTCCTTTTTAGCATTCACTAGCTTCCTTTTCCTGATCCTTTGATAGTGTTA
```

FIG. 8-29

```
CCAGAAAGGGGGTCCCAACCCAGACCCTAAGAGAAGTTCTTAGATCTCGTG
TGAGAAAGAATTTGGGGCAAGTCTACACAGTAAAGTGAAAGCAAGAAAGTA
AAGGAATAAAAGAACGGCTACTCTACAGGCAGAGCATCAGCTTCTGGACTA
AGGATACTGATATGGTTTGGCTGTGTCCCCACCTAACTCTCATCTTAAATT
CCCACATATTGTGGGAGGGACCTGGTGGGAGGTAATTGAATCATGGGGGCA
GGTCTTTCCCTGAGTAATTTATACTGCTGTTCTCATGATAGTCAATAAGTT
TCATGAGACCTGATGGTTTTATAGAAAGGAATTTCCCTGCACAAGCTCTTT
GCCTGCTGCCATCCATGTAAGACCTGACTTGCTCCTCCTTGCCTTCTGCTG
TGGTTGTGAGGTCTCCCCAGACACGTGGGACTGTAAGAGCATGAAACATTT
TTTCCTGGTATAAATTACTCAGTCTCAGGTATGTCTGGATCAGCAGTGTGA
AAATGGACTAATACAGATACTTACAGTTATTTCTTGATTATGTACTAAACA
AGGAGTGGATTATTCATATGTTTTCTGGGAAAGATGTGGGCAATTCCCAGA
ACCAAGCGTTCCTCCCCTTTTTAGACTATATAGGGTAGCTTCCTGACATCG
CCATGGTATTTATAAACCACTATGGAGCTGGTGGGAATGCCTTCTAACTTG
CTAACACATTATAATTCGTGTATAATGAGCAATGAGAATGACTAGAGGCCA
CTCTTGTTGCCATCTTGATTTTGGTGGGTTTTGGTCAGCTTCTTTACTGCA
ACCTGTTTTATCAGCAAGATCTTTATGACCTGTGTCTTGTGCCAACTGCCT
ATTTCATCCTGTGACTTACAATGCCTAACTTCCTGGGAATGCAGCCCAGTA
GGTCTCAGCCTTATTTTACCTAGCCCCCATTCAAAATGGAGTCATTCTGGT
TTGAACACCTCTGACAATAGGACAGATCTGGAATGAGCCATGCCTGGGTAC
AGAGTCACATCCACAACAATGAAAGTTGTAGATATCTGCAAGGACTCATCG
TGGGACCAAGGATTCAGGGGCTCATTCTTTCTCCTCTCTCTGTGTGCTGGT
TGCCTCAGGAGTAGAATGTCCCATGCTATGCATGGGGTCTGCAACCATCAT
GCCAGGGCATGATGAATCGTAGGTGGCAAAACAACAGAAGGCTCTGTGAGC
ACCCAGGAGGGTGCAGTGCTGAAGAGTCTTCTGCTTGGTATAGGAAGAAAG
GAACGTGTTTCCCAATCTTGCCTTTATTTTGAGTAGTTGGACCAGAGGGAT
TGCAGCTGGGCCAAACTCCATGTTCCATTGGCTATCAGGGTCAGCAGGCAG
GCCAGGGGCCCAGACAGGCCAGTGGCTCCCAGAATTCAAGTTTAATTTCTC
CTCCCACCTGTGTCCTGAGCTCCCCTTACTGGTTCCCTTGGACCACTGCAT
CTACTTAAGCCAGCATTTATTATGTTGTTATCATAAATGCCTCTTACACCT
GAGACTTATAAATGTGACAAGCTCTTATTGTGAGATAGTAATCCATCTTTT
TTCCCCATGAAATAATAATTCTAACGGGTGGTGATAGTACTTTTCCTTTCA
TTTTGAAGTGGAGAAGCTGGAGCTAAGTCATTAAGGACTTGACCCTGGACC
CCACAGCCTTTTCTCCACAAAGCACAAAGCAGAGTGATGGTCCCAGGGATC
CCACACAGCTCTAAGCTGGGGGCACTCACTGCTGGGCCACTAGTGACTCCC
ATTTTCTATCCTGGCTGACCCTCGCTATTGAAGAAGATCTGAGTCCTGCAG
AAGGACAGCAAGGAGAAAAACAAGACACAGAACGGGACAGAGAAGAATAGA
AAGCTGACTCAGATGAATTTTGTGATGCCAATGAGTCCTACTGCTGTTACC
ACCCCTTTTTCCACCACACCCTTCAGAGCAGTTATAGAACCACAAGCAACC
CATAAATAGCAAAAGAAGTAACATCAGCTAGGAAGGCTTAAGGACTCCCAA
GGGAGTTGGTGGCAAAAGTAGAAAGATCTCAAATCAGAGTCTGTGAACTGA
ACCTCTGCAGGCTTCCTGTTTTTAGATACTCTGTGTTGGGGTCACATGATA
GTTTACAGGGTTATTAATTGGTTCCTTCTTTTTATTGCTGTAAAAGAAGGA
TATTTCTTCCTACGTTTCCCCCTCCTTTACCGGAGAGGCGGAGTGCAAAT
GATATGAACAACGTCACTAGTTTTCTCCTAAATCTTATGAGCCCCGCCTCC
CACAGTAGTTTCACTTCTCAGTTTAATCCGGTCTGAGTTAACTTCCTGACC
```

FIG. 8-30

```
CAGGAAGTGGCAGCAACAGAGGGGACTAGCAGCGAATATGTAAGTGTCTGA
GCAGTGAAGGTTACGGAAAAGGTCCAGGCTAAGGTTTTCTCAGTGGATATG
TGAGTGTGTACTGATGGCAAGTGGGGTGGGGAATATATTTCGTGACAGCAG
GGCCCCTCCAACTCTGAAAATGGTCAGGACTTTCTTTGTTTTACAGCTCTC
ACCTCTTTCCTGCTCTTTCTTTCACCAGACTTTACACCAAATCTCAGAAGA
TTCAGAACTTAGATGAGTGGGGCCCAGGACAGGAACCCTGGAGCCTTGGAA
GGAGGGGAGCCCCATCTCCCCAGAAGAGCAGTGACCCCAGCAGAGAGGGGC
CTGGTGTATCACTGGAGGAAATAGCCTGCCAAGGAATACACGTCTTCAGAA
GAAATTCTGTGTGGCTTCAAGAGACTGATCAAATTGTGAGAGGAAAACAGC
CTACCCGGTAATTGTAGTTAAATTACTGTTTTTTATTCTAGGCACTCTTCA
AACTTCCTCCTGACTCTGCCCCTGTCCTAGAGGAGCTCCCAGGAGTAGGGG
TGTGGGGGCGGGCGGGGGGAGGGATCGGGGGTACAGGGAGAGCCCAGCTA
GGTTCTCAGAAGAGGCAGGCTTTTTCGCTCCTGGTCACTCCTCTGTTGCCT
ATCCCTGGCCTCCCCCATCTTCTTTCTGCCTTCCCTACCTCCTTGGGTCTG
CAAACTCTTTATGTTGCAATCACTCTGAACATGTCTCTTGAGATAGGTCCT
GTCCTGGAGAAGAGATAGTAAAAGTAAACTCCCCAGTTCTGCAGGAGCTCT
GATCCCATAGAAATAACTGCTCCTCAGGAGCAAACCCTCTGCTCTGCAGCC
TTCTTTCCAATTCTTATTCCCTCAGTTTAGGGAGAGGGCACAAAAAGGATA
AACCGGTTCTTCTGGTTGTTCTGGTTGCCTTGATTGCTTCCATTATCCTCC
TGGTTGGGTCTCTAGCAAGACGTTATTAGCCAGGGAAGTCCCACTTAGGCA
CCCCTCTCTGCAGAAGAGGTATTCACTATTCTCCTTTCTCTTTCTTTTGCC
TATTATACCTCTGCTCCTGAAAGCAAAAACAACAACAACAAAAACACAAAC
AAAAAACAACCGACCTTATTAACCAGTGTTGGTTGTTGTTCTTTGTGGGGG
ATGGGGGGGGTCGAGGTGGAGTCAAATTTTATTGTCATGATGGTGTAGGAG
CCAAGGGAACACTTCCCCTTTGCCTTCTGAAGTTCACTGAAAAATCGACTC
ACAAAAGGCAGGCTAATTGGAGAAAAGGCATACAAATTTATTAACAAGTAC
ATGGGCTAGAATCACAGAGTGATTACCCCCTCTGCCAATGGGGGTAGATAC
TTATATAGCCTTATTTATAAATACTTATGTATAAATACATAAATATAAATA
TGTATGCATATGTATGTATGTATAAATATGTATGTATACTGTATAAATATG
TATGTATAACGTTTATACATGTATACATATTTATTTCAGAGGGGAAGGGTG
ATATCAGGAGAATATAGGTAATTCTTTGAGGGGCAGTAAATGATTACTAGG
GAGAATAAATGAATATTTGGGAGGATGAATGAATGGAGGAACAGAGTTTAA
CTTGTAAATGTTCTCTTTGGAAAATGAATGAGCCTGAGAGACAGACATTAT
TTTGTGAAAGTGTCTGATTAGGTCTGGTAACATTCTTAGTCCTCTTTTCTT
CAGTACAAAATGAGATAATAGGGGTTGGAAGGAAAAACAATTGTTCTTCTT
GTCTAGTGTGACTGGTCTTTATGTAGATAGGGGAAAAGTCTCTTCCAGCAT
CTGCTGATCTCTAAGGGCCTTTAATTCAAAATACTCATTATACCAGGGAGT
CATATATTGGGGTGAAGCTCCCCATACTCCTTCAATGGAATCTGTCACAGA
TCACCCAATTGCATAAGTGTTACTACTAATTACAAAGAGTAATTCTGGTAC
CAATTATTCTTTTTTTTTTTTTAAGACAGATTCTCGCTCTTTCACCCAGG
CTGGAGTGCAGTGGTGTAATCTGGGCTCACTGCAACCTCCCCCTCCGGAGC
TCAAGTCATTCTCCTTCCTCAGCCTCCTGAGCAGCTGGGATTACAGGTGTG
CACCACCACATCTAGCTAACTTTTTGTATTTTTAGTAGAGATGAGGTTTTG
CCATGTTGGTCAGGCTGGTCTCAAACTCCTGACCTCAGGTGATCTGCCCGC
CTCGGCTTCCCAAAGTGCTAGGATTACAGGCGTGAGCCACCGTGCTGGCCT
GGTAACAATTATTCTTGAAGTTAACTAGAATAGGAAAGAGTTTCACACTCC
```

FIG. 8-31

```
CTGAGTTCTCTCTTTTACAGCTTTTGTGAGGAAGCCTGCATTGCTTCTCCC
AGCACTTGGTCCAAGGTAACTTTCTGTGATAACAGAATGTTGTATATTGAG
GCTGTTATGTAGCCACTAGTCACATGCAACTATTAAGCAATCAAAATGTGG
CAACTGGAACAGAAAAACTGAATTTTTTCATTTTAATTTTTATTAAGTTAA
ATTTAAATTCCTACTCATGATAGTGGCTACTGTATTAGCTATACAGCTAGA
TGTTTGTGTATCCTCTAAATTCCAATGCATTTCTTCTTTCTGGAGAGAAGA
CTTTAGCTGGACATGGTGGCACATACCTGTAGTCCCAGCCACTCTGCCAGG
GTGAGGCAGGAGGATTGCTTAAACCCAGGAGGTCGAGGCTGCAGTGAGCTG
TGGTCATGCCACTGCCCTCCACTACAGCCTGGGCAAGAGAGCGAGAACTTG
TCTTATAAGAAAAGAAAAAGAGGCTGGGCACGGTGGCTCATGCCTGTAATC
CTGGCACTTTGGGAGGCTGAGGCGGGTGGATCACAAGGTCAAGAGATCGAG
CCAACCAACATGGTGAAACCCCATCTCTACTAAAAATACAAAAATTAGCTG
GGCGTAGTGGTGCACACCTGTAGACCCAGCTACTACTCGGGAGGCTGAGGC
AGGAGAATCGCTTGAACCCGGGAGGCGGAGGTGCAGTGAGCCGAGATAGCG
TCACTGCACTCCAGCCTGGGTGACAGAGTGAGACTCCGTCTCATTAAAAAA
AAAAAAAAAAGTTAGAAGACTGAGAAAAGAAAAATAATGAAATAATTTAGA
GCAGTCTGAGCTATGTGAGGTATGCAAAATTTATCAGGACAAGTGAGGCAG
GAGTATAGGTCTTCCAGTTAAGACCCCATGTTTTAAAAGCATTTTGTTCCT
GACTGGCTGCCTCATCTATTACCTACATATTCCCGAGATTTGTTAATACAA
AGAAACAATGTTATAGCCAGTCCAAAAGCTTATGCTATTTTAATGTTAAAT
CCTTGGCAAACAACTTTAAAACTGCTTTAAACTGCTTTTTTCCTCTAACAC
ACTTGTACTGCTTGCTAATGAGGCACTTGAACTCTGCACTTGGTTGCAGTT
TCTCAAAGTGCCCCAAACAACCTTCACTCAATTTCTTCCTTTTAGTTCCTC
TTTTCTTCAATACAAAATGAGATAATAGGGGTTGGAAGGAAAACTTTCAAG
ACCTATGGAAGTCAGTTGCAGCCAGCTCATCACATAGAGGTGCAGGTGAGG
TGTATTTTCATCACGGTGGAAAATTCTGGCTGCTTCATCTCCATCTCTAGA
GCCAATATTGGAGCTTTTCAATAAAAGCTATGGCCTCAACCACCAGCACCA
AGAAGATGATGGAGGAAGCCACCTGCTCCATCTGCCTGAGCCTGATGACGA
ACCCAGTAAGCATCAACTGTGGACACAGCTACTGCCACTTGTGTATAACAG
ACTTCTTTAAAAACCCAAGCCAAAAGCAACTGAGGCAGGAGACATTCTGCT
GTCCCCAGTGTCGGGCTCCATTTCATATGGATAGCCTCCGACCCAACAAGC
AGCTGGGAAGCCTCATTGAAGCCCTCAAAGAGACGGATCAAGAAATGTCAT
GTGAGGAACACGGAGAGCAGTTCCACCTGTTCTGCGAAGACGAGGGGCAGC
TCATCTGCTGGCGCTGTGAGCGGGCACCACAGCACAAAGGGCACACCACAG
CTCTTGTTGAAGACGTATGCCAGGGCTACAAGGTGAGTGTGTGGGCCCGGG
AGCTTTGGTAAGTACCAAGTCTTATCCTGCTCCCCAGGAGCTGAGATGATT
TAACTTGAAACCTAACATTATGACTTGGAAATACAGCTTTCATCATGTCAT
TCTTCTGAAAAATAGTTTATGATGATTTCTTGCTCAATTATCTAGACTGTC
CATCCTGACCTTCAATGGGATGGTTGGACTCTTATCTCTATCCATTTGTGT
TATGATGAATTTCTTTTTGCTTTAGAACAGGTTGTTCTCAAACCAAACACC
CGCATTTTTCTTGTTTCACACCATGAATATCATTTGAAAAACCACAATAT
GTAAAGCCATGCAGTAGGGCCTGAAAACAGGGAAGAAAGACCCATCACCTT
TTAGGTATCTACAGTCTAGTAAAGAAAACAAACCATCAAAAATGTCTGCCT
GGAGGTCCCTGGTTTTGGTGGTGGGGAGGGACATTTAGGGTAGAGAGTGGT
TCATCTTAGAAGTAACTCCTGAAGGACACGTAAAAATTGAACACCTATTGG
GGGATTTTCATTTGGGGAATGAAGGGTCAGTGACATTGAAAATATCACTCT
```

FIG. 8-32

```
GGTACCTCTACTTTTTTTTTTTTTTTTTTTTTTTCCTGAGGTAGGGTC
TTGCTCTGTATCCCAGGTTGGAGTACAATGGTGCAATCTCGGCTCACTGCA
GCCTCAACCTTCTGGGGCTCAAGCAATCCTCCCACCTCAGCCTCCCAAGTA
GCTAGGACTACAGGGATGCCCCACCATACCTGGATAATTTTTTTATTTTTT
GTAGAGACATGGTCTGCCTTTCTTGCTTATACTGGCCTCAAACCCCTGGTC
TCCCTCCCATCTCAGCCTCCCAAAATGCTGGGATTAGAGGCATGAACCACT
GTGCCCAGCTACTGTGGCATGTCTATGATAAAAGGAATATCAAGGAGTAAA
ATTCAAACTATCCGTATAAGAAAGGGAGGAGAGGGCAGATTTTAAGCACGA
TTCAGGAAGAAGAGTCAAAGATTTGGAAATGCTTGGTTGTGGAAGGTGAAG
CAGAGGGAGAGGTTTTGTGTACCATCCAGATTTCTTGCCAGAAAGCATATT
AAGGAAGGTGGGACTTTGCTGTTGGCAGCATGGAGGAATGGGCATAGTCCT
GATGTCCTTTTTCCTTCTCTGTCCTGCCTAAATTTGAGGAAAATGTTGTCT
CCAGTGTCAGGCTCCTTATTCTGTCCTCCATGAGGCAGAGGTGGTCTTGTA
TGAAGGCTCTAAGTCCTTCTAAGGACATGTCAATCATGACCACCACTCAGC
TCATGGCAGCTCTTCCTTAAACTCCATGGAGCAGCTAATAACTGCGATGAT
CATATTCCCATTTGAATTACTTTTCCACCAAGTAGTAAGAAAAGGAACCAG
CTTATGTTGAAATTGAGTTTTGTCACTTACTAGATGGGCAATTTTGGGCAC
GTTACTTAATGTCTTCACACCTTGGTTTCTCCATCTGTAAATGGGGATAAT
AGCAGTGTCCTCCCTCCCTAAAACACATACACAGGAGGTGGTTATAAGCTT
TGAGGACATTAAAATATAGAATGCATAGAATAGCACTTGGCATATAGTAAG
GACAATGTCATCTTTTGCTAAAACAGTTACATAGAACCTTTTCCTGAGAAC
ACTCGAGAATGAATGAGTATACTTGTTGGGTTTACAGAGGACAGGAGACAA
TTCTTTCAGCATTGACTACAATTAGCAATTTGGGTCAGCTTCAAATCACTT
TCAATAGAAATATGAGAAACTGTTTTGAAGAATAAGCTAAAAGCTTGACAT
GAATACTAAATCATTTTAAATTGGATTCATGATACCATTGTTCAAAAGATA
CCAGAATTCCCCTCTTCCATGAACTGTTTCTAATAACCAGCTGGCATCCTG
ATTTTTCCTGACTCATAAGACACAAAATTTCATGTTGTTGCCAAACACTGG
TATTGGTTTTGCTTGGTTCAGCATGTTGTTTTACAAAATCTTTTAGATGAT
GATTACCTTGTTCTATATCCAACTTTTTCCTGGCAGGACTCTAGTGGTGGA
CATAGCTCAGGCTCTGGGTCAGCAGATGAGATTGCAATTGTTGCTCCACCA
CCTGGCAGTCATAGCCCTTTGGGCAAGTTATTTTACCCCTTTCTTAGTCTC
ATTTCTACAGCACAGAAATGAAGTTTAAAATCCTACCAACTATTCAGGGT
TGCCAAGGGGATCAGTATGTTCCTGCACATATAGCCTTTAGCATGCTCTCT
AGCAAAAAACAATGAGGACTCTATAAATATTCACTATTATTCAAATATATC
TTAGAAGATTGGGATTCCCCCTAGGTCCCTAATGAAGAGTCAAATTGAATA
GGCTTCACTTATCAAATTTTTCCTTCAGGAAAAGCTCCAGAAAGCTGTGAC
AAAACTGAAGCAACTTGAAGACAGATGTACGGAGCAGAAGCTGTCCACAGC
AATGCGAATAACTAAATGGAAAGTAAGAATCTGACTTCATTGATCTCAAGC
TATTTTCCATTCTAGAGCTTAGGCATAGGGGATGATTGAGGAAAAGCACAA
TGAGGATTTATTCTCACTAAACCAGATTGAAAAAATGAAACCCAAGGAAGA
AACCATTATTTGTACTTATGCCCCTGGTTCCAGGTTTACATCCATGAGTAT
TTAGCACCAATCTTTCCATCTTTAAACTGTAGTTGGCTGGGATTCCTGATA
CTTCAGTCAGAAGAAGCAGAATTAGTATGACTATTTACCTAGAAAAAGCAT
CGAGTGGGTCTCAAACTTTAAATACGTCAAAATAAACCTGGTTTGCAGGCC
TCAACTCATTACCCTGGCACTTTTACCACAGTGGAGCATCTGGCTCTCAAC
TTTACAGGTACAGAAACCAAGCTTTGTGAACACTTAGAAAACAGGATCACT
```

FIG. 8-33

```
CCAGATTGAAATTCATACTACTCTAGCTCATGAAGCTGATGAAAGAAATAT
ACTTTATTTATTTATTTTTAAATTATTACTATTTTTGAGATGGAGT
CTTGCTGGAGTGTAGTGGTGCGATCTCAGCTCACTGCAATGTCCACCTCCC
GGGTTCAAGCAATTCCCCTGCCTCAGCCTCTTGAGTAGCTGGGATTACAGG
CATGTGCTACCATGCCTGGCTAATTTTTTGTATTTTAGTAGAGACGGGGTT
TCACCATGTTGGCCAGGATGGTCTTGATCTCCTGACCTCGTGATTCACCCA
CCTCAGCCTCCCAAAGTGCTGGGATTACAGGCGTGAGCCACTGCACCCGGC
CTATACTTGATTTATAAGTACATCACAAGTAATGCAACAACCTACACACTT
GCAACTACAAACTTTCAGATTATTTCCGTGGCTGACTAACCTCCACATTAT
CAGAGCCACATTCTTTTATGGAAATATTTAGGTTTGTGCAAAAGTAATTGC
GGTCTTTGCCATTAAAGTAAAGGCAAAAACCACAATTACTTTTGCACCAAT
CTTTATATTTATATAATTCACTAGCTTGCAGTAAAATCCCACAAGCTGATT
ACCAATTTTCTCTCTTTCAGGAGTCCTCTCTAACCTCTACCCTGATCTTTG
TTTGTGGATGTTGCTCTTGAGCTCCTGAGTACACTCTTACTTCCCCCATTT
CTAGGATCTTGGGCAATGGGGAAGACCTTGATTGTAACTAACATATATGAA
AACCCGTCTATACAAGAGTTAAAGCTGCACCTGTCTCCTACACAAAAATTC
CACCTCATCCTAAGTCAAAGACCCTTCTTCTATATCATAGTCATCAAAACA
CTGTATGAATTTATTTTTATTTTTAATTTTTATTTTTTAAGATAAGTAG
AGAGTTTATTTGGGCCAAGTTTGAAGACTGCAATCCAAGAACATAGATTCA
AATTGCCCTGAATACACACTCCCACTGCATTAATTTAGACAGCACTAATGG
AAATTGCAACTTTACATCTCCTCAGATGAGAGTTTCACTTGATTTCTGTCA
GTCTTACACATAGGAATGCTTAAGATGACCCTAGGGTAGTAGAACAGTATT
TCTCAGTTAACCATAATAAATGCCTGTCACACTCAAAGCTCCCCCTGCCAA
GAATTATGGACCCTCTTACCAGCCTGGTTGTCTTAAAATCCAGTCTGGGTG
ATGTTCATTATAAGCTTTTACTTCAAGAAAATCGCTCCAACTCAGAAATCT
AACTTCTTAAATCATAAGTAAAAACCTCTTTTTATCCTTGTAACTGATAAA
GTGTTTGAACTTGGCCCTAGTTTCACAATTAAATTATCTAGCACTCCTAAC
CCAGCTTTCTCCTGTGTCTTGGCTGAAGAACAAGAAAATTAATTGGGTGAC
TATAAGGAATCTGAGGCAACCTCTTCCACATCTGAGTGCCTGCCTCCCACA
CATGACTCTGCAGCAGGAAACTGGGGACATTCTTCCAGCTTCAGTGACTCA
TGAGAAAATAATGTCCCAGTGGCTGATTGTGTGTGTGTGTGTTTGTGTG
AAAATATATATAACACTTAAGCATTTAACCACTTTTAAGTATATAGTTCAG
TAGAATTAAGTGCTTTTACATTGTTACATTGTTGTGCAACCATCACCATTC
CCATCTCCAAACTGCAACTCAGTTTCATCTTTCATCTTCTAAACTGAAACT
CACTACCCATTAAACAATAACTGTCCATTTTCTGGTCTTGCCAACACCTTG
TAACCACTATTTTACTTTCTGTCTCTATGAACTTAACTACTCCAGATGCCT
TGTATAAGCAAAGTCTTACAATATTTGCCCTTTTGTTTCTGGCTTATTTTG
CTTGAATGTCTTCAAGGCTTGTCATGTAGTAGCGTGTGTCAGACTTTCATT
CTTGTTTATCCATTCATCCATAGATGGACATTTGGTTTACTTCCACCTTTT
GACCATACTTTCTTGACTCCAGGAGAAGGTACAGATTCAGAGACAAAAAAT
CCGGTCTGACTTTAAGAATCTCCAGTGTTTCCTACATGAGGAAGAGAAGTC
TTATCTCTGGAGGCTGGAGAAAGAAGAACAACAGACTCTGAGTAGACTGAG
GGACTATGAGGCTGGTCTGGGGCTGAAGAGCAATGAACTCAAGAGCCACAT
CCTGGAACTGGAGGAAAAATGTCAGGGCTCAGCCCAGAAATTGCTGCAGGT
GAGGCTGTGTACTTGGAGTAGGGAAAAAAGGTATGTTATAGTGCTATTAAA
GGAGAATGGTAAGGAAGCATGGGAAGATAAAGTAATGTTTCTTTTAGATGT
```

FIG. 8-34

```
ACATCAGTGCCATCAGGCTGGCCTTCACTAATTTATAGGGTACCTTTATGT
CAATTAGAAAAATAAACTTCTGAGGGAACACAGCTTGGCCAAATGAAACCA
CGGGATAACATTTACCACTGTTTGCCTCCTTGGCCCATGTGCAGAGAACCC
TGGTTGTTGACTCTCTCCTGAAATACTCCACTAGGTGACTGATGGGTGATG
AAGTGGGGCAGCCAAAATGAGTGATAACCTTTTCCCTGATTTGCTTGTAGA
ACCCTTGCTCCAGAGCTGTTATGGTACAATCTACAGCTTTATCTGTAGGAA
GATAAACATCTGGAGCCATTAATTCTGGTTCTAACAACAGGATTGGTGACT
ATACTGTAAGGCTGAGTGTATAGCATGATTGCTTTACCACTGTGTGATACC
TGCTACCACCATCTTAGTGGCAGTGGCCCAGTCTCAGGGCTGTGCACAGAT
TCACCACTAAGGACCTTTATGATAAGTGTTCTCTAATCTGGGCTCACTGTG
AAGGAAATCCGATCACCAAAAGCTAGTCCTTACAGAGGGAGCATGGACAAA
GCTCCTGGCCCTCAGACTTCAGCAAGGATGAGAATAGATGCAAATGTTGAT
AAACATCCTGCCATGCTGAATCTCCCAGAAGCTGGTAGGAATTATTCCATC
TGGGTATCCATCAATACCTAAGACTGGTGGGAATTACTTTGTTTGAGTATC
CATCAATATCTAAGACTAAGACTAGGGTAACTCTCTTTACTTCTTCGGGTA
AAGCAAAGAAGAATAGCCCTGCATGACAAGCCCCATGAAATACCGATGTTC
CCATGCTCACCTTTTCTTTTTGTTTCTTTATAGAATGTGAATGACACTTTG
AGCAGGTAAGTCCTGTTTGAATGCAGGAGGGGAGGGGTGTGCGTATATAGA
AATGAATGGAATGCACCTCTGAAGAAATCTCTCGCCTCTGCTTATTCTAGG
AGTTGGGCTGTGAAGCTGGAAACATCAGAGGCTGTCTCCTTGGAACTTCAT
ACTATGTGCAATGTTTCCAAGCTTTACTTCGATGTGAAGAAAATGTTAAGG
AGTCATCAAGGTATGTTCACTAAAGAATTCCTGAATACTGTGGATAGAAGG
GGCCTTATGCAGTAACCAAGTTTACCACCTGTCCCTTGGCAGGCTCACAGC
CAGAGAGGTTGTTTAGTTAATTTCAGTAGAGCTTTCATACTTTCTCTAGTT
AGTATGATTCACTGCTCAGTGAATGTGATGAGCATTGCATTCTGGTTATCT
GTGCAAACCTTTCAAATTCTTATTCTTTCACTTATTAGCCATGTTACTCCA
AGTGACTTGGTTTCCCCCTCTGAAAAATGAAAATATTAACAGCTCCTACTT
CATTGAGTTATCATCAAAATTAAATGCATCAACATGTACAAAGTGCTTAGC
CCTGTGACTGACACATGATCATAATAGCACATCATGGTATTAGATCTGATC
ATAGTGTTTATTATCAATAGCTCAGCCAACTCTTAGAGCAATGCAAGAAAA
GTAGGTGAGTATGATAACCTATCATTCACATATTTTAGGAACTTGACTTAG
ATAACACAGATGACAAATGTTACAACCAATTTACAGATTCCAAAATGTTAG
AACCATTTACTGAGTTTCCTGCTCCCTTGATTTTTTAAATCAGTGCTGACT
ATACTTTCACAAATTTGTATCCGTAAGTACAAAATCAAAAAAACCCCTGAA
AATGGAAAGTTTTATCATGATTCATTTGGCTACAAAAATCTGGCCTAACCT
GAAATGATTTGGTGGTTATATTAGTTATCTATTAGTACAAACAAATTACCA
TAATTTAGAACCTTAATACAACACTGATATGTTATCTCAATTTTTGTGGTT
CAGGAATCTGGGCACAGCTTAGTTGGGCCTGCTGCTTAGGGTCTGATAAGG
CTGCAGTTAAGGTGTTGGTCAGGCTGTGTTCTTATCTGGAGGCTAGGCTAA
GGAAGAATCCACTTCCAAGCTCACTGAGGTAGCAGGCAGAATTTCTTTCCT
GATGGTTGCAGGACTTTGGCCCTGGTTATTTCTGGCTGTTGGCTGGAGGTT
GCCCACAGCTTCTACAGGCCACCCCTCAGCTCTTTGCACATGGGCTTCTAA
CATGGCCAGTTATTTCTTCAGAGAGAGCTCAGGAGACAGACTCTTTAGAGA
AAATCTGCCAGCAAGATGGAGTCTTACATAATGAAACGTAATCATAGAAAT
TATATCCCATCATCTTTGCCATATCCTATTGGTCA
```

FIG. 8-35

```
GAAGCAATTCATAAGCCCTGCTCACACTCAAAGACAAGGAATTTTACGAGG
GTGTGAACACCAAGAGGCAGGAATCATAGAAGGCCACCCTTGAGTCTGTCT
TCCACAGTGGCCAACCCTGAACGGCACTGAGATGAGACTATTTAAAAGTCT
TTATTTATCCCACTTAATTTGAATAAATGTTTTGCTGCAGATATATTGATG
AATTTGATTACAGGGCTCTGCCTTAGGCCATGATGGGGTTGAACTTTAGAG
TATATGCATTTTTTTGCCTTTATAACTTCTAAACTAATTTGAATGGCAAAG
CCCATTTTGTTCCAGGGATTTCAGAAAAGGAATTATAGACCTGTGTTCCCC
TCAAATACACAACAACAAACAACAACAAAACCCAAAAGCACTCTGTATTTC
ATCCTATACAGATGACAGGAAGGAAGAACAAGACTTTGTGTAAGTTTTGCT
GGGATTTCACTGAGTCAATTTGCCTACTCTCATCTTTTACAGAAGGAATCA
TAATATGGTTCAAGTGAAACTATTTCTTTCTTTCTTTCTTTCTTTTTTTT
TTTTTTGAGACAGAGTCTCGCTCTGTCGCCCAGGCTGGAGTGCAGTGGTGC
GATCTCGGCTCACTGCAAGCTCCGCCTTCCGGGTCAAGTGAAACTATTTCT
TAAATGGGCTTATCTTTTAACTAAATATTTCTCCCCTCTTAAACACTGTTT
ATTAAAATTTTTCTTTTTTCAAATTTTTTTTTGAGATGGAGTCTCGCTGTT
ACCCAGGCTGGCTTGCAGTGCCGCAATCTCAGCTCACTGCAGCCTCTGCCT
CCTGGGTTCCAGCGCCTCAGCCTCCCGGGTAGCGTGGGATTACAGGTACGC
ACCACTATGCCTGGCTGATTTTTGTATTTTTAGTAGAGATGGGGTTTCACA
ATGTTGGCCAGGCTGGTCTCAAACCCCTGACCTCAGGTGATCTGCCTGTCT
CTGCCTCCCAAAGTGCTAGGATTACAAGTGTTAGTCACTGTGCCCAGCTTT
ATTACAAAAGTGATAGGAATAAATTTTATTTTTATTTTTAAATGTATGTTT
ATTTTATTTTACATTGCCTTCAAGCAGATGCAACAAATACATTTTAATCAG
TCAAACAATATAAAGGATATAAGGAGAAAGTTCAAGGTTTTTCCCACCCGT
CTCCAATCTGACTTCTCTAGGTAGGGTGATCTATATCTTTCCCTAAGTTTG
TACAAACGTAACATATATACACTGTCTCTTCTATGTTACTCGTTACTTTTT
ATGTCTAATATTCCATAAGAATATAATAAATATATGTAACCATATCCCTAC
TGATGGAGCTTCAGGCTGTTTTTAGAACTTAGTTATTACAATGTTGCTACA
ATAACTTTCTAGTCCATGCATCCTTATATCCTGGTGCTTTCATTTCTTTTG
GGAACATACCCCAAACTGGGATTGCCGAGGTTGTTGTTAATCTTAATATAT
GGTACCATATTACTTGACTCAAAGTTGTAACATACACTCCTACCAGCACCA
GGAATAATGACTCACATATACTGAGCACTCTTTAGTCTGTGACAGATTAGA
AAAGCTTTACTTTTCTTGGTTCTTGTTTTATATCACAGTCCTCTCTATATG
GGGCATTTTTGCTTTATAGAGGAGGAAATATGACACAGAGAGGTTAGGTGA
GTGTTGTAGGATCTCATAACTAGAAGGTAGTCATAGAAAGAGTCTAGAGTC
TAGAAACCACTCTCTCACCATTTTGCAATGTGGCAGAAAATGCAAAGTTGT
TATTTACTTATCTCTTTTAGACAGGGTCTCACTCTGTCACCCAGGCTGGAG
TGCAATGGCCCCATCATGGCTCCCTGCAGCCTTAAATTCCTGGGCTTAAGC
AATCCTCCCACGTCAGCTTCCCCAGTAGCTGGGACCACAGGCAAGCACTGC
CACGTCTGGCTAATTTTTTAAAAATTTTTTGTAGAAACACTATCTCTTTAT
TTGTTCAGGCTGGTCTTGAACTCCTGGGCTCAAGCAGTCCTCTCGCCTCG
GCCTTCTAAAGTGTTGGGATTACAGGCATGAACCACCATCTCCGGCCTGAA
GTTTATTTAATCCATTGCCTTGTGGACTGGGCATTGAAGTTGTGTGTAGTT
GGGTTTTTTGTTGTTGTTGCTGTTGCAGACAATACTACTGTGAACATTCT
TATCCATGCTTCCTTGTGTCCCGTAAATGTTCCCTCCAGGGAGATACCTTG
GAGTGACATGCTGGTGTGAGGGATGCATATCATAATTTTACCAGATACTAC
AGATCTTGAAATTGTTCCAATTCTACCCCACAAGCAATATAAGAGCTCTCA
```

FIG. 8-36
```
CTCCTCCAAAACTCCCTGAGTCTTTACTTATATAATTTATGATTTTGACAG
TCTTACAGATTTAAAATGGTACCTAATTGTGTACTTAATTTGTGCTTTTCT
GATTTCACTAGTGAGATTGAGATTCTTTTTGTATGTCCATTAGCCCTTCAG
GCCTCTGTGATTTACCCATGATTTACTGTGGTTTAATAATTTTTATTGGGT
TCTTTTCCTTATTGATTTATGGGAACTTATTATAGCTGATATCTTCTGGCA
TGTGGATGGCATTTTGCATTTTCATCCTGTTTTTTGATAAATAGGGTTTCA
AAATTAAGTAGACACATTTTCCTTCAAGGTCTGTGTCTTTTATGTCCAAAG
AGCTTAGTCATCAGTGGGCAGTGAATTTTATCACCTAATTAATTTTATTAG
CCCCGTGTGCTATGCCTGTAGTTCCAGCTACTGGGGAGACTAGGGCAGGAG
GATCTCCTGAGCCCAGGAGTTCGAGGCTGCAGTAAGCTATGATCACGCCAC
TGTACCCAGCCTGGGCAACAGAGCTAGACCCTGTCTATTAAAGGAGGAGGC
CGGGTACAGTGGCTTACGCCTGTAATCCCAGCACATTGGGAGGCCGAGGCA
GGAGGATCACTTGAGGGCAGGAGTTTGAGACCAGCCTGGCCAGCATTGTGA
AACCCTATCTCTACTAAAAATACAAAAATTAGCCAGGTGTGGTGGTGTGCA
CTTGCAGTCCTAGCTACTCTGGAGGCTTAGGCAGAATTGCTTGAACCCAGA
AGGCAGAGGTTGCAGTGAGCTGAGATTGTGCCACTGCACTCCAGCTTGAGC
GACAGAGTAAGACTCCATCTCAAAAAAAAAAAGAAGAGAGATGAAGGAGGA
GGAGGAAGAGAAAGAGGTGGGGGAGGGGAAGGAAGAGAAAGAAGAAGAAAG
GGACAAAAAAATTTAGCTGTCATCTTTGCTCTGATAGCATTATAATGATGA
TGAAGACAATTGCTAGGTTGGTGAGAGAAGGCTATATACACACCAGAACTC
TCCACGTATATGGCAAGTTCATATATTTTGTTAAGTATGTCTCATTGGAGA
CCTTCTTTTCCCGTAACTATGACCAGTGCTCTGCCAGCTCAGTCAACAACA
ACATTGCATGTTGGCTCCATACCTGGACTCTTGGTCCAATTGGTAATGAAA
CCATCCCACCAGTGTCTTCATAATATATATATACACACACACATATATATA
TAGTATTCTCTCCCAGTGTCTTCATAATATATATATATACACATACACACA
TATATTATATTCTCTCTATACATATTTATTTATATATCTATATCTATATCC
TTCCACCTCAGGTCTCCCTCTGTCTCCCAGGCTGAGTGGTGCAGTAGTGCG
ATTATGGCTCAACCAATGAGAGGATCAATGGCAATCCTCTCATTTCAGCCT
CCCCAGTAGCTGGGACTACAGGCATGGGCCACCACATCTGGCTGATGTTTA
AATTTTTTTGAGACAGCATCTCTATATGCTATAGATATATATAGTATCCTC
TCTCTAATATGGATAGAGGATACTATGTCTATATCTGTATCTATCTATCTA
TGGAGAAGGAATACTATATATCTAATAAGATGTAATCTATATTATATATAA
AAGTGAAGCATTGATTGGTACATATAATATATATATTGATTACTGTGTGTA
TATATTTGTTTTTTCGAGACAGGCTCTCACTCTGTTGCCCAAGCCGAGTGG
TACAGTGGTGCGATCATGGCTCCACCACCTGAGCTAAAGTGATCTTCTCAC
CTCAGCCTCCCCAGTTGCTGGGACTACAGGAACAGGCCACCATACCTGGCT
AATTTTTTAATTTTTTTTTGAGACAGGGTCTCCCTTTGCCACCCAGGCTGG
AGTGCACTGGCGCAATCTCGACTCACTGCAATCTCCACCTCCCAGGCTCAA
GTGATCCTCTCACCTCAGCTTCCCGAGTAGCTGGGACTATTGGTGTGCACC
ACAATGCCTGGATAATTTTTCATATTTTTTGTAGAGATGGAATTTGGCCAT
ATTGACCAGGCTGGTCTCAAACTCTTGGACTCAAGTGATTGACCCGCCTCA
GCCTCCCAACGTGCTGGGATTACAGGCATGAGTCACTGTGCCTGGCCTGAT
TATTGTACACATTTTTGATGTAATGTATTATATATGTCATATATGACAATC
TAGATGAATATATTAAAGATTGGGTTTTCATTTATATATTGTAAAATACAT
ACACTATACATATATAATATGTAGAACATATGCTATACATATTATATA
TGTATATGTTAACATATATAATACATACACATATAATATGTATAGTTG
```

FIG. 8-37

```
CAAATATAAAATTTGGTTTGTTATTTATATTATTTTGTGCAGGAGTTCTAT
ATCTATGTCTATAAGCGGGAGCCATAATTTTCTATTCTTTGTAGGATTTGG
TATGAGATTGGCATTACTCATGCCTTGACTTCTAAATTTCCTATAAAACTG
ACAAGTTCCATTTTTGCTTGATAAAGATGCACGTTTTATTATCTGTCGGTA
AAATTTAAAGTAGTGATTTCATTTCTTTAATGTTAGGTCTGCCCATGCTTT
ATTTGTTTTTTGAGTGAGTTTTACTCAGAAATATTTTTTCTAGGAAGTAAT
AATTTTATCAGTACTTTCAATTTTATTAGTAGCATAAGATTTATTATAAAG
TTCTGTAATATTTAAAAAGTTTCTGTATTCATTCCATTTGTGCCTTCTGTC
TTACTTTGATAAATCTCATTGGAGGTATGTCTATTTTATTAAATTTCTTTT
AAAAGAAGCTACCTTTTTTTTGTTTGTTTTCCTCTTTATTGCATTCTTG
TTTTCTTTAACTTCACTGTTATATTGTTTAATATCTATTTTTTCTTTTTAA
AAAATTATATTTGGCTTTCTATGTTCTTTTTAAAATTTAAATTAGATGCTT
GGCTCATTAATGTTCAGCTTTTTAATTTTTCTAAGATAAGCATTTAAAGCC
TACAAATTTTCCTTAAAATTCTGCTTTAGCTTCATTGTATATTTTTATAAA
TAACTTTTTATTATTGTTCCATTCTATACATCTTCTAATGACTTATTAGTA
GTTTACATTTCCTAATATTTAGAATCTTTTTAGTCATCTTTTTATTATTGG
TTTATAATCTTATATTGAGGCTAGAGAAAATGATCTGTGTAATACAGATTT
ATTGAAACTTGTTCAGACTGTTTTCTGCCTAGTATTTACTCAGTTAGTGCA
TGTTCCATCTATACCTGAGAAAACTGCATATTCTCTGCTTACTATTATTAA
ACAATTGCTGAGCTTTATGTATTGACTATGAGATTGCGCTTCTTAGATTGT
TCAGACCTTCCGTATCTTCCCTTATTTCTTTCTTTTGGTCTGCCTGATCTA
TCAATTATGGAAAGAAGAATGTTAAAACATCCCATGATGATTGTAGATTTG
TCCATTTCTCCTATAATTCTACAATTTTTGCTTTGTATATTAACACAATTC
TAAACATGAATTCACTAATAATGTAGTACATTTATGTTTAAAATTGTGTTA
TCTTTTTTAGGTGACTCCTTTCATTCTTTCTTTTTTTTTTTTTGAGACA
GAATCTCTCTCTGTCACCCAGGCTGTAGTGTAGTGGCGAAATCTCAGCTCA
CTGCAACCTCTGCCTCCCCGGTTCAAGTGATTCTTGTGCTTCAGCCTCCCA
AGTAGCTGGGATTACAGGCATGTGCCACAATGCCCAGCTAATTGTTGTATT
TTTGGTAGAGCCAGGGTTTTGCCATGTTGGGCAGGCTGGTCTTGAACTCCT
GGCTTCAAGTGATCCGCCTGCCTTGGCCTCCCAAAGTGCTGGGATTACAGG
CATGAGCCACCACACCTGGCCCTTCTTCCATTCTTAATAATGCTCTGACTT
AATATCTTTTGATATAATACTATAACAGTATATGACTATATTATCTATCTT
TTAGCTTCCAATCTTTCTATATGTTTTTGTTGATGTGTCACACCAATAGAT
AGGTGGAATTTTAAAAATCCAATTGATATTTTTTCTCTTAAGTGGTATTAC
CACCCCGTAAACATTTTAATTTCTCAACATGGGTTTTCCTGGGTCATTCAG
GTAATATGAATTGAAACCCCAAACTTCTGTGAGTCAGGCTGATAAAAGCTA
ACTGAATAGAGTTTGAAAAAGGAGGGTATTTACAAAGGTGAGGAGTTGGGA
AATCCACAAGGAACAGGAAGCACCCAGAACTAGGAACAGTTAGAGAGCCAT
CACCTCCTCTGGGCCTCAAGTGGCAGGTGTAGGGAGCTGTAACTATACTAG
AGTGTGCCCAGAGGCAGAGGAATGCAGACCCTCCAAATCATAGCGTGGGAC
TGGGGTACTGAATACTCCCAAGGCTGCTTCTTTGTGCCCTATGGTCTCCTC
TGGTGCTTCCCATTGGCTGAACCAAGCCAGAGGGCGGAAAGCCTGGTTAAT
CTGTCCATGTCAGCCTTCCTGGGCACAGAGCAAGACAGGGAAAAGTGAGGG
ATTATTTGGAAGAACAAACAGAGAGCATCCAGCACAGGAAGTGTTTCTGAA
TACTTGAATTCCTTAATTGTCACAGACCAACTGATCAACATTTAACTCAGT
AGCACAGTGGTTTCCTTAACTCTCTTGTTAGAACATCCTATTACCATTTTT
```

FIG. 8-38

```
TATTTTTAAAAACTGCATACTGTTCCAGTATCTCACTTTAGTTATCAGATCT
TTTTCTGTCTTGTTTGATTCTAGTCTGATATTTTTCCATGTTATATTGGTC
CTCCAGTGTATTATTATCTCATACTAATGCTTATGGAACATTATCTGAGGG
GAAAGAGAAGAGCTTACAATTAAAAGTCATGGGACTAGGCATGTGTCATGA
GACCTGGGTCTTCCAATAACAAGCTAAGACATTAGCTGAGTCATTTTCCCT
CTCTGATTCTCAATGTTGGTGGTTATTCAGTAGAGAAGGGAAAAGGTATCT
TTCTGCTCAACTGTCTCATGATTCCTGGAAGTCCTGCATGGGAGAAGAACT
TTGGACAGGATGGTAACCATATTAACAGGTTAGTTCTGTACCTTGGCATCC
TTGAATAATTAAGACGAAGATGATGTTGATGATATCATTATTACTACATGT
TGTTAGAAGAGCTGAAGCAGGACTGGCTTGTCTGTCATAATGTAAAAGAGT
CTTGGAAGATGTCCGGGGTCCAGGGTCCAAAACCCCTCGTGGCCTTTGGAA
CACCAAGCTCTGTGCCAAATGGTGGAAGGCTGCCCTGCCGCACCACAAATC
TAAGCCTAGGGCATAAAACCCCTTGTGGCTTGGATGGAACCCAGGGCTCAG
GGCATAAAACCCCTCATAGCCTCTGGAAAGTGCACAGACTTGTTGGTTCCT
TGCTTTTCACTCATAAACGTGTCCTCTACTATCTCAAGCAGCAGAGTATAT
TCTACATGTGTCAAAGAAAATGCTAAACTGTCACAGCTACGCTTAATGCAC
CACTACCTTTCTACCCCCATGTCCTCATGCCCTCACCTGTTTACCCTCACG
TCCTCACCACCTGCTTCTTTGTTTGATCACCAATAAATAGTGTGGGCTCCC
AGAGCTTAGGGCCTTTGCAGCCTCCAATCTAGTGCTGGCACCCTGGACCCA
CTTTATGCACTCTTAACTTGTCTTTTCTCATTCCTTTGACCCCGCCGGACT
TTGTAGCCCCCACGGCCTGGTGTTGGGCCTGATCACCCCAACAACTACCAC
TTATTAGTGGTTACCATGTACCAGGAAATTTTACCAAGCATTAAGCAAACA
TAAGCTTATTCAATCCTACCCACCATTCTCTGCAACAAATACGGTAATTTC
CACTTTATAGTTAACAAACTGAGGCTCAGAAAGTTAAATGATTTGCCTAAG
CTCACCCAGTTTATAAGAAACAATAGTTGGGTTTGAACACAGGCTGGTTTT
ATTGAAAATAACTTGTGGCTGGGCATGGTGGCTCACACCTGTGTAATCCAG
CACTTTGGGAGGCCGAGGTGGGTGGAACACTTCAGGTCAGGAGTTTGAGAC
CAGCCTGGCCAACATGGCGAAACCCCATCTCTACAGAAAATTTAAAAAAAT
TAGCCACTTGTGGTGGTGCGCACCTGTAGTCGCAGTTACTCCGGAGGCTGA
GGCAGGAGAATTGCCTGAATCCAGGAGGTGGAGGTTGCAGTGAGTTGAGAT
AGTGCCAGTGCACTCCAGCCTGGGTGACAGCAACACTCCATCTCAAAATAA
AATAAAATAAAATAACCTGTGTTCTTCACAGCAACAAAATTATTTTTGTTT
GTTTGTTTTGTTTTGCAGTTAGTGTGACTCTGGATCCAGATACAGCTCAT
CACGAACTAATTCTCTCTGAGGATCGGAGACAAGTGACTCGTGGATACACC
CAGGAGAATCAGGACACATCTTCCAGGAGATTTACTGCCTTCCCCTGTGTC
TTGGGTTGTGAAGGCTTCACCTCAGGAAGACGTTACTTTGAAGTGGATGTT
GGCGAAGGAACCGGATGGGATTTAGGAGTTTGTATGGAAAATGTGCAGAGG
GGCACTGGCATGAAGCAAGAGCCTCAGTCTGGATTCTGGACCCTCAGGCTG
TGCAAAAGAAAGGCTATGTAGCACTTACTTCTCCCCCAACTTCCCTTCAT
CTGCATGAGCAGCCCTGCTTGTGGGAATTTTTCTGGACTATGAGGCCGGA
GTTGTATCCTTTTATAACGGGAATACTGGCTGCCACATCTTTACTTTCCCG
AAGGCTTCCTTCTCTGATACTCTCCGGCCCTATTTCCAGGTTTATCAATAT
TCTCCTTTGTTTCTGCCTCCCCCAGGTGACTAAGGAAAAGAGCAGAAGCTC
CTTGGTTTAACCAGCACAGAGAAAATAATATAAATCCCATAAGGGCAGACG
TTTGGTCTGTTTTCTTCGCTGTCATTTCCTTAGTAGTTAGACTAGTGCTGA
GATTTTAGTGGATATATAATTGATTTATGTTGAATATATGGACTTAGCAAC
```

FIG. 8-39

```
TAAAAATACCACAGATGGTTAACCTGGACTGGGGCAAAGCAAGATAATAGT
GATGATCGTATGTTGCTGTCTCCATCCGTCTTTAATGGGTCAGGGCTTTGA
TTTCCAAGGGTCTTCAGGTGATGAGTAGGGGTACCCACAAGTCAGAAGGTC
TGCGTTCTCCTAGTTTGTTTGCTGCCATTTGAACTCATGTAGGGAATGAAA
GAAAGCTGCAATTATCCGCCAACTGCATTTAAAACAAAACAAAACAGAAAA
ATCAAAATAACATTGACTCTTCCAACCACTGACATGTTGTTTAATAATCTA
AGCGGCAGTCCTGGAGGCTACCAGACTTACTGAGTTCTACCTGAGAAACAG
CCAAGCAAAGTGTGAGAGAAGGGTTAAGACTGGCTTACAATGAGATGCTTC
AAATGAAAAGGGAATTATGAGTAAAATTGAACTTTGATGGGGGATTCAGTT
CTGGAAAAGAATTTGGTATTTTCCAGTCTGCTAGGACCAATTACCTTGAAA
TATTTTAAAATCTCAGTAAATAGTTATTGCTGAAATGGCTGTTGGCAGTTC
TTATTATGATTCAGAGAAGAGCAAATAGACCTTAACTTCATTTTGAAAAAG
ACCAAATTACCATACCCGAGTGAGTAATGACAGGACTACAACTAAAACATA
AACAACATTAATGATGACCATAAAAAGTCACAAAATTGCTAAATGTTATAA
TTTAGAGTTGACATAAAAATTGATGGCCAGGCATGGTGGCTCACGCCTGTA
ATCCCAGAACTATGTGAGGCTGAGGCAGGTGGATCACTTGAGGTCAGGAGT
TCAACACCAGCCTGGCCAACATGGTGAAACCCTGTCTCTACTAAAAATACA
AAAATTAGCCGGGCATGGTGGTAGGGGCCTGTAACCCAGCTACTCGTGAGG
CCAAGGCAGGAGAATTGCTTGAGCCTGCAGCAGCTGCAGTAAGCCAAGATC
ATGCTGTGCCTCAAGGAAAAAAAAAATTAATGTTTACTGATATTTGTTGAA
GTCCTACAACATCACCTCTGAGAATAGGAGAAATGAAGCAACAGTTGTGTC
TAGATGTCAGAGGCATGGCTGGGCCTCCATCTCTGCCTAAGGGAGATATAA
AAGAGTTCAAACTATTGCCCATGTTCCCCAGGGTCAGAAGTTCTAATTATG
ATGATAGAGGCTGGGTTGTAAGTAGTAAGTGAAGGGTAGCAGAATATGCCA
TCTTTGGCATAAGAAGTATTTTGAGTTGAAGACAATTGAGAAAAAAAATAG
ATTAAAAACAAACAAACACCTCTGCCCTCTCCCTATTTGCCTAAAAGCAGG
ATATGAAATTGTGAAGGTGTCTTCTTACTCGGGGAAGAACAAAAGTTAGTC
ACCAGAGACTTTAGACTCTTATCAGCCTGGACATAGCACCAGAGAAGTCTT
TTTTTTTAAAAAAAAAAAAAAAAAAAGGGAAAGAAAAAGTTGCCTTCCCAC
AATTTACTGCACTAGAAACTCAAAGTCCTTTTCGTCTTCCTTGTCACTTAA
AAAATGTATTCTTTTCTTAAAATGCTATATAAGCCCAAGTTCTAAATCCTC
TTTTGAGTATTCATCTCAGTACTCCCCTGTGTTTGTACAATGCACATGCTT
TGTTTCTGTCTTGTCAATCTGTCTTTTGTTAGTCTACTTGATAGGGCCACA
GATGGAGAACCTAAGATGAATAGAAAAAAAAGATTTTTCTCCCCAACAGAA
GGATTATCGCCAGTTGCACTTGTTCTATATACCCGTAGTCTCGGTATGCTG
ACCCAGACTTGGGTAATAGGACCCAGTGGGTAACCGAGGAACCCCACCTTT
GTGCAGGATCAGTGAAGATGTAATCTGGATATTCATAAGCTCTTCTCTACC
TCTTGGCATCCCACAGTCCTGTGTTAATGTAAGTGTGGTCTTCCCCAGAAA
GGGGAGGCCTCCCTAACATTGTTAAAGCCTAGCATATGCTGCTTAGAGGAA
ATTCTATATCCCTAAGCACTTAGATTGCTGAATAAGAAAGAATGATAATAA
AATAAACAATTAAATAAAAGTTTTAAAAAATGAATAAAATAAACCTGTGGA
AACTATAAGGAAGGCCAGAAGAAATATAAAATTGGAGATTAATTGGGGTGC
AGGAAAGTTATGGAAAGAATATAAGTCCTGCTAGATAAATCATTAGCTATT
TTAATAAAGAATACAGAAGAAAATAGGAACAAAAGAATATATACTGGAATA
ATTTTGAGAGTAATTTGAAGAATTAGATGCAAATAAATTTGAAAACCTTTA
AAAAGAAACCAATGGCCTAACTGACCCAAGAAGGAAAGAAAATCTAAACAG
```

FIG. 8-40

```
ACTGATAAATACAAAATGAAATTCAGACACTTACAGAGCAGCCAGGCATGG
TGGCTCACACCTGTAATCCTGTCACTTTGGGAGGCTGAGATGGGAGGATCA
CTTGAGGCTAGGAGTTTGAGACTAGCCTGGGCAAGCTCCCATCTCTAAAAG
AAAAGAAATTAGCTGGGCATGGTGGCATGTGCCTTAGTTTCAGTACTCAGG
AGGCTGAGACGAGGATTGCTTGAGCCTAGGAGGGCAAGGCTGCAGTGAGCC
ATGGTCATGCCACTGAATTCCAGCCTAAGTGACAGAGCAAGACCTTGTCTC
AAAAAAAAAAAAAAAAAAAGTTACAGAGCTCCAACTAAATAATGTGGGGAA
CAAAAGAAAAAGAAGATGATTTTATGGCTGATTTTTTTTTAAGGAAAAG
CAATTCATGTACCCTTGAAGATTAGATTAAGTTCTATAAAATAGCCCAAAA
TGACAGTGGCTGAAACAAGTTTATTTATCTCCCATTTAAAGCAAGTCTAGA
TGTGGAAGTCTGGGAAGCCCAGAAAATCCAGGTCTTGTTTGTGTATGGAAA
CTCCAGAAAATCACAGATTCCTTCCAGCCACCCCTCAATTACCCCTGGGAT
CCAAGAGAGCCACTAAAGTTCCAGCCATCATACTCACAACCCAAGTTGTAG
GATGGAAAAAAGGACACAAAAGTAGGGTGAAGAGCATGTGTGCAACAGCTC
TCTTTTACTCTAGTGTCCTAAAACCTATCATAAAACCTTTGGCTTGCCTTG
CATTAGCCAGAATTTAGTACATGGCCACACTTAAGAAGTCAGAAAGATTAG
CTTTTTTTCCAGGGTAGTTGGCTGAAAATCAGGAGTTCTCATATTAAAAAA
CAGAGAAGGGACATCGAATAGATGACCAACAATCTCCTTCACACTCATACT
ATTTAAACTGTCCTAGTCAATGACCAAAAAAGAAAAGCCTACAAACTCATT
GATATAAAAGCTTAACAAAGGTACTCCCCGCCCCCCGCCCGCCACACACCA
TCCCCAAAAGGAAATTTCTAATCCAATTAACAGTCTTAGGTTGGGCTGCTG
AAACAAAATACCACAGCCTGAGTGACTTAAACAACGACAATTTATCTCTCA
CTGTTCTGAGGTCTGAGTTGATTCTTTGTGAAGGCCCTTTCCTAGCTTGCA
GATGGCTACCTTCCTGCTATGTCTTCACATGGCAAAGAGAGAGCTAGCTTT
CTGGTCTTTTCTTATAAGGGACCAGTCCCATCATGCCCATCATGAAGACTC
GATCTGCTAGGATCTCAACTAAACCTAACTATCACCCAAAGAGCCCACCTC
CAAAGACCATCACATTGAATGTGAGAGTTTCTACATATGCATTGTGGGAAA
CACAAACATTTACTTCAACTGTAACTATTGAAGCAAAAATGTCCCCCCACC
ATAGACATCCAGCACCACAGTAGTACATTTATTACAATTGAACTTACATTG
ACACGTCATTATCAACGAAAGTCTGTAATTTACATTAGGGTTTATTCTTGG
TGTTGTGCTTTCTATGGGTTTTGACAAATGTATAATGTCATGTATTCACCA
TTATAGTATCACAGAAGTTTCACTGCCCTAAAAATCCTGTGTTCTGCCTTT
TCAACACTTCCTGTCACCCAATTTCTATCAACTAATCTTTTGACTGTGTCC
ATAGTTACTGTCTTTTCTAGAGTGTCATACAGTTGTGAAGCAGGAAGCAGG
AGTGAACTCCGGAGGCAGGGACTTTACTCCGGACCAGATTGAAGACTAGCC
GAAACAGGGACGAGGTTAAAGCACCTCTCCATAAGACACGCCCACCAGCGC
CATGTCAGTTTTTCGTTGCCATGGCAACAACAGGACATTATCGACTTCTTT
CCTCTGTACCTACTCCGAAGTTACCACTCTTTTTCTAGAAATTTCTGCATA
ATCCCCCTTAACATGCACTTAACTAAAAGCAGGTATATTACTGCAGAACTG
CCCCTGAGCTGCTACTCTGGGCACATTACTTATGGGTTAGCCCTGCTCAGC
AAGGAGCAGTACCTGTTCTGCTGTTGTACACTGCTGCTTCAGTAAAAGTTG
CTAACACCACCACTTCACCCTTGAATTCTTCCCGGGCTAAGCCCTAATTTT
TGGCTTGCTTGCCCTGCATCAGTTGGAGTCATATAGTATGCAGTCTTTTCA
GGTTGGCTTTTTAGTAACATACATTTAAGTTTCCTTCATGTGTTTTCATGG
CTTGATCGTTTCTTTTCTTTTTCTTTTTCTTTTTCTTTTCTTTCTTTTT
TTTTTTTTTTTGAGACAGAGGAGTCTTGCTCTGTTGCCCAGGCTGAAGTGC
```

FIG. 8-41

```
AGTGGCACTGGCTCACTGCAACCTCCATCTCCCAGGTTCAAACGATTCTCA
TATCTCAGCCTCCCGAGTAGCTGGGATTACAGGCTCACGCCACTATGCCCG
GCTAATTGGGGTTTTCCCATGTTGACCAGGCTGGTCTCAAACTCCTGGCCT
CAAGCAATCCACCCACTTCGGCCTCCCAAAGTGAATGCATTTCTTTTTAAC
TCTAAATAACATTCCATTATTCAGAAGTACCACAGTTATCCACTTACCTAC
TGAAAGACATCTTGTTTCCAAGTTTTGGATAAATTATGAATAAAGCTGCTA
TAAACATCTATGTGCAGGTTTTTGTGTGGAGATAAGTTTTCAATTCCTTTG
GATAAATACTAAGGAGTGTGATTGGTGAATCTTATGGTAAAAGTATGGTTA
CTTTTGTAAGAAACCACCAAACTGTCTTCCAAAGTGATTGCACATTTTGCA
TTCTCACCAGTAATGAACAAGTTACTATTGCTACATATCTTTGCAACCTTT
GGTGCTGACAGTGTTCTAAATTTTGGTCATTCTACTAGGTATGCAGTGGTA
TCTACTTGTTTTAATTTGCAGTTCCCTAATGACATGATGTCAAGCATCTTT
TCATATGCATACTTGCATCTGTGTATCTTCTTTGGTGAACAGATGTTCAGG
TCATTGGCCTGCTTTAAATCAGGTTATTTTCTTACTGTTGAGTTTTAAGTA
TTCTTTGTATATTCTAAAAATATTGTTCTTCATCAGATCTGTCTTTTGCAA
ACATTACCTGCCAATGTGTGGCTTTTCTTCAACACTTCTTTGTAAATTTGC
AAGTCCTTTGAGAAAAGAAATGCACCCAAAGTATTAATTTGGCAATCTCAT
ATCACGAGAGTACTCTAAAGCTAAATAAATTACAGTTTTTCAAATTTTGAA
TTAATTGATCTTTGCTATTGTTAGCAAGGTCTTGTATTCTTTTTTTTTTTT
TTTTTTTTTTTAATAGAGACGGGTCTTGCTACAGTGCCCAGGCTGGTCTC
GAACTCCAGGCCTAAAATGATCCTCCTGCCTTGGCCTTCCAAAGTACTGGG
ATTACAGGCATAAGTCACCACGCTCAGCCATCTGGTATTCTTTAGCAACTG
TTTGGTAACTTAATCTTTCACTTTTGAAAACAAAAAATAGTTTTTTCTC
ATAGTTTTCTAACAAAATCTTCATAACTGAAATAATTTCTCTTTATCACCT
CTTCTTATAAATATGGTTTTCTTTTTTAAATAAAAATTTAAGACATTTTA
TAACTGGCCAAATTTACTAGCTTAGATACTATTAGATAGTCAATATTTTT
GTTGGATATTTGATTTTTATTTCAGGCAACTAATATCTATTCATTTTTGCA
CTGTTGGAAGAAAATTACTGATCAAATTCACTATGTATTTGCAGAAAATGG
CTTTCAATATTGTCTACTTTATCATCCTTTTTTTTTTTCTTTCTTCCTT
TTTAGATACAGGGTCTCACTATGTTGCCCAGGCTGGTCTCCAACTTCTGGG
CTCAAACAATCCTCCCTCCTTGGCCTTCCAAAGGGTTGGATATGTTTTATC
TACAGTTTTGTTGTTTTGTTCTGCTACAGGATATTTGCAATTGCCATTTAT
CATGAAATTCATGACATACCTTCTTCCACTCTCCTTTTTATCTTTATTGTT
CTGGTTATAGGACTAGCTTTGCATCTCTACTCAATTCTGTATCAGTAGTAT
GCTTTCATTTTAAATTTTAAGTTTGTCCATATGTATATTGACACAGGGTCT
TGCTCTGTTGCCCAGACTGGAGTGCAGTGGCAAGATCAGGGCTCACTGCAG
CCTTGACTGCCTAGGCTCAAGTCATCCTCCCACCTCAGCCTCCAGAATGGC
TGGGACTACAGGCACGCACCACCACACATGGCTCATTTTTTTGTATTGAGA
CAGGGTTTCTCCATGTTGCCCAGGCTGGTCTTGAACTACTGGGCTCAAGCA
ATCCTCCCACCTTAGCCTCCCAAAGTGTTGGGATTACAGGCTTGAGCCACC
ATGCCTCGCTTCTACACTTATTTTTAATTCTAAAATAATTTATAATAATAA
ATATTAACAATTAGATTTAATTACTGATAAATATTAAATGTTAAATAGGTT
TTATTAAATAATTAAATAAAAATGAAAATAATCAGTATTTCAATTTAATTA
CTAATTATAATTCACAGTTATCCTTGTAACTCCTAATGTCTATATAAAAGA
TTTTTATATTTTTTAATTCTTAAAATTTTATTATTTATTTCACACCAGGCC
ATCACTGTGATACATTTTTTAAAACACATTAAATTATCACCAGAAAAGTGC
```

FIG. 8-42

```
TGTGATGGAAAATATAAATTGAAATACCTTTTCTGGTTAGGAGAGTAATTC
TGTTTTTCTGATAGAGAATAGAAGAGTCCTTCAGGCCCCTCCAAACTGTCA
TATTCCGGGCATCGGGTGTCCCCATCCTCACTTCAGTCCACAGGCAGGGTC
CTCAGTCTTCAGCGCTCCTTCTCTTTCCCCTTTGTCTTGTGTCTCCTTGGG
TCTCTTTTCTCCAAGACCTAAACTCCCTGAGGACAGGACTATTTTTTACAT
CTTGATGTCACTCCTGAGCACTTGCTTTAATGTGTTGGACACTGGGTCCAT
TAAAGATTGTATGTGAAATTATAAAAGAAACGTTTTCACCTTTCTGTGGTA
CAGCTATAATTTCTGGTTTCATTTACCAACTGGGTGAAAGTGGACCAGTGA
CACCATTTGTCTGGGCCTTCCTTTCCTGAAATATAATATTGGGGCAATAGT
CCCTGGTTCTTGTAAGGTGTTCAGGCACAAAACGCTAGGCATGTAACATAC
TAAATGAGGTTTTCCCAGTTAATTTATATGATTGCAAAGGACGTTCATATA
CACGGTCTGCTAAAGAATTCTGGGGCCAATTAATCTCTGTGGCATGATGGG
TAAGTCGATCCCTTCTCTGGGCGTCTATTACTTCAGAAAAGGCATGAACTC
AATTTTAGGGACCACACAAAAAAATTTATTCACTATCGTGTAGGACTTGGT
CATTAGAGAGCTTTTGTTTCTTTTTTTTAAAATTTTTTTTAATTTTTATTT
TCGTGTATGTGAATTTAATGGAGAGCTTTTAAATAACCAGATATTTAAATA
ACCAGATAATACAGATGCCCGGCCTGCTCCAGACAAATTAGAAAAGTATGT
AGGTGAGGAGGGACCAGCCAGAAGGCGGTTTCAGCTCTGGAGTGACACTGA
ACGTACTTCTCTTCCAGGGATGTCACGAGGTGTCAATTTCTCTGGCCTTAC
CCAGGTCCATGCCCGCCCCAGGGGCCCCAAGAATGACTTCAGCACCCCAC
CCCCACCTCCCTCTCCAGATGTGGGTCCTGGGAGCGTTCAAGGCCCGTCAG
TCACTCGAGCCACCCCTTGGCGGCTGGACCAAATCTTGGGCTGCCGCCTGG
ATCTGCAGCTGGAAAGCGCCGTGACCACCGGTGTCCCCAGCTGGAGCAGGG
CGGGCTGCACGACTCGCGAGGACGCCCTGAACCGCGGCTTCCTCTTTCATA
GCCGCAGGACTCGTGGTCAGAAGGCCGACTCCAAGCCTCAGCGGATCCACG
AAATGGCCTCTTTGAGGCTGTGGTGAAATTTAAGATACCCTTTCCCTGCCA
TTGTTACTGACGTACTTCAGCAAACAGGTTAAAGTTCTGAAAGGACGTGGT
CACGACTTTATATTTCTTACAGATTTGTGTCTCATGTTTTGTGCGTAAAAA
CCATTCGTCCTCATTTGAGATTCTCATATCCGTAATTCAGTTATACATAAA
ACTGAATTCAGTTATATCATAAAATGTTCCCATGCGGGGAATGATTCGTTG
GGGTCTCAGCCTGAGGCCAGACGCAGCAGAGAGATCGGGAGTTGGGGGATG
GCGGGCGGGGAGCGGAGAGGAGGCCGCCCGCCGCCAGACTCAGGGTCCAGC
AGAGCAGCAAATGCTCCCCGGCTCCCAGCCAGGGCGCAGCTGCTGGCCTGG
GGCCGCCCCTCACGCCGCAGGAGCCCCGCCCGCAGCGCCGGCCCTGCCCCT
GGCCTGTGAGGGCGCCAGCGCCCCCTACAGCTTGCAGTCGCCCTGCGCGCC
TCCCCGCGAGGCTTGTTTTCTAGCGCCTCTGGTGGGCCGCCTCCCGCAGGC
CTGGTGTGAGCCTGGGGTCCGTTCTCACAGCTGGATCTGGGGTCTGAATGC
CGCGCCCTCTGGAGAGCCACAGATGGGTCTCCGCTGATGCTTCTCTCAATT
TCCTCTAAGAGCGAGAGCTCCGGGAAAGGAGCCGATCCTGGTGGAAGACTA
CAGGTCTGAGTCCACTGGACGAAAAACGAGGTGCGTTAAGAGACCGCGGGA
GTGGGGAAATGGGGAAGTGAGGGTGGGGACTGGGCAATGGGGGCGGGACGA
GAGGTCTGGGGCTGGCGGGACAGGGCTTAAGAGAGAGCCACCCCTCCTAG
CCTTGAAGCTGTACCGAGCTTCCCTGTGATATTTTAAAATGCAAAAGTACA
AAAATTGAAGTAATGGAACTATGCGTACGCACCTCCTAGATTTTTAAAGGT
TAACGTGTGACTGTGTTTACTTCAGATGTTCCTGAAATAAATGAAAATGAC
CAGTTAAAATGAAGGAAGAACGCGCTTGCGTCCCTCCTAGAGGTCAAACAC
```

FIG. 8-43

```
TCTTCTGAGGATAGGTTGTATGCTCTCAGCGCCTCTTTTTATTAAAAGTAT
TAAGAAGTACTTTTCCAAATATTAGATGTAGTGTGTCATATCATTTAAACG
ATTTTTTTGTTTAAAATAGTCTTTTAAAAATAATCTTTTTATTTTTAGAT
TTTTTTGAGACAGAGTCTCGCTGTGTTGCTCAGGCTGGAGTGCAGTGGCGC
CATCTCCCCTCACTGCAACCTCTGCCTCCCAGGTTCAAGTGATTCTCCTGC
CTCAGACTCCCAAGTAGCTGGGATTAAAAGCGTGAGCCACCACACCCTACC
AATTTTTGTATTTTAGTAGAGATGGGGTTTCACTATGTTGTCCAGGCTGGT
CTCGAAATCATGACCTCCACTAATCCACCTACCTCGGCCTCCCAGAGTGCT
GAGATTACAGGCATAAGCCACCGTGCCTGGCCACTTTAATCATTTTTGTTT
TTGCATCTAGTCTAAGAAATTCTGCACTAAAATTCTGCACTATTTTCTTCT
AAAATTTTAAAACATTTTCTATCTGTGTCTTTGTTAGATGTAGAAACTTTT
GTGTATGATATGGGGTATAGCTATAATTTTATTTTTATTCCATATGAAAGC
CAGTTTCTCAGCCCAGGTAATTGAATAGACCATCCTTTCTCCACCAACTCT
TAAGGCTACTTCTGCTCTATTGTGTTCATAGTAGTTTCTAGGCTTTCTGTT
TTGTTGTACTGATTTCTTCACCTATTTTTGCATCAAGGCTCTCCTCTTGGG
GAAATAAAACAATCCTGCCAACCAAAGACCCCTCTGGATCCTCAAACACGC
CATCAGCATGGAAGGCCGCTATGGCATAGCGAGAGATAAATAGGATTCAGG
CAGTGCTGTCCTTACATCGCAATCATTCAGGTAGTTAGCAGGAGCATCAAT
CAGTACAGATATCCAGAGCTGATGGTCTTATTTGTATGAATGCCCAGTGCA
TATGGGATTGGAGGGGAGGGCTTGGAGTGGGATGAGGGGCTAGTGGGATCC
AGAAAGGGGCTAGTCTTCAGGTCTTCCCTGGAGAGTATGTAATCTCTTATA
ACTAAGTGTTGATTTTTGTTTTGTTTGTACCTTCTTTAGATATTGAAGTAT
TCGCTAAGGCTTAACATGTAATATATTTAAATCTTCATATGAATACGTTTA
TCTGATAGATTTTGGTGAGACATAAACTATGAAACAAACAGAAAGATGGAA
CATGAGAAAGGGTCAAGGGTGGCCTTGGTTAGGGATGGCAGCTTTTACAAC
TATGAGCTAAGATAAAATTTAGAAGGTTTTCTTTTTATTTTAATTAATCAT
ACCACTATTTTTCTCCTTTAATTTCCATATATAATGAGTTGATTGTAGTAT
TTTTATTGTGCTTAACTATTTTAAGATAATAGTTGTCTCTCCTCATTTTAG
CAAATAATATATTTAATGAAAAATCAACTTTATTGAGGAATAATTTATACA
CAGTAAAATACACCTGTATTAATTATACAATTTGATGCGTTTTATATACCC
AAACAGTTACTACTGTAATCAAGTTACAGAACACTTCCGTCAACCTAGATA
GTTTCCATTTGTAGTATCACCTGTGCCGCCTCTTCCATCCTCTTGGCCCCA
GGCAGCCACTGATGTACTTTCCATAATTACAGCTTAGTTTTCCCATTCCTA
AAATTTCATATGAATGGAATTTATATCATATGTATTTTTTATTTTCCTTCA
CATTTTGAGATTCATCCATTTTGTGTATATATCAGTAGTTTATTCCCTTT
TATTGCTTTATAATATTCCAAGATATAGATATATTGCAATTTTTTTTTTTT
TTGAGATGGAGTTTCCATCTTGTTGCCCAGGCTGAAGTGCAATGGCATGGT
CTTGGCTCACTGCAACCTCCGCCTCTTCGGTTCAAGTGATTCTCTTGCCTC
AGCCTTCCGAGTAGCTGGGATTACAGGCGCCCGTGACCATGCCCAGCTAAT
TTTTTAGTAGAGATGGGGTTTCACCATGTTGGATGGCTGGTCTCAAACTC
CTGATCTCAGGTGATCCGTACATCTTGGCCTCCCAAAGTTCTGGGATTACA
GGCATGAACCACTGCGTCTGGCCGATATATTACAATTTATTTACCCATTCA
CCTGTTGATGGACACGTGGGTTGTTCCAGTTTATAGCATTGTGAAACAAA
GCCAGTATGAACATTTGTACATGTCATAGTATGGACATGTGTTCATTTATC
TGGGAGAAATGACCCAGAAATATTGCTGGGCTGTATAAGTGTTTAATTTTA
TGTTAGAAACAGCCAAACTTTTTTCAAAGTAGTTGTAACATTGTCCTCTTA
```

FIG. 8-44

```
CATTCACAATATATGAGAGTAGTTTCCTCCACACCCTTGCTCACCCTGGGG
ATTGTCAGTCCTTTTAACATTAGCTATTCTGTTGAATGTGAAGTATCTCAT
TGTGGTTTTGACTTGCATTTCCCTAGTAACTAATGATGTTTAAAATCTTTT
CATGTGCATACTGGCCATTTGTATGTTTTCTTTTGTGAAATGTCTGTTGAA
AACTTTTACTCTTTGTTTTGGCTTGTCATCTTACTAAGTTATAAGGTTCCT
TATATTTTCCAGGTGCGAGTCCTTTGTCAGATACATGTATTATAAATATTT
TCTCTCAGCCTGTGATTTTCTTTTTCTTTTCTATTTATTTATTTATTTAT
TTATTTTTAGGAAGAGTCTCACTTTGTCACCCAGGCTGGAGTGCAGTGGC
ACCATCTTGGCTCACTGCAACCTGTAGCTCCCGGGTTCCAGTGATTCTCAT
GCCTCAGCCTCCTGCTTTTCATTTTATAATGTTTTTTGAAAAGCAAATTTT
CACTTTTGATGAAATTTATCATTTTGTTATTTATGTTTTATAAACTATAAA
CCTGTTGTTTTGTTTTAAAGAAATCTTTGCTAATCCTAGGGTGTTGATGAT
TTTCTCCTATTTTTTAAAGAAGTTTTATAATTTTAGCTTTTACATTTAAGT
CTATGGTCTATTTTGAGTTAATTTTTGCATAAAGTTTGAGGTAAGGCTCCT
GCTCCTCTCCCCCACACCGGATGTCTACTTGTTCAAGAAACATTTACTGAA
AAGACGATTTTTTTACTTATTAAATAGCCTTGACACCTTTGTCAAAACCAG
TTGTCCATAGATGTGTGAATCTATTTCTGGGTTCTCTGTTTTGTTTCACTG
ATCTTTGTGTCTAACCTTATACCAATTCATTCTGAAATACTTTCCAGATTA
CTATAGCATTTTAATAAAATTTTGATTGAATAGTTTAAGCCCTCGGACTTT
TTTCCTTTTAAGTATATCAACTTGGAGAGGATTGATTCATATTTGTGTTTC
ATTTTTTCATTTTTCAAAATTATGTTTCAAATTGACATAATAATTATATGT
ATATATGGGGTGCATAGTGATGTTCTTTTTTTAAAAAATATTTATTTATGT
ATTTATTTATTTTTGAAACAGAGCCTTGCTCTGTTACCCAGGCTGGAGTGC
AGTGGCGCGATTTCGGCTCACTGCAACCTCCGCCTCCTGGGTTCAAGCAAT
TCTCTTGCCTCAGCCTCCTGAGTAGCTGGGATTACAGGCACATGCCACCAC
GCCTGGCTGATTTTTGTATTTTTAGTAGGGATGGAGTTTCACTATGTTGGC
CAGACTGGTCTCTAACTCCTGACCTCAAGTGATCTGCTTACCTTGGCCTCC
CAAAGTGCTGGGATTACAGGTGTGAGCCACTGCGCCCAGCCCATAGTGTTA
TTTTTATACATACTGTGTATAGTGATCAGATCAGGGTAATTAATTAGAATA
TCCATTATTTCAAGCATTTCTCATTTCTTTGTGTTGGAAACATTCAATGTC
CTCTTTTCTAGCTCTTTGAAATTATTTATTACTGTTAACTATTGCCATTCT
GTAGTACAAATAGAACACTAGAACTGATTGCTCTTATCTAGCTGTAACTTA
TTTTAACGAATCTCTCTTTATCATCTCTTTCCCCTACCATTCCCAGCCTCT
AGTAATCTCTGTTGTACTTTTTACTTCAATGAGATAAACTTATTTACTTAG
TTAGCTAGCTTCTGCATATAAGTGAGAACATGTGGTGTTTAACTTTCTGTT
TCTGGCTTATTTCACTTAATGTAGTATCCTGCAATTCCATCCATGTTGCTA
CAAATGACAGGATTTCATCCTGTCATGAACAAACAAAAATTTGCCAAAACA
AAAATTACCTTAGTTATCACATTTCTTTTATTGACATAATTCATAATCATC
AGAATCATCTGACTTGTACATCATTGTATCAGTTGGTTTTATGCTCAAGAT
GTTGTATTGGTTCATTATTGTCTTAATATCCCAACCAACCCAATCTAGACA
TAAATGCTGGCCCCTGTGACATGGCAGGAAAGGGAGACAGGCCTGGGCCAA
GCATAGTGATAGCAATGCACCTGTGTTTGAAGCTGTTAAATATTTGCTACA
GTCGTATTCCTAGACTCAAAATTAGATTCTTGTTAAGTCCTACTTGTCAGT
GTCTATGGCTGTGTGAGTTCTGGTTAGTAGAAGGTGGGCAAAAGTGATGTG
TATTCTTCCATAACTGGTCCATAACCACCTACCACTCACAATACTCCATGC
CTTTTTTTCTCTTCAGGCTCCTTGGATTAGAGACCATCCTGAGGACATCCT
TGGGAGCCATGTGCTGAAGATGGCCAAGCCACAGGATGAAAGGAGCTGCAT
```

FIG. 8-45

```
CTTTGAGTCACCACTGGAGAAAGGTCTCTCTAAATGGATTTGCAGAGACGT
CTTCTCGAATACTCCCCTTCTAAGTTCCACTTGTAATCCACTTCTTCTATT
CTCCCAGCAATCAATGTGGTTTGGGGAAATTCCAGAATCTCATAATACCTT
GGTCATGGGTAAATAAGGAAAGGACCTTTACATACATGTGATGCAAAGCAG
ATCAAAACAAGCAGAGCAGCCTAAGAGCAGCAAGACCCCAAAGGATAAGGG
AAGTCCTGCAGAAGAGCAGAGCGGTGCTGCAAAGGCAGGCAGGTAAGGTAA
GCAGACAGGGCCATCAGGATGGATCCTTTGGGCATGCCAGCATCCACCAGG
GACTGGTAGAGCTATTTAGAGAAACTGATAAAAAGCTCTGCCAACTACAGT
CACAAAAGATGGAGCTCAGAATGATGAGTAGATGCCTAAAACATCTCCATT
TTGTTGATGAAGAAAGTAAAGTTTATAGAGCTTAGATTATTTGCTTTTGTA
CCTAGCACAGTACTTAGTTTATAGTAGATGCACAATAAGTATTTGTTTAAT
GAGTGAATGAGTCACTAGCCTAAGACCTTTAATATAACATGCTTAAACCTG
CTACCAGGGATTGGGAACTCACCTATTTAGTAGTGAGTAGAGGGGTGTGGT
ACTGGTACTTAAGACAGATGCATTGTGGTTGGGTATGGTGTGTTTTTGTTT
TTGTTTTGAGACAGGTTCTCCCTCTGTTGCCCAGGCTGAGATGCAGTGGCA
TTATCATGGCTCACTGCAGCCTTAACCTCCCGGGGCTCAAGCGATCCTCCC
ACCTCAGCCTCTGAGTAGCTGGGACCACAGGTACGCATCACCGTGCCTGGC
TAATTTTGTTTTTTGTTTGTTTGTTTTGTAGGGACGGGATTTTGCCATGTT
GCCCAGGTTGGTCTCGAACTCCTGGGCTCAAGCTACACCCGCCCGCCTCGG
CCTCCCAAAGTTGTAGGATTAAGGTGTGAGCCACTGTGTCCAGCAGATATA
ATGTTTTTAAAAGTTTGAGAGTTAATATGCTCTCTGGTGTGCCCTAGGTCC
CACTACTCCTATTGCCTTAAAACTCACGCAGTACACATTTGTCTTCCATGG
GCTTCAGTTGTAAGAGAACCCTTTCTACTCTTTGCTGTTCACAAGTCTCCT
TTTAAACAGAGCTTGTTCCCAATGCTGTTTTGTTTTGCCCTCTGCCATGTT
CTTCCGGCCATCACCTCCTGTGGGGAAAAGAGAGAGAGATCACATTGTTAC
TGTGTCTGTGTAGAAAGAAGTAGACATAGGAGACTCCATTTTGTTCTGTAC
TAAGAAAAATTCTTCTGCCTTGAGATGCTGTTAATCTAACCCTAGCCCCAA
CCCTGTGCTCCCTGAGACATATGCTGTGTCAACTCAGGGTTAAATGGATTA
AGGGCTGTGCAAGATGTGCTTTGTTAAAGAAATGCTTGAAGGCAGCATGCT
CGTTAAGAGTCATCTCCACTCCCTAATCTCAAGTACTCAGGGACACAAAAC
ACTGAGGAAGGCCACAGGGACCTCTGCCTAGGAAAGCCAGGTATTGTCCAA
GGTTTCTCCCCATGTGATAGTCTGAAATGTGGCCTCGTGGGAAGGGAAAGA
CCTGACCGTCCCCCAGCCCGACACCCGTAAAGGGTCTGTGCTGAGGAGGAT
TAGTAAAAGAGGAAGGAACGCCTCTTTGCAGTTGAGACAAGAGGAAGGCAT
CTGTCTCCTGCTCGTCCCTGGGCAATGGAATGTCTCAGTGTAAAACCCGAT
TGTATATTCCATCTACTGAGATAGGGGAAAACTGCCTTAGGGCTGGAGGTG
GGACATGCTGGCAGCAATACTGCTCTTCAAGTCATTGAGATGTTTATGTGT
ATGCATATCTAAAGCACAGCACTTAATTCTTTACCTTGTTTATGATGCAGA
GACCTTTGTTCACGTGTTTACCTGCTGACCTTCTCTCCACTATTATCCTTT
GACCCTGCCACATCCCCCTCTCCGAGAAACACCCAATAATGATCAATAAAT
ACTAAGGGAACTCAGAGGCCGGTGGGATCCTCCGTATGCTGAACACCGGTC
CCCTGGACCCCTTTTTTTCTTTCTCTATACTTTGTCTCTGTGTCTCTTTCT
TTTCCAAGTCTCTCATTCCACCTAACGAGAAACAACCACAGGTGTGGAGGG
GCAGCCCAACCCTTCAACCTACCTATCTTATCTCTTCCATTATCTATCCAC
ATATGTCCTCTGTATTTTTTGAGTAACATTTATAAGCATAAGTCCTTAGG
TAGCTATGCCACTTACATAATGAACTAGAAAAGGTAACCAAACAGAATAGG
```

FIG. 8-46

```
GTTGTACTCAGATATACCTTCTACAAGTTTGTGTTACACATATTTACACAT
ATTTAAAAATATATACATATTATTATTGTGCTGTGTGGTTATTAGGCAAAC
TCAATAAGCAGTTCTTATAAAGTATACTCAATGTAACTTTTATAAACTTAC
CATATTTTATAGTTATTCTGTTTTTATTAGCTGCTATAAACTACCTGGGTG
TCTTGCATGAGTCATTTTATTGTAATGTTTTTGTATCTGTTGAATGAGGAG
TTAGAAGGCATCATCTTTAAGGAGCTTTACAGGTACATGTCCAGGGCTCAA
TAATTTTATTATTATTTCCTGGACAGATAAAACCTAAGCAGGTGAAGGGGA
AAGAATAAAAGTGCAGGGTGGAAGTTGCTTGAATGCTAACTGGGTCAACGA
TCTCCCAGAAAACCCCTGTAAAAGAAACCTAAGAACCTACATCACCAGGAG
ACCATTGGGACCAGTTCCTCTGGAATCCCTGAGGCCAGATAATCAGCTGAA
GCTTTACATTCTGTCCCTTTCTGGTCATGACTTTCTCCACAGTCTGCTTGG
TGCCTCCTCCTCTGTGACTCTAAATTCTTAGGATCAACCCCTCTTGCATAT
GCACATCCGCAGTGCCTGTGGGATACGGTGTGGTGTGGGGAGGAAACTCTC
TTCTGCCTTAATATTTTCCTGTGTGCCCCAGGCCTTGACGGAATCCTGTCT
CTCCATAATGTTGCTTTTCGAGGAGACTGATTGATTGAGATGGCGTCTCAC
TTTGTCGCCCAGGCTGGAATGCAGTGGCGTGATCTCGGCTCACCAACCTCC
ACCTCCAAGGCTCGAGTGATTCTCCCACTTAAGTCTCTTGAGTAGCTGGGA
CTACAGGTGCATGCCACCACGCCTGACAAATTTTTTATTTTTTGTAGAGA
TGAGGTTTCGCCATGTTGACCAGGCTGGTCTCAAACTCCTGGACTCAAGTG
ATCTGCCCACCTCGGCCTCCCAAAGTACTGGGATTACAGGCATGAGCCAAT
GTGCCCGTCCTGAGGAGTTTTCTTCTGGAATTCCTGCTGGGTTTTTGTAGT
CAGTCCTCTCCCCATTTCCCACATTGGCTCTTGCAGACCTTCCTTTTCCCC
ATTTCTATTTGCTACCATGTCAGACATGACTTTTGCCATAGGATCTCTATT
CTACTATAGAGGAAACCAAAGCCATCAGTAGAAATTTCACTAACATGGAAT
CAGATTTATAGAAGAAAGGGGGAGGAAAGTTTTGCCTTAACACCTGGAAGG
GTTTCGTTTCTTTTAGTAGCTGGGAGACAGAAACATAAGAAAGTAGCTTAG
TAAGCTTTCTGCTGTTCAACTGATGATGTGTGAGCTGTCAGTAGTTCAAAC
TAGTCATTATCTTTATGAATTAATTATGTAATAACTTAAACAATGTCATAA
ACCTTCAAATCAGTTTAAGTCTAAATGTGTCATATTTAATAACAAGAGCAA
GAAACATACGTTATGATGAAGAGCTCTTATATTTTCTTTGGATAAAAGTCA
GTAGGCGGGGCGCGGTGGCTCATGCCTGTGATCCTAGCACTTTGGGAGGCT
GAGGTGGGCAGATCATGAGGTCAGGAGATCGAGACCATCCCGGCTAACACG
GTGAAACCCTGTCTCTACTAAAAATACAAAAAATTAGCTGGGCGTGGTGGC
GGGCGCCTGTGGTCCCAGCTACTCGGGAGGTTGAGGCAGGAGAATGGCGTG
AATCCGGGAGGCGGAGGTTGCAGTGAGCCGAGATTGTGCCACTGCATTCCA
GCCTGGGCGACAGAGCAAGACTCCGTCTCAGAAAAAGAAAAAAAAAAAAAG
TCAGTAAAATTTAAGAGAAAAATGCATTTGCTTTGGGACTTTTAATATTTA
GTCTACAAATCTAGCCACCATAGAAATCTGCTGATTAAATACGGGTTCTGT
TAAAATGGAAACATGCATTTTGGGGGAAAAAAGAGGGAGTGTTTTAGTGAT
TTTGTTTTTTACACTTGTTTATAATAAAATTTTAAGCAATCTTGAGGGGAA
CATTTTATTTCTACTTGTAACTGCATAAAGTTATGAGATAAAGTTACAAGC
TATATCACATACAGTTTGTAGCTTTATAAATTATGAAATTCTAACAGAATA
AATATGCTAATATGATGAAAATGTCATAAATTACATTAGAATATATTTTAA
TAAACCAATTCAGAAGGAGCCAATACCCAATTTCAAAATCATATTAATTGT
AAAATTAATTAGGGCAGCCAAAATATTCTGGAATTCTTTCTAATAAAACAA
ATGAGTGTAAATACAGTCGTACTGACAAATCTGAAGAATTATGCAGCATAA
```

FIG. 8-47

```
AAAGTGATTATCCCAGCACTTTGGGAGGCCAAGGTGGGCAGATCATGAGGT
CAGGAGTTGGAGACCAGCCTGACCAACATGGTGAAACCCGTCTTTACTAA
AAATACAAAAATTAGCCGGGCTTGGTGGTGCACACCTGTAATCCCAGCTGC
TCAGGAGGCTAAGGCAGGAGAACTGCTTGAATCCAGGAGGTGGAAGTTGCA
GTAAGCCAAGATCACGCCACTGCACTCCAGCCTGGGCGACAGAGTGTGACT
CTGACTCAAAAAAAAAATAAATAAATAAAAATAAAAGTTTTAAAAAAGTGA
TTATTATGAACACAGAGTAATCTAGTAAAAATGGTTAAGTGAAAACAGCAA
AATACAAAATTGAATATGTACTATAACAATATATGCAAAATATACTCAGAT
TTATAAAAATTAGAATGTAGAAAAGTAAATATAGCTCTTCATAATTTTGTT
CTGAAGTTTAAAAATATATATATTTTTGAATGGATAACTTTCTTTTTCTAA
ATGCTTACAGTAGAGCCCACGATGGTTGTTAAAAGCCCCCAGGTTCAGCCT
TCTTTAATTGTGTGGTCAGCCTGCCATCAACCCGAGGCCTCCCTCTGCTGG
GCAAATTTGGGAACACATTGAGAAATCCTTACACGTAATTCCTTCTCTTCA
TGTTCCTGGTGAGCATTTTTCCCATTGGGTTTCCATACTCTGCCCTCTTGA
AGTCCTGCACCCTGACATTGCAGTGTCATTCCTCTTCTACTGAAGTCTACA
ACTATTAGCTTATTGTCTCTAGCAAGTCTCCCTTTAGCTACAAATATCATT
CAGAGTTTTACCTTTCAGAAACTTTCTCCATGAGCATTCTGGAGTAGACTC
TAGGTGCACTAGGTGCAGTTAGAAAAAGTTCTGATTTGTTGGTGGAGCTAT
AGGAGGAGAGACAATGGTGGGCTGGAGAAGGGTGTCTACATGCAGAGAAAC
TGACTGGAAACTCAGAGAGATGATGGGGATTAAAATAATCCTATTGAATCT
GCACAAAAGTGTTTTATTATAATTGATCCTGAACTATGTAAAGGTAAGCTC
CAGTGAGTAGTTACAGTCTGTCCCTAAGATGGACTCTTTCTTTTTGCTTTT
ATTTTTATTGTATTTATTTTATTGTATTTTTTTTTCTAAAGACAGGGTCT
TGCTATGTTACCCAGGGTGGTCTCAAGTGGTCCTCCTGGCATCAAATGATC
CTCCCACCTCAGCCTCCCAAAGCGCTAGGATTACAGGTGTGAGCTACCACA
CCCAAATGATTCTTTCTTTTCAAATACAGAGTTCAGCAGCAATTTTAAAGA
AGTACTGAACTCTACTGCCTGGAAGATGGAATGGCCCTCACAATTCTTCCA
GGCAAGCTCTGCACTCAGTGGTATGGACCACAAGGCAAGCCCATTAAGGGG
TTAAATTACTGACAAACAATAATTTCTAAATATGAACATTTCAGGAGGAAC
TAAGATGGCTCCTTCTTGGAGAATAAGTTGGCCGGCTTCTCTAGTTATCAG
ACTATCAGATGGGGAGGAAAGAGCCCCTCTGTCCCGGTGAGACAGGACCCG
CCAGCGCCCAAGCTCTAAGGCTTTCTGATGAGCAAATGGGGTTTCCATCTT
TCTAGCTTCAGGACTCGTAACTACTCAGATTATTTCCTTCAATCTGGATAT
TCAAGACAAGAACAGTTCATGGTGTTGCGAAGGCCCAGATTTAAATCACAT
ATGCAAAGATACTGACATTCAGTGGAGGGTCACTTAGATTATAGCCAGATG
ACTTTCCCTAAATTGATAGCTCAAATGGTAGTTGTGGATATTTTGCTCTT
AGTTACTTGCATAGTCACTTGCCAGAGGTAATAAAGTTTTAGTGTGGTTGT
GGAAAATAATGGCCATATATTTAGGAACAAAATTTTAATGATGATTGAAAA
CTGAATTAGCTTTAACATGTGAATATGCTCAGGGGACATAGGACCACAGAT
CTCTGTTCCTTCCTATTGCCACTTCTTTCCTTTCCCTGGTAGCATGCTTCC
ATTACCCATTACTTCAAACACTGTTTCTGTGTCTCCAACTCCCTTGCATCA
TGGTCTTTTCATTATTCAGACACAGACACAGCTCGATTATGGGTAAACTTT
TTTCTGTGGCTACAGAAGAGTTGAGCATGGCTGAAGCATCGTTGAGCATGA
CTGAAGAAAACACCTAACCTTGAATTTTTTGATCAATATAAATTTATATC
CACAGATTTTACCTGACTGATCTTCATTGCCCACCAGTCCTACAAAGTTTG
CCAGATTGGTTCTGTTTCCACTTTACATACTCAGCAAATACTTATTAAGCA
```

FIG. 8-48

```
CACACTTTGTGTTAGGCTTAAGTGTAGATATTGAAGAGGCACTGGTGAATG
AGCAGAGGCTCTGCCCCCATGGGACCTGCATGCTATTTGGCAGCTCTTTCA
GACATTCTCCTCTCAAAGCTTTGAGCCCCTCTATACCCCTATAAGCACC
TACTTTCAGCTGCTCCCTCACTCCCCCCTTCATGGGGGAAATAACAGCCAT
CGTGGTAAAACCTCCACTGCCTGACAGAGCTATATTTACCATCTTTTCTTT
AATTTTTATTTTTAATGGACACAGTTGTATATATTTATGGGGTACTATGTG
ATATTTGATACATGTATAGATTGTGTAATGATCAAATCAGGAATTAGATC
AGTTTTTTGTCTTTTTTTTGGTAAAAGATAATCTTTTATACTCTTTTGGTC
CTGAAAAATGGAGGAGTGCCATATTAGGATTCCAACAGAAAAAGTTAAACC
AAAAGAATATATGAAGGGCATATAATGAAGGGATATCTACAAAGTTGTGAC
AGGGCTAATGGGAAGAACAGGGGATATGAGGCAGCCCAAGATCAGCAACAG
TAGTGATCCAGTGTCACCCTGTGCTGGTTATGAAGATTTAGTCTCTTCTAT
CTTTTCCAATACCGCTTTGCTAGCCACCTCCCCAAACCCTACCAATAGAAA
GCACTGGAGGAAGACTAGAGGGCTGGAAGGATGTGAAAAGATTTCCCACTT
TGTTTGTTGACATCCTCACAGAATGGGTTCTTCAACCTGGCAGTGGCAGTT
GAATCCAGTAACAGCAGTTGGCTTCAGTTTGGAGATCTTCCATGCTCCTAA
AATCAGCCTCATCATGCCTCTATCTACAGACATATCATCATCAGTGGTCCA
GCATACACTCCTCAGAGGTCCCAGTTCTGGGGATCTCTTCAAAGAATCTTT
TCCTTGTTCTCCTAAACCTGGAGGTGGTAGTTGCTTTCTGTCATTACTATC
TCTGATACGTTTGTCCACTTTTCCATTTTCAGTCCTCTTATAACTAGTTAA
CAACCATTCCCATAAAATTCTTTGTTCAATTTCAGTGCAATTTCTAGCTCC
CAGTTATACCCTGACAGACACACCTTTAAATCTGAAGAGGCAATGGGAGGG
AACCTGTAACCAGAGCTAGGCCAGAGCTGGGACTGTGGAGGAAGAGCTGCC
CACCAAGCAGGGGGGTGATGCAGGGAATAAGTACACTAACCTCTCTCTCCT
TTGCCATCTACATTCCTGCTGGGCTGATCACTGGCCAAATCCAGCTGTTGC
AAGAGGGCAGGGCTGCCCAGCTAATGCTATCTGTAGAAGCTGGGCTTCTGG
GGCACAGAGCAAGTCAGAGACAGGCAGAACAGGGATGTGGGTTTGGACCAA
ACACTGAATAAACCAGATCAAGGATTCTTCTATCAAGACAAGTTTATATAC
TTGCAGCTTGATCCCATTGTTTCCCTTAGATAACTGTGCACTTGTTTTTGT
CTGCCCTCTTTCCTGTGTCTACACTCTTCCTGTCTTATTCTATTTACACAT
AGCTCAGTCTTTTCCAATTAAAAAAAAAAAAAAAAAAGCTTTCCCTCTCCCA
AATCTCCATGCAGCTGCTGACTTCTCTCTTCCAAAGCCACACTGTGGGAGA
GTCAGTTACACCTCCTGACCTCTGACAGGTGCAACACACTATAGTGAGGCT
TCTGCCCTTGGTATTCCTCTGGCTCCATTATTTACAAGGTCACTAATGACT
TCCTATTTCTAAATCCAGAGTGCCTTTTTAGTTATCTTCCTTGCCTTCTTG
GCATCTCTAGATAACAATACTTGTCTCATTCTAACTTTTGTCTCTCCTTAC
AGCTCTTTCATTCATAATTCATTGTTATTCAGTTGGAGCCTTGATGGTGTT
AGGGAGAAGCAGCATTCTGTAGTCAAAGTGTTAAGCCTCAGTTTATTAGCA
TGCCTATATCTTGGGGCTGGGACCGTCACAAGTGTTTATAATGATACAACT
CCTCCTCCTCCTCCTTCTCCTCCTCCTCTTCCTCAAGTGTTTATAATGATA
CAACTCCTCCTCCTCCTTCTCCTCCTCCTCTTCCTCAAGTGTTTATAATGA
TACAACTCCTCCTCCTCCTCCTTCTCCTCCTCTTCCTCAAGTATTTATAAT
GATACAACTCCTCTTCCTCCTTCTCCTCCTCCTCAGACCTTTGCTCCTTTC
CTGGCTGCACCATTTCCAATTTATTTTCATGAAGCTCTGATCCCTGTTGAC
TAATTTTCTTCCCTTAAGTGAGACAGAAAGCCTAGATGAGGCTGCAGTGGG
AAGAATTACCTTCTCCCAGCTGGGATAAGACTCTGGCAAAATGTTTTCCCC
```

FIG. 8-49
TTGAGAGTAGGCCTTTGTTTTGAAGAAGGTTCTGGGGTGTATTTCATAATA
ATTCTTCTCTCCCTGCCAAAGCCACAAGAGGATCCTTCTCAGATCTTCACT
GCAGGAACCTGGTGGGCTTTCTGATGCCCACAAAAGTGTGGGAGCTTCTCA
CTCTCATGGGCATTCACAGTTGGCCTCCAGCTTTTTGTCAGAGTTACCAAT
TTAAATGTTCTCAAATGTGATACTGTCTCAACTTCCAGGACATCACACACT
CATGATTTTCTACTATCCTGACATTTGCAGTCTTTTTAGCAGATCTCCCTC
CCTCTCCCTGCACCATGGGTATTGGTCATCTCAGGATCTGTCCCAGGCTTT
CTACTCTTCATGCCCTTTGAGACAACACATGATCTGACCTGCCCTTTCAGG
AAGAAATGTTCTGTCTACCTACTTGCTCCAGTTAAAAACCCTAGTGTCATC
TTTGACCCTTCTCATCCCTACATCTAATCTGTTGATTCTACCTCCTAATTT
TCTCTCAAACGCATCTATTTTCTTCAATTTCAGTGCTACTCTCTTGCTCT
AATTGTACATCATCTTTTTTAGAATTACTGTGACATTTTCTTGCCTCCAGT
TCTGCCTCAGTCCATCCACTTCACAGCTAAATTTTGGATGTACACTTTTGA
ACTATTACTGTAGCAAAAGTAATATGTAATAACTGTAATGCAGAAATATAA
AATATGCAATATAAAAGAAATACATGCATAAATGATCCCAACACTAAGGAA
ACAATATTGATCAATAATTAAATAATTGGTGGATAGTGAATGACAACATAG
AGCAAAGTGTTCAGTAGGTTTTAAAAGCTGTGGGTTCAATAAATGCTCATG
AAGCTTGTTCAGGGGCTTGCAAAATATGTAATTTGAATTTTTAAAGAAAAG
GAATTTCAGATAAGAAAAAACATACATAACATGAAACAATACTTGTGGTGG
TTTCAGGGAGGTCATGTTCTCACATTCAGGTGCCAAGGCCACCGTACATCC
GGACACTGAGGCCACGGACTTGGTCTGCAACCTCCATGACAGCCTTGTAGA
TTTGAAACCGAACTCCAAGGAGCAGTTGTGCTGTGAGTTCCAGAGTTTGGG
GACAGAGGAAACACCATTCTTTGGAAGTCTAACTTCCTTAAGAGGTGTCCC
TTAGACATCTAGTGTCCGGTGTTATGGAGGTCCTTGTGCTCTGAGGAAGGA
GCCCCTTGTTGATTGATGGAGCAAAATTTTTTAAACAAGGAACTGTACCC
GTATCTGGGCATGAAGCCAGAGAAATCCCTGAGGGCAGGGCCAAGGCTCTC
AAAGATTTTCAGGGAGATTCCCAGCCTTTTTAAGTCTCGCCTATTCTTTTT
TTTTTCTCTAACTGGCCATTTTGTATATATGGAGGTTATTGATTTTTTTGC
TTTTATATCCTGATATTTTAATAACTGTTCATTTTTTAGTTATTTGAATTA
TCTACATTGATTATTTGAATGTTCTTTTTTTTGTTTTTTTGAGACGAAGTC
TCGCTCTGTCGCCCAGGGTGGGGTGCAGTGACAGGAACTTGGCTCACTGCA
ACCTCTGCCTCCTGGGTTCAAGCGATTCTCCTGCCTCAGTCTCCTGATTAG
CTGGGATTACAGGTGCCCGCCACCACACCCAGCTAATTTTTGTATTTTTAC
TAGAGATGAGGTTTCACCATGTTGGCCAGTCTGGTCTCAAACTCCTGACCT
CAGGTGATCCACCCACATCGGCCTCCCAAAGTGCTGGTATTACAGACATGA
GCTATTGCACTTGGGCTTTGAATTTTCTACGTATCTGACTTCTACGAAGAA
AACTATAATGTATTACTCAGATAAATTAAACAGGAAAACTAAATAATGGAG
GAGTATATTTACAGTTGAAGCGGTCAATATTTTAAAGGTATTAATTGTCCC
CAAACTGATCTACAAAACCATTGTAATCCTAATCAGATTCCCAATAAGCTT
TATTATAGAAATTGACAAACAGGGTTCAAATTTAATACACAAATCCAAGGG
CCCAAAATAAACAAATCTGTTGCTTTATTAAATATCAAAACTGATAAAATG
ACAATAATCAGGGCAGTGTTGTCCAAAAATAGACAAACGAATGGAACAGGC
TCAAACAAATATGGACATTGATTTACATCTAAAGTGGCACCATACAACAAT
GGTGAAAGGACTCTTGTAAATAAATGGCATGGGACAATTGTATAGCCTTTT
AAACAGAAAAAGAACAAAAAGGAAAAAAAAAGAAACTTGACCCCCTACTTC
ACACTATACACAAAAAACAATTCCAGGGGAACTAACATGAAAAGCAAAATA

FIG. 8-50

```
AAGTTAAACATGAAAAGCAAAATAAAGTATATGGTAAAAAATTTATCTTAC
CCAAAAAGAGGTCTAGCCTTTGCCCTCAGCTACTGGGAGATGAATTTTAGA
CCCTTGAAATGTTCTCACTGATAAGTGTGTCTTTGTTTACCTGGAGGTTTT
GACCACCACACAGTCAACAATGTGATTTATAATAGGAACTTTGAGCCACAC
AGTATCAGCTCTACCTGTGGAGGTAGACTAAAAGATCGGCCATGTGAGCAG
TCAACCATGGCAGGCCATTAAAACTGCACACTGAGGCTCGGGTGAAATACA
GTTCTCTTGTATACGGTTTCTACATGGTTTTAGTTCCTGTGGTCTACTGCA
GTCCAAAAATAATAAACGGTAAATTTCAGAAATAAACATTCACCTAACTTT
TATACAGTATATTCTTAACAATTATTCTAATTTATTGTTATTAATCTCTTA
CTGTGCCTAATTTATAAATTAAGCCTTATCATAGCTGTGTCTGTATAGGAA
AAAACAGCTATATAGAGTTCAGTACTATCCATGGTTTCAGACATCCACTGG
AGGTCCTGGAACATATGTTTTGTGCATAAGTGGGGACTGCTCTGTACGTCA
TGTGTATTGTCACACATTAATGCTGGGAAAGTAATACTGTTCATATTACTG
GGAGAGGACAACTGGAAGCTCATATTTGGAACTTGCCTGGATTGTGCCTAT
ATTAGTTTCCTAGGGCTGCTGTAACAAAGAGCTAGAAGCTAGGGTGGCTTA
AAACAACAAATATATTCTCTTGTAGTTCTGGAAGCTAGAAATCTGACATGA
AGGTATCATTAGATCTATGCTTCCACTGAAGCCTGTAGGAAAATCCTTCCT
TGACTCTTCCTAGCTTCTCGTACTTGCTGGCAACCTTTGACATTCCTTGAC
CTGCAGCTGCATAACCTCAGTCTCTGCCTGTGTGTCTGTCTTCACGTGA
CCACCTTAGAAGAATACTAGTTCTATTAAAAAATATATATATACTACTTCT
TCTAAGTCACCAGCCCATCATACTGTACTATAACCTCATCTTAACTAATTA
TATCTGCAACTATCCTATTTCCAAATAAGGCCACAATTCTGAGGTACTGGG
AGTTGGGACTTTAAACATATCTTCTGGGGGCAAGGGAGATCTGCATACAAT
TCGATCCATAATACTGCCTTGTGTGTTTCTTTTCTCAGCTGATTTTAATCT
TTATTCCTTGAGTTGTTTCCCCTTTTCAACTATTACAAACAATGAATTTTG
CTGTGTATGTGTCTTGGTATATATGTGCACACATATCTGCTGTTTGTATAC
CTCAGAGTGAAATTGTTGGGTCAAATGCTAAAATCTTTTTAAAAGTAGTTG
TATAATTTTACATTGCATTGGAATGACATAATAAGCTATATATCCTATAAT
AAATTGTAACCATGAGGCTAACAGCTTCAGCAAGTTCTGTGAGTCCTTTTA
GCAAATTACTAACCTAAGGTTGATTGGGAACCACAGACCTCCCAACTTATA
ATTGGTGTTAGAAGTGAGGGTAGTCTTGAGAACTAATTTCACAAGAAGGTA
TTATAAAATAAGATCTTCATGACCTTGAAATAGAAAATGATTTTTTAAATA
AGATACAAAAAAGGTTGTGCATAAAAGGGCAGTGTGCTTAATTTGAGTACA
CTAAATTAATGACTTTAATGCATCATGAGATATCATTGGCTGGGTGCAGTG
GTGGCTCACACCTCTAGTCCCAACACTTTGGGAGGCCAAGGTTGATGGATT
GCTTGAGCTCAGGAGTTTGAGACCAACTTGGGCAACAGCACCATCTCTACA
AAAAAATACAAAGATTAGCTGGGCATGGTGGCCTGCACATGTAGTCCCACC
TACTAAGGAGGATAAGATGGGAGGATCGCTTGATCCTGGGAGGTGGAGGCT
GCAGTGAGCTGTGATTGTGCCACTGCACTCCAGCCTCTGACAGAGTGAAGA
CAAGTTACAGAGGAAATACCTGCAACACATAAAATGGATAAAGGGTTCGTG
AGCAAAATTTAAAAACTTAAAACAGAAAAGACAGGCCAGGTTTGGTGGCTC
ACACCTGTAATCTCAGCATTTTGGGAGGCCGAGGCAGGTGGATCACCTGAG
GTCAGGAGTTTGAGACCAGCCTGGCCAACATGGTGAAACCCCGTCTCTATC
AAAAATACAAAAATTAGCAGGGCGCGGTGGTATGCACCTGTAGTCCCAGCT
ACTTGGGAGGAGGAGAATTTCTTGAACCCAGGAGGTGGAGGTTGCAGTGAG
CTGAGACAGCGCCACTGCACTCCAACCCGGGTGACACAGCAAGAGTCCACC
```

FIG. 8-51

```
TCAAAAAAAAAGAAAGGACAAAAAGGACAAAAAGACAGCTATCTTAAACCA
ACAAGAAAAAACACAATCTTTTTGGCCTAAATTGTGTTCCCCCAAAATTGA
TGTTGAAACTCTAACACCCAATGTGCCTATATTTGGAGATAGGGATTTTGG
GACTTTATGGAGATATTTAAGGTTAAATGAGGTCATAAGAGTAGGCCAGTA
GTCTGATAGATCTGGTGTCCTTATAAGAAAAGGAAGAGACATGAGGTCATT
TTATGGGCATATGAAGAGGCCACATGAGGACACAAAAGGCGACTGCTGTGG
TTTGAATATGAGATGACATCTCACATCTGCCATAACAGTAAGAAGGCCCTT
GCCAGAGGTGGGCCCCTCGACCATAGGCTTTATAGCCACCAGAATTGTAAG
AAATAAATCTGTATTCTTTATAAATTATTTGGTCTCTGGTATTCTGTTCAG
CACCAAACAATCTAAGACAGCAACTATCTTCAGGTCAATAAGAGAGCCCTC
ACTAGAAACTGAATCTCTTGGCACCTCAATTTAGGATTTCTGGCCTGGCCT
TTAGAACTGTGAGGTAATAAACTCCTTTTGTTCAAGCTACCTAGTCTAGTA
TTTTTGTTATGGCAGCCCAAGTCGACTGATATACAATCCAATTAAGAAAAA
ATGGGCAAAAGATGTAAAATAAAACCATAATGAGATAATACTGCACATCTG
CCACAATGGATAACATCTTCAAAAGATTAACAATTTTAATTGGAAAAAAAT
ATTGGGAAGTATATGGAAGAACAGGAATTCCCAGCTAGATTCCATCAACAT
TAGGTTTGTGAGGTTCATCCATGCTGTTTATAACTGTGGTTTTAATTTTCA
TTTCATCGCATGTAAACCTAATATCACCACTTTCAAAAAGAGTTTAGCATT
TGACCCAACAATTCCTCTCCTAGGTATACAAACAAAATATGTATTCCTATA
TATACCAAGACACATACACAGGAATATTCACGGTATTGTTTATATTAGCTG
AAAAAGGGAAGCAAATATGCATCAACAGTAGACACCTAAATTGTTGCACTC
ATAACATGGAATATTACATAACAATAAAAATGAATTAAAGTTATACACAGC
AACACAGATGAATCTATTCAAACCTAATGTTCTGGAGTGAAATATGTCAGG
TACATAGGATTACATTTGTTTTATTTCCATTTTATATGTTTCAAAAACAGG
CATACTAAATTACAGCATTGGAAATCAAAATAGGGGTTATGTTTAGGGCAG
ATGGAGTGATAATGTGACTGGAAGCAAGCATCAGGCGGCTCTGGGAGGGTT
GGCTGATTTTCTGTTTTTTACTTGTGTGGCAATTATTATGGTGTTCACTT
TGTGTTCATTTATTGAGCTTTGCATTTTTGTTTTGCTGTGGTTTTCTGTTT
ATATGTTATGCTTCTCAGTTTAAAGAATGTTGAAATCTTCTAATACGAAAT
TTTTTTTCAATGAGAAGGATTTTAAGCATCCAGAATCAATTTTAAAATCTC
CAATTTGCTTTATATGTAGGTTTATGGACTGCTTAACTGCTACTCATTTTT
TCCTTCATTTATCAATAGTGAAATATGAAATTAAAATAATGACTATTTGTG
GCAAAATTAGGGACTATGTAGCATATTAACAACTTTATAAATAAAAGAATA
AATCAACTCACCTGGGAGTTGTTACTGTCATTGACCTAATGCTATTTCCCA
TGGTACTCCTTGTCCCCATTGAGAGACATGAGATACTGCAGATTTATGGGT
CACTTTCAACATGTCTCCTCCAGGCCTCATTTTAGAGAAGCATAACATCAT
GAGGTTCTATACAGGCAAGATCTAGGCTTGTGTCCTTGAACCTTGCATTCC
CTCTCAAGAGCCAACCAATAATTGAATGATCCTATAAAAAACACAGAAACA
CAGAGAATGGTAGCAGAAAGCGGATGCTTACCAAACCTATTTTCTCTTTTT
CTAAGCAAGGAATAAGAATAACTTACCTTCCTCCCTTGGAGTTAGGAGTTC
TTATGTAGAAAGGGAGGCAGAGTGACCTTCAAGAGAGTTTGGAAGGGGGAG
TGATAAATCAGTTTAAAGAGAGCACCCACTGATTCTTAGATAACTTATTCT
ACTTTCCTTCTCACTCTTTTGCATTGACCATGGCTTAGAATATATTTGAGG
AAAAGCATACTGTCCATAAGGTATTATTGCCCTTTAAAGCTGTTGGGGGGT
ACTATGGGATGGTATTCAGTGAGAGCAGGACAGAGTCTCTACAGAATTTTC
TCTGACAAAACAAAAACTAAATGACTTCCAAGGCTTCTCTAGCTCTAAGCA
```

FIG. 8-52

```
TTCCACAATTCTTTGGAAAGCTGGAATCTAAAATTGCCTTAAAATTAAAAA
ATAAGAACAGTTAGGGTGTACAGTCTTTACCATATTTATATAGAATCATCA
GTCTTCAGTGTGATACTGTGCTTGAACCAACAGAAGGACTGATGAAACAGA
AGACAAAGTCCAGGTCTGGCGCCATGGCTCACACCTGTAATCCCAGCACTT
CGGGAGGCCGAGGTGGCCAGATCACTTGAGGCCAGGAGTTTGAGACCAGTC
TGGCCAACATGGTGAAACCCCATCTCTCCTAAAAATACAAAAATTAGCCAG
GCCTGGTGGCAGGTGCCTGTAATCCCAGCTACTCGGGAGACCAGAGGCATG
AGAATCGCTTGAACTCAGGAGGCAAAGGTTGCAACTGAGGTCATGGCACTG
TACTCCACCATGGGTGACAGAGTAAGACTCTGTCTAAATAAATAAATAAAT
AAATAAAATAATAAAATACAACCTAAAACCTAGCAATCTCAGCCCTGGAAT
TCTATTCAATTGCACCATGTTCAGCAGTGGTAACTGGAAACATCAATGCTT
ATCAATAAGAAATGGATGAATAACTTATGCTATTCCATGTGAAGGATTTCT
TTTTTCATGACAGGGTTTTAGAAAAGTTTGGTTAAGAGAAAAGCAACATGC
AGAAGTGTATATAACATCGTTGTAAAAAATTTTTATTATTTTTGTTTTGAG
ACTGGGTCTCATTCTGTCACCTAGGCTTGAGTGCAGTGGCACGATCTCTGC
TCACTGCAGCCTCTACCTCCCAGGTTCCAGTCATCTTCCCACCCCAGCCTC
CCAAGTAGCTGGGACTATAAGTGCGTGCCACTGGGCCTTGCTAATTTTTTG
TATTTTTGTCAAGATGGGATTTCACCATGTTGCCCAGGCTGGTCTTGAAC
TCCTGAGCTCAAGTAATCTGCCCATCTGGCTTCCTAAAGTGCTGGGATTAC
AGATGTGAGCCACTGCGTCCAGGCTTTGTTTTTTAAATTAATAACCCTAAT
CAAAAGACAAAACAATTATGCATACAAGGCCAGGCACAGTGACCGTAATCC
CAACACTTTGGGAGGTCGATGATCACTTGAGGCCATTTCTAGACCAGCTTG
GACAACATGGTGTGACTGTCTCCACAAAAAATAAAAACAAAAAGCCCGGCT
TGGTGGTGCGTGCATGCAATCCCAGCTACTCCGGATGCTGAGGCTGCAGGA
TAGCCTGAGCCCAGGAGTTGGAGTTGGAGGTTACAGTGTGCTGTGATTATG
CCACTGCAGTCCAGTCTGGGCAACAGACTGAGACCCAGTCTCAAAAGATAA
CGTGTTTTTTTTTTTTTTTTAAAAAAACAAAACCACAAGTATGCATGT
ATATAGATAGGTGTATGTAAAATACTTAGTTCAAAGAAAAACATGTATATT
TCTCACAAAAATAGGTGAGAATTTTTGTTTTAAAGGATAAACCTAGGTAGC
TACATATTAGTTTGAGGAAGGGGGAACAGGGATGTGATGTGCCTGTATCCC
TGACTTTAGACGATGGAAGGAGCTAAGCAAAACAATTGAAAAAAGACCGTT
TGAAAAATACAACTGATTATTAACTCATATGCACACACGCAAAAATAAACT
TTTAGAATTGAACTGCACTAAGTAAAAGTGAGTAAACTTGGCTCATCATAT
ACTCTTGTCAGATGTAAACAAAAAAGTCCAATTATTAAAATCTGACCCCCA
GAATTAAAATTGCAAAAGCTTAAAGGGGCAGTTCTGAGAAAAGGATCTTCA
GTTTGAATGTGTGGGCTCCACCAGGGTTGAAAATCCTGCACGACTGATGA
AACACGATCCAGTTAAGCACAGTAATTTTCAAATATCCAATCAGGGCGCTT
CCGTTTCTAAAAACAGAGAAACCGAGCAAGGGATTTTGGGTTGCAGCTCTA
AAACTCCAACAAACTAAGCTCCTTTGTCCTGACAAGGGCCTAAACCAAGTC
GACAGCCCGTAAGTGCACCCATGGTAAGGCGCTGCACAAAGAAAGCATTTT
GCGTTTCAAAGCTTTGTCATGATGGCGCTGCAGAAAGCAAGCGAGCTAGGC
CTACCTGGCGGGGCTTTCAGAGGACGCCAACGTGGGCGCCAGCCACGCCAG
CAGGGTCACCGTCCTTCCCAAGGACAGACAGCTCGCTAGCCACTCCTGTGG
AGAGGGCGTGGTTAAGCCATATATTTTGCCAACTATCCCAGAAGCATTTCT
TAGGACCACCCAATTTCGGAAAATGCTACTTTAGCAATATTGACCCCAAAA
CGCAATATCCCCACTTTAACCTTGTATAATAAAAAGCCTCAAGCCTGGGAC
```

FIG. 8-53

```
TGGGCTTCAACCTTGGTTCAATACGGTTATGACTAATTAGCTTGGAGTCGT
GAGACGCGGGACTTCCGGCTACCGAAACCCAGGTGACTTTAAAACTCGATT
TTAACTCGGTGCATTTGAATTCACCTTGCTATCTTTGATAGATTGAGTAGT
AAATTCTTACTAGATGAGGCTATGTTAAAGTTCTATCGACTCTCCAAGTGA
TTCTAATATAATTGAGGGCGTGTTGCATTTGCTTGGGGGATTTCATCTGTG
TACTACAGCTCTTTTCCTGAAATGCGTAGGTGGCTCTTAAAAGAGCCGTTG
GGTTACTAGAAGAAACTTCTAACTGAATTTACTTTTTCTTGGGTGCCGCTT
TCTTGGGTTTGGCAGTCTTTGGCTTCGTCACCCTAGCCTTGGCCGCCTTGG
GTTTTACAGCCTTAGCTTTAGCAGGGCTTTTAGCTACTTTCTTGGGCTTTA
CAGTTTTGGGTTTTTTTGGATTCTTGGAGGATTTCCTTGTTGCCGCAGGCT
TTTTAGCCTTTTTCGGAGTCTTGACGCTCTTTTTGCTAGCCCCGTGGCCT
TTTTGAGCTTTTTAGATGCACCCGTTGCCTTAGTTTTTGTAGCCACCTTTG
AGGCGCCGGGCTTGGTTTCCACGGAGGACGCCTTCTTGTTGAGCTTGAAGG
AACCCGAGGCTCCGGTACCCTTTGTCTGCACCAACGTTCCCTTGCTTACCA
GGCTCTTAATGCCCAGCTTAATGCGGCTGTTGTTCTTCTCCACGTCGTAGC
CTGCGGCCGCCAGCGCCTTTTTAAGAGCTGCCAACGACACACCACCACGCT
CCTTAGAGGAGGAAGCAGCCTGCACGATCAGCTCTGACACGGAAGGGCCAG
CGGGTTTTTTCTTGGAGGCTGCTGCAGCCTTAGCAGGTTTCTTTGCCTTCT
TGCCAGCTAAAGGTTTCTCAGGAGCAGCAGAAGCGGCGGGGGCGGGAGGCA
CTGTTTCAGACATGGTGACTAACACAGCACACCAAATAAAGTGGTATAAAC
CTGACGAAGCAGGATGCGAAAAAAAGGCCCCAACGCAGCCTATTTATAGGG
TGGGACTGCGCCGTGATTGGTGCCCGTCAGTGCCCGCCCCTCGCGCCCTAG
CGCCCCTGCGCGCTGCCGAGGGTTTCGCCCAGTCTCAGAAGGCAGCTGGG
GGCCTCTAGGGCCTATGGTCCTGCTCCCCTCAACGCAAGCAAACACACAGA
AAAAGCCGCTCTGGTTGCCTCATTGTGAAGGAAATTGTAGGCAGACTGCCG
CCCAGTAACATCAGAGGGTACCGCTTCTCTCTCAAAAAGCAGCTCTTTTTT
AGGGAGTAGGTTGAGAGGGGGCGGTTTACAAATGCAGTGCCACAAGCATCC
GAGGAGTTTTATTAGAAATTTTTAGAGGTCCGTTGCCAGAGATGTTAGTTT
TTAATTTGCAAGAAATGTAAAATACAGTGTTTTGAATAGTTGCGGAGGGAG
AGAAAGTGCGAGTTTTAGGCCGTGTTAGGGCCAGTTGTCATCAACTCTAT
TACATTTTCTGGCAATGTTTTAGAGCGATGTGTCTCGCGAATACCTTTCAC
GTCAAACAAGAATGAATCGTAGACAACACCAGAATTCACAAACGCTGCAAT
TAATACTCAAACTGCAAGTGTGGAAACGTTTCTGCACTTGCAACTTATTTC
CACAGTCCAATGTGGGATGCACTTCAGGAATTTCCAATGCCCTTTTCATCC
ATACAACATGCCCCAAATTGGTATTAAGGTTTACAACCTGTGTTCCATGTC
AGCACACGCAATCAGCGCACCATGACATGGTCAACTCATTCTTTTATTCAA
CAAATATTTATGGGCCTCACAAGCCTGCGAAAGGCGTTAAATGCTGGGTCC
ACGAAACCGGTTCCCTGACAGGCATTCTGCTGGGGAGTTAAGTCCACTTAG
TGTGAAAGCAAACACGGGTGATAAATGCAAGCACACCCTGGGGATAAGATT
TTATGGTAACAACCCTTTAACTTGTTTGTGGCTGTTAAGTGCATTTCAAAG
TATCAATAAGCTAAAACGATCTCACATTGCCAATCAGAGACTCAGCTAATG
GGAGAATAAAAAACTATTAAATCGACATCCACTTCTACAATCCTATTCTGG
ATAACCCCTAGCACAGCACAGCAGAGAGTGAGGTAATGCGGTCTTATTTC
CGCTCCTGCTGTGGTAGTTTTCAAATAAGTCCGAACCATGCTAAGTAACCT
GAGCTTTTCCCCTTTTTGTTCAAACAACGTGCCAACCAAATAATGGAGTGG
TCCCAGATAAGTATTGTACCCATCTTCTGCACCAGTGCTTCCTACGTCCCA
```

FIG. 8-54

```
TTTTATTGAGAAGGCATGCATTCAAATATTTCACGTAATTTCTAAAAATTT
GGAAAATAACGGTTGGAAACTCTACATCTTGGTTTGACGGCTAGTCAGTTA
TGAAACACAGGTATACAAAATTGGAAGATTTTTGTAAGTAAACCCTTTGTG
AAAGATATAAACCTTTCTTAGTGTAATAAGCGAGGTATCTGAAAAAACGCA
ACTTTTGAAAAGGAAATACTCCTAATTATCTGATTCAGGAGTTTCCACTTT
AAATAATGGGTTCTGCCTCCCTTTTTCTATTGGGTTAAACTGGTTTCAAA
TAAAATGGGAACGCTCCATGCAAATGAAGGATGATAGATCTGCTTTCTAAA
TGGCTGTTCAAGAAAATAGCCTAAACCAATCAAAAGATAGAATGTGGCCTG
TCTCTTGTGAATTTAAAAAGGTCACAATCCACTTTTCAGTGTTTTGAGATT
TTCAAAATGATTGCATTAGCTCTTGGCAATGCTAAATTATGTTCCTTGCGA
ACCACTATCCAGTTTCTCTTGGGCCAAGTCCACCTCCTGCTCCGCAAGAGG
AACAACTCCCAGCTGGTGGTACCTGGCGGCAGTGCTGGAGAAACGCCATTT
TGTGACTGGCAGAGTACACCTAGGCTTTAGAAAACAAAAGCTGCAGAACGC
TGCAAGTTTAGGATTCAAAGAGCATAATCAAGAGAAAGACGTCTCATAGAA
AATGTTTCTGAGTAATAGTGTAATCCTACTATGTTTGAGATGCTTTGTAGA
TTTCAATAACACTCCTAAGTCAATTAAAGCATTACAAAGGAATCCAATTCT
TGTGAAAGGTTTCAGAAATTCCCGTAAAGGGTACATTTCCGGAGAGGAGGT
GAGCAGTATTCCCTCTTTTTTTTTTTTTTTTTTTTCCTAAAGAGCTGA
AGGTTATACGGAATTGGGGAATTATAATACCTTTGGAATCAATGCCTTGTT
TTATGGAAAATAAACACAGCCTTCAGGTTATGAAAACCAGATGTAGAAGAG
GACAAGTTTAAAAAATTAAAGTCCAAGCCGGCGCAGTGGGGCTCCCCTGTA
ATCCCAGCTACTCTGGATGCTGAGGCGGGAAGATCCTTTGAGCCCAAGTTT
AAGACCAGCTTGGGGAACAAAGCAAAAGTAAAATAAAATAATAGTAGTAAT
AAAATACCACTTAAATAATCATCTGTAGAGTTGGAATAGAATATAGTAGCC
GGTGAAACTGCACGATTGTTGCTGGCTTAAAGATAGACCAATCAGAGTGTG
TAACGTCATATTTAGCGTCTTCTATCATCCAATCACTGCACTTTACACACT
ATAAATAGAGCAGCTCATGGGCGTATTTGCGCTAGTGTTGGGTGTTCCGCT
GTGCTGTTTTCCGTCATGGCTCGCACTAAGCAAACTGCTCGGAAGTCTAC
TGGTGGCAAGGCGCCACGCAAACAGTTGGCCACTAAGGCAGCCCGCAAAAG
CGCTCCGGCCACCGGCGGCGTGAAAAAGCCCCACCGCTACCGGCCGGGCAC
CGTGGCTCTGCGCGAGATCCGCCGTTATCAGAAGTCCACTGAACTGCTTAT
TCGTAAACTACCTTTCCAGCGCCTGGTGCGCGAGATTGCGCAGGACTTTAA
AACAGACCTGCGTTTCCAGAGCTCCGCTGTGATGGCTCTGCAGGAGGCGTG
CGAGGCCTACTTGGTAGGGCTATTTGAGGACACTAACCTGTGCGCCATCCA
CGCCAAGCGCGTCACTATCATGCCCAAGGACATCCAGCTCGCCCGCCGCAT
CCGCGGAGAGAGGGCGTGATTACTGTGGTCTCTCTGACGGTCCAAGCAAAG
GCTCTTTTCAGAGCCACCACCTTTTCAAGTAAAGTAGCTGTAAGAAACCAA
TTTAAGACAAAAGGGAATGCATTGGGAGCACTTTTCGTTTTAATGCTACTG
AAGGCTTCAAAACCAATCGATTTCGGCCGGTCGCGGTGACTCACGCCTGTA
ATTCAAGCACTTTGAGAGGCTGAGGCGGGCGGATTACCAGAAATCAGGAGT
TCGGGATCAGCCTGGCCAACATGGCCGAATCCCGTCTCTACGAAAAATACA
AAAACACGCCGGGCGCGACGGCGAGCGCTTGTAATCCCAGCTACACTCTGA
AGGCTGAGGCAGGAGAAACACTTGAACCTGAGAGGCAGAGGTTTCAGTGAA
TCGAGATGGCTCTAATGTACTCCAGTCTGGGCGACAGAGAGATTCGGTTAA
AAAAAAAGTTCGACTTAAAATAATTCTGGAGTCAGAATGGGTTTACATTTA
ATTCTTAACCCAGTTCCTCAAAGCCTGTAGCTCTGTTAAGAAAATAAAGGC
```

FIG. 8-55

```
CATTGGTCAAGCCTGCTTGGTCCCACCCTCATCTCCCCACCCTCCCCCAAT
CGCTGCTCCCGCCATTTCCTGGGGCTTGGAGGAGGGGTTAAAGGAGCGGAC
TGTAGGCGTCACATTTCCCGCCTGCGCGCTTTTCAGTCTCAGTGTCCGCTG
GAGGTGGGGGCAGGGGTAACGTAGATATATAAAGATCGGTTTCCTATTCTC
TCACTTGCTCTTGGTTCACTTCTTGGGAAGTCATGTCTGGACGTGGTAAGG
GCGGGAAGGGTTTGGGTAAGGGGGGTGCCAAGCGCCACCGCAAGGTGTTGC
GTGACAACATCCAGGGCATCACCAAGCCGGCCATCCGGCGTCTGGCCCGGC
GTGGCGGTGTGAAGCGGATCTCTGGTCTGATCTACGAGGAGACTCGCGGGG
TGCTCAAGGTGTTTTTGGAGAACGTGATCCGTGACGCTGTCACCTATACGG
AGCACGCCAAGCGCAAGACAGTCACTGCCATGGACGTGGTCTACGCGCTTA
AGCGCCAGGGACGCACCCTTTATGGCTTTGGCGGTTAAGGTTGCTGATTTC
TCCACAGCTTGCATTTCTGAACCAAAGGCCCTTTTCAGGGCCGCCCAACTA
AACAAAAGAAGAGCTGTATCCATTAAGTCAAGAAGCTCAATGTGTAATTAA
GATGAATGATACTGAGCTGACATCCTAAAAAGGAAAGATTAGGGGAACTCC
AAGTTTGCCCTCCACTCACTACATATGGGTAGGGGAGCAACGATATTCCAA
CTCTGAAGAAAGAGTGGAAAAAAAGTAGTGTTAAAAATTTGTATTAGTTTC
CAAGGGACAAAGAAGCGCTGCCCAATCAATGAGGGCCATTCGTAGCTGTCA
ACCAATCAGAACTGATGAGCTAATATTTCCTGAGGCAAGCCAGGGAGCCGG
AGGGGAAGCTAAGAAGCTTATTGAGAAAAAACAAAAACCCTGTTTTAGGAA
AAAAAAAAACCATCTTTTAGCGATTATGAAATAAAATCACAGAGACATTTA
AGTATCCCTCAATCATGTACTGAGAGCAATACTAAATTTATCGCCACCAAT
ACAGTTTTACTCTATTAAAAAGACCCTGAAAATTGAAACCCTATTCAGACT
CCTGGAATACCCAGGACACTAAATTCAGGGGAGATTAAAATCTGTTTTAGA
GAGAAAAGGCACCTTTTTCAGTGTTACCGCGGCCTTCAGCAGTTAACCTTT
TTTTTTCCCCCTTTACGCAGAAATGGAAATTTGGGTGATAGAAATATTCCG
AAATTAAATTGTGATGATGGTTGTACAACTAAGAAAACACGGTAAAATTCA
TTGAACTGTACCTAAAGTGGGCAAATTTTGTGGTACATTAAATATCAATAA
AGCTGATTATATACATACACATATATTTTTATATATGCAGAGAGAGAAATG
ATGCAAGCAGGGTGGTAGGACATGAGGTTGGTAGCATAGGCAATGTTGGTC
TGTGAAGGGCCACCTGTGCTAAACCTGGAAGCCTGGGGTTTGTCCAGTCAA
GCCATGGTAGCCATAGTTTTAAAGGATGTTCCTGATGCAGTTATGTGTTCC
AGTTAAGTACATCTAGCTTCAGAACTCAGCTGGAAAAGGGATGTGAACTTC
AGGTTAGCTGATAGGGAAATATCTTACTCTCATCTGAGTAAATATTCACAA
ATGCCTCTCATTGTGCTCTTTTTGGTACCATTGTTATAGGACTGATTTCAG
CCTCACGATGTTAGCTTCAGTGATGGATGTCTCTTTATTTTGAGGTCCTGT
TTTCCACCTGACAGTTTTCATCCAGGATTTCTTGAGGAATTACACAAGTAC
CCAGCTTGGCTTAATTTAAAACTGACAATGGAGAGAATTCATAGCTGCATT
CTGGATAGTTTCAGGAATCAGAGGAGCAAAAATGAGCCTGGTATGGAGGGT
GGGTCATTTTATGTCTTTCTTAGTTGGTATTTTAAAGATATTTATTGATCT
CATATGCCAGATATTGTTGAAATCATTGGGGTACATAAGTTAGAAAATTTT
AATTCCCTTTCCTGAATTCCAGAGTCAATGTAGAGGGGTGTGTGGATATCG
ATTACCCATATGGGAGGTATAGTCGTTGTAACAATAAGCCACGACTAGCTC
CTGTTACGTTTTGCCTGGCCTTTCATAGCATTGCTATGTTCATAGCATTGC
TGATATGTCATACTCATCTTAGGCATACCCACCACCACCTTGGGCCTTCTT
CAGTCCTAACACTCATGCAGTCCTTGTTCAGAACAAAGATAATGTTGCTTA
ATTTGCAACCCCTAGACTATCCCCCAGATTTTCTAAAGAGAAACTGCACGC
```

FIG. 8-56

```
TGATTGCTTCAGGCAGTGGCAGGTCAAGGAATGAGATGGGGAATTGATTGT
GTTAGCATTCTGGTGGGCTTAGTGGAGAGCCTGGAGACTTACATAGAAAAT
TCACACATCCTTTCATTCAACAAACCTCCATAAACTACCTGTTAAACGTCA
GCCCTGTTCAAGGTGCTAGGGATACTTCTGGGACAAAACAAAGTCCCTACC
TTCAAAAAATATATTCCAGTTGGGGGAGAGAGAACAAACACAAAATAAAAT
ATATCTAGTTATATGTATTTTTTGTTAAATATATTATTACATATATAATTC
TAGGTGGGGAAATGTTATATATATATGCTATTGAGGATAGTCAACTATATA
TATATATGCTAAATGAGCAGAAAAGCTTATTTTACAAGGGATGATTATGGG
AGGTCTCTTTCGTAAGGTTGGTATTTGAGGAGAGGCTTGAATGAAATGAGA
TCTAGAGCCATTCAGATATCCAGGACAAGACCCTTCTAGGGAGAAAGAATA
GATATAAAGGTGCTGATGCTGGAAATGCTTGGTCCATTCCAGAAACAGCAA
GGTCAGTGAAGAGAAAGAACTGCGAAGAGAATGAGGTCAGAGGGTAGCCAG
AGTACAGATCTAGTAGGTTGAGCAGCTCATCCTAGTTTGCTTGGAACTTTC
TAAGTTTCAGCACTGTAAGTCTTACACCCTGAGAAACCCCTGAGAGTCAGG
CAAACTGTAATGGTTGGTCATCTTACTTGTAGGCTATGATAAGGATGCTGG
TTTTTATTATGAAGGTGATGGAAAGCCAGTGGAATCTTTTCAGCAGACAGT
GGACATAATACCTTCAAAAAGGATCACTGTTGATGCTGGATAGAGAAAAAA
CTGTATGACAGGGGGATTAAAAGTGAAAACAAAGACCAGTTTGGGGTCACT
GTGGTCATTCAGACAAACCGCCATGGCAGCTTGCTCCTAGAGAAGCAGCAA
AGAAAACAATGAAAGGTATTCTGATTGATTTTCAACAGAGCTGACTGCATT
GGGTGAAAGTTGTAAGAAGCTCAGGACAAACAATATTGCACAATTCCTGGC
CCAAGCTGCTTGAAGAATGGAGTTCTATTGATTGACATGACAAATATCAGA
GGAAGAACAGACTTGGTGTTTACGTATAAACATATTTTGGACAAGTTCGAG
ATGCCCATTATTCAATTAGATACATCAAATATGCAGTTGTATATGAGTCTA
GAGATTTAAGGTCAGGGAGATGGTTTATAATTGCAAACACTTATTTAGAGA
CACAGTTTCACTCTTGTCTCCCAGGCCTAAGTGTAATAGCGCGATCTCAAC
TCACTGCAACTTCTGCCTCCCGAGTTCAAGCTATTCTCCTGTCTCACCCTC
CCGAGTAGCTTGGATTACAGTCGCCCGCAACCATGCCCAGCTAATTTTTTT
TTTTTTTTTAGTAGAGACGGGGTTTCACAATATTGGCCAGGCTGGTCTCGA
ACCCCTGACCCCAGGTGATCCACCAGGCTCAGCTTTCCAAAGTGCCGGGAT
TACAGGCGTGAGCCACCTTGCCGGGCCTATATTTCTTAAGCTCTATGTTTC
GTTCTGAAGCTTGAAGTGGGTGGAAGCAAACTGATAGAATTTGGAGAGGTG
GTTAGGCATCCCGGGAATGAGAAACAGCCCGAAGCTGCCACTATCACAGGC
TTTGGCATTGCTAGAAGTTAACGTGGCACTTACAGCTAGGCCGTGGTGTTC
TGTTGAACAAACTATTTGACAGAGCACAGAGCATGTAAGTGGTGAGGCCAG
TTGAGTTAGCCAAGAAAAGAGGAGTCCAAGAACTGAGCCAGAGTACACCAG
AGTATGTAGTGGAGTACAGCTTTCTCATTCTTTAGTAGGGCTGTGTAGAGA
AATACTCTATTTTATGGATGTATAGATCACTCTAGTCCTTTCTGATGAAAA
CTTTACAGTTGCCACTCATTTACTATTACAAACAATGCTGCACTACATTAT
GTTTCAGTTTTTAGCCATCTCATCTGGTCTCAGCATTTATTTATCTGCTGA
TGACTCACACATTTTTATCTCCAGCTCAGACCTCTCACCCGAACTCACTTA
TTCAACTGCCTATTCACTATATCCTCCTGTCAGGAGAAGCTTGTTAGCAAA
GTAACCAGAAAACAAAGTTGATTTTTTTTGCTGAAGTAGCCATCAATATAT
TTGTTACTAAATCAAAGATGCTGAATATTTGGCTGACTTCTAAAAATCTGG
TCACCTAACTTTGACACTTCCTAGGTCGTACAGTTTGAAACTTTCACAATT
AAATCAGTTTTGGAATTTACAATTTAAGGCAGGAATAGAAGACTATTGGGT
```

FIG. 8-57

```
TGACAGGTACAGTGAAGATGCAAGTCATCTGAGAATCTTACATCAGAGGGG
GCTTCCATCTTATAGCTGCTGCCACGGACCTCGGAGTCAGAAGAAATTTGA
GTCCTTATTTATAAAACAGACTCCCTTAGTCTACTAAGTGGGAATTTACGA
ACTGCGTAGGCAGCCTGCTTAGGGGAGCCTCCAGCCTGAGGACTGAAAATA
GCAAAGCAGCTTTAACCGCCAGTCCTACTCCAGAGAAGGGGGAGGTGACGT
CACTCAGCAGGACGCCAAGCTCAACTAGAAATGGAAGTAAAGGCTTCTGGC
GCTACCGGCAGGGGGCGGTTAAGGACGGCAGGTGTTACCAGGGAAGCTAAA
AGTACAGCTTTTGCTGACGTTAAGTCAGATACGCCTGGGAAAACAGACCTG
ACACCCATTTTAATCCACCTACTCAGTTCCAGGCAGCTAGCATCTTAGGCT
CTCGTACAAATAACGCACAACTCGTTTTTAAAACTAAAAAGCTGAGCTACT
CATTTATCGGACTCGCGCTGCACGTTAAGTTGCTTGACATGTCAAAACTAT
AGCATTGAAGTTTATAGCTCACTTATCTCGGAGACCTCGTTTACTTAGCTG
ATTTCTGCTTTAGCAGCCACTCAGACCAAACAACCTGGTCTCTCCCAACTG
GTTTATAATAGTTCTACATACTAGGCAGAATAGCCGAGTAAAGCCATTGAG
ATGTTACCATCCGAAAGAATACAATCACAGCTCTTTCTGAGAGGGAGTGGG
CGGCCCTGAAAAGGGCCATTGGAAGAAAACTGACGAAAAGATTAACCGCCG
AAGCCGTACAGAGTGCGTCCTTGACGCTTGAGCGCGTAAACCACATCCATG
GCAGTGACAGTCTTGCGCTTGGCGTGCTCCGTGTAGGTCACGGCGTCCCGG
ATCACGTTCTCCAGAAACACCTTGAGAACGCCACGAGTCTCCTCATAAATC
AAACCGGAAATTCGCTTAACCCCACCACGCCTAGCAAGGCGCCGAATGGCC
GGTTTGGTGATGCCTTGGATGTTATCCCGCAGCACTTTTCGGTGACGCTTG
GCACCTCCCTTACCCAAACCTTTACCGCCTTTGCCGCGACCAGACATGTCT
AACCAGCTGACAACAAAAACCAGGTACGCGAAAAGAAAGCAAGCCACGAGC
ATTTATACACGAACATCGGACCTTATTGAGAACTGAAAGCGGGAGCGAGGA
TAAGGAGGCGTTGCTGCCTCACTTTTTGCTCCGCCCCTCGAGGGGCAGTGA
CCTAAGGACTGCGAGGGAGAACACAATAGTTTCACTTTTTAATCCCTTTAG
TTTTTCCCTCCCGTTTACGACACTACTATTTGAATCTGAATTTATACCCTC
GACTGAGAATTTTAATAAGGGCTTATATTAAGGGCTTTCACTAATATGCCG
GAGTGGTAAACTTTTTAAGTCTTTCAAGTGCTTGAAGACATATTGACTATT
CAAAGGTACTTAAAAGAGCAGGCGTGAAAAGATCACTCTGGCCTTATGTTT
TCTTGAAAGCTGACCTGTTTCTTAGAAGCAGTAGGTGAAATTCTCATATGA
AAGATGTTCTCACTGTAGTTTAAAAAAAGCAACATTCTTCTCAAGGATAGG
AGGCTGAGGCCAAGAGAATTCTGTACAAACCTTGCACTAGCCCTTGCTGGG
CGCTTCTCTACACAGTTATATATTCTAGCCTAAATCCCTTTGCTTTAGCGC
ATTTTACATTTTACTAATTGTCCAATTCATTATATAAGTAGCTAACTGCT
TTTTTTGGGCTTTCATTACCTTATGAGAGCACCTGTGTCACGTAAAACCTG
TGTTAAATAAATGCATATACCTTTCTCCTGTTAATCCATTTTACATTAATT
TAATTTGCTGGTCCAGCCAGAGCCCTAAGAGGATGGGAGTGGAGTTTTGCT
ATCCTTCACACTGTACTGTCTCATTCAGAAGAGGGTGATAGCTCATTGCAA
CCGTGCCTTCATCTGTAAATCGGGTTATGATGATACTCAGGGGACTTTTAA
TTAGCTAATGTGAACGAGGCATGAGAAGAGACTGTGGAAAAGAAATAAATA
TTACATAATATGGTTTAATTTTAGATGTTACTACTTAAAAAAATCTGCTCA
GAGTTGGGATATTGTCCTGAACTCTCATTTTCGTGTTTTTACTCCCAACAC
TATATTGCTAGCAGCAACTATGTATGTATTAGTAAGGATTGTTTTTTTAAA
ATCACAGCCTGTAATAACGTACAAGGTGTTGACAGATTCCGTTTAGCTTTT
CATATGTGACATGTTAAAATTGTCCGAAAATATTCCTTTGTTCTCTTTTCC
```

FIG. 8-58

```
AAGGTGCAATACAATAGCAGCATTCGTGCTTTCCTATAGCCAAGTCTGGAG
TGTAGTTCAACTCTCCATACACGCTTCTCACTGTTGTTTTAAATTTCCTGA
AAACATTCTTAAATCACTTCTATTGGAAAAACTGCAAGGGCTACTGCTAAA
TTTTTAAGTCTGAAAAATGCACCCCAAACTTGACTTCTTTCTCTGAGAATC
TTAGCCATCTCACCCAAATCTAACAAACCAAAACTGATTTTAGACTTCAAC
AGCATTAGCTGTAAACTTCAGCCTGCAGCATAACATCACTTTGTTGTGACT
GGGCAGGAAAAACCCTGTTAAACTGTTTCAGGCGCGTCCGTGTGAAGAGAC
CATCAAACAGGGTTTGTGTGAGCAACAAGGCTGTTTATTCTACCTGGGTGC
AGGCGGGCTGAGTCCGAAAAGAGTCAGCGAAGGGAGATGGGGTGGGTCCGT
TTTATAAGATTTGGGTAGATAGTGGAAAATTACAGTCAAAGGGGGTTGTTC
TCTGGCTGGCAGGGGTGGGGGTCACAAGGTGCTCAGTGGGGGAGCTTTTGA
GTCAGGATGAGCCAGGAGAAGGAATTTCACAAGGTAATGTCATCAGTTAAG
GCAGGAACAGGGCATTTTCACTTCTTTTGTGTTTCTTCAGTTACTTCAGGC
CATCTAGAGGCATACGTGCAGTTCACAGGGGATATGATGGCTTAGCTTCGG
CTCAGAGGCCTGACAAACTGAACAACTGGGAACAAACAACATTTAATGCAC
ACAATCTCTATCTTGTAGGGAGGCAAAATTTTACCTCTACTCTGTTAGGGT
CTCCAGCTGGACCTGATAATTCATTTGCCATAAAACAGATTAGCAGAATGA
AAGCATACAAATGTATTTAATGTAAATTTTATGGGACAGGAGAACCCTCAT
AAAAAAGTGAAGCCCCAAAGAAATGGCAAAAGCTAAATGCTTTCACATTAA
GTTAAAGAGAGGCAATTGTGGGAAAGTAAACCATATGAGGAGATTAAAGGA
ATATATGATTATTTTAACAAGGTTTGTTTGTGTATAGAAGTCTCTCGGCTA
TGACTCCCTGCTGTGTTTGTGCAGAATTATCTCATCTATGCCTCTGGGCTG
AAGAATATGTCTTTTCACCTGGTACAAGCAGAGCATTTTTCACATTGGAAC
TTTTATCTCCTGTTTTCAGAAAGAAAAGTTTAGAAGAATTCCCTTCTTGAA
TGCTGTTTTGAAGTGCCTTTAGCTCAAAAGAATCCTGATCCCACAGTGGT
CTATTTTGGATGGTATATTCTGCAAACAACACCCCCTTTTTGTCTCCAAT
CTCTCCTTAATTACTCCTCTAATACAAAACAATAGATTCTTAATATAATAT
TAAAATGTTTGCACTACTCACAAATACAAAATGCTCAATAAATTTTCTTTC
ACAAATGAGAATTTCATCCATTCGTTAATTTTTAAATATCAACTGTCAATG
AAGAGTTACAGCAGAATCCTTGTTCTGTTGAGGAGGGGGCAAAGAATGTAA
GTGAGGGAGTGGAAAATAGCTGGACTGAGCTACCACCCCCTGTCCATCTGA
TCCTCAGACAGTAATGTAACTTTATTCTTTTATGCTATTCGTCAGACCCAG
TACCTCCAACACATTTGTTTCCTACAGATAAAGAAAATATAAAAAGTCAAG
CGCTATACATCAGATCCAGCACATCTATAACTGGAAAAAAAATACTTGACC
TTCAGCTGGGCCCAGAGCTTGTGAGTAGTCACCTTGGCATAGACCAAGTCC
ATTGGCATCTCTAACATATCTATACTGTCTGTGGATAACAAATGTCTATGC
CAGTTAGAGTCGCTTGTATAAGAGTCAAGAAAAACGAATCATAAAACAAAC
TGACATATTCATTTTCATAATTTTTAAAATGCAAATATTACTTTATAAACC
AAAAACTGCCTTATTAAAAGCTGGAACACAAATGAATTTAAGTAAACGATG
CAATTCAAATTTAATCTTTTGTGTGTGTGATTTGTTGTTGTTGACAGTTGG
TCAGGCGATTTTAGTATGGTACATCAGTTTACATTCTAGATGTAGGCCAAG
AAAGAATGTTAGGTGTAAAAAATATTTATTGTAAAAAAGAATGTGAGGCAA
GGTCTTTGGAATTAGTAGTTTTAATGTTGGACATTCTGTGGTTGTTCTAAA
GTTAGTCTGTAAAATGTGATGTAAAAGCTATATGATAAAAAAATACAAAAT
ATAAAAATTTTAAAGTAAATATTACTTTTGTTTGCGTACAGTATTCCCATC
CCTCTAAATTTTCTTCCAGTACTCAATCCCCAACCTCCAAAACCGAAAAGC
```

FIG. 8-59

```
AAGATCAACAGAAAGAAAATGGTTAAAACTTGTAAATTCTAGATTTTAATA
ACTACAGGCAAGAAGTACTGAAAAAAAGAATGTGGCATGTCATGGTGCATA
GTCCTAGAGGAGACAAAGCAATGCAACCAGATAGACTATTTACAAGCAAAG
CCACACATATAAAAATTCATATATAAGGGATTAAATTATGCTTGGTCGACA
GACTGACAGATTTAAAGTGGGTAGCTAGCTATGGATAAAATGAGAGCCAGT
TAGATCCCTGCCTCACATTTTGCACCAGAATAAATTTCAGGTTAATGTTAA
CAGCCAAATGAATTTAACAGTATATATATATATATATATATATATAATATA
TGAGAAAACCTAGGGGACTATGTATTGAGCTGAGAAAATCTTCCTAAGCAT
TTTGAGGAAGACACTGGAACTCGCAAGACACAATTTTCTAATCTTTTCAAA
GCTTTGCAAAAATGCCTAGTAAGCGCCAGTTAACTACTTACCAGATTTTTC
CCTTACTCTTACAAAGTTGTTTAAACAAATGCTAATCATAGCAAGCTAGAG
GCCTGAATGATAGTGGACTTACACAGCTTCTCTCCAAATAGCACCTTAATA
AGGTCAGAAATAACCTACACTGCAAGACTGACCAAACCGTTATTTCTGTTA
ATCAACTTTAAGACCATAGTCTAATGCTTTCGGGGGGGTCCTTAGAAATT
TGTTCTGTTAAGACAACAAAAAATTATCACAGCTACTTTCGTTGGAATAAG
TGGGTGGCTCTGAAAAGAGCCTTTGGGTTTTAAGACTGATGAAAAAGTGAC
TTTACATTTACGCTCTTTCTCCGCGAATGCGGCGAGCGAGCTGGATGTCTT
TGGGCATAATAGTCACTCGCTTAGCATGGATGGCGCAAAGGTTTGTGTCCT
CAAAGAGCCCTACCAAGTAGGCCTCACAAGCCTCCTGCAGCGCCATCACCG
CAGAGCTCTGGAAGCGAAGATCGGTCTTGAAGTCTTGGGCGATTTCTCGCA
CCAGGCGCTGGAACGGCAGCTTCCGAATCAGCAACTCGGTCGACTTTTGGT
AGCGGCGGATCTCGCGCAGAGCCACAGTGCCCGGGCGGTAACGGTGAGGCT
TTTTCACGCCGCCGGTAGCCGGCGCGCTCTTGCGAGCAGCCTTGGTAGCCA
GCTGCTTGCGTGGCGCTTTACCGCCGGTGGATTTCCGAGCTGTCTGTTTAG
TACGAGCCATGGCAAAACCACAGAAAAGCTTGCCTGCAGAGACGTCTGTGG
AGGAAAGGAAAGAGCTACTCTTCTTTTATAGAGTCAGACCACCAACTATTG
GACCCAAGAAAATTCAAAAATCCCCGCGCCCTTCTTGGATTGGTCCATCTC
TGTGCCTGGTTGCAGATTAAGAGAGGCTCCTGCCCATTACCGTAGCTACTC
TGACGTCATTTTGTTAACCCCTTAGCTGCTATATCCACTGTGGACAAGTCT
TGTACTGGAAAAGTTTCCTGAAGTCTTAAAATTTACAACCACACAAAGCAA
CGCGGAAACCTCCAATTGTTTCTAGTTAAAATATAAAAAAGAAATCAGAGA
ATATTGGAGACGATTAGGGAAATTTGCATATGCGCTTTATTTAAAATTGTA
TTTTTCTGGGTGTCGCATAAGAAGTGTGGGCAATTAGAAAAATGCTCTTAG
CCGGGCGTGGCGGCTCTCGCCTGTAATCCCAGCTACTCAGAAGGCTGTCAA
GAGGATCGCTTGAGCCCGAGTTCGAGGTTACAGTGAGCTGTTATCACGCCG
CTGCACTGCAGCTTGGGCGAGAGGGAGACTCCACCCCAAAACAAAGCAAAA
CATCCCCAAACTGGAAAAAAGCTCATTTTGGGAAATACATACTCAAATGTT
CAGTGGTAATGTGTGTGCTCTCAATTGTGTATGCCATTAATTGCTACAGCA
AATGGTATGACATATTCAAACTTGTGTGGGGCATGCGGGTTTTAACACTTC
CATTCAAGATAGTTAGGAATGCACTCATGGGTATAATTTCCTTCCTCTAAA
ATGTAGTAACTGCTGTGTGTGAAACTTAACGCGAATCACCCCTGTAAACAT
GTTTTGTGCTGCATGGCACTTCTCCCACATACCTAGAATTCCTGAGGTTTC
TATGGATCTAATTTCTGCAGGACAAATTACTAAAAGTGCCACACTCAAAGC
CATTAAAAACACCTCAAAAACATCTTTATGGGCGGCATAATCCAAAGCACA
ACAGCTCATTTAATGGAAGTCGTAGGTGGCTCTGAAAAGAGCCTTTGCTGT
TAGGCTGATTTTGTCTGCTGACAGAAAAACAGCAGTGCATGAAGCGTTAAC
```

FIG. 8-60

```
TCTTCACTTTCCCTTGGCCTTATGATGGCTCTCAGTTTTCTTAGGCAGCAG
CACCGCCTGAATATTAGGCAAAACGCCACCCTGCGCGATGGTCACACGCCC
CAAGAGTTTATTAAGCTCCTCGTCATTGCGGATGGCCAATTGCAGGTGGCG
CGGGATGATGCGGGTCTTCTTGTTGTCGCGGGCCGCATTGCCCGCCAGCTC
CAGGATCTCGGCGGTCAGGTACTCAAGCACCGCCGCGAGATACACCGGCGC
GCCAGCCCCGACGCGCTCGGAGTAGTTGCCTTTGCGGAGCAGGCGGTGCAC
TCGGCCCACAGGAAACTGCAAACCTGCACGAGAAGACCGAGTCTTAGCCTT
GGCGCGAGCTTTACCGCCTTGTTTGCCGCGACCAGACATAACTACTTCTGA
TAAGGGAAAATCGCCACAAGAAAATGTAATGAAACTACATTAGAACGCAAG
GCAGAGAAGTATTTATACTGACTGGAGGTAGGCTGTGAGGAATTCTCCCAT
TGGCTAATGTCAAATACCCAATGGGAAATCAGAATCTGCATCCTTCATTTG
CATGTAATCCTTCCGTCTGGTGTAAGGTTTATGTTTGACCCAATCCCCAGT
CTGGCTTGACGAGCCTTCGACTTGAATACTAATAATAATTGGCCGAATTAG
GATTTTGTCAAAATACCTTTTTTAAGCATGAGTGGAGGTTTTGTTCTGGTT
ATTTTGACTTTCAGCCGCTCGTGCTTTTCCCGGATTGTGACTCATGTTTTT
GGAAAGGAGTGGACTCCGACCAATTTCTAAATAGATATTTAAGAGGTCCTT
CAAATCGGGCGCAGTGGCTCATGCCCGTAATACCAGCACTTTGGGAGGCCG
AGGACGGCGGGTCAGGCGTTCGAGACCAGCGTGGACAACATGGAGAAACCC
TGTCTCCAGTAAAATAACCAAAAAAGAAACGGGGGAGAAAAAGAAAAAAAA
AAGCCGGGCTTGGTAGTGCACGCCTGTAGTTCCAGTTACTCGAGAAGCTGA
GGTGGGAGGATCGCTTGAACCCGAGAGGAGGAGGTTGCAGTGAGTTCACAT
AGAGCCACCACACTCCAGCGTGGGCGACAGAGCCAGAAGACTGTGTCTCAA
AGACAAAAAAGGGGAGGGGAGTGGGAGGGAAGAAAAGCGAATACCCCAA
ATCCCAGTGAACTGTAGAAGCTTATAAGCTCTCTTGATTCATAAGGGAGAA
AGAAGGGGGATGTAGGCAACTTAGGGGAGAGTATATGATTTTGGAGAAAAA
TAAATGGGTGTTTCAAAGAATAGGTGACAGCTGTGACAAAGTCTGTTTAGA
TGGTGTTAACCACCAGTCTCCTCTCCTGTGATACAGTTAATCTTCTCTGGT
TGATGAGATTCCCCAGGGAAGTGAATCTTAACAACTAAATTCCTTTTTGAA
TTTTTTTTTAATTTTCAAATTTTTGATTAGAGTTCAGCGAAAGCCCTTCCT
TGAATTTACTGTTTCCTAGGTGCCCTCAGTTCAAAGAAATCAGCGTAACAA
AGTGGCACATTTTTGAGTTGCATTTCCTGAACTTTTTCACAACACTGAATG
AGGAGTCTCTGGAATCTTTCAGGAAATGAGAGAACAAACATTCCATAACAC
AGAAATACTCAAAATGGGATTATGATTATAAAAGTGTTTCACTGACCACCT
TCTGCCTTCCTGTCTGTAAGTCCCATTCTCCCCAAAGTCTAGCCATAGAAA
CCAGAATTCCTCCTCAAGGTAGGCCATACAAACCAGAACTCCTTTTCCCTA
GAACCAGCCATAAAACCTAAAAGTATTACTCTAACCTACCTTGTTTGCCTG
TAGGTCATAAGACCCCCCATTCTAAAAGAGAGTCTTGTCCTATAACCAGAA
GGAAGAAATGCTGCACTGAGAGGTCAAGAAGAATCTTGACAGACAAGCCTT
GCGGGGCTTCCCCACTCAGTCTGTTAGCATTAGATCGTACCCTATACAGCT
GTTTATCTTGTTGAACCTAAGCATAAAAATGGGCAATTTCCCCTGTATCTT
TCAGTCTTAATTCTAAAATCTCCTGTAAAATTGTGATGAAATAAATATATA
TGCCTTTTCTCCAGTTAATCTGTGTTTTGCCAGTAATTTTCCATAAACCTT
GGGAGGGCAAAGGGGAAGTTTTTCCTTGGCCGGGACAATATTATTACAGCC
ATTGTCTGGCTCTCCTGTTGAGGAACCTAAAATCAAGACAGATTGCCTAGG
GAAATCTTGGTGTTTTTCCTTTTATATTCCATGAGATAGGAGCAGATGGAG
TACAGATGAACGTGGATTAATTATTCCAGGAATTTCTGAGGTATCTACTAC
```

FIG. 8-61

```
TTCTATCTGTGGTCTGCTTATACTGAAACAGGATGACAGAAGGAAAAAGAA
ACATGAGTGTAAAAAAATCTGCTCCTGGCTGGGCACGGTGGCTGATGCCTG
TAATCCCAACACTTTGGGAGGCCAAGGCGGGCAGATCACTTGAGAACAGGA
GTTCGTAACCAGCCTGGCCAACATGGTGAAACCCCAGTCTTCACTAAAAAT
ACAAAAAATTAGCTGGGCGTGGTTGTGGGAGCCTGTAATCCCAGCTACTCC
ATAGGCTGAAGCAGGAGAATCGCTTGAACCCTGGAGACAGAGGTTGCAGTG
AGCCGAGATCGTGCCACTGCACTCCAGCCTGGGCAAGAGCGAAACTCCATT
TCAAAAAAAAAAAAAAAAAAAATCTGCTTCTAAGCCAACGCTGTCACAGAA
CTATGGATTTGATTCAGAGAAACTGTCAGGAGACTAAAAGTGCTCATTTTT
AGTTTGTTTTTTGCCTTCTCCCAAGTCTTCTGACTCTAGTGTTATCTTTCC
CTTCACAATATTCAACTTCCCTTTTCAAAATTATAATGATCTTCACCCTCA
ACAATAGCCGTAAACATCAGTAATCACTGGCTCATTTTCTTTGAAAAGGTA
CAAGATTCATGATGGAGATGTTAAAAAGTTATCTCAGATAGTGCCCTGAAG
AGATTATACTCAGAGAAGGGAGGACTTACGTACATGAAGATTAAATAGCAG
TGCACGTTCTGCATATAAAATAAAGATTTTGAGCAATAAATCATACAAAAG
CACATGGAAAAGAAGATTGATCAATGTAAATTAGAAGGATTTAGAGAGTTC
ATGAGGGAGATGTATATCCAGCATTATTAGTTCAGCATATATTTACTGAAA
ACCTGCTAAGTGCCAGAGAGTGTTCTAGGTGCAGGGAGCATAGCAGTGAAA
AAGCAGACAACCTGTTTCCTTACGGTGCTACTTGTCTTGTAGTGGGAGGTG
CACAATAAGGTAAATACATAATGAAAATGTAGAGATAAGTGATGAGTGCTG
TGGAGAAAAATAAAGAAAGGGGATAAGAAAAAAGAATAGAAATAAGGATGG
AAAGTTTCATCAGGAGAATGTCATTTGAATTCAGACCTGAAGGCAAGGAAG
AAGCCAGCCAAGTAGGAAGGATAAATACTTCGATAAAATGCTGGATGTGTT
TGAAGTCCAGAAAATGTCAGGAACCGTGGTTCAGAAAGTACAGCTATTCTA
ACTTCCTAAACAAATCGTAGACCATTTTGGAAAGAGCCTTGGATATGTACA
GGGCTAGATAAAATTGAAACCAAGATTAAGGGTAGCTTCAAAAACTCAGAC
TAGAAAGCAGGAGTACATCCAGTCACAATATCAGTAATCTATACTCCACTG
AGCCATGGATGAGAAAAACTCTTCTTCTCATCCAAGTTACCTTGAATTAAG
CAAACCAACAAGCGCCTGGCATGTACTATTAGCAAAACAACTTGATGGCAA
TCCTTTCAGTAAGTGCTTCAAAAACAGTAAATTCTAGGCACTTGCCTTCAA
AAAACATACAAAAGGCAGATATTGGGGAGGGAAATATTGGGGGTTATTTAT
TCCATATAAATATAAGAGGAAAATAAGTTGTTTCCCAATAACAACTCCAAC
ACCAGGAGCAGAGAAAGTAAGACAATCTATGCCTCGTGGTTTGCGAAAACA
ATAAAAAAAATCTGTTAATTGCATAATACAATTCACCCTTGAACACGCTCC
AAATCAGTGCCCACTAGCTACAAGTAGCTACTGTGAAGTTGAAAAAGGGTA
CTTCAGATTGAGCTATTCTGTAAATATGAAATAGACTTAGTGTGTTAGTTC
GTTCTTGCATTACTATAAGGGAATCCCTGAAACTGACTAATTTATAAAGAA
AAGTAATTTTTTTGGCTCACGGTTGTGCAGGCTGTACAGGAGGTGTGGTG
CAGGCATCTGCTACTGGCAAGTCCTCAGGAAACTTCCAATCATGGTGGAAG
GTGAAGAGGGAGTAGGCATATCATATGGTGAGAGCTGAGCGAGAGAGATGG
GGGAGGTGTCACACTCTTTTAAAGAACCAGATCTCTTGTGAACTCAAAGTG
AGAACCCATTGATTACCCTGAAGAGTGCGCTTCATGAGGGGTTCACCCTCA
CGATCCAAAAACCTTTCACCAGGCTTCACTTCCAACATTGGAGATTACATT
TCAACATGAGATTTAGAGGGGACAAATATCCAAACCATATCACTTAGTATG
AAGAAAGAATGTAAAACATCTGACTAATAATTATGCATATTGAATACATGT
TATAATGACATTTTGACTACAAAAGTTAACGAAAATATACTATTGAAGATA
```

FIG. 8-62

```
CTCAAAAATTTAAAAATACATATATAATTTGTAGTACATTTGTACTGGGCA
GAGGAACCTCTAACAATGTTCCAAATGTGGCCTGTGTATGTGTATGATGTA
GGAGGGATCAGTCATGTAAGATGATCATAATATAGTTACTTAGTCCATTTT
GTGATACTATAACAGAATACCACAGACTGGCTAACTTTTAAAGAAAAGAAA
TTTATTTCCTACTGTTCTAGAACCTGGGAAGCTAAGGGCATGGAATTAGTA
TCTGGTGAGGGCCTTCTTACTGCATCATAACATGTTGAGAGAGCAAGGGTA
TGTGTGTCAGCTCAGGTGTCTCTTCCTTTTCTTATAAGGCCACCAGTCTAA
AGGAAATCAAAATATTTTACCCCAAAATATATTTCTTTGACATATTTTGAA
ATGGCTGCTGCTTGGCCAGCAGGCAGAAATGGGCTTGCAAAGCTGCCTTAA
ATGGGAAAAATTTTACATCTGTAGAGAATCTCCATTAATGCAGCCATGCCT
CCTCACCTTTCTATACCTTTCCCCAGATCCAGGAGAGACTGAGAGTCTGAC
ACTTAAAAATCATAAAAGAAACATTTACCATCTGTTCTTTCTGAGGGAGGC
TTCACCTACCTAACAAGGCCACCTTTGCAAGCCAAACCTCTTTTGCCTCCC
ATAACCTGTTTTACCAGAATCTAAGCCCCAATTCTTTCTGTGATCTAAAAA
TGGTATATAAGCATCTATAACTCATTGGGAAGTTAGGTAATTAATTCTGAA
TGCTCCCACATAGACACGTTAAACAATAGGTAAAATGCCTTTTCACCTATT
AATCAATCTGCCTTGTCAGTGATTTCTGGCAAACATTTAGTGGGCCAAGAG
ACTATGGTTCCCACACTACCCTTCATGAACTTAAGCCCTAAGATATCAATA
ATTGCATTAAATGTGTGTGGTATAAATACACCCATAAAAAAACAGTTTGGC
TGGGCGCGAGGTCTCACACCTGTAATCCCAGCACTTTGGTAGGCCGAGGCT
GGCGGATCACTTGAGGTCAGGAGTTCGAGACCAGCCTGGGCAACATGGTGA
ATCCTGTCTCTACTAAAAATACAAAAATTAGCCGGGTGTGGTGGCGCATGG
CTGCAATCCCAGCTGCTCAAGAGGCTGAGGCAGGAGAATCCCTTGAACCCA
GGAGGCGGAGGTTGCAGTGAGCTGAGACTGTGCCACTGCACCCCAGCCTGG
ACAACAAGAGTGAAATTCCATCTCAAAAAAAAAAAAACAACAACTGTACAC
TGTCTGCAAGAATCTCACTTCAAATATAAACATAACGCAGGTTGAAATTAA
AGGCTGCAAAAAAGATAAGCCATATAAACATCAGCCCAAAACTGCAAGAGT
ATCTGTATTAATAATATCTGGGATCTGAAAGACCAAAATAGATGCCCCTAT
ACCAACTAAGACAGACTCTAAGATTAAGCAAACAAAGTTACCTACTGGTAG
AGCATTCATGGCTTGGCTGGCATGGCAAATTCCTAAATTCCAAAGACTACC
AAAAAACTCACACTTGCTAAATTCCTTAACTATAGGAGCTATCAGAAGCCC
TCCTAACTCTGATTTACAGTCCAGTCCACTACAACTCTGATTGGACAGAGG
ACCGCCTTGACACACATTCTATTCTTACACGTAATTGTAGACCTTAAGCCA
TTTTCAGCCAGCTGCTAGAGGCAGCACGTAAACTTTGTTCCTATAGTTCAC
CTTGTGATGTAAAGACCTAAATTCTACCTCATTTTAACCAAAATTTAACCT
CGAAGTGAACATGGGAGGTATATTACACGTGTTTATCCATTGTGAATGCAC
TTGGCACCCCTCATAATATATATAGCTGTCCCCCCAAACGTGCTAAATATG
TATGACTCTATTGTGTAATATATAGCCTATGAGGCATAAAAATAACCAACC
TGCTCCTTCTCCCCAAAGAGAGAGTAATTTTGGCAGGTTCTGGGACCATCT
CTTCCTGGCTTGCAAATTAGTATTGCCAGTAAATCTCTCCTTTCTACTCTT
TAGCCATCCTGGTGGTCTTTTGGATGATATATCAGATAAGTATATTTCAGA
GCAAAGAAAATTACTAGGAACAGACAGGGATATTACATAATGATAACAGGG
TCAATCCAATACGAAAAACAAGCAATTCTAAATGTATATGCACCAAATAAC
AGAACTGCAAAATATGTGTAGCAAAACCTGATAGAACCGAAAGGAGAAATA
GACACATACATGATTTAAAGGTAGAGATTTCAACACCCCTTCCCCAATAAT
TGATAGAACAACGAAACAAAAAAATTACCAGGTGTATAGAACTCAGTAAGT
```

FIG. 8-63

```
GACTGTATTACTTGTTTTGATCTGTAAAACAATGATAATAATAGTACTCAC
ACTTCATTGAGTTTTGGTGAAGATTGAATGAATTTATACTTATAAAGAATT
TAGAAATGTGGCCGGGCCCAGTGGCTCATACCTGTAATCCCAGCACTTTGG
GAGGCCGAGGCGGGTGGATCACCTGAGGTCGGCAGTTCGAGACCAGTCTGA
CCAACATGGAGAAACCTCATCTCTAATAAAAATACAAAATTAGCCAGGCGT
GGTGGCGCTTGCCAGTAGTCCCAATTACTGGGGAGGCTGAGGCAGGAGAAT
TGCTTGAACCCTGGAGGCGGAGGTTGCGGTGAGCCGAGATCGCACCATTGC
ACTCCAGCCTGGGCAACAAGTGTGAAACTCCGTCTCAAAAAAAAAAAAAAA
AAAAATCTTAGAAATGTAACTGACATATCATAAGCCCTCAAACTTAATAAT
CTTTTAATACATGGAGCTATCTATTTAAAATAATGTACATAAGGCAACATC
CCAAAAGAAAATGGGCAAGAATCATGAGTAATCAAACCATAATAGAAGAAA
TGTTATTATCAAAATGTGCAGTCTCAAACAATAATTGTCTTAAAAATAAAA
ACAACAATGAGATTTAATTGTTCATGTCGGCAATTTGAACAGACTAACACA
CCCACTGTTCAAGAGCATTTGTGGAAGTCAGGAAAAAACACCCTGTTGGTG
AGAGTGTAAACAGACCTTCAGGAGGCAACTTGGTAACATGTATTAAAAATC
AAAATATGTATATCAATGGATGCATGATTCCTATCTCTATTTTTGCCCTTA
CAGCAATCTTGTGTGTAGAGAAATACTGAAAAGCATTTTCATGGTAACATG
GTTTAAATTTTTAAAAAGCGAAGGTCAGTGAATAAAGGGCAATTATCTACT
TCCCTACAATGAAATGCAGTAATGAAAATAATCATTAGAATCTCTTTTATT
AATTTAAAAGGATACTAGAAAAGTGAAATACAATCTCACTTATAGAAGATT
TACATATTGGTTTGCATAGACTTGCACAAGATAAAATTTCTGTAAGATTGG
TCACCAAAATGTCCTGAATGATAACATTACAATTAATGTTTATATTGTAGG
GGAAAAGAAAATTCTGTTTTTCTCACCCATCAGTAAGTTCATGCTTGAGGC
CCCTCTACAAAAAGACAGATTGGTCGGGTGCAGTGGCTCACGTCTGTAATC
CGAGCACTTTGGCAGGACGAGGCGGGCGGATCACGAGGTAAGGAGATTGAG
AACATCCTGGCCAACACGGTGAAACCCTGTCTCTACTAAAAATACAAAAAT
TAGCGGGGCATGGTGGCACGTATCTGTGGTCCCAGCTACTCGGGAGGGCGA
GGCAGTAGAATCGCTTGAACCTGGGAAGCGGAGGTTGCAGTGAGCCGAGAT
CGCGCCATTGCACTCCAGCCTGGGTGACAGAGCAAGGCTCAGTCTCAAAAA
ACAAAAAAAAAGATTAGCAAGAGAAAAGCATACAAATGTATTTAATATAAG
TTTTATATTACATGGGACCCTTCGGAAATGAAAACTCGAGGGAAGCGGGAA
ACCTGTGAATTTTTATGGCAAGTTTTGTGAAATGCATAGTTGTGGATTAAT
ATGATTGACAGTAGGCATATGATCTAATGGTAATAAACTGAGGGGGACATA
GCAAGGCTTGTTTGTTAATTACCTATTAACGATCAGCCGAGTATCAGCAGA
GACAGCAAAACATCCTAGTTTTGAGTTAGAAGACCTAGGTTTTTGTTTTGG
CTTATCAATTATGGGTATTGTTTTAGATGAAACATCAAGTATTCTTGATTT
CTTATTTCAAAAATAAAAAATAAAAAATAAAGGAAGGAAAAAAGAAGAAAA
AAAGAGAAGAAAAGTGTCAGAGTTACTTGAACCAGAGTAACTCCATTTTGA
GTGAGGGCTAGGAAAATGAGGCTGAGACTTTCTGGGCTGCATTCCCAGAAA
GTCAGTCATTCCTAGCTTCTAGATGTTTACGGTTAAGGGAACAAATAAATA
ATGTTTACTAAACAGACTCAGACTTAGGAGTGTCCAGATATCCCTATATCT
GGAGAACAAAGGCATTCTTAATTTTGTTTAAAGATAATAATGTTGATTCTT
GCAAAATATAGTAACTAAGAAAATTAATCCTTTATCACAAACTTGTAGCAG
AGCACATCTCCCCATATATACAAGTATTGTACCTAGGGTGGATGCCTTCCT
CCTCTTACTTTCGGGAATGTCCTGCTCCGTCTATGGAGTAGTTGTCGTTTC
ACCACTTTACTTTCTTAGTAAACTTGCATTTACTTTGCACTGCGGACTCAC
```

FIG. 8-64

```
CCTGAACTCTTTCTTGCGCGGGATCCAAGAACCCTCTCTTGGGGTCTGGAT
GGGGACCTCTTTCCTGTAACATATTTCTGGCCACCACAGAAGGGACTATAG
TACAGAAACCCTGACCCAACAGCTACCTTTGGGTAAGTGTTGGAGTTCTGT
AACAAAGGAAGAAGGCAGGCAGGCAAAAAATTTATGAAAGAACATACGACA
AAATAATTTCTGCTTCAAAACTTCATATTTTTTAATTTTTTTTTTTTTT
TTTTTTGAGACGGAGTCTCGCTCTGTCACCCAGGCTGGAGTGCCATGGCGC
GATCTCGGCTCACTGCAAGCTCCGCCTCCCGCGTTCACGCCATTCTCCTGC
CTCAGCCTCCCGAGTAGCTGGGACTACAGGCGCCCACCATCACGCCCAGCT
AATTATTTTGTATTTTTAGTAGAGACGGGGTTTCATCGTGTTAAGCAGGAT
GGTCTCCATCTCCTGACCTCGTGATCCGCCCGCCTCGGCCTCCCAAATTGC
CGGGATTAAAGGCAAGAGGCACCGCGCACGGCCCCGTCCAAGTTAACCTTG
GCTCTAAAACTTGTCTTCGCTAACATTCCAGTTGATCCTCTAGAACTGAAA
CAGAATAGCAGCAGCACCACCTTAAGAAATTGTGGTTATAGCTCTCCTTGT
GACAAAGTAGGTGGCTCTGAAAAGAGCCTTTGGGTTTGGAAGTGCTTACAT
AAGCACTTATTTAGAGCTAGTGTACTTGGTAACTGCCTTAGTGCCCTCGGA
CACAGCATGCTTAGCCAGCTCCCCAGGCAGCAGCAGGCGCACAGCCGTCTG
AATCTCCCTGGAGGTGATGGTCGAGCGCTTATTGTAGTGAGCCAGGCGAGA
AGCCTCGCCCGCGATGCGCTCGAAGATGTCGTTGACGAAGGAATTCATGAT
CCCCATGGCCTTGGATGAGATGCCGGTGTCGGGGTGGACCTGCTTCAGAAC
CTTGTACACATAGATAGAATAGCTCTCCTTGCGGCTGCGCTTACGCTTCTT
ACCATCCTTCTTCTGCGCCTTAGTGATAGCCTTCTTAGAACCCTTTTTAGG
GGCTGGAGCAGACTTAGAGGGTTCAGGCATTGCTATTCCTAAACAGAATAG
AAAAGCTACTAACACTCTCCACTACAGAGTAGTACAGAGAACAGTTCAGAG
CCCATGTATTTATAGTCCTGAGATTCAAATGACGGTTTAAGATTCCTCACT
TCTGATTGGACAAAAGAAACACGGTTTCACTGAGGGGTGGGGTTTATGCAA
ATATGGAATTTATGTTATCTTTTTCTATTGGATAAAGCACCAAACATAATT
GACCAATAGGATAGCTTCCTATTGCAGCCTTGCAGTTTGTATAAAAGGATT
TGTTCAGGCGCCATTCCAGCTTGCTTGTCTTTCACAGTTTTCCGCTGCTTT
CATAGGTCGCTATTTGCGGACGTGGAAAATGGAGCTAAAGCAAAAACTTGT
TCGTCGCTACCGGGCTTGCAGTTCCCAATAGGGCAGAGTCCGTCATCTTTT
TCGAAAGGGCAATTATTTTGAGCCGGTCGGAGCCGGTGCGCCAGTGTACTT
ACAATACCTGGCCGCCGAGATCTTAGAACTGGTGGGCAGCGCCATACGTGA
CAAGACCCGCAGCATCATCCCCCGCCACCTGCAGCTGGCCATCCGAAACGA
CGAGGAGGTCAACAAGCAGCTGGGCAACGTCACTATTGCTCAGGGAGGCGT
CCTGTCCAATATTCAGGCCGTCCTGTTGCCAAAATAACAGAGCCACGATAA
GGCCAAGGTCAAGTAAACACTCAAATCAGAAAACGTAGCTTACACTTGAAA
CGGCATTTTTCAGAGCCGTCCATAGTTACACAAGAAAGGATGATAACTTGC
TTCTGTTAGGGTATTTTTTGCTTTTCGTTTGGATTGGTTTGTTTGAGACA
GTCTAGTTCTGTCACCCAGGCTGGAGTGCAGCGGCGCGATATCGGCTTACT
GCAACCTCCACCCCGCCGCTTCACGCGGTTCTCATGCCTCAGCCTCCTGTG
TACTTGGGATTACAGGCGTCTGCTACCGCGCCCAGCTAGTTTTTGTATTTT
TATGCGAGACGGGGTTTCACCATTTTAGCCAGGGTTGTCTTGAACTCCTGG
CCTCTAGTGATCGTCCCATCTCGCCCTCCCAAAATGCTGGGATTACAGGCG
TGAGCCACCGCCCCCTAGCCTAATGGTGTTAAAAAGTTAAGTTTCGAGAA
AATAACACCTTCCTTTAGAAAGTACATTTTAGAGTATACAAAGTGAAACTT
AAGGCCAACCAAAATAAGACATTTTGAGAACAGGCAGGGTGGGAATGTGAC
```

FIG. 8-65

```
TTGGACTTAGAAAACAAAGGGCAAGGAAACTTGCTGTTCGCCAGTAACAAA
ATAGCATGGAATCTCATTCTCTGAATATAAGCGTTATTTCCCGACATGAGT
CTGAACGTTTCTGGTGGTTTAGTGAGTGTTCACCAGCATTGATAACTTGCG
AGACTGTCAGGAATGCAGAATTTCAAGTCCCACTCAAACTTACTGAATCGG
AATTTACATTTTAAAAATCCTTAGATACCTTGTTATACACTCTGTTCTTTG
GGACTGGATGAACTAGAATTTTAGACAATTTGTCGCTGCAGATAACTGAAA
CGAAAAGGACAGGATGGGCGGTGGGGCAACTCATCCAATAAGATTGTCTAG
TAATGAACCAATCAGTCTGGTCACTCTTCAGCCAATGATTTTATCGCGCGG
GACTTTTGAAATATTACAGGACCAATCAGAATGTTTCTCACTATATTTAAA
GGCCACTTGCTCTCAGTTCACTACACTTTTGTGTGTGCTCTCATTGCAAAT
GGCTCGTACGAAGCAAACAGCTCGCAAGTCTACCGGCGGCAAAGCTCCGCG
CAAGCAGCTTGCTACTAAAGCAGCCCGTAAGAGCGCTCCGGCCACCGGTGG
CGTGAAGAAACCTCATCGCTACCGCCCGGGCACCGTGGCCTTGCGCGAAAT
CCGTCGCTACCAGAAGTCCACCGAGCTGCTGATCCGGAAGCTGCCGTTCCA
GCGCCTGGTGCGAGAAATCGCCCAGGACTTCAAAACCGACCTGCGTTTCCA
GAGCTCTGCGGTGATGGCGCTGCAGGAGGCTTGTGAGGCCTACCTGGTGGG
ACTCTTCGAAGACACCAATCTGTGCGCTATTCACGCTAAACGCGTCACCAT
CATGCCCAAAGATATCCAGCTGGCACGTCGCATCCGTGGGGAAAGGGCATA
AGTCTGCCCGTTTCTTCCTCATTGAAAAGGCTCTTTTCAGAGCCACTCACA
ATTTCACTTAAAAACAGTTGTAACCCATTCGGTTGTCTATGTTAGTTTCCA
GGAGATATAAAGGTGATAACTACACACAAGTTTTGTAACTGCAGACAAGTC
TATCAGGCCTTTTCAACCGGTTTTACTGCGAGAAAACAAGCTGAGTTACTG
TTTTGCCCTTGTTAAAAAATTCCTAGGGGTCTTTTTAGCATGTATATGTGT
AAATACTTACATATTGAAAGGCTCCTGGGGACACCACCGTCACTCCTTTTA
ATCCACGTGACAATTTTAGTTCTGATGGCAGTATTATTAAAGCTATCATAA
AGACAATGTGTGTGTAGTTACCTAAGTCCACAAAAACAATAGCTGACCCCA
AAATTCAGTATTGGTTTTGGGCTGCTGGAGGTGGAGTCAGAGCTCAGGTGG
AAGAAACTGGCCTCAGTACACACTGCCAAAAGTCCACTAAATAGATTTATG
TAACAAGTACACAAGACTTGCGTATGACCATCCAAAGATTATGCGGTCATC
CTTATCCAGGGAATTTGAGAATGAAGGGTGGCAACTGCAAAGCTCTTTTAC
CCATGTCCTCTTTTAATAAATATTTAAAAATATTCAAATGCTGATTTCATC
CATTTTCTAAATATATTAGTATACTTAACTGATGGGGTAGATCAAGGTTTT
CTGGGGATCAAACCTTTTACAACTTGTTAACTATTAAAAACTATAATGTAA
AATTAAAAATGCAAAAGTACTGCAGACTGTAAATATAAATTTATAATGGGA
AAATAAAATCAAATTCCAATTTTATAAAAGCTGACAAAACAACAGCCATCA
CAAAATTCAGAAAATAGCATATTTTATTAACTTCTGAATATGACACTACCA
AGTATATTTTCCTGTAGTTTTGACTGAATACTCTGATTCCATCTTCAGATC
GAAATTATTTTGTAATGTTGTCTATAGGTAATGGAAATAGAATTCAATCTT
TCCTCCAGGGTGGCTGATGATAATATGTTTTCTTCATAACTTAGAAGTATT
TCAGTTTCAAAACACATTATTGGTAATGTCAAGTAAGTTTTTAGGATTGTT
TTCAAATTTGGAAAATCCTCTGTTAAGCTCCTTTCACATGTAAGTTGTAAA
CTTTGTAAGAATTCTTTCCAGACTAGCTTCTGGCTCTATACGTTTCTACTC
TCCACTAGACACTCACTCTCAGTGCTGGGAATGTGTTTTGAATACTTAGAT
GTCATAACATTTTATCTAGACCTGCATCTTGCCAGGAATTTAGGTGAGTTA
TTCCAGTGAGCAGTAGGAACATTCCTTGAAGCCATTCTTTTTTTTTTTTTT
TTGAGACGGAGTCTCGCTGTGTCTCCCAGGTTGGAGTGCAGTGGCGCAATC
```

FIG. 8-66

```
TCGGCTCACTGCAAGCTCCGCCTCCCAGGTTCATGCCATTCTCCTGCCTCA
GCCTCCCAAGTAGCTGGGACTACAGGCGCCCGCCAACACGCCCGGCTAATT
TTTTGTATTTTTAGTAGAAACGGGGTTTCACCGTGTTAGCCAAGATGGTCT
CGATCTCCTGACCTCGTGATCCGCCCGTCTCGGCCTCCCAAAGTGCTAGGA
TTACAGGCGTGAGCCACCGCGCCCGGCCTCCTTGAAGCCATTCTTACGTCA
GATTGGCTGGCAACGAATGAAGTACACATGATCACATATGCAAATCACGTA
ACTTATTATCCCCATACTAGATACATCTTCAACTAAACTTTCTCTTACTCA
AATTCCAAATATTTTCATCAGGATTCTAACATAATCAGACAATGGTGATTT
TAATAAAAAGGAGGATTGAGTGAAAATAGCAGCCTGAACCATCCGTGATTA
AAGTACCTTAATACTGCAAATTTTAAAATCAGAGAGAGAGAGAGAGACAAA
CTAACACATTTGTAGGGCCCCTCTCTGCACCTTGGAAGTACAGGCCCTTAC
ACTTGTGTTTCATTAGCTTCAGGATAAATCTGCCCCAGATCACTGGCCAAA
TTTTACGTGGCCTTCTTCAGCATCCTACCACTCTATTCAAATACATCTCTG
CAGGAGCACCCTGTGAGTTGAGAATTACTGGTCTGGGATGACCACTGTTTG
CATGATGCTTTGGATGGTGGTGCTGTTCTCAGAAGAAATACCAGAAGGAGA
AAGGTTAGTCAGGAGAATATAAAGTCAACCTTAAGCAATTTGAACACTTCA
GTGGTTAAGTGAGTTCCCTGGGACAACTCTGCAAGCTGTTTTAACTTTATT
TGTATTGAATATTACCTTCTTTTAGAGAGGCCAACGTGTAGAAGGAAATAA
CAATGAAACAAAGGATTCATTAATAGTATAAACTATAAACTAACTGTCATT
GATAGTCTTCCACGGGCCAAGTACCACATGAAGTGGTTGGTCTGAATTATT
GTGTAAAATTCTTACTTCAGCATTGTAAGGCAAATTATCTCACTGTCTCCA
TTTTACAGAAGTGGAGGTTCAGCCTCAGGAATTTCACTAAATTCGCCAAAT
TCTTACTACCAGCAGATATCATTGCCAGGCAGTGTCACACTTTAATATCTT
CTAATCAATAAGATAACCCTAAAATTGATTATCATATATAATTTCCTTCTC
ATATATAGTTTCATACTATCATATATAGTTTCCTTTGTTTCAGAAATTGGA
CTCCCTCAGGGTGGATAAGGAGACATGGTGGTGTCCTGGCCTAAGTATTGT
TGGAATCCTCTAGTCAGAGGCCTGATGTGAGGTGAAGTGGACAGTGAAACT
GCCTTTGCAAAAATCATAACTGAGAAAATTATTACAGTGAAAGAGATCTTA
CCTAACCGACTCCATCTAACGTCTAAACTCCAAGCTGTCCTTTTCATTCCT
GAGTTTGGGATTAACTAACTTTGGGAGGAGCTTAGTTTATACTTTTGCTTT
TAAACAAAAACAATAACAGCCCTTTCAGAAACAAACCCCTTTCCTGCCTGG
GGACCAGACTGCTTTTGCAGGACTAACAAATTAGCCACAAGATTATAAATT
ATGGTTTAGGAGTCATGCAGCTGGAAGCTACAAGATTCTAAACCTCAAATT
GCTCCTGGGGATAAAATCACTATTTTAAAACCTAAGATCAATGCTTGAGCT
ATTTTGCAGACCCTGAACACAATGGATTAGCTGGCACCACCCATATAGATA
AACTGGATTATCTGGTCTTGAGTCCCCCACCCCACCACTCCCAGGAACTGA
TTTAGCACAAGAGGACAGCTTAGGCTCCCTATAATTTCATCTCTGACCCAA
CCAAGCAGCACTCCCGACTCACTGGTCCCCTACAATCAAATTATCCTTAAA
AACTTTGGTCCCCAAATTCTCAAGGAGACTGATTTGAGTAATAATAAAACT
CTAGTCTCCTGTAGCGCTGGCTCCTTATTGCAATTCCCCTGTCTTGATAAA
TCAGCTCTGTCTAGGAAGTGGACAAGGAGAGCCCGTTGGGTGGTTACAATA
GGACAAACCAATAAAATATAAAGTATTAGAGACACTACCTGGGTTTCAGGA
ACAGGTCAGAAAAGTGTTTTCTTGGAAAACATCTGGATTCTGCTGCAGAG
CAAGTATTTGCTTGTGTCTTCCCAGAGTATAAAAGCTGTCCTGTCCAAGAT
AGTTGCCACTAACCATATGTGAGTATTAAGCATTGGAAATGTGGCTACTCC
AAACTGTGATGTGCTTTAAGTGTAAAATACACACCAGATTTCAAAGAACTA
```

FIG. 8-67
```
GTAAAATAACAAAGTAAAAACTCAATATTTTAATATTAGATACCTTGTTGA
AACAATTTTTGGTTACACTGGATTCAAATCATTAAAATAGATTTCTTTTTT
CACTTTTTAAAATGTGCCTATTAAAAAATTTAAAATTACATATGTGGACCC
TATGTTTCTGAGGAACAGTGCCAGGACATAGAGGATAGTTATATTCACTCA
CAGATCAAAAACTAGCAAAACTATGAAATACCTAATAATTTAATTTTTCAC
CTTAACTTTTGGCATATTCCACAGATCTGTAGTATATTTGAGTGTGATAGC
TTAGGAATAAATATGATTGGAACTCATTCATGTTTAGAGAGAAAGGGTGTC
AAATTGAGAACCAGGCAGATACACCTAATCTTAAAATGACCCCAAAGTAAA
GTGGTTGAAGAAATTAAATCCCAAAGATTTTTGGTGAAGAATGTTGTAGTT
TTCATCAGTATGTGTATGTTCAAATGGAGATTAAAGAAGGCAAAATAAGGC
CGGGTGCAGTGGCTCACACCTGTAATCCCAGCACTTTGAGAGGCCAAGGCA
GGCGGATCATGAGGTCAGGAGTTTGAGATCAGCCTGGCCAACATAGTGAAA
CCCTGTCTCTAATAAAAATACAAAAATTAGCCGAGCACGATGGCATGCGCC
TGTGGTCCCAGCTACTAAGGAGGCTGAGGCAGGAGAATCACTTGAACCCGG
GAGGCAGAGGTTGCAGCGAGCCGAGATCACGCCACTGCCCAGCAGCCTGGG
TGACAGTGAGAGACTCCGTCTCAAAAAAAAAAAAAAAAAAAAGTCAAAATA
AAAGAACTGTGGGCTGACAACTGTGGATTAAGCATCAGTTCTATTAAGAAG
GGCTAACTTGAAGATGAATCTTTTGAAGATACATTTTGACTCCAGCTCTTT
AGAGGAACAAAGTTTACCTTGATGTGAAATTCTTCAAATAAAAATTTATTG
ACTTTAAATTTAAAAAAAAATGCACACACACACACACACACACACACAGCT
AACTAGCTACATCCTTAATGACACCAAGCTTTAGTCCTTCACCCTGAAGTG
GGAATGACAATGGCACTTACTTCAAAGTGCTGTGACAAGAATGTGTTTGAA
AATAAATATAGAGTAATCAGCAACAGTGCTTGGCATATTGTAAATAAGTGC
TCAAAAAATGCTAGTTCCCAAAACTGTTGTTGCCACTGTACCCTAAATCCC
TATTCTCTTCTGATATCCTTTAGTGATGTAATTCTGTCTTGCACTGGGCCT
GTTCATCTCTGGTATGAATTTCAACCACAATGTCCTTACTACATTTCCCTC
AGGCTTATATAGCCAAAATATCCAGAGCTTTGCCTAGGAGTGTATAATATG
ATACTTCAATTTGTAGCCATGATAGCACTGTGTATGAAAGTTTGGAATAAT
GCGCCGGGCATGGTGGCTCACGCCTGTAATCCTAGCACTTTGGGAGGCCGA
GGTAGGTGGATCACTGAGGTCAGGAGTTCGAGACTAGCCTGGCAAACATGG
CGAAACCCCGTCTCTACTAAAAATACAAAAAAATTAGCCGGGTTTGGTGTC
AGGTGCCTGTAATCCCAGTTACTCAGGAGGCTGAGGCAGGAGAATTGCTTG
AACCGGGGAAGTGGAGGCTGCAGTGAACCAAGATCACGCCATTGCACTCCA
ACCTGGGTGACAGAGAGAGACTATGTCTCAAAATAAATAAATAAATAAATA
AAAAACAGAAAGTTTGGAATAATGCATTACAAGTAGCCTCTAGTTTTTATG
TTACTCATAGTTTTATCACACAAGAACAATGTCATAAATTTTCATGGTTGA
ATTATCAGTTGTTTATGCAATATTCATTGATGTTTTTGGCTTATCAGCAGT
GTTTCTGGAATTATTTGAATATTATTACCGTTTTTCAAAATTATTTTATAA
AACTAATTTAAAAATCAAAAATGATATAATTACTAATGTGAAATTAAATAT
AAGTTTTGAAGAATATCAGGATGTCACCCCCAAATTATTCTACTTTGGCAT
AAAAGTTATTTTCAGCTGAAGGCAATTGAAAATCAACAGGTGTAGGAAGAG
GTCTCTGTCTTCTCTTTACCCAAATTTCCCTTTGTGAAGGTGACAGAAATT
TCCCTTGTAAAAGTGTCCCCAACTGCTATACCAGGAAAAAGAGAGCAATTC
TTATCACTAGATATGGAAGGTTGGCACTGAGATGACTCTGCAAAAACAAAC
CTTACTACAATTATTTCTATCTTTCATTTTATCTTCCATGGTTTTTATTGC
CCATGTATTTATTTCCTTGTCACATTCCCAAATTCGTCATCCCATGAAGTG
```

FIG. 8-68

```
CAAACTCCCTTTCCTTTGTTGGAATGGTGTATAAGTCTGTGAGTCTAACCG
CGTTTTTAAGGTTTCAATTTTTTTTCTTTGGGAACTCTGTGCATGTAATA
TACTAATAAAATTGCATGCTCTTTTTTTCGCATGTTAATCTGTCCTTTGTC
AGTTAAATTTGCAAGACACTACTTAGTGAATCTAAGAGTACAGAAAAACAT
GTGTCCTCATTGACAGTTTCAAAAACTAAGTAAAATTGAGGCAAGAATCTT
TTTCATCTTAAAATGGCCAATTTTAATTTCCAAATGAATGGTTCATTAGAC
CTAAGCCAGTAAGCTATGTGAACAATTGTGATGGAATAAAACAAAACTAAA
GAGCATGAACAAAATTGAGAAAACATATGCAAGACTGAATCTAAAGGCCAA
ATAGAATTGAAAATTTTTCTAATTTTTAACTCTATAAATTAAAGGAATGTG
TTTCATTTGACGAGTTTCATCTGTGGAAACATGTTTGCAGAAGACATTCGA
GGTTAGGATTAATTGAAAGTACATAAATCAAATGGATTAAGACCCCAAAGG
GCATTGAAGGAAAATTAGAAAATCAGCTATTTTTGCTTGGGTTGATTCCTC
TCCTGACTAACTCTTGGAGATGATAAGAACATCAATTAAATGGGTAGCCAT
GAAAGTATCTAAGGGAGAAAGGAACACAGAAGTTCAATGTACCATAACTTT
ATTTTTATTTATTTAGTTTTTTGAGAGAGAGTCTGGCTCTGTCGCCCAGAT
GGAGTGCAGTGGCGTCATCTTAACTCACTGCAACCTCTGCCTCCTGGGTTC
AAGTGATTCTCCTGTCTCAGCCTCCCGAGTAGCTAGGATTACAGGTGTGTG
ACACCACGCCCAGCTAATTTATTGTGTGTTTTCATGGCCAGGCTGTATTTT
CATGGCCAGGCTGGTCCTGAACTCCTGACCTCAGGTAATCTGCCTGACTCA
GCCTCCCAAAGTGCTGGAATTACAGGCGTGAGCCACTGCTTCCGGCTTTTT
TTTTTTATGACGGAGTCTCGCTGTGTCACCCAGGCTGGAGTGCAAGGTCTC
GCCTCACTGCAACCTCCGCCTCCCAGGTTCAAGCAATTCTCTGCCTCAGCC
TCCCGAGTAGCCGGGATTACAGGCGCCTGCCACCATGGTTGGCTAATTTTT
ATACTTTTAGTAGAGACGGGATTTCACCATCTTGGCGAGGCTGGTCTTGAA
CTCCTGACCTCGTGATCCACCCGCCTAGGCCTCCCAAAGAGCTGGGATTAT
AGGCGTGAGCCACCGCGCCCAGCCTTTTTTTTTTTTTAATTGTTTGATGT
TGAGATGGAGAAACAGGAGGAGGTGGAAGAGATCTTAATATACATATGGAA
AAATAAAAAATGGAATAACCAGGAAAATTCTGAAAAAGAAGAGTAATGAGA
GAAAATTAGCTCTATCTGCTATTAAAGTCACGTTACAACATCTCAGTTAAT
TAGTCTCCCAAAGGGGAGACTAATGTAAATGCATGTTTAATAAACTGCACC
CCCAGTGGATGCCTGAAACCACAGATAGTACTGAACCGTATATACACTGTT
TTTTTCTATATACACATGGCAATGATGAATTTAATTTATAAATCAGGCACT
GTAAGAGATTAGCAATAACTGATAATAAAACAACAATTATAACAATATACT
GTAATAAAAATGATTTGAGTCTGTGAACGGTGGTTCACGCCTGTAATCTAA
GCACTTTGGCAGGATGAGGTGGGCGGATAACCTGAGGTCAGGAGTTCGAGA
CCAGCCTGGCCAACTTAGTGAAACCCCGTCTCTACTAAAAATACAAAAATT
AGCCGGGCATGGTGGCAGGCCCCTGTAATCTCAGCTACTCGGGAGGCGGAG
GCAGGAGAATCGCTTGAACCCGTGAGGCGGAGGTTGCAGTGAGCCGAGAAC
GTGCCACAGCACTCCAGCCTGGGTGACAGAGGGAAACTCCGTCTCATAAAT
AAATAAATAAATATAAATATAAATTATATGACTGTGATCTCTCTCAAAATA
GCTTACCGTTTTACTTGTGATGATGTGAGATGACAGAATGCCAGTAATGAG
ATAAAGTGAGGTGAATGGAGTAGGCATTGTGAAGTAGCATTAGGCTTGATA
AGATACTACAGATTTAGGTATTAGTTGAACACTTGCCATTTGTCACATAAT
CATCTCAGCATTGAGGATAGCACACAACACAATGTTTAAAACAATACAATT
CTACCTTAAGAATTGTGGGAATGACTAAAGGAACAAAATAGAAACCTGAGA
AACCTAAGACAGTCCAACTGTCCATGAAATTATAGCGTATTAGCCTATGAC
```

FIG. 8-69
```
AAAACAGCCAAAATTGATAGGAGCGTGGAGGGTGGCACGGGAGGAAGAAGG
GGGAAGCAGAAATGAAAGTTCATAAATGGTCTTGGGAAAAATATGTCCATA
TGTTAAACCTTACACCAAAATAGAGGGTTCACCATGTTAAACCGTGTTGTA
ATGTAAAATTAACAACACAAAATTACTTAAACCATGGGAGAATGTTTTCTC
CTTCTTCCCTGCCTCTGTCTTCCTGTCTCTCTGCTTGCCTCCCTCCCCTTT
CTCTTTCTTGGGATGAATCCGTGGTCACTATCACTAACAAATCAACTCACT
ATATTAATCATTGTGGAGATGGTAGAATAATTGAGCAGCTTATCTCCAGAA
GCCCCAGTCCCCATAATTTAGGTCTCACCAAAATGTGCCCACCAGATTTTA
AAAGAAGCGAATATAAGACGCTAGGCTTTCTGTATTCAGAAGCACCATGGA
TGTCAAACAGAGGGAACCATTAACGAAGGCCTTTATTAGAAATGTCTCCCA
TTTATCCATACACTCTTCATAGTTAATAGTACAAATACTGTTTTCTGCATA
GAAACATTTGGACTGCCAAACAAAATACGTTTAAAGGAACTTCGATTTTTA
AATGTTGCTGTCTGTCTAAACAGGATAAGCAACCGTAGTCATGCGAGGACA
AAATGGCTGGCTAAAAGTTGTGCTTTCGATACGCTCAAAATCGATACGCTC
AAACCTGTCAGTTTAGCGGAAGGCTACATGTTATGTGGCACAAAAAACTCC
CTAGGTCCACGATTGCCTTGGGTGGAGGAAGGGCTATTGCCGCTGTTGTGG
CTGTTTTTTAAATGCATTCCTTCGTTGCCACAGGAATGAGAAATTAACAGC
AGAGGAATGTAGGACAAAGGTACCTGCACGCACTCTCCTCCCAGGGCTGGA
TGTTGCCACTACCTCCAGGAGACATCAACTTGACTACCAACAACATGGAAA
GCGTCCGAAATCCCAGACATTAATATAAAGAGAAAAGAGGCAAAACTTTTA
AGTCACAGTAAAGCAAAAAACACAGAATAAGCAACGTCTTCCACCATCCAA
TTAAATACAGAATGAAAGTCATGTACTAGAAGAACGGACCAACCCGGGAGC
AGGGCGGGACTTTTGAAAATTTTTTAGTCCAATCCGGACATCCCTTTAGAC
TAAGAAACTGGCTCTTGTTTTGCGGTCTTTTCTGCCGTTCACAGGCCTGGG
GCGGGACTGCCATCCCAAAACCATCCGCCAGCGAGAAAAGCCTCCGGTCAG
GGACCTAGAAGCCGCAATAAAGGTTTAAATGCTGTAACCTCACCACGGCCA
CTCTCCAACCCCGTCACCCAATTCGTCTGATACCTCAGTAACTCCCATACG
ACTAACCTTAAGTAACAGGGCAGAACAAGAAAAGGCAGATAGTAAAGAAAT
TATCCAGCTCTTTTATTGAGATCAGTGGTGGCTCTGAAAAGAGCCTTTTGG
GTTTTAGAAGTAGGCGTTCGCCTATTTCTTCTTGGGCGCCGCCTTCTTAGG
CTTGACAACCTTGGGCTTAGCGGCCTTGGGCTTCACAGCCTTAGCAGCACT
TTTGGCAGCTTTCTTGGGCTTCGCAACCTTGGCCTTCTTTGGGCTCTTAGC
CACTTTCTTGGTTACAGTGGCCGCGGCCGGCTTCTTCGCTTTCTTCGGTGT
TTTCTTAGCGCTCTTCTTCGGAGTTGCGCCGCCAGCCGCCTTCTTGGGCTT
CTTGGCTGCCCCAACTGGCTTCTTAGGTTTGGTTCCGCCCGCCTTTTTAAC
CTTGGGCTTGGCTTCCCCGGAGGCTGCCTTCTTGTTGAGTTTAAAGGAGCC
AGAAGCACCGGTGCCTTTCGTTTGCACCAGAGTGCCCTTGCTCACCAGGCT
CTTGAGACCAAGTTTGATACGGCTGTTGTTTTCTCCACATCATAGCCGGC
GGCAGCCAACGCTTTTTTCAGAGCAGCCAGAGAAACTCCGCTACGCTCTTT
AGAGGCGGCCACAGCCTTGGTGATGAGCTCTGACACCGGGGACCAGACGC
CTTACGAGGCGTACCCCCAGCCTTTTTGGCCGCCTTCTTCTTTACAGGGGC
CTTCTCCGCAGGAGGCGCGGCAGCGGGAGCGGCAGGAGCAGTCTCGGACAT
GTTGAGAATCAAAAACTCGGGTACAAGTGGCAAAGCGCCGATGAAGCAGCG
CCTGGGCAGGGCCGCTGTATATATAGAGCGCAGGCGCGCTCTGATTGGTGC
TCTGGTCGCCCGCCTGGCTGGCAGGCTCTGAGCCGCTGCGCTGCTCCCAAG
TTGTGTTTGTTCCACCTCACAAAAGGGGAAAAATATTAAAATTCCCCGCAC
```

FIG. 8-70

```
CAAATCACTTGGGTTTGGTCAGGAAAGGATCTCAGAAGCCTCGGGCTTCAT
GCTCTTCATTTATTTTTCCACAAACACAAAAACAACGCGTCCAGGCGTCC
CCAATTCCCCCAACTCCGAAGGAAGTCTGGGGCAGTCAGAGACCACTTTCT
GTTTTTCTTATAAATTACCTGTTCGCTCCTTTGCCCCTGAAGGTTCTTTTT
CCCAGGGGTGGTTGGGCACATGCTTCCCTTATTTTTGAAGAAAAAAGCGAA
ATGGTTTCCACCTAAATTTTCATGATAATTCTGTTTCTTCACAAGGGAAGT
AACACAGGTCCTCTGTGAATTCTTCGTGCAGTCGCACAGGAACTGTGGACT
GGGACAAGGATTCCACGGCCAGTCCAAAGCAATTAGGGCGGGATGGGAGGG
GGTTCATGAGCCTTGCTAGGGTCCGGGGTGGTGGGGGGCTACAGACTTAAA
TCTTTGATTTGAAGACATTGAAACTATCAAATCCCTCTTTTCATAGATGGG
GGTGGGGCATCCTTTTCACTTCTCTACAGGCGAGAAATTGGGCTCTTTTTA
AAGAGCTCTGAGGTCCCCCTCTGAGTTGTGTAAGGCAGGAGGTCTGGCCCT
CAAGATAGAGATCATAAAGGAACAAGGGAGAGCCCTTAAGCCTGCAAAAAA
GCCAATAGATTTGGCAGTTAGAGGCACTGAGATAATATGTTTTCAAAGAAA
ACAAGCATTTTTTATTTATTTATTTTTGTACGCTGCAATATAGAAATGAAT
TTCAGCCCATGAAAATTGTAGGTTACTTTCAGTAACCATACCTTACGCAAG
TTACCATATAGGACAATCTCCAGTTGGGAACTCAAATATATCTTTTGAGTT
GCAAATAAAGCAACTGACTTTAATAAAACACACTCTTGACTTTTAAGATGA
ACAATGTATTTGAAATTTATTTTTTAAATAGCAAAATTTAACACAGAAAG
ACAAGAAAAGTACCAGAACATGTAATTTATTATAAGATCTGTTGTTGATGA
GCTGAAAAATCACCTCTTCTCATCCCCTCTGAAACTATTCTGTTCTAAAGT
TTGCTACTTTAAGGTTCACTACTTCTTATTTTACTCTCCGACCCCAAGTAA
TTGCTATTTTTTTCTTGAGATTAAAGGCAAAGTAAATTGTCTGCCCATATA
TTTGATATAATTATAGATTCATATTTAGGGACAAAGGTAATATTACAACTC
CCCAACAATTTCTGCTCAAATATATGTTTTCATGAAAATATGTGTTAAAGA
GAACAGCCTTAGATTGTGGGAAAGTCAAAAGGGAACCTACAAATAAGAGTT
CAATGACAAATGAAAAGTGAAACATCTTTTAGACTAAGGGTGACCCCATTG
TTTTATTAAATAACATTTGTCCAACATTTGTAAACATTGTCTGCTTGTGTG
CTTATGTCCTCTGGGAATTAACAGTCTAATGAGATTAGTGATGGATGAATT
AGCAGTGGTGGAAAAACACTTAGACCGGCTATTCCTCAGAGTGACAGGGTA
TAAGAATTATACAAAATTATGGAAAGTGTATAAACAATTGAAGCACCTGCA
TCATACTAATATATTGTAGTAAAAGAAATAATATAAGGCTGGGCCCCGTGG
CCCACGCCTGTAATCCTAGCACTTTGGGAGACTCGGGGGCGGATCACCTGA
GGCCAGGAGTTTGAGATCAGCCTAGCCGACATGGTGAAACACCATCTCTAC
TAAAAGTACAAAAATTAGCTGGGGGTGGTGGCACTCAGGAGGCTGAGGCAA
GGGAATCGCTTGAACCCGGGAAGCAGAGGTTGCAATGAGCCGAAATGACGC
CACTGCACTCCAGCCTGTGCAACAGGGTGAGACTCAGTCGAAAAAAAAAGA
AAGAAAGGAACAATATAAGAACATGTCACTTAGGCCAGGCTTGGTGGCTCA
CGCCTGTAATCCTAGCACTTTGGGAGGCTGAGGCGGGCAGATCGCCTGAGG
TCAGGAGTTCGAGACCAGCCTGGCCAGCATGGTGAAACCCCATCTCTACTA
AAAAAAATACAAAAATTAGCCTGGCGTGGTGGCAGGCAACTCTAATCCCAG
CTACTCAGGAAACTGAGGCAGGAGAATCATTTGAACCCGGGAGGTGGAGGT
TGCAGTGAGCCGAGATTGCCTCGTTGCACTCCAGAAGCCGAGATTGCCTCA
TTGCACTCCAGAAGCCGAGATTGCCTCATTGCACTCCAGCCTGGGCAACAG
AGCAAGACTCCATGTCAAAAAAAAAAAAATAAAATAAACATTTCACTTAGA
TCTTATTCTATGTGCAATGAACCCCCTTCTCATTTAAAACTCAGCTAAGTA
```

FIG. 8-71

```
TATCCATCATGAAAATAGCTATGAAACGTCTTGATTACCAGGTAACTGGAC
CTTCTTTCACTATAAATTGGTGTCCTGGTTTATAAATCGACATGTAAATTT
AATCGCTGTGATTCAGTTCTCTAATATGATTTTTCTAGTCGACTCAATCTA
ATCACATCTCTTTATATGCAAATCTCAAGTCCAGACCTCAAGCCATTAGGA
CATCCAGCCACCCAGAATCTTGTCCCCAACCTCCTGGCAACATGGTGGAGG
CCAGAAGACAGAGAAACATGTAACCAACCCTTTTCTAGATCCTTTATAAAG
TGTGTTGAAAAAGTTATGCAAAACTTAAAAGCAACGCAAAAATATTTCTCC
ATATCCTTCCAAGCTATATTAGAGAATTATCTAAAAAGCCTACTTATGGGG
TACCTGATGATGTAAGGCAATACTAGACAGTAAAATAGAATGTGAATCACA
TAAATACTTTCCAGATTTCTAGTGGTCACATTGAAAGAATGAAAAGAAACA
AGTAAAATTAATTTTAAGATATTTTATTTAACTTAATATATCTAAACTATT
ATCACTTCAACATATAATAAATAAGCTAAAAAAAAAGACAGTTGACATTCT
TTTTTAAATGATAAATCTTCAGAACCTGGTGTGTATTTTACACTTTTAGAA
CATTTTAAATCAGTCTAGCTATAGTCCAAATGGTCAATGATCACGTGTAGC
TAGTGGTACCTTATTGGACAACACTGTCCTACGTGAAAGTAACTCTGACTT
AATGTTTACATTTTATTGGGTCCAGACTATCTAAAAGTAAACATTCACTTG
TAGAAGTTTAATAAATTAATAAGGATTTTGTCATAGAGATGGAAATGAATT
CTTAATATAGAAAAAATGACCCTAAAAGTTATTATTGTATTGCCTAATAAG
TCATTAAACAACTTTATATCTGATTTTCCCTTCCTCTTCCAGTATACATCC
TTTCCCTGACCAAATACATATTTTATTCTCCCGTATCTTCCTTTGACCTAA
TTGTGATTCTGCTTCCTCCTTCATTAATGAATTAAATCATTCATTGACACA
TACACAAGCTCACTATATATAGTACATATATGTCAGTCATGTTTTTAACTT
CCTGAATGTTGTACTTTGACACTTGGTTGTTCAATTTCGCCTAAGAGCTCT
GAATCAGAACCTTTAGAAGCCATTCTGAAAAACTGGAAGATACAAAGCTTT
TGACTATCAACTCCATAGCAACCTGATATCTGGTTGGTGTTCCATGGAAAC
TGTATTTCTCAAATTTTGAAATAAGATTGAACAAGCCTGTGAGCAACAACA
AAAAAAAAGTCTATTAGAATGACCTCTGGCCGGGCGGGGTGGCTCACGCCT
GTAATCCCAGCACTTTAGGAGGCTGAGGTGGGCAGATCATGAGGTCAGGAG
TTTAAGACCAGCCTGACCAACATGGTGAAATTCCGTCTCTTCTAAAAATAC
AAAAATTAGCTCGGCATGGTGGCGTGCATCTGTAATCCCAGCTACTTGGAA
GGCTGAGGCAGGAGAATCACTTGAACCCAGGAGGCGGACGTTGCAGTGAGC
TGAGATTGCGCCACTGCACTCCAGCCTGGGTGACAGAGCGAGACTCTATTT
CAAAAAAAAAAGAATGACCTCCAAGGGAAAGTTCAGATTAAGGATGTGGTC
GTCCCACCCAAAACTGATGTCCTCAAGAAAGCCACAAACAAATTGAGGACA
CAGTTAAAATATTGTAATGCAATATATTGTGTATTCTTTTATTTACACACA
CATCATAAATATTATAGGTTGACTAGTTTTGTTTCATGCCACACTCTTCAG
GGTCTGGAAACCCTGGTAGAAAAGTTAAAAATGCAGAGCAAAATGTCAAGT
CCAAACAGCAGTAATGGGGCTAGAGAGAGACTCAAACAGCCAAGATATATT
CAAAGGATAGTGAGAGGAGTTGTTAGGACAGGTGTAAGGAATGAGGGTGAC
AGCTGGTTTTTCTTTCACTTTTTCCTTCTACTATGCCAATTAGAGTTCTTT
GTTTTTGATAGAGACAGGGGTCTCACTATGTTGCTCAGGCTGGTCTCAAAC
TCTTGGCACCAAGTGATCCTCCTGCCTCAGCCTCCCAAAGTTTTGAGATTA
TAGGTGTGAACCACCAAGCCCAGCCTTAGAGTAGGGTTCTGTCATCTTTTG
GATGTAGCTAACCTAATATTACTAAATCCTGTATAGGCCAGAACTTTGAAT
GATTTAAAGCTGTTTTTTCCTGACTCACCAATTAATGAAGCTAATAATAAC
AGCCACCCCACTGGCAGTGCCTGCCTCAAAGAGTAAGTGTTAGTGTTGCTA
```

FIG. 8-72

```
TCTGCTTGAGACCAACAATACAGGGACTCCAGGATATTTTCAGCCTAAATA
AGATTGTAGGGGCTCTTGTCTGTTGCCTGGCTTCAGCCCCATAAACTTTTT
TTTAACATATAACCCAGAGCCACAGTTTTGCTCATATTTCAATCTTTGAAG
GCAAATGGCCAACAATTAGATTAAACCTGAGGCTAAATATTTCCTCACCTC
AAGGGCTGAGACGAAAGTTACTGCATCTGTATTCCCTAACACGCCCTCAAA
ATGGGTTGCAGAAAACAACAGAAAATATACTAAAGCACACAGTAGGAGCAT
AATAAATAGTGATTAGCTGGGTGCAGTGGCATGCGCCTGTAGTTCCCGCTA
CTCTACTCATGAGGCTGAGGCAGGAGGATCACTTTTGCCAAGCAGTTTGAA
GTTGCAGAGAGCTATGATCACAACACTTCACTCTAACCTGGGCAACAGAGC
AAGACTCTGTCCAGAAAAATAAATACATAAATATAAATTTAAAAATATAA
ATAAATACATAGAGAGTATTACAAAAGGAACAATATATTGCAAAATATATT
TACCTAACATTTTGAAATTGCCATTATAATTGTATAAGTGACATAGGAAAC
TGGGTCATTAACAGCTATCTTATTCTTCAAGCTTCTTTCAAATGATGTCAA
AGCATTTCAGAAAGTCAAACCTACCCTCAAAGGATAAGAATTTGTCAATTG
TGAGGATATGCACATTTTTACACCTTCTCAATCTGTGTCTATATGAAGGCA
GTTATAAAGCACAAGATGCAAACGTATATTAGGCAATAGTCTTCATCAGAA
TAAGTACATAACCTGACACAATGACTATATTGGAAGAAACATGGAAATGCA
AATTTCAATAGATTGGTTGACATTATTTTTTAATGTCTAGTTTTTTACTGT
GCTGTGTTTTTACACACTTAATGAGCACTTGTTAAGCACAGGACACCAGGA
GAAATAATAAAAACTAAGATCAGCCTAGCAGTGTGTCCTCTCAAGAACTTA
TACCTGGTGGGACAGATACAGACAAATATAACCATCATACAGTGTGAGAAA
TCGATAGAAAAGACACAGCCACTGAGAGCACAAAAGAATAAAAACATAAAA
TGTTAATGTGCTGGCTAAACGTTTGCCTTCAAGTATTTACCAGTCTAGCTG
GGAAAATAAGACAGAAGACAACAGCCTAAAATAGTGGTTCTTAAACATTTA
GATATCAGGACTTCTTTACACTCCTAAAAACTATCAGGCCTCCAAAAAATA
TTTTGCTAAATATAGGCATTTATCACTTTGGAAAACAAAGCTGAGTATTAA
TTATTTAATTATTTATATTAATATTTATTTGATAACCTTTAAAATATTATA
AAATTAATATTTATTTATAATGCATATATGTGATTATATAGTTCATATGTA
GCCATATATTTATCATATATACCATAGATTTATGTTATATATTACATATGT
ATGAAGAAAAAATGGAAAGTAAACCCAAAAGTTCCCCATTCCCTAACCCAT
TCAAAACCCTGGAAGTCCCAGGCTAATCTGAAACTTGTAAAACTGCCTGCA
TGTAGAGAGCACAGCTGAGCTGGTAGTGTGGAAGAGCAGAAAGACAGCAGT
TCTGGAGCAAGGAAGCTTTATATTTAATCCCAGTTTCTCCATTCATGAGCT
TGGTTACCCTGCCAAGTTCCTTCTCTGTAAAATGGGAATAATACTCCCAGA
AATACAGTGAGGATTAAATTAGATAATGTGCATACAGTTCCTGGGATTGGG
ATCAGCACACAGTAGCCTCTCATTTGAGGCATATTTGCATTAGATCCTTGC
TGTATGATATCCTTCTGTTTCTTTCTTTTTTTTTTTTCCTTTGGTGACC
CTAAGAAAGATGGTACTCTCCTTAACTTGGAGGGCTGGATGCGAAGAGACC
AAATCCAACAAGCTGGTTCATTCTTTCTAATTATGTGTGCTTCCCTTAGCT
GCCTCTGAAAGGATACAGGCCCTAGGTACTAGCCCCAAGAAGCCTAATGAT
AAGAGATAGAGCTGGACCACCAGAGAAGAGATGAGTGTGTATGTGTGTGTG
TGCAAGCAATTATATGTGTGCATTTAGGAGTGGTAGGTGTGTAAACAGTCT
AGAACACTCATTCTCACTGTGATGTGAGGATGTATCCCCACATCACTGTTC
TGGGAGCTCACTCCTTGTCCATCATCCAAGCTTATGATGGACAATTCTTTC
CCAAGTGGGAAAGAATTCTGATGACACTCACATAACTACCCAGTCCCAACT
TTCTGTATCCAAGGTGTGTGCATACCTTTGATAGCAGGCAGGTGTGCCTAG
```

FIG. 8-73

```
CCAATATATTAGGAGCATGGTATTCCAGCACTCTGCACTTTTTTACTATAG
AATTCATCTCAACCTGCTTACATTACATGAAAGTTTTGATTGATATCAAAT
TTTTATTATGTTTGCTTATCAAAGGATTTGTAATTATGCTTCAGTTGATAC
ATAGATTGTTTATATTTTTCATGGTTACTTGAAGCACTTATATTTTCCTCA
TACTTTTACAAAGTAATCAAGGAAAAATACAGAGGCAGCTTAGTATATTAG
TCAAAAGAATAATTAGACTGTCTTGGAACCTGGAATGTCTGAGTTCAAATT
CAATTTTGCCGTTTTACCAGCTGTGTGACTTTGGGTGAGTTAATAAACCTT
TTCGTGTCTCAGTGTTCTCACATGTAAAGAGACAATAATAAGCCTACCTGT
TTCATGGGTCATTATGAGGATTAAGGAGTTAACATTTAAATAGTTCTTAGA
ACAACCTCTGACATATTTTAAGTACAAAAATATATACATATATTAAATAAT
AACTTTTCTAAAACATCCTACCTACAATCTTGTGTGCAAATTGGTGGCTCA
ATTCTGCAACTGTTGTTGGTGGTGTTGTTGTTAAGCTTTTGTTTGTCATGA
CTGTTATCAGTAATATTAATACAGACAGTTAACTGAACCCTTCCTCTGCAC
CAGGCATTATATGGACTATTTTCATTCTGACTCCCTGCATTCTATGAGACA
ACCACCATTGTAATCATTCTCACGTTGCCAATAAGGAAATGGAGAATGAGA
ATTCAGACTTCTCCAAGAAGTGCTGCAGACTGATTATAAATCATGCATCCT
AAACACACACATATTAAAGTATCAACTAAATCAAACAGAATAAAACTTTTG
TTTTTCTATCTACAAAATGCATGAATTAAAATATGCCCCAACTACTTAACT
AATATATTTAGTAAGTAGAGGGATGGAAGCGTTTTCACTCCTTCAATACAT
TCTTCATCAACCTCTCTCACCTTACCCCTCTGTCACAGGCATTTCCTATGT
CATGCGGTTTTTCTGATGTACGCTAGGTGGCAGTCAAAACCACGAACTCTT
GAAAGAGAGTATATTCCTATTTTTCTGCAGCCTCAACCTCCAGGGCTCAAA
CGATCCTCCTGCCTCAGCCTCCTGAGTAGCTGGGGCCACAGGTGCGAGCCA
CCACACCTGGCTAACTTTTACATTTTTGATAGAGACGGGGTCGCCATGTTA
GCCAGCCTGGTATCGAATTCCTGACCTCAGGTGATCTGCCCGCCTCAGCCT
CCCAAAATGTTGGAATAACAGGAGTGAGCCACAGTACCTGGCCGGTAATTT
TTAACTTCTAGCTATACACTTAGTTTTTTGTCCTTTTCAGTGGACAGAAAT
TATAATGCCTGTTTGACAGGGGATAATTCTGAGGCACTGGGAAGCCATGAG
ACTGCATGGATTGCACAGGCAGGCAAGAACATGGGAAGGAACAAGTGTCTT
AGACACTTGTCTCAGTGGTCTAGAAAAATCATGCTAGCTGATTCATTCACT
CCACAAACAACTGATCAACATCTTCAAGAAGCCTAACAATGTACTGAGTTC
AGGGGACAAGAAAATAATTCAGACAGGCTCTACCTTCATGGTGGTGTTTGA
AGAATAGGGATCTAGAAAACGGTAGGTAATAGTGGCTGTGCAAAAGATATC
AGAGATGATATGAAAAGGAGGGACTAGACCATTTTACCCAGGAGTGGAGGT
TAAACATAGGGTCTTTAAGGGAAACGTAAAAATATTAATTCTTTTCATTTT
TGAAGTAAAATGACCATCGCTTCTCGGCCGTTTGGCTAAGAACAAGTGAAG
TAAAATGACTGAGGATGACAGACATAAATACTGCTATACAAACATGGTAGC
ACTGAAATTGGCTCTTGCCTGACAGGAAGCAAAATTATAAAATTCATTATT
TAGATATATCAATAATGATGGTGATCAGGCTGTAATAATAATGTTATTAAT
CATTATGTATCAATAAGAATACAGGTGTGTGACTTTACAATGTGCCTAAGA
GCAACCCAATATTTTGATTGTAAACCACATTCCCTTAAACACACACACACC
TCAAACAAGACCCCATAAAGCAGACTGCACTAAAGTGGAGGTTATGTAAAA
GTCCAACAGAATAAGAACCCTCCCCCATTGTGTATTAATCTGTGAACTAAA
AAAAAATTTCATTAAATTGAAAATATCTAATTGTCAACTAGCAATTTTAAA
GAGTTTAGGCAGAAAATGAAATATAAAGCTTTTTTTTAACTTTTAGATTTT
TCAAAGCTAGCAGAACTGCTGAAGAATAACAATTCAAAACATAGGTTTGCT
```

FIG. 8-74

```
TTGGTTTCAATCTCTGTAGCCAAAGGCATTTACAATGTAGGATGTTGTTTG
TGCTTTCAGACACTAGATGACGCTCCAAATCAAAATGCCGGTAGTTGGACA
GCCCCTGATCAAGCCGCCCGGCAAATCATTAACTGGGTTGACACTGTATTA
CTCAGCAGATTTCAAAACTCATTCACATACAGAGTCTTTTGGTGGACAAAA
ATAATTATTACCCACAATTGACAGTGACAGTACTGAGAAGCTGGGAAACTG
AAGTAGGACCCTGGAGCAGCCAAGTACAGAGACTGGCTCCCAGGACCTTAG
GAGTTAATACTATTCCTAAAGAGAATAAATTGTCAAATAGACAAGAAATTC
ATGTGGGTTGATGCATTCACTTCCCCAAAACAATTATTAAGCAGTAGAAAT
GATAACTACGCTGGTAGTGGAAATAGTTTACAGTAAAAGGGAGAAGACATG
CAAAAACCAAAAAAAAAAACGGGGCCGGGCGCAGTGGCTCACTCCTGTAAT
CCCAGCACTTTGGGAGGCTGAGGCGGGCCGATCACGAGGTCAGGAGATCGA
GACCATCCTGGTTAACAAAGTGAAACCCCGTATCTACTAAAAATACAAAAA
TTAGCCGGGCTTGGTGGTGGGTGCCTGTAGTCCCAGCTGCTCAGGAGGCTG
AGGCAGGAGAATGGCGTGAATCCGGGAGGCGGAGCTTGCAGTGAGCGGAGA
TCACACCACTGCACTCCAGCCTGGGCAACAGAGCAAGACTCCGTCTCCAAA
CAACAACAACAAAAAAACAGGCAGTGATGTTTTATGTGGGTCAGTGTGAAG
TAGAGATCAAAGGAGAAAACGGCCAATCTTACCAAATAATGGATGCAGAAA
TAATCTTCATGGAGAAGCCACTTTAATTATGTCTTAAATGAGAGTAACAAA
TTAAACATAAGAACCTGTAGGGGCTAAGGGAAAACTTACTCTTTGGCCTCT
GAAGAGTCGCTGAAAACCACCGACAAGAGGAAGATTAATAGGATAAAATGC
ATCCAATTTATTATTATTATTATTATTATTATTATTATTATTATTATTATT
ATTTTTAGACGGAGTCTCACTCTGTCACCAGGCTGGAGTGCAGTGGCGCAA
TCTCGGCTCGCTGCAACCTCCGCCTCCCGAGTTCAAGCAATTCTCCTGCCT
CAGCCTCCCCAGTAGCTGGGACTACAGGCATGTGCCACCACGCCCAGCTAA
CTTTTGTATTTTTAATAGAGACGGGGTTTCACCATTTCGGCTAGGGTGGTC
TTGACCTCGTGGTCTGCCCGCCTCAGCTCCCAAAGTGCTGGGATTACAGGC
GTGAGCCATTGCACCCGGCTGCATCCAATTTATTAATGTGTATATTAATAA
ATTATCCAATTTATATCCAATTTATTAATGTGTATTAACATGTACAGGGGA
AATTGTCCATTTTTATTTTTTAGATTCAACAAAGTATGGGCCGCCGTGTAG
AAATAGGATTGCTAATAAACAGAGTAGGGAAACCCAGCAAGGCCTGTCTGT
CTAGATTCTTCTTCGCCTCTCTGTGCAGCATTCCTTCCTTCTGGATCCTCT
CTGGAATGCGGTCTGGTGATCTATGATCAAATAAGGTAGTTCAGATAATTT
CTTTATGGCCAGTTTTTACACAGAAAAACAGAGGGAAAGTTAGAGTAATAT
TTTTAGGTTTTATGGCTGGGCTCTGGGGAAAAGGTGTTTTGATTTCTATGA
CCTAACTTGAGGAAGAGGAATTCTCATTTCTATGGCTAGACTCCGGGGAGA
ATGGGACTCAGAGACAGGAGGGCAGGAGAAGATCAGAGAAAAACTTTGGCT
TCTGCGGTCTTTATTTTGGGGTATTGTTTTCTGAGTTCCAACAAACCCCAA
GGACCTACAAAGACTGCATACTTTTTTTTTCCTTTTTATTAATTGTGAGAT
AACCACAGCATAGGCAATTTGTTTTTTGTTTTTGTTTTTGAGACAGGATTT
TGCATTGTTGCCCAGGCTGGAGTGCAGTGGCATAATCATAGCTCACTGCGT
CCCCAAACTTCTAGGCTCAAGAGATCCTCCCAGCTTAGCCACAACTGAGAG
GTGCTACTAGCATTTAGTGAGTAGAGAACAGATATGACTAGAGGTTCATTA
AGTGTTTTGAGCCTTTACAGCTTCAAAATTGTCTTTGCTAACCCCTAACTT
TTGGATGCTACAGAGGGCCCCTGGAGTATCCAAAGGAGAGGTAAACAGGAT
CATTTGACACGTTTAGTTATATAGGATTGTTGAAATAAGGTGATATTTGAT
CTTCAGGTCATATTTCAGTGAAAACTGTGAATGTGTGTTCCAAAATTATAG
```

FIG. 8-75

```
GGGATTTCTAGAGTTCTGATATCTGAGTTTGTGTCATCAGTTATAATTAGA
GTTATTGTGTTAGGCTATTGTAAATCACAGAGGTGACTAAATTTCTTTGTC
AATTGTGTTTTTGACTGTGACTACCCTAGGACATTTTAACATTCATAGACA
AATGTTGTCTTGTTTTGAAACTCTGCAAAGAATGGATTATAACCCTCAATT
GCAGGTTTCTGATAACTTTGAAGATTGTGAACAGGAGTTAACTAGGTGAGC
TGAACTATTGGAAAACTAATCTTCTTGACTCTTGCCTCTGTACCTAATTCT
TCCTGGATGCAGGACAAGAACTCAGGCAAAGGTGCTGCAGCATAAAGTCTG
GCCAGAGAAACTGACACTCCAGAGGTTTTGTAACAATATTTTATGTTAAAT
AATTTATACGTATTTCCTATTCTAAGCATTTCAAGTGATTGTAAAAACTCA
ACTCATGAAAACTTATAGCTGAGATGATGTATCCTGTGATTTTTAACTCAA
CTTTATACCAATCTAAGTTGATTAGCATTCTTACAAAGTTTAAGAAGTTAA
GATTTGCCATATTAAGTATTGTCTTAAGATTTTTAAGAATTGAAAAATTTG
GAGCAGTTTTGTTCATTAGTCAATTGGATACTTTAAAAGTCCAGTATGTCA
GATTTAAAAATTGCAATTTATAAGTTTTCTTCTTAAAGTTCGTCAAATTGC
AAAAGCCTTGCCAAAAATGAATGTTAAAAATTTGGTAGATTATTTGTTCTA
TGGGTTCTATGGGAAAAAATTGGTAGATTAATAAATGCCAATAGTAAGCAT
TGTAAATTGAATTTAAAAGTTTAAGGAAGAGCTATTAATTTAATTTTGTCA
TAATAATGAATTGAATGTTGTTTTTTAAGTACCATAGTACTTGCTGAATGA
TCTTTCTGTATGGAAAAGGACATAAAAATGCACATTGGTAACATCAACTCT
ATTTCAGCGGCGGGATTGTGGGGTGAGCTTATCTCCAGGTTTGGGAAGGAT
GTGTTGTATCATCTGCCTCTTGTGTGTGTACTACCTGCCATTGCTGCTTGG
CCACCAGCATCCATCTTGGTGAGTCCTGTCTCCCTCTAAAAGACTCGAGCT
GTGCTGTTCAATCCAGTAGCCCCTAGCTACATGTAGCTATTGTAATGAATT
AAAATTAAGTAAAATTAAACATTCTGCTCCTCAGACACCAGTCACATTTCA
AGTGCACAATAGTCACAAGTGGCCAGTAGCTAGTTTTGAACAGTGTGGAAA
GATTTCTGTCATCACAGAGCATTCTATTATCACGTTGTAAAGCATTCTCTA
GCTCTTGCAAACTTGTCAGATCCCTTAAAAGTTCTTAAAAATAATTCATCA
TTCGAATTTTGCTCAGACTAATTTTTAGGGAAGTCTTTTTCTGGAGGCGTG
GACTTGTGATCTCCATAATTCATCCCTTCTACTATGTTAGTTACCTTGAGC
TGCTGTAATAAAATACTATAGACTTAGTCGCTAAAAAAAAAAATAACTTTCT
CACAGTTCTGGAAGCTCAGAAGTCCAAGATCCAGGTGCTGGCCAATTCAGT
TTCTAGGTGAACGCTCTCTTCCTGACTTGTTGGTGGCAGCAGCATTCTCAC
TATGTGCTCATGTGGTGTCCTTTTTGTGCTTGTAGGGCTTAGGCAGTGGAG
AGAAGGAGGAGAGAAAAGAGTTTCACTGTTTTCTCCTTTTCCCGAGACAGT
TTTTGTGTAGCCCAGGTGGACAGCAATGGCTCACTGCAGCTTCTTCCTGGG
GTCAAGCAATCTTCCCACTTCAGCTTCCAGAGTAGCTGGAGCTTCAGATGT
GTACCACCACACCCAGTTCATTTTTAAATTTTTAGAAGTTGGGGGTCTCA
CTATTTGTCCAAGCTGGTCTTGAACTCCTGGGCTAAAGCGAGCCTCCTGC
TTCAGCCTCTCATAGTGTTGGAATTACAGGCATCAGCTGCAGCACCTGGCT
CTATTGTCTTTTTTTTTTTTTTTTGAGATGGAGTCTCTATCACCCAGGC
TAGAGTACAGTGGTGTGATCTCACTGCAACTTCCACCTCCTGGTTTCAAGG
GATTCTCCTGCCTCAGCCTCCCAGGTAGCTGGGAGTACAAGCGTGCACCAC
CACACCTGGCCAATTTTTGTATTTTTAGTAGACATGGGGTTTTACCATGTT
GGCCAGGCTGGTCTCAAACTCCCAACCTCAGGTGATCCATCCACCTCAGCC
TCCCAAAGTGCTGGGATTACAGGCATGAGCCACTGCACCTGGCCTGTTGTC
TCTTTTAATAAGGGCATGAATTTCATCATGAGAGACACATCCTGATGAGTT
```

FIG. 8-76
```
TGTCTAAATATAATGACTTCCCAAACGCCCCAGCTCCAAGTACCATCACAC
TGGGGGTTAGGGTTTCAACATATGAATTTTGCGACGGGGAGTCAATTCAGT
CCATAGTACCTACTGTATTAGTTTTCTGGGGCTGCAGTAACAAAGTACCTC
AAACTCGTTGGCTTAACAACAGATATTTATCGTCACACAGTCCTGGAAGCT
GGAAGTCTGAAATCAAAGTATCATCAGGTTTGATTCCTTCTGAAGGCAATG
AGGGATAATCTGTTCCAGGTTTCTCTCCCAGCTTCTGGTATCCCCAGACTC
ATTGCTTGACTTGAATGGTGATTCTCCCTGTGTCTACTCACCACATTTTCT
CTCTATAGGTGTCAGTCTCTGTGTATGACATTTCTCCTTTTTATAAGGACA
CCCTTTATGTTGGGTTAGAGCCCACTCTTATCTTAACTGATGAAGTGCAAA
GACCCTATTTCCAAATAAGGCCACATTCACAGGTCCTGATACAGGAGGGGG
AAAGTGCTGGGAAGGGAAGGGCATGGTCCCTTTAAATGATATGGAAGTGGG
GAAGGGAAGGGCGTGGTCCCCGGCTAGGGCTCCACCCCCAGGCCTGTGCCC
AGGGACCACGGTGAGGACAGGCATTTTTGTTTTCCTGCCCAAATGTTGCAT
TTCCCAAGACCTCCCCTGGCCTGCCACAAGACACGAATAGCTGGACGTCCA
GGGGAGCACACTGGCAGAAGAGCACACAACAAACGTTTGCCTGGCAAAATG
AGGCGGAATTTGACTGGGGTGGTTGGAGGAGAGCCTGGGCCACTGAGTGGC
TGACTCCAAGGGAAAACTTTCCCACTCCATCCACTTTTGGCTTTGCCCAAC
TGCTGAGAGCTACCTCCACTTAATAAAACCTTGCACTCTTTCTCTAAGCCC
AGGTGTGGTCTGATTTATTCCGGTACACCAAGGCAAGAACCTGGGATACAG
AAAGCCTTCTTCTGTCCTTGGGACAAGGTAGACGGTCTAATTGAGTTGGTT
AACACCAGCTGCCTATAAATGGCAAAACTAAAAGAGCACCCTGTAACACAC
ACCCACTGTGGCTTCAGGAGCTGTAAACATTCAACCCTAGACACTGTGGTG
GGGTCATGGGGTTGGAGACCCACAACCTGCCCGTCTTAATGTTCCCCTAGA
GGTTTGAGCAGCCAGGCACTGAAGAAATTAGCCACACTCCTATCACATGCC
ATGCGAGCGGGACAAGGGAACTTTTCCCATTTCAGTACTGGTGGTTAGGAC
TTCAACAACTTTATTTTTGTGGGAATGCATACTTCAACCCATATTATGAGG
GTTCCTAGAATGTGGACTGCTGAGGCTGAAGCACTACCTAAGTGCCTGAGG
CCAGCCTGCAGTTGGTTTCTGGCTCTCATGAGTTAGCTAACATCTCGGGAG
AGAGGAAGACAGGCCTAGGAAGAGCAGAGCCCACGATTCATTCTTCATTCC
ACCTCTGCTCTTCAGAATCTCCTTCAGTCTATGTGATGAGCCATCAGACCT
CTTGGTGGGAAATGGTGCTGCCGTGCCTAGCCCTTTTCGATTGTGCTACCA
TGCTGAGATTACTGAGGGACCAGGAAGGCCTGGACTCAGACCATATAGGGT
GCCACCCTAGTGGGAATGGAACCTGTCAGTGCTGGGTGAATGTGACCGTCC
CATGAGGAGAAGACAGATACTCTTGCCAAGCTGAGCATGGAGACCTGATGG
GACACTCATTATCATGAGGGGATGAAGATCCAGGCTTCCAAAGTTGGTACC
ACAGGGTGGCTATGGCATGAACAGGGGGTTAGGATGAAGGACCCAGAATCT
AACATGCTGGAGAGGTAGGGAAAGGAGTCAGAAATTCAGTCTTGTTGAACC
CTAAATATTGCATCTCTCTCTCTTTATTTTTTTTTCTGGAGATGGGGG
TCTGGCTCTATCATCCAGGCTGGGGTGTAGTGGCATGATCTCTGCTCACTG
CAGTCTCCGCCTTCTGGGTCAAGAGATCCTCCCACCTCAGCTTCCTGAGT
AGCTGGGACTACAGGTGCGCGCCACCACTCCCAGCTCATTTTTGTACGTTT
TTGTAGAGACACGGTCTCACCATGTTGTCCAGACTGGTCTCGATCTCCTGA
GCTTAAGCGATCTGTCGCCTCGGCCTCCCAAGAAGGATTGGGATTACAGGG
CCTGAGCCACTGTGACCAGCCAACATTGCATCTAATTTTAGGGTATTCATC
TGACTTTCCTGAACACTGCTTCTTGGGTGCTCATTTTAGCAGGCATTTGGC
CATAGGTAGATTTAAAGTTTTGGTGGGTTTTGTTGTTGTTGTTGAGACAAA
```

FIG. 8-77
GTGTCACTCTGTTGCCCAGGCTGGAGTGCAGTGGCAAGATCTCAGCTAACT
TCAACCTCCATCACTGTGCTTCAAGTGAGTCTCCTGCCTCAGGCTCCCGAG
TAGCTGGGATGACAGGTGTGTGCCACCATGCCCTGCTAATTTTTTATATTT
TTAGTAGAGATGGGGTTTCGCCATGTTGGCCAGGCTGGTCTGGAACTTCTG
ACCTCAGATGATCTGCCCGCCTCAGCCTCCCAAAGTGCTGGGATTACAGGT
GTGAGCCACAACCCCTGGCCAACGTTTTCTGAAAAAGCTATTCTAATCAGG
TAGGAAAGATGGGAAGCGGGGTGGCGGGGTGTACTTTTTTCTGCATATTCA
GTTGCAGGGTCCCAGACCAGGGAACAATCTTCAATCTCTTACCTTCAATCT
CCCTTCATGGAAGTCAGTGCTCAGCCTGGCCATTTACTGTGTGCAGTAGGT
GTGATGTAGAAAGCCTCTAAACCTCCATGCCTACCTGCCAGGAACAATATA
CACAAAGGTGTGTGTGTGTGTGTGTGTGTGTATCTTACGGATTCTTC
CACGTAACTATGTGGACATCTAATCCATTGCTTCCAACTCTATATTGTGCA
GTGACTTCATTTTACCTCCACCTCTCTCAGTGAAGGATATCAGTCAGCCCA
CACTTTCCTGTCACCTTTATGGGATATGTTTGAGATGATATTTGGAAAATA
TTCCCAGGGAGTGGGCACTCCCATCAGCAGTGTATGAGGATTCCTGAGTCT
CCATATCCACACCAATACTGAGCATTATTCAGCTCTCTAATTTGTTAATGC
TCTCTTTTAAATGCAAAAGGACACATCACTTTACCTTTCTTTCATTACCAA
GTGCTTTGGATTTTCCTGTATCTAAATTTCTTGTTCATTTATTTCATATAT
ATATATATATATATATATATATATATATATATATAATTTTTTTTTTTT
TGAGACAGAGTCTCACACTGTCACCCAGGCTGGAGTGCAATGGTGTGATCT
CAGCTCACTGCAACCTCTGCCTCCTGAGTTTAAGTGATTCTCCTGCCTCAG
CCTCCCAAGTAGCTGGGATTATAGGCACCCACCACCACGCCCGGCTAATTT
TTTGTATTTTTTGTAGAGATGGGGTTTCACAATGTTGGCCAGCCTGGTCTC
AAACTCCTGATCGGCCCGCCCTGGCCTCCCAAAGCGCTGGGATTACTGGCA
TGAGCCACCGCGCCCGGCCTCATACATTTTTTATGTGGAGTTTCTGTTTTG
TTCTTCTTGGCCTTGTGCATTCTAATTACTCATCCTTTCGTCTGATTCAGA
CATTTAATTCTCTACCATCCTTACAGCAGTGTCTTAACTTTATCCATGGGA
TCCTTCATTGAACCGGAATTCTTAATTTTGACACAAACAAATTTATCAATT
TCTTTTTTGTGTGTGTTTTTTTTTCTGTGTGTGGTTTTTGTTTTTCACAT
TTCTGAGTATGACCTAGATTTATCCTTTGATAACTTCTTCTCTCTTCCCCA
TTTTCCTCCACTGGAGGTCAGCTATATGTGTGTGAGAGGGTTAGGTATATG
TGGATATATAGAGAAAGTTTAGGTATACATATGTGGAGAGGTCAGATAAAT
ATGTATATATGGGAGAGATATTGGGTATATATTTTGGGGAGGGGAGGTCAG
GTATATGTGGACATATGGGGAGGGGAGACCACAGCTCTCCTGGAGTCACCC
TCTTCCTCTTCCCTTCTGGGCAGGTAACGGTGGGGAGTGAGAGGGTGTTCC
TCCCTTCTTATTATTAGCCCCTGGGTACTTTAGGGTCTCTAGTGGTTATTT
TTCACAGAATTTTAACTGATAACTAATGAACAAATGTTTTCCCCACAGAAA
TATCTTTACGCCTTTTACAATCATTTTTATTTTCTATGCCATAACTTTATT
AATATTTGCCAATTTACTTGGGGTAGGACTTTGAAAATTTTGTTTAAATTA
AGGGAGGAGACCACCCCTCATATTGTCTTATGCCCAATTTCTGCCTCCAAA
GAAAGAAAAGTAAAAATTAAAAGGGAGAAATGAAATCCACAGGCAAACAG
CCCGGCACCGCACCCTGGGTCTGGTTAAAGATCGACCTTTGACCTAACAGG
TTATGTTATCTATAGATTCCAGACATTGTATGGAAAAGCATTGTGAAAATC
CCTGTGCTGTTCTGTTCTGTTCTGATTACTGATGCATGCAGCCCCAGTCAC
GTACCCGCTGCTTGCTCAATCAATCACGACCCTCTCATGCAGACCCCCTTA
GAGTTGTAAGCCCTTAAAAGGGACAGGAATTGCTCACTCAGGGAGCTGGTT

FIG. 8-78

```
TTTGGAGACAGAGGTGATTAACGGACGGTCAAGGCAGCCCCTTAGGCGACT
TAGGCCTGCCCTGTGGAGCATCCCTACGGGGAACTCCAGCCAGTTTGAGCG
ACACAGATCTGGAGAGCGCTCCCAGGTAGGCAATTGCCCCGGTGGAACGCC
TCACCAGAGCAGCACGTGGCAGGCCCTCGTGGAGGATCAACGCAGTGGCTG
AACACCGGGAAGGAACTGGCACTTTGTTGTCAGGGCATATTCCAAAAGCAT
TAAGGCCTTCCTATCAAAAATCCTTAACCCAGTAACCCGCGGATGGCCCAA
ATGCATTCAATCTGTAGCGGCAACTGCTTTGCTAACAGAAGAAAGTAAAAA
AATAACTTTTACAGGAAACCTCATTGTGAGCACACCTCACCGGTTCAGAAG
TATCCTAAGGAAAAAAGAAAAAAGAAGATGATTTAACATTAACCACTGAAA
ATTCTCTTAACCCGGCAGGTTTCCTAACAGGGGATCTAAATCTTAATTACC
ATACAAAGCTCTGACCAGACCTAGGGGATTCCCTTCAGGACAGGAGGATAG
ATGGTTCTTCCCAGGTAATTAAAAAAAAAAAAAAGCCATCTATACCAATTC
TAAGTTAATTTGGACTAAATAAGGTCTTATTAATAGCAAAGGATAATTGAA
ATCCCAAACTTACAAGGTTTTCAACAAAAGTAAAGTTTGCTAAAAGTTAAC
AGTGTAACATGTATTATAGTAACTTCTAATCTTGTGGCCTTAGACAGTCTA
GTCCACAGACATAAAAGAAGTTCGCTTTGGAAAAGAATGGTTATCATCCTC
GGAAAAAAAAAAAGGAAATAAAGAGGAGGCAGAATTTATATAAAAAAGAA
TGTTGTATGGAAAATCCTTGTCCTGAGATAAATTAACTAGTTGTTTAAAGA
AAGGGATGTTTGCAATAAGTCAGAAAGTTGAGGCATGTCGAAGAATTGTCT
GTGAAAGTCATGAAAAAATGTGTGTTAGAAAAATAAATTTATGTAAGAAA
TGTTGTATAATTTAAAAGTAATTAGGCCTCCTTCTAAATGTAAAACTATTG
AATAAACAGTTTATGTGCAAGGTATGTAAGGAAAGTAAAATATACCTTTGG
TAAAAGGATTATGAGGATGCATAAGAATGTGGATTTTTACCTACATTAAAA
GGTTACAAAAATTGTTTTGAAGGTTTAAGCAAGTTTTGAAACCTTAATTGT
AAAGAAAATTCTGTGTCTAAACATATTGGCTAAAGTTAAGGGGTATCATAC
AGTTTTTCTGTGAACTGAACATTAAAATAAAAACACAACGGGTTTTTCTTA
AAGCACTAACCTGTTCTTTAACAAAAATTATAAAAGGTTAAAGAAAAGTCT
ATAAAAATCTTACCTTATGGTCAGACATTAAAAATCAAATAAATATGTCTA
CAGAGTTTTATTAAAACTAAGTTTAACATTAATAACACACCAATATAAAGG
TGAAATCTAGCTTATCTGGTATAAACATACAAGAAGCGTTGTCAAATATAA
AATGGCATTTGACTTTCTTTGGTCTAAAAACTAATAAAAATAGGTGCTAAA
GGAAATTTCTCAGTAAGAAGGCACCAAGGACTATAAAGTCCACTGCTGATG
TCCCCACATTTAAAACAAAAGGTCAACTTCTTAAAAGTTATATACTTGGTT
TATCTTCCACTTTCCTTTCCCTCAAAACTAAAAGTCTTTTAGCACATGTAC
CACCCCTAGAATTTTCTGTAAACCAGCACCAGCCTGAAGATCATGTTCTCA
TCAAAGGGTGGAAAGAAGGAAAAACTTGAGCCAGCCTAGGAAGGACCCTACC
TTGTGCTGCTAACCACCGAGACTGTTGTTCATACGGTGAAAAAGGGATGGA
CTCATCACACCCGAGTCAAGAAAGTGCCACCCCCTCCAGAGTCATGGGCCA
TAGTCCCAGGGGAAAACCCTACCAAACTAAAGCTAAGAAAAATTTAACTCC
TTCATCTATTCTATTACTCTTTCTTCTTCCCTCACTCTATTTCTGACCATC
TAGTTATTAACATAACCAAGTCAATTTTGCCTCAAACTATTGAATTTAATG
CTTGCCTTGTTATACCCTGTGGGGACTTGCCAAGTCGAAGACATCTCTGTA
CTTCAGAAAAGTACCTCTGTCCCTCCTGACTCTCCTCAGACTGAGCCTTAG
TAAACTGAGACCATTTATTCCAGAGAGATTTCAATAAAGACCCCAGTGTCA
ACGAGGAGTCTTGCCCCCCGATGTAGAGCTTTTATGCCATAGTTGGTCGAA
TGTTGTGTGGACCACTAAAGAGCAAGGATGGACTGCCCCAACCGGTTTTTG
```

FIG. 8-79

```
TAATTTCCTAAAATCATACATTCATTTTACTAGAGGGTCATAGAAGTTAAA
GACTTAAAACAAACTTTGATAATTAAGCAGGATACCAAGATGCAAATGCCC
AGTTGGAATGGATCAAATATTCTGTCCACACATTAAACAAAACCAATTGTT
ATGCTTGTGCACATGGCAGGCCAGAGGGCCAGATTATCCCCTTTCCACTAA
GGTGGTCCTCCTGTTGACCAGGCATGGGCTGCATGGTAACTGTTTTCCAGG
ATTCTACAGCCTGGAGTAATAAGTCGTGCCAAGCTCTCTCTGCTATATCCC
AAAGTCCAGCACCCTGCAGGTCAACCCCTGAGGGCCATCCAGCTTCCATCT
CCCAAAACTAAGTTCACTTCTTGTCTCTCATGACAGGGAGGAAACTTAGCA
TTCCTTGGAGACCTGAAGGGATGCAGTGAGCTTAAGAATTTTCAGGAGCTT
CTCAATCAGTCAGCCTTTGTTCATCCCCAAGCGGATGTGTGGTGGTATTGT
GGTGGACCTTTACTGGGCACTCTGCCAAATAACTGGAGCGGCACTTGTACT
TTAGTCCAATTGGCTATCCCTTTCACCCTAGCATTTCATCAACCAGAGGGA
GGAAAAATAAGACATCGTAAAGCAAGAGAAGACCCTTATGTGTCTTTCAAC
TCTCACATCTATTTAGATGCAATTGGAGTCCCACAGGGAATAGCAGATCAA
TTTAAATCCCAAAATCAAATAGCTGCAGGATTTGAGTCAATATTTTGGTGG
GTGACAGTTAATAAAAATGTAGATTGGATAAACTACATCTATTACAACCAA
CAGCAATGAGTTTTTCATGAGTTAAAAGAAAAACTCATGTCGGCCCCAGCC
CTGGGGCTACCTGACCTGACAAAACCCTTTACACTCTATGTGTCAGAAAGA
GAAAAAATGGCGGTTGGAGTTTTGACCCAGACTGTGGGGCCCTGGCCGAGG
CTGGGCCTCCAAACAACTAGATGGAGTTTCTAAGGGTTGGCCTCCATGCTT
AAGAGCCTTGGCAGCAACAGCCCTGCTAGCACAAGAGGCAGATAAGCTAAC
TCTTGGACAAAACCTAAACTTAAAGGCCCTCCATGCTGTGGTGACTTTAAT
AAATACATCATTGGCTAACAAATGCTAGATTAACCAAGTACCAAAGTTTGC
TATGTGAAAATCCCTGCATAACCATTGAAATTTGCAACACCCTAAAACCTG
CCACCTTGCTCCTGGTATCAGAAAGCCCAGTTGAAAGTGACTGAGTAGAGG
TATTGGACTCAGTTAATTCTAGTGGGCCCAACTTCCAAGACCATCCTTGAA
CATCAGTAGACTGTGAGCTGTACGTGGCAGCTTCGCCAACGCCTGCAAAGT
GACTGAAGAAGACAACAAGCCCTGCTCCAGTCACACCCGGAAGCTGACTGG
TCCATGCATGGCCGAAACATGAGAAAACTCATCAAGGGACTCATTTTCCTT
AAAATTTGGACTTGCACAGTAAAGACTTCAACTAACCTTCCTCAGACTGAG
GGCTGTTCCCAGTGTATACATCAAGTCACTGAGGTAGGACAAAAAGTTGCT
ACAGTCTTATTATTTTATGGTTATTATAAGTGTACAAAGACTCTAAAAATA
ACTTGTTTGTATAATGCTATTCTATACAAGGTAGGTAGCCCAAGAAATGAC
CAACCTGATGTGTGTTATGACCCATCTGAGCCTCCCACGACCACAGTTTTT
GAAATAAGATTGAGGACTGAGGACTGGTGGGGGTTCATAAACGATACGAGT
AAAGTGTTAGCCAAAACAGAAGAAAAAGGAATGCCCAAACAAGTCACCTTG
AAATTTGATGCCTGTGCTGTCATTAATAGTAATAAGTTAGAAATAGGATGT
GGTTCTGTTCATTAGGAAGAGGCTATATGGCAGAAAATAAGTACGCTTGT
CATGAATTAAGACTGCGTGGAAATAAATGTAGATACTGGTCTTGTGTCATT
TAGGCAACTTGGTTAAAAAATAAAAAGAATCCTGTCCACCTTCAGAAAGGG
AAAAGTGGCCCTTCCTGTACCAGTGGTCAGTGTAACCCCTTAGAACTAGTA
ATAACCAACCCCCTTGATTCTCACTGGAAAAAAGGGGATCGTGTAACCTTA
GAAATAGTTGGGGCTGGACTGGATCCTTGAGTAAATATGGTGGTTTGAGGA
GAAGTTTATAAATGCTCCCCTGAGCCAGTATTTCAAACCTTCTTATGATGA
ACTGAATGTGCCAGTACTAGAAATTCCAGGAAAAACAAGAAATTTGTTTTT
GCAATTAGCTGAGCATGTAGCCCAGTCTCTCAATGTCACTTCATGTTATGT
```

FIG. 8-80

```
ATGTATGTGGAGGAACTGTAATGGGAGATCAATGGCCATGGGAAGCACGAG
AATTAGTACCTACAGACCCAGTTCCTGATAAATTCCCAGCTCAAAAGACTC
ACCCTGATAACTTCTGGGTCCTAAAAGCCTCAATCATTAGACAATACTGTA
TAGCAAAAGTGGGGAAGGACTTCACCCTTCCTGTGGGAAGACTCAGCTGCC
TTGGGCAAAAACTGTATAATAGTACTATAAAAACAGCCACCTAGTGGAGTT
CAAACCACACTAAGAAAAATCTATTTAGTAAATTCCCAAAGTTGCAAACTG
TGTGGACCCACCCAGAGTCCCACCGGGACTGGACAGCCCCCACTGGATTAT
ACTGGATATGTGGGCATACAGCTTATGCCAAATTACCTGACCAGTGGGCAG
GTAGTTGTGTTATTGACACTACTAAACCATCTTTCTTCCTACTGCCCATAA
AGACAGGCAAACTCCTGGGCTTCCCCTGTATATGCTTCCCGCAAAAAAAAA
AAAAAAAAAAAAAAAAAAAAAAAAAAGCATAGCTATAGAAAATTGGAAA
AATAATGAATGGCCCCCTGAGAGAATCATACAATATTATGGGCCTGCTACT
TGGGCACAAGACGGCTTGTGGGGATATGGGACCCCCATTTACATGCTCAAC
TGAATCATACGGTTACAAGCTGTCTTAGAAATAATTACTAATAAGACCAGC
AGAGCCCTGACTACTGTGGCCTGGCAAGAAACTCAGATGCAAAATGCTATC
TATCCAAAATGGATTGGCTCTCGACTACTTGCTAGCAACTGAAGGAGGGGT
CTGTAGGAAATTTAACCTTACTAATTGCTGTCTACACATAGATGATTAAGG
GCAAGTAGTTGAAGACATAGTTAGAAATATGACAAAAGTGGCACATGTGCC
CATGTAGGTGTGGTATGGATTTGTTTCTGGGGCCATGTTTGAAAAATGGTT
CCGAGTGCTAAGAAGATTTAAAACTCTTATAATAGGAGTTATAATATTAAT
AGAAACCTGCTTACTGCTTCCTTGTTTGCTACCTGTACTTCTCCAAATGAT
AAAAAGCTTCATCACTACCTTAGCTCACCAAAATGCTTCAGCACAAGTGTA
CTATATGAATCATTATCAATCTGTCTTTCAAGAAGACATAGGTAGTGAGAA
TAAAAGTGAGAACTCCCACTAATGAGTGAGATTCTCAAAGGGGGTGAATAA
GTGAGGCGACCACCCCTCATATTGTCTTATGCCCAATTTCTGCCTCCAAAG
AAAGAAAAGTAAAAGCTAAAAGGCAGAAATGAAATCCACAGGCAGACAGC
CTGGTGTTGCACCCTGGGTCTGGTTAAAGATTGACCCCCGACCTAACCGGT
TATGTTATCTATAGATTCCAGACATTGTGTGGAAAAACACTGTGAAAATCC
CTGTTCTGTTCTGATTACTGGTGCATGCAGCTGCCAGTCACATACCCCCAC
TTGCTCAGTCGATCATGACCCTCTCACACAGACCCCCTTAGAGTTGCAAGC
CCTTAAAAGGGACAGGAATTGCTCACTCAGGGAGCTCGGTTTTTGGAGATG
TGAGTCTTGCCAAAGCTCCCAGCTGAATAAAGCCCTTCCTTCTTTAACTCA
GTGTCTGAGGGGTTTTGTCTGTAGCTTGTCCTGCTACAAAAATAAGTGTTA
AACATGAGTTTTATATTACCTCATAGGTGGAAGAAGACAGGCCAAAAAAGC
TGTTTTAACAACAACAAAATGCACAAATATTTATACTAACAAGACAGATAT
CCATTGCAGTATGACACGAGAAACAAATAAATGAGACAAGCAGTCAATTCA
GACATTTTAGGAAGTGATTTTTACAGAACATAGTGACAATTGCTGAGATCT
GGTAGCCTTGCAAGATTCCTTTGTTATAATAAAAATAACATTGGCAAAGAC
CATTTTATGATGCAGACTTCTGCTTTTTTAAAGTTTGGGGGGAAGGGGAAA
CATTTTTATTCTATAATGCTGAAATTTCATTTTTCTTTTCTCTTTTTTAAG
ACCAAGTCTTGCTCTCTCACCAAGGCTAGAGTGCAGTGGCGTGATCTCAGT
TCACTGCAACCTCCACCTCCCGGGTTCAAGCAATTCTCCTGCCTCAGCCTC
CTGAGTAGCTGGGACTACAGGCACCATGCCCGGCTAGGATAACATTTTTTG
TTTTTAGTAGAGATGGGGTTTCACCATGTTGGCCAGAGTAGTCTAGAACTC
CTGACCTCAAGTGATCTGCCCGCCTCATCCTCCCGAAGTGCTGAGATTACA
GGTGTGAGGTACAGCATCTGGCCTCATGCTGAGATTTCTTTCATTACCAGT
```

FIG. 8-81

```
TCAAACACCTTTCACTTTTCAAGGCACAAGGAGAGGAATTCCATGTGTTGA
CACTGGGAGGAAGGGTACAGACCTACTTAAAAGATTCAAAACTTCTATGAC
AGTAAAAGAAATGTATATCAAGTTCCTTAGGGCTGCCGTAACAAAGTACTA
TCAACTGGGTGGCTTAGAACAAAAGAAATTTATTCTCTCACAGTTACGTAG
GCCAGTTGAGATCAAGGTATTATCAGGGCCAAGATCCCTCTGTAGCCTCTG
GGGAAGGATTCTTTCTTGCCTGTTTCCACTTCTAGCAGCTTCCTGTGTTTG
GTTTGTGGCAGCATAACTCCAATCTCTGCCTCCATCTCTACCTGGCCATCA
TCCCTCTGTGTCTGTGAGGACCCCAGTCATTGGTTGGAGGACTCACCCTAT
TCCACTATAATCTCTTCTTAACCAGTGAACTCACCGTATTCCAGATAAGGT
CAGGTTCACAGCTACTGAGGGTTAGGACAGAGTATCTTTTGGGGAGATGCA
ATTCATCCCATAAGTGGGTGGAAAAGGATGATTAACAAGTGGTATGTGGGG
ATGTATTGTTTGCATCTACGTAGCTCTCACCCCATTTCTTTCCACAACAC
ACATTTGTCACTCTATTCTTTATTAGGTTTACAGAGAAAAGTAGATCTTCA
ACCACTTTCCTGGGATGTGGATACAGCTCTTTTTTTGGAGACAGGGTCTCA
TTCTGTCACCTAGACTGGTGTGCAGTAGCACTATCATGGCTGACTACAGCC
TCAATGTCCCAGGCTTAAGTGATCTTCCCAACCTCCTGAGTGGCTGGGACC
ACAAGTGTGTGCCACCACACCTGACTAATTTTATTTTTAATTGTTTTGTG
AAGACAGCATCTCCCTATGTTTCCCAGGCTGGTCTTGAATTCCTGGGCTCA
AGCCATCCTCCTGCCTCGGCCTCCCAAAGTGCTGGGATTACAGGCAAGAGC
CTCCATGCCTGGCCTTCAACTCTTGACCTTATGAACACAGCCCTATACCAG
TTCCCTTCATGCATGTGCCTATAAGCTAAACCCTTCCCAAGTGTACATGAA
AATCTGAAACCCCAACAAATATGGCCTAATTCTAAATCTGACTTTCCCAGG
AGTAATTTTGTCATTTCCAGCTTACCAGCCTTTGTGAGTGTTGAATTTCA
GCATTTCTGTTTGCTTGCAGCAGAAGGTGGAGCCAGGATAGGGTGGCTCAA
GATTAGAGTTTCTTCCTTAACAGTTCAGTCAACTTTTTAATCTTGGATTTA
TAGCTTCCTACCTGCTCTCTTAAAGGTGAAATGATCTATTCACCTTCAGAC
CATTTGCCCTCGGGGTCTCACTGAGCAATCTATGGCTTAAGTCTTCTAAGT
CTCTTAATGGCCAAATACAATGGACAATTTTCAGGTATATCTGACACCATT
TCTCTGCAGCCTTTGGCACCTATAACCACTCCATGGCTTCCACAATGTGAT
TGGTCATTTCTTTTTTGTTTATATGACAAGTTTTTATTCTTCTTCTGCCTG
TTAAATGCGCCTGACCCCCAGTGTTCTGATTTTCACTATTTTTCTTAAAAA
AAAAAGTTTAAATGAAAAAAGTTTCTTATGAAAATATTAAAACATATACAA
AAATAGAATAGACATTGATAATAGATCCTAAAATTCCTAGGGAAATTCAGC
AGACTGAGAATAGCTAATATAGTCTTCCAAAAAAAGATCAAATTTGAAGTT
GAGAAACTTCTTGAATTCAATTTACTAAAAAGCTATAGTAATCAAGACAGT
GTAGTCCTGACATAAAGATAGGATTATAGTCTGGGTGTGGTGGCTCATGCC
TGTAATCCCAGCACTTTGGGAGGCTGAGGTGGGCAGATCACCTGAGGTCAG
GAGTTCCAGACCAGCCTGACCAACATGGTGAAACCCCGTCTCTACTAAAAA
TACAAAAATTAACCAGGCATGGTGGCAGGTACCTGTAATCCCAGCTGCTTG
GGAGGCTGAGGCAGGAGAATTGCTTGAACCTGGGAGGAGGAGCCAGTGGCC
GGGATTGGGCCACTGCACTCCAACCTGGGCAATAGAGTGAGGCTCTGTCAA
AAAAAAAAAAGATAGGATTATAGATTATAGCATAATGGGATAAAATTGAG
ACTCCAGAAATAAACTCTCACATTTATGGTAGATTGATTTTTGATAAGGGT
GCCAAAACACTTCAATGAAAAAGAGTCTTCTCAACAAGTGATGGTGGAAC
AACTGAATAACCACATTTTGTTCTATCTGGGGCCCTGATTCAAAAACCCA
GGCAAAGATGGAGAGAAATCAGAACTCTCATACACTGCTGATAGGAGGATA
```

FIG. 8-82

```
AAATGCTTACTTTGGAAAAGAATGTGGCAATTCCTCAAAAGGTTAAACAGT
GTTACCATATGACCCAGCAAACCCACTTCTAGATATATAACCAAAAGAAAT
CAAAACATAAGTCTACAAAAAAACTTGTACATAAATGTTTATAACAGCACT
ATTCCCAATAGCCATAAAGTAGAAACAAACCAATGTCCATCGGCTGATGAA
TGAATAAATAAAATATGTTGTGGTATGTCCTTATAATAGATATTATTGGTC
CATGAAAAACATACATAAAAACATTATGCTAAATGAAAGAAGCCAGTCACG
GCAAAGCAATATATTATATGCCTCTATGTATACTAAATGTTCCAAATAGAA
AGAAAGTAGATTAAAGATTGTCTAGGGCTGGGAGGGGAGGAGGAGGAGAAT
GGAGGAATCTGGGAGGCGATGAATTAAGGGTACTGAATTAGGGGAACATGG
TTTCTTTTTGGGGAGATAGAAATGTAAAATTTTGGTAATGGTTGCACATCT
CTGTAAATATACTAAAATCCATTAATTTTTGCATTTTATTTTATTTATTTT
ATTTTTGAGACGGAGTTTCGCTCTTGTTGCCCAGGCTGGAGTGCAATGGCA
TGATCTCGGCTCACCACAACCTCCGCCTCCCAGGTTCAAGCGATTCTCCTG
TCTCAGCTTCCCGAGTAGCTGGAATTACAGGTGCATGCCACCACACCCAGC
TAATTTTTTTTTTTGAGATGAAGTCTTGCTCTTGTCTCCCATGCTGGAGT
GTGATGGCACGATCTTAGCTCACTGCAACCTACGCCTCCCGGGTTCAAGCG
ATTCTCCTGCCTCAGCCTCTAATGTAGCTGGGATTACAGTTGCCTGCTATC
ACGCCCGGCTAATTTTTGTATTTTTAGTAAAGACGGGGTTTCACCATGTTG
GCCAGGCTGGTCTCGAACCCCTGATCTCAGGTGATCTGCCTTCCTCGGCCG
CCCAAAGTGCTGGGATTACAAGCGTGAGCCACTGAGCCGGGCCAATTTTTG
CATTTACATAGATGAATTATATGGTATGCTAATTATATCTTACCAAAAAT
TGAAAAAAAGGAATAGTACTATCAGCCCCAATGTGCCCATCATCAATATTC
TACATGTTTCCAATGTTATTGTATCTGTTTGCCTACAGTCGAGGCCCTGAT
ATCCTGTTTGATTTTCTTGAATTGCCAAAATTTGCATACATGCTTACAAAA
ATAATGCCTGTTGAATTTGCTAGATATGTAAAGGTTTGGAGCAAATCAGGT
GTATTAAATTTATTAATATTGTTTGAAATGTCTAAGGCAATAATTCCCAAA
CTTCGTTGAGGGAGAAGGAAAGCTTTTAAAATCCCATTGCCCAGGTGGCAT
CCCATACTGTTACTGGGAATTATGCATTGGGATGGATCCTTTAACCGAGGA
GATTATTATAGCCGGAGCTCTGAACCAGCAATCTCAGTTCTTGTGATAGTG
AGCAAAGAACTACAAACTAACACCAAAATGCAAGCTTAAAGCAAAGTTTAT
TGAAGCACAATAATACACTCTGAGGGACAGCGGGCTTATTTCTGCGAAGTG
AACTCAGCACTTCTTTACAGAGCTCAAGGTGCTTTTATGGGGTTTGTGGGG
AGGAGTTGAGGTTTGGGCTGTATCTGAGTGACAGGATGATGTTATTTGATT
GAAGTGTATAGCTATACAATCTAAAATTAAACTGTGCATGGTCTTACCTAT
AATTTGTTAAGAAAAGCCTCCCAGGGATGGGGGGGCAAAACTGTATGTAAA
TTCTATTATAATGATGGCATGATGAACTTGGGGTGAACTTGAAGACAGGCT
TTTGTGTTGTTGGGCATGTGCCACCTTAGGGAATTTCCACCTGTACCCTCC
TTTCTCTTTCTCCAGGATATTTTGGCCACAGACTTTATCATAAACTCCATC
CCTTAGGGTGGCATTAGGGTAGTCTTGGGCCTGAATTTAGGTGGGCCAGTG
GCTGTCTTAGTGACAGCCTTTCCGCTCTCTTCTGTCATCCCCTCCCAACTG
CTAATGTCTAACTACCTAACAATTACCCATTAAATCAGTGTGTCTGGGGTT
AGGAGCAGGCCTCAATATGTTTAATCATTCTCCAGATAATCCCAATACTGT
AAAGTTTGTGAAACACTTGTCAGATAATTCAATTATGAAGGCTGTGGAAGG
TGTTTCAGTAGGATCTAATTGGTTAATGTTATGACTTAATTAATTTGAATC
AAAAAACAAAATGAAAAAGCTTTATATTTCTAAGTCAAATAAGACATAAGT
TGGTCTAAGGTTGAGATAAAATTTTTAAATGTATGATTGAATTTTGAAAAT
```

FIG. 8-83

```
CATAAATATTTAAATATCTAAAGTTCAGATCAGAACATTGCGAAGCTACTT
TCCCCAATCAACAACACCCCTTCAGGATTTAAAAACCAAGGGGGACACTGG
ATCACCTAGTGTTTCACAAGCAGGTACCTTCTGCTGTAGGAGAGAGAGAAC
TAAAGTTCTGAAAGACCTGTTGCTTTTCACCAGGAAGTTTTACTGGGCATC
TCCTGAGCCTAGGCAATAGCTGTAGGGTGACTTCTGGAGCCATCCCCGTTT
CCCCGCCCCCCAAAAGAAGCGGAGATTTAACGGGGACGTGCGGCCAGAGCT
GGGGAAATGGGCCCGCGAGCCAGGCCGGCGCTTCTCCTCCTGATGCTTTTG
CAGACCGCGGTCCTGCAGGGGCGCTTGCTGCGTGAGTCCGAGGGCTGCGGG
CGAACTAGGGGCGCGGCGGGGGTGGAAAAATCGAAACTAGCTTTTTCTTTG
CGCTTGGGAGTTTGCTAACTTTGGAGGACCTGCTCAACCCTATCCGCAAGC
CCCTCTCCCTACTTTCTGCGTCCAGACCCCGTGAGGGAGTGCCTACCACTG
AACTGCAGATAGGGGTCCCTCGCCCCAGGACCTGCCCCCTCCCCCGGCTGT
CCCGGCTCTGCGGAGTGACTTTTGGAACCGCCCACTCCCTTCCCCCAACTA
GAATGCTTTTAAATAAATCTCGTAGTTCCTCACTTGAGCTGAGCTAAGCCT
GGGGCTCCTTGAACCTGGAACTCGGGTTTATTTCCAATGTCAGCTGTGCAG
TTTTTTCCCCAGTCATCTCCAAACAGGAAGTTCTTCCCTGAGTGCTTGCCG
AGAAGGCTGAGCAAACCCACAGCAGGATCCGCACGGGGTTTCCACCTCAGA
ACGAATGCGTTGGGCGGTGGGGGCGCGAAAGAGTGGCGTTGGGGATCTGAA
TTCTTCACCATTCCACCCACTTTTGGTGAGACCTGGGGTGGAGGTCTCTAG
GGTGGGAGGCTCCTGAGAGAGGCCTACCTCGGGCCTTTCCCCACTCTTGGC
AATTGTTCTTTTGCCTGGAAAATTAAGTATATGTTAGTTTTGAACGTTTGA
ACTGAACAATTCTCTTTTCGGCTAGGCTTTATTGATTTGCAATGTGCTGTG
TAATTAAGAGGCCTCTCTACAAAGTACTGATAATGAACATGTAAGCAATGC
ACTCACTTCTAAGTTACATTCATATCTGATCTTATTTGATTTTCACTAGGC
ATAGGGAGGTAGGAGCTAATAATACGTTTATTTTACTAGAAGTTAACTGGA
ATTCAGATTATATAACTCTTTTCAGGTTACAAAGAACATAAATAATCTGGT
TTTCTGATGTTATTTCAAGTACTACAGCTGCTTCTAATCTTAGTTGACAGT
GATTTTGCCCTGTAGTGTAGCACAGTGTTCTGTGGGTCACACGCCGGCCTC
AGCACAGCACTTTGAGTTTTGGTACTACGTGTATCCACATTTTACACATGA
CAAGAATGAGGCATGGCACGGCCTGCTTCCTGGCAAATTTATTCAATGGTA
CACTGGGCTTTGGTGGCAGAGCTCATGTCTCCACTTCATAGCTATGATTCT
TAAACATCACACTGCATTAGAGGTTGAATAATAAAATTTCATGTTGAGCAG
AAATATTCATTGTTTACAAGTGTAAATGAGTCCCAGCCATGTGTTGCACTG
TTCAAGCCCCAAGGGAGAGAGCAGGGAAACAAGTCTTTACCCTTTGATATT
TTGCATTCTAGTGGGAGAGATGACAATAAGCAAATGAGCAGAAAGATATAC
AACATCAGGAAATCATGGGTGTTGTGAGAAGCAGAGAAGTCAGGGCAAGTC
ACTCTGGGGCTGACACTTGAGCAGAGACATGAAGGAAATAAGAATGATATT
GACTGGGAGCAGTATTTCCCAGGCAAACTGAGTGGGCCTGGCAAGTTGGAT
TAAAAAGCGGGTTTTCTCAGCACTACTCATGTGTGTGTGTGGGGGGGGG
GGGCGGCGTGGGGGTGGGAAGGGGGACTACCATCTGCATGTAGGATGTCTA
GCAGTATCCTGTCCTCCCTACTCACTAGGTGCTAGGAGCACTCCCCCAGTC
TTGACAACCAAAAATGTCTCTAAACTTTGCCACATGTCACCTAGTAGACAA
ACTCCTGGTTAAGAAGCTCGGGTTGAAAAAAATAAACAAGTAGTGCTGGGG
AGTAGAGGCCAAGAAGTAGGTAATGGGCTCAGAAGAGGAGCCACAAACAAG
GTTGTGCAGGCGCCTGTAGGCTGTGGTGTGAATTCTAGCCAAGGAGTAACA
GTGATCTGTCACAGGCTTTTAAAAGATTGCTCTGGCTGCTATGTGGAAAGC
```

FIG. 8-84

```
AGAATGAAGGGAGCAACAGTAAAAGCAGGGAGCCCAGCCAGGAAGCTGTTA
CACAGTCCAGGCAAGAGGTAGTGGAGTGGGCTGGGTGGGAACAGAAAAGGG
AGTGACAAACCATTGTCTCCTGAATATATTCTGAAGGAAGTTGCTGAAGGA
TTCTATGTTGTGTGAGAGAAAGAGAAGAATTGGCTGGGTGTAGTAGCTCAT
GCCAAGGAGGAGGCCAAGGAGAGCAGATTCCTGAGCTCAGGAGTTCAAGAC
CAGCCTGGGCAACACAGCAAAACCCCTTCTCTACAAAAAATACAAAAATTA
GCTGGGTGTGGTGGCATGCACCTGTGATCCTAGCTACTCGGGAGGCTGAGG
TGGAGGGTATTGCTTGAGCCCAGGAAGTTGAGGCTGCAGTGAGCCATGACT
GTGCCACTGTACTTCAGCCTAGGTGACAGAGCAAGACCCTGTCTCCCCTGA
CCCCCTGAAAAAGAGAAGAGTTAAAGTTGACTTTGTTCTTTATTTTAATTT
TATTGGCCTGAGCAGTGGGGTAATTGGCAATGCCATTTCTGAGATGGTGAA
GGCAGAGGAAAGAGCAGTTTGGGGTAAATCAAGGATCTGCATTTGGGACAT
GTTAAGTTTGAGATTCCAGTCAGGCTTCCAAGTGGTGAGGCCACATAGGCA
GTTCAGTGTAAGAATTCAGGACCAAGGCTGGGCACGGTGGCTCACTTCTGT
AATCCCAGCACTTTGGTGGCTGAGGCAGGTAGATCATTTGAGGTCAGGAGT
TTGAGACAAGCTTGGCCAACATGGTGAAACCCCATGTCTACTAAAAATACA
AAAATTAGCCTGGTGTGGTGGCGCACGCCTATAGTCCCAGGTTTTCAGGAG
GCTTAGGTAGGAGAATCCCTTGAACCCAGGAGGTGCAGGTTGCAGTGAGCT
GAGATTGTGCCACTGCACTCCAGCCTGGGTGATAGAGTGAGACTCTGTCTC
AAAAAAAAAAAAAAAAAAAAAAAAAAAAACTGAAGGAATTATTCCTCAGGA
TTTGGGTCTAATTTGCCCTGAGCACCAACTCCTGAGTTCAACTACCATGGC
TAGACACACCTTAACATTTTCTAGAATCCACCAGCTTTAGTGGAGTCTGTC
TAATCATGAGTATTGGAATAGGATCTGGGGGCAGTGAGGGGGTGGCAGCCA
CGTGTGGCAGAGAAAAGCACACAAGGAAAGAGCACCCAGGACTGTCATATG
GAAGAAAGACAGGACTGCAACTCACCCTTCACAAAATGAGGACCAGACACA
GCTGATGGTATGAGTTGATGCAGGTGTGTGGAGCCTCAACATCCTGCTCCC
CTCCTACTACACATGGTTAAGGCCTGTTGCTCTGTCTCCAGGTTCACACTC
TCTGCACTACCTCTTCATGGGTGCCTCAGAGCAGGACCTTGGTCTTTCCTT
GTTTGAAGCTTTGGGCTACGTGGATGACCAGCTGTTCGTGTTCTATGATCA
TGAGAGTCGCCGTGTGGAGCCCCGAACTCCATGGGTTTCCAGTAGAATTTC
AAGCCAGATGTGGCTGCAGCTGAGTCAGAGTCTGAAAGGGTGGGATCACAT
GTTCACTGTTGACTTCTGGACTATTATGGAAAATCACAACCACAGCAAGGG
TATGTGGAGAGGGGGCCTCACCTTCCTGAGGTTGTCAGAGCTTTTCATCTT
TTCATGCATCTTGAAGGAAACAGCTGGAAGTCTGAGGTCTTGTGGGAGCAG
GGAAGAGGGAAGGAATTTGCTTCCTGAGATCATTTGGTCCTTGGGGATGGT
GGAAATAGGGACCTATTCCTTTGGTTGCAGTTAACAAGGCTGGGGATTTTT
CCAGAGTCCCACACCCTGCAGGTCATCCTGGGCTGTGAAATGCAAGAAGAC
AACAGTACCGAGGGCTACTGGAAGTACGGGTATGATGGGCAGGACCACCTT
GAATTCTGCCCTGACACACTGGATTGGAGAGCAGCAGAACCCAGGGCCTGG
CCCACCAAGCTGGAGTGGGAAAGGCACAAGATTCGGGCCAGGCAGAACAGG
GCCTACCTGGAGAGGGACTGCCCTGCACAGCTGCAGCAGTTGCTGGAGCTG
GGGAGAGGTGTTTTGGACCAACAAGGTATGGTGGAAACACACTTCTGCCCC
TATACTCTAGTGGCAGAGTGGAGGAGGTTGCAGGGCACGGAATCCCTGGTT
GGAGTTTCAGAGGTGGCTGAGGCTGTGTGCCTCTCCAAATTCTGGGAAGGG
ACTTTCTCAATCCTAGAGTCTCTACCTTATAATTGAGATGTATGAGACAGC
CACAAGTCATGGGTTTAATTTCTTTTCTCCATGCATATGGCTCAAAGGGAA
```

FIG. 8-85

```
GTGTCTATGGCCCTTGCTTTTTATTTAACCAATAATCTTTTGTATATTTAT
ACCTGTTAAAAATTCAGAAATGTCAAGGCCGGGCACGGTGGCTCACCCCTG
TAATCCCAGCACTTTGGGAGGCCGAGGCGGGTGGTCACAAGGTCAGGAGTT
TGAGACCAGCCTGACCAACATGGTGAAACCCGTCTCTAAAAAAATACAAAA
ATTAGCTGGTCACAGTCATGCGCACCTGTAGTCCCAGCTAATTGGAAGGCT
GAGGCAGGAGCATCGCTTGAACCTGGGAAGCGGAAGTTGCACTGAGCCAAG
ATCGCGCCACTGCACTCCAGCCTAGGCAGCAGAGTGAGACTCCATCTTAAA
AAAAAAAAAAAAAAAAAAAGAGAATTCAGAGATCTCAGCTATCATATGAA
TACCAGGACAAAATATCAAGTGAGGCCACTTATCAGAGTAGAAGAATCCTT
TAGGTTAAAAGTTTCTTTCATAGAACATAGCAATAATCACTGAAGCTACCT
ATCTTACAAGTCCGCTTCTTATAACAATGCCTCCTAGGTTGACCCAGGTGA
AACTGACCATCTGTATTCAATCATTTTCAATGCACATAAAGGGCAATTTTA
TCTATCAGAACAAAGAACATGGGTAACAGATATGTATATTTACATGTGAGG
AGAACAAGCTGATCTGACTGCTCTCCAAGTGACACTGTGTTAGAGTCCAAT
CTTAGGACACAAAATGGTGTCTCTCCTGTAGCTTGTTTTTTTCTGAAAAGG
GTATTTCCTTCCTCCAACCTATAGAAGGAAGTGAAAGTTCCAGTCTTCCTG
GCAAGGGTAAACAGATCCCCTCTCCTCATCCTTCCTCTTTCCTGTCAAGTG
CCTCCTTTGGTGAAGGTGACACATCATGTGACCTCTTCAGTGACCACTCTA
CGGTGTCGGGCCTTGAACTACTACCCCCAGAACATCACCATGAAGTGGCTG
AAGGATAAGCAGCCAATGGATGCCAAGGAGTTCGAACCTAAAGACGTATTG
CCCAATGGGGATGGGACCTACCAGGGCTGGATAACCTTGGCTGTACCCCCT
GGGGAAGAGCAGAGATATACGTGCCAGGTGGAGCACCCAGGCCTGGATCAG
CCCCTCATTGTGATCTGGGGTATGTGACTGATGAGAGCCAGGAGCTGAGAA
AATCTATTGGGGGTTGAGAGGAGTGCCTGAGGAGGTAATTATGGCAGTGAG
ATGAGGATCTGCTCTTTGTTAGGGGGTGGGCTGAGGGTGGCAATCAAAGGC
TTTAACTTGCTTTTTCTGTTTAGAGCCCTCACCGTCTGGCACCCTAGTCA
TTGGAGTCATCAGTGGAATTGCTGTTTTTGTCGTCATCTTGTTCATTGGAA
TTTTGTTCATAATATTAAGGAAGAGGCAGGGTTCAAGTGAGTAGGAACAAG
GGGGAAGTCTCTTAGTACCTCTGCCCCAGGGCACAGTGGGAAGAGGGGCAG
AGGGGATCTGGCATCCATGGGAAGCATTTTTCTCATTTATATTCTTTGGGG
ACACCAGCAGCTCCCTGGGAGACAGAAAATAATGGTTCTCCCCAGAATGAA
AGTCTCTAATTCAACAAACATCTTCAGAGCACCTACTATTTTGCAAGAGCT
GTTTAAGGTAGTACAGGGGCTTTGAGGTTGAGAAGTCACTGTGGCTATTCT
CAGAACCCAAATCTGGTAGGGAATGAAATTGATAGCAAGTAAATGTAGTTA
AAGAAGACCCCATGAGGTCCTAAAGCAGGCAGGAAGCAAATGCTTAGGGTG
TCAAAGGAAAGAATGATCACATTCAGCTGGGGATCAAGATAGCCTTCTGGA
TCTTGAAGGAGAAGCTGGATTCCATTAGGTGAGGTTGAAGATGATGGGAGG
TCTACACAGACGGAGCAACCATGCCAAGTAGGAGAGTATAAGGCATACTGG
GAGATTAGAAATAATTACTGTACCTTAACCCTGAGTTTGCGTAGCTATCAC
TCACCAATTATGCATTTCTACCCCCTGAACATCTGTGGTGTAGGGAAAAGA
GAATCAGAAAGAAGCCAGCTCATACAGAGTCCAAGGGTCTTTTGGGATATT
GGGTTATGATCACTGGGGTGTCATTGAAGGATCCTAAGAAAGGAGGACCAC
GATCTCCCTTATATGGTGAATGTGTTGTTAAGAAGTTAGATGAGAGGTGAG
GAGACCAGTTAGAAAGCCAATAAGCATTTCCAGATGAGAGATAATGGTTCT
TGAAATCCAATAGTGCCCAGGTCTAAATTGAGATGGGTGAATGAGGAAAAT
AAGGAAGAGAGAAGAGGCAAGATGGTGCCTAGGTTTGTGATGCCTCTTTCC
```

FIG. 8-86

```
TGGGTCTCTTGTCTCCACAGGAGGAGCCATGGGGCACTACGTCTTAGCTGA
ACGTGAGTGACACGCAGCCTGCAGACTCACTGTGGGAAGGAGACAAAACTA
GAGACTCAAAGAGGGAGTGCATTTATGAGCTCTTCATGTTTCAGGAGAGAG
TTGAACCTAAACATAGAAATTGCCTGACGAACTCCTTGATTTTAGCCTTCT
CTGTTCATTTCCTCAAAAAGATTTCCCCATTTAGGTTTCTGAGTTCCTGCA
TGCCGGTGATCCCTAGCTGTGACCTCTCCCCTGGAACTGTCTCTCATGAAC
CTCAAGCTGCATCTAGAGGCTTCCTTCATTTCCTCCGTCACCTCAGAGACA
TACACCTATGTCATTTCATTTCCTATTTTTGGAAGAGGACTCCTTAAATTT
GGGGGACTTACATGATTCATTTTAACATCTGAGAAAAGCTTTGAACCCTGG
GACGTGGCTAGTCATAACCTTACCAGATTTTTACACATGTATCTATGCATT
TTCTGGACCCGTTCAACTTTTCCTTTGAATCCTCTCTCTGTGTTACCCAGT
AACTCATCTGTCACCAAGCCTTGGGGATTCTTCCATCTGATTGTGATGTGA
GTTGCACAGCTATGAAGGCTGTACACTGCACGAATGGAAGAGGCACCTGTC
CCAGAAAAAGCATCATGGCTATCTGTGGGTAGTATGATGGGTGTTTTTAGC
AGGTAGGAGGCAAATATCTTGAAAGGGGTTGTGAAGAGGTGTTTTTTCTAA
TTGGCATGAAGGTGTCATACAGATTTGCAAAGTTTAATGGTGCCTTCATTT
GGGATGCTACTCTAGTATTCCAGACCTGAAGAATCACAATAATTTTCTACC
TGGTCTCTCCTTGTTCTGATAATGAAAATTATGATAAGGATGATAAAAGCA
CTTACTTCGTGTCCGACTCTTCTGAGCACCTACTTACATGCATTACTGCAT
GCACTTCTTACAATAATTCTATGAGATAGGTACTATTATCCCCATTTCTTT
TTTAAATGAAGAAAGTGAAGTAGGCCGGGCACGGTGGCTCACGCCTGTAAT
CCCAGCACTTTGGGAGGCCAAAGCGGGTGGATCACGAGGTCAGGAGATCGA
GACCATCCTGGCTAACATGGTGAAACCCCATCTCTAATAAAAATACAAAAA
ATTAGCTGGGCGTGGTGGCAGACGCCTGTAGTCCCAGCTACTCGGAAGGCT
GAGGCAGGAGAATGGCATGAACCCAGGAGGCAGAGCTTGCAGTGAGCCGAG
TTTGCGCCACTGCACTCCAGCCTAGGTGACAGAGTGAGACTCCATCTCAAA
AAAATAAAAATAAAAATAAAAAAATGAAAAAAAAAGAAAGTGAAGTATAG
AGTATCTCATAGTTTGTCAGTGATAGAAACAGGTTTCAAACTCAGTCAATC
TGACCGTTTGATACATCTCAGACACCACTACATTCAGTAGTTTAGATGCCT
AGAATAAATAGAGAAGGAAGGAGATGGCTCTTCTCTTGTCTCATTGTGTTT
CTTCTGAGTGAGCTTGAATCACATGAAGGGGAACAGCAGAAAACAACCAAC
TGATCCTCAGCTGTCATGTTTCCTTTAAAAGTCCCTGAAGGAAGGTCCTGG
AATGTGACTCCCTTGCTCCTCTGTTGCTCTCTTTGGCATTCATTTCTTTGG
ACCCTACGCAAGGACTGTAATTGGTGGGGACAGCTAGTGGCCCTGCTGGGC
TTCACACACGGTGTCCTCCCTAGGCCAGTGCCTCTGGAGTCAGAACTCTGG
TGGTATTTCCCTCAATGAAGTGGAGTAAGCTCTCTCATTTTGAGATGGTAT
AATGGAAGCCACCAAGTGGCTTAGAGGATGCCCAGGTCCTTCCATGGAGCC
ACTGGGGTTCCGGTGCACATTAAAAAAAAAATCTAACCAGGACATTCAGGA
ATTGCTAGATTCTGGGAAATCAGTTCACCATGTTCAAAAGAGTCTTTTTTT
TTTTTTTGAGACTCTATTGCCCAGGCTGGAGTGCAATGGCATGATCTCGGC
TCACTGTAACCTCTGCCTCCCAGGTTCAAGCGATTCTCCTGTCTCAGCCTC
CCAAGTAGCTGGGATTACAGGCGTGCACCACCATGCCCGGCTAATTTTTGT
ATTTTTAGTAGAGACAGGGTTTCACCATGTTGGCCAGGCTGGTCTCGAACT
CTCCTGACCTCGTGATCCGCCTGCCTCGGCCTCCCAAAGTGCTGAGATTAC
AGGTGTGAGCCACCCTGCCCAGCCGTCAAAAGAGTCTTAATATATATATCC
AGATGGCATGTGTTTACTTTATGTTACTACATGCACTTGGCTGCATAAATG
```

FIG. 8-87

```
TGGTACAAGCATTCTGTCTTGAAGGGCAGGTGCTTCAGGATACCATATACA
GCTCAGAAGTTTCTTCTTTAGGCATTAAATTTTAGCAAAGATATCTCATCT
CTTCTTTTAAACCATTTTCTTTTTTTGTGGTTAGAAAAGTTATGTAGAAAA
AAGTAAATGTGATTTACGCTCATTGTAGAAAAGCTATAAAATGAATACAAT
TAAAGCTGTTATTTAATTAGCCAGTGAAAAACTATTAACAACTTGTCTATT
ACCTGTTAGTATTATTGTTGCATTAAAAATGCATATACTTTAATAAATGTA
TATTGTATTGTATACTGCATGATTTTATTGAAGTTCTTGTTCATCTTGTGT
ATATACTTAATCGCTTTGTCATTTTGGAGACATTTATTTTGCTTCTAATTT
CTTTACATTTTGTCTTACGGAATATTTTCATTCAACTGTGGTAGCCGAATT
AATCGTGTTTCTTCACTCTAGGGACATTGTCGTCTAAGTTGTAAGACATTG
GTTATTTTACCAGCAAACCATTCTGAAAGCATATGACAAATTATTTCTCTC
TTAATATCTTACTATACTGAAAGCAGACTGCTATAAGGCTTCACTTACTCT
TCTACCTCATAAGGAATATGTTACAATTAATTTATTAGGTAAGCATTTGTT
TTATATTGGTTTTATTTCACCTGGGCTGAGATTTCAAGAAACACCCCAGTC
TTCACAGTAACACATTTCACTAACACATTTACTAAACATCAGCAACTGTGG
CCTGTTAATTTTTTTAATAGAAATTTTAAGTCCTCATTTTCTTTCGGTGTT
TTTTAAGCTTAATTTTTCTGGCTTTATTCATAAATTCTTAAGGTCAACTAC
ATTTGAAAAATCAAAGACCTGCATTTTAAATTCTTATTCACCTCTGGCAAA
ACCATTCACAAACCATGGTAGTAAAGAGAAGGGTGACACCTGGTGGCCATA
GGTAAATGTACCACGGTGGTCCGGTGACCAGAGATGCAGCGCTGAGGGTTT
TCCTGAAGGTAAAGGAATAAAGAATGGGTGGAGGGGCGTGCACTGGAAATC
ACTTGTAGAGAAAAGCCCCTGAAAATTTGAGAAAACAAACAAGAAACTACT
TACCAGCTATTTGAATTGCTGGAATCACAGGCCATTGCTGAGCTGCCTGAA
CTGGGAACACAACAGAAGGAAAACAAACCACTCTGATAATCATTGAGTCAA
GTACAGCAGGTGATTGAGGACTGCTGAGAGGTACAGGCCAAAATTCTTATG
TTGTATTATAATAATGTCATCTTATAATACTGTCAGTATTTTATAAAACAT
TCTTCACAAACTCACACACATTTAAAAACAAAACACTGTCTCTAAAATCCC
CAAATTTTTCATAAACTCAGTTTTAAACTAACTTTTTTTCAAACCACAATC
TGATTTAACAATGACTATCATTTAAATATTTCTGACTTTCAAATTAAAGAT
TTTCACATGCAGGCTGATATTTGTAATTGTGATTCTCTCTGTAGGCTTTGG
GTATAATGTGTTCTTTTCCTTTTTTGCATCAGCGATTAACTTCTACACTCT
AACATGTAGAATGTTACTACAATATTAAAGTATTTTGTATGACAATTTTAT
TTGAAAGCCTAGGATGCGTTGACATCCTGCATGCATTTATTACTTGATATG
CATGCATTCTGGTATCTCAAGCATTCTATTTCTGAGTAATTGTTTAAGGTG
TAGAAGAGATAGATATGGTGGATTTGGAGTTGATACTTATATATTTTCTAT
TTCTTGGATGGATGAATTTGTACATTAAAAGTTTTCCATGGCAGAAATCTT
TTCAAAAACTTTTTTTTTCCGGGATGGATTGAAGGCCCTGATTTCACCACA
ATGCAATATATTAATGTAGCAAAATTGTACTTGTACCCCATGAATATATAT
AATCTTAAGAAAATTTTTTAGCCAATTATTATTACTTACTAGATATTAGG
CTGTGTTCTGAATCTTAATTTAATTCCTCCAAAGAATCTTATGAGGTAGGT
AGGAGCTATTGCTGCTATTCTGTTATGCTTATGTTGCTGTTATGAAACCAA
GGCACAGAGAGGTTAGTTAACTTGCTGAAGAAAATGATGTGCTGGATTTTT
ATTCTAGCTATTCTGGAATAACAACTACACAACCTTATGTCTGAGCCAAGG
AAACATACGGTGTGGCAACAGTTACCATGTTTTTAGGAACAGCAGCACTCC
TAATGTTTGCTGCAGGGAAAAAGGAATCTCAGAATTTGCCTGATCCCTATA
ATTTTTTTCCTAAATATTTTGAAATATCTTTCAGATGTATTTTAAAATTTA
```

FIG. 8-88

```
AGGATATTTTGTTCAGTTCATACAGAATTTTTTTTTTTCTCGAGATGGA
GTCTCACTCTATCACCCAGGCTGGAATGCAGTGGCATGATCTCGGCTCACT
GCAACCTCTGCCTCCTGGGTTCAAGCAATTTTCCTGCCTCAGCCTCCCAAG
TGGCTGAGACTACAGGCGCATGCCACCATGCACGGCTAATTTTTTTTGTAT
TTTTAGTAGAGATGGAGTTTCACCATGTTGGCCAGGCTGGTCTCGAACTCC
TGACCTCAAATGATCCGCCCTTTTTGGCCTCCCAAAGTGCTGGGATTACAG
GCGTGAGCTACCGCGCCCAGCCAAATTTCTAACTTGTTTTGTTGTTGTTGA
GACAGGGTCTCAGTCTGACACCAAGGCTGGTGTGCAGTACTGCGATCACGG
CTCACTGCAGTCTCGACCTCCTGAGCTCAAGTGATCCTCCCACCTCAGCCT
ACTGAGTAGCTGGGACCACCACGCCTGGCTCATTTTTTCTATTATTTATT
GAAACGGGTTCTGGCTATGTTGCCCAGGTTGGTCTTGAACTCCGGAGCTCA
TGCGATCCACCCACCTCAGCGTCCGAAAGGATTATCAGGAGTGAGCCACCG
TGCCCGGCCAAATTTCTAACTTTTGAATTGACATATTCATTTATTCTCTTT
ATCATTCAGGGAGAAATTTGGGGATGGATAGCCTTGAAGCATCATCCACCA
AGTTATTTTATACACCAGATTTAGATACAAAGTATTTTTTTATTATTTAAA
AAAATCAAATTCTAGCTTTTACTCTGAAGATTCTAAAAAGAATTTTGGAGT
CTTTAATTCATACTTCAGGGGCAGGGGAATAAGTACCAATATTCGTATAAC
TTTCAGTGCAAGTCACGTTAGCTAACTGTAGTCTATTGAGTTAAATATCCT
TGATTTATTCCTTAAAACTGAGTCACTATGACGGCACTTTTTGTTTTTTT
TTTTCGAGACGGAGCTCGCCCTGTCTCCCAGGCTGGAGTGCGGTGGTGCGA
TCTCGGCTCACTGCAATCTCCGCCTCCCAGGTTCAAGCGATTCTCCTGCCC
CAGCCTCCTGAGTAGCTGGGACTACAGGCACACACCACCACGCCCAGCTAA
TGTTTGTATTTTTAGTAGAGACAGGGTTTCATCATTTTGGTCAGGCTGGTC
TTGAACTCCTGACCTCGTGATCAGCCTGCCTCGACCTCCCAAAGTGCTGGG
ATTACAGTCATGAGCCACTGCACCCGGCTGAATGGCACTTTCATAAAACAG
TAAATAACCAACTTCACTACTGCCCCCAAGAGTTTTACTATGTATATGAGG
GCATCTGTTTTAAGTATGGGTATAATGTTACGGGTTTTTCTTTGTGTAAGT
TTGGGTTCACAATTTCATCATTAAAACAAATGTAAAATACTTTGTGCTTTC
TGTGTGCTATTAAGAAAGTATTCAAGGGAATTTTGAAAATCAAATTTAATT
ACTCTCATGTTTGTAAAATTTTTGAAACAAATGTTTAAGAGAGGATAATGT
TAGAAATTATCTTTCCAGCCAGACCTGGTGGCTCACGCCAGTAATCCTAGC
ATTTTGGGAGGACAAGGTGGGCAGATCACTTAAGCCCAGGAATTCAAGACC
AGCCTGGACAACACAGGGAAAGCCCATCTCTACAAAATATACAAAATTAGT
GGCCGAGCGTGGTGGCTCACGCCTGTAATCCCAGCACTTTGGGAGGCCGAG
GCGGGCAGATCACCTGAGGTCAGGAGTTCCAGACCAGCCTCAACATGGAGA
AACCCCGTCTCTACTAAAAATACAAAATTAGCTGGGCGTGGTGATGCATGC
CTGTAATCCCAGCTACTCGGGAGGCTGAGGCAGGAGAATTGCTTGAACCTG
GGAGGTAGAGGTTGCGGTGAGCCGAGATCCCGCCATTGCACTCCAGCCTGG
GCAACAAGAGCGAAACTCCATCTCAAAAAACAAAACAAACAAATAAACAAA
ATTAGTCAGGTGTGGTTGTGCACACCTGTAGTCCCAGCTACTTGGGAGGCT
GAGGTGGGAGGATCACTTGAGCCCGGGGAAGTGTAGGCTACCATGAGCCAT
CATGGTGCCACTGTACTCCAGTCTAGGAAAAAAATAAACATTAAAAATTTT
AAAATCTTAAAAAAAGAAAAGAAATTTTCTGTCCAGATATCTTTATTTTTA
ACAAATCGAAGTGTATTAATAGTGTTTATGGGAGCGTGCCCACACAAGGAC
AGCAAGCCTAGGAAGTGCAAGTCAAGAAAACTTTTTGTGAAATAATTTAAA
CTGAAAAGAAAAAGCAGAGATTTTTTTCTAGAAAAGTAAGGAGTGGAGGTA
```

FIG. 8-89
```
AAAAAAAAACACAGCAGAGACACAGGTATGCTACGGAACCAAAGGTGTGCC
AATGGTACTGACAGTTTAATTCAGAAAAAAATGAATCAGAAAATGGATATT
TTTAAATAAGTTAGGTTGCTGAAAAAGAGAAATGCAGTGAAGCCTTAGATG
GGAGTGAGATAAATCAGCCATTGGCTAGAGGAGTTTCTTGCCCAAGACCAG
TGGTGATGTCCCCAAATGCCTGGAAACAACTGTTGTGACATTATAAAGCCC
CCATAGTCTAAGTTGGGTGAGACTATACTTATGCATTTTCTCACCTGTAAT
ATAGCTTAAAAGTATTTCTACTCTGGGATTTCTTTACATTTTACTAAAGCG
CAATTATATACTTAAAACTGATAGTGTATGCTGGGCTGCTAGTCATTCTCA
ACCCTGGCCAATTATCAGAATTGTTTGTTGAATATATAGGTGCCATATATA
GGTGCATACACACACACACACACACATACACACACACACACACACAC
ACACCATATTTCATTCCTCATATCGAATATTCTGAGAGAGTTAGTTTGTGG
AGGGTAGTTCTGGACAATTTATATTTTCATAACACCTCTGGTTATTTTTT
TTAAGTAGAGATGAAGACTTGCTATGTTGCCCAAAATGGTCTTGAACTCCT
GAGCTCAAGCGATTCTCCCAACTCAGCCTCCTGAAGTGCTGGGATTACAGC
CGTGAGCCACTGCATTAACCTCTGATTAATATCATAGATTAACCTCTGATT
AATATCATAGATTTATTTGTTTGAATGCTTCATGTATCCTCTCAACCACAA
CTTGTTTGCAGAGTTTTAATCTGAAGGGCTTAGGTCTCTTGTTCAATGAAT
GAGTTTGATCTGATGGGTGAGAGGAAGGTGAAATGGAAAGCGAACGAGAAG
CCATACAGATTAGGCGAGTGAGCCTAATCTCTCCCTAACCATAAGATTGAG
TATGCCTGAATTCTTCGCAGAGTGGAAGAATCCATTTTAAATATATATATC
TACATGTACAGATCCTTTAAATATTTGTTCTGACATTCATTGTTTTTGAGT
CACTGTCATTGAGAAAAGTTTAGAAAGGAGATATTAGGAGCAGGAAATAGA
AAGTAAATAAAATATCAAAATAAAAATGGGGTTTTATAAATGATATAATAG
GCAAAATAAAGGAAAGGCATCCTAGACCTCTGGTTAAAATGAAGATGGCAC
TTGGCGAGATGTGTTCCAGGGTAGTTCACATGATGTATGTTTTCAGAGAAT
TGTCATATTGCATATGCTGCTATATTTTTATTTTCATGAATTAAAAGGCA
TGTTGAGATTTCAGAGTTTTACTTATGATCTCAGACTCTGCATTTTTTCTC
TGTAATGTTTGACATTTCTTCCTAGCTAAGTCTCTAGTTATAAGGTCTGTG
TTGTGGCATGTGGACAGTGAGTGGAAGAACCTAAGAACTCAATTTGGGGCA
GAAGAATGTAATCAATTATTTCAGAAGTGATACAAACAATATGACATGTAG
AGCATTCTGGCCTTTCCTGGGTCTTTTTTCTCCATTCCTGGATTTCTTCTC
TTCATGTGAGCAAGTCTGAGGTTACTATATAATGTCTCTCACAGGCCACAG
CCCCATTCTAAATATTCCCAATAGAAATTCATTTATTAACCAGAGAGTGGT
GGGTGGGGTTGTTTTTGTTTTTTAAACAAAAGTGGATCTTATGGGCATTCT
GGAAAGCTCCCGCAGGAAGCTAAGAATAAAATTTTGAATTGAGAAGTCCCT
TTCTTCAAACCACATTCAGACCCAATTCTGCTATTCTATTTATTTTTCAAG
GGGATTAGCCTTATTTTAACACCAATAATCTTATCACAAAAACCTCCCAGA
GGAAGACCCTGTAGATTTTGTAATGACCTTAATCAAGTATTAGCCCTACAC
TTCAATTAATCCCCAACTGTACAAAACGAATGTTCTTTTCTCTAAAGCTGT
AGCAAGTTGAAAGGGGATTAAAAACGGAGGGAAGGGAAGAGTGTTTGGAAT
TTCAGGCACAGCAAACAGGCACAGCAGACCAGGAAGAGCGTCCCGGGAAAA
CATATTATCCAGACTTAAGTTTATATTCCCTGTCTCTCTCAGACTTTTGCA
GAAAAATGAGTCATTCAACAAATATTTGAATCGAGATAGGGAAAGTGACGA
GGAAGAAGTTTGCACTTATGAGGTTTTAATTTGCAATTATTTGGCTACCTT
TTTGCCTTCCCAAAACATAGGGTCTTTAGGAGTGAAACTTCATAGCCAAAC
TTATACCTTGTCCAGCACAGAGAAGGCCATCAAAATGCCTGGTTTAAATAA
```

FIG. 8-90

```
AAATATTAAAATGATTGGGAGGGTAAATCCCTTGACCTATAAATCTGACCT
CCTTTAAACATTATTTGTATGTTCCCCAATAAACTATTCCGTAATTTATTA
GTTAGCAAGTGGAAATAAAAAGAAATGTGGAATGGGGCTATGCTTAGCGTC
ATTAAGCTGACAGGAATACAGCGCATTCAACTTGCAAACACCCTTCCACTC
CCACAAAGAGCAAGCTGTCACTGGCCAATCAAAACAATGAACCATAATGAA
ACAGTTTTTCTTGCTCCACCCACTTGGTGACCAAATTTGAAAAAAAAAAAA
AACCGCGCCAACTCATGTTGTTTTCAATCAGGTCCGCCAAGTTTGTATTTA
AGGAACTGTTTCAGTTCATACCTTCCACTGCGATAGGAATCATGTCTGGTC
GCGGCAAAGGCGGAAAAGGCTTGGGGAAGGGTGGTGCTAAGCGCCATCGTA
AGGTGCTCCGGGATAACATCCAGGGCATTACAAAACCGGCTATTCGCCGTT
TGGCTCGGCGCGGTGGCGTCAAGCGCATTTCCGGTCTTATCTATGAGGAGA
CTCGAGGTGTGCTTAAGGTTTTCTTAGAGAACGTTATTCGAGACGCCGTCA
CCTATACGGAGCACGCCAAGCGCAAAACTGTCACAGCCATGGATGTAGTAT
ATGCCCTAAAACGTCAGGGGCGCACTCTGTATGGCTTCGGCGGCTGAATCT
AAGAATACGCGGTCTCCTGAGAACTTCAAAAAACAAAAACAAAAAAACCCA
AAGGCCCTTTTCAGGGCCGCTCACAAAGTCGTTTAAAGAGCTGAAATGCGT
TGCGAGAATGAGTTTGGATGACAGAAATAACCGTGACATCCTGCATAAGAA
TGAATTGTGTTTGCCATGACCGGCCACACTGTGACAAAATTTCAAAGCATA
AAGTAGGCATAGAGAGGTAAGCGCTAATAAAGTGATTGGCTCCACAAAAAG
CATTTTGCTGGGCGCAGTGGCTCACGACTGTAATCCCAGCACTTTGGGAGG
CCAAAGCTAGTGTATCACTTGAGATCAAGAATCCGAGACCAGCCTGGCCAA
AATGGTGAAACCCCTCTACCAAAAAAAATACAAAACTTAGCCGGGCGTGG
TGGTCTGCACCTGTAGGCCCAGCTAGCCCGGAAGCAGAGATTGCAGTGAGC
CGAGATCGCGCCACTCCCCTCCAGCCTGGGAGACAGAGAGAGACTCCTCAA
AAAAAAAAAAAAAAAAAAAAAAAAAATTATGTATTTTAGAGCATTCTAAG
AATGGTACTTTGGACTTAACCGAAGGGCTGGAGGCGCGTGTTGAACAAAGG
TTATCACCTTTTGGCTCATGCGGCACACAGCTATGTAAATAAAGCATCTTT
AGGGACAAGCTCTCATTTGCGGAGGGTTCTATGGCTGTTGTCCTATTGGCC
AAAACAAAGTGGTCTAAGTCCGGGCGCGGTGGCTCACGCCTGTATTCCCAG
CAGTTTGGTAGGCCAAGGTGGGTGGATCACGAGGTCTGGCGTTCAAGACCA
GCCTGGCCAAGATGGTGAAACCCCGTCTACTAAAAATACAAAAATTAGCCG
GGCGTGGTGGCGGGCACCTGTAATCCCAGCTACGTGGGAGGCTGAGCCAGA
GAACTGCTTGAACCCAGGAGGCAGAGGTTGCAGTGAACCGAGATTGTGCCA
CTGCACTCTAGCCTGGGTGACAGAGCGAGGCTCCATCCAAAACAAAACAAA
ACAAAAAAGTGGTCTAATAATCCCCAGAACTGGAGGAAGAACCATAACTTA
TTGATTTTGTTTTTAACCTTATGTATGCCAGGCATGCTAGCCTTGTATACA
TACAAGGCTAGAGGAGCAAAGGTGCAGGAAGCCATCTTGAGGGAGTCCCAT
ATTATTGAGAGACCGGCCAGCTGCTGGGAGAGGCTAGTTGTTCATCCTCAC
TGTATGTGATGAGAATCTGGTGACAGTCCATTGCTGGGCACAGCATTTAGG
CAAAATGGCTCTCTGCTATGTCAGGCAAGTGAGGCATATTTTTGCACAATC
CTAGTAATTCCGAACTCATTGGGAAACAATGGCAATTACATCCAAGCAAGG
AAAGGTCTGTGGTTGATTTTATCTATACAAATTTAAAACATAATGTTTACA
ACCTTTCATTATAGGACACAATTTTTAAAAAGATGCCAAACTATACAAATA
AGTTCAGAAAAGTGAGGTACTATTGAACCGTCTGGAAAACATAAATGTATG
TGAAATAATGCAATGCATAGTTTTGCAGGGGACTTTGTTCAAAGTTTCTCG
AAATACCATGGTCCAAAGTAGACTAACATTAGCATTGGTTATTTATGATGA
```

FIG. 8-91

```
TCAGTAAGAATACTAAATCAAAAATCAAAGGAAAATTAAACTATGTCTGTT
TAAAGAGAAACGTAGTTTACCTCAGACTGAGAGTTAAAACAAGTTTGTGAT
TCAGGAAGGTGGAATTCAGAACCTAATTGGGCAGCCTCCAACATTTCCATT
AAGGTTTGGATTCTTAAAATTTTTCAGTCTTCGGTATGCTCTGGTAGTCTG
ATGAAACTTACAGATTCTTTTCATAAATAAGATACTTAAAGTAATTCATAG
GGTTACAATTGTATTAGACCAATAATATTAAAATAATTATCAAACCACTTG
ACCGTAATATGTGTGTTTTTGTTGATATACCTAATAGTACTTCGGAAATAA
GCAAGCACGATTTCCAGATTCTTGCAACAACTATAACCTACAAATTTGTTA
TTTCTATCAGTCACACACAATGGAAGAAAATTCTAAATTTCAGCTACAGGA
TAATGAATAGATGAAAAACAACAACAACAACAACAACAAAAAAACTCCCCT
AATCCATATTCTGGGACACCTTGATTCCTATTTATTGATCCCTTGAAGTCA
GTGGATAGCATATTAAGAAACAATAGTTACAATGACACCACAGAAAGACTA
GAATGTAGTACTTGTGTTAAAAAAAAAAAAAAGTATCAGCAAGTTATGTTTG
GATGCCAAATTGCTCTCCACTTCCCTTCCCTGACACTGGCATTTCCAGAAC
TTAGATGCTCTTACATGTAAAAGCCTCCTCTAGTGCACCATCGAGCTTTTC
AGGATTGGACATCAGACTTTTTAGTTCCTGGACCTCTAGATATACGGCAGT
CTCTGACAAGAAGCCCTTTTTCTGTTTTAACTTTTTTTTTTTTAAGTTTT
GAGACAACGTCTGACTCGCTGTCACCCAGGCTGGAGTGAGGTAGCACCATC
ATAGCTCACTGTATCCTTAAACGCCTGGGTGCAGGGACTAAGGGAGCGTGC
CAACCATGCTTGACTAATTTACTTTTTTGTAAAACCAGTAGTCTCCAACCT
TTTTGACACAAGAGACCGTTTTGTGTAAGACAATTATACCACGGACCAGGG
GGTGCAGGGGCTGGGAGCAATGATTTCCGGACTAAAACTGCTCCAACCTCA
GATCATCAGGCATTAGATTGTCACAAGGAGCCTGAAACCTAGATCCCTTGC
ATGTGCCATTCACAATACAGTTTGAGCTTATGAGAATCTATCTAATGCTGC
AGCTAACCTGACAGGCGGTGGAGCTCAGTTGGTTAATGTTCGCTCACCCCT
CAGCTGTGCGGCTCAATTCATAACGTGCCATGGACAGGGACCGGTTACCGG
TCGGTGGCCGGGGAAATGAGGACCCCTGGTATAGATGGTAGTCTGGCTATG
TTGCCCAGGATGGTCTTGAAGCCTGGCCTGAATTAATTCTCCAATCTCAAG
CCTTTTCAACTCAGCTGCATCACAACTTAAACCTATAGATAACTGTCACAG
AAACTTGTTTCCAGTGTTACGCCATCTTAAAATAATGTGGGTGGCTCTTAA
AAGAGCCTTTGGGTTCTTTCCAAATTGGCCTCCCGGAAAGCTCTTTACTTC
TTAGATGTGGCCTTTCTAACATTAACTTCATGATGTTGGGTCAATTTTGAC
TTCGAAGCCCTTGCCTTCACTGGGCTCTTCTGCTGTTGCTTACCCTTGGCT
CCTTTAGCCTTTCTCCCGCTCCTAACAGTTTTAGGAGTTGTCGCTCTCGGC
TTCTTGGCTCTCTTATTGGTTTTAGCAGTCTTTGGTGACTTGGAGTCCCTG
GATAAAACCAGCTTCTTGGTCTTGGCAGAAACTGACTTTTTAGCCTTGCTT
CTGGTAGATTTAGGAATCACCTTCTTACTAAGCTTAAAGGAACCGGAAGCA
CCAGTACCCCTGGTTTGCACCAGGATTCCCTTGTTCACTAAGCTCTTGAGG
GACAGTTTGATGCGGCTGTTATTCTTCTCTACGTCGTAGCCAGCAGCGGCC
AATGCCTTCTTGAGCGCAACCAAAGACATACCTACTCGTTCCTGTGACACT
GAAAGGGCCTCGGTGATCAACTTGGACACAGAGAGGTTCGGCACTTTGCGA
CTTGCACTTATCAAGCCAGCCGGCTTCCTCCCTCGCTTCTTGGTTGGAAGT
TTCTCCATAGCGGCTACACCAGCACTGGCAGAAGCTGCAGGCACGGTTTCA
GACATAACAACAGAGAAACGCAAGATGTAATAACCAGCGAAAAGCATGAAA
CACCCGGGCGGCCTCGGGGCCTTATATAGGGTAGGGCGCGCTGTGATTGGT
GCATCACCTAGGCACCGCCCCCGCCCCTTGGAGGAGGAGTATTTGTGTTTG
```

FIG. 8-92

```
TTTTACCCGGAAAAGTTGAGTATAACAAAACCCCTCTTTACAGAATCTCCC
AGGGTCTAGTGCTGAATAATCTGCGGAAATTCATATTTGACATGACTTTTC
TCTTTTTAATGAAAAATGACCCTGGATGCCAAAACTATTCGAGAAAGCCCT
CGATTTTCAATCAAATTCACGGAGAGGAACAAAACTTCCCCTTTTCCTTGT
AAATTAATAAGTAATCTTTGGCAGAAGACTTATTTCATCTCTTCAGAGTGG
TCTTCCAAATGGATAGCTTCAAATCGGTAGAGGAAAGAAATTATTCACGCC
ATGATTTTTATTTAAAATTATTTATATATGTGAGGGAAGTAACACAGATCT
CTTAGCTGTCTAATTGCGGAGTCAGAAGATGCTTATAGAATTGTCAAAAGA
CTGCAGAGGATGTCTTTATTTAGGCATGTGCAATCTAATAAATCATAATCC
ACAGGAACATGGGTTGTCTGTAATTAAAGGTGCTCCCAAGTCCCTGTAGCT
TTATAGAGGACTCTCAAGGATGGGGTAATATCAAGATCTCACACATTATGT
AAGATTGGCCATAATCAGGCCACTCTCATGACCGGTGTCCTCAACTGAGTT
TTGCTTCTGGTTTCATTAATTGAAGTCCCCTCTATCCCCCTGCCCACCCCT
ACATCCCCAGATAAACAGACACAGTCCCTCCCCTAAATTAACTATAAAACA
TGAGGTAGGAACCCTAGACTCAAGAACCTACTAGAAACTACAGACCCCATG
TCTAACAAGACTGGGCGGGTTGGCTGGGCGCAGTGATTCATGCCTGTAATT
ACAGCACTTCGGAAGGCTGGAGGCCAGGAGTTCAAGACTAGGTTGGCCTGG
TCCCTACTGAAAAAAAAAAAAAATTAGCTGGGTGTGGTGGCACATGCCTGCA
GTCCCAGCTTCTGGGTAGACTGAAGAGGATCACTTAGAGCCCAGGAGCTTG
AGGTCGCAGCTACTGCACTCCAGCCTGGGCAGACCCTCATCTCTGAATTGC
TTAATTAATTAACTGAGCTGGCAGATTTGGCTGCATAGCTGTGGGGAAAGG
GTTGTTGGAATAATGTCCAGTGTGCTCCCCTGAGCTTCTACTGGAACAGGT
CTTTGTGAGAGGCCTGGAGATAAGAGCTTGCTCACAAAGGCTGAGGCCTTT
CTGGGATGCTGAATGAGTTTAGTGTGGCCAGAGCATAGGGTCTCAGCAAAG
GAAAACTCCATAAGGGCCATTTGTGAAGATCCCCAAATACTTGTGTGAAAC
ATTTGGTAGATATTAGAAGTTTTGTTTTGGTTTGGTTTGAGACAGAGTTTT
GCTCTTGTTGCCCAGGCTGGAGTGCAATGGTGTGATCTTGGCTCAGTGCAA
CCTCCACCTCCCAGGTTCAGGCAATTCTCCTGCCTCAGCCTCCCAATTAGC
TGGGATTATAGGCGCCCACCACCATGCCTGGCTAATTTTTTGTATTTTTAG
TAGAGATGGGGTTTCATCATGTTGGCCAGGCTAGTCTCGAACTCCCCACCT
CAAGTGATCTGCCCGCCTCTGCCTCCAAAGTGCTGGGAATACATGCGTGAG
CCGCCGCGCCCGGCAGACATTGGAAGTTTTTAAGCAGAGAATTTGTTGTAT
TGTTGTAGTTGTCTTGGGTTTAGATTTATTGCATAAACAATCATTTTTGAG
AAGGGCCCACAGTCAGAAGTTGGGAGTCTGTTGCAATAGTCTCAGAAGAAT
GGCAAAGACCTTGCCTAAGGGGACAGTGTGGTAAAGGAGAGAGTCTACATT
TGAAATATTTCTGAAACAAAAGCCAAAAGATAAGACTTCAAACTTCTGATT
GCAAAGTGAGATAGAAAAGTTTCTTTCTCTCTGTCTCTCTGTTATACCCAT
ACACACACACATATGCACAAACACCTGAAAGAAAAAAAAATTCAGGGAACA
GGCCAGGTAGGGTGGCTCATGCCTATAATCCCATAAATTTGGGAGGCTGAG
GCTAGTGGATCACTAGAGCCCAGGAGTTCACAAGGCCAGCCTAAGCACATA
GCAAGACCCTGTCTCTACAATTAAAAAATTACCCGGGTGTGGTGGCACGTA
CCTGTGGTCCCAGTTACTCAAAAGGCTGAGGTGGGAGAATCACTTGGGCCC
AGGAGGTCAAGGCTGCAGTGAGCATGATTGTGCCACTGCACTTCAGCCTGG
GCAAGAGCGAGACCCTGTCTCAAAAAAAAAAAATTTTTTTTTTTTTCCAG
AAAACAATACTATCTTAAGCACCAGCACTTTAGTATATTCTACTGTGGACT
AGTTCATTTTTAAAAGAACACTAGGTTGGAAATCATGAGATTGATTCCACA
```

FIG. 8-93

```
ACTCACTAAAGCACCGTGTCACTCAGTTTGGAAAATATTTCTCCTTAGAGA
GATTACAGGTGCATCTTTCTGAGCACCTGTATGTTTTTACATTTGTTTGGC
TTCTCTGACCTTTGATAATTTCTGAGTGTTGTACTATTAAATATTAGTGGC
TAGGGGTCAAATTGTGGATCAGGTTGATCCTTATATTTACAAGTTGACAGA
TACGTTACTCCATTGCTTTAAAACTAACACAGAATTAGAGAATTTAGAAAA
TTCTTACATTCCATAATTTAAGACCCAGAAAAAAAAGATTCATATTTTGCA
TTAGATAGCTAAAATGGTACCATAAAAACAAATGATATCCACATATATATA
GTATATAGTGCTTCTTCTGTGCCAGTCACTATCCTAAGTTTTTCTCTCCCT
TCCCCAAAAATGTAGGAATTAACTTTATAGATGAAGAAACTGAGGCACAGG
AATGTCACATGACTTGCCCAAAGGAAATTCAGTCTTCCTTTTTCAATTCTT
TTTTCTTTTTACTTTGCTGCAGGGTCTCGCTGTGTTGCCCAGGATGCTCTT
GAACTCCCGGACTCAAGCGATCCTCCTTCTTCAGCCTCTCAAAGTGCTGGG
ATTACAGGCATGAGCCACTGCGCCCAGTCAGGAAATTCAGTCTTCTAAACA
TTCATTATTGAAATAATATTTCCATAAACATTTTCTTAGATAAACTTTGGC
ATCTCTAACTTCTAAGTAGCAAAGTCATGGAAACAGTCACAGAGAAAATAA
CTTTATTTTAAAAATAATAAATTCTTATCTCCGGTGATAAGAAAAGTATAC
AGCCCATTTTTTAAAGTATTAATTTTACATTCTAATTTGGTTTTTTTAATG
TTTACCATATATTTCTCTTCTACATATGTGTGTGAGTGAATAAAATAAAG
GCATCTACAGATTTTTACATGTTCAGTGAGATTAGCAGGGTTTCACTTGAC
AGCACTCTTACCATACTCACTTCTTGGCTTTTCCTGATATCTAACATTTTT
AAAATGAGTAGTCCCTTTTCATATGATTCTTCCTTTTTCAAGCACTATTTT
TGAACTTTATATTTGATTGGCAATAATTTTTACAGACATTATTTTACGATT
AACTTTAACTCTGTTCAAATGATTTCTTCATTTTCAAGTATTTTATTTGAA
CTGCTTTTTTTGGTTCAACTACTGAGTATTTAATTTGTCTGTTTTGTAGAA
AGGGTATGTAGATAATTCCATGTTTTGTAAAAGTTGTCTCTAAAAATCTAA
CAAGTGTAAGTACGATGCTATTACAGGGCTGAGAGACACAGAAAAAACACA
CACACACACACAAAATTTTTTTTAAGTATTACTTGGTCTCTAAACTAAAG
AATTTACCATCTATTTTGGGAGATGAAATCCAAACATAAGCAATGACAACA
ATTATTATGTGCTTAAATCAATGTCCAAGACAATAATTGACCCCAAGGCAG
GGAAATCACTGAGAGAGTATAGCAGAGAAGGTGTCCTCTCTGTTCAGATGA
GCCTGAATAATTTGTTCAGTAGGTTTCTGCTACTCATTTATAAACTGCACA
TCTTCTGTAGTCCTGGAAAATGTCTAAGAGGAGAGAGGAACTAAGATCAGG
GCCACCATTTAATTAGGAAGTTCTGGGAGTACCTGACCCAGAAGAAAGATC
AGCATAGCTGAAAATCACCCATAGGAGAAACATCTAGGTAATCTTATTTCT
GTTCCACCTGACATTTCAACCTCTCTTTTCAGCTATAAGTATATAAGTACT
TATATGTAAGTAAAGAAATTTACCCACATCATGTTGTTTTTTATTCAATGC
TTAACATGTATAATGCTAACAACACAGACTTGATGTCCAAAACATTTCTAT
GAACAGCTCATTACTGGATGACTGAAATAATTTTTCCAAGCCACGTGGAGG
TTAATGAGTCAGTTTTTGAAAGCAAGGAGAGAAAAACATTAGAATTTAAGG
TGACGTTTCTGTTGCGTTGTAATCCAGAATACAGAATAGTCAGAGAAAAGC
AGAAAGTCTTTCTTCTTAAATTTTCTGAAAACCAAGGTGTGCATTAAAATG
GTACATGCCTACTTCCCTTTCCCTTTACCCTTTTTTCCTGCATGGAACATA
GATATGACCCCTAGACATGCTGCAGATGACCATGAGGTTGAAAGATACATG
GAAGATGGTTAACACAGGATGATAGAAGAGACCTGCATACTTGGGCAGCCT
AGACAGCTCCTGCCAGCCCCCAACAAAACAGCCTAGCCTTCTTGCCAATCA
AGAAAAAAAATCCCTTCTGGTAACCCACTGTAAGTGAATTTCTGTAAATGT
```

FIG. 8-94

```
GGCCCAATGTATCCATAATTGATATACAAATATTAGTTTAGTGGGTAGCAC
CTCTCCATGAGCATGTCGACTTCATGAGACTGAGATTTTTGACTGTCATGT
GCAGTTGTCCCATTACAGTGCCTGGTGCATGGGAACAGCTCAACTGTGCAT
ACCCATTGAAGAAATAGATGCATGGTCAATCGAATTTCCAGGTATATCATA
TGTTTCCATAAAAAAAGTAAACATACAGCATATCTCCTTCCAGTTTATTTA
TTTTTCTCTCTAGGACCAATTTACAGTCTATCAGCAGTGCGTGAGCACCTG
TTTCACCACATATACAAACCCCTCCAAGACTATAAGGATATCATTAAGCTT
TTTATCACTGTCAGTTAAGTGGTAAACATAGTTTTCTACATACTTTGCATT
TTTGTTTCTCATGAGATTCAATGTTTTACATGGGTAAGTTGTTAGATCATA
TTTATTCAAGATGAGGCATTTGTCTCCTGGTAAGACATCTTGGTCTAATGC
TGACTCTGGGGTGTGGACATTTGGCTGTTGACTGTGAGGTGGCTATCTACA
TGTGGAGTGGAGGAGTCCTGGCCTTGGATTGAGGAGAACAAGGTCAACTTC
TCACCTCACTTGTTTCTGGCTTTTGTGACCTTGGACAAGTTTAACTTTTCT
CTCTCCTAGTCTTAGTTTTCTTGTCTGTAAGTGACAGCAATGATGCTGTCT
TTGTTGGGGTGGGCTGCCATAAAAAAATACCATAGATTGTGTGGTTTAAAC
AACAAAATTTTATCACAGTTCTGGAGGCTGGAAGTCTCAGAGCAGGGTATA
GCATGGCTGGATTCTGTGGAGAGGGCTCTCTTGCTGGCTTGTAGAGTGCTA
CCTTCTCACTGTGAGAGCTCACATAGCCTTTCCTCAGTATATGTGCAGAGC
TCCCTCTCTTCCTCTTTTTTTTTTTCTTTTAAATAAATTATTTAATTTGG
AAGACCAAGTGCAGAATCTTCCTCTTCTTATAAGGCCACCAATCCTATCCA
GTTAGGAACCCATCCTAATGACCTCATTTAACCTTAATTACCTCTTATAAG
TCCTGTCTAGGAATAGAGTCATATTGGGGTTTATGGCTTCAATATATGAAT
TTGGGGGGATGGGGAGACAATTCAGTCCATAGTAAACACTTCCTCAAAGAG
TAGTTATAATGTTTATAAGAGACAATGTAGGTAAAAGTAGTTTCAGTTGCA
TGCAGCTAAATGCAGTTTAGTATCCCTTCAGAGTCCTCCGCAGAAAAGGCA
CCTGATAAATATTTATGTGGCCTTAACCTAAGGTATTATTCTTTATATAGT
GCCTTCCCATGTAATGATTGATGTCATGTTTATCATTTGCAGTGCAGTTTA
TTTCTTATAGGTCATGGCTACAGAAACATGGGAGAATGACCATCATTAATA
GGTCATTAGAATATGTAATTTCAATTTTTTTTCTTTTGAAGGACTATTAG
GTTAACAATGATTTTTAAAATTTATAGTAGATATGAGTGCTATAAAACAGG
AATTTCCATATTATTTTGGGATTATAAATTGGTATGATCCTGAATAGCAAT
TTGGCAATGTATATGTTAAGAACCTTAGAAAATGTTTTTCACTTTTGATTT
AGTATTTCCACTTCATGAAGTCTATCCTTAGGAAATAATATTTGAACAAAG
ATTTATGTACAAAGATGTGTGAGCTATATAATCTATAATATAATGCATAAA
AATGGGAATCAATTGAAGTAGTCAATAACAAATACATAATTATCAATATAT
CCATAAATTATACATCCATAAAAAAGTTTCTAAGTATATTTATCTAAATAT
ATATCATGACACCTAAATTTATTTTATATATGATACATGATGTGAGATATA
TGTATATATGAATATGAGTATATATAATATACATATAAAAAGAATAGGAGA
TACTAGGAGTTATTTTAATTTTGTCTTTATGTTTCCTGTGTCATAAATTTC
TATGAAGAATATTTTAATAGTTTTATGCATAGAAAAAAGAGCTAATTTTTC
TCAGCCAGGTGTTCATTTGTCCTTCTTTGATTGTTCAAAATACCTCCATTT
ATCTTCTTCTAGGATCACTCATTTTCATTGGTTTATTTGCAAGATGAAACA
GTGTCCAGCAGTGACGACTGTTGGAAAAGATATGTCTAAAAGCTGTTGTCT
CCCCCTGGAGAAAAGAGAGAGAGTGATTGATTCACTTCTGTAATTTATCAG
ATATGAGATATTGTATTTGACTCTGAGAACAATGATAATGATGATGGCTAA
AGTTCACTGGATGTTTGCTCTGTGCCAGGCAGTGTTTTAAGCACTTTACAC
```

FIG. 8-95
```
AATAGATACCAATGCATTTAGTTGTTCCAACAACCTTATGAGATACCTACT
GTCATTCTCCCTGCGTTATAGATGAGGAAATTAAGGCACAGAGAGGTTAAG
TTTCCCAGGTAGCACAGCTGTTGGATAATGAGCCTGTGCAGTAAACCCACA
TCCTCTAGCCCTTGAATGTCTGTACGCTCTTAAAAGATGAATGTAACCTAG
TCAGTGTCCTAAAGTTCCATTTGATCTAAACTTGAAGGATAAAAATTTATC
CAGTGAGGAAAAAGACTTAGTGTTTTTCATAAAGAAGATACAGCGACGAAG
GCCAGGCCGTGGGGACTGTCTGATTTTTAGAGCCTAGAACCCTGAGCACAC
TCTCTAAACCCTCCAACATGCTCTTACTCTGTTGCCTGCTGAGCATCTTTG
ATCCACTCTTGAGGCTAGCAGTTTTCCTTCCATTCAAGATCTCACAACGTG
TATTGTTCTCTGCAGATTTTTAAACATGCAATTTTATTTTTTAATTGTTA
AAAATATATTTATTTCAGTGCACTGAAGCTCAAATGTGTGTGTTTTAAAAT
CTAGTGTCCAAGGTTCATTACCCCAATTGTTTAAGCAAGTCTAACAACAAA
AGGGGCACATTTTAATTTTCAATTTTTTTTGTTCTAGCCTACAGTTGAGT
TTGGGCAAATAATAGTAGACAAAAAAGTGAAAAGAAAACTAAGGACAAGAA
AATAAAGGAAGGGAGAATGGGGGGAGAGGAGGGAGAAAAGTGAAAACAAAA
GTTTATTCATATTTCTCTTGAATCCAATTCTTTTACCATTTGAAAACTTGA
TATGGTCAGAGAATAAGCCTAGAATTTTAAGTGATGAGGATAAGGTTTTAC
CACAGGTAGCCTCCTCTACATAGGTCTATTTCCTCATAGAATGAGAGAAGC
CCCATCATTTCTGCTCTTTTACCCTTCTGAGCCAGCAGCAAGGAGATCTAC
TATCAAGGCATGAGCAACTGTAGAAACATGAGACCAGATGTCTCTATTAAT
TATTCTACAAATTGCGCATTGGATGATAAGGTTACATGAATCTTTAAATCA
GCAAACCAAAGTCCCATTATTATTACATATTTTTCCTCCTCAGAACTGAA
GTGGGGCGGGGTACAGTGACTCACACTAGTAATCCCAACAATTTGGGAGGC
TGAGGCAGGAGGATCACTTAAGCCCAGGAGTTTGAGACCAGCCTGGGCAAC
ATAGTAAGACCCCATCTCTACAAAAAACTTTTTAAAAAATTAGCTTGGCAT
GGTGGTGTGCACCTGCTGTGGTTCCAGATACTCAGGATGCTGAGGCAGGAG
GATGGCTTCAGCCCAGAAGGTGGAGGTTACAATGAGATGCGATTGCGCCAC
TACACTCCAGCCTGGCAGCCTGGGCAACAAAGTGAGACCCTGTCTCTGAAA
AAAAGAACTGAGGTCAAGGAGTAGTAAGAAAGTGGCTCATTCTCCAGATTT
ACTCTCTTTTTCTTAATTATAATGAACTCATGATACTTGAGGATATGTCAA
ACTGATCTTCAGACCCCAAAGAAATTACTCAGAGCCTAGAATACCTTTCAG
GAAATGTTACAGTGGTATACTCTACTCAATTTAATTTTATGCTTGGTCATC
CAGGATTACACAGGCTAAAGGTAGGAAAAGTTTCACTAATTTTTAATGTCT
TTTAATTTAGGACTACTGGGATTGTCTGTCAATGTGCTGAATATATATATC
CTTCCAAATCTGGAAGATTTAAGAGAAATGATAGTTATCATTCTTTAAGTC
CTTAGGAATATGCCTAGAGAGCTAATTTCATATGTTCAGGGAAAAAAAGTG
TATTTTTCTCAACCTGTTGGACCCCGGTAAACATACTATGATCAACTGGC
ATTTCATATCAAATAATTTATGAAATTCTTATAATTTATAGAAGGCCAAC
TCCTACCAAAGTCTTCAGTCATAAGCTGCTTCAAGTCCTTTTAGGAGCGTA
AAGATGGTTATAAATAAAATTTGTCAAACAGCAGTAAACACAGTGGTTTAT
ATGCATTAAGGATCTTTAATCTTCACATACTTCTAGAAGGTAGGTGCTATT
ACCATCACTGTAAAGGTATAGAGAAGGATACTAATGCACAGAGAGATTAAA
TGACCTGCCTCAGAGTCCCACATCTTATATGTGGTGATCTGGGAGTCAAAC
TTGGAGTCTGTCTCCAGAAGCTTCACTTTTTGTCATCATTGAGCAGTGCTG
TGCAGCCATTTTACTAGCATGATACCACGTCTGGAACTAGTGTTCTATAGG
TGCTATTTCATTTAATCTTCACCCCATCTTTATGAGTAGGGCAATTATTAC
```

FIG. 8-96

```
CACTCTATAGGCTCAGGGTAGTTGAGTTTGTCAAACTGTGACTGAAAGACA
TTTAATTTTTGGCATACTATTTACTTGTGCTCAAGGTATATCAAGCAATGG
ACTGATTTCACTCAACAAAGTATTTTAAAAAGATGATTTATAAAATAGAAA
TGGGAGAAAAAAACTACAAACTGTCTAGGAATAGGATGTTATGTTTGCACA
TTATTTTCAGTAGAAAAGAGTTTAGTATGGATACTCTCTTCTTGTATAAAC
CAAGAATGTTAAAAGAAAACAATTAGTGATTCTCTAGAAACAATTAGTGAT
TCTCTAGAAACACTTAAGATTGGCTGTGCAGCACTATGGCTATCTCTGTGT
AGTATTTTCCACTGACAACCAACATTTCCATGTTAGGTAGGCCATGTCTTC
ACGATTTCTGGCACCAGAGTTTTTCAACTCCTCCATTTTTGGTAAAAATAT
CTCATAAGGAGCAAGTCTAACCATGTGAGTTTGTTTAGTTTTTTGTTTTT
TGTTTTTTTGACAATGGCTTTGTAACAACATTTAATAATCTGCATATTAGA
GAAGCACAGAAGTAGGGCAAAAAAAAAAGTTATGAGGGTAATTACAAATAT
TATAAGAATTCCTTAAAGTACAAATTGTCTCCAAGAATTTAATTGGCTTGT
CTTAGATGAATAGGTCTCAAAGATCAGTTTGGTCAAAGATCAGTTTGGTCA
ACTTTAGTTAAACAAGTTCATTTTTCCTAATTGATTATTTTGACTCAAATG
TGGGCCACAGGCAGAAATAAATTTTCTAGTAAATATTCTTATTTAGGAACT
TTTAGTCAAGTTATAAAGGTCCTTGTTACAAACCTGCAAAAAGTTAGCATG
CCAATATCTTAGTAAAATATAACTGAGATTTGTTTATTTGCTTGTTTTTTA
ATACTTGGGAGGGCCAGATCAAAATTTCATCACTGGAAAGACAGATAATGG
AGAAAAGGACAAAACAGAATAATACCACAGGTAAAAGAAGGAAGAAGCTGT
CTATTTCAGACCTCATCTTCCTCTGTAGACTTTGAAGAGGAAACTTCCTAC
TTCCAGAATTCTGGAGGTCTTTTAATGAATCTCAGAACTGTATTTTTAGTG
ATAGTGTATTTCTCAGTGAGATTCCAAATGTGTTTACACTGGGAAGCACAT
ATCCATCTGCTCTGAAGTATAAAAGCAGTATTTGTTGTTTGAAGTACTGAA
AATGGAGGTTCCAGCATTGTTATAATGTTGTCAGAGAAGATTGGTTATTAC
ATTAAGATATGAATATAAATCATGGCTATATAAAAATAAGAAAAAGATTGA
AGTCTTATTTTAGAGTGACAATCCATAGTAAATTGAATGTACCACATTAAC
AAACAGTAACAACTTTTTAAATAAGTAAAGGCTCAAGGTAGTCATTATCTC
GAATGCTTACTTGTGTTTCTCTGTAGCTATAGTACTTGATAGAGTCAGAGC
TGTTTGGATTAACCATAGCCCTTAAACAAAGCAGGCAATTGTGTTCCCGCA
TAGGCATGACGAAAACAGAGGCAGTCATCCAAAACCTGCATGGTCCTCTAC
GCCCACACGTATACAGTACGTGATTTACAAATCTAAAGTGGCGAAAGCAAC
AGTATCTATTCTAAGGCAATCATATGTTCTCTTATCTGTTTATCAATGGTT
ATTCTAAACTGTGTAAAAATGTTATTTGCATAAAACTACACTGTTTCTTGT
GATTTGTATTTTGTACCCTCCAATTTAGAAATTGTCCAGGTATCCAAAGAT
TGAGAATTAATTTACTCAATTTAATAATATTCACCTAAATTCTTAAAGTTA
TCATACACTGTGAACTCAGTACTTAAGCTCACACATTGAATCCTTATAATT
AGTAACATAAAATTTAATTCCATTTTTAAAAATGACATTATCTATTATCAT
TTAATTTGGTTCAATGAATAATTTACAATTTTAGAATAATAAATAAAGTGA
TGTTAACTCATGTAACCAGTACAACTAGTGGAAGAAATTTAGTAAATGCAA
GTTAAATTAGCTTTTGTTTTTGTTTTTAGAATATGAACCCTAAACTTGTG
TATACTATAATATTCTGCTAATATTATTTTTACAGTATAAGAATAAAGAAG
CCATTTTTAAAATGAAATTATTAAGCCAATTTGTCCAAAAAAAATCTTGAT
TAGATGTATTATATATTTTCCTTATTAAAAAAACCTAATAAAAGAGGTATT
AATATTTTTAAGTTATTTAAAAATTGTGAAGTATTTTTTTTACAAAATACT
TTAAGCTGTTAACTAAGACCACTAATGAAACTCACAGTTAAACTTTTTTTC
```

FIG. 8-97
```
TCTTAATTAGAACTTAAAGAGGTAGCACATTTAAAGCACAAGGAAAATTTT
TGATTTTTTTTAGACAAATGAGTTTTTATTTAAATTGATGTATTTTAAGT
CTTTATGTAAGCCAACTAAAATTTAAGATTACATTATAATTTATTAATTCC
CTTAAGTGGATAATTTCACAATTATTTAAATTCATAAAATAAGATAGTCTT
TTCTGGGCACGGTGGCTCACGCCTGTAATCTCATCACTTTGGGAGGCCGAG
GTGGATCACCTGAGTTCGAGACCAGTTTGGCCAACATGGCGAAACCCCATC
TCTACTAAAAATGCACAAATTAGCCAGGCGTGGTGGTGCACCTGTAATCCC
AGCTACTGGGGAGGCTGAGGCAGGAAAATTGCTAGAACCCTGGAGGCAGAG
GTTGCAGTGAGCCGAGATTGTGCCACTGCACCCCAGCCTGGGCCACAGAGC
AAAATTCTGTCTCAAAAAAAAAAAAAAGATAGTCTCAATCTTATTGCCAAT
TAGGAAAGCTAACCGTGCTAATAGAACAGAATTTAAAGTGGGTAAAAACAG
AGCCATAGGTTATCTATTTAGCATGTTGATCAGTTAAAGAAATAAAAGTAT
GTAATTAAGATCAGAAGTCCCTCAGGTGGCACCACTGCTGAGAATATGAAT
AATTCTGATTCTCAGTTTAGAAGAAAATTCTAGTTTCCTAGTTTCCAGCAT
CACATCCCTTACAATAAACTCGTTAAGGTTTAGAAAATATTAAATCTTTGT
TTTATTCAGATATTGAAAGCACTCTTTTTTTTCCCTGACTCAATAGTCCAA
TTTGTAACAACATTATGTTTCTTCTGTCCTCTAACCTTACTTAAAGAACGT
GAAGGGGCAATAATGTGAAATTACTAAAATTAATAATAAGCTGTAGAGCCT
CTGCCATAGCAGTTATTGAGACCAGACATTCGGTTTCCTTGATTTCCTTTT
TGTCTCCTGTTAGTCCTAACACTTTCTTAAAGTCAAAAGTTATAACAGGGC
AGCCATTTTATATTCATATCATCTTAACACAGGAATACTGGTTTTGCAGAT
ATCGACAACTATTTGGACTCAAAAAAGACAAGTTTTGGAAGGTGGAAAGAG
GCATACAAGCACAAAACATCAAATCCCATGTAAAGTCAGAAAGAAAAACAC
CAACTCTAACCCTGTGTCCTCACAGAGAATATCAACATCTTCAAACAAAAA
CACCCCAAAAAAAGGTTAATAAATAAACCAGATTTCCTGTCCTCTCCACTG
ACTAATCACTTAATGATGTGACCAGAAAACCAGAATTCAAATTCTACTACT
GCCACCAATATGCAACCAATCAGCCAAGTCCAATTAGAATAACCAAAACAA
ACAAACGCGGACGATAAACTTTTAGCATGCAAAAGCCAAAGGAAAGTGAAC
AGAAAACTCAAAGGGTCCAGGGATAGACAACCTGTTTCCAAGACACACATT
TCTGTTGGTTCTTATTGTATGACTCACATAAACACTGTCTTGGTGGAAAAT
TCAGAAATAAATGACCAAGAAGTTAATAATTTGCTTACTGGGTACTTGTAC
AGAAGAGAGAACAAGCAATAGAATTATTTCATCTAACACAGGCAAAAACAT
AATCTATGTAAGAGAAAGGGGAAAAGGCGGGGGAAACAATACTGAATTTTG
TTTGCAGATTTTGGTTACACTGATTAGTTAGTTGGCAGGTAAGAAAACGGT
CAGTCTGAATGGGAATAAGTGACCAGGTCCATTACAGGCATAGAAAAAAAA
AAAACCATTTAGGCCCGGCGCGGTGGCTCAAGCCTGTAATCCAGGACTTTG
GGAGGCCAAGGCGGGCAAATCACCTGATGTCCGGAGTTCGAGACCAGCCTG
ACCGACATGGAGAAACCTCGTCTCTACTAAAAATACAAAATTAGCCAGGGT
GTCGTGGCGCATGCCTGTAATCCCAGCTACTCCGGAGGCTGAGGCAGGAGA
ATGGCTTGAACCCGGGAGGCGGAGGTTGCTGTGAGCCAAGATCGCGCCATT
GCACTCCAGCCTGGGAAACAAGAGAGAAACTTCGTCTCTAAAAAAAAAAAA
AAAAAGAAAAAAAAATTTACTTGTGAGGGACTCTGGAAATTTCATTTCTCA
TCAGAATTTCTCAGATAAGTTATCTAGGCAAGGCAGCCTGTGATTGCACAG
CAGTGTTCAAGTATAAGGCCTTGTCTGGCACCAAAGACAGGCCTTAGTTTA
TTTCCCAGGTGTGAAAGAAATTGCAGATTTAAGATCACACAGTCCTTATGT
TAAATAACTGTAACCTAAATTACATGGTATTTAAGTTTGTAAAAATCTGCT
```

FIG. 8-98

```
TTAACACTAATTTTATTTATTGTATATTCCCGGTTTTTAATGGAGAAAGCA
AACTTCTAGGTGCTAAAAACGTGTTCTAGACTTGAATAAAAAGATAGGTAG
ACTACGTCTAACCCTTCATCTTAAAATCTTTACCTGGAAAAGACCATGAGT
AAAATACTTAAGGGAATGTGGAATTTCCCAGGCCACAAAGCGGCCTGCAGT
TGTCTAGGAAGGGAGAGTCCTCTAGGAGATACAGTGTATGTGCTAAGTTTA
ATGACGTCTCCTCTTCATTCTCCCCCACCCAGCGCCTAGTCCTTACTGGCC
TTCAGTTCAGTGTTCGAAGGCTTGTCAATTTACCCAGCAGTTAAGAGTTGG
CTTCTCCTAAAGCAACTTTCAAACTTGTCTGCATGTTACAAGCCCCCTACG
GAGATTTTAAGTTTCAATCAGGCAACACACCATTTATGGCTGACTGAGCAC
TGGGATTCAAGCAAAATTTGATTTGATTTGAATCTTGAATAAACCAGTTGA
ATAGAATAAGATGTATGAAGCAACATCTGGCGCAGTGCTTACATCTTTAGT
TCTGTACTGCCTTAGTGTTGTTATCAAAACTGACGCATATTAGTTAAAAGA
CTATTACCGGGGCAGTTGGAAACCCAGGAGACACACCTTCAGTATACTACG
AAGGTGTGCGCCACGAAAACAGAGGGGGAGTCCTTCCTTAGGCAGTTACTG
CCCAGGTTCCCACTCCGGTCCGCTATGTAAATCAGAGTCTCAAAACAGCTT
TCCCTCGATTGGTTAATATTTAAAATGACAGGACAGCCTATTGGCTAGAAG
CTGGTGGCGAAATTATGACATTACGGCAACCGTTGATCCTGGCGACGTAGA
CAGGGACAGACAGCTGGGTCTGAAACCTAAGCGAGCCTGCGGTTTCTTCCG
GGAACGCCGAGTTAGCAAAATGGCCGCTTGTCTCCATTTTAAATTTAAGCA
CAACGAATTGACCCCAAAGCCATTTTAATGGCTGGCTTCTTTCGGGTTCA
GGACCCTTTGTCCCTCTCTAAGCTGCAACACTTGTCCCCACCCCTCTCCAG
TTCCTATATTCTAATACCCCTCCGCCGCCAAATAAAATTTGGCGTCTGGCC
ACAGCTCTTTTAGTGGGTATCTGGGTGGCTCTTAAAAGAGCCTTTGGGGTT
AGGTGTTAAGACGCTTACTTGGAATGTTTACTTGGAGCTGGTGTACTTGGT
GACGGCCTTGGTGCCCTCCGACACGGCGTGCTTGGCCAGCTCTCCGGGAAG
CAGCAGGCGCACGGCCGTCTGGATCTCCCTGGAGGTGATGGTCGAGCGCTT
GTTGTAATGCGCCAGGCGGGAAGCCTCGCCCGCGATGCGCTCAAATATGTC
GTTAACGAAAGAATTCATGATGCCCATGGCCTTGGAAGAGATGCCAGTGTC
GGGATGGACCTGTTTCAGCACCTTGTACACGTACACAGAGTAACTCTCCTT
GCGGCTGCGCTTGCGCTTCTTGCCATCTTTCTTCTGCGCTTTGGTCACTGC
CTTCTTGGAGCCCTTCTTCGGGGCGGGAGCAGACTTGGCTGGCTCAGGCAT
CTTAAAACACCAGAAATGTGTCGAAAGTAAAGAGCGGATTTCTGCTACTTA
TAGGGCTTTTATGCTAATGAGGGATGGAGAGTACCTCTTAGTTAATTGGAA
GACAAACTGCACAGTTGTCATCCGTGGGCAGAGCTATGCAAATGAGGTATG
AAAGTACAGCTTTTCTATTGGCTATCTGACTAGCATTTGCTACCGACCAAT
CAAAAAGTCGGATTTACTCCCCAGGAACTACCTATAAAAGCGGCCATGTTT
TACATATTTCTTGATTTTGTTTGTTTCTCGTGAGCTTAGGCCGCTGGTTT
TGGTGATTTTTGTCTGATTGCAATGTCTGGACGTGGTAAGCAAGGAGGCAA
AGCTCGCGCCAAAGCGAAATCCCGCTCTTCTCGCGCTGGTCTCCAGTTCCC
GGTGGGCCGAGTGCACCGCCTGCTCCGTAAAGGCAACTACGCAGAGCGGGT
TGGGGCAGGCGCGCCGGTGTACCTGGCGGCGGTGTTAGAGTACCTGACCGC
CGAGATCCTGGAGCTGGCCGGCAACGCGGCTCGCGACAACAAGAAGACTCG
CATCATCCCGCGCCACTTGCAGCTGGCCATCCGCAACGACGAGGAGCTCAA
CAAACTGCTAGGCCGGGTGACCATTGCTCAGGGCGGCGTCCTTCCTAACAT
CCAGGCCGTGCTTCTGCCTAAGAAGACCGAGAGTCACCACAAGGCCAAGGG
CAAGTGATTTGACAGGTATCTGAGCTCCCGGAAACGCTATCAAACCCAAAG
```

FIG. 8-99
```
GCTCTTTTCAGAGCCCCCCTACCGTTTCAAAGGAAGAGCTAACCTCACTGC
TTGTAGGTAGAAGGAAAAAAGGCACTAAGGTAAGTTAATTTTATGCCAACC
TTGAGCAAAGCGTATTACTGCTTTTCGGTTTTTGGGGAGCGCTGTTACTAA
AGGTTGGTCTGTTTGTATGTAATAGTAGGTCAGTTACGTACTATCATACTC
TAAAGAAATATTCTAGTTAATGCTTTGTAAGATCGACCATAGTTAGTGCCT
AACAGTTTACATGCAGGGATGCCTCGTGATCTAAACACTTCGTTGTGATTA
CTTTAAAAATGTAAATTGAAGGCAAAACTCTAACGTGTTGGTAACCTTGTT
TGGTCCTCCGACTAGTCCCCCGTCTATTTTTTCTCAATTTAGGCTGTAGG
CAGCCTCACTTTCCTAATTCTGTGAGAGTTATAGGTCCCATTCCTGCTAAA
GTGCAGAGTATATTACCTAAAAGTTAACCAGGGAGTTGAAAGGTGTCTGTA
AAACAGACTAATGTCCCTAATGTAGAACGGTGCCTGACATGCAACTTACTC
TTGTATTTTAAGAAGCTCAAGCGTCTAGGTTGCCATTACAGGCAGAAAAGG
AAATAGAGTGGGGCCTGTGGCCACTCAAAAACCTTTGCTTTCTGCTCACCC
CTCTAATCCTACCACTTTGGGAGGCCGAGGGGGCTGATCACCTGAGGTCAC
GACTTCGACACTAACCTGGCCAACATGGTGAAACACCTCTCTACTAAATAA
AAATAATAAATAAAAAAATAAGTTGGGCGTGGTGGCACATACCTTGTAATC
CCAGCTACTCTTGAAGCTGACGCAGGAGAGTCGCTTGAGCCTGGGAGGCGG
AGGTTGTAGTAAGCCGAGATCGTGCCACTGCCCTCCAGCCTGGGCAACAGT
GAGACACGGTCCCCCAAAAAAACCTTTGCTTCTAGGGATCTGGTAACAGCT
GCCCCACCCACAAGAAATGGAGATCTGGGACCATGGACAAATTTCTAGAGA
CCTATTTTCCTGGATTCTGTGAATCTCGCCGAGGTTTTCTTCCGGATCTCG
GTTTCTGCATTTTTTGTTTGTTTGCTTGCTTTTTTGAAACGGAGTTTTGC
TCCTGTTGCCCAAGCTGGAATGCAGTGGCGCGATCTCGGCTCACTGCATAC
AAACTCCGCCTCCCGGGTTCAGACGACTCTCCGGCCTCAGCCTCCCTAGTA
GATGGGATTACAAGCGCCCGCCACCAGTAGAAACGGAGTTTCACCAGGTTA
GCCGGGCTGGTCTCGAACTCCTGACCTCAGGTGATCCGCCAGCCTCTGCCT
ACCAAAGTGCTGGGATTACAGGCGTGAGCCACCGCGCCCGGCCGGTTTCTG
CTTTGATCGGAATTAAGTGGGCAGAAAAGTCTAGGCGGGCTAAGTCTTGCC
TATGCATCTGCGCCCAGCTGCTCAGACTGGCCAAACAGACCCAGTCGTTTA
GTCTAACGCTTCTGGAACTCCACTGAAGCGTTTTGCATTGTTTCGTTTGGA
GCCTTCAAATCCGAGTGTGTGGCAGGAGATAATAATCCTAGCAGAAGCTGT
TTACTGCTGACGCGCCTCCCACTTCCCAGATACTGACACCGGCTCAGGGCG
GATCCAGCCTTTTCCGCTCTTCCCTCCCTCCACCCCCTCCTTTCCCTACAA
CTACTCTCAAAGGAAAAGGGTTGGATGTCCCATTTGGGTGAAAACAAAGTG
GCATAAAAGCAAATGATCACCTTTGATAGCCACATATTAGAATTTTCCGAG
GGTATTTTTAAATTACAACGATTCTAATGGGCAGCTGGGCTGAGAATCATC
AGATTTGAAGGTCTGGTTTCACATGGCTCTTGGGCTGAGAAGACCGGATTT
TCCCCCCCCAGCATTTCCTGTATGTCCGAGAATTTCGATCCTAAGGTTAGA
ATTGCCTTATGGGCCTTGGAATCCTTTTTATTCACTGACCAAATTGCCTTT
GATTCCAGCTCCCAATCGGTGTGTGACCTTGGCCTAGGGCTTAATCTCTTC
CTACCTCCATCTCTTCCTTGTATGCTTTTGCTCACCTTGAAATGAAAAGAA
CCTGGCTCAGCAAGTGTAGATTCTGAAATCAGAAAACAGGCTGAATAAGAG
AGATGGTTTATTAGGCACTACTGTGTGCCAGGCACATTTCATGAGCTTCCA
GTATGTTAATTCATTTAATCCAACAATCTAAGAGATAGGTTTTATCCTTAT
TCCGAATTTTGAGATGAGCAAACTAAGAAACAGCTTAAAGAACTTAAGTTG
TAAGGCCAGGAAAACAGTACTTATAACAGCTGACTATTCTATAACCACACC
```

FIG. 8-100

```
TCCTTAAGAGATTATTGTCAGAAAAATAGAAAGAGTAAAACATCCATACAT
AATGGGTAAACTTTGTCCACATACCAGAATGTTACTAATGGCTTTCTAACC
TCTGAAGAATTTAAGGGAAGGAGGAAAGGTAATTTTCCCCAGGGAATCTAC
ACGAAGAGGTAAATCTTGACAATGTATTAATACTGTAAACCCAGGGAAAAA
AAGCCAGTACAATTTTTATTTAGGGTGTGGCAAATAAAACAAAGGGACACG
TGAAAACATGGCTCAGTAAAGAGCTACAAGACTTGGTGCAACTGACTTATT
GTGGTGAGTGAGAAAAGGAGAGAGAGAAAACTTGAATTTCAATTCTTCTCT
CTGGGCTCCAATAACAAGATTTTGTATTCGGTCTATTTAGTAGTGAATGAT
ACATTGTGTTAAGTTTGTTAACCTAGAGGCTTTCATCTTAAGCAGTACTTA
AGATGTAGACCCCCTCTTATTCAAATACTGATAATCAGCATAGAACTTGGC
ATACAAGAGACACTTGGCTGTTGGGCATTGAGAAAATGTTGAACTGAATGA
ATCAATGACTTAGGCAGCCAGGAAGCACTTTGTTGTAGAGAGTTGGTTTAT
TACTAAGGAAGACATTAAGTATTAAATATTAGACTAATAGGTTGCTAATAG
TGTTTTCTCTTTCCAATAGAAAATGTCTTCTGAGGCTGATCTGGTGTCTCA
CATCTGTAATCCCAGCACTTGGGGAGGCTGAGGTGGGTAGATCACCTGAGG
TCAGGAGTTTGAGACCAGCCTGGCCAACATGGCGAAACCCCATCTCTAATA
AAACTACACAAATTAGTCAGGTGTGGCGGTGTTCACCTGTAGGCGCCTGTA
GTCCCAGCTACTCAGGAGACTGAGGCAGAAGAATCACTTGAACCCCGGGAG
GTGGAGGTTGTAGTGAGCCAAGATCGTGCCACTGCACTCCAGCCTGGGCGA
CAAAGTGAAACTCCGTCTCAAAAAAAACCAACCCCATCTCTACTAAAAAA
TACAAAAATTAGCTGGGCATGCTAGTGCACGCCTGTAGTCCCAGCTACTCG
GGAGGCTGAGGCAAGAGAATCACTTGAATATAGGAGGGGGAGGTTGCAGTG
AGAGTGAGACTCTCAAAAAAAAACAACAAAACAAAAAGTAACAAGAAAAAA
GAAACTATATTCCAAAAATCCAAATTTCACTGGCAGTTTGTTCTGGGAGCT
TCAGACACATAGAAGGTGTCAGTTAACCAGTTCTTACCTAAGAGGTACTGC
TAAGAGCCTAGTCCCTAAGCAAAGGGAGCTTCAGAGAAACACAGAAGGTGC
CAGTTAACCAGTTCTTACCTAAGAGGTACTGCTAAGAGCCTAGTCCCTAAG
CAAAGGACATTCCTCGTAGCTCTGTCCTGTCTCCTCATCTCCAAAATACTT
TACCTTCTACTTTGAAATGCCCACTATTATATTCAAAAGCCCTAGTTACTT
CCAGGGAAAATTATCTATTGAGCAATGAATTTCGGTAGCTTCAGTTGGATT
CCAACTCTTGAGCAAGTTTTCATCTCCCTTGCCTGAATGGCCCTGGGGAGG
ACTATTTAAATTGGGCGAGTGGATGAGGATGCTAAACCTAGAGGTCTCCC
AATTACCAAAGGCACCTGGGCACCAGGGACTAAAGTTTGTCTCAGGAATTT
ACTGAGATATGAGGCTGAGATAAAATCATTTTTTGGTACATAAGGTATCTT
GAACAAAGCAGATCAGTTTAACACAAAATCAACAATCGTAATTTCCCTTTT
TAAATTTCCAAATCTATGTAGCAATATCCTTTCCTTTAATTCATTCATCAT
CTCTATTCACTTTTTGTATTCTGTAAATCATTTGAACTTTTATAAGAATTA
TATTTTCCCCTTGAGGTCACAAAAAAGAAAGTATTAGAAATTTTATAACCA
ATTTTTAAAAAATTATATTTTAAGGTTAAATACAAACCTTCTAAAGGTTTG
TCATCTGTTGATCCTAAATTATAATTATAAATTTATATATTCCTGTTGAAT
ATAATGCATGTGTGTTACAAGATTATTAGCAATTTGAGAATTTCCCGTGCA
TATTGGAGATGAGCAAATGGAATAAGTGCTCATGTGTAGCGACAGGATTCT
CTATTTTATTTCAATACTTAATATTGTACCAAACCAAGTAAGAGGAGCATC
ATGAGAAAATGTACTAAAGGACAGTCATTACCTATATTTACACCTAGAAAA
GAAAACTATATTATTGATAAACTGATAAATCTATTTTATGTATTTATTTAT
TATTTTGCTCTGTCATCCAGGCTGGAGTGTACTGGTGCGATTTCCACTCAT
```

FIG. 8-101

```
TGCAACCTCCTGCTCCCAGGTTCAAGCAATTCTACCTCAGCCTCCCTAGTA
ACTGGGACTACAGGCATGCACCACCACACCCAGCTAATTTTTATATTTATA
GTAGAGACAGGGTTTCACCATGTTGGCCAGCCTGGTCTCAAACTCCTGACC
TCAGGTGATATGCCCACCTCAGCCTCTCAAATGCTAGGATTACAGGTATGA
GCCACCGCGCCCAGTCTGATAAATCTATATTAAAAAGAATAAATATAACCA
TTGCATCTTCAACAGAAATTGGAATATGGCATGTAGATTTCAAAATAAAAT
GAATTCTCTGGCATTGAATTACTGTACTCATGTTGAAGAAATGTCAGAACT
TCATTGGATGTTATTATATTACAGTTGTTTGTTTGAGTTGTAGTTTGGGCA
GAGTAAAGGAGCCAACATGTCTTAGGATTTAGAACTTGTGCACATTGCCTA
CAGTTGAAAGAAGAAAGCATGCTAAATTCCAGCCTCTTTGGTATGTGGTTG
GGACGTAAAGTTTTACCACATCCTTCATTGTCTTAGCCTACTCAGGCTGCC
ATAACAAAATACCAGAGACTGGATGGCTTAAACAACAGAATCTTTTTTTCC
ATATCTAAGAGGCTTGGAACAGAAATTCATTTTCTCACAGTTTTGGAGCCT
GGAAGTTTAAGATCAAGGTGCCAACATAGTTTATGGTGAGAATCTGTTCCT
GGCTAACAGATGGCTGCCATCTCACTGTGTGTTTGTATGGTGTTTCCTTGG
TGCCTGCGTGGAGAGAGAGCTCTAAGTGTCTCATCTTCTGTAAGGACACCA
GCCCCAATGGGATTAGGGCCCTATCCTGTGATCTTTAGTTTTATGTACCCC
CTAAAGGCTCTATGTCCAAATGCAGTCACACTGGGGTTTAGGGTTTTAATA
AATGAATTTTGGGGGACACAGTTTAGTCCATAACATTCTGTCCTTGACCTG
CCAAAATGTATGTCCTTCTCCCATACAAGATAAATTTATTCCATCCCAGCC
GGGCATGGTGGCTCACACGTGTAATCCCAGCACTTTGGGAAGCCAAGGCAG
GCGGATCAGAAGGTCAAGAGATCGAGACCATTCTGGCTAACACGGTGAAAC
CCCATCTCTACTAAAATAAAAAAAAAATTAGCCAGGCGTGGTGGCGGGCGC
CTGTAGTCCCAGCTACTCTGGAGGCTGAGACATGAGAATGGCATAAACCCG
GGAGGCAGAGCTTGCAGTGAGCCAAGATGGTGCCACTGCACTCCAGCCTGG
GCGACAGAGCTAGACTCCGTCTCAAAAAAAAAAAAAAATTATTCCATCCC
AACAGCCCCTGAAAGTCTTAACTCATTCTAGCATCAATTCTAAAGTTCAA
AGTGTCATCTAAAAAATCATCTAAATCAGGTTACGGGTGAGGCTCAATGTG
TGATTCATCCAGAGACAAAATTCCTTTCCAGCTTTGAACGTGTGAAACCAG
AAATGTTACATGCTTCTAAGGTACAATGGTGAAACAGGCATAATAGACATT
CCCATTAGAAAATGGAGAAATAGGAAAGAAGGAAGGTGTAATGTGTCCTAA
TCAAGTCCAAAACCTGGCAAGGCAAATTCTGTTAGGTCTTAAGAAAAACCC
TCTTTGGCTTGATGCCCTGATTTCCAGGCCCAGTGGTGTCTCAGTGTCACC
TCTGGCTCTGTAGTTGGCCTACTCCATCTGCCCTGCCTGAAGTCTCGGTCT
TTCAGTTTGGTGGGGTCCCACCCAGGCAGCCATCTGTGAGAGACTCCCACA
CAGTTCTGCAGGGCATCTTTGAAACAGGTAGAGTCAGCCTTGACTACATGT
TCCCACCCCCACCCTATCCCATCTGTACTCTCTGAGTCTGACATCAAAGTG
GCAGCCCTGGCGGCTCCTGCCTGTAATCCCAGCACTTTGGGAGGCCAATGA
GAATGGATCACTGGAGGTCAGGAGTTCCAAACTAGCCTGGCCAACATAGTG
AAACCCCATCTCTACTAAAAATACAAAAATTAGCTGGGCAAGTGGTGGCAG
GAGCGCTACTCGGGAGGGTACAGATTTAGAGCCTGTAATCCCAGCTACTTG
GGAGTCTAAGGCAAGAGAATCCCTTGAACCTGGGAGGTGGAGATTGCAGTG
AGCTGAGATCACACCATTGCCCTACAGCCTGGGTGACAGTGAGACTGCCTC
AAGAAAAAACAAAAGAGTCAGCCCTAGTGATCTTGTAAGTTGCCTTTGGTG
GGTCAGTCTTTCCTTTTCTTAAAGAATAGTACACATTGACAGCCAGGTAGC
TCTATGATCCTGTTCTATAGAATTCAAAAAGTCGACAACCTTCCTTTGTTC
```

FIG. 8-102

```
CTTTCTGTTTTCTCTGCCTACGTTAGTTTAAATTGGCAGTGTCTCTGCTGG
AATAATCCCATCTCTCTTCCTGGCTTCTGCTGAGATGGCTGATTAAATCCT
TGGGTCACACCCATTATCTCTTTATCAAATGGTTGTTCAGGCTAGGCTCAG
TGTTTCACGCCTGTAATCCCAACACTTTGGGAGACTGAGGAGGGCAGATCA
CTTGAGCTCAGGAGTTAGAGACCAGCCTAGGCAACATGTCAAAACCCCATC
TCTATAAACAACAACAAAAAATTAGCCAGGGTGTGGTGGTGCATACATGTA
GTCCCAGCTACTTAGGAGGCTGAGGTGGGAGGATTGCTTGAGCCTGAAGGC
AAAGGTTGCACTGAACTGAGATTGTGCCACTGCACTCCAGCCTGGATGACA
TAGCCAGACCCTGTCTCAAAAAACATAAAAATAAAAATAAAACCAAGAAAA
AAAAAGAAAAAGAAAACATTGTTCAACCATACCTCTTCAAGAAAAACTTTC
TCAATTTTTACAATATAGATTGAGAAATCTATCCCAAATCTCCAAGTTCTG
ATTGTGTTTTGCTTAAAAATTCCTTCTTTATTTCGGCTCTTTCCTCTCACA
TTTCACTTTAAGCAGTAAGGAGGACCTAAATCACACCTTCAATACTTTGCT
TAGACATCTCTTCTGGTAAATATCCAGTTTTACTGCTTATAAGTTCTTTCC
AGTAAACACTACAGCGTAATTCAGCCAAGTTCTTGACACATTGTAACAAGA
ACAGTGATTTCTACAGTTTCCAATAACCTGTCCCTCATTTTCATCTGAGAC
CTCACAAGAGTTGACTTTAATGTCCATATATATATATTTTTTGTGTGTGTG
TGGCGGGGGGAGTGGAGTCCTGCTCTGTATCCCAGGCTGGAGTGCAGTGGT
GTGATCTTGGGTCACTGCAACCTCCACCCCCGGGTTTAAGCGATTCTTCA
GCCTCAGCCTCCCGAGTAGCTGGGACCACAGAAGCACATCACCATGCCCAG
CTAATTTTTGTATTTTTAGTAGAGACAGGGTTTCGCCATATTGGCCAGGCT
GGTCTCAAACTCCCGACCTCGTGATCTGTGCCCTCAGCCTCCCAAAGTGCT
GAGATTACAGGCGTGAGCCACCACGCCTGGCCTAAAGTCCATATTTTAACC
AGCATATTTAATATTCTATCCATGATCGTTATAAATCTAAGTTTCTATGAA
AATGGAAGCTTTCTGTCCAGCTCTCTTCCTTTCTGAGCCTTTGCCAGAATT
GCCTTTAATGTCCATATTTCTTTCAATAGTCCCTTCACAATTGGCTTTTTC
TAGTATGAACCTCAAACTCTTCCAGCCTTTACCCATCACCAATTTCCAAAG
CCACTTCCCCATGTTTAGGTATTTGTTGTTGCAGCATCCCACGCCTGGGTA
CCAAAACTTAGTCAGCTTGGACTGCCATAACAAAATACTACAGACTGGTGG
CTTAAACGATAGACATTTATTTTCTAACAATTCTGCAGGCTGGAAATCTAA
GATCCAAGTTGCCAGCATAGTCAGTTTCTGGTGAGGATCTCTTCCTGGCTT
AAATTATTTCACAGACACCAGGCAGATAACCATATCCATTCTTTCCTGTAT
TCGTTAATAGTCAGAGCTAAAAGTGTAGGGCTCTAAATTTACACTTCAACA
AATTGTTCTGTTATTAAGTATTCACCTCAAAATGACCAGACTATACTATCC
TCTAAATTTTAGAAACTTGGAGCTTGGCTCTGGTCCCTAGTCTTTGTTCTG
TCTCATTAATGGCTTCATCAATACTACGGTTCCAAAGACTATCTATATGCA
GTAAACTTCCAATTTTACATCTCCAGCCTGACCTTTTTCTGAAATGCAAA
TGTGTGTAGCCACATTTTCACTTGACATCTCCATTTAGAACTCTAATAGGT
CTTTCACCCTAAACACTTCCAAGACACAGGAATAAACGTGCTCCTTAAGCC
TGTTATCCCTTCCAGTTCTCCCCAGTTCAATAACTGACACTACCATTTACT
CAAATCAACATTCTAAGAGTGTCACTTGCTACATTTCCTTCATCTCTACAA
ATCCAAAGTATCTGTGAGTCACGTCACCTACATATTCAATACATGCAATAA
TTCATTCTCCATACTCCTTACCATGACTTAAGGGCCCACTCAGTGACCATC
TCTGGCCTCTGTTCACCTCTTCTGCTGTTCTCCTTTGCTGTTCCAGCCACG
CTGGTCTCTTTTCACATCAAGCAGCTAAGCTCTGCCCATTTAAGACATTTA
ACTTCTTGGCCTCAATCTCTGAAATGCCTGTTTGATTTTTCTTCTGGTGAG
```

FIG. 8-103

```
CTCATTTTCACTCATCAGGTCCCAGCTCTGTTTCAGACAAGGCTATCTAAA
ATAGACCTACCTAAATGGATTAAAAATCTGAGAATATGAAATAACAAATAT
CAGATGACATTTTAGGAGACCCTTTATATACCTCATTTGTGTGTGTGTGTG
TGTGTGTGTGTGTGTGTGTTTGGAAATGGTGATGGAGGGTGTCATTG
CTAAGTGAGGAGGAAACACAAAAGCCATCTAGGAAAGGACACAGACTAGAT
AGGTCCAAAAGTGGTTTAAGACAGAATATATGTAAAGAGAGTTATAGAAAG
AGCAATAAGTTGGGATAAAGGATTTCCAAAACATATACGGGGTTAGTAACC
TCAATTTACAGGGACAAACTGCAAAACGTTAGTGAAAAGGCAAACAACATA
ATATAAAAGATGATTAAACGGTATTTTATATCATGTATTAAATTCATATGG
CCAATACATATGAAAAACAAGAAACAAAAAACCTTCCTAGTAATTCAAAAT
TATGCATATTAATACAACAAAGGGATACCACTTCTTTTTTTTTTTTTTTT
TGAGACAGAGTCTTGCTCAGGTACCCAGGCTGGAGTGTAGTGGCATGATCT
CAACTCACTGCAACTTCCACCCCCTGGGTTCAAGCGATTCTCCTGCCTCAG
CCTCCCGAGTAGCTGGGACTACAGGCGCCTGCTACCACGCTCAGCTAACTT
TTGTATTTTTATTAGAGATGGGGTTTTACCATGTTGGTTGGCCAGGATGGT
CTCGGTCTCTTGACCTCGTGATCTGACGGCCTCAGCCTCCCAAAGTGCTGT
GATTACAGGCGTGAACCACTGCACCTGGCCTAATTTTTGTATTATTAGTAG
AGATGGGGTTTCACCATATTGGCCAGGCTGGTGTCGAACTCCTCCTGACCT
CAGATGATCCACCCACTTCAGGCTCCCAAAGTGCTGGGATTACAGGCATGA
GCCACTGTGCCCAGCCTGGGATACCATTTCTTACCTATGAATAGACAACCA
CTAAAGCCAGTATACTCAGGACTGCAAAGGATGAGGAAGAATTGCCATTGT
CATATAGTTTTTCATAACTTTTCCTGACAATGTCTATTAAATTGTATTAAT
AGACATTTGGAAAGGGAGAGTGTCAACAATCTAGAATAAAGGCCCCACTAG
GTAAGGTTACATATGTAAGGACTCTTTCAAAACTGTCACAAGAATTCAGGT
ACGGTGGCTCATGCCTGTAATCCTAGCATTTTGGGAGGCTGAGGCGGGTGG
ATCACTTGAGGTCAGGGGTTTGAGACCCGCCTGGCCAACATGGTTAAAACC
TATCTCTACTAAAAATACAACGATTAGCCATGCATGGTGGCACATGCCTGT
AATCCCAGCTACTCGGTAGCCTGAGGCAGGAGAATAGCTTGAACCCAAGAG
GCAGAGGTTACAGTGAGCCGAGATCGCACCACTCCAGCCTGGGCAACAGAG
TGAGACTCCATCTCAAAACAAAACAAAAAAACTACTCAAAACTGTAATAAG
AAAAAAAAAAACCTAATTATACATGTAAAACATTTAAATAACTAAAATAAG
AATACTGTTGACATAGTGAGACATCCATTTATACTATGGAATGTTATGCAG
CTACCTGAAACAATAATCCGGTGAAACAAAATCACACACACAACTGATGAG
AGTAAATAGAGAACCGTATGGAAGAAAACATACCACAGTAATTATCTCAGA
TAGCTGAAACTAAGTTGGTGCAAAAGTAATTGTGGTTCTTACCATTACTTT
CACTGGCAAAAGCTGCAATTACTTTTGTACCAACCTAATAGAATGGGGTGA
GGAGAGGTAAACCTTTATAAACATCTCTGTGTGAACTGTTAAAATGAGCAA
GTATATTTTTTTAAAGTATAAAGAGAGAAAAAAGTAAACTTTCTCCATTT
CCCACCTCAAATTATGTTCTGTCACTCATCCTGTTTAGATTCTTTCAAATG
CAGTTTGAAGTTTTATTTATGAGATTCCTTGTTGTTTGCCTCTTTCCATTA
AACCTAGCTCCACAAAGTAGGGACCTGATGTATTCATTCACTGTTATATCC
CAGCATCTAGCAGAGGGCCTGACACTTAGTGGGAACGCAAGTATCTGGTAT
ATAAACCAGAGAATAGATATTTTTTTAGCCCAGAAAGCTGTTTCACTGCAC
AGAGTGTAATTATCTGAATTTCTATAAAAATGTCTATCTATAAATCATTGT
CAATACATTACCTACTCACCTTACCCAGCTACCAGGAACACTATGAAGTTT
TGAATTACACCCCATTTGTTTTCCACACTCTTACCATTTTCCCAGTTTCTG
```

FIG. 8-104
```
CACTGACCTCTCCAGACATCATGTGTACTGATAATTCTAAGTTGTCTAGAT
TGTTAATTCTTTTAAGGGCCTGTTCTCTGCTAGCTGGCATCATGCATAAAA
TAATTCTCTTTAATATGCTCTGGGTCTAGGGTTAATAGATGTTTGCTTAAA
ATCATGGAAAGAAAATGGTCACACAGCTGGTATGTGTGATCAAATTTGTGC
TGTTTCATCCACTTAATGTTTACTTTGTGGTAATGGAACCTCCCAGCTTTT
ATTTTCCTTCCTTCCTTCCTTCCTTCCTTCCTTCCTTCCTTCCTTCCTTCC
TCCCTCCCTCCCTCCCTCCCTCCCTTCCTTTCTTTCTTCACAGAGTCTAGC
TCTGTTGCCCAGGCTGGAATGCAGTGGTGCGATCTCAGCTCACTGCAACCT
CTGCCTCCCGGGTTCAAGCGATTCTCCTGCCTCAGCCTCCCAAGTATCTAG
GATTACAGGTGCATGCTGCCACACCTGGCTAGTTTTTGTATTTTTAGTAAA
GATGGAGTTTCAGATGTTGGCCAGGCTGGTCTCCAACACCAGGCCTCAAGT
GATCCGCCTGCCTTGGCCTCCCAAATTGCTGGGATTAACAGGCCTCAGCCA
CTGTGCCCGACCCCAGCTTTTATATTCTAATGCTGAGATTATTCAGTTAAC
ACTCTTACCTGCTAGGATAAGTTTGTTGGAGAATTTTACCTTACCTTGTAC
CCTTTACCTTCACATCTACCTGTACCCTGGCCCTTCACATCCTTTCCATAT
AATATATCTTCAGTAAATACAGGGAAAAAAACCCAGAATGATTATGTTGAC
AGCAAAACATGTTTGTGCAGAAACGGAGTAGTCACTATCTAAGCCACAGAG
ACTTAGGAGTGTATTCCTGAGTTATGTATCATTTTAACCATCACTGGATCT
TAAATCCCAGTTGCTAAATTGAAGGGAGATACATGACTCTTTTTAGGGCTT
TGCTCTCTGATACAGTAGCCATTAGCCACATGTGATATTTTAAATTTAAAT
AATTAAGTCAAAAATTCAGTTTCCTCAGTCTCACCACATTTCAGGTTGCTG
GTGTCTACTGTATTGGATACACAGACATAGAACATGTCTATCATCACAGAA
AATTCTATTGCATTGCACTGGGATAGGTACTTTTTGTGCCCTTGGGCTGAT
AAGTTCAAGTGCACTTAACTAGCTTCCTCCAAGTGGAATCAGAGGATAAAT
TTACCATACAAAATACAGGATACCCAATTATATTTGAATTTCAAACAGGCA
ACAAATAATTGCTTAAGTATGCCCCTCACTGCACACCCAAATATTACATGA
GACATTCTATACATATATATATATATATATATATATATATATATATATATA
TATATATATATATTTGAAATTCAGATTTAACTGGACATTTGGTATTTTT
AATGTGCCAAATCTAGCAACCCTATCTGAAGAGCAAAACTGGAGTGTCTAG
TCTGGATAGGTCCTTTTACACCACAGGGAGTTATTTGAGGAATTGAGAAGG
GCTGTGGTACCTGTAAAGAACTAACTCATTATGAAGAAAAGGATCTGTAAG
TTTTTCTGTATGTGTAAGGAAGGCCAAGAAGGTGGTTTCCAGATATATTTA
CTTTTTCTTCTCTCTCTTAGGTTGCAAAAGCTTCTCATTTCAGAGAGAT
GCCAGGATCCTAAGTGCCTGCCAAACTTACCAATTCTAAGGAATAAGTGGA
TGGATGGCATTACTGATTCCTACATTACTGATTGATTCTGCATCCGCAAAT
TGTTTTATTAAAAACATTCTACATCATGTGTGGGGAGATAAGGAGGATAAA
ATGAAGAGAAAGAATATTATTGAGGGGAAGTTCTTCTGAATACAAAATGTG
TTTAATTTTTTAAATAAGTATTACATTCACAGGGTTCAAACTATTTGAAGT
AAAGAGATTATATATAAAGAATCCATCCCTCAACTTACCCAGGTGGTCACT
TTTCTTTTTCTTGTGTATCTGCCCAGTATTCATTCCTGCTGATATCAGTCA
ATAATGAATGATACGTGTTTTCTTCACTTTTTTCATTCTTGTCAGGTAGCA
GACTGTGTAGACTTTTCTGCACTTGCCCTTTTCATAACAATCTATCTTGGA
GAACTTTCCCTATGAGAACATACAGAGCTTCCTGTACACAGTTGCATGTAC
TGCATTATGCAAATGCATTATATTTTATGTAACCTGTCCACTGTTGGTAGG
CACTTGAGTTGTTTTAGTCTTTTGCTATCAAACAGTTCTGGGATGATTAAC
CCTGATTTACTGCAAAATTGAAATTGCTCTGCTATTCTGCTGGAATGGTGG
```

FIG. 8-105

```
TAAGTGAACTGAAAATTCCAGTCACTCTTGGGCTAGACTCAACGTTCTTAA
AAACTATGTGGCCATCACCAAATTAGTTATTTTGAACCTTAATTTCTTCAC
CTCTAAAATGGAGGTAATACTTACCTTAAGTGGCTATGAGAATGAAGATCA
TGTGTATGAATTGTTGGTGCTCTAAAGAACAGCACAAATAAAATTATTTTC
AAATTTAATTTTAATTGAACTATGTGTAATTTCTTAATTTTGAAATAATTT
TATTTGTAATGTGCATAATCTTATTTAATGTATAATGTATACATTGTAATA
GAAACAGATTTCCCAAATTCCAGCCTGGCATGAGGTAATAAAAGGTAATGC
AAAGGGAGAGGAAAGCATGTGTCATTAATTTTCTGCCTAGGACACCTCCCT
GGTTAAATTGCCATTTCCTTTCTTCCTTGCATAATGATTAGGAAACACATC
CTCCTGACCTGCCTGCCCTCTTTTGCCTACTTTTTCATCTGCAGTCAAGGT
CTGGTTTTAAGACTGACTGTTACTTTTACAAATCTGTGTGTATTGGTGGCT
AAGGGCCTGTATGGTCCACTGCTGTATTCCCAGGTCCCAGCATGGTGCCTG
ACGCTGCCTGGCAAATAGTAGTCACCCGAGAAATGGCTGATGAATTCATGA
GGCCTACTCTGTATGGAAATTTCAATTCTGGCCCCGAATTTTCAGGAGCTG
GCAAGAGAGCCACCTTAATATCATAGGCTGAGTTGGAAGAAGGGAACACCC
AATTTATTCTTAAGAAGTACTTTGCCCAGGTACTGTGGCTTAGGCCAGTAA
TCCTAGCATTTGGGGAAGCCAAGTTGGGCAGATGGCTTGAACCCAGGATTT
CGAGATCAGCCTGGACAACATGGAGAAACCCCATCTCTACAAAATATGTAA
AATTTAACTGCTTGGTGGGCCTGCACTTCTGGTCCCAGCTACTCCAGGGCT
AGGGTGGGAGGATTGTTTGATCCCTGGAGGTCAAGGCTGCAGTGAGCCATG
ATCACAGCAATGCGCTCCAGCTCTGGGCAACAGAGCGAGACCCTGTCTCAA
AAAAAACAAAAATGCCTATACAATAAATCTATAAAAAGTGGGTTTTGTGTG
TCTATACACACACACACACACACACCTGCATAGACACTCAGGTGTTCTG
GAAAGACACAGGAATCTGAAGCCAAAATACTTGTGATTTTTTTTCAGCTCT
GCCACTCACCAAATGTCTGATGGGATTAGTTACCTGCCATCTCAGAATTTC
TCTTCTGTAAAATAAGGTAATAGTACCTCCCAGAGTTATGAAAAACTATCA
AATGAGATGGCAGATGAGAAAACACTATATTCCTTGTAAAACCTGACAAAT
ATGTGCAAGATTATATAAAGACTGTCTTCTGTCCATTTTCAAATGTGGAAA
AGTGAAAGCAGGACAGGATGTTGGGATTTCTGTCAGAGATTTGCTGGCTTC
CACCTGCAGAAATTGAAGTAATTGGGGTTCTTACACCTAAGTACTAACTGA
GTCTGGTTGCAGTTTGCCCCCATGGCTACATGAAGCTTTTAGAAGAGTCAG
CATGGTAGACATGGAATGTTGAATGGTGGTGGAGTGTACCCACACACCTCC
CACCAAGTCAGCTCCAGGTTCAGAAGCAGCAGCCCCAGTGGAAGGCATGCG
TGTTTGTAACTCAGCTGAGCCACCTTTCAAGAAGCAGAAGCTTTCCAAACA
GGGATGCCCCCTGCTTTTGGTTCAACTTGACTTCCTACCTTCAGTGAGGAC
ATGGAGAATTCATCTAGACTGGGTACCTGAGCAAACTTGGCAGAGCAAAGA
GAAATGTGGAAGGCCCTAGGTAGACAGGCCCTGTGGAAGGAAAGAATGAAA
GAGGACAGAAAGAAACTCCCATTTTCTTTAGCACAGTCCCTTCAGATTAAG
GATGAAGAGGCTGGGGTTCTGAATTGGTTGGCCTTAGGTAATGGTCACAAA
AACAAGTCAATGGCTTTTCCACATCCGTACATTGAGATATATTTCTGCCCT
TGGTATTCATTTTCTCTGACCTCCAATTAAAGATCTATGCGTCATTTTAAA
GCCTTCCTTCCTTTCTACTCTGTGGTCAGCGTAACATTGGTGGTTTGAAAC
TGGCCATAATAGCAGCATTTACATCATGGGAACTAGCATATGTTACATCAG
GGTTTTTTGTTTTGTTTCTGGAGAGCCAGTAAACATACATCGTCACACCA
CTTAAATATTCTCTGCTTAAATATTCTCTGCTC
```

FIG. 8-106

>HLA-H.CONTIG
TTTGTAAGTATTCTATTTTATTTATATGTGTTTGTGTTTCTGAGTATGTCC
TGAGTTGCACGATAATACTATATTTCTTATTGGGTAACATTGTCAGAAAAG
TTTCTAAAAACTTTCTCTGCTGCACTTATTTTATACATTTTATTTATGTTA
ATAATCTCACATTTAACACACTTATGATTTATTCTCAACAGAAAAAGGTGG
TATTTCTTTCATTTAGTCTTTTAAAAAGCTCACATTATCAAATGATTGCTC
AATCATTTAATCTCTTTGCTTCTCTTATATGCATTGATTTAATAAATATGT
ATACTAGTTTCTCCATCGATTCTTTAGATTTGAAACTTATTTTCCTTTTAT
TCTTACAAAACTGACTTGTCTATAGGCCCACTTCTACTTCCTTTATTCTAT
CATCTTCCTCAACTTATTCTGTGGTCAAAGAATGGAGAAATAATATTAATA
ATATGTTTTTCTCATCAATGACTTCCACCTGTTCTCTGAGAAATTCAGCTT
CAAGAACTTTAGTTTGATATGACTGCAAAGATAATACACAGTCTAAATCAT
AAAAATGTCTCAAAGGTTTTTTTTTATTTGTTTCTTTGAAATATCCATGA
ACAGGCATGTTTCTCCCCCTGTAGTGCAATTTGTGTGAAATTCTGGCATGC
ACTTAAGAGGATGTCCTAAAATACCAATATTTAATTGATTCTAAGTCATGT
ATTGTATCACATTTTTGCCCATGGATTGTTGAAATCCATGGACAAAACTGA
TAGCATTTTAGAACTTCCTTTGTCTAGTGGCAGTCTTGATATATTCACACT
ATCTATTGACAAAAAATCTAAAGCACCAGGCTCAAAGCTTGTAGAGTAGGT
GTCAGTGATTTGGAGGACATCTCTAGGGCAATAGTAGAGGCATTTTTAACC
CCTAACAACTAAATGATCATCAGAAGTGAGTGATATCCTCACTCATGACCC
CAACTGCTCTAATTTCTATTGTTTTCTTGCAGAAATGAGAGCAGGTGGGGT
CATGGGTGAGGAATGAGGTGTTGAAAGTGAATGGGGTGTTGAAAGCAAGGT
GTTTAGCAGTGTTCTGAAAGCATACATTTAAGTAGGCTATCCGGGCACTGT
CAATAGCTAAGTGTCAAGCTAAGTACTCTATTTTATTCTAAGAACTATTTT
TAGAAATGCTGAATCAACAAATCTCAGATGGCACAGAGGTTGTCATTTTTG
AATAATATGAATATCAGTAATTTTAGTTGGAAAAGAAGATTTTCAAAGAGC
CATCTAAGTTTCCAAAATAAGTGTTGCAGTCATATTAACTATTATATTTTC
CTGCCTGTTGATCTACTGCCTGTGAATTGCTTATCAAACCAACAACCAACT
GGAATACATAGACTGCATGTCTTGTTCATTTCCTGCATTCTCAAGTAATGG
TTTAACAAACTCATGAGCTTACTCTTTAATCTGAACCATGCTTAACTTCAA
TTATGTTGATTTAGTCTAAGGATGCAGAATTTATTTTATAGTTATGTAGGA
ACTGGAATCCAAAATGTAATATGCCTCCAAGCTTTTCTTTGTTGGCCTCTG
AAGGAGCATCACCTCTACAACTTCAACGTTGTTATGAATACCTCTGGGGAG
GTGTTCACCTCAGGACCCAAATTTGGAAAAAGGGAAGTGCCACTTTGGAGG
AGTGCTCTGAGCAGCTGATCCATTAAATGTCCCGATCACATGCACGTGGAA
GTGTCATTGCAATATCTGCACTAACAGAAGCTCAGTGACTTGAGAAGTGAG
TCTGGAATTCTAAGAAAAAGGCAAGGCATCTCTCTTGCCACTTGTTATTTT
TCCAGTCAAGCAACTGTGATAAGAGGGCATGGAGAGCAGGAAGAAGTGAAA
AATCCCAGGAAAGTCTGGAGTGGAATCATTAAACCAATTCTGCTCCCTCTC
TAGGCCAACTTGGGCCTATTATGAATAAGGAGGTCTCTTATAATCCATCTA
ACTCCACTCAGGAACAATTTGGGGATCTGAGACTGTGAACTCAGTGGGCAA
AAAAATATTTCTTGGCCTATCATTATTCTCTGTAGGATGTTAAGGACAGGT
TTCTGTATGTGGAGTCCTCAGTTTTTGCCTTCTCTCCTTGAGATATTTTTA
TGCTATTTAGTAATTGATGGCCACAGTTGATCGACCACATTTCTGGGCAAC
TCTAATAATCCTTGTTATATTAATCATTGGACCAATCTTGATTGTGTATGA
CCATCATCTTGTAGCTACCACCTCTATGTGGATGCTCTCCTCACCCTGCTT
AAGTGCCAATGTCTGTGCTATGGGCCTACCTGTCACATGGATAATCTCTTC

FIG. 8-107

```
ACTCCAGTCAGGCTCCAACATTAACACAGGGCTGTTCTCTTGTCCCCCTTT
GAAGACAGCTTCATCACCCTATTCAAGTTGCAGTACTCTCACTGGGCCTCC
ACTGTTGCCTCTCTCTCACTCTGCTTAGGTTTCTTCACTCCACTCCAGGCA
ACTGTCACTAAACATCCTTTCCCCCATATATAACACAGACATCTACCTTGC
TTGGCCAAACCCACTGGATTTCAGACTCACTCATTCAGAGAGTAAGACAGA
GAGGGGTTCATTTTTTATTTTATTTTATTTTTTATTTTTTGAGACGTTGTC
TCACCCTGTCGCCCAGGCTGGAGTGCAGTGGTGCAGTCTTGGCTCACTGCA
ATCCCCACGTCCCAGGTTCAAACGATTCTCCTGCCTCAGTCTCCCAAGCAG
CTGGGATTACAGGTGCCTGCCACCATGCCCAGCTAATTTTTGTATTTTTAG
TAGAGACAGGGTTTCGCCGTGTTGGCCAGGCTGGTCTCGAACTCCTGACCT
CAAGTGATCTACCCGCCTCGGCCTCCCAAAGTGCTGGGATTACAGGTGTGA
GCCACTGCGCCCAGCCGGGGTTCATCCTTAATACATACATTAGAGATATAG
ATTCTGTTTTTATCTAAAAAGTCTTTATAAGGCCGGGCGCGGTGGCTCACG
CCTGTAATCCCAGCACTTTGGGAGGCCGAGGCGGGCGGATCACGAGGTCAG
GAGATCGAGACCATCCCGGCTAAAACGGTGAAACCCCGTCTCTACTAAAAA
TACAAAAAATTAGCCGGGCGTAGTGGCGGGCGCCTGTAGTCCCAGCTACTT
GGGAGGCTGAGGCAGGAGAATGGCGTGAACCCGGGAGGCGGAGCTTGCAGT
GAGCCGAGATCCCGCCACTGCACTCCAGCCTGGGCGACAGAGCAAGACTCC
GTCTCAAAAAAAAAAAAAAAAAAAAAAAAAAAAAAGTCTTTATAAAAATCTG
ATTGAATGGTTGAATGCTGTGCTAAAATCTGCATAATATCTTACAACACTT
CTGTGAATCACGAGACAGTTTTGAATGCTAAATGTCAGTTAACAGATCTAA
AGGGACCAACATCTGCTTTCCCAAATTATATGAAAGAAGATCCTGATCCCT
CATCAGGTGAAACTCACATCAGACAACAGTGTCTGCATTTCTCCAAAACCC
GCCTCAGCCCCATGGCCACTTTCCAGGGTTATCCTGCCTACCAAGCACTCT
CTTTCCTCAGAAAAACTTGGGGGAAAATGTAGAATAATAATTTTTTGAAGT
TCTGACCAACTTCTTGAATCACTCAGCATGTTTTTGACTGCAGGTACAGAA
AACGCTGACTCAACAAATTTAAACACTATATAAATTTCTTATCTCCCCAAA
CAGGACATCAAAGGCAGAAAGGTTCCAGAGCAGGGTGATCAGAGCTCTGGC
TCCACTGCCCTCAGTCTTCTTGCCTCTGCTCTCCTTCACAGCAGGCTTTAC
CCCCCATGCTGGTCACAGTTTCAAGTGTCCATGCAGACACAAGTTAAAGGC
AGGAAGAAACAGTGCGTTTCTCTTGGAGATCAAGGAATGCCTTTCCAGAAA
ACTCCCCCTTATGTCTCATTTGCCAAAACTTGGCCTAGTCTCAGGTGCTGC
CTGAGCTAATCAGCTACAGAAGAAGGGACCACATGACTGGTGTGGACCAGT
CAGAATTCACCACATGAAGCTAGTAATGTGGCTCACACTTCCAGGGGGAT
ATGGCCAGGTAGCAGACAGTGGATCGCTGAACAGAATACTGATAGATTTCA
GCACCAAGGTTAGAATGGCTACCACACCTAATCCCACCCTATCCCCGTTTC
CTTCTTTAATTTTTTCCATAGCACTTATCAGTAGCTGACAAACTGTATATG
TTTTTACTTTTTTATTGTCTGTAGCTCCCAAGTAGAATACAAACATCTGAA
ACTCACTGTATCCATCCTGAGTAATGTTCTTTTCAGCTCAGTCACAATCAT
TTTTTGATAGCCTATCCTATAAGCTTAACTTATAGTGTTAATCAGTATTAA
TACATCTTAGTGGGAAAGAAGGAAAAAATAAACGATCACACACACACACAC
ACACACACACACACATACATTTACGTAACAGAGCAAGTGTGAAAATACC
TAAAGGCTTTATAGCTCCTTTTGTCAATGGATACATGACAGCATTTTTGGC
ATTCTTTACTACTCTTATTCTATGCTCCATTTGTCTTCAGTCAGCACCTCA
GCTGCCCTTATGTTTTACTTGGTAAGGCAAATTCCTAAATGAGCCTGGTAA
TTAGTCATCCAGCTTATAGGAAGGTACTATAGTTTTTCATTAACTTTTTCA
```

FIG. 8-108

```
CTGGGCTTGAGAGTAGTAAGGACTCCCAGAGAATTCCTTGTGTTCCAAAAG
TACTTCTCCTTGACATCTTGGTATAGGATTAATAACTGTTTACCTTTGATA
ATCAGGAAGAATGACTCCAGCTAGTACAGTTACGTGATGCCTATACATTCC
TTTTTTTCTGGGAAAAATGTAATGTGAAATTAAGTGCAAAAACCATGCCTT
GTTTATGTATGTATCAAACACTTCTAGAGCTTTCCCAATACAGTTCTCTTC
TCAGCAAACAAGAGGACTATACCCTCATCCCCACCCCTGCACTTAGGTGTA
GCCAATGTGTTGTAACTTAAAGAGGAGAGGGCACTGGATGAAGGGAAATCT
GTCTAACAAGCTTCTTTATTTCACCTAGTGGAAAAAAGCCTTAATCTGCAG
TGGGGCAGTTTTCAAGGACATAGACTGAATTGGCTCATGCATTTATGGAAG
ATGAGGAGTCCCATGATCTGTAATCTGCAAGCTGGAGACCCAGGAAAGCTG
GTGGTATGATTCAGTCTGAATCTGAAGGCCTGAGAACCAGAGGAACTGATG
ATGTAAATCCCAGTTCAAGAGCAGGAGACCAGATGAGATGTCCCAGCTCAA
GCAGTGAGGCAGAAAAAAGGCCCAAATTCCCCCTTCCTCTGCCTTTTCTT
CTATTCAGACCCTGAATATCAGGTGGCATAATGCCATCCACACTGGGAAAG
ACAGTTTACTTTACTAGGATCACCTATTCAAAGGCTAATCTCATCCAGAAA
CACGCTCACAAACACAGCCAGAAATAATGTTTAACCAGATAGCTGGTTATC
CCCTGACTCAGTCAAGTTGACACAAAAAATGAACTATTTCAAAGCTTACTG
TAATCAACAGTTTTGTCAAAAAGATAGACACAAATCAGTGGAATGAGATAA
ACAGTCTAGAAATAAACCAACAAAAATATTGCCAACTAAGGCAAAGGTAAT
CAATGGAAAAAGATAGTCTTAGCAACAAATAGTACTGGAACACCACAATG
TGTTAATAAAGTGAAACTGGAGACATCTCTCACACCTTATACAAAAGTAAC
TAAAAATAAATCAAAGGACTAGATGTAATGTATCAAACATTACATCTTTTA
GAATGTATCAAACATTACAAGCTTTTAGAATAAAATATAGAAGAAAATTTA
CATGATCTAAGATTTGGCCCCAATGAAGTTTTAGCTATAATAACAAAAGTA
TTAGTCATGGAAGAAAACAAAATTGATAAGTTCAGGTGGGCTAAATTAAGG
GAAAAAAATCACTTTGCAGTAGAGAAACCTGAAACATTACCTAAACCACAT
GATGAAGGTTAATATCAGTGATGTCATGTGGATATCATGTTCTCCCTAAAA
TGATGTGACAAGAAGGGCCCTTTGCCCTTGTGGTATTATTTCAAAAAATCT
ATAACTCCGGTGTAATTATGAAAAAAAGCAAATGATCTTCAGGACTGTTA
AGGTCATGAAAAGCAAGAAAAGACTGAGACATTGTCACAGACAAAAAAAGA
CTAGGGAGATATGACAAGAAAATGCAGTGTGGTATTCCAGATTGGACCTTG
GAACAGAAAGAAAACATTAGTGGAAACAGTGGTGAAATCCACATAAAGTCT
AGGGTTTGGTTAATAGAGTTTCATGTATCAATGTGAGTTGCTTATATTTGA
CAAATGTATCATAATAATGTAAAATCCTAACAATGGGGGAAAGCTAGGTGA
AAGATATATGGGAACTCTCCTGTACTGTCTTTGTACTATCTTTGCAACTTT
CCTGAAAATCCAAATTATTCTAAAACAGAAAAGTTCATGCTATTAGAAGTG
AGGATAGAGGTTACCTTGAAGAAGCTGAGGTCTAGAAGAGACCATGAAGGG
TCTAATTAGCTAACACACGTTGAGTATCCCTTATGCTTAGAACCAGAAGTA
TTTCAGATTTTTTCAGATTTGGAATGTTTGCATTATACTGAGTATCTCAAA
TCCAAAAATCCAAAATCTGAAATATTCCATGAGCACTCCTTTGAGAATCAT
GTTAGCATTCAAAAAGTTGCCGATTTTGGAGCATTTTGAATTTCCAATTTT
TAGATTAGGAATACTCAACCTGAGTAGAGGCTGCCTGCTAATTACCTGGGA
GCTAATTACATGGATATGTCATTTTGAGAAAGTTTAGCTTGCTGATATGGA
TGATTTTCTGGATAAAAATTATACTTTGATAACAATTCTTTTAAAGGAGAC
AATAATTATTAACTTTTAAGTACTTTTTAGCTCTACAATTCAGAATTCTTT
AGTGCTAAATATTACATATTTTGAAACAAAAGTTTTGTTTATATTTATTTA
```

FIG. 8-109

```
TTTGTTTCCCCCCCCCTTTTTTTTTTTTGAGACAAGTTCTCACCTTATTG
CCCATGCTATAGTGCAGTGGGTGATTATAGCTCACTGCAGCCTCAAACTCC
TGGACTCAAAGGATCCTCCTGCCTCAACCTCCCAAGTAGCTAGGAGTACAA
GCATGCACCACCATATCCAGCTAATTTTTGTTTATTTCTACAGAGGCAGGG
TCTCACTATGTTGCCCAGGCTGATCTCAAATTCCTGGCCTCAAGTATCCTC
CCACCTCTGCTTCCCAAAGCGCTGGGATTACAGGTGTAAGTCATTGCACCC
AGCCAAAAGTTTTATTTTAAACTTATTATTATGAGCATGTAACAGATTTAT
GTGGTTTGAAATTCAAACCTACAAAAGAAAATAATAAAAAGCTAACAGATA
GACAAACAAAAACAAAAGCAAAACCCCACTTGGCCATGCTCTCTAGTTCCT
CATTTCTCTCTTGGAAGAAACCAGAGCAATGTTCCCTGTGTATCCTTCCAG
AGATAATTTTTTAAAATACTTTTTTCTTTTTAACAGAAGAGATGGTAGACT
ACTTCTTTTAAATTAAATTAATATACATTTACTTGTTTCTTTTTATTGCTA
TAGAAAATGAAGTTGGGGAAACAGGAAAAATGACCTAGTATTATCATACTA
ACATACCAAAATTTTTCAGTTATATGTATTTCCTGTTTCAGTTTTTACCCC
ACCTGTTTTTTATTTGGTTTGAAATCATAGTACAGATAAAAACTTGAGGCA
GGTATTTTAGACTTGTTTTTCTTTTGTAACATAAAACTTTGAGAGCACCAG
GAAATCTGGAAATATTCATTTAGTTATTCATAATTCAAAATATTGTTATAT
CCACTTTGTGTCAGACTATTTGTTAAGAACTAAACTAAAAGAAAAAGATGG
GGCTGGACATGGTGGCTCACACCTGTAATCCCAGCACTTTGGGAGGCTGAG
GCGGGTGGATCACCTGAGTTTGGGAGTTCGAGGAAAGCCTTGCCAACACGG
TGAAACCCTGTCTCTACTAAAAATACAAAAATTAGCCAGGTGTGGTGACAC
ACGTCTGTAATCCCAGCTACTCAGGAGGCTGAGGCAGGAGAATCACTTGAA
CCCAGGAGGTGGAGGTTGCTGTGAGCCGAGATCATGCCACTGCACTCCAGC
CTGGGCAGCAAAGCAAGATTCCATCTCAAAAAAAAAGATGATAACACCCTC
TGGGAGATTACATTCAGATAGAACAAATAAAGGTGTAGAACCTAAGATGTG
ACAAGGACACTGTTGGGTGACTGATTCTTCCTGGGAACATTTATAAAGGCT
TCCTAGGGGAGGGCGTGTTTGTGTAAGAGCTTTCCAGGTCAGAAAGTATGT
ACAGTGGAAAATGTATATGAAAAGACCGTGTTTGGGAATCAGGGATTATAT
ATTGTGATTAGAGGAAAGAGTCCTAGGGTTTGATACCTACAAAGAATTAGA
GTTTCTAGGTGCTTCTGGACATGTGGATTGATGACAGCAATACTAAAAATA
CAAAAATTAGTGGGGCATAGTGGTGAGCGCCTGTAGTCCCAGCTACTTGGG
AGGCTGAGGCAGGAGAATAGCTTGAACCCGGGAGGCGGAGGTTGCAGTGAG
CCGAGATTGTGCCACTGCACTCCAGCCTGGGTGACAGAACGAGACTCCGTC
TCAAAAAAAAAAAAGAAAAAAAGCAGGAGTTAGCAGAAAACCAACAAGAC
ATGGGAAGGAGAGAGAGAGCTGCAACACCCAAGAGAAAAAATAGCAATGCT
GAAATCAAAGTATAATGAAGGAGAGAGGATGCTGGAAGCTATGAAATTCTT
TCTGTGAGGCAATGGGGCAATGACCCTAGAACTGCTGAGTTAGCAGCAGTG
ACAGACTCAGTGCCAAATCATATATTAGAAAAAAAAAATCAGATAGAGGTAA
AGTCCAGATCCAAAGAAGAGGGTTTTTAGCAGTAAAGCAGACAGTAGAACC
CACCCAGCTTTCTAGGGTGCAGGGGCCTCCCTTTCAGGCATCATGAACAG
TGGGGGACCATAACTAGGCATGATGGCTTCAGATACAGGGCTTGTTCATCT
CTTGTTGTGGTCAGGCACTGCCTAATGAGAGCAACCCCTTCCAAATGCTAC
TGCTGTGTTTAACTAGGGCTCTTGATAATCTGACCAGCTTCTGTCTTACTG
ATTTTAGGAGAAAAATGGAGCAACCTGCAAGATGAGTGGGATTAGCTTCGT
GCTGTCTCCCATGCACACCACTCATGCACACTTGGCGAGCATGGCAGTTCC
ATTTATTTTGCACCCAGTTGTGATTTAAAAACTTTTAATTAATTAGTCTTA
```

FIG. 8-110

```
TTAGTCTTCAGTTGGATTTAAATGCCAAATAATAACCTTCTACCTTGTAAG
AGGAGCCCTTTTACCTAAAGCAAGGCTTAAGTTTGGATAAATTTTGTCCTA
TTTATTATTCATCCACAAGCTCTCTTAAAACACTGAATACACACTAAGAAG
GCTCTCAGCACTCCGAATAGTGTGATAAATCAAAAGCCAGTAACTTCTCAA
AGTCATTGTGTATTAGTCAGGGCTCTCCAGAAAAATAAAACCAATAGAACA
TATATACATGGGCTTTTACCCAAATGTCATCTTTTCAATGAGTCCTCTTGC
CTGCTTAATTTTTCTTTTTAGCATTTGCCACCTCCATATAACATGCACTTT
ACTTATTTATTGTCTTATTCTCTTTCACATGGGCAGGGGTTGCATTTGTCT
GTTTACTGCTGTATCCCTAGCACCTAGAGTGGTGCCTGGCATACGGCTGGT
GTGTGATACATATATTTGGAGTGGAGGTAAAAGTCACCACTTAGGCTATCC
ACTTTTGTGACAGGGACAACACACGTATCACTTGTCATTGTACCTATAGCA
TCTCACCCAGAGCCACAAAAAAAGTGGCTCAAAGTATATATTAACAAAGAA
CAAAATGGAATAATCCCATCTGAAGGCGAGGATATAATAAAAGCAACATAC
CTTTTTTTGGAAGGACATGGAGAGCATCAACCTTAAGACTAAAGACTAAAC
TTGAGAAGCAATTATTACATTTCTATTAAAAATTACCAAATACAAATAGTT
AACTTTGAAGAAATATATGAATAATGATGGTATCTGCAAAAGAGGAAAAGA
CTTACTCAATTTCATTGTACCTTAGTTGTAAATAGTATTCAGGCCACCATT
TGGAACCTATGTGACACAGTTTAGTTCCTGTCTATGTTCATAAGAGAGGGC
AAAGGCCCGTTTACATCCAACCTCTGTATGCCAGCAGCCACGTATGCCACA
CTCTAAAATGGCTAAACAGTCATTCATCAGAATCGGTTCCAAGAACTCCAA
CAAAAATTAGAGCTCATGGTGCCAGATTGGCCTGGATTTTCATGCTCCTGG
GTGATTACAAAGTTGTAAATAATGATGCTGTCCACTGATTTTCATCATGCG
GGGCTCTCTGCTTCACTGTGCCTTCCTCTTATGTCCATGGCACCAATTTCT
CTGATAGTTCCCCCAGGGGATAGGGTTAGATGTGGGTTCATAAGCGCTGGA
CCACTGAGGGTAATTCACTCTTAAGACTAGCGAGCACTTTCTGAATCTGAG
GAGTCACATATTAAAAGAGGCAGAATCATCTTCTGATTTCAAAAAAGCAAC
TACATGACCACCCTGAAAGTGATTTCAAAACAGTTGAAAGCTAGCTGTTCA
AGTTGATAAAAGCCACTGCAGTTCCCTGCAGGGAATGCTGATGGGCTCCGT
TCCCTCTGCACATTAGAGCCATTTAAATGAAATAATTGATCATATTAACTG
AAATCACCTGGCTTATAGCTCAGGTCCTAAGAATTGTTAGTGGCACTTGGA
GCTACAAAGAGGAGTCCCCAAAAGAAACGATTCTCACTTTATTTTGGCAAA
TGGGTGGCTTAAGTAGAACTGGTCCTATTCCATAACAATAAAAAAGGAAAA
AATAAATTTTATATAAACTTATTTCCAAGATTTCTTACCCCTTCTTGTCAG
CATTTCAACTTTATTTGGTGGAACTATCTTTTCTCAATTATGTGTGATGTA
TTGTGGTCGTGAATCATGGTGTCCTGAACTCCCTTTGGAAGCTAAAACGGT
CTGTTGAGGCTCTGCCTACCAGCTCTCTAGGGTTTGTTAAAGCAAAAGAGT
GAGCACTTTACTTAAATTTCACCAATTATATTATCTTCTGAGACCTTAAAT
GTTGAGTAGAGGGAAAATACAAGTTCAAGCCTATTTATTTCAACAATGGAG
CAAGTTGCTACAGCTAAGACCTTTTGAGGCTGCCTGTTTCTTCAGGTTTTC
CTTTGATTCTCAGAGTAACCCCACCTCAATTTATTTGAATACATGTACTTA
TGGCTTAACCAACACACAGGTGGTTTCTTTAACTACAGTGCAAAAATCTTC
ACACATACAAACTTTTTAAAAAACAATTCTCAATATGAAAAAGAGAAATCA
ATATAATTGGCTACAAATTATTGGCATCTTTTCAGAGATTTTCTCAAGAAA
GTAACTGAATTCCTAAAATTCTTATGACTTTGTTAAAGGACTCAAAATGAA
CATATATTCTGGCTGGGCAGGTGGCTCATGCTTGTAATCATAGCACTTTGG
GAGGCCAAGGATTGTGGATCACTTGAGGTCAGGAGTTCGAGACCAGCCTGG
```

FIG. 8-111

```
CCAACATGGTGAAACCCCGTCTCTACCAGAAATACAAAAATTAGCCAGGCG
TGGTAGTGGGTGCCTGTAATCCCAGCTACTTGGAAGGCTGAGGCAGGAGAA
TTGCTTGAACCCAGGAGGCAGAGGTTGCAGTGAGCCAAGATTGCGCCATTG
CACTCCAGCACGGGCAACAGAGGGAGACTGCATCTCCAAAAAAAAAAAAAA
ACAAAAACCTCATATGTCCTACAAAGCAAGTGATAAAAATCAAAATATGAC
AATGGGCTGAGAGGAAAGGGAAACTAGTAGTATTAAAGAAAGTTTTTAATG
AACAAATAATGTTAAGGCGGATTTTTTTGTTTGTTTATTTGTTTTTGGCCT
TTTTTTTTTTTTTTTTTTTTTTTTGAGACAGAGTCTCACTCTGTCGCC
GAGGCTGGAGGGCAGTGGCACTGTGTTGGCTCACTGCAACCTCCGTCTCCT
GGGTTCAAGCAATTCTCCTGTGCTAAGGCAAATTTTTAAGGATTATAAATA
GTAAATATTAGAAGGGATACTGCTTAAAAATAAACAATTTGGATAGCTAAA
TGGTCTTCAGACTCTTTTGATTGTACAACATGTAAAAGAATTTTGAAAACT
TTAGGCATTCCTTTGAATATTTTTAACTTGATTTCTAAAACTTTTCATCAA
AAAATAAATTGTTTTGTAAATAAAAGAAAACATTAAACATGTTATAAGATG
AAATAAGATGAAGAGTGACTATAATTAGAATAAGTATTTCATGACATAAGT
TTATTTTAATAAAAGTTCTAACCACTTTATTGTATCATTCATATCAAGTTT
TTTAAATATATATTGAAATTTGGTGCTCTGGGAAAATATGCCAGCTTCATT
TGAAAGAATGAGTTCCTATCCTGTACTGCTTCAGTTATTCTGAATTCAGAA
CATTCCCACTCTGGCCAGTCCTCTCTTATAATAAAACATACAATACTGTGC
ATATTCTCAGTGATTAAAAAAAATACACACAGCAGATAAAAGAAGAGGGAG
CAGGCAAACCAAGAGCCAAGGTGAATGTGTTAATCATTAGCAGGTTATCCC
CAAACCAATATTTGGAAGTACTCCTTTGTTGACAACCAGGAAGTGTTTACA
CTTCAGGCATTGCACCTAAATAAAGTGTGGATGCCTTTCCTTTCTAAAGTG
GAAGGAGGGATATTGTGGACATAGGCACATTCTGAGGCAATTTTAGGAAAT
AAGTTGAAATTGATGGAAATTGAGAAAGACTTTGGAAAGTGTTTGCCTGCC
TCCACTACCAAAAAGTCCATGGAGAAAGCAAAGTAAAAGGTCCAAAAATGA
AAGTCAGCAGAAACCAGAAAGATGGGCAACAAGGTTTTACCATACAGATAA
ATAGAAGAGAGATTCTTAGTAAAGAAAACAAATTGAGGACAATCACTAAAT
AAAACAAAATCGAAGGAAACTCTAAGACCACCAGCCAAAAAGCAAGAGAAA
ATGATTAACACCTTGGCACATCTTGGTGAAGGAATTCCAGGATAAAGAGAA
TCCTATAGCACCTAGCCTAAACATAGCTCTCCTACAAAAAGTAGCTGGCTA
ACTAGACTTCCTCATATTGGACATCAGAAGAGACTAGCAGGAAGTCAATAC
TGTTTTGAATAAGACAAATTGTGGAACAAAATTTCTGTTCCCAGCTAAGTT
AATATTACAATGTTTTAAGGCTCCACAGTGATCATAAAGAGTACTATGAAA
TAAATTCTCAGCTACTGTGGGACTCAGAGGCTCATCCAAGTACTGCTCCAA
AAAAATACTCCATTGAAATGTTTTGAGATGAAGAAGGATAAAGGATGGACA
TGAAAAAACAAAACAAAAACACTTCATTGTCCAGGGGTATGCTAAGTGAG
CAAGAAGTGTCCAGCACTCAAAATTAAGGAGGCACTCACTCTCATGTGCCA
ATTCTGTTCTTGCATGAGCCTAAGAAAGGATGCCTCCTTAAATATTGCTTC
TTGGGCACCTCACTTGCCTCATCTTGGTTTCAGCCCTCAAATTATGTTCAA
ATAACAGTGAAAAGTATAATACCCAACAGAATGCAAATGGTATAATTCTTC
TATGGAAACTACTCAATGCAAAATTAATACATTAACTGCAAAAGGTCAGAG
CAAAACTTCCAGAGAACAGTAGTGAAACCAAGAGTGAGATGATAGGATGCC
TCAGTGTGTCTGTTTTCTTATTATATATAAGGAGAGAGACATGGCTAGGCA
TGGTGTCTCATGTCTGTCATCCCAGCATTTTGTGAGACCAAGGCAGGAGGA
TCCCTTGAAGCCAGCAGTTTCAGACCAGCCTGAGCAACACAGCAAGATCCC
```

FIG. 8-112

```
TGTATCTACAAAAAAAAAAAAAAAAAAAAAAAAAGCTGAGAGTCAACAGCCAC
TTTTTACTATATAGGTTATTAACTTGAGAAATAAAGCATTAAAAGAACAA
TGAATTTGGGAGCACAACACAGCAAAATGTAATCTGCCCACAAAATTGGAC
TTAGAGGAGCAATTTTCCTCTAAGCTTTAACCTGTTTCATAATTAAATGAA
AAATAAATAAACTATCCAAAACAAAATTTATATGAAGTAAAGCAAAGGGAA
ATAGGACATAAGCTTGATAAAAGATAAAGCTAATCAAATATAAAATAAAAA
GACAAGCAGGGCTGGGCGCAGTGGCTCATGCCTGTAATCCCAGCACTTTGG
GAGGCCAAGGTGGGTAGATCATCTAAGGTCAGGAGTTTGAGACCAGCTTGG
CCAACATAGCAAAACCCCATCTCTATTAAAAATACAGAAATTAGCCAGACA
TGGTGGTGCATGACTGTAATCCCAGCTACTCGGGAGTCTGAGGCAGGAGAA
TCACTTGAACCCGGGAGGCGGAGGTTGCAGTGAGCCGAGATCGCGCCACTG
CACTCCAGCCTGGGTGACAGAGTGAGACTCCGTCTCAAAAATAAATAAGTA
AATAAATAAAAGACAAGCTATTCTTAAAATTAGTAAATGACTAAGTAGTCT
AATGAAGGAGAAAGAAAGCACACATGCAATTGGGTCAGAAGTACAAAGAAG
CTAAAACCTCAGATATAGATAAAATGATATATTATTAAAAAGATAGCCTGA
TAAAACAGTTGAATTTTTGCAAATATACTTTAAATAGTGTGTAAAATAGAT
GATCCTCCAGATAACATAAATGGTCCAAATTGATCAAAGAAAAATATAAAA
CCCCTTAAAAGACCAGTAACTGAAGGAAATTGAGAAAGTTATCAAAGTCTC
CTCAAAATGGCTTTCAGCCTGCATGATTTTTACAAACCAATGCTTTCAAGC
TTTCAAATAACAACAGCAATTATAAAAATTCCATTCTAGTCAATCTTTTTC
AGAGTAATGGGGAAAAGGAAAGTTCTCCTTTCTTGTTTTTGAAATCAGCA
TAAGCTCCATATCCAGACACAAAAAAGATACACAAAACACATGTATGCATA
CAGAGCCAATCTCATATATCAGTACATCAGCCAAAGTCCTAAATAAACTAT
TAGTGAATCAAATTCTGTCGTACATCAAAAGAATATTCAAGGGAAAGCTCA
ACATTAAGAAATACATTAATATAATTCATAATATTTAACAGTCAAGGAGAA
AAAGTAAGTCATCTCATCATTAGGTAGATGACAATAAACTATTTGAGAAAA
GTGAATTAATTTTCATGACTATTGTTAGAAACAATCCTTTAGGGATGGGGA
GGGGAGATGAATTAGAAATGTTTCCTATCAGTTCACAATTGCATCTATTCT
GAAGCCATTAGGAATGTGAATGGTAACTCTTCCTCAAACCATCACATAAGG
AAAGATACCCTGAAAGTCTGACACACCGAAGTCATCTGTCAGGAATCAATC
AGAGAAGCTGCTGGGAAAACCTCAGAGAAGCTGCTGGGAAAACCTAGGCAT
TCTGAGTCATCATTGTTCTTATCACCCGTGGCAACTGATGCAATTGGAAGC
AACTGATGCTTTCAGGGTCATGGTTTCTTCAAAGCCTGAGCTCATTAATTT
TGCTGTTTGAGAACTTGCAGTTTGATCCAAAAGCTGACAGCATCGATTGAC
CCATTGCCTTCCTTCCTGCTCTGATACTGGAAGTTCCAACAAAAGAGGAGG
AGGAACAGGACCAAGAAGAACATGAAAGCAGAGGACCAGGGGCCGGGCGCG
GTGGCTCACACCTGTAATCCCAGCACTTTGGGAGGCTCAGGTGGGCGGATC
ACGAGGTCAGGAGATCGAGACCATCCTGGCTAACATGGTGAAACCCCGTCT
CTACTAAAAATACAAAAAATTAGCCGGGCATGGTGGCAGGTGCCTGTAGT
CCCAGCTACTGGGGAGGCTGAGGCAGGAGAATGGCATGAACCCGGGAGGCA
AAGCTTTCAGTGAGCTAAGATCGAGCCACTGCACTCCAGCCCGGGCGACAG
AGTAAGACTCTGTCTAAAAAAAAAAAAAAAAAAAAAAAAGCAAAGGACCG
AAGGACCAAGACCCCTTCCCAACTGCTCCATTGGTCAAAACGAAGTCAGAG
CAGAAGCTCTCAAAAGGATGATACTTTGAATTTGCTTTCTGTTTTATTTTC
TACATTCATAAACGTGCACAAATCATAAATGTACAATATTCACAAAGTAAA
CACACATCCAAGTCAAGAAATAAAATATTTCTAGTACCCCAGGAGCACTTC
```

FIG. 8-113

```
TTAAGTACCATCCATCCAGCCACAACCCCCATCCCTGCACAAGGGAAATCG
CTCACTGATTTTTAACAGGACAGATTGGTTGTAGCTGTTTTTAAAAAGTAT
TTTATAAACCTTTAAAAGAATGTGCGTTTTGTCTTCCTTTAATCAATATTG
TGCTTATGAGACCCATTCATCTATTATATATTGGGGTCTGTTAATTCTCAT
TGCTATACAAATAGACCGTGGTTTATTTACTCATTCTTTTTTTAACAGACA
ACTTCCTGTTCAGGCTATTACAGATAGTGCTCCTATGAACATTGTTGTACA
TGTTTTATGGATGTATATGTGCATTTCTAAGTAAAATGTTTGAGTCACTGG
AATTGTACATTTAGCTTTAGGAGATATTGCCGAGCAGCTTTCCAAAGTTCA
CATTCGTAACGTATGAAAGTTCCAGTTGCTCCACATGTCTGGCAACATTTT
GTTTTCCATCTCCTTTCATTTTATCCATTAGTTAATTTTATAGTGGTATTT
CATTGTAGTTTTGATTTTCATTTCTGTAATGACTAATGAAGTTGAACATCT
TTTTATATGTTAAGGAGCCACTTACATTTTCTCTTTTATGAAGTCCCTGTT
CAAGTCATTGGCCCATTTTTTAGTTGGGTTGTCTGTCCCCCACCCTTTTTT
GTTTTTTTTTCTCTTTTTTCTGTACATAATTTGACTACCTATTATACTAT
GTCTTTCTTTTTCTTCTACTTCTTCTTTTAGTTTTCTGCAAACCCCCTTT
CCTCTTTGTGTTGTCAATATCATGAAGGCAAAATCAATGTTCTCATCTTAG
TACCACCCTCAGGGCCTGACACTCTGTTTTTCTGAAAAACTTGCTCAAAAA
TACCCATTGATTTGCATTAGGAGATTCTCTTCATCTGCTGAATTAACCCAA
GGTTCTTGTCCAAGCAGTTTTTTAATAGGATTTAAAATATGGTGGGAACTT
CTTCTCTAGACATGTTGTGGCAAAACCAGAATCAGTTCTGTGTGAGGAGAC
AAACTAAAGGATATGTCTTAAGTGTTAGGAGCCAAATTAATTCCTGTTAGA
GTTGACGCTGCCTATCTGAGTATCTTGGGAAAGTAAGAAAAATATGAAGAA
GGTTAAATTATCTTTTTCTACGCTCAAAAGGAACTTCTCTTGTATGTGATA
CACTTCTATGCCTTGTATGTGATACATTTCTATGCCTTTTCTCATCTTGTT
ATGTCTTCAATATTTTTCTCCCCCATATAAATTGTCATTTCACTTGAAAGT
GTCTCTGTCATCTCTCTCCAATTTTCATTATATGGTCTAAACTATATTGCT
ATCCCTTCTGGAAGTGTCTACATTGCCTTCCTTCACATTCATTCTTCTCAC
AATACAAGCCTTCCAGTTCTATCTTCTCTGTCCTTGATTTCTAAGTTAACC
TCATTTATTTAATCTTGTATTGGTCATTTTCTCATCATTAATCTCTTGCAA
TTGGGCTAGGATAAATAAATATCTGTTTAATCTGATGGAAATATCTGGATC
TAAATAATTTGAAAATGGTCTATTTTATTTTAGCATGTAAATTTTAATAGA
ATTTAATCACATAAATAAACGTCTATGTTTTACAATGTATAAAAAATAATA
AAAACTTTAATTCTGGGGATTATAGCTTTACAGTTCCGATCGGTGCTGAGA
TCTGTAACATATGGCTACAATTCCGAGCAGATCTTCTCTGCATCCAATAAC
CTGCCCCACCATGAAGATATTTATCAGTGATCATTTTCACATGAATTTTTA
TTTATTTAGTACTTTCCAATGAGGAAAATTCAAAGGCCACATGAATTGACT
TTTCAAGTTTGTCCAGCTGTTGTCAACCCCGGGCGCATGCTAGAAACCTCT
AAGGAGTATCTAAAAATTAGTAGTATCTGGGTTCCACCCCAGACCAATTCA
TTCAGAATCTCTGGAGTGGGTCCCAAGTATCAGTGTCTTATAAAGGCTCCC
CAGGGAAGACTAACACACAGCCAGAGTTAAGAACTGCTGAGTCTATGGTCA
GGAATATGGAGAGAAGTAAAAAATGTTTAAAAAGTTCATGCTCAGTACCAC
ATTTAAGTTTGTAACTTTATGTCCTCAGAGGCGGGTAAGGGTCCTCTCTTT
GGCCCAGTCTTGAAGTTCTGCTTGTCCAAACGTGAGGTAAAAGACCAGGCC
AAACATGTTGACTGCAGCAGACAGGAAAAAGACATTCCTCCAACCAGACTC
AAAATCCTAGATGTAAAAAACAGAGAAAATGATCAATCTCACAAGTTCCTT
CTACACCAGTTCTAGTAGCCCTCCCAGTTGTGTATTGCAATGTTGATCACA
```

FIG. 8-114

AGGAATATAAGGAACAATGTGCAGTAGTTACTTAAGAAAGTTTATGAAACT
ATTGGAAACAAAATGGCCAAAATGCACATGGGGTTCTGAGTTGAGATGGTT
ATTTCTTTAAACAAAAATAAAATACACTAATGTTTTTCTGAAAATTTGGAT
TTCAACATATAATATTACTCATTTAAAATTATGCCTAAAATGGCATTGTGG
CATTGTGTTTGTGTCTTCTCTGTTTTTTTTGTTGTTGTTGTTGCTGTTTG
TTTTGTTTTTTTTTGTTTCTGTATTGGCTGTTGACAACTATCACTACAACC
CATCTCAATTCAACATGAGTTCTCTTTGGTCTTCTGTGTGACCCTCCTCAG
AAAGCCCTACTAAGTCATTTCCAGCATTATAGTCACAGTGGATTCCTAGCA
GTTTAGTCAAATATTAACCTGGGAACTTGATCACATAGAAATGTAGTAAAA
ACAAAACTTCTCTTTGTAAGTTGGTTCTCGTCAGTCCTTCCATCCCTGCCT
GGGTCTGTCTTTTCATCTTCCTCATGAGCCTGCATTTCCAAACACCGAGCA
AGCCTCCTTGCAATGTCTCACAGCCGATCTGTTTCCAGACATTAAATTATC
TTTAAACTGGCCTAGGACACTTTGTTTCCCTTTTGTGATTTTTTAAAAATT
GGATTAGTCTGAACATATTCTTCATGATCTTCTTTTGCCCCTCTGTCTTCG
TCTCTTGCTATTCCTTGACATGTGTCTTTCATTCTGGTCATAACTAAGAAC
TGTTTCATGCTCATGTACCTCTAGGAAGTCACACGTGCTGTCTTCTGCACC
GGAACAGCTCATTTTAATCAATCTAACATCTATTCATCTTGAGAAAATAAG
CTTATATTTTTCTTCCTCTGGGAAATCTGACCTACCAGAGTCTGATTTAGA
GGCTCATGTAAATAGAGTAATTGTGTTGCCATCCAGATCTTTAGAGCACCG
TGTGTATCTCCAACACCTAAAACAATACCTGCCACTTGAAGATGTTCAATA
AACTGGCCCAACCTGACTGATGAGGAATCCAGTGGCAGTGGAAGAGATGAT
TCCTGCGATGAGCCCAAATCCCCTTGAGATTCCCATGAGGAAACTTGCATA
TCTGTGGGAAGATGATTTTATAAATGATTTTATATAGAAAGCCACCTACAG
CTTCTGCAGCAACTCAACTTTAATGCAATTCAGCTCTAATGGCAAAGTCAT
TTTGCTTAATGCAGTTTTTCATTCACCTAAAGACATTCAGGGCAATGTCTA
TTTGCCAAACCTGAAATTACCAATCTACCAAGTCAATAACCAGGGAGCAAT
GCAGTCTCTCTGGGAACCACGTTTCTTTACCCCGGCTGCTCAGTGGAGAAG
CCAGTTTGTGCAACGGGCAGGACACAGACTCCAAAGCCAGACTCCCCCAGT
CCAAATCCTGGCTCTGCCTTTATGTGACCATAGTCACACCATTTAACCTCC
TTGTGCCTCAGCCTTCTCCCTTATAAAATGGGGATAACAATAGGGCCTACC
TAATATAACTGTGAGGATTAGATGTGTTGATATATGGCAAGTCTTGGCACA
GGAGCTGGCTTATTGTGACTGTATATATATATATATATATATATATATATA
TATGGTAGCTAATATGAACAACACCATGGAAACTTTTCCAAATCACCTGTG
TGTGGGCCTTTTCCCAGCATACACAGTTCAATCTCTGTTAGGGAAGCTTGG
GAAGGTTTTTGTCAAAATGATTACTGGCCAAGATTGGAAATTGTTGTTCTA
AAAATGCCACATTTGTTGTTCTAAAAATGGCCACAGACAGATATTTGTAGT
TATTTGTCATTCTGCCATTAGTGCAATGTCAGTAACATTAAAGAGTTTCAC
GGCGACCACTGAGGTCTAACACCTCTGGAGGGGTCTGGAGGAGGGGAAAAA
ACAGGTAGAGCTCTTACCTGGGGGCGATATCTAAGGTGTTGATGATAAACC
CTGAGTCACATAGGTTACTGGTCCCAGGAATAAGTATCAGCAAAATAATGG
TTATCACGTAACTGGAGGCCACAAAGGGCAGGGCCACAGCACATATTGATG
GAAGGAGGAGCCCTGGGCAATGAGGACATGCTGTCAGGGAACCCTCTGAGA
CCATGTGCAGAAAAGGGATTGGTTAAATGGGCCCACACGCTTATCCTTACC
AAGAGATGAAAAGAGCTTTCGCACAGTGATCAATCTGAGAAGATTCCTGGA
CAAAAGGAAATCTGCCAGCTGACCTCCTAAAATTGTACAGCTTGCAGCAGC
AATAAAAGGCAGGGAGGACAGAACTCCACTCTGAAGGAAGGAAGTTTATAC

FIG. 8-115

```
AGAGTAGTTATAGAGATACGTTAGCACCAAAATTTGTCAGTTACACAGACC
AGCCATTAACTTACCCCCATGATACTGTGGGTTGTTTGGGGGAAAATTAGC
ATCCTTTTTCACACTAAAAGAACACTGTCTCAGATAAGAGGGCCAGAAGCT
GCATCACTCTGGGCTCCAGATAAAAGCAATATTAATTTCTTGGGTTTTTTG
TTTTTGAAACGGAGTCTTACTCTGTCGCCCAGGCTGGAGTGCAGTGGCATG
ATCTTGGCTCAATGCAACCTCCACCTCCTGGGTTCAAGCGATTCTCCTGTC
TCAGCCTCCTGAATAGCTGGGATTACAGGTGCCTGCCACCACACCTGGCTA
ATTTTTGTATTTTTAGTAGATGATATTTAGTAAACCATATTGGTCAGGCTG
GTCTTGCATTCCTGACCTCATGATCTGCCTGCCTCGGCCTCCCAAAGTGCT
GGAATTACAGGCATGACCACCATGCCTGGCCCAGCAATATTATTTCTAAAA
GAAGCTTTGGAATCAGCTGGTGTGGTAGTATAGCATAGTGGTTAAGAATAT
GGATGCTGCAGCAGCTCTATCACTTAGTATTGTGCAACCTGGGGCAAGTTA
TCTCACCTCTAAGTGTCCTGTTTCCACATCTGTGAAAAGGGAATTATAACA
ATGCCTCTCTCAAGGTCATTGTGAAGGTTAAATTAATGGTTATATGTAAAG
CCAGAATGTAATAGGTAACACAGAACTGTTTCTCCTTATTACCATTATCAT
TTTCGTAGAAGTATAGGAAGTAAACTCACATCTCTGATGTTAACATGGAGC
AGAGTACTGATATACGTTGGTAGGTATGTTAGGATGATGGTGCACAACCAG
AAATGGCTGAAAAAACCCAGGAAAATGGCCCAAAGTGGTAGGCATGTGACC
ATCGCCTTTATGGGGACAGCTCGTCCAGGAGAACTGGGCTGAAAAGAAAGA
TCTAATCAGCATGAGTATTAGAGCAGCCAAGATGGTGCCTCTCAGAGGAGA
TCCACACCCTGCCCTAGAGACCTCTGCATGGGCCACAGGTACAAGGTGTGC
ACTGTACCTGTTGAGCCAGTGAGGACAGGATGTGCTCCTTTTCCCTAACAC
TTATGCACGGGTGATGCATGGGGTCATCATAAATCACTGTGAACCATAGGA
GACAGCAGACACAGCCAGTGCTACCTGGGAAGAAGGGATAAAATTAGTTTT
TAGGTAGATTTGTTTACTGGGGGAAGGAAGTTTCCTCTGAAGTGGCATGCC
TCTCCCTTCTACACACTAATCAATTAATGCTTATTCTACCATAAGGACCTA
AATGTTCCCATTCTTTCTTTCAATCCTTCTACAAACCTGTTAAAGCTTTTT
AGATATTACGTCTCAAATAGAAAGCCACCATTTGTCAATGTCAGAGCCCTC
TGGAGATAACAGGAGCGTGGCATTGCATAGCTGATTAATTACTTTAAAGTC
TCCAATGATTACAGTGTTATGTATTTTAGGCAGCAACTTCTTAATGCACAC
ATAAGTTGTCTTGTTGCGGAAGATCTGAATAGTCAGGTTTGCAGTCATACA
TACACGAAACAACCTTCCATGAAATCATGTGGCAGGGAAAAATTTCCAATG
CACTTACAAGAGACAGTATTATTTGTATTCAAGCCATACATCCATTATGGA
TTCCCAAAAGAAATATTTTTGTACAATACCTGGTTAACATGTACAAACCAA
AATAATTAGCATCATTAATGAGAAAGCCATTCAGGCCAGGACTATATTTAA
TGACACCATTTGGCTATAAAAACAAATCAAGTGTAGAAAATTGTCTTATTA
TTGGAATTCCTTATTTGAAGAACATTCTATGTTAAAAGATTCTGAGGACTA
GTTTTCTTTAAATCCCCTCTAATTACTGGATTCACTGATTCTTTTATTTTA
AAGCTAAAAATCAGGCACCATGATGACACCCAAGTGATGAAAACATAGAAT
GGATTCCTTGCCTCAAGCATTTCACAGTCTAGTGGAAAGAAAAGGAGAAAT
AAATAATTACACACCAACATAACCTAGAGAGGAAATATCATAAAGGAGAGA
ATGCCAGAATCTGATAGGGTAAGCCCTGGAAGGGCCCATGGGGAAGGGAAC
ATTTGAATTGAACTTTGCAAGATTAACTTGGTAGAGAACAGGTGAAAGGCA
TCTTGGACAGAAATAATAATTATAATGAAATATGAAGACACATTGAAAATG
TACTTCACTATCTTTGACATCTTAACTGCATATAGCAGGCACTTCAGATGT
GGTGGTAGAGATTCTGCAGAAGGTGCTTGATATGGAAGGACAAGACTGCAT
```

FIG. 8-116

```
CACAAGTCGGTGGGTGCCATGTGAATAGTCAACTCCTCTACCTTGTGCGTG
TGGCTTCCCAGAACCACCAGGAAGGTGTTAATCAGGTTGTGTGACTAGATT
AAAAATGATACCAACCGTTGACATTTTTTATCATCTTCCATTTGATAAAGG
ACATTTTCTTTCATATAGGAAGAATGTGGGTGGTGTAGGTGCCAAAATGGA
TGCTCAGGAAATGGAGGCGTTAGGATTTAAGAGAAAGTGACTCACCAAAGA
TGTACAAGATAAAAGGCCAGCTCAAGGCCTGTGAGATTAGTCCCCCCACAC
AGAGGATGATGAAGGATCCAAATGCTGACCCTAAAGGAAAAAGGGAGAAAA
ACACTTATGAAAATATCAAAGGCTGAGACTTCGTGGCCTCCCTAAACAATG
TCCCAACAGTGAGGTGGCAGACTTAGAATTATTGGGCAATGAGAGTATTTA
TTTCTAAAATAGCTCACAGATTTTCCCCAGTAAAGTAATATGATATAATTA
AAATTAACAAATAATAGTAACACACTCTCTGATTCTTCAATGGCTCCTCAA
CACCAATGTGACCAAATCTAAATCCCTTAGTTTGTCACAGTAACTCTCTGC
TATCACAGCCCATTAGCATTTTCTTGTGATTACAGTTGCATTCTTGCATGA
TCTAATATGAGGCTAGGGGCAGGAAATGAAAGACTTACAAAAATCGGTAAG
ATACAGCCCCTGCCCTCAAAGAGCTTCTGGTCCAATTGGAGAGAAAAATGT
GAATAAAATTGATTGTCACTAGTGAAATGCCATGTAGGCTTTGGAAGTCTA
CATTAAAAAACAACAAGACACATATTTCACAGAGACCTATAGTAAGAAATG
CATTTTACAGGGTAACATAACACACACACCAATATGCATAAACACTTGTAC
ATACAACCACACACATATGCCTCAAACGATGGTTTCATGAATCGATATTTA
ACTTTACCATGTCCAATGCACTCCAACAATTTCTATTCTATTCTATTCATT
TTTTAAAATAATGATTTTAACCCGCTCAATGGATTTTATGACTCACTAATG
GGTCCCAAACTGAAATTTGAAAAAAAAGATGTAAAATATAAATATAATAAA
ACTACAATGTACGTGGAAGTATATCTGAGGATAAATTGATAATAATTATAA
GATTTAGGAAGTTTTGGCCGGGCGCGGTGGCTCACGCCTGTAATCCCAGCA
CTTTGGGAGGCCGAGGCGGGCGGATCACGAGGTCAGGAGATTGAGACCATC
CTGGCTTGAAACCCCGTCTCTACTAAAAATACAAAAAATTAGCCGGTCATG
GTGGCAGGCGCCTGTAGTCCCAGCTACTCGGGAGGCTGAGGCAGGAAAATG
GCGTGAACCCGGGAGGCGGAGCTTGCAGTGAGCCGAGATAGCGCTACTGCA
GTCCGGCCTGGGCGAAAGAGTGAGACACCGTCTCAAAAAAAAAAAAAAAAA
AAAAAAAAAAAGGTTTAGGAAGTTTTTACATAAGCTATGCAATAGGATAGA
TGGAATTTTGGCACAAGGAACAGGGGCAAAGAACTTTCCAGGCATATAAAC
TAACGGGAGCAGAGCCAGAGGGAAGTGCAGTGCAGATCTATGTGGAGAGCA
GCCAATGTCCAGTGCCACTGGAGCCATGCTTGCACAGGGGAGTTGAGTGGA
ACAAGGTTGGGGCCAGATGGCTAAGAACTTTTGTATTCATGCAATAAAGAG
GTCAGGCTTTACTCTGTAAGCATGAAGGAACACATTGAAAATTCTCAAGCG
GGTGAGTAAAAATGTGCCATCTTTATTTTAGCAAGCTAACTTGGTTTTGGT
GGGAAGAAGGTTGAAAGAAACCAGTCTAGAAGAGAGAGATCAGCAGATAGT
ATTTGCAAATAGAGGAGATGGTTACAACTATGATGGAAGGAAGCAAGAACG
CAGGAGGGTTGCTTGAGGTAAAAGTCTGCAGGATGCAGCTGTGTAGTGGAC
CTAGGAGTGAGAAGCTGGATGGAATTTTAGTTCTGCTCTTCGAGTATATAC
TCTCAGCACGACAGGCTGGGGAGAACAGCAATGATAAAGCTGTAGAGGCCT
GAGTAGGATCACATACCATGGAAAGGCAGTCTAGCATAGTGATTGAGAATG
TCTGCTCTGGGGCTAAAATCTGCATGGGCTTAAATCTCAGACCTACCACCT
GCTGGCTATTTGTATTTGGGCAATTTTCTTAATCTCCACCTTCCTTAACTC
CCTTCTCTGTAAAATAAGAATTTAAAATGGTACTTATATGAGAGGGTTGTT
GTGAGAATTAATGAGCTCATAATAGAATAGTAAAGAGCTTAGAATAATACA
```

FIG. 8-117

```
GAAACTTCAAACTCTTCCAGCCTGATTTCTCTCCTTACCACCTGGAGCTGT
GGTAGCCTTAATTCTCACTTCAAAATCATTGCTAAGATGGTGTATATATAG
CTTACTTGATCTTTTTCCATGTGTGCAATTCTTAAAGGTTTAAACTTTTTC
CGACAAGGCTTTTCTGACTACTAAGGCTTTTCTGACTACTAAGGCTTTTCT
GAGCTGAAACCTAGCTCACAATGGTTTTTTCTACTTCTAAGCTTCAATGTC
TTTACTGCACAGATGCATCTTTCCTATTTGTGATGCAAGTGTCTTATATTG
TTGAATTTTTCAGCAGTACTTTTTCTCTCTCTTCCCCAAACCATTTGATTC
ATAGAAGATAAGACACAGTGGGATGGAACAGATGACAAAGCTATGACCCAT
CTGTGCACACTTACCTGATCCTGCAATGGTGGTGAGCTTGCTTCGTTCAAG
TGGAGGAGCCCACTTTGCCCAAATAGTAAACTGACCTGTCCATGCCATTCC
CTGAAATGAAAATCATTAAGACCTTTGATATTTTGTAGAATTCAGAAATCT
GGATCCCACCAAGAATGAGAAAGTATCTGGATACCTGGGCCAAGCCCTGGA
CTGTCCGAACCATGATGACCAAAATCACTCCGAAGTCAGCAGCCAGTGGTG
TAAAGAGGGTGAGAAGGGAAGAGATCAGCAAACCAGCACCAAGCATTTTTT
TTGCTCCAAATATCCCTGCTAAATATCCACTTGGGATCAGAGTCAGTATTA
TCCCATAGTTGATGGAGCTAAAGATGATACCCTGAGTTTCTGGGCTCCATT
GATACACAGAGGCCTGGGGGAAAAATAGGAAAACTCTTTGTCAAGAAGTCC
TATTATGAAAATCTACTTTACAGTCAGAGTTGCTTGAGGTTAGTGAGACCC
TAGTATAAAATATTGATTTTGTTTCTCTCTATATTCTTCCTACCTTCCCA
AATAACCAATTATACCCCTAATTTGCTTGTCTTAGTAGAAGGAGAGAAAAA
CAGAAGAAATGAAGAAAAGAGGTAAAGAAAATGATTATATAGATGAATAAT
AGGAAGAAGTAAATGGAAGAAAACATTGAGAGATATTTCATCTGTGAAAGC
ACTTCCTCTATTTTGCTTCTAGTAAAAGTTGAGTAACATCTTGACTCTTAT
ATCAAAGAATTTTTTAAAACACACACACAAAACTTTACTGAACTCTTAACC
AAAATCAGTGCCTAATTAAAAAGAAAAGTCAAGTTTGGGAATCATGGTCTG
CCCTGGCTGAACTGAGTTCCTAAAACACATATTACAAATGAATAAGATCAC
ATTCTTCTGATATAACTCAATAAATAATTTGAATTATTTTAAAATAACTAC
CTAAAATTCCTAAATAATTACATAAATTATATTACCTGAATATTTACCTAA
AAATAAATAGATTTTAAAATAAATAAATAAAAAATAAAATAGATTTTAAAA
TAAAATAAAAAATAAATGCAATAAGGCCCCTAAATATCTGGCATCATGCTA
TAAAGTAGAGAGCCAAAGAATATAAAATATGAAATATTTTACCCACTCAAA
AAAACTATAAATAATACAAGGTATATGATTCATGTGAGAATCAAGATTTGA
GGATGAACATAAATAAAACAGAGACTTTGAGAGGAGAAAATAATAATTTGG
GAAGGTCCCAGAAAGGAAGCAATACTTGAACTATCCCTTGAAAAATGACTA
TGATTTGTAGAAAGTCAAAAAGGAAAATTTTATCTCATCGGAAAAAATAGC
AAAAGTGAACTTGTAGCATTTGGAAGAAACTAACAGGGACTCTGGCTTGCT
CAGGGCAAAAACTTTCCATGGGTCATTGATAGCAGATGTGAGTGTGCTGAG
AAGCAGGCCCAAATTCTGAAGGAACACAGCATGTCCAGTGAACACTGCATG
TTTGGCAACTTGAAGGTGTCCAAGATTCCTGAGTAGTGAATCTACTCAGTG
TGGATATGTAGACGGGATAATGGAGGAAAGACTGGAGACAATAAATTTATG
TACTCATTGTAAATAAGCTAGGTCCAATGTAATAAAATCATTAATCATGAA
TTATAGGGATGACATGGGAAATGTACAGTACAAGATAATTTAAAGGATAAT
TTTTTTAATTGGGTAAATTCATGGTTTTCATATAAATGTAAAATAAACATA
CAACAAAGATTTTATTTAACTCATTGATTAATGGAGGAAGTAAGTAAGATG
TTATAACTGGTTCAAAGGAAAACTCAAAGAATCACGCATAACACAAGCAGG
AAGCAATGCTGAAATAGACTTTAAATATACAGCAGAGCCTGGCACAGTGGC
```

FIG. 8-118

```
TCACACCTGTAATCCCAACACTTTGGGAGGCCGAGGCGGGTGGATCACCTG
AGGTCAGGAGTTCGAGACCAGCCTAGTGAAACCCTGTCTTTACTAAAAATA
CAAAAATTAGCCAGCCGCGGTGGCATGCCCCCTTACTCCCAGCTACTTGGG
AGGCCGAGACAGGAAAATCTCTTGAACCCGGGAGGCGGAGGCTGCAGTGAG
CTGAGATCATGCCACTGCACTCCAGCCTGAATGACAGAGGAAGACTCTATC
TCAAAAAACAAACAAACAAACAAACAGCAAAATTGGCTAATTCAACTGGGA
GGTGAGTGGAGAAAAGTTTTAACTGATTTTTCTCTTGGCAAAATTTATTTG
CAAAGCTATGGACAAGAATCGTTTGCATTTCTATTGGTTATATAGAATTTA
CAGGGATATAAAATTGCTCAGAAACAATAAAACAGGCAGAGAACTGAATAG
GATTGAGTAACCTATAAGAATGTGCCCAGGTAATACCTAGTTTTTCATTGA
AGACATCACATAAACTGTTCCATTTTTAAATTTTTCACATTTAACTCTACA
GTTCCCCCACCTTATAATCATAATAACCTCAATGAAATCTTATTTTTATTA
TTGAAGTAAGCAATGTCTCAAAGAAAAATAGTTCCAGTCAGTTTTAATTTG
TCATTGGAAATGTATACTTCCATACTCCACAGAATCAAGATCTATGCCTTC
CTTTCAAAGTTTTTTCTCTCAACAAAGAGCCCTATTTTCCATCATACTTAC
CTTTGTATCAAATTCCTTGATGGATATGCTGGAGTTATTGAAGGCATCTGC
AACAGGCCCCTCAGTGGAGGCATTAGATAGACCTTGCTGCTGAGTGGTGTT
CACCATGGCGATGATCGCAATGCTCAGACTCACACGCTGCGTTATCATGGT
GAAGTTTGAGAAGTGCATGATAAGAGCCAGCCCATAGCGTAATGAACAGAA
ATCTGGACCTAGACAACAACACAGATGTATGTAGTGAGCATCCTGACTGAG
ACCCCTTTCTTTTCCTTTCTCTCACAGCTCGATCTGATAGAACTTTGGATG
ACACATGAAGTCTCATTGTCTTTTTTTCACCAAAATAGCCAGCACTACAAA
CCCACTTTGTCAAATTATTTGGTTGGCTTCAAGACAGCGAATATGGGATCT
TATAACCAAGTAAAGCAAATATGGCCATCTTTCAAGGGGATAGGAAACACA
TGATAAATAGAGAAAACCCACATGTAAGGCATTTATGTCATATTGCTCCAA
AATGAAGTGAATGGGGATGACAGTGGCAGAGCCAGTCACATAACCTTCTCA
GCGTCAATAAAATTCCCTGGGCTGTAAGTGAATAGTCCCATCTGTTATGCA
CATTTGTTTATCACAAAGCTTGAGAGTTTATACATAACGAGCTGCCTTTGA
ATTAAGGTATTGCACATCCAAGGATTCTCTTTTAATACATTTGAGAGATGG
TACTTTAAATGAGCACTTCGACTAATTCCCTAGTGTAATGTCTACTTGGAA
ATGTTATTGCTATGTGTCACTAGGTCCTGCCTTCACATATGTTCAACTTAA
AAAAAAAAAAAAACTACGTGGGGTGCAGTGGCTCACGCCTGTAGTCCCAGC
ATTTTGGGAGGCTAAGGCAGGTGGATCACTTGAGGTCAGGAGTTTGAGACC
AGCCTGGTCAACATGGTGAAACCCCATCTCTACTAAAAATACAAAAATTAC
CCAGGCATGGTGATGCATGCCTGTAATCCCAGCTACTCGGGAGGCTGAGTC
AGGAGAATCACTTGAACCCAGGAGGCAGAGGTTGCAATGAGCCAAGATCAT
GTCACTGTACTCCAGCCTGGGTGACAGAATGAGACTCAATCTCAAAAAAAA
AAAAAAATTAATATGTAGAACTATTTTTACAAAGCTTGCAGGTGATGTGG
TGCTGGAAGATATTCAATATATTGAAAGGACAAATTTTTTCTTTAAAAGCA
TCCCCATAAAATGGAACAACCACAGACCAATATTGAAAGGGTTCCCATGTG
CATGATAGATTGGATTTTTCCTGCTTATTTGAAGAAAAGCACTAAAGTGAA
AGAAAGAGAAAACCTGTGAAGACACAGATAAAAATATAATGGAAGAAATAA
TTTTTAATGGCCAAAAAAGCTCACAGATAAGAGTGGTGGTCTGGGAAATAA
TTATTTCCATTTTACTGGAGGTTTCCAAGCTCAGGAGAAAGAGCCAGCCGC
TTGGTGAGAATATTATAGTAGGGATTCATACATAGGTTGGTTTAAAATGAC
TTTCCCGGGCCAGGCGTGGTGGCCCATGCCTGTAATCCCAGCACTTTGGGA
GGCCGAGGCCGGTGGATCACGAGGTCAGGAGATCGAGACCATCCTGGCTAA
```

FIG. 8-119

```
CACGGCGAAACTCCATCTCTACTAAAAATACAAAAATTCATCTGGGCATGG
TGGTGTGTGCCTGTAGTCCAAGCTACTCGGGAGGCTGAGGCAGGAGAATCA
CTTGAACCCGGGAGGCAGAGGTTGCAGTGAGCCGAGATCGCACCACTGCAC
TCCAGCCTGTGAGACAGAGCAAGACTCAGTCAAAAAAAAAAAAAAAAAAGA
CTTTCCCAAAACTTATTCCACTCCCTAGATCCCAGGATTTATTGCTTATTT
GGCTTAATTTCTCACAGATGATTTCATGGGGCTAAGGAAAAAGCAACAGGA
TCAGGGGCTGGAGCTGGCTCCAATGTTACACTGGGAGTATCTTTACGAAGG
GTCAGTGTGATGCAGAGATGTGTAAATGTGTCGGAATAAGCTTCAGCTTAT
TAACATAGCCTGCAAACAAGAGCAGTGGCTTTACCTTTCCTGGTGGCAGGC
TTCCCGTCCATTTAGCTTCTGTGGGAAATGGTACCACGCTTTGTGGTGGAG
TTTCCCTGTGCCCTGAATCTCTTTTACTACGACAGTCTTTTATCTATGGAG
AGAACATAATCCAAAACATAATACACAAATAATTTCCCCTTGTTAATGTTG
CCTCCTCTTAGCATCAGTAAAAGTTTTGACCCAACACAGCTCTATAACTTA
CATTTTATGGGGCACTACTGGTATGCTTTTGGTTACAGGATTGTTAAAAGG
AAATCTGGCTGTAAGTTCCAGCTGTGTGACCTAGAGCTAGTCATTTAAATT
CTCTAATCATTCATTTCCTCATCTGTTCAATAAAGATAAGGCTCCTTTCTT
AGTGCAGCTGGAAGAATTAAATGAAAAATTGCATGTACTTTATCAAACCAC
AGAGAAGCATGCGAAGGTGAAGAGTGGTATTGCTTGTAGCAGACCATAAGA
CAGGACAATTAAACTAAGCTCAAGAGCTAAGGAGGAAGGTTCCAGAGCGGT
CTTTCCTTTCATTCTGATGGTGTTTCTCTCCCCTCTGTACCACCAGAACAA
TGTTCCATGTGCCTTCGAACATGAAGGATGACATTACATAACACTAATATG
TATTACATTTAAAAGTTTAAAATGTTTATTCTCATGTTTGCTACACACAAT
GTGGACACTTGCTTGGACTGACAAAGTCTTCATATCACCTAGAAAATTATA
ATGAACAGGGACTAATTACTACAATTGTGAATAAATCCAGCTATTGTGACA
GGCAAAGAGAATTCATGGCTCTAAATATGGACATGTTTAATTTAATATTTG
TATACTAATCAAATTATCTTTGGGGATGCATACATTTGTTTCTTTTAGGAA
AAATCCATATCCTAAGAATATCATCAATTTTCCATTCATTCCTAAATTGAA
GCTTCTATGACTTTATTTTTAAATTGCTTAAAATCCTTCAAGACATCTGA
AATTTCTGTGACTTTAAAAACACATGTATCGGCCGGGTGCAGTGGCTCACA
CCTGTAATCCCAGCACTTTGGGAGACTGAGGTGGGTGGATCACTTGAGGTC
AGGTGTTCGAGATCATCCTGGCCAACATGGTGAAACCCCATCTCTACTAAA
AATACAAAAACAGCCGGGTGTGGTGGCACATGCCTGTAGACCCTGCTACTA
AGGAGGCTGAGGCAGGATAATTGCTTGAACCCAAGAGGCAAAGGTTGCAGT
GAGCCAAGATCGTGCCACTGCACTACAGCTTGGGGACAGAGCAGGAATCC
GTCTCAAAACAAACAAACAAAAAAACACATATATCAAACCTCTATTTTATC
ATTCAAGGCTTTGCACTGTTTTTGCACACAAAATTTAAAAGACTTGTCCGT
ACTTTAAAGATATTCATAATCTGTGACCTTAGGATGAAGGATTATAAAGAA
AGGCATAGATGAAAAATTGTGTCCAAAAATATCCTTTGTAGTATTACTCAT
GACTGCATAATGTTAGAGATAAATTAACCTAATAATGAGAGTCTGGCAAGT
CAATTTGATAGATTATTGTGATGGAAGCTATTTTAAAATGTTTTCGACAAT
ATTGAATTACATTAGAAAAATGCTAGTACTCTAGTGTACAAAGCAGGATAC
GCTGTGCACATCCACATACAGGAATAGAAACTGATTCACACAAGTGCCAGT
AATGACTATTTCTGGGTTACAAAACAGGATGATCACTTCATTCTTTGTGAC
TTTCTATATTTACCAAGTGATTTTGTAAATAATTAGTAGATACTCATTTTA
TATTCAGAAGTAGCTAAATGTATTTAAAAGAGCAATAATTGGACTTCATCA
GCATGGCAAGTATAGTTTTCTGCTTTCCAAATATCTCTAGAATTCTGGGAA
```

FIG. 8-120
```
TAGTATCTCTCCATCTAAATTTTGAATTTTGGGTGTTTGGAGATTTTATTG
TTGTTGTTGTTGTTGTTTTGTACAATGGACCCAAATGGAGGCCCAATTGCT
AGTAAGATCAGGTCAGCACCAGGACAGATACTGGTTGTTGCTCTGCCTTAG
AAGGCCTCCAAGTCTTGCTAACATCTGGATATCAGGAGTTCAGCTCATTGC
TCTACACTCAGATCCTAGCTGAAGTCATCTGTGGTCAAACCCAGAGTTTGG
ACCATTTCTATTTGATTTCACTTTTTATGCAAGATCCCGTGGCTTGGCTG
AAGGCAACTCTTTAACTGTACATGCAGCTGCAATTACTTACACTCCACTTA
AAGCTTTCCCACCAACTTCTCCAATCTTATAAACACTGAAAGCTGAAAGAG
ACTCAGAGATCCTCTGGCCCAACTGTTTATTTTATTGATAAGAAAATTTGC
GTAGAAAATTTGAAAAGTTGCCTGAAACCACATGATGCACAGAGCCAGCAC
CAGATCCCCTAATGCCTAGACTACTGCTTGTTCTACCTATTACAACTTCCC
CTTTGTTTTCGTAATATTTTAATCACAAGCTTAAAACTCAATGGGGTAGCT
CCATTTTGAGGTATTATAAAGGAGAATTTGTATATTTTAAATCAAGTTTTA
ATCATTTATTCTAGAAGGAAGTTTGATAATGAAAAATACTTTTAGGTTGAG
CTTTGAATATTAAACATAAACACAACAAAACTACTTCTCCTTGCTCTTTAT
GTTACTGGAATTGTATCACAAACCCATCACTTTAGTTTTTCTTCCCATTCT
CTGTTGCTGTCTAACGAGAAAGGATGAAAAGCCCTACTTAAGTTTTATGGT
TTCAAATGCTACTTTGATTTTGTATCAATAGGTAATTTCAGTTCTTCGTTT
CCTATTTTCCTTTGCATGAGACGAATGCAGAAATCAGGCTAACATACCAAA
CCATCCTAAACTGAGGTCTTTCATGGTAATGGGAAATGTTTTTCCAAAATA
AGCACAGAAGCTAATAAAATTATGGAGGCTGAACACTGGCATGGTTGATAT
GTACTTAGAGACACTGGAATAATTATTAACCTATTTGCAAACAATTGAGAA
CATGTAACAGTGTCAGAACCCTTCCCTTTAAGGAGATATACCTCTAAAAAA
AAATTGTGAATTCTAGTGCCAAAGTTGTAAGTAGACACAGAAAAATGAATT
GAAATTAAGTTAAAGGAAAATGTTATATTAAAAAAAATTACTTGACACAGT
ATAGGTTGAATTTGAGAAAAAAATAAATAATGTAAATATTATGGTATACGC
ATAAGCAAAAAAACAGGTTTTTCCCTTTTTTTAAGTCTAGAACTCATGATT
TTATTATAATGGTCGTTAGATTGCTCTTAGATTCTCCTAATATCCAGCCTG
TCTTGCTTCATCTCTGTTAGCCCAGAGTCCTAGTTTACTCAGAGTAAATGT
TACACCTAGATCAAAGAGCATGAACCTGCAGTGGGAGGATATTCAAGGACT
GAATTCTGCTCTGCCATTCCCAAATTGAGTAAACCAGGTAAAGTTTCAAAA
ACTCTTAGGGCTTTCACTGTTTCATAGGAAGAATTGGGATAATGTTACTTC
ACTGGGCAGTTGGAGTGAAAACAAAAGTATGAGACATGCCTCGTAAATTG
CAAAGTGTTATATGTTGTATAATATTCTAGATACTAGCAACAGCAATAATA
ATAAACAGTCACAATATTGGCAGTCTAGCCCTCTCAGATCCATAAATACAG
GCCTACAGCAAATGAAATGTATTTCTATAAAAGTGCCTTTGATTGGTTGTT
AAATTGGTTTTAAATGTTTCTTTTTTAAAGTGGATTCTTCTGGCCTGGAAT
CCTCAAGATGAGTGGGGAGGAGTTCACCAGAAAACATAGAAGCAATTCCTT
CAGTGTTAGAAAAACTGAGGGCCCTCTCATCATCTGCCTATCTTTCTGAGA
AATTGGTGCTGACCACAATGTCCCTGGGTGCCTTTTCTTAGCTGTACAATG
AGGGCAACAAGCTAGGTGATCTCTACAAGCGTACAATTTTCTTGCCTTCAG
TCTTATTCATAACTTTGGTCATGTTCTCCTTTTCTTTTATTATTATTATTT
TTTTGAGACAGAGTCTTACTCTGTCACCTAGGCTGGAGTGCAGTGGTATGA
TCTCAACTACTGCAACCTCTACGTCCTGGGTTCAAGCAATTCTCCTGCCTC
AGCCTTCTGAATAGCTGGCACGCGCACTATGCATGCGCATAGGTGCACGCG
CCGCTACGCCCTGCTAATTTTTGTATTTTTAGTGGAGACAGGGTTTCACCA
```

FIG. 8-121

```
TGTTGGCCAGGCTGGTCTCAAACTCCTGACCTCAAGTGATCTGCCCGCCTC
AGCCTGCCAAAGTGCTGGGATTACAGGCGTGAGCCACCAGGCCCGGCCATG
TTCTCCTTTTCCTGAGAGACCATTTCAAATTCATATAGAAGTCTGAAAAGA
CTCGTTAGCCACAGTCCCAAACACAAATCTTGTCAGTTCTGATCAGTATTT
CATTCCACAGCCAATCCCAGTCTGACTAATCACAGCATCACAGTTAATACT
CACAGCGTCCTTGGAGAAATGACCATTGTCCACAGTGTCCATTGGTACCAG
TGGCTTCTCAAGCCTTGCCCTAGGGTCTTCATTGAATCAGTTATCTTTTTC
AGAGAGTCTCTTCATTTTGGAATTAGGCAATATTACCAGATGGAGATCCTT
ATGTTGCTGTTAATGTCTTTTCTCTGACTTCTCCTAAAACTGTTCCCTCCC
CTTAATGGACCTTTGGTAAGTTAGTAATAATCCTTCTACCCAAAAAGAAGA
AAAGCACTTACCTTCACCATTAAACCAGTATTTTAAGCCCTAGACTATAAG
GCTAACTTGGAAAAGGAGGGAGTTTTCTGTCCCTTCTTCCCTTTCAAATAC
TTTTGCAGATTTTTACAGGGATAAATAGTGAGCCACGTGGCAGTCAGACGG
CAACAGGTTTGGCCCCACTTTCTCAGAAAGCCTCGGCTTGGTTTTGCCGCT
TAATTTTTAACTTCATTTTCAAGTTCTCACTGTTAGAGTATCTCAAAAGAT
GTCATCGTGTGTTTCTGCTTTGAACTGTGCATACAACCATTCAGTCAACAA
GCCTTTTTTTCTGAAAGCAAGGGGGCATGGTGTGGAGGAAAGGGCAGGGCT
CCTGAAATCAGTGATGGAGTCAGACCCATATTCACTTCCTAGTGTTTTCCC
TGAGCTTGGACAAGTCACTGAACCTCTTTGAATTGGCTTCCGCTTTAGTAA
AGCAAGGATTGTGTTACTGTACTCATGGGGTTATTGAACAAATGAAATACA
TATTCTAATTGGTAGTAGCTCCTCAATAAATGAGGTGTTCATTCCTCTTCA
GGAGTTCAGTTAAGTCAGCTAGATTTTCCATATGCATTTGGTGCCCACAGC
CTAATGAATGTGAACTGTGACTGCCCTGGCAACTTCCCAGGAAGCTGCCTT
GTACCCCTCCTTCCTGTTTCATATCATCCATGTCTTCCCTAATCCATTTTC
TGCTTGGCTCCCGACTCTTGGAATTGTGTCCTATTTGTAATCATTAATTTT
GAGACTGTGGTTGCTATTGGATCTTCCTAGTGTGACGCAACCCTTATAAAA
TGAAATGAGAGCCTTCCCTCTCTGGCTTATCAGCTTCAGACTTCCTTAATT
GAGTTCCGCCATCCTAGTGAGTCTCACCATACTCCCGAAATAACCTGCTGG
AGTAGGCTTATCCTACTCAACTCCTCAGATCTCTGTATTTAATTCTATTTT
ATTGCTGTTGTAGTAAATTACCACAACTGTGATGGCTTGAAACAACACAAA
ATTATTTATTTATTTACAATTCTAAAGGTCAGAAGTCCAAAATGGGTTTCA
CTGAGCCAAAATCAAGGTATTGGCAAGGTTGTGCCCCCTCCAGAGGCTTTA
GGGGAAAATCCATTTCTTTTTCTTTTCAGCTTGTAGTGACCACTGCATTTT
TTGGCTCTTGGCCTTTCCTCCACCTTAAAGCCAGCAGTGTAACATCTTGAA
GTATTTTCTCTTATTCTGACTCTTCTGCCTGTCTCTTATAAGGACCCTTG
TGATTACACTAGGGCCCATCTGCAAAATTCAGGAAAATCTGCCCATCTCAA
AATTCTTAACTTATTAAACATGTAAAGTCCCTTTTGTCATATAAGGTAATA
TATTTACAGGTTCTGGGGATTAGGACATGGATATCTTTGGAGGACAACATT
CAGCCTACCCTTTTGAGGGATAGAGGGGTAGCAGGAAGAGTTGAAACAATT
CCTTCCTTTCTTTATTTAAAAATTCTGGTTATTGATTTATTATAGTTATCA
TGTGCCTGATAAGCCAATGAAAATAGTTATAATGGCCAGGGGCAGTGGCTC
ATGCCTGTAATCCCAGGACTTTGGGAGGCTGAGGCAGGAGAATCGCATAAG
CCCAGGAATCCAAGACCAGCCTTAGCAACATAGGGAGATCCCGTCTCCACA
AAAAAATGCAAAAATTAGCTTGATGTTGTGGCACATGCCTATAGTCCCAGC
TACTCAGGAGGATTGCTTGAGCCCTGGAGTTCAAGGCTGCAGTGAGCTGAG
ATTGCACCACTGCACTCCAGCCTAGGCAATAGAGCAAGACCCTGTCAGAAA
```

FIG. 8-122

```
GAAAAAGAAAGAAAGAAAGAAAGAAAGAAAGAAAGAAAGAAAGAAAGAAAGAGAG
AGAGAGAAAGAAAGAAAGAGAAAGAGAGAAAGAAAGAAAGAGAGAAAGAGA
AGAAAGGAGAACTTTCTTGGCTTAATTTACCCAAAAGGTATGATATTTTCT
TAATTTGCATAAGGCAGAGCATGAGCTGATACCAGTTCTGGTAGAAAAAGT
AGGTGAGACTGGATCCCCCAAACAAGAGTAAATATTTAATATAATAAGGAA
AGAGTGGCCGAAAGTATTCAATGCCACAAGTAAGATTCAGAGTAGATTTTT
CAAACTGCATAATTTGTTTAAAAAGCATAATTTTATAGCTGGATTTTGCAA
GCTCTCTGAGGGGATCTTGTTCATTTTGAGAATCACTATATCCACAATTCT
TGGCACAGTGTCTGTCCTATGGTGTGTGCTATGATCCAAATGTCTGTATCC
TCTCAAAACTCATGTTGAAATCCTAACCCACAAAGTGATAATATTAGAAGG
AGGGGTCTTTGGGCAGTAGTTATACCATGAGGGCAGAAACCTCATCACTAG
GATTAGTGTCCTTATAAAAGAAACCCAAGGAAGTTTATTCAACCCTTCTGC
CATGTTAGGACTCAGCAAAAAGATGGCTACCTGTCCTCACCAGACACTAAA
TTTGCCAGGGCCTTAATCTTAGACTTCCCACCTCCAGAACTGTAAGAAATA
AATTTTTTGTTGTTTATAAGTCACCCAGTTTATGATATTTTGTTACAGCAG
TCTGAACAGACTAAGACAGTACACGCTTAATAAACATTAGTTTACTGAATG
AATGAATTCTTGCATTGCTTCACCACCAACAATCAAGATCTCTGTAGCTGG
TTTAACCCCCTCACTCCCAATCATGATTTTCATATAACAAAGTTAACTCAG
TTAAATCAACTCAATAAGGTATACATTAAATGAAATTAAAGAAGTTGTAAC
ATTTATAAACATCAAGAGTAATGTAGAAGAAAAGTCCAGAGATCCTTAAAA
ATTTAAGCCTCTCTGGCCTGACATTAACAGCTAAGGCAGGAACAGAAAACC
AAACACCTCATGTTCTCACTTATGAGTGGGAGCTGAACAATGAGAACATGT
GGACACAGGGAGGGGAACAACACTCACTGGGGCCTGTTGGGGGAGGATGGG
GTGGGGGTGTGGGAGAACATTAGGTAAAAGAGCTAATGCATGCTGTACTTA
ATACCTAGGTGATGGGTTGATAGGTGCAGCAAATCACCATGGCACACGTTT
ACCTATGTAACAAACCTGCACATCCTGTACTTGTACCCAGGAACTTAAAAA
ATAATAATTTTTTAAAAAACAGCTATTTCCAATCAGAGCAGTTCAATTCCA
TACAATTATTATTATTATTATTATTATTATTATTATTTTGAGATG
GAGTCTCACTGTCGCCCAGGCTGGAGTGCAGTGGCATGATCTCAGCTCATT
GCAATCTCTGCCTCCCAGGTTCAAGTGATCCTCCCGCTTCAGCCTCCTGAG
TAGCTGGGATTACAGGTGGGCACCACCACGCCTGGCTACTTTTTGTATTTT
TAGTAGAGATGAGGTTTCACCATTTTGGCCAGGCTGGTCTTGAATTTCTGA
CCTCATGTGATCCTCCTGCCTCGGCCTCCCAAAGTGCTGGGATTACGGGCT
TGATCCACTGCGCCCAGCCAACATACTATATTTTTTTTGATAAATTTTCT
GTATTCTAGACATGACATTAGCTTCCGACAATATTAATTTATTAAGATCTG
ACCCATGACATGACTTCATAAGAGTTCAGAGTCCACTGAATGAGACCACAC
ACAGAGACAGACAACTAGAATGAAGGATGATAAACATGAACAATACAAACT
TGCACAGGTGACTAGAAAAGAACAAATGAAGACTCCTGCCAACTGGGGGTA
TCAGGGGAAGGCTTCCCAGGCAGAACAGGGCTGCGCCAGTCTCCATGTGTG
GTATGAATAAGTCAGTAATACAGGGGAAGCACCTTCCAGAAAGAGCAAACC
CGTTGAGGCTTGGTGTGAGGAATAAGAAGTGTCCAACATGACTGGGGATTA
AAGTACAAAGGTATAAAGGAAATGTGGTGAACTGACTGGAAAGATAAGAAT
TTTTTTTAACAGTTACTTTTCCCAATAGTAGAATTAACTAGACAGGAATAG
AAATGGAAGAAGTTTTTATGTTCCCTTAGAATGAAAACTATACATTTTTTA
AGAATTATATGAACAAGGAAAATGTGACTCAAAGGCAGAAAATGATAGAAT
TTTATTATAGGGCAGAAAACAGGATCTGGCTAAATTAAACTAAGTACTCTA
```

FIG. 8-123
```
CTATACTATACCATATGCTATATTCTTGAATGGGAGAAGTAATACCATAAA
AACTATTGATTCTTCCTAAATTAGTAAACACATTGAGTGAAAATCCAAGAG
GAAGAAAGAAAAATGGAAGACAAACTGGAAATAGCCCAAATTTTCATCAGT
GGAAGACTGAGTACTTTGTGATACATAGTCATTGCAGAAAAATAACACAGT
TAAAAAGAATGAATCACATCTATAACATTTGACCTGAATACTTTCATATAA
TGTAATACATTTTTAAATGAGTAAAGCAGATACTAAGGACGTATAAAGGGA
CTCCATTTTTTCTGAATATTAATCAAGAAAATTCTATATATCTGTATCTT
TGTTTACATAAGATTGTGTGAGCCATAATAGCTGTTGACTTGGGTTATCAG
GTTTGGGTAAACAGTTTAGTGGTAAAAAAAAGATGTGTAAGACTTGGCCGG
GTGCAGTGGCTCACATCTGTAATCCCAGAACTTTGGGAATCTGAGGCAGGC
AGATCACTTGAGGTCAGGAGTTCCAGACCAGCTTGGCCAACATGGTGAAAC
CTCGTCTCTATAAAAAAACTACAAAAATTAGCCAGGCATGGTGGCGCACAC
CTGTAGTACCAGCTACTCAGGAGGCTAAGGCAGGAGAACCGCTTGAACCCG
GGAGGTCGAGGTTGCAGTGAGGTGAGATCGCGCTACTGCACTAAGCCTGGG
CAATGACAACAAAACTCCGTCTCAAAAAAAAAAAAAAAAAAGTGTAAGACTT
AGCAAAAAGGTGACCAAAAAAAAGCAACATTTATAAACTATGGATGTAAAA
CTCTATGTATGTGTGAGTGTGTATACATGTGTGAATATACATAGGATACAT
TTTTGTCTGTATGTGTATATGTACATACATGCATGTATGTGTATGTGTGTG
TATATATACAAGCTTTTTTAAAATGTTTTCAACAATATTGAATTACATTAG
AAAAATGCTAGTACTGTAGTGTACAAAGCAGGATGCGTTGTGCACATCCAC
ATACAGGAATAGAAACAGATATATACATACACACACACTACACACACCCCT
ATACCTACACCAAATATACATTGAGAGAGAGAGATAGAGAAAATAGTAACT
AAGGTAGTTAATTCTGGCCACAAGGATTTTTAGATGAATCTGACTTTCTTC
CTTAGGTTTTTTTTGTATTGTTTAAAGTTTCACACAAATAGCATTTATTTA
CTGTATAATCATAAAAGGCAAAAACCTATTTTGATTTTAGGAAAACACAAA
GCATCCAAACCAAAAATCTCAACTTAGGAAATAGCGGGAAATCTAGGGAAG
TCAACAGGACCAGGTCATGACGGTCTTTTATGCAATGTCCAGGAGCTTGAA
CTTTATCTTGTCGTTCCTATATTTCCTCAAAACAAATGTGTGTGGACGCAG
AAATGGAAATGCACAGCAGTGCACTGAGGTCACAGGAAAAATACAAAACAG
TTTTTCTGAAGTACTAACTTCACTCAAAACTTCGGGAAACATTTTAAAAAT
GGTTTTAAACAAATTTGACTAAATTTGACAAATTTAGTCAAATGCAAAATT
TTCATTTTTAAAAGGAAATAAATTTTAGAGGAAAAAACAGATGTGAAAAAG
AATACATGAAATAGTACATGAAGGAATACATGCACGTGGCATACACTTGAA
TCCATGTATATGCCAGGTTTTCTTGTGTTGCACACAAGACCAACTCTGAAG
TTAAAGATAACCCAGTAGAAAAAATTAAATGATGGGGAGTAATTAAAATGT
TTTCAGCAGGAGTAGGACATGATTTTTATATTTAGACTGTTTAGTCGGCTA
GTTATGTCTGACGGATAGAAGTGAGGACACTCCTAATTGAAAAGTAAGTGC
TACTAAGAAACTCAACGTGGGGGTCATAGAATGAAGCCAGACTTTTGTTCC
CAAGCAGGAGACAGATGCAGATAAGAGGGAATGAAGATGAAGTAAGGGCTG
AACCACAGAAGCTTCGCATCATAAGTCATTGTATTTCTCTGAGTGAACATC
ATAGAACTTATTTACTATCTGGTCACAAAATGCCACTGACATGAAAAGAAA
TCGGGTTGAAATGGCTCTAGACCAAGATTCCCAAGACATCAAGAAATCACC
AAAAGTTGCCTCAGGTTCACAAAAAAAGATATTCCAAGGGAGTTCTCCAAG
TAAGTAAACACTCATTATTTCTATAAGGCTTAGGCCACAAGACCTTGGCTG
AGACCCCTGTCTCTGTGATCTGGTCTGTACCACATTGGAAGGGCCATGACT
GATTTCTACCTAGACATTTAAGGCTGAACGGAGGCTGAAGAACCTCTTGCT
```

FIG. 8-124
```
TGCTTTCCCATAGACTCACATCTGATAACAGCCCTCATCTTAGGCCCCAGA
GGGCAAGAAGAGGTTAAGAAGGATCAACCAAAGGTAAAGTACACCAAGAAA
AGAGCAGCTCTTTGGTTAGAATTTTAAGATAAAGAGAGACACATAAAAGCT
ACTGTTGAAAAATAACAGAAGGAACAACGTTTTATCTAATCAATAGATGGA
ACAAGACAATAGAGGACCATCTCAACAATAACCTAGAATACCATGGAAGAC
AGACATAAATCATCTGTATTTGTCCTGCTCAAGACTTGCCATATGCCAGGT
ATGGTGGCTTATACCTATAATCCCAGAACTTTTAGGCTAAGGCAGGAGAAT
TGCTTGAGCGCAGGAGTTCCAGACCAGCTTGTCTCTACAAAGTTCTCTGGG
GGTTTTTTTCGTTTGTTTGTTTTTAGGCAGGTGTGATGGCACACACTTG
TGGTCCCAGCTACTCAGGATGCTGAGGTGGGAGAACAGATTGATTCTGGGA
GGTCAAGGCTGCAGTGAGCTATGATTGCTCCACTGCACTCCACCCTGGGTG
ACAGGAACTGCAGACAGCCTCTAGAAGTTGAATCAGCCTCTACCAAGAAGC
TTCTACCGGTGCAAAGAACTGAATTTTTCAACAAACCTGAGGGAGCTTGGA
AGTGGAAATTTCCACAATCAAGCCTCTGATGAGAATTCAGACTCAGCCAAC
ACCTGGATTGCAGCCACATGAGGCTTGAAGCAGGGAACCCAGTTAAGCCAT
GTCAGAACTTCTATCCACAGACCTTAGGTAATAATAAATGTGTGTTGCTTT
AAGCCACTAAGTTTTTGCTAATTTGTTTTGTAACAATTATATATAACTAGT
ACACATGAATAGTAGAATCTAATATCAGCCATTGACTTCAATGAAGGAAAA
AACAGATGTGAAAAAGAATACATGAAATAGTACATGAAAGAATACCTGCAC
ATGGCATACACTTGAATCCATGTATATGCCAGGCTTTCTTGTGTTGCACAC
CCAGACCAACCCTGTAGTTAAAGATAACACAGTAGAAAAACTGAAGAGTTA
CTGAGAGTAATTAAAATGTCTTAAGCAGGAGTGGGGCATGATTTTATTTT
TAGACCGTTTAGTCTGCTAGTTATATCTGATGGTTAGAAGTGAGCCTATCT
CTGGTCCCATGTTCTTAGAGAGAGTACTTTTATCTCTTTATCCATCTAACA
TCTCTAATTTATGTAACATCCCAAGTCCTCATTAATCCTGTGTTATTGCTG
TTGGAAGTCCATCTATCCCCTCAAGAACAGAGCCTGAAATTCCTCTTTGAA
AAATTTCCATTCATCATAATCTCAAATTTCTCCAATGTCATTTTCCACCTA
AATTTCATGTGTGACTTGAATCTCAAGACTATTCATCTGCCCCAGGTATCT
GTTTGATGCCTGGATATGTCTGAATTATTATTATTGTTATTATTATTATTT
TTTTTTTAAATGGAGTCTTGCTCTGTCACCCAGGCTGGAGTGCAGTGGTGC
GATCTCAGCTCACTACAACCTCTGCCTCCTGAGTTCAAGTGATTGTCCTCC
CTCAGCCTCCCCAGTAGCTGGGATTACAGGTGCCTGGCACCTCGCCCAGCT
AATTTTTTTGTATTCTTAGTAGAGATGGGTTTTCACCATGTTGGCCAGGCT
GGTTTTGAACTCCTGACCTCAAGTGATCCACCCACCTCAGTCTCCCAAAGT
GCTGGGATTACAGGTATGAGCCGCCACACCCAACCTTAGACCTCATCCTAC
CCAGCTCACGTGTCTTTTAATCCTTTAGCTGAGGTTGTAGTTTTAACTTAT
TGCTGCTTGAACCTATTTCAATGCAAAAGTTCTAAAAGAACTCAGCCACCA
AAATTCCCTTGATTTGCTGCACTGTACCAAATATTAGTCTTAATGAAATAC
AAGATTTGTTTCAGGATCTCAAGCCCAATATTTTCAACTGTAGGCTTCCCA
GTATCCAAGGTTTACGCAGGAGATTGGCAGTGGGTACATTCCCAGGGTCAG
TGGTTTTTATCCAGGAAGGAACCTCAGAATCACCTGGGGAATTTTAGCAAC
ATACACACCAGTGTTCTCAGGAGTGAGGCTCAGGTATGTGGATGGCAACAA
TACTTCCCTTATCAAAAAGCTGCCACCACACCAGACAAATGAAAACTGCTC
TTTAATTATACAGCTTGGCCTTACCTAATGGTTCTCAATTTTGGATGGACA
TTCAAATCACAAGGGTAGTTGGTTTTTTTTGTTTGTTTTGTTGAGACAGA
CTCTCACTCTGTCGCCCAGGTTGGAGTGCAGTGGCGCCATCTCGGCTCACT
```

FIG. 8-125

```
GCAACCTCCACCTCATGAACGTAGTTTTAAACAGCACTAGTGCCTAAACCA
GACTCCAGAGATCATGATCCCTAATCCTATCCCTACCCTGCGGTACTCATT
CTGAGATATGCCCTGGGTAATAAGAATTTTAGAAGGTACTCAGGTGATTCT
AATGTTCAACCAGTCTGAGAACCATTCGCAGACTTCATATAGATACTTTAT
TCCAAACAGCTGAGCTGGACCATAGCTAGAAGAAGGAATAGAGATGAATGA
GAGTTCATATTTTCCATAGAAAGCCGCTGCCCTCTTCTAAATGTGAATGGA
AGTTCTGGAGACCCCTATCCTAAGGTAGACAGATGACAGATACACTGGAGA
ATGCTGAAGGAAGCAGATAGGAGTCTAGGCTTTAGACCACACCTTCCAAGA
CGTACTACTCATGCCTGATGAAGTATTACCAAACATACCCCTGGGCCAATA
AACAAAGCAGGAGCAAATGTGTTTGTGTGTGTATAACTTTCTACACAAAAT
ACAGAAAAAAGTGATTCAATGTTCAGCATAAATAAAATTTTGTGTTTTAGT
ATTGTTTTATTTCAAAGTACATCTTGGTGAGAATGCATTATTTTGAACTGG
ATAAAAGCCCCCCACTACTGAATCCCAGGTCTCTCTATGAAGCCTGAATAG
AGGCACTGTAACTCTAATGGCCAAAGGGCTGGCCTGGAAATTCTCCCTTCA
GCTGCAAAAAGAGAAAAAGAATAATCCAAGCAAACAAACAAAACAAAGAAA
TGAGCAAACCACTACAACACAAAACCCTTGGGATGAGATGAGTACTAGACT
GGGAAAGTGATAGCTCTGGTATTCATGTGTGTGTGTGTGTGTGTGTGTGT
TGTGTGAGAGAGAGAGAGAGAGAGAGCACATGAGAGCACACACAAGACC
CTATAGAGGAACCAAGTAGCTTATCTTCTTCCTTGGATTCCTCTATCTCAT
AGCCTAGAAGACATGGGGTGATCCTAGCCCCTGGTAGTGTAGGACAAGGTA
GAGTGGGACTGTGGTTTTAAAATACTTTTTAGACCGGGTGTGGTGGCTCAT
CAACACTTTCGGAGGCGGAGGTGGGTGGATCACCTGAGGTCAGGAGTTTGA
GACAAGCTTGACCAACATGCTGAAACCCCGTCTCTACTAAAAATATAAAAA
TTAGCTGGGCATGGTGGCAGGCACCTGTAATCTCAGCTACTCAGGAGTCTG
AGGCAAGAGAATCGCTTAAACACAGGAGGCAGAGTTTGCAGTGAGCCAACA
TCATGCCATTGCACTCCAGCCTGGGTGACAAGGGTGAAACTCTGACTCAAA
GTTAATTAGTTAATTAAAATAAAATACTTTTTTATTTGGGGCTGGGTGCAG
TGGCTCATGCCTATAATTCTAGCACTTTGGGAGGCCAAAGTGGGAGGATCA
CTTGGGGGCAGGAGTTTGAGACTAGCCTGGGTGACATAGCAACATGCCATC
TCTACAAAAATTTAAAAAATAAAAATTAGCTGAGTGCAGTGGTGCACACCT
GAAGTACCAGCTACTCATGAGCCTGAGGTAGGGGGAATTACTGGAGCCCAG
GAAGTTGAGGCTGCAGTGAGCAATGATTGGGCCACTGAGCTACAGCCTGGT
GACAGAATAAGATGCTGTCTCTAAAAACAAAAAACAAACAAAAAAAACCCA
AAAACCTTCTTATTTTAAAATGATTTCAAACATATAGAAAATCAGAAAAA
CAGTACAAAGAACACTCATATACTTTTTACCTAGATTGTTAATATTATACA
TTTGCTTTTTCTCTACCTATCCATTTATTTATATGTCTTTATATCTCTTTA
TATATATATATACTTACTGAAACATTTGAAAGTTGCAGATAATCATCTTCC
TATATTACTCAATACTTTATCTTTAAATTCAAATTCAAATTTTACCAGCTG
TCCCAATCATGTCTCTGACAACACTTTTTCCCCTCAATCCAGGATCACAAA
TTGCATTTGGTTGCTATCTCTTTAGTCTCTATTAACCTGGAACAGTTTCCT
GGCCTTTCTTTATCTTTCATGATATGAAATGACAATGAATTTTTAAAGGTT
AGGTGTTTTGTAGATTAGTTCAGTTTTAAAACTTCACAACAAAGTGCCAAA
GATGTCTTGGCAGCAGTGCTCAAAACAGGTTGGAGATGCATAGGAGCCACA
GAGAAGGGTCTGGTTCAAAGGCCAGTGGTCGTCTCATTACAGCACTGCTCC
ATCAGGTCTAGGTCTGGAGACTTGGTAGCACGTCTATGGCCCCAAAGTGTG
TAGAGAATGTTGAGAATTGCCTAGGGTGGCAGACTTAGAGGAAGAAAGGTT
```

FIG. 8-126

```
GGTATGAGGCCTGTCTAAAATTGAATTTGGCTATAGAGTTATGGAAGGGTT
TTAGGCCATGTCTGGGTGGAATCAGATTCAGTCAGCAAGTAAGGGGTCTTT
GGGAGGTGAGCTTAGGCTGTCTGGGCCCCTTCGAGGAGGGCAGATTTTATG
GGGAAGGGCTCTCCTAGAAGAACCTAGTTTAGGATGAGCAAATCACGCAGG
TTCATTCTCCACTTTACCCTAGCACTTCCTAGGCTCAGTGGTGGTTTTGAA
CTTTTCCCATCCCTGCAATTACTCCATAAAGGGAATGTGCAAGGAAGAGGG
GAGGAAAGAGATGTGAGTTCTGCCAGAGGCTTCACTGTTTCATTCCCAGAT
TTATTTGAAACCAACCCTCCTCCTGTACTTCATGCTCTCCAAGCTCATGGT
CCTGGAACTTCACATTTACATAATACGGAATTTTTTTATTACCCTTGATC
TTTATGCATGCAATCTTTCTGAACACCCTGGACCCCCTCCTTCTCTTGGTG
ACCTTTTCCTTCTCCAAAACATGGTTCACCAGTTATTACCTCTGCAGCAGT
GGTCCTTCCAGGAGTTGCTTGCTGCTTTGTTCTTCTCTCAGCCTCAACACT
TTTTCTTATCTTGTTACAGCATTTAGAATGTAATGTTTTGTTTTGTTTTTA
AAACACATCTTGGCTTTCTGGAAACTTATATAGAAAATAATTTTTTTTCCC
TCAATAGATATATGGCTAGGGTCCAGCCTAATGTCTGCCATAGAGAAGCCT
AATGTCCAGCCTAATGTCAATAAATGTTTATTGTGGGCATAAAGGAATACA
TTTTAAAATAATGGAGTGTTTAGGTAAAATTAGGATTATTAGCTTGAGTCA
TTTAAAATCATCCACAAGAACCAGATCAAATGTACATGTCTTTAATACTGG
TGAAAGAAGTAGTTACGCTGTCTTAAAGGCAAAACGATATGGACATAGCCA
CCAGAAATACAAGAGTGCCATCTCTTGGTAAACCTGTTAGCAGACAGAGAA
GACACTGAGAAGCCATGTAAAATATACTTGATAATGTGTCTCTTATGTAGG
TTATGTAAAATGTGGAAGAAAGATGGAAACAAAATTGAGAGACGTGGTTAT
GGCATTTTCCAGGAAAATTGGAAAATATTTTCTCCTAATAATTCATGCAAA
ATGTAATGATATTTTTTAATGCAGAAGAAAACAGTGTAACAAAAAGCATTA
TAATTATGGCAAATTGTTGAATGCTTTCTCCACCCCTGCCCTTTCCACTCA
GAGTAGGAATGAAATAAGGATGTCAGTTATCACACTTTATGTTCAATATTA
TATGGGAGATGCTAGCCAGTGTACTGTGGAAAGAAAAATAAATGTTAATGT
TAGATGTTAATGGTGTAAATATTTCAATTGAAAGGCAAAGATTGTTAGAAT
CGACTTAAAAATGCAAGAACCAAACACGTTGGCTAGAAGAGAAACATCTTA
AATATAAAAACACAGATAACTTGAGAATAAACATATTAAAATATATACACT
ATGCAAACAGAAAGCATAAAAAGACTAAAATGGCTATAATAATAACAGCTA
AAATAGAGTTTAAGACAGAGAGTGTTACCAGAGACAGAGTGATATTTTGTA
TTGTTAAAGGAGTCAGTTGCCAGCCTGGCCAACATAGAAAAACCCCATCTC
TACTAAAAATACAAAAATTAGCCAGTCATGGTGGTATGTGCCTGTAATCCC
AGCTACTCGGGAGGCTGAGGCATGGGAATTGCTTGAACCCAGGAGGCGGAG
GTTGCAGTGAGCCAAGATCACACCACCGCATTCTACCCTGGGTGACAGAGT
GAGACTCTGTCTCAAAAAAATAAAATAAAATAAAAATGCCGAGGTGGGCGG
ATCACCTGAGGTCAGAGGTTCGAGACCAGCCTGGCCAACGTGGTGAAACTC
TGTCTCTAATAAAAATACAAAATTAGTTTGGCATGCTGGCACATGCCTGTA
ATCCCAGCTACTTGGAGGCTGAGTCAGGAGACTCGCTTGAACCCAGGAGGT
GGAGGTTGCAGTGAACCAAGATTGTGCCACTGTACTCCAGCCTGGGCAACA
GAGTGAGACTCCATTTCAGAAAAAACAAAAACAATGACAATAGAAAAGTGT
CATTTCATCAAGAAAACATAATAATCATAAATGTATGATTCTAACAACAGA
GTTTCAAAATACATAACGAAGTTTTAAAATACATAGCAAAATGTCATAACA
GAGTTTCAAAATACATAAAGTAAAAATGGAAAAGAAAAGACAAAATAGACA
ATTCTACAATCACATTTGGAGAGTTTAACACCCTTTTTTTGGTAATGATGC
```

FIG. 8-127

```
AATAACTAGACAAAATATCAGTAAAGACACAGAAGATCTGAACAATCCTAT
CTATTATCTTGAGCTAATTGATTTATAGAACATTATACACAATATCTGCAT
GCACATTTTGCTCAAGTACACATGATATATACATCATGATAGATCATATTC
TTTTTTTCTTTTATTTTTAGTTGACATATAATAACTGTACATATATACGGG
ATAAAGAGTGATATTTTTATATGTGTACACAATGTGTAATAATCAAATCAG
AGTAATTAGTATATCCATCACCTTAAACATTTATCATTTATTTTGTTGTGA
GTATTCAAAATTCTTTTCTAGCTTTTTGAAAATATACAATAAATGAGAGTT
AACCATATGCACCCTACAATGGTGCAGAACACCGGAACTCATTTCTACAAT
CTAGCTGTAATTTTGTCACCATTAACCAACCTCTCCCTATCCTCCCCTCCT
TGCTACCCTTCCCAGCTTCCGGTACCCACAGTTCTGTTCTCTAAATCCATG
AGCTAAAAATTTTTCTCTACTTTCACATATGAGTGATAACATGTAGTATTT
ATCTTTCCAATCCTAGCTTATCTTACTTAACATAATGTTCTCCAGTTTCAT
CTACGTTGCCACAAATGACAAGATTGCATTCTTCTCATGGCCAAATAGTAT
TTCATTGTGTATATATGCCACATTTTCTATCCATTTGTCTGTTAATGAACA
TTTAGGGTTGACTCTATATATCAGCTCTTGTGAAGAGTGACGCAATAAACA
TGGGGATGTAGGTGTCTCTTTGTATACTGATTTCCTTCCCTTTGGATAAAT
AGCCAGTAGCAGATTTTCAGCCTCATCTGGTAGATCTATTTTTAGGTTTCT
GAGAAACCTCTGTTGTCAGTAGGCTGGTTCAGATTCTTGAATTCCCTGCAC
AAAAGAATTTGAAAGCCAGTCCAAAGTAAAAGTAGGCAAAGGAGTTTATTG
CAAGGTGAAAGTACACGCTGATAGCAGAGTCAGGGTCGGCTACTTCAGCAC
CAATTGACACTGAAGAAACTCCCGTTATGGGAGTCCTACGTGATTATCCAT
GAGGGGGTGGGAATGGGCATTGTTGTTAAATATGTTTTGGGTGGTCTCTTG
AATGTGCATGCAATATTGCCATACACGCTAGTACATACATCACATGTATTA
TTAGCATTTTAATTCTCTACCCAAGGGTGTGTTTCTTACTATTAAAATGAG
TATATGTCAACCTGAGAACACAGCTTGTGGGTTTCTGCACTTGCACGAACT
TAGGGATTTTCCCTCCTGCTCTTCTACCTCCTTGACTGAGGATATTCTAAC
CACTAGCCCCAGATGCAGTTTGTGTAATGTCAAGAGATTTGTTCTCTCCAT
CAATTTGACAAGTTTCTTGTTTCCTTTCAAGGGAGGCTGTGACCACCCTAT
GTAACCTACCTCACTTCCATACTATTTTGCATAATGGCTATGCTAATTGAC
ATTTCCACCAGTGGGACATAAGAGTCCCCTCTTCTGTACATCCTCACCAGC
ATTTGTTATTTTTGTTTTTTTGACAATAGCCATTCTAACTGGGGTGAGAT
GATACCTTATTGTGGTTTTGATTTGCATTTCCCTGATGATTAGTTATTTAT
ATGGTTTGGCTGTGTCCCTACCCAAATCTCATCTTGAATTGTAACTCCCAC
AATTCCCATGTGTCCTGGGAGGAACCCAGTGGGAGGTGACTGAATTATGGG
CCGGGTCTTTCCTATGCTGTTCTTATGATAGTGAATGAGTCTCACGAGATC
TGATGGTTTTAAAAACGGGAGTTTCCCTGCACAAGCTCTCTCTTTGCCTGC
TGCCATCCATGTAAGATGTGACTTGCTCCTCCTTGCCTTCCACCATGATTG
TGAGATCTCTCCAGCCATGTGGAACTGTAAGTCCATTAAACCTCTTTCTCT
TGTAAATTCCCCAGTCTCAGGTTAAGTCTTTATTAGCAGCATGAAAACAGA
CTAATACAGTGATGTTGAGCATTCTTTCATATATTTGTTGGCCAATTGTAT
GCCTTCTTTTGAGAAATGTCTGTTCAGTTCACTTGCCCACTTTTTAAATGA
ATTGTTGGTTGTGCACGGGTGGCTCGTGCCTATAATCCCAGCACTTTGGGT
GGCTGAGGCAGGAGAACTGCTTGGGACTAGGAGTTTGGGACAAACCTGGGC
AACACAGAAAGGCCCTGTCTCTAAAAAAATGAAAATAATAAAAATAAATGA
ATTATTAAATCTGACTACAGTAGAAATAAATTTGAAATCAATAAAAATAAG
AAATGTAGAAAAAAACACACATATTTGGAAATTAAACATCATTCTAATTAA
```

FIG. 8-128

```
TCAATCTCTCCAAACAAATCACAAAAAATTACAAAATACATTGTACTATAT
AATAATGACAATAAAGCACATCAAAATTCATGGGATGCAACTTAAACAGTG
TGTAGAGAGATCTGTAACTTAAATTGCTTATAGTAGAAAACAAATAAAGTC
TAAAATGAAAGTCCAGATTCTACAAAGGTGGTATGTCTAATAAGAGATACT
TGTGTTCTCCCAGTAATACTGCGATCCCAAAGGATGATAAAAGTAAACTAG
AAGTAATCCCATCCTACTCTCTGGAAACTGCTAGAATGTTTGCTCTGCTTC
TCAGCAGAGCAAGGGATGTGAGAGAGGTGGGGAGAGACAGAGAGAGAGAGA
GAGAGAGAGAGATCATCAATCCTGATAAGTTGTAACCACAAGCCAACTT
TTATACACATTTAGGCTAAAAAATAAAAAGTCTTGGCTAGCCACAGAGGCT
CATGCCTGTAACCCCAGCACTTTGGGAGACCAAGGTGGGAGGATCACTTGA
GCCCAGGAGCTCGAGACTGGCCTGGGCAACAAAGTGAGCCCCATCTCTAAA
AAAAATATTTAAAAAATTAGTCAGGCATGGTGGCACACACCTGTAGTCCTA
GCTATACAGAATGGTGAGGCAGAAGGATTGCTTGAGCTCAGTAGGTTGAGG
CTGCAGTGAGCCATGTTCACACCGCTGCACTCCAGCCTGGGTGACAGAGTA
GGACTCTGCGTAAAAAAAAAAAAAAAAAAAAAAAGTCTCAATTCATGAATTG
AGTTTAAAGTAATACTTGACTGGTGGTACCCCAGCTTCCTGGCAAAAGCAG
ACACAAACCCCCTCTAGAAGAAAGAACATCCCAGTCCTCAGTGACCCATAA
GTAATTTTACCAGAAAAATAAAGAAGTTACTGGCAAAATCATCAAATGCAC
AAAATGGATTGGAGGAAGCGTAGCAAGAATAAATGAAGAGGAGCTGGGTGC
TGTGGCTCACGCCTGTAATCCCAGCACTTTGGGAGGCTGAGGTCAGGCGTT
TGAGACCAACCTGGCCAACATGGCAAAACCCCGTCTCTACTAAAAATATAA
TAATTAGCTGGGCATGGTGGCATGTGCCTATAGTCCCAGCTACTTGGGAGG
CCTGAGGCAGGAGAATCGCTTGAACCCGAGAGGTAGAGGCTGCAGTGAGCC
TAGATGGTGCCACTGCACTCCAGCCTGGGCAACAGAGTCAGACTCTGTCTC
AAAAATAAATAAATAAATAAATAAATAAATAAATAAATAAATAAATAAATA
GGGATCAGGAGGTTTGAGTAAATAAGGTTAAAAGTGATGGTGTTCTAGACT
ATTTGTGTCTTTATATTAAAGTGAATTTTTTGTAGGCAGCATGTTGTGGCT
CTTTTTTTGCTTTTTTTGTTGTTGTCTGTTTTTTTAATTCAATCTGACAA
CCTCTGCTTTTGTATTAGAGTATTTAGATCATTTACCTTAAGTGTGATAAT
CTATATGGGTAGAGTTAAGTCTATCATCTTGCTATTACTTTCCCATTTGTC
CCATCTGTTCTTTGTTCTCTTTTTCCTCTTTTTTTTCCCATCTGTTGAACA
ACTTAAATATTTTTTCTCATTCTATTTTATTTCTTTTTGTGGCTTGTTAGC
CATAATTCTTCGTTTCATTATTTCAGTGGTTGCCTTAGAGTTTATAGTATA
CATCATTAATTTATCGTAGTTCATCTAAAAGTATACCACTTATATAAAATA
ACATTATTTTCATTTCCACTTCTTTTGCACTGTTGTTGTCATACACTTTTC
TTTTGTGTGTGTGTGTGTGTGACAGAGTCTAGCTCTGTTGCCTAGGCTG
GAGCACAGTGGTATAATTTTGCCTCACTGCAACTTCCACCTCCTGGATTCA
AGTGATTCTTGTGCCTCAGCCTCCAGAGTAGCTGGGATTACAGGCGTGCAC
CACCACGCCTGGTTAATTTTTGTATTTTTAGTAGAGATGGGGTTTTGCCAT
GTTAGCCAGGCTGGTCTTGAACTCCTGTCCTCAAGTGATCTGCACGCCTCG
GCCTCCAAAAGTGCTGGGATTACAGGCACGAACCTTTGTGCCCGGCCTGTT
TTACTTTTAAATGCTATAAATCACACATTACATTGTTAACTATTTTGTGA
AAATAGTCAACCACATTTTATGGAGAAAAAATATTATCTGTTTACTCACAT
AGTTACAATTTTCTAGTACTGTTTATTCCTTTGTATAAATAGGAATTTCAA
TATGCCTAAGGGACTTTTATCATTCTGCCTAAAGGACTTTTAAAAAATATT
TTTTATTGTTCTAGTCTGCTGATTAGATGTTTATTGCCTTTAGGCAGGGAG
```

FIG. 8-129

```
ATAAAAAAATACTACAATATTTTAGTTAATGACTGTGTCAATCAAAAAGAA
GCAAGACAATCTACCATTTAATTGCACGGTTGATTTTTTAAATGAAATAGA
AAACATCCACATATACAGTACAAAATGTATCATAAAACTCTCACATATGAC
TAGATAAATTCCTTCCTCTTTTCTCTGTATTAAATTGTCTTATTTCACCCT
CATTTGGGGGGAGTTTTTTTGCTTGGTACAGAATTGTAGGTCTTTCATTAA
TCTAAAAAATTTTGCTCCACTGTCTTTTTGCTTATATTGTGTCTATGAGAA
ATATGTGATCTATACACTTGTTCTTCTGTACATAATGTGCCTTTTGTTCTT
GGCTGCTTTGAAATTTTTCATTTTCCTCTTGCTTGCTTTGGGTTTGATTTG
TTCTTATTTTTCTAGTTTCTTTTTTTTTTTAATTTTGAGACGGAGTCTCG
CTCTGTCTCCCAGGCTGGAATGCAGTGGCGCGATCTCAGCTCACTGCAATC
TCTGCCTCCTGGGTTCAAGTGATTCTCCTGCCTCAGTGTCCCGAGTAGCTG
GGACTACAGGCAGATGCCACCAGGCCTGGCTAATTTTTGTATTTTGTTAGT
AGAGACAGGGTTTCACCATGTTGGTCAGGCTGGTCTCAAACTCCTGACCTC
GTGATCTGTCCGCCTTGGCCTCCCAAAGTGCTGGGATTACAGGCGTGAGCC
ATCACGCCCAGCCTAGTTATTGATTTCTATCTTCATTCCACTTTGGTCAGA
GAATATATACTCTATTATTATAGTCCTTTTACATTTATTGAGACTTATTTC
ATGAAGTAATATACAGTCTATCCTGAAAAATGTTTCATGTGAGCTTCAGAA
GGATGTTTATTCTGCTGTTTTGGGGTGTAGTGACCTATAGATTTATGTTAG
GGTCAGGTTAGGTGTTTTCAAGTGTTAAGTCTTCTATTTTTTGTTGATCT
TGTCTAACTAGTGAGGTATTGATGTCTCCAACTATTATTGTCGAATTTTCT
ATTTCTCCCTTCAATTCTGTCAGTTTTGTTTCATGAATATTAGGGCTCTGT
TGTTAGGTGCATGTATGTTTATAATGTTATGTTTTCTTGATGAATTGACAC
TTTTATCATTACAAAATACCTTTCTTTATTTATTATAACAATGCTTATCTT
AAAGTTTATTTTGTCTGATATTAGTATACCTACTCCAGACATCTTTTGAGT
ACTATTTGTATGTGATGAATTGTTCCTTTCTTTCTGCTCTCAAGATTCATC
TTCTTCATCTTTTGATAATCTGATTATGATGTGTCTAGGTATGGATCTCTT
TGAGTGTATCCTACTTGGAATTCATTGAGCTCCTAAAATATGTATGCAAGT
TAATGCTTTTTGCCAAACATGGGAAGCTTTGAGAAATTATTTCTCCAAAC
ATTCTCTCTCCCTGTCCTCTCACTTTTCTCCTTCTAGGAGTCCCATTATGC
ATATATTAGTATGCTTGATGGTATCCCCTGTCTCTAAGGCTCTATTTCTTT
TTCTTCATTCTGTCTTCTTTCTGTTTTTCAGAGTAGATCATTTCAATTGAC
CTATCTTTGAGTTCACTGATTACTTCTTTTTGCTGCTCAAATTTGCTGTTA
AAGCCCTCTAGTAATTTTTTTTTCTTACAGATGAGATATCATGCTGTCGTT
CAGGCTGGAGTGACCATGATCCTCTTACTGGGATCACAGATCACGCATGCT
CCAGTCTGAGCAGCAGCATGAGCTCCAGCTTGCTCCAGCCTGAACAGCAGC
AATACATTCTTTCACACACAAAAGGGTTATTGGATCTCACACAAGAAGGAA
TTTGGGGCTAGTCCATACAGTAAAGTGAAAACAAGTTTATTAAGAAAGTAA
AGAAGGGCCGAGCGCAGTGATTTATGCCTGTAATCACAGCACTTTGGGAGG
CTGAGGCAGGCAGACCACTTGAGGTTAGGAGTTCGAGACAAGCCTGACAAA
CATGGCAAGACACTGTCTCTACTAAAAATACAAAATTAGCTGGGTGTAGTG
GCACATGTCTGTAGTCCCAGCTCCTCAGGAGACTGAGGCAGAAGAATCGCT
TGAACCCAGGAGGCAGAGGTTGCAGTGAACCAAGATCGCACCACTGCACTC
CAGCCTCTAGCCTGGGTGACAGAGTGAGACTCTGTCTCAAAAAAACAAAAA
AAAGTTAAGAAATAAAAGAATGGGTCATGCATAGTGGGTAATGCCTGTAAT
CCTAGCACTTTGGGAGGCCAAGGCAAGTGGATCGCTTGAGGCCAGGAGTTC
GAGACCAGCCTGGCCAACATGGCGAAACCCCATCTCTACTAATAATACAAA
```

FIG. 8-130

```
AATTAGCCAGGCATGGTGGCACCCACCTGTGGTCCCAGCTAGTTGGGAGGC
TGAGGCAGGAGAATTGCTTGAACCCGGGAGGTGAAGGTTGCAGTGAGCCAA
AACACGTCACTGCACTCCAGACTCCAGCCTGAGTGACAGAGCGAGTCTTTA
TCTAAAAAATAAAAATAAAAGAAAAGAATGGCTACTCCATAGGCAGAGCAG
CAGTATGGACTGCTCAAATAAGCAGACGTATAGTTATTTCTGGATTATGTG
CTAAACTAATGGATTATTCAAGAATTTTTCAGGAAAGAGGTGGACAATTCC
CAGAACTAAGGGTTCTTCCCCGTTTTAGACCATATAAGGTAACGTCCAGAT
GTTGTCATGGTATTTGTAAACTGTCGTGGCACTGGTGGGAGTGTCTTGTAG
CATGCTAATGCAGTATAATTAGTGTATATGAGCAGTGAGGATGACAAGAGG
TCACTTTTGTGGCCATGTTGGTTTTGGTGGGCTTTAGCTGGCTTCTTTACC
GTTACCTATTTTATCAGCAAGGTCTTTGTGACGGGTACCTTGTGCAACCTT
CTATCTCATCCTGTGACTAAACTCCTGGTTAGAATGCCTAACCTAACCCAG
CAGGCCTCAGCCTTATTTTACCCAGCCCCTATTCAAGATGGAGTCACTCTG
ATTCAAATGCCTCTGACATATTTTCCCACTCCCTTTTACCAGGGAACCCTT
AATCCTAAGGATTGCAGTGGGATAAAGATCCGTCTTCTATAACTTCTTCAG
ACTAAATAGGGGCAATGATATTCCTGTCTAATTATTAGGGTCTCTTGTGTC
CAGGGTAGAGAGGAGCTCAGTCACAAAGTGTCAGTATGGTGAGACATTCAT
AACTCTGAGGCTTCCCAAAGTGTTGAGATTACAGGCGTGAGCCACTGTGCC
TGGCCAGGGTCCCATTTTATACCAGATCCTGGATCCCAAAAGAGGGAATC
AGCCCTCTTTTGGGGGATCAGCCATCTCCCCTGGGAATCTTATCTCTCGGT
GGGGATGGAGACATTTCCATACCTTCTAGGTAGTCAAGAGAATGCTTCTTG
TGATCCAAAAGTGCAAATAGCCAAGTATTCACCTATATTTGCCTTTAGCTA
TCCCCAGAAGTATATTTCCTACCTGGTTATTACACACCAGATCTCCCTCAT
AATGCAAAGTAATTTCTGATACCCCCAAAAGTCAAAAACATCAGATAACAT
AATGCAAAGCCAAACAGAGCCTTAGATTTTGCGAAGGATCTATCCACTTCC
AGTTCCTGGGGTTTCATGAGGAAAACAGAGGTTTTCCCAAAATGGGGTCTG
TGGTGCCTCCTCTGCTTTTCCCAAGGAGTCCCAGGCTTTTAGAGATTGAAT
ATCCACTTTTAATTAAGCTTTTAACCATAAACCATAGCACTCTAAAGCAAA
AAAAAAAGGAGTCCTTTTAAGTTTCTTATTACTCAACTTTAGCCATCCCAC
ACGGCCATTATTTCTGGCTTTTGAACTTTACCAAAGATAATCTCCCAGGTT
CTCAGAGAGAGGAAAACTCAAGACAGTGTGTGGAGGGGAAGAGAACAGAAT
CAACAAATGGTAAAGGTCACACAGATATCAATCAGAAAGTACTCATTCCCT
AAGCCAGGATTGAACCTTGGCCGCCATTATAAAATGACAAATCCTTAGCTG
CTGAGCTACAACACTGGTTAGTTTCCATTGCCCTTCCCAGAAGGGGTCCAG
AGCAGCCAATTTTGAGCTTGCAATGGCTTGAGATAATTTTTAGAGTTAACT
ATTACATAAACCCCAAAATTCCTGTTCCCTGGATGGCAGAGACCAAGAGAA
AGTACCGCCACGTGGTTACAAGGTGAAGCTCCAAAGGACATAAAACAAGAT
GAGAAGGAAACTTCATCCAGTTTTTATTTTTTTTTTTTCCAGGGACCTGT
AATAAACTTTGCAACGGACCAGTTTACTGGGCTGGCTTGAACAGCAGGCTT
ATGGAGTCCTGAGCCCATGTTCTATCCTACCATATTCCTCTTTATGACAGA
GTAATACAGAAAGACAAATTGATATCACAAAGTATACCAGATTCATTACAG
CTTAAGACTAGCCCCACAAATCCTTGTTCCCATTAATCAAAACTTTACAGA
GGTGATAAACAGTGATTTTTACCATTCATTCAGTTTTCACTAAGAGAGAGA
GGCCAGAAGCCTGACTGGTAAGAAATCTTTACCCTTTTGCTGGCATGCCAG
GTTTCTGGGTTCTCTTTCACTGAGCAGCACTAGCAACCTTGCTCACTGCAA
AGCCCTTGGGTCCAAGCTACGACACAAAAGAAAACCAACTTTTTTCTGTTT
```

FIG. 8-131

```
CATGGAACCACAGGCAAATAAATGTCTCTCACTTTTGTAAGATGCTGCCCA
ATGGCCACATAAAGTAACCAAATTAACGTTTTCCATTTCAGCCAGAGCAAT
ATACATGTGACAAAACATAGACATTGGCCACTCCACTTAGCACCCAATATC
TAACTGGGAAGGCTCAAACTTGCCCCCAGATAGGCCCTTTCATCTTTAATC
AAACTTCTGACCAGGAGTTTCAACATATGGTCTCTGGGCAAGATGGTTGTC
TCAAGTAACAGAAAAGACAGAAAAGAGAAAAGAGAGAAAGGGAGAAAAGCA
TTGCCTGTGGTGAGATGGGGAAGGTGAGGAGTTCACAGAGGCCAGAGAAAG
ACCCACCCATTGCAGCAACACTGAATCAAAAGTTCAGGCGGCTGCTTGTCA
TAGCAAAGGGATCTTTTCCAACAGTCCTATCAGCTGTCAAGCTTCCCCTTT
TGGAGAGAAGAAAAGTTCCCAATGTCCGTGATCCTGTACATGCCTAATCC
TGTCACCCATAGCTGTCAGCAAAGAGCACAGGGAAGATTAATACAAACAGA
ATAGCAGTTAACATCCCCTAATGCTAAATCCGTTTTTAACCAAGAGAGACT
TTACTGAGAGGGGCCTCTAACCCCTTAAATCTTAAGGACTGTAGCCTTCCT
AAGTTGGGTCTCAAACCCAAGTTCGGTCAAGCATTCTTGCCCTTTATTAAG
AGCGGACTGAAACCCTCTCTGTCTTAGGAGAGACCCTATCTCCCCTAAGTT
GCACCTCTAACCCAATCCTATCCTTTACCCGGGGACTCCACCACTTACCCA
AAGTCAGCCAGTTGGTGCTGTAGTCTGTTTCCTTTGGCTTCAGAGTCTCCT
CAGTATTGTCCCTTCGTGGTCACAGAAAGATTTACCAGAAANGGGTCTTGA
TCCAGACCCCAAGAGAGGGTTCTTGGATCTCACACAAGAAAGAATTTAGGG
CAAGTCCATACAGTAAAGTGAAAGCAGGTTTATTAAGAAAGTAAGGAAATA
AAAGAATGGCTACTCTGTAGGCAGAACAGCAGCGTGGTCTGCTCAAATAAG
CATACTTATAGTTATTTCTGGATTATGTGCTAAACAAGGGGTGGATTATTC
ATGAGCATTCCAAAAAAGGGGTGGACAATTCCCAAAATTGAGGGTTCCTCC
ACCTTTTAGACCATATAAGGTAAAGTCCAGATATTGCCGCAGTATTTGTAA
GCTGTCATGATGCTGGTAGGAGTGTCTTTTAGCATGTTAATACATTATAAT
TAACATATAATGAGCAGTGAAGACAACCAGAGGTCCCTTTGGTGGCCATGT
TGGTTTTGATGGGTTTTGGCCAACTTCTTTACCACAACCTATTTTATCAGC
AAGGTCTTTGTGATGTGTACCTTGTGCTGACTTCCTATCTCATCCTGTGAC
TAAGAATGCCTAACATACTGGAAATGCAGCCTAGCAGGTGTCAGCCTTATT
TTATCCAGCGCCTATTCAAGATAGAGTCATTCTGGTTCAAATGCCTCTGAC
AATGCAGCCTTGAATTCCTGGGCTGAAGCCATCTTCCCACTTCAGCCTCCT
GAGTAGCAGGGACTACAGGCACACACCATCATGCCTGGCTAATTTTTTTGT
ATTTTTTTTTTAGAGATGGGGTCTCACTGTGTTGCCCAGGCTGGTCTTGA
GCTCCTAGGCTAAAGCAATCCTCCTGTGTCATCCTCCCAAAGTGTTGGGCT
TGTCAGAGGTATTTGAACAAGAAAGACTCCATCTTGAATAGGAGCTGGGTG
AAATAAGGCTGAGTCCTGCTGGGCTGCATTCCCTGTAAGTTAGGCATTGTA
AGCCACAGGATGAGGCAGGCAGTGGGCACAAAATACAGGTCATAAAGACCT
TGCTGATAAAACAGGTTGCAGTAAAGAAGCCGGCTAGGCCAGGTGGGGTGG
CTCACACCTATAAGCCCAGCACTTTGGGAGGCTAAGGTGGCTGGATGGCTT
GAGCGCAGGAGTTGGAGATCAGCGTAGGCAACATGGCGAAACCCGGTCTCT
ATTAAAAATATAAAAAATTAGCTGGGTGTGGTGGCACATGCCTGTAATCCC
AGCTACTTGGGAGGCTGAGGCACGAGAATCGCTTGAACTCAGAAATTGGAG
GTTTCAGTGAGCTGAGATCGTGCCACTGCACTCCAGCCTGGGCAAAAAAAA
AAAAGAAAAAAGTAAAGAAGCTGGCTAAACCCCACCAAATCCAAGATGGCG
ATGAGAGTGACCTCTGGTCATCCTCACTGCTCCCCACCAAATCCAAGATGG
CGATGAGAGTGACCTCTGGTCGTCCTCACTGCTATGCTCATACCAGCGCCA
```

FIG. 8-132

```
CGACAGTTTACGAATGCCATGGCAACGTCAGGAAGTTACTTTATATGGTCT
AAAAAATGGAGGCATGAATTATCCACCCCTTGTTTAGCACATAATCAAGAA
ATAACCATAAAAATGAGCGACCAGCAGCCCTCAGAGCTGCTCTGCCTATGG
AGTAGCCGTTCTTTTATTCCTCTACTTTCTTAATAAACTTGCTTTCACTTT
ACAGACTCGCCCGAATTCTTTCTTGTGTGAGATCCAAGAACCCTCTCTTGG
GGTCTGGATCTGGACGGACCCCTTTCCGGTAACAGGATTACAGGTGTGAGT
GAGCCACCATCCCCAGCCTTAGTAAATTTTTATTTCAGTTATTATATATTT
TTATTTATTTTCTGTTTTTCAGTTATTATATTTGAAACTCCAGAATTTTTA
TTTAGAATGTATTAACAAATCAGGAGTACTGGCATAAGCCTGGCACAAAGC
AAATGTTGACATAGGTCTGGCACAAAACAAGTGTTCAATGCATTTTAGCTA
CCTTTAAGTGTATTATTACTAGCTGCTTCTGGGGCTATCCGGGGAAAATTA
TCCTTGCAAAACCCCCACTCACTTCCAGAGCAGGCTTCAGTGAAGCAGTCA
TCTGTGTCATGACAAGAGCCAAACTCTGTAAAACATTTGAAGAGATTTATT
CTGAGCCAAATTTGAGTGACCATGGCCCATGACACAGCCCTCAGGAGGTCC
TGAGAACAAGCGCTCAAGGTGGTTGGGATGCACCTTGGCTTTATACATTTT
AGGGAGGCATGGGACATCAATCAAATACGTTTAAGAAATGTACACTGGTTT
GGTCCAGAGAGGCGGGACAACTGGAAGCAGCGGAGGAGTGGGGTGGAGGTG
ATGACAATTGGTTGAGTTTGTATAAAGATTTGGGATTAATAGAAAGGAGCA
CTAGGTTGTGATAACAGGTTGTGAAGACCAAAGTTGTACTATGGGATGAAG
TTTTTAGCTAGCAGGCTTCAGAGAGAATAGGTTGTAAAATGTTCTTATCAG
ACTTAAAAGCTGTGTTGATGTTAATGCCAGAGAGGAATAATGAGGCATGTT
CAACCCCCACTTCCCTTAATGGCCTGAGCCAGTCTTTCAGGTTACATTTTA
AGAAGCCTGACTGAAGAGAAAGTCTATTCAGATGGTTGGGGGCTTTAGAAT
TTTATTTTTGTTTTATACCTTTGCCCTTGGAAGTTTTGCTGAAAAATGAAC
ACAAAAAAGGCAGATTCATAAGATAAAAGGCTTTACAATTTAATTACTCT
GTGGTTCTCCTCATGCACATAGTACCAATATCCCAGTGGAATTTAGAAGCT
TATATGCCACCTTGAAGTTGAAGAAATAACAGGGGCTTGATCCTTGCAAAA
TAGGTTATGGGAAACAGAAGAAGAGGAATTCTGTTGAGGGGCAATATGTAA
CTACCAGGAGAGACTAATTGGATCAAAGAACAGATAAATTTGTAAATAGTT
CTCCTTGGAATTTAAATGATGCTTAGAGACTGATTATCTTATAAAAGGGTC
TGTTCAGGTGTGGTTACATTCTTGGTCTTTCCTATAATGCACAATGAGATA
ACAGAGAGGGAGAAAAGAACAATTGTTCTCGCTGGTGGGGCCATCCTATTT
TTATGTACCTAGGGAAAAGTCTCTTTAGTGTCTGTTGATCTCTAAGAGTTT
TCATTCAAAATACTCATTATATCAGGAAGCCACATTTTGGGGTGAAATTC
ACTACTCCCTTTTAGAGATACGGGTACAAACTGTTTGTAAAGAATGCTAAG
ACTTTGCCGGGTGCAGTGACTCACGCCTGTAATCCCAGCACTATGGAGGGG
CCAAGGTGGGCAGATCACTTGAGGTCAGGAGTTCAAGACCTGCCTGGTTAA
CATGGCAAAACCCCATCTCTATTAAAAAAAACAAAAATTAGCCAGGCGTGG
TGGTGGGCATCTGTAATCCCAGCTACTTGGGAGGCTGAAGGCAGGGAGAAT
TGCTTGAGCCTGGGAGGCAGCTGTTGCAGTGAGCCGAGATCACGCCACTGA
ACTTCAGCCTGGGCAACACAGCGAGACTGTCTCAAAAAAAAAAAAAAAATG
CTAAGACTTACTTTGGGACATCCTTTGTCAGGGTCCATGATTCTGATTAGC
TCAAGGCAGGTATTTTTTTTTTTAATAGAGACAGCATCTTGCTATGTTGG
CCAGGCTCGTCTCGAACTCCTGGCCTCCAGTGACTCCCCCCACCTCAGCCT
CCCCAAGTGCTGTGATTACAGGTGTGAGCCACCACACCGGTCTGGTTTTTT
TTGGTGGTTGTTGTTTTAATCCTATAATCCTGTGTCCTTTCTTCCTACCTC
```

FIG. 8-133

```
TGAGTAGTGCTTACTCTCTCCCCTTTAGTCATTTGAAAAGTTTATCAGAAA
GTGGGTGCAGTTTCAGGCTGGGTACCGTGGCTCATGCCTGTAATCCCAACA
CTTTGAAATGCTTAGATGGGAGGATCATTTGAACCCAGTTCAAGATTACAG
TGAGCTGTGATCGTACCATTGTACTTCAGCCAGGGTGACAGTGCAAGAGCC
TGTCTCTAAAAACAAACAAAAAATTGCTTTCACACTGTGATGCTATCACAT
CTCTCCTAAGCTCTTGTTGGGGCTCAGAAATTGATACCCTAATATATGGCC
CTTGGTCATATTGAACTGAAGAAGCCTCAAAGTCTCTCTGACATCCCTGCC
ACCAACTATCCCTACCAAAACACATCGTGGAATTAAAGTTTCTTTATCTAC
CTAAGATCCAGACCCACCAAAAAGAGCAATTATTTTTATTTACCCTTCCTG
TAAGACCAAGAATGTAACCATGCCCGAACGGACTTTCACAAGATAATGTTC
AAGTTAATCTCTGTTCCCTGATCTACTTACTCTCCCTAGTAATGAAAGGAG
TTGGCCAGCTTGCTTTAGGCAGACAGTAAGGGAATGGTACCCAGAGAACCT
CTGACCTGCCCCACAAGTGCTTACACCGGATGTTTTGTGCAGATAAGGGAA
CTTGCACAGGGGGCTTGCCTAAACATGCCTGCAGTGGATGATTCCTTTCCT
TAACACATGCACAGTTCAGGAAATTAATCAATATGGAGTAGCTCAGTCTAA
AGGCCTGCATGCACTGGTAGGACAGGGTGGAGTTGTCAGGAATTTGAGTCT
TAAGCCCTAGTATTCAACTGTGAAGAGCAAACCAGAAATCTGCTTTCAGGA
CCCTTGTCTTTGCTGAGAGCTTTCCTTTCACTTAATAAATTCTACTCCACT
CATTCTTTGATGGCTGCATGCCTAATTCTTCCTGGCTGTGAGACAAAAACC
CGGACCTAGCTGAGCGAAGGAGCAAAAATCCGCAACAGTAATCCCATCAAC
AGAGTTTCTCTTCTTCCCCTCCCATAATCTGTTTTGCCAGGATAATATATA
AGCTTTTAAGCCCTCTTGGGAAGTGGATAATCATTCTATGGTTCTCCCTGT
GTACATGTTAATAAATTTGTGAGTTGATTTTTCAGCAAAGTTTCCCCAGAA
GCCAAAGGGGAAATTTCCCTTGGCCCCTCCACTCTCTTTTCCCAGCTCTTC
TTTTACTTTCGTTTTTATTTCCTCAGCCCAGTAGGTCACAGCCTTCTTTTT
ATTTCTTCTCTGTCCAAACCATCAGTATATCCTACAGGTGGGAGAGAAGCA
GCTCTCTGGGAAACCAGTAAGCACCATGAGTTCTGATACTTTCTAGTACCA
TTTGACATATTAACATCCCCGCCACCCCTAATATGTATGGACACGCACACA
CATACCACATCACATGCATCACACTAACACAAACTATGTATCACATACCAC
ACACAGCACACACAGTACCACATACCCCACACAACACCCACACCACACTAC
GTGCATCATGCACATATGTGCACACACCTCTTGTGATGTGTGTTTAGTGCA
ATTCAGAAAGTTACTCTTTGATTTAATGCACATCACTATGCTTAGAAATAT
TCTAGTTACTGGGATTCATCAGTGAACAATATTGAAAAAAATCCATCCCTT
TGCATTCTCATGAGGGAAGCAAACACTAAACAAAATAAATTAGTAAAATAT
TCAGTGATAAGTGCCATGGGAACAAAATAGATTTGAAAATGTTTGGGAGGG
AGAGAGGGGTACACTTGCTAACAAGTGGTCAGGATAGGGTTAGTTGAGAGG
CAAAATCTGAAGGAGTTGAGGAAAGGCATTCTAGGAATAGCTGAGTGCTGA
CTCTTGCCCACAGTGGGAACACACAGTACAGAGCTTCTGAAGGAGACTCTA
GTGACCTACTTCCCATTGTGAGTCTTTGGACTCCTATATCCCATAATCACA
GGATCAAGCCTAACTTTACATATTAGAGATAATGCATTCCTCCTTGGGGAT
AGTTCAGGTTGATTTCTCCCTAGGCCTGCCTTTGTCAACATATTCCTGAAG
TCTCATCTGCACCCCATCTCTGCTTCTAATATTGGCCACTCTGTGCATGAA
CCAGCCCCTCCTTCCTGCAATGGGAAACAGGTGTGAGATGGGACAGCTGTC
ACAATCCGTTTTGCTTTTGTCTTGCTGTTATTATTGGTAATGGTAGTTTGT
TTCCTTTTTAGCATTCACTAGCTTCCTTTTCCTGATCCTTTGATAGTGTTA
CCAGAAAGGGGGTCCCAACCCAGACCCTAAGAGAAGTTCTTAGATCTCGTG
```

FIG. 8-134
```
TGAGAAAGAATTTGGGGCAAGTCTACACAGTAAAGTGAAAGCAAGAAAGTA
AAGGAATAAAAGAACGGCTACTCTACAGGCAGAGCATCAGCTTCTGGACTA
AGGATACTGATATGGTTTGGCTGTGTCCCCACCTAACTCTCATCTTAAATT
CCCACATATTGTGGGAGGGACCTGGTGGGAGGTAATTGAATCATGGGGGCA
GGTCTTTCCCTGAGTAATTTATACTGCTGTTCTCATGATAGTCAATAAGTT
TCATGAGACCTGATGGTTTTATAGAAAGGAATTTCCCTGCACAAGCTCTTT
GCCTGCTGCCATCCATGTAAGACCTGACTTGCTCCTCCTTGCCTTCTGCTG
TGGTTGTGAGGTCTCCCCAGACACGTGGGACTGTAAGAGCATGAAACATTT
TTTCCTGGTATAAATTACTCAGTCTCAGGTATGTCTGGATCAGCAGTGTGA
AAATGGACTAATACAGATACTTACAGTTATTTCTTGATTATGTACTAAACA
AGGAGTGGATTATTCATATGTTTTCTGGGAAAGATGTGGGCAATTCCCAGA
ACCAAGCGTTCCTCCCCTTTTTAGACTATATAGGGTAGCTTCCTGACATCG
CCATGGTATTTATAAACCACTATGGAGCTGGTGGGAATGCCTTCTAACTTG
CTAACACATTATAATTCGTGTATAATGAGCAATGAGAATGACTAGAGGCCA
CTCTTGTTGCCATCTTGATTTTGGTGGGTTTTGGTCAGCTTCTTTACTGCA
ACCTGTTTTATCAGCAAGATCTTTATGACCTGTGTCTTGTGCCAACTGCCT
ATTTCATCCTGTGACTTACAATGCCTAACTTCCTGGGAATGCAGCCCAGTA
GGTCTCAGCCTTATTTTACCTAGCCCCCATTCAAAATGGAGTCATTCTGGT
TTGAACACCTCTGACAATAGGACAGATCTGGAATGAGCCATGCCTGGGTAC
AGAGTCACATCCACAACAATGAAAGTTGTAGATATCTGCAAGGACTCATCG
TGGGACCAAGGATTCAGGGGCTCATTCTTTCTCCTCTCTGTGTGCTGGT
TGCCTCAGGAGTAGAATGTCCCATGCTATGCATGGGGTCTGCAACCATCAT
GCCAGGGCATGATGAATCGTAGGTGGCAAAACAACAGAAGGCTCTGTGAGC
ACCCAGGAGGGTGCAGTGCTGAAGAGTCTTCTGCTTGGTATAGGAAGAAAG
GAACGTGTTTCCCAATCTTGCCTTTATTTTGAGTAGTTGGACCAGAGGGAT
TGCAGCTGGGCCAAACTCCATGTTCCATTGGCTATCAGGGTCAGCAGGCAG
GCCAGGGGCCCAGACAGGCCAGTGGCTCCCAGAATTCAAGTTTAATTTCTC
CTCCCACCTGTGTCCTGAGCTCCCCTTACTGGTTCCCTTGGACCACTGCAT
CTACTTAAGCCAGCATTTATTATGTTGTTATCATAAATGCCTCTTACACCT
GAGACTTATAAATGTGACAAGCTCTTATTGTGAGATAGTAATCCATCTTTT
TTCCCCATGAAATAATAATTCTAACGGGTGGTGATAGTACTTTTCCTTTCA
TTTTGAAGTGGAGAAGCTGGAGCTAAGTCATTAAGGACTTGACCCTGGACC
CCACAGCCTTTTCTCCACAAAGCACAAAGCAGAGTGATGGTCCCAGGGATC
CCACACAGCTCTAAGCTGGGGGCACTCACTGCTGGGCCACTAGTGACTCCC
ATTTTCTATCCTGGCTGACCCTCGCTATTGAAGAAGATCTGAGTCCTGCAG
AAGGACAGCAAGGAGAAAAACAAGACACAGAACGGGACAGAGAAGAATAGA
AAGCTGACTCAGATGAATTTTGTGATGCCAATGAGTCCTACTGCTGTTACC
ACCCCTTTTTCCACCACACCCTTCAGAGCAGTTATAGAACCACAAGCAACC
CATAAATAGCAAAAGAAGTAACATCAGCTAGGAAGGCTTAAGGACTCCCAA
GGGAGTTGGTGGCAAAAGTAGAAAGATCTCAAATCAGAGTCTGTGAACTGA
ACCTCTGCAGGCTTCCTGTTTTAGATACTCTGTGTTGGGGTCACATGATA
GTTTACAGGGTTATTAATTGGTTCCTTCTTTTTATTGCTGTAAAAGAAGGA
TATTTCTTCCTACGTTTCCCCCTCCTTTACCGGAGAGGCGGAGTGCAAAT
GATATGAACAACGTCACTAGTTTTCTCCTAAATCTTATGAGCCCCGCCTCC
CACAGTAGTTTCACTTCTCAGTTTAATCCGGTCTGAGTTAACTTCCTGACC
CAGGAAGTGGCAGCAACAGAGGGGACTAGCAGCGAATATGTAAGTGTCTGA
```

FIG. 8-135
```
GCAGTGAAGGTTACGGAAAAGGTCCAGGCTAAGGTTTTCTCAGTGGATATG
TGAGTGTGTACTGATGGCAAGTGGGGTGGGGAATATATTTCGTGACAGCAG
GGCCCCTCCAACTCTGAAAATGGTCAGGACTTTCTTTGTTTTACAGCTCTC
ACCTCTTTCCTGCTCTTTCTTTCACCAGACTTTACACCAAATCTCAGAAGA
TTCAGAACTTAGATGAGTGGGGCCCAGGACAGGAACCCTGGAGCCTTGGAA
GGAGGGGAGCCCCATCTCCCCAGAAGAGCAGTGACCCCAGCAGAGAGGGGC
CTGGTGTATCACTGGAGGAAATAGCCTGCCAAGGAATACACGTCTTCAGAA
GAAATTCTGTGTGGCTTCAAGAGACTGATCAAATTGTGAGAGGAAAACAGC
CTACCCGGTAATTGTAGTTAAATTACTGTTTTTTATTCTAGGCACTCTTCA
AACTTCCTCCTGACTCTGCCCCTGTCCTAGAGGAGCTCCCAGGAGTAGGGG
TGTGGGGGCGGGCGGGGGGAGGGATCGGGGGTACAGGGAGAGCCCAGCTA
GGTTCTCAGAAGAGGCAGGCTTTTTCGCTCCTGGTCACTCCTCTGTTGCCT
ATCCCTGGCCTCCCCCATCTTCTTTCTGCCTTCCCTACCTCCTTGGGTCTG
CAAACTCTTTATGTTGCAATCACTCTGAACATGTCTCTTGAGATAGGTCCT
GTCCTGGAGAAGAGATAGTAAAAGTAAACTCCCCAGTTCTGCAGGAGCTCT
GATCCCATAGAAATAACTGCTCCTCAGGAGCAAACCCTCTGCTCTGCAGCC
TTCTTTCCAATTCTTATTCCCTCAGTTTAGGGAGAGGGCACAAAAAGGATA
AACCGGTTCTTCTGGTTGTTCTGGTTGCCTTGATTGCTTCCATTATCCTCC
TGGTTGGGTCTCTAGCAAGACGTTATTAGCCAGGGAAGTCCCACTTAGGCA
CCCCTCTCTGCAGAAGAGGTATTCACTATTCTCCTTTCTCTTTCTTTTGCC
TATTATACCTCTGCTCCTGAAAGCAAAACAACAACAACAAAAACACAAAC
AAAAAACAACCGACCTTATTAACCAGTGTTGGTTGTTGTTCTTTGTGGGGG
ATGGGGGGGTCGAGGTGGAGTCAAATTTTATTGTCATGATGGTGTAGGAG
CCAAGGGAACACTTCCCCTTTGCCTTCTGAAGTTCACTGAAAAATCGACTC
ACAAAAGGCAGGCTAATTGGAGAAAAGGCATACAAATTTATTAACAAGTAC
ATGGGCTAGAATCACAGAGTGATTACCCCCTCTGCCAATGGGGGTAGATAC
TTATATAGCCTTATTTATAAATACTTATGTATAAATACATAAATATAAATA
TGTATGCATATGTATGTATGTATAAATATGTATGTATACTGTATAAATATG
TATGTATAACGTTTATACATGTATACATATTTATTTCAGAGGGGAAGGGTG
ATATCAGGAGAATATAGGTAATTCTTTGAGGGGCAGTAAATGATTACTAGG
GAGAATAAATGAATATTTGGGAGGATGAATGAATGGAGGAACAGAGTTTAA
CTTGTAAATGTTCTCTTTGGAAAATGAATGAGCCTGAGAGACAGACATTAT
TTTGTGAAAGTGTCTGATTAGGTCTGGTAACATTCTTAGTCCTCTTTTCTT
CAGTACAAAATGAGATAATAGGGGTTGGAAGGAAAAACAATTGTTCTTCTT
GTCTAGTGTGACTGGTCTTTATGTAGATAGGGGAAAAGTCTCTTCCAGCAT
CTGCTGATCTCTAAGGGCCTTTAATTCAAAATACTCATTATACCAGGGAGT
CATATATTGGGGTGAAGCTCCCCATACTCCTTCAATGGAATCTGTCACAGA
TCACCCAATTGCATAAGTGTTACTACTAATTACAAAGAGTAATTCTGGTAC
CAATTATTCTTTTTTTTTTTTAAGACAGATTCTCGCTCTTTCACCCAGG
CTGGAGTGCAGTGGTGTAATCTGGGCTCACTGCAACCTCCCCCTCCGGAGC
TCAAGTCATTCTCCTTCCTCAGCCTCCTGAGCAGCTGGGATTACAGGTGTG
CACCACCACATCTAGCTAACTTTTTGTATTTTTAGTAGAGATGAGGTTTTG
CCATGTTGGTCAGGCTGGTCTCAAACTCCTGACCTCAGGTGATCTGCCCGC
CTCGGCTTCCCAAAGTGCTAGGATTACAGGCGTGAGCCACCGTGCTGGCCT
GGTAACAATTATTCTTGAAGTTAACTAGAATAGGAAAGAGTTTCACACTCC
CTGAGTTCTCTCTTTTACAGCTTTTGTGAGGAAGCCTGCATTGCTTCTCCC
```

FIG. 8-136
```
AGCACTTGGTCCAAGGTAACTTTCTGTGATAACAGAATGTTGTATATTGAG
GCTGTTATGTAGCCACTAGTCACATGCAACTATTAAGCAATCAAAATGTGG
CAACTGGAACAGAAAAACTGAATTTTTTCATTTTAATTTTTATTAAGTTAA
ATTTAAATTCCTACTCATGATAGTGGCTACTGTATTAGCTATACAGCTAGA
TGTTTGTGTATCCTCTAAATTCCAATGCATTTCTTCTTTCTGGAGAGAAGA
CTTTAGCTGGACATGGTGGCACATACCTGTAGTCCCAGCCACTCTGCCAGG
GTGAGGCAGGAGGATTGCTTAAACCCAGGAGGTCGAGGCTGCAGTGAGCTG
TGGTCATGCCACTGCCCTCCACTACAGCCTGGGCAAGAGAGCGAGAACTTG
TCTTATAAGAAAAGAAAAAGAGGCTGGGCACGGTGGCTCATGCCTGTAATC
CTGGCACTTTGGGAGGCTGAGGCGGGTGGATCACAAGGTCAAGAGATCGAG
CCAACCAACATGGTGAAACCCCATCTCTACTAAAAATACAAAAATTAGCTG
GGCGTAGTGGTGCACACCTGTAGACCCAGCTACTACTCGGGAGGCTGAGGC
AGGAGAATCGCTTGAACCCGGGAGGCGGAGGTGCAGTGAGCCGAGATAGCG
TCACTGCACTCCAGCCTGGGTGACAGAGTGAGACTCCGTCTCATTAAAAAA
AAAAAAAAAAGTTAGAAGACTGAGAAAAGAAAAATAATGAAATAATTTAGA
GCAGTCTGAGCTATGTGAGGTATGCAAAATTTATCAGGACAAGTGAGGCAG
GAGTATAGGTCTTCCAGTTAAGACCCCATGTTTTAAAAGCATTTTGTTCCT
GACTGGCTGCCTCATCTATTACCTACATATTCCCGAGATTTGTTAATACAA
AGAAACAATGTTATAGCCAGTCCAAAAGCTTATGCTATTTTAATGTTAAAT
CCTTGGCAAACAACTTTAAAACTGCTTTAAACTGCTTTTTTCCTCTAACAC
ACTTGTACTGCTTGCTAATGAGGCACTTGAACTCTGCACTTGGTTGCAGTT
TCTCAAAGTGCCCCAAACAACCTTCACTCAATTTCTTCCTTTTAGTTCCTC
TTTTCTTCAATACAAAATGAGATAATAGGGGTTGGAAGGAAAACTTTCAAG
ACCTATGGAAGTCAGTTGCAGCCAGCTCATCACATAGAGGTGCAGGTGAGG
TGTATTTTCATCACGGTGGAAAATTCTGGCTGCTTCATCTCCATCTCTAGA
GCCAATATTGGAGCTTTTCAATAAAAGCTATGGCCTCAACCACCAGCACCA
AGAAGATGATGGAGGAAGCCACCTGCTCCATCTGCCTGAGCCTGATGACGA
ACCCAGTAAGCATCAACTGTGGACACAGCTACTGCCACTTGTGTATAACAG
ACTTCTTTAAAAACCCAAGCCAAAAGCAACTGAGGCAGGAGACATTCTGCT
GTCCCCAGTGTCGGGCTCCATTTCATATGGATAGCCTCCGACCCAACAAGC
AGCTGGGAAGCCTCATTGAAGCCCTCAAAGAGACGGATCAAGAAATGTCAT
GTGAGGAACACGGAGAGCAGTTCCACCTGTTCTGCGAAGACGAGGGGCAGC
TCATCTGCTGGCGCTGTGAGCGGGCACCACAGCACAAAGGGCACACCACAG
CTCTTGTTGAAGACGTATGCCAGGGCTACAAGGTGAGTGTGTGGGCCCGGG
AGCTTTGGTAAGTACCAAGTCTTATCCTGCTCCCCAGGAGCTGAGATGATT
TAACTTGAAACCTAACATTATGACTTGGAAATACAGCTTTCATCATGTCAT
TCTTCTGAAAAATAGTTTATGATGATTTCTTGCTCAATTATCTAGACTGTC
CATCCTGACCTTCAATGGGATGGTTGGACTCTTATCTCTATCCATTTGTGT
TATGATGAATTTCTTTTTGCTTTAGAACAGGTTGTTCTCAAACCAAACACC
CGCATTTTTCTTGTTTCACACCATGAATATCATTTGAAAAACCACAATAT
GTAAAGCCATGCAGTAGGGCCTGAAAACAGGGAAGAAAGACCCATCACCTT
TTAGGTATCTACAGTCTAGTAAAGAAAACAAACCATCAAAAATGTCTGCCT
GGAGGTCCCTGGTTTTGGTGGTGGGGAGGGACATTTAGGGTAGAGAGTGGT
TCATCTTAGAAGTAACTCCTGAAGGACACGTAAAAATTGAACACCTATTGG
GGGATTTTCATTTGGGGAATGAAGGGTCAGTGACATTGAAAATATCACTCT
GGTACCTCTACTTTTTTTTTTTTTTTTTTTTTTTCCTGAGGTAGGGTC
```

FIG. 8-137

```
TTGCTCTGTATCCCAGGTTGGAGTACAATGGTGCAATCTCGGCTCACTGCA
GCCTCAACCTTCTGGGGCTCAAGCAATCCTCCCACCTCAGCCTCCCAAGTA
GCTAGGACTACAGGGATGCCCCACCATACCTGGATAATTTTTTTATTTTTT
GTAGAGACATGGTCTGCCTTTCTTGCTTATACTGGCCTCAAACCCCTGGTC
TCCCTCCCATCTCAGCCTCCCAAAATGCTGGGATTAGAGGCATGAACCACT
GTGCCCAGCTACTGTGGCATGTCTATGATAAAAGGAATATCAAGGAGTAAA
ATTCAAACTATCCGTATAAGAAAGGGAGGAGAGGGCAGATTTTAAGCACGA
TTCAGGAAGAAGAGTCAAAGATTTGGAAATGCTTGGTTGTGGAAGGTGAAG
CAGAGGGAGAGGTTTTGTGTACCATCCAGATTTCTTGCCAGAAAGCATATT
AAGGAAGGTGGGACTTTGCTGTTGGCAGCATGGAGGAATGGGCATAGTCCT
GATGTCCTTTTTCCTTCTCTGTCCTGCCTAAATTTGAGGAAAATGTTGTCT
CCAGTGTCAGGCTCCTTATTCTGTCCTCCATGAGGCAGAGGTGGTCTTGTA
TGAAGGCTCTAAGTCCTTCTAAGGACATGTCAATCATGACCACCACTCAGC
TCATGGCAGCTCTTCCTTAAACTCCATGGAGCAGCTAATAACTGCGATGAT
CATATTCCCATTTGAATTACTTTTCCACCAAGTAGTAAGAAAAGGAACCAG
CTTATGTTGAAATTGAGTTTTGTCACTTACTAGATGGGCAATTTTGGGCAC
GTTACTTAATGTCTTCACACCTTGGTTTCTCCATCTGTAAATGGGGATAAT
AGCAGTGTCCTCCCTCCCTAAAACACATACACAGGAGGTGGTTATAAGCTT
TGAGGACATTAAAATATAGAATGCATAGAATAGCACTTGGCATATAGTAAG
GACAATGTCATCTTTTGCTAAAACAGTTACATAGAACCTTTTCCTGAGAAC
ACTCGAGAATGAATGAGTATACTTGTTGGGTTTACAGAGGACAGGAGACAA
TTCTTTCAGCATTGACTACAATTAGCAATTTGGGTCAGCTTCAAATCACTT
TCAATAGAAATATGAGAAACTGTTTTGAAGAATAAGCTAAAAGCTTGACAT
GAATACTAAATCATTTTAAATTGGATTCATGATACCATTGTTCAAAAGATA
CCAGAATTCCCCTCTTCCATGAACTGTTTCTAATAACCAGCTGGCATCCTG
ATTTTCCTGACTCATAAGACACAAAATTTCATGTTGTTGCCAAACACTGG
TATTGGTTTTGCTTGGTTCAGCATGTTGTTTTACAAAATCTTTTAGATGAT
GATTACCTTGTTCTATATCCAACTTTTTCCTGGCAGGACTCTAGTGGTGGA
CATAGCTCAGGCTCTGGGTCAGCAGATGAGATTGCAATTGTTGCTCCACCA
CCTGGCAGTCATAGCCCTTTGGGCAAGTTATTTTACCCCTTTCTTAGTCTC
ATTTTCTACAGCACAGAAATGAAGTTTAAAATCCTACCAACTATTCAGGGT
TGCCAAGGGGATCAGTATGTTCCTGCACATATAGCCTTTAGCATGCTCTCT
AGCAAAAAACAATGAGGACTCTATAAATATTCACTATTATTCAAATATATC
TTAGAAGATTGGGATTCCCCCTAGGTCCCTAATGAAGAGTCAAATTGAATA
GGCTTCACTTATCAAATTTTTCCTTCAGGAAAAGCTCCAGAAAGCTGTGAC
AAAACTGAAGCAACTTGAAGACAGATGTACGGAGCAGAAGCTGTCCACAGC
AATGCGAATAACTAAATGGAAAGTAAGAATCTGACTTCATTGATCTCAAGC
TATTTTCCATTCTAGAGCTTAGGCATAGGGGATGATTGAGGAAAAGCACAA
TGAGGATTTATTCTCACTAAACCAGATTGAAAAAATGAAACCCAAGGAAGA
AACCATTATTTGTACTTATGCCCCTGGTTCCAGGTTTACATCCATGAGTAT
TTAGCACCAATCTTTCCATCTTTAAACTGTAGTTGGCTGGGATTCCTGATA
CTTCAGTCAGAAGAAGCAGAATTAGTATGACTATTTACCTAGAAAAAGCAT
CGAGTGGGTCTCAAACTTTAAATACGTCAAAATAAACCTGGTTTGCAGGCC
TCAACTCATTACCCTGGCACTTTTACCACAGTGGAGCATCTGGCTCTCAAC
TTTACAGGTACAGAAACCAAGCTTTGTGAACACTTAGAAAACAGGATCACT
CCAGATTGAAATTCATACTACTCTAGCTCATGAAGCTGATGAAAGAAATAT
```

FIG. 8-138
```
ACTTTATTTATTTATTTATTTTTAAATTATTACTATTTTTTGAGATGGAGT
CTTGCTGGAGTGTAGTGGTGCGATCTCAGCTCACTGCAATGTCCACCTCCC
GGGTTCAAGCAATTCCCCTGCCTCAGCCTCTTGAGTAGCTGGGATTACAGG
CATGTGCTACCATGCCTGGCTAATTTTTTGTATTTTAGTAGAGACGGGGTT
TCACCATGTTGGCCAGGATGGTCTTGATCTCCTGACCTCGTGATTCACCCA
CCTCAGCCTCCCAAAGTGCTGGGATTACAGGCGTGAGCCACTGCACCCGGC
CTATACTTGATTTATAAGTACATCACAAGTAATGCAACAACCTACACACTT
GCAACTACAAACTTTCAGATTATTTCCGTGGCTGACTAACCTCCACATTAT
CAGAGCCACATTCTTTTATGGAAATATTTAGGTTTGTGCAAAAGTAATTGC
GGTCTTTGCCATTAAAGTAAAGGCAAAAACCACAATTACTTTTGCACCAAT
CTTTATATTTATATAATTCACTAGCTTGCAGTAAAATCCCACAAGCTGATT
ACCAATTTTCTCTCTTTCAGGAGTCCTCTCTAACCTCTACCCTGATCTTTG
TTTGTGGATGTTGCTCTTGAGCTCCTGAGTACACTCTTACTTCCCCCATTT
CTAGGATCTTGGGCAATGGGGAAGACCTTGATTGTAACTAACATATATGAA
AACCCGTCTATACAAGAGTTAAAGCTGCACCTGTCTCCTACACAAAAATTC
CACCTCATCCTAAGTCAAAGACCCTTCTTCTATATCATAGTCATCAAAACA
CTGTATGAATTTATTTTTATTTTTTAATTTTTATTTTTTAAGATAAGTAG
AGAGTTTATTTGGGCCAAGTTTGAAGACTGCAATCCAAGAACATAGATTCA
AATTGCCCTGAATACACACTCCCACTGCATTAATTTAGACAGCACTAATGG
AAATTGCAACTTTACATCTCCTCAGATGAGAGTTTCACTTGATTTCTGTCA
GTCTTACACATAGGAATGCTTAAGATGACCCTAGGGTAGTAGAACAGTATT
TCTCAGTTAACCATAATAAATGCCTGTCACACTCAAAGCTCCCCCTGCCAA
GAATTATGGACCCTCTTACCAGCCTGGTTGTCTTAAAATCCAGTCTGGGTG
ATGTTCATTATAAGCTTTTACTTCAAGAAAATCGCTCCAACTCAGAAATCT
AACTTCTTAAATCATAAGTAAAAACCTCTTTTTATCCTTGTAACTGATAAA
GTGTTTGAACTTGGCCCTAGTTTCACAATTAAATTATCTAGCACTCCTAAC
CCAGCTTTCTCCTGTGTCTTGGCTGAAGAACAAGAAAATTAATTGGGTGAC
TATAAGGAATCTGAGGCAACCTCTTCCACATCTGAGTGCCTGCCTCCCACA
CATGACTCTGCAGCAGGAAACTGGGGACATTCTTCCAGCTTCAGTGACTCA
TGAGAAAATAATGTCCCAGTGGCTGATTGTGTGTGTGTGTGTTTGTGTG
AAAATATATATAACACTTAAGCATTTAACCACTTTTAAGTATATAGTTCAG
TAGAATTAAGTGCTTTTACATTGTTACATTGTTGTGCAACCATCACCATTC
CCATCTCCAAACTGCAACTCAGTTTCATCTTTCATCTTCTAAACTGAAACT
CACTACCCATTAAACAATAACTGTCCATTTTCTGGTCTTGCCAACACCTTG
TAACCACTATTTTACTTTCTGTCTCTATGAACTTAACTACTCCAGATGCCT
TGTATAAGCAAAGTCTTACAATATTTGCCCTTTTGTTTCTGGCTTATTTG
CTTGAATGTCTTCAAGGCTTGTCATGTAGTAGCGTGTGTCAGACTTTCATT
CTTGTTTATCCATTCATCCATAGATGGACATTTGGTTTACTTCCACCTTTT
GACCATACTTTCTTGACTCCAGGAGAAGGTACAGATTCAGAGACAAAAAAT
CCGGTCTGACTTTAAGAATCTCCAGTGTTTCCTACATGAGGAAGAGAAGTC
TTATCTCTGGAGGCTGGAGAAGAAGAACAACAGACTCTGAGTAGACTGAG
GGACTATGAGGCTGGTCTGGGGCTGAAGAGCAATGAACTCAAGAGCCACAT
CCTGGAACTGGAGGAAAAATGTCAGGGCTCAGCCCAGAAATTGCTGCAGGT
GAGGCTGTGTACTTGGAGTAGGGAAAAAAGGTATGTTATAGTGCTATTAAA
GGAGAATGGTAAGGAAGCATGGGAAGATAAAGTAATGTTTCTTTTAGATGT
ACATCAGTGCCATCAGGCTGGCCTTCACTAATTTATAGGGTACCTTTATGT
```

FIG. 8-139

```
CAATTAGAAAAATAAACTTCTGAGGGAACACAGCTTGGCCAAATGAAACCA
CGGGATAACATTTACCACTGTTTGCCTCCTTGGCCCATGTGCAGAGAACCC
TGGTTGTTGACTCTCTCCTGAAATACTCCACTAGGTGACTGATGGGTGATG
AAGTGGGGCAGCCAAAATGAGTGATAACCTTTTCCCTGATTTGCTTGTAGA
ACCCTTGCTCCAGAGCTGTTATGGTACAATCTACAGCTTTATCTGTAGGAA
GATAAACATCTGGAGCCATTAATTCTGGTTCTAACTAACAGGATTGGTGAC
TATACTGTAAGGCTGAGTGTATAGCATGATTGCTTTACCACTGTGTGATAC
CTGCTACCACCATCTTAGTGGCAGTGGCCCAGTCTCAGGGCTGTGCACAGA
TTCACCACTAAGGACCTTTATGATAAGTGTTCTCTAATCTGGGCTCACTGT
GAAGGAAATCCGATCACCAAAAGCTAGTCCTTACAGAGGGAGCATGGACAA
AGCTCCTGGCCCTCAGACTTCAGCAAGGATGAGAATAGATGCAAATGTTGA
TAAACATCCTGCCATGCTGAATCTCCCAGAAGCTGGTAGGAATTATTCCAT
CTGGGTATCCATCAATACCTAAGACTGGTGGGAATTACTTTGTTTGAGTAT
CCATCAATATCTAAGACTAAGACTAGGGTAACTCTCTTTACTTCTTCGGGT
AAAGCAAAGAAGAATAGCCCTGCATGACAAGCCCCATGAAATACCGATGTT
CCCATGCTCACCTTTTCTTTTTGTTTCTTTATAGAATGTGAATGACACTTT
GAGCAGGTAAGTCCTGTTTGAATGCAGGAGGGGAGGGGTGTGCGTATATAG
AAATGAATGGAATGCACCTCTGAAGAAATCTCTCGCCTCTGCTTATTCTAG
GAGTTGGGCTGTGAAGCTGGAAACATCAGAGGCTGTCTCCTTGGAACTTCA
TACTATGTGCAATGTTTCCAAGCTTTACTTCGATGTGAAGAAAATGTTAAG
GAGTCATCAAGGTATGTTCACTAAAGAATTCCTGAATACTGTGGATAGAAG
GGGCCTTATGCAGTAACCAAGTTTACCACCTGTCCCTTGGCAGGCTCACAG
CCAGAGAGGTTGTTTAGTTAATTTCAGTAGAGCTTTCATACTTTCTCTAGT
TAGTATGATTCACTGCTCAGTGAATGTGATGAGCATTGCATTCTGGTTATC
TGTGCAAACCTTTCAAATTCTTATTCTTTCACTTATTAGCCATGTTACTCC
AAGTGACTTGGTTTCCCCCTCTGAAAAATGAAAATATTAACAGCTCCTACT
TCATTGAGTTATCATCAAAATTAAATGCATCAACATGTACAAAGTGCTTAG
CCCTGTGACTGACACATGATCATAATAGCACATCATGGTATTAGATCTGAT
CATAGTGTTTATTATCAATAGCTCAGCCAACTCTTAGAGCAATGCAAGAAA
AGTAGGTGAGTATGATAACCTATCATTCACATATTTTAGGAACTTGACTTA
GATAACACAGATGACAAATGTTACAACCAATTTACAGATTCCAAAATGTTA
GAACCATTTACTGAGTTTCCTGCTCCCTTGATTTTTTAAATCAGTGCTGAC
TATACTTTCACAAATTTGTATCCGTAAGTACAAAATCAAAAAAACCCCTGA
AAATGGAAAGTTTTATCATGATTCATTTGGCTACAAAAATCTGGCCTAACC
TGAAATGATTTGGTGGTTATATTAGTTATCTATTAGTACAAACAAATTACC
ATAATTTAGAACCTTAATACAACACTGATATGTTATCTCAATTTTTGTGGT
TCAGGAATCTGGGCACAGCTTAGTTGGGCCTGCTGCTTAGGGTCTGATAAG
GCTGCAGTTAAGGTGTTGGTCAGGCTGTGTTCTTATCTGGAGGCTAGGCTA
AGGAAGAATCCACTTCCAAGCTCACTGAGGTAGCAGGCAGAATTTCTTTCC
TGATGGTTGCAGGACTTTGGCCCTGGTTATTTCTGGCTGTTGGCTGGAGGT
TGCCCACAGCTTCTACAGGCCACCCCTCAGCTCTTTGCACATGGGCTTCTA
ACATGGCCAGTTATTTCTTCAGAGAGAGCTCAGGAGACAGACTCTTTAGAG
AAAATCTGCCAGCAAGATGGAGTCTTACATAATGAAACGTAATCATAGAAA
TTATATCCCATCATCTTTGCCATATCCTATTGGTCAGAAGCAATTCATAAG
CCCTGCTCACACTCAAAGACAAGGAATTTTACGAGGGTGTGAACACCAAGA
GGCAGGAATCATAGAAGGCCACCCTTGAGTCTGTCTTCCACAGTGGCCAAC
```

FIG. 8-140

```
CCTGAACGGCACTGAGATGAGACTATTTAAAAGTCTTTATTTATCCCACTT
AATTTGAATAAATGTTTTGCTGCAGATATATTGATGAATTTGATTACAGGG
CTCTGCCTTAGGCCATGATGGGGTTGAACTTTAGAGTATATGCATTTTTT
GCCTTTATAACTTCTAAACTAATTTGAATGGCAAAGCCCATTTTGTTCCAG
GGATTTCAGAAAAGGAATTATAGACCTGTGTTCCCCTCAAATACACAACAA
CAAACAACAACAAAACCCAAAAGCACTCTGTATTTCATCCTATACAGATGA
CAGGAAGGAAGAACAAGACTTTGTGTAAGTTTTGCTGGGATTTCACTGAGT
CAATTTGCCTACTCTCATCTTTTACAGAAGGAATCATAATATGGTTCAAGT
GAAACTATTTCTTTCTTTCTTTCTTTTTTTTTTTTTTGAGACAGAG
TCTCGCTCTGTCGCCCAGGCTGGAGTGCAGTGGTGCGATCTCGGCTCACTG
CAAGCTCCGCCTTCCGGGTCAAGTGAAACTATTTCTTAAATGGGCTTATCT
TTTAACTAAATATTTCTCCCCTCTTAAACACTGTTTATTAAAATTTTTCTT
TTTTCAAATTTTTTTTTGAGATGGAGTCTCGCTGTTACCCAGGCTGGCTTG
CAGTGCCGCAATCTCAGCTCACTGCAGCCTCTGCCTCCTGGGTTCCAGCGC
CTCAGCCTCCCGGGTAGCGTGGGATTACAGGTACGCACCACTATGCCTGGC
TGATTTTTGTATTTTTAGTAGAGATGGGGTTTCACAATGTTGGCCAGGCTG
GTCTCAAACCCCTGACCTCAGGTGATCTGCCTGTCTCTGCCTCCCAAAGTG
CTAGGATTACAAGTGTTAGTCACTGTGCCCAGCTTATTACAAAAGTGATA
GGAATAAATTTTATTTTTATTTTTAAATGTATGTTTATTTTATTTTACATT
GCCTTCAAGCAGATGCAACAAATACATTTTAATCAGTCAAACAATATAAAG
GATATAAGGAGAAAGTTCAAGGTTTTTCCCACCCGTCTCCAATCTGACTTC
TCTAGGTAGGGTGATCTATATCTTTCCCTAAGTTTGTACAAACGTAACATA
TATACACTGTCTCTTCTATGTTACTCGTTACTTTTTATGTCTAATATTCCA
TAAGAATATAATAAATATATGTAACCATATCCCTACTGATGGAGCTTCAGG
CTGTTTTAGAACTTAGTTATTACAATGTTGCTACAATAACTTTCTAGTCC
ATGCATCCTTATATCCTGGTGCTTTCATTTCTTTTGGGAACATACCCCAAA
CTGGGATTGCCGAGGTTGTTGTTAATCTTAATATATGGTACCATATTACTT
GACTCAAAGTTGTAACATACACTCCTACCAGCACCAGGAATAATGACTCAC
ATATACTGAGCACTCTTTAGTCTGTGACAGATTAGAAAAGCTTTACTTTTC
TTGGTTCTTGTTTTATATCACAGTCCTCTCTATATGGGGCATTTTTGCTTT
ATAGAGGAGGAAATATGACACAGAGAGGTTAGGTGAGTGTTGTAGGATCTC
ATAACTAGAAGGTAGTCATAGAAAGAGTCTAGAGTCTAGAAACCACTCTCT
CACCATTTTGCAATGTGGCAGAAAATGCAAAGTTGTTATTTACTTATCTCT
TTTAGACAGGGTCTCACTCTGTCACCCAGGCTGGAGTGCAATGGCCCCATC
ATGGCTCCCTGCAGCCTTAAATTCCTGGGCTTAAGCAATCCTCCCACGTCA
GCTTCCCCAGTAGCTGGGACCACAGGCAAGCACTGCCACGTCTGGCTAATT
TTTTAAAAATTTTTTGTAGAAACACTATCTCTTTATTTTGTTCAGGCTGGT
CTTGAACTCCTGGGCTCAAGCAGTCCTCTCGCCTCGGCCTTCTAAAGTGTT
GGGATTACAGGCATGAACCACCATCTCCGGCCTGAAGTTTATTTAATCCAT
TGCCTTGTGGACTGGGCATTGAAGTTGTGTGTAGTTGGGTTTTTTGTTGT
TGTTGCTGTTGCAGACAATACTACTGTGAACATTCTTATCCATGCTTCCTT
GTGTCCCGTAAATGTTCCCTCCAGGGAGATACCTTGGAGTGACATGCTGGT
GTGAGGGATGCATATCATAATTTTACCAGATACTACAGATCTTGAAATTGT
TCCAATTCTACCCCACAAGCAATATAAGAGCTCTCACTCCTCCAAAACTCC
CTGAGTCTTTACTTATATAATTTATGATTTTGACAGTCTTACAGATTTAAA
ATGGTACCTAATTGTGTACTTAATTTGTGCTTTTCTGATTTCACTAGTGAG
```

FIG. 8-141

```
ATTGAGATTCTTTTTGTATGTCCATTAGCCCTTCAGGCCTCTGTGATTTAC
CCATGATTTACTGTGGTTTAATAATTTTTATTGGGTTCTTTTCCTTATTGA
TTTATGGGAACTTATTATAGCTGATATCTTCTGGCATGTGGATGGCATTTT
GCATTTTCATCCTGTTTTTTGATAAATAGGGTTTCAAAATTAAGTAGACAC
ATTTTCCTTCAAGGTCTGTGTCTTTTATGTCCAAAGAGCTTAGTCATCAGT
GGGCAGTGAATTTTATCACCTAATTAATTTTATTAGCCCCGTGTGCTATGC
CTGTAGTTCCAGCTACTGGGGAGACTAGGGCAGGAGGATCTCCTGAGCCCA
GGAGTTCGAGGCTGCAGTAAGCTATGATCACGCCACTGTACCCAGCCTGGG
CAACAGAGCTAGACCCTGTCTATTAAAGGAGGAGGCCGGGTACAGTGGCTT
ACGCCTGTAATCCCAGCACATTGGGAGGCCGAGGCAGGAGGATCACTTGAG
GGCAGGAGTTTGAGACCAGCCTGGCCAGCATTGTGAAACCCTATCTCTACT
AAAAATACAAAAATTAGCCAGGTGTGGTGGTGTGCACTTGCAGTCCTAGCT
ACTCTGGAGGCTTAGGCAGAATTGCTTGAACCCAGAAGGCAGAGGTTGCAG
TGAGCTGAGATTGTGCCACTGCACTCCAGCTTGAGCGACAGAGTAAGACTC
CATCTCAAAAAAAAAAAGAAGAGAGATGAAGGAGGAGGAGGAAGAGAAAGA
GGTGGGGGAGGGGAAGGAAGAGAAAGAAGAAGAAAGGGACAAAAAAATTTA
GCTGTCATCTTTGCTCTGATAGCATTATAATGATGATGAAGACAATTGCTA
GGTTGGTGAGAGAAGGCTATATACACACCAGAACTCTCCACGTATATGGCA
AGTTCATATATTTTGTTAAGTATGTCTCATTGGAGACCTTCTTTTCCCGTA
ACTATGACCAGTGCTCTGCCAGCTCAGTCAACAACAACATTGCATGTTGGC
TCCATACCTGGACTCTTGGTCCAATTGGTAATGAAACCATCCCACCAGTGT
CTTCATAATATATATATACACACACACATATATATAGTATTCTCTCCCA
GTGTCTTCATAATATATATATATACACATACACACATATATTATATTCTCT
CTATACATATTTATTTATATCTATATCTATATCCTTCCACCTCAGGTCT
CCCTCTGTCTCCCAGGCTGAGTGGTGCAGTAGTGCGATTATGGCTCAACCA
ATGAGAGGATCAATGGCAATCCTCTCATTTCAGCCTCCCCAGTAGCTGGGA
CTACAGGCATGGGCCACCACATCTGGCTGATGTTTAAATTTTTTGAGACA
GCATCTCTATATGCTATAGATATATATAGTATCCTCTCTCTAATATGGATA
GAGGATACTATGTCTATATCTGTATCTATCTATCTATGGAGAAGGAATACT
ATATATCTAATAAGATGTAATCTATATTATATATAAAAGTGAAGCATTGAT
TGGTACATATAATATATATATTGATTACTGTGTGTATATATTTGTTTTTTC
GAGACAGGCTCTCACTCTGTTGCCCAAGCCGAGTGGTACAGTGGTGCGATC
ATGGCTCCACCACCTGAGCTAAAGTGATCTTCTCACCTCAGCCTCCCCAGT
TGCTGGGACTACAGGAACAGGCCACCATACCTGGCTAATTTTTTAATTTTT
TTTTGAGACAGGGTCTCCCTTTGCCACCCAGGCTGGAGTGCACTGGCGCAA
TCTCGACTCACTGCAATCTCCACCTCCCAGGCTCAAGTGATCCTCTCACCT
CAGCTTCCCGAGTAGCTGGGACTATTGGTGTGCACCACAATGCCTGGATAA
TTTTTCATATTTTTTGTAGAGATGGAATTTGGCCATATTGACCAGGCTGGT
CTCAAACTCTTGGACTCAAGTGATTGACCCGCCTCAGCCTCCCAACGTGCT
GGGATTACAGGCATGAGTCACTGTGCCTGGCCTGATTATTGTACACATTTT
TGATGTAATGTATTATATATGTCATATATGACAATCTAGATGAATATATTA
AAGATTGGGTTTTCATTTATATATTGTAAAATACATACACTATACATATAT
AATATGTAGAACATATGCTATACATATTATATATGTATATGTTAACATATA
TAATACATACACATATAATATGTATAGTTGCAAATATAAAATTTGGTTTGT
TATTTATATTATTTTGTGCAGGAGTTCTATATCTATGTCTATAAGCGGGAG
CCATAATTTTCTATTCTTTGTAGGATTTGGTATGAGATTGGCATTACTCAT
```

FIG. 8-142

```
GCCTTGACTTCTAAATTTCCTATAAAACTGACAAGTTCCATTTTTGCTTGA
TAAAGATGCACGTTTTATTATCTGTCGGTAAAATTTAAAGTAGTGATTTCA
TTTCTTTAATGTTAGGTCTGCCCATGCTTTATTTGTTTTTTGAGTGAGTTT
TACTCAGAAATATTTTTCTAGGAAGTAATAATTTTATCAGTACTTTCAAT
TTTATTAGTAGCATAAGATTTATTATAAAGTTCTGTAATATTTAAAAAGTT
TCTGTATTCATTCCATTTGTGCCTTCTGTCTTACTTTGATAAATCTCATTG
GAGGTATGTCTATTTTATTAAATTTCTTTTAAAAGAAGCTACCTTTTTTTT
TGTTTGTTTTTCCTCTTTATTGCATTCTTGTTTTCTTTAACTTCACTGTTA
TATTGTTTAATATCTATTTTTTCTTTTTAAAAAATTATATTTGGCTTTCTA
TGTTCTTTTTAAAATTTAAATTAGATGCTTGGCTCATTAATGTTCAGCTTT
TTAATTTTTCTAAGATAAGCATTTAAAGCCTACAAATTTTCCTTAAAATTC
TGCTTTAGCTTCATTGTATATTTTTATAAATAACTTTTTATTATTGTTCCA
TTCTATACATCTTCTAATGACTTATTAGTAGTTTACATTTCCTAATATTTA
GAATCTTTTTAGTCATCTTTTTATTATTGGTTTATAATCTTATATTGAGGC
TAGAGAAAATGATCTGTGTAATACAGATTTATTGAAACTTGTTCAGACTGT
TTTCTGCCTAGTATTTACTCAGTTAGTGCATGTTCCATCTATACCTGAGAA
AACTGCATATTCTCTGCTTACTATTATTAAACAATTGCTGAGCTTTATGTA
TTGACTATGAGATTGCGCTTCTTAGATTGTTCAGACCTTCCGTATCTTCCC
TTATTTCTTTCTTTTGGTCTGCCTGATCTATCAATTATGGAAAGAAGAATG
TTAAAACATCCCATGATGATTGTAGATTTGTCCATTTCTCCTATAATTCTA
CAATTTTTGCTTTGTATATTAACACAATTCTAAACATGAATTCACTAATAA
TGTAGTACATTTATGTTTAAAATTGTGTTATCTTTTTTAGGTGACTCCTTT
CATTCTTTCTTTTTTTTTTTTTGAGACAGAATCTCTCTCTGTCACCCAG
GCTGTAGTGTAGTGGCGAAATCTCAGCTCACTGCAACCTCTGCCTCCCCGG
TTCAAGTGATTCTTGTGCTTCAGCCTCCCAAGTAGCTGGGATTACAGGCAT
GTGCCACAATGCCCAGCTAATTGTTGTATTTTTGGTAGAGCCAGGGTTTTG
CCATGTTGGGCAGGCTGGTCTTGAACTCCTGGCTTCAAGTGATCCGCCTGC
CTTGGCCTCCCAAAGTGCTGGGATTACAGGCATGAGCCACCACACCTGGCC
CTTCTTCCATTCTTAATAATGCTCTGACTTAATATCTTTTGATATAATACT
ATAACAGTATATGACTATATTATCTATCTTTTAGCTTCCAATCTTTCTATA
TGTTTTTGTTGATGTGTCACACCAATAGATAGGTGGAATTTTAAAAATCCA
ATTGATATTTTTCTCTTAAGTGGTATTACCACCCCGTAAACATTTTAATT
TCTCAACATGGGTTTTCCTGGGTCATTCAGGTAATATGAATTGAAACCCCA
AACTTCTGTGAGTCAGGCTGATAAAAGCTAACTGAATAGAGTTTGAAAAAG
GAGGGTATTTACAAAGGTGAGGAGTTGGGAAATCCACAAGGAACAGGAAGC
ACCCAGAACTAGGAACAGTTAGAGAGCCATCACCTCCTCTGGGCCTCAAGT
GGCAGGTGTAGGGAGCTGTAACTATACTAGAGTGTGCCCAGAGGCAGAGGA
ATGCAGACCCTCCAAATCATAGCGTGGGACTGGGGTACTGAATACTCCCAA
GGCTGCTTCTTTGTGCCCTATGGTCTCCTCTGGTGCTTCCCATTGGCTGAA
CCAAGCCAGAGGGCGGAAAGCCTGGTTAATCTGTCCATGTCAGCCTTCCTG
GGCACAGAGCAAGACAGGGAAAAGTGAGGGATTATTTGGAAGAACAAACAG
AGAGCATCCAGCACAGGAAGTGTTTCTGAATACTTGAATTCCTTAATTGTC
ACAGACCAACTGATCAACATTTAACTCAGTAGCACAGTGGTTTCCTTAACT
CTCTTGTTAGAACATCCTATTACCATTTTTATTTTTAAAACTGCATACTG
TTCCAGTATCTCACTTTAGTTATCAGATCTTTTTCTGTCTTGTTTGATTCT
AGTCTGATATTTTTCCATGTTATATTGGTCCTCCAGTGTATTATTATCTCA
```

FIG. 8-143

```
TACTAATGCTTATGGAACATTATCTGAGGGGAAAGAGAAGAGCTTACAATT
AAAAGTCATGGGACTAGGCATGTGTCATGAGACCTGGGTCTTCCAATAACA
AGCTAAGACATTAGCTGAGTCATTTTCCCTCTCTGATTCTCAATGTTGGTG
GTTATTCAGTAGAGAAGGGAAAAGGTATCTTTCTGCTCAACTGTCTCATGA
TTCCTGGAAGTCCTGCATGGGAGAAGAACTTTGGACAGGATGGTAACCATA
TTAACAGGTTAGTTCTGTACCTTGGCATCCTTGAATAATTAAGACGAAGAT
GATGTTGATGATATCATTATTACTACATGTTGTTAGAAGAGCTGAAGCAGG
ACTGGCTTGTCTGTCATAATGTAAAAGAGTCTTGGAAGATGTCCGGGGTCC
AGGGTCCAAAACCCCTCGTGGCCTTTGGAACACCAAGCTCTGTGCCAAATG
GTGGAAGGCTGCCCTGCCGCACCACAAATCTAAGCCTAGGGCATAAAACCC
CTTGTGGCTTGGATGGAACCCAGGGCTCAGGGCATAAAACCCCTCATAGCC
TCTGGAAAGTGCACAGACTTGTTGGTTCCTTGCTTTTCACTCATAAACGTG
TCCTCTACTATCTCAAGCAGCAGAGTATATTCTACATGTGTCAAAGAAAAT
GCTAAACTGTCACAGCTACGCTTAATGCACCACTACCTTTCTACCCCCATG
TCCTCATGCCCTCACCTGTTTACCCTCACGTCCTCACCACCTGCTTCTTTG
TTTGATCACCAATAAATAGTGTGGGCTCCCAGAGCTTAGGGCCTTTGCAGC
CTCCAATCTAGTGCTGGCACCCTGGACCCACTTTATGCACTCTTAACTTGT
CTTTTCTCATTCCTTTGACCCCGCCGGACTTTGTAGCCCCCACGGCCTGGT
GTTGGGCCTGATCACCCCAACAACTACCACTTATTAGTGGTTACCATGTAC
CAGGAAATTTTACCAAGCATTAAGCAAACATAAGCTTATTCAATCCTACCC
ACCATTCTCTGCAACAAATACGGTAATTTCCACTTTATAGTTAACAAACTG
AGGCTCAGAAAGTTAAATGATTTGCCTAAGCTCACCCAGTTTATAAGAAAC
AATAGTTGGGTTTGAACACAGGCTGGTTTTATTGAAAATAACTTGTGGCTG
GGCATGGTGGCTCACACCTGTGTAATCCAGCACTTTGGGAGGCCGAGGTGG
GTGGAACACTTCAGGTCAGGAGTTTGAGACCAGCCTGGCCAACATGGCGAA
ACCCCATCTCTACAGAAAATTTAAAAAAATTAGCCACTTGTGGTGGTGCGC
ACCTGTAGTCGCAGTTACTCCGGAGGCTGAGGCAGGAGAATTGCCTGAATC
CAGGAGGTGGAGGTTGCAGTGAGTTGAGATAGTGCCAGTGCACTCCAGCCT
GGGTGACAGCAACACTCCATCTCAAAATAAAATAAAATAAAATAACCTGTG
TTCTTCACAGCAACAAAATTATTTTTGTTTGTTTGTTTTGTTTTGCAGTT
AGTGTGACTCTGGATCCAGATACAGCTCATCACGAACTAATTCTCTCTGAG
GATCGGAGACAAGTGACTCGTGGATACACCCAGGAGAATCAGGACACATCT
TCCAGGAGATTTACTGCCTTCCCCTGTGTCTTGGGTTGTGAAGGCTTCACC
TCAGGAAGACGTTACTTTGAAGTGGATGTTGGCGAAGGAACCGGATGGGAT
TTAGGAGTTTGTATGGAAAATGTGCAGAGGGGCACTGGCATGAAGCAAGAG
CCTCAGTCTGGATTCTGGACCCTCAGGCTGTGCAAAAAGAAAGGCTATGTA
GCACTTACTTCTCCCCCAACTTCCCTTCATCTGCATGAGCAGCCCCTGCTT
GTGGGAATTTTTCTGGACTATGAGGCCGGAGTTGTATCCTTTTATAACGGG
AATACTGGCTGCCACATCTTTACTTTCCCGAAGGCTTCCTTCTCTGATACT
CTCCGGCCCTATTTCCAGGTTTATCAATATTCTCCTTTGTTTCTGCCTCCC
CCAGGTGACTAAGGAAAAGAGCAGAAGCTCCTTGGTTTAACCAGCACAGAG
AAAATAATATAAATCCCATAAGGGCAGACGTTTGGTCTGTTTTCTTCGCTG
TCATTTCCTTAGTAGTTAGACTAGTGCTGAGATTTTAGTGGATATATAATT
GATTTATGTTGAATATATGGACTTAGCAACTAAAAATACCACAGATGGTTA
ACCTGGACTGGGGCAAAGCAAGATAATAGTGATGATCGTATGTTGCTGTCT
CCATCCGTCTTTAATGGGTCAGGGCTTTGATTTCCAAGGGTCTTCAGGTGA
```

FIG. 8-144

```
TGAGTAGGGGTACCCACAAGTCAGAAGGTCTGCGTTCTCCTAGTTTGTTTG
CTGCCATTTGAACTCATGTAGGGAATGAAAGAAAGCTGCAATTATCCGCCA
ACTGCATTTAAAACAAAACAAAACAGAAAAATCAAAATAACATTGACTCTT
CCAACCACTGACATGTTGTTTAATAATCTAAGCGGCAGTCCTGGAGGCTAC
CAGACTTACTGAGTTCTACCTGAGAAACAGCCAAGCAAAGTGTGAGAGAAG
GGTTAAGACTGGCTTACAATGAGATGCTTCAAATGAAAAGGGAATTATGAG
TAAAATTGAACTTTGATGGGGGATTCAGTTCTGGAAAAGAATTTGGTATTT
TCCAGTCTGCTAGGACCAATTACCTTGAAATATTTTAAAATCTCAGTAAAT
AGTTATTGCTGAAATGGCTGTTGGCAGTTCTTATTATGATTCAGAGAAGAG
CAAATAGACCTTAACTTCATTTTGAAAAAGACCAAATTACCATACCCGAGT
GAGTAATGACAGGACTACAACTAAAACATAAACAACATTAATGATGACCAT
AAAAAGTCACAAAATTGCTAAATGTTATAATTTAGAGTTGACATAAAAATT
GATGGCCAGGCATGGTGGCTCACGCCTGTAATCCCAGAACTATGTGAGGCT
GAGGCAGGTGGATCACTTGAGGTCAGGAGTTCAACACCAGCCTGGCCAACA
TGGTGAAACCCTGTCTCTACTAAAAATACAAAAATTAGCCGGGCATGGTGG
TAGGGGCCTGTAACCCAGCTACTCGTGAGGCCAAGGCAGGAGAATTGCTTG
AGCCTGCAGCAGCTGCAGTAAGCCAAGATCATGCTGTGCCTCAAGGAAAAA
AAAAATTAATGTTTACTGATATTTGTTGAAGTCCTACAACATCACCTCTGA
GAATAGGAGAAATGAAGCAACAGTTGTGTCTAGATGTCAGAGGCATGGCTG
GGCCTCCATCTCTGCCTAAGGGAGATATAAAAGAGTTCAAACTATTGCCCA
TGTTCCCCAGGGTCAGAAGTTCTAATTATGATGATAGAGGCTGGGTTGTAA
GTAGTAAGTGAAGGGTAGCAGAATATGCCATCTTTGGCATAAGAAGTATTT
TGAGTTGAAGACAATTGAGAAAAAAAATAGATTAAAAACAAACAAACACCT
CTGCCCTCTCCCTATTTGCCTAAAAGCAGGATATGAAATTGTGAAGGTGTC
TTCTTACTCGGGGAAGAACAAAAGTTAGTCACCAGAGACTTTAGACTCTTA
TCAGCCTGGACATAGCACCAGAGAAGTCTTTTTTTTAAAAAAAAAAAAAA
AAAAAGGGAAAGAAAAAGTTGCCTTCCCACAATTTACTGCACTAGAAACTC
AAAGTCCTTTTCGTCTTCCTTGTCACTTAAAAAATGTATTCTTTTCTTAAA
ATGCTATATAAGCCCAAGTTCTAAATCCTCTTTTGAGTATTCATCTCAGTA
CTCCCCTGTGTTTGTACAATGCACATGCTTTGTTTCTGTCTTGTCAATCTG
TCTTTTGTTAGTCTACTTGATAGGGCCACAGATGGAGAACCTAAGATGAAT
AGAAAAAAAAGATTTTTCTCCCCAACAGAAGGATTATCGCCAGTTGCACTT
GTTCTATATACCCGTAGTCTCGGTATGCTGACCCAGACTTGGGTAATAGGA
CCCAGTGGGTAACCGAGGAACCCCACCTTTGTGCAGGATCAGTGAAGATGT
AATCTGGATATTCATAAGCTCTTCTCTACCTCTTGGCATCCCACAGTCCTG
TGTTAATGTAAGTGTGGTCTTCCCCAGAAAGGGGAGGCCTCCCTAACATTG
TTAAAGCCTAGCATATGCTGCTTAGAGGAAATTCTATATCCCTAAGCACTT
AGATTGCTGAATAAGAAAGAATGATAATAAAATAAACAATTAAATAAAAGT
TTTAAAAAATGAATAAAATAAACCTGTGGAAACTATAAGGAAGGCCAGAAG
AAATATAAAATTGGAGATTAATTGGGGTGCAGGAAAGTTATGGAAAGAATA
TAAGTCCTGCTAGATAAATCATTAGCTATTTTAATAAAGAATACAGAAGAA
AATAGGAACAAAAGAATATATACTGGAATAATTTTGAGAGTAATTTGAAGA
ATTAGATGCAAATAAATTTGAAAACCTTTAAAAAGAAACCAATGGCCTAAC
TGACCCAAGAAGGAAAGAAAATCTAAACAGACTGATAAATACAAAATGAAA
TTCAGACACTTACAGAGCAGCCAGGCATGGTGGCTCACACCTGTAATCCTG
TCACTTTGGGAGGCTGAGATGGGAGGATCACTTGAGGCTAGGAGTTTGAGA
```

FIG. 8-145

```
CTAGCCTGGGCAAGCTCCCATCTCTAAAAGAAAAGAAATTAGCTGGGCATG
GTGGCATGTGCCTTAGTTTCAGTACTCAGGAGGCTGAGACGAGGATTGCTT
GAGCCTAGGAGGGCAAGGCTGCAGTGAGCCATGGTCATGCCACTGAATTCC
AGCCTAAGTGACAGAGCAAGACCTTGTCTCAAAAAAAAAAAAAAAAAAAGT
TACAGAGCTCCAACTAAATAATGTGGGGAACAAAAGAAAAAAGAAGATGAT
TTTATGGCTGATTTTTTTTTTAAGGAAAAGCAATTCATGTACCCTTGAAGA
TTAGATTAAGTTCTATAAAATAGCCCAAAATGACAGTGGCTGAAACAAGTT
TATTTATCTCCCATTTAAAGCAAGTCTAGATGTGGAAGTCTGGGAAGCCCA
GAAAATCCAGGTCTTGTTTGTGTATGGAAACTCCAGAAAATCACAGATTCC
TTCCAGCCACCCCTCAATTACCCCTGGGATCCAAGAGAGCCACTAAAGTTC
CAGCCATCATACTCACAACCCAAGTTGTAGGATGGAAAAAAGGACACAAAA
GTAGGGTGAAGAGCATGTGTGCAACAGCTCTCTTTTACTCTAGTGTCCTAA
AACCTATCATAAAACCTTTGGCTTGCCTTGCATTAGCCAGAATTTAGTACA
TGGCCACACTTAAGAAGTCAGAAAGATTAGCTTTTTTTCCAGGGTAGTTGG
CTGAAAATCAGGAGTTCTCATATTAAAAAACAGAGAAGGGACATCGAATAG
ATGACCAACAATCTCCTTCACACTCATACTATTTAAACTGTCCTAGTCAAT
GACCAAAAAGAAAAGCCTACAAACTCATTGATATAAAAGCTTAACAAAGG
TACTCCCCGCCCCCGCCCGCCACACACCATCCCCAAAAGGAAATTTCTAA
TCCAATTAACAGTCTTAGGTTGGGCTGCTGAAACAAAATACCACAGCCTGA
GTGACTTAAACAACGACAATTTATCTCTCACTGTTCTGAGGTCTGAGTTGA
TTCTTTGTGAAGGCCCTTTCCTAGCTTGCAGATGGCTACCTTCCTGCTATG
TCTTCACATGGCAAAGAGAGAGCTAGCTTTCTGGTCTTTTCTTATAAGGGA
CCAGTCCCATCATGCCCATCATGAAGACTCGATCTGCTAGGATCTCAACTA
AACCTAACTATCACCCAAAGAGCCCACCTCCAAAGACCATCACATTGAATG
TGAGAGTTTCTACATATGCATTGTGGGAAACACAAACATTTACTTCAACTG
TAACTATTGAAGCAAAAATGTCCCCCCACCATAGACATCCAGCACCACAGT
AGTACATTTATTACAATTGAACTTACATTGACACGTCATTATCAACGAAAG
TCTGTAATTTACATTAGGGTTTATTCTTGGTGTTGTGCTTTCTATGGGTTT
TGACAAATGTATAATGTCATGTATTCACCATTATAGTATCACAGAAGTTTC
ACTGCCCTAAAAATCCTGTGTTCTGCCTTTTCAACACTTCCTGTCACCCAA
TTTCTATCAACTAATCTTTTGACTGTGTCCATAGTTACTGTCTTTTCTAGA
GTGTCATACAGTTGTGAAGCAGGAAGCAGGAGTGAACTCCGGAGGCAGGGA
CTTTACTCCGGACCAGATTGAAGACTAGCCGAAACAGGGACGAGGTTAAAG
CACCTCTCCATAAGACACGCCCACCAGCGCCATGTCAGTTTTTCGTTGCCA
TGGCAACAACAGGACATTATCGACTTCTTTCCTCTGTACCTACTCCGAAGT
TACCACTCTTTTTCTAGAAATTTCTGCATAATCCCCCTTAACATGCACTTA
ACTAAAAGCAGGTATATTACTGCAGAACTGCCCCTGAGCTGCTACTCTGGG
CACATTACTTATGGGTTAGCCCTGCTCAGCAAGGAGCAGTACCTGTTCTGC
TGTTGTACACTGCTGCTTCAGTAAAAGTTGCTAACACCACCACTTCACCCT
TGAATTCTTCCCGGGCTAAGCCCTAATTTTGGCTTGCTTGCCCTGCATCA
GTTGGAGTCATATAGTATGCAGTCTTTTCAGGTTGGCTTTTTAGTAACATA
CATTTAAGTTTCCTTCATGTGTTTTCATGGCTTGATCGTTTCTTTTCTTTT
TCTTTTTCTTTTTTCTTTTCTTTCTTTTTTTTTTTTTTTTGAGACAGAGG
AGTCTTGCTCTGTTGCCCAGGCTGAAGTGCAGTGGCACTGGCTCACTGCAA
CCTCCATCTCCCAGGTTCAAACGATTCTCATATCTCAGCCTCCCGAGTAGC
TGGGATTACAGGCTCACGCCACTATGCCCGGCTAATTGGGGTTTTCCCATG
```

FIG. 8-146

```
TTGACCAGGCTGGTCTCAAACTCCTGGCCTCAAGCAATCCACCCACTTCGG
CCTCCCAAAGTGAATGCATTTCTTTTTAACTCTAAATAACATTCCATTATT
CAGAAGTACCACAGTTATCCACTTACCTACTGAAAGACATCTTGTTTCCAA
GTTTTGGATAAATTATGAATAAAGCTGCTATAAACATCTATGTGCAGGTTT
TTGTGTGGAGATAAGTTTTCAATTCCTTTGGATAAATACTAAGGAGTGTGA
TTGGTGAATCTTATGGTAAAAGTATGGTTACTTTTGTAAGAAACCACCAAA
CTGTCTTCCAAAGTGATTGCACATTTTGCATTCTCACCAGTAATGAACAAG
TTACTATTGCTACATATCTTTGCAACCTTTGGTGCTGACAGTGTTCTAAAT
TTTGGTCATTCTACTAGGTATGCAGTGGTATCTACTTGTTTTAATTTGCAG
TTCCCTAATGACATGATGTCAAGCATCTTTTCATATGCATACTTGCATCTG
TGTATCTTCTTTGGTGAACAGATGTTCAGGTCATTGGCCTGCTTTAAATCA
GGTTATTTTCTTACTGTTGAGTTTTAAGTATTCTTTGTATATTCTAAAAAT
ATTGTTCTTCATCAGATCTGTCTTTTGCAAACATTACCTGCCAATGTGTGG
CTTTTCTTCAACACTTCTTTGTAAATTTGCAAGTCCTTTGAGAAAAGAAAT
GCACCCAAAGTATTAATTTGGCAATCTCATATCACGAGAGTACTCTAAAGC
TAAATAAATTACAGTTTTTCAAATTTTGAATTAATTGATCTTTGCTATTGT
TAGCAAGGTCTTGTATTCTTTTTTTTTTTTTTTTTTTTTAATAGAGAC
GGGTCTTGCTACAGTGCCCAGGCTGGTCTCGAACTCCAGGCCTAAAATGAT
CCTCCTGCCTTGGCCTTCCAAAGTACTGGGATTACAGGCATAAGTCACCAC
GCTCAGCCATCTGGTATTCTTTAGCAACTGTTTGGTAACTTAATCTTTCAC
TTTTTGAAAACAAAAAATAGTTTTTTTCTCATAGTTTTCTAACAAAATCTT
CATAACTGAAATAATTTCTCTTTATCACCTCTTCTTATAAATATGGTTTTC
TTTTTTAAATAAAATTTAAGACATTTTATAACTGGCCAAATTTACTAGC
TTAGATACTATTAGATAGTCAATATTTTTGTTGGATATTTGATTTTTATT
TCAGGCAACTAATATCTATTCATTTTTGCACTGTTGGAAGAAAATTACTGA
TCAAATTCACTATGTATTTGCAGAAAATGGCTTTCAATATTGTCTACTTTA
TCATCCTTTTTTTTTTTCTTTCTTCCTTTTTAGATACAGGGTCTCACTA
TGTTGCCCAGGCTGGTCTCCAACTTCTGGGCTCAAACAATCCTCCCTCCTT
GGCCTTCCAAAGGGTTGGATATGTTTTATCTACAGTTTTGTTGTTTTGTTC
TGCTACAGGATATTTGCAATTGCCATTTATCATGAAATTCATGACATACCT
TCTTCCACTCTCCTTTTTATCTTTATTGTTCTGGTTATAGGACTAGCTTTG
CATCTCTACTCAATTCTGTATCAGTAGTATGCTTTCATTTTAAATTTTAAG
TTTGTCCATATGTATATTGACACAGGGTCTTGCTCTGTTGCCCAGACTGGA
GTGCAGTGGCAAGATCAGGGCTCACTGCAGCCTTGACTGCCTAGGCTCAAG
TCATCCTCCCACCTCAGCCTCCAGAATGGCTGGGACTACAGGCACGCACCA
CCACACATGGCTCATTTTTTGTATTGAGACAGGGTTTCTCCATGTTGCCC
AGGCTGGTCTTGAACTACTGGGCTCAAGCAATCCTCCCACCTTAGCCTCCC
AAAGTGTTGGGATTACAGGCTTGAGCCACCATGCCTCGCTTCTACACTTAT
TTTTAATTCTAAAATAATTTATAATAATAAATATTAACAATTAGATTTAAT
TACTGATAAATATTAAATGTTAAATAGGTTTTATTAAATAATTAAATAAAA
ATGAAAATAATCAGTATTTCAATTTAATTACTAATTATAATTCACAGTTAT
CCTTGTAACTCCTAATGTCTATATAAAAGATTTTTATATTTTTTAATTCTT
AAAATTTTATTATTTATTTCACACCAGGCCATCACTGTGATACATTTTTTA
AAACACATTAAATTATCACCAGAAAAGTGCTGTGATGGAAAATATAAATTG
AAATACCTTTTCTGGTTAGGAGAGTAATTCTGTTTTTCTGATAGAGAATAG
AAGAGTCCTTCAGGCCCCTCCAAACTGTCATATTCCGGGCATCGGGTGTCC
```

FIG. 8-147

```
CCATCCTCACTTCAGTCCACAGGCAGGGTCCTCAGTCTTCAGCGCTCCTTC
TCTTTCCCCTTTGTCTTGTGTCTCCTTGGGTCTCTTTTCTCCAAGACCTAA
ACTCCCTGAGGACAGGACTATTTTTTACATCTTGATGTCACTCCTGAGCAC
TTGCTTTAATGTGTTGGACACTGGGTCCATTAAAGATTGTATGTGAAATTA
TAAAAGAAACGTTTTCACCTTTCTGTGGTACAGCTATAATTTCTGGTTTCA
TTTACCAACTGGGTGAAAGTGGACCAGTGACACCATTTGTCTGGGCCTTCC
TTTCCTGAAATATAATATTGGGGCAATAGTCCCTGGTTCTTGTAAGGTGTT
CAGGCACAAAACGCTAGGCATGTAACATACTAAATGAGGTTTTCCCAGTTA
ATTTATATGATTGCAAAGGACGTTCATATACACGGTCTGCTAAAGAATTCT
GGGGCCAATTAATCTCTGTGGCATGATGGGTAAGTCGATCCCTTCTCTGGG
CGTCTATTACTTCAGAAAAGGCATGAACTCAATTTTAGGGACCACACAAAA
AAATTTATTCACTATCGTGTAGGACTTGGTCATTAGAGAGCTTTTGTTTCT
TTTTTTTAAAATTTTTTTTAATTTTTATTTTCGTGTATGTGAATTTAATGG
AGAGCTTTTAAATAACCAGATATTTAAATAACCAGATAATACAGATGCCCG
GCCTGCTCCAGACAAATTAGAAAAGTATGTAGGTGAGGAGGGACCAGCCAG
AAGGCGGTTTCAGCTCTGGAGTGACACTGAACGTACTTCTCTTCCAGGGAT
GTCACGAGGTGTCAATTTCTCTGGCCTTACCCAGGTCCATGCCCGCCCCCA
GGGGCCCCAAGAATGACTTCAGCACCCCACCCCCACCTCCCTCTCCAGATG
TGGGTCCTGGGAGCGTTCAAGGCCCGTCAGTCACTCGAGCCACCCCTTGGC
GGCTGGACCAAATCTTGGGCTGCCGCCTGGATCTGCAGCTGGAAAGCGCCG
TGACCACCGGTGTCCCCAGCTGGAGCAGGGCGGGCTGCACGACTCGCGAGG
ACGCCCTGAACCGCGGCTTCCTCTTTCATAGCCGCAGGACTCGTGGTCAGA
AGGCCGACTCCAAGCCTCAGCGGATCCACGAAATGGCCTCTTTGAGGCTGT
GGTGAAATTTAAGATACCCTTTCCCTGCCATTGTTACTGACGTACTTCAGC
AAACAGGTTAAAGTTCTGAAAGGACGTGGTCACGACTTTATATTTCTTACA
GATTTGTGTCTCATGTTTTGTGCGTAAAAACCATTCGTCCTCATTTGAGAT
TCTCATATCCGTAATTCAGTTATACATAAAACTGAATTCAGTTATATCATA
AAATGTTCCCATGCGGGGAATGATTCGTTGGGGTCTCAGCCTGAGGCCAGA
CGCAGCAGAGAGATCGGGAGTTGGGGGATGGCGGGCGGGGAGCGGAGAGGA
GGCCGCCCGCCGCCAGACTCAGGGTCCAGCAGAGCAGCAAATGCTCCCCGG
CTCCCAGCCAGGGCGCAGCTGCTGGCCTGGGGCCGCCCCTCACGCCGCAGG
AGCCCCGCCCGCAGCGCCGGCCCTGCCCCTGGCCTGTGAGGGCGCCAGCGC
CCCCTACAGCTTGCAGTCGCCCTGCGCGCCTCCCCGCGAGGCTTGTTTTCT
AGCGCCTCTGGTGGGCCGCCTCCCGCAGGCCTGGTGTGAGCCTGGGGTCCG
TTCTCACAGCTGGATCTGGGGTCTGAATGCCGCGCCCTCTGGAGAGCCACA
GATGGGTCTCCGCTGATGCTTCTCTCAATTTCCTCTAAGAGCGAGAGCTCC
GGGAAAGGAGCCGATCCTGGTGGAAGACTACAGGTCTGAGTCCACTGGACG
AAAAACGAGGTGCGTTAAGAGACCGCGGGAGTGGGGAAATGGGGAAGTGAG
GGTGGGGACTGGGCAATGGGGGCGGGACGAGAGGTCTGGGGCTGGCGGGGA
CAGGGCTTAAGAGAGAGCCACCCCTCCTAGCCTTGAAGCTGTACCGAGCTT
CCCTGTGATATTTTAAAATGCAAAAGTACAAAAATTGAAGTAATGGAACTA
TGCGTACGCACCTCCTAGATTTTTAAAGGTTAACGTGTGACTGTGTTTACT
TCAGATGTTCCTGAAATAAATGAAAATGACCAGTTAAAATGAAGGAAGAAC
GCGCTTGCGTCCCTCCTAGAGGTCAAACACTCTTCTGAGGATAGGTTGTAT
GCTCTCAGCGCCTCTTTTTATTAAAAGTATTAAGAAGTACTTTTCCAAATA
TTAGATGTAGTGTGTCATATCATTTAAACGATTTTTTTTGTTTAAAATAGT
```

FIG. 8-148

```
CTTTTAAAAATAATCTTTTTATTTTTAGATTTTTTTGAGACAGAGTCTCGC
TGTGTTGCTCAGGCTGGAGTGCAGTGGCGCCATCTCCCCTCACTGCAACCT
CTGCCTCCCAGGTTCAAGTGATTCTCCTGCCTCAGACTCCCAAGTAGCTGG
GATTAAAAGCGTGAGCCACCACACCCTACCAATTTTTGTATTTTAGTAGAG
ATGGGGTTTCACTATGTTGTCCAGGCTGGTCTCGAAATCATGACCTCCACT
AATCCACCTACCTCGGCCTCCCAGAGTGCTGAGATTACAGGCATAAGCCAC
CGTGCCTGGCCACTTTAATCATTTTTGTTTTTGCATCTAGTCTAAGAAATT
CTGCACTAAAATTCTGCACTATTTTCTTCTAAAATTTAAAACATTTTCTA
TCTGTGTCTTTGTTAGATGTAGAAACTTTTGTGTATGATATGGGGTATAGC
TATAATTTTATTTTTATTCCATATGAAAGCCAGTTTCTCAGCCCAGGTAAT
TGAATAGACCATCCTTTCTCCACCAACTCTTAAGGCTACTTCTGCTCTATT
GTGTTCATAGTAGTTTCTAGGCTTTCTGTTTTGTTGTACTGATTTCTTCAC
CTATTTTGCATCAAGGCTCTCCTCTTGGGGAAATAAAACAATCCTGCCAA
CCAAAGACCCCTCTGGATCCTCAAACACGCCATCAGCATGGAAGGCCGCTA
TGGCATAGCGAGAGATAAATAGGATTCAGGCAGTGCTGTCCTTACATCGCA
ATCATTCAGGTAGTTAGCAGGAGCATCAATCAGTACAGATATCCAGAGCTG
ATGGTCTTATTTGTATGAATGCCCAGTGCATATGGGATTGGAGGGGAGGGC
TTGGAGTGGGATGAGGGGCTAGTGGGATCCAGAAAGGGGCTAGTCTTCAGG
TCTTCCCTGGAGAGTATGTAATCTCTTATAACTAAGTGTTGATTTTTGTTT
TGTTTGTACCTTCTTTAGATATTGAAGTATTCGCTAAGGCTTAACATGTAA
TATATTTAAATCTTCATATGAATACGTTTATCTGATAGATTTTGGTGAGAC
ATAAACTATGAAACAAACAGAAAGATGGAACATGAGAAAGGGTCAAGGGTG
GCCTTGGTTAGGGATGGCAGCTTTTACAACTATGAGCTAAGATAAAATTTA
GAAGGTTTTCTTTTTATTTTAATTAATCATACCACTATTTTCTCCTTTAA
TTTCCATATATAATGAGTTGATTGTAGTATTTTTATTGTGCTTAACTATTT
TAAGATAATAGTTGTCTCTCCTCATTTTAGCAAATAATATATTTAATGAAA
AATCAACTTTATTGAGGAATAATTTATACACAGTAAAATACACCTGTATTA
ATTATACAATTTGATGCGTTTTATATACCCAAACAGTTACTACTGTAATCA
AGTTACAGAACACTTCCGTCAACCTAGATAGTTTCCATTTGTAGTATCACC
TGTGCCGCCTCTTCCATCCTCTTGGCCCCAGGCAGCCACTGATGTACTTTC
CATAATTACAGCTTAGTTTTCCCATTCCTAAAATTTCATATGAATGGAATT
TATATCATATGTATTTTTATTTTCCTTCACATTTTTGAGATTCATCCATT
TTGTGTATATATCAGTAGTTTATTCCCTTTTATTGCTTTATAATATTCCAA
GATATAGATATATTGCAATTTTTTTTTTTTTGAGATGGAGTTTCCATCTT
GTTGCCCAGGCTGAAGTGCAATGGCATGGTCTTGGCTCACTGCAACCTCCG
CCTCTTCGGTTCAAGTGATTCTCTTGCCTCAGCCTTCCGAGTAGCTGGGAT
TACAGGCGCCCGTGACCATGCCCAGCTAATTTTTTAGTAGAGATGGGGTTT
CACCATGTTGGATGGGCTGGTCTCAAACTCCTGATCTCAGGTGATCCGTAC
ATCTTGGCCTCCCAAAGTTCTGGGATTACAGGCATGAACCACTGCGTCTGG
CCGATATATTACAATTTATTTACCCATTCACCTGTTGATGGACACGTGGGT
TGTTTCCAGTTTATAGCATTGTGAAACAAAGCCAGTATGAACATTTGTACA
TGTCATAGTATGGACATGTGTTCATTTATCTGGGAGAAATGACCCAGAAAT
ATTGCTGGGCTGTATAAGTGTTTAATTTTATGTTAGAAACAGCCAAACTTT
TTTCAAGTAGTTGTAACATTGTCCTCTTACATTCACAATATATGAGAGTA
GTTTCCTCCACACCCTTGCTCACCCTGGGGATTGTCAGTCCTTTTAACATT
AGCTATTCTGTTGAATGTGAAGTATCTCATTGTGGTTTTGACTTGCATTTC
```

FIG. 8-149

```
CCTAGTAACTAATGATGTTTAAAATCTTTTCATGTGCATACTGGCCATTTG
TATGTTTTCTTTTGTGAAATGTCTGTTGAAAACTTTTACTCTTTGTTTTGG
CTTGTCATCTTACTAAGTTATAAGGTTCCTTATATTTTCCAGGTGCGAGTC
CTTTGTCAGATACATGTATTATAAATATTTTCTCTCAGCCTGTGATTTTTC
TTTTTCTTTTCTATTTATTTATTTATTTATTTATTTTTAGGAAGAGTCTC
ACTTTGTCACCCAGGCTGGAGTGCAGTGGCACCATCTTGGCTCACTGCAAC
CTGTAGCTCCCGGGTTCCAGTGATTCTCATGCCTCAGCCTCCTGCTTTTCA
TTTTATAATGTTTTTTGAAAAGCAAATTTTCACTTTTGATGAAATTTATCA
TTTTGTTATTTATGTTTTATAAACTATAAACCTGTTGTTTTGTTTTAAAGA
AATCTTTGCTAATCCTAGGGTGTTGATGATTTTCTCCTATTTTTAAAGAA
GTTTATAATTTTAGCTTTTACATTTAAGTCTATGGTCTATTTTGAGTTAA
TTTTTGCATAAAGTTTGAGGTAAGGCTCCTGCTCCTCTCCCCCACACCGGA
TGTCTACTTGTTCAAGAAACATTTACTGAAAAGACGATTTTTTTACTTATT
AAATAGCCTTGACACCTTTGTCAAAACCAGTTGTCCATAGATGTGTGAATC
TATTTCTGGGTTCTCTGTTTTGTTTCACTGATCTTTGTGTCTAACCTTATA
CCAATTCATTCTGAAATACTTTCCAGATTACTATAGCATTTTAATAAAATT
TTGATTGAATAGTTTAAGCCCTCGGACTTTTTTCCTTTTAAGTATATCAAC
TTGGAGAGGATTGATTCATATTTGTGTTTCATTTTTTCATTTTTCAAAATT
ATGTTTCAAATTGACATAATAATTATATGTATATATGGGGTGCATAGTGAT
GTTCTTTTTTAAAAAATATTTATTTATGTATTTATTTATTTTTGAAACAG
AGCCTTGCTCTGTTACCCAGGCTGGAGTGCAGTGGCGCGATTTCGGCTCAC
TGCAACCTCCGCCTCCTGGGTTCAAGCAATTCTCTTGCCTCAGCCTCCTGA
GTAGCTGGGATTACAGGCACATGCCACCACGCCTGGCTGATTTTTGTATTT
TTAGTAGGGATGGAGTTTCACTATGTTGGCCAGACTGGTCTCTAACTCCTG
ACCTCAAGTGATCTGCTTACCTTGGCCTCCCAAAGTGCTGGGATTACAGGT
GTGAGCCACTGCGCCCAGCCCATAGTGTTATTTTTATACATACTGTGTATA
GTGATCAGATCAGGGTAATTAATTAGAATATCCATTATTTCAAGCATTTCT
CATTTCTTTGTGTTGGAAACATTCAATGTCCTCTTTTCTAGCTCTTTGAAA
TTATTTATTACTGTTAACTATTGCCATTCTGTAGTACAAATAGAACACTAG
AACTGATTGCTCTTATCTAGCTGTAACTTATTTTAACGAATCTCTCTTTAT
CATCTCTTTCCCCTACCATTCCCAGCCTCTAGTAATCTCTGTTGTACTTTT
TACTTCAATGAGATAAACTTATTTACTTAGTTAGCTAGCTTCTGCATATAA
GTGAGAACATGTGGTGTTTAACTTTCTGTTTCTGGCTTATTTCACTTAATG
TAGTATCCTGCAATTCCATCCATGTTGCTACAAATGACAGGATTTCATCCT
GTCATGAACAAACAAAAATTTGCCAAAACAAAAATTACCTTAGTTATCACA
TTTCTTTTATTGACATAATTCATAATCATCAGAATCATCTGACTTGTACAT
CATTGTATCAGTTGGTTTTATGCTCAAGATGTTGTATTGGTTCATTATTGT
CTTAATATCCCAACCAACCCAATCTAGACATAAATGCTGGCCCCTGTGACA
TGGCAGGAAAGGGAGACAGGCCTGGGCCAAGCATAGTGATAGCAATGCACC
TGTGTTTGAAGCTGTTAAATATTTGCTACAGTCGTATTCCTAGACTCAAAA
TTAGATTCTTGTTAAGTCCTACTTGTCAGTGTCTATGGCTGTGTGAGTTCT
GGTTAGTAGAAGGTGGGCAAAAGTGATGTGTATTCTTCCATAACTGGTCCA
TAACCACCTACCACTCACAATACTCCATGCCTTTTTTTCTCTTCAGGCTCC
TTGGATTAGAGACCATCCTGAGGACATCCTTGGGAGCCATGTGCTGAAGAT
GGCCAAGCCACAGGATGAAAGGAGCTGCATCTTTGAGTCACCACTGGAGAA
AGGTCTCTCTAAATGGATTTGCAGAGACGTCTTCTCGAATACTCCCCTTCT
```

FIG. 8-150

```
AAGTTCCACTTGTAATCCACTTCTTCTATTCTCCCAGCAATCAATGTGGTT
TGGGGAAATTCCAGAATCTCATAATACCTTGGTCATGGGTAAATAAGGAAA
GGACCTTTACATACATGTGATGCAAAGCAGATCAAAACAAGCAGAGCAGCC
TAAGAGCAGCAAGACCCCAAAGGATAAGGGAAGTCCTGCAGAAGAGCAGAG
CGGTGCTGCAAAGGCAGGCAGGTAAGGTAAGCAGACAGGGCCATCAGGATG
GATCCTTTGGGCATGCCAGCATCCACCAGGGACTGGTAGAGCTATTTAGAG
AAACTGATAAAAAGCTCTGCCAACTACAGTCACAAAAGATGGAGCTCAGAA
TGATGAGTAGATGCCTAAAACATCTCCATTTTGTTGATGAAGAAAGTAAAG
TTTATAGAGCTTAGATTATTTGCTTTTGTACCTAGCACAGTACTTAGTTTA
TAGTAGATGCACAATAAGTATTTGTTTAATGAGTGAATGAGTCACTAGCCT
AAGACCTTTAATATAACATGCTTAAACCTGCTACCAGGGATTGGGAACTCA
CCTATTTAGTAGTGAGTAGAGGGGTGTGGTACTGGTACTTAAGACAGATGC
ATTGTGGTTGGGTATGGTGTGTTTTTGTTTTTGTTTTGAGACAGGTTCTCC
CTCTGTTGCCCAGGCTGAGATGCAGTGGCATTATCATGGCTCACTGCAGCC
TTAACCTCCCGGGGCTCAAGCGATCCTCCCACCTCAGCCTCTGAGTAGCTG
GGACCACAGGTACGCATCACCGTGCCTGGCTAATTTTGTTTTTTGTTTGTT
TGTTTTGTAGGGACGGGATTTTGCCATGTTGCCCAGGTTGGTCTCGAACTC
CTGGGCTCAAGCTACACCCGCCCGCCTCGGCCTCCCAAAGTTGTAGGATTA
AGGTGTGAGCCACTGTGTCCAGCAGATATAATGTTTTTAAAAGTTTGAGAG
TTAATATGCTCTCTGGTGTGCCCTAGGTCCCACTACTCCTATTGCCTTAAA
ACTCACGCAGTACACATTTGTCTTCCATGGGCTTCAGTTGTAAGAGAACCC
TTTCTACTCTTTGCTGTTCACAAGTCTCCTTTTAAACAGAGCTTGTTCCCA
ATGCTGTTTTGTTTTGCCCTCTGCCATGTTCTTCCGGCCATCACCTCCTGT
GGGGAAAAGAGAGAGAGATCACATTGTTACTGTGTCTGTGTAGAAAGAAGT
AGACATAGGAGACTCCATTTTGTTCTGTACTAAGAAAAATTCTTCTGCCTT
GAGATGCTGTTAATCTAACCCTAGCCCCAACCCTGTGCTCCCTGAGACATA
TGCTGTGTCAACTCAGGGTTAAATGGATTAAGGGCTGTGCAAGATGTGCTT
TGTTAAAGAAATGCTTGAAGGCAGCATGCTCGTTAAGAGTCATCTCCACTC
CCTAATCTCAAGTACTCAGGGACACAAAACACTGAGGAAGGCCACAGGGAC
CTCTGCCTAGGAAAGCCAGGTATTGTCCAAGGTTTCTCCCCATGTGATAGT
CTGAAATGTGGCCTCGTGGGAAGGGAAAGACCTGACCGTCCCCCAGCCCGA
CACCCGTAAAGGGTCTGTGCTGAGGAGGATTAGTAAAAGAGGAAGGAACGC
CTCTTTGCAGTTGAGACAAGAGGAAGGCATCTGTCTCCTGCTCGTCCCTGG
GCAATGGAATGTCTCAGTGTAAAACCCGATTGTATATTCCATCTACTGAGA
TAGGGGAAAACTGCCTTAGGGCTGGAGGTGGGACATGCTGGCAGCAATACT
GCTCTTCAAGTCATTGAGATGTTTATGTGTATGCATATCTAAAGCACAGCA
CTTAATTCTTTACCTTGTTTATGATGCAGAGACCTTTGTTCACGTGTTTAC
CTGCTGACCTTCTCTCCACTATTATCCTTTGACCCTGCCACATCCCCCTCT
CCGAGAAACACCCAATAATGATCAATAAATACTAAGGGAACTCAGAGGCCG
GTGGGATCCTCCGTATGCTGAACACCGGTCCCCTGGACCCCTTTTTTCTT
TCTCTATACTTTGTCTCTGTGTCTCTTTCTTTTCCAAGTCTCTCATTCCAC
CTAACGAGAAACAACCACAGGTGTGGAGGGGCAGCCCAACCCTTCAACCTA
CCTATCTTATCTCTTCCATTATCTATCCACATATGTCCTCTGTATTTTTTT
GAGTAACATTTATAAGCATAAGTCCTTAGGTAGCTATGCCACTTACATAAT
GAACTAGAAAAGGTAACCAAACAGAATAGGGTTGTACTCAGATATACCTTC
TACAAGTTTGTGTTACACATATTTACACATATTTAAAAATATATACATATT
```

FIG. 8-151

```
ATTATTGTGCTGTGTGGTTATTAGGCAAACTCAATAAGCAGTTCTTATAAA
GTATACTCAATGTAACTTTTATAAACTTACCATATTTTATAGTTATTCTGT
TTTTATTAGCTGCTATAAACTACCTGGGTGTCTTGCATGAGTCATTTTATT
GTAATGTTTTTGTATCTGTTGAATGAGGAGTTAGAAGGCATCATCTTTAAG
GAGCTTTACAGGTACATGTCCAGGGCTCAATAATTTTATTATTATTTCCTG
GACAGATAAAACCTAAGCAGGTGAAGGGGAAAGAATAAAAGTGCAGGGTGG
AAGTTGCTTGAATGCTAACTGGGTCAACGATCTCCCAGAAAACCCCTGTAA
AAGAAACCTAAGAACCTACATCACCAGGAGACCATTGGGACCAGTTCCTCT
GGAATCCCTGAGGCCAGATAATCAGCTGAAGCTTTACATTCTGTCCCTTTC
TGGTCATGACTTTCTCCACAGTCTGCTTGGTGCCTCCTCCTCTGTGACTCT
AAATTCTTAGGATCAACCCCTCTTGCATATGCACATCCGCAGTGCCTGTGG
GATACGGTGTGGTGTGGGGAGGAAACTCTCTTCTGCCTTAATATTTTCCTG
TGTGCCCCAGGCCTTGACGGAATCCTGTCTCTCCATAATGTTGCTTTTCGA
GGAGACTGATTGATTGAGATGGCGTCTCACTTTGTCGCCCAGGCTGGAATG
CAGTGGCGTGATCTCGGCTCACCAACCTCCACCTCCAAGGCTCGAGTGATT
CTCCCACTTAAGTCTCTTGAGTAGCTGGGACTACAGGTGCATGCCACCACG
CCTGACAAATTTTTTATTTTTGTAGAGATGAGGTTTCGCCATGTTGACC
AGGCTGGTCTCAAACTCCTGGACTCAAGTGATCTGCCCACCTCGGCCTCCC
AAAGTACTGGGATTACAGGCATGAGCCAATGTGCCCGTCCTGAGGAGTTTT
CTTCTGGAATTCCTGCTGGGTTTTGTAGTCAGTCCTCTCCCCATTTCCCA
CATTGGCTCTTGCAGACCTTCCTTTTCCCCATTTCTATTTGCTACCATGTC
AGACATGACTTTTGCCATAGGATCTCTATTCTACTATAGAGGAAACCAAAG
CCATCAGTAGAAATTTCACTAACATGGAATCAGATTTATAGAAGAAAGGGG
GAGGAAAGTTTTGCCTTAACACCTGGAAGGGTTTCGTTTCTTTTAGTAGCT
GGGAGACAGAAACATAAGAAAGTAGCTTAGTAAGCTTTCTGCTGTTCAACT
GATGATGTGTGAGCTGTCAGTAGTTCAAACTAGTCATTATCTTTATGAATT
AATTATGTAATAACTTAAACAATGTCATAAACCTTCAAATCAGTTTAAGTC
TAAATGTGTCATATTTAATAACAAGAGCAAGAAACATACGTTATGATGAAG
AGCTCTTATATTTTCTTTGGATAAAAGTCAGTAGGCGGGGCGCGGTGGCTC
ATGCCTGTGATCCTAGCACTTTGGGAGGCTGAGGTGGGCAGATCATGAGGT
CAGGAGATCGAGACCATCCCGGCTAACACGGTGAAACCCTGTCTCTACTAA
AAATACAAAAAATTAGCTGGGCGTGGTGGCGGGCGCCTGTGGTCCCAGCTA
CTCGGGAGGTTGAGGCAGGAGAATGGCGTGAATCCGGGAGGCGGAGGTTGC
AGTGAGCCGAGATTGTGCCACTGCATTCCAGCCTGGGCGACAGAGCAAGAC
TCCGTCTCAGAAAAAGAAAAAAAAAAAAGTCAGTAAAATTTAAGAGAAAA
ATGCATTTGCTTTGGGACTTTTAATATTTAGTCTACAAATCTAGCCACCAT
AGAAATCTGCTGATTAAATACGGGTTCTGTTAAAATGGAAACATGCATTTT
GGGGGAAAAAGAGGGAGTGTTTTAGTGATTTTGTTTTTTACACTTGTTTA
TAATAAAATTTTAAGCAATCTTGAGGGGAACATTTTATTTCTACTTGTAAC
TGCATAAAGTTATGAGATAAAGTTACAAGCTATATCACATACAGTTTGTAG
CTTTATAAATTATGAAATTCTAACAGAATAAATATGCTAATATGATGAAAA
TGTCATAAATTACATTAGAATATATTTTAATAAACCAATTCAGAAGGAGCC
AATACCCAATTTCAAAATCATATTAATTGTAAAATTAATTAGGGCAGCCAA
AATATTCTGGAATTCTTTCTAATAAAACAAATGAGTGTAAATACAGTCGTA
CTGACAAATCTGAAGAATTATGCAGCATAAAAAGTGATTATCCCAGCACTT
TGGGAGGCCAAGGTGGGCAGATCATGAGGTCAGGAGTTGGAGACCAGCCTG
```

FIG. 8-152
```
ACCAACATGGTGAAACCCCGTCTTTACTAAAAATACAAAAATTAGCCGGGC
TTGGTGGTGCACACCTGTAATCCCAGCTGCTCAGGAGGCTAAGGCAGGAGA
ACTGCTTGAATCCAGGAGGTGGAAGTTGCAGTAAGCCAAGATCACGCCACT
GCACTCCAGCCTGGGCGACAGAGTGTGACTCTGACTCAAAAAAAAAATAAA
TAAATAAAAATAAAAGTTTTAAAAAAGTGATTATTATGAACACAGAGTAAT
CTAGTAAAAATGGTTAAGTGAAAACAGCAAAATACAAAATTGAATATGTAC
TATAACAATATATGCAAAATATACTCAGATTTATAAAAATTAGAATGTAGA
AAAGTAAATATAGCTCTTCATAATTTTGTTCTGAAGTTTAAAAATATATAT
ATTTTTGAATGGATAACTTTCTTTTTCTAAATGCTTACAGTAGAGCCCACG
ATGGTTGTTAAAAGCCCCCAGGTTCAGCCTTCTTTAATTGTGTGGTCAGCC
TGCCATCAACCCGAGGCCTCCCTCTGCTGGGCAAATTTGGGAACACATTGA
GAAATCCTTACACGTAATTCCTTCTCTTCATGTTCCTGGTGAGCATTTTTC
CCATTGGGTTTCCATACTCTGCCCTCTTGAAGTCCTGCACCCTGACATTGC
AGTGTCATTCCTCTTCTACTGAAGTCTACAACTATTAGCTTATTGTCTCTA
GCAAGTCTCCCTTTAGCTACAAATATCATTCAGAGTTTTACCTTTCAGAAA
CTTTCTCCATGAGCATTCTGGAGTAGACTCTAGGTGCACTAGGTGCAGTTA
GAAAAGTTCTGATTTGTTGGTGGAGCTATAGGAGGAGAGACAATGGTGGG
CTGGAGAAGGGTGTCTACATGCAGAGAAACTGACTGGAAACTCAGAGAGAT
GATGGGGATTAAAATAATCCTATTGAATCTGCACAAAAGTGTTTTATTATA
ATTGATCCTGAACTATGTAAAGGTAAGCTCCAGTGAGTAGTTACAGTCTGT
CCCTAAGATGGACTCTTTCTTTTTGCTTTTATTTTTATTGTATTTATTTTA
TTGTATTTTTTTTTCTAAAGACAGGGTCTTGCTATGTTACCCAGGGTGGT
CTCAAGTGGTCCTCCTGGCATCAAATGATCCTCCCACCTCAGCCTCCCAAA
GCGCTAGGATTACAGGTGTGAGCTACCACACCCAAATGATTCTTTCTTTTC
AAATACAGAGTTCAGCAGCAATTTTAAAGAAGTACTGAACTCTACTGCCTG
GAAGATGGAATGGCCCTCACAATTCTTCCAGGCAAGCTCTGCACTCAGTGG
TATGGACCACAAGGCAAGCCCATTAAGGGGTTAAATTACTGACAAACAATA
ATTTCTAAATATGAACATTTCAGGAGGAACTAAGATGGCTCCTTCTTGGAG
AATAAGTTGGCCGGCTTCTCTAGTTATCAGACTATCAGATGGGGAGGAAAG
AGCCCCTCTGTCCCGGTGAGACAGGACCCGCCAGCGCCCAAGCTCTAAGGC
TTTCTGATGAGCAAATGGGGTTTCCATCTTTCTAGCTTCAGGACTCGTAAC
TACTCAGATTATTTCCTTCAATCTGGATATTCAAGACAAGAACAGTTCATG
GTGTTGCGAAGGCCCAGATTTAAATCACATATGCAAAGATACTGACATTCA
GTGGAGGGTCACTTAGATTATAGCCAGATGACTTTCCCTAAATTGATAGCT
CAAATGGTAGTTGTGGATATTTTGCTCTTAGTTACTTGCATAGTCACTTG
CCAGAGGTAATAAAGTTTTAGTGTGGTTGTGGAAAATAATGGCCATATATT
TAGGAACAAAATTTTAATGATGATTGAAAACTGAATTAGCTTTAACATGTG
AATATGCTCAGGGGACATAGGACCACAGATCTCTGTTCCTTCCTATTGCCA
CTTCTTTCCTTTCCCTGGTAGCATGCTTCCATTACCCATTACTTCAAACAC
TGTTTCTGTGTCTCCAACTCCCTTGCATCATGGTCTTTTCATTATTCAGAC
ACAGACACAGCTCGATTATGGGTAAACTTTTTCTGTGGCTACAGAAGAGT
TGAGCATGGCTGAAGCATCGTTGAGCATGACTGAAGAAAAACACCTAACCT
TGAATTTTTTGATCAATATAAATTTATATCCACAGATTTTACCTGACTGAT
CTTCATTGCCCACCAGTCCTACAAAGTTTGCCAGATTGGTTCTGTTTCCAC
TTTACATACTCAGCAAATACTTATTAAGCACACACTTTGTGTTAGGCTTAA
GTGTAGATATTGAAGAGGCACTGGTGAATGAGCAGAGGCTCTGCCCCCATG
```

FIG. 8-153

```
GGACCTGCATGCTATTTGGCAGCTCTTTCAGACATTCTCCTCTCTCAAAGC
TTTGAGCCCCTCTATACCCCTATAAGCACCTACTTTCAGCTGCTCCCTCAC
TCCCCCCTTCATGGGGGAAATAACAGCCATCGTGGTAAAACCTCCACTGCC
TGACAGAGCTATATTTACCATCTTTTCTTTAATTTTTATTTTTAATGGACA
CAGTTGTATATATTTATGGGGTACTATGTGATATTTTGATACATGTATAGA
TTGTGTAATGATCAAATCAGGAATTAGATCAGTTTTTTGTCTTTTTTTTGG
TAAAAGATAATCTTTTATACTCTTTTGGTCCTGAAAAATGGAGGAGTGCCA
TATTAGGATTCCAACAGAAAAAGTTAAACCAAAAGAATATATGAAGGGCAT
ATAATGAAGGGATATCTACAAAGTTGTGACAGGGCTAATGGGAAGAACAGG
GGATATGAGGCAGCCCAAGATCAGCAACAGTAGTGATCCAGTGTCACCCTG
TGCTGGTTATGAAGATTTAGTCTCTTCTATCTTTTCCAATACCGCTTTGCT
AGCCACCTCCCCAAACCCTACCAATAGAAAGCACTGGAGGAAGACTAGAGG
GCTGGAAGGATGTGAAAAGATTTCCCACTTTGTTTGTTGACATCCTCACAG
AATGGGTTCTTCAACCTGGCAGTGGCAGTTGAATCCAGTAACAGCAGTTGG
CTTCAGTTTGGAGATCTTCCATGCTCCTAAAATCAGCCTCATCATGCCTCT
ATCTACAGACATATCATCATCAGTGGTCCAGCATACACTCCTCAGAGGTCC
CAGTTCTGGGGATCTCTTCAAAGAATCTTTTCCTTGTTCTCCTAAACCTGG
AGGTGGTAGTTGCTTTCTGTCATTACTATCTCTGATACGTTTGTCCACTTT
TCCATTTTCAGTCCTCTTATAACTAGTTAACAACCATTCCCATAAAATTCT
TTGTTCAATTTCAGTGCAATTTCTAGCTCCCAGTTATACCCTGACAGACAC
ACCTTTAAATCTGAAGAGGCAATGGGAGGGAACCTGTAACCAGAGCTAGGC
CAGAGCTGGGACTGTGGAGGAAGAGCTGCCCACCAAGCAGGGGGGTGATGC
AGGGAATAAGTACACTAACCTCTCTCTCCTTTGCCATCTACATTCCTGCTG
GGCTGATCACTGGCCAAATCCAGCTGTTGCAAGAGGGCAGGGCTGCCCAGC
TAATGCTATCTGTAGAAGCTGGGCTTCTGGGGCACAGAGCAAGTCAGAGAC
AGGCAGAACAGGGATGTGGGTTTGGACCAAACACTGAATAAACCAGATCAA
GGATTCTTCTATCAAGACAAGTTTATATACTTGCAGCTTGATCCCATTGTT
TCCCTTAGATAACTGTGCACTTGTTTTTGTCTGCCCTCTTTCCTGTGTCTA
CACTCTTCCTGTCTTATTCTATTTACACATAGCTCAGTCTTTTCCAATTAA
AAAAAAAAAAAAAAGCTTTCCCTCTCCCAAATCTCCATGCAGCTGCTGAC
TTCTCTCTTCCAAAGCCACACTGTGGGAGAGTCAGTTACACCTCCTGACCT
CTGACAGGTGCAACACACTATAGTGAGGCTTCTGCCCTTGGTATTCCTCTG
GCTCCATTATTTACAAGGTCACTAATGACTTCCTATTTCTAAATCCAGAGT
GCCTTTTTAGTTATCTTCCTTGCCTTCTTGGCATCTCTAGATAACAATACT
TGTCTCATTCTAACTTTTGTCTCTCCTTACAGCTCTTTCATTCATAATTCA
TTGTTATTCAGTTGGAGCCTTGATGGTGTTAGGGAGAAGCAGCATTCTGTA
GTCAAAGTGTTAAGCCTCAGTTTATTAGCATGCCTATATCTTGGGGCTGGG
ACCGTCACAAGTGTTTATAATGATACAACTCCTCCTCCTCCTCCTTCTCCT
CCTCCTCTTCCTCAAGTGTTTATAATGATACAACTCCTCCTCCTCCTTCTC
CTCCTCCTCTTCCTCAAGTGTTTATAATGATACAACTCCTCCTCCTCCTCC
TTCTCCTCCTCTTCCTCAAGTATTTATAATGATACAACTCCTCTTCCTCCT
TCTCCTCCTCCTCAGACCTTTGCTCCTTTCCTGGCTGCACCATTTCCAATT
TATTTTCATGAAGCTCTGATCCCTGTTGACTAATTTTCTTCCCTTAAGTGA
GACAGAAAGCCTAGATGAGGCTGCAGTGGGAAGAATTACCTTCTCCCAGCT
GGGATAAGACTCTGGCAAAATGTTTTCCCCTTGAGAGTAGGCCTTTGTTTT
GAAGAAGGTTCTGGGGTGTATTTCATAATAATTCTTCTCTCCCTGCCAAAG
```

FIG. 8-154

```
CCACAAGAGGATCCTTCTCAGATCTTCACTGCAGGAACCTGGTGGGCTTTC
TGATGCCCACAAAAGTGTGGGAGCTTCTCACTCTCATGGGCATTCACAGTT
GGCCTCCAGCTTTTTGTCAGAGTTACCAATTTAAATGTTCTCAAATGTGAT
ACTGTCTCAACTTCCAGGACATCACACACTCATGATTTTCTACTATCCTGA
CATTTGCAGTCTTTTTAGCAGATCTCCCTCCCTCTCCCTGCACCATGGGTA
TTGGTCATCTCAGGATCTGTCCCAGGCTTTCTACTCTTCATGCCCTTTGAG
ACAACACATGATCTGACCTGCCCTTTCAGGAAGAAATGTTCTGTCTACCTA
CTTGCTCCAGTTAAAAACCCTAGTGTCATCTTTGACCCTTCTCATCCCTAC
ATCTAATCTGTTGATTCTACCTCCTAATTTTCTCTCAAACGCATCTATTTT
TCTTCAATTTCAGTGCTACTCTCTTGCTCTAATTGTACATCATCTTTTTA
GAATTACTGTGACATTTTCTTGCCTCCAGTTCTGCCTCAGTCCATCCACTT
CACAGCTAAATTTTGGATGTACACTTTTGAACTATTACTGTAGCAAAAGTA
ATATGTAATAACTGTAATGCAGAAATATAAAATATGCAATATAAAAGAAAT
ACATGCATAAATGATCCCAACACTAAGGAAACAATATTGATCAATAATTAA
ATAATTGGTGGATAGTGAATGACAACATAGAGCAAAGTGTTCAGTAGGTTT
TAAAAGCTGTGGGTTCAATAAATGCTCATGAAGCTTGTTCAGGGGCTTGCA
AAATATGTAATTTGAATTTTTAAAGAAAAGGAATTTCAGATAAGAAAAAAC
ATACATAACATGAAACAATACTTGTGGTGGTTTCAGGGAGGTCATGTTCTC
ACATTCAGGTGCCAAGGCCACCGTACATCCGGACACTGAGGCCACGGACTT
GGTCTGCAACCTCCATGACAGCCTTGTAGATTTGAAACCGAACTCCAAGGA
GCAGTTGTGCTGTGAGTTCCAGAGTTTGGGGACAGAGGAAACACCATTCTT
TGGAAGTCTAACTTCCTTAAGAGGTGTCCCTTAGACATCTAGTGTCCGGTG
TTATGGAGGTCCTTGTGCTCTGAGGAAGGAGCCCCTTGTTGATTGATGGAG
CAAAATTTTTTTAAACAAGGAACTGTACCCGTATCTGGGCATGAAGCCAGA
GAAATCCCTGAGGGCAGGGCCAAGGCTCTCAAAGATTTTCAGGGAGATTCC
CAGCCTTTTTAAGTCTCGCCTATTCTTTTTTTTTCTCTAACTGGCCATTT
TGTATATATGGAGGTTATTGATTTTTTGCTTTTATATCCTGATATTTTAA
TAACTGTTCATTTTTTAGTTATTTGAATTATCTACATTGATTATTTGAATG
TTCTTTTTTTTGTTTTTTTGAGACGAAGTCTCGCTCTGTCGCCCAGGGTGG
GGTGCAGTGACAGGAACTTGGCTCACTGCAACCTCTGCCTCCTGGGTTCAA
GCGATTCTCCTGCCTCAGTCTCCTGATTAGCTGGGATTACAGGTGCCCGCC
ACCACACCCAGCTAATTTTTGTATTTTTACTAGAGATGAGGTTTCACCATG
TTGGCCAGTCTGGTCTCAAACTCCTGACCTCAGGTGATCCACCCACATCGG
CCTCCCAAAGTGCTGGTATTACAGACATGAGCTATTGCACTTGGGCTTTGA
ATTTTCTACGTATCTGACTTCTACGAAGAAAACTATAATGTATTACTCAGA
TAAATTAAACAGGAAAACTAAATAATGGAGGAGTATATTTACAGTTGAAGC
GGTCAATATTTTAAAGGTATTAATTGTCCCCAAACTGATCTACAAAACCAT
TGTAATCCTAATCAGATTCCCAATAAGCTTTATTATAGAAATTGACAAACA
GGGTTCAAATTTAATACACAAATCCAAGGGCCCAAAATAAACAAATCTGTT
GCTTTATTAAATATCAAAACTGATAAAATGACAATAATCAGGGCAGTGTTG
TCCAAAAATAGACAAACGAATGGAACAGGCTCAAACAAATATGGACATTGA
TTTACATCTAAAGTGGCACCATACAACAATGGTGAAAGGACTCTTGTAAAT
AAATGGCATGGGACAATTGTATAGCCTTTTAAACAGAAAAAGAACAAAAAG
GAAAAAAAAGAAACTTGACCCCCTACTTCACACTATACACAAAAAACAAT
TCCAGGGGAACTAACATGAAAAGCAAAATAAAGTTAAACATGAAAAGCAAA
ATAAAGTATATGGTAAAAAATTTATCTTACCCAAAAAGAGGTCTAGCCTTT
```

FIG. 8-155

```
GCCCTCAGCTACTGGGAGATGAATTTTAGACCCTTGAAATGTTCTCACTGA
TAAGTGTGTCTTTGTTTACCTGGAGGTTTTGACCACCACACAGTCAACAAT
GTGATTTATAATAGGAACTTTGAGCCACACAGTATCAGCTCTACCTGTGGA
GGTAGACTAAAAGATCGGCCATGTGAGCAGTCAACCATGGCAGGCCATTAA
AACTGCACACTGAGGCTCGGGTGAAATACAGTTCTCTTGTATACGGTTTCT
ACATGGTTTTAGTTCCTGTGGTCTACTGCAGTCCAAAAATAATAAACGGTA
AATTTCAGAAATAAACATTCACCTAACTTTTATACAGTATATTCTTAACAA
TTATTCTAATTTATTGTTATTAATCTCTTACTGTGCCTAATTTATAAATTA
AGCCTTATCATAGCTGTGTCTGTATAGGAAAAAACAGCTATATAGAGTTCA
GTACTATCCATGGTTTCAGACATCCACTGGAGGTCCTGGAACATATGTTTT
GTGCATAAGTGGGGACTGCTCTGTACGTCATGTGTATTGTCACACATTAAT
GCTGGGAAAGTAATACTGTTCATATTACTGGGAGAGGACAACTGGAAGCTC
ATATTTGGAACTTGCCTGGATTGTGCCTATATTAGTTTCCTAGGGCTGCTG
TAACAAAGAGCTAGAAGCTAGGGTGGCTTAAAACAACAAATATATTCTCTT
GTAGTTCTGGAAGCTAGAAATCTGACATGAAGGTATCATTAGATCTATGCT
TCCACTGAAGCCTGTAGGAAAATCCTTCCTTGACTCTTCCTAGCTTCTCGT
ACTTGCTGGCAACCTTTGACATTCCTTGACCTGCAGCTGCATAACCTCAGT
CTCTGCCTGTGTGTCTGTCTTCACGTGACCACCTTAGAAGAATACTAGT
TCTATTAAAAAATATATATACTACTTCTTCTAAGTCACCAGCCCATCAT
ACTGTACTATAACCTCATCTTAACTAATTATATCTGCAACTATCCTATTTC
CAAATAAGGCCACAATTCTGAGGTACTGGGAGTTGGGACTTTAAACATATC
TTCTGGGGGCAAGGGAGATCTGCATACAATTCGATCCATAATACTGCCTTG
TGTGTTTCTTTTCTCAGCTGATTTTAATCTTTATTCCTTGAGTTGTTTCCC
CTTTTCAACTATTACAAACAATGAATTTTGCTGTGTATGTGTCTTGGTATA
TATGTGCACACATATCTGCTGTTTGTATACCTCAGAGTGAAATTGTTGGGT
CAAATGCTAAAATCTTTTTAAAAGTAGTTGTATAATTTTACATTGCATTGG
AATGACATAATAAGCTATATATCCTATAATAAATTGTAACCATGAGGCTAA
CAGCTTCAGCAAGTTCTGTGAGTCCTTTTAGCAAATTACTAACCTAAGGTT
GATTGGGAACCACAGACCTCCCAACTTATAATTGGTGTTAGAAGTGAGGGT
AGTCTTGAGAACTAATTTCACAAGAAGGTATTATAAAATAAGATCTTCATG
ACCTTGAAATAGAAAATGATTTTTTAAATAAGATACAAAAAAGGTTGTGCA
TAAAAGGGCAGTGTGCTTAATTTGAGTACACTAAATTAATGACTTTAATGC
ATCATGAGATATCATTGGCTGGGTGCAGTGGTGGCTCACACCTCTAGTCCC
AACACTTTGGGAGGCCAAGGTTGATGGATTGCTTGAGCTCAGGAGTTTGAG
ACCAACTTGGGCAACAGCACCATCTCTACAAAAAAATACAAAGATTAGCTG
GGCATGGTGGCCTGCACATGTAGTCCCACCTACTAAGGAGGATAAGATGGG
AGGATCGCTTGATCCTGGGAGGTGGAGGCTGCAGTGAGCTGTGATTGTGCC
ACTGCACTCCAGCCTCTGACAGAGTGAAGACAAGTTACAGAGGAAATACCT
GCAACACATAAAATGGATAAAGGGTTCGTGAGCAAAATTTAAAAACTTAAA
ACAGAAAAGACAGGCCAGGTTTGGTGGCTCACACCTGTAATCTCAGCATTT
TGGGAGGCCGAGGCAGGTGGATCACCTGAGGTCAGGAGTTTGAGACCAGCC
TGGCCAACATGGTGAAACCCCGTCTCTATCAAAAATACAAAAATTAGCAGG
GCGCGGTGGTATGCACCTGTAGTCCCAGCTACTTGGGAGGAGGAGAATTTC
TTGAACCCAGGAGGTGGAGGTTGCAGTGAGCTGAGACAGCGCCACTGCACT
CCAACCCGGGTGACACAGCAAGAGTCCACCTCAAAAAAAAAGAAAGGACAA
AAAGGACAAAAAGACAGCTATCTTAAACCAACAAGAAAAAACACAATCTTT
```

FIG. 8-156

```
TTGGCCTAAATTGTGTTCCCCCAAAATTGATGTTGAAACTCTAACACCCAA
TGTGCCTATATTTGGAGATAGGGATTTTGGGACTTTATGGAGATATTTAAG
GTTAAATGAGGTCATAAGAGTAGGCCAGTAGTCTGATAGATCTGGTGTCCT
TATAAGAAAAGGAAGAGACATGAGGTCATTTTATGGGCATATGAAGAGGCC
ACATGAGGACACAAAAGGCGACTGCTGTGGTTTGAATATGAGATGACATCT
CACATCTGCCATAACAGTAAGAAGGCCCTTGCCAGAGGTGGGCCCCTCGAC
CATAGGCTTTATAGCCACCAGAATTGTAAGAAATAAATCTGTATTCTTTAT
AAATTATTTGGTCTCTGGTATTCTGTTCAGCACCAAACAATCTAAGACAGC
AACTATCTTCAGGTCAATAAGAGAGCCCTCACTAGAAACTGAATCTCTTGG
CACCTCAATTTAGGATTTCTGGCCTGGCCTTTAGAACTGTGAGGTAATAAA
CTCCTTTTGTTCAAGCTACCTAGTCTAGTATTTTTGTTATGGCAGCCCAAG
TCGACTGATATACAATCCAATTAAGAAAAAATGGGCAAAAGATGTAAAATA
AAACCATAATGAGATAATACTGCACATCTGCCACAATGGATAACATCTTCA
AAAGATTAACAATTTTAATTGGAAAAAAATATTGGGAAGTATATGGAAGAA
CAGGAATTCCCAGCTAGATTCCATCAACATTAGGTTTGTGAGGTTCATCCA
TGCTGTTTATAACTGTGGTTTTAATTTTCATTTCATCGCATGTAAACCTAA
TATCACCACTTTCAAAAAGAGTTTAGCATTTGACCCAACAATTCCTCTCCT
AGGTATACAAACAAAATATGTATTCCTATATATACCAAGACACATACACAG
GAATATTCACGGTATTGTTTATATTAGCTGAAAAAGGGAAGCAAATATGCA
TCAACAGTAGACACCTAAATTGTTGCACTCATAACATGGAATATTACATAA
CAATAAAAATGAATTAAAGTTATACACAGCAACACAGATGAATCTATTCAA
ACCTAATGTTCTGGAGTGAAATATGTCAGGTACATAGGATTACATTTGTTT
TATTTCCATTTTATATGTTTCAAAAACAGGCATACTAAATTACAGCATTGG
AAATCAAAATAGGGGTTATGTTTAGGGCAGATGGAGTGATAATGTGACTGG
AAGCAAGCATCAGGCGGCTCTGGGAGGGTTGGCTGATTTTCTGTTTTTTA
CTTGTGTGGCAATTATTATGGTGTTCACTTTGTGTTCATTTATTGAGCTTT
GCATTTTGTTTTGCTGTGGTTTTCTGTTTATATGTTATGCTTCTCAGTTT
AAAGAATGTTGAAATCTTCTAATACGAAATTTTTTTTCAATGAGAAGGATT
TTAAGCATCCAGAATCAATTTTAAAATCTCCAATTTGCTTTATATGTAGGT
TTATGGACTGCTTAACTGCTACTCATTTTTTCCTTCATTTATCAATAGTGA
AATATGAAATTAAAATAATGACTATTTGTGGCAAAATTAGGGACTATGTAG
CATATTAACAACTTTATAAATAAAAGAATAAATCAACTCACCTGGGAGTTG
TTACTGTCATTGACCTAATGCTATTTCCCATGGTACTCCTTGTCCCCATTG
AGAGACATGAGATACTGCAGATTTATGGGTCACTTTCAACATGTCTCCTCC
AGGCCTCATTTTAGAGAAGCATAACATCATGAGGTTCTATACAGGCAAGAT
CTAGGCTTGTGTCCTTGAACCTTGCATTCCCTCTCAAGAGCCAACCAATAA
TTGAATGATCCTATAAAAAACACAGAAACACAGAGAATGGTAGCAGAAAGC
GGATGCTTACCAAACCTATTTTCTCTTTTTCTAAGCAAGGAATAAGAATAA
CTTACCTTCCTCCCTTGGAGTTAGGAGTTCTTATGTAGAAAGGGAGGCAGA
GTGACCTTCAAGAGAGTTTGGAAGGGGGAGTGATAAATCAGTTTAAAGAGA
GCACCCACTGATTCTTAGATAACTTATTCTACTTTCCTTCTCACTCTTTTG
CATTGACCATGGCTTAGAATATATTTGAGGAAAAGCATACTGTCCATAAGG
TATTATTGCCCTTTAAAGCTGTTGGGGGGTACTATGGGATGGTATTCAGTG
AGAGCAGGACAGAGTCTCTACAGAATTTTCTCTGACAAAACAAAAACTAAA
TGACTTCCAAGGCTTCTCTAGCTCTAAGCATTCCACAATTCTTTGGAAAGC
TGGAATCTAAAATTGCCTTAAAATTAAAAAATAAGAACAGTTAGGGTGTAC
```

FIG. 8-157

```
AGTCTTTACCATATTTATATAGAATCATCAGTCTTCAGTGTGATACTGTGC
TTGAACCAACAGAAGGACTGATGAAACAGAAGACAAAGTCCAGGTCTGGCG
CCATGGCTCACACCTGTAATCCCAGCACTTCGGGAGGCCGAGGTGGCCAGA
TCACTTGAGGCCAGGAGTTTGAGACCAGTCTGGCCAACATGGTGAAACCCC
ATCTCTCCTAAAAATACAAAAATTAGCCAGGCCTGGTGGCAGGTGCCTGTA
ATCCCAGCTACTCGGGAGACCAGAGGCATGAGAATCGCTTGAACTCAGGAG
GCAAAGGTTGCAACTGAGGTCATGGCACTGTACTCCACCATGGGTGACAGA
GTAAGACTCTGTCTAAATAAATAAATAAATAAATAAAATAATAAAATACAA
CCTAAAACCTAGCAATCTCAGCCCTGGAATTCTATTCAATTGCACCATGTT
CAGCAGTGGTAACTGGAAACATCAATGCTTATCAATAAGAAATGGATGAAT
AACTTATGCTATTCCATGTGAAGGATTTCTTTTTTCATGACAGGGTTTTAG
AAAAGTTTGGTTAAGAGAAAAGCAACATGCAGAAGTGTATATAACATCGTT
GTAAAAAATTTTTATTATTTTTGTTTTGAGACTGGGTCTCATTCTGTCACC
TAGGCTTGAGTGCAGTGGCACGATCTCTGCTCACTGCAGCCTCTACCTCCC
AGGTTCCAGTCATCTTCCCACCCCAGCCTCCCAAGTAGCTGGGACTATAAG
TGCGTGCCACTGGGCCTTGCTAATTTTTTGTATTTTTTGTCAAGATGGGAT
TTCACCATGTTGCCCAGGCTGGTCTTGAACTCCTGAGCTCAAGTAATCTGC
CCATCTGGCTTCCTAAAGTGCTGGGATTACAGATGTGAGCCACTGCGTCCA
GGCTTTGTTTTTAAATTAATAACCCTAATCAAAAGACAAAACAATTATGC
ATACAAGGCCAGGCACAGTGACCGTAATCCCAACACTTTGGGAGGTCGATG
ATCACTTGAGGCCATTTCTAGACCAGCTTGGACAACATGGTGTGACTGTCT
CCACAAAAAATAAAAACAAAAAGCCCGGCTTGGTGGTGCGTGCATGCAATC
CCAGCTACTCCGGATGCTGAGGCTGCAGGATAGCCTGAGCCCAGGAGTTGG
AGTTGGAGGTTACAGTGTGCTGTGATTATGCCACTGCAGTCCAGTCTGGGC
AACAGACTGAGACCCAGTCTCAAAAGATAACGTGTTTTTTTTTTTTTTTT
TTAAAAAAACAAAACCACAAGTATGCATGTATATAGATAGGTGTATGTAAA
ATACTTAGTTCAAAGAAAAACATGTATATTTCTCACAAAAATAGGTGAGAA
TTTTTGTTTTAAAGGATAAACCTAGGTAGCTACATATTAGTTTGAGGAAGG
GGGAACAGGGATGTGATGTGCCTGTATCCCTGACTTTAGACGATGGAAGGA
GCTAAGCAAAACAATTGAAAAAGACCGTTTGAAAAATACAACTGATTATT
AACTCATATGCACACACGCAAAAATAAACTTTTAGAATTGAACTGCACTAA
GTAAAAGTGAGTAAACTTGGCTCATCATATACTCTTGTCAGATGTAAACAA
AAAAGTCCAATTATTAAAATCTGACCCCCAGAATTAAAATTGCAAAAGCTT
AAAGGGGCAGTTCTGAGAAAAGGATCTTCAGTTTTGAATGTGTGGGCTCCA
CCAGGGTTGAAAATCCTGCACGACTGATGAAACACGATCCAGTTAAGCACA
GTAATTTTCAAATATCCAATCAGGGCGCTTCCGTTTCTAAAAACAGAGAAA
CCGAGCAAGGGATTTTGGGTTGCAGCTCTAAAACTCCAACAAACTAAGCTC
CTTTGTCCTGACAAGGGCCTAAACCAAGTCGACAGCCCGTAAGTGCACCCA
TGGTAAGGCGCTGCACAAAGAAAGCATTTTGCGTTTCAAAGCTTTGTCATG
ATGGCGCTGCAGAAAGCAAGCGAGCTAGGCCTACCTGGCGGGGCTTTCAGA
GGACGCCAACGTGGGCGCCAGCCACGCCAGCAGGGTCACCGTCCTTCCCAA
GGACAGACAGCTCGCTAGCCACTCCTGTGGAGAGGGCGTGGTTAAGCCATA
TATTTTGCCAACTATCCCAGAAGCATTTCTTAGGACCACCCAATTTCGGAA
AATGCTACTTTAGCAATATTGACCCCAAAACGCAATATCCCCACTTTAACC
TTGTATAATAAAAAGCCTCAAGCCTGGGACTGGGCTTCAACCTTGGTTCAA
TACGGTTATGACTAATTAGCTTGGAGTCGTGAGACGCGGGACTTCCGGCTA
```

FIG. 8-158
```
CCGAAACCCAGGTGACTTTAAAACTCGATTTTAACTCGGTGCATTTGAATT
CACCTTGCTATCTTTGATAGATTGAGTAGTAAATTCTTACTAGATGAGGCT
ATGTTAAAGTTCTATCGACTCTCCAAGTGATTCTAATATAATTGAGGGCGT
GTTGCATTTGCTTGGGGGATTTCATCTGTGTACTACAGCTCTTTTCCTGAA
ATGCGTAGGTGGCTCTTAAAAGAGCCGTTGGGTTACTAGAAGAAACTTCTA
ACTGAATTTACTTTTTCTTGGGTGCCGCTTTCTTGGGTTTGGCAGTCTTTG
GCTTCGTCACCCTAGCCTTGGCCGCCTTGGGTTTTACAGCCTTAGCTTTAG
CAGGGCTTTTAGCTACTTTCTTGGGCTTTACAGTTTTGGGTTTTTTTGGAT
TCTTGGAGGATTTCCTTGTTGCCGCAGGCTTTTTAGCCTTTTTCGGAGTCT
TGACGCTCTTTTTGCTAGCCCCCGTGGCCTTTTTGAGCTTTTTAGATGCAC
CCGTTGCCTTAGTTTTTGTAGCCACCTTTGAGGCGCCGGGCTTGGTTTCCA
CGGAGGACGCCTTCTTGTTGAGCTTGAAGGAACCCGAGGCTCCGGTACCCT
TTGTCTGCACCAACGTTCCCTTGCTTACCAGGCTCTTAATGCCCAGCTTAA
TGCGGCTGTTGTTCTTCTCCACGTCGTAGCCTGCGGCCGCCAGCGCCTTTT
TAAGAGCTGCCAACGACACACCACCACGCTCCTTAGAGGAGGAAGCAGCCT
GCACGATCAGCTCTGACACGGAAGGGCCAGCGGGTTTTTCTTGGAGGCTG
CTGCAGCCTTAGCAGGTTTCTTTGCCTTCTTGCCAGCTAAAGGTTTCTCAG
GAGCAGCAGAAGCGGCGGGGGCGGGAGGCACTGTTTCAGACATGGTGACTA
ACACAGCACACCAAATAAAGTGGTATAAACCTGACGAAGCAGGATGCGAAA
AAAAGGCCCCAACGCAGCCTATTTATAGGGTGGGACTGCGCCGTGATTGGT
GCCCGTCAGTGCCCGCCCCTCGCGCCCTAGCGCCCCTGCGCGCTGCCGAG
GGTTTCGCCCAGTCTCAGAAGGCAGCTGGGGGCCTCTAGGGCCTATGGTCC
TGCTCCCCTCAACGCAAGCAAACACACAGAAAAAGCCGCTCTGGTTGCCTC
ATTGTGAAGGAAATTGTAGGCAGACTGCCGCCCAGTAACATCAGAGGGTAC
CGCTTCTCTCTCAAAAAGCAGCTCTTTTTTAGGGAGTAGGTTGAGAGGGGG
CGGTTTACAAATGCAGTGCCACAAGCATCCGAGGAGTTTTATTAGAAATTT
TTAGAGGTCCGTTGCCAGAGATGTTAGTTTTTAATTTGCAAGAAATGTAAA
ATACAGTGTTTTGAATAGTTGCGGAGGGAGAGAAAAGTGCGAGTTTTAGGC
CGTGTTAGGGCCAGTTGTCATCAACTCTATTACATTTTCTGGCAATGTTTT
AGAGCGATGTGTCTCGCGAATACCTTTCACGTCAAACAAGAATGAATCGTA
GACAACACCAGAATTCACAAACGCTGCAATTAATACTCAAACTGCAAGTGT
GGAAACGTTTCTGCACTTGCAACTTATTTCCACAGTCCAATGTGGGATGCA
CTTCAGGAATTTCCAATGCCCTTTTCATCCATACAACATGCCCCAAATTGG
TATTAAGGTTTACAACCTGTGTTCCATGTCAGCACACGCAATCAGCGCACC
ATGACATGGTCAACTCATTCTTTTATTCAACAAATATTTATGGGCCTCACA
AGCCTGCGAAAGGCGTTAAATGCTGGGTCCACGAAACCGGTTCCCTGACAG
GCATTCTGCTGGGGAGTTAAGTCCACTTAGTGTGAAAGCAAACACGGGTGA
TAAATGCAAGCACACCCTGGGGATAAGATTTTATGGTAACAACCCTTTAAC
TTGTTTGTGGCTGTTAAGTGCATTTCAAAGTATCAATAAGCTAAAACGATC
TCACATTGCCAATCAGAGACTCAGCTAATGGGAGAATAAAAAACTATTAAA
TCGACATCCACTTCTACAATCCTATTCTGGATAACCCCCTAGCACAGCACA
GCAGAGAGTGAGGTAATGCGGTCTTATTTCCGCTCCTGCTGTGGTAGTTTT
CAAATAAGTCCGAACCATGCTAAGTAACCTGAGCTTTTCCCCTTTTTGTTC
AAACAACGTGCCAACCAAATAATGGAGTGGTCCCAGATAAGTATTGTACCC
ATCTTCTGCACCAGTGCTTCCTACGTCCCATTTTATTGAGAAGGCATGCAT
TCAAATATTTCACGTAATTTCTAAAAATTTGGAAAATAACGGTTGGAAACT
```

FIG. 8-159
CTACATCTTGGTTTGACGGCTAGTCAGTTATGAAACACAGGTATACAAAAT
TGGAAGATTTTTGTAAGTAAACCCTTTGTGAAAGATATAAACCTTTCTTAG
TGTAATAAGCGAGGTATCTGAAAAAACGCAACTTTTGAAAAGGAAATACTC
CTAATTATCTGATTCAGGAGTTTCCACTTTAAATAATGGGTTCTGCCTCCC
TTTTTTCTATTGGGTTAAACTGGTTTCAAATAAAATGGGAACGCTCCATGC
AAATGAAGGATGATAGATCTGCTTTCTAAATGGCTGTTCAAGAAAATAGCC
TAAACCAATCAAAAGATAGAATGTGGCCTGTCTCTTGTGAATTTAAAAAGG
TCACAATCCACTTTTCAGTGTTTTGAGATTTTCAAAATGATTGCATTAGCT
CTTGGCAATGCTAAATTATGTTCCTTGCGAACCACTATCCAGTTTCTCTTG
GGCCAAGTCCACCTCCTGCTCCGCAAGAGGAACAACTCCCAGCTGGTGGTA
CCTGGCGGCAGTGCTGGAGAAACGCCATTTTGTGACTGGCAGAGTACACCT
AGGCTTTAGAAAACAAAAGCTGCAGAACGCTGCAAGTTTAGGATTCAAAGA
GCATAATCAAGAGAAAGACGTCTCATAGAAAATGTTTCTGAGTAATAGTGT
AATCCTACTATGTTTGAGATGCTTTGTAGATTTCAATAACACTCCTAAGTC
AATTAAAGCATTACAAAGGAATCCAATTCTTGTGAAAGGTTTCAGAAATTC
CCGTAAAGGGTACATTTCCGGAGAGGAGGTGAGCAGTATTCCCTCTTTTTT
TTTTTTTTTTTTTTTTCCTAAAGAGCTGAAGGTTATACGGAATTGGGGAA
TTATAATACCTTTGGAATCAATGCCTTGTTTTATGGAAAATAAACACAGCC
TTCAGGTTATGAAAACCAGATGTAGAAGAGGACAAGTTTAAAAAAATTAAAG
TCCAAGCCGGCGCAGTGGGGCTCCCCTGTAATCCCAGCTACTCTGGATGCT
GAGGCGGGAAGATCCTTTGAGCCCAAGTTTAAGACCAGCTTGGGGAACAAA
GCAAAAGTAAAATAAAATAATAGTAGTAATAAAATACCACTTAAATAATCA
TCTGTAGAGTTGGAATAGAATATAGTAGCCGGTGAAACTGCACGATTGTTG
CTGGCTTAAAGATAGACCAATCAGAGTGTGTAACGTCATATTTAGCGTCTT
CTATCATCCAATCACTGCACTTTACACACTATAAATAGAGCAGCTCATGGG
CGTATTTGCGCTAGTGTTGGGTGTTCCGCTGTGCTGTTTTTCCGTCATGGC
TCGCACTAAGCAAACTGCTCGGAAGTCTACTGGTGGCAAGGCGCCACGCAA
ACAGTTGGCCACTAAGGCAGCCCGCAAAAGCGCTCCGGCCACCGGCGGCGT
GAAAAAGCCCCACCGCTACCGGCCGGGCACCGTGGCTCTGCGCGAGATCCG
CCGTTATCAGAAGTCCACTGAACTGCTTATTCGTAAACTACCTTTCCAGCG
CCTGGTGCGCGAGATTGCGCAGGACTTTAAAACAGACCTGCGTTTCCAGAG
CTCCGCTGTGATGGCTCTGCAGGAGGCGTGCGAGGCCTACTTGGTAGGGCT
ATTTGAGGACACTAACCTGTGCGCCATCCACGCCAAGCGCGTCACTATCAT
GCCCAAGGACATCCAGCTCGCCCGCCGCATCCGCGGAGAGAGGGCGTGATT
ACTGTGGTCTCTCTGACGGTCCAAGCAAAGGCTCTTTTCAGAGCCACCACC
TTTTCAAGTAAAGTAGCTGTAAGAAACCAATTTAAGACAAAAGGGAATGCA
TTGGGAGCACTTTTCGTTTTAATGCTACTGAAGGCTTCAAAACCAATCGAT
TTCGGCCGGTCGCGGTGACTCACGCCTGTAATTCAAGCACTTTGAGAGGCT
GAGGCGGGCGGATTACCAGAAATCAGGAGTTCGGGATCAGCCTGGCCAACA
TGGCCGAATCCCGTCTCTACGAAAAATACAAAAACACGCCGGGCGCGACGG
CGAGCGCTTGTAATCCCAGCTACACTCTGAAGGCTGAGGCAGGAGAAACAC
TTGAACCTGAGAGGCAGAGGTTTCAGTGAATCGAGATGGCTCTAATGTACT
CCAGTCTGGGCGACAGAGAGATTCGGTTAAAAAAAAAGTTCGACTTAAAAT
AATTCTGGAGTCAGAATGGGTTTACATTTAATTCTTAACCCAGTTCCTCAA
AGCCTGTAGCTCTGTTAAGAAAATAAAGGCCATTGGTCAAGCCTGCTTGGT
CCCACCCTCATCTCCCCACCCTCCCCCAATCGCTGCTCCCGCCATTTCCTG

FIG. 8-160

```
GGGCTTGGAGGAGGGGTTAAAGGAGCGGACTGTAGGCGTCACATTTCCCGC
CTGCGCGCTTTTCAGTCTCAGTGTCCGCTGGAGGTGGGGGCAGGGGTAACG
TAGATATATAAAGATCGGTTTCCTATTCTCTCACTTGCTCTTGGTTCACTT
CTTGGGAAGTCATGTCTGGACGTGGTAAGGGCGGGAAGGGTTTGGGTAAGG
GGGGTGCCAAGCGCCACCGCAAGGTGTTGCGTGACAACATCCAGGGCATCA
CCAAGCCGGCCATCCGGCGTCTGGCCCGGCGTGGCGGTGTGAAGCGGATCT
CTGGTCTGATCTACGAGGAGACTCGCGGGGTGCTCAAGGTGTTTTTGGAGA
ACGTGATCCGTGACGCTGTCACCTATACGGAGCACGCCAAGCGCAAGACAG
TCACTGCCATGGACGTGGTCTACGCGCTTAAGCGCCAGGGACGCACCCTTT
ATGGCTTTGGCGGTTAAGGTTGCTGATTTCTCCACAGCTTGCATTTCTGAA
CCAAAGGCCCTTTTCAGGGCCGCCCAACTAAACAAAAGAAGAGCTGTATCC
ATTAAGTCAAGAAGCTCAATGTGTAATTAAGATGAATGATACTGAGCTGAC
ATCCTAAAAAGGAAAGATTAGGGGAACTCCAAGTTTGCCCTCCACTCACTA
CATATGGGTAGGGGAGCAACGATATTCCAACTCTGAAGAAAGAGTGGAAAA
AAAGTAGTGTTAAAAATTTGTATTAGTTTCCAAGGGACAAAGAAGCGCTGC
CCAATCAATGAGGGCCATTCGTAGCTGTCAACCAATCAGAACTGATGAGCT
AATATTTCCTGAGGCAAGCCAGGGAGCCGGAGGGGAAGCTAAGAAGCTTAT
TGAGAAAAAACAAAAACCCTGTTTTAGGAAAAAAAAAAACCATCTTTTAGC
GATTATGAAATAAAATCACAGAGACATTTAAGTATCCCTCAATCATGTACT
GAGAGCAATACTAAATTTATCGCCACCAATACAGTTTTACTCTATTAAAAA
GACCCTGAAAATTGAAACCCTATTCAGACTCCTGGAATACCCAGGACACTA
AATTCAGGGGAGATTAAAATCTGTTTTAGAGAGAAAAGGCACCTTTTTCAG
TGTTACCGCGGCCTTCAGCAGTTAACCTTTTTTTTTCCCCCTTTACGCAGA
AATGGAAATTTGGGTGATAGAAATATTCCGAAATTAAATTGTGATGATGGT
TGTACAACTAAGAAAACACGGTAAAATTCATTGAACTGTACCTAAAGTGGG
CAAATTTTGTGGTACATTAAATATCAATAAAGCTGATTATATACATACACA
TATATTTTATATATGCAGAGAGAGAAATGATGCAAGCAGGGTGGTAGGAC
ATGAGGTTGGTAGCATAGGCAATGTTGGTCTGTGAAGGGCCACCTGTGCTA
AACCTGGAAGCCTGGGGTTTGTCCAGTCAAGCCATGGTAGCCATAGTTTTA
AAGGATGTTCCTGATGCAGTTATGTGTTCCAGTTAAGTACATCTAGCTTCA
GAACTCAGCTGGAAAAGGGATGTGAACTTCAGGTTAGCTGATAGGGAAATA
TCTTACTCTCATCTGAGTAAATATTCACAAATGCCTCTCATTGTGCTCTTT
TTGGTACCATTGTTATAGGACTGATTTCAGCCTCACGATGTTAGCTTCAGT
GATGGATGTCTCTTTATTTTGAGGTCCTGTTTTCCACCTGACAGTTTTCAT
CCAGGATTTCTTGAGGAATTACACAAGTACCCAGCTTGGCTTAATTTAAAA
CTGACAATGGAGAGAATTCATAGCTGCATTCTGGATAGTTTCAGGAATCAG
AGGAGCAAAAATGAGCCTGGTATGGAGGGTGGGTCATTTTATGTCTTTCTT
AGTTGGTATTTTAAAGATATTTATTGATCTCATATGCCAGATATTGTTGAA
ATCATTGGGGTACATAAGTTAGAAAATTTTAATTCCCTTTCCTGAATTCCA
GAGTCAATGTAGAGGGGTGTGTGGATATCGATTACCCATATGGGAGGTATA
GTCGTTGTAACAATAAGCCACGACTAGCTCCTGTTACGTTTTGCCTGGCCT
TTCATAGCATTGCTATGTTCATAGCATTGCTGATATGTCATACTCATCTTA
GGCATACCCACCACCACCTTGGGCCTTCTTCAGTCCTAACACTCATGCAGT
CCTTGTTCAGAACAAAGATAATGTTGCTTAATTTGCAACCCCTAGACTATC
CCCCAGATTTTCTAAAGAGAAACTGCACGCTGATTGCTTCAGGCAGTGGCA
GGTCAAGGAATGAGATGGGGAATTGATTGTGTTAGCATTCTGGTGGGCTTA
```

FIG. 8-161

```
GTGGAGAGCCTGGAGACTTACATAGAAAATTCACACATCCTTTCATTCAAC
AAACCTCCATAAACTACCTGTTAAACGTCAGCCCTGTTCAAGGTGCTAGGG
ATACTTCTGGGACAAAACAAAGTCCCTACCTTCAAAAAATATATTCCAGTT
GGGGGAGAGAGAACAAACACAAAATAAAATATATCTAGTTATATGTATTTT
TTGTTAAATATATTATTACATATATAATTCTAGGTGGGGAAATGTTATATA
TATATGCTATTGAGGATAGTCAACTATATATATATGCTAAATGAGCAGA
AAAGCTTATTTTACAAGGGATGATTATGGGAGGTCTCTTTCGTAAGGTTGG
TATTTGAGGAGAGGCTTGAATGAAATGAGATCTAGAGCCATTCAGATATCC
AGGACAAGACCCTTCTAGGGAGAAAGAATAGATATAAAGGTGCTGATGCTG
GAAATGCTTGGTCCATTCCAGAAACAGCAAGGTCAGTGAAGAGAAAGAACT
GCGAAGAGAATGAGGTCAGAGGGTAGCCAGAGTACAGATCTAGTAGGTTGA
GCAGCTCATCCTAGTTTGCTTGGAACTTTCTAAGTTTCAGCACTGTAAGTC
TTACACCCTGAGAAACCCCTGAGAGTCAGGCAAACTGTAATGGTTGGTCAT
CTTACTTGTAGGCTATGATAAGGATGCTGGTTTTTATTATGAAGGTGATGG
AAAGCCAGTGGAATCTTTTCAGCAGACAGTGGACATAATACCTTCAAAAAG
GATCACTGTTGATGCTGGATAGAGAAAAAACTGTATGACAGGGGGATTAAA
AGTGAAAACAAAGACCAGTTTGGGGTCACTGTGGTCATTCAGACAAACCGC
CATGGCAGCTTGCTCCTAGAGAAGCAGCAAAGAAAACAATGAAAGGTATTC
TGATTGATTTTCAACAGAGCTGACTGCATTGGGTGAAAGTTGTAAGAAGCT
CAGGACAAACAATATTGCACAATTCCTGGCCCAAGCTGCTTGAAGAATGGA
GTTCTATTGATTGACATGACAAATATCAGAGGAAGAACAGACTTGGTGTTT
ACGTATAAACATATTTTGGACAAGTTCGAGATGCCCATTATTCAATTAGAT
ACATCAAATATGCAGTTGTATATGAGTCTAGAGATTTAAGGTCAGGGAGAT
GGTTTATAATTGCAAACACTTATTTAGAGACACAGTTTCACTCTTGTCTCC
CAGGCCTAAGTGTAATAGCGCGATCTCAACTCACTGCAACTTCTGCCTCCC
GAGTTCAAGCTATTCTCCTGTCTCACCCTCCCGAGTAGCTTGGATTACAGT
CGCCCGCAACCATGCCCAGCTAATTTTTTTTTTTTTTAGTAGAGACGGG
GTTTCACAATATTGGCCAGGCTGGTCTCGAACCCCTGACCCCAGGTGATCC
ACCAGGCTCAGCTTTCCAAAGTGCCGGGATTACAGGCGTGAGCCACCTTGC
CGGGCCTATATTTCTTAAGCTCTATGTTTCGTTCTGAAGCTTGAAGTGGGT
GGAAGCAAACTGATAGAATTTGGAGAGGTGGTTAGGCATCCCGGGAATGAG
AAACAGCCCGAAGCTGCCACTATCACAGGCTTTGGCATTGCTAGAAGTTAA
CGTGGCACTTACAGCTAGGCCGTGGTGTTCTGTTGAACAAACTATTTGACA
GAGCACAGAGCATGTAAGTGGTGAGGCCAGTTGAGTTAGCCAAGAAAAGAG
GAGTCCAAGAACTGAGCCAGAGTACACCAGAGTATGTAGTGGAGTACAGCT
TTCTCATTCTTTAGTAGGGCTGTGTAGAGAAATACTCTATTTTATGGATGT
ATAGATCACTCTAGTCCTTTCTGATGAAAACTTTACAGTTGCCACTCATTT
ACTATTACAAACAATGCTGCACTACATTATGTTTCAGTTTTTAGCCATCTC
ATCTGGTCTCAGCATTTATTTATCTGCTGATGACTCACACATTTTTATCTC
CAGCTCAGACCTCTCACCCGAACTCACTTATTCAACTGCCTATTCACTATA
TCCTCCTGTCAGGAGAAGCTTGTTAGCAAAGTAACCAGAAAACAAAGTTGA
TTTTTTTGCTGAAGTAGCCATCAATATATTTGTTACTAAATCAAAGATGC
TGAATATTTGGCTGACTTCTAAAAATCTGGTCACCTAACTTTGACACTTCC
TAGGTCGTACAGTTTGAAACTTTCACAATTAAATCAGTTTTGGAATTTACA
ATTTAAGGCAGGAATAGAAGACTATTGGGTTGACAGGTACAGTGAAGATGC
AAGTCATCTGAGAATCTTACATCAGAGGGGGCTTCCATCTTATAGCTGCTG
```

FIG. 8-162

CCACGGACCTCGGAGTCAGAAGAAATTTGAGTCCTTATTTATAAAACAGAC
TCCCTTAGTCTACTAAGTGGGAATTTACGAACTGCGTAGGCAGCCTGCTTA
GGGGAGCCTCCAGCCTGAGGACTGAAAATAGCAAAGCAGCTTTAACCGCCA
GTCCTACTCCAGAGAAGGGGGAGGTGACGTCACTCAGCAGGACGCCAAGCT
CAACTAGAAATGGAAGTAAAGGCTTCTGGCGCTACCGGCAGGGGGCGGTTA
AGGACGGCAGGTGTTACCAGGGAAGCTAAAAGTACAGCTTTTGCTGACGTT
AAGTCAGATACGCCTGGGAAAACAGACCTGACACCCATTTTAATCCACCTA
CTCAGTTCCAGGCAGCTAGCATCTTAGGCTCTCGTACAAATAACGCACAAC
TCGTTTTTAAAACTAAAAAGCTGAGCTACTCATTTATCGGACTCGCGCTGC
ACGTTAAGTTGCTTGACATGTCAAAACTATAGCATTGAAGTTTATAGCTCA
CTTATCTCGGAGACCTCGTTTACTTAGCTGATTTCTGCTTTAGCAGCCACT
CAGACCAAACAACCTGGTCTCTCCCAACTGGTTTATAATAGTTCTACATAC
TAGGCAGAATAGCCGAGTAAAGCCATTGAGATGTTACCATCCGAAAGAATA
CAATCACAGCTCTTTCTGAGAGGGAGTGGGCGGCCCTGAAAAGGGCCATTG
GAAGAAAACTGACGAAAAGATTAACCGCCGAAGCCGTACAGAGTGCGTCCT
TGACGCTTGAGCGCGTAAACCACATCCATGGCAGTGACAGTCTTGCGCTTG
GCGTGCTCCGTGTAGGTCACGGCGTCCCGGATCACGTTCTCCAGAAACACC
TTGAGAACGCCACGAGTCTCCTCATAAATCAAACCGGAAATTCGCTTAACC
CCACCACGCCTAGCAAGGCGCCGAATGGCCGGTTTGGTGATGCCTTGGATG
TTATCCCGCAGCACTTTTCGGTGACGCTTGGCACCTCCCTTACCCAAACCT
TTACCGCCTTTGCCGCGACCAGACATGTCTAACCAGCTGACAACAAAAACC
AGGTACGCGAAAAGAAAGCAAGCCACGAGCATTTATACACGAACATCGGAC
CTTATTGAGAACTGAAAGCGGGAGCGAGGATAAGGAGGCGTTGCTGCCTCA
CTTTTTGCTCCGCCCCTCGAGGGGCAGTGACCTAAGGACTGCGAGGGAGAA
CACAATAGTTTCACTTTTTAATCCCTTTAGTTTTTCCCTCCCGTTTACGAC
ACTACTATTTGAATCTGAATTTATACCCTCGACTGAGAATTTTAATAAGGG
CTTATATTAAGGGCTTTCACTAATATGCCGGAGTGGTAAACTTTTTAAGTC
TTTCAAGTGCTTGAAGACATATTGACTATTCAAAGGTACTTAAAAGAGCAG
GCGTGAAAAGATCACTCTGGCCTTATGTTTTCTTGAAAGCTGACCTGTTTC
TTAGAAGCAGTAGGTGAAATTCTCATATGAAAGATGTTCTCACTGTAGTTT
AAAAAAAGCAACATTCTTCTCAAGGATAGGAGGCTGAGGCCAAGAGAATTC
TGTACAAACCTTGCACTAGCCCTTGCTGGGCGCTTCTCTACACAGTTATAT
ATTCTAGCCTAAATCCCTTTGCTTAGCGCATTTTTACATTTTACTAATTG
TCCAATTCATTATATAAGTAGCTAACTGCTTTTTTTGGGCTTTCATTACCT
TATGAGAGCACCTGTGTCACGTAAAACCTGTGTTAAATAAATGCATATACC
TTTCTCCTGTTAATCCATTTTACATTAATTTAATTTGCTGGTCCAGCCAGA
GCCCTAAGAGGATGGGAGTGGAGTTTTGCTATCCTTCACACTGTACTGTCT
CATTCAGAAGAGGGTGATAGCTCATTGCAACCGTGCCTTCATCTGTAAATC
GGGTTATGATGATACTCAGGGGACTTTTAATTAGCTAATGTGAACGAGGCA
TGAGAAGAGACTGTGGAAAAGAAATAAATATTACATAATATGGTTTAATTT
TAGATGTTACTACTTAAAAAAATCTGCTCAGAGTTGGGATATTGTCCTGAA
CTCTCATTTTCGTGTTTTTACTCCCAACACTATATTGCTAGCAGCAACTAT
GTATGTATTAGTAAGGATTGTTTTTTTAAAATCACAGCCTGTAATAACGTA
CAAGGTGTTGACAGATTCCGTTTAGCTTTTCATATGTGACATGTTAAAATT
GTCCGAAAATATTCCTTTGTTCTCTTTTCCAAGGTGCAATACAATAGCAGC
ATTCGTGCTTTCCTATAGCCAAGTCTGGAGTGTAGTTCAACTCTCCATACA

FIG. 8-163

```
CGCTTCTCACTGTTGTTTTAAATTTCCTGAAAACATTCTTAAATCACTTCT
ATTGGAAAAACTGCAAGGGCTACTGCTAAATTTTTAAGTCTGAAAAATGCA
CCCCAAACTTGACTTCTTTCTCTGAGAATCTTAGCCATCTCACCCAAATCT
AACAAACCAAAACTGATTTTAGACTTCAACAGCATTAGCTGTAAACTTCAG
CCTGCAGCATAACATCACTTTGTTGTGACTGGGCAGGAAAAACCCTGTTAA
ACTGTTTCAGGCGCGTCCGTGTGAAGAGACCATCAAACAGGGTTTGTGTGA
GCAACAAGGCTGTTTATTCTACCTGGGTGCAGGCGGGCTGAGTCCGAAAAG
AGTCAGCGAAGGGAGATGGGGTGGGTCCGTTTTATAAGATTTGGGTAGATA
GTGGAAAATTACAGTCAAAGGGGGTTGTTCTCTGGCTGGCAGGGGTGGGGG
TCACAAGGTGCTCAGTGGGGGAGCTTTTGAGTCAGGATGAGCCAGGAGAAG
GAATTTCACAAGGTAATGTCATCAGTTAAGGCAGGAACAGGGCATTTTCAC
TTCTTTTGTGTTTCTTCAGTTACTTCAGGCCATCTAGAGGCATACGTGCAG
TTCACAGGGGATATGATGGCTTAGCTTCGGCTCAGAGGCCTGACAAACTGA
ACAACTGGGAACAAACAACATTTAATGCACACAATCTCTATCTTGTAGGGA
GGCAAAATTTTACCTCTACTCTGTTAGGGTCTCCAGCTGGACCTGATAATT
CATTTGCCATAAAACAGATTAGCAGAATGAAAGCATACAAATGTATTTAAT
GTAAATTTTATGGGACAGGAGAACCCTCATAAAAAAGTGAAGCCCCAAAGA
AATGGCAAAAGCTAAATGCTTTCACATTAAGTTAAAGAGAGGCAATTGTGG
GAAAGTAAACCATATGAGGAGATTAAAGGAATATATGATTATTTTAACAAG
GTTTGTTTGTGTATAGAAGTCTCTCGGCTATGACTCCCTGCTGTGTTTGTG
CAGAATTATCTCATCTATGCCTCTGGGCTGAAGAATATGTCTTTTCACCTG
GTACAAGCAGAGCATTTTTCACATTGGAACTTTTATCTCCTGTTTTCAGAA
AGAAAAGTTTAGAAGAATTCCCTTCTTGAATGCTGTTTTTGAAGTGCCTTT
AGCTCAAAAGAATCCTGATCCCACAGTGGTCTATTTTTGGATGGTATATTC
TGCAAACAACACCCCCTTTTTGTCTCCAATCTCTCCTTAATTACTCCTCTA
ATACAAAACAATAGATTCTTAATATAATATTAAAATGTTTGCACTACTCAC
AAATACAAAATGCTCAATAAATTTTCTTTCACAAATGAGAATTTCATCCAT
TCGTTAATTTTTAAATATCAACTGTCAATGAAGAGTTACAGCAGAATCCTT
GTTCTGTTGAGGAGGGGGCAAAGAATGTAAGTGAGGGAGTGGAAAATAGCT
GGACTGAGCTACCACCCCCTGTCCATCTGATCCTCAGACAGTAATGTAACT
TTATTCTTTTATGCTATTCGTCAGACCCAGTACCTCCAACACATTTGTTTC
CTACAGATAAAGAAAATATAAAAAGTCAAGCGCTATACATCAGATCCAGCA
CATCTATAACTGGAAAAAAAATACTTGACCTTCAGCTGGGCCCAGAGCTTG
TGAGTAGTCACCTTGGCATAGACCAAGTCCATTGGCATCTCTAACATATCT
ATACTGTCTGTGGATAACAAATGTCTATGCCAGTTAGAGTCGCTTGTATAA
GAGTCAAGAAAAACGAATCATAAAACAAACTGACATATTCATTTTCATAAT
TTTTAAAATGCAAATATTACTTTATAAACCAAAAACTGCCTTATTAAAAGC
TGGAACACAAATGAATTTAAGTAAACGATGCAATTCAAATTTAATCTTTTG
TGTGTGTGATTTGTTGTTGTTGACAGTTGGTCAGGCGATTTTAGTATGGTA
CATCAGTTTACATTCTAGATGTAGGCCAAGAAAGAATGTTAGGTGTAAAAA
ATATTTATTGTAAAAAGAATGTGAGGCAAGGTCTTTGGAATTAGTAGTTT
TAATGTTGGACATTCTGTGGTTGTTCTAAAGTTAGTCTGTAAAATGTGATG
TAAAAGCTATATGATAAAAAAATACAAAATATAAAAATTTTAAAGTAAATA
TTACTTTTGTTTGCGTACAGTATTCCCATCCCTCTAAATTTTCTTCCAGTA
CTCAATCCCCAACCTCCAAAACCGAAAAGCAAGATCAACAGAAAGAAAATG
GTTAAAACTTGTAAATTCTAGATTTTAATAACTACAGGCAAGAAGTACTGA
```

FIG. 8-164

```
AAAAAAGAATGTGGCATGTCATGGTGCATAGTCCTAGAGGAGACAAAGCAA
TGCAACCAGATAGACTATTTACAAGCAAAGCCACACATATAAAAATTCATA
TATAAGGGATTAAATTATGCTTGGTCGACAGACTGACAGATTTAAAGTGGG
TAGCTAGCTATGGATAAAATGAGAGCCAGTTAGATCCCTGCCTCACATTTT
GCACCAGAATAAATTTCAGGTTAATGTTAACAGCCAAATGAATTTAACAGT
ATATATATATATATATATATATAATATATGAGAAAACCTAGGGGACTAT
GTATTGAGCTGAGAAAATCTTCCTAAGCATTTTGAGGAAGACACTGGAACT
CGCAAGACACAATTTTCTAATCTTTTCAAAGCTTTGCAAAAATGCCTAGTA
AGCGCCAGTTAACTACTTACCAGATTTTTCCCTTACTCTTACAAAGTTGTT
TAAACAAATGCTAATCATAGCAAGCTAGAGGCCTGAATGATAGTGGACTTA
CACAGCTTCTCTCCAAATAGCACCTTAATAAGGTCAGAAATAACCTACACT
GCAAGACTGACCAAACCGTTATTTCTGTTAATCAACTTTAAGACCATAGTC
TAATGCTTTCCGGGGGGGTCCTTAGAAATTTGTTCTGTTAAGACAACAAAA
AATTATCACAGCTACTTTCGTTGGAATAAGTGGGTGGCTCTGAAAAGAGCC
TTTGGGTTTTAAGACTGATGAAAAAGTGACTTTACATTTACGCTCTTTCTC
CGCGAATGCGGCGAGCGAGCTGGATGTCTTTGGGCATAATAGTCACTCGCT
TAGCATGGATGGCGCAAAGGTTTGTGTCCTCAAAGAGCCCTACCAAGTAGG
CCTCACAAGCCTCCTGCAGCGCCATCACCGCAGAGCTCTGGAAGCGAAGAT
CGGTCTTGAAGTCTTGGGCGATTTCTCGCACCAGGCGCTGGAACGGCAGCT
TCCGAATCAGCAACTCGGTCGACTTTTGGTAGCGGCGGATCTCGCGCAGAG
CCACAGTGCCCGGCGGTAACGGTGAGGCTTTTTCACGCCGCCGGTAGCCG
GCGCGCTCTTGCGAGCAGCCTTGGTAGCCAGCTGCTTGCGTGGCGCTTTAC
CGCCGGTGGATTTCCGAGCTGTCTGTTTAGTACGAGCCATGGCAAAACCAC
AGAAAAGCTTGCCTGCAGAGACGTCTGTGGAGGAAAGGAAAGAGCTACTCT
TCTTTTATAGAGTCAGACCACCAACTATTGGACCCAAGAAAATTCAAAAAT
CCCCGCGCCCTTCTTGGATTGGTCCATCTCTGTGCCTGGTTGCAGATTAAG
AGAGGCTCCTGCCCATTACCGTAGCTACTCTGACGTCATTTTGTTAACCCC
TTAGCTGCTATATCCACTGTGGACAAGTCTTGTACTGGAAAAGTTTCCTGA
AGTCTTAAAATTTACAACCACACAAAGCAACGCGGAAACCTCCAATTGTTT
CTAGTTAAAATATAAAAAAGAAATCAGAGAATATTGGAGACGATTAGGGAA
ATTTGCATATGCGCTTTATTTAAAATTGTATTTTTCTGGGTGTCGCATAAG
AAGTGTGGGCAATTAGAAAAATGCTCTTAGCCGGGCGTGGCGGCTCTCGCC
TGTAATCCCAGCTACTCAGAAGGCTGTCAAGAGGATCGCTTGAGCCCGAGT
TCGAGGTTACAGTGAGCTGTTATCACGCCGCTGCACTGCAGCTTGGGCGAG
AGGGAGACTCCACCCCAAAACAAAGCAAAACATCCCCAAACTGGAAAAAAG
CTCATTTTGGGAAATACATACTCAAATGTTCAGTGGTAATGTGTGTGCTCT
CAATTGTGTATGCCATTAATTGCTACAGCAAATGGTATGACATATTCAAAC
TTGTGTGGGGCATGCGGGTTTTAACACTTCCATTCAAGATAGTTAGGAATG
CACTCATGGGTATAATTTCCTTCCTCTAAAATGTAGTAACTGCTGTGTGTG
AAACTTAACGCGAATCACCCCTGTAAACATGTTTTGTGCTGCATGGCACTT
CTCCCACATACCTAGAATTCCTGAGGTTTCTATGGATCTAATTTCTGCAGG
ACAAATTACTAAAAGTGCCACACTCAAAGCCATTAAAAACACCTCAAAAAC
ATCTTTATGGGCGGCATAATCCAAAGCACAACAGCTCATTTAATGGAAGTC
GTAGGTGGCTCTGAAAAGAGCCTTTGCTGTTAGGCTGATTTTGTCTGCTGA
CAGAAAAACAGCAGTGCATGAAGCGTTAACTCTTCACTTTCCCTTGGCCTT
ATGATGGCTCTCAGTTTTCTTAGGCAGCAGCACCGCCTGAATATTAGGCAA
```

FIG. 8-165

```
AACGCCACCCTGCGCGATGGTCACACGCCCCAAGAGTTTATTAAGCTCCTC
GTCATTGCGGATGGCCAATTGCAGGTGGCGCGGGATGATGCGGGTCTTCTT
GTTGTCGCGGGCCGCATTGCCCGCCAGCTCCAGGATCTCGGCGGTCAGGTA
CTCAAGCACCGCCGCGAGATACACCGGCGCGCCAGCCCCGACGCGCTCGGA
GTAGTTGCCTTTGCGGAGCAGGCGGTGCACTCGGCCCACAGGAAACTGCAA
ACCTGCACGAGAAGACCGAGTCTTAGCCTTGGCGCGAGCTTTACCGCCTTG
TTTGCCGCGACCAGACATAACTACTTCTGATAAGGGAAAATCGCCACAAGA
AAATGTAATGAAACTACATTAGAACGCAAGGCAGAGAAGTATTTATACTGA
CTGGAGGTAGGCTGTGAGGAATTCTCCCATTGGCTAATGTCAAATACCCAA
TGGGAAATCAGAATCTGCATCCTTCATTTGCATGTAATCCTTCCGTCTGGT
GTAAGGTTTATGTTTGACCCAATCCCCAGTCTGGCTTGACGAGCCTTCGAC
TTGAATACTAATAATAATTGGCCGAATTAGGATTTTGTCAAAATACCTTTT
TTAAGCATGAGTGGAGGTTTTGTTCTGGTTATTTTGACTTTCAGCCGCTCG
TGCTTTTCCCGGATTGTGACTCATGTTTTTGGAAAGGAGTGGACTCCGACC
AATTTCTAAATAGATATTTAAGAGGTCCTTCAAATCGGGCGCAGTGGCTCA
TGCCCGTAATACCAGCACTTTGGGAGGCCGAGGACGGCGGGTCAGGCGTTC
GAGACCAGCGTGGACAACATGGAGAAACCCTGTCTCCAGTAAAATAACCAA
AAAAGAAACGGGGGAGAAAAAGAAAAAAAAAAGCCGGGCTTGGTAGTGCAC
GCCTGTAGTTCCAGTTACTCGAGAAGCTGAGGTGGGAGGATCGCTTGAACC
CGAGAGGAGGAGGTTGCAGTGAGTTCACATAGAGCCACCACACTCCAGCGT
GGGCGACAGAGCCAGAAGACTGTGTCTCAAAGACAAAAAAAGGGGAGGGGG
AGTGGGAGGGAAGAAAAGCGAATACCCCAAATCCCAGTGAACTGTAGAAGC
TTATAAGCTCTCTTGATTCATAAGGGAGAAAGAAGGGGGATGTAGGCAACT
TAGGGGAGAGTATATGATTTTGGAGAAAAATAAATGGGTGTTTCAAAGAAT
AGGTGACAGCTGTGACAAAGTCTGTTTAGATGGTGTTAACCACCAGTCTCC
TCTCCTGTGATACAGTTAATCTTCTCTGGTTGATGAGATTCCCCAGGGAAG
TGAATCTTAACAACTAAATTCCTTTTTGAATTTTTTTTTAATTTTCAAATT
TTTGATTAGAGTTCAGCGAAAGCCCTTCCTTGAATTTACTGTTTCCTAGGT
GCCCTCAGTTCAAAGAAATCAGCGTAACAAAGTGGCACATTTTTGAGTTGC
ATTTCCTGAACTTTTTCACAACACTGAATGAGGAGTCTCTGGAATCTTTCA
GGAAATGAGAGAACAAACATTCCATAACACAGAAATACTCAAAATGGGATT
ATGATTATAAAAGTGTTTCACTGACCACCTTCTGCCTTCCTGTCTGTAAGT
CCCATTCTCCCCAAAGTCTAGCCATAGAAACCAGAATTCCTCCTCAAGGTA
GGCCATACAAACCAGAACTCCTTTTCCCTAGAACCAGCCATAAAACCTAAA
AGTATTACTCTAACCTACCTTGTTTGCCTGTAGGTCATAAGACCCCCCATT
CTAAAAGAGAGTCTTGTCCTATAACCAGAAGGAAGAAATGCTGCACTGAGA
GGTCAAGAAGAATCTTGACAGACAAGCCTTGCGGGGCTTCCCCACTCAGTC
TGTTAGCATTAGATCGTACCCTATACAGCTGTTTATCTTGTTGAACCTAAG
CATAAAAATGGGCAATTTCCCCTGTATCTTTCAGTCTTAATTCTAAAATCT
CCTGTAAAATTGTGATGAAATAAATATATGCCTTTTCTCCAGTTAATCT
GTGTTTTGCCAGTAATTTTCCATAAACCTTGGGAGGGCAAAGGGGAAGTTT
TTCCTTGGCCGGGACAATATTATTACAGCCATTGTCTGGCTCTCCTGTTGA
GGAACCTAAAATCAAGACAGATTGCCTAGGGAAATCTTGGTGTTTTTCCTT
TTATATTCCATGAGATAGGAGCAGATGGAGTACAGATGAACGTGGATTAAT
TATTCCAGGAATTTCTGAGGTATCTACTACTTCTATCTGTGGTCTGCTTAT
ACTGAAACAGGATGACAGAAGGAAAAGAAACATGAGTGTAAAAAAATCTG
```

FIG. 8-166

```
CTCCTGGCTGGGCACGGTGGCTGATGCCTGTAATCCCAACACTTTGGGAGG
CCAAGGCGGGCAGATCACTTGAGAACAGGAGTTCGTAACCAGCCTGGCCAA
CATGGTGAAACCCCAGTCTTCACTAAAAATACAAAAAATTAGCTGGGCGTG
GTTGTGGGAGCCTGTAATCCCAGCTACTCCATAGGCTGAAGCAGGAGAATC
GCTTGAACCCTGGAGACAGAGGTTGCAGTGAGCCGAGATCGTGCCACTGCA
CTCCAGCCTGGGCAAGAGCGAAACTCCATTTCAAAAAAAAAAAAAAAAAAA
ATCTGCTTCTAAGCCAACGCTGTCACAGAACTATGGATTTGATTCAGAGAA
ACTGTCAGGAGACTAAAAGTGCTCATTTTTAGTTTGTTTTTTGCCTTCTCC
CAAGTCTTCTGACTCTAGTGTTATCTTTCCCTTCACAATATTCAACTTCCC
TTTTCAAAATTATAATGATCTTCACCCTCAACAATAGCCGTAAACATCAGT
AATCACTGGCTCATTTTCTTTGAAAAGGTACAAGATTCATGATGGAGATGT
TAAAAAGTTATCTCAGATAGTGCCCTGAAGAGATTATACTCAGAGAAGGGA
GGACTTACGTACATGAAGATTAAATAGCAGTGCACGTTCTGCATATAAAAT
AAAGATTTTGAGCAATAAATCATACAAAAGCACATGGAAAAGAAGATTGAT
CAATGTAAATTAGAAGGATTTAGAGAGTTCATGAGGGAGATGTATATCCAG
CATTATTAGTTCAGCATATATTTACTGAAAACCTGCTAAGTGCCAGAGAGT
GTTCTAGGTGCAGGGAGCATAGCAGTGAAAAAGCAGACAACCTGTTTCCTT
ACGGTGCTACTTGTCTTGTAGTGGGAGGTGCACAATAAGGTAAATACATAA
TGAAAATGTAGAGATAAGTGATGAGTGCTGTGGAGAAAAATAAAGAAAGGG
GATAAGAAAAAGAATAGAAATAAGGATGGAAAGTTTCATCAGGAGAATGT
CATTTGAATTCAGACCTGAAGGCAAGGAAGAAGCCAGCCAAGTAGGAAGGA
TAAATACTTCGATAAAATGCTGGATGTGTTTGAAGTCCAGAAAATGTCAGG
AACCGTGGTTCAGAAAGTACAGCTATTCTAACTTCCTAAACAAATCGTAGA
CCATTTTGGAAAGAGCCTTGGATATGTACAGGGCTAGATAAAATTGAAACC
AAGATTAAGGGTAGCTTCAAAAACTCAGACTAGAAAGCAGGAGTACATCCA
GTCACAATATCAGTAATCTATACTCCACTGAGCCATGGATGAGAAAAACTC
TTCTTCTCATCCAAGTTACCTTGAATTAAGCAAACCAACAAGCGCCTGGCA
TGTACTATTAGCAAAACAACTTGATGGCAATCCTTTCAGTAAGTGCTTCAA
AAACAGTAAATTCTAGGCACTTGCCTTCAAAAAACATACAAAAGGCAGATA
TTGGGGAGGGAAATATTGGGGGTTATTTATTCCATATAAATATAAGAGGAA
AATAAGTTGTTTCCCAATAACAACTCCAACACCAGGAGCAGAGAAAGTAAG
ACAATCTATGCCTCGTGGTTTGCGAAAACAATAAAAAAAATCTGTTAATTG
CATAATACAATTCACCCTTGAACACGCTCCAAATCAGTGCCCACTAGCTAC
AAGTAGCTACTGTGAAGTTGAAAAAGGGTACTTCAGATTGAGCTATTCTGT
AAATATGAAATAGACTTAGTGTGTTAGTTCGTTCTTGCATTACTATAAGGG
AATCCCTGAAACTGACTAATTTATAAAGAAAAGTAATTTTTTTTGGCTCAC
GGTTGTGCAGGCTGTACAGGAGGTGTGGTGCAGGCATCTGCTACTGGCAAG
TCCTCAGGAAACTTCCAATCATGGTGGAAGGTGAAGAGGGAGTAGGCATAT
CATATGGTGAGAGCTGAGCGAGAGAGATGGGGGAGGTGTCACACTCTTTTA
AAGAACCAGATCTCTTGTGAACTCAAAGTGAGAACCCATTGATTACCCTGA
AGAGTGCGCTTCATGAGGGGTTCACCCTCACGATCCAAAAACCTTTCACCA
GGCTTCACTTCCAACATTGGAGATTACATTTCAACATGAGATTTAGAGGGG
ACAAATATCCAAACCATATCACTTAGTATGAAGAAAGAATGTAAAACATCT
GACTAATAATTATGCATATTGAATACATGTTATAATGACATTTTGACTACA
AAAGTTAACGAAAATATACTATTGAAGATACTCAAAAATTTAAAAATACAT
ATATAATTTGTAGTACATTTGTACTGGGCAGAGGAACCTCTAACAATGTTC
```

FIG. 8-167

```
CAAATGTGGCCTGTGTATGTGTATGATGTAGGAGGGATCAGTCATGTAAGA
TGATCATAATATAGTTACTTAGTCCATTTTGTGATACTATAACAGAATACC
ACAGACTGGCTAACTTTTAAAGAAAAGAAATTTATTTCCTACTGTTCTAGA
ACCTGGGAAGCTAAGGGCATGGAATTAGTATCTGGTGAGGGCCTTCTTACT
GCATCATAACATGTTGAGAGAGCAAGGGTATGTGTGTCAGCTCAGGTGTCT
CTTCCTTTTCTTATAAGGCCACCAGTCTAAAGGAAATCAAAATATTTTACC
CCAAAATATATTTCTTTGACATATTTTGAAATGGCTGCTGCTTGGCCAGCA
GGCAGAAATGGGCTTGCAAAGCTGCCTTAAATGGGAAAAATTTTACATCTG
TAGAGAATCTCCATTAATGCAGCCATGCCTCCTCACCTTTCTATACCTTTC
CCCAGATCCAGGAGAGACTGAGAGTCTGACACTTAAAAATCATAAAAGAAA
CATTTACCATCTGTTCTTTCTGAGGGAGGCTTCACCTACCTAACAAGGCCA
CCTTTGCAAGCCAAACCTCTTTTGCCTCCCATAACCTGTTTTACCAGAATC
TAAGCCCCAATTCTTTCTGTGATCTAAAAATGGTATATAAGCATCTATAAC
TCATTGGGAAGTTAGGTAATTAATTCTGAATGCTCCCACATAGACACGTTA
AACAATAGGTAAAATGCCTTTTCACCTATTAATCAATCTGCCTTGTCAGTG
ATTTCTGGCAAACATTTAGTGGGCCAAGAGACTATGGTTCCCACACTACCC
TTCATGAACTTAAGCCCTAAGATATCAATAATTGCATTAAATGTGTGTGGT
ATAAATACACCCATAAAAAAACAGTTTGGCTGGGCGCGAGGTCTCACACCT
GTAATCCCAGCACTTTGGTAGGCCGAGGCTGGCGGATCACTTGAGGTCAGG
AGTTCGAGACCAGCCTGGGCAACATGGTGAATCCTGTCTCTACTAAAAATA
CAAAAATTAGCCGGGTGTGGTGGCGCATGGCTGCAATCCCAGCTGCTCAAG
AGGCTGAGGCAGGAGAATCCCTTGAACCCAGGAGGCGGAGGTTGCAGTGAG
CTGAGACTGTGCCACTGCACCCCAGCCTGGACAACAAGAGTGAAATTCCAT
CTCAAAAAAAAAAAAACAACAACTGTACACTGTCTGCAAGAATCTCACTTC
AAATATAAACATAACGCAGGTTGAAATTAAAGGCTGCAAAAAAGATAAGCC
ATATAAACATCAGCCCAAAACTGCAAGAGTATCTGTATTAATAATATCTGG
GATCTGAAAGACCAAAATAGATGCCCCTATACCAACTAAGACAGACTCTAA
GATTAAGCAAACAAAGTTACCTACTGGTAGAGCATTCATGGCTTGGCTGGC
ATGGCAAATTCCTAAATTCCAAAGACTACCAAAAAACTCACACTTGCTAAA
TTCCTTAACTATAGGAGCTATCAGAAGCCCTCCTAACTCTGATTTACAGTC
CAGTCCACTACAACTCTGATTGGACAGAGGACCGCCTTGACACACATTCTA
TTCTTACACGTAATTGTAGACCTTAAGCCATTTTCAGCCAGCTGCTAGAGG
CAGCACGTAAACTTTGTTCCTATAGTTCACCTTGTGATGTAAAGACCTAAA
TTCTACCTCATTTTAACCAAAATTTAACCTCGAAGTGAACATGGGAGGTAT
ATTACACGTGTTTATCCATTGTGAATGCACTTGGCACCCCTCATAATATAT
ATAGCTGTCCCCCCAAACGTGCTAAATATGTATGACTCTATTGTGTAATAT
ATAGCCTATGAGGCATAAAAATAACCAACCTGCTCCTTCTCCCCAAAGAGA
GAGTAATTTTGGCAGGTTCTGGGACCATCTCTTCCTGGCTTGCAAATTAGT
ATTGCCAGTAAATCTCTCCTTTCTACTCTTTAGCCATCCTGGTGGTCTTTT
GGATGATATATCAGATAAGTATATTTCAGAGCAAAGAAAATTACTAGGAAC
AGACAGGGATATTACATAATGATAACAGGGTCAATCCAATACGAAAACAA
GCAATTCTAAATGTATATGCACCAAATAACAGAACTGCAAAATATGTGTAG
CAAAACCTGATAGAACCGAAAGGAGAAATAGACACATACATGATTTAAAGG
TAGAGATTTCAACACCCCTTCCCCAATAATTGATAGAACAACGAAACAAAA
AAATTACCAGGTGTATAGAACTCAGTAAGTGACTGTATTACTTGTTTTGAT
CTGTAAAACAATGATAATAATAGTACTCACACTTCATTGAGTTTTGGTGAA
```

FIG. 8-168

```
GATTGAATGAATTTATACTTATAAAGAATTTAGAAATGTGGCCGGGCCCAG
TGGCTCATACCTGTAATCCCAGCACTTTGGGAGGCCGAGGCGGGTGGATCA
CCTGAGGTCGGCAGTTCGAGACCAGTCTGACCAACATGGAGAAACCTCATC
TCTAATAAAAATACAAAATTAGCCAGGCGTGGTGGCGCTTGCCAGTAGTCC
CAATTACTGGGGAGGCTGAGGCAGGAGAATTGCTTGAACCCTGGAGGCGGA
GGTTGCGGTGAGCCGAGATCGCACCATTGCACTCCAGCCTGGGCAACAAGT
GTGAAACTCCGTCTCAAAAAAAAAAAAAAAAAAAATCTTAGAAATGTAACT
GACATATCATAAGCCCTCAAACTTAATAATCTTTTAATACATGGAGCTATC
TATTTAAAATAATGTACATAAGGCAACATCCCAAAAGAAAATGGGCAAGAA
TCATGAGTAATCAAACCATAATAGAAGAAATGTTATTATCAAAATGTGCAG
TCTCAAACAATAATTGTCTTAAAAATAAAAACAACAATGAGATTTAATTGT
TCATGTCGGCAATTTGAACAGACTAACACACCCACTGTTCAAGAGCATTTG
TGGAAGTCAGGAAAAAACACCCTGTTGGTGAGAGTGTAAACAGACCTTCAG
GAGGCAACTTGGTAACATGTATTAAAAATCAAAATATGTATATCAATGGAT
GCATGATTCCTATCTCTATTTTTGCCCTTACAGCAATCTTGTGTGTAGAGA
AATACTGAAAAGCATTTTCATGGTAACATGGTTTAAATTTTTAAAAAGCGA
AGGTCAGTGAATAAAGGGCAATTATCTACTTCCCTACAATGAAATGCAGTA
ATGAAAATAATCATTAGAATCTCTTTTATTAATTTAAAAGGATACTAGAAA
AGTGAAATACAATCTCACTTATAGAAGATTTACATATTGGTTTGCATAGAC
TTGCACAAGATAAAATTTCTGTAAGATTGGTCACCAAAATGTCCTGAATGA
TAACATTACAATTAATGTTTATATTGTAGGGGAAAAGAAAATTCTGTTTTT
CTCACCCATCAGTAAGTTCATGCTTGAGGCCCCTCTACAAAAAGACAGATT
GGTCGGGTGCAGTGGCTCACGTCTGTAATCCGAGCACTTTGGCAGGACGAG
GCGGGCGGATCACGAGGTAAGGAGATTGAGAACATCCTGGCCAACACGGTG
AAACCCTGTCTCTACTAAAAATACAAAAATTAGCGGGGCATGGTGGCACGT
ATCTGTGGTCCCAGCTACTCGGGAGGGCGAGGCAGTAGAATCGCTTGAACC
TGGGAAGCGGAGGTTGCAGTGAGCCGAGATCGCGCCATTGCACTCCAGCCT
GGGTGACAGAGCAAGGCTCAGTCTCAAAAAACAAAAAAAAAGATTAGCAAG
AGAAAAGCATACAAATGTATTTAATATAAGTTTTATATTACATGGGACCCT
TCGGAAATGAAAACTCGAGGGAAGCGGGAAACCTGTGAATTTTTATGGCAA
GTTTTGTGAAATGCATAGTTGTGGATTAATATGATTGACAGTAGGCATATG
ATCTAATGGTAATAAACTGAGGGGGACATAGCAAGGCTTGTTTGTTAATTA
CCTATTAACGATCAGCCGAGTATCAGCAGAGACAGCAAAACATCCTAGTTT
TGAGTTAGAAGACCTAGGTTTTTGTTTTGGCTTATCAATTATGGGTATTGT
TTTAGATGAAACATCAAGTATTCTTGATTTCTTATTTCAAAAATAAAAAAT
AAAAAATAAAGGAAGGAAAAAAGAAGAAAAAAGAGAAGAAAAGTGTCAGA
GTTACTTGAACCAGAGTAACTCCATTTTGAGTGAGGGCTAGGAAAATGAGG
CTGAGACTTTCTGGGCTGCATTCCCAGAAAGTCAGTCATTCCTAGCTTCTA
GATGTTTACGGTTAAGGGAACAAATAAATAATGTTTACTAAACAGACTCAG
ACTTAGGAGTGTCCAGATATCCCTATATCTGGAGAACAAAGGCATTCTTAA
TTTTGTTTAAAGATAATAATGTTGATTCTTGCAAAATATAGTAACTAAGAA
AATTAATCCTTTATCACAAACTTGTAGCAGAGCACATCTCCCCATATATAC
AAGTATTGTACCTAGGGTGGATGCCTTCCTCCTCTTACTTTCGGGAATGTC
CTGCTCCGTCTATGGAGTAGTTGTCGTTTCACCACTTTACTTTCTTAGTAA
ACTTGCATTTACTTTGCACTGCGGACTCACCCTGAACTCTTTCTTGCGCGG
GATCCAAGAACCCTCTCTTGGGGTCTGGATGGGGACCTCTTTCCTGTAACA
```

FIG. 8-169

```
TATTTCTGGCCACCACAGAAGGGACTATAGTACAGAAACCCTGACCCAACA
GCTACCTTTGGGTAAGTGTTGGAGTTCTGTAACAAAGGAAGAAGGCAGGCA
GGCAAAAAATTTATGAAAGAACATACGACAAAATAATTTCTGCTTCAAAAC
TTCATATTTTTTAATTTTTTTTTTTTTTTTTTTGAGACGGAGTCTCGC
TCTGTCACCCAGGCTGGAGTGCCATGGCGCGATCTCGGCTCACTGCAAGCT
CCGCCTCCCGCGTTCACGCCATTCTCCTGCCTCAGCCTCCCGAGTAGCTGG
GACTACAGGCGCCCACCATCACGCCCAGCTAATTATTTTGTATTTTTAGTA
GAGACGGGGTTTCATCGTGTTAAGCAGGATGGTCTCCATCTCCTGACCTCG
TGATCCGCCCGCCTCGGCCTCCCAAATTGCCGGGATTAAAGGCAAGAGGCA
CCGCGCACGGCCCCGTCCAAGTTAACCTTGGCTCTAAAACTTGTCTTCGCT
AACATTCCAGTTGATCCTCTAGAACTGAAACAGAATAGCAGCAGCACCACC
TTAAGAAATTGTGGTTATAGCTCTCCTTGTGACAAAGTAGGTGGCTCTGAA
AAGAGCCTTTGGGTTTGGAAGTGCTTACATAAGCACTTATTTAGAGCTAGT
GTACTTGGTAACTGCCTTAGTGCCCTCGGACACAGCATGCTTAGCCAGCTC
CCCAGGCAGCAGCAGGCGCACAGCCGTCTGAATCTCCCTGGAGGTGATGGT
CGAGCGCTTATTGTAGTGAGCCAGGCGAGAAGCCTCGCCCGCGATGCGCTC
GAAGATGTCGTTGACGAAGGAATTCATGATCCCCATGGCCTTGGATGAGAT
GCCGGTGTCGGGGTGGACCTGCTTCAGAACCTTGTACACATAGATAGAATA
GCTCTCCTTGCGGCTGCGCTTACGCTTCTTACCATCCTTCTTCTGCGCCTT
AGTGATAGCCTTCTTAGAACCCTTTTAGGGGCTGGAGCAGACTTAGAGGG
TTCAGGCATTGCTATTCCTAAACAGAATAGAAAAGCTACTAACACTCTCCA
CTACAGAGTAGTACAGAGAACAGTTCAGAGCCCATGTATTTATAGTCCTGA
GATTCAAATGACGGTTTAAGATTCCTCACTTCTGATTGGACAAAAGAAACA
CGGTTTCACTGAGGGGTGGGGTTTATGCAAATATGGAATTTATGTTATCTT
TTTCTATTGGATAAAGCACCAAACATAATTGACCAATAGGATAGCTTCCTA
TTGCAGCCTTGCAGTTTGTATAAAAGGATTTGTTCAGGCGCCATTCCAGCT
TGCTTGTCTTTCACAGTTTTCCGCTGCTTTCATAGGTCGCTATTTGCGGAC
GTGGAAAATGGAGCTAAAGCAAAAACTTGTTCGTCGCTACCGGGCTTGCAG
TTCCCAATAGGGCAGAGTCCGTCATCTTTTTCGAAAGGGCAATTATTTTGA
GCCGGTCGGAGCCGGTGCGCCAGTGTACTTACAATACCTGGCCGCCGAGAT
CTTAGAACTGGTGGGCAGCGCCATACGTGACAAGACCCGCAGCATCATCCC
CCGCCACCTGCAGCTGGCCATCCGAAACGACGAGGAGGTCAACAAGCAGCT
GGGCAACGTACTATTGCTCAGGGAGGCGTCCTGTCCAATATTCAGGCCGT
CCTGTTGCCAAAATAACAGAGCCACGATAAGGCCAAGGTCAAGTAAACACT
CAAATCAGAAAACGTAGCTTACACTTGAAACGGCATTTTTCAGAGCCGTCC
ATAGTTACACAAGAAAGGATGATAACTTGCTTCTGTTAGGGTATTTTTTGC
TTTTCGTTTGGATTGGTTTGTTTTGAGACAGTCTAGTTCTGTCACCCAGGC
TGGAGTGCAGCGGCGCGATATCGGCTTACTGCAACCTCCACCCCGCCGCTT
CACGCGGTTCTCATGCCTCAGCCTCCTGTGTACTTGGGATTACAGGCGTCT
GCTACCGCGCCCAGCTAGTTTTTGTATTTTTATGCGAGACGGGGTTTCACC
ATTTTAGCCAGGGTTGTCTTGAACTCCTGGCCTCTAGTGATCGTCCCATCT
CGCCCTCCCAAAATGCTGGGATTACAGGCGTGAGCCACCGCCCCCCTAGCC
TAATGGTGTTAAAAAGTTAAGTTTCGAGAAAATAACACCTTCCTTTAGAAA
GTACATTTTAGAGTATACAAAGTGAAACTTAAGGCCAACCAAAATAAGACA
TTTTGAGAACAGGCAGGGTGGGAATGTGACTTGGACTTAGAAAACAAAGGG
CAAGGAAACTTGCTGTTCGCCAGTAACAAAATAGCATGGAATCTCATTCTC
```

FIG. 8-170

```
TGAATATAAGCGTTATTTCCCGACATGAGTCTGAACGTTTCTGGTGGTTTA
GTGAGTGTTCACCAGCATTGATAACTTGCGAGACTGTCAGGAATGCAGAAT
TTCAAGTCCCACTCAAACTTACTGAATCGGAATTTACATTTTAAAAATCCT
TAGATACCTTGTTATACACTCTGTTCTTTGGGACTGGATGAACTAGAATTT
TAGACAATTTGTCGCTGCAGATAACTGAAACGAAAAGGACAGGATGGGCGG
TGGGGCAACTCATCCAATAAGATTGTCTAGTAATGAACCAATCAGTCTGGT
CACTCTTCAGCCAATGATTTTATCGCGCGGGACTTTTGAAATATTACAGGA
CCAATCAGAATGTTTCTCACTATATTTAAAGGCCACTTGCTCTCAGTTCAC
TACACTTTTGTGTGTGCTCTCATTGCAAATGGCTCGTACGAAGCAAACAGC
TCGCAAGTCTACCGGCGGCAAAGCTCCGCGCAAGCAGCTTGCTACTAAAGC
AGCCCGTAAGAGCGCTCCGGCCACCGGTGGCGTGAAGAAACCTCATCGCTA
CCGCCCGGGCACCGTGGCCTTGCGCGAAATCCGTCGCTACCAGAAGTCCAC
CGAGCTGCTGATCCGGAAGCTGCCGTTCCAGCGCCTGGTGCGAGAAATCGC
CCAGGACTTCAAAACCGACCTGCGTTTCCAGAGCTCTGCGGTGATGGCGCT
GCAGGAGGCTTGTGAGGCCTACCTGGTGGGACTCTTCGAAGACACCAATCT
GTGCGCTATTCACGCTAAACGCGTCACCATCATGCCCAAAGATATCCAGCT
GGCACGTCGCATCCGTGGGGAAGGGCATAAGTCTGCCCGTTTCTTCCTCA
TTGAAAAGGCTCTTTTCAGAGCCACTCACAATTTCACTTAAAAACAGTTGT
AACCCATTCGGTTGTCTATGTTAGTTTCCAGGAGATATAAAGGTGATAACT
ACACACAAGTTTTGTAACTGCAGACAAGTCTATCAGGCCTTTTCAACCGGT
TTTACTGCGAGAAAACAAGCTGAGTTACTGTTTTGCCCTTGTTAAAAAATT
CCTAGGGGTCTTTTTAGCATGTATATGTGTAAATACTTACATATTGAAAGG
CTCCTGGGGACACCACCGTCACTCCTTTTAATCCACGTGACAATTTTAGTT
CTGATGGCAGTATTATTAAAGCTATCATAAAGACAATGTGTGTGTAGTTAC
CTAAGTCCACAAAAACAATAGCTGACCCCAAAATTCAGTATTGGTTTTGGG
CTGCTGGAGGTGGAGTCAGAGCTCAGGTGGAAGAAACTGGCCTCAGTACAC
ACTGCCAAAAGTCCACTAAATAGATTTATGTAACAAGTACACAAGACTTGC
GTATGACCATCCAAAGATTATGCGGTCATCCTTATCCAGGGAATTTGAGAA
TGAAGGGTGGCAACTGCAAAGCTCTTTTACCCATGTCCTCTTTTAATAAAT
ATTTAAAAATATTCAAATGCTGATTTCATCCATTTTCTAAATATATTAGTA
TACTTAACTGATGGGGTAGATCAAGGTTTTCTGGGGATCAAACCTTTTACA
ACTTGTTAACTATTAAAAACTATAATGTAAAATTAAAAATGCAAAAGTACT
GCAGACTGTAAATATAAATTTATAATGGGAAAATAAAATCAAATTCCAATT
TTATAAAAGCTGACAAAACAACAGCCATCACAAAATTCAGAAAATAGCATA
TTTTATTAACTTCTGAATATGACACTACCAAGTATATTTTCCTGTAGTTTT
GACTGAATACTCTGATTCCATCTTCAGATCGAAATTATTTTGTAATGTTGT
CTATAGGTAATGGAAATAGAATTCAATCTTTCCTCCAGGGTGGCTGATGAT
AATATGTTTTCTTCATAACTTAGAAGTATTTCAGTTTCAAAACACATTATT
GGTAATGTCAAGTAAGTTTTAGGATTGTTTTCAAATTTGGAAAATCCTCT
GTTAAGCTCCTTTCACATGTAAGTTGTAAACTTTGTAAGAATTCTTTCCAG
ACTAGCTTCTGGCTCTATACGTTTCTACTCTCCACTAGACACTCACTCTCA
GTGCTGGGAATGTGTTTTGAATACTTAGATGTCATAACATTTTATCTAGAC
CTGCATCTTGCCAGGAATTTAGGTGAGTTATTCCAGTGAGCAGTAGGAACA
TTCCTTGAAGCCATTCTTTTTTTTTTTTTTGAGACGGAGTCTCGCTGTG
TCTCCCAGGTTGGAGTGCAGTGGCGCAATCTCGGCTCACTGCAAGCTCCGC
CTCCCAGGTTCATGCCATTCTCCTGCCTCAGCCTCCCAAGTAGCTGGGACT
```

FIG. 8-171

```
ACAGGCGCCCGCCAACACGCCCGGCTAATTTTTTGTATTTTTAGTAGAAAC
GGGGTTTCACCGTGTTAGCCAAGATGGTCTCGATCTCCTGACCTCGTGATC
CGCCCGTCTCGGCCTCCCAAAGTGCTAGGATTACAGGCGTGAGCCACCGCG
CCCGGCCTCCTTGAAGCCATTCTTACGTCAGATTGGCTGGCAACGAATGAA
GTACACATGATCACATATGCAAATCACGTAACTTATTATCCCCATACTAGA
TACATCTTCAACTAAACTTTCTCTTACTCAAATTCCAAATATTTTCATCAG
GATTCTAACATAATCAGACAATGGTGATTTTAATAAAAAGGAGGATTGAGT
GAAAATAGCAGCCTGAACCATCCGTGATTAAAGTACCTTAATACTGCAAAT
TTTAAAATCAGAGAGAGAGAGAGAGACAAACTAACACATTTGTAGGGCCCC
TCTCTGCACCTTGGAAGTACAGGCCCTTACACTTGTGTTTCATTAGCTTCA
GGATAAATCTGCCCCAGATCACTGGCCAAATTTTACGTGGCCTTCTTCAGC
ATCCTACCACTCTATTCAAATACATCTCTGCAGGAGCACCCTGTGAGTTGA
GAATTACTGGTCTGGGATGACCACTGTTTGCATGATGCTTTGGATGGTGGT
GCTGTTCTCAGAAGAAATACCAGAAGGAGAAAGGTTAGTCAGGAGAATATA
AAGTCAACCTTAAGCAATTTGAACACTTCAGTGGTTAAGTGAGTTCCCTGG
GACAACTCTGCAAGCTGTTTAACTTTATTTGTATTGAATATTACCTTCTT
TTAGAGAGGCCAACGTGTAGAAGGAAATAACAATGAAACAAAGGATTCATT
AATAGTATAAACTATAAACTAACTGTCATTGATAGTCTTCCACGGGCCAAG
TACCACATGAAGTGGTTGGTCTGAATTATTGTGTAAAATTCTTACTTCAGC
ATTGTAAGGCAAATTATCTCACTGTCTCCATTTTACAGAAGTGGAGGTTCA
GCCTCAGGAATTTCACTAAATTCGCCAAATTCTTACTACCAGCAGATATCA
TTGCCAGGCAGTGTCACACTTTAATATCTTCTAATCAATAAGATAACCCTA
AAATTGATTATCATATATAATTTCCTTCTCATATATAGTTTCATACTATCA
TATATAGTTTCCTTTGTTTCAGAAATTGGACTCCCTCAGGGTGGATAAGGA
GACATGGTGGTGTCCTGGCCTAAGTATTGTTGGAATCCTCTAGTCAGAGGC
CTGATGTGAGGTGAAGTGGACAGTGAAACTGCCTTTGCAAAAATCATAACT
GAGAAAATTATTACAGTGAAAGAGATCTTACCTAACCGACTCCATCTAACG
TCTAAACTCCAAGCTGTCCTTTTCATTCCTGAGTTTGGGATTAACTAACTT
TGGGAGGAGCTTAGTTTATACTTTTGCTTTTAAACAAAAACAATAACAGCC
CTTTCAGAAACAAACCCCTTTCCTGCCTGGGGACCAGACTGCTTTTGCAGG
ACTAACAAATTAGCCACAAGATTATAAATTATGGTTTAGGAGTCATGCAGC
TGGAAGCTACAAGATTCTAAACCTCAAATTGCTCCTGGGGATAAAATCACT
ATTTTAAAACCTAAGATCAATGCTTGAGCTATTTTGCAGACCCTGAACACA
ATGGATTAGCTGGCACCACCCATATAGATAAACTGGATTATCTGGTCTTGA
GTCCCCCACCCCACCACTCCCAGGAACTGATTTAGCACAAGAGGACAGCTT
AGGCTCCCTATAATTTCATCTCTGACCCAACCAAGCAGCACTCCCGACTCA
CTGGTCCCCTACAATCAAATTATCCTTAAAAACTTTGGTCCCCAAATTCTC
AAGGAGACTGATTTGAGTAATAATAAAACTCTAGTCTCCTGTAGCGCTGGC
TCCTTATTGCAATTCCCCTGTCTTGATAAATCAGCTCTGTCTAGGAAGTGG
ACAAGGAGAGCCCGTTGGGTGGTTACAATAGGACAAACCAATAAAATATAA
AGTATTAGAGACACTACCTGGGTTTCAGGAACAGGTCAGAAAAAGTGTTTT
CTTGGAAAACATCTGGATTCTGCTGCAGAGCAAGTATTTGCTTGTGTCTTC
CCAGAGTATAAAAGCTGTCCTGTCCAAGATAGTTGCCACTAACCATATGTG
AGTATTAAGCATTGGAAATGTGGCTACTCCAAACTGTGATGTGCTTTAAGT
GTAAAATACACACCAGATTTCAAAGAACTAGTAAAATAACAAAGTAAAAAC
TCAATATTTTAATATTAGATACCTTGTTGAAACAATTTTTGGTTACACTGG
```

FIG. 8-172

```
ATTCAAATCATTAAAATAGATTTCTTTTTTCACTTTTTAAAATGTGCCTAT
TAAAAAATTTAAAATTACATATGTGGACCCTATGTTTCTGAGGAACAGTGC
CAGGACATAGAGGATAGTTATATTCACTCACAGATCAAAAACTAGCAAAAC
TATGAAATACCTAATAATTTAATTTTTCACCTTAACTTTTGGCATATTCCA
CAGATCTGTAGTATATTTGAGTGTGATAGCTTAGGAATAAATATGATTGGA
ACTCATTCATGTTTAGAGAGAAAGGGTGTCAAATTGAGAACCAGGCAGATA
CACCTAATCTTAAAATGACCCCAAAGTAAAGTGGTTGAAGAAATTAAATCC
CAAAGATTTTTGGTGAAGAATGTTGTAGTTTTCATCAGTATGTGTATGTTC
AAATGGAGATTAAAGAAGGCAAAATAAGGCCGGGTGCAGTGGCTCACACCT
GTAATCCCAGCACTTTGAGAGGCCAAGGCAGGCGGATCATGAGGTCAGGAG
TTTGAGATCAGCCTGGCCAACATAGTGAAACCCTGTCTCTAATAAAAATAC
AAAAATTAGCCGAGCACGATGGCATGCGCCTGTGGTCCCAGCTACTAAGGA
GGCTGAGGCAGGAGAATCACTTGAACCCGGGAGGCAGAGGTTGCAGCGAGC
CGAGATCACGCCACTGCCCAGCAGCCTGGGTGACAGTGAGAGACTCCGTCT
CAAAAAAAAAAAAAAAAAAAGTCAAAATAAAAGAACTGTGGGCTGACAAC
TGTGGATTAAGCATCAGTTCTATTAAGAAGGGCTAACTTGAAGATGAATCT
TTTGAAGATACATTTTGACTCCAGCTCTTTAGAGGAACAAAGTTTACCTTG
ATGTGAAATTCTTCAAATAAAAATTTATTGACTTTAAATTTAAAAAAAAAT
GCACACACACACACACACACACAGCTAACTAGCTACATCCTTAATGA
CACCAAGCTTTAGTCCTTCACCCTGAAGTGGGAATGACAATGGCACTTACT
TCAAAGTGCTGTGACAAGAATGTGTTTGAAAATAAATATAGAGTAATCAGC
AACAGTGCTTGGCATATTGTAAATAAGTGCTCAAAAAATGCTAGTTCCCAA
AACTGTTGTTGCCACTGTACCCTAAATCCCTATTCTCTTCTGATATCCTTT
AGTGATGTAATTCTGTCTTGCACTGGGCCTGTTCATCTCTGGTATGAATTT
CAACCACAATGTCCTTACTACATTTCCCTCAGGCTTATATAGCCAAAATAT
CCAGAGCTTTGCCTAGGAGTGTATAATATGATACTTCAATTTGTAGCCATG
ATAGCACTGTGTATGAAAGTTTGGAATAATGCGCCGGGCATGGTGGCTCAC
GCCTGTAATCCTAGCACTTTGGGAGGCCGAGGTAGGTGGATCACTGAGGTC
AGGAGTTCGAGACTAGCCTGGCAAACATGGCGAAACCCCGTCTCTACTAAA
AATACAAAAAATTAGCCGGGTTTGGTGTCAGGTGCCTGTAATCCCAGTTA
CTCAGGAGGCTGAGGCAGGAGAATTGCTTGAACCGGGGAAGTGGAGGCTGC
AGTGAACCAAGATCACGCCATTGCACTCCAACCTGGGTGACAGAGAGAGAC
TATGTCTCAAAATAAATAAATAAATAAAAAACAGAAAGTTTGGAATA
ATGCATTACAAGTAGCCTCTAGTTTTTATGTTACTCATAGTTTTATCACAC
AAGAACAATGTCATAAATTTTCATGGTTGAATTATCAGTTGTTTATGCAAT
ATTCATTGATGTTTTTGGCTTATCAGCAGTGTTTCTGGAATTATTTGAATA
TTATTACCGTTTTTCAAAATTATTTTATAAAACTAATTTAAAAATCAAAAA
TGATATAATTACTAATGTGAAATTAAATATAAGTTTTGAAGAATATCAGGA
TGTCACCCCCAAATTATTCTACTTTGGCATAAAAGTTATTTTCAGCTGAAG
GCAATTGAAAATCAACAGGTGTAGGAAGAGGTCTCTGTCTTCTCTTTACCC
AAATTTCCCTTTGTGAAGGTGACAGAAATTTCCCTTGTAAAAGTGTCCCCA
ACTGCTATACCAGGAAAAAGAGAGCAATTCTTATCACTAGATATGGAAGGT
TGGCACTGAGATGACTCTGCAAAAACAAACCTTACTACAATTATTTCTATC
TTTCATTTTATCTTCCATGGTTTTTATTGCCCATGTATTTATTTCCTTGTC
ACATTCCCAAATTCGTCATCCCATGAAGTGCAAACTCCCTTTCCTTTGTTG
GAATGGTGTATAAGTCTGTGAGTCTAACCGCGTTTTTAAGGTTTCAATTTT
```

FIG. 8-173

```
TTTTTCTTTGGGAACTCTGTGCATGTAATATACTAATAAAATTGCATGCTC
TTTTTTTCGCATGTTAATCTGTCCTTTGTCAGTTAAATTTGCAAGACACTA
CTTAGTGAATCTAAGAGTACAGAAAAACATGTGTCCTCATTGACAGTTTCA
AAAACTAAGTAAAATTGAGGCAAGAATCTTTTTCATCTTAAAATGGCCAAT
TTTAATTTCCAAATGAATGGTTCATTAGACCTAAGCCAGTAAGCTATGTGA
ACAATTGTGATGGAATAAAACAAAACTAAAGAGCATGAACAAAATTGAGAA
AACATATGCAAGACTGAATCTAAAGGCCAAATAGAATTGAAAATTTTTCTA
ATTTTTAACTCTATAAATTAAAGGAATGTGTTTCATTTGACGAGTTTCATC
TGTGGAAACATGTTTGCAGAAGACATTCGAGGTTAGGATTAATTGAAAGTA
CATAAATCAAATGGATTAAGACCCCAAAGGGCATTGAAGGAAAATTAGAAA
ATCAGCTATTTTTGCTTGGGTTGATTCCTCTCCTGACTAACTCTTGGAGAT
GATAAGAACATCAATTAAATGGGTAGCCATGAAAGTATCTAAGGGAGAAAG
GAACACAGAAGTTCAATGTACCATAACTTTATTTTTATTTATTTAGTTTTT
TGAGAGAGAGTCTGGCTCTGTCGCCCAGATGGAGTGCAGTGGCGTCATCTT
AACTCACTGCAACCTCTGCCTCCTGGGTTCAAGTGATTCTCCTGTCTCAGC
CTCCCGAGTAGCTAGGATTACAGGTGTGTGACACCACGCCCAGCTAATTTA
TTGTGTGTTTTCATGGCCAGGCTGTATTTTCATGGCCAGGCTGGTCCTGAA
CTCCTGACCTCAGGTAATCTGCCTGACTCAGCCTCCCAAAGTGCTGGAATT
ACAGGCGTGAGCCACTGCTTCCGGCTTTTTTTTTTATGACGGAGTCTCGC
TGTGTCACCCAGGCTGGAGTGCAAGGTCTCGCCTCACTGCAACCTCCGCCT
CCCAGGTTCAAGCAATTCTCTGCCTCAGCCTCCCGAGTAGCCGGGATTACA
GGCGCCTGCCACCATGGTTGGCTAATTTTTATACTTTTAGTAGAGACGGGA
TTTCACCATCTTGGCGAGGCTGGTCTTGAACTCCTGACCTCGTGATCCACC
CGCCTAGGCCTCCCAAAGAGCTGGGATTATAGGCGTGAGCCACCGCGCCCA
GCCTTTTTTTTTTTTAATTGTTTGATGTTGAGATGGAGAAACAGGAGGA
GGTGGAAGAGATCTTAATATACATATGGAAAAATAAAAAATGGAATAACCA
GGAAAATTCTGAAAAAGAAGAGTAATGAGAGAAAATTAGCTCTATCTGCTA
TTAAAGTCACGTTACAACATCTCAGTTAATTAGTCTCCCAAAGGGGAGACT
AATGTAAATGCATGTTTAATAAACTGCACCCCCAGTGGATGCCTGAAACCA
CAGATAGTACTGAACCGTATATACACTGTTTTTTCTATATACACATGGCA
ATGATGAATTTAATTTATAAATCAGGCACTGTAAGAGATTAGCAATAACTG
ATAATAAAACAACAATTATAACAATATACTGTAATAAAAATGATTTGAGTC
TGTGAACGGTGGTTCACGCCTGTAATCTAAGCACTTTGGCAGGATGAGGTG
GGCGGATAACCTGAGGTCAGGAGTTCGAGACCAGCCTGGCCAACTTAGTGA
AACCCCGTCTCTACTAAAAATACAAAAATTAGCCGGGCATGGTGGCAGGCC
CCTGTAATCTCAGCTACTCGGGAGGCGGAGGCAGGAGAATCGCTTGAACCC
GTGAGGCGGAGGTTGCAGTGAGCCGAGAACGTGCCACAGCACTCCAGCCTG
GGTGACAGAGGGAAACTCCGTCTCATAAATAAATAAATAAATATAAATATA
AATTATATGACTGTGATCTCTCTCAAAATAGCTTACCGTTTTACTTGTGAT
GATGTGAGATGACAGAATGCCAGTAATGAGATAAAGTGAGGTGAATGGAGT
AGGCATTGTGAAGTAGCATTAGGCTTGATAAGATACTACAGATTTAGGTAT
TAGTTGAACACTTGCCATTTGTCACATAATCATCTCAGCATTGAGGATAGC
ACACAACACAATGTTTAAAACAATACAATTCTACCTTAAGAATTGTGGGAA
TGACTAAAGGAACAAAATAGAAACCTGAGAAACCTAAGACAGTCCAACTGT
CCATGAAATTATAGCGTATTAGCCTATGACAAAACAGCCAAAATTGATAGG
AGCGTGGAGGGTGGCACGGGAGGAAGAAGGGGGAAGCAGAAATGAAAGTTC
```

FIG. 8-174

```
ATAAATGGTCTTGGGAAAAATATGTCCATATGTTAAACCTTACACCAAAAT
AGAGGGTTCACCATGTTAAACCGTGTTGTAATGTAAAATTAACAACACAAA
ATTACTTAAACCATGGGAGAATGTTTTCTCCTTCTTCCCTGCCTCTGTCTT
CCTGTCTCTGCTTGCCTCCCTCCCCTTTCTCTTTCTTGGGATGAATCCG
TGGTCACTATCACTAACAAATCAACTCACTATATTAATCATTGTGGAGATG
GTAGAATAATTGAGCAGCTTATCTCCAGAAGCCCCAGTCCCCATAATTTAG
GTCTCACCAAAATGTGCCCACCAGATTTTAAAAGAAGCGAATATAAGACGC
TAGGCTTTCTGTATTCAGAAGCACCATGGATGTCAAACAGAGGGAACCATT
AACGAAGGCCTTTATTAGAAATGTCTCCCATTTATCCATACACTCTTCATA
GTTAATAGTACAAATACTGTTTTCTGCATAGAAACATTTGGACTGCCAAAC
AAAATACGTTTAAAGGAACTTCGATTTTTAAATGTTGCTGTCTGTCTAAAC
AGGATAAGCAACCGTAGTCATGCGAGGACAAAATGGCTGGCTAAAAGTTGT
GCTTTCGATACGCTCAAAATCGATACGCTCAAACCTGTCAGTTTAGCGGAA
GGCTACATGTTATGTGGCACAAAAAACTCCCTAGGTCCACGATTGCCTTGG
GTGGAGGAAGGGCTATTGCCGCTGTTGTGGCTGTTTTTTAAATGCATTCCT
TCGTTGCCACAGGAATGAGAAATTAACAGCAGAGGAATGTAGGACAAAGGT
ACCTGCACGCACTCTCCTCCCAGGGCTGGATGTTGCCACTACCTCCAGGAG
ACATCAACTTGACTACCAACAACATGGAAAGCGTCCGAAATCCCAGACATT
AATATAAAGAGAAAAGAGGCAAAACTTTTAAGTCACAGTAAAGCAAAAAAC
ACAGAATAAGCAACGTCTTCCACCATCCAATTAAATACAGAATGAAAGTCA
TGTACTAGAAGAACGGACCAACCCGGGAGCAGGGCGGGACTTTTGAAAATT
TTTTAGTCCAATCCGGACATCCCTTTAGACTAAGAAACTGGCTCTTGTTTT
GCGGTCTTTTCTGCCGTTCACAGGCCTGGGGCGGGACTGCCATCCCAAAAC
CATCCGCCAGCGAGAAAAGCCTCCGGTCAGGGACCTAGAAGCCGCAATAAA
GGTTTAAATGCTGTAACCTCACCACGGCCACTCTCCAACCCCGTCACCCAA
TTCGTCTGATACCTCAGTAACTCCCATACGACTAACCTTAAGTAACAGGGC
AGAACAAGAAAGGCAGATAGTAAAGAAATTATCCAGCTCTTTTATTGAGA
TCAGTGGTGGCTCTGAAAAGAGCCTTTTGGGTTTTAGAAGTAGGCGTTCGC
CTATTTCTTCTTGGGCGCCGCCTTCTTAGGCTTGACAACCTTGGGCTTAGC
GGCCTTGGGCTTCACAGCCTTAGCAGCACTTTTGGCAGCTTTCTTGGGCTT
CGCAACCTTGGCCTTCTTTGGGCTCTTAGCCACTTTCTTGGTTACAGTGGC
CGCGGCCGGCTTCTTCGCTTTCTTCGGTGTTTTCTTAGCGCTCTTCTTCGG
AGTTGCGCCGCCAGCCGCCTTCTTGGGCTTCTTGGCTGCCCCAACTGGCTT
CTTAGGTTTGGTTCCGCCCGCCTTTTTAACCTTGGGCTTGGCTTCCCCGGA
GGCTGCCTTCTTGTTGAGTTTAAAGGAGCCAGAAGCACCGGTGCCTTTCGT
TTGCACCAGAGTGCCCTTGCTCACCAGGCTCTTGAGACCAAGTTTGATACG
GCTGTTGTTTTCTCCACATCATAGCCGGCGGCAGCCAACGCTTTTTTCAG
AGCAGCCAGAGAAACTCCGCTACGCTCTTTAGAGGCGGCCACAGCCTTGGT
GATGAGCTCTGACACCGGGGGACCAGACGCCTTACGAGGCGTACCCCCAGC
CTTTTTGGCCGCCTTCTTCTTTACAGGGGCCTTCTCCGCAGGAGGCGCGGC
AGCGGGAGCGGCAGGAGCAGTCTCGGACATGTTGAGAATCAAAAACTCGGG
TACAAGTGGCAAAGCGCCGATGAAGCAGCGCCTGGGCAGGGCCGCTGTATA
TATAGAGCGCAGGCGCGCTCTGATTGGTGCTCTGGTCGCCCGCCTGGCTGG
CAGGCTCTGAGCCGCTGCGCTGCTCCCAAGTTGTGTTTGTTCCACCTCACA
AAAGGGGAAAAATATTAAAATTCCCCGCACCAAATCACTTGGGTTTGGTCA
GGAAAGGATCTCAGAAGCCTCGGGCTTCATGCTCTTCATTTATTTTTTCCA
```

FIG. 8-175

```
CAAACACAAAAACAACGCGTCCAGGCGTCCCCAATTCCCCCAACTCCGAAG
GAAGTCTGGGGCAGTCAGAGACCACTTTCTGTTTTTCTTATAAATTACCTG
TTCGCTCCTTTGCCCCTGAAGGTTCTTTTTCCCAGGGGTGGTTGGGCACAT
GCTTCCCTTATTTTTGAAGAAAAAAGCGAAATGGTTTCCACCTAAATTTTC
ATGATAATTCTGTTTCTTCACAAGGGAAGTAACACAGGTCCTCTGTGAATT
CTTCGTGCAGTCGCACAGGAACTGTGGACTGGGACAAGGATTCCACGGCCA
GTCCAAAGCAATTAGGGCGGGATGGGAGGGGGTTCATGAGCCTTGCTAGGG
TCCGGGGTGGTGGGGGGCTACAGACTTAAATCTTTGATTTGAAGACATTGA
AACTATCAAATCCCTCTTTTCATAGATGGGGGTGGGGCATCCTTTTCACTT
CTCTACAGGCGAGAAATTGGGCTCTTTTTAAAGAGCTCTGAGGTCCCCCTC
TGAGTTGTGTAAGGCAGGAGGTCTGGCCCTCAAGATAGAGATCATAAAGGA
ACAAGGGAGAGCCCTTAAGCCTGCAAAAAAGCCAATAGATTTGGCAGTTAG
AGGCACTGAGATAATATGTTTTCAAAGAAAACAAGCATTTTTTATTTATTT
ATTTTTGTACGCTGCAATATAGAAATGAATTTCAGCCCATGAAAATTGTAG
GTTACTTTCAGTAACCATACCTTACGCAAGTTACCATATAGGACAATCTCC
AGTTGGGAACTCAAATATATCTTTTGAGTTGCAAATAAAGCAACTGACTTT
AATAAAACACACTCTTGACTTTTAAGATGAACAATGTATTTGAAATTTATT
TTTTTAAATAGCAAAATTTAACACAGAAAGACAAGAAAAGTACCAGAACAT
GTAATTTATTATAAGATCTGTTGTTGATGAGCTGAAAAATCACCTCTTCTC
ATCCCCTCTGAAACTATTCTGTTCTAAAGTTTGCTACTTTAAGGTTCACTA
CTTCTTATTTTACTCTCCGACCCCAAGTAATTGCTATTTTTTCTTGAGAT
TAAAGGCAAAGTAAATTGTCTGCCCATATATTTGATATAATTATAGATTCA
TATTTAGGGACAAAGGTAATATTACAACTCCCCAACAATTTCTGCTCAAAT
ATATGTTTTCATGAAAATATGTGTTAAAGAGAACAGCCTTAGATTGTGGGA
AAGTCAAAAGGGAACCTACAAATAAGAGTTCAATGACAAATGAAAAGTGAA
ACATCTTTTAGACTAAGGGTGACCCCATTGTTTTATTAAATAACATTTGTC
CAACATTTGTAAACATTGTCTGCTTGTGTGCTTATGTCCTCTGGGAATTAA
CAGTCTAATGAGATTAGTGATGGATGAATTAGCAGTGGTGGAAAAACACTT
AGACCGGCTATTCCTCAGAGTGACAGGGTATAAGAATTATACAAAATTATG
GAAAGTGTATAAACAATTGAAGCACCTGCATCATACTAATATATTGTAGTA
AAAGAAATAATATAAGGCTGGGCCCGTGGCCCACGCCTGTAATCCTAGCA
CTTTGGGAGACTCGGGGGCGGATCACCTGAGGCCAGGAGTTTGAGATCAGC
CTAGCCGACATGGTGAAACACCATCTCTACTAAAAGTACAAAAAATTAGCTG
GGGGTGGTGGCACTCAGGAGGCTGAGGCAAGGGAATCGCTTGAACCCGGGA
AGCAGAGGTTGCAATGAGCCGAAATGACGCCACTGCACTCCAGCCTGTGCA
ACAGGGTGAGACTCAGTCGAAAAAAAAAGAAAGAAAGGAACAATATAAGAA
CATGTCACTTAGGCCAGGCTTGGTGGCTCACGCCTGTAATCCTAGCACTTT
GGGAGGCTGAGGCGGGCAGATCGCCTGAGGTCAGGAGTTCGAGACCAGCCT
GGCCAGCATGGTGAAACCCCATCTCTACTAAAAAAATACAAAAATTAGCC
TGGCGTGGTGGCAGGCAACTCTAATCCCAGCTACTCAGGAAACTGAGGCAG
GAGAATCATTTGAACCCGGGAGGTGGAGGTTGCAGTGAGCCGAGATTGCCT
CGTTGCACTCCAGAAGCCGAGATTGCCTCATTGCACTCCAGAAGCCGAGAT
TGCCTCATTGCACTCCAGCCTGGGCAACAGAGCAAGACTCCATGTCAAAAA
AAAAAAAATAAAATAAACATTTCACTTAGATCTTATTCTATGTGCAATGAA
CCCCCTTCTCATTTAAAACTCAGCTAAGTATATCCATCATGAAAATAGCTA
TGAAACGTCTTGATTACCAGGTAACTGGACCTTCTTTCACTATAAATTGGT
```

FIG. 8-176

```
GTCCTGGTTTATAAATCGACATGTAAATTTAATCGCTGTGATTCAGTTCTC
TAATATGATTTTTCTAGTCGACTCAATCTAATCACATCTCTTTATATGCAA
ATCTCAAGTCCAGACCTCAAGCCATTAGGACATCCAGCCACCCAGAATCTT
GTCCCCAACCTCCTGGCAACATGGTGGAGGCCAGAAGACAGAGAAACATGT
AACCAACCCTTTTCTAGATCCTTTATAAAGTGTGTTGAAAAAGTTATGCAA
AACTTAAAAGCAACGCAAAAATATTTCTCCATATCCTTCCAAGCTATATTA
GAGAATTATCTAAAAAGCCTACTTATGGGGTACCTGATGATGTAAGGCAAT
ACTAGACAGTAAAATAGAATGTGAATCACATAAATACTTTCCAGATTTCTA
GTGGTCACATTGAAAGAATGAAAAGAAACAAGTAAAATTAATTTTAAGATA
TTTTATTTAACTTAATATATCTAAACTATTATCACTTCAACATATAATAAA
TAAGCTAAAAAAAAAGACAGTTGACATTCTTTTTTAAATGATAAATCTTCA
GAACCTGGTGTGTATTTTACACTTTTAGAACATTTTAAATCAGTCTAGCTA
TAGTCCAAATGGTCAATGATCACGTGTAGCTAGTGGTACCTTATTGGACAA
CACTGTCCTACGTGAAAGTAACTCTGACTTAATGTTTACATTTTATTGGGT
CCAGACTATCTAAAAGTAAACATTCACTTGTAGAAGTTTAATAAATTAATA
AGGATTTTGTCATAGAGATGGAAATGAATTCTTAATATAGAAAAAATGACC
CTAAAAGTTATTATTGTATTGCCTAATAAGTCATTAAACAACTTTATATCT
GATTTTCCCTTCCTCTTCCAGTATACATCCTTTCCCTGACCAAATACATAT
TTTATTCTCCCGTATCTTCCTTTGACCTAATTGTGATTCTGCTTCCTCCTT
CATTAATGAATTAAATCATTCATTGACACATACACAAGCTCACTATATATA
GTACATATATGTCAGTCATGTTTTTAACTTCCTGAATGTTGTACTTTGACA
CTTGGTTGTTCAATTTCGCCTAAGAGCTCTGAATCAGAACCTTTAGAAGCC
ATTCTGAAAAACTGGAAGATACAAAGCTTTTGACTATCAACTCCATAGCAA
CCTGATATCTGGTTGGTGTTCCATGGAAACTGTATTTCTCAAATTTTGAAA
TAAGATTGAACAAGCCTGTGAGCAACAACAAAAAAAAAGTCTATTAGAATG
ACCTCTGGCCGGGCGGGTGGCTCACGCCTGTAATCCCAGCACTTTAGGAG
GCTGAGGTGGGCAGATCATGAGGTCAGGAGTTTAAGACCAGCCTGACCAAC
ATGGTGAAATTCCGTCTCTTCTAAAAATACAAAAATTAGCTCGGCATGGTG
GCGTGCATCTGTAATCCCAGCTACTTGGAAGGCTGAGGCAGGAGAATCACT
TGAACCCAGGAGGCGGACGTTGCAGTGAGCTGAGATTGCGCCACTGCACTC
CAGCCTGGGTGACAGAGCGAGACTCTATTTCAAAAAAAAAAGAATGACCTC
CAAGGGAAAGTTCAGATTAAGGATGTGGTCGTCCCACCCAAAACTGATGTC
CTCAAGAAAGCCACAAACAAATTGAGGACACAGTTAAAATATTGTAATGCA
ATATATTGTGTATTCTTTTATTTACACACACATCATAAATATTATAGGTTG
ACTAGTTTTGTTTCATGCCACACTCTTCAGGGTCTGGAAACCCTGGTAGAA
AAGTTAAAAATGCAGAGCAAAATGTCAAGTCCAAACAGCAGTAATGGGGCT
AGAGAGAGACTCAAACAGCCAAGATATATTCAAAGGATAGTGAGAGGAGTT
GTTAGGACAGGTGTAAGGAATGAGGGTGACAGCTGGTTTTTCTTTCACTTT
TTCCTTCTACTATGCCAATTAGAGTTCTTTGTTTTTGATAGAGACAGGGGT
CTCACTATGTTGCTCAGGCTGGTCTCAAACTCTTGGCACCAAGTGATCCTC
CTGCCTCAGCCTCCCAAAGTTTTGAGATTATAGGTGTGAACCACCAAGCCC
AGCCTTAGAGTAGGGTTCTGTCATCTTTTGGATGTAGCTAACCTAATATTA
CTAAATCCTGTATAGGCCAGAACTTTGAATGATTTAAAGCTGTTTTTTCCT
GACTCACCAATTAATGAAGCTAATAATAACAGCCACCCCACTGGCAGTGCC
TGCCTCAAAGAGTAAGTGTTAGTGTTGCTATCTGCTTGAGACCAACAATAC
AGGGACTCCAGGATATTTTCAGCCTAAATAAGATTGTAGGGGCTCTTGTCT
```

FIG. 8-177

```
GTTGCCTGGCTTCAGCCCCATAAACTTTTTTTTAACATATAACCCAGAGCC
ACAGTTTTGCTCATATTTCAATCTTTGAAGGCAAATGGCCAACAATTAGAT
TAAACCTGAGGCTAAATATTTCCTCACCTCAAGGGCTGAGACGAAAGTTAC
TGCATCTGTATTCCCTAACACGCCCTCAAAATGGGTTGCAGAAAACAACAG
AAAATATACTAAAGCACACAGTAGGAGCATAATAAATAGTGATTAGCTGGG
TGCAGTGGCATGCGCCTGTAGTTCCCGCTACTCTACTCATGAGGCTGAGGC
AGGAGGATCACTTTTGCCAAGCAGTTTGAAGTTGCAGAGAGCTATGATCAC
AACACTTCACTCTAACCTGGGCAACAGAGCAAGACTCTGTCCAGAAAAATA
AATACATAAATATAAAATTTAAAAATATAAATAAATACATAGAGAGTATTA
CAAAAGGAACAATATATTGCAAAATATATTTACCTAACATTTTGAAATTGC
CATTATAATTGTATAAGTGACATAGGAAACTGGGTCATTAACAGCTATCTT
ATTCTTCAAGCTTCTTTCAAATGATGTCAAAGCATTTCAGAAAGTCAAACC
TACCCTCAAAGGATAAGAATTTGTCAATTGTGAGGATATGCACATTTTTAC
ACCTTCTCAATCTGTGTCTATATGAAGGCAGTTATAAAGCACAAGATGCAA
ACGTATATTAGGCAATAGTCTTCATCAGAATAAGTACATAACCTGACACAA
TGACTATATTGGAAGAAACATGGAAATGCAAATTTCAATAGATTGGTTGAC
ATTATTTTTAATGTCTAGTTTTTTACTGTGCTGTGTTTTTACACACTTAA
TGAGCACTTGTTAAGCACAGGACACCAGGAGAAATAATAAAAACTAAGATC
AGCCTAGCAGTGTGTCCTCTCAAGAACTTATACCTGGTGGGACAGATACAG
ACAAATATAACCATCATACAGTGTGAGAAATCGATAGAAAAGACACAGCCA
CTGAGAGCACAAAAGAATAAAAACATAAAATGTTAATGTGCTGGCTAAACG
TTTGCCTTCAAGTATTTACCAGTCTAGCTGGGAAAATAAGACAGAAGACAA
CAGCCTAAAATAGTGGTTCTTAAACATTTAGATATCAGGACTTCTTTACAC
TCCTAAAAACTATCAGGCCTCCAAAAAATATTTTGCTAAATATAGGCATTT
ATCACTTTGGAAAACAAAGCTGAGTATTAATTATTTAATTATTTATATTAA
TATTTATTTGATAACCTTTAAAATATTATAAAATTAATATTTATTTATAAT
GCATATATGTGATTATATAGTTCATATGTAGCCATATATTTATCATATATA
CCATAGATTTATGTTATATATTACATATGTATGAAGAAAAATGGAAAGTA
AACCCAAAAGTTCCCCATTCCCTAACCCATTCAAAACCCTGGAAGTCCCAG
GCTAATCTGAAACTTGTAAAACTGCCTGCATGTAGAGAGCACAGCTGAGCT
GGTAGTGTGGAAGAGCAGAAAGACAGCAGTTCTGGAGCAAGGAAGCTTTAT
ATTTAATCCCAGTTTCTCCATTCATGAGCTTGGTTACCCTGCCAAGTTCCT
TCTCTGTAAAATGGGAATAATACTCCCAGAAATACAGTGAGGATTAAATTA
GATAATGTGCATACAGTTCCTGGGATTGGGATCAGCACACAGTAGCCTCTC
ATTTGAGGCATATTTGCATTAGATCCTTGCTGTATGATATCCTTCTGTTTC
TTTCTTTTTTTTTTTTCCTTTGGTGACCCTAAGAAAGATGGTACTCTCC
TTAACTTGGAGGGCTGGATGCGAAGAGACCAAATCCAACAAGCTGGTTCAT
TCTTTCTAATTATGTGTGCTTCCCTTAGCTGCCTCTGAAAGGATACAGGCC
CTAGGTACTAGCCCCAAGAAGCCTAATGATAAGAGATAGAGCTGGACCACC
AGAGAAGAGATGAGTGTGTATGTGTGTGTGCAAGCAATTATATGTGTGC
ATTTAGGAGTGGTAGGTGTGTAAACAGTCTAGAACACTCATTCTCACTGTG
ATGTGAGGATGTATCCCCACATCACTGTTCTGGGAGCTCACTCCTTGTCCA
TCATCCAAGCTTATGATGGACAATTCTTTCCCAAGTGGGAAAGAATTCTGA
TGACACTCACATAACTACCCAGTCCCAACTTTCTGTATCCAAGGTGTGTGC
ATACCTTTGATAGCAGGCAGGTGTGCCTAGCCAATATATTAGGAGCATGGT
ATTCCAGCACTCTGCACTTTTTTACTATAGAATTCATCTCAACCTGCTTAC
```

FIG. 8-178

```
ATTACATGAAAGTTTTGATTGATATCAAATTTTTATTATGTTTGCTTATCA
AAGGATTTGTAATTATGCTTCAGTTGATACATAGATTGTTTATATTTTCA
TGGTTACTTGAAGCACTTATATTTTCCTCATACTTTTACAAAGTAATCAAG
GAAAAATACAGAGGCAGCTTAGTATATTAGTCAAAAGAATAATTAGACTGT
CTTGGAACCTGGAATGTCTGAGTTCAAATTCAATTTTGCCGTTTTACCAGC
TGTGTGACTTTGGGTGAGTTAATAAACCTTTTCGTGTCTCAGTGTTCTCAC
ATGTAAAGAGACAATAATAAGCCTACCTGTTTCATGGGTCATTATGAGGAT
TAAGGAGTTAACATTTAAATAGTTCTTAGAACAACCTCTGACATATTTTAA
GTACAAAAATATATACATATATTAAATAATAACTTTTCTAAAACATCCTAC
CTACAATCTTGTGTGCAAATTGGTGGCTCAATTCTGCAACTGTTGTTGGTG
GTGTTGTTGTTAAGCTTTTGTTTGTCATGACTGTTATCAGTAATATTAATA
CAGACAGTTAACTGAACCCTTCCTCTGCACCAGGCATTATATGGACTATTT
TCATTCTGACTCCCTGCATTCTATGAGACAACCACCATTGTAATCATTCTC
ACGTTGCCAATAAGGAAATGGAGAATGAGAATTCAGACTTCTCCAAGAAGT
GCTGCAGACTGATTATAAATCATGCATCCTAAACACACACATATTAAAGTA
TCAACTAAATCAAACAGAATAAAACTTTTGTTTTTCTATCTACAAAATGCA
TGAATTAAAATATGCCCCAACTACTTAACTAATATATTTAGTAAGTAGAGG
GATGGAAGCGTTTTCACTCCTTCAATACATTCTTCATCAACCTCTCTCACC
TTACCCCTCTGTCACAGGCATTTCCTATGTCATGCGGTTTTTCTGATGTAC
GCTAGGTGGCAGTCAAAACCACGAACTCTTGAAAGAGAGTATATTCCTATT
TTTCTGCAGCCTCAACCTCCAGGGCTCAAACGATCCTCCTGCCTCAGCCTC
CTGAGTAGCTGGGGCCACAGGTGCGAGCCACCACACCTGGCTAACTTTTAC
ATTTTTGATAGAGACGGGGTCGCCATGTTAGCCAGCCTGGTATCGAATTCC
TGACCTCAGGTGATCTGCCCGCCTCAGCCTCCCAAAATGTTGGAATAACAG
GAGTGAGCCACAGTACCTGGCCGGTAATTTTTAACTTCTAGCTATACACTT
AGTTTTTGTCCTTTTCAGTGGACAGAAATTATAATGCCTGTTTGACAGGG
GATAATTCTGAGGCACTGGGAAGCCATGAGACTGCATGGATTGCACAGGCA
GGCAAGAACATGGGAAGGAACAAGTGTCTTAGACACTTGTCTCAGTGGTCT
AGAAAAATCATGCTAGCTGATTCATTCACTCCACAAACAACTGATCAACAT
CTTCAAGAAGCCTAACAATGTACTGAGTTCAGGGGACAAGAAAATAATTCA
GACAGGCTCTACCTTCATGGTGGTGTTTGAAGAATAGGGATCTAGAAAACG
GTAGGTAATAGTGGCTGTGCAAAAGATATCAGAGATGATATGAAAAGGAGG
GACTAGACCATTTTACCCAGGAGTGGAGGTTAAACATAGGGTCTTTAAGGG
AAACGTAAAAATATTAATTCTTTTCATTTTTGAAGTAAAATGACCATCGCT
TCTCGGCCGTTTGGCTAAGAACAAGTGAAGTAAAATGACTGAGGATGACAG
ACATAAATACTGCTATACAAACATGGTAGCACTGAAATTGGCTCTTGCCTG
ACAGGAAGCAAAATTATAAAATTCATTATTTAGATATATCAATAATGATGG
TGATCAGGCTGTAATAATAATGTTATTAATCATTATGTATCAATAAGAATA
CAGGTGTGTGACTTTACAATGTGCCTAAGAGCAACCCAATATTTTGATTGT
AAACCACATTCCCTTAAACACACACACACCTCAAACAAGACCCCATAAAGC
AGACTGCACTAAAGTGGAGGTTATGTAAAAGTCCAACAGAATAAGAACCCT
CCCCCATTGTGTATTAATCTGTGAACTAAAAAAAAATTTCATTAAATTGAA
AATATCTAATTGTCAACTAGCAATTTTAAAGAGTTTAGGCAGAAAATGAAA
TATAAAGCTTTTTTTTAACTTTTAGATTTTTCAAAGCTAGCAGAACTGCTG
AAGAATAACAATTCAAAACATAGGTTTGCTTTGGTTTCAATCTCTGTAGCC
AAAGGCATTTACAATGTAGGATGTTGTTTGTGCTTTCAGACACTAGATGAC
GCTCCAAATCAAAATGCCGGTAGTTGGACAGCCCCTGATCAAGCCGCCCGG
```

FIG. 8-179

```
CAAATCATTAACTGGGTTGACACTGTATTACTCAGCAGATTTCAAAACTCA
TTCACATACAGAGTCTTTTGGTGGACAAAAATAATTATTACCCACAATTGA
CAGTGACAGTACTGAGAAGCTGGGAAACTGAAGTAGGACCCTGGAGCAGCC
AAGTACAGAGACTGGCTCCCAGGACCTTAGGAGTTAATACTATTCCTAAAG
AGAATAAATTGTCAAATAGACAAGAAATTCATGTGGGTTGATGCATTCACT
TCCCCAAAACAATTATTAAGCAGTAGAAATGATAACTACGCTGGTAGTGGA
AATAGTTTACAGTAAAAGGGAGAAGACATGCAAAAACCAAAAAAAAAAACG
GGGCCGGGCGCAGTGGCTCACTCCTGTAATCCCAGCACTTTGGGAGGCTGA
GGCGGGCCGATCACGAGGTCAGGAGATCGAGACCATCCTGGTTAACAAAGT
GAAACCCCGTATCTACTAAAAATACAAAAATTAGCCGGGCTTGGTGGTGGG
TGCCTGTAGTCCCAGCTGCTCAGGAGGCTGAGGCAGGAGAATGGCGTGAAT
CCGGGAGGCGGAGCTTGCAGTGAGCGGAGATCACACCACTGCACTCCAGCC
TGGGCAACAGAGCAAGACTCCGTCTCCAAACAACAACAACAAAAAAACAGG
CAGTGATGTTTTATGTGGGTCAGTGTGAAGTAGAGATCAAAGGAGAAAACG
GCCAATCTTACCAAATAATGGATGCAGAAATAATCTTCATGGAGAAGCCAC
TTTAATTATGTCTTAAATGAGAGTAACAAATTAAACATAAGAACCTGTAGG
GGCTAAGGGAAAACTTACTCTTTGGCCTCTGAAGAGTCGCTGAAAACCACC
GACAAGAGGAAGATTAATAGGATAAAATGCATCCAATTTATTATTATTATT
ATTATTATTATTATTATTATTATTATTTTTAGACGGAGTCTCACT
CTGTCACCAGGCTGGAGTGCAGTGGCGCAATCTCGGCTCGCTGCAACCTCC
GCCTCCCGAGTTCAAGCAATTCTCCTGCCTCAGCCTCCCCAGTAGCTGGGA
CTACAGGCATGTGCCACCACGCCCAGCTAACTTTTGTATTTTTAATAGAGA
CGGGGTTTCACCATTTCGGCTAGGGTGGTCTTGACCTCGTGGTCTGCCCGC
CTCAGCTCCCAAAGTGCTGGGATTACAGGCGTGAGCCATTGCACCCGGCTG
CATCCAATTTATTAATGTGTATATTAATAAATTATCCAATTTATATCCAAT
TTATTAATGTGTATTAACATGTACAGGGGAAATTGTCCATTTTTATTTTTT
AGATTCAACAAAGTATGGGCCGCCGTGTAGAAATAGGATTGCTAATAAACA
GAGTAGGGAAACCCAGCAAGGCCTGTCTGTCTAGATTCTTCTTCGCCTCTC
TGTGCAGCATTCCTTCCTTCTGGATCCTCTCTGGAATGCGGTCTGGTGATC
TATGATCAAATAAGGTAGTTCAGATAATTTCTTTATGGCCAGTTTTTACAC
AGAAAAACAGAGGGAAAGTTAGAGTAATATTTTTAGGTTTTATGGCTGGGC
TCTGGGGAAAAGGTGTTTTGATTTCTATGACCTAACTTGAGGAAGAGGAAT
TCTCATTTCTATGGCTAGACTCCGGGGAGAATGGGACTCAGAGACAGGAGG
GCAGGAGAAGATCAGAGAAAAACTTTGGCTTCTGCGGTCTTTATTTTGGGG
TATTGTTTTCTGAGTTCCAACAAACCCCAAGGACCTACAAAGACTGCATAC
TTTTTTTTTCCTTTTTATTAATTGTGAGATAACCACAGCATAGGCAATTTG
TTTTTTGTTTTTGTTTTTGAGACAGGATTTTGCATTGTTGCCCAGGCTGGA
GTGCAGTGGCATAATCATAGCTCACTGCGTCCCCAAACTTCTAGGCTCAAG
AGATCCTCCCAGCTTAGCCACAACTGAGAGGTGCTACTAGCATTTAGTGAG
TAGAGAACAGATATGACTAGAGGTTCATTAAGTGTTTTGAGCCTTTACAGC
TTCAAAATTGTCTTTGCTAACCCCTAACTTTTGGATGCTACAGAGGGCCCC
TGGAGTATCCAAAGGAGAGGTAAACAGGATCATTTGACACGTTTAGTTATA
TAGGATTGTTGAAATAAGGTGATATTTGATCTTCAGGTCATATTTCAGTGA
AAACTGTGAATGTGTGTTCCAAAATTATAGGGGATTTCTAGAGTTCTGATA
TCTGAGTTTGTGTCATCAGTTATAATTAGAGTTATTGTGTTAGGCTATTGT
AAATCACAGAGGTGACTAAATTTCTTTGTCAATTGTGTTTTTGACTGTGAC
```

FIG. 8-180

```
TACCCTAGGACATTTTAACATTCATAGACAAATGTTGTCTTGTTTTGAAAC
TCTGCAAAGAATGGATTATAACCCTCAATTGCAGGTTTCTGATAACTTTGA
AGATTGTGAACAGGAGTTAACTAGGTGAGCTGAACTATTGGAAAACTAATC
TTCTTGACTCTTGCCTCTGTACCTAATTCTTCCTGGATGCAGGACAAGAAC
TCAGGCAAAGGTGCTGCAGCATAAAGTCTGGCCAGAGAAACTGACACTCCA
GAGGTTTTGTAACAATATTTTATGTTAAATAATTTATACGTATTTCCTATT
CTAAGCATTTCAAGTGATTGTAAAAACTCAACTCATGAAAACTTATAGCTG
AGATGATGTATCCTGTGATTTTTAACTCAACTTTATACCAATCTAAGTTGA
TTAGCATTCTTACAAAGTTTAAGAAGTTAAGATTTGCCATATTAAGTATTG
TCTTAAGATTTTTAAGAATTGAAAAATTTGGAGCAGTTTTGTTCATTAGTC
AATTGGATACTTTAAAAGTCCAGTATGTCAGATTTAAAAATTGCAATTTAT
AAGTTTTCTTCTTAAAGTTCGTCAAATTGCAAAAGCCTTGCCAAAAATGAA
TGTTAAAAATTTGGTAGATTATTTGTTCTATGGGTTCTATGGGAAAAAATT
GGTAGATTAATAAATGCCAATAGTAAGCATTGTAAATTGAATTTAAAAGTT
TAAGGAAGAGCTATTAATTTAATTTTGTCATAATAATGAATTGAATGTTGT
TTTTTAAGTACCATAGTACTTGCTGAATGATCTTTCTGTATGGAAAAGGAC
ATAAAAATGCACATTGGTAACATCAACTCTATTTCAGCGGCGGGATTGTGG
GGTGAGCTTATCTCCAGGTTTGGGAAGGATGTGTTGTATCATCTGCCTCTT
GTGTGTGTACTACCTGCCATTGCTGCTTGGCCACCAGCATCCATCTTGGTG
AGTCCTGTCTCCCTCTAAAAGACTCGAGCTGTGCTGTTCAATCCAGTAGCC
CCTAGCTACATGTAGCTATTGTAATGAATTAAAATTAAGTAAAATTAAACA
TTCTGCTCCTCAGACACCAGTCACATTTCAAGTGCACAATAGTCACAAGTG
GCCAGTAGCTAGTTTTGAACAGTGTGGAAAGATTTCTGTCATCACAGAGCA
TTCTATTATCACGTTGTAAAGCATTCTCTAGCTCTTGCAAACTTGTCAGAT
CCCTTAAAAGTTCTTAAAAATAATTCATCATTCGAATTTTGCTCAGACTAA
TTTTTAGGGAAGTCTTTTTCTGGAGGCGTGGACTTGTGATCTCCATAATTC
ATCCCTTCTACTATGTTAGTTACCTTGAGCTGCTGTAATAAAATACTATAG
ACTTAGTCGCTAAAAAAAAAATAACTTTCTCACAGTTCTGGAAGCTCAGAA
GTCCAAGATCCAGGTGCTGGCCAATTCAGTTTCTAGGTGAACGCTCTCTTC
CTGACTTGTTGGTGGCAGCAGCATTCTCACTATGTGCTCATGTGGTGTCCT
TTTTGTGCTTGTAGGGCTTAGGCAGTGGAGAGAAGGAGGAGAGAAAAGAGT
TTCACTGTTTTCTCCTTTTCCCGAGACAGTTTTTGTGTAGCCCAGGTGGAC
AGCAATGGCTCACTGCAGCTTCTTCCTGGGGTCAAGCAATCTTCCCACTTC
AGCTTCCAGAGTAGCTGGAGCTTCAGATGTGTACCACCACACCCAGTTCAT
TTTTTAAATTTTTAGAAGTTGGGGGTCTCACTATTTTGTCCAAGCTGGTCT
TGAACTCCTGGGCTAAAGCGAGCCTCCTGCTTCAGCCTCTCATAGTGTTGG
AATTACAGGCATCAGCTGCAGCACCTGGCTCTATTGTCTTTTTTTTTTTT
TTTTTGAGATGGAGTCTCTATCACCCAGGCTAGAGTACAGTGGTGTGATCT
CACTGCAACTTCCACCTCCTGGTTTCAAGGGATTCTCCTGCCTCAGCCTCC
CAGGTAGCTGGGAGTACAAGCGTGCACCACCACACCTGGCCAATTTTGTA
TTTTTAGTAGACATGGGGTTTTACCATGTTGGCCAGGCTGGTCTCAAACTC
CCAACCTCAGGTGATCCATCCACCTCAGCCTCCCAAAGTGCTGGGATTACA
GGCATGAGCCACTGCACCTGGCCTGTTGTCTCTTTTAATAAGGGCATGAAT
TTCATCATGAGAGACACATCCTGATGAGTTTGTCTAAATATAATGACTTCC
CAAACGCCCCAGCTCCAAGTACCATCACACTGGGGGTTAGGGTTTCAACAT
ATGAATTTTGCGACGGGGAGTCAATTCAGTCCATAGTACCTACTGTATTAG
```

FIG. 8-181

```
TTTTCTGGGGCTGCAGTAACAAAGTACCTCAAACTCGTTGGCTTAACAACA
GATATTTATCGTCACACAGTCCTGGAAGCTGGAAGTCTGAAATCAAAGTAT
CATCAGGTTTGATTCCTTCTGAAGGCAATGAGGGATAATCTGTTCCAGGTT
TCTCTCCCAGCTTCTGGTATCCCCAGACTCATTGCTTGACTTGAATGGTGA
TTCTCCCTGTGTCTACTCACCACATTTTCTCTCTATAGGTGTCAGTCTCTG
TGTATGACATTTCTCCTTTTTATAAGGACACCCTTTATGTTGGGTTAGAGC
CCACTCTTATCTTAACTGATGAAGTGCAAAGACCCTATTTCCAAATAAGGC
CACATTCACAGGTCCTGATACAGGAGGGGGAAAGTGCTGGGAAGGGAAGGG
CATGGTCCCTTTAAATGATATGGAAGTGGGGAAGGGAAGGGCGTGGTCCCC
GGCTAGGGCTCCACCCCCAGGCCTGTGCCCAGGGACCACGGTGAGGACAGG
CATTTTTGTTTTCCTGCCCAAATGTTGCATTTCCCAAGACCTCCCCTGGCC
TGCCACAAGACACGAATAGCTGGACGTCCAGGGGAGCACACTGGCAGAAGA
GCACACAACAAACGTTTGCCTGGCAAAATGAGGCGGAATTTGACTGGGGTG
GTTGGAGGAGAGCCTGGGCCACTGAGTGGCTGACTCCAAGGGAAAACTTTC
CCACTCCATCCACTTTTGGCTTTGCCCAACTGCTGAGAGCTACCTCCACTT
AATAAAACCTTGCACTCTTTCTCTAAGCCCAGGTGTGGTCTGATTTATTCC
GGTACACCAAGGCAAGAACCTGGGATACAGAAAGCCTTCTTCTGTCCTTGG
GACAAGGTAGACGGTCTAATTGAGTTGGTTAACACCAGCTGCCTATAAATG
GCAAAACTAAAAGAGCACCCTGTAACACACACCCACTGTGGCTTCAGGAGC
TGTAAACATTCAACCCTAGACACTGTGGTGGGGTCATGGGGTTGGAGACCC
ACAACCTGCCCGTCTTAATGTTCCCCTAGAGGTTTGAGCAGCCAGGCACTG
AAGAAATTAGCCACACTCCTATCACATGCCATGCGAGCGGGACAAGGGAAC
TTTTCCCATTTCAGTACTGGTGGTTAGGACTTCAACAACTTTATTTTTGTG
GGAATGCATACTTCAACCCATATTATGAGGGTTCCTAGAATGTGGACTGCT
GAGGCTGAAGCACTACCTAAGTGCCTGAGGCCAGCCTGCAGTTGGTTTCTG
GCTCTCATGAGTTAGCTAACATCTCGGGAGAGAGGAAGACAGGCCTAGGAA
GAGCAGAGCCCACGATTCATTCTTCATTCCACCTCTGCTCTTCAGAATCTC
CTTCAGTCTATGTGATGAGCCATCAGACCTCTTGGTGGGAAATGGTGCTGC
CGTGCCTAGCCCTTTTCGATTGTGCTACCATGCTGAGATTACTGAGGGACC
AGGAAGGCCTGGACTCAGACCATATAGGGTGCCACCCTAGTGGGAATGGAA
CCTGTCAGTGCTGGGTGAATGTGACCGTCCCATGAGGAGAAGACAGATACT
CTTGCCAAGCTGAGCATGGAGACCTGATGGACACTCATTATCATGAGGGG
ATGAAGATCCAGGCTTCCAAAGTTGGTACCACAGGGTGGCTATGGCATGAA
CAGGGGGTTAGGATGAAGGACCCAGAATCTAACATGCTGGAGAGGTAGGGA
AAGGAGTCAGAAATTCAGTCTTGTTGAACCCTAAATATTGCATCTCTCTCT
CTCTTTATTTTTTTTTCTGGAGATGGGGGTCTGGCTCTATCATCCAGGCT
GGGGTGTAGTGGCATGATCTCTGCTCACTGCAGTCTCCGCCTTCTGGGTTC
AAGAGATCCTCCCACCTCAGCTTCCTGAGTAGCTGGGACTACAGGTGCGCG
CCACCACTCCCAGCTCATTTTGTACGTTTTTGTAGAGACACGGTCTCACC
ATGTTGTCCAGACTGGTCTCGATCTCCTGAGCTTAAGCGATCTGTCGCCTC
GGCCTCCCAAGAAGGATTGGGATTACAGGGCCTGAGCCACTGTGACCAGCC
AACATTGCATCTAATTTTAGGGTATTCATCTGACTTTCCTGAACACTGCTT
CTTGGGTGCTCATTTTAGCAGGCATTTGGCCATAGGTAGATTTAAAGTTTT
GGTGGGTTTTGTTGTTGTTGTTGAGACAAAGTGTCACTCTGTTGCCCAGGC
TGGAGTGCAGTGGCAAGATCTCAGCTAACTTCAACCTCCATCACTGTGCTT
CAAGTGAGTCTCCTGCCTCAGGCTCCCGAGTAGCTGGGATGACAGGTGTGT
```

FIG. 8-182

```
GCCACCATGCCCTGCTAATTTTTTATATTTTTAGTAGAGATGGGGTTTCGC
CATGTTGGCCAGGCTGGTCTGGAACTTCTGACCTCAGATGATCTGCCCGCC
TCAGCCTCCCAAAGTGCTGGGATTACAGGTGTGAGCCACAACCCCTGGCCA
ACGTTTTCTGAAAAAGCTATTCTAATCAGGTAGGAAAGATGGGAAGCGGGG
TGGCGGGGTGTACTTTTTTCTGCATATTCAGTTGCAGGGTCCCAGACCAGG
GAACAATCTTCAATCTCTTACCTTCAATCTCCCTTCATGGAAGTCAGTGCT
CAGCCTGGCCATTTACTGTGTGCAGTAGGTGTGATGTAGAAAGCCTCTAAA
CCTCCATGCCTACCTGCCAGGAACAATATACACAAAGGTGTGTGTGTGTGT
GTGTGTGTGTGTATCTTACGGATTCTTCCACGTAACTATGTGGACATCT
AATCCATTGCTTCCAACTCTATATTGTGCAGTGACTTCATTTTACCTCCAC
CTCTCTCAGTGAAGGATATCAGTCAGCCCACACTTTCCTGTCACCTTTATG
GGATATGTTTGAGATGATATTTGGAAAATATTCCCAGGGAGTGGGCACTCC
CATCAGCAGTGTATGAGGATTCCTGAGTCTCCATATCCACACCAATACTGA
GCATTATTCAGCTCTCTAATTTGTTAATGCTCTCTTTTAAATGCAAAAGGA
CACATCACTTTACCTTTCTTTCATTACCAAGTGCTTTGGATTTTCCTGTAT
CTAAATTTCTTGTTCATTTATTTCATATATATATATATATATATATATATA
TATATATATATATAATTTTTTTTTTTTGAGACAGAGTCTCACACTGT
CACCCAGGCTGGAGTGCAATGGTGTGATCTCAGCTCACTGCAACCTCTGCC
TCCTGAGTTTAAGTGATTCTCCTGCCTCAGCCTCCCAAGTAGCTGGGATTA
TAGGCACCCACCACCACGCCCGGCTAATTTTTTGTATTTTTTGTAGAGATG
GGGTTTCACAATGTTGGCCAGCCTGGTCTCAAACTCCTGATCGGCCCGCCC
TGGCCTCCCAAAGCGCTGGGATTACTGGCATGAGCCACCGCGCCCGGCCTC
ATACATTTTTTATGTGGAGTTTCTGTTTTGTTCTTCTTGGCCTTGTGCATT
CTAATTACTCATCCTTTCGTCTGATTCAGACATTTAATTCTCTACCATCCT
TACAGCAGTGTCTTAACTTTATCCATGGGATCCTTCATTGAACCGGAATTC
TTAATTTTGACACAAACAAATTTATCAATTTCTTTTTTGTGTGTGTTTTTT
TTTTCTGTGTGTGGTTTTTGTTTTTCACATTTCTGAGTATGACCTAGATTT
ATCCTTTGATAACTTCTTCTCTCTTCCCCATTTTCCTCCACTGGAGGTCAG
CTATATGTGTGTGAGAGGGTTAGGTATATGTGGATATATAGAGAAAGTTTA
GGTATACATATGTGGAGAGGTCAGATAAATATGTATATATGGGAGAGATAT
TGGGTATATATTTTGGGGAGGGGAGGTCAGGTATATGTGGACATATGGGGA
GGGGAGACCACAGCTCTCCTGGAGTCACCCTCTTCCTCTTCCCTTCTGGGC
AGGTAACGGTGGGGAGTGAGAGGGTGTTCCTCCCTTCTTATTATTAGCCCC
TGGGTACTTTAGGGTCTCTAGTGGTTATTTTTCACAGAATTTTAACTGATA
ACTAATGAACAAATGTTTTCCCCACAGAAATATCTTTACGCCTTTTACAAT
CATTTTTATTTTCTATGCCATAACTTTATTAATATTTGCCAATTTACTTGG
GGTAGGACTTTGAAAATTTTGTTTAAATTAAGGGAGGAGACCACCCCTCAT
ATTGTCTTATGCCCAATTTCTGCCTCCAAAGAAAGAAAAAGTAAAAATTAA
AAGGGAGAAATGAAATCCACAGGCAAACAGCCCGGCACCGCACCCTGGGTC
TGGTTAAAGATCGACCTTTGACCTAACAGGTTATGTTATCTATAGATTCCA
GACATTGTATGGAAAAGCATTGTGAAAATCCCTGTGCTGTTCTGTTCTGTT
CTGATTACTGATGCATGCAGCCCCAGTCACGTACCCGCTGCTTGCTCAATC
AATCACGACCCTCTCATGCAGACCCCCTTAGAGTTGTAAGCCCTTAAAAGG
GACAGGAATTGCTCACTCAGGGAGCTGGTTTTTGGAGACAGAGGTGATTAA
CGGACGGTCAAGGCAGCCCCTTAGGCGACTTAGGCCTGCCCTGTGGAGCAT
CCCTACGGGGAACTCCAGCCAGTTTGAGCGACACAGATCTGGAGAGCGCTC
```

FIG. 8-183

```
CCAGGTAGGCAATTGCCCCGGTGGAACGCCTCACCAGAGCAGCACGTGGCA
GGCCCTCGTGGAGGATCAACGCAGTGGCTGAACACCGGGAAGGAACTGGCA
CTTTGTTGTCAGGGCATATTCCAAAAGCATTAAGGCCTTCCTATCAAAAAT
CCTTAACCCAGTAACCCGCGGATGGCCCAAATGCATTCAATCTGTAGCGGC
AACTGCTTTGCTAACAGAAGAAAGTAAAAAAATAACTTTTACAGGAAACCT
CATTGTGAGCACACCTCACCGGTTCAGAAGTATCCTAAGGAAAAAAGAAAA
AAGAAGATGATTTAACATTAACCACTGAAAATTCTCTTAACCCGGCAGGTT
TCCTAACAGGGGATCTAAATCTTAATTACCATACAAAGCTCTGACCAGACC
TAGGGGATTCCCTTCAGGACAGGAGGATAGATGGTTCTTCCCAGGTAATTA
AAAAAAAAAAAAAGCCATCTATACCAATTCTAAGTTAATTTGGACTAAATA
AGGTCTTATTAATAGCAAAGGATAATTGAAATCCCAAACTTACAAGGTTTT
CAACAAAAGTAAAGTTTGCTAAAAGTTAACAGTGTAACATGTATTATAGTA
ACTTCTAATCTTGTGGCCTTAGACAGTCTAGTCCACAGACATAAAAGAAGT
TCGCTTTGGAAAAGAATGGTTATCATCCTCGGAAAAAAAAAAAAGGAAATA
AAGAGGAGGCAGAATTTATATAAAAAAGAATGTTGTATGGAAAATCCTTGT
CCTGAGATAAATTAACTAGTTGTTTAAAGAAAGGGATGTTTGCAATAAGTC
AGAAAGTTGAGGCATGTCGAAGAATTGTCTGTGAAAGTCATGAAAAAAATG
TGTGTTAGAAAAATAAATTTATGTAAGAAATGTTGTATAATTTAAAAGTAA
TTAGGCCTCCTTCTAAATGTAAAACTATTGAATAAACAGTTTATGTGCAAG
GTATGTAAGGAAAGTAAAATATACCTTTGGTAAAAGGATTATGAGGATGCA
TAAGAATGTGGATTTTTACCTACATTAAAAGGTTACAAAAATTGTTTTGAA
GGTTTAAGCAAGTTTTGAAACCTTAATTGTAAAGAAAATTCTGTGTCTAAA
CATATTGGCTAAAGTTAAGGGGTATCATACAGTTTTTCTGTGAACTGAACA
TTAAAATAAAAACACAACGGGTTTTTCTTAAAGCACTAACCTGTTCTTTAA
CAAAAATTATAAAAGGTTAAAGAAAAGTCTATAAAAATCTTACCTTATGGT
CAGACATTAAAAATCAAATAAATATGTCTACAGAGTTTTATTAAAACTAAG
TTTAACATTAATAACACACCAATATAAAGGTGAAATCTAGCTTATCTGGTA
TAAACATACAAGAAGCGTTGTCAAATATAAAATGGCATTTGACTTTCTTTG
GTCTAAAAACTAATAAAAATAGGTGCTAAAGGAAATTTCTCAGTAAGAAGG
CACCAAGGACTATAAAGTCCACTGCTGATGTCCCCACATTTAAAACAAAAG
GTCAACTTCTTAAAAGTTATATACTTGGTTTATCTTCCACTTTCCTTTCCC
TCAAAACTAAAAGTCTTTTAGCACATGTACCACCCCTAGAATTTTCTGTAA
ACCAGCACCAGCCTGAAGATCATGTTCTCATCAAAGGGTGGAAAGAAGGAA
AACTTGAGCCAGCCTAGGAAGGACCCTACCTTGTGCTGCTAACCACCGAGA
CTGTTGTTCATACGGTGAAAAAGGGATGGACTCATCACACCCGAGTCAAGA
AAGTGCCACCCCCTCCAGAGTCATGGGCCATAGTCCCAGGGGAAAACCCTA
CCAAACTAAAGCTAAGAAAAATTTAACTCCTTCATCTATTCTATTACTCTT
TCTTCTTCCCTCACTCTATTTCTGACCATCTAGTTATTAACATAACCAAGT
CAATTTTGCCTCAAACTATTGAATTTAATGCTTGCCTTGTTATACCCTGTG
GGGACTTGCCAAGTCGAAGACATCTCTGTACTTCAGAAAAGTACCTCTGTC
CCTCCTGACTCTCCTCAGACTGAGCCTTAGTAAACTGAGACCATTTATTCC
AGAGAGATTTCAATAAAGACCCCAGTGTCAACGAGGAGTCTTGCCCCCCGA
TGTAGAGCTTTTATGCCATAGTTGGTCGAATGTTGTGTGGACCACTAAAGA
GCAAGGATGGACTGCCCCAACCGGTTTTTGTAATTTCCTAAAATCATACAT
TCATTTTACTAGAGGGTCATAGAAGTTAAAGACTTAAAACAAACTTTGATA
ATTAAGCAGGATACCAAGATGCAAATGCCCAGTTGGAATGGATCAAATATT
```

FIG. 8-184

```
CTGTCCACACATTAAACAAAACCAATTGTTATGCTTGTGCACATGGCAGGC
CAGAGGGCCAGATTATCCCCTTTCCACTAAGGTGGTCCTCCTGTTGACCAG
GCATGGGCTGCATGGTAACTGTTTTCCAGGATTCTACAGCCTGGAGTAATA
AGTCGTGCCAAGCTCTCTCTGCTATATCCCAAAGTCCAGCACCCTGCAGGT
CAACCCCTGAGGGCCATCCAGCTTCCATCTCCCAAAACTAAGTTCACTTCT
TGTCTCTCATGACAGGGAGGAAACTTAGCATTCCTTGGAGACCTGAAGGGA
TGCAGTGAGCTTAAGAATTTTCAGGAGCTTCTCAATCAGTCAGCCTTTGTT
CATCCCCAAGCGGATGTGTGGTGGTATTGTGGTGGACCTTTACTGGGCACT
CTGCCAAATAACTGGAGCGGCACTTGTACTTTAGTCCAATTGGCTATCCCT
TTCACCCTAGCATTTCATCAACCAGAGGGAGGAAAAATAAGACATCGTAAA
GCAAGAGAAGACCCTTATGTGTCTTTCAACTCTCACATCTATTTAGATGCA
ATTGGAGTCCCACAGGGAATAGCAGATCAATTTAAATCCCAAAATCAAATA
GCTGCAGGATTTGAGTCAATATTTTGGTGGGTGACAGTTAATAAAAATGTA
GATTGGATAAACTACATCTATTACAACCAACAGCAATGAGTTTTTCATGAG
TTAAAAGAAAAACTCATGTCGGCCCCAGCCCTGGGGCTACCTGACCTGACA
AAACCCTTTACACTCTATGTGTCAGAAAGAGAAAAAATGGCGGTTGGAGTT
TTGACCCAGACTGTGGGGCCCTGGCCGAGGCTGGGCCTCCAAACAACTAGA
TGGAGTTTCTAAGGGTTGGCCTCCATGCTTAAGAGCCTTGGCAGCAACAGC
CCTGCTAGCACAAGAGGCAGATAAGCTAACTCTTGGACAAAACCTAAACTT
AAAGGCCCTCCATGCTGTGGTGACTTTAATAAATACATCATTGGCTAACAA
ATGCTAGATTAACCAAGTACCAAAGTTTGCTATGTGAAAATCCCTGCATAA
CCATTGAAATTTGCAACACCCTAAAACCTGCCACCTTGCTCCTGGTATCAG
AAAGCCCAGTTGAAAGTGACTGAGTAGAGGTATTGGACTCAGTTAATTCTA
GTGGGCCCAACTTCCAAGACCATCCTTGAACATCAGTAGACTGTGAGCTGT
ACGTGGCAGCTTCGCCAACGCCTGCAAAGTGACTGAAGAAGACAACAAGCC
CTGCTCCAGTCACACCCGGAAGCTGACTGGTCCATGCATGGCCGAAACATG
AGAAAACTCATCAAGGGACTCATTTTCCTTAAAATTTGGACTTGCACAGTA
AAGACTTCAACTAACCTTCCTCAGACTGAGGGCTGTTCCCAGTGTATACAT
CAAGTCACTGAGGTAGGACAAAAAGTTGCTACAGTCTTATTATTTTATGGT
TATTATAAGTGTACAAAGACTCTAAAAATAACTTGTTTGTATAATGCTATT
CTATACAAGGTAGGTAGCCCAAGAAATGACCAACCTGATGTGTGTTATGAC
CCATCTGAGCCTCCACGACCACAGTTTTTGAAATAAGATTGAGGACTGAG
GACTGGTGGGGGTTCATAAACGATACGAGTAAAGTGTTAGCCAAAACAGAA
GAAAAAGGAATGCCCAAACAAGTCACCTTGAAATTTGATGCCTGTGCTGTC
ATTAATAGTAATAAGTTAGAAATAGGATGTGGTTCTGTTCATTAGGAAAGA
GGCTATATGGCAGAAAATAAGTACGCTTGTCATGAATTAAGACTGCGTGGA
AATAAATGTAGATACTGGTCTTGTGTCATTTAGGCAACTTGGTTAAAAAAT
AAAAAGAATCCTGTCCACCTTCAGAAAGGGAAAAGTGGCCCTTCCTGTACC
AGTGGTCAGTGTAACCCCTTAGAACTAGTAATAACCAACCCCCTTGATTCT
CACTGGAAAAAGGGGATCGTGTAACCTTAGAAATAGTTGGGGCTGGACTG
GATCCTTGAGTAAATATGGTGGTTTGAGGAGAAGTTTATAAATGCTCCCCT
GAGCCAGTATTTCAAACCTTCTTATGATGAACTGAATGTGCCAGTACTAGA
AATTCCAGGAAAAACAAGAAATTTGTTTTTGCAATTAGCTGAGCATGTAGC
CCAGTCTCTCAATGTCACTTCATGTTATGTATGTATGTGGAGGAACTGTAA
TGGGAGATCAATGGCCATGGGAAGCACGAGAATTAGTACCTACAGACCCAG
TTCCTGATAAATTCCCAGCTCAAAAGACTCACCCTGATAACTTCTGGGTCC
```

FIG. 8-185

```
TAAAAGCCTCAATCATTAGACAATACTGTATAGCAAAAGTGGGGAAGGACT
TCACCCTTCCTGTGGGAAGACTCAGCTGCCTTGGGCAAAAACTGTATAATA
GTACTATAAAAACAGCCACCTAGTGGAGTTCAAACCACACTAAGAAAAATC
TATTTAGTAAATTCCCAAAGTTGCAAACTGTGTGGACCCACCCAGAGTCCC
ACCGGGACTGGACAGCCCCCACTGGATTATACTGGATATGTGGGCATACAG
CTTATGCCAAATTACCTGACCAGTGGGCAGGTAGTTGTGTTATTGACACTA
CTAAACCATCTTTCTTCCTACTGCCCATAAAGACAGGCAAACTCCTGGGCT
TCCCCTGTATATGCTTCCCGCAAAAAAAAAAAAAAAAAAAAAAAAAAAAAA
AAAAAAAGCATAGCTATAGAAAATTGGAAAAATAATGAATGGCCCCCTGAG
AGAATCATACAATATTATGGGCCTGCTACTTGGGCACAAGACGGCTTGTGG
GGATATGGGACCCCCATTTACATGCTCAACTGAATCATACGGTTACAAGCT
GTCTTAGAAATAATTACTAATAAGACCAGCAGAGCCCTGACTACTGTGGCC
TGGCAAGAAACTCAGATGCAAATGCTATCTATCCAAAATGGATTGGCTCT
CGACTACTTGCTAGCAACTGAAGGAGGGGTCTGTAGGAAATTTAACCTTAC
TAATTGCTGTCTACACATAGATGATTAAGGGCAAGTAGTTGAAGACATAGT
TAGAAATATGACAAAAGTGGCACATGTGCCCATGTAGGTGTGGTATGGATT
TGTTTCTGGGGCCATGTTTGAAAAATGGTTCCGAGTGCTAAGAAGATTTAA
AACTCTTATAATAGGAGTTATAATATTAATAGAAACCTGCTTACTGCTTCC
TTGTTTGCTACCTGTACTTCTCCAAATGATAAAAAGCTTCATCACTACCTT
AGCTCACCAAAATGCTTCAGCACAAGTGTACTATATGAATCATTATCAATC
TGTCTTTCAAGAAGACATAGGTAGTGAGAATAAAAGTGAGAACTCCCACTA
ATGAGTGAGATTCTCAAAGGGGGTGAATAAGTGAGGCGACCACCCCTCATA
TTGTCTTATGCCCAATTTCTGCCTCCAAAGAAAGAAAAAGTAAAAGCTAAA
AGGCAGAAATGAAATCCACAGGCAGACAGCCTGGTGTTGCACCCTGGGTCT
GGTTAAAGATTGACCCCCGACCTAACCGGTTATGTTATCTATAGATTCCAG
ACATTGTGTGGAAAAACACTGTGAAAATCCCTGTTCTGTTCTGATTACTGG
TGCATGCAGCTGCCAGTCACATACCCCCACTTGCTCAGTCGATCATGACCC
TCTCACACAGACCCCCTTAGAGTTGCAAGCCCTTAAAAGGGACAGGAATTG
CTCACTCAGGGAGCTCGGTTTTTGGAGATGTGAGTCTTGCCAAAGCTCCCA
GCTGAATAAAGCCCTTCCTTCTTTAACTCAGTGTCTGAGGGGTTTTGTCTG
TAGCTTGTCCTGCTACAAAAATAAGTGTTAAACATGAGTTTTATATTACCT
CATAGGTGGAAGAAGACAGGCCAAAAAAGCTGTTTTAACAACAACAAAATG
CACAAATATTTATACTAACAAGACAGATATCCATTGCAGTATGACACGAGA
AACAAATAAATGAGACAAGCAGTCAATTCAGACATTTTAGGAAGTGATTTT
TACAGAACATAGTGACAATTGCTGAGATCTGGTAGCCTTGCAAGATTCCTT
TGTTATAATAAAAATAACATTGGCAAAGACCATTTTATGATGCAGACTTCT
GCTTTTTAAAGTTTGGGGGGAAGGGGAAACATTTTTATTCTATAATGCTG
AAATTTCATTTTTCTTTTCTCTTTTTAAGACCAAGTCTTGCTCTCTCACC
AAGGCTAGAGTGCAGTGGCGTGATCTCAGTTCACTGCAACCTCCACCTCCC
GGGTTCAAGCAATTCTCCTGCCTCAGCCTCCTGAGTAGCTGGGACTACAGG
CACCATGCCCGGCTAGGATAACATTTTTTGTTTTTAGTAGAGATGGGGTTT
CACCATGTTGGCCAGAGTAGTCTAGAACTCCTGACCTCAAGTGATCTGCCC
GCCTCATCCTCCCGAAGTGCTGAGATTACAGGTGTGAGGTACAGCATCTGG
CCTCATGCTGAGATTTCTTTCATTACCAGTTCAAACACCTTTCACTTTTCA
AGGCACAAGGAGAGGAATTCCATGTGTTGACACTGGGAGGAAGGGTACAGA
CCTACTTAAAAGATTCAAAACTTCTATGACAGTAAAAGAAATGTATATCAA
```

FIG. 8-186

```
GTTCCTTAGGGCTGCCGTAACAAAGTACTATCAACTGGGTGGCTTAGAACA
AAAGAAATTTATTCTCTCACAGTTACGTAGGCCAGTTGAGATCAAGGTATT
ATCAGGGCCAAGATCCCTCTGTAGCCTCTGGGGAAGGATTCTTTCTTGCCT
GTTTCCACTTCTAGCAGCTTCCTGTGTTTGGTTTGTGGCAGCATAACTCCA
ATCTCTGCCTCCATCTCTACCTGGCCATCATCCCTCTGTGTCTGTGAGGAC
CCCAGTCATTGGTTGGAGGACTCACCCTATTCCACTATAATCTCTTCTTAA
CCAGTGAACTCACCGTATTCCAGATAAGGTCAGGTTCACAGCTACTGAGGG
TTAGGACAGAGTATCTTTTGGGGAGATGCAATTCATCCCATAAGTGGGTGG
AAAAGGATGATTAACAAGTGGTATGTGGGGATGTATTGTTTTGCATCTACG
TAGCTCTCACCCCATTTCTTTCCACAACACACATTTGTCACTCTATTCTTT
ATTAGGTTTACAGAGAAAAGTAGATCTTCAACCACTTTCCTGGGATGTGGA
TACAGCTCTTTTTTTGGAGACAGGGTCTCATTCTGTCACCTAGACTGGTGT
GCAGTAGCACTATCATGGCTGACTACAGCCTCAATGTCCCAGGCTTAAGTG
ATCTTCCCAACCTCCTGAGTGGCTGGGACCACAAGTGTGTGCCACCACACC
TGACTAATTTTATTTTTAATTGTTTTGTGAAGACAGCATCTCCCTATGTT
TCCCAGGCTGGTCTTGAATTCCTGGGCTCAAGCCATCCTCCTGCCTCGGCC
TCCCAAAGTGCTGGGATTACAGGCAAGAGCCTCCATGCCTGGCCTTCAACT
CTTGACCTTATGAACACAGCCCTATACCAGTTCCCTTCATGCATGTGCCTA
TAAGCTAAACCCTTCCCAAGTGTACATGAAAATCTGAAACCCCAACAAATA
TGGCCTAATTCTAAATCTGACTTTCCCAGGAGTAATTTTTGTCATTTCCAG
CTTACCAGCCTTTGTGAGTGTTGAATTTCAGCATTTCTGTTTGCTTGCAGC
AGAAGGTGGAGCCAGGATAGGGTGGCTCAAGATTAGAGTTTCTTCCTTAAC
AGTTCAGTCAACTTTTTAATCTTGGATTTATAGCTTCCTACCTGCTCTCTT
AAAGGTGAAATGATCTATTCACCTTCAGACCATTTGCCCTCGGGGTCTCAC
TGAGCAATCTATGGCTTAAGTCTTCTAAGTCTCTTAATGGCCAAATACAAT
GGACAATTTTCAGGTATATCTGACACCATTTCTCTGCAGCCTTTGGCACCT
ATAACCACTCCATGGCTTCCACAATGTGATTGGTCATTTCTTTTTTGTTTA
TATGACAAGTTTTTATTCTTCTTCTGCCTGTTAAATGCGCCTGACCCCCAG
TGTTCTGATTTTCACTATTTTCTTAAAAAAAAAAGTTTAAATGAAAAAAG
TTTCTTATGAAAATATTAAAACATATACAAAAATAGAATAGACATTGATAA
TAGATCCTAAAATTCCTAGGGAAATTCAGCAGACTGAGAATAGCTAATATA
GTCTTCCAAAAAAAGATCAAATTTGAAGTTGAGAAACTTCTTGAATTCAAT
TTACTAAAAAGCTATAGTAATCAAGACAGTGTAGTCCTGACATAAAGATAG
GATTATAGTCTGGGTGTGGTGGCTCATGCCTGTAATCCCAGCACTTTGGGA
GGCTGAGGTGGGCAGATCACCTGAGGTCAGGAGTTCCAGACCAGCCTGACC
AACATGGTGAAACCCCGTCTCTACTAAAAATACAAAAATTAACCAGGCATG
GTGGCAGGTACCTGTAATCCCAGCTGCTTGGGAGGCTGAGGCAGGAGAATT
GCTTGAACCTGGGAGGAGGAGCCAGTGGCCGGGATTGGGCCACTGCACTCC
AACCTGGGCAATAGAGTGAGGCTCTGTCAAAAAAAAAAAAAGATAGGATTA
TAGATTATAGCATAATGGGATAAAATTGAGACTCCAGAAATAAACTCTCAC
ATTTATGGTAGATTGATTTTTGATAAGGGTGCCAAAACACTTCAATGAAAA
AAGAGTCTTCTCAACAAGTGATGGTGGAACAACTGAATAACCACATTTTTG
TTCTATCTGGGGCCCTGATTCAAAAACCCAGGCAAAGATGGAGAGAAATCA
GAACTCTCATACACTGCTGATAGGAGGATAAAATGCTTACTTTGGAAAAGA
ATGTGGCAATTCCTCAAAAGGTTAAACAGTGTTACCATATGACCCAGCAAA
CCCACTTCTAGATATATAACCAAAAGAAATCAAAACATAAGTCTACAAAAA
```

FIG. 8-187

```
AACTTGTACATAAATGTTTATAACAGCACTATTCCCAATAGCCATAAAGTA
GAAACAAACCAATGTCCATCGGCTGATGAATGAATAAATAAAATATGTTGT
GGTATGTCCTTATAATAGATATTATTGGTCCATGAAAAACATACATAAAAA
CATTATGCTAAATGAAAGAAGCCAGTCACGGCAAAGCAATATATTATATGC
CTCTATGTATACTAAATGTTCCAAATAGAAAGAAAGTAGATTAAAGATTGT
CTAGGGCTGGGAGGGGAGGAGGAGGAGAATGGAGGAATCTGGGAGGCGATG
AATTAAGGGTACTGAATTAGGGGAACATGGTTTCTTTTTGGGGAGATAGAA
ATGTAAAATTTTGGTAATGGTTGCACATCTCTGTAAATATACTAAAATCCA
TTAATTTTTGCATTTTATTTTATTTATTTTATTTTTGAGACGGAGTTTCGC
TCTTGTTGCCCAGGCTGGAGTGCAATGGCATGATCTCGGCTCACCACAACC
TCCGCCTCCCAGGTTCAAGCGATTCTCCTGTCTCAGCTTCCCGAGTAGCTG
GAATTACAGGTGCATGCCACCACACCCAGCTAATTTTTTTTTTTGAGATG
AAGTCTTGCTCTTGTCTCCCATGCTGGAGTGTGATGGCACGATCTTAGCTC
ACTGCAACCTACGCCTCCCGGGTTCAAGCGATTCTCCTGCCTCAGCCTCTA
ATGTAGCTGGGATTACAGTTGCCTGCTATCACGCCCGGCTAATTTTTGTAT
TTTTAGTAAAGACGGGGTTTCACCATGTTGGCCAGGCTGGTCTCGAACCCC
TGATCTCAGGTGATCTGCCTTCCTCGGCCGCCCAAAGTGCTGGGATTACAA
GCGTGAGCCACTGAGCCGGGCCAATTTTTGCATTTTACATAGATGAATTAT
ATGGTATGCTAATTATATCTTACCAAAAATTGAAAAAAAGGAATAGTACTA
TCAGCCCCAATGTGCCCATCATCAATATTCTACATGTTTCCAATGTTATTG
TATCTGTTTGCCTACAGTCGAGGCCCTGATATCCTGTTTGATTTTCTTGAA
TTGCCAAAATTTGCATACATGCTTACAAAAATAATGCCTGTTGAATTTGCT
AGATATGTAAAGGTTTGGAGCAAATCAGGTGTATTAAATTTATTAATATTG
TTTGAAATGTCTAAGGCAATAATTCCCAAACTTCGTTGAGGGAGAAGGAAA
GCTTTTAAAATCCCATTGCCCAGGTGGCATCCCATACTGTTACTGGGAATT
ATGCATTGGGATGGATCCTTTAACCGAGGAGATTATTATAGCCGGAGCTCT
GAACCAGCAATCTCAGTTCTTGTGATAGTGAGCAAAGAACTACAAACTAAC
ACCAAAATGCAAGCTTAAAGCAAAGTTTATTGAAGCACAATAATACACTCT
GAGGGACAGCGGGCTTATTTCTGCGAAGTGAACTCAGCACTTCTTTACAGA
GCTCAAGGTGCTTTTATGGGGTTTGTGGGGAGGAGTTGAGGTTTGGGCTGT
ATCTGAGTGACAGGATGATGTTATTTGATTGAAGTGTATAGCTATACAATC
TAAAATTAAACTGTGCATGGTCTTACCTATAATTTGTTAAGAAAAGCCTCC
CAGGGATGGGGGGGCAAAACTGTATGTAAATTCTATTATAATGATGGCATG
ATGAACTTGGGGTGAACTTGAAGACAGGCTTTTGTGTTGTTGGGCATGTGC
CACCTTAGGGAATTTCCACCTGTACCCTCCTTTCTCTTTCTCCAGGATATT
TTGGCCACAGACTTTATCATAAACTCCATCCCTTAGGGTGGCATTAGGGTA
GTCTTGGGCCTGAATTTAGGTGGGCCAGTGGCTGTCTTAGTGACAGCCTTT
CCGCTCTCTTCTGTCATCCCCTCCCAACTGCTAATGTCTAACTACCTAACA
ATTACCCATTAAATCAGTGTGTCTGGGGTTAGGAGCAGGCCTCAATATGTT
TAATCATTCTCCAGATAATCCCAATACTGTAAAGTTTGTGAAACACTTGTC
AGATAATTCAATTATGAAGGCTGTGGAAGGTGTTTCAGTAGGATCTAATTG
GTTAATGTTATGACTTAATTAATTTGAATCAAAAAACAAAATGAAAAAGCT
TTATATTTCTAAGTCAAATAAGACATAAGTTGGTCTAAGGTTGAGATAAAA
TTTTTAAATGTATGATTGAATTTTGAAAATCATAAATATTTAAATATCTAA
AGTTCAGATCAGAACATTGCGAAGCTACTTTCCCCAATCAACAACACCCCT
TCAGGATTTAAAAACCAAGGGGGACACTGGATCACCTAGTGTTTCACAAGC
```

FIG. 8-188

```
AGGTACCTTCTGCTGTAGGAGAGAGAGAACTAAAGTTCTGAAAGACCTGTT
GCTTTTCACCAGGAAGTTTTACTGGGCATCTCCTGAGCCTAGGCAATAGCT
GTAGGGTGACTTCTGGAGCCATCCCCGTTTCCCCGCCCCCCAAAAGAAGCG
GAGATTTAACGGGGACGTGCGGCCAGAGCTGGGGAAATGGGCCCGCGAGCC
AGGCCGGCGCTTCTCCTCCTGATGCTTTTGCAGACCGCGGTCCTGCAGGGG
CGCTTGCTGCGTGAGTCCGAGGGCTGCGGGCGAACTAGGGGCGCGGCGGGG
GTGGAAAAATCGAAACTAGCTTTTTCTTTGCGCTTGGGAGTTTGCTAACTT
TGGAGGACCTGCTCAACCCTATCCGCAAGCCCCTCTCCCTACTTTCTGCGT
CCAGACCCCGTGAGGGAGTGCCTACCACTGAACTGCAGATAGGGGTCCCTC
GCCCCAGGACCTGCCCCCTCCCCGGCTGTCCCGGCTCTGCGGAGTGACTT
TTGGAACCGCCCACTCCCTTCCCCCAACTAGAATGCTTTTAAATAAATCTC
GTAGTTCCTCACTTGAGCTGAGCTAAGCCTGGGGCTCCTTGAACCTGGAAC
TCGGGTTTATTTCCAATGTCAGCTGTGCAGTTTTTTCCCCAGTCATCTCCA
AACAGGAAGTTCTTCCCTGAGTGCTTGCCGAGAAGGCTGAGCAAACCCACA
GCAGGATCCGCACGGGGTTTCCACCTCAGAACGAATGCGTTGGGCGGTGGG
GGCGCGAAAGAGTGGCGTTGGGGATCTGAATTCTTCACCATTCCACCCACT
TTTGGTGAGACCTGGGGTGGAGGTCTCTAGGGTGGGAGGCTCCTGAGAGAG
GCCTACCTCGGGCCTTTCCCCACTCTTGGCAATTGTTCTTTTGCCTGGAAA
ATTAAGTATATGTTAGTTTTGAACGTTTGAACTGAACAATTCTCTTTTCGG
CTAGGCTTTATTGATTTGCAATGTGCTGTGTAATTAAGAGGCCTCTCTACA
AAGTACTGATAATGAACATGTAAGCAATGCACTCACTTCTAAGTTACATTC
ATATCTGATCTTATTTGATTTTCACTAGGCATAGGGAGGTAGGAGCTAATA
ATACGTTTATTTTACTAGAAGTTAACTGGAATTCAGATTATATAACTCTTT
TCAGGTTACAAAGAACATAAATAATCTGGTTTTCTGATGTTATTTCAAGTA
CTACAGCTGCTTCTAATCTTAGTTGACAGTGATTTTGCCCTGTAGTGTAGC
ACAGTGTTCTGTGGGTCACACGCCGGCCTCAGCACAGCACTTTGAGTTTTG
GTACTACGTGTATCCACATTTTACACATGACAAGAATGAGGCATGGCACGG
CCTGCTTCCTGGCAAATTTATTCAATGGTACACTGGGCTTTGGTGGCAGAG
CTCATGTCTCCACTTCATAGCTATGATTCTTAAACATCACACTGCATTAGA
GGTTGAATAATAAAATTTCATGTTGAGCAGAAATATTCATTGTTTACAAGT
GTAAATGAGTCCCAGCCATGTGTTGCACTGTTCAAGCCCCAAGGGAGAGAG
CAGGGAAACAAGTCTTTACCCTTTGATATTTTGCATTCTAGTGGGAGAGAT
GACAATAAGCAAATGAGCAGAAAGATATACAACATCAGGAAATCATGGGTG
TTGTGAGAAGCAGAGAAGTCAGGGCAAGTCACTCTGGGGCTGACACTTGAG
CAGAGACATGAAGGAAATAAGAATGATATTGACTGGGAGCAGTATTTCCCA
GGCAAACTGAGTGGGCCTGGCAAGTTGGATTAAAAAGCGGGTTTTCTCAGC
ACTACTCATGTGTGTGTGTGGGGGGGGGGGCGGCGTGGGGGTGGGAAG
GGGGACTACCATCTGCATGTAGGATGTCTAGCAGTATCCTGTCCTCCCTAC
TCACTAGGTGCTAGGAGCACTCCCCCAGTCTTGACAACCAAAAATGTCTCT
AAACTTTGCCACATGTCACCTAGTAGACAAACTCCTGGTTAAGAAGCTCGG
GTTGAAAAAATAAACAAGTAGTGCTGGGGAGTAGAGGCCAAGAAGTAGGT
AATGGGCTCAGAAGAGGAGCCACAAACAAGGTTGTGCAGGCGCCTGTAGGC
TGTGGTGTGAATTCTAGCCAAGGAGTAACAGTGATCTGTCACAGGCTTTTA
AAAGATTGCTCTGGCTGCTATGTGGAAAGCAGAATGAAGGGAGCAACAGTA
AAAGCAGGGAGCCCAGCCAGGAAGCTGTTACACAGTCCAGGCAAGAGGTAG
TGGAGTGGGCTGGGTGGGAACAGAAAAGGGAGTGACAAACCATTGTCTCCT
```

FIG. 8-189

```
GAATATATTCTGAAGGAAGTTGCTGAAGGATTCTATGTTGTGTGAGAGAAA
GAGAAGAATTGGCTGGGTGTAGTAGCTCATGCCAAGGAGGAGGCCAAGGAG
AGCAGATTCCTGAGCTCAGGAGTTCAAGACCAGCCTGGGCAACACAGCAAA
ACCCCTTCTCTACAAAAAATACAAAAATTAGCTGGGTGTGGTGGCATGCAC
CTGTGATCCTAGCTACTCGGGAGGCTGAGGTGGAGGGTATTGCTTGAGCCC
AGGAAGTTGAGGCTGCAGTGAGCCATGACTGTGCCACTGTACTTCAGCCTA
GGTGACAGAGCAAGACCCTGTCTCCCCTGACCCCCTGAAAAAGAGAAGAGT
TAAAGTTGACTTTGTTCTTTATTTTAATTTTATTGGCCTGAGCAGTGGGGT
AATTGGCAATGCCATTTCTGAGATGGTGAAGGCAGAGGAAAGAGCAGTTTG
GGGTAAATCAAGGATCTGCATTTGGGACATGTTAAGTTTGAGATTCCAGTC
AGGCTTCCAAGTGGTGAGGCCACATAGGCAGTTCAGTGTAAGAATTCAGGA
CCAAGGCTGGGCACGGTGGCTCACTTCTGTAATCCCAGCACTTTGGTGGCT
GAGGCAGGTAGATCATTTGAGGTCAGGAGTTTGAGACAAGCTTGGCCAACA
TGGTGAAACCCCATGTCTACTAAAAATACAAAAATTAGCCTGGTGTGGTGG
CGCACGCCTATAGTCCCAGGTTTTCAGGAGGCTTAGGTAGGAGAATCCCTT
GAACCCAGGAGGTGCAGGTTGCAGTGAGCTGAGATTGTGCCACTGCACTCC
AGCCTGGGTGATAGAGTGAGACTCTGTCTCAAAAAAAAAAAAAAAAAAAAA
AAAAAAAACTGAAGGAATTATTCCTCAGGATTTGGGTCTAATTTGCCCTGA
GCACCAACTCCTGAGTTCAACTACCATGGCTAGACACACCTTAACATTTTC
TAGAATCCACCAGCTTTAGTGGAGTCTGTCTAATCATGAGTATTGGAATAG
GATCTGGGGGCAGTGAGGGGTGGCAGCCACGTGTGGCAGAGAAAAGCACA
CAAGGAAAGAGCACCCAGGACTGTCATATGGAAGAAAGACAGGACTGCAAC
TCACCCTTCACAAAATGAGGACCAGACACAGCTGATGGTATGAGTTGATGC
AGGTGTGTGGAGCCTCAACATCCTGCTCCCCTCCTACTACACATGGTTAAG
GCCTGTTGCTCTGTCTCCAGGTTCACACTCTCTGCACTACCTCTTCATGGG
TGCCTCAGAGCAGGACCTTGGTCTTTCCTTGTTTGAAGCTTTGGGCTACGT
GGATGACCAGCTGTTCGTGTTCTATGATCATGAGAGTCGCCGTGTGGAGCC
CCGAACTCCATGGGTTTCCAGTAGAATTTCAAGCCAGATGTGGCTGCAGCT
GAGTCAGAGTCTGAAAGGGTGGGATCACATGTTCACTGTTGACTTCTGGAC
TATTATGGAAAATCACAACCACAGCAAGGGTATGTGGAGAGGGGGCCTCAC
CTTCCTGAGGTTGTCAGAGCTTTTCATCTTTTCATGCATCTTGAAGGAAAC
AGCTGGAAGTCTGAGGTCTTGTGGGAGCAGGGAAGAGGGAAGGAATTTGCT
TCCTGAGATCATTTGGTCCTTGGGGATGGTGGAAATAGGGACCTATTCCTT
TGGTTGCAGTTAACAAGGCTGGGGATTTTTCCAGAGTCCCACACCCTGCAG
GTCATCCTGGGCTGTGAAATGCAAGAAGACAACAGTACCGAGGGCTACTGG
AAGTACGGGTATGATGGGCAGGACCACCTTGAATTCTGCCCTGACACACTG
GATTGGAGAGCAGCAGAACCCAGGGCCTGGCCCACCAAGCTGGAGTGGGAA
AGGCACAAGATTCGGGCCAGGCAGAACAGGGCCTACCTGGAGAGGGACTGC
CCTGCACAGCTGCAGCAGTTGCTGGAGCTGGGGAGAGGTGTTTTGGACCAA
CAAGGTATGGTGGAAACACACTTCTGCCCCTATACTCTAGTGGCAGAGTGG
AGGAGGTTGCAGGGCACGGAATCCCTGGTTGGAGTTTCAGAGGTGGCTGAG
GCTGTGTGCCTCTCCAAATTCTGGGAAGGGACTTTCTCAATCCTAGAGTCT
CTACCTTATAATTGAGATGTATGAGACAGCCACAAGTCATGGGTTTAATTT
CTTTTCTCCATGCATATGGCTCAAAGGGAAGTGTCTATGGCCCTTGCTTTT
TATTTAACCAATAATCTTTTGTATATTTATACCTGTTAAAAATTCAGAAAT
GTCAAGGCCGGGCACGGTGGCTCACCCCTGTAATCCCAGCACTTTGGGAGG
```

FIG. 8-190

```
CCGAGGCGGGTGGTCACAAGGTCAGGAGTTTGAGACCAGCCTGACCAACAT
GGTGAAACCCGTCTCTAAAAAAATACAAAAATTAGCTGGTCACAGTCATGC
GCACCTGTAGTCCCAGCTAATTGGAAGGCTGAGGCAGGAGCATCGCTTGAA
CCTGGGAAGCGGAAGTTGCACTGAGCCAAGATCGCGCCACTGCACTCCAGC
CTAGGCAGCAGAGTGAGACTCCATCTTAAAAAAAAAAAAAAAAAAAAAAAG
AGAATTCAGAGATCTCAGCTATCATATGAATACCAGGACAAAATATCAAGT
GAGGCCACTTATCAGAGTAGAAGAATCCTTTAGGTTAAAAGTTTCTTTCAT
AGAACATAGCAATAATCACTGAAGCTACCTATCTTACAAGTCCGCTTCTTA
TAACAATGCCTCCTAGGTTGACCCAGGTGAAACTGACCATCTGTATTCAAT
CATTTTCAATGCACATAAAGGGCAATTTTATCTATCAGAACAAAGAACATG
GGTAACAGATATGTATATTTACATGTGAGGAGAACAAGCTGATCTGACTGC
TCTCCAAGTGACACTGTGTTAGAGTCCAATCTTAGGACACAAAATGGTGTC
TCTCCTGTAGCTTGTTTTTTTCTGAAAAGGGTATTTCCTTCCTCCAACCTA
TAGAAGGAAGTGAAAGTTCCAGTCTTCCTGGCAAGGGTAAACAGATCCCCT
CTCCTCATCCTTCCTCTTTCCTGTCAAGTGCCTCCTTTGGTGAAGGTGACA
CATCATGTGACCTCTTCAGTGACCACTCTACGGTGTCGGGCCTTGAACTAC
TACCCCCAGAACATCACCATGAAGTGGCTGAAGGATAAGCAGCCAATGGAT
GCCAAGGAGTTCGAACCTAAAGACGTATTGCCCAATGGGGATGGGACCTAC
CAGGGCTGGATAACCTTGGCTGTACCCCTGGGGAAGAGCAGAGATATACG
TGCCAGGTGGAGCACCCAGGCCTGGATCAGCCCCTCATTGTGATCTGGGGT
ATGTGACTGATGAGAGCCAGGAGCTGAGAAAATCTATTGGGGGTTGAGAGG
AGTGCCTGAGGAGGTAATTATGGCAGTGAGATGAGGATCTGCTCTTTGTTA
GGGGGTGGGCTGAGGGTGGCAATCAAAGGCTTTAACTTGCTTTTTCTGTTT
TAGAGCCCTCACCGTCTGGCACCCTAGTCATTGGAGTCATCAGTGGAATTG
CTGTTTTTGTCGTCATCTTGTTCATTGGAATTTTGTTCATAATATTAAGGA
AGAGGCAGGGTTCAAGTGAGTAGGAACAAGGGGGAAGTCTCTTAGTACCTC
TGCCCCAGGGCACAGTGGGAAGAGGGGCAGAGGGGATCTGGCATCCATGGG
AAGCATTTTCTCATTTATATTCTTTGGGGACACCAGCAGCTCCCTGGGAG
ACAGAAAATAATGGTTCTCCCCAGAATGAAAGTCTCTAATTCAACAAACAT
CTTCAGAGCACCTACTATTTTGCAAGAGCTGTTTAAGGTAGTACAGGGGCT
TTGAGGTTGAGAAGTCACTGTGGCTATTCTCAGAACCCAAATCTGGTAGGG
AATGAAATTGATAGCAAGTAAATGTAGTTAAAGAAGACCCCATGAGGTCCT
AAAGCAGGCAGGAAGCAAATGCTTAGGGTGTCAAAGGAAAGAATGATCACA
TTCAGCTGGGGATCAAGATAGCCTTCTGGATCTTGAAGGAGAAGCTGGATT
CCATTAGGTGAGGTTGAAGATGATGGGAGGTCTACACAGACGGAGCAACCA
TGCCAAGTAGGAGAGTATAAGGCATACTGGGAGATTAGAAATAATTACTGT
ACCTTAACCCTGAGTTTGCGTAGCTATCACTCACCAATTATGCATTTCTAC
CCCCTGAACATCTGTGGTGTAGGGAAAAGAGAATCAGAAAGAAGCCAGCTC
ATACAGAGTCCAAGGGTCTTTTGGGATATTGGGTTATGATCACTGGGGTGT
CATTGAAGGATCCTAAGAAAGGAGGACCACGATCTCCCTTATATGGTGAAT
GTGTTGTTAAGAAGTTAGATGAGAGGTGAGGAGACCAGTTAGAAAGCCAAT
AAGCATTTCCAGATGAGAGATAATGGTTCTTGAAATCCAATAGTGCCCAGG
TCTAAATTGAGATGGGTGAATGAGGAAAATAAGGAAGAGAGAAGAGGCAAG
ATGGTGCCTAGGTTTGTGATGCCTCTTTCCTGGGTCTCTTGTCTCCACAGG
AGGAGCCATGGGGCACTACGTCTTAGCTGAACGTGAGTGACACGCAGCCTG
CAGACTCACTGTGGGAAGGAGACAAAACTAGAGACTCAAAGAGGGAGTGCA
```

FIG. 8-191

```
TTTATGAGCTCTTCATGTTTCAGGAGAGAGTTGAACCTAAACATAGAAATT
GCCTGACGAACTCCTTGATTTTAGCCTTCTCTGTTCATTTCCTCAAAAAGA
TTTCCCCATTTAGGTTTCTGAGTTCCTGCATGCCGGTGATCCCTAGCTGTG
ACCTCTCCCCTGGAACTGTCTCTCATGAACCTCAAGCTGCATCTAGAGGCT
TCCTTCATTTCCTCCGTCACCTCAGAGACATACACCTATGTCATTTCATTT
CCTATTTTGGAAGAGGACTCCTTAAATTTGGGGGACTTACATGATTCATT
TTAACATCTGAGAAAAGCTTTGAACCCTGGGACGTGGCTAGTCATAACCTT
ACCAGATTTTTACACATGTATCTATGCATTTTCTGGACCCGTTCAACTTTT
CCTTTGAATCCTCTCTCTGTGTTACCCAGTAACTCATCTGTCACCAAGCCT
TGGGGATTCTTCCATCTGATTGTGATGTGAGTTGCACAGCTATGAAGGCTG
TACACTGCACGAATGGAAGAGGCACCTGTCCCAGAAAAAGCATCATGGCTA
TCTGTGGGTAGTATGATGGGTGTTTTTAGCAGGTAGGAGGCAAATATCTTG
AAAGGGGTTGTGAAGAGGTGTTTTTCTAATTGGCATGAAGGTGTCATACA
GATTTGCAAAGTTTAATGGTGCCTTCATTTGGGATGCTACTCTAGTATTCC
AGACCTGAAGAATCACAATAATTTTCTACCTGGTCTCTCCTTGTTCTGATA
ATGAAAATTATGATAAGGATGATAAAAGCACTTACTTCGTGTCCGACTCTT
CTGAGCACCTACTTACATGCATTACTGCATGCACTTCTTACAATAATTCTA
TGAGATAGGTACTATTATCCCCATTTCTTTTTTAAATGAAGAAAGTGAAGT
AGGCCGGGCACGGTGGCTCACGCCTGTAATCCCAGCACTTTGGGAGGCCAA
AGCGGGTGGATCACGAGGTCAGGAGATCGAGACCATCCTGGCTAACATGGT
GAAACCCCATCTCTAATAAAAATACAAAAAATTAGCTGGGCGTGGTGGCAG
ACGCCTGTAGTCCCAGCTACTCGGAAGGCTGAGGCAGGAGAATGGCATGAA
CCCAGGAGGCAGAGCTTGCAGTGAGCCGAGTTTGCGCCACTGCACTCCAGC
CTAGGTGACAGAGTGAGACTCCATCTCAAAAAAATAAAAATAAAAATAAAA
AAATGAAAAAAAAAGAAAGTGAAGTATAGAGTATCTCATAGTTTGTCAGT
GATAGAAACAGGTTTCAAACTCAGTCAATCTGACCGTTTGATACATCTCAG
ACACCACTACATTCAGTAGTTTAGATGCCTAGAATAAATAGAGAAGGAAGG
AGATGGCTCTTCTCTTGTCTCATTGTGTTTCTTCTGAGTGAGCTTGAATCA
CATGAAGGGGAACAGCAGAAAACAACCAACTGATCCTCAGCTGTCATGTTT
CCTTTAAAAGTCCCTGAAGGAAGGTCCTGGAATGTGACTCCCTTGCTCCTC
TGTTGCTCTCTTTGGCATTCATTTCTTTGGACCCTACGCAAGGACTGTAAT
TGGTGGGGACAGCTAGTGGCCCTGCTGGGCTTCACACACGGTGTCCTCCCT
AGGCCAGTGCCTCTGGAGTCAGAACTCTGGTGGTATTTCCCTCAATGAAGT
GGAGTAAGCTCTCTCATTTTGAGATGGTATAATGGAAGCCACCAAGTGGCT
TAGAGGATGCCCAGGTCCTTCCATGGAGCCACTGGGGTTCCGGTGCACATT
AAAAAAAAAATCTAACCAGGACATTCAGGAATTGCTAGATTCTGGGAAATC
AGTTCACCATGTTCAAAAGAGTCTTTTTTTTTTTTTGAGACTCTATTGCC
CAGGCTGGAGTGCAATGGCATGATCTCGGCTCACTGTAACCTCTGCCTCCC
AGGTTCAAGCGATTCTCCTGTCTCAGCCTCCCAAGTAGCTGGGATTACAGG
CGTGCACCACCATGCCCGGCTAATTTTTGTATTTTTAGTAGAGACAGGGTT
TCACCATGTTGGCCAGGCTGGTCTCGAACTCTCCTGACCTCGTGATCCGCC
TGCCTCGGCCTCCCAAAGTGCTGAGATTACAGGTGTGAGCCACCCTGCCCA
GCCGTCAAAAGAGTCTTAATATATATATCCAGATGGCATGTGTTTACTTTA
TGTTACTACATGCACTTGGCTGCATAAATGTGGTACAAGCATTCTGTCTTG
AAGGGCAGGTGCTTCAGGATACCATATACAGCTCAGAAGTTTCTTCTTTAG
GCATTAAATTTTAGCAAAGATATCTCATCTCTTCTTTTAAACCATTTTCTT
```

FIG. 8-192

```
TTTTTGTGGTTAGAAAAGTTATGTAGAAAAAAGTAAATGTGATTTACGCTC
ATTGTAGAAAAGCTATAAAATGAATACAATTAAAGCTGTTATTTAATTAGC
CAGTGAAAAACTATTAACAACTTGTCTATTACCTGTTAGTATTATTGTTGC
ATTAAAAATGCATATACTTTAATAAATGTATATTGTATTGTATACTGCATG
ATTTTATTGAAGTTCTTGTTCATCTTGTGTATATACTTAATCGCTTTGTCA
TTTTGGAGACATTTATTTTGCTTCTAATTTCTTTACATTTTGTCTTACGGA
ATATTTTCATTCAACTGTGGTAGCCGAATTAATCGTGTTTCTTCACTCTAG
GGACATTGTCGTCTAAGTTGTAAGACATTGGTTATTTTACCAGCAAACCAT
TCTGAAAGCATATGACAAATTATTTCTCTCTTAATATCTTACTATACTGAA
AGCAGACTGCTATAAGGCTTCACTTACTCTTCTACCTCATAAGGAATATGT
TACAATTAATTTATTAGGTAAGCATTTGTTTTATATTGGTTTTATTTCACC
TGGGCTGAGATTTCAAGAAACACCCCAGTCTTCACAGTAACACATTTCACT
AACACATTTACTAAACATCAGCAACTGTGGCCTGTTAATTTTTTTAATAGA
AATTTTAAGTCCTCATTTTCTTTCGGTGTTTTTTAAGCTTAATTTTTCTGG
CTTTATTCATAAATTCTTAAGGTCAACTACATTTGAAAAATCAAAGACCTG
CATTTTAAATTCTTATTCACCTCTGGCAAAACCATTCACAAACCATGGTAG
TAAAGAGAAGGGTGACACCTGGTGGCCATAGGTAAATGTACCACGGTGGTC
CGGTGACCAGAGATGCAGCGCTGAGGGTTTTCCTGAAGGTAAAGGAATAAA
GAATGGGTGGAGGGGCGTGCACTGGAAATCACTTGTAGAGAAAAGCCCCTG
AAAATTTGAGAAAACAAACAAGAAACTACTTACCAGCTATTTGAATTGCTG
GAATCACAGGCCATTGCTGAGCTGCCTGAACTGGGAACACAACAGAAGGAA
AACAAACCACTCTGATAATCATTGAGTCAAGTACAGCAGGTGATTGAGGAC
TGCTGAGAGGTACAGGCCAAAATTCTTATGTTGTATTATAATAATGTCATC
TTATAATACTGTCAGTATTTTATAAAACATTCTTCACAAACTCACACACAT
TTAAAAACAAAACACTGTCTCTAAAATCCCCAAATTTTTCATAAACTCAGT
TTTAAACTAACTTTTTTTCAAACCACAATCTGATTTAACAATGACTATCAT
TTAAATATTTCTGACTTTCAAATTAAAGATTTTCACATGCAGGCTGATATT
TGTAATTGTGATTCTCTCTGTAGGCTTTGGGTATAATGTGTTCTTTTCCTT
TTTTGCATCAGCGATTAACTTCTACACTCTAACATGTAGAATGTTACTACA
ATATTAAAGTATTTTGTATGACAATTTTATTTGAAAGCCTAGGATGCGTTG
ACATCCTGCATGCATTTATTACTTGATATGCATGCATTCTGGTATCTCAAG
CATTCTATTTCTGAGTAATTGTTTAAGGTGTAGAAGAGATAGATATGGTGG
ATTTGGAGTTGATACTTATATATTTTCTATTTCTTGGATGGATGAATTTGT
ACATTAAAAGTTTTCCATGGCAGAAATCTTTTCAAAAACTTTTTTTTTCCG
GGATGGATTGAAGGCCCTGATTTCACCACAATGCAATATATTAATGTAGCA
AAATTGTACTTGTACCCCATGAATATATATAATCTTAAGAAAATTTTTTA
GCCAATTATTATTACTTACTAGATATTAGGCTGTGTTCTGAATCTTAATTT
AATTCCTCCAAAGAATCTTATGAGGTAGGTAGGAGCTATTGCTGCTATTCT
GTTATGCTTATGTTGCTGTTATGAAACCAAGGCACAGAGAGGTTAGTTAAC
TTGCTGAAGAAAATGATGTGCTGGATTTTTATTCTAGCTATTCTGGAATAA
CAACTACACAACCTTATGTCTGAGCCAAGGAAACATACGGTGTGGCAACAG
TTACCATGTTTTTAGGAACAGCAGCACTCCTAATGTTTGCTGCAGGGAAAA
AGGAATCTCAGAATTTGCCTGATCCCTATAATTTTTTCCTAAATATTTTG
AAATATCTTTCAGATGTATTTAAAATTTAAGGATATTTTGTTCAGTTCAT
ACAGAATTTTTTTTTTTTCTCGAGATGGAGTCTCACTCTATCACCCAGGC
TGGAATGCAGTGGCATGATCTCGGCTCACTGCAACCTCTGCCTCCTGGGTT
```

FIG. 8-193

```
CAAGCAATTTTCCTGCCTCAGCCTCCCAAGTGGCTGAGACTACAGGCGCAT
GCCACCATGCACGGCTAATTTTTTTTGTATTTTTAGTAGAGATGGAGTTTC
ACCATGTTGGCCAGGCTGGTCTCGAACTCCTGACCTCAAATGATCCGCCCT
TTTTGGCCTCCCAAAGTGCTGGGATTACAGGCGTGAGCTACCGCGCCCAGC
CAAATTTCTAACTTGTTTTGTTGTTGTTGAGACAGGGTCTCAGTCTGACAC
CAAGGCTGGTGTGCAGTACTGCGATCACGGCTCACTGCAGTCTCGACCTCC
TGAGCTCAAGTGATCCTCCCACCTCAGCCTACTGAGTAGCTGGGACCACCA
CGCCTGGCTCATTTTTTCTATTATTTATTGAAACGGGTTCTGGCTATGTT
GCCCAGGTTGGTCTTGAACTCCGGAGCTCATGCGATCCACCCACCTCAGCG
TCCGAAAGGATTATCAGGAGTGAGCCACCGTGCCCGGCCAAATTTCTAACT
TTTGAATTGACATATTCATTTATTCTCTTTATCATTCAGGGAGAAATTTGG
GGATGGATAGCCTTGAAGCATCATCCACCAAGTTATTTTATACACCAGATT
TAGATACAAAGTATTTTTTTATTATTTAAAAAAATCAAATTCTAGCTTTTA
CTCTGAAGATTCTAAAAAGAATTTTGGAGTCTTTAATTCATACTTCAGGGG
CAGGGGAATAAGTACCAATATTCGTATAACTTTCAGTGCAAGTCACGTTAG
CTAACTGTAGTCTATTGAGTTAAATATCCTTGATTTATTCCTTAAAACTGA
GTCACTATGACGGCACTTTTTGTTTTTTTTTTCGAGACGGAGCTCGCCC
TGTCTCCCAGGCTGGAGTGCGGTGGTGCGATCTCGGCTCACTGCAATCTCC
GCCTCCCAGGTTCAAGCGATTCTCCTGCCCCAGCCTCCTGAGTAGCTGGGA
CTACAGGCACACACCACCACGCCCAGCTAATGTTTGTATTTTTAGTAGAGA
CAGGGTTTCATCATTTTGGTCAGGCTGGTCTTGAACTCCTGACCTCGTGAT
CAGCCTGCCTCGACCTCCCAAAGTGCTGGGATTACAGTCATGAGCCACTGC
ACCCGGCTGAATGGCACTTTCATAAAACAGTAAATAACCAACTTCACTACT
GCCCCCAAGAGTTTTACTATGTATATGAGGGCATCTGTTTTAAGTATGGGT
ATAATGTTACGGGTTTTTCTTTGTGTAAGTTTGGGTTCACAATTTCATCAT
TAAAACAAATGTAAAATACTTTGTGCTTTCTGTGTGCTATTAAGAAAGTAT
TCAAGGGAATTTTGAAAATCAAATTTAATTACTCTCATGTTTGTAAAATTT
TTGAAACAAATGTTTAAGAGAGGATAATGTTAGAAATTATCTTTCCAGCCA
GACCTGGTGGCTCACGCCAGTAATCCTAGCATTTTGGGAGGACAAGGTGGG
CAGATCACTTAAGCCCAGGAATTCAAGACCAGCCTGGACAACACAGGGAAA
GCCCATCTCTACAAAATATACAAAATTAGTGGCCGAGCGTGGTGGCTCACG
CCTGTAATCCCAGCACTTTGGGAGGCCGAGGCGGGCAGATCACCTGAGGTC
AGGAGTTCCAGACCAGCCTCAACATGGAGAAACCCCGTCTCTACTAAAAAT
ACAAAATTAGCTGGGCGTGGTGATGCATGCCTGTAATCCCAGCTACTCGGG
AGGCTGAGGCAGGAGAATTGCTTGAACCTGGGAGGTAGAGGTTGCGGTGAG
CCGAGATCCCGCCATTGCACTCCAGCCTGGGCAACAAGAGCGAAACTCCAT
CTCAAAAAACAAAACAAACAAATAAACAAAATTAGTCAGGTGTGGTTGTGC
ACACCTGTAGTCCCAGCTACTTGGGAGGCTGAGGTGGGAGGATCACTTGAG
CCCGGGGAAGTGTAGGCTACCATGAGCCATCATGGTGCCACTGTACTCCAG
TCTAGGAAAAAATAAACATTAAAAATTTTAAAATCTTAAAAAAGAAAAG
AAATTTTCTGTCCAGATATCTTTATTTTTAACAAATCGAAGTGTATTAATA
GTGTTTATGGGAGCGTGCCCACACAAGGACAGCAAGCCTAGGAAGTGCAAG
TCAAGAAAACTTTTTGTGAAATAATTTAAACTGAAAAGAAAAAGCAGAGAT
TTTTTTCTAGAAAAGTAAGGAGTGGAGGTAAAAAAAAAACACAGCAGAGAC
ACAGGTATGCTACGGAACCAAAGGTGTGCCAATGGTACTGACAGTTTAATT
CAGAAAAAAATGAATCAGAAAATGGATATTTTTAAATAAGTTAGGTTGCTG
```

FIG. 8-194

```
AAAAAGAGAAATGCAGTGAAGCCTTAGATGGGAGTGAGATAAATCAGCCAT
TGGCTAGAGGAGTTTCTTGCCCAAGACCAGTGGTGATGTCCCCAAATGCCT
GGAAACAACTGTTGTGACATTATAAAGCCCCCATAGTCTAAGTTGGGTGAG
ACTATACTTATGCATTTCTCACCTGTAATATAGCTTAAAAGTATTTCTAC
TCTGGGATTTCTTTACATTTTACTAAAGCGCAATTATATACTTAAAACTGA
TAGTGTATGCTGGGCTGCTAGTCATTCTCAACCCTGGCCAATTATCAGAAT
TGTTTGTTGAATATATAGGTGCCATATATAGGTGCATACACACACACACAC
ACACACATACACACACACACACACACACACACACCATATTTCATTCCTCAT
ATCGAATATTCTGAGAGAGTTAGTTTGTGGAGGGTAGTTCTGGACAATTTA
TATTTTCATAACACCTCTGGTTATTTTTTTTAAGTAGAGATGAAGACTTG
CTATGTTGCCCAAAATGGTCTTGAACTCCTGAGCTCAAGCGATTCTCCCAA
CTCAGCCTCCTGAAGTGCTGGGATTACAGCCGTGAGCCACTGCATTAACCT
CTGATTAATATCATAGATTAACCTCTGATTAATATCATAGATTTATTTGTT
TGAATGCTTCATGTATCCTCTCAACCACAACTTGTTTGCAGAGTTTTAATC
TGAAGGGCTTAGGTCTCTTGTTCAATGAATGAGTTTGATCTGATGGGTGAG
AGGAAGGTGAAATGGAAAGCGAACGAGAAGCCATACAGATTAGGCGAGTGA
GCCTAATCTCTCCCTAACCATAAGATTGAGTATGCCTGAATTCTTCGCAGA
GTGGAAGAATCCATTTTAAATATATATATCTACATGTACAGATCCTTTAAA
TATTTGTTCTGACATTCATTGTTTTGAGTCACTGTCATTGAGAAAAGTTT
AGAAAGGAGATATTAGGAGCAGGAAATAGAAAGTAAATAAAATATCAAAAT
AAAAATGGGGTTTTATAAATGATATAATAGGCAAAATAAAGGAAAGGCATC
CTAGACCTCTGGTTAAAATGAAGATGGCACTTGGCGAGATGTGTTCCAGGG
TAGTTCACATGATGTATGTTTTCAGAGAATTGTCATATTGCATATGCTGCT
ATATTTTTATTTTCATGAATTAAAAGGCATGTTGAGATTTCAGAGTTTTA
CTTATGATCTCAGACTCTGCATTTTTTCTCTGTAATGTTTGACATTTCTTC
CTAGCTAAGTCTCTAGTTATAAGGTCTGTGTTGTGGCATGTGGACAGTGAG
TGGAAGAACCTAAGAACTCAATTTGGGGCAGAAGAATGTAATCAATTATTT
CAGAAGTGATACAAACAATATGACATGTAGAGCATTCTGGCCTTTCCTGGG
TCTTTTTTCTCCATTCCTGGATTTCTTCTCTTCATGTGAGCAAGTCTGAGG
TTACTATATAATGTCTCTCACAGGCCACAGCCCCATTCTAAATATTCCCAA
TAGAAATTCATTTATTAACCAGAGAGTGGTGGGTGGGGTTGTTTTTGTTTT
TTAAACAAAAGTGGATCTTATGGGCATTCTGGAAAGCTCCCGCAGGAAGCT
AAGAATAAAATTTTGAATTGAGAAGTCCCTTTCTTCAAACCACATTCAGAC
CCAATTCTGCTATTCTATTTATTTTTCAAGGGGATTAGCCTTATTTTAACA
CCAATAATCTTATCACAAAAACCTCCCAGAGGAAGACCCTGTAGATTTTGT
AATGACCTTAATCAAGTATTAGCCCTACACTTCAATTAATCCCCAACTGTA
CAAAACGAATGTTCTTTTCTCTAAAGCTGTAGCAAGTTGAAAGGGGATTAA
AAACGGAGGGAAGGGAAGAGTGTTTGGAATTTCAGGCACAGCAAACAGGCA
CAGCAGACCAGGAAGAGCGTCCCGGGAAAACATATTATCCAGACTTAAGTT
TATATTCCCTGTCTCTCAGACTTTTGCAGAAAAATGAGTCATTCAACAA
ATATTTGAATCGAGATAGGGAAAGTGACGAGGAAGAAGTTTGCACTTATGA
GGTTTTAATTTGCAATTATTTGGCTACCTTTTTGCCTTCCCAAAACATAGG
GTCTTTAGGAGTGAAACTTCATAGCCAAACTTATACCTTGTCCAGCACAGA
GAAGGCCATCAAAATGCCTGGTTTAAATAAAAATATTAAAATGATTGGGAG
GGTAAATCCCTTGACCTATAAATCTGACCTCCTTTAAACATTATTTGTATG
TTCCCCAATAAACTATTCCGTAATTTATTAGTTAGCAAGTGGAAATAAAAA
```

FIG. 8-195

```
GAAATGTGGAATGGGGCTATGCTTAGCGTCATTAAGCTGACAGGAATACAG
CGCATTCAACTTGCAAACACCCTTCCACTCCCACAAAGAGCAAGCTGTCAC
TGGCCAATCAAAACAATGAACCATAATGAAACAGTTTTTCTTGCTCCACCC
ACTTGGTGACCAAATTTGAAAAAAAAAAAAAACCGCGCCAACTCATGTTGT
TTTCAATCAGGTCCGCCAAGTTTGTATTTAAGGAACTGTTTCAGTTCATAC
CTTCCACTGCGATAGGAATCATGTCTGGTCGCGGCAAAGGCGGAAAAGGCT
TGGGGAAGGGTGGTGCTAAGCGCCATCGTAAGGTGCTCCGGGATAACATCC
AGGGCATTACAAAACCGGCTATTCGCCGTTTGGCTCGGCGCGGTGGCGTCA
AGCGCATTTCCGGTCTTATCTATGAGGAGACTCGAGGTGTGCTTAAGGTTT
TCTTAGAGAACGTTATTCGAGACGCCGTCACCTATACGGAGCACGCCAAGC
GCAAAACTGTCACAGCCATGGATGTAGTATATGCCCTAAAACGTCAGGGGC
GCACTCTGTATGGCTTCGGCGGCTGAATCTAAGAATACGCGGTCTCCTGAG
AACTTCAAAAAACAAAAACAAAAAAACCCAAAGGCCCTTTTCAGGGCCGCT
CACAAAGTCGTTTAAAGAGCTGAAATGCGTTGCGAGAATGAGTTTGGATGA
CAGAAATAACCGTGACATCCTGCATAAGAATGAATTGTGTTTGCCATGACC
GGCCACACTGTGACAAAATTTCAAAGCATAAAGTAGGCATAGAGAGGTAAG
CGCTAATAAAGTGATTGGCTCCACAAAAAGCATTTTGCTGGGCGCAGTGGC
TCACGACTGTAATCCCAGCACTTTGGGAGGCCAAAGCTAGTGTATCACTTG
AGATCAAGAATCCGAGACCAGCCTGGCCAAAATGGTGAAACCCCCTCTACC
AAAAAAAATACAAAACTTAGCCGGGCGTGGTGGTCTGCACCTGTAGGCCCA
GCTAGCCCGGAAGCAGAGATTGCAGTGAGCCGAGATCGCGCCACTCCCCTC
CAGCCTGGGAGACAGAGAGAGACTCCTCAAAAAAAAAAAAAAAAAAAAAAA
AAAAAATTATGTATTTTAGAGCATTCTAAGAATGGTACTTTGGACTTAACC
GAAGGGCTGGAGGCGCGTGTTGAACAAAGGTTATCACCTTTTGGCTCATGC
GGCACACAGCTATGTAAATAAAGCATCTTTAGGGACAAGCTCTCATTTGCG
GAGGGTTCTATGGCTGTTGTCCTATTGGCCAAAACAAAGTGGTCTAAGTCC
GGGCGCGGTGGCTCACGCCTGTATTCCCAGCAGTTTGGTAGGCCAAGGTGG
GTGGATCACGAGGTCTGGCGTTCAAGACCAGCCTGGCCAAGATGGTGAAAC
CCCGTCTACTAAAAATACAAAAATTAGCCGGGCGTGGTGGCGGGCACCTGT
AATCCCAGCTACGTGGGAGGCTGAGCCAGAGAACTGCTTGAACCCAGGAGG
CAGAGGTTGCAGTGAACCGAGATTGTGCCACTGCACTCTAGCCTGGGTGAC
AGAGCGAGGCTCCATCCAAAACAAAACAAAACAAAAAAGTGGTCTAATAAT
CCCCAGAACTGGAGGAAGAACCATAACTTATTGATTTTGTTTTTAACCTTA
TGTATGCCAGGCATGCTAGCCTTGTATACATACAAGGCTAGAGGAGCAAAG
GTGCAGGAAGCCATCTTGAGGGAGTCCCATATTATTGAGAGACCGGCCAGC
TGCTGGGAGAGGCTAGTTGTTCATCCTCACTGTATGTGATGAGAATCTGGT
GACAGTCCATTGCTGGGCACAGCATTTAGGCAAAATGGCTCTCTGCTATGT
CAGGCAAGTGAGGCATATTTTTGCACAATCCTAGTAATTCCGAACTCATTG
GGAAACAATGGCAATTACATCCAAGCAAGGAAAGGTCTGTGGTTGATTTTA
TCTATACAAATTTAAAACATAATGTTTACAACCTTTCATTATAGGACACAA
TTTTTAAAAAGATGCCAAACTATACAAATAAGTTCAGAAAAGTGAGGTACT
ATTGAACCGTCTGGAAAACATAAATGTATGTGAAATAATGCAATGCATAGT
TTTGCAGGGGACTTTGTTCAAAGTTTCTCGAAATACCATGGTCCAAAGTAG
ACTAACATTAGCATTGGTTATTTATGATGATCAGTAAGAATACTAAATCAA
AAATCAAAGGAAAATTAAACTATGTCTGTTTAAAGAGAAACGTAGTTTACC
TCAGACTGAGAGTTAAAACAAGTTTGTGATTCAGGAAGGTGGAATTCAGAA
```

FIG. 8-196
```
CCTAATTGGGCAGCCTCCAACATTTCCATTAAGGTTTGGATTCTTAAAATT
TTTCAGTCTTCGGTATGCTCTGGTAGTCTGATGAAACTTACAGATTCTTTT
CATAAATAAGATACTTAAAGTAATTCATAGGGTTACAATTGTATTAGACCA
ATAATATTAAAATAATTATCAAACCACTTGACCGTAATATGTGTGTTTTTG
TTGATATACCTAATAGTACTTCGGAAATAAGCAAGCACGATTTCCAGATTC
TTGCAACAACTATAACCTACAAATTTGTTATTTCTATCAGTCACACACAAT
GGAAGAAAATTCTAAATTTCAGCTACAGGATAATGAATAGATGAAAAACAA
CAACAACAACAACAAAAAAACTCCCCTAATCCATATTCTGGGACACCT
TGATTCCTATTTATTGATCCCTTGAAGTCAGTGGATAGCATATTAAGAAAC
AATAGTTACAATGACACCACAGAAAGACTAGAATGTAGTACTTGTGTTAAA
AAAAAAAAAAGTATCAGCAAGTTATGTTTGGATGCCAAATTGCTCTCCACT
TCCCTTCCCTGACACTGGCATTTCCAGAACTTAGATGCTCTTACATGTAAA
AGCCTCCTCTAGTGCACCATCGAGCTTTTCAGGATTGGACATCAGACTTTT
TAGTTCCTGGACCTCTAGATATACGGCAGTCTCTGACAAGAAGCCCTTTTT
CTGTTTTAACTTTTTTTTTTTTAAGTTTTGAGACAACGTCTGACTCGCTG
TCACCCAGGCTGGAGTGAGGTAGCACCATCATAGCTCACTGTATCCTTAAA
CGCCTGGGTGCAGGGACTAAGGGAGCGTGCCAACCATGCTTGACTAATTTA
CTTTTTTGTAAAACCAGTAGTCTCCAACCTTTTTGACACAAGAGACCGTTT
TGTGTAAGACAATTATACCACGGACCAGGGGGTGCAGGGGCTGGGAGCAAT
GATTTCCGGACTAAAACTGCTCCAACCTCAGATCATCAGGCATTAGATTGT
CACAAGGAGCCTGAAACCTAGATCCCTTGCATGTGCCATTCACAATACAGT
TTGAGCTTATGAGAATCTATCTAATGCTGCAGCTAACCTGACAGGCGGTGG
AGCTCAGTTGGTTAATGTTCGCTCACCCCTCAGCTGTGCGGCTCAATTCAT
AACGTGCCATGGACAGGGACCGGTTACCGGTCGGTGGCCGGGGAAATGAGG
ACCCCTGGTATAGATGGTAGTCTGGCTATGTTGCCCAGGATGGTCTTGAAG
CCTGGCCTGAATTAATTCTCCAATCTCAAGCCTTTTCAACTCAGCTGCATC
ACAACTTAAACCTATAGATAACTGTCACAGAAACTTGTTTCCAGTGTTACG
CCATCTTAAAATAATGTGGGTGGCTCTTAAAAGAGCCTTTGGGTTCTTTCC
AAATTGGCCTCCCGGAAAGCTCTTTACTTCTTAGATGTGGCCTTTCTAACA
TTAACTTCATGATGTTGGGTCAATTTTGACTTCGAAGCCCTTGCCTTCACT
GGGCTCTTCTGCTGTTGCTTACCCTTGGCTCCTTTAGCCTTTCTCCCGCTC
CTAACAGTTTTAGGAGTTGTCGCTCTCGGCTTCTTGGCTCTCTTATTGGTT
TTAGCAGTCTTTGGTGACTTGGAGTCCCTGGATAAAACCAGCTTCTTGGTC
TTGGCAGAAACTGACTTTTTAGCCTTGCTTCTGGTAGATTTAGGAATCACC
TTCTTACTAAGCTTAAAGGAACCGGAAGCACCAGTACCCCTGGTTTGCACC
AGGATTCCCTTGTTCACTAAGCTCTTGAGGGACAGTTTGATGCGGCTGTTA
TTCTTCTCTACGTCGTAGCCAGCAGCGGCCAATGCCTTCTTGAGCGCAACC
AAAGACATACCTACTCGTTCCTGTGACACTGAAAGGGCCTCGGTGATCAAC
TTGGACACAGAGAGGTTCGGCACTTTGCGACTTGCACTTATCAAGCCAGCC
GGCTTCCTCCCTCGCTTCTTGGTTGGAAGTTTCTCCATAGCGGCTACACCA
GCACTGGCAGAAGCTGCAGGCACGGTTTCAGACATAACAACAGAGAAACGC
AAGATGTAATAACCAGCGAAAAGCATGAAACACCCGGGCGGCCTCGGGGCC
TTATATAGGGTAGGGCGCGCTGTGATTGGTGCATCACCTAGGCACCGCCCC
CGCCCCTTGGAGGAGGAGTATTTGTGTTTGTTTTACCCGGAAAAGTTGAGT
ATAACAAAACCCCTCTTTACAGAATCTCCCAGGGTCTAGTGCTGAATAATC
TGCGGAAATTCATATTTGACATGACTTTTCTCTTTTTAATGAAAAATGACC
```

FIG. 8-197

```
CTGGATGCCAAAACTATTCGAGAAAGCCCTCGATTTTCAATCAAATTCACG
GAGAGGAACAAAACTTCCCCTTTTCCTTGTAAATTAATAAGTAATCTTTGG
CAGAAGACTTATTTCATCTCTTCAGAGTGGTCTTCCAAATGGATAGCTTCA
AATCGGTAGAGGAAAGAAATTATTCACGCCATGATTTTTATTTAAAATTAT
TTATATATGTGAGGGAAGTAACACAGATCTCTTAGCTGTCTAATTGCGGAG
TCAGAAGATGCTTATAGAATTGTCAAAAGACTGCAGAGGATGTCTTTATTT
AGGCATGTGCAATCTAATAAATCATAATCCACAGGAACATGGGTTGTCTGT
AATTAAAGGTGCTCCCAAGTCCCTGTAGCTTTATAGAGGACTCTCAAGGAT
GGGGTAATATCAAGATCTCACACATTATGTAAGATTGGCCATAATCAGGCC
ACTCTCATGACCGGTGTCCTCAACTGAGTTTTGCTTCTGGTTTCATTAATT
GAAGTCCCCTCTATCCCCCTGCCCACCCCTACATCCCCAGATAAACAGACA
CAGTCCCTCCCCTAAATTAACTATAAAACATGAGGTAGGAACCCTAGACTC
AAGAACCTACTAGAAACTACAGACCCCATGTCTAACAAGACTGGGCGGGTT
GGCTGGGCGCAGTGATTCATGCCTGTAATTACAGCACTTCGGAAGGCTGGA
GGCCAGGAGTTCAAGACTAGGTTGGCCTGGTCCCTACTGAAAAAAAAAAAA
ATTAGCTGGGTGTGGTGGCACATGCCTGCAGTCCCAGCTTCTGGGTAGACT
GAAGAGGATCACTTAGAGCCCAGGAGCTTGAGGTCGCAGCTACTGCACTCC
AGCCTGGGCAGACCCTCATCTCTGAATTGCTTAATTAATTAACTGAGCTGG
CAGATTTGGCTGCATAGCTGTGGGGAAAGGGTTGTTGGAATAATGTCCAGT
GTGCTCCCCTGAGCTTCTACTGGAACAGGTCTTTGTGAGAGGCCTGGAGAT
AAGAGCTTGCTCACAAAGGCTGAGGCCTTTCTGGGATGCTGAATGAGTTTA
GTGTGGCCAGAGCATAGGGTCTCAGCAAAGGAAAACTCCATAAGGGCCATT
TGTGAAGATCCCCAAATACTTGTGTGAAACATTTGGTAGATATTAGAAGTT
TTGTTTTGGTTTGGTTTGAGACAGAGTTTTGCTCTTGTTGCCCAGGCTGGA
GTGCAATGGTGTGATCTTGGCTCAGTGCAACCTCCACCTCCCAGGTTCAGG
CAATTCTCCTGCCTCAGCCTCCCAATTAGCTGGGATTATAGGCGCCCACCA
CCATGCCTGGCTAATTTTTTGTATTTTTAGTAGAGATGGGGTTTCATCATG
TTGGCCAGGCTAGTCTCGAACTCCCCACCTCAAGTGATCTGCCCGCCTCTG
CCTCCAAAGTGCTGGGAATACATGCGTGAGCCGCCGCGCCCGGCAGACATT
GGAAGTTTTTAAGCAGAGAATTTGTTGTATTGTTGTAGTTGTCTTGGGTTT
AGATTTATTGCATAAACAATCATTTTTGAGAAGGGCCCACAGTCAGAAGTT
GGGAGTCTGTTGCAATAGTCTCAGAAGAATGGCAAAGACCTTGCCTAAGGG
GACAGTGTGGTAAAGGAGAGAGTCTACATTTGAAATATTTCTGAAACAAAA
GCCAAAAGATAAGACTTCAAACTTCTGATTGCAAAGTGAGATAGAAAAGTT
TCTTTCTCTCTGTCTCTCTGTTATACCCATACACACACACATATGCACAAA
CACCTGAAAGAAAAAAAAATTCAGGGAACAGGCCAGGTAGGGTGGCTCATG
CCTATAATCCCATAAATTTGGGAGGCTGAGGCTAGTGGATCACTAGAGCCC
AGGAGTTCACAAGGCCAGCCTAAGCACATAGCAAGACCCTGTCTCTACAAT
TAAAAAATTACCCGGGTGTGGTGGCACGTACCTGTGGTCCCAGTTACTCAA
AAGGCTGAGGTGGGAGAATCACTTGGGCCCAGGAGGTCAAGGCTGCAGTGA
GCATGATTGTGCCACTGCACTTCAGCCTGGGCAAGAGCGAGACCCTGTCTC
AAAAAAAAAAAATTTTTTTTTTTTCCAGAAAACAATACTATCTTAAGCA
CCAGCACTTTAGTATATTCTACTGTGGACTAGTTCATTTTTAAAAGAACAC
TAGGTTGGAAATCATGAGATTGATTCCACAACTCACTAAAGCACCGTGTCA
CTCAGTTTGGAAAATATTTCTCCTTAGAGAGATTACAGGTGCATCTTTCTG
AGCACCTGTATGTTTTTACATTTGTTTGGCTTCTCTGACCTTTGATAATTT
```

FIG. 8-198

```
CTGAGTGTTGTACTATTAAATATTAGTGGCTAGGGGTCAAATTGTGGATCA
GGTTGATCCTTATATTTACAAGTTGACAGATACGTTACTCCATTGCTTTAA
AACTAACACAGAATTAGAGAATTTAGAAAATTCTTACATTCCATAATTTAA
GACCCAGAAAAAAAAGATTCATATTTTGCATTAGATAGCTAAAATGGTACC
ATAAAAACAAATGATATCCACATATATATAGTATATAGTGCTTCTTCTGTG
CCAGTCACTATCCTAAGTTTTTCTCTCCCTTCCCCAAAAATGTAGGAATTA
ACTTTATAGATGAAGAAACTGAGGCACAGGAATGTCACATGACTTGCCCAA
AGGAAATTCAGTCTTCCTTTTTCAATTCTTTTTTCTTTTTACTTTGCTGCA
GGGTCTCGCTGTGTTGCCCAGGATGCTCTTGAACTCCCGGACTCAAGCGAT
CCTCCTTCTTCAGCCTCTCAAAGTGCTGGGATTACAGGCATGAGCCACTGC
GCCCAGTCAGGAAATTCAGTCTTCTAAACATTCATTATTGAAATAATATTT
CCATAAACATTTTCTTAGATAAACTTTGGCATCTCTAACTTCTAAGTAGCA
AAGTCATGGAAACAGTCACAGAGAAAATAACTTTATTTTAAAAATAATAAA
TTCTTATCTCCGGTGATAAGAAAAGTATACAGCCCATTTTTTAAAGTATTA
ATTTTACATTCTAATTTGGTTTTTTTAATGTTTACCATATATTTCTCTTTC
TACATATGTGTGTGAGTGAATAAAATAAAGGCATCTACAGATTTTTACATG
TTCAGTGAGATTAGCAGGGTTTCACTTGACAGCACTCTTACCATACTCACT
TCTTGGCTTTTCCTGATATCTAACATTTTTAAAATGAGTAGTCCCTTTTCA
TATGATTCTTCCTTTTTCAAGCACTATTTTTGAACTTTATATTTGATTGGC
AATAATTTTTACAGACATTATTTTACGATTAACTTTAACTCTGTTCAAATG
ATTTCTTCATTTTCAAGTATTTTATTTGAACTGCTTTTTTTGGTTCAACTA
CTGAGTATTTAATTTGTCTGTTTTGTAGAAAGGGTATGTAGATAATTCCAT
GTTTTGTAAAAGTTGTCTCTAAAAATCTAACAAGTGTAAGTACGATGCTAT
TACAGGGCTGAGAGACACAGAAAAAACACACACACACACACAAAATTTTTT
TTTAAGTATTACTTGGTCTCTAAACTAAAGAATTTACCATCTATTTTGGGA
GATGAAATCCAAACATAAGCAATGACAACAATTATTATGTGCTTAAATCAA
TGTCCAAGACAATAATTGACCCCAAGGCAGGGAAATCACTGAGAGAGTATA
GCAGAGAAGGTGTCCTCTCTGTTCAGATGAGCCTGAATAATTTGTTCAGTA
GGTTTCTGCTACTCATTTATAAACTGCACATCTTCTGTAGTCCTGGAAAAT
GTCTAAGAGGAGAGAGGAACTAAGATCAGGGCCACCATTTAATTAGGAAGT
TCTGGGAGTACCTGACCCAGAAGAAAGATCAGCATAGCTGAAAATCACCCA
TAGGAGAAACATCTAGGTAATCTTATTTCTGTTCCACCTGACATTTCAACC
TCTCTTTTCAGCTATAAGTATATAAGTACTTATATGTAAGTAAAGAAATTT
ACCCACATCATGTTGTTTTTATTCAATGCTTAACATGTATAATGCTAACA
ACACAGACTTGATGTCCAAAACATTTCTATGAACAGCTCATTACTGGATGA
CTGAAATAATTTTTCCAAGCCACGTGGAGGTTAATGAGTCAGTTTTTGAAA
GCAAGGAGAGAAAAACATTAGAATTTAAGGTGACGTTTCTGTTGCGTTGTA
ATCCAGAATACAGAATAGTCAGAGAAAAGCAGAAAGTCTTTCTTCTTAAAT
TTTCTGAAAACCAAGGTGTGCATTAAAATGGTACATGCCTACTTCCCTTTC
CCTTTACCCTTTTTTCCTGCATGGAACATAGATATGACCCCTAGACATGCT
GCAGATGACCATGAGGTTGAAAGATACATGGAAGATGGTTAACACAGGATG
ATAGAAGAGACCTGCATACTTGGGCAGCCTAGACAGCTCCTGCCAGCCCCC
AACAAAACAGCCTAGCCTTCTTGCCAATCAAGAAAAAAAATCCCTTCTGGT
AACCCACTGTAAGTGAATTTCTGTAAATGTGGCCCAATGTATCCATAATTG
ATATACAAATATTAGTTTAGTGGGTAGCACCTCTCCATGAGCATGTCGACT
TCATGAGACTGAGATTTTTGACTGTCATGTGCAGTTGTCCCATTACAGTGC
```

FIG. 8-199

```
CTGGTGCATGGGAACAGCTCAACTGTGCATACCCATTGAAGAAATAGATGC
ATGGTCAATCGAATTTCCAGGTATATCATATGTTTCCATAAAAAAAGTAAA
CATACAGCATATCTCCTTCCAGTTTATTTATTTTTCTCTCTAGGACCAATT
TACAGTCTATCAGCAGTGCGTGAGCACCTGTTTCACCACATATACAAACCC
CTCCAAGACTATAAGGATATCATTAAGCTTTTTATCACTGTCAGTTAAGTG
GTAAACATAGTTTTCTACATACTTTGCATTTTTGTTTCTCATGAGATTCAA
TGTTTTACATGGGTAAGTTGTTAGATCATATTTATTCAAGATGAGGCATTT
GTCTCCTGGTAAGACATCTTGGTCTAATGCTGACTCTGGGGTGTGGACATT
TGGCTGTTGACTGTGAGGTGGCTATCTACATGTGGAGTGGAGGAGTCCTGG
CCTTGGATTGAGGAGAACAAGGTCAACTTCTCACCTCACTTGTTTCTGGCT
TTTGTGACCTTGGACAAGTTTAACTTTTCTCTCTCCTAGTCTTAGTTTTCT
TGTCTGTAAGTGACAGCAATGATGCTGTCTTTGTTGGGGTGGGCTGCCATA
AAAAAATACCATAGATTGTGTGGTTTAAACAACAAAATTTTATCACAGTTC
TGGAGGCTGGAAGTCTCAGAGCAGGGTATAGCATGGCTGGATTCTGTGGAG
AGGGCTCTCTTGCTGGCTTGTAGAGTGCTACCTTCTCACTGTGAGAGCTCA
CATAGCCTTTCCTCAGTATATGTGCAGAGCTCCCTCTCTTCCTCTTTTTTT
TTTTTCTTTTAAATAAATTATTTAATTTGGAAGACCAAGTGCAGAATCTTC
CTCTTCTTATAAGGCCACCAATCCTATCCAGTTAGGAACCCATCCTAATGA
CCTCATTTAACCTTAATTACCTCTTATAAGTCCTGTCTAGGAATAGAGTCA
TATTGGGGTTTATGGCTTCAATATATGAATTTGGGGGGATGGGGAGACAAT
TCAGTCCATAGTAAACACTTCCTCAAAGAGTAGTTATAATGTTTATAAGAG
ACAATGTAGGTAAAAGTAGTTTCAGTTGCATGCAGCTAAATGCAGTTTAGT
ATCCCTTCAGAGTCCTCCGCAGAAAAGGCACCTGATAAATATTTATGTGGC
CTTAACCTAAGGTATTATTCTTTATATAGTGCCTTCCCATGTAATGATTGA
TGTCATGTTTATCATTTGCAGTGCAGTTTATTTCTTATAGGTCATGGCTAC
AGAAACATGGGAGAATGACCATCATTAATAGGTCATTAGAATATGTAATTT
CAATTTTTTTTCTTTTGAAGGACTATTAGGTTAACAATGATTTTTAAAAT
TTATAGTAGATATGAGTGCTATAAAACAGGAATTTCCATATTATTTTGGGA
TTATAAATTGGTATGATCCTGAATAGCAATTTGGCAATGTATATGTTAAGA
ACCTTAGAAAATGTTTTTCACTTTTGATTTAGTATTTCCACTTCATGAAGT
CTATCCTTAGGAAATAATATTTGAACAAAGATTTATGTACAAAGATGTGTG
AGCTATATAATCTATAATATAATGCATAAAAATGGGAATCAATTGAAGTAG
TCAATAACAAATACATAATTATCAATATATCCATAAATTATACATCCATAA
AAAAGTTTCTAAGTATATTTATCTAAATATATATCATGACACCTAAATTTA
TTTTATATATGATACATGATGTGAGATATATGTATATATGAATATGAGTAT
ATATAATATACATATAAAAAGAATAGGAGATACTAGGAGTTATTTTAATTT
TGTCTTTATGTTTCCTGTGTCATAAATTTCTATGAAGAATATTTTAATAGT
TTTATGCATAGAAAAAGAGCTAATTTTCTCAGCCAGGTGTTCATTTGTC
CTTCTTTGATTGTTCAAAATACCTCCATTTATCTTCTTCTAGGATCACTCA
TTTTCATTGGTTTATTTGCAAGATGAAACAGTGTCCAGCAGTGACGACTGT
TGGAAAAGATATGTCTAAAAGCTGTTGTCTCCCCCTGGAGAAAAGAGAGAG
AGTGATTGATTCACTTCTGTAATTTATCAGATATGAGATATTGTATTTGAC
TCTGAGAACAATGATAATGATGATGGCTAAAGTTCACTGGATGTTTGCTCT
GTGCCAGGCAGTGTTTTAAGCACTTTACACAATAGATACCAATGCATTTAG
TTGTTCCAACAACCTTATGAGATACCTACTGTCATTCTCCCTGCGTTATAG
ATGAGGAAATTAAGGCACAGAGAGGTTAAGTTTCCCAGGTAGCACAGCTGT
```

FIG. 8-200

```
TGGATAATGAGCCTGTGCAGTAAACCCACATCCTCTAGCCCTTGAATGTCT
GTACGCTCTTAAAAGATGAATGTAACCTAGTCAGTGTCCTAAAGTTCCATT
TGATCTAAACTTGAAGGATAAAAATTTATCCAGTGAGGAAAAAGACTTAGT
GTTTTTCATAAAGAAGATACAGCGACGAAGGCCAGGCCGTGGGGACTGTCT
GATTTTTAGAGCCTAGAACCCTGAGCACACTCTCTAAACCCTCCAACATGC
TCTTACTCTGTTGCCTGCTGAGCATCTTTGATCCACTCTTGAGGCTAGCAG
TTTTCCTTCCATTCAAGATCTCACAACGTGTATTGTTCTCTGCAGATTTTT
TAAACATGCAATTTTATTTTTAATTGTTAAAAATATATTTATTTCAGTGC
ACTGAAGCTCAAATGTGTGTGTTTTAAAATCTAGTGTCCAAGGTTCATTAC
CCCAATTGTTTAAGCAAGTCTAACAACAAAAGGGGCACATTTTAATTTTCA
ATTTTTTTTTGTTCTAGCCTACAGTTGAGTTTGGGCAAATAATAGTAGACA
AAAAAGTGAAAAGAAAACTAAGGACAAGAAAATAAAGGAAGGGAGAATGGG
GGGAGAGGAGGGAGAAAAGTGAAAACAAAAGTTTATTCATATTTCTCTTGA
ATCCAATTCTTTTACCATTTGAAAACTTGATATGGTCAGAGAATAAGCCTA
GAATTTAAGTGATGAGGATAAGGTTTTACCACAGGTAGCCTCCTCTACAT
AGGTCTATTTCCTCATAGAATGAGAGAAGCCCCATCATTTCTGCTCTTTTA
CCCTTCTGAGCCAGCAGCAAGGAGATCTACTATCAAGGCATGAGCAACTGT
AGAAACATGAGACCAGATGTCTCTATTAATTATTCTACAAATTGCGCATTG
GATGATAAGGTTACATGAATCTTTAAATCAGCAAACCAAAGTCCCATTATT
ATTACATATTTTTTCCTCCTCAGAACTGAAGTGGGGCGGGGTACAGTGACT
CACACTAGTAATCCCAACAATTTGGGAGGCTGAGGCAGGAGGATCACTTAA
GCCCAGGAGTTTGAGACCAGCCTGGGCAACATAGTAAGACCCCATCTCTAC
AAAAAAACTTTTTAAAAAATTAGCTTGGCATGGTGGTGTGCACCTGCTGTGG
TTCCAGATACTCAGGATGCTGAGGCAGGAGGATGGCTTCAGCCCAGAAGGT
GGAGGTTACAATGAGATGCGATTGCGCCACTACACTCCAGCCTGGCAGCCT
GGGCAACAAAGTGAGACCCTGTCTCTGAAAAAAAGAACTGAGGTCAAGGAG
TAGTAAGAAAGTGGCTCATTCTCCAGATTTACTCTCTTTTTCTTAATTATA
ATGAACTCATGATACTTGAGGATATGTCAAACTGATCTTCAGACCCCAAAG
AAATTACTCAGAGCCTAGAATACCTTTCAGGAAATGTTACAGTGGTATACT
CTACTCAATTTAATTTTATGCTTGGTCATCCAGGATTACACAGGCTAAAGG
TAGGAAAAGTTTCACTAATTTTTAATGTCTTTTAATTTAGGACTACTGGGA
TTGTCTGTCAATGTGCTGAATATATATATCCTTCCAAATCTGGAAGATTTA
AGAGAAATGATAGTTATCATTCTTTAAGTCCTTAGGAATATGCCTAGAGAG
CTAATTTCATATGTTCAGGGAAAAAAGTGTATTTTTTCTCAACCTGTTGG
ACCCCGGTAAACATACTATGATCAACTGGCATTTTCATATCAAATAATTTA
TGAAATTCTTATAATTTATAGAAGGCCAACTCCTACCAAAGTCTTCAGTCA
TAAGCTGCTTCAAGTCCTTTTAGGAGCGTAAAGATGGTTATAAATAAAATT
TGTCAAACAGCAGTAAACACAGTGGTTTATATGCATTAAGGATCTTTAATC
TTCACATACTTCTAGAAGGTAGGTGCTATTACCATCACTGTAAAGGTATAG
AGAAGGATACTAATGCACAGAGAGATTAAATGACCTGCCTCAGAGTCCCAC
ATCTTATATGTGGTGATCTGGGAGTCAAACTTGGAGTCTGTCTCCAGAAGC
TTCACTTTTTGTCATCATTGAGCAGTGCTGTGCAGCCATTTTACTAGCATG
ATACCACGTCTGGAACTAGTGTTCTATAGGTGCTATTTCATTTAATCTTCA
CCCCATCTTTATGAGTAGGGCAATTATTACCACTCTATAGGCTCAGGGTAG
TTGAGTTTGTCAAACTGTGACTGAAAGACATTTAATTTTTGGCATACTATT
TACTTGTGCTCAAGGTATATCAAGCAATGGACTGATTTCACTCAACAAAGT
```

FIG. 8-201  ATTTTAAAAAGATGATTTATAAAATAGAAATGGGAGAAAAAAACTACAAAC
TGTCTAGGAATAGGATGTTATGTTTGCACATTATTTTCAGTAGAAAAGAGT
TTAGTATGGATACTCTCTTCTTGTATAAACCAAGAATGTTAAAAGAAAACA
ATTAGTGATTCTCTAGAAACAATTAGTGATTCTCTAGAAACACTTAAGATT
GGCTGTGCAGCACTATGGCTATCTCTGTGTAGTATTTTCCACTGACAACCA
ACATTTCCATGTTAGGTAGGCCATGTCTTCACGATTTCTGGCACCAGAGTT
TTTCAACTCCTCCATTTTTGGTAAAAATATCTCATAAAGGAGCAAGTCTAA
CCATGTGAGTTTGTTTAGTTTTTGTTTTTTGTTTTTTTGACAATGGCTTT
GTAACAACATTTAATAATCTGCATATTAGAGAAGCACAGAAGTAGGGCAAA
AAAAAAAGTTATGAGGGTAATTACAAATATTATAAGAATTCCTTAAAGTAC
AAATTGTCTCCAAGAATTTAATTGGCTTGTCTTAGATGAATAGGTCTCAAA
GATCAGTTTGGTCAAAGATCAGTTTGGTCAACTTTAGTTAAACAAGTTCAT
TTTTCCTAATTGATTATTTTGACTCAAATGTGGGCCACAGGCAGAAATAAA
TTTTCTAGTAAATATTCTTATTTAGGAACTTTTAGTCAAGTTATAAAGGTC
CTTGTTACAAACCTGCAAAAAGTTAGCATGCCAATATCTTAGTAAAATATA
ACTGAGATTTGTTTATTTGCTTGTTTTTTAATACTTGGGAGGGCCAGATCA
AAATTTCATCACTGGAAAGACAGATAATGGAGAAAAGGACAAAACAGAATA
ATACCACAGGTAAAAGAAGGAAGAAGCTGTCTATTTCAGACCTCATCTTCC
TCTGTAGACTTTGAAGAGGAAACTTCCTACTTCCAGAATTCTGGAGGTCTT
TTAATGAATCTCAGAACTGTATTTTTAGTGATAGTGTATTTCTCAGTGAGA
TTCCAAATGTGTTTACACTGGGAAGCACATATCCATCTGCTCTGAAGTATA
AAAGCAGTATTTGTTGTTTGAAGTACTGAAAATGGAGGTTCCAGCATTGTT
ATAATGTTGTCAGAGAAGATTGGTTATTACATTAAGATATGAATATAAATC
ATGGCTATATAAAAATAAGAAAAAGATTGAAGTCTTATTTTAGAGTGACAA
TCCATAGTAAATTGAATGTACCACATTAACAAACAGTAACAACTTTTTAAA
TAAGTAAAGGCTCAAGGTAGTCATTATCTCGAATGCTTACTTGTGTTTCTC
TGTAGCTATAGTACTTGATAGAGTCAGAGCTGTTTGGATTAACCATAGCCC
TTAAACAAAGCAGGCAATTGTGTTCCCGCATAGGCATGACGAAAACAGAGG
CAGTCATCCAAAACCTGCATGGTCCTCTACGCCCACACGTATACAGTACGT
GATTTACAAATCTAAAGTGGCGAAAGCAACAGTATCTATTCTAAGGCAATC
ATATGTTCTCTTATCTGTTTATCAATGGTTATTCTAAACTGTGTAAAAATG
TTATTTGCATAAAACTACACTGTTTCTTGTGATTTGTATTTTGTACCCTCC
AATTTAGAAATTGTCCAGGTATCCAAAGATTGAGAATTAATTTACTCAATT
TAATAATATTCACCTAAATTCTTAAAGTTATCATACACTGTGAACTCAGTA
CTTAAGCTCACACATTGAATCCTTATAATTAGTAACATAAAATTTAATTCC
ATTTTTAAAAATGACATTATCTATTATCATTTAATTTGGTTCAATGAATAA
TTTACAATTTTAGAATAATAAATAAAGTGATGTTAACTCATGTAACCAGTA
CAACTAGTGGAAGAAATTTAGTAAATGCAAGTTAAATTAGCTTTTGTTTTT
GTTTTTTAGAATATGAACCCTAAACTTGTGTATACTATAATATTCTGCTAA
TATTATTTTTACAGTATAAGAATAAAGAAGCCATTTTTAAAATGAAATTAT
TAAGCCAATTTGTCCAAAAAAAATCTTGATTAGATGTATTATATATTTTCC
TTATTAAAAAAACCTAATAAAAGAGGTATTAATATTTTTAAGTTATTTAAA
AATTGTGAAGTATTTTTTTTACAAAATACTTTAAGCTGTTAACTAAGACCA
CTAATGAAACTCACAGTTAAACTTTTTTTCTCTTAATTAGAACTTAAAGAG
GTAGCACATTTAAAGCACAAGGAAAATTTTTGATTTTTTTTAGACAAATG
AGTTTTTATTTAAATTGATGTATTTTAAGTCTTTATGTAAGCCAACTAAAA

FIG. 8-202

```
TTTAAGATTACATTATAATTTATTAATTCCCTTAAGTGGATAATTTCACAA
TTATTTAAATTCATAAAATAAGATAGTCTTTTCTGGGCACGGTGGCTCACG
CCTGTAATCTCATCACTTTGGGAGGCCGAGGTGGATCACCTGAGTTCGAGA
CCAGTTTGGCCAACATGGCGAAACCCCATCTCTACTAAAAATGCACAAATT
AGCCAGGCGTGGTGGTGCACCTGTAATCCCAGCTACTGGGGAGGCTGAGGC
AGGAAAATTGCTAGAACCCTGGAGGCAGAGGTTGCAGTGAGCCGAGATTGT
GCCACTGCACCCCAGCCTGGGCCACAGAGCAAAATTCTGTCTCAAAAAAAA
AAAAAAGATAGTCTCAATCTTATTGCCAATTAGGAAAGCTAACCGTGCTAA
TAGAACAGAATTTAAAGTGGGTAAAAACAGAGCCATAGGTTATCTATTTAG
CATGTTGATCAGTTAAAGAAATAAAAGTATGTAATTAAGATCAGAAGTCCC
TCAGGTGGCACCACTGCTGAGAATATGAATAATTCTGATTCTCAGTTTAGA
AGAAAATTCTAGTTTCCTAGTTTCCAGCATCACATCCCTTACAATAAACTC
GTTAAGGTTTAGAAAATATTAAATCTTTGTTTTATTCAGATATTGAAAGCA
CTCTTTTTTTTCCCTGACTCAATAGTCCAATTTGTAACAACATTATGTTTC
TTCTGTCCTCTAACCTTACTTAAAGAACGTGAAGGGGCAATAATGTGAAAT
TACTAAAATTAATAATAAGCTGTAGAGCCTCTGCCATAGCAGTTATTGAGA
CCAGACATTCGGTTTCCTTGATTTCCTTTTTGTCTCCTGTTAGTCCTAACA
CTTTCTTAAAGTCAAAAGTTATAACAGGGCAGCCATTTTATATTCATATCA
TCTTAACACAGGAATACTGGTTTTGCAGATATCGACAACTATTTGGACTCA
AAAAAGACAAGTTTTGGAAGGTGGAAAGAGGCATACAAGCACAAAACATCA
AATCCCATGTAAAGTCAGAAAGAAAAACACCAACTCTAACCCTGTGTCCTC
ACAGAGAATATCAACATCTTCAAACAAAAACACCCCAAAAAAAGGTTAATA
AATAAACCAGATTTCCTGTCCTCTCCACTGACTAATCACTTAATGATGTGA
CCAGAAAACCAGAATTCAAATTCTACTACTGCCACCAATATGCAACCAATC
AGCCAAGTCCAATTAGAATAACCAAAACAAACAAACGCGGACGATAAACTT
TTAGCATGCAAAAGCCAAAGGAAAGTGAACAGAAAACTCAAAGGGTCCAGG
GATAGACAACCTGTTTCCAAGACACACATTTCTGTTGGTTCTTATTGTATG
ACTCACATAAACACTGTCTTGGTGGAAAATTCAGAAATAAATGACCAAGAA
GTTAATAATTTGCTTACTGGGTACTTGTACAGAAGAGAGAACAAGCAATAG
AATTATTTCATCTAACACAGGCAAAAACATAATCTATGTAAGAGAAAGGGG
AAAAGGCGGGGGAAACAATACTGAATTTTGTTTGCAGATTTTGGTTACACT
GATTAGTTAGTTGGCAGGTAAGAAAACGGTCAGTCTGAATGGGAATAAGTG
ACCAGGTCCATTACAGGCATAGAAAAAAAAAAAACCATTTAGGCCCGGCGC
GGTGGCTCAAGCCTGTAATCCAGGACTTTGGGAGGCCAAGGCGGGCAAATC
ACCTGATGTCCGGAGTTCGAGACCAGCCTGACCGACATGGAGAAACCTCGT
CTCTACTAAAAATACAAAATTAGCCAGGGTGTCGTGGCGCATGCCTGTAAT
CCCAGCTACTCCGGAGGCTGAGGCAGGAGAATGGCTTGAACCCGGGAGGCG
GAGGTTGCTGTGAGCCAAGATCGCGCCATTGCACTCCAGCCTGGGAAACAA
GAGAGAAACTTCGTCTCTAAAAAAAAAAAAAAAAGAAAAAAAAATTTACT
TGTGAGGGACTCTGGAAATTTCATTTCTCATCAGAATTTCTCAGATAAGTT
ATCTAGGCAAGGCAGCCTGTGATTGCACAGCAGTGTTCAAGTATAAGGCCT
TGTCTGGCACCAAAGACAGGCCTTAGTTTATTTCCCAGGTGTGAAAGAAAT
TGCAGATTTAAGATCACACAGTCCTTATGTTAAATAACTGTAACCTAAATT
ACATGGTATTTAAGTTTGTAAAAATCTGCTTTAACACTAATTTTATTTATT
GTATATTCCCGGTTTTTAATGGAGAAAGCAAACTTCTAGGTGCTAAAAACG
TGTTCTAGACTTGAATAAAAAGATAGGTAGACTACGTCTAACCCTTCATCT
```

FIG. 8-203

```
TAAAATCTTTACCTGGAAAAGACCATGAGTAAAATACTTAAGGGAATGTGG
AATTTCCCAGGCCACAAAGCGGCCTGCAGTTGTCTAGGAAGGGAGAGTCCT
CTAGGAGATACAGTGTATGTGCTAAGTTTAATGACGTCTCCTCTTCATTCT
CCCCCACCCAGCGCCTAGTCCTTACTGGCCTTCAGTTCAGTGTTCGAAGGC
TTGTCAATTTACCCAGCAGTTAAGAGTTGGCTTCTCCTAAAGCAACTTTCA
AACTTGTCTGCATGTTACAAGCCCCCTACGGAGATTTTAAGTTTCAATCAG
GCAACACACCATTTATGGCTGACTGAGCACTGGGATTCAAGCAAAATTTGA
TTTGATTTGAATCTTGAATAAACCAGTTGAATAGAATAAGATGTATGAAGC
AACATCTGGCGCAGTGCTTACATCTTTAGTTCTGTACTGCCTTAGTGTTGT
TATCAAAACTGACGCATATTAGTTAAAAGACTATTACCGGGGCAGTTGGAA
ACCCAGGAGACACACCTTCAGTATACTACGAAGGTGTGCGCCACGAAAACA
GAGGGGGAGTCCTTCCTTAGGCAGTTACTGCCCAGGTTCCCACTCCGGTCC
GCTATGTAAATCAGAGTCTCAAAACAGCTTTCCCTCGATTGGTTAATATTT
AAAATGACAGGACAGCCTATTGGCTAGAAGCTGGTGGCGAAATTATGACAT
TACGGCAACCGTTGATCCTGGCGACGTAGACAGGGACAGACAGCTGGGTCT
GAAACCTAAGCGAGCCTGCGGTTTCTTCCGGGAACGCCGAGTTAGCAAAAT
GGCCGCTTGTCTCCATTTTAAATTTAAGCACAACGAATTGACCCCAAAGCC
ATTTTTAATGGCTGGCTTCTTTCGGGTTCAGGACCCTTTGTCCCTCTCTAA
GCTGCAACACTTGTCCCCACCCCTCTCCAGTTCCTATATTCTAATACCCCT
CCGCCGCCAAATAAAATTTGGCGTCTGGCCACAGCTCTTTTAGTGGGTATC
TGGGTGGCTCTTAAAAGAGCCTTTGGGGTTAGGTGTTAAGACGCTTACTTG
GAATGTTTACTTGGAGCTGGTGTACTTGGTGACGGCCTTGGTGCCCTCCGA
CACGGCGTGCTTGGCCAGCTCTCCGGGAAGCAGCAGGCGCACGGCCGTCTG
GATCTCCCTGGAGGTGATGGTCGAGCGCTTGTTGTAATGCGCCAGGCGGGA
AGCCTCGCCCGCGATGCGCTCAAATATGTCGTTAACGAAAGAATTCATGAT
GCCCATGGCCTTGGAAGAGATGCCAGTGTCGGGATGGACCTGTTTCAGCAC
CTTGTACACGTACACAGAGTAACTCTCCTTGCGGCTGCGCTTGCGCTTCTT
GCCATCTTTCTTCTGCGCTTTGGTCACTGCCTTCTTGGAGCCCTTCTTCGG
GGCGGGAGCAGACTTGGCTGGCTCAGGCATCTTAAAACACCAGAAATGTGT
CGAAAGTAAAGAGCGGATTTCTGCTACTTATAGGGCTTTTATGCTAATGAG
GGATGGAGAGTACCTCTTAGTTAATTGGAAGACAAACTGCACAGTTGTCAT
CCGTGGGCAGAGCTATGCAAATGAGGTATGAAAGTACAGCTTTTCTATTGG
CTATCTGACTAGCATTTGCTACCGACCAATCAAAAAGTCGGATTTACTCCC
CAGGAACTACCTATAAAAGCGGCCATGTTTTACATATTTCTTGATTTTGTT
TGTTTTCTCGTGAGCTTAGGCCGCTGGTTTTGGTGATTTTTGTCTGATTGC
AATGTCTGGACGTGGTAAGCAAGGAGGCAAAGCTCGCGCCAAAGCGAAATC
CCGCTCTTCTCGCGCTGGTCTCCAGTTCCCGGTGGGCCGAGTGCACCGCCT
GCTCCGTAAAGGCAACTACGCAGAGCGGGTTGGGGCAGGCGCGCCGGTGTA
CCTGGCGGCGGTGTTAGAGTACCTGACCGCCGAGATCCTGGAGCTGGCCGG
CAACGCGGCTCGCGACAACAAGAAGACTCGCATCATCCCGCGCCACTTGCA
GCTGGCCATCCGCAACGACGAGGAGCTCAACAAACTGCTAGGCCGGGTGAC
CATTGCTCAGGGCGGCGTCCTTCCTAACATCCAGGCCGTGCTTCTGCCTAA
GAAGACCGAGAGTCACCACAAGGCCAAGGGCAAGTGATTTGACAGGTATCT
GAGCTCCCGGAAACGCTATCAAACCCAAAGGCTCTTTTCAGAGCCCCCCTA
CCGTTTCAAAGGAAGAGCTAACCTCACTGCTTGTAGGTAGAAGGAAAAAAG
GCACTAAGGTAAGTTAATTTTATGCCAACCTTGAGCAAAGCGTATTACTGC
```

FIG. 8-204

```
TTTTCGGTTTTTGGGGAGCGCTGTTACTAAAGGTTGGTCTGTTTGTATGTA
ATAGTAGGTCAGTTACGTACTATCATACTCTAAAGAAATATTCTAGTTAAT
GCTTTGTAAGATCGACCATAGTTAGTGCCTAACAGTTTACATGCAGGGATG
CCTCGTGATCTAAACACTTCGTTGTGATTACTTTAAAAATGTAAATTGAAG
GCAAAACTCTAACGTGTTGGTAACCTTGTTTGGTCCTCCGACTAGTCCCCC
GTCTATTTTTTTCTCAATTTAGGCTGTAGGCAGCCTCACTTTCCTAATTCT
GTGAGAGTTATAGGTCCCATTCCTGCTAAAGTGCAGAGTATATTACCTAAA
AGTTAACCAGGGAGTTGAAAGGTGTCTGTAAAACAGACTAATGTCCCTAAT
GTAGAACGGTGCCTGACATGCAACTTACTCTTGTATTTTAAGAAGCTCAAG
CGTCTAGGTTGCCATTACAGGCAGAAAAGGAAATAGAGTGGGGCCTGTGGC
CACTCAAAAACCTTTGCTTTCTGCTCACCCCTCTAATCCTACCACTTTGGG
AGGCCGAGGGGGCTGATCACCTGAGGTCACGACTTCGACACTAACCTGGCC
AACATGGTGAAACACCTCTCTACTAAATAAAAATAATAAATAAAAAAATAA
GTTGGGCGTGGTGGCACATACCTTGTAATCCCAGCTACTCTTGAAGCTGAC
GCAGGAGAGTCGCTTGAGCCTGGGAGGCGGAGGTTGTAGTAAGCCGAGATC
GTGCCACTGCCCTCCAGCCTGGGCAACAGTGAGACACGGTCCCCCAAAAAA
ACCTTTGCTTCTAGGGATCTGGTAACAGCTGCCCCACCCACAAGAAATGGA
GATCTGGGACCATGGACAAATTTCTAGAGACCTATTTTCCTGGATTCTGTG
AATCTCGCCGAGGTTTTCTTCCGGATCTCGGTTTCTGCATTTTTTTGTTTG
TTTGCTTGCTTTTTTGAAACGGAGTTTTGCTCCTGTTGCCCAAGCTGGAAT
GCAGTGGCGCGATCTCGGCTCACTGCATACAAACTCCGCCTCCCGGGTTCA
GACGACTCTCCGGCCTCAGCCTCCCTAGTAGATGGGATTACAAGCGCCCGC
CACCAGTAGAAACGGAGTTTCACCAGGTTAGCCGGGCTGGTCTCGAACTCC
TGACCTCAGGTGATCCGCCAGCCTCTGCCTACCAAAGTGCTGGGATTACAG
GCGTGAGCCACCGCGCCCGGCCGGTTTCTGCTTTGATCGGAATTAAGTGGG
CAGAAAAGTCTAGGCGGGCTAAGTCTTGCCTATGCATCTGCGCCCAGCTGC
TCAGACTGGCCAAACAGACCCAGTCGTTTAGTCTAACGCTTCTGGAACTCC
ACTGAAGCGTTTTGCATTGTTTCGTTTGGAGCCTTCAAATCCGAGTGTGTG
GCAGGAGATAATAATCCTAGCAGAAGCTGTTTACTGCTGACGCGCCTCCCA
CTTCCCAGATACTGACACCGGCTCAGGGCGGATCCAGCCTTTTCCGCTCTT
CCCTCCCTCCACCCCCTCCTTTCCCTACAACTACTCTCAAAGGAAAAGGGT
TGGATGTCCCATTTGGGTGAAAACAAAGTGGCATAAAAGCAAATGATCACC
TTTGATAGCCACATATTAGAATTTTCCGAGGGTATTTTTAAATTACAACGA
TTCTAATGGGCAGCTGGGCTGAGAATCATCAGATTTGAAGGTCTGGTTTCA
CATGGCTCTTGGGCTGAGAAGACCGGATTTTCCCCCCCCAGCATTTCCTGT
ATGTCCGAGAATTTCGATCCTAAGGTTAGAATTGCCTTATGGGCCTTGGAA
TCCTTTTTATTCACTGACCAAATTGCCTTTGATTCCAGCTCCCAATCGGTG
TGTGACCTTGGCCTAGGGCTTAATCTCTTCCTACCTCCATCTCTTCCTTGT
ATGCTTTTGCTCACCTTGAAATGAAAAGAACCTGGCTCAGCAAGTGTAGAT
TCTGAAATCAGAAAACAGGCTGAATAAGAGAGATGGTTTATTAGGCACTAC
TGTGTGCCAGGCACATTTCATGAGCTTCCAGTATGTTAATTCATTTAATCC
AACAATCTAAGAGATAGGTTTTATCCTTATTCCGAATTTTGAGATGAGCAA
ACTAAGAAACAGCTTAAAGAACTTAAGTTGTAAGGCCAGGAAAACAGTACT
TATAACAGCTGACTATTCTATAACCACACCTCCTTAAGAGATTATTGTCAG
AAAAATAGAAAGAGTAAAACATCCATACATAATGGGTAAACTTTGTCCACA
TACCAGAATGTTACTAATGGCTTTCTAACCTCTGAAGAATTTAAGGGAAGG
```

FIG. 8-205

```
AGGAAAGGTAATTTTCCCCAGGGAATCTACACGAAGAGGTAAATCTTGACA
ATGTATTAATACTGTAAACCCAGGGAAAAAAAGCCAGTACAATTTTTATTT
AGGGTGTGGCAAATAAAACAAAGGGACACGTGAAAACATGGCTCAGTAAAG
AGCTACAAGACTTGGTGCAACTGACTTATTGTGGTGAGTGAGAAAAGGAGA
GAGAGAAAACTTGAATTTCAATTCTTCTCTCTGGGCTCCAATAACAAGATT
TTGTATTCGGTCTATTTAGTAGTGAATGATACATTGTGTTAAGTTTGTTAA
CCTAGAGGCTTTCATCTTAAGCAGTACTTAAGATGTAGACCCCCTCTTATT
CAAATACTGATAATCAGCATAGAACTTGGCATACAAGAGACACTTGGCTGT
TGGGCATTGAGAAAATGTTGAACTGAATGAATCAATGACTTAGGCAGCCAG
GAAGCACTTTGTTGTAGAGAGTTGGTTTATTACTAAGGAAGACATTAAGTA
TTAAATATTAGACTAATAGGTTGCTAATAGTGTTTTCTCTTTCCAATAGAA
AATGTCTTCTGAGGCTGATCTGGTGTCTCACATCTGTAATCCCAGCACTTG
GGGAGGCTGAGGTGGGTAGATCACCTGAGGTCAGGAGTTTGAGACCAGCCT
GGCCAACATGGCGAAACCCCATCTCTAATAAAACTACACAAATTAGTCAGG
TGTGGCGGTGTTCACCTGTAGGCGCCTGTAGTCCCAGCTACTCAGGAGACT
GAGGCAGAAGAATCACTTGAACCCCGGGAGGTGGAGGTTGTAGTGAGCCAA
GATCGTGCCACTGCACTCCAGCCTGGGCGACAAAGTGAAACTCCGTCTCAA
AAAAAAACCAACCCCATCTCTACTAAAAAATACAAAAATTAGCTGGGCATG
CTAGTGCACGCCTGTAGTCCCAGCTACTCGGGAGGCTGAGGCAAGAGAATC
ACTTGAATATAGGAGGGGGAGGTTGCAGTGAGAGTGAGACTCTCAAAAAAA
AACAACAAAACAAAAGTAACAAGAAAAAAGAAACTATATTCCAAAAATCC
AAATTTCACTGGCAGTTTGTTCTGGGAGCTTCAGACACATAGAAGGTGTCA
GTTAACCAGTTCTTACCTAAGAGGTACTGCTAAGAGCCTAGTCCCTAAGCA
AAGGGAGCTTCAGAGAAACACAGAAGGTGCCAGTTAACCAGTTCTTACCTA
AGAGGTACTGCTAAGAGCCTAGTCCCTAAGCAAAGGACATTCCTCGTAGCT
CTGTCCTGTCTCCTCATCTCCAAAATACTTTACCTTCTACTTTGAAATGCC
CACTATTATATTCAAAAGCCCTAGTTACTTCCAGGGAAAATTATCTATTGA
GCAATGAATTTCGGTAGCTTCAGTTGGATTCCAACTCTTGAGCAAGTTTTC
ATCTCCCTTGCCTGAATGGCCCTGGGGAGGACTATTTAAATTGGGGCGAGT
GGATGAGGATGCTAAACCTAGAGGTCTCCCAATTACCAAAGGCACCTGGGC
ACCAGGGACTAAAGTTTGTCTCAGGAATTTACTGAGATATGAGGCTGAGAT
AAAATCATTTTTTGGTACATAAGGTATCTTGAACAAAGCAGATCAGTTTAA
CACAAAATCAACAATCGTAATTTCCCTTTTTAAATTTCCAAATCTATGTAG
CAATATCCTTTCCTTTAATTCATTCATCATCTCTATTCACTTTTTGTATTC
TGTAAATCATTTGAACTTTTATAAGAATTATATTTTCCCCTTGAGGTCACA
AAAAAGAAAGTATTAGAAATTTTATAACCAATTTTTAAAAAATTATATTTT
AAGGTTAAATACAAACCTTCTAAAGGTTTGTCATCTGTTGATCCTAAATTA
TAATTATAAATTTATATATTCCTGTTGAATATAATGCATGTGTGTTACAAG
ATTATTAGCAATTTGAGAATTTCCCGTGCATATTGGAGATGAGCAAATGGA
ATAAGTGCTCATGTGTAGCGACAGGATTCTCTATTTTATTTCAATACTTAA
TATTGTACCAAACCAAGTAAGAGGAGCATCATGAGAAAATGTACTAAAGGA
CAGTCATTACCTATATTTACACCTAGAAAAGAAAACTATATTATTGATAAA
CTGATAAATCTATTTTATGTATTTATTTATTATTTTGCTCTGTCATCCAGG
CTGGAGTGTACTGGTGCGATTTCCACTCATTGCAACCTCCTGCTCCCAGGT
TCAAGCAATTCTACCTCAGCCTCCCTAGTAACTGGGACTACAGGCATGCAC
CACCACACCCAGCTAATTTTTATATTTATAGTAGAGACAGGGTTTCACCAT
```

FIG. 8-206

```
GTTGGCCAGCCTGGTCTCAAACTCCTGACCTCAGGTGATATGCCCACCTCA
GCCTCTCAAATGCTAGGATTACAGGTATGAGCCACCGCGCCCAGTCTGATA
AATCTATATTAAAAAGAATAAATATAACCATTGCATCTTCAACAGAAATTG
GAATATGGCATGTAGATTTCAAAATAAAATGAATTCTCTGGCATTGAATTA
CTGTACTCATGTTGAAGAAATGTCAGAACTTCATTGGATGTTATTATATTA
CAGTTGTTTGTTTGAGTTGTAGTTTGGGCAGAGTAAAGGAGCCAACATGTC
TTAGGATTTAGAACTTGTGCACATTGCCTACAGTTGAAAGAAGAAAGCATG
CTAAATTCCAGCCTCTTTGGTATGTGGTTGGGACGTAAAGTTTTACCACAT
CCTTCATTGTCTTAGCCTACTCAGGCTGCCATAACAAAATACCAGAGACTG
GATGGCTTAAACAACAGAATCTTTTTTTCCATATCTAAGAGGCTTGGAACA
GAAATTCATTTTCTCACAGTTTTGGAGCCTGGAAGTTTAAGATCAAGGTGC
CAACATAGTTTATGGTGAGAATCTGTTCCTGGCTAACAGATGGCTGCCATC
TCACTGTGTGTTTGTATGGTGTTTCCTTGGTGCCTGCGTGGAGAGAGAGCT
CTAAGTGTCTCATCTTCTGTAAGGACACCAGCCCCAATGGGATTAGGGCCC
TATCCTGTGATCTTTAGTTTTATGTACCCCCTAAAGGCTCTATGTCCAAAT
GCAGTCACACTGGGGTTTAGGGTTTTAATAAATGAATTTTGGGGGACACAG
TTTAGTCCATAACATTCTGTCCTTGACCTGCCAAAATGTATGTCCTTCTCC
CATACAAGATAAATTTATTCCATCCCAGCCGGGCATGGTGGCTCACACGTG
TAATCCCAGCACTTTGGGAAGCCAAGGCAGGCGGATCAGAAGGTCAAGAGA
TCGAGACCATTCTGGCTAACACGGTGAAACCCCATCTCTACTAAAATAAAA
AAAAAATTAGCCAGGCGTGGTGGCGGGCGCCTGTAGTCCCAGCTACTCTGG
AGGCTGAGACATGAGAATGGCATAAACCCGGGAGGCAGAGCTTGCAGTGAG
CCAAGATGGTGCCACTGCACTCCAGCCTGGGCGACAGAGCTAGACTCCGTC
TCAAAAAAAAAAAAAAAATTATTCCATCCCAACAGCCCCCTGAAAGTCTTA
ACTCATTCTAGCATCAATTCTAAAGTTCAAAGTGTCATCTAAAAAATCATC
TAAATCAGGTTACGGGTGAGGCTCAATGTGTGATTCATCCAGAGACAAAAT
TCCTTTCCAGCTTTGAACGTGTGAAACCAGAAATGTTACATGCTTCTAAGG
TACAATGGTGAAACAGGCATAATAGACATTCCCATTAGAAAATGGAGAAAT
AGGAAAGAAGGAAGGTGTAATGTGTCCTAATCAAGTCCAAAACCTGGCAAG
GCAAATTCTGTTAGGTCTTAAGAAAAACCCTCTTTGGCTTGATGCCCTGAT
TTCCAGGCCCAGTGGTGTCTCAGTGTCACCTCTGGCTCTGTAGTTGGCCTA
CTCCATCTGCCCTGCCTGAAGTCTCGGTCTTTCAGTTTGGTGGGGTCCCAC
CCAGGCAGCCATCTGTGAGAGACTCCCACACAGTTCTGCAGGGCATCTTTG
AAACAGGTAGAGTCAGCCTTGACTACATGTTCCCACCCCCACCCTATCCCA
TCTGTACTCTCTGAGTCTGACATCAAAGTGGCAGCCCTGGCGGCTCCTGCC
TGTAATCCCAGCACTTTGGGAGGCCAATGAGAATGGATCACTGGAGGTCAG
GAGTTCCAAACTAGCCTGGCCAACATAGTGAAACCCCATCTCTACTAAAAA
TACAAAAATTAGCTGGGCAAGTGGTGGCAGGAGCGCTACTCGGGAGGGTAC
AGATTTAGAGCCTGTAATCCCAGCTACTTGGGAGTCTAAGGCAAGAGAATC
CCTTGAACCTGGGAGGTGGAGATTGCAGTGAGCTGAGATCACACCATTGCC
CTACAGCCTGGGTGACAGTGAGACTGCCTCAAGAAAAAACAAAAGAGTCAG
CCCTAGTGATCTTGTAAGTTGCCTTTGGTGGGTCAGTCTTTCCTTTTCTTA
AAGAATAGTACACATTGACAGCCAGGTAGCTCTATGATCCTGTTCTATAGA
ATTCAAAAAGTCGACAACCTTCCTTTGTTCCTTTCTGTTTTCTCTGCCTAC
GTTAGTTTAAATTGGCAGTGTCTCTGCTGGAATAATCCCATCTCTCTTCCT
GGCTTCTGCTGAGATGGCTGATTAAATCCTTGGGTCACACCCATTATCTCT
```

FIG. 8-207

```
TTATCAAATGGTTGTTCAGGCTAGGCTCAGTGTTTCACGCCTGTAATCCCA
ACACTTTGGGAGACTGAGGAGGGCAGATCACTTGAGCTCAGGAGTTAGAGA
CCAGCCTAGGCAACATGTCAAAACCCCATCTCTATAAACAACAACAAAAAA
TTAGCCAGGGTGTGGTGGTGCATACATGTAGTCCCAGCTACTTAGGAGGCT
GAGGTGGGAGGATTGCTTGAGCCTGAAGGCAAAGGTTGCACTGAACTGAGA
TTGTGCCACTGCACTCCAGCCTGGATGACATAGCCAGACCCTGTCTCAAAA
AACATAAAAATAAAAATAAAACCAAGAAAAAAAAGAAAAAGAAAACATTG
TTCAACCATACCTCTTCAAGAAAAACTTTCTCAATTTTTACAATATAGATT
GAGAAATCTATCCCAAATCTCCAAGTTCTGATTGTGTTTTGCTTAAAAATT
CCTTCTTTATTTCGGCTCTTTCCTCTCACATTTCACTTTAAGCAGTAAGGA
GGACCTAAATCACACCTTCAATACTTTGCTTAGACATCTCTTCTGGTAAAT
ATCCAGTTTTACTGCTTATAAGTTCTTTCCAGTAAACACTACAGCGTAATT
CAGCCAAGTTCTTGACACATTGTAACAAGAACAGTGATTTCTACAGTTTCC
AATAACCTGTCCCTCATTTTCATCTGAGACCTCACAAGAGTTGACTTTAAT
GTCCATATATATATATTTTTTGTGTGTGTGGCGGGGGGAGTGGAGTCCT
GCTCTGTATCCCAGGCTGGAGTGCAGTGGTGTGATCTTGGGTCACTGCAAC
CTCCACCCCCGGGTTTAAGCGATTCTTCAGCCTCAGCCTCCCGAGTAGCT
GGGACCACAGAAGCACATCACCATGCCCAGCTAATTTTTGTATTTTTAGTA
GAGACAGGGTTTCGCCATATTGGCCAGGCTGGTCTCAAACTCCCGACCTCG
TGATCTGTGCCCTCAGCCTCCCAAAGTGCTGAGATTACAGGCGTGAGCCAC
CACGCCTGGCCTAAAGTCCATATTTTAACCAGCATATTTAATATTCTATCC
ATGATCGTTATAAATCTAAGTTTCTATGAAAATGGAAGCTTTCTGTCCAGC
TCTCTTCCTTTCTGAGCCTTTGCCAGAATTGCCTTTAATGTCCATATTTCT
TTCAATAGTCCCTTCACAATTGGCTTTTTCTAGTATGAACCTCAAACTCTT
CCAGCCTTTACCCATCACCAATTTCCAAAGCCACTTCCCCATGTTTAGGTA
TTTGTTGTTGCAGCATCCCACGCCTGGGTACCAAAACTTAGTCAGCTTGGA
CTGCCATAACAAAATACTACAGACTGGTGGCTTAAACGATAGACATTTATT
TTCTAACAATTCTGCAGGCTGGAAATCTAAGATCCAAGTTGCCAGCATAGT
CAGTTTCTGGTGAGGATCTCTTCCTGGCTTAAATTATTTCACAGACACCAG
GCAGATAACCATATCCATTCTTTCCTGTATTCGTTAATAGTCAGAGCTAAA
AGTGTAGGGCTCTAAATTTACACTTCAACAAATTGTTCTGTTATTAAGTAT
TCACCTCAAAATGACCAGACTATACTATCCTCTAAATTTTAGAAACTTGGA
GCTTGGCTCTGGTCCCTAGTCTTTGTTCTGTCTCATTAATGGCTTCATCAA
TACTACGGTTCCAAAGACTATCTATATGCAGTAAACTTCCAATTTTACATC
TCCAGCCTGACCTTTTTTCTGAAATGCAAATGTGTGTAGCCACATTTTCAC
TTGACATCTCCATTTAGAACTCTAATAGGTCTTTCACCCTAAACACTTCCA
AGACACAGGAATAAACGTGCTCCTTAAGCCTGTTATCCCTTCCAGTTCTCC
CCAGTTCAATAACTGACACTACCATTTACTCAAATCAACATTCTAAGAGTG
TCACTTGCTACATTTCCTTCATCTCTACAAATCCAAAGTATCTGTGAGTCA
CGTCACCTACATATTCAATACATGCAATAATTCATTCTCCATACTCCTTAC
CATGACTTAAGGGCCCACTCAGTGACCATCTCTGGCCTCTGTTCACCTCTT
CTGCTGTTCTCCTTTGCTGTTCCAGCCACGCTGGTCTCTTTTCACATCAAG
CAGCTAAGCTCTGCCCATTTAAGACATTTAACTTCTTGGCCTCAATCTCTG
AAATGCCTGTTTGATTTTTCTTCTGGTGAGCTCATTTTCACTCATCAGGTC
CCAGCTCTGTTTCAGACAAGGCTATCTAAAATAGACCTACCTAAATGGATT
AAAAATCTGAGAATATGAAATAACAAATATCAGATGACATTTTAGGAGACC
```

FIG. 8-208
```
CTTTATATACCTCATTTGTGTGTGTGTGTGTGTGTGTGTGTGTGTGT
GTTTGGAAATGGTGATGGAGGGTGTCATTGCTAAGTGAGGAGGAAACACAA
AAGCCATCTAGGAAAGGACACAGACTAGATAGGTCCAAAAGTGGTTTAAGA
CAGAATATATGTAAAGAGAGTTATAGAAAGAGCAATAAGTTGGGATAAAGG
ATTTCCAAAACATATACGGGGTTAGTAACCTCAATTTACAGGGACAAACTG
CAAAACGTTAGTGAAAAGGCAAACAACATAATATAAAAGATGATTAAACGG
TATTTTATATCATGTATTAAATTCATATGGCCAATACATATGAAAAACAAG
AAACAAAAAACCTTCCTAGTAATTCAAAATTATGCATATTAATACAACAAA
GGGATACCACTTCTTTTTTTTTTTTTTTTTGAGACAGAGTCTTGCTCAGG
TACCCAGGCTGGAGTGTAGTGGCATGATCTCAACTCACTGCAACTTCCACC
CCCTGGGTTCAAGCGATTCTCCTGCCTCAGCCTCCCGAGTAGCTGGGACTA
CAGGCGCCTGCTACCACGCTCAGCTAACTTTTGTATTTTTATTAGAGATGG
GGTTTTACCATGTTGGTTGGCCAGGATGGTCTCGGTCTCTTGACCTCGTGA
TCTGACGGCCTCAGCCTCCCAAAGTGCTGTGATTACAGGCGTGAACCACTG
CACCTGGCCTAATTTTTGTATTATTAGTAGAGATGGGGTTTCACCATATTG
GCCAGGCTGGTGTCGAACTCCTCCTGACCTCAGATGATCCACCCACTTCAG
GCTCCCAAAGTGCTGGGATTACAGGCATGAGCCACTGTGCCCAGCCTGGGA
TACCATTTCTTACCTATGAATAGACAACCACTAAAGCCAGTATACTCAGGA
CTGCAAAGGATGAGGAAGAATTGCCATTGTCATATAGTTTTTCATAACTTT
TCCTGACAATGTCTATTAAATTGTATTAATAGACATTTGGAAAGGGAGAGT
GTCAACAATCTAGAATAAAGGCCCCACTAGGTAAGGTTACATATGTAAGGA
CTCTTTCAAAACTGTCACAAGAATTCAGGTACGGTGGCTCATGCCTGTAAT
CCTAGCATTTTGGGAGGCTGAGGCGGGTGGATCACTTGAGGTCAGGGGTTT
GAGACCCGCCTGGCCAACATGGTTAAAACCTATCTCTACTAAAAATACAAC
GATTAGCCATGCATGGTGGCACATGCCTGTAATCCCAGCTACTCGGTAGCC
TGAGGCAGGAGAATAGCTTGAACCCAAGAGGCAGAGGTTACAGTGAGCCGA
GATCGCACCACTCCAGCCTGGGCAACAGAGTGAGACTCCATCTCAAAACAA
AACAAAAAAACTACTCAAAACTGTAATAAGAAAAAAAAAAACCTAATTATA
CATGTAAAACATTTAAATAACTAAAATAAGAATACTGTTGACATAGTGAGA
CATCCATTTATACTATGGAATGTTATGCAGCTACCTGAAACAATAATCCGG
TGAAACAAAATCACACACACAACTGATGAGAGTAAATAGAGAACCGTATGG
AAGAAAACATACCACAGTAATTATCTCAGATAGCTGAAACTAAGTTGGTGC
AAAAGTAATTGTGGTTCTTACCATTACTTTCACTGGCAAAAGCTGCAATTA
CTTTTGTACCAACCTAATAGAATGGGGTGAGGAGAGGTAAACCTTTATAAA
CATCTCTGTGTGAACTGTTAAAATGAGCAAGTATATTTTTTTAAAGTATA
AAGAGAGAAAAAAGTAAACTTTCTCCATTTCCCACCTCAAATTATGTTCTG
TCACTCATCCTGTTTAGATTCTTTCAAATGCAGTTTGAAGTTTTATTTATG
AGATTCCTTGTTGTTTGCCTCTTTCCATTAAACCTAGCTCCACAAAGTAGG
GACCTGATGTATTCATTCACTGTTATATCCCAGCATCTAGCAGAGGGCCTG
ACACTTAGTGGGAACGCAAGTATCTGGTATATAAACCAGAGAATAGATATT
TTTTTAGCCCAGAAAGCTGTTTCACTGCACAGAGTGTAATTATCTGAATTT
CTATAAAAATGTCTATCTATAAATCATTGTCAATACATTACCTACTCACCT
TACCCAGCTACCAGGAACACTATGAAGTTTTGAATTACACCCCATTTGTTT
TCCACACTCTTACCATTTTCCCAGTTTCTGCACTGACCTCTCCAGACATCA
TGTGTACTGATAATTCTAAGTTGTCTAGATTGTTAATTCTTTTAAGGGCCT
GTTCTCTGCTAGCTGGCATCATGCATAAAATAATTCTCTTTAATATGCTCT
```

FIG. 8-209

```
GGGTCTAGGGTTAATAGATGTTTGCTTAAAATCATGGAAAGAAAATGGTCA
CACAGCTGGTATGTGTGATCAAATTTGTGCTGTTTCATCCACTTAATGTTT
ACTTTGTGGTAATGGAACCTCCCAGCTTTTATTTTCCTTCCTTCCTTCCTT
CCTTCCTTCCTTCCTTCCTTCCTTCCTTCCTCCCTCCCTCCCTCCCTCCCT
CCCTTCCTTTCTTTCTTCACAGAGTCTAGCTCTGTTGCCCAGGCTGGAATG
CAGTGGTGCGATCTCAGCTCACTGCAACCTCTGCCTCCCGGGTTCAAGCGA
TTCTCCTGCCTCAGCCTCCCAAGTATCTAGGATTACAGGTGCATGCTGCCA
CACCTGGCTAGTTTTTGTATTTTTAGTAAAGATGGAGTTTCAGATGTTGGC
CAGGCTGGTCTCCAACACCAGGCCTCAAGTGATCCGCCTGCCTTGGCCTCC
CAAATTGCTGGGATTAACAGGCCTCAGCCACTGTGCCCGACCCCAGCTTTT
ATATTCTAATGCTGAGATTATTCAGTTAACACTCTTACCTGCTAGGATAAG
TTTGTTGGAGAATTTTACCTTACCTTGTACCCTTTACCTTCACATCTACCT
GTACCCTGGCCCTTCACATCCTTTCCATATAATATATCTTCAGTAAATACA
GGGAAAAAAACCCAGAATGATTATGTTGACAGCAAAACATGTTTGTGCAGA
AACGGAGTAGTCACTATCTAAGCCACAGAGACTTAGGAGTGTATTCCTGAG
TTATGTATCATTTTAACCATCACTGGATCTTAAATCCCAGTTGCTAAATTG
AAGGGAGATACATGACTCTTTTTAGGGCTTTGCTCTCTGATACAGTAGCCA
TTAGCCACATGTGATATTTTAAATTTAAATAATTAAGTCAAAAATTCAGTT
TCCTCAGTCTCACCACATTTCAGGTTGCTGGTGTCTACTGTATTGGATACA
CAGACATAGAACATGTCTATCATCACAGAAAATTCTATTGCATTGCACTGG
GATAGGTACTTTTTGTGCCCTTGGGCTGATAAGTTCAAGTGCACTTAACTA
GCTTCCTCCAAGTGGAATCAGAGGATAAATTTACCATACAAAATACAGGAT
ACCCAATTATATTTGAATTTCAAACAGGCAACAAATAATTGCTTAAGTATG
CCCCTCACTGCACACCCAAATATTACATGAGACATTCTATACATATATATA
TATATATATATATATATATATATATATATATATATATATATATATATTTGAAA
TTCAGATTTAACTGGACATTTGGTATTTTTAATGTGCCAAATCTAGCAACC
CTATCTGAAGAGCAAAACTGGAGTGTCTAGTCTGGATAGGTCCTTTTACAC
CACAGGGAGTTATTTGAGGAATTGAGAAGGGCTGTGGTACCTGTAAAGAAC
TAACTCATTATGAAGAAAAGGATCTGTAAGTTTTTCTGTATGTGTAAGGAA
GGCCAAGAAGGTGGTTTCCAGATATATTTACTTTTTCTTCTCTCTCTCTTA
GGTTGCAAAAGCTTCTCATTTCAGAGAGATGCCAGGATCCTAAGTGCCTGC
CAAACTTACCAATTCTAAGGAATAAGTGGATGGATGGCATTACTGATTCCT
ACATTACTGATTGATTCTGCATCCGCAAATTGTTTTATTAAAAACATTCTA
CATCATGTGTGGGGAGATAAGGAGGATAAAATGAAGAGAAAGAATATTATT
GAGGGGAAGTTCTTCTGAATACAAAATGTGTTTAATTTTTTAAATAAGTAT
TACATTCACAGGGTTCAAACTATTTGAAGTAAAGAGATTATATATAAAGAA
TCCATCCCTCAACTTACCCAGGTGGTCACTTTTCTTTTTCTTGTGTATCTG
CCCAGTATTCATTCCTGCTGATATCAGTCAATAATGAATGATACGTGTTTT
CTTCACTTTTTTCATTCTTGTCAGGTAGCAGACTGTGTAGACTTTTCTGCA
CTTGCCCTTTTCATAACAATCTATCTTGGAGAACTTTCCCTATGAGAACAT
ACAGAGCTTCCTGTACACAGTTGCATGTACTGCATTATGCAAATGCATTAT
ATTTTATGTAACCTGTCCACTGTTGGTAGGCACTTGAGTTGTTTTAGTCTT
TTGCTATCAAACAGTTCTGGGATGATTAACCCTGATTTACTGCAAAATTGA
AATTGCTCTGCTATTCTGCTGGAATGGTGGTAAGTGAACTGAAAATTCCAG
TCACTCTTGGGCTAGACTCAACGTTCTTAAAAACTATGTGGCCATCACCAA
ATTAGTTATTTTGAACCTTAATTTCTTCACCTCTAAAATGGAGGTAATACT
```

FIG. 8-210

```
TACCTTAAGTGGCTATGAGAATGAAGATCATGTGTATGAATTGTTGGTGCT
CTAAAGAACAGCACAAATAAAATTATTTTCAAATTTAATTTTAATTGAACT
ATGTGTAATTTCTTAATTTTGAAATAATTTTATTTGTAATGTGCATAATCT
TATTTAATGTATAATGTATACATTGTAATAGAAACAGATTTCCCAAATTCC
AGCCTGGCATGAGGTAATAAAAGGTAATGCAAAGGGAGAGGAAAGCATGTG
TCATTAATTTTCTGCCTAGGACACCTCCCTGGTTAAATTGCCATTTCCTTT
CTTCCTTGCATAATGATTAGGAAACACATCCTCCTGACCTGCCTGCCCTCT
TTTGCCTACTTTTTCATCTGCAGTCAAGGTCTGGTTTTAAGACTGACTGT
TACTTTTACAAATCTGTGTGTATTGGTGGCTAAGGGCCTGTATGGTCCAC
TGCTGTATTCCCAGGTCCCAGCATGGTGCCTGACGCTGCCTGGCAAATAG
TAGTCACCCGAGAAATGGCTGATGAATTCATGAGGCCTACTCTGTATGGA
AATTTCAATTCTGGCCCCGAATTTTCAGGAGCTGGCAAGAGAGCCACCTT
AATATCATAGGCTGAGTTGGAAGAAGGGAACACCCAATTTATTCTTAAGA
AGTACTTTGCCCAGGTACTGTGGCTTAGGCCAGTAATCCTAGCATTTGGG
GAAGCCAAGTTGGGCAGATGGCTTGAACCCAGGATTTCGAGATCAGCCTG
GACAACATGGAGAAACCCCATCTCTACAAAATATGTAAAATTTAACTGCT
TGGTGGGCCTGCACTTCTGGTCCCAGCTACTCCAGGGCTAGGGTGGGAGG
ATTGTTTGATCCCTGGAGGTCAAGGCTGCAGTGAGCCATGATCACAGCAA
TGCGCTCCAGCTCTGGGCAACAGAGCGAGACCCTGTCTCAAAAAAAACAA
AAATGCCTATACAATAAATCTATAAAAAGTGGGTTTTGTGTGTCTATACA
CACACACACACACACACACCTGCATAGACACTCAGGTGTTCTGGAAAGAC
ACAGGAATCTGAAGCCAAAATACTTGTGATTTTTTTTCAGCTCTGCCACT
CACCAAATGTCTGATGGGATTAGTTACCTGCCATCTCAGAATTTCTCTTC
TGTAAAATAAGGTAATAGTACCTCCCAGAGTTATGAAAAACTATCAAATG
AGATGGCAGATGAGAAAACACTATATTCCTTGTAAAACCTGACAAATATG
TGCAAGATTATATAAAGACTGTCTTCTGTCCATTTTCAAATGTGGAAAAG
TGAAAGCAGGACAGGATGTTGGGATTTCTGTCAGAGATTTGCTGGCTTCC
ACCTGCAGAAATTGAAGTAATTGGGGTTCTTACACCTAAGTACTAACTGA
GTCTGGTTGCAGTTTGCCCCCATGGCTACATGAAGCTTTTAGAAGAGTCA
GCATGGTAGACATGGAATGTTGAATGGTGGTGGAGTGTACCCACACACCT
CCCACCAAGTCAGCTCCAGGTTCAGAAGCAGCAGCCCCAGTGGAAGGCAT
GCGTGTTTGTAACTCAGCTGAGCCACCTTTCAAGAAGCAGAAGCTTTCCA
AACAGGGATGCCCCCTGCTTTTGGTTCAACTTGACTTCCTACCTTCAGTG
AGGACATGGAGAATTCATCTAGACTGGGTACCTGAGCAAACTTGGCAGAG
CAAAGAGAAATGTGGAAGGCCCTAGGTAGACAGGCCCTGTGGAAGGAAAG
AATGAAAGAGGACAGAAAGAAACTCCCATTTTCTTTAGCACAGTCCCTTC
AGATTAAGGATGAAGAGGCTGGGGTTCTGAATTGGTTGGCCTTAGGTAAT
GGTCACAAAAACAAGTCAATGGCTTTTCCACATCCGTACATTGAGATATA
TTTCTGCCCTTGGTATTCATTTTCTCTGACCTCCAATTAAAGATCTATGC
GTCATTTTAAAGCCTTCCTTCCTTTCTACTCTGTGGTCAGCGTAACATTG
GTGGTTTGAAACTGGCCATAATAGCAGCATTTACATCATGGGAACTAGCA
TATGTTACATCAGGGTTTTTTGTTTTGTTTCTGGAGAGCCAGTAAACAT
ACATCGTCACACCACTTAAATATTCTCTGCTTAAATATTCTCTGCTC
```

FIG. 8-211 >HLA-H.CONTIG

```
TTTGTAAGTATTCTATTTTATTTATATGTGTTTGTGTTTCTGAGTATGTCCTGA
GTTGCACGATAATACTATATTTCTTATTGGGTAACATTGTCAGAAAAGTTTCTA
AAAACTTTCTCTGCTGCACTTATTTTATACATTTTATTTATGTTAATAATCTCA
CATTTAACACACTTATGATTTATTCTCAACAGAAAAAGGTGGTATTTCTTTCATT
TAGTCTTTTAAAAAGCTCACATTATCAAATGATTGCTCAATCATTTAATCTCTTT
GCTTCTCTTATATGCATTGATTTAATAAATATGTATACTAGTTTCTCCATCGATT
CTTTAGATTTGAAACTTATTTTCCTTTTATTCTTACAAAACTGACTTGTCTATAG
GCCCACTTCTACTTCCTTTATTCTATCATCTTCCTCAACTTATTCTGTGGTCAAA
GAATGGAGAAATAATATTAATAATATGTTTTTCTCATCAATGACTTCCACCTGTT
CTCTGAGAAATTCAGCTTCAAGAACTTTAGTTTGATATGACTGCAAAGATAATAC
ACAGTCTAAATCATAAAAATGTCTCAAAGGTTTTTTTTTATTTGTTTCTTTGAA
ATATCCATGAACAGGCATGTTTCTCCCCCTGTAGTGCAATTTGTGTGAAATTCTG
GCATGCACTTAAGAGGATGTCCTAAAATACCAATATTTAATTGATTCTAAGTCAT
GTATTGTATCACATTTTTGCCCATGGATTGTTGAAATCCATGGACAAAACTGATA
GCATTTTAGAACTTCCTTTGTCTAGTGGCAGTCTTGATATATTCACACTATCTAT
TGACAAAAAATCTAAAGCACCAGGCTCAAAGCTTGTAGAGTAGGTGTCAGTGATT
TGGAGGACATCTCTAGGGCAATAGTAGAGGCATTTTTAACCCCTAACAACTAAAT
GATCATCAGAAGTGAGTGATATCCTCACTCATGACCCCAACTGCTCTAATTTCT
ATTGTTTTCTTGCAGAAATGAGAGCAGGTGGGGTCATGGGTGAGGAATGAGGTG
TTGAAAGTGAATGGGGTGTTGAAAGCAAGGTGTTTAGCAGTGTTCTGAAAGCAT
ACATTTAAGTAGGCTATCCGGGCACTGTCAATAGCTAAGTGTCAAGCTAAGTAC
TCTATTTTATTCTAAGAACTATTTTTAGAAATGCTGAATCAACAAATCTCAGAT
GGCACAGAGGTTGTCATTTTTGAATAATATGAATATCAGTAATTTTAGTTGGAA
AAGAAGATTTTCAAAGAGCCATCTAAGTTTCCAAAATAAGTGTTGCAGTCATAT
TAACTATTATATTTTCCTGCCTGTTGATCTACTGCCTGTGAATTGCTTATCAAA
CCAACAACCAACTGGAATACATAGACTGCATGTCTTGTTCATTTCCTGCATTCT
CAAGTAATGGTTTAACAAACTCATGAGCTTACTCTTTAATCTGAACCATGCTTA
ACTTCAATTATGTTGATTTAGTCTAAGGATGCAGAATTTATTTTATAGTTATGT
AGGAACTGGAATCCAAAATGTAATATGCCTCCAAGCTTTTCTTTGTTGGCCTCT
GAAGGAGCATCACCTCTACAACTTCAACGTTGTTATGAATACCTCTGGGGAGGT
GTTCACCTCAGGACCCAAATTTGGAAAAAGGGAAGTGCCACTTTGGAGGAGTGC
TCTGAGCAGCTGATCCATTAAATGTCCCGATCACATGCACGTGGAAGTGTCATT
GCAATATCTGCACTAACAGAAGCTCAGTGACTTGAGAAGTGAGTCTGGAATTCT
AAGAAAAAGGCAAGGCATCTCTCTTGCCACTTGTTATTTTTCCAGTCAAGCAAC
TGTGATAAGAGGGCATGGAGAGCAGGAAGAAGTGAAAAATCCCAGGAAAGTCTG
GAGTGGAATCATTAAACCAATTCTGCTCCCTCTCTAGGCCAACTTGGGCCTATT
ATGAATAAGGAGGTCTCTTATAATCCATCTAACTCCACTCAGGAACAATTTGGG
GATCTGAGACTGTGAACTCAGTGGGCAAAAAAATATTTCTTGGCCTATCATTAT
TCTCTGTAGGATGTTAAGGACAGGTTTCTGTATGTGGAGTCCTCAGTTTTTGCC
TTCTCTCCTTGAGATATTTTTATGCTATTTAGTAATTGATGGCCACAGTTGATC
GACCACATTTCTGGGCAACTCTAATAATCCTTGTTATATTAATCATTGGACCAA
TCTTGATTGTGTATGACCATCATCTTGTAGCTACCACCTCTATGTGGATGCTCT
CCTCACCCTGCTTAAGTGCCAATGTCTGTGCTATGGGCCTACCTGTCACATGGA
TAATCTCTTCACTCCAGTCAGGCTCCAACATTAACACAGGGCTGTTCTCTTGTC
CCCCTTTGAAGACAGCTTCATCACCCTATTCAAGTTGCAGTACTCTCACTGGGC
TCCACTGTTGCCTCTCTCTCACTCTGCTTAGGTTTCTTCACTCCACTCCAGGCA
```

FIG. 8-212  ACTGTCACTAAACATCCTTTCCCCCATATATAACACAGACATCTACCTTGC
TTGGCCAAACCCACTGGATTTCAGACTCACTCATTCAGAGAGTAAGACAGA
GAGGGGTTCATTTTTTATTTTATTTTATTTTTTATTTTTTGAGACGTTGTC
TCACCCTGTCGCCCAGGCTGGAGTGCAGTGGTGCAGTCTTGGCTCACTGCA
ATCCCCACGTCCCAGGTTCAAACGATTCTCCTGCCTCAGTCTCCCAAGCAG
CTGGGATTACAGGTGCCTGCCACCATGCCCAGCTAATTTTTGTATTTTTAG
TAGAGACAGGGTTTCGCCGTGTTGGCCAGGCTGGTCTCGAACTCCTGACCT
CAAGTGATCTACCCGCCTCGGCCTCCCAAAGTGCTGGGATTACAGGTGTGA
GCCACTGCGCCCAGCCGGGGTTCATCCTTAATACATACATTAGAGATATAG
ATTCTGTTTTTATCTAAAAAGTCTTTATAAGGCCGGGCGCGGTGGCTCACG
CCTGTAATCCCAGCACTTTGGGAGGCCGAGGCGGGCGGATCACGAGGTCAG
GAGATCGAGACCATCCCGGCTAAAACGGTGAAACCCCGTCTCTACTAAAAA
TACAAAAAATTAGCCGGGCGTAGTGGCGGGCGCCTGTAGTCCCAGCTACTT
GGGAGGCTGAGGCAGGAGAATGGCGTGAACCCGGGAGGCGGAGCTTGCAGT
GAGCCGAGATCCCGCCACTGCACTCCAGCCTGGGCGACAGAGCAAGACTCC
GTCTCAAAAAAAAAAAAAAAAAAAAAAAAAAAAGTCTTTATAAAAATCTG
ATTGAATGGTTGAATGCTGTGCTAAAATCTGCATAATATCTTACAACACTT
CTGTGAATCACGAGACAGTTTTGAATGCTAAATGTCAGTTAACAGATCTAA
AGGGACCAACATCTGCTTTCCCAAATTATATGAAAGAAGATCCTGATCCCT
CATCAGGTGAAACTCACATCAGACAACAGTGTCTGCATTTCTCCAAAACCC
GCCTCAGCCCCATGGCCACTTTCCAGGGTTATCCTGCCTACCAAGCACTCT
CTTTCCTCAGAAAAACTTGGGGGAAAATGTAGAATAATAATTTTTTGAAGT
TCTGACCAACTTCTTGAATCACTCAGCATGTTTTTGACTGCAGGTACAGAA
AACGCTGACTCAACAAATTTAAACACTATATAAATTTCTTATCTCCCCAAA
CAGGACATCAAAGGCAGAAAGGTTCCAGAGCAGGGTGATCAGAGCTCTGGC
TCCACTGCCCTCAGTCTTCTTGCCTCTGCTCTCCTTCACAGCAGGCTTTAC
CCCCCATGCTGGTCACAGTTTCAAGTGTCCATGCAGACACAAGTTAAAGGC
AGGAAGAAACAGTGCGTTTCTCTTGGAGATCAAGGAATGCCTTTCCAGAAA
ACTCCCCCTTATGTCTCATTTGCCAAAACTTGGCCTAGTCTCAGGTGCTGC
CTGAGCTAATCAGCTACAGAAGAAGGGACCACATGACTGGTGTGGACCAGT
CAGAATTCACCACATGAAGCTAGTAATGTGGCTCACACTTCCCAGGGGGAT
ATGGCCAGGTAGCAGACAGTGGATCGCTGAACAGAATACTGATAGATTTCA
GCACCAAGGTTAGAATGGCTACCACACCTAATCCCACCCTATCCCCGTTTC
CTTCTTTAATTTTTTCCATAGCACTTATCAGTAGCTGACAAACTGTATATG
TTTTTACTTTTTTATTGTCTGTAGCTCCCAAGTAGAATACAAACATCTGAA
ACTCACTGTATCCATCCTGAGTAATGTTCTTTTCAGCTCAGTCACAATCAT
TTTTTGATAGCCTATCCTATAAGCTTAACTTATAGTGTTAATCAGTATTAA
TACATCTTAGTGGGAAAGAAGGAAAAAATAAACGATCACACACACACACAC
ACACACACACACACATACATTTACGTAACAGAGCAAGTGTGAAAATACC
TAAAGGCTTTATAGCTCCTTTTGTCAATGGATACATGACAGCATTTTTGGC
ATTCTTTACTACTCTTATTCTATGCTCCATTTGTCTTCAGTCAGCACCTCA
GCTGCCCTTATGTTTTACTTGGTAAGGCAAATTCCTAAATGAGCCTGGTAA
TTAGTCATCCAGCTTATAGGAAGGTACTATAGTTTTTCATTAACTTTTTCA
CTGGGCTTGAGAGTAGTAAGGACTCCCAGAGAATTCCTTGTGTTCCAAAAG
TACTTCTCCTTGACATCTTGGTATAGGATTAATAACTGTTTACCTTTGATA
ATCAGGAAGAATGACTCCAGCTAGTACAGTTACGTGATGCCTATACATTCC

FIG. 8-213

```
TTTTTTTCTGGGAAAAATGTAATGTGAAATTAAGTGCAAAAACCATGCCTT
GTTTATGTATGTATCAAACACTTCTAGAGCTTTCCCAATACAGTTCTCTTC
TCAGCAAACAAGAGGACTATACCCTCATCCCCACCCCTGCACTTAGGTGTA
GCCAATGTGTTGTAACTTAAAGAGGAGAGGGCACTGGATGAAGGGAAATCT
GTCTAACAAGCTTCTTTATTTCACCTAGTGGAAAAAAGCCTTAATCTGCAG
TGGGGCAGTTTTCAAGGACATAGACTGAATTGGCTCATGCATTTATGGAAG
ATGAGGAGTCCCATGATCTGTAATCTGCAAGCTGGAGACCCAGGAAAGCTG
GTGGTATGATTCAGTCTGAATCTGAAGGCCTGAGAACCAGAGGAACTGATG
ATGTAAATCCCAGTTCAAGAGCAGGAGACCAGATGAGATGTCCCAGCTCAA
GCAGTGAGGCAGAAAAAAGGCCCAAATTCCCCCTTCCTCTGCCTTTTCTT
CTATTCAGACCCTGAATATCAGGTGGCATAATGCCATCCACACTGGGAAAG
ACAGTTTACTTTACTAGGATCACCTATTCAAAGGCTAATCTCATCCAGAAA
CACGCTCACAAACACAGCCAGAAATAATGTTTAACCAGATAGCTGGTTATC
CCCTGACTCAGTCAAGTTGACACAAAAAATGAACTATTTCAAAGCTTACTG
TAATCAACAGTTTTGTCAAAAAGATAGACACAAATCAGTGGAATGAGATAA
ACAGTCTAGAAATAAACCAACAAAAATATTGCCAACTAAGGCAAAGGTAAT
CAATGGAAAAAGATAGTCTTAGCAACAAATAGTACTGGAACACCACAATG
TGTTAATAAAGTGAAACTGGAGACATCTCTCACACCTTATACAAAAGTAAC
TAAAAATAAATCAAAGGACTAGATGTAATGTATCAAACATTACATCTTTTA
GAATGTATCAAACATTACAAGCTTTTAGAATAAAATATAGAAGAAAATTTA
CATGATCTAAGATTTGGCCCCAATGAAGTTTTAGCTATAATAACAAAAGTA
TTAGTCATGGAAGAAAACAAAATTGATAAGTTCAGGTGGGCTAAATTAAGG
GAAAAAAATCACTTTGCAGTAGAGAAACCTGAAACATTACCTAAACCACAT
GATGAAGGTTAATATCAGTGATGTCATGTGGATATCATGTTCTCCCTAAAA
TGATGTGACAAGAAGGGCCCTTTGCCCTTGTGGTATTATTTCAAAAAATCT
ATAACTCCGGTGTAATTATGAAAAAAAGCAAATGATCTTCAGGACTGTTA
AGGTCATGAAAAGCAAGAAAAGACTGAGACATTGTCACAGACAAAAAAAGA
CTAGGGAGATATGACAAGAAAATGCAGTGTGGTATTCCAGATTGGACCTTG
GAACAGAAAGAAAACATTAGTGGAAACAGTGGTGAAATCCACATAAAGTCT
AGGGTTTGGTTAATAGAGTTTCATGTATCAATGTGAGTTGCTTATATTTGA
CAAATGTATCATAATAATGTAAAATCCTAACAATGGGGGAAAGCTAGGTGA
AAGATATATGGGAACTCTCCTGTACTGTCTTTGTACTATCTTTGCAACTTT
CCTGAAAATCCAAATTATTCTAAAACAGAAAAGTTCATGCTATTAGAAGTG
AGGATAGAGGTTACCTTGAAGAAGCTGAGGTCTAGAAGAGACCATGAAGGG
TCTAATTAGCTAACACACGTTGAGTATCCCTTATGCTTAGAACCAGAAGTA
TTTCAGATTTTTTCAGATTTGGAATGTTTGCATTATACTGAGTATCTCAAA
TCCAAAAATCCAAAATCTGAAATATTCCATGAGCACTCCTTTGAGAATCAT
GTTAGCATTCAAAAAGTTGCCGATTTTGGAGCATTTTGAATTTCCAATTTT
TAGATTAGGAATACTCAACCTGAGTAGAGGCTGCCTGCTAATTACCTGGGA
GCTAATTACATGGATATGTCATTTTGAGAAAGTTTAGCTTGCTGATATGGA
TGATTTTCTGGATAAAAATTATACTTTGATAACAATTCTTTTAAAGGAGAC
AATAATTATTAACTTTTAAGTACTTTTTAGCTCTACAATTCAGAATTCTTT
AGTGCTAAATATTACATATTTTGAAACAAAAGTTTTGTTTATATTTATTTA
TTTGTTTCCCCCCCCCTTTTTTTTTTTTGAGACAAGTTCTCACCTTATTG
CCCATGCTATAGTGCAGTGGGTGATTATAGCTCACTGCAGCCTCAAACTCC
TGGACTCAAAGGATCCTCCTGCCTCAACCTCCCAAGTAGCTAGGAGTACAA
```

FIG. 8-214

```
GCATGCACCACCATATCCAGCTAATTTTTGTTTATTTCTACAGAGGCAGGG
TCTCACTATGTTGCCCAGGCTGATCTCAAATTCCTGGCCTCAAGTATCCTC
CCACCTCTGCTTCCCAAAGCGCTGGGATTACAGGTGTAAGTCATTGCACCC
AGCCAAAAGTTTTATTTTAAACTTATTATTATGAGCATGTAACAGATTTAT
GTGGTTTGAAATTCAAACCTACAAAAGAAAATAATAAAAAGCTAACAGATA
GACAAACAAAAACAAAAGCAAAACCCCACTTGGCCATGCTCTCTAGTTCCT
CATTTCTCTCTTGGAAGAAACCAGAGCAATGTTCCCTGTGTATCCTTCCAG
AGATAATTTTTTAAAATACTTTTTTCTTTTTAACAGAAGAGATGGTAGACT
ACTTCTTTTAAATTAAATTAATATACATTTACTTGTTTCTTTTTATTGCTA
TAGAAAATGAAGTTGGGGAAACAGGAAAAATGACCTAGTATTATCATACTA
ACATACCAAAATTTTTCAGTTATATGTATTTCCTGTTTCAGTTTTTACCCC
ACCTGTTTTTTATTTGGTTTGAAATCATAGTACAGATAAAAACTTGAGGCA
GGTATTTTAGACTTGTTTTTCTTTTGTAACATAAAACTTTGAGAGCACCAG
GAAATCTGGAAATATTCATTTAGTTATTCATAATTCAAAATATTGTTATAT
CCACTTTGTGTCAGACTATTTGTTAAGAACTAAACTAAAAGAAAAAGATGG
GGCTGGACATGGTGGCTCACACCTGTAATCCCAGCACTTTGGGAGGCTGAG
GCGGGTGGATCACCTGAGTTTGGGAGTTCGAGGAAAGCCTTGCCAACACGG
TGAAACCCTGTCTCTACTAAAAATACAAAAATTAGCCAGGTGTGGTGACAC
ACGTCTGTAATCCCAGCTACTCAGGAGGCTGAGGCAGGAGAATCACTTGAA
CCCAGGAGGTGGAGGTTGCTGTGAGCCGAGATCATGCCACTGCACTCCAGC
CTGGGCAGCAAAGCAAGATTCCATCTCAAAAAAAAAGATGATAACACCCTC
TGGGAGATTACATTCAGATAGAACAAATAAAGGTGTAGAACCTAAGATGTG
ACAAGGACACTGTTGGGTGACTGATTCTTCCTGGGAACATTTATAAAGGCT
TCCTAGGGGAGGGCGTGTTTGTGTAAGAGCTTTCCAGGTCAGAAAGTATGT
ACAGTGGAAAATGTATATGAAAAGACCGTGTTTGGGAATCAGGGATTATAT
ATTGTGATTAGAGGAAAGAGTCCTAGGGTTTGATACCTACAAAGAATTAGA
GTTTCTAGGTGCTTCTGGACATGTGGATTGATGACAGCAATACTAAAAATA
CAAAAATTAGTGGGGCATAGTGGTGAGCGCCTGTAGTCCCAGCTACTTGGG
AGGCTGAGGCAGGAGAATAGCTTGAACCCGGGAGGCGGAGGTTGCAGTGAG
CCGAGATTGTGCCACTGCACTCCAGCCTGGGTGACAGAACGAGACTCCGTC
TCAAAAAAAAAAAAAGAAAAAAAGCAGGAGTTAGCAGAAAACCAACAAGAC
ATGGGAAGGAGAGAGAGAGCTGCAACACCCAAGAGAAAAAATAGCAATGCT
GAAATCAAAGTATAATGAAGGAGAGAGGATGCTGGAAGCTATGAAATTCTT
TCTGTGAGGCAATGGGGCAATGACCCTAGAACTGCTGAGTTAGCAGCAGTG
ACAGACTCAGTGCCAAATCATATATTAGAAAAAAAAATCAGATAGAGGTAA
AGTCCAGATCCAAAGAAGAGGGTTTTTAGCAGTAAAGCAGACAGTAGAACC
CACCCAGCTTTCTAGGGTGCAGGGGGCCTCCCTTTCAGGCATCATGAACAG
TGGGGGACCATAACTAGGCATGATGGCTTCAGATACAGGGCTTGTTCATCT
CTTGTTGTGGTCAGGCACTGCCTAATGAGAGCAACCCCTTCCAAATGCTAC
TGCTGTGTTTAACTAGGGCTCTTGATAATCTGACCAGCTTCTGTCTTACTG
ATTTTAGGAGAAAATGGAGCAACCTGCAAGATGAGTGGGATTAGCTTCGT
GCTGTCTCCCATGCACACCACTCATGCACACTTGGCGAGCATGGCAGTTCC
ATTTATTTGCACCCAGTTGTGATTTAAAAACTTTTAATTAATTAGTCTTA
TTAGTCTTCAGTTGGATTTAAATGCCAAATAATAACCTTCTACCTTGTAAG
AGGAGCCCTTTTACCTAAAGCAAGGCTTAAGTTTGGATAAATTTTGTCCTA
TTTATTATTCATCCACAAGCTCTCTTAAAACACTGAATACACACTAAGAAG
```

FIG. 8-215

```
GCTCTCAGCACTCCGAATAGTGTGATAAATCAAAAGCCAGTAACTTCTCAA
AGTCATTGTGTATTAGTCAGGGCTCTCCAGAAAAATAAAACCAATAGAACA
TATATACATGGGCTTTTACCCAAATGTCATCTTTTCAATGAGTCCTCTTGC
CTGCTTAATTTTTCTTTTTAGCATTTGCCACCTCCATATAACATGCACTTT
ACTTATTTATTGTCTTATTCTCTTTCACATGGGCAGGGGTTGCATTTGTCT
GTTTACTGCTGTATCCCTAGCACCTAGAGTGGTGCCTGGCATACGGCTGGT
GTGTGATACATATATTTGGAGTGGAGGTAAAAGTCACCACTTAGGCTATCC
ACTTTTGTGACAGGGACAACACACGTATCACTTGTCATTGTACCTATAGCA
TCTCACCCAGAGCCACAAAAAAAGTGGCTCAAAGTATATATTAACAAAGAA
CAAAATGGAATAATCCCATCTGAAGGCGAGGATATAATAAAAGCAACATAC
CTTTTTTTGGAAGGACATGGAGAGCATCAACCTTAAGACTAAAGACTAAAC
TTGAGAAGCAATTATTACATTTCTATTAAAAATTACCAAATACAAATAGTT
AACTTTGAAGAAATATATGAATAATGATGGTATCTGCAAAAGAGGAAAAGA
CTTACTCAATTTCATTGTACCTTAGTTGTAAATAGTATTCAGGCCACCATT
TGGAACCTATGTGACACAGTTTAGTTCCTGTCTATGTTCATAAGAGAGGGC
AAAGGCCCGTTTACATCCAACCTCTGTATGCCAGCAGCCACGTATGCCACA
CTCTAAAATGGCTAAACAGTCATTCATCAGAATCGGTTCCAAGAACTCCAA
CAAAAATTAGAGCTCATGGTGCCAGATTGGCCTGGATTTTCATGCTCCTGG
GTGATTACAAAGTTGTAAATAATGATGCTGTCCACTGATTTTCATCATGCG
GGGCTCTCTGCTTCACTGTGCCTTCCTCTTATGTCCATGGCACCAATTTCT
CTGATAGTTCCCCCAGGGGATAGGGTTAGATGTGGGTTCATAAGCGCTGGA
CCACTGAGGGTAATTCACTCTTAAGACTAGCGAGCACTTTCTGAATCTGAG
GAGTCACATATTAAAAGAGGCAGAATCATCTTCTGATTTCAAAAAAGCAAC
TACATGACCACCCTGAAAGTGATTTCAAAACAGTTGAAAGCTAGCTGTTCA
AGTTGATAAAAGCCACTGCAGTTCCCTGCAGGGAATGCTGATGGGCTCCGT
TCCCTCTGCACATTAGAGCCATTTAAATGAAATAATTGATCATATTAACTG
AAATCACCTGGCTTATAGCTCAGGTCCTAAGAATTGTTAGTGGCACTTGGA
GCTACAAGAGGAGTCCCCAAAAGAAACGATTCTCACTTTATTTTGGCAAA
TGGGTGGCTTAAGTAGAACTGGTCCTATTCCATAACAATAAAAAAGGAAAA
AATAAATTTTATATAAACTTATTTCCAAGATTTCTTACCCCTTCTTGTCAG
CATTTCAACTTTATTTGGTGGAACTATCTTTTCTCAATTATGTGTGATGTA
TTGTGGTCGTGAATCATGGTGTCCTGAACTCCCTTTGGAAGCTAAAACGGT
CTGTTGAGGCTCTGCCTACCAGCTCTCTAGGGTTTGTTAAAGCAAAAGAGT
GAGCACTTTACTTAAATTTCACCAATTATATTATCTTCTGAGACCTTAAAT
GTTGAGTAGAGGGAAAATACAAGTTCAAGCCTATTTATTTCAACAATGGAG
CAAGTTGCTACAGCTAAGACCTTTTGAGGCTGCCTGTTTCTTCAGGTTTTC
CTTTGATTCTCAGAGTAACCCCACCTCAATTTATTTGAATACATGTACTTA
TGGCTTAACCAACACACAGGTGGTTTCTTTAACTACAGTGCAAAAATCTTC
ACACATACAAACTTTTTAAAAAACAATTCTCAATATGAAAAAGAGAAATCA
ATATAATTGGCTACAAATTATTGGCATCTTTTCAGAGATTTTCTCAAGAAA
GTAACTGAATTCCTAAAATTCTTATGACTTTGTTAAAGGACTCAAAATGAA
CATATATTCTGGCTGGGCAGGTGGCTCATGCTTGTAATCATAGCACTTTGG
GAGGCCAAGGATTGTGGATCACTTGAGGTCAGGAGTTCGAGACCAGCCTGG
CCAACATGGTGAAACCCCGTCTCTACCAGAAATACAAAAATTAGCCAGGCG
TGGTAGTGGGTGCCTGTAATCCCAGCTACTTGGAAGGCTGAGGCAGGAGAA
TTGCTTGAACCCAGGAGGCAGAGGTTGCAGTGAGCCAAGATTGCGCCATTG
```

FIG. 8-216

```
CACTCCAGCACGGGCAACAGAGGGAGACTGCATCTCCAAAAAAAAAAAAAA
ACAAAAACCTCATATGTCCTACAAAGCAAGTGATAAAAATCAAAATATGAC
AATGGGCTGAGAGGAAAGGGAAACTAGTAGTATTAAAGAAAGTTTTTAATG
AACAAATAATGTTAAGGCGGATTTTTTTGTTTGTTTATTTGTTTTTGGCCT
TTTTTTTTTTTTTTTTTTTTTTTTGAGACAGAGTCTCACTCTGTCGCC
GAGGCTGGAGGGCAGTGGCACTGTGTTGGCTCACTGCAACCTCCGTCTCCT
GGGTTCAAGCAATTCTCCTGTGCTAAGGCAAATTTTTAAGGATTATAAATA
GTAAATATTAGAAGGGATACTGCTTAAAAATAAACAATTTGGATAGCTAAA
TGGTCTTCAGACTCTTTTGATTGTACAACATGTAAAAGAATTTTGAAAACT
TTAGGCATTCCTTTGAATATTTTTAACTTGATTTCTAAAACTTTTCATCAA
AAAATAAATTGTTTTGTAAATAAAAGAAAACATTAAACATGTTATAAGATG
AAATAAGATGAAGAGTGACTATAATTAGAATAAGTATTTCATGACATAAGT
TTATTTTAATAAAAGTTCTAACCACTTTATTGTATCATTCATATCAAGTTT
TTTAAATATATATTGAAATTTGGTGCTCTGGGAAAATATGCCAGCTTCATT
TGAAAGAATGAGTTCCTATCCTGTACTGCTTCAGTTATTCTGAATTCAGAA
CATTCCCACTCTGGCCAGTCCTCTCTTATAATAAAACATACAATACTGTGC
ATATTCTCAGTGATTAAAAAAAATACACACAGCAGATAAAAGAAGAGGGAG
CAGGCAAACCAAGAGCCAAGGTGAATGTGTTAATCATTAGCAGGTTATCCC
CAAACCAATATTTGGAAGTACTCCTTTGTTGACAACCAGGAAGTGTTTACA
CTTCAGGCATTGCACCTAAATAAAGTGTGGATGCCTTTCCTTTCTAAAGTG
GAAGGAGGGATATTGTGGACATAGGCACATTCTGAGGCAATTTTAGGAAAT
AAGTTGAAATTGATGGAAATTGAGAAAGACTTTGGAAAGTGTTTGCCTGCC
TCCACTACCAAAAAGTCCATGGAGAAAGCAAAGTAAAAGGTCCAAAAATGA
AAGTCAGCAGAAACCAGAAAGATGGGCAACAAGGTTTTACCATACAGATAA
ATAGAAGAGAGATTCTTAGTAAAGAAAACAAATTGAGGACAATCACTAAAT
AAAACAAAATCGAAGGAAACTCTAAGACCACCAGCCAAAAAGCAAGAGAAA
ATGATTAACACCTTGGCACATCTTGGTGAAGGAATTCCAGGATAAAGAGAA
TCCTATAGCACCTAGCCTAAACATAGCTCTCCTACAAAAAGTAGCTGGCTA
ACTAGACTTCCTCATATTGGACATCAGAAGAGACTAGCAGGAAGTCAATAC
TGTTTTGAATAAGACAAATTGTGGAACAAAATTCTGTTCCCAGCTAAGTT
AATATTACAATGTTTTAAGGCTCCACAGTGATCATAAAGAGTACTATGAAA
TAAATTCTCAGCTACTGTGGGACTCAGAGGCTCATCCAAGTACTGCTCCAA
AAAAATACTCCATTGAAATGTTTTGAGATGAAGAAGGATAAAGGATGGACA
TGAAAAAACAAAACAAAAAACACTTCATTGTCCAGGGGTATGCTAAGTGAG
CAAGAAGTGTCCAGCACTCAAAATTAAGGAGGCACTCACTCTCATGTGCCA
ATTCTGTTCTTGCATGAGCCTAAGAAAGGATGCCTCCTTAAATATTGCTTC
TTGGGCACCTCACTTGCCTCATCTTGGTTTCAGCCCTCAAATTATGTTCAA
ATAACAGTGAAAAGTATAATACCCAACAGAATGCAAATGGTATAATTCTTC
TATGGAAACTACTCAATGCAAAATTAATACATTAACTGCAAAAGGTCAGAG
CAAAACTTCCAGAGAACAGTAGTGAAACCAAGAGTGAGATGATAGGATGCC
TCAGTGTGTCTGTTTTCTTATTATATATAAGGAGAGAGACATGGCTAGGCA
TGGTGTCTCATGTCTGTCATCCCAGCATTTTGTGAGACCAAGGCAGGAGGA
TCCCTTGAAGCCAGCAGTTTCAGACCAGCCTGAGCAACACAGCAAGATCCC
TGTATCTACAAAAAAAAAAAAAAAAAAAAAGCTGAGAGTCAACAGCCAC
TTTTTTACTATATAGGTTATTAACTTGAGAAATAAAGCATTAAAAGAACAA
TGAATTTGGGAGCACAACACAGCAAAATGTAATCTGCCCACAAAATTGGAC
```

FIG. 8-217

```
TTAGAGGAGCAATTTTCCTCTAAGCTTTAACCTGTTTCATAATTAAATGAA
AAATAAATAAACTATCCAAAACAAAATTTATATGAAGTAAAGCAAAGGGAA
ATAGGACATAAGCTTGATAAAAGATAAAGCTAATCAAATATAAAATAAAAA
GACAAGCAGGGCTGGGCGCAGTGGCTCATGCCTGTAATCCCAGCACTTTGG
GAGGCCAAGGTGGGTAGATCATCTAAGGTCAGGAGTTTGAGACCAGCTTGG
CCAACATAGCAAAACCCCATCTCTATTAAAAATACAGAAATTAGCCAGACA
TGGTGGTGCATGACTGTAATCCCAGCTACTCGGGAGTCTGAGGCAGGAGAA
TCACTTGAACCCGGGAGGCGGAGGTTGCAGTGAGCCGAGATCGCGCCACTG
CACTCCAGCCTGGGTGACAGAGTGAGACTCCGTCTCAAAAATAAATAAGTA
AATAAATAAAAGACAAGCTATTCTTAAAATTAGTAAATGACTAAGTAGTCT
AATGAAGGAGAAAGAAAGCACACATGCAATTGGGTCAGAAGTACAAAGAAG
CTAAAACCTCAGATATAGATAAAATGATATATTATTAAAAAGATAGCCTGA
TAAAACAGTTGAATTTTTGCAAATATACTTTAAATAGTGTGTAAAATAGAT
GATCCTCCAGATAACATAAATGGTCCAAATTGATCAAAGAAAAATATAAAA
CCCCTTAAAAGACCAGTAACTGAAGGAAATTGAGAAAGTTATCAAAGTCTC
CTCAAAATGGCTTTCAGCCTGCATGATTTTTACAAACCAATGCTTTCAAGC
TTTCAAATAACAACAGCAATTATAAAAATTCCATTCTAGTCAATCTTTTTC
AGAGTAATGGGGAAAAAGGAAAGTTCTCCTTTCTTGTTTTTGAAATCAGCA
TAAGCTCCATATCCAGACACAAAAAAGATACACAAAACACATGTATGCATA
CAGAGCCAATCTCATATATCAGTACATCAGCCAAAGTCCTAAATAAACTAT
TAGTGAATCAAATTCTGTCGTACATCAAAAGAATATTCAAGGGAAAGCTCA
ACATTAAGAAATACATTAATATAATTCATAATATTTAACAGTCAAGGAGAA
AAAGTAAGTCATCTCATCATTAGGTAGATGACAATAAACTATTTGAGAAAA
GTGAATTAATTTTCATGACTATTGTTAGAAACAATCCTTTAGGGATGGGGA
GGGGAGATGAATTAGAAATGTTTCCTATCAGTTCACAATTGCATCTATTCT
GAAGCCATTAGGAATGTGAATGGTAACTCTTCCTCAAACCATCACATAAGG
AAAGATACCCTGAAAGTCTGACACACCGAAGTCATCTGTCAGGAATCAATC
AGAGAAGCTGCTGGGAAAACCTCAGAGAAGCTGCTGGGAAAACCTAGGCAT
TCTGAGTCATCATTGTTCTTATCACCCGTGGCAACTGATGCAATTGGAAGC
AACTGATGCTTTCAGGGTCATGGTTTCTTCAAAGCCTGAGCTCATTAATTT
TGCTGTTTGAGAACTTGCAGTTTGATCCAAAAGCTGACAGCATCGATTGAC
CCATTGCCTTCCTTCCTGCTCTGATACTGGAAGTTCCAACAAAAGAGGAGG
AGGAACAGGACCAAGAAGAACATGAAAGCAGAGGACCAGGGGCCGGGCGCG
GTGGCTCACACCTGTAATCCCAGCACTTTGGGAGGCTCAGGTGGGCGGATC
ACGAGGTCAGGAGATCGAGACCATCCTGGCTAACATGGTGAAACCCCGTCT
CTACTAAAAAATACAAAAAATTAGCCGGGCATGGTGGCAGGTGCCTGTAGT
CCCAGCTACTGGGGAGGCTGAGGCAGGAGAATGGCATGAACCCGGGAGGCA
AAGCTTTCAGTGAGCTAAGATCGAGCCACTGCACTCCAGCCCGGGCGACAG
AGTAAGACTCTGTCTAAAAAAAAAAAAAAAAAAAAAAAAAGCAAAGGACCG
AAGGACCAAGACCCCTTCCCAACTGCTCCATTGGTCAAAACGAAGTCAGAG
CAGAAGCTCTCAAAAGGATGATACTTTGAATTTGCTTTCTGTTTTATTTTC
TACATTCATAAACGTGCACAAATCATAAATGTACAATATTCACAAAGTAAA
CACACATCCAAGTCAAGAAATAAAATATTTCTAGTACCCCAGGAGCACTTC
TTAAGTACCATCCATCCAGCCACAACCCCCATCCCTGCACAAGGGAAATCG
CTCACTGATTTTTAACAGGACAGATTGGTTGTAGCTGTTTTTAAAAAGTAT
TTTATAAACCTTTAAAAGAATGTGCGTTTTGTCTTCCTTTAATCAATATTG
```

FIG. 8-218

```
TGCTTATGAGACCCATTCATCTATTATATATTGGGGTCTGTTAATTCTCAT
TGCTATACAAATAGACCGTGGTTTATTTACTCATTCTTTTTTTAACAGACA
ACTTCCTGTTCAGGCTATTACAGATAGTGCTCCTATGAACATTGTTGTACA
TGTTTTATGGATGTATATGTGCATTTCTAAGTAAAATGTTTGAGTCACTGG
AATTGTACATTTAGCTTTAGGAGATATTGCCGAGCAGCTTTCCAAAGTTCA
CATTCGTAACGTATGAAAGTTCCAGTTGCTCCACATGTCTGGCAACATTTT
GTTTCCATCTCCTTTCATTTTATCCATTAGTTAATTTTATAGTGGTATTT
CATTGTAGTTTTGATTTTCATTTCTGTAATGACTAATGAAGTTGAACATCT
TTTTATATGTTAAGGAGCCACTTACATTTTCTCTTTTATGAAGTCCCTGTT
CAAGTCATTGGCCCATTTTTAGTTGGGTTGTCTGTCCCCCACCCTTTTT
GTTTTTTTTTCTCTTTTTTCTGTACATAATTTGACTACCTATTATACTAT
GTCTTTCTTTTTCTTCTACTTCTTCTTTTAGTTTTCTGCAAACCCCCTTT
CCTCTTTGTGTTGTCAATATCATGAAGGCAAAATCAATGTTCTCATCTTAG
TACCACCCTCAGGGCCTGACACTCTGTTTTTCTGAAAAACTTGCTCAAAAA
TACCCATTGATTTGCATTAGGAGATTCTCTTCATCTGCTGAATTAACCCAA
GGTTCTTGTCCAAGCAGTTTTTTAATAGGATTTAAAATATGGTGGGAACTT
CTTCTCTAGACATGTTGTGGCAAAACCAGAATCAGTTCTGTGTGAGGAGAC
AAACTAAAGGATATGTCTTAAGTGTTAGGAGCCAAATTAATTCCTGTTAGA
GTTGACGCTGCCTATCTGAGTATCTTGGGAAAGTAAGAAAAATATGAAGAA
GGTTAAATTATCTTTTTCTACGCTCAAAAGGAACTTCTCTTGTATGTGATA
CACTTCTATGCCTTGTATGTGATACATTTCTATGCCTTTTCTCATCTTGTT
ATGTCTTCAATATTTTTCTCCCCCATATAAATTGTCATTTCACTTGAAAGT
GTCTCTGTCATCTCTCCAATTTTCATTATATGGTCTAAACTATATTGCT
ATCCCTTCTGGAAGTGTCTACATTGCCTTCCTTCACATTCATTCTTCTCAC
AATACAAGCCTTCCAGTTCTATCTTCTCTGTCCTTGATTTCTAAGTTAACC
TCATTTATTTAATCTTGTATTGGTCATTTTCTCATCATTAATCTCTTGCAA
TTGGGCTAGGATAAATAAATATCTGTTTAATCTGATGGAAATATCTGGATC
TAAATAATTTGAAAATGGTCTATTTTATTTTAGCATGTAAATTTTAATAGA
ATTTAATCACATAAATAAACGTCTATGTTTTACAATGTATAAAAAATAATA
AAAACTTTAATTCTGGGGATTATAGCTTTACAGTTCCGATCGGTGCTGAGA
TCTGTAACATATGGCTACAATTCCGAGCAGATCTTCTCTGCATCCAATAAC
CTGCCCCACCATGAAGATATTTATCAGTGATCATTTTCACATGAATTTTTA
TTTATTTAGTACTTTCCAATGAGGAAAATTCAAAGGCCACATGAATTGACT
TTTCAAGTTTGTCCAGCTGTTGTCAACCCCGGGCGCATGCTAGAAACCTCT
AAGGAGTATCTAAAAATTAGTAGTATCTGGGTTCCACCCCAGACCAATTCA
TTCAGAATCTCTGGAGTGGGTCCCAAGTATCAGTGTCTTATAAAGGCTCCC
CAGGGAAGACTAACACACAGCCAGAGTTAAGAACTGCTGAGTCTATGGTCA
GGAATATGGAGAGAAGTAAAAAATGTTTAAAAAGTTCATGCTCAGTACCAC
ATTTAAGTTTGTAACTTTATGTCCTCAGAGGCGGGTAAGGGTCCTCTCTTT
GGCCCAGTCTTGAAGTTCTGCTTGTCCAAACGTGAGGTAAAAGACCAGGCC
AAACATGTTGACTGCAGCAGACAGGAAAAAGACATTCCTCCAACCAGACTC
AAAATCCTAGATGTAAAAAACAGAGAAAATGATCAATCTCACAAGTTCCTT
CTACACCAGTTCTAGTAGCCCTCCCAGTTGTGTATTGCAATGTTGATCACA
AGGAATATAAGGAACAATGTGCAGTAGTTACTTAAGAAAGTTTATGAAACT
ATTGGAAACAAAATGGCCAAAATGCACATGGGGTTCTGAGTTGAGATGGTT
ATTTCTTTAAACAAAAATAAAATACACTAATGTTTTCTGAAAATTTGGAT
```

FIG. 8-219

```
TTCAACATATAATATTACTCATTTAAAATTATGCCTAAAATGGCATTGTGG
CATTGTGTTTGTGTCTTCTCTGTTTTTTTTGTTGTTGTTGTTGCTGTTTG
TTTTGTTTTTTTTGTTTCTGTATTGGCTGTTGACAACTATCACTACAACC
CATCTCAATTCAACATGAGTTCTCTTTGGTCTTCTGTGTGACCCTCCTCAG
AAAGCCCTACTAAGTCATTTCCAGCATTATAGTCACAGTGGATTCCTAGCA
GTTTAGTCAAATATTAACCTGGGAACTTGATCACATAGAAATGTAGTAAAA
ACAAAACTTCTCTTTGTAAGTTGGTTCTCGTCAGTCCTTCCATCCCTGCCT
GGGTCTGTCTTTTCATCTTCCTCATGAGCCTGCATTTCCAAACACCGAGCA
AGCCTCCTTGCAATGTCTCACAGCCGATCTGTTTCCAGACATTAAATTATC
TTTAAACTGGCCTAGGACACTTTGTTTCCCTTTTGTGATTTTTTAAAAATT
GGATTAGTCTGAACATATTCTTCATGATCTTCTTTTGCCCCTCTGTCTTCG
TCTCTTGCTATTCCTTGACATGTGTCTTTCATTCTGGTCATAACTAAGAAC
TGTTTCATGCTCATGTACCTCTAGGAAGTCACACGTGCTGTCTTCTGCACC
GGAACAGCTCATTTTAATCAATCTAACATCTATTCATCTTGAGAAAATAAG
CTTATATTTTCTTCCTCTGGGAAATCTGACCTACCAGAGTCTGATTTAGA
GGCTCATGTAAATAGAGTAATTGTGTTGCCATCCAGATCTTTAGAGCACCG
TGTGTATCTCCAACACCTAAAACAATACCTGCCACTTGAAGATGTTCAATA
AACTGGCCCAACCTGACTGATGAGGAATCCAGTGGCAGTGGAAGAGATGAT
TCCTGCGATGAGCCCAAATCCCCTTGAGATTCCCATGAGGAAACTTGCATA
TCTGTGGGAAGATGATTTTATAAATGATTTTATATAGAAAGCCACCTACAG
CTTCTGCAGCAACTCAACTTTAATGCAATTCAGCTCTAATGGCAAAGTCAT
TTTGCTTAATGCAGTTTTTCATTCACCTAAAGACATTCAGGGCAATGTCTA
TTTGCCAAACCTGAAATTACCAATCTACCAAGTCAATAACCAGGGAGCAAT
GCAGTCTCTCTGGGAACCACGTTTCTTTACCCCGGCTGCTCAGTGGAGAAG
CCAGTTTGTGCAACGGGCAGGACACAGACTCCAAAGCCAGACTCCCCCAGT
CCAAATCCTGGCTCTGCCTTTATGTGACCATAGTCACACCATTTAACCTCC
TTGTGCCTCAGCCTTCTCCCTTATAAAATGGGGATAACAATAGGGCCTACC
TAATATAACTGTGAGGATTAGATGTGTTGATATATGGCAAGTCTTGGCACA
GGAGCTGGCTTATTGTGACTGTATATATATATATATATATATATATATATA
TATGGTAGCTAATATGAACAACACCATGGAAACTTTTCCAAATCACCTGTG
TGTGGGCCTTTTCCCAGCATACACAGTTCAATCTCTGTTAGGGAAGCTTGG
GAAGGTTTTTGTCAAAATGATTACTGGCCAAGATTGGAAATTGTTGTTCTA
AAAATGCCACATTTGTTGTTCTAAAAATGGCCACAGACAGATATTTGTAGT
TATTTGTCATTCTGCCATTAGTGCAATGTCAGTAACATTAAAGAGTTTCAC
GGCGACCACTGAGGTCTAACACCTCTGGAGGGGTCTGGAGGAGGGGAAAAA
ACAGGTAGAGCTCTTACCTGGGGGCGATATCTAAGGTGTTGATGATAAACC
CTGAGTCACATAGGTTACTGGTCCCAGGAATAAGTATCAGCAAAATAATGG
TTATCACGTAACTGGAGGCCACAAAGGGCAGGGCCACAGCACATATTGATG
GAAGGAGGAGCCCTGGGCAATGAGGACATGCTGTCAGGGAACCCTCTGAGA
CCATGTGCAGAAAAGGGATTGGTTAAATGGGCCCACACGCTTATCCTTACC
AAGAGATGAAAAGAGCTTTCGCACAGTGATCAATCTGAGAAGATTCCTGGA
CAAAAGGAAATCTGCCAGCTGACCTCCTAAAATTGTACAGCTTGCAGCAGC
AATAAAAGGCAGGGAGGACAGAACTCCACTCTGAAGGAAGGAAGTTTATAC
AGAGTAGTTATAGAGATACGTTAGCACCAAAATTTGTCAGTTACACAGACC
AGCCATTAACTTACCCCCATGATACTGTGGGTTGTTTGGGGGAAAATTAGC
ATCCTTTTTCACACTAAAAGAACACTGTCTCAGATAAGAGGGCCAGAAGCT
```

FIG. 8-220

```
GCATCACTCTGGGCTCCAGATAAAAGCAATATTAATTTCTTGGGTTTTTTG
TTTTTGAAACGGAGTCTTACTCTGTCGCCCAGGCTGGAGTGCAGTGGCATG
ATCTTGGCTCAATGCAACCTCCACCTCCTGGGTTCAAGCGATTCTCCTGTC
TCAGCCTCCTGAATAGCTGGGATTACAGGTGCCTGCCACCACACCTGGCTA
ATTTTTGTATTTTTAGTAGATGATATTTAGTAAACCATATTGGTCAGGCTG
GTCTTGCATTCCTGACCTCATGATCTGCCTGCCTCGGCCTCCCAAAGTGCT
GGAATTACAGGCATGACCACCATGCCTGGCCCAGCAATATTATTTCTAAAA
GAAGCTTGGAATCAGCTGGTGTGGTAGTATAGCATAGTGGTTAAGAATAT
GGATGCTGCAGCAGCTCTATCACTTAGTATTGTGCAACCTGGGGCAAGTTA
TCTCACCTCTAAGTGTCCTGTTTCCACATCTGTGAAAAGGGAATTATAACA
ATGCCTCTCAAGGTCATTGTGAAGGTTAAATTAATGGTTATATGTAAAG
CCAGAATGTAATAGGTAACACAGAACTGTTTCTCCTTATTACCATTATCAT
TTTCGTAGAAGTATAGGAAGTAAACTCACATCTCTGATGTTAACATGGAGC
AGAGTACTGATATACGTTGGTAGGTATGTTAGGATGATGGTGCACAACCAG
AAATGGCTGAAAAAACCCAGGAAAATGGCCCAAAGTGGTAGGCATGTGACC
ATCGCCTTTATGGGGACAGCTCGTCCAGGAGAACTGGGCTGAAAAGAAAGA
TCTAATCAGCATGAGTATTAGAGCAGCCAAGATGGTGCCTCTCAGAGGAGA
TCCACACCCTGCCCTAGAGACCTCTGCATGGGCCACAGGTACAAGGTGTGC
ACTGTACCTGTTGAGCCAGTGAGGACAGGATGTGCTCCTTTTCCCTAACAC
TTATGCACGGGTGATGCATGGGGTCATCATAAATCACTGTGAACCATAGGA
GACAGCAGACACAGCCAGTGCTACCTGGGAAGAAGGGATAAAATTAGTTTT
TAGGTAGATTTGTTTACTGGGGGAAGGAAGTTTCCTCTGAAGTGGCATGCC
TCTCCCTTCTACACACTAATCAATTAATGCTTATTCTACCATAAGGACCTA
AATGTTCCCATTCTTTCTTTCAATCCTTCTACAAACCTGTTAAAGCTTTTT
AGATATTACGTCTCAAATAGAAAGCCACCATTTGTCAATGTCAGAGCCCTC
TGGAGATAACAGGAGCGTGGCATTGCATAGCTGATTAATTACTTTAAAGTC
TCCAATGATTACAGTGTTATGTATTTTAGGCAGCAACTTCTTAATGCACAC
ATAAGTTGTCTTGTTGCGGAAGATCTGAATAGTCAGGTTTGCAGTCATACA
TACACGAAACAACCTTCCATGAAATCATGTGGCAGGGAAAAATTTCCAATG
CACTTACAAGAGACAGTATTATTTGTATTCAAGCCATACATCCATTATGGA
TTCCCAAAAGAAATATTTTTGTACAATACCTGGTTAACATGTACAAACCAA
AATAATTAGCATCATTAATGAGAAAGCCATTCAGGCCAGGACTATATTTAA
TGACACCATTTGGCTATAAAAACAAATCAAGTGTAGAAAATTGTCTTATTA
TTGGAATTCCTTATTTGAAGAACATTCTATGTTAAAAGATTCTGAGGACTA
GTTTTCTTTAAATCCCCTCTAATTACTGGATTCACTGATTCTTTTATTTTA
AAGCTAAAAATCAGGCACCATGATGACACCCAAGTGATGAAAACATAGAAT
GGATTCCTTGCCTCAAGCATTTCACAGTCTAGTGGAAAGAAAAGGAGAAAT
AAATAATTACACACCAACATAACCTAGAGAGGAAATATCATAAAGGAGAGA
ATGCCAGAATCTGATAGGGTAAGCCCTGGAAGGGCCCATGGGGAAGGGAAC
ATTTGAATTGAACTTTGCAAGATTAACTTGGTAGAGAACAGGTGAAAGGCA
TCTTGGACAGAAATAATAATTATAATGAAATATGAAGACACATTGAAAATG
TACTTCACTATCTTTGACATCTTAACTGCATATAGCAGGCACTTCAGATGT
GGTGGTAGAGATTCTGCAGAAGGTGCTTGATATGGAAGGACAAGACTGCAT
CACAAGTCGGTGGGTGCCATGTGAATAGTCAACTCCTCTACCTTGTGCGTG
TGGCTTCCCAGAACCACCAGGAAGGTGTTAATCAGGTTGTGTGACTAGATT
AAAAATGATACCAACCGTTGACATTTTTTATCATCTTCCATTTGATAAAGG
```

FIG. 8-221

```
ACATTTTCTTTCATATAGGAAGAATGTGGGTGGTGTAGGTGCCAAAATGGA
TGCTCAGGAAATGGAGGCGTTAGGATTTAAGAGAAAGTGACTCACCAAAGA
TGTACAAGATAAAAGGCCAGCTCAAGGCCTGTGAGATTAGTCCCCCCACAC
AGAGGATGATGAAGGATCCAAATGCTGACCCTAAAGGAAAAAGGGAGAAAA
ACACTTATGAAAATATCAAAGGCTGAGACTTCGTGGCCTCCCTAAACAATG
TCCCAACAGTGAGGTGGCAGACTTAGAATTATTGGGCAATGAGAGTATTTA
TTTCTAAAATAGCTCACAGATTTTCCCCAGTAAAGTAATATGATATAATTA
AAATTAACAAATAATAGTAACACACTCTCTGATTCTTCAATGGCTCCTCAA
CACCAATGTGACCAAATCTAAATCCCTTAGTTTGTCACAGTAACTCTCTGC
TATCACAGCCCATTAGCATTTTCTTGTGATTACAGTTGCATTCTTGCATGA
TCTAATATGAGGCTAGGGGCAGGAAATGAAAGACTTACAAAAATCGGTAAG
ATACAGCCCCTGCCCTCAAAGAGCTTCTGGTCCAATTGGAGAGAAAAATGT
GAATAAAATTGATTGTCACTAGTGAAATGCCATGTAGGCTTTGGAAGTCTA
CATTAAAAAACAACAAGACACATATTTCACAGAGACCTATAGTAAGAAATG
CATTTTACAGGGTAACATAACACACACACCAATATGCATAAACACTTGTAC
ATACAACCACACACATATGCCTCAAACGATGGTTTCATGAATCGATATTTA
ACTTTACCATGTCCAATGCACTCCAACAATTTCTATTCTATTCTATTCATT
TTTTAAAATAATGATTTTAACCCGCTCAATGGATTTTATGACTCACTAATG
GGTCCCAAACTGAAATTTGAAAAAAAAGATGTAAAATATAAATATAATAAA
ACTACAATGTACGTGGAAGTATATCTGAGGATAAATTGATAATAATTATAA
GATTTAGGAAGTTTTGGCCGGGCGCGGTGGCTCACGCCTGTAATCCCAGCA
CTTTGGGAGGCCGAGGCGGGCGGATCACGAGGTCAGGAGATTGAGACCATC
CTGGCTTGAAACCCCGTCTCTACTAAAAATACAAAAAATTAGCCGGTCATG
GTGGCAGGCGCCTGTAGTCCCAGCTACTCGGGAGGCTGAGGCAGGAAAATG
GCGTGAACCCGGGAGGCGGAGCTTGCAGTGAGCCGAGATAGCGCTACTGCA
GTCCGGCCTGGGCGAAAGAGTGAGACACCGTCTCAAAAAAAAAAAAAAAAA
AAAAAAAAAAAGGTTTAGGAAGTTTTTACATAAGCTATGCAATAGGATAGA
TGGAATTTTGGCACAAGGAACAGGGGCAAAGAACTTTCCAGGCATATAAAC
TAACGGGAGCAGAGCCAGAGGGAAGTGCAGTGCAGATCTATGTGGAGAGCA
GCCAATGTCCAGTGCCACTGGAGCCATGCTTGCACAGGGGAGTTGAGTGGA
ACAAGGTTGGGGCCAGATGGCTAAGAACTTTTGTATTCATGCAATAAAGAG
GTCAGGCTTTACTCTGTAAGCATGAAGGAACACATTGAAAATTCTCAAGCG
GGTGAGTAAAAATGTGCCATCTTTATTTTAGCAAGCTAACTTGGTTTTGGT
GGGAAGAAGGTTGAAAGAAACCAGTCTAGAAGAGAGAGATCAGCAGATAGT
ATTTGCAAATAGAGGAGATGGTTACAACTATGATGGAAGGAAGCAAGAACG
CAGGAGGGTTGCTTGAGGTAAAAGTCTGCAGGATGCAGCTGTGTAGTGGAC
CTAGGAGTGAGAAGCTGGATGGAATTTTAGTTCTGCTCTTCGAGTATATAC
TCTCAGCACGACAGGCTGGGGAGAACAGCAATGATAAAGCTGTAGAGGCCT
GAGTAGGATCACATACCATGGAAAGGCAGTCTAGCATAGTGATTGAGAATG
TCTGCTCTGGGGCTAAAATCTGCATGGGCTTAAATCTCAGACCTACCACCT
GCTGGCTATTTGTATTTGGGCAATTTTCTTAATCTCCACCTTCCTTAACTC
CCTTCTCTGTAAAATAAGAATTTAAAATGGTACTTATATGAGAGGGTTGTT
GTGAGAATTAATGAGCTCATAATAGAATAGTAAAGAGCTTAGAATAATACA
GAAACTTCAAACTCTTCCAGCCTGATTTCTCTCCTTACCACCTGGAGCTGT
GGTAGCCTTAATTCTCACTTCAAAATCATTGCTAAGATGGTGTATATATAG
CTTACTTGATCTTTTTCCATGTGTGCAATTCTTAAAGGTTTAAACTTTTTC
```

FIG. 8-222

```
CGACAAGGCTTTTCTGACTACTAAGGCTTTTCTGACTACTAAGGCTTTTCT
GAGCTGAAACCTAGCTCACAATGGTTTTTTCTACTTCTAAGCTTCAATGTC
TTTACTGCACAGATGCATCTTTCCTATTTGTGATGCAAGTGTCTTATATTG
TTGAATTTTTCAGCAGTACTTTTTCTCTCTCTTCCCCAAACCATTTGATTC
ATAGAAGATAAGACACAGTGGGATGGAACAGATGACAAAGCTATGACCCAT
CTGTGCACACTTACCTGATCCTGCAATGGTGGTGAGCTTGCTTCGTTCAAG
TGGAGGAGCCCACTTTGCCCAAATAGTAAACTGACCTGTCCATGCCATTCC
CTGAAATGAAAATCATTAAGACCTTTGATATTTTGTAGAATTCAGAAATCT
GGATCCCACCAAGAATGAGAAAGTATCTGGATACCTGGGCCAAGCCCTGGA
CTGTCCGAACCATGATGACCAAAATCACTCCGAAGTCAGCAGCCAGTGGTG
TAAAGAGGGTGAGAAGGGAAGAGATCAGCAAACCAGCACCAAGCATTTTTT
TTGCTCCAAATATCCCTGCTAAATATCCACTTGGGATCAGAGTCAGTATTA
TCCCATAGTTGATGGAGCTAAAGATGATACCCTGAGTTTCTGGGCTCCATT
GATACACAGAGGCCTGGGGGAAAAATAGGAAAACTCTTTGTCAAGAAGTCC
TATTATGAAAATCTACTTTACAGTCAGAGTTGCTTGAGGTTAGTGAGACCC
TAGTATAAAATATTGATTTTTGTTTCTCTCTATATTCTTCCTACCTTCCCA
AATAACCAATTATACCCCTAATTTGCTTGTCTTAGTAGAAGGAGAGAAAAA
CAGAAGAAATGAAGAAAAGAGGTAAAGAAAATGATTATATAGATGAATAAT
AGGAAGAAGTAAATGGAAGAAAACATTGAGAGATATTTCATCTGTGAAAGC
ACTTCCTCTATTTTGCTTCTAGTAAAAGTTGAGTAACATCTTGACTCTTAT
ATCAAAGAATTTTTTAAAACACACACACAAAACTTTACTGAACTCTTAACC
AAAATCAGTGCCTAATTAAAAAGAAAAGTCAAGTTTGGGAATCATGGTCTG
CCCTGGCTGAACTGAGTTCCTAAAACACATATTACAAATGAATAAGATCAC
ATTCTTCTGATATAACTCAATAAATAATTTGAATTATTTTAAAATAACTAC
CTAAAATTCCTAAATAATTACATAAATTATATTACCTGAATATTTACCTAA
AAATAAATAGATTTTAAAATAAATAAATAAAAAATAAAATAGATTTTAAAA
TAAAATAAAAAATAAATGCAATAAGGCCCCTAAATATCTGGCATCATGCTA
TAAAGTAGAGAGCCAAAGAATATAAAATATGAAATATTTTACCCACTCAAA
AAAACTATAAATAATACAAGGTATATGATTCATGTGAGAATCAAGATTTGA
GGATGAACATAAATAAAACAGAGACTTTGAGAGGAGAAAATAATAATTTGG
GAAGGTCCCAGAAAGGAAGCAATACTTGAACTATCCCTTGAAAAATGACTA
TGATTTGTAGAAAGTCAAAAAGGAAAATTTTATCTCATCGGAAAAAATAGC
AAAAGTGAACTTGTAGCATTTGGAAGAAACTAACAGGGACTCTGGCTTGCT
CAGGGCAAAAACTTTCCATGGGTCATTGATAGCAGATGTGAGTGTGCTGAG
AAGCAGGCCCAAATTCTGAAGGAACACAGCATGTCCAGTGAACACTGCATG
TTTGGCAACTTGAAGGTGTCCAAGATTCCTGAGTAGTGAATCTACTCAGTG
TGGATATGTAGACGGGATAATGGAGGAAAGACTGGAGACAATAAATTTATG
TACTCATTGTAAATAAGCTAGGTCCAATGTAATAAAATCATTAATCATGAA
TTATAGGGATGACATGGGAAATGTACAGTACAAGATAATTTAAAGGATAAT
TTTTTTAATTGGGTAAATTCATGGTTTTCATATAAATGTAAAATAAACATA
CAACAAAGATTTTATTTAACTCATTGATTAATGGAGGAAGTAAGTAAGATG
TTATAACTGGTTCAAAGGAAAACTCAAAGAATCACGCATAACACAAGCAGG
AAGCAATGCTGAAATAGACTTTAAATATACAGCAGAGCCTGGCACAGTGGC
TCACACCTGTAATCCCAACACTTTGGGAGGCCGAGGCGGGTGGATCACCTG
AGGTCAGGAGTTCGAGACCAGCCTAGTGAAACCCTGTCTTTACTAAAAATA
CAAAAATTAGCCAGCCGCGGTGGCATGCCCCCTTACTCCCAGCTACTTGGG
```

FIG. 8-223

```
AGGCCGAGACAGGAAAATCTCTTGAACCCGGGAGGCGGAGGCTGCAGTGAG
CTGAGATCATGCCACTGCACTCCAGCCTGAATGACAGAGGAAGACTCTATC
TCAAAAAACAAACAAACAAACAAACAGCAAAATTGGCTAATTCAACTGGGA
GGTGAGTGGAGAAAAGTTTTAACTGATTTTTCTCTTGGCAAAATTTATTTG
CAAAGCTATGGACAAGAATCGTTTGCATTTCTATTGGTTATATAGAATTTA
CAGGGATATAAAATTGCTCAGAAACAATAAAACAGGCAGAGAACTGAATAG
GATTGAGTAACCTATAAGAATGTGCCCAGGTAATACCTAGTTTTTCATTGA
AGACATCACATAAACTGTTCCATTTTTAAATTTTTCACATTTAACTCTACA
GTTCCCCCACCTTATAATCATAATAACCTCAATGAAATCTTATTTTTATTA
TTGAAGTAAGCAATGTCTCAAAGAAAAATAGTTCCAGTCAGTTTTAATTTG
TCATTGGAAATGTATACTTCCATACTCCACAGAATCAAGATCTATGCCTTC
CTTTCAAAGTTTTTTCTCTCAACAAAGAGCCCTATTTTCCATCATACTTAC
CTTTGTATCAAATTCCTTGATGGATATGCTGGAGTTATTGAAGGCATCTGC
AACAGGCCCCTCAGTGGAGGCATTAGATAGACCTTGCTGCTGAGTGGTGTT
CACCATGGCGATGATCGCAATGCTCAGACTCACACGCTGCGTTATCATGGT
GAAGTTTGAGAAGTGCATGATAAGAGCCAGCCCATAGCGTAATGAACAGAA
ATCTGGACCTAGACAACAACACAGATGTATGTAGTGAGCATCCTGACTGAG
ACCCCTTTCTTTTCCTTTCTCTCACAGCTCGATCTGATAGAACTTTGGATG
ACACATGAAGTCTCATTGTCTTTTTTTCACCAAAATAGCCAGCACTACAAA
CCCACTTTGTCAAATTATTTGGTTGGCTTCAAGACAGCGAATATGGGATCT
TATAACCAAGTAAAGCAAATATGGCCATCTTTCAAGGGGATAGGAAACACA
TGATAAATAGAGAAAACCCACATGTAAGGCATTTATGTCATATTGCTCCAA
AATGAAGTGAATGGGGATGACAGTGGCAGAGCCAGTCACATAACCTTCTCA
GCGTCAATAAAATTCCCTGGGCTGTAAGTGAATAGTCCCATCTGTTATGCA
CATTTGTTTATCACAAAGCTTGAGAGTTTATACATAACGAGCTGCCTTTGA
ATTAAGGTATTGCACATCCAAGGATTCTCTTTTAATACATTTGAGAGATGG
TACTTTAAATGAGCACTTCGACTAATTCCCTAGTGTAATGTCTACTTGGAA
ATGTTATTGCTATGTGTCACTAGGTCCTGCCTTCACATATGTTCAACTTAA
AAAAAAAAAAAAACTACGTGGGGTGCAGTGGCTCACGCCTGTAGTCCCAGC
ATTTTGGGAGGCTAAGGCAGGTGGATCACTTGAGGTCAGGAGTTTGAGACC
AGCCTGGTCAACATGGTGAAACCCCATCTCTACTAAAAATACAAAAATTAC
CCAGGCATGGTGATGCATGCCTGTAATCCCAGCTACTCGGGAGGCTGAGTC
AGGAGAATCACTTGAACCCAGGAGGCAGAGGTTGCAATGAGCCAAGATCAT
GTCACTGTACTCCAGCCTGGGTGACAGAATGAGACTCAATCTCAAAAAAAA
AAAAAAATTAATATGTAGAACTATTTTTACAAAGCTTGCAGGTGATGTGG
TGCTGGAAGATATTCAATATATTGAAAGGACAAATTTTTTCTTTAAAAGCA
TCCCCATAAAATGGAACAACCACAGACCAATATTGAAAGGGTTCCCATGTG
CATGATAGATTGGATTTTTCCTGCTTATTTGAAGAAAAGCACTAAAGTGAA
AGAAAGAGAAAACCTGTGAAGACACAGATAAAAATATAATGGAAGAAATAA
TTTTTAATGGCCAAAAAAGCTCACAGATAAGAGTGGTGGTCTGGGAAATAA
TTATTTCCATTTTACTGGAGGTTTCCAAGCTCAGGAGAAAGAGCCAGCCGC
TTGGTGAGAATATTATAGTAGGGATTCATACATAGGTTGGTTTAAAATGAC
TTTCCCGGGCCAGGCGTGGTGGCCCATGCCTGTAATCCCAGCACTTTGGGA
GGCCGAGGCCGGTGGATCACGAGGTCAGGAGATCGAGACCATCCTGGCTAA
CACGGCGAAACTCCATCTCTACTAAAAATACAAAAATTCATCTGGGCATGG
TGGTGTGTGCCTGTAGTCCAAGCTACTCGGGAGGCTGAGGCAGGAGAATCA
```

FIG. 8-224

```
CTTGAACCCGGGAGGCAGAGGTTGCAGTGAGCCGAGATCGCACCACTGCAC
TCCAGCCTGTGAGACAGAGCAAGACTCAGTCAAAAAAAAAAAAAAAAAAGA
CTTTCCCAAAACTTATTCCACTCCCTAGATCCCAGGATTTATTGCTTATTT
GGCTTAATTTCTCACAGATGATTTCATGGGGCTAAGGAAAAAGCAACAGGA
TCAGGGGCTGGAGCTGGCTCCAATGTTACACTGGGAGTATCTTTACGAAGG
GTCAGTGTGATGCAGAGATGTGTAAATGTGTCGGAATAAGCTTCAGCTTAT
TAACATAGCCTGCAAACAAGAGCAGTGGCTTTACCTTTCCTGGTGGCAGGC
TTCCCGTCCATTTAGCTTCTGTGGGAAATGGTACCACGCTTTGTGGTGGAG
TTTCCCTGTGCCCTGAATCTCTTTTACTACGACAGTCTTTTATCTATGGAG
AGAACATAATCCAAAACATAATACACAAATAATTTCCCCTTGTTAATGTTG
CCTCCTCTTAGCATCAGTAAAAGTTTTGACCCAACACAGCTCTATAACTTA
CATTTTATGGGGCACTACTGGTATGCTTTTGGTTACAGGATTGTTAAAAGG
AAATCTGGCTGTAAGTTCCAGCTGTGTGACCTAGAGCTAGTCATTTAAATT
CTCTAATCATTCATTTCCTCATCTGTTCAATAAAGATAAGGCTCCTTTCTT
AGTGCAGCTGGAAGAATTAAATGAAAAATTGCATGTACTTTATCAAACCAC
AGAGAAGCATGCGAAGGTGAAGAGTGGTATTGCTTGTAGCAGACCATAAGA
CAGGACAATTAAACTAAGCTCAAGAGCTAAGGAGGAAGGTTCCAGAGCGGT
CTTTCCTTTCATTCTGATGGTGTTTCTCTCCCCTCTGTACCACCAGAACAA
TGTTCCATGTGCCTTCGAACATGAAGGATGACATTACATAACACTAATATG
TATTACATTTAAAAGTTTAAAATGTTTATTCTCATGTTTGCTACACACAAT
GTGGACACTTGCTTGGACTGACAAAGTCTTCATATCACCTAGAAAATTATA
ATGAACAGGGACTAATTACTACAATTGTGAATAAATCCAGCTATTGTGACA
GGCAAAGAGAATTCATGGCTCTAAATATGGACATGTTTAATTTAATATTTG
TATACTAATCAAATTATCTTTGGGGATGCATACATTTGTTTCTTTTAGGAA
AAATCCATATCCTAAGAATATCATCAATTTTCCATTCATTCCTAAATTGAA
GCTTCTATGACTTTATTTTTTAAATTGCTTAAAATCCTTCAAGACATCTGA
AATTTCTGTGACTTTAAAAACACATGTATCGGCCGGGTGCAGTGGCTCACA
CCTGTAATCCCAGCACTTTGGGAGACTGAGGTGGGTGGATCACTTGAGGTC
AGGTGTTCGAGATCATCCTGGCCAACATGGTGAAACCCCATCTCTACTAAA
AATACAAAAACAGCCGGGTGTGGTGGCACATGCCTGTAGACCCTGCTACTA
AGGAGGCTGAGGCAGGATAATTGCTTGAACCCAAGAGGCAAAGGTTGCAGT
GAGCCAAGATCGTGCCACTGCACTACAGCTTGGGGGACAGAGCAGGAATCC
GTCTCAAAACAAACAAACAAAAAAACACATATATCAAACCTCTATTTTATC
ATTCAAGGCTTTGCACTGTTTTGCACACAAAATTTAAAAGACTTGTCCGT
ACTTTAAAGATATTCATAATCTGTGACCTTAGGATGAAGGATTATAAAGAA
AGGCATAGATGAAAAATTGTGTCCAAAAATATCCTTTGTAGTATTACTCAT
GACTGCATAATGTTAGAGATAAATTAACCTAATAATGAGAGTCTGGCAAGT
CAATTTGATAGATTATTGTGATGGAAGCTATTTTAAAATGTTTTCGACAAT
ATTGAATTACATTAGAAAAATGCTAGTACTCTAGTGTACAAAGCAGGATAC
GCTGTGCACATCCACATACAGGAATAGAAACTGATTCACACAAGTGCCAGT
AATGACTATTTCTGGGTTACAAAACAGGATGATCACTTCATTCTTTGTGAC
TTTCTATATTTACCAAGTGATTTTGTAAATAATTAGTAGATACTCATTTTA
TATTCAGAAGTAGCTAAATGTATTTAAAAGAGCAATAATTGGACTTCATCA
GCATGGCAAGTATAGTTTTCTGCTTTCCAAATATCTCTAGAATTCTGGGAA
TAGTATCTCTCCATCTAAATTTTGAATTTTGGGTGTTTGGAGATTTTATTG
TTGTTGTTGTTGTTTTGTACAATGGACCCAAATGGAGGCCCAATTGCT
```

FIG. 8-225

```
AGTAAGATCAGGTCAGCACCAGGACAGATACTGGTTGTTGCTCTGCCTTAG
AAGGCCTCCAAGTCTTGCTAACATCTGGATATCAGGAGTTCAGCTCATTGC
TCTACACTCAGATCCTAGCTGAAGTCATCTGTGGTCAAACCCAGAGTTTGG
ACCATTTTCTATTTGATTTCACTTTTTATGCAAGATCCCGTGGCTTGGCTG
AAGGCAACTCTTTAACTGTACATGCAGCTGCAATTACTTACACTCCACTTA
AAGCTTTCCCACCAACTTCTCCAATCTTATAAACACTGAAAGCTGAAAGAG
ACTCAGAGATCCTCTGGCCCAACTGTTTATTTTATTGATAAGAAAATTTGC
GTAGAAAATTTGAAAAGTTGCCTGAAACCACATGATGCACAGAGCCAGCAC
CAGATCCCCTAATGCCTAGACTACTGCTTGTTCTACCTATTACAACTTCCC
CTTTGTTTTCGTAATATTTTAATCACAAGCTTAAAACTCAATGGGGTAGCT
CCATTTTGAGGTATTATAAAGGAGAATTTGTATATTTTAAATCAAGTTTTA
ATCATTTATTCTAGAAGGAAGTTTGATAATGAAAAATACTTTTAGGTTGAG
CTTTGAATATTAAACATAAACACAACAAAACTACTTCTCCTTGCTCTTTAT
GTTACTGGAATTGTATCACAAACCCATCACTTTAGTTTTTCTTCCCATTCT
CTGTTGCTGTCTAACGAGAAAGGATGAAAAGCCCTACTTAAGTTTTATGGT
TTCAAATGCTACTTTGATTTTGTATCAATAGGTAATTTCAGTTCTTCGTTT
CCTATTTTCCTTTGCATGAGACGAATGCAGAAATCAGGCTAACATACCAAA
CCATCCTAAACTGAGGTCTTTCATGGTAATGGGAAATGTTTTTCCAAAATA
AGCACAGAAGCTAATAAAATTATGGAGGCTGAACACTGGCATGGTTGATAT
GTACTTAGAGACACTGGAATAATTATTAACCTATTTGCAAACAATTGAGAA
CATGTAACAGTGTCAGAACCCTTCCCTTTAAGGAGATATACCTCTAAAAAA
AAATTGTGAATTCTAGTGCCAAAGTTGTAAGTAGACACAGAAAAATGAATT
GAAATTAAGTTAAAGGAAATGTTATATTAAAAAAAATTACTTGACACAGT
ATAGGTTGAATTTGAGAAAAAAATAAATAATGTAAATATTATGGTATACGC
ATAAGCAAAAAAACAGGTTTTTCCCTTTTTTTAAGTCTAGAACTCATGATT
TTATTATAATGGTCGTTAGATTGCTCTTAGATTCTCCTAATATCCAGCCTG
TCTTGCTTCATCTCTGTTAGCCCAGAGTCCTAGTTTACTCAGAGTAAATGT
TACACCTAGATCAAAGAGCATGAACCTGCAGTGGGAGGATATTCAAGGACT
GAATTCTGCTCTGCCATTCCCAAATTGAGTAAACCAGGTAAAGTTTCAAAA
ACTCTTAGGGCTTTCACTGTTTCATAGGAAGAATTGGGATAATGTTACTTC
ACTGGGCAGTTTGGAGTGAAAACAAAAGTATGAGACATGCCTCGTAAATTG
CAAAGTGTTATATGTTGTATAATATTCTAGATACTAGCAACAGCAATAATA
ATAAACAGTCACAATATTGGCAGTCTAGCCCTCTCAGATCCATAAATACAG
GCCTACAGCAAATGAAATGTATTTCTATAAAAGTGCCTTTGATTGGTTGTT
AAATTGGTTTTAAATGTTTCTTTTTTAAAGTGGATTCTTCTGGCCTGGAAT
CCTCAAGATGAGTGGGGAGGAGTTCACCAGAAAACATAGAAGCAATTCCTT
CAGTGTTAGAAAAACTGAGGGCCCTCTCATCATCTGCCTATCTTTCTGAGA
AATTGGTGCTGACCACAATGTCCCTGGGTGCCTTTTCTTAGCTGTACAATG
AGGGCAACAAGCTAGGTGATCTCTACAAGCGTACAATTTTCTTGCCTTCAG
TCTTATTCATAACTTTGGTCATGTTCTCCTTTTCTTTTATTATTATTATTT
TTTTGAGACAGAGTCTTACTCTGTCACCTAGGCTGGAGTGCAGTGGTATGA
TCTCAACTACTGCAACCTCTACGTCCTGGGTTCAAGCAATTCTCCTGCCTC
AGCCTTCTGAATAGCTGGCACGCGCACTATGCATGCGCATAGGTGCACGCG
CCGCTACGCCCTGCTAATTTTGTATTTTTAGTGGAGACAGGGTTTCACCA
TGTTGGCCAGGCTGGTCTCAAACTCCTGACCTCAAGTGATCTGCCCGCCTC
AGCCTGCCAAAGTGCTGGGATTACAGGCGTGAGCCACCAGGCCCGGCCATG
```

FIG. 8-226

```
TTCTCCTTTTCCTGAGAGACCATTTCAAATTCATATAGAAGTCTGAAAAGA
CTCGTTAGCCACAGTCCCAAACACAAATCTTGTCAGTTCTGATCAGTATTT
CATTCCACAGCCAATCCCAGTCTGACTAATCACAGCATCACAGTTAATACT
CACAGCGTCCTTGGAGAAATGACCATTGTCCACAGTGTCCATTGGTACCAG
TGGCTTCTCAAGCCTTGCCCTAGGGTCTTCATTGAATCAGTTATCTTTTTC
AGAGAGTCTCTTCATTTTGGAATTAGGCAATATTACCAGATGGAGATCCTT
ATGTTGCTGTTAATGTCTTTTCTCTGACTTCTCCTAAAACTGTTCCCTCCC
CTTAATGGACCTTTGGTAAGTTAGTAATAATCCTTCTACCCAAAAAGAAGA
AAAGCACTTACCTTCACCATTAAACCAGTATTTTAAGCCCTAGACTATAAG
GCTAACTTGGAAAAGGAGGGAGTTTTCTGTCCCTTCTTCCCTTTCAAATAC
TTTTGCAGATTTTTACAGGGATAAATAGTGAGCCACGTGGCAGTCAGACGG
CAACAGGTTTGGCCCCACTTTCTCAGAAAGCCTCGGCTTGGTTTTGCCGCT
TAATTTTTAACTTCATTTTCAAGTTCTCACTGTTAGAGTATCTCAAAAGAT
GTCATCGTGTGTTTCTGCTTTGAACTGTGCATACAACCATTCAGTCAACAA
GCCTTTTTTTCTGAAAGCAAGGGGGCATGGTGTGGAGGAAAGGGCAGGGCT
CCTGAAATCAGTGATGGAGTCAGACCCATATTCACTTCCTAGTGTTTTCCC
TGAGCTTGGACAAGTCACTGAACCTCTTTGAATTGGCTTCCGCTTTAGTAA
AGCAAGGATTGTGTTACTGTACTCATGGGGTTATTGAACAAATGAAATACA
TATTCTAATTGGTAGTAGCTCCTCAATAAATGAGGTGTTCATTCCTCTTCA
GGAGTTCAGTTAAGTCAGCTAGATTTTCCATATGCATTTGGTGCCCACAGC
CTAATGAATGTGAACTGTGACTGCCCTGGCAACTTCCCAGGAAGCTGCCTT
GTACCCCTCCTTCCTGTTTCATATCATCCATGTCTTCCCTAATCCATTTTC
TGCTTGGCTCCCGACTCTTGGAATTGTGTCCTATTTGTAATCATTAATTTT
GAGACTGTGGTTGCTATTGGATCTTCCTAGTGTGACGCAACCCTTATAAAA
TGAAATGAGAGCCTTCCCTCTCTGGCTTATCAGCTTCAGACTTCCTTAATT
GAGTTCCGCCATCCTAGTGAGTCTCACCATACTCCCGAAATAACCTGCTGG
AGTAGGCTTATCCTACTCAACTCCTCAGATCTCTGTATTTAATTCTATTTT
ATTGCTGTTGTAGTAAATTACCACAACTGTGATGGCTTGAAACAACACAAA
ATTATTTATTTATTTACAATTCTAAAGGTCAGAAGTCCAAAATGGGTTTCA
CTGAGCCAAAATCAAGGTATTGGCAAGGTTGTGCCCCCTCCAGAGGCTTTA
GGGGAAAATCCATTTCTTTTTCTTTTCAGCTTGTAGTGACCACTGCATTTT
TTGGCTCTTGGCCTTTCCTCCACCTTAAAGCCAGCAGTGTAACATCTTGAA
GTATTTTCTCTTATTCTGACTCTTCTGCCTGTCTCTTATAAGGACCCTTG
TGATTACACTAGGGCCCATCTGCAAAATTCAGGAAAATCTGCCCATCTCAA
AATTCTTAACTTATTAAACATGTAAAGTCCCTTTTGTCATATAAGGTAATA
TATTTACAGGTTCTGGGGATTAGGACATGGATATCTTTGGAGGACAACATT
CAGCCTACCCTTTTGAGGGATAGAGGGGTAGCAGGAAGAGTTGAAACAATT
CCTTCCTTTCTTTATTTAAAAATTCTGGTTATTGATTTATTATAGTTATCA
TGTGCCTGATAAGCCAATGAAAATAGTTATAATGGCCAGGGGCAGTGGCTC
ATGCCTGTAATCCCAGGACTTTGGGAGGCTGAGGCAGGAGAATCGCATAAG
CCCAGGAATCCAAGACCAGCCTTAGCAACATAGGGAGATCCCGTCTCCACA
AAAAAATGCAAAAATTAGCTTGATGTTGTGGCACATGCCTATAGTCCCAGC
TACTCAGGAGGATTGCTTGAGCCCTGGAGTTCAAGGCTGCAGTGAGCTGAG
ATTGCACCACTGCACTCCAGCCTAGGCAATAGAGCAAGACCCTGTCAGAAA
GAAAAAGAAAGAAAGAAAGAAAGAAAGAAAGAAAGAAAGAAAGAGAG
AGAGAGAAAGAAAGAAAGAGAAAGAGAGAAAGAAAGAAAGAGAGAAAGAGA
```

FIG. 8-227

```
AGAAAGGAGAACTTTCTTGGCTTAATTTACCCAAAAGGTATGATATTTTCT
TAATTTGCATAAGGCAGAGCATGAGCTGATACCAGTTCTGGTAGAAAAAGT
AGGTGAGACTGGATCCCCCAAACAAGAGTAAATATTTAATATAATAAGGAA
AGAGTGGCCGAAAGTATTCAATGCCACAAGTAAGATTCAGAGTAGATTTTT
CAAACTGCATAATTTGTTTAAAAAGCATAATTTTATAGCTGGATTTTGCAA
GCTCTCTGAGGGGATCTTGTTCATTTTGAGAATCACTATATCCACAATTCT
TGGCACAGTGTCTGTCCTATGGTGTGTGCTATGATCCAAATGTCTGTATCC
TCTCAAAACTCATGTTGAAATCCTAACCCACAAAGTGATAATATTAGAAGG
AGGGGTCTTTGGGCAGTAGTTATACCATGAGGGCAGAAACCTCATCACTAG
GATTAGTGTCCTTATAAAAGAAACCCAAGGAAGTTTATTCAACCCTTCTGC
CATGTTAGGACTCAGCAAAAGATGGCTACCTGTCCTCACCAGACACTAAA
TTTGCCAGGGCCTTAATCTTAGACTTCCCACCTCCAGAACTGTAAGAAATA
AATTTTTTGTTGTTTATAAGTCACCCAGTTTATGATATTTTGTTACAGCAG
TCTGAACAGACTAAGACAGTACACGCTTAATAAACATTAGTTTACTGAATG
AATGAATTCTTGCATTGCTTCACCACCAACAATCAAGATCTCTGTAGCTGG
TTTAACCCCCTCACTCCCAATCATGATTTTCATATAACAAAGTTAACTCAG
TTAAATCAACTCAATAAGGTATACATTAAATGAAATTAAAGAAGTTGTAAC
ATTTATAAACATCAAGAGTAATGTAGAAGAAAAGTCCAGAGATCCTTAAAA
ATTTAAGCCTCTCTGGCCTGACATTAACAGCTAAGGCAGGAACAGAAAACC
AAACACCTCATGTTCTCACTTATGAGTGGGAGCTGAACAATGAGAACATGT
GGACACAGGGAGGGGAACAACACTCACTGGGGCCTGTTGGGGGAGGATGGG
GTGGGGGTGTGGGAGAACATTAGGTAAAAGAGCTAATGCATGCTGTACTTA
ATACCTAGGTGATGGGTTGATAGGTGCAGCAAATCACCATGGCACACGTTT
ACCTATGTAACAAACCTGCACATCCTGTACTTGTACCCAGGAACTTAAAAA
ATAATAATTTTTTAAAAAACAGCTATTTCCAATCAGAGCAGTTCAATTCCA
TACAATTATTATTATTATTATTATTATTATTATTATTTTGAGATG
GAGTCTCACTGTCGCCCAGGCTGGAGTGCAGTGGCATGATCTCAGCTCATT
GCAATCTCTGCCTCCCAGGTTCAAGTGATCCTCCCGCTTCAGCCTCCTGAG
TAGCTGGGATTACAGGTGGGCACCACCACGCCTGGCTACTTTTGTATTTT
TAGTAGAGATGAGGTTTCACCATTTTGGCCAGGCTGGTCTTGAATTTCTGA
CCTCATGTGATCCTCCTGCCTCGGCCTCCCAAAGTGCTGGGATTACGGGCT
TGATCCACTGCGCCCAGCCAACATACTATATTTTTTTTGATAAATTTTCT
GTATTCTAGACATGACATTAGCTTCCGACAATATTAATTTATTAAGATCTG
ACCCATGACATGACTTCATAAGAGTTCAGAGTCCACTGAATGAGACCACAC
ACAGAGACAGACAACTAGAATGAAGGATGATAAACATGAACAATACAAACT
TGCACAGGTGACTAGAAAAGAACAAATGAAGACTCCTGCCAACTGGGGGTA
TCAGGGGAAGGCTTCCCAGGCAGAACAGGGCTGCGCCAGTCTCCATGTGTG
GTATGAATAAGTCAGTAATACAGGGGAAGCACCTTCCAGAAAGAGCAAACC
CGTTGAGGCTTGGTGTGAGGAATAAGAAGTGTCCAACATGACTGGGGATTA
AAGTACAAAGGTATAAAGGAAATGTGGTGAACTGACTGGAAAGATAAGAAT
TTTTTTAACAGTTACTTTTCCCAATAGTAGAATTAACTAGACAGGAATAG
AAATGGAAGAAGTTTTTATGTTCCCTTAGAATGAAAACTATACATTTTTA
AGAATTATATGAACAAGGAAAATGTGACTCAAAGGCAGAAAATGATAGAAT
TTTATTATAGGGCAGAAAACAGGATCTGGCTAAATTAAACTAAGTACTCTA
CTATACTATACCATATGCTATATTCTTGAATGGGAGAAGTAATACCATAAA
AACTATTGATTCTTCCTAAATTAGTAAACACATTGAGTGAAAATCCAAGAG
```

FIG. 8-228

```
GAAGAAAGAAAAATGGAAGACAAACTGGAAATAGCCCAAATTTTCATCAGT
GGAAGACTGAGTACTTTGTGATACATAGTCATTGCAGAAAAATAACACAGT
TAAAAAGAATGAATCACATCTATAACATTTGACCTGAATACTTTCATATAA
TGTAATACATTTTTAAATGAGTAAAGCAGATACTAAGGACGTATAAAGGGA
CTCCATTTTTTCTGAATATTAATCAAGAAAATTCTATATATCTGTATCTT
TGTTTACATAAGATTGTGTGAGCCATAATAGCTGTTGACTTGGGTTATCAG
GTTTGGGTAAACAGTTTAGTGGTAAAAAAAGATGTGTAAGACTTGGCCGG
GTGCAGTGGCTCACATCTGTAATCCCAGAACTTTGGGAATCTGAGGCAGGC
AGATCACTTGAGGTCAGGAGTTCCAGACCAGCTTGGCCAACATGGTGAAAC
CTCGTCTCTATAAAAAAACTACAAAAATTAGCCAGGCATGGTGGCGCACAC
CTGTAGTACCAGCTACTCAGGAGGCTAAGGCAGGAGAACCGCTTGAACCCG
GGAGGTCGAGGTTGCAGTGAGGTGAGATCGCGCTACTGCACTAAGCCTGGG
CAATGACAACAAAACTCCGTCTCAAAAAAAAAAAAAAAAGTGTAAGACTT
AGCAAAAAGGTGACCAAAAAAAAGCAACATTTATAAACTATG
GATGTAAAACTCTATGTATGTGTGAGTGTGTATACATGTGTGAATATACAT
AGGATACATTTTTGTCTGTATGTGTATATGTACATACATGCATGTATGTGT
ATGTGTGTGTATATATACAAGCTTTTTTAAAATGTTTTCAACAATATTGAA
TTACATTAGAAAAATGCTAGTACTGTAGTGTACAAAGCAGGATGCGTTGTG
CACATCCACATACAGGAATAGAAACAGATATATACATACACACACACTACA
CACACCCCTATACCTACACCAAATATACATTGAGAGAGAGAGATAGAGAAA
ATAGTAACTAAGGTAGTTAATTCTGGCCACAAGGATTTTTAGATGAATCTG
ACTTTCTTCCTTAGGTTTTTTTGTATTGTTTAAAGTTTCACACAAATAGC
ATTTATTTACTGTATAATCATAAAAGGCAAAAACCTATTTTGATTTTAGGA
AAACACAAAGCATCCAAACCAAAAATCTCAACTTAGGAAATAGCGGGAAAT
CTAGGGAAGTCAACAGGACCAGGTCATGACGGTCTTTTATGCAATGTCCAG
GAGCTTGAACTTTATCTTGTCGTTCCTATATTTCCTCAAAACAAATGTGTG
TGGACGCAGAAATGGAAATGCACAGCAGTGCACTGAGGTCACAGGAAAAAT
ACAAAACAGTTTTTCTGAAGTACTAACTTCACTCAAAACTTCGGGAAACAT
TTTAAAAATGGTTTTAAACAAATTTGACTAAATTTGACAAATTTAGTCAAA
TGCAAAATTTTCATTTTTAAAAGGAAATAAATTTTAGAGGAAAAAACAGAT
GTGAAAAAGAATACATGAAATAGTACATGAAGGAATACATGCACGTGGCAT
ACACTTGAATCCATGTATATGCCAGGTTTTCTTGTGTTGCACACAAGACCA
ACTCTGAAGTTAAAGATAACCCAGTAGAAAAAATTAAATGATGGGGAGTAA
TTAAAATGTTTTCAGCAGGAGTAGGACATGATTTTTATATTTAGACTGTTT
AGTCGGCTAGTTATGTCTGACGGATAGAAGTGAGGACACTCCTAATTGAAA
AGTAAGTGCTACTAAGAAACTCAACGTGGGGGTCATAGAATGAAGCCAGAC
TTTTGTTCCCAAGCAGGAGACAGATGCAGATAAGAGGGAATGAAGATGAAG
TAAGGGCTGAACCACAGAAGCTTCGCATCATAAGTCATTGTATTTCTCTGA
GTGAACATCATAGAACTTATTTACTATCTGGTCACAAAATGCCACTGACAT
GAAAAGAAATCGGGTTGAAATGGCTCTAGACCAAGATTCCCAAGACATCAA
GAAATCACCAAAAGTTGCCTCAGGTTCACAAAAAAAGATATTCCAAGGGAG
TTCTCCAAGTAAGTAAACACTCATTATTTCTATAAGGCTTAGGCCACAAGA
CCTTGGCTGAGACCCCTGTCTCTGTGATCTGGTCTGTACCACATTGGAAGG
GCCATGACTGATTTCTACCTAGACATTTAAGGCTGAACGGAGGCTGAAGAA
CCTCTTGCTTGCTTTCCCATAGACTCACATCTGATAACAGCCCTCATCTTA
GGCCCCAGAGGGCAAGAAGAGGTTAAGAAGGATCAACCAAAGGTAAAGTAC
```

FIG. 8-229

```
ACCAAGAAAAGAGCAGCTCTTTGGTTAGAATTTTAAGATAAAGAGAGACAC
ATAAAAGCTACTGTTGAAAAATAACAGAAGGAACAACGTTTTATCTAATCA
ATAGATGGAACAAGACAATAGAGGACCATCTCAACAATAACCTAGAATACC
ATGGAAGACAGACATAAATCATCTGTATTTGTCCTGCTCAAGACTTGCCAT
ATGCCAGGTATGGTGGCTTATACCTATAATCCCAGAACTTTTAGGCTAAGG
CAGGAGAATTGCTTGAGCGCAGGAGTTCCAGACCAGCTTGTCTCTACAAAG
TTCTCTGGGGGTTTTTTTTCGTTTGTTTGTTTTTAGGCAGGTGTGATGGC
ACACACTTGTGGTCCCAGCTACTCAGGATGCTGAGGTGGGAGAACAGATTG
ATTCTGGGAGGTCAAGGCTGCAGTGAGCTATGATTGCTCCACTGCACTCCA
CCCTGGGTGACAGGAACTGCAGACAGCCTCTAGAAGTTGAATCAGCCTCTA
CCAAGAAGCTTCTACCGGTGCAAAGAACTGAATTTTTCAACAAACCTGAGG
GAGCTTGGAAGTGGAAATTTCCACAATCAAGCCTCTGATGAGAATTCAGAC
TCAGCCAACACCTGGATTGCAGCCACATGAGGCTTGAAGCAGGGAACCCAG
TTAAGCCATGTCAGAACTTCTATCCACAGACCTTAGGTAATAATAAATGTG
TGTTGCTTTAAGCCACTAAGTTTTGCTAATTTGTTTTGTAACAATTATAT
ATAACTAGTACACATGAATAGTAGAATCTAATATCAGCCATTGACTTCAAT
GAAGGAAAAAACAGATGTGAAAAAGAATACATGAAATAGTACATGAAAGAA
TACCTGCACATGGCATACACTTGAATCCATGTATATGCCAGGCTTTCTTGT
GTTGCACACCCAGACCAACCCTGTAGTTAAAGATAACACAGTAGAAAAACT
GAAGAGTTACTGAGAGTAATTAAAATGTCTTAAGCAGGAGTGGGGCATGAT
TTTTATTTTTAGACCGTTTAGTCTGCTAGTTATATCTGATGGTTAGAAGTG
AGCCTATCTCTGGTCCCATGTTCTTAGAGAGAGTACTTTTATCTCTTTATC
CATCTAACATCTCTAATTTATGTAACATCCCAAGTCCTCATTAATCCTGTG
TTATTGCTGTTGGAAGTCCATCTATCCCCTCAAGAACAGAGCCTGAAATTC
CTCTTTGAAAAATTTCCATTCATCATAATCTCAAATTTCTCCAATGTCATT
TTCCACCTAAATTTCATGTGTGACTTGAATCTCAAGACTATTCATCTGCCC
CAGGTATCTGTTTGATGCCTGGATATGTCTGAATTATTATTATTGTTATTA
TTATTATTTTTTTTTAAATGGAGTCTTGCTCTGTCACCCAGGCTGGAGTG
CAGTGGTGCGATCTCAGCTCACTACAACCTCTGCCTCCTGAGTTCAAGTGA
TTGTCCTCCCTCAGCCTCCCCAGTAGCTGGGATTACAGGTGCCTGGCACCT
CGCCCAGCTAATTTTTTGTATTCTTAGTAGAGATGGGTTTTCACCATGTT
GGCCAGGCTGGTTTTGAACTCCTGACCTCAAGTGATCCACCCACCTCAGTC
TCCCAAAGTGCTGGGATTACAGGTATGAGCCGCCACACCCAACCTTAGACC
TCATCCTACCCAGCTCACGTGTCTTTTAATCCTTTAGCTGAGGTTGTAGTT
TTAACTTATTGCTGCTTGAACCTATTTCAATGCAAAAGTTCTAAAAGAACT
CAGCCACCAAAATTCCCTTGATTTGCTGCACTGTACCAAATATTAGTCTTA
ATGAAATACAAGATTTGTTTCAGGATCTCAAGCCCAATATTTTCAACTGTA
GGCTTCCCAGTATCCAAGGTTTACGCAGGAGATTGGCAGTGGGTACATTCC
CAGGGTCAGTGGTTTTTATCCAGGAAGGAACCTCAGAATCACCTGGGGAAT
TTTAGCAACATACACACCAGTGTTCTCAGGAGTGAGGCTCAGGTATGTGGA
TGGCAACAATACTTCCCTTATCAAAAAGCTGCCACCACACCAGACAAATGA
AAACTGCTCTTTAATTATACAGCTTGGCCTTACCTAATGGTTCTCAATTTT
GGATGGACATTCAAATCACAAGGGTAGTTGGTTTTTTTTGTTTTGTTTTGT
TGAGACAGACTCTCACTCTGTCGCCCAGGTTGGAGTGCAGTGGCGCCATCT
CGGCTCACTGCAACCTCCACCTCATGAACGTAGTTTTAAACAGCACTAGTG
CCTAAACCAGACTCCAGAGATCATGATCCCTAATCCTATCCCTACCCTGCG
```

FIG. 8-230

GTACTCATTCTGAGATATGCCCTGGGTAATAAGAATTTTAGAAGGTACTCA
GGTGATTCTAATGTTCAACCAGTCTGAGAACCATTCGCAGACTTCATATAG
ATACTTTATTCCAAACAGCTGAGCTGGACCATAGCTAGAAGAAGGAATAGA
GATGAATGAGAGTTCATATTTTCCATAGAAAGCCGCTGCCCTCTTCTAAAT
GTGAATGGAAGTTCTGGAGACCCCTATCCTAAGGTAGACAGATGACAGATA
CACTGGAGAATGCTGAAGGAAGCAGATAGGAGTCTAGGCTTTAGACCACAC
CTTCCAAGACGTACTACTCATGCCTGATGAAGTATTACCAAACATACCCCT
GGGCCAATAAACAAAGCAGGAGCAAATGTGTTTGTGTGTGTATAACTTTCT
ACACAAAATACAGAAAAAAGTGATTCAATGTTCAGCATAAATAAAATTTTG
TGTTTTAGTATTGTTTTATTTCAAAGTACATCTTGGTGAGAATGCATTATT
TTGAACTGGATAAAAGCCCCCCACTACTGAATCCCAGGTCTCTCTATGAAG
CCTGAATAGAGGCACTGTAACTCTAATGGCCAAAGGGCTGGCCTGGAAATT
CTCCCTTCAGCTGCAAAAGAGAAAAAGAATAATCCAAGCAAACAAACAAA
ACAAAGAAATGAGCAAACCACTACAACACAAAACCCTTGGGATGAGATGAG
TACTAGACTGGGAAAGTGATAGCTCTGGTATTCATGTGTGTGTGTGTGTGT
GTGTGTGTGTGTGAGAGAGAGAGAGAGAGAGAGAGCACATGAGAGCACA
CACAAGACCCTATAGAGGAACCAAGTAGCTTATCTTCTTCCTTGGATTCCT
CTATCTCATAGCCTAGAAGACATGGGGTGATCCTAGCCCCTGGTAGTGTAG
GACAAGGTAGAGTGGGACTGTGGTTTTAAAATACTTTTTAGACCGGGTGTG
GTGGCTCATCAACACTTTCGGAGGCGGAGGTGGGTGGATCACCTGAGGTCA
GGAGTTTGAGACAAGCTTGACCAACATGCTGAAACCCCGTCTCTACTAAAA
ATATAAAAATTAGCTGGGCATGGTGGCAGGCACCTGTAATCTCAGCTACTC
AGGAGTCTGAGGCAAGAGAATCGCTTAAACACAGGAGGCAGAGTTTGCAGT
GAGCCAACATCATGCCATTGCACTCCAGCCTGGGTGACAAGGGTGAAACTC
TGACTCAAAGTTAATTAGTTAATTAAAATAAAATACTTTTTTATTTGGGGC
TGGGTGCAGTGGCTCATGCCTATAATTCTAGCACTTTGGGAGGCCAAAGTG
GGAGGATCACTTGGGGGCAGGAGTTTGAGACTAGCCTGGGTGACATAGCAA
CATGCCATCTCTACAAAAATTTAAAAAATAAAAATTAGCTGAGTGCAGTGG
TGCACACCTGAAGTACCAGCTACTCATGAGCCTGAGGTAGGGGGAATTACT
GGAGCCCAGGAAGTTGAGGCTGCAGTGAGCAATGATTGGGCCACTGAGCTA
CAGCCTGGTGACAGAATAAGATGCTGTCTCTAAAAACAAAAAACAAACAAA
AAAAACCCAAAAACCTTCTTATTTTAAAATGATTTCAAACATATAGAAAAA
TCAGAAAAACAGTACAAAGAACACTCATATACTTTTTACCTAGATTGTTAA
TATTATACATTTGCTTTTTCTCTACCTATCCATTTATTTATATGTCTTTAT
ATCTCTTTATATATATATACTTACTGAAACATTTGAAAGTTGCAGATAA
TCATCTTCCTATATTACTCAATACTTTATCTTTAAATTCAAATTCAAATTT
TACCAGCTGTCCCAATCATGTCTCTGACAACACTTTTTCCCCTCAATCCAG
GATCACAAATTGCATTTGGTTGCTATCTCTTTAGTCTCTATTAACCTGGAA
CAGTTTCCTGGCCTTTCTTTATCTTTCATGATATGAAATGACAATGAATTT
TTAAAGGTTAGGTGTTTTGTAGATTAGTTCAGTTTTAAAACTTCACAACAA
AGTGCCAAAGATGTCTTGGCAGCAGTGCTCAAAACAGGTTGGAGATGCATA
GGAGCCACAGAGAAGGGTCTGGTTCAAAGGCCAGTGGTCGTCTCATTACAG
CACTGCTCCATCAGGTCTAGGTCTGGAGACTTGGTAGCACGTCTATGGCCC
CAAAGTGTGTAGAGAATGTTGAGAATTGCCTAGGGTGGCAGACTTAGAGGA
AGAAAGGTTGGTATGAGGCCTGTCTAAAATTGAATTTGGCTATAGAGTTAT
GGAAGGGTTTTAGGCCATGTCTGGGTGGAATCAGATTCAGTCAGCAAGTAA

FIG. 8-231

```
GGGGTCTTTGGGAGGTGAGCTTAGGCTGTCTGGGCCCCTTCGAGGAGGGCA
GATTTTATGGGGAAGGGCTCTCCTAGAAGAACCTAGTTTAGGATGAGCAAA
TCACGCAGGTTCATTCTCCACTTTACCCTAGCACTTCCTAGGCTCAGTGGT
GGTTTTGAACTTTTCCCATCCCTGCAATTACTCCATAAAGGGAATGTGCAA
GGAAGAGGGGAGGAAAGAGATGTGAGTTCTGCCAGAGGCTTCACTGTTTCA
TTCCCAGATTTATTTGAAACCAACCCTCCTCCTGTACTTCATGCTCTCCAA
GCTCATGGTCCTGGAACTTCACATTTACATAATACGGAATTTTTTTATTA
CCCTTGATCTTTATGCATGCAATCTTTCTGAACACCCTGGACCCCCTCCTT
CTCTTGGTGACCTTTTCCTTCTCCAAAACATGGTTCACCAGTTATTACCTC
TGCAGCAGTGGTCCTTCCAGGAGTTGCTTGCTGCTTTGTTCTTCTCTCAGC
CTCAACACTTTTTCTTATCTTGTTACAGCATTTAGAATGTAATGTTTTGTT
TTGTTTTTAAAACACATCTTGGCTTTCTGGAAACTTATATAGAAAATAATT
TTTTTTCCCTCAATAGATATATGGCTAGGGTCCAGCCTAATGTCTGCCATA
GAGAAGCCTAATGTCCAGCCTAATGTCAATAAATGTTTATTGTGGGCATAA
AGGAATACATTTTAAAATAATGGAGTGTTTAGGTAAAATTAGGATTATTAG
CTTGAGTCATTTAAAATCATCCACAAGAACCAGATCAAATGTACATGTCTT
TAATACTGGTGAAAGAAGTAGTTACGCTGTCTTAAAGGCAAAACGATATGG
ACATAGCCACCAGAAATACAAGAGTGCCATCTCTTGGTAAACCTGTTAGCA
GACAGAGAAGACACTGAGAAGCCATGTAAAATATACTTGATAATGTGTCTC
TTATGTAGGTTATGTAAAATGTGGAAGAAAGATGGAAACAAAATTGAGAGA
CGTGGTTATGGCATTTTCCAGGAAAATTGGAAAATATTTTCTCCTAATAAT
TCATGCAAAATGTAATGATATTTTTTAATGCAGAAGAAAACAGTGTAACAA
AAAGCATTATAATTATGGCAAATTGTTGAATGCTTTCTCCACCCCTGCCCT
TTCCACTCAGAGTAGGAATGAAATAAGGATGTCAGTTATCACACTTTATGT
TCAATATTATATGGGAGATGCTAGCCAGTGTACTGTGGAAAGAAAAATAAA
TGTTAATGTTAGATGTTAATGGTGTAAATATTTCAATTGAAAGGCAAAGAT
TGTTAGAATCGACTTAAAAATGCAAGAACCAAACACGTTGGCTAGAAGAGA
AACATCTTAAATATAAAAACACAGATAACTTGAGAATAAACATATTAAAAT
ATATACACTATGCAAACAGAAAGCATAAAAAGACTAAAATGGCTATAATAA
TAACAGCTAAAATAGAGTTTAAGACAGAGAGTGTTACCAGAGACAGAGTGA
TATTTTGTATTGTTAAAGGAGTCAGTTGCCAGCCTGGCCAACATAGAAAAA
CCCCATCTCTACTAAAAATACAAAAATTAGCCAGTCATGGTGGTATGTGCC
TGTAATCCCAGCTACTCGGGAGGCTGAGGCATGGGAATTGCTTGAACCCAG
GAGGCGGAGGTTGCAGTGAGCCAAGATCACACCACCGCATTCTACCCTGGG
TGACAGAGTGAGACTCTGTCTCAAAAAAATAAAATAAAATAAAAATGCCGA
GGTGGGCGGATCACCTGAGGTCAGAGGTTCGAGACCAGCCTGGCCAACGTG
GTGAAACTCTGTCTCTAATAAAAATACAAAATTAGTTTGGCATGCTGGCAC
ATGCCTGTAATCCCAGCTACTTGGAGGCTGAGTCAGGAGACTCGCTTGAAC
CCAGGAGGTGGAGGTTGCAGTGAACCAAGATTGTGCCACTGTACTCCAGCC
TGGGCAACAGAGTGAGACTCCATTTCAGAAAAAACAAAAACAATGACAATA
GAAAAGTGTCATTTCATCAAGAAAACATAATAATCATAAATGTATGATTCT
AACAACAGAGTTTCAAAATACATAACGAAGTTTTAAAATACATAGCAAAAT
GTCATAACAGAGTTTCAAAATACATAAAGTAAAAATGGAAAAGAAAAGACA
AAATAGACAATTCTACAATCACATTTGGAGAGTTTAACACCCTTTTTTTGG
TAATGATGCAATAACTAGACAAAATATCAGTAAAGACACAGAAGATCTGAA
CAATCCTATCTATTATCTTGAGCTAATTGATTTATAGAACATTATACACAA
```

FIG. 8-232

```
TATCTGCATGCACATTTTGCTCAAGTACACATGATATATACATCATGATAG
ATCATATTCTTTTTTTCTTTTATTTTTAGTTGACATATAATAACTGTACAT
ATATACGGGATAAAGAGTGATATTTTTATATGTGTACACAATGTGTAATAA
TCAAATCAGAGTAATTAGTATATCCATCACCTTAAACATTTATCATTTATT
TTGTTGTGAGTATTCAAAATTCTTTTCTAGCTTTTTGAAAATATACAATAA
ATGAGAGTTAACCATATGCACCCTACAATGGTGCAGAACACCGGAACTCAT
TTCTACAATCTAGCTGTAATTTTGTCACCATTAACCAACCTCTCCCTATCC
TCCCCTCCTTGCTACCCTTCCCAGCTTCCGGTACCCACAGTTCTGTTCTCT
AAATCCATGAGCTAAAAATTTTTCTCTACTTTCACATATGAGTGATAACAT
GTAGTATTTATCTTTCCAATCCTAGCTTATCTTACTTAACATAATGTTCTC
CAGTTTCATCTACGTTGCCACAAATGACAAGATTGCATTCTTCTCATGGCC
AAATAGTATTTCATTGTGTATATATGCCACATTTTCTATCCATTTGTCTGT
TAATGAACATTTAGGGTTGACTCTATATATCAGCTCTTGTGAAGAGTGACG
CAATAAACATGGGGATGTAGGTGTCTCTTTGTATACTGATTTCCTTCCCTT
TGGATAAATAGCCAGTAGCAGATTTTCAGCCTCATCTGGTAGATCTATTTT
TAGGTTTCTGAGAAACCTCTGTTGTCAGTAGGCTGGTTCAGATTCTTGAAT
TCCCTGCACAAAAGAATTTGAAAGCCAGTCCAAAGTAAAAGTAGGCAAAGG
AGTTTATTGCAAGGTGAAAGTACACGCTGATAGCAGAGTCAGGGTCGGCTA
CTTCAGCACCAATTGACACTGAAGAAACTCCCGTTATGGGAGTCCTACGTG
ATTATCCATGAGGGGGTGGGAATGGGCATTGTTGTTAAATATGTTTTGGGT
GGTCTCTTGAATGTGCATGCAATATTGCCATACACGCTAGTACATACATCA
CATGTATTATTAGCATTTTAATTCTCTACCCAAGGGTGTGTTTCTTACTAT
TAAAATGAGTATATGTCAACCTGAGAACACAGCTTGTGGGTTTCTGCACTT
GCACGAACTTAGGGATTTTCCCTCCTGCTCTTCTACCTCCTTGACTGAGGA
TATTCTAACCACTAGCCCCAGATGCAGTTTGTGTAATGTCAAGAGATTTGT
TCTCTCCATCAATTTGACAAGTTTCTTGTTTCCTTTCAAGGGAGGCTGTGA
CCACCCTATGTAACCTACCTCACTTCCATACTATTTGCATAATGGCTATG
CTAATTGACATTTCCACCAGTGGGACATAAGAGTCCCCTCTTCTGTACATC
CTCACCAGCATTTGTTATTTTTGTTTTTTTGACAATAGCCATTCTAACTG
GGGTGAGATGATACCTTATTGTGGTTTTGATTTGCATTTCCCTGATGATTA
GTTATTTATATGGTTTGGCTGTGTCCCTACCCAAATCTCATCTTGAATTGT
AACTCCCACAATTCCCATGTGTCCTGGGAGGAACCCAGTGGGAGGTGACTG
AATTATGGGCCGGGTCTTTCCTATGCTGTTCTTATGATAGTGAATGAGTCT
CACGAGATCTGATGGTTTTAAAAACGGGAGTTTCCCTGCACAAGCTCTCTC
TTTGCCTGCTGCCATCCATGTAAGATGTGACTTGCTCCTCCTTGCCTTCCA
CCATGATTGTGAGATCTCTCCAGCCATGTGGAACTGTAAGTCCATTAAACC
TCTTTCTCTTGTAAATTCCCCAGTCTCAGGTTAAGTCTTTATTAGCAGCAT
GAAAACAGACTAATACAGTGATGTTGAGCATTCTTTCATATATTTGTTGGC
CAATTGTATGCCTTCTTTTGAGAAATGTCTGTTCAGTTCACTTGCCCACTT
TTTAAATGAATTGTTGGTTGTGCACGGGTGGCTCGTGCCTATAATCCCAGC
ACTTTGGGTGGCTGAGGCAGGAGAACTGCTTGGGACTAGGAGTTTGGGACA
AACCTGGGCAACACAGAAAGGCCCTGTCTCTAAAAAAATGAAAATAATAAA
AATAAATGAATTATTAAATCTGACTACAGTAGAAATAAATTTGAAATCAAT
AAAAATAAGAAATGTAGAAAAAAACACACATATTTGGAAATTAAACATCAT
TCTAATTAATCAATCTCTCCAAACAAATCACAAAAAATTACAAAATACATT
GTACTATATAATAATGACAATAAAGCACATCAAAATTCATGGGATGCAACT
```

FIG. 8-233

```
TAAACAGTGTGTAGAGAGATCTGTAACTTAAATTGCTTATAGTAGAAAACA
AATAAAGTCTAAAATGAAAGTCCAGATTCTACAAAGGTGGTATGTCTAATA
AGAGATACTTGTGTTCTCCCAGTAATACTGCGATCCCAAAGGATGATAAAA
GTAAACTAGAAGTAATCCCATCCTACTCTCTGGAAACTGCTAGAATGTTTG
CTCTGCTTCTCAGCAGAGCAAGGGATGTGAGAGAGGTGGGGAGAGACAGAG
AGAGAGAGAGAGAGAGAGAGAGATCATCAATCCTGATAAGTTGTAACCACA
AGCCAACTTTTATACACATTTAGGCTAAAAAATAAAAAGTCTTGGCTAGCC
ACAGAGGCTCATGCCTGTAACCCCAGCACTTTGGGAGACCAAGGTGGGAGG
ATCACTTGAGCCCAGGAGCTCGAGACTGGCCTGGGCAACAAAGTGAGCCCC
ATCTCTAAAAAAAATATTTAAAAAATTAGTCAGGCATGGTGGCACACACCT
GTAGTCCTAGCTATACAGAATGGTGAGGCAGAAGGATTGCTTGAGCTCAGT
AGGTTGAGGCTGCAGTGAGCCATGTTCACACCGCTGCACTCCAGCCTGGGT
GACAGAGTAGGACTCTGCGTAAAAAAAAAAAAAAAAAAAAAAAGTCTCAATT
CATGAATTGAGTTTAAAGTAATACTTGACTGGTGGTACCCCAGCTTCCTGG
CAAAAGCAGACACAAACCCCCTCTAGAAGAAAGAACATCCCAGTCCTCAGT
GACCCATAAGTAATTTTACCAGAAAAATAAAGAAGTTACTGGCAAAATCAT
CAAATGCACAAAATGGATTGGAGGAAGCGTAGCAAGAATAAATGAAGAGGA
GCTGGGTGCTGTGGCTCACGCCTGTAATCCCAGCACTTTGGGAGGCTGAGG
TCAGGCGTTTGAGACCAACCTGGCCAACATGGCAAAACCCCGTCTCTACTA
AAAATATAATAATTAGCTGGGCATGGTGGCATGTGCCTATAGTCCCAGCTA
CTTGGGAGGCCTGAGGCAGGAGAATCGCTTGAACCCGAGAGGTAGAGGCTG
CAGTGAGCCTAGATGGTGCCACTGCACTCCAGCCTGGGCAACAGAGTCAGA
CTCTGTCTCAAAAATAAATAAATAAATAAATAAATAAATAAATAAATAAAT
AAATAAATAGGGATCAGGAGGTTTGAGTAAATAAGGTTAAAAGTGATGGTG
TTCTAGACTATTTGTGTCTTTATATTAAAGTGAATTTTTGTAGGCAGCAT
GTTGTGGCTCTTTTTTTGCTTTTTTTTGTTGTTGTCTGTTTTTTTAATTCA
ATCTGACAACCTCTGCTTTTGTATTAGAGTATTTAGATCATTTACCTTAAG
TGTGATAATCTATATGGGTAGAGTTAAGTCTATCATCTTGCTATTACTTTC
CCATTTGTCCCATCTGTTCTTTGTTCTCTTTTCCTCTTTTTTTTCCCATC
TGTTGAACAACTTAAATATTTTTTCTCATTCTATTTTATTTCTTTTTGTGG
CTTGTTAGCCATAATTCTTCGTTTCATTATTTCAGTGGTTGCCTTAGAGTT
TATAGTATACATCATTAATTTATCGTAGTTCATCTAAAAGTATACCACTTA
TATAAAATAACATTATTTTCATTTCCACTTCTTTTGCACTGTTGTTGTCAT
ACACTTTTCTTTTGTGTGTGTGTGTGTGTGACAGAGTCTAGCTCTGTTG
CCTAGGCTGGAGCACAGTGGTATAATTTTGCCTCACTGCAACTTCCACCTC
CTGGATTCAAGTGATTCTTGTGCCTCAGCCTCCAGAGTAGCTGGGATTACA
GGCGTGCACCACCACGCCTGGTTAATTTTTGTATTTTTAGTAGAGATGGGG
TTTTGCCATGTTAGCCAGGCTGGTCTTGAACTCCTGTCCTCAAGTGATCTG
CACGCCTCGGCCTCCAAAAGTGCTGGGATTACAGGCACGAACCTTTGTGCC
CGGCCTGTTTTACTTTTAAATGCTATAAATCACACATTACATTGTTAACTA
TTTTTGTGAAAATAGTCAACCACATTTTATGGAGAAAAAATATTATCTGTT
TACTCACATAGTTACAATTTTCTAGTACTGTTTATTCCTTTGTATAAATAG
GAATTTCAATATGCCTAAGGGACTTTTATCATTCTGCCTAAAGGACTTTTA
AAAAATATTTTTTATTGTTCTAGTCTGCTGATTAGATGTTTATTGCCTTTA
GGCAGGGAGATAAAAAAATACTACAATATTTTAGTTAATGACTGTGTCAAT
CAAAAAGAAGCAAGACAATCTACCATTTAATTGCACGGTTGATTTTTTAAA
```

FIG. 8-234

```
TGAAATAGAAAACATCCACATATACAGTACAAAATGTATCATAAAACTCTC
ACATATGACTAGATAAATTCCTTCCTCTTTTCTCTGTATTAAATTGTCTTA
TTTCACCCTCATTTGGGGGGAGTTTTTTTGCTTGGTACAGAATTGTAGGTC
TTTCATTAATCTAAAAAATTTTGCTCCACTGTCTTTTTGCTTATATTGTGT
CTATGAGAAATATGTGATCTATACACTTGTTCTTCTGTACATAATGTGCCT
TTTGTTCTTGGCTGCTTTGAAATTTTTCATTTTCCTCTTGCTTGCTTTGGG
TTTGATTTGTTCTTATTTTCTAGTTTCTTTTTTTTTTTAATTTTGAGAC
GGAGTCTCGCTCTGTCTCCCAGGCTGGAATGCAGTGGCGCGATCTCAGCTC
ACTGCAATCTCTGCCTCCTGGGTTCAAGTGATTCTCCTGCCTCAGTGTCCC
GAGTAGCTGGGACTACAGGCAGATGCCACCAGGCCTGGCTAATTTTTGTAT
TTTGTTAGTAGAGACAGGGTTTCACCATGTTGGTCAGGCTGGTCTCAAACT
CCTGACCTCGTGATCTGTCCGCCTTGGCCTCCCAAAGTGCTGGGATTACAG
GCGTGAGCCATCACGCCCAGCCTAGTTATTGATTTCTATCTTCATTCCACT
TTGGTCAGAGAATATATACTCTATTATTATAGTCCTTTTACATTTATTGAG
ACTTATTTCATGAAGTAATATACAGTCTATCCTGAAAAATGTTTCATGTGA
GCTTCAGAAGGATGTTTATTCTGCTGTTTTGGGGTGTAGTGACCTATAGAT
TTATGTTAGGGTCAGGTTAGGTGTTTTCAAGTGTTAAGTCTTCTATTTTTT
TGTTGATCTTGTCTAACTAGTGAGGTATTGATGTCTCCAACTATTATTGTC
GAATTTTCTATTTCTCCCTTCAATTCTGTCAGTTTTGTTTCATGAATATTA
GGGCTCTGTTGTTAGGTGCATGTATGTTTATAATGTTATGTTTTCTTGATG
AATTGACACTTTTATCATTACAAAATACCTTTCTTTATTTATTATAACAAT
GCTTATCTTAAAGTTTATTTTGTCTGATATTAGTATACCTACTCCAGACAT
CTTTTGAGTACTATTTGTATGTGATGAATTGTTCCTTTCTTTCTGCTCTCA
AGATTCATCTTCTTCATCTTTTGATAATCTGATTATGATGTGTCTAGGTAT
GGATCTCTTTGAGTGTATCCTACTTGGAATTCATTGAGCTCCTAAAATATG
TATGCAAGTTAATGCTTTTTTGCCAAACATGGGAAGCTTTGAGAAATTATT
TCTCCAAACATTCTCTCTCCCTGTCCTCTCACTTTTCTCCTTCTAGGAGTC
CCATTATGCATATATTAGTATGCTTGATGGTATCCCCTGTCTCTAAGGCTC
TATTTCTTTTTCTTCATTCTGTCTTCTTTCTGTTTTTCAGAGTAGATCATT
TCAATTGACCTATCTTTGAGTTCACTGATTACTTCTTTTTGCTGCTCAAAT
TTGCTGTTAAAGCCCTCTAGTAATTTTTTTTTCTTACAGATGAGATATCAT
GCTGTCGTTCAGGCTGGAGTGACCATGATCCTCTTACTGGGATCACAGATC
ACGCATGCTCCAGTCTGAGCAGCAGCATGAGCTCCAGCTTGCTCCAGCCTG
AACAGCAGCAATACATTCTTTCACACACAAAAGGGTTATTGGATCTCACAC
AAGAAGGAATTTGGGGCTAGTCCATACAGTAAAGTGAAAACAAGTTTATTA
AGAAAGTAAAGAAGGGCCGAGCGCAGTGATTTATGCCTGTAATCACAGCAC
TTTGGGAGGCTGAGGCAGGCAGACCACTTGAGGTTAGGAGTTCGAGACAAG
CCTGACAAACATGGCAAGACACTGTCTCTACTAAAAATACAAAATTAGCTG
GGTGTAGTGGCACATGTCTGTAGTCCCAGCTCCTCAGGAGACTGAGGCAGA
AGAATCGCTTGAACCCAGGAGGCAGAGGTTGCAGTGAACCAAGATCGCACC
ACTGCACTCCAGCCTCTAGCCTGGGTGACAGAGTGAGACTCTGTCTCAAAA
AAACAAAAAAAGTTAAGAAATAAAAGAATGGGTCATGCATAGTGGGTAAT
GCCTGTAATCCTAGCACTTTGGGAGGCCAAGGCAAGTGGATCGCTTGAGGC
CAGGAGTTCGAGACCAGCCTGGCCAACATGGCGAAACCCCATCTCTACTAA
TAATACAAAAATTAGCCAGGCATGGTGGCACCCACCTGTGGTCCCAGCTAG
TTGGGAGGCTGAGGCAGGAGAATTGCTTGAACCCGGGAGGTGAAGGTTGCA
```

FIG. 8-235

```
GTGAGCCAAAACACGTCACTGCACTCCAGACTCCAGCCTGAGTGACAGAGC
GAGTCTTTATCTAAAAAATAAAAATAAAAGAAAAGAATGGCTACTCCATAG
GCAGAGCAGCAGTATGGACTGCTCAAATAAGCAGACGTATAGTTATTTCTG
GATTATGTGCTAAACTAATGGATTATTCAAGAATTTTTCAGGAAAGAGGTG
GACAATTCCCAGAACTAAGGGTTCTTCCCCGTTTTAGACCATATAAGGTAA
CGTCCAGATGTTGTCATGGTATTTGTAAACTGTCGTGGCACTGGTGGGAGT
GTCTTGTAGCATGCTAATGCAGTATAATTAGTGTATATGAGCAGTGAGGAT
GACAAGAGGTCACTTTTGTGGCCATGTTGGTTTTGGTGGGCTTTAGCTGGC
TTCTTTACCGTTACCTATTTTATCAGCAAGGTCTTTGTGACGGGTACCTTG
TGCAACCTTCTATCTCATCCTGTGACTAAACTCCTGGTTAGAATGCCTAAC
CTAACCCAGCAGGCCTCAGCCTTATTTTACCCAGCCCCTATTCAAGATGGA
GTCACTCTGATTCAAATGCCTCTGACATATTTTCCCACTCCCTTTTACCAG
GGAACCCTTAATCCTAAGGATTGCAGTGGGATAAAGATCCGTCTTCTATAA
CTTCTTCAGACTAAATAGGGGCAATGATATTCCTGTCTAATTATTAGGGTC
TCTTGTGTCCAGGGTAGAGAGGAGCTCAGTCACAAAGTGTCAGTATGGTGA
GACATTCATAACTCTGAGGCTTCCCAAAGTGTTGAGATTACAGGCGTGAGC
CACTGTGCCTGGCCAGGGTCCCATTTTTATACCAGATCCTGGATCCCAAAA
GAGGGAATCAGCCCTCTTTTGGGGGATCAGCCATCTCCCCTGGGAATCTTA
TCTCTCGGTGGGGATGGAGACATTTCCATACCTTCTAGGTAGTCAAGAGAA
TGCTTCTTGTGATCCAAAAGTGCAAATAGCCAAGTATTCACCTATATTTGC
CTTTAGCTATCCCCAGAAGTATATTTCCTACCTGGTTATTACACACCAGAT
CTCCCTCATAATGCAAAGTAATTTCTGATACCCCCAAAAGTCAAAAACATC
AGATAACATAATGCAAAGCCAAACAGAGCCTTAGATTTTGCGAAGGATCTA
TCCACTTCCAGTTCCTGGGGTTTCATGAGGAAAACAGAGGTTTTCCCAAAA
TGGGGTCTGTGGTGCCTCCTCTGCTTTTCCCAAGGAGTCCCAGGCTTTTAG
AGATTGAATATCCACTTTTAATTAAGCTTTTAACCATAAACCATAGCACTC
TAAAGCAAAAAAAAAAGGAGTCCTTTTAAGTTTCTTATTACTCAACTTTAG
CCATCCCACACGGCCATTATTTCTGGCTTTTGAACTTTACCAAAGATAATC
TCCCAGGTTCTCAGAGAGAGGAAAACTCAAGACAGTGTGTGGAGGGGAAGA
GAACAGAATCAACAAATGGTAAAGGTCACACAGATATCAATCAGAAAGTAC
TCATTCCCTAAGCCAGGATTGAACCTTGGCCGCCATTATAAAATGACAAAT
CCTTAGCTGCTGAGCTACAACACTGGTTAGTTTCCATTGCCCTTCCCAGAA
GGGGTCCAGAGCAGCCAATTTTGAGCTTGCAATGGCTTGAGATAATTTTTA
GAGTTAACTATTACATAAACCCCAAAATTCCTGTTCCCTGGATGGCAGAGA
CCAAGAGAAAGTACCGCCACGTGGTTACAAGGTGAAGCTCCAAAGGACATA
AAACAAGATGAGAAGGAAACTTCATCCAGTTTTTATTTTTTTTTTTTTCCA
GGGACCTGTAATAAACTTTGCAACGGACCAGTTTACTGGGCTGGCTTGAAC
AGCAGGCTTATGGAGTCCTGAGCCCATGTTCTATCCTACCATATTCCTCTT
TATGACAGAGTAATACAGAAAGACAAATTGATATCACAAAGTATACCAGAT
TCATTACAGCTTAAGACTAGCCCCACAAATCCTTGTTCCCATTAATCAAAA
CTTTACAGAGGTGATAAACAGTGATTTTTACCATTCATTCAGTTTTCACTA
AGAGAGAGAGGCCAGAAGCCTGACTGGTAAGAAATCTTTACCCTTTTGCTG
GCATGCCAGGTTTCTGGGTTCTCTTTCACTGAGCAGCACTAGCAACCTTGC
TCACTGCAAAGCCCTTGGGTCCAAGCTACGACACAAAAGAAAACCAACTTT
TTTCTGTTTCATGGAACCACAGGCAAATAAATGTCTCTCACTTTTGTAAGA
TGCTGCCCAATGGCCACATAAAGTAACCAAATTAACGTTTTCCATTTCAGC
```

FIG. 8-236

```
CAGAGCAATATACATGTGACAAAACATAGACATTGGCCACTCCACTTAGCA
CCCAATATCTAACTGGGAAGGCTCAAACTTGCCCCCAGATAGGCCCTTTCA
TCTTTAATCAAACTTCTGACCAGGAGTTTCAACATATGGTCTCTGGGCAAG
ATGGTTGTCTCAAGTAACAGAAAAGACAGAAAAGAGAAAAGAGAGAAAGGG
AGAAAAGCATTGCCTGTGGTGAGATGGGGAAGGTGAGGAGTTCACAGAGGC
CAGAGAAAGACCCACCCATTGCAGCAACACTGAATCAAAAGTTCAGGCGGC
TGCTTGTCATAGCAAAGGGATCTTTTCCAACAGTCCTATCAGCTGTCAAGC
TTCCCCTTTTGGAGAGAAGAAAAGTTCCCAATGTCCCGTGATCCTGTACAT
GCCTAATCCTGTCACCCATAGCTGTCAGCAAAGAGCACAGGGAAGATTAAT
ACAAACAGAATAGCAGTTAACATCCCCTAATGCTAAATCCGTTTTTAACCA
AGAGAGACTTTACTGAGAGGGGCCTCTAACCCCTTAAATCTTAAGGACTGT
AGCCTTCCTAAGTTGGGTCTCAAACCCAAGTTCGGTCAAGCATTCTTGCCC
TTTATTAAGAGCGGACTGAAACCCTCTCTGTCTTAGGAGAGACCCTATCTC
CCCTAAGTTGCACCTCTAACCCAATCCTATCCTTTACCCGGGGACTCCACC
ACTTACCCAAAGTCAGCCAGTTGGTGCTGTAGTCTGTTTCCTTTGGCTTCA
GAGTCTCCTCAGTATTGTCCCTTCGTGGTCACAGAAAGATTTACCAGAAAN
GGGTCTTGATCCAGACCCCAAGAGAGGGTTCTTGGATCTCACACAAGAAAG
AATTTAGGGCAAGTCCATACAGTAAAGTGAAAGCAGGTTTATTAAGAAAGT
AAGGAAATAAAAGAATGGCTACTCTGTAGGCAGAACAGCAGCGTGGTCTGC
TCAAATAAGCATACTTATAGTTATTTCTGGATTATGTGCTAAACAAGGGGT
GGATTATTCATGAGCATTCCAAAAAAGGGGTGGACAATTCCCAAAATTGAG
GGTTCCTCCACCTTTTAGACCATATAAGGTAAAGTCCAGATATTGCCGCAG
TATTTGTAAGCTGTCATGATGCTGGTAGGAGTGTCTTTTAGCATGTTAATA
CATTATAATTAACATATAATGAGCAGTGAAGACAACCAGAGGTCCCTTTGG
TGGCCATGTTGGTTTTGATGGGTTTTGGCCAACTTCTTTACCACAACCTAT
TTTATCAGCAAGGTCTTTGTGATGTGTACCTTGTGCTGACTTCCTATCTCA
TCCTGTGACTAAGAATGCCTAACATACTGGAAATGCAGCCTAGCAGGTGTC
AGCCTTATTTTATCCAGCGCCTATTCAAGATAGAGTCATTCTGGTTCAAAT
GCCTCTGACAATGCAGCCTTGAATTCCTGGGCTGAAGCCATCTTCCCACTT
CAGCCTCCTGAGTAGCAGGGACTACAGGCACACACCATCATGCCTGGCTAA
TTTTTTTGTATTTTTTTTTTAGAGATGGGGTCTCACTGTGTTGCCCAGGC
TGGTCTTGAGCTCCTAGGCTAAAGCAATCCTCCTGTGTCATCCTCCCAAAG
TGTTGGGCTTGTCAGAGGTATTTGAACAAGAAAGACTCCATCTTGAATAGG
AGCTGGGTGAAATAAGGCTGAGTCCTGCTGGGCTGCATTCCCTGTAAGTTA
GGCATTGTAAGCCACAGGATGAGGCAGGCAGTGGGCACAAAATACAGGTCA
TAAAGACCTTGCTGATAAAACAGGTTGCAGTAAAGAAGCCGGCTAGGCCAG
GTGGGGTGGCTCACACCTATAAGCCCAGCACTTTGGGAGGCTAAGGTGGCT
GGATGGCTTGAGCGCAGGAGTTGGAGATCAGCGTAGGCAACATGGCGAAAC
CCGGTCTCTATTAAAAATATAAAAAATTAGCTGGGTGTGGTGGCACATGCC
TGTAATCCCAGCTACTTGGGAGGCTGAGGCACGAGAATCGCTTGAACTCAG
AAATTGGAGGTTTCAGTGAGCTGAGATCGTGCCACTGCACTCCAGCCTGGG
CAAAAAAAAAAAGAAAAAAGTAAAGAAGCTGGCTAAACCCCACCAAATCC
AAGATGGCGATGAGAGTGACCTCTGGTCATCCTCACTGCTCCCCACCAAAT
CCAAGATGGCGATGAGAGTGACCTCTGGTCGTCCTCACTGCTATGCTCATA
CCAGCGCCACGACAGTTTACGAATGCCATGGCAACGTCAGGAAGTTACTTT
ATATGGTCTAAAAAATGGAGGCATGAATTATCCACCCCTTGTTTAGCACAT
```

FIG. 8-237

```
AATCAAGAAATAACCATAAAAATGAGCGACCAGCAGCCCTCAGAGCTGCTC
TGCCTATGGAGTAGCCGTTCTTTTATTCCTCTACTTTCTTAATAAACTTGC
TTTCACTTTACAGACTCGCCCGAATTCTTTCTTGTGTGAGATCCAAGAACC
CTCTCTTGGGGTCTGGATCTGGACGGACCCCTTTCCGGTAACAGGATTACA
GGTGTGAGTGAGCCACCATCCCCAGCCTTAGTAAATTTTTATTTCAGTTAT
TATATATTTTTATTTATTTCTGTTTTTCAGTTATTATATTTGAAACTCCA
GAATTTTTATTTAGAATGTATTAACAAATCAGGAGTACTGGCATAAGCCTG
GCACAAAGCAAATGTTGACATAGGTCTGGCACAAAACAAGTGTTCAATGCA
TTTTAGCTACCTTTAAGTGTATTATTACTAGCTGCTTCTGGGGCTATCCGG
GGAAAATTATCCTTGCAAAACCCCCACTCACTTCCAGAGCAGGCTTCAGTG
AAGCAGTCATCTGTGTCATGACAAGAGCCAAACTCTGTAAAACATTTGAAG
AGATTTATTCTGAGCCAAATTTGAGTGACCATGGCCCATGACACAGCCCTC
AGGAGGTCCTGAGAACAAGCGCTCAAGGTGGTTGGGATGCACCTTGGCTTT
ATACATTTTAGGGAGGCATGGGACATCAATCAAATACGTTTAAGAAATGTA
CACTGGTTTGGTCCAGAGAGGCGGGACAACTGGAAGCAGCGGAGGAGTGGG
GTGGAGGTGATGACAATTGGTTGAGTTTGTATAAAGATTTGGGATTAATAG
AAAGGAGCACTAGGTTGTGATAACAGGTTGTGAAGACCAAAGTTGTACTAT
GGGATGAAGTTTTTAGCTAGCAGGCTTCAGAGAGAATAGGTTGTAAAATGT
TCTTATCAGACTTAAAAGCTGTGTTGATGTTAATGCCAGAGAGGAATAATG
AGGCATGTTCAACCCCCACTTCCCTTAATGGCCTGAGCCAGTCTTTCAGGT
TACATTTTAAGAAGCCTGACTGAAGAGAAAGTCTATTCAGATGGTTGGGGG
CTTTAGAATTTTATTTTGTTTTATACCTTTGCCCTTGGAAGTTTTGCTGA
AAAATGAACACAAAAAAAGGCAGATTCATAAGATAAAAGGCTTTACAATTT
AATTACTCTGTGGTTCTCCTCATGCACATAGTACCAATATCCCAGTGGAAT
TTAGAAGCTTATATGCCACCTTGAAGTTGAAGAAATAACAGGGGCTTGATC
CTTGCAAAATAGGTTATGGGAAACAGAAGAAGAGGAATTCTGTTGAGGGGC
AATATGTAACTACCAGGAGAGACTAATTGGATCAAAGAACAGATAAATTTG
TAAATAGTTCTCCTTGGAATTTAAATGATGCTTAGAGACTGATTATCTTAT
AAAAGGGTCTGTTCAGGTGTGGTTACATTCTTGGTCTTTCCTATAATGCAC
AATGAGATAACAGAGAGGGAGAAAAGAACAATTGTTCTCGCTGGTGGGGCC
ATCCTATTTTTATGTACCTAGGGAAAAGTCTCTTTAGTGTCTGTTGATCTC
TAAGAGTTTTTCATTCAAAATACTCATTATATCAGGAAGCCACATTTTGGG
GTGAAATTCACTACTCCCTTTTAGAGATACGGGTACAAACTGTTTGTAAAG
AATGCTAAGACTTTGCCGGGTGCAGTGACTCACGCCTGTAATCCCAGCACT
ATGGAGGGGCCAAGGTGGGCAGATCACTTGAGGTCAGGAGTTCAAGACCTG
CCTGGTTAACATGGCAAAACCCCATCTCTATTAAAAAAAACAAAAATTAGC
CAGGCGTGGTGGTGGGCATCTGTAATCCCAGCTACTTGGGAGGCTGAAGGC
AGGGAGAATTGCTTGAGCCTGGGAGGCAGCTGTTGCAGTGAGCCGAGATCA
CGCCACTGAACTTCAGCCTGGGCAACACAGCGAGACTGTCTCAAAAAAAAA
AAAAAAATGCTAAGACTTACTTTGGGACATCCTTTGTCAGGGTCCATGATT
CTGATTAGCTCAAGGCAGGTATTTTTTTTTTTAATAGAGACAGCATCTTG
CTATGTTGGCCAGGCTCGTCTCGAACTCCTGGCCTCCAGTGACTCCCCCCA
CCTCAGCCTCCCCAAGTGCTGTGATTACAGGTGTGAGCCACCACACCGGTC
TGGTTTTTTTGGTGGTTGTTGTTTTAATCCTATAATCCTGTGTCCTTTCT
TCCTACCTCTGAGTAGTGCTTACTCTCTCCCCTTTAGTCATTTGAAAAGTT
TATCAGAAAGTGGGTGCAGTTTCAGGCTGGGTACCGTGGCTCATGCCTGTA
```

FIG. 8-238

```
ATCCCAACACTTTGAAATGCTTAGATGGGAGGATCATTTGAACCCAGTTCA
AGATTACAGTGAGCTGTGATCGTACCATTGTACTTCAGCCAGGGTGACAGT
GCAAGAGCCTGTCTCTAAAAACAAACAAAAAATTGCTTTCACACTGTGATG
CTATCACATCTCTCCTAAGCTCTTGTTGGGGCTCAGAAATTGATACCCTAA
TATATGGCCCTTGGTCATATTGAACTGAAGAAGCCTCAAAGTCTCTCTGAC
ATCCCTGCCACCAACTATCCCTACCAAAACACATCGTGGAATTAAAGTTTC
TTTATCTACCTAAGATCCAGACCCACCAAAAAGAGCAATTATTTTTATTTA
CCCTTCCTGTAAGACCAAGAATGTAACCATGCCCGAACGGACTTTCACAAG
ATAATGTTCAAGTTAATCTCTGTTCCCTGATCTACTTACTCTCCCTAGTAA
TGAAAGGAGTTGGCCAGCTTGCTTTAGGCAGACAGTAAGGGAATGGTACCC
AGAGAACCTCTGACCTGCCCCACAAGTGCTTACACCGGATGTTTTGTGCAG
ATAAGGGAACTTGCACAGGGGGCTTGCCTAAACATGCCTGCAGTGGATGAT
TCCTTTCCTTAACACATGCACAGTTCAGGAAATTAATCAATATGGAGTAGC
TCAGTCTAAAGGCCTGCATGCACTGGTAGGACAGGGTGGAGTTGTCAGGAA
TTTGAGTCTTAAGCCCTAGTATTCAACTGTGAAGAGCAAACCAGAAATCTG
CTTTCAGGACCCTTGTCTTTGCTGAGAGCTTTCCTTTCACTTAATAAATTC
TACTCCACTCATTCTTTGATGGCTGCATGCCTAATTCTTCCTGGCTGTGAG
ACAAAAACCCGGACCTAGCTGAGCGAAGGAGCAAAAATCCGCAACAGTAAT
CCCATCAACAGAGTTTCTCTTCTTCCCCTCCCATAATCTGTTTTGCCAGGA
TAATATATAAGCTTTTAAGCCCTCTTGGGAAGTGGATAATCATTCTATGGT
TCTCCCTGTGTACATGTTAATAAATTTGTGAGTTGATTTTTCAGCAAAGTT
TCCCCAGAAGCCAAAGGGGAAATTTCCCTTGGCCCCTCCACTCTCTTTTCC
CAGCTCTTCTTTTACTTTCGTTTTTATTTCCTCAGCCCAGTAGGTCACAGC
CTTCTTTTATTTCTTCTCTGTCCAAACCATCAGTATATCCTACAGGTGGG
AGAGAAGCAGCTCTCTGGGAAACCAGTAAGCACCATGAGTTCTGATACTTT
CTAGTACCATTTGACATATTAACATCCCCGCCACCCCTAATATGTATGGAC
ACGCACACACATACCACATCACATGCATCACACTAACACAAACTATGTATC
ACATACCACACAGCACACACAGTACCACATACCCCACACAACACCCACA
CCACACTACGTGCATCATGCACATATGTGCACACACCTCTTGTGATGTGTG
TTTAGTGCAATTCAGAAAGTTACTCTTTGATTTAATGCACATCACTATGCT
TAGAAATATTCTAGTTACTGGGATTCATCAGTGAACAATATTGAAAAAAAT
CCATCCCTTTGCATTCTCATGAGGGAAGCAAACACTAAACAAAATAAATTA
GTAAAATATTCAGTGATAAGTGCCATGGGAACAAAATAGATTTGAAAATGT
TTGGGAGGGAGAGAGGGGTACACTTGCTAACAAGTGGTCAGGATAGGGTTA
GTTGAGAGGCAAAATCTGAAGGAGTTGAGGAAAGGCATTCTAGGAATAGCT
GAGTGCTGACTCTTGCCCACAGTGGGAACACACAGTACAGAGCTTCTGAAG
GAGACTCTAGTGACCTACTTCCCATTGTGAGTCTTTGGACTCCTATATCCC
ATAATCACAGGATCAAGCCTAACTTTACATATTAGAGATAATGCATTCCTC
CTTGGGGATAGTTCAGGTTGATTTCTCCCTAGGCCTGCCTTTGTCAACATA
TTCCTGAAGTCTCATCTGCACCCCATCTCTGCTTCTAATATTGGCCACTCT
GTGCATGAACCAGCCCCTCCTTCCTGCAATGGGAAACAGGTGTGAGATGGG
ACAGCTGTCACAATCCGTTTTGCTTTTGTCTTGCTGTTATTATTGGTAATG
GTAGTTTGTTTCCTTTTTAGCATTCACTAGCTTCCTTTTCCTGATCCTTTG
ATAGTGTTACCAGAAGGGGGTCCCAACCCAGACCCTAAGAGAAGTTCTTA
GATCTCGTGTGAGAAAGAATTTGGGGCAAGTCTACACAGTAAAGTGAAAGC
AAGAAAGTAAAGGAATAAAAGAACGGCTACTCTACAGGCAGAGCATCAGCT
```

FIG. 8-239

```
TCTGGACTAAGGATACTGATATGGTTTGGCTGTGTCCCCACCTAACTCTCA
TCTTAAATTCCCACATATTGTGGGAGGGACCTGGTGGGAGGTAATTGAATC
ATGGGGGCAGGTCTTTCCCTGAGTAATTTATACTGCTGTTCTCATGATAGT
CAATAAGTTTCATGAGACCTGATGGTTTTATAGAAAGGAATTTCCCTGCAC
AAGCTCTTTGCCTGCTGCCATCCATGTAAGACCTGACTTGCTCCTCCTTGC
CTTCTGCTGTGGTTGTGAGGTCTCCCCAGACACGTGGGACTGTAAGAGCAT
GAAACATTTTTTCCTGGTATAAATTACTCAGTCTCAGGTATGTCTGGATCA
GCAGTGTGAAAATGGACTAATACAGATACTTACAGTTATTTCTTGATTATG
TACTAAACAAGGAGTGGATTATTCATATGTTTTCTGGGAAAGATGTGGGCA
ATTCCCAGAACCAAGCGTTCCTCCCCTTTTTAGACTATATAGGGTAGCTTC
CTGACATCGCCATGGTATTTATAAACCACTATGGAGCTGGTGGGAATGCCT
TCTAACTTGCTAACACATTATAATTCGTGTATAATGAGCAATGAGAATGAC
TAGAGGCCACTCTTGTTGCCATCTTGATTTTGGTGGGTTTTGGTCAGCTTC
TTTACTGCAACCTGTTTTATCAGCAAGATCTTTATGACCTGTGTCTTGTGC
CAACTGCCTATTTCATCCTGTGACTTACAATGCCTAACTTCCTGGGAATGC
AGCCCAGTAGGTCTCAGCCTTATTTTACCTAGCCCCCATTCAAAATGGAGT
CATTCTGGTTTGAACACCTCTGACAATAGGACAGATCTGGAATGAGCCATG
CCTGGGTACAGAGTCACATCCACAACAATGAAAGTTGTAGATATCTGCAAG
GACTCATCGTGGGACCAAGGATTCAGGGGCTCATTCTTTCTCCTCTCTCTG
TGTGCTGGTTGCCTCAGGAGTAGAATGTCCCATGCTATGCATGGGGTCTGC
AACCATCATGCCAGGGCATGATGAATCGTAGGTGGCAAAACAACAGAAGGC
TCTGTGAGCACCCAGGAGGGTGCAGTGCTGAAGAGTCTTCTGCTTGGTATA
GGAAGAAAGGAACGTGTTTCCCAATCTTGCCTTTATTTTGAGTAGTTGGAC
CAGAGGGATTGCAGCTGGGCCAAACTCCATGTTCCATTGGCTATCAGGGTC
AGCAGGCAGGCCAGGGGCCCAGACAGGCCAGTGGCTCCCAGAATTCAAGTT
TAATTTCTCCTCCCACCTGTGTCCTGAGCTCCCCTTACTGGTTCCCTTGGA
CCACTGCATCTACTTAAGCCAGCATTTATTATGTTGTTATCATAAATGCCT
CTTACACCTGAGACTTATAAATGTGACAAGCTCTTATTGTGAGATAGTAAT
CCATCTTTTTTCCCCATGAAATAATAATTCTAACGGGTGGTGATAGTACTT
TTCCTTTCATTTTGAAGTGGAGAAGCTGGAGCTAAGTCATTAAGGACTTGA
CCCTGGACCCCACAGCCTTTTCTCCACAAAGCACAAAGCAGAGTGATGGTC
CCAGGGATCCCACACAGCTCTAAGCTGGGGGCACTCACTGCTGGGCCACTA
GTGACTCCCATTTTCTATCCTGGCTGACCCTCGCTATTGAAGAAGATCTGA
GTCCTGCAGAAGGACAGCAAGGAGAAAAACAAGACACAGAACGGGACAGAG
AAGAATAGAAAGCTGACTCAGATGAATTTTGTGATGCCAATGAGTCCTACT
GCTGTTACCACCCCTTTTTCCACCACACCCTTCAGAGCAGTTATAGAACCA
CAAGCAACCCATAAATAGCAAAAGAAGTAACATCAGCTAGGAAGGCTTAAG
GACTCCCAAGGGAGTTGGTGGCAAAAGTAGAAAGATCTCAAATCAGAGTCT
GTGAACTGAACCTCTGCAGGCTTCCTGTTTTTAGATACTCTGTGTTGGGGT
CACATGATAGTTTACAGGGTTATTAATTGGTTCCTTCTTTTTATTGCTGTA
AAAGAAGGATATTTTCTTCCTACGTTTCCCCCTCCTTTACCGGAGAGGCGG
AGTGCAAATGATATGAACAACGTCACTAGTTTTCTCCTAAATCTTATGAGC
CCCGCCTCCCACAGTAGTTTCACTTCTCAGTTTAATCCGGTCTGAGTTAAC
TTCCTGACCCAGGAAGTGGCAGCAACAGAGGGGACTAGCAGCGAATATGTA
AGTGTCTGAGCAGTGAAGGTTACGGAAAAGGTCCAGGCTAAGGTTTTCTCA
GTGGATATGTGAGTGTGTACTGATGGCAAGTGGGGTGGGGAATATATTTCG
```

FIG. 8-240

```
TGACAGCAGGGCCCCTCCAACTCTGAAAATGGTCAGGACTTTCTTTGTTTT
ACAGCTCTCACCTCTTTCCTGCTCTTTCTTTCACCAGACTTTACACCAAAT
CTCAGAAGATTCAGAACTTAGATGAGTGGGGCCCAGGACAGGAACCCTGGA
GCCTTGGAAGGAGGGGAGCCCCATCTCCCCAGAAGAGCAGTGACCCCAGCA
GAGAGGGGCCTGGTGTATCACTGGAGGAAATAGCCTGCCAAGGAATACACG
TCTTCAGAAGAAATTCTGTGTGGCTTCAAGAGACTGATCAAATTGTGAGAG
GAAAACAGCCTACCCGGTAATTGTAGTTAAATTACTGTTTTTTATTCTAGG
CACTCTTCAAACTTCCTCCTGACTCTGCCCCTGTCCTAGAGGAGCTCCCAG
GAGTAGGGGTGTGGGGGCGGGCGGGGGGGAGGGATCGGGGGTACAGGGAGA
GCCCAGCTAGGTTCTCAGAAGAGGCAGGCTTTTTCGCTCCTGGTCACTCCT
CTGTTGCCTATCCCTGGCCTCCCCCATCTTCTTTCTGCCTTCCCTACCTCC
TTGGGTCTGCAAACTCTTTATGTTGCAATCACTCTGAACATGTCTCTTGAG
ATAGGTCCTGTCCTGGAGAAGAGATAGTAAAAGTAAACTCCCCAGTTCTGC
AGGAGCTCTGATCCCATAGAAATAACTGCTCCTCAGGAGCAAACCCTCTGC
TCTGCAGCCTTCTTTCCAATTCTTATTCCCTCAGTTTAGGGAGAGGGCACA
AAAAGGATAAACCGGTTCTTCTGGTTGTTCTGGTTGCCTTGATTGCTTCCA
TTATCCTCCTGGTTGGGTCTCTAGCAAGACGTTATTAGCCAGGGAAGTCCC
ACTTAGGCACCCCTCTCTGCAGAAGAGGTATTCACTATTCTCCTTTCTCTT
TCTTTTGCCTATTATACCTCTGCTCCTGAAAGCAAAAACAACAACAACAAA
AACACAAACAAAAAACAACCGACCTTATTAACCAGTGTTGGTTGTTGTTCT
TTGTGGGGATGGGGGGGGTCGAGGTGGAGTCAAATTTTATTGTCATGATG
GTGTAGGAGCCAAGGGAACACTTCCCCTTTGCCTTCTGAAGTTCACTGAAA
AATCGACTCACAAAAGGCAGGCTAATTGGAGAAAAGGCATACAAATTTATT
AACAAGTACATGGGCTAGAATCACAGAGTGATTACCCCCTCTGCCAATGGG
GGTAGATACTTATATAGCCTTATTTATAAATACTTATGTATAAATACATAA
ATATAAATATGTATGCATATGTATGTATGTATAAATATGTATGTATACTGT
ATAAATATGTATGTATAACGTTTATACATGTATACATATTTATTTCAGAGG
GGAAGGGTGATATCAGGAGAATATAGGTAATTCTTTGAGGGGCAGTAAATG
ATTACTAGGGAGAATAAATGAATATTTGGGAGGATGAATGAATGGAGGAAC
AGAGTTTAACTTGTAAATGTTCTCTTTGGAAAATGAATGAGCCTGAGAGAC
AGACATTATTTTGTGAAAGTGTCTGATTAGGTCTGGTAACATTCTTAGTCC
TCTTTTCTTCAGTACAAAATGAGATAATAGGGGTTGGAAGGAAAAACAATT
GTTCTTCTTGTCTAGTGTGACTGGTCTTTATGTAGATAGGGGAAAAGTCTC
TTCCAGCATCTGCTGATCTCTAAGGGCCTTTAATTCAAAATACTCATTATA
CCAGGGAGTCATATATTGGGGTGAAGCTCCCCATACTCCTTCAATGGAATC
TGTCACAGATCACCCAATTGCATAAGTGTTACTACTAATTACAAAGAGTAA
TTCTGGTACCAATTATTCTTTTTTTTTTTTAAGACAGATTCTCGCTCTT
TCACCCAGGCTGGAGTGCAGTGGTGTAATCTGGGCTCACTGCAACCTCCCC
CTCCGGAGCTCAAGTCATTCTCCTTCCTCAGCCTCCTGAGCAGCTGGGATT
ACAGGTGTGCACCACCACATCTAGCTAACTTTTTGTATTTTTAGTAGAGAT
GAGGTTTTGCCATGTTGGTCAGGCTGGTCTCAAACTCCTGACCTCAGGTGA
TCTGCCCGCCTCGGCTTCCCAAAGTGCTAGGATTACAGGCGTGAGCCACCG
TGCTGGCCTGGTAACAATTATTCTTGAAGTTAACTAGAATAGGAAAGAGTT
TCACACTCCCTGAGTTCTCTCTTTTACAGCTTTTGTGAGGAAGCCTGCATT
GCTTCTCCCAGCACTTGGTCCAAGGTAACTTTCTGTGATAACAGAATGTTG
TATATTGAGGCTGTTATGTAGCCACTAGTCACATGCAACTATTAAGCAATC
```

FIG. 8-241

```
AAAATGTGGCAACTGGAACAGAAAAACTGAATTTTTTCATTTTAATTTTTA
TTAAGTTAAATTTAAATTCCTACTCATGATAGTGGCTACTGTATTAGCTAT
ACAGCTAGATGTTTGTGTATCCTCTAAATTCCAATGCATTTCTTCTTTCTG
GAGAGAAGACTTTAGCTGGACATGGTGGCACATACCTGTAGTCCCAGCCAC
TCTGCCAGGGTGAGGCAGGAGGATTGCTTAAACCCAGGAGGTCGAGGCTGC
AGTGAGCTGTGGTCATGCCACTGCCCTCCACTACAGCCTGGGCAAGAGAGC
GAGAACTTGTCTTATAAGAAAAGAAAAAGAGGCTGGGCACGGTGGCTCATG
CCTGTAATCCTGGCACTTTGGGAGGCTGAGGCGGGTGGATCACAAGGTCAA
GAGATCGAGCCAACCAACATGGTGAAACCCCATCTCTACTAAAAATACAAA
AATTAGCTGGGCGTAGTGGTGCACACCTGTAGACCCAGCTACTACTCGGGA
GGCTGAGGCAGGAGAATCGCTTGAACCCGGGAGGCGGAGGTGCAGTGAGCC
GAGATAGCGTCACTGCACTCCAGCCTGGGTGACAGAGTGAGACTCCGTCTC
ATTAAAAAAAAAAAAAAAAGTTAGAAGACTGAGAAAAGAAAAATAATGAAA
TAATTTAGAGCAGTCTGAGCTATGTGAGGTATGCAAAATTTATCAGGACAA
GTGAGGCAGGAGTATAGGTCTTCCAGTTAAGACCCCATGTTTTAAAAGCAT
TTTGTTCCTGACTGGCTGCCTCATCTATTACCTACATATTCCCGAGATTTG
TTAATACAAAGAAACAATGTTATAGCCAGTCCAAAAGCTTATGCTATTTTA
ATGTTAAATCCTTGGCAAACAACTTTAAAACTGCTTTAAACTGCTTTTTTC
CTCTAACACACTTGTACTGCTTGCTAATGAGGCACTTGAACTCTGCACTTG
GTTGCAGTTTCTCAAAGTGCCCCAAACAACCTTCACTCAATTTCTTCCTTT
TAGTTCCTCTTTTCTTCAATACAAAATGAGATAATAGGGGTTGGAAGGAAA
ACTTTCAAGACCTATGGAAGTCAGTTGCAGCCAGCTCATCACATAGAGGTG
CAGGTGAGGTGTATTTTCATCACGGTGGAAAATTCTGGCTGCTTCATCTCC
ATCTCTAGAGCCAATATTGGAGCTTTTCAATAAAAGCTATGGCCTCAACCA
CCAGCACCAAGAAGATGATGGAGGAAGCCACCTGCTCCATCTGCCTGAGCC
TGATGACGAACCCAGTAAGCATCAACTGTGGACACAGCTACTGCCACTTGT
GTATAACAGACTTCTTTAAAAACCCAAGCCAAAAGCAACTGAGGCAGGAGA
CATTCTGCTGTCCCCAGTGTCGGGCTCCATTTCATATGGATAGCCTCCGAC
CCAACAAGCAGCTGGGAAGCCTCATTGAAGCCCTCAAAGAGACGGATCAAG
AAATGTCATGTGAGGAACACGGAGAGCAGTTCCACCTGTTCTGCGAAGACG
AGGGGCAGCTCATCTGCTGGCGCTGTGAGCGGGCACCACAGCACAAAGGGC
ACACCACAGCTCTTGTTGAAGACGTATGCCAGGGCTACAAGGTGAGTGTGT
GGGCCCGGGAGCTTTGGTAAGTACCAAGTCTTATCCTGCTCCCCAGGAGCT
GAGATGATTTAACTTGAAACCTAACATTATGACTTGGAAATACAGCTTTCA
TCATGTCATTCTTCTGAAAAATAGTTTATGATGATTTCTTGCTCAATTATC
TAGACTGTCCATCCTGACCTTCAATGGGATGGTTGGACTCTTATCTCTATC
CATTTGTGTTATGATGAATTTCTTTTTGCTTTAGAACAGGTTGTTCTCAAA
CCAAACACCCGCATTTTTTCTTGTTTCACACCATGAATATCATTTGAAAAA
CCACAATATGTAAAGCCATGCAGTAGGGCCTGAAAACAGGGAAGAAAGACC
CATCACCTTTTAGGTATCTACAGTCTAGTAAAGAAAACAAACCATCAAAAA
TGTCTGCCTGGAGGTCCCTGGTTTTGGTGGTGGGGAGGGACATTTAGGGTA
GAGAGTGGTTCATCTTAGAAGTAACTCCTGAAGGACACGTAAAAATTGAAC
ACCTATTGGGGGATTTTCATTTGGGGAATGAAGGGTCAGTGACATTGAAAA
TATCACTCTGGTACCTCTACTTTTTTTTTTTTTTTTTTTTTTTTCCTGA
GGTAGGGTCTTGCTCTGTATCCCAGGTTGGAGTACAATGGTGCAATCTCGG
CTCACTGCAGCCTCAACCTTCTGGGGCTCAAGCAATCCTCCCACCTCAGCC
```

FIG. 8-242

```
TCCCAAGTAGCTAGGACTACAGGGATGCCCCACCATACCTGGATAATTTTT
TTATTTTTGTAGAGACATGGTCTGCCTTTCTTGCTTATACTGGCCTCAAA
CCCCTGGTCTCCCTCCCATCTCAGCCTCCCAAAATGCTGGGATTAGAGGCA
TGAACCACTGTGCCCAGCTACTGTGGCATGTCTATGATAAAAGGAATATCA
AGGAGTAAAATTCAAACTATCCGTATAAGAAAGGGAGGAGAGGGCAGATTT
TAAGCACGATTCAGGAAGAAGAGTCAAAGATTTGGAAATGCTTGGTTGTGG
AAGGTGAAGCAGAGGGAGAGGTTTTGTGTACCATCCAGATTTCTTGCCAGA
AAGCATATTAAGGAAGGTGGGACTTTGCTGTTGGCAGCATGGAGGAATGGG
CATAGTCCTGATGTCCTTTTTCCTTCTCTGTCCTGCCTAAATTTGAGGAAA
ATGTTGTCTCCAGTGTCAGGCTCCTTATTCTGTCCTCCATGAGGCAGAGGT
GGTCTTGTATGAAGGCTCTAAGTCCTTCTAAGGACATGTCAATCATGACCA
CCACTCAGCTCATGGCAGCTCTTCCTTAAACTCCATGGAGCAGCTAATAAC
TGCGATGATCATATTCCCATTTGAATTACTTTTCCACCAAGTAGTAAGAAA
AGGAACCAGCTTATGTTGAAATTGAGTTTTGTCACTTACTAGATGGGCAAT
TTTGGGCACGTTACTTAATGTCTTCACACCTTGGTTTCTCCATCTGTAAAT
GGGGATAATAGCAGTGTCCTCCCTCCCTAAAACACATACACAGGAGGTGGT
TATAAGCTTTGAGGACATTAAAATATAGAATGCATAGAATAGCACTTGGCA
TATAGTAAGGACAATGTCATCTTTTGCTAAAACAGTTACATAGAACCTTTT
CCTGAGAACACTCGAGAATGAATGAGTATACTTGTTGGGTTTACAGAGGAC
AGGAGACAATTCTTTCAGCATTGACTACAATTAGCAATTTGGGTCAGCTTC
AAATCACTTTCAATAGAAATATGAGAAACTGTTTTGAAGAATAAGCTAAAA
GCTTGACATGAATACTAAATCATTTTAAATTGGATTCATGATACCATTGTT
CAAAAGATACCAGAATTCCCCTCTTCCATGAACTGTTTCTAATAACCAGCT
GGCATCCTGATTTTTCCTGACTCATAAGACACAAAATTTCATGTTGTTGCC
AAACACTGGTATTGGTTTTGCTTGGTTCAGCATGTTGTTTTACAAAATCTT
TTAGATGATGATTACCTTGTTCTATATCCAACTTTTTCCTGGCAGGACTCT
AGTGGTGGACATAGCTCAGGCTCTGGGTCAGCAGATGAGATTGCAATTGTT
GCTCCACCACCTGGCAGTCATAGCCCTTTGGGCAAGTTATTTTACCCCTTT
CTTAGTCTCATTTTCTACAGCACAGAAATGAAGTTTAAAATCCTACCAACT
ATTCAGGGTTGCCAAGGGGATCAGTATGTTCCTGCACATATAGCCTTTAGC
ATGCTCTCTAGCAAAAAACAATGAGGACTCTATAAATATTCACTATTATTC
AAATATATCTTAGAAGATTGGGATTCCCCCTAGGTCCCTAATGAAGAGTCA
AATTGAATAGGCTTCACTTATCAAATTTTTCCTTCAGGAAAAGCTCCAGAA
AGCTGTGACAAAACTGAAGCAACTTGAAGACAGATGTACGGAGCAGAAGCT
GTCCACAGCAATGCGAATAACTAAATGGAAAGTAAGAATCTGACTTCATTG
ATCTCAAGCTATTTTCCATTCTAGAGCTTAGGCATAGGGGATGATTGAGGA
AAAGCACAATGAGGATTTATTCTCACTAAACCAGATTGAAAAAATGAAACC
CAAGGAAGAAACCATTATTTGTACTTATGCCCCTGGTTCCAGGTTTACATC
CATGAGTATTTAGCACCAATCTTTCCATCTTTAAACTGTAGTTGGCTGGGA
TTCCTGATACTTCAGTCAGAAGAAGCAGAATTAGTATGACTATTTACCTAG
AAAAAGCATCGAGTGGGTCTCAAACTTTAAATACGTCAAAATAAACCTGGT
TTGCAGGCCTCAACTCATTACCCTGGCACTTTTACCACAGTGGAGCATCTG
GCTCTCAACTTTACAGGTACAGAAACCAAGCTTTGTGAACACTTAGAAAAC
AGGATCACTCCAGATTGAAATTCATACTACTCTAGCTCATGAAGCTGATGA
AAGAAATATACTTTATTTATTTATTTTTAAATTATTACTATTTTTG
AGATGGAGTCTTGCTGGAGTGTAGTGGTGCGATCTCAGCTCACTGCAATGT
```

FIG. 8-243

```
CCACCTCCCGGGTTCAAGCAATTCCCCTGCCTCAGCCTCTTGAGTAGCTGG
GATTACAGGCATGTGCTACCATGCCTGGCTAATTTTTTGTATTTTAGTAGA
GACGGGGTTTCACCATGTTGGCCAGGATGGTCTTGATCTCCTGACCTCGTG
ATTCACCCACCTCAGCCTCCCAAAGTGCTGGGATTACAGGCGTGAGCCACT
GCACCCGGCCTATACTTGATTTATAAGTACATCACAAGTAATGCAACAACC
TACACACTTGCAACTACAAACTTTCAGATTATTTCCGTGGCTGACTAACCT
CCACATTATCAGAGCCACATTCTTTTATGGAAATATTTAGGTTTGTGCAAA
AGTAATTGCGGTCTTTGCCATTAAAGTAAAGGCAAAAACCACAATTACTTT
TGCACCAATCTTTATATTTATATAATTCACTAGCTTGCAGTAAAATCCCAC
AAGCTGATTACCAATTTTCTCTCTTTCAGGAGTCCTCTCTAACCTCTACCC
TGATCTTTGTTTGTGGATGTTGCTCTTGAGCTCCTGAGTACACTCTTACTT
CCCCCATTTCTAGGATCTTGGGCAATGGGGAAGACCTTGATTGTAACTAAC
ATATATGAAAACCCGTCTATACAAGAGTTAAAGCTGCACCTGTCTCCTACA
CAAAAATTCCACCTCATCCTAAGTCAAAGACCCTTCTTCTATATCATAGTC
ATCAAAACACTGTATGAATTTATTTTTATTTTTAATTTTTATTTTTTTAA
GATAAGTAGAGAGTTTATTTGGGCCAAGTTTGAAGACTGCAATCCAAGAAC
ATAGATTCAAATTGCCCTGAATACACACTCCCACTGCATTAATTTAGACAG
CACTAATGGAAATTGCAACTTTACATCTCCTCAGATGAGAGTTTCACTTGA
TTTCTGTCAGTCTTACACATAGGAATGCTTAAGATGACCCTAGGGTAGTAG
AACAGTATTTCTCAGTTAACCATAATAAATGCCTGTCACACTCAAAGCTCC
CCCTGCCAAGAATTATGGACCCTCTTACCAGCCTGGTTGTCTTAAAATCCA
GTCTGGGTGATGTTCATTATAAGCTTTTACTTCAAGAAAATCGCTCCAACT
CAGAAATCTAACTTCTTAAATCATAAGTAAAAACCTCTTTTTATCCTTGTA
ACTGATAAAGTGTTTGAACTTGGCCCTAGTTTCACAATTAAATTATCTAGC
ACTCCTAACCCAGCTTTCTCCTGTGTCTTGGCTGAAGAACAAGAAAATTAA
TTGGGTGACTATAAGGAATCTGAGGCAACCTCTTCCACATCTGAGTGCCTG
CCTCCCACACATGACTCTGCAGCAGGAAACTGGGGACATTCTTCCAGCTTC
AGTGACTCATGAGAAAATAATGTCCCAGTGGCTGATTGTGTGTGTGTGTGT
GTTTGTGTGAAAATATATATAACACTTAAGCATTTAACCACTTTTAAGTAT
ATAGTTCAGTAGAATTAAGTGCTTTTACATTGTTACATTGTTGTGCAACCA
TCACCATTCCCATCTCCAAACTGCAACTCAGTTTCATCTTTCATCTTCTAA
ACTGAAACTCACTACCCATTAAACAATAACTGTCCATTTTCTGGTCTTGCC
AACACCTTGTAACCACTATTTTACTTTCTGTCTCTATGAACTTAACTACTC
CAGATGCCTTGTATAAGCAAAGTCTTACAATATTTGCCCTTTTGTTTCTGG
CTTATTTTGCTTGAATGTCTTCAAGGCTTGTCATGTAGTAGCGTGTGTCAG
ACTTTCATTCTTGTTTATCCATTCATCCATAGATGGACATTTGGTTTACTT
CCACCTTTTGACCATACTTTCTTGACTCCAGGAGAAGGTACAGATTCAGAG
ACAAAAAATCCGGTCTGACTTTAAGAATCTCCAGTGTTTCCTACATGAGGA
AGAGAAGTCTTATCTCTGGAGGCTGGAGAAAGAAGAACAACAGACTCTGAG
TAGACTGAGGGACTATGAGGCTGGTCTGGGGCTGAAGAGCAATGAACTCAA
GAGCCACATCCTGGAACTGGAGGAAAAATGTCAGGGCTCAGCCCAGAAATT
GCTGCAGGTGAGGCTGTGTACTTGGAGTAGGGAAAAAAGGTATGTTATAGT
GCTATTAAAGGAGAATGGTAAGGAAGCATGGGAAGATAAAGTAATGTTTCT
TTTAGATGTACATCAGTGCCATCAGGCTGGCCTTCACTAATTTATAGGGTA
CCTTTATGTCAATTAGAAAAATAAACTTCTGAGGGAACACAGCTTGGCCAA
ATGAAACCACGGGATAACATTTACCACTGTTTGCCTCCTTGGCCCATGTGC
```

FIG. 8-244

AGAGAACCCTGGTTGTTGACTCTCTCCTGAAATACTCCACTAGGTGACTGA
TGGGTGATGAAGTGGGGCAGCCAAAATGAGTGATAACCTTTTCCCTGATTT
GCTTGTAGAACCCTTGCTCCAGAGCTGTTATGGTACAATCTACAGCTTTAT
CTGTAGGAAGATAAACATCTGGAGCCATTAATTCTGGTTCTAACTAACAGG
ATTGGTGACTATACTGTAAGGCTGAGTGTATAGCATGATTGCTTTACCACT
GTGTGATACCTGCTACCACCATCTTAGTGGCAGTGGCCCAGTCTCAGGGCT
GTGCACAGATTCACCACTAAGGACCTTTATGATAAGTGTTCTCTAATCTGG
GCTCACTGTGAAGGAAATCCGATCACCAAAAGCTAGTCCTTACAGAGGGAG
CATGGACAAAGCTCCTGGCCCTCAGACTTCAGCAAGGATGAGAATAGATGC
AAATGTTGATAAACATCCTGCCATGCTGAATCTCCCAGAAGCTGGTAGGAA
TTATTCCATCTGGGTATCCATCAATACCTAAGACTGGTGGGAATTACTTTG
TTTGAGTATCCATCAATATCTAAGACTAAGACTAGGGTAACTCTCTTTACT
TCTTCGGGTAAAGCAAAGAAGAATAGCCCTGCATGACAAGCCCCATGAAAT
ACCGATGTTCCCATGCTCACCTTTTCTTTTTGTTTCTTTATAGAATGTGAA
TGACACTTTGAGCAGGTAAGTCCTGTTTGAATGCAGGAGGGGAGGGGTGTG
CGTATATAGAAATGAATGGAATGCACCTCTGAAGAAATCTCTCGCCTCTGC
TTATTCTAGGAGTTGGGCTGTGAAGCTGGAAACATCAGAGGCTGTCTCCTT
GGAACTTCATACTATGTGCAATGTTTCCAAGCTTTACTTCGATGTGAAGAA
AATGTTAAGGAGTCATCAAGGTATGTTCACTAAAGAATTCCTGAATACTGT
GGATAGAAGGGGCCTTATGCAGTAACCAAGTTTACCACCTGTCCCTTGGCA
GGCTCACAGCCAGAGAGGTTGTTTAGTTAATTTCAGTAGAGCTTTCATACT
TTCTCTAGTTAGTATGATTCACTGCTCAGTGAATGTGATGAGCATTGCATT
CTGGTTATCTGTGCAAACCTTTCAAATTCTTATTCTTTCACTTATTAGCCA
TGTTACTCCAAGTGACTTGGTTTCCCCCTCTGAAAAATGAAAATATTAACA
GCTCCTACTTCATTGAGTTATCATCAAAATTAAATGCATCAACATGTACAA
AGTGCTTAGCCCTGTGACTGACACATGATCATAATAGCACATCATGGTATT
AGATCTGATCATAGTGTTTATTATCAATAGCTCAGCCAACTCTTAGAGCAA
TGCAAGAAAAGTAGGTGAGTATGATAACCTATCATTCACATATTTTAGGAA
CTTGACTTAGATAACACAGATGACAAATGTTACAACCAATTTACAGATTCC
AAAATGTTAGAACCATTTACTGAGTTTCCTGCTCCCTTGATTTTTTAAATC
AGTGCTGACTATACTTTCACAAATTTGTATCCGTAAGTACAAAATCAAAAA
AACCCCTGAAAATGGAAAGTTTTATCATGATTCATTTGGCTACAAAAATCT
GGCCTAACCTGAAATGATTTGGTGGTTATATTAGTTATCTATTAGTACAAA
CAAATTACCATAATTTAGAACCTTAATACAACACTGATATGTTATCTCAAT
TTTTGTGGTTCAGGAATCTGGGCACAGCTTAGTTGGGCCTGCTGCTTAGGG
TCTGATAAGGCTGCAGTTAAGGTGTTGGTCAGGCTGTGTTCTTATCTGGAG
GCTAGGCTAAGGAAGAATCCACTTCCAAGCTCACTGAGGTAGCAGGCAGAA
TTTCTTTCCTGATGGTTGCAGGACTTTGGCCCTGGTTATTTCTGGCTGTTG
GCTGGAGGTTGCCCACAGCTTCTACAGGCCACCCCTCAGCTCTTTGCACAT
GGGCTTCTAACATGGCCAGTTATTTCTTCAGAGAGAGCTCAGGAGACAGAC
TCTTTAGAGAAAATCTGCCAGCAAGATGGAGTCTTACATAATGAAACGTAA
TCATAGAAATTATATCCCATCATCTTTGCCATATCCTATTGGTCAGAAGCA
ATTCATAAGCCCTGCTCACACTCAAAGACAAGGAATTTTACGAGGGTGTGA
ACACCAAGAGGCAGGAATCATAGAAGGCCACCCTTGAGTCTGTCTTCCACA
GTGGCCAACCCTGAACGGCACTGAGATGAGACTATTTAAAAGTCTTTATTT
ATCCCACTTAATTTGAATAAATGTTTTGCTGCAGATATATTGATGAATTTG

FIG. 8-245
```
ATTACAGGGCTCTGCCTTAGGCCATGATGGGGTTGAACTTTAGAGTATATG
CATTTTTTTGCCTTTATAACTTCTAAACTAATTTGAATGGCAAAGCCCATT
TTGTTCCAGGGATTTCAGAAAAGGAATTATAGACCTGTGTTCCCCTCAAAT
ACACAACAACAAACAACAACAAAACCCAAAAGCACTCTGTATTTCATCCTA
TACAGATGACAGGAAGGAAGAACAAGACTTTGTGTAAGTTTTGCTGGGATT
TCACTGAGTCAATTTGCCTACTCTCATCTTTTACAGAAGGAATCATAATAT
GGTTCAAGTGAAACTATTTCTTTCTTTCTTTCTTTCTTTTTTTTTTTTTT
GAGACAGAGTCTCGCTCTGTCGCCCAGGCTGGAGTGCAGTGGTGCGATCTC
GGCTCACTGCAAGCTCCGCCTTCCGGGTCAAGTGAAACTATTTCTTAAATG
GGCTTATCTTTTAACTAAATATTTCTCCCCTCTTAAACACTGTTTATTAAA
ATTTTTCTTTTTTCAAATTTTTTTTGAGATGGAGTCTCGCTGTTACCCAG
GCTGGCTTGCAGTGCCGCAATCTCAGCTCACTGCAGCCTCTGCCTCCTGGG
TTCCAGCGCCTCAGCCTCCGGGTAGCGTGGGATTACAGGTACGCACCACT
ATGCCTGGCTGATTTTTGTATTTTTAGTAGAGATGGGGTTTCACAATGTTG
GCCAGGCTGGTCTCAAACCCCTGACCTCAGGTGATCTGCCTGTCTCTGCCT
CCCAAAGTGCTAGGATTACAAGTGTTAGTCACTGTGCCCAGCTTTATTACA
AAAGTGATAGGAATAAATTTTATTTTTATTTTTAAATGTATGTTTATTTTA
TTTTACATTGCCTTCAAGCAGATGCAACAAATACATTTTAATCAGTCAAAC
AATATAAAGGATATAAGGAGAAAGTTCAAGGTTTTTCCCACCCGTCTCCAA
TCTGACTTCTCTAGGTAGGGTGATCTATATCTTTCCCTAAGTTTGTACAAA
CGTAACATATATACACTGTCTCTTCTATGTTACTCGTTACTTTTTATGTCT
AATATTCCATAAGAATATAATAAATATATGTAACCATATCCCTACTGATGG
AGCTTCAGGCTGTTTTTAGAACTTAGTTATTACAATGTTGCTACAATAACT
TTCTAGTCCATGCATCCTTATATCCTGGTGCTTTCATTTCTTTTGGGAACA
TACCCCAAACTGGGATTGCCGAGGTTGTTGTTAATCTTAATATATGGTACC
ATATTACTTGACTCAAAGTTGTAACATACACTCCTACCAGCACCAGGAATA
ATGACTCACATATACTGAGCACTCTTTAGTCTGTGACAGATTAGAAAAGCT
TTACTTTTCTTGGTTCTTGTTTTATATCACAGTCCTCTCTATATGGGGCAT
TTTTGCTTTATAGAGGAGGAAATATGACACAGAGAGGTTAGGTGAGTGTTG
TAGGATCTCATAACTAGAAGGTAGTCATAGAAAGAGTCTAGAGTCTAGAAA
CCACTCTCTCACCATTTTGCAATGTGGCAGAAAATGCAAAGTTGTTATTTA
CTTATCTCTTTTAGACAGGGTCTCACTCTGTCACCCAGGCTGGAGTGCAAT
GGCCCCATCATGGCTCCCTGCAGCCTTAAATTCCTGGGCTTAAGCAATCCT
CCCACGTCAGCTTCCCCAGTAGCTGGGACCACAGGCAAGCACTGCCACGTC
TGGCTAATTTTTTAAAAATTTTTTGTAGAAACACTATCTCTTTATTTTGTT
CAGGCTGGTCTTGAACTCCTGGGCTCAAGCAGTCCTCTCGCCTCGGCCTTC
TAAAGTGTTGGGATTACAGGCATGAACCACCATCTCCGGCCTGAAGTTTAT
TTAATCCATTGCCTTGTGGACTGGGCATTGAAGTTGTGTGTAGTTGGGTTT
TTTTGTTGTTGTTGCTGTTGCAGACAATACTACTGTGAACATTCTTATCCA
TGCTTCCTTGTGTCCCGTAAATGTTCCCTCCAGGGAGATACCTTGGAGTGA
CATGCTGGTGTGAGGGATGCATATCATAATTTTACCAGATACTACAGATCT
TGAAATTGTTCCAATTCTACCCCACAAGCAATATAAGAGCTCTCACTCCTC
CAAAACTCCCTGAGTCTTTACTTATATAATTTATGATTTTGACAGTCTTAC
AGATTTAAAATGGTACCTAATTGTGTACTTAATTTGTGCTTTTCTGATTTC
ACTAGTGAGATTGAGATTCTTTTTGTATGTCCATTAGCCCTTCAGGCCTCT
GTGATTTACCCATGATTTACTGTGGTTTAATAATTTTTATTGGGTTCTTTT
```

FIG. 8-246
```
CCTTATTGATTTATGGGAACTTATTATAGCTGATATCTTCTGGCATGTGGA
TGGCATTTTGCATTTTCATCCTGTTTTTTGATAAATAGGGTTTCAAAATTA
AGTAGACACATTTTCCTTCAAGGTCTGTGTCTTTTATGTCCAAAGAGCTTA
GTCATCAGTGGGCAGTGAATTTTATCACCTAATTAATTTTATTAGCCCCGT
GTGCTATGCCTGTAGTTCCAGCTACTGGGGAGACTAGGGCAGGAGGATCTC
CTGAGCCCAGGAGTTCGAGGCTGCAGTAAGCTATGATCACGCCACTGTACC
CAGCCTGGGCAACAGAGCTAGACCCTGTCTATTAAAGGAGGAGGCCGGGTA
CAGTGGCTTACGCCTGTAATCCCAGCACATTGGGAGGCCGAGGCAGGAGGA
TCACTTGAGGGCAGGAGTTTGAGACCAGCCTGGCCAGCATTGTGAAACCCT
ATCTCTACTAAAAATACAAAAATTAGCCAGGTGTGGTGGTGTGCACTTGCA
GTCCTAGCTACTCTGGAGGCTTAGGCAGAATTGCTTGAACCCAGAAGGCAG
AGGTTGCAGTGAGCTGAGATTGTGCCACTGCACTCCAGCTTGAGCGACAGA
GTAAGACTCCATCTCAAAAAAAAAAAGAAGAGAGATGAAGGAGGAGGAGGA
AGAGAAGAGGTGGGGGAGGGGAAGGAAGAGAAAGAAGAAGAAAGGGACAA
AAAAATTTAGCTGTCATCTTTGCTCTGATAGCATTATAATGATGATGAAGA
CAATTGCTAGGTTGGTGAGAGAAGGCTATATACACACCAGAACTCTCCACG
TATATGGCAAGTTCATATATTTTGTTAAGTATGTCTCATTGGAGACCTTCT
TTTCCCGTAACTATGACCAGTGCTCTGCCAGCTCAGTCAACAACAACATTG
CATGTTGGCTCCATACCTGGACTCTTGGTCCAATTGGTAATGAAACCATCC
CACCAGTGTCTTCATAATATATATATACACACACACATATATATAGTAT
TCTCTCCCAGTGTCTTCATAATATATATATATACACATACACACATATATT
ATATTCTCTCTATACATATTTATTTATATATCTATATCTATATCCTTCCAC
CTCAGGTCTCCCTCTGTCTCCCAGGCTGAGTGGTGCAGTAGTGCGATTATG
GCTCAACCAATGAGAGGATCAATGGCAATCCTCTCATTTCAGCCTCCCCAG
TAGCTGGGACTACAGGCATGGGCCACCACATCTGGCTGATGTTTAAATTTT
TTTGAGACAGCATCTCTATATGCTATAGATATATATAGTATCCTCTCTCTA
ATATGGATAGAGGATACTATGTCTATATCTGTATCTATCTATCTATGGAGA
AGGAATACTATATATCTAATAAGATGTAATCTATATTATATATAAAAGTGA
AGCATTGATTGGTACATATAATATATATATTGATTACTGTGTGTATATATT
TGTTTTTTCGAGACAGGCTCTCACTCTGTTGCCCAAGCCGAGTGGTACAGT
GGTGCGATCATGGCTCCACCACCTGAGCTAAAGTGATCTTCTCACCTCAGC
CTCCCCAGTTGCTGGGACTACAGGAACAGGCCACCATACCTGGCTAATTTT
TTAATTTTTTTTTGAGACAGGGTCTCCCTTTGCCACCCAGGCTGGAGTGCA
CTGGCGCAATCTCGACTCACTGCAATCTCCACCTCCCAGGCTCAAGTGATC
CTCTCACCTCAGCTTCCCGAGTAGCTGGGACTATTGGTGTGCACCACAATG
CCTGGATAATTTTTCATATTTTTTGTAGAGATGGAATTTGGCCATATTGAC
CAGGCTGGTCTCAAACTCTTGGACTCAAGTGATTGACCCGCCTCAGCCTCC
CAACGTGCTGGGATTACAGGCATGAGTCACTGTGCCTGGCCTGATTATTGT
ACACATTTTGATGTAATGTATTATATATGTCATATATGACAATCTAGATG
AATATATTAAAGATTGGGTTTTCATTTATATATTGTAAAATACATACACTA
TACATATATAATATGTAGAACATATGCTATACATATTATATATGTATATGT
TAACATATATAATACATACACATATAATATGTATAGTTGCAAATATAAAAT
TTGGTTTGTTATTTATATTATTTTGTGCAGGAGTTCTATATCTATGTCTAT
AAGCGGGAGCCATAATTTTCTATTCTTTGTAGGATTTGGTATGAGATTGGC
ATTACTCATGCCTTGACTTCTAAATTTCCTATAAAACTGACAAGTTCCATT
TTTGCTTGATAAAGATGCACGTTTTATTATCTGTCGGTAAAATTTAAAGTA
```

FIG. 8-247

```
GTGATTTCATTTCTTTAATGTTAGGTCTGCCCATGCTTTATTTGTTTTTTG
AGTGAGTTTTACTCAGAAATATTTTTTCTAGGAAGTAATAATTTTATCAGT
ACTTTCAATTTTATTAGTAGCATAAGATTTATTATAAAGTTCTGTAATATT
TAAAAAGTTTCTGTATTCATTCCATTTGTGCCTTCTGTCTTACTTTGATAA
ATCTCATTGGAGGTATGTCTATTTTATTAAATTTCTTTTAAAAGAAGCTAC
CTTTTTTTTTGTTTGTTTTTCCTCTTTATTGCATTCTTGTTTTCTTTAACT
TCACTGTTATATTGTTTAATATCTATTTTTTCTTTTTAAAAAATTATATTT
GGCTTTCTATGTTCTTTTTAAAATTTAAATTAGATGCTTGGCTCATTAATG
TTCAGCTTTTTAATTTTTCTAAGATAAGCATTTAAAGCCTACAAATTTTCC
TTAAAATTCTGCTTTAGCTTCATTGTATATTTTTATAAATAACTTTTTATT
ATTGTTCCATTCTATACATCTTCTAATGACTTATTAGTAGTTTACATTTCC
TAATATTTAGAATCTTTTTAGTCATCTTTTTATTATTGGTTTATAATCTTA
TATTGAGGCTAGAGAAAATGATCTGTGTAATACAGATTTATTGAAACTTGT
TCAGACTGTTTTCTGCCTAGTATTTACTCAGTTAGTGCATGTTCCATCTAT
ACCTGAGAAAACTGCATATTCTCTGCTTACTATTATTAAACAATTGCTGAG
CTTTATGTATTGACTATGAGATTGCGCTTCTTAGATTGTTCAGACCTTCCG
TATCTTCCCTTATTTCTTTCTTTTGGTCTGCCTGATCTATCAATTATGGAA
AGAAGAATGTTAAAACATCCCATGATGATTGTAGATTTGTCCATTTCTCCT
ATAATTCTACAATTTTTGCTTTGTATATTAACACAATTCTAAACATGAATT
CACTAATAATGTAGTACATTTATGTTTAAAATTGTGTTATCTTTTTAGGT
GACTCCTTTCATTCTTTCTTTTTTTTTTTTTTGAGACAGAATCTCTCTCT
GTCACCCAGGCTGTAGTGTAGTGGCGAAATCTCAGCTCACTGCAACCTCTG
CCTCCCCGGTTCAAGTGATTCTTGTGCTTCAGCCTCCCAAGTAGCTGGGAT
TACAGGCATGTGCCACAATGCCCAGCTAATTGTTGTATTTTTGGTAGAGCC
AGGGTTTTGCCATGTTGGGCAGGCTGGTCTTGAACTCCTGGCTTCAAGTGA
TCCGCCTGCCTTGGCCTCCCAAAGTGCTGGGATTACAGGCATGAGCCACCA
CACCTGGCCCTTCTTCCATTCTTAATAATGCTCTGACTTAATATCTTTTGA
TATAATACTATAACAGTATATGACTATATTATCTATCTTTTAGCTTCCAAT
CTTTCTATATGTTTTTGTTGATGTGTCACACCAATAGATAGGTGGAATTTT
AAAAATCCAATTGATATTTTTTCTCTTAAGTGGTATTACCACCCCGTAAAC
ATTTTAATTTCTCAACATGGGTTTTCCTGGGTCATTCAGGTAATATGAATT
GAAACCCCAAACTTCTGTGAGTCAGGCTGATAAAAGCTAACTGAATAGAGT
TTGAAAAAGGAGGGTATTTACAAAGGTGAGGAGTTGGGAAATCCACAAGGA
ACAGGAAGCACCCAGAACTAGGAACAGTTAGAGAGCCATCACCTCCTCTGG
GCCTCAAGTGGCAGGTGTAGGGAGCTGTAACTATACTAGAGTGTGCCCAGA
GGCAGAGGAATGCAGACCCTCCAAATCATAGCGTGGGACTGGGGTACTGAA
TACTCCCAAGGCTGCTTCTTTGTGCCCTATGGTCTCCTCTGGTGCTTCCCA
TTGGCTGAACCAAGCCAGAGGGCGGAAAGCCTGGTTAATCTGTCCATGTCA
GCCTTCCTGGGCACAGAGCAAGACAGGGAAAAGTGAGGGATTATTTGGAAG
AACAAACAGAGAGCATCCAGCACAGGAAGTGTTTCTGAATACTTGAATTCC
TTAATTGTCACAGACCAACTGATCAACATTTAACTCAGTAGCACAGTGGTT
TCCTTAACTCTCTTGTTAGAACATCCTATTACCATTTTTTATTTTTAAAAC
TGCATACTGTTCCAGTATCTCACTTTAGTTATCAGATCTTTTTCTGTCTTG
TTTGATTCTAGTCTGATATTTTTCCATGTTATATTGGTCCTCCAGTGTATT
ATTATCTCATACTAATGCTTATGGAACATTATCTGAGGGGAAAGAGAAGAG
CTTACAATTAAAAGTCATGGGACTAGGCATGTGTCATGAGACCTGGGTCTT
```

FIG. 8-248
```
CCAATAACAAGCTAAGACATTAGCTGAGTCATTTTCCCTCTCTGATTCTCA
ATGTTGGTGGTTATTCAGTAGAGAAGGGAAAAGGTATCTTTCTGCTCAACT
GTCTCATGATTCCTGGAAGTCCTGCATGGGAGAAGAACTTTGGACAGGATG
GTAACCATATTAACAGGTTAGTTCTGTACCTTGGCATCCTTGAATAATTAA
GACGAAGATGATGTTGATGATATCATTATTACTACATGTTGTTAGAAGAGC
TGAAGCAGGACTGGCTTGTCTGTCATAATGTAAAAGAGTCTTGGAAGATGT
CCGGGGTCCAGGGTCCAAAACCCCTCGTGGCCTTTGGAACACCAAGCTCTG
TGCCAAATGGTGGAAGGCTGCCCTGCCGCACCACAAATCTAAGCCTAGGGC
ATAAAACCCCTTGTGGCTTGGATGGAACCCAGGGCTCAGGGCATAAAACCC
CTCATAGCCTCTGGAAAGTGCACAGACTTGTTGGTTCCTTGCTTTTCACTC
ATAAACGTGTCCTCTACTATCTCAAGCAGCAGAGTATATTCTACATGTGTC
AAAGAAAATGCTAAACTGTCACAGCTACGCTTAATGCACCACTACCTTTCT
ACCCCCATGTCCTCATGCCCTCACCTGTTTACCCTCACGTCCTCACCACCT
GCTTCTTTGTTTGATCACCAATAAATAGTGTGGGCTCCCAGAGCTTAGGGC
CTTTGCAGCCTCCAATCTAGTGCTGGCACCCTGGACCCACTTTATGCACTC
TTAACTTGTCTTTTCTCATTCCTTTGACCCCGCCGGACTTTGTAGCCCCCA
CGGCCTGGTGTTGGGCCTGATCACCCCAACAACTACCACTTATTAGTGGTT
ACCATGTACCAGGAAATTTTACCAAGCATTAAGCAAACATAAGCTTATTCA
ATCCTACCCACCATTCTCTGCAACAAATACGGTAATTTCCACTTTATAGTT
AACAAACTGAGGCTCAGAAAGTTAAATGATTTGCCTAAGCTCACCCAGTTT
ATAAGAAACAATAGTTGGGTTTGAACACAGGCTGGTTTTATTGAAAATAAC
TTGTGGCTGGGCATGGTGGCTCACACCTGTGTAATCCAGCACTTTGGGAGG
CCGAGGTGGGTGGAACACTTCAGGTCAGGAGTTTGAGACCAGCCTGGCCAA
CATGGCGAAACCCCATCTCTACAGAAAATTTAAAAAAATTAGCCACTTGTG
GTGGTGCGCACCTGTAGTCGCAGTTACTCCGGAGGCTGAGGCAGGAGAATT
GCCTGAATCCAGGAGGTGGAGGTTGCAGTGAGTTGAGATAGTGCCAGTGCA
CTCCAGCCTGGGTGACAGCAACACTCCATCTCAAAATAAAATAAAATAAAA
TAACCTGTGTTCTTCACAGCAACAAAATTATTTTTGTTTGTTTTGTTTTGT
TTTGCAGTTAGTGTGACTCTGGATCCAGATACAGCTCATCACGAACTAATT
CTCTCTGAGGATCGGAGACAAGTGACTCGTGGATACACCCAGGAGAATCAG
GACACATCTTCCAGGAGATTTACTGCCTTCCCCTGTGTCTTGGGTTGTGAA
GGCTTCACCTCAGGAAGACGTTACTTTGAAGTGGATGTTGGCGAAGGAACC
GGATGGGATTTAGGAGTTTGTATGGAAAATGTGCAGAGGGGCACTGGCATG
AAGCAAGAGCCTCAGTCTGGATTCTGGACCCTCAGGCTGTGCAAAAAGAAA
GGCTATGTAGCACTTACTTCTCCCCCAACTTCCCTTCATCTGCATGAGCAG
CCCCTGCTTGTGGGAATTTTTCTGGACTATGAGGCCGGAGTTGTATCCTTT
TATAACGGGAATACTGGCTGCCACATCTTTACTTTCCCGAAGGCTTCCTTC
TCTGATACTCTCCGGCCCTATTTCCAGGTTTATCAATATTCTCCTTTGTTT
CTGCCTCCCCCAGGTGACTAAGGAAAAGAGCAGAAGCTCCTTGGTTTAACC
AGCACAGAGAAAATAATATAAATCCCATAAGGGCAGACGTTTGGTCTGTTT
TCTTCGCTGTCATTTCCTTAGTAGTTAGACTAGTGCTGAGATTTTAGTGGA
TATATAATTGATTTATGTTGAATATATGGACTTAGCAACTAAAAATACCAC
AGATGGTTAACCTGGACTGGGGCAAAGCAAGATAATAGTGATGATCGTATG
TTGCTGTCTCCATCCGTCTTTAATGGGTCAGGGCTTTGATTTCCAAGGGTC
TTCAGGTGATGAGTAGGGGTACCCACAAGTCAGAAGGTCTGCGTTCTCCTA
GTTTGTTTGCTGCCATTTGAACTCATGTAGGGAATGAAAGAAAGCTGCAAT
```

FIG. 8-249

```
TATCCGCCAACTGCATTTAAAACAAAACAAAACAGAAAAATCAAAATAACA
TTGACTCTTCCAACCACTGACATGTTGTTTAATAATCTAAGCGGCAGTCCT
GGAGGCTACCAGACTTACTGAGTTCTACCTGAGAAACAGCCAAGCAAAGTG
TGAGAGAAGGGTTAAGACTGGCTTACAATGAGATGCTTCAAATGAAAAGGG
AATTATGAGTAAAATTGAACTTTGATGGGGGATTCAGTTCTGGAAAAGAAT
TTGGTATTTTCCAGTCTGCTAGGACCAATTACCTTGAAATATTTTAAAATC
TCAGTAAATAGTTATTGCTGAAATGGCTGTTGGCAGTTCTTATTATGATTC
AGAGAAGAGCAAATAGACCTTAACTTCATTTTGAAAAAGACCAAATTACCA
TACCCGAGTGAGTAATGACAGGACTACAACTAAAACATAAACAACATTAAT
GATGACCATAAAAAGTCACAAAATTGCTAAATGTTATAATTTAGAGTTGAC
ATAAAAATTGATGGCCAGGCATGGTGGCTCACGCCTGTAATCCCAGAACTA
TGTGAGGCTGAGGCAGGTGGATCACTTGAGGTCAGGAGTTCAACACCAGCC
TGGCCAACATGGTGAAACCCTGTCTCTACTAAAAATACAAAAATTAGCCGG
GCATGGTGGTAGGGGCCTGTAACCCAGCTACTCGTGAGGCCAAGGCAGGAG
AATTGCTTGAGCCTGCAGCAGCTGCAGTAAGCCAAGATCATGCTGTGCCTC
AAGGAAAAAAAAAATTAATGTTTACTGATATTTGTTGAAGTCCTACAACAT
CACCTCTGAGAATAGGAGAAATGAAGCAACAGTTGTGTCTAGATGTCAGAG
GCATGGCTGGGCCTCCATCTCTGCCTAAGGGAGATATAAAAGAGTTCAAAC
TATTGCCCATGTTCCCCAGGGTCAGAAGTTCTAATTATGATGATAGAGGCT
GGGTTGTAAGTAGTAAGTGAAGGGTAGCAGAATATGCCATCTTTGGCATAA
GAAGTATTTTGAGTTGAAGACAATTGAGAAAAAAAATAGATTAAAAACAAA
CAAACACCTCTGCCCTCTCCCTATTTGCCTAAAAGCAGGATATGAAATTGT
GAAGGTGTCTTCTTACTCGGGGAAGAACAAAAGTTAGTCACCAGAGACTTT
AGACTCTTATCAGCCTGGACATAGCACCAGAGAAGTCTTTTTTTTTAAAAA
AAAAAAAAAAAAAGGGAAAGAAAAAGTTGCCTTCCCACAATTTACTGCAC
TAGAAACTCAAAGTCCTTTTCGTCTTCCTTGTCACTTAAAAAATGTATTCT
TTTCTTAAAATGCTATATAAGCCCAAGTTCTAAATCCTCTTTTGAGTATTC
ATCTCAGTACTCCCCTGTGTTTGTACAATGCACATGCTTTGTTTCTGTCTT
GTCAATCTGTCTTTTGTTAGTCTACTTGATAGGGCCACAGATGGAGAACCT
AAGATGAATAGAAAAAAAGATTTTTCTCCCCAACAGAAGGATTATCGCCA
GTTGCACTTGTTCTATATACCCGTAGTCTCGGTATGCTGACCCAGACTTGG
GTAATAGGACCCAGTGGGTAACCGAGGAACCCCACCTTTGTGCAGGATCAG
TGAAGATGTAATCTGGATATTCATAAGCTCTTCTCTACCTCTTGGCATCCC
ACAGTCCTGTGTTAATGTAAGTGTGGTCTTCCCCAGAAAGGGGAGGCCTCC
CTAACATTGTTAAAGCCTAGCATATGCTGCTTAGAGGAAATTCTATATCCC
TAAGCACTTAGATTGCTGAATAAGAAAGAATGATAATAAAATAAACAATTA
AATAAAAGTTTTAAAAAATGAATAAAATAAACCTGTGGAAACTATAAGGAA
GGCCAGAAGAAATATAAAATTGGAGATTAATTGGGGTGCAGGAAAGTTATG
GAAAGAATATAAGTCCTGCTAGATAAATCATTAGCTATTTTAATAAAGAAT
ACAGAAGAAATAGGAACAAAAGAATATATACTGGAATAATTTTGAGAGTA
ATTTGAAGAATTAGATGCAAATAAATTTGAAAACCTTTAAAAAGAAACCAA
TGGCCTAACTGACCCAAGAAGGAAAGAAAATCTAAACAGACTGATAAATAC
AAAATGAAATTCAGACACTTACAGAGCAGCCAGGCATGGTGGCTCACACCT
GTAATCCTGTCACTTTGGGAGGCTGAGATGGGAGGATCACTTGAGGCTAGG
AGTTTGAGACTAGCCTGGGCAAGCTCCCATCTCTAAAAGAAAAGAAATTAG
CTGGGCATGGTGGCATGTGCCTTAGTTTCAGTACTCAGGAGGCTGAGACGA
```

FIG. 8-250

```
GGATTGCTTGAGCCTAGGAGGGCAAGGCTGCAGTGAGCCATGGTCATGCCA
CTGAATTCCAGCCTAAGTGACAGAGCAAGACCTTGTCTCAAAAAAAAAAAA
AAAAAAAGTTACAGAGCTCCAACTAAATAATGTGGGGAACAAAAGAAAAAA
GAAGATGATTTTATGGCTGATTTTTTTTTAAGGAAAAGCAATTCATGTAC
CCTTGAAGATTAGATTAAGTTCTATAAAATAGCCCAAAATGACAGTGGCTG
AAACAAGTTTATTTATCTCCCATTTAAAGCAAGTCTAGATGTGGAAGTCTG
GGAAGCCCAGAAAATCCAGGTCTTGTTTGTGTATGGAAACTCCAGAAAATC
ACAGATTCCTTCCAGCCACCCCTCAATTACCCCTGGGATCCAAGAGAGCCA
CTAAAGTTCCAGCCATCATACTCACAACCCAAGTTGTAGGATGGAAAAAAG
GACACAAAAGTAGGGTGAAGAGCATGTGTGCAACAGCTCTCTTTTACTCTA
GTGTCCTAAAACCTATCATAAAACCTTTGGCTTGCCTTGCATTAGCCAGAA
TTTAGTACATGGCCACACTTAAGAAGTCAGAAAGATTAGCTTTTTTTCCAG
GGTAGTTGGCTGAAAATCAGGAGTTCTCATATTAAAAAACAGAGAAGGGAC
ATCGAATAGATGACCAACAATCTCCTTCACACTCATACTATTTAAACTGTC
CTAGTCAATGACCAAAAAAGAAAAGCCTACAAACTCATTGATATAAAAGCT
TAACAAAGGTACTCCCCGCCCCCCGCCCGCCACACACCATCCCCAAAAGGA
AATTTCTAATCCAATTAACAGTCTTAGGTTGGGCTGCTGAAACAAAATACC
ACAGCCTGAGTGACTTAAACAACGACAATTTATCTCTCACTGTTCTGAGGT
CTGAGTTGATTCTTTGTGAAGGCCCTTTCCTAGCTTGCAGATGGCTACCTT
CCTGCTATGTCTTCACATGGCAAAGAGAGAGCTAGCTTTCTGGTCTTTTCT
TATAAGGGACCAGTCCCATCATGCCCATCATGAAGACTCGATCTGCTAGGA
TCTCAACTAAACCTAACTATCACCCAAAGAGCCCACCTCCAAAGACCATCA
CATTGAATGTGAGAGTTTCTACATATGCATTGTGGGAAACACAAACATTTA
CTTCAACTGTAACTATTGAAGCAAAAATGTCCCCCCACCATAGACATCCAG
CACCACAGTAGTACATTTATTACAATTGAACTTACATTGACACGTCATTAT
CAACGAAAGTCTGTAATTTACATTAGGGTTTATTCTTGGTGTTGTGCTTTC
TATGGGTTTTGACAAATGTATAATGTCATGTATTCACCATTATAGTATCAC
AGAAGTTTCACTGCCCTAAAAATCCTGTGTTCTGCCTTTTCAACACTTCCT
GTCACCCAATTTCTATCAACTAATCTTTTGACTGTGTCCATAGTTACTGTC
TTTTCTAGAGTGTCATACAGTTGTGAAGCAGGAAGCAGGAGTGAACTCCGG
AGGCAGGGACTTTACTCCGGACCAGATTGAAGACTAGCCGAAACAGGGACG
AGGTTAAAGCACCTCTCCATAAGACACGCCCACCAGCGCCATGTCAGTTTT
TCGTTGCCATGGCAACAACAGGACATTATCGACTTCTTTCCTCTGTACCTA
CTCCGAAGTTACCACTCTTTTTCTAGAAATTTCTGCATAATCCCCCTTAAC
ATGCACTTAACTAAAAGCAGGTATATTACTGCAGAACTGCCCCTGAGCTGC
TACTCTGGGCACATTACTTATGGGTTAGCCCTGCTCAGCAAGGAGCAGTAC
CTGTTCTGCTGTTGTACACTGCTGCTTCAGTAAAAGTTGCTAACACCACCA
CTTCACCCTTGAATTCTTCCCGGGCTAAGCCCTAATTTTGGCTTGCTTGC
CCTGCATCAGTTGGAGTCATATAGTATGCAGTCTTTTCAGGTTGGCTTTTT
AGTAACATACATTTAAGTTTCCTTCATGTGTTTTCATGGCTTGATCGTTTC
TTTTCTTTTTCTTTTTCTTTTTCTTTTCTTTCTTTTTTTTTTTTTTTTTG
AGACAGAGGAGTCTTGCTCTGTTGCCCAGGCTGAAGTGCAGTGGCACTGGC
TCACTGCAACCTCCATCTCCCAGGTTCAAACGATTCTCATATCTCAGCCTC
CCGAGTAGCTGGGATTACAGGCTCACGCCACTATGCCCGGCTAATTGGGGT
TTTCCCATGTTGACCAGGCTGGTCTCAAACTCCTGGCCTCAAGCAATCCAC
CCACTTCGGCCTCCCAAAGTGAATGCATTTCTTTTTAACTCTAAATAACAT
```

FIG. 8-251
```
TCCATTATTCAGAAGTACCACAGTTATCCACTTACCTACTGAAAGACATCT
TGTTTCCAAGTTTTGGATAAATTATGAATAAAGCTGCTATAAACATCTATG
TGCAGGTTTTTGTGTGGAGATAAGTTTTCAATTCCTTTGGATAAATACTAA
GGAGTGTGATTGGTGAATCTTATGGTAAAAGTATGGTTACTTTTGTAAGAA
ACCACCAAACTGTCTTCCAAAGTGATTGCACATTTTGCATTCTCACCAGTA
ATGAACAAGTTACTATTGCTACATATCTTTGCAACCTTTGGTGCTGACAGT
GTTCTAAATTTTGGTCATTCTACTAGGTATGCAGTGGTATCTACTTGTTTT
AATTTGCAGTTCCCTAATGACATGATGTCAAGCATCTTTTCATATGCATAC
TTGCATCTGTGTATCTTCTTTGGTGAACAGATGTTCAGGTCATTGGCCTGC
TTTAAATCAGGTTATTTTCTTACTGTTGAGTTTTAAGTATTCTTTGTATAT
TCTAAAAATATTGTTCTTCATCAGATCTGTCTTTTGCAAACATTACCTGCC
AATGTGTGGCTTTTCTTCAACACTTCTTTGTAAATTTGCAAGTCCTTTGAG
AAAAGAAATGCACCCAAAGTATTAATTTGGCAATCTCATATCACGAGAGTA
CTCTAAAGCTAAATAAATTACAGTTTTTCAAATTTTGAATTAATTGATCTT
TGCTATTGTTAGCAAGGTCTTGTATTCTTTTTTTTTTTTTTTTTTTTTT
AATAGAGACGGGTCTTGCTACAGTGCCCAGGCTGGTCTCGAACTCCAGGCC
TAAAATGATCCTCCTGCCTTGGCCTTCCAAAGTACTGGGATTACAGGCATA
AGTCACCACGCTCAGCCATCTGGTATTCTTTAGCAACTGTTTGGTAACTTA
ATCTTTCACTTTTTGAAAACAAAAAATAGTTTTTTTCTCATAGTTTTCTAA
CAAAATCTTCATAACTGAAATAATTTCTCTTTATCACCTCTTCTTATAAAT
ATGGTTTTCTTTTTTTAAATAAAAATTTAAGACATTTTATAACTGGCCAAA
TTTACTAGCTTAGATACTATTAGATAGTCAATATTTTTGTTGGATATTTG
ATTTTTATTTCAGGCAACTAATATCTATTCATTTTTGCACTGTTGGAAGAA
AATTACTGATCAAATTCACTATGTATTTGCAGAAAATGGCTTTCAATATTG
TCTACTTTATCATCCTTTTTTTTTTTTTCTTTCTTCCTTTTTAGATACAGG
GTCTCACTATGTTGCCCAGGCTGGTCTCCAACTTCTGGGCTCAAACAATCC
TCCCTCCTTGGCCTTCCAAAGGGTTGGATATGTTTTATCTACAGTTTTGTT
GTTTTGTTCTGCTACAGGATATTTGCAATTGCCATTTATCATGAAATTCAT
GACATACCTTCTTCCACTCTCCTTTTTATCTTTATTGTTCTGGTTATAGGA
CTAGCTTTGCATCTCTACTCAATTCTGTATCAGTAGTATGCTTTCATTTTA
AATTTTAAGTTTGTCCATATGTATATTGACACAGGGTCTTGCTCTGTTGCC
CAGACTGGAGTGCAGTGGCAAGATCAGGGCTCACTGCAGCCTTGACTGCCT
AGGCTCAAGTCATCCTCCCACCTCAGCCTCCAGAATGGCTGGGACTACAGG
CACGCACCACCACACATGGCTCATTTTTTGTATTGAGACAGGGTTTCTCC
ATGTTGCCCAGGCTGGTCTTGAACTACTGGGCTCAAGCAATCCTCCCACCT
TAGCCTCCCAAAGTGTTGGGATTACAGGCTTGAGCCACCATGCCTCGCTTC
TACACTTATTTTTAATTCTAAAATAATTTATAATAATAAATATTAACAATT
AGATTTAATTACTGATAAATATTAAATGTTAAATAGGTTTTATTAAATAAT
TAAATAAAAATGAAAATAATCAGTATTTCAATTTAATTACTAATTATAATT
CACAGTTATCCTTGTAACTCCTAATGTCTATATAAAAGATTTTTATATTTT
TTAATTCTTAAAATTTTATTATTTATTTCACACCAGGCCATCACTGTGATA
CATTTTTTAAAACACATTAAATTATCACCAGAAAAGTGCTGTGATGGAAAA
TATAAATTGAAATACCTTTTCTGGTTAGGAGAGTAATTCTGTTTTTCTGAT
AGAGAATAGAAGAGTCCTTCAGGCCCCTCCAAACTGTCATATTCCGGGCAT
CGGGTGTCCCCATCCTCACTTCAGTCCACAGGCAGGGTCCTCAGTCTTCAG
CGCTCCTTCTCTTTCCCCTTTGTCTTGTGTCTCCTTGGGTCTCTTTTCTCC
```

FIG. 8-252

```
AAGACCTAAACTCCCTGAGGACAGGACTATTTTTTACATCTTGATGTCACT
CCTGAGCACTTGCTTTAATGTGTTGGACACTGGGTCCATTAAAGATTGTAT
GTGAAATTATAAAAGAAACGTTTTCACCTTTCTGTGGTACAGCTATAATTT
CTGGTTTCATTTACCAACTGGGTGAAAGTGGACCAGTGACACCATTTGTCT
GGGCCTTCCTTTCCTGAAATATAATATTGGGGCAATAGTCCCTGGTTCTTG
TAAGGTGTTCAGGCACAAAACGCTAGGCATGTAACATACTAAATGAGGTTT
TCCCAGTTAATTTATATGATTGCAAAGGACGTTCATATACACGGTCTGCTA
AAGAATTCTGGGGCCAATTAATCTCTGTGGCATGATGGGTAAGTCGATCCC
TTCTCTGGGCGTCTATTACTTCAGAAAAGGCATGAACTCAATTTTAGGGAC
CACACAAAAAAATTTATTCACTATCGTGTAGGACTTGGTCATTAGAGAGCT
TTTGTTTCTTTTTTTAAAATTTTTTTTAATTTTTATTTTCGTGTATGTGA
ATTTAATGGAGAGCTTTTAAATAACCAGATATTTAAATAACCAGATAATAC
AGATGCCCGGCCTGCTCCAGACAAATTAGAAAAGTATGTAGGTGAGGAGGG
ACCAGCCAGAAGGCGGTTTCAGCTCTGGAGTGACACTGAACGTACTTCTCT
TCCAGGGATGTCACGAGGTGTCAATTTCTCTGGCCTTACCCAGGTCCATGC
CCGCCCCCAGGGGCCCCAAGAATGACTTCAGCACCCCACCCCCACCTCCCT
CTCCAGATGTGGGTCCTGGGAGCGTTCAAGGCCCGTCAGTCACTCGAGCCA
CCCCTTGGCGGCTGGACCAAATCTTGGGCTGCCGCCTGGATCTGCAGCTGG
AAAGCGCCGTGACCACCGGTGTCCCCAGCTGGAGCAGGGCGGGCTGCACGA
CTCGCGAGGACGCCCTGAACCGCGGCTTCCTCTTTCATAGCCGCAGGACTC
GTGGTCAGAAGGCCGACTCCAAGCCTCAGCGGATCCACGAAATGGCCTCTT
TGAGGCTGTGGTGAAATTTAAGATACCCTTTCCCTGCCATTGTTACTGACG
TACTTCAGCAAACAGGTTAAAGTTCTGAAAGGACGTGGTCACGACTTTATA
TTTCTTACAGATTTGTGTCTCATGTTTTGTGCGTAAAAACCATTCGTCCTC
ATTTGAGATTCTCATATCCGTAATTCAGTTATACATAAAACTGAATTCAGT
TATATCATAAAATGTTCCCATGCGGGGAATGATTCGTTGGGGTCTCAGCCT
GAGGCCAGACGCAGCAGAGAGATCGGGAGTTGGGGGATGGCGGGCGGGGAG
CGGAGAGGAGGCCGCCCGCCGCCAGACTCAGGGTCCAGCAGAGCAGCAAAT
GCTCCCCGGCTCCCAGCCAGGGCGCAGCTGCTGGCCTGGGGCCGCCCCTCA
CGCCGCAGGAGCCCCGCCCCGCAGCGCCGGCCCTGCCCCTGGCCTGTGAGGG
CGCCAGCGCCCCTACAGCTTGCAGTCGCCCTGCGCGCCTCCCCGCGAGGC
TTGTTTTCTAGCGCCTCTGGTGGGCCGCCTCCCGCAGGCCTGGTGTGAGCC
TGGGGTCCGTTCTCACAGCTGGATCTGGGGTCTGAATGCCGCGCCCTCTGG
AGAGCCACAGATGGGTCTCCGCTGATGCTTCTCTCAATTTCCTCTAAGAGC
GAGAGCTCCGGGAAAGGAGCCGATCCTGGTGGAAGACTACAGGTCTGAGTC
CACTGGACGAAAAACGAGGTGCGTTAAGAGACCGCGGGAGTGGGGAAATGG
GGAAGTGAGGGTGGGGACTGGGCAATGGGGGCGGGACGAGAGGTCTGGGGC
TGGCGGGGACAGGGCTTAAGAGAGAGCCACCCCTCCTAGCCTTGAAGCTGT
ACCGAGCTTCCCTGTGATATTTTAAAATGCAAAGTACAAAAATTGAAGTA
ATGGAACTATGCGTACGCACCTCCTAGATTTTTAAAGGTTAACGTGTGACT
GTGTTTACTTCAGATGTTCCTGAAATAAATGAAAATGACCAGTTAAAATGA
AGGAAGAACGCGCTTGCGTCCCTCCTAGAGGTCAAACACTCTTCTGAGGAT
AGGTTGTATGCTCTCAGCGCCTCTTTTATTAAAAGTATTAAGAAGTACTT
TTCCAAATATTAGATGTAGTGTGTCATATCATTTAAACGATTTTTTTGTT
TAAAATAGTCTTTTAAAAATAATCTTTTTATTTTTAGATTTTTTTGAGACA
GAGTCTCGCTGTGTTGCTCAGGCTGGAGTGCAGTGGCGCCATCTCCCCTCA
```

FIG. 8-253
```
CTGCAACCTCTGCCTCCCAGGTTCAAGTGATTCTCCTGCCTCAGACTCCCA
AGTAGCTGGGATTAAAAGCGTGAGCCACCACACCCTACCAATTTTTGTATT
TTAGTAGAGATGGGGTTTCACTATGTTGTCCAGGCTGGTCTCGAAATCATG
ACCTCCACTAATCCACCTACCTCGGCCTCCCAGAGTGCTGAGATTACAGGC
ATAAGCCACCGTGCCTGGCCACTTTAATCATTTTGTTTTTGCATCTAGTC
TAAGAAATTCTGCACTAAAATTCTGCACTATTTTCTTCTAAAATTTTAAAA
CATTTTCTATCTGTGTCTTTGTTAGATGTAGAAACTTTTGTGTATGATATG
GGGTATAGCTATAATTTTATTTTTATTCCATATGAAAGCCAGTTTCTCAGC
CCAGGTAATTGAATAGACCATCCTTTCTCCACCAACTCTTAAGGCTACTTC
TGCTCTATTGTGTTCATAGTAGTTTCTAGGCTTTCTGTTTTGTTGTACTGA
TTTCTTCACCTATTTTTGCATCAAGGCTCTCCTCTTGGGGAAATAAAACAA
TCCTGCCAACCAAAGACCCCTCTGGATCCTCAAACACGCCATCAGCATGGA
AGGCCGCTATGGCATAGCGAGAGATAAATAGGATTCAGGCAGTGCTGTCCT
TACATCGCAATCATTCAGGTAGTTAGCAGGAGCATCAATCAGTACAGATAT
CCAGAGCTGATGGTCTTATTTGTATGAATGCCCAGTGCATATGGGATTGGA
GGGGAGGGCTTGGAGTGGGATGAGGGGCTAGTGGGATCCAGAAAGGGGCTA
GTCTTCAGGTCTTCCCTGGAGAGTATGTAATCTCTTATAACTAAGTGTTGA
TTTTTGTTTTGTTTGTACCTTCTTTAGATATTGAAGTATTCGCTAAGGCTT
AACATGTAATATATTTAAATCTTCATATGAATACGTTTATCTGATAGATTT
TGGTGAGACATAAACTATGAAACAAACAGAAAGATGGAACATGAGAAAGGG
TCAAGGGTGGCCTTGGTTAGGGATGGCAGCTTTTACAACTATGAGCTAAGA
TAAAATTTAGAAGGTTTTCTTTTTATTTTAATTAATCATACCACTATTTTT
CTCCTTTAATTTCCATATATAATGAGTTGATTGTAGTATTTTTATTGTGCT
TAACTATTTTAAGATAATAGTTGTCTCTCCTCATTTTAGCAAATAATATAT
TTAATGAAAAATCAACTTTATTGAGGAATAATTTATACACAGTAAAATACA
CCTGTATTAATTATACAATTTGATGCGTTTTATATACCCAAACAGTTACTA
CTGTAATCAAGTTACAGAACACTTCCGTCAACCTAGATAGTTTCCATTTGT
AGTATCACCTGTGCCGCCTCTTCCATCCTCTTGGCCCCAGGCAGCCACTGA
TGTACTTTCCATAATTACAGCTTAGTTTCCCATTCCTAAAATTTCATATG
AATGGAATTTATATCATATGTATTTTTATTTTCCTTCACATTTTTGAGAT
TCATCCATTTTGTGTATATATCAGTAGTTTATTCCCTTTTATTGCTTTATA
ATATTCCAAGATATAGATATATTGCAATTTTTTTTTTTTTGAGATGGAGT
TTCCATCTTGTTGCCCAGGCTGAAGTGCAATGGCATGGTCTTGGCTCACTG
CAACCTCCGCCTCTTCGGTTCAAGTGATTCTCTTGCCTCAGCCTTCCGAGT
AGCTGGGATTACAGGCGCCCGTGACCATGCCCAGCTAATTTTTTAGTAGAG
ATGGGGTTTCACCATGTTGGATGGGCTGGTCTCAAACTCCTGATCTCAGGT
GATCCGTACATCTTGGCCTCCCAAAGTTCTGGGATTACAGGCATGAACCAC
TGCGTCTGGCCGATATATTACAATTTATTTACCCATTCACCTGTTGATGGA
CACGTGGGTTGTTTCCAGTTTATAGCATTGTGAAACAAAGCCAGTATGAAC
ATTTGTACATGTCATAGTATGGACATGTGTTCATTTATCTGGGAGAAATGA
CCCAGAAATATTGCTGGGCTGTATAAGTGTTTAATTTTATGTTAGAAACAG
CCAAACTTTTTTCAAAGTAGTTGTAACATTGTCCTCTTACATTCACAATAT
ATGAGAGTAGTTTCCTCCACACCCTTGCTCACCCTGGGGATTGTCAGTCCT
TTTAACATTAGCTATTCTGTTGAATGTGAAGTATCTCATTGTGGTTTTGAC
TTGCATTTCCCTAGTAACTAATGATGTTTAAAATCTTTTCATGTGCATACT
GGCCATTTGTATGTTTTCTTTTGTGAAATGTCTGTTGAAAACTTTTACTCT
```

FIG. 8-254

```
TTGTTTTGGCTTGTCATCTTACTAAGTTATAAGGTTCCTTATATTTTCCAG
GTGCGAGTCCTTTGTCAGATACATGTATTATAAATATTTTCTCTCAGCCTG
TGATTTTTCTTTTTCTTTTCTATTTATTTATTTATTTATTTTTTAGG
AAGAGTCTCACTTTGTCACCCAGGCTGGAGTGCAGTGGCACCATCTTGGCT
CACTGCAACCTGTAGCTCCCGGGTTCCAGTGATTCTCATGCCTCAGCCTCC
TGCTTTTCATTTTATAATGTTTTTTGAAAAGCAAATTTTCACTTTTGATGA
AATTTATCATTTTGTTATTTATGTTTTATAAACTATAAACCTGTTGTTTTG
TTTTAAAGAAATCTTTGCTAATCCTAGGGTGTTGATGATTTTCTCCTATTT
TTTAAAGAAGTTTTATAATTTTAGCTTTTACATTTAAGTCTATGGTCTATT
TTGAGTTAATTTTTGCATAAAGTTTGAGGTAAGGCTCCTGCTCCTCTCCCC
CACACCGGATGTCTACTTGTTCAAGAAACATTTACTGAAAAGACGATTTTT
TTACTTATTAAATAGCCTTGACACCTTTGTCAAAACCAGTTGTCCATAGAT
GTGTGAATCTATTTCTGGGTTCTCTGTTTTGTTTCACTGATCTTTGTGTCT
AACCTTATACCAATTCATTCTGAAATACTTTCCAGATTACTATAGCATTTT
AATAAAATTTTGATTGAATAGTTTAAGCCCTCGGACTTTTTTCCTTTTAAG
TATATCAACTTGGAGAGGATTGATTCATATTTGTGTTTCATTTTTTCATTT
TTCAAAATTATGTTTCAAATTGACATAATAATTATATGTATATATGGGGTG
CATAGTGATGTTCTTTTTTTAAAAAATATTTATTTATGTATTTATTTATTT
TTGAAACAGAGCCTTGCTCTGTTACCCAGGCTGGAGTGCAGTGGCGCGATT
TCGGCTCACTGCAACCTCCGCCTCCTGGGTTCAAGCAATTCTCTTGCCTCA
GCCTCCTGAGTAGCTGGGATTACAGGCACATGCCACCACGCCTGGCTGATT
TTTGTATTTTTAGTAGGGATGGAGTTTCACTATGTTGGCCAGACTGGTCTC
TAACTCCTGACCTCAAGTGATCTGCTTACCTTGGCCTCCCAAAGTGCTGGG
ATTACAGGTGTGAGCCACTGCGCCCAGCCCATAGTGTTATTTTTATACATA
CTGTGTATAGTGATCAGATCAGGGTAATTAATTAGAATATCCATTATTTCA
AGCATTTCTCATTTCTTTGTGTTGGAAACATTCAATGTCCTCTTTTCTAGC
TCTTTGAAATTATTTATTACTGTTAACTATTGCCATTCTGTAGTACAAATA
GAACACTAGAACTGATTGCTCTTATCTAGCTGTAACTTATTTTAACGAATC
TCTCTTTATCATCTCTTTCCCCTACCATTCCCAGCCTCTAGTAATCTCTGT
TGTACTTTTTACTTCAATGAGATAAACTTATTTACTTAGTTAGCTAGCTTC
TGCATATAAGTGAGAACATGTGGTGTTTAACTTTCTGTTTCTGGCTTATTT
CACTTAATGTAGTATCCTGCAATTCCATCCATGTTGCTACAAATGACAGGA
TTTCATCCTGTCATGAACAAACAAAAATTTGCCAAAACAAAAATTACCTTA
GTTATCACATTTCTTTTATTGACATAATTCATAATCATCAGAATCATCTGA
CTTGTACATCATTGTATCAGTTGGTTTTATGCTCAAGATGTTGTATTGGTT
CATTATTGTCTTAATATCCCAACCAACCCAATCTAGACATAAATGCTGGCC
CCTGTGACATGGCAGGAAAGGGAGACAGGCCTGGGCCAAGCATAGTGATAG
CAATGCACCTGTGTTTGAAGCTGTTAAATATTTGCTACAGTCGTATTCCTA
GACTCAAAATTAGATTCTTGTTAAGTCCTACTTGTCAGTGTCTATGGCTGT
GTGAGTTCTGGTTAGTAGAAGGTGGGCAAAAGTGATGTGTATTCTTCCATA
ACTGGTCCATAACCACCTACCACTCACAATACTCCATGCCTTTTTTCTCT
TCAGGCTCCTTGGATTAGAGACCATCCTGAGGACATCCTTGGGAGCCATGT
GCTGAAGATGGCCAAGCCACAGGATGAAAGGAGCTGCATCTTTGAGTCACC
ACTGGAGAAAGGTCTCTCTAAATGGATTTGCAGAGACGTCTTCTCGAATAC
TCCCCTTCTAAGTTCCACTTGTAATCCACTTCTTCTATTCTCCCAGCAATC
AATGTGGTTTGGGGAAATTCCAGAATCTCATAATACCTTGGTCATGGGTAA
```

FIG. 8-255
```
ATAAGGAAAGGACCTTTACATACATGTGATGCAAAGCAGATCAAAACAAGC
AGAGCAGCCTAAGAGCAGCAAGACCCCAAAGGATAAGGGAAGTCCTGCAGA
AGAGCAGAGCGGTGCTGCAAAGGCAGGCAGGTAAGGTAAGCAGACAGGGCC
ATCAGGATGGATCCTTTGGGCATGCCAGCATCCACCAGGGACTGGTAGAGC
TATTTAGAGAAACTGATAAAAAGCTCTGCCAACTACAGTCACAAAAGATGG
AGCTCAGAATGATGAGTAGATGCCTAAAACATCTCCATTTTGTTGATGAAG
AAAGTAAAGTTTATAGAGCTTAGATTATTTGCTTTTGTACCTAGCACAGTA
CTTAGTTTATAGTAGATGCACAATAAGTATTTGTTTAATGAGTGAATGAGT
CACTAGCCTAAGACCTTTAATATAACATGCTTAAACCTGCTACCAGGGATT
GGGAACTCACCTATTTAGTAGTGAGTAGAGGGGTGTGGTACTGGTACTTAA
GACAGATGCATTGTGGTTGGGTATGGTGTGTTTTTGTTTTTGTTTTGAGAC
AGGTTCTCCCTCTGTTGCCCAGGCTGAGATGCAGTGGCATTATCATGGCTC
ACTGCAGCCTTAACCTCCCGGGGCTCAAGCGATCCTCCCACCTCAGCCTCT
GAGTAGCTGGGACCACAGGTACGCATCACCGTGCCTGGCTAATTTTGTTTT
TTGTTTGTTTGTTTTGTAGGGACGGGATTTTGCCATGTTGCCCAGGTTGGT
CTCGAACTCCTGGGCTCAAGCTACACCCGCCCGCCTCGGCCTCCCAAAGTT
GTAGGATTAAGGTGTGAGCCACTGTGTCCAGCAGATATAATGTTTTTAAAA
GTTTGAGAGTTAATATGCTCTCTGGTGTGCCCTAGGTCCCACTACTCCTAT
TGCCTTAAAACTCACGCAGTACACATTTGTCTTCCATGGGCTTCAGTTGTA
AGAGAACCCTTTCTACTCTTTGCTGTTCACAAGTCTCCTTTTAAACAGAGC
TTGTTCCCAATGCTGTTTTGTTTTGCCCTCTGCCATGTTCTTCCGGCCATC
ACCTCCTGTGGGGAAAAGAGAGAGAGATCACATTGTTACTGTGTCTGTGTA
GAAAGAAGTAGACATAGGAGACTCCATTTTGTTCTGTACTAAGAAAAATTC
TTCTGCCTTGAGATGCTGTTAATCTAACCCTAGCCCCAACCCTGTGCTCCC
TGAGACATATGCTGTGTCAACTCAGGGTTAAATGGATTAAGGGCTGTGCAA
GATGTGCTTTGTTAAAGAAATGCTTGAAGGCAGCATGCTCGTTAAGAGTCA
TCTCCACTCCCTAATCTCAAGTACTCAGGGACACAAAACACTGAGGAAGGC
CACAGGGACCTCTGCCTAGGAAAGCCAGGTATTGTCCAAGGTTTCTCCCCA
TGTGATAGTCTGAAATGTGGCCTCGTGGGAAGGGAAAGACCTGACCGTCCC
CCAGCCCGACACCCGTAAAGGGTCTGTGCTGAGGAGGATTAGTAAAAGAGG
AAGGAACGCCTCTTTGCAGTTGAGACAAGAGGAAGGCATCTGTCTCCTGCT
CGTCCCTGGGCAATGGAATGTCTCAGTGTAAAACCCGATTGTATATTCCAT
CTACTGAGATAGGGGAAAACTGCCTTAGGGCTGGAGGTGGGACATGCTGGC
AGCAATACTGCTCTTCAAGTCATTGAGATGTTTATGTGTATGCATATCTAA
AGCACAGCACTTAATTCTTTACCTTGTTTATGATGCAGAGACCTTTGTTCA
CGTGTTTACCTGCTGACCTTCTCTCCACTATTATCCTTTGACCCTGCCACA
TCCCCCTCTCCGAGAAACACCCAATAATGATCAATAAATACTAAGGGAACT
CAGAGGCCGGTGGGATCCTCCGTATGCTGAACACCGGTCCCCTGGACCCCT
TTTTTCTTTCTCTATACTTTGTCTCTGTGTCTCTTTCTTTTCCAAGTCTC
TCATTCCACCTAACGAGAAACAACCACAGGTGTGGAGGGGCAGCCCAACCC
TTCAACCTACCTATCTTATCTCTTCCATTATCTATCCACATATGTCCTCTG
TATTTTTTTGAGTAACATTTATAAGCATAAGTCCTTAGGTAGCTATGCCAC
TTACATAATGAACTAGAAAAGGTAACCAAACAGAATAGGGTTGTACTCAGA
TATACCTTCTACAAGTTTGTGTTACACATATTTACACATATTTAAAAATAT
ATACATATTATTATTGTGCTGTGTGGTTATTAGGCAAACTCAATAAGCAGT
TCTTATAAAGTATACTCAATGTAACTTTTATAAACTTACCATATTTTATAG
```

FIG. 8-256

```
TTATTCTGTTTTTATTAGCTGCTATAAACTACCTGGGTGTCTTGCATGAGT
CATTTTATTGTAATGTTTTTGTATCTGTTGAATGAGGAGTTAGAAGGCATC
ATCTTTAAGGAGCTTTACAGGTACATGTCCAGGGCTCAATAATTTTATTAT
TATTTCCTGGACAGATAAAACCTAAGCAGGTGAAGGGGAAAGAATAAAAGT
GCAGGGTGGAAGTTGCTTGAATGCTAACTGGGTCAACGATCTCCCAGAAAA
CCCCTGTAAAAGAAACCTAAGAACCTACATCACCAGGAGACCATTGGGACC
AGTTCCTCTGGAATCCCTGAGGCCAGATAATCAGCTGAAGCTTTACATTCT
GTCCCTTTCTGGTCATGACTTTCTCCACAGTCTGCTTGGTGCCTCCTCCTC
TGTGACTCTAAATTCTTAGGATCAACCCCTCTTGCATATGCACATCCGCAG
TGCCTGTGGGATACGGTGTGGTGTGGGGAGGAAACTCTCTTCTGCCTTAAT
ATTTTCCTGTGTGCCCCAGGCCTTGACGGAATCCTGTCTCTCCATAATGTT
GCTTTTCGAGGAGACTGATTGATTGAGATGGCGTCTCACTTTGTCGCCCAG
GCTGGAATGCAGTGGCGTGATCTCGGCTCACCAACCTCCACCTCCAAGGCT
CGAGTGATTCTCCCACTTAAGTCTCTTGAGTAGCTGGGACTACAGGTGCAT
GCCACCACGCCTGACAAATTTTTTATTTTTTGTAGAGATGAGGTTTCGCC
ATGTTGACCAGGCTGGTCTCAAACTCCTGGACTCAAGTGATCTGCCCACCT
CGGCCTCCCAAAGTACTGGGATTACAGGCATGAGCCAATGTGCCCGTCCTG
AGGAGTTTTCTTCTGGAATTCCTGCTGGGTTTTTGTAGTCAGTCCTCTCCC
CATTTCCCACATTGGCTCTTGCAGACCTTCCTTTTCCCCATTTCTATTTGC
TACCATGTCAGACATGACTTTTGCCATAGGATCTCTATTCTACTATAGAGG
AAACCAAAGCCATCAGTAGAAATTTCACTAACATGGAATCAGATTTATAGA
AGAAAGGGGGAGGAAAGTTTTGCCTTAACACCTGGAAGGGTTTCGTTTCTT
TTAGTAGCTGGGAGACAGAAACATAAGAAAGTAGCTTAGTAAGCTTTCTGC
TGTTCAACTGATGATGTGTGAGCTGTCAGTAGTTCAAACTAGTCATTATCT
TTATGAATTAATTATGTAATAACTTAAACAATGTCATAAACCTTCAAATCA
GTTTAAGTCTAAATGTGTCATATTTAATAACAAGAGCAAGAAACATACGTT
ATGATGAAGAGCTCTTATATTTTCTTTGGATAAAAGTCAGTAGGCGGGGCG
CGGTGGCTCATGCCTGTGATCCTAGCACTTTGGGAGGCTGAGGTGGGCAGA
TCATGAGGTCAGGAGATCGAGACCATCCCGGCTAACACGGTGAAACCCTGT
CTCTACTAAAAATACAAAAAATTAGCTGGGCGTGGTGGCGGGCGCCTGTGG
TCCCAGCTACTCGGGAGGTTGAGGCAGGAGAATGGCGTGAATCCGGGAGGC
GGAGGTTGCAGTGAGCCGAGATTGTGCCACTGCATTCCAGCCTGGGCGACA
GAGCAAGACTCCGTCTCAGAAAAAGAAAAAAAAAAAAGTCAGTAAAATTT
AAGAGAAAAATGCATTTGCTTTGGGACTTTTAATATTTAGTCTACAAATCT
AGCCACCATAGAAATCTGCTGATTAAATACGGGTTCTGTTAAAATGGAAAC
ATGCATTTTGGGGGAAAAAGAGGGAGTGTTTTAGTGATTTTGTTTTTTAC
ACTTGTTTATAATAAAATTTTAAGCAATCTTGAGGGGAACATTTTATTTCT
ACTTGTAACTGCATAAAGTTATGAGATAAAGTTACAAGCTATATCACATAC
AGTTTGTAGCTTTATAAATTATGAAATTCTAACAGAATAAATATGCTAATA
TGATGAAAATGTCATAAATTACATTAGAATATATTTTAATAAACCAATTCA
GAAGGAGCCAATACCCAATTTCAAAATCATATTAATTGTAAAATTAATTAG
GGCAGCCAAAATATTCTGGAATTCTTTCTAATAAAACAAATGAGTGTAAAT
ACAGTCGTACTGACAAATCTGAAGAATTATGCAGCATAAAAAGTGATTATC
CCAGCACTTTGGGAGGCCAAGGTGGGCAGATCATGAGGTCAGGAGTTGGAG
ACCAGCCTGACCAACATGGTGAAACCCCGTCTTTACTAAAAATACAAAAAT
TAGCCGGGCTTGGTGGTGCACACCTGTAATCCCAGCTGCTCAGGAGGCTAA
```

FIG. 8-257

```
GGCAGGAGAACTGCTTGAATCCAGGAGGTGGAAGTTGCAGTAAGCCAAGAT
CACGCCACTGCACTCCAGCCTGGGCGACAGAGTGTGACTCTGACTCAAAAA
AAAAATAAATAAATAAAAATAAAAGTTTTAAAAAAGTGATTATTATGAACA
CAGAGTAATCTAGTAAAAATGGTTAAGTGAAAACAGCAAAATACAAAATTG
AATATGTACTATAACAATATATGCAAAATATACTCAGATTTATAAAAATTA
GAATGTAGAAAAGTAAATATAGCTCTTCATAATTTTGTTCTGAAGTTTAAA
AATATATATATTTTTGAATGGATAACTTTCTTTTTCTAAATGCTTACAGTA
GAGCCCACGATGGTTGTTAAAAGCCCCCAGGTTCAGCCTTCTTTAATTGTG
TGGTCAGCCTGCCATCAACCCGAGGCCTCCCTCTGCTGGGCAAATTTGGGA
ACACATTGAGAAATCCTTACACGTAATTCCTTCTCTTCATGTTCCTGGTGA
GCATTTTCCCATTGGGTTTCCATACTCTGCCCTCTTGAAGTCCTGCACCC
TGACATTGCAGTGTCATTCCTCTTCTACTGAAGTCTACAACTATTAGCTTA
TTGTCTCTAGCAAGTCTCCCTTTAGCTACAAATATCATTCAGAGTTTTACC
TTTCAGAAACTTTCTCCATGAGCATTCTGGAGTAGACTCTAGGTGCACTAG
GTGCAGTTAGAAAAAGTTCTGATTTGTTGGTGGAGCTATAGGAGGAGAGAC
AATGGTGGGCTGGAGAAGGGTGTCTACATGCAGAGAAACTGACTGGAAACT
CAGAGAGATGATGGGGATTAAAATAATCCTATTGAATCTGCACAAAAGTGT
TTTATTATAATTGATCCTGAACTATGTAAAGGTAAGCTCCAGTGAGTAGTT
ACAGTCTGTCCCTAAGATGGACTCTTTCTTTTTGCTTTTATTTTTATTGTA
TTTATTTTATTGTATTTTTTTTTCTAAAGACAGGGTCTTGCTATGTTACC
CAGGGTGGTCTCAAGTGGTCCTCCTGGCATCAAATGATCCTCCCACCTCAG
CCTCCCAAAGCGCTAGGATTACAGGTGTGAGCTACCACACCCAAATGATTC
TTTCTTTTCAAATACAGAGTTCAGCAGCAATTTTAAAGAAGTACTGAACTC
TACTGCCTGGAAGATGGAATGGCCCTCACAATTCTTCCAGGCAAGCTCTGC
ACTCAGTGGTATGGACCACAAGGCAAGCCCATTAAGGGGTTAAATTACTGA
CAAACAATAATTTCTAAATATGAACATTTCAGGAGGAACTAAGATGGCTCC
TTCTTGGAGAATAAGTTGGCCGGCTTCTCTAGTTATCAGACTATCAGATGG
GGAGGAAAGAGCCCCTCTGTCCCGGTGAGACAGGACCCGCCAGCGCCCAAG
CTCTAAGGCTTTCTGATGAGCAAATGGGGTTTCCATCTTTCTAGCTTCAGG
ACTCGTAACTACTCAGATTATTTCCTTCAATCTGGATATTCAAGACAAGAA
CAGTTCATGGTGTTGCGAAGGCCCAGATTTAAATCACATATGCAAAGATAC
TGACATTCAGTGGAGGGTCACTTAGATTATAGCCAGATGACTTTCCCTAAA
TTGATAGCTCAAATGGTAGTTGTGGATATTTTTGCTCTTAGTTACTTGCAT
AGTCACTTGCCAGAGGTAATAAAGTTTTAGTGTGGTTGTGGAAAATAATGG
CCATATATTTAGGAACAAAATTTTAATGATGATTGAAAACTGAATTAGCTT
TAACATGTGAATATGCTCAGGGGACATAGGACCACAGATCTCTGTTCCTTC
CTATTGCCACTTCTTTCCTTTCCCTGGTAGCATGCTTCCATTACCCATTAC
TTCAAACACTGTTTCTGTGTCTCCAACTCCCTTGCATCATGGTCTTTTCAT
TATTCAGACACAGACACAGCTCGATTATGGGTAAACTTTTTTCTGTGGCTA
CAGAAGAGTTGAGCATGGCTGAAGCATCGTTGAGCATGACTGAAGAAAAAC
ACCTAACCTTGAATTTTTTGATCAATATAAATTTATATCCACAGATTTTAC
CTGACTGATCTTCATTGCCCACCAGTCCTACAAAGTTTGCCAGATTGGTTC
TGTTTCCACTTTACATACTCAGCAAATACTTATTAAGCACACACTTTGTGT
TAGGCTTAAGTGTAGATATTGAAGAGGCACTGGTGAATGAGCAGAGGCTCT
GCCCCCATGGGACCTGCATGCTATTTGGCAGCTCTTTCAGACATTCTCCTC
TCTCAAAGCTTTGAGCCCCTCTATACCCCTATAAGCACCTACTTTCAGCTG
```

FIG. 8-258

```
CTCCCTCACTCCCCCCTTCATGGGGGAAATAACAGCCATCGTGGTAAAACC
TCCACTGCCTGACAGAGCTATATTTACCATCTTTTCTTTAATTTTTATTTT
TAATGGACACAGTTGTATATATTTATGGGGTACTATGTGATATTTTGATAC
ATGTATAGATTGTGTAATGATCAAATCAGGAATTAGATCAGTTTTTTGTCT
TTTTTTGGTAAAAGATAATCTTTTATACTCTTTTGGTCCTGAAAAATGGA
GGAGTGCCATATTAGGATTCCAACAGAAAAAGTTAAACCAAAAGAATATAT
GAAGGGCATATAATGAAGGGATATCTACAAAGTTGTGACAGGGCTAATGGG
AAGAACAGGGGATATGAGGCAGCCCAAGATCAGCAACAGTAGTGATCCAGT
GTCACCCTGTGCTGGTTATGAAGATTTAGTCTCTTCTATCTTTTCCAATAC
CGCTTTGCTAGCCACCTCCCCAAACCCTACCAATAGAAAGCACTGGAGGAA
GACTAGAGGGCTGGAAGGATGTGAAAAGATTTCCCACTTTGTTTGTTGACA
TCCTCACAGAATGGGTTCTTCAACCTGGCAGTGGCAGTTGAATCCAGTAAC
AGCAGTTGGCTTCAGTTTGGAGATCTTCCATGCTCCTAAAATCAGCCTCAT
CATGCCTCTATCTACAGACATATCATCATCAGTGGTCCAGCATACACTCCT
CAGAGGTCCCAGTTCTGGGGATCTCTTCAAAGAATCTTTTCCTTGTTCTCC
TAAACCTGGAGGTGGTAGTTGCTTTCTGTCATTACTATCTCTGATACGTTT
GTCCACTTTTCCATTTTCAGTCCTCTTATAACTAGTTAACAACCATTCCCA
TAAAATTCTTTGTTCAATTTCAGTGCAATTTCTAGCTCCCAGTTATACCCT
GACAGACACACCTTTAAATCTGAAGAGGCAATGGGAGGGAACCTGTAACCA
GAGCTAGGCCAGAGCTGGGACTGTGGAGGAAGAGCTGCCCACCAAGCAGGG
GGGTGATGCAGGGAATAAGTACACTAACCTCTCTCTCCTTTGCCATCTACA
TTCCTGCTGGGCTGATCACTGGCCAAATCCAGCTGTTGCAAGAGGGCAGGG
CTGCCCAGCTAATGCTATCTGTAGAAGCTGGGCTTCTGGGGCACAGAGCAA
GTCAGAGACAGGCAGAACAGGGATGTGGGTTTGGACCAAACACTGAATAAA
CCAGATCAAGGATTCTTCTATCAAGACAAGTTTATATACTTGCAGCTTGAT
CCCATTGTTTCCCTTAGATAACTGTGCACTTGTTTTTGTCTGCCCTCTTTC
CTGTGTCTACACTCTTCCTGTCTTATTCTATTTACACATAGCTCAGTCTTT
TCCAATTAAAAAAAAAAAAAAAAAGCTTTCCCTCTCCCAAATCTCCATGCA
GCTGCTGACTTCTCTCTTCCAAAGCCACACTGTGGGAGAGTCAGTTACACC
TCCTGACCTCTGACAGGTGCAACACACTATAGTGAGGCTTCTGCCCTTGGT
ATTCCTCTGGCTCCATTATTTACAAGGTCACTAATGACTTCCTATTTCTAA
ATCCAGAGTGCCTTTTTAGTTATCTTCCTTGCCTTCTTGGCATCTCTAGAT
AACAATACTTGTCTCATTCTAACTTTTGTCTCTCCTTACAGCTCTTTCATT
CATAATTCATTGTTATTCAGTTGGAGCCTTGATGGTGTTAGGGAGAAGCAG
CATTCTGTAGTCAAAGTGTTAAGCCTCAGTTTATTAGCATGCCTATATCTT
GGGGCTGGGACCGTCACAAGTGTTTATAATGATACAACTCCTCCTCCTCCT
CCTTCTCCTCCTCCTCTTCCTCAAGTGTTTATAATGATACAACTCCTCCTC
CTCCTTCTCCTCCTCCTCTTCCTCAAGTGTTTATAATGATACAACTCCTCC
TCCTCCTCCTTCTCCTCCTCTTCCTCAAGTATTTATAATGATACAACTCCT
CTTCCTCCTTCTCCTCCTCCTCAGACCTTTGCTCCTTTCCTGGCTGCACCA
TTTCCAATTTATTTTCATGAAGCTCTGATCCCTGTTGACTAATTTTCTTCC
CTTAAGTGAGACAGAAAGCCTAGATGAGGCTGCAGTGGGAAGAATTACCTT
CTCCCAGCTGGGATAAGACTCTGGCAAAATGTTTTCCCCTTGAGAGTAGGC
CTTTGTTTTGAAGAAGGTTCTGGGGTGTATTTCATAATAATTCTTCTCTCC
CTGCCAAAGCCACAAGAGGATCCTTCTCAGATCTTCACTGCAGGAACCTGG
TGGGCTTTCTGATGCCCACAAAAGTGTGGGAGCTTCTCACTCTCATGGGCA
```

FIG. 8-259

```
TTCACAGTTGGCCTCCAGCTTTTTGTCAGAGTTACCAATTTAAATGTTCTC
AAATGTGATACTGTCTCAACTTCCAGGACATCACACACTCATGATTTTCTA
CTATCCTGACATTTGCAGTCTTTTTAGCAGATCTCCCTCCCTCTCCCTGCA
CCATGGGTATTGGTCATCTCAGGATCTGTCCCAGGCTTTCTACTCTTCATG
CCCTTTGAGACAACACATGATCTGACCTGCCCTTTCAGGAAGAAATGTTCT
GTCTACCTACTTGCTCCAGTTAAAAACCCTAGTGTCATCTTTGACCCTTCT
CATCCCTACATCTAATCTGTTGATTCTACCTCCTAATTTTCTCTCAAACGC
ATCTATTTTCTTCAATTTCAGTGCTACTCTCTTGCTCTAATTGTACATCA
TCTTTTTTAGAATTACTGTGACATTTTCTTGCCTCCAGTTCTGCCTCAGTC
CATCCACTTCACAGCTAAATTTTGGATGTACACTTTTGAACTATTACTGTA
GCAAAAGTAATATGTAATAACTGTAATGCAGAAATATAAAATATGCAATAT
AAAAGAAATACATGCATAAATGATCCCAACACTAAGGAAACAATATTGATC
AATAATTAAATAATTGGTGGATAGTGAATGACAACATAGAGCAAAGTGTTC
AGTAGGTTTTAAAAGCTGTGGGTTCAATAAATGCTCATGAAGCTTGTTCAG
GGGCTTGCAAAATATGTAATTTGAATTTTTAAAGAAAAGGAATTTCAGATA
AGAAAAAACATACATAACATGAAACAATACTTGTGGTGGTTTCAGGGAGGT
CATGTTCTCACATTCAGGTGCCAAGGCCACCGTACATCCGGACACTGAGGC
CACGGACTTGGTCTGCAACCTCCATGACAGCCTTGTAGATTTGAAACCGAA
CTCCAAGGAGCAGTTGTGCTGTGAGTTCCAGAGTTTGGGGACAGAGGAAAC
ACCATTCTTTGGAAGTCTAACTTCCTTAAGAGGTGTCCCTTAGACATCTAG
TGTCCGGTGTTATGGAGGTCCTTGTGCTCTGAGGAAGGAGCCCCTTGTTGA
TTGATGGAGCAAAATTTTTTTAAACAAGGAACTGTACCCGTATCTGGGCAT
GAAGCCAGAGAAATCCCTGAGGGCAGGGCCAAGGCTCTCAAAGATTTTCAG
GGAGATTCCCAGCCTTTTTAAGTCTCGCCTATTCTTTTTTTTTTCTCTAAC
TGGCCATTTTGTATATATGGAGGTTATTGATTTTTTTGCTTTTATATCCTG
ATATTTTAATAACTGTTCATTTTTTAGTTATTTGAATTATCTACATTGATT
ATTTGAATGTTCTTTTTTTTGTTTTTTTGAGACGAAGTCTCGCTCTGTCGC
CCAGGGTGGGGTGCAGTGACAGGAACTTGGCTCACTGCAACCTCTGCCTCC
TGGGTTCAAGCGATTCTCCTGCCTCAGTCTCCTGATTAGCTGGGATTACAG
GTGCCCGCCACCACACCCAGCTAATTTTTGTATTTTTACTAGAGATGAGGT
TTCACCATGTTGGCCAGTCTGGTCTCAAACTCCTGACCTCAGGTGATCCAC
CCACATCGGCCTCCCAAAGTGCTGGTATTACAGACATGAGCTATTGCACTT
GGGCTTTGAATTTTCTACGTATCTGACTTCTACGAAGAAAACTATAATGTA
TTACTCAGATAAATTAAACAGGAAAACTAAATAATGGAGGAGTATATTTAC
AGTTGAAGCGGTCAATATTTTAAAGGTATTAATTGTCCCCAAACTGATCTA
CAAAACCATTGTAATCCTAATCAGATTCCCAATAAGCTTTATTATAGAAAT
TGACAAACAGGGTTCAAATTTAATACACAAATCCAAGGGCCCAAAATAAAC
AAATCTGTTGCTTTATTAAATATCAAAACTGATAAAATGACAATAATCAGG
GCAGTGTTGTCCAAAAATAGACAAACGAATGGAACAGGCTCAAACAAATAT
GGACATTGATTTACATCTAAAGTGGCACCATACAACAATGGTGAAAGGACT
CTTGTAAATAAATGGCATGGGACAATTGTATAGCCTTTTAAACAGAAAAAG
AACAAAAAGGAAAAAAAAAGAAACTTGACCCCCTACTTCACACTATACACA
AAAAACAATTCCAGGGGAACTAACATGAAAAGCAAAATAAAGTTAAACATG
AAAAGCAAAATAAAGTATATGGTAAAAAATTTATCTTACCCAAAAAGAGGT
CTAGCCTTTGCCCTCAGCTACTGGGAGATGAATTTTAGACCCTTGAAATGT
TCTCACTGATAAGTGTGTCTTTGTTTACCTGGAGGTTTTGACCACCACACA
```

FIG. 8-260

```
GTCAACAATGTGATTTATAATAGGAACTTTGAGCCACACAGTATCAGCTCT
ACCTGTGGAGGTAGACTAAAAGATCGGCCATGTGAGCAGTCAACCATGGCA
GGCCATTAAAACTGCACACTGAGGCTCGGGTGAAATACAGTTCTCTTGTAT
ACGGTTTCTACATGGTTTTAGTTCCTGTGGTCTACTGCAGTCCAAAAATAA
TAAACGGTAAATTTCAGAAATAAACATTCACCTAACTTTTATACAGTATAT
TCTTAACAATTATTCTAATTTATTGTTATTAATCTCTTACTGTGCCTAATT
TATAAATTAAGCCTTATCATAGCTGTGTCTGTATAGGAAAAAACAGCTATA
TAGAGTTCAGTACTATCCATGGTTTCAGACATCCACTGGAGGTCCTGGAAC
ATATGTTTTGTGCATAAGTGGGGACTGCTCTGTACGTCATGTGTATTGTCA
CACATTAATGCTGGGAAAGTAATACTGTTCATATTACTGGGAGAGGACAAC
TGGAAGCTCATATTTGGAACTTGCCTGGATTGTGCCTATATTAGTTTCCTA
GGGCTGCTGTAACAAAGAGCTAGAAGCTAGGGTGGCTTAAAACAACAAATA
TATTCTCTTGTAGTTCTGGAAGCTAGAAATCTGACATGAAGGTATCATTAG
ATCTATGCTTCCACTGAAGCCTGTAGGAAAATCCTTCCTTGACTCTTCCTA
GCTTCTCGTACTTGCTGGCAACCTTTGACATTCCTTGACCTGCAGCTGCAT
AACCTCAGTCTCTGCCTGTGTGTCTGTCTTCACGTGACCACCTTAGAAG
AATACTAGTTCTATTAAAAAATATATATATACTACTTCTTCTAAGTCACCA
GCCCATCATACTGTACTATAACCTCATCTTAACTAATTATATCTGCAACTA
TCCTATTTCCAAATAAGGCCACAATTCTGAGGTACTGGGAGTTGGGACTTT
AAACATATCTTCTGGGGGCAAGGGAGATCTGCATACAATTCGATCCATAAT
ACTGCCTTGTGTGTTTCTTTTCTCAGCTGATTTTAATCTTTATTCCTTGAG
TTGTTTCCCCTTTTCAACTATTACAAACAATGAATTTTGCTGTGTATGTGT
CTTGGTATATATGTGCACACATATCTGCTGTTTGTATACCTCAGAGTGAAA
TTGTTGGGTCAAATGCTAAAATCTTTTTAAAAGTAGTTGTATAATTTTACA
TTGCATTGGAATGACATAATAAGCTATATATCCTATAATAAATTGTAACCA
TGAGGCTAACAGCTTCAGCAAGTTCTGTGAGTCCTTTTAGCAAATTACTAA
CCTAAGGTTGATTGGGAACCACAGACCTCCCAACTTATAATTGGTGTTAGA
AGTGAGGGTAGTCTTGAGAACTAATTTCACAAGAAGGTATTATAAAATAAG
ATCTTCATGACCTTGAAATAGAAAATGATTTTTTAAATAAGATACAAAAAA
GGTTGTGCATAAAAGGGCAGTGTGCTTAATTTGAGTACACTAAATTAATGA
CTTTAATGCATCATGAGATATCATTGGCTGGGTGCAGTGGTGGCTCACACC
TCTAGTCCCAACACTTTGGGAGGCCAAGGTTGATGGATTGCTTGAGCTCAG
GAGTTTGAGACCAACTTGGGCAACAGCACCATCTCTACAAAAAAATACAAA
GATTAGCTGGGCATGGTGGCCTGCACATGTAGTCCCACCTACTAAGGAGGA
TAAGATGGGAGGATCGCTTGATCCTGGGAGGTGGAGGCTGCAGTGAGCTGT
GATTGTGCCACTGCACTCCAGCCTCTGACAGAGTGAAGACAAGTTACAGAG
GAAATACCTGCAACACATAAAATGGATAAAGGGTTCGTGAGCAAAATTTAA
AAACTTAAAACAGAAAAGACAGGCCAGGTTGGTGGCTCACACCTGTAATC
TCAGCATTTTGGGAGGCCGAGGCAGGTGGATCACCTGAGGTCAGGAGTTTG
AGACCAGCCTGGCCAACATGGTGAAACCCCGTCTCTATCAAAAATACAAAA
ATTAGCAGGGCGCGGTGGTATGCACCTGTAGTCCCAGCTACTTGGGAGGAG
GAGAATTTCTTGAACCCAGGAGGTGGAGGTTGCAGTGAGCTGAGACAGCGC
CACTGCACTCCAACCCGGGTGACACAGCAAGAGTCCACCTCAAAAAAAAAG
AAAGGACAAAAGGACAAAAAGACAGCTATCTTAAACCAACAAGAAAAAAC
ACAATCTTTTTGGCCTAAATTGTGTTCCCCCAAAATTGATGTTGAAACTCT
AACACCCAATGTGCCTATATTTGGAGATAGGGATTTTGGGACTTTATGGAG
```

FIG. 8-261

```
ATATTTAAGGTTAAATGAGGTCATAAGAGTAGGCCAGTAGTCTGATAGATC
TGGTGTCCTTATAAGAAAAGGAAGAGACATGAGGTCATTTTATGGGCATAT
GAAGAGGCCACATGAGGACACAAAAGGCGACTGCTGTGGTTTGAATATGAG
ATGACATCTCACATCTGCCATAACAGTAAGAAGGCCCTTGCCAGAGGTGGG
CCCCTCGACCATAGGCTTTATAGCCACCAGAATTGTAAGAAATAAATCTGT
ATTCTTTATAAATTATTTGGTCTCTGGTATTCTGTTCAGCACCAAACAATC
TAAGACAGCAACTATCTTCAGGTCAATAAGAGAGCCCTCACTAGAAACTGA
ATCTCTTGGCACCTCAATTTAGGATTTCTGGCCTGGCCTTTAGAACTGTGA
GGTAATAAACTCCTTTTGTTCAAGCTACCTAGTCTAGTATTTTTGTTATGG
CAGCCCAAGTCGACTGATATACAATCCAATTAAGAAAAAATGGGCAAAAGA
TGTAAAATAAAACCATAATGAGATAATACTGCACATCTGCCACAATGGATA
ACATCTTCAAAAGATTAACAATTTTAATTGGAAAAAAATATTGGGAAGTAT
ATGGAAGAACAGGAATTCCCAGCTAGATTCCATCAACATTAGGTTTGTGAG
GTTCATCCATGCTGTTTATAACTGTGGTTTTAATTTTCATTTCATCGCATG
TAAACCTAATATCACCACTTTCAAAAAGAGTTTAGCATTTGACCCAACAAT
TCCTCTCCTAGGTATACAAACAAAATATGTATTCCTATATATACCAAGACA
CATACACAGGAATATTCACGGTATTGTTTATATTAGCTGAAAAAGGGAAGC
AAATATGCATCAACAGTAGACACCTAAATTGTTGCACTCATAACATGGAAT
ATTACATAACAATAAAAATGAATTAAAGTTATACACAGCAACACAGATGAA
TCTATTCAAACCTAATGTTCTGGAGTGAAATATGTCAGGTACATAGGATTA
CATTTGTTTTATTTCCATTTTATATGTTTCAAAAACAGGCATACTAAATTA
CAGCATTGGAAATCAAAATAGGGGTTATGTTTAGGGCAGATGGAGTGATAA
TGTGACTGGAAGCAAGCATCAGGCGGCTCTGGGAGGGTTGGCTGATTTTCT
GTTTTTTTACTTGTGTGGCAATTATTATGGTGTTCACTTTGTGTTCATTTA
TTGAGCTTTGCATTTTTGTTTTGCTGTGGTTTTCTGTTTATATGTTATGCT
TCTCAGTTTAAAGAATGTTGAAATCTTCTAATACGAAATTTTTTTTCAATG
AGAAGGATTTTAAGCATCCAGAATCAATTTTAAAATCTCCAATTTGCTTTA
TATGTAGGTTTATGGACTGCTTAACTGCTACTCATTTTTTCCTTCATTTAT
CAATAGTGAAATATGAAATTAAAATAATGACTATTTGTGGCAAAATTAGGG
ACTATGTAGCATATTAACAACTTTATAAATAAAAGAATAAATCAACTCACC
TGGGAGTTGTTACTGTCATTGACCTAATGCTATTTCCCATGGTACTCCTTG
TCCCCATTGAGAGACATGAGATACTGCAGATTTATGGGTCACTTTCAACAT
GTCTCCTCCAGGCCTCATTTAGAGAAGCATAACATCATGAGGTTCTATAC
AGGCAAGATCTAGGCTTGTGTCCTTGAACCTTGCATTCCCTCTCAAGAGCC
AACCAATAATTGAATGATCCTATAAAAAACACAGAAACACAGAGAATGGTA
GCAGAAAGCGGATGCTTACCAAACCTATTTTCTCTTTTTCTAAGCAAGGAA
TAAGAATAACTTACCTTCCTCCCTTGGAGTTAGGAGTTCTTATGTAGAAAG
GGAGGCAGAGTGACCTTCAAGAGAGTTTGGAAGGGGGAGTGATAAATCAGT
TTAAAGAGAGCACCCACTGATTCTTAGATAACTTATTCTACTTTCCTTCTC
ACTCTTTTGCATTGACCATGGCTTAGAATATATTTGAGGAAAAGCATACTG
TCCATAAGGTATTATTGCCCTTTAAAGCTGTTGGGGGGTACTATGGGATGG
TATTCAGTGAGAGCAGGACAGAGTCTCTACAGAATTTTCTCTGACAAAACA
AAAACTAAATGACTTCCAAGGCTTCTCTAGCTCTAAGCATTCCACAATTCT
TTGGAAAGCTGGAATCTAAAATTGCCTTAAAATTAAAAAATAAGAACAGTT
AGGGTGTACAGTCTTTACCATATTTATATAGAATCATCAGTCTTCAGTGTG
ATACTGTGCTTGAACCAACAGAAGGACTGATGAAACAGAAGACAAAGTCCA
```

FIG. 8-262

```
GGTCTGGCGCCATGGCTCACACCTGTAATCCCAGCACTTCGGGAGGCCGAG
GTGGCCAGATCACTTGAGGCCAGGAGTTTGAGACCAGTCTGGCCAACATGG
TGAAACCCCATCTCTCCTAAAAATACAAAAATTAGCCAGGCCTGGTGGCAG
GTGCCTGTAATCCCAGCTACTCGGGAGACCAGAGGCATGAGAATCGCTTGA
ACTCAGGAGGCAAAGGTTGCAACTGAGGTCATGGCACTGTACTCCACCATG
GGTGACAGAGTAAGACTCTGTCTAAATAAATAAATAAATAAATAAAATAAT
AAAATACAACCTAAAACCTAGCAATCTCAGCCCTGGAATTCTATTCAATTG
CACCATGTTCAGCAGTGGTAACTGGAAACATCAATGCTTATCAATAAGAAA
TGGATGAATAACTTATGCTATTCCATGTGAAGGATTTCTTTTTTCATGACA
GGGTTTTAGAAAAGTTTGGTTAAGAGAAAAGCAACATGCAGAAGTGTATAT
AACATCGTTGTAAAAAATTTTTATTATTTTTGTTTTGAGACTGGGTCTCAT
TCTGTCACCTAGGCTTGAGTGCAGTGGCACGATCTCTGCTCACTGCAGCCT
CTACCTCCCAGGTTCCAGTCATCTTCCCACCCCAGCCTCCCAAGTAGCTGG
GACTATAAGTGCGTGCCACTGGGCCTTGCTAATTTTTTGTATTTTTTGTCA
AGATGGGATTTCACCATGTTGCCCAGGCTGGTCTTGAACTCCTGAGCTCAA
GTAATCTGCCCATCTGGCTTCCTAAAGTGCTGGGATTACAGATGTGAGCCA
CTGCGTCCAGGCTTTGTTTTTTAAATTAATAACCCTAATCAAAAGACAAAA
CAATTATGCATACAAGGCCAGGCACAGTGACCGTAATCCCAACACTTTGGG
AGGTCGATGATCACTTGAGGCCATTTCTAGACCAGCTTGGACAACATGGTG
TGACTGTCTCCACAAAAAATAAAAACAAAAAGCCCGGCTTGGTGGTGCGTG
CATGCAATCCCAGCTACTCCGGATGCTGAGGCTGCAGGATAGCCTGAGCCC
AGGAGTTGGAGTTGGAGGTTACAGTGTGCTGTGATTATGCCACTGCAGTCC
AGTCTGGGCAACAGACTGAGACCCAGTCTCAAAAGATAACGTGTTTTTTTT
TTTTTTTTTTAAAAAAACAAAACCACAAGTATGCATGTATATAGATAGGT
GTATGTAAAATACTTAGTTCAAAGAAAAACATGTATATTTCTCACAAAAAT
AGGTGAGAATTTTTGTTTTAAAGGATAAACCTAGGTAGCTACATATTAGTT
TGAGGAAGGGGGAACAGGGATGTGATGTGCCTGTATCCCTGACTTTAGACG
ATGGAAGGAGCTAAGCAAAACAATTGAAAAAGACCGTTTGAAAAATACAA
CTGATTATTAACTCATATGCACACACGCAAAATAAACTTTTAGAATTGAA
CTGCACTAAGTAAAAGTGAGTAAACTTGGCTCATCATATACTCTTGTCAGA
TGTAAACAAAAAAGTCCAATTATTAAAATCTGACCCCCAGAATTAAAATTG
CAAAAGCTTAAAGGGGCAGTTCTGAGAAAAGGATCTTCAGTTTTGAATGTG
TGGGCTCCACCAGGGTTGAAAATCCTGCACGACTGATGAAACACGATCCAG
TTAAGCACAGTAATTTTCAAATATCCAATCAGGGCGCTTCCGTTTCTAAAA
ACAGAGAAACCGAGCAAGGGATTTTGGGTTGCAGCTCTAAAACTCCAACAA
ACTAAGCTCCTTTGTCCTGACAAGGGCCTAAACCAAGTCGACAGCCCGTAA
GTGCACCCATGGTAAGGCGCTGCACAAAGAAAGCATTTTGCGTTTCAAAGC
TTTGTCATGATGGCGCTGCAGAAAGCAAGCGAGCTAGGCCTACCTGGCGGG
GCTTTCAGAGGACGCCAACGTGGGCGCCAGCCACGCCAGCAGGGTCACCGT
CCTTCCCAAGGACAGACAGCTCGCTAGCCACTCCTGTGGAGAGGGCGTGGT
TAAGCCATATATTTTGCCAACTATCCCAGAAGCATTTCTTAGGACCACCCA
ATTTCGGAAAATGCTACTTTAGCAATATTGACCCCAAAACGCAATATCCCC
ACTTTAACCTTGTATAATAAAAAGCCTCAAGCCTGGGACTGGGCTTCAACC
TTGGTTCAATACGGTTATGACTAATTAGCTTGGAGTCGTGAGACGCGGGAC
TTCCGGCTACCGAAACCCAGGTGACTTTAAAACTCGATTTAACTCGGTGC
ATTTGAATTCACCTTGCTATCTTTGATAGATTGAGTAGTAAATTCTTACTA
```

FIG. 8-263

```
GATGAGGCTATGTTAAAGTTCTATCGACTCTCCAAGTGATTCTAATATAAT
TGAGGGCGTGTTGCATTTGCTTGGGGGATTTCATCTGTGTACTACAGCTCT
TTTCCTGAAATGCGTAGGTGGCTCTTAAAAGAGCCGTTGGGTTACTAGAAG
AAACTTCTAACTGAATTTACTTTTTCTTGGGTGCCGCTTTCTTGGGTTTGG
CAGTCTTTGGCTTCGTCACCCTAGCCTTGGCCGCCTTGGGTTTTACAGCCT
TAGCTTTAGCAGGGCTTTTAGCTACTTTCTTGGGCTTTACAGTTTTGGGTT
TTTTTGGATTCTTGGAGGATTTCCTTGTTGCCGCAGGCTTTTTAGCCTTTT
TCGGAGTCTTGACGCTCTTTTGCTAGCCCCCGTGGCCTTTTTGAGCTTTT
TAGATGCACCCGTTGCCTTAGTTTTTGTAGCCACCTTTGAGGCGCCGGGCT
TGGTTTCCACGGAGGACGCCTTCTTGTTGAGCTTGAAGGAACCCGAGGCTC
CGGTACCCTTTGTCTGCACCAACGTTCCCTTGCTTACCAGGCTCTTAATGC
CCAGCTTAATGCGGCTGTTGTTCTTCTCCACGTCGTAGCCTGCGGCCGCCA
GCGCCTTTTTAAGAGCTGCCAACGACACACCACCACGCTCCTTAGAGGAGG
AAGCAGCCTGCACGATCAGCTCTGACACGGAAGGGCCAGCGGGTTTTTTCT
TGGAGGCTGCTGCAGCCTTAGCAGGTTTCTTTGCCTTCTTGCCAGCTAAAG
GTTTCTCAGGAGCAGCAGAAGCGGCGGGGGCGGGAGGCACTGTTTCAGACA
TGGTGACTAACACAGCACACCAAATAAAGTGGTATAAACCTGACGAAGCAG
GATGCGAAAAAAAGGCCCCAACGCAGCCTATTTATAGGGTGGGACTGCGCC
GTGATTGGTGCCCGTCAGTGCCCGCCCCTCGCGCCCTAGCGCCCCCTGCGC
GCTGCCGAGGGTTTCGCCCAGTCTCAGAAGGCAGCTGGGGGCCTCTAGGGC
CTATGGTCCTGCTCCCCTCAACGCAAGCAAACACACAGAAAAAGCCGCTCT
GGTTGCCTCATTGTGAAGGAAATTGTAGGCAGACTGCCGCCCAGTAACATC
AGAGGGTACCGCTTCTCTCTCAAAAAGCAGCTCTTTTTTAGGGAGTAGGTT
GAGAGGGGGCGGTTTACAAATGCAGTGCCACAAGCATCCGAGGAGTTTTAT
TAGAAATTTTTAGAGGTCCGTTGCCAGAGATGTTAGTTTTTAATTTGCAAG
AAATGTAAAATACAGTGTTTTGAATAGTTGCGGAGGGAGAGAAAAGTGCGA
GTTTTAGGCCGTGTTAGGGCCAGTTGTCATCAACTCTATTACATTTTCTGG
CAATGTTTTAGAGCGATGTGTCTCGCGAATACCTTTCACGTCAAACAAGAA
TGAATCGTAGACAACACCAGAATTCACAAACGCTGCAATTAATACTCAAAC
TGCAAGTGTGGAAACGTTTCTGCACTTGCAACTTATTTCCACAGTCCAATG
TGGGATGCACTTCAGGAATTTCCAATGCCCTTTTCATCCATACAACATGCC
CCAAATTGGTATTAAGGTTTACAACCTGTGTTCCATGTCAGCACACGCAAT
CAGCGCACCATGACATGGTCAACTCATTCTTTTATTCAACAAATATTTATG
GGCCTCACAAGCCTGCGAAAGGCGTTAAATGCTGGGTCCACGAAACCGGTT
CCCTGACAGGCATTCTGCTGGGGAGTTAAGTCCACTTAGTGTGAAAGCAAA
CACGGGTGATAAATGCAAGCACACCCTGGGGATAAGATTTTATGGTAACAA
CCCTTTAACTTGTTTGTGGCTGTTAAGTGCATTTCAAAGTATCAATAAGCT
AAAACGATCTCACATTGCCAATCAGAGACTCAGCTAATGGGAGAATAAAAA
ACTATTAAATCGACATCCACTTCTACAATCCTATTCTGGATAACCCCCTAG
CACAGCACAGCAGAGAGTGAGGTAATGCGGTCTTATTTCCGCTCCTGCTGT
GGTAGTTTTCAAATAAGTCCGAACCATGCTAAGTAACCTGAGCTTTTCCCC
TTTTTGTTCAAACAACGTGCCAACCAAATAATGGAGTGGTCCCAGATAAGT
ATTGTACCCATCTTCTGCACCAGTGCTTCCTACGTCCCATTTTATTGAGAA
GGCATGCATTCAAATATTTCACGTAATTTCTAAAAATTTGGAAAATAACGG
TTGGAAACTCTACATCTTGGTTTGACGGCTAGTCAGTTATGAAACACAGGT
ATACAAAATTGGAAGATTTTTGTAAGTAAACCCTTTGTGAAAGATATAAAC
```

FIG. 8-264
```
CTTTCTTAGTGTAATAAGCGAGGTATCTGAAAAAACGCAACTTTTGAAAAG
GAAATACTCCTAATTATCTGATTCAGGAGTTTCCACTTTAAATAATGGGTT
CTGCCTCCCTTTTTCTATTGGGTTAAACTGGTTTCAAATAAAATGGGAAC
GCTCCATGCAAATGAAGGATGATAGATCTGCTTTCTAAATGGCTGTTCAAG
AAAATAGCCTAAACCAATCAAAAGATAGAATGTGGCCTGTCTCTTGTGAAT
TTAAAAAGGTCACAATCCACTTTTCAGTGTTTTGAGATTTTCAAAATGATT
GCATTAGCTCTTGGCAATGCTAAATTATGTTCCTTGCGAACCACTATCCAG
TTTCTCTTGGGCCAAGTCCACCTCCTGCTCCGCAAGAGGAACAACTCCCAG
CTGGTGGTACCTGGCGGCAGTGCTGGAGAAACGCCATTTTGTGACTGGCAG
AGTACACCTAGGCTTTAGAAAACAAAAGCTGCAGAACGCTGCAAGTTTAGG
ATTCAAAGAGCATAATCAAGAGAAAGACGTCTCATAGAAAATGTTTCTGAG
TAATAGTGTAATCCTACTATGTTTGAGATGCTTTGTAGATTTCAATAACAC
TCCTAAGTCAATTAAAGCATTACAAAGGAATCCAATTCTTGTGAAAGGTTT
CAGAAATTCCCGTAAAGGGTACATTTCCGGAGAGGAGGTGAGCAGTATTCC
CTCTTTTTTTTTTTTTTTTTTTTCCTAAAGAGCTGAAGGTTATACGGA
ATTGGGGAATTATAATACCTTTGGAATCAATGCCTTGTTTTATGGAAAATA
AACACAGCCTTCAGGTTATGAAAACCAGATGTAGAAGAGGACAAGTTTAAA
AAATTAAAGTCCAAGCCGGCGCAGTGGGGCTCCCCTGTAATCCCAGCTACT
CTGGATGCTGAGGCGGGAAGATCCTTTGAGCCCAAGTTTAAGACCAGCTTG
GGGAACAAAGCAAAAGTAAAATAAAATAATAGTAGTAATAAAATACCACTT
AAATAATCATCTGTAGAGTTGGAATAGAATATAGTAGCCGGTGAAACTGCA
CGATTGTTGCTGGCTTAAAGATAGACCAATCAGAGTGTGTAACGTCATATT
TAGCGTCTTCTATCATCCAATCACTGCACTTTACACACTATAAATAGAGCA
GCTCATGGGCGTATTTGCGCTAGTGTTGGGTGTTCCGCTGTGCTGTTTTTC
CGTCATGGCTCGCACTAAGCAAACTGCTCGGAAGTCTACTGGTGGCAAGGC
GCCACGCAAACAGTTGGCCACTAAGGCAGCCCGCAAAAGCGCTCCGGCCAC
CGGCGGCGTGAAAAAGCCCCACCGCTACCGGCCGGGCACCGTGGCTCTGCG
CGAGATCCGCCGTTATCAGAAGTCCACTGAACTGCTTATTCGTAAACTACC
TTTCCAGCGCCTGGTGCGCGAGATTGCGCAGGACTTTAAAACAGACCTGCG
TTTCCAGAGCTCCGCTGTGATGGCTCTGCAGGAGGCGTGCGAGGCCTACTT
GGTAGGGCTATTTGAGGACACTAACCTGTGCGCCATCCACGCCAAGCGCGT
CACTATCATGCCCAAGGACATCCAGCTCGCCCGCCGCATCCGCGGAGAGAG
GGCGTGATTACTGTGGTCTCTCTGACGGTCCAAGCAAAGGCTCTTTTCAGA
GCCACCACCTTTTCAAGTAAAGTAGCTGTAAGAAACCAATTTAAGACAAAA
GGGAATGCATTGGGAGCACTTTTCGTTTTAATGCTACTGAAGGCTTCAAAA
CCAATCGATTTCGGCCGGTCGCGGTGACTCACGCCTGTAATTCAAGCACTT
TGAGAGGCTGAGGCGGGCGGATTACCAGAAATCAGGAGTTCGGGATCAGCC
TGGCCAACATGGCCGAATCCCGTCTCTACGAAAAATACAAAAACACGCCGG
GCGCGACGGCGAGCGCTTGTAATCCCAGCTACACTCTGAAGGCTGAGGCAG
GAGAAACACTTGAACCTGAGAGGCAGAGGTTTCAGTGAATCGAGATGGCTC
TAATGTACTCCAGTCTGGGCGACAGAGAGATTCGGTTAAAAAAAAAGTTCG
ACTTAAAATAATTCTGGAGTCAGAATGGGTTTACATTTAATTCTTAACCCA
GTTCCTCAAAGCCTGTAGCTCTGTTAAGAAAATAAAGGCCATTGGTCAAGC
CTGCTTGGTCCCACCCTCATCTCCCCACCCTCCCCCAATCGCTGCTCCCGC
CATTTCCTGGGGCTTGGAGGAGGGGTTAAAGGAGCGGACTGTAGGCGTCAC
ATTTCCCGCCTGCGCGCTTTTCAGTCTCAGTGTCCGCTGGAGGTGGGGGCA
```

FIG. 8-265

```
GGGGTAACGTAGATATATAAAGATCGGTTTCCTATTCTCTCACTTGCTCTT
GGTTCACTTCTTGGGAAGTCATGTCTGGACGTGGTAAGGGCGGGAAGGGTT
TGGGTAAGGGGGGTGCCAAGCGCCACCGCAAGGTGTTGCGTGACAACATCC
AGGGCATCACCAAGCCGGCCATCCGGCGTCTGGCCCGGCGTGGCGGTGTGA
AGCGGATCTCTGGTCTGATCTACGAGGAGACTCGCGGGGTGCTCAAGGTGT
TTTTGGAGAACGTGATCCGTGACGCTGTCACCTATACGGAGCACGCCAAGC
GCAAGACAGTCACTGCCATGGACGTGGTCTACGCGCTTAAGCGCCAGGGAC
GCACCCTTTATGGCTTTGGCGGTTAAGGTTGCTGATTTCTCCACAGCTTGC
ATTTCTGAACCAAAGGCCCTTTTCAGGGCCGCCCAACTAAACAAAAGAAGA
GCTGTATCCATTAAGTCAAGAAGCTCAATGTGTAATTAAGATGAATGATAC
TGAGCTGACATCCTAAAAAGGAAAGATTAGGGGAACTCCAAGTTTGCCCTC
CACTCACTACATATGGGTAGGGGAGCAACGATATTCCAACTCTGAAGAAAG
AGTGGAAAAAAGTAGTGTTAAAAATTTGTATTAGTTTCCAAGGGACAAAG
AAGCGCTGCCCAATCAATGAGGGCCATTCGTAGCTGTCAACCAATCAGAAC
TGATGAGCTAATATTTCCTGAGGCAAGCCAGGGAGCCGGAGGGGAAGCTAA
GAAGCTTATTGAGAAAAAACAAAAACCCTGTTTTAGGAAAAAAAAAAACCA
TCTTTTAGCGATTATGAAATAAAATCACAGAGACATTTAAGTATCCCTCAA
TCATGTACTGAGAGCAATACTAAATTTATCGCCACCAATACAGTTTTACTC
TATTAAAAAGACCCTGAAAATTGAAACCCTATTCAGACTCCTGGAATACCC
AGGACACTAAATTCAGGGGAGATTAAAATCTGTTTTAGAGAGAAAAGGCAC
CTTTTTCAGTGTTACCGCGGCCTTCAGCAGTTAACCTTTTTTTTTCCCCCT
TTACGCAGAAATGGAAATTTGGGTGATAGAAATATTCCGAAATTAAATTGT
GATGATGGTTGTACAACTAAGAAAACACGGTAAAATTCATTGAACTGTACC
TAAAGTGGGCAAATTTTGTGGTACATTAAATATCAATAAAGCTGATTATAT
ACATACACATATATTTTTATATATGCAGAGAGAGAAATGATGCAAGCAGGG
TGGTAGGACATGAGGTTGGTAGCATAGGCAATGTTGGTCTGTGAAGGGCCA
CCTGTGCTAAACCTGGAAGCCTGGGGTTTGTCCAGTCAAGCCATGGTAGCC
ATAGTTTTAAAGGATGTTCCTGATGCAGTTATGTGTTCCAGTTAAGTACAT
CTAGCTTCAGAACTCAGCTGGAAAAGGGATGTGAACTTCAGGTTAGCTGAT
AGGGAAATATCTTACTCTCATCTGAGTAAATATTCACAAATGCCTCTCATT
GTGCTCTTTTTGGTACCATTGTTATAGGACTGATTTCAGCCTCACGATGTT
AGCTTCAGTGATGGATGTCTCTTTATTTTGAGGTCCTGTTTTCCACCTGAC
AGTTTTCATCCAGGATTTCTTGAGGAATTACACAAGTACCCAGCTTGGCTT
AATTTAAAACTGACAATGGAGAGAATTCATAGCTGCATTCTGGATAGTTTC
AGGAATCAGAGGAGCAAAAATGAGCCTGGTATGGAGGGTGGGTCATTTTAT
GTCTTTCTTAGTTGGTATTTTAAAGATATTTATTGATCTCATATGCCAGAT
ATTGTTGAAATCATTGGGGTACATAAGTTAGAAAATTTTAATTCCCTTTCC
TGAATTCCAGAGTCAATGTAGAGGGGTGTGTGGATATCGATTACCCATATG
GGAGGTATAGTCGTTGTAACAATAAGCCACGACTAGCTCCTGTTACGTTTT
GCCTGGCCTTTCATAGCATTGCTATGTTCATAGCATTGCTGATATGTCATA
CTCATCTTAGGCATACCCACCACCACCTTGGGCCTTCTTCAGTCCTAACAC
TCATGCAGTCCTTGTTCAGAACAAAGATAATGTTGCTTAATTTGCAACCCC
TAGACTATCCCCCAGATTTTCTAAAGAGAAACTGCACGCTGATTGCTTCAG
GCAGTGGCAGGTCAAGGAATGAGATGGGGAATTGATTGTGTTAGCATTCTG
GTGGGCTTAGTGGAGAGCCTGGAGACTTACATAGAAAATTCACACATCCTT
TCATTCAACAAACCTCCATAAACTACCTGTTAAACGTCAGCCCTGTTCAAG
```

FIG. 8-266

```
GTGCTAGGGATACTTCTGGGACAAAACAAAGTCCCTACCTTCAAAAAATAT
ATTCCAGTTGGGGGAGAGAGAACAAACACAAAATAAAATATATCTAGTTAT
ATGTATTTTTGTTAAATATATTATTACATATATAATTCTAGGTGGGGAAA
TGTTATATATATGCTATTGAGGATAGTCAACTATATATATATATGCTAA
ATGAGCAGAAAAGCTTATTTTACAAGGGATGATTATGGGAGGTCTCTTTCG
TAAGGTTGGTATTTGAGGAGAGGCTTGAATGAAATGAGATCTAGAGCCATT
CAGATATCCAGGACAAGACCCTTCTAGGGAGAAAGAATAGATATAAAGGTG
CTGATGCTGGAAATGCTTGGTCCATTCCAGAAACAGCAAGGTCAGTGAAGA
GAAAGAACTGCGAAGAGAATGAGGTCAGAGGGTAGCCAGAGTACAGATCTA
GTAGGTTGAGCAGCTCATCCTAGTTTGCTTGGAACTTTCTAAGTTTCAGCA
CTGTAAGTCTTACACCCTGAGAAACCCCTGAGAGTCAGGCAAACTGTAATG
GTTGGTCATCTTACTTGTAGGCTATGATAAGGATGCTGGTTTTTATTATGA
AGGTGATGGAAAGCCAGTGGAATCTTTTCAGCAGACAGTGGACATAATACC
TTCAAAAAGGATCACTGTTGATGCTGGATAGAGAAAAAACTGTATGACAGG
GGGATTAAAAGTGAAAACAAAGACCAGTTTGGGGTCACTGTGGTCATTCAG
ACAAACCGCCATGGCAGCTTGCTCCTAGAGAAGCAGCAAAGAAAACAATGA
AAGGTATTCTGATTGATTTTCAACAGAGCTGACTGCATTGGGTGAAAGTTG
TAAGAAGCTCAGGACAAACAATATTGCACAATTCCTGGCCCAAGCTGCTTG
AAGAATGGAGTTCTATTGATTGACATGACAAATATCAGAGGAAGAACAGAC
TTGGTGTTTACGTATAAACATATTTTGGACAAGTTCGAGATGCCCATTATT
CAATTAGATACATCAAATATGCAGTTGTATATGAGTCTAGAGATTTAAGGT
CAGGGAGATGGTTTATAATTGCAAACACTTATTTAGAGACACAGTTTCACT
CTTGTCTCCCAGGCCTAAGTGTAATAGCGCGATCTCAACTCACTGCAACTT
CTGCCTCCCGAGTTCAAGCTATTCTCCTGTCTCACCCTCCCGAGTAGCTTG
GATTACAGTCGCCCGCAACCATGCCCAGCTAATTTTTTTTTTTTTTTAGT
AGAGACGGGGTTTCACAATATTGGCCAGGCTGGTCTCGAACCCCTGACCCC
AGGTGATCCACCAGGCTCAGCTTTCCAAAGTGCCGGGATTACAGGCGTGAG
CCACCTTGCCGGGCCTATATTTCTTAAGCTCTATGTTTCGTTCTGAAGCTT
GAAGTGGGTGGAAGCAAACTGATAGAATTTGGAGAGGTGGTTAGGCATCCC
GGGAATGAGAAACAGCCCGAAGCTGCCACTATCACAGGCTTTGGCATTGCT
AGAAGTTAACGTGGCACTTACAGCTAGGCCGTGGTGTTCTGTTGAACAAAC
TATTTGACAGAGCACAGAGCATGTAAGTGGTGAGGCCAGTTGAGTTAGCCA
AGAAAAGAGGAGTCCAAGAACTGAGCCAGAGTACACCAGAGTATGTAGTGG
AGTACAGCTTTCTCATTCTTTAGTAGGGCTGTGTAGAGAAATACTCTATTT
TATGGATGTATAGATCACTCTAGTCCTTTCTGATGAAAACTTTACAGTTGC
CACTCATTTACTATTACAAACAATGCTGCACTACATTATGTTTCAGTTTTT
AGCCATCTCATCTGGTCTCAGCATTTATTTATCTGCTGATGACTCACACAT
TTTTATCTCCAGCTCAGACCTCTCACCCGAACTCACTTATTCAACTGCCTA
TTCACTATATCCTCCTGTCAGGAGAAGCTTGTTAGCAAAGTAACCAGAAAA
CAAAGTTGATTTTTTTTGCTGAAGTAGCCATCAATATATTTGTTACTAAAT
CAAAGATGCTGAATATTTGGCTGACTTCTAAAAATCTGGTCACCTAACTTT
GACACTTCCTAGGTCGTACAGTTTGAAACTTTCACAATTAAATCAGTTTTG
GAATTTACAATTTAAGGCAGGAATAGAAGACTATTGGGTTGACAGGTACAG
TGAAGATGCAAGTCATCTGAGAATCTTACATCAGAGGGGGCTTCCATCTTA
TAGCTGCTGCCACGGACCTCGGAGTCAGAAGAAATTTGAGTCCTTATTTAT
AAAACAGACTCCCTTAGTCTACTAAGTGGGAATTTACGAACTGCGTAGGCA
```

FIG. 8-267

```
GCCTGCTTAGGGGAGCCTCCAGCCTGAGGACTGAAAATAGCAAAGCAGCTT
TAACCGCCAGTCCTACTCCAGAGAAGGGGGAGGTGACGTCACTCAGCAGGA
CGCCAAGCTCAACTAGAAATGGAAGTAAAGGCTTCTGGCGCTACCGGCAGG
GGGCGGTTAAGGACGGCAGGTGTTACCAGGGAAGCTAAAAGTACAGCTTTT
GCTGACGTTAAGTCAGATACGCCTGGGAAAACAGACCTGACACCCATTTTA
ATCCACCTACTCAGTTCCAGGCAGCTAGCATCTTAGGCTCTCGTACAAATA
ACGCACAACTCGTTTTTAAAACTAAAAAGCTGAGCTACTCATTTATCGGAC
TCGCGCTGCACGTTAAGTTGCTTGACATGTCAAAACTATAGCATTGAAGTT
TATAGCTCACTTATCTCGGAGACCTCGTTTACTTAGCTGATTTCTGCTTTA
GCAGCCACTCAGACCAAACAACCTGGTCTCTCCCAACTGGTTTATAATAGT
TCTACATACTAGGCAGAATAGCCGAGTAAAGCCATTGAGATGTTACCATCC
GAAAGAATACAATCACAGCTCTTTCTGAGAGGGAGTGGGCGGCCCTGAAAA
GGGCCATTGGAAGAAAACTGACGAAAAGATTAACCGCCGAAGCCGTACAGA
GTGCGTCCTTGACGCTTGAGCGCGTAAACCACATCCATGGCAGTGACAGTC
TTGCGCTTGGCGTGCTCCGTGTAGGTCACGGCGTCCCGGATCACGTTCTCC
AGAAACACCTTGAGAACGCCACGAGTCTCCTCATAAATCAAACCGGAAATT
CGCTTAACCCCACCACGCCTAGCAAGGCGCCGAATGGCCGGTTTGGTGATG
CCTTGGATGTTATCCCGCAGCACTTTTCGGTGACGCTTGGCACCTCCCTTA
CCCAAACCTTTACCGCCTTTGCCGCGACCAGACATGTCTAACCAGCTGACA
ACAAAAACCAGGTACGCGAAAAGAAAGCAAGCCACGAGCATTTATACACGA
ACATCGGACCTTATTGAGAACTGAAAGCGGGAGCGAGGATAAGGAGGCGTT
GCTGCCTCACTTTTTGCTCCGCCCCTCGAGGGGCAGTGACCTAAGGACTGC
GAGGGAGAACACAATAGTTTCACTTTTTAATCCCTTTAGTTTTTCCCTCCC
GTTTACGACACTACTATTTGAATCTGAATTTATACCCTCGACTGAGAATTT
TAATAAGGGCTTATATTAAGGGCTTTCACTAATATGCCGGAGTGGTAAACT
TTTTAAGTCTTTCAAGTGCTTGAAGACATATTGACTATTCAAAGGTACTTA
AAAGAGCAGGCGTGAAAAGATCACTCTGGCCTTATGTTTTCTTGAAAGCTG
ACCTGTTTCTTAGAAGCAGTAGGTGAAATTCTCATATGAAAGATGTTCTCA
CTGTAGTTTAAAAAAAGCAACATTCTTCTCAAGGATAGGAGGCTGAGGCCA
AGAGAATTCTGTACAAACCTTGCACTAGCCCTTGCTGGGCGCTTCTCTACA
CAGTTATATATTCTAGCCTAAATCCCTTTGCTTTAGCGCATTTTTACATTT
TACTAATTGTCCAATTCATTATATAAGTAGCTAACTGCTTTTTTTGGGCTT
TCATTACCTTATGAGAGCACCTGTGTCACGTAAAACCTGTGTTAAATAAAT
GCATATACCTTTCTCCTGTTAATCCATTTTACATTAATTTAATTTGCTGGT
CCAGCCAGAGCCCTAAGAGGATGGGAGTGGAGTTTTGCTATCCTTCACACT
GTACTGTCTCATTCAGAAGAGGGTGATAGCTCATTGCAACCGTGCCTTCAT
CTGTAAATCGGGTTATGATGATACTCAGGGGACTTTTAATTAGCTAATGTG
AACGAGGCATGAGAAGAGACTGTGGAAAAGAAATAAATATTACATAATATG
GTTTAATTTTAGATGTTACTACTTAAAAAAATCTGCTCAGAGTTGGGATAT
TGTCCTGAACTCTCATTTTCGTGTTTTTACTCCCAACACTATATTGCTAGC
AGCAACTATGTATGTATTAGTAAGGATTGTTTTTTTAAAATCACAGCCTGT
AATAACGTACAAGGTGTTGACAGATTCCGTTTAGCTTTTCATATGTGACAT
GTTAAAATTGTCCGAAAATATTCCTTTGTTCTCTTTTCCAAGGTGCAATAC
AATAGCAGCATTCGTGCTTTCCTATAGCCAAGTCTGGAGTGTAGTTCAACT
CTCCATACACGCTTCTCACTGTTGTTTTAAATTTCCTGAAAACATTCTTAA
ATCACTTCTATTGGAAAAACTGCAAGGGCTACTGCTAAATTTTTAAGTCTG
```

FIG. 8-268

```
AAAAATGCACCCCAAACTTGACTTCTTTCTCTGAGAATCTTAGCCATCTCA
CCCAAATCTAACAAACCAAAACTGATTTTAGACTTCAACAGCATTAGCTGT
AAACTTCAGCCTGCAGCATAACATCACTTTGTTGTGACTGGGCAGGAAAAA
CCCTGTTAAACTGTTTCAGGCGCGTCCGTGTGAAGAGACCATCAAACAGGG
TTTGTGTGAGCAACAAGGCTGTTTATTCTACCTGGGTGCAGGCGGGCTGAG
TCCGAAAAGAGTCAGCGAAGGGAGATGGGGTGGGTCCGTTTTATAAGATTT
GGGTAGATAGTGGAAAATTACAGTCAAAGGGGGTTGTTCTCTGGCTGGCAG
GGGTGGGGGTCACAAGGTGCTCAGTGGGGGAGCTTTTGAGTCAGGATGAGC
CAGGAGAAGGAATTTCACAAGGTAATGTCATCAGTTAAGGCAGGAACAGGG
CATTTTCACTTCTTTTGTGTTTCTTCAGTTACTTCAGGCCATCTAGAGGCA
TACGTGCAGTTCACAGGGGATATGATGGCTTAGCTTCGGCTCAGAGGCCTG
ACAAACTGAACAACTGGGAACAAACAACATTTAATGCACACAATCTCTATC
TTGTAGGGAGGCAAAATTTTACCTCTACTCTGTTAGGGTCTCCAGCTGGAC
CTGATAATTCATTTGCCATAAAACAGATTAGCAGAATGAAAGCATACAAAT
GTATTTAATGTAAATTTTATGGGACAGGAGAACCCTCATAAAAAAGTGAAG
CCCCAAAGAAATGGCAAAAGCTAAATGCTTTCACATTAAGTTAAAGAGAGG
CAATTGTGGGAAAGTAAACCATATGAGGAGATTAAAGGAATATATGATTAT
TTTAACAAGGTTTGTTTGTGTATAGAAGTCTCTCGGCTATGACTCCCTGCT
GTGTTTGTGCAGAATTATCTCATCTATGCCTCTGGGCTGAAGAATATGTCT
TTTCACCTGGTACAAGCAGAGCATTTTTCACATTGGAACTTTTATCTCCTG
TTTTCAGAAAGAAAAGTTTAGAAGAATTCCCTTCTTGAATGCTGTTTTTGA
AGTGCCTTTAGCTCAAAAGAATCCTGATCCCACAGTGGTCTATTTTTGGAT
GGTATATTCTGCAAACAACACCCCCTTTTTGTCTCCAATCTCTCCTTAATT
ACTCCTCTAATACAAAACAATAGATTCTTAATATAATATTAAAATGTTTGC
ACTACTCACAAATACAAAATGCTCAATAAATTTTCTTTCACAAATGAGAAT
TTCATCCATTCGTTAATTTTTAAATATCAACTGTCAATGAAGAGTTACAGC
AGAATCCTTGTTCTGTTGAGGAGGGGGCAAAGAATGTAAGTGAGGGAGTGG
AAAATAGCTGGACTGAGCTACCACCCCCTGTCCATCTGATCCTCAGACAGT
AATGTAACTTTATTCTTTTATGCTATTCGTCAGACCCAGTACCTCCAACAC
ATTTGTTTCCTACAGATAAAGAAAATATAAAAAGTCAAGCGCTATACATCA
GATCCAGCACATCTATAACTGGAAAAAAAATACTTGACCTTCAGCTGGGCC
CAGAGCTTGTGAGTAGTCACCTTGGCATAGACCAAGTCCATTGGCATCTCT
AACATATCTATACTGTCTGTGGATAACAAATGTCTATGCCAGTTAGAGTCG
CTTGTATAAGAGTCAAGAAAAACGAATCATAAAACAAACTGACATATTCAT
TTTCATAATTTTTAAAATGCAAATATTACTTTATAAACCAAAAACTGCCTT
ATTAAAAGCTGGAACACAAATGAATTTAAGTAAACGATGCAATTCAAATTT
AATCTTTTGTGTGTGATTTGTTGTTGTTGACAGTTGGTCAGGCGATTTT
AGTATGGTACATCAGTTTACATTCTAGATGTAGGCCAAGAAAGAATGTTAG
GTGTAAAAAATATTTATTGTAAAAAAGAATGTGAGGCAAGGTCTTTGGAAT
TAGTAGTTTTAATGTTGGACATTCTGTGGTTGTTCTAAAGTTAGTCTGTAA
AATGTGATGTAAAAGCTATATGATAAAAAAATACAAAATATAAAAATTTTA
AAGTAAATATTACTTTTGTTTGCGTACAGTATTCCCATCCCTCTAAATTTT
CTTCCAGTACTCAATCCCCAACCTCCAAAACCGAAAAGCAAGATCAACAGA
AAGAAAATGGTTAAAACTTGTAAATTCTAGATTTTAATAACTACAGGCAAG
AAGTACTGAAAAAAAGAATGTGGCATGTCATGGTGCATAGTCCTAGAGGAG
ACAAAGCAATGCAACCAGATAGACTATTTACAAGCAAAGCCACACATATAA
```

FIG. 8-269

```
AAATTCATATATAAGGGATTAAATTATGCTTGGTCGACAGACTGACAGATT
TAAAGTGGGTAGCTAGCTATGGATAAAATGAGAGCCAGTTAGATCCCTGCC
TCACATTTTGCACCAGAATAAATTTCAGGTTAATGTTAACAGCCAAATGAA
TTTAACAGTATATATATATATATATATATATAATATATGAGAAAACCTA
GGGGACTATGTATTGAGCTGAGAAAATCTTCCTAAGCATTTGAGGAAGAC
ACTGGAACTCGCAAGACACAATTTTCTAATCTTTTCAAAGCTTTGCAAAAA
TGCCTAGTAAGCGCCAGTTAACTACTTACCAGATTTTTCCCTTACTCTTAC
AAAGTTGTTTAAACAAATGCTAATCATAGCAAGCTAGAGGCCTGAATGATA
GTGGACTTACACAGCTTCTCTCCAAATAGCACCTTAATAAGGTCAGAAATA
ACCTACACTGCAAGACTGACCAAACCGTTATTTCTGTTAATCAACTTTAAG
ACCATAGTCTAATGCTTTCCGGGGGGGTCCTTAGAAATTTGTTCTGTTAAG
ACAACAAAAAATTATCACAGCTACTTTCGTTGGAATAAGTGGGTGGCTCTG
AAAAGAGCCTTTGGGTTTTAAGACTGATGAAAAAGTGACTTTACATTTACG
CTCTTTCTCCGCGAATGCGGCGAGCGAGCTGGATGTCTTTGGGCATAATAG
TCACTCGCTTAGCATGGATGGCGCAAAGGTTTGTGTCCTCAAAGAGCCCTA
CCAAGTAGGCCTCACAAGCCTCCTGCAGCGCCATCACCGCAGAGCTCTGGA
AGCGAAGATCGGTCTTGAAGTCTTGGGCGATTTCTCGCACCAGGCGCTGGA
ACGGCAGCTTCCGAATCAGCAACTCGGTCGACTTTTGGTAGCGGCGGATCT
CGCGCAGAGCCACAGTGCCCGGGCGGTAACGGTGAGGCTTTTTCACGCCGC
CGGTAGCCGGCGCGCTCTTGCGAGCAGCCTTGGTAGCCAGCTGCTTGCGTG
GCGCTTTACCGCCGGTGGATTTCCGAGCTGTCTGTTTAGTACGAGCCATGG
CAAAACCACAGAAAAGCTTGCCTGCAGAGACGTCTGTGGAGGAAAGGAAAG
AGCTACTCTTCTTTTATAGAGTCAGACCACCAACTATTGGACCCAAGAAAA
TTCAAAAATCCCCGCGCCCTTCTTGGATTGGTCCATCTCTGTGCCTGGTTG
CAGATTAAGAGAGGCTCCTGCCCATTACCGTAGCTACTCTGACGTCATTTT
GTTAACCCCTTAGCTGCTATATCCACTGTGGACAAGTCTTGTACTGGAAAA
GTTTCCTGAAGTCTTAAAATTTACAACCACACAAAGCAACGCGGAAACCTC
CAATTGTTTCTAGTTAAAATATAAAAAAGAAATCAGAGAATATTGGAGACG
ATTAGGGAAATTTGCATATGCGCTTTATTTAAAATTGTATTTTTCTGGGTG
TCGCATAAGAAGTGTGGGCAATTAGAAAAATGCTCTTAGCCGGGCGTGGCG
GCTCTCGCCTGTAATCCCAGCTACTCAGAAGGCTGTCAAGAGGATCGCTTG
AGCCCGAGTTCGAGGTTACAGTGAGCTGTTATCACGCCGCTGCACTGCAGC
TTGGGCGAGAGGGAGACTCCACCCCAAAACAAAGCAAAACATCCCCAAACT
GGAAAAAAGCTCATTTTGGGAAATACATACTCAAATGTTCAGTGGTAATGT
GTGTGCTCTCAATTGTGTATGCCATTAATTGCTACAGCAAATGGTATGACA
TATTCAAACTTGTGTGGGGCATGCGGGTTTTAACACTTCCATTCAAGATAG
TTAGGAATGCACTCATGGGTATAATTTCCTTCCTCTAAAATGTAGTAACTG
CTGTGTGTGAAACTTAACGCGAATCACCCCTGTAAACATGTTTTGTGCTGC
ATGGCACTTCTCCCACATACCTAGAATTCCTGAGGTTTCTATGGATCTAAT
TTCTGCAGGACAAATTACTAAAAGTGCCACACTCAAAGCCATTAAAAACAC
CTCAAAAACATCTTTATGGGCGGCATAATCCAAAGCACAACAGCTCATTTA
ATGGAAGTCGTAGGTGGCTCTGAAAAGAGCCTTTGCTGTTAGGCTGATTTT
GTCTGCTGACAGAAAAACAGCAGTGCATGAAGCGTTAACTCTTCACTTTCC
CTTGGCCTTATGATGGCTCTCAGTTTTCTTAGGCAGCAGCACCGCCTGAAT
ATTAGGCAAAACGCCACCCTGCGCGATGGTCACACGCCCCAAGAGTTTATT
AAGCTCCTCGTCATTGCGGATGGCCAATTGCAGGTGGCGCGGGATGATGCG
```

FIG. 8-270

```
GGTCTTCTTGTTGTCGCGGGCCGCATTGCCCGCCAGCTCCAGGATCTCGGC
GGTCAGGTACTCAAGCACCGCCGCGAGATACACCGGCGCGCCAGCCCCGAC
GCGCTCGGAGTAGTTGCCTTTGCGGAGCAGGCGGTGCACTCGGCCCACAGG
AAACTGCAAACCTGCACGAGAAGACCGAGTCTTAGCCTTGGCGCGAGCTTT
ACCGCCTTGTTTGCCGCGACCAGACATAACTACTTCTGATAAGGGAAAATC
GCCACAAGAAAATGTAATGAAACTACATTAGAACGCAAGGCAGAGAAGTAT
TTATACTGACTGGAGGTAGGCTGTGAGGAATTCTCCCATTGGCTAATGTCA
AATACCCAATGGGAAATCAGAATCTGCATCCTTCATTTGCATGTAATCCTT
CCGTCTGGTGTAAGGTTTATGTTTGACCCAATCCCCAGTCTGGCTTGACGA
GCCTTCGACTTGAATACTAATAATAATTGGCCGAATTAGGATTTTGTCAAA
ATACCTTTTTTAAGCATGAGTGGAGGTTTTGTTCTGGTTATTTTGACTTTC
AGCCGCTCGTGCTTTTCCCGGATTGTGACTCATGTTTTTGGAAAGGAGTGG
ACTCCGACCAATTTCTAAATAGATATTTAAGAGGTCCTTCAAATCGGGCGC
AGTGGCTCATGCCCGTAATACCAGCACTTTGGGAGGCCGAGGACGGCGGGT
CAGGCGTTCGAGACCAGCGTGGACAACATGGAGAAACCCTGTCTCCAGTAA
AATAACCAAAAAAGAAACGGGGGAGAAAAAGAAAAAAAAAAGCCGGGCTTG
GTAGTGCACGCCTGTAGTTCCAGTTACTCGAGAAGCTGAGGTGGGAGGATC
GCTTGAACCCGAGAGGAGGAGGTTGCAGTGAGTTCACATAGAGCCACCACA
CTCCAGCGTGGGCGACAGAGCCAGAAGACTGTGTCTCAAAGACAAAAAAAG
GGGAGGGGGAGTGGGAGGGAAGAAAAGCGAATACCCCAAATCCCAGTGAAC
TGTAGAAGCTTATAAGCTCTCTTGATTCATAAGGGAGAAAGAAGGGGGATG
TAGGCAACTTAGGGGAGAGTATATGATTTTGGAGAAAAATAAATGGGTGTT
TCAAAGAATAGGTGACAGCTGTGACAAAGTCTGTTTAGATGGTGTTAACCA
CCAGTCTCCTCTCCTGTGATACAGTTAATCTTCTCTGGTTGATGAGATTCC
CCAGGGAAGTGAATCTTAACAACTAAATTCCTTTTTGAATTTTTTTTTAAT
TTTCAAATTTTTGATTAGAGTTCAGCGAAAGCCCTTCCTTGAATTTACTGT
TTCCTAGGTGCCCTCAGTTCAAAGAAATCAGCGTAACAAAGTGGCACATTT
TTGAGTTGCATTTCCTGAACTTTTTCACAACACTGAATGAGGAGTCTCTGG
AATCTTTCAGGAAATGAGAGAACAAACATTCCATAACACAGAAATACTCAA
AATGGGATTATGATTATAAAAGTGTTTCACTGACCACCTTCTGCCTTCCTG
TCTGTAAGTCCCATTCTCCCCAAAGTCTAGCCATAGAAACCAGAATTCCTC
CTCAAGGTAGGCCATACAAACCAGAACTCCTTTTCCCTAGAACCAGCCATA
AAACCTAAAAGTATTACTCTAACCTACCTTGTTTGCCTGTAGGTCATAAGA
CCCCCCATTCTAAAAGAGAGTCTTGTCCTATAACCAGAAGGAAGAAATGCT
GCACTGAGAGGTCAAGAAGAATCTTGACAGACAAGCCTTGCGGGGCTTCCC
CACTCAGTCTGTTAGCATTAGATCGTACCCTATACAGCTGTTTATCTTGTT
GAACCTAAGCATAAAAATGGGCAATTTCCCCTGTATCTTTCAGTCTTAATT
CTAAAATCTCCTGTAAAATTGTGATGAAATAAATATATATGCCTTTTCTCC
AGTTAATCTGTGTTTTGCCAGTAATTTTCCATAAACCTTGGGAGGGCAAAG
GGGAAGTTTTTCCTTGGCCGGGACAATATTATTACAGCCATTGTCTGGCTC
TCCTGTTGAGGAACCTAAAATCAAGACAGATTGCCTAGGGAAATCTTGGTG
TTTTTCCTTTTATATTCCATGAGATAGGAGCAGATGGAGTACAGATGAACG
TGGATTAATTATTCCAGGAATTTCTGAGGTATCTACTACTTCTATCTGTGG
TCTGCTTATACTGAAACAGGATGACAGAAGGAAAAAGAAACATGAGTGTAA
AAAAATCTGCTCCTGGCTGGGCACGGTGGCTGATGCCTGTAATCCCAACAC
TTTGGGAGGCCAAGGCGGGCAGATCACTTGAGAACAGGAGTTCGTAACCAG
```

FIG. 8-271

```
CCTGGCCAACATGGTGAAACCCCAGTCTTCACTAAAAATACAAAAAATTAG
CTGGGCGTGGTTGTGGGAGCCTGTAATCCCAGCTACTCCATAGGCTGAAGC
AGGAGAATCGCTTGAACCCTGGAGACAGAGGTTGCAGTGAGCCGAGATCGT
GCCACTGCACTCCAGCCTGGGCAAGAGCGAAACTCCATTTCAAAAAAAAAA
AAAAAAAAAATCTGCTTCTAAGCCAACGCTGTCACAGAACTATGGATTTGA
TTCAGAGAAACTGTCAGGAGACTAAAAGTGCTCATTTTTAGTTTGTTTTTT
GCCTTCTCCCAAGTCTTCTGACTCTAGTGTTATCTTTCCCTTCACAATATT
CAACTTCCCTTTTCAAAATTATAATGATCTTCACCCTCAACAATAGCCGTA
AACATCAGTAATCACTGGCTCATTTTCTTTGAAAAGGTACAAGATTCATGA
TGGAGATGTTAAAAAGTTATCTCAGATAGTGCCCTGAAGAGATTATACTCA
GAGAAGGGAGGACTTACGTACATGAAGATTAAATAGCAGTGCACGTTCTGC
ATATAAAATAAAGATTTTGAGCAATAAATCATACAAAAGCACATGGAAAAG
AAGATTGATCAATGTAAATTAGAAGGATTTAGAGAGTTCATGAGGGAGATG
TATATCCAGCATTATTAGTTCAGCATATATTTACTGAAAACCTGCTAAGTG
CCAGAGAGTGTTCTAGGTGCAGGGAGCATAGCAGTGAAAAAGCAGACAACC
TGTTTCCTTACGGTGCTACTTGTCTTGTAGTGGGAGGTGCACAATAAGGTA
AATACATAATGAAAATGTAGAGATAAGTGATGAGTGCTGTGGAGAAAAATA
AAGAAAGGGGATAAGAAAAAAGAATAGAAATAAGGATGGAAAGTTTCATCA
GGAGAATGTCATTTGAATTCAGACCTGAAGGCAAGGAAGAAGCCAGCCAAG
TAGGAAGGATAAATACTTCGATAAAATGCTGGATGTGTTTGAAGTCCAGAA
AATGTCAGGAACCGTGGTTCAGAAAGTACAGCTATTCTAACTTCCTAAACA
AATCGTAGACCATTTTGGAAAGAGCCTTGGATATGTACAGGGCTAGATAAA
ATTGAAACCAAGATTAAGGGTAGCTTCAAAAACTCAGACTAGAAAGCAGGA
GTACATCCAGTCACAATATCAGTAATCTATACTCCACTGAGCCATGGATGA
GAAAAACTCTTCTTCTCATCCAAGTTACCTTGAATTAAGCAAACCAACAAG
CGCCTGGCATGTACTATTAGCAAAACAACTTGATGGCAATCCTTTCAGTAA
GTGCTTCAAAAACAGTAAATTCTAGGCACTTGCCTTCAAAAAACATACAAA
AGGCAGATATTGGGGAGGGAAATATTGGGGGTTATTTATTCCATATAAATA
TAAGAGGAAAATAAGTTGTTTCCCAATAACAACTCCAACACCAGGAGCAGA
GAAAGTAAGACAATCTATGCCTCGTGGTTTGCGAAAACAATAAAAAAAATC
TGTTAATTGCATAATACAATTCACCCTTGAACACGCTCCAAATCAGTGCCC
ACTAGCTACAAGTAGCTACTGTGAAGTTGAAAAAGGGTACTTCAGATTGAG
CTATTCTGTAAATATGAAATAGACTTAGTGTGTTAGTTCGTTCTTGCATTA
CTATAAGGGAATCCCTGAAACTGACTAATTTATAAAGAAAAGTAATTTTTT
TTGGCTCACGGTTGTGCAGGCTGTACAGGAGGTGTGGTGCAGGCATCTGCT
ACTGGCAAGTCCTCAGGAAACTTCCAATCATGGTGGAAGGTGAAGAGGGAG
TAGGCATATCATATGGTGAGAGCTGAGCGAGAGAGATGGGGGAGGTGTCAC
ACTCTTTTAAAGAACCAGATCTCTTGTGAACTCAAAGTGAGAACCCATTGA
TTACCCTGAAGAGTGCGCTTCATGAGGGGTTCACCCTCACGATCCAAAAAC
CTTTCACCAGGCTTCACTTCCAACATTGGAGATTACATTTCAACATGAGAT
TTAGAGGGGACAAATATCCAAACCATATCACTTAGTATGAAGAAAGAATGT
AAAACATCTGACTAATAATTATGCATATTGAATACATGTTATAATGACATT
TTGACTACAAAAGTTAACGAAAATATACTATTGAAGATACTCAAAAATTTA
AAAATACATATATAATTTGTAGTACATTTGTACTGGGCAGAGGAACCTCTA
ACAATGTTCCAAATGTGGCCTGTGTATGTGTATGATGTAGGAGGGATCAGT
CATGTAAGATGATCATAATATAGTTACTTAGTCCATTTTGTGATACTATAA
```

FIG. 8-272

```
CAGAATACCACAGACTGGCTAACTTTTAAAGAAAAGAAATTTATTTCCTAC
TGTTCTAGAACCTGGGAAGCTAAGGGCATGGAATTAGTATCTGGTGAGGGC
CTTCTTACTGCATCATAACATGTTGAGAGAGCAAGGGTATGTGTGTCAGCT
CAGGTGTCTCTTCCTTTTCTTATAAGGCCACCAGTCTAAAGGAAATCAAAA
TATTTTACCCCAAAATATATTTCTTTGACATATTTTGAAATGGCTGCTGCT
TGGCCAGCAGGCAGAAATGGGCTTGCAAAGCTGCCTTAAATGGGAAAAATT
TTACATCTGTAGAGAATCTCCATTAATGCAGCCATGCCTCCTCACCTTTCT
ATACCTTTCCCCAGATCCAGGAGAGACTGAGAGTCTGACACTTAAAAATCA
TAAAAGAAACATTTACCATCTGTTCTTTCTGAGGGAGGCTTCACCTACCTA
ACAAGGCCACCTTTGCAAGCCAAACCTCTTTTGCCTCCCATAACCTGTTTT
ACCAGAATCTAAGCCCCAATTCTTTCTGTGATCTAAAAATGGTATATAAGC
ATCTATAACTCATTGGGAAGTTAGGTAATTAATTCTGAATGCTCCCACATA
GACACGTTAAACAATAGGTAAAATGCCTTTTCACCTATTAATCAATCTGCC
TTGTCAGTGATTTCTGGCAAACATTTAGTGGGCCAAGAGACTATGGTTCCC
ACACTACCCTTCATGAACTTAAGCCCTAAGATATCAATAATTGCATTAAAT
GTGTGTGGTATAAATACACCCATAAAAAAACAGTTTGGCTGGGCGCGAGGT
CTCACACCTGTAATCCCAGCACTTTGGTAGGCCGAGGCTGGCGGATCACTT
GAGGTCAGGAGTTCGAGACCAGCCTGGGCAACATGGTGAATCCTGTCTCTA
CTAAAAATACAAAAATTAGCCGGGTGTGGTGGCGCATGGCTGCAATCCCAG
CTGCTCAAGAGGCTGAGGCAGGAGAATCCCTTGAACCCAGGAGGCGGAGGT
TGCAGTGAGCTGAGACTGTGCCACTGCACCCCAGCCTGGACAACAAGAGTG
AAATTCCATCTCAAAAAAAAAAAACAACAACTGTACACTGTCTGCAAGAA
TCTCACTTCAAATATAAACATAACGCAGGTTGAAATTAAAGGCTGCAAAAA
AGATAAGCCATATAAACATCAGCCCAAAACTGCAAGAGTATCTGTATTAAT
AATATCTGGGATCTGAAAGACCAAAATAGATGCCCCTATACCAACTAAGAC
AGACTCTAAGATTAAGCAAACAAAGTTACCTACTGGTAGAGCATTCATGGC
TTGGCTGGCATGGCAAATTCCTAAATTCCAAAGACTACCAAAAAACTCACA
CTTGCTAAATTCCTTAACTATAGGAGCTATCAGAAGCCCTCCTAACTCTGA
TTTACAGTCCAGTCCACTACAACTCTGATTGGACAGAGGACCGCCTTGACA
CACATTCTATTCTTACACGTAATTGTAGACCTTAAGCCATTTTCAGCCAGC
TGCTAGAGGCAGCACGTAAACTTTGTTCCTATAGTTCACCTTGTGATGTAA
AGACCTAAATTCTACCTCATTTTAACCAAAATTTAACCTCGAAGTGAACAT
GGGAGGTATATTACACGTGTTTATCCATTGTGAATGCACTTGGCACCCCTC
ATAATATATAGCTGTCCCCCCAAACGTGCTAAATATGTATGACTCTATT
GTGTAATATATAGCCTATGAGGCATAAAAATAACCAACCTGCTCCTTCTCC
CCAAAGAGAGTAATTTTGGCAGGTTCTGGGACCATCTCTTCCTGGCTTG
CAAATTAGTATTGCCAGTAAATCTCTCCTTTCTACTCTTTAGCCATCCTGG
TGGTCTTTTGGATGATATATCAGATAAGTATATTTCAGAGCAAAGAAAATT
ACTAGGAACAGACAGGGATATTACATAATGATAACAGGGTCAATCCAATAC
GAAAACAAGCAATTCTAAATGTATATGCACCAAATAACAGAACTGCAAAA
TATGTGTAGCAAAACCTGATAGAACCGAAAGGAGAAATAGACACATACATG
ATTTAAAGGTAGAGATTTCAACACCCCTTCCCCAATAATTGATAGAACAAC
GAAACAAAAAATTACCAGGTGTATAGAACTCAGTAAGTGACTGTATTACT
TGTTTTGATCTGTAAAACAATGATAATAATAGTACTCACACTTCATTGAGT
TTTGGTGAAGATTGAATGAATTTATACTTATAAAGAATTTAGAAATGTGGC
CGGGCCCAGTGGCTCATACCTGTAATCCCAGCACTTTGGGAGGCCGAGGCG
```

FIG. 8-273

```
GGTGGATCACCTGAGGTCGGCAGTTCGAGACCAGTCTGACCAACATGGAGA
AACCTCATCTCTAATAAAAATACAAAATTAGCCAGGCGTGGTGGCGCTTGC
CAGTAGTCCCAATTACTGGGGAGGCTGAGGCAGGAGAATTGCTTGAACCCT
GGAGGCGGAGGTTGCGGTGAGCCGAGATCGCACCATTGCACTCCAGCCTGG
GCAACAAGTGTGAAACTCCGTCTCAAAAAAAAAAAAAAAAAAAATCTTAGA
AATGTAACTGACATATCATAAGCCCTCAAACTTAATAATCTTTTAATACAT
GGAGCTATCTATTTAAAATAATGTACATAAGGCAACATCCCAAAAGAAAAT
GGGCAAGAATCATGAGTAATCAAACCATAATAGAAGAAATGTTATTATCAA
AATGTGCAGTCTCAAACAATAATTGTCTTAAAAATAAAAACAACAATGAGA
TTTAATTGTTCATGTCGGCAATTTGAACAGACTAACACACCCACTGTTCAA
GAGCATTTGTGGAAGTCAGGAAAAAACACCCTGTTGGTGAGAGTGTAAACA
GACCTTCAGGAGGCAACTTGGTAACATGTATTAAAAATCAAATATGTATA
TCAATGGATGCATGATTCCTATCTCTATTTTTGCCCTTACAGCAATCTTGT
GTGTAGAGAAATACTGAAAAGCATTTTCATGGTAACATGGTTTAAATTTTT
AAAAAGCGAAGGTCAGTGAATAAAGGGCAATTATCTACTTCCCTACAATGA
AATGCAGTAATGAAAATAATCATTAGAATCTCTTTTATTAATTTAAAAGGA
TACTAGAAAAGTGAAATACAATCTCACTTATAGAAGATTTACATATTGGTT
TGCATAGACTTGCACAAGATAAAATTTCTGTAAGATTGGTCACCAAAATGT
CCTGAATGATAACATTACAATTAATGTTTATATTGTAGGGGAAAAGAAAAT
TCTGTTTTTCTCACCCATCAGTAAGTTCATGCTTGAGGCCCCTCTACAAAA
AGACAGATTGGTCGGGTGCAGTGGCTCACGTCTGTAATCCGAGCACTTTGG
CAGGACGAGGCGGGCGGATCACGAGGTAAGGAGATTGAGAACATCCTGGCC
AACACGGTGAAACCCTGTCTCTACTAAAAATACAAAAATTAGCGGGGCATG
GTGGCACGTATCTGTGGTCCCAGCTACTCGGGAGGGCGAGGCAGTAGAATC
GCTTGAACCTGGGAAGCGGAGGTTGCAGTGAGCCGAGATCGCGCCATTGCA
CTCCAGCCTGGGTGACAGAGCAAGGCTCAGTCTCAAAAAACAAAAAAAAAG
ATTAGCAAGAGAAAAGCATACAAATGTATTTAATATAAGTTTTATATTACA
TGGGACCCTTCGGAAATGAAAACTCGAGGGAAGCGGGAAACCTGTGAATTT
TTATGGCAAGTTTTGTGAAATGCATAGTTGTGGATTAATATGATTGACAGT
AGGCATATGATCTAATGGTAATAAACTGAGGGGGACATAGCAAGGCTTGTT
TGTTAATTACCTATTAACGATCAGCCGAGTATCAGCAGAGACAGCAAAACA
TCCTAGTTTTGAGTTAGAAGACCTAGGTTTTTGTTTTGGCTTATCAATTAT
GGGTATTGTTTTAGATGAAACATCAAGTATTCTTGATTTCTTATTTCAAAA
ATAAAAAATAAAAAATAAAGGAAGGAAAAAAGAAGAAAAAAAGAGAAGAAA
AGTGTCAGAGTTACTTGAACCAGAGTAACTCCATTTTGAGTGAGGGCTAGG
AAAATGAGGCTGAGACTTTCTGGGCTGCATTCCCAGAAAGTCAGTCATTCC
TAGCTTCTAGATGTTTACGGTTAAGGGAACAAATAAATAATGTTTACTAAA
CAGACTCAGACTTAGGAGTGTCCAGATATCCCTATATCTGGAGAACAAAGG
CATTCTTAATTTTGTTTAAAGATAATAATGTTGATTCTTGCAAAATATAGT
AACTAAGAAAATTAATCCTTTATCACAAACTTGTAGCAGAGCACATCTCCC
CATATATACAAGTATTGTACCTAGGGTGGATGCCTTCCTCCTCTTACTTTC
GGGAATGTCCTGCTCCGTCTATGGAGTAGTTGTCGTTTCACCACTTTACTT
TCTTAGTAAACTTGCATTTACTTTGCACTGCGGACTCACCCTGAACTCTTT
CTTGCGCGGGATCCAAGAACCCTCTCTTGGGGTCTGGATGGGGACCTCTTT
CCTGTAACATATTTCTGGCCACCACAGAAGGGACTATAGTACAGAAACCCT
GACCCAACAGCTACCTTTGGGTAAGTGTTGGAGTTCTGTAACAAAGGAAGA
```

FIG. 8-274

```
AGGCAGGCAGGCAAAAAATTTATGAAAGAACATACGACAAAATAATTTCTG
CTTCAAAACTTCATATTTTTTTAATTTTTTTTTTTTTTTTTTGAGACG
GAGTCTCGCTCTGTCACCCAGGCTGGAGTGCCATGGCGCGATCTCGGCTCA
CTGCAAGCTCCGCCTCCCGCGTTCACGCCATTCTCCTGCCTCAGCCTCCCG
AGTAGCTGGGACTACAGGCGCCCACCATCACGCCCAGCTAATTATTTTGTA
TTTTTAGTAGAGACGGGGTTTCATCGTGTTAAGCAGGATGGTCTCCATCTC
CTGACCTCGTGATCCGCCCGCCTCGGCCTCCCAAATTGCCGGGATTAAAGG
CAAGAGGCACCGCGCACGGCCCCGTCCAAGTTAACCTTGGCTCTAAAACTT
GTCTTCGCTAACATTCCAGTTGATCCTCTAGAACTGAAACAGAATAGCAGC
AGCACCACCTTAAGAAATTGTGGTTATAGCTCTCCTTGTGACAAAGTAGGT
GGCTCTGAAAAGAGCCTTTGGGTTTGGAAGTGCTTACATAAGCACTTATTT
AGAGCTAGTGTACTTGGTAACTGCCTTAGTGCCCTCGGACACAGCATGCTT
AGCCAGCTCCCCAGGCAGCAGCAGGCGCACAGCCGTCTGAATCTCCCTGGA
GGTGATGGTCGAGCGCTTATTGTAGTGAGCCAGGCGAGAAGCCTCGCCCGC
GATGCGCTCGAAGATGTCGTTGACGAAGGAATTCATGATCCCCATGGCCTT
GGATGAGATGCCGGTGTCGGGGTGGACCTGCTTCAGAACCTTGTACACATA
GATAGAATAGCTCTCCTTGCGGCTGCGCTTACGCTTCTTACCATCCTTCTT
CTGCGCCTTAGTGATAGCCTTCTTAGAACCCTTTTTAGGGGCTGGAGCAGA
CTTAGAGGGTTCAGGCATTGCTATTCCTAAACAGAATAGAAAAGCTACTAA
CACTCTCCACTACAGAGTAGTACAGAGAACAGTTCAGAGCCCATGTATTTA
TAGTCCTGAGATTCAAATGACGGTTTAAGATTCCTCACTTCTGATTGGACA
AAAGAAACACGGTTTCACTGAGGGGTGGGGTTTATGCAAATATGGAATTTA
TGTTATCTTTTTCTATTGGATAAAGCACCAAACATAATTGACCAATAGGAT
AGCTTCCTATTGCAGCCTTGCAGTTTGTATAAAAGGATTTGTTCAGGCGCC
ATTCCAGCTTGCTTGTCTTTCACAGTTTTCCGCTGCTTTCATAGGTCGCTA
TTTGCGGACGTGGAAAATGGAGCTAAAGCAAAAACTTGTTCGTCGCTACCG
GGCTTGCAGTTCCCAATAGGGCAGAGTCCGTCATCTTTTTCGAAAGGGCAA
TTATTTTGAGCCGGTCGGAGCCGGTGCGCCAGTGTACTTACAATACCTGGC
CGCCGAGATCTTAGAACTGGTGGGCAGCGCCATACGTGACAAGACCCGCAG
CATCATCCCCCGCCACCTGCAGCTGGCCATCCGAAACGACGAGGAGGTCAA
CAAGCAGCTGGGCAACGTCACTATTGCTCAGGGAGGCGTCCTGTCCAATAT
TCAGGCCGTCCTGTTGCCAAAATAACAGAGCCACGATAAGGCCAAGGTCAA
GTAAACACTCAAATCAGAAAACGTAGCTTACACTTGAAACGGCATTTTTCA
GAGCCGTCCATAGTTACACAAGAAAGGATGATAACTTGCTTCTGTTAGGGT
ATTTTTTGCTTTTCGTTTGGATTGGTTTGTTTTGAGACAGTCTAGTTCTGT
CACCCAGGCTGGAGTGCAGCGGCGCGATATCGGCTTACTGCAACCTCCACC
CCGCCGCTTCACGCGGTTCTCATGCCTCAGCCTCCTGTGTACTTGGGATTA
CAGGCGTCTGCTACCGCGCCCAGCTAGTTTTTGTATTTTTATGCGAGACGG
GGTTTCACCATTTTAGCCAGGGTTGTCTTGAACTCCTGGCCTCTAGTGATC
GTCCCATCTCGCCCTCCCAAAATGCTGGGATTACAGGCGTGAGCCACCGCC
CCCCTAGCCTAATGGTGTTAAAAAGTTAAGTTTCGAGAAAATAACACCTTC
CTTTAGAAAGTACATTTTAGAGTATACAAAGTGAAACTTAAGGCCAACCAA
AATAAGACATTTTGAGAACAGGCAGGGTGGGAATGTGACTTGGACTTAGAA
AACAAAGGGCAAGGAAACTTGCTGTTCGCCAGTAACAAAATAGCATGGAAT
CTCATTCTCTGAATATAAGCGTTATTTCCCGACATGAGTCTGAACGTTTCT
GGTGGTTTAGTGAGTGTTCACCAGCATTGATAACTTGCGAGACTGTCAGGA
```

FIG. 8-275 
```
ATGCAGAATTTCAAGTCCCACTCAAACTTACTGAATCGGAATTTACATTTT
AAAAATCCTTAGATACCTTGTTATACACTCTGTTCTTTGGGACTGGATGAA
CTAGAATTTTAGACAATTTGTCGCTGCAGATAACTGAAACGAAAAGGACAG
GATGGGCGGTGGGGCAACTCATCCAATAAGATTGTCTAGTAATGAACCAAT
CAGTCTGGTCACTCTTCAGCCAATGATTTTATCGCGCGGGACTTTTGAAAT
ATTACAGGACCAATCAGAATGTTTCTCACTATATTTAAAGGCCACTTGCTC
TCAGTTCACTACACTTTTGTGTGTGCTCTCATTGCAAATGGCTCGTACGAA
GCAAACAGCTCGCAAGTCTACCGGCGGCAAAGCTCCGCGCAAGCAGCTTGC
TACTAAAGCAGCCCGTAAGAGCGCTCCGGCCACCGGTGGCGTGAAGAAACC
TCATCGCTACCGCCCGGGCACCGTGGCCTTGCGCGAAATCCGTCGCTACCA
GAAGTCCACCGAGCTGCTGATCCGGAAGCTGCCGTTCCAGCGCCTGGTGCG
AGAAATCGCCCAGGACTTCAAAACCGACCTGCGTTTCCAGAGCTCTGCGGT
GATGGCGCTGCAGGAGGCTTGTGAGGCCTACCTGGTGGGACTCTTCGAAGA
CACCAATCTGTGCGCTATTCACGCTAAACGCGTCACCATCATGCCCAAAGA
TATCCAGCTGGCACGTCGCATCCGTGGGGAAAGGGCATAAGTCTGCCCGTT
TCTTCCTCATTGAAAAGGCTCTTTTCAGAGCCACTCACAATTTCACTTAAA
AACAGTTGTAACCCATTCGGTTGTCTATGTTAGTTTCCAGGAGATATAAAG
GTGATAACTACACACAAGTTTTGTAACTGCAGACAAGTCTATCAGGCCTTT
TCAACCGGTTTTACTGCGAGAAAACAAGCTGAGTTACTGTTTTGCCCTTGT
TAAAAAATTCCTAGGGGTCTTTTTAGCATGTATATGTGTAAATACTTACAT
ATTGAAAGGCTCCTGGGGACACCACCGTCACTCCTTTTAATCCACGTGACA
ATTTTAGTTCTGATGGCAGTATTATTAAAGCTATCATAAAGACAATGTGTG
TGTAGTTACCTAAGTCCACAAAAACAATAGCTGACCCCAAAATTCAGTATT
GGTTTTGGGCTGCTGGAGGTGGAGTCAGAGCTCAGGTGGAAGAAACTGGCC
TCAGTACACACTGCCAAAAGTCCACTAAATAGATTTATGTAACAAGTACAC
AAGACTTGCGTATGACCATCCAAAGATTATGCGGTCATCCTTATCCAGGGA
ATTTGAGAATGAAGGGTGGCAACTGCAAAGCTCTTTTACCCATGTCCTCTT
TTAATAAATATTTAAAAATATTCAAATGCTGATTTCATCCATTTTCTAAAT
ATATTAGTATACTTAACTGATGGGGTAGATCAAGGTTTTCTGGGGATCAAA
CCTTTTACAACTTGTTAACTATTAAAAACTATAATGTAAAATTAAAAATGC
AAAAGTACTGCAGACTGTAAATATAAATTTATAATGGGAAAATAAAATCAA
ATTCCAATTTTATAAAAGCTGACAAAACAACAGCCATCACAAAATTCAGAA
AATAGCATATTTTATTAACTTCTGAATATGACACTACCAAGTATATTTTCC
TGTAGTTTTGACTGAATACTCTGATTCCATCTTCAGATCGAAATTATTTTG
TAATGTTGTCTATAGGTAATGGAAATAGAATTCAATCTTTCCTCCAGGGTG
GCTGATGATAATATGTTTTCTTCATAACTTAGAAGTATTTCAGTTTCAAAA
CACATTATTGGTAATGTCAAGTAAGTTTTTAGGATTGTTTTCAAATTTGGA
AAATCCTCTGTTAAGCTCCTTTCACATGTAAGTTGTAAACTTTGTAAGAAT
TCTTTCCAGACTAGCTTCTGGCTCTATACGTTTCTACTCTCCACTAGACAC
TCACTCTCAGTGCTGGGAATGTGTTTTGAATACTTAGATGTCATAACATTT
TATCTAGACCTGCATCTTGCCAGGAATTTAGGTGAGTTATTCCAGTGAGCA
GTAGGAACATTCCTTGAAGCCATTCTTTTTTTTTTTTTTGAGACGGAGT
CTCGCTGTGTCTCCCAGGTTGGAGTGCAGTGGCGCAATCTCGGCTCACTGC
AAGCTCCGCCTCCCAGGTTCATGCCATTCTCCTGCCTCAGCCTCCCAAGTA
GCTGGGACTACAGGCGCCCGCCAACACGCCCGGCTAATTTTTTGTATTTTT
AGTAGAAACGGGGTTTCACCGTGTTAGCCAAGATGGTCTCGATCTCCTGAC
```

FIG. 8-276

```
CTCGTGATCCGCCCGTCTCGGCCTCCCAAAGTGCTAGGATTACAGGCGTGA
GCCACCGCGCCCGGCCTCCTTGAAGCCATTCTTACGTCAGATTGGCTGGCA
ACGAATGAAGTACACATGATCACATATGCAAATCACGTAACTTATTATCCC
CATACTAGATACATCTTCAACTAAACTTTCTCTTACTCAAATTCCAAATAT
TTTCATCAGGATTCTAACATAATCAGACAATGGTGATTTTAATAAAAAGGA
GGATTGAGTGAAAATAGCAGCCTGAACCATCCGTGATTAAAGTACCTTAAT
ACTGCAAATTTTAAAATCAGAGAGAGAGAGAGAGACAAACTAACACATTTG
TAGGGCCCCTCTCTGCACCTTGGAAGTACAGGCCCTTACACTTGTGTTTCA
TTAGCTTCAGGATAAATCTGCCCCAGATCACTGGCCAAATTTTACGTGGCC
TTCTTCAGCATCCTACCACTCTATTCAAATACATCTCTGCAGGAGCACCCT
GTGAGTTGAGAATTACTGGTCTGGGATGACCACTGTTTGCATGATGCTTTG
GATGGTGGTGCTGTTCTCAGAAGAAATACCAGAAGGAGAAAGGTTAGTCAG
GAGAATATAAAGTCAACCTTAAGCAATTTGAACACTTCAGTGGTTAAGTGA
GTTCCCTGGGACAACTCTGCAAGCTGTTTTAACTTTATTTGTATTGAATAT
TACCTTCTTTTAGAGAGGCCAACGTGTAGAAGGAAATAACAATGAAACAAA
GGATTCATTAATAGTATAAACTATAAACTAACTGTCATTGATAGTCTTCCA
CGGGCCAAGTACCACATGAAGTGGTTGGTCTGAATTATTGTGTAAAATTCT
TACTTCAGCATTGTAAGGCAAATTATCTCACTGTCTCCATTTTACAGAAGT
GGAGGTTCAGCCTCAGGAATTTCACTAAATTCGCCAAATTCTTACTACCAG
CAGATATCATTGCCAGGCAGTGTCACACTTTAATATCTTCTAATCAATAAG
ATAACCCTAAAATTGATTATCATATATAATTTCCTTCTCATATATAGTTTC
ATACTATCATATATAGTTTCCTTTGTTTCAGAAATTGGACTCCCTCAGGGT
GGATAAGGAGACATGGTGGTGTCCTGGCCTAAGTATTGTTGGAATCCTCTA
GTCAGAGGCCTGATGTGAGGTGAAGTGGACAGTGAAACTGCCTTTGCAAAA
ATCATAACTGAGAAAATTATTACAGTGAAAGAGATCTTACCTAACCGACTC
CATCTAACGTCTAAACTCCAAGCTGTCCTTTTCATTCCTGAGTTTGGGATT
AACTAACTTTGGGAGGAGCTTAGTTTATACTTTTGCTTTTAAACAAAAACA
ATAACAGCCCTTTCAGAAACAAACCCCTTTCCTGCCTGGGGACCAGACTGC
TTTTGCAGGACTAACAAATTAGCCACAAGATTATAAATTATGGTTTAGGAG
TCATGCAGCTGGAAGCTACAAGATTCTAAACCTCAAATTGCTCCTGGGGAT
AAAATCACTATTTTAAAACCTAAGATCAATGCTTGAGCTATTTTGCAGACC
CTGAACACAATGGATTAGCTGGCACCACCCATATAGATAAACTGGATTATC
TGGTCTTGAGTCCCCCACCCCACCACTCCCAGGAACTGATTTAGCACAAGA
GGACAGCTTAGGCTCCCTATAATTTCATCTCTGACCCAACCAAGCAGCACT
CCCGACTCACTGGTCCCCTACAATCAAATTATCCTTAAAAACTTTGGTCCC
CAAATTCTCAAGGAGACTGATTTGAGTAATAATAAAACTCTAGTCTCCTGT
AGCGCTGGCTCCTTATTGCAATTCCCCTGTCTTGATAAATCAGCTCTGTCT
AGGAAGTGGACAAGGAGAGCCCGTTGGGTGGTTACAATAGGACAAACCAAT
AAAATATAAAGTATTAGAGACACTACCTGGGTTTCAGGAACAGGTCAGAAA
AAGTGTTTTCTTGGAAAACATCGGATTCTGCTGCAGAGCAAGTATTTGCT
TGTGTCTTCCCAGAGTATAAAAGCTGTCCTGTCCAAGATAGTTGCCACTAA
CCATATGTGAGTATTAAGCATTGGAAATGTGGCTACTCCAAACTGTGATGT
GCTTTAAGTGTAAAATACACACCAGATTTCAAAGAACTAGTAAAATAACAA
AGTAAAAACTCAATATTTTAATATTAGATACCTTGTTGAAACAATTTTTGG
TTACACTGGATTCAAATCATTAAAATAGATTTCTTTTTTCACTTTTTAAAA
TGTGCCTATTAAAAAATTTAAAATTACATATGTGGACCCTATGTTTCTGAG
```

FIG. 8-277

```
GAACAGTGCCAGGACATAGAGGATAGTTATATTCACTCACAGATCAAAAAC
TAGCAAAACTATGAAATACCTAATAATTTAATTTTTCACCTTAACTTTTGG
CATATTCCACAGATCTGTAGTATATTTGAGTGTGATAGCTTAGGAATAAAT
ATGATTGGAACTCATTCATGTTTAGAGAGAAAGGGTGTCAAATTGAGAACC
AGGCAGATACACCTAATCTTAAAATGACCCCAAAGTAAAGTGGTTGAAGAA
ATTAAATCCCAAAGATTTTTGGTGAAGAATGTTGTAGTTTTCATCAGTATG
TGTATGTTCAAATGGAGATTAAAGAAGGCAAAATAAGGCCGGGTGCAGTGG
CTCACACCTGTAATCCCAGCACTTTGAGAGGCCAAGGCAGGCGGATCATGA
GGTCAGGAGTTTGAGATCAGCCTGGCCAACATAGTGAAACCCTGTCTCTAA
TAAAAATACAAAAATTAGCCGAGCACGATGGCATGCGCCTGTGGTCCCAGC
TACTAAGGAGGCTGAGGCAGGAGAATCACTTGAACCCGGGAGGCAGAGGTT
GCAGCGAGCCGAGATCACGCCACTGCCCAGCAGCCTGGGTGACAGTGAGAG
ACTCCGTCTCAAAAAAAAAAAAAAAAAAAGTCAAATAAAAGAACTGTGG
GCTGACAACTGTGGATTAAGCATCAGTTCTATTAAGAAGGGCTAACTTGAA
GATGAATCTTTTGAAGATACATTTGACTCCAGCTCTTTAGAGGAACAAAG
TTTACCTTGATGTGAAATTCTTCAAATAAAAATTTATTGACTTTAAATTTA
AAAAAAAATGCACACACACACACACACACACACAGCTAACTAGCTACAT
CCTTAATGACACCAAGCTTTAGTCCTTCACCCTGAAGTGGGAATGACAATG
GCACTTACTTCAAAGTGCTGTGACAAGAATGTGTTTGAAAATAAATATAGA
GTAATCAGCAACAGTGCTTGGCATATTGTAAATAAGTGCTCAAAAAATGCT
AGTTCCCAAAACTGTTGTTGCCACTGTACCCTAAATCCCTATTCTCTTCTG
ATATCCTTTAGTGATGTAATTCTGTCTTGCACTGGGCCTGTTCATCTCTGG
TATGAATTTCAACCACAATGTCCTTACTACATTTCCCTCAGGCTTATATAG
CCAAAATATCCAGAGCTTTGCCTAGGAGTGTATAATATGATACTTCAATTT
GTAGCCATGATAGCACTGTGTATGAAAGTTTGGAATAATGCGCCGGGCATG
GTGGCTCACGCCTGTAATCCTAGCACTTTGGGAGGCCGAGGTAGGTGGATC
ACTGAGGTCAGGAGTTCGAGACTAGCCTGGCAAACATGGCGAAACCCCGTC
TCTACTAAAAATACAAAAAAATTAGCCGGGTTTGGTGTCAGGTGCCTGTAA
TCCCAGTTACTCAGGAGGCTGAGGCAGGAGAATTGCTTGAACCGGGGAAGT
GGAGGCTGCAGTGAACCAAGATCACGCCATTGCACTCCAACCTGGGTGACA
GAGAGAGACTATGTCTCAAAATAAATAAATAAATAAATAAAAAACAGAAAG
TTTGGAATAATGCATTACAAGTAGCCTCTAGTTTTTATGTTACTCATAGTT
TTATCACACAAGAACAATGTCATAAATTTTCATGGTTGAATTATCAGTTGT
TTATGCAATATTCATTGATGTTTTGGCTTATCAGCAGTGTTTCTGGAATT
ATTTGAATATTATTACCGTTTTCAAAATTATTTTATAAAACTAATTTAAA
AATCAAAAATGATATAATTACTAATGTGAAATTAAATATAAGTTTTGAAGA
ATATCAGGATGTCACCCCCAAATTATTCTACTTTGGCATAAAAGTTATTTT
CAGCTGAAGGCAATTGAAAATCAACAGGTGTAGGAAGAGGTCTCTGTCTTC
TCTTTACCCAAATTTCCCTTTGTGAAGGTGACAGAAATTTCCCTTGTAAAA
GTGTCCCCAACTGCTATACCAGGAAAAAGAGAGCAATTCTTATCACTAGAT
ATGGAAGGTTGGCACTGAGATGACTCTGCAAAAACAAACCTTACTACAATT
ATTTCTATCTTTCATTTTATCTTCCATGGTTTTTATTGCCCATGTATTTAT
TTCCTTGTCACATTCCCAAATTCGTCATCCCATGAAGTGCAAACTCCCTTT
CCTTTGTTGGAATGGTGTATAAGTCTGTGAGTCTAACCGCGTTTTTAAGGT
TTCAATTTTTTTTTCTTTGGGAACTCTGTGCATGTAATATACTAATAAAAT
TGCATGCTCTTTTTTTCGCATGTTAATCTGTCCTTTGTCAGTTAAATTTGC
```

FIG. 8-278

```
AAGACACTACTTAGTGAATCTAAGAGTACAGAAAAACATGTGTCCTCATTG
ACAGTTTCAAAAACTAAGTAAAATTGAGGCAAGAATCTTTTTCATCTTAAA
ATGGCCAATTTTAATTTCCAAATGAATGGTTCATTAGACCTAAGCCAGTAA
GCTATGTGAACAATTGTGATGGAATAAAACAAAACTAAAGAGCATGAACAA
AATTGAGAAAACATATGCAAGACTGAATCTAAAGGCCAAATAGAATTGAAA
ATTTTTCTAATTTTTAACTCTATAAATTAAAGGAATGTGTTTCATTTGACG
AGTTTCATCTGTGGAAACATGTTTGCAGAAGACATTCGAGGTTAGGATTAA
TTGAAAGTACATAAATCAAATGGATTAAGACCCCAAAGGGCATTGAAGGAA
AATTAGAAAATCAGCTATTTTTGCTTGGGTTGATTCCTCTCCTGACTAACT
CTTGGAGATGATAAGAACATCAATTAAATGGGTAGCCATGAAAGTATCTAA
GGGAGAAAGGAACACAGAAGTTCAATGTACCATAACTTTATTTTTATTTAT
TTAGTTTTTTGAGAGAGAGTCTGGCTCTGTCGCCCAGATGGAGTGCAGTGG
CGTCATCTTAACTCACTGCAACCTCTGCCTCCTGGGTTCAAGTGATTCTCC
TGTCTCAGCCTCCCGAGTAGCTAGGATTACAGGTGTGTGACACCACGCCCA
GCTAATTTATTGTGTGTTTTCATGGCCAGGCTGTATTTTCATGGCCAGGCT
GGTCCTGAACTCCTGACCTCAGGTAATCTGCCTGACTCAGCCTCCCAAAGT
GCTGGAATTACAGGCGTGAGCCACTGCTTCCGGCTTTTTTTTTTTATGACG
GAGTCTCGCTGTGTCACCCAGGCTGGAGTGCAAGGTCTCGCCTCACTGCAA
CCTCCGCCTCCCAGGTTCAAGCAATTCTCTGCCTCAGCCTCCCGAGTAGCC
GGGATTACAGGCGCCTGCCACCATGGTTGGCTAATTTTTATACTTTTAGTA
GAGACGGGATTTCACCATCTTGGCGAGGCTGGTCTTGAACTCCTGACCTCG
TGATCCACCCGCCTAGGCCTCCCAAAGAGCTGGGATTATAGGCGTGAGCCA
CCGCGCCCAGCCTTTTTTTTTTTTTAATTGTTTGATGTTGAGATGGAGAA
ACAGGAGGAGGTGGAAGAGATCTTAATATACATATGGAAAAATAAAAAATG
GAATAACCAGGAAAATTCTGAAAAAGAAGAGTAATGAGAGAAAATTAGCTC
TATCTGCTATTAAAGTCACGTTACAACATCTCAGTTAATTAGTCTCCCAAA
GGGGAGACTAATGTAAATGCATGTTTAATAAACTGCACCCCCAGTGGATGC
CTGAAACCACAGATAGTACTGAACCGTATATACACTGTTTTTTTCTATATA
CACATGGCAATGATGAATTTAATTTATAAATCAGGCACTGTAAGAGATTAG
CAATAACTGATAATAAAACAACAATTATAACAATATACTGTAATAAAAATG
ATTTGAGTCTGTGAACGGTGGTTCACGCCTGTAATCTAAGCACTTTGGCAG
GATGAGGTGGGCGGATAACCTGAGGTCAGGAGTTCGAGACCAGCCTGGCCA
ACTTAGTGAAACCCCGTCTCTACTAAAAATACAAAAATTAGCCGGGCATGG
TGGCAGGCCCCTGTAATCTCAGCTACTCGGGAGGCGGAGGCAGGAGAATCG
CTTGAACCCGTGAGGCGGAGGTTGCAGTGAGCCGAGAACGTGCCACAGCAC
TCCAGCCTGGGTGACAGAGGGAAACTCCGTCTCATAAATAAATAAATAAAT
ATAAATATAAATTATATGACTGTGATCTCTCTCAAAATAGCTTACCGTTTT
ACTTGTGATGATGTGAGATGACAGAATGCCAGTAATGAGATAAAGTGAGGT
GAATGGAGTAGGCATTGTGAAGTAGCATTAGGCTTGATAAGATACTACAGA
TTTAGGTATTAGTTGAACACTTGCCATTTGTCACATAATCATCTCAGCATT
GAGGATAGCACACAACACAATGTTTAAAACAATACAATTCTACCTTAAGAA
TTGTGGGAATGACTAAAGGAACAAAATAGAAACCTGAGAAACCTAAGACAG
TCCAACTGTCCATGAAATTATAGCGTATTAGCCTATGACAAAACAGCCAAA
ATTGATAGGAGCGTGGAGGGTGGCACGGGAGGAAGAAGGGGGAAGCAGAAA
TGAAAGTTCATAAATGGTCTTGGGAAAAATATGTCCATATGTTAAACCTTA
CACCAAAATAGAGGGTTCACCATGTTAAACCGTGTTGTAATGTAAAATTAA
```

FIG. 8-279
CAACACAAAATTACTTAAACCATGGGAGAATGTTTTCTCCTTCTTCCCTGC
CTCTGTCTTCCTGTCTCTCTGCTTGCCTCCCTCCCCTTTCTCTTTCTTGGG
ATGAATCCGTGGTCACTATCACTAACAAATCAACTCACTATATTAATCATT
GTGGAGATGGTAGAATAATTGAGCAGCTTATCTCCAGAAGCCCCAGTCCCC
ATAATTTAGGTCTCACCAAAATGTGCCCACCAGATTTTAAAAGAAGCGAAT
ATAAGACGCTAGGCTTTCTGTATTCAGAAGCACCATGGATGTCAAACAGAG
GGAACCATTAACGAAGGCCTTTATTAGAAATGTCTCCCATTTATCCATACA
CTCTTCATAGTTAATAGTACAAATACTGTTTTCTGCATAGAAACATTTGGA
CTGCCAAACAAAATACGTTTAAAGGAACTTCGATTTTTAAATGTTGCTGTC
TGTCTAAACAGGATAAGCAACCGTAGTCATGCGAGGACAAAATGGCTGGCT
AAAAGTTGTGCTTTCGATACGCTCAAAATCGATACGCTCAAACCTGTCAGT
TTAGCGGAAGGCTACATGTTATGTGGCACAAAAAACTCCCTAGGTCCACGA
TTGCCTTGGGTGGAGGAAGGGCTATTGCCGCTGTTGTGGCTGTTTTTTAAA
TGCATTCCTTCGTTGCCACAGGAATGAGAAATTAACAGCAGAGGAATGTAG
GACAAAGGTACCTGCACGCACTCTCCTCCCAGGGCTGGATGTTGCCACTAC
CTCCAGGAGACATCAACTTGACTACCAACAACATGGAAAGCGTCCGAAATC
CCAGACATTAATATAAAGAGAAAAGAGGCAAAACTTTTAAGTCACAGTAAA
GCAAAAAACACAGAATAAGCAACGTCTTCCACCATCCAATTAAATACAGAA
TGAAAGTCATGTACTAGAAGAACGGACCAACCCGGGAGCAGGGCGGGACTT
TTGAAAATTTTTTAGTCCAATCCGGACATCCCTTTAGACTAAGAAACTGGC
TCTTGTTTTGCGGTCTTTTCTGCCGTTCACAGGCCTGGGGCGGGACTGCCA
TCCCAAAACCATCCGCCAGCGAGAAAAGCCTCCGGTCAGGGACCTAGAAGC
CGCAATAAAGGTTTAAATGCTGTAACCTCACCACGGCCACTCTCCAACCCC
GTCACCCAATTCGTCTGATACCTCAGTAACTCCCATACGACTAACCTTAAG
TAACAGGGCAGAACAAGAAAAGGCAGATAGTAAAGAAATTATCCAGCTCTT
TTATTGAGATCAGTGGTGGCTCTGAAAAGAGCCTTTTGGGTTTTAGAAGTA
GGCGTTCGCCTATTTCTTCTTGGGCGCCGCCTTCTTAGGCTTGACAACCTT
GGGCTTAGCGGCCTTGGGCTTCACAGCCTTAGCAGCACTTTTGGCAGCTTT
CTTGGGCTTCGCAACCTTGGCCTTCTTTGGGCTCTTAGCCACTTTCTTGGT
TACAGTGGCCGCGGCCGGCTTCTTCGCTTTCTTCGGTGTTTTCTTAGCGCT
CTTCTTCGGAGTTGCGCCGCCAGCCGCCTTCTTGGGCTTCTTGGCTGCCCC
AACTGGCTTCTTAGGTTTGGTTCCGCCCGCCTTTTTAACCTTGGGCTTGGC
TTCCCCGGAGGCTGCCTTCTTGTTGAGTTTAAAGGAGCCAGAAGCACCGGT
GCCTTTCGTTTGCACCAGAGTGCCCTTGCTCACCAGGCTCTTGAGACCAAG
TTTGATACGGCTGTTGTTTTCTCCACATCATAGCCGGCGGCAGCCAACGC
TTTTTTCAGAGCAGCCAGAGAAACTCCGCTACGCTCTTTAGAGGCGGCCAC
AGCCTTGGTGATGAGCTCTGACACCGGGGGACCAGACGCCTTACGAGGCGT
ACCCCCAGCCTTTTTGGCCGCCTTCTTCTTTACAGGGGCCTTCTCCGCAGG
AGGCGCGGCAGCGGGAGCGGCAGGAGCAGTCTCGGACATGTTGAGAATCAA
AAACTCGGGTACAAGTGGCAAAGCGCCGATGAAGCAGCGCCTGGGCAGGGC
CGCTGTATATATAGAGCGCAGGCGCGCTCTGATTGGTGCTCTGGTCGCCCG
CCTGGCTGGCAGGCTCTGAGCCGCTGCGCTGCTCCCAAGTTGTGTTTGTTC
CACCTCACAAAAGGGGAAAAATATTAAAATTCCCCGCACCAAATCACTTGG
GTTTGGTCAGGAAAGGATCTCAGAAGCCTCGGGCTTCATGCTCTTCATTTA
TTTTTTCCACAAACACAAAAACAACGCGTCCAGGCGTCCCCAATTCCCCCA
ACTCCGAAGGAAGTCTGGGGCAGTCAGAGACCACTTTCTGTTTTTCTTATA

FIG. 8-280

```
AATTACCTGTTCGCTCCTTTGCCCCTGAAGGTTCTTTTTCCCAGGGGTGGT
TGGGCACATGCTTCCCTTATTTTTGAAGAAAAAAGCGAAATGGTTTCCACC
TAAATTTTCATGATAATTCTGTTTCTTCACAAGGGAAGTAACACAGGTCCT
CTGTGAATTCTTCGTGCAGTCGCACAGGAACTGTGGACTGGGACAAGGATT
CCACGGCCAGTCCAAAGCAATTAGGGCGGGATGGGAGGGGGTTCATGAGCC
TTGCTAGGGTCCGGGGTGGTGGGGGGCTACAGACTTAAATCTTTGATTTGA
AGACATTGAAACTATCAAATCCCTCTTTTCATAGATGGGGGTGGGGCATCC
TTTTCACTTCTCTACAGGCGAGAAATTGGGCTCTTTTTAAAGAGCTCTGAG
GTCCCCCTCTGAGTTGTGTAAGGCAGGAGGTCTGGCCCTCAAGATAGAGAT
CATAAAGGAACAAGGGAGAGCCCTTAAGCCTGCAAAAAAGCCAATAGATTT
GGCAGTTAGAGGCACTGAGATAATATGTTTTCAAAGAAAACAAGCATTTTT
TATTTATTTATTTTTGTACGCTGCAATATAGAAATGAATTTCAGCCCATGA
AAATTGTAGGTTACTTTCAGTAACCATACCTTACGCAAGTTACCATATAGG
ACAATCTCCAGTTGGGAACTCAAATATATCTTTTGAGTTGCAAATAAAGCA
ACTGACTTTAATAAAACACACTCTTGACTTTTAAGATGAACAATGTATTTG
AAATTTATTTTTTAAATAGCAAAATTTAACACAGAAAGACAAGAAAAGTA
CCAGAACATGTAATTTATTATAAGATCTGTTGTTGATGAGCTGAAAAATCA
CCTCTTCTCATCCCCTCTGAAACTATTCTGTTCTAAAGTTTGCTACTTTAA
GGTTCACTACTTCTTATTTTACTCTCCGACCCCAAGTAATTGCTATTTTTT
TCTTGAGATTAAAGGCAAAGTAAATTGTCTGCCCATATATTTGATATAATT
ATAGATTCATATTTAGGGACAAAGGTAATATTACAACTCCCCAACAATTTC
TGCTCAAATATATGTTTTCATGAAAATATGTGTTAAAGAGAACAGCCTTAG
ATTGTGGGAAAGTCAAAAGGGAACCTACAAATAAGAGTTCAATGACAAATG
AAAAGTGAAACATCTTTTAGACTAAGGGTGACCCCATTGTTTTATTAAATA
ACATTTGTCCAACATTTGTAAACATTGTCTGCTTGTGTGCTTATGTCCTCT
GGGAATTAACAGTCTAATGAGATTAGTGATGGATGAATTAGCAGTGGTGGA
AAAACACTTAGACCGGCTATTCCTCAGAGTGACAGGGTATAAGAATTATAC
AAAATTATGGAAAGTGTATAAACAATTGAAGCACCTGCATCATACTAATAT
ATTGTAGTAAAAGAAATAATATAAGGCTGGGCCCCGTGGCCCACGCCTGTA
ATCCTAGCACTTTGGGAGACTCGGGGGCGGATCACCTGAGGCCAGGAGTTT
GAGATCAGCCTAGCCGACATGGTGAAACACCATCTCTACTAAAAGTACAAA
AATTAGCTGGGGGTGGTGGCACTCAGGAGGCTGAGGCAAGGGAATCGCTTG
AACCCGGGAAGCAGAGGTTGCAATGAGCCGAAATGACGCCACTGCACTCCA
GCCTGTGCAACAGGGTGAGACTCAGTCGAAAAAAAAAGAAAGAAAGGAACA
ATATAAGAACATGTCACTTAGGCCAGGCTTGGTGGCTCACGCCTGTAATCC
TAGCACTTTGGGAGGCTGAGGCGGGCAGATCGCCTGAGGTCAGGAGTTCGA
GACCAGCCTGGCCAGCATGGTGAAACCCCATCTCTACTAAAAAAAATACAA
AAATTAGCCTGGCGTGGTGGCAGGCAACTCTAATCCCAGCTACTCAGGAAA
CTGAGGCAGGAGAATCATTTGAACCCGGGAGGTGGAGGTTGCAGTGAGCCG
AGATTGCCTCGTTGCACTCCAGAAGCCGAGATTGCCTCATTGCACTCCAGA
AGCCGAGATTGCCTCATTGCACTCCAGCCTGGGCAACAGAGCAAGACTCCA
TGTCAAAAAAAAAAAATAAAATAAACATTTCACTTAGATCTTATTCTATG
TGCAATGAACCCCCTTCTCATTTAAAACTCAGCTAAGTATATCCATCATGA
AAATAGCTATGAAACGTCTTGATTACCAGGTAACTGGACCTTCTTTCACTA
TAAATTGGTGTCCTGGTTTATAAATCGACATGTAAATTTAATCGCTGTGAT
TCAGTTCTCTAATATGATTTTTCTAGTCGACTCAATCTAATCACATCTCTT
```

FIG. 8-281

```
TATATGCAAATCTCAAGTCCAGACCTCAAGCCATTAGGACATCCAGCCACC
CAGAATCTTGTCCCCAACCTCCTGGCAACATGGTGGAGGCCAGAAGACAGA
GAAACATGTAACCAACCCTTTTCTAGATCCTTTATAAAGTGTGTTGAAAAA
GTTATGCAAAACTTAAAAGCAACGCAAAAATATTTCTCCATATCCTTCCAA
GCTATATTAGAGAATTATCTAAAAAGCCTACTTATGGGGTACCTGATGATG
TAAGGCAATACTAGACAGTAAAATAGAATGTGAATCACATAAATACTTTCC
AGATTTCTAGTGGTCACATTGAAAGAATGAAAAGAAACAAGTAAAATTAAT
TTTAAGATATTTTATTTAACTTAATATATCTAAACTATTATCACTTCAACA
TATAATAAATAAGCTAAAAAAAAAGACAGTTGACATTCTTTTTTAAATGAT
AAATCTTCAGAACCTGGTGTGTATTTTACACTTTTAGAACATTTTAAATCA
GTCTAGCTATAGTCCAAATGGTCAATGATCACGTGTAGCTAGTGGTACCTT
ATTGGACAACACTGTCCTACGTGAAAGTAACTCTGACTTAATGTTTACATT
TTATTGGGTCCAGACTATCTAAAAGTAAACATTCACTTGTAGAAGTTTAAT
AAATTAATAAGGATTTTGTCATAGAGATGGAAATGAATTCTTAATATAGAA
AAAATGACCCTAAAAGTTATTATTGTATTGCCTAATAAGTCATTAAACAAC
TTTATATCTGATTTTCCCTTCCTCTTCCAGTATACATCCTTTCCCTGACCA
AATACATATTTTATTCTCCCGTATCTTCCTTTGACCTAATTGTGATTCTGC
TTCCTCCTTCATTAATGAATTAAATCATTCATTGACACATACACAAGCTCA
CTATATATAGTACATATATGTCAGTCATGTTTTTAACTTCCTGAATGTTGT
ACTTTGACACTTGGTTGTTCAATTTCGCCTAAGAGCTCTGAATCAGAACCT
TTAGAAGCCATTCTGAAAAACTGGAAGATACAAAGCTTTTGACTATCAACT
CCATAGCAACCTGATATCTGGTTGGTGTTCCATGGAAACTGTATTTCTCAA
ATTTTGAAATAAGATTGAACAAGCCTGTGAGCAACAACAAAAAAAAAGTCT
ATTAGAATGACCTCTGGCCGGGCGGGGTGGCTCACGCCTGTAATCCCAGCA
CTTTAGGAGGCTGAGGTGGGCAGATCATGAGGTCAGGAGTTTAAGACCAGC
CTGACCAACATGGTGAAATTCCGTCTCTTCTAAAAATACAAAAATTAGCTC
GGCATGGTGGCGTGCATCTGTAATCCCAGCTACTTGGAAGGCTGAGGCAGG
AGAATCACTTGAACCCAGGAGGCGGACGTTGCAGTGAGCTGAGATTGCGCC
ACTGCACTCCAGCCTGGGTGACAGAGCGAGACTCTATTTCAAAAAAAAAAG
AATGACCTCCAAGGGAAAGTTCAGATTAAGGATGTGGTCGTCCCACCCAAA
ACTGATGTCCTCAAGAAAGCCACAAACAAATTGAGGACACAGTTAAAATAT
TGTAATGCAATATATTGTGTATTCTTTTATTTACACACACATCATAAATAT
TATAGGTTGACTAGTTTTGTTTCATGCCACACTCTTCAGGGTCTGGAAACC
CTGGTAGAAAAGTTAAAAATGCAGAGCAAAATGTCAAGTCCAAACAGCAGT
AATGGGGCTAGAGAGAGACTCAAACAGCCAAGATATATTCAAAGGATAGTG
AGAGGAGTTGTTAGGACAGGTGTAAGGAATGAGGGTGACAGCTGGTTTTTC
TTTCACTTTTTCCTTCTACTATGCCAATTAGAGTTCTTTGTTTTTGATAGA
GACAGGGGTCTCACTATGTTGCTCAGGCTGGTCTCAAACTCTTGGCACCAA
GTGATCCTCCTGCCTCAGCCTCCCAAAGTTTTGAGATTATAGGTGTGAACC
ACCAAGCCCAGCCTTAGAGTAGGGTTCTGTCATCTTTTGGATGTAGCTAAC
CTAATATTACTAAATCCTGTATAGGCCAGAACTTTGAATGATTTAAAGCTG
TTTTTTCCTGACTCACCAATTAATGAAGCTAATAATAACAGCCACCCCACT
GGCAGTGCCTGCCTCAAAGAGTAAGTGTTAGTGTTGCTATCTGCTTGAGAC
CAACAATACAGGGACTCCAGGATATTTCAGCCTAAATAAGATTGTAGGGG
CTCTTGTCTGTTGCCTGGCTTCAGCCCCATAAACTTTTTTTTAACATATAA
CCCAGAGCCACAGTTTTGCTCATATTTCAATCTTTGAAGGCAAATGGCCAA
```

FIG. 8-282

```
CAATTAGATTAAACCTGAGGCTAAATATTTCCTCACCTCAAGGGCTGAGAC
GAAAGTTACTGCATCTGTATTCCCTAACACGCCCTCAAAATGGGTTGCAGA
AAACAACAGAAAATATACTAAAGCACACAGTAGGAGCATAATAAATAGTGA
TTAGCTGGGTGCAGTGGCATGCGCCTGTAGTTCCCGCTACTCTACTCATGA
GGCTGAGGCAGGAGGATCACTTTTGCCAAGCAGTTTGAAGTTGCAGAGAGC
TATGATCACAACACTTCACTCTAACCTGGGCAACAGAGCAAGACTCTGTCC
AGAAAAATAAATACATAAATATAAATTTAAAAATATAAATAAATACATAG
AGAGTATTACAAAAGGAACAATATATTGCAAAATATATTTACCTAACATTT
TGAAATTGCCATTATAATTGTATAAGTGACATAGGAAACTGGGTCATTAAC
AGCTATCTTATTCTTCAAGCTTCTTTCAAATGATGTCAAAGCATTTCAGAA
AGTCAAACCTACCCTCAAAGGATAAGAATTTGTCAATTGTGAGGATATGCA
CATTTTTACACCTTCTCAATCTGTGTCTATATGAAGGCAGTTATAAAGCAC
AAGATGCAAACGTATATTAGGCAATAGTCTTCATCAGAATAAGTACATAAC
CTGACACAATGACTATATTGGAAGAAACATGGAAATGCAAATTTCAATAGA
TTGGTTGACATTATTTTTTAATGTCTAGTTTTTTACTGTGCTGTGTTTTTA
CACACTTAATGAGCACTTGTTAAGCACAGGACACCAGGAGAAATAATAAAA
ACTAAGATCAGCCTAGCAGTGTGTCCTCTCAAGAACTTATACCTGGTGGGA
CAGATACAGACAAATATAACCATCATACAGTGTGAGAAATCGATAGAAAAG
ACACAGCCACTGAGAGCACAAAAGAATAAAAACATAAAATGTTAATGTGCT
GGCTAAACGTTTGCCTTCAAGTATTTACCAGTCTAGCTGGGAAAATAAGAC
AGAAGACAACAGCCTAAAATAGTGGTTCTTAAACATTTAGATATCAGGACT
TCTTTACACTCCTAAAAACTATCAGGCCTCCAAAAAATATTTTGCTAAATA
TAGGCATTTATCACTTTGGAAAACAAAGCTGAGTATTAATTATTTAATTAT
TTATATTAATATTTATTTGATAACCTTTAAAATATTATAAAATTAATATTT
ATTTATAATGCATATATGTGATTATATAGTTCATATGTAGCCATATATTTA
TCATATATACCATAGATTTATGTTATATATTACATATGTATGAAGAAAAAA
TGGAAAGTAAACCCAAAAGTTCCCCATTCCCTAACCCATTCAAAACCCTGG
AAGTCCCAGGCTAATCTGAAACTTGTAAAACTGCCTGCATGTAGAGAGCAC
AGCTGAGCTGGTAGTGTGGAAGAGCAGAAAGACAGCAGTTCTGGAGCAAGG
AAGCTTTATATTTAATCCCAGTTTCTCCATTCATGAGCTTGGTTACCCTGC
CAAGTTCCTTCTCTGTAAAATGGGAATAATACTCCCAGAAATACAGTGAGG
ATTAAATTAGATAATGTGCATACAGTTCCTGGGATTGGGATCAGCACACAG
TAGCCTCTCATTTGAGGCATATTTGCATTAGATCCTTGCTGTATGATATCC
TTCTGTTTCTTTCTTTTTTTTTTTTCCTTTGGTGACCCTAAGAAAGATG
GTACTCTCCTTAACTTGGAGGGCTGGATGCGAAGAGACCAAATCCAACAAG
CTGGTTCATTCTTTCTAATTATGTGTGCTTCCCTTAGCTGCCTCTGAAAGG
ATACAGGCCCTAGGTACTAGCCCCAAGAAGCCTAATGATAAGAGATAGAGC
TGGACCACCAGAGAAGAGATGAGTGTGTATGTGTGTGTGCAAGCAATTA
TATGTGTGCATTTAGGAGTGGTAGGTGTGTAAACAGTCTAGAACACTCATT
CTCACTGTGATGTGAGGATGTATCCCCACATCACTGTTCTGGGAGCTCACT
CCTTGTCCATCATCCAAGCTTATGATGGACAATTCTTTCCCAAGTGGGAAA
GAATTCTGATGACACTCACATAACTACCCAGTCCCAACTTTCTGTATCCAA
GGTGTGTGCATACCTTTGATAGCAGGCAGGTGTGCCTAGCCAATATATTAG
GAGCATGGTATTCCAGCACTCTGCACTTTTTTACTATAGAATTCATCTCAA
CCTGCTTACATTACATGAAAGTTTTGATTGATATCAAATTTTTATTATGTT
TGCTTATCAAAGGATTTGTAATTATGCTTCAGTTGATACATAGATTGTTTA
```

FIG. 8-283

```
TATTTTTCATGGTTACTTGAAGCACTTATATTTTCCTCATACTTTTACAAA
GTAATCAAGGAAAAATACAGAGGCAGCTTAGTATATTAGTCAAAAGAATAA
TTAGACTGTCTTGGAACCTGGAATGTCTGAGTTCAAATTCAATTTTGCCGT
TTTACCAGCTGTGTGACTTTGGGTGAGTTAATAAACCTTTTCGTGTCTCAG
TGTTCTCACATGTAAAGAGACAATAATAAGCCTACCTGTTTCATGGGTCAT
TATGAGGATTAAGGAGTTAACATTTAAATAGTTCTTAGAACAACCTCTGAC
ATATTTAAGTACAAAAATATATACATATATTAAATAATAACTTTTCTAAA
ACATCCTACCTACAATCTTGTGTGCAAATTGGTGGCTCAATTCTGCAACTG
TTGTTGGTGGTGTTGTTGTTAAGCTTTTGTTTGTCATGACTGTTATCAGTA
ATATTAATACAGACAGTTAACTGAACCCTTCCTCTGCACCAGGCATTATAT
GGACTATTTTCATTCTGACTCCCTGCATTCTATGAGACAACCACCATTGTA
ATCATTCTCACGTTGCCAATAAGGAAATGGAGAATGAGAATTCAGACTTCT
CCAAGAAGTGCTGCAGACTGATTATAAATCATGCATCCTAAACACACACAT
ATTAAAGTATCAACTAAATCAAACAGAATAAAACTTTTGTTTTTCTATCTA
CAAAATGCATGAATTAAAATATGCCCCAACTACTTAACTAATATATTTAGT
AAGTAGAGGGATGGAAGCGTTTTCACTCCTTCAATACATTCTTCATCAACC
TCTCTCACCTTACCCCTCTGTCACAGGCATTTCCTATGTCATGCGGTTTTT
CTGATGTACGCTAGGTGGCAGTCAAAACCACGAACTCTTGAAAGAGAGTAT
ATTCCTATTTTTCTGCAGCCTCAACCTCCAGGGCTCAAACGATCCTCCTGC
CTCAGCCTCCTGAGTAGCTGGGGCCACAGGTGCGAGCCACCACACCTGGCT
AACTTTTACATTTTTGATAGAGACGGGGTCGCCATGTTAGCCAGCCTGGTA
TCGAATTCCTGACCTCAGGTGATCTGCCCGCCTCAGCCTCCCAAAATGTTG
GAATAACAGGAGTGAGCCACAGTACCTGGCCGGTAATTTTTAACTTCTAGC
TATACACTTAGTTTTTTGTCCTTTTCAGTGGACAGAAATTATAATGCCTGT
TTGACAGGGGATAATTCTGAGGCACTGGGAAGCCATGAGACTGCATGGATT
GCACAGGCAGGCAAGAACATGGGAAGGAACAAGTGTCTTAGACACTTGTCT
CAGTGGTCTAGAAAAATCATGCTAGCTGATTCATTCACTCCACAAACAACT
GATCAACATCTTCAAGAAGCCTAACAATGTACTGAGTTCAGGGGACAAGAA
AATAATTCAGACAGGCTCTACCTTCATGGTGGTGTTTGAAGAATAGGGATC
TAGAAAACGGTAGGTAATAGTGGCTGTGCAAAAGATATCAGAGATGATATG
AAAAGGAGGGACTAGACCATTTTACCCAGGAGTGGAGGTTAAACATAGGGT
CTTTAAGGGAAACGTAAAAATATTAATTCTTTTCATTTTTGAAGTAAAATG
ACCATCGCTTCTCGGCCGTTTGGCTAAGAACAAGTGAAGTAAAATGACTGA
GGATGACAGACATAAATACTGCTATACAAACATGGTAGCACTGAAATTGGC
TCTTGCCTGACAGGAAGCAAAATTATAAAATTCATTATTTAGATATATCAA
TAATGATGGTGATCAGGCTGTAATAATAATGTTATTAATCATTATGTATCA
ATAAGAATACAGGTGTGTGACTTTACAATGTGCCTAAGAGCAACCCAATAT
TTTGATTGTAAACCACATTCCCTTAAACACACACACACCTCAAACAAGACC
CCATAAAGCAGACTGCACTAAAGTGGAGGTTATGTAAAAGTCCAACAGAAT
AAGAACCCTCCCCCATTGTGTATTAATCTGTGAACTAAAAAAAAATTTCAT
TAAATTGAAAATATCTAATTGTCAACTAGCAATTTTAAAGAGTTTAGGCAG
AAAATGAAATATAAAGCTTTTTTTTAACTTTTAGATTTTTCAAAGCTAGCA
GAACTGCTGAAGAATAACAATTCAAAACATAGGTTTGCTTTGGTTTCAATC
TCTGTAGCCAAAGGCATTTACAATGTAGGATGTTGTTTGTGCTTTCAGACA
CTAGATGACGCTCCAAATCAAAATGCCGGTAGTTGGACAGCCCCTGATCAA
GCCGCCCGGCAAATCATTAACTGGGTTGACACTGTATTACTCAGCAGATTT
```

FIG. 8-284

```
CAAAACTCATTCACATACAGAGTCTTTTGGTGGACAAAAATAATTATTACC
CACAATTGACAGTGACAGTACTGAGAAGCTGGGAAACTGAAGTAGGACCCT
GGAGCAGCCAAGTACAGAGACTGGCTCCCAGGACCTTAGGAGTTAATACTA
TTCCTAAAGAGAATAAATTGTCAAATAGACAAGAAATTCATGTGGGTTGAT
GCATTCACTTCCCCAAAACAATTATTAAGCAGTAGAAATGATAACTACGCT
GGTAGTGGAAATAGTTTACAGTAAAAGGGAGAAGACATGCAAAAACCAAAA
AAAAAAACGGGGCCGGGCGCAGTGGCTCACTCCTGTAATCCCAGCACTTTG
GGAGGCTGAGGCGGGCCGATCACGAGGTCAGGAGATCGAGACCATCCTGGT
TAACAAAGTGAAACCCCGTATCTACTAAAAATACAAAAATTAGCCGGGCTT
GGTGGTGGGTGCCTGTAGTCCCAGCTGCTCAGGAGGCTGAGGCAGGAGAAT
GGCGTGAATCCGGGAGGCGGAGCTTGCAGTGAGCGGAGATCACACCACTGC
ACTCCAGCCTGGGCAACAGAGCAAGACTCCGTCTCCAAACAACAACAACAA
AAAAACAGGCAGTGATGTTTATGTGGGTCAGTGTGAAGTAGAGATCAAAG
GAGAAAACGGCCAATCTTACCAAATAATGGATGCAGAAATAATCTTCATGG
AGAAGCCACTTTAATTATGTCTTAAATGAGAGTAACAAATTAAACATAAGA
ACCTGTAGGGGCTAAGGGAAAACTTACTCTTTGGCCTCTGAAGAGTCGCTG
AAAACCACCGACAAGAGGAAGATTAATAGGATAAAATGCATCCAATTTATT
ATTATTATTATTATTATTATTATTATTATTATTATTTTTAGACGG
AGTCTCACTCTGTCACCAGGCTGGAGTGCAGTGGCGCAATCTCGGCTCGCT
GCAACCTCCGCCTCCCGAGTTCAAGCAATTCTCCTGCCTCAGCCTCCCCAG
TAGCTGGGACTACAGGCATGTGCCACCACGCCCAGCTAACTTTTGTATTTT
TAATAGAGACGGGGTTTCACCATTTCGGCTAGGGTGGTCTTGACCTCGTGG
TCTGCCCGCCTCAGCTCCCAAAGTGCTGGGATTACAGGCGTGAGCCATTGC
ACCCGGCTGCATCCAATTTATTAATGTGTATATTAATAAATTATCCAATTT
ATATCCAATTTATTAATGTGTATTAACATGTACAGGGGAAATTGTCCATTT
TTATTTTTTAGATTCAACAAAGTATGGGCCGCCGTGTAGAAATAGGATTGC
TAATAAACAGAGTAGGGAAACCCAGCAAGGCCTGTCTGTCTAGATTCTTCT
TCGCCTCTCTGTGCAGCATTCCTTCCTTCTGGATCCTCTCTGGAATGCGGT
CTGGTGATCTATGATCAAATAAGGTAGTTCAGATAATTTCTTTATGGCCAG
TTTTTACACAGAAAAACAGAGGGAAAGTTAGAGTAATATTTTTAGGTTTTA
TGGCTGGGCTCTGGGGAAAAGGTGTTTTGATTTCTATGACCTAACTTGAGG
AAGAGGAATTCTCATTTCTATGGCTAGACTCCGGGGAGAATGGGACTCAGA
GACAGGAGGGCAGGAGAAGATCAGAGAAAAACTTTGGCTTCTGCGGTCTTT
ATTTTGGGGTATTGTTTTCTGAGTTCCAACAAACCCCAAGGACCTACAAAG
ACTGCATACTTTTTTTTCCTTTTTATTAATTGTGAGATAACCACAGCATA
GGCAATTTGTTTTTTGTTTTTGTTTTTGAGACAGGATTTTGCATTGTTGCC
CAGGCTGGAGTGCAGTGGCATAATCATAGCTCACTGCGTCCCCAAACTTCT
AGGCTCAAGAGATCCTCCCAGCTTAGCCACAACTGAGAGGTGCTACTAGCA
TTTAGTGAGTAGAGAACAGATATGACTAGAGGTTCATTAAGTGTTTTGAGC
CTTTACAGCTTCAAAATTGTCTTTGCTAACCCCTAACTTTTGGATGCTACA
GAGGGCCCCTGGAGTATCCAAAGGAGAGGTAAACAGGATCATTTGACACGT
TTAGTTATATAGGATTGTTGAAATAAGGTGATATTTGATCTTCAGGTCATA
TTTCAGTGAAAACTGTGAATGTGTGTTCCAAAATTATAGGGGATTTCTAGA
GTTCTGATATCTGAGTTTGTGTCATCAGTTATAATTAGAGTTATTGTGTTA
GGCTATTGTAAATCACAGAGGTGACTAAATTTCTTTGTCAATTGTGTTTTT
GACTGTGACTACCCTAGGACATTTTAACATTCATAGACAAATGTTGTCTTG
```

FIG. 8-285

```
TTTTGAAACTCTGCAAAGAATGGATTATAACCCTCAATTGCAGGTTTCTGA
TAACTTTGAAGATTGTGAACAGGAGTTAACTAGGTGAGCTGAACTATTGGA
AAACTAATCTTCTTGACTCTTGCCTCTGTACCTAATTCTTCCTGGATGCAG
GACAAGAACTCAGGCAAAGGTGCTGCAGCATAAAGTCTGGCCAGAGAAACT
GACACTCCAGAGGTTTTGTAACAATATTTTATGTTAAATAATTTATACGTA
TTTCCTATTCTAAGCATTTCAAGTGATTGTAAAAACTCAACTCATGAAAAC
TTATAGCTGAGATGATGTATCCTGTGATTTTTAACTCAACTTTATACCAAT
CTAAGTTGATTAGCATTCTTACAAAGTTTAAGAAGTTAAGATTTGCCATAT
TAAGTATTGTCTTAAGATTTTTAAGAATTGAAAAATTTGGAGCAGTTTTGT
TCATTAGTCAATTGGATACTTTAAAAGTCCAGTATGTCAGATTTAAAAATT
GCAATTTATAAGTTTTCTTCTTAAAGTTCGTCAAATTGCAAAAGCCTTGCC
AAAAATGAATGTTAAAAATTTGGTAGATTATTTGTTCTATGGGTTCTATGG
GAAAAAATTGGTAGATTAATAAATGCCAATAGTAAGCATTGTAAATTGAAT
TTAAAAGTTTAAGGAAGAGCTATTAATTTAATTTTGTCATAATAATGAATT
GAATGTTGTTTTTTAAGTACCATAGTACTTGCTGAATGATCTTTCTGTATG
GAAAAGGACATAAAAATGCACATTGGTAACATCAACTCTATTTCAGCGGCG
GGATTGTGGGGTGAGCTTATCTCCAGGTTTGGGAAGGATGTGTTGTATCAT
CTGCCTCTTGTGTGTGTACTACCTGCCATTGCTGCTTGGCCACCAGCATCC
ATCTTGGTGAGTCCTGTCTCCCTCTAAAAGACTCGAGCTGTGCTGTTCAAT
CCAGTAGCCCCTAGCTACATGTAGCTATTGTAATGAATTAAAATTAAGTAA
AATTAAACATTCTGCTCCTCAGACACCAGTCACATTTCAAGTGCACAATAG
TCACAAGTGGCCAGTAGCTAGTTTTGAACAGTGTGGAAAGATTTCTGTCAT
CACAGAGCATTCTATTATCACGTTGTAAAGCATTCTCTAGCTCTTGCAAAC
TTGTCAGATCCCTTAAAAGTTCTTAAAAATAATTCATCATTCGAATTTTGC
TCAGACTAATTTTTAGGGAAGTCTTTTTCTGGAGGCGTGGACTTGTGATCT
CCATAATTCATCCCTTCTACTATGTTAGTTACCTTGAGCTGCTGTAATAAA
ATACTATAGACTTAGTCGCTAAAAAAAAAATAACTTTCTCACAGTTCTGGA
AGCTCAGAAGTCCAAGATCCAGGTGCTGGCCAATTCAGTTTCTAGGTGAAC
GCTCTCTTCCTGACTTGTTGGTGGCAGCAGCATTCTCACTATGTGCTCATG
TGGTGTCCTTTTTGTGCTTGTAGGGCTTAGGCAGTGGAGAGAAGGAGGAGA
GAAAAGAGTTTCACTGTTTTCTCCTTTTCCCGAGACAGTTTTTGTGTAGCC
CAGGTGGACAGCAATGGCTCACTGCAGCTTCTTCCTGGGGTCAAGCAATCT
TCCCACTTCAGCTTCCAGAGTAGCTGGAGCTTCAGATGTGTACCACCACAC
CCAGTTCATTTTTAAATTTTTAGAAGTTGGGGGTCTCACTATTTTGTCCA
AGCTGGTCTTGAACTCCTGGGCTAAAGCGAGCCTCCTGCTTCAGCCTCTCA
TAGTGTTGGAATTACAGGCATCAGCTGCAGCACCTGGCTCTATTGTCTTTT
TTTTTTTTTTTTTGAGATGGAGTCTCTATCACCCAGGCTAGAGTACAGTG
GTGTGATCTCACTGCAACTTCCACCTCCTGGTTTCAAGGGATTCTCCTGCC
TCAGCCTCCCAGGTAGCTGGGAGTACAAGCGTGCACCACCACACCTGGCCA
ATTTTTGTATTTTTAGTAGACATGGGGTTTTACCATGTTGGCCAGGCTGGT
CTCAAACTCCCAACCTCAGGTGATCCATCCACCTCAGCCTCCCAAAGTGCT
GGGATTACAGGCATGAGCCACTGCACCTGGCCTGTTGTCTCTTTTAATAAG
GGCATGAATTTCATCATGAGAGACACATCCTGATGAGTTTGTCTAAATATA
ATGACTTCCCAAACGCCCCAGCTCCAAGTACCATCACACTGGGGGTTAGGG
TTTCAACATATGAATTTTGCGACGGGGAGTCAATTCAGTCCATAGTACCTA
CTGTATTAGTTTTCTGGGGCTGCAGTAACAAAGTACCTCAAACTCGTTGGC
```

FIG. 8-286

```
TTAACAACAGATATTTATCGTCACACAGTCCTGGAAGCTGGAAGTCTGAAA
TCAAAGTATCATCAGGTTTGATTCCTTCTGAAGGCAATGAGGGATAATCTG
TTCCAGGTTTCTCTCCCAGCTTCTGGTATCCCCAGACTCATTGCTTGACTT
GAATGGTGATTCTCCCTGTGTCTACTCACCACATTTTCTCTCTATAGGTGT
CAGTCTCTGTGTATGACATTTCTCCTTTTTATAAGGACACCCTTTATGTTG
GGTTAGAGCCCACTCTTATCTTAACTGATGAAGTGCAAAGACCCTATTTCC
AAATAAGGCCACATTCACAGGTCCTGATACAGGAGGGGGAAAGTGCTGGGA
AGGGAAGGGCATGGTCCCTTTAAATGATATGGAAGTGGGGAAGGGAAGGGC
GTGGTCCCCGGCTAGGGCTCCACCCCCAGGCCTGTGCCCAGGGACCACGGT
GAGGACAGGCATTTTTGTTTTCCTGCCCAAATGTTGCATTTCCCAAGACCT
CCCCTGGCCTGCCACAAGACACGAATAGCTGGACGTCCAGGGGAGCACACT
GGCAGAAGAGCACACAACAAACGTTTGCCTGGCAAAATGAGGCGGAATTTG
ACTGGGGTGGTTGGAGGAGAGCCTGGGCCACTGAGTGGCTGACTCCAAGGG
AAAACTTTCCCACTCCATCCACTTTTGGCTTTGCCCAACTGCTGAGAGCTA
CCTCCACTTAATAAAACCTTGCACTCTTTCTCTAAGCCCAGGTGTGGTCTG
ATTTATTCCGGTACACCAAGGCAAGAACCTGGGATACAGAAAGCCTTCTTC
TGTCCTTGGGACAAGGTAGACGGTCTAATTGAGTTGGTTAACACCAGCTGC
CTATAAATGGCAAAACTAAAAGAGCACCCTGTAACACACACCCACTGTGGC
TTCAGGAGCTGTAAACATTCAACCCTAGACACTGTGGTGGGGTCATGGGGT
TGGAGACCCACAACCTGCCCGTCTTAATGTTCCCCTAGAGGTTTGAGCAGC
CAGGCACTGAAGAAATTAGCCACACTCCTATCACATGCCATGCGAGCGGGA
CAAGGGAACTTTTCCCATTTCAGTACTGGTGGTTAGGACTTCAACAACTTT
ATTTTTGTGGGAATGCATACTTCAACCCATATTATGAGGGTTCCTAGAATG
TGGACTGCTGAGGCTGAAGCACTACCTAAGTGCCTGAGGCCAGCCTGCAGT
TGGTTTCTGGCTCTCATGAGTTAGCTAACATCTCGGGAGAGAGGAAGACAG
GCCTAGGAAGAGCAGAGCCCACGATTCATTCTTCATTCCACCTCTGCTCTT
CAGAATCTCCTTCAGTCTATGTGATGAGCCATCAGACCTCTTGGTGGGAAA
TGGTGCTGCCGTGCCTAGCCCTTTTCGATTGTGCTACCATGCTGAGATTAC
TGAGGGACCAGGAAGGCCTGGACTCAGACCATATAGGGTGCCACCCTAGTG
GGAATGGAACCTGTCAGTGCTGGGTGAATGTGACCGTCCCATGAGGAGAAG
ACAGATACTCTTGCCAAGCTGAGCATGGAGACCTGATGGGACACTCATTAT
CATGAGGGGATGAAGATCCAGGCTTCCAAAGTTGGTACCACAGGGTGGCTA
TGGCATGAACAGGGGGTTAGGATGAAGGACCCAGAATCTAACATGCTGGAG
AGGTAGGGAAAGGAGTCAGAAATTCAGTCTTGTTGAACCCTAAATATTGCA
TCTCTCTCTCTTTATTTTTTTTTCTGGAGATGGGGGTCTGGCTCTATC
ATCCAGGCTGGGGTGTAGTGGCATGATCTCTGCTCACTGCAGTCTCCGCCT
TCTGGGTTCAAGAGATCCTCCCACCTCAGCTTCCTGAGTAGCTGGGACTAC
AGGTGCGCGCCACCACTCCCAGCTCATTTTTGTACGTTTTTGTAGAGACAC
GGTCTCACCATGTTGTCCAGACTGGTCTCGATCTCCTGAGCTTAAGCGATC
TGTCGCCTCGGCCTCCCAAGAAGGATTGGGATTACAGGGCCTGAGCCACTG
TGACCAGCCAACATTGCATCTAATTTTAGGGTATTCATCTGACTTTCCTGA
ACACTGCTTCTTGGGTGCTCATTTTAGCAGGCATTTGGCCATAGGTAGATT
TAAAGTTTTGGTGGGTTTTGTTGTTGTTGTTGAGACAAAGTGTCACTCTGT
TGCCCAGGCTGGAGTGCAGTGGCAAGATCTCAGCTAACTTCAACCTCCATC
ACTGTGCTTCAAGTGAGTCTCCTGCCTCAGGCTCCCGAGTAGCTGGGATGA
CAGGTGTGTGCCACCATGCCCTGCTAATTTTTTATATTTTTAGTAGAGATG
```

FIG. 8-287

```
GGGTTTCGCCATGTTGGCCAGGCTGGTCTGGAACTTCTGACCTCAGATGAT
CTGCCCGCCTCAGCCTCCCAAAGTGCTGGGATTACAGGTGTGAGCCACAAC
CCCTGGCCAACGTTTTCTGAAAAAGCTATTCTAATCAGGTAGGAAAGATGG
GAAGCGGGGTGGCGGGGTGTACTTTTTTCTGCATATTCAGTTGCAGGGTCC
CAGACCAGGGAACAATCTTCAATCTCTTACCTTCAATCTCCCTTCATGGAA
GTCAGTGCTCAGCCTGGCCATTTACTGTGTGCAGTAGGTGTGATGTAGAAA
GCCTCTAAACCTCCATGCCTACCTGCCAGGAACAATATACACAAAGGTGTG
TGTGTGTGTGTGTGTGTGTATCTTACGGATTCTTCCACGTAACTATG
TGGACATCTAATCCATTGCTTCCAACTCTATATTGTGCAGTGACTTCATTT
TACCTCCACCTCTCTCAGTGAAGGATATCAGTCAGCCCACACTTTCCTGTC
ACCTTTATGGGATATGTTTGAGATGATATTTGGAAAATATTCCCAGGGAGT
GGGCACTCCCATCAGCAGTGTATGAGGATTCCTGAGTCTCCATATCCACAC
CAATACTGAGCATTATTCAGCTCTCTAATTTGTTAATGCTCTCTTTTAAAT
GCAAAAGGACACATCACTTTACCTTTCTTTCATTACCAAGTGCTTTGGATT
TTCCTGTATCTAAATTTCTTGTTCATTTATTTCATATATATATATATATAT
ATATATATATATATATATATAATTTTTTTTTTTTGAGACAGAGTC
TCACACTGTCACCCAGGCTGGAGTGCAATGGTGTGATCTCAGCTCACTGCA
ACCTCTGCCTCCTGAGTTTAAGTGATTCTCCTGCCTCAGCCTCCCAAGTAG
CTGGGATTATAGGCACCCACCACCACGCCCGGCTAATTTTTTGTATTTTTT
GTAGAGATGGGGTTTCACAATGTTGGCCAGCCTGGTCTCAAACTCCTGATC
GGCCCGCCCTGGCCTCCCAAAGCGCTGGGATTACTGGCATGAGCCACCGCG
CCCGGCCTCATACATTTTTATGTGGAGTTTCTGTTTTGTTCTTCTTGGCC
TTGTGCATTCTAATTACTCATCCTTTCGTCTGATTCAGACATTTAATTCTC
TACCATCCTTACAGCAGTGTCTTAACTTTATCCATGGGATCCTTCATTGAA
CCGGAATTCTTAATTTTGACACAAACAAATTTATCAATTTCTTTTTTGTGT
GTGTTTTTTTTTCTGTGTGTGGTTTTTGTTTTTCACATTTCTGAGTATGA
CCTAGATTTATCCTTTGATAACTTCTTCTCTCTTCCCCATTTTCCTCCACT
GGAGGTCAGCTATATGTGTGTGAGAGGGTTAGGTATATGTGGATATATAGA
GAAAGTTTAGGTATACATATGTGGAGAGGTCAGATAAATATGTATATATGG
GAGAGATATTGGGTATATATTTTGGGGAGGGGAGGTCAGGTATATGTGGAC
ATATGGGGAGGGGAGACCACAGCTCTCCTGGAGTCACCCTCTTCCTCTTCC
CTTCTGGGCAGGTAACGGTGGGGAGTGAGAGGGTGTTCCTCCCTTCTTATT
ATTAGCCCCTGGGTACTTTAGGGTCTCTAGTGGTTATTTTTCACAGAATTT
TAACTGATAACTAATGAACAAATGTTTTCCCCACAGAAATATCTTTACGCC
TTTTACAATCATTTTTATTTCTATGCCATAACTTTATTAATATTTGCCAA
TTTACTTGGGGTAGGACTTTGAAAATTTTGTTTAAATTAAGGGAGGAGACC
ACCCCTCATATTGTCTTATGCCCAATTTCTGCCTCCAAAGAAAGAAAAAGT
AAAAATTAAAAGGGAGAAATGAAATCCACAGGCAAACAGCCCGGCACCGCA
CCCTGGGTCTGGTTAAAGATCGACCTTTGACCTAACAGGTTATGTTATCTA
TAGATTCCAGACATTGTATGGAAAAGCATTGTGAAAATCCCTGTGCTGTTC
TGTTCTGTTCTGATTACTGATGCATGCAGCCCCAGTCACGTACCCGCTGCT
TGCTCAATCAATCACGACCCTCTCATGCAGACCCCCTTAGAGTTGTAAGCC
CTTAAAAGGGACAGGAATTGCTCACTCAGGGAGCTGGTTTTTGGAGACAGA
GGTGATTAACGGACGGTCAAGGCAGCCCCTTAGGCGACTTAGGCCTGCCCT
GTGGAGCATCCCTACGGGGAACTCCAGCCAGTTTGAGCGACACAGATCTGG
AGAGCGCTCCCAGGTAGGCAATTGCCCCGGTGGAACGCCTCACCAGAGCAG
```

FIG. 8-288

```
CACGTGGCAGGCCCTCGTGGAGGATCAACGCAGTGGCTGAACACCGGGAAG
GAACTGGCACTTTGTTGTCAGGGCATATTCCAAAAGCATTAAGGCCTTCCT
ATCAAAAATCCTTAACCCAGTAACCCGCGGATGGCCCAAATGCATTCAATC
TGTAGCGGCAACTGCTTTGCTAACAGAAGAAAGTAAAAAAATAACTTTTAC
AGGAAACCTCATTGTGAGCACACCTCACCGGTTCAGAAGTATCCTAAGGAA
AAAAGAAAAAGAAGATGATTTAACATTAACCACTGAAAATTCTCTTAACC
CGGCAGGTTTCCTAACAGGGGATCTAAATCTTAATTACCATACAAAGCTCT
GACCAGACCTAGGGGATTCCCTTCAGGACAGGAGGATAGATGGTTCTTCCC
AGGTAATTAAAAAAAAAAAAAGCCATCTATACCAATTCTAAGTTAATTTG
GACTAAATAAGGTCTTATTAATAGCAAAGGATAATTGAAATCCCAAACTTA
CAAGGTTTTCAACAAAAGTAAAGTTTGCTAAAAGTTAACAGTGTAACATGT
ATTATAGTAACTTCTAATCTTGTGGCCTTAGACAGTCTAGTCCACAGACAT
AAAAGAAGTTCGCTTTGGAAAAGAATGGTTATCATCCTCGGAAAAAAAAAA
AAGGAAATAAAGAGGAGGCAGAATTTATATAAAAAAGAATGTTGTATGGAA
AATCCTTGTCCTGAGATAAATTAACTAGTTGTTTAAAGAAAGGGATGTTTG
CAATAAGTCAGAAAGTTGAGGCATGTCGAAGAATTGTCTGTGAAAGTCATG
AAAAAAATGTGTGTTAGAAAAATAAATTTATGTAAGAAATGTTGTATAATT
TAAAAGTAATTAGGCCTCCTTCTAAATGTAAAACTATTGAATAAACAGTTT
ATGTGCAAGGTATGTAAGGAAAGTAAAATATACCTTTGGTAAAAGGATTAT
GAGGATGCATAAGAATGTGGATTTTTACCTACATTAAAAGGTTACAAAAAT
TGTTTTGAAGGTTTAAGCAAGTTTTGAAACCTTAATTGTAAAGAAAATTCT
GTGTCTAAACATATTGGCTAAAGTTAAGGGGTATCATACAGTTTTTCTGTG
AACTGAACATTAAAATAAAAACACAACGGGTTTTTCTTAAAGCACTAACCT
GTTCTTTAACAAAAATTATAAAAGGTTAAAGAAAAGTCTATAAAAATCTTA
CCTTATGGTCAGACATTAAAAATCAAATAAATATGTCTACAGAGTTTTATT
AAAACTAAGTTTAACATTAATAACACACCAATATAAAGGTGAAATCTAGCT
TATCTGGTATAAACATACAAGAAGCGTTGTCAAATATAAAATGGCATTTGA
CTTTCTTTGGTCTAAAAACTAATAAAAATAGGTGCTAAAGGAAATTTCTCA
GTAAGAAGGCACCAAGGACTATAAAGTCCACTGCTGATGTCCCCACATTTA
AAACAAAAGGTCAACTTCTTAAAAGTTATATACTTGGTTTATCTTCCACTT
TCCTTTCCCTCAAAACTAAAAGTCTTTTAGCACATGTACCACCCCTAGAAT
TTTCTGTAAACCAGCACCAGCCTGAAGATCATGTTCTCATCAAAGGGTGGA
AAGAAGGAAAACTTGAGCCAGCCTAGGAAGGACCCTACCTTGTGCTGCTAA
CCACCGAGACTGTTGTTCATACGGTGAAAAAGGGATGGACTCATCACACCC
GAGTCAAGAAAGTGCCACCCCCTCCAGAGTCATGGGCCATAGTCCCAGGGG
AAAACCCTACCAAACTAAAGCTAAGAAAAATTTAACTCCTTCATCTATTCT
ATTACTCTTTCTTCTTCCCTCACTCTATTTCTGACCATCTAGTTATTAACA
TAACCAAGTCAATTTTGCCTCAAACTATTGAATTTAATGCTTGCCTTGTTA
TACCCTGTGGGACTTGCCAAGTCGAAGACATCTCTGTACTTCAGAAAAGT
ACCTCTGTCCCTCCTGACTCTCCTCAGACTGAGCCTTAGTAAACTGAGACC
ATTTATTCCAGAGAGATTTCAATAAAGACCCCAGTGTCAACGAGGAGTCTT
GCCCCCCGATGTAGAGCTTTTATGCCATAGTTGGTCGAATGTTGTGTGGAC
CACTAAAGAGCAAGGATGGACTGCCCCAACCGGTTTTTGTAATTTCCTAAA
ATCATACATTCATTTTACTAGAGGGTCATAGAAGTTAAAGACTTAAAACAA
ACTTTGATAATTAAGCAGGATACCAAGATGCAAATGCCCAGTTGGAATGGA
TCAAATATTCTGTCCACACATTAAACAAAACCAATTGTTATGCTTGTGCAC
```

FIG. 8-289

```
ATGGCAGGCCAGAGGGCCAGATTATCCCCTTTCCACTAAGGTGGTCCTCCT
GTTGACCAGGCATGGGCTGCATGGTAACTGTTTTCCAGGATTCTACAGCCT
GGAGTAATAAGTCGTGCCAAGCTCTCTCTGCTATATCCCAAAGTCCAGCAC
CCTGCAGGTCAACCCCTGAGGGCCATCCAGCTTCCATCTCCCAAAACTAAG
TTCACTTCTTGTCTCTCATGACAGGGAGGAAACTTAGCATTCCTTGGAGAC
CTGAAGGGATGCAGTGAGCTTAAGAATTTTCAGGAGCTTCTCAATCAGTCA
GCCTTTGTTCATCCCCAAGCGGATGTGTGGTGGTATTGTGGTGGACCTTTA
CTGGGCACTCTGCCAAATAACTGGAGCGGCACTTGTACTTTAGTCCAATTG
GCTATCCCTTTCACCCTAGCATTTCATCAACCAGAGGGAGGAAAAATAAGA
CATCGTAAAGCAAGAGAAGACCCTTATGTGTCTTTCAACTCTCACATCTAT
TTAGATGCAATTGGAGTCCCACAGGGAATAGCAGATCAATTTAAATCCCAA
AATCAAATAGCTGCAGGATTTGAGTCAATATTTTGGTGGGTGACAGTTAAT
AAAAATGTAGATTGGATAAACTACATCTATTACAACCAACAGCAATGAGTT
TTTCATGAGTTAAAAGAAAAACTCATGTCGGCCCCAGCCCTGGGGCTACCT
GACCTGACAAAACCCTTTACACTCTATGTGTCAGAAAGAGAAAAAATGGCG
GTTGGAGTTTTGACCCAGACTGTGGGGCCCTGGCCGAGGCTGGGCCTCCAA
ACAACTAGATGGAGTTTCTAAGGGTTGGCCTCCATGCTTAAGAGCCTTGGC
AGCAACAGCCCTGCTAGCACAAGAGGCAGATAAGCTAACTCTTGGACAAAA
CCTAAACTTAAAGGCCCTCCATGCTGTGGTGACTTTAATAAATACATCATT
GGCTAACAAATGCTAGATTAACCAAGTACCAAAGTTTGCTATGTGAAAATC
CCTGCATAACCATTGAAATTTGCAACACCCTAAAACCTGCCACCTTGCTCC
TGGTATCAGAAAGCCCAGTTGAAAGTGACTGAGTAGAGGTATTGGACTCAG
TTAATTCTAGTGGGCCCAACTTCCAAGACCATCCTTGAACATCAGTAGACT
GTGAGCTGTACGTGGCAGCTTCGCCAACGCCTGCAAAGTGACTGAAGAAGA
CAACAAGCCCTGCTCCAGTCACACCCGGAAGCTGACTGGTCCATGCATGGC
CGAAACATGAGAAAACTCATCAAGGGACTCATTTTCCTTAAAATTTGGACT
TGCACAGTAAAGACTTCAACTAACCTTCCTCAGACTGAGGGCTGTTCCCAG
TGTATACATCAAGTCACTGAGGTAGGACAAAAAGTTGCTACAGTCTTATTA
TTTTATGGTTATTATAAGTGTACAAAGACTCTAAAAATAACTTGTTTGTAT
AATGCTATTCTATACAAGGTAGGTAGCCCAAGAAATGACCAACCTGATGTG
TGTTATGACCCATCTGAGCCTCCCACGACCACAGTTTTTGAAATAAGATTG
AGGACTGAGGACTGGTGGGGGTTCATAAACGATACGAGTAAAGTGTTAGCC
AAAACAGAAGAAAAGGAATGCCCAAACAAGTCACCTTGAAATTTGATGCC
TGTGCTGTCATTAATAGTAATAAGTTAGAAATAGGATGTGGTTCTGTTCAT
TAGGAAAGAGGCTATATGGCAGAAAATAAGTACGCTTGTCATGAATTAAGA
CTGCGTGGAAATAAATGTAGATACTGGTCTTGTGTCATTTAGGCAACTTGG
TTAAAAAATAAAAAGAATCCTGTCCACCTTCAGAAAGGGAAAAGTGGCCCT
TCCTGTACCAGTGGTCAGTGTAACCCCTTAGAACTAGTAATAACCAACCCC
CTTGATTCTCACTGGAAAAAGGGGATCGTGTAACCTTAGAAATAGTTGGG
GCTGGACTGGATCCTTGAGTAAATATGGTGGTTTGAGGAGAAGTTTATAAA
TGCTCCCCTGAGCCAGTATTTCAAACCTTCTTATGATGAACTGAATGTGCC
AGTACTAGAAATTCCAGGAAAAACAAGAAATTTGTTTTTGCAATTAGCTGA
GCATGTAGCCCAGTCTCTCAATGTCACTTCATGTTATGTATGTATGTGGAG
GAACTGTAATGGGAGATCAATGGCCATGGGAAGCACGAGAATTAGTACCTA
CAGACCCAGTTCCTGATAAATTCCCAGCTCAAAAGACTCACCCTGATAACT
TCTGGGTCCTAAAAGCCTCAATCATTAGACAATACTGTATAGCAAAAGTGG
```

FIG. 8-290

```
GGAAGGACTTCACCCTTCCTGTGGGAAGACTCAGCTGCCTTGGGCAAAAAC
TGTATAATAGTACTATAAAAACAGCCACCTAGTGGAGTTCAAACCACACTA
AGAAAAATCTATTTAGTAAATTCCCAAAGTTGCAAACTGTGTGGACCCACC
CAGAGTCCCACCGGGACTGGACAGCCCCCACTGGATTATACTGGATATGTG
GGCATACAGCTTATGCCAAATTACCTGACCAGTGGGCAGGTAGTTGTGTTA
TTGACACTACTAAACCATCTTTCTTCCTACTGCCCATAAAGACAGGCAAAC
TCCTGGGCTTCCCCTGTATATGCTTCCCGCAAAAAAAAAAAAAAAAAAAAA
AAAAAAAAAAAAAAAAGCATAGCTATAGAAAATTGGAAAAATAATGAATGG
CCCCCTGAGAGAATCATACAATATTATGGGCCTGCTACTTGGGCACAAGAC
GGCTTGTGGGGATATGGGACCCCCATTTACATGCTCAACTGAATCATACGG
TTACAAGCTGTCTTAGAAATAATTACTAATAAGACCAGCAGAGCCCTGACT
ACTGTGGCCTGGCAAGAAACTCAGATGCAAAATGCTATCTATCCAAAATGG
ATTGGCTCTCGACTACTTGCTAGCAACTGAAGGAGGGGTCTGTAGGAAATT
TAACCTTACTAATTGCTGTCTACACATAGATGATTAAGGGCAAGTAGTTGA
AGACATAGTTAGAAATATGACAAAAGTGGCACATGTGCCCATGTAGGTGTG
GTATGGATTTGTTTCTGGGGCCATGTTTGAAAAATGGTTCCGAGTGCTAAG
AAGATTTAAAACTCTTATAATAGGAGTTATAATATTAATAGAAACCTGCTT
ACTGCTTCCTTGTTTGCTACCTGTACTTCTCCAAATGATAAAAAGCTTCAT
CACTACCTTAGCTCACCAAAATGCTTCAGCACAAGTGTACTATATGAATCA
TTATCAATCTGTCTTTCAAGAAGACATAGGTAGTGAGAATAAAAGTGAGAA
CTCCCACTAATGAGTGAGATTCTCAAAGGGGGTGAATAAGTGAGGCGACCA
CCCCTCATATTGTCTTATGCCCAATTTCTGCCTCCAAAGAAAGAAAAAGTA
AAAGCTAAAAGGCAGAAATGAAATCCACAGGCAGACAGCCTGGTGTTGCAC
CCTGGGTCTGGTTAAAGATTGACCCCCGACCTAACCGGTTATGTTATCTAT
AGATTCCAGACATTGTGTGGAAAAACACTGTGAAAATCCCTGTTCTGTTCT
GATTACTGGTGCATGCAGCTGCCAGTCACATACCCCCACTTGCTCAGTCGA
TCATGACCCTCTCACACAGACCCCCTTAGAGTTGCAAGCCCTTAAAAGGGA
CAGGAATTGCTCACTCAGGGAGCTCGGTTTTTGGAGATGTGAGTCTTGCCA
AAGCTCCCAGCTGAATAAAGCCCTTCCTTCTTTAACTCAGTGTCTGAGGGG
TTTTGTCTGTAGCTTGTCCTGCTACAAAAATAAGTGTTAAACATGAGTTTT
ATATTACCTCATAGGTGGAAGAAGACAGGCCAAAAAAGCTGTTTTAACAAC
AACAAAATGCACAAATATTTATACTAACAAGACAGATATCCATTGCAGTAT
GACACGAGAAACAAATAAATGAGACAAGCAGTCAATTCAGACATTTTAGGA
AGTGATTTTTACAGAACATAGTGACAATTGCTGAGATCTGGTAGCCTTGCA
AGATTCCTTTGTTATAATAAAAATAACATTGGCAAAGACCATTTTATGATG
CAGACTTCTGCTTTTTTAAAGTTTGGGGGGAAGGGGAAACATTTTTATTCT
ATAATGCTGAAATTTCATTTTTCTTTTCTCTTTTTTAAGACCAAGTCTTGC
TCTCTCACCAAGGCTAGAGTGCAGTGGCGTGATCTCAGTTCACTGCAACCT
CCACCTCCCGGGTTCAAGCAATTCTCCTGCCTCAGCCTCCTGAGTAGCTGG
GACTACAGGCACCATGCCCGGCTAGGATAACATTTTTTGTTTTTAGTAGAG
ATGGGGTTTCACCATGTTGGCCAGAGTAGTCTAGAACTCCTGACCTCAAGT
GATCTGCCCGCCTCATCCTCCCGAAGTGCTGAGATTACAGGTGTGAGGTAC
AGCATCTGGCCTCATGCTGAGATTTCTTTCATTACCAGTTCAAACACCTTT
CACTTTTCAAGGCACAAGGAGAGGAATTCCATGTGTTGACACTGGGAGGAA
GGGTACAGACCTACTTAAAAGATTCAAAACTTCTATGACAGTAAAAGAAAT
GTATATCAAGTTCCTTAGGGCTGCCGTAACAAAGTACTATCAACTGGGTGG
```

FIG. 8-291

```
CTTAGAACAAAAGAAATTTATTCTCTCACAGTTACGTAGGCCAGTTGAGAT
CAAGGTATTATCAGGGCCAAGATCCCTCTGTAGCCTCTGGGGAAGGATTCT
TTCTTGCCTGTTTCCACTTCTAGCAGCTTCCTGTGTTTGGTTTGTGGCAGC
ATAACTCCAATCTCTGCCTCCATCTCTACCTGGCCATCATCCCTCTGTGTC
TGTGAGGACCCCAGTCATTGGTTGGAGGACTCACCCTATTCCACTATAATC
TCTTCTTAACCAGTGAACTCACCGTATTCCAGATAAGGTCAGGTTCACAGC
TACTGAGGGTTAGGACAGAGTATCTTTTGGGGAGATGCAATTCATCCCATA
AGTGGGTGGAAAAGGATGATTAACAAGTGGTATGTGGGGATGTATTGTTTT
GCATCTACGTAGCTCTCACCCCATTTCTTTCCACAACACACATTTGTCACT
CTATTCTTTATTAGGTTTACAGAGAAAAGTAGATCTTCAACCACTTTCCTG
GGATGTGGATACAGCTCTTTTTTTGGAGACAGGGTCTCATTCTGTCACCTA
GACTGGTGTGCAGTAGCACTATCATGGCTGACTACAGCCTCAATGTCCCAG
GCTTAAGTGATCTTCCCAACCTCCTGAGTGGCTGGGACCACAAGTGTGTGC
CACCACACCTGACTAATTTTATTTTTTAATTGTTTTGTGAAGACAGCATCT
CCCTATGTTTCCCAGGCTGGTCTTGAATTCCTGGGCTCAAGCCATCCTCCT
GCCTCGGCCTCCCAAAGTGCTGGGATTACAGGCAAGAGCCTCCATGCCTGG
CCTTCAACTCTTGACCTTATGAACACAGCCCTATACCAGTTCCCTTCATGC
ATGTGCCTATAAGCTAAACCCTTCCCAAGTGTACATGAAAATCTGAAACCC
CAACAAATATGGCCTAATTCTAAATCTGACTTTCCCAGGAGTAATTTTTGT
CATTTCCAGCTTACCAGCCTTTGTGAGTGTTGAATTTCAGCATTTCTGTTT
GCTTGCAGCAGAAGGTGGAGCCAGGATAGGGTGGCTCAAGATTAGAGTTTC
TTCCTTAACAGTTCAGTCAACTTTTTAATCTTGGATTTATAGCTTCCTACC
TGCTCTCTTAAAGGTGAAATGATCTATTCACCTTCAGACCATTTGCCCTCG
GGGTCTCACTGAGCAATCTATGGCTTAAGTCTTCTAAGTCTCTTAATGGCC
AAATACAATGGACAATTTTCAGGTATATCTGACACCATTTCTCTGCAGCCT
TTGGCACCTATAACCACTCCATGGCTTCCACAATGTGATTGGTCATTTCTT
TTTTGTTTATATGACAAGTTTTTATTCTTCTTCTGCCTGTTAAATGCGCCT
GACCCCCAGTGTTCTGATTTTCACTATTTTTCTTAAAAAAAAAAGTTTAAA
TGAAAAAAGTTTCTTATGAAAATATTAAAACATATACAAAAATAGAATAGA
CATTGATAATAGATCCTAAAATTCCTAGGGAAATTCAGCAGACTGAGAATA
GCTAATATAGTCTTCCAAAAAAAGATCAAATTTGAAGTTGAGAAACTTCTT
GAATTCAATTTACTAAAAAGCTATAGTAATCAAGACAGTGTAGTCCTGACA
TAAAGATAGGATTATAGTCTGGGTGTGGTGGCTCATGCCTGTAATCCCAGC
ACTTTGGGAGGCTGAGGTGGGCAGATCACCTGAGGTCAGGAGTTCCAGACC
AGCCTGACCAACATGGTGAAACCCCGTCTCTACTAAAAATACAAAAATTAA
CCAGGCATGGTGGCAGGTACCTGTAATCCCAGCTGCTTGGGAGGCTGAGGC
AGGAGAATTGCTTGAACCTGGGAGGAGGAGCCAGTGGCCGGGATTGGGCCA
CTGCACTCCAACCTGGGCAATAGAGTGAGGCTCTGTCAAAAAAAAAAAAAG
ATAGGATTATAGATTATAGCATAATGGGATAAAATTGAGACTCCAGAAATA
AACTCTCACATTTATGGTAGATTGATTTTTGATAAGGGTGCCAAAACACTT
CAATGAAAAAGAGTCTTCTCAACAAGTGATGGTGGAACAACTGAATAACC
ACATTTTTGTTCTATCTGGGGCCCTGATTCAAAAACCCAGGCAAAGATGGA
GAGAAATCAGAACTCTCATACACTGCTGATAGGAGGATAAAATGCTTACTT
TGGAAAAGAATGTGGCAATTCCTCAAAAGGTTAAACAGTGTTACCATATGA
CCCAGCAAACCCACTTCTAGATATATAACCAAAAGAAATCAAAACATAAGT
CTACAAAAAAACTTGTACATAAATGTTTATAACAGCACTATTCCCAATAGC
```

FIG. 8-292

CATAAAGTAGAAACAAACCAATGTCCATCGGCTGATGAATGAATAAATAAA
ATATGTTGTGGTATGTCCTTATAATAGATATTATTGGTCCATGAAAAACAT
ACATAAAAACATTATGCTAAATGAAAGAAGCCAGTCACGGCAAAGCAATAT
ATTATATGCCTCTATGTATACTAAATGTTCCAAATAGAAAGAAAGTAGATT
AAAGATTGTCTAGGGCTGGGAGGGGAGGAGGAGGAGAATGGAGGAATCTGG
GAGGCGATGAATTAAGGGTACTGAATTAGGGGAACATGGTTTCTTTTTGGG
GAGATAGAAATGTAAAATTTTGGTAATGGTTGCACATCTCTGTAAATATAC
TAAAATCCATTAATTTTTGCATTTTATTTTATTTATTTTATTTTTGAGACG
GAGTTTCGCTCTTGTTGCCCAGGCTGGAGTGCAATGGCATGATCTCGGCTC
ACCACAACCTCCGCCTCCCAGGTTCAAGCGATTCTCCTGTCTCAGCTTCCC
GAGTAGCTGGAATTACAGGTGCATGCCACCACACCCAGCTAATTTTTTTTT
TTTGAGATGAAGTCTTGCTCTTGTCTCCCATGCTGGAGTGTGATGGCACGA
TCTTAGCTCACTGCAACCTACGCCTCCCGGGTTCAAGCGATTCTCCTGCCT
CAGCCTCTAATGTAGCTGGGATTACAGTTGCCTGCTATCACGCCCGGCTAA
TTTTTGTATTTTTAGTAAAGACGGGGTTTCACCATGTTGGCCAGGCTGGTC
TCGAACCCCTGATCTCAGGTGATCTGCCTTCCTCGGCCGCCCAAAGTGCTG
GGATTACAAGCGTGAGCCACTGAGCCGGGCCAATTTTTGCATTTTACATAG
ATGAATTATATGGTATGCTAATTATATCTTACCAAAAATTGAAAAAAAGGA
ATAGTACTATCAGCCCCAATGTGCCCATCATCAATATTCTACATGTTTCCA
ATGTTATTGTATCTGTTTGCCTACAGTCGAGGCCCTGATATCCTGTTTGAT
TTTCTTGAATTGCCAAAATTTGCATACATGCTTACAAAAATAATGCCTGTT
GAATTTGCTAGATATGTAAAGGTTTGGAGCAAATCAGGTGTATTAAATTTA
TTAATATTGTTTGAAATGTCTAAGGCAATAATTCCCAAACTTCGTTGAGGG
AGAAGGAAAGCTTTTAAAATCCCATTGCCCAGGTGGCATCCCATACTGTTA
CTGGGAATTATGCATTGGGATGGATCCTTTAACCGAGGAGATTATTATAGC
CGGAGCTCTGAACCAGCAATCTCAGTTCTTGTGATAGTGAGCAAAGAACTA
CAAACTAACACCAAAATGCAAGCTTAAAGCAAAGTTTATTGAAGCACAATA
ATACACTCTGAGGGACAGCGGGCTTATTTCTGCGAAGTGAACTCAGCACTT
CTTTACAGAGCTCAAGGTGCTTTTATGGGGTTTGTGGGGAGGAGTTGAGGT
TTGGGCTGTATCTGAGTGACAGGATGATGTTATTTGATTGAAGTGTATAGC
TATACAATCTAAAATTAAACTGTGCATGGTCTTACCTATAATTTGTTAAGA
AAAGCCTCCCAGGGATGGGGGGGCAAAACTGTATGTAAATTCTATTATAAT
GATGGCATGATGAACTTGGGGTGAACTTGAAGACAGGCTTTTGTGTTGTTG
GGCATGTGCCACCTTAGGGAATTTCCACCTGTACCCTCCTTTCTCTTTCTC
CAGGATATTTTGGCCACAGACTTTATCATAAACTCCATCCCTTAGGGTGGC
ATTAGGGTAGTCTTGGGCCTGAATTTAGGTGGGCCAGTGGCTGTCTTAGTG
ACAGCCTTTCCGCTCTCTTCTGTCATCCCCTCCCAACTGCTAATGTCTAAC
TACCTAACAATTACCCATTAAATCAGTGTGTCTGGGGTTAGGAGCAGGCCT
CAATATGTTTAATCATTCTCCAGATAATCCCAATACTGTAAAGTTTGTGAA
ACACTTGTCAGATAATTCAATTATGAAGGCTGTGGAAGGTGTTTCAGTAGG
ATCTAATTGGTTAATGTTATGACTTAATTAATTTGAATCAAAAAACAAAAT
GAAAAAGCTTTATATTTCTAAGTCAAATAAGACATAAGTTGGTCTAAGGTT
GAGATAAAATTTTTAAATGTATGATTGAATTTTGAAAATCATAAATATTTA
AATATCTAAAGTTCAGATCAGAACATTGCGAAGCTACTTTCCCCAATCAAC
AACACCCCTTCAGGATTTAAAAACCAAGGGGGACACTGGATCACCTAGTGT
TTCACAAGCAGGTACCTTCTGCTGTAGGAGAGAGAGAACTAAAGTTCTGAA

FIG. 8-293
```
AGACCTGTTGCTTTTCACCAGGAAGTTTTACTGGGCATCTCCTGAGCCTAG
GCAATAGCTGTAGGGTGACTTCTGGAGCCATCCCCGTTTCCCCGCCCCCCA
AAAGAAGCGGAGATTTAACGGGGACGTGCGGCCAGAGCTGGGGAAATGGGC
CCGCGAGCCAGGCCGGCGCTTCTCCTCCTGATGCTTTTGCAGACCGCGGTC
CTGCAGGGGCGCTTGCTGCGTGAGTCCGAGGGCTGCGGGCGAACTAGGGGC
GCGGCGGGGGTGGAAAAATCGAAACTAGCTTTTCTTTGCGCTTGGGAGTT
TGCTAACTTTGGAGGACCTGCTCAACCCTATCCGCAAGCCCTCTCCCTAC
TTTCTGCGTCCAGACCCCGTGAGGGAGTGCCTACCACTGAACTGCAGATAG
GGGTCCCTCGCCCCAGGACCTGCCCCCTCCCCCGGCTGTCCCGGCTCTGCG
GAGTGACTTTTGGAACCGCCCACTCCCTTCCCCCAACTAGAATGCTTTTAA
ATAAATCTCGTAGTTCCTCACTTGAGCTGAGCTAAGCCTGGGGCTCCTTGA
ACCTGGAACTCGGGTTTATTTCCAATGTCAGCTGTGCAGTTTTTTCCCCAG
TCATCTCCAAACAGGAAGTTCTTCCCTGAGTGCTTGCCGAGAAGGCTGAGC
AAACCCACAGCAGGATCCGCACGGGGTTTCCACCTCAGAACGAATGCGTTG
GGCGGTGGGGGCGCGAAAGAGTGGCGTTGGGGATCTGAATTCTTCACCATT
CCACCCACTTTTGGTGAGACCTGGGGTGGAGGTCTCTAGGGTGGGAGGCTC
CTGAGAGAGGCCTACCTCGGGCCTTTCCCCACTCTTGGCAATTGTTCTTTT
GCCTGGAAAATTAAGTATATGTTAGTTTTGAACGTTTGAACTGAACAATTC
TCTTTTCGGCTAGGCTTTATTGATTTGCAATGTGCTGTGTAATTAAGAGGC
CTCTCTACAAAGTACTGATAATGAACATGTAAGCAATGCACTCACTTCTAA
GTTACATTCATATCTGATCTTATTTGATTTTCACTAGGCATAGGGAGGTAG
GAGCTAATAATACGTTTATTTTACTAGAAGTTAACTGGAATTCAGATTATA
TAACTCTTTTCAGGTTACAAAGAACATAAATAATCTGGTTTTCTGATGTTA
TTTCAAGTACTACAGCTGCTTCTAATCTTAGTTGACAGTGATTTTGCCCTG
TAGTGTAGCACAGTGTTCTGTGGGTCACACGCCGGCCTCAGCACAGCACTT
TGAGTTTTGGTACTACGTGTATCCACATTTTACACATGACAAGAATGAGGC
ATGGCACGGCCTGCTTCCTGGCAAATTTATTCAATGGTACACTGGGCTTTG
GTGGCAGAGCTCATGTCTCCACTTCATAGCTATGATTCTTAAACATCACAC
TGCATTAGAGGTTGAATAATAAAATTTCATGTTGAGCAGAAATATTCATTG
TTTACAAGTGTAAATGAGTCCCAGCCATGTGTTGCACTGTTCAAGCCCCAA
GGGAGAGAGCAGGGAAACAAGTCTTTACCCTTTGATATTTTGCATTCTAGT
GGGAGAGATGACAATAAGCAAATGAGCAGAAAGATATACAACATCAGGAAA
TCATGGGTGTTGTGAGAAGCAGAGAAGTCAGGGCAAGTCACTCTGGGGCTG
ACACTTGAGCAGAGACATGAAGGAAATAAGAATGATATTGACTGGGAGCAG
TATTTCCCAGGCAAACTGAGTGGGCCTGGCAAGTTGGATTAAAAAGCGGGT
TTTCTCAGCACTACTCATGTGTGTGTGTGGGGGGGGGGGCGGCGTGGG
GGTGGGAAGGGGACTACCATCTGCATGTAGGATGTCTAGCAGTATCCTGT
CCTCCCTACTCACTAGGTGCTAGGAGCACTCCCCAGTCTTGACAACCAAA
AATGTCTCTAAACTTTGCCACATGTCACCTAGTAGACAAACTCCTGGTTAA
GAAGCTCGGGTTGAAAAAAATAAACAAGTAGTGCTGGGGAGTAGAGGCCAA
GAAGTAGGTAATGGGCTCAGAAGAGGAGCCACAAACAAGGTTGTGCAGGCG
CCTGTAGGCTGTGGTGTGAATTCTAGCCAAGGAGTAACAGTGATCTGTCAC
AGGCTTTTAAAAGATTGCTCTGGCTGCTATGTGGAAAGCAGAATGAAGGGA
GCAACAGTAAAAGCAGGGAGCCCAGCCAGGAAGCTGTTACACAGTCCAGGC
AAGAGGTAGTGGAGTGGGCTGGGTGGGAACAGAAAAGGGAGTGACAAACCA
TTGTCTCCTGAATATATTCTGAAGGAAGTTGCTGAAGGATTCTATGTTGTG
```

FIG. 8-294

```
TGAGAGAAAGAGAAGAATTGGCTGGGTGTAGTAGCTCATGCCAAGGAGGAG
GCCAAGGAGAGCAGATTCCTGAGCTCAGGAGTTCAAGACCAGCCTGGGCAA
CACAGCAAAACCCCTTCTCTACAAAAAATACAAAAATTAGCTGGGTGTGGT
GGCATGCACCTGTGATCCTAGCTACTCGGGAGGCTGAGGTGGAGGGTATTG
CTTGAGCCCAGGAAGTTGAGGCTGCAGTGAGCCATGACTGTGCCACTGTAC
TTCAGCCTAGGTGACAGAGCAAGACCCTGTCTCCCCTGACCCCCTGAAAAA
GAGAAGAGTTAAAGTTGACTTTGTTCTTTATTTTAATTTTATTGGCCTGAG
CAGTGGGGTAATTGGCAATGCCATTTCTGAGATGGTGAAGGCAGAGGAAAG
AGCAGTTTGGGGTAAATCAAGGATCTGCATTTGGGACATGTTAAGTTTGAG
ATTCCAGTCAGGCTTCCAAGTGGTGAGGCCACATAGGCAGTTCAGTGTAAG
AATTCAGGACCAAGGCTGGGCACGGTGGCTCACTTCTGTAATCCCAGCACT
TTGGTGGCTGAGGCAGGTAGATCATTTGAGGTCAGGAGTTTGAGACAAGCT
TGGCCAACATGGTGAAACCCCATGTCTACTAAAAATACAAAAATTAGCCTG
GTGTGGTGGCGCACGCCTATAGTCCCAGGTTTTCAGGAGGCTTAGGTAGGA
GAATCCCTTGAACCCAGGAGGTGCAGGTTGCAGTGAGCTGAGATTGTGCCA
CTGCACTCCAGCCTGGGTGATAGAGTGAGACTCTGTCTCAAAAAAAAAAAA
AAAAAAAAAAAAAAAAACTGAAGGAATTATTCCTCAGGATTTGGGTCTAAT
TTGCCCTGAGCACCAACTCCTGAGTTCAACTACCATGGCTAGACACACCTT
AACATTTTCTAGAATCCACCAGCTTTAGTGGAGTCTGTCTAATCATGAGTA
TTGGAATAGGATCTGGGGGCAGTGAGGGGGTGGCAGCCACGTGTGGCAGAG
AAAAGCACACAAGGAAAGAGCACCCAGGACTGTCATATGGAAGAAAGACAG
GACTGCAACTCACCCTTCACAAAATGAGGACCAGACACAGCTGATGGTATG
AGTTGATGCAGGTGTGTGGAGCCTCAACATCCTGCTCCCCTCCTACTACAC
ATGGTTAAGGCCTGTTGCTCTGTCTCCAGGTTCACACTCTCTGCACTACCT
CTTCATGGGTGCCTCAGAGCAGGACCTTGGTCTTTCCTTGTTTGAAGCTTT
GGGCTACGTGGATGACCAGCTGTTCGTGTTCTATGATCATGAGAGTCGCCG
TGTGGAGCCCCGAACTCCATGGGTTTCCAGTAGAATTTCAAGCCAGATGTG
GCTGCAGCTGAGTCAGAGTCTGAAAGGGTGGGATCACATGTTCACTGTTGA
CTTCTGGACTATTATGGAAAATCACAACCACAGCAAGGGTATGTGGAGAGG
GGGCCTCACCTTCCTGAGGTTGTCAGAGCTTTTCATCTTTTCATGCATCTT
GAAGGAAACAGCTGGAAGTCTGAGGTCTTGTGGGAGCAGGGAAGAGGGAAG
GAATTTGCTTCCTGAGATCATTTGGTCCTTGGGGATGGTGGAAATAGGGAC
CTATTCCTTTGGTTGCAGTTAACAAGGCTGGGGATTTTTCCAGAGTCCCAC
ACCCTGCAGGTCATCCTGGGCTGTGAAATGCAAGAAGACAACAGTACCGAG
GGCTACTGGAAGTACGGGTATGATGGGCAGGACCACCTTGAATTCTGCCCT
GACACACTGGATTGGAGAGCAGCAGAACCCAGGGCCTGGCCCACCAAGCTG
GAGTGGGAAAGGCACAAGATTCGGGCCAGGCAGAACAGGGCCTACCTGGAG
AGGGACTGCCCTGCACAGCTGCAGCAGTTGCTGGAGCTGGGGAGAGGTGTT
TTGGACCAACAAGGTATGGTGGAAACACACTTCTGCCCCTATACTCTAGTG
GCAGAGTGGAGGAGGTTGCAGGGCACGGAATCCCTGGTTGGAGTTTCAGAG
GTGGCTGAGGCTGTGTGCCTCTCCAAATTCTGGGAAGGGACTTTCTCAATC
CTAGAGTCTCTACCTTATAATTGAGATGTATGAGACAGCCACAAGTCATGG
GTTTAATTTCTTTTCTCCATGCATATGGCTCAAAGGGAAGTGTCTATGGCC
CTTGCTTTTTATTTAACCAATAATCTTTTGTATATTTATACCTGTTAAAAA
TTCAGAAATGTCAAGGCCGGGCACGGTGGCTCACCCCTGTAATCCCAGCAC
TTTGGGAGGCCGAGGCGGGTGGTCACAAGGTCAGGAGTTTGAGACCAGCCT
```

FIG. 8-295

```
GACCAACATGGTGAAACCCGTCTCTAAAAAAATACAAAAATTAGCTGGTCA
CAGTCATGCGCACCTGTAGTCCCAGCTAATTGGAAGGCTGAGGCAGGAGCA
TCGCTTGAACCTGGGAAGCGGAAGTTGCACTGAGCCAAGATCGCGCCACTG
CACTCCAGCCTAGGCAGCAGAGTGAGACTCCATCTTAAAAAAAAAAAAAAA
AAAAAAAAGAGAATTCAGAGATCTCAGCTATCATATGAATACCAGGACAAA
ATATCAAGTGAGGCCACTTATCAGAGTAGAAGAATCCTTTAGGTTAAAAGT
TTCTTTCATAGAACATAGCAATAATCACTGAAGCTACCTATCTTACAAGTC
CGCTTCTTATAACAATGCCTCCTAGGTTGACCCAGGTGAAACTGACCATCT
GTATTCAATCATTTTCAATGCACATAAAGGGCAATTTTATCTATCAGAACA
AAGAACATGGGTAACAGATATGTATATTTACATGTGAGGAGAACAAGCTGA
TCTGACTGCTCTCCAAGTGACACTGTGTTAGAGTCCAATCTTAGGACACAA
AATGGTGTCTCTCCTGTAGCTTGTTTTTTTCTGAAAAGGGTATTTCCTTCC
TCCAACCTATAGAAGGAAGTGAAAGTTCCAGTCTTCCTGGCAAGGGTAAAC
AGATCCCCTCTCCTCATCCTTCCTCTTTCCTGTCAAGTGCCTCCTTTGGTG
AAGGTGACACATCATGTGACCTCTTCAGTGACCACTCTACGGTGTCGGGCC
TTGAACTACTACCCCAGAACATCACCATGAAGTGGCTGAAGGATAAGCAG
CCAATGGATGCCAAGGAGTTCGAACCTAAAGACGTATTGCCCAATGGGGAT
GGGACCTACCAGGGCTGGATAACCTTGGCTGTACCCCCTGGGGAAGAGCAG
AGATATACGTGCCAGGTGGAGCACCCAGGCCTGGATCAGCCCCTCATTGTG
ATCTGGGGTATGTGACTGATGAGAGCCAGGAGCTGAGAAAATCTATTGGGG
GTTGAGAGGAGTGCCTGAGGAGGTAATTATGGCAGTGAGATGAGGATCTGC
TCTTTGTTAGGGGGTGGGCTGAGGGTGGCAATCAAAGGCTTTAACTTGCTT
TTTCTGTTTTAGAGCCCTCACCGTCTGGCACCCTAGTCATTGGAGTCATCA
GTGGAATTGCTGTTTTTGTCGTCATCTTGTTCATTGGAATTTTGTTCATAA
TATTAAGGAAGAGGCAGGGTTCAAGTGAGTAGGAACAAGGGGGAAGTCTCT
TAGTACCTCTGCCCCAGGGCACAGTGGGAAGAGGGGCAGAGGGGATCTGGC
ATCCATGGGAAGCATTTTTCTCATTTATATTCTTTGGGGACACCAGCAGCT
CCCTGGGAGACAGAAAATAATGGTTCTCCCCAGAATGAAAGTCTCTAATTC
AACAAACATCTTCAGAGCACCTACTATTTTGCAAGAGCTGTTTAAGGTAGT
ACAGGGGCTTTGAGGTTGAGAAGTCACTGTGGCTATTCTCAGAACCCAAAT
CTGGTAGGGAATGAAATTGATAGCAAGTAAATGTAGTTAAAGAAGACCCCA
TGAGGTCCTAAAGCAGGCAGGAAGCAAATGCTTAGGGTGTCAAAGGAAAGA
ATGATCACATTCAGCTGGGGATCAAGATAGCCTTCTGGATCTTGAAGGAGA
AGCTGGATTCCATTAGGTGAGGTTGAAGATGATGGGAGGTCTACACAGACG
GAGCAACCATGCCAAGTAGGAGAGTATAAGGCATACTGGGAGATTAGAAAT
AATTACTGTACCTTAACCCTGAGTTTGCGTAGCTATCACTCACCAATTATG
CATTTCTACCCCCTGAACATCTGTGGTGTAGGGAAAAGAGAATCAGAAAGA
AGCCAGCTCATACAGAGTCCAAGGGTCTTTTGGGATATTGGGTTATGATCA
CTGGGGTGTCATTGAAGGATCCTAAGAAAGGAGGACCACGATCTCCCTTAT
ATGGTGAATGTGTTGTTAAGAAGTTAGATGAGAGGTGAGGAGACCAGTTAG
AAAGCCAATAAGCATTTCCAGATGAGAGATAATGGTTCTTGAAATCCAATA
GTGCCCAGGTCTAAATTGAGATGGGTGAATGAGGAAAATAAGGAAGAGAGA
AGAGGCAAGATGGTGCCTAGGTTTGTGATGCCTCTTTCCTGGGTCTCTTGT
CTCCACAGGAGGAGCCATGGGCACTACGTCTTAGCTGAACGTGAGTGACA
CGCAGCCTGCAGACTCACTGTGGGAAGGAGACAAAACTAGAGACTCAAAGA
GGGAGTGCATTTATGAGCTCTTCATGTTTCAGGAGAGAGTTGAACCTAAAC
```

FIG. 8-296

```
ATAGAAATTGCCTGACGAACTCCTTGATTTTAGCCTTCTCTGTTCATTTCC
TCAAAAAGATTTCCCCATTTAGGTTTCTGAGTTCCTGCATGCCGGTGATCC
CTAGCTGTGACCTCTCCCCTGGAACTGTCTCTCATGAACCTCAAGCTGCAT
CTAGAGGCTTCCTTCATTTCCTCCGTCACCTCAGAGACATACACCTATGTC
ATTTCATTTCCTATTTTTGGAAGAGGACTCCTTAAATTTGGGGGACTTACA
TGATTCATTTTAACATCTGAGAAAAGCTTTGAACCCTGGGACGTGGCTAGT
CATAACCTTACCAGATTTTTACACATGTATCTATGCATTTTCTGGACCCGT
TCAACTTTTCCTTTGAATCCTCTCTCTGTGTTACCCAGTAACTCATCTGTC
ACCAAGCCTTGGGGATTCTTCCATCTGATTGTGATGTGAGTTGCACAGCTA
TGAAGGCTGTACACTGCACGAATGGAAGAGGCACCTGTCCCAGAAAAAGCA
TCATGGCTATCTGTGGGTAGTATGATGGGTGTTTTTAGCAGGTAGGAGGCA
AATATCTTGAAAGGGGTTGTGAAGAGGTGTTTTTTCTAATTGGCATGAAGG
TGTCATACAGATTTGCAAAGTTTAATGGTGCCTTCATTTGGGATGCTACTC
TAGTATTCCAGACCTGAAGAATCACAATAATTTTCTACCTGGTCTCTCCTT
GTTCTGATAATGAAAATTATGATAAGGATGATAAAAGCACTTACTTCGTGT
CCGACTCTTCTGAGCACCTACTTACATGCATTACTGCATGCACTTCTTACA
ATAATTCTATGAGATAGGTACTATTATCCCCATTTCTTTTTTAAATGAAGA
AAGTGAAGTAGGCCGGGCACGGTGGCTCACGCCTGTAATCCCAGCACTTTG
GGAGGCCAAAGCGGGTGGATCACGAGGTCAGGAGATCGAGACCATCCTGGC
TAACATGGTGAAACCCCATCTCTAATAAAAATACAAAAAATTAGCTGGGCG
TGGTGGCAGACGCCTGTAGTCCCAGCTACTCGGAAGGCTGAGGCAGGAGAA
TGGCATGAACCCAGGAGGCAGAGCTTGCAGTGAGCCGAGTTTGCGCCACTG
CACTCCAGCCTAGGTGACAGAGTGAGACTCCATCTCAAAAAAATAAAAATA
AAAATAAAAAATGAAAAAAAAAGAAAGTGAAGTATAGAGTATCTCATAG
TTTGTCAGTGATAGAAACAGGTTTCAAACTCAGTCAATCTGACCGTTTGAT
ACATCTCAGACACCACTACATTCAGTAGTTTAGATGCCTAGAATAAATAGA
GAAGGAAGGAGATGGCTCTTCTCTTGTCTCATTGTGTTTCTTCTGAGTGAG
CTTGAATCACATGAAGGGGAACAGCAGAAAACAACCAACTGATCCTCAGCT
GTCATGTTTCCTTTAAAAGTCCCTGAAGGAAGGTCCTGGAATGTGACTCCC
TTGCTCCTCTGTTGCTCTCTTTGGCATTCATTTCTTTGGACCCTACGCAAG
GACTGTAATTGGTGGGGACAGCTAGTGGCCCTGCTGGGCTTCACACACGGT
GTCCTCCCTAGGCCAGTGCCTCTGGAGTCAGAACTCTGGTGGTATTTCCCT
CAATGAAGTGGAGTAAGCTCTCTCATTTTGAGATGGTATAATGGAAGCCAC
CAAGTGGCTTAGAGGATGCCCAGGTCCTTCCATGGAGCCACTGGGGTTCCG
GTGCACATTAAAAAAAAAATCTAACCAGGACATTCAGGAATTGCTAGATTC
TGGGAAATCAGTTCACCATGTTCAAAAGAGTCTTTTTTTTTTTTTGAGAC
TCTATTGCCCAGGCTGGAGTGCAATGGCATGATCTCGGCTCACTGTAACCT
CTGCCTCCCAGGTTCAAGCGATTCTCCTGTCTCAGCCTCCCAAGTAGCTGG
GATTACAGGCGTGCACCACCATGCCCGGCTAATTTTTGTATTTTTAGTAGA
GACAGGGTTTCACCATGTTGGCCAGGCTGGTCTCGAACTCTCCTGACCTCG
TGATCCGCCTGCCTCGGCCTCCCAAAGTGCTGAGATTACAGGTGTGAGCCA
CCCTGCCCAGCCGTCAAAAGAGTCTTAATATATATATCCAGATGGCATGTG
TTTACTTTATGTTACTACATGCACTTGGCTGCATAAATGTGGTACAAGCAT
TCTGTCTTGAAGGGCAGGTGCTTCAGGATACCATATACAGCTCAGAAGTTT
CTTCTTTAGGCATTAAATTTTAGCAAAGATATCTCATCTCTTCTTTTAAAC
CATTTCTTTTTTTGTGGTTAGAAAAGTTATGTAGAAAAAAGTAAATGTGA
```

FIG. 8-297

```
TTTACGCTCATTGTAGAAAAGCTATAAAATGAATACAATTAAAGCTGTTAT
TTAATTAGCCAGTGAAAAACTATTAACAACTTGTCTATTACCTGTTAGTAT
TATTGTTGCATTAAAAATGCATATACTTTAATAAATGTATATTGTATTGTA
TACTGCATGATTTTATTGAAGTTCTTGTTCATCTTGTGTATATACTTAATC
GCTTTGTCATTTTGGAGACATTTATTTTGCTTCTAATTTCTTTACATTTTG
TCTTACGGAATATTTTCATTCAACTGTGGTAGCCGAATTAATCGTGTTTCT
TCACTCTAGGGACATTGTCGTCTAAGTTGTAAGACATTGGTTATTTTACCA
GCAAACCATTCTGAAAGCATATGACAAATTATTTCTCTCTTAATATCTTAC
TATACTGAAAGCAGACTGCTATAAGGCTTCACTTACTCTTCTACCTCATAA
GGAATATGTTACAATTAATTTATTAGGTAAGCATTTGTTTTATATTGGTTT
TATTTCACCTGGGCTGAGATTTCAAGAAACACCCCAGTCTTCACAGTAACA
CATTTCACTAACACATTTACTAAACATCAGCAACTGTGGCCTGTTAATTTT
TTTAATAGAAATTTTAAGTCCTCATTTTCTTTCGGTGTTTTTAAGCTTAA
TTTTTCTGGCTTTATTCATAAATTCTTAAGGTCAACTACATTTGAAAAATC
AAAGACCTGCATTTTAAATTCTTATTCACCTCTGGCAAAACCATTCACAAA
CCATGGTAGTAAAGAGAAGGGTGACACCTGGTGGCCATAGGTAAATGTACC
ACGGTGGTCCGGTGACCAGAGATGCAGCGCTGAGGGTTTTCCTGAAGGTAA
AGGAATAAAGAATGGGTGGAGGGGCGTGCACTGGAAATCACTTGTAGAGAA
AAGCCCCTGAAAATTTGAGAAAACAAACAAGAAACTACTTACCAGCTATTT
GAATTGCTGGAATCACAGGCCATTGCTGAGCTGCCTGAACTGGGAACACAA
CAGAAGGAAAACAAACCACTCTGATAATCATTGAGTCAAGTACAGCAGGTG
ATTGAGGACTGCTGAGAGGTACAGGCCAAAATTCTTATGTTGTATTATAAT
AATGTCATCTTATAATACTGTCAGTATTTTATAAAACATTCTTCACAAACT
CACACACATTTAAAAACAAAACACTGTCTCTAAAATCCCCAAATTTTTCAT
AAACTCAGTTTTAAACTAACTTTTTTTCAAACCACAATCTGATTTAACAAT
GACTATCATTTAAATATTTCTGACTTTCAAATTAAAGATTTTCACATGCAG
GCTGATATTTGTAATTGTGATTCTCTCTGTAGGCTTTGGGTATAATGTGTT
CTTTTCCTTTTTTGCATCAGCGATTAACTTCTACACTCTAACATGTAGAAT
GTTACTACAATATTAAAGTATTTTGTATGACAATTTTATTTGAAAGCCTAG
GATGCGTTGACATCCTGCATGCATTTATTACTTGATATGCATGCATTCTGG
TATCTCAAGCATTCTATTTCTGAGTAATTGTTTAAGGTGTAGAAGAGATAG
ATATGGTGGATTTGGAGTTGATACTTATATATTTTCTATTTCTTGGATGGA
TGAATTTGTACATTAAAAGTTTTCCATGGCAGAAATCTTTTCAAAAACTTT
TTTTTTCCGGGATGGATTGAAGGCCCTGATTTCACCACAATGCAATATATT
AATGTAGCAAAATTGTACTTGTACCCCATGAATATATATAATCTTAAGAAA
ATTTTTTAGCCAATTATTATTACTTACTAGATATTAGGCTGTGTTCTGAA
TCTTAATTTAATTCCTCCAAAGAATCTTATGAGGTAGGTAGGAGCTATTGC
TGCTATTCTGTTATGCTTATGTTGCTGTTATGAAACCAAGGCACAGAGAGG
TTAGTTAACTTGCTGAAGAAAATGATGTGCTGGATTTTTATTCTAGCTATT
CTGGAATAACAACTACACAACCTTATGTCTGAGCCAAGGAAACATACGGTG
TGGCAACAGTTACCATGTTTTAGGAACAGCAGCACTCCTAATGTTTGCTG
CAGGGAAAAAGGAATCTCAGAATTTGCCTGATCCCTATAATTTTTTCCTA
AATATTTTGAAATATCTTTCAGATGTATTTTAAAATTTAAGGATATTTTGT
TCAGTTCATACAGAATTTTTTTTTTTCTCGAGATGGAGTCTCACTCTAT
CACCCAGGCTGGAATGCAGTGGCATGATCTCGGCTCACTGCAACCTCTGCC
TCCTGGGTTCAAGCAATTTTCCTGCCTCAGCCTCCCAAGTGGCTGAGACTA
```

FIG. 8-298

```
CAGGCGCATGCCACCATGCACGGCTAATTTTTTTGTATTTTTAGTAGAGA
TGGAGTTTCACCATGTTGGCCAGGCTGGTCTCGAACTCCTGACCTCAAATG
ATCCGCCCTTTTTGGCCTCCCAAAGTGCTGGGATTACAGGCGTGAGCTACC
GCGCCCAGCCAAATTTCTAACTTGTTTTGTTGTTGTTGAGACAGGGTCTCA
GTCTGACACCAAGGCTGGTGTGCAGTACTGCGATCACGGCTCACTGCAGTC
TCGACCTCCTGAGCTCAAGTGATCCTCCCACCTCAGCCTACTGAGTAGCTG
GGACCACCACGCCTGGCTCATTTTTTCTATTATTTATTGAAACGGGTTCT
GGCTATGTTGCCCAGGTTGGTCTTGAACTCCGGAGCTCATGCGATCCACCC
ACCTCAGCGTCCGAAAGGATTATCAGGAGTGAGCCACCGTGCCCGGCCAAA
TTTCTAACTTTTGAATTGACATATTCATTTATTCTCTTTATCATTCAGGGA
GAAATTTGGGGATGGATAGCCTTGAAGCATCATCCACCAAGTTATTTTATA
CACCAGATTTAGATACAAAGTATTTTTTATTATTTAAAAAAATCAAATTC
TAGCTTTTACTCTGAAGATTCTAAAAAGAATTTTGGAGTCTTTAATTCATA
CTTCAGGGGCAGGGGAATAAGTACCAATATTCGTATAACTTTCAGTGCAAG
TCACGTTAGCTAACTGTAGTCTATTGAGTTAAATATCCTTGATTTATTCCT
TAAAACTGAGTCACTATGACGGCACTTTTTGTTTTTTTTTTCGAGACGG
AGCTCGCCCTGTCTCCCAGGCTGGAGTGCGGTGGTGCGATCTCGGCTCACT
GCAATCTCCGCCTCCCAGGTTCAAGCGATTCTCCTGCCCCAGCCTCCTGAG
TAGCTGGGACTACAGGCACACACCACCACGCCCAGCTAATGTTTGTATTTT
TAGTAGAGACAGGGTTTCATCATTTTGGTCAGGCTGGTCTTGAACTCCTGA
CCTCGTGATCAGCCTGCCTCGACCTCCCAAAGTGCTGGGATTACAGTCATG
AGCCACTGCACCCGGCTGAATGGCACTTTCATAAAACAGTAAATAACCAAC
TTCACTACTGCCCCCAAGAGTTTTACTATGTATATGAGGGCATCTGTTTTA
AGTATGGGTATAATGTTACGGGTTTTTCTTTGTGTAAGTTTGGGTTCACAA
TTTCATCATTAAAACAAATGTAAAATACTTTGTGCTTTCTGTGTGCTATTA
AGAAAGTATTCAAGGGAATTTTGAAAATCAAATTTAATTACTCTCATGTTT
GTAAAATTTTTGAAACAAATGTTTAAGAGAGGATAATGTTAGAAATTATCT
TTCCAGCCAGACCTGGTGGCTCACGCCAGTAATCCTAGCATTTTGGGAGGA
CAAGGTGGGCAGATCACTTAAGCCCAGGAATTCAAGACCAGCCTGGACAAC
ACAGGGAAAGCCCATCTCTACAAAATATACAAAATTAGTGGCCGAGCGTGG
TGGCTCACGCCTGTAATCCCAGCACTTTGGGAGGCCGAGGCGGGCAGATCA
CCTGAGGTCAGGAGTTCCAGACCAGCCTCAACATGGAGAAACCCCGTCTCT
ACTAAAAATACAAAATTAGCTGGGCGTGGTGATGCATGCCTGTAATCCCAG
CTACTCGGGAGGCTGAGGCAGGAGAATTGCTTGAACCTGGGAGGTAGAGGT
TGCGGTGAGCCGAGATCCCGCCATTGCACTCCAGCCTGGGCAACAAGAGCG
AAACTCCATCTCAAAAAACAAAACAAACAAATAAACAAAATTAGTCAGGTG
TGGTTGTGCACACCTGTAGTCCCAGCTACTTGGGAGGCTGAGGTGGGAGGA
TCACTTGAGCCCGGGGAAGTGTAGGCTACCATGAGCCATCATGGTGCCACT
GTACTCCAGTCTAGGAAAAAATAAACATTAAAAATTTTAAAATCTTAAAA
AAAGAAAAGAAATTTTCTGTCCAGATATCTTTATTTTTAACAAATCGAAGT
GTATTAATAGTGTTTATGGGAGCGTGCCCACACAAGGACAGCAAGCCTAGG
AAGTGCAAGTCAAGAAAACTTTTGTGAAATAATTTAAACTGAAAAGAAAA
AGCAGAGATTTTTTCTAGAAAAGTAAGGAGTGGAGGTAAAAAAAAAACAC
AGCAGAGACACAGGTATGCTACGGAACCAAAGGTGTGCCAATGGTACTGAC
AGTTTAATTCAGAAAAAATGAATCAGAAAATGGATATTTTAAATAAGTT
AGGTTGCTGAAAAAGAGAAATGCAGTGAAGCCTTAGATGGGAGTGAGATAA
```

FIG. 8-299

```
ATCAGCCATTGGCTAGAGGAGTTTCTTGCCCAAGACCAGTGGTGATGTCCC
CAAATGCCTGGAAACAACTGTTGTGACATTATAAAGCCCCCATAGTCTAAG
TTGGGTGAGACTATACTTATGCATTTTCTCACCTGTAATATAGCTTAAAAG
TATTTCTACTCTGGGATTTCTTTACATTTTACTAAAGCGCAATTATATACT
TAAAACTGATAGTGTATGCTGGGCTGCTAGTCATTCTCAACCCTGGCCAAT
TATCAGAATTGTTTGTTGAATATATAGGTGCCATATATAGGTGCATACACA
CACACACACACACACATACACACACACACACACACACACACCATATTTC
ATTCCTCATATCGAATATTCTGAGAGAGTTAGTTTGTGGAGGGTAGTTCTG
GACAATTTATATTTTCATAACACCTCTGGTTATTTTTTTTTAAGTAGAGAT
GAAGACTTGCTATGTTGCCCAAAATGGTCTTGAACTCCTGAGCTCAAGCGA
TTCTCCCAACTCAGCCTCCTGAAGTGCTGGGATTACAGCCGTGAGCCACTG
CATTAACCTCTGATTAATATCATAGATTAACCTCTGATTAATATCATAGAT
TTATTTGTTTGAATGCTTCATGTATCCTCTCAACCACAACTTGTTTGCAGA
GTTTTAATCTGAAGGGCTTAGGTCTCTTGTTCAATGAATGAGTTTGATCTG
ATGGGTGAGAGGAAGGTGAAATGGAAAGCGAACGAGAAGCCATACAGATTA
GGCGAGTGAGCCTAATCTCTCCCTAACCATAAGATTGAGTATGCCTGAATT
CTTCGCAGAGTGGAAGAATCCATTTTAAATATATATATCTACATGTACAGA
TCCTTTAAATATTTGTTCTGACATTCATTGTTTTTGAGTCACTGTCATTGA
GAAAAGTTTAGAAAGGAGATATTAGGAGCAGGAAATAGAAAGTAAATAAAA
TATCAAAATAAAAATGGGGTTTTATAAATGATATAATAGGCAAAATAAAGG
AAAGGCATCCTAGACCTCTGGTTAAAATGAAGATGGCACTTGGCGAGATGT
GTTCCAGGGTAGTTCACATGATGTATGTTTTCAGAGAATTGTCATATTGCA
TATGCTGCTATATTTTTTATTTTCATGAATTAAAAGGCATGTTGAGATTTC
AGAGTTTTACTTATGATCTCAGACTCTGCATTTTTTCTCTGTAATGTTTGA
CATTTCTTCCTAGCTAAGTCTCTAGTTATAAGGTCTGTGTTGTGGCATGTG
GACAGTGAGTGGAAGAACCTAAGAACTCAATTTGGGGCAGAAGAATGTAAT
CAATTATTTCAGAAGTGATACAAACAATATGACATGTAGAGCATTCTGGCC
TTTCCTGGGTCTTTTTTCTCCATTCCTGGATTTCTTCTCTTCATGTGAGCA
AGTCTGAGGTTACTATATAATGTCTCTCACAGGCCACAGCCCCATTCTAAA
TATTCCCAATAGAAATTCATTTATTAACCAGAGAGTGGTGGGTGGGGTTGT
TTTTGTTTTTTAAACAAAAGTGGATCTTATGGGCATTCTGGAAAGCTCCCG
CAGGAAGCTAAGAATAAAATTTTGAATTGAGAAGTCCCTTTCTTCAAACCA
CATTCAGACCCAATTCTGCTATTCTATTTATTTTTCAAGGGGATTAGCCTT
ATTTTAACACCAATAATCTTATCACAAAAACCTCCCAGAGGAAGACCCTGT
AGATTTTGTAATGACCTTAATCAAGTATTAGCCCTACACTTCAATTAATCC
CCAACTGTACAAAACGAATGTTCTTTTCTCTAAAGCTGTAGCAAGTTGAAA
GGGGATTAAAAACGGAGGGAAGGGAAGAGTGTTTGGAATTTCAGGCACAGC
AAACAGGCACAGCAGACCAGGAAGAGCGTCCCGGGAAAACATATTATCCAG
ACTTAAGTTTATATTCCCTGTCTCTCTCAGACTTTGCAGAAAAATGAGTC
ATTCAACAAATATTTGAATCGAGATAGGGAAAGTGACGAGGAAGAAGTTTG
CACTTATGAGGTTTTAATTTGCAATTATTTGGCTACCTTTTTGCCTTCCCA
AAACATAGGGTCTTTAGGAGTGAAACTTCATAGCCAAACTTATACCTTGTC
CAGCACAGAGAAGGCCATCAAAATGCCTGGTTTAAATAAAAATATTAAAAT
GATTGGGAGGGTAAATCCCTTGACCTATAAATCTGACCTCCTTTAAACATT
ATTTGTATGTTCCCCAATAAACTATTCCGTAATTTATTAGTTAGCAAGTGG
AAATAAAAAGAAATGTGGAATGGGGCTATGCTTAGCGTCATTAAGCTGACA
```

FIG. 8-300

```
GGAATACAGCGCATTCAACTTGCAAACACCCTTCCACTCCCACAAAGAGCA
AGCTGTCACTGGCCAATCAAAACAATGAACCATAATGAAACAGTTTTTCTT
GCTCCACCCACTTGGTGACCAAATTTGAAAAAAAAAAAAAACCGCGCCAAC
TCATGTTGTTTTCAATCAGGTCCGCCAAGTTTGTATTTAAGGAACTGTTTC
AGTTCATACCTTCCACTGCGATAGGAATCATGTCTGGTCGCGGCAAAGGCG
GAAAAGGCTTGGGGAAGGGTGGTGCTAAGCGCCATCGTAAGGTGCTCCGGG
ATAACATCCAGGGCATTACAAAACCGGCTATTCGCCGTTTGGCTCGGCGCG
GTGGCGTCAAGCGCATTTCCGGTCTTATCTATGAGGAGACTCGAGGTGTGC
TTAAGGTTTTCTTAGAGAACGTTATTCGAGACGCCGTCACCTATACGGAGC
ACGCCAAGCGCAAAACTGTCACAGCCATGGATGTAGTATATGCCCTAAAAC
GTCAGGGGCGCACTCTGTATGGCTTCGGCGGCTGAATCTAAGAATACGCGG
TCTCCTGAGAACTTCAAAAAACAAAAACAAAAAAACCCAAAGGCCCTTTTC
AGGGCCGCTCACAAAGTCGTTTAAAGAGCTGAAATGCGTTGCGAGAATGAG
TTTGGATGACAGAAATAACCGTGACATCCTGCATAAGAATGAATTGTGTTT
GCCATGACCGGCCACACTGTGACAAAATTTCAAAGCATAAAGTAGGCATAG
AGAGGTAAGCGCTAATAAAGTGATTGGCTCCACAAAAAGCATTTTGCTGGG
CGCAGTGGCTCACGACTGTAATCCCAGCACTTTGGGAGGCCAAAGCTAGTG
TATCACTTGAGATCAAGAATCCGAGACCAGCCTGGCCAAAATGGTGAAACC
CCCTCTACCAAAAAAATACAAAACTTAGCCGGGCGTGGTGGTCTGCACCT
GTAGGCCCAGCTAGCCCGGAAGCAGAGATTGCAGTGAGCCGAGATCGCGCC
ACTCCCCTCCAGCCTGGGAGACAGAGAGAGACTCCTCAAAAAAAAAAAAAA
AAAAAAAAAAAAAATTATGTATTTTAGAGCATTCTAAGAATGGTACTTTG
GACTTAACCGAAGGGCTGGAGGCGCGTGTTGAACAAAGGTTATCACCTTTT
GGCTCATGCGGCACACAGCTATGTAAATAAAGCATCTTTAGGGACAAGCTC
TCATTTGCGGAGGGTTCTATGGCTGTTGTCCTATTGGCCAAAACAAAGTGG
TCTAAGTCCGGGCGCGGTGGCTCACGCCTGTATTCCCAGCAGTTTGGTAGG
CCAAGGTGGGTGGATCACGAGGTCTGGCGTTCAAGACCAGCCTGGCCAAGA
TGGTGAAACCCCGTCTACTAAAAATACAAAAATTAGCCGGGCGTGGTGGCG
GGCACCTGTAATCCCAGCTACGTGGGAGGCTGAGCCAGAGAACTGCTTGAA
CCCAGGAGGCAGAGGTTGCAGTGAACCGAGATTGTGCCACTGCACTCTAGC
CTGGGTGACAGAGCGAGGCTCCATCCAAAACAAAACAAAACAAAAAAGTGG
TCTAATAATCCCCAGAACTGGAGGAAGAACCATAACTTATTGATTTTGTTT
TTAACCTTATGTATGCCAGGCATGCTAGCCTTGTATACATACAAGGCTAGA
GGAGCAAAGGTGCAGGAAGCCATCTTGAGGGAGTCCCATATTATTGAGAGA
CCGGCCAGCTGCTGGGAGAGGCTAGTTGTTCATCCTCACTGTATGTGATGA
GAATCTGGTGACAGTCCATTGCTGGGCACAGCATTTAGGCAAAATGGCTCT
CTGCTATGTCAGGCAAGTGAGGCATATTTTTGCACAATCCTAGTAATTCCG
AACTCATTGGGAAACAATGGCAATTACATCCAAGCAAGGAAAGGTCTGTGG
TTGATTTTATCTATACAAATTTAAAACATAATGTTTACAACCTTTCATTAT
AGGACACAATTTTTAAAAAGATGCCAAACTATACAAATAAGTTCAGAAAAG
TGAGGTACTATTGAACCGTCTGGAAAACATAAATGTATGTGAAATAATGCA
ATGCATAGTTTTGCAGGGGACTTTGTTCAAAGTTTCTCGAAATACCATGGT
CCAAAGTAGACTAACATTAGCATTGGTTATTTATGATGATCAGTAAGAATA
CTAAATCAAAAATCAAAGGAAAATTAAACTATGTCTGTTTAAAGAGAAACG
TAGTTTACCTCAGACTGAGAGTTAAAACAAGTTTGTGATTCAGGAAGGTGG
AATTCAGAACCTAATTGGGCAGCCTCCAACATTTCCATTAAGGTTTGGATT
```

FIG. 8-301

```
CTTAAAATTTTTCAGTCTTCGGTATGCTCTGGTAGTCTGATGAAACTTACA
GATTCTTTTCATAAATAAGATACTTAAAGTAATTCATAGGGTTACAATTGT
ATTAGACCAATAATATTAAAATAATTATCAAACCACTTGACCGTAATATGT
GTGTTTTGTTGATATACCTAATAGTACTTCGGAAATAAGCAAGCACGATT
TCCAGATTCTTGCAACAACTATAACCTACAAATTTGTTATTTCTATCAGTC
ACACACAATGGAAGAAAATTCTAAATTTCAGCTACAGGATAATGAATAGAT
GAAAACAACAACAACAACAACAAAAAAACTCCCCTAATCCATATTCT
GGGACACCTTGATTCCTATTTATTGATCCCTTGAAGTCAGTGGATAGCATA
TTAAGAAACAATAGTTACAATGACACCACAGAAAGACTAGAATGTAGTACT
TGTGTTAAAAAAAAAAAAAGTATCAGCAAGTTATGTTTGGATGCCAAATTG
CTCTCCACTTCCCTTCCCTGACACTGGCATTTCCAGAACTTAGATGCTCTT
ACATGTAAAAGCCTCCTCTAGTGCACCATCGAGCTTTTCAGGATTGGACAT
CAGACTTTTTAGTTCCTGGACCTCTAGATATACGGCAGTCTCTGACAAGAA
GCCCTTTTCTGTTTTAACTTTTTTTTTTTTAAGTTTTGAGACAACGTCT
GACTCGCTGTCACCCAGGCTGGAGTGAGGTAGCACCATCATAGCTCACTGT
ATCCTTAAACGCCTGGGTGCAGGGACTAAGGGAGCGTGCCAACCATGCTTG
ACTAATTTACTTTTTTGTAAAACCAGTAGTCTCCAACCTTTTTGACACAAG
AGACCGTTTTGTGTAAGACAATTATACCACGGACCAGGGGGTGCAGGGGCT
GGGAGCAATGATTTCCGGACTAAAACTGCTCCAACCTCAGATCATCAGGCA
TTAGATTGTCACAAGGAGCCTGAAACCTAGATCCCTTGCATGTGCCATTCA
CAATACAGTTTGAGCTTATGAGAATCTATCTAATGCTGCAGCTAACCTGAC
AGGCGGTGGAGCTCAGTTGGTTAATGTTCGCTCACCCCTCAGCTGTGCGGC
TCAATTCATAACGTGCCATGGACAGGGACCGGTTACCGGTCGGTGGCCGGG
GAAATGAGGACCCCTGGTATAGATGGTAGTCTGGCTATGTTGCCCAGGATG
GTCTTGAAGCCTGGCCTGAATTAATTCTCCAATCTCAAGCCTTTTCAACTC
AGCTGCATCACAACTTAAACCTATAGATAACTGTCACAGAAACTTGTTTCC
AGTGTTACGCCATCTTAAAATAATGTGGGTGGCTCTTAAAAGAGCCTTTGG
GTTCTTTCCAAATTGGCCTCCCGGAAAGCTCTTTACTTCTTAGATGTGGCC
TTTCTAACATTAACTTCATGATGTTGGGTCAATTTTGACTTCGAAGCCCTT
GCCTTCACTGGGCTCTTCTGCTGTTGCTTACCCTTGGCTCCTTTAGCCTTT
CTCCCGCTCCTAACAGTTTTAGGAGTTGTCGCTCTCGGCTTCTTGGCTCTC
TTATTGGTTTTAGCAGTCTTTGGTGACTTGGAGTCCCTGGATAAAACCAGC
TTCTTGGTCTTGGCAGAAACTGACTTTTTAGCCTTGCTTCTGGTAGATTTA
GGAATCACCTTCTTACTAAGCTTAAAGGAACCGGAAGCACCAGTACCCCTG
GTTTGCACCAGGATTCCCTTGTTCACTAAGCTCTTGAGGGACAGTTTGATG
CGGCTGTTATTCTTCTACGTCGTAGCCAGCAGCGGCCAATGCCTTCTTG
AGCGCAACCAAAGACATACCTACTCGTTCCTGTGACACTGAAAGGGCCTCG
GTGATCAACTTGGACACAGAGAGGTTCGGCACTTTGCGACTTGCACTTATC
AAGCCAGCCGGCTTCCTCCCTCGCTTCTTGGTTGGAAGTTTCTCCATAGCG
GCTACACCAGCACTGGCAGAAGCTGCAGGCACGGTTTCAGACATAACAACA
GAGAAACGCAAGATGTAATAACCAGCGAAAAGCATGAAACACCCGGGCGGC
CTCGGGGCCTTATATAGGGTAGGGCGCGCTGTGATTGGTGCATCACCTAGG
CACCGCCCCGCCCCTTGGAGGAGGAGTATTTGTGTTTGTTTTACCCGGAA
AAGTTGAGTATAACAAAACCCCTCTTTACAGAATCTCCCAGGGTCTAGTGC
TGAATAATCTGCGGAAATTCATATTTGACATGACTTTTCTCTTTTTAATGA
AAAATGACCCTGGATGCCAAAACTATTCGAGAAAGCCCTCGATTTTCAATC
```

FIG. 8-302

```
AAATTCACGGAGAGGAACAAAACTTCCCCTTTTCCTTGTAAATTAATAAGT
AATCTTTGGCAGAAGACTTATTTCATCTCTTCAGAGTGGTCTTCCAAATGG
ATAGCTTCAAATCGGTAGAGGAAAGAAATTATTCACGCCATGATTTTTATT
TAAAATTATTTATATATGTGAGGGAAGTAACACAGATCTCTTAGCTGTCTA
ATTGCGGAGTCAGAAGATGCTTATAGAATTGTCAAAAGACTGCAGAGGATG
TCTTTATTTAGGCATGTGCAATCTAATAAATCATAATCCACAGGAACATGG
GTTGTCTGTAATTAAAGGTGCTCCCAAGTCCCTGTAGCTTTATAGAGGACT
CTCAAGGATGGGGTAATATCAAGATCTCACACATTATGTAAGATTGGCCAT
AATCAGGCCACTCTCATGACCGGTGTCCTCAACTGAGTTTTGCTTCTGGTT
TCATTAATTGAAGTCCCCTCTATCCCCCTGCCCACCCCTACATCCCCAGAT
AAACAGACACAGTCCCTCCCCTAAATTAACTATAAAACATGAGGTAGGAAC
CCTAGACTCAAGAACCTACTAGAAACTACAGACCCCATGTCTAACAAGACT
GGGCGGGTTGGCTGGGCGCAGTGATTCATGCCTGTAATTACAGCACTTCGG
AAGGCTGGAGGCCAGGAGTTCAAGACTAGGTTGGCCTGGTCCCTACTGAAA
AAAAAAAAAATTAGCTGGGTGTGGTGGCACATGCCTGCAGTCCCAGCTTCT
GGGTAGACTGAAGAGGATCACTTAGAGCCCAGGAGCTTGAGGTCGCAGCTA
CTGCACTCCAGCCTGGGCAGACCCTCATCTCTGAATTGCTTAATTAATTAA
CTGAGCTGGCAGATTTGGCTGCATAGCTGTGGGGAAAGGGTTGTTGGAATA
ATGTCCAGTGTGCTCCCCTGAGCTTCTACTGGAACAGGTCTTTGTGAGAGG
CCTGGAGATAAGAGCTTGCTCACAAAGGCTGAGGCCTTTCTGGGATGCTGA
ATGAGTTTAGTGTGGCCAGAGCATAGGGTCTCAGCAAAGGAAAACTCCATA
AGGGCCATTTGTGAAGATCCCCAAATACTTGTGTGAAACATTTGGTAGATA
TTAGAAGTTTTGTTTTGGTTTGGTTTGAGACAGAGTTTTGCTCTTGTTGCC
CAGGCTGGAGTGCAATGGTGTGATCTTGGCTCAGTGCAACCTCCACCTCCC
AGGTTCAGGCAATTCTCCTGCCTCAGCCTCCCAATTAGCTGGGATTATAGG
CGCCCACCACCATGCCTGGCTAATTTTTTGTATTTTTAGTAGAGATGGGGT
TTCATCATGTTGGCCAGGCTAGTCTCGAACTCCCCACCTCAAGTGATCTGC
CCGCCTCTGCCTCCAAAGTGCTGGGAATACATGCGTGAGCCGCCGCGCCCG
GCAGACATTGGAAGTTTTTAAGCAGAGAATTTGTTGTATTGTTGTAGTTGT
CTTGGGTTTAGATTTATTGCATAAACAATCATTTTTGAGAAGGGCCCACAG
TCAGAAGTTGGGAGTCTGTTGCAATAGTCTCAGAAGAATGGCAAAGACCTT
GCCTAAGGGGACAGTGTGGTAAAGGAGAGAGTCTACATTTGAAATATTTCT
GAAACAAAAGCCAAAAGATAAGACTTCAAACTTCTGATTGCAAAGTGAGAT
AGAAAAGTTTCTTTCTCTCTGTCTCTCTGTTATACCCATACACACACACAT
ATGCACAAACACCTGAAAGAAAAAAAAATTCAGGGAACAGGCCAGGTAGGG
TGGCTCATGCCTATAATCCCATAAATTTGGGAGGCTGAGGCTAGTGGATCA
CTAGAGCCCAGGAGTTCACAAGGCCAGCCTAAGCACATAGCAAGACCCTGT
CTCTACAATTAAAAAATTACCCGGGTGTGGTGGCACGTACCTGTGGTCCCA
GTTACTCAAAAGGCTGAGGTGGGAGAATCACTTGGGCCCAGGAGGTCAAGG
CTGCAGTGAGCATGATTGTGCCACTGCACTTCAGCCTGGGCAAGAGCGAGA
CCCTGTCTCAAAAAAAAAAAATTTTTTTTTTTTCCAGAAAACAATACTA
TCTTAAGCACCAGCACTTTAGTATATTCTACTGTGGACTAGTTCATTTTTA
AAAGAACACTAGGTTGGAAATCATGAGATTGATTCCACAACTCACTAAAGC
ACCGTGTCACTCAGTTTGGAAAATATTTCTCCTTAGAGAGATTACAGGTGC
ATCTTTCTGAGCACCTGTATGTTTTTACATTTGTTTGGCTTCTCTGACCTT
TGATAATTTCTGAGTGTTGTACTATTAAATATTAGTGGCTAGGGGTCAAAT
```

FIG. 8-303

```
TGTGGATCAGGTTGATCCTTATATTTACAAGTTGACAGATACGTTACTCCA
TTGCTTTAAAACTAACACAGAATTAGAGAATTTAGAAAATTCTTACATTCC
ATAATTTAAGACCCAGAAAAAAAAGATTCATATTTTGCATTAGATAGCTAA
AATGGTACCATAAAAACAAATGATATCCACATATATATAGTATATAGTGCT
TCTTCTGTGCCAGTCACTATCCTAAGTTTTTCTCTCCCTTCCCCAAAAATG
TAGGAATTAACTTTATAGATGAAGAAACTGAGGCACAGGAATGTCACATGA
CTTGCCCAAAGGAAATTCAGTCTTCCTTTTTCAATTCTTTTTTCTTTTTAC
TTTGCTGCAGGGTCTCGCTGTGTTGCCCAGGATGCTCTTGAACTCCCGGAC
TCAAGCGATCCTCCTTCTTCAGCCTCTCAAAGTGCTGGGATTACAGGCATG
AGCCACTGCGCCCAGTCAGGAAATTCAGTCTTCTAAACATTCATTATTGAA
ATAATATTTCCATAAACATTTTCTTAGATAAACTTTGGCATCTCTAACTTC
TAAGTAGCAAAGTCATGGAAACAGTCACAGAGAAAATAACTTTATTTTAAA
AATAATAAATTCTTATCTCCGGTGATAAGAAAAGTATACAGCCCATTTTTT
AAAGTATTAATTTTACATTCTAATTTGGTTTTTTTAATGTTTACCATATAT
TTCTCTTTCTACATATGTGTGTGAGTGAATAAAATAAAGGCATCTACAGAT
TTTTACATGTTCAGTGAGATTAGCAGGGTTTCACTTGACAGCACTCTTACC
ATACTCACTTCTTGGCTTTTCCTGATATCTAACATTTTTAAAATGAGTAGT
CCCTTTTCATATGATTCTTCCTTTTTCAAGCACTATTTTTGAACTTTATAT
TTGATTGGCAATAATTTTTACAGACATTATTTTACGATTAACTTTAACTCT
GTTCAAATGATTTCTTCATTTTCAAGTATTTTATTTGAACTGCTTTTTTTG
GTTCAACTACTGAGTATTTAATTTGTCTGTTTTGTAGAAAGGGTATGTAGA
TAATTCCATGTTTTGTAAAAGTTGTCTCTAAAAATCTAACAAGTGTAAGTA
CGATGCTATTACAGGGCTGAGAGACACAGAAAAAACACACACACACACACA
AAATTTTTTTTAAGTATTACTTGGTCTCTAAACTAAAGAATTTACCATCT
ATTTTGGGAGATGAAATCCAAACATAAGCAATGACAACAATTATTATGTGC
TTAAATCAATGTCCAAGACAATAATTGACCCCAAGGCAGGGAAATCACTGA
GAGAGTATAGCAGAGAAGGTGTCCTCTCTGTTCAGATGAGCCTGAATAATT
TGTTCAGTAGGTTTCTGCTACTCATTTATAAACTGCACATCTTCTGTAGTC
CTGGAAAATGTCTAAGAGGAGAGAGGAACTAAGATCAGGGCCACCATTTAA
TTAGGAAGTTCTGGGAGTACCTGACCCAGAAGAAAGATCAGCATAGCTGAA
AATCACCCATAGGAGAAACATCTAGGTAATCTTATTTCTGTTCCACCTGAC
ATTTCAACCTCTCTTTTCAGCTATAAGTATATAAGTACTTATATGTAAGTA
AAGAAATTTACCCACATCATGTTGTTTTTTATTCAATGCTTAACATGTATA
ATGCTAACAACACAGACTTGATGTCCAAAACATTTCTATGAACAGCTCATT
ACTGGATGACTGAAATAATTTTTCCAAGCCACGTGGAGGTTAATGAGTCAG
TTTTTGAAAGCAAGGAGAGAAAAACATTAGAATTTAAGGTGACGTTTCTGT
TGCGTTGTAATCCAGAATACAGAATAGTCAGAGAAAAGCAGAAAGTCTTTC
TTCTTAAATTTTCTGAAAACCAAGGTGTGCATTAAAATGGTACATGCCTAC
TTCCCTTTCCCTTTACCCTTTTTCCTGCATGGAACATAGATATGACCCCT
AGACATGCTGCAGATGACCATGAGGTTGAAAGATACATGGAAGATGGTTAA
CACAGGATGATAGAAGAGACCTGCATACTTGGGCAGCCTAGACAGCTCCTG
CCAGCCCCCAACAAAACAGCCTAGCCTTCTTGCCAATCAAGAAAAAAAATC
CCTTCTGGTAACCCACTGTAAGTGAATTTCTGTAAATGTGGCCCAATGTAT
CCATAATTGATATACAAATATTAGTTTAGTGGGTAGCACCTCTCCATGAGC
ATGTCGACTTCATGAGACTGAGATTTTTGACTGTCATGTGCAGTTGTCCCA
TTACAGTGCCTGGTGCATGGGAACAGCTCAACTGTGCATACCCATTGAAGA
```

FIG. 8-304

```
AATAGATGCATGGTCAATCGAATTTCCAGGTATATCATATGTTTCCATAAA
AAAAGTAAACATACAGCATATCTCCTTCCAGTTTATTTATTTTTCTCTCTA
GGACCAATTTACAGTCTATCAGCAGTGCGTGAGCACCTGTTTCACCACATA
TACAAACCCCTCCAAGACTATAAGGATATCATTAAGCTTTTTATCACTGTC
AGTTAAGTGGTAAACATAGTTTTCTACATACTTTGCATTTTTGTTTCTCAT
GAGATTCAATGTTTTACATGGGTAAGTTGTTAGATCATATTTATTCAAGAT
GAGGCATTTGTCTCCTGGTAAGACATCTTGGTCTAATGCTGACTCTGGGGT
GTGGACATTTGGCTGTTGACTGTGAGGTGGCTATCTACATGTGGAGTGGAG
GAGTCCTGGCCTTGGATTGAGGAGAACAAGGTCAACTTCTCACCTCACTTG
TTTCTGGCTTTTGTGACCTTGGACAAGTTTAACTTTTCTCTCTCCTAGTCT
TAGTTTTCTTGTCTGTAAGTGACAGCAATGATGCTGTCTTTGTTGGGGTGG
GCTGCCATAAAAAAATACCATAGATTGTGTGGTTTAAACAACAAAATTTTA
TCACAGTTCTGGAGGCTGGAAGTCTCAGAGCAGGGTATAGCATGGCTGGAT
TCTGTGGAGAGGGCTCTCTTGCTGGCTTGTAGAGTGCTACCTTCTCACTGT
GAGAGCTCACATAGCCTTTCCTCAGTATATGTGCAGAGCTCCCTCTCTTCC
TCTTTTTTTTTTTCTTTTAAATAAATTATTTAATTTGGAAGACCAAGTGC
AGAATCTTCCTCTTCTTATAAGGCCACCAATCCTATCCAGTTAGGAACCCA
TCCTAATGACCTCATTTAACCTTAATTACCTCTTATAAGTCCTGTCTAGGA
ATAGAGTCATATTGGGGTTTATGGCTTCAATATATGAATTTGGGGGGATGG
GGAGACAATTCAGTCCATAGTAAACACTTCCTCAAAGAGTAGTTATAATGT
TTATAAGAGACAATGTAGGTAAAAGTAGTTTCAGTTGCATGCAGCTAAATG
CAGTTTAGTATCCCTTCAGAGTCCTCCGCAGAAAAGGCACCTGATAAATAT
TTATGTGGCCTTAACCTAAGGTATTATTCTTTATATAGTGCCTTCCCATGT
AATGATTGATGTCATGTTTATCATTTGCAGTGCAGTTTATTTCTTATAGGT
CATGGCTACAGAAACATGGGAGAATGACCATCATTAATAGGTCATTAGAAT
ATGTAATTTCAATTTTTTTTCTTTTGAAGGACTATTAGGTTAACAATGAT
TTTTAAAATTTATAGTAGATATGAGTGCTATAAAACAGGAATTTCCATATT
ATTTTGGGATTATAAATTGGTATGATCCTGAATAGCAATTTGGCAATGTAT
ATGTTAAGAACCTTAGAAAATGTTTTTCACTTTTGATTTAGTATTTCCACT
TCATGAAGTCTATCCTTAGGAAATAATATTTGAACAAAGATTTATGTACAA
AGATGTGTGAGCTATATAATCTATAATATAATGCATAAAAATGGGAATCAA
TTGAAGTAGTCAATAACAAATACATAATTATCAATATATCCATAAATTATA
CATCCATAAAAAAGTTTCTAAGTATATTTATCTAAATATATATCATGACAC
CTAAATTTATTTTATATATGATACATGATGTGAGATATATGTATATATGAA
TATGAGTATATATAATATACATATAAAAAGAATAGGAGATACTAGGAGTTA
TTTTAATTTTGTCTTTATGTTTCCTGTGTCATAAATTTCTATGAAGAATAT
TTTAATAGTTTTATGCATAGAAAAAGAGCTAATTTTTCTCAGCCAGGTGT
TCATTTGTCCTTCTTTGATTGTTCAAAATACCTCCATTTATCTTCTTCTAG
GATCACTCATTTTCATTGGTTTATTTGCAAGATGAAACAGTGTCCAGCAGT
GACGACTGTTGGAAAAGATATGTCTAAAAGCTGTTGTCTCCCCCTGGAGAA
AAGAGAGAGAGTGATTGATTCACTTCTGTAATTTATCAGATATGAGATATT
GTATTTGACTCTGAGAACAATGATAATGATGATGGCTAAAGTTCACTGGAT
GTTTGCTCTGTGCCAGGCAGTGTTTTAAGCACTTTACACAATAGATACCAA
TGCATTTAGTTGTTCCAACAACCTTATGAGATACCTACTGTCATTCTCCCT
GCGTTATAGATGAGGAAATTAAGGCACAGAGAGGTTAAGTTTCCCAGGTAG
CACAGCTGTTGGATAATGAGCCTGTGCAGTAAACCCACATCCTCTAGCCCT
```

FIG. 8-305

```
TGAATGTCTGTACGCTCTTAAAAGATGAATGTAACCTAGTCAGTGTCCTAA
AGTTCCATTTGATCTAAACTTGAAGGATAAAAATTTATCCAGTGAGGAAAA
AGACTTAGTGTTTTTCATAAAGAAGATACAGCGACGAAGGCCAGGCCGTGG
GGACTGTCTGATTTTTAGAGCCTAGAACCCTGAGCACACTCTCTAAACCCT
CCAACATGCTCTTACTCTGTTGCCTGCTGAGCATCTTTGATCCACTCTTGA
GGCTAGCAGTTTTCCTTCCATTCAAGATCTCACAACGTGTATTGTTCTCTG
CAGATTTTTTAAACATGCAATTTTATTTTTAATTGTTAAAAATATATTTA
TTTCAGTGCACTGAAGCTCAAATGTGTGTGTTTTAAAATCTAGTGTCCAAG
GTTCATTACCCCAATTGTTTAAGCAAGTCTAACAACAAAAGGGGCACATTT
TAATTTTCAATTTTTTTTTGTTCTAGCCTACAGTTGAGTTTGGGCAAATAA
TAGTAGACAAAAAAGTGAAAAGAAAACTAAGGACAAGAAAATAAAGGAAGG
GAGAATGGGGGGAGAGGAGGGAGAAAAGTGAAAACAAAAGTTTATTCATAT
TTCTCTTGAATCCAATTCTTTTACCATTTGAAAACTTGATATGGTCAGAGA
ATAAGCCTAGAATTTTAAGTGATGAGGATAAGGTTTTACCACAGGTAGCCT
CCTCTACATAGGTCTATTTCCTCATAGAATGAGAGAAGCCCCATCATTTCT
GCTCTTTTACCCTTCTGAGCCAGCAGCAAGGAGATCTACTATCAAGGCATG
AGCAACTGTAGAAACATGAGACCAGATGTCTCTATTAATTATTCTACAAAT
TGCGCATTGGATGATAAGGTTACATGAATCTTTAAATCAGCAAACCAAAGT
CCCATTATTATTACATATTTTTCCTCCTCAGAACTGAAGTGGGGCGGGGT
ACAGTGACTCACACTAGTAATCCCAACAATTTGGGAGGCTGAGGCAGGAGG
ATCACTTAAGCCCAGGAGTTTGAGACCAGCCTGGGCAACATAGTAAGACCC
CATCTCTACAAAAAACTTTTTAAAAAATTAGCTTGGCATGGTGGTGTGCAC
CTGCTGTGGTTCCAGATACTCAGGATGCTGAGGCAGGAGGATGGCTTCAGC
CCAGAAGGTGGAGGTTACAATGAGATGCGATTGCGCCACTACACTCCAGCC
TGGCAGCCTGGGCAACAAAGTGAGACCCTGTCTCTGAAAAAAAGAACTGAG
GTCAAGGAGTAGTAAGAAAGTGGCTCATTCTCCAGATTTACTCTCTTTTTC
TTAATTATAATGAACTCATGATACTTGAGGATATGTCAAACTGATCTTCAG
ACCCCAAAGAAATTACTCAGAGCCTAGAATACCTTTCAGGAAATGTTACAG
TGGTATACTCTACTCAATTTAATTTTATGCTTGGTCATCCAGGATTACACA
GGCTAAAGGTAGGAAAAGTTTCACTAATTTTTAATGTCTTTTAATTTAGGA
CTACTGGGATTGTCTGTCAATGTGCTGAATATATATATCCTTCCAAATCTG
GAAGATTTAAGAGAAATGATAGTTATCATTCTTTAAGTCCTTAGGAATATG
CCTAGAGAGCTAATTTCATATGTTCAGGGAAAAAAAGTGTATTTTTTCTCA
ACCTGTTGGACCCCGGTAAACATACTATGATCAACTGGCATTTTCATATCA
AATAATTTATGAAATTCTTATAATTTATAGAAGGCCAACTCCTACCAAAGT
CTTCAGTCATAAGCTGCTTCAAGTCCTTTTAGGAGCGTAAAGATGGTTATA
AATAAAATTTGTCAAACAGCAGTAAACACAGTGGTTTATATGCATTAAGGA
TCTTTAATCTTCACATACTTCTAGAAGGTAGGTGCTATTACCATCACTGTA
AAGGTATAGAGAAGGATACTAATGCACAGAGAGATTAAATGACCTGCCTCA
GAGTCCCACATCTTATATGTGGTGATCTGGGAGTCAAACTTGGAGTCTGTC
TCCAGAAGCTTCACTTTTGTCATCATTGAGCAGTGCTGTGCAGCCATTTT
ACTAGCATGATACCACGTCTGGAACTAGTGTTCTATAGGTGCTATTTCATT
TAATCTTCACCCCATCTTTATGAGTAGGGCAATTATTACCACTCTATAGGC
TCAGGGTAGTTGAGTTTGTCAAACTGTGACTGAAAGACATTTAATTTTTGG
CATACTATTTACTTGTGCTCAAGGTATATCAAGCAATGGACTGATTTCACT
CAACAAAGTATTTTAAAAAGATGATTTATAAAATAGAAATGGGAGAAAAAA
```

FIG. 8-306

```
ACTACAAACTGTCTAGGAATAGGATGTTATGTTTGCACATTATTTTCAGTA
GAAAAGAGTTTAGTATGGATACTCTCTTCTTGTATAAACCAAGAATGTTAA
AAGAAAACAATTAGTGATTCTCTAGAAACAATTAGTGATTCTCTAGAAACA
CTTAAGATTGGCTGTGCAGCACTATGGCTATCTCTGTGTAGTATTTTCCAC
TGACAACCAACATTTCCATGTTAGGTAGGCCATGTCTTCACGATTTCTGGC
ACCAGAGTTTTTCAACTCCTCCATTTTGGTAAAAATATCTCATAAAGGAG
CAAGTCTAACCATGTGAGTTTGTTTAGTTTTTTGTTTTTTGTTTTTTTGAC
AATGGCTTTGTAACAACATTTAATAATCTGCATATTAGAGAAGCACAGAAG
TAGGGCAAAAAAAAAGTTATGAGGGTAATTACAAATATTATAAGAATTCC
TTAAAGTACAAATTGTCTCCAAGAATTTAATTGGCTTGTCTTAGATGAATA
GGTCTCAAAGATCAGTTTGGTCAAAGATCAGTTTGGTCAACTTTAGTTAAA
CAAGTTCATTTTTCCTAATTGATTATTTTGACTCAAATGTGGGCCACAGGC
AGAAATAAATTTTCTAGTAAATATTCTTATTTAGGAACTTTTAGTCAAGTT
ATAAAGGTCCTTGTTACAAACCTGCAAAAAGTTAGCATGCCAATATCTTAG
TAAAATATAACTGAGATTTGTTTATTTGCTTGTTTTTTAATACTTGGGAGG
GCCAGATCAAAATTTCATCACTGGAAAGACAGATAATGGAGAAAAGGACAA
AACAGAATAATACCACAGGTAAAAGAAGGAAGAAGCTGTCTATTTCAGACC
TCATCTTCCTCTGTAGACTTTGAAGAGGAAACTTCCTACTTCCAGAATTCT
GGAGGTCTTTTAATGAATCTCAGAACTGTATTTTTAGTGATAGTGTATTTC
TCAGTGAGATTCCAAATGTGTTTACACTGGGAAGCACATATCCATCTGCTC
TGAAGTATAAAAGCAGTATTTGTTGTTTGAAGTACTGAAAATGGAGGTTCC
AGCATTGTTATAATGTTGTCAGAGAAGATTGGTTATTACATTAAGATATGA
ATATAAATCATGGCTATATAAAAATAAGAAAAAGATTGAAGTCTTATTTTA
GAGTGACAATCCATAGTAAATTGAATGTACCACATTAACAAACAGTAACAA
CTTTTTAAATAAGTAAAGGCTCAAGGTAGTCATTATCTCGAATGCTTACTT
GTGTTTCTCTGTAGCTATAGTACTTGATAGAGTCAGAGCTGTTTGGATTAA
CCATAGCCCTTAAACAAAGCAGGCAATTGTGTTCCCGCATAGGCATGACGA
AAACAGAGGCAGTCATCCAAAACCTGCATGGTCCTCTACGCCCACACGTAT
ACAGTACGTGATTTACAAATCTAAAGTGGCGAAAGCAACAGTATCTATTCT
AAGGCAATCATATGTTCTCTTATCTGTTTATCAATGGTTATTCTAAACTGT
GTAAAAATGTTATTTGCATAAAACTACACTGTTTCTTGTGATTTGTATTTT
GTACCCTCCAATTTAGAAATTGTCCAGGTATCCAAAGATTGAGAATTAATT
TACTCAATTTAATAATATTCACCTAAATTCTTAAAGTTATCATACACTGTG
AACTCAGTACTTAAGCTCACACATTGAATCCTTATAATTAGTAACATAAAA
TTTAATTCCATTTTTAAAAATGACATTATCTATTATCATTTAATTTGGTTC
AATGAATAATTTACAATTTTAGAATAATAAATAAAGTGATGTTAACTCATG
TAACCAGTACAACTAGTGGAAGAAATTTAGTAAATGCAAGTTAAATTAGCT
TTTGTTTTTGTTTTTAGAATATGAACCCTAAACTTGTGTATACTATAATA
TTCTGCTAATATTATTTTTACAGTATAAGAATAAAGAAGCCATTTTTAAAA
TGAAATTATTAAGCCAATTTGTCCAAAAAAAATCTTGATTAGATGTATTAT
ATATTTCCTTATTAAAAAACCTAATAAAAGAGGTATTAATATTTTTAAG
TTATTTAAAAATTGTGAAGTATTTTTTTTACAAAATACTTTAAGCTGTTAA
CTAAGACCACTAATGAAACTCACAGTTAAACTTTTTTTCTCTTAATTAGAA
CTTAAAGAGGTAGCACATTTAAAGCACAAGGAAAATTTTTGATTTTTTTTT
AGACAAATGAGTTTTTATTTAAATTGATGTATTTTAAGTCTTTATGTAAGC
CAACTAAAATTTAAGATTACATTATAATTTATTAATTCCCTTAAGTGGATA
```

FIG. 8-307

```
ATTTCACAATTATTTAAATTCATAAAATAAGATAGTCTTTTCTGGGCACGG
TGGCTCACGCCTGTAATCTCATCACTTTGGGAGGCCGAGGTGGATCACCTG
AGTTCGAGACCAGTTTGGCCAACATGGCGAAACCCCATCTCTACTAAAAAT
GCACAAATTAGCCAGGCGTGGTGGTGCACCTGTAATCCCAGCTACTGGGGA
GGCTGAGGCAGGAAAATTGCTAGAACCCTGGAGGCAGAGGTTGCAGTGAGC
CGAGATTGTGCCACTGCACCCCAGCCTGGGCCACAGAGCAAAATTCTGTCT
CAAAAAAAAAAAAAAGATAGTCTCAATCTTATTGCCAATTAGGAAAGCTAA
CCGTGCTAATAGAACAGAATTTAAAGTGGGTAAAAACAGAGCCATAGGTTA
TCTATTTAGCATGTTGATCAGTTAAAGAAATAAAAGTATGTAATTAAGATC
AGAAGTCCCTCAGGTGGCACCACTGCTGAGAATATGAATAATTCTGATTCT
CAGTTTAGAAGAAAATTCTAGTTTCCTAGTTTCCAGCATCACATCCCTTAC
AATAAACTCGTTAAGGTTTAGAAAATATTAAATCTTTGTTTTATTCAGATA
TTGAAAGCACTCTTTTTTTTCCCTGACTCAATAGTCCAATTTGTAACAACA
TTATGTTTCTTCTGTCCTCTAACCTTACTTAAAGAACGTGAAGGGGCAATA
ATGTGAAATTACTAAAATTAATAATAAGCTGTAGAGCCTCTGCCATAGCAG
TTATTGAGACCAGACATTCGGTTTCCTTGATTTCCTTTTTGTCTCCTGTTA
GTCCTAACACTTTCTTAAAGTCAAAAGTTATAACAGGGCAGCCATTTTATA
TTCATATCATCTTAACACAGGAATACTGGTTTTGCAGATATCGACAACTAT
TTGGACTCAAAAAAGACAAGTTTTGGAAGGTGGAAAGAGGCATACAAGCAC
AAAACATCAAATCCCATGTAAAGTCAGAAAGAAAAACACCAACTCTAACCC
TGTGTCCTCACAGAGAATATCAACATCTTCAAACAAAAACACCCCAAAAAA
AGGTTAATAAATAAACCAGATTTCCTGTCCTCTCCACTGACTAATCACTTA
ATGATGTGACCAGAAAACCAGAATTCAAATTCTACTACTGCCACCAATATG
CAACCAATCAGCCAAGTCCAATTAGAATAACCAAAACAAACAAACGCGGAC
GATAAACTTTTAGCATGCAAAAGCCAAAGGAAAGTGAACAGAAAACTCAAA
GGGTCCAGGGATAGACAACCTGTTTCCAAGACACACATTTCTGTTGGTTCT
TATTGTATGACTCACATAAACACTGTCTTGGTGGAAAATTCAGAAATAAAT
GACCAAGAAGTTAATAATTTGCTTACTGGGTACTTGTACAGAAGAGAGAAC
AAGCAATAGAATTATTTCATCTAACACAGGCAAAAACATAATCTATGTAAG
AGAAAGGGGAAAAGGCGGGGGAAACAATACTGAATTTTGTTTGCAGATTTT
GGTTACACTGATTAGTTAGTTGGCAGGTAAGAAAACGGTCAGTCTGAATGG
GAATAAGTGACCAGGTCCATTACAGGCATAGAAAAAAAAAAAACCATTTAG
GCCCGGCGCGGTGGCTCAAGCCTGTAATCCAGGACTTTGGGAGGCCAAGGC
GGGCAAATCACCTGATGTCCGGAGTTCGAGACCAGCCTGACCGACATGGAG
AAACCTCGTCTCTACTAAAAATACAAAATTAGCCAGGGTGTCGTGGCGCAT
GCCTGTAATCCCAGCTACTCCGGAGGCTGAGGCAGGAGAATGGCTTGAACC
CGGGAGGCGGAGGTTGCTGTGAGCCAAGATCGCGCCATTGCACTCCAGCCT
GGGAAACAAGAGAGAAACTTCGTCTCTAAAAAAAAAAAAAAAAAGAAAAAA
AAATTTACTTGTGAGGGACTCTGGAAATTTCATTTCTCATCAGAATTTCTC
AGATAAGTTATCTAGGCAAGGCAGCCTGTGATTGCACAGCAGTGTTCAAGT
ATAAGGCCTTGTCTGGCACCAAAGACAGGCCTTAGTTTATTTCCCAGGTGT
GAAAGAAATTGCAGATTTAAGATCACACAGTCCTTATGTTAAATAACTGTA
ACCTAAATTACATGGTATTTAAGTTTGTAAAAATCTGCTTTAACACTAATT
TTATTTATTGTATATTCCCGGTTTTTAATGGAGAAAGCAAACTTCTAGGTG
CTAAAAACGTGTTCTAGACTTGAATAAAAAGATAGGTAGACTACGTCTAAC
CCTTCATCTTAAAATCTTTACCTGGAAAAGACCATGAGTAAAATACTTAAG
```

FIG. 8-308

```
GGAATGTGGAATTTCCCAGGCCACAAAGCGGCCTGCAGTTGTCTAGGAAGG
GAGAGTCCTCTAGGAGATACAGTGTATGTGCTAAGTTTAATGACGTCTCCT
CTTCATTCTCCCCCACCCAGCGCCTAGTCCTTACTGGCCTTCAGTTCAGTG
TTCGAAGGCTTGTCAATTTACCCAGCAGTTAAGAGTTGGCTTCTCCTAAAG
CAACTTTCAAACTTGTCTGCATGTTACAAGCCCCCTACGGAGATTTTAAGT
TTCAATCAGGCAACACACCATTTATGGCTGACTGAGCACTGGGATTCAAGC
AAAATTTGATTTGATTTGAATCTTGAATAAACCAGTTGAATAGAATAAGAT
GTATGAAGCAACATCTGGCGCAGTGCTTACATCTTTAGTTCTGTACTGCCT
TAGTGTTGTTATCAAAACTGACGCATATTAGTTAAAAGACTATTACCGGGG
CAGTTGGAAACCCAGGAGACACACCTTCAGTATACTACGAAGGTGTGCGCC
ACGAAAACAGAGGGGGAGTCCTTCCTTAGGCAGTTACTGCCCAGGTTCCCA
CTCCGGTCCGCTATGTAAATCAGAGTCTCAAAACAGCTTTCCCTCGATTGG
TTAATATTTAAAATGACAGGACAGCCTATTGGCTAGAAGCTGGTGGCGAAA
TTATGACATTACGGCAACCGTTGATCCTGGCGACGTAGACAGGGACAGACA
GCTGGGTCTGAAACCTAAGCGAGCCTGCGGTTCTTCCGGGAACGCCGAGT
TAGCAAAATGGCCGCTTGTCTCCATTTTAAATTTAAGCACAACGAATTGAC
CCCAAAGCCATTTTTAATGGCTGGCTTCTTTCGGGTTCAGGACCCTTTGTC
CCTCTCTAAGCTGCAACACTTGTCCCCACCCCTCTCCAGTTCCTATATTCT
AATACCCCTCCGCCGCCAAATAAAATTTGGCGTCTGGCCACAGCTCTTTTA
GTGGGTATCTGGGTGGCTCTTAAAAGAGCCTTTGGGGTTAGGTGTTAAGAC
GCTTACTTGGAATGTTTACTTGGAGCTGGTGTACTTGGTGACGGCCTTGGT
GCCCTCCGACACGGCGTGCTTGGCCAGCTCTCCGGGAAGCAGCAGGCGCAC
GGCCGTCTGGATCTCCCTGGAGGTGATGGTCGAGCGCTTGTTGTAATGCGC
CAGGCGGGAAGCCTCGCCCGCGATGCGCTCAAATATGTCGTTAACGAAAGA
ATTCATGATGCCCATGGCCTTGGAAGAGATGCCAGTGTCGGGATGGACCTG
TTTCAGCACCTTGTACACGTACACAGAGTAACTCTCCTTGCGGCTGCGCTT
GCGCTTCTTGCCATCTTTCTTCTGCGCTTTGGTCACTGCCTTCTTGGAGCC
CTTCTTCGGGGCGGGAGCAGACTTGGCTGGCTCAGGCATCTTAAAACACCA
GAAATGTGTCGAAAGTAAAGAGCGGATTTCTGCTACTTATAGGGCTTTTAT
GCTAATGAGGGATGGAGAGTACCTCTTAGTTAATTGGAAGACAAACTGCAC
AGTTGTCATCCGTGGGCAGAGCTATGCAAATGAGGTATGAAAGTACAGCTT
TTCTATTGGCTATCTGACTAGCATTTGCTACCGACCAATCAAAAAGTCGGA
TTTACTCCCCAGGAACTACCTATAAAAGCGGCCATGTTTTACATATTTCTT
GATTTTGTTTGTTTTCTCGTGAGCTTAGGCCGCTGGTTTTGGTGATTTTTG
TCTGATTGCAATGTCTGGACGTGGTAAGCAAGGAGGCAAAGCTCGCGCCAA
AGCGAAATCCCGCTCTTCTCGCGCTGGTCTCCAGTTCCCGGTGGGCCGAGT
GCACCGCCTGCTCCGTAAAGGCAACTACGCAGAGCGGGTTGGGGCAGGCGC
GCCGGTGTACCTGGCGGCGGTGTTAGAGTACCTGACCGCCGAGATCCTGGA
GCTGGCCGGCAACGCGGCTCGCGACAACAAGAAGACTCGCATCATCCCGCG
CCACTTGCAGCTGGCCATCCGCAACGACGAGGAGCTCAACAAACTGCTAGG
CCGGGTGACCATTGCTCAGGGCGGCGTCCTTCCTAACATCCAGGCCGTGCT
TCTGCCTAAGAAGACCGAGAGTCACCACAAGGCCAAGGGCAAGTGATTTGA
CAGGTATCTGAGCTCCCGGAAACGCTATCAAACCCAAAGGCTCTTTTCAGA
GCCCCCCTACCGTTTCAAAGGAAGAGCTAACCTCACTGCTTGTAGGTAGAA
GGAAAAAAGGCACTAAGGTAAGTTAATTTTATGCCAACCTTGAGCAAAGCG
TATTACTGCTTTTCGGTTTTTGGGGAGCGCTGTTACTAAAGGTTGGTCTGT
```

FIG. 8-309

```
TTGTATGTAATAGTAGGTCAGTTACGTACTATCATACTCTAAAGAAATATT
CTAGTTAATGCTTTGTAAGATCGACCATAGTTAGTGCCTAACAGTTTACAT
GCAGGGATGCCTCGTGATCTAAACACTTCGTTGTGATTACTTTAAAAATGT
AAATTGAAGGCAAAACTCTAACGTGTTGGTAACCTTGTTTGGTCCTCCGAC
TAGTCCCCCGTCTATTTTTTCTCAATTTAGGCTGTAGGCAGCCTCACTTT
CCTAATTCTGTGAGAGTTATAGGTCCCATTCCTGCTAAAGTGCAGAGTATA
TTACCTAAAAGTTAACCAGGGAGTTGAAAGGTGTCTGTAAAACAGACTAAT
GTCCCTAATGTAGAACGGTGCCTGACATGCAACTTACTCTTGTATTTTAAG
AAGCTCAAGCGTCTAGGTTGCCATTACAGGCAGAAAAGGAAATAGAGTGGG
GCCTGTGGCCACTCAAAAACCTTTGCTTTCTGCTCACCCCTCTAATCCTAC
CACTTTGGGAGGCCGAGGGGGCTGATCACCTGAGGTCACGACTTCGACACT
AACCTGGCCAACATGGTGAAACACCTCTCTACTAAATAAAAATAATAAATA
AAAAATAAGTTGGGCGTGGTGGCACATACCTTGTAATCCCAGCTACTCTT
GAAGCTGACGCAGGAGAGTCGCTTGAGCCTGGGAGGCGGAGGTTGTAGTAA
GCCGAGATCGTGCCACTGCCCTCCAGCCTGGGCAACAGTGAGACACGGTCC
CCCAAAAAAACCTTTGCTTCTAGGGATCTGGTAACAGCTGCCCCACCCACA
AGAAATGGAGATCTGGGACCATGGACAAATTCTAGAGACCTATTTTCCTG
GATTCTGTGAATCTCGCCGAGGTTTTCTTCCGGATCTCGGTTTCTGCATTT
TTTTGTTTGTTTGCTTGCTTTTTTGAAACGGAGTTTTGCTCCTGTTGCCCA
AGCTGGAATGCAGTGGCGCGATCTCGGCTCACTGCATACAAACTCCGCCTC
CCGGGTTCAGACGACTCTCCGGCCTCAGCCTCCCTAGTAGATGGGATTACA
AGCGCCCGCCACCAGTAGAAACGGAGTTTCACCAGGTTAGCCGGGCTGGTC
TCGAACTCCTGACCTCAGGTGATCCGCCAGCCTCTGCCTACCAAAGTGCTG
GGATTACAGGCGTGAGCCACCGCGCCCGGCCGGTTTCTGCTTTGATCGGAA
TTAAGTGGGCAGAAAAGTCTAGGCGGGCTAAGTCTTGCCTATGCATCTGCG
CCCAGCTGCTCAGACTGGCCAAACAGACCCAGTCGTTTAGTCTAACGCTTC
TGGAACTCCACTGAAGCGTTTTGCATTGTTTCGTTTGGAGCCTTCAAATCC
GAGTGTGTGGCAGGAGATAATAATCCTAGCAGAAGCTGTTTACTGCTGACG
CGCCTCCCACTTCCCAGATACTGACACCGGCTCAGGGCGGATCCAGCCTTT
TCCGCTCTTCCCTCCCTCCACCCCCTCCTTTCCCTACAACTACTCTCAAAG
GAAAAGGGTTGGATGTCCCATTTGGGTGAAAACAAAGTGGCATAAAAGCAA
ATGATCACCTTTGATAGCCACATATTAGAATTTTCCGAGGGTATTTTTAAA
TTACAACGATTCTAATGGGCAGCTGGGCTGAGAATCATCAGATTTGAAGGT
CTGGTTTCACATGGCTCTTGGGCTGAGAAGACCGGATTTTCCCCCCCCAGC
ATTTCCTGTATGTCCGAGAATTTCGATCCTAAGGTTAGAATTGCCTTATGG
GCCTTGGAATCCTTTTTATTCACTGACCAAATTGCCTTTGATTCCAGCTCC
CAATCGGTGTGTGACCTTGGCCTAGGGCTTAATCTCTTCCTACCTCCATCT
CTTCCTTGTATGCTTTTGCTCACCTTGAAATGAAAAGAACCTGGCTCAGCA
AGTGTAGATTCTGAAATCAGAAAACAGGCTGAATAAGAGAGATGGTTTATT
AGGCACTACTGTGTGCCAGGCACATTTCATGAGCTTCCAGTATGTTAATTC
ATTTAATCCAACAATCTAAGAGATAGGTTTTATCCTTATTCCGAATTTTGA
GATGAGCAAACTAAGAAACAGCTTAAAGAACTTAAGTTGTAAGGCCAGGAA
AACAGTACTTATAACAGCTGACTATTCTATAACCACACCTCCTTAAGAGAT
TATTGTCAGAAAATAGAAAGAGTAAAACATCCATACATAATGGGTAAACT
TTGTCCACATACCAGAATGTTACTAATGGCTTTCTAACCTCTGAAGAATTT
AAGGGAAGGAGGAAAGGTAATTTTCCCCAGGGAATCTACACGAAGAGGTAA
```

FIG. 8-310
```
ATCTTGACAATGTATTAATACTGTAAACCCAGGGAAAAAAAGCCAGTACAA
TTTTTATTTAGGGTGTGGCAAATAAAACAAAGGGACACGTGAAAACATGGC
TCAGTAAAGAGCTACAAGACTTGGTGCAACTGACTTATTGTGGTGAGTGAG
AAAAGGAGAGAGAGAAAACTTGAATTTCAATTCTTCTCTCTGGGCTCCAAT
AACAAGATTTTGTATTCGGTCTATTTAGTAGTGAATGATACATTGTGTTAA
GTTTGTTAACCTAGAGGCTTTCATCTTAAGCAGTACTTAAGATGTAGACCC
CCTCTTATTCAAATACTGATAATCAGCATAGAACTTGGCATACAAGAGACA
CTTGGCTGTTGGGCATTGAGAAAATGTTGAACTGAATGAATCAATGACTTA
GGCAGCCAGGAAGCACTTTGTTGTAGAGAGTTGGTTTATTACTAAGGAAGA
CATTAAGTATTAAATATTAGACTAATAGGTTGCTAATAGTGTTTTCTCTTT
CCAATAGAAAATGTCTTCTGAGGCTGATCTGGTGTCTCACATCTGTAATCC
CAGCACTTGGGGAGGCTGAGGTGGGTAGATCACCTGAGGTCAGGAGTTTGA
GACCAGCCTGGCCAACATGGCGAAACCCCATCTCTAATAAAACTACACAAA
TTAGTCAGGTGTGGCGGTGTTCACCTGTAGGCGCCTGTAGTCCCAGCTACT
CAGGAGACTGAGGCAGAAGAATCACTTGAACCCCGGGAGGTGGAGGTTGTA
GTGAGCCAAGATCGTGCCACTGCACTCCAGCCTGGGCGACAAAGTGAAACT
CCGTCTCAAAAAAAAACCAACCCCATCTCTACTAAAAAATACAAAAATTAG
CTGGGCATGCTAGTGCACGCCTGTAGTCCCAGCTACTCGGGAGGCTGAGGC
AAGAGAATCACTTGAATATAGGAGGGGGAGGTTGCAGTGAGAGTGAGACTC
TCAAAAAAAAACAACAAAACAAAAAGTAACAAGAAAAAAGAAACTATATTC
CAAAAATCCAAATTTCACTGGCAGTTTGTTCTGGGAGCTTCAGACACATAG
AAGGTGTCAGTTAACCAGTTCTTACCTAAGAGGTACTGCTAAGAGCCTAGT
CCCTAAGCAAAGGGAGCTTCAGAGAAACACAGAAGGTGCCAGTTAACCAGT
TCTTACCTAAGAGGTACTGCTAAGAGCCTAGTCCCTAAGCAAAGGACATTC
CTCGTAGCTCTGTCCTGTCTCCTCATCTCCAAAATACTTTACCTTCTACTT
TGAAATGCCCACTATTATATTCAAAAGCCCTAGTTACTTCCAGGGAAAATT
ATCTATTGAGCAATGAATTTCGGTAGCTTCAGTTGGATTCCAACTCTTGAG
CAAGTTTTCATCTCCCTTGCCTGAATGGCCCTGGGGAGGACTATTTAAATT
GGGGCGAGTGGATGAGGATGCTAAACCTAGAGGTCTCCCAATTACCAAAGG
CACCTGGGCACCAGGGACTAAAGTTTGTCTCAGGAATTTACTGAGATATGA
GGCTGAGATAAAATCATTTTTTGGTACATAAGGTATCTTGAACAAAGCAGA
TCAGTTTAACACAAAATCAACAATCGTAATTTCCCTTTTTAAATTTCCAAA
TCTATGTAGCAATATCCTTTCCTTTAATTCATTCATCATCTCTATTCACTT
TTTGTATTCTGTAAATCATTTGAACTTTTATAAGAATTATATTTTCCCCTT
GAGGTCACAAAAAAGAAAGTATTAGAAATTTTATAACCAATTTTTAAAAAA
TTATATTTTAAGGTTAAATACAAACCTTCTAAAGGTTTGTCATCTGTTGAT
CCTAAATTATAATTATAAATTTATATATTCCTGTTGAATATAATGCATGTG
TGTTACAAGATTATTAGCAATTTGAGAATTTCCCGTGCATATTGGAGATGA
GCAAATGGAATAAGTGCTCATGTGTAGCGACAGGATTCTCTATTTTATTTC
AATACTTAATATTGTACCAAACCAAGTAAGAGGAGCATCATGAGAAAATGT
ACTAAAGGACAGTCATTACCTATATTTACACCTAGAAAAGAAAACTATATT
ATTGATAAACTGATAAATCTATTTTATGTATTTATTTATTATTTTGCTCTG
TCATCCAGGCTGGAGTGTACTGGTGCGATTTCCACTCATTGCAACCTCCTG
CTCCCAGGTTCAAGCAATTCTACCTCAGCCTCCCTAGTAACTGGGACTACA
GGCATGCACCACCACACCCAGCTAATTTTTATATTTATAGTAGAGACAGGG
TTTCACCATGTTGGCCAGCCTGGTCTCAAACTCCTGACCTCAGGTGATATG
```

FIG. 8-311

```
CCCACCTCAGCCTCTCAAATGCTAGGATTACAGGTATGAGCCACCGCGCCC
AGTCTGATAAATCTATATTAAAAAGAATAAATATAACCATTGCATCTTCAA
CAGAAATTGGAATATGGCATGTAGATTTCAAAATAAAATGAATTCTCTGGC
ATTGAATTACTGTACTCATGTTGAAGAAATGTCAGAACTTCATTGGATGTT
ATTATATTACAGTTGTTTGTTTGAGTTGTAGTTTGGGCAGAGTAAAGGAGC
CAACATGTCTTAGGATTTAGAACTTGTGCACATTGCCTACAGTTGAAAGAA
GAAAGCATGCTAAATTCCAGCCTCTTTGGTATGTGGTTGGGACGTAAAGTT
TTACCACATCCTTCATTGTCTTAGCCTACTCAGGCTGCCATAACAAAATAC
CAGAGACTGGATGGCTTAAACAACAGAATCTTTTTTTCCATATCTAAGAGG
CTTGGAACAGAAATTCATTTTCTCACAGTTTTGGAGCCTGGAAGTTTAAGA
TCAAGGTGCCAACATAGTTTATGGTGAGAATCTGTTCCTGGCTAACAGATG
GCTGCCATCTCACTGTGTGTTTGTATGGTGTTTCCTTGGTGCCTGCGTGGA
GAGAGAGCTCTAAGTGTCTCATCTTCTGTAAGGACACCAGCCCCAATGGGA
TTAGGGCCCTATCCTGTGATCTTTAGTTTTATGTACCCCCTAAAGGCTCTA
TGTCCAAATGCAGTCACACTGGGGTTTAGGGTTTTAATAAATGAATTTTGG
GGGACACAGTTTAGTCCATAACATTCTGTCCTTGACCTGCCAAAATGTATG
TCCTTCTCCCATACAAGATAAATTTATTCCATCCCAGCCGGGCATGGTGGC
TCACACGTGTAATCCCAGCACTTTGGGAAGCCAAGGCAGGCGGATCAGAAG
GTCAAGAGATCGAGACCATTCTGGCTAACACGGTGAAACCCCATCTCTACT
AAAATAAAAAAAAAATTAGCCAGGCGTGGTGGCGGGCGCCTGTAGTCCCAG
CTACTCTGGAGGCTGAGACATGAGAATGGCATAAACCCGGGAGGCAGAGCT
TGCAGTGAGCCAAGATGGTGCCACTGCACTCCAGCCTGGGCGACAGAGCTA
GACTCCGTCTCAAAAAAAAAAAAAAAATTATTCCATCCCAACAGCCCCCTG
AAAGTCTTAACTCATTCTAGCATCAATTCTAAAGTTCAAAGTGTCATCTAA
AAAATCATCTAAATCAGGTTACGGGTGAGGCTCAATGTGTGATTCATCCAG
AGACAAAATTCCTTTCCAGCTTTGAACGTGTGAAACCAGAAATGTTACATG
CTTCTAAGGTACAATGGTGAAACAGGCATAATAGACATTCCCATTAGAAAA
TGGAGAAATAGGAAAGAAGGAAGGTGTAATGTGTCCTAATCAAGTCCAAAA
CCTGGCAAGGCAAATTCTGTTAGGTCTTAAGAAAAACCCTCTTTGGCTTGA
TGCCCTGATTTCCAGGCCCAGTGGTGTCTCAGTGTCACCTCTGGCTCTGTA
GTTGGCCTACTCCATCTGCCCTGCCTGAAGTCTCGGTCTTTCAGTTTGGTG
GGGTCCCACCCAGGCAGCCATCTGTGAGAGACTCCCACACAGTTCTGCAGG
GCATCTTTGAAACAGGTAGAGTCAGCCTTGACTACATGTTCCCACCCCCAC
CCTATCCCATCTGTACTCTCTGAGTCTGACATCAAAGTGGCAGCCCTGGCG
GCTCCTGCCTGTAATCCCAGCACTTTGGGAGGCCAATGAGAATGGATCACT
GGAGGTCAGGAGTTCCAAACTAGCCTGGCCAACATAGTGAAACCCCATCTC
TACTAAAAATACAAAAATTAGCTGGGCAAGTGGTGGCAGGAGCGCTACTCG
GGAGGGTACAGATTTAGAGCCTGTAATCCCAGCTACTTGGGAGTCTAAGGC
AAGAGAATCCCTTGAACCTGGGAGGTGGAGATTGCAGTGAGCTGAGATCAC
ACCATTGCCCTACAGCCTGGGTGACAGTGAGACTGCCTCAAGAAAAAACAA
AAGAGTCAGCCCTAGTGATCTTGTAAGTTGCCTTTGGTGGGTCAGTCTTTC
CTTTTCTTAAAGAATAGTACACATTGACAGCCAGGTAGCTCTATGATCCTG
TTCTATAGAATTCAAAAGTCGACAACCTTCCTTTGTTCCTTTCTGTTTTC
TCTGCCTACGTTAGTTTAAATTGGCAGTGTCTCTGCTGGAATAATCCCATC
TCTCTTCCTGGCTTCTGCTGAGATGGCTGATTAAATCCTTGGGTCACACCC
ATTATCTCTTTATCAAATGGTTGTTCAGGCTAGGCTCAGTGTTTCACGCCT
```

FIG. 8-312

```
GTAATCCCAACACTTTGGGAGACTGAGGAGGGCAGATCACTTGAGCTCAGG
AGTTAGAGACCAGCCTAGGCAACATGTCAAAACCCCATCTCTATAAACAAC
AACAAAAAATTAGCCAGGGTGTGGTGGTGCATACATGTAGTCCCAGCTACT
TAGGAGGCTGAGGTGGGAGGATTGCTTGAGCCTGAAGGCAAAGGTTGCACT
GAACTGAGATTGTGCCACTGCACTCCAGCCTGGATGACATAGCCAGACCCT
GTCTCAAAAAACATAAAAATAAAAATAAAACCAAGAAAAAAAAAGAAAAAG
AAAACATTGTTCAACCATACCTCTTCAAGAAAAACTTTCTCAATTTTTACA
ATATAGATTGAGAAATCTATCCCAAATCTCCAAGTTCTGATTGTGTTTTGC
TTAAAAATTCCTTCTTTATTTCGGCTCTTTCCTCTCACATTTCACTTTAAG
CAGTAAGGAGGACCTAAATCACACCTTCAATACTTTGCTTAGACATCTCTT
CTGGTAAATATCCAGTTTTACTGCTTATAAGTTCTTTCCAGTAAACACTAC
AGCGTAATTCAGCCAAGTTCTTGACACATTGTAACAAGAACAGTGATTTCT
ACAGTTTCCAATAACCTGTCCCTCATTTTCATCTGAGACCTCACAAGAGTT
GACTTTAATGTCCATATATATATATTTTTGTGTGTGTGGCGGGGGGAG
TGGAGTCCTGCTCTGTATCCCAGGCTGGAGTGCAGTGGTGTGATCTTGGGT
CACTGCAACCTCCACCCCCGGGTTTAAGCGATTCTTCAGCCTCAGCCTCC
CGAGTAGCTGGGACCACAGAAGCACATCACCATGCCCAGCTAATTTTTGTA
TTTTTAGTAGAGACAGGGTTTCGCCATATTGGCCAGGCTGGTCTCAAACTC
CCGACCTCGTGATCTGTGCCCTCAGCCTCCCAAAGTGCTGAGATTACAGGC
GTGAGCCACCACGCCTGGCCTAAAGTCCATATTTTAACCAGCATATTTAAT
ATTCTATCCATGATCGTTATAAATCTAAGTTTCTATGAAAATGGAAGCTTT
CTGTCCAGCTCTCTTCCTTTCTGAGCCTTTGCCAGAATTGCCTTTAATGTC
CATATTTCTTTCAATAGTCCCTTCACAATTGGCTTTTTCTAGTATGAACCT
CAAACTCTTCCAGCCTTTACCCATCACCAATTTCCAAAGCCACTTCCCCAT
GTTTAGGTATTTGTTGTTGCAGCATCCCACGCCTGGGTACCAAAACTTAGT
CAGCTTGGACTGCCATAACAAAATACTACAGACTGGTGGCTTAAACGATAG
ACATTTATTTTCTAACAATTCTGCAGGCTGGAAATCTAAGATCCAAGTTGC
CAGCATAGTCAGTTTCTGGTGAGGATCTCTTCCTGGCTTAAATTATTTCAC
AGACACCAGGCAGATAACCATATCCATTCTTTCCTGTATTCGTTAATAGTC
AGAGCTAAAAGTGTAGGGCTCTAAATTTACACTTCAACAAATTGTTCTGTT
ATTAAGTATTCACCTCAAAATGACCAGACTATACTATCCTCTAAATTTTAG
AAACTTGGAGCTTGGCTCTGGTCCCTAGTCTTTGTTCTGTCTCATTAATGG
CTTCATCAATACTACGGTTCCAAAGACTATCTATATGCAGTAAACTTCCAA
TTTTACATCTCCAGCCTGACCTTTTTTCTGAAATGCAAATGTGTGTAGCCA
CATTTTCACTTGACATCTCCATTTAGAACTCTAATAGGTCTTTCACCCTAA
ACACTTCCAAGACACAGGAATAAACGTGCTCCTTAAGCCTGTTATCCCTTC
CAGTTCTCCCCAGTTCAATAACTGACACTACCATTTACTCAAATCAACATT
CTAAGAGTGTCACTTGCTACATTTCCTTCATCTCTACAAATCCAAAGTATC
TGTGAGTCACGTCACCTACATATTCAATACATGCAATAATTCATTCTCCAT
ACTCCTTACCATGACTTAAGGGCCCACTCAGTGACCATCTCTGGCCTCTGT
TCACCTCTTCTGCTGTTCTCCTTTGCTGTTCCAGCCACGCTGGTCTCTTTT
CACATCAAGCAGCTAAGCTCTGCCCATTTAAGACATTTAACTTCTTGGCCT
CAATCTCTGAAATGCCTGTTTGATTTTTCTTCTGGTGAGCTCATTTTCACT
CATCAGGTCCCAGCTCTGTTTCAGACAAGGCTATCTAAAATAGACCTACCT
AAATGGATTAAAAATCTGAGAATATGAAATAACAAATATCAGATGACATTT
TAGGAGACCCTTTATATACCTCATTTGTGTGTGTGTGTGTGTGTGTGTGTG
```

FIG. 8-313

```
TGTGTGTGTGTTTGGAAATGGTGATGGAGGGTGTCATTGCTAAGTGAGGAG
GAAACACAAAAGCCATCTAGGAAAGGACACAGACTAGATAGGTCCAAAAGT
GGTTTAAGACAGAATATATGTAAAGAGAGTTATAGAAAGAGCAATAAGTTG
GGATAAAGGATTTCCAAAACATATACGGGGTTAGTAACCTCAATTTACAGG
GACAAACTGCAAAACGTTAGTGAAAAGGCAAACAACATAATATAAAAGATG
ATTAAACGGTATTTTATATCATGTATTAAATTCATATGGCCAATACATATG
AAAAACAAGAAACAAAAAACCTTCCTAGTAATTCAAAATTATGCATATTAA
TACAACAAAGGGATACCACTTCTTTTTTTTTTTTTTTTGAGACAGAGTC
TTGCTCAGGTACCCAGGCTGGAGTGTAGTGGCATGATCTCAACTCACTGCA
ACTTCCACCCCCTGGGTTCAAGCGATTCTCCTGCCTCAGCCTCCCGAGTAG
CTGGGACTACAGGCGCCTGCTACCACGCTCAGCTAACTTTTGTATTTTTAT
TAGAGATGGGGTTTTACCATGTTGGTTGGCCAGGATGGTCTCGGTCTCTTG
ACCTCGTGATCTGACGGCCTCAGCCTCCCAAAGTGCTGTGATTACAGGCGT
GAACCACTGCACCTGGCCTAATTTTTGTATTATTAGTAGAGATGGGGTTTC
ACCATATTGGCCAGGCTGGTGTCGAACTCCTCCTGACCTCAGATGATCCAC
CCACTTCAGGCTCCCAAAGTGCTGGGATTACAGGCATGAGCCACTGTGCCC
AGCCTGGGATACCATTTCTTACCTATGAATAGACAACCACTAAAGCCAGTA
TACTCAGGACTGCAAAGGATGAGGAAGAATTGCCATTGTCATATAGTTTTT
CATAACTTTTCCTGACAATGTCTATTAAATTGTATTAATAGACATTTGGAA
AGGGAGAGTGTCAACAATCTAGAATAAAGGCCCCACTAGGTAAGGTTACAT
ATGTAAGGACTCTTTCAAAACTGTCACAAGAATTCAGGTACGGTGGCTCAT
GCCTGTAATCCTAGCATTTTGGGAGGCTGAGGCGGGTGGATCACTTGAGGT
CAGGGGTTTGAGACCCGCCTGGCCAACATGGTTAAAACCTATCTCTACTAA
AAATACAACGATTAGCCATGCATGGTGGCACATGCCTGTAATCCCAGCTAC
TCGGTAGCCTGAGGCAGGAGAATAGCTTGAACCCAAGAGGCAGAGGTTACA
GTGAGCCGAGATCGCACCACTCCAGCCTGGGCAACAGAGTGAGACTCCATC
TCAAAACAAAACAAAAAAACTACTCAAAACTGTAATAAGAAAAAAAAAAC
CTAATTATACATGTAAAACATTTAAATAACTAAAATAAGAATACTGTTGAC
ATAGTGAGACATCCATTTATACTATGGAATGTTATGCAGCTACCTGAAACA
ATAATCCGGTGAAACAAAATCACACACACAACTGATGAGAGTAAATAGAGA
ACCGTATGGAAGAAAACATACCACAGTAATTATCTCAGATAGCTGAAACTA
AGTTGGTGCAAAAGTAATTGTGGTTCTTACCATTACTTTCACTGGCAAAAG
CTGCAATTACTTTTGTACCAACCTAATAGAATGGGGTGAGGAGAGGTAAAC
CTTTATAAACATCTCTGTGTGAACTGTTAAAATGAGCAAGTATATTTTTTT
TAAAGTATAAAGAGAGAAAAAGTAAACTTTCTCCATTTCCCACCTCAAAT
TATGTTCTGTCACTCATCCTGTTTAGATTCTTTCAAATGCAGTTTGAAGTT
TTATTTATGAGATTCCTTGTTGTTTGCCTCTTTCCATTAAACCTAGCTCCA
CAAAGTAGGGACCTGATGTATTCATTCACTGTTATATCCCAGCATCTAGCA
GAGGGCCTGACACTTAGTGGGAACGCAAGTATCTGGTATATAAACCAGAGA
ATAGATATTTTTTAGCCCAGAAAGCTGTTTCACTGCACAGAGTGTAATTA
TCTGAATTTCTATAAAAATGTCTATCTATAAATCATTGTCAATACATTACC
TACTCACCTTACCCAGCTACCAGGAACACTATGAAGTTTTGAATTACACCC
CATTTGTTTTCCACACTCTTACCATTTTCCCAGTTTCTGCACTGACCTCTC
CAGACATCATGTGTACTGATAATTCTAAGTTGTCTAGATTGTTAATTCTTT
TAAGGGCCTGTTCTCTGCTAGCTGGCATCATGCATAAAATAATTCTCTTTA
ATATGCTCTGGGTCTAGGGTTAATAGATGTTTGCTTAAAATCATGGAAAGA
```

FIG. 8-314

```
AAATGGTCACACAGCTGGTATGTGTGATCAAATTTGTGCTGTTTCATCCAC
TTAATGTTTACTTTGTGGTAATGGAACCTCCCAGCTTTTATTTTCCTTCCT
TCCTTCCTTCCTTCCTTCCTTCCTTCCTTCCTTCCTCCCTCCCTCCC
TCCCTCCCTCCCTTCCTTTCTTTCTTCACAGAGTCTAGCTCTGTTGCCCAG
GCTGGAATGCAGTGGTGCGATCTCAGCTCACTGCAACCTCTGCCTCCCGGG
TTCAAGCGATTCTCCTGCCTCAGCCTCCCAAGTATCTAGGATTACAGGTGC
ATGCTGCCACACCTGGCTAGTTTTTGTATTTTTAGTAAAGATGGAGTTTCA
GATGTTGGCCAGGCTGGTCTCCAACACCAGGCCTCAAGTGATCCGCCTGCC
TTGGCCTCCCAAATTGCTGGGATTAACAGGCCTCAGCCACTGTGCCCGACC
CCAGCTTTTATATTCTAATGCTGAGATTATTCAGTTAACACTCTTACCTGC
TAGGATAAGTTTGTTGGAGAATTTTACCTTACCTTGTACCCTTTACCTTCA
CATCTACCTGTACCCTGGCCCTTCACATCCTTTCCATATAATATATCTTCA
GTAAATACAGGGAAAAAAACCCAGAATGATTATGTTGACAGCAAAACATGT
TTGTGCAGAAACGGAGTAGTCACTATCTAAGCCACAGAGACTTAGGAGTGT
ATTCCTGAGTTATGTATCATTTTAACCATCACTGGATCTTAAATCCCAGTT
GCTAAATTGAAGGGAGATACATGACTCTTTTTAGGGCTTTGCTCTCTGATA
CAGTAGCCATTAGCCACATGTGATATTTTAAATTTAAATAATTAAGTCAAA
AATTCAGTTTCCTCAGTCTCACCACATTTCAGGTTGCTGGTGTCTACTGTA
TTGGATACACAGACATAGAACATGTCTATCATCACAGAAAATTCTATTGCA
TTGCACTGGGATAGGTACTTTTTGTGCCCTTGGGCTGATAAGTTCAAGTGC
ACTTAACTAGCTTCCTCCAAGTGGAATCAGAGGATAAATTTACCATACAAA
ATACAGGATACCCAATTATATTTGAATTTCAAACAGGCAACAAATAATTGC
TTAAGTATGCCCCTCACTGCACACCCAAATATTACATGAGACATTCTATAC
ATATATATATATATATATATATATATATATATATATATATATATATATA
TATTTGAAATTCAGATTTAACTGGACATTTGGTATTTTTAATGTGCCAAAT
CTAGCAACCCTATCTGAAGAGCAAAACTGGAGTGTCTAGTCTGGATAGGTC
CTTTTACACCACAGGGAGTTATTTGAGGAATTGAGAAGGGCTGTGGTACCT
GTAAAGAACTAACTCATTATGAAGAAAAGGATCTGTAAGTTTTTCTGTATG
TGTAAGGAAGGCCAAGAAGGTGGTTTCCAGATATATTTACTTTTTCTTCTC
TCTCTCTTAGGTTGCAAAAGCTTCTCATTTCAGAGAGATGCCAGGATCCTA
AGTGCCTGCCAAACTTACCAATTCTAAGGAATAAGTGGATGGATGGCATTA
CTGATTCCTACATTACTGATTGATTCTGCATCCGCAAATTGTTTTATTAAA
AACATTCTACATCATGTGTGGGGAGATAAGGAGGATAAAATGAAGAGAAAG
AATATTATTGAGGGGAAGTTCTTCTGAATACAAAATGTGTTTAATTTTTA
AATAAGTATTACATTCACAGGGTTCAAACTATTTGAAGTAAAGAGATTATA
TATAAAGAATCCATCCCTCAACTTACCCAGGTGGTCACTTTTCTTTTTCTT
GTGTATCTGCCCAGTATTCATTCCTGCTGATATCAGTCAATAATGAATGAT
ACGTGTTTTCTTCACTTTTTTCATTCTTGTCAGGTAGCAGACTGTGTAGAC
TTTTCTGCACTTGCCCTTTTCATAACAATCTATCTTGGAGAACTTTCCCTA
TGAGAACATACAGAGCTTCCTGTACACAGTTGCATGTACTGCATTATGCAA
ATGCATTATATTTTATGTAACCTGTCCACTGTTGGTAGGCACTTGAGTTGT
TTTAGTCTTTTGCTATCAAACAGTTCTGGGATGATTAACCCTGATTTACTG
CAAAATTGAAATTGCTCTGCTATTCTGCTGGAATGGTGGTAAGTGAACTGA
AAATTCCAGTCACTCTTGGGCTAGACTCAACGTTCTTAAAAACTATGTGGC
CATCACCAAATTAGTTATTTTGAACCTTAATTTCTTCACCTCTAAAATGGA
GGTAATACTTACCTTAAGTGGCTATGAGAATGAAGATCATGTGTATGAATT
```

FIG. 8-315

```
GTTGGTGCTCTAAAGAACAGCACAAATAAAATTATTTTCAAATTTAATTTT
AATTGAACTATGTGTAATTTCTTAATTTTGAAATAATTTTATTTGTAATGT
GCATAATCTTATTTAATGTATAATGTATACATTGTAATAGAAACAGATTTC
CCAAATTCCAGCCTGGCATGAGGTAATAAAAGGTAATGCAAAGGGAGAGGA
AAGCATGTGTCATTAATTTTCTGCCTAGGACACCTCCCTGGTTAAATTGCC
ATTTCCTTTCTTCCTTGCATAATGATTAGGAAACACATCCTCCTGACCTGC
CTGCCCTCTTTTGCCTACTTTTTCATCTGCAGTCAAGGTCTGGTTTTAAGA
CTGACTGTTACTTTTACAAATCTGTGTGTATTGGTGGCTAAGGGCCTGTAT
GGTCCACTGCTGTATTCCCAGGTCCCAGCATGGTGCCTGACGCTGCCTGGC
AAATAGTAGTCACCCGAGAAATGGCTGATGAATTCATGAGGCCTACTCTGT
ATGGAAATTTCAATTCTGGCCCCGAATTTTCAGGAGCTGGCAAGAGAGCCA
CCTTAATATCATAGGCTGAGTTGGAAGAAGGGAACACCCAATTTATTCTTA
AGAAGTACTTTGCCCAGGTACTGTGGCTTAGGCCAGTAATCCTAGCATTTG
GGGAAGCCAAGTTGGGCAGATGGCTTGAACCCAGGATTTCGAGATCAGCCT
GGACAACATGGAGAAACCCCATCTCTACAAAATATGTAAAATTTAACTGCT
TGGTGGGCCTGCACTTCTGGTCCCAGCTACTCCAGGGCTAGGGTGGGAGGA
TTGTTTGATCCCTGGAGGTCAAGGCTGCAGTGAGCCATGATCACAGCAATG
CGCTCCAGCTCTGGGCAACAGAGCGAGACCCTGTCTCAAAAAAAACAAAAA
TGCCTATACAATAAATCTATAAAAAGTGGGTTTTGTGTGTCTATACACACA
CACACACACACACACCTGCATAGACACTCAGGTGTTCTGGAAAGACACAGG
AATCTGAAGCCAAAATACTTGTGATTTTTTTTCAGCTCTGCCACTCACCAA
ATGTCTGATGGGATTAGTTACCTGCCATCTCAGAATTTCTCTTCTGTAAAA
TAAGGTAATAGTACCTCCCAGAGTTATGAAAAACTATCAAATGAGATGGCA
GATGAGAAAACACTATATTCCTTGTAAAACCTGACAAATATGTGCAAGATT
ATATAAAGACTGTCTTCTGTCCATTTTCAAATGTGGAAAAGTGAAAGCAGG
ACAGGATGTTGGGATTTCTGTCAGAGATTTGCTGGCTTCCACCTGCAGAAA
TTGAAGTAATTGGGGTTCTTACACCTAAGTACTAACTGAGTCTGGTTGCAG
TTTGCCCCCATGGCTACATGAAGCTTTTAGAAGAGTCAGCATGGTAGACAT
GGAATGTTGAATGGTGGTGGAGTGTACCCACACACCTCCCACCAAGTCAGC
TCCAGGTTCAGAAGCAGCAGCCCCAGTGGAAGGCATGCGTGTTTGTAACTC
AGCTGAGCCACCTTTCAAGAAGCAGAAGCTTTCCAAACAGGGATGCCCCCT
GCTTTTGGTTCAACTTGACTTCCTACCTTCAGTGAGGACATGGAGAATTCA
TCTAGACTGGGTACCTGAGCAAACTTGGCAGAGCAAAGAGAAATGTGGAAG
GCCCTAGGTAGACAGGCCCTGTGGAAGGAAAGAATGAAAGAGGACAGAAAG
AAACTCCCATTTTCTTTAGCACAGTCCCTTCAGATTAAGGATGAAGAGGCT
GGGGTTCTGAATTGGTTGGCCTTAGGTAATGGTCACAAAAACAAGTCAATG
GCTTTTCCACATCCGTACATTGAGATATATTTCTGCCCTTGGTATTCATTT
TCTCTGACCTCCAATTAAAGATCTATGCGTCATTTTAAAGCCTTCCTTCCT
TTCTACTCTGTGGTCAGCGTAACATTGGTGGTTTGAAACTGGCCATAATAG
CAGCATTTACATCATGGGAACTAGCATATGTTACATCAGGGTTTTTTGTT
TTGTTTCTGGAGAGCCAGTAAACATACATCGTCACACCACTTAAATATTCT
CTGCTTAAATATTCTCTGCTC
```

MEGABASE TRANSCRIPT MAP: NOVEL SEQUENCES AND ANTIBODIES THERETO

BACKGROUND INFORMATION FOR APPLICATION

This application is a continuation-in-part of U.S. patent application Ser. No. 08/630,912, now abandoned, filed Apr. 4, 1996, and U.S. patent application Ser. No. 08/652,265, filed May 23, 1996, now pending, which are incorporated by reference in their entirety for all purposes.

BACKGROUND OF THE INVENTION

Hemochromatosis is an autosomal disorder of iron metabolism wherein the body accumulates excess iron. The hemochromatosis (HH) gene was originally shown to be linked to the MHC on chromosome 6p21 (Simon et al. *Gut* 17:332–334 (1976)). The HH gene was recently cloned by Feder et al. (*Nature Genetics* 13:399–408 (1996)).

Fine structure mapping of the region to which the HH gene was mapped makes possible the identification of candidate sequences comprising the HH genes, along with structural elements for regulation and expression and neighboring genes.

A variety of techniques is available for fine structure mapping, including direct cDNA selection, exon-trapping, and genomic sample sequencing. The direct selection approach (Lovett et al. *Proc. Natl. Acad. Sci. U.S.A.* 88:9628–9623 (1991)) involves the hybridization of cDNA fragments to genomic DNA. This technique is extremely sensitive and capable of isolating portions of rare transcripts. Exon-trapping (Church et al. *Nature Genetics* 6:98–105 (1994)) recovers spliced introns from in vivo expressed genomic DNA clones and produces candidate exons without requiring any prior knowledge of the target's gene expression. High-through-put genomic DNA sequencing with comparison of the sequence data to databases of expressed sequences has also been used, such as in the positional cloning of the Werner syndrome gene (Yu et al. *Science* 277:258–262 (1996)) and in cloning by homology of the second Alzheimer's disease gene on chromosome 1 (Levy-Lahad et al. *Science* 269:973–977 (1995)).

Thus, a need exists for both methods for fine structure mapping and a fine structure map of the region of the chromosome to which the HH locus maps. This and other needs are addressed by the present invention.

SUMMARY OF THE INVENTION

One aspect of the invention is an isolated nucleic acid sequence comprising a nucleic acid sequence substantially identical to BTF1.

A further aspect of the invention is an isolated nucleic acid sequence comprising a nucleic acid sequence substantially identical to BTF2.

A further aspect of the invention is an isolated nucleic acid sequence comprising a nucleic acid sequence substantially identical to BTF3.

A further aspect of the invention is an isolated nucleic acid sequence comprising a nucleic acid sequence substantially identical to BTF4.

A further aspect of the invention is an isolated nucleic acid sequence comprising a nucleic acid sequence substantially identical to BTF5.

A further aspect of the invention is an isolated nucleic acid sequence comprising a nucleic acid sequence substantially identical to NPT3.

A further aspect of the invention is an isolated nucleic acid sequence comprising a nucleic acid sequence substantially identical to NPT4.

A further aspect of the invention is an isolated nucleic acid sequence comprising a nucleic acid sequence substantially identical to RoRet.

Additional aspects of the invention include nucleic acid sequences that are cDNAs, polypeptides encoded by the nucleic acids of the invention and antibodies specifically immunoreactive thereto, vectors comprising the nucleic acid sequences of the invention, and host cells stably transfected with the nucleic acids of the invention.

A further aspect of the invention is a 250 KB sequence of the HH subregion shown in FIG. 8.

A further aspect of the invention is an isolated nucleic acid sequence comprising at least 18 contiguous nucleotides substantially identical to at least 18 contiguous nucleotides of BTF1.

A further aspect of the invention is an isolated nucleic acid sequence comprising at least 18 contiguous nucleotides substantially identical to at least 18 contiguous nucleotides of BTF2.

A further aspect of the invention is an isolated nucleic acid sequence comprising at least 18 contiguous nucleotides substantially identical to at least 18 contiguous nucleotides of BTF3.

A further aspect of the invention is an isolated nucleic acid sequence comprising at least 18 contiguous nucleotides substantially identical to at least 18 contiguous nucleotides of BTF4.

A further aspect of the invention is an isolated nucleic acid sequence comprising at least 18 contiguous nucleotides substantially identical to at least 18 contiguous nucleotides of BTF5.

A further aspect of the invention is an isolated nucleic acid sequence comprising at least 18 contiguous nucleotides substantially identical to at least 18 contiguous nucleotides of NPT3.

A further aspect of the invention is an isolated nucleic acid sequence comprising at least 18 contiguous nucleotides substantially identical to at least 18 contiguous nucleotides of NPT4.

A further aspect of the invention is an isolated nucleic acid sequence comprising at least 18 contiguous nucleotides substantially identical to at least 18 contiguous nucleotides of RoRet.

Additional aspects of the invention include isolated nucleic acids of about 18 to 100 nucleotides substantially identical to about 18 to 100 contiguous nucleotides of the nucleic acids of the invention, and the use of these isolated nucleic acids as PCR probes.

BRIEF DESCRIPTION OF THE DRAWINGS

FIG. 3 (SEQ ID NOS:1–6) depicts an alignment of the predicted amino acid sequence of the BTF proteins. Sequences were aligned in a pair-wise fashion using CLUSTAL W (Thompson et al. *Nucl. Acids Res.* 22:4673–4680) to deduce the most parsimonious arrangement. The asterisks under the alignment represent amino acids conserved in all 6 proteins; the "dots" represent conserved amino acids substitutions. Boxed are the regions within the proteins which correspond to three conserved motifs: 1) the B-G domain, 2) the transmembrane domain (TM), and 3) the B30-2 exon domain.

FIG. 5(A) (SEQ ID NOS:7–8) depicts an alignment of the predicted amino acid sequence of the RoRet gene to the 52 kD Ro/SSA auto-antigen protein. The asterisks under the alignment represent conserved amino acids; the "dots" represent conserved amino acids substitutions. The putative DNA binding cysteine-rich domain and the B30-2 exon domain are boxed. FIG. 5(B) (SEQ ID NOS:9–10) depicts an alignment of the predicted amino acid sequence of the two novel putative sodium phosphate transport proteins to that of the NPT1.

FIG. 7 depicts the sequences of cDNA 21 (BTF1) (SEQ ID NO:12), cDNA 29 (BTF3) (SEQ ID NO:13), cDNA 23 (BTF4) (SEQ ID NO:14), cDNA 44 (BTF5) (SEQ ID NO:15), cDNA 32 (BTF2) (SEQ ID NO:16), cDNA 27 (RoRet) (SEQ ID NO:17), cDNA 22B (NPT3) (SEQ ID NO:18), cDNA22E (NPT4) (SEQ ID NO:19).

FIG. 8 (SEQ ID NOS:20–22) depicts the nucleotide sequence of approximately 250 KB in the HH subregion.

DETAILED DESCRIPTION OF THE SPECIFIC EMBODIMENT

A. Definitions

Figure 1:
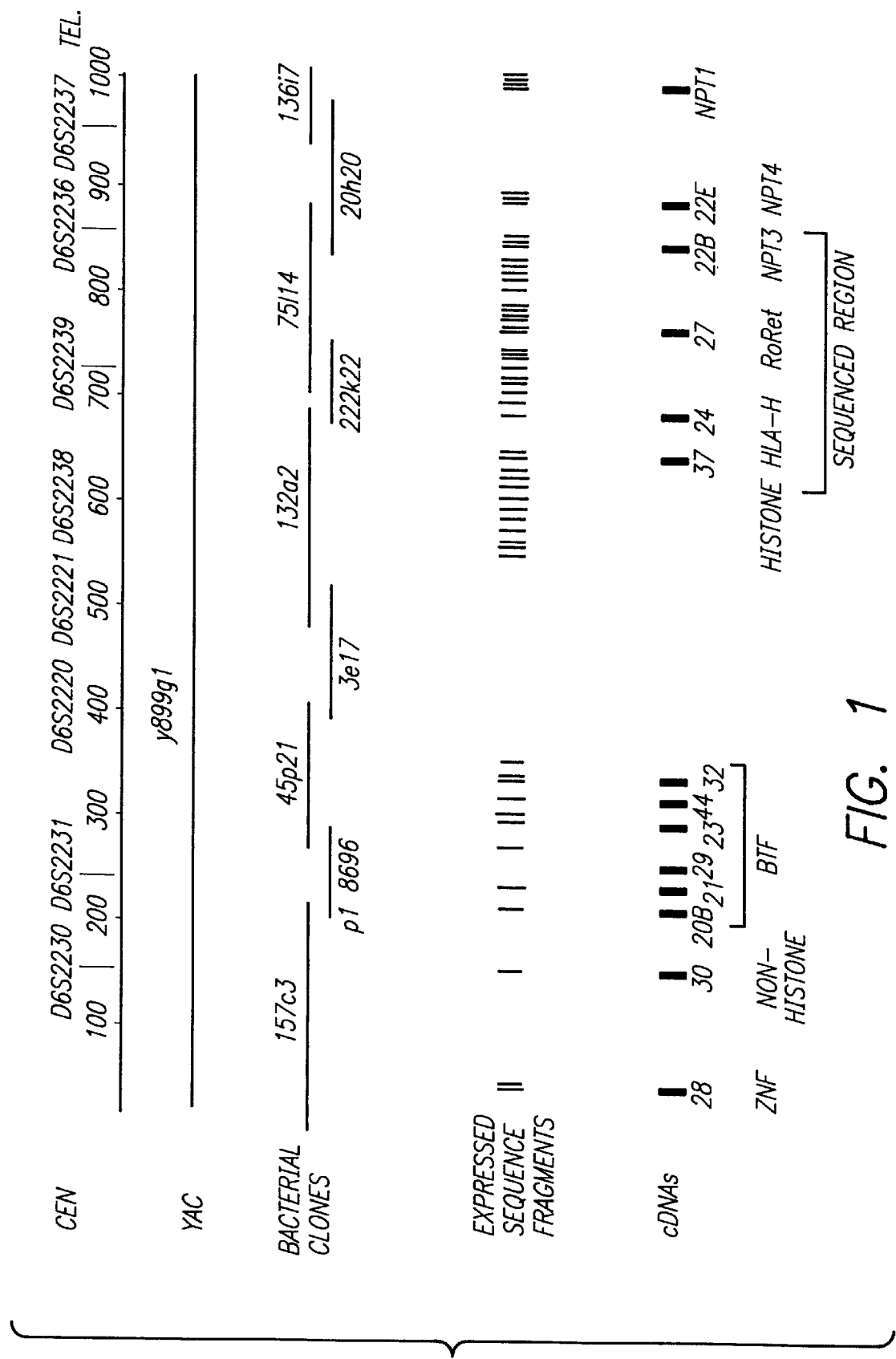
FIG. 1 depicts a combination genetic, physical and transcription map of the HH candidate gene region. The first line shows the relative positions of selected genetic markers that define the HH region. The heavy bar below represents the YAC clone used in the direct selection experiment. The order and positions of the bacterial clones employed in the exon-trapping and sample sequencing is indicated under the YAC. The thin bar under the bacterial clones represents the approximate locations of a subset of the expressed sequence fragments mapped to the contig. The thicker bars show the location of the cDNAs cloned. Two regions are bracketed; the butyrophilin family of genes (BTF), and the region where complete genomic sequencing was carried out.

Abbreviations for the twenty naturally occurring amino acids follow conventional usage. In the polypeptide notation used herein, the left-hand direction is the amino terminal direction and the right-hand direction is the carboxyl-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

The phrase "isolated" or "substantially pure" refers to nucleic acid preparations that lack at least one protein or nucleic acid normally associated with the nucleic acid in a host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. U.S.A.* 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologies. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

As used herein, "EST" or "Expressed Sequence Tag" is meant a partial DNA or cDNA sequence of about 150 to 500, more preferably about 300, sequential nucleotides of a longer sequence obtained from a genomic or cDNA library prepared from a selected cell, cell type, tissue or tissue type, or organisms which longer sequence corresponds to an mRNA or a gene found in that library. An EST is generally DNA. One or more libraries made from a single tissue type typically provide at least 3000 different (i.e. unique) EST's and potentially the full complement of all possible EST's representing all possible cDNAs, e.g., 50,000–100,000 in an animal such as a human. (See, for example, Adams et al. *Science* 252:1651–1656 (1991)).

B. Nucleic Acid Markers and the Proteins Encoded Thereby

The instant invention provides a fine structure map of the 1 megabase region surrounding the candidate HH gene. As part of that map the instant invention provides 250 KB of DNA sequence (FIG. 8) and eight loci of particular interest corresponding to candidate genes within the 1 megabase region. These loci are useful as genetic and physical markers for further mapping studies. Additionally, the eight cDNA sequences corresponding to those loci are useful, for example, for the isolation of other genes in putative gene families, the identification of homologs from other species, and as probes for diagnostic assays. In particular, isolated nucleic acid sequences of at least 18 nucleotides substantially identical to contiguous nucleotides of a cDNA of the invention are useful as PCR primers. Typically, the PCR primer will be used as part of a pair of primers in a PCR reaction. Isolated nucleic acid sequences preferably comprising about 18–100 nucleotides, more preferably at least 18 nucleotides, substantially identical to contiguous nucleotides in a cDNA of the invention are useful in the design of PCR primers and probes for hybridization assays. Additionally, the proteins encoded by those cDNAs are useful in the generation of antibodies for analysis of gene expression and in diagnostic assays, and in the purification of related proteins.

Thus, in one embodiment of the invention, a 250 KB sequence is provided for the HH subregion within the 1 megabase region mapped. This sequence can serve as a reference in genetic or physical analysis of deletions, substitutions, and insertions in that region. Additionally, the sequence information provides a resource for the further identification of new genes in that region. Thus, nucleic acid sequences substantially identically to the 250 KB sequence are also included in the scope of this invention.

In a further embodiment of the invention, a family of five genes, BTF1-5, is provided which are related by sequence homology to the milk protein butyrophilin (BT) (FIGS. 1, 3, and 7). The predicted amino acid sequences of the proteins encoded by these genes are provided in FIG. 3. These cDNAs are useful for the identification of further members of the BT family and to study regulation of expression of this family of genes. The proteins encoded by these cDNAs can be useful in the identification and isolation of ligands for the BT protein, and in the generation of agonists or antagonists of BT function. Nucleic acid sequences substantially identically to BTF1-5 and the proteins encoded by them are also included in the scope of this invention, including allelic forms.

In a further embodiment of the invention, a novel gene RoRet is provide, which is related by sequence homology to the 52 KD Ro/SSA Lupus and Sjogren's syndrome autoantigen. This sequence is especially useful in the identification of other genes that may be involved in Lupus or Sjorgen's syndrome. The protein encoded by this cDNA can be useful in the identification and isolation of ligands for the autoantigen, and in the generation of agonists or antagonists of the antigen. Nucleic acid sequences substantially identically to RoRet and the proteins encoded by them are also included in the scope of this invention.

In a further embodiment of the invention, two genes, NPT3 and NPT4, with structural homology to a type 1 sodium transport gene are provided. These cDNAs and the proteins expressed by them are useful in determining the etiology of hypophosphatemia, along with being useful as probes in the identification and isolation of further members of the gene family. Nucleic acid sequences substantially identically to the NPT1-like sequences and the proteins encoded by them are also included in the scope of this invention.

C. General Methods

The nucleic acid compositions of this invention, whether RNA, cDNA, genomic DNA, or a hybrid of the various combinations, may be isolated from natural sources, including cloned DNA, or may be synthesized in vitro. The nucleic acids claimed may be present in transformed or transfected whole cells, in a transformed or transfected cell lysate, or in a partially purified or substantially pure form.

The nucleic acid sequences of the invention are typically identical to or show substantial sequence identity (determined as described above) to the nucleic acid sequences of FIGS. 7 and 8. Included in this definition are nucleic acids which hybridize to the nucleic acid sequences of FIGS. 7 and 8 under stringent conditions. "Stringent" as used herein refers to hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Techniques for nucleic acid manipulation of the nucleic acid sequences of the invention such as subcloning nucleic acid sequences encoding polypeptides into expression vectors, labelling probes, DNA hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., (1989), which is incorporated herein by reference. This manual is hereinafter referred to as "Sambrook et al."

There are various methods of isolating the nucleic acid sequences of the invention. For example, DNA is isolated from a genomic or cDNA library using labelled oligonucleotide probes having sequences complementary to the sequences disclosed herein. Such probes can be used directly in hybridization assays. Alternatively probes can be designed for use in amplification techniques such as PCR.

To prepare a cDNA library, mRNA is isolated from tissue such as heart or pancreas, preferably a tissue wherein expression of the gene or gene family is likely to occur. cDNA is prepared from the mRNA and ligated into a recombinant vector. The vector is transfected into a recombinant host for propagation, screening and cloning. Methods for making and screening cDNA libraries are well known. See Gubler, U. and Hoffman, B. J. *Gene* 25:263–269 (1983) and Sambrook et al.

For a genomic library, the DNA is extracted from tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science* 196:180–182 (1977). Colony hybridization is carried out as generally described in M. Grunstein et al. *Proc. Natl. Acad. Sci. USA*. 72:3961–3965 (1975).

DNA of interest is identified in either cDNA or genomic libraries by its ability to hybridize with nucleic acid probes, for example on Southern blots, and these DNA regions are isolated by standard methods familiar to those of skill in the art. See Sambrook, et al.

Various methods of amplifying target sequences, such as the polymerase chain reaction, can also be used to prepare DNA encoding ATP-sensitive potassium channel protein. Polymerase chain reaction (PCR) technology is used to amplify such nucleic acid sequences directly from mRNA, from cDNA, and from genomic libraries or cDNA libraries. The isolated sequences encoding ATP-sensitive potassium channel protein may also be used as templates for PCR amplification.

In PCR techniques, oligonucleotide primers complementary to the two 3' borders of the DNA region to be amplified are synthesized. The polymerase chain reaction is then carried out using the two primers. See *PCR Protocols: A Guide to Methods and Applications* (Innis, M, Gelfand, D., Sninsky, J. and White, T., eds.), Academic Press, San Diego (1990). Primers can be selected to amplify the entire regions encoding a full-length sequence of interest or to amplify smaller DNA segments as desired.

PCR can be used in a variety of protocols to isolate cDNA's encoding a sequence of interest. In these protocols, appropriate primers and probes for amplifying DNA encoding a sequence of interest are generated from analysis of the DNA sequences listed herein. Once such regions are PCR-amplified, they can be sequenced and oligonucleotide probes can be prepared from sequence obtained.

Oligonucleotides for use as probes are chemically synthesized according to the solid phase phosphoramidite triester method first described by Beaucage, S. L. and Carruthers, M. H., *Tetrahedron Lett.*, 22(20):1859–1862 (1981) using an automated synthesizer, as described in Needham-VanDevanter, D. R., et al., *Nucleic Acids Res.* 12:6159–6168 (1984). Purification of oligonucleotides is by either native acrylamide gel electrophoresis or by anion-exchange HPLC as described in Pearson, J. D. and Regnier, F. E., *J. Chrom.*, 255:137–149 (1983). The sequence of the synthetic oligonucleotide can be verified using the chemical degradation method of Maxam, A. M. and Gilbert, W., in Grossman, L. and Moldave, D., eds. Academic Press, New York, *Methods in Enzymology* 65:499–560 (1980).

C. Expression

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding A. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al. Examples of expression of ATP-sensitive potassium channel proteins in both prokaryotic and eukaryotic systems are described below.

1. Expression in Prokaryotes

A variety of procaryotic expression systems may be used to express the proteins of the invention. Examples include *E. coli,* Bacillus, Streptomyces, and the like.

It is preferred to construct expression plasmids which contain, at the minimum, a strong promoter to direct transcription, a ribosome binding site for translational initiation, and a transcription/translation terminator. Examples of regulatory regions suitable for this purpose in E. coli are the promoter and operator region of the E. coli tryptophan biosynthetic pathway as described by Yanofsky, C., J. Bacteriol. 158:1018–1024 (1984) and the leftward promoter of phage lambda (Pλ) as described by Herskowitz, I. and Hagen, D., Ann. Rev. Genet. 14:399–445 (1980). The inclusion of selection markers in DNA vectors transformed in E. coli is also useful. Examples of such markers include genes specifying resistance to ampicillin, tetracycline, or chloramphenicol. See Sambrook et al. for details concerning selection markers for use in E. coli.

To enhance proper folding of the expressed recombinant protein, during purification from E. coli, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from E. coli can be achieved following procedures such as those described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, a sequence of interest may be expressed in these eukaryotic systems.

Synthesis of heterologous proteins in yeast is well known. *Methods in Yeast Genetics,* Sherman, F., et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8:17–24 (1979); Broach, et al., *Gene* 8:121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London) 275:104–109 (1978); and Hinnen, A., et al., *Proc. Natl. Acad. Sci. U.S.A.* 75:1929–1933 (1978). The second procedure does not involve removal of the cell wall. Instead the cells are treated with lithium chloride or acetate and PEG and put on selective plates (Ito, H., et al., *J. Bact.* 153:163–168 (1983)).

The proteins of the invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding the proteins of the invention can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of ATP-sensitive potassium channel proteins are available, for instance, from the American Type Culture Collection Catalogue of Cell Lines and Hybridomas (7th edition, (1992)).

Appropriate vectors for expressing the proteins of the invention in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27:353–365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773–781 (1983)).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. *Biochemical Methods in Cell Culture and Virology,* Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

D. Purification

The proteins produced by recombinant DNA technology may be purified by standard techniques well known to those of skill in the art. Recombinantly produced proteins can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982), incorporated herein by reference. For example, antibodies may be raised to the proteins of the invention as described herein. Cell membranes are isolated from a cell line expressing the recombinant protein, the protein is extracted from the membranes and immunoprecipitated. The proteins may then be further purified by standard protein chemistry techniques as described above.

E. In Vitro Diagnostic Methods

The present invention provides methods for detecting DNA or RNA encoding the proteins of the invention and for measuring the proteins by immunoassay techniques. These methods are useful for two general purposes. First, assays for detection of nucleic acids encoding the proteins of the invention are useful for the isolation of these nucleic acids from a variety of vertebrate species according to the methods described in section (B) above and by use of the nucleic acid hybridization assays described below.

The nucleic acid hybridization assays and the immunoassays described below are also useful as in vitro diagnostic assays for disorders in which alterations in the proteins of the invention or related proteins play a role.

1. Nucleic Acid Hybridization Assays

A variety of methods for specific DNA and RNA measurement using nucleic acid hybridization techniques are known to those of skill in the art. See Sambrook, et al. For example, one method for evaluating the presence or absence of the nucleic acids of the invention in a sample involves a Southern transfer. Briefly, the digested genomic DNA is run on agarose slab gels in buffer and transferred to membranes. Hybridization is carried out using the nucleic acid probes discussed above. As described above, nucleic acid probes are designed based on the nucleic acid sequences of the invention. The probes can be full length or less than the full length of the nucleic acid sequence encoding the potassium channel protein. Shorter probes are empirically tested for specificity. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA encoding ATP-sensitive potassium channel proteins.

Similarly, a Northern transfer may be used for the detection of mRNA encoding the proteins of the invention. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the proteins of the invention A variety of nucleic acid hybridization formats are known to those skilled in the art. For example, common formats include sandwich assays and competition or displacement assays. Hybridization techniques are generally described in *Nucleic Acid Hybridization, A Practical Approach* Ed. Hames, B. D. and Higgins, S. J., IRL Press (1985); Gall and Pardue *Proc. Natl. Acad. Sci. U.S.A.* 63:378–383 (1969); and John, Burnsteil and Jones *Nature* 223:582–587 (1969).

For example, sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Biochemistry and Molecular Biology* Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding the proteins of the invention is in situ hybridization. In situ hybridization assays are well known and are generally described in Angerer et al. *Methods Enzymol.* 152:649–660 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to the proteins of the invention. The probes are preferably labelled with radioisotopes or fluorescent reporters.

2. Production of Antibodies and Development of Immunoassays

Immunoassays can be used to qualitatively or quantitatively analyze for the proteins of the invention. A general overview of the applicable technology can be found in Harlow and Lane, *Antibodies: A Laboratory Manual,* Cold Spring Harbor Pubs., N.Y. (1988), incorporated herein by reference.

a. Antibody Production

A number of immunogens may be used to produce antibodies specifically reactive with the proteins of the invention. Recombinant protein is the preferred immunogen for the production of monoclonal or polyclonal antibodies. Naturally occurring protein may also be used either in pure or impure form. Synthetic peptides made using the protein sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the ATP-sensitive potassium channel protein. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. *Science* 246:1275–1281 (1989).

Methods of production of synthetic peptides are known to those of skill in the art. Peptides preferably at least 10 amino acids in length are synthesized corresponding to these regions and the peptides are conjugated to larger protein molecules for subsequent immunization. Preferably, peptide sequences corresponding to regions of interest of a recombinant protein of the invention is used to generate antibodies specifically immunoreactive with the protein. Production of monoclonal or polyclonal antibodies is then carried out as described above.

b. Immunoassays

A particular protein can be measured by a variety of immunoassay methods. For a review of immunological and immunoassay procedures in general, see *Basic and Clinical Immunology* 7th Edition (D. Stites and A. Terr ed.) (1991). Moreover, immunoassays can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, *Antibodies, A Laboratory Manual*, supra, each of which is incorporated herein by reference.

Immunoassays for measurement of the proteins of the invention can be performed by a variety of methods known to those skilled in the art. In brief, immunoassays to measure the protein can be either competitive or noncompetitive binding assays. In competitive binding assays, the sample analyte competes with a labeled analyte for specific binding sites on a capture agent bound to a solid surface. Preferably the capture agent is an antibody specifically reactive with a recombinant protein of the invention produced as described above. The concentration of labeled analyte bound to the capture agent is inversely proportional to the amount of free analyte present in the sample.

Western blot analysis can also be done to determine the presence of a protein of the invention in a sample. Electrophoresis is carried out, for example, on a tissue sample suspected of containing the protein. Following electrophoresis to separate the proteins, and transfer of the proteins to a suitable solid support such as a nitrocellulose filter, the solid support is then incubated with an antibody reactive with the protein. This antibody may be labelled, or alternatively may be it may be detected by subsequent incubation with a second labelled antibody that binds the primary antibody.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3$H, $^{125}$I, $^{35}$S, $^{14}$C, or $^{32}$P was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see *Basic and Clinical Immunology* 7th Edition (D. Stites and A. Terr ed.) supra, *Enzyme Immunoassay*, E. T. Maggio, ed., supra, and Harlow and Lane, *Antibodies, A Laboratory Manual*, supra.

This invention also embraces kits for detecting the presence of a protein of the invention in tissue or blood samples which comprise a container containing antibodies selectively immunoreactive to the protein and instructional material for performing the test. The kit may also contain other components such as a protein of the invention, controls, buffer solutions, and secondary antibodies. Kits for detecting antibodies to a protein of the invention comprise a container containing an a protein of the invention, instructional material and may comprise other materials such as secondary antibodies and labels as described herein.

This invention further embraces diagnostic kits for detecting DNA or RNA encoding proteins of interest in tissue or blood samples which comprise nucleic probes as described herein and instructional material. The kit may also contain additional components such as labeled compounds, as described herein, for identification of duplexed nucleic acids.

The following examples are provided to illustrate the invention but not to limit its scope. Other variants of the invention will be readily apparent to one of ordinary skill in the art and are encompassed by the appended claims.

EXAMPLE

In these studies direct selection, exon-trapping, and genomic sample sequencing were used to generate a transcript map of a 1 megabase region approximately 8.5 megabases telomeric to HLA-A in the vicinity of HH, the candidate hematochromatosis gene. This region 6p21.3 was flanked by the genetic markers D6S2242 and D6S2241. The starting material for these experiments was a 1 megabase YAC labeled y899g1 and a bacterial clone contig of this region (Feder et al. *Nature Genetics* 13:399–408 (1996)). These techniques and other methods used in the study are outlined below.

Direct Selection (DS)

Poly A$^+$ RNA from human fetal brain, liver and small intestine (Clontech, Palo Alto, Calif.) were converted into cDNA using random primers and a Superscript cDNA synthesis kit (Life Technologies, Gaithersburg, Md.). The cDNA was digested with Mbo I and ligated to cDNA Mbo I linker-adaptors. Unligated linker-adaptor were removed by passage through cDNA spun columns (Pharmacia, Piscataway, N.J.). The 5 ng of each of the ligated cDNAs were amplified using the cDNA Mbo I-S primer (SEQ ID NO:23) (5'-CCTGATGCTCGAGTGAATTC-3'). The amplified products were purified on S-400 spin columns (Pharmacia, Piscataway, N.J.), ethanol precipitated and resuspended at 1 mg/ml in TE. Gel-purified yac899g1 (Centre d'Etude du Polymorphisme Humain) was processed as described by Morgan et al. (*Nucl. Acids Res.* 20:5173–5179 (1992)). The cDNAs were mixed in equal molar amounts for a total of 3 mg, and blocked with a mixture of 4 mg Cot-1 DNA (Life Technologies, Gaithersburg, Md.), and a cocktail of Sau 3A-digested ribosomal and five different histone DNAs. The blocked cDNAs were hybridized to biotinylated yac899g1 DNA and streptavidin capture was carried out as described by Morgan et al. (ibid). After the second round of selection, the eluted cDNAs were amplified using the cDNA Mbo I-S primer which included a (CUA)4 repeat at the 5' end to facilitate cloning into a version of pSP72 (Promega, Madison, Wis.) constructed for use with uracil-DNA glycolyase cloning (UDG, Life Technologies, Gaithersburg, Md.). Recombinants were transformed in DH5a, 1000 clones picked into a 96 well format, and clones prepped for DNA sequencing using AGTC boiling 96-well mini-prep system (Advance Genetic Technologies, Gaitherburg, Md.).

Four hundred and sixty five clones were sequenced and the resulting data searched by BLAST (Altschul et al. *J. Mol. Biol.* 215:403–410 (1990)). Those clones representing repetitive, bacterial, yeast, mitochondrial and histone sequences were eliminated from future considerations. The remaining sequences were then searched for overlaps and assembled into 108 unique DS contigs. The number of clones per DS contig varied between 1 to 22 with the length of each contig ranging from 250bp to 850 bp. Small sequence-tag-sites PCR assays were developed for each DS contig and two experiments were carried out concomitantly; mapping each DS contig back to the bacterial clone contig of the region and testing for the presence of each DS contig in cDNA libraries. Overall, 86 or 80% of the DS contigs mapped back to the region and were found to be in cDNA libraries. The number of 80% mapping to the region was probably an underestimate of the fidelity of the direct-selection since PCR assays which cross exon-intron boundaries would be expected to fail or give larger size products, thereby being scored negative.

Exon-Trapping

CsCl-purified genomic P1 (Genome Systems), BAC (Research Genetics) and PAC (Genome Systems) DNAs were digested with BamHI, Bgl II, Pst I Sac 1 and Xho I and 125 ng of each digest ligated into 500 ng pSPL3 (Church et al. *Nature Genetics* 6:98–105 (1994)) (Life Technologies, Gaithersburg, Md.) digested with the appropriate restriction enzyme and phosphatased with calf intestinal alkaline phosphatase (USB, Cleveland, Ohio). One tenth of the ligation was used to transform XL1-Blue MRF' cells (Stratagene, La Jolla, Calif.) by electroporation. Nine tenths of the electroporation was used to inoculate 10 ml of LB+100 mg/ml of carbenicillen and after overnight growth, DNA was prepared using Qiagen Q-20 tips (Qiagen GmbH, Hilden Germany). The remaining one tenth was plated on LB+100 mg/ml carbenicillen plates to evaluated the efficiency on cloning and to test individual clones for the present of single inserts. COS-7 cells were seed overnight at a density of 1.4×10$^5$/well in 6 well dishes. One mg of DNA was transfected using 6 ml of Lipofect-Ace. Cytoplasmic RNA was isolated 48 hr post-transfection. RT-PCR was carried out as described by Church et al. (ibid) using commercially available reagents Life Technologies, Gaithersburg, Md.). The resulting CUA-tailed PCR fragments for each restriction digested bacterial clone were pooled and UDG cloned into pSP72-U (a derivative of pSP72). The DNA was transformed in DH5a and the cells plated onto nylon membranes. After overnight growth, duplicates were made and the DNA hybridized to $^{32}$p end-labeled oligos designed to detect various background products associated with the pSPL3 vector. One set of filters was hybridized with the following gel-purified oligos in 6×SSC aqueous hybridization solution at 42° C.:

| | |
|---|---|
| vector-vector splicing | 5'-CGACCCAGCAACCTGGAGAT-3' (SEQ ID NO:24) |
| cryptic donor-1021 | 5'-AGCTCGAGCGGCCGCTGCAG-3' (SEQ ID NO:25) |
| cryptic donor-1134 | 5'-AGACCCCAACCCACAAGAAG-3' (SEQ ID NO:26) |

The filters were washed twice in 6×SSC, 10 mM sodium pyrophosphate (NaPPi) at 60° C., 30 mins.

After overnight autoradiography, non-hybridizing clones were picked and grown in 250 ml of LB+100 mg/ml of carbenicillin in 96 well mini-rack tubes. The samples were analyzed by PCR using the secondary PCR primers supplied in the kit (Life Technologies, Gaithersburg, Md.) and those clones with inserts greater than 200 bp were selected for sequencing.

Ninety-six exon traps per bacterial clone were sequenced for a total of 768 reactions and the resulting data analyzed by BLAST. In addition, each potential exon was searched against a database of the 86 DS contigs to eliminate redundant sequences. PCR assays were developed for each of the potential exons and they were tested for their presence in cDNA libraries. A total of 48 potential exons remained after these screening steps.

Sample Sequencing

A minimal set of bacterial clones chosen to cover y899g1 were prepped with the Qiagen Maxi-Prep system and purified on CsCl. Ten micrograms of DNA from each bacterial clone was sonicated in a Heat Systems Sonicator XL and end-repaired with Klenow (USB) and T4 polymerase (USB). The sheared fragments were size selected between three to four kilobases on a 0.7% agarose gel and then ligated to BstXI linkers (Invitrogen). The ligations were gel purified on a 0.7% agarose gel and cloned into a pSP72 derivative plasmid vector. The resulting plasmids were transformed into electrocompetent DH5a cells and plated on LB-carbenicillin plates. A sufficient number of colonies was picked to achieve 15-fold clone coverage. The appropriate number of colonies was calculated by the following equation to generate a single-fold sequence coverage: Number of colonies=size of bacterial clone (in kb)/average sequence read length (0.4 kb). These colonies were prepped in the 96-well AGCT system and end-sequenced with oligo MAP1 using standard ABI Dye Terminator protocols. MAP1 was CGTTAGAACGCGGCTACAAT (SEQ ID NO:27). The MAP1 sequences were screened locally with the BLAST algorithm against all available public databases. All expressed sequence fragments (ESF). The ESF represent a collection of ESTs and other expressed sequence fragments that were selected due to their sequence identity over a significant portion of genomic DNA. The ESF were cross referenced against the DS and exon-trapped databases to eliminate redundancies. 58 unique ESF remained, representing 39 distinct clones (Table 1).

TABLE 1

EST's found by Sample Sequencing large bacterial clones.

| Clone name | Bacterial clone | Homology 5' blastx | Homology 3' blastx | Poly A+ signal[1] | Genomic poly (A)$_{□8}$ | cDNA Homology |
|---|---|---|---|---|---|---|
| EST03556 | pc157c3 | na[2] | none[3] | + | − | cDNA 28 |
| ym33fl1 | pc157c3 | ZNF | na | na | na | |
| EST04698 | pc157c3 | na | NSH[4] | + | − | |
| EST04812 | pc157c3 | na | NSH | − | − | |
| yb89b08 | pc157c3 | NSH | na | na | na | |
| yd88g11 | pc157c3 | na | NSH | + | − | |
| yj49b01 | pc157c3 | NSH | na | na | na | |
| yv81d05 | pc157c3 | HGI7 Human | NSH | + | − | cDNA 30 |
| Yg57h09 | p196e20 | BUTYBOVIN | NSH | + | − | cDNA 21 |
| yq23d08 | p196e20 | BUTYBOVIN | NSH | + | − | cDNA 21 |
| yo65f06 | p196e20 | NSH | na | na | na | cDNA 29 |
| yv88c09 | p196e20 | BUTYBOVIN | na | na | na | cDNA 29 |
| yd17d06 | p196e20 | NSH | na | na | na | cDNA 23 |
| ye25g03 | p196e20 | BUTYBOVIN | NSH | na | na | cDNA 44 |
| ys04h08 | pc45p21 | NSH | NSH | + | − | cDNA 44 |
| yn01c05 | p196e20 | BUTYBOVIN | na | na | na | cDNA 32 |
| yg78f10 | pc45p21 | NSH | NSH | na | na | |
| yh54f11 | p196e20 | none | NSH | − | − | |
| ys05b08 | pc157c3 | NSH | Alu | − | + | |
| yb12h11 | b132a12 | NSH | Histone H3.1 | − | − | |
| HSC2EE082 | b132a12 | na | NSH | + | − | |
| HUM160H11B | b132a12 | none | na | na | na | |
| yg04f09 | b132a12 | Line element | Alu | − | + | |
| yd37d11 | b132a12 | NSH | Alu | − | + | |
| ym29g03 | b132a12 | Histone H2A | NSH | + | − | cDNA 37 |
| yi77b02 | b132a12 | NSH | NSH | − | − | cDNA 37 |
| yh76b05 | b132a12 | NSH | Alu | − | − | |
| yu98e02 | b132a12 | NSH | Alu | − | + | |
| yd72h12 | b132a12 | Alu | NSH | + | + | |
| yf19d03 | pc222k22 | Histone H2B.1 | NSH | + | − | |
| ye98g01 | b132a12 | NSH | NSH | + | − | cDNA 24 |
| yi61f07 | b132a12 | NSH | NSH | − | + | |
| EST05340 | b3e17 | na | Alu | − | + | |
| yd35d05 | pc222k22 | NSH | NSH | − | + | |
| yc52a05 | pc75L14 | NSH | na | na | na | |
| yd84a05 | pc75L14 | none | none | − | ?[5] | |
| yr42a05 | pc75L14 | NaPi transport | none | + | − | cDNA 22B |
| yd83h08 | b20h20 | NSH | none | − | + | |
| ye38c09 | b20h20 | NSH | Alu | − | + | |
| yp74c05 | b20h20 | NaPi transport | Alu | ?[6] | na | | racketed area is the critical region
[1]Signal of ATAAA or ATTAA
[2]not available
[3]"NONE" reported by blast
[4]No Sigificant Homologies
[5]3' splice that is not on contig
[6]Poor EST sequence sequence identities were catalogued and cross referenced to the DS and exon-trapped databases.

A total of 3794 end sequence reactions were run to achieve the theoretical 1× coverage. Eighty-five percent of these sequences contained non-bacterial non-vector inserts. An additional 1060 end sequence reactions were run from the opposite end of the cloning vector to augment the sequence coverage and to prepare for contigging across selected regions. BLAST searches to all publicly available databases identified 12 histone genes and 74 unique Included in these ESF are 5 sequences homologous to histone genes.

cDNA library screening

Superscript plasmid cDNA libraries, brain, liver and testis, were purchased by Life Technologies, Gaithersburg, Md. Colonies were plated on Hybond N filters (Amersham) using standard techniques. Insert probes from DS, exons and EST (I.M.A.G.E. clones; Genome Systems) were all isolated by PCR followed by purification in low-melting point agarose gels (Seakmen). The DNAs were labeled in gel using the Prime-it II kit (Stratagene, La Jolla, Calif.). Small exon probes were labeled using their respective STS PCR primers instead of random primers. Up to 5 different probes were pooled in a hybridization. Filters were hybridized in duplicate using standard techniques. Putative positives were screened by PCR using the probe's STSs to identify clones. Inserts from positive clones were subcloned in pSP72 and sequenced.

Northern blots and RT-PCR analysis

Multiple tissue northern blots were purchased from Clontech and hybridized according the manufacturer's instructions. RT-PCR was carried out on random primed first strand cDNA made from poly A+ RNA (Clontech) using AmpliTaq Gold (Perkin-Elmer). Control reactions were performed on RNA samples processed in the absence of reverse transcriptase to control for genomic DNA contamination.

Genomic Sequencing

The MAP1 sequences from the bacterial clones b132a2, 222K22, and 75L14 were assembled into contigs with the Staden package (available from Roger Staden, MRC). A minimal set of 3 kb clones was selected for sequencing with oligo labeled MAP2 that sits on the opposite end of the plasmid vector. The sequence of MAP2 was GCCGAT-TCATTAATGCAGGT (SEQ ID NO:28). The MAP2 sequences were entered into the Staden database in conjunction with the MAP1 sequences to generate a tiling path of 3 kb clones across the region. These sequences were also screened with the BLAST algorithm and all novel sequence identities were noted. The plasmid 3 kb libraries were concurrently transformed in 96 well format into pox38UR (available from C. Martin, Lawrence Berkeley Laboratories). The transformants were subsequently mated with JGM (Strathman et al. *P.N.A.S.* 88:1247–1250 (1991)) in 96 well format. All matings of the 3 kb clones within the tiling path were streaked on LB-carbenicillin-kanamycin plates and a random selection of 12 colonies per 3 kb clone was prepped in the AGCT system. The oligos -21: CTG-TAAAACGACGGCCAGTC (SEQ ID NO:29), and REV: GCAGGAAACAGCTATGACC (SEQ ID NO:30) were used to sequence off both ends of the transposon. Each 3 kb clone was assembled in conjunction with the end sequence information from all bacterial clones to generate complete sequence across the region. The genomic sequence was analyzed with the BLAST nucleotide and protein homology algorithms and the GRAIL 1.2 software to identify novel open reading frames (ORF) for gene finding.

Discussion

A compilation of 174 ESF led to the construction of an expressed sequence map of the region that served as the framework for the isolation of full-length cDNAs (FIG. 1). (The map shows the subset of ESF that were actually mapped). Probes were developed for 82 best ESFs which appeared to be derived from the coding portions of cDNAs and the appropriate cDNA libraries were screened. This led to the isolation of 19 cDNAs, 17 of which represented novel sequences. 70 of the 174 ESF were included in the cDNAs isolated (40%). 36 probes failed to produce any clones even after repeated screening of several libraries. 51 ESF which were not accounted for in the cDNAs cloned were not used in any screen. Therefore, it is possible that some additional genes within this 1 megabase region may have escaped detection.

A list of these cDNAs cloned and a comparison of the methods used to find them is presented in Table 2. Direct selection found 14 out of the 18 cDNAs contained within the boundaries of the YAC used in the experiment. Exon trapping found 15 out of the 19 cDNAs contained within the boundaries of the large insert bacterial clone contig. Sample sequencing identified 11 genes that had corresponding ESTs in the public database.

TABLE 2

Comparison of gene finding methods

| Bacterial clone | CDNA# | homology | EST | DS | Exon trap |
|---|---|---|---|---|---|
| 157c3 | 28 | zinc finger | EST03556 | 2 | 1 |
| 157c3 | 30 | nonhistone | yv81d05 yvh07a10 | 1 | none |
| 157c3 | 46 | ORF | yd88g11 | 1 | |
| 157c3 | 20 | BT | none | none | 3 |
| P18696 | 21 | BTF1 | yn01g05 yg23d08 yg57h09 yu15h03 | 4 | 5 |
| 45p21 | 32 | BTF2 | yg78f10 yn01c05 | 7 | 3 |
| 45p21 | 29 | BTF3 | ye25g03 yo65f06 | 2 | 9 |
| 45p21 | 23 | BTF4 | yd17d06 | 4 | 6 |
| 45p21 | 44 | BTF5 | ys04h08 | 2 | 4 |
| 3e17 | 41 | genomic? | none | none | 1 |
| 132a2 | 43 | genomic? | none | none | 3 |
| 132a2 | 36 | genomic? | none | 1 | none |
| 132a2 | 37 | histone 2A | ym29g03 yh87a03 | 3 | none |
| 75l14 | 24 | MHC class 1 | ye98g01 | 1 | 2 |
| 132a2 | 39 | genomic? | none | none | 4 |
| 132a2 | 27 | Ro/SSA | none | 3 | 4 |
| 132a2 | 22B | NPT1-like | yr42a05 yf09g06 | 1 | 7 |
| 20h20 | 22E | NPT1-like | none | 2 | 5 |
| 20h20 | NPT1 | NPT1 | yp74c05 | N/A | 3 |

Figure 2:
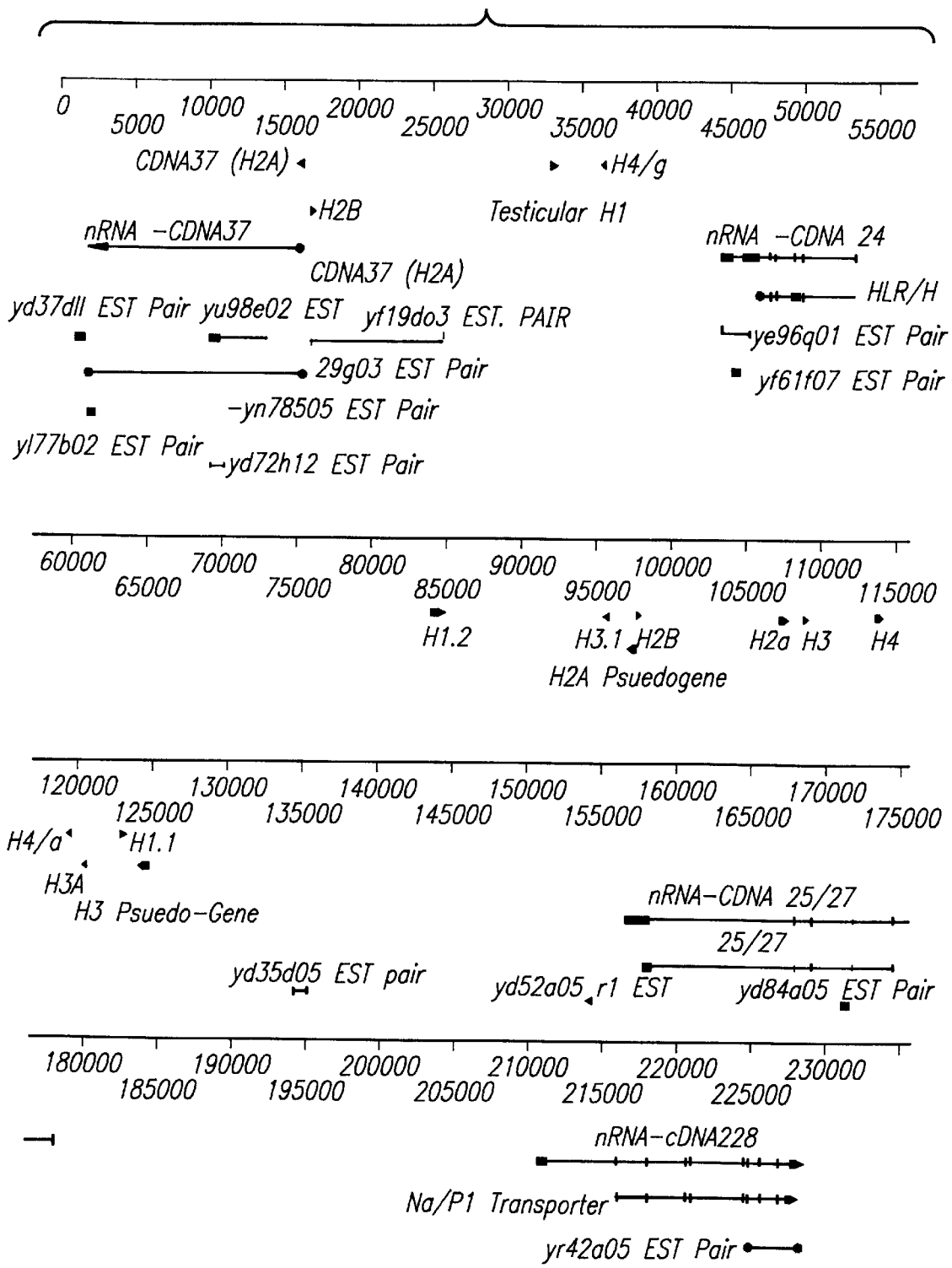
FIG. 2 is a schematic of the 250 kb of genomic sequence including the HH candidate gene, HLA-H. Both the structure of the overall cDNA (top) and that corresponding to the coding regions (bottom), as well as the direction of transcription are shown. The positions of the histone genes, the zinc a-2 glycoprotein pseudogene, and the ESTs are also shown.

As a final approach, a tiling path with overlapping end sequences from the sample sequence database was generated. Each 3 kb clone within the path was shotgunned-sequenced using transposable elements as platforms for dual end sequencing. These individual clones were assembled in conjunction with the end sequences from all bacterial clones in the region. The resulting sequence (FIG. 2) was analyzed systematically with BLAST homology searches and the Grail 1.2 program to identify novel open reading frames (ORF) and other gene-like structures. The BLAST homology searches did not produce any probes that had not already been identified by sample sequencing. Grail predicted exons for all the genes in the region, but was only able assemble the histones into any representative form. A detailed analysis of BLAST homology searches to protein databases identified an enticing homology to a zinc alpha 2 glycoprotein approximately 25 kb upstream of HLA-H, but the lack of a substantial ORF and the presence of a stop codon suggested that it was a pseudogene. FIG. 2 shows the positions, the exon and intron structures, and the relative orientation of transcription of novel genes within this region. Also shown are the positions and transcriptional orientations of the histone genes. A total of 12 histone genes were identified in this study.

In an effort to account for the ESTs that did not associate with the characterized genes in the 250 kb region, the genomic sequence around the putative 3' ends were examined for polyadenylation signals to determine whether certain EST sequences may have originated from genomic DNA contamination in the normalized cDNA libraries used in EST generation. The positions of the 14 ESTs found in this region are indicated in FIG. 2 to show those associated with the cDNAs cloned and those which did not associate with genomic DNA of obvious coding potential. Four ESTs corresponded to 3 of the 4 cDNAs cloned from the region (Table 1). One EST encoded a histone H2B.1 gene and another was a repetitive element. Of the remaining 8, 6 EST clones were used as probes of cDNA libraries with negative results. Those sequences representing putative 3' ends of cDNA were searched for the presence of poly (A)+ addition signals. Five of the 13 ESTs which had 3' end sequence, had the sequence ATAAA or ATTAA. Five of the remaining 8 ESTs that did not have a poly (A)+ addition signal had genomic encoded stretches of poly (A) near the end of EST sequence and, therefore, may have been created by oligo d(T) priming of contaminating genomic DNA. This analysis was expanded to include all ESTs in the large-insert bacterial contigs with definitive 3' ends. Of the remaining 26, 15 had 3' end sequence and of these 8 had poly (A)+ addition signals. Five of these 8 ESTs were associated with the cloned cDNAs. Of the remaining 7 which did not have poly (A)+ addition signals, 4 had genomic encoded stretches of poly (A).

Butyrophilin gene family

The human homolog of the bovine butyrophilin gene (BT) was cloned and mapped to approximately 480 kb centromeric to HLA-H (FIG. 1). ET is a transmembrane protein of unknown function which constitutes 40% of the total protein associated with the fat globule of bovine milk (Jack et al. *J. Biol. Chem.* 265:14481–14486 (1990)). A human homolog of BT has recently been cloned by Tayloer et al. (*Biocem Biophys Acta* 1306:1–4 (1996)). The results in this study indicated that BT is a member of a gene family with at least five other members of the family residing in this region (FIG. 1). A comparison of these proteins is shown in FIG. 3. The proteins were aligned based on their descending order of relatedness and to minimized gaps in the sequence. Each of the five proteins display varying degrees of homology to ET. BTF1 (cDNA 21), BTF2 (cDNA 32), BTF5 (cDNA 44), and BTF3 (cDNA 29) are 45%, 48%, 46%, and 49%, identical to BT, whereas BTF4 (cDNA 32), which is more similar to BTF3 (cDNA 29), is only 26% identical. This low degree of identity to BT is largely due to a truncation at the carboxyl terminus of the protein. The BTF family falls into two groups: BTF1 and 2 which are more related to each other than to BT or the other BTF members, and BTF5, 3 and 4, which appear to have a common evolutionary origin. The order of these genes on the chromosome suggests that the BT gene has duplicated two times, giving rise to BTF1 and BTF5. Subsequently, it appears likely these two genes experienced further duplication events to give rise to the other members in their groups.

The three major components of BT, the B-G immunoglobulin superfamily domain (containing the V consensus sequence) (Miller et al. *Proc. Natl. Acad. Sci. U.S.A.* 88:4377–4381 (1991)), the transmembrane region, and the B30-2 exon are found in all of these proteins (with the exception of BTF4 (cDNA 29) which lacks the B30-2 exon by virtue of the carboxyl terminal truncation). The exon B30-2 is a previously noted feature of the MHC class 1 region found approximately 200 kb centromeric to the HLA-A gene (Vernet et al., (1993)). In addition this exon is found in several genes of diverse function telomeric to HLA-A namely MOG (approximately 200 kb) and RFP (approximately 1 megabase) (Amadou et al. *Genomics* 26:9–20 (1995)).

Figure 4A:
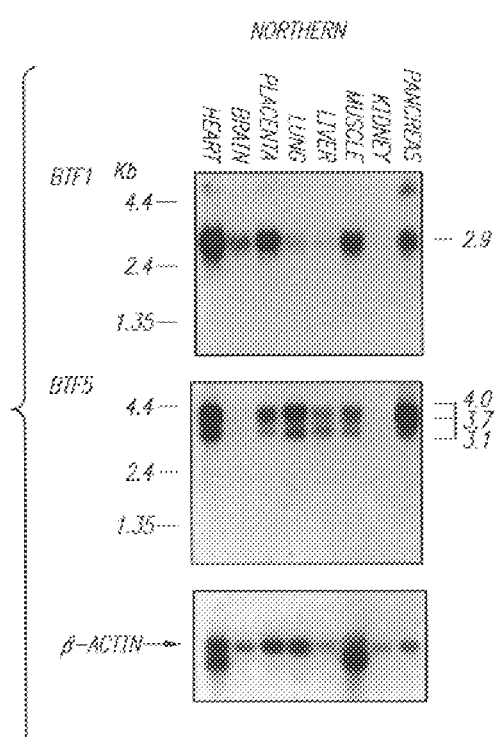
FIG. 4, panel (A) depicts a Northern blot analysis of representative members of the two groups of BTF proteins, BTF1 and BTF5. BTF1 hybridized to all tissues on the blot as a major transcript at 2.9 kb and a minor one at 5.0 kb. BTF5 hybridized to several transcripts ranging between 4.0 and 3.1 kb and as a similar expression profile to BTF1. Autoradiography was for 24 hours. The b-actin hybridization demonstrated the variation in ploy (A)+ RNA between the lanes. Autoradiography was for 1 hour. In panel (B), RT-PCR analysis demonstrated that the expression of both genes was widespread. Included in the (+) lane are cDNA 21 and 44 as positive controls; the (−) lane represents the no-DNA control. Amplification using primers for the RFP gene (Isomura et al. *Nucleic Acid Res.* 20:5305–5310 (1992)) controlled for the integrity of the cDNA. All first strand cDNAs were checked for contaminating genomic DNA amplification by carrying out an identical experiment excluding the reverse transcriptase. In all cases, no amplification was obtained (data not shown).
Figure 4B:
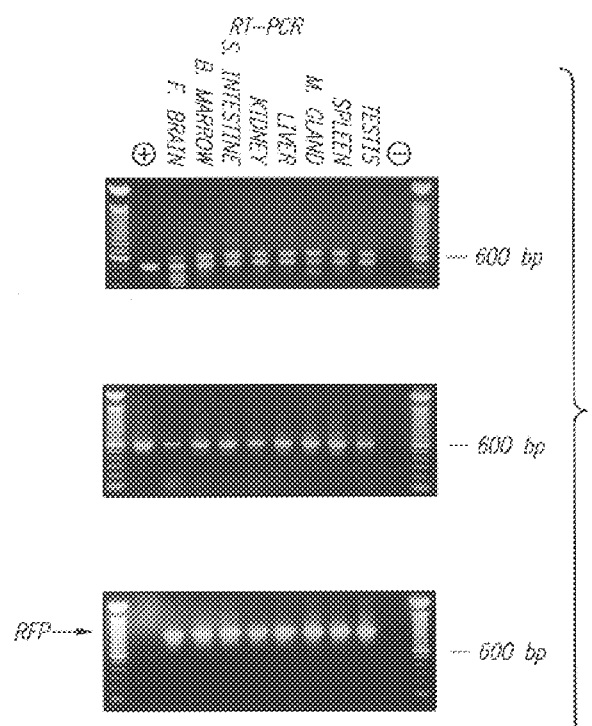

The levels of the BTF mRNA were analyzed by northern blot analysis (FIG. 4A). The expression of the BTF genes fell into two patterns. BTF1 and BTF2 were expressed as a single major transcript of 2.9 kb and one minor transcript of 5.0 kb. These genes were expressed at high levels in all the tissues tested with the exception of the kidney where the expression level was less. The two genes are 900 identical at the DNA sequence level, therefore, it is possible that the signal observed on the northerns was the result of cross-hybridization and only one of the two genes was actually expressed. To address this possibility RT-PCR experiments were carried out on a panel of different tissues in order to detect possible tissue dependent expression that would suggest that both genes are expressed. Identical, and thus equivocal, results were obtained with both BTF1 and BTF2 amplification (FIG. 4B).

The second group of genes, BTF3-5, are expressed as three (BTF5) (FIG. 4A) and two (BTF3 and 4) transcripts ranging from 4.0 to 3.3 kb (data not shown). BTF5 is expressed at moderate levels in all tissues tested with the exception of the kidney where the expression level is less. RT-PCR experiments showed that mRNA from the BTF5 gene can be found in all tissues tested, including the kidney (FIG. 4B). Identical results were obtained with primers from the other genes of this group (data not shown). These genes are also 90% identical to each other at the DNA sequence level (but only 58% identical to BTF1 and 2), hence like BTF1 and BTF2, cross-hybridization could account for the similarity in size and patterns on the northern blots and RT-PCR. This might be particularly true for BTF4 which lacks the B30-2 exon but still hybridizes to larger size transcripts like BTF5 and BTF3 (data not shown).

A gene with similarity to 52 kD Ro/SSA auto-antigen

Figures 6A, 6B:
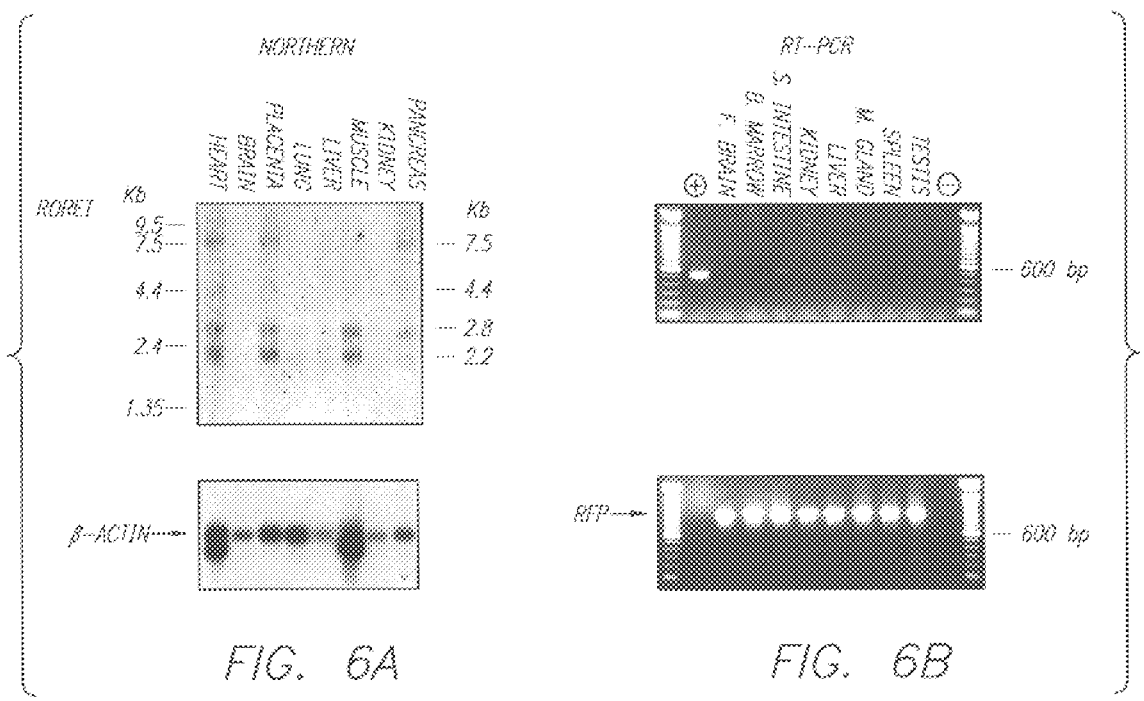
FIG. 6, panel (A) depicts a Northern blot analysis of the RoRet gene. The RoRet cDNA hybridized to 4 different transcripts, ranging from 7.1 kb to 2.2 kb. Autoradiography was performed for 4 days. The re-hybridization of the blot with a b-actin probe showed the variation in poly (A)+ RNA between the lanes. Autoradiography was for 1 hour. Panel (B) depicts RT-PCR analysis of the RoRet gene. Included in the (+) lane was a cDNA 27 positive control. Weak amplification of the correct size was observed in the small intestine, kidney and liver. The other tissues were negative as was the no DNA control lane (−). The RFP primers demonstrated the integrity of the cDNA. Panel (C) depicts Northern blot analysis of NPT3 and NPT4. NPT3 was expressed at high abundance in the heart and muscle as a single 7.2 kb transcript. Lesser amounts were found in the other tissues. The expression pattern of NPT4 was more restricted, being found only in the liver and kidney as a smear of transcripts ranging from 2.6 to 1.7 kb. Panel (D) depicts RT-PCR analysis of the NPT3 and NPT4 genes. Included in the (+) lane were the respective cDNA22E and 22B positive controls. The NPT3 gene was expressed as the proper size PCR fragment in kidney, liver, spleen and testis. A smaller fragment was detected in all tissues with the exception of the liver. The no DNA control lane (−) was negative. NPT4 was expressed as the proper size fragment in the small intestine, kidney, liver and testis. Larger and smaller size fragments were found in all other tissues with the exception of the brain. For both genes these different size fragments may indicate alternative splice events. The no DNA control lane (−) was negative. The RFP primers demonstrated the integrity of the cDNA.

Located approximately 120 kb telomeric to the HLA-H gene is a gene, RoRet, that has 58% amino acid similarity to the 52 kD Ro/SSA protein, an auto-antigen of unknown function that is frequently recognized by antibodies in patients with systemic lupus and Sjogren's syndrome (Anderson et al. *Lancet* 2:456–560 (1961); Clark et al. *J. Immunol.* 102:117–122 (1969)) (FIGS. 1 and 2). Alignment of the predicted amino acid sequence of this cDNA with that of 52 kD Ro/SSA indicated two features associated with the 52 kD Ro/SSA protein: a putative DNA binding cysteine rich motif (C-X-(I,V)-C-X(11–30)-C-X-H-X-(F,I,L)-C-X(2)-C-(I,L,M)-X(10–18)-C-P-X-C) (SEQ ID NO:31) found at the N terminus (Freemont et al. *Cell* 64: 483–484 (1991)) and the B30-2 exon found near the carboxyl terminus, are both conserved in RoRet (FIG. 5). Northern blot analysis indicated the RoRet gene was expressed as two major transcripts of 2.8 and 2.2 kb and two minor transcripts of 7.1 and 4.4 kb in all of the tissues on the blot at levels reflective of the RNA amounts as determined by b-actin probing (FIG. 6A). Using RT-PCR, expression can also be detected in small intestine, kidney liver, and spleen (FIG. 6B).

Two genes with homology to a sodium phosphate transporter

Figure 6C:
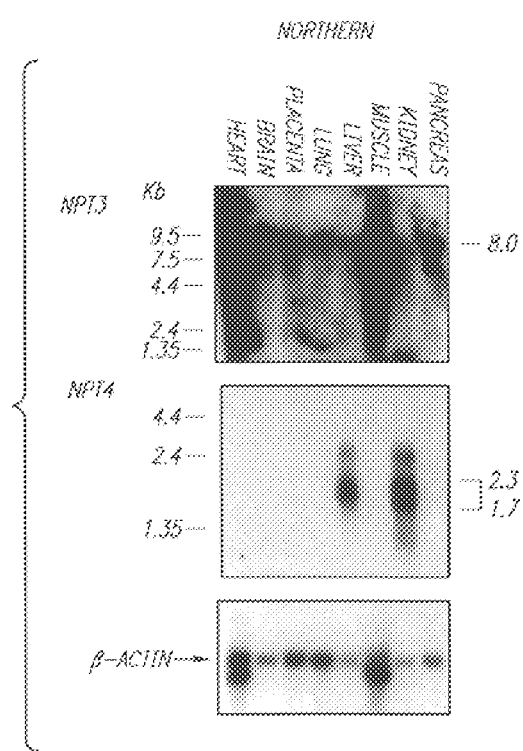
Figure 6D:
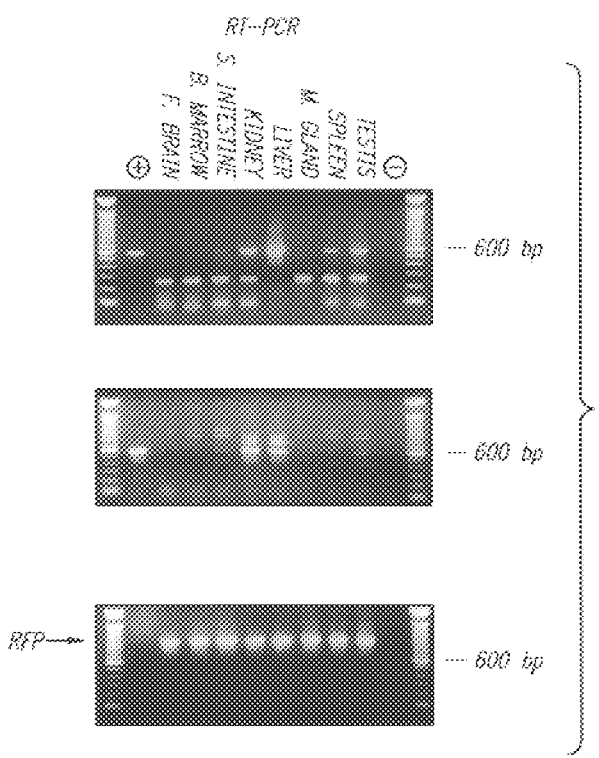

A cDNA for a sodium phosphate transport protein (NPT1) was previously cloned and mapped to 6p21.3 using a somatic cell hybrid panel (Chong et al. *Genomics* 18:355–359 (1993)). NPT1 maps 320 kb telomeric to the HLA-H gene (FIGS. 1 and 2). Two additional cDNAs were cloned which show appreciable homology to NPT1 (FIG. 5). These genes, NPT3 and NPT4, mapped 1.5 megabases and 1.3 megabases centromeric to the NPT1 gene (FIG. 1). Like NPT1, the gene products of NPT3 and NPT4 were extremely hydrophobic, which may reflect a membrane location. Both proteins gave hydrophilicity profiles which were indistinguishable from NPT1 in this study (data not shown). Northern blot analysis indicated that the two genes have different patterns of expression (FIG. 6C). NPT3 was expressed at high levels as a 7.2 kb transcript predominately in muscle and heart. Lesser amount of the mRNA were also found in brain, placenta, lung, liver and pancreas. RT-PCR analysis indicated that expression of the proper size PCR fragment for NPT3 was clearly absent in fetal brain, bone marrow and small intestine (FIG. 6D). A smaller size fragment was detectable in all tissues with the exception of the liver, which may represent evidence for alternative splicing. Although expression was apparently absent from the kidney by northern blot analysis, it was detectable by RT-PCR. Expression was also noted in the mammary gland, spleen and testis. NPT4, on the other hand, was expressed only in the liver and the kidney as a smear of transcripts approximately 2.6–1.7 kb (FIG. 6C). RT-PCR confirmed these results, although a small amount of the proper size PCR fragment was also found in the small intestine and testis (FIG. 6D). Other tissues showed amplification, but the fragments were of larger and smaller size than that produced by the cDNA 22E positive control. Hence, these two genes which apparently have the structural characteristics of a sodium phosphate transporter, appeared to be under the control of different regulatory mechanism that lead to differential patterns of expression.

All publications, patents, and patent applications cited herein are hereby incorporated by reference in their entirety.

What is claimed is:

1. An isolated nucleic acid sequence of approximately 250 kb comprising the sequence of SEQ ID NO:20.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 589 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..589
        ( D ) OTHER INFORMATION: /note= "BT"

( x i ) SEQUENCE DESCRIPTION: SEQ ID NO:1:

```
Met  Ala  Val  Phe  Pro  Ser  Ser  Gly  Leu  Pro  Arg  Cys  Leu  Xaa  Xaa  Xaa
  1              5                        10                       15

Leu  Thr  Leu  Ile  Leu  Leu  Gln  Leu  Pro  Lys  Leu  Asp  Ser  Ala  Pro  Phe
               20                        25                  30

Asp  Val  Ile  Gly  Pro  Pro  Glu  Pro  Ile  Leu  Ala  Val  Val  Gly  Glu  Asp
               35                  40                       45

Ala  Glu  Leu  Pro  Cys  Arg  Leu  Ser  Pro  Asn  Ala  Ser  Ala  Glu  His  Leu
     50                       55                       60

Glu  Leu  Arg  Trp  Phe  Arg  Lys  Lys  Val  Ser  Pro  Ala  Val  Leu  Val  His
 65                      70                       75                        80

Arg  Asp  Gly  Arg  Glu  Gln  Glu  Ala  Glu  Gln  Met  Pro  Glu  Tyr  Arg  Gly
                    85                       90                       95

Arg  Ala  Thr  Leu  Val  Gln  Asp  Gly  Ile  Ala  Lys  Gly  Arg  Val  Ala  Leu
               100                      105                      110

Arg  Ile  Arg  Gly  Val  Arg  Val  Ser  Asp  Asp  Gly  Glu  Tyr  Thr  Cys  Phe
          115                      120                      125

Phe  Arg  Glu  Asp  Gly  Ser  Tyr  Glu  Glu  Ala  Leu  Val  His  Leu  Lys  Val
     130                      135                      140

Ala  Ala  Leu  Gly  Ser  Asp  Pro  His  Ile  Ser  Met  Gln  Val  Gln  Glu  Asn
145                      150                      155                      160

Gly  Glu  Ile  Cys  Leu  Glu  Cys  Thr  Ser  Val  Gly  Trp  Tyr  Pro  Glu  Pro
                    165                      170                      175

Gln  Val  Gln  Trp  Arg  Thr  Ser  Lys  Gly  Glu  Lys  Phe  Pro  Ser  Thr  Ser
```

180                          185                            190
        Glu  Ser  Arg  Asn  Pro  Asp  Glu  Glu  Gly  Leu  Phe  Thr  Val  Ala  Ala  Ser
                  195                      200                 205
        Val  Ile  Ile  Arg  Asp  Thr  Ser  Thr  Lys  Asn  Val  Ser  Cys  Tyr  Ile  Gln
             210                      215                      220
        Asn  Leu  Leu  Leu  Gly  Gln  Glu  Lys  Lys  Val  Glu  Ile  Ser  Ile  Pro  Ala
        225                      230                      235                           240
        Ser  Ser  Leu  Pro  Arg  Leu  Thr  Pro  Trp  Ile  Val  Ala  Val  Ala  Val  Xaa
                            245                      250                           255
        Xaa  Xaa  Xaa  Xaa  Xaa  Xaa  Xaa  Xaa  Xaa  Xaa  Xaa  Xaa  Ile  Leu  Met  Val
                       260                      265                      270
        Leu  Gly  Leu  Leu  Thr  Ile  Gly  Ser  Ile  Phe  Phe  Thr  Trp  Arg  Leu  Tyr
                  275                      280                      285
        Asn  Glu  Arg  Xaa  Xaa  Xaa  Xaa  Xaa  Xaa  Xaa  Pro  Arg  Glu  Arg  Xaa  Xaa
             290                      295                      300
        Xaa  Xaa  Xaa  Xaa  Xaa  Xaa  Xaa  Arg  Asn  Glu  Phe  Ser  Xaa  Xaa  Xaa  Xaa
        305                      310                      315                           320
        Xaa  Xaa  Xaa  Xaa  Ser  Lys  Glu  Arg  Leu  Leu  Glu  Glu  Leu  Lys  Trp  Lys
                            325                      330                           335
        Lys  Ala  Thr  Leu  His  Ala  Xaa  Xaa  Xaa  Xaa  Xaa  Xaa  Xaa  Xaa  Xaa  Xaa
                       340                      345                      350
        Xaa  Xaa  Xaa  Xaa  Xaa  Xaa  Xaa  Xaa  Val  Asp  Val  Thr  Leu  Asp  Pro  Asp
                       355                      360                      365
        Thr  Ala  His  Pro  His  Leu  Phe  Leu  Tyr  Glu  Asp  Ser  Lys  Ser  Val  Arg
                  370                      375                      380
        Leu  Glu  Asp  Ser  Arg  Gln  Lys  Xaa  Xaa  Xaa  Leu  Pro  Glu  Lys  Thr  Glu
        385                      390                      395                           400
        Arg  Phe  Asp  Ser  Trp  Pro  Cys  Val  Leu  Gly  Arg  Glu  Thr  Phe  Thr  Ser
                            405                      410                           415
        Gly  Arg  His  Tyr  Trp  Glu  Val  Glu  Val  Gly  Asp  Arg  Thr  Asp  Trp  Ala
                            420                      425                           430
        Ile  Gly  Val  Cys  Arg  Glu  Asn  Val  Met  Lys  Lys  Xaa  Gly  Phe  Asp  Pro
                       435                      440                      445
        Met  Thr  Pro  Glu  Asn  Gly  Phe  Trp  Ala  Val  Glu  Leu  Tyr  Xaa  Gly  Asn
             450                      455                      460
        Gly  Tyr  Trp  Ala  Leu  Thr  Pro  Leu  Arg  Thr  Pro  Leu  Pro  Leu  Ala  Gly
        465                      470                      475                           480
        Pro  Pro  Arg  Arg  Val  Gly  Ile  Phe  Leu  Asp  Tyr  Glu  Ser  Gly  Asp  Ile
                            485                      490                           495
        Ser  Phe  Tyr  Asn  Met  Asn  Asp  Gly  Ser  Asp  Ile  Tyr  Thr  Phe  Ser  Asn
                       500                      505                      510
        Val  Thr  Phe  Ser  Gly  Pro  Leu  Arg  Phe  Phe  Cys  Leu  Trp  Ser  Ser
                  515                      520                      525
        Gly  Lys  Lys  Pro  Leu  Thr  Ile  Cys  Pro  Ile  Ala  Asp  Gly  Pro  Glu  Arg
             530                      535                      540
        Val  Thr  Val  Ile  Ala  Asn  Ala  Gln  Asp  Leu  Ser  Lys  Glu  Ile  Pro  Leu
        545                      550                      555                           560
        Ser  Pro  Met  Gly  Glu  Glu  Ser  Ala  Pro  Arg  Asp  Ala  Asp  Thr  Leu  His
                       565                      570                      575
        Ser  Lys  Leu  Ile  Pro  Thr  Gln  Pro  Ser  Gln  Gly  Ala  Pro
                       580                      585

( 2 ) INFORMATION FOR SEQ ID NO:2:

(i) SEQUENCE CHARACTERISTICS:
  (A) LENGTH: 581 amino acids
  (B) TYPE: amino acid
  (C) STRANDEDNESS: Not Relevant
  (D) TOPOLOGY: Not Relevant (ii) MOLECULE TYPE: peptide (ix) FEATURE:
  (A) NAME/KEY: Region
  (B) LOCATION: 1..581
  (D) OTHER INFORMATION: /note= "BTF1"

(xi) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Ser | Ala | Ala | Ala | Leu | His | Phe | Ser | Arg | Pro | Ala | Ser | Xaa | Xaa |
| 1 | | | | 5 | | | | | 10 | | | | | 15 | |
| Xaa | Xaa | Leu | Leu | Leu | Leu | Leu | Leu | Ser | Leu | Cys | Ala | Leu | Val | Ser | Ala |
| | | | 20 | | | | | 25 | | | | | 30 | | |
| Gln | Phe | Ile | Val | Val | Gly | Pro | Thr | Asp | Pro | Ile | Leu | Ala | Thr | Val | Gly |
| | | 35 | | | | | 40 | | | | | 45 | | | |
| Glu | Asn | Thr | Thr | Leu | Arg | Cys | His | Leu | Ser | Pro | Glu | Lys | Asn | Ala | Glu |
| | 50 | | | | | 55 | | | | | 60 | | | | |
| Asp | Met | Glu | Val | Arg | Trp | Phe | Arg | Ser | Gln | Phe | Ser | Pro | Ala | Val | Phe |
| 65 | | | | | 70 | | | | | 75 | | | | | 80 |
| Val | Tyr | Lys | Gly | Gly | Arg | Glu | Arg | Thr | Glu | Glu | Gln | Met | Glu | Glu | Tyr |
| | | | | 85 | | | | | 90 | | | | | 95 | |
| Arg | Gly | Arg | Thr | Thr | Phe | Val | Ser | Lys | Asp | Ile | Ser | Arg | Gly | Ser | Val |
| | | | 100 | | | | | 105 | | | | | 110 | | |
| Ala | Leu | Val | Ile | His | Asn | Ile | Thr | Ala | Gln | Glu | Asn | Gly | Thr | Tyr | Arg |
| | | 115 | | | | | 120 | | | | | 125 | | | |
| Cys | Tyr | Phe | Gln | Glu | Gly | Arg | Ser | Tyr | Asp | Glu | Ala | Ile | Leu | His | Leu |
| | 130 | | | | | 135 | | | | | 140 | | | | |
| Val | Val | Ala | Gly | Leu | Gly | Ser | Lys | Pro | Leu | Ile | Ser | Met | Arg | Gly | His |
| 145 | | | | | 150 | | | | | 155 | | | | | 160 |
| Glu | Asp | Gly | Gly | Ile | Arg | Leu | Glu | Cys | Ile | Ser | Arg | Gly | Trp | Tyr | Pro |
| | | | | 165 | | | | | 170 | | | | | 175 | |
| Lys | Pro | Leu | Thr | Val | Trp | Arg | Asp | Pro | Tyr | Gly | Gly | Val | Ala | Pro | Ala |
| | | | 180 | | | | | 185 | | | | | 190 | | |
| Leu | Lys | Glu | Val | Ser | Met | Pro | Asp | Ala | Asp | Gly | Leu | Phe | Met | Val | Thr |
| | | 195 | | | | | 200 | | | | | 205 | | | |
| Thr | Ala | Val | Ile | Ile | Arg | Asp | Lys | Ser | Val | Arg | Asn | Met | Ser | Cys | Ser |
| | 210 | | | | | 215 | | | | | 220 | | | | |
| Ile | Asn | Asn | Thr | Leu | Leu | Gly | Gln | Lys | Lys | Glu | Ser | Val | Ile | Phe | Ile |
| 225 | | | | | 230 | | | | | 235 | | | | | 240 |
| Pro | Glu | Ser | Phe | Met | Pro | Ser | Val | Ser | Pro | Cys | Ala | Val | Ala | Leu | Pro |
| | | | | 245 | | | | | 250 | | | | | 255 | |
| Xaa | Xaa | Xaa | Xaa | Xaa | Xaa | Xaa | Xaa | Xaa | Xaa | Xaa | Xaa | Xaa | Ile | Ile | Val |
| | | | 260 | | | | | 265 | | | | | 270 | | |
| Val | Ile | Leu | Met | Ile | Pro | Ile | Ala | Val | Cys | Ile | Tyr | Trp | Ile | Asn | Lys |
| | | 275 | | | | | 280 | | | | | 285 | | | |
| Leu | Gln | Lys | Glu | Lys | Lys | Ile | Leu | Ser | Gly | Glu | Lys | Glu | Phe | Glu | Arg |
| | 290 | | | | | 295 | | | | | 300 | | | | |
| Glu | Thr | Arg | Glu | Ile | Ala | Leu | Lys | Glu | Leu | Glu | Lys | Glu | Arg | Val | Gln |
| 305 | | | | | 310 | | | | | 315 | | | | | 320 |
| Lys | Glu | Glu | Glu | Leu | Gln | Val | Lys | Glu | Lys | Leu | Gln | Glu | Glu | Leu | Arg |
| | | | | 325 | | | | | 330 | | | | | 335 | |
| Trp | Arg | Arg | Thr | Phe | Leu | His | Ala | Xaa | Xaa | Xaa | Xaa | Xaa | Xaa | Xaa | Xaa |
| | | | 340 | | | | | 345 | | | | | 350 | | |

Xaa   Xaa   Xaa   Xaa   Xaa   Xaa   Xaa   Xaa   Xaa   Xaa   Val   Asp   Val   Val   Leu   Asp
                                355                           360                     365

Pro   Asp   Thr   Ala   His   Pro   Asp   Leu   Phe   Leu   Ser   Glu   Asp   Arg   Arg   Ser
                          370                           375                     380

Val   Arg   Arg   Cys   Pro   Phe   Arg   His   Leu   Gly   Glu   Ser   Val   Pro   Asp   Asn
                    385                           390                     395                                 400

Pro   Glu   Arg   Phe   Asp   Ser   Gln   Pro   Cys   Val   Leu   Gly   Arg   Glu   Ser   Phe
                                            405                           410                           415

Ala   Ser   Gly   Lys   His   Tyr   Trp   Glu   Val   Glu   Val   Glu   Asn   Val   Ile   Glu
                                      420                           425                     430

Trp   Thr   Val   Gly   Val   Cys   Arg   Asp   Ser   Val   Glu   Arg   Lys   Xaa   Gly   Glu
                                435                           440                     445

Val   Leu   Leu   Ile   Pro   Gln   Asn   Gly   Phe   Trp   Thr   Leu   Glu   Met   His   Xaa
                    450                           455                           460

Lys   Gly   Gln   Tyr   Arg   Ala   Val   Ser   Ser   Pro   Asp   Arg   Ile   Leu   Pro   Leu
                    465                           470                           475                           480

Lys   Glu   Ser   Leu   Cys   Arg   Val   Gly   Val   Phe   Leu   Asp   Tyr   Glu   Ala   Gly
                                            485                           490                           495

Asp   Val   Ser   Phe   Tyr   Asn   Met   Arg   Asp   Arg   Ser   His   Ile   Tyr   Thr   Cys
                                      500                           505                           510

Pro   Arg   Ser   Ala   Phe   Ser   Val   Pro   Val   Arg   Phe   Phe   Phe   Arg   Leu   Gly
                                515                           520                           525

Cys   Xaa   Glu   Asp   Ser   Pro   Ile   Phe   Ile   Cys   Pro   Ala   Leu   Thr   Gly   Ala
                          530                           535                           540

Asn   Gly   Val   Thr   Val   Pro   Xaa   Xaa   Xaa   Xaa   Xaa   Xaa   Xaa   Xaa   Xaa   Xaa
                    545                           550                           555                           560

Xaa   Xaa   Xaa   Xaa   Xaa   Xaa   Glu   Glu   Gly   Leu   Thr   Leu   His   Arg   Val   Gly
                                            565                           570                           575

Thr   His   Gln   Ser   Leu
                                            580

( 2 ) INFORMATION FOR SEQ ID NO:3:

( i ) SEQUENCE CHARACTERISTICS:
        ( A ) LENGTH: 581 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..581
        ( D ) OTHER INFORMATION: /note= "BTF2"

( x i ) SEQUENCE DESCRIPTION: SEQ ID NO:3:

Met   Glu   Pro   Ala   Ala   Ala   Leu   His   Phe   Ser   Leu   Pro   Ala   Ser   Leu   Leu
                    1                 5                           10                          15

Leu   Leu   Leu   Leu   Leu   Leu   Leu   Leu   Ser   Leu   Cys   Ala   Leu   Val   Ser   Ala
                                            20                          25                          30

Gln   Phe   Thr   Val   Val   Gly   Pro   Ala   Asn   Pro   Ile   Leu   Ala   Met   Val   Gly
                                35                          40                          45

Glu   Asn   Thr   Thr   Leu   Arg   Cys   His   Leu   Ser   Pro   Glu   Lys   Asn   Ala   Glu
                          50                          55                          60

Asp   Met   Glu   Val   Arg   Trp   Phe   Arg   Ser   Gln   Phe   Ser   Pro   Ala   Val   Phe
                    65                          70                          75                          80

Val   Tyr   Lys   Gly   Gly   Arg   Glu   Arg   Thr   Glu   Glu   Gln   Met   Glu   Glu   Tyr

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| Arg | Gly | Arg | Ile<br>100 | Thr | Phe | Val | Ser | Lys<br>105 | Asp | Ile | Asn | Arg | Gly<br>110 | Ser | Val |
| Ala | Leu | Val<br>115 | Ile | His | Asn | Val | Thr<br>120 | Ala | Gln | Glu | Asn | Gly<br>125 | Ile | Tyr | Arg |
| Cys | Tyr<br>130 | Phe | Gln | Glu | Gly | Arg<br>135 | Ser | Tyr | Asp | Glu | Ala<br>140 | Ile | Leu | Arg | Leu |
| Val<br>145 | Val | Ala | Gly | Leu | Gly<br>150 | Ser | Lys | Pro | Leu | Ile<br>155 | Glu | Ile | Lys | Ala | Gln<br>160 |
| Glu | Asp | Gly | Ser | Ile<br>165 | Trp | Leu | Glu | Cys | Ile<br>170 | Ser | Gly | Gly | Trp | Tyr<br>175 | Pro |
| Glu | Pro | Leu | Thr<br>180 | Val | Trp | Arg | Asp | Pro<br>185 | Tyr | Gly | Glu | Val | Val<br>190 | Pro | Ala |
| Leu | Lys | Glu<br>195 | Val | Ser | Ile | Ala | Asp<br>200 | Ala | Asp | Gly | Leu | Phe<br>205 | Met | Val | Thr |
| Thr | Ala<br>210 | Val | Ile | Ile | Arg | Asp<br>215 | Lys | Tyr | Val | Arg | Asn<br>220 | Val | Ser | Cys | Ser |
| Val<br>225 | Asn | Asn | Thr | Leu | Leu<br>230 | Gly | Gln | Glu | Lys | Glu<br>235 | Thr | Val | Ile | Phe | Ile<br>240 |
| Pro | Glu | Ser | Phe | Met<br>245 | Pro | Ser | Ala | Ser | Pro<br>250 | Trp | Met | Val | Ala | Leu<br>255 | Ala |
| Val | Ile | Leu | Thr<br>260 | Ala | Ser | Pro | Trp | Met<br>265 | Val | Ser | Met | Thr | Val<br>270 | Ile | Leu |
| Ala | Val | Phe<br>275 | Ile | Ile | Phe | Met | Ala<br>280 | Val | Ser | Ile | Cys | Cys<br>285 | Ile | Lys | Lys |
| Leu | Gln<br>290 | Arg | Glu | Lys | Lys | Ile<br>295 | Leu | Ser | Gly | Glu | Lys<br>300 | Lys | Val | Glu | Gln |
| Glu<br>305 | Xaa | Xaa | Xaa | Xaa | Xaa<br>310 | Xaa | Xaa | Xaa | Glu | Lys<br>315 | Glu | Xaa | Xaa | Xaa<br>320 |     |
| Xaa | Xaa | Xaa | Xaa | Xaa<br>325 | Xaa | Ile | Ala | Gln | Gln<br>330 | Leu | Gln | Glu | Glu | Leu<br>335 | Arg |
| Trp | Arg | Arg | Thr<br>340 | Phe | Leu | His | Ala | Xaa<br>345 | Xaa | Xaa | Xaa | Xaa | Xaa<br>350 | Xaa | Xaa |
| Xaa | Xaa | Xaa<br>355 | Xaa | Xaa | Xaa | Xaa | Xaa<br>360 | Xaa | Xaa | Ala | Asp | Val<br>365 | Val | Leu | Asp |
| Pro | Asp<br>370 | Thr | Ala | His | Pro | Glu<br>375 | Leu | Phe | Leu | Ser | Glu<br>380 | Asp | Arg | Arg | Ser |
| Val<br>385 | Arg | Arg | Gly | Pro | Tyr<br>390 | Arg | Gln | Arg | Xaa | Xaa<br>395 | Val | Pro | Asp | Asn<br>400 |     |
| Pro | Glu | Arg | Phe | Asp<br>405 | Ser | Gln | Pro | Cys | Val<br>410 | Leu | Gly | Trp | Glu | Ser<br>415 | Phe |
| Ala | Ser | Gly | Lys<br>420 | His | Tyr | Trp | Glu | Val<br>425 | Glu | Val | Glu | Asn | Val<br>430 | Met | Val |
| Trp | Thr | Val<br>435 | Gly | Val | Cys | Arg | His<br>440 | Ser | Val | Glu | Arg | Lys<br>445 | Xaa | Gly | Glu |
| Val | Leu<br>450 | Leu | Ile | Pro | Gln | Asn<br>455 | Gly | Phe | Trp | Thr | Leu<br>460 | Glu | Met | Phe | Xaa |
| Gly<br>465 | Asn | Gln | Tyr | Arg | Ala<br>470 | Leu | Ser | Ser | Pro | Glu<br>475 | Arg | Ile | Leu | Pro | Leu<br>480 |
| Lys | Glu | Ser | Leu | Cys<br>485 | Arg | Val | Gly | Val | Phe<br>490 | Leu | Asp | Tyr | Glu | Ala<br>495 | Gly |
| Asp | Val | Ser | Phe<br>500 | Tyr | Asn | Met | Arg | Asp<br>505 | Arg | Ser | His | Ile | Tyr<br>510 | Thr | Cys |

```
Pro  Arg  Ser  Ala  Phe  Thr  Val  Pro  Val  Arg  Phe  Phe  Arg  Leu  Gly
     515                520                     525

Ser  Xaa  Asp  Asp  Ser  Pro  Ile  Phe  Ile  Cys  Pro  Ala  Leu  Thr  Gly  Ala
     530                535                     540

Ser  Gly  Val  Met  Val  Pro  Xaa  Xaa  Xaa  Xaa  Xaa  Xaa  Xaa  Xaa  Xaa
545                      550                     555                      560

Xaa  Xaa  Xaa  Xaa  Xaa  Xaa  Glu  Glu  Gly  Leu  Lys  Leu  His  Arg  Val  Gly
               565                     570                          575

Thr  His  Gln  Ser  Leu
                    580
```

( 2 ) INFORMATION FOR SEQ ID NO:4:

( i ) SEQUENCE CHARACTERISTICS:
        ( A ) LENGTH: 540 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..540
        ( D ) OTHER INFORMATION: /note= "BTF5"

( x i ) SEQUENCE DESCRIPTION: SEQ ID NO:4:

```
Met  Lys  Met  Ala  Ser  Phe  Leu  Ala  Phe  Leu  Leu  Asn  Phe  Arg  Xaa
1                   5                     10                     15

Xaa  Xaa  Val  Cys  Leu  Leu  Leu  Leu  Gln  Leu  Leu  Met  Pro  His  Ser  Ala
               20                     25                     30

Gln  Phe  Ser  Val  Leu  Gly  Pro  Ser  Gly  Pro  Ile  Leu  Ala  Met  Val  Gly
          35                     40                     45

Glu  Asp  Ala  Asp  Leu  Pro  Cys  His  Leu  Phe  Pro  Thr  Met  Ser  Ala  Glu
     50                     55                     60

Thr  Met  Glu  Leu  Lys  Trp  Val  Ser  Ser  Leu  Arg  Gln  Val  Val  Asn
65                   70                     75                     80

Val  Tyr  Ala  Asp  Gly  Lys  Glu  Val  Glu  Asp  Arg  Gln  Ser  Ala  Pro  Tyr
               85                     90                          95

Arg  Gly  Arg  Thr  Ser  Ile  Leu  Arg  Asp  Gly  Ile  Thr  Ala  Gly  Lys  Ala
                    100                    105                    110

Ala  Leu  Arg  Ile  His  Asn  Val  Thr  Ala  Ser  Asp  Ser  Gly  Lys  Tyr  Leu
               115                    120                    125

Cys  Tyr  Phe  Gln  Asp  Gly  Asp  Phe  Tyr  Glu  Lys  Ala  Leu  Val  Glu  Leu
     130                    135                    140

Lys  Val  Ala  Ala  Leu  Gly  Ser  Asp  Leu  His  Val  Asp  Val  Lys  Gly  Tyr
145                      150                    155                         160

Lys  Asp  Gly  Gly  Ile  His  Leu  Glu  Cys  Arg  Ser  Thr  Gly  Trp  Tyr  Pro
               165                    170                         175

Gln  Pro  Gln  Ile  Gln  Trp  Ser  Asn  Asn  Lys  Gly  Glu  Asn  Ile  Pro  Thr
               180                    185                         190

Val  Glu  Ala  Pro  Val  Val  Ala  Asp  Gly  Val  Gly  Leu  Tyr  Ala  Val  Ala
          195                    200                    205

Ala  Ser  Val  Ile  Met  Arg  Gly  Ser  Ser  Gly  Glu  Gly  Val  Ser  Cys  Thr
     210                    215                    220

Ile  Arg  Ser  Ser  Leu  Leu  Gly  Leu  Glu  Lys  Thr  Ala  Ser  Ile  Ser  Ile
225                      230                    235                         240

Ala  Asp  Pro  Phe  Phe  Arg  Ser  Ala  Gln  Arg  Trp  Ile  Ala  Ala  Leu  Ala
               245                    250                         255
```

|     |     |     |     |     |     |     |     |     |     |     |     |     |     |     |
|-----|-----|-----|-----|-----|-----|-----|-----|-----|-----|-----|-----|-----|-----|-----|
| Arg | Xaa | Xaa | Xaa | Xaa | Xaa | Xaa | Xaa | Xaa | Xaa | Xaa | Xaa | Xaa | Thr | Leu |
|     |     | 260 |     |     |     |     | 265 |     |     |     |     | 270 |     |     |
| Pro | Val | Leu | Leu | Leu | Leu | Leu | Gly | Gly | Ala | Gly | Tyr | Phe | Leu | Trp | Gln |
|     |     | 275 |     |     |     |     | 280 |     |     |     |     | 285 |     |     |
| Gln | Gln | Gln | Glu | Glu | Lys | Lys | Thr | Gln | Phe | Arg | Lys | Lys | Lys | Arg | Glu | Gln |
|     | 290 |     |     |     |     |     | 295 |     |     |     |     | 300 |     |     |     |
| Glu | Leu | Arg | Glu | Met | Ala | Trp | Ser | Thr | Met | Lys | Gln | Glu | Gln | Ser | Xaa |
| 305 |     |     |     |     | 310 |     |     |     |     | 315 |     |     |     |     | 320 |
| Xaa | Xaa | Xaa | Xaa | Xaa | Xaa | Thr | Arg | Val | Lys | Leu | Leu | Glu | Glu | Leu | Arg |
|     |     |     |     | 325 |     |     |     |     | 330 |     |     |     |     | 335 |     |
| Trp | Arg | Ser | Ile | Gln | Tyr | Ala | Ser | Arg | Gly | Glu | Arg | His | Ser | Ala | Tyr |
|     |     |     | 340 |     |     |     |     | 345 |     |     |     |     | 350 |     |     |
| Asn | Glu | Trp | Lys | Lys | Ala | Leu | Phe | Lys | Pro | Ala | Asp | Val | Ile | Leu | Asp |
|     |     | 355 |     |     |     |     | 360 |     |     |     |     | 365 |     |     |     |
| Pro | Lys | Thr | Ala | Asn | Pro | Ile | Leu | Leu | Val | Ser | Glu | Asp | Gln | Arg | Ser |
|     | 370 |     |     |     |     | 375 |     |     |     |     | 380 |     |     |     |     |
| Val | Gln | Arg | Ala | Lys | Glu | Pro | Gln | Asp | Xaa | Xaa | Xaa | Leu | Pro | Asp | Asn |
| 385 |     |     |     |     | 390 |     |     |     |     | 395 |     |     |     |     | 400 |
| Pro | Glu | Arg | Phe | Asn | Trp | His | Tyr | Cys | Val | Leu | Gly | Cys | Glu | Ser | Phe |
|     |     |     |     | 405 |     |     |     |     | 410 |     |     |     |     | 415 |     |
| Ile | Ser | Gly | Arg | His | Tyr | Trp | Glu | Val | Gly | Asp | Arg | Lys | Glu |
|     |     |     | 420 |     |     |     |     | 425 |     |     |     |     | 430 |     |
| Trp | His | Ile | Gly | Val | Cys | Ser | Lys | Asn | Val | Gln | Arg | Lys | Xaa | Gly | Trp |
|     |     | 435 |     |     |     |     | 440 |     |     |     |     | 445 |     |     |     |
| Val | Lys | Met | Thr | Pro | Glu | Asn | Gly | Phe | Trp | Thr | Met | Gly | Leu | Thr | Asp |
|     | 450 |     |     |     |     | 455 |     |     |     |     | 460 |     |     |     |     |
| Gly | Asn | Lys | Tyr | Arg | Thr | Leu | Thr | Glu | Pro | Arg | Thr | Asn | Leu | Lys | Leu |
| 465 |     |     |     |     | 470 |     |     |     |     | 475 |     |     |     |     | 480 |
| Pro | Lys | Pro | Pro | Lys | Lys | Val | Gly | Val | Phe | Leu | Asp | Tyr | Glu | Thr | Gly |
|     |     |     |     | 485 |     |     |     |     | 490 |     |     |     |     | 495 |     |
| Asp | Ile | Ser | Phe | Tyr | Asn | Ala | Val | Asp | Gly | Ser | His | Ile | His | Thr | Phe |
|     |     |     | 500 |     |     |     |     | 505 |     |     |     |     | 510 |     |     |
| Leu | Asp | Val | Ser | Phe | Ser | Glu | Ala | Leu | Tyr | Phe | Val | Phe | Arg | Ile | Leu |
|     |     | 515 |     |     |     |     | 520 |     |     |     |     | 525 |     |     |     |
| Thr | Leu | Glu | Pro | Thr | Ala | Leu | Ser | Ile | Cys | Pro | Ala |
|     | 530 |     |     |     |     | 535 |     |     |     |     | 540 |

( 2 ) INFORMATION FOR SEQ ID NO:5:

( i ) SEQUENCE CHARACTERISTICS:
        ( A ) LENGTH: 610 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..610
        ( D ) OTHER INFORMATION: /note= "BTF3"

( x i ) SEQUENCE DESCRIPTION: SEQ ID NO:5:

|     |     |     |     |     |     |     |     |     |     |     |     |     |     |     |
|-----|-----|-----|-----|-----|-----|-----|-----|-----|-----|-----|-----|-----|-----|-----|
| Met | Lys | Met | Ala | Ser | Ser | Leu | Ala | Phe | Leu | Leu | Leu | Asn | Phe | His | Xaa |
| 1   |     |     |     | 5   |     |     |     |     | 10  |     |     |     |     | 15  |     |
| Xaa | Xaa | Val | Ser | Leu | Phe | Leu | Val | Gln | Leu | Leu | Thr | Pro | Cys | Ser | Ala |
|     |     |     | 20  |     |     |     |     | 25  |     |     |     |     | 30  |     |     |
| Gln | Phe | Ser | Val | Leu | Gly | Pro | Ser | Gly | Pro | Ile | Leu | Ala | Met | Val | Gly |

|   |   |   | 35 |   |   |   | 40 |   |   |   | 45 |   |   |   |
|---|---|---|---|---|---|---|---|---|---|---|---|---|---|---|
| Glu | Asp | Ala | Asp | Leu | Pro | Cys | His | Leu | Phe | Pro | Thr | Met | Ser | Ala | Glu |
|  | 50 |  |  |  |  | 55 |  |  |  |  | 60 |  |  |  |  |
| Thr | Met | Glu | Leu | Arg | Trp | Val | Ser | Ser | Leu | Arg | Gln | Val | Val | Asn |
| 65 |  |  |  |  | 70 |  |  |  |  | 75 |  |  |  |  | 80 |
| Val | Tyr | Ala | Asp | Gly | Lys | Glu | Val | Glu | Asp | Arg | Gln | Ser | Ala | Pro | Tyr |
|  |  |  |  | 85 |  |  |  |  | 90 |  |  |  |  | 95 |  |
| Arg | Gly | Arg | Thr | Ser | Ile | Leu | Arg | Asp | Gly | Ile | Thr | Ala | Gly | Lys | Ala |
|  |  |  | 100 |  |  |  |  | 105 |  |  |  |  | 110 |  |  |
| Ala | Leu | Arg | Ile | His | Asn | Val | Thr | Ala | Ser | Asp | Ser | Gly | Lys | Tyr | Leu |
|  |  | 115 |  |  |  |  | 120 |  |  |  |  | 125 |  |  |  |
| Cys | Tyr | Phe | Gln | Asp | Gly | Asp | Phe | Tyr | Glu | Lys | Ala | Leu | Val | Glu | Leu |
|  | 130 |  |  |  |  | 135 |  |  |  |  | 140 |  |  |  |  |
| Lys | Val | Ala | Ala | Leu | Gly | Ser | Asp | Leu | His | Ile | Glu | Val | Lys | Gly | Tyr |
| 145 |  |  |  |  | 150 |  |  |  |  | 155 |  |  |  |  | 160 |
| Glu | Asp | Gly | Gly | Ile | His | Leu | Glu | Cys | Arg | Ser | Thr | Gly | Trp | Tyr | Pro |
|  |  |  |  | 165 |  |  |  |  | 170 |  |  |  |  | 175 |  |
| Gln | Pro | Gln | Ile | Lys | Trp | Ser | Asp | Thr | Lys | Gly | Glu | Asn | Ile | Pro | Ala |
|  |  |  | 180 |  |  |  |  | 185 |  |  |  |  | 190 |  |  |
| Val | Glu | Ala | Pro | Val | Val | Ala | Asp | Gly | Val | Gly | Leu | Tyr | Ala | Val | Ala |
|  |  | 195 |  |  |  |  | 200 |  |  |  |  | 205 |  |  |  |
| Ala | Ser | Val | Ile | Met | Arg | Gly | Ser | Ser | Gly | Gly | Gly | Val | Ser | Cys | Ile |
|  | 210 |  |  |  |  | 215 |  |  |  |  | 220 |  |  |  |  |
| Ile | Arg | Asn | Ser | Leu | Leu | Gly | Leu | Glu | Lys | Thr | Ala | Ser | Ile | Ser | Ile |
| 225 |  |  |  |  | 230 |  |  |  |  | 235 |  |  |  |  | 240 |
| Ala | Asp | Pro | Phe | Phe | Arg | Ser | Ala | Gln | Pro | Trp | Ile | Ala | Ala | Leu | Ala |
|  |  |  |  | 245 |  |  |  |  | 250 |  |  |  |  | 255 |  |
| Gly | Xaa | Xaa | Xaa | Xaa | Xaa | Xaa | Xaa | Xaa | Xaa | Xaa | Xaa | Xaa | Thr | Leu |
|  |  |  | 260 |  |  |  |  | 265 |  |  |  |  | 270 |  |  |
| Pro | Ile | Ser | Leu | Leu | Leu | Leu | Ala | Gly | Ala | Ser | Tyr | Phe | Leu | Trp | Arg |
|  |  |  | 275 |  |  |  |  | 280 |  |  |  |  | 285 |  |  |
| Gln | Gln | Lys | Glu | Lys | Ile | Ala | Leu | Ser | Arg | Glu | Thr | Glu | Arg | Glu | Arg |
|  | 290 |  |  |  |  | 295 |  |  |  |  | 300 |  |  |  |  |
| Glu | Met | Lys | Glu | Met | Gly | Tyr | Ala | Ala | Thr | Glu | Gln | Glu | Ile | Ser | Xaa |
| 305 |  |  |  |  | 310 |  |  |  |  | 315 |  |  |  |  | 320 |
| Xaa | Xaa | Xaa | Xaa | Xaa | Xaa | Leu | Arg | Glu | Lys | Leu | Gln | Glu | Glu | Leu | Lys |
|  |  |  |  | 325 |  |  |  |  | 330 |  |  |  |  | 335 |  |
| Trp | Arg | Lys | Ile | Gln | Tyr | Met | Ala | Arg | Gly | Glu | Lys | Ser | Leu | Ala | Tyr |
|  |  |  | 340 |  |  |  |  | 345 |  |  |  |  | 350 |  |  |
| His | Glu | Trp | Lys | Met | Ala | Leu | Phe | Lys | Pro | Ala | Asp | Val | Ile | Leu | Asp |
|  |  | 355 |  |  |  |  | 360 |  |  |  |  | 365 |  |  |  |
| Pro | Asp | Thr | Ala | Asn | Ala | Ile | Leu | Leu | Val | Ser | Glu | Asp | Gln | Arg | Ser |
|  | 370 |  |  |  |  | 375 |  |  |  |  | 380 |  |  |  |  |
| Val | Gln | Arg | Ala | Glu | Glu | Pro | Arg | Asp | Xaa | Xaa | Xaa | Leu | Pro | Asp | Asn |
| 385 |  |  |  |  | 390 |  |  |  |  | 395 |  |  |  |  | 400 |
| Pro | Glu | Arg | Phe | Glu | Trp | Arg | Tyr | Cys | Val | Leu | Gly | Cys | Glu | Asn | Phe |
|  |  |  |  | 405 |  |  |  |  | 410 |  |  |  |  | 415 |  |
| Thr | Ser | Gly | Arg | His | Tyr | Trp | Glu | Val | Glu | Val | Gly | Asp | Arg | Lys | Glu |
|  |  |  | 420 |  |  |  |  | 425 |  |  |  |  | 430 |  |  |
| Trp | His | Ile | Gly | Val | Cys | Ser | Lys | Asn | Val | Glu | Arg | Lys | Lys | Gly | Trp |
|  |  | 435 |  |  |  |  | 440 |  |  |  |  | 445 |  |  |  |
| Val | Lys | Met | Thr | Pro | Glu | Asn | Gly | Tyr | Trp | Thr | Met | Gly | Leu | Thr | Asp |
|  | 450 |  |  |  |  | 455 |  |  |  |  | 460 |  |  |  |  |

```
Gly  Asn  Lys  Tyr  Arg  Ala  Leu  Thr  Glu  Pro  Arg  Thr  Asn  Leu  Lys  Leu
465                 470                      475                      480

Pro  Glu  Pro  Pro  Arg  Lys  Val  Gly  Ile  Phe  Leu  Asp  Tyr  Glu  Thr  Gly
               485                      490                      495

Glu  Ile  Ser  Phe  Tyr  Asn  Ala  Thr  Asp  Gly  Ser  His  Ile  Tyr  Thr  Phe
               500                      505                      510

Pro  His  Ala  Ser  Phe  Ser  Glu  Pro  Leu  Tyr  Phe  Val  Phe  Arg  Ile  Leu
          515                      520                      525

Thr  Leu  Glu  Pro  Thr  Ala  Leu  Thr  Ile  Cys  Pro  Ile  Pro  Lys  Glu  Val
     530                      535                      540

Glu  Ser  Ser  Pro  Asp  Pro  Asp  Leu  Val  Pro  Asp  His  Ser  Leu  Glu  Thr
545                      550                      555                      560

Pro  Leu  Thr  Pro  Gly  Leu  Ala  Asn  Glu  Ser  Gly  Glu  Pro  Gln  Ala  Glu
               565                      570                      575

Val  Thr  Ser  Leu  Leu  Leu  Pro  Ala  His  Pro  Gly  Ala  Glu  Val  Ser  Pro
               580                      585                      590

Ser  Ala  Thr  Thr  Asn  Gln  Asn  His  Lys  Leu  Gln  Ala  Arg  Thr  Glu  Ala
          595                      600                      605

Leu  Tyr
     610
```

( 2 ) INFORMATION FOR SEQ ID NO:6:

( i ) SEQUENCE CHARACTERISTICS:
        ( A ) LENGTH: 342 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..342
        ( D ) OTHER INFORMATION: /note= "BTF4"

( x i ) SEQUENCE DESCRIPTION: SEQ ID NO:6:

```
Met  Lys  Met  Ala  Ser  Ser  Leu  Ala  Phe  Leu  Leu  Leu  Asn  Phe  His  Xaa
1                   5                        10                       15

Xaa  Xaa  Val  Ser  Leu  Leu  Leu  Val  Gln  Leu  Leu  Thr  Pro  Cys  Ser  Ala
               20                       25                       30

Gln  Phe  Ser  Val  Leu  Gly  Pro  Ser  Gly  Pro  Ile  Leu  Ala  Met  Val  Gly
          35                       40                       45

Glu  Asp  Ala  Asp  Leu  Pro  Cys  His  Leu  Phe  Pro  Thr  Met  Ser  Ala  Glu
     50                       55                       60

Thr  Met  Glu  Leu  Lys  Trp  Val  Ser  Ser  Ser  Leu  Arg  Gln  Val  Val  Asn
65                       70                       75                       80

Val  Tyr  Ala  Asp  Gly  Lys  Glu  Val  Glu  Asp  Arg  Gln  Ser  Ala  Pro  Tyr
               85                       90                       95

Arg  Gly  Arg  Thr  Ser  Ile  Leu  Arg  Asp  Gly  Ile  Thr  Ala  Gly  Lys  Ala
               100                      105                      110

Ala  Leu  Arg  Ile  His  Asn  Val  Thr  Ala  Ser  Asp  Ser  Gly  Lys  Tyr  Leu
          115                      120                      125

Cys  Tyr  Phe  Gln  Asp  Gly  Asp  Phe  Tyr  Glu  Lys  Ala  Leu  Val  Glu  Leu
     130                      135                      140

Lys  Val  Ala  Ala  Leu  Gly  Ser  Asn  Leu  His  Val  Glu  Val  Lys  Gly  Tyr
145                      150                      155                      160

Glu  Asp  Gly  Gly  Ile  His  Leu  Glu  Cys  Arg  Ser  Thr  Gly  Trp  Tyr  Pro
               165                      170                      175
```

|  |  |  |  |  |  |  |  |  |  |  |  |  |  |  |
|---|---|---|---|---|---|---|---|---|---|---|---|---|---|---|
| Gln | Pro | Gln | Ile<br>180 | Gln | Trp | Ser | Asn | Ala<br>185 | Lys | Gly | Glu | Asn | Ile<br>190 | Pro | Ala |
| Val | Glu | Ala<br>195 | Pro | Val | Val | Ala | Asp<br>200 | Gly | Val | Gly | Leu | Tyr<br>205 | Glu | Val | Ala |
| Ala | Ser<br>210 | Val | Ile | Met | Arg | Gly<br>215 | Gly | Ser | Gly | Glu | Gly<br>220 | Val | Ser | Cys | Ile |
| Ile<br>225 | Arg | Asn | Ser | Leu | Leu<br>230 | Gly | Leu | Glu | Lys | Thr<br>235 | Ala | Ser | Ile | Ser | Ile<br>240 |
| Ala | Asp | Pro | Phe | Phe<br>245 | Arg | Ser | Ala | Gln | Pro<br>250 | Trp | Ile | Ala | Ala | Leu<br>255 | Ala |
| Gly | Xaa | Xaa | Xaa<br>260 | Xaa | Xaa | Xaa | Xaa | Xaa<br>265 | Xaa | Xaa | Xaa | Xaa<br>270 | Thr | Leu |
| Pro | Ile | Leu<br>275 | Leu | Leu | Leu | Leu | Ala<br>280 | Gly | Ala | Ser | Tyr | Phe<br>285 | Leu | Trp | Arg |
| Gln | Gln<br>290 | Lys | Glu | Ile | Thr | Ala<br>295 | Leu | Ser | Ser | Glu | Ile<br>300 | Glu | Ser | Glu | Gln |
| Glu<br>305 | Met | Lys | Glu | Met | Gly<br>310 | Tyr | Ala | Ala | Thr | Glu<br>315 | Arg | Glu | Ile | Ser | Xaa<br>320 |
| Xaa | Xaa | Xaa | Xaa | Xaa<br>325 | Xaa | Leu | Arg | Glu | Ser<br>330 | Leu | Gln | Glu | Glu | Leu<br>335 | Lys |
| Arg | Lys | Lys | Ser<br>340 | Ser | Thr |  |  |  |  |  |  |  |  |  |

( 2 ) INFORMATION FOR SEQ ID NO:7:

( i ) SEQUENCE CHARACTERISTICS:
        ( A ) LENGTH: 487 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..487
        ( D ) OTHER INFORMATION: /note= "52 kD Ro"

( x i ) SEQUENCE DESCRIPTION: SEQ ID NO:7:

|  |  |  |  |  |  |  |  |  |  |  |  |  |  |  |
|---|---|---|---|---|---|---|---|---|---|---|---|---|---|---|
| Met<br>1 | Ala | Ser | Ala | Ala<br>5 | Arg | Leu | Thr | Met | Met<br>10 | Trp | Glu | Glu | Val | Thr<br>15 | Cys |
| Pro | Ile | Cys | Leu<br>20 | Asp | Pro | Phe | Val | Glu<br>25 | Pro | Val | Ser | Ile | Glu<br>30 | Cys | Gly |
| His | Ser | Phe<br>35 | Cys | Gln | Glu | Cys | Ile<br>40 | Ser | Gln | Val | Gly | Lys<br>45 | Gly | Gly | Gly |
| Ser<br>50 | Xaa | Xaa | Xaa | Xaa | Xaa<br>55 | Xaa | Xaa | Val | Cys | Pro<br>60 | Val | Cys | Arg | Gln |
| Arg<br>65 | Phe | Leu | Leu | Lys | Asn<br>70 | Leu | Arg | Pro | Asn | Arg<br>75 | Gln | Leu | Ala | Asn | Met<br>80 |
| Val | Asn | Asn | Leu | Lys<br>85 | Glu | Ile | Ser | Gln | Glu<br>90 | Ala | Arg | Glu | Gly | Thr<br>95 | Gln |
| Gly | Glu | Arg | Cys<br>100 | Ala | Val | His | Gly<br>105 | Glu | Arg | Leu | His | Leu<br>110 | Phe | Cys | Glu |
| Lys | Asp | Gly<br>115 | Lys | Ala | Leu | Cys | Trp<br>120 | Val | Cys | Ala | Gln | Ser<br>125 | Arg | Lys | His |
| Arg | Asp<br>130 | His | Ala | Met | Val | Pro<br>135 | Leu | Glu | Glu | Ala | Ala<br>140 | Gln | Glu | Tyr | Gln |
| Glu | Lys | Leu | Gln | Val | Ala | Leu | Gly | Glu | Leu | Arg | Arg | Lys | Gln | Glu | Leu |

-continued

|  |  |  |  | 145 |  |  |  | 150 |  |  |  | 155 |  |  | 160 |
|---|---|---|---|---|---|---|---|---|---|---|---|---|---|---|---|
| Ala | Glu | Lys | Leu | Glu | Val | Glu | Ile | Ala | Ile | Lys | Arg | Ala | Asp | Trp | Lys |
|  |  |  |  | 165 |  |  |  |  | 170 |  |  |  |  | 175 |  |
| Lys | Thr | Val | Glu | Thr | Gln | Lys | Ser | Arg | Ile | His | Ala | Glu | Phe | Val | Gln |
|  |  |  | 180 |  |  |  |  | 185 |  |  |  |  | 190 |  |  |
| Gln | Lys | Asn | Phe | Leu | Val | Glu | Glu | Gln | Arg | Gln | Leu | Gln | Glu | Leu |
|  |  | 195 |  |  |  |  | 200 |  |  |  |  | 205 |  |  |  |
| Glu | Lys | Asp | Glu | Arg | Glu | Gln | Leu | Arg | Ile | Leu | Gly | Glu | Lys | Glu | Ala |
|  | 210 |  |  |  |  | 215 |  |  |  |  | 220 |  |  |  |  |
| Lys | Leu | Ala | Gln | Gln | Ser | Gln | Ala | Leu | Gln | Glu | Leu | Ile | Ser | Glu | Leu |
| 225 |  |  |  |  | 230 |  |  |  |  | 235 |  |  |  |  | 240 |
| Asp | Arg | Arg | Cys | His | Ser | Ser | Ala | Leu | Glu | Leu | Leu | Gln | Glu | Val | Ile |
|  |  |  |  | 245 |  |  |  |  | 250 |  |  |  |  | 255 |  |
| Ile | Val | Leu | Glu | Arg | Ser | Glu | Ser | Trp | Asn | Leu | Lys | Asp | Leu | Asp | Ile |
|  |  |  | 260 |  |  |  |  | 265 |  |  |  |  | 270 |  |  |
| Thr | Ser | Pro | Glu | Leu | Arg | Ser | Val | Cys | His | Val | Pro | Xaa | Xaa | Xaa |
|  |  | 275 |  |  |  |  | 280 |  |  |  |  | 285 |  |  |  |
| Gly | Leu | Lys | Lys | Met | Leu | Arg | Thr | Cys | Ala | Val | His | Ile | Thr | Leu | Asp |
|  | 290 |  |  |  |  | 295 |  |  |  |  | 300 |  |  |  |  |
| Pro | Asp | Thr | Ala | Asn | Pro | Trp | Leu | Ile | Leu | Ser | Glu | Asp | Arg | Arg | Gln |
| 305 |  |  |  |  | 310 |  |  |  |  | 315 |  |  |  |  | 320 |
| Val | Arg | Leu | Gly | Asp | Thr | Gln | Gln | Ser | Ile | Pro | Gly | Asn | Glu | Glu | Arg |
|  |  |  |  | 325 |  |  |  |  | 330 |  |  |  |  | 335 |  |
| Phe | Asp | Ser | Tyr | Pro | Met | Val | Leu | Gly | Ala | Gln | His | Phe | His | Ser | Gly |
|  |  |  | 340 |  |  |  |  | 345 |  |  |  |  | 350 |  |  |
| Lys | His | Tyr | Trp | Glu | Val | Asp | Val | Thr | Gly | Lys | Glu | Ala | Trp | Asp | Leu |
|  |  | 355 |  |  |  |  | 360 |  |  |  |  | 365 |  |  |  |
| Gly | Val | Cys | Arg | Asp | Ser | Val | Arg | Arg | Lys | Gly | His | Phe | Leu | Leu | Ser |
|  | 370 |  |  |  |  | 375 |  |  |  |  | 380 |  |  |  |  |
| Ser | Lys | Ser | Gly | Phe | Trp | Thr | Ile | Trp | Leu | Trp | Asn | Lys | Gln | Lys | Tyr |
| 385 |  |  |  |  | 390 |  |  |  |  | 395 |  |  |  |  | 400 |
| Glu | Ala | Gly | Thr | Tyr | Pro | Gln | Thr | Pro | Leu | His | Leu | Gln | Val | Pro | Pro |
|  |  |  |  | 405 |  |  |  |  | 410 |  |  |  |  | 415 |  |
| Cys | Gln | Val | Gly | Ile | Phe | Leu | Asp | Tyr | Glu | Ala | Gly | Met | Val | Ser | Phe |
|  |  |  | 420 |  |  |  |  | 425 |  |  |  |  | 430 |  |  |
| Tyr | Asn | Ile | Thr | Asp | His | Gly | Ser | Leu | Ile | Tyr | Ser | Phe | Ser | Glu | Cys |
|  |  | 435 |  |  |  |  | 440 |  |  |  |  | 445 |  |  |  |
| Ala | Phe | Thr | Gly | Pro | Leu | Arg | Pro | Phe | Phe | Ser | Pro | Gly | Phe | Asn | Asp |
|  | 450 |  |  |  |  | 455 |  |  |  |  | 460 |  |  |  |  |
| Gly | Gly | Lys | Asn | Thr | Ala | Pro | Leu | Thr | Leu | Cys | Pro | Leu | Asn | Ile | Gly |
| 465 |  |  |  |  | 470 |  |  |  |  | 475 |  |  |  |  | 480 |
| Ser | Gln | Gly | Ser | Thr | Asp | Tyr |  |  |  |  |  |  |  |  |  |
|  |  |  |  | 485 |  |  |  |  |  |  |  |  |  |  |  |

( 2 ) INFORMATION FOR SEQ ID NO:8:

( i ) SEQUENCE CHARACTERISTICS:
        ( A ) LENGTH: 485 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..485
        ( D ) OTHER INFORMATION: /note= "RoRet"

( x i ) SEQUENCE DESCRIPTION: SEQ ID NO:8:

| Met | Ala | Ser | Thr | Thr | Ser | Thr | Lys | Lys | Met | Met | Glu | Glu | Ala | Thr | Cys |
|---|---|---|---|---|---|---|---|---|---|---|---|---|---|---|---|
| 1 | | | | 5 | | | | | 10 | | | | | 15 | |
| Ser | Ile | Cys | Leu | Ser | Leu | Met | Thr | Asn | Pro | Val | Ser | Ile | Asn | Cys | Gly |
| | | | 20 | | | | | 25 | | | | | | 30 | |
| His | Ser | Tyr | Cys | His | Leu | Cys | Ile | Thr | Asp | Phe | Phe | Lys | Asn | Pro | Ser |
| | | | 35 | | | | | 40 | | | | | 45 | | |
| Gln | Lys | Gln | Leu | Arg | Gln | Glu | Thr | Phe | Cys | Cys | Pro | Gln | Cys | Arg | Ala |
| | | 50 | | | | | 55 | | | | | 60 | | | |
| Pro | Phe | His | Met | Asp | Ser | Leu | Arg | Pro | Asn | Lys | Gln | Leu | Gly | Ser | Leu |
| 65 | | | | | 70 | | | | | 75 | | | | | 80 |
| Ile | Glu | Ala | Leu | Lys | Glu | Thr | Asp | Gln | Glu | Met | Xaa | Xaa | Xaa | Xaa | Xaa |
| | | | | 85 | | | | | 90 | | | | | 95 | |
| Xaa | Xaa | Ser | Cys | Glu | Glu | His | Gly | Glu | Gln | Phe | His | Leu | Phe | Cys | Glu |
| | | | 100 | | | | | 105 | | | | | 110 | | |
| Asp | Glu | Gly | Gln | Leu | Ile | Cys | Trp | Arg | Cys | Glu | Arg | Ala | Pro | Gln | His |
| | | | 115 | | | | | 120 | | | | | 125 | | |
| Lys | Gly | His | Thr | Thr | Ala | Leu | Val | Glu | Asp | Val | Cys | Gln | Gly | Tyr | Lys |
| | | 130 | | | | | 135 | | | | | 140 | | | |
| Glu | Lys | Leu | Gln | Lys | Ala | Val | Thr | Lys | Leu | Lys | Gln | Leu | Glu | Asp | Arg |
| 145 | | | | | 150 | | | | | 155 | | | | | 160 |
| Cys | Thr | Glu | Gln | Lys | Leu | Ser | Thr | Ala | Met | Arg | Ile | Thr | Lys | Trp | Lys |
| | | | | 165 | | | | | 170 | | | | | 175 | |
| Glu | Lys | Val | Gln | Ile | Gln | Arg | Gln | Lys | Ile | Arg | Ser | Asp | Phe | Lys | Asn |
| | | | 180 | | | | | 185 | | | | | 190 | | |
| Leu | Gln | Cys | Phe | Leu | His | Glu | Glu | Lys | Ser | Tyr | Leu | Trp | Arg | Leu |
| | | 195 | | | | | 200 | | | | | 205 | | | |
| Glu | Lys | Glu | Glu | Gln | Thr | Leu | Ser | Arg | Leu | Arg | Asp | Tyr | Glu | Ala |
| | 210 | | | | | 215 | | | | | 220 | | | | |
| Gly | Leu | Gly | Leu | Lys | Ser | Asn | Glu | Leu | Lys | Ser | His | Ile | Leu | Glu | Leu |
| 225 | | | | | 230 | | | | | 235 | | | | | 240 |
| Glu | Glu | Lys | Cys | Gln | Gly | Ser | Ala | Gln | Lys | Leu | Leu | Gln | Asn | Val | Asn |
| | | | | 245 | | | | | 250 | | | | | 255 | |
| Asp | Thr | Leu | Ser | Arg | Ser | Trp | Ala | Val | Lys | Leu | Glu | Thr | Ser | Glu | Ala |
| | | | 260 | | | | | 265 | | | | | 270 | | |
| Val | Ser | Leu | Glu | Leu | His | Thr | Met | Cys | Asn | Val | Ser | Lys | Leu | Tyr | Phe |
| | | 275 | | | | | 280 | | | | | 285 | | | |
| Asp | Val | Lys | Lys | Met | Leu | Arg | Ser | His | Gln | Val | Ser | Val | Thr | Leu | Asp |
| | 290 | | | | | 295 | | | | | 300 | | | | |
| Pro | Asp | Thr | Ala | His | His | Glu | Leu | Ile | Leu | Ser | Glu | Asp | Arg | Arg | Gln |
| 305 | | | | | 310 | | | | | 315 | | | | | 320 |
| Val | Thr | Arg | Gly | Tyr | Thr | Gln | Glu | Asn | Gln | Asp | Thr | Ser | Ser | Arg | Arg |
| | | | | 325 | | | | | 330 | | | | | 335 | |
| Phe | Thr | Ala | Phe | Pro | Cys | Val | Leu | Gly | Cys | Glu | Gly | Phe | Thr | Ser | Gly |
| | | | 340 | | | | | 345 | | | | | 350 | | |
| Arg | Arg | Tyr | Phe | Glu | Val | Asp | Val | Gly | Glu | Gly | Thr | Gly | Trp | Asp | Leu |
| | | | 355 | | | | | 360 | | | | | 365 | | |
| Gly | Val | Cys | Met | Glu | Asn | Val | Gln | Arg | Gly | Thr | Gly | Met | Lys | Gln | Glu |
| | | 370 | | | | | 375 | | | | | 380 | | | |
| Pro | Gln | Ser | Gly | Phe | Trp | Thr | Leu | Arg | Leu | Cys | Lys | Lys | Lys | Gly | Tyr |
| 385 | | | | | 390 | | | | | 395 | | | | | 400 |
| Val | Ala | Leu | Thr | Ser | Pro | Pro | Thr | Ser | Leu | His | Leu | His | Glu | Gln | Pro |
| | | | | 405 | | | | | 410 | | | | | 415 | |

```
Leu  Leu  Val  Gly  Ile  Phe  Leu  Asp  Tyr  Glu  Ala  Gly  Val  Val  Ser  Phe
               420                 425                      430

Tyr  Asn  Gly  Xaa  Asn  Thr  Gly  Cys  His  Ile  Phe  Thr  Phe  Pro  Lys  Ala
          435                      440                 445

Ser  Phe  Ser  Asp  Thr  Leu  Arg  Pro  Tyr  Phe  Gln  Val  Tyr  Gln  Tyr  Ser
     450                      455                 460

Xaa  Xaa  Xaa  Xaa  Xaa  Xaa  Pro  Leu  Phe  Leu  Pro  Pro  Xaa  Xaa  Gly
465                      470                      475                      480

Xaa  Xaa  Xaa  Xaa  Asp
               485
```

( 2 ) INFORMATION FOR SEQ ID NO:9:

( i ) SEQUENCE CHARACTERISTICS:
      ( A ) LENGTH: 480 amino acids
      ( B ) TYPE: amino acid
      ( C ) STRANDEDNESS: Not Relevant
      ( D ) TOPOLOGY: Not Relevant ( i i ) MOLECULE TYPE: peptide ( i x ) FEATURE:
      ( A ) NAME/KEY: Region
      ( B ) LOCATION: 1..480
      ( D ) OTHER INFORMATION: /note= "NPT1"

( x i ) SEQUENCE DESCRIPTION: SEQ ID NO:9:

```
Met  Gln  Met  Asp  Asn  Arg  Leu  Pro  Pro  Lys  Lys  Val  Pro  Gly  Phe  Cys
1                   5                        10                      15

Ser  Phe  Arg  Tyr  Gly  Leu  Ser  Phe  Leu  Val  His  Cys  Cys  Asn  Val  Ile
               20                     25                      30

Ile  Thr  Ala  Gln  Arg  Ala  Cys  Leu  Asn  Leu  Thr  Met  Val  Val  Met  Val
          35                      40                 45

Asn  Ser  Thr  Asp  Pro  His  Gly  Leu  Pro  Asn  Thr  Ser  Thr  Lys  Lys  Leu
     50                      55                      60

Leu  Asp  Asn  Ile  Lys  Asn  Xaa  Xaa  Xaa  Xaa  Xaa  Xaa  Xaa  Xaa  Xaa
65                       70                      75                      80

Xaa  Xaa  Xaa  Pro  Met  Tyr  Asn  Trp  Ser  Pro  Asp  Ile  Gln  Gly  Ile  Ile
               85                      90                           95

Leu  Ser  Ser  Thr  Ser  Tyr  Gly  Val  Ile  Ile  Gln  Val  Pro  Val  Gly
          100                     105                     110

Tyr  Phe  Ser  Gly  Ile  Tyr  Ser  Thr  Lys  Lys  Met  Ile  Gly  Phe  Ala  Leu
          115                     120                     125

Cys  Leu  Ser  Ser  Val  Leu  Ser  Leu  Leu  Ile  Pro  Pro  Ala  Ala  Gly  Ile
     130                     135                     140

Gly  Val  Ala  Trp  Val  Val  Val  Cys  Arg  Ala  Val  Gln  Gly  Ala  Ala  Gln
145                      150                     155                     160

Gly  Ile  Val  Ala  Thr  Ala  Gln  Phe  Glu  Ile  Tyr  Val  Lys  Trp  Ala  Pro
               165                     170                     175

Pro  Leu  Glu  Arg  Gly  Arg  Leu  Thr  Ser  Met  Ser  Thr  Ser  Gly  Phe  Leu
               180                     185                     190

Leu  Gly  Pro  Phe  Ile  Val  Leu  Leu  Val  Thr  Gly  Val  Ile  Cys  Glu  Ser
          195                     200                     205

Leu  Gly  Trp  Pro  Met  Val  Phe  Tyr  Ile  Phe  Gly  Ala  Cys  Gly  Cys  Ala
     210                     215                     220

Val  Cys  Leu  Leu  Trp  Phe  Val  Leu  Phe  Tyr  Asp  Asp  Pro  Lys  Asp  His
225                     230                     235                     240

Pro  Cys  Ile  Ser  Ile  Ser  Glu  Lys  Glu  Tyr  Ile  Thr  Ser  Ser  Leu  Val
```

```
                         245                       250                       255
    Gln  Gln  Val  Ser  Ser  Ser  Arg  Gln  Ser  Leu  Pro  Ile  Lys  Ala  Ile  Leu
                        260                       265                       270

Lys  Ser  Leu  Pro  Val  Trp  Ala  Ile  Ser  Ile  Gly  Ser  Phe  Thr  Phe  Phe
                   275                       280                       285

Trp  Ser  His  Asn  Ile  Met  Thr  Leu  Tyr  Thr  Pro  Met  Phe  Ile  Asn  Ser
                   290                       295                       300

Met  Leu  His  Val  Asn  Ile  Lys  Glu  Asn  Gly  Phe  Leu  Ser  Ser  Leu  Pro
    305                      310                       315                       320

Tyr  Leu  Phe  Ala  Trp  Ile  Cys  Gly  Asn  Leu  Ala  Gly  Gln  Leu  Ser  Asp
                        325                       330                       335

Phe  Phe  Leu  Thr  Arg  Asn  Ile  Leu  Ser  Val  Ile  Ala  Val  Arg  Lys  Leu
                   340                       345                       350

Phe  Thr  Ala  Ala  Gly  Phe  Leu  Leu  Pro  Ala  Ile  Phe  Gly  Val  Cys  Leu
                   355                       360                       365

Pro  Tyr  Leu  Ser  Ser  Thr  Phe  Tyr  Ser  Ile  Val  Ile  Phe  Leu  Ile  Leu
         370                       375                       380

Ala  Gly  Ala  Thr  Gly  Ser  Phe  Cys  Leu  Gly  Gly  Val  Phe  Ile  Asn  Gly
    385                       390                       395                       400

Leu  Asp  Ile  Ala  Pro  Arg  Tyr  Phe  Gly  Phe  Ile  Lys  Ala  Cys  Ser  Thr
                        405                       410                       415

Leu  Thr  Gly  Met  Ile  Gly  Gly  Leu  Ile  Ala  Ser  Thr  Leu  Thr  Gly  Leu
                   420                       425                       430

Ile  Leu  Lys  Gln  Asp  Pro  Glu  Ser  Ala  Trp  Phe  Lys  Thr  Phe  Ile  Leu
                   435                       440                       445

Met  Ala  Ala  Ile  Asn  Val  Thr  Gly  Leu  Ile  Phe  Tyr  Leu  Ile  Val  Ala
         450                       455                       460

Thr  Ala  Glu  Ile  Gln  Asp  Trp  Ala  Lys  Glu  Lys  Gln  His  Thr  Arg  Leu
    465                       470                       475                       480
```

( 2 ) INFORMATION FOR SEQ ID NO:10:

( i ) SEQUENCE CHARACTERISTICS:
        ( A ) LENGTH: 470 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Region
        ( B ) LOCATION: 1..470
        ( D ) OTHER INFORMATION: /note= "NPT3"

( x i ) SEQUENCE DESCRIPTION: SEQ ID NO:10:

```
    Met  Asp  Gly  Lys  Pro  Ala  Thr  Arg  Lys  Gly  Pro  Asp  Phe  Cys  Ser  Leu
    1                   5                         10                        15

Arg  Tyr  Gly  Leu  Ala  Leu  Ile  Met  His  Phe  Ser  Asn  Phe  Thr  Met  Ile
                   20                        25                        30

Thr  Gln  Arg  Val  Ser  Leu  Ser  Ile  Ala  Ile  Ile  Ala  Met  Val  Asn  Thr
                   35                        40                        45

Thr  Gln  Gln  Gln  Gly  Leu  Ser  Asn  Ala  Ser  Thr  Glu  Gly  Pro  Val  Ala
              50                        55                        60

Asp  Ala  Phe  Asn  Asn  Ser  Ser  Ile  Ser  Ile  Lys  Glu  Phe  Asp  Thr  Lys
    65                        70                        75                        80

Ala  Ser  Val  Tyr  Gln  Trp  Ser  Pro  Glu  Thr  Gln  Gly  Ile  Ile  Phe  Ser
                        85                        90                        95
```

| | | | | | | | | | | | | | | |
|---|---|---|---|---|---|---|---|---|---|---|---|---|---|---|
|Ser|Ile|Asn|Tyr|Gly|Ile|Ile|Leu|Thr|Leu|Ile|Pro|Ser|Gly|Tyr|Leu|
| | | |100| | | |105| | | |110| | | |
|Ala|Gly|Ile|Phe|Gly|Ala|Lys|Lys|Met|Leu|Gly|Ala|Gly|Leu|Leu|Ile|
| | |115| | | |120| | | |125| | | | |
|Ser|Ser|Leu|Leu|Thr|Leu|Phe|Thr|Pro|Leu|Ala|Ala|Asp|Phe|Gly|Val|
| |130| | | |135| | | |140| | | | | |
|Ile|Leu|Val|Ile|Met|Val|Arg|Thr|Val|Gln|Gly|Met|Ala|Gln|Gly|Met|
|145| | | |150| | | |155| | | | | | |160|
|Ala|Trp|Thr|Gly|Gln|Phe|Thr|Ile|Trp|Ala|Lys|Trp|Ala|Pro|Pro|Leu|
| | | |165| | | |170| | | |175| | | |
|Glu|Arg|Ser|Lys|Leu|Thr|Thr|Ile|Ala|Gly|Ser|Gly|Ser|Ala|Phe|Gly|
| | |180| | | |185| | | |190| | | | |
|Ser|Phe|Ile|Ile|Leu|Cys|Val|Gly|Gly|Leu|Ile|Ser|Gln|Ala|Leu|Ser|
| |195| | | |200| | | |205| | | | | |
|Trp|Pro|Phe|Ile|Phe|Tyr|Ile|Phe|Gly|Ser|Thr|Gly|Cys|Val|Cys|Cys|
|210| | | |215| | | |220| | | | | | |
|Leu|Leu|Trp|Phe|Thr|Val|Ile|Tyr|Asp|Asp|Pro|Met|His|His|Pro|Cys|
|225| | | |230| | | |235| | | | | | |240|
|Ile|Ser|Val|Arg|Glu|Lys|Glu|His|Ile|Leu|Ser|Ser|Leu|Ala|Gln|Gln|
| | | |245| | | |250| | | |255| | | |
|Pro|Ser|Ser|Pro|Gly|Arg|Ala|Val|Pro|Ile|Lys|Ala|Met|Val|Thr|Cys|
| | |260| | | |265| | | |270| | | | |
|Leu|Pro|Leu|Trp|Ala|Ile|Phe|Leu|Gly|Phe|Phe|Ser|His|Phe|Trp|Leu|
| |275| | | |280| | | |285| | | | | |
|Cys|Thr|Ile|Ile|Leu|Thr|Tyr|Leu|Pro|Thr|Tyr|Ile|Ser|Thr|Leu|Leu|
|290| | | |295| | | |300| | | | | | |
|His|Val|Asn|Ile|Arg|Asp|Ser|Gly|Val|Leu|Ser|Ser|Leu|Pro|Phe|Ile|
|305| | | |310| | | |315| | | | | | |320|
|Ala|Ala|Ala|Ser|Cys|Thr|Ile|Leu|Gly|Gly|Gln|Leu|Ala|Asp|Phe|Leu|
| | |325| | | |330| | | |335| | | | |
|Leu|Ser|Arg|Asn|Leu|Leu|Arg|Leu|Ile|Thr|Val|Arg|Lys|Leu|Phe|Ser|
| |340| | | |345| | | |350| | | | | |
|Ser|Leu|Asp|Met|Gln|Val|Ser|Ser|Trp|Glu|Xaa|Xaa|Xaa|Xaa|Xaa|
| |355| | | |360| | | |365| | | | | |
|Xaa|Xaa|Xaa|Xaa|Xaa|Xaa|Xaa|Xaa|Xaa|Xaa|Xaa|Xaa|Xaa|Ser|Gln|Gly|
|370| | | |375| | | |380| | | | | | |
|Asp|Leu|Gly|Ser|Ser|Gln|Glu|Ser|Xaa|Ser|Leu|Pro|Leu|Pro|Leu|Asp|
|385| | | |390| | | |395| | | | | | |400|
|Ser|Ser|Ser|Xaa|Xaa|Xaa|Xaa|Xaa|Xaa|Xaa|Xaa|Val|Arg|Ile|Leu|
| | |405| | | |410| | | |415| | | | |
|Ser|Leu|Val|Gly|Gly|Met|Ser|Phe|Ser|Cys|Leu|Leu|Xaa|Xaa|Xaa|Xaa|
| | |420| | | |425| | | |430| | | | |
|Xaa|Gln|Ser|Thr|Cys|Leu|Ala|Trp|Ser|Phe|Thr|Ser|Arg|Leu|Asp|Lys|
| |435| | | |440| | | |445| | | | | |
|Gln|Asn|Phe|Lys|Thr|Gly|Pro|Lys|Arg|Gly|Pro|Leu|Pro|Ala|Ser|Glu|
|450| | | |455| | | |460| | | | | | |
|Asp|Ile|Lys|Leu|Gln|Thr|
|465| | | |470| |

( 2 ) INFORMATION FOR SEQ ID NO:11:

( i ) SEQUENCE CHARACTERISTICS:
    ( A ) LENGTH: 480 amino acids
    ( B ) TYPE: amino acid
    ( C ) STRANDEDNESS: Not Relevant
    ( D ) TOPOLOGY: Not Relevant ( i i ) MOLECULE TYPE: peptide ( i x ) FEATURE:
      ( A ) NAME/KEY: Region
      ( B ) LOCATION: 1..480
      ( D ) OTHER INFORMATION: /note= "NPT4"

( x i ) SEQUENCE DESCRIPTION: SEQ ID NO:11:

| Met | Gln | Val | Asp | Glu | Thr | Leu | Ile | Pro | Arg | Lys | Gly | Pro | Ser | Leu | Cys |
|---|---|---|---|---|---|---|---|---|---|---|---|---|---|---|---|
| 1 | | | | 5 | | | | | 10 | | | | | 15 | |
| Ser | Ala | Arg | Tyr | Gly | Ile | Ala | Leu | Val | Leu | His | Phe | Cys | Asn | Phe | Thr |
| | | | 20 | | | | | 25 | | | | | 30 | | |
| Thr | Ile | Ala | Gln | Asn | Val | Ile | Met | Asn | Ile | Thr | Met | Val | Ala | Met | Val |
| | | | 35 | | | | 40 | | | | | 45 | | | |
| Asn | Ser | Thr | Ser | Pro | Gln | Ser | Gln | Leu | Asn | Asp | Ser | Glu | Xaa | Xaa | |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | | 80 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 85 | | | | | 90 | | | | | 95 | |
| Xaa | Xaa | Xaa | Xaa | Xaa | Xaa | Xaa | Xaa | Xaa | Xaa | Xaa | Val | Leu | Pro | Val | Asp |
| | | | 100 | | | | | 105 | | | | | 110 | | |
| Ser | Phe | Gly | Gly | Leu | Ser | Lys | Ala | Pro | Lys | Ser | Leu | Pro | Xaa | Xaa | Xaa |
| | | | 115 | | | | 120 | | | | | 125 | | | |
| Xaa | Xaa | Xaa | Xaa | Xaa | Xaa | Xaa | Xaa | Xaa | Xaa | Xaa | Xaa | Xaa | Xaa | Xaa | Xaa |
| | 130 | | | | | 135 | | | | | 140 | | | | |
| Xaa | Xaa | Xaa | Xaa | Xaa | Xaa | Xaa | Xaa | Xaa | Xaa | Xaa | Xaa | Xaa | Xaa | Ala | Lys |
| 145 | | | | | 150 | | | | | 155 | | | | | 160 |
| Ser | Ser | Ile | Leu | Gly | Gly | Gln | Phe | Ala | Ile | Trp | Glu | Lys | Trp | Gly | Pro |
| | | | | 165 | | | | | 170 | | | | | 175 | |
| Pro | Gln | Glu | Arg | Ser | Arg | Leu | Cys | Ser | Ile | Ala | Leu | Ser | Gly | Met | Leu |
| | | | 180 | | | | | 185 | | | | | 190 | | |
| Leu | Gly | Cys | Phe | Thr | Ala | Ile | Leu | Ile | Gly | Gly | Phe | Ile | Ser | Glu | Thr |
| | | | 195 | | | | 200 | | | | | 205 | | | |
| Leu | Gly | Trp | Pro | Phe | Val | Phe | Tyr | Ile | Phe | Gly | Gly | Val | Gly | Cys | Val |
| | | 210 | | | | | 215 | | | | | 220 | | | |
| Cys | Cys | Leu | Leu | Trp | Phe | Val | Val | Ile | Tyr | Asp | Asp | Pro | Phe | Ser | Tyr |
| 225 | | | | | 230 | | | | | 235 | | | | | 240 |
| Pro | Trp | Ile | Ser | Thr | Ser | Glu | Lys | Glu | Tyr | Ile | Ile | Ser | Ser | Leu | Lys |
| | | | | 245 | | | | | 250 | | | | | 255 | |
| Gln | Gln | Val | Gly | Ser | Ser | Lys | Gln | Pro | Leu | Pro | Ile | Lys | Ala | Met | Leu |
| | | | 260 | | | | | 265 | | | | | 270 | | |
| Arg | Ser | Leu | Pro | Ile | Trp | Ser | Ile | Cys | Leu | Gly | Cys | Phe | Ser | His | Gln |
| | | | 275 | | | | 280 | | | | | 285 | | | |
| Trp | Leu | Val | Ser | Thr | Met | Val | Val | Tyr | Ile | Pro | Thr | Tyr | Ile | Ser | Ser |
| | | 290 | | | | | 295 | | | | | 300 | | | |
| Val | Tyr | His | Val | Asn | Ile | Arg | Asp | Asn | Gly | Leu | Leu | Ser | Ala | Leu | Pro |
| 305 | | | | | 310 | | | | | 315 | | | | | 320 |
| Phe | Ile | Val | Ala | Trp | Val | Ile | Gly | Met | Val | Gly | Gly | Tyr | Leu | Ala | Asp |
| | | | | 325 | | | | | 330 | | | | | 335 | |
| Phe | Leu | Leu | Thr | Lys | Xaa | Lys | Phe | Arg | Leu | Ile | Thr | Val | Arg | Lys | Ile |
| | | | 340 | | | | | 345 | | | | | 350 | | |
| Ala | Thr | Ile | Leu | Gly | Ser | Leu | Pro | Ser | Ser | Ala | Leu | Ile | Val | Ser | Leu |
| | | | 355 | | | | | 360 | | | | | 365 | | |
| Pro | Tyr | Leu | Asn | Ser | Gly | Tyr | Ile | Thr | Ala | Thr | Ala | Leu | Leu | Thr | Leu |

|  | 370 |  |  |  | 375 |  |  |  | 380 |  |  |  |
|---|---|---|---|---|---|---|---|---|---|---|---|---|
| Ser 385 | Cys | Gly | Leu | Ser | Thr 390 | Leu | Cys | Gln | Ser | Gly 395 | Ile | Tyr | Ile | Asn | Val 400 |
| Leu | Asp | Ile | Ala | Pro 405 | Arg | Tyr | Ser | Ser | Phe 410 | Leu | Met | Gly | Ala | Ser 415 | Arg |
| Gly | Phe | Ser | Ser 420 | Ile | Ala | Pro | Val | Ile 425 | Val | Pro | Thr | Val | Ser 430 | Gly | Phe |
| Leu | Leu | Ser 435 | Gln | Asp | Pro | Glu | Phe 440 | Gly | Trp | Arg | Asn | Val 445 | Phe | Phe | Leu |
| Leu | Phe 450 | Ala | Val | Asn | Leu | Leu 455 | Gly | Leu | Leu | Phe | Tyr 460 | Leu | Ile | Phe | Gly |
| Glu 465 | Ala | Asp | Val | Gln | Glu 470 | Trp | Ala | Lys | Glu | Arg 475 | Lys | Leu | Thr | Arg | Leu 480 |

( 2 ) INFORMATION FOR SEQ ID NO:12:

( i ) SEQUENCE CHARACTERISTICS:
  ( A ) LENGTH: 2882 base pairs
  ( B ) TYPE: nucleic acid
  ( C ) STRANDEDNESS: Not Relevant
  ( D ) TOPOLOGY: Not Relevant ( i i ) MOLECULE TYPE: cDNA ( i x ) FEATURE:
  ( A ) NAME/KEY: misc_feature
  ( B ) LOCATION: 1..2882
  ( D ) OTHER INFORMATION: /note= "cDNA 21"

( x i ) SEQUENCE DESCRIPTION: SEQ ID NO:12:

```
CGACCCACGC GTCCGAACAT GGCGACCTAG GAGAAAGGGA AGAACAATTT TTTCTCCTCT      60
TTTGGGAAGG TTTGCGTCTA GTAGTGCCTG TGCCCCTGGG CAGATTGGAG AGAAGAGGGA     120
CGACTGGAGA ATCGTCGAGA ACCAGCGGAG AAAAGAAAAA GCAACGTTTA ATTCTAGAAG     180
GCCTCCTGTC CCTGCCTGCT CTGGGTGCTC ATGGAATCAG CTGCTGCCCT GCACTTCTCC     240
CGGCCAGCCT CCCTCCTCCT CCTCCTCCTC AGCCTGTGTG CACTGGTCTC AGCCCAGTTT     300
ATTGTCGTGG GGCCCACTGA TCCCATCTTG GCCACGGTTG GAGAAAACAC TACGTTACGC     360
TGCCATCTGT CACCCGAGAA AAATGCTGAG GACATGGAGG TGCGGTGGTT CCGGTCTCAG     420
TTCTCCCCCG CAGTGTTTGT GTATAAAGGT GGCAGAGAGA GAACAGAGGA GCAGATGGAG     480
GAGTACCGAG GAAGAACCAC CTTTGTGAGC AAAGACATCA GCAGGGGCAG CGTGGCCCTG     540
GTCATACACA ACATCACAGC CCAGGAAAAC GGCACCTACC GCTGTTACTT CCAAGAAGGC     600
AGGTCCTACG ATGAGGCCAT CCTGCACCTC GTAGTGGCAG GACTAGGCTC TAAGCCCCTC     660
ATTTCAATGA GGGGCCATGA AGACGGGGGC ATCCGGCTGG AGTGCATATC TAGAGGGTGG     720
TACCCAAAGC CCCTCACAGT GTGGAGGGAC CCCTACGGTG GGGTTGCGCC TGCCCTGAAA     780
GAGGTCTCCA TGCCTGATGC AGACGGCCTC TTCATGGTCA CCACGGCTGT GATCATCAGA     840
GACAAGTCTG TGAGGAACAT GTCCTGCTCT ATCAACAACA CCCTGCTCGG CCAGAAGAAA     900
GAAAGTGTCA TTTTTATTCC AGAATCCTTT ATGCCCAGTG TGTCTCCCTG TGCAGTGGCC     960
CTGCCTATCA TTGTGGTTAT TCTGATGATA CCCATTGCCG TATGCATCTA TTGGATCAAC    1020
AAACTCCAAA AGGAAAAAAA GATTCTGTCA GGGGAAAAGG AGTTTGAACG GGAAACAAGA    1080
GAAATTGCTC TAAAGGAACT GGAGAAAGAA CGTGTGCAAA AAGAGGAAGA ACTTCAAGTA    1140
AAAGAGAAAC TTCAAGAAGA ATTGCGATGG AGAAGAACAT TCTTACATGC TGTTGATGTG    1200
GTCCTGGATC CAGACACCGC TCATCCCGAT CTCTTCCTGT CAGAGGACCG GAGAAGTGTG    1260
```

| | | | | | |
|---|---|---|---|---|---|
| AGAAGGTGCC | CCTTCAGGCA | CCTAGGGGAG | AGCGTGCCTG | ACAACCCAGA | GAGATTCGAC | 1320 |
| AGTCAGCCTT | GTGTCCTAGG | CCGGGAGAGC | TTCGCTTCAG | GGAAACATTA | CTGGGAGGTG | 1380 |
| GAGGTGGAAA | ACGTGATTGA | GTGGACTGTG | GGGGTCTGTA | GAGACAGTGT | TGAGAGGAAA | 1440 |
| GGGGAGGTCC | TGCTGATTCC | TCAGAATGGC | TTCTGGACCT | TGGAGATGCA | TAAAGGGCAA | 1500 |
| TACCGGGCCG | TGTCCTCCCC | TGATAGGATT | CTCCCTTTGA | AGGAGTCCCT | TTGCCGGGTG | 1560 |
| GGCGTCTTCC | TGGACTATGA | AGCTGGAGAT | GTCTCCTTCT | ACAACATGAG | GGACAGATCG | 1620 |
| CACATCTACA | CATGTCCCCG | TTCAGCCTTT | TCCGTGCCTG | TGAGGCCCTT | CTTCAGGTTG | 1680 |
| GGGTGTGAGG | ACAGCCCCAT | CTTCATCTGC | CCTGCACTCA | CAGGAGCCAA | TGGGGTCACG | 1740 |
| GTGCCTGAAG | AGGGCCTGAC | ACTTCACAGA | GTGGGACCC | ACCAGAGCCT | ATAGAATCAA | 1800 |
| TTCCTTGGTC | TCACAGCCAT | GTAGACAAGC | CCTGGTCATC | TCAGCAGCCA | CCGCACAACA | 1860 |
| CCCCTGGTGG | AAGACACGCC | CTCCTCCCCT | CTGGTCACAC | AAGAGAACAT | CTTCCAGCTG | 1920 |
| CCTCTTTCAC | ACCCACTACA | GACCTCAGCC | CCAGTTTTCT | CCTCCTCACT | AGGCTGTGTT | 1980 |
| TTTAGTAGTT | CCTTTGCTTG | TAACTATGGG | ATGGGATCCA | GGCATAGGGA | ACTAGTTGTT | 2040 |
| ACACAGCTCC | CAGCCAAGAA | GAAAGTGTGA | GAAGTTGATG | GGCAGCAAAC | CTGCTGTTTA | 2100 |
| ACATCAGGGT | GACCACATTA | AGCCCAGTAT | TCCAGTTGGC | ACCAGAAGAT | ATGGACTTGG | 2160 |
| AATGAGGCCT | ACAGGGTTCA | CCAGGATGTA | AGAGGAGAGA | GGAATCCACA | GGACCACCAG | 2220 |
| AGAGGAGAGG | GAACCAGATA | TGCAGATCAG | AGATAGAGGA | AGTGGAACCA | GAGAGCTGGG | 2280 |
| AGGGACCAAG | GTTGTAAGGG | TGGCTAAGTC | CCACCATAAC | AGCTAAGGGG | ACCTGGGAGA | 2340 |
| TGATGGCTCA | TTTCCACCCA | GCCCCAGGAT | TTCCAGAGCG | CACATCCACA | GGCCTGGACC | 2400 |
| TGGGATGAAG | ATGAATGAAG | AACATGGATG | CACGTGGATG | TAGTTTGGCT | CAGGTGTCCC | 2460 |
| TGCAGTTGGC | AAGGAGTCAG | TACTCAGTCC | CTGAGTGTGG | CTGAAATTTG | AGGTCCTGGC | 2520 |
| TGAGCCAAGG | AGTAATGGAC | CAGATCTACC | TCAGTATTCA | AGTTCAGTGG | GGACACCAGT | 2580 |
| GGCTTCAAAC | TTCCTGGTTT | CATGATATCT | TGAGACGCCT | TACAAATGAT | GGAGGATTCC | 2640 |
| AAAGAGTTTT | TGTTTATTTG | GGTTAATATT | TGTTGGTATT | TATGGCATTT | GAGATTGAAA | 2700 |
| CTAAGAAATG | TTTTAATTTA | TTACCTTTAC | AACATTTATT | TACATTACAT | ACATACATTT | 2760 |
| ACAACATTTA | TTAATTTATA | TTAAAATAGC | ATGAATAAGC | CAATTATAGG | TTAATATAAG | 2820 |
| TAGAATGTTT | GTGAAAAATA | AGTATGGTAT | CCAAAGCAAA | ATAAATTTTA | TTGTGAAGTG | 2880 |
| TG | | | | | | 2882 |

( 2 ) INFORMATION FOR SEQ ID NO:13:

( i ) SEQUENCE CHARACTERISTICS:
        ( A ) LENGTH: 2926 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..2926
        ( D ) OTHER INFORMATION: /note= "cDNA 29"

( x i ) SEQUENCE DESCRIPTION: SEQ ID NO:13:

| | | | | | |
|---|---|---|---|---|---|
| ACGCGTCCGC | TTCGGAATGA | GAGACTCAAC | CATAATAGAA | AGAATGGAGA | ACTATTAACC | 60 |
| ACCATTCTTC | AGTGGGCTGT | GATTTTCAGA | GGGGAATACT | AAGAAATGGT | TTTCCATACT | 120 |
| GGAACCCAAA | GGTAAAGACA | CTCAAGGACA | GACATTTTTG | GCAGAGCATA | GATGAAAATG | 180 |

-continued

| | | | | | | |
|---|---|---|---|---|---|---|
| GCAAGTTCCC | TGGCTTTCCT | TCTGCTCAAC | TTTCATGTCT | CCCTCTTCTT | GGTCCAGCTG | 240 |
| CTCACTCCTT | GCTCAGCTCA | GTTTTCTGTG | CTTGGACCCT | CTGGGCCCAT | CCTGGCCATG | 300 |
| GTGGGTGAAG | ACGCTGATCT | GCCCTGTCAC | CTGTTCCCGA | CCATGAGTGC | AGAGACCATG | 360 |
| GAGCTGAGGT | GGGTGAGTTC | CAGCCTAAGG | CAGGTGGTGA | ACGTGTATGC | AGATGGAAAG | 420 |
| GAAGTGGAAG | ACAGGCAGAG | TGCACCATAT | CGAGGGAGAA | CTTCGATTCT | GCGGGATGGC | 480 |
| ATCACTGCAG | GGAAGGCTGC | TCTCCGAATA | CACAACGTCA | CAGCCTCTGA | CAGTGGAAAG | 540 |
| TACTTGTGTT | ATTTCCAAGA | TGGTGACTTC | TACGAAAAAG | CCCTGGTGGA | GCTGAAGGTT | 600 |
| GCAGCATTGG | GTTCTGATCT | TCACATTGAA | GTGAAGGGTT | ATGAGGATGG | AGGGATCCAT | 660 |
| CTGGAGTGCA | GGTCCACTGG | CTGGTACCCC | CAACCCCAAA | TAAAGTGGAG | CGACACCAAG | 720 |
| GGAGAGAACA | TCCCGGCTGT | GGAAGCACCT | GTGGTTGCAG | ATGGAGTGGG | CCTGTATGCA | 780 |
| GTAGCAGCAT | CTGTGATCAT | GAGAGGCAGC | TCTGGTGGGG | GTGTATCCTG | CATCATCAGA | 840 |
| AATTCCCTCC | TCGGCCTGGA | AAAGACAGCC | AGCATATCCA | TCGCAGACCC | CTTCTTCAGG | 900 |
| AGCGCCCAGC | CCTGGATCGC | GGCCCTGGCA | GGGACCCTGC | CTATCTCGTT | GCTGCTTCTC | 960 |
| GCAGGAGCCA | GTTACTTCTT | GTGGAGACAA | CAGAAGGAAA | AAATTGCTCT | GTCCAGGGAG | 1020 |
| ACAGAAAGAG | AGCGAGAGAT | GAAAGAAATG | GGATACGCTG | CAACAGAGCA | AGAAATAAGC | 1080 |
| CTAAGAGAGA | AGCTCCAGGA | GGAACTCAAG | TGGAGGAAAA | TCCAGTACAT | GGCTCGTGGA | 1140 |
| GAGAAGTCTT | TGGCCTATCA | TGAATGGAAA | ATGGCCCTCT | TCAAACCTGC | GGATGTGATT | 1200 |
| CTGGATCCAG | ACACGGCAAA | CGCCATCCTC | CTTGTTTCTG | AGGACCAGAG | GAGTGTGCAG | 1260 |
| CGTGCTGAAG | AGCCGCGGGA | TCTGCCAGAC | AACCCTGAGA | GATTTGAATG | GCGTTACTGT | 1320 |
| GTCCTTGGCT | GTGAAAACTT | CACATCAGGG | AGACATTACT | GGGAGGTGGA | AGTGGGGGAC | 1380 |
| AGAAAAGAGT | GGCATATTGG | GGTATGTAGT | AAGAACGTGG | AGAGGAAAAA | AGGTTGGGTC | 1440 |
| AAAATGACAC | CGGAGAACGG | ATACTGGACT | ATGGGCCTGA | CTGATGGGAA | TAAGTATCGG | 1500 |
| GCTCTCACTG | AGCCCAGAAC | CAACCTGAAA | CTTCCTGAGC | CTCCTAGGAA | AGTGGGGATC | 1560 |
| TTCCTGGACT | ATGAGACTGG | AGAGATCTCG | TTCTATAATG | CCACAGATGG | ATCTCATATC | 1620 |
| TACACCTTTC | CGCACGCCTC | TTTCTCTGAG | CCTCTATATC | CTGTTTTCAG | AATTTTGACC | 1680 |
| TTGGAGCCCA | CTGCCCTGAC | CATTTGCCCA | ATACCAAAAG | AAGTAGAGAG | TTCCCCCGAT | 1740 |
| CCTGACCTAG | TGCCTGATCA | TTCCCTGGAG | ACACCACTGA | CCCCGGGCTT | AGCTAATGAA | 1800 |
| AGTGGGGAGC | CTCAGGCTGA | AGTAACATCT | CTGCTTCTCC | CTGCCCACCC | TGGAGCTGAG | 1860 |
| GTCTCCCCTT | CTGCAACAAC | CAATCAGAAC | CATAAGCTAC | AGGCACGCAC | TGAAGCACTT | 1920 |
| TACTGATATT | CATTCCATTA | TTCCATATGA | CAGTTGTTTT | GAGTTTCGTA | CCACCTTATT | 1980 |
| GTCCCCTTAT | ACAGATAAGG | AAACTGGGGT | GCAGAAAGGT | GAATTAACTT | TACAAAGTAG | 2040 |
| ACATGACAAG | TGAACAGCAG | AGCTGGGATC | TAAACAGCAA | TAACTAACAT | TAACAGAGAA | 2100 |
| TTTAAAATGT | TCTTAGTGCT | GTGTTATAAG | CTTTGGTGGA | TGTCACTCCT | TTAATCCTCA | 2160 |
| CAACACCCTG | TCGGGTAGTC | ATATTTTGCA | AGTATGGAAG | CTGAGGCAGG | GCAACATGAA | 2220 |
| GTAACTTACA | TAATTCATAC | AGTAATTTGT | GCAGTTGGGA | GATGTTCAGC | CTTAGTCCCT | 2280 |
| GGCTAATTGC | CTGTTCTTTT | CCAGCCTGAT | TTTTTTTCCC | ACAGGAAGAG | CCCACATGTA | 2340 |
| GCCCTGAGGT | TTCCTTCCCA | GGACAGCTGC | AGGGTAGAGA | TCATTTAAG | TGCTTGTGGA | 2400 |
| GTTGACATCC | CTATTGACTC | TTTCCCAGCT | GATATCAGAG | ACTTAGACCC | AGCACTCCTT | 2460 |
| GGATTAGCTC | TGCAGAGTGT | CTTGGTTGAG | AGAATAACCT | CATAGTACCA | ACATGACATG | 2520 |
| TGACTTGGAA | AGAGACTAGA | GGCCACACTT | GATAAATCAT | GGGGCACAGA | TATGTTCCCA | 2580 |

| | | | | | |
|---|---|---|---|---|---|
| CCCAACAAAT | GTGATAAGTG | ATTGTGCAGC | CAGAGCCAGC | CTTCCTTCAA | TCAAGGTTTC | 2640 |
| CAGGCAGAGC | AAATACCCTA | GAGATTCTCT | GTGATATAGG | AAATTTGGAT | CAAGGAAGCT | 2700 |
| AAAAGAATTA | CAGGGATGTT | TTTAATCCCA | CTATGGACTC | AGTCTCCTGG | AAATAGGTCT | 2760 |
| GTCCACTCCT | GGTCATTGGT | GGATGTTAAA | CCCATATTCC | TTTCAACTGC | TGCCTGCTAG | 2820 |
| GGAAAACTGC | TCCTCATTAT | CATCACTATT | ATTGCTCACC | ACTGTATCCC | CTCTACTTGG | 2880 |
| CAAGTGGTTG | TCAAGTTCTA | GTTGTTCAAT | AAATGTGTTA | ATAATG | | 2926 |

( 2 ) INFORMATION FOR SEQ ID NO:14:

( i ) SEQUENCE CHARACTERISTICS:
        ( A ) LENGTH: 1645 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..1645
        ( D ) OTHER INFORMATION: /note= "cDNA 23"

( x i ) SEQUENCE DESCRIPTION: SEQ ID NO:14:

| | | | | | |
|---|---|---|---|---|---|
| ATTTGCTTTC | TCTTTTTCCT | TTCTTCCGGA | TGAGAGGCTA | AGCCATAATA | GAAAGAATGG | 60 |
| AGAATTATTG | ATTGACCGTC | TTTATTCTGT | GGGCTCTGAT | TCTCCAATGG | AATACCAAG | 120 |
| GGATGGTTTT | CCATACTGGA | ACCCAAAGGT | AAAGACACTC | AAGGACAGAC | ATTTTGGCA | 180 |
| GAGCATAGAT | GAAAATGGCA | AGTTCCCTGG | CTTTCCTTCT | GCTCAACTTT | CATGTCTCCC | 240 |
| TCCTCTTGGT | CCAGCTGCTC | ACTCCTTGCT | CAGCTCAGTT | TTCTGTGCTT | GGACCCTCTG | 300 |
| GGCCCATCCT | GGCCATGGTG | GGTGAAGACG | CTGATCTGCC | CTGTCACCTG | TTCCCGACCA | 360 |
| TGAGTGCAGA | GACCATGGAG | CTGAAGTGGG | TAAGTTCCAG | CCTAAGGCAG | GTGGTGAACG | 420 |
| TGTATGCAGA | TGGAAAGGAA | GTGGAAGACA | GGCAGAGTGC | ACCGTATCGA | GGGAGAACTT | 480 |
| CGATTCTGCG | GGATGGCATC | ACTGCAGGGA | AGGCTGCTCT | CCGAATACAC | AACGTCACAG | 540 |
| CCTCTGACAG | TGGAAAGTAC | TTGTGTTATT | CCAAGATGG | TGACTTCTAT | GAAAAAGCCC | 600 |
| TGGTGGAGCT | GAAGGTTGCA | GCACTGGGTT | CTAATCTTCA | CGTCGAAGTG | AAGGGTTATG | 660 |
| AGGATGGAGG | GATCCATCTG | GAGTGCAGGT | CCACCGGCTG | GTACCCCAA | CCCCAAATAC | 720 |
| AGTGGAGCAA | CGCCAAGGGA | GAGAACATCC | CAGCTGTGGA | AGCACCTGTG | GTTGCAGATG | 780 |
| GAGTGGGCCT | ATATGAAGTA | GCAGCATCTG | TGATCATGAG | AGGCGGCTCC | GGGGAGGGTG | 840 |
| TATCCTGCAT | CATCAGAAAT | TCCCTCCTCG | GCCTGGAAAA | GACAGCCAGC | ATTTCCATCG | 900 |
| CAGACCCCTT | CTTCAGGAGC | GCCCAGCCCT | GGATCGCAGC | CCTGGCAGGG | ACCCTGCCTA | 960 |
| TCTTGCTGCT | GCTTCTCGCC | GGAGCCAGTT | ACTTCTTGTG | GAGACAACAG | AAGGAAATAA | 1020 |
| CTGCTCTGTC | CAGTGAGATA | GAAAGTGAGC | AAGAGATGAA | AGAAATGGGA | TATGCTGCAA | 1080 |
| CAGAGCGGGA | AATAAGCCTA | AGAGAGAGCC | TCCAGGAGGA | ACTCAAGAGG | AAAAAATCCA | 1140 |
| GTACTTGACT | CGTGGAGAGG | AGTCTTCGTC | CGATACCAAT | AAGTCAGCCT | GATGCTCTAA | 1200 |
| TGGAAAAATG | GCCCTCTTCA | AGCCTGGTGA | GGAAATGCTT | CAGATGAGGC | TCCACCTTGT | 1260 |
| TAAATAAATT | GGATGTATGG | AAAAATAGAC | TGCAGAAAAG | GGGAACTCAT | TTAGCTCACG | 1320 |
| AGTGGTCGAG | TGAAGATTGA | AAATTAACCT | CTGAGGGCCA | GCACAGCAGC | TCATGCCTGT | 1380 |
| AATCCTAGCA | CTTTGGAAGG | CTGAGGAGGG | CGGATCACAA | GGTCAGGAGA | TCAAGACCAT | 1440 |
| CCTGGCTAAC | ACGGTGAAAC | CCCGTCTCTA | CTAAAAATAC | AAAAAATAAA | AAATTAGCCG | 1500 |

| | | | | | | |
|---|---|---|---|---|---|---|
| GGCATGGTGA | CGGGCACCTG | TAGTCCCAGC | TACTCGGGAG | GCTGAGGCAG | GAGAATGGCA | 1560 |
| TGAACCCGGA | AGGCAGAGCT | TGCAGTGAGC | CGAGATCACG | CCACTGCACT | CCAGCCTGGG | 1620 |
| AGACAGAGCG | AGACTCTGTC | TCAAG | | | | 1645 |

( 2 ) INFORMATION FOR SEQ ID NO:15:

( i ) SEQUENCE CHARACTERISTICS:
        ( A ) LENGTH: 3416 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..3416
        ( D ) OTHER INFORMATION: /note= "cDNA 44"

( x i ) SEQUENCE DESCRIPTION: SEQ ID NO:15:

| | | | | | | |
|---|---|---|---|---|---|---|
| CTGAAGCTTG | CATGCCTGCA | GGTCGACCCA | CGCGTCCGCG | GACGCGTGGG | CGGACGCGTG | 60 |
| GGTTTTTCCT | TTCTTCCAGA | AGGAGATTTA | ACCATAGTAG | AAAGAATGGA | GAACTATTAA | 120 |
| CTGCCTTCCT | TCTGTGGGCT | GTGATTTTCA | GAGGGGAATG | CTAAGAGGTG | ATTTTCAATG | 180 |
| TTGGGACTCA | AAGGTGAAGA | CACTGAAGGA | CAGAATTTTT | GGCAGAGGAA | AGATCTTCTT | 240 |
| CGGTCACCAT | ACTTGAGTTA | GCTCTAGGGA | AGTGGAGGTT | TCCATTTGGA | ATTCTATAGC | 300 |
| TTCTTCCAGG | TCATAGTGTC | TGCCCCCCAC | CTTCCAGTAT | CTCCTGATAT | GCAGCATGAA | 360 |
| TGAAAATGGC | AAGTTTCCTG | GCCTTCCTTC | TGCTCAACTT | TCGTGTCTGC | CTCCTTTTGC | 420 |
| TTCAGCTGCT | CATGCCTCAC | TCAGCTCAGT | TTTCTGTGCT | TGGACCCTCT | GGGCCCATCC | 480 |
| TGGCCATGGT | GGGTGAAGAC | GCTGATCTGC | CCTGTCACCT | GTTCCCGACC | ATGAGTGCAG | 540 |
| AGACCATGGA | GCTGAAGTGG | GTGAGTTCCA | GCCTAAGGCA | GGTGGTGAAC | GTGTATGCAG | 600 |
| ATGGAAAGGA | AGTGGAAGAC | AGGCAGAGTG | CACCGTATCG | AGGGAGAACT | TCGATTCTGC | 660 |
| GGGATGGCAT | CACTGCAGGG | AAGGCTGCTC | TCCAATACA | CAACGTCACA | GCCTCTGACA | 720 |
| GTGGAAAGTA | CTTGTGTTAT | TTCCAAGATG | GTGACTTCTA | TGAAAAAGCC | CTGGTGGAGC | 780 |
| TGAAGGTTGC | AGCACTGGGT | TCTGATCTTC | ACGTTGATGT | GAAGGGTTAC | AAGGATGGAG | 840 |
| GGATCCATCT | GGAGTGCAGG | TCCACTGGCT | GGTACCCCCA | ACCCCAAATA | CAGTGGAGCA | 900 |
| ACAACAAGGG | AGAGAACATC | CCGACTGTGG | AAGCACCTGT | GGTTGCAGAC | GGAGTGGGCC | 960 |
| TGTATGCAGT | AGCAGCATCT | GTGATCATGA | GAGGCAGCTC | TGGGGAGGGT | GTATCCTGTA | 1020 |
| CCATCAGAAG | TTCCCTCCTC | GGCCTGGAAA | AGACAGCCAG | CATTTCCATC | GCAGACCCCT | 1080 |
| TCTTCAGGAG | CGCCCAGAGG | TGGATCGCCG | CCCTGGCACG | GACCCTGCCT | GTCTTGCTGC | 1140 |
| TGCTTCTTGG | GGGAGCCGGT | TACTTCCTGT | GGCAACAGCA | GGAGGAAAAA | AAGACTCAGT | 1200 |
| TCAGAAAGAA | AAAGAGAGAG | CAAGAGTTGA | GAGAAATGGC | ATGGAGCACA | ATGAAGCAAG | 1260 |
| AACAAAGCAC | AAGAGTGAAG | CTCCTGGAGG | AACTCAGATG | GAGAAGTATC | CAGTATGCAT | 1320 |
| CTCGGGGAGA | GAGACATTCA | GCCTATAATG | AATGGAAAAA | GGCCCTCTTC | AAGCCTGCGG | 1380 |
| ATGTGATTCT | GGATCCAAAA | ACAGCAAACC | CCATCCTCCT | TGTTTCTGAG | GACCAGAGGA | 1440 |
| GTGTGCAGCG | TGCCAAGGAG | CCCCAGGATC | TGCCAGACAA | CCCTGAGAGA | TTTAATTGGC | 1500 |
| ATTATTGTGT | TCTCGGCTGT | GAGAGCTTCA | TATCAGGGAG | ACATTACTGG | GAGGTGGAGG | 1560 |
| TAGGGGACAG | GAAAGAGTGG | CATATAGGGG | TGTGCAGTAA | GAATGTGCAG | AGAAAAGGCT | 1620 |
| GGGTCAAAAT | GACACCTGAG | AATGGATTCT | GGACTATGGG | GCTGACTGAT | GGGAATAAGT | 1680 |

| | | | | | | |
|---|---|---|---|---|---|---|
| ATCGGACTCT | AACTGAGCCC | AGAACCAACC | TGAAACTTCC | TAAGCCCCCT | AAGAAAGTGG | 1740 |
| GGGTCTTCCT | GGACTATGAG | ACTGGAGATA | TCTCATTCTA | CAATGCTGTG | GATGGATCGC | 1800 |
| ATATTCATAC | TTTCCTGGAC | GTCTCCTTCT | CTGAGGCTCT | ATATCCTGTT | TTCAGAATTT | 1860 |
| TGACCTTGGA | GCCCACGGCC | CTGAGTATTT | GTCCAGCGTG | AAAAGAAGAA | GAGAGTTCCT | 1920 |
| CCAATTCTGA | CCGAGTGCTG | ATCATTCCT | AGAGACACCA | GTAACCCCGG | GCTTAGCTAA | 1980 |
| CGAAAGTGGG | GAGCCTCAGG | CTGAAGTAAC | TTTTCTCTGC | TTCTCCCTGC | CCAGCTCAGA | 2040 |
| GCTGAGGGCC | TCCCCCTCCA | CAGCAACCAA | TCACAACCAT | AAAGCTACAA | GCACGCACTG | 2100 |
| AAGCACTTTA | CTGATACTCA | TTCAATTATT | CATATGACAG | TTGTTTGAGT | TTGGTACCAT | 2160 |
| CTTATTTTCC | CCTTATACAG | ATAAGGAAAC | TGGGGTGCAG | AAAAGTGAAT | TGACTACAAA | 2220 |
| GTAGACATGA | CTAGTTAACA | ACACAGCTGG | GATCTAAACA | GCAATAACTA | ACATTAATGG | 2280 |
| AGAACTTAAA | ATGCTCTGAG | TGCTGTGTTA | TGAGCTTTGG | TGGATGTCAC | TCCTTTAATC | 2340 |
| CTCGCAACAC | CCTGTCGGGT | AGTCTCATTT | AGCAAGTATG | GAAGTTGAGG | CAGGGCAACA | 2400 |
| TTAAGCAACT | TACATAACTC | ATGCAGTAAT | TTCTGCAGTT | GGGAGATGTT | CAGCTTCAGT | 2460 |
| CCCCGGCCCT | ATGGCCGTTC | TTTTCCACCC | TGTTTCTTCC | CCCATAGGAA | GAACCCACCT | 2520 |
| GTAGCCCTGA | GGTTCTTTTC | CCAGGATGGC | TCCAGGATAA | GGATCACTGT | AGGTGGTTGT | 2580 |
| GGAGTTGACA | CCCCTGTTGA | CTCCTTCCCA | GCTGATTGTC | AGAGCCTTAG | ACCCAGCACG | 2640 |
| CCTTGGATTA | GCTTTGCAGA | GTGTCTTGGT | TGAGAGAATA | ACCTCACCGT | ACCCACATGA | 2700 |
| CACGTGATTT | GGAAAGAGAC | TAGAGGCCAC | ACTTGATAAA | TCATGGGGAA | CAGATGTGTT | 2760 |
| CCACCCAACA | AATGTGATAA | GTGATCATGC | AGCCAGAGCC | AGCCTTCCTT | CAATCAAGGT | 2820 |
| TTCCAGGCAG | AGCAAATACC | CTAGAGATTT | TCTGTGATAT | AGGAAATTTG | GATGAAGGGA | 2880 |
| GCTAGAAGAA | ATACAGGGAT | TTTTTTTTTT | TTTAAGATG | GAGTCTTACT | CTGTTGCTAG | 2940 |
| GCTGGAGTGC | AGTGGTGCGA | TCTCAGCTCC | CTGCAACCTC | CACCTCCTGG | GTTCAAACAA | 3000 |
| TTCTCCTGCC | TCAGCCTCCC | GAGTACTGGG | AATATAGGTG | CACGCCACCA | CACCCAACAA | 3060 |
| ATTTTTGTAC | TTTTAGTACA | GATGAGGGTT | CACTATGTTG | GCCAGGATGG | TCTCGATCTC | 3120 |
| TTGACCTCAT | GATCCACCCA | CCTCGGTCTC | CCAAAGTGCT | GGGATTACAG | GCTTGAGCCA | 3180 |
| CCGGGTGACC | GGCTTACAGG | GATATTTTA | ATCCCGTTAT | GGACTCTGTC | TCCAGGAGAG | 3240 |
| GGGTCTATCC | ACCCCTGCTC | ATTGGTGGAT | GTTAAACCAA | TATTCCTTTC | AACTGCTGCC | 3300 |
| TGCTAGGGAA | AAACTACTCC | TCATTATCAT | CATTATTATT | GCTCTCCACT | GTATCCCCTC | 3360 |
| TACCTGGCAT | GTGCTTGTCA | AGTTCTAGTT | GTTCAATAAA | TTTGTTAATA | ATGCTG | 3416 |

( 2 ) INFORMATION FOR SEQ ID NO:16:

( i ) SEQUENCE CHARACTERISTICS:
        ( A ) LENGTH: 3502 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..3502
        ( D ) OTHER INFORMATION: /note= "cDNA 32"

( x i ) SEQUENCE DESCRIPTION: SEQ ID NO:16:

| | | | | | | |
|---|---|---|---|---|---|---|
| AGAGAACAGG | TCCCAGATAC | CGAGTCCGCA | ACCCCAAACA | TCGCGATTAA | TAGGAGGCCT | 60 |
| CTGGTCTCTG | CCTGCCCTGG | GTGCTCATGG | AACCAGCTGC | TGCTCTGCAC | TTCTCCCTGC | 120 |

| | | | | | | |
|---|---|---|---|---|---|---|
|CAGCCTCCCT|CCTCCTCCTC|CTGCTCCTCC|TCCTTCTCAG|CCTGTGTGCA|CTGGTCTCAG|180|
|CCCAGTTTAC|TGTCGTGGGG|CCAGCTAATC|CCATCCTGGC|CATGGTGGGA|GAAAACACTA|240|
|CATTACGCTG|CCATCTGTCA|CCCGAGAAAA|ATGCTGAGGA|CATGGAGGTG|CGGTGGTTCC|300|
|GGTCTCAGTT|CTCCCCCGCA|GTGTTTGTGT|ATAAGGGTGG|GAGAGAGAGA|ACAGAGGAGC|360|
|AGATGGAGGA|GTACCGGGGA|AGAATCACCT|TTGTGAGCAA|AGACATCAAC|AGGGGCAGCG|420|
|TGGCCCTGGT|CATACATAAC|GTCACAGCCC|AGGAGAATGG|GATCTACCGC|TGTTACTTCC|480|
|AAGAAGGCAG|GTCCTACGAT|GAGGCCATCC|TACGCCTCGT|GGTGGCAGGC|CTTGGGTCTA|540|
|AGCCCCTCAT|TGAAATCAAG|GCCCAAGAGG|ATGGGAGCAT|CTGGCTGGAG|TGCATATCTG|600|
|GAGGGTGGTA|CCCAGAGCCC|CTCACAGTGT|GGAGGGACCC|CTACGGTGAG|GTTGTGCCCG|660|
|CCCTGAAGGA|GGTTTCCATC|GCTGATGCTG|ACGGCCTCTT|CATGGTCACC|ACAGCTGTGA|720|
|TCATCAGAGA|CAAGTATGTG|AGGAATGTGT|CCTGCTCTGT|CAACAACACC|CTGCTCGGCC|780|
|AGGAGAAGGA|AACTGTCATT|TTTATTCCAG|AATCCTTTAT|GCCCAGCGCA|TCTCCCTGGA|840|
|TGGTGGCCCT|AGCTGTCATC|CTGACCGCAT|CTCCCTGGAT|GGTGTCCATG|ACTGTCATCC|900|
|TGGCTGTTTT|CATCATCTTC|ATGGCTGTCA|GCATCTGTTG|CATCAAGAAA|CTTCAAAGGG|960|
|AAAAAAAGAT|TCTGTCAGGG|GAAAAGAAAG|TTGAACAAGA|GGAAAAAGAA|ATTGCACAGC|1020|
|AACTTCAAGA|AGAATTGCGA|TGGAGAAGAA|CATTCTTACA|TGCTGCTGAT|GTGGTCCTGG|1080|
|ATCCAGACAC|CGCTCATCCC|GAGCTCTTCC|TGTCAGAGGA|CCGGAGAAGT|GTGAGGCGGG|1140|
|GCCCCTACAG|GCAGAGAGTG|CCTGACAACC|CAGAGAGATT|CGACAGTCAG|CCTTGTGTCC|1200|
|TGGGATGGGA|GAGCTTCGCC|TCAGGGAAAC|ATTACTGGGA|GGTGGAGGTG|GAAAACGTGA|1260|
|TGGTGTGGAC|TGTGGGGGTC|TGCAGACACA|GTGTTGAGAG|GAAAGGGGAG|GTCCTGCTGA|1320|
|TTCCTCAGAA|TGGCTTCTGG|ACCCTGGAGA|TGTTTGGAAA|CCAATACCGG|GCCCTGTCCT|1380|
|CCCCTGAGAG|GATTCTCCCT|TTGAAGGAGT|CCCTTTGCCG|GGTGGGCGTC|TTCCTGGACT|1440|
|ATGAAGCTGG|AGATGTCTCC|TTCTACAACA|TGAGGGACAG|ATCACACATC|TACACATGTC|1500|
|CCCGTTCAGC|CTTTACTGTG|CCTGTGAGGC|CCTTCTTCAG|GTTAGGGTCT|GATGACAGCC|1560|
|CCATCTTCAT|CTGCCCTGCA|CTCACAGGAG|CCAGTGGGGT|CATGGTGCCT|GAAGAGGGCC|1620|
|TGAAACTTCA|CAGAGTGGGG|ACCCACCAGA|GCCTATAGAA|TCAATTCCTT|GGACTCACAG|1680|
|CCATGCAGAT|AAGCCCTGGC|CATCTCAGCA|GCCACCGCAC|AACCCCCTA|ATGAAAGACA|1740|
|CGCCCTCCTC|CCCTCTGGTC|ACGTAAGAGA|ACATCTTCCA|GCTGCCTTTT|TCACACCCAC|1800|
|TCCAGCCCTC|TGCCCCAGTT|TTCTCCTCCT|CACTAGTCTG|TGGCTTTAGT|AGTTCCTTTG|1860|
|CTTGTAATTA|TGGGATGGGA|TCCAGGCATA|GGGAACTAGT|TGTTTCATAG|CTCCCAGTCA|1920|
|AAAAGAAAGT|GAGAGAAGCT|GTTGGGCAGT|GAACCTACTG|TTTAAAATCA|GGATAACCAC|1980|
|ATTAAGCCCA|ATATGCCAGT|TGGCACCAGA|TGCTGTGGAC|TTGGAATGAG|GCCAACAGGG|2040|
|TTCACCAGGA|TGAGAGAGGA|GAGAGGAATC|CACAGGACCA|CCAGAAGGGA|GAGGGAACCA|2100|
|GATATGCAGA|TCAGAGATAG|AGGAAGTGGA|ACCAGAGAGC|TGGGAGGGAC|CAAGGTTGTA|2160|
|AGGATGGCTA|AGTCCCACCA|TAAGAGCTAA|AGGGTCCTGG|GAGATGATGG|CTCATTTCCA|2220|
|CCCAACCCCA|GGATTTCCAC|AGCACACACC|CACAGGCCTG|GACCTGGGAT|GAAGATGAAT|2280|
|GAAGAACATG|GACTCATGTG|GATGTGGTTT|GGCTCAGATG|TCCCTGCAAT|AAACAAGGGG|2340|
|TCAGTACTTA|GTCCCTGAGT|GTGGTTGAGG|TTTGAGGTCC|TGGTCGAGCA|GGGCAGTACT|2400|
|GGACCAGGTC|TACGTCAGCA|TTCAGGTTCA|ATGGGACAC|CAGTGGCTTC|AAACTTCCTG|2460|
|ATCTAATTAT|GTTTTTAGAC|ACTTAGAAGT|TATTGAGGAC|TTTAAAGAGC|TTTTGTTTAT|2520|

-continued

| | | | | | | |
|---|---|---|---|---|---|---|
| TTGGGTTAAT | ATTTATGACA | TTTGACATTG | AAACAAAAAT | TTAAAATGTT | ATCTTTTAAT | 2580 |
| TTATGTTAAA | ATAGCATTAA | TAAATCAGTT | ATAGGTTAAT | GTAGATAGGA | TGTTTTGTGA | 2640 |
| AAAAGCAATC | TATTGTGTCC | AAATAAAAAA | AACAAAAAGT | GTGACACTGG | TTAACTTTTT | 2700 |
| CCAGATCTCA | TGTCTGGCTT | AATAAGAGAT | ATTTGTATTA | TCATATCTGC | CTTTGTATTA | 2760 |
| AACCTATTGG | TATATCATAG | GTCATGTTAG | CTCAAAAAAA | CTTTACTGCA | CACTACTGAG | 2820 |
| AGAATGAGAT | GAAAAACGAT | TAATGTTTCA | TTATTATTAT | TGTGAAAATA | TTATTAACAC | 2880 |
| TGGGGACTCC | TTAAGAGTAC | ATCAGAGTTC | TCTCTAGGAA | TCCCAAAACC | ACATTTTGAA | 2940 |
| ACTAGAATAG | TGGATCCTGG | AAGTTAATCC | ATGTGCTGGT | TAATTTTAGA | TGTCAACCTG | 3000 |
| GTGTTTCCAG | AAGAGATTGG | CAAGTGAGTC | AGTGGGAAAT | TCTCTCCTTC | TGTTGGCTGG | 3060 |
| GTGCCCAATA | CAACAAAAG | GCAGAGGAAA | GGCAAATTCT | TCTCTCCTCT | GGAGCTGAGA | 3120 |
| CACTCTTCTT | CTTCTGCCCT | TGGACATCAG | AACTCCTGGC | TCTCCGGCCT | TGAACTTCA | 3180 |
| GGACTTGTAC | CAGGAGGCCC | TGGGTTCTCA | GGCCTTTGGC | TTTGGACTGA | GAGTTACACA | 3240 |
| ATCAGCTTCC | CTGGTTCTGA | GGCTTTCAGA | CTTAAACTGA | GCCATGCTAC | CAGCATCCCA | 3300 |
| GGGTCTCCAG | CCTACAGATG | AGCTGTTGTG | CGATTTCTTA | GCCTCCATAA | TCACATGAGC | 3360 |
| CAATCTCCTT | AATAAATGCC | TGCTCATAGA | TCTGTATCTA | CATCTATATC | TGTATGTGCA | 3420 |
| TCTATATCTA | TGCCTATATC | TATATCTATA | TCATATTGAT | TTTGTCTCTC | TGGAGAACCC | 3480 |
| TGACTAATAA | AATGAGGCAT | CT | | | | 3502 |

( 2 ) INFORMATION FOR SEQ ID NO:17:

( i ) SEQUENCE CHARACTERISTICS:
        ( A ) LENGTH: 2854 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..2854
        ( D ) OTHER INFORMATION: /note= "cDNA 27"

( x i ) SEQUENCE DESCRIPTION: SEQ ID NO:17:

| | | | | | | |
|---|---|---|---|---|---|---|
| GACCCACGCG | TCCGAAAAGC | TATGGCCTCA | ACCACCAGCA | CCAAGAAGAT | GATGGAGGAA | 60 |
| GCCACCTGCT | CCATCTGCCT | GAGCCTGATG | ACGAACCCAG | TAAGCATCAA | CTGTGGACAC | 120 |
| AGCTACTGCC | ACTTGTGTAT | AACAGACTTC | TTTAAAAACC | CAAGCCAAAA | GCAACTGAGG | 180 |
| CAGGAGACAT | TCTGCTGTCC | CCAGTGTCGG | GCTCCATTTC | ATATGGATAG | CCTCCGACCC | 240 |
| AACAAGCAGC | TGGGAAGCCT | CATTGAAGCC | CTCAAAGAGA | CGGATCAAGA | AATGTCATGT | 300 |
| GAGGAACACG | GAGAGCAGTT | CCACCTGTTC | TGCGAAGACG | AGGGGCAGCT | CATCTGCTGG | 360 |
| CGCTGTGAGC | GGGCACCACA | GCACAAAGGG | CACACCACAG | CTCTTGTTGA | AGACGTATGC | 420 |
| CAGGGCTACA | AGGAAAAGCT | CCAGAAAGCT | GTGACAAAAC | TGAAGCAACT | TGAAGACAGA | 480 |
| TGTACGGAGC | AGAAGCTGTC | CACAGCAATG | CGAATAACTA | AATGGAAAGA | GAAGGTACAG | 540 |
| ATTCAGAGAC | AAAAAATCCG | GTCTGACTTT | AAGAATCTCC | AGTGTTTCCT | ACATGAGGAA | 600 |
| GAGAAGTCTT | ATCTCTGGAG | GCTGGAGAAA | GAAGAACAAC | AGACTCTGAG | TAGACTGAGG | 660 |
| GACTATGAGG | CTGGTCTGGG | GCTGAAGAGC | AATGAACTCA | AGAGCCACAT | CCTGGAACTG | 720 |
| GAGGAAAAAT | GTCAGGGCTC | AGCCCAGAAA | TTGCTGCAGA | ATGTGAATGA | CACTTTGAGC | 780 |
| AGGAGTTGGG | CTGTGAAGCT | GGAAACATCA | GAGGCTGTCT | CCTTGGAACT | TCATACTATG | 840 |

| | | | | | | |
|---|---|---|---|---|---|---|
| TGCAATGTTT | CCAAGCTTTA | CTTCGATGTG | AAGAAAATGT | TAAGGAGTCA | TCAAGTTAGT | 900 |
| GTGACTCTGG | ATCCAGATAC | AGCTCATCAC | GAACTAATTC | TCTCTGAGGA | TCGGAGACAA | 960 |
| GTGACTCGTG | GATACACCCA | GGAGAATCAG | GACACATCTT | CCAGGAGATT | TACTGCCTTC | 1020 |
| CCCTGTGTCT | TGGGTTGTGA | AGGCTTCACC | TCAGGAAGAC | GTTACTTTGA | AGTGGATGTT | 1080 |
| GGCGAAGGAA | CCGGATGGGA | TTTAGGAGTT | TGTATGGAAA | ATGTGCAGAG | GGCACTGGC | 1140 |
| ATGAAGCAAG | AGCCTCAGTC | TGGATTCTGG | ACCCTCAGGC | TGTGCAAAAA | GAAAGGCTAT | 1200 |
| GTAGCACTTA | CTTCTCCCCC | AACTTCCCTT | CATCTGCATG | AGCAGCCCCT | GCTTGTGGGA | 1260 |
| ATTTTTCTGG | ACTATGAGGC | CGGAGTTGTA | TCCTTTTATA | ACGGGAATAC | TGGCTGCCAC | 1320 |
| ATCTTTACTT | TCCCGAAGGC | TTCCTTCTCT | GATACTCTCC | GGCCCTATTT | CCAGGTTTAT | 1380 |
| CAATATTCTC | CTTTGTTTCT | GCCTCCCCCA | GGTGACTAAG | GAAAAGAGCA | GAAGCTCCTT | 1440 |
| GGTTAACCA | GCACAGAGAA | AATAATATAA | ATCCATAAG | GGCAGACGTT | TGGTCTGTTT | 1500 |
| TCTTCGCTGT | CATTTCCTTA | GTAGTTAGAC | TAGTGCTGAG | ATTTTAGTGG | ATATATAATT | 1560 |
| GATTTATGTT | GAATATATGG | ACTTAGCAAC | TAAAAATACC | ACAGATGGTT | AACCTGGACT | 1620 |
| GGGGCAAAGC | AAGATAATAG | TGATGATCGT | ATGTTGCTGT | CTCCATCCGT | CTTTAATGGG | 1680 |
| TCAGGGCTTT | GATTTCCAAG | GGTCTTCAGG | TGATGAGTAG | GGGTACCCAC | AAGTCAGAAG | 1740 |
| GTCTGCGTTC | TCCTAGTTTG | TTTGCTGCCA | TTTGAACTCA | TGTAGGGAAT | GAAAGAAAGC | 1800 |
| TGCAATTATC | CGCCAACTGC | ATTTAAAACA | AACAAAACA | GAAAAATCAA | AATAACATTG | 1860 |
| ACTCTTCCAA | CCACTGACAT | GTTGTTTAAT | AATCTAAGCG | GCAGTCCTGG | AGGCTACCAG | 1920 |
| ACTTACTGAG | TTCTACCTGA | GAAACAGCCA | AGCAAAGTGT | GAGAGAAGGG | TTAAGACTGG | 1980 |
| CTTACAATGA | GATGCTTCAA | ATGAAAGGG | AATTATGAGT | AAAATTGAAC | TTTGATGGGG | 2040 |
| GATTCAGTTC | TGGAAAAGAA | TTTGGTATTT | TCCAGTCTGC | TAGGACCAAT | TACCTTGAAA | 2100 |
| TATTTTAAAA | TCTCAGTAAA | TAGTTATTGC | TGAAATGGCT | GTTGGCAGTT | CTTATTATGA | 2160 |
| TTCAGAGAAG | AGCAAATAGA | CCTTAACTTC | ATTTTGAAAA | AGACCAAATT | ACCATACCCG | 2220 |
| AGTGAGTAAT | GACAGGACTA | CAACTAAAAC | ATAAACAACA | TTAATGATGA | CCATAAAAAG | 2280 |
| TCACAAAATT | GCTAAATGTT | ATAATTTAGA | GTTGACATAA | AAATTGATGG | CCAGGCATGG | 2340 |
| TGGCTCACGC | CTGTAATCCC | AGAACTATGT | GAGGCTGAGG | CAGGTGGATC | ACTTGAGGTC | 2400 |
| AGGAGTTCAA | CACCAGCCTG | GCCAACATGG | TGAAACCCTG | TCTCTACTAA | AAATACAAAA | 2460 |
| ATTAGCCGGG | CATGGTGGTA | GGGGCCTGTA | ACCCAGCTAC | TCGTGAGGCC | AAGGCAGGAG | 2520 |
| AATTGCTTGA | GCCTGCAGCA | GCTGCAGTAA | GCCAAGATCA | TGCTGTGCCT | CAAGGAAAAA | 2580 |
| AAAAATTAAT | GTTACTGAT | ATTTGTTGAA | GTCCTACAAC | ATCACCTCTG | AGAATAGGAG | 2640 |
| AAATGAAGCA | ACAGTTGTGT | CTAGATGTCA | GAGGCATGGC | TGGGCCTCCA | TCTCTGCCTA | 2700 |
| AGGGAGATAT | AAAAGAGTTC | AAACTATTGC | CCATGTTCCC | CAGGGTCAGA | AGTTCTAATT | 2760 |
| ATGATGATAG | AGGCTGGGTT | GTAAGTAGTA | AGTGAAGGGT | AGCAGAATAT | GCCATCTTTG | 2820 |
| GCATAAGAAG | TATTTTGAGT | TGAAGACAAT | TGAG | | | 2854 |

( 2 ) INFORMATION FOR SEQ ID NO:18:

( i ) SEQUENCE CHARACTERISTICS:
        ( A ) LENGTH: 2266 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:

(A) NAME/KEY: misc_feature
(B) LOCATION: 1..2266
(D) OTHER INFORMATION: /note= "cDNA 22B"

(xi) SEQUENCE DESCRIPTION: SEQ ID NO:18:

| | | | | | |
|---|---|---|---|---|---|
| GGACAGAAAA | CTCCCTCCTT | TTCCAAGTTA | GCCTTATAGT | CTAGGGCTTA | AAATACTGGT | 60 |
| TTAATGGTGA | AGGTAAGTGC | TTTTCTTCTT | TTTGGGTAGA | AGGATTATTA | CTAACTTACC | 120 |
| AAAGGTCCAT | TAAGGGGAGG | GAACAGTTTT | AGGAGAAGTC | AGAGAAAAGA | CATTAACAGC | 180 |
| AACATAAGGA | TCTCCATCTG | GTAATATTGC | CTAATTCCAA | AATGAAGAGA | CTCTCTGAAA | 240 |
| AAGATAACTG | ATTCAATGAA | GACCCTAGGG | CAAGGCTTGA | GAAGCCACTG | GTACCAATGG | 300 |
| ACACTGTGGA | CAATGGTCAT | TTCTCCAAGG | ACGCTATAAA | AGACTGTCGT | AGTAAAAGAG | 360 |
| ATTCAGGGCA | CAGGGAAACT | CCACCACAAA | GCGTGGTACC | ATTTCCCACA | GAAGCTAAAT | 420 |
| GGACGGGAAG | CCTGCCACCA | GGAAAGGTCC | AGATTTCTGT | TCATTACGCT | ATGGGCTGGC | 480 |
| TCTTATCATG | CACTTCTCAA | ACTTCACCAT | GATAACGCAG | CGTGTGAGTC | TGAGCATTGC | 540 |
| GATCATCGCC | ATGGTGAACA | CCACTCAGCA | GCAAGGTCTA | TCTAATGCCT | CCACTGAGGG | 600 |
| GCCTGTTGCA | GATGCCTTCA | ATAACTCCAG | CATATCCATC | AAGGAATTTG | ATACAAAGGC | 660 |
| CTCTGTGTAT | CAATGGAGCC | CAGAAACTCA | GGGTATCATC | TTTAGCTCCA | TCAACTATGG | 720 |
| GATAATACTG | ACTCTGATCC | CAAGTGGATA | TTTAGCAGGG | ATATTTGGAG | CAAAAAAAAT | 780 |
| GCTTGGTGCT | GGTTTGCTGA | TCTCTTCCCT | TCTCACCCTC | TTTACACCAC | TGGCTGCTGA | 840 |
| CTTCGGAGTG | ATTTTGGTCA | TCATGGTTCG | GACAGTCCAG | GGCATGGCCC | AGGGAATGGC | 900 |
| ATGGACAGGT | CAGTTACTA | TTTGGGCAAA | GTGGGCTCCT | CCACTTGAAC | GAAGCAAGCT | 960 |
| CACCACCATT | GCAGGATCAG | GGTCAGCATT | TGGATCCTTC | ATCATCCTCT | GTGTGGGGGG | 1020 |
| ACTAATCTCA | CAGGCCTTGA | GCTGGCCTTT | TATCTTCTAC | ATCTTTGGTA | GCACTGGCTG | 1080 |
| TGTCTGCTGT | CTCCTATGGT | TCACAGTGAT | TTATGATGAC | CCCATGCATC | ACCCGTGCAT | 1140 |
| AAGTGTTAGG | GAAAAGGAGC | ACATCCTGTC | CTCACTGGCT | CAACAGCCCA | GTTCTCCTGG | 1200 |
| ACGAGCTGTC | CCCATAAAGG | CGATGGTCAC | ATGCCTACCA | CTTTGGGCCA | TTTTCCTGGG | 1260 |
| TTTTTTCAGC | CATTTCTGGT | TATGCACCAT | CATCCTAACA | TACCTACCAA | CGTATATCAG | 1320 |
| TACTCTGCTC | CATGTTAACA | TCAGAGATAG | TGGAGTTCTG | TCCTCCCTGC | CTTTTATTGC | 1380 |
| TGCTGCAAGC | TGTACAATTT | TAGGAGGTCA | GCTGGCAGAT | TTCCTTTTGT | CCAGGAATCT | 1440 |
| TCTCAGATTG | ATCACTGTGC | GAAAGCTCTT | TTCATCTCTT | GATATGCAAG | TTTCCTCATG | 1500 |
| GGAATCTCAA | GGGGATTTGG | GCTCATCGCA | GGAATCATCT | CTTCCACTGC | CACTGGATTC | 1560 |
| CTCATCAGTC | AGGATTTTGA | GTCTGGTTGG | AGGAATGTCT | TTTTCCTGTC | TGCTGCAGTC | 1620 |
| AACATGTTTG | GCCTGGTCTT | TTACCTCACG | TTTGGACAAG | CAGAACTTCA | AGACTGGGCC | 1680 |
| AAAGAGAGGA | CCCTTACCCG | CCTCTGAGGA | CATAAAGTTA | CAAACTTAAA | TGTGGTACTG | 1740 |
| AGCATGAACT | TTTTAAACAT | TTTTTACTTC | TCTCCATATT | CCTGACCATA | GACTCAGCAG | 1800 |
| TTCTTAACTC | TGGCTGTGTG | TTAGTCTTCC | CTGGGGAGCC | TTTATAAGAC | ACTGATACTT | 1860 |
| GGGACCCACT | CCAGAGATTC | TGAATGAATT | GGTCTGGGGT | GGAACCCAGA | TACTACTAAT | 1920 |
| TTTTAGATAC | TCCTTAGAGG | TTTCTAGCAT | GCGCCGGGG | TTGACAACAG | CTGGACAAAC | 1980 |
| TTGAAAAGTC | AATTCATGTG | GCCTTTGAAT | TTTCCTCATT | GGAAAGTACT | AAATAAATAA | 2040 |
| AAATTCATGT | GAAAATGATC | ACTGATAAAT | ATCTTCATGG | TGGGCAGGT | TATTGGATGC | 2100 |
| AGAGAAGATC | TGCTCGGAAT | TGTAGCCATA | TGTTACAGAT | CTCAGCACCG | ATCAGAACTG | 2160 |
| TAAAGCTATA | ATCCCCAGAA | TTAAAGTTTT | TATTATTTTT | TATACATTGT | AAAACATAGA | 2220 |

| | | | | | | |
|---|---|---|---|---|---|---|
| CGTTTATTTA | TGTGATTAAA | TTCTATTAAA | ATTTACATGC | TAAAAT | | 2266 |

( 2 ) INFORMATION FOR SEQ ID NO:19:

( i ) SEQUENCE CHARACTERISTICS:
        ( A ) LENGTH: 1780 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..1780
        ( D ) OTHER INFORMATION: /note= "cDNA 22E"

( x i ) SEQUENCE DESCRIPTION: SEQ ID NO:19:

| | | | | | | |
|---|---|---|---|---|---|---|
| ACGCGTCCGC | CCACGCGTCC | GCCCACGCGT | CCGGTCGGGG | CCAGAGCGCA | GGTGTACCTG | 60 |
| GCGGCCGTGC | TGGAGCACCT | GACCGCCGAG | ATCCTGGAGC | TGGCTGGCAA | CCCGGCCCGC | 120 |
| GACAAGAAGA | CCCGCATCAT | CCTGCGCCAC | CTGTAGCTGG | CCATTCGCAA | CGGCGAGGAG | 180 |
| CTTAACAAGC | TGCTGGGCGA | AGTCACCATC | GCGCAGGGCG | GTGTCCTGCC | CAACATTCAG | 240 |
| GGCGTGCTTC | TGCCCCAGAA | GACCAAGAGC | CACCACAAGG | CCAAGGGTGA | AAACCATTCA | 300 |
| CTAGGAGAGG | AGAAACACAA | TGGCCACCAA | GACAGAGTTG | AGTCCCACAG | CAAGGGAGAG | 360 |
| CAAGAACGCA | CAAGATATGC | AAGTGGATGA | GACACTGATC | CCCAGGAAAG | GTCCAAGTTT | 420 |
| ATGTTCTGCT | CGCTATGGAA | TAGCCCTCGT | CTTACATTTC | TGCAATTTCA | CAACGATAGC | 480 |
| ACAAAATGTC | ATCATGAACA | TCACCATGGT | AGCCATGGTC | AACAGCACAA | GCCCTCAATC | 540 |
| CCAGCTCAAT | GATTCCTCTG | AGGTGCTGCC | TGTTGACTCA | TTTGGTGGCC | TAAGTAAAGC | 600 |
| CCCAAAGAGT | CTTCCTGCAA | AGTCCTCAAT | ACTTGGGGGT | CAGTTTGCAA | TTTGGGAAAA | 660 |
| GTGGGGCCCT | CCACAAGAAC | GAAGCAGACT | CTGCAGCATT | GCTTATCAG | GAATGTTACT | 720 |
| GGGATGCTTT | ACTGCCATCC | TCATAGGTGG | CTTCATTAGT | GAAACCCTTG | GGTGGCCCTT | 780 |
| TGTCTTCTAT | ATCTTTGGAG | GTGTTGGCTG | TGTCTGCTGC | CTTCTCTGGT | TTGTTGTGAT | 840 |
| TTATGATGAC | CCCTTTTCCT | ATCCATGGAT | AAGCACCTCA | GAAAAGAAT | ACATCATATC | 900 |
| CTCCTTGAAA | CAACAGGTCG | GGTCTTCTAA | GCAGCCTCTT | CCCATCAAAG | CTATGCTCAG | 960 |
| ATCTCTACCC | ATTTGGTCCA | TATGTTTAGG | CTGTTTCAGC | CATCAATGGT | TAGTTAGCAC | 1020 |
| AATGGTTGTA | TACATACCAA | CTTACATCAG | CTCTGTGTAC | CATGTTAACA | TCAGAGACAA | 1080 |
| TGGACTTCTA | TCTGCCCTTC | CTTTTATTGT | TGCCTGGGTC | ATAGGCATGG | TGGGAGGCTA | 1140 |
| TCTGGCAGAT | TTCCTTCTAA | CCAAAAAGTT | TAGACTCATC | ACTGTGAGGA | AAATTGCCAC | 1200 |
| AATTTTAGGA | AGTCTCCCCT | CTTCAGCACT | CATTGTGTCT | CTGCCTTACC | TCAATTCCGG | 1260 |
| CTATATCACA | GCAACTGCCT | TGCTGACGCT | CTCTTGCGGA | TTAAGCACAT | TGTGTCAGTC | 1320 |
| AGGGATTTAT | ATCAATGTCT | TAGATATTGC | TCCAAGGTAT | TCCAGTTTTC | TCATGGGAGC | 1380 |
| ATCAAGAGGA | TTTTCGAGCA | TAGCACCTGT | CATTGTACCC | ACTGTCAGCG | GATTCTTCT | 1440 |
| TAGTCAGGAC | CCTGAGTTTG | GGTGGAGGAA | TGTCTTCTTC | TTGCTGTTTG | CCGTTAACCT | 1500 |
| GTTAGGACTA | CTCTTCTACC | TCATATTTGG | AGAAGCAGAT | GTCCAAGAAT | GGGCTAAAGA | 1560 |
| GAGAAAACTC | ACTCGTTTAT | GAAGTTATCC | CACCTTGGAT | GGAAAGTCA | TTAGGCACCG | 1620 |
| TATTGCATAA | AATAGAAGGC | TTCCGTGATG | AAAATACCAG | TGAAAAGATT | TTTTTTTCCT | 1680 |
| GTGGCTCTTT | TCAATTATGA | GATCAGTTCA | TTATTTTATT | CAGACTTTTT | TTTGAGAGAA | 1740 |
| ATGTAAGATG | AATAAAAATT | CAAATAAAAT | GATAACTAAG | | | 1780 |

( 2 ) INFORMATION FOR SEQ ID NO:20:

( i ) SEQUENCE CHARACTERISTICS:
        ( A ) LENGTH: 246240 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..246240
        ( D ) OTHER INFORMATION: /note= "HLA-H.CONTIG"

( x i ) SEQUENCE DESCRIPTION: SEQ ID NO:20:

```
TTTGTAAGTA  TTCTATTTTA  TTTATATGTG  TTTGTGTTTC  TGAGTATGTC  CTGAGTTGCA    60
CGATAATACT  ATATTTCTTA  TTGGGTAACA  TTGTCAGAAA  AGTTTCTAAA  AACTTTCTCT   120
GCTGCACTTA  TTTTATACAT  TTTATTTATG  TTAATAATCT  CACATTTAAC  ACACTTATGA   180
TTTATTCTCA  ACAGAAAAAG  GTGGTATTTC  TTTCATTTAG  TCTTTTAAAA  AGCTCACATT   240
ATCAAATGAT  TGCTCAATCA  TTTAATCTCT  TTGCTTCTCT  TATATGCATT  GATTTAATAA   300
ATATGTATAC  TAGTTTCTCC  ATCGATTCTT  TAGATTTGAA  ACTTATTTTC  CTTTTATTCT   360
TACAAAACTG  ACTTGTCTAT  AGGCCCACTT  CTACTTCCTT  TATTCTATCA  TCTTCCTCAA   420
CTTATTCTGT  GGTCAAAGAA  TGGAGAAATA  ATATTAATAA  TATGTTTTTC  TCATCAATGA   480
CTTCCACCTG  TTCTCTGAGA  AATTCAGCTT  CAAGAACTTT  AGTTGATAT   GACTGCAAAG   540
ATAATACACA  GTCTAAATCA  TAAAAATGTC  TCAAAGGTTT  TTTTTTATT   TGTTTCTTTG   600
AAATATCCAT  GAACAGGCAT  GTTTCTCCCC  CTGTAGTGCA  ATTTGTGTGA  AATTCTGGCA   660
TGCACTTAAG  AGGATGTCCT  AAAATACCAA  TATTTAATTG  ATTCTAAGTC  ATGTATTGTA   720
TCACATTTTT  GCCCATGGAT  TGTTGAAATC  CATGGACAAA  ACTGATAGCA  TTTTAGAACT   780
TCCTTTGTCT  AGTGGCAGTC  TTGATATATT  CACACTATCT  ATTGACAAAA  AATCTAAAGC   840
ACCAGGCTCA  AAGCTTGTAG  AGTAGGTGTC  AGTGATTTGG  AGGACATCTC  TAGGGCAATA   900
GTAGAGGCAT  TTTTAACCCC  TAACAACTAA  ATGATCATCA  GAAGTGAGTG  ATATCCTCAC   960
TCATGACCCC  AACTGCTCTA  ATTTCTATTG  TTTTCTTGCA  GAAATGAGAG  CAGGTGGGGT  1020
CATGGGTGAG  GAATGAGGTG  TTGAAAGTGA  ATGGGGTGTT  GAAAGCAAGG  TGTTTAGCAG  1080
TGTTCTGAAA  GCATACATTT  AAGTAGGCTA  TCCGGGCACT  GTCAATAGCT  AAGTGTCAAG  1140
CTAAGTACTC  TATTTTATTC  TAAGAACTAT  TTTAGAAAT   GCTGAATCAA  CAAATCTCAG  1200
ATGGCACAGA  GGTTGTCATT  TTTGAATAAT  ATGAATATCA  GTAATTTTAG  TTGGAAAAGA  1260
AGATTTTCAA  AGAGCCATCT  AAGTTTCCAA  AATAAGTGTT  GCAGTCATAT  TAACTATTAT  1320
ATTTTCCTGC  CTGTTGATCT  ACTGCCTGTG  AATTGCTTAT  CAAACCAACA  ACCAACTGGA  1380
ATACATAGAC  TGCATGTCTT  GTTCATTTCC  TGCATTCTCA  AGTAATGGTT  TAACAAACTC  1440
ATGAGCTTAC  TCTTTAATCT  GAACCATGCT  TAACTTCAAT  TATGTTGATT  TAGTCTAAGG  1500
ATGCAGAATT  TATTTTATAG  TTATGTAGGA  ACTGGAATCC  AAAATGTAAT  ATGCCTCCAA  1560
GCTTTTCTTT  GTTGGCCTCT  GAAGGAGCAT  CACCTCTACA  ACTTCAACGT  TGTTATGAAT  1620
ACCTCTGGGG  AGGTGTTCAC  CTCAGGACCC  AAATTTGGAA  AAAGGGAAGT  GCCACTTTGG  1680
AGGAGTGCTC  TGAGCAGCTG  ATCCATTAAA  TGTCCCGATC  ACATGCACGT  GGAAGTGTCA  1740
TTGCAATATC  TGCACTAACA  GAAGCTCAGT  GACTTGAGAA  GTGAGTCTGG  AATTCTAAGA  1800
AAAAGGCAAG  GCATCTCTCT  TGCCACTTGT  TATTTTTCCA  GTCAAGCAAC  TGTGATAAGA  1860
```

```
GGGCATGGAG  AGCAGGAAGA  AGTGAAAAAT  CCCAGGAAAG  TCTGGAGTGG  AATCATTAAA   1920
CCAATTCTGC  TCCCTCTCTA  GGCCAACTTG  GGCCTATTAT  GAATAAGGAG  GTCTCTTATA   1980
ATCCATCTAA  CTCCACTCAG  GAACAATTTG  GGGATCTGAG  ACTGTGAACT  CAGTGGGCAA   2040
AAAAATATTT  CTTGGCCTAT  CATTATTCTC  TGTAGGATGT  TAAGGACAGG  TTTCTGTATG   2100
TGGAGTCCTC  AGTTTTGCC   TTCTCTCCTT  GAGATATTTT  TATGCTATTT  AGTAATTGAT   2160
GGCCACAGTT  GATCGACCAC  ATTTCTGGGC  AACTCTAATA  ATCCTTGTTA  TATTAATCAT   2220
TGGACCAATC  TTGATTGTGT  ATGACCATCA  TCTTGTAGCT  ACCACCTCTA  TGTGGATGCT   2280
CTCCTCACCC  TGCTTAAGTG  CCAATGTCTG  TGCTATGGGC  CTACCTGTCA  CATGGATAAT   2340
CTCTTCACTC  CAGTCAGGCT  CCAACATTAA  CACAGGGCTG  TTCTCTTGTC  CCCCTTTGAA   2400
GACAGCTTCA  TCACCCTATT  CAAGTTGCAG  TACTCTCACT  GGGCCTCCAC  TGTTGCCTCT   2460
CTCTCACTCT  GCTTAGGTTT  CTTCACTCCA  CTCCAGGCAA  CTGTCACTAA  ACATCCTTTC   2520
CCCCATATAT  AACACAGACA  TCTACCTTGC  TTGGCCAAAC  CCACTGGATT  TCAGACTCAC   2580
TCATTCAGAG  AGTAAGACAG  AGAGGGGTTC  ATTTTTATT   TTATTTTATT  TTTTATTTTT   2640
TGAGACGTTG  TCTCACCCTG  TCGCCCAGGC  TGGAGTGCAG  TGGTGCAGTC  TTGGCTCACT   2700
GCAATCCCCA  CGTCCCAGGT  TCAAACGATT  CTCCTGCCTC  AGTCTCCCAA  GCAGCTGGGA   2760
TTACAGGTGC  CTGCCACCAT  GCCCAGCTAA  TTTTTGTATT  TTTAGTAGAG  ACAGGGTTTC   2820
GCCGTGTTGG  CCAGGCTGGT  CTCGAACTCC  TGACCTCAAG  TGATCTACCC  GCCTCGGCCT   2880
CCCAAAGTGC  TGGGATTACA  GGTGTGAGCC  ACTGCGCCCA  GCCGGGGTTC  ATCCTTAATA   2940
CATACATTAG  AGATATAGAT  TCTGTTTTTA  TCTAAAAAGT  CTTTATAAGG  CCGGGCGCGG   3000
TGGCTCACGC  CTGTAATCCC  AGCACTTTGG  GAGGCCGAGG  CGGGCGGATC  ACGAGGTCAG   3060
GAGATCGAGA  CCATCCCGGC  TAAAACGGTG  AAACCCCGTC  TCTACTAAAA  ATACAAAAAA   3120
TTAGCCGGGC  GTAGTGGCGG  GCGCCTGTAG  TCCCAGCTAC  TTGGGAGGCT  GAGGCAGGAG   3180
AATGGCGTGA  ACCCGGGAGG  CGGAGCTTGC  AGTGAGCCGA  GATCCCGCCA  CTGCACTCCA   3240
GCCTGGGCGA  CAGAGCAAGA  CTCCGTCTCA  AAAAAAAAA   AAAAAAAAA   AAAAAAAGT   3300
CTTTATAAAA  ATCTGATTGA  ATGGTTGAAT  GCTGTGCTAA  AATCTGCATA  ATATCTTACA   3360
ACACTTCTGT  GAATCACGAG  ACAGTTTTGA  ATGCTAAATG  TCAGTTAACA  GATCTAAAGG   3420
GACCAACATC  TGCTTTCCCA  AATTATATGA  AGAAGATCC   TGATCCCTCA  TCAGGTGAAA   3480
CTCACATCAG  ACAACAGTGT  CTGCATTTCT  CCAAACCCG   CCTCAGCCCC  ATGGCCACTT   3540
TCCAGGGTTA  TCCTGCCTAC  CAAGCACTCT  CTTTCCTCAG  AAAAACTTGG  GGGAAAATGT   3600
AGAATAATAA  TTTTTTGAAG  TTCTGACCAA  CTTCTTGAAT  CACTCAGCAT  GTTTTTGACT   3660
GCAGGTACAG  AAAACGCTGA  CTCAACAAAT  TTAAACACTA  TATAAATTTC  TTATCTCCCC   3720
AAACAGGACA  TCAAAGGCAG  AAAGGTTCCA  GAGCAGGGTG  ATCAGAGCTC  TGGCTCCACT   3780
GCCCTCAGTC  TTCTTGCCTC  TGCTCTCCTT  CACAGCAGGC  TTTACCCCCC  ATGCTGGTCA   3840
CAGTTTCAAG  TGTCCATGCA  GACACAAGTT  AAAGGCAGGA  AGAAACAGTG  CGTTTCTCTT   3900
GGAGATCAAG  GAATGCCTTT  CCAGAAAACT  CCCCCTTATG  TCTCATTTGC  CAAAACTTGG   3960
CCTAGTCTCA  GGTGCTGCCT  GAGCTAATCA  GCTACAGAAG  AAGGGACCAC  ATGACTGGTG   4020
TGGACCAGTC  AGAATTCACC  ACATGAAGCT  AGTAATGTGG  CTCACACTTC  CCAGGGGAT   4080
ATGGCCAGGT  AGCAGACAGT  GGATCGCTGA  ACAGAATACT  GATAGATTTC  AGCACCAAGG   4140
TTAGAATGGC  TACCACACCT  AATCCCACCC  TATCCCCGTT  TCCTTCTTTA  ATTTTTTCCA   4200
TAGCACTTAT  CAGTAGCTGA  CAAACTGTAT  ATGTTTTTAC  TTTTTTATTG  TCTGTAGCTC   4260
```

| | | | | | | |
|---|---|---|---|---|---|---|
| CCAAGTAGAA | TACAAACATC | TGAAACTCAC | TGTATCCATC | CTGAGTAATG | TTCTTTTCAG | 4320 |
| CTCAGTCACA | ATCATTTTTT | GATAGCCTAT | CCTATAAGCT | TAACTTATAG | TGTTAATCAG | 4380 |
| TATTAATACA | TCTTAGTGGG | AAAGAAGGAA | AAAATAAACG | ATCACACACA | CACACACACA | 4440 |
| CACACACACA | CACATACATT | TACGTAACAG | AGCAAGTGTG | AAAATACCTA | AAGGCTTTAT | 4500 |
| AGCTCCTTTT | GTCAATGGAT | ACATGACAGC | ATTTTTGGCA | TTCTTTACTA | CTCTTATTCT | 4560 |
| ATGCTCCATT | TGTCTTCAGT | CAGCACCTCA | GCTGCCCTTA | TGTTTTACTT | GGTAAGGCAA | 4620 |
| ATTCCTAAAT | GAGCCTGGTA | ATTAGTCATC | CAGCTTATAG | GAAGGTACTA | TAGTTTTTCA | 4680 |
| TTAACTTTTT | CACTGGGCTT | GAGAGTAGTA | AGGACTCCCA | GAGAATTCCT | TGTGTTCCAA | 4740 |
| AAGTACTTCT | CCTTGACATC | TTGGTATAGG | ATTAATAACT | GTTTACCTTT | GATAATCAGG | 4800 |
| AAGAATGACT | CCAGCTAGTA | CAGTTACGTG | ATGCCTATAC | ATTCCTTTTT | TTCTGGGAAA | 4860 |
| AATGTAATGT | GAAATTAAGT | GCAAAACCA | TGCCTTGTTT | ATGTATGTAT | CAAACACTTC | 4920 |
| TAGAGCTTTC | CCAATACAGT | TCTCTTCTCA | GCAAACAAGA | GGACTATACC | CTCATCCCCA | 4980 |
| CCCCTGCACT | TAGGTGTAGC | CAATGTGTTG | TAACTTAAAG | AGGAGAGGGC | ACTGGATGAA | 5040 |
| GGGAAATCTG | TCTAACAAGC | TTCTTTATTT | CACCTAGTGG | AAAAAGCCT | TAATCTGCAG | 5100 |
| TGGGGCAGTT | TTCAAGGACA | TAGACTGAAT | TGGCTCATGC | ATTTATGGAA | GATGAGGAGT | 5160 |
| CCCATGATCT | GTAATCTGCA | AGCTGGAGAC | CCAGGAAAGC | TGGTGGTATG | ATTCAGTCTG | 5220 |
| AATCTGAAGG | CCTGAGAACC | AGAGGAACTG | ATGATGTAAA | TCCCAGTTCA | AGAGCAGGAG | 5280 |
| ACCAGATGAG | ATGTCCCAGC | TCAAGCAGTG | AGGCAGAAAA | AAAGGCCCAA | ATTCCCCCTT | 5340 |
| CCTCTGCCTT | TTCTTCTATT | CAGACCCTGA | ATATCAGGTG | GCATAATGCC | ATCCACACTG | 5400 |
| GGAAAGACAG | TTTACTTTAC | TAGGATCACC | TATTCAAAGG | CTAATCTCAT | CCAGAAACAC | 5460 |
| GCTCACAAAC | ACAGCCAGAA | ATAATGTTTA | ACCAGATAGC | TGGTTATCCC | CTGACTCAGT | 5520 |
| CAAGTTGACA | CAAAAAATGA | ACTATTTCAA | AGCTTACTGT | AATCAACAGT | TTTGTCAAAA | 5580 |
| AGATAGACAC | AAATCAGTGG | AATGAGATAA | ACAGTCTAGA | AATAAACCAA | CAAAATATT | 5640 |
| GCCAACTAAG | GCAAAGGTAA | TCAATGGAAA | AAAGATAGTC | TTAGCAACAA | ATAGTACTGG | 5700 |
| AACACCACAA | TGTGTTAATA | AAGTGAAACT | GGAGACATCT | CTCACACCTT | ATACAAAGT | 5760 |
| AACTAAAAAT | AAATCAAAGG | ACTAGATGTA | ATGTATCAAA | CATTACATCT | TTTAGAATGT | 5820 |
| ATCAAACATT | ACAAGCTTTT | AGAATAAAAT | ATAGAAGAAA | ATTTACATGA | TCTAAGATTT | 5880 |
| GGCCCCAATG | AAGTTTTAGC | TATAATAACA | AAAGTATTAG | TCATGGAAGA | AAACAAAATT | 5940 |
| GATAAGTTCA | GGTGGGCTAA | ATTAAGGGAA | AAAAATCACT | TTGCAGTAGA | GAAACCTGAA | 6000 |
| ACATTACCTA | AACCACATGA | TGAAGGTTAA | TATCAGTGAT | GTCATGTGGA | TATCATGTTC | 6060 |
| TCCCTAAAAT | GATGTGACAA | GAAGGGCCCT | TGCCCTTGT | GGTATTATTT | CAAAAAATCT | 6120 |
| ATAACTCCGG | TGTAATTATG | AAAAAAAAGC | AAATGATCTT | CAGGACTGTT | AAGGTCATGA | 6180 |
| AAAGCAAGAA | AAGACTGAGA | CATTGTCACA | GACAAAAAAA | GACTAGGGAG | ATATGACAAG | 6240 |
| AAAATGCAGT | GTGGTATTCC | AGATTGGACC | TTGAACAGA | AAGAAACAT | TAGTGGAAAC | 6300 |
| AGTGGTGAAA | TCCACATAAA | GTCTAGGGTT | TGGTTAATAG | AGTTTCATGT | ATCAATGTGA | 6360 |
| GTTGCTTATA | TTTGACAAAT | GTATCATAAT | AATGTAAAAT | CCTAACAATG | GGGAAAGCT | 6420 |
| AGGTGAAAGA | TATATGGGAA | CTCTCCTGTA | CTGTCTTTGT | ACTATCTTTG | CAACTTTCCT | 6480 |
| GAAAATCCAA | ATTATTCTAA | AACAGAAAAG | TTCATGCTAT | TAGAAGTGAG | GATAGAGGTT | 6540 |
| ACCTTGAAGA | AGCTGAGGTC | TAGAAGAGAC | CATGAAGGGT | CTAATTAGCT | AACACACGTT | 6600 |
| GAGTATCCCT | TATGCTTAGA | ACCAGAAGTA | TTTCAGATTT | TTTCAGATTT | GGAATGTTTG | 6660 |

| | | | | | | |
|---|---|---|---|---|---|---|
| CATTATACTG | AGTATCTCAA | ATCCAAAAAT | CCAAAATCTG | AAATATTCCA | TGAGCACTCC | 6720 |
| TTTGAGAATC | ATGTTAGCAT | TCAAAAGTT | GCCGATTTTG | GAGCATTTTG | AATTTCCAAT | 6780 |
| TTTTAGATTA | GGAATACTCA | ACCTGAGTAG | AGGCTGCCTG | CTAATTACCT | GGGAGCTAAT | 6840 |
| TACATGGATA | TGTCATTTTG | AGAAAGTTTA | GCTTGCTGAT | ATGGATGATT | TTCTGGATAA | 6900 |
| AAATTATACT | TTGATAACAA | TTCTTTTAAA | GGAGACAATA | ATTATTAACT | TTAAGTACT | 6960 |
| TTTTAGCTCT | ACAATTCAGA | ATTCTTTAGT | GCTAAATATT | ACATATTTTG | AAACAAAAGT | 7020 |
| TTTGTTTATA | TTTATTTATT | TGTTTCCCCC | CCCCTTTTTT | TTTTTTGAG | ACAAGTTCTC | 7080 |
| ACCTTATTGC | CCATGCTATA | GTGCAGTGGG | TGATTATAGC | TCACTGCAGC | CTCAAACTCC | 7140 |
| TGGACTCAAA | GGATCCTCCT | GCCTCAACCT | CCCAAGTAGC | TAGGAGTACA | AGCATGCACC | 7200 |
| ACCATATCCA | GCTAATTTTT | GTTTATTTCT | ACAGAGGCAG | GGTCTCACTA | TGTTGCCCAG | 7260 |
| GCTGATCTCA | AATTCCTGGC | CTCAAGTATC | CTCCCACCTC | TGCTTCCCAA | AGCGCTGGGA | 7320 |
| TTACAGGTGT | AAGTCATTGC | ACCCAGCCAA | AAGTTTTATT | TTAAACTTAT | TATTATGAGC | 7380 |
| ATGTAACAGA | TTTATGTGGT | TTGAAATTCA | AACCTACAAA | AGAAAATAAT | AAAAAGCTAA | 7440 |
| CAGATAGACA | AACAAAAACA | AAAGCAAAAC | CCCACTTGGC | CATGCTCTCT | AGTTCCTCAT | 7500 |
| TTCTCTCTTG | GAAGAAACCA | GAGCAATGTT | CCCTGTGTAT | CCTTCCAGAG | ATAATTTTTT | 7560 |
| AAAATACTTT | TTTCTTTTA | ACAGAAGAGA | TGGTAGACTA | CTTCTTTTAA | ATTAAATTAA | 7620 |
| TATACATTTA | CTTGTTTCTT | TTTATTGCTA | TAGAAAATGA | AGTTGGGGAA | ACAGGAAAAA | 7680 |
| TGACCTAGTA | TTATCATACT | AACATACCAA | AATTTTTCAG | TTATATGTAT | TTCCTGTTTC | 7740 |
| AGTTTTTACC | CCACCTGTTT | TTTATTTGGT | TTGAAATCAT | AGTACAGATA | AAAACTTGAG | 7800 |
| GCAGGTATTT | TAGACTTGTT | TTTCTTTTGT | AACATAAAAC | TTTGAGAGCA | CCAGGAAATC | 7860 |
| TGGAAATATT | CATTTAGTTA | TTCATAATTC | AAAATATTGT | TATATCCACT | TTGTGTCAGA | 7920 |
| CTATTTGTTA | AGAACTAAAC | TAAAAGAAAA | AGATGGGGCT | GGACATGGTG | GCTCACACCT | 7980 |
| GTAATCCCAG | CACTTTGGGA | GGCTGAGGCG | GGTGGATCAC | CTGAGTTTGG | GAGTTCGAGG | 8040 |
| AAAGCCTTGC | CAACACGGTG | AAACCCTGTC | TCTACTAAAA | ATACAAAAAT | TAGCCAGGTG | 8100 |
| TGGTGACACA | CGTCTGTAAT | CCCAGCTACT | CAGGAGGCTG | AGGCAGGAGA | ATCACTTGAA | 8160 |
| CCCAGGAGGT | GGAGGTTGCT | GTGAGCCGAG | ATCATGCCAC | TGCACTCCAG | CCTGGGCAGC | 8220 |
| AAAGCAAGAT | TCCATCTCAA | AAAAAAGAT | GATAACACCC | TCTGGGAGAT | TACATTCAGA | 8280 |
| TAGAACAAAT | AAGGTGTAG | AACCTAAGAT | GTGACAAGGA | CACTGTTGGG | TGACTGATTC | 8340 |
| TTCCTGGGAA | CATTTATAAA | GGCTTCCTAG | GGGAGGGCGT | GTTTGTGTAA | GAGCTTTCCA | 8400 |
| GGTCAGAAAG | TATGTACAGT | GGAAAATGTA | TATGAAAAGA | CCGTGTTTGG | GAATCAGGGA | 8460 |
| TTATATATTG | TGATTAGAGG | AAAGAGTCCT | AGGGTTTGAT | ACCTACAAAG | AATTAGAGTT | 8520 |
| TCTAGGTGCT | TCTGGACATG | TGGATTGATG | ACAGCAATAC | TAAAAATACA | AAATTAGTG | 8580 |
| GGGCATAGTG | GTGAGCGCCT | GTAGTCCCAG | CTACTTGGGA | GGCTGAGGCA | GGAGAATAGC | 8640 |
| TTGAACCCGG | GAGGCGGAGG | TTGCAGTGAG | CCGAGATTGT | GCCACTGCAC | TCCAGCCTGG | 8700 |
| GTGACAGAAC | GAGACTCCGT | CTCAAAAAAA | AAAAAGAAA | AAAGCAGGA | GTTAGCAGAA | 8760 |
| AACCAACAAG | ACATGGGAAG | GAGAGAGAGA | GCTGCAACAC | CAAGAGAAA | AAATAGCAAT | 8820 |
| GCTGAAATCA | AAGTATAATG | AAGGAGAGAG | GATGCTGGAA | GCTATGAAAT | TCTTTCTGTG | 8880 |
| AGGCAATGGG | GCAATGACCC | TAGAACTGCT | GAGTTAGCAG | CAGTGACAGA | CTCAGTGCCA | 8940 |
| AATCATATAT | TAGAAAAAAA | AATCAGATAG | AGGTAAAGTC | CAGATCCAAA | GAAGAGGGTT | 9000 |
| TTTAGCAGTA | AAGCAGACAG | TAGAACCCAC | CCAGCTTTCT | AGGGTGCAGG | GGGCCTCCCT | 9060 |

```
TTCAGGCATC  ATGAACAGTG  GGGGACCATA  ACTAGGCATG  ATGGCTTCAG  ATACAGGGCT    9120

TGTTCATCTC  TTGTTGTGGT  CAGGCACTGC  CTAATGAGAG  CAACCCCTTC  CAAATGCTAC    9180

TGCTGTGTTT  AACTAGGGCT  CTTGATAATC  TGACCAGCTT  CTGTCTTACT  GATTTTAGGA    9240

GAAAAATGGA  GCAACCTGCA  AGATGAGTGG  GATTAGCTTC  GTGCTGTCTC  CCATGCACAC    9300

CACTCATGCA  CACTTGGCGA  GCATGGCAGT  TCCATTTATT  TTGCACCCAG  TTGTGATTTA    9360

AAAACTTTTA  ATTAATTAGT  CTTATTAGTC  TTCAGTTGGA  TTTAAATGCC  AAATAATAAC    9420

CTTCTACCTT  GTAAGAGGAG  CCCTTTTACC  TAAAGCAAGG  CTTAAGTTTG  GATAAATTTT    9480

GTCCTATTTA  TTATTCATCC  ACAAGCTCTC  TTAAAACACT  GAATACACAC  TAAGAAGGCT    9540

CTCAGCACTC  CGAATAGTGT  GATAAATCAA  AAGCCAGTAA  CTTCTCAAAG  TCATTGTGTA    9600

TTAGTCAGGG  CTCTCCAGAA  AAATAAAACC  AATAGAACAT  ATATACATGG  GCTTTTACCC    9660

AAATGTCATC  TTTTCAATGA  GTCCTCTTGC  CTGCTTAATT  TTTCTTTTTA  GCATTGCCA     9720

CCTCCATATA  ACATGCACTT  TACTTATTTA  TTGTCTTATT  CTCTTTCACA  TGGGCAGGGG    9780

TTGCATTTGT  CTGTTTACTG  CTGTATCCCT  AGCACCTAGA  GTGGTGCCTG  GCATACGGCT    9840

GGTGTGTGAT  ACATATATTT  GGAGTGGAGG  TAAAAGTCAC  CACTTAGGCT  ATCCACTTTT    9900

GTGACAGGGA  CAACACACGT  ATCACTTGTC  ATTGTACCTA  TAGCATCTCA  CCCAGAGCCA    9960

CAAAAAAAGT  GGCTCAAAGT  ATATATTAAC  AAAGAACAAA  ATGGAATAAT  CCCATCTGAA   10020

GGCGAGGATA  TAATAAAAGC  AACATACCTT  TTTTTGGAAG  GACATGGAGA  GCATCAACCT   10080

TAAGACTAAA  GACTAAACTT  GAGAAGCAAT  TATTACATTT  CTATTAAAAA  TTACCAAATA   10140

CAAATAGTTA  ACTTTGAAGA  AATATATGAA  TAATGATGGT  ATCTGCAAAA  GAGGAAAAGA   10200

CTTACTCAAT  TTCATTGTAC  CTTAGTTGTA  AATAGTATTC  AGGCCACCAT  TTGGAACCTA   10260

TGTGACACAG  TTTAGTTCCT  GTCTATGTTC  ATAAGAGAGG  GCAAAGGCCC  GTTTACATCC   10320

AACCTCTGTA  TGCCAGCAGC  CACGTATGCC  ACACTCTAAA  ATGGCTAAAC  AGTCATTCAT   10380

CAGAATCGGT  TCCAAGAACT  CCAACAAAAA  TTAGAGCTCA  TGGTGCCAGA  TTGGCCTGGA   10440

TTTTCATGCT  CCTGGGTGAT  TACAAAGTTG  TAAATAATGA  TGCTGTCCAC  TGATTTTCAT   10500

CATGCGGGGC  TCTCTGCTTC  ACTGTGCCTT  CCTCTTATGT  CCATGGCACC  AATTTCTCTG   10560

ATAGTTCCCC  CAGGGGATAG  GGTTAGATGT  GGGTTCATAA  GCGCTGGACC  ACTGAGGGTA   10620

ATTCACTCTT  AAGACTAGCG  AGCACTTTCT  GAATCTGAGG  AGTCACATAT  TAAAAGAGGC   10680

AGAATCATCT  TCTGATTTCA  AAAAAGCAAC  TACATGACCA  CCCTGAAAGT  GATTTCAAAA   10740

CAGTTGAAAG  CTAGCTGTTC  AAGTTGATAA  AAGCCACTGC  AGTTCCCTGC  AGGGAATGCT   10800

GATGGGCTCC  GTTCCCTCTG  CACATTAGAG  CCATTAAAT   GAAATAATTG  ATCATATTAA   10860

CTGAAATCAC  CTGGCTTATA  GCTCAGGTCC  TAAGAATTGT  TAGTGGCACT  TGGAGCTACA   10920

AAGAGGAGTC  CCCAAAAGAA  ACGATTCTCA  CTTTATTTTG  GCAAATGGGT  GGCTTAAGTA   10980

GAACTGGTCC  TATTCCATAA  CAATAAAAAA  GGAAAAAATA  AATTTTATAT  AAACTTATTT   11040

CCAAGATTTC  TTACCCCTTC  TTGTCAGCAT  TTCAACTTTA  TTTGGTGGAA  CTATCTTTTC   11100

TCAATTATGT  GTGATGTATT  GTGGTCGTGA  ATCATGGTGT  CCTGAACTCC  CTTTGGAAGC   11160

TAAAACGGTC  TGTTGAGGCT  CTGCCTACCA  GCTCTCTAGG  GTTTGTTAAA  GCAAAGAGT    11220

GAGCACTTTA  CTTAAATTTC  ACCAATTATA  TTATCTTCTG  AGACCTTAAA  TGTTGAGTAG   11280

AGGGAAAATA  CAAGTTCAAG  CCTATTTATT  TCAACAATGG  AGCAAGTTGC  TACAGCTAAG   11340

ACCTTTTGAG  GCTGCCTGTT  TCTTCAGGTT  TTCCTTTGAT  TCTCAGAGTA  ACCCCACCTC   11400

AATTTATTTG  AATACATGTA  CTTATGGCTT  AACCAACACA  CAGGTGGTTT  CTTTAACTAC   11460
```

| | | | | | | |
|---|---|---|---|---|---|---|
| AGTGCAAAAA | TCTTCACACA | TACAAACTTT | TTAAAAAACA | ATTCTCAATA | TGAAAAGAG | 11520 |
| AAATCAATAT | AATTGGCTAC | AAATTATTGG | CATCTTTTCA | GAGATTTTCT | CAAGAAAGTA | 11580 |
| ACTGAATTCC | TAAAATTCTT | ATGACTTTGT | TAAAGGACTC | AAAATGAACA | TATATTCTGG | 11640 |
| CTGGGCAGGT | GGCTCATGCT | TGTAATCATA | GCACTTTGGG | AGGCCAAGGA | TTGTGGATCA | 11700 |
| CTTGAGGTCA | GGAGTTCGAG | ACCAGCCTGG | CCAACATGGT | GAAACCCCGT | CTCTACCAGA | 11760 |
| AATACAAAAA | TTAGCCAGGC | GTGGTAGTGG | GTGCCTGTAA | TCCCAGCTAC | TTGGAAGGCT | 11820 |
| GAGGCAGGAG | AATTGCTTGA | ACCCAGGAGG | CAGAGGTTGC | AGTGAGCCAA | GATTGCGCCA | 11880 |
| TTGCACTCCA | GCACGGGCAA | CAGAGGGAGA | CTGCATCTCC | AAAAAAAAAA | AAAAACAAAA | 11940 |
| ACCTCATATG | TCCTACAAAG | CAAGTGATAA | AAATCAAAAT | ATGACAATGG | CTGAGAGGA | 12000 |
| AAGGGAAACT | AGTAGTATTA | AAGAAAGTTT | TTAATGAACA | AATAATGTTA | AGGCGGATTT | 12060 |
| TTTTGTTTGT | TTATTTGTTT | TTGGCCTTTT | TTTTTTTTT | TTTTTTTTT | TTTTGAGACA | 12120 |
| GAGTCTCACT | CTGTCGCCGA | GGCTGGAGGG | CAGTGGCACT | GTGTTGGCTC | ACTGCAACCT | 12180 |
| CCGTCTCCTG | GGTTCAAGCA | ATTCTCCTGT | GCTAAGGCAA | ATTTTTAAGG | ATTATAAATA | 12240 |
| GTAAATATTA | GAAGGGATAC | TGCTTAAAAA | TAAACAATTT | GGATAGCTAA | ATGGTCTTCA | 12300 |
| GACTCTTTTG | ATTGTACAAC | ATGTAAAAGA | ATTTTGAAAA | CTTTAGGCAT | TCCTTTGAAT | 12360 |
| ATTTTTAACT | TGATTTCTAA | AACTTTTCAT | CAAAAAATAA | ATTGTTTTGT | AAATAAAAGA | 12420 |
| AAACATTAAA | CATGTTATAA | GATGAAATAA | GATGAAGAGT | GACTATAATT | AGAATAAGTA | 12480 |
| TTTCATGACA | TAAGTTTATT | TTAATAAAAG | TTCTAACCAC | TTTATTGTAT | CATTCATATC | 12540 |
| AAGTTTTTTA | AATATATATT | GAAATTTGGT | GCTCTGGGAA | AATATGCCAG | CTTCATTTGA | 12600 |
| AAGAATGAGT | TCCTATCCTG | TACTGCTTCA | GTTATTCTGA | ATTCAGAACA | TTCCCACTCT | 12660 |
| GGCCAGTCCT | CTCTTATAAT | AAAACATACA | ATACTGTGCA | TATTCTCAGT | GATTAAAAAA | 12720 |
| AATACACACA | GCAGATAAAA | GAAGAGGGAG | CAGGCAAACC | AAGAGCCAAG | GTGAATGTGT | 12780 |
| TAATCATTAG | CAGGTTATCC | CCAAACCAAT | ATTTGGAAGT | ACTCCTTTGT | TGACAACCAG | 12840 |
| GAAGTGTTTA | CACTTCAGGC | ATTGCACCTA | AATAAAGTGT | GGATGCCTTT | CCTTTCTAAA | 12900 |
| GTGGAAGGAG | GGATATTGTG | GACATAGGCA | CATTCTGAGG | CAATTTTAGG | AAATAAGTTG | 12960 |
| AAATTGATGG | AAATTGAGAA | AGACTTTGGA | AAGTGTTTGC | CTGCCTCCAC | TACCAAAAAG | 13020 |
| TCCATGGAGA | AAGCAAAGTA | AAAGGTCCAA | AAATGAAAGT | CAGCAGAAAC | CAGAAAGATG | 13080 |
| GGCAACAAGG | TTTTACCATA | CAGATAAATA | GAAGAGAGAT | TCTTAGTAAA | GAAAACAAAT | 13140 |
| TGAGGACAAT | CACTAAATAA | AACAAAATCG | AAGGAAACTC | TAAGACCACC | AGCCAAAAAG | 13200 |
| CAAGAGAAAA | TGATTAACAC | CTTGGCACAT | CTTGGTGAAG | GAATTCCAGG | ATAAAGAGAA | 13260 |
| TCCTATAGCA | CCTAGCCTAA | ACATAGCTCT | CCTACAAAAA | GTAGCTGGCT | AACTAGACTT | 13320 |
| CCTCATATTG | GACATCAGAA | GAGACTAGCA | GGAAGTCAAT | ACTGTTTTGA | ATAAGACAAA | 13380 |
| TTGTGGAACA | AAATTTCTGT | TCCCAGCTAA | GTTAATATTA | CAATGTTTTA | AGGCTCCACA | 13440 |
| GTGATCATAA | AGAGTACTAT | GAAATAAATT | CTCAGCTACT | GTGGGACTCA | GAGGCTCATC | 13500 |
| CAAGTACTGC | TCCAAAAAAA | TACTCCATTG | AAATGTTTTG | AGATGAAGAA | GGATAAAGGA | 13560 |
| TGGACATGAA | AAAACAAAAC | AAAAAACACT | TCATTGTCCA | GGGGTATGCT | AAGTGAGCAA | 13620 |
| GAAGTGTCCA | GCACTCAAAA | TTAAGGAGGC | ACTCACTCTC | ATGTGCCAAT | TCTGTTCTTG | 13680 |
| CATGAGCCTA | AGAAAGGATG | CCTCCTTAAA | TATTGCTTCT | TGGGCACCTC | ACTTGCCTCA | 13740 |
| TCTTGGTTTC | AGCCCTCAAA | TTATGTTCAA | ATAACAGTGA | AAAGTATAAT | ACCCAACAGA | 13800 |
| ATGCAAATGG | TATAATTCTT | CTATGGAAAC | TACTCAATGC | AAAATTAATA | CATTAACTGC | 13860 |

-continued

| | | | | | | |
|---|---|---|---|---|---|---|
| AAAAGGTCAG | AGCAAAACTT | CCAGAGAACA | GTAGTGAAAC | CAAGAGTGAG | ATGATAGGAT | 13920 |
| GCCTCAGTGT | GTCTGTTTTC | TTATTATATA | TAAGGAGAGA | GACATGGCTA | GGCATGGTGT | 13980 |
| CTCATGTCTG | TCATCCCAGC | ATTTTGTGAG | ACCAAGGCAG | GAGGATCCCT | TGAAGCCAGC | 14040 |
| AGTTTCAGAC | CAGCCTGAGC | AACACAGCAA | GATCCCTGTA | TCTACAAAAA | AAAAAAAAA | 14100 |
| AAAAAAAGC | TGAGAGTCAA | CAGCCACTTT | TTTACTATAT | AGGTTATTAA | CTTGAGAAAT | 14160 |
| AAAGCATTAA | AAGAACAATG | AATTTGGGAG | CACAACACAG | CAAAATGTAA | TCTGCCCACA | 14220 |
| AAATTGGACT | TAGAGGAGCA | ATTTTCCTCT | AAGCTTTAAC | CTGTTTCATA | ATTAAATGAA | 14280 |
| AAATAAATAA | ACTATCCAAA | ACAAAATTTA | TATGAAGTAA | AGCAAAGGGA | AATAGGACAT | 14340 |
| AAGCTTGATA | AAAGATAAAG | CTAATCAAAT | ATAAATAAA | AAGACAAGCA | GGGCTGGGCG | 14400 |
| CAGTGGCTCA | TGCCTGTAAT | CCCAGCACTT | TGGGAGGCCA | AGGTGGGTAG | ATCATCTAAG | 14460 |
| GTCAGGAGTT | TGAGACCAGC | TTGGCCAACA | TAGCAAAACC | CCATCTCTAT | TAAAAATACA | 14520 |
| GAAATTAGCC | AGACATGGTG | GTGCATGACT | GTAATCCCAG | CTACTCGGGA | GTCTGAGGCA | 14580 |
| GGAGAATCAC | TTGAACCCGG | GAGGCGGAGG | TTGCAGTGAG | CCGAGATCGC | GCCACTGCAC | 14640 |
| TCCAGCCTGG | GTGACAGAGT | GAGACTCCGT | CTCAAAAATA | AATAAGTAAA | TAAATAAAAG | 14700 |
| ACAAGCTATT | CTTAAAATTA | GTAAATGACT | AAGTAGTCTA | ATGAAGGAGA | AAGAAAGCAC | 14760 |
| ACATGCAATT | GGGTCAGAAG | TACAAAGAAG | CTAAAACCTC | AGATATAGAT | AAAATGATAT | 14820 |
| ATTATTAAAA | AGATAGCCTG | ATAAAACAGT | TGAATTTTTG | CAAATATACT | TTAAATAGTG | 14880 |
| TGTAAAATAG | ATGATCCTCC | AGATAACATA | AATGGTCCAA | ATTGATCAAA | GAAAAATATA | 14940 |
| AAACCCCTTA | AAAGACCAGT | AACTGAAGGA | AATTGAGAAA | GTTATCAAAG | TCTCCTCAAA | 15000 |
| ATGGCTTTCA | GCCTGCATGA | TTTTTACAAA | CCAATGCTTT | CAAGCTTTCA | AATAACAACA | 15060 |
| GCAATTATAA | AAATTCCATT | CTAGTCAATC | TTTTTCAGAG | TAATGGGGAA | AAAGGAAAGT | 15120 |
| TCTCCTTTCT | TGTTTTGAA | ATCAGCATAA | GCTCCATATC | CAGACACAAA | AAAGATACAC | 15180 |
| AAAACACATG | TATGCATACA | GAGCCAATCT | CATATATCAG | TACATCAGCC | AAAGTCCTAA | 15240 |
| ATAAACTATT | AGTGAATCAA | ATTCTGTCGT | ACATCAAAAG | AATATTCAAG | GGAAAGCTCA | 15300 |
| ACATTAAGAA | ATACATTAAT | ATAATTCATA | ATATTTAACA | GTCAAGGAGA | AAAAGTAAGT | 15360 |
| CATCTCATCA | TTAGGTAGAT | GACAATAAAC | TATTTGAGAA | AAGTGAATTA | ATTTTCATGA | 15420 |
| CTATTGTTAG | AAACAATCCT | TTAGGGATGG | GGAGGGGAGA | TGAATTAGAA | ATGTTTCCTA | 15480 |
| TCAGTTCACA | ATTGCATCTA | TTCTGAAGCC | ATTAGGAATG | TGAATGGTAA | CTCTTCCTCA | 15540 |
| AACCATCACA | TAAGGAAAGA | TACCCTGAAA | GTCTGACACA | CCGAAGTCAT | CTGTCAGGAA | 15600 |
| TCAATCAGAG | AAGCTGCTGG | GAAAACCTCA | GAGAAGCTGC | TGGGAAAACC | TAGGCATTCT | 15660 |
| GAGTCATCAT | TGTTCTTATC | ACCCGTGGCA | ACTGATGCAA | TTGGAAGCAA | CTGATGCTTT | 15720 |
| CAGGGTCATG | GTTTCTTCAA | AGCCTGAGCT | CATTAATTTT | GCTGTTGAG | AACTTGCAGT | 15780 |
| TTGATCCAAA | AGCTGACAGC | ATCGATTGAC | CCATTGCCTT | CCTTCCTGCT | CTGATACTGG | 15840 |
| AAGTTCCAAC | AAAAGAGGAG | GAGGAACAGG | ACCAAGAAGA | ACATGAAAGC | AGAGGACCAG | 15900 |
| GGGCCGGGCG | CGGTGGCTCA | CACCTGTAAT | CCCAGCACTT | TGGGAGGCTC | AGGTGGGCGG | 15960 |
| ATCACGAGGT | CAGGAGATCG | AGACCATCCT | GGCTAACATG | GTGAAACCCC | GTCTCTACTA | 16020 |
| AAAATACAA | AAAATTAGCC | GGGCATGGTG | GCAGGTGCCT | GTAGTCCCAG | CTACTGGGA | 16080 |
| GGCTGAGGCA | GGAGAATGGC | ATGAACCCGG | GAGGCAAAGC | TTTCAGTGAG | CTAAGATCGA | 16140 |
| GCCACTGCAC | TCCAGCCCGG | GCGACAGAGT | AAGACTCTGT | CTAAAAAAA | AAAAAAAA | 16200 |
| AAAAAAGCA | AAGGACCGAA | GGACCAAGAC | CCCTTCCCAA | CTGCTCCATT | GGTCAAAACG | 16260 |

| | | | | | | |
|---|---|---|---|---|---|---|
| AAGTCAGAGC | AGAAGCTCTC | AAAAGGATGA | TACTTTGAAT | TTGCTTTCTG | TTTTATTTTC | 16320 |
| TACATTCATA | AACGTGCACA | AATCATAAAT | GTACAATATT | CACAAAGTAA | ACACACATCC | 16380 |
| AAGTCAAGAA | ATAAAATATT | TCTAGTACCC | CAGGAGCACT | TCTTAAGTAC | CATCCATCCA | 16440 |
| GCCACAACCC | CCATCCCTGC | ACAAGGGAAA | TCGCTCACTG | ATTTTTAACA | GGACAGATTG | 16500 |
| GTTGTAGCTG | TTTTTAAAAA | GTATTTTATA | AACCTTTAAA | AGAATGTGCG | TTTTGTCTTC | 16560 |
| CTTTAATCAA | TATTGTGCTT | ATGAGACCCA | TTCATCTATT | ATATATTGGG | GTCTGTTAAT | 16620 |
| TCTCATTGCT | ATACAAATAG | ACCGTGGTTT | ATTTACTCAT | TCTTTTTTA | ACAGACAACT | 16680 |
| TCCTGTTCAG | GCTATTACAG | ATAGTGCTCC | TATGAACATT | GTTGTACATG | TTTTATGGAT | 16740 |
| GTATATGTGC | ATTTCTAAGT | AAAATGTTTG | AGTCACTGGA | ATTGTACATT | TAGCTTTAGG | 16800 |
| AGATATTGCC | GAGCAGCTTT | CCAAAGTTCA | CATTCGTAAC | GTATGAAAGT | TCCAGTTGCT | 16860 |
| CCACATGTCT | GGCAACATTT | TGTTTTCCAT | CTCCTTTCAT | TTTATCCATT | AGTTAATTTT | 16920 |
| ATAGTGGTAT | TTCATTGTAG | TTTTGATTTT | CATTTCTGTA | ATGACTAATG | AAGTTGAACA | 16980 |
| TCTTTTTATA | TGTTAAGGAG | CCACTTACAT | TTTCTCTTTT | ATGAAGTCCC | TGTTCAAGTC | 17040 |
| ATTGGCCCAT | TTTTTAGTTG | GGTTGTCTGT | CCCCCACCCT | TTTTTGTTTT | TTTTTTCTCT | 17100 |
| TTTTTCTGTA | CATAATTTGA | CTACCTATTA | TACTATGTCT | TTCTTTTTTC | TTCTACTTCT | 17160 |
| TCTTTTAGTT | TTCTGCAAAC | CCCCTTTCCT | CTTTGTGTTG | TCAATATCAT | GAAGGCAAAA | 17220 |
| TCAATGTTCT | CATCTTAGTA | CCACCCTCAG | GGCCTGACAC | TCTGTTTTC | TGAAAAACTT | 17280 |
| GCTCAAAAAT | ACCCATTGAT | TTGCATTAGG | AGATTCTCTT | CATCTGCTGA | ATTAACCCAA | 17340 |
| GGTTCTTGTC | CAAGCAGTTT | TTTAATAGGA | TTTAAAATAT | GGTGGGAACT | TCTTCTCTAG | 17400 |
| ACATGTTGTG | GCAAAACCAG | AATCAGTTCT | GTGTGAGGAG | ACAAACTAAA | GGATATGTCT | 17460 |
| TAAGTGTTAG | GAGCCAAATT | AATTCCTGTT | AGAGTTGACG | CTGCCTATCT | GAGTATCTTG | 17520 |
| GGAAAGTAAG | AAAAATATGA | AGAAGGTTAA | ATTATCTTTT | TCTACGCTCA | AAAGGAACTT | 17580 |
| CTCTTGTATG | TGATACACTT | CTATGCCTTG | TATGTGATAC | ATTTCTATGC | CTTTTCTCAT | 17640 |
| CTTGTTATGT | CTTCAATATT | TTTCTCCCCC | ATATAAATTG | TCATTTCACT | TGAAAGTGTC | 17700 |
| TCTGTCATCT | CTCTCCAATT | TTCATTATAT | GGTCTAAACT | ATATTGCTAT | CCCTTCTGGA | 17760 |
| AGTGTCTACA | TTGCCTTCCT | TCACATTCAT | TCTTCTCACA | ATACAAGCCT | TCCAGTTCTA | 17820 |
| TCTTCTCTGT | CCTTGATTTC | TAAGTTAACC | TCATTTATTT | AATCTTGTAT | TGGTCATTTT | 17880 |
| CTCATCATTA | ATCTCTTGCA | ATTGGGCTAG | GATAAATAAA | TATCTGTTTA | ATCTGATGGA | 17940 |
| AATATCTGGA | TCTAAATAAT | TTGAAAATGG | TCTATTTTAT | TTTAGCATGT | AAATTTTAAT | 18000 |
| AGAATTTAAT | CACATAAATA | AACGTCTATG | TTTTACAATG | TATAAAAAAT | AATAAAAACT | 18060 |
| TTAATTCTGG | GGATTATAGC | TTTACAGTTC | CGATCGGTGC | TGAGATCTGT | AACATATGGC | 18120 |
| TACAATTCCG | AGCAGATCTT | CTCTGCATCC | AATAACCTGC | CCCACCATGA | AGATATTTAT | 18180 |
| CAGTGATCAT | TTTCACATGA | ATTTTTATTT | ATTTAGTACT | TTCCAATGAG | GAAAATTCAA | 18240 |
| AGGCCACATG | AATTGACTTT | TCAAGTTTGT | CCAGCTGTTG | TCAACCCCGG | GCGCATGCTA | 18300 |
| GAAACCTCTA | AGGAGTATCT | AAAAATTAGT | AGTATCTGGG | TTCCACCCCA | GACCAATTCA | 18360 |
| TTCAGAATCT | CTGGAGTGGG | TCCCAAGTAT | CAGTGTCTTA | TAAAGGCTCC | CCAGGGAAGA | 18420 |
| CTAACACACA | GCCAGAGTTA | AGAACTGCTG | AGTCTATGGT | CAGGAATATG | GAGAGAAGTA | 18480 |
| AAAAATGTTT | AAAAAGTTCA | TGCTCAGTAC | CACATTTAAG | TTTGTAACTT | TATGTCCTCA | 18540 |
| GAGGCGGGTA | AGGGTCCTCT | CTTTGGCCCA | GTCTTGAAGT | TCTGCTTGTC | CAAACGTGAG | 18600 |
| GTAAAAGACC | AGGCCAAACA | TGTTGACTGC | AGCAGACAGG | AAAAAGACAT | TCCTCCAACC | 18660 |

| | | | | | | |
|---|---|---|---|---|---|---|
| AGACTCAAAA | TCCTAGATGT | AAAAAACAGA | GAAAATGATC | AATCTCACAA | GTTCCTTCTA | 18720 |
| CACCAGTTCT | AGTAGCCCTC | CCAGTTGTGT | ATTGCAATGT | TGATCACAAG | GAATATAAGG | 18780 |
| AACAATGTGC | AGTAGTTACT | TAAGAAAGTT | TATGAAACTA | TTGGAAACAA | AATGGCCAAA | 18840 |
| ATGCACATGG | GGTTCTGAGT | TGAGATGGTT | ATTTCTTTAA | ACAAAATAA | AATACACTAA | 18900 |
| TGTTTTTCTG | AAAATTTGGA | TTTCAACATA | TAATATTACT | CATTTAAAAT | TATGCCTAAA | 18960 |
| ATGGCATTGT | GGCATTGTGT | TTGTGTCTTC | TCTGTTTTTT | TTTGTTGTTG | TTGTTGCTGT | 19020 |
| TTGTTTTGTT | TTTTTTGTT | TCTGTATTGG | CTGTTGACAA | CTATCACTAC | AACCCATCTC | 19080 |
| AATTCAACAT | GAGTTCTCTT | TGGTCTTCTG | TGTGACCCTC | CTCAGAAAGC | CCTACTAAGT | 19140 |
| CATTTCCAGC | ATTATAGTCA | CAGTGGATTC | CTAGCAGTTT | AGTCAAATAT | TAACCTGGGA | 19200 |
| ACTTGATCAC | ATAGAAATGT | AGTAAAAACA | AAACTTCTCT | TTGTAAGTTG | GTTCTCGTCA | 19260 |
| GTCCTTCCAT | CCCTGCCTGG | GTCTGTCTTT | TCATCTTCCT | CATGAGCCTG | CATTTCCAAA | 19320 |
| CACCGAGCAA | GCCTCCTTGC | AATGTCTCAC | AGCCGATCTG | TTTCCAGACA | TTAAATTATC | 19380 |
| TTTAAACTGG | CCTAGGACAC | TTTGTTTCCC | TTTTGTGATT | TTTTAAAAAT | TGGATTAGTC | 19440 |
| TGAACATATT | CTTCATGATC | TTCTTTTGCC | CCTCTGTCTT | CGTCTCTTGC | TATTCCTTGA | 19500 |
| CATGTGTCTT | TCATTCTGGT | CATAACTAAG | AACTGTTTCA | TGCTCATGTA | CCTCTAGGAA | 19560 |
| GTCACACGTG | CTGTCTTCTG | CACCGGAACA | GCTCATTTTA | ATCAATCTAA | CATCTATTCA | 19620 |
| TCTTGAGAAA | ATAAGCTTAT | ATTTTCTTC | CTCTGGGAAA | TCTGACCTAC | CAGAGTCTGA | 19680 |
| TTTAGAGGCT | CATGTAAATA | GAGTAATTGT | GTTGCCATCC | AGATCTTTAG | AGCACCGTGT | 19740 |
| GTATCTCCAA | CACCTAAAAC | AATACCTGCC | ACTTGAAGAT | GTTCAATAAA | CTGGCCCAAC | 19800 |
| CTGACTGATG | AGGAATCCAG | TGGCAGTGGA | AGAGATGATT | CCTGCGATGA | GCCCAAATCC | 19860 |
| CCTTGAGATT | CCCATGAGGA | AACTTGCATA | TCTGTGGGAA | GATGATTTTA | TAAATGATTT | 19920 |
| TATATAGAAA | GCCACCTACA | GCTTCTGCAG | CAACTCAACT | TTAATGCAAT | TCAGCTCTAA | 19980 |
| TGGCAAAGTC | ATTTTGCTTA | ATGCAGTTTT | TCATTCACCT | AAAGACATTC | AGGGCAATGT | 20040 |
| CTATTTGCCA | AACCTGAAAT | TACCAATCTA | CCAAGTCAAT | AACCAGGGAG | CAATGCAGTC | 20100 |
| TCTCTGGGAA | CCACGTTTCT | TTACCCCGGC | TGCTCAGTGG | AGAAGCCAGT | TTGTGCAACG | 20160 |
| GGCAGGACAC | AGACTCCAAA | GCCAGACTCC | CCCAGTCCAA | ATCCTGGCTC | TGCCTTTATG | 20220 |
| TGACCATAGT | CACACCATTT | AACCTCCTTG | TGCCTCAGCC | TTCTCCCTTA | TAAAATGGGG | 20280 |
| ATAACAATAG | GGCCTACCTA | ATATAACTGT | GAGGATTAGA | TGTGTTGATA | TATGGCAAGT | 20340 |
| CTTGGCACAG | GAGCTGGCTT | ATTGTGACTG | TATATATATA | TATATATATA | TATATATATA | 20400 |
| TATGGTAGCT | AATATGAACA | ACACCATGGA | AACTTTTCCA | AATCACCTGT | GTGTGGGCCT | 20460 |
| TTTCCCAGCA | TACACAGTTC | AATCTCTGTT | AGGGAAGCTT | GGGAAGGTTT | TTGTCAAAAT | 20520 |
| GATTACTGGC | CAAGATTGGA | AATTGTTGTT | CTAAAAATGC | CACATTTGTT | GTTCTAAAAA | 20580 |
| TGGCCACAGA | CAGATATTTG | TAGTTATTTG | TCATTCTGCC | ATTAGTGCAA | TGTCAGTAAC | 20640 |
| ATTAAAGAGT | TTCACGGCGA | CCACTGAGGT | CTAACACCTC | TGGAGGGGTC | TGGAGGAGGG | 20700 |
| GAAAAAACAG | GTAGAGCTCT | TACCTGGGGG | CGATATCTAA | GGTGTTGATG | ATAAACCCTG | 20760 |
| AGTCACATAG | GTTACTGGTC | CCAGGAATAA | GTATCAGCAA | AATAATGGTT | ATCACGTAAC | 20820 |
| TGGAGGCCAC | AAAGGGCAGG | GCCACAGCAC | ATATTGATGG | AAGGAGGAGC | CCTGGGCAAT | 20880 |
| GAGGACATGC | TGTCAGGGAA | CCCTCTGAGA | CCATGTGCAG | AAAAGGGATT | GGTTAAATGG | 20940 |
| GCCCACACGC | TTATCCTTAC | CAAGAGATGA | AAAGAGCTTT | CGCACAGTGA | TCAATCTGAG | 21000 |
| AAGATTCCTG | GACAAAAGGA | AATCTGCCAG | CTGACCTCCT | AAAATTGTAC | AGCTTGCAGC | 21060 |

-continued

| | | | | | | |
|---|---|---|---|---|---|---|
| AGCAATAAAA | GGCAGGGAGG | ACAGAACTCC | ACTCTGAAGG | AAGGAAGTTT | ATACAGAGTA | 21120 |
| GTTATAGAGA | TACGTTAGCA | CCAAAATTTG | TCAGTTACAC | AGACCAGCCA | TTAACTTACC | 21180 |
| CCCATGATAC | TGTGGGTTGT | TTGGGGGAAA | ATTAGCATCC | TTTTTCACAC | TAAAAGAACA | 21240 |
| CTGTCTCAGA | TAAGAGGGCC | AGAAGCTGCA | TCACTCTGGG | CTCCAGATAA | AAGCAATATT | 21300 |
| AATTTCTTGG | GTTTTTTGTT | TTTGAAACGG | AGTCTTACTC | TGTCGCCCAG | GCTGGAGTGC | 21360 |
| AGTGGCATGA | TCTTGGCTCA | ATGCAACCTC | CACCTCCTGG | GTTCAAGCGA | TTCTCCTGTC | 21420 |
| TCAGCCTCCT | GAATAGCTGG | GATTACAGGT | GCCTGCCACC | ACACCTGGCT | AATTTTTGTA | 21480 |
| TTTTTAGTAG | ATGATATTTA | GTAAACCATA | TTGGTCAGGC | TGGTCTTGCA | TTCCTGACCT | 21540 |
| CATGATCTGC | CTGCCTCGGC | CTCCCAAAGT | GCTGGAATTA | CAGGCATGAC | CACCATGCCT | 21600 |
| GGCCCAGCAA | TATTATTTCT | AAAAGAAGCT | TTGGAATCAG | CTGGTGTGGT | AGTATAGCAT | 21660 |
| AGTGGTTAAG | AATATGGATG | CTGCAGCAGC | TCTATCACTT | AGTATTGTGC | AACCTGGGGC | 21720 |
| AAGTTATCTC | ACCTCTAAGT | GTCCTGTTTC | CACATCTGTG | AAAAGGGAAT | TATAACAATG | 21780 |
| CCTCTCTCAA | GGTCATTGTG | AAGGTTAAAT | TAATGGTTAT | ATGTAAAGCC | AGAATGTAAT | 21840 |
| AGGTAACACA | GAACTGTTTC | TCCTTATTAC | CATTATCATT | TTCGTAGAAG | TATAGGAAGT | 21900 |
| AAACTCACAT | CTCTGATGTT | AACATGGAGC | AGAGTACTGA | TATACGTTGG | TAGGTATGTT | 21960 |
| AGGATGATGG | TGCACAACCA | GAAATGGCTG | AAAAAACCCA | GGAAAATGGC | CCAAAGTGGT | 22020 |
| AGGCATGTGA | CCATCGCCTT | TATGGGGACA | GCTCGTCCAG | GAGAACTGGG | CTGAAAAGAA | 22080 |
| AGATCTAATC | AGCATGAGTA | TTAGAGCAGC | CAAGATGGTG | CCTCTCAGAG | GAGATCCACA | 22140 |
| CCCTGCCCTA | GAGACCTCTG | CATGGGCCAC | AGGTACAAGG | TGTGCACTGT | ACCTGTTGAG | 22200 |
| CCAGTGAGGA | CAGGATGTGC | TCCTTTTCCC | TAACACTTAT | GCACGGGTGA | TGCATGGGGT | 22260 |
| CATCATAAAT | CACTGTGAAC | CATAGGAGAC | AGCAGACACA | GCCAGTGCTA | CCTGGGAAGA | 22320 |
| AGGGATAAAA | TTAGTTTTTA | GGTAGATTTG | TTTACTGGGG | GAAGGAAGTT | TCCTCTGAAG | 22380 |
| TGGCATGCCT | CTCCCTTCTA | CACACTAATC | AATTAATGCT | TATTCTACCA | TAAGGACCTA | 22440 |
| AATGTTCCCA | TTCTTTCTTT | CAATCCTTCT | ACAAACCTGT | TAAAGCTTTT | TAGATATTAC | 22500 |
| GTCTCAAATA | GAAAGCCACC | ATTTGTCAAT | GTCAGAGCCC | TCTGGAGATA | ACAGGAGCGT | 22560 |
| GGCATTGCAT | AGCTGATTAA | TTACTTTAAA | GTCTCCAATG | ATTACAGTGT | TATGTATTTT | 22620 |
| AGGCAGCAAC | TTCTTAATGC | ACACATAAGT | TGTCTTGTTG | CGGAAGATCT | GAATAGTCAG | 22680 |
| GTTTGCAGTC | ATACATACAC | GAAACAACCT | TCCATGAAAT | CATGTGGCAG | GGAAAAATTT | 22740 |
| CCAATGCACT | TACAAGAGAC | AGTATTATTT | GTATTCAAGC | CATACATCCA | TTATGGATTC | 22800 |
| CCAAAAGAAA | TATTTTTGTA | CAATACCTGG | TTAACATGTA | CAAACCAAAA | TAATTAGCAT | 22860 |
| CATTAATGAG | AAAGCCATTC | AGGCCAGGAC | TATATTTAAT | GACACCATTT | GGCTATAAAA | 22920 |
| ACAAATCAAG | TGTAGAAAAT | TGTCTTATTA | TTGGAATTCC | TTATTTGAAG | AACATTCTAT | 22980 |
| GTTAAAAGAT | TCTGAGGACT | AGTTTTCTTT | AAATCCCCTC | TAATTACTGG | ATTCACTGAT | 23040 |
| TCTTTTATTT | TAAAGCTAAA | AATCAGGCAC | CATGATGACA | CCCAAGTGAT | GAAAACATAG | 23100 |
| AATGGATTCC | TTGCCTCAAG | CATTTCACAG | TCTAGTGGAA | AGAAAGGAG | AAATAAATAA | 23160 |
| TTACACACCA | ACATAACCTA | GAGAGGAAAT | ATCATAAAGG | AGAGAATGCC | AGAATCTGAT | 23220 |
| AGGGTAAGCC | CTGGAAGGGC | CCATGGGGAA | GGGAACATTT | GAATTGAACT | TTGCAAGATT | 23280 |
| AACTTGGTAG | AGAACAGGTG | AAAGGCATCT | TGGACAGAAA | TAATAATTAT | AATGAAATAT | 23340 |
| GAAGACACAT | TGAAAATGTA | CTTCACTATC | TTTGACATCT | TAACTGCATA | TAGCAGGCAC | 23400 |
| TTCAGATGTG | GTGGTAGAGA | TTCTGCAGAA | GGTGCTTGAT | ATGGAAGGAC | AAGACTGCAT | 23460 |

| | | | | | | |
|---|---|---|---|---|---|---|
| CACAAGTCGG | TGGGTGCCAT | GTGAATAGTC | AACTCCTCTA | CCTTGTGCGT | GTGGCTTCCC | 23520 |
| AGAACCACCA | GGAAGGTGTT | AATCAGGTTG | TGTGACTAGA | TTAAAAATGA | TACCAACCGT | 23580 |
| TGACATTTTT | TATCATCTTC | CATTTGATAA | AGGACATTTT | CTTTCATATA | GGAAGAATGT | 23640 |
| GGGTGGTGTA | GGTGCCAAAA | TGGATGCTCA | GGAAATGGAG | GCGTTAGGAT | TTAAGAGAAA | 23700 |
| GTGACTCACC | AAAGATGTAC | AAGATAAAAG | GCCAGCTCAA | GGCCTGTGAG | ATTAGTCCCC | 23760 |
| CCACACAGAG | GATGATGAAG | GATCCAAATG | CTGACCCTAA | AGGAAAAAGG | GAGAAAAACA | 23820 |
| CTTATGAAAA | TATCAAAGGC | TGAGACTTCG | TGGCCTCCCT | AAACAATGTC | CCAACAGTGA | 23880 |
| GGTGGCAGAC | TTAGAATTAT | TGGGCAATGA | GAGTATTTAT | TTCTAAAATA | GCTCACAGAT | 23940 |
| TTTCCCCAGT | AAAGTAATAT | GATATAATTA | AAATTAACAA | ATAATAGTAA | CACACTCTCT | 24000 |
| GATTCTTCAA | TGGCTCCTCA | ACACCAATGT | GACCAAATCT | AAATCCCTTA | GTTTGTCACA | 24060 |
| GTAACTCTCT | GCTATCACAG | CCCATTAGCA | TTTTCTTGTG | ATTACAGTTG | CATTCTTGCA | 24120 |
| TGATCTAATA | TGAGGCTAGG | GGCAGGAAAT | GAAAGACTTA | CAAAAATCGG | TAAGATACAG | 24180 |
| CCCCTGCCCT | CAAAGAGCTT | CTGGTCCAAT | TGGAGAGAAA | AATGTGAATA | AAATTGATTG | 24240 |
| TCACTAGTGA | AATGCCATGT | AGGCTTTGGA | AGTCTACATT | AAAAAACAAC | AAGACACATA | 24300 |
| TTTCACAGAG | ACCTATAGTA | AGAAATGCAT | TTTACAGGGT | AACATAACAC | ACACACCAAT | 24360 |
| ATGCATAAAC | ACTTGTACAT | ACAACCACAC | ACATATGCCT | CAAACGATGG | TTTCATGAAT | 24420 |
| CGATATTTAA | CTTTACCATG | TCCAATGCAC | TCCAACAATT | TCTATTCTAT | TCTATTCATT | 24480 |
| TTTTAAAATA | ATGATTTTAA | CCCGCTCAAT | GGATTTTATG | ACTCACTAAT | GGGTCCCAAA | 24540 |
| CTGAAATTTG | AAAAAAAAGA | TGTAAAATAT | AAATATAATA | AAACTACAAT | GTACGTGGAA | 24600 |
| GTATATCTGA | GGATAAATTG | ATAATAATTA | TAAGATTTAG | GAAGTTTTGG | CCGGGCGCGG | 24660 |
| TGGCTCACGC | CTGTAATCCC | AGCACTTTGG | GAGGCCGAGG | CGGGCGGATC | ACGAGGTCAG | 24720 |
| GAGATTGAGA | CCATCCTGGC | TTGAAACCCC | GTCTCTACTA | AAAATACAAA | AAATTAGCCG | 24780 |
| GTCATGGTGG | CAGGCGCCTG | TAGTCCCAGC | TACTCGGGAG | GCTGAGGCAG | GAAAATGGCG | 24840 |
| TGAACCCGGG | AGGCGGAGCT | TGCAGTGAGC | CGAGATAGCG | CTACTGCAGT | CCGGCCTGGG | 24900 |
| CGAAAGAGTG | AGACACCGTC | TCAAAAAAAA | AAAAAAAAA | AAAAAAAAA | GGTTTAGGAA | 24960 |
| GTTTTTACAT | AAGCTATGCA | ATAGGATAGA | TGGAATTTTG | GCACAAGGAA | CAGGGGCAAA | 25020 |
| GAACTTTCCA | GGCATATAAA | CTAACGGGAG | CAGAGCCAGA | GGGAAGTGCA | GTGCAGATCT | 25080 |
| ATGTGGAGAG | CAGCCAATGT | CCAGTGCCAC | TGGAGCCATG | CTTGCACAGG | GGAGTTGAGT | 25140 |
| GGAACAAGGT | TGGGGCCAGA | TGGCTAAGAA | CTTTTGTATT | CATGCAATAA | AGAGGTCAGG | 25200 |
| CTTTACTCTG | TAAGCATGAA | GGAACACATT | GAAAATTCTC | AAGCGGGTGA | GTAAAAATGT | 25260 |
| GCCATCTTTA | TTTTAGCAAG | CTAACTTGGT | TTTGGTGGGA | AGAAGGTTGA | AAGAAACCAG | 25320 |
| TCTAGAAGAG | AGAGATCAGC | AGATAGTATT | TGCAAATAGA | GGAGATGGTT | ACAACTATGA | 25380 |
| TGGAAGGAAG | CAAGAACGCA | GGAGGGTTGC | TTGAGGTAAA | AGTCTGCAGG | ATGCAGCTGT | 25440 |
| GTAGTGGACC | TAGGAGTGAG | AAGCTGGATG | GAATTTTAGT | TCTGCTCTTC | GAGTATATAC | 25500 |
| TCTCAGCACG | ACAGGCTGGG | GAGAACAGCA | ATGATAAAGC | TGTAGAGGCC | TGAGTAGGAT | 25560 |
| CACATACCAT | GGAAAGGCAG | TCTAGCATAG | TGATTGAGAA | TGTCTGCTCT | GGGGCTAAAA | 25620 |
| TCTGCATGGG | CTTAAATCTC | AGACCTACCA | CCTGCTGGCT | ATTTGTATTT | GGGCAATTTT | 25680 |
| CTTAATCTCC | ACCTTCCTTA | ACTCCCTTCT | CTGTAAAATA | AGAATTTAAA | ATGGTACTTA | 25740 |
| TATGAGAGGG | TTGTTGTGAG | AATTAATGAG | CTCATAATAG | AATAGTAAAG | AGCTTAGAAT | 25800 |
| AATACAGAAA | CTTCAAACTC | TTCCAGCCTG | ATTTCTCTCC | TTACCACCTG | GAGCTGTGGT | 25860 |

| | | | | | | |
|---|---|---|---|---|---|---|
| AGCCTTAATT | CTCACTTCAA | AATCATTGCT | AAGATGGTGT | ATATATAGCT | TACTTGATCT | 25920 |
| TTTTCCATGT | GTGCAATTCT | TAAAGGTTTA | AACTTTTTCC | GACAAGGCTT | TTCTGACTAC | 25980 |
| TAAGGCTTTT | CTGACTACTA | AGGCTTTTCT | GAGCTGAAAC | CTAGCTCACA | ATGGTTTTT | 26040 |
| CTACTTCTAA | GCTTCAATGT | CTTTACTGCA | CAGATGCATC | TTTCCTATTT | GTGATGCAAG | 26100 |
| TGTCTTATAT | TGTTGAATTT | TTCAGCAGTA | CTTTTTCTCT | CTCTTCCCCA | AACCATTTGA | 26160 |
| TTCATAGAAG | ATAAGACACA | GTGGGATGGA | ACAGATGACA | AAGCTATGAC | CCATCTGTGC | 26220 |
| ACACTTACCT | GATCCTGCAA | TGGTGGTGAG | CTTGCTTCGT | TCAAGTGGAG | GAGCCCACTT | 26280 |
| TGCCCAAATA | GTAAACTGAC | CTGTCCATGC | CATTCCCTGA | AATGAAAATC | ATTAAGACCT | 26340 |
| TTGATATTTT | GTAGAATTCA | GAAATCTGGA | TCCCACCAAG | AATGAGAAAG | TATCTGGATA | 26400 |
| CCTGGGCCAA | GCCCTGGACT | GTCCGAACCA | TGATGACCAA | AATCACTCCG | AAGTCAGCAG | 26460 |
| CCAGTGGTGT | AAAGAGGGTG | AGAAGGGAAG | AGATCAGCAA | ACCAGCACCA | AGCATTTTTT | 26520 |
| TTGCTCCAAA | TATCCCTGCT | AAATATCCAC | TTGGGATCAG | AGTCAGTATT | ATCCCATAGT | 26580 |
| TGATGGAGCT | AAAGATGATA | CCCTGAGTTT | CTGGGCTCCA | TTGATACACA | GAGGCCTGGG | 26640 |
| GGAAAAATAG | GAAAACTCTT | TGTCAAGAAG | TCCTATTATG | AAAATCTACT | TTACAGTCAG | 26700 |
| AGTTGCTTGA | GGTTAGTGAG | ACCCTAGTAT | AAAATATTGA | TTTTGTTTC | TCTCTATATT | 26760 |
| CTTCCTACCT | TCCCAAATAA | CCAATTATAC | CCCTAATTTG | CTTGTCTTAG | TAGAAGGAGA | 26820 |
| GAAAACAGA | AGAAATGAAG | AAAAGAGGTA | AGAAAATGA | TTATATAGAT | GAATAATAGG | 26880 |
| AAGAAGTAAA | TGGAAGAAAA | CATTGAGAGA | TATTTCATCT | GTGAAAGCAC | TTCCTCTATT | 26940 |
| TTGCTTCTAG | TAAAAGTTGA | GTAACATCTT | GACTCTTATA | TCAAAGAATT | TTTTAAAACA | 27000 |
| CACACACAAA | ACTTACTGA | ACTCTTACCC | AAAATCAGTG | CCTAATTAAA | AAGAAAAGTC | 27060 |
| AAGTTTGGGA | ATCATGGTCT | GCCCTGGCTG | AACTGAGTTC | CTAAAACACA | TATTACAAAT | 27120 |
| GAATAAGATC | ACATTCTTCT | GATATAACTC | AATAAATAAT | TTGAATTATT | TTAAAATAAC | 27180 |
| TACCTAAAAT | TCCTAAATAA | TTACATAAAT | TATATTACCT | GAATATTTAC | CTAAAAATAA | 27240 |
| ATAGATTTTA | AAATAAATAA | ATAAAAAATA | AAATAGATTT | TAAAATAAAA | TAAAAAATAA | 27300 |
| ATGCAATAAG | GCCCCTAAAT | ATCTGGCATC | ATGCTATAAA | GTAGAGAGCC | AAAGAATATA | 27360 |
| AAATATGAAA | TATTTTACCC | ACTCAAAAAA | ACTATAAATA | ATACAAGGTA | TATGATTCAT | 27420 |
| GTGAGAATCA | AGATTTGAGG | ATGAACATAA | ATAAAACAGA | GACTTTGAGA | GGAGAAAATA | 27480 |
| ATAATTTGGG | AAGGTCCCAG | AAAGGAAGCA | ATACTTGAAC | TATCCCTTGA | AAAATGACTA | 27540 |
| TGATTTGTAG | AAAGTCAAAA | AGGAAAATTT | TATCTCATCG | GAAAAAATAG | CAAAAGTGAA | 27600 |
| CTTGTAGCAT | TTGGAAGAAA | CTAACAGGGA | CTCTGGCTTG | CTCAGGGCAA | AAACTTTCCA | 27660 |
| TGGGTCATTG | ATAGCAGATG | TGAGTGTGCT | GAGAAGCAGG | CCCAAATTCT | GAAGGAACAC | 27720 |
| AGCATGTCCA | GTGAACACTG | CATGTTTGGC | AACTTGAAGG | TGTCCAAGAT | TCCTGAGTAG | 27780 |
| TGAATCTACT | CAGTGTGGAT | ATGTAGACGG | GATAATGGAG | GAAAGACTGG | AGACAATAAA | 27840 |
| TTTATGTACT | CATTGTAAAT | AAGCTAGGTC | CAATGTAATA | AAATCATTAA | TCATGAATTA | 27900 |
| TAGGGATGAC | ATGGGAAATG | TACAGTACAA | GATAATTTAA | AGGATAATTT | TTTTAATTGG | 27960 |
| GTAAATTCAT | GGTTTTCATA | TAAATGTAAA | ATAAACATAC | AACAAAGATT | TTATTTAACT | 28020 |
| CATTGATTAA | TGGAGGAAGT | AAGTAAGATG | TTATAACTGG | TTCAAAGGAA | AACTCAAAGA | 28080 |
| ATCACGCATA | ACACAAGCAG | GAAGCAATGC | TGAAATAGAC | TTTAAATATA | CAGCAGAGCC | 28140 |
| TGGCACAGTG | GCTCACACCT | GTAATCCCAA | CACTTTGGGA | GGCCGAGGCG | GGTGGATCAC | 28200 |
| CTGAGGTCAG | GAGTTCGAGA | CCAGCCTAGT | GAAACCCTGT | CTTTACTAAA | AATACAAAAA | 28260 |

| | | | | | | |
|---|---|---|---|---|---|---|
| TTAGCCAGCC | GCGGTGGCAT | GCCCCCTTAC | TCCCAGCTAC | TTGGGAGGCC | GAGACAGGAA | 28320 |
| AATCTCTTGA | ACCCGGGAGG | CGGAGGCTGC | AGTGAGCTGA | GATCATGCCA | CTGCACTCCA | 28380 |
| GCCTGAATGA | CAGAGGAAGA | CTCTATCTCA | AAAAACAAAC | AAACAAACAA | ACAGCAAAAT | 28440 |
| TGGCTAATTC | AACTGGGAGG | TGAGTGGAGA | AAAGTTTTAA | CTGATTTTTC | TCTTGGCAAA | 28500 |
| ATTTATTTGC | AAAGCTATGG | ACAAGAATCG | TTTGCATTTC | TATTGGTTAT | ATAGAATTTA | 28560 |
| CAGGGATATA | AAATTGCTCA | GAAACAATAA | AACAGGCAGA | GAACTGAATA | GGATTGAGTA | 28620 |
| ACCTATAAGA | ATGTGCCCAG | GTAATACCTA | GTTTTTCATT | GAAGACATCA | CATAAACTGT | 28680 |
| TCCATTTTTA | AATTTTTCAC | ATTAACTCT | ACAGTTCCCC | CACCTTATAA | TCATAATAAC | 28740 |
| CTCAATGAAA | TCTTATTTTT | ATTATTGAAG | TAAGCAATGT | CTCAAAGAAA | AATAGTTCCA | 28800 |
| GTCAGTTTTA | ATTTGTCATT | GGAAATGTAT | ACTTCCATAC | TCCACAGAAT | CAAGATCTAT | 28860 |
| GCCTTCCTTT | CAAAGTTTTT | TCTCTCAACA | AAGAGCCCTA | TTTTCCATCA | TACTTACCTT | 28920 |
| TGTATCAAAT | TCCTTGATGG | ATATGCTGGA | GTTATTGAAG | GCATCTGCAA | CAGGCCCCTC | 28980 |
| AGTGGAGGCA | TTAGATAGAC | CTTGCTGCTG | AGTGGTGTTC | ACCATGGCGA | TGATCGCAAT | 29040 |
| GCTCAGACTC | ACACGCTGCG | TTATCATGGT | GAAGTTTGAG | AAGTGCATGA | TAAGAGCCAG | 29100 |
| CCCATAGCGT | AATGAACAGA | AATCTGGACC | TAGACAACAA | CACAGATGTA | TGTAGTGAGC | 29160 |
| ATCCTGACTG | AGACCCCTTT | CTTTTCCTTT | CTCTCACAGC | TCGATCTGAT | AGAACTTTGG | 29220 |
| ATGACACATG | AAGTCTCATT | GTCTTTTTTT | CACCAAAATA | GCCAGCACTA | CAAACCCACT | 29280 |
| TTGTCAAATT | ATTTGGTTGG | CTTCAAGACA | GCGAATATGG | GATCTTATAA | CCAAGTAAAG | 29340 |
| CAAATATGGC | CATCTTTCAA | GGGGATAGGA | AACACATGAT | AAATAGAGAA | AACCCACATG | 29400 |
| TAAGGCATTT | ATGTCATATT | GCTCCAAAAT | GAAGTGAATG | GGGATGACAG | TGGCAGAGCC | 29460 |
| AGTCACATAA | CCTTCTCAGC | GTCAATAAAA | TTCCCTGGGC | TGTAAGTGAA | TAGTCCCATC | 29520 |
| TGTTATGCAC | ATTTGTTTAT | CACAAAGCTT | GAGAGTTTAT | ACATAACGAG | CTGCCTTTGA | 29580 |
| ATTAAGGTAT | TGCACATCCA | AGGATTCTCT | TTTAATACAT | TTGAGAGATG | GTACTTTAAA | 29640 |
| TGAGCACTTC | GACTAATTCC | CTAGTGTAAT | GTCTACTTGG | AAATGTTATT | GCTATGTGTC | 29700 |
| ACTAGGTCCT | GCCTTCACAT | ATGTTCAACT | TAAAAAAAAA | AAAAAACTAC | GTGGGGTGCA | 29760 |
| GTGGCTCACG | CCTGTAGTCC | CAGCATTTTG | GGAGGCTAAG | GCAGGTGGAT | CACTTGAGGT | 29820 |
| CAGGAGTTTG | AGACCAGCCT | GGTCAACATG | GTGAAACCCC | ATCTCTACTA | AAAATACAAA | 29880 |
| AATTACCCAG | GCATGGTGAT | GCATGCCTGT | AATCCCAGCT | ACTCGGGAGG | CTGAGTCAGG | 29940 |
| AGAATCACTT | GAACCCAGGA | GGCAGAGGTT | GCAATGAGCC | AAGATCATGT | CACTGTACTC | 30000 |
| CAGCCTGGGT | GACAGAATGA | GACTCAATCT | CAAAAAAAAA | AAAAAATTA | ATATGTAGAA | 30060 |
| CTATTTTTAC | AAAGCTTGCA | GGTGATGTGG | TGCTGGAAGA | TATTCAATAT | ATTGAAAGGA | 30120 |
| CAAATTTTTT | CTTTAAAAGC | ATCCCCATAA | AATGGAACAA | CCACAGACCA | ATATTGAAAG | 30180 |
| GGTTCCCATG | TGCATGATAG | ATTGGATTTT | TCCTGCTTAT | TTGAAGAAAA | GCACTAAAGT | 30240 |
| GAAAGAAAGA | GAAAACCTGT | GAAGACACAG | ATAAAAATAT | AATGGAAGAA | ATAATTTTA | 30300 |
| ATGGCCAAAA | AAGCTCACAG | ATAAGAGTGG | TGGTCTGGGA | AATAATTATT | TCCATTTTAC | 30360 |
| TGGAGGTTTC | CAAGCTCAGG | AGAAAGAGCC | AGCCGCTTGG | TGAGAATATT | ATAGTAGGGA | 30420 |
| TTCATACATA | GGTTGGTTTA | AAATGACTTT | CCCGGGCCAG | GCGTGGTGGC | CCATGCCTGT | 30480 |
| AATCCCAGCA | CTTTGGGAGG | CCGAGGCGGG | TGGATCACGA | GGTCAGGAGA | TCGAGACCAT | 30540 |
| CCTGGCTAAC | ACGGCGAAAC | TCCATCTCTA | CTAAAAATAC | AAAAATTCAT | CTGGGCATGG | 30600 |
| TGGTGTGTGC | CTGTAGTCCA | AGCTACTCGG | GAGGCTGAGG | CAGGAGAATC | ACTTGAACCC | 30660 |

| | | | | | | |
|---|---|---|---|---|---|---|
| GGGAGGCAGA | GGTTGCAGTG | AGCCGAGATC | GCACCACTGC | ACTCCAGCCT | GTGAGACAGA | 30720 |
| GCAAGACTCA | GTCAAAAAAA | AAAAAAAAAA | AGACTTTCCC | AAAACTTATT | CCACTCCCTA | 30780 |
| GATCCCAGGA | TTTATTGCTT | ATTTGGCTTA | ATTTCTCACA | GATGATTTCA | TGGGGCTAAG | 30840 |
| GAAAAAGCAA | CAGGATCAGG | GGCTGGAGCT | GGCTCCAATG | TTACACTGGG | AGTATCTTTA | 30900 |
| CGAAGGGTCA | GTGTGATGCA | GAGATGTGTA | AATGTGTCGG | AATAAGCTTC | AGCTTATTAA | 30960 |
| CATAGCCTGC | AAACAAGAGC | AGTGGCTTTA | CCTTTCCTGG | TGGCAGGCTT | CCCGTCCATT | 31020 |
| TAGCTTCTGT | GGGAAATGGT | ACCACGCTTT | GTGGTGGAGT | TTCCCTGTGC | CCTGAATCTC | 31080 |
| TTTTACTACG | ACAGTCTTTT | ATCTATGGAG | AGAACATAAT | CCAAAACATA | ATACACAAAT | 31140 |
| AATTTCCCCT | TGTTAATGTT | GCCTCCTCTT | AGCATCAGTA | AAAGTTTTGA | CCCAACACAG | 31200 |
| CTCTATAACT | TACATTTTAT | GGGGCACTAC | TGGTATGCTT | TTGGTTACAG | GATTGTTAAA | 31260 |
| AGGAAATCTG | GCTGTAAGTT | CCAGCTGTGT | GACCTAGAGC | TAGTCATTTA | AATTCTCTAA | 31320 |
| TCATTCATTT | CCTCATCTGT | TCAATAAAGA | TAAGGCTCCT | TTCTTAGTGC | AGCTGGAAGA | 31380 |
| ATTAAATGAA | AAATTGCATG | TACTTTATCA | AACCACAGAG | AAGCATGCGA | AGGTGAAGAG | 31440 |
| TGGTATTGCT | TGTAGCAGAC | CATAAGACAG | GACAATTAAA | CTAAGCTCAA | GAGCTAAGGA | 31500 |
| GGAAGGTTCC | AGAGCGGTCT | TTCCTTTCAT | TCTGATGGTG | TTTCTCTCCC | CTCTGTACCA | 31560 |
| CCAGAACAAT | GTTCCATGTG | CCTTCGAACA | TGAAGGATGA | CATTACATAA | CACTAATATG | 31620 |
| TATTACATTT | AAAAGTTTAA | AATGTTTATT | CTCATGTTTG | CTACACACAA | TGTGGACACT | 31680 |
| TGCTTGGACT | GACAAAGTCT | TCATATCACC | TAGAAAATTA | TAATGAACAG | GGACTAATTA | 31740 |
| CTACAATTGT | GAATAAATCC | AGCTATTGTG | ACAGGCAAAG | AGAATTCATG | GCTCTAAATA | 31800 |
| TGGACATGTT | TAATTTAATA | TTTGTATACT | AATCAAATTA | TCTTTGGGGA | TGCATACATT | 31860 |
| TGTTTCTTTT | AGGAAAAATC | CATATCCTAA | GAATATCATC | AATTTTCCAT | TCATTCCTAA | 31920 |
| ATTGAAGCTT | CTATGACTTT | ATTTTTAAA | TTGCTTAAAA | TCCTTCAAGA | CATCTGAAAT | 31980 |
| TTCTGTGACT | TTAAAAACAC | ATGTATCGGC | CGGGTGCAGT | GGCTCACACC | TGTAATCCCA | 32040 |
| GCACTTTGGG | AGACTGAGGT | GGGTGGATCA | CTTGAGGTCA | GGTGTTCGAG | ATCATCCTGG | 32100 |
| CCAACATGGT | GAAACCCCAT | CTCTACTAAA | AATACAAAAA | CAGCCGGGTG | TGGTGGCACA | 32160 |
| TGCCTGTAGA | CCCTGCTACT | AAGGAGGCTG | AGGCAGGATA | ATTGCTTGAA | CCCAAGAGGC | 32220 |
| AAAGGTTGCA | GTGAGCCAAG | ATCGTGCCAC | TGCACTACAG | CTTGGGGAC | AGAGCAGGAA | 32280 |
| TCCGTCTCAA | AACAAACAAA | CAAAAAAACA | CATATATCAA | ACCTCTATTT | TATCATTCAA | 32340 |
| GGCTTTGCAC | TGTTTTTGCA | CACAAAATTT | AAAAGACTTG | TCCGTACTTT | AAAGATATTC | 32400 |
| ATAATCTGTG | ACCTTAGGAT | GAAGGATTAT | AAAGAAAGGC | ATAGATGAAA | AATTGTGTCC | 32460 |
| AAAAATATCC | TTTGTAGTAT | TACTCATGAC | TGCATAATGT | TAGAGATAAA | TTAACCTAAT | 32520 |
| AATGAGAGTC | TGGCAAGTCA | ATTTGATAGA | TTATTGTGAT | GGAAGCTATT | TTAAAATGTT | 32580 |
| TTCGACAATA | TTGAATTACA | TTAGAAAAAT | GCTAGTACTC | TAGTGTACAA | AGCAGGATAC | 32640 |
| GCTGTGCACA | TCCACATACA | GGAATAGAAA | CTGATTCACA | CAAGTGCCAG | TAATGACTAT | 32700 |
| TTCTGGGTTA | CAAAACAGGA | TGATCACTTC | ATTCTTTGTG | ACTTCTATA | TTACCAAGT | 32760 |
| GATTTTGTAA | ATAATTAGTA | GATACTCATT | TTATATTCAG | AAGTAGCTAA | ATGTATTTAA | 32820 |
| AAGAGCAATA | ATTGGACTTC | ATCAGCATGG | CAAGTATAGT | TTTCTGCTTT | CCAAATATCT | 32880 |
| CTAGAATTCT | GGGAATAGTA | TCTCTCCATC | TAAATTTTGA | ATTTGGGTG | TTTGGAGATT | 32940 |
| TTATTGTTGT | TGTTGTTGTT | GTTTTGTACA | ATGGACCCAA | ATGGAGGCCC | AATTGCTAGT | 33000 |
| AAGATCAGGT | CAGCACCAGG | ACAGATACTG | GTTGTTGCTC | TGCCTTAGAA | GGCCTCCAAG | 33060 |

| | | | | | |
|---|---|---|---|---|---|
| TCTTGCTAAC | ATCTGGATAT | CAGGAGTTCA | GCTCATTGCT | CTACACTCAG | ATCCTAGCTG | 33120 |
| AAGTCATCTG | TGGTCAAACC | CAGAGTTTGG | ACCATTTTCT | ATTTGATTTC | ACTTTTTATG | 33180 |
| CAAGATCCCG | TGGCTTGGCT | GAAGGCAACT | CTTTAACTGT | ACATGCAGCT | GCAATTACTT | 33240 |
| ACACTCCACT | TAAAGCTTTC | CCACCAACTT | CTCCAATCTT | ATAAACACTG | AAAGCTGAAA | 33300 |
| GAGACTCAGA | GATCCTCTGG | CCCAACTGTT | TATTTTATTG | ATAAGAAAAT | TTGCGTAGAA | 33360 |
| AATTTGAAAA | GTTGCCTGAA | ACCACATGAT | GCACAGAGCC | AGCACCAGAT | CCCCTAATGC | 33420 |
| CTAGACTACT | GCTTGTTCTA | CCTATTACAA | CTTCCCCTTT | GTTTCGTAA | TATTTTAATC | 33480 |
| ACAAGCTTAA | AACTCAATGG | GGTAGCTCCA | TTTTGAGGTA | TTATAAAGGA | GAATTTGTAT | 33540 |
| ATTTTAAATC | AAGTTTTAAT | CATTTATTCT | AGAAGGAAGT | TTGATAATGA | AAAATACTTT | 33600 |
| TAGGTTGAGC | TTTGAATATT | AAACATAAAC | ACAACAAAAC | TACTTCTCCT | TGCTCTTTAT | 33660 |
| GTTACTGGAA | TTGTATCACA | AACCCATCAC | TTTAGTTTTT | CTTCCCATTC | TCTGTTGCTG | 33720 |
| TCTAACGAGA | AAGGATGAAA | AGCCCTACTT | AAGTTTTATG | GTTTCAAATG | CTACTTTGAT | 33780 |
| TTTGTATCAA | TAGGTAATTT | CAGTTCTTCG | TTTCCTATTT | TCCTTTGCAT | GAGACGAATG | 33840 |
| CAGAAATCAG | GCTAACATAC | CAAACCATCC | TAAACTGAGG | TCTTTCATGG | TAATGGGAAA | 33900 |
| TGTTTTTCCA | AAATAAGCAC | AGAAGCTAAT | AAAATTATGG | AGGCTGAACA | CTGGCATGGT | 33960 |
| TGATATGTAC | TTAGAGACAC | TGGAATAATT | ATTAACCTAT | TTGCAAACAA | TTGAGAACAT | 34020 |
| GTAACAGTGT | CAGAACCCTT | CCCTTTAAGG | AGATATACCT | CTAAAAAAAA | ATTGTGAATT | 34080 |
| CTAGTGCCAA | AGTTGTAAGT | AGACACAGAA | AAATGAATTG | AAATTAAGTT | AAAGGAAAAT | 34140 |
| GTTATATTAA | AAAAAATTAC | TTGACACAGT | ATAGGTTGAA | TTTGAGAAAA | AAATAAATAA | 34200 |
| TGTAAATATT | ATGGTATACG | CATAAGCAAA | AAAACAGGTT | TTTCCCTTTT | TTAAGTCTA | 34260 |
| GAACTCATGA | TTTTATTATA | ATGGTCGTTA | GATTGCTCTT | AGATTCTCCT | AATATCCAGC | 34320 |
| CTGTCTTGCT | TCATCTCTGT | TAGCCCAGAG | TCCTAGTTTA | CTCAGAGTAA | ATGTTACACC | 34380 |
| TAGATCAAAG | AGCATGAACC | TGCAGTGGGA | GGATATTCAA | GGACTGAATT | CTGCTCTGCC | 34440 |
| ATTCCCAAAT | TGAGTAAACC | AGGTAAAGTT | TCAAAAACTC | TTAGGGCTTT | CACTGTTTCA | 34500 |
| TAGGAAGAAT | TGGGATAATG | TTACTTCACT | GGGCAGTTTG | GAGTGAAAAC | AAAAGTATGA | 34560 |
| GACATGCCTC | GTAAATTGCA | AAGTGTTATA | TGTTGTATAA | TATTCTAGAT | ACTAGCAACA | 34620 |
| GCAATAATAA | TAAACAGTCA | CAATATTGGC | AGTCTAGCCC | TCTCAGATCC | ATAAATACAG | 34680 |
| GCCTACAGCA | AATGAAATGT | ATTTCTATAA | AAGTGCCTTT | GATTGGTTGT | TAAATTGGTT | 34740 |
| TTAAATGTTT | CTTTTTTAAA | GTGGATTCTT | CTGGCCTGGA | ATCCTCAAGA | TGAGTGGGGA | 34800 |
| GGAGTTCACC | AGAAAACATA | GAAGCAATTC | CTTCAGTGTT | AGAAAAACTG | AGGGCCCTCT | 34860 |
| CATCATCTGC | CTATCTTTCT | GAGAAATTGG | TGCTGACCAC | AATGTCCCTG | GGTGCCTTTT | 34920 |
| CTTAGCTGTA | CAATGAGGGC | AACAAGCTAG | GTGATCTCTA | CAAGCGTACA | ATTTTCTTGC | 34980 |
| CTTCAGTCTT | ATTCATAACT | TTGGTCATGT | TCTCCTTTTC | TTTTATTATT | ATTATTTTTT | 35040 |
| TGAGACAGAG | TCTTACTCTG | TCACCTAGGC | TGGAGTGCAG | TGGTATGATC | TCAACTACTG | 35100 |
| CAACCTCTAC | GTCCTGGGTT | CAAGCAATTC | TCCTGCCTCA | GCCTTCTGAA | TAGCTGGCAC | 35160 |
| GCGCACTATG | CATGCGCATA | GGTGCACGCG | CCGCTACGCC | CTGCTAATTT | TTGTATTTTT | 35220 |
| AGTGGAGACA | GGGTTTCACC | ATGTTGGCCA | GGCTGGTCTC | AAACTCCTGA | CCTCAAGTGA | 35280 |
| TCTGCCCGCC | TCAGCCTGCC | AAAGTGCTGG | GATTACAGGC | GTGAGCCACC | AGGCCCGGCC | 35340 |
| ATGTTCTCCT | TTTCCTGAGA | GACCATTTCA | AATTCATATA | GAAGTCTGAA | AAGACTCGTT | 35400 |
| AGCCACAGTC | CCAAACACAA | ATCTTGTCAG | TTCTGATCAG | TATTTCATTC | CACAGCCAAT | 35460 |

| | | | | | | |
|---|---|---|---|---|---|---|
| CCCAGTCTGA | CTAATCACAG | CATCACAGTT | AATACTCACA | GCGTCCTTGG | AGAAATGACC | 35520 |
| ATTGTCCACA | GTGTCCATTG | GTACCAGTGG | CTTCTCAAGC | CTTGCCCTAG | GGTCTTCATT | 35580 |
| GAATCAGTTA | TCTTTTTCAG | AGAGTCTCTT | CATTTTGGAA | TTAGGCAATA | TTACCAGATG | 35640 |
| GAGATCCTTA | TGTTGCTGTT | AATGTCTTTT | CTCTGACTTC | TCCTAAAACT | GTTCCCTCCC | 35700 |
| CTTAATGGAC | CTTTGGTAAG | TTAGTAATAA | TCCTTCTACC | CAAAAAGAAG | AAAAGCACTT | 35760 |
| ACCTTCACCA | TTAAACCAGT | ATTTTAAGCC | CTAGACTATA | AGGCTAACTT | GGAAAAGGAG | 35820 |
| GGAGTTTTCT | GTCCCTTCTT | CCCTTTCAAA | TACTTTTGCA | GATTTTTACA | GGGATAAATA | 35880 |
| GTGAGCCACG | TGGCAGTCAG | ACGGCAACAG | GTTTGGCCCC | ACTTTCTCAG | AAAGCCTCGG | 35940 |
| CTTGGTTTTG | CCGCTTAATT | TTTAACTTCA | TTTTCAAGTT | CTCACTGTTA | GAGTATCTCA | 36000 |
| AAAGATGTCA | TCGTGTGTTT | CTGCTTTGAA | CTGTGCATAC | AACCATTCAG | TCAACAAGCC | 36060 |
| TTTTTTTCTG | AAAGCAAGGG | GGCATGGTGT | GGAGGAAAGG | GCAGGGCTCC | TGAAATCAGT | 36120 |
| GATGGAGTCA | GACCCATATT | CACTTCCTAG | TGTTTTCCCT | GAGCTTGGAC | AAGTCACTGA | 36180 |
| ACCTCTTTGA | ATTGGCTTCC | GCTTTAGTAA | AGCAAGGATT | GTGTTACTGT | ACTCATGGGG | 36240 |
| TTATTGAACA | AATGAAATAC | ATATTCTAAT | TGGTAGTAGC | TCCTCAATAA | ATGAGGTGTT | 36300 |
| CATTCCTCTT | CAGGAGTTCA | GTTAAGTCAG | CTAGATTTTC | CATATGCATT | TGGTGCCCAC | 36360 |
| AGCCTAATGA | ATGTGAACTG | TGACTGCCCT | GGCAACTTCC | CAGGAAGCTG | CCTTGTACCC | 36420 |
| CTCCTTCCTG | TTTCATATCA | TCCATGTCTT | CCCTAATCCA | TTTTCTGCTT | GGCTCCCGAC | 36480 |
| TCTTGGAATT | GTGTCCTATT | TGTAATCATT | AATTTTGAGA | CTGTGGTTGC | TATTGGATCT | 36540 |
| TCCTAGTGTG | ACGCAACCCT | TATAAAATGA | AATGAGAGCC | TTCCCTCTCT | GGCTTATCAG | 36600 |
| CTTCAGACTT | CCTTAATTGA | GTTCCGCCAT | CCTAGTGAGT | CTCACCATAC | TCCCGAAATA | 36660 |
| ACCTGCTGGA | GTAGGCTTAT | CCTACTCAAC | TCCTCAGATC | TCTGTATTTA | ATTCTATTTT | 36720 |
| ATTGCTGTTG | TAGTAAATTA | CCACAACTGT | GATGGCTTGA | AACAACACAA | AATTATTTAT | 36780 |
| TTATTTACAA | TTCTAAAGGT | CAGAAGTCCA | AAATGGGTTT | CACTGAGCCA | AAATCAAGGT | 36840 |
| ATTGGCAAGG | TTGTGCCCCC | TCCAGAGGCT | TTAGGGGAAA | ATCCATTTCT | TTTTCTTTTC | 36900 |
| AGCTTGTAGT | GACCACTGCA | TTTTTTGGCT | CTTGGCCTTT | CCTCCACCTT | AAAGCCAGCA | 36960 |
| GTGTAACATC | TTGAAGTATT | TTTCTCTTAT | TCTGACTCTT | CTGCCTGTCT | CTTATAAGGA | 37020 |
| CCCTTGTGAT | TACACTAGGG | CCCATCTGCA | AAATTCAGGA | AAATCTGCCC | ATCTCAAAAT | 37080 |
| TCTTAACTTA | TTAAACATGT | AAAGTCCCTT | TTGTCATATA | AGGTAATATA | TTTACAGGTT | 37140 |
| CTGGGGATTA | GGACATGGAT | ATCTTTGGAG | GACAACATTC | AGCCTACCCT | TTTGAGGGAT | 37200 |
| AGAGGGGTAG | CAGGAAGAGT | TGAAACAATT | CCTTCCTTTC | TTTATTTAAA | AATTCTGGTT | 37260 |
| ATTGATTTAT | TATAGTTATC | ATGTGCCTGA | TAAGCCAATG | AAAATAGTTA | TAATGGCCAG | 37320 |
| GGGCAGTGGC | TCATGCCTGT | AATCCCAGGA | CTTTGGGAGG | CTGAGGCAGG | AGAATCGCAT | 37380 |
| AAGCCCAGGA | ATCCAAGACC | AGCCTTAGCA | ACATAGGGAG | ATCCCGTCTC | CACAAAAAAA | 37440 |
| TGCAAAAATT | AGCTTGATGT | TGTGGCACAT | GCCTATAGTC | CCAGCTACTC | AGGAGGATTG | 37500 |
| CTTGAGCCCT | GGAGTTCAAG | GCTGCAGTGA | GCTGAGATTG | CACCACTGCA | CTCCAGCCTA | 37560 |
| GGCAATAGAG | CAAGACCCTG | TCAGAAAGAA | AAAGAAAGAA | AGAAAGAAAG | AAAGAAAGAA | 37620 |
| AGAAAGAAAG | AAAGAGAGAG | AGAGAAAGAA | AGAAAGAGAA | AGAGAGAAAG | AAAGAAAGAG | 37680 |
| AGAAAGAGAA | GAAAGGAGAA | CTTTCTTGGC | TTAATTTACC | CAAAAGGTAT | GATATTTTCT | 37740 |
| TAATTTGCAT | AAGGCAGAGC | ATGAGCTGAT | ACCAGTTCTG | GTAGAAAAAG | TAGGTGAGAC | 37800 |
| TGGATCCCCC | AAACAAGAGT | AAATATTTAA | TATAATAAGG | AAAGAGTGGC | CGAAAGTATT | 37860 |

-continued

| | | | | | | |
|---|---|---|---|---|---|---|
| CAATGCCACA | AGTAAGATTC | AGAGTAGATT | TTTCAAACTG | CATAATTTGT | TTAAAAAGCA | 37920 |
| TAATTTTATA | GCTGGATTTT | GCAAGCTCTC | TGAGGGGATC | TTGTTCATTT | TGAGAATCAC | 37980 |
| TATATCCACA | ATTCTTGGCA | CAGTGTCTGT | CCTATGGTGT | GTGCTATGAT | CCAAATGTCT | 38040 |
| GTATCCTCTC | AAAACTCATG | TTGAAATCCT | AACCCACAAA | GTGATAATAT | TAGAAGGAGG | 38100 |
| GGTCTTTGGG | CAGTAGTTAT | ACCATGAGGG | CAGAAACCTC | ATCACTAGGA | TTAGTGTCCT | 38160 |
| TATAAAAGAA | ACCCAAGGAA | GTTTATTCAA | CCCTTCTGCC | ATGTTAGGAC | TCAGCAAAAA | 38220 |
| GATGGCTACC | TGTCCTCACC | AGACACTAAA | TTTGCCAGGG | CCTTAATCTT | AGACTTCCCA | 38280 |
| CCTCCAGAAC | TGTAAGAAAT | AAATTTTTG | TTGTTTATAA | GTCACCCAGT | TTATGATATT | 38340 |
| TTGTTACAGC | AGTCTGAACA | GACTAAGACA | GTACACGCTT | AATAAACATT | AGTTTACTGA | 38400 |
| ATGAATGAAT | TCTTGCATTG | CTTCACCACC | AACAATCAAG | ATCTCTGTAG | CTGGTTTAAC | 38460 |
| CCCCTCACTC | CCAATCATGA | TTTTCATATA | ACAAGTTAA | CTCAGTTAAA | TCAACTCAAT | 38520 |
| AAGGTATACA | TTAAATGAAA | TTAAGAAGT | TGTAACATTT | ATAAACATCA | AGAGTAATGT | 38580 |
| AGAAGAAAAG | TCCAGAGATC | CTTAAAAATT | TAAGCCTCTC | TGGCCTGACA | TTAACAGCTA | 38640 |
| AGGCAGGAAC | AGAAAACCAA | ACACCTCATG | TTCTCACTTA | TGAGTGGGAG | CTGAACAATG | 38700 |
| AGAACATGTG | GACACAGGGA | GGGGAACAAC | ACTCACTGGG | GCCTGTTGGG | GGAGGATGGG | 38760 |
| GTGGGGGTGT | GGGAGAACAT | TAGGTAAAAG | AGCTAATGCA | TGCTGTACTT | AATACCTAGG | 38820 |
| TGATGGGTTG | ATAGGTGCAG | CAAATCACCA | TGGCACACGT | TTACCTATGT | AACAAACCTG | 38880 |
| CACATCCTGT | ACTTGTACCC | AGGAACTTAA | AAAATAATAA | TTTTTAAAA | AACAGCTATT | 38940 |
| TCCAATCAGA | GCAGTTCAAT | TCCATACAAT | TATTATTATT | ATTATTATTA | TTATTATTAT | 39000 |
| TATTATTTTG | AGATGGAGTC | TCACTGTCGC | CCAGGCTGGA | GTGCAGTGGC | ATGATCTCAG | 39060 |
| CTCATTGCAA | TCTCTGCCTC | CCAGGTTCAA | GTGATCCTCC | CGCTTCAGCC | TCCTGAGTAG | 39120 |
| CTGGGATTAC | AGGTGGGCAC | CACCACGCCT | GGCTACTTTT | TGTATTTTA | GTAGAGATGA | 39180 |
| GGTTTCACCA | TTTTGGCCAG | GCTGGTCTTG | AATTTCTGAC | CTCATGTGAT | CCTCCTGCCT | 39240 |
| CGGCCTCCCA | AAGTGCTGGG | ATTACGGGCT | TGATCCACTG | CGCCCAGCCA | ACATACTATA | 39300 |
| TTTTTTTTTG | ATAAATTTTC | TGTATTCTAG | ACATGACATT | AGCTTCCGAC | AATATTAATT | 39360 |
| TATTAAGATC | TGACCCATGA | CATGACTTCA | TAAGAGTTCA | GAGTCCACTG | AATGAGACCA | 39420 |
| CACACAGAGA | CAGACAACTA | GAATGAAGGA | TGATAAACAT | GAACAATACA | AACTTGCACA | 39480 |
| GGTGACTAGA | AAAGAACAAA | TGAAGACTCC | TGCCAACTGG | GGGTATCAGG | GGAAGGCTTC | 39540 |
| CCAGGCAGAA | CAGGGCTGCG | CCAGTCTCCA | TGTGTGGTAT | GAATAAGTCA | GTAATACAGG | 39600 |
| GGAAGCACCT | TCCAGAAAGA | GCAAACCCGT | TGAGGCTTGG | TGTGAGGAAT | AAGAAGTGTC | 39660 |
| CAACATGACT | GGGGATTAAA | GTACAAAGGT | ATAAAGGAAA | TGTGGTGAAC | TGACTGGAAA | 39720 |
| GATAAGAATT | TTTTTTAACA | GTTACTTTTC | CCAATAGTAG | AATTAACTAG | ACAGGAATAG | 39780 |
| AAATGGAAGA | AGTTTTTATG | TTCCCTTAGA | ATGAAAACTA | TACATTTTTT | AAGAATTATA | 39840 |
| TGAACAAGGA | AAATGTGACT | CAAAGGCAGA | AAATGATAGA | ATTTTATTAT | AGGGCAGAAA | 39900 |
| ACAGGATCTG | GCTAAATTAA | ACTAAGTACT | CTACTATACT | ATACCATATG | CTATATTCTT | 39960 |
| GAATGGGAGA | AGTAATACCA | TAAAACTAT | TGATTCTTCC | TAAATTAGTA | AACACATTGA | 40020 |
| GTGAAAATCC | AAGAGGAAGA | AAGAAAAATG | GAAGACAAAC | TGGAAATAGC | CCAAATTTTC | 40080 |
| ATCAGTGGAA | GACTGAGTAC | TTTGTGATAC | ATAGTCATTG | CAGAAAAATA | ACACAGTTAA | 40140 |
| AAAGAATGAA | TCACATCTAT | AACATTTGAC | CTGAATACTT | TCATATAATG | TAATACATTT | 40200 |
| TTAAATGAGT | AAAGCAGATA | CTAAGGACGT | ATAAAGGGAC | TCCATTTTTT | TCTGAATATT | 40260 |

| | | | | | | |
|---|---|---|---|---|---|---|
| AATCAAGAAA | ATTCTATATA | TCTGTATCTT | TGTTTACATA | AGATTGTGTG | AGCCATAATA | 40320 |
| GCTGTTGACT | TGGGTTATCA | GGTTTGGGTA | AACAGTTTAG | TGGTAAAAAA | AAGATGTGTA | 40380 |
| AGACTTGGCC | GGGTGCAGTG | GCTCACATCT | GTAATCCCAG | AACTTTGGGA | ATCTGAGGCA | 40440 |
| GGCAGATCAC | TTGAGGTCAG | GAGTTCCAGA | CCAGCTTGGC | CAACATGGTG | AAACCTCGTC | 40500 |
| TCTATAAAAA | AACTACAAAA | ATTAGCCAGG | CATGGTGGCG | CACACCTGTA | GTACCAGCTA | 40560 |
| CTCAGGAGGC | TAAGGCAGGA | GAACCGCTTG | AACCCGGGAG | GTCGAGGTTG | CAGTGAGGTG | 40620 |
| AGATCGCGCT | ACTGCACTAA | GCCTGGGCAA | TGACAACAAA | ACTCCGTCTC | AAAAAAAAA | 40680 |
| AAAAAAGTG | TAAGACTTAG | CAAAAGGTG | ACCAAAAAA | AGCAACATTT | ATAAACTATG | 40740 |
| GATGTAAAAC | TCTATGTATG | TGTGAGTGTG | TATACATGTG | TGAATATACA | TAGGATACAT | 40800 |
| TTTTGTCTGT | ATGTGTATAT | GTACATACAT | GCATGTATGT | GTATGTGTGT | GTATATATAC | 40860 |
| AAGCTTTTTT | AAAATGTTTT | CAACAATATT | GAATTACATT | AGAAAATGC | TAGTACTGTA | 40920 |
| GTGTACAAAG | CAGGATGCGT | TGTGCACATC | CACATACAGG | AATAGAAACA | GATATATACA | 40980 |
| TACACACACA | CTACACACAC | CCCTATACCT | ACACCAAATA | TACATTGAGA | GAGAGAGATA | 41040 |
| GAGAAAATAG | TAACTAAGGT | AGTTAATTCT | GGCCACAAGG | ATTTTAGAT | GAATCTGACT | 41100 |
| TTCTTCCTTA | GGTTTTTTTT | GTATTGTTTA | AAGTTTCACA | CAAATAGCAT | TTATTTACTG | 41160 |
| TATAATCATA | AAAGGCAAAA | ACCTATTTTG | ATTTTAGGAA | AACACAAAGC | ATCCAAACCA | 41220 |
| AAAATCTCAA | CTTAGGAAAT | AGCGGGAAAT | CTAGGGAAGT | CAACAGGACC | AGGTCATGAC | 41280 |
| GGTCTTTTAT | GCAATGTCCA | GGAGCTTGAA | CTTATCTTG | TCGTTCCTAT | ATTTCCTCAA | 41340 |
| AACAAATGTG | TGTGGACGCA | GAAATGGAAA | TGCACAGCAG | TGCACTGAGG | TCACAGGAAA | 41400 |
| AATACAAAAC | AGTTTTCTG | AAGTACTAAC | TTCACTCAAA | ACTTCGGGAA | ACATTTTAAA | 41460 |
| AATGGTTTTA | AACAAATTTG | ACTAAATTTG | ACAAATTTAG | TCAAATGCAA | AATTTTCATT | 41520 |
| TTTAAAGGA | AATAAATTTT | AGAGGAAAAA | ACAGATGTGA | AAAAGAATAC | ATGAAATAGT | 41580 |
| ACATGAAGGA | ATACATGCAC | GTGGCATACA | CTTGAATCCA | TGTATATGCC | AGGTTTTCTT | 41640 |
| GTGTTGCACA | CAAGACCAAC | TCTGAAGTTA | AAGATAACCC | AGTAGAAAAA | ATTAAATGAT | 41700 |
| GGGGAGTAAT | TAAAATGTTT | TCAGCAGGAG | TAGGACATGA | TTTTTATATT | TAGACTGTTT | 41760 |
| AGTCGGCTAG | TTATGTCTGA | CGGATAGAAG | TGAGGACACT | CCTAATTGAA | AAGTAAGTGC | 41820 |
| TACTAAGAAA | CTCAACGTGG | GGGTCATAGA | ATGAAGCCAG | ACTTTTGTTC | CCAAGCAGGA | 41880 |
| GACAGATGCA | GATAAGAGGG | AATGAAGATG | AAGTAAGGGC | TGAACCACAG | AAGCTTCGCA | 41940 |
| TCATAAGTCA | TTGTATTTCT | CTGAGTGAAC | ATCATAGAAC | TTATTTACTA | TCTGGTCACA | 42000 |
| AAATGCCACT | GACATGAAAA | GAAATCGGGT | TGAAATGGCT | CTAGACCAAG | ATTCCCAAGA | 42060 |
| CATCAAGAAA | TCACCAAAAG | TTGCCTCAGG | TTCACAAAAA | AAGATATTCC | AAGGGAGTTC | 42120 |
| TCCAAGTAAG | TAAACACTCA | TTATTTCTAT | AAGGCTTAGG | CCACAAGACC | TTGGCTGAGA | 42180 |
| CCCCTGTCTC | TGTGATCTGG | TCTGTACCAC | ATTGGAAGGG | CCATGACTGA | TTTCTACCTA | 42240 |
| GACATTTAAG | GCTGAACGGA | GGCTGAAGAA | CCTCTTGCTT | GCTTTCCCAT | AGACTCACAT | 42300 |
| CTGATAACAG | CCCTCATCTT | AGGCCCCAGA | GGGCAAGAAG | AGGTTAAGAA | GGATCAACCA | 42360 |
| AAGGTAAAGT | ACACCAAGAA | AAGAGCAGCT | CTTTGGTTAG | AATTTTAAGA | TAAAGAGAGA | 42420 |
| CACATAAAAG | CTACTGTTGA | AAAATAACAG | AAGGAACAAC | GTTTTATCTA | ATCAATAGAT | 42480 |
| GGAACAAGAC | AATAGAGGAC | CATCTCAACA | ATAACCTAGA | ATACCATGGA | AGACAGACAT | 42540 |
| AAATCATCTG | TATTTGTCCT | GCTCAAGACT | TGCCATATGC | CAGGTATGGT | GGCTTATACC | 42600 |
| TATAATCCCA | GAACTTTTAG | GCTAAGGCAG | GAGAATTGCT | TGAGCGCAGG | AGTTCCAGAC | 42660 |

```
CAGCTTGTCT CTACAAAGTT CTCTGGGGGT TTTTTTTCGT TTGTTTGTTT TTTAGGCAGG    42720
TGTGATGGCA CACACTTGTG GTCCCAGCTA CTCAGGATGC TGAGGTGGGA GAACAGATTG    42780
ATTCTGGGAG GTCAAGGCTG CAGTGAGCTA TGATTGCTCC ACTGCACTCC ACCCTGGGTG    42840
ACAGGAACTG CAGACAGCCT CTAGAAGTTG AATCAGCCTC TACCAAGAAG CTTCTACCGG    42900
TGCAAAGAAC TGAATTTTTC AACAAACCTG AGGGAGCTTG GAAGTGGAAA TTTCCACAAT    42960
CAAGCCTCTG ATGAGAATTC AGACTCAGCC AACACCTGGA TTGCAGCCAC ATGAGGCTTG    43020
AAGCAGGGAA CCCAGTTAAG CCATGTCAGA ACTTCTATCC ACAGACCTTA GGTAATAATA    43080
AATGTGTGTT GCTTTAAGCC ACTAAGTTTT TGCTAATTTG TTTTGTAACA ATTATATATA    43140
ACTAGTACAC ATGAATAGTA GAATCTAATA TCAGCCATTG ACTTCAATGA AGGAAAAAAC    43200
AGATGTGAAA AAGAATACAT GAAATAGTAC ATGAAAGAAT ACCTGCACAT GGCATACACT    43260
TGAATCCATG TATATGCCAG GCTTTCTTGT GTTGCACACC CAGACCAACC CTGTAGTTAA    43320
AGATAACACA GTAGAAAAAC TGAAGAGTTA CTGAGAGTAA TTAAAATGTC TTAAGCAGGA    43380
GTGGGGCATG ATTTTTATTT TTAGACCGTT TAGTCTGCTA GTTATATCTG ATGGTTAGAA    43440
GTGAGCCTAT CTCTGGTCCC ATGTTCTTAG AGAGAGTACT TTTATCTCTT TATCCATCTA    43500
ACATCTCTAA TTTATGTAAC ATCCCAAGTC CTCATTAATC CTGTGTTATT GCTGTTGGAA    43560
GTCCATCTAT CCCCTCAAGA ACAGAGCCTG AAATTCCTCT TTGAAAAATT TCCATTCATC    43620
ATAATCTCAA ATTTCTCCAA TGTCATTTTC CACCTAAATT TCATGTGTGA CTTGAATCTC    43680
AAGACTATTC ATCTGCCCCA GGTATCTGTT TGATGCCTGG ATATGTCTGA ATTATTATTA    43740
TTGTTATTAT TATTATTTTT TTTTAAATG GAGTCTTGCT CTGTCACCCA GGCTGGAGTG    43800
CAGTGGTGCG ATCTCAGCTC ACTACAACCT CTGCCTCCTG AGTTCAAGTG ATTGTCCTCC    43860
CTCAGCCTCC CCAGTAGCTG GGATTACAGG TGCCTGGCAC CTCGCCCAGC TAATTTTTTT    43920
GTATTCTTAG TAGAGATGGG TTTTCACCAT GTTGGCCAGG CTGGTTTTGA ACTCCTGACC    43980
TCAAGTGATC CACCCACCTC AGTCTCCCAA AGTGCTGGGA TTACAGGTAT GAGCCGCCAC    44040
ACCCAACCTT AGACCTCATC CTACCCAGCT CACGTGTCTT TTAATCCTTT AGCTGAGGTT    44100
GTAGTTTTAA CTTATTGCTG CTTGAACCTA TTTCAATGCA AAAGTTCTAA AAGAACTCAG    44160
CCACCAAAAT TCCCTTGATT TGCTGCACTG TACCAAATAT TAGTCTTAAT GAAATACAAG    44220
ATTTGTTTCA GGATCTCAAG CCCAATATTT TCAACTGTAG GCTTCCCAGT ATCCAAGGTT    44280
TACGCAGGAG ATTGGCAGTG GGTACATTCC CAGGGTCAGT GGTTTTATC CAGGAAGGAA    44340
CCTCAGAATC ACCTGGGGAA TTTTAGCAAC ATACACACCA GTGTTCTCAG GAGTGAGGCT    44400
CAGGTATGTG GATGGCAACA ATACTTCCCT TATCAAAAAG CTGCCACCAC ACCAGACAAA    44460
TGAAAACTGC TCTTTAATTA TACAGCTTGG CCTTACCTAA TGGTTCTCAA TTTTGGATGG    44520
ACATTCAAAT CACAAGGGTA GTTGGTTTTT TTGTTTTGT TTTGTTGAGA CAGACTCTCA    44580
CTCTGTCGCC CAGGTTGGAG TGCAGTGGCG CCATCTCGGC TCACTGCAAC CTCCACCTCA    44640
TGAACGTAGT TTTAAACAGC ACTAGTGCCT AAACCAGACT CCAGAGATCA TGATCCCTAA    44700
TCCTATCCCT ACCCTGCGGT ACTCATTCTG AGATATGCCC TGGGTAATAA GAATTTTAGA    44760
AGGTACTCAG GTGATTCTAA TGTTCAACCA GTCTGAGAAC CATTCGCAGA CTTCATATAG    44820
ATACTTTATT CCAAACAGCT GAGCTGGACC ATAGCTAGAA GAAGGAATAG AGATGAATGA    44880
GAGTTCATAT TTTCCATAGA AAGCCGCTGC CCTCTTCTAA ATGTGAATGG AAGTTCTGGA    44940
GACCCCTATC CTAAGGTAGA CAGATGACAG ATACACTGGA GAATGCTGAA GGAAGCAGAT    45000
AGGAGTCTAG GCTTTAGACC ACACCTTCCA AGACGTACTA CTCATGCCTG ATGAAGTATT    45060
```

-continued

| | | | | | | |
|---|---|---|---|---|---|---|
| ACCAAACATA | CCCCTGGGCC | AATAAACAAA | GCAGGAGCAA | ATGTGTTTGT | GTGTGTATAA | 45120 |
| CTTTCTACAC | AAAATACAGA | AAAAAGTGAT | TCAATGTTCA | GCATAAATAA | AATTTTGTGT | 45180 |
| TTTAGTATTG | TTTTATTTCA | AAGTACATCT | TGGTGAGAAT | GCATTATTTT | GAACTGGATA | 45240 |
| AAAGCCCCCC | ACTACTGAAT | CCCAGGTCTC | TCTATGAAGC | CTGAATAGAG | GCACTGTAAC | 45300 |
| TCTAATGGCC | AAAGGGCTGG | CCTGGAAATT | CTCCCTTCAG | CTGCAAAAAG | AGAAAAGAA | 45360 |
| TAATCCAAGC | AAACAAACAA | AACAAAGAAA | TGAGCAAACC | ACTACAACAC | AAAACCCTTG | 45420 |
| GGATGAGATG | AGTACTAGAC | TGGGAAAGTG | ATAGCTCTGG | TATTCATGTG | TGTGTGTGTG | 45480 |
| TGTGTGTGTG | TGTGTGTGAG | AGAGAGAGAG | AGAGAGAGAG | CACATGAGAG | CACACACAAG | 45540 |
| ACCCTATAGA | GGAACCAAGT | AGCTTATCTT | CTTCCTTGGA | TTCCTCTATC | TCATAGCCTA | 45600 |
| GAAGACATGG | GGTGATCCTA | GCCCCTGGTA | GTGTAGGACA | AGGTAGAGTG | GGACTGTGGT | 45660 |
| TTTAAAATAC | TTTTTAGACC | GGGTGTGGTG | GCTCATCAAC | ACTTTCGGAG | GCGGAGGTGG | 45720 |
| GTGGATCACC | TGAGGTCAGG | AGTTTGAGAC | AAGCTTGACC | AACATGCTGA | AACCCCGTCT | 45780 |
| CTACTAAAAA | TATAAAAATT | AGCTGGGCAT | GGTGGCAGGC | ACCTGTAATC | TCAGCTACTC | 45840 |
| AGGAGTCTGA | GGCAAGAGAA | TCGCTTAAAC | ACAGGAGGCA | GAGTTTGCAG | TGAGCCAACA | 45900 |
| TCATGCCATT | GCACTCCAGC | CTGGGTGACA | AGGGTGAAAC | TCTGACTCAA | AGTTAATTAG | 45960 |
| TTAATTAAAA | TAAAATACTT | TTTTATTTGG | GGCTGGGTGC | AGTGGCTCAT | GCCTATAATT | 46020 |
| CTAGCACTTT | GGGAGGCCAA | AGTGGGAGGA | TCACTTGGGG | GCAGGAGTTT | GAGACTAGCC | 46080 |
| TGGGTGACAT | AGCAACATGC | CATCTCTACA | AAAATTTAAA | AATAAAAAT | TAGCTGAGTG | 46140 |
| CAGTGGTGCA | CACCTGAAGT | ACCAGCTACT | CATGAGCCTG | AGGTAGGGGG | AATTACTGGA | 46200 |
| GCCCAGGAAG | TTGAGGCTGC | AGTGAGCAAT | GATTGGGCCA | CTGAGCTACA | GCCTGGTGAC | 46260 |
| AGAATAAGAT | GCTGTCTCTA | AAAACAAAAA | ACAAACAAAA | AAAACCCAAA | AACCTTCTTA | 46320 |
| TTTTAAAATG | ATTTCAAACA | TATAGAAAAA | TCAGAAAAAC | AGTACAAAGA | ACACTCATAT | 46380 |
| ACTTTTTACC | TAGATTGTTA | ATATTATACA | TTTGCTTTTT | CTCTACCTAT | CCATTTATTT | 46440 |
| ATATGTCTTT | ATATCTCTTT | ATATATATAT | ATACTTACTG | AAACATTTGA | AAGTTGCAGA | 46500 |
| TAATCATCTT | CCTATATTAC | TCAATACTTT | ATCTTTAAAT | TCAAATTCAA | ATTTTACCAG | 46560 |
| CTGTCCCAAT | CATGTCTCTG | ACAACACTTT | TTCCCCTCAA | TCCAGGATCA | CAAATTGCAT | 46620 |
| TTGGTTGCTA | TCTCTTTAGT | CTCTATTAAC | CTGGAACAGT | TTCCTGGCCT | TTCTTTATCT | 46680 |
| TTCATGATAT | GAAATGACAA | TGAATTTTA | AAGGTTAGGT | GTTTTGTAGA | TTAGTTCAGT | 46740 |
| TTTAAAACTT | CACAACAAAG | TGCCAAAGAT | GTCTTGGCAG | CAGTGCTCAA | AACAGGTTGG | 46800 |
| AGATGCATAG | GAGCCACAGA | GAAGGGTCTG | GTTCAAAGGC | CAGTGGTCGT | CTCATTACAG | 46860 |
| CACTGCTCCA | TCAGGTCTAG | GTCTGGAGAC | TTGGTAGCAC | GTCTATGGCC | CCAAAGTGTG | 46920 |
| TAGAGAATGT | TGAGAATTGC | CTAGGGTGGC | AGACTTAGAG | GAAGAAAGGT | TGGTATGAGG | 46980 |
| CCTGTCTAAA | ATTGAATTTG | GCTATAGAGT | TATGGAAGGG | TTTTAGGCCA | TGTCTGGGTG | 47040 |
| GAATCAGATT | CAGTCAGCAA | GTAAGGGGTC | TTTGGGAGGT | GAGCTTAGGC | TGTCTGGGCC | 47100 |
| CCTTCGAGGA | GGGCAGATTT | TATGGGGAAG | GGCTCTCCTA | GAAGAACCTA | GTTTAGGATG | 47160 |
| AGCAAATCAC | GCAGGTTCAT | TCTCCACTTT | ACCCTAGCAC | TTCCTAGGCT | CAGTGGTGGT | 47220 |
| TTTGAACTTT | TCCCATCCCT | GCAATTACTC | CATAAAGGGA | ATGTGCAAGG | AAGAGGGGAG | 47280 |
| GAAAGAGATG | TGAGTTCTGC | CAGAGGCTTC | ACTGTTTCAT | TCCCAGATTT | ATTTGAAACC | 47340 |
| AACCCTCCTC | CTGTACTTCA | TGCTCTCCAA | GCTCATGGTC | CTGGAACTTC | ACATTTACAT | 47400 |
| AATACGGAAT | TTTTTTTATT | ACCCTTGATC | TTTATGCATG | CAATCTTTCT | GAACACCCTG | 47460 |

| | | | | | | |
|---|---|---|---|---|---|---|
| GACCCCCTCC | TTCTCTTGGT | GACCTTTTCC | TTCTCCAAAA | CATGGTTCAC | CAGTTATTAC | 47520 |
| CTCTGCAGCA | GTGGTCCTTC | CAGGAGTTGC | TTGCTGCTTT | GTTCTTCTCT | CAGCCTCAAC | 47580 |
| ACTTTTTCTT | ATCTTGTTAC | AGCATTTAGA | ATGTAATGTT | TTGTTTTGTT | TTTAAAACAC | 47640 |
| ATCTTGGCTT | TCTGGAAACT | TATATAGAAA | ATAATTTTTT | TTCCCTCAAT | AGATATATGG | 47700 |
| CTAGGGTCCA | GCCTAATGTC | TGCCATAGAG | AAGCCTAATG | TCCAGCCTAA | TGTCAATAAA | 47760 |
| TGTTTATTGT | GGGCATAAAG | GAATACATTT | TAAAATAATG | GAGTGTTTAG | GTAAAATTAG | 47820 |
| GATTATTAGC | TTGAGTCATT | TAAAATCATC | CACAAGAACC | AGATCAAATG | TACATGTCTT | 47880 |
| TAATACTGGT | GAAAGAAGTA | GTTACGCTGT | CTTAAAGGCA | AAACGATATG | GACATAGCCA | 47940 |
| CCAGAAATAC | AAGAGTGCCA | TCTCTTGGTA | AACCTGTTAG | CAGACAGAGA | AGACACTGAG | 48000 |
| AAGCCATGTA | AAATATACTT | GATAATGTGT | CTCTTATGTA | GGTTATGTAA | AATGTGGAAG | 48060 |
| AAAGATGGAA | ACAAAATTGA | GAGACGTGGT | TATGGCATTT | TCCAGGAAAA | TTGGAAAATA | 48120 |
| TTTTCTCCTA | ATAATTCATG | CAAAATGTAA | TGATATTTTT | TAATGCAGAA | GAAACAGTG | 48180 |
| TAACAAAAAG | CATTATAATT | ATGGCAAATT | GTTGAATGCT | TTCTCCACCC | CTGCCCTTTC | 48240 |
| CACTCAGAGT | AGGAATGAAA | TAAGGATGTC | AGTTATCACA | CTTTATGTTC | AATATTATAT | 48300 |
| GGGAGATGCT | AGCCAGTGTA | CTGTGGAAAG | AAAAATAAAT | GTTAATGTTA | GATGTTAATG | 48360 |
| GTGTAAATAT | TTCAATTGAA | AGGCAAAGAT | TGTTAGAATC | GACTTAAAAA | TGCAAGAACC | 48420 |
| AAACACGTTG | GCTAGAAGAG | AAACATCTTA | AATATAAAAA | CACAGATAAC | TTGAGAATAA | 48480 |
| ACATATTAAA | ATATATACAC | TATGCAAACA | GAAAGCATAA | AAAGACTAAA | ATGGCTATAA | 48540 |
| TAATAACAGC | TAAAATAGAG | TTTAAGACAG | AGAGTGTTAC | CAGAGACAGA | GTGATATTTT | 48600 |
| GTATTGTTAA | AGGAGTCAGT | TGCCAGCCTG | GCCAACATAG | AAAAACCCCA | TCTCTACTAA | 48660 |
| AAATACAAAA | ATTAGCCAGT | CATGGTGGTA | TGTGCCTGTA | ATCCCAGCTA | CTCGGGAGGC | 48720 |
| TGAGGCATGG | GAATTGCTTG | AACCCAGGAG | GCGGAGGTTG | CAGTGAGCCA | AGATCACACC | 48780 |
| ACCGCATTCT | ACCCTGGGTG | ACAGAGTGAG | ACTCTGTCTC | AAAAAAATAA | AATAAAATAA | 48840 |
| AAATGCCGAG | GTGGGCGGAT | CACCTGAGGT | CAGAGGTTCG | AGACCAGCCT | GGCCAACGTG | 48900 |
| GTGAAACTCT | GTCTCTAATA | AAAATACAAA | ATTAGTTTGG | CATGCTGGCA | CATGCCTGTA | 48960 |
| ATCCCAGCTA | CTTGGAGGCT | GAGTCAGGAG | ACTCGCTTGA | ACCCAGGAGG | TGGAGGTTGC | 49020 |
| AGTGAACCAA | GATTGTGCCA | CTGTACTCCA | GCCTGGGCAA | CAGAGTGAGA | CTCCATTTCA | 49080 |
| GAAAAAACAA | AAACAATGAC | AATAGAAAAG | TGTCATTTCA | TCAAGAAAAC | ATAATAATCA | 49140 |
| TAAATGTATG | ATTCTAACAA | CAGAGTTTCA | AAATACATAA | CGAAGTTTTA | AAATACATAG | 49200 |
| CAAAATGTCA | TAACAGAGTT | TCAAAATACA | TAAAGTAAAA | ATGGAAAAGA | AAAGACAAAA | 49260 |
| TAGACAATTC | TACAATCACA | TTTGGAGAGT | TTAACACCCT | TTTTTGGTA | ATGATGCAAT | 49320 |
| AACTAGACAA | AATATCAGTA | AAGACACAGA | AGATCTGAAC | AATCCTATCT | ATTATCTTGA | 49380 |
| GCTAATTGAT | TTATAGAACA | TTATACACAA | TATCTGCATG | CACATTTTGC | TCAAGTACAC | 49440 |
| ATGATATATA | CATCATGATA | GATCATATTC | TTTTTTTCTT | TTATTTTTAG | TTGACATATA | 49500 |
| ATAACTGTAC | ATATATACGG | GATAAAGAGT | GATATTTTTA | TATGTGTACA | CAATGTGTAA | 49560 |
| TAATCAAATC | AGAGTAATTA | GTATATCCAT | CACCTTAAAC | ATTTATCATT | TATTTTGTTG | 49620 |
| TGAGTATTCA | AAATTCTTTT | CTAGCTTTTT | GAAAATATAC | AATAAATGAG | AGTTAACCAT | 49680 |
| ATGCACCCTA | CAATGGTGCA | GAACACCGGA | ACTCATTTCT | ACAATCTAGC | TGTAATTTTG | 49740 |
| TCACCATTAA | CCAACCTCTC | CCTATCCTCC | CCTCCTTGCT | ACCCTTCCCA | GCTTCCGGTA | 49800 |
| CCCACAGTTC | TGTTCTCTAA | ATCCATGAGC | TAAAAATTTT | TCTCTACTTT | CACATATGAG | 49860 |

-continued

| | | | | | | |
|---|---|---|---|---|---|---|
| TGATAACATG | TAGTATTTAT | CTTTCCAATC | CTAGCTTATC | TTACTTAACA | TAATGTTCTC | 49920 |
| CAGTTTCATC | TACGTTGCCA | CAAATGACAA | GATTGCATTC | TTCTCATGGC | CAAATAGTAT | 49980 |
| TTCATTGTGT | ATATATGCCA | CATTTTCTAT | CCATTGTCT | GTTAATGAAC | ATTTAGGGTT | 50040 |
| GACTCTATAT | ATCAGCTCTT | GTGAAGAGTG | ACGCAATAAA | CATGGGGATG | TAGGTGTCTC | 50100 |
| TTTGTATACT | GATTTCCTTC | CCTTTGGATA | AATAGCCAGT | AGCAGATTTT | CAGCCTCATC | 50160 |
| TGGTAGATCT | ATTTTTAGGT | TTCTGAGAAA | CCTCTGTTGT | CAGTAGGCTG | GTTCAGATTC | 50220 |
| TTGAATTCCC | TGCACAAAAG | AATTTGAAAG | CCAGTCCAAA | GTAAAAGTAG | GCAAAGGAGT | 50280 |
| TTATTGCAAG | GTGAAAGTAC | ACGCTGATAG | CAGAGTCAGG | GTCGGCTACT | TCAGCACCAA | 50340 |
| TTGACACTGA | AGAAACTCCC | GTTATGGGAG | TCCTACGTGA | TTATCCATGA | GGGGTGGGA | 50400 |
| ATGGGCATTG | TTGTTAAATA | TGTTTTGGGT | GGTCTCTTGA | ATGTGCATGC | AATATTGCCA | 50460 |
| TACACGCTAG | TACATACATC | ACATGTATTA | TTAGCATTTT | AATTCTCTAC | CCAAGGGTGT | 50520 |
| GTTCTTACT | ATTAAAATGA | GTATATGTCA | ACCTGAGAAC | ACAGCTTGTG | GGTTTCTGCA | 50580 |
| CTTGCACGAA | CTTAGGGATT | TTCCCTCCTG | CTCTTCTACC | TCCTTGACTG | AGGATATTCT | 50640 |
| AACCACTAGC | CCCAGATGCA | GTTTGTGTAA | TGTCAAGAGA | TTTGTTCTCT | CCATCAATTT | 50700 |
| GACAAGTTTC | TTGTTTCCTT | TCAAGGGAGG | CTGTGACCAC | CCTATGTAAC | CTACCTCACT | 50760 |
| TCCATACTAT | TTTGCATAAT | GGCTATGCTA | ATTGACATTT | CCACCAGTGG | GACATAAGAG | 50820 |
| TCCCCTCTTC | TGTACATCCT | CACCAGCATT | TGTTATTTTT | TGTTTTTTG | ACAATAGCCA | 50880 |
| TTCTAACTGG | GGTGAGATGA | TACCTTATTG | TGGTTTTGAT | TTGCATTTCC | CTGATGATTA | 50940 |
| GTTATTTATA | TGGTTTGGCT | GTGTCCCTAC | CCAAATCTCA | TCTTGAATTG | TAACTCCCAC | 51000 |
| AATTCCCATG | TGTCCTGGGA | GGAACCCAGT | GGGAGGTGAC | TGAATTATGG | GCCGGGTCTT | 51060 |
| TCCTATGCTG | TTCTTATGAT | AGTGAATGAG | TCTCACGAGA | TCTGATGGTT | TAAAAACGG | 51120 |
| GAGTTTCCCT | GCACAAGCTC | TCTCTTTGCC | TGCTGCCATC | CATGTAAGAT | GTGACTTGCT | 51180 |
| CCTCCTTGCC | TTCCACCATG | ATTGTGAGAT | CTCTCCAGCC | ATGTGGAACT | GTAAGTCCAT | 51240 |
| TAAACCTCTT | TCTCTTGTAA | ATTCCCCAGT | CTCAGGTTAA | GTCTTTATTA | GCAGCATGAA | 51300 |
| AACAGACTAA | TACAGTGATG | TTGAGCATTC | TTTCATATAT | TTGTTGGCCA | ATTGTATGCC | 51360 |
| TTCTTTTGAG | AAATGTCTGT | TCAGTTCACT | TGCCCACTTT | TTAAATGAAT | TGTTGGTTGT | 51420 |
| GCACGGGTGG | CTCGTGCCTA | TAATCCCAGC | ACTTTGGGTG | GCTGAGGCAG | GAGAACTGCT | 51480 |
| TGGGACTAGG | AGTTTGGGAC | AAACCTGGGC | AACACAGAAA | GGCCCTGTCT | CTAAAAAAT | 51540 |
| GAAAATAATA | AAAATAAATG | AATTATTAAA | TCTGACTACA | GTAGAAATAA | ATTTGAAATC | 51600 |
| AATAAAAATA | AGAAATGTAG | AAAAAAACAC | ACATATTTGG | AAATTAAACA | TCATTCTAAT | 51660 |
| TAATCAATCT | CTCCAAACAA | ATCACAAAAA | ATTACAAAAT | ACATTGTACT | ATATAATAAT | 51720 |
| GACAATAAAG | CACATCAAAA | TTCATGGGAT | GCAACTTAAA | CAGTGTGTAG | AGAGATCTGT | 51780 |
| AACTTAAATT | GCTTATAGTA | GAAAACAAAT | AAAGTCTAAA | ATGAAAGTCC | AGATTCTACA | 51840 |
| AAGGTGGTAT | GTCTAATAAG | AGATACTTGT | GTTCTCCCAG | TAATACTGCG | ATCCCAAGG | 51900 |
| ATGATAAAAG | TAAACTAGAA | GTAATCCCAT | CCTACTCTCT | GGAAACTGCT | AGAATGTTTG | 51960 |
| CTCTGCTTCT | CAGCAGAGCA | AGGGATGTGA | GAGAGGTGGG | GAGAGACAGA | GAGAGAGAGA | 52020 |
| GAGAGAGAGA | GAGATCATCA | ATCCTGATAA | GTTGTAACCA | CAAGCCAACT | TTTATACACA | 52080 |
| TTTAGGCTAA | AAAATAAAAA | GTCTTGGCTA | GCCACAGAGG | CTCATGCCTG | TAACCCCAGC | 52140 |
| ACTTTGGGAG | ACCAAGGTGG | GAGGATCACT | TGAGCCCAGG | AGCTCGAGAC | TGGCCTGGGC | 52200 |
| AACAAAGTGA | GCCCCATCTC | TAAAAAAAAT | ATTTAAAAAA | TTAGTCAGGC | ATGGTGGCAC | 52260 |

| | | | | | | |
|---|---|---|---|---|---|---|
| ACACCTGTAG | TCCTAGCTAT | ACAGAATGGT | GAGGCAGAAG | GATTGCTTGA | GCTCAGTAGG | 52320 |
| TTGAGGCTGC | AGTGAGCCAT | GTTCACACCG | CTGCACTCCA | GCCTGGGTGA | CAGAGTAGGA | 52380 |
| CTCTGCGTAA | AAAAAAAAAA | AAAAAAAAA | GTCTCAATTC | ATGAATTGAG | TTTAAAGTAA | 52440 |
| TACTTGACTG | GTGGTACCCC | AGCTTCCTGG | CAAAAGCAGA | CACAAACCCC | CTCTAGAAGA | 52500 |
| AAGAACATCC | CAGTCCTCAG | TGACCCATAA | GTAATTTTAC | CAGAAAAATA | AAGAAGTTAC | 52560 |
| TGGCAAAATC | ATCAAATGCA | CAAAATGGAT | TGGAGGAAGC | GTAGCAAGAA | TAAATGAAGA | 52620 |
| GGAGCTGGGT | GCTGTGGCTC | ACGCCTGTAA | TCCCAGCACT | TGGGAGGCT | GAGGTCAGGC | 52680 |
| GTTTGAGACC | AACCTGGCCA | ACATGGCAAA | ACCCCGTCTC | TACTAAAAAT | ATAATAATTA | 52740 |
| GCTGGGCATG | GTGGCATGTG | CCTATAGTCC | CAGCTACTTG | GGAGGCCTGA | GGCAGGAGAA | 52800 |
| TCGCTTGAAC | CCGAGAGGTA | GAGGCTGCAG | TGAGCCTAGA | TGGTGCCACT | GCACTCCAGC | 52860 |
| CTGGGCAACA | GAGTCAGACT | CTGTCTCAAA | AATAAATAAA | TAAATAAATA | AATAAATAAA | 52920 |
| TAAATAAATA | AATAAATAGG | GATCAGGAGG | TTTGAGTAAA | TAAGGTTAAA | AGTGATGGTG | 52980 |
| TTCTAGACTA | TTTGTGTCTT | TATATTAAAG | TGAATTTTTT | GTAGGCAGCA | TGTTGTGGCT | 53040 |
| CTTTTTTTGC | TTTTTTTTGT | TGTTGTCTGT | TTTTTAATT | CAATCTGACA | ACCTCTGCTT | 53100 |
| TTGTATTAGA | GTATTTAGAT | CATTTACCTT | AAGTGTGATA | ATCTATATGG | GTAGAGTTAA | 53160 |
| GTCTATCATC | TTGCTATTAC | TTTCCCATTT | GTCCCATCTG | TTCTTTGTTC | TCTTTTTCCT | 53220 |
| CTTTTTTTC | CCATCTGTTG | AACAACTTAA | ATATTTTTC | TCATTCTATT | TTATTTCTTT | 53280 |
| TTGTGGCTTG | TTAGCCATAA | TTCTTCGTTT | CATTATTTCA | GTGGTTGCCT | TAGAGTTTAT | 53340 |
| AGTATACATC | ATTAATTTAT | CGTAGTTCAT | CTAAAAGTAT | ACCACTTATA | TAAAATAACA | 53400 |
| TTATTTTCAT | TTCCACTTCT | TTTGCACTGT | TGTTGTCATA | CACTTTTCTT | TTGTGTGTGT | 53460 |
| GTGTGTGTGT | GACAGAGTCT | AGCTCTGTTG | CCTAGGCTGG | AGCACAGTGG | TATAATTTTG | 53520 |
| CCTCACTGCA | ACTTCCACCT | CCTGGATTCA | AGTGATTCTT | GTGCCTCAGC | CTCCAGAGTA | 53580 |
| GCTGGGATTA | CAGGCGTGCA | CCACCACGCC | TGGTTAATTT | TTGTATTTTT | AGTAGAGATG | 53640 |
| GGGTTTTGCC | ATGTTAGCCA | GGCTGGTCTT | GAACTCCTGT | CCTCAAGTGA | TCTGCACGCC | 53700 |
| TCGGCCTCCA | AAAGTGCTGG | GATTACAGGC | ACGAACCTTT | GTGCCCGGCC | TGTTTTACTT | 53760 |
| TTAAATGCTA | TAAATCACAC | ATTACATTGT | TAACTATTTT | TGTGAAAATA | GTCAACCACA | 53820 |
| TTTTATGGAG | AAAAAATATT | ATCTGTTTAC | TCACATAGTT | ACAATTTTCT | AGTACTGTTT | 53880 |
| ATTCCTTTGT | ATAAATAGGA | ATTTCAATAT | GCCTAAGGGA | CTTTTATCAT | TCTGCCTAAA | 53940 |
| GGACTTTTAA | AAAATATTTT | TTATTGTTCT | AGTCTGCTGA | TTAGATGTTT | ATTGCCTTTA | 54000 |
| GGCAGGGAGA | TAAAAAAATA | CTACAATATT | TTAGTTAATG | ACTGTGTCAA | TCAAAAGAA | 54060 |
| GCAAGACAAT | CTACCATTTA | ATTGCACGGT | TGATTTTTTA | AATGAAATAG | AAAACATCCA | 54120 |
| CATATACAGT | ACAAAATGTA | TCATAAAACT | CTCACATATG | ACTAGATAAA | TTCCTTCCTC | 54180 |
| TTTTCTCTGT | ATTAAATTGT | CTTATTTCAC | CCTCATTTGG | GGGGAGTTTT | TTTGCTTGGT | 54240 |
| ACAGAATTGT | AGGTCTTTCA | TTAATCTAAA | AAATTTTGCT | CCACTGTCTT | TTTGCTTATA | 54300 |
| TTGTGTCTAT | GAGAAATATG | TGATCTATAC | ACTTGTTCTT | CTGTACATAA | TGTGCCTTTT | 54360 |
| GTTCTTGGCT | GCTTTGAAAT | TTTTCATTTT | CCTCTTGCTT | GCTTGGGTT | TGATTGTTC | 54420 |
| TTATTTTCT | AGTTCTTTT | TTTTTTTAA | TTTTGAGACG | GAGTCTCGCT | CTGTCTCCCA | 54480 |
| GGCTGGAATG | CAGTGGCGCG | ATCTCAGCTC | ACTGCAATCT | CTGCCTCCTG | GGTTCAAGTG | 54540 |
| ATTCTCCTGC | CTCAGTGTCC | CGAGTAGCTG | GGACTACAGG | CAGATGCCAC | CAGGCCTGGC | 54600 |
| TAATTTTTGT | ATTTTGTTAG | TAGAGACAGG | GTTTCACCAT | GTTGGTCAGG | CTGGTCTCAA | 54660 |

-continued

| | | | | | | |
|---|---|---|---|---|---|---|
| ACTCCTGACC | TCGTGATCTG | TCCGCCTTGG | CCTCCCAAAG | TGCTGGGATT | ACAGGCGTGA | 54720 |
| GCCATCACGC | CCAGCCTAGT | TATTGATTTC | TATCTTCATT | CCACTTTGGT | CAGAGAATAT | 54780 |
| ATACTCTATT | ATTATAGTCC | TTTTACATTT | ATTGAGACTT | ATTTCATGAA | GTAATATACA | 54840 |
| GTCTATCCTG | AAAAATGTTT | CATGTGAGCT | TCAGAAGGAT | GTTTATTCTG | CTGTTTTGGG | 54900 |
| GTGTAGTGAC | CTATAGATTT | ATGTTAGGGT | CAGGTTAGGT | GTTTTCAAGT | GTTAAGTCTT | 54960 |
| CTATTTTTTT | GTTGATCTTG | TCTAACTAGT | GAGGTATTGA | TGTCTCCAAC | TATTATTGTC | 55020 |
| GAATTTTCTA | TTTCTCCCTT | CAATTCTGTC | AGTTTGTTT | CATGAATATT | AGGGCTCTGT | 55080 |
| TGTTAGGTGC | ATGTATGTTT | ATAATGTTAT | GTTTCTTGA | TGAATTGACA | CTTTTATCAT | 55140 |
| TACAAAATAC | CTTTCTTTAT | TTATTATAAC | AATGCTTATC | TTAAAGTTTA | TTTTGTCTGA | 55200 |
| TATTAGTATA | CCTACTCCAG | ACATCTTTTG | AGTACTATTT | GTATGTGATG | AATTGTTCCT | 55260 |
| TTCTTTCTGC | TCTCAAGATT | CATCTTCTTC | ATCTTTGAT | AATCTGATTA | TGATGTGTCT | 55320 |
| AGGTATGGAT | CTCTTTGAGT | GTATCCTACT | TGGAATTCAT | TGAGCTCCTA | AAATATGTAT | 55380 |
| GCAAGTTAAT | GCTTTTTTGC | CAAACATGGG | AAGCTTTGAG | AAATTATTTC | TCCAAACATT | 55440 |
| CTCTCTCCCT | GTCCTCTCAC | TTTTCTCCTT | CTAGGAGTCC | CATTATGCAT | ATATTAGTAT | 55500 |
| GCTTGATGGT | ATCCCCTGTC | TCTAAGGCTC | TATTTCTTTT | TCTTCATTCT | GTCTTCTTTC | 55560 |
| TGTTTTTCAG | AGTAGATCAT | TTCAATTGAC | CTATCTTTGA | GTTCACTGAT | TACTTCTTTT | 55620 |
| TGCTGCTCAA | ATTTGCTGTT | AAAGCCCTCT | AGTAATTTTT | TTTTCTTACA | GATGAGATAT | 55680 |
| CATGCTGTCG | TTCAGGCTGG | AGTGACCATG | ATCCTCTTAC | TGGGATCACA | GATCACGCAT | 55740 |
| GCTCCAGTCT | GAGCAGCAGC | ATGAGCTCCA | GCTTGCTCCA | GCCTGAACAG | CAGCAATACA | 55800 |
| TTCTTTCACA | CACAAAAGGG | TTATTGGATC | TCACACAAGA | AGGAATTTGG | GGCTAGTCCA | 55860 |
| TACAGTAAAG | TGAAAACAAG | TTTATTAAGA | AAGTAAAGAA | GGGCCGAGCG | CAGTGATTTA | 55920 |
| TGCCTGTAAT | CACAGCACTT | TGGGAGGCTG | AGGCAGGCAG | ACCACTGAG | GTTAGGAGTT | 55980 |
| CGAGACAAGC | CTGACAAACA | TGGCAAGACA | CTGTCTCTAC | TAAAAATACA | AAATTAGCTG | 56040 |
| GGTGTAGTGG | CACATGTCTG | TAGTCCCAGC | TCCTCAGGAG | ACTGAGGCAG | AAGAATCGCT | 56100 |
| TGAACCCAGG | AGGCAGAGGT | TGCAGTGAAC | CAAGATCGCA | CCACTGCACT | CCAGCCTCTA | 56160 |
| GCCTGGGTGA | CAGAGTGAGA | CTCTGTCTCA | AAAAAACAAA | AAAAAGTTAA | GAAATAAAAG | 56220 |
| AATGGGTCAT | GCATAGTGGG | TAATGCCTGT | AATCCTAGCA | CTTTGGGAGG | CCAAGGCAAG | 56280 |
| TGGATCGCTT | GAGGCCAGGA | GTTCGAGACC | AGCCTGGCCA | ACATGGCGAA | ACCCCATCTC | 56340 |
| TACTAATAAT | ACAAAAATTA | GCCAGGCATG | GTGGCACCCA | CCTGTGGTCC | CAGCTAGTTG | 56400 |
| GGAGGCTGAG | GCAGGAGAAT | TGCTTGAACC | CGGGAGGTGA | AGGTTGCAGT | GAGCCAAAAC | 56460 |
| ACGTCACTGC | ACTCCAGACT | CCAGCCTGAG | TGACAGAGCG | AGTCTTTATC | TAAAAAATAA | 56520 |
| AAATAAAAGA | AAAGAATGGC | TACTCCATAG | GCAGAGCAGC | AGTATGGACT | GCTCAAATAA | 56580 |
| GCAGACGTAT | AGTTATTTCT | GGATTATGTG | CTAAACTAAT | GGATTATTCA | AGAATTTTTC | 56640 |
| AGGAAAGAGG | TGGACAATTC | CCAGAACTAA | GGGTTCTTCC | CCGTTTAGA | CCATATAAGG | 56700 |
| TAACGTCCAG | ATGTTGTCAT | GGTATTTGTA | AACTGTCGTG | GCACTGGTGG | GAGTGTCTTG | 56760 |
| TAGCATGCTA | ATGCAGTATA | ATTAGTGTAT | ATGAGCAGTG | AGGATGACAA | GAGGTCACTT | 56820 |
| TTGTGGCCAT | GTTGGTTTTG | GTGGGCTTTA | GCTGGCTTCT | TTACCGTTAC | CTATTTTATC | 56880 |
| AGCAAGGTCT | TTGTGACGGG | TACCTTGTGC | AACCTTCTAT | CTCATCCTGT | GACTAAACTC | 56940 |
| CTGGTTAGAA | TGCCTAACCT | AACCCAGCAG | GCCTCAGCCT | TATTTTACCC | AGCCCCTATT | 57000 |
| CAAGATGGAG | TCACTCTGAT | TCAAATGCCT | CTGACATATT | TTCCCACTCC | CTTTTACCAG | 57060 |

| | | | | | | |
|---|---|---|---|---|---|---|
| GGAACCCTTA | ATCCTAAGGA | TTGCAGTGGG | ATAAAGATCC | GTCTTCTATA | ACTTCTTCAG | 57120 |
| ACTAAATAGG | GGCAATGATA | TTCCTGTCTA | ATTATTAGGG | TCTCTTGTGT | CCAGGGTAGA | 57180 |
| GAGGAGCTCA | GTCACAAAGT | GTCAGTATGG | TGAGACATTC | ATAACTCTGA | GGCTTCCCAA | 57240 |
| AGTGTTGAGA | TTACAGGCGT | GAGCCACTGT | GCCTGGCCAG | GGTCCCATTT | TTATACCAGA | 57300 |
| TCCTGGATCC | CAAAAGAGGG | AATCAGCCCT | CTTTTGGGGG | ATCAGCCATC | TCCCTGGGA | 57360 |
| ATCTTATCTC | TCGGTGGGGA | TGGAGACATT | TCCATACCTT | CTAGGTAGTC | AAGAGAATGC | 57420 |
| TTCTTGTGAT | CCAAAAGTGC | AAATAGCCAA | GTATTCACCT | ATATTTGCCT | TTAGCTATCC | 57480 |
| CCAGAAGTAT | ATTTCCTACC | TGGTTATTAC | ACACCAGATC | TCCCTCATAA | TGCAAAGTAA | 57540 |
| TTTCTGATAC | CCCCAAAAGT | CAAAAACATC | AGATAACATA | ATGCAAAGCC | AAACAGAGCC | 57600 |
| TTAGATTTTG | CGAAGGATCT | ATCCACTTCC | AGTTCCTGGG | GTTTCATGAG | GAAAACAGAG | 57660 |
| GTTTTCCCAA | AATGGGGTCT | GTGGTGCCTC | CTCTGCTTTT | CCCAAGGAGT | CCCAGGCTTT | 57720 |
| TAGAGATTGA | ATATCCACTT | TTAATTAAGC | TTTTAACCAT | AAACCATAGC | ACTCTAAAGC | 57780 |
| AAAAAAAAAA | GGAGTCCTTT | TAAGTTTCTT | ATTACTCAAC | TTTAGCCATC | CCACACGGCC | 57840 |
| ATTATTTCTG | GCTTTTGAAC | TTTACCAAAG | ATAATCTCCC | AGGTTCTCAG | AGAGAGGAAA | 57900 |
| ACTCAAGACA | GTGTGTGGAG | GGGAAGAGAA | CAGAATCAAC | AAATGGTAAA | GGTCACACAG | 57960 |
| ATATCAATCA | GAAAGTACTC | ATTCCCTAAG | CCAGGATTGA | ACCTTGGCCG | CCATTATAAA | 58020 |
| ATGACAAATC | CTTAGCTGCT | GAGCTACAAC | ACTGGTTAGT | TTCCATTGCC | CTTCCCAGAA | 58080 |
| GGGGTCCAGA | GCAGCCAATT | TTGAGCTTGC | AATGGCTTGA | GATAATTTTT | AGAGTTAACT | 58140 |
| ATTACATAAA | CCCCAAAATT | CCTGTTCCCT | GGATGGCAGA | GACCAAGAGA | AAGTACCGCC | 58200 |
| ACGTGGTTAC | AAGGTGAAGC | TCCAAAGGAC | ATAAACAAG | ATGAGAAGGA | AACTTCATCC | 58260 |
| AGTTTTTATT | TTTTTTTTTT | TCCAGGGACC | TGTAATAAAC | TTTGCAACGG | ACCAGTTTAC | 58320 |
| TGGGCTGGCT | TGAACAGCAG | GCTTATGGAG | TCCTGAGCCC | ATGTTCTATC | CTACCATATT | 58380 |
| CCTCTTTATG | ACAGAGTAAT | ACAGAAAGAC | AAATTGATAT | CACAAAGTAT | ACCAGATTCA | 58440 |
| TTACAGCTTA | AGACTAGCCC | CACAAATCCT | TGTTCCCATT | AATCAAAACT | TTACAGAGGT | 58500 |
| GATAAACAGT | GATTTTTACC | ATTCATTCAG | TTTTCACTAA | GAGAGAGAGG | CCAGAAGCCT | 58560 |
| GACTGGTAAG | AAATCTTTAC | CCTTTTGCTG | GCATGCCAGG | TTTCTGGGTT | CTCTTTCACT | 58620 |
| GAGCAGCACT | AGCAACCTTG | CTCACTGCAA | AGCCCTTGGG | TCCAAGCTAC | GACACAAAAG | 58680 |
| AAAACCAACT | TTTTTCTGTT | TCATGGAACC | ACAGGCAAAT | AAATGTCTCT | CACTTTTGTA | 58740 |
| AGATGCTGCC | CAATGGCCAC | ATAAAGTAAC | CAAATTAACG | TTTTCCATTT | CAGCCAGAGC | 58800 |
| AATATACATG | TGACAAAACA | TAGACATTGG | CCACTCCACT | TAGCACCCAA | TATCTAACTG | 58860 |
| GGAAGGCTCA | AACTTGCCCC | CAGATAGGCC | CTTTCATCTT | TAATCAAACT | TCTGACCAGG | 58920 |
| AGTTTCAACA | TATGGTCTCT | GGGCAAGATG | GTTGTCTCAA | GTAACAGAAA | AGACAGAAAA | 58980 |
| GAGAAAAGAG | AGAAAGGGAG | AAAAGCATTG | CCTGTGGTGA | GATGGGGAAG | GTGAGGAGTT | 59040 |
| CACAGAGGCC | AGAGAAAGAC | CCACCCATTG | CAGCAACACT | GAATCAAAAG | TTCAGGCGGC | 59100 |
| TGCTTGTCAT | AGCAAAGGGA | TCTTTTCCAA | CAGTCCTATC | AGCTGTCAAG | CTTCCCCTTT | 59160 |
| TGGAGAGAAG | AAAAGTTCCC | AATGTCCCGT | GATCCTGTAC | ATGCCTAATC | CTGTCACCCA | 59220 |
| TAGCTGTCAG | CAAAGAGCAC | AGGGAAGATT | AATACAAACA | GAATAGCAGT | TAACATCCCC | 59280 |
| TAATGCTAAA | TCCGTTTTTA | ACCAAGAGAG | ACTTTACTGA | GAGGGGCCTC | TAACCCCTTA | 59340 |
| AATCTTAAGG | ACTGTAGCCT | TCCTAAGTTG | GGTCTCAAAC | CCAAGTTCGG | TCAAGCATTC | 59400 |
| TTGCCCTTTA | TTAAGAGCGG | ACTGAAACCC | TCTCTGTCTT | AGGAGAGACC | CTATCTCCCC | 59460 |

-continued

| | | | | | |
|---|---|---|---|---|---|
| TAAGTTGCAC | CTCTAACCCA | ATCCTATCCT | TTACCCGGGG | ACTCCACCAC | TTACCCAAAG | 59520 |
| TCAGCCAGTT | GGTGCTGTAG | TCTGTTTCCT | TTGGCTTCAG | AGTCTCCTCA | GTATTGTCCC | 59580 |
| TTCGTGGTCA | CAGAAAGATT | TACCAGAAAN | GGGTCTTGAT | CCAGACCCCA | AGAGAGGGTT | 59640 |
| CTTGGATCTC | ACACAAGAAA | GAATTTAGGG | CAAGTCCATA | CAGTAAAGTG | AAAGCAGGTT | 59700 |
| TATTAAGAAA | GTAAGGAAAT | AAAAGAATGG | CTACTCTGTA | GGCAGAACAG | CAGCGTGGTC | 59760 |
| TGCTCAAATA | AGCATACTTA | TAGTTATTTC | TGGATTATGT | GCTAAACAAG | GGGTGGATTA | 59820 |
| TTCATGAGCA | TTCCAAAAAA | GGGGTGGACA | ATTCCCAAAA | TTGAGGGTTC | CTCCACCTTT | 59880 |
| TAGACCATAT | AAGGTAAAGT | CCAGATATTG | CCGCAGTATT | TGTAAGCTGT | CATGATGCTG | 59940 |
| GTAGGAGTGT | CTTTTAGCAT | GTTAATACAT | TATAATTAAC | ATATAATGAG | CAGTGAAGAC | 60000 |
| AACCAGAGGT | CCCTTTGGTG | GCCATGTTGG | TTTTGATGGG | TTTTGGCCAA | CTTCTTTACC | 60060 |
| ACAACCTATT | TTATCAGCAA | GGTCTTTGTG | ATGTGTACCT | TGTGCTGACT | TCCTATCTCA | 60120 |
| TCCTGTGACT | AAGAATGCCT | AACATACTGG | AAATGCAGCC | TAGCAGGTGT | CAGCCTTATT | 60180 |
| TTATCCAGCG | CCTATTCAAG | ATAGAGTCAT | TCTGGTTCAA | ATGCCTCTGA | CAATGCAGCC | 60240 |
| TTGAATTCCT | GGGCTGAAGC | CATCTTCCCA | CTTCAGCCTC | CTGAGTAGCA | GGGACTACAG | 60300 |
| GCACACACCA | TCATGCCTGG | CTAATTTTTT | TGTATTTTTT | TTTTAGAGA | TGGGGTCTCA | 60360 |
| CTGTGTTGCC | CAGGCTGGTC | TTGAGCTCCT | AGGCTAAAGC | AATCCTCCTG | TGTCATCCTC | 60420 |
| CCAAAGTGTT | GGGCTTGTCA | GAGGTATTTG | AACAAGAAAG | ACTCCATCTT | GAATAGGAGC | 60480 |
| TGGGTGAAAT | AAGGCTGAGT | CCTGCTGGGC | TGCATTCCCT | GTAAGTTAGG | CATTGTAAGC | 60540 |
| CACAGGATGA | GGCAGGCAGT | GGGCACAAAA | TACAGGTCAT | AAAGACCTTG | CTGATAAAAC | 60600 |
| AGGTTGCAGT | AAAGAAGCCG | GCTAGGCCAG | GTGGGGTGGC | TCACACCTAT | AAGCCCAGCA | 60660 |
| CTTTGGGAGG | CTAAGGTGGC | TGGATGGCTT | GAGCGCAGGA | GTTGGAGATC | AGCGTAGGCA | 60720 |
| ACATGGCGAA | ACCCGGTCTC | TATTAAAAAT | ATAAAAAATT | AGCTGGGTGT | GGTGGCACAT | 60780 |
| GCCTGTAATC | CCAGCTACTT | GGGAGGCTGA | GGCACGAGAA | TCGCTTGAAC | TCAGAAATTG | 60840 |
| GAGGTTTCAG | TGAGCTGAGA | TCGTGCCACT | GCACTCCAGC | CTGGGCAAAA | AAAAAAAGA | 60900 |
| AAAAGTAAA | GAAGCTGGCT | AAACCCCACC | AAATCCAAGA | TGGCGATGAG | AGTGACCTCT | 60960 |
| GGTCATCCTC | ACTGCTCCCC | ACCAAATCCA | AGATGGCGAT | GAGAGTGACC | TCTGGTCGTC | 61020 |
| CTCACTGCTA | TGCTCATACC | AGCGCCACGA | CAGTTTACGA | ATGCCATGGC | AACGTCAGGA | 61080 |
| AGTTACTTTA | TATGGTCTAA | AAAATGGAGG | CATGAATTAT | CCACCCCTTG | TTTAGCACAT | 61140 |
| AATCAAGAAA | TAACCATAAA | AATGAGCGAC | CAGCAGCCCT | CAGAGCTGCT | CTGCCTATGG | 61200 |
| AGTAGCCGTT | CTTTTATTCC | TCTACTTTCT | TAATAAACTT | GCTTTCACTT | TACAGACTCG | 61260 |
| CCCGAATTCT | TTCTTGTGTG | AGATCCAAGA | ACCCTCTCTT | GGGGTCTGGA | TCTGGACGGA | 61320 |
| CCCCTTTCCG | GTAACAGGAT | TACAGGTGTG | AGTGAGCCAC | CATCCCAGC | CTTAGTAAAT | 61380 |
| TTTTATTTCA | GTTATTATAT | ATTTTTATTT | ATTTTCTGTT | TTTCAGTTAT | TATATTTGAA | 61440 |
| ACTCCAGAAT | TTTTATTTAG | AATGTATTAA | CAAATCAGGA | GTACTGGCAT | AAGCCTGGCA | 61500 |
| CAAAGCAAAT | GTTGACATAG | GTCTGGCACA | AAACAAGTGT | TCAATGCATT | TTAGCTACCT | 61560 |
| TTAAGTGTAT | TATTACTAGC | TGCTTCTGGG | GCTATCGGG | GAAAATTATC | CTTGCAAAAC | 61620 |
| CCCCACTCAC | TTCCAGAGCA | GGCTTCAGTG | AAGCAGTCAT | CTGTGTCATG | ACAAGAGCCA | 61680 |
| AACTCTGTAA | AACATTTGAA | GAGATTTATT | CTGAGCCAAA | TTTGAGTGAC | CATGGCCCAT | 61740 |
| GACACAGCCC | TCAGGAGGTC | CTGAGAACAA | GCGCTCAAGG | TGGTTGGGAT | GCACCTTGGC | 61800 |
| TTTATACATT | TTAGGGAGGC | ATGGACATC | AATCAAATAC | GTTTAAGAAA | TGTACACTGG | 61860 |

| | | | | | | |
|---|---|---|---|---|---|---|
| TTTGGTCCAG | AGAGGCGGGA | CAACTGGAAG | CAGCGGAGGA | GTGGGGTGGA | GGTGATGACA | 61920 |
| ATTGGTTGAG | TTTGTATAAA | GATTTGGGAT | TAATAGAAAG | GAGCACTAGG | TTGTGATAAC | 61980 |
| AGGTTGTGAA | GACCAAAGTT | GTACTATGGG | ATGAAGTTTT | TAGCTAGCAG | GCTTCAGAGA | 62040 |
| GAATAGGTTG | TAAAATGTTC | TTATCAGACT | TAAAAGCTGT | GTTGATGTTA | ATGCCAGAGA | 62100 |
| GGAATAATGA | GGCATGTTCA | ACCCCACTT | CCCTTAATGG | CCTGAGCCAG | TCTTTCAGGT | 62160 |
| TACATTTTAA | GAAGCCTGAC | TGAAGAGAAA | GTCTATTCAG | ATGGTTGGGG | GCTTTAGAAT | 62220 |
| TTTATTTTTG | TTTTATACCT | TTGCCCTTGG | AAGTTTTGCT | GAAAAATGAA | CACAAAAAAA | 62280 |
| GGCAGATTCA | TAAGATAAAA | GGCTTTACAA | TTTAATTACT | CTGTGGTTCT | CCTCATGCAC | 62340 |
| ATAGTACCAA | TATCCCAGTG | GAATTTAGAA | GCTTATATGC | CACCTTGAAG | TTGAAGAAAT | 62400 |
| AACAGGGGCT | TGATCCTTGC | AAAATAGGTT | ATGGGAAACA | GAAGAAGAGG | AATTCTGTTG | 62460 |
| AGGGGCAATA | TGTAACTACC | AGGAGAGACT | AATTGGATCA | AGAACAGAT | AAATTTGTAA | 62520 |
| ATAGTTCTCC | TTGGAATTTA | AATGATGCTT | AGAGACTGAT | TATCTTATAA | AAGGGTCTGT | 62580 |
| TCAGGTGTGG | TTACATTCTT | GGTCTTTCCT | ATAATGCACA | ATGAGATAAC | AGAGAGGGAG | 62640 |
| AAAAGAACAA | TTGTTCTCGC | TGGTGGGCC | ATCCTATTTT | TATGTACCTA | GGGAAAAGTC | 62700 |
| TCTTTAGTGT | CTGTTGATCT | CTAAGAGTTT | TTCATTCAAA | ATACTCATTA | TATCAGGAAG | 62760 |
| CCACATTTTG | GGGTGAAATT | CACTACTCCC | TTTTAGAGAT | ACGGGTACAA | ACTGTTTGTA | 62820 |
| AAGAATGCTA | AGACTTTGCC | GGGTGCAGTG | ACTCACGCCT | GTAATCCCAG | CACTATGGAG | 62880 |
| GGGCCAAGGT | GGGCAGATCA | CTTGAGGTCA | GGAGTTCAAG | ACCTGCCTGG | TTAACATGGC | 62940 |
| AAAACCCCAT | CTCTATTAAA | AAAAACAAAA | ATTAGCCAGG | CGTGGTGGTG | GGCATCTGTA | 63000 |
| ATCCAGCTA | CTTGGGAGGC | TGAAGGCAGG | GAGAATTGCT | TGAGCCTGGG | AGGCAGCTGT | 63060 |
| TGCAGTGAGC | CGAGATCACG | CCACTGAACT | TCAGCCTGGG | CAACACAGCG | AGACTGTCTC | 63120 |
| AAAAAAAAAA | AAAAAATGCT | AAGACTTACT | TTGGGACATC | CTTTGTCAGG | GTCCATGATT | 63180 |
| CTGATTAGCT | CAAGGCAGGT | ATTTTTTTTT | TTAATAGAG | ACAGCATCTT | GCTATGTTGG | 63240 |
| CCAGGCTCGT | CTCGAACTCC | TGGCCTCCAG | TGACTCCCCC | CACCTCAGCC | TCCCCAAGTG | 63300 |
| CTGTGATTAC | AGGTGTGAGC | CACCACACCG | GTCTGGTTTT | TTTTGGTGGT | TGTTGTTTTA | 63360 |
| ATCCTATAAT | CCTGTGTCCT | TTCTTCCTAC | CTCTGAGTAG | TGCTTACTCT | CTCCCCTTTA | 63420 |
| GTCATTTGAA | AAGTTTATCA | GAAAGTGGGT | GCAGTTTCAG | GCTGGGTACC | GTGGCTCATG | 63480 |
| CCTGTAATCC | CAACACTTTG | AAATGCTTAG | ATGGGAGGAT | CATTTGAACC | CAGTTCAAGA | 63540 |
| TTACAGTGAG | CTGTGATCGT | ACCATTGTAC | TTCAGCCAGG | GTGACAGTGC | AAGAGCCTGT | 63600 |
| CTCTAAAAAC | AAACAAAAAA | TTGCTTTCAC | ACTGTGATGC | TATCACATCT | CTCCTAAGCT | 63660 |
| CTTGTTGGGG | CTCAGAAATT | GATACCCTAA | TATATGGCCC | TTGGTCATAT | TGAACTGAAG | 63720 |
| AAGCCTCAAA | GTCTCTCTGA | CATCCCTGCC | ACCAACTATC | CCTACCAAAA | CACATCGTGG | 63780 |
| AATTAAAGTT | TCTTTATCTA | CCTAAGATCC | AGACCCACCA | AAAAGAGCAA | TTATTTTTAT | 63840 |
| TTACCCTTCC | TGTAAGACCA | AGAATGTAAC | CATGCCCGAA | CGGACTTTCA | CAAGATAATG | 63900 |
| TTCAAGTTAA | TCTCTGTTCC | CTGATCTACT | TACTCTCCCT | AGTAATGAAA | GGAGTTGGCC | 63960 |
| AGCTTGCTTT | AGGCAGACAG | TAAGGGAATG | GTACCCAGAG | AACCTCTGAC | CTGCCCCACA | 64020 |
| AGTGCTTACA | CCGGATGTTT | TGTGCAGATA | AGGGAACTTG | CACAGGGGC | TTGCCTAAAC | 64080 |
| ATGCCTGCAG | TGGATGATTC | CTTTCCTTAA | CACATGCACA | GTTCAGGAAA | TTAATCAATA | 64140 |
| TGGAGTAGCT | CAGTCTAAAG | GCCTGCATGC | ACTGGTAGGA | CAGGGTGGAG | TTGTCAGGAA | 64200 |
| TTTGAGTCTT | AAGCCCTAGT | ATTCAACTGT | GAAGAGCAAA | CCAGAAATCT | GCTTTCAGGA | 64260 |

| | | | | | | |
|---|---|---|---|---|---|---|
| CCCTTGTCTT | TGCTGAGAGC | TTTCCTTTCA | CTTAATAAAT | TCTACTCCAC | TCATTCTTTG | 64320 |
| ATGGCTGCAT | GCCTAATTCT | TCCTGGCTGT | GAGACAAAAA | CCCGGACCTA | GCTGAGCGAA | 64380 |
| GGAGCAAAAA | TCCGCAACAG | TAATCCCATC | AACAGAGTTT | CTCTTCTTCC | CCTCCCATAA | 64440 |
| TCTGTTTTGC | CAGGATAATA | TATAAGCTTT | TAAGCCCTCT | TGGGAAGTGG | ATAATCATTC | 64500 |
| TATGGTTCTC | CCTGTGTACA | TGTTAATAAA | TTTGTGAGTT | GATTTTCAG | CAAAGTTTCC | 64560 |
| CCAGAAGCCA | AAGGGGAAAT | TTCCCTTGGC | CCCTCCACTC | TCTTTTCCCA | GCTCTTCTTT | 64620 |
| TACTTTCGTT | TTTATTTCCT | CAGCCCAGTA | GGTCACAGCC | TTCTTTTTAT | TTCTTCTCTG | 64680 |
| TCCAAACCAT | CAGTATATCC | TACAGGTGGG | AGAGAAGCAG | CTCTCTGGGA | AACCAGTAAG | 64740 |
| CACCATGAGT | TCTGATACTT | TCTAGTACCA | TTTGACATAT | TAACATCCCC | GCCACCCCTA | 64800 |
| ATATGTATGG | ACACGCACAC | ACATACCACA | TCACATGCAT | CACACTAACA | CAAACTATGT | 64860 |
| ATCACATACC | ACACACAGCA | CACACAGTAC | CACATACCCC | ACACAACACC | CACACCACAC | 64920 |
| TACGTGCATC | ATGCACATAT | GTGCACACAC | CTCTTGTGAT | GTGTGTTTAG | TGCAATTCAG | 64980 |
| AAAGTTACTC | TTTGATTTAA | TGCACATCAC | TATGCTTAGA | AATATTCTAG | TTACTGGGAT | 65040 |
| TCATCAGTGA | ACAATATTGA | AAAAAATCCA | TCCCTTTGCA | TTCTCATGAG | GGAAGCAAAC | 65100 |
| ACTAAACAAA | ATAAATTAGT | AAAATATTCA | GTGATAAGTG | CCATGGGAAC | AAAATAGATT | 65160 |
| TGAAAATGTT | TGGGAGGGAG | AGAGGGGTAC | ACTTGCTAAC | AAGTGGTCAG | GATAGGGTTA | 65220 |
| GTTGAGAGGC | AAAATCTGAA | GGAGTTGAGG | AAAGGCATTC | TAGGAATAGC | TGAGTGCTGA | 65280 |
| CTCTTGCCCA | CAGTGGGAAC | ACACAGTACA | GAGCTTCTGA | AGGAGACTCT | AGTGACCTAC | 65340 |
| TTCCCATTGT | GAGTCTTTGG | ACTCCTATAT | CCCATAATCA | CAGGATCAAG | CCTAACTTTA | 65400 |
| CATATTAGAG | ATAATGCATT | CCTCCTTGGG | GATAGTTCAG | GTTGATTTCT | CCCTAGGCCT | 65460 |
| GCCTTTGTCA | ACATATTCCT | GAAGTCTCAT | CTGCACCCCA | TCTCTGCTTC | TAATATTGGC | 65520 |
| CACTCTGTGC | ATGAACCAGC | CCCTCCTTCC | TGCAATGGGA | AACAGGTGTG | AGATGGGACA | 65580 |
| GCTGTCACAA | TCCGTTTTGC | TTTTGTCTTG | CTGTTATTAT | TGGTAATGGT | AGTTTGTTTC | 65640 |
| CTTTTTAGCA | TTCACTAGCT | TCCTTTTCCT | GATCCTTTGA | TAGTGTTACC | AGAAAGGGGG | 65700 |
| TCCCAACCCA | GACCCTAAGA | GAAGTTCTTA | GATCTCGTGT | GAGAAAGAAT | TGGGGCAAG | 65760 |
| TCTACACAGT | AAAGTGAAAG | CAAGAAAGTA | AAGGAATAAA | AGAACGGCTA | CTCTACAGGC | 65820 |
| AGAGCATCAG | CTTCTGGACT | AAGGATACTG | ATATGGTTTG | GCTGTGTCCC | CACCTAACTC | 65880 |
| TCATCTTAAA | TTCCCACATA | TTGTGGGAGG | GACCTGGTGG | GAGGTAATTG | AATCATGGGG | 65940 |
| GCAGGTCTTT | CCCTGAGTAA | TTTATACTGC | TGTTCTCATG | ATAGTCAATA | AGTTTCATGA | 66000 |
| GACCTGATGG | TTTTATAGAA | AGGAATTTCC | CTGCACAAGC | TCTTTGCCTG | CTGCCATCCA | 66060 |
| TGTAAGACCT | GACTTGCTCC | TCCTTGCCTT | CTGCTGTGGT | TGTGAGGTCT | CCCCAGACAC | 66120 |
| GTGGGACTGT | AAGAGCATGA | AACATTTTTT | CCTGGTATAA | ATTACTCAGT | CTCAGGTATG | 66180 |
| TCTGGATCAG | CAGTGTGAAA | ATGGACTAAT | ACAGATACTT | ACAGTTATTT | CTTGATTATG | 66240 |
| TACTAAACAA | GGAGTGGATT | ATTCATATGT | TTTCTGGGAA | AGATGTGGGC | AATTCCCAGA | 66300 |
| ACCAAGCGTT | CCTCCCCTTT | TTAGACTATA | TAGGGTAGCT | TCCTGACATC | GCCATGGTAT | 66360 |
| TTATAAACCA | CTATGGAGCT | GGTGGGAATG | CCTTCTAACT | TGCTAACACA | TTATAATTCG | 66420 |
| TGTATAATGA | GCAATGAGAA | TGACTAGAGG | CCACTCTTGT | TGCCATCTTG | ATTTGGTGG | 66480 |
| GTTTTGGTCA | GCTTCTTTAC | TGCAACCTGT | TTATCAGCA | AGATCTTTAT | GACCTGTGTC | 66540 |
| TTGTGCCAAC | TGCCTATTTC | ATCCTGTGAC | TTACAATGCC | TAACTTCCTG | GGAATGCAGC | 66600 |
| CCAGTAGGTC | TCAGCCTTAT | TTTACCTAGC | CCCCATTCAA | AATGGAGTCA | TTCTGGTTTG | 66660 |

-continued

| | | | | | | |
|---|---|---|---|---|---|---|
| AACACCTCTG | ACAATAGGAC | AGATCTGGAA | TGAGCCATGC | CTGGGTACAG | AGTCACATCC | 66720 |
| ACAACAATGA | AAGTTGTAGA | TATCTGCAAG | GACTCATCGT | GGGACCAAGG | ATTCAGGGGC | 66780 |
| TCATTCTTTC | TCCTCTCTCT | GTGTGCTGGT | TGCCTCAGGA | GTAGAATGTC | CCATGCTATG | 66840 |
| CATGGGGTCT | GCAACCATCA | TGCCAGGGCA | TGATGAATCG | TAGGTGGCAA | AACAACAGAA | 66900 |
| GGCTCTGTGA | GCACCCAGGA | GGGTGCAGTG | CTGAAGAGTC | TTCTGCTTGG | TATAGGAAGA | 66960 |
| AAGGAACGTG | TTTCCCAATC | TTGCCTTTAT | TTTGAGTAGT | TGGACCAGAG | GGATTGCAGC | 67020 |
| TGGGCCAAAC | TCCATGTTCC | ATTGGCTATC | AGGGTCAGCA | GGCAGGCCAG | GGCCCAGAC | 67080 |
| AGGCCAGTGG | CTCCCAGAAT | TCAAGTTTAA | TTTCTCCTCC | CACCTGTGTC | CTGAGCTCCC | 67140 |
| CTTACTGGTT | CCCTTGGACC | ACTGCATCTA | CTTAAGCCAG | CATTTATTAT | GTTGTTATCA | 67200 |
| TAAATGCCTC | TTACACCTGA | GACTTATAAA | TGTGACAAGC | TCTTATTGTG | AGATAGTAAT | 67260 |
| CCATCTTTTT | TCCCCATGAA | ATAATAATTC | TAACGGGTGG | TGATAGTACT | TTTCCTTTCA | 67320 |
| TTTTGAAGTG | GAGAAGCTGG | AGCTAAGTCA | TTAAGGACTT | GACCCTGGAC | CCCACAGCCT | 67380 |
| TTTCTCCACA | AAGCACAAAG | CAGAGTGATG | GTCCCAGGGA | TCCCACACAG | CTCTAAGCTG | 67440 |
| GGGGCACTCA | CTGCTGGGCC | ACTAGTGACT | CCCATTTTCT | ATCCTGGCTG | ACCCTCGCTA | 67500 |
| TTGAAGAAGA | TCTGAGTCCT | GCAGAAGGAC | AGCAAGGAGA | AAAACAAGAC | ACAGAACGGG | 67560 |
| ACAGAGAAGA | ATAGAAAGCT | GACTCAGATG | AATTTGTGA | TGCCAATGAG | TCCTACTGCT | 67620 |
| GTTACCACCC | CTTTTTCCAC | CACACCCTTC | AGAGCAGTTA | TAGAACCACA | AGCAACCCAT | 67680 |
| AAATAGCAAA | AGAAGTAACA | TCAGCTAGGA | AGGCTTAAGG | ACTCCCAAGG | GAGTTGGTGG | 67740 |
| CAAAAGTAGA | AAGATCTCAA | ATCAGAGTCT | GTGAACTGAA | CCTCTGCAGG | CTTCCTGTTT | 67800 |
| TTAGATACTC | TGTGTTGGGG | TCACATGATA | GTTACAGGG | TTATTAATTG | GTTCCTTCTT | 67860 |
| TTTATTGCTG | TAAAAGAAGG | ATATTTTCTT | CCTACGTTTC | CCCCTCCTTT | ACCGGAGAGG | 67920 |
| CGGAGTGCAA | ATGATATGAA | CAACGTCACT | AGTTTCTCC | TAAATCTTAT | GAGCCCCGCC | 67980 |
| TCCCACAGTA | GTTTCACTTC | TCAGTTTAAT | CCGGTCTGAG | TTAACTTCCT | GACCCAGGAA | 68040 |
| GTGGCAGCAA | CAGAGGGGAC | TAGCAGCGAA | TATGTAAGTG | TCTGAGCAGT | GAAGGTTACG | 68100 |
| GAAAAGGTCC | AGGCTAAGGT | TTTCTCAGTG | GATATGTGAG | TGTGTACTGA | TGGCAAGTGG | 68160 |
| GGTGGGGAAT | ATATTTCGTG | ACAGCAGGGC | CCCTCCAACT | CTGAAAATGG | TCAGGACTTT | 68220 |
| CTTTGTTTTA | CAGCTCTCAC | CTCTTTCCTG | CTCTTTCTTT | CACCAGACTT | TACACCAAAT | 68280 |
| CTCAGAAGAT | TCAGAACTTA | GATGAGTGGG | GCCCAGGACA | GGAACCCTGG | AGCCTTGGAA | 68340 |
| GGAGGGGAGC | CCCATCTCCC | CAGAAGAGCA | GTGACCCCAG | CAGAGAGGGG | CCTGGTGTAT | 68400 |
| CACTGGAGGA | AATAGCCTGC | CAAGGAATAC | ACGTCTTCAG | AAGAAATTCT | GTGTGGCTTC | 68460 |
| AAGAGACTGA | TCAAATTGTG | AGAGGAAAAC | AGCCTACCCG | GTAATTGTAG | TTAAATTACT | 68520 |
| GTTTTTTATT | CTAGGCACTC | TTCAAACTTC | CTCCTGACTC | TGCCCCTGTC | CTAGAGGAGC | 68580 |
| TCCCAGGAGT | AGGGGTGTGG | GGGCGGGCGG | GGGGAGGGA | TCGGGGTAC | AGGGAGAGCC | 68640 |
| CAGCTAGGTT | CTCAGAAGAG | GCAGGCTTTT | TCGCTCCTGG | TCACTCCTCT | GTTGCCTATC | 68700 |
| CCTGGCCTCC | CCCATCTTCT | TTCTGCCTTC | CCTACCTCCT | TGGGTCTGCA | AACTCTTTAT | 68760 |
| GTTGCAATCA | CTCTGAACAT | GTCTCTTGAG | ATAGGTCCTG | TCCTGGAGAA | GAGATAGTAA | 68820 |
| AAGTAAACTC | CCCAGTTCTG | CAGGAGCTCT | GATCCCATAG | AAATAACTGC | TCCTCAGGAG | 68880 |
| CAAACCCTCT | GCTCTGCAGC | CTTCTTTCCA | ATTCTTATTC | CCTCAGTTTA | GGGAGAGGGC | 68940 |
| ACAAAAGGA | TAAACCGGTT | CTTCTGGTTG | TTCTGGTTGC | CTTGATTGCT | TCCATTATCC | 69000 |
| TCCTGGTTGG | GTCTCTAGCA | AGACGTTATT | AGCCAGGGAA | GTCCACTTA | GGCACCCCTC | 69060 |

| | | | | | | |
|---|---|---|---|---|---|---|
| TCTGCAGAAG | AGGTATTCAC | TATTCTCCTT | TCTCTTTCTT | TTGCCTATTA | TACCTCTGCT | 69120 |
| CCTGAAAGCA | AAAACAACAA | CAACAAAAAC | ACAAACAAAA | AACAACCGAC | CTTATTAACC | 69180 |
| AGTGTTGGTT | GTTGTTCTTT | GTGGGGGATG | GGGGGGGTCG | AGGTGGAGTC | AAATTTTATT | 69240 |
| GTCATGATGG | TGTAGGAGCC | AAGGGAACAC | TTCCCCTTTG | CCTTCTGAAG | TTCACTGAAA | 69300 |
| AATCGACTCA | CAAAAGGCAG | GCTAATTGGA | GAAAAGGCAT | ACAAATTTAT | TAACAAGTAC | 69360 |
| ATGGGCTAGA | ATCACAGAGT | GATTACCCCC | TCTGCCAATG | GGGGTAGATA | CTTATATAGC | 69420 |
| CTTATTTATA | AATACTTATG | TATAAATACA | TAAATATAAA | TATGTATGCA | TATGTATGTA | 69480 |
| TGTATAAATA | TGTATGTATA | CTGTATAAAT | ATGTATGTAT | AACGTTTATA | CATGTATACA | 69540 |
| TATTTATTTC | AGAGGGGAAG | GGTGATATCA | GGAGAATATA | GGTAATTCTT | TGAGGGGCAG | 69600 |
| TAAATGATTA | CTAGGGAGAA | TAAATGAATA | TTTGGGAGGA | TGAATGAATG | GAGGAACAGA | 69660 |
| GTTTAACTTG | TAAATGTTCT | CTTTGGAAAA | TGAATGAGCC | TGAGAGACAG | ACATTATTTT | 69720 |
| GTGAAAGTGT | CTGATTAGGT | CTGGTAACAT | TCTTAGTCCT | CTTTTCTTCA | GTACAAAATG | 69780 |
| AGATAATAGG | GGTTGGAAGG | AAAAACAATT | GTTCTTCTTG | TCTAGTGTGA | CTGGTCTTTA | 69840 |
| TGTAGATAGG | GGAAAAGTCT | CTTCCAGCAT | CTGCTGATCT | CTAAGGGCCT | TTAATTCAAA | 69900 |
| ATACTCATTA | TACCAGGGAG | TCATATATTG | GGGTGAAGCT | CCCCATACTC | CTTCAATGGA | 69960 |
| ATCTGTCACA | GATCACCCAA | TTGCATAAGT | GTTACTACTA | ATTACAAAGA | GTAATTCTGG | 70020 |
| TACCAATTAT | TCTTTTTTTT | TTTTTTAAGA | CAGATTCTCG | CTCTTTCACC | CAGGCTGGAG | 70080 |
| TGCAGTGGTG | TAATCTGGGC | TCACTGCAAC | CTCCCCCTCC | GGAGCTCAAG | TCATTCTCCT | 70140 |
| TCCTCAGCCT | CCTGAGCAGC | TGGGATTACA | GGTGTGCACC | ACCACATCTA | GCTAACTTTT | 70200 |
| TGTATTTTTA | GTAGAGATGA | GGTTTTGCCA | TGTTGGTCAG | GCTGGTCTCA | AACTCCTGAC | 70260 |
| CTCAGGTGAT | CTGCCCGCCT | CGGCTTCCCA | AAGTGCTAGG | ATTACAGGCG | TGAGCCACCG | 70320 |
| TGCTGGCCTG | GTAACAATTA | TTCTTGAAGT | TAACTAGAAT | AGGAAAGAGT | TTCACACTCC | 70380 |
| CTGAGTTCTC | TCTTTTACAG | CTTTTGTGAG | GAAGCCTGCA | TTGCTTCTCC | CAGCACTTGG | 70440 |
| TCCAAGGTAA | CTTTCTGTGA | TAACAGAATG | TTGTATATTG | AGGCTGTTAT | GTAGCCACTA | 70500 |
| GTCACATGCA | ACTATTAAGC | AATCAAAATG | TGGCAACTGG | AACAGAAAAA | CTGAATTTTT | 70560 |
| TCATTTTAAT | TTTTATTAAG | TTAAATTTAA | ATTCCTACTC | ATGATAGTGG | CTACTGTATT | 70620 |
| AGCTATACAG | CTAGATGTTT | GTGTATCCTC | TAAATTCCAA | TGCATTTCTT | CTTTCTGGAG | 70680 |
| AGAAGACTTT | AGCTGGACAT | GGTGGCACAT | ACCTGTAGTC | CCAGCCACTC | TGCCAGGGTG | 70740 |
| AGGCAGGAGG | ATTGCTTAAA | CCCAGGAGGT | CGAGGCTGCA | GTGAGCTGTG | GTCATGCCAC | 70800 |
| TGCCCTCCAC | TACAGCCTGG | GCAAGAGAGC | GAGAACTTGT | CTTATAAGAA | AAGAAAAAGA | 70860 |
| GGCTGGGCAC | GGTGGCTCAT | GCCTGTAATC | CTGGCACTTT | GGGAGGCTGA | GGCGGGTGGA | 70920 |
| TCACAAGGTC | AAGAGATCGA | GCCAACCAAC | ATGGTGAAAC | CCCATCTCTA | CTAAAAATAC | 70980 |
| AAAAATTAGC | TGGGCGTAGT | GGTGCACACC | TGTAGACCCA | GCTACTACTC | GGGAGGCTGA | 71040 |
| GGCAGGAGAA | TCGCTTGAAC | CCGGGAGGCG | GAGGTGCAGT | GAGCCGAGAT | AGCGTCACTG | 71100 |
| CACTCCAGCC | TGGGTGACAG | AGTGAGACTC | CGTCTCATTA | AAAAAAAAA | AAAAGTTAG | 71160 |
| AAGACTGAGA | AAAGAAAAAT | AATGAAATAA | TTTAGAGCAG | TCTGAGCTAT | GTGAGGTATG | 71220 |
| CAAAATTTAT | CAGGACAAGT | GAGGCAGGAG | TATAGGTCTT | CCAGTTAAGA | CCCCATGTTT | 71280 |
| TAAAAGCATT | TTGTTCCTGA | CTGGCTGCCT | CATCTATTAC | CTACATATTC | CCGAGATTTG | 71340 |
| TTAATACAAA | GAAACAATGT | TATAGCCAGT | CCAAAAGCTT | ATGCTATTTT | AATGTTAAAT | 71400 |
| CCTTGGCAAA | CAACTTTAAA | ACTGCTTTAA | ACTGCTTTTT | TCCTCTAACA | CACTTGTACT | 71460 |

-continued

| | | | | | | |
|---|---|---|---|---|---|---|
| GCTTGCTAAT | GAGGCACTTG | AACTCTGCAC | TTGGTTGCAG | TTTCTCAAAG | TGCCCCAAAC | 71520 |
| AACCTTCACT | CAATTTCTTC | CTTTTAGTTC | CTCTTTTCTT | CAATACAAAA | TGAGATAATA | 71580 |
| GGGGTTGGAA | GGAAAACTTT | CAAGACCTAT | GGAAGTCAGT | TGCAGCCAGC | TCATCACATA | 71640 |
| GAGGTGCAGG | TGAGGTGTAT | TTTCATCACG | GTGGAAAATT | CTGGCTGCTT | CATCTCCATC | 71700 |
| TCTAGAGCCA | ATATTGGAGC | TTTTCAATAA | AAGCTATGGC | CTCAACCACC | AGCACCAAGA | 71760 |
| AGATGATGGA | GGAAGCCACC | TGCTCCATCT | GCCTGAGCCT | GATGACGAAC | CCAGTAAGCA | 71820 |
| TCAACTGTGG | ACACAGCTAC | TGCCACTTGT | GTATAACAGA | CTTCTTTAAA | AACCCAAGCC | 71880 |
| AAAAGCAACT | GAGGCAGGAG | ACATTCTGCT | GTCCCCAGTG | TCGGGCTCCA | TTTCATATGG | 71940 |
| ATAGCCTCCG | ACCCAACAAG | CAGCTGGGAA | GCCTCATTGA | AGCCCTCAAA | GAGACGGATC | 72000 |
| AAGAAATGTC | ATGTGAGGAA | CACGGAGAGC | AGTTCCACCT | GTTCTGCGAA | GACGAGGGGC | 72060 |
| AGCTCATCTG | CTGGCGCTGT | GAGCGGGCAC | CACAGCACAA | AGGGCACACC | ACAGCTCTTG | 72120 |
| TTGAAGACGT | ATGCCAGGGC | TACAAGGTGA | GTGTGTGGGC | CCGGGAGCTT | TGGTAAGTAC | 72180 |
| CAAGTCTTAT | CCTGCTCCCC | AGGAGCTGAG | ATGATTTAAC | TTGAAACCTA | ACATTATGAC | 72240 |
| TTGGAAATAC | AGCTTTCATC | ATGTCATTCT | TCTGAAAAAT | AGTTTATGAT | GATTTCTTGC | 72300 |
| TCAATTATCT | AGACTGTCCA | TCCTGACCTT | CAATGGGATG | GTTGGACTCT | TATCTCTATC | 72360 |
| CATTTGTGTT | ATGATGAATT | TCTTTTTGCT | TTAGAACAGG | TTGTTCTCAA | ACCAAACACC | 72420 |
| CGCATTTTTT | CTTGTTTCAC | ACCATGAATA | TCATTTGAAA | AACCACAATA | TGTAAAGCCA | 72480 |
| TGCAGTAGGG | CCTGAAAACA | GGGAAGAAAG | ACCCATCACC | TTTTAGGTAT | CTACAGTCTA | 72540 |
| GTAAAGAAAA | CAAACCATCA | AAAATGTCTG | CCTGGAGGTC | CCTGGTTTTG | GTGGTGGGGA | 72600 |
| GGGACATTTA | GGGTAGAGAG | TGGTTCATCT | TAGAAGTAAC | TCCTGAAGGA | CACGTAAAAA | 72660 |
| TTGAACACCT | ATTGGGGGAT | TTTCATTTGG | GGAATGAAGG | GTCAGTGACA | TTGAAAATAT | 72720 |
| CACTCTGGTA | CCTCTACTTT | TTTTTTTTTT | TTTTTTTTTT | TTTCCTGAGG | TAGGGTCTTG | 72780 |
| CTCTGTATCC | CAGGTTGGAG | TACAATGGTG | CAATCTCGGC | TCACTGCAGC | CTCAACCTTC | 72840 |
| TGGGGCTCAA | GCAATCCTCC | CACCTCAGCC | TCCCAAGTAG | CTAGGACTAC | AGGGATGCCC | 72900 |
| CACCATACCT | GGATAATTTT | TTTATTTTTT | GTAGAGACAT | GGTCTGCCTT | TCTTGCTTAT | 72960 |
| ACTGGCCTCA | AACCCCTGGT | CTCCCTCCCA | TCTCAGCCTC | CCAAAATGCT | GGGATTAGAG | 73020 |
| GCATGAACCA | CTGTGCCCAG | CTACTGTGGC | ATGTCTATGA | TAAAAGGAAT | ATCAAGGAGT | 73080 |
| AAAATTCAAA | CTATCCGTAT | AAGAAAGGGA | GGAGAGGGCA | GATTTTAAGC | ACGATTCAGG | 73140 |
| AAGAAGAGTC | AAAGATTTGG | AAATGCTTGG | TTGTGGAAGG | TGAAGCAGAG | GGAGAGGTTT | 73200 |
| TGTGTACCAT | CCAGATTTCT | TGCCAGAAAG | CATATTAAGG | AAGGTGGGAC | TTTGCTGTTG | 73260 |
| GCAGCATGGA | GGAATGGGCA | TAGTCCTGAT | GTCCTTTTTC | CTTCTCTGTC | CTGCCTAAAT | 73320 |
| TTGAGGAAAA | TGTTGTCTCC | AGTGTCAGGC | TCCTTATTCT | GTCCTCCATG | AGGCAGAGGT | 73380 |
| GGTCTTGTAT | GAAGGCTCTA | AGTCCTTCTA | AGGACATGTC | AATCATGACC | ACCACTCAGC | 73440 |
| TCATGGCAGC | TCTTCCTTAA | ACTCCATGGA | GCAGCTAATA | ACTGCGATGA | TCATATTCCC | 73500 |
| ATTTGAATTA | CTTTTCCACC | AAGTAGTAAG | AAAAGGAACC | AGCTTATGTT | GAAATTGAGT | 73560 |
| TTTGTCACTT | ACTAGATGGG | CAATTTTGGG | CACGTTACTT | AATGTCTTCA | CACCTTGGTT | 73620 |
| TCTCCATCTG | TAAATGGGGA | TAATAGCAGT | GTCCTCCCTC | CCTAAAACAC | ATACACAGGA | 73680 |
| GGTGGTTATA | AGCTTTGAGG | ACATTAAAAT | ATAGAATGCA | TAGAATAGCA | CTTGGCATAT | 73740 |
| AGTAAGGACA | ATGTCATCTT | TTGCTAAAAC | AGTTACATAG | AACCTTTTCC | TGAGAACACT | 73800 |
| CGAGAATGAA | TGAGTATACT | TGTTGGGTTT | ACAGAGGACA | GGAGACAATT | CTTTCAGCAT | 73860 |

| | | | | | | |
|---|---|---|---|---|---|---|
| TGACTACAAT | TAGCAATTTG | GGTCAGCTTC | AAATCACTTT | CAATAGAAAT | ATGAGAAACT | 73920 |
| GTTTTGAAGA | ATAAGCTAAA | AGCTTGACAT | GAATACTAAA | TCATTTTAAA | TTGGATTCAT | 73980 |
| GATACCATTG | TTCAAAAGAT | ACCAGAATTC | CCCTCTTCCA | TGAACTGTTT | CTAATAACCA | 74040 |
| GCTGGCATCC | TGATTTTTCC | TGACTCATAA | GACACAAAAT | TTCATGTTGT | TGCCAAACAC | 74100 |
| TGGTATTGGT | TTTGCTTGGT | TCAGCATGTT | GTTTTACAAA | ATCTTTTAGA | TGATGATTAC | 74160 |
| CTTGTTCTAT | ATCCAACTTT | TTCCTGGCAG | GACTCTAGTG | GTGGACATAG | CTCAGGCTCT | 74220 |
| GGGTCAGCAG | ATGAGATTGC | AATTGTTGCT | CCACCACCTG | GCAGTCATAG | CCCTTTGGGC | 74280 |
| AAGTTATTTT | ACCCCTTTCT | TAGTCTCATT | TTCTACAGCA | CAGAAATGAA | GTTTAAAATC | 74340 |
| CTACCAACTA | TTCAGGGTTG | CCAAGGGGAT | CAGTATGTTC | CTGCACATAT | AGCCTTTAGC | 74400 |
| ATGCTCTCTA | GCAAAAAACA | ATGAGGACTC | TATAAATATT | CACTATTATT | CAAATATATC | 74460 |
| TTAGAAGATT | GGGATTCCCC | CTAGGTCCCT | AATGAAGAGT | CAAATTGAAT | AGGCTTCACT | 74520 |
| TATCAAATTT | TTCCTTCAGG | AAAAGCTCCA | GAAAGCTGTG | ACAAAACTGA | AGCAACTTGA | 74580 |
| AGACAGATGT | ACGGAGCAGA | AGCTGTCCAC | AGCAATGCGA | ATAACTAAAT | GGAAAGTAAG | 74640 |
| AATCTGACTT | CATTGATCTC | AAGCTATTTT | CCATTCTAGA | GCTTAGGCAT | AGGGGATGAT | 74700 |
| TGAGGAAAAG | CACAATGAGG | ATTTATTCTC | ACTAAACCAG | ATTGAAAAAA | TGAAACCCAA | 74760 |
| GGAAGAAACC | ATTATTTGTA | CTTATGCCCC | TGGTTCCAGG | TTTACATCCA | TGAGTATTTA | 74820 |
| GCACCAATCT | TTCCATCTTT | AAACTGTAGT | TGGCTGGGAT | TCCTGATACT | TCAGTCAGAA | 74880 |
| GAAGCAGAAT | TAGTATGACT | ATTTACCTAG | AAAAAGCATC | GAGTGGGTCT | CAAACTTTAA | 74940 |
| ATACGTCAAA | ATAAACCTGG | TTTGCAGGCC | TCAACTCATT | ACCCTGGCAC | TTTTACCACA | 75000 |
| GTGGAGCATC | TGGCTCTCAA | CTTTACAGGT | ACAGAAACCA | AGCTTTGTGA | ACACTTAGAA | 75060 |
| AACAGGATCA | CTCCAGATTG | AAATTCATAC | TACTCTAGCT | CATGAAGCTG | ATGAAAGAAA | 75120 |
| TATACTTTAT | TTATTTATTT | ATTTTTAAAT | TATTACTATT | TTTTGAGATG | GAGTCTTGCT | 75180 |
| GGAGTGTAGT | GGTGCGATCT | CAGCTCACTG | CAATGTCCAC | CTCCCGGGTT | CAAGCAATTC | 75240 |
| CCCTGCCTCA | GCCTCTTGAG | TAGCTGGGAT | TACAGGCATG | TGCTACCATG | CCTGGCTAAT | 75300 |
| TTTTTGTATT | TTAGTAGAGA | CGGGGTTTCA | CCATGTTGGC | CAGGATGGTC | TTGATCTCCT | 75360 |
| GACCTCGTGA | TTCACCCACC | TCAGCCTCCC | AAAGTGCTGG | GATTACAGGC | GTGAGCCACT | 75420 |
| GCACCCGGCC | TATACTTGAT | TTATAAGTAC | ATCACAAGTA | ATGCAACAAC | CTACACACTT | 75480 |
| GCAACTACAA | ACTTTCAGAT | TATTTCCGTG | GCTGACTAAC | CTCCACATTA | TCAGAGCCAC | 75540 |
| ATTCTTTTAT | GGAAATATTT | AGGTTTGTGC | AAAAGTAATT | GCGGTCTTTG | CCATTAAAGT | 75600 |
| AAAGGCAAAA | ACCACAATTA | CTTTTGCACC | AATCTTTATA | TTTATATAAT | TCACTAGCTT | 75660 |
| GCAGTAAAAT | CCCACAAGCT | GATTACCAAT | TTTCTCTCTT | TCAGGAGTCC | TCTCTAACCT | 75720 |
| CTACCCTGAT | CTTTGTTTGT | GGATGTTGCT | CTTGAGCTCC | TGAGTACACT | CTTACTTCCC | 75780 |
| CCATTTCTAG | GATCTTGGGC | AATGGGGAAG | ACCTTGATTG | TAACTAACAT | ATATGAAAAC | 75840 |
| CCGTCTATAC | AAGAGTTAAA | GCTGCACCTG | TCTCCTACAC | AAAAATTCCA | CCTCATCCTA | 75900 |
| AGTCAAAGAC | CCTTCTTCTA | TATCATAGTC | ATCAAAACAC | TGTATGAATT | TATTTTTATT | 75960 |
| TTTTAATTTT | TATTTTTTTA | AGATAAGTAG | AGAGTTTATT | TGGGCCAAGT | TTGAAGACTG | 76020 |
| CAATCCAAGA | ACATAGATTC | AAATTGCCCT | GAATACACAC | TCCCACTGCA | TTAATTTAGA | 76080 |
| CAGCACTAAT | GGAAATTGCA | ACTTTACATC | TCCTCAGATG | AGAGTTTCAC | TTGATTTCTG | 76140 |
| TCAGTCTTAC | ACATAGGAAT | GCTTAAGATG | ACCCTAGGGT | AGTAGAACAG | TATTTCTCAG | 76200 |
| TTAACCATAA | TAAATGCCTG | TCACACTCAA | AGCTCCCCCT | GCCAAGAATT | ATGGACCCTC | 76260 |

-continued

| | | | | | | |
|---|---|---|---|---|---|---|
| TTACCAGCCT | GGTTGTCTTA | AAATCCAGTC | TGGGTGATGT | TCATTATAAG | CTTTTACTTC | 76320 |
| AAGAAAATCG | CTCCAACTCA | GAAATCTAAC | TTCTTAAATC | ATAAGTAAAA | ACCTCTTTTT | 76380 |
| ATCCTTGTAA | CTGATAAAGT | GTTTGAACTT | GGCCCTAGTT | TCACAATTAA | ATTATCTAGC | 76440 |
| ACTCCTAACC | CAGCTTTCTC | CTGTGTCTTG | GCTGAAGAAC | AAGAAAATTA | ATTGGGTGAC | 76500 |
| TATAAGGAAT | CTGAGGCAAC | CTCTTCCACA | TCTGAGTGCC | TGCCTCCCAC | ACATGACTCT | 76560 |
| GCAGCAGGAA | ACTGGGACA | TTCTTCCAGC | TTCAGTGACT | CATGAGAAAA | TAATGTCCCA | 76620 |
| GTGGCTGATT | GTGTGTGTGT | GTGTGTTTGT | GTGAAAATAT | ATATAACACT | TAAGCATTTA | 76680 |
| ACCACTTTTA | AGTATATAGT | TCAGTAGAAT | TAAGTGCTTT | TACATTGTTA | CATTGTTGTG | 76740 |
| CAACCATCAC | CATTCCCATC | TCCAAACTGC | AACTCAGTTT | CATCTTTCAT | CTTCTAAACT | 76800 |
| GAAACTCACT | ACCCATTAAA | CAATAACTGT | CCATTTTCTG | GTCTTGCCAA | CACCTTGTAA | 76860 |
| CCACTATTTT | ACTTTCTGTC | TCTATGAACT | TAACTACTCC | AGATGCCTTG | TATAAGCAAA | 76920 |
| GTCTTACAAT | ATTTGCCCTT | TTGTTTCTGG | CTTATTTGC | TTGAATGTCT | TCAAGGCTTG | 76980 |
| TCATGTAGTA | GCGTGTGTCA | GACTTTCATT | CTTGTTTATC | CATTCATCCA | TAGATGGACA | 77040 |
| TTTGGTTTAC | TTCCACCTTT | TGACCATACT | TTCTTGACTC | CAGGAGAAGG | TACAGATTCA | 77100 |
| GAGACAAAAA | ATCCGGTCTG | ACTTTAAGAA | TCTCCAGTGT | TTCCTACATG | AGGAAGAGAA | 77160 |
| GTCTTATCTC | TGGAGGCTGG | AGAAAGAAGA | ACAACAGACT | CTGAGTAGAC | TGAGGGACTA | 77220 |
| TGAGGCTGGT | CTGGGGCTGA | AGAGCAATGA | ACTCAAGAGC | CACATCCTGG | AACTGGAGGA | 77280 |
| AAAATGTCAG | GGCTCAGCCC | AGAAATTGCT | GCAGGTGAGG | CTGTGTACTT | GGAGTAGGGA | 77340 |
| AAAAGGTAT | GTTATAGTGC | TATTAAAGGA | GAATGGTAAG | GAAGCATGGG | AAGATAAAGT | 77400 |
| AATGTTTCTT | TTAGATGTAC | ATCAGTGCCA | TCAGGCTGGC | CTTCACTAAT | TTATAGGGTA | 77460 |
| CCTTTATGTC | AATTAGAAAA | ATAAACTTCT | GAGGGAACAC | AGCTTGGCCA | AATGAAACCA | 77520 |
| CGGGATAACA | TTTACCACTG | TTTGCCTCCT | TGGCCCATGT | GCAGAGAACC | CTGGTTGTTG | 77580 |
| ACTCTCTCCT | GAAATACTCC | ACTAGGTGAC | TGATGGGTGA | TGAAGTGGGG | CAGCCAAAAT | 77640 |
| GAGTGATAAC | CTTTTCCCTG | ATTTGCTTGT | AGAACCCTTG | CTCCAGAGCT | GTTATGGTAC | 77700 |
| AATCTACAGC | TTTATCTGTA | GGAAGATAAA | CATCTGGAGC | CATTAATTCT | GGTTCTAACT | 77760 |
| AACAGGATTG | GTGACTATAC | TGTAAGGCTG | AGTGTATAGC | ATGATTGCTT | TACCACTGTG | 77820 |
| TGATACCTGC | TACCACCATC | TTAGTGGCAG | TGGCCCAGTC | TCAGGGCTGT | GCACAGATTC | 77880 |
| ACCACTAAGG | ACCTTTATGA | TAAGTGTTCT | CTAATCTGGG | CTCACTGTGA | AGGAAATCCG | 77940 |
| ATCACCAAAA | GCTAGTCCTT | ACAGAGGGAG | CATGGACAAA | GCTCCTGGCC | CTCAGACTTC | 78000 |
| AGCAAGGATG | AGAATAGATG | CAAATGTTGA | TAAACATCCT | GCCATGCTGA | ATCTCCCAGA | 78060 |
| AGCTGGTAGG | AATTATTCCA | TCTGGGTATC | CATCAATACC | TAAGACTGGT | GGGAATTACT | 78120 |
| TTGTTTGAGT | ATCCATCAAT | ATCTAAGACT | AAGACTAGGG | TAACTCTCTT | TACTTCTTCG | 78180 |
| GGTAAAGCAA | AGAAGAATAG | CCCTGCATGA | CAAGCCCCAT | GAAATACCGA | TGTTCCCATG | 78240 |
| CTCACCTTTT | CTTTTTGTTT | CTTTATAGAA | TGTGAATGAC | ACTTTGAGCA | GGTAAGTCCT | 78300 |
| GTTTGAATGC | AGGAGGGGAG | GGGTGTGCGT | ATATAGAAAT | GAATGGAATG | CACCTCTGAA | 78360 |
| GAAATCTCTC | GCCTCTGCTT | ATTCTAGGAG | TTGGGCTGTG | AAGCTGGAAA | CATCAGAGGC | 78420 |
| TGTCTCCTTG | GAACTTCATA | CTATGTGCAA | TGTTTCCAAG | CTTTACTTCG | ATGTGAAGAA | 78480 |
| AATGTTAAGG | AGTCATCAAG | GTATGTTCAC | TAAAGAATTC | CTGAATACTG | TGGATAGAAG | 78540 |
| GGGCCTTATG | CAGTAACCAA | GTTTACCACC | TGTCCCTTGG | CAGGCTCACA | GCCAGAGAGG | 78600 |
| TTGTTTAGTT | AATTTCAGTA | GAGCTTTCAT | ACTTTCTCTA | GTTAGTATGA | TTCACTGCTC | 78660 |

-continued

| | | | | | |
|---|---|---|---|---|---|
| AGTGAATGTG | ATGAGCATTG | CATTCTGGTT | ATCTGTGCAA | ACCTTTCAAA | TTCTTATTCT | 78720 |
| TTCACTTATT | AGCCATGTTA | CTCCAAGTGA | CTTGGTTTCC | CCCTCTGAAA | AATGAAAATA | 78780 |
| TTAACAGCTC | CTACTTCATT | GAGTTATCAT | CAAAATTAAA | TGCATCAACA | TGTACAAAGT | 78840 |
| GCTTAGCCCT | GTGACTGACA | CATGATCATA | ATAGCACATC | ATGGTATTAG | ATCTGATCAT | 78900 |
| AGTGTTTATT | ATCAATAGCT | CAGCCAACTC | TTAGAGCAAT | GCAAGAAAAG | TAGGTGAGTA | 78960 |
| TGATAACCTA | TCATTCACAT | ATTTTAGGAA | CTTGACTTAG | ATAACACAGA | TGACAAATGT | 79020 |
| TACAACCAAT | TTACAGATTC | CAAAATGTTA | GAACCATTTA | CTGAGTTTCC | TGCTCCCTTG | 79080 |
| ATTTTTTAAA | TCAGTGCTGA | CTATACTTTC | ACAAATTTGT | ATCCGTAAGT | ACAAAATCAA | 79140 |
| AAAACCCCT | GAAAATGGAA | AGTTTTATCA | TGATTCATTT | GGCTACAAAA | ATCTGGCCTA | 79200 |
| ACCTGAAATG | ATTTGGTGGT | TATATTAGTT | ATCTATTAGT | ACAAACAAAT | TACCATAATT | 79260 |
| TAGAACCTTA | ATACAACACT | GATATGTTAT | CTCAATTTTT | GTGGTTCAGG | AATCTGGGCA | 79320 |
| CAGCTTAGTT | GGGCCTGCTG | CTTAGGGTCT | GATAAGGCTG | CAGTTAAGGT | GTTGGTCAGG | 79380 |
| CTGTGTTCTT | ATCTGGAGGC | TAGGCTAAGG | AAGAATCCAC | TTCCAAGCTC | ACTGAGGTAG | 79440 |
| CAGGCAGAAT | TTCTTTCCTG | ATGGTTGCAG | GACTTTGGCC | CTGGTTATTT | CTGGCTGTTG | 79500 |
| GCTGGAGGTT | GCCCACAGCT | TCTACAGGCC | ACCCCTCAGC | TCTTTGCACA | TGGGCTTCTA | 79560 |
| ACATGGCCAG | TTATTTCTTC | AGAGAGAGCT | CAGGAGACAG | ACTCTTAGA | GAAAATCTGC | 79620 |
| CAGCAAGATG | GAGTCTTACA | TAATGAAACG | TAATCATAGA | AATTATATCC | CATCATCTTT | 79680 |
| GCCATATCCT | ATTGGTCAGA | AGCAATTCAT | AAGCCCTGCT | CACACTCAAA | GACAAGGAAT | 79740 |
| TTACGAGGG | TGTGAACACC | AAGAGGCAGG | AATCATAGAA | GGCCACCCTT | GAGTCTGTCT | 79800 |
| TCCACAGTGG | CCAACCCTGA | ACGGCACTGA | GATGAGACTA | TTTAAAAGTC | TTTATTTATC | 79860 |
| CCACTTAATT | TGAATAAATG | TTTTGCTGCA | GATATATTGA | TGAATTTGAT | TACAGGGCTC | 79920 |
| TGCCTTAGGC | CATGATGGGG | TTGAACTTTA | GAGTATATGC | ATTTTTTTGC | CTTTATAACT | 79980 |
| TCTAAACTAA | TTTGAATGGC | AAAGCCCATT | TTGTTCCAGG | GATTTCAGAA | AAGGAATTAT | 80040 |
| AGACCTGTGT | TCCCCTCAAA | TACACAACAA | CAAACAACAA | CAAAACCCAA | AAGCACTCTG | 80100 |
| TATTTCATCC | TATACAGATG | ACAGGAAGGA | AGAACAAGAC | TTTGTGTAAG | TTTTGCTGGG | 80160 |
| ATTTCACTGA | GTCAATTTGC | CTACTCTCAT | CTTTACAGA | AGGAATCATA | ATATGGTTCA | 80220 |
| AGTGAAACTA | TTTCTTTCTT | TCTTTCTTTC | TTTTTTTTT | TTTTGAGAC | AGAGTCTCGC | 80280 |
| TCTGTCGCCC | AGGCTGGAGT | GCAGTGGTGC | GATCTCGGCT | CACTGCAAGC | TCCGCCTTCC | 80340 |
| GGGTCAAGTG | AAACTATTTC | TTAAATGGGC | TTATCTTTTA | ACTAAATATT | TCTCCCTCT | 80400 |
| TAAACACTGT | TTATTAAAAT | TTTTCTTTTT | TCAAATTTTT | TTTTGAGATG | GAGTCTCGCT | 80460 |
| GTTACCCAGG | CTGGCTTGCA | GTGCCGCAAT | CTCAGCTCAC | TGCAGCCTCT | GCCTCCTGGG | 80520 |
| TTCCAGCGCC | TCAGCCTCCC | GGGTAGCGTG | GGATTACAGG | TACGCACCAC | TATGCCTGGC | 80580 |
| TGATTTTTGT | ATTTTTAGTA | GAGATGGGGT | TTCACAATGT | TGGCCAGGCT | GGTCTCAAAC | 80640 |
| CCCTGACCTC | AGGTGATCTG | CCTGTCTCTG | CCTCCCAAAG | TGCTAGGATT | ACAAGTGTTA | 80700 |
| GTCACTGTGC | CCAGCTTTAT | TACAAAAGTG | ATAGGAATAA | ATTTTATTTT | TATTTTTAAA | 80760 |
| TGTATGTTTA | TTTTATTTTA | CATTGCCTTC | AAGCAGATGC | AACAAATACA | TTTTAATCAG | 80820 |
| TCAAACAATA | TAAAGGATAT | AAGGAGAAAG | TTCAAGGTTT | TTCCCACCCG | TCTCCAATCT | 80880 |
| GACTTCTCTA | GGTAGGGTGA | TCTATATCTT | TCCCTAAGTT | TGTACAAACG | TAACATATAT | 80940 |
| ACACTGTCTC | TTCTATGTTA | CTCGTTACTT | TTTATGTCTA | ATATTCCATA | AGAATATAAT | 81000 |
| AAATATATGT | AACCATATCC | CTACTGATGG | AGCTTCAGGC | TGTTTTAGA | ACTTAGTTAT | 81060 |

| | | | | | | |
|---|---|---|---|---|---|---|
| TACAATGTTG | CTACAATAAC | TTTCTAGTCC | ATGCATCCTT | ATATCCTGGT | GCTTTCATTT | 81120 |
| CTTTTGGGAA | CATACCCCAA | ACTGGGATTG | CCGAGGTTGT | TGTTAATCTT | AATATATGGT | 81180 |
| ACCATATTAC | TTGACTCAAA | GTTGTAACAT | ACACTCCTAC | CAGCACCAGG | AATAATGACT | 81240 |
| CACATATACT | GAGCACTCTT | TAGTCTGTGA | CAGATTAGAA | AAGCTTTACT | TTTCTTGGTT | 81300 |
| CTTGTTTTAT | ATCACAGTCC | TCTCTATATG | GGGCATTTTT | GCTTTATAGA | GGAGGAAATA | 81360 |
| TGACACAGAG | AGGTTAGGTG | AGTGTTGTAG | GATCTCATAA | CTAGAAGGTA | GTCATAGAAA | 81420 |
| GAGTCTAGAG | TCTAGAAACC | ACTCTCTCAC | CATTTTGCAA | TGTGGCAGAA | AATGCAAAGT | 81480 |
| TGTTATTTAC | TTATCTCTTT | TAGACAGGGT | CTCACTCTGT | CACCCAGGCT | GGAGTGCAAT | 81540 |
| GGCCCCATCA | TGGCTCCCTG | CAGCCTTAAA | TTCCTGGGCT | TAAGCAATCC | TCCCACGTCA | 81600 |
| GCTTCCCCAG | TAGCTGGGAC | CACAGGCAAG | CACTGCCACG | TCTGGCTAAT | TTTTAAAAA | 81660 |
| TTTTTGTAG | AAACACTATC | TCTTTATTTT | GTTCAGGCTG | GTCTTGAACT | CCTGGGCTCA | 81720 |
| AGCAGTCCTC | TCGCCTCGGC | CTTCTAAAGT | GTTGGGATTA | CAGGCATGAA | CCACCATCTC | 81780 |
| CGGCCTGAAG | TTTATTTAAT | CCATTGCCTT | GTGGACTGGG | CATTGAAGTT | GTGTGTAGTT | 81840 |
| GGGTTTTTTT | GTTGTTGTTG | CTGTTGCAGA | CAATACTACT | GTGAACATTC | TTATCCATGC | 81900 |
| TTCCTTGTGT | CCCGTAAATG | TTCCCTCCAG | GGAGATACCT | TGGAGTGACA | TGCTGGTGTG | 81960 |
| AGGGATGCAT | ATCATAATTT | TACCAGATAC | TACAGATCTT | GAAATTGTTC | CAATTCTACC | 82020 |
| CCACAAGCAA | TATAAGAGCT | CTCACTCCTC | CAAAACTCCC | TGAGTCTTTA | CTTATATAAT | 82080 |
| TTATGATTTT | GACAGTCTTA | CAGATTTAAA | ATGGTACCTA | ATTGTGTACT | TAATTTGTGC | 82140 |
| TTTTCTGATT | TCACTAGTGA | GATTGAGATT | CTTTTGTAT | GTCCATTAGC | CCTTCAGGCC | 82200 |
| TCTGTGATTT | ACCCATGATT | TACTGTGGTT | TAATAATTTT | TATTGGGTTC | TTTTCCTTAT | 82260 |
| TGATTTATGG | GAACTTATTA | TAGCTGATAT | CTTCTGGCAT | GTGGATGGCA | TTTTGCATTT | 82320 |
| TCATCCTGTT | TTTTGATAAA | TAGGGTTTCA | AAATTAAGTA | GACACATTTT | CCTTCAAGGT | 82380 |
| CTGTGTCTTT | TATGTCCAAA | GAGCTTAGTC | ATCAGTGGGC | AGTGAATTTT | ATCACCTAAT | 82440 |
| TAATTTATT | AGCCCCGTGT | GCTATGCCTG | TAGTTCCAGC | TACTGGGGAG | ACTAGGGCAG | 82500 |
| GAGGATCTCC | TGAGCCCAGG | AGTTCGAGGC | TGCAGTAAGC | TATGATCACG | CCACTGTACC | 82560 |
| CAGCCTGGGC | AACAGAGCTA | GACCCTGTCT | ATTAAAGGAG | GAGGCCGGGT | ACAGTGGCTT | 82620 |
| ACGCCTGTAA | TCCCAGCACA | TTGGGAGGCC | GAGGCAGGAG | GATCACTTGA | GGGCAGGAGT | 82680 |
| TTGAGACCAG | CCTGGCCAGC | ATTGTGAAAC | CCTATCTCTA | CTAAAAATAC | AAAAATTAGC | 82740 |
| CAGGTGTGGT | GGTGTGCACT | TGCAGTCCTA | GCTACTCTGG | AGGCTTAGGC | AGAATTGCTT | 82800 |
| GAACCCAGAA | GGCAGAGGTT | GCAGTGAGCT | GAGATTGTGC | CACTGCACTC | CAGCTTGAGC | 82860 |
| GACAGAGTAA | GACTCCATCT | CAAAAAAAAA | AAGAAGAGAG | ATGAAGGAGG | AGGAGGAAGA | 82920 |
| GAAAGAGGTG | GGGGAGGGGA | AGGAAGAGAA | AGAAGAAGAA | AGGGACAAAA | AAATTTAGCT | 82980 |
| GTCATCTTTG | CTCTGATAGC | ATTATAATGA | TGATGAAGAC | AATTGCTAGG | TTGGTGAGAG | 83040 |
| AAGGCTATAT | ACACACCAGA | ACTCTCCACG | TATATGGCAA | GTTCATATAT | TTTGTTAAGT | 83100 |
| ATGTCTCATT | GGAGACCTTC | TTTTCCCGTA | ACTATGACCA | GTGCTCTGCC | AGCTCAGTCA | 83160 |
| ACAACAACAT | TGCATGTTGG | CTCCATACCT | GGACTCTTGG | TCCAATTGGT | AATGAAACCA | 83220 |
| TCCCACCAGT | GTCTTCATAA | TATATATATA | CACACACACA | TATATATATA | GTATTCTCTC | 83280 |
| CCAGTGTCTT | CATAATATAT | ATATATACAC | ATACACACAT | ATATTATATT | CTCTCTATAC | 83340 |
| ATATTTATTT | ATATATCTAT | ATCTATATCC | TTCCACCTCA | GGTCTCCCTC | TGTCTCCCAG | 83400 |
| GCTGAGTGGT | GCAGTAGTGC | GATTATGGCT | CAACCAATGA | GAGGATCAAT | GGCAATCCTC | 83460 |

-continued

| | | | | | |
|---|---|---|---|---|---|
|TCATTTCAGC|CTCCCCAGTA|GCTGGGACTA|CAGGCATGGG|CCACCACATC|TGGCTGATGT|83520|
|TTAAATTTTT|TTGAGACAGC|ATCTCTATAT|GCTATAGATA|TATATAGTAT|CCTCTCTCTA|83580|
|ATATGGATAG|AGGATACTAT|GTCTATATCT|GTATCTATCT|ATCTATGGAG|AAGGAATACT|83640|
|ATATATCTAA|TAAGATGTAA|TCTATATTAT|ATATAAAAGT|GAAGCATTGA|TTGGTACATA|83700|
|TAATATATAT|ATTGATTACT|GTGTGTATAT|ATTTGTTTTT|TCGAGACAGG|CTCTCACTCT|83760|
|GTTGCCCAAG|CCGAGTGGTA|CAGTGGTGCG|ATCATGGCTC|CACCACCTGA|GCTAAAGTGA|83820|
|TCTTCTCACC|TCAGCCTCCC|CAGTTGCTGG|GACTACAGGA|ACAGGCCACC|ATACCTGGCT|83880|
|AATTTTTTAA|TTTTTTTTTG|AGACAGGGTC|TCCCTTTGCC|ACCCAGGCTG|GAGTGCACTG|83940|
|GCGCAATCTC|GACTCACTGC|AATCTCCACC|TCCCAGGCTC|AAGTGATCCT|CTCACCTCAG|84000|
|CTTCCCGAGT|AGCTGGGACT|ATTGGTGTGC|ACCACAATGC|CTGGATAATT|TTTCATATTT|84060|
|TTTGTAGAGA|TGGAATTTGG|CCATATTGAC|CAGGCTGGTC|TCAAACTCTT|GGACTCAAGT|84120|
|GATTGACCCG|CCTCAGCCTC|CCAACGTGCT|GGGATTACAG|GCATGAGTCA|CTGTGCCTGG|84180|
|CCTGATTATT|GTACACATTT|TTGATGTAAT|GTATTATATA|TGTCATATAT|GACAATCTAG|84240|
|ATGAATATAT|TAAAGATTGG|GTTTTCATTT|ATATATTGTA|AAATACATAC|ACTATACATA|84300|
|TATAATATGT|AGAACATATG|CTATACATAT|TATATATGTA|TATGTTAACA|TATATAATAC|84360|
|ATACACATAT|AATATGTATA|GTTGCAAATA|TAAAATTTGG|TTTGTTATTT|ATATTATTTT|84420|
|GTGCAGGAGT|TCTATATCTA|TGTCTATAAG|CGGGAGCCAT|AATTTTCTAT|TCTTTGTAGG|84480|
|ATTTGGTATG|AGATTGGCAT|TACTCATGCC|TTGACTTCTA|AATTTCCTAT|AAAACTGACA|84540|
|AGTTCCATTT|TTGCTTGATA|AAGATGCACG|TTTTATTATC|TGTCGGTAAA|ATTTAAAGTA|84600|
|GTGATTTCAT|TTCTTTAATG|TTAGGTCTGC|CCATGCTTTA|TTTGTTTTTT|GAGTGAGTTT|84660|
|TACTCAGAAA|TATTTTTTCT|AGGAAGTAAT|AATTTTATCA|GTACTTTCAA|TTTTATTAGT|84720|
|AGCATAAGAT|TTATTATAAA|GTTCTGTAAT|ATTTAAAAAG|TTTCTGTATT|CATTCCATTT|84780|
|GTGCCTTCTG|TCTTACTTTG|ATAAATCTCA|TTGGAGGTAT|GTCTATTTTA|TTAAATTTCT|84840|
|TTTAAAAGAA|GCTACCTTTT|TTTTGTTTG|TTTTCCTCT|TTATTGCATT|CTTGTTTTCT|84900|
|TTAACTTCAC|TGTTATATTG|TTTAATATCT|ATTTTTCTT|TTTAAAAAAT|TATATTTGGC|84960|
|TTTCTATGTT|CTTTTAAAA|TTTAAATTAG|ATGCTTGGCT|CATTAATGTT|CAGCTTTTA|85020|
|ATTTTTCTAA|GATAAGCATT|TAAAGCCTAC|AAATTTTCCT|TAAAATTCTG|CTTTAGCTTC|85080|
|ATTGTATATT|TTTATAAATA|ACTTTTTATT|ATTGTTCCAT|TCTATACATC|TTCTAATGAC|85140|
|TTATTAGTAG|TTTACATTTC|CTAATATTTA|GAATCTTTTT|AGTCATCTTT|TTATTATTGG|85200|
|TTTATAATCT|TATATTGAGG|CTAGAGAAAA|TGATCTGTGT|AATACAGATT|TATTGAAACT|85260|
|TGTTCAGACT|GTTTTCTGCC|TAGTATTTAC|TCAGTTAGTG|CATGTTCCAT|CTATACCTGA|85320|
|GAAAACTGCA|TATTCTCTGC|TTACTATTAT|TAAACAATTG|CTGAGCTTTA|TGTATTGACT|85380|
|ATGAGATTGC|GCTTCTTAGA|TTGTTCAGAC|CTTCCGTATC|TTCCCTTATT|TCTTTCTTTT|85440|
|GGTCTGCCTG|ATCTATCAAT|TATGGAAAGA|AGAATGTTAA|AACATCCAT|GATGATTGTA|85500|
|GATTTGTCCA|TTTCTCCTAT|AATTCTACAA|TTTTGCTTT|GTATATTAAC|ACAATTCTAA|85560|
|ACATGAATTC|ACTAATAATG|TAGTACATTT|ATGTTTAAAA|TTGTGTTATC|TTTTTAGGT|85620|
|GACTCCTTTC|ATTCTTTCTT|TTTTTTTTTT|TTGAGACAG|AATCTCTCTC|TGTCACCCAG|85680|
|GCTGTAGTGT|AGTGGCGAAA|TCTCAGCTCA|CTGCAACCTC|TGCCTCCCCG|GTTCAAGTGA|85740|
|TTCTTGTGCT|TCAGCCTCCC|AAGTAGCTGG|GATTACAGGC|ATGTGCCACA|ATGCCCAGCT|85800|
|AATTGTTGTA|TTTTTGGTAG|AGCCAGGGTT|TTGCCATGTT|GGGCAGGCTG|GTCTTGAACT|85860|

-continued

| | | | | | | |
|---|---|---|---|---|---|---|
| CCTGGCTTCA | AGTGATCCGC | CTGCCTTGGC | CTCCCAAAGT | GCTGGGATTA | CAGGCATGAG | 85920 |
| CCACCACACC | TGGCCCTTCT | TCCATTCTTA | ATAATGCTCT | GACTTAATAT | CTTTTGATAT | 85980 |
| AATACTATAA | CAGTATATGA | CTATATTATC | TATCTTTTAG | CTTCCAATCT | TTCTATATGT | 86040 |
| TTTTGTTGAT | GTGTCACACC | AATAGATAGG | TGGAATTTTA | AAAATCCAAT | TGATATTTTT | 86100 |
| TCTCTTAAGT | GGTATTACCA | CCCCGTAAAC | ATTTTAATTT | CTCAACATGG | GTTTTCCTGG | 86160 |
| GTCATTCAGG | TAATATGAAT | TGAAACCCCA | AACTTCTGTG | AGTCAGGCTG | ATAAAAGCTA | 86220 |
| ACTGAATAGA | GTTTGAAAAA | GGAGGGTATT | TACAAAGGTG | AGGAGTTGGG | AAATCCACAA | 86280 |
| GGAACAGGAA | GCACCCAGAA | CTAGGAACAG | TTAGAGAGCC | ATCACCTCCT | CTGGGCCTCA | 86340 |
| AGTGGCAGGT | GTAGGGAGCT | GTAACTATAC | TAGAGTGTGC | CCAGAGGCAG | AGGAATGCAG | 86400 |
| ACCCTCCAAA | TCATAGCGTG | GGACTGGGGT | ACTGAATACT | CCCAAGGCTG | CTTCTTTGTG | 86460 |
| CCCTATGGTC | TCCTCTGGTG | CTTCCCATTG | GCTGAACCAA | GCCAGAGGGC | GGAAAGCCTG | 86520 |
| GTTAATCTGT | CCATGTCAGC | CTTCCTGGGC | ACAGAGCAAG | ACAGGGAAAA | GTGAGGGATT | 86580 |
| ATTTGGAAGA | ACAAACAGAG | AGCATCCAGC | ACAGGAAGTG | TTTCTGAATA | CTTGAATTCC | 86640 |
| TTAATTGTCA | CAGACCAACT | GATCAACATT | TAACTCAGTA | GCACAGTGGT | TTCCTTAACT | 86700 |
| CTCTTGTTAG | AACATCCTAT | TACCATTTTT | TATTTTTAAA | ACTGCATACT | GTTCCAGTAT | 86760 |
| CTCACTTTAG | TTATCAGATC | TTTTTCTGTC | TTGTTGATT | CTAGTCTGAT | ATTTTCCAT | 86820 |
| GTTATATTGG | TCCTCCAGTG | TATTATTATC | TCATACTAAT | GCTTATGGAA | CATTATCTGA | 86880 |
| GGGGAAAGAG | AAGAGCTTAC | AATTAAAAGT | CATGGGACTA | GGCATGTGTC | ATGAGACCTG | 86940 |
| GGTCTTCCAA | TAACAAGCTA | AGACATTAGC | TGAGTCATTT | TCCCTCTCTG | ATTCTCAATG | 87000 |
| TTGGTGGTTA | TTCAGTAGAG | AAGGGAAAAG | GTATCTTTCT | GCTCAACTGT | CTCATGATTC | 87060 |
| CTGGAAGTCC | TGCATGGGAG | AAGAACTTTG | GACAGGATGG | TAACCATATT | AACAGGTTAG | 87120 |
| TTCTGTACCT | TGGCATCCTT | GAATAATTAA | GACGAAGATG | ATGTTGATGA | TATCATTATT | 87180 |
| ACTACATGTT | GTTAGAAGAG | CTGAAGCAGG | ACTGGCTTGT | CTGTCATAAT | GTAAAAGAGT | 87240 |
| CTTGGAAGAT | GTCCGGGGTC | CAGGGTCCAA | AACCCCTCGT | GGCCTTTGGA | ACACCAAGCT | 87300 |
| CTGTGCCAAA | TGGTGGAAGG | CTGCCCTGCC | GCACCACAAA | TCTAAGCCTA | GGGCATAAAA | 87360 |
| CCCCTTGTGG | CTTGGATGGA | ACCCAGGGCT | CAGGGCATAA | AACCCCTCAT | AGCCTCTGGA | 87420 |
| AAGTGCACAG | ACTTGTTGGT | TCCTTGCTTT | TCACTCATAA | ACGTGTCCTC | TACTATCTCA | 87480 |
| AGCAGCAGAG | TATATTCTAC | ATGTGTCAAA | GAAAATGCTA | AACTGTCACA | GCTACGCTTA | 87540 |
| ATGCACCACT | ACCTTTCTAC | CCCCATGTCC | TCATGCCCTC | ACCTGTTTAC | CCTCACGTCC | 87600 |
| TCACCACCTG | CTTCTTTGTT | TGATCACCAA | TAAATAGTGT | GGGCTCCCAG | AGCTTAGGGC | 87660 |
| CTTTGCAGCC | TCCAATCTAG | TGCTGGCACC | CTGGACCCAC | TTTATGCACT | CTTAACTTGT | 87720 |
| CTTTTCTCAT | TCCTTTGACC | CCGCCGGACT | TTGTAGCCCC | CACGGCCTGG | TGTTGGGCCT | 87780 |
| GATCACCCCA | ACAACTACCA | CTTATTAGTG | GTTACCATGT | ACCAGGAAAT | TTACCAAGC | 87840 |
| ATTAAGCAAA | CATAAGCTTA | TTCAATCCTA | CCCACCATTC | TCTGCAACAA | ATACGGTAAT | 87900 |
| TTCCACTTTA | TAGTTAACAA | ACTGAGGCTC | AGAAAGTTAA | ATGATTTGCC | TAAGCTCACC | 87960 |
| CAGTTTATAA | GAAACAATAG | TTGGGTTTGA | ACACAGGCTG | GTTTTATTGA | AAATAACTTG | 88020 |
| TGGCTGGGCA | TGGTGGCTCA | CACCTGTGTA | ATCCAGCACT | TGGGAGGCC | GAGGTGGGTG | 88080 |
| GAACACTTCA | GGTCAGGAGT | TTGAGACCAG | CCTGGCCAAC | ATGGCGAAAC | CCCATCTCTA | 88140 |
| CAGAAAATTT | AAAAAAATTA | GCCACTTGTG | GTGGTGCGCA | CCTGTAGTCG | CAGTTACTCC | 88200 |
| GGAGGCTGAG | GCAGGAGAAT | TGCCTGAATC | CAGGAGGTGG | AGGTTGCAGT | GAGTTGAGAT | 88260 |

-continued

| | | | | | | |
|---|---|---|---|---|---|---|
| AGTGCCAGTG | CACTCCAGCC | TGGGTGACAG | CAACACTCCA | TCTCAAAATA | AAATAAAATA | 88320 |
| AAATAACCTG | TGTTCTTCAC | AGCAACAAAA | TTATTTTTGT | TTGTTTTGTT | TTGTTTTGCA | 88380 |
| GTTAGTGTGA | CTCTGGATCC | AGATACAGCT | CATCACGAAC | TAATTCTCTC | TGAGGATCGG | 88440 |
| AGACAAGTGA | CTCGTGGATA | CACCCAGGAG | AATCAGGACA | CATCTTCCAG | GAGATTTACT | 88500 |
| GCCTTCCCCT | GTGTCTTGGG | TTGTGAAGGC | TTCACCTCAG | GAAGACGTTA | CTTTGAAGTG | 88560 |
| GATGTTGGCG | AAGGAACCGG | ATGGGATTTA | GGAGTTTGTA | TGGAAAATGT | GCAGAGGGGC | 88620 |
| ACTGGCATGA | AGCAAGAGCC | TCAGTCTGGA | TTCTGGACCC | TCAGGCTGTG | CAAAAAGAAA | 88680 |
| GGCTATGTAG | CACTTACTTC | TCCCCCAACT | TCCCTTCATC | TGCATGAGCA | GCCCTGCTT | 88740 |
| GTGGGAATTT | TTCTGGACTA | TGAGGCCGGA | GTTGTATCCT | TTTATAACGG | GAATACTGGC | 88800 |
| TGCCACATCT | TTACTTTCCC | GAAGGCTTCC | TTCTCTGATA | CTCTCCGGCC | CTATTTCCAG | 88860 |
| GTTTATCAAT | ATTCTCCTTT | GTTTCTGCCT | CCCCCAGGTG | ACTAAGGAAA | AGAGCAGAAG | 88920 |
| CTCCTTGGTT | TAACCAGCAC | AGAGAAAATA | ATATAAATCC | CATAAGGGCA | GACGTTTGGT | 88980 |
| CTGTTTTCTT | CGCTGTCATT | TCCTTAGTAG | TTAGACTAGT | GCTGAGATTT | TAGTGGATAT | 89040 |
| ATAATTGATT | TATGTTGAAT | ATATGGACTT | AGCAACTAAA | AATACCACAG | ATGGTTAACC | 89100 |
| TGGACTGGGG | CAAAGCAAGA | TAATAGTGAT | GATCGTATGT | TGCTGTCTCC | ATCCGTCTTT | 89160 |
| AATGGGTCAG | GGCTTTGATT | TCCAAGGGTC | TTCAGGTGAT | GAGTAGGGGT | ACCCACAAGT | 89220 |
| CAGAAGGTCT | GCGTTCTCCT | AGTTTGTTTG | CTGCCATTTG | AACTCATGTA | GGGAATGAAA | 89280 |
| GAAAGCTGCA | ATTATCCGCC | AACTGCATTT | AAAACAAAAC | AAAACAGAAA | AATCAAAATA | 89340 |
| ACATTGACTC | TTCCAACCAC | TGACATGTTG | TTTAATAATC | TAAGCGGCAG | TCCTGGAGGC | 89400 |
| TACCAGACTT | ACTGAGTTCT | ACCTGAGAAA | CAGCCAAGCA | AAGTGTGAGA | GAAGGGTTAA | 89460 |
| GACTGGCTTA | CAATGAGATG | CTTCAAATGA | AAAGGGAATT | ATGAGTAAAA | TTGAACTTTG | 89520 |
| ATGGGGATT | CAGTTCTGGA | AAAGAATTTG | GTATTTTCCA | GTCTGCTAGG | ACCAATTACC | 89580 |
| TTGAAATATT | TTAAAATCTC | AGTAAATAGT | TATTGCTGAA | ATGGCTGTTG | GCAGTTCTTA | 89640 |
| TTATGATTCA | GAGAAGAGCA | AATAGACCTT | AACTTCATTT | TGAAAAAGAC | CAAATTACCA | 89700 |
| TACCCGAGTG | AGTAATGACA | GGACTACAAC | TAAAACATAA | ACAACATTAA | TGATGACCAT | 89760 |
| AAAAAGTCAC | AAAATTGCTA | AATGTTATAA | TTTAGAGTTG | ACATAAAAAT | TGATGGCCAG | 89820 |
| GCATGGTGGC | TCACGCCTGT | AATCCCAGAA | CTATGTGAGG | CTGAGGCAGG | TGGATCACTT | 89880 |
| GAGGTCAGGA | GTTCAACACC | AGCCTGGCCA | ACATGGTGAA | ACCCTGTCTC | TACTAAAAAT | 89940 |
| ACAAAAATTA | GCCGGGCATG | GTGGTAGGGG | CCTGTAACCC | AGCTACTCGT | GAGGCCAAGG | 90000 |
| CAGGAGAATT | GCTTGAGCCT | GCAGCAGCTG | CAGTAAGCCA | AGATCATGCT | GTGCCTCAAG | 90060 |
| GAAAAAAAAA | ATTAATGTTT | ACTGATATTT | GTTGAAGTCC | TACAACATCA | CCTCTGAGAA | 90120 |
| TAGGAGAAAT | GAAGCAACAG | TTGTGTCTAG | ATGTCAGAGG | CATGGCTGGG | CCTCCATCTC | 90180 |
| TGCCTAAGGG | AGATATAAAA | GAGTTCAAAC | TATTGCCCAT | GTTCCCAGG | GTCAGAAGTT | 90240 |
| CTAATTATGA | TGATAGAGGC | TGGGTTGTAA | GTAGTAAGTG | AAGGGTAGCA | GAATATGCCA | 90300 |
| TCTTTGGCAT | AAGAAGTATT | TTGAGTTGAA | GACAATTGAG | AAAAAAAATA | GATTAAAAAC | 90360 |
| AAACAAACAC | CTCTGCCCTC | TCCCTATTTG | CCTAAAAGCA | GGATATGAAA | TTGTGAAGGT | 90420 |
| GTCTTCTTAC | TCGGGGAAGA | ACAAAAGTTA | GTCACCAGAG | ACTTTAGACT | CTTATCAGCC | 90480 |
| TGGACATAGC | ACCAGAGAAG | TCTTTTTTTT | TAAAAAAAAA | AAAAAAAAA | GGGAAAGAAA | 90540 |
| AAGTTGCCTT | CCCACAATTT | ACTGCACTAG | AAACTCAAAG | TCCTTTTCGT | CTTCCTTGTC | 90600 |
| ACTTAAAAAA | TGTATTCTTT | TCTTAAAATG | CTATATAAGC | CCAAGTTCTA | AATCCTCTTT | 90660 |

```
TGAGTATTCA  TCTCAGTACT  CCCCTGTGTT  TGTACAATGC  ACATGCTTTG  TTTCTGTCTT  90720
GTCAATCTGT  CTTTTGTTAG  TCTACTTGAT  AGGGCCACAG  ATGGAGAACC  TAAGATGAAT  90780
AGAAAAAAAA  GATTTTTCTC  CCCAACAGAA  GGATTATCGC  CAGTTGCACT  TGTTCTATAT  90840
ACCCGTAGTC  TCGGTATGCT  GACCCAGACT  TGGGTAATAG  GACCCAGTGG  GTAACCGAGG  90900
AACCCCACCT  TTGTGCAGGA  TCAGTGAAGA  TGTAATCTGG  ATATTCATAA  GCTCTTCTCT  90960
ACCTCTTGGC  ATCCCACAGT  CCTGTGTTAA  TGTAAGTGTG  GTCTTCCCCA  GAAAGGGGAG  91020
GCCTCCCTAA  CATTGTTAAA  GCCTAGCATA  TGCTGCTTAG  AGGAAATTCT  ATATCCCTAA  91080
GCACTTAGAT  TGCTGAATAA  GAAAGAATGA  TAATAAAATA  AACAATTAAA  TAAAGTTTT   91140
AAAAAATGAA  TAAATAAAC   CTGTGGAAAC  TATAAGGAAG  GCCAGAAGAA  ATATAAAATT  91200
GGAGATTAAT  TGGGGTGCAG  GAAAGTTATG  GAAAGAATAT  AAGTCCTGCT  AGATAAATCA  91260
TTAGCTATTT  TAATAAAGAA  TACAGAAGAA  AATAGGAACA  AAGAATATA   TACTGGAATA  91320
ATTTTGAGAG  TAATTTGAAG  AATTAGATGC  AAATAAATTT  GAAACCTTT   AAAAGAAAC   91380
CAATGGCCTA  ACTGACCCAA  GAAGGAAAGA  AAATCTAAAC  AGACTGATAA  ATACAAAATG  91440
AAATTCAGAC  ACTTACAGAG  CAGCCAGGCA  TGGTGGCTCA  CACCTGTAAT  CCTGTCACTT  91500
TGGGAGGCTG  AGATGGGAGG  ATCACTTGAG  GCTAGGAGTT  TGAGACTAGC  CTGGGCAAGC  91560
TCCCATCTCT  AAAAGAAAAG  AAATTAGCTG  GGCATGGTGG  CATGTGCCTT  AGTTTCAGTA  91620
CTCAGGAGGC  TGAGACGAGG  ATTGCTTGAG  CCTAGGAGGG  CAAGGCTGCA  GTGAGCCATG  91680
GTCATGCCAC  TGAATTCCAG  CCTAAGTGAC  AGAGCAAGAC  CTTGTCTCAA  AAAAAAAAA   91740
AAAAAAAGTT  ACAGAGCTCC  AACTAAATAA  TGTGGGGAAC  AAAAGAAAAA  AGAAGATGAT  91800
TTTATGGCTG  ATTTTTTTTT  TAAGGAAAAG  CAATTCATGT  ACCCTTGAAG  ATTAGATTAA  91860
GTTCTATAAA  ATAGCCCAAA  ATGACAGTGG  CTGAAACAAG  TTTATTTATC  TCCCATTTAA  91920
AGCAAGTCTA  GATGTGGAAG  TCTGGGAAGC  CCAGAAAATC  CAGGTCTTGT  TTGTGTATGG  91980
AAACTCCAGA  AAATCACAGA  TTCCTTCCAG  CCACCCCTCA  ATTACCCCTG  GGATCCAAGA  92040
GAGCCACTAA  AGTTCCAGCC  ATCATACTCA  CAACCCAAGT  TGTAGGATGG  AAAAAAGGAC  92100
ACAAAGTAG   GGTGAAGAGC  ATGTGTGCAA  CAGCTCTCTT  TTACTCTAGT  GTCCTAAAAC  92160
CTATCATAAA  ACCTTTGGCT  TGCCTTGCAT  TAGCCAGAAT  TTAGTACATG  GCCACACTTA  92220
AGAAGTCAGA  AAGATTAGCT  TTTTTTCCAG  GGTAGTTGGC  TGAAAATCAG  GAGTTCTCAT  92280
ATTAAAAAAC  AGAGAAGGGA  CATCGAATAG  ATGACCAACA  ATCTCCTTCA  CACTCATACT  92340
ATTTAAACTG  TCCTAGTCAA  TGACCAAAAA  AGAAAAGCCT  ACAAACTCAT  TGATATAAAA  92400
GCTTAACAAA  GGTACTCCCC  GCCCCCCGCC  CGCCACACAC  CATCCCCAAA  AGGAAATTTC  92460
TAATCCAATT  AACAGTCTTA  GGTTGGGCTG  CTGAAACAAA  ATACCACAGC  CTGAGTGACT  92520
TAAACAACGA  CAATTTATCT  CTCACTGTTC  TGAGGTCTGA  GTTGATTCTT  TGTGAAGGCC  92580
CTTTCCTAGC  TTGCAGATGG  CTACCTTCCT  GCTATGTCTT  CACATGGCAA  AGAGAGAGCT  92640
AGCTTTCTGG  TCTTTTCTTA  TAAGGGACCA  GTCCCATCAT  GCCCATCATG  AAGACTCGAT  92700
CTGCTAGGAT  CTCAACTAAA  CCTAACTATC  ACCCAAAGAG  CCCACCTCCA  AAGACCATCA  92760
CATTGAATGT  GAGAGTTTCT  ACATATGCAT  TGTGGGAAAC  ACAAACATTT  ACTTCAACTG  92820
TAACTATTGA  AGCAAAAATG  TCCCCCCACC  ATAGACATCC  AGCACCACAG  TAGTACATTT  92880
ATTACAATTG  AACTTACATT  GACACGTCAT  TATCAACGAA  AGTCTGTAAT  TTACATTAGG  92940
GTTTATTCTT  GGTGTTGTGC  TTTCTATGGG  TTTTGACAAA  TGTATAATGT  CATGTATTCA  93000
CCATTATAGT  ATCACAGAAG  TTTCACTGCC  CTAAAAATCC  TGTGTTCTGC  CTTTTCAACA  93060
```

| | | | | | | |
|---|---|---|---|---|---|---|
| CTTCCTGTCA | CCCAATTTCT | ATCAACTAAT | CTTTTGACTG | TGTCCATAGT | TACTGTCTTT | 93120 |
| TCTAGAGTGT | CATACAGTTG | TGAAGCAGGA | AGCAGGAGTG | AACTCCGGAG | GCAGGGACTT | 93180 |
| TACTCCGGAC | CAGATTGAAG | ACTAGCCGAA | ACAGGGACGA | GGTTAAAGCA | CCTCTCCATA | 93240 |
| AGACACGCCC | ACCAGCGCCA | TGTCAGTTTT | TCGTTGCCAT | GGCAACAACA | GGACATTATC | 93300 |
| GACTTCTTTC | CTCTGTACCT | ACTCCGAAGT | TACCACTCTT | TTTCTAGAAA | TTTCTGCATA | 93360 |
| ATCCCCCTTA | ACATGCACTT | AACTAAAAGC | AGGTATATTA | CTGCAGAACT | GCCCCTGAGC | 93420 |
| TGCTACTCTG | GGCACATTAC | TTATGGGTTA | GCCCTGCTCA | GCAAGGAGCA | GTACCTGTTC | 93480 |
| TGCTGTTGTA | CACTGCTGCT | TCAGTAAAAG | TTGCTAACAC | CACCACTTCA | CCCTTGAATT | 93540 |
| CTTCCCGGGC | TAAGCCCTAA | TTTTTGGCTT | GCTTGCCCTG | CATCAGTTGG | AGTCATATAG | 93600 |
| TATGCAGTCT | TTTCAGGTTG | GCTTTTTAGT | AACATACATT | TAAGTTTCCT | TCATGTGTTT | 93660 |
| TCATGGCTTG | ATCGTTTCTT | TTCTTTTTCT | TTTTCTTTTT | TCTTTTCTTT | CTTTTTTTTT | 93720 |
| TTTTTTTTGA | GACAGAGGAG | TCTTGCTCTG | TTGCCCAGGC | TGAAGTGCAG | TGGCACTGGC | 93780 |
| TCACTGCAAC | CTCCATCTCC | CAGGTTCAAA | CGATTCTCAT | ATCTCAGCCT | CCCGAGTAGC | 93840 |
| TGGGATTACA | GGCTCACGCC | ACTATGCCCG | GCTAATTGGG | GTTTTCCCAT | GTTGACCAGG | 93900 |
| CTGGTCTCAA | ACTCCTGGCC | TCAAGCAATC | CACCCACTTC | GGCCTCCCAA | AGTGAATGCA | 93960 |
| TTTCTTTTTA | ACTCTAAATA | ACATTCCATT | ATTCAGAAGT | ACCACAGTTA | TCCACTTACC | 94020 |
| TACTGAAAGA | CATCTTGTTT | CCAAGTTTTG | GATAAATTAT | GAATAAAGCT | GCTATAAACA | 94080 |
| TCTATGTGCA | GGTTTTTGTG | TGGAGATAAG | TTTTCAATTC | CTTTGGATAA | ATACTAAGGA | 94140 |
| GTGTGATTGG | TGAATCTTAT | GGTAAAAGTA | TGGTTACTTT | TGTAAGAAAC | CACCAAACTG | 94200 |
| TCTTCCAAAG | TGATTGCACA | TTTTGCATTC | TCACCAGTAA | TGAACAAGTT | ACTATTGCTA | 94260 |
| CATATCTTTG | CAACCTTTGG | TGCTGACAGT | GTTCTAAATT | TTGGTCATTC | TACTAGGTAT | 94320 |
| GCAGTGGTAT | CTACTTGTTT | TAATTTGCAG | TTCCCTAATG | ACATGATGTC | AAGCATCTTT | 94380 |
| TCATATGCAT | ACTTGCATCT | GTGTATCTTC | TTTGGTGAAC | AGATGTTCAG | GTCATTGGCC | 94440 |
| TGCTTTAAAT | CAGGTTATTT | TCTTACTGTT | GAGTTTTAAG | TATTCTTTGT | ATATTCTAAA | 94500 |
| AATATTGTTC | TTCATCAGAT | CTGTCTTTTG | CAAACATTAC | CTGCCAATGT | GTGGCTTTTC | 94560 |
| TTCAACACTT | CTTTGTAAAT | TTGCAAGTCC | TTTGAGAAAA | GAAATGCACC | CAAAGTATTA | 94620 |
| ATTTGGCAAT | CTCATATCAC | GAGAGTACTC | TAAAGCTAAA | TAAATTACAG | TTTTTCAAAT | 94680 |
| TTTGAATTAA | TTGATCTTTG | CTATTGTTAG | CAAGGTCTTG | TATTCTTTTT | TTTTTTTTTT | 94740 |
| TTTTTTTTTA | ATAGAGACGG | GTCTTGCTAC | AGTGCCCAGG | CTGGTCTCGA | ACTCCAGGCC | 94800 |
| TAAAATGATC | CTCCTGCCTT | GGCCTTCCAA | AGTACTGGGA | TTACAGGCAT | AAGTCACCAC | 94860 |
| GCTCAGCCAT | CTGGTATTCT | TTAGCAACTG | TTTGGTAACT | TAATCTTTCA | CTTTTTGAAA | 94920 |
| ACAAAAATA | GTTTTTTTCT | CATAGTTTTC | TAACAAAATC | TTCATAACTG | AAATAATTTC | 94980 |
| TCTTTATCAC | CTCTTCTTAT | AAATATGGTT | TTCTTTTTTT | AAATAAAAAT | TTAAGACATT | 95040 |
| TTATAACTGG | CCAAATTTAC | TAGCTTAGAT | ACTATTAGAT | AGTCAATATT | TTTTGTTGGA | 95100 |
| TATTTGATTT | TTATTTCAGG | CAACTAATAT | CTATTCATTT | TTGCACTGTT | GGAAGAAAAT | 95160 |
| TACTGATCAA | ATTCACTATG | TATTTGCAGA | AAATGGCTTT | CAATATTGTC | TACTTTATCA | 95220 |
| TCCTTTTTTT | TTTTTCTTT | CTTCCTTTTT | AGATACAGGG | TCTCACTATG | TTGCCCAGGC | 95280 |
| TGGTCTCCAA | CTTCTGGGCT | CAAACAATCC | TCCCTCCTTG | GCCTTCCAAA | GGGTTGGATA | 95340 |
| TGTTTTATCT | ACAGTTTTGT | TGTTTTGTTC | TGCTACAGGA | TATTTGCAAT | TGCCATTTAT | 95400 |
| CATGAAATTC | ATGACATACC | TTCTTCCACT | CTCCTTTTA | TCTTTATTGT | TCTGGTTATA | 95460 |

| | | | | | |
|---|---|---|---|---|---|
| GGACTAGCTT | TGCATCTCTA | CTCAATTCTG | TATCAGTAGT | ATGCTTTCAT | TTTAAATTTT | 95520 |
| AAGTTTGTCC | ATATGTATAT | TGACACAGGG | TCTTGCTCTG | TTGCCCAGAC | TGGAGTGCAG | 95580 |
| TGGCAAGATC | AGGGCTCACT | GCAGCTTGA | CTGCCTAGGC | TCAAGTCATC | CTCCCACCTC | 95640 |
| AGCCTCCAGA | ATGGCTGGGA | CTACAGGCAC | GCACCACCAC | ACATGGCTCA | TTTTTTTGTA | 95700 |
| TTGAGACAGG | GTTTCTCCAT | GTTGCCCAGG | CTGGTCTTGA | ACTACTGGGC | TCAAGCAATC | 95760 |
| CTCCCACCTT | AGCCTCCCAA | AGTGTTGGGA | TTACAGGCTT | GAGCCACCAT | GCCTCGCTTC | 95820 |
| TACACTTATT | TTTAATTCTA | AAATAATTTA | TAATAATAAA | TATTAACAAT | TAGATTTAAT | 95880 |
| TACTGATAAA | TATTAAATGT | TAAATAGGTT | TTATTAAATA | ATTAAATAAA | AATGAAAATA | 95940 |
| ATCAGTATTT | CAATTTAATT | ACTAATTATA | ATTCACAGTT | ATCCTTGTAA | CTCCTAATGT | 96000 |
| CTATATAAAA | GATTTTTATA | TTTTTAATT | CTTAAAATTT | TATTATTTAT | TTCACACCAG | 96060 |
| GCCATCACTG | TGATACATTT | TTTAAAACAC | ATTAAATTAT | CACCAGAAAA | GTGCTGTGAT | 96120 |
| GGAAAATATA | AATTGAAATA | CCTTTTCTGG | TTAGGAGAGT | AATTCTGTTT | TTCTGATAGA | 96180 |
| GAATAGAAGA | GTCCTTCAGG | CCCCTCCAAA | CTGTCATATT | CCGGGCATCG | GGTGTCCCCA | 96240 |
| TCCTCACTTC | AGTCCACAGG | CAGGGTCCTC | AGTCTTCAGC | GCTCCTTCTC | TTTCCCCTTT | 96300 |
| GTCTTGTGTC | TCCTTGGGTC | TCTTTTCTCC | AAGACCTAAA | CTCCCTGAGG | ACAGGACTAT | 96360 |
| TTTTTACATC | TTGATGTCAC | TCCTGAGCAC | TTGCTTTAAT | GTGTTGGACA | CTGGGTCCAT | 96420 |
| TAAAGATTGT | ATGTGAAATT | ATAAAAGAAA | CGTTTTCACC | TTTCTGTGGT | ACAGCTATAA | 96480 |
| TTTCTGGTTT | CATTTACCAA | CTGGGTGAAA | GTGGACCAGT | GACACCATTT | GTCTGGGCCT | 96540 |
| TCCTTTCCTG | AAATATAATA | TTGGGGCAAT | AGTCCCTGGT | TCTTGTAAGG | TGTTCAGGCA | 96600 |
| CAAAACGCTA | GGCATGTAAC | ATACTAAATG | AGGTTTTCCC | AGTTAATTTA | TATGATTGCA | 96660 |
| AAGGACGTTC | ATATACACGG | TCTGCTAAAG | AATTCTGGGG | CCAATTAATC | TCTGTGGCAT | 96720 |
| GATGGGTAAG | TCGATCCCTT | CTCTGGGCGT | CTATTACTTC | AGAAAAGGCA | TGAACTCAAT | 96780 |
| TTTAGGGACC | ACACAAAAAA | ATTTATTCAC | TATCGTGTAG | GACTTGGTCA | TTAGAGAGCT | 96840 |
| TTTGTTTCTT | TTTTTTAAAA | TTTTTTTAA | TTTTTATTTT | CGTGTATGTG | AATTTAATGG | 96900 |
| AGAGCTTTTA | AATAACCAGA | TATTTAAATA | ACCAGATAAT | ACAGATGCCC | GGCCTGCTCC | 96960 |
| AGACAAATTA | GAAAAGTATG | TAGGTGAGGA | GGGACCAGCC | AGAAGGCGGT | TTCAGCTCTG | 97020 |
| GAGTGACACT | GAACGTACTT | CTCTTCCAGG | GATGTCACGA | GGTGTCAATT | TCTCTGGCCT | 97080 |
| TACCCAGGTC | CATGCCCGCC | CCCAGGGGCC | CCAAGAATGA | CTTCAGCACC | CCACCCCCAC | 97140 |
| CTCCCTCTCC | AGATGTGGGT | CCTGGGAGCG | TTCAAGGCCC | GTCAGTCACT | CGAGCCACCC | 97200 |
| CTTGGCGGCT | GGACCAAATC | TTGGGCTGCC | GCCTGGATCT | GCAGCTGGAA | AGCGCCGTGA | 97260 |
| CCACCGGTGT | CCCCAGCTGG | AGCAGGGCGG | GCTGCACGAC | TCGCGAGGAC | GCCCTGAACC | 97320 |
| GCGGCTTCCT | CTTTCATAGC | CGCAGGACTC | GTGGTCAGAA | GGCCGACTCC | AAGCCTCAGC | 97380 |
| GGATCCACGA | AATGGCCTCT | TTGAGGCTGT | GGTGAAATTT | AAGATACCCT | TTCCCTGCCA | 97440 |
| TTGTTACTGA | CGTACTTCAG | CAAACAGGTT | AAAGTTCTGA | AAGGACGTGG | TCACGACTTT | 97500 |
| ATATTTCTTA | CAGATTTGTG | TCTCATGTTT | TGTGCGTAAA | AACCATTCGT | CCTCATTTGA | 97560 |
| GATTCTCATA | TCCGTAATTC | AGTTATACAT | AAAACTGAAT | TCAGTTATAT | CATAAAATGT | 97620 |
| TCCCATGCGG | GGAATGATTC | GTTGGGGTCT | CAGCCTGAGG | CCAGACGCAG | CAGAGAGATC | 97680 |
| GGGAGTTGGG | GGATGGCGGG | CGGGGAGCGG | AGAGGAGGCC | GCCCGCCGCC | AGACTCAGGG | 97740 |
| TCCAGCAGAG | CAGCAAATGC | TCCCCGGCTC | CCAGCCAGGG | CGCAGCTGCT | GGCCTGGGGC | 97800 |
| CGCCCCTCAC | GCCGCAGGAG | CCCCGCCCGC | AGCGCCGGCC | CTGCCCCTGG | CCTGTGAGGG | 97860 |

| | | | | | |
|---|---|---|---|---|---|
|CGCCAGCGCC|CCCTACAGCT|TGCAGTCGCC|CTGCGCGCCT|CCCCGCGAGG|CTTGTTTTCT 97920|
|AGCGCCTCTG|GTGGGCCGCC|TCCCGCAGGC|CTGGTGTGAG|CCTGGGGTCC|GTTCTCACAG 97980|
|CTGGATCTGG|GGTCTGAATG|CCGCGCCCTC|TGGAGAGCCA|CAGATGGGTC|TCCGCTGATG 98040|
|CTTCTCTCAA|TTTCCTCTAA|GAGCGAGAGC|TCCGGGAAAG|GAGCCGATCC|TGGTGGAAGA 98100|
|CTACAGGTCT|GAGTCCACTG|GACGAAAAAC|GAGGTGCGTT|AAGAGACCGC|GGGAGTGGGG 98160|
|AAATGGGGAA|GTGAGGGTGG|GGACTGGGCA|ATGGGGGCGG|GACGAGAGGT|CTGGGGCTGG 98220|
|CGGGGACAGG|GCTTAAGAGA|GAGCCACCCC|TCCTAGCCTT|GAAGCTGTAC|CGAGCTTCCC 98280|
|TGTGATATTT|TAAAATGCAA|AAGTACAAAA|ATTGAAGTAA|TGGAACTATG|CGTACGCACC 98340|
|TCCTAGATTT|TTAAAGGTTA|ACGTGTGACT|GTGTTTACTT|CAGATGTTCC|TGAAATAAAT 98400|
|GAAAATGACC|AGTTAAAATG|AAGGAAGAAC|GCGCTTGCGT|CCCTCCTAGA|GGTCAAACAC 98460|
|TCTTCTGAGG|ATAGGTTGTA|TGCTCTCAGC|GCCTCTTTTT|ATTAAAAGTA|TTAAGAAGTA 98520|
|CTTTTCCAAA|TATTAGATGT|AGTGTGTCAT|ATCATTTAAA|CGATTTTTTT|TGTTTAAAAT 98580|
|AGTCTTTTAA|AAATAATCTT|TTTATTTTTA|GATTTTTTG|AGACAGAGTC|TCGCTGTGTT 98640|
|GCTCAGGCTG|GAGTGCAGTG|GCGCCATCTC|CCCTCACTGC|AACCTCTGCC|TCCCAGGTTC 98700|
|AAGTGATTCT|CCTGCCTCAG|ACTCCCAAGT|AGCTGGGATT|AAAAGCGTGA|GCCACCACAC 98760|
|CCTACCAATT|TTTGTATTTT|AGTAGAGATG|GGGTTTCACT|ATGTTGTCCA|GGCTGGTCTC 98820|
|GAAATCATGA|CCTCCACTAA|TCCACCTACC|TCGGCCTCCC|AGAGTGCTGA|GATTACAGGC 98880|
|ATAAGCCACC|GTGCCTGGCC|ACTTTAATCA|TTTTTGTTTT|TGCATCTAGT|CTAAGAAATT 98940|
|CTGCACTAAA|ATTCTGCACT|ATTTTCTTCT|AAAATTTTAA|AACATTTTCT|ATCTGTGTCT 99000|
|TTGTTAGATG|TAGAAACTTT|TGTGTATGAT|ATGGGGTATA|GCTATAATTT|TATTTTTATT 99060|
|CCATATGAAA|GCCAGTTTCT|CAGCCCAGGT|AATTGAATAG|ACCATCCTTT|CTCCACCAAC 99120|
|TCTTAAGGCT|ACTTCTGCTC|TATTGTGTTC|ATAGTAGTTT|CTAGGCTTTC|TGTTTTGTTG 99180|
|TACTGATTTC|TTCACCTATT|TTTGCATCAA|GGCTCTCCTC|TTGGGGAAAT|AAAACAATCC 99240|
|TGCCAACCAA|AGACCCTCT|GGATCCTCAA|ACACGCCATC|AGCATGGAAG|GCCGCTATGG 99300|
|CATAGCGAGA|GATAAATAGG|ATTCAGGCAG|TGCTGTCCTT|ACATCGCAAT|CATTCAGGTA 99360|
|GTTAGCAGGA|GCATCAATCA|GTACAGATAT|CCAGAGCTGA|TGGTCTTATT|TGTATGAATG 99420|
|CCCAGTGCAT|ATGGGATTGG|AGGGGAGGGC|TTGGAGTGGG|ATGAGGGGCT|AGTGGGATCC 99480|
|AGAAAGGGGC|TAGTCTTCAG|GTCTTCCCTG|GAGAGTATGT|AATCTCTTAT|AACTAAGTGT 99540|
|TGATTTTTGT|TTTGTTTGTA|CCTTCTTTAG|ATATTGAAGT|ATTCGCTAAG|GCTTAACATG 99600|
|TAATATATTT|AAATCTTCAT|ATGAATACGT|TTATCTGATA|GATTTTGGTG|AGACATAAAC 99660|
|TATGAAACAA|ACAGAAAGAT|GGAACATGAG|AAAGGGTCAA|GGGTGGCCTT|GGTTAGGGAT 99720|
|GGCAGCTTTT|ACAACTATGA|GCTAAGATAA|AATTTAGAAG|GTTTTCTTTT|TATTTTAATT 99780|
|AATCATACCA|CTATTTTTCT|CCTTTAATTT|CCATATATAA|TGAGTTGATT|GTAGTATTTT 99840|
|TATTGTGCTT|AACTATTTTA|AGATAATAGT|TGTCTCTCCT|CATTTTAGCA|AATAATATAT 99900|
|TTAATGAAAA|ATCAACTTTA|TTGAGGAATA|ATTTATACAC|AGTAAAATAC|ACCTGTATTA 99960|
|ATTATACAAT|TTGATGCGTT|TTATATACCC|AAACAGTTAC|TACTGTAATC|AAGTTACAGA 100020|
|ACACTTCCGT|CAACCTAGAT|AGTTTCCATT|TGTAGTATCA|CCTGTGCCGC|CTCTTCCATC 100080|
|CTCTTGGCCC|CAGGCAGCCA|CTGATGTACT|TTCCATAATT|ACAGCTTAGT|TTTCCCATTC 100140|
|CTAAAATTTC|ATATGAATGG|AATTTATATC|ATATGTATTT|TTATTTTCC|TTCACATTTT 100200|
|TGAGATTCAT|CCATTTTGTG|TATATATCAG|TAGTTTATTC|CCTTTTATTG|CTTTATAATA 100260|

```
TTCCAAGATA  TAGATATATT  GCAATTTTTT  TTTTTTTTGA  GATGGAGTTT  CCATCTTGTT  100320
GCCCAGGCTG  AAGTGCAATG  GCATGGTCTT  GGCTCACTGC  AACCTCCGCC  TCTTCGGTTC  100380
AAGTGATTCT  CTTGCCTCAG  CCTTCCGAGT  AGCTGGGATT  ACAGGCGCCC  GTGACCATGC  100440
CCAGCTAATT  TTTTAGTAGA  GATGGGGTTT  CACCATGTTG  GATGGGCTGG  TCTCAAACTC  100500
CTGATCTCAG  GTGATCCGTA  CATCTTGGCC  TCCCAAAGTT  CTGGGATTAC  AGGCATGAAC  100560
CACTGCGTCT  GGCCGATATA  TTACAATTTA  TTTACCCATT  CACCTGTTGA  TGGACACGTG  100620
GGTTGTTTCC  AGTTTATAGC  ATTGTGAAAC  AAAGCCAGTA  TGAACATTTG  TACATGTCAT  100680
AGTATGGACA  TGTGTTCATT  TATCTGGGAG  AAATGACCCA  GAAATATTGC  TGGGCTGTAT  100740
AAGTGTTTAA  TTTTATGTTA  GAAACAGCCA  AACTTTTTTC  AAAGTAGTTG  TAACATTGTC  100800
CTCTTACATT  CACAATATAT  GAGAGTAGTT  TCCTCCACAC  CCTTGCTCAC  CCTGGGGATT  100860
GTCAGTCCTT  TTAACATTAG  CTATTCTGTT  GAATGTGAAG  TATCTCATTG  TGGTTTTGAC  100920
TTGCATTTCC  CTAGTAACTA  ATGATGTTTA  AAATCTTTTC  ATGTGCATAC  TGGCCATTTG  100980
TATGTTTTCT  TTTGTGAAAT  GTCTGTTGAA  AACTTTTACT  CTTTGTTTTG  GCTTGTCATC  101040
TTACTAAGTT  ATAAGGTTCC  TTATATTTTC  CAGGTGCGAG  TCCTTTGTCA  GATACATGTA  101100
TTATAAATAT  TTTCTCTCAG  CCTGTGATTT  TTCTTTTTCT  TTTCTATTTA  TTTATTTATT  101160
TATTTATTTT  TTAGGAAGAG  TCTCACTTTG  TCACCCAGGC  TGGAGTGCAG  TGGCACCATC  101220
TTGGCTCACT  GCAACCTGTA  GCTCCCGGGT  TCCAGTGATT  CTCATGCCTC  AGCCTCCTGC  101280
TTTTCATTTT  ATAATGTTTT  TTGAAAAGCA  AATTTTCACT  TTTGATGAAA  TTTATCATTT  101340
TGTTATTTAT  GTTTTATAAA  CTATAAACCT  GTTGTTTTGT  TTTAAAGAAA  TCTTTGCTAA  101400
TCCTAGGGTG  TTGATGATTT  TCTCCTATTT  TTTAAAGAAG  TTTTATAATT  TTAGCTTTTA  101460
CATTTAAGTC  TATGGTCTAT  TTTGAGTTAA  TTTTTGCATA  AAGTTTGAGG  TAAGGCTCCT  101520
GCTCCTCTCC  CCCACACCGG  ATGTCTACTT  GTTCAAGAAA  CATTTACTGA  AAAGACGATT  101580
TTTTTACTTA  TTAAATAGCC  TTGACACCTT  TGTCAAAACC  AGTTGTCCAT  AGATGTGTGA  101640
ATCTATTTCT  GGGTTCTCTG  TTTTGTTTCA  CTGATCTTTG  TGTCTAACCT  TATACCAATT  101700
CATTCTGAAA  TACTTTCCAG  ATTACTATAG  CATTTTAATA  AAATTTTGAT  TGAATAGTTT  101760
AAGCCCTCGG  ACTTTTTTCC  TTTTAAGTAT  ATCAACTTGG  AGAGGATTGA  TTCATATTTG  101820
TGTTTCATTT  TTTCATTTTT  CAAAATTATG  TTTCAAATTG  ACATAATAAT  TATATGTATA  101880
TATGGGGTGC  ATAGTGATGT  TCTTTTTTTA  AAAAATATTT  ATTTATGTAT  TTATTTATTT  101940
TTGAAACAGA  GCCTTGCTCT  GTTACCCAGG  CTGGAGTGCA  GTGGCGCGAT  TTCGGCTCAC  102000
TGCAACCTCC  GCCTCCTGGG  TTCAAGCAAT  TCTCTTGCCT  CAGCCTCCTG  AGTAGCTGGG  102060
ATTACAGGCA  CATGCCACCA  CGCCTGGCTG  ATTTTTGTAT  TTTTAGTAGG  GATGGAGTTT  102120
CACTATGTTG  GCCAGACTGG  TCTCTAACTC  CTGACCTCAA  GTGATCTGCT  TACCTTGGCC  102180
TCCCAAAGTG  CTGGGATTAC  AGGTGTGAGC  CACTGCGCCC  AGCCCATAGT  GTTATTTTA   102240
TACATACTGT  GTATAGTGAT  CAGATCAGGG  TAATTAATTA  GAATATCCAT  TATTTCAAGC  102300
ATTTCTCATT  TCTTTGTGTT  GGAAACATTC  AATGTCCTCT  TTTCTAGCTC  TTTGAAATTA  102360
TTTATTACTG  TTAACTATTG  CCATTCTGTA  GTACAAATAG  AACACTAGAA  CTGATTGCTC  102420
TTATCTAGCT  GTAACTTATT  TTAACGAATC  TCTCTTTATC  ATCTCTTTCC  CCTACCATTC  102480
CCAGCCTCTA  GTAATCTCTG  TTGTACTTTT  TACTTCAATG  AGATAAACTT  ATTTACTTAG  102540
TTAGCTAGCT  TCTGCATATA  AGTGAGAACA  TGTGGTGTTT  AACTTTCTGT  TTCTGGCTTA  102600
TTTCACTTAA  TGTAGTATCC  TGCAATTCCA  TCCATGTTGC  TACAAATGAC  AGGATTTCAT  102660
```

```
CCTGTCATGA  ACAAACAAAA  ATTTGCCAAA  ACAAAAATTA  CCTTAGTTAT  CACATTTCTT  102720
TTATTGACAT  AATTCATAAT  CATCAGAATC  ATCTGACTTG  TACATCATTG  TATCAGTTGG  102780
TTTTATGCTC  AAGATGTTGT  ATTGGTTCAT  TATTGTCTTA  ATATCCCAAC  CAACCCAATC  102840
TAGACATAAA  TGCTGGCCCC  TGTGACATGG  CAGGAAAGGG  AGACAGGCCT  GGGCCAAGCA  102900
TAGTGATAGC  AATGCACCTG  TGTTTGAAGC  TGTTAAATAT  TTGCTACAGT  CGTATTCCTA  102960
GACTCAAAAT  TAGATTCTTG  TTAAGTCCTA  CTTGTCAGTG  TCTATGGCTG  TGTGAGTTCT  103020
GGTTAGTAGA  AGGTGGGCAA  AAGTGATGTG  TATTCTTCCA  TAACTGGTCC  ATAACCACCT  103080
ACCACTCACA  ATACTCCATG  CCTTTTTTTC  TCTTCAGGCT  CCTTGGATTA  GAGACCATCC  103140
TGAGGACATC  CTTGGGAGCC  ATGTGCTGAA  GATGGCCAAG  CCACAGGATG  AAAGGAGCTG  103200
CATCTTTGAG  TCACCACTGG  AGAAAGGTCT  CTCTAAATGG  ATTTGCAGAG  ACGTCTTCTC  103260
GAATACTCCC  CTTCTAAGTT  CCACTTGTAA  TCCACTTCTT  CTATTCTCCC  AGCAATCAAT  103320
GTGGTTTGGG  GAAATTCCAG  AATCTCATAA  TACCTTGGTC  ATGGGTAAAT  AAGGAAAGGA  103380
CCTTTACATA  CATGTGATGC  AAAGCAGATC  AAAACAAGCA  GAGCAGCCTA  AGAGCAGCAA  103440
GACCCCAAAG  GATAAGGGAA  GTCCTGCAGA  AGAGCAGAGC  GGTGCTGCAA  AGGCAGGCAG  103500
GTAAGGTAAG  CAGACAGGGC  CATCAGGATG  GATCCTTTGG  GCATGCCAGC  ATCCACCAGG  103560
GACTGGTAGA  GCTATTTAGA  GAAACTGATA  AAAAGCTCTG  CCAACTACAG  TCACAAAAGA  103620
TGGAGCTCAG  AATGATGAGT  AGATGCCTAA  AACATCTCCA  TTTTGTTGAT  GAAGAAAGTA  103680
AAGTTTATAG  AGCTTAGATT  ATTTGCTTTT  GTACCTAGCA  CAGTACTTAG  TTTATAGTAG  103740
ATGCACAATA  AGTATTTGTT  TAATGAGTGA  ATGAGTCACT  AGCCTAAGAC  CTTTAATATA  103800
ACATGCTTAA  ACCTGCTACC  AGGGATTGGG  AACTCACCTA  TTTAGTAGTG  AGTAGAGGGG  103860
TGTGGTACTG  GTACTTAAGA  CAGATGCATT  GTGGTTGGGT  ATGGTGTGTT  TTTGTTTTTG  103920
TTTTGAGACA  GGTTCTCCCT  CTGTTGCCCA  GGCTGAGATG  CAGTGGCATT  ATCATGGCTC  103980
ACTGCAGCCT  TAACCTCCCG  GGGCTCAAGC  GATCCTCCCA  CCTCAGCCTC  TGAGTAGCTG  104040
GGACCACAGG  TACGCATCAC  CGTGCCTGGC  TAATTTTGTT  TTTTGTTTGT  TTGTTTTGTA  104100
GGGACGGGAT  TTTGCCATGT  TGCCCAGGTT  GGTCTCGAAC  TCCTGGGCTC  AAGCTACACC  104160
CGCCCGCCTC  GGCCTCCCAA  AGTTGTAGGA  TTAAGGTGTG  AGCCACTGTG  TCCAGCAGAT  104220
ATAATGTTTT  TAAAAGTTTG  AGAGTTAATA  TGCTCTCTGG  TGTGCCCTAG  GTCCCACTAC  104280
TCCTATTGCC  TTAAAACTCA  CGCAGTACAC  ATTTGTCTTC  CATGGGCTTC  AGTTGTAAGA  104340
GAACCCTTTC  TACTCTTTGC  TGTTCACAAG  TCTCCTTTTA  AACAGAGCTT  GTTCCCAATG  104400
CTGTTTTGTT  TTGCCCTCTG  CCATGTTCTT  CCGGCCATCA  CCTCCTGTGG  GGAAAAGAGA  104460
GAGAGATCAC  ATTGTTACTG  TGTCTGTGTA  GAAAGAAGTA  GACATAGGAG  ACTCCATTTT  104520
GTTCTGTACT  AAGAAAAATT  CTTCTGCCTT  GAGATGCTGT  TAATCTAACC  CTAGCCCCAA  104580
CCCTGTGCTC  CCTGAGACAT  ATGCTGTGTC  AACTCAGGGT  TAAATGGATT  AAGGGCTGTG  104640
CAAGATGTGC  TTTGTTAAAG  AAATGCTTGA  AGGCAGCATG  CTCGTTAAGA  GTCATCTCCA  104700
CTCCCTAATC  TCAAGTACTC  AGGGACACAA  AACACTGAGG  AAGGCCACAG  GGACCTCTGC  104760
CTAGGAAAGC  CAGGTATTGT  CCAAGGTTTC  TCCCCATGTG  ATAGTCTGAA  ATGTGGCCTC  104820
GTGGGAAGGG  AAAGACCTGA  CCGTCCCCCA  GCCCGACACC  CGTAAAGGGT  CTGTGCTGAG  104880
GAGGATTAGT  AAAAGAGGAA  GGAACGCCTC  TTTGCAGTTG  AGACAAGAGG  AAGGCATCTG  104940
TCTCCTGCTC  GTCCCTGGGC  AATGGAATGT  CTCAGTGTAA  AACCCGATTG  TATATTCCAT  105000
CTACTGAGAT  AGGGGAAAAC  TGCCTTAGGG  CTGGAGGTGG  GACATGCTGG  CAGCAATACT  105060
```

| | | | | | | |
|---|---|---|---|---|---|---|
| GCTCTTCAAG | TCATTGAGAT | GTTTATGTGT | ATGCATATCT | AAAGCACAGC | ACTTAATTCT | 105120 |
| TTACCTTGTT | TATGATGCAG | AGACCTTTGT | TCACGTGTTT | ACCTGCTGAC | CTTCTCTCCA | 105180 |
| CTATTATCCT | TTGACCCTGC | CACATCCCCC | TCTCCGAGAA | ACACCCAATA | ATGATCAATA | 105240 |
| AATACTAAGG | GAACTCAGAG | GCCGGTGGGA | TCCTCCGTAT | GCTGAACACC | GGTCCCCTGG | 105300 |
| ACCCCTTTTT | TTCTTTCTCT | ATACTTTGTC | TCTGTGTCTC | TTTCTTTTCC | AAGTCTCTCA | 105360 |
| TTCCACCTAA | CGAGAAACAA | CCACAGGTGT | GGAGGGGCAG | CCCAACCCTT | CAACCTACCT | 105420 |
| ATCTTATCTC | TTCCATTATC | TATCCACATA | TGTCCTCTGT | ATTTTTTTGA | GTAACATTTA | 105480 |
| TAAGCATAAG | TCCTTAGGTA | GCTATGCCAC | TTACATAATG | AACTAGAAAA | GGTAACCAAA | 105540 |
| CAGAATAGGG | TTGTACTCAG | ATATACCTTC | TACAAGTTTG | TGTTACACAT | ATTTACACAT | 105600 |
| ATTTAAAAAT | ATATACATAT | TATTATTGTG | CTGTGTGGTT | ATTAGGCAAA | CTCAATAAGC | 105660 |
| AGTTCTTATA | AAGTATACTC | AATGTAACTT | TTATAAACTT | ACCATATTTT | ATAGTTATTC | 105720 |
| TGTTTTTATT | AGCTGCTATA | AACTACCTGG | GTGTCTTGCA | TGAGTCATTT | TATTGTAATG | 105780 |
| TTTTTGTATC | TGTTGAATGA | GGAGTTAGAA | GGCATCATCT | TTAAGGAGCT | TTACAGGTAC | 105840 |
| ATGTCCAGGG | CTCAATAATT | TTATTATTAT | TTCCTGGACA | GATAAAACCT | AAGCAGGTGA | 105900 |
| AGGGGAAAGA | ATAAAAGTGC | AGGGTGGAAG | TTGCTTGAAT | GCTAACTGGG | TCAACGATCT | 105960 |
| CCCAGAAAAC | CCCTGTAAAA | GAAACCTAAG | AACCTACATC | ACCAGGAGAC | CATTGGGACC | 106020 |
| AGTTCCTCTG | GAATCCCTGA | GGCCAGATAA | TCAGCTGAAG | CTTTACATTC | TGTCCCTTTC | 106080 |
| TGGTCATGAC | TTTCTCCACA | GTCTGCTTGG | TGCCTCCTCC | TCTGTGACTC | TAAATTCTTA | 106140 |
| GGATCAACCC | CTCTTGCATA | TGCACATCCG | CAGTGCCTGT | GGGATACGGT | GTGGTGTGGG | 106200 |
| GAGGAAACTC | TCTTCTGCCT | TAATATTTTC | CTGTGTGCCC | CAGGCCTTGA | CGGAATCCTG | 106260 |
| TCTCTCCATA | ATGTTGCTTT | TCGAGGAGAC | TGATTGATTG | AGATGGCGTC | TCACTTTGTC | 106320 |
| GCCCAGGCTG | GAATGCAGTG | GCGTGATCTC | GGCTCACCAA | CCTCCACCTC | CAAGGCTCGA | 106380 |
| GTGATTCTCC | CACTTAAGTC | TCTTGAGTAG | CTGGGACTAC | AGGTGCATGC | CACCACGCCT | 106440 |
| GACAAATTTT | TTTATTTTTT | GTAGAGATGA | GGTTTCGCCA | TGTTGACCAG | GCTGGTCTCA | 106500 |
| AACTCCTGGA | CTCAAGTGAT | CTGCCCACCT | CGGCCTCCCA | AAGTACTGGG | ATTACAGGCA | 106560 |
| TGAGCCAATG | TGCCCGTCCT | GAGGAGTTTT | CTTCTGGAAT | TCCTGCTGGG | TTTTTGTAGT | 106620 |
| CAGTCCTCTC | CCCATTTCCC | ACATTGGCTC | TTGCAGACCT | TCCTTTTCCC | CATTTCTATT | 106680 |
| TGCTACCATG | TCAGACATGA | CTTTTGCCAT | AGGATCTCTA | TTCTACTATA | GAGGAAACCA | 106740 |
| AAGCCATCAG | TAGAAATTTC | ACTAACATGG | AATCAGATTT | ATAGAAGAAA | GGGGGAGGAA | 106800 |
| AGTTTTGCCT | TAACACCTGG | AAGGGTTTCG | TTTCTTTTAG | TAGCTGGGAG | ACAGAAACAT | 106860 |
| AAGAAAGTAG | CTTAGTAAGC | TTTCTGCTGT | TCAACTGATG | ATGTGTGAGC | TGTCAGTAGT | 106920 |
| TCAAACTAGT | CATTATCTTT | ATGAATTAAT | TATGTAATAA | CTTAAACAAT | GTCATAAACC | 106980 |
| TTCAAATCAG | TTTAAGTCTA | AATGTGTCAT | ATTTAATAAC | AAGAGCAAGA | AACATACGTT | 107040 |
| ATGATGAAGA | GCTCTTATAT | TTTCTTTGGA | TAAAAGTCAG | TAGGCGGGGC | GCGGTGGCTC | 107100 |
| ATGCCTGTGA | TCCTAGCACT | TTGGGAGGCT | GAGGTGGGCA | GATCATGAGG | TCAGGAGATC | 107160 |
| GAGACCATCC | CGGCTAACAC | GGTGAAACCC | TGTCTCTACT | AAAAATACAA | AAATTAGCT | 107220 |
| GGGCGTGGTG | GCGGGCGCCT | GTGGTCCCAG | CTACTCGGGA | GGTTGAGGCA | GGAGAATGGC | 107280 |
| GTGAATCCGG | GAGGCGGAGG | TTGCAGTGAG | CCGAGATTGT | GCCACTGCAT | TCCAGCCTGG | 107340 |
| GCGACAGAGC | AAGACTCCGT | CTCAGAAAAA | GAAAAAAAAA | AAAGTCAGT | AAAATTTAAG | 107400 |
| AGAAAAATGC | ATTTGCTTTG | GGACTTTTAA | TATTTAGTCT | ACAAATCTAG | CCACCATAGA | 107460 |

-continued

| | | | | | |
|---|---|---|---|---|---|
| AATCTGCTGA | TTAAATACGG | GTTCTGTTAA | AATGGAAACA | TGCATTTTGG | GGGAAAAAAG 107520 |
| AGGGAGTGTT | TTAGTGATTT | TGTTTTTTAC | ACTTGTTTAT | AATAAAATTT | TAAGCAATCT 107580 |
| TGAGGGGAAC | ATTTTATTTC | TACTTGTAAC | TGCATAAAGT | TATGAGATAA | AGTTACAAGC 107640 |
| TATATCACAT | ACAGTTTGTA | GCTTTATAAA | TTATGAAATT | CTAACAGAAT | AAATATGCTA 107700 |
| ATATGATGAA | AATGTCATAA | ATTACATTAG | AATATATTTT | AATAAACCAA | TTCAGAAGGA 107760 |
| GCCAATACCC | AATTTCAAAA | TCATATTAAT | TGTAAAATTA | ATTAGGGCAG | CCAAAATATT 107820 |
| CTGGAATTCT | TTCTAATAAA | ACAAATGAGT | GTAAATACAG | TCGTACTGAC | AAATCTGAAG 107880 |
| AATTATGCAG | CATAAAAAGT | GATTATCCCA | GCACTTTGGG | AGGCCAAGGT | GGGCAGATCA 107940 |
| TGAGGTCAGG | AGTTGGAGAC | CAGCCTGACC | AACATGGTGA | AACCCCGTCT | TTACTAAAAA 108000 |
| TACAAAAATT | AGCCGGGCTT | GGTGGTGCAC | ACCTGTAATC | CCAGCTGCTC | AGGAGGCTAA 108060 |
| GGCAGGAGAA | CTGCTTGAAT | CCAGGAGGTG | GAAGTTGCAG | TAAGCCAAGA | TCACGCCACT 108120 |
| GCACTCCAGC | CTGGGCGACA | GAGTGTGACT | CTGACTCAAA | AAAAAAATAA | ATAAATAAAA 108180 |
| ATAAAGTTT | TAAAAAGTG | ATTATTATGA | ACACAGAGTA | ATCTAGTAAA | AATGGTTAAG 108240 |
| TGAAAACAGC | AAAATACAAA | ATTGAATATG | TACTATAACA | ATATATGCAA | AATATACTCA 108300 |
| GATTTATAAA | AATTAGAATG | TAGAAAAGTA | AATATAGCTC | TTCATAATTT | TGTTCTGAAG 108360 |
| TTTAAAAATA | TATATATTTT | TGAATGGATA | ACTTTCTTTT | TCTAAATGCT | TACAGTAGAG 108420 |
| CCCACGATGG | TTGTTAAAAG | CCCCCAGGTT | CAGCCTTCTT | TAATTGTGTG | GTCAGCCTGC 108480 |
| CATCAACCCG | AGGCCTCCCT | CTGCTGGGCA | AATTTGGGAA | CACATTGAGA | AATCCTTACA 108540 |
| CGTAATTCCT | TCTCTTCATG | TTCCTGGTGA | GCATTTTCC | CATTGGGTTT | CCATACTCTG 108600 |
| CCCTCTTGAA | GTCCTGCACC | CTGACATTGC | AGTGTCATTC | CTCTTCTACT | GAAGTCTACA 108660 |
| ACTATTAGCT | TATTGTCTCT | AGCAAGTCTC | CCTTTAGCTA | CAAATATCAT | TCAGAGTTTT 108720 |
| ACCTTTCAGA | AACTTTCTCC | ATGAGCATTC | TGGAGTAGAC | TCTAGGTGCA | CTAGGTGCAG 108780 |
| TTAGAAAAAG | TTCTGATTTG | TTGGTGGAGC | TATAGGAGGA | GAGACAATGG | TGGGCTGGAG 108840 |
| AAGGGTGTCT | ACATGCAGAG | AAACTGACTG | GAAACTCAGA | GAGATGATGG | GGATTAAAAT 108900 |
| AATCCTATTG | AATCTGCACA | AAAGTGTTTT | ATTATAATTG | ATCCTGAACT | ATGTAAAGGT 108960 |
| AAGCTCCAGT | GAGTAGTTAC | AGTCTGTCCC | TAAGATGGAC | TCTTTCTTTT | TGCTTTTATT 109020 |
| TTTATTGTAT | TTATTTTATT | GTATTTTTTT | TTTCTAAAGA | CAGGGTCTTG | CTATGTTACC 109080 |
| CAGGGTGGTC | TCAAGTGGTC | CTCCTGGCAT | CAAATGATCC | TCCCACCTCA | GCCTCCCAAA 109140 |
| GCGCTAGGAT | TACAGGTGTG | AGCTACCACA | CCCAAATGAT | TCTTTCTTTT | CAAATACAGA 109200 |
| GTTCAGCAGC | AATTTTAAAG | AAGTACTGAA | CTCTACTGCC | TGGAAGATGG | AATGGCCCTC 109260 |
| ACAATTCTTC | CAGGCAAGCT | CTGCACTCAG | TGGTATGGAC | CACAAGGCAA | GCCCATTAAG 109320 |
| GGGTTAAATT | ACTGACAAAC | AATAATTTCT | AAATATGAAC | ATTTCAGGAG | GAACTAAGAT 109380 |
| GGCTCCTTCT | TGGAGAATAA | GTTGGCCGGC | TTCTCTAGTT | ATCAGACTAT | CAGATGGGA 109440 |
| GGAAAGAGCC | CCTCTGTCCC | GGTGAGACAG | GACCCGCCAG | CGCCCAAGCT | CTAAGGCTTT 109500 |
| CTGATGAGCA | AATGGGGTTT | CCATCTTTCT | AGCTTCAGGA | CTCGTAACTA | CTCAGATTAT 109560 |
| TTCCTTCAAT | CTGGATATTC | AAGACAAGAA | CAGTTCATGG | TGTTGCGAAG | GCCCAGATTT 109620 |
| AAATCACATA | TGCAAAGATA | CTGACATTCA | GTGGAGGGTC | ACTTAGATTA | TAGCCAGATG 109680 |
| ACTTTCCCTA | AATTGATAGC | TCAAATGGTA | GTTGTGGATA | TTTTTGCTCT | TAGTTACTTG 109740 |
| CATAGTCACT | TGCCAGAGGT | AATAAAGTTT | TAGTGTGGTT | GTGGAAAATA | ATGGCCATAT 109800 |
| ATTTAGGAAC | AAAATTTTAA | TGATGATTGA | AAACTGAATT | AGCTTTAACA | TGTGAATATG 109860 |

| | | | | | |
|---|---|---|---|---|---|
| CTCAGGGGAC | ATAGGACCAC | AGATCTCTGT | TCCTTCCTAT | TGCCACTTCT | TTCCTTTCCC 109920 |
| TGGTAGCATG | CTTCCATTAC | CCATTACTTC | AAACACTGTT | TCTGTGTCTC | CAACTCCCTT 109980 |
| GCATCATGGT | CTTTTCATTA | TTCAGACACA | GACACAGCTC | GATTATGGGT | AAACTTTTTT 110040 |
| CTGTGGCTAC | AGAAGAGTTG | AGCATGGCTG | AAGCATCGTT | GAGCATGACT | GAAGAAAAAC 110100 |
| ACCTAACCTT | GAATTTTTTG | ATCAATATAA | ATTTATATCC | ACAGATTTTA | CCTGACTGAT 110160 |
| CTTCATTGCC | CACCAGTCCT | ACAAAGTTTG | CCAGATTGGT | TCTGTTTCCA | CTTTACATAC 110220 |
| TCAGCAAATA | CTTATTAAGC | ACACACTTTG | TGTTAGGCTT | AAGTGTAGAT | ATTGAAGAGG 110280 |
| CACTGGTGAA | TGAGCAGAGG | CTCTGCCCCC | ATGGGACCTG | CATGCTATTT | GGCAGCTCTT 110340 |
| TCAGACATTC | TCCTCTCTCA | AAGCTTTGAG | CCCCTCTATA | CCCCTATAAG | CACCTACTTT 110400 |
| CAGCTGCTCC | CTCACTCCCC | CCTTCATGGG | GGAAATAACA | GCCATCGTGG | TAAAACCTCC 110460 |
| ACTGCCTGAC | AGAGCTATAT | TTACCATCTT | TTCTTTAATT | TTTATTTTTA | ATGGACACAG 110520 |
| TTGTATATAT | TTATGGGGTA | CTATGTGATA | TTTTGATACA | TGTATAGATT | GTGTAATGAT 110580 |
| CAAATCAGGA | ATTAGATCAG | TTTTTTGTCT | TTTTTTTGGT | AAAAGATAAT | CTTTTATACT 110640 |
| CTTTTGGTCC | TGAAAAATGG | AGGAGTGCCA | TATTAGGATT | CCAACAGAAA | AAGTTAAACC 110700 |
| AAAAGAATAT | ATGAAGGGCA | TATAATGAAG | GGATATCTAC | AAAGTTGTGA | CAGGGCTAAT 110760 |
| GGGAAGAACA | GGGGATATGA | GGCAGCCCAA | GATCAGCAAC | AGTAGTGATC | CAGTGTCACC 110820 |
| CTGTGCTGGT | TATGAAGATT | TAGTCTCTTC | TATCTTTTCC | AATACCGCTT | TGCTAGCCAC 110880 |
| CTCCCCAAAC | CCTACCAATA | GAAAGCACTG | GAGGAAGACT | AGAGGGCTGG | AAGGATGTGA 110940 |
| AAAGATTTCC | CACTTTGTTT | GTTGACATCC | TCACAGAATG | GGTTCTTCAA | CCTGGCAGTG 111000 |
| GCAGTTGAAT | CCAGTAACAG | CAGTTGGCTT | CAGTTGGAG | ATCTTCCATG | CTCCTAAAAT 111060 |
| CAGCCTCATC | ATGCCTCTAT | CTACAGACAT | ATCATCATCA | GTGGTCCAGC | ATACACTCCT 111120 |
| CAGAGGTCCC | AGTTCTGGGG | ATCTCTTCAA | AGAATCTTTT | CCTTGTTCTC | CTAAACCTGG 111180 |
| AGGTGGTAGT | TGCTTTCTGT | CATTACTATC | TCTGATACGT | TTGTCCACTT | TTCCATTTTC 111240 |
| AGTCCTCTTA | TAACTAGTTA | ACAACCATTC | CCATAAAATT | CTTTGTTCAA | TTTCAGTGCA 111300 |
| ATTTCTAGCT | CCCAGTTATA | CCCTGACAGA | CACACCTTTA | AATCTGAAGA | GGCAATGGGA 111360 |
| GGGAACCTGT | AACCAGAGCT | AGGCCAGAGC | TGGGACTGTG | GAGGAAGAGC | TGCCCACCAA 111420 |
| GCAGGGGGT | GATGCAGGGA | ATAAGTACAC | TAACCTCTCT | CTCCTTTGCC | ATCTACATTC 111480 |
| CTGCTGGGCT | GATCACTGGC | CAAATCCAGC | TGTTGCAAGA | GGGCAGGGCT | GCCCAGCTAA 111540 |
| TGCTATCTGT | AGAAGCTGGG | CTTCTGGGGC | ACAGAGCAAG | TCAGAGACAG | GCAGAACAGG 111600 |
| GATGTGGGTT | TGGACCAAAC | ACTGAATAAA | CCAGATCAAG | GATTCTTCTA | TCAAGACAAG 111660 |
| TTTATATACT | TGCAGCTTGA | TCCCATTGTT | TCCCTTAGAT | AACTGTGCAC | TTGTTTTTGT 111720 |
| CTGCCCTCTT | TCCTGTGTCT | ACACTCTTCC | TGTCTTATTC | TATTTACACA | TAGCTCAGTC 111780 |
| TTTTCCAATT | AAAAAAAAAA | AAAAAAGCT | TTCCCTCTCC | CAAATCTCCA | TGCAGCTGCT 111840 |
| GACTTCTCTC | TTCCAAAGCC | ACACTGTGGG | AGAGTCAGTT | ACACCTCCTG | ACCTCTGACA 111900 |
| GGTGCAACAC | ACTATAGTGA | GGCTTCTGCC | CTTGGTATTC | CTCTGGCTCC | ATTATTTACA 111960 |
| AGGTCACTAA | TGACTTCCTA | TTTCTAAATC | CAGAGTGCCT | TTTTAGTTAT | CTTCCTTGCC 112020 |
| TTCTTGGCAT | CTCTAGATAA | CAATACTTGT | CTCATTCTAA | CTTTTGTCTC | TCCTTACAGC 112080 |
| TCTTTCATTC | ATAATTCATT | GTTATTCAGT | TGGAGCCTTG | ATGGTGTTAG | GGAGAAGCAG 112140 |
| CATTCTGTAG | TCAAAGTGTT | AAGCCTCAGT | TTATTAGCAT | GCCTATATCT | TGGGGCTGGG 112200 |
| ACCGTCACAA | GTGTTTATAA | TGATACAACT | CCTCCTCCTC | CTCCTTCTCC | TCCTCCTCTT 112260 |

| | | | | | |
|---|---|---|---|---|---|
| CCTCAAGTGT | TTATAATGAT | ACAACTCCTC | CTCCTCCTTC | TCCTCCTCCT | CTTCCTCAAG 112320 |
| TGTTTATAAT | GATACAACTC | CTCCTCCTCC | TCCTTCTCCT | CCTCTTCCTC | AAGTATTTAT 112380 |
| AATGATACAA | CTCCTCTTCC | TCCTTCTCCT | CCTCCTCAGA | CCTTTGCTCC | TTTCCTGGCT 112440 |
| GCACCATTTC | CAATTTATTT | TCATGAAGCT | CTGATCCCTG | TTGACTAATT | TTCTTCCCTT 112500 |
| AAGTGAGACA | GAAAGCCTAG | ATGAGGCTGC | AGTGGGAAGA | ATTACCTTCT | CCCAGCTGGG 112560 |
| ATAAGACTCT | GGCAAAATGT | TTTCCCCTTG | AGAGTAGGCC | TTTGTTTTGA | AGAAGGTTCT 112620 |
| GGGGTGTATT | TCATAATAAT | TCTTCTCTCC | CTGCCAAAGC | CACAAGAGGA | TCCTTCTCAG 112680 |
| ATCTTCACTG | CAGGAACCTG | GTGGGCTTTC | TGATGCCCAC | AAAAGTGTGG | GAGCTTCTCA 112740 |
| CTCTCATGGG | CATTCACAGT | TGGCCTCCAG | CTTTTTGTCA | GAGTTACCAA | TTTAAATGTT 112800 |
| CTCAAATGTG | ATACTGTCTC | AACTTCCAGG | ACATCACACA | CTCATGATTT | TCTACTATCC 112860 |
| TGACATTTGC | AGTCTTTTTA | GCAGATCTCC | CTCCCTCTCC | CTGCACCATG | GGTATTGGTC 112920 |
| ATCTCAGGAT | CTGTCCCAGG | CTTTCTACTC | TTCATGCCCT | TGAGACAAC | ACATGATCTG 112980 |
| ACCTGCCCTT | TCAGGAAGAA | ATGTTCTGTC | TACCTACTTG | CTCCAGTTAA | AAACCCTAGT 113040 |
| GTCATCTTTG | ACCCTTCTCA | TCCCTACATC | TAATCTGTTG | ATTCTACCTC | CTAATTTTCT 113100 |
| CTCAAACGCA | TCTATTTTTC | TTCAATTTCA | GTGCTACTCT | CTTGCTCTAA | TTGTACATCA 113160 |
| TCTTTTTTAG | AATTACTGTG | ACATTTTCTT | GCCTCCAGTT | CTGCCTCAGT | CCATCCACTT 113220 |
| CACAGCTAAA | TTTTGGATGT | ACACTTTTGA | ACTATTACTG | TAGCAAAAGT | AATATGTAAT 113280 |
| AACTGTAATG | CAGAAATATA | AAATATGCAA | TATAAAAGAA | ATACATGCAT | AAATGATCCC 113340 |
| AACACTAAGG | AAACAATATT | GATCAATAAT | TAAATAATTG | GTGGATAGTG | AATGACAACA 113400 |
| TAGAGCAAAG | TGTTCAGTAG | GTTTTAAAAG | CTGTGGGTTC | AATAAATGCT | CATGAAGCTT 113460 |
| GTTCAGGGGC | TTGCAAAATA | TGTAATTTGA | ATTTTTAAAG | AAAAGGAATT | TCAGATAAGA 113520 |
| AAAAACATAC | ATAACATGAA | ACAATACTTG | TGGTGGTTTC | AGGGAGGTCA | TGTTCTCACA 113580 |
| TTCAGGTGCC | AAGGCCACCG | TACATCCGGA | CACTGAGGCC | ACGGACTTGG | TCTGCAACCT 113640 |
| CCATGACAGC | CTTGTAGATT | TGAAACCGAA | CTCCAAGGAG | CAGTTGTGCT | GTGAGTTCCA 113700 |
| GAGTTTGGGG | ACAGAGGAAA | CACCATTCTT | TGGAAGTCTA | ACTTCCTTAA | GAGGTGTCCC 113760 |
| TTAGACATCT | AGTGTCCGGT | GTTATGGAGG | TCCTTGTGCT | CTGAGGAAGG | AGCCCCTTGT 113820 |
| TGATTGATGG | AGCAAAATTT | TTTTAAACAA | GGAACTGTAC | CCGTATCTGG | GCATGAAGCC 113880 |
| AGAGAAATCC | CTGAGGGCAG | GGCCAAGGCT | CTCAAAGATT | TCAGGGAGA | TTCCCAGCCT 113940 |
| TTTTAAGTCT | CGCCTATTCT | TTTTTTTTTC | TCTAACTGGC | CATTTTGTAT | ATATGGAGGT 114000 |
| TATTGATTTT | TTTGCTTTTA | TATCCTGATA | TTTTAATAAC | TGTTCATTTT | TTAGTTATTT 114060 |
| GAATTATCTA | CATTGATTAT | TTGAATGTTC | TTTTTTTTGT | TTTTTTGAGA | CGAAGTCTCG 114120 |
| CTCTGTCGCC | CAGGGTGGGG | TGCAGTGACA | GGAACTTGGC | TCACTGCAAC | CTCTGCCTCC 114180 |
| TGGGTTCAAG | CGATTCTCCT | GCCTCAGTCT | CCTGATTAGC | TGGGATTACA | GGTGCCCGCC 114240 |
| ACCACACCCA | GCTAATTTTT | GTATTTTTAC | TAGAGATGAG | GTTTCACCAT | GTTGGCCAGT 114300 |
| CTGGTCTCAA | ACTCCTGACC | TCAGGTGATC | CACCCACATC | GGCCTCCCAA | AGTGCTGGTA 114360 |
| TTACAGACAT | GAGCTATTGC | ACTTGGGCTT | TGAATTTTCT | ACGTATCTGA | CTTCTACGAA 114420 |
| GAAAACTATA | ATGTATTACT | CAGATAAATT | AAACAGGAAA | ACTAAATAAT | GGAGGAGTAT 114480 |
| ATTTACAGTT | GAAGCGGTCA | ATATTTTAAA | GGTATTAATT | GTCCCCAAAC | TGATCTACAA 114540 |
| AACCATTGTA | ATCCTAATCA | GATTCCCAAT | AAGCTTTATT | ATAGAAATTG | ACAAACAGGG 114600 |
| TTCAAATTTA | ATACACAAAT | CCAAGGGCCC | AAAATAAACA | AATCTGTTGC | TTTATTAAAT 114660 |

| | | | | | | |
|---|---|---|---|---|---|---|
| ATCAAAACTG | ATAAAATGAC | AATAATCAGG | GCAGTGTTGT | CCAAAAATAG | ACAAACGAAT | 114720 |
| GGAACAGGCT | CAAACAAATA | TGGACATTGA | TTTACATCTA | AAGTGGCACC | ATACAACAAT | 114780 |
| GGTGAAAGGA | CTCTTGTAAA | TAAATGGCAT | GGGACAATTG | TATAGCCTTT | TAAACAGAAA | 114840 |
| AAGAACAAAA | AGGAAAAAAA | AAGAAACTTG | ACCCCCTACT | TCACACTATA | CACAAAAAAC | 114900 |
| AATTCCAGGG | GAACTAACAT | GAAAAGCAAA | ATAAAGTTAA | ACATGAAAAG | CAAAATAAAG | 114960 |
| TATATGGTAA | AAAATTTATC | TTACCCAAAA | AGAGGTCTAG | CCTTTGCCCT | CAGCTACTGG | 115020 |
| GAGATGAATT | TTAGACCCTT | GAAATGTTCT | CACTGATAAG | TGTGTCTTTG | TTTACCTGGA | 115080 |
| GGTTTTGACC | ACCACACAGT | CAACAATGTG | ATTTATAATA | GGAACTTTGA | GCCACACAGT | 115140 |
| ATCAGCTCTA | CCTGTGGAGG | TAGACTAAAA | GATCGGCCAT | GTGAGCAGTC | AACCATGGCA | 115200 |
| GGCCATTAAA | ACTGCACACT | GAGGCTCGGG | TGAAATACAG | TTCTCTTGTA | TACGGTTTCT | 115260 |
| ACATGGTTTT | AGTTCCTGTG | GTCTACTGCA | GTCCAAAAAT | AATAAACGGT | AAATTTCAGA | 115320 |
| AATAAACATT | CACCTAACTT | TTATACAGTA | TATTCTTAAC | AATTATTCTA | ATTTATTGTT | 115380 |
| ATTAATCTCT | TACTGTGCCT | AATTTATAAA | TTAAGCCTTA | TCATAGCTGT | GTCTGTATAG | 115440 |
| GAAAAAACAG | CTATATAGAG | TTCAGTACTA | TCCATGGTTT | CAGACATCCA | CTGGAGGTCC | 115500 |
| TGGAACATAT | GTTTTGTGCA | TAAGTGGGGA | CTGCTCTGTA | CGTCATGTGT | ATTGTCACAC | 115560 |
| ATTAATGCTG | GGAAAGTAAT | ACTGTTCATA | TTACTGGGAG | AGGACAACTG | GAAGCTCATA | 115620 |
| TTTGGAACTT | GCCTGGATTG | TGCCTATATT | AGTTTCCTAG | GGCTGCTGTA | ACAAAGAGCT | 115680 |
| AGAAGCTAGG | GTGGCTTAAA | ACAACAAATA | TATTCTCTTG | TAGTTCTGGA | AGCTAGAAAT | 115740 |
| CTGACATGAA | GGTATCATTA | GATCTATGCT | TCCACTGAAG | CCTGTAGGAA | AATCCTTCCT | 115800 |
| TGACTCTTCC | TAGCTTCTCG | TACTTGCTGG | CAACCTTTGA | CATTCCTTGA | CCTGCAGCTG | 115860 |
| CATAACCTCA | GTCTCTGCCT | GTGTGTGTCT | GTCTTCACGT | GACCACCTTA | GAAGAATACT | 115920 |
| AGTTCTATTA | AAAAATATAT | ATATACTACT | TCTTCTAAGT | CACCAGCCCA | TCATACTGTA | 115980 |
| CTATAACCTC | ATCTTAACTA | ATTATATCTG | CAACTATCCT | ATTTCCAAAT | AAGGCCACAA | 116040 |
| TTCTGAGGTA | CTGGGAGTTG | GGACTTTAAA | CATATCTTCT | GGGGGCAAGG | GAGATCTGCA | 116100 |
| TACAATTCGA | TCCATAATAC | TGCCTTGTGT | GTTTCTTTTC | TCAGCTGATT | TTAATCTTTA | 116160 |
| TTCCTTGAGT | TGTTTCCCCT | TTTCAACTAT | TACAAACAAT | GAATTTGCT | GTGTATGTGT | 116220 |
| CTTGGTATAT | ATGTGCACAC | ATATCTGCTG | TTTGTATACC | TCAGAGTGAA | ATTGTTGGGT | 116280 |
| CAAATGCTAA | AATCTTTTTA | AAAGTAGTTG | TATAATTTTA | CATTGCATTG | GAATGACATA | 116340 |
| ATAAGCTATA | TATCCTATAA | TAAATTGTAA | CCATGAGGCT | AACAGCTTCA | GCAAGTTCTG | 116400 |
| TGAGTCCTTT | TAGCAAATTA | CTAACCTAAG | GTTGATTGGG | AACCACAGAC | CTCCCAACTT | 116460 |
| ATAATTGGTG | TTAGAAGTGA | GGGTAGTCTT | GAGAACTAAT | TTCACAAGAA | GGTATTATAA | 116520 |
| AATAAGATCT | TCATGACCTT | GAAATAGAAA | ATGATTTTTT | AAATAAGATA | CAAAAAGGT | 116580 |
| TGTGCATAAA | AGGGCAGTGT | GCTTAATTTG | AGTACACTAA | ATTAATGACT | TTAATGCATC | 116640 |
| ATGAGATATC | ATTGGCTGGG | TGCAGTGGTG | GCTCACACCT | CTAGTCCCAA | CACTTTGGGA | 116700 |
| GGCCAAGGTT | GATGGATTGC | TTGAGCTCAG | GAGTTTGAGA | CCAACTTGGG | CAACAGCACC | 116760 |
| ATCTCTACAA | AAAAATACAA | AGATTAGCTG | GGCATGGTGG | CCTGCACATG | TAGTCCCACC | 116820 |
| TACTAAGGAG | GATAAGATGG | GAGGATCGCT | TGATCCTGGG | AGGTGGAGGC | TGCAGTGAGC | 116880 |
| TGTGATTGTG | CCACTGCACT | CCAGCCTCTG | ACAGAGTGAA | GACAAGTTAC | AGAGGAAATA | 116940 |
| CCTGCAACAC | ATAAAATGGA | TAAAGGGTTC | GTGAGCAAAA | TTTAAAAACT | TAAAACAGAA | 117000 |
| AAGACAGGCC | AGGTTTGGTG | GCTCACACCT | GTAATCTCAG | CATTTTGGGA | GGCCGAGGCA | 117060 |

-continued

| | | | | | | |
|---|---|---|---|---|---|---|
|GGTGGATCAC|CTGAGGTCAG|GAGTTTGAGA|CCAGCCTGGC|CAACATGGTG|AAACCCCGTC|117120|
|TCTATCAAAA|ATACAAAAAT|TAGCAGGGCG|CGGTGGTATG|CACCTGTAGT|CCCAGCTACT|117180|
|TGGGAGGAGG|AGAATTTCTT|GAACCCAGGA|GGTGGAGGTT|GCAGTGAGCT|GAGACAGCGC|117240|
|CACTGCACTC|CAACCCGGGT|GACACAGCAA|GAGTCCACCT|CAAAAAAAAA|GAAAGGACAA|117300|
|AAAGGACAAA|AAGACAGCTA|TCTTAAACCA|ACAAGAAAAA|ACACAATCTT|TTTGGCCTAA|117360|
|ATTGTGTTCC|CCCAAAATTG|ATGTTGAAAC|TCTAACACCC|AATGTGCCTA|TATTTGGAGA|117420|
|TAGGGATTTT|GGGACTTTAT|GGAGATATTT|AAGGTTAAAT|GAGGTCATAA|GAGTAGGCCA|117480|
|GTAGTCTGAT|AGATCTGGTG|TCCTTATAAG|AAAAGGAAGA|GACATGAGGT|CATTTTATGG|117540|
|GCATATGAAG|AGGCCACATG|AGGACACAAA|AGGCGACTGC|TGTGGTTTGA|ATATGAGATG|117600|
|ACATCTCACA|TCTGCCATAA|CAGTAAGAAG|GCCCTTGCCA|GAGGTGGGCC|CCTCGACCAT|117660|
|AGGCTTTATA|GCCACCAGAA|TTGTAAGAAA|TAAATCTGTA|TTCTTTATAA|ATTATTTGGT|117720|
|CTCTGGTATT|CTGTTCAGCA|CCAAACAATC|TAAGACAGCA|ACTATCTTCA|GGTCAATAAG|117780|
|AGAGCCCTCA|CTAGAAACTG|AATCTCTTGG|CACCTCAATT|TAGGATTTCT|GGCCTGGCCT|117840|
|TTAGAACTGT|GAGGTAATAA|ACTCCTTTTG|TTCAAGCTAC|CTAGTCTAGT|ATTTTGTTA|117900|
|TGGCAGCCCA|AGTCGACTGA|TATACAATCC|AATTAAGAAA|AAATGGGCAA|AAGATGTAAA|117960|
|ATAAAACCAT|AATGAGATAA|TACTGCACAT|CTGCCACAAT|GGATAACATC|TTCAAAAGAT|118020|
|TAACAATTTT|AATTGGAAAA|AAATATTGGG|AAGTATATGG|AAGAACAGGA|ATTCCAGCT|118080|
|AGATTCCATC|AACATTAGGT|TTGTGAGGTT|CATCCATGCT|GTTTATAACT|GTGGTTTTAA|118140|
|TTTTCATTTC|ATCGCATGTA|AACCTAATAT|CACCACTTTC|AAAAGAGTT|TAGCATTTGA|118200|
|CCCAACAATT|CCTCTCCTAG|GTATACAAAC|AAAATATGTA|TTCCTATATA|TACCAAGACA|118260|
|CATACACAGG|AATATTCACG|GTATTGTTTA|TATTAGCTGA|AAAAGGGAAG|CAAATATGCA|118320|
|TCAACAGTAG|ACACCTAAAT|TGTTGCACTC|ATAACATGGA|ATATTACATA|ACAATAAAAA|118380|
|TGAATTAAAG|TTATACACAG|CAACACAGAT|GAATCTATTC|AAACCTAATG|TTCTGGAGTG|118440|
|AAATATGTCA|GGTACATAGG|ATTACATTTG|TTTTATTTCC|ATTTATATG|TTTCAAAAAC|118500|
|AGGCATACTA|AATTACAGCA|TTGGAAATCA|AAATAGGGGT|TATGTTTAGG|GCAGATGGAG|118560|
|TGATAATGTG|ACTGGAAGCA|AGCATCAGGC|GGCTCTGGGA|GGGTTGGCTG|ATTTTCTGTT|118620|
|TTTTTACTTG|TGTGGCAATT|ATTATGGTGT|TCACTTTGTG|TTCATTTATT|GAGCTTTGCA|118680|
|TTTTTGTTTT|GCTGTGGTTT|TCTGTTTATA|TGTTATGCTT|CTCAGTTTAA|AGAATGTTGA|118740|
|AATCTTCTAA|TACGAAATTT|TTTTCAATG|AGAAGGATTT|TAAGCATCCA|GAATCAATTT|118800|
|TAAAATCTCC|AATTTGCTTT|ATATGTAGGT|TTATGGACTG|CTTAACTGCT|ACTCATTTTT|118860|
|TCCTTCATTT|ATCAATAGTG|AAATATGAAA|TTAAATAAT|GACTATTTGT|GGCAAAATTA|118920|
|GGGACTATGT|AGCATATTAA|CAACTTTATA|AATAAAAGAA|TAAATCAACT|CACCTGGGAG|118980|
|TTGTTACTGT|CATTGACCTA|ATGCTATTTC|CCATGGTACT|CCTTGTCCCC|ATTGAGAGAC|119040|
|ATGAGATACT|GCAGATTTAT|GGGTCACTTT|CAACATGTCT|CCTCCAGGCC|TCATTTTAGA|119100|
|GAAGCATAAC|ATCATGAGGT|TCTATACAGG|CAAGATCTAG|GCTTGTGTCC|TTGAACCTTG|119160|
|CATTCCCTCT|CAAGAGCCAA|CCAATAATTG|AATGATCCTA|TAAAAACAC|AGAAACACAG|119220|
|AGAATGGTAG|CAGAAAGCGG|ATGCTTACCA|AACCTATTTT|CTCTTTTTCT|AAGCAAGGAA|119280|
|TAAGAATAAC|TTACCTTCCT|CCCTTGGAGT|TAGGAGTTCT|TATGTAGAAA|GGGAGGCAGA|119340|
|GTGACCTTCA|AGAGAGTTTG|GAAGGGGGAG|TGATAAATCA|GTTTAAAGAG|AGCACCCACT|119400|
|GATTCTTAGA|TAACTTATTC|TACTTTCCTT|CTCACTCTTT|TGCATTGACC|ATGGCTTAGA|119460|

| | | | | | | |
|---|---|---|---|---|---|---|
| ATATATTTGA | GGAAAAGCAT | ACTGTCCATA | AGGTATTATT | GCCCTTTAAA | GCTGTTGGGG | 119520 |
| GGTACTATGG | GATGGTATTC | AGTGAGAGCA | GGACAGAGTC | TCTACAGAAT | TTTCTCTGAC | 119580 |
| AAAACAAAAA | CTAAATGACT | TCCAAGGCTT | CTCTAGCTCT | AAGCATTCCA | CAATTCTTTG | 119640 |
| GAAAGCTGGA | ATCTAAAATT | GCCTTAAAAT | TAAAAAATAA | GAACAGTTAG | GGTGTACAGT | 119700 |
| CTTTACCATA | TTTATATAGA | ATCATCAGTC | TTCAGTGTGA | TACTGTGCTT | GAACCAACAG | 119760 |
| AAGGACTGAT | GAAACAGAAG | ACAAAGTCCA | GGTCTGGCGC | CATGGCTCAC | ACCTGTAATC | 119820 |
| CCAGCACTTC | GGGAGGCCGA | GGTGGCCAGA | TCACTTGAGG | CCAGGAGTTT | GAGACCAGTC | 119880 |
| TGGCCAACAT | GGTGAAACCC | CATCTCTCCT | AAAAATACAA | AAATTAGCCA | GGCCTGGTGG | 119940 |
| CAGGTGCCTG | TAATCCCAGC | TACTCGGGAG | ACCAGAGGCA | TGAGAATCGC | TTGAACTCAG | 120000 |
| GAGGCAAAGG | TTGCAACTGA | GGTCATGGCA | CTGTACTCCA | CCATGGGTGA | CAGAGTAAGA | 120060 |
| CTCTGTCTAA | ATAAATAAAT | AAATAAATAA | AATAATAAAA | TACAACCTAA | AACCTAGCAA | 120120 |
| TCTCAGCCCT | GGAATTCTAT | TCAATTGCAC | CATGTTCAGC | AGTGGTAACT | GGAAACATCA | 120180 |
| ATGCTTATCA | ATAAGAAATG | GATGAATAAC | TTATGCTATT | CCATGTGAAG | GATTTCTTTT | 120240 |
| TTCATGACAG | GGTTTTAGAA | AAGTTTGGTT | AAGAGAAAAG | CAACATGCAG | AAGTGTATAT | 120300 |
| AACATCGTTG | TAAAAAATTT | TTATTATTTT | TGTTTTGAGA | CTGGGTCTCA | TTCTGTCACC | 120360 |
| TAGGCTTGAG | TGCAGTGGCA | CGATCTCTGC | TCACTGCAGC | CTCTACCTCC | CAGGTTCCAG | 120420 |
| TCATCTTCCC | ACCCCAGCCT | CCCAAGTAGC | TGGGACTATA | AGTGCGTGCC | ACTGGGCCTT | 120480 |
| GCTAATTTTT | TGTATTTTTT | GTCAAGATGG | GATTTCACCA | TGTTGCCCAG | GCTGGTCTTG | 120540 |
| AACTCCTGAG | CTCAAGTAAT | CTGCCCATCT | GGCTTCCTAA | AGTGCTGGGA | TTACAGATGT | 120600 |
| GAGCCACTGC | GTCCAGGCTT | TGTTTTTTAA | ATTAATAACC | CTAATCAAAA | GACAAACAA | 120660 |
| TTATGCATAC | AAGGCCAGGC | ACAGTGACCG | TAATCCCAAC | ACTTTGGGAG | GTCGATGATC | 120720 |
| ACTTGAGGCC | ATTTCTAGAC | CAGCTTGGAC | AACATGGTGT | GACTGTCTCC | ACAAAAAATA | 120780 |
| AAAACAAAAA | GCCCGGCTTG | GTGGTGCGTG | CATGCAATCC | CAGCTACTCC | GGATGCTGAG | 120840 |
| GCTGCAGGAT | AGCCTGAGCC | CAGGAGTTGG | AGTGGAGGT | TACAGTGTGC | TGTGATTATG | 120900 |
| CCACTGCAGT | CCAGTCTGGG | CAACAGACTG | AGACCCAGTC | TCAAAGATA | ACGTGTTTTT | 120960 |
| TTTTTTTTT | TTTTAAAAAA | ACAAACCAC | AAGTATGCAT | GTATATAGAT | AGGTGTATGT | 121020 |
| AAAATACTTA | GTTCAAAGAA | AAACATGTAT | ATTTCTCACA | AAAATAGGTG | AGAATTTTTG | 121080 |
| TTTTAAGGA | TAAACCTAGG | TAGCTACATA | TTAGTTTGAG | GAAGGGGGAA | CAGGGATGTG | 121140 |
| ATGTGCCTGT | ATCCCTGACT | TTAGACGATG | GAAGGAGCTA | AGCAAAACAA | TTGAAAAAG | 121200 |
| ACCGTTTGAA | AAATACAACT | GATTATTAAC | TCATATGCAC | ACACGCAAAA | ATAAACTTTT | 121260 |
| AGAATTGAAC | TGCACTAAGT | AAAAGTGAGT | AAACTTGGCT | CATCATATAC | TCTTGTCAGA | 121320 |
| TGTAAACAAA | AAAGTCCAAT | TATTAAAATC | TGACCCCCAG | AATTAAAATT | GCAAAAGCTT | 121380 |
| AAAGGGGCAG | TTCTGAGAAA | AGGATCTTCA | GTTTTGAATG | TGTGGGCTCC | ACCAGGGTTG | 121440 |
| AAAATCCTGC | ACGACTGATG | AAACACGATC | CAGTTAAGCA | CAGTAATTTT | CAAATATCCA | 121500 |
| ATCAGGGCGC | TTCCGTTTCT | AAAAACAGAG | AAACCGAGCA | AGGGATTTTG | GGTTGCAGCT | 121560 |
| CTAAAACTCC | AACAAACTAA | GCTCCTTTGT | CCTGACAAGG | GCCTAAACCA | AGTCGACAGC | 121620 |
| CCGTAAGTGC | ACCCATGGTA | AGGCGCTGCA | CAAAGAAAGC | ATTTTGCGTT | TCAAAGCTTT | 121680 |
| GTCATGATGG | CGCTGCAGAA | AGCAAGCGAG | CTAGGCCTAC | CTGGCGGGGC | TTTCAGAGGA | 121740 |
| CGCCAACGTG | GGCGCCAGCC | ACGCCAGCAG | GGTCACCGTC | CTTCCCAAGG | ACAGACAGCT | 121800 |
| CGCTAGCCAC | TCCTGTGGAG | AGGGCGTGGT | TAAGCCATAT | ATTTTGCCAA | CTATCCCAGA | 121860 |

```
AGCATTTCTT  AGGACCACCC  AATTTCGGAA  AATGCTACTT  TAGCAATATT  GACCCCAAAA  121920
CGCAATATCC  CCACTTTAAC  CTTGTATAAT  AAAAAGCCTC  AAGCCTGGGA  CTGGGCTTCA  121980
ACCTTGGTTC  AATACGGTTA  TGACTAATTA  GCTTGGAGTC  GTGAGACGCG  GGACTTCCGG  122040
CTACCGAAAC  CCAGGTGACT  TTAAAACTCG  ATTTTAACTC  GGTGCATTTG  AATTCACCTT  122100
GCTATCTTTG  ATAGATTGAG  TAGTAAATTC  TTACTAGATG  AGGCTATGTT  AAAGTTCTAT  122160
CGACTCTCCA  AGTGATTCTA  ATATAATTGA  GGGCGTGTTG  CATTTGCTTG  GGGGATTTCA  122220
TCTGTGTACT  ACAGCTCTTT  TCCTGAAATG  CGTAGGTGGC  TCTTAAAAGA  GCCGTTGGGT  122280
TACTAGAAGA  AACTTCTAAC  TGAATTTACT  TTTTCTTGGG  TGCCGCTTTC  TTGGGTTTGG  122340
CAGTCTTTGG  CTTCGTCACC  CTAGCCTTGG  CCGCCTTGGG  TTTTACAGCC  TTAGCTTTAG  122400
CAGGGCTTTT  AGCTACTTTC  TTGGGCTTTA  CAGTTTTGGG  TTTTTTTGGA  TTCTTGGAGG  122460
ATTTCCTTGT  TGCCGCAGGC  TTTTTAGCCT  TTTTCGGAGT  CTTGACGCTC  TTTTTGCTAG  122520
CCCCCGTGGC  CTTTTTGAGC  TTTTTAGATG  CACCCGTTGC  CTTAGTTTTT  GTAGCCACCT  122580
TTGAGGCGCC  GGGCTTGGTT  TCCACGGAGG  ACGCCTTCTT  GTTGAGCTTG  AAGGAACCCG  122640
AGGCTCCGGT  ACCCTTTGTC  TGCACCAACG  TTCCCTTGCT  TACCAGGCTC  TTAATGCCCA  122700
GCTTAATGCG  GCTGTTGTTC  TTCTCCACGT  CGTAGCCTGC  GGCCGCCAGC  GCCTTTTTAA  122760
GAGCTGCCAA  CGACACACCA  CCACGCTCCT  TAGAGGAGGA  AGCAGCCTGC  ACGATCAGCT  122820
CTGACACGGA  AGGGCCAGCG  GGTTTTTTCT  TGGAGGCTGC  TGCAGCCTTA  GCAGGTTTCT  122880
TTGCCTTCTT  GCCAGCTAAA  GGTTTCTCAG  GAGCAGCAGA  AGCGGCGGGG  GCGGGAGGCA  122940
CTGTTTCAGA  CATGGTGACT  AACACAGCAC  ACCAAATAAA  GTGGTATAAA  CCTGACGAAG  123000
CAGGATGCGA  AAAAAAGGCC  CCAACGCAGC  CTATTTATAG  GGTGGGACTG  CGCCGTGATT  123060
GGTGCCCGTC  AGTGCCCGCC  CCTCGCGCCC  TAGCGCCCCC  TGCGCGCTGC  CGAGGGTTTC  123120
GCCCAGTCTC  AGAAGGCAGC  TGGGGGCCTC  TAGGGCCTAT  GGTCCTGCTC  CCCTCAACGC  123180
AAGCAAACAC  ACAGAAAAAG  CCGCTCTGGT  TGCCTCATTG  TGAAGGAAAT  TGTAGGCAGA  123240
CTGCCGCCCA  GTAACATCAG  AGGGTACCGC  TTCTCTCTCA  AAAAGCAGCT  CTTTTTAGG   123300
GAGTAGGTTG  AGAGGGGGCG  GTTTACAAAT  GCAGTGCCAC  AAGCATCCGA  GGAGTTTTAT  123360
TAGAAATTTT  TAGAGGTCCG  TTGCCAGAGA  TGTTAGTTTT  TAATTTGCAA  GAAATGTAAA  123420
ATACAGTGTT  TTGAATAGTT  GCGGAGGGAG  AGAAAAGTGC  GAGTTTTAGG  CCGTGTTAGG  123480
GCCAGTTGTC  ATCAACTCTA  TTACATTTTC  TGGCAATGTT  TTAGAGCGAT  GTGTCTCGCG  123540
AATACCTTTC  ACGTCAAACA  AGAATGAATC  GTAGACAACA  CCAGAATTCA  CAAACGCTGC  123600
AATTAATACT  CAAACTGCAA  GTGTGGAAAC  GTTTCTGCAC  TTGCAACTTA  TTTCCACAGT  123660
CCAATGTGGG  ATGCACTTCA  GGAATTTCCA  ATGCCCTTTT  CATCCATACA  ACATGCCCCA  123720
AATTGGTATT  AAGGTTTACA  ACCTGTGTTC  CATGTCAGCA  CACGCAATCA  GCGCACCATG  123780
ACATGGTCAA  CTCATTCTTT  TATTCAACAA  ATATTTATGG  GCCTCACAAG  CCTGCGAAAG  123840
GCGTTAAATG  CTGGGTCCAC  GAAACCGGTT  CCCTGACAGG  CATTCTGCTG  GGGAGTTAAG  123900
TCCACTTAGT  GTGAAAGCAA  ACACGGGTGA  TAAATGCAAG  CACACCCTGG  GGATAAGATT  123960
TTATGGTAAC  AACCCTTTAA  CTTGTTTGTG  GCTGTTAAGT  GCATTTCAAA  GTATCAATAA  124020
GCTAAAACGA  TCTCACATTG  CCAATCAGAG  ACTCAGCTAA  TGGGAGAATA  AAAAACTATT  124080
AAATCGACAT  CCACTTCTAC  AATCCTATTC  TGGATAACCC  CCTAGCACAG  CACAGCAGAG  124140
AGTGAGGTAA  TGCGGTCTTA  TTTCCGCTCC  TGCTGTGGTA  GTTTTCAAAT  AAGTCCGAAC  124200
CATGCTAAGT  AACCTGAGCT  TTTCCCCTTT  TTGTTCAAAC  AACGTGCCAA  CCAAATAATG  124260
```

```
GAGTGGTCCC  AGATAAGTAT  TGTACCCATC  TTCTGCACCA  GTGCTTCCTA  CGTCCCATTT  124320
TATTGAGAAG  GCATGCATTC  AAATATTTCA  CGTAATTTCT  AAAAATTTGG  AAAATAACGG  124380
TTGGAAACTC  TACATCTTGG  TTTGACGGCT  AGTCAGTTAT  GAAACACAGG  TATACAAAAT  124440
TGGAAGATTT  TTGTAAGTAA  ACCCTTTGTG  AAAGATATAA  ACCTTTCTTA  GTGTAATAAG  124500
CGAGGTATCT  GAAAAACGC   AACTTTTGAA  AAGGAAATAC  TCCTAATTAT  CTGATTCAGG  124560
AGTTTCCACT  TTAAATAATG  GGTTCTGCCT  CCCTTTTTTC  TATTGGGTTA  AACTGGTTTC  124620
AAATAAATG   GGAACGCTCC  ATGCAAATGA  AGGATGATAG  ATCTGCTTTC  TAAATGGCTG  124680
TTCAAGAAAA  TAGCCTAAAC  CAATCAAAAG  ATAGAATGTG  GCCTGTCTCT  TGTGAATTTA  124740
AAAAGGTCAC  AATCCACTTT  TCAGTGTTTT  GAGATTTTCA  AAATGATTGC  ATTAGCTCTT  124800
GGCAATGCTA  AATTATGTTC  CTTGCGAACC  ACTATCCAGT  TTCTCTTGGG  CCAAGTCCAC  124860
CTCCTGCTCC  GCAAGAGGAA  CAACTCCCAG  CTGGTGGTAC  CTGGCGGCAG  TGCTGGAGAA  124920
ACGCCATTTT  GTGACTGGCA  GAGTACACCT  AGGCTTTAGA  AAACAAAAGC  TGCAGAACGC  124980
TGCAAGTTTA  GGATTCAAAG  AGCATAATCA  AGAGAAAGAC  GTCTCATAGA  AAATGTTTCT  125040
GAGTAATAGT  GTAATCCTAC  TATGTTTGAG  ATGCTTTGTA  GATTTCAATA  ACACTCCTAA  125100
GTCAATTAAA  GCATTACAAA  GGAATCCAAT  TCTTGTGAAA  GGTTTCAGAA  ATTCCCGTAA  125160
AGGGTACATT  TCCGGAGAGG  AGGTGAGCAG  TATTCCCTCT  TTTTTTTTT   TTTTTTTTT   125220
TTCCTAAAGA  GCTGAAGGTT  ATACGGAATT  GGGGAATTAT  AATACCTTTG  GAATCAATGC  125280
CTTGTTTTAT  GGAAAATAAA  CACAGCCTTC  AGGTTATGAA  AACCAGATGT  AGAAGAGGAC  125340
AAGTTTAAAA  AATTAAAGTC  CAAGCCGGCG  CAGTGGGGCT  CCCCTGTAAT  CCCAGCTACT  125400
CTGGATGCTG  AGGCGGGAAG  ATCCTTTGAG  CCCAAGTTTA  AGACCAGCTT  GGGGAACAAA  125460
GCAAAGTAA   AATAAAATAA  TAGTAGTAAT  AAAATACCAC  TTAAATAATC  ATCTGTAGAG  125520
TTGGAATAGA  ATATAGTAGC  CGGTGAAACT  GCACGATTGT  TGCTGGCTTA  AAGATAGACC  125580
AATCAGAGTG  TGTAACGTCA  TATTTAGCGT  CTTCTATCAT  CCAATCACTG  CACTTTACAC  125640
ACTATAAATA  GAGCAGCTCA  TGGGCGTATT  TGCGCTAGTG  TTGGGTGTTC  CGCTGTGCTG  125700
TTTTTCCGTC  ATGGCTCGCA  CTAAGCAAAC  TGCTCGGAAG  TCTACTGGTG  GCAAGGCGCC  125760
ACGCAAACAG  TTGGCCACTA  AGGCAGCCCG  CAAAAGCGCT  CCGGCCACCG  GCGGCGTGAA  125820
AAAGCCCCAC  CGCTACCGGC  CGGGCACCGT  GGCTCTGCGC  GAGATCCGCC  GTTATCAGAA  125880
GTCCACTGAA  CTGCTTATTC  GTAAACTACC  TTTCCAGCGC  CTGGTGCGCG  AGATTGCGCA  125940
GGACTTTAAA  ACAGACCTGC  GTTTCCAGAG  CTCCGCTGTG  ATGGCTCTGC  AGGAGGCGTG  126000
CGAGGCCTAC  TTGGTAGGGC  TATTTGAGGA  CACTAACCTG  TGCGCCATCC  ACGCCAAGCG  126060
CGTCACTATC  ATGCCCAAGG  ACATCCAGCT  CGCCCGCCGC  ATCCGCGGAG  AGAGGGCGTG  126120
ATTACTGTGG  TCTCTCTGAC  GGTCCAAGCA  AAGGCTCTTT  TCAGAGCCAC  CACCTTTTCA  126180
AGTAAAGTAG  CTGTAAGAAA  CCAATTTAAG  ACAAAAGGGA  ATGCATTGGG  AGCACTTTTC  126240
GTTTTAATGC  TACTGAAGGC  TTCAAAACCA  ATCGATTTCG  GCCGGTCGCG  GTGACTCACG  126300
CCTGTAATTC  AAGCACTTTG  AGAGGCTGAG  GCGGGCGGAT  TACCAGAAAT  CAGGAGTTCG  126360
GGATCAGCCT  GGCCAACATG  GCCGAATCCC  GTCTCTACGA  AAAATACAAA  AACACGCCGG  126420
GCGCGACGGC  GAGCGCTTGT  AATCCCAGCT  ACACTCTGAA  GGCTGAGGCA  GGAGAAACAC  126480
TTGAACCTGA  GAGGCAGAGG  TTTCAGTGAA  TCGAGATGGC  TCTAATGTAC  TCCAGTCTGG  126540
GCGACAGAGA  GATTCGGTTA  AAAAAAAAGT  TCGACTTAAA  ATAATTCTGG  AGTCAGAATG  126600
GGTTTACATT  TAATTCTTAA  CCCAGTTCCT  CAAAGCCTGT  AGCTCTGTTA  AGAAAATAAA  126660
```

```
GGCCATTGGT  CAAGCCTGCT  TGGTCCCACC  CTCATCTCCC  CACCCTCCCC  CAATCGCTGC  126720
TCCCGCCATT  TCCTGGGGCT  TGGAGGAGGG  GTTAAAGGAG  CGGACTGTAG  GCGTCACATT  126780
TCCCGCCTGC  GCGCTTTTCA  GTCTCAGTGT  CCGCTGGAGG  TGGGGGCAGG  GGTAACGTAG  126840
ATATATAAAG  ATCGGTTTCC  TATTCTCTCA  CTTGCTCTTG  GTTCACTTCT  TGGGAAGTCA  126900
TGTCTGGACG  TGGTAAGGGC  GGGAAGGGTT  TGGGTAAGGG  GGGTGCCAAG  CGCCACCGCA  126960
AGGTGTTGCG  TGACAACATC  CAGGGCATCA  CCAAGCCGGC  CATCCGGCGT  CTGGCCCGGC  127020
GTGGCGGTGT  GAAGCGGATC  TCTGGTCTGA  TCTACGAGGA  GACTCGCGGG  GTGCTCAAGG  127080
TGTTTTTGGA  GAACGTGATC  CGTGACGCTG  TCACCTATAC  GGAGCACGCC  AAGCGCAAGA  127140
CAGTCACTGC  CATGGACGTG  GTCTACGCGC  TTAAGCGCCA  GGGACGCACC  CTTTATGGCT  127200
TTGGCGGTTA  AGGTTGCTGA  TTTCTCCACA  GCTTGCATTT  CTGAACCAAA  GGCCCTTTTC  127260
AGGGCCGCCC  AACTAAACAA  AAGAAGAGCT  GTATCCATTA  AGTCAAGAAG  CTCAATGTGT  127320
AATTAAGATG  AATGATACTG  AGCTGACATC  CTAAAAAGGA  AAGATTAGGG  GAACTCCAAG  127380
TTTGCCCTCC  ACTCACTACA  TATGGGTAGG  GGAGCAACGA  TATTCCAACT  CTGAAGAAAG  127440
AGTGGAAAAA  AAGTAGTGTT  AAAAATTTGT  ATTAGTTTCC  AAGGGACAAA  GAAGCGCTGC  127500
CCAATCAATG  AGGGCCATTC  GTAGCTGTCA  ACCAATCAGA  ACTGATGAGC  TAATATTTCC  127560
TGAGGCAAGC  CAGGGAGCCG  GAGGGGAAGC  TAAGAAGCTT  ATTGAGAAAA  AACAAAAACC  127620
CTGTTTTAGG  AAAAAAAAAA  ACCATCTTTT  AGCGATTATG  AAATAAAATC  ACAGAGACAT  127680
TTAAGTATCC  CTCAATCATG  TACTGAGAGC  AATACTAAAT  TTATCGCCAC  CAATACAGTT  127740
TTACTCTATT  AAAAAGACCC  TGAAAATTGA  AACCCTATTC  AGACTCCTGG  AATACCCAGG  127800
ACACTAAATT  CAGGGGAGAT  TAAAATCTGT  TTTAGAGAGA  AAAGGCACCT  TTTTCAGTGT  127860
TACCGCGGCC  TTCAGCAGTT  AACCTTTTTT  TTTCCCCCTT  TACGCAGAAA  TGGAAATTTG  127920
GGTGATAGAA  ATATTCCGAA  ATTAAATTGT  GATGATGGTT  GTACAACTAA  GAAAACACGG  127980
TAAAATTCAT  TGAACTGTAC  CTAAAGTGGG  CAAATTTTGT  GGTACATTAA  ATATCAATAA  128040
AGCTGATTAT  ATACATACAC  ATATATTTTT  ATATATGCAG  AGAGAGAAAT  GATGCAAGCA  128100
GGGTGGTAGG  ACATGAGGTT  GGTAGCATAG  GCAATGTTGG  TCTGTGAAGG  GCCACCTGTG  128160
CTAAACCTGG  AAGCCTGGGG  TTTGTCCAGT  CAAGCCATGG  TAGCCATAGT  TTTAAAGGAT  128220
GTTCCTGATG  CAGTTATGTG  TTCCAGTTAA  GTACATCTAG  CTTCAGAACT  CAGCTGGAAA  128280
AGGGATGTGA  ACTTCAGGTT  AGCTGATAGG  GAAATATCTT  ACTCTCATCT  GAGTAAATAT  128340
TCACAAATGC  CTCTCATTGT  GCTCTTTTTG  GTACCATTGT  TATAGGACTG  ATTTCAGCCT  128400
CACGATGTTA  GCTTCAGTGA  TGGATGTCTC  TTTATTTTGA  GGTCCTGTTT  TCCACCTGAC  128460
AGTTTTCATC  CAGGATTTCT  TGAGGAATTA  CACAAGTACC  CAGCTTGGCT  TAATTTAAAA  128520
CTGACAATGG  AGAGAATTCA  TAGCTGCATT  CTGGATAGTT  TCAGGAATCA  GAGGAGCAAA  128580
AATGAGCCTG  GTATGGAGGG  TGGGTCATTT  TATGTCTTTC  TTAGTTGGTA  TTTTAAAGAT  128640
ATTTATTGAT  CTCATATGCC  AGATATTGTT  GAAATCATTG  GGGTACATAA  GTTAGAAAAT  128700
TTTAATTCCC  TTTCCTGAAT  TCCAGAGTCA  ATGTAGAGGG  GTGTGTGGAT  ATCGATTACC  128760
CATATGGGAG  GTATAGTCGT  TGTAACAATA  AGCCACGACT  AGCTCCTGTT  ACGTTTTGCC  128820
TGGCCTTTCA  TAGCATTGCT  ATGTTCATAG  CATTGCTGAT  ATGTCATACT  CATCTTAGGC  128880
ATACCCACCA  CCACCTTGGG  CCTTCTTCAG  TCCTAACACT  CATGCAGTCC  TTGTTCAGAA  128940
CAAAGATAAT  GTTGCTTAAT  TTGCAACCCC  TAGACTATCC  CCCAGATTTT  CTAAAGAGAA  129000
ACTGCACGCT  GATTGCTTCA  GGCAGTGGCA  GGTCAAGGAA  TGAGATGGGG  AATTGATTGT  129060
```

```
GTTAGCATTC TGGTGGGCTT AGTGGAGAGC CTGGAGACTT ACATAGAAAA TTCACACATC  129120
CTTTCATTCA ACAAACCTCC ATAAACTACC TGTTAAACGT CAGCCCTGTT CAAGGTGCTA  129180
GGGATACTTC TGGGACAAAA CAAAGTCCCT ACCTTCAAAA AATATATTCC AGTTGGGGGA  129240
GAGAGAACAA ACACAAAATA AAATATATCT AGTTATATGT ATTTTTTGTT AAATATATTA  129300
TTACATATAT AATTCTAGGT GGGGAAATGT TATATATATA TGCTATTGAG GATAGTCAAC  129360
TATATATATA TATGCTAAAT GAGCAGAAAA GCTTATTTTA CAAGGGATGA TTATGGGAGG  129420
TCTCTTTCGT AAGGTTGGTA TTTGAGGAGA GGCTTGAATG AAATGAGATC TAGAGCCATT  129480
CAGATATCCA GGACAAGACC CTTCTAGGGA GAAAGAATAG ATATAAAGGT GCTGATGCTG  129540
GAAATGCTTG GTCCATTCCA GAAACAGCAA GGTCAGTGAA GAGAAAGAAC TGCGAAGAGA  129600
ATGAGGTCAG AGGGTAGCCA GAGTACAGAT CTAGTAGGTT GAGCAGCTCA TCCTAGTTTG  129660
CTTGGAACTT TCTAAGTTTC AGCACTGTAA GTCTTACACC CTGAGAAACC CCTGAGAGTC  129720
AGGCAAACTG TAATGGTTGG TCATCTTACT TGTAGGCTAT GATAAGGATG CTGGTTTTTA  129780
TTATGAAGGT GATGGAAAGC CAGTGGAATC TTTTCAGCAG ACAGTGGACA TAATACCTTC  129840
AAAAGGATC ACTGTTGATG CTGGATAGAG AAAAAACTGT ATGACAGGGG GATTAAAAGT  129900
GAAAACAAAG ACCAGTTTGG GGTCACTGTG GTCATTCAGA CAAACCGCCA TGGCAGCTTG  129960
CTCCTAGAGA AGCAGCAAAG AAAACAATGA AAGGTATTCT GATTGATTTT CAACAGAGCT  130020
GACTGCATTG GGTGAAAGTT GTAAGAAGCT CAGGACAAAC AATATTGCAC AATTCCTGGC  130080
CCAAGCTGCT TGAAGAATGG AGTTCTATTG ATTGACATGA CAAATATCAG AGGAAGAACA  130140
GACTTGGTGT TTACGTATAA ACATATTTTG GACAAGTTCG AGATGCCCAT TATTCAATTA  130200
GATACATCAA ATATGCAGTT GTATATGAGT CTAGAGATTT AAGGTCAGGG AGATGGTTTA  130260
TAATTGCAAA CACTTATTTA GAGACACAGT TTCACTCTTG TCTCCCAGGC CTAAGTGTAA  130320
TAGCGCGATC TCAACTCACT GCAACTTCTG CCTCCCGAGT TCAAGCTATT CTCCTGTCTC  130380
ACCCTCCCGA GTAGCTTGGA TTACAGTCGC CCGCAACCAT GCCCAGCTAA TTTTTTTTTT  130440
TTTTTAGTA GAGACGGGGT TTCACAATAT TGGCCAGGCT GGTCTCGAAC CCCTGACCCC  130500
AGGTGATCCA CCAGGCTCAG CTTTCCAAAG TGCCGGGATT ACAGGCGTGA GCCACCTTGC  130560
CGGGCCTATA TTTCTTAAGC TCTATGTTTC GTTCTGAAGC TTGAAGTGGG TGGAAGCAAA  130620
CTGATAGAAT TTGGAGAGGT GGTTAGGCAT CCCGGGAATG AGAAACAGCC CGAAGCTGCC  130680
ACTATCACAG GCTTTGGCAT TGCTAGAAGT TAACGTGGCA CTTACAGCTA GGCCGTGGTG  130740
TTCTGTTGAA CAAACTATTT GACAGAGCAC AGAGCATGTA AGTGGTGAGG CCAGTTGAGT  130800
TAGCCAAGAA AAGAGGAGTC CAAGAACTGA GCCAGAGTAC ACCAGAGTAT GTAGTGGAGT  130860
ACAGCTTTCT CATTCTTTAG TAGGGCTGTG TAGAGAAATA CTCTATTTTA TGGATGTATA  130920
GATCACTCTA GTCCTTTCTG ATGAAACTT TACAGTTGCC ACTCATTTAC TATTACAAAC  130980
AATGCTGCAC TACATTATGT TTCAGTTTTT AGCCATCTCA TCTGGTCTCA GCATTTATTT  131040
ATCTGCTGAT GACTCACACA TTTTTATCTC CAGCTCAGAC CTCTCACCCG AACTCACTTA  131100
TTCAACTGCC TATTCACTAT ATCCTCCTGT CAGGAGAAGC TTGTTAGCAA AGTAACCAGA  131160
AAACAAAGTT GATTTTTTTT GCTGAAGTAG CCATCAATAT ATTTGTTACT AAATCAAAGA  131220
TGCTGAATAT TTGGCTGACT TCTAAAAATC TGGTCACCTA ACTTTGACAC TTCCTAGGTC  131280
GTACAGTTTG AAACTTTCAC AATTAAATCA GTTTTGGAAT TTACAATTTA AGGCAGGAAT  131340
AGAAGACTAT TGGGTTGACA GGTACAGTGA AGATGCAAGT CATCTGAGAA TCTTACATCA  131400
GAGGGGGCTT CCATCTTATA GCTGCTGCCA CGGACCTCGG AGTCAGAAGA AATTTGAGTC  131460
```

| | | | | | | |
|---|---|---|---|---|---|---|
| CTTATTTATA | AAACAGACTC | CCTTAGTCTA | CTAAGTGGGA | ATTTACGAAC | TGCGTAGGCA | 131520 |
| GCCTGCTTAG | GGGAGCCTCC | AGCCTGAGGA | CTGAAAATAG | CAAAGCAGCT | TTAACCGCCA | 131580 |
| GTCCTACTCC | AGAGAAGGGG | GAGGTGACGT | CACTCAGCAG | GACGCCAAGC | TCAACTAGAA | 131640 |
| ATGGAAGTAA | AGGCTTCTGG | CGCTACCGGC | AGGGGCGGT | TAAGGACGGC | AGGTGTTACC | 131700 |
| AGGGAAGCTA | AAAGTACAGC | TTTTGCTGAC | GTTAAGTCAG | ATACGCCTGG | GAAAACAGAC | 131760 |
| CTGACACCCA | TTTTAATCCA | CCTACTCAGT | TCCAGGCAGC | TAGCATCTTA | GGCTCTCGTA | 131820 |
| CAAATAACGC | ACAACTCGTT | TTTAAAACTA | AAAAGCTGAG | CTACTCATTT | ATCGGACTCG | 131880 |
| CGCTGCACGT | TAAGTTGCTT | GACATGTCAA | AACTATAGCA | TTGAAGTTTA | TAGCTCACTT | 131940 |
| ATCTCGGAGA | CCTCGTTTAC | TTAGCTGATT | TCTGCTTTAG | CAGCCACTCA | GACCAAACAA | 132000 |
| CCTGGTCTCT | CCCAACTGGT | TTATAATAGT | TCTACATACT | AGGCAGAATA | GCCGAGTAAA | 132060 |
| GCCATTGAGA | TGTTACCATC | CGAAAGAATA | CAATCACAGC | TCTTTCTGAG | AGGGAGTGGG | 132120 |
| CGGCCCTGAA | AAGGGCCATT | GGAAGAAAAC | TGACGAAAAG | ATTAACCGCC | GAAGCCGTAC | 132180 |
| AGAGTGCGTC | CTTGACGCTT | GAGCGCGTAA | ACCACATCCA | TGGCAGTGAC | AGTCTTGCGC | 132240 |
| TTGGCGTGCT | CCGTGTAGGT | CACGGCGTCC | CGGATCACGT | TCTCCAGAAA | CACCTTGAGA | 132300 |
| ACGCCACGAG | TCTCCTCATA | AATCAAACCG | GAAATTCGCT | TAACCCCACC | ACGCCTAGCA | 132360 |
| AGGCGCCGAA | TGGCCGGTTT | GGTGATGCCT | TGGATGTTAT | CCCGCAGCAC | TTTTCGGTGA | 132420 |
| CGCTTGGCAC | CTCCCTTACC | CAAACCTTTA | CCGCCTTTGC | CGCGACCAGA | CATGTCTAAC | 132480 |
| CAGCTGACAA | CAAAAACCAG | GTACGCGAAA | AGAAAGCAAG | CCACGAGCAT | TTATACACGA | 132540 |
| ACATCGGACC | TTATTGAGAA | CTGAAAGCGG | GAGCGAGGAT | AAGGAGGCGT | TGCTGCCTCA | 132600 |
| CTTTTTGCTC | CGCCCCTCGA | GGGGCAGTGA | CCTAAGGACT | GCGAGGGAGA | ACACAATAGT | 132660 |
| TTCACTTTTT | AATCCCTTTA | GTTTTTCCCT | CCCGTTTACG | ACACTACTAT | TTGAATCTGA | 132720 |
| ATTTATACCC | TCGACTGAGA | ATTTTAATAA | GGGCTTATAT | TAAGGGCTTT | CACTAATATG | 132780 |
| CCGGAGTGGT | AAACTTTTTA | AGTCTTTCAA | GTGCTTGAAG | ACATATTGAC | TATTCAAAGG | 132840 |
| TACTTAAAAG | AGCAGGCGTG | AAAAGATCAC | TCTGGCCTTA | TGTTTTCTTG | AAAGCTGACC | 132900 |
| TGTTTCTTAG | AAGCAGTAGG | TGAAATTCTC | ATATGAAAGA | TGTTCTCACT | GTAGTTTAAA | 132960 |
| AAAAGCAACA | TTCTTCTCAA | GGATAGGAGG | CTGAGGCCAA | GAGAATTCTG | TACAAACCTT | 133020 |
| GCACTAGCCC | TTGCTGGGCG | CTTCTCTACA | CAGTTATATA | TTCTAGCCTA | AATCCCTTTG | 133080 |
| CTTTAGCGCA | TTTTTACATT | TTACTAATTG | TCCAATTCAT | TATATAAGTA | GCTAACTGCT | 133140 |
| TTTTTGGGC | TTTCATTACC | TTATGAGAGC | ACCTGTGTCA | CGTAAAACCT | GTGTTAAATA | 133200 |
| AATGCATATA | CCTTTCTCCT | GTTAATCCAT | TTTACATTAA | TTTAATTTGC | TGGTCCAGCC | 133260 |
| AGAGCCCTAA | GAGGATGGGA | GTGGAGTTTT | GCTATCCTTC | ACACTGTACT | GTCTCATTCA | 133320 |
| GAAGAGGGTG | ATAGCTCATT | GCAACCGTGC | CTTCATCTGT | AAATCGGGTT | ATGATGATAC | 133380 |
| TCAGGGGACT | TTTAATTAGC | TAATGTGAAC | GAGGCATGAG | AAGAGACTGT | GGAAAAGAAA | 133440 |
| TAAATATTAC | ATAATATGGT | TTAATTTAG | ATGTTACTAC | TTAAAAAAAT | CTGCTCAGAG | 133500 |
| TTGGGATATT | GTCCTGAACT | CTCATTTTCG | TGTTTTACT | CCCAACACTA | TATTGCTAGC | 133560 |
| AGCAACTATG | TATGTATTAG | TAAGGATTGT | TTTTTAAAA | TCACAGCCTG | TAATAACGTA | 133620 |
| CAAGGTGTTG | ACAGATTCCG | TTTAGCTTTT | CATATGTGAC | ATGTTAAAAT | TGTCCGAAAA | 133680 |
| TATTCCTTTG | TTCTCTTTTC | CAAGGTGCAA | TACAATAGCA | GCATTCGTGC | TTTCCTATAG | 133740 |
| CCAAGTCTGG | AGTGTAGTTC | AACTCTCCAT | ACACGCTTCT | CACTGTTGTT | TTAAATTTCC | 133800 |
| TGAAAACATT | CTTAAATCAC | TTCTATTGGA | AAAACTGCAA | GGGCTACTGC | TAAATTTTTA | 133860 |

```
AGTCTGAAAA  ATGCACCCCA  AACTTGACTT  CTTTCTCTGA  GAATCTTAGC  CATCTCACCC  133920
AAATCTAACA  AACCAAAACT  GATTTTAGAC  TTCAACAGCA  TTAGCTGTAA  ACTTCAGCCT  133980
GCAGCATAAC  ATCACTTTGT  TGTGACTGGG  CAGGAAAAAC  CCTGTTAAAC  TGTTTCAGGC  134040
GCGTCCGTGT  GAAGAGACCA  TCAAACAGGG  TTTGTGTGAG  CAACAAGGCT  GTTTATTCTA  134100
CCTGGGTGCA  GGCGGGCTGA  GTCCGAAAAG  AGTCAGCGAA  GGGAGATGGG  GTGGGTCCGT  134160
TTTATAAGAT  TTGGGTAGAT  AGTGGAAAAT  TACAGTCAAA  GGGGGTTGTT  CTCTGGCTGG  134220
CAGGGGTGGG  GGTCACAAGG  TGCTCAGTGG  GGGAGCTTTT  GAGTCAGGAT  GAGCCAGGAG  134280
AAGGAATTTC  ACAAGGTAAT  GTCATCAGTT  AAGGCAGGAA  CAGGGCATTT  TCACTTCTTT  134340
TGTGTTTCTT  CAGTTACTTC  AGGCCATCTA  GAGGCATACG  TGCAGTTCAC  AGGGGATATG  134400
ATGGCTTAGC  TTCGGCTCAG  AGGCCTGACA  AACTGAACAA  CTGGGAACAA  ACAACATTTA  134460
ATGCACACAA  TCTCTATCTT  GTAGGGAGGC  AAAATTTTAC  CTCTACTCTG  TTAGGGTCTC  134520
CAGCTGGACC  TGATAATTCA  TTTGCCATAA  AACAGATTAG  CAGAATGAAA  GCATACAAAT  134580
GTATTTAATG  TAAATTTTAT  GGGACAGGAG  AACCCTCATA  AAAAGTGAA   GCCCAAAGA   134640
AATGGCAAAA  GCTAAATGCT  TTCACATTAA  GTTAAAGAGA  GGCAATTGTG  GGAAAGTAAA  134700
CCATATGAGG  AGATTAAAGG  AATATATGAT  TATTTTAACA  AGGTTTGTTT  GTGTATAGAA  134760
GTCTCTCGGC  TATGACTCCC  TGCTGTGTTT  GTGCAGAATT  ATCTCATCTA  TGCCTCTGGG  134820
CTGAAGAATA  TGTCTTTTCA  CCTGGTACAA  GCAGAGCATT  TTTCACATTG  GAACTTTTAT  134880
CTCCTGTTTT  CAGAAAGAAA  AGTTTAGAAG  AATTCCCTTC  TTGAATGCTG  TTTTGAAGT   134940
GCCTTTAGCT  CAAAAGAATC  CTGATCCCAC  AGTGGTCTAT  TTTTGGATGG  TATATTCTGC  135000
AAACAACACC  CCCTTTTTGT  CTCCAATCTC  TCCTTAATTA  CTCCTCTAAT  ACAAAACAAT  135060
AGATTCTTAA  TATAATATTA  AAATGTTTGC  ACTACTCACA  AATACAAAAT  GCTCAATAAA  135120
TTTTCTTTCA  CAAATGAGAA  TTTCATCCAT  TCGTTAATTT  TAAATATCA   ACTGTCAATG  135180
AAGAGTTACA  GCAGAATCCT  TGTTCTGTTG  AGGAGGGGGC  AAAGAATGTA  AGTGAGGGAG  135240
TGGAAAATAG  CTGGACTGAG  CTACCACCCC  CTGTCCATCT  GATCCTCAGA  CAGTAATGTA  135300
ACTTTATTCT  TTTATGCTAT  TCGTCAGACC  CAGTACCTCC  AACACATTTG  TTTCCTACAG  135360
ATAAAGAAAA  TATAAAAAGT  CAAGCGCTAT  ACATCAGATC  CAGCACATCT  ATAACTGGAA  135420
AAAAAATACT  TGACCTTCAG  CTGGGCCCAG  AGCTTGTGAG  TAGTCACCTT  GGCATAGACC  135480
AAGTCCATTG  GCATCTCTAA  CATATCTATA  CTGTCTGTGG  ATAACAAATG  TCTATGCCAG  135540
TTAGAGTCGC  TTGTATAAGA  GTCAAGAAAA  ACGAATCATA  AAACAAACTG  ACATATTCAT  135600
TTTCATAATT  TTTAAAATGC  AAATATTACT  TTATAAACCA  AAAACTGCCT  TATTAAAAGC  135660
TGGAACACAA  ATGAATTTAA  GTAAACGATG  CAATTCAAAT  TTAATCTTTT  GTGTGTGTGA  135720
TTTGTTGTTG  TTGACAGTTG  GTCAGGCGAT  TTTAGTATGG  TACATCAGTT  TACATTCTAG  135780
ATGTAGGCCA  AGAAAGAATG  TTAGGTGTAA  AAAATATTTA  TTGTAAAAAA  GAATGTGAGG  135840
CAAGGTCTTT  GGAATTAGTA  GTTTTAATGT  TGGACATTCT  GTGGTTGTTC  TAAAGTTAGT  135900
CTGTAAAATG  TGATGTAAAA  GCTATATGAT  AAAAAAATAC  AAAATATAAA  AATTTTAAAG  135960
TAAATATTAC  TTTTGTTTGC  GTACAGTATT  CCCATCCCTC  TAAATTTTCT  TCCAGTACTC  136020
AATCCCCAAC  CTCCAAAACC  GAAAAGCAAG  ATCAACAGAA  AGAAATGGT   TAAAACTTGT  136080
AAATTCTAGA  TTTTAATAAC  TACAGGCAAG  AAGTACTGAA  AAAAAGAATG  TGGCATGTCA  136140
TGGTGCATAG  TCCTAGAGGA  GACAAAGCAA  TGCAACCAGA  TAGACTATTT  ACAAGCAAAG  136200
CCACACATAT  AAAAATTCAT  ATATAAGGGA  TTAAATTATG  CTTGGTCGAC  AGACTGACAG  136260
```

```
ATTTAAAGTG GGTAGCTAGC TATGGATAAA ATGAGAGCCA GTTAGATCCC TGCCTCACAT    136320
TTTGCACCAG AATAAATTTC AGGTTAATGT TAACAGCCAA ATGAATTTAA CAGTATATAT    136380
ATATATATAT ATATATATAA TATATGAGAA AACCTAGGGG ACTATGTATT GAGCTGAGAA    136440
AATCTTCCTA AGCATTTTGA GGAAGACACT GGAACTCGCA AGACACAATT TTCTAATCTT    136500
TTCAAAGCTT TGCAAAAATG CCTAGTAAGC GCCAGTTAAC TACTTACCAG ATTTTCCCT     136560
TACTCTTACA AAGTTGTTTA AACAAATGCT AATCATAGCA AGCTAGAGGC CTGAATGATA    136620
GTGGACTTAC ACAGCTTCTC TCCAAATAGC ACCTTAATAA GGTCAGAAAT AACCTACACT    136680
GCAAGACTGA CCAAACCGTT ATTTCTGTTA ATCAACTTTA AGACCATAGT CTAATGCTTT    136740
CCGGGGGGGT CCTTAGAAAT TTGTTCTGTT AAGACAACAA AAAATTATCA CAGCTACTTT    136800
CGTTGGAATA AGTGGGTGGC TCTGAAAAGA GCCTTTGGGT TTAAGACTG ATGAAAAGT      136860
GACTTTACAT TTACGCTCTT TCTCCGCGAA TGCGGCGAGC GAGCTGGATG TCTTTGGGCA    136920
TAATAGTCAC TCGCTTAGCA TGGATGGCGC AAAGGTTTGT GTCCTCAAAG AGCCCTACCA    136980
AGTAGGCCTC ACAAGCCTCC TGCAGCGCCA TCACCGCAGA GCTCTGGAAG CGAAGATCGG    137040
TCTTGAAGTC TTGGGCGATT TCTCGCACCA GGCGCTGGAA CGGCAGCTTC CGAATCAGCA    137100
ACTCGGTCGA CTTTTGGTAG CGGCGGATCT CGCGCAGAGC CACAGTGCCC GGGCGGTAAC    137160
GGTGAGGCTT TTTCACGCCG CCGGTAGCCG GCGCGCTCTT GCGAGCAGCC TTGGTAGCCA    137220
GCTGCTTGCG TGGCGCTTTA CCGCCGGTGG ATTTCCGAGC TGTCTGTTTA GTACGAGCCA    137280
TGGCAAAACC ACAGAAAAGC TTGCCTGCAG AGACGTCTGT GGAGGAAAGG AAAGAGCTAC    137340
TCTTCTTTTA TAGAGTCAGA CCACCAACTA TTGGACCCAA GAAAATTCAA AAATCCCCGC    137400
GCCCTTCTTG GATTGGTCCA TCTCTGTGCC TGGTTGCAGA TTAAGAGAGG CTCCTGCCCA    137460
TTACCGTAGC TACTCTGACG TCATTTTGTT AACCCCTTAG CTGCTATATC CACTGTGGAC    137520
AAGTCTTGTA CTGGAAAAGT TTCCTGAAGT CTTAAAATTT ACAACCACAC AAAGCAACGC    137580
GGAAACCTCC AATTGTTTCT AGTTAAAATA TAAAAAGAA ATCAGAGAAT ATTGGAGACG     137640
ATTAGGGAAA TTTGCATATG CGCTTTATTT AAAATTGTAT TTTTCTGGGT GTCGCATAAG    137700
AAGTGTGGGC AATTAGAAAA ATGCTCTTAG CCGGGCGTGG CGGCTCTCGC CTGTAATCCC    137760
AGCTACTCAG AAGGCTGTCA AGAGGATCGC TTGAGCCCGA GTTCGAGGTT ACAGTGAGCT    137820
GTTATCACGC CGCTGCACTG CAGCTTGGGC GAGAGGGAGA CTCCACCCCA AAACAAAGCA    137880
AAACATCCCC AAACTGGAAA AAAGCTCATT TTGGGAAATA CATACTCAAA TGTTCAGTGG    137940
TAATGTGTGT GCTCTCAATT GTGTATGCCA TTAATTGCTA CAGCAAATGG TATGACATAT    138000
TCAAACTTGT GTGGGGCATG CGGGTTTTAA CACTTCCATT CAAGATAGTT AGGAATGCAC    138060
TCATGGGTAT AATTTCCTTC CTCTAAAATG TAGTAACTGC TGTGTGTGAA ACTTAACGCG    138120
AATCACCCCT GTAAACATGT TTTGTGCTGC ATGGCACTTC TCCCACATAC CTAGAATTCC    138180
TGAGGTTTCT ATGGATCTAA TTTCTGCAGG ACAAATTACT AAAAGTGCCA CACTCAAAGC    138240
CATTAAAAAC ACCTCAAAAA CATCTTTATG GGCGGCATAA TCCAAAGCAC AACAGCTCAT    138300
TTAATGGAAG TCGTAGGTGG CTCTGAAAAG AGCCTTTGCT GTTAGGCTGA TTTTGTCTGC    138360
TGACAGAAAA ACAGCAGTGC ATGAAGCGTT AACTCTTCAC TTTCCCTTGG CCTTATGATG    138420
GCTCTCAGTT TTCTTAGGCA GCAGCACCGC CTGAATATTA GGCAAAACGC CACCCTGCGC    138480
GATGGTCACA CGCCCCAAGA GTTTATTAAG CTCCTCGTCA TTGCGGATGG CCAATTGCAG    138540
GTGGCGCGGG ATGATGCGGG TCTTCTTGTT GTCGCGGGCC GCATTGCCCG CCAGCTCCAG    138600
GATCTCGGCG GTCAGGTACT CAAGCACCGC CGCGAGATAC ACCGGCGCGC CAGCCCCGAC    138660
```

| | | | | | |
|---|---|---|---|---|---|
| GCGCTCGGAG | TAGTTGCCTT | TGCGGAGCAG | GCGGTGCACT | CGGCCCACAG | GAAACTGCAA 138720 |
| ACCTGCACGA | GAAGACCGAG | TCTTAGCCTT | GGCGCGAGCT | TTACCGCCTT | GTTTGCCGCG 138780 |
| ACCAGACATA | ACTACTTCTG | ATAAGGGAAA | ATCGCCACAA | GAAAATGTAA | TGAAACTACA 138840 |
| TTAGAACGCA | AGGCAGAGAA | GTATTTATAC | TGACTGGAGG | TAGGCTGTGA | GGAATTCTCC 138900 |
| CATTGGCTAA | TGTCAAATAC | CCAATGGGAA | ATCAGAATCT | GCATCCTTCA | TTTGCATGTA 138960 |
| ATCCTTCCGT | CTGGTGTAAG | GTTTATGTTT | GACCCAATCC | CCAGTCTGGC | TTGACGAGCC 139020 |
| TTCGACTTGA | ATACTAATAA | TAATTGGCCG | AATTAGGATT | TTGTCAAAAT | ACCTTTTTTA 139080 |
| AGCATGAGTG | GAGGTTTTGT | TCTGGTTATT | TTGACTTTCA | GCCGCTCGTG | CTTTTCCCGG 139140 |
| ATTGTGACTC | ATGTTTTTGG | AAAGGAGTGG | ACTCCGACCA | ATTTCTAAAT | AGATATTTAA 139200 |
| GAGGTCCTTC | AAATCGGGCG | CAGTGGCTCA | TGCCCGTAAT | ACCAGCACTT | TGGGAGGCCG 139260 |
| AGGACGGCGG | GTCAGGCGTT | CGAGACCAGC | GTGGACAACA | TGGAGAAACC | CTGTCTCCAG 139320 |
| TAAAATAACC | AAAAAGAAA | CGGGGGAGAA | AAAGAAAAAA | AAAGCCGGG | CTTGGTAGTG 139380 |
| CACGCCTGTA | GTTCCAGTTA | CTCGAGAAGC | TGAGGTGGGA | GGATCGCTTG | AACCCGAGAG 139440 |
| GAGGAGGTTG | CAGTGAGTTC | ACATAGAGCC | ACCACACTCC | AGCGTGGGCG | ACAGAGCCAG 139500 |
| AAGACTGTGT | CTCAAAGACA | AAAAAAGGGG | AGGGGGAGTG | GGAGGGAAGA | AAAGCGAATA 139560 |
| CCCCAAATCC | CAGTGAACTG | TAGAAGCTTA | TAAGCTCTCT | TGATTCATAA | GGGAGAAAGA 139620 |
| AGGGGGATGT | AGGCAACTTA | GGGGAGAGTA | TATGATTTTG | GAGAAAAATA | AATGGGTGTT 139680 |
| TCAAAGAATA | GGTGACAGCT | GTGACAAAGT | CTGTTTAGAT | GGTGTTAACC | ACCAGTCTCC 139740 |
| TCTCCTGTGA | TACAGTTAAT | CTTCTCTGGT | TGATGAGATT | CCCCAGGGAA | GTGAATCTTA 139800 |
| ACAACTAAAT | TCCTTTTTGA | ATTTTTTTT | AATTTCAAA | TTTTTGATTA | GAGTTCAGCG 139860 |
| AAAGCCCTTC | CTTGAATTTA | CTGTTTCCTA | GGTGCCCTCA | GTTCAAAGAA | ATCAGCGTAA 139920 |
| CAAAGTGGCA | CATTTTTGAG | TTGCATTTCC | TGAACTTTTT | CACAACACTG | AATGAGGAGT 139980 |
| CTCTGGAATC | TTTCAGGAAA | TGAGAGAACA | AACATTCCAT | AACACAGAAA | TACTCAAAAT 140040 |
| GGGATTATGA | TTATAAAAGT | GTTTCACTGA | CCACCTTCTG | CCTTCCTGTC | TGTAAGTCCC 140100 |
| ATTCTCCCCA | AAGTCTAGCC | ATAGAAACCA | GAATTCCTCC | TCAAGGTAGG | CCATACAAAC 140160 |
| CAGAACTCCT | TTTCCCTAGA | ACCAGCCATA | AAACCTAAAA | GTATTACTCT | AACCTACCTT 140220 |
| GTTTGCCTGT | AGGTCATAAG | ACCCCCCATT | CTAAAAGAGA | GTCTTGTCCT | ATAACCAGAA 140280 |
| GGAAGAAATG | CTGCACTGAG | AGGTCAAGAA | GAATCTTGAC | AGACAAGCCT | TGCGGGGCTT 140340 |
| CCCCACTCAG | TCTGTTAGCA | TTAGATCGTA | CCCTATACAG | CTGTTTATCT | TGTTGAACCT 140400 |
| AAGCATAAAA | ATGGGCAATT | TCCCCTGTAT | CTTTCAGTCT | TAATTCTAAA | ATCTCCTGTA 140460 |
| AAATTGTGAT | GAAATAAATA | TATATGCCTT | TTCTCCAGTT | AATCTGTGTT | TTGCCAGTAA 140520 |
| TTTTCCATAA | ACCTTGGGAG | GGCAAGGGG | AAGTTTTCC | TTGGCCGGGA | CAATATTATT 140580 |
| ACAGCCATTG | TCTGGCTCTC | CTGTTGAGGA | ACCTAAAATC | AAGACAGATT | GCCTAGGGAA 140640 |
| ATCTTGGTGT | TTTTCCTTTT | ATATTCCATG | AGATAGGAGC | AGATGGAGTA | CAGATGAACG 140700 |
| TGGATTAATT | ATTCCAGGAA | TTTCTGAGGT | ATCTACTACT | TCTATCGTG | GTCTGCTTAT 140760 |
| ACTGAAACAG | GATGACAGAA | GGAAAAGAA | ACATGAGTGT | AAAAAAATCT | GCTCCTGGCT 140820 |
| GGGCACGGTG | GCTGATGCCT | GTAATCCCAA | CACTTTGGGA | GGCCAAGGCG | GGCAGATCAC 140880 |
| TTGAGAACAG | GAGTTCGTAA | CCAGCCTGGC | CAACATGGTG | AAACCCCAGT | CTTCACTAAA 140940 |
| AATACAAAAA | ATTAGCTGGG | CGTGGTTGTG | GGAGCCTGTA | ATCCCAGCTA | CTCCATAGGC 141000 |
| TGAAGCAGGA | GAATCGCTTG | AACCCTGGAG | ACAGAGGTTG | CAGTGAGCCG | AGATCGTGCC 141060 |

-continued

```
ACTGCACTCC AGCCTGGGCA AGAGCGAAAC TCCATTTCAA AAAAAAAAAA AAAAAAAATC 141120
TGCTTCTAAG CCAACGCTGT CACAGAACTA TGGATTTGAT TCAGAGAAAC TGTCAGGAGA 141180
CTAAAAGTGC TCATTTTTAG TTTGTTTTTT GCCTTCTCCC AAGTCTTCTG ACTCTAGTGT 141240
TATCTTTCCC TTCACAATAT TCAACTTCCC TTTTCAAAAT TATAATGATC TTCACCCTCA 141300
ACAATAGCCG TAAACATCAG TAATCACTGG CTCATTTTCT TTGAAAAGGT ACAAGATTCA 141360
TGATGGAGAT GTTAAAAAGT TATCTCAGAT AGTGCCCTGA AGAGATTATA CTCAGAGAAG 141420
GGAGGACTTA CGTACATGAA GATTAAATAG CAGTGCACGT TCTGCATATA AATAAAGAT 141480
TTTGAGCAAT AAATCATACA AAAGCACATG GAAAGAAGA TTGATCAATG TAAATTAGAA 141540
GGATTTAGAG AGTTCATGAG GGAGATGTAT ATCCAGCATT ATTAGTTCAG CATATATTTA 141600
CTGAAAACCT GCTAAGTGCC AGAGAGTGTT CTAGGTGCAG GGAGCATAGC AGTGAAAAAG 141660
CAGACAACCT GTTTCCTTAC GGTGCTACTT GTCTTGTAGT GGGAGGTGCA CAATAAGGTA 141720
AATACATAAT GAAAATGTAG AGATAAGTGA TGAGTGCTGT GGAGAAAAAT AAAGAAGGG 141780
GATAAGAAAA AAGAATAGAA ATAAGGATGG AAAGTTTCAT CAGGAGAATG TCATTTGAAT 141840
TCAGACCTGA AGGCAAGGAA GAAGCCAGCC AAGTAGGAAG GATAAATACT TCGATAAAAT 141900
GCTGGATGTG TTTGAAGTCC AGAAAATGTC AGGAACCGTG GTTCAGAAAG TACAGCTATT 141960
CTAACTTCCT AAACAAATCG TAGACCATTT TGGAAAGAGC CTTGGATATG TACAGGGCTA 142020
GATAAAATTG AAACCAAGAT TAAGGGTAGC TTCAAAAACT CAGACTAGAA AGCAGGAGTA 142080
CATCCAGTCA CAATATCAGT AATCTATACT CCACTGAGCC ATGGATGAGA AAAACTCTTC 142140
TTCTCATCCA AGTTACCTTG AATTAAGCAA ACCAACAAGC GCCTGGCATG TACTATTAGC 142200
AAAACAACTT GATGGCAATC CTTTCAGTAA GTGCTTCAAA AACAGTAAAT TCTAGGCACT 142260
TGCCTTCAAA AAACATACAA AAGGCAGATA TTGGGGAGGG AAATATTGGG GGTTATTTAT 142320
TCCATATAAA TATAAGAGGA AAATAAGTTG TTTCCCAATA ACAACTCCAA CACCAGGAGC 142380
AGAGAAAGTA AGACAATCTA TGCCTCGTGG TTTGCGAAAA CAATAAAAAA AATCTGTTAA 142440
TTGCATAATA CAATTCACCC TTGAACACGC TCCAAATCAG TGCCCACTAG CTACAAGTAG 142500
CTACTGTGAA GTTGAAAAAG GGTACTTCAG ATTGAGCTAT TCTGTAAATA TGAAATAGAC 142560
TTAGTGTGTT AGTTCGTTCT TGCATTACTA TAAGGGAATC CCTGAAACTG ACTAATTTAT 142620
AAAGAAAAGT AATTTTTTTT GGCTCACGGT TGTGCAGGCT GTACAGGAGG TGTGGTGCAG 142680
GCATCTGCTA CTGGCAAGTC CTCAGGAAAC TTCCAATCAT GGTGGAAGGT GAAGAGGGAG 142740
TAGGCATATC ATATGGTGAG AGCTGAGCGA GAGAGATGGG GGAGGTGTCA CACTCTTTTA 142800
AAGAACCAGA TCTCTTGTGA ACTCAAAGTG AGAACCCATT GATTACCCTG AAGAGTGCGC 142860
TTCATGAGGG GTTCACCCTC ACGATCCAAA AACCTTTCAC CAGGCTTCAC TTCCAACATT 142920
GGAGATTACA TTTCAACATG AGATTTAGAG GGGACAAATA TCCAAACCAT ATCACTTAGT 142980
ATGAAGAAAG AATGTAAAAC ATCTGACTAA TAATTATGCA TATTGAATAC ATGTTATAAT 143040
GACATTTTGA CTACAAAAGT TAACGAAAAT ATACTATTGA AGATACTCAA AAATTTAAAA 143100
ATACATATAT AATTTGTAGT ACATTTGTAC TGGGCAGAGG AACCTCTAAC AATGTTCCAA 143160
ATGTGGCCTG TGTATGTGTA TGATGTAGGA GGGATCAGTC ATGTAAGATG ATCATAATAT 143220
AGTTACTTAG TCCATTTTGT GATACTATAA CAGAATACCA CAGACTGGCT AACTTTTAAA 143280
GAAAAGAAAT TTATTTCCTA CTGTTCTAGA ACCTGGGAAG CTAAGGGCAT GGAATTAGTA 143340
TCTGGTGAGG GCCTTCTTAC TGCATCATAA CATGTTGAGA GAGCAAGGGT ATGTGTGTCA 143400
GCTCAGGTGT CTCTTCCTTT TCTTATAAGG CCACCAGTCT AAAGGAAATC AAAATATTTT 143460
```

| | | | | | | |
|---|---|---|---|---|---|---|
| ACCCCAAAAT | ATATTTCTTT | GACATATTTT | GAAATGGCTG | CTGCTTGGCC | AGCAGGCAGA | 143520 |
| AATGGGCTTG | CAAAGCTGCC | TTAAATGGGA | AAAATTTTAC | ATCTGTAGAG | AATCTCCATT | 143580 |
| AATGCAGCCA | TGCCTCCTCA | CCTTTCTATA | CCTTTCCCCA | GATCCAGGAG | AGACTGAGAG | 143640 |
| TCTGACACTT | AAAAATCATA | AAAGAAACAT | TTACCATCTG | TTCTTTCTGA | GGGAGGCTTC | 143700 |
| ACCTACCTAA | CAAGGCCACC | TTTGCAAGCC | AAACCTCTTT | TGCCTCCCAT | AACCTGTTTT | 143760 |
| ACCAGAATCT | AAGCCCCAAT | TCTTTCTGTG | ATCTAAAAAT | GGTATATAAG | CATCTATAAC | 143820 |
| TCATTGGGAA | GTTAGGTAAT | TAATTCTGAA | TGCTCCACA | TAGACACGTT | AAACAATAGG | 143880 |
| TAAAATGCCT | TTTCACCTAT | TAATCAATCT | GCCTTGTCAG | TGATTTCTGG | CAAACATTTA | 143940 |
| GTGGGCCAAG | AGACTATGGT | TCCCACACTA | CCCTTCATGA | ACTTAAGCCC | TAAGATATCA | 144000 |
| ATAATTGCAT | TAAATGTGTG | TGGTATAAAT | ACACCCATAA | AAAAACAGTT | TGGCTGGGCG | 144060 |
| CGAGGTCTCA | CACCTGTAAT | CCCAGCACTT | TGGTAGGCCG | AGGCTGGCGG | ATCACTTGAG | 144120 |
| GTCAGGAGTT | CGAGACCAGC | CTGGGCAACA | TGGTGAATCC | TGTCTCTACT | AAAAATACAA | 144180 |
| AAATTAGCCG | GGTGTGGTGG | CGCATGGCTG | CAATCCCAGC | TGCTCAAGAG | GCTGAGGCAG | 144240 |
| GAGAATCCCT | TGAACCCAGG | AGGCGGAGGT | TGCAGTGAGC | TGAGACTGTG | CCACTGCACC | 144300 |
| CCAGCCTGGA | CAACAAGAGT | GAAATTCCAT | CTCAAAAAAA | AAAAAACAAC | AACTGTACAC | 144360 |
| TGTCTGCAAG | AATCTCACTT | CAAATATAAA | CATAACGCAG | GTTGAAATTA | AAGGCTGCAA | 144420 |
| AAAAGATAAG | CCATATAAAC | ATCAGCCCAA | AACTGCAAGA | GTATCTGTAT | TAATAATATC | 144480 |
| TGGGATCTGA | AAGACCAAAA | TAGATGCCCC | TATACCAACT | AAGACAGACT | CTAAGATTAA | 144540 |
| GCAAACAAAG | TTACCTACTG | GTAGAGCATT | CATGGCTTGG | CTGGCATGGC | AAATTCCTAA | 144600 |
| ATTCCAAAGA | CTACCAAAAA | ACTCACACTT | GCTAAATTCC | TTAACTATAG | GAGCTATCAG | 144660 |
| AAGCCCTCCT | AACTCTGATT | TACAGTCCAG | TCCACTACAA | CTCTGATTGG | ACAGAGGACC | 144720 |
| GCCTTGACAC | ACATTCTATT | CTTACACGTA | ATTGTAGACC | TTAAGCCATT | TTCAGCCAGC | 144780 |
| TGCTAGAGGC | AGCACGTAAA | CTTTGTTCCT | ATAGTTCACC | TTGTGATGTA | AAGACCTAAA | 144840 |
| TTCTACCTCA | TTTTAACCAA | AATTTAACCT | CGAAGTGAAC | ATGGGAGGTA | TATTACACGT | 144900 |
| GTTTATCCAT | TGTGAATGCA | CTTGGCACCC | CTCATAATAT | ATATAGCTGT | CCCCCCAAAC | 144960 |
| GTGCTAAATA | TGTATGACTC | TATTGTGTAA | TATATAGCCT | ATGAGGCATA | AAAATAACCA | 145020 |
| ACCTGCTCCT | TCTCCCCAAA | GAGAGAGTAA | TTTTGGCAGG | TTCTGGGACC | ATCTCTTCCT | 145080 |
| GGCTTGCAAA | TTAGTATTGC | CAGTAAATCT | CTCCTTTCTA | CTCTTTAGCC | ATCCTGGTGG | 145140 |
| TCTTTTGGAT | GATATATCAG | ATAAGTATAT | TTCAGAGCAA | AGAAAATTAC | TAGGAACAGA | 145200 |
| CAGGGATATT | ACATAATGAT | AACAGGGTCA | ATCCAATACG | AAAAACAAGC | AATTCTAAAT | 145260 |
| GTATATGCAC | CAAATAACAG | AACTGCAAAA | TATGTGTAGC | AAAACCTGAT | AGAACCGAAA | 145320 |
| GGAGAAATAG | ACACATACAT | GATTTAAAGG | TAGAGATTTC | AACACCCCTT | CCCCAATAAT | 145380 |
| TGATAGAACA | ACGAAACAAA | AAAATTACCA | GGTGTATAGA | ACTCAGTAAG | TGACTGTATT | 145440 |
| ACTTGTTTTG | ATCTGTAAAA | CAATGATAAT | AATAGTACTC | ACACTTCATT | GAGTTTTGGT | 145500 |
| GAAGATTGAA | TGAATTTATA | CTTATAAAGA | ATTTAGAAAT | GTGGCCGGGC | CCAGTGGCTC | 145560 |
| ATACCTGTAA | TCCCAGCACT | TTGGGAGGCC | GAGGCGGGTG | GATCACCTGA | GGTCGGCAGT | 145620 |
| TCGAGACCAG | TCTGACCAAC | ATGGAGAAAC | CTCATCTCTA | ATAAAAATAC | AAAATTAGCC | 145680 |
| AGGCGTGGTG | GCGCTTGCCA | GTAGTCCCAA | TTACTGGGA | GGCTGAGGCA | GGAGAATTGC | 145740 |
| TTGAACCCTG | GAGGCGGAGG | TTGCGGTGAG | CCGAGATCGC | ACCATTGCAC | TCCAGCCTGG | 145800 |
| GCAACAAGTG | TGAAACTCCG | TCTCAAAAAA | AAAAAAAAA | AAAATCTTAG | AAATGTAACT | 145860 |

```
GACATATCAT  AAGCCCTCAA  ACTTAATAAT  CTTTTAATAC  ATGGAGCTAT  CTATTTAAAA  145920

TAATGTACAT  AAGGCAACAT  CCCAAAAGAA  AATGGGCAAG  AATCATGAGT  AATCAAACCA  145980

TAATAGAAGA  AATGTTATTA  TCAAAATGTG  CAGTCTCAAA  CAATAATTGT  CTTAAAAATA  146040

AAAACAACAA  TGAGATTTAA  TTGTTCATGT  CGGCAATTTG  AACAGACTAA  CACACCCACT  146100

GTTCAAGAGC  ATTTGTGGAA  GTCAGGAAAA  ACACCCTGT   TGGTGAGAGT  GTAAACAGAC  146160

CTTCAGGAGG  CAACTTGGTA  ACATGTATTA  AAAATCAAAA  TATGTATATC  AATGGATGCA  146220

TGATTCCTAT  CTCTATTTTT  GCCCTTACAG  CAATCTTGTG  TGTAGAGAAA  TACTGAAAAG  146280

CATTTTCATG  GTAACATGGT  TTAAATTTTT  AAAAGCGAA   GGTCAGTGAA  TAAAGGGCAA  146340

TTATCTACTT  CCCTACAATG  AAATGCAGTA  ATGAAAATAA  TCATTAGAAT  CTCTTTTATT  146400

AATTTAAAAG  GATACTAGAA  AAGTGAAATA  CAATCTCACT  TATAGAAGAT  TTACATATTG  146460

GTTGCATAG   ACTTGCACAA  GATAAAATTT  CTGTAAGATT  GGTCACCAAA  ATGTCCTGAA  146520

TGATAACATT  ACAATTAATG  TTTATATTGT  AGGGGAAAAG  AAAATTCTGT  TTTTCTCACC  146580

CATCAGTAAG  TTCATGCTTG  AGGCCCCTCT  ACAAAAGAC   AGATTGGTCG  GGTGCAGTGG  146640

CTCACGTCTG  TAATCCGAGC  ACTTTGGCAG  GACGAGGCGG  GCGGATCACG  AGGTAAGGAG  146700

ATTGAGAACA  TCCTGGCCAA  CACGGTGAAA  CCCTGTCTCT  ACTAAAAATA  CAAAATTAG   146760

CGGGGCATGG  TGGCACGTAT  CTGTGGTCCC  AGCTACTCGG  GAGGGCGAGG  CAGTAGAATC  146820

GCTTGAACCT  GGGAAGCGGA  GGTTGCAGTG  AGCCGAGATC  GCGCCATTGC  ACTCCAGCCT  146880

GGGTGACAGA  GCAAGGCTCA  GTCTCAAAAA  ACAAAAAAAA  AGATTAGCAA  GAGAAAAGCA  146940

TACAAATGTA  TTTAATATAA  GTTTTATATT  ACATGGGACC  CTTCGGAAAT  GAAAACTCGA  147000

GGGAAGCGGG  AAACCTGTGA  ATTTTATGG   CAAGTTTTGT  GAAATGCATA  GTTGTGGATT  147060

AATATGATTG  ACAGTAGGCA  TATGATCTAA  TGGTAATAAA  CTGAGGGGA   CATAGCAAGG  147120

CTTGTTTGTT  AATTACCTAT  TAACGATCAG  CCGAGTATCA  GCAGAGACAG  CAAAACATCC  147180

TAGTTTTGAG  TTAGAAGACC  TAGGTTTTTG  TTTTGGCTTA  TCAATTATGG  GTATTGTTTT  147240

AGATGAAACA  TCAAGTATTC  TTGATTTCTT  ATTTCAAAAA  TAAAAAATAA  AAAATAAAGG  147300

AAGGAAAAAA  GAAGAAAAAA  AGAGAAGAAA  AGTGTCAGAG  TTACTTGAAC  CAGAGTAACT  147360

CCATTTTGAG  TGAGGGCTAG  GAAAATGAGG  CTGAGACTTT  CTGGGCTGCA  TTCCCAGAAA  147420

GTCAGTCATT  CCTAGCTTCT  AGATGTTTAC  GGTTAAGGGA  ACAAATAAAT  AATGTTTACT  147480

AAACAGACTC  AGACTTAGGA  GTGTCCAGAT  ATCCCTATAT  CTGGAGAACA  AAGGCATTCT  147540

TAATTTTGTT  TAAAGATAAT  AATGTTGATT  CTTGCAAAAT  ATAGTAACTA  AGAAAATTAA  147600

TCCTTTATCA  CAAACTTGTA  GCAGAGCACA  TCTCCCCATA  TATACAAGTA  TTGTACCTAG  147660

GGTGGATGCC  TTCCTCCTCT  TACTTTCGGG  AATGTCCTGC  TCCGTCTATG  GAGTAGTTGT  147720

CGTTTCACCA  CTTTACTTTC  TTAGTAAACT  TGCATTACT   TTGCACTGCG  GACTCACCCT  147780

GAACTCTTTC  TTGCGCGGGA  TCCAAGAACC  CTCTCTTGGG  GTCTGGATGG  GGACCTCTTT  147840

CCTGTAACAT  ATTTCTGGCC  ACCACAGAAG  GGACTATAGT  ACAGAAACCC  TGACCCAACA  147900

GCTACCTTTG  GGTAAGTGTT  GGAGTTCTGT  AACAAAGGAA  GAAGGCAGGC  AGGCAAAAAA  147960

TTTATGAAAG  AACATACGAC  AAAATAATTT  CTGCTTCAAA  ACTTCATATT  TTTTAATTT   148020

TTTTTTTTT   TTTTTTTGA   GACGGAGTCT  CGCTCTGTCA  CCCAGGCTGG  AGTGCCATGG  148080

CGCGATCTCG  GCTCACTGCA  AGCTCCGCCT  CCCGCGTTCA  CGCCATTCTC  CTGCCTCAGC  148140

CTCCCGAGTA  GCTGGGACTA  CAGGCGCCCA  CCATCACGCC  CAGCTAATTA  TTTTGTATTT  148200

TTAGTAGAGA  CGGGGTTTCA  TCGTGTTAAG  CAGGATGGTC  TCCATCTCCT  GACCTCGTGA  148260
```

```
TCCGCCCGCC  TCGGCCTCCC  AAATTGCCGG  GATTAAAGGC  AAGAGGCACC  GCGCACGGCC   148320
CCGTCCAAGT  TAACCTTGGC  TCTAAAACTT  GTCTTCGCTA  ACATTCCAGT  TGATCCTCTA   148380
GAACTGAAAC  AGAATAGCAG  CAGCACCACC  TTAAGAAATT  GTGGTTATAG  CTCTCCTTGT   148440
GACAAAGTAG  GTGGCTCTGA  AAAGAGCCTT  TGGGTTTGGA  AGTGCTTACA  TAAGCACTTA   148500
TTTAGAGCTA  GTGTACTTGG  TAACTGCCTT  AGTGCCCTCG  GACACAGCAT  GCTTAGCCAG   148560
CTCCCCAGGC  AGCAGCAGGC  GCACAGCCGT  CTGAATCTCC  CTGGAGGTGA  TGGTCGAGCG   148620
CTTATTGTAG  TGAGCCAGGC  GAGAAGCCTC  GCCCGCGATG  CGCTCGAAGA  TGTCGTTGAC   148680
GAAGGAATTC  ATGATCCCCA  TGGCCTTGGA  TGAGATGCCG  GTGTCGGGGT  GGACCTGCTT   148740
CAGAACCTTG  TACACATAGA  TAGAATAGCT  CTCCTTGCGG  CTGCGCTTAC  GCTTCTTACC   148800
ATCCTTCTTC  TGCGCCTTAG  TGATAGCCTT  CTTAGAACCC  TTTTTAGGGG  CTGGAGCAGA   148860
CTTAGAGGGT  TCAGGCATTG  CTATTCCTAA  ACAGAATAGA  AAAGCTACTA  ACACTCTCCA   148920
CTACAGAGTA  GTACAGAGAA  CAGTTCAGAG  CCCATGTATT  TATAGTCCTG  AGATTCAAAT   148980
GACGGTTTAA  GATTCCTCAC  TTCTGATTGG  ACAAAGAAA   CACGGTTTCA  CTGAGGGGTG   149040
GGGTTTATGC  AAATATGGAA  TTTATGTTAT  CTTTTTCTAT  TGGATAAAGC  ACCAAACATA   149100
ATTGACCAAT  AGGATAGCTT  CCTATTGCAG  CCTTGCAGTT  TGTATAAAAG  GATTTGTTCA   149160
GGCGCCATTC  CAGCTTGCTT  GTCTTTCACA  GTTTTCCGCT  GCTTTCATAG  GTCGCTATTT   149220
GCGGACGTGG  AAAATGGAGC  TAAAGCAAAA  ACTTGTTCGT  CGCTACCGGG  CTTGCAGTTC   149280
CCAATAGGGC  AGAGTCCGTC  ATCTTTTCG   AAAGGGCAAT  TATTTTGAGC  CGGTCGGAGC   149340
CGGTGCGCCA  GTGTACTTAC  AATACCTGGC  CGCCGAGATC  TTAGAACTGG  TGGGCAGCGC   149400
CATACGTGAC  AAGACCCGCA  GCATCATCCC  CCGCCACCTG  CAGCTGGCCA  TCCGAAACGA   149460
CGAGGAGGTC  AACAAGCAGC  TGGGCAACGT  CACTATTGCT  CAGGGAGGCG  TCCTGTCCAA   149520
TATTCAGGCC  GTCCTGTTGC  CAAAATAACA  GAGCCACGAT  AAGGCCAAGG  TCAAGTAAAC   149580
ACTCAAATCA  GAAAACGTAG  CTTACACTTG  AAACGGCATT  TTTCAGAGCC  GTCCATAGTT   149640
ACACAAGAAA  GGATGATAAC  TTGCTTCTGT  TAGGGTATTT  TTTGCTTTC   GTTTGGATTG   149700
GTTTGTTTTG  AGACAGTCTA  GTTCTGTCAC  CCAGGCTGGA  GTGCAGCGGC  GCGATATCGG   149760
CTTACTGCAA  CCTCCACCCC  GCCGCTTCAC  GCGGTTCTCA  TGCCTCAGCC  TCCTGTGTAC   149820
TTGGGATTAC  AGGCGTCTGC  TACCGCGCCC  AGCTAGTTTT  TGTATTTTA   TGCGAGACGG   149880
GGTTTCACCA  TTTTAGCCAG  GGTTGTCTTG  AACTCCTGGC  CTCTAGTGAT  CGTCCCATCT   149940
CGCCCTCCCA  AAATGCTGGG  ATTACAGGCG  TGAGCCACCG  CCCCCCTAGC  CTAATGGTGT   150000
TAAAAGTTA   AGTTTCGAGA  AAATAACACC  TTCCTTTAGA  AAGTACATTT  TAGAGTATAC   150060
AAAGTGAAAC  TTAAGGCCAA  CCAAAATAAG  ACATTTTGAG  AACAGGCAGG  GTGGGAATGT   150120
GACTTGGACT  TAGAAAACAA  AGGGCAAGGA  AACTTGCTGT  TCGCCAGTAA  CAAAATAGCA   150180
TGGAATCTCA  TTCTCTGAAT  ATAAGCGTTA  TTTCCCGACA  TGAGTCTGAA  CGTTTCTGGT   150240
GGTTTAGTGA  GTGTTCACCA  GCATTGATAA  CTTGCGAGAC  TGTCAGGAAT  GCAGAATTTC   150300
AAGTCCCACT  CAAACTTACT  GAATCGGAAT  TTACATTTTA  AAAATCCTTA  GATACCTTGT   150360
TATACACTCT  GTTCTTTGGG  ACTGGATGAA  CTAGAATTTT  AGACAATTTG  TCGCTGCAGA   150420
TAACTGAAAC  GAAAAGGACA  GGATGGGCGG  TGGGCAACT   CATCCAATAA  GATTGTCTAG   150480
TAATGAACCA  ATCAGTCTGG  TCACTCTTCA  GCCAATGATT  TTATCGCGCG  GGACTTTTGA   150540
AATATTACAG  GACCAATCAG  AATGTTTCTC  ACTATATTTA  AAGGCCACTT  GCTCTCAGTT   150600
CACTACACTT  TTGTGTGTGC  TCTCATTGCA  AATGGCTCGT  ACGAAGCAAA  CAGCTCGCAA   150660
```

```
GTCTACCGGC GGCAAAGCTC CGCGCAAGCA GCTTGCTACT AAAGCAGCCC GTAAGAGCGC    150720
TCCGGCCACC GGTGGCGTGA AGAAACCTCA TCGCTACCGC CCGGGCACCG TGGCCTTGCG    150780
CGAAATCCGT CGCTACCAGA AGTCCACCGA GCTGCTGATC CGGAAGCTGC CGTTCCAGCG    150840
CCTGGTGCGA GAAATCGCCC AGGACTTCAA AACCGACCTG CGTTTCCAGA GCTCTGCGGT    150900
GATGGCGCTG CAGGAGGCTT GTGAGGCCTA CCTGGTGGGA CTCTTCGAAG ACACCAATCT    150960
GTGCGCTATT CACGCTAAAC GCGTCACCAT CATGCCCAAA GATATCCAGC TGGCACGTCG    151020
CATCCGTGGG GAAAGGGCAT AAGTCTGCCC GTTTCTTCCT CATTGAAAAG CTCTTTTCA    151080
GAGCCACTCA CAATTTCACT TAAAAACAGT TGTAACCCAT TCGGTTGTCT ATGTTAGTTT    151140
CCAGGAGATA TAAAGGTGAT AACTACACAC AAGTTTTGTA ACTGCAGACA AGTCTATCAG    151200
GCCTTTTCAA CCGGTTTTAC TGCGAGAAAA CAAGCTGAGT TACTGTTTTG CCCTTGTTAA    151260
AAAATTCCTA GGGGTCTTTT TAGCATGTAT ATGTGTAAAT ACTTACATAT TGAAAGGCTC    151320
CTGGGGACAC CACCGTCACT CCTTTTAATC CACGTGACAA TTTTAGTTCT GATGGCAGTA    151380
TTATTAAAGC TATCATAAAG ACAATGTGTG TGTAGTTACC TAAGTCCACA AAAACAATAG    151440
CTGACCCCAA AATTCAGTAT TGGTTTTGGG CTGCTGGAGG TGGAGTCAGA GCTCAGGTGG    151500
AAGAAACTGG CCTCAGTACA CACTGCCAAA AGTCCACTAA ATAGATTTAT GTAACAAGTA    151560
CACAAGACTT GCGTATGACC ATCCAAAGAT TATGCGGTCA TCCTTATCCA GGGAATTTGA    151620
GAATGAAGGG TGGCAACTGC AAAGCTCTTT TACCCATGTC CTCTTTTAAT AAATATTTAA    151680
AAATATTCAA ATGCTGATTT CATCCATTTT CTAAATATAT TAGTATACTT AACTGATGGG    151740
GTAGATCAAG GTTTTCTGGG GATCAAACCT TTTACAACTT GTTAACTATT AAAAACTATA    151800
ATGTAAAATT AAAAATGCAA AAGTACTGCA GACTGTAAAT ATAAATTTAT AATGGGAAAA    151860
TAAAATCAAA TTCCAATTTT ATAAAGCTG ACAAAACAAC AGCCATCACA AAATTCAGAA    151920
AATAGCATAT TTTATTAACT TCTGAATATG ACACTACCAA GTATATTTC CTGTAGTTTT    151980
GACTGAATAC TCTGATTCCA TCTTCAGATC GAAATTATTT TGTAATGTTG TCTATAGGTA    152040
ATGGAAATAG AATTCAATCT TTCCTCCAGG GTGGCTGATG ATAATATGTT TTCTTCATAA    152100
CTTAGAAGTA TTTCAGTTTC AAAACACATT ATTGGTAATG TCAAGTAAGT TTTTAGGATT    152160
GTTTTCAAAT TTGGAAAATC CTCTGTTAAG CTCCTTTCAC ATGTAAGTTG TAAACTTTGT    152220
AAGAATTCTT TCCAGACTAG CTTCTGGCTC TATACGTTTC TACTCTCCAC TAGACACTCA    152280
CTCTCAGTGC TGGGAATGTG TTTTGAATAC TTAGATGTCA TAACATTTTA TCTAGACCTG    152340
CATCTTGCCA GGAATTTAGG TGAGTTATTC CAGTGAGCAG TAGGAACATT CCTTGAAGCC    152400
ATTCTTTTTT TTTTTTTTT GAGACGGAGT CTCGCTGTGT CTCCCAGGTT GGAGTGCAGT    152460
GGCGCAATCT CGGCTCACTG CAAGCTCCGC CTCCCAGGTT CATGCCATTC TCCTGCCTCA    152520
GCCTCCCAAG TAGCTGGGAC TACAGGCGCC CGCCAACACG CCCGGCTAAT TTTTTGTATT    152580
TTTAGTAGAA ACGGGGTTTC ACCGTGTTAG CCAAGATGGT CTCGATCTCC TGACCTCGTG    152640
ATCCGCCCGT CTCGGCCTCC CAAAGTGCTA GGATTACAGG CGTGAGCCAC CGCGCCCGGC    152700
CTCCTTGAAG CCATTCTTAC GTCAGATTGG CTGGCAACGA ATGAAGTACA CATGATCACA    152760
TATGCAAATC ACGTAACTTA TTATCCCCAT ACTAGATACA TCTTCAACTA AACTTTCTCT    152820
TACTCAAATT CCAAATATTT TCATCAGGAT TCTAACATAA TCAGACAATG GTGATTTTAA    152880
TAAAAGGAG GATTGAGTGA AAATAGCAGC CTGAACCATC CGTGATTAAA GTACCTTAAT    152940
ACTGCAAATT TTAAAATCAG AGAGAGAGAG AGAGACAAAC TAACACATTT GTAGGGCCCC    153000
TCTCTGCACC TTGGAAGTAC AGGCCCTTAC ACTTGTGTTT CATTAGCTTC AGGATAAATC    153060
```

| | | | | | | |
|---|---|---|---|---|---|---|
| TGCCCCAGAT | CACTGGCCAA | ATTTTACGTG | GCCTTCTTCA | GCATCCTACC | ACTCTATTCA | 153120 |
| AATACATCTC | TGCAGGAGCA | CCCTGTGAGT | TGAGAATTAC | TGGTCTGGGA | TGACCACTGT | 153180 |
| TTGCATGATG | CTTTGGATGG | TGGTGCTGTT | CTCAGAAGAA | ATACCAGAAG | GAGAAAGGTT | 153240 |
| AGTCAGGAGA | ATATAAAGTC | AACCTTAAGC | AATTTGAACA | CTTCAGTGGT | TAAGTGAGTT | 153300 |
| CCCTGGGACA | ACTCTGCAAG | CTGTTTTAAC | TTTATTTGTA | TTGAATATTA | CCTTCTTTTA | 153360 |
| GAGAGGCCAA | CGTGTAGAAG | GAAATAACAA | TGAAACAAAG | GATTCATTAA | TAGTATAAAC | 153420 |
| TATAAACTAA | CTGTCATTGA | TAGTCTTCCA | CGGGCCAAGT | ACCACATGAA | GTGGTTGGTC | 153480 |
| TGAATTATTG | TGTAAAATTC | TTACTTCAGC | ATTGTAAGGC | AAATTATCTC | ACTGTCTCCA | 153540 |
| TTTTACAGAA | GTGGAGGTTC | AGCCTCAGGA | ATTTCACTAA | ATTCGCCAAA | TTCTTACTAC | 153600 |
| CAGCAGATAT | CATTGCCAGG | CAGTGTCACA | CTTTAATATC | TTCTAATCAA | TAAGATAACC | 153660 |
| CTAAAATTGA | TTATCATATA | TAATTTCCTT | CTCATATATA | GTTTCATACT | ATCATATATA | 153720 |
| GTTTCCTTTG | TTTCAGAAAT | TGGACTCCCT | CAGGGTGGAT | AAGGAGACAT | GGTGGTGTCC | 153780 |
| TGGCCTAAGT | ATTGTTGGAA | TCCTCTAGTC | AGAGGCCTGA | TGTGAGGTGA | AGTGGACAGT | 153840 |
| GAAACTGCCT | TTGCAAAAAT | CATAACTGAG | AAAATTATTA | CAGTGAAAGA | GATCTTACCT | 153900 |
| AACCGACTCC | ATCTAACGTC | TAAACTCCAA | GCTGTCCTTT | TCATTCCTGA | GTTTGGGATT | 153960 |
| AACTAACTTT | GGGAGGAGCT | TAGTTTATAC | TTTTGCTTTT | AAACAAAAAC | AATAACAGCC | 154020 |
| CTTTCAGAAA | CAAACCCCTT | TCCTGCCTGG | GGACCAGACT | GCTTTTGCAG | GACTAACAAA | 154080 |
| TTAGCCACAA | GATTATAAAT | TATGGTTTAG | GAGTCATGCA | GCTGGAAGCT | ACAAGATTCT | 154140 |
| AAACCTCAAA | TTGCTCCTGG | GGATAAAATC | ACTATTTTAA | AACCTAAGAT | CAATGCTTGA | 154200 |
| GCTATTTTGC | AGACCCTGAA | CACAATGGAT | TAGCTGGCAC | CACCCATATA | GATAAACTGG | 154260 |
| ATTATCTGGT | CTTGAGTCCC | CCACCCCACC | ACTCCCAGGA | ACTGATTTAG | CACAAGAGGA | 154320 |
| CAGCTTAGGC | TCCCTATAAT | TTCATCTCTG | ACCCAACCAA | GCAGCACTCC | CGACTCACTG | 154380 |
| GTCCCCTACA | ATCAAATTAT | CCTTAAAAAC | TTTGGTCCCC | AAATTCTCAA | GGAGACTGAT | 154440 |
| TTGAGTAATA | ATAAAACTCT | AGTCTCCTGT | AGCGCTGGCT | CCTTATTGCA | ATTCCCTGT | 154500 |
| CTTGATAAAT | CAGCTCTGTC | TAGGAAGTGG | ACAAGGAGAG | CCCGTTGGGT | GGTTACAATA | 154560 |
| GGACAAACCA | ATAAAATATA | AAGTATTAGA | GACACTACCT | GGGTTTCAGG | AACAGGTCAG | 154620 |
| AAAAAGTGTT | TTCTTGGAAA | ACATCTGGAT | TCTGCTGCAG | AGCAAGTATT | TGCTTGTGTC | 154680 |
| TTCCCAGAGT | ATAAAAGCTG | TCCTGTCCAA | GATAGTTGCC | ACTAACCATA | TGTGAGTATT | 154740 |
| AAGCATTGGA | AATGTGGCTA | CTCCAAACTG | TGATGTGCTT | TAAGTGTAAA | ATACACACCA | 154800 |
| GATTTCAAAG | AACTAGTAAA | ATAACAAAGT | AAAAACTCAA | TATTTTAATA | TTAGATACCT | 154860 |
| TGTTGAAACA | ATTTTTGGTT | ACACTGGATT | CAAATCATTA | AAATAGATTT | CTTTTTTCAC | 154920 |
| TTTTTAAAAT | GTGCCTATTA | AAAAATTTAA | AATTACATAT | GTGGACCCTA | TGTTTCTGAG | 154980 |
| GAACAGTGCC | AGGACATAGA | GGATAGTTAT | ATTCACTCAC | AGATCAAAAA | CTAGCAAAAC | 155040 |
| TATGAAATAC | CTAATAATTT | AATTTTTCAC | CTTAACTTTT | GGCATATTCC | ACAGATCTGT | 155100 |
| AGTATATTTG | AGTGTGATAG | CTTAGGAATA | AATATGATTG | GAACTCATTC | ATGTTTAGAG | 155160 |
| AGAAAGGGTG | TCAAATTGAG | AACCAGGCAG | ATACACCTAA | TCTTAAAATG | ACCCCAAAGT | 155220 |
| AAAGTGGTTG | AAGAAATTAA | ATCCCAAAGA | TTTTTGGTGA | AGAATGTTGT | AGTTTTCATC | 155280 |
| AGTATGTGTA | TGTTCAAATG | GAGATTAAAG | AAGGCAAAAT | AAGGCCGGGT | GCAGTGGCTC | 155340 |
| ACACCTGTAA | TCCCAGCACT | TTGAGAGGCC | AAGGCAGGCG | GATCATGAGG | TCAGGAGTTT | 155400 |
| GAGATCAGCC | TGGCCAACAT | AGTGAAACCC | TGTCTCTAAT | AAAAATACAA | AAATTAGCCG | 155460 |

| | | | | | | |
|---|---|---|---|---|---|---|
| AGCACGATGG | CATGCGCCTG | TGGTCCCAGC | TACTAAGGAG | GCTGAGGCAG | GAGAATCACT | 155520 |
| TGAACCCGGG | AGGCAGAGGT | TGCAGCGAGC | CGAGATCACG | CCACTGCCCA | GCAGCCTGGG | 155580 |
| TGACAGTGAG | AGACTCCGTC | TCAAAAAAAA | AAAAAAAAA | AAGTCAAAAT | AAAAGAACTG | 155640 |
| TGGGCTGACA | ACTGTGGATT | AAGCATCAGT | TCTATTAAGA | AGGGCTAACT | TGAAGATGAA | 155700 |
| TCTTTTGAAG | ATACATTTTG | ACTCCAGCTC | TTTAGAGGAA | CAAAGTTTAC | CTTGATGTGA | 155760 |
| AATTCTTCAA | ATAAAAATTT | ATTGACTTTA | AATTTAAAAA | AAAATGCACA | CACACACACA | 155820 |
| CACACACACA | CAGCTAACTA | GCTACATCCT | TAATGACACC | AAGCTTTAGT | CCTTCACCCT | 155880 |
| GAAGTGGGAA | TGACAATGGC | ACTTACTTCA | AAGTGCTGTG | ACAAGAATGT | GTTTGAAAAT | 155940 |
| AAATATAGAG | TAATCAGCAA | CAGTGCTTGG | CATATTGTAA | ATAAGTGCTC | AAAAAATGCT | 156000 |
| AGTTCCCAAA | ACTGTTGTTG | CCACTGTACC | CTAAATCCCT | ATTCTCTTCT | GATATCCTTT | 156060 |
| AGTGATGTAA | TTCTGTCTTG | CACTGGGCCT | GTTCATCTCT | GGTATGAATT | TCAACCACAA | 156120 |
| TGTCCTTACT | ACATTTCCCT | CAGGCTTATA | TAGCCAAAAT | ATCCAGAGCT | TTGCCTAGGA | 156180 |
| GTGTATAATA | TGATACTTCA | ATTTGTAGCC | ATGATAGCAC | TGTGTATGAA | AGTTTGGAAT | 156240 |
| AATGCGCCGG | GCATGGTGGC | TCACGCCTGT | AATCCTAGCA | CTTTGGGAGG | CCGAGGTAGG | 156300 |
| TGGATCACTG | AGGTCAGGAG | TTCGAGACTA | GCCTGGCAAA | CATGGCGAAA | CCCCGTCTCT | 156360 |
| ACTAAAAATA | CAAAAAATT | AGCCGGGTTT | GGTGTCAGGT | GCCTGTAATC | CCAGTTACTC | 156420 |
| AGGAGGCTGA | GGCAGGAGAA | TTGCTTGAAC | CGGGGAAGTG | GAGGCTGCAG | TGAACCAAGA | 156480 |
| TCACGCCATT | GCACTCCAAC | CTGGGTGACA | GAGAGAGACT | ATGTCTCAAA | ATAAATAAAT | 156540 |
| AAATAAATAA | AAAACAGAAA | GTTTGGAATA | ATGCATTACA | AGTAGCCTCT | AGTTTTTATG | 156600 |
| TTACTCATAG | TTTTATCACA | CAAGAACAAT | GTCATAAATT | TCATGGTTG | AATTATCAGT | 156660 |
| TGTTTATGCA | ATATTCATTG | ATGTTTTGG | CTTATCAGCA | GTGTTTCTGG | AATTATTTGA | 156720 |
| ATATTATTAC | CGTTTTTCAA | AATTATTTA | TAAAACTAAT | TTAAAAATCA | AAAATGATAT | 156780 |
| AATTACTAAT | GTGAAATTAA | ATATAAGTTT | TGAAGAATAT | CAGGATGTCA | CCCCCAAATT | 156840 |
| ATTCTACTTT | GGCATAAAAG | TTATTTCAG | CTGAAGGCAA | TTGAAAATCA | ACAGGTGTAG | 156900 |
| GAAGAGGTCT | CTGTCTTCTC | TTTACCCAAA | TTTCCCTTTG | TGAAGGTGAC | AGAAATTTCC | 156960 |
| CTTGTAAAAG | TGTCCCCAAC | TGCTATACCA | GGAAAAAGAG | AGCAATTCTT | ATCACTAGAT | 157020 |
| ATGGAAGGTT | GGCACTGAGA | TGACTCTGCA | AAAACAAACC | TTACTACAAT | TATTTCTATC | 157080 |
| TTTCATTTTA | TCTTCCATGG | TTTTTATTGC | CCATGTATTT | ATTTCCTTGT | CACATTCCCA | 157140 |
| AATTCGTCAT | CCCATGAAGT | GCAAACTCCC | TTTCCTTTGT | TGGAATGGTG | TATAAGTCTG | 157200 |
| TGAGTCTAAC | CGCGTTTTA | AGGTTTCAAT | TTTTTTTCT | TTGGGAACTC | TGTGCATGTA | 157260 |
| ATATACTAAT | AAAATTGCAT | GCTCTTTTTT | TCGCATGTTA | ATCTGTCCTT | TGTCAGTTAA | 157320 |
| ATTTGCAAGA | CACTACTTAG | TGAATCTAAG | AGTACAGAAA | AACATGTGTC | CTCATTGACA | 157380 |
| GTTTCAAAAA | CTAAGTAAAA | TTGAGGCAAG | AATCTTTTTC | ATCTTAAAAT | GGCCAATTTT | 157440 |
| AATTTCCAAA | TGAATGGTTC | ATTAGACCTA | AGCCAGTAAG | CTATGTGAAC | AATTGTGATG | 157500 |
| GAATAAAACA | AAACTAAAGA | GCATGAACAA | AATTGAGAAA | ACATATGCAA | GACTGAATCT | 157560 |
| AAAGGCCAAA | TAGAATTGAA | AATTTTTCTA | ATTTTTAACT | CTATAAATTA | AAGGAATGTG | 157620 |
| TTTCATTTGA | CGAGTTTCAT | CTGTGGAAAC | ATGTTTGCAG | AAGACATTCG | AGGTTAGGAT | 157680 |
| TAATTGAAAG | TACATAAATC | AAATGGATTA | AGACCCCAAA | GGGCATTGAA | GGAAAATTAG | 157740 |
| AAAATCAGCT | ATTTTTGCTT | GGGTTGATTC | CTCTCCTGAC | TAACTCTTGG | AGATGATAAG | 157800 |
| AACATCAATT | AAATGGGTAG | CCATGAAAGT | ATCTAAGGGA | GAAAGGAACA | CAGAAGTTCA | 157860 |

```
ATGTACCATA ACTTTATTTT TATTTATTTA GTTTTTTGAG AGAGAGTCTG GCTCTGTCGC 157920
CCAGATGGAG TGCAGTGGCG TCATCTTAAC TCACTGCAAC CTCTGCCTCC TGGGTTCAAG 157980
TGATTCTCCT GTCTCAGCCT CCCGAGTAGC TAGGATTACA GGTGTGTGAC ACCACGCCCA 158040
GCTAATTTAT TGTGTGTTTT CATGGCCAGG CTGTATTTTC ATGGCCAGGC TGGTCCTGAA 158100
CTCCTGACCT CAGGTAATCT GCCTGACTCA GCCTCCCAAA GTGCTGGAAT TACAGGCGTG 158160
AGCCACTGCT TCCGGCTTTT TTTTTTTATG ACGGAGTCTC GCTGTGTCAC CCAGGCTGGA 158220
GTGCAAGGTC TCGCCTCACT GCAACCTCCG CCTCCCAGGT TCAAGCAATT CTCTGCCTCA 158280
GCCTCCCGAG TAGCCGGGAT TACAGGCGCC TGCCACCATG GTTGGCTAAT TTTTATACTT 158340
TTAGTAGAGA CGGGATTTCA CCATCTTGGC GAGGCTGGTC TTGAACTCCT GACCTCGTGA 158400
TCCACCCGCC TAGGCCTCCC AAAGAGCTGG GATTATAGGC GTGAGCCACC GCGCCCAGCC 158460
TTTTTTTTTT TTTTAATTGT TTGATGTTGA GATGGAGAAA CAGGAGGAGG TGGAAGAGAT 158520
CTTAATATAC ATATGGAAAA ATAAAAAATG GAATAACCAG GAAAATTCTG AAAAAGAAGA 158580
GTAATGAGAG AAAATTAGCT CTATCTGCTA TTAAAGTCAC GTTACAACAT CTCAGTTAAT 158640
TAGTCTCCCA AAGGGGAGAC TAATGTAAAT GCATGTTTAA TAAACTGCAC CCCCAGTGGA 158700
TGCCTGAAAC CACAGATAGT ACTGAACCGT ATATACACTG TTTTTTTCTA TATACACATG 158760
GCAATGATGA ATTTAATTTA TAAATCAGGC ACTGTAAGAG ATTAGCAATA ACTGATAATA 158820
AAACAACAAT TATAACAATA TACTGTAATA AAAATGATTT GAGTCTGTGA ACGGTGGTTC 158880
ACGCCTGTAA TCTAAGCACT TTGGCAGGAT GAGGTGGGCG GATAACCTGA GGTCAGGAGT 158940
TCGAGACCAG CCTGGCCAAC TTAGTGAAAC CCCGTCTCTA CTAAAAATAC AAAAATTAGC 159000
CGGGCATGGT GGCAGGCCCC TGTAATCTCA GCTACTCGGG AGGCGGAGGC AGGAGAATCG 159060
CTTGAACCCG TGAGGCGGAG GTTGCAGTGA GCCGAGAACG TGCCACAGCA CTCCAGCCTG 159120
GGTGACAGAG GGAAACTCCG TCTCATAAAT AAATAAATAA ATATAAATAT AAATTATATG 159180
ACTGTGATCT CTCTCAAAAT AGCTTACCGT TTTACTTGTG ATGATGTGAG ATGACAGAAT 159240
GCCAGTAATG AGATAAAGTG AGGTGAATGG AGTAGGCATT GTGAAGTAGC ATTAGGCTTG 159300
ATAAGATACT ACAGATTTAG GTATTAGTTG AACACTTGCC ATTTGTCACA TAATCATCTC 159360
AGCATTGAGG ATAGCACACA ACACAATGTT TAAAACAATA CAATTCTACC TTAAGAATTG 159420
TGGGAATGAC TAAAGGAACA AAATAGAAAC CTGAGAAACC TAAGACAGTC CAACTGTCCA 159480
TGAAATTATA GCGTATTAGC CTATGACAAA ACAGCCAAAA TTGATAGGAG CGTGGAGGGT 159540
GGCACGGGAG GAAGAAGGGG GAAGCAGAAA TGAAAGTTCA TAAATGGTCT TGGGAAAAAT 159600
ATGTCCATAT GTTAAACCTT ACACCAAAAT AGAGGGTTCA CCATGTTAAA CCGTGTTGTA 159660
ATGTAAAATT AACAACACAA AATTACTTAA ACCATGGGAG AATGTTTTCT CCTTCTTCCC 159720
TGCCTCTGTC TTCCTGTCTC TCTGCTTGCC TCCCTCCCCT TTCTCTTTCT TGGGATGAAT 159780
CCGTGGTCAC TATCACTAAC AAATCAACTC ACTATATTAA TCATTGTGGA GATGGTAGAA 159840
TAATTGAGCA GCTTATCTCC AGAAGCCCCA GTCCCCATAA TTTAGGTCTC ACCAAAATGT 159900
GCCCACCAGA TTTTAAAAGA AGCGAATATA AGACGCTAGG CTTTCTGTAT TCAGAAGCAC 159960
CATGGATGTC AAACAGAGGG AACCATTAAC GAAGGCCTTT ATTAGAAATG TCTCCCATTT 160020
ATCCATACAC TCTTCATAGT TAATAGTACA AATACTGTTT TCTGCATAGA AACATTTGGA 160080
CTGCCAAACA AAATACGTTT AAAGGAACTT CGATTTTTAA ATGTTGCTGT CTGTCTAAAC 160140
AGGATAAGCA ACCGTAGTCA TGCGAGGACA AAATGGCTGG CTAAAAGTTG TGCTTTCGAT 160200
ACGCTCAAAA TCGATACGCT CAAACCTGTC AGTTTAGCGG AAGGCTACAT GTTATGTGGC 160260
```

| | | | | | |
|---|---|---|---|---|---|
| ACAAAAAACT | CCCTAGGTCC | ACGATTGCCT | TGGGTGGAGG | AAGGGCTATT | GCCGCTGTTG 160320 |
| TGGCTGTTTT | TTAAATGCAT | TCCTTCGTTG | CCACAGGAAT | GAGAAATTAA | CAGCAGAGGA 160380 |
| ATGTAGGACA | AAGGTACCTG | CACGCACTCT | CCTCCCAGGG | CTGGATGTTG | CCACTACCTC 160440 |
| CAGGAGACAT | CAACTTGACT | ACCAACAACA | TGGAAAGCGT | CCGAAATCCC | AGACATTAAT 160500 |
| ATAAAGAGAA | AAGAGGCAAA | ACTTTTAAGT | CACAGTAAAG | CAAAAAACAC | AGAATAAGCA 160560 |
| ACGTCTTCCA | CCATCCAATT | AAATACAGAA | TGAAAGTCAT | GTACTAGAAG | AACGGACCAA 160620 |
| CCCGGGAGCA | GGGCGGGACT | TTTGAAAATT | TTTTAGTCCA | ATCCGGACAT | CCCTTTAGAC 160680 |
| TAAGAAACTG | GCTCTTGTTT | TGCGGTCTTT | TCTGCCGTTC | ACAGGCCTGG | GGCGGGACTG 160740 |
| CCATCCCAAA | ACCATCCGCC | AGCGAGAAAA | GCCTCCGGTC | AGGGACCTAG | AAGCCGCAAT 160800 |
| AAAGGTTTAA | ATGCTGTAAC | CTCACCACGG | CCACTCTCCA | ACCCCGTCAC | CCAATTCGTC 160860 |
| TGATACCTCA | GTAACTCCCA | TACGACTAAC | CTTAAGTAAC | AGGGCAGAAC | AAGAAAAGGC 160920 |
| AGATAGTAAA | GAAATTATCC | AGCTCTTTTA | TTGAGATCAG | TGGTGGCTCT | GAAAAGAGCC 160980 |
| TTTTGGGTTT | TAGAAGTAGG | CGTTCGCCTA | TTTCTTCTTG | GGCGCCGCCT | TCTTAGGCTT 161040 |
| GACAACCTTG | GGCTTAGCGG | CCTTGGGCTT | CACAGCCTTA | GCAGCACTTT | TGGCAGCTTT 161100 |
| CTTGGGCTTC | GCAACCTTGG | CCTTCTTTGG | GCTCTTAGCC | ACTTTCTTGG | TTACAGTGGC 161160 |
| CGCGGCCGGC | TTCTTCGCTT | TCTTCGGTGT | TTTCTTAGCG | CTCTTCTTCG | GAGTTGCGCC 161220 |
| GCCAGCCGCC | TTCTTGGGCT | TCTTGGCTGC | CCCAACTGGC | TTCTTAGGTT | TGGTTCCGCC 161280 |
| CGCCTTTTTA | ACCTTGGGCT | TGGCTTCCCC | GGAGGCTGCC | TTCTTGTTGA | GTTAAAGGA 161340 |
| GCCAGAAGCA | CCGGTGCCTT | TCGTTTGCAC | CAGAGTGCCC | TTGCTCACCA | GGCTCTTGAG 161400 |
| ACCAAGTTTG | ATACGGCTGT | TGTTTTTCTC | CACATCATAG | CCGGCGGCAG | CCAACGCTTT 161460 |
| TTTCAGAGCA | GCCAGAGAAA | CTCCGCTACG | CTCTTTAGAG | GCGGCCACAG | CCTTGGTGAT 161520 |
| GAGCTCTGAC | ACCGGGGGAC | CAGACGCCTT | ACGAGGCGTA | CCCCCAGCCT | TTTTGGCCGC 161580 |
| CTTCTTCTTT | ACAGGGGCCT | TCTCCGCAGG | AGGCGCGGCA | GCGGGAGCGG | CAGGAGCAGT 161640 |
| CTCGGACATG | TTGAGAATCA | AAAACTCGGG | TACAAGTGGC | AAAGCGCCGA | TGAAGCAGCG 161700 |
| CCTGGGCAGG | GCCGCTGTAT | ATATAGAGCG | CAGGCGCGCT | CTGATTGGTG | CTCTGGTCGC 161760 |
| CCGCCTGGCT | GGCAGGCTCT | GAGCCGCTGC | GCTGCTCCCA | AGTTGTGTTT | GTTCCACCTC 161820 |
| ACAAAGGGG | AAAAATATTA | AAATTCCCCG | CACCAAATCA | CTTGGGTTTG | GTCAGGAAAG 161880 |
| GATCTCAGAA | GCCTCGGGCT | TCATGCTCTT | CATTTATTTT | TTCCACAAAC | ACAAAAACAA 161940 |
| CGCGTCCAGG | CGTCCCCAAT | TCCCCCAACT | CCGAAGGAAG | TCTGGGGCAG | TCAGAGACCA 162000 |
| CTTTCTGTTT | TTCTTATAAA | TTACCTGTTC | GCTCCTTTGC | CCCTGAAGGT | TCTTTTTCCC 162060 |
| AGGGGTGGTT | GGGCACATGC | TTCCCTTATT | TTTGAAGAAA | AAAGCGAAAT | GGTTTCCACC 162120 |
| TAAATTTTCA | TGATAATTCT | GTTTCTTCAC | AAGGGAAGTA | ACACAGGTCC | TCTGTGAATT 162180 |
| CTTCGTGCAG | TCGCACAGGA | ACTGTGGACT | GGGACAAGGA | TTCCACGGCC | AGTCCAAAGC 162240 |
| AATTAGGGCG | GGATGGGAGG | GGGTTCATGA | GCCTTGCTAG | GGTCCGGGGT | GGTGGGGGC 162300 |
| TACAGACTTA | AATCTTTGAT | TTGAAGACAT | TGAAACTATC | AAATCCCTCT | TTTCATAGAT 162360 |
| GGGGGTGGGG | CATCCTTTTC | ACTTCTCTAC | AGGCGAGAAA | TTGGGCTCTT | TTTAAAGAGC 162420 |
| TCTGAGGTCC | CCCTCTGAGT | TGTGTAAGGC | AGGAGGTCTG | GCCCTCAAGA | TAGAGATCAT 162480 |
| AAAGGAACAA | GGGAGAGCCC | TTAAGCCTGC | AAAAAAGCCA | ATAGATTTGG | CAGTTAGAGG 162540 |
| CACTGAGATA | ATATGTTTTC | AAAGAAAACA | AGCATTTTTT | ATTTATTTAT | TTTTGTACGC 162600 |
| TGCAATATAG | AAATGAATTT | CAGCCCATGA | AAATTGTAGG | TTACTTTCAG | TAACCATACC 162660 |

| | | | | | | |
|---|---|---|---|---|---|---|
|TTACGCAAGT|TACCATATAG|GACAATCTCC|AGTTGGGAAC|TCAAATATAT|CTTTTGAGTT|162720|
|GCAAATAAAG|CAACTGACTT|TAATAAAACA|CACTCTTGAC|TTTTAAGATG|AACAATGTAT|162780|
|TTGAAATTTA|TTTTTTTAAA|TAGCAAAATT|TAACACAGAA|AGACAAGAAA|AGTACCAGAA|162840|
|CATGTAATTT|ATTATAAGAT|CTGTTGTTGA|TGAGCTGAAA|AATCACCTCT|TCTCATCCCC|162900|
|TCTGAAACTA|TTCTGTTCTA|AAGTTTGCTA|CTTTAAGGTT|CACTACTTCT|TATTTTACTC|162960|
|TCCGACCCCA|AGTAATTGCT|ATTTTTTTCT|TGAGATTAAA|GGCAAAGTAA|ATTGTCTGCC|163020|
|CATATATTTG|ATATAATTAT|AGATTCATAT|TTAGGGACAA|AGGTAATATT|ACAACTCCCC|163080|
|AACAATTTCT|GCTCAAATAT|ATGTTTTCAT|GAAAATATGT|GTTAAAGAGA|ACAGCCTTAG|163140|
|ATTGTGGGAA|AGTCAAAAGG|GAACCTACAA|ATAAGAGTTC|AATGACAAAT|GAAAAGTGAA|163200|
|ACATCTTTTA|GACTAAGGGT|GACCCCATTG|TTTTATTAAA|TAACATTTGT|CCAACATTTG|163260|
|TAAACATTGT|CTGCTTGTGT|GCTTATGTCC|TCTGGGAATT|AACAGTCTAA|TGAGATTAGT|163320|
|GATGGATGAA|TTAGCAGTGG|TGGAAAAACA|CTTAGACCGG|CTATTCCTCA|GAGTGACAGG|163380|
|GTATAAGAAT|TATACAAAAT|TATGGAAAGT|GTATAAACAA|TTGAAGCACC|TGCATCATAC|163440|
|TAATATATTG|TAGTAAAAGA|AATAATATAA|GGCTGGGCCC|CGTGGCCCAC|GCCTGTAATC|163500|
|CTAGCACTTT|GGGAGACTCG|GGGGCGGATC|ACCTGAGGCC|AGGAGTTTGA|GATCAGCCTA|163560|
|GCCGACATGG|TGAAACACCA|TCTCTACTAA|AAGTACAAAA|ATTAGCTGGG|GGTGGTGGCA|163620|
|CTCAGGAGGC|TGAGGCAAGG|GAATCGCTTG|AACCCGGGAA|GCAGAGGTTG|CAATGAGCCG|163680|
|AAATGACGCC|ACTGCACTCC|AGCCTGTGCA|ACAGGGTGAG|ACTCAGTCGA|AAAAAAAAGA|163740|
|AAGAAAGGAA|CAATATAAGA|ACATGTCACT|TAGGCCAGGC|TTGGTGGCTC|ACGCCTGTAA|163800|
|TCCTAGCACT|TTGGGAGGCT|GAGGCGGGCA|GATCGCCTGA|GGTCAGGAGT|TCGAGACCAG|163860|
|CCTGGCCAGC|ATGGTGAAAC|CCCATCTCTA|CTAAAAAAAA|TACAAAAATT|AGCCTGGCGT|163920|
|GGTGGCAGGC|AACTCTAATC|CCAGCTACTC|AGGAAACTGA|GGCAGGAGAA|TCATTTGAAC|163980|
|CCGGGAGGTG|GAGGTTGCAG|TGAGCCGAGA|TTGCCTCGTT|GCACTCCAGA|AGCCGAGATT|164040|
|GCCTCATTGC|ACTCCAGAAG|CCGAGATTGC|CTCATTGCAC|TCCAGCCTGG|GCAACAGAGC|164100|
|AAGACTCCAT|GTCAAAAAAA|AAAAATAAA|ATAAACATTT|CACTTAGATC|TTATTCTATG|164160|
|TGCAATGAAC|CCCCTTCTCA|TTTAAAACTC|AGCTAAGTAT|ATCCATCATG|AAAATAGCTA|164220|
|TGAAACGTCT|TGATTACCAG|GTAACTGGAC|CTTCTTTCAC|TATAAATTGG|TGTCCTGGTT|164280|
|TATAAATCGA|CATGTAAATT|TAATCGCTGT|GATTCAGTTC|TCTAATATGA|TTTTTCTAGT|164340|
|CGACTCAATC|TAATCACATC|TCTTTATATG|CAAATCTCAA|GTCCAGACCT|CAAGCCATTA|164400|
|GGACATCCAG|CCACCCAGAA|TCTTGTCCCC|AACCTCCTGG|CAACATGGTG|GAGGCCAGAA|164460|
|GACAGAGAAA|CATGTAACCA|ACCCTTTTCT|AGATCCTTTA|TAAAGTGTGT|TGAAAAAGTT|164520|
|ATGCAAAACT|TAAAAGCAAC|GCAAAATAT|TTCTCCATAT|CCTTCCAAGC|TATATTAGAG|164580|
|AATTATCTAA|AAAGCCTACT|TATGGGGTAC|CTGATGATGT|AAGGCAATAC|TAGACAGTAA|164640|
|AATAGAATGT|GAATCACATA|AATACTTCC|AGATTTCTAG|TGGTCACATT|GAAAGAATGA|164700|
|AAAGAAACAA|GTAAAATTAA|TTTTAAGATA|TTTTATTTAA|CTTAATATAT|CTAAACTATT|164760|
|ATCACTTCAA|CATATAATAA|ATAAGCTAAA|AAAAAGACA|GTTGACATTC|TTTTTAAAT|164820|
|GATAAATCTT|CAGAACCTGG|TGTGTATTTT|ACACTTTTAG|AACATTTTAA|ATCAGTCTAG|164880|
|CTATAGTCCA|AATGGTCAAT|GATCACGTGT|AGCTAGTGGT|ACCTTATTGG|ACAACACTGT|164940|
|CCTACGTGAA|AGTAACTCTG|ACTTAATGTT|TACATTTTAT|TGGGTCCAGA|CTATCTAAAA|165000|
|GTAAACATTC|ACTTGTAGAA|GTTTAATAAA|TTAATAAGGA|TTTTGTCATA|GAGATGGAAA|165060|

```
TGAATTCTTA ATATAGAAAA AATGACCCTA AAAGTTATTA TTGTATTGCC TAATAAGTCA 165120
TTAAACAACT TTATATCTGA TTTTCCCTTC CTCTTCCAGT ATACATCCTT TCCCTGACCA 165180
AATACATATT TTATTCTCCC GTATCTTCCT TTGACCTAAT TGTGATTCTG CTTCCTCCTT 165240
CATTAATGAA TTAAATCATT CATTGACACA TACACAAGCT CACTATATAT AGTACATATA 165300
TGTCAGTCAT GTTTTAACT TCCTGAATGT TGTACTTTGA CACTTGGTTG TTCAATTTCG 165360
CCTAAGAGCT CTGAATCAGA ACCTTTAGAA GCCATTCTGA AAAACTGGAA GATACAAAGC 165420
TTTTGACTAT CAACTCCATA GCAACCTGAT ATCTGGTTGG TGTTCCATGG AAACTGTATT 165480
TCTCAAATTT TGAAATAAGA TTGAACAAGC CTGTGAGCAA CAACAAAAAA AAAGTCTATT 165540
AGAATGACCT CTGGCCGGGC GGGGTGGCTC ACGCCTGTAA TCCCAGCACT TTAGGAGGCT 165600
GAGGTGGGCA GATCATGAGG TCAGGAGTTT AAGACCAGCC TGACCAACAT GGTGAAATTC 165660
CGTCTCTTCT AAAAATACAA AAATTAGCTC GGCATGGTGG CGTGCATCTG TAATCCCAGC 165720
TACTTGGAAG GCTGAGGCAG GAGAATCACT TGAACCCAGG AGGCGGACGT TGCAGTGAGC 165780
TGAGATTGCG CCACTGCACT CCAGCCTGGG TGACAGAGCG AGACTCTATT TCAAAAAAAA 165840
AAGAATGACC TCCAAGGGAA AGTTCAGATT AAGGATGTGG TCGTCCCACC CAAAACTGAT 165900
GTCCTCAAGA AAGCCACAAA CAAATTGAGG ACACAGTTAA AATATTGTAA TGCAATATAT 165960
TGTGTATTCT TTTATTTACA CACACATCAT AAATATTATA GGTTGACTAG TTTTGTTTCA 166020
TGCCACACTC TTCAGGGTCT GGAAACCCTG GTAGAAAAGT TAAAAATGCA GAGCAAAATG 166080
TCAAGTCCAA ACAGCAGTAA TGGGGCTAGA GAGAGACTCA AACAGCCAAG ATATATTCAA 166140
AGGATAGTGA GAGGAGTTGT TAGGACAGGT GTAAGGAATG AGGGTGACAG CTGGTTTTTC 166200
TTTCACTTTT TCCTTCTACT ATGCCAATTA GAGTTCTTTG TTTTGATAG AGACAGGGGT 166260
CTCACTATGT TGCTCAGGCT GGTCTCAAAC TCTTGGCACC AAGTGATCCT CCTGCCTCAG 166320
CCTCCCAAAG TTTTGAGATT ATAGGTGTGA ACCACCAAGC CCAGCCTTAG AGTAGGGTTC 166380
TGTCATCTTT TGGATGTAGC TAACCTAATA TTACTAAATC CTGTATAGGC CAGAACTTTG 166440
AATGATTTAA AGCTGTTTTT TCCTGACTCA CCAATTAATG AAGCTAATAA TAACAGCCAC 166500
CCCACTGGCA GTGCCTGCCT CAAAGAGTAA GTGTTAGTGT TGCTATCTGC TTGAGACCAA 166560
CAATACAGGG ACTCCAGGAT ATTTTCAGCC TAAATAAGAT TGTAGGGGCT CTTGTCTGTT 166620
GCCTGGCTTC AGCCCCATAA ACTTTTTTTT AACATATAAC CCAGAGCCAC AGTTTTGCTC 166680
ATATTTCAAT CTTTGAAGGC AAATGGCCAA CAATTAGATT AAACCTGAGG CTAAATATTT 166740
CCTCACCTCA AGGGCTGAGA CGAAAGTTAC TGCATCTGTA TTCCCTAACA CGCCCTCAAA 166800
ATGGGTTGCA GAAAACAACA GAAAATATAC TAAAGCACAC AGTAGGAGCA TAATAAATAG 166860
TGATTAGCTG GGTGCAGTGG CATGCGCCTG TAGTTCCCGC TACTCTACTC ATGAGGCTGA 166920
GGCAGGAGGA TCACTTTTGC CAAGCAGTTT GAAGTTGCAG AGAGCTATGA TCACAACACT 166980
TCACTCTAAC CTGGGCAACA GAGCAAGACT CTGTCCAGAA AAATAAATAC ATAAATATAA 167040
AATTTAAAAA TATAAATAAA TACATAGAGA GTATTACAAA AGGAACAATA TATTGCAAAA 167100
TATATTTACC TAACATTTTG AAATTGCCAT TATAATTGTA TAAGTGACAT AGGAAACTGG 167160
GTCATTAACA GCTATCTTAT TCTTCAAGCT TCTTTCAAAT GATGTCAAAG CATTTCAGAA 167220
AGTCAAACCT ACCCTCAAAG GATAAGAATT TGTCAATTGT GAGGATATGC ACATTTTTAC 167280
ACCTTCTCAA TCTGTGTCTA TATGAAGGCA GTTATAAAGC ACAAGATGCA AACGTATATT 167340
AGGCAATAGT CTTCATCAGA ATAAGTACAT AACCTGACAC AATGACTATA TTGGAAGAAA 167400
CATGGAAATG CAAATTTCAA TAGATTGGTT GACATTATTT TTTAATGTCT AGTTTTTTAC 167460
```

| | | | | | | |
|---|---|---|---|---|---|---|
|TGTGCTGTGT|TTTTACACAC|TTAATGAGCA|CTTGTTAAGC|ACAGGACACC|AGGAGAAATA|167520|
|ATAAAAACTA|AGATCAGCCT|AGCAGTGTGT|CCTCTCAAGA|ACTTATACCT|GGTGGGACAG|167580|
|ATACAGACAA|ATATAACCAT|CATACAGTGT|GAGAAATCGA|TAGAAAAGAC|ACAGCCACTG|167640|
|AGAGCACAAA|AGAATAAAAA|CATAAAATGT|TAATGTGCTG|GCTAAACGTT|TGCCTTCAAG|167700|
|TATTTACCAG|TCTAGCTGGG|AAAATAAGAC|AGAAGACAAC|AGCCTAAAAT|AGTGGTTCTT|167760|
|AAACATTTAG|ATATCAGGAC|TTCTTTACAC|TCCTAAAAAC|TATCAGGCCT|CCAAAAAATA|167820|
|TTTTGCTAAA|TATAGGCATT|TATCACTTTG|GAAAACAAAG|CTGAGTATTA|ATTATTTAAT|167880|
|TATTTATATT|AATATTTATT|TGATAACCTT|TAAAATATTA|TAAAATTAAT|ATTTATTTAT|167940|
|AATGCATATA|TGTGATTATA|TAGTTCATAT|GTAGCCATAT|ATTTATCATA|TATACCATAG|168000|
|ATTTATGTTA|TATATTACAT|ATGTATGAAG|AAAAAATGGA|AAGTAAACCC|AAAAGTTCCC|168060|
|CATTCCCTAA|CCCATTCAAA|ACCCTGGAAG|TCCCAGGCTA|ATCTGAAACT|TGTAAAACTG|168120|
|CCTGCATGTA|GAGAGCACAG|CTGAGCTGGT|AGTGTGGAAG|AGCAGAAAGA|CAGCAGTTCT|168180|
|GGAGCAAGGA|AGCTTTATAT|TTAATCCCAG|TTTCTCCATT|CATGAGCTTG|GTTACCCTGC|168240|
|CAAGTTCCTT|CTCTGTAAAA|TGGGAATAAT|ACTCCCAGAA|ATACAGTGAG|GATTAAATTA|168300|
|GATAATGTGC|ATACAGTTCC|TGGGATTGGG|ATCAGCACAC|AGTAGCCTCT|CATTTGAGGC|168360|
|ATATTTGCAT|TAGATCCTTG|CTGTATGATA|TCCTTCTGTT|TCTTTCTTTT|TTTTTTTTT|168420|
|CCTTTGGTGA|CCCTAAGAAA|GATGGTACTC|TCCTTAACTT|GGAGGGCTGG|ATGCGAAGAG|168480|
|ACCAAATCCA|ACAAGCTGGT|TCATTCTTTC|TAATTATGTG|TGCTTCCCTT|AGCTGCCTCT|168540|
|GAAAGGATAC|AGGCCCTAGG|TACTAGCCCC|AAGAAGCCTA|ATGATAAGAG|ATAGAGCTGG|168600|
|ACCACCAGAG|AAGAGATGAG|TGTGTATGTG|TGTGTGTGCA|AGCAATTATA|TGTGTGCATT|168660|
|TAGGAGTGGT|AGGTGTGTAA|ACAGTCTAGA|ACACTCATTC|TCACTGTGAT|GTGAGGATGT|168720|
|ATCCCCACAT|CACTGTTCTG|GGAGCTCACT|CCTTGTCCAT|CATCCAAGCT|TATGATGGAC|168780|
|AATTCTTTCC|CAAGTGGGAA|AGAATTCTGA|TGACACTCAC|ATAACTACCC|AGTCCCAACT|168840|
|TTCTGTATCC|AAGGTGTGTG|CATACCTTTG|ATAGCAGGCA|GGTGTGCCTA|GCCAATATAT|168900|
|TAGGAGCATG|GTATTCCAGC|ACTCTGCACT|TTTTTACTAT|AGAATTCATC|TCAACCTGCT|168960|
|TACATTACAT|GAAAGTTTTG|ATTGATATCA|AATTTTTATT|ATGTTTGCTT|ATCAAAGGAT|169020|
|TTGTAATTAT|GCTTCAGTTG|ATACATAGAT|TGTTTATATT|TTTCATGGTT|ACTTGAAGCA|169080|
|CTTATATTTT|CCTCATACTT|TTACAAAGTA|ATCAAGGAAA|AATACAGAGG|CAGCTTAGTA|169140|
|TATTAGTCAA|AAGAATAATT|AGACTGTCTT|GGAACCTGGA|ATGTCTGAGT|TCAAATTCAA|169200|
|TTTTGCCGTT|TTACCAGCTG|TGTGACTTTG|GGTGAGTTAA|TAAACCTTTT|CGTGTCTCAG|169260|
|TGTTCTCACA|TGTAAAGAGA|CAATAATAAG|CCTACCTGTT|TCATGGGTCA|TTATGAGGAT|169320|
|TAAGGAGTTA|ACATTTAAAT|AGTTCTTAGA|ACAACCTCTG|ACATATTTTA|AGTACAAAAA|169380|
|TATATACATA|TATTAAATAA|TAACTTTTCT|AAAACATCCT|ACCTACAATC|TTGTGTGCAA|169440|
|ATTGGTGGCT|CAATTCTGCA|ACTGTTGTTG|GTGGTGTTGT|TGTTAAGCTT|TTGTTTGTCA|169500|
|TGACTGTTAT|CAGTAATATT|AATACAGACA|GTTAACTGAA|CCCTTCCTCT|GCACCAGGCA|169560|
|TTATATGGAC|TATTTTCATT|CTGACTCCCT|GCATTCTATG|AGACAACCAC|CATTGTAATC|169620|
|ATTCTCACGT|TGCCAATAAG|GAAATGGAGA|ATGAGAATTC|AGACTTCTCC|AAGAAGTGCT|169680|
|GCAGACTGAT|TATAAATCAT|GCATCCTAAA|CACACACATA|TTAAAGTATC|AACTAAATCA|169740|
|AACAGAATAA|AACTTTTGTT|TTTCTATCTA|CAAAATGCAT|GAATTAAAAT|ATGCCCCAAC|169800|
|TACTTAACTA|ATATATTTAG|TAAGTAGAGG|GATGGAAGCG|TTTTCACTCC|TTCAATACAT|169860|

```
TCTTCATCAA CCTCTCTCAC CTTACCCCTC TGTCACAGGC ATTTCCTATG TCATGCGGTT   169920
TTTCTGATGT ACGCTAGGTG GCAGTCAAAA CCACGAACTC TTGAAAGAGA GTATATTCCT   169980
ATTTTTCTGC AGCCTCAACC TCCAGGGCTC AAACGATCCT CCTGCCTCAG CCTCCTGAGT   170040
AGCTGGGGCC ACAGGTGCGA GCCACCACAC CTGGCTAACT TTTACATTTT TGATAGAGAC   170100
GGGGTCGCCA TGTTAGCCAG CCTGGTATCG AATTCCTGAC CTCAGGTGAT CTGCCCGCCT   170160
CAGCCTCCCA AAATGTTGGA ATAACAGGAG TGAGCCACAG TACCTGGCCG GTAATTTTTA   170220
ACTTCTAGCT ATACACTTAG TTTTTTGTCC TTTTCAGTGG ACAGAAATTA TAATGCCTGT   170280
TTGACAGGGG ATAATTCTGA GGCACTGGGA AGCCATGAGA CTGCATGGAT TGCACAGGCA   170340
GGCAAGAACA TGGGAAGGAA CAAGTGTCTT AGACACTTGT CTCAGTGGTC TAGAAAAATC   170400
ATGCTAGCTG ATTCATTCAC TCCACAAACA ACTGATCAAC ATCTTCAAGA AGCCTAACAA   170460
TGTACTGAGT TCAGGGGACA AGAAAATAAT TCAGACAGGC TCTACCTTCA TGGTGGTGTT   170520
TGAAGAATAG GGATCTAGAA AACGGTAGGT AATAGTGGCT GTGCAAAAGA TATCAGAGAT   170580
GATATGAAAA GGAGGGACTA GACCATTTTA CCCAGGAGTG GAGGTTAAAC ATAGGGTCTT   170640
TAAGGGAAAC GTAAAAATAT TAATTCTTTT CATTTTGAA GTAAAATGAC CATCGCTTCT   170700
CGGCCGTTTG GCTAAGAACA AGTGAAGTAA AATGACTGAG GATGACAGAC ATAAATACTG   170760
CTATACAAAC ATGGTAGCAC TGAAATTGGC TCTTGCCTGA CAGGAAGCAA AATTATAAAA   170820
TTCATTATTT AGATATATCA ATAATGATGG TGATCAGGCT GTAATAATAA TGTTATTAAT   170880
CATTATGTAT CAATAAGAAT ACAGGTGTGT GACTTTACAA TGTGCCTAAG AGCAACCCAA   170940
TATTTTGATT GTAAACCACA TTCCCTTAAA CACACACACA CCTCAAACAA GACCCCATAA   171000
AGCAGACTGC ACTAAAGTGG AGGTTATGTA AAAGTCCAAC AGAATAAGAA CCCTCCCCCA   171060
TTGTGTATTA ATCTGTGAAC TAAAAAAAAA TTTCATTAAA TTGAAAATAT CTAATTGTCA   171120
ACTAGCAATT TTAAAGAGTT TAGGCAGAAA ATGAAATATA AAGCTTTTT TTAACTTTTA   171180
GATTTTTCAA AGCTAGCAGA ACTGCTGAAG AATAACAATT CAAAACATAG GTTTGCTTTG   171240
GTTTCAATCT CTGTAGCCAA AGGCATTTAC AATGTAGGAT GTTGTTTGTG CTTTCAGACA   171300
CTAGATGACG CTCCAAATCA AAATGCCGGT AGTTGGACAG CCCCTGATCA AGCCGCCCGG   171360
CAAATCATTA ACTGGGTTGA CACTGTATTA CTCAGCAGAT TTCAAAACTC ATTCACATAC   171420
AGAGTCTTTT GGTGGACAAA AATAATTATT ACCCACAATT GACAGTGACA GTACTGAGAA   171480
GCTGGGAAAC TGAAGTAGGA CCCTGGAGCA GCCAAGTACA GAGACTGGCT CCCAGGACCT   171540
TAGGAGTTAA TACTATTCCT AAAGAGAATA AATTGTCAAA TAGACAAGAA ATTCATGTGG   171600
GTTGATGCAT TCACTTCCCC AAAACAATTA TTAAGCAGTA GAAATGATAA CTACGCTGGT   171660
AGTGGAAATA GTTTACAGTA AAAGGGAGAA GACATGCAAA AACCAAAAAA AAAAACGGGG   171720
CCGGGCGCAG TGGCTCACTC CTGTAATCCC AGCACTTTGG GAGGCTGAGG CGGGCCGATC   171780
ACGAGGTCAG GAGATCGAGA CCATCCTGGT TAACAAAGTG AAACCCCGTA TCTACTAAAA   171840
ATACAAAAAT TAGCCGGGCT TGGTGGTGGG TGCCTGTAGT CCCAGCTGCT CAGGAGGCTG   171900
AGGCAGGAGA ATGGCGTGAA TCCGGGAGGC GGAGCTTGCA GTGAGCGGAG ATCACACCAC   171960
TGCACTCCAG CCTGGGCAAC AGAGCAAGAC TCCGTCTCCA AACAACAACA ACAAAAAAAC   172020
AGGCAGTGAT GTTTTATGTG GGTCAGTGTG AAGTAGAGAT CAAAGGAGAA AACGGCCAAT   172080
CTTACCAAAT AATGGATGCA GAAATAATCT TCATGGAGAA GCCACTTTAA TTATGTCTTA   172140
AATGAGAGTA ACAAATTAAA CATAAGAACC TGTAGGGGCT AAGGGAAAAC TTACTCTTTG   172200
GCCTCTGAAG AGTCGCTGAA AACCACCGAC AAGAGGAAGA TTAATAGGAT AAAATGCATC   172260
```

| | | | | | | |
|---|---|---|---|---|---|---|
| CAATTTATTA | TTATTATTAT | TATTATTATT | ATTATTATTA | TTATTATTAT | TTTTAGACGG | 172320 |
| AGTCTCACTC | TGTCACCAGG | CTGGAGTGCA | GTGGCGCAAT | CTCGGCTCGC | TGCAACCTCC | 172380 |
| GCCTCCCGAG | TTCAAGCAAT | TCTCCTGCCT | CAGCCTCCCC | AGTAGCTGGG | ACTACAGGCA | 172440 |
| TGTGCCACCA | CGCCCAGCTA | ACTTTTGTAT | TTTTAATAGA | GACGGGGTTT | CACCATTTCG | 172500 |
| GCTAGGGTGG | TCTTGACCTC | GTGGTCTGCC | CGCCTCAGCT | CCCAAAGTGC | TGGGATTACA | 172560 |
| GGCGTGAGCC | ATTGCACCCG | GCTGCATCCA | ATTTATTAAT | GTGTATATTA | ATAAATTATC | 172620 |
| CAATTTATAT | CCAATTTATT | AATGTGTATT | AACATGTACA | GGGGAAATTG | TCCATTTTTA | 172680 |
| TTTTTTAGAT | TCAACAAAGT | ATGGGCCGCC | GTGTAGAAAT | AGGATTGCTA | ATAAACAGAG | 172740 |
| TAGGGAAACC | CAGCAAGGCC | TGTCTGTCTA | GATTCTTCTT | CGCCTCTCTG | TGCAGCATTC | 172800 |
| CTTCCTTCTG | GATCCTCTCT | GGAATGCGGT | CTGGTGATCT | ATGATCAAAT | AAGGTAGTTC | 172860 |
| AGATAATTTC | TTTATGGCCA | GTTTTACAC | AGAAAACAG | AGGGAAAGTT | AGAGTAATAT | 172920 |
| TTTTAGGTTT | TATGGCTGGG | CTCTGGGGAA | AAGGTGTTTT | GATTTCTATG | ACCTAACTTG | 172980 |
| AGGAAGAGGA | ATTCTCATTT | CTATGGCTAG | ACTCCGGGGA | GAATGGGACT | CAGAGACAGG | 173040 |
| AGGGCAGGAG | AAGATCAGAG | AAAAACTTTG | GCTTCTGCGG | TCTTTATTTT | GGGGTATTGT | 173100 |
| TTTCTGAGTT | CCAACAAACC | CCAAGGACCT | ACAAAGACTG | CATACTTTTT | TTTTCCTTTT | 173160 |
| TATTAATTGT | GAGATAACCA | CAGCATAGGC | AATTTGTTTT | TTGTTTTTGT | TTTTGAGACA | 173220 |
| GGATTTTGCA | TTGTTGCCCA | GGCTGGAGTG | CAGTGGCATA | ATCATAGCTC | ACTGCGTCCC | 173280 |
| CAAACTTCTA | GGCTCAAGAG | ATCCTCCAG | CTTAGCCACA | ACTGAGAGGT | GCTACTAGCA | 173340 |
| TTTAGTGAGT | AGAGAACAGA | TATGACTAGA | GGTTCATTAA | GTGTTTTGAG | CCTTTACAGC | 173400 |
| TTCAAAATTG | TCTTTGCTAA | CCCCTAACTT | TTGGATGCTA | CAGAGGGCCC | CTGGAGTATC | 173460 |
| CAAAGGAGAG | GTAAACAGGA | TCATTTGACA | CGTTTAGTTA | TATAGGATTG | TTGAAATAAG | 173520 |
| GTGATATTTG | ATCTTCAGGT | CATATTTCAG | TGAAAACTGT | GAATGTGTGT | TCCAAAATTA | 173580 |
| TAGGGGATTT | CTAGAGTTCT | GATATCTGAG | TTTGTGTCAT | CAGTTATAAT | TAGAGTTATT | 173640 |
| GTGTTAGGCT | ATTGTAAATC | ACAGAGGTGA | CTAAATTTCT | TTGTCAATTG | TGTTTTTGAC | 173700 |
| TGTGACTACC | CTAGGACATT | TTAACATTCA | TAGACAAATG | TTGTCTTGTT | TTGAAACTCT | 173760 |
| GCAAAGAATG | GATTATAACC | CTCAATTGCA | GGTTTCTGAT | AACTTTGAAG | ATTGTGAACA | 173820 |
| GGAGTTAACT | AGGTGAGCTG | AACTATTGGA | AAACTAATCT | TCTTGACTCT | TGCCTCTGTA | 173880 |
| CCTAATTCTT | CCTGGATGCA | GGACAAGAAC | TCAGGCAAAG | GTGCTGCAGC | ATAAAGTCTG | 173940 |
| GCCAGAGAAA | CTGACACTCC | AGAGGTTTTG | TAACAATATT | TTATGTTAAA | TAATTTATAC | 174000 |
| GTATTTCCTA | TTCTAAGCAT | TTCAAGTGAT | TGTAAAAACT | CAACTCATGA | AAACTTATAG | 174060 |
| CTGAGATGAT | GTATCCTGTG | ATTTTTAACT | CAACTTTATA | CCAATCTAAG | TTGATTAGCA | 174120 |
| TTCTTACAAA | GTTAAGAAG | TTAAGATTTG | CCATATTAAG | TATTGTCTTA | AGATTTTAA | 174180 |
| GAATTGAAAA | ATTTGGAGCA | GTTTTGTTCA | TTAGTCAATT | GGATACTTTA | AAAGTCCAGT | 174240 |
| ATGTCAGATT | TAAAAATTGC | AATTTATAAG | TTTTCTTCTT | AAAGTTCGTC | AAATTGCAAA | 174300 |
| AGCCTTGCCA | AAAATGAATG | TTAAAAATTT | GGTAGATTAT | TTGTTCTATG | GGTTCTATGG | 174360 |
| GAAAAAATTG | GTAGATTAAT | AAATGCCAAT | AGTAAGCATT | GTAAATTGAA | TTAAAAGTT | 174420 |
| TAAGGAAGAG | CTATTAATTT | AATTTTGTCA | TAATAATGAA | TTGAATGTTG | TTTTTAAGT | 174480 |
| ACCATAGTAC | TTGCTGAATG | ATCTTTCTGT | ATGGAAAGG | ACATAAAAAT | GCACATTGGT | 174540 |
| AACATCAACT | CTATTTCAGC | GGCGGGATTG | TGGGGTGAGC | TTATCTCCAG | GTTTGGGAAG | 174600 |
| GATGTGTTGT | ATCATCTGCC | TCTTGTGTGT | GTACTACCTG | CCATTGCTGC | TTGGCCACCA | 174660 |

| | | | | | | |
|---|---|---|---|---|---|---|
| GCATCCATCT | TGGTGAGTCC | TGTCTCCCTC | TAAAAGACTC | GAGCTGTGCT | GTTCAATCCA | 174720 |
| GTAGCCCCTA | GCTACATGTA | GCTATTGTAA | TGAATTAAAA | TTAAGTAAAA | TTAAACATTC | 174780 |
| TGCTCCTCAG | ACACCAGTCA | CATTTCAAGT | GCACAATAGT | CACAAGTGGC | CAGTAGCTAG | 174840 |
| TTTTGAACAG | TGTGGAAAGA | TTTCTGTCAT | CACAGAGCAT | TCTATTATCA | CGTTGTAAAG | 174900 |
| CATTCTCTAG | CTCTTGCAAA | CTTGTCAGAT | CCCTTAAAAG | TTCTTAAAAA | TAATTCATCA | 174960 |
| TTCGAATTTT | GCTCAGACTA | ATTTTAGGG | AAGTCTTTTT | CTGGAGGCGT | GGACTTGTGA | 175020 |
| TCTCCATAAT | TCATCCCTTC | TACTATGTTA | GTTACCTTGA | GCTGCTGTAA | TAAATACTA | 175080 |
| TAGACTTAGT | CGCTAAAAAA | AAAATAACTT | TCTCACAGTT | CTGGAAGCTC | AGAAGTCCAA | 175140 |
| GATCCAGGTG | CTGGCCAATT | CAGTTTCTAG | GTGAACGCTC | TCTTCCTGAC | TTGTTGGTGG | 175200 |
| CAGCAGCATT | CTCACTATGT | GCTCATGTGG | TGTCCTTTTT | GTGCTTGTAG | GGCTTAGGCA | 175260 |
| GTGGAGAGAA | GGAGGAGAGA | AAAGAGTTTC | ACTGTTTTCT | CCTTTTCCCG | AGACAGTTTT | 175320 |
| TGTGTAGCCC | AGGTGGACAG | CAATGGCTCA | CTGCAGCTTC | TTCCTGGGGT | CAAGCAATCT | 175380 |
| TCCCACTTCA | GCTTCCAGAG | TAGCTGGAGC | TTCAGATGTG | TACCACCACA | CCCAGTTCAT | 175440 |
| TTTTAAATT | TTTAGAAGTT | GGGGGTCTCA | CTATTTGTC | CAAGCTGGTC | TTGAACTCCT | 175500 |
| GGGCTAAAGC | GAGCCTCCTG | CTTCAGCCTC | TCATAGTGTT | GGAATTACAG | GCATCAGCTG | 175560 |
| CAGCACCTGG | CTCTATTGTC | TTTTTTTTT | TTTTTTTGA | GATGGAGTCT | CTATCACCCA | 175620 |
| GGCTAGAGTA | CAGTGGTGTG | ATCTCACTGC | AACTTCCACC | TCCTGGTTTC | AAGGGATTCT | 175680 |
| CCTGCCTCAG | CCTCCCAGGT | AGCTGGGAGT | ACAAGCGTGC | ACCACCACAC | CTGGCCAATT | 175740 |
| TTTGTATTTT | TAGTAGACAT | GGGGTTTTAC | CATGTTGGCC | AGGCTGGTCT | CAAACTCCCA | 175800 |
| ACCTCAGGTG | ATCCATCCAC | CTCAGCCTCC | CAAAGTGCTG | GGATTACAGG | CATGAGCCAC | 175860 |
| TGCACCTGGC | CTGTTGTCTC | TTTTAATAAG | GGCATGAATT | TCATCATGAG | AGACACATCC | 175920 |
| TGATGAGTTT | GTCTAAATAT | AATGACTTCC | CAAACGCCCC | AGCTCCAAGT | ACCATCACAC | 175980 |
| TGGGGGTTAG | GGTTTCAACA | TATGAATTTT | GCGACGGGGA | GTCAATTCAG | TCCATAGTAC | 176040 |
| CTACTGTATT | AGTTTTCTGG | GGCTGCAGTA | ACAAAGTACC | TCAAACTCGT | TGGCTTAACA | 176100 |
| ACAGATATTT | ATCGTCACAC | AGTCCTGGAA | GCTGGAAGTC | TGAAATCAAA | GTATCATCAG | 176160 |
| GTTTGATTCC | TTCTGAAGGC | AATGAGGGAT | AATCTGTTCC | AGGTTTCTCT | CCCAGCTTCT | 176220 |
| GGTATCCCCA | GACTCATTGC | TTGACTTGAA | TGGTGATTCT | CCCTGTGTCT | ACTCACCACA | 176280 |
| TTTTCTCTCT | ATAGGTGTCA | GTCTCTGTGT | ATGACATTTC | TCCTTTTTAT | AAGGACACCC | 176340 |
| TTTATGTTGG | GTTAGAGCCC | ACTCTTATCT | TAACTGATGA | AGTGCAAAGA | CCCTATTTCC | 176400 |
| AAATAAGGCC | ACATTCACAG | GTCCTGATAC | AGGAGGGGA | AAGTGCTGGG | AAGGGAAGGG | 176460 |
| CATGGTCCCT | TTAAATGATA | TGGAAGTGGG | GAAGGGAAGG | GCGTGGTCCC | CGGCTAGGGC | 176520 |
| TCCACCCCCA | GGCCTGTGCC | CAGGGACCAC | GGTGAGGACA | GGCATTTTG | TTTTCCTGCC | 176580 |
| CAAATGTTGC | ATTTCCCAAG | ACCTCCCCTG | GCCTGCCACA | AGACACGAAT | AGCTGGACGT | 176640 |
| CCAGGGGAGC | ACACTGGCAG | AAGAGCACAC | AACAAACGTT | TGCCTGGCAA | AATGAGGCGG | 176700 |
| AATTTGACTG | GGGTGGTTGG | AGGAGAGCCT | GGGCCACTGA | GTGGCTGACT | CCAAGGGAAA | 176760 |
| ACTTTCCCAC | TCCATCCACT | TTTGGCTTTG | CCCAACTGCT | GAGAGCTACC | TCCACTTAAT | 176820 |
| AAAACCTTGC | ACTCTTTCTC | TAAGCCCAGG | TGTGGTCTGA | TTTATTCCGG | TACACCAAGG | 176880 |
| CAAGAACCTG | GGATACAGAA | AGCCTTCTTC | TGTCCTTGGG | ACAAGGTAGA | CGGTCTAATT | 176940 |
| GAGTTGGTTA | ACACCAGCTG | CCTATAAATG | GCAAAACTAA | AAGAGCACCC | TGTAACACAC | 177000 |
| ACCCACTGTG | GCTTCAGGAG | CTGTAAACAT | TCAACCCTAG | ACACTGTGGT | GGGGTCATGG | 177060 |

| | | | | | | |
|---|---|---|---|---|---|---|
| GGTTGGAGAC | CCACAACCTG | CCCGTCTTAA | TGTTCCCCTA | GAGGTTTGAG | CAGCCAGGCA | 177120 |
| CTGAAGAAAT | TAGCCACACT | CCTATCACAT | GCCATGCGAG | CGGGACAAGG | GAACTTTTCC | 177180 |
| CATTTCAGTA | CTGGTGGTTA | GGACTTCAAC | AACTTTATTT | TTGTGGGAAT | GCATACTTCA | 177240 |
| ACCCATATTA | TGAGGGTTCC | TAGAATGTGG | ACTGCTGAGG | CTGAAGCACT | ACCTAAGTGC | 177300 |
| CTGAGGCCAG | CCTGCAGTTG | GTTTCTGGCT | CTCATGAGTT | AGCTAACATC | TCGGGAGAGA | 177360 |
| GGAAGACAGG | CCTAGGAAGA | GCAGAGCCCA | CGATTCATTC | TTCATTCCAC | CTCTGCTCTT | 177420 |
| CAGAATCTCC | TTCAGTCTAT | GTGATGAGCC | ATCAGACCTC | TTGGTGGGAA | ATGGTGCTGC | 177480 |
| CGTGCCTAGC | CCTTTTCGAT | TGTGCTACCA | TGCTGAGATT | ACTGAGGGAC | CAGGAAGGCC | 177540 |
| TGGACTCAGA | CCATATAGGG | TGCCACCCTA | GTGGGAATGG | AACCTGTCAG | TGCTGGGTGA | 177600 |
| ATGTGACCGT | CCCATGAGGA | GAAGACAGAT | ACTCTTGCCA | AGCTGAGCAT | GGAGACCTGA | 177660 |
| TGGACACTC | ATTATCATGA | GGGGATGAAG | ATCCAGGCTT | CCAAAGTTGG | TACCACAGGG | 177720 |
| TGGCTATGGC | ATGAACAGGG | GGTTAGGATG | AAGGACCCAG | AATCTAACAT | GCTGGAGAGG | 177780 |
| TAGGGAAAGG | AGTCAGAAAT | TCAGTCTTGT | TGAACCCTAA | ATATTGCATC | TCTCTCTCTC | 177840 |
| TTTATTTTTT | TTTTCTGGAG | ATGGGGGTCT | GGCTCTATCA | TCCAGGCTGG | GGTGTAGTGG | 177900 |
| CATGATCTCT | GCTCACTGCA | GTCTCCGCCT | TCTGGGTTCA | AGAGATCCTC | CCACCTCAGC | 177960 |
| TTCCTGAGTA | GCTGGGACTA | CAGGTGCGCG | CCACCACTCC | CAGCTCATTT | TTGTACGTTT | 178020 |
| TTGTAGAGAC | ACGGTCTCAC | CATGTTGTCC | AGACTGGTCT | CGATCTCCTG | AGCTTAAGCG | 178080 |
| ATCTGTCGCC | TCGGCCTCCC | AAGAAGGATT | GGGATTACAG | GCCTGAGCC | ACTGTGACCA | 178140 |
| GCCAACATTG | CATCTAATTT | TAGGGTATTC | ATCTGACTTT | CCTGAACACT | GCTTCTTGGG | 178200 |
| TGCTCATTTT | AGCAGGCATT | TGGCCATAGG | TAGATTTAAA | GTTTGGTGG | GTTTGTTGT | 178260 |
| TGTTGTTGAG | ACAAAGTGTC | ACTCTGTTGC | CCAGGCTGGA | GTGCAGTGGC | AAGATCTCAG | 178320 |
| CTAACTTCAA | CCTCCATCAC | TGTGCTTCAA | GTGAGTCTCC | TGCCTCAGGC | TCCCGAGTAG | 178380 |
| CTGGGATGAC | AGGTGTGTGC | CACCATGCCC | TGCTAATTTT | TTATATTTTT | AGTAGAGATG | 178440 |
| GGGTTTCGCC | ATGTTGGCCA | GGCTGGTCTG | GAACTTCTGA | CCTCAGATGA | TCTGCCCGCC | 178500 |
| TCAGCCTCCC | AAAGTGCTGG | GATTACAGGT | GTGAGCCACA | ACCCCTGGCC | AACGTTTTCT | 178560 |
| GAAAAGCTA | TTCTAATCAG | GTAGGAAAGA | TGGGAAGCGG | GGTGGCGGGG | TGTACTTTTT | 178620 |
| TCTGCATATT | CAGTTGCAGG | GTCCCAGACC | AGGGAACAAT | CTTCAATCTC | TTACCTTCAA | 178680 |
| TCTCCCTTCA | TGGAAGTCAG | TGCTCAGCCT | GGCCATTTAC | TGTGTGCAGT | AGGTGTGATG | 178740 |
| TAGAAAGCCT | CTAAACCTCC | ATGCCTACCT | GCCAGGAACA | ATATACACAA | AGGTGTGTGT | 178800 |
| GTGTGTGTGT | GTGTGTGTGT | ATCTTACGGA | TTCTTCCACG | TAACTATGTG | GACATCTAAT | 178860 |
| CCATTGCTTC | CAACTCTATA | TTGTGCAGTG | ACTTCATTTT | ACCTCCACCT | CTCTCAGTGA | 178920 |
| AGGATATCAG | TCAGCCCACA | CTTTCCTGTC | ACCTTTATGG | GATATGTTTG | AGATGATATT | 178980 |
| TGGAAAATAT | TCCCAGGGAG | TGGGCACTCC | CATCAGCAGT | GTATGAGGAT | TCCTGAGTCT | 179040 |
| CCATATCCAC | ACCAATACTG | AGCATTATTC | AGCTCTCTAA | TTTGTTAATG | CTCTCTTTA | 179100 |
| AATGCAAAAG | GACACATCAC | TTTACCTTTC | TTTCATTACC | AAGTGCTTTG | GATTTTCCTG | 179160 |
| TATCTAAATT | TCTTGTTCAT | TTATTTCATA | TATATATATA | TATATATATA | TATATATATA | 179220 |
| TATATATATA | ATTTTTTTTT | TTTTGAGAC | AGAGTCTCAC | ACTGTCACCC | AGGCTGGAGT | 179280 |
| GCAATGGTGT | GATCTCAGCT | CACTGCAACC | TCTGCCTCCT | GAGTTTAAGT | GATTCTCCTG | 179340 |
| CCTCAGCCTC | CCAAGTAGCT | GGGATTATAG | GCACCCACCA | CCACGCCCGG | CTAATTTTTT | 179400 |
| GTATTTTTTG | TAGAGATGGG | GTTTCACAAT | GTTGGCCAGC | CTGGTCTCAA | ACTCCTGATC | 179460 |

| | | | | | | |
|---|---|---|---|---|---|---|
| GGCCCGCCCT | GGCCTCCCAA | AGCGCTGGGA | TTACTGGCAT | GAGCCACCGC | GCCCGGCCTC | 179520 |
| ATACATTTTT | TATGTGGAGT | TTCTGTTTTG | TTCTTCTTGG | CCTTGTGCAT | TCTAATTACT | 179580 |
| CATCCTTTCG | TCTGATTCAG | ACATTTAATT | CTCTACCATC | CTTACAGCAG | TGTCTTAACT | 179640 |
| TTATCCATGG | GATCCTTCAT | TGAACCGGAA | TTCTTAATTT | TGACACAAAC | AAATTTATCA | 179700 |
| ATTTCTTTTT | TGTGTGTGTT | TTTTTTTTCT | GTGTGTGGTT | TTTGTTTTTC | ACATTCTGA | 179760 |
| GTATGACCTA | GATTTATCCT | TTGATAACTT | CTTCTCTCTT | CCCCATTTTC | CTCCACTGGA | 179820 |
| GGTCAGCTAT | ATGTGTGTGA | GAGGGTTAGG | TATATGTGGA | TATATAGAGA | AAGTTTAGGT | 179880 |
| ATACATATGT | GGAGAGGTCA | GATAAATATG | TATATATGGG | AGAGATATTG | GGTATATATT | 179940 |
| TTGGGGAGGG | GAGGTCAGGT | ATATGTGGAC | ATATGGGGAG | GGGAGACCAC | AGCTCTCCTG | 180000 |
| GAGTCACCCT | CTTCCTCTTC | CCTTCTGGGC | AGGTAACGGT | GGGGAGTGAG | AGGGTGTTCC | 180060 |
| TCCCTTCTTA | TTATTAGCCC | CTGGGTACTT | TAGGGTCTCT | AGTGGTTATT | TTTCACAGAA | 180120 |
| TTTTAACTGA | TAACTAATGA | ACAAATGTTT | TCCCCACAGA | AATATCTTTA | CGCCTTTTAC | 180180 |
| AATCATTTTT | ATTTTCTATG | CCATAACTTT | ATTAATATTT | GCCAATTTAC | TTGGGGTAGG | 180240 |
| ACTTTGAAAA | TTTTGTTTAA | ATTAAGGGAG | GAGACCACCC | CTCATATTGT | CTTATGCCCA | 180300 |
| ATTTCTGCCT | CCAAAGAAAG | AAAAAGTAAA | AATTAAAAGG | GAGAAATGAA | ATCCACAGGC | 180360 |
| AAACAGCCCG | GCACCGCACC | CTGGGTCTGG | TTAAAGATCG | ACCTTTGACC | TAACAGGTTA | 180420 |
| TGTTATCTAT | AGATTCCAGA | CATTGTATGG | AAAAGCATTG | TGAAAATCCC | TGTGCTGTTC | 180480 |
| TGTTCTGTTC | TGATTACTGA | TGCATGCAGC | CCCAGTCACG | TACCCGCTGC | TTGCTCAATC | 180540 |
| AATCACGACC | CTCTCATGCA | GACCCCCTTA | GAGTTGTAAG | CCCTTAAAAG | GGACAGGAAT | 180600 |
| TGCTCACTCA | GGGAGCTGGT | TTTTGGAGAC | AGAGGTGATT | AACGGACGGT | CAAGGCAGCC | 180660 |
| CCTTAGGCGA | CTTAGGCCTG | CCCTGTGGAG | CATCCCTACG | GGGAACTCCA | GCCAGTTTGA | 180720 |
| GCGACACAGA | TCTGGAGAGC | GCTCCCAGGT | AGGCAATTGC | CCCGGTGGAA | CGCCTCACCA | 180780 |
| GAGCAGCACG | TGGCAGGCCC | TCGTGGAGGA | TCAACGCAGT | GGCTGAACAC | CGGGAAGGAA | 180840 |
| CTGGCACTTT | GTTGTCAGGG | CATATTCCAA | AAGCATTAAG | GCCTTCCTAT | CAAAAATCCT | 180900 |
| TAACCCAGTA | ACCCGCGGAT | GGCCCAAATG | CATTCAATCT | GTAGCGGCAA | CTGCTTTGCT | 180960 |
| AACAGAAGAA | AGTAAAAAAA | TAACTTTTAC | AGGAAACCTC | ATTGTGAGCA | CACCTCACCG | 181020 |
| GTTCAGAAGT | ATCCTAAGGA | AAAAGAAAA | AAGAAGATGA | TTTAACATTA | ACCACTGAAA | 181080 |
| ATTCTCTTAA | CCCGGCAGGT | TTCCTAACAG | GGGATCTAAA | TCTTAATTAC | CATACAAAGC | 181140 |
| TCTGACCAGA | CCTAGGGGAT | TCCCTTCAGG | ACAGGAGGAT | AGATGGTTCT | TCCCAGGTAA | 181200 |
| TTAAAAAAAA | AAAAAAGCCA | TCTATACCAA | TTCTAAGTTA | ATTTGGACTA | AATAAGGTCT | 181260 |
| TATTAATAGC | AAAGGATAAT | TGAAATCCCA | AACTTACAAG | GTTTTCAACA | AAAGTAAAGT | 181320 |
| TTGCTAAAAG | TTAACAGTGT | AACATGTATT | ATAGTAACTT | CTAATCTTGT | GGCCTTAGAC | 181380 |
| AGTCTAGTCC | ACAGACATAA | AAGAAGTTCG | CTTTGGAAAA | GAATGGTTAT | CATCCTCGGA | 181440 |
| AAAAAAAAAA | AGGAAATAAA | GAGGAGGCAG | AATTTATATA | AAAAGAATG | TTGTATGGAA | 181500 |
| AATCCTTGTC | CTGAGATAAA | TTAACTAGTT | GTTAAAGAA | AGGGATGTTT | GCAATAAGTC | 181560 |
| AGAAAGTTGA | GGCATGTCGA | AGAATTGTCT | GTGAAAGTCA | TGAAAAAAAT | GTGTGTTAGA | 181620 |
| AAAATAAATT | TATGTAAGAA | ATGTTGTATA | ATTTAAAAGT | AATTAGGCCT | CCTTCTAAAT | 181680 |
| GTAAAACTAT | TGAATAAACA | GTTTATGTGC | AAGGTATGTA | AGGAAAGTAA | AATATACCTT | 181740 |
| TGGTAAAAGG | ATTATGAGGA | TGCATAAGAA | TGTGGATTTT | TACCTACATT | AAAAGGTTAC | 181800 |
| AAAAATTGTT | TTGAAGGTTT | AAGCAAGTTT | TGAAACCTTA | ATTGTAAAGA | AAATTCTGTG | 181860 |

| | | | | | | |
|---|---|---|---|---|---|---|
| TCTAAACATA | TTGGCTAAAG | TTAAGGGGTA | TCATACAGTT | TTTCTGTGAA | CTGAACATTA | 181920 |
| AAATAAAAAC | ACAACGGGTT | TTTCTTAAAG | CACTAACCTG | TTCTTTAACA | AAAATTATAA | 181980 |
| AAGGTTAAAG | AAAAGTCTAT | AAAAATCTTA | CCTTATGGTC | AGACATTAAA | AATCAAATAA | 182040 |
| ATATGTCTAC | AGAGTTTTAT | TAAAACTAAG | TTTAACATTA | ATAACACACC | AATATAAAGG | 182100 |
| TGAAATCTAG | CTTATCTGGT | ATAAACATAC | AAGAAGCGTT | GTCAAATATA | AAATGGCATT | 182160 |
| TGACTTTCTT | TGGTCTAAAA | ACTAATAAAA | ATAGGTGCTA | AAGGAAATTT | CTCAGTAAGA | 182220 |
| AGGCACCAAG | GACTATAAAG | TCCACTGCTG | ATGTCCCCAC | ATTTAAAACA | AAAGGTCAAC | 182280 |
| TTCTTAAAAG | TTATATACTT | GGTTTATCTT | CCACTTTCCT | TTCCCTCAAA | ACTAAAAGTC | 182340 |
| TTTTAGCACA | TGTACCACCC | CTAGAATTTT | CTGTAAACCA | GCACCAGCCT | GAAGATCATG | 182400 |
| TTCTCATCAA | AGGGTGGAAA | GAAGGAAAAC | TTGAGCCAGC | CTAGGAAGGA | CCCTACCTTG | 182460 |
| TGCTGCTAAC | CACCGAGACT | GTTGTTCATA | CGGTGAAAAA | GGGATGGACT | CATCACACCC | 182520 |
| GAGTCAAGAA | AGTGCCACCC | CCTCCAGAGT | CATGGGCCAT | AGTCCCAGGG | GAAAACCCTA | 182580 |
| CCAAACTAAA | GCTAAGAAAA | ATTAACTCC | TTCATCTATT | CTATTACTCT | TTCTTCTTCC | 182640 |
| CTCACTCTAT | TTCTGACCAT | CTAGTTATTA | ACATAACCAA | GTCAATTTTG | CCTCAAACTA | 182700 |
| TTGAATTTAA | TGCTTGCCTT | GTTATACCCT | GTGGGACTT | GCCAAGTCGA | AGACATCTCT | 182760 |
| GTACTTCAGA | AAAGTACCTC | TGTCCCTCCT | GACTCCTC | AGACTGAGCC | TTAGTAAACT | 182820 |
| GAGACCATTT | ATTCCAGAGA | GATTTCAATA | AAGACCCCAG | TGTCAACGAG | GAGTCTTGCC | 182880 |
| CCCCGATGTA | GAGCTTTTAT | GCCATAGTTG | GTCGAATGTT | GTGTGGACCA | CTAAAGAGCA | 182940 |
| AGGATGGACT | GCCCCAACCG | GTTTTTGTAA | TTTCCTAAAA | TCATACATTC | ATTTTACTAG | 183000 |
| AGGGTCATAG | AAGTTAAAGA | CTTAAAACAA | ACTTTGATAA | TTAAGCAGGA | TACCAAGATG | 183060 |
| CAAATGCCCA | GTTGGAATGG | ATCAAATATT | CTGTCCACAC | ATTAAACAAA | ACCAATTGTT | 183120 |
| ATGCTTGTGC | ACATGGCAGG | CCAGAGGGCC | AGATTATCCC | CTTTCCACTA | AGGTGGTCCT | 183180 |
| CCTGTTGACC | AGGCATGGGC | TGCATGGTAA | CTGTTTTCCA | GGATTCTACA | GCCTGGAGTA | 183240 |
| ATAAGTCGTG | CCAAGCTCTC | TCTGCTATAT | CCCAAAGTCC | AGCACCCTGC | AGGTCAACCC | 183300 |
| CTGAGGGCCA | TCCAGCTTCC | ATCTCCCAAA | ACTAAGTTCA | CTTCTTGTCT | CTCATGACAG | 183360 |
| GGAGGAAACT | TAGCATTCCT | TGGAGACCTG | AAGGGATGCA | GTGAGCTTAA | GAATTTTCAG | 183420 |
| GAGCTTCTCA | ATCAGTCAGC | CTTTGTTCAT | CCCCAAGCGG | ATGTGTGGTG | GTATTGTGGT | 183480 |
| GGACCTTTAC | TGGGCACTCT | GCCAAATAAC | TGGAGCGGCA | CTTGTACTTT | AGTCCAATTG | 183540 |
| GCTATCCCTT | TCACCCTAGC | ATTTCATCAA | CCAGAGGGAG | GAAAAATAAG | ACATCGTAAA | 183600 |
| GCAAGAGAAG | ACCCTTATGT | GTCTTTCAAC | TCTCACATCT | ATTTAGATGC | AATTGGAGTC | 183660 |
| CCACAGGGAA | TAGCAGATCA | ATTTAAATCC | CAAAATCAAA | TAGCTGCAGG | ATTTGAGTCA | 183720 |
| ATATTTGGT | GGGTGACAGT | TAATAAAAAT | GTAGATTGGA | TAAACTACAT | CTATTACAAC | 183780 |
| CAACAGCAAT | GAGTTTTTCA | TGAGTTAAAA | GAAAAACTCA | TGTCGGCCCC | AGCCCTGGGG | 183840 |
| CTACCTGACC | TGACAAAACC | CTTTACACTC | TATGTGTCAG | AAAGAGAAAA | AATGGCGGTT | 183900 |
| GGAGTTTTGA | CCCAGACTGT | GGGGCCCTGG | CCGAGGCTGG | GCCTCCAAAC | AACTAGATGG | 183960 |
| AGTTTCTAAG | GGTTGGCCTC | CATGCTTAAG | AGCCTTGGCA | GCAACAGCCC | TGCTAGCACA | 184020 |
| AGAGGCAGAT | AAGCTAACTC | TTGGACAAAA | CCTAAACTTA | AAGGCCCTCC | ATGCTGTGGT | 184080 |
| GACTTTAATA | AATACATCAT | TGGCTAACAA | ATGCTAGATT | AACCAAGTAC | CAAAGTTTGC | 184140 |
| TATGTGAAAA | TCCCTGCATA | ACCATTGAAA | TTTGCAACAC | CCTAAAACCT | GCCACCTTGC | 184200 |
| TCCTGGTATC | AGAAAGCCCA | GTTGAAAGTG | ACTGAGTAGA | GGTATTGGAC | TCAGTTAATT | 184260 |

```
CTAGTGGGCC CAACTTCCAA GACCATCCTT GAACATCAGT AGACTGTGAG CTGTACGTGG 184320
CAGCTTCGCC AACGCCTGCA AAGTGACTGA AGAAGACAAC AAGCCCTGCT CCAGTCACAC 184380
CCGGAAGCTG ACTGGTCCAT GCATGGCCGA AACATGAGAA AACTCATCAA GGGACTCATT 184440
TTCCTTAAAA TTTGGACTTG CACAGTAAAG ACTTCAACTA ACCTTCCTCA GACTGAGGGC 184500
TGTTCCCAGT GTATACATCA AGTCACTGAG GTAGGACAAA AAGTTGCTAC AGTCTTATTA 184560
TTTTATGGTT ATTATAAGTG TACAAAGACT CTAAAAATAA CTTGTTTGTA TAATGCTATT 184620
CTATACAAGG TAGGTAGCCC AAGAAATGAC CAACCTGATG TGTGTTATGA CCCATCTGAG 184680
CCTCCCACGA CCACAGTTTT TGAAATAAGA TTGAGGACTG AGGACTGGTG GGGGTTCATA 184740
AACGATACGA GTAAAGTGTT AGCCAAAACA GAAGAAAAAG GAATGCCCAA ACAAGTCACC 184800
TTGAAATTTG ATGCCTGTGC TGTCATTAAT AGTAATAAGT TAGAAATAGG ATGTGGTTCT 184860
GTTCATTAGG AAAGAGGCTA TATGGCAGAA AATAAGTACG CTTGTCATGA ATTAAGACTG 184920
CGTGGAAATA AATGTAGATA CTGGTCTTGT GTCATTTAGG CAACTTGGTT AAAAAATAAA 184980
AAGAATCCTG TCCACCTTCA GAAAGGGAAA AGTGGCCCTT CCTGTACCAG TGGTCAGTGT 185040
AACCCCTTAG AACTAGTAAT AACCAACCCC CTTGATTCTC ACTGGAAAAA AGGGGATCGT 185100
GTAACCTTAG AAATAGTTGG GGCTGGACTG GATCCTTGAG TAAATATGGT GGTTTGAGGA 185160
GAAGTTTATA AATGCTCCCC TGAGCCAGTA TTTCAAACCT TCTTATGATG AACTGAATGT 185220
GCCAGTACTA GAAATTCCAG GAAAAACAAG AAATTTGTTT TTGCAATTAG CTGAGCATGT 185280
AGCCCAGTCT CTCAATGTCA CTTCATGTTA TGTATGTATG TGGAGGAACT GTAATGGGAG 185340
ATCAATGGCC ATGGGAAGCA CGAGAATTAG TACCTACAGA CCCAGTTCCT GATAAATTCC 185400
CAGCTCAAAA GACTCACCCT GATAACTTCT GGGTCCTAAA AGCCTCAATC ATTAGACAAT 185460
ACTGTATAGC AAAAGTGGGG AAGGACTTCA CCCTTCCTGT GGGAAGACTC AGCTGCCTTG 185520
GGCAAAAACT GTATAATAGT ACTATAAAAA CAGCCACCTA GTGGAGTTCA AACCACACTA 185580
AGAAAAATCT ATTTAGTAAA TTCCCAAAGT TGCAAACTGT GTGGACCCAC CCAGAGTCCC 185640
ACCGGGACTG GACAGCCCCC ACTGGATTAT ACTGGATATG TGGGCATACA GCTTATGCCA 185700
AATTACCTGA CCAGTGGGCA GGTAGTTGTG TTATTGACAC TACTAAACCA TCTTTCTTCC 185760
TACTGCCCAT AAAGACAGGC AAACTCCTGG GCTTCCCCTG TATATGCTTC CCGCAAAAAA 185820
AAAAAAAAAA AAAAAAAAAA AAAAAAAAA AGCATAGCTA TAGAAAATTG GAAAATAAT 185880
GAATGGCCCC CTGAGAGAAT CATACAATAT TATGGGCCTG CTACTTGGGC ACAAGACGGC 185940
TTGTGGGGAT ATGGGACCCC CATTTACATG CTCAACTGAA TCATACGGTT ACAAGCTGTC 186000
TTAGAAATAA TTACTAATAA GACCAGCAGA GCCCTGACTA CTGTGGCCTG GCAAGAAACT 186060
CAGATGCAAA ATGCTATCTA TCCAAAATGG ATTGGCTCTC GACTACTTGC TAGCAACTGA 186120
AGGAGGGGTC TGTAGGAAAT TTAACCTTAC TAATTGCTGT CTACACATAG ATGATTAAGG 186180
GCAAGTAGTT GAAGACATAG TTAGAAATAT GACAAAAGTG GCACATGTGC CCATGTAGGT 186240
GTGGTATGGA TTTGTTTCTG GGGCCATGTT TGAAAATGG TTCCGAGTGC TAAGAAGATT 186300
TAAAACTCTT ATAATAGGAG TTATAATATT AATAGAAACC TGCTTACTGC TTCCTTGTTT 186360
GCTACCTGTA CTTCTCCAAA TGATAAAAAG CTTCATCACT ACCTTAGCTC ACCAAAATGC 186420
TTCAGCACAA GTGTACTATA TGAATCATTA TCAATCTGTC TTTCAAGAAG ACATAGGTAG 186480
TGAGAATAAA AGTGAGAACT CCCACTAATG AGTGAGATTC TCAAGGGGG TGAATAAGTG 186540
AGGCGACCAC CCCTCATATT GTCTTATGCC CAATTTCTGC CTCCAAAGAA AGAAAAAGTA 186600
AAAGCTAAAA GGCAGAAATG AAATCCACAG GCAGACAGCC TGGTGTTGCA CCCTGGGTCT 186660
```

```
GGTTAAAGAT  TGACCCCCGA  CCTAACCGGT  TATGTTATCT  ATAGATTCCA  GACATTGTGT  186720
GGAAAAACAC  TGTGAAAATC  CCTGTTCTGT  TCTGATTACT  GGTGCATGCA  GCTGCCAGTC  186780
ACATACCCCC  ACTTGCTCAG  TCGATCATGA  CCCTCTCACA  CAGACCCCCT  TAGAGTTGCA  186840
AGCCCTTAAA  AGGGACAGGA  ATTGCTCACT  CAGGGAGCTC  GGTTTTTGGA  GATGTGAGTC  186900
TTGCCAAAGC  TCCCAGCTGA  ATAAAGCCCT  TCCTTCTTTA  ACTCAGTGTC  TGAGGGGTTT  186960
TGTCTGTAGC  TTGTCCTGCT  ACAAAATAA   GTGTTAAACA  TGAGTTTTAT  ATTACCTCAT  187020
AGGTGGAAGA  AGACAGGCCA  AAAAGCTGT   TTAACAACA   ACAAAATGCA  CAAATATTTA  187080
TACTAACAAG  ACAGATATCC  ATTGCAGTAT  GACACGAGAA  ACAAATAAAT  GAGACAAGCA  187140
GTCAATTCAG  ACATTTTAGG  AAGTGATTTT  TACAGAACAT  AGTGACAATT  GCTGAGATCT  187200
GGTAGCCTTG  CAAGATTCCT  TTGTTATAAT  AAAAATAACA  TTGGCAAAGA  CCATTTTATG  187260
ATGCAGACTT  CTGCTTTTTT  AAAGTTTGGG  GGGAAGGGGA  AACATTTTTA  TTCTATAATG  187320
CTGAAATTTC  ATTTTTCTTT  TCTCTTTTTT  AAGACCAAGT  CTTGCTCTCT  CACCAAGGCT  187380
AGAGTGCAGT  GGCGTGATCT  CAGTTCACTG  CAACCTCCAC  CTCCGGGTT   CAAGCAATTC  187440
TCCTGCCTCA  GCCTCCTGAG  TAGCTGGGAC  TACAGGCACC  ATGCCCGGCT  AGGATAACAT  187500
TTTTTGTTTT  TAGTAGAGAT  GGGGTTTCAC  CATGTTGGCC  AGAGTAGTCT  AGAACTCCTG  187560
ACCTCAAGTG  ATCTGCCCGC  CTCATCCTCC  CGAAGTGCTG  AGATTACAGG  TGTGAGGTAC  187620
AGCATCTGGC  CTCATGCTGA  GATTTCTTTC  ATTACCAGTT  CAAACACCTT  TCACTTTTCA  187680
AGGCACAAGG  AGAGGAATTC  CATGTGTTGA  CACTGGGAGG  AAGGGTACAG  ACCTACTTAA  187740
AAGATTCAAA  ACTTCTATGA  CAGTAAAAGA  AATGTATATC  AAGTTCCTTA  GGGCTGCCGT  187800
AACAAAGTAC  TATCAACTGG  GTGGCTTAGA  ACAAAGAAA   TTTATTCTCT  CACAGTTACG  187860
TAGGCCAGTT  GAGATCAAGG  TATTATCAGG  GCCAAGATCC  CTCTGTAGCC  TCTGGGGAAG  187920
GATTCTTTCT  TGCCTGTTTC  CACTTCTAGC  AGCTTCCTGT  GTTTGGTTTG  TGGCAGCATA  187980
ACTCCAATCT  CTGCCTCCAT  CTCTACCTGG  CCATCATCCC  TCTGTGTCTG  TGAGGACCCC  188040
AGTCATTGGT  TGGAGGACTC  ACCCTATTCC  ACTATAATCT  CTTCTTAACC  AGTGAACTCA  188100
CCGTATTCCA  GATAAGGTCA  GGTTCACAGC  TACTGAGGGT  TAGGACAGAG  TATCTTTTGG  188160
GGAGATGCAA  TTCATCCCAT  AAGTGGGTGG  AAAAGGATGA  TTAACAAGTG  GTATGTGGGG  188220
ATGTATTGTT  TTGCATCTAC  GTAGCTCTCA  CCCCATTTCT  TTCCACAACA  CACATTTGTC  188280
ACTCTATTCT  TTATTAGGTT  TACAGAGAAA  AGTAGATCTT  CAACCACTTT  CCTGGGATGT  188340
GGATACAGCT  CTTTTTTTGG  AGACAGGGTC  TCATTCTGTC  ACCTAGACTG  GTGTGCAGTA  188400
GCACTATCAT  GGCTGACTAC  AGCCTCAATG  TCCCAGGCTT  AAGTGATCTT  CCCAACCTCC  188460
TGAGTGGCTG  GGACCACAAG  TGTGTGCCAC  CACACCTGAC  TAATTTTATT  TTTTAATTGT  188520
TTTGTGAAGA  CAGCATCTCC  CTATGTTCC   CAGGCTGGTC  TTGAATTCCT  GGGCTCAAGC  188580
CATCCTCCTG  CCTCGGCCTC  CCAAAGTGCT  GGGATTACAG  GCAAGAGCCT  CCATGCCTGG  188640
CCTTCAACTC  TTGACCTTAT  GAACACAGCC  CTATACCAGT  TCCCTTCATG  CATGTGCCTA  188700
TAAGCTAAAC  CCTTCCCAAG  TGTACATGAA  AATCTGAAAC  CCCAACAAAT  ATGGCCTAAT  188760
TCTAAATCTG  ACTTTCCCAG  GAGTAATTTT  TGTCATTTCC  AGCTTACCAG  CCTTTGTGAG  188820
TGTTGAATTT  CAGCATTTCT  GTTTGCTTGC  AGCAGAAGGT  GGAGCCAGGA  TAGGGTGGCT  188880
CAAGATTAGA  GTTTCTTCCT  TAACAGTTCA  GTCAACTTTT  TAATCTTGGA  TTTATAGCTT  188940
CCTACCTGCT  CTCTTAAAGG  TGAAATGATC  TATTCACCTT  CAGACCATTT  GCCCTCGGGG  189000
TCTCACTGAG  CAATCTATGG  CTTAAGTCTT  CTAAGTCTCT  TAATGGCCAA  ATACAATGGA  189060
```

```
CAATTTTCAG  GTATATCTGA  CACCATTTCT  CTGCAGCCTT  TGGCACCTAT  AACCACTCCA  189120
TGGCTTCCAC  AATGTGATTG  GTCATTTCTT  TTTTGTTTAT  ATGACAAGTT  TTTATTCTTC  189180
TTCTGCCTGT  TAAATGCGCC  TGACCCCCAG  TGTTCTGATT  TTCACTATTT  TTCTTAAAAA  189240
AAAAGTTTA   AATGAAAAAA  GTTTCTTATG  AAAATATTAA  AACATATACA  AAAATAGAAT  189300
AGACATTGAT  AATAGATCCT  AAAATTCCTA  GGGAAATTCA  GCAGACTGAG  AATAGCTAAT  189360
ATAGTCTTCC  AAAAAAAGAT  CAAATTTGAA  GTTGAGAAAC  TTCTTGAATT  CAATTTACTA  189420
AAAAGCTATA  GTAATCAAGA  CAGTGTAGTC  CTGACATAAA  GATAGGATTA  TAGTCTGGGT  189480
GTGGTGGCTC  ATGCCTGTAA  TCCCAGCACT  TTGGGAGGCT  GAGGTGGGCA  GATCACCTGA  189540
GGTCAGGAGT  TCCAGACCAG  CCTGACCAAC  ATGGTGAAAC  CCCGTCTCTA  CTAAAATAC   189600
AAAATTAAC   CAGGCATGGT  GGCAGGTACC  TGTAATCCCA  GCTGCTTGGG  AGGCTGAGGC  189660
AGGAGAATTG  CTTGAACCTG  GGAGGAGGAG  CCAGTGGCCG  GGATTGGGCC  ACTGCACTCC  189720
AACCTGGGCA  ATAGAGTGAG  GCTCTGTCAA  AAAAAAAAA   AGATAGGATT  ATAGATTATA  189780
GCATAATGGG  ATAAAATTGA  GACTCCAGAA  ATAAACTCTC  ACATTTATGG  TAGATTGATT  189840
TTTGATAAGG  GTGCCAAAAC  ACTTCAATGA  AAAAGAGTC   TTCTCAACAA  GTGATGGTGG  189900
AACAACTGAA  TAACCACATT  TTTGTTCTAT  CTGGGGCCCT  GATTCAAAAA  CCCAGGCAAA  189960
GATGGAGAGA  AATCAGAACT  CTCATACACT  GCTGATAGGA  GGATAAAATG  CTTACTTTGG  190020
AAAAGAATGT  GGCAATTCCT  CAAAAGGTTA  AACAGTGTTA  CCATATGACC  CAGCAAACCC  190080
ACTTCTAGAT  ATATAACCAA  AAGAAATCAA  AACATAAGTC  TACAAAAAA   CTTGTACATA  190140
AATGTTTATA  ACAGCACTAT  TCCCAATAGC  CATAAAGTAG  AAACAAACCA  ATGTCCATCG  190200
GCTGATGAAT  GAATAAATAA  AATATGTTGT  GGTATGTCCT  TATAATAGAT  ATTATTGGTC  190260
CATGAAAAAC  ATACATAAAA  ACATTATGCT  AAATGAAAGA  AGCCAGTCAC  GGCAAAGCAA  190320
TATATTATAT  GCCTCTATGT  ATACTAAATG  TTCCAAATAG  AAAGAAAGTA  GATTAAAGAT  190380
TGTCTAGGGC  TGGGAGGGGA  GGAGGAGGAG  AATGGAGGAA  TCTGGGAGGC  GATGAATTAA  190440
GGGTACTGAA  TTAGGGAAC   ATGGTTTCTT  TTTGGGGAGA  TAGAAATGTA  AAATTTTGGT  190500
AATGGTTGCA  CATCTCTGTA  AATATACTAA  AATCCATTAA  TTTTTGCATT  TTATTTTATT  190560
TATTTTATTT  TTGAGACGGA  GTTTCGCTCT  TGTTGCCCAG  GCTGGAGTGC  AATGGCATGA  190620
TCTCGGCTCA  CCACAACCTC  CGCCTCCCAG  GTTCAAGCGA  TTCTCCTGTC  TCAGCTTCCC  190680
GAGTAGCTGG  AATTACAGGT  GCATGCCACC  ACACCCAGCT  AATTTTTTTT  TTTTGAGATG  190740
AAGTCTTGCT  CTTGTCTCCC  ATGCTGGAGT  GTGATGGCAC  GATCTTAGCT  CACTGCAACC  190800
TACGCCTCCC  GGGTTCAAGC  GATTCTCCTG  CCTCAGCCTC  TAATGTAGCT  GGGATTACAG  190860
TTGCCTGCTA  TCACGCCCGG  CTAATTTTTG  TATTTTTAGT  AAAGACGGGG  TTTCACCATG  190920
TTGGCCAGGC  TGGTCTCGAA  CCCCTGATCT  CAGGTGATCT  GCCTTCCTCG  GCCGCCCAAA  190980
GTGCTGGGAT  TACAAGCGTG  AGCCACTGAG  CCGGGCCAAT  TTTTGCATTT  TACATAGATG  191040
AATTATATGG  TATGCTAATT  ATATCTTACC  AAAAATTGAA  AAAAGGAAT   AGTACTATCA  191100
GCCCCAATGT  GCCCATCATC  AATATTCTAC  ATGTTTCCAA  TGTTATTGTA  TCTGTTTGCC  191160
TACAGTCGAG  GCCCTGATAT  CCTGTTTGAT  TTTCTTGAAT  TGCCAAAATT  TGCATACATG  191220
CTTACAAAAA  TAATGCCTGT  TGAATTTGCT  AGATATGTAA  AGGTTTGGAG  CAAATCAGGT  191280
GTATTAAATT  TATTAATATT  GTTTGAAATG  TCTAAGGCAA  TAATTCCCAA  ACTTCGTTGA  191340
GGGAGAAGGA  AAGCTTTTAA  AATCCCATTG  CCCAGGTGGC  ATCCCATACT  GTTACTGGGA  191400
ATTATGCATT  GGGATGGATC  CTTTAACCGA  GGAGATTATT  ATAGCCGGAG  CTCTGAACCA  191460
```

-continued

```
GCAATCTCAG TTCTTGTGAT AGTGAGCAAA GAACTACAAA CTAACACCAA AATGCAAGCT  191520
TAAAGCAAAG TTTATTGAAG CACAATAATA CACTCTGAGG GACAGCGGGC TTATTTCTGC  191580
GAAGTGAACT CAGCACTTCT TTACAGAGCT CAAGGTGCTT TTATGGGGTT TGTGGGGAGG  191640
AGTTGAGGTT TGGGCTGTAT CTGAGTGACA GGATGATGTT ATTTGATTGA AGTGTATAGC  191700
TATACAATCT AAAATTAAAC TGTGCATGGT CTTACCTATA ATTTGTTAAG AAAAGCCTCC  191760
CAGGGATGGG GGGGCAAAAC TGTATGTAAA TTCTATTATA ATGATGGCAT GATGAACTTG  191820
GGGTGAACTT GAAGACAGGC TTTTGTGTTG TTGGGCATGT GCCACCTTAG GGAATTTCCA  191880
CCTGTACCCT CCTTTCTCTT TCTCCAGGAT ATTTTGGCCA CAGACTTTAT CATAAACTCC  191940
ATCCCTTAGG GTGGCATTAG GGTAGTCTTG GGCCTGAATT TAGGTGGGCC AGTGGCTGTC  192000
TTAGTGACAG CCTTTCCGCT CTCTTCTGTC ATCCCTCCC  AACTGCTAAT GTCTAACTAC  192060
CTAACAATTA CCCATTAAAT CAGTGTGTCT GGGGTTAGGA GCAGGCCTCA ATATGTTAA   192120
TCATTCTCCA GATAATCCCA ATACTGTAAA GTTGTGAAA  CACTTGTCAG ATAATTCAAT  192180
TATGAAGGCT GTGGAAGGTG TTTCAGTAGG ATCTAATTGG TTAATGTTAT GACTTAATTA  192240
ATTTGAATCA AAAAACAAAA TGAAAAGCT  TTATATTTCT AAGTCAAATA AGACATAAGT  192300
TGGTCTAAGG TTGAGATAAA ATTTTTAAAT GTATGATTGA ATTTGAAAA  TCATAAATAT  192360
TTAAATATCT AAAGTTCAGA TCAGAACATT GCGAAGCTAC TTTCCCCAAT CAACAACACC  192420
CCTTCAGGAT TTAAAAACCA AGGGGGACAC TGGATCACCT AGTGTTTCAC AAGCAGGTAC  192480
CTTCTGCTGT AGGAGAGAGA GAACTAAAGT TCTGAAAGAC CTGTTGCTTT TCACCAGGAA  192540
GTTTTACTGG GCATCTCCTG AGCCTAGGCA ATAGCTGTAG GGTGACTTCT GGAGCCATCC  192600
CCGTTTCCCC GCCCCCAAA  AGAAGCGGAG ATTAACGGG  GACGTGCGGC CAGAGCTGGG  192660
GAAATGGGCC CGCGAGCCAG GCCGGCGCTT CTCCTCCTGA TGCTTTTGCA GACCGCGGTC  192720
CTGCAGGGGC GCTTGCTGCG TGAGTCCGAG GGCTGCGGGC GAACTAGGGG CGCGGCGGGG  192780
GTGGAAAAAT CGAAACTAGC TTTTTCTTTG CGCTTGGGAG TTTGCTAACT TTGGAGGACC  192840
TGCTCAACCC TATCCGCAAG CCCCTCTCCC TACTTTCTGC GTCCAGACCC CGTGAGGGAG  192900
TGCCTACCAC TGAACTGCAG ATAGGGTCC  CTCGCCCCAG GACCTGCCCC CTCCCCGGC   192960
TGTCCCGGCT CTGCGGAGTG ACTTTGGAA  CCGCCCACTC CCTTCCCCA  ACTAGAATGC  193020
TTTTAAATAA ATCTCGTAGT TCCTCACTTG AGCTGAGCTA AGCCTGGGC  TCCTTGAACC  193080
TGGAACTCGG GTTTATTTCC AATGTCAGCT GTGCAGTTTT TTCCCCAGTC ATCTCCAAAC  193140
AGGAAGTTCT TCCCTGAGTG CTTGCCGAGA AGGCTGAGCA AACCCACAGC AGGATCCGCA  193200
CGGGGTTTCC ACCTCAGAAC GAATGCGTTG GGCGGTGGGG GCGCGAAAGA GTGGCGTTGG  193260
GGATCTGAAT TCTTCACCAT TCCACCCACT TTTGGTGAGA CCTGGGGTGG AGGTCTCTAG  193320
GGTGGGAGGC TCCTGAGAGA GGCCTACCTC GGGCCTTTCC CCACTCTTGG CAATTGTTCT  193380
TTTGCCTGGA AAATTAAGTA TATGTTAGTT TTGAACGTTT GAACTGAACA ATTCTCTTTT  193440
CGGCTAGGCT TTATTGATTT GCAATGTGCT GTGTAATTAA GAGGCCTCTC TACAAAGTAC  193500
TGATAATGAA CATGTAAGCA ATGCACTCAC TTCTAAGTTA CATTCATATC TGATCTTATT  193560
TGATTTTCAC TAGGCATAGG GAGGTAGGAG CTAATAATAC GTTTATTTTA CTAGAAGTTA  193620
ACTGGAATTC AGATTATATA ACTCTTTTCA GGTTACAAAG AACATAAATA ATCTGGTTTT  193680
CTGATGTTAT TTCAAGTACT ACAGCTGCTT CTAATCTTAG TTGACAGTGA TTTTGCCCTG  193740
TAGTGTAGCA CAGTGTTCTG TGGGTCACAC GCCGGCCTCA GCACAGCACT TTGAGTTTTG  193800
GTACTACGTG TATCCACATT TTACACATGA CAAGAATGAG GCATGGCACG GCCTGCTTCC  193860
```

```
TGGCAAATTT  ATTCAATGGT  ACACTGGGCT  TTGGTGGCAG  AGCTCATGTC  TCCACTTCAT  193920
AGCTATGATT  CTTAAACATC  ACACTGCATT  AGAGGTTGAA  TAATAAAATT  TCATGTTGAG  193980
CAGAAATATT  CATTGTTTAC  AAGTGTAAAT  GAGTCCCAGC  CATGTGTTGC  ACTGTTCAAG  194040
CCCCAAGGGA  GAGAGCAGGG  AAACAAGTCT  TTACCCTTTG  ATATTTGCA   TTCTAGTGGG  194100
AGAGATGACA  ATAAGCAAAT  GAGCAGAAAG  ATATACAACA  TCAGGAAATC  ATGGGTGTTG  194160
TGAGAAGCAG  AGAAGTCAGG  GCAAGTCACT  CTGGGGCTGA  CACTTGAGCA  GAGACATGAA  194220
GGAAATAAGA  ATGATATTGA  CTGGGAGCAG  TATTTCCCAG  GCAAACTGAG  TGGGCCTGGC  194280
AAGTTGGATT  AAAAAGCGGG  TTTTCTCAGC  ACTACTCATG  TGTGTGTGTG  TGGGGGGGGG  194340
GGGCGGCGTG  GGGGTGGGAA  GGGGGACTAC  CATCTGCATG  TAGGATGTCT  AGCAGTATCC  194400
TGTCCTCCCT  ACTCACTAGG  TGCTAGGAGC  ACTCCCCCAG  TCTTGACAAC  CAAAAATGTC  194460
TCTAAACTTT  GCCACATGTC  ACCTAGTAGA  CAAACTCCTG  GTTAAGAAGC  TCGGGTTGAA  194520
AAAAATAAAC  AAGTAGTGCT  GGGGAGTAGA  GGCCAAGAAG  TAGGTAATGG  GCTCAGAAGA  194580
GGAGCCACAA  ACAAGGTTGT  GCAGGCGCCT  GTAGGCTGTG  GTGTGAATTC  TAGCCAAGGA  194640
GTAACAGTGA  TCTGTCACAG  GCTTTTAAAA  GATTGCTCTG  GCTGCTATGT  GGAAAGCAGA  194700
ATGAAGGGAG  CAACAGTAAA  AGCAGGGAGC  CCAGCCAGGA  AGCTGTTACA  CAGTCCAGGC  194760
AAGAGGTAGT  GGAGTGGGCT  GGGTGGGAAC  AGAAAAGGGA  GTGACAAACC  ATTGTCTCCT  194820
GAATATATTC  TGAAGGAAGT  TGCTGAAGGA  TTCTATGTTG  TGTGAGAGAA  AGAGAAGAAT  194880
TGGCTGGGTG  TAGTAGCTCA  TGCCAAGGAG  GAGGCCAAGG  AGAGCAGATT  CCTGAGCTCA  194940
GGAGTTCAAG  ACCAGCCTGG  GCAACACAGC  AAAACCCCTT  CTCTACAAAA  AATACAAAAA  195000
TTAGCTGGGT  GTGGTGGCAT  GCACCTGTGA  TCCTAGCTAC  TCGGGAGGCT  GAGGTGGAGG  195060
GTATTGCTTG  AGCCCAGGAA  GTTGAGGCTG  CAGTGAGCCA  TGACTGTGCC  ACTGTACTTC  195120
AGCCTAGGTG  ACAGAGCAAG  ACCCTGTCTC  CCCTGACCCC  CTGAAAAAGA  GAAGAGTTAA  195180
AGTTGACTTT  GTTCTTTATT  TTAATTTTAT  TGGCCTGAGC  AGTGGGGTAA  TTGGCAATGC  195240
CATTTCTGAG  ATGGTGAAGG  CAGAGGAAAG  AGCAGTTTGG  GGTAAATCAA  GGATCTGCAT  195300
TTGGGACATG  TTAAGTTTGA  GATTCCAGTC  AGGCTTCCAA  GTGGTGAGGC  CACATAGGCA  195360
GTTCAGTGTA  AGAATTCAGG  ACCAAGGCTG  GGCACGGTGG  CTCACTTCTG  TAATCCCAGC  195420
ACTTTGGTGG  CTGAGGCAGG  TAGATCATTT  GAGGTCAGGA  GTTTGAGACA  AGCTTGGCCA  195480
ACATGGTGAA  ACCCCATGTC  TACTAAAAAT  ACAAAATTA   GCCTGGTGTG  GTGGCGCACG  195540
CCTATAGTCC  CAGGTTTTCA  GGAGGCTTAG  GTAGGAGAAT  CCCTTGAACC  CAGGAGGTGC  195600
AGGTTGCAGT  GAGCTGAGAT  TGTGCCACTG  CACTCCAGCC  TGGGTGATAG  AGTGAGACTC  195660
TGTCTCAAAA  AAAAAAAAAA  AAAAAAAAAA  AAAACTGAA   GGAATTATTC  CTCAGGATTT  195720
GGGTCTAATT  TGCCCTGAGC  ACCAACTCCT  GAGTTCAACT  ACCATGGCTA  GACACACCTT  195780
AACATTTTCT  AGAATCCACC  AGCTTTAGTG  GAGTCTGTCT  AATCATGAGT  ATTGGAATAG  195840
GATCTGGGGG  CAGTGAGGGG  GTGGCAGCCA  CGTGTGGCAG  AGAAAGCAC   ACAAGGAAAG  195900
AGCACCCAGG  ACTGTCATAT  GGAAGAAAGA  CAGGACTGCA  ACTCACCCTT  CACAAAATGA  195960
GGACCAGACA  CAGCTGATGG  TATGAGTTGA  TGCAGGTGTG  TGGAGCCTCA  ACATCCTGCT  196020
CCCCTCCTAC  TACACATGGT  TAAGGCCTGT  TGCTCTGTCT  CCAGGTTCAC  ACTCTCTGCA  196080
CTACCTCTTC  ATGGGTGCCT  CAGAGCAGGA  CCTTGGTCTT  TCCTTGTTTG  AAGCTTTGGG  196140
CTACGTGGAT  GACCAGCTGT  TCGTGTTCTA  TGATCATGAG  AGTCGCCGTG  TGGAGCCCCG  196200
AACTCCATGG  GTTTCCAGTA  GAATTTCAAG  CCAGATGTGG  CTGCAGCTGA  GTCAGAGTCT  196260
```

```
GAAAGGGTGG GATCACATGT TCACTGTTGA CTTCTGGACT ATTATGGAAA ATCACAACCA  196320
CAGCAAGGGT ATGTGGAGAG GGGGCCTCAC CTTCCTGAGG TTGTCAGAGC TTTTCATCTT  196380
TTCATGCATC TTGAAGGAAA CAGCTGGAAG TCTGAGGTCT TGTGGGAGCA GGGAAGAGGG  196440
AAGGAATTTG CTTCCTGAGA TCATTTGGTC CTTGGGGATG GTGGAAATAG GGACCTATTC  196500
CTTTGGTTGC AGTTAACAAG GCTGGGGATT TTTCCAGAGT CCCACACCCT GCAGGTCATC  196560
CTGGGCTGTG AAATGCAAGA AGACAACAGT ACCGAGGGCT ACTGGAAGTA CGGGTATGAT  196620
GGGCAGGACC ACCTTGAATT CTGCCCTGAC ACACTGGATT GGAGAGCAGC AGAACCCAGG  196680
GCCTGGCCCA CCAAGCTGGA GTGGGAAAGG CACAAGATTC GGGCCAGGCA GAACAGGGCC  196740
TACCTGGAGA GGGACTGCCC TGCACAGCTG CAGCAGTTGC TGGAGCTGGG GAGAGGTGTT  196800
TTGGACCAAC AAGGTATGGT GGAAACACAC TTCTGCCCCT ATACTCTAGT GGCAGAGTGG  196860
AGGAGGTTGC AGGGCACGGA ATCCTGGTT GGAGTTTCAG AGGTGGCTGA GGCTGTGTGC  196920
CTCTCCAAAT TCTGGGAAGG GACTTTCTCA ATCCTAGAGT CTCTACCTTA TAATTGAGAT  196980
GTATGAGACA GCCACAAGTC ATGGGTTTAA TTTCTTTTCT CCATGCATAT GGCTCAAAGG  197040
GAAGTGTCTA TGGCCCTTGC TTTTTATTTA ACCAATAATC TTTTGTATAT TTATACCTGT  197100
TAAAAATTCA GAAATGTCAA GGCCGGGCAC GGTGGCTCAC CCCTGTAATC CCAGCACTTT  197160
GGGAGGCCGA GGCGGGTGGT CACAAGGTCA GGAGTTTGAG ACCAGCCTGA CCAACATGGT  197220
GAAACCCGTC TCTAAAAAAA TACAAAAATT AGCTGGTCAC AGTCATGCGC ACCTGTAGTC  197280
CCAGCTAATT GGAAGGCTGA GGCAGGAGCA TCGCTTGAAC CTGGGAAGCG GAAGTTGCAC  197340
TGAGCCAAGA TCGCGCCACT GCACTCCAGC CTAGGCAGCA GAGTGAGACT CCATCTTAAA  197400
AAAAAAAAAA AAAAAAAAA GAGAATTCAG AGATCTCAGC TATCATATGA ATACCAGGAC  197460
AAAATATCAA GTGAGGCCAC TTATCAGAGT AGAAGAATCC TTTAGGTTAA AAGTTTCTTT  197520
CATAGAACAT AGCAATAATC ACTGAAGCTA CCTATCTTAC AAGTCCGCTT CTTATAACAA  197580
TGCCTCCTAG GTTGACCCAG GTGAAACTGA CCATCTGTAT TCAATCATTT TCAATGCACA  197640
TAAAGGGCAA TTTTATCTAT CAGAACAAAG AACATGGGTA ACAGATATGT ATATTACAT  197700
GTGAGGAGAA CAAGCTGATC TGACTGCTCT CCAAGTGACA CTGTGTTAGA GTCCAATCTT  197760
AGGACACAAA ATGGTGTCTC TCCTGTAGCT TGTTTTTTC TGAAAAGGGT ATTTCCTTCC  197820
TCCAACCTAT AGAAGGAAGT GAAAGTTCCA GTCTTCCTGG CAAGGGTAAA CAGATCCCCT  197880
CTCCTCATCC TTCCTCTTTC CTGTCAAGTG CCTCCTTTGG TGAAGGTGAC ACATCATGTG  197940
ACCTCTTCAG TGACCACTCT ACGGTGTCGG GCCTTGAACT ACTACCCCA GAACATCACC  198000
ATGAAGTGGC TGAAGGATAA GCAGCCAATG GATGCCAAGG AGTTCGAACC TAAAGACGTA  198060
TTGCCCAATG GGGATGGGAC CTACCAGGGC TGGATAACCT TGGCTGTACC CCCTGGGGAA  198120
GAGCAGAGAT ATACGTGCCA GGTGGAGCAC CCAGGCCTGG ATCAGCCCCT CATTGTGATC  198180
TGGGGTATGT GACTGATGAG AGCCAGGAGC TGAGAAAATC TATTGGGGGT TGAGAGGAGT  198240
GCCTGAGGAG GTAATTATGG CAGTGAGATG AGGATCTGCT CTTTGTTAGG GGGTGGGCTG  198300
AGGGTGGCAA TCAAAGGCTT TAACTTGCTT TTTCTGTTTT AGAGCCCTCA CCGTCTGGCA  198360
CCCTAGTCAT TGGAGTCATC AGTGGAATTG CTGTTTTTGT CGTCATCTTG TTCATTGGAA  198420
TTTTGTTCAT AATATTAAGG AAGAGGCAGG GTTCAAGTGA GTAGGAACAA GGGGGAAGTC  198480
TCTTAGTACC TCTGCCCCAG GGCACAGTGG GAAGAGGGGC AGAGGGATC TGGCATCCAT  198540
GGGAAGCATT TTTCTCATTT ATATTCTTTG GGGACACCAG CAGCTCCCTG GGAGACAGAA  198600
AATAATGGTT CTCCCCAGAA TGAAAGTCTC TAATTCAACA AACATCTTCA GAGCACCTAC  198660
```

-continued

| | | | | | |
|---|---|---|---|---|---|
| TATTTTGCAA | GAGCTGTTTA | AGGTAGTACA | GGGGCTTTGA | GGTTGAGAAG | TCACTGTGGC 198720 |
| TATTCTCAGA | ACCCAAATCT | GGTAGGGAAT | GAAATTGATA | GCAAGTAAAT | GTAGTTAAAG 198780 |
| AAGACCCCAT | GAGGTCCTAA | AGCAGGCAGG | AAGCAAATGC | TTAGGGTGTC | AAAGGAAAGA 198840 |
| ATGATCACAT | TCAGCTGGGG | ATCAAGATAG | CCTTCTGGAT | CTTGAAGGAG | AAGCTGGATT 198900 |
| CCATTAGGTG | AGGTTGAAGA | TGATGGGAGG | TCTACACAGA | CGGAGCAACC | ATGCCAAGTA 198960 |
| GGAGAGTATA | AGGCATACTG | GGAGATTAGA | AATAATTACT | GTACCTTAAC | CCTGAGTTTG 199020 |
| CGTAGCTATC | ACTCACCAAT | TATGCATTTC | TACCCCTGA | ACATCTGTGG | TGTAGGGAAA 199080 |
| AGAGAATCAG | AAAGAAGCCA | GCTCATACAG | AGTCCAAGGG | TCTTTTGGGA | TATTGGGTTA 199140 |
| TGATCACTGG | GGTGTCATTG | AAGGATCCTA | AGAAGGAGG | ACCACGATCT | CCCTTATATG 199200 |
| GTGAATGTGT | TGTTAAGAAG | TTAGATGAGA | GGTGAGGAGA | CCAGTTAGAA | AGCCAATAAG 199260 |
| CATTTCCAGA | TGAGAGATAA | TGGTTCTTGA | AATCCAATAG | TGCCCAGGTC | TAAATTGAGA 199320 |
| TGGGTGAATG | AGGAAAATAA | GGAAGAGAGA | AGAGGCAAGA | TGGTGCCTAG | GTTTGTGATG 199380 |
| CCTCTTTCCT | GGGTCTCTTG | TCTCCACAGG | AGGAGCCATG | GGGCACTACG | TCTTAGCTGA 199440 |
| ACGTGAGTGA | CACGCAGCCT | GCAGACTCAC | TGTGGGAAGG | AGACAAAACT | AGAGACTCAA 199500 |
| AGAGGGAGTG | CATTTATGAG | CTCTTCATGT | TTCAGGAGAG | AGTTGAACCT | AAACATAGAA 199560 |
| ATTGCCTGAC | GAACTCCTTG | ATTTTAGCCT | TCTCTGTTCA | TTTCCTCAAA | AAGATTTCCC 199620 |
| CATTTAGGTT | TCTGAGTTCC | TGCATGCCGG | TGATCCCTAG | CTGTGACCTC | TCCCTGGAA 199680 |
| CTGTCTCTCA | TGAACCTCAA | GCTGCATCTA | GAGGCTTCCT | TCATTCCTC | CGTCACCTCA 199740 |
| GAGACATACA | CCTATGTCAT | TTCATTTCCT | ATTTTGGAA | GAGGACTCCT | TAAATTTGGG 199800 |
| GGACTTACAT | GATTCATTTT | AACATCTGAG | AAAAGCTTTG | AACCCTGGGA | CGTGGCTAGT 199860 |
| CATAACCTTA | CCAGATTTTT | ACACATGTAT | CTATGCATTT | TCTGGACCCG | TTCAACTTTT 199920 |
| CCTTTGAATC | CTCTCTCTGT | GTTACCCAGT | AACTCATCTG | TCACCAAGCC | TTGGGGATTC 199980 |
| TTCCATCTGA | TTGTGATGTG | AGTTGCACAG | CTATGAAGGC | TGTACACTGC | ACGAATGGAA 200040 |
| GAGGCACCTG | TCCCAGAAAA | AGCATCATGG | CTATCTGTGG | GTAGTATGAT | GGGTGTTTTT 200100 |
| AGCAGGTAGG | AGGCAAATAT | CTTGAAAGGG | GTTGTGAAGA | GGTGTTTTTT | CTAATTGGCA 200160 |
| TGAAGGTGTC | ATACAGATTT | GCAAAGTTTA | ATGGTGCCTT | CATTTGGGAT | GCTACTCTAG 200220 |
| TATTCCAGAC | CTGAAGAATC | ACAATAATTT | TCTACCTGGT | CTCTCCTTGT | TCTGATAATG 200280 |
| AAAATTATGA | TAAGGATGAT | AAAAGCACTT | ACTTCGTGTC | CGACTCTTCT | GAGCACCTAC 200340 |
| TTACATGCAT | TACTGCATGC | ACTTCTTACA | ATAATTCTAT | GAGATAGGTA | CTATTATCCC 200400 |
| CATTTCTTTT | TTAAATGAAG | AAAGTGAAGT | AGGCCGGGCA | CGGTGGCTCA | CGCCTGTAAT 200460 |
| CCCAGCACTT | TGGGAGGCCA | AAGCGGGTGG | ATCACGAGGT | CAGGAGATCG | AGACCATCCT 200520 |
| GGCTAACATG | GTGAAACCCC | ATCTCTAATA | AAAATACAAA | AAATTAGCTG | GGCGTGGTGG 200580 |
| CAGACGCCTG | TAGTCCCAGC | TACTCGGAAG | GCTGAGGCAG | GAGAATGGCA | TGAACCCAGG 200640 |
| AGGCAGAGCT | TGCAGTGAGC | CGAGTTTGCG | CCACTGCACT | CCAGCCTAGG | TGACAGAGTG 200700 |
| AGACTCCATC | TCAAAAAAAT | AAAAATAAAA | ATAAAAAAT | GAAAAAAAA | AGAAAGTGAA 200760 |
| GTATAGAGTA | TCTCATAGTT | TGTCAGTGAT | AGAAACAGGT | TTCAAACTCA | GTCAATCTGA 200820 |
| CCGTTTGATA | CATCTCAGAC | ACCACTACAT | TCAGTAGTTT | AGATGCCTAG | AATAAATAGA 200880 |
| GAAGGAAGGA | GATGGCTCTT | CTCTTGTCTC | ATTGTGTTTC | TTCTGAGTGA | GCTTGAATCA 200940 |
| CATGAAGGGG | AACAGCAGAA | AACAACCAAC | TGATCCTCAG | CTGTCATGTT | TCCTTTAAAA 201000 |
| GTCCCTGAAG | GAAGGTCCTG | GAATGTGACT | CCCTTGCTCC | TCTGTTGCTC | TCTTTGGCAT 201060 |

```
TCATTTCTTT  GGACCCTACG  CAAGGACTGT  AATTGGTGGG  GACAGCTAGT  GGCCCTGCTG  201120
GGCTTCACAC  ACGGTGTCCT  CCCTAGGCCA  GTGCCTCTGG  AGTCAGAACT  CTGGTGGTAT  201180
TTCCCTCAAT  GAAGTGGAGT  AAGCTCTCTC  ATTTTGAGAT  GGTATAATGG  AAGCCACCAA  201240
GTGGCTTAGA  GGATGCCCAG  GTCCTTCCAT  GGAGCCACTG  GGGTTCCGGT  GCACATTAAA  201300
AAAAAAATCT  AACCAGGACA  TTCAGGAATT  GCTAGATTCT  GGGAAATCAG  TTCACCATGT  201360
TCAAAGAGT   CTTTTTTTT   TTTTTGAGAC  TCTATTGCCC  AGGCTGGAGT  GCAATGGCAT  201420
GATCTCGGCT  CACTGTAACC  TCTGCCTCCC  AGGTTCAAGC  GATTCTCCTG  TCTCAGCCTC  201480
CCAAGTAGCT  GGGATTACAG  GCGTGCACCA  CCATGCCCGG  CTAATTTTTG  TATTTTTAGT  201540
AGAGACAGGG  TTTCACCATG  TTGGCCAGGC  TGGTCTCGAA  CTCTCCTGAC  CTCGTGATCC  201600
GCCTGCCTCG  GCCTCCCAAA  GTGCTGAGAT  TACAGGTGTG  AGCCACCCTG  CCCAGCCGTC  201660
AAAGAGTCT   TAATATATAT  ATCCAGATGG  CATGTGTTTA  CTTTATGTTA  CTACATGCAC  201720
TTGGCTGCAT  AAATGTGGTA  CAAGCATTCT  GTCTTGAAGG  GCAGGTGCTT  CAGGATACCA  201780
TATACAGCTC  AGAAGTTTCT  TCTTTAGGCA  TTAAATTTTA  GCAAAGATAT  CTCATCTCTT  201840
CTTTTAAACC  ATTTTCTTTT  TTTGTGGTTA  GAAAAGTTAT  GTAGAAAAAA  GTAAATGTGA  201900
TTTACGCTCA  TTGTAGAAAA  GCTATAAAAT  GAATACAATT  AAAGCTGTTA  TTTAATTAGC  201960
CAGTGAAAAA  CTATTAACAA  CTTGTCTATT  ACCTGTTAGT  ATTATTGTTG  CATTAAAAAT  202020
GCATATACTT  TAATAAATGT  ATATTGTATT  GTATACTGCA  TGATTTTATT  GAAGTTCTTG  202080
TTCATCTTGT  GTATATACTT  AATCGCTTTG  TCATTTTGGA  GACATTTATT  TTGCTTCTAA  202140
TTTCTTTACA  TTTTGTCTTA  CGGAATATTT  TCATTCAACT  GTGGTAGCCG  AATTAATCGT  202200
GTTCTTCAC   TCTAGGGACA  TTGTCGTCTA  AGTTGTAAGA  CATTGGTTAT  TTTACCAGCA  202260
AACCATTCTG  AAAGCATATG  ACAAATTATT  TCTCTCTTAA  TATCTTACTA  TACTGAAAGC  202320
AGACTGCTAT  AAGGCTTCAC  TTACTCTTCT  ACCTCATAAG  GAATATGTTA  CAATTAATTT  202380
ATTAGGTAAG  CATTTGTTTT  ATATTGGTTT  TATTTCACCT  GGGCTGAGAT  TTCAAGAAAC  202440
ACCCCAGTCT  TCACAGTAAC  ACATTTCACT  AACACATTTA  CTAAACATCA  GCAACTGTGG  202500
CCTGTTAATT  TTTTAATAG   AAATTTTAAG  TCCTCATTTT  CTTTCGGTGT  TTTTTAAGCT  202560
TAATTTTTCT  GGCTTTATTC  ATAAATTCTT  AAGGTCAACT  ACATTTGAAA  AATCAAAGAC  202620
CTGCATTTTA  AATTCTTATT  CACCTCTGGC  AAAACCATTC  ACAAACCATG  GTAGTAAAGA  202680
GAAGGGTGAC  ACCTGGTGGC  CATAGGTAAA  TGTACCACGG  TGGTCCGGTG  ACCAGAGATG  202740
CAGCGCTGAG  GGTTTTCCTG  AAGGTAAAGG  AATAAAGAAT  GGGTGGAGGG  GCGTGCACTG  202800
GAAATCACTT  GTAGAGAAAA  GCCCCTGAAA  ATTTGAGAAA  ACAAACAAGA  AACTACTTAC  202860
CAGCTATTTG  AATTGCTGGA  ATCACAGGCC  ATTGCTGAGC  TGCCTGAACT  GGGAACACAA  202920
CAGAAGGAAA  ACAAACCACT  CTGATAATCA  TTGAGTCAAG  TACAGCAGGT  GATTGAGGAC  202980
TGCTGAGAGG  TACAGGCCAA  AATTCTTATG  TTGTATTATA  ATAATGTCAT  CTTATAATAC  203040
TGTCAGTATT  TTATAAAACA  TTCTTCACAA  ACTCACACAC  ATTTAAAAAC  AAAACACTGT  203100
CTCTAAAATC  CCCAAATTTT  TCATAAACTC  AGTTTTAAAC  TAACTTTTTT  TCAAACCACA  203160
ATCTGATTTA  ACAATGACTA  TCATTTAAAT  ATTTCTGACT  TTCAAATTAA  AGATTTTCAC  203220
ATGCAGGCTG  ATATTTGTAA  TTGTGATTCT  CTCTGTAGGC  TTTGGGTATA  ATGTGTTCTT  203280
TTCCTTTTTT  GCATCAGCGA  TTAACTTCTA  CACTCTAACA  TGTAGAATGT  TACTACAATA  203340
TTAAAGTATT  TTGTATGACA  ATTTTATTTG  AAAGCCTAGG  ATGCGTTGAC  ATCCTGCATG  203400
CATTTATTAC  TTGATATGCA  TGCATTCTGG  TATCTCAAGC  ATTCTATTTC  TGAGTAATTG  203460
```

| | | | | | |
|---|---|---|---|---|---|
| TTTAAGGTGT | AGAAGAGATA | GATATGGTGG | ATTTGGAGTT | GATACTTATA | TATTTTCTAT 203520 |
| TTCTTGGATG | GATGAATTTG | TACATTAAAA | GTTTTCCATG | GCAGAAATCT | TTTCAAAAAC 203580 |
| TTTTTTTTTC | CGGGATGGAT | TGAAGGCCCT | GATTTCACCA | CAATGCAATA | TATTAATGTA 203640 |
| GCAAAATTGT | ACTTGTACCC | CATGAATATA | TATAATCTTA | AGAAATTTT | TTTAGCCAAT 203700 |
| TATTATTACT | TACTAGATAT | TAGGCTGTGT | TCTGAATCTT | AATTTAATTC | CTCCAAAGAA 203760 |
| TCTTATGAGG | TAGGTAGGAG | CTATTGCTGC | TATTCTGTTA | TGCTTATGTT | GCTGTTATGA 203820 |
| AACCAAGGCA | CAGAGAGGTT | AGTTAACTTG | CTGAAGAAAA | TGATGTGCTG | GATTTTATT 203880 |
| CTAGCTATTC | TGGAATAACA | ACTACACAAC | CTTATGTCTG | AGCCAAGGAA | ACATACGGTG 203940 |
| TGGCAACAGT | TACCATGTTT | TTAGGAACAG | CAGCACTCCT | AATGTTTGCT | GCAGGGAAAA 204000 |
| AGGAATCTCA | GAATTTGCCT | GATCCCTATA | ATTTTTTTCC | TAAATATTTT | GAAATATCTT 204060 |
| TCAGATGTAT | TTTAAAATTT | AAGGATATTT | TGTTCAGTTC | ATACAGAATT | TTTTTTTTT 204120 |
| TCTCGAGATG | GAGTCTCACT | CTATCACCCA | GGCTGGAATG | CAGTGGCATG | ATCTCGGCTC 204180 |
| ACTGCAACCT | CTGCCTCCTG | GGTTCAAGCA | ATTTTCCTGC | CTCAGCCTCC | CAAGTGGCTG 204240 |
| AGACTACAGG | CGCATGCCAC | CATGCACGGC | TAATTTTTTT | TGTATTTTA | GTAGAGATGG 204300 |
| AGTTTCACCA | TGTTGGCCAG | GCTGGTCTCG | AACTCCTGAC | CTCAAATGAT | CCGCCCTTTT 204360 |
| TGGCCTCCCA | AAGTGCTGGG | ATTACAGGCG | TGAGCTACCG | CGCCCAGCCA | AATTTCTAAC 204420 |
| TTGTTTTGTT | GTTGTTGAGA | CAGGGTCTCA | GTCTGACACC | AAGGCTGGTG | TGCAGTACTG 204480 |
| CGATCACGGC | TCACTGCAGT | CTCGACCTCC | TGAGCTCAAG | TGATCCTCCC | ACCTCAGCCT 204540 |
| ACTGAGTAGC | TGGGACCACC | ACGCCTGGCT | CATTTTTTC | TATTATTTAT | TGAAACGGGT 204600 |
| TCTGGCTATG | TTGCCCAGGT | TGGTCTTGAA | CTCCGGAGCT | CATGCGATCC | ACCCACCTCA 204660 |
| GCGTCCGAAA | GGATTATCAG | GAGTGAGCCA | CCGTGCCCGG | CCAAATTTCT | AACTTTTGAA 204720 |
| TTGACATATT | CATTTATTCT | CTTTATCATT | CAGGGAGAAA | TTTGGGGATG | GATAGCCTTG 204780 |
| AAGCATCATC | CACCAAGTTA | TTTTATACAC | CAGATTTAGA | TACAAAGTAT | TTTTTTATTA 204840 |
| TTTAAAAAAA | TCAAATTCTA | GCTTTTACTC | TGAAGATTCT | AAAAAGAATT | TTGGAGTCTT 204900 |
| TAATTCATAC | TTCAGGGGCA | GGGGAATAAG | TACCAATATT | CGTATAACTT | TCAGTGCAAG 204960 |
| TCACGTTAGC | TAACTGTAGT | CTATTGAGTT | AAATATCCTT | GATTTATTCC | TTAAAACTGA 205020 |
| GTCACTATGA | CGGCACTTTT | TTGTTTTTTT | TTTTCGAGAC | GGAGCTCGCC | CTGTCTCCCA 205080 |
| GGCTGGAGTG | CGGTGGTGCG | ATCTCGGCTC | ACTGCAATCT | CCGCCTCCCA | GGTTCAAGCG 205140 |
| ATTCTCCTGC | CCCAGCCTCC | TGAGTAGCTG | GGACTACAGG | CACACACCAC | CACGCCCAGC 205200 |
| TAATGTTTGT | ATTTTTAGTA | GAGACAGGGT | TTCATCATTT | TGGTCAGGCT | GGTCTTGAAC 205260 |
| TCCTGACCTC | GTGATCAGCC | TGCCTCGACC | TCCCAAAGTG | CTGGGATTAC | AGTCATGAGC 205320 |
| CACTGCACCC | GGCTGAATGG | CACTTTCATA | AAACAGTAAA | TAACCAACTT | CACTACTGCC 205380 |
| CCCAAGAGTT | TTACTATGTA | TATGAGGGCA | TCTGTTTTAA | GTATGGGTAT | AATGTTACGG 205440 |
| GTTTTTCTTT | GTGTAAGTTT | GGGTTCACAA | TTTCATCATT | AAAACAAATG | TAAAATACTT 205500 |
| TGTGCTTTCT | GTGTGCTATT | AAGAAAGTAT | TCAAGGGAAT | TTTGAAAATC | AAATTTAATT 205560 |
| ACTCTCATGT | TTGTAAAATT | TTTGAAACAA | ATGTTTAAGA | GAGGATAATG | TTAGAAATTA 205620 |
| TCTTTCCAGC | CAGACCTGGT | GGCTCACGCC | AGTAATCCTA | GCATTTGGG | AGGACAAGGT 205680 |
| GGGCAGATCA | CTTAAGCCCA | GGAATTCAAG | ACCAGCCTGG | ACAACACAGG | GAAAGCCCAT 205740 |
| CTCTACAAAA | TATACAAAAT | TAGTGGCCGA | GCGTGGTGGC | TCACGCCTGT | AATCCCAGCA 205800 |
| CTTTGGGAGG | CCGAGGCGGG | CAGATCACCT | GAGGTCAGGA | GTTCCAGACC | AGCCTCAACA 205860 |

| | | | | | | |
|---|---|---|---|---|---|---|
|TGGAGAAACC|CCGTCTCTAC|TAAAAATACA|AAATTAGCTG|GGCGTGGTGA|TGCATGCCTG|205920|
|TAATCCCAGC|TACTCGGGAG|GCTGAGGCAG|GAGAATTGCT|TGAACCTGGG|AGGTAGAGGT|205980|
|TGCGGTGAGC|CGAGATCCCG|CCATTGCACT|CCAGCCTGGG|CAACAAGAGC|GAAACTCCAT|206040|
|CTCAAAAAAC|AAAACAAACA|AATAAACAAA|ATTAGTCAGG|TGTGGTTGTG|CACACCTGTA|206100|
|GTCCAGCTA|CTTGGGAGGC|TGAGGTGGGA|GGATCACTTG|AGCCCGGGGA|AGTGTAGGCT|206160|
|ACCATGAGCC|ATCATGGTGC|CACTGTACTC|CAGTCTAGGA|AAAAATAAA|CATTAAAAAT|206220|
|TTTAAAATCT|TAAAAAAGA|AAAGAAATTT|TCTGTCCAGA|TATCTTTATT|TTTAACAAAT|206280|
|CGAAGTGTAT|TAATAGTGTT|TATGGGAGCG|TGCCCACACA|AGGACAGCAA|GCCTAGGAAG|206340|
|TGCAAGTCAA|GAAAACTTTT|TGTGAAATAA|TTTAAACTGA|AAAGAAAAG|CAGAGATTTT|206400|
|TTTCTAGAAA|AGTAAGGAGT|GGAGGTAAAA|AAAAACACA|GCAGAGACAC|AGGTATGCTA|206460|
|CGGAACCAAA|GGTGTGCCAA|TGGTACTGAC|AGTTTAATTC|AGAAAAAAT|GAATCAGAAA|206520|
|ATGGATATTT|TTAAATAAGT|TAGGTTGCTG|AAAAAGAGAA|ATGCAGTGAA|GCCTTAGATG|206580|
|GGAGTGAGAT|AAATCAGCCA|TTGGCTAGAG|GAGTTTCTTG|CCCAAGACCA|GTGGTGATGT|206640|
|CCCCAAATGC|CTGGAAACAA|CTGTTGTGAC|ATTATAAAGC|CCCCATAGTC|TAAGTTGGGT|206700|
|GAGACTATAC|TTATGCATTT|TCTCACCTGT|AATATAGCTT|AAAAGTATTT|CTACTCTGGG|206760|
|ATTTCTTTAC|ATTTACTAA|AGCGCAATTA|TATACTTAAA|ACTGATAGTG|TATGCTGGGC|206820|
|TGCTAGTCAT|TCTCAACCCT|GGCCAATTAT|CAGAATTGTT|TGTTGAATAT|ATAGGTGCCA|206880|
|TATATAGGTG|CATACACACA|CACACACACA|CACATACACA|CACACACACA|CACACACACA|206940|
|CCATATTTCA|TTCCTCATAT|CGAATATTCT|GAGAGAGTTA|GTTTGTGGAG|GGTAGTTCTG|207000|
|GACAATTTAT|ATTTTCATAA|CACCTCTGGT|TATTTTTTT|TAAGTAGAGA|TGAAGACTTG|207060|
|CTATGTTGCC|CAAAATGGTC|TTGAACTCCT|GAGCTCAAGC|GATTCTCCCA|ACTCAGCCTC|207120|
|CTGAAGTGCT|GGGATTACAG|CCGTGAGCCA|CTGCATTAAC|CTCTGATTAA|TATCATAGAT|207180|
|TAACCTCTGA|TTAATATCAT|AGATTTATTT|GTTTGAATGC|TTCATGTATC|CTCTCAACCA|207240|
|CAACTTGTTT|GCAGAGTTTT|AATCTGAAGG|GCTTAGGTCT|CTTGTTCAAT|GAATGAGTTT|207300|
|GATCTGATGG|GTGAGAGGAA|GGTGAAATGG|AAAGCGAACG|AGAAGCCATA|CAGATTAGGC|207360|
|GAGTGAGCCT|AATCTCTCCC|TAACCATAAG|ATTGAGTATG|CCTGAATTCT|TCGCAGAGTG|207420|
|GAAGAATCCA|TTTTAAATAT|ATATATCTAC|ATGTACAGAT|CCTTTAAATA|TTTGTTCTGA|207480|
|CATTCATTGT|TTTTGAGTCA|CTGTCATTGA|GAAAGTTTA|GAAGGAGAT|ATTAGGAGCA|207540|
|GGAAATAGAA|AGTAAATAAA|ATATCAAAAT|AAAATGGGG|TTTTATAAAT|GATATAATAG|207600|
|GCAAAATAAA|GGAAAGGCAT|CCTAGACCTC|TGGTTAAAAT|GAAGATGGCA|CTTGGCGAGA|207660|
|TGTGTTCCAG|GGTAGTTCAC|ATGATGTATG|TTTTCAGAGA|ATTGTCATAT|TGCATATGCT|207720|
|GCTATATTTT|TTATTTTCAT|GAATTAAAAG|GCATGTTGAG|ATTTCAGAGT|TTACTTATG|207780|
|ATCTCAGACT|CTGCATTTTT|TCTCTGTAAT|GTTTGACATT|TCTTCCTAGC|TAAGTCTCTA|207840|
|GTTATAAGGT|CTGTGTTGTG|GCATGTGGAC|AGTGAGTGGA|AGAACCTAAG|AACTCAATTT|207900|
|GGGGCAGAAG|AATGTAATCA|ATTATTTCAG|AAGTGATACA|AACAATATGA|CATGTAGAGC|207960|
|ATTCTGGCCT|TTCCTGGGTC|TTTTTTCTCC|ATTCCTGGAT|TTCTTCTCTT|CATGTGAGCA|208020|
|AGTCTGAGGT|TACTATATAA|TGTCTCTCAC|AGGCCACAGC|CCCATTCTAA|ATATTCCCAA|208080|
|TAGAAATTCA|TTTATTAACC|AGAGAGTGGT|GGGTGGGGTT|GTTTTTGTTT|TTTAAACAAA|208140|
|AGTGGATCTT|ATGGGCATTC|TGGAAAGCTC|CCGCAGGAAG|CTAAGAATAA|AATTTTGAAT|208200|
|TGAGAAGTCC|CTTTCTTCAA|ACCACATTCA|GACCCAATTC|TGCTATTCTA|TTTATTTTTC|208260|

```
AAGGGGATTA   GCCTTATTTT   AACACCAATA   ATCTTATCAC   AAAAACCTCC   CAGAGGAAGA   208320
CCCTGTAGAT   TTTGTAATGA   CCTTAATCAA   GTATTAGCCC   TACACTTCAA   TTAATCCCCA   208380
ACTGTACAAA   ACGAATGTTC   TTTTCTCTAA   AGCTGTAGCA   AGTTGAAAGG   GGATTAAAAA   208440
CGGAGGGAAG   GGAAGAGTGT   TTGGAATTTC   AGGCACAGCA   AACAGGCACA   GCAGACCAGG   208500
AAGAGCGTCC   CGGGAAAACA   TATTATCCAG   ACTTAAGTTT   ATATTCCCTG   TCTCTCTCAG   208560
ACTTTTGCAG   AAAAATGAGT   CATTCAACAA   ATATTTGAAT   CGAGATAGGG   AAAGTGACGA   208620
GGAAGAAGTT   TGCACTTATG   AGGTTTTAAT   TTGCAATTAT   TTGGCTACCT   TTTTGCCTTC   208680
CCAAAACATA   GGGTCTTTAG   GAGTGAAACT   TCATAGCCAA   ACTTATACCT   TGTCCAGCAC   208740
AGAGAAGGCC   ATCAAAATGC   CTGGTTTAAA   TAAAAATATT   AAAATGATTG   GGAGGGTAAA   208800
TCCCTTGACC   TATAAATCTG   ACCTCCTTTA   AACATTATTT   GTATGTTCCC   CAATAAACTA   208860
TTCCGTAATT   TATTAGTTAG   CAAGTGGAAA   TAAAAGAAA   TGTGGAATGG   GGCTATGCTT   208920
AGCGTCATTA   AGCTGACAGG   AATACAGCGC   ATTCAACTTG   CAAACACCCT   TCCACTCCCA   208980
CAAAGAGCAA   GCTGTCACTG   GCCAATCAAA   ACAATGAACC   ATAATGAAAC   AGTTTTTCTT   209040
GCTCCACCCA   CTTGGTGACC   AAATTTGAAA   AAAAAAAAAA   ACCGCGCCAA   CTCATGTTGT   209100
TTTCAATCAG   GTCCGCCAAG   TTTGTATTTA   AGGAACTGTT   TCAGTTCATA   CCTTCCACTG   209160
CGATAGGAAT   CATGTCTGGT   CGCGGCAAAG   GCGGAAAAGG   CTTGGGGAAG   GGTGGTGCTA   209220
AGCGCCATCG   TAAGGTGCTC   CGGGATAACA   TCCAGGGCAT   TACAAAACCG   GCTATTCGCC   209280
GTTTGGCTCG   GCGCGGTGGC   GTCAAGCGCA   TTTCCGGTCT   TATCTATGAG   GAGACTCGAG   209340
GTGTGCTTAA   GGTTTTCTTA   GAGAACGTTA   TTCGAGACGC   CGTCACCTAT   ACGGAGCACG   209400
CCAAGCGCAA   AACTGTCACA   GCCATGGATG   TAGTATATGC   CCTAAAACGT   CAGGGGCGCA   209460
CTCTGTATGG   CTTCGGCGGC   TGAATCTAAG   AATACGCGGT   CTCCTGAGAA   CTTCAAAAAA   209520
CAAAAACAAA   AAAACCCAAA   GGCCCTTTTC   AGGGCCGCTC   ACAAAGTCGT   TTAAAGAGCT   209580
GAAATGCGTT   GCGAGAATGA   GTTTGGATGA   CAGAAATAAC   CGTGACATCC   TGCATAAGAA   209640
TGAATTGTGT   TTGCCATGAC   CGGCCACACT   GTGACAAAAT   TTCAAAGCAT   AAAGTAGGCA   209700
TAGAGAGGTA   AGCGCTAATA   AAGTGATTGG   CTCCACAAAA   AGCATTTTGC   TGGGCGCAGT   209760
GGCTCACGAC   TGTAATCCCA   GCACTTTGGG   AGGCCAAAGC   TAGTGTATCA   CTTGAGATCA   209820
AGAATCCGAG   ACCAGCCTGG   CCAAAATGGT   GAAACCCCCT   CTACCAAAAA   AATACAAAA   209880
CTTAGCCGGG   CGTGGTGGTC   TGCACCTGTA   GGCCCAGCTA   GCCCGGAAGC   AGAGATTGCA   209940
GTGAGCCGAG   ATCGCGCCAC   TCCCCTCCAG   CCTGGGAGAC   AGAGAGAGAC   TCCTCAAAAA   210000
AAAAAAAAAA   AAAAAAAAAA   AAAATTATGT   ATTTTAGAGC   ATTCTAAGAA   TGGTACTTTG   210060
GACTTAACCG   AAGGGCTGGA   GGCGCGTGTT   GAACAAAGGT   TATCACCTTT   TGGCTCATGC   210120
GGCACACAGC   TATGTAAATA   AAGCATCTTT   AGGGACAAGC   TCTCATTTGC   GGAGGGTTCT   210180
ATGGCTGTTG   TCCTATTGGC   CAAAACAAAG   TGGTCTAAGT   CCGGGCGCGG   TGGCTCACGC   210240
CTGTATTCCC   AGCAGTTTGG   TAGGCCAAGG   TGGGTGGATC   ACGAGGTCTG   GCGTTCAAGA   210300
CCAGCCTGGC   CAAGATGGTG   AAACCCGTC   TACTAAAAAT   ACAAAATTA   GCCGGGCGTG   210360
GTGGCGGGCA   CCTGTAATCC   CAGCTACGTG   GGAGGCTGAG   CCAGAGAACT   GCTTGAACCC   210420
AGGAGGCAGA   GGTTGCAGTG   AACCGAGATT   GTGCCACTGC   ACTCTAGCCT   GGGTGACAGA   210480
GCGAGGCTCC   ATCCAAAACA   AAACAAAACA   AAAAGTGGT   CTAATAATCC   CCAGAACTGG   210540
AGGAAGAACC   ATAACTTATT   GATTTTGTTT   TTAACCTTAT   GTATGCCAGG   CATGCTAGCC   210600
TTGTATACAT   ACAAGGCTAG   AGGAGCAAAG   GTGCAGGAAG   CCATCTTGAG   GGAGTCCCAT   210660
```

```
ATTATTGAGA GACCGGCCAG CTGCTGGGAG AGGCTAGTTG TTCATCCTCA CTGTATGTGA    210720
TGAGAATCTG GTGACAGTCC ATTGCTGGGC ACAGCATTTA GGCAAAATGG CTCTCTGCTA    210780
TGTCAGGCAA GTGAGGCATA TTTTTGCACA ATCCTAGTAA TTCCGAACTC ATTGGGAAAC    210840
AATGGCAATT ACATCCAAGC AAGGAAAGGT CTGTGGTTGA TTTTATCTAT ACAAATTTAA    210900
AACATAATGT TTACAACCTT TCATTATAGG ACACAATTTT TAAAAAGATG CCAAACTATA    210960
CAAATAAGTT CAGAAAAGTG AGGTACTATT GAACCGTCTG GAAAACATAA ATGTATGTGA    211020
AATAATGCAA TGCATAGTTT TGCAGGGGAC TTTGTTCAAA GTTTCTCGAA ATACCATGGT    211080
CCAAAGTAGA CTAACATTAG CATTGGTTAT TTATGATGAT CAGTAAGAAT ACTAAATCAA    211140
AAATCAAAGG AAAATTAAAC TATGTCTGTT TAAAGAGAAA CGTAGTTTAC CTCAGACTGA    211200
GAGTTAAAAC AAGTTTGTGA TTCAGGAAGG TGGAATTCAG AACCTAATTG GGCAGCCTCC    211260
AACATTTCCA TTAAGGTTTG GATTCTTAAA ATTTTTCAGT CTTCGGTATG CTCTGGTAGT    211320
CTGATGAAAC TTACAGATTC TTTTCATAAA TAAGATACTT AAAGTAATTC ATAGGGTTAC    211380
AATTGTATTA GACCAATAAT ATTAAATAA TTATCAAACC ACTTGACCGT AATATGTGTG    211440
TTTTTGTTGA TATACCTAAT AGTACTTCGG AAATAAGCAA GCACGATTTC CAGATTCTTG    211500
CAACAACTAT AACCTACAAA TTTGTTATTT CTATCAGTCA CACACAATGG AAGAAAATTC    211560
TAAATTTCAG CTACAGGATA ATGAATAGAT GAAAACAAC AACAACAACA ACAACAAAAA    211620
AACTCCCCTA ATCCATATTC TGGGACACCT TGATTCCTAT TTATTGATCC CTTGAAGTCA    211680
GTGGATAGCA TATTAAGAAA CAATAGTTAC AATGACACCA CAGAAAGACT AGAATGTAGT    211740
ACTTGTGTTA AAAAAAAAA AAGTATCAGC AAGTTATGTT TGGATGCCAA ATTGCTCTCC    211800
ACTTCCTTC CCTGACACTG GCATTCCAG AACTTAGATG CTCTTACATG TAAAAGCCTC    211860
CTCTAGTGCA CCATCGAGCT TTTCAGGATT GGACATCAGA CTTTTTAGTT CCTGGACCTC    211920
TAGATATACG GCAGTCTCTG ACAAGAAGCC CTTTTTCTGT TTTAACTTTT TTTTTTTTTA    211980
AGTTTTGAGA CAACGTCTGA CTCGCTGTCA CCCAGGCTGG AGTGAGGTAG CACCATCATA    212040
GCTCACTGTA TCCTTAAACG CCTGGGTGCA GGGACTAAGG GAGCGTGCCA ACCATGCTTG    212100
ACTAATTTAC TTTTTTGTAA AACCAGTAGT CTCCAACCTT TTTGACACAA GAGACCGTTT    212160
TGTGTAAGAC AATTATACCA CGGACCAGGG GGTGCAGGGG CTGGGAGCAA TGATTTCCGG    212220
ACTAAAACTG CTCCAACCTC AGATCATCAG GCATTAGATT GTCACAAGGA GCCTGAAACC    212280
TAGATCCCTT GCATGTGCCA TTCACAATAC AGTTTGAGCT TATGAGAATC TATCTAATGC    212340
TGCAGCTAAC CTGACAGGCG GTGGAGCTCA GTTGGTTAAT GTTCGCTCAC CCCTCAGCTG    212400
TGCGGCTCAA TTCATAACGT GCCATGGACA GGGACCGGTT ACCGGTCGGT GGCCGGGGAA    212460
ATGAGGACCC CTGGTATAGA TGGTAGTCTG GCTATGTTGC CCAGGATGGT CTTGAAGCCT    212520
GGCCTGAATT AATTCTCCAA TCTCAAGCCT TTTCAACTCA GCTGCATCAC AACTTAAACC    212580
TATAGATAAC TGTCACAGAA ACTTGTTTCC AGTGTTACGC CATCTTAAAA TAATGTGGGT    212640
GGCTCTTAAA AGAGCCTTTG GGTTCTTTCC AAATTGGCCT CCCGGAAAGC TCTTTACTTC    212700
TTAGATGTGG CCTTTCTAAC ATTAACTTCA TGATGTTGGG TCAATTTTGA CTTCGAAGCC    212760
CTTGCCTTCA CTGGGCTCTT CTGCTGTTGC TTACCCTTGG CTCCTTTAGC CTTTCTCCCG    212820
CTCCTAACAG TTTTAGGAGT TGTCGCTCTC GGCTTCTTGG CTCTCTTATT GGTTTTAGCA    212880
GTCTTTGGTG ACTTGGAGTC CCTGGATAAA ACCAGCTTCT TGGTCTTGGC AGAAACTGAC    212940
TTTTTAGCCT TGCTTCTGGT AGATTTAGGA ATCACCTTCT TACTAAGCTT AAAGGAACCG    213000
GAAGCACCAG TACCCCTGGT TTGCACCAGG ATTCCCTTGT TCACTAAGCT CTTGAGGGAC    213060
```

-continued

| | | | | | |
|---|---|---|---|---|---|
| AGTTTGATGC | GGCTGTTATT | CTTCTCTACG | TCGTAGCCAG | CAGCGGCCAA | TGCCTTCTTG 213120 |
| AGCGCAACCA | AAGACATACC | TACTCGTTCC | TGTGACACTG | AAAGGGCCTC | GGTGATCAAC 213180 |
| TTGGACACAG | AGAGGTTCGG | CACTTTGCGA | CTTGCACTTA | TCAAGCCAGC | CGGCTTCCTC 213240 |
| CCTCGCTTCT | TGGTTGGAAG | TTTCTCCATA | GCGGCTACAC | CAGCACTGGC | AGAAGCTGCA 213300 |
| GGCACGGTTT | CAGACATAAC | AACAGAGAAA | CGCAAGATGT | AATAACCAGC | GAAAAGCATG 213360 |
| AAACACCCGG | GCGGCCTCGG | GGCCTTATAT | AGGGTAGGGC | GCGCTGTGAT | TGGTGCATCA 213420 |
| CCTAGGCACC | GCCCCCGCCC | CTTGGAGGAG | GAGTATTTGT | GTTTGTTTTA | CCCGGAAAAG 213480 |
| TTGAGTATAA | CAAAACCCCT | CTTTACAGAA | TCTCCCAGGG | TCTAGTGCTG | AATAATCTGC 213540 |
| GGAAATTCAT | ATTTGACATG | ACTTTTCTCT | TTTTAATGAA | AAATGACCCT | GGATGCCAAA 213600 |
| ACTATTCGAG | AAAGCCCTCG | ATTTTCAATC | AAATTCACGG | AGAGGAACAA | AACTTCCCCT 213660 |
| TTTCCTTGTA | AATTAATAAG | TAATCTTTGG | CAGAAGACTT | ATTTCATCTC | TTCAGAGTGG 213720 |
| TCTTCCAAAT | GGATAGCTTC | AAATCGGTAG | AGGAAAGAAA | TTATTCACGC | CATGATTTTT 213780 |
| ATTTAAAATT | ATTTATATAT | GTGAGGGAAG | TAACACAGAT | CTCTTAGCTG | TCTAATTGCG 213840 |
| GAGTCAGAAG | ATGCTTATAG | AATTGTCAAA | AGACTGCAGA | GGATGTCTTT | ATTTAGGCAT 213900 |
| GTGCAATCTA | ATAAATCATA | ATCCACAGGA | ACATGGGTTG | TCTGTAATTA | AAGGTGCTCC 213960 |
| CAAGTCCCTG | TAGCTTTATA | GAGGACTCTC | AAGGATGGGG | TAATATCAAG | ATCTCACACA 214020 |
| TTATGTAAGA | TTGGCCATAA | TCAGGCCACT | CTCATGACCG | GTGTCCTCAA | CTGAGTTTTG 214080 |
| CTTCTGGTTT | CATTAATTGA | AGTCCCTCT | ATCCCCTGC | CCACCCCTAC | ATCCCAGAT 214140 |
| AAACAGACAC | AGTCCCTCCC | CTAAATTAAC | TATAAAACAT | GAGGTAGGAA | CCCTAGACTC 214200 |
| AAGAACCTAC | TAGAAACTAC | AGACCCCATG | TCTAACAAGA | CTGGGCGGGT | TGGCTGGGCG 214260 |
| CAGTGATTCA | TGCCTGTAAT | TACAGCACTT | CGGAAGGCTG | GAGGCCAGGA | GTTCAAGACT 214320 |
| AGGTTGGCCT | GGTCCCTACT | GAAAAAAAAA | AAAATTAGCT | GGGTGTGGTG | GCACATGCCT 214380 |
| GCAGTCCCAG | CTTCTGGGTA | GACTGAAGAG | GATCACTTAG | AGCCCAGGAG | CTTGAGGTCG 214440 |
| CAGCTACTGC | ACTCCAGCCT | GGGCAGACCC | TCATCTCTGA | ATTGCTTAAT | TAATTAACTG 214500 |
| AGCTGGCAGA | TTTGGCTGCA | TAGCTGTGGG | GAAAGGGTTG | TTGGAATAAT | GTCCAGTGTG 214560 |
| CTCCCCTGAG | CTTCTACTGG | AACAGGTCTT | TGTGAGAGGC | CTGGAGATAA | GAGCTTGCTC 214620 |
| ACAAAGGCTG | AGGCCTTTCT | GGGATGCTGA | ATGAGTTTAG | TGTGGCCAGA | GCATAGGGTC 214680 |
| TCAGCAAAGG | AAAACTCCAT | AAGGGCCATT | TGTGAAGATC | CCCAAATACT | TGTGTGAAAC 214740 |
| ATTTGGTAGA | TATTAGAAGT | TTTGTTTTGG | TTTGGTTTGA | GACAGAGTTT | TGCTCTTGTT 214800 |
| GCCCAGGCTG | GAGTGCAATG | GTGTGATCTT | GGCTCAGTGC | AACCTCCACC | TCCCAGGTTC 214860 |
| AGGCAATTCT | CCTGCCTCAG | CCTCCCAATT | AGCTGGGATT | ATAGGCGCCC | ACCACCATGC 214920 |
| CTGGCTAATT | TTTTGTATTT | TTAGTAGAGA | TGGGGTTTCA | TCATGTTGGC | CAGGCTAGTC 214980 |
| TCGAACTCCC | CACCTCAAGT | GATCTGCCCG | CCTCTGCCTC | CAAAGTGCTG | GGAATACATG 215040 |
| CGTGAGCCGC | CGCGCCCGGC | AGACATTGGA | AGTTTTAAG | CAGAGAATTT | GTTGTATTGT 215100 |
| TGTAGTTGTC | TTGGGTTTAG | ATTTATTGCA | TAAACAATCA | TTTTTGAGAA | GGGCCCACAG 215160 |
| TCAGAAGTTG | GGAGTCTGTT | GCAATAGTCT | CAGAAGAATG | GCAAAGACCT | TGCCTAAGGG 215220 |
| GACAGTGTGG | TAAAGGAGAG | AGTCTACATT | TGAAATATTT | CTGAAACAAA | AGCCAAAAGA 215280 |
| TAAGACTTCA | AACTTCTGAT | TGCAAAGTGA | GATAGAAAAG | TTTCTTTCTC | TCTGTCTCTC 215340 |
| TGTTATACCC | ATACACACAC | ACATATGCAC | AAACACCTGA | AAGAAAAAAA | AATTCAGGGA 215400 |
| ACAGGCCAGG | TAGGGTGGCT | CATGCCTATA | ATCCCATAAA | TTTGGGAGGC | TGAGGCTAGT 215460 |

| | | | | | |
|---|---|---|---|---|---|
| GGATCACTAG | AGCCCAGGAG | TTCACAAGGC | CAGCCTAAGC | ACATAGCAAG | ACCCTGTCTC 215520 |
| TACAATTAAA | AAATTACCCG | GGTGTGGTGG | CACGTACCTG | TGGTCCCAGT | TACTCAAAAG 215580 |
| GCTGAGGTGG | GAGAATCACT | TGGGCCCAGG | AGGTCAAGGC | TGCAGTGAGC | ATGATTGTGC 215640 |
| CACTGCACTT | CAGCCTGGGC | AAGAGCGAGA | CCCTGTCTCA | AAAAAAAAAA | ATTTTTTTTT 215700 |
| TTTTTCCAGA | AAACAATACT | ATCTTAAGCA | CCAGCACTTT | AGTATATTCT | ACTGTGGACT 215760 |
| AGTTCATTTT | TAAAAGAACA | CTAGGTTGGA | AATCATGAGA | TTGATTCCAC | AACTCACTAA 215820 |
| AGCACCGTGT | CACTCAGTTT | GGAAAATATT | TCTCCTTAGA | GAGATTACAG | GTGCATCTTT 215880 |
| CTGAGCACCT | GTATGTTTTT | ACATTTGTTT | GGCTTCTCTG | ACCTTTGATA | ATTTCTGAGT 215940 |
| GTTGTACTAT | TAAATATTAG | TGGCTAGGGG | TCAAATTGTG | GATCAGGTTG | ATCCTTATAT 216000 |
| TTACAAGTTG | ACAGATACGT | TACTCCATTG | CTTTAAAACT | AACACAGAAT | TAGAGAATTT 216060 |
| AGAAAATTCT | TACATTCCAT | AATTTAAGAC | CCAGAAAAAA | AAGATTCATA | TTTTGCATTA 216120 |
| GATAGCTAAA | ATGGTACCAT | AAAAACAAAT | GATATCCACA | TATATATAGT | ATATAGTGCT 216180 |
| TCTTCTGTGC | CAGTCACTAT | CCTAAGTTTT | TCTCTCCCTT | CCCCAAAAAT | GTAGGAATTA 216240 |
| ACTTTATAGA | TGAAGAAACT | GAGGCACAGG | AATGTCACAT | GACTTGCCCA | AAGGAAATTC 216300 |
| AGTCTTCCTT | TTTCAATTCT | TTTTTCTTTT | TACTTTGCTG | CAGGGTCTCG | CTGTGTTGCC 216360 |
| CAGGATGCTC | TTGAACTCCC | GGACTCAAGC | GATCCTCCTT | CTTCAGCCTC | TCAAAGTGCT 216420 |
| GGGATTACAG | GCATGAGCCA | CTGCGCCCAG | TCAGGAAATT | CAGTCTTCTA | AACATTCATT 216480 |
| ATTGAAATAA | TATTTCCATA | AACATTTCT | TAGATAAACT | TTGGCATCTC | TAACTTCTAA 216540 |
| GTAGCAAAGT | CATGGAAACA | GTCACAGAGA | AAATAACTTT | ATTTAAAAA | TAATAAATTC 216600 |
| TTATCTCCGG | TGATAAGAAA | AGTATACAGC | CCATTTTTA | AAGTATTAAT | TTTACATTCT 216660 |
| AATTTGGTTT | TTTTAATGTT | TACCATATAT | TTCTCTTTCT | ACATATGTGT | GTGAGTGAAT 216720 |
| AAAATAAAGG | CATCTACAGA | TTTTTACATG | TTCAGTGAGA | TTAGCAGGGT | TTCACTTGAC 216780 |
| AGCACTCTTA | CCATACTCAC | TTCTTGGCTT | TTCCTGATAT | CTAACATTTT | TAAAATGAGT 216840 |
| AGTCCCTTTT | CATATGATTC | TTCCTTTTC | AAGCACTATT | TTTGAACTTT | ATATTTGATT 216900 |
| GGCAATAATT | TTTACAGACA | TTATTTTACG | ATTAACTTTA | ACTCTGTTCA | AATGATTTCT 216960 |
| TCATTTTCAA | GTATTTTATT | TGAACTGCTT | TTTTTGGTTC | AACTACTGAG | TATTTAATTT 217020 |
| GTCTGTTTTG | TAGAAAGGGT | ATGTAGATAA | TTCCATGTTT | TGTAAAAGTT | GTCTCTAAAA 217080 |
| ATCTAACAAG | TGTAAGTACG | ATGCTATTAC | AGGGCTGAGA | GACACAGAAA | AAACACACAC 217140 |
| ACACACACAA | AATTTTTTTT | TAAGTATTAC | TTGGTCTCTA | AACTAAAGAA | TTTACCATCT 217200 |
| ATTTTGGGAG | ATGAAATCCA | AACATAAGCA | ATGACAACAA | TTATTATGTG | CTTAAATCAA 217260 |
| TGTCCAAGAC | AATAATTGAC | CCCAAGGCAG | GGAAATCACT | GAGAGAGTAT | AGCAGAGAAG 217320 |
| GTGTCCTCTC | TGTTCAGATG | AGCCTGAATA | ATTTGTTCAG | TAGGTTTCTG | CTACTCATTT 217380 |
| ATAAACTGCA | CATCTTCTGT | AGTCCTGGAA | AATGTCTAAG | AGGAGAGAGG | AACTAAGATC 217440 |
| AGGGCCACCA | TTTAATTAGG | AAGTTCTGGG | AGTACCTGAC | CCAGAAGAAA | GATCAGCATA 217500 |
| GCTGAAAATC | ACCCATAGGA | GAAACATCTA | GGTAATCTTA | TTTCTGTTCC | ACCTGACATT 217560 |
| TCAACCTCTC | TTTTCAGCTA | TAAGTATATA | AGTACTTATA | TGTAAGTAAA | GAAATTTACC 217620 |
| CACATCATGT | TGTTTTTTAT | TCAATGCTTA | ACATGTATAA | TGCTAACAAC | ACAGACTTGA 217680 |
| TGTCCAAAAC | ATTTCTATGA | ACAGCTCATT | ACTGGATGAC | TGAAATAATT | TTTCCAAGCC 217740 |
| ACGTGGAGGT | TAATGAGTCA | GTTTTTGAAA | GCAAGGAGAG | AAAAACATTA | GAATTTAAGG 217800 |
| TGACGTTTCT | GTTGCGTTGT | AATCCAGAAT | ACAGAATAGT | CAGAGAAAAG | CAGAAAGTCT 217860 |

-continued

| | | | | | |
|---|---|---|---|---|---|
| TTCTTCTTAA | ATTTTCTGAA | AACCAAGGTG | TGCATTAAAA | TGGTACATGC | CTACTTCCCT 217920 |
| TTCCCTTTAC | CCTTTTTTCC | TGCATGGAAC | ATAGATATGA | CCCCTAGACA | TGCTGCAGAT 217980 |
| GACCATGAGG | TTGAAAGATA | CATGGAAGAT | GGTTAACACA | GGATGATAGA | AGAGACCTGC 218040 |
| ATACTTGGGC | AGCCTAGACA | GCTCCTGCCA | GCCCCCAACA | AAACAGCCTA | GCCTTCTTGC 218100 |
| CAATCAAGAA | AAAAATCCC | TTCTGGTAAC | CCACTGTAAG | TGAATTTCTG | TAAATGTGGC 218160 |
| CCAATGTATC | CATAATTGAT | ATACAAATAT | TAGTTTAGTG | GGTAGCACCT | CTCCATGAGC 218220 |
| ATGTCGACTT | CATGAGACTG | AGATTTTGA | CTGTCATGTG | CAGTTGTCCC | ATTACAGTGC 218280 |
| CTGGTGCATG | GGAACAGCTC | AACTGTGCAT | ACCCATTGAA | GAAATAGATG | CATGGTCAAT 218340 |
| CGAATTTCCA | GGTATATCAT | ATGTTTCCAT | AAAAAAAGTA | AACATACAGC | ATATCTCCTT 218400 |
| CCAGTTTATT | TATTTTTCTC | TCTAGGACCA | ATTTACAGTC | TATCAGCAGT | GCGTGAGCAC 218460 |
| CTGTTTCACC | ACATATACAA | ACCCCTCCAA | GACTATAAGG | ATATCATTAA | GCTTTTTATC 218520 |
| ACTGTCAGTT | AAGTGGTAAA | CATAGTTTTC | TACATACTTT | GCATTTTGT | TTCTCATGAG 218580 |
| ATTCAATGTT | TTACATGGGT | AAGTTGTTAG | ATCATATTTA | TTCAAGATGA | GGCATTTGTC 218640 |
| TCCTGGTAAG | ACATCTTGGT | CTAATGCTGA | CTCTGGGGTG | TGGACATTTG | GCTGTTGACT 218700 |
| GTGAGGTGGC | TATCTACATG | TGGAGTGGAG | GAGTCCTGGC | CTTGGATTGA | GGAGAACAAG 218760 |
| GTCAACTTCT | CACCTCACTT | GTTTCTGGCT | TTTGTGACCT | TGGACAAGTT | TAACTTTTCT 218820 |
| CTCTCCTAGT | CTTAGTTTTC | TTGTCTGTAA | GTGACAGCAA | TGATGCTGTC | TTTGTTGGGG 218880 |
| TGGGCTGCCA | TAAAAAAATA | CCATAGATTG | TGTGGTTTAA | ACAACAAAAT | TTTATCACAG 218940 |
| TTCTGGAGGC | TGGAAGTCTC | AGAGCAGGGT | ATAGCATGGC | TGGATTCTGT | GGAGAGGGCT 219000 |
| CTCTTGCTGG | CTTGTAGAGT | GCTACCTTCT | CACTGTGAGA | GCTCACATAG | CCTTTCCTCA 219060 |
| GTATATGTGC | AGAGCTCCCT | CTCTTCCTCT | TTTTTTTTT | TCTTTTAAAT | AAATTATTTA 219120 |
| ATTTGGAAGA | CCAAGTGCAG | AATCTTCCTC | TTCTTATAAG | GCCACCAATC | CTATCCAGTT 219180 |
| AGGAACCCAT | CCTAATGACC | TCATTTAACC | TTAATTACCT | CTTATAAGTC | CTGTCTAGGA 219240 |
| ATAGAGTCAT | ATTGGGGTTT | ATGGCTTCAA | TATATGAATT | TGGGGGGATG | GGGAGACAAT 219300 |
| TCAGTCCATA | GTAAACACTT | CCTCAAAGAG | TAGTTATAAT | GTTATAAGA | GACAATGTAG 219360 |
| GTAAAGTAG | TTTCAGTTGC | ATGCAGCTAA | ATGCAGTTTA | GTATCCCTTC | AGAGTCCTCC 219420 |
| GCAGAAAAGG | CACCTGATAA | ATATTTATGT | GGCCTTAACC | TAAGGTATTA | TTCTTTATAT 219480 |
| AGTGCCTTCC | CATGTAATGA | TTGATGTCAT | GTTTATCATT | TGCAGTGCAG | TTTATTTCTT 219540 |
| ATAGGTCATG | GCTACAGAAA | CATGGGAGAA | TGACCATCAT | TAATAGGTCA | TTAGAATATG 219600 |
| TAATTTCAAT | TTTTTTTTCT | TTTGAAGGAC | TATTAGGTTA | ACAATGATTT | TTAAAATTTA 219660 |
| TAGTAGATAT | GAGTGCTATA | AAACAGGAAT | TTCCATATTA | TTTTGGGATT | ATAAATTGGT 219720 |
| ATGATCCTGA | ATAGCAATTT | GGCAATGTAT | ATGTTAAGAA | CCTTAGAAAA | TGTTTTCAC 219780 |
| TTTTGATTTA | GTATTTCCAC | TTCATGAAGT | CTATCCTTAG | GAAATAATAT | TTGAACAAAG 219840 |
| ATTTATGTAC | AAAGATGTGT | GAGCTATATA | ATCTATAATA | TAATGCATAA | AAATGGGAAT 219900 |
| CAATTGAAGT | AGTCAATAAC | AAATACATAA | TTATCAATAT | ATCCATAAAT | TATACATCCA 219960 |
| TAAAAAGTT | TCTAAGTATA | TTTATCTAAA | TATATATCAT | GACACCTAAA | TTTATTTTAT 220020 |
| ATATGATACA | TGATGTGAGA | TATATGTATA | TATGAATATG | AGTATATATA | ATATACATAT 220080 |
| AAAAGAATA | GGAGATACTA | GGAGTTATTT | TAATTTTGTC | TTTATGTTTC | CTGTGTCATA 220140 |
| AATTTCTATG | AAGAATATTT | TAATAGTTTT | ATGCATAGAA | AAAAGAGCTA | ATTTTCTCA 220200 |
| GCCAGGTGTT | CATTTGTCCT | TCTTTGATTG | TTCAAAATAC | CTCCATTTAT | CTTCTTCTAG 220260 |

-continued

| | | | | | | |
|---|---|---|---|---|---|---|
| GATCACTCAT | TTTCATTGGT | TTATTTGCAA | GATGAAACAG | TGTCCAGCAG | TGACGACTGT | 220320 |
| TGGAAAAGAT | ATGTCTAAAA | GCTGTTGTCT | CCCCCTGGAG | AAAAGAGAGA | GAGTGATTGA | 220380 |
| TTCACTTCTG | TAATTTATCA | GATATGAGAT | ATTGTATTTG | ACTCTGAGAA | CAATGATAAT | 220440 |
| GATGATGGCT | AAAGTTCACT | GGATGTTTGC | TCTGTGCCAG | GCAGTGTTTT | AAGCACTTTA | 220500 |
| CACAATAGAT | ACCAATGCAT | TTAGTTGTTC | CAACAACCTT | ATGAGATACC | TACTGTCATT | 220560 |
| CTCCCTGCGT | TATAGATGAG | GAAATTAAGG | CACAGAGAGG | TTAAGTTTCC | CAGGTAGCAC | 220620 |
| AGCTGTTGGA | TAATGAGCCT | GTGCAGTAAA | CCCACATCCT | CTAGCCCTTG | AATGTCTGTA | 220680 |
| CGCTCTTAAA | AGATGAATGT | AACCTAGTCA | GTGTCCTAAA | GTTCCATTTG | ATCTAAACTT | 220740 |
| GAAGGATAAA | AATTTATCCA | GTGAGGAAAA | AGACTTAGTG | TTTTTCATAA | AGAAGATACA | 220800 |
| GCGACGAAGG | CCAGGCCGTG | GGGACTGTCT | GATTTTTAGA | GCCTAGAACC | CTGAGCACAC | 220860 |
| TCTCTAAACC | CTCCAACATG | CTCTTACTCT | GTTGCCTGCT | GAGCATCTTT | GATCCACTCT | 220920 |
| TGAGGCTAGC | AGTTTTCCTT | CCATTCAAGA | TCTCACAACG | TGTATTGTTC | TCTGCAGATT | 220980 |
| TTTAAACAT | GCAATTTTAT | TTTTTAATTG | TTAAAAATAT | ATTTATTTCA | GTGCACTGAA | 221040 |
| GCTCAAATGT | GTGTGTTTTA | AAATCTAGTG | TCCAAGGTTC | ATTACCCCAA | TTGTTTAAGC | 221100 |
| AAGTCTAACA | ACAAAGGGG | CACATTTTAA | TTTTCAATTT | TTTTTGTTC | TAGCCTACAG | 221160 |
| TTGAGTTTGG | GCAAATAATA | GTAGACAAAA | AAGTGAAAAG | AAAACTAAGG | ACAAGAAAAT | 221220 |
| AAAGGAAGGG | AGAATGGGGG | GAGAGGAGGG | AGAAAAGTGA | AAACAAAAGT | TTATTCATAT | 221280 |
| TTCTCTTGAA | TCCAATTCTT | TTACCATTTG | AAAACTTGAT | ATGGTCAGAG | AATAAGCCTA | 221340 |
| GAATTTTAAG | TGATGAGGAT | AAGGTTTTAC | CACAGGTAGC | CTCCTCTACA | TAGGTCTATT | 221400 |
| TCCTCATAGA | ATGAGAGAAG | CCCCATCATT | TCTGCTCTTT | TACCCTTCTG | AGCCAGCAGC | 221460 |
| AAGGAGATCT | ACTATCAAGG | CATGAGCAAC | TGTAGAAACA | TGAGACCAGA | TGTCTCTATT | 221520 |
| AATTATTCTA | CAAATTGCGC | ATTGGATGAT | AAGGTTACAT | GAATCTTTAA | ATCAGCAAAC | 221580 |
| CAAAGTCCCA | TTATTATTAC | ATATTTTTC | CTCCTCAGAA | CTGAAGTGGG | GCGGGGTACA | 221640 |
| GTGACTCACA | CTAGTAATCC | CAACAATTTG | GGAGGCTGAG | GCAGGAGGAT | CACTTAAGCC | 221700 |
| CAGGAGTTTG | AGACCAGCCT | GGGCAACATA | GTAAGACCCC | ATCTCTACAA | AAAACTTTTT | 221760 |
| AAAAAATTAG | CTTGGCATGG | TGGTGTGCAC | CTGCTGTGGT | TCCAGATACT | CAGGATGCTG | 221820 |
| AGGCAGGAGG | ATGGCTTCAG | CCCAGAAGGT | GGAGGTTACA | ATGAGATGCG | ATTGCGCCAC | 221880 |
| TACACTCCAG | CCTGGCAGCC | TGGGCAACAA | AGTGAGACCC | TGTCTCTGAA | AAAAAGAACT | 221940 |
| GAGGTCAAGG | AGTAGTAAGA | AAGTGGCTCA | TTCTCCAGAT | TTACTCTCTT | TTTCTTAATT | 222000 |
| ATAATGAACT | CATGATACTT | GAGGATATGT | CAAACTGATC | TTCAGACCCC | AAAGAAATTA | 222060 |
| CTCAGAGCCT | AGAATACCTT | TCAGGAAATG | TTACAGTGGT | ATACTCTACT | CAATTTAATT | 222120 |
| TTATGCTTGG | TCATCCAGGA | TTACACAGGC | TAAAGGTAGG | AAAAGTTTCA | CTAATTTTTA | 222180 |
| ATGTCTTTTA | ATTTAGGACT | ACTGGGATTG | TCTGTCAATG | TGCTGAATAT | ATATATCCTT | 222240 |
| CCAAATCTGG | AAGATTTAAG | AGAAATGATA | GTTATCATTC | TTTAAGTCCT | TAGGAATATG | 222300 |
| CCTAGAGAGC | TAATTTCATA | TGTTCAGGGA | AAAAAAGTGT | ATTTTTTCTC | AACCTGTTGG | 222360 |
| ACCCCGGTAA | ACATACTATG | ATCAACTGGC | ATTTTCATAT | CAAATAATTT | ATGAAATTCT | 222420 |
| TATAATTTAT | AGAAGGCCAA | CTCCTACCAA | AGTCTTCAGT | CATAAGCTGC | TTCAAGTCCT | 222480 |
| TTTAGGAGCG | TAAAGATGGT | TATAAATAAA | ATTTGTCAAA | CAGCAGTAAA | CACAGTGGTT | 222540 |
| TATATGCATT | AAGGATCTTT | AATCTTCACA | TACTTCTAGA | AGGTAGGTGC | TATTACCATC | 222600 |
| ACTGTAAAGG | TATAGAGAAG | GATACTAATG | CACAGAGAGA | TTAAATGACC | TGCCTCAGAG | 222660 |

```
TCCCACATCT  TATATGTGGT  GATCTGGGAG  TCAAACTTGG  AGTCTGTCTC  CAGAAGCTTC  222720
ACTTTTTGTC  ATCATTGAGC  AGTGCTGTGC  AGCCATTTTA  CTAGCATGAT  ACCACGTCTG  222780
GAACTAGTGT  TCTATAGGTG  CTATTTCATT  TAATCTTCAC  CCCATCTTTA  TGAGTAGGGC  222840
AATTATTACC  ACTCTATAGG  CTCAGGGTAG  TTGAGTTTGT  CAAACTGTGA  CTGAAAGACA  222900
TTTAATTTTT  GGCATACTAT  TTACTTGTGC  TCAAGGTATA  TCAAGCAATG  GACTGATTTC  222960
ACTCAACAAA  GTATTTTAAA  AAGATGATTT  ATAAATAGA   AATGGGAGAA  AAAAACTACA  223020
AACTGTCTAG  GAATAGGATG  TTATGTTTGC  ACATTATTTT  CAGTAGAAAA  GAGTTTAGTA  223080
TGGATACTCT  CTTCTTGTAT  AAACCAAGAA  TGTTAAAAGA  AAACAATTAG  TGATTCTCTA  223140
GAAACAATTA  GTGATTCTCT  AGAAACACTT  AAGATTGGCT  GTGCAGCACT  ATGGCTATCT  223200
CTGTGTAGTA  TTTTCCACTG  ACAACCAACA  TTTCCATGTT  AGGTAGGCCA  TGTCTTCACG  223260
ATTTCTGGCA  CCAGAGTTTT  TCAACTCCTC  CATTTTTGGT  AAAAATATCT  CATAAAGGAG  223320
CAAGTCTAAC  CATGTGAGTT  TGTTTAGTTT  TTTGTTTTTT  GTTTTTTGA   CAATGGCTTT  223380
GTAACAACAT  TTAATAATCT  GCATATTAGA  GAAGCACAGA  AGTAGGGCAA  AAAAAAAGT   223440
TATGAGGGTA  ATTACAAATA  TTATAAGAAT  TCCTTAAAGT  ACAAATTGTC  TCCAAGAATT  223500
TAATTGGCTT  GTCTTAGATG  AATAGGTCTC  AAAGATCAGT  TTGGTCAAAG  ATCAGTTTGG  223560
TCAACTTTAG  TTAAACAAGT  TCATTTTCC   TAATTGATTA  TTTTGACTCA  AATGTGGGCC  223620
ACAGGCAGAA  ATAAATTTTC  TAGTAAATAT  TCTTATTTAG  GAACTTTTAG  TCAAGTTATA  223680
AAGGTCCTTG  TTACAAACCT  GCAAAAGTT   AGCATGCCAA  TATCTTAGTA  AAATATAACT  223740
GAGATTTGTT  TATTTGCTTG  TTTTTTAATA  CTTGGGAGGG  CCAGATCAAA  ATTTCATCAC  223800
TGGAAAGACA  GATAATGGAG  AAAAGGACAA  AACAGAATAA  TACCACAGGT  AAAAGAAGGA  223860
AGAAGCTGTC  TATTTCAGAC  CTCATCTTCC  TCTGTAGACT  TTGAAGAGGA  AACTTCCTAC  223920
TTCCAGAATT  CTGGAGGTCT  TTTAATGAAT  CTCAGAACTG  TATTTTAGT   GATAGTGTAT  223980
TTCTCAGTGA  GATTCCAAAT  GTGTTTACAC  TGGGAAGCAC  ATATCCATCT  GCTCTGAAGT  224040
ATAAAGCAG   TATTTGTTGT  TTGAAGTACT  GAAAATGGAG  GTTCCAGCAT  TGTTATAATG  224100
TTGTCAGAGA  AGATTGGTTA  TTACATTAAG  ATATGAATAT  AAATCATGGC  TATATAAAAA  224160
TAAGAAAAAG  ATTGAAGTCT  TATTTTAGAG  TGACAATCCA  TAGTAAATTG  AATGTACCAC  224220
ATTAACAAAC  AGTAACAACT  TTTTAAATAA  GTAAAGGCTC  AAGGTAGTCA  TTATCTCGAA  224280
TGCTTACTTG  TGTTTCTCTG  TAGCTATAGT  ACTTGATAGA  GTCAGAGCTG  TTTGGATTAA  224340
CCATAGCCCT  TAAACAAAGC  AGGCAATTGT  GTTCCCGCAT  AGGCATGACG  AAAACAGAGG  224400
CAGTCATCCA  AAACCTGCAT  GGTCCTCTAC  GCCCACACGT  ATACAGTACG  TGATTACAA   224460
ATCTAAAGTG  GCGAAAGCAA  CAGTATCTAT  TCTAAGGCAA  TCATATGTTC  TCTTATCTGT  224520
TTATCAATGG  TTATTCTAAA  CTGTGTAAAA  ATGTTATTTG  CATAAAACTA  CACTGTTTCT  224580
TGTGATTTGT  ATTTTGTACC  CTCCAATTTA  GAAATTGTCC  AGGTATCCAA  AGATTGAGAA  224640
TTAATTTACT  CAATTTAATA  ATATTCACCT  AAATTCTTAA  AGTTATCATA  CACTGTGAAC  224700
TCAGTACTTA  AGCTCACACA  TTGAATCCTT  ATAATTAGTA  ACATAAAATT  TAATTCCATT  224760
TTTAAAAATG  ACATTATCTA  TTATCATTTA  ATTTGGTTCA  ATGAATAATT  TACAATTTTA  224820
GAATAATAAA  TAAAGTGATG  TTAACTCATG  TAACCAGTAC  AACTAGTGGA  AGAAATTTAG  224880
TAAATGCAAG  TTAAATTAGC  TTTTGTTTTT  GTTTTTAGA   ATATGAACCC  TAAACTTGTG  224940
TATACTATAA  TATTCTGCTA  ATATTATTTT  TACAGTATAA  GAATAAAGAA  GCCATTTTA   225000
AAATGAAATT  ATTAAGCCAA  TTTGTCCAAA  AAAAATCTTG  ATTAGATGTA  TTATATATTT  225060
```

```
TCCTTATTAA AAAAACCTAA TAAAAGAGGT ATTAATATTT TTAAGTTATT TAAAAATTGT 225120
GAAGTATTTT TTTTACAAAA TACTTTAAGC TGTTAACTAA GACCACTAAT GAAACTCACA 225180
GTTAAACTTT TTTTCTCTTA ATTAGAACTT AAAGAGGTAG CACATTTAAA GCACAAGGAA 225240
AATTTTTGAT TTTTTTTTAG ACAAATGAGT TTTTATTTAA ATTGATGTAT TTTAAGTCTT 225300
TATGTAAGCC AACTAAAATT TAAGATTACA TTATAATTTA TTAATTCCCT TAAGTGGATA 225360
ATTTCACAAT TATTTAAATT CATAAAATAA GATAGTCTTT TCTGGGCACG GTGGCTCACG 225420
CCTGTAATCT CATCACTTTG GGAGGCCGAG GTGGATCACC TGAGTTCGAG ACCAGTTTGG 225480
CCAACATGGC GAAACCCCAT CTCTACTAAA AATGCACAAA TTAGCCAGGC GTGGTGGTGC 225540
ACCTGTAATC CCAGCTACTG GGAGGCTGA GGCAGGAAAA TTGCTAGAAC CCTGGAGGCA 225600
GAGGTTGCAG TGAGCCGAGA TTGTGCCACT GCACCCCAGC CTGGGCCACA GAGCAAAATT 225660
CTGTCTCAAA AAAAAAAAAA AGATAGTCTC AATCTTATTG CCAATTAGGA AAGCTAACCG 225720
TGCTAATAGA ACAGAATTTA AAGTGGGTAA AAACAGAGCC ATAGGTTATC TATTTAGCAT 225780
GTTGATCAGT TAAAGAAATA AAAGTATGTA ATTAAGATCA GAAGTCCCTC AGGTGGCACC 225840
ACTGCTGAGA ATATGAATAA TTCTGATTCT CAGTTTAGAA GAAAATTCTA GTTTCCTAGT 225900
TTCCAGCATC ACATCCCTTA CAATAAACTC GTTAAGGTTT AGAAAATATT AAATCTTTGT 225960
TTTATTCAGA TATTGAAAGC ACTCTTTTTT TTCCCTGACT CAATAGTCCA ATTTGTAACA 226020
ACATTATGTT TCTTCTGTCC TCTAACCTTA CTTAAAGAAC GTGAAGGGGC AATAATGTGA 226080
AATTACTAAA ATTAATAATA AGCTGTAGAG CCTCTGCCAT AGCAGTTATT GAGACCAGAC 226140
ATTCGGTTTC CTTGATTTCC TTTTTGTCTC CTGTTAGTCC TAACACTTTC TTAAAGTCAA 226200
AAGTTATAAC AGGGCAGCCA TTTTATATTC ATATCATCTT AACACAGGAA TACTGGTTTT 226260
GCAGATATCG ACAACTATTT GGACTCAAAA AAGACAAGTT TTGGAAGGTG GAAAGAGGCA 226320
TACAAGCACA AAACATCAAA TCCCATGTAA AGTCAGAAAG AAAAACACCA ACTCTAACCC 226380
TGTGTCCTCA CAGAGAATAT CAACATCTTC AAACAAAAAC ACCCCAAAAA AAGGTTAATA 226440
AATAAACCAG ATTTCCTGTC CTCTCCACTG ACTAATCACT TAATGATGTG ACCAGAAAAC 226500
CAGAATTCAA ATTCTACTAC TGCCACCAAT ATGCAACCAA TCAGCCAAGT CCAATTAGAA 226560
TAACCAAAAC AAACAAACGC GGACGATAAA CTTTTAGCAT GCAAAAGCCA AAGGAAAGTG 226620
AACAGAAAAC TCAAAGGGTC CAGGGATAGA CAACCTGTTT CCAAGACACA CATTTCTGTT 226680
GGTTCTTATT GTATGACTCA CATAAACACT GTCTTGGTGG AAAATTCAGA AATAAATGAC 226740
CAAGAAGTTA ATAATTTGCT TACTGGGTAC TTGTACAGAA GAGAGAACAA GCAATAGAAT 226800
TATTTCATCT AACACAGGCA AAAACATAAT CTATGTAAGA GAAAGGGGAA AAGGCGGGGG 226860
AAACAATACT GAATTTTGTT TGCAGATTTT GGTTACACTG ATTAGTTAGT TGGCAGGTAA 226920
GAAAACGGTC AGTCTGAATG GGAATAAGTG ACCAGGTCCA TTACAGGCAT AGAAAAAAAA 226980
AAAACCATTT AGGCCCGGCG CGGTGGCTCA AGCCTGTAAT CCAGGACTTT GGGAGGCCAA 227040
GGCGGGCAAA TCACCTGATG TCCGGAGTTC GAGACCAGCC TGACCGACAT GGAGAACCT 227100
CGTCTCTACT AAAAATACAA AATTAGCCAG GGTGTCGTGG CGCATGCCTG TAATCCCAGC 227160
TACTCCGGAG GCTGAGGCAG GAGAATGGCT TGAACCCGGG AGGCGGAGGT TGCTGTGAGC 227220
CAAGATCGCG CCATTGCACT CCAGCCTGGG AAACAAGAGA GAAACTTCGT CTCTAAAAAA 227280
AAAAAAAAAA AGAAAAAAAA ATTTACTTGT GAGGGACTCT GGAAATTTCA TTTCTCATCA 227340
GAATTTCTCA GATAAGTTAT CTAGGCAAGG CAGCCTGTGA TTGCACAGCA GTGTTCAAGT 227400
ATAAGGCCTT GTCTGGCACC AAAGACAGGC CTTAGTTTAT TTCCCAGGTG TGAAAGAAAT 227460
```

| | | | | | | |
|---|---|---|---|---|---|---|
| TGCAGATTTA | AGATCACACA | GTCCTTATGT | TAAATAACTG | TAACCTAAAT | TACATGGTAT | 227520 |
| TTAAGTTTGT | AAAAATCTGC | TTTAACACTA | ATTTTATTTA | TTGTATATTC | CCGGTTTTTA | 227580 |
| ATGGAGAAAG | CAAACTTCTA | GGTGCTAAAA | ACGTGTTCTA | GACTTGAATA | AAAAGATAGG | 227640 |
| TAGACTACGT | CTAACCCTTC | ATCTTAAAAT | CTTTACCTGG | AAAAGACCAT | GAGTAAAATA | 227700 |
| CTTAAGGGAA | TGTGGAATTT | CCCAGGCCAC | AAAGCGGCCT | GCAGTTGTCT | AGGAAGGGAG | 227760 |
| AGTCCTCTAG | GAGATACAGT | GTATGTGCTA | AGTTTAATGA | CGTCTCCTCT | TCATTCTCCC | 227820 |
| CCACCCAGCG | CCTAGTCCTT | ACTGGCCTTC | AGTTCAGTGT | TCGAAGGCTT | GTCAATTTAC | 227880 |
| CCAGCAGTTA | AGAGTTGGCT | TCTCCTAAAG | CAACTTTCAA | ACTTGTCTGC | ATGTTACAAG | 227940 |
| CCCCCTACGG | AGATTTTAAG | TTTCAATCAG | GCAACACACC | ATTTATGGCT | GACTGAGCAC | 228000 |
| TGGGATTCAA | GCAAAATTTG | ATTTGATTTG | AATCTTGAAT | AAACCAGTTG | AATAGAATAA | 228060 |
| GATGTATGAA | GCAACATCTG | GCGCAGTGCT | TACATCTTTA | GTTCTGTACT | GCCTTAGTGT | 228120 |
| TGTTATCAAA | ACTGACGCAT | ATTAGTTAAA | AGACTATTAC | CGGGGCAGTT | GGAAACCCAG | 228180 |
| GAGACACACC | TTCAGTATAC | TACGAAGGTG | TGCGCCACGA | AAACAGAGGG | GGAGTCCTTC | 228240 |
| CTTAGGCAGT | TACTGCCCAG | GTTCCCACTC | CGGTCCGCTA | TGTAAATCAG | AGTCTCAAAA | 228300 |
| CAGCTTTCCC | TCGATTGGTT | AATATTTAAA | ATGACAGGAC | AGCCTATTGG | CTAGAAGCTG | 228360 |
| GTGGCGAAAT | TATGACATTA | CGGCAACCGT | TGATCCTGGC | GACGTAGACA | GGGACAGACA | 228420 |
| GCTGGGTCTG | AAACCTAAGC | GAGCCTGCGG | TTTCTTCCGG | GAACGCCGAG | TTAGCAAAAT | 228480 |
| GGCCGCTTGT | CTCCATTTTA | AATTTAAGCA | CAACGAATTG | ACCCCAAAGC | CATTTTTAAT | 228540 |
| GGCTGGCTTC | TTTCGGGTTC | AGGACCCTTT | GTCCCTCTCT | AAGCTGCAAC | ACTTGTCCCC | 228600 |
| ACCCCTCTCC | AGTTCCTATA | TTCTAATACC | CCTCCGCCGC | CAAATAAAAT | TTGGCGTCTG | 228660 |
| GCCACAGCTC | TTTTAGTGGG | TATCTGGGTG | GCTCTTAAAA | GAGCCTTTGG | GGTTAGGTGT | 228720 |
| TAAGACGCTT | ACTTGGAATG | TTTACTTGGA | GCTGGTGTAC | TTGGTGACGG | CCTTGGTGCC | 228780 |
| CTCCGACACG | GCGTGCTTGG | CCAGCTCTCC | GGGAAGCAGC | AGGCGCACGG | CCGTCTGGAT | 228840 |
| CTCCCTGGAG | GTGATGGTCG | AGCGCTTGTT | GTAATGCGCC | AGGCGGGAAG | CCTCGCCCGC | 228900 |
| GATGCGCTCA | AATATGTCGT | TAACGAAAGA | ATTCATGATG | CCCATGGCCT | TGGAAGAGAT | 228960 |
| GCCAGTGTCG | GGATGGACCT | GTTTCAGCAC | CTTGTACACG | TACACAGAGT | AACTCTCCTT | 229020 |
| GCGGCTGCGC | TTGCGCTTCT | TGCCATCTTT | CTTCTGCGCT | TTGGTCACTG | CCTTCTTGGA | 229080 |
| GCCCTTCTTC | GGGGCGGGAG | CAGACTTGGC | TGGCTCAGGC | ATCTTAAAAC | ACCAGAAATG | 229140 |
| TGTCGAAAGT | AAAGAGCGGA | TTTCTGCTAC | TTATAGGGCT | TTTATGCTAA | TGAGGGATGG | 229200 |
| AGAGTACCTC | TTAGTTAATT | GGAAGACAAA | CTGCACAGTT | GTCATCCGTG | GCAGAGCTA | 229260 |
| TGCAAATGAG | GTATGAAAGT | ACAGCTTTTC | TATTGGCTAT | CTGACTAGCA | TTTGCTACCG | 229320 |
| ACCAATCAAA | AAGTCGGATT | TACTCCCCAG | GAACTACCTA | TAAAAGCGGC | CATGTTTTAC | 229380 |
| ATATTTCTTG | ATTTTGTTTG | TTTTCTCGTG | AGCTTAGGCC | GCTGGTTTTG | GTGATTTTTG | 229440 |
| TCTGATTGCA | ATGTCTGGAC | GTGGTAAGCA | AGGAGGCAAA | GCTCGCGCCA | AAGCGAAATC | 229500 |
| CCGCTCTTCT | CGCGCTGGTC | TCCAGTTCCC | GGTGGGCCGA | GTGCACCGCC | TGCTCCGTAA | 229560 |
| AGGCAACTAC | GCAGAGCGGG | TTGGGGCAGG | CGCGCCGGTG | TACCTGGCGG | CGGTGTTAGA | 229620 |
| GTACCTGACC | GCCGAGATCC | TGGAGCTGGC | CGGCAACGCG | GCTCGCGACA | ACAAGAAGAC | 229680 |
| TCGCATCATC | CCGCGCCACT | TGCAGCTGGC | CATCCGCAAC | GACGAGGAGC | TCAACAAACT | 229740 |
| GCTAGGCCGG | GTGACCATTG | CTCAGGGCGG | CGTCCTTCCT | AACATCCAGG | CCGTGCTTCT | 229800 |
| GCCTAAGAAG | ACCGAGAGTC | ACCACAAGGC | CAAGGGCAAG | TGATTTGACA | GGTATCTGAG | 229860 |

| | | | | | |
|---|---|---|---|---|---|
| CTCCCGGAAA | CGCTATCAAA | CCCAAAGGCT | CTTTTCAGAG | CCCCCCTACC | GTTTCAAAGG 229920 |
| AAGAGCTAAC | CTCACTGCTT | GTAGGTAGAA | GGAAAAAAGG | CACTAAGGTA | AGTTAATTTT 229980 |
| ATGCCAACCT | TGAGCAAAGC | GTATTACTGC | TTTTCGGTTT | TTGGGGAGCG | CTGTTACTAA 230040 |
| AGGTTGGTCT | GTTTGTATGT | AATAGTAGGT | CAGTTACGTA | CTATCATACT | CTAAAGAAAT 230100 |
| ATTCTAGTTA | ATGCTTTGTA | AGATCGACCA | TAGTTAGTGC | CTAACAGTTT | ACATGCAGGG 230160 |
| ATGCCTCGTG | ATCTAAACAC | TTCGTTGTGA | TTACTTTAAA | AATGTAAATT | GAAGGCAAAA 230220 |
| CTCTAACGTG | TTGGTAACCT | TGTTTGGTCC | TCCGACTAGT | CCCCCGTCTA | TTTTTTTCTC 230280 |
| AATTTAGGCT | GTAGGCAGCC | TCACTTTCCT | AATTCTGTGA | GAGTTATAGG | TCCCATTCCT 230340 |
| GCTAAAGTGC | AGAGTATATT | ACCTAAAAGT | TAACCAGGGA | GTTGAAAGGT | GTCTGTAAAA 230400 |
| CAGACTAATG | TCCCTAATGT | AGAACGGTGC | CTGACATGCA | ACTTACTCTT | GTATTTAAG 230460 |
| AAGCTCAAGC | GTCTAGGTTG | CCATTACAGG | CAGAAAAGGA | AATAGAGTGG | GGCCTGTGGC 230520 |
| CACTCAAAAA | CCTTTGCTTT | CTGCTCACCC | CTCTAATCCT | ACCACTTTGG | GAGGCCGAGG 230580 |
| GGGCTGATCA | CCTGAGGTCA | CGACTTCGAC | ACTAACCTGG | CCAACATGGT | GAAACACCTC 230640 |
| TCTACTAAAT | AAAAATAATA | AATAAAAAAA | TAAGTTGGGC | GTGGTGGCAC | ATACCTTGTA 230700 |
| ATCCAGCTA | CTCTTGAAGC | TGACGCAGGA | GAGTCGCTTG | AGCCTGGGAG | GCGGAGGTTG 230760 |
| TAGTAAGCCG | AGATCGTGCC | ACTGCCCTCC | AGCCTGGGCA | ACAGTGAGAC | ACGGTCCCCC 230820 |
| AAAAAAACCT | TTGCTTCTAG | GGATCTGGTA | ACAGCTGCCC | CACCCACAAG | AAATGGAGAT 230880 |
| CTGGGACCAT | GGACAAATTT | CTAGAGACCT | ATTTTCCTGG | ATTCTGTGAA | TCTCGCCGAG 230940 |
| GTTTTCTTCC | GGATCTCGGT | TTCTGCATTT | TTTTGTTTGT | TTGCTTGCTT | TTTTGAAACG 231000 |
| GAGTTTTGCT | CCTGTTGCCC | AAGCTGGAAT | GCAGTGGCGC | GATCTCGGCT | CACTGCATAC 231060 |
| AAACTCCGCC | TCCCGGGTTC | AGACGACTCT | CCGGCCTCAG | CCTCCCTAGT | AGATGGGATT 231120 |
| ACAAGCGCCC | GCCACCAGTA | GAAACGGAGT | TTCACCAGGT | TAGCCGGGCT | GGTCTCGAAC 231180 |
| TCCTGACCTC | AGGTGATCCG | CCAGCCTCTG | CCTACCAAAG | TGCTGGGATT | ACAGGCGTGA 231240 |
| GCCACCGCGC | CCGGCCGGTT | TCTGCTTTGA | TCGGAATTAA | GTGGGCAGAA | AAGTCTAGGC 231300 |
| GGGCTAAGTC | TTGCCTATGC | ATCTGCGCCC | AGCTGCTCAG | ACTGGCCAAA | CAGACCCAGT 231360 |
| CGTTTAGTCT | AACGCTTCTG | GAACTCCACT | GAAGCGTTTT | GCATTGTTTC | GTTTGGAGCC 231420 |
| TTCAAATCCG | AGTGTGTGGC | AGGAGATAAT | AATCCTAGCA | GAAGCTGTTT | ACTGCTGACG 231480 |
| CGCCTCCCAC | TTCCCAGATA | CTGACACCGG | CTCAGGGCGG | ATCCAGCCTT | TTCCGCTCTT 231540 |
| CCCTCCCTCC | ACCCCCTCCT | TTCCCTACAA | CTACTCTCAA | AGGAAAAGGG | TTGGATGTCC 231600 |
| CATTTGGGTG | AAAACAAAGT | GGCATAAAAG | CAAATGATCA | CCTTTGATAG | CCACATATTA 231660 |
| GAATTTTCCG | AGGGTATTTT | TAAATTACAA | CGATTCTAAT | GGGCAGCTGG | GCTGAGAATC 231720 |
| ATCAGATTTG | AAGGTCTGGT | TTCACATGGC | TCTTGGGCTG | AGAAGACCGG | ATTTTCCCCC 231780 |
| CCCAGCATTT | CCTGTATGTC | CGAGAATTTC | GATCCTAAGG | TTAGAATTGC | CTTATGGGCC 231840 |
| TTGGAATCCT | TTTTATTCAC | TGACCAAATT | GCCTTTGATT | CCAGCTCCCA | ATCGGTGTGT 231900 |
| GACCTTGGCC | TAGGGCTTAA | TCTCTTCCTA | CCTCCATCTC | TTCCTTGTAT | GCTTTTGCTC 231960 |
| ACCTTGAAAT | GAAAAGAACC | TGGCTCAGCA | AGTGTAGATT | CTGAAATCAG | AAAACAGGCT 232020 |
| GAATAAGAGA | GATGGTTTAT | TAGGCACTAC | TGTGTGCCAG | GCACATTTCA | TGAGCTTCCA 232080 |
| GTATGTTAAT | TCATTTAATC | CAACAATCTA | AGAGATAGGT | TTTATCCTTA | TTCCGAATTT 232140 |
| TGAGATGAGC | AAACTAAGAA | ACAGCTTAAA | GAACTTAAGT | TGTAAGGCCA | GGAAAACAGT 232200 |
| ACTTATAACA | GCTGACTATT | CTATAACCAC | ACCTCCTTAA | GAGATTATTG | TCAGAAAAAT 232260 |

| | | | | | | |
|---|---|---|---|---|---|---|
| AGAAAGAGTA | AAACATCCAT | ACATAATGGG | TAAACTTTGT | CCACATACCA | GAATGTTACT | 232320 |
| AATGGCTTTC | TAACCTCTGA | AGAATTTAAG | GGAAGGAGGA | AAGGTAATTT | TCCCCAGGGA | 232380 |
| ATCTACACGA | AGAGGTAAAT | CTTGACAATG | TATTAATACT | GTAAACCCAG | GGAAAAAAAG | 232440 |
| CCAGTACAAT | TTTTATTTAG | GGTGTGGCAA | ATAAACAAA | GGGACACGTG | AAAACATGGC | 232500 |
| TCAGTAAAGA | GCTACAAGAC | TTGGTGCAAC | TGACTTATTG | TGGTGAGTGA | GAAAAGGAGA | 232560 |
| GAGAGAAAAC | TTGAATTTCA | ATTCTTCTCT | CTGGGCTCCA | ATAACAAGAT | TTTGTATTCG | 232620 |
| GTCTATTTAG | TAGTGAATGA | TACATTGTGT | TAAGTTTGTT | AACCTAGAGG | CTTTCATCTT | 232680 |
| AAGCAGTACT | TAAGATGTAG | ACCCCCTCTT | ATTCAAATAC | TGATAATCAG | CATAGAACTT | 232740 |
| GGCATACAAG | AGACACTTGG | CTGTTGGGCA | TTGAGAAAAT | GTTGAACTGA | ATGAATCAAT | 232800 |
| GACTTAGGCA | GCCAGGAAGC | ACTTTGTTGT | AGAGAGTTGG | TTTATTACTA | AGGAAGACAT | 232860 |
| TAAGTATTAA | ATATTAGACT | AATAGGTTGC | TAATAGTGTT | TTCTCTTTCC | AATAGAAAAT | 232920 |
| GTCTTCTGAG | GCTGATCTGG | TGTCTCACAT | CTGTAATCCC | AGCACTTGGG | GAGGCTGAGG | 232980 |
| TGGGTAGATC | ACCTGAGGTC | AGGAGTTTGA | GACCAGCCTG | GCCAACATGG | CGAAACCCCA | 233040 |
| TCTCTAATAA | AACTACACAA | ATTAGTCAGG | TGTGGCGGTG | TTCACCTGTA | GGCGCCTGTA | 233100 |
| GTCCAGCTA | CTCAGGAGAC | TGAGGCAGAA | GAATCACTTG | AACCCCGGGA | GGTGGAGGTT | 233160 |
| GTAGTGAGCC | AAGATCGTGC | CACTGCACTC | CAGCCTGGGC | GACAAAGTGA | AACTCCGTCT | 233220 |
| CAAAAAAAAA | CCAACCCCAT | CTCTACTAAA | AAATACAAAA | ATTAGCTGGG | CATGCTAGTG | 233280 |
| CACGCCTGTA | GTCCAGCTA | CTCGGGAGGC | TGAGGCAAGA | GAATCACTTG | AATATAGGAG | 233340 |
| GGGGAGGTTG | CAGTGAGAGT | GAGACTCTCA | AAAAAAAACA | ACAAAACAAA | AAGTAACAAG | 233400 |
| AAAAAGAAA | CTATATTCCA | AAAATCCAAA | TTTCACTGGC | AGTTGTTCT | GGGAGCTTCA | 233460 |
| GACACATAGA | AGGTGTCAGT | TAACCAGTTC | TTACCTAAGA | GGTACTGCTA | AGAGCCTAGT | 233520 |
| CCCTAAGCAA | AGGGAGCTTC | AGAGAAACAC | AGAAGGTGCC | AGTTAACCAG | TTCTTACCTA | 233580 |
| AGAGGTACTG | CTAAGAGCCT | AGTCCCTAAG | CAAAGGACAT | TCCTCGTAGC | TCTGTCCTGT | 233640 |
| CTCCTCATCT | CCAAAATACT | TTACCTTCTA | CTTTGAAATG | CCCACTATTA | TATTCAAAG | 233700 |
| CCCTAGTTAC | TTCCAGGGAA | AATTATCTAT | TGAGCAATGA | ATTTCGGTAG | CTTCAGTTGG | 233760 |
| ATTCCAACTC | TTGAGCAAGT | TTTCATCTCC | CTTGCCTGAA | TGGCCCTGGG | GAGGACTATT | 233820 |
| TAAATTGGGG | CGAGTGGATG | AGGATGCTAA | ACCTAGAGGT | CTCCCAATTA | CCAAAGGCAC | 233880 |
| CTGGGCACCA | GGGACTAAAG | TTTGTCTCAG | GAATTACTG | AGATATGAGG | CTGAGATAAA | 233940 |
| ATCATTTTTT | GGTACATAAG | GTATCTTGAA | CAAAGCAGAT | CAGTTTAACA | CAAAATCAAC | 234000 |
| AATCGTAATT | TCCCTTTTTA | AATTTCCAAA | TCTATGTAGC | AATATCCTTT | CCTTTAATTC | 234060 |
| ATTCATCATC | TCTATTCACT | TTTTGTATTC | TGTAAATCAT | TTGAACTTTT | ATAAGAATTA | 234120 |
| TATTTTCCCC | TTGAGGTCAC | AAAAAAGAAA | GTATTAGAAA | TTTTATAACC | AATTTTTAAA | 234180 |
| AAATTATATT | TTAAGGTTAA | ATACAAACCT | TCTAAAGGTT | TGTCATCTGT | TGATCCTAAA | 234240 |
| TTATAATTAT | AAATTTATAT | ATTCCTGTTG | AATATAATGC | ATGTGTGTTA | CAAGATTATT | 234300 |
| AGCAATTTGA | GAATTTCCCG | TGCATATTGG | AGATGAGCAA | ATGGAATAAG | TGCTCATGTG | 234360 |
| TAGCGACAGG | ATTCTCTATT | TTATTTCAAT | ACTTAATATT | GTACCAAACC | AAGTAAGAGG | 234420 |
| AGCATCATGA | GAAAATGTAC | TAAAGGACAG | TCATTACCTA | TATTTACACC | TAGAAAAGAA | 234480 |
| AACTATATTA | TTGATAAACT | GATAAATCTA | TTTTATGTAT | TTATTTATTA | TTTTGCTCTG | 234540 |
| TCATCCAGGC | TGGAGTGTAC | TGGTGCGATT | TCCACTCATT | GCAACCTCCT | GCTCCCAGGT | 234600 |
| TCAAGCAATT | CTACCTCAGC | CTCCCTAGTA | ACTGGGACTA | CAGGCATGCA | CCACCACACC | 234660 |

```
CAGCTAATTT TTATATTTAT AGTAGAGACA GGGTTTCACC ATGTTGGCCA GCCTGGTCTC 234720
AAACTCCTGA CCTCAGGTGA TATGCCCACC TCAGCCTCTC AAATGCTAGG ATTACAGGTA 234780
TGAGCCACCG CGCCCAGTCT GATAAATCTA TATTAAAAAG AATAAATATA ACCATTGCAT 234840
CTTCAACAGA AATTGGAATA TGGCATGTAG ATTTCAAAAT AAAATGAATT CTCTGGCATT 234900
GAATTACTGT ACTCATGTTG AAGAAATGTC AGAACTTCAT TGGATGTTAT TATATTACAG 234960
TTGTTTGTTT GAGTTGTAGT TTGGGCAGAG TAAAGGAGCC AACATGTCTT AGGATTTAGA 235020
ACTTGTGCAC ATTGCCTACA GTTGAAAGAA GAAAGCATGC TAAATTCCAG CCTCTTTGGT 235080
ATGTGGTTGG GACGTAAAGT TTTACCACAT CCTTCATTGT CTTAGCCTAC TCAGGCTGCC 235140
ATAACAAAAT ACCAGAGACT GGATGGCTTA AACAACAGAA TCTTTTTTTC CATATCTAAG 235200
AGGCTTGGAA CAGAAATTCA TTTTCTCACA GTTTTGGAGC CTGGAAGTTT AAGATCAAGG 235260
TGCCAACATA GTTTATGGTG AGAATCTGTT CCTGGCTAAC AGATGGCTGC CATCTCACTG 235320
TGTGTTTGTA TGGTGTTTCC TTGGTGCCTG CGTGGAGAGA GAGCTCTAAG TGTCTCATCT 235380
TCTGTAAGGA CACCAGCCCC AATGGGATTA GGGCCCTATC CTGTGATCTT TAGTTTTATG 235440
TACCCCCTAA AGGCTCTATG TCCAAATGCA GTCACACTGG GGTTTAGGGT TTTAATAAAT 235500
GAATTTTGGG GGACACAGTT TAGTCCATAA CATTCTGTCC TTGACCTGCC AAAATGTATG 235560
TCCTTCTCCC ATACAAGATA AATTTATTCC ATCCCAGCCG GGCATGGTGG CTCACACGTG 235620
TAATCCCAGC ACTTTGGGAA GCCAAGGCAG GCGGATCAGA AGGTCAAGAG ATCGAGACCA 235680
TTCTGGCTAA CACGGTGAAA CCCCATCTCT ACTAAAATAA AAAAAAATT AGCCAGGCGT 235740
GGTGGCGGGC GCCTGTAGTC CCAGCTACTC TGGAGGCTGA GACATGAGAA TGGCATAAAC 235800
CCGGGAGGCA GAGCTTGCAG TGAGCCAAGA TGGTGCCACT GCACTCCAGC CTGGGCGACA 235860
GAGCTAGACT CCGTCTCAAA AAAAAAAAA AAATTATTCC ATCCAACAG CCCCCTGAAA 235920
GTCTTAACTC ATTCTAGCAT CAATTCTAAA GTTCAAAGTG TCATCTAAAA AATCATCTAA 235980
ATCAGGTTAC GGGTGAGGCT CAATGTGTGA TTCATCCAGA GACAAAATTC CTTTCCAGCT 236040
TTGAACGTGT GAAACCAGAA ATGTTACATG CTTCTAAGGT ACAATGGTGA AACAGGCATA 236100
ATAGACATTC CCATTAGAAA ATGGAGAAAT AGGAAAGAAG GAAGGTGTAA TGTGTCCTAA 236160
TCAAGTCCAA AACCTGGCAA GGCAAATTCT GTTAGGTCTT AAGAAAAACC CTCTTTGGCT 236220
TGATGCCCTG ATTTCCAGGC CCAGTGGTGT CTCAGTGTCA CCTCTGGCTC TGTAGTTGGC 236280
CTACTCCATC TGCCCTGCCT GAAGTCTCGG TCTTTCAGTT TGGTGGGGTC CCACCCAGGC 236340
AGCCATCTGT GAGAGACTCC CACACAGTTC TGCAGGGCAT CTTTGAAACA GGTAGAGTCA 236400
GCCTTGACTA CATGTTCCCA CCCCCACCCT ATCCATCTG TACTCTCTGA GTCTGACATC 236460
AAAGTGGCAG CCCTGGCGGC TCCTGCCTGT AATCCCAGCA CTTTGGGAGG CCAATGAGAA 236520
TGGATCACTG GAGGTCAGGA GTTCCAAACT AGCCTGGCCA ACATAGTGAA ACCCCATCTC 236580
TACTAAAAAT ACAAAAATTA GCTGGGCAAG TGGTGGCAGG AGCGCTACTC GGGAGGGTAC 236640
AGATTTAGAG CCTGTAATCC CAGCTACTTG GGAGTCTAAG GCAAGAGAAT CCCTTGAACC 236700
TGGGAGGTGG AGATTGCAGT GAGCTGAGAT CACACCATTG CCCTACAGCC TGGGTGACAG 236760
TGAGACTGCC TCAAGAAAAA ACAAAAGAGT CAGCCCTAGT GATCTTGTAA GTTGCCTTTG 236820
GTGGGTCAGT CTTTCCTTTT CTTAAAGAAT AGTACACATT GACAGCCAGG TAGCTCTATG 236880
ATCCTGTTCT ATAGAATTCA AAAAGTCGAC AACCTTCCTT TGTTCCTTTC TGTTTTCTCT 236940
GCCTACGTTA GTTTAAATTG GCAGTGTCTC TGCTGGAATA ATCCCATCTC TCTTCCTGGC 237000
TTCTGCTGAG ATGGCTGATT AAATCCTTGG GTCACACCCA TTATCTCTTT ATCAAATGGT 237060
```

| | | | | | | |
|---|---|---|---|---|---|---|
| TGTTCAGGCT | AGGCTCAGTG | TTTCACGCCT | GTAATCCCAA | CACTTTGGGA | GACTGAGGAG | 237120 |
| GGCAGATCAC | TTGAGCTCAG | GAGTTAGAGA | CCAGCCTAGG | CAACATGTCA | AAACCCCATC | 237180 |
| TCTATAAACA | ACAACAAAAA | ATTAGCCAGG | GTGTGGTGGT | GCATACATGT | AGTCCCAGCT | 237240 |
| ACTTAGGAGG | CTGAGGTGGG | AGGATTGCTT | GAGCCTGAAG | GCAAAGGTTG | CACTGAACTG | 237300 |
| AGATTGTGCC | ACTGCACTCC | AGCCTGGATG | ACATAGCCAG | ACCCTGTCTC | AAAAAACATA | 237360 |
| AAAATAAAAA | TAAAACCAAG | AAAAAAAAAG | AAAAGAAAA | CATTGTTCAA | CCATACCTCT | 237420 |
| TCAAGAAAAA | CTTTCTCAAT | TTTTACAATA | TAGATTGAGA | AATCTATCCC | AAATCTCCAA | 237480 |
| GTTCTGATTG | TGTTTTGCTT | AAAAATTCCT | TCTTTATTTC | GGCTCTTTCC | TCTCACATTT | 237540 |
| CACTTTAAGC | AGTAAGGAGG | ACCTAAATCA | CACCTTCAAT | ACTTTGCTTA | GACATCTCTT | 237600 |
| CTGGTAAATA | TCCAGTTTTA | CTGCTTATAA | GTTCTTTCCA | GTAAACACTA | CAGCGTAATT | 237660 |
| CAGCCAAGTT | CTTGACACAT | TGTAACAAGA | ACAGTGATTT | CTACAGTTTC | AATAACCTG | 237720 |
| TCCCTCATTT | TCATCTGAGA | CCTCACAAGA | GTTGACTTTA | ATGTCCATAT | ATATATATTT | 237780 |
| TTTGTGTGTG | TGTGGCGGGG | GGAGTGGAGT | CCTGCTCTGT | ATCCCAGGCT | GGAGTGCAGT | 237840 |
| GGTGTGATCT | TGGGTCACTG | CAACCTCCAC | CCCCCGGGTT | TAAGCGATTC | TTCAGCCTCA | 237900 |
| GCCTCCCGAG | TAGCTGGGAC | CACAGAAGCA | CATCACCATG | CCCAGCTAAT | TTTTGTATTT | 237960 |
| TTAGTAGAGA | CAGGGTTTCG | CCATATTGGC | CAGGCTGGTC | TCAAACTCCC | GACCTCGTGA | 238020 |
| TCTGTGCCCT | CAGCCTCCCA | AAGTGCTGAG | ATTACAGGCG | TGAGCCACCA | CGCCTGGCCT | 238080 |
| AAAGTCCATA | TTTTAACCAG | CATATTTAAT | ATTCTATCCA | TGATCGTTAT | AAATCTAAGT | 238140 |
| TTCTATGAAA | ATGGAAGCTT | TCTGTCCAGC | TCTCTTCCTT | TCTGAGCCTT | TGCCAGAATT | 238200 |
| GCCTTTAATG | TCCATATTTC | TTTCAATAGT | CCCTTCACAA | TTGGCTTTTT | CTAGTATGAA | 238260 |
| CCTCAAACTC | TTCCAGCCTT | TACCCATCAC | CAATTTCCAA | AGCCACTTCC | CCATGTTTAG | 238320 |
| GTATTTGTTG | TTGCAGCATC | CCACGCCTGG | GTACCAAAAC | TTAGTCAGCT | TGGACTGCCA | 238380 |
| TAACAAAATA | CTACAGACTG | GTGGCTTAAA | CGATAGACAT | TTATTTCTA | ACAATTCTGC | 238440 |
| AGGCTGGAAA | TCTAAGATCC | AAGTTGCCAG | CATAGTCAGT | TTCTGGTGAG | GATCTCTTCC | 238500 |
| TGGCTTAAAT | TATTTCACAG | ACACCAGGCA | GATAACCATA | TCCATTCTTT | CCTGTATTCG | 238560 |
| TTAATAGTCA | GAGCTAAAAG | TGTAGGGCTC | TAAATTTACA | CTTCAACAAA | TTGTTCTGTT | 238620 |
| ATTAAGTATT | CACCTCAAAA | TGACCAGACT | ATACTATCCT | CTAAATTTTA | GAAACTTGGA | 238680 |
| GCTTGGCTCT | GGTCCCTAGT | CTTTGTTCTG | TCTCATTAAT | GGCTTCATCA | ATACTACGGT | 238740 |
| TCCAAAGACT | ATCTATATGC | AGTAAACTTC | CAATTTTACA | TCTCCAGCCT | GACCTTTTTT | 238800 |
| CTGAAATGCA | AATGTGTGTA | GCCACATTTT | CACTTGACAT | CTCCATTTAG | AACTCTAATA | 238860 |
| GGTCTTTCAC | CCTAAACACT | TCCAAGACAC | AGGAATAAAC | GTGCTCCTTA | AGCCTGTTAT | 238920 |
| CCCTTCCAGT | TCTCCCCAGT | TCAATAACTG | ACACTACCAT | TTACTCAAAT | CAACATTCTA | 238980 |
| AGAGTGTCAC | TTGCTACATT | TCCTTCATCT | CTACAAATCC | AAAGTATCTG | TGAGTCACGT | 239040 |
| CACCTACATA | TTCAATACAT | GCAATAATTC | ATTCTCCATA | CTCCTTACCA | TGACTTAAGG | 239100 |
| GCCCACTCAG | TGACCATCTC | TGGCCTCTGT | TCACCTCTTC | TGCTGTTCTC | CTTTGCTGTT | 239160 |
| CCAGCCACGC | TGGTCTCTTT | TCACATCAAG | CAGCTAAGCT | CTGCCCATTT | AAGACATTTA | 239220 |
| ACTTCTTGGC | CTCAATCTCT | GAAATGCCTG | TTTGATTTTT | CTTCTGGTGA | GCTCATTTTC | 239280 |
| ACTCATCAGG | TCCCAGCTCT | GTTTCAGACA | AGGCTATCTA | AAATAGACCT | ACCTAAATGG | 239340 |
| ATTAAAAATC | TGAGAATATG | AAATAACAAA | TATCAGATGA | CATTTTAGGA | GACCCTTTAT | 239400 |
| ATACCTCATT | TGTGTGTGTG | TGTGTGTGTG | TGTGTGTGTG | TGTGTGTTTG | GAAATGGTGA | 239460 |

| | | | | | |
|---|---|---|---|---|---|
| TGGAGGGTGT | CATTGCTAAG | TGAGGAGGAA | ACACAAAAGC | CATCTAGGAA | AGGACACAGA 239520 |
| CTAGATAGGT | CCAAAAGTGG | TTTAAGACAG | AATATATGTA | AAGAGAGTTA | TAGAAAGAGC 239580 |
| AATAAGTTGG | GATAAAGGAT | TTCCAAAACA | TATACGGGGT | TAGTAACCTC | AATTTACAGG 239640 |
| GACAAACTGC | AAAACGTTAG | TGAAAAGGCA | AACAACATAA | TATAAAGAT | GATTAAACGG 239700 |
| TATTTTATAT | CATGTATTAA | ATTCATATGG | CCAATACATA | TGAAAAACAA | GAAACAAAAA 239760 |
| ACCTTCCTAG | TAATTCAAAA | TTATGCATAT | TAATACAACA | AAGGGATACC | ACTTCTTTTT 239820 |
| TTTTTTTTTT | TTTGAGACAG | AGTCTTGCTC | AGGTACCCAG | GCTGGAGTGT | AGTGGCATGA 239880 |
| TCTCAACTCA | CTGCAACTTC | CACCCCCTGG | GTTCAAGCGA | TTCTCCTGCC | TCAGCCTCCC 239940 |
| GAGTAGCTGG | GACTACAGGC | GCCTGCTACC | ACGCTCAGCT | AACTTTGTA | TTTTTATTAG 240000 |
| AGATGGGGTT | TTACCATGTT | GGTTGGCCAG | GATGGTCTCG | GTCTCTTGAC | CTCGTGATCT 240060 |
| GACGGCCTCA | GCCTCCCAAA | GTGCTGTGAT | TACAGGCGTG | AACCACTGCA | CCTGGCCTAA 240120 |
| TTTTTGTATT | ATTAGTAGAG | ATGGGGTTTC | ACCATATTGG | CCAGGCTGGT | GTCGAACTCC 240180 |
| TCCTGACCTC | AGATGATCCA | CCCACTTCAG | GCTCCCAAAG | TGCTGGGATT | ACAGGCATGA 240240 |
| GCCACTGTGC | CCAGCCTGGG | ATACCATTTC | TTACCTATGA | ATAGACAACC | ACTAAAGCCA 240300 |
| GTATACTCAG | GACTGCAAAG | GATGAGGAAG | AATTGCCATT | GTCATATAGT | TTTTCATAAC 240360 |
| TTTTCCTGAC | AATGTCTATT | AAATTGTATT | AATAGACATT | TGGAAAGGGA | GAGTGTCAAC 240420 |
| AATCTAGAAT | AAAGGCCCCA | CTAGGTAAGG | TTACATATGT | AAGGACTCTT | TCAAAACTGT 240480 |
| CACAAGAATT | CAGGTACGGT | GGCTCATGCC | TGTAATCCTA | GCATTTGGG | AGGCTGAGGC 240540 |
| GGGTGGATCA | CTTGAGGTCA | GGGGTTTGAG | ACCCGCCTGG | CCAACATGGT | TAAAACCTAT 240600 |
| CTCTACTAAA | AATACAACGA | TTAGCCATGC | ATGGTGGCAC | ATGCCTGTAA | TCCCAGCTAC 240660 |
| TCGGTAGCCT | GAGGCAGGAG | AATAGCTTGA | ACCCAAGAGG | CAGAGGTTAC | AGTGAGCCGA 240720 |
| GATCGCACCA | CTCCAGCCTG | GGCAACAGAG | TGAGACTCCA | TCTCAAAACA | AAACAAAAAA 240780 |
| ACTACTCAAA | ACTGTAATAA | GAAAAAAAAA | AACCTAATTA | TACATGTAAA | ACATTTAAAT 240840 |
| AACTAAAATA | AGAATACTGT | TGACATAGTG | AGACATCCAT | TTATACTATG | GAATGTTATG 240900 |
| CAGCTACCTG | AAACAATAAT | CCGGTGAAAC | AAAATCACAC | ACACAACTGA | TGAGAGTAAA 240960 |
| TAGAGAACCG | TATGGAAGAA | AACATACCAC | AGTAATTATC | TCAGATAGCT | GAAACTAAGT 241020 |
| TGGTGCAAAA | GTAATTGTGG | TTCTTACCAT | TACTTTCACT | GGCAAAAGCT | GCAATTACTT 241080 |
| TTGTACCAAC | CTAATAGAAT | GGGGTGAGGA | GAGGTAAACC | TTTATAAACA | TCTCTGTGTG 241140 |
| AACTGTTAAA | ATGAGCAAGT | ATATTTTTT | TAAAGTATAA | AGAGAGAAAA | AAGTAAACTT 241200 |
| TCTCCATTTC | CCACCTCAAA | TTATGTTCTG | TCACTCATCC | TGTTTAGATT | CTTTCAAATG 241260 |
| CAGTTTGAAG | TTTTATTTAT | GAGATTCCTT | GTTGTTTGCC | TCTTTCCATT | AAACCTAGCT 241320 |
| CCACAAAGTA | GGGACCTGAT | GTATTCATTC | ACTGTTATAT | CCCAGCATCT | AGCAGAGGGC 241380 |
| CTGACACTTA | GTGGGAACGC | AAGTATCTGG | TATATAAACC | AGAGAATAGA | TATTTTTTA 241440 |
| GCCCAGAAAG | CTGTTTCACT | GCACAGAGTG | TAATTATCTG | AATTTCTATA | AAATGTCTA 241500 |
| TCTATAAATC | ATTGTCAATA | CATTACCTAC | TCACCTTACC | CAGCTACCAG | GAACACTATG 241560 |
| AAGTTTTGAA | TTACACCCCA | TTTGTTTTCC | ACACTCTTAC | CATTTTCCCA | GTTTCTGCAC 241620 |
| TGACCTCTCC | AGACATCATG | TGTACTGATA | ATTCTAAGTT | GTCTAGATTG | TTAATTCTTT 241680 |
| TAAGGGCCTG | TTCTCTGCTA | GCTGGCATCA | TGCATAAAAT | AATTCTCTTT | AATATGCTCT 241740 |
| GGGTCTAGGG | TTAATAGATG | TTTGCTTAAA | ATCATGGAAA | GAAAATGGTC | ACACAGCTGG 241800 |
| TATGTGTGAT | CAAATTTGTG | CTGTTTCATC | CACTTAATGT | TTACTTTGTG | GTAATGGAAC 241860 |

```
CTCCCAGCTT TTATTTTCCT TCCTTCCTTC CTTCCTTCCT TCCTTCCTTC CTTCCTTCCT 241920
TCCTCCCTCC CTCCCTCCCT CCCTCCCTTC CTTTCTTTCT TCACAGAGTC TAGCTCTGTT 241980
GCCCAGGCTG GAATGCAGTG GTGCGATCTC AGCTCACTGC AACCTCTGCC TCCCGGGTTC 242040
AAGCGATTCT CCTGCCTCAG CCTCCCAAGT ATCTAGGATT ACAGGTGCAT GCTGCCACAC 242100
CTGGCTAGTT TTTGTATTTT TAGTAAAGAT GGAGTTTCAG ATGTTGGCCA GGCTGGTCTC 242160
CAACACCAGG CCTCAAGTGA TCCGCCTGCC TTGGCCTCCC AAATTGCTGG GATTAACAGG 242220
CCTCAGCCAC TGTGCCCGAC CCCAGCTTTT ATATTCTAAT GCTGAGATTA TTCAGTTAAC 242280
ACTCTTACCT GCTAGGATAA GTTTGTTGGA GAATTTTACC TTACCTTGTA CCCTTTACCT 242340
TCACATCTAC CTGTACCCTG GCCCTTCACA TCCTTTCCAT ATAATATATC TTCAGTAAAT 242400
ACAGGGAAAA AAACCCAGAA TGATTATGTT GACAGCAAAA CATGTTTGTG CAGAAACGGA 242460
GTAGTCACTA TCTAAGCCAC AGAGACTTAG GAGTGTATTC CTGAGTTATG TATCATTTTA 242520
ACCATCACTG GATCTTAAAT CCCAGTTGCT AAATTGAAGG GAGATACATG ACTCTTTTA 242580
GGGCTTTGCT CTCTGATACA GTAGCCATTA GCCACATGTG ATATTTAAA TTTAAATAAT 242640
TAAGTCAAAA ATTCAGTTTC CTCAGTCTCA CCACATTTCA GGTTGCTGGT GTCTACTGTA 242700
TTGGATACAC AGACATAGAA CATGTCTATC ATCACAGAAA ATTCTATTGC ATTGCACTGG 242760
GATAGGTACT TTTTGTGCCC TTGGGCTGAT AAGTTCAAGT GCACTTAACT AGCTTCCTCC 242820
AAGTGGAATC AGAGGATAAA TTTACCATAC AAAATACAGG ATACCCAATT ATATTTGAAT 242880
TTCAAACAGG CAACAAATAA TTGCTTAAGT ATGCCCCTCA CTGCACACCC AAATATTACA 242940
TGAGACATTC TATACATATA TATATATATA TATATATATA TATATATATA TATATATATA 243000
TATATATATT TGAAATTCAG ATTTAACTGG ACATTGGTA TTTTTAATGT GCCAAATCTA 243060
GCAACCCTAT CTGAAGAGCA AAACTGGAGT GTCTAGTCTG GATAGGTCCT TTTACACCAC 243120
AGGGAGTTAT TTGAGGAATT GAGAAGGGCT GTGGTACCTG TAAAGAACTA ACTCATTATG 243180
AAGAAAAGGA TCTGTAAGTT TTTCTGTATG TGTAAGGAAG GCCAAGAAGG TGGTTTCCAG 243240
ATATATTTAC TTTTTCTTCT CTCTCTCTTA GGTTGCAAAA GCTTCTCATT TCAGAGAGAT 243300
GCCAGGATCC TAAGTGCCTG CCAAACTTAC CAATTCTAAG GAATAAGTGG ATGGATGGCA 243360
TTACTGATTC CTACATTACT GATTGATTCT GCATCCGCAA ATTGTTTAT TAAAAACATT 243420
CTACATCATG TGTGGGGAGA TAAGGAGGAT AAAATGAAGA GAAAGAATAT TATTGAGGGG 243480
AAGTTCTTCT GAATACAAAA TGTGTTTAAT TTTTAAATA AGTATTACAT TCACAGGGTT 243540
CAAACTATTT GAAGTAAAGA GATTATATAT AAAGAATCCA TCCCTCAACT TACCCAGGTG 243600
GTCACTTTTC TTTTTCTTGT GTATCTGCCC AGTATTCATT CCTGCTGATA TCAGTCAATA 243660
ATGAATGATA CGTGTTTTCT TCACTTTTTT CATTCTTGTC AGGTAGCAGA CTGTGTAGAC 243720
TTTTCTGCAC TTGCCCTTTT CATAACAATC TATCTTGGAG AACTTTCCCT ATGAGAACAT 243780
ACAGAGCTTC CTGTACACAG TTGCATGTAC TGCATTATGC AAATGCATTA TATTTTATGT 243840
AACCTGTCCA CTGTTGGTAG GCACTTGAGT TGTTTAGTC TTTTGCTATC AAACAGTTCT 243900
GGGATGATTA ACCCTGATTT ACTGCAAAAT TGAAATTGCT CTGCTATTCT GCTGGAATGG 243960
TGGTAAGTGA ACTGAAAATT CCAGTCACTC TTGGGCTAGA CTCAACGTTC TTAAAAACTA 244020
TGTGGCCATC ACCAAATTAG TTATTTTGAA CCTTAATTTC TTCACCTCTA AAATGGAGGT 244080
AATACTTACC TTAAGTGGCT ATGAGAATGA AGATCATGTG TATGAATTGT TGGTGCTCTA 244140
AAGAACAGCA CAAATAAAAT TATTTTCAAA TTTAATTTTA ATTGAACTAT GTGTAATTTC 244200
TTAATTTTGA AATAATTTTA TTTGTAATGT GCATAATCTT ATTTAATGTA TAATGTATAC 244260
```

-continued

| | | | | | | |
|---|---|---|---|---|---|---|
| ATTGTAATAG | AAACAGATTT | CCCAAATTCC | AGCCTGGCAT | GAGGTAATAA | AAGGTAATGC | 244320 |
| AAAGGGAGAG | GAAAGCATGT | GTCATTAATT | TTCTGCCTAG | GACACCTCCC | TGGTTAAATT | 244380 |
| GCCATTTCCT | TTCTTCCTTG | CATAATGATT | AGGAAACACA | TCCTCCTGAC | CTGCCTGCCC | 244440 |
| TCTTTTGCCT | ACTTTTTCAT | CTGCAGTCAA | GGTCTGGTTT | TAAGACTGAC | TGTTACTTTT | 244500 |
| ACAAATCTGT | GTGTATTGGT | GGCTAAGGGC | CTGTATGGTC | CACTGCTGTA | TTCCCAGGTC | 244560 |
| CCAGCATGGT | GCCTGACGCT | GCCTGGCAAA | TAGTAGTCAC | CCGAGAAATG | GCTGATGAAT | 244620 |
| TCATGAGGCC | TACTCTGTAT | GGAAATTTCA | ATTCTGGCCC | CGAATTTTCA | GGAGCTGGCA | 244680 |
| AGAGAGCCAC | CTTAATATCA | TAGGCTGAGT | TGGAAGAAGG | GAACACCCAA | TTTATTCTTA | 244740 |
| AGAAGTACTT | TGCCCAGGTA | CTGTGGCTTA | GGCCAGTAAT | CCTAGCATTT | GGGGAAGCCA | 244800 |
| AGTTGGGCAG | ATGGCTTGAA | CCCAGGATTT | CGAGATCAGC | CTGGACAACA | TGGAGAAACC | 244860 |
| CCATCTCTAC | AAAATATGTA | AAATTTAACT | GCTTGGTGGG | CCTGCACTTC | TGGTCCCAGC | 244920 |
| TACTCCAGGG | CTAGGGTGGG | AGGATTGTTT | GATCCCTGGA | GGTCAAGGCT | GCAGTGAGCC | 244980 |
| ATGATCACAG | CAATGCGCTC | CAGCTCTGGG | CAACAGAGCG | AGACCCTGTC | TCAAAAAAA | 245040 |
| CAAAAATGCC | TATACAATAA | ATCTATAAAA | AGTGGGTTTT | GTGTGTCTAT | ACACACACAC | 245100 |
| ACACACACAC | ACCTGCATAG | ACACTCAGGT | GTTCTGGAAA | GACACAGGAA | TCTGAAGCCA | 245160 |
| AAATACTTGT | GATTTTTTTT | CAGCTCTGCC | ACTCACCAAA | TGTCTGATGG | GATTAGTTAC | 245220 |
| CTGCCATCTC | AGAATTTCTC | TTCTGTAAAA | TAAGGTAATA | GTACCTCCCA | GAGTTATGAA | 245280 |
| AAACTATCAA | ATGAGATGGC | AGATGAGAAA | ACACTATATT | CCTTGTAAAA | CCTGACAAAT | 245340 |
| ATGTGCAAGA | TTATATAAAG | ACTGTCTTCT | GTCCATTTTC | AAATGTGGAA | AAGTGAAAGC | 245400 |
| AGGACAGGAT | GTTGGGATTT | CTGTCAGAGA | TTTGCTGGCT | TCCACCTGCA | GAAATTGAAG | 245460 |
| TAATTGGGGT | TCTTACACCT | AAGTACTAAC | TGAGTCTGGT | TGCAGTTTGC | CCCCATGGCT | 245520 |
| ACATGAAGCT | TTTAGAAGAG | TCAGCATGGT | AGACATGGAA | TGTTGAATGG | TGGTGGAGTG | 245580 |
| TACCCACACA | CCTCCCACCA | AGTCAGCTCC | AGGTTCAGAA | GCAGCAGCCC | CAGTGGAAGG | 245640 |
| CATGCGTGTT | TGTAACTCAG | CTGAGCCACC | TTTCAAGAAG | CAGAAGCTTT | CCAAACAGGG | 245700 |
| ATGCCCCTG | CTTTTGGTTC | AACTTGACTT | CCTACCTTCA | GTGAGGACAT | GGAGAATTCA | 245760 |
| TCTAGACTGG | GTACCTGAGC | AAACTTGGCA | GAGCAAAGAG | AAATGTGGAA | GGCCCTAGGT | 245820 |
| AGACAGGCCC | TGTGGAAGGA | AAGAATGAAA | GAGGACAGAA | AGAAACTCCC | ATTTTCTTTA | 245880 |
| GCACAGTCCC | TTCAGATTAA | GGATGAAGAG | GCTGGGGTTC | TGAATTGGTT | GGCCTTAGGT | 245940 |
| AATGGTCACA | AAAACAAGTC | AATGGCTTTT | CCACATCCGT | ACATTGAGAT | ATATTTCTGC | 246000 |
| CCTTGGTATT | CATTTTCTCT | GACCTCCAAT | TAAAGATCTA | TGCGTCATTT | TAAAGCCTTC | 246060 |
| CTTCCTTTCT | ACTCTGTGGT | CAGCGTAACA | TTGGTGGTTT | GAAACTGGCC | ATAATAGCAG | 246120 |
| CATTTACATC | ATGGGAACTA | GCATATGTTA | CATCAGGGTT | TTTTGTTTT | GTTTCTGGAG | 246180 |
| AGCCAGTAAA | CATACATCGT | CACACCACTT | AAATATTCTC | TGCTTAAATA | TTCTCTGCTC | 246240 |

( 2 ) INFORMATION FOR SEQ ID NO:21:

( i ) SEQUENCE CHARACTERISTICS:
        ( A ) LENGTH: 246240 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..246240

( D ) OTHER INFORMATION: /note= "HLA-H.CONTIG"

( x i ) SEQUENCE DESCRIPTION: SEQ ID NO:21:

```
TTTGTAAGTA  TTCTATTTTA  TTTATATGTG  TTTGTGTTTC  TGAGTATGTC  CTGAGTTGCA    60
CGATAATACT  ATATTTCTTA  TTGGGTAACA  TTGTCAGAAA  AGTTTCTAAA  AACTTTCTCT   120
GCTGCACTTA  TTTTATACAT  TTTATTTATG  TTAATAATCT  CACATTTAAC  ACACTTATGA   180
TTTATTCTCA  ACAGAAAAAG  GTGGTATTTC  TTTCATTTAG  TCTTTTAAAA  AGCTCACATT   240
ATCAAATGAT  TGCTCAATCA  TTTAATCTCT  TTGCTTCTCT  TATATGCATT  GATTTAATAA   300
ATATGTATAC  TAGTTTCTCC  ATCGATTCTT  TAGATTTGAA  ACTTATTTTC  CTTTTATTCT   360
TACAAAACTG  ACTTGTCTAT  AGGCCCACTT  CTACTTCCTT  TATTCTATCA  TCTTCCTCAA   420
CTTATTCTGT  GGTCAAAGAA  TGGAGAAATA  ATATTAATAA  TATGTTTTTC  TCATCAATGA   480
CTTCCACCTG  TTCTCTGAGA  AATTCAGCTT  CAAGAACTTT  AGTTTGATAT  GACTGCAAAG   540
ATAATACACA  GTCTAAATCA  TAAAAATGTC  TCAAAGGTTT  TTTTTTTATT  TGTTTCTTTG   600
AAATATCCAT  GAACAGGCAT  GTTTCTCCCC  CTGTAGTGCA  ATTTGTGTGA  AATTCTGGCA   660
TGCACTTAAG  AGGATGTCCT  AAAATACCAA  TATTTAATTG  ATTCTAAGTC  ATGTATTGTA   720
TCACATTTTT  GCCCATGGAT  TGTTGAAATC  CATGGACAAA  ACTGATAGCA  TTTTAGAACT   780
TCCTTTGTCT  AGTGGCAGTC  TTGATATATT  CACACTATCT  ATTGACAAAA  AATCTAAAGC   840
ACCAGGCTCA  AAGCTTGTAG  AGTAGGTGTC  AGTGATTTGG  AGGACATCTC  TAGGGCAATA   900
GTAGAGGCAT  TTTTAACCCC  TAACAACTAA  ATGATCATCA  GAAGTGAGTG  ATATCCTCAC   960
TCATGACCCC  AACTGCTCTA  ATTTCTATTG  TTTTCTTGCA  GAAATGAGAG  CAGGTGGGGT  1020
CATGGGTGAG  GAATGAGGTG  TTGAAAGTGA  ATGGGGTGTT  GAAAGCAAGG  TGTTTAGCAG  1080
TGTTCTGAAA  GCATACATTT  AAGTAGGCTA  TCCGGGCACT  GTCAATAGCT  AAGTGTCAAG  1140
CTAAGTACTC  TATTTTATTC  TAAGAACTAT  TTTTAGAAAT  GCTGAATCAA  CAAATCTCAG  1200
ATGGCACAGA  GGTTGTCATT  TTTGAATAAT  ATGAATATCA  GTAATTTTAG  TTGGAAAAGA  1260
AGATTTTCAA  AGAGCCATCT  AAGTTTCCAA  AATAAGTGTT  GCAGTCATAT  TAACTATTAT  1320
ATTTTCCTGC  CTGTTGATCT  ACTGCCTGTG  AATTGCTTAT  CAAACCAACA  ACCAACTGGA  1380
ATACATAGAC  TGCATGTCTT  GTTCATTTCC  TGCATTCTCA  AGTAATGGTT  TAACAAACTC  1440
ATGAGCTTAC  TCTTTAATCT  GAACCATGCT  TAACTTCAAT  TATGTTGATT  TAGTCTAAGG  1500
ATGCAGAATT  TATTTTATAG  TTATGTAGGA  ACTGGAATCC  AAAATGTAAT  ATGCCTCCAA  1560
GCTTTTCTTT  GTTGGCCTCT  GAAGGAGCAT  CACCTCTACA  ACTTCAACGT  TGTTATGAAT  1620
ACCTCTGGGG  AGGTGTTCAC  CTCAGGACCC  AAATTTGGAA  AAAGGGAAGT  GCCACTTTGG  1680
AGGAGTGCTC  TGAGCAGCTG  ATCCATTAAA  TGTCCCGATC  ACATGCACGT  GGAAGTGTCA  1740
TTGCAATATC  TGCACTAACA  GAAGCTCAGT  GACTTGAGAA  GTGAGTCTGG  AATTCTAAGA  1800
AAAAGGCAAG  GCATCTCTCT  TGCCACTTGT  TATTTTTCCA  GTCAAGCAAC  TGTGATAAGA  1860
GGGCATGGAG  AGCAGGAAGA  AGTGAAAAAT  CCCAGGAAAG  TCTGGAGTGG  AATCATTAAA  1920
CCAATTCTGC  TCCCTCTCTA  GGCCAACTTG  GGCCTATTAT  GAATAAGGAG  GTCTCTTATA  1980
ATCCATCTAA  CTCCACTCAG  GAACAATTTG  GGGATCTGAG  ACTGTGAACT  CAGTGGGCAA  2040
AAAAATATTT  CTTGGCCTAT  CATTATTCTC  TGTAGGATGT  TAAGGACAGG  TTTCTGTATG  2100
TGGAGTCCTC  AGTTTTTGCC  TTCTCTCCTT  GAGATATTTT  TATGCTATTT  AGTAATTGAT  2160
GGCCACAGTT  GATCGACCAC  ATTTCTGGGC  AACTCTAATA  ATCCTTGTTA  TATTAATCAT  2220
TGGACCAATC  TTGATTGTGT  ATGACCATCA  TCTTGTAGCT  ACCACCTCTA  TGTGGATGCT  2280
```

| | | | | | | |
|---|---|---|---|---|---|---|
| CTCCTCACCC | TGCTTAAGTG | CCAATGTCTG | TGCTATGGGC | CTACCTGTCA | CATGGATAAT | 2340 |
| CTCTTCACTC | CAGTCAGGCT | CCAACATTAA | CACAGGGCTG | TTCTCTTGTC | CCCCTTTGAA | 2400 |
| GACAGCTTCA | TCACCCTATT | CAAGTTGCAG | TACTCTCACT | GGGCCTCCAC | TGTTGCCTCT | 2460 |
| CTCTCACTCT | GCTTAGGTTT | CTTCACTCCA | CTCCAGGCAA | CTGTCACTAA | ACATCCTTTC | 2520 |
| CCCCATATAT | AACACAGACA | TCTACCTTGC | TTGGCCAAAC | CCACTGGATT | TCAGACTCAC | 2580 |
| TCATTCAGAG | AGTAAGACAG | AGAGGGGTTC | ATTTTTTATT | TTATTTTATT | TTTTATTTTT | 2640 |
| TGAGACGTTG | TCTCACCCTG | TCGCCCAGGC | TGGAGTGCAG | TGGTGCAGTC | TTGGCTCACT | 2700 |
| GCAATCCCCA | CGTCCCAGGT | TCAAACGATT | CTCCTGCCTC | AGTCTCCCAA | GCAGCTGGGA | 2760 |
| TTACAGGTGC | CTGCCACCAT | GCCCAGCTAA | TTTTTGTATT | TTTAGTAGAG | ACAGGGTTTC | 2820 |
| GCCGTGTTGG | CCAGGCTGGT | CTCGAACTCC | TGACCTCAAG | TGATCTACCC | GCCTCGGCCT | 2880 |
| CCCAAAGTGC | TGGGATTACA | GGTGTGAGCC | ACTGCGCCCA | GCCGGGGTTC | ATCCTTAATA | 2940 |
| CATACATTAG | AGATATAGAT | TCTGTTTTTA | TCTAAAAAGT | CTTTATAAGG | CCGGGCGCGG | 3000 |
| TGGCTCACGC | CTGTAATCCC | AGCACTTTGG | GAGGCCGAGG | CGGGCGGATC | ACGAGGTCAG | 3060 |
| GAGATCGAGA | CCATCCCGGC | TAAAACGGTG | AAACCCCGTC | TCTACTAAAA | ATACAAAAAA | 3120 |
| TTAGCCGGGC | GTAGTGGCGG | GCGCCTGTAG | TCCCAGCTAC | TTGGGAGGCT | GAGGCAGGAG | 3180 |
| AATGGCGTGA | ACCCGGGAGG | CGGAGCTTGC | AGTGAGCCGA | GATCCCGCCA | CTGCACTCCA | 3240 |
| GCCTGGGCGA | CAGAGCAAGA | CTCCGTCTCA | AAAAAAAAAA | AAAAAAAAAA | AAAAAAAGT | 3300 |
| CTTTATAAAA | ATCTGATTGA | ATGGTTGAAT | GCTGTGCTAA | AATCTGCATA | ATATCTTACA | 3360 |
| ACACTTCTGT | GAATCACGAG | ACAGTTTTGA | ATGCTAAATG | TCAGTTAACA | GATCTAAAGG | 3420 |
| GACCAACATC | TGCTTTCCCA | AATTATATGA | AAGAAGATCC | TGATCCCTCA | TCAGGTGAAA | 3480 |
| CTCACATCAG | ACAACAGTGT | CTGCATTTCT | CCAAAACCCG | CCTCAGCCCC | ATGGCCACTT | 3540 |
| TCCAGGGTTA | TCCTGCCTAC | CAAGCACTCT | CTTTCCTCAG | AAAAACTTGG | GGGAAAATGT | 3600 |
| AGAATAATAA | TTTTTTGAAG | TTCTGACCAA | CTTCTTGAAT | CACTCAGCAT | GTTTTTGACT | 3660 |
| GCAGGTACAG | AAAACGCTGA | CTAACAAAT | TTAAACACTA | TATAAATTTC | TTATCTCCCC | 3720 |
| AAACAGGACA | TCAAAGGCAG | AAAGGTTCCA | GAGCAGGGTG | ATCAGAGCTC | TGGCTCCACT | 3780 |
| GCCCTCAGTC | TTCTTGCCTC | TGCTCTCCTT | CACAGCAGGC | TTTACCCCCC | ATGCTGGTCA | 3840 |
| CAGTTTCAAG | TGTCCATGCA | GACACAAGTT | AAAGGCAGGA | AGAAACAGTG | CGTTTCTCTT | 3900 |
| GGAGATCAAG | GAATGCCTTT | CCAGAAAACT | CCCCCTTATG | TCTCATTTGC | CAAAACTTGG | 3960 |
| CCTAGTCTCA | GGTGCTGCCT | GAGCTAATCA | GCTACAGAAG | AAGGGACCAC | ATGACTGGTG | 4020 |
| TGGACCAGTC | AGAATTCACC | ACATGAAGCT | AGTAATGTGG | CTCACACTTC | CCAGGGGAT | 4080 |
| ATGGCCAGGT | AGCAGACAGT | GGATCGCTGA | ACAGAATACT | GATAGATTTC | AGCACCAAGG | 4140 |
| TTAGAATGGC | TACCACACCT | AATCCCACCC | TATCCCCGTT | TCCTTCTTTA | ATTTTTTCCA | 4200 |
| TAGCACTTAT | CAGTAGCTGA | CAAACTGTAT | ATGTTTTTAC | TTTTTTATTG | TCTGTAGCTC | 4260 |
| CCAAGTAGAA | TACAAACATC | TGAAACTCAC | TGTATCCATC | CTGAGTAATG | TTCTTTTCAG | 4320 |
| CTCAGTCACA | ATCATTTTTT | GATAGCCTAT | CCTATAAGCT | TAACTTATAG | TGTTAATCAG | 4380 |
| TATTAATACA | TCTTAGTGGG | AAAGAAGGAA | AAAATAAACG | ATCACACACA | CACACACACA | 4440 |
| CACACACACA | CACATACATT | TACGTAACAG | AGCAAGTGTG | AAAATACCTA | AAGGCTTTAT | 4500 |
| AGCTCCTTTT | GTCAATGGAT | ACATGACAGC | ATTTTTGGCA | TTCTTTACTA | CTCTTATTCT | 4560 |
| ATGCTCCATT | TGTCTTCAGT | CAGCACCTCA | GCTGCCCTTA | TGTTTTACTT | GGTAAGGCAA | 4620 |
| ATTCCTAAAT | GAGCCTGGTA | ATTAGTCATC | CAGCTTATAG | GAAGGTACTA | TAGTTTTTCA | 4680 |

| | | | | | | |
|---|---|---|---|---|---|---|
| TTAACTTTTT | CACTGGGCTT | GAGAGTAGTA | AGGACTCCCA | GAGAATTCCT | TGTGTTCCAA | 4740 |
| AAGTACTTCT | CCTTGACATC | TTGGTATAGG | ATTAATAACT | GTTTACCTTT | GATAATCAGG | 4800 |
| AAGAATGACT | CCAGCTAGTA | CAGTTACGTG | ATGCCTATAC | ATTCCTTTTT | TTCTGGGAAA | 4860 |
| AATGTAATGT | GAAATTAAGT | GCAAAAACCA | TGCCTTGTTT | ATGTATGTAT | CAAACACTTC | 4920 |
| TAGAGCTTTC | CCAATACAGT | TCTCTTCTCA | GCAAACAAGA | GGACTATACC | CTCATCCCCA | 4980 |
| CCCCTGCACT | TAGGTGTAGC | CAATGTGTTG | TAACTTAAAG | AGGAGAGGGC | ACTGGATGAA | 5040 |
| GGGAAATCTG | TCTAACAAGC | TTCTTTATTT | CACCTAGTGG | AAAAAAGCCT | TAATCTGCAG | 5100 |
| TGGGGCAGTT | TTCAAGGACA | TAGACTGAAT | TGGCTCATGC | ATTTATGGAA | GATGAGGAGT | 5160 |
| CCCATGATCT | GTAATCTGCA | AGCTGGAGAC | CCAGGAAAGC | TGGTGGTATG | ATTCAGTCTG | 5220 |
| AATCTGAAGG | CCTGAGAACC | AGAGGAACTG | ATGATGTAAA | TCCCAGTTCA | AGAGCAGGAG | 5280 |
| ACCAGATGAG | ATGTCCCAGC | TCAAGCAGTG | AGGCAGAAAA | AAAGGCCCAA | ATTCCCCCTT | 5340 |
| CCTCTGCCTT | TTCTTCTATT | CAGACCCTGA | ATATCAGGTG | GCATAATGCC | ATCCACACTG | 5400 |
| GGAAAGACAG | TTTACTTTAC | TAGGATCACC | TATTCAAAGG | CTAATCTCAT | CCAGAAACAC | 5460 |
| GCTCACAAAC | ACAGCCAGAA | ATAATGTTTA | ACCAGATAGC | TGGTTATCCC | CTGACTCAGT | 5520 |
| CAAGTTGACA | CAAAAAATGA | ACTATTTCAA | AGCTTACTGT | AATCAACAGT | TTTGTCAAAA | 5580 |
| AGATAGACAC | AAATCAGTGG | AATGAGATAA | ACAGTCTAGA | AATAAACCAA | CAAAAATATT | 5640 |
| GCCAACTAAG | GCAAAGGTAA | TCAATGGAAA | AAAGATAGTC | TTAGCAACAA | ATAGTACTGG | 5700 |
| AACACCACAA | TGTGTTAATA | AAGTGAAACT | GGAGACATCT | CTCACACCTT | ATACAAAAGT | 5760 |
| AACTAAAAAT | AAATCAAAGG | ACTAGATGTA | ATGTATCAAA | CATTACATCT | TTTAGAATGT | 5820 |
| ATCAAACATT | ACAAGCTTTT | AGAATAAAAT | ATAGAAGAAA | ATTTACATGA | TCTAAGATTT | 5880 |
| GGCCCCAATG | AAGTTTTAGC | TATAATAACA | AAAGTATTAG | TCATGGAAGA | AAACAAAATT | 5940 |
| GATAAGTTCA | GGTGGGCTAA | ATTAAGGGAA | AAAAATCACT | TTGCAGTAGA | GAAACCTGAA | 6000 |
| ACATTACCTA | AACCACATGA | TGAAGGTTAA | TATCAGTGAT | GTCATGTGGA | TATCATGTTC | 6060 |
| TCCCTAAAAT | GATGTGACAA | GAAGGGCCCT | TTGCCCTTGT | GGTATTATTT | CAAAAAATCT | 6120 |
| ATAACTCCGG | TGTAATTATG | AAAAAAAAGC | AAATGATCTT | CAGGACTGTT | AAGGTCATGA | 6180 |
| AAAGCAAGAA | AAGACTGAGA | CATTGTCACA | GACAAAAAAA | GACTAGGGAG | ATATGACAAG | 6240 |
| AAAATGCAGT | GTGGTATTCC | AGATTGGACC | TTGGAACAGA | AAGAAAACAT | TAGTGGAAAC | 6300 |
| AGTGGTGAAA | TCCACATAAA | GTCTAGGGTT | TGGTTAATAG | AGTTTCATGT | ATCAATGTGA | 6360 |
| GTTGCTTATA | TTTGACAAAT | GTATCATAAT | AATGTAAAAT | CCTAACAATG | GGGGAAAGCT | 6420 |
| AGGTGAAAGA | TATATGGGAA | CTCTCCTGTA | CTGTCTTTGT | ACTATCTTTG | CAACTTTCCT | 6480 |
| GAAAATCCAA | ATTATTCTAA | AACAGAAAAG | TTCATGCTAT | TAGAAGTGAG | GATAGAGGTT | 6540 |
| ACCTTGAAGA | AGCTGAGGTC | TAGAAGAGAC | CATGAAGGGT | CTAATTAGCT | AACACACGTT | 6600 |
| GAGTATCCCT | TATGCTTAGA | ACCAGAAGTA | TTTCAGATTT | TTTCAGATTT | GGAATGTTTG | 6660 |
| CATTATACTG | AGTATCTCAA | ATCCAAAAAT | CCAAATCTG | AAATATTCCA | TGAGCACTCC | 6720 |
| TTTGAGAATC | ATGTTAGCAT | TCAAAAGTT | GCCGATTTTG | GAGCATTTTG | AATTTCCAAT | 6780 |
| TTTTAGATTA | GGAATACTCA | ACCTGAGTAG | AGGCTGCCTG | CTAATTACCT | GGGAGCTAAT | 6840 |
| TACATGGATA | TGTCATTTTG | AGAAAGTTTA | GCTTGCTGAT | ATGGATGATT | TTCTGGATAA | 6900 |
| AAATTATACT | TTGATAACAA | TTCTTTTAAA | GGAGACAATA | ATTATTAACT | TTAAGTACT | 6960 |
| TTTTAGCTCT | ACAATTCAGA | ATTCTTTAGT | GCTAAATATT | ACATATTTTG | AAACAAAAGT | 7020 |
| TTTGTTTATA | TTTATTTATT | TGTTTCCCCC | CCCCTTTTTT | TTTTTTGAG | ACAAGTTCTC | 7080 |

| | | | | | | |
|---|---|---|---|---|---|---|
| ACCTTATTGC | CCATGCTATA | GTGCAGTGGG | TGATTATAGC | TCACTGCAGC | CTCAAACTCC | 7140 |
| TGGACTCAAA | GGATCCTCCT | GCCTCAACCT | CCCAAGTAGC | TAGGAGTACA | AGCATGCACC | 7200 |
| ACCATATCCA | GCTAATTTTT | GTTTATTTCT | ACAGAGGCAG | GGTCTCACTA | TGTTGCCCAG | 7260 |
| GCTGATCTCA | AATTCCTGGC | CTCAAGTATC | CTCCCACCTC | TGCTTCCCAA | AGCGCTGGGA | 7320 |
| TTACAGGTGT | AAGTCATTGC | ACCCAGCCAA | AAGTTTTATT | TTAAACTTAT | TATTATGAGC | 7380 |
| ATGTAACAGA | TTTATGTGGT | TTGAAATTCA | AACCTACAAA | AGAAAATAAT | AAAAAGCTAA | 7440 |
| CAGATAGACA | AACAAAAACA | AAAGCAAAAC | CCCACTTGGC | CATGCTCTCT | AGTTCCTCAT | 7500 |
| TTCTCTCTTG | GAAGAAACCA | GAGCAATGTT | CCCTGTGTAT | CCTTCCAGAG | ATAATTTTTT | 7560 |
| AAAATACTTT | TTTCTTTTTA | ACAGAAGAGA | TGGTAGACTA | CTTCTTTTAA | ATTAAATTAA | 7620 |
| TATACATTTA | CTTGTTTCTT | TTTATTGCTA | TAGAAAATGA | AGTTGGGGAA | ACAGGAAAAA | 7680 |
| TGACCTAGTA | TTATCATACT | AACATACCAA | AATTTTTCAG | TTATATGTAT | TTCCTGTTTC | 7740 |
| AGTTTTTACC | CCACCTGTTT | TTTATTTGGT | TTGAAATCAT | AGTACAGATA | AAAACTTGAG | 7800 |
| GCAGGTATTT | TAGACTTGTT | TTTCTTTTGT | AACATAAAAC | TTTGAGAGCA | CCAGGAAATC | 7860 |
| TGGAAATATT | CATTTAGTTA | TTCATAATTC | AAAATATTGT | TATATCCACT | TTGTGTCAGA | 7920 |
| CTATTTGTTA | AGAACTAAAC | TAAAAGAAAA | AGATGGGGCT | GGACATGGTG | GCTCACACCT | 7980 |
| GTAATCCCAG | CACTTTGGGA | GGCTGAGGCG | GGTGGATCAC | CTGAGTTTGG | GAGTTCGAGG | 8040 |
| AAAGCCTTGC | CAACACGGTG | AAACCCTGTC | TCTACTAAAA | ATACAAAAAT | TAGCCAGGTG | 8100 |
| TGGTGACACA | CGTCTGTAAT | CCCAGCTACT | CAGGAGGCTG | AGGCAGGAGA | ATCACTTGAA | 8160 |
| CCCAGGAGGT | GGAGGTTGCT | GTGAGCCGAG | ATCATGCCAC | TGCACTCCAG | CCTGGGCAGC | 8220 |
| AAAGCAAGAT | TCCATCTCAA | AAAAAAGAT | GATAACACCC | TCTGGGAGAT | TACATTCAGA | 8280 |
| TAGAACAAAT | AAAGGTGTAG | AACCTAAGAT | GTGACAAGGA | CACTGTTGGG | TGACTGATTC | 8340 |
| TTCCTGGGAA | CATTTATAAA | GGCTTCCTAG | GGGAGGGCGT | GTTTGTGTAA | GAGCTTTCCA | 8400 |
| GGTCAGAAAG | TATGTACAGT | GGAAAATGTA | TATGAAAAGA | CCGTGTTTGG | GAATCAGGGA | 8460 |
| TTATATATTG | TGATTAGAGG | AAAGAGTCCT | AGGGTTTGAT | ACCTACAAAG | AATTAGAGTT | 8520 |
| TCTAGGTGCT | TCTGGACATG | TGGATTGATG | ACAGCAATAC | TAAAAATACA | AAAATTAGTG | 8580 |
| GGGCATAGTG | GTGAGCGCCT | GTAGTCCAG | CTACTTGGGA | GGCTGAGGCA | GGAGAATAGC | 8640 |
| TTGAACCCGG | GAGGCGGAGG | TTGCAGTGAG | CCGAGATTGT | GCCACTGCAC | TCCAGCCTGG | 8700 |
| GTGACAGAAC | GAGACTCCGT | CTCAAAAAAA | AAAAAGAAA | AAAAGCAGGA | GTTAGCAGAA | 8760 |
| AACCAACAAG | ACATGGGAAG | GAGAGAGAGA | GCTGCAACAC | CCAAGAGAAA | AAATAGCAAT | 8820 |
| GCTGAAATCA | AAGTATAATG | AAGGAGAGAG | GATGCTGGAA | GCTATGAAAT | TCTTTCTGTG | 8880 |
| AGGCAATGGG | GCAATGACCC | TAGAACTGCT | GAGTTAGCAG | CAGTGACAGA | CTCAGTGCCA | 8940 |
| AATCATATAT | TAGAAAAAAA | AATCAGATAG | AGGTAAAGTC | CAGATCCAAA | GAAGAGGGTT | 9000 |
| TTTAGCAGTA | AAGCAGACAG | TAGAACCCAC | CCAGCTTTCT | AGGGTGCAGG | GGGCCTCCCT | 9060 |
| TTCAGGCATC | ATGAACAGTG | GGGGACCATA | ACTAGGCATG | ATGGCTTCAG | ATACAGGGCT | 9120 |
| TGTTCATCTC | TTGTTGTGGT | CAGGCACTGC | CTAATGAGAG | CAACCCCTTC | CAAATGCTAC | 9180 |
| TGCTGTGTTT | AACTAGGGCT | CTTGATAATC | TGACCAGCTT | CTGTCTTACT | GATTTAGGA | 9240 |
| GAAAATGGA | GCAACCTGCA | AGATGAGTGG | GATTAGCTTC | GTGCTGTCTC | CCATGCACAC | 9300 |
| CACTCATGCA | CACTTGGCGA | GCATGGCAGT | TCCATTTATT | TTGCACCCAG | TTGTGATTTA | 9360 |
| AAAACTTTTA | ATTAATTAGT | CTTATTAGTC | TTCAGTTGGA | TTTAAATGCC | AAATAATAAC | 9420 |
| CTTCTACCTT | GTAAGAGGAG | CCCTTTTACC | TAAAGCAAGG | CTTAAGTTTG | GATAAATTTT | 9480 |

```
GTCCTATTTA  TTATTCATCC  ACAAGCTCTC  TTAAAACACT  GAATACACAC  TAAGAAGGCT   9540
CTCAGCACTC  CGAATAGTGT  GATAAATCAA  AAGCCAGTAA  CTTCTCAAAG  TCATTGTGTA   9600
TTAGTCAGGG  CTCTCCAGAA  AAATAAAACC  AATAGAACAT  ATATACATGG  GCTTTTACCC   9660
AAATGTCATC  TTTTCAATGA  GTCCTCTTGC  CTGCTTAATT  TTTCTTTTTA  GCATTTGCCA   9720
CCTCCATATA  ACATGCACTT  TACTTATTTA  TTGTCTTATT  CTCTTTCACA  TGGGCAGGGG   9780
TTGCATTTGT  CTGTTTACTG  CTGTATCCCT  AGCACCTAGA  GTGGTGCCTG  GCATACGGCT   9840
GGTGTGTGAT  ACATATATTT  GGAGTGGAGG  TAAAAGTCAC  CACTTAGGCT  ATCCACTTTT   9900
GTGACAGGGA  CAACACACGT  ATCACTTGTC  ATTGTACCTA  TAGCATCTCA  CCCAGAGCCA   9960
CAAAAAAGT  GGCTCAAAGT  ATATATTAAC  AAAGAACAAA  ATGGAATAAT  CCCATCTGAA  10020
GGCGAGGATA  TAATAAAAGC  AACATACCTT  TTTTGGAAG   GACATGGAGA  GCATCAACCT  10080
TAAGACTAAA  GACTAAACTT  GAGAAGCAAT  TATTACATTT  CTATTAAAAA  TTACCAAATA  10140
CAAATAGTTA  ACTTTGAAGA  AATATATGAA  TAATGATGGT  ATCTGCAAAA  GAGGAAAAGA  10200
CTTACTCAAT  TTCATTGTAC  CTTAGTTGTA  AATAGTATTC  AGGCCACCAT  TTGGAACCTA  10260
TGTGACACAG  TTTAGTTCCT  GTCTATGTTC  ATAAGAGAGG  GCAAAGGCCC  GTTTACATCC  10320
AACCTCTGTA  TGCCAGCAGC  CACGTATGCC  ACACTCTAAA  ATGGCTAAAC  AGTCATTCAT  10380
CAGAATCGGT  TCCAAGAACT  CCAACAAAAA  TTAGAGCTCA  TGGTGCCAGA  TTGGCCTGGA  10440
TTTTCATGCT  CCTGGGTGAT  TACAAAGTTG  TAAATAATGA  TGCTGTCCAC  TGATTTTCAT  10500
CATGCGGGGC  TCTCTGCTTC  ACTGTGCCTT  CCTCTTATGT  CCATGGCACC  AATTTCTCTG  10560
ATAGTTCCCC  CAGGGGATAG  GGTTAGATGT  GGGTTCATAA  GCGCTGGACC  ACTGAGGGTA  10620
ATTCACTCTT  AAGACTAGCG  AGCACTTTCT  GAATCTGAGG  AGTCACATAT  TAAAAGAGGC  10680
AGAATCATCT  TCTGATTTCA  AAAAGCAAC   TACATGACCA  CCCTGAAAGT  GATTTCAAAA  10740
CAGTTGAAAG  CTAGCTGTTC  AAGTTGATAA  AAGCCACTGC  AGTTCCCTGC  AGGGAATGCT  10800
GATGGGCTCC  GTTCCCTCTG  CACATTAGAG  CCATTTAAAT  GAAATAATTG  ATCATATTAA  10860
CTGAAATCAC  CTGGCTTATA  GCTCAGGTCC  TAAGAATTGT  TAGTGGCACT  TGGAGCTACA  10920
AAGAGGAGTC  CCCAAAAGAA  ACGATTCTCA  CTTTATTTTG  GCAAATGGGT  GGCTTAAGTA  10980
GAACTGGTCC  TATTCCATAA  CAATAAAAAA  GGAAAAATA   AATTTTATAT  AAACTTATTT  11040
CCAAGATTTC  TTACCCCTTC  TTGTCAGCAT  TTCAACTTTA  TTTGGTGGAA  CTATCTTTTC  11100
TCAATTATGT  GTGATGTATT  GTGGTCGTGA  ATCATGGTGT  CCTGAACTCC  CTTTGGAAGC  11160
TAAAACGGTC  TGTTGAGGCT  CTGCCTACCA  GCTCTCTAGG  GTTTGTTAAA  GCAAAGAGT   11220
GAGCACTTTA  CTTAAATTTC  ACCAATTATA  TTATCTTCTG  AGACCTAAA   TGTTGAGTAG  11280
AGGGAAAATA  CAAGTTCAAG  CCTATTTATT  TCAACAATGG  AGCAAGTTGC  TACAGCTAAG  11340
ACCTTTTGAG  GCTGCCTGTT  TCTTCAGGTT  TTCCTTTGAT  TCTCAGAGTA  ACCCCACCTC  11400
AATTTATTTG  AATACATGTA  CTTATGGCTT  AACCAACACA  CAGGTGGTTT  CTTTAACTAC  11460
AGTGCAAAAA  TCTTCACACA  TACAAACTTT  TTAAAAAACA  ATTCTCAATA  TGAAAAGAG   11520
AAATCAATAT  AATTGGCTAC  AAATTATTGG  CATCTTTTCA  GAGATTTTCT  CAAGAAAGTA  11580
ACTGAATTCC  TAAAATTCTT  ATGACTTTGT  TAAAGGACTC  AAAATGAACA  TATATTCTGG  11640
CTGGGCAGGT  GGCTCATGCT  TGTAATCATA  GCACTTTGGG  AGGCCAAGGA  TTGTGGATCA  11700
CTTGAGGTCA  GGAGTTCGAG  ACCAGCCTGG  CCAACATGGT  GAAACCCCGT  CTCTACCAGA  11760
AATACAAAAA  TTAGCCAGGC  GTGGTAGTGG  GTGCCTGTAA  TCCCAGCTAC  TTGGAAGGCT  11820
GAGGCAGGAG  AATTGCTTGA  ACCCAGGAGG  CAGAGGTTGC  AGTGAGCCAA  GATTGCGCCA  11880
```

```
TTGCACTCCA GCACGGGCAA CAGAGGGAGA CTGCATCTCC AAAAAAAAAA AAAAACAAAA  11940
ACCTCATATG TCCTACAAAG CAAGTGATAA AAATCAAAAT ATGACAATGG GCTGAGAGGA  12000
AAGGGAAACT AGTAGTATTA AAGAAAGTTT TTAATGAACA AATAATGTTA AGGCGGATTT  12060
TTTTGTTTGT TTATTTGTTT TTGGCCTTTT TTTTTTTTTT TTTTTTTTT TTTTGAGACA  12120
GAGTCTCACT CTGTCGCCGA GGCTGGAGGG CAGTGGCACT GTGTTGGCTC ACTGCAACCT  12180
CCGTCTCCTG GGTTCAAGCA ATTCTCCTGT GCTAAGGCAA ATTTTAAGG ATTATAAATA  12240
GTAAATATTA GAAGGGATAC TGCTTAAAAA TAAACAATTT GGATAGCTAA ATGGTCTTCA  12300
GACTCTTTTG ATTGTACAAC ATGTAAAAGA ATTTTGAAAA CTTTAGGCAT TCCTTTGAAT  12360
ATTTTTAACT TGATTTCTAA AACTTTTCAT CAAAAATAA ATTGTTTGT AAATAAAAGA   12420
AAACATTAAA CATGTTATAA GATGAAATAA GATGAAGAGT GACTATAATT AGAATAAGTA  12480
TTTCATGACA TAAGTTTATT TTAATAAAAG TTCTAACCAC TTTATTGTAT CATTCATATC  12540
AAGTTTTTTA AATATATATT GAAATTTGGT GCTCTGGGAA AATATGCCAG CTTCATTTGA  12600
AAGAATGAGT TCCTATCCTG TACTGCTTCA GTTATTCTGA ATTCAGAACA TTCCCACTCT  12660
GGCCAGTCCT CTCTTATAAT AAAACATACA ATACTGTGCA TATTCTCAGT GATTAAAAAA  12720
AATACACACA GCAGATAAAA GAAGAGGGAG CAGGCAAACC AAGAGCCAAG GTGAATGTGT  12780
TAATCATTAG CAGGTTATCC CCAAACCAAT ATTTGGAAGT ACTCCTTTGT TGACAACCAG  12840
GAAGTGTTTA CACTTCAGGC ATTGCACCTA AATAAAGTGT GGATGCCTTT CCTTTCTAAA  12900
GTGGAAGGAG GGATATTGTG GACATAGGCA CATTCTGAGG CAATTTAGG AAATAAGTTG   12960
AAATTGATGG AAATTGAGAA AGACTTTGGA AAGTGTTTGC CTGCCTCCAC TACCAAAAG   13020
TCCATGGAGA AAGCAAAGTA AAAGGTCCAA AAATGAAAGT CAGCAGAAAC CAGAAAGATG  13080
GGCAACAAGG TTTTACCATA CAGATAAATA GAAGAGAGAT TCTTAGTAAA GAAAACAAAT  13140
TGAGGACAAT CACTAAATAA AACAAAATCG AAGGAAACTC TAAGACCACC AGCCAAAAAG  13200
CAAGAGAAAA TGATTAACAC CTTGGCACAT CTTGGTGAAG GAATTCCAGG ATAAAGAGAA  13260
TCCTATAGCA CCTAGCCTAA ACATAGCTCT CCTACAAAAA GTAGCTGGCT AACTAGACTT  13320
CCTCATATTG GACATCAGAA GAGACTAGCA GGAAGTCAAT ACTGTTTTGA ATAAGACAAA  13380
TTGTGGAACA AAATTTCTGT TCCAGCTAA GTTAATATTA CAATGTTTTA AGGCTCCACA   13440
GTGATCATAA AGAGTACTAT GAAATAAATT CTCAGCTACT GTGGGACTCA GAGGCTCATC  13500
CAAGTACTGC TCCAAAAAAA TACTCCATTG AAATGTTTTG AGATGAAGAA GGATAAAGGA  13560
TGGACATGAA AAAACAAAAC AAAAAACACT TCATTGTCCA GGGGTATGCT AAGTGAGCAA  13620
GAAGTGTCCA GCACTCAAAA TTAAGGAGGC ACTCACTCTC ATGTGCCAAT TCTGTTCTTG  13680
CATGAGCCTA AGAAAGGATG CCTCCTTAAA TATTGCTTCT TGGGCACCTC ACTTGCCTCA  13740
TCTTGGTTTC AGCCCTCAAA TTATGTTCAA ATAACAGTGA AAAGTATAAT ACCCAACAGA  13800
ATGCAAATGG TATAATTCTT CTATGGAAAC TACTCAATGC AAAATTAATA CATTAACTGC  13860
AAAAGGTCAG AGCAAAACTT CCAGAGAACA GTAGTGAAAC CAAGAGTGAG ATGATAGGAT  13920
GCCTCAGTGT GTCTGTTTTC TTATTATATA TAAGGAGAGA GACATGGCTA GGCATGGTGT  13980
CTCATGTCTG TCATCCCAGC ATTTTGTGAG ACCAAGGCAG GAGGATCCCT TGAAGCCAGC  14040
AGTTTCAGAC CAGCCTGAGC AACACAGCAA GATCCCTGTA TCTACAAAAA AAAAAAAAA   14100
AAAAAAAGC TGAGAGTCAA CAGCCACTTT TTTACTATAT AGGTTATTAA CTTGAGAAAT   14160
AAAGCATTAA AAGAACAATG AATTTGGGAG CACAACACAG CAAAATGTAA TCTGCCCACA  14220
AAATTGGACT TAGAGGAGCA ATTTTCCTCT AAGCTTTAAC CTGTTTCATA ATTAAATGAA  14280
```

-continued

| | | | | | | |
|---|---|---|---|---|---|---|
| AAATAAATAA | ACTATCCAAA | ACAAAATTTA | TATGAAGTAA | AGCAAAGGGA | AATAGGACAT | 14340 |
| AAGCTTGATA | AAAGATAAAG | CTAATCAAAT | ATAAATAAA | AAGACAAGCA | GGGCTGGGCG | 14400 |
| CAGTGGCTCA | TGCCTGTAAT | CCCAGCACTT | TGGGAGGCCA | AGGTGGGTAG | ATCATCTAAG | 14460 |
| GTCAGGAGTT | TGAGACCAGC | TTGGCCAACA | TAGCAAAACC | CCATCTCTAT | TAAAAATACA | 14520 |
| GAAATTAGCC | AGACATGGTG | GTGCATGACT | GTAATCCCAG | CTACTCGGGA | GTCTGAGGCA | 14580 |
| GGAGAATCAC | TTGAACCCGG | GAGGCGGAGG | TTGCAGTGAG | CCGAGATCGC | GCCACTGCAC | 14640 |
| TCCAGCCTGG | GTGACAGAGT | GAGACTCCGT | CTCAAAATA | AATAAGTAAA | TAAATAAAAG | 14700 |
| ACAAGCTATT | CTTAAAATTA | GTAAATGACT | AAGTAGTCTA | ATGAAGGAGA | AAGAAAGCAC | 14760 |
| ACATGCAATT | GGGTCAGAAG | TACAAAGAAG | CTAAAACCTC | AGATATAGAT | AAAATGATAT | 14820 |
| ATTATTAAAA | AGATAGCCTG | ATAAAACAGT | TGAATTTTTG | CAAATATACT | TTAAATAGTG | 14880 |
| TGTAAAATAG | ATGATCCTCC | AGATAACATA | AATGGTCCAA | ATTGATCAAA | GAAAAATATA | 14940 |
| AAACCCCTTA | AAAGACCAGT | AACTGAAGGA | AATTGAGAAA | GTTATCAAAG | TCTCCTCAAA | 15000 |
| ATGGCTTTCA | GCCTGCATGA | TTTTTACAAA | CCAATGCTTT | CAAGCTTTCA | AATAACAACA | 15060 |
| GCAATTATAA | AAATTCCATT | CTAGTCAATC | TTTTTCAGAG | TAATGGGGAA | AAAGGAAAGT | 15120 |
| TCTCCTTTCT | TGTTTTTGAA | ATCAGCATAA | GCTCCATATC | CAGACACAAA | AAAGATACAC | 15180 |
| AAAACACATG | TATGCATACA | GAGCCAATCT | CATATATCAG | TACATCAGCC | AAAGTCCTAA | 15240 |
| ATAAACTATT | AGTGAATCAA | ATTCTGTCGT | ACATCAAAAG | AATATTCAAG | GGAAAGCTCA | 15300 |
| ACATTAAGAA | ATACATTAAT | ATAATTCATA | ATATTTAACA | GTCAAGGAGA | AAAAGTAAGT | 15360 |
| CATCTCATCA | TTAGGTAGAT | GACAATAAAC | TATTTGAGAA | AAGTGAATTA | ATTTTCATGA | 15420 |
| CTATTGTTAG | AAACAATCCT | TTAGGGATGG | GGAGGGGAGA | TGAATTAGAA | ATGTTTCCTA | 15480 |
| TCAGTTCACA | ATTGCATCTA | TTCTGAAGCC | ATTAGGAATG | TGAATGGTAA | CTCTTCCTCA | 15540 |
| AACCATCACA | TAAGGAAAGA | TACCCTGAAA | GTCTGACACA | CCGAAGTCAT | CTGTCAGGAA | 15600 |
| TCAATCAGAG | AAGCTGCTGG | GAAAACCTCA | GAGAAGCTGC | TGGGAAAACC | TAGGCATTCT | 15660 |
| GAGTCATCAT | TGTTCTTATC | ACCCGTGGCA | ACTGATGCAA | TTGGAAGCAA | CTGATGCTTT | 15720 |
| CAGGGTCATG | GTTTCTTCAA | AGCCTGAGCT | CATTAATTTT | GCTGTTTGAG | AACTTGCAGT | 15780 |
| TTGATCCAAA | AGCTGACAGC | ATCGATTGAC | CCATTGCCTT | CCTTCCTGCT | CTGATACTGG | 15840 |
| AAGTTCCAAC | AAAAGAGGAG | GAGGAACAGG | ACCAAGAAGA | ACATGAAAGC | AGAGGACCAG | 15900 |
| GGGCCGGGCG | CGGTGGCTCA | CACCTGTAAT | CCCAGCACTT | TGGGAGGCTC | AGGTGGGCGG | 15960 |
| ATCACGAGGT | CAGGAGATCG | AGACCATCCT | GGCTAACATG | GTGAAACCCC | GTCTCTACTA | 16020 |
| AAAAATACAA | AAAATTAGCC | GGGCATGGTG | GCAGGTGCCT | GTAGTCCCAG | CTACTGGGGA | 16080 |
| GGCTGAGGCA | GGAGAATGGC | ATGAACCCGG | GAGGCAAAGC | TTTCAGTGAG | CTAAGATCGA | 16140 |
| GCCACTGCAC | TCCAGCCCGG | GCGACAGAGT | AAGACTCTGT | CTAAAAAAAA | AAAAAAAAA | 16200 |
| AAAAAAAGCA | AAGGACCGAA | GGACCAAGAC | CCCTTCCCAA | CTGCTCCATT | GGTCAAAACG | 16260 |
| AAGTCAGAGC | AGAAGCTCTC | AAAAGGATGA | TACTTTGAAT | TTGCTTTCTG | TTTTATTTTC | 16320 |
| TACATTCATA | AACGTGCACA | AATCATAAAT | GTACAATATT | CACAAAGTAA | ACACACATCC | 16380 |
| AAGTCAAGAA | ATAAAATATT | TCTAGTACCC | CAGGAGCACT | TCTTAAGTAC | CATCCATCCA | 16440 |
| GCCACAACCC | CCATCCCTGC | ACAAGGGAAA | TCGCTCACTG | ATTTTTAACA | GGACAGATTG | 16500 |
| GTTGTAGCTG | TTTTTAAAAA | GTATTTTATA | AACCTTTAAA | AGAATGTGCG | TTTTGTCTTC | 16560 |
| CTTTAATCAA | TATTGTGCTT | ATGAGACCCA | TTCATCTATT | ATATATTGGG | GTCTGTTAAT | 16620 |
| TCTCATTGCT | ATACAAATAG | ACCGTGGTTT | ATTTACTCAT | TCTTTTTTTA | ACAGACAACT | 16680 |

| | | | | | |
|---|---|---|---|---|---|
|TCCTGTTCAG|GCTATTACAG|ATAGTGCTCC|TATGAACATT|GTTGTACATG|TTTTATGGAT 16740|
|GTATATGTGC|ATTTCTAAGT|AAAATGTTTG|AGTCACTGGA|ATTGTACATT|TAGCTTTAGG 16800|
|AGATATTGCC|GAGCAGCTTT|CCAAAGTTCA|CATTCGTAAC|GTATGAAAGT|TCCAGTTGCT 16860|
|CCACATGTCT|GGCAACATTT|TGTTTTCCAT|CTCCTTTCAT|TTTATCCATT|AGTTAATTTT 16920|
|ATAGTGGTAT|TTCATTGTAG|TTTTGATTTT|CATTTCTGTA|ATGACTAATG|AAGTTGAACA 16980|
|TCTTTTTATA|TGTTAAGGAG|CCACTTACAT|TTTCTCTTTT|ATGAAGTCCC|TGTTCAAGTC 17040|
|ATTGGCCCAT|TTTTAGTTG|GGTTGTCTGT|CCCCCACCCT|TTTTGTTTT|TTTTTCTCT 17100|
|TTTTTCTGTA|CATAATTTGA|CTACCTATTA|TACTATGTCT|TTCTTTTTC|TTCTACTTCT 17160|
|TCTTTTAGTT|TTCTGCAAAC|CCCCTTTCCT|CTTTGTGTTG|TCAATATCAT|GAAGGCAAAA 17220|
|TCAATGTTCT|CATCTTAGTA|CCACCCTCAG|GGCCTGACAC|TCTGTTTTC|TGAAAACTT 17280|
|GCTCAAAAAT|ACCCATTGAT|TTGCATTAGG|AGATTCTCTT|CATCTGCTGA|ATTAACCCAA 17340|
|GGTTCTTGTC|CAAGCAGTTT|TTAATAGGA|TTAAAATAT|GGTGGGAACT|TCTTCTCTAG 17400|
|ACATGTTGTG|GCAAAACCAG|AATCAGTTCT|GTGTGAGGAG|ACAAACTAAA|GGATATGTCT 17460|
|TAAGTGTTAG|GAGCCAAATT|AATTCCTGTT|AGAGTTGACG|CTGCCTATCT|GAGTATCTTG 17520|
|GGAAAGTAAG|AAAAATATGA|AGAAGGTTAA|ATTATCTTTT|TCTACGCTCA|AAAGGAACTT 17580|
|CTCTTGTATG|TGATACACTT|CTATGCCTTG|TATGTGATAC|ATTTCTATGC|CTTTTCTCAT 17640|
|CTTGTTATGT|CTTCAATATT|TTTCTCCCCC|ATATAAATTG|TCATTTCACT|TGAAAGTGTC 17700|
|TCTGTCATCT|CTCTCCAATT|TTCATTATAT|GGTCTAAACT|ATATTGCTAT|CCCTTCTGGA 17760|
|AGTGTCTACA|TTGCCTTCCT|TCACATTCAT|TCTTCTCACA|ATACAAGCCT|TCCAGTTCTA 17820|
|TCTTCTCTGT|CCTTGATTTC|TAAGTTAACC|TCATTTATTT|AATCTTGTAT|TGGTCATTTT 17880|
|CTCATCATTA|ATCTCTTGCA|ATTGGGCTAG|GATAAATAAA|TATCTGTTTA|ATCTGATGGA 17940|
|AATATCTGGA|TCTAAATAAT|TTGAAAATGG|TCTATTTTAT|TTTAGCATGT|AAATTTTAAT 18000|
|AGAATTTAAT|CACATAAATA|AACGTCTATG|TTTTACAATG|TATAAAAAAT|AATAAAAACT 18060|
|TTAATTCTGG|GGATTATAGC|TTTACAGTTC|CGATCGGTGC|TGAGATCTGT|AACATATGGC 18120|
|TACAATTCCG|AGCAGATCTT|CTCTGCATCC|AATAACCTGC|CCCACCATGA|AGATATTTAT 18180|
|CAGTGATCAT|TTTCACATGA|ATTTTATTT|ATTAGTACT|TTCCAATGAG|GAAAATTCAA 18240|
|AGGCCACATG|AATTGACTTT|TCAAGTTTGT|CCAGCTGTTG|TCAACCCCGG|GCGCATGCTA 18300|
|GAAACCTCTA|AGGAGTATCT|AAAAATTAGT|AGTATCTGGG|TTCCACCCCA|GACCAATTCA 18360|
|TTCAGAATCT|CTGGAGTGGG|TCCCAAGTAT|CAGTGTCTTA|TAAAGGCTCC|CCAGGGAAGA 18420|
|CTAACACACA|GCCAGAGTTA|AGAACTGCTG|AGTCTATGGT|CAGGAATATG|GAGAGAAGTA 18480|
|AAAAATGTTT|AAAAAGTTCA|TGCTCAGTAC|CACATTTAAG|TTTGTAACTT|TATGTCCTCA 18540|
|GAGGCGGGTA|AGGGTCCTCT|CTTTGGCCCA|GTCTTGAAGT|TCTGCTTGTC|CAAACGTGAG 18600|
|GTAAAAGACC|AGGCCAAACA|TGTTGACTGC|AGCAGACAGG|AAAAAGACAT|TCCTCCAACC 18660|
|AGACTCAAAA|TCCTAGATGT|AAAAAACAGA|GAAATGATC|AATCTCACAA|GTTCCTTCTA 18720|
|CACCAGTTCT|AGTAGCCCTC|CCAGTTGTGT|ATTGCAATGT|TGATCACAAG|GAATATAAGG 18780|
|AACAATGTGC|AGTAGTTACT|TAAGAAAGTT|TATGAAACTA|TTGGAAACAA|AATGGCCAAA 18840|
|ATGCACATGG|GGTTCTGAGT|TGAGATGGTT|ATTTCTTTAA|ACAAAAATAA|AATACACTAA 18900|
|TGTTTTTCTG|AAAATTTGGA|TTTCAACATA|TAATATTACT|CATTTAAAAT|TATGCCTAAA 18960|
|ATGGCATTGT|GGCATTGTGT|TTGTGTCTTC|TCTGTTTTTT|TTTGTTGTTG|TTGTTGCTGT 19020|
|TTGTTTTGTT|TTTTTTTGTT|TCTGTATTGG|CTGTTGACAA|CTATCACTAC|AACCCATCTC 19080|

| | | | | | | |
|---|---|---|---|---|---|---|
| AATTCAACAT | GAGTTCTCTT | TGGTCTTCTG | TGTGACCCTC | CTCAGAAAGC | CCTACTAAGT | 19140 |
| CATTTCCAGC | ATTATAGTCA | CAGTGGATTC | CTAGCAGTTT | AGTCAAATAT | TAACCTGGGA | 19200 |
| ACTTGATCAC | ATAGAAATGT | AGTAAAAACA | AAACTTCTCT | TTGTAAGTTG | GTTCTCGTCA | 19260 |
| GTCCTTCCAT | CCCTGCCTGG | GTCTGTCTTT | TCATCTTCCT | CATGAGCCTG | CATTTCCAAA | 19320 |
| CACCGAGCAA | GCCTCCTTGC | AATGTCTCAC | AGCCGATCTG | TTTCCAGACA | TTAAATTATC | 19380 |
| TTTAAACTGG | CCTAGGACAC | TTTGTTTCCC | TTTTGTGATT | TTTTAAAAAT | TGGATTAGTC | 19440 |
| TGAACATATT | CTTCATGATC | TTCTTTTGCC | CCTCTGTCTT | CGTCTCTTGC | TATTCCTTGA | 19500 |
| CATGTGTCTT | TCATTCTGGT | CATAACTAAG | AACTGTTTCA | TGCTCATGTA | CCTCTAGGAA | 19560 |
| GTCACACGTG | CTGTCTTCTG | CACCGGAACA | GCTCATTTTA | ATCAATCTAA | CATCTATTCA | 19620 |
| TCTTGAGAAA | ATAAGCTTAT | ATTTTCTTC | CTCTGGGAAA | TCTGACCTAC | CAGAGTCTGA | 19680 |
| TTTAGAGGCT | CATGTAAATA | GAGTAATTGT | GTTGCCATCC | AGATCTTTAG | AGCACCGTGT | 19740 |
| GTATCTCCAA | CACCTAAAAC | AATACCTGCC | ACTTGAAGAT | GTTCAATAAA | CTGGCCCAAC | 19800 |
| CTGACTGATG | AGGAATCCAG | TGGCAGTGGA | AGAGATGATT | CCTGCGATGA | GCCCAAATCC | 19860 |
| CCTTGAGATT | CCCATGAGGA | AACTTGCATA | TCTGTGGGAA | GATGATTTTA | TAAATGATTT | 19920 |
| TATATAGAAA | GCCACCTACA | GCTTCTGCAG | CAACTCAACT | TTAATGCAAT | TCAGCTCTAA | 19980 |
| TGGCAAAGTC | ATTTGCTTA | ATGCAGTTTT | TCATTCACCT | AAAGACATTC | AGGGCAATGT | 20040 |
| CTATTTGCCA | AACCTGAAAT | TACCAATCTA | CCAAGTCAAT | AACCAGGGAG | CAATGCAGTC | 20100 |
| TCTCTGGGAA | CCACGTTTCT | TTACCCCGGC | TGCTCAGTGG | AGAAGCCAGT | TTGTGCAACG | 20160 |
| GGCAGGACAC | AGACTCCAAA | GCCAGACTCC | CCCAGTCCAA | ATCCTGGCTC | TGCCTTTATG | 20220 |
| TGACCATAGT | CACACCATTT | AACCTCCTTG | TGCCTCAGCC | TTCTCCCTTA | TAAAATGGGG | 20280 |
| ATAACAATAG | GGCCTACCTA | ATATAACTGT | GAGGATTAGA | TGTGTTGATA | TATGGCAAGT | 20340 |
| CTTGGCACAG | GAGCTGGCTT | ATTGTGACTG | TATATATATA | TATATATATA | TATATATATA | 20400 |
| TATGGTAGCT | AATATGAACA | ACACCATGGA | AACTTTTCCA | AATCACCTGT | GTGTGGGCCT | 20460 |
| TTTCCCAGCA | TACACAGTTC | AATCTCTGTT | AGGGAAGCTT | GGGAAGGTTT | TTGTCAAAAT | 20520 |
| GATTACTGGC | CAAGATTGGA | AATTGTTGTT | CTAAAAATGC | CACATTTGTT | GTTCTAAAAA | 20580 |
| TGGCCACAGA | CAGATATTTG | TAGTTATTTG | TCATTCTGCC | ATTAGTGCAA | TGTCAGTAAC | 20640 |
| ATTAAAGAGT | TTCACGGCGA | CCACTGAGGT | CTAACACCTC | TGGAGGGGTC | TGGAGGAGGG | 20700 |
| GAAAAAACAG | GTAGAGCTCT | TACCTGGGGG | CGATATCTAA | GGTGTTGATG | ATAAACCCTG | 20760 |
| AGTCACATAG | GTTACTGGTC | CCAGGAATAA | GTATCAGCAA | AATAATGGTT | ATCACGTAAC | 20820 |
| TGGAGGCCAC | AAAGGGCAGG | GCCACAGCAC | ATATTGATGG | AAGGAGGAGC | CCTGGGCAAT | 20880 |
| GAGGACATGC | TGTCAGGGAA | CCCTCTGAGA | CCATGTGCAG | AAAAGGGATT | GGTTAAATGG | 20940 |
| GCCCACACGC | TTATCCTTAC | CAAGAGATGA | AAAGAGCTTT | CGCACAGTGA | TCAATCTGAG | 21000 |
| AAGATTCCTG | GACAAAAGGA | AATCTGCCAG | CTGACCTCCT | AAAATTGTAC | AGCTTGCAGC | 21060 |
| AGCAATAAAA | GGCAGGGAGG | ACAGAACTCC | ACTCTGAAGG | AAGGAAGTTT | ATACAGAGTA | 21120 |
| GTTATAGAGA | TACGTTAGCA | CCAAAATTTG | TCAGTTACAC | AGACCAGCCA | TTAACTTACC | 21180 |
| CCCATGATAC | TGTGGGTTGT | TTGGGGGAAA | ATTAGCATCC | TTTTCACAC | TAAAAGAACA | 21240 |
| CTGTCTCAGA | TAAGAGGGCC | AGAAGCTGCA | TCACTCTGGG | CTCCAGATAA | AAGCAATATT | 21300 |
| AATTTCTTGG | GTTTTTTGTT | TTTGAAACGG | AGTCTTACTC | TGTCGCCCAG | GCTGGAGTGC | 21360 |
| AGTGGCATGA | TCTTGGCTCA | ATGCAACCTC | CACCTCCTGG | GTTCAAGCGA | TTCTCCTGTC | 21420 |
| TCAGCCTCCT | GAATAGCTGG | GATTACAGGT | GCCTGCCACC | ACACCTGGCT | AATTTTTGTA | 21480 |

| | | | | | | |
|---|---|---|---|---|---|---|
| TTTTTAGTAG | ATGATATTTA | GTAAACCATA | TTGGTCAGGC | TGGTCTTGCA | TTCCTGACCT | 21540 |
| CATGATCTGC | CTGCCTCGGC | CTCCCAAAGT | GCTGGAATTA | CAGGCATGAC | CACCATGCCT | 21600 |
| GGCCCAGCAA | TATTATTTCT | AAAAGAAGCT | TTGGAATCAG | CTGGTGTGGT | AGTATAGCAT | 21660 |
| AGTGGTTAAG | AATATGGATG | CTGCAGCAGC | TCTATCACTT | AGTATTGTGC | AACCTGGGGC | 21720 |
| AAGTTATCTC | ACCTCTAAGT | GTCCTGTTTC | CACATCTGTG | AAAAGGGAAT | TATAACAATG | 21780 |
| CCTCTCTCAA | GGTCATTGTG | AAGGTTAAAT | TAATGGTTAT | ATGTAAAGCC | AGAATGTAAT | 21840 |
| AGGTAACACA | GAACTGTTTC | TCCTTATTAC | CATTATCATT | TTCGTAGAAG | TATAGGAAGT | 21900 |
| AAACTCACAT | CTCTGATGTT | AACATGGAGC | AGAGTACTGA | TATACGTTGG | TAGGTATGTT | 21960 |
| AGGATGATGG | TGCACAACCA | GAAATGGCTG | AAAAAACCCA | GGAAAATGGC | CCAAAGTGGT | 22020 |
| AGGCATGTGA | CCATCGCCTT | TATGGGGACA | GCTCGTCCAG | GAGAACTGGG | CTGAAAAGAA | 22080 |
| AGATCTAATC | AGCATGAGTA | TTAGAGCAGC | CAAGATGGTG | CCTCTCAGAG | GAGATCCACA | 22140 |
| CCCTGCCCTA | GAGACCTCTG | CATGGGCCAC | AGGTACAAGG | TGTGCACTGT | ACCTGTTGAG | 22200 |
| CCAGTGAGGA | CAGGATGTGC | TCCTTTTCCC | TAACACTTAT | GCACGGGTGA | TGCATGGGGT | 22260 |
| CATCATAAAT | CACTGTGAAC | CATAGGAGAC | AGCAGACACA | GCCAGTGCTA | CCTGGGAAGA | 22320 |
| AGGGATAAAA | TTAGTTTTTA | GGTAGATTTG | TTTACTGGGG | GAAGGAAGTT | TCCTCTGAAG | 22380 |
| TGGCATGCCT | CTCCCTTCTA | CACACTAATC | AATTAATGCT | TATTCTACCA | TAAGGACCTA | 22440 |
| AATGTTCCCA | TTCTTTCTTT | CAATCCTTCT | ACAAACCTGT | TAAAGCTTTT | TAGATATTAC | 22500 |
| GTCTCAAATA | GAAAGCCACC | ATTTGTCAAT | GTCAGAGCCC | TCTGGAGATA | ACAGGAGCGT | 22560 |
| GGCATTGCAT | AGCTGATTAA | TTACTTTAAA | GTCTCCAATG | ATTACAGTGT | TATGTATTTT | 22620 |
| AGGCAGCAAC | TTCTTAATGC | ACACATAAGT | TGTCTTGTTG | CGGAAGATCT | GAATAGTCAG | 22680 |
| GTTTGCAGTC | ATACATACAC | GAAACAACCT | TCCATGAAAT | CATGTGGCAG | GGAAAAATTT | 22740 |
| CCAATGCACT | TACAAGAGAC | AGTATTATTT | GTATTCAAGC | CATACATCCA | TTATGGATTC | 22800 |
| CCAAAAGAAA | TATTTTTGTA | CAATACCTGG | TTAACATGTA | CAAACCAAAA | TAATTAGCAT | 22860 |
| CATTAATGAG | AAAGCCATTC | AGGCCAGGAC | TATATTTAAT | GACACCATTT | GGCTATAAAA | 22920 |
| ACAAATCAAG | TGTAGAAAAT | TGTCTTATTA | TTGGAATTCC | TTATTTGAAG | AACATTCTAT | 22980 |
| GTTAAAAGAT | TCTGAGGACT | AGTTTTCTTT | AAATCCCCTC | TAATTACTGG | ATTCACTGAT | 23040 |
| TCTTTTATTT | TAAAGCTAAA | AATCAGGCAC | CATGATGACA | CCCAAGTGAT | GAAAACATAG | 23100 |
| AATGGATTCC | TTGCCTCAAG | CATTTCACAG | TCTAGTGGAA | AGAAAAGGAG | AAATAAATAA | 23160 |
| TTACACACCA | ACATAACCTA | GAGAGGAAAT | ATCATAAAGG | AGAGAATGCC | AGAATCTGAT | 23220 |
| AGGGTAAGCC | CTGGAAGGGC | CCATGGGGAA | GGGAACATTT | GAATTGAACT | TTGCAAGATT | 23280 |
| AACTTGGTAG | AGAACAGGTG | AAAGGCATCT | TGGACAGAAA | TAATAATTAT | AATGAAATAT | 23340 |
| GAAGACACAT | TGAAAATGTA | CTTCACTATC | TTTGACATCT | TAACTGCATA | TAGCAGGCAC | 23400 |
| TTCAGATGTG | GTGGTAGAGA | TTCTGCAGAA | GGTGCTTGAT | ATGGAAGGAC | AAGACTGCAT | 23460 |
| CACAAGTCGG | TGGGTGCCAT | GTGAATAGTC | AACTCCTCTA | CCTTGTGCGT | GTGGCTTCCC | 23520 |
| AGAACCACCA | GGAAGGTGTT | AATCAGGTTG | TGTGACTAGA | TTAAAAATGA | TACCAACCGT | 23580 |
| TGACATTTTT | TATCATCTTC | CATTTGATAA | AGGACATTTT | CTTTCATATA | GGAAGAATGT | 23640 |
| GGGTGGTGTA | GGTGCCAAAA | TGGATGCTCA | GGAAATGGAG | GCGTTAGGAT | TTAAGAGAAA | 23700 |
| GTGACTCACC | AAAGATGTAC | AAGATAAAAG | GCCAGCTCAA | GGCCTGTGAG | ATTAGTCCCC | 23760 |
| CCACACAGAG | GATGATGAAG | GATCCAAATG | CTGACCCTAA | AGGAAAAAGG | GAGAAAAACA | 23820 |
| CTTATGAAAA | TATCAAAGGC | TGAGACTTCG | TGGCCTCCCT | AAACAATGTC | CCAACAGTGA | 23880 |

| | | | | | | |
|---|---|---|---|---|---|---|
| GGTGGCAGAC | TTAGAATTAT | TGGGCAATGA | GAGTATTTAT | TTCTAAAATA | GCTCACAGAT | 23940 |
| TTTCCCCAGT | AAAGTAATAT | GATATAATTA | AAATTAACAA | ATAATAGTAA | CACACTCTCT | 24000 |
| GATTCTTCAA | TGGCTCCTCA | ACACCAATGT | GACCAAATCT | AAATCCCTTA | GTTTGTCACA | 24060 |
| GTAACTCTCT | GCTATCACAG | CCCATTAGCA | TTTTCTTGTG | ATTACAGTTG | CATTCTTGCA | 24120 |
| TGATCTAATA | TGAGGCTAGG | GGCAGGAAAT | GAAAGACTTA | CAAAAATCGG | TAAGATACAG | 24180 |
| CCCCTGCCCT | CAAAGAGCTT | CTGGTCCAAT | TGGAGAGAAA | AATGTGAATA | AAATTGATTG | 24240 |
| TCACTAGTGA | AATGCCATGT | AGGCTTTGGA | AGTCTACATT | AAAAACAAC | AAGACACATA | 24300 |
| TTTCACAGAG | ACCTATAGTA | AGAAATGCAT | TTTACAGGGT | AACATAACAC | ACACACCAAT | 24360 |
| ATGCATAAAC | ACTTGTACAT | ACAACCACAC | ACATATGCCT | CAAACGATGG | TTTCATGAAT | 24420 |
| CGATATTTAA | CTTTACCATG | TCCAATGCAC | TCCAACAATT | TCTATTCTAT | TCTATTCATT | 24480 |
| TTTTAAAATA | ATGATTTTAA | CCCGCTCAAT | GGATTTTATG | ACTCACTAAT | GGGTCCCAAA | 24540 |
| CTGAAATTTG | AAAAAAAAGA | TGTAAAATAT | AAATATAATA | AAACTACAAT | GTACGTGGAA | 24600 |
| GTATATCTGA | GGATAAATTG | ATAATAATTA | TAAGATTTAG | GAAGTTTTGG | CCGGGCGCGG | 24660 |
| TGGCTCACGC | CTGTAATCCC | AGCACTTTGG | GAGGCCGAGG | CGGGCGGATC | ACGAGGTCAG | 24720 |
| GAGATTGAGA | CCATCCTGGC | TTGAAACCCC | GTCTCTACTA | AAAATACAAA | AAATTAGCCG | 24780 |
| GTCATGGTGG | CAGGCGCCTG | TAGTCCCAGC | TACTCGGGAG | GCTGAGGCAG | GAAAATGGCG | 24840 |
| TGAACCCGGG | AGGCGGAGCT | TGCAGTGAGC | CGAGATAGCG | CTACTGCAGT | CCGGCCTGGG | 24900 |
| CGAAAGAGTG | AGACACCGTC | TCAAAAAAAA | AAAAAAAAA | AAAAAAAAA | GGTTTAGGAA | 24960 |
| GTTTTTACAT | AAGCTATGCA | ATAGGATAGA | TGGAATTTTG | GCACAAGGAA | CAGGGGCAAA | 25020 |
| GAACTTTCCA | GGCATATAAA | CTAACGGGAG | CAGAGCCAGA | GGGAAGTGCA | GTGCAGATCT | 25080 |
| ATGTGGAGAG | CAGCCAATGT | CCAGTGCCAC | TGGAGCCATG | CTTGCACAGG | GGAGTTGAGT | 25140 |
| GGAACAAGGT | TGGGGCCAGA | TGGCTAAGAA | CTTTTGTATT | CATGCAATAA | AGAGGTCAGG | 25200 |
| CTTTACTCTG | TAAGCATGAA | GGAACACATT | GAAAATTCTC | AAGCGGGTGA | GTAAAAATGT | 25260 |
| GCCATCTTTA | TTTTAGCAAG | CTAACTTGGT | TTTGGTGGGA | AGAAGGTTGA | AAGAAACCAG | 25320 |
| TCTAGAAGAG | AGAGATCAGC | AGATAGTATT | TGCAAATAGA | GGAGATGGTT | ACAACTATGA | 25380 |
| TGGAAGGAAG | CAAGAACGCA | GGAGGGTTGC | TTGAGGTAAA | AGTCTGCAGG | ATGCAGCTGT | 25440 |
| GTAGTGGACC | TAGGAGTGAG | AAGCTGGATG | GAATTTTAGT | TCTGCTCTTC | GAGTATATAC | 25500 |
| TCTCAGCACG | ACAGGCTGGG | GAGAACAGCA | ATGATAAAGC | TGTAGAGGCC | TGAGTAGGAT | 25560 |
| CACATACCAT | GGAAAGGCAG | TCTAGCATAG | TGATTGAGAA | TGTCTGCTCT | GGGGCTAAAA | 25620 |
| TCTGCATGGG | CTTAAATCTC | AGACCTACCA | CCTGCTGGCT | ATTTGTATTT | GGGCAATTTT | 25680 |
| CTTAATCTCC | ACCTTCCTTA | ACTCCCTTCT | CTGTAAAATA | AGAATTTAAA | ATGGTACTTA | 25740 |
| TATGAGAGGG | TTGTTGTGAG | AATTAATGAG | CTCATAATAG | AATAGTAAAG | AGCTTAGAAT | 25800 |
| AATACAGAAA | CTTCAAACTC | TTCCAGCCTG | ATTTCTCTCC | TTACCACCTG | GAGCTGTGGT | 25860 |
| AGCCTTAATT | CTCACTTCAA | AATCATTGCT | AAGATGGTGT | ATATATAGCT | TACTTGATCT | 25920 |
| TTTTCCATGT | GTGCAATTCT | TAAAGGTTTA | AACTTTTTCC | GACAAGGCTT | TTCTGACTAC | 25980 |
| TAAGGCTTTT | CTGACTACTA | AGGCTTTTCT | GAGCTGAAAC | CTAGCTCACA | ATGGTTTTTT | 26040 |
| CTACTTCTAA | GCTTCAATGT | CTTTACTGCA | CAGATGCATC | TTTCCTATTT | GTGATGCAAG | 26100 |
| TGTCTTATAT | TGTTGAATTT | TTCAGCAGTA | CTTTTTCTCT | CTCTTCCCCA | AACCATTTGA | 26160 |
| TTCATAGAAG | ATAAGACACA | GTGGGATGGA | ACAGATGACA | AAGCTATGAC | CCATCTGTGC | 26220 |
| ACACTTACCT | GATCCTGCAA | TGGTGGTGAG | CTTGCTTCGT | TCAAGTGGAG | GAGCCCACTT | 26280 |

-continued

| | | | | | | |
|---|---|---|---|---|---|---|
| TGCCCAAATA | GTAAACTGAC | CTGTCCATGC | CATTCCCTGA | AATGAAAATC | ATTAAGACCT | 26340 |
| TTGATATTTT | GTAGAATTCA | GAAATCTGGA | TCCCACCAAG | AATGAGAAAG | TATCTGGATA | 26400 |
| CCTGGGCCAA | GCCCTGGACT | GTCCGAACCA | TGATGACCAA | AATCACTCCG | AAGTCAGCAG | 26460 |
| CCAGTGGTGT | AAAGAGGGTG | AGAAGGGAAG | AGATCAGCAA | ACCAGCACCA | AGCATTTTTT | 26520 |
| TTGCTCCAAA | TATCCCTGCT | AAATATCCAC | TTGGGATCAG | AGTCAGTATT | ATCCCATAGT | 26580 |
| TGATGGAGCT | AAAGATGATA | CCCTGAGTTT | CTGGGCTCCA | TTGATACACA | GAGGCCTGGG | 26640 |
| GGAAAAATAG | GAAAACTCTT | TGTCAAGAAG | TCCTATTATG | AAAATCTACT | TTACAGTCAG | 26700 |
| AGTTGCTTGA | GGTTAGTGAG | ACCCTAGTAT | AAAATATTGA | TTTTTGTTTC | TCTCTATATT | 26760 |
| CTTCCTACCT | TCCCAAATAA | CCAATTATAC | CCCTAATTTG | CTTGTCTTAG | TAGAAGGAGA | 26820 |
| GAAAACAGA | AGAAATGAAG | AAAAGAGGTA | AAGAAATGA | TTATATAGAT | GAATAATAGG | 26880 |
| AAGAAGTAAA | TGGAAGAAAA | CATTGAGAGA | TATTTCATCT | GTGAAAGCAC | TTCCTCTATT | 26940 |
| TTGCTTCTAG | TAAAAGTTGA | GTAACATCTT | GACTCTTATA | TCAAAGAATT | TTTTAAAACA | 27000 |
| CACACACAAA | ACTTTACTGA | ACTCTTAACC | AAAATCAGTG | CCTAATTAAA | AAGAAAAGTC | 27060 |
| AAGTTTGGGA | ATCATGGTCT | GCCCTGGCTG | AACTGAGTTC | CTAAAACACA | TATTACAAAT | 27120 |
| GAATAAGATC | ACATTCTTCT | GATATAACTC | AATAAATAAT | TTGAATTATT | TTAAAATAAC | 27180 |
| TACCTAAAAT | TCCTAAATAA | TTACATAAAT | TATATTACCT | GAATATTTAC | CTAAAAATAA | 27240 |
| ATAGATTTTA | AAATAAATAA | ATAAAAAATA | AAATAGATTT | TAAAATAAAA | TAAAAAATAA | 27300 |
| ATGCAATAAG | GCCCCTAAAT | ATCTGGCATC | ATGCTATAAA | GTAGAGAGCC | AAAGAATATA | 27360 |
| AAATATGAAA | TATTTTACCC | ACTCAAAAAA | ACTATAAATA | ATACAAGGTA | TATGATTCAT | 27420 |
| GTGAGAATCA | AGATTTGAGG | ATGAACATAA | ATAAAACAGA | GACTTTGAGA | GGAGAAAATA | 27480 |
| ATAATTTGGG | AAGGTCCCAG | AAAGGAAGCA | ATACTTGAAC | TATCCCTTGA | AAAATGACTA | 27540 |
| TGATTTGTAG | AAAGTCAAAA | AGGAAAATTT | TATCTCATCG | GAAAAAATAG | CAAAAGTGAA | 27600 |
| CTTGTAGCAT | TTGGAAGAAA | CTAACAGGGA | CTCTGGCTTG | CTCAGGGCAA | AAACTTTCCA | 27660 |
| TGGGTCATTG | ATAGCAGATG | TGAGTGTGCT | GAGAAGCAGG | CCCAAATTCT | GAAGGAACAC | 27720 |
| AGCATGTCCA | GTGAACACTG | CATGTTTGGC | AACTTGAAGG | TGTCCAAGAT | TCCTGAGTAG | 27780 |
| TGAATCTACT | CAGTGTGGAT | ATGTAGACGG | GATAATGGAG | GAAAGACTGG | AGACAATAAA | 27840 |
| TTTATGTACT | CATTGTAAAT | AAGCTAGGTC | CAATGTAATA | AAATCATTAA | TCATGAATTA | 27900 |
| TAGGGATGAC | ATGGGAAATG | TACAGTACAA | GATAATTTAA | AGGATAATTT | TTTTAATTGG | 27960 |
| GTAAATTCAT | GGTTTTCATA | TAAATGTAAA | ATAAACATAC | AACAAAGATT | TTATTTAACT | 28020 |
| CATTGATTAA | TGGAGGAAGT | AAGTAAGATG | TTATAACTGG | TTCAAAGGAA | AACTCAAAGA | 28080 |
| ATCACGCATA | ACACAAGCAG | GAAGCAATGC | TGAAATAGAC | TTTAAATATA | CAGCAGAGCC | 28140 |
| TGGCACAGTG | GCTCACACCT | GTAATCCCAA | CACTTTGGGA | GGCCGAGGCG | GGTGGATCAC | 28200 |
| CTGAGGTCAG | GAGTTCGAGA | CCAGCCTAGT | GAAACCCTGT | CTTTACTAAA | AATACAAAAA | 28260 |
| TTAGCCAGCC | GCGGTGGCAT | GCCCCCTTAC | TCCCAGCTAC | TTGGGAGGCC | GAGACAGGAA | 28320 |
| AATCTCTTGA | ACCCGGGAGG | CGGAGGCTGC | AGTGAGCTGA | GATCATGCCA | CTGCACTCCA | 28380 |
| GCCTGAATGA | CAGAGGAAGA | CTCTATCTCA | AAAACAAAC | AAACAAACAA | ACAGCAAAAT | 28440 |
| TGGCTAATTC | AACTGGGAGG | TGAGTGGAGA | AAAGTTTTAA | CTGATTTTTC | TCTTGGCAAA | 28500 |
| ATTTATTTGC | AAAGCTATGG | ACAAGAATCG | TTTGCATTTC | TATTGGTTAT | ATAGAATTTA | 28560 |
| CAGGGATATA | AAATTGCTCA | GAAACAATAA | AACAGGCAGA | GAACTGAATA | GGATTGAGTA | 28620 |
| ACCTATAAGA | ATGTGCCCAG | GTAATACCTA | GTTTTTCATT | GAAGACATCA | CATAAACTGT | 28680 |

| | | | | | | |
|---|---|---|---|---|---|---|
| TCCATTTTTA | AATTTTTCAC | ATTTAACTCT | ACAGTTCCCC | CACCTTATAA | TCATAATAAC | 28740 |
| CTCAATGAAA | TCTTATTTTT | ATTATTGAAG | TAAGCAATGT | CTCAAAGAAA | AATAGTTCCA | 28800 |
| GTCAGTTTTA | ATTTGTCATT | GGAAATGTAT | ACTTCCATAC | TCCACAGAAT | CAAGATCTAT | 28860 |
| GCCTTCCTTT | CAAAGTTTTT | TCTCTCAACA | AAGAGCCCTA | TTTTCCATCA | TACTTACCTT | 28920 |
| TGTATCAAAT | TCCTTGATGG | ATATGCTGGA | GTTATTGAAG | GCATCTGCAA | CAGGCCCCTC | 28980 |
| AGTGGAGGCA | TTAGATAGAC | CTTGCTGCTG | AGTGGTGTTC | ACCATGGCGA | TGATCGCAAT | 29040 |
| GCTCAGACTC | ACACGCTGCG | TTATCATGGT | GAAGTTTGAG | AAGTGCATGA | TAAGAGCCAG | 29100 |
| CCCATAGCGT | AATGAACAGA | AATCTGGACC | TAGACAACAA | CACAGATGTA | TGTAGTGAGC | 29160 |
| ATCCTGACTG | AGACCCCTTT | CTTTTCCTTT | CTCTCACAGC | TCGATCTGAT | AGAACTTTGG | 29220 |
| ATGACACATG | AAGTCTCATT | GTCTTTTTTT | CACCAAAATA | GCCAGCACTA | CAAACCCACT | 29280 |
| TTGTCAAATT | ATTTGGTTGG | CTTCAAGACA | GCGAATATGG | GATCTTATAA | CCAAGTAAAG | 29340 |
| CAAATATGGC | CATCTTTCAA | GGGGATAGGA | AACACATGAT | AAATAGAGAA | AACCCACATG | 29400 |
| TAAGGCATTT | ATGTCATATT | GCTCCAAAAT | GAAGTGAATG | GGGATGACAG | TGGCAGAGCC | 29460 |
| AGTCACATAA | CCTTCTCAGC | GTCAATAAAA | TTCCCTGGGC | TGTAAGTGAA | TAGTCCCATC | 29520 |
| TGTTATGCAC | ATTTGTTTAT | CACAAAGCTT | GAGAGTTTAT | ACATAACGAG | CTGCCTTTGA | 29580 |
| ATTAAGGTAT | TGCACATCCA | AGGATTCTCT | TTTAATACAT | TTGAGAGATG | GTACTTTAAA | 29640 |
| TGAGCACTTC | GACTAATTCC | CTAGTGTAAT | GTCTACTTGG | AAATGTTATT | GCTATGTGTC | 29700 |
| ACTAGGTCCT | GCCTTCACAT | ATGTTCAACT | TAAAAAAAAA | AAAAAACTAC | GTGGGGTGCA | 29760 |
| GTGGCTCACG | CCTGTAGTCC | CAGCATTTTG | GGAGGCTAAG | GCAGGTGGAT | CACTTGAGGT | 29820 |
| CAGGAGTTTG | AGACCAGCCT | GGTCAACATG | GTGAAACCCC | ATCTCTACTA | AAAATACAAA | 29880 |
| AATTACCCAG | GCATGGTGAT | GCATGCCTGT | AATCCCAGCT | ACTCGGGAGG | CTGAGTCAGG | 29940 |
| AGAATCACTT | GAACCCAGGA | GGCAGAGGTT | GCAATGAGCC | AAGATCATGT | CACTGTACTC | 30000 |
| CAGCCTGGGT | GACAGAATGA | GACTCAATCT | CAAAAAAAAA | AAAAAATTA | ATATGTAGAA | 30060 |
| CTATTTTTAC | AAAGCTTGCA | GGTGATGTGG | TGCTGGAAGA | TATTCAATAT | ATTGAAAGGA | 30120 |
| CAAATTTTTT | CTTTAAAAGC | ATCCCCATAA | AATGGAACAA | CCACAGACCA | ATATTGAAAG | 30180 |
| GGTTCCCATG | TGCATGATAG | ATTGGATTTT | TCCTGCTTAT | TTGAAGAAAA | GCACTAAAGT | 30240 |
| GAAAGAAAGA | GAAAACCTGT | GAAGACACAG | ATAAAAATAT | AATGGAAGAA | ATAATTTTTA | 30300 |
| ATGGCCAAAA | AAGCTCACAG | ATAAGAGTGG | TGGTCTGGGA | AATAATTATT | TCCATTTTAC | 30360 |
| TGGAGGTTTC | CAAGCTCAGG | AGAAAGAGCC | AGCCGCTTGG | TGAGAATATT | ATAGTAGGGA | 30420 |
| TTCATACATA | GGTTGGTTTA | AAATGACTTT | CCCGGGCCAG | GCGTGGTGGC | CCATGCCTGT | 30480 |
| AATCCCAGCA | CTTTGGGAGG | CCGAGGCCGG | TGGATCACGA | GGTCAGGAGA | TCGAGACCAT | 30540 |
| CCTGGCTAAC | ACGGCGAAAC | TCCATCTCTA | CTAAAAATAC | AAAAATTCAT | CTGGGCATGG | 30600 |
| TGGTGTGTGC | CTGTAGTCCA | AGCTACTCGG | GAGGCTGAGG | CAGGAGAATC | ACTTGAACCC | 30660 |
| GGGAGGCAGA | GGTTGCAGTG | AGCCGAGATC | GCACCACTGC | ACTCCAGCCT | GTGAGACAGA | 30720 |
| GCAAGACTCA | GTCAAAAAAA | AAAAAAAAAA | AGACTTTCCC | AAAACTTATT | CCACTCCCTA | 30780 |
| GATCCCAGGA | TTTATTGCTT | ATTTGGCTTA | ATTTCTCACA | GATGATTTCA | TGGGGCTAAG | 30840 |
| GAAAAAGCAA | CAGGATCAGG | GGCTGGAGCT | GGCTCCAATG | TTACACTGGG | AGTATCTTTA | 30900 |
| CGAAGGGTCA | GTGTGATGCA | GAGATGTGTA | AATGTGTCGG | AATAAGCTTC | AGCTTATTAA | 30960 |
| CATAGCCTGC | AAACAAGAGC | AGTGGCTTTA | CCTTTCCTGG | TGGCAGGCTT | CCCGTCCATT | 31020 |
| TAGCTTCTGT | GGGAAATGGT | ACCACGCTTT | GTGGTGGAGT | TTCCCTGTGC | CCTGAATCTC | 31080 |

| | | | | | | |
|---|---|---|---|---|---|---|
| TTTTACTACG | ACAGTCTTTT | ATCTATGGAG | AGAACATAAT | CCAAAACATA | ATACACAAAT | 31140 |
| AATTTCCCCT | TGTTAATGTT | GCCTCCTCTT | AGCATCAGTA | AAAGTTTTGA | CCCAACACAG | 31200 |
| CTCTATAACT | TACATTTTAT | GGGGCACTAC | TGGTATGCTT | TTGGTTACAG | GATTGTTAAA | 31260 |
| AGGAAATCTG | GCTGTAAGTT | CCAGCTGTGT | GACCTAGAGC | TAGTCATTTA | AATTCTCTAA | 31320 |
| TCATTCATTT | CCTCATCTGT | TCAATAAAGA | TAAGGCTCCT | TTCTTAGTGC | AGCTGGAAGA | 31380 |
| ATTAAATGAA | AAATTGCATG | TACTTTATCA | AACCACAGAG | AAGCATGCGA | AGGTGAAGAG | 31440 |
| TGGTATTGCT | TGTAGCAGAC | CATAAGACAG | GACAATTAAA | CTAAGCTCAA | GAGCTAAGGA | 31500 |
| GGAAGGTTCC | AGAGCGGTCT | TTCCTTTCAT | TCTGATGGTG | TTTCTCTCCC | CTCTGTACCA | 31560 |
| CCAGAACAAT | GTTCCATGTG | CCTTCGAACA | TGAAGGATGA | CATTACATAA | CACTAATATG | 31620 |
| TATTACATTT | AAAAGTTTAA | AATGTTTATT | CTCATGTTTG | CTACACACAA | TGTGGACACT | 31680 |
| TGCTTGGACT | GACAAAGTCT | TCATATCACC | TAGAAAATTA | TAATGAACAG | GGACTAATTA | 31740 |
| CTACAATTGT | GAATAAATCC | AGCTATTGTG | ACAGGCAAAG | AGAATTCATG | GCTCTAAATA | 31800 |
| TGGACATGTT | TAATTTAATA | TTTGTATACT | AATCAAATTA | TCTTTGGGGA | TGCATACATT | 31860 |
| TGTTTCTTTT | AGGAAAAATC | CATATCCTAA | GAATATCATC | AATTTTCCAT | TCATTCCTAA | 31920 |
| ATTGAAGCTT | CTATGACTTT | ATTTTTTAAA | TTGCTTAAAA | TCCTTCAAGA | CATCTGAAAT | 31980 |
| TTCTGTGACT | TTAAAAACAC | ATGTATCGGC | CGGGTGCAGT | GGCTCACACC | TGTAATCCCA | 32040 |
| GCACTTTGGG | AGACTGAGGT | GGGTGGATCA | CTTGAGGTCA | GGTGTTCGAG | ATCATCCTGG | 32100 |
| CCAACATGGT | GAAACCCCAT | CTCTACTAAA | AATACAAAAA | CAGCCGGGTG | TGGTGGCACA | 32160 |
| TGCCTGTAGA | CCCTGCTACT | AAGGAGGCTG | AGGCAGGATA | ATTGCTTGAA | CCCAAGAGGC | 32220 |
| AAAGGTTGCA | GTGAGCCAAG | ATCGTGCCAC | TGCACTACAG | CTTGGGGGAC | AGAGCAGGAA | 32280 |
| TCCGTCTCAA | AACAAACAAA | CAAAAAAACA | CATATATCAA | ACCTCTATTT | TATCATTCAA | 32340 |
| GGCTTTGCAC | TGTTTTTGCA | CACAAAATTT | AAAAGACTTG | TCCGTACTTT | AAAGATATTC | 32400 |
| ATAATCTGTG | ACCTTAGGAT | GAAGGATTAT | AAAGAAAGGC | ATAGATGAAA | AATTGTGTCC | 32460 |
| AAAAATATCC | TTTGTAGTAT | TACTCATGAC | TGCATAATGT | TAGAGATAAA | TTAACCTAAT | 32520 |
| AATGAGAGTC | TGGCAAGTCA | ATTTGATAGA | TTATTGTGAT | GGAAGCTATT | TTAAAATGTT | 32580 |
| TTCGACAATA | TTGAATTACA | TTAGAAAAAT | GCTAGTACTC | TAGTGTACAA | AGCAGGATAC | 32640 |
| GCTGTGCACA | TCCACATACA | GGAATAGAAA | CTGATTCACA | CAAGTGCCAG | TAATGACTAT | 32700 |
| TTCTGGGTTA | CAAAACAGGA | TGATCACTTC | ATTCTTTGTG | ACTTTCTATA | TTTACCAAGT | 32760 |
| GATTTTGTAA | ATAATTAGTA | GATACTCATT | TTATATTCAG | AAGTAGCTAA | ATGTATTTAA | 32820 |
| AAGAGCAATA | ATTGGACTTC | ATCAGCATGG | CAAGTATAGT | TTTCTGCTTT | CCAAATATCT | 32880 |
| CTAGAATTCT | GGGAATAGTA | TCTCTCCATC | TAAATTTTGA | ATTTTGGGTG | TTTGGAGATT | 32940 |
| TTATTGTTGT | TGTTGTTGTT | GTTTTGTACA | ATGGACCCAA | ATGGAGGCCC | AATTGCTAGT | 33000 |
| AAGATCAGGT | CAGCACCAGG | ACAGATACTG | GTTGTTGCTC | TGCCTTAGAA | GGCCTCCAAG | 33060 |
| TCTTGCTAAC | ATCTGGATAT | CAGGAGTTCA | GCTCATTGCT | CTACACTCAG | ATCCTAGCTG | 33120 |
| AAGTCATCTG | TGGTCAAACC | CAGAGTTTGG | ACCATTTTCT | ATTTGATTTC | ACTTTTTATG | 33180 |
| CAAGATCCCG | TGGCTTGGCT | GAAGGCAACT | CTTTAACTGT | ACATGCAGCT | GCAATTACTT | 33240 |
| ACACTCCACT | TAAAGCTTTC | CCACCAACTT | CTCCAATCTT | ATAAACACTG | AAAGCTGAAA | 33300 |
| GAGACTCAGA | GATCCTCTGG | CCCAACTGTT | TATTTTATTG | ATAAGAAAAT | TTGCGTAGAA | 33360 |
| AATTTGAAAA | GTTGCCTGAA | ACCACATGAT | GCACAGAGCC | AGCACCAGAT | CCCCTAATGC | 33420 |
| CTAGACTACT | GCTTGTTCTA | CCTATTACAA | CTTCCCCTTT | GTTTTCGTAA | TATTTTAATC | 33480 |

-continued

| | | | | | | |
|---|---|---|---|---|---|---|
| ACAAGCTTAA | AACTCAATGG | GGTAGCTCCA | TTTGAGGTA | TTATAAAGGA | GAATTTGTAT | 33540 |
| ATTTTAAATC | AAGTTTTAAT | CATTTATTCT | AGAAGGAAGT | TTGATAATGA | AAAATACTTT | 33600 |
| TAGGTTGAGC | TTTGAATATT | AAACATAAAC | ACAACAAAAC | TACTTCTCCT | TGCTCTTTAT | 33660 |
| GTTACTGGAA | TTGTATCACA | AACCCATCAC | TTTAGTTTTT | CTTCCCATTC | TCTGTTGCTG | 33720 |
| TCTAACGAGA | AAGGATGAAA | AGCCCTACTT | AAGTTTATG | GTTTCAAATG | CTACTTTGAT | 33780 |
| TTTGTATCAA | TAGGTAATTT | CAGTTCTTCG | TTTCCTATTT | TCCTTTGCAT | GAGACGAATG | 33840 |
| CAGAAATCAG | GCTAACATAC | CAAACCATCC | TAAACTGAGG | TCTTTCATGG | TAATGGGAAA | 33900 |
| TGTTTTTCCA | AAATAAGCAC | AGAAGCTAAT | AAAATTATGG | AGGCTGAACA | CTGGCATGGT | 33960 |
| TGATATGTAC | TTAGAGACAC | TGGAATAATT | ATTAACCTAT | TTGCAAACAA | TTGAGAACAT | 34020 |
| GTAACAGTGT | CAGAACCCTT | CCCTTTAAGG | AGATATACCT | CTAAAAAAAA | ATTGTGAATT | 34080 |
| CTAGTGCCAA | AGTTGTAAGT | AGACACAGAA | AAATGAATTG | AAATTAAGTT | AAAGGAAAAT | 34140 |
| GTTATATTAA | AAAAAATTAC | TTGACACAGT | ATAGGTTGAA | TTTGAGAAAA | AATAAATAA | 34200 |
| TGTAAATATT | ATGGTATACG | CATAAGCAAA | AAAACAGGTT | TTTCCCTTTT | TTTAAGTCTA | 34260 |
| GAACTCATGA | TTTTATTATA | ATGGTCGTTA | GATTGCTCTT | AGATTCTCCT | AATATCCAGC | 34320 |
| CTGTCTTGCT | TCATCTCTGT | TAGCCCAGAG | TCCTAGTTTA | CTCAGAGTAA | ATGTTACACC | 34380 |
| TAGATCAAAG | AGCATGAACC | TGCAGTGGGA | GGATATTCAA | GGACTGAATT | CTGCTCTGCC | 34440 |
| ATTCCCAAAT | TGAGTAAACC | AGGTAAAGTT | TCAAAAACTC | TTAGGGCTTT | CACTGTTTCA | 34500 |
| TAGGAAGAAT | TGGGATAATG | TTACTTCACT | GGGCAGTTTG | GAGTGAAAAC | AAAAGTATGA | 34560 |
| GACATGCCTC | GTAAATTGCA | AAGTGTTATA | TGTTGTATAA | TATTCTAGAT | ACTAGCAACA | 34620 |
| GCAATAATAA | TAAACAGTCA | CAATATTGGC | AGTCTAGCCC | TCTCAGATCC | ATAAATACAG | 34680 |
| GCCTACAGCA | AATGAAATGT | ATTTCTATAA | AAGTGCCTTT | GATTGGTTGT | TAAATTGGTT | 34740 |
| TTAAATGTTT | CTTTTTTAAA | GTGGATTCTT | CTGGCCTGGA | ATCCTCAAGA | TGAGTGGGA | 34800 |
| GGAGTTCACC | AGAAAACATA | GAAGCAATTC | CTTCAGTGTT | AGAAAAACTG | AGGGCCCTCT | 34860 |
| CATCATCTGC | CTATCTTTCT | GAGAAATTGG | TGCTGACCAC | AATGTCCCTG | GGTGCCTTTT | 34920 |
| CTTAGCTGTA | CAATGAGGGC | AACAAGCTAG | GTGATCTCTA | CAAGCGTACA | ATTTCTTGC | 34980 |
| CTTCAGTCTT | ATTCATAACT | TTGGTCATGT | TCTCCTTTTC | TTTTATTATT | ATTATTTTT | 35040 |
| TGAGACAGAG | TCTTACTCTG | TCACCTAGGC | TGGAGTGCAG | TGGTATGATC | TCAACTACTG | 35100 |
| CAACCTCTAC | GTCCTGGGTT | CAAGCAATTC | TCCTGCCTCA | GCCTTCTGAA | TAGCTGGCAC | 35160 |
| GCGCACTATG | CATGCGCATA | GGTGCACGCG | CCGCTACGCC | CTGCTAATTT | TTGTATTTTT | 35220 |
| AGTGGAGACA | GGGTTTCACC | ATGTTGGCCA | GGCTGGTCTC | AAACTCCTGA | CCTCAAGTGA | 35280 |
| TCTGCCCGCC | TCAGCCTGCC | AAAGTGCTGG | GATTACAGGC | GTGAGCCACC | AGGCCCGGCC | 35340 |
| ATGTTCTCCT | TTTCCTGAGA | GACCATTTCA | AATTCATATA | GAAGTCTGAA | AAGACTCGTT | 35400 |
| AGCCACAGTC | CCAAACACAA | ATCTTGTCAG | TTCTGATCAG | TATTTCATTC | CACAGCCAAT | 35460 |
| CCCAGTCTGA | CTAATCACAG | CATCACAGTT | AATACTCACA | GCGTCCTTGG | AGAAATGACC | 35520 |
| ATTGTCCACA | GTGTCCATTG | GTACCAGTGG | CTTCTCAAGC | CTTGCCCTAG | GGTCTTCATT | 35580 |
| GAATCAGTTA | TCTTTTTCAG | AGAGTCTCTT | CATTTTGGAA | TTAGGCAATA | TTACCAGATG | 35640 |
| GAGATCCTTA | TGTTGCTGTT | AATGTCTTTT | CTCTGACTTC | TCCTAAAACT | GTTCCCTCCC | 35700 |
| CTTAATGGAC | CTTTGGTAAG | TTAGTAATAA | TCCTTCTACC | CAAAAGAAG | AAAAGCACTT | 35760 |
| ACCTTCACCA | TTAAACCAGT | ATTTTAAGCC | CTAGACTATA | AGGCTAACTT | GGAAAAGGAG | 35820 |
| GGAGTTTTCT | GTCCCTTCTT | CCCTTTCAAA | TACTTTTGCA | GATTTTTACA | GGGATAAATA | 35880 |

-continued

| | | | | | | |
|---|---|---|---|---|---|---|
| GTGAGCCACG | TGGCAGTCAG | ACGGCAACAG | GTTGGCCCCC | ACTTTCTCAG | AAAGCCTCGG | 35940 |
| CTTGGTTTTG | CCGCTTAATT | TTTAACTTCA | TTTTCAAGTT | CTCACTGTTA | GAGTATCTCA | 36000 |
| AAAGATGTCA | TCGTGTGTTT | CTGCTTTGAA | CTGTGCATAC | AACCATTCAG | TCAACAAGCC | 36060 |
| TTTTTTTCTG | AAAGCAAGGG | GGCATGGTGT | GGAGGAAAGG | GCAGGGCTCC | TGAAATCAGT | 36120 |
| GATGGAGTCA | GACCCATATT | CACTTCCTAG | TGTTTTCCCT | GAGCTTGGAC | AAGTCACTGA | 36180 |
| ACCTCTTTGA | ATTGGCTTCC | GCTTTAGTAA | AGCAAGGATT | GTGTTACTGT | ACTCATGGGG | 36240 |
| TTATTGAACA | AATGAAATAC | ATATTCTAAT | TGGTAGTAGC | TCCTCAATAA | ATGAGGTGTT | 36300 |
| CATTCCTCTT | CAGGAGTTCA | GTTAAGTCAG | CTAGATTTTC | CATATGCATT | TGGTGCCCAC | 36360 |
| AGCCTAATGA | ATGTGAACTG | TGACTGCCCT | GGCAACTTCC | CAGGAAGCTG | CCTTGTACCC | 36420 |
| CTCCTTCCTG | TTTCATATCA | TCCATGTCTT | CCCTAATCCA | TTTTCTGCTT | GGCTCCCGAC | 36480 |
| TCTTGGAATT | GTGTCCTATT | TGTAATCATT | AATTTTGAGA | CTGTGGTTGC | TATTGGATCT | 36540 |
| TCCTAGTGTG | ACGCAACCCT | TATAAAATGA | AATGAGAGCC | TTCCCTCTCT | GGCTTATCAG | 36600 |
| CTTCAGACTT | CCTTAATTGA | GTTCCGCCAT | CCTAGTGAGT | CTCACCATAC | TCCCGAAATA | 36660 |
| ACCTGCTGGA | GTAGGCTTAT | CCTACTCAAC | TCCTCAGATC | TCTGTATTTA | ATTCTATTTT | 36720 |
| ATTGCTGTTG | TAGTAAATTA | CCACAACTGT | GATGGCTTGA | ACAACACAA | AATTATTTAT | 36780 |
| TTATTTACAA | TTCTAAAGGT | CAGAAGTCCA | AAATGGGTTT | CACTGAGCCA | AAATCAAGGT | 36840 |
| ATTGGCAAGG | TTGTGCCCCC | TCCAGAGGCT | TTAGGGGAAA | ATCCATTTCT | TTTTCTTTTC | 36900 |
| AGCTTGTAGT | GACCACTGCA | TTTTTTGGCT | CTTGGCCTTT | CCTCCACCTT | AAAGCCAGCA | 36960 |
| GTGTAACATC | TTGAAGTATT | TTTCTCTTAT | TCTGACTCTT | CTGCCTGTCT | CTTATAAGGA | 37020 |
| CCCTTGTGAT | TACACTAGGG | CCCATCTGCA | AAATTCAGGA | AAATCTGCCC | ATCTCAAAAT | 37080 |
| TCTTAACTTA | TTAAACATGT | AAAGTCCCTT | TTGTCATATA | AGGTAATATA | TTTACAGGTT | 37140 |
| CTGGGGATTA | GGACATGGAT | ATCTTTGGAG | GACAACATTC | AGCCTACCCT | TTTGAGGGAT | 37200 |
| AGAGGGGTAG | CAGGAAGAGT | TGAAACAATT | CCTTCCTTTC | TTTATTTAAA | AATTCTGGTT | 37260 |
| ATTGATTTAT | TATAGTTATC | ATGTGCCTGA | TAAGCCAATG | AAAATAGTTA | TAATGGCCAG | 37320 |
| GGGCAGTGGC | TCATGCCTGT | AATCCCAGGA | CTTTGGGAGG | CTGAGGCAGG | AGAATCGCAT | 37380 |
| AAGCCCAGGA | ATCCAAGACC | AGCCTTAGCA | ACATAGGGAG | ATCCGTCTC | CACAAAAAAA | 37440 |
| TGCAAAAATT | AGCTTGATGT | TGTGGCACAT | GCCTATAGTC | CCAGCTACTC | AGGAGGATTG | 37500 |
| CTTGAGCCCT | GGAGTTCAAG | GCTGCAGTGA | GCTGAGATTG | CACCACTGCA | CTCCAGCCTA | 37560 |
| GGCAATAGAG | CAAGACCCTG | TCAGAAAGAA | AAAGAAAGAA | AGAAAGAAAG | AAAGAAAGAA | 37620 |
| AGAAAGAAAG | AAAGAGAGAG | AGAGAAAGAA | AGAAAGAGAA | AGAGAGAAAG | AAAGAAAGAG | 37680 |
| AGAAAGAGAA | GAAAGGAGAA | CTTTCTTGGC | TTAATTTACC | CAAAAGGTAT | GATATTTTCT | 37740 |
| TAATTTGCAT | AAGGCAGAGC | ATGAGCTGAT | ACCAGTTCTG | GTAGAAAAG | TAGGTGAGAC | 37800 |
| TGGATCCCCC | AAACAAGAGT | AAATATTTAA | TATAATAAGG | AAAGAGTGGC | CGAAAGTATT | 37860 |
| CAATGCCACA | AGTAAGATTC | AGAGTAGATT | TTTCAAACTG | CATAATTTGT | TTAAAAGCA | 37920 |
| TAATTTTATA | GCTGGATTTT | GCAAGCTCTC | TGAGGGGATC | TTGTTCATTT | TGAGAATCAC | 37980 |
| TATATCCACA | ATTCTTGGCA | CAGTGTCTGT | CCTATGGTGT | GTGCTATGAT | CCAAATGTCT | 38040 |
| GTATCCTCTC | AAAACTCATG | TTGAAATCCT | AACCCACAAA | GTGATAATAT | TAGAAGGAGG | 38100 |
| GGTCTTTGGG | CAGTAGTTAT | ACCATGAGGG | CAGAAACCTC | ATCACTAGGA | TTAGTGTCCT | 38160 |
| TATAAAAGAA | ACCCAAGGAA | GTTTATTCAA | CCCTTCTGCC | ATGTTAGGAC | TCAGCAAAAA | 38220 |
| GATGGCTACC | TGTCCTCACC | AGACACTAAA | TTTGCCAGGG | CCTTAATCTT | AGACTTCCCA | 38280 |

-continued

| | | | | | | |
|---|---|---|---|---|---|---|
| CCTCCAGAAC | TGTAAGAAAT | AAATTTTTTG | TTGTTTATAA | GTCACCCAGT | TTATGATATT | 38340 |
| TTGTTACAGC | AGTCTGAACA | GACTAAGACA | GTACACGCTT | AATAAACATT | AGTTTACTGA | 38400 |
| ATGAATGAAT | TCTTGCATTG | CTTCACCACC | AACAATCAAG | ATCTCTGTAG | CTGGTTTAAC | 38460 |
| CCCCTCACTC | CCAATCATGA | TTTTCATATA | ACAAAGTTAA | CTCAGTTAAA | TCAACTCAAT | 38520 |
| AAGTATACA | TTAAATGAAA | TTAAGAAGT | TGTAACATTT | ATAAACATCA | AGAGTAATGT | 38580 |
| AGAAGAAAAG | TCCAGAGATC | CTTAAAAATT | TAAGCCTCTC | TGGCCTGACA | TTAACAGCTA | 38640 |
| AGGCAGGAAC | AGAAAACCAA | ACACCTCATG | TTCTCACTTA | TGAGTGGGAG | CTGAACAATG | 38700 |
| AGAACATGTG | GACACAGGGA | GGGGAACAAC | ACTCACTGGG | GCCTGTTGGG | GGAGGATGGG | 38760 |
| GTGGGGGTGT | GGGAGAACAT | TAGGTAAAAG | AGCTAATGCA | TGCTGTACTT | AATACCTAGG | 38820 |
| TGATGGGTTG | ATAGGTGCAG | CAAATCACCA | TGGCACACGT | TTACCTATGT | AACAAACCTG | 38880 |
| CACATCCTGT | ACTTGTACCC | AGGAACTTAA | AAAATAATAA | TTTTTAAAA | AACAGCTATT | 38940 |
| TCCAATCAGA | GCAGTTCAAT | TCCATACAAT | TATTATTATT | ATTATTATTA | TTATTATTAT | 39000 |
| TATTATTTTG | AGATGGAGTC | TCACTGTCGC | CCAGGCTGGA | GTGCAGTGGC | ATGATCTCAG | 39060 |
| CTCATTGCAA | TCTCTGCCTC | CCAGGTTCAA | GTGATCCTCC | CGCTTCAGCC | TCCTGAGTAG | 39120 |
| CTGGGATTAC | AGGTGGGCAC | CACCACGCCT | GGCTACTTTT | TGTATTTTA | GTAGAGATGA | 39180 |
| GGTTTCACCA | TTTTGGCCAG | GCTGGTCTTG | AATTTCTGAC | CTCATGTGAT | CCTCCTGCCT | 39240 |
| CGGCCTCCCA | AAGTGCTGGG | ATTACGGGCT | TGATCCACTG | CGCCCAGCCA | ACATACTATA | 39300 |
| TTTTTTTTG | ATAAATTTTC | TGTATTCTAG | ACATGACATT | AGCTTCCGAC | AATATTAATT | 39360 |
| TATTAAGATC | TGACCCATGA | CATGACTTCA | TAAGAGTTCA | GAGTCCACTG | AATGAGACCA | 39420 |
| CACACAGAGA | CAGACAACTA | GAATGAAGGA | TGATAAACAT | GAACAATACA | AACTTGCACA | 39480 |
| GGTGACTAGA | AAAGAACAAA | TGAAGACTCC | TGCCAACTGG | GGGTATCAGG | GGAAGGCTTC | 39540 |
| CCAGGCAGAA | CAGGGCTGCG | CCAGTCTCCA | TGTGTGGTAT | GAATAAGTCA | GTAATACAGG | 39600 |
| GGAAGCACCT | TCCAGAAAGA | GCAAACCCGT | TGAGGCTTGG | TGTGAGGAAT | AAGAAGTGTC | 39660 |
| CAACATGACT | GGGGATTAAA | GTACAAAGGT | ATAAAGGAAA | TGTGGTGAAC | TGACTGGAAA | 39720 |
| GATAAGAATT | TTTTTTAACA | GTTACTTTC | CCAATAGTAG | AATTAACTAG | ACAGGAATAG | 39780 |
| AAATGGAAGA | AGTTTTATG | TTCCCTTAGA | ATGAAAACTA | TACATTTTTT | AAGAATTATA | 39840 |
| TGAACAAGGA | AAATGTGACT | CAAAGGCAGA | AAATGATAGA | ATTTATTAT | AGGGCAGAAA | 39900 |
| ACAGGATCTG | GCTAAATTAA | ACTAAGTACT | CTACTATACT | ATACCATATG | CTATATTCTT | 39960 |
| GAATGGGAGA | AGTAATACCA | TAAAAACTAT | TGATTCTTCC | TAAATTAGTA | AACACATTGA | 40020 |
| GTGAAAATCC | AAGAGGAAGA | AAGAAAAATG | GAAGACAAAC | TGGAAATAGC | CCAAATTTTC | 40080 |
| ATCAGTGGAA | GACTGAGTAC | TTTGTGATAC | ATAGTCATTG | CAGAAAAATA | ACACAGTTAA | 40140 |
| AAAGAATGAA | TCACATCTAT | AACATTTGAC | CTGAATACTT | TCATATAATG | TAATACATTT | 40200 |
| TTAAATGAGT | AAAGCAGATA | CTAAGGACGT | ATAAAGGGAC | TCCATTTTTT | TCTGAATATT | 40260 |
| AATCAAGAAA | ATTCTATATA | TCTGTATCTT | TGTTTACATA | AGATTGTGTG | AGCCATAATA | 40320 |
| GCTGTTGACT | TGGGTTATCA | GGTTTGGGTA | AACAGTTTAG | TGGTAAAAAA | AAGATGTGTA | 40380 |
| AGACTTGGCC | GGGTGCAGTG | GCTCACATCT | GTAATCCCAG | AACTTTGGGA | ATCTGAGGCA | 40440 |
| GGCAGATCAC | TTGAGGTCAG | GAGTTCCAGA | CCAGCTTGGC | CAACATGGTG | AAACCTCGTC | 40500 |
| TCTATAAAAA | AACTACAAAA | ATTAGCCAGG | CATGGTGGCG | CACACCTGTA | GTACCAGCTA | 40560 |
| CTCAGGAGGC | TAAGGCAGGA | GAACCGCTTG | AACCCGGGAG | GTCGAGGTTG | CAGTGAGGTG | 40620 |
| AGATCGCGCT | ACTGCACTAA | GCCTGGGCAA | TGACAACAAA | ACTCCGTCTC | AAAAAAAAA | 40680 |

-continued

| | | | | | | |
|---|---|---|---|---|---|---|
| AAAAAAAGTG | TAAGACTTAG | CAAAAAGGTG | ACCAAAAAAA | AGCAACATTT | ATAAACTATG | 40740 |
| GATGTAAAAC | TCTATGTATG | TGTGAGTGTG | TATACATGTG | TGAATATACA | TAGGATACAT | 40800 |
| TTTTGTCTGT | ATGTGTATAT | GTACATACAT | GCATGTATGT | GTATGTGTGT | GTATATATAC | 40860 |
| AAGCTTTTTT | AAAATGTTTT | CAACAATATT | GAATTACATT | AGAAAATGC | TAGTACTGTA | 40920 |
| GTGTACAAAG | CAGGATGCGT | TGTGCACATC | CACATACAGG | AATAGAAACA | GATATATACA | 40980 |
| TACACACACA | CTACACACAC | CCCTATACCT | ACACCAAATA | TACATTGAGA | GAGAGAGATA | 41040 |
| GAGAAAATAG | TAACTAAGGT | AGTTAATTCT | GGCCACAAGG | ATTTTTAGAT | GAATCTGACT | 41100 |
| TTCTTCCTTA | GGTTTTTTTT | GTATTGTTTA | AAGTTTCACA | CAAATAGCAT | TTATTTACTG | 41160 |
| TATAATCATA | AAAGGCAAAA | ACCTATTTTG | ATTTTAGGAA | AACACAAAGC | ATCCAAACCA | 41220 |
| AAAATCTCAA | CTTAGGAAAT | AGCGGGAAAT | CTAGGGAAGT | CAACAGGACC | AGGTCATGAC | 41280 |
| GGTCTTTTAT | GCAATGTCCA | GGAGCTTGAA | CTTTATCTTG | TCGTTCCTAT | ATTTCCTCAA | 41340 |
| AACAAATGTG | TGTGGACGCA | GAAATGGAAA | TGCACAGCAG | TGCACTGAGG | TCACAGGAAA | 41400 |
| AATACAAAAC | AGTTTTTCTG | AAGTACTAAC | TTCACTCAAA | ACTTCGGGAA | ACATTTTAAA | 41460 |
| AATGGTTTTA | AACAAATTTG | ACTAAATTTG | ACAAATTTAG | TCAAATGCAA | AATTTTCATT | 41520 |
| TTTAAAAGGA | AATAAATTTT | AGAGGAAAAA | ACAGATGTGA | AAAAGAATAC | ATGAAATAGT | 41580 |
| ACATGAAGGA | ATACATGCAC | GTGGCATACA | CTTGAATCCA | TGTATATGCC | AGGTTTTCTT | 41640 |
| GTGTTGCACA | CAAGACCAAC | TCTGAAGTTA | AAGATAACCC | AGTAGAAAAA | ATTAAATGAT | 41700 |
| GGGGAGTAAT | TAAAATGTTT | TCAGCAGGAG | TAGGACATGA | TTTTTATATT | TAGACTGTTT | 41760 |
| AGTCGGCTAG | TTATGTCTGA | CGGATAGAAG | TGAGGACACT | CCTAATTGAA | AAGTAAGTGC | 41820 |
| TACTAAGAAA | CTCAACGTGG | GGGTCATAGA | ATGAAGCCAG | ACTTTTGTTC | CCAAGCAGGA | 41880 |
| GACAGATGCA | GATAAGAGGG | AATGAAGATG | AAGTAAGGGC | TGAACCACAG | AAGCTTCGCA | 41940 |
| TCATAAGTCA | TTGTATTTCT | CTGAGTGAAC | ATCATAGAAC | TTATTACTA | TCTGGTCACA | 42000 |
| AAATGCCACT | GACATGAAAA | GAAATCGGGT | TGAAATGGCT | CTAGACCAAG | ATTCCCAAGA | 42060 |
| CATCAAGAAA | TCACCAAAAG | TTGCCTCAGG | TTCACAAAAA | AAGATATTCC | AAGGGAGTTC | 42120 |
| TCCAAGTAAG | TAAACACTCA | TTATTTCTAT | AAGGCTTAGG | CCACAAGACC | TTGGCTGAGA | 42180 |
| CCCCTGTCTC | TGTGATCTGG | TCTGTACCAC | ATTGGAAGGG | CCATGACTGA | TTTCTACCTA | 42240 |
| GACATTTAAG | GCTGAACGGA | GGCTGAAGAA | CCTCTTGCTT | GCTTTCCCAT | AGACTCACAT | 42300 |
| CTGATAACAG | CCCTCATCTT | AGGCCCCAGA | GGGCAAGAAG | AGGTTAAGAA | GGATCAACCA | 42360 |
| AAGGTAAAGT | ACACCAAGAA | AAGAGCAGCT | CTTTGGTTAG | AATTTTAAGA | TAAAGAGAGA | 42420 |
| CACATAAAAG | CTACTGTTGA | AAAATAACAG | AAGGAACAAC | GTTTATCTA | ATCAATAGAT | 42480 |
| GGAACAAGAC | AATAGAGGAC | CATCTCAACA | ATAACCTAGA | ATACCATGGA | AGACAGACAT | 42540 |
| AAATCATCTG | TATTTGTCCT | GCTCAAGACT | TGCCATATGC | CAGGTATGGT | GGCTTATACC | 42600 |
| TATAATCCCA | GAACTTTTAG | GCTAAGGCAG | GAGAATTGCT | TGAGCGCAGG | AGTTCCAGAC | 42660 |
| CAGCTTGTCT | CTACAAAGTT | CTCTGGGGGT | TTTTTTTCGT | TTGTTTGTTT | TTTAGGCAGG | 42720 |
| TGTGATGGCA | CACACTTGTG | GTCCCAGCTA | CTCAGGATGC | TGAGGTGGGA | GAACAGATTG | 42780 |
| ATTCTGGGAG | GTCAAGGCTG | CAGTGAGCTA | TGATTGCTCC | ACTGCACTCC | ACCCTGGGTG | 42840 |
| ACAGGAACTG | CAGACAGCCT | CTAGAAGTTG | AATCAGCCTC | TACCAAGAAG | CTTCTACCGG | 42900 |
| TGCAAAGAAC | TGAATTTTTC | AACAAACCTG | AGGGAGCTTG | GAAGTGGAAA | TTTCCACAAT | 42960 |
| CAAGCCTCTG | ATGAGAATTC | AGACTCAGCC | AACACCTGGA | TTGCAGCCAC | ATGAGGCTTG | 43020 |
| AAGCAGGGAA | CCCAGTTAAG | CCATGTCAGA | ACTTCTATCC | ACAGACCTTA | GGTAATAATA | 43080 |

| | | | | | | |
|---|---|---|---|---|---|---|
| AATGTGTGTT | GCTTTAAGCC | ACTAAGTTTT | TGCTAATTTG | TTTTGTAACA | ATTATATATA | 43140 |
| ACTAGTACAC | ATGAATAGTA | GAATCTAATA | TCAGCCATTG | ACTTCAATGA | AGGAAAAAAC | 43200 |
| AGATGTGAAA | AAGAATACAT | GAAATAGTAC | ATGAAAGAAT | ACCTGCACAT | GGCATACACT | 43260 |
| TGAATCCATG | TATATGCCAG | GCTTTCTTGT | GTTGCACACC | CAGACCAACC | CTGTAGTTAA | 43320 |
| AGATAACACA | GTAGAAAAAC | TGAAGAGTTA | CTGAGAGTAA | TTAAAATGTC | TTAAGCAGGA | 43380 |
| GTGGGGCATG | ATTTTTATTT | TTAGACCGTT | TAGTCTGCTA | GTTATATCTG | ATGGTTAGAA | 43440 |
| GTGAGCCTAT | CTCTGGTCCC | ATGTTCTTAG | AGAGTACT | TTTATCTCTT | TATCCATCTA | 43500 |
| ACATCTCTAA | TTTATGTAAC | ATCCCAAGTC | CTCATTAATC | CTGTGTTATT | GCTGTTGGAA | 43560 |
| GTCCATCTAT | CCCCTCAAGA | ACAGAGCCTG | AAATTCCTCT | TTGAAAATT | TCCATTCATC | 43620 |
| ATAATCTCAA | ATTTCTCCAA | TGTCATTTTC | CACCTAAATT | TCATGTGTGA | CTTGAATCTC | 43680 |
| AAGACTATTC | ATCTGCCCCA | GGTATCTGTT | TGATGCCTGG | ATATGTCTGA | ATTATTATTA | 43740 |
| TTGTTATTAT | TATTATTTTT | TTTTAAATG | GAGTCTTGCT | CTGTCACCCA | GGCTGGAGTG | 43800 |
| CAGTGGTGCG | ATCTCAGCTC | ACTACAACCT | CTGCCTCCTG | AGTTCAAGTG | ATTGTCCTCC | 43860 |
| CTCAGCCTCC | CCAGTAGCTG | GGATTACAGG | TGCCTGGCAC | CTCGCCCAGC | TAATTTTTTT | 43920 |
| GTATTCTTAG | TAGAGATGGG | TTTTCACCAT | GTTGGCCAGG | CTGGTTTTGA | ACTCCTGACC | 43980 |
| TCAAGTGATC | CACCCACCTC | AGTCTCCAA | AGTGCTGGGA | TTACAGGTAT | GAGCCGCCAC | 44040 |
| ACCCAACCTT | AGACCTCATC | CTACCCAGCT | CACGTGTCTT | TTAATCCTTT | AGCTGAGGTT | 44100 |
| GTAGTTTTAA | CTTATTGCTG | CTTGAACCTA | TTTCAATGCA | AAAGTTCTAA | AAGAACTCAG | 44160 |
| CCACCAAAAT | TCCCTTGATT | TGCTGCACTG | TACCAAATAT | TAGTCTTAAT | GAAATACAAG | 44220 |
| ATTTGTTTCA | GGATCTCAAG | CCCAATATTT | TCAACTGTAG | GCTTCCCAGT | ATCCAAGGTT | 44280 |
| TACGCAGGAG | ATTGGCAGTG | GGTACATTCC | CAGGGTCAGT | GGTTTTTATC | CAGGAAGGAA | 44340 |
| CCTCAGAATC | ACCTGGGGAA | TTTTAGCAAC | ATACACACCA | GTGTTCTCAG | GAGTGAGGCT | 44400 |
| CAGGTATGTG | GATGGCAACA | ATACTTCCCT | TATCAAAAAG | CTGCCACCAC | ACCAGACAAA | 44460 |
| TGAAAACTGC | TCTTTAATTA | TACAGCTTGG | CCTTACCTAA | TGGTTCTCAA | TTTTGGATGG | 44520 |
| ACATTCAAAT | CACAAGGGTA | GTTGGTTTTT | TTGTTTTGT | TTTGTTGAGA | CAGACTCTCA | 44580 |
| CTCTGTCGCC | CAGGTTGGAG | TGCAGTGGCG | CCATCTCGGC | TCACTGCAAC | CTCCACCTCA | 44640 |
| TGAACGTAGT | TTTAAACAGC | ACTAGTGCCT | AAACCAGACT | CCAGAGATCA | TGATCCCTAA | 44700 |
| TCCTATCCCT | ACCCTGCGGT | ACTCATTCTG | AGATATGCCC | TGGGTAATAA | GAATTTTAGA | 44760 |
| AGGTACTCAG | GTGATTCTAA | TGTTCAACCA | GTCTGAGAAC | CATTCGCAGA | CTTCATATAG | 44820 |
| ATACTTTATT | CCAAACAGCT | GAGCTGGACC | ATAGCTAGAA | GAAGGAATAG | AGATGAATGA | 44880 |
| GAGTTCATAT | TTTCCATAGA | AAGCCGCTGC | CCTCTTCTAA | ATGTGAATGG | AAGTTCTGGA | 44940 |
| GACCCCTATC | CTAAGGTAGA | CAGATGACAG | ATACACTGGA | GAATGCTGAA | GGAAGCAGAT | 45000 |
| AGGAGTCTAG | GCTTTAGACC | ACACCTTCCA | AGACGTACTA | CTCATGCCTG | ATGAAGTATT | 45060 |
| ACCAAACATA | CCCCTGGGCC | AATAAACAAA | GCAGGAGCAA | ATGTGTTTGT | GTGTGTATAA | 45120 |
| CTTTCTACAC | AAAATACAGA | AAAAAGTGAT | TCAATGTTCA | GCATAAATAA | AATTTTGTGT | 45180 |
| TTTAGTATTG | TTTTATTTCA | AAGTACATCT | TGGTGAGAAT | GCATTATTTT | GAACTGGATA | 45240 |
| AAAGCCCCCC | ACTACTGAAT | CCCAGGTCTC | TCTATGAAGC | CTGAATAGAG | GCACTGTAAC | 45300 |
| TCTAATGGCC | AAAGGGCTGG | CCTGGAAATT | CTCCCTTCAG | CTGCAAAAAG | AGAAAAGAA | 45360 |
| TAATCCAAGC | AAACAAACAA | AACAAAGAAA | TGAGCAAACC | ACTACAACAC | AAAACCCTTG | 45420 |
| GGATGAGATG | AGTACTAGAC | TGGGAAAGTG | ATAGCTCTGG | TATTCATGTG | TGTGTGTGTG | 45480 |

| | | | | | | |
|---|---|---|---|---|---|---|
| TGTGTGTGTG | TGTGTGTGAG | AGAGAGAGAG | AGAGAGAGAG | CACATGAGAG | CACACACAAG | 45540 |
| ACCCTATAGA | GGAACCAAGT | AGCTTATCTT | CTTCCTTGGA | TTCCTCTATC | TCATAGCCTA | 45600 |
| GAAGACATGG | GGTGATCCTA | GCCCCTGGTA | GTGTAGGACA | AGGTAGAGTG | GGACTGTGGT | 45660 |
| TTTAAAATAC | TTTTTAGACC | GGGTGTGGTG | GCTCATCAAC | ACTTTCGGAG | GCGGAGGTGG | 45720 |
| GTGGATCACC | TGAGGTCAGG | AGTTTGAGAC | AAGCTTGACC | AACATGCTGA | AACCCCGTCT | 45780 |
| CTACTAAAAA | TATAAAAATT | AGCTGGGCAT | GGTGGCAGGC | ACCTGTAATC | TCAGCTACTC | 45840 |
| AGGAGTCTGA | GGCAAGAGAA | TCGCTTAAAC | ACAGGAGGCA | GAGTTTGCAG | TGAGCCAACA | 45900 |
| TCATGCCATT | GCACTCCAGC | CTGGGTGACA | AGGGTGAAAC | TCTGACTCAA | AGTTAATTAG | 45960 |
| TTAATTAAAA | TAAAATACTT | TTTTATTTGG | GGCTGGGTGC | AGTGGCTCAT | GCCTATAATT | 46020 |
| CTAGCACTTT | GGGAGGCCAA | AGTGGGAGGA | TCACTTGGGG | GCAGGAGTTT | GAGACTAGCC | 46080 |
| TGGGTGACAT | AGCAACATGC | CATCTCTACA | AAAATTTAAA | AATAAAAAT | TAGCTGAGTG | 46140 |
| CAGTGGTGCA | CACCTGAAGT | ACCAGCTACT | CATGAGCCTG | AGGTAGGGGG | AATTACTGGA | 46200 |
| GCCCAGGAAG | TTGAGGCTGC | AGTGAGCAAT | GATTGGGCCA | CTGAGCTACA | GCCTGGTGAC | 46260 |
| AGAATAAGAT | GCTGTCTCTA | AAAACAAAAA | ACAAACAAAA | AAAACCCAAA | AACCTTCTTA | 46320 |
| TTTTAAAATG | ATTTCAAACA | TATAGAAAAA | TCAGAAAAAC | AGTACAAAGA | ACACTCATAT | 46380 |
| ACTTTTTACC | TAGATTGTTA | ATATTATACA | TTTGCTTTTT | CTCTACCTAT | CCATTTATTT | 46440 |
| ATATGTCTTT | ATATCTCTTT | ATATATATAT | ATACTTACTG | AAACATTTGA | AAGTTGCAGA | 46500 |
| TAATCATCTT | CCTATATTAC | TCAATACTTT | ATCTTTAAAT | TCAAATTCAA | ATTTTACCAG | 46560 |
| CTGTCCCAAT | CATGTCTCTG | ACAACACTTT | TTCCCCTCAA | TCCAGGATCA | CAAATTGCAT | 46620 |
| TTGGTTGCTA | TCTCTTTAGT | CTCTATTAAC | CTGGAACAGT | TTCCTGGCCT | TTCTTTATCT | 46680 |
| TTCATGATAT | GAAATGACAA | TGAATTTTTA | AAGGTTAGGT | GTTTTGTAGA | TTAGTTCAGT | 46740 |
| TTTAAAACTT | CACAACAAAG | TGCCAAAGAT | GTCTTGGCAG | CAGTGCTCAA | AACAGGTTGG | 46800 |
| AGATGCATAG | GAGCCACAGA | GAAGGGTCTG | GTTCAAAGGC | CAGTGGTCGT | CTCATTACAG | 46860 |
| CACTGCTCCA | TCAGGTCTAG | GTCTGGAGAC | TTGGTAGCAC | GTCTATGGCC | CCAAAGTGTG | 46920 |
| TAGAGAATGT | TGAGAATTGC | CTAGGGTGGC | AGACTTAGAG | GAAGAAAGGT | TGGTATGAGG | 46980 |
| CCTGTCTAAA | ATTGAATTTG | GCTATAGAGT | TATGGAAGGG | TTTTAGGCCA | TGTCTGGGTG | 47040 |
| GAATCAGATT | CAGTCAGCAA | GTAAGGGGTC | TTTGGGAGGT | GAGCTTAGGC | TGTCTGGGCC | 47100 |
| CCTTCGAGGA | GGGCAGATTT | TATGGGGAAG | GGCTCTCCTA | GAAGAACCTA | GTTAGGATG | 47160 |
| AGCAAATCAC | GCAGGTTCAT | TCTCCACTTT | ACCCTAGCAC | TTCCTAGGCT | CAGTGGTGGT | 47220 |
| TTTGAACTTT | TCCCATCCCT | GCAATTACTC | CATAAAGGGA | ATGTGCAAGG | AAGAGGGGAG | 47280 |
| GAAAGAGATG | TGAGTTCTGC | CAGAGGCTTC | ACTGTTTCAT | TCCCAGATTT | ATTTGAAACC | 47340 |
| AACCCTCCTC | CTGTACTTCA | TGCTCTCCAA | GCTCATGGTC | CTGGAACTTC | ACATTTACAT | 47400 |
| AATACGGAAT | TTTTTTTATT | ACCCTTGATC | TTTATGCATG | CAATCTTTCT | GAACACCCTG | 47460 |
| GACCCCCTCC | TTCTCTTGGT | GACCTTTTCC | TTCTCCAAAA | CATGGTTCAC | CAGTTATTAC | 47520 |
| CTCTGCAGCA | GTGGTCCTTC | CAGGAGTTGC | TTGCTGCTTT | GTTCTTCTCT | CAGCCTCAAC | 47580 |
| ACTTTTTCTT | ATCTTGTTAC | AGCATTTAGA | ATGTAATGTT | TTGTTTTGTT | TTTAAAACAC | 47640 |
| ATCTTGGCTT | TCTGGAAACT | TATATAGAAA | ATAATTTTTT | TTCCCTCAAT | AGATATATGG | 47700 |
| CTAGGGTCCA | GCCTAATGTC | TGCCATAGAG | AAGCCTAATG | TCCAGCCTAA | TGTCAATAAA | 47760 |
| TGTTTATTGT | GGGCATAAAG | GAATACATTT | TAAAATAATG | GAGTGTTTAG | GTAAAATTAG | 47820 |
| GATTATTAGC | TTGAGTCATT | TAAAATCATC | CACAAGAACC | AGATCAAATG | TACATGTCTT | 47880 |

| | | | | | | |
|---|---|---|---|---|---|---|
| TAATACTGGT | GAAAGAAGTA | GTTACGCTGT | CTTAAAGGCA | AAACGATATG | GACATAGCCA | 47940 |
| CCAGAAATAC | AAGAGTGCCA | TCTCTTGGTA | AACCTGTTAG | CAGACAGAGA | AGACACTGAG | 48000 |
| AAGCCATGTA | AAATATACTT | GATAATGTGT | CTCTTATGTA | GGTTATGTAA | AATGTGGAAG | 48060 |
| AAAGATGGAA | ACAAAATTGA | GAGACGTGGT | TATGGCATTT | TCCAGGAAAA | TTGGAAAATA | 48120 |
| TTTTCTCCTA | ATAATTCATG | CAAAATGTAA | TGATATTTT | TAATGCAGAA | GAAACAGTG | 48180 |
| TAACAAAAAG | CATTATAATT | ATGGCAAATT | GTTGAATGCT | TTCTCCACCC | CTGCCCTTTC | 48240 |
| CACTCAGAGT | AGGAATGAAA | TAAGGATGTC | AGTTATCACA | CTTTATGTTC | AATATTATAT | 48300 |
| GGGAGATGCT | AGCCAGTGTA | CTGTGGAAAG | AAAAATAAAT | GTTAATGTTA | GATGTTAATG | 48360 |
| GTGTAAATAT | TTCAATTGAA | AGGCAAAGAT | TGTTAGAATC | GACTTAAAAA | TGCAAGAACC | 48420 |
| AAACACGTTG | GCTAGAAGAG | AAACATCTTA | AATATAAAAA | CACAGATAAC | TTGAGAATAA | 48480 |
| ACATATTAAA | ATATATACAC | TATGCAAACA | GAAAGCATAA | AAAGACTAAA | ATGGCTATAA | 48540 |
| TAATAACAGC | TAAAATAGAG | TTTAAGACAG | AGAGTGTTAC | CAGAGACAGA | GTGATATTTT | 48600 |
| GTATTGTTAA | AGGAGTCAGT | TGCCAGCCTG | GCCAACATAG | AAAAACCCCA | TCTCTACTAA | 48660 |
| AAATACAAAA | ATTAGCCAGT | CATGGTGGTA | TGTGCCTGTA | ATCCAGCTA | CTCGGGAGGC | 48720 |
| TGAGGCATGG | GAATTGCTTG | AACCCAGGAG | GCGGAGGTTG | CAGTGAGCCA | AGATCACACC | 48780 |
| ACCGCATTCT | ACCCTGGGTG | ACAGAGTGAG | ACTCTGTCTC | AAAAAAATAA | AATAAAATAA | 48840 |
| AAATGCCGAG | GTGGGCGGAT | CACCTGAGGT | CAGAGGTTCG | AGACCAGCCT | GGCCAACGTG | 48900 |
| GTGAAACTCT | GTCTCTAATA | AAAATACAAA | ATTAGTTTGG | CATGCTGGCA | CATGCCTGTA | 48960 |
| ATCCAGCTA | CTTGGAGGCT | GAGTCAGGAG | ACTCGCTTGA | ACCCAGGAGG | TGGAGGTTGC | 49020 |
| AGTGAACCAA | GATTGTGCCA | CTGTACTCCA | GCCTGGGCAA | CAGAGTGAGA | CTCCATTTCA | 49080 |
| GAAAAAACAA | AAACAATGAC | AATAGAAAAG | TGTCATTTCA | TCAAGAAAAC | ATAATAATCA | 49140 |
| TAAATGTATG | ATTCTAACAA | CAGAGTTTCA | AAATACATAA | CGAAGTTTTA | AAATACATAG | 49200 |
| CAAAATGTCA | TAACAGAGTT | TCAAAATACA | TAAAGTAAAA | ATGGAAAAGA | AAAGACAAAA | 49260 |
| TAGACAATTC | TACAATCACA | TTTGGAGAGT | TTAACACCCT | TTTTTTGGTA | ATGATGCAAT | 49320 |
| AACTAGACAA | AATATCAGTA | AAGACACAGA | AGATCTGAAC | AATCCTATCT | ATTATCTTGA | 49380 |
| GCTAATTGAT | TTATAGAACA | TTATACACAA | TATCTGCATG | CACATTTTGC | TCAAGTACAC | 49440 |
| ATGATATATA | CATCATGATA | GATCATATTC | TTTTTTTCTT | TTATTTTTAG | TTGACATATA | 49500 |
| ATAACTGTAC | ATATATACGG | GATAAAGAGT | GATATTTTA | TATGTGTACA | CAATGTGTAA | 49560 |
| TAATCAAATC | AGAGTAATTA | GTATATCCAT | CACCTTAAAC | ATTTATCATT | TATTTTGTTG | 49620 |
| TGAGTATTCA | AAATTCTTTT | CTAGCTTTTT | GAAAATATAC | AATAAATGAG | AGTTAACCAT | 49680 |
| ATGCACCCTA | CAATGGTGCA | GAACACCGGA | ACTCATTTCT | ACAATCTAGC | TGTAATTTTG | 49740 |
| TCACCATTAA | CCAACCTCTC | CCTATCCTCC | CCTCCTTGCT | ACCCTTCCCA | GCTTCCGGTA | 49800 |
| CCCACAGTTC | TGTTCTCTAA | ATCCATGAGC | TAAAAATTTT | TCTCTACTTT | CACATATGAG | 49860 |
| TGATAACATG | TAGTATTTAT | CTTTCCAATC | CTAGCTTATC | TTACTTAACA | TAATGTTCTC | 49920 |
| CAGTTTCATC | TACGTTGCCA | CAAATGACAA | GATTGCATTC | TTCTCATGGC | CAAATAGTAT | 49980 |
| TTCATTGTGT | ATATATGCCA | CATTTTCTAT | CCATTGTCT | GTTAATGAAC | ATTTAGGGTT | 50040 |
| GACTCTATAT | ATCAGCTCTT | GTGAAGAGTG | ACGCAATAAA | CATGGGGATG | TAGGTGTCTC | 50100 |
| TTTGTATACT | GATTTCCTTC | CCTTTGGATA | AATAGCCAGT | AGCAGATTTT | CAGCCTCATC | 50160 |
| TGGTAGATCT | ATTTTTAGGT | TTCTGAGAAA | CCTCTGTTGT | CAGTAGGCTG | GTTCAGATTC | 50220 |
| TTGAATTCCC | TGCACAAAAG | AATTTGAAAG | CCAGTCCAAA | GTAAAAGTAG | GCAAAGGAGT | 50280 |

| | | | | | | |
|---|---|---|---|---|---|---|
| TTATTGCAAG | GTGAAAGTAC | ACGCTGATAG | CAGAGTCAGG | GTCGGCTACT | TCAGCACCAA | 50340 |
| TTGACACTGA | AGAAACTCCC | GTTATGGGAG | TCCTACGTGA | TTATCCATGA | GGGGGTGGGA | 50400 |
| ATGGGCATTG | TTGTTAAATA | TGTTTGGGT | GGTCTCTTGA | ATGTGCATGC | AATATTGCCA | 50460 |
| TACACGCTAG | TACATACATC | ACATGTATTA | TTAGCATTTT | AATTCTCTAC | CCAAGGGTGT | 50520 |
| GTTTCTTACT | ATTAAAATGA | GTATATGTCA | ACCTGAGAAC | ACAGCTTGTG | GGTTTCTGCA | 50580 |
| CTTGCACGAA | CTTAGGGATT | TTCCCTCCTG | CTCTTCTACC | TCCTTGACTG | AGGATATTCT | 50640 |
| AACCACTAGC | CCCAGATGCA | GTTTGTGTAA | TGTCAAGAGA | TTTGTTCTCT | CCATCAATTT | 50700 |
| GACAAGTTTC | TTGTTTCCTT | TCAAGGGAGG | CTGTGACCAC | CCTATGTAAC | CTACCTCACT | 50760 |
| TCCATACTAT | TTTGCATAAT | GGCTATGCTA | ATTGACATTT | CCACCAGTGG | GACATAAGAG | 50820 |
| TCCCTCTTC | TGTACATCCT | CACCAGCATT | TGTTATTTTT | TGTTTTTTTG | ACAATAGCCA | 50880 |
| TTCTAACTGG | GGTGAGATGA | TACCTTATTG | TGGTTTTGAT | TTGCATTTCC | CTGATGATTA | 50940 |
| GTTATTTATA | TGGTTTGGCT | GTGTCCCTAC | CCAAATCTCA | TCTTGAATTG | TAACTCCCAC | 51000 |
| AATTCCCATG | TGTCCTGGGA | GGAACCCAGT | GGGAGGTGAC | TGAATTATGG | GCCGGGTCTT | 51060 |
| TCCTATGCTG | TTCTTATGAT | AGTGAATGAG | TCTCACGAGA | TCTGATGGTT | TAAAAACGG | 51120 |
| GAGTTTCCCT | GCACAAGCTC | TCTCTTTGCC | TGCTGCCATC | CATGTAAGAT | GTGACTTGCT | 51180 |
| CCTCCTTGCC | TTCCACCATG | ATTGTGAGAT | CTCTCCAGCC | ATGTGGAACT | GTAAGTCCAT | 51240 |
| TAAACCTCTT | TCTCTTGTAA | ATTCCCCAGT | CTCAGGTTAA | GTCTTTATTA | GCAGCATGAA | 51300 |
| AACAGACTAA | TACAGTGATG | TTGAGCATTC | TTTCATATAT | TTGTTGGCCA | ATTGTATGCC | 51360 |
| TTCTTTTGAG | AAATGTCTGT | TCAGTTCACT | TGCCCACTTT | TTAAATGAAT | TGTTGGTTGT | 51420 |
| GCACGGGTGG | CTCGTGCCTA | TAATCCCAGC | ACTTTGGGTG | GCTGAGGCAG | GAGAACTGCT | 51480 |
| TGGGACTAGG | AGTTTGGGAC | AAACCTGGGC | AACACAGAAA | GGCCCTGTCT | CTAAAAAAAT | 51540 |
| GAAATAATA | AAAATAAATG | AATTATTAAA | TCTGACTACA | GTAGAAATAA | ATTTGAAATC | 51600 |
| AATAAAAATA | AGAAATGTAG | AAAAAAACAC | ACATATTTGG | AAATTAAACA | TCATTCTAAT | 51660 |
| TAATCAATCT | CTCCAAACAA | ATCACAAAAA | ATTACAAAAT | ACATTGTACT | ATATAATAAT | 51720 |
| GACAATAAAG | CACATCAAAA | TTCATGGGAT | GCAACTTAAA | CAGTGTGTAG | AGAGATCTGT | 51780 |
| AACTTAAATT | GCTTATAGTA | GAAAACAAAT | AAAGTCTAAA | ATGAAAGTCC | AGATTCTACA | 51840 |
| AAGGTGGTAT | GTCTAATAAG | AGATACTTGT | GTTCTCCCAG | TAATACTGCG | ATCCCAAAGG | 51900 |
| ATGATAAAAG | TAAACTAGAA | GTAATCCCAT | CCTACTCTCT | GGAAACTGCT | AGAATGTTTG | 51960 |
| CTCTGCTTCT | CAGCAGAGCA | AGGGATGTGA | GAGAGGTGGG | GAGAGACAGA | GAGAGAGAGA | 52020 |
| GAGAGAGAGA | GAGATCATCA | ATCCTGATAA | GTTGTAACCA | CAAGCCAACT | TTTATACACA | 52080 |
| TTTAGGCTAA | AAAATAAAAA | GTCTTGGCTA | GCCACAGAGG | CTCATGCCTG | TAACCCCAGC | 52140 |
| ACTTTGGGAG | ACCAAGGTGG | GAGGATCACT | TGAGCCCAGG | AGCTCGAGAC | TGGCCTGGGC | 52200 |
| AACAAAGTGA | GCCCCATCTC | TAAAAAAAAT | ATTTAAAAAA | TTAGTCAGGC | ATGGTGGCAC | 52260 |
| ACACCTGTAG | TCCTAGCTAT | ACAGAATGGT | GAGGCAGAAG | GATTGCTTGA | GCTCAGTAGG | 52320 |
| TTGAGGCTGC | AGTGAGCCAT | GTTCACACCG | CTGCACTCCA | GCCTGGGTGA | CAGAGTAGGA | 52380 |
| CTCTGCGTAA | AAAAAAAAA | AAAAAAAAA | GTCTCAATTC | ATGAATTGAG | TTTAAAGTAA | 52440 |
| TACTTGACTG | GTGGTACCCC | AGCTTCCTGG | CAAAAGCAGA | CACAAACCCC | CTCTAGAAGA | 52500 |
| AAGAACATCC | CAGTCCTCAG | TGACCCATAA | GTAATTTTAC | CAGAAAAATA | AAGAAGTTAC | 52560 |
| TGGCAAAATC | ATCAAATGCA | CAAAATGGAT | TGGAGGAAGC | GTAGCAAGAA | TAAATGAAGA | 52620 |
| GGAGCTGGGT | GCTGTGGCTC | ACGCCTGTAA | TCCCAGCACT | TTGGGAGGCT | GAGGTCAGGC | 52680 |

| | | | | | | |
|---|---|---|---|---|---|---|
| GTTTGAGACC | AACCTGGCCA | ACATGGCAAA | ACCCCGTCTC | TACTAAAAAT | ATAATAATTA | 52740 |
| GCTGGGCATG | GTGGCATGTG | CCTATAGTCC | CAGCTACTTG | GGAGGCCTGA | GGCAGGAGAA | 52800 |
| TCGCTTGAAC | CCGAGAGGTA | GAGGCTGCAG | TGAGCCTAGA | TGGTGCCACT | GCACTCCAGC | 52860 |
| CTGGGCAACA | GAGTCAGACT | CTGTCTCAAA | AATAAATAAA | TAAATAAATA | AATAAATAAA | 52920 |
| TAAATAAATA | AATAAATAGG | GATCAGGAGG | TTTGAGTAAA | TAAGGTTAAA | AGTGATGGTG | 52980 |
| TTCTAGACTA | TTTGTGTCTT | TATATTAAAG | TGAATTTTTT | GTAGGCAGCA | TGTTGTGGCT | 53040 |
| CTTTTTTTGC | TTTTTTTTGT | TGTTGTCTGT | TTTTTAATT | CAATCTGACA | ACCTCTGCTT | 53100 |
| TTGTATTAGA | GTATTTAGAT | CATTTACCTT | AAGTGTGATA | ATCTATATGG | GTAGAGTTAA | 53160 |
| GTCTATCATC | TTGCTATTAC | TTTCCCATTT | GTCCCATCTG | TTCTTTGTTC | TCTTTTTCCT | 53220 |
| CTTTTTTTTC | CCATCTGTTG | AACAACTTAA | ATATTTTTC | TCATTCTATT | TTATTTCTTT | 53280 |
| TTGTGGCTTG | TTAGCCATAA | TTCTTCGTTT | CATTATTTCA | GTGGTTGCCT | TAGAGTTTAT | 53340 |
| AGTATACATC | ATTAATTTAT | CGTAGTTCAT | CTAAAAGTAT | ACCACTTATA | TAAAATAACA | 53400 |
| TTATTTTCAT | TTCCACTTCT | TTTGCACTGT | TGTTGTCATA | CACTTTTCTT | TTGTGTGTGT | 53460 |
| GTGTGTGTGT | GACAGAGTCT | AGCTCTGTTG | CCTAGGCTGG | AGCACAGTGG | TATAATTTTG | 53520 |
| CCTCACTGCA | ACTTCCACCT | CCTGGATTCA | AGTGATTCTT | GTGCCTCAGC | CTCCAGAGTA | 53580 |
| GCTGGGATTA | CAGGCGTGCA | CCACCACGCC | TGGTTAATTT | TTGTATTTTT | AGTAGAGATG | 53640 |
| GGGTTTTGCC | ATGTTAGCCA | GGCTGGTCTT | GAACTCCTGT | CCTCAAGTGA | TCTGCACGCC | 53700 |
| TCGGCCTCCA | AAAGTGCTGG | GATTACAGGC | ACGAACCTTT | GTGCCCGGCC | TGTTTTACTT | 53760 |
| TTAAATGCTA | TAAATCACAC | ATTACATTGT | TAACTATTTT | TGTGAAAATA | GTCAACCACA | 53820 |
| TTTTATGGAG | AAAAAATATT | ATCTGTTTAC | TCACATAGTT | ACAATTTTCT | AGTACTGTTT | 53880 |
| ATTCCTTTGT | ATAAATAGGA | ATTTCAATAT | GCCTAAGGGA | CTTTTATCAT | TCTGCCTAAA | 53940 |
| GGACTTTTAA | AAAATATTTT | TTATTGTTCT | AGTCTGCTGA | TTAGATGTTT | ATTGCCTTTA | 54000 |
| GGCAGGGAGA | TAAAAAAATA | CTACAATATT | TTAGTTAATG | ACTGTGTCAA | TCAAAAGAA | 54060 |
| GCAAGACAAT | CTACCATTTA | ATTGCACGGT | TGATTTTTTA | AATGAAATAG | AAAACATCCA | 54120 |
| CATATACAGT | ACAAAATGTA | TCATAAAACT | CTCACATATG | ACTAGATAAA | TTCCTTCCTC | 54180 |
| TTTTCTCTGT | ATTAAATTGT | CTTATTTCAC | CCTCATTTGG | GGGGAGTTTT | TTTGCTTGGT | 54240 |
| ACAGAATTGT | AGGTCTTTCA | TTAATCTAAA | AAATTTTGCT | CCACTGTCTT | TTTGCTTATA | 54300 |
| TTGTGTCTAT | GAGAAATATG | TGATCTATAC | ACTTGTTCTT | CTGTACATAA | TGTGCCTTTT | 54360 |
| GTTCTTGGCT | GCTTTGAAAT | TTTTCATTTT | CCTCTTGCTT | GCTTTGGGTT | TGATTTGTTC | 54420 |
| TTATTTTCT | AGTTTCTTTT | TTTTTTTAA | TTTTGAGACG | GAGTCTCGCT | CTGTCTCCCA | 54480 |
| GGCTGGAATG | CAGTGGCGCG | ATCTCAGCTC | ACTGCAATCT | CTGCCTCCTG | GGTTCAAGTG | 54540 |
| ATTCTCCTGC | CTCAGTGTCC | CGAGTAGCTG | GGACTACAGG | CAGATGCCAC | CAGGCCTGGC | 54600 |
| TAATTTTTGT | ATTTTGTTAG | TAGAGACAGG | GTTTCACCAT | GTTGGTCAGG | CTGGTCTCAA | 54660 |
| ACTCCTGACC | TCGTGATCTG | TCCGCCTTGG | CCTCCCAAAG | TGCTGGGATT | ACAGGCGTGA | 54720 |
| GCCATCACGC | CCAGCCTAGT | TATTGATTTC | TATCTTCATT | CCACTTTGGT | CAGAGAATAT | 54780 |
| ATACTCTATT | ATTATAGTCC | TTTTACATTT | ATTGAGACTT | ATTTCATGAA | GTAATATACA | 54840 |
| GTCTATCCTG | AAAAATGTTT | CATGTGAGCT | TCAGAAGGAT | GTTATTCTG | CTGTTTGGG | 54900 |
| GTGTAGTGAC | CTATAGATTT | ATGTTAGGGT | CAGGTTAGGT | GTTTCAAGT | GTTAAGTCTT | 54960 |
| CTATTTTTT | GTTGATCTTG | TCTAACTAGT | GAGGTATTGA | TGTCTCCAAC | TATTATTGTC | 55020 |
| GAATTTTCTA | TTTCTCCCTT | CAATTCTGTC | AGTTTTGTTT | CATGAATATT | AGGGCTCTGT | 55080 |

```
TGTTAGGTGC  ATGTATGTTT  ATAATGTTAT  GTTTCTTGA   TGAATTGACA  CTTTTATCAT   55140
TACAAAATAC  CTTTCTTTAT  TTATTATAAC  AATGCTTATC  TTAAAGTTTA  TTTTGTCTGA   55200
TATTAGTATA  CCTACTCCAG  ACATCTTTTG  AGTACTATTT  GTATGTGATG  AATTGTTCCT   55260
TTCTTTCTGC  TCTCAAGATT  CATCTTCTTC  ATCTTTTGAT  AATCTGATTA  TGATGTGTCT   55320
AGGTATGGAT  CTCTTTGAGT  GTATCCTACT  TGGAATTCAT  TGAGCTCCTA  AAATATGTAT   55380
GCAAGTTAAT  GCTTTTTTGC  CAAACATGGG  AAGCTTTGAG  AAATTATTTC  TCCAAACATT   55440
CTCTCTCCCT  GTCCTCTCAC  TTTTCTCCTT  CTAGGAGTCC  CATTATGCAT  ATATTAGTAT   55500
GCTTGATGGT  ATCCCCTGTC  TCTAAGGCTC  TATTTCTTTT  TCTTCATTCT  GTCTTCTTTC   55560
TGTTTTTCAG  AGTAGATCAT  TTCAATTGAC  CTATCTTTGA  GTTCACTGAT  TACTTCTTTT   55620
TGCTGCTCAA  ATTTGCTGTT  AAAGCCCTCT  AGTAATTTTT  TTTTCTTACA  GATGAGATAT   55680
CATGCTGTCG  TTCAGGCTGG  AGTGACCATG  ATCCTCTTAC  TGGGATCACA  GATCACGCAT   55740
GCTCCAGTCT  GAGCAGCAGC  ATGAGCTCCA  GCTTGCTCCA  GCCTGAACAG  CAGCAATACA   55800
TTCTTTCACA  CACAAAGGG   TTATTGGATC  TCACACAAGA  AGGAATTTGG  GGCTAGTCCA   55860
TACAGTAAAG  TGAAAACAAG  TTTATTAAGA  AAGTAAAGAA  GGGCCGAGCG  CAGTGATTTA   55920
TGCCTGTAAT  CACAGCACTT  TGGGAGGCTG  AGGCAGGCAG  ACCACTTGAG  GTTAGGAGTT   55980
CGAGACAAGC  CTGACAAACA  TGGCAAGACA  CTGTCTCTAC  TAAAAATACA  AAATTAGCTG   56040
GGTGTAGTGG  CACATGTCTG  TAGTCCCAGC  TCCTCAGGAG  ACTGAGGCAG  AAGAATCGCT   56100
TGAACCCAGG  AGGCAGAGGT  TGCAGTGAAC  CAAGATCGCA  CCACTGCACT  CCAGCCTCTA   56160
GCCTGGGTGA  CAGAGTGAGA  CTCTGTCTCA  AAAAAACAAA  AAAAGTTAA   GAAATAAAAG   56220
AATGGGTCAT  GCATAGTGGG  TAATGCCTGT  AATCCTAGCA  CTTTGGGAGG  CCAAGGCAAG   56280
TGGATCGCTT  GAGGCCAGGA  GTTCGAGACC  AGCCTGGCCA  ACATGGCGAA  ACCCCATCTC   56340
TACTAATAAT  ACAAAAATTA  GCCAGGCATG  GTGGCACCCA  CCTGTGGTCC  CAGCTAGTTG   56400
GGAGGCTGAG  GCAGGAGAAT  TGCTTGAACC  CGGGAGGTGA  AGGTTGCAGT  GAGCCAAAAC   56460
ACGTCACTGC  ACTCCAGACT  CCAGCCTGAG  TGACAGAGCG  AGTCTTTATC  TAAAAAATAA   56520
AAATAAAAGA  AAAGAATGGC  TACTCCATAG  GCAGAGCAGC  AGTATGGACT  GCTCAAATAA   56580
GCAGACGTAT  AGTTATTTCT  GGATTATGTG  CTAAACTAAT  GGATTATTCA  AGAATTTTTC   56640
AGGAAAGAGG  TGGACAATTC  CCAGAACTAA  GGGTTCTTCC  CCGTTTAGA   CCATATAAGG   56700
TAACGTCCAG  ATGTTGTCAT  GGTATTTGTA  AACTGTCGTG  GCACTGGTGG  GAGTGTCTTG   56760
TAGCATGCTA  ATGCAGTATA  ATTAGTGTAT  ATGAGCAGTG  AGGATGACAA  GAGGTCACTT   56820
TTGTGGCCAT  GTTGGTTTTG  GTGGGCTTTA  GCTGGCTTCT  TTACCGTTAC  CTATTTTATC   56880
AGCAAGGTCT  TTGTGACGGG  TACCTTGTGC  AACCTTCTAT  CTCATCCTGT  GACTAAACTC   56940
CTGGTTAGAA  TGCCTAACCT  AACCCAGCAG  GCCTCAGCCT  TATTTACCC   AGCCCTATT    57000
CAAGATGGAG  TCACTCTGAT  TCAAATGCCT  CTGACATATT  TTCCCACTCC  CTTTTACCAG   57060
GGAACCCTTA  ATCCTAAGGA  TTGCAGTGGG  ATAAAGATCC  GTCTTCTATA  ACTTCTTCAG   57120
ACTAAATAGG  GGCAATGATA  TTCCTGTCTA  ATTATTAGGG  TCTCTTGTGT  CCAGGGTAGA   57180
GAGGAGCTCA  GTCACAAAGT  GTCAGTATGG  TGAGACATTC  ATAACTCTGA  GGCTTCCCAA   57240
AGTGTTGAGA  TTACAGGCGT  GAGCCACTGT  GCCTGGCCAG  GGTCCCATTT  TTATACCAGA   57300
TCCTGGATCC  CAAAAGAGGG  AATCAGCCCT  CTTTTGGGGG  ATCAGCCATC  TCCCTGGGA    57360
ATCTTATCTC  TCGGTGGGGA  TGGAGACATT  TCCATACCTT  CTAGGTAGTC  AAGAGAATGC   57420
TTCTTGTGAT  CCAAAAGTGC  AAATAGCCAA  GTATTCACCT  ATATTGCCT   TTAGCTATCC   57480
```

-continued

| | | | | | |
|---|---|---|---|---|---|
| CCAGAAGTAT | ATTTCCTACC | TGGTTATTAC | ACACCAGATC | TCCCTCATAA | TGCAAAGTAA | 57540 |
| TTTCTGATAC | CCCCAAAAGT | CAAAAACATC | AGATAACATA | ATGCAAAGCC | AAACAGAGCC | 57600 |
| TTAGATTTTG | CGAAGGATCT | ATCCACTTCC | AGTTCCTGGG | GTTTCATGAG | GAAAACAGAG | 57660 |
| GTTTTCCCAA | AATGGGGTCT | GTGGTGCCTC | CTCTGCTTTT | CCCAAGGAGT | CCCAGGCTTT | 57720 |
| TAGAGATTGA | ATATCCACTT | TTAATTAAGC | TTTTAACCAT | AAACCATAGC | ACTCTAAAGC | 57780 |
| AAAAAAAAAA | GGAGTCCTTT | TAAGTTTCTT | ATTACTCAAC | TTTAGCCATC | CCACACGGCC | 57840 |
| ATTATTTCTG | GCTTTTGAAC | TTTACCAAAG | ATAATCTCCC | AGGTTCTCAG | AGAGAGGAAA | 57900 |
| ACTCAAGACA | GTGTGTGGAG | GGGAAGAGAA | CAGAATCAAC | AAATGGTAAA | GGTCACACAG | 57960 |
| ATATCAATCA | GAAAGTACTC | ATTCCCTAAG | CCAGGATTGA | ACCTTGGCCG | CCATTATAAA | 58020 |
| ATGACAAATC | CTTAGCTGCT | GAGCTACAAC | ACTGGTTAGT | TTCCATTGCC | CTTCCCAGAA | 58080 |
| GGGGTCCAGA | GCAGCCAATT | TTGAGCTTGC | AATGGCTTGA | GATAATTTTT | AGAGTTAACT | 58140 |
| ATTACATAAA | CCCCAAAATT | CCTGTTCCCT | GGATGGCAGA | GACCAAGAGA | AAGTACCGCC | 58200 |
| ACGTGGTTAC | AAGGTGAAGC | TCCAAGGAC | ATAAACAAG | ATGAGAAGGA | AACTTCATCC | 58260 |
| AGTTTTTATT | TTTTTTTTT | TCCAGGGACC | TGTAATAAAC | TTTGCAACGG | ACCAGTTTAC | 58320 |
| TGGGCTGGCT | TGAACAGCAG | GCTTATGGAG | TCCTGAGCCC | ATGTTCTATC | CTACCATATT | 58380 |
| CCTCTTTATG | ACAGAGTAAT | ACAGAAAGAC | AAATTGATAT | CACAAAGTAT | ACCAGATTCA | 58440 |
| TTACAGCTTA | AGACTAGCCC | CACAAATCCT | TGTTCCCATT | AATCAAAACT | TTACAGAGGT | 58500 |
| GATAAACAGT | GATTTTTACC | ATTCATTCAG | TTTTCACTAA | GAGAGAGAGG | CCAGAAGCCT | 58560 |
| GACTGGTAAG | AAATCTTTAC | CCTTTTGCTG | GCATGCCAGG | TTTCTGGGTT | CTCTTTCACT | 58620 |
| GAGCAGCACT | AGCAACCTTG | CTCACTGCAA | AGCCCTTGGG | TCCAAGCTAC | GACACAAAAG | 58680 |
| AAAACCAACT | TTTTTCTGTT | TCATGGAACC | ACAGGCAAAT | AAATGTCTCT | CACTTTTGTA | 58740 |
| AGATGCTGCC | CAATGGCCAC | ATAAAGTAAC | CAAATTAACG | TTTTCCATTT | CAGCCAGAGC | 58800 |
| AATATACATG | TGACAAAACA | TAGACATTGG | CCACTCCACT | TAGCACCCAA | TATCTAACTG | 58860 |
| GGAAGGCTCA | AACTTGCCCC | CAGATAGGCC | CTTTCATCTT | TAATCAAACT | TCTGACCAGG | 58920 |
| AGTTTCAACA | TATGGTCTCT | GGGCAAGATG | GTTGTCTCAA | GTAACAGAAA | AGACAGAAAA | 58980 |
| GAGAAAAGAG | AGAAAGGGAG | AAAAGCATTG | CCTGTGGTGA | GATGGGGAAG | GTGAGGAGTT | 59040 |
| CACAGAGGCC | AGAGAAAGAC | CCACCCATTG | CAGCAACACT | GAATCAAAAG | TTCAGGCGGC | 59100 |
| TGCTTGTCAT | AGCAAAGGGA | TCTTTTCCAA | CAGTCCTATC | AGCTGTCAAG | CTTCCCCTTT | 59160 |
| TGGAGAGAAG | AAAAGTTCCC | AATGTCCCGT | GATCCTGTAC | ATGCCTAATC | CTGTCACCCA | 59220 |
| TAGCTGTCAG | CAAAGAGCAC | AGGGAAGATT | AATACAAACA | GAATAGCAGT | TAACATCCCC | 59280 |
| TAATGCTAAA | TCCGTTTTTA | ACCAAGAGAG | ACTTTACTGA | GAGGGGCCTC | TAACCCCTTA | 59340 |
| AATCTTAAGG | ACTGTAGCCT | TCCTAAGTTG | GGTCTCAAAC | CCAAGTTCGG | TCAAGCATTC | 59400 |
| TTGCCCTTTA | TTAAGAGCGG | ACTGAAACCC | TCTCTGTCTT | AGGAGAGACC | CTATCTCCCC | 59460 |
| TAAGTTGCAC | CTCTAACCCA | ATCCTATCCT | TTACCGGGG | ACTCCACCAC | TTACCCAAAG | 59520 |
| TCAGCCAGTT | GGTGCTGTAG | TCTGTTTCCT | TTGGCTTCAG | AGTCTCCTCA | GTATTGTCCC | 59580 |
| TTCGTGGTCA | CAGAAAGATT | TACCAGAAAN | GGGTCTTGAT | CCAGACCCCA | AGAGAGGGTT | 59640 |
| CTTGGATCTC | ACACAAGAAA | GAATTTAGGG | CAAGTCCATA | CAGTAAAGTG | AAAGCAGGTT | 59700 |
| TATTAAGAAA | GTAAGGAAAT | AAAAGAATGG | CTACTCTGTA | GGCAGAACAG | CAGCGTGGTC | 59760 |
| TGCTCAAATA | AGCATACTTA | TAGTTATTTC | TGGATTATGT | GCTAAACAAG | GGGTGGATTA | 59820 |
| TTCATGAGCA | TTCCAAAAAA | GGGGTGGACA | ATTCCCAAAA | TTGAGGGTTC | CTCCACCTTT | 59880 |

-continued

| | | | | | | |
|---|---|---|---|---|---|---|
| TAGACCATAT | AAGGTAAAGT | CCAGATATTG | CCGCAGTATT | TGTAAGCTGT | CATGATGCTG | 59940 |
| GTAGGAGTGT | CTTTTAGCAT | GTTAATACAT | TATAATTAAC | ATATAATGAG | CAGTGAAGAC | 60000 |
| AACCAGAGGT | CCCTTTGGTG | GCCATGTTGG | TTTTGATGGG | TTTTGGCCAA | CTTCTTTACC | 60060 |
| ACAACCTATT | TTATCAGCAA | GGTCTTTGTG | ATGTGTACCT | TGTGCTGACT | TCCTATCTCA | 60120 |
| TCCTGTGACT | AAGAATGCCT | AACATACTGG | AAATGCAGCC | TAGCAGGTGT | CAGCCTTATT | 60180 |
| TTATCCAGCG | CCTATTCAAG | ATAGAGTCAT | TCTGGTTCAA | ATGCCTCTGA | CAATGCAGCC | 60240 |
| TTGAATTCCT | GGGCTGAAGC | CATCTTCCCA | CTTCAGCCTC | CTGAGTAGCA | GGGACTACAG | 60300 |
| GCACACACCA | TCATGCCTGG | CTAATTTTTT | TGTATTTTTT | TTTTAGAGA | TGGGGTCTCA | 60360 |
| CTGTGTTGCC | CAGGCTGGTC | TTGAGCTCCT | AGGCTAAAGC | AATCCTCCTG | TGTCATCCTC | 60420 |
| CCAAAGTGTT | GGGCTTGTCA | GAGGTATTTG | AACAAGAAAG | ACTCCATCTT | GAATAGGAGC | 60480 |
| TGGGTGAAAT | AAGGCTGAGT | CCTGCTGGGC | TGCATTCCCT | GTAAGTTAGG | CATTGTAAGC | 60540 |
| CACAGGATGA | GGCAGGCAGT | GGGCACAAAA | TACAGGTCAT | AAAGACCTTG | CTGATAAAAC | 60600 |
| AGGTTGCAGT | AAAGAAGCCG | GCTAGGCCAG | GTGGGGTGGC | TCACACCTAT | AAGCCCAGCA | 60660 |
| CTTTGGGAGG | CTAAGGTGGC | TGGATGGCTT | GAGCGCAGGA | GTTGGAGATC | AGCGTAGGCA | 60720 |
| ACATGGCGAA | ACCCGGTCTC | TATTAAAAAT | ATAAAAATT | AGCTGGGTGT | GGTGGCACAT | 60780 |
| GCCTGTAATC | CCAGCTACTT | GGGAGGCTGA | GGCACGAGAA | TCGCTTGAAC | TCAGAAATTG | 60840 |
| GAGGTTTCAG | TGAGCTGAGA | TCGTGCCACT | GCACTCCAGC | CTGGGCAAAA | AAAAAAAGA | 60900 |
| AAAAGTAAA | GAAGCTGGCT | AAACCCCACC | AAATCCAAGA | TGGCGATGAG | AGTGACCTCT | 60960 |
| GGTCATCCTC | ACTGCTCCCC | ACCAAATCCA | AGATGGCGAT | GAGAGTGACC | TCTGGTCGTC | 61020 |
| CTCACTGCTA | TGCTCATACC | AGCGCCACGA | CAGTTACGA | ATGCCATGGC | AACGTCAGGA | 61080 |
| AGTTACTTTA | TATGGTCTAA | AAAATGGAGG | CATGAATTAT | CCACCCCTTG | TTTAGCACAT | 61140 |
| AATCAAGAAA | TAACCATAAA | AATGAGCGAC | CAGCAGCCCT | CAGAGCTGCT | CTGCCTATGG | 61200 |
| AGTAGCCGTT | CTTTTATTCC | TCTACTTTCT | TAATAAACTT | GCTTTCACTT | TACAGACTCG | 61260 |
| CCCGAATTCT | TTCTTGTGTG | AGATCCAAGA | ACCCTCTCTT | GGGGTCTGGA | TCTGGACGGA | 61320 |
| CCCCTTTCCG | GTAACAGGAT | TACAGGTGTG | AGTGAGCCAC | CATCCCCAGC | CTTAGTAAAT | 61380 |
| TTTTATTTCA | GTTATTATAT | ATTTTTATTT | ATTTTCTGTT | TTTCAGTTAT | TATATTTGAA | 61440 |
| ACTCCAGAAT | TTTTATTTAG | AATGTATTAA | CAAATCAGGA | GTACTGGCAT | AAGCCTGGCA | 61500 |
| CAAAGCAAAT | GTTGACATAG | GTCTGGCACA | AAACAAGTGT | TCAATGCATT | TTAGCTACCT | 61560 |
| TTAAGTGTAT | TATTACTAGC | TGCTTCTGGG | GCTATCCGGG | GAAAATTATC | CTTGCAAAAC | 61620 |
| CCCCACTCAC | TTCCAGAGCA | GGCTTCAGTG | AAGCAGTCAT | CTGTGTCATG | ACAAGAGCCA | 61680 |
| AACTCTGTAA | AACATTTGAA | GAGATTTATT | CTGAGCCAAA | TTTGAGTGAC | CATGGCCCAT | 61740 |
| GACACAGCCC | TCAGGAGGTC | CTGAGAACAA | GCGCTCAAGG | TGGTTGGGAT | GCACCTTGGC | 61800 |
| TTTATACATT | TTAGGGAGGC | ATGGACATC | AATCAAATAC | GTTAAGAAA | TGTACACTGG | 61860 |
| TTTGGTCCAG | AGAGGCGGGA | CAACTGGAAG | CAGCGGAGGA | GTGGGGTGGA | GGTGATGACA | 61920 |
| ATTGGTTGAG | TTTGTATAAA | GATTTGGGAT | TAATAGAAAG | GAGCACTAGG | TTGTGATAAC | 61980 |
| AGGTTGTGAA | GACCAAAGTT | GTACTATGGG | ATGAAGTTTT | TAGCTAGCAG | GCTTCAGAGA | 62040 |
| GAATAGGTTG | TAAAATGTTC | TTATCAGACT | TAAAAGCTGT | GTTGATGTTA | ATGCCAGAGA | 62100 |
| GGAATAATGA | GGCATGTTCA | ACCCCCACTT | CCCTTAATGG | CCTGAGCCAG | TCTTTCAGGT | 62160 |
| TACATTTTAA | GAAGCCTGAC | TGAAGAGAAA | GTCTATTCAG | ATGGTTGGGG | GCTTTAGAAT | 62220 |
| TTTATTTTTG | TTTTATACCT | TTGCCCTTGG | AAGTTTTGCT | GAAAAATGAA | CACAAAAAAA | 62280 |

-continued

| | | | | | | |
|---|---|---|---|---|---|---|
| GGCAGATTCA | TAAGATAAAA | GGCTTTACAA | TTTAATTACT | CTGTGGTTCT | CCTCATGCAC | 62340 |
| ATAGTACCAA | TATCCCAGTG | GAATTTAGAA | GCTTATATGC | CACCTTGAAG | TTGAAGAAAT | 62400 |
| AACAGGGGCT | TGATCCTTGC | AAAATAGGTT | ATGGGAAACA | GAAGAAGAGG | AATTCTGTTG | 62460 |
| AGGGGCAATA | TGTAACTACC | AGGAGAGACT | AATTGGATCA | AAGAACAGAT | AAATTTGTAA | 62520 |
| ATAGTTCTCC | TTGGAATTTA | AATGATGCTT | AGAGACTGAT | TATCTTATAA | AAGGGTCTGT | 62580 |
| TCAGGTGTGG | TTACATTCTT | GGTCTTTCCT | ATAATGCACA | ATGAGATAAC | AGAGAGGGAG | 62640 |
| AAAAGAACAA | TTGTTCTCGC | TGGTGGGGCC | ATCCTATTTT | TATGTACCTA | GGGAAAAGTC | 62700 |
| TCTTTAGTGT | CTGTTGATCT | CTAAGAGTTT | TTCATTCAAA | ATACTCATTA | TATCAGGAAG | 62760 |
| CCACATTTTG | GGGTGAAATT | CACTACTCCC | TTTTAGAGAT | ACGGGTACAA | ACTGTTTGTA | 62820 |
| AAGAATGCTA | AGACTTTGCC | GGGTGCAGTG | ACTCACGCCT | GTAATCCCAG | CACTATGGAG | 62880 |
| GGGCCAAGGT | GGGCAGATCA | CTTGAGGTCA | GGAGTTCAAG | ACCTGCCTGG | TTAACATGGC | 62940 |
| AAAACCCCAT | CTCTATTAAA | AAAAACAAAA | ATTAGCCAGG | CGTGGTGGTG | GGCATCTGTA | 63000 |
| ATCCAGCTA | CTTGGGAGGC | TGAAGGCAGG | GAGAATTGCT | TGAGCCTGGG | AGGCAGCTGT | 63060 |
| TGCAGTGAGC | CGAGATCACG | CCACTGAACT | TCAGCCTGGG | CAACACAGCG | AGACTGTCTC | 63120 |
| AAAAAAAAAA | AAAAAATGCT | AAGACTTACT | TTGGGACATC | CTTTGTCAGG | GTCCATGATT | 63180 |
| CTGATTAGCT | CAAGGCAGGT | ATTTTTTTT | TTAATAGAG | ACAGCATCTT | GCTATGTTGG | 63240 |
| CCAGGCTCGT | CTCGAACTCC | TGGCCTCCAG | TGACTCCCCC | CACCTCAGCC | TCCCCAAGTG | 63300 |
| CTGTGATTAC | AGGTGTGAGC | CACCACACCG | GTCTGGTTTT | TTTTGGTGGT | TGTTGTTTTA | 63360 |
| ATCCTATAAT | CCTGTGTCCT | TTCTTCCTAC | CTCTGAGTAG | TGCTTACTCT | CTCCCCTTTA | 63420 |
| GTCATTTGAA | AAGTTTATCA | GAAAGTGGGT | GCAGTTTCAG | GCTGGGTACC | GTGGCTCATG | 63480 |
| CCTGTAATCC | CAACACTTTG | AAATGCTTAG | ATGGGAGGAT | CATTTGAACC | CAGTTCAAGA | 63540 |
| TTACAGTGAG | CTGTGATCGT | ACCATTGTAC | TTCAGCCAGG | GTGACAGTGC | AAGAGCCTGT | 63600 |
| CTCTAAAAAC | AAACAAAAAA | TTGCTTTCAC | ACTGTGATGC | TATCACATCT | CTCCTAAGCT | 63660 |
| CTTGTTGGGG | CTCAGAAATT | GATACCCTAA | TATATGGCCC | TTGGTCATAT | TGAACTGAAG | 63720 |
| AAGCCTCAAA | GTCTCTCTGA | CATCCCTGCC | ACCAACTATC | CCTACCAAAA | CACATCGTGG | 63780 |
| AATTAAAGTT | TCTTTATCTA | CCTAAGATCC | AGACCCACCA | AAAAGAGCAA | TTATTTTTAT | 63840 |
| TTACCCTTCC | TGTAAGACCA | AGAATGTAAC | CATGCCCGAA | CGGACTTTCA | CAAGATAATG | 63900 |
| TTCAAGTTAA | TCTCTGTTCC | CTGATCTACT | TACTCTCCCT | AGTAATGAAA | GGAGTTGGCC | 63960 |
| AGCTTGCTTT | AGGCAGACAG | TAAGGGAATG | GTACCAGAG | AACCTCTGAC | CTGCCCCACA | 64020 |
| AGTGCTTACA | CCGGATGTTT | TGTGCAGATA | AGGGAACTTG | CACAGGGGC | TTGCCTAAAC | 64080 |
| ATGCCTGCAG | TGGATGATTC | CTTTCCTTAA | CACATGCACA | GTTCAGGAAA | TTAATCAATA | 64140 |
| TGGAGTAGCT | CAGTCTAAAG | GCCTGCATGC | ACTGGTAGGA | CAGGGTGGAG | TTGTCAGGAA | 64200 |
| TTTGAGTCTT | AAGCCCTAGT | ATTCAACTGT | GAAGAGCAAA | CCAGAAATCT | GCTTTCAGGA | 64260 |
| CCCTTGTCTT | TGCTGAGAGC | TTTCCTTTCA | CTTAATAAAT | TCTACTCCAC | TCATTCTTTG | 64320 |
| ATGGCTGCAT | GCCTAATTCT | TCCTGGCTGT | GAGACAAAAA | CCCGGACCTA | GCTGAGCGAA | 64380 |
| GGAGCAAAAA | TCCGCAACAG | TAATCCCATC | AACAGAGTTT | CTCTTCTTCC | CCTCCCATAA | 64440 |
| TCTGTTTTGC | CAGGATAATA | TATAAGCTTT | TAAGCCCTCT | TGGGAAGTGG | ATAATCATTC | 64500 |
| TATGGTTCTC | CCTGTGTACA | TGTTAATAAA | TTTGTGAGTT | GATTTTCAG | CAAAGTTTCC | 64560 |
| CCAGAAGCCA | AAGGGGAAAT | TTCCCTTGGC | CCCTCCACTC | TCTTTTCCCA | GCTCTTCTTT | 64620 |
| TACTTTCGTT | TTTATTTCCT | CAGCCCAGTA | GGTCACAGCC | TTCTTTTTAT | TTCTTCTCTG | 64680 |

| | | | | | | |
|---|---|---|---|---|---|---|
| TCCAAACCAT | CAGTATATCC | TACAGGTGGG | AGAGAAGCAG | CTCTCTGGGA | AACCAGTAAG | 64740 |
| CACCATGAGT | TCTGATACTT | TCTAGTACCA | TTTGACATAT | TAACATCCCC | GCCACCCCTA | 64800 |
| ATATGTATGG | ACACGCACAC | ACATACCACA | TCACATGCAT | CACACTAACA | CAAACTATGT | 64860 |
| ATCACATACC | ACACACAGCA | CACACAGTAC | CACATACCCC | ACACAACACC | CACACCACAC | 64920 |
| TACGTGCATC | ATGCACATAT | GTGCACACAC | CTCTTGTGAT | GTGTGTTTAG | TGCAATTCAG | 64980 |
| AAAGTTACTC | TTTGATTTAA | TGCACATCAC | TATGCTTAGA | AATATTCTAG | TTACTGGGAT | 65040 |
| TCATCAGTGA | ACAATATTGA | AAAAAATCCA | TCCCTTTGCA | TTCTCATGAG | GGAAGCAAAC | 65100 |
| ACTAAACAAA | ATAAATTAGT | AAAATATTCA | GTGATAAGTG | CCATGGGAAC | AAAATAGATT | 65160 |
| TGAAAATGTT | TGGGAGGGAG | AGAGGGGTAC | ACTTGCTAAC | AAGTGGTCAG | GATAGGGTTA | 65220 |
| GTTGAGAGGC | AAAATCTGAA | GGAGTTGAGG | AAAGGCATTC | TAGGAATAGC | TGAGTGCTGA | 65280 |
| CTCTTGCCCA | CAGTGGGAAC | ACACAGTACA | GAGCTTCTGA | AGGAGACTCT | AGTGACCTAC | 65340 |
| TTCCCATTGT | GAGTCTTTGG | ACTCCTATAT | CCCATAATCA | CAGGATCAAG | CCTAACTTTA | 65400 |
| CATATTAGAG | ATAATGCATT | CCTCCTTGGG | GATAGTTCAG | GTTGATTTCT | CCCTAGGCCT | 65460 |
| GCCTTTGTCA | ACATATTCCT | GAAGTCTCAT | CTGCACCCCA | TCTCTGCTTC | TAATATTGGC | 65520 |
| CACTCTGTGC | ATGAACCAGC | CCCTCCTTCC | TGCAATGGGA | AACAGGTGTG | AGATGGGACA | 65580 |
| GCTGTCACAA | TCCGTTTTGC | TTTTGTCTTG | CTGTTATTAT | TGGTAATGGT | AGTTTGTTTC | 65640 |
| CTTTTTAGCA | TTCACTAGCT | TCCTTTTCCT | GATCCTTTGA | TAGTGTTACC | AGAAAGGGGG | 65700 |
| TCCCAACCCA | GACCCTAAGA | GAAGTTCTTA | GATCTCGTGT | GAGAAAGAAT | TTGGGGCAAG | 65760 |
| TCTACACAGT | AAAGTGAAAG | CAAGAAAGTA | AAGGAATAAA | AGAACGGCTA | CTCTACAGGC | 65820 |
| AGAGCATCAG | CTTCTGGACT | AAGGATACTG | ATATGGTTTG | GCTGTGTCCC | CACCTAACTC | 65880 |
| TCATCTTAAA | TTCCCACATA | TTGTGGGAGG | GACCTGGTGG | GAGGTAATTG | AATCATGGGG | 65940 |
| GCAGGTCTTT | CCCTGAGTAA | TTTATACTGC | TGTTCTCATG | ATAGTCAATA | AGTTTCATGA | 66000 |
| GACCTGATGG | TTTTATAGAA | AGGAATTTCC | CTGCACAAGC | TCTTTGCCTG | CTGCCATCCA | 66060 |
| TGTAAGACCT | GACTTGCTCC | TCCTTGCCTT | CTGCTGTGGT | TGTGAGGTCT | CCCCAGACAC | 66120 |
| GTGGGACTGT | AAGAGCATGA | AACATTTTTT | CCTGGTATAA | ATTACTCAGT | CTCAGGTATG | 66180 |
| TCTGGATCAG | CAGTGTGAAA | ATGGACTAAT | ACAGATACTT | ACAGTTATTT | CTTGATTATG | 66240 |
| TACTAAACAA | GGAGTGGATT | ATTCATATGT | TTTCTGGGAA | AGATGTGGGC | AATTCCCAGA | 66300 |
| ACCAAGCGTT | CCTCCCCTTT | TTAGACTATA | TAGGGTAGCT | TCCTGACATC | GCCATGGTAT | 66360 |
| TTATAAACCA | CTATGGAGCT | GGTGGGAATG | CCTTCTAACT | TGCTAACACA | TTATAATTCG | 66420 |
| TGTATAATGA | GCAATGAGAA | TGACTAGAGG | CCACTCTTGT | TGCCATCTTG | ATTTTGGTGG | 66480 |
| GTTTTGGTCA | GCTTCTTTAC | TGCAACCTGT | TTATCAGCA | AGATCTTTAT | GACCTGTGTC | 66540 |
| TTGTGCCAAC | TGCCTATTTC | ATCCTGTGAC | TTACAATGCC | TAACTTCCTG | GGAATGCAGC | 66600 |
| CCAGTAGGTC | TCAGCCTTAT | TTTACCTAGC | CCCCATTCAA | AATGGAGTCA | TTCTGGTTTG | 66660 |
| AACACCTCTG | ACAATAGGAC | AGATCTGGAA | TGAGCCATGC | CTGGGTACAG | AGTCACATCC | 66720 |
| ACAACAATGA | AAGTTGTAGA | TATCTGCAAG | GACTCATCGT | GGGACCAAGG | ATTCAGGGC | 66780 |
| TCATTCTTTC | TCCTCTCTCT | GTGTGCTGGT | TGCCTCAGGA | GTAGAATGTC | CCATGCTATG | 66840 |
| CATGGGGTCT | GCAACCATCA | TGCCAGGGCA | TGATGAATCG | TAGGTGGCAA | AACAACAGAA | 66900 |
| GGCTCTGTGA | GCACCCAGGA | GGGTGCAGTG | CTGAAGAGTC | TTCTGCTTGG | TATAGGAAGA | 66960 |
| AAGGAACGTG | TTTCCCAATC | TTGCCTTTAT | TTTGAGTAGT | TGGACCAGAG | GGATTGCAGC | 67020 |
| TGGGCCAAAC | TCCATGTTCC | ATTGGCTATC | AGGGTCAGCA | GGCAGGCCAG | GGGCCCAGAC | 67080 |

| | | | | | | |
|---|---|---|---|---|---|---|
| AGGCCAGTGG | CTCCCAGAAT | TCAAGTTTAA | TTTCTCCTCC | CACCTGTGTC | CTGAGCTCCC | 67140 |
| CTTACTGGTT | CCCTTGGACC | ACTGCATCTA | CTTAAGCCAG | CATTTATTAT | GTTGTTATCA | 67200 |
| TAAATGCCTC | TTACACCTGA | GACTTATAAA | TGTGACAAGC | TCTTATTGTG | AGATAGTAAT | 67260 |
| CCATCTTTTT | TCCCCATGAA | ATAATAATTC | TAACGGGTGG | TGATAGTACT | TTTCCTTTCA | 67320 |
| TTTTGAAGTG | GAGAAGCTGG | AGCTAAGTCA | TTAAGGACTT | GACCCTGGAC | CCCACAGCCT | 67380 |
| TTTCTCCACA | AAGCACAAAG | CAGAGTGATG | GTCCCAGGGA | TCCCACACAG | CTCTAAGCTG | 67440 |
| GGGGCACTCA | CTGCTGGGCC | ACTAGTGACT | CCCATTTTCT | ATCCTGGCTG | ACCCTCGCTA | 67500 |
| TTGAAGAAGA | TCTGAGTCCT | GCAGAAGGAC | AGCAAGGAGA | AAAACAAGAC | ACAGAACGGG | 67560 |
| ACAGAGAAGA | ATAGAAAGCT | GACTCAGATG | AATTTTGTGA | TGCCAATGAG | TCCTACTGCT | 67620 |
| GTTACCACCC | CTTTTTCCAC | CACACCCTTC | AGAGCAGTTA | TAGAACCACA | AGCAACCCAT | 67680 |
| AAATAGCAAA | AGAAGTAACA | TCAGCTAGGA | AGGCTTAAGG | ACTCCCAAGG | GAGTTGGTGG | 67740 |
| CAAAAGTAGA | AAGATCTCAA | ATCAGAGTCT | GTGAACTGAA | CCTCTGCAGG | CTTCCTGTTT | 67800 |
| TTAGATACTC | TGTGTTGGGG | TCACATGATA | GTTACAGGG | TTATTAATTG | GTTCCTTCTT | 67860 |
| TTTATTGCTG | TAAAAGAAGG | ATATTTTCTT | CCTACGTTTC | CCCCTCCTTT | ACCGGAGAGG | 67920 |
| CGGAGTGCAA | ATGATATGAA | CAACGTCACT | AGTTTTCTCC | TAAATCTTAT | GAGCCCCGCC | 67980 |
| TCCCACAGTA | GTTTCACTTC | TCAGTTTAAT | CCGGTCTGAG | TTAACTTCCT | GACCCAGGAA | 68040 |
| GTGGCAGCAA | CAGAGGGGAC | TAGCAGCGAA | TATGTAAGTG | TCTGAGCAGT | GAAGGTTACG | 68100 |
| GAAAAGGTCC | AGGCTAAGGT | TTTCTCAGTG | GATATGTGAG | TGTGTACTGA | TGGCAAGTGG | 68160 |
| GGTGGGGAAT | ATATTTCGTG | ACAGCAGGGC | CCCTCCAACT | CTGAAAATGG | TCAGGACTTT | 68220 |
| CTTTGTTTTA | CAGCTCTCAC | CTCTTTCCTG | CTCTTTCTTT | CACCAGACTT | TACACCAAAT | 68280 |
| CTCAGAAGAT | TCAGAACTTA | GATGAGTGGG | GCCCAGGACA | GGAACCCTGG | AGCCTTGGAA | 68340 |
| GGAGGGGAGC | CCCATCTCCC | CAGAAGAGCA | GTGACCCCAG | CAGAGAGGGG | CCTGGTGTAT | 68400 |
| CACTGGAGGA | AATAGCCTGC | CAAGGAATAC | ACGTCTTCAG | AAGAAATTCT | GTGTGGCTTC | 68460 |
| AAGAGACTGA | TCAAATTGTG | AGAGGAAAAC | AGCCTACCCG | GTAATTGTAG | TTAAATTACT | 68520 |
| GTTTTTATT | CTAGGCACTC | TTCAAACTTC | CTCCTGACTC | TGCCCCTGTC | CTAGAGGAGC | 68580 |
| TCCCAGGAGT | AGGGGTGTGG | GGGCGGGCGG | GGGGGAGGGA | TCGGGGGTAC | AGGGAGAGCC | 68640 |
| CAGCTAGGTT | CTCAGAAGAG | GCAGGCTTTT | TCGCTCCTGG | TCACTCCTCT | GTTGCCTATC | 68700 |
| CCTGGCCTCC | CCCATCTTCT | TTCTGCCTTC | CCTACCTCCT | TGGGTCTGCA | AACTCTTTAT | 68760 |
| GTTGCAATCA | CTCTGAACAT | GTCTCTTGAG | ATAGGTCCTG | TCCTGGAGAA | GAGATAGTAA | 68820 |
| AAGTAAACTC | CCCAGTTCTG | CAGGAGCTCT | GATCCCATAG | AAATAACTGC | TCCTCAGGAG | 68880 |
| CAAACCCTCT | GCTCTGCAGC | CTTCTTTCCA | ATTCTTATTC | CCTCAGTTTA | GGGAGAGGGC | 68940 |
| ACAAAAGGA | TAAACCGGTT | CTTCTGGTTG | TTCTGGTTGC | CTTGATTGCT | TCCATTATCC | 69000 |
| TCCTGGTTGG | GTCTCTAGCA | AGACGTTATT | AGCCAGGGAA | GTCCCACTTA | GGCACCCCTC | 69060 |
| TCTGCAGAAG | AGGTATTCAC | TATTCTCCTT | TCTCTTTCTT | TTGCCTATTA | TACCTCTGCT | 69120 |
| CCTGAAAGCA | AAAACAACAA | CAACAAAAAC | ACAAACAAAA | AACAACCGAC | CTTATTAACC | 69180 |
| AGTGTTGGTT | GTTGTTCTTT | GTGGGGATG | GGGGGGTCG | AGGTGGAGTC | AAATTTTATT | 69240 |
| GTCATGATGG | TGTAGGAGCC | AAGGGAACAC | TTCCCCTTTG | CCTTCTGAAG | TTCACTGAAA | 69300 |
| AATCGACTCA | CAAAAGGCAG | GCTAATTGGA | GAAAAGGCAT | ACAAATTTAT | TAACAAGTAC | 69360 |
| ATGGGCTAGA | ATCACAGAGT | GATTACCCCC | TCTGCCAATG | GGGTAGATA | CTTATATAGC | 69420 |
| CTTATTTATA | AATACTTATG | TATAAATACA | TAAATATAAA | TATGTATGCA | TATGTATGTA | 69480 |

-continued

| | | | | | | |
|---|---|---|---|---|---|---|
| TGTATAAATA | TGTATGTATA | CTGTATAAAT | ATGTATGTAT | AACGTTTATA | CATGTATACA | 69540 |
| TATTTATTTC | AGAGGGGAAG | GGTGATATCA | GGAGAATATA | GGTAATTCTT | TGAGGGGCAG | 69600 |
| TAAATGATTA | CTAGGGAGAA | TAAATGAATA | TTTGGGAGGA | TGAATGAATG | GAGGAACAGA | 69660 |
| GTTTAACTTG | TAAATGTTCT | CTTTGGAAAA | TGAATGAGCC | TGAGAGACAG | ACATTATTTT | 69720 |
| GTGAAAGTGT | CTGATTAGGT | CTGGTAACAT | TCTTAGTCCT | CTTTTCTTCA | GTACAAAATG | 69780 |
| AGATAATAGG | GGTTGGAAGG | AAAAACAATT | GTTCTTCTTG | TCTAGTGTGA | CTGGTCTTTA | 69840 |
| TGTAGATAGG | GGAAAAGTCT | CTTCCAGCAT | CTGCTGATCT | CTAAGGGCCT | TTAATTCAAA | 69900 |
| ATACTCATTA | TACCAGGGAG | TCATATATTG | GGGTGAAGCT | CCCCATACTC | CTTCAATGGA | 69960 |
| ATCTGTCACA | GATCACCCAA | TTGCATAAGT | GTTACTACTA | ATTACAAAGA | GTAATTCTGG | 70020 |
| TACCAATTAT | TCTTTTTTTT | TTTTTAAGA | CAGATTCTCG | CTCTTTCACC | CAGGCTGGAG | 70080 |
| TGCAGTGGTG | TAATCTGGGC | TCACTGCAAC | CTCCCCCTCC | GGAGCTCAAG | TCATTCTCCT | 70140 |
| TCCTCAGCCT | CCTGAGCAGC | TGGGATTACA | GGTGTGCACC | ACCACATCTA | GCTAACTTTT | 70200 |
| TGTATTTTTA | GTAGAGATGA | GGTTTTGCCA | TGTTGGTCAG | GCTGGTCTCA | AACTCCTGAC | 70260 |
| CTCAGGTGAT | CTGCCCGCCT | CGGCTTCCCA | AAGTGCTAGG | ATTACAGGCG | TGAGCCACCG | 70320 |
| TGCTGGCCTG | GTAACAATTA | TTCTTGAAGT | TAACTAGAAT | AGGAAAGAGT | TTCACACTCC | 70380 |
| CTGAGTTCTC | TCTTTTACAG | CTTTTGTGAG | GAAGCCTGCA | TTGCTTCTCC | CAGCACTTGG | 70440 |
| TCCAAGGTAA | CTTTCTGTGA | TAACAGAATG | TTGTATATTG | AGGCTGTTAT | GTAGCCACTA | 70500 |
| GTCACATGCA | ACTATTAAGC | AATCAAAATG | TGGCAACTGG | AACAGAAAAA | CTGAATTTTT | 70560 |
| TCATTTTAAT | TTTTATTAAG | TTAAATTTAA | ATTCCTACTC | ATGATAGTGG | CTACTGTATT | 70620 |
| AGCTATACAG | CTAGATGTTT | GTGTATCCTC | TAAATTCCAA | TGCATTCTT | CTTTCTGGAG | 70680 |
| AGAAGACTTT | AGCTGGACAT | GGTGGCACAT | ACCTGTAGTC | CCAGCCACTC | TGCCAGGGTG | 70740 |
| AGGCAGGAGG | ATTGCTTAAA | CCCAGGAGGT | CGAGGCTGCA | GTGAGCTGTG | GTCATGCCAC | 70800 |
| TGCCCTCCAC | TACAGCCTGG | GCAAGAGAGC | GAGAACTTGT | CTTATAAGAA | AAGAAAAAGA | 70860 |
| GGCTGGGCAC | GGTGGCTCAT | GCCTGTAATC | CTGGCACTTT | GGGAGGCTGA | GGCGGGTGGA | 70920 |
| TCACAAGGTC | AAGAGATCGA | GCCAACCAAC | ATGGTGAAAC | CCCATCTCTA | CTAAAAATAC | 70980 |
| AAAAATTAGC | TGGGCGTAGT | GGTGCACACC | TGTAGACCCA | GCTACTACTC | GGGAGGCTGA | 71040 |
| GGCAGGAGAA | TCGCTTGAAC | CCGGGAGGCG | GAGGTGCAGT | GAGCCGAGAT | AGCGTCACTG | 71100 |
| CACTCCAGCC | TGGGTGACAG | AGTGAGACTC | CGTCTCATTA | AAAAAAAAA | AAAAAGTTAG | 71160 |
| AAGACTGAGA | AAAGAAAAAT | AATGAAATAA | TTTAGAGCAG | TCTGAGCTAT | GTGAGGTATG | 71220 |
| CAAAATTTAT | CAGGACAAGT | GAGGCAGGAG | TATAGGTCTT | CCAGTTAAGA | CCCCATGTTT | 71280 |
| TAAAAGCATT | TTGTTCCTGA | CTGGCTGCCT | CATCTATTAC | CTACATATTC | CCGAGATTTG | 71340 |
| TTAATACAAA | GAAACAATGT | TATAGCCAGT | CCAAAAGCTT | ATGCTATTTT | AATGTTAAAT | 71400 |
| CCTTGGCAAA | CAACTTTAAA | ACTGCTTTAA | ACTGCTTTTT | TCCTCTAACA | CACTTGTACT | 71460 |
| GCTTGCTAAT | GAGGCACTTG | AACTCTGCAC | TTGGTTGCAG | TTTCTCAAAG | TGCCCCAAAC | 71520 |
| AACCTTCACT | CAATTTCTTC | CTTTTAGTTC | CTCTTTTCTT | CAATACAAAA | TGAGATAATA | 71580 |
| GGGGTTGGAA | GGAAAACTTT | CAAGACCTAT | GGAAGTCAGT | TGCAGCCAGC | TCATCACATA | 71640 |
| GAGGTGCAGG | TGAGGTGTAT | TTTCATCACG | GTGGAAAATT | CTGGCTGCTT | CATCTCCATC | 71700 |
| TCTAGAGCCA | ATATTGGAGC | TTTTCAATAA | AAGCTATGGC | CTCAACCACC | AGCACCAAGA | 71760 |
| AGATGATGGA | GGAAGCCACC | TGCTCCATCT | GCCTGAGCCT | GATGACGAAC | CCAGTAAGCA | 71820 |
| TCAACTGTGG | ACACAGCTAC | TGCCACTTGT | GTATAACAGA | CTTCTTTAAA | AACCCAAGCC | 71880 |

| | | | | | | |
|---|---|---|---|---|---|---|
| AAAAGCAACT | GAGGCAGGAG | ACATTCTGCT | GTCCCCAGTG | TCGGGCTCCA | TTTCATATGG | 71940 |
| ATAGCCTCCG | ACCCAACAAG | CAGCTGGGAA | GCCTCATTGA | AGCCCTCAAA | GAGACGGATC | 72000 |
| AAGAAATGTC | ATGTGAGGAA | CACGGAGAGC | AGTTCCACCT | GTTCTGCGAA | GACGAGGGGC | 72060 |
| AGCTCATCTG | CTGGCGCTGT | GAGCGGGCAC | CACAGCACAA | AGGGCACACC | ACAGCTCTTG | 72120 |
| TTGAAGACGT | ATGCCAGGGC | TACAAGGTGA | GTGTGTGGGC | CCGGGAGCTT | TGGTAAGTAC | 72180 |
| CAAGTCTTAT | CCTGCTCCCC | AGGAGCTGAG | ATGATTTAAC | TTGAAACCTA | ACATTATGAC | 72240 |
| TTGGAAATAC | AGCTTTCATC | ATGTCATTCT | TCTGAAAAAT | AGTTTATGAT | GATTTCTTGC | 72300 |
| TCAATTATCT | AGACTGTCCA | TCCTGACCTT | CAATGGGATG | GTTGGACTCT | TATCTCTATC | 72360 |
| CATTTGTGTT | ATGATGAATT | TCTTTTTGCT | TTAGAACAGG | TTGTTCTCAA | ACCAAACACC | 72420 |
| CGCATTTTTT | CTTGTTTCAC | ACCATGAATA | TCATTTGAAA | AACCACAATA | TGTAAAGCCA | 72480 |
| TGCAGTAGGG | CCTGAAAACA | GGGAAGAAAG | ACCCATCACC | TTTTAGGTAT | CTACAGTCTA | 72540 |
| GTAAAGAAAA | CAAACCATCA | AAAATGTCTG | CCTGGAGGTC | CCTGGTTTTG | GTGGTGGGA | 72600 |
| GGGACATTTA | GGGTAGAGAG | TGGTTCATCT | TAGAAGTAAC | TCCTGAAGGA | CACGTAAAAA | 72660 |
| TTGAACACCT | ATTGGGGGAT | TTTCATTTGG | GGAATGAAGG | GTCAGTGACA | TTGAAAATAT | 72720 |
| CACTCTGGTA | CCTCTACTTT | TTTTTTTTTT | TTTTTTTTT | TTTCCTGAGG | TAGGGTCTTG | 72780 |
| CTCTGTATCC | CAGGTTGGAG | TACAATGGTG | CAATCTCGGC | TCACTGCAGC | CTCAACCTTC | 72840 |
| TGGGGCTCAA | GCAATCCTCC | CACCTCAGCC | TCCCAAGTAG | CTAGGACTAC | AGGGATGCCC | 72900 |
| CACCATACCT | GGATAATTTT | TTTATTTTT | GTAGAGACAT | GGTCTGCCTT | TCTTGCTTAT | 72960 |
| ACTGGCCTCA | AACCCCTGGT | CTCCCTCCCA | TCTCAGCCTC | CCAAAATGCT | GGGATTAGAG | 73020 |
| GCATGAACCA | CTGTGCCCAG | CTACTGTGGC | ATGTCTATGA | TAAAAGGAAT | ATCAAGGAGT | 73080 |
| AAAATTCAAA | CTATCCGTAT | AAGAAAGGGA | GGAGAGGGCA | GATTTTAAGC | ACGATTCAGG | 73140 |
| AAGAAGAGTC | AAAGATTTGG | AAATGCTTGG | TTGTGGAAGG | TGAAGCAGAG | GGAGAGGTTT | 73200 |
| TGTGTACCAT | CCAGATTTCT | TGCCAGAAAG | CATATTAAGG | AAGGTGGGAC | TTTGCTGTTG | 73260 |
| GCAGCATGGA | GGAATGGGCA | TAGTCCTGAT | GTCCTTTTTC | CTTCTCTGTC | CTGCCTAAAT | 73320 |
| TTGAGGAAAA | TGTTGTCTCC | AGTGTCAGGC | TCCTTATTCT | GTCCTCCATG | AGGCAGAGGT | 73380 |
| GGTCTTGTAT | GAAGGCTCTA | AGTCCTTCTA | AGGACATGTC | AATCATGACC | ACCACTCAGC | 73440 |
| TCATGGCAGC | TCTTCCTTAA | ACTCCATGGA | GCAGCTAATA | ACTGCGATGA | TCATATTCCC | 73500 |
| ATTTGAATTA | CTTTTCCACC | AAGTAGTAAG | AAAAGGAACC | AGCTTATGTT | GAAATTGAGT | 73560 |
| TTTGTCACTT | ACTAGATGGG | CAATTTTGGG | CACGTTACTT | AATGTCTTCA | CACCTTGGTT | 73620 |
| TCTCCATCTG | TAAATGGGGA | TAATAGCAGT | GTCCTCCCTC | CCTAAAACAC | ATACACAGGA | 73680 |
| GGTGGTTATA | AGCTTTGAGG | ACATTAAAAT | ATAGAATGCA | TAGAATAGCA | CTTGGCATAT | 73740 |
| AGTAAGGACA | ATGTCATCTT | TTGCTAAAAC | AGTTACATAG | AACCTTTTCC | TGAGAACACT | 73800 |
| CGAGAATGAA | TGAGTATACT | TGTTGGGTTT | ACAGAGGACA | GGAGACAATT | CTTTCAGCAT | 73860 |
| TGACTACAAT | TAGCAATTTG | GGTCAGCTTC | AAATCACTTT | CAATAGAAAT | ATGAGAAACT | 73920 |
| GTTTTGAAGA | ATAAGCTAAA | AGCTTGACAT | GAATACTAAA | TCATTTAAA | TTGGATTCAT | 73980 |
| GATACCATTG | TTCAAAGAT | ACCAGAATTC | CCCTCTTCCA | TGAACTGTTT | CTAATAACCA | 74040 |
| GCTGGCATCC | TGATTTTTCC | TGACTCATAA | GACACAAAAT | TTCATGTTGT | TGCCAAACAC | 74100 |
| TGGTATTGGT | TTTGCTTGGT | TCAGCATGTT | GTTTTACAAA | ATCTTTTAGA | TGATGATTAC | 74160 |
| CTTGTTCTAT | ATCCAACTTT | TTCCTGGCAG | GACTCTAGTG | GTGGACATAG | CTCAGGCTCT | 74220 |
| GGGTCAGCAG | ATGAGATTGC | AATTGTTGCT | CCACCACCTG | GCAGTCATAG | CCCTTTGGGC | 74280 |

-continued

| | | | | | | |
|---|---|---|---|---|---|---|
| AAGTTATTTT | ACCCCTTTCT | TAGTCTCATT | TTCTACAGCA | CAGAAATGAA | GTTTAAAATC | 74340 |
| CTACCAACTA | TTCAGGGTTG | CCAAGGGGAT | CAGTATGTTC | CTGCACATAT | AGCCTTTAGC | 74400 |
| ATGCTCTCTA | GCAAAAAACA | ATGAGGACTC | TATAAATATT | CACTATTATT | CAAATATATC | 74460 |
| TTAGAAGATT | GGGATTCCCC | CTAGGTCCCT | AATGAAGAGT | CAAATTGAAT | AGGCTTCACT | 74520 |
| TATCAAATTT | TTCCTTCAGG | AAAAGCTCCA | GAAAGCTGTG | ACAAAACTGA | AGCAACTTGA | 74580 |
| AGACAGATGT | ACGGAGCAGA | AGCTGTCCAC | AGCAATGCGA | ATAACTAAAT | GGAAAGTAAG | 74640 |
| AATCTGACTT | CATTGATCTC | AAGCTATTTT | CCATTCTAGA | GCTTAGGCAT | AGGGGATGAT | 74700 |
| TGAGGAAAAG | CACAATGAGG | ATTTATTCTC | ACTAAACCAG | ATTGAAAAAA | TGAAACCCAA | 74760 |
| GGAAGAAACC | ATTATTTGTA | CTTATGCCCC | TGGTTCCAGG | TTTACATCCA | TGAGTATTTA | 74820 |
| GCACCAATCT | TTCCATCTTT | AAACTGTAGT | TGGCTGGGAT | TCCTGATACT | TCAGTCAGAA | 74880 |
| GAAGCAGAAT | TAGTATGACT | ATTTACCTAG | AAAAAGCATC | GAGTGGGTCT | CAAACTTTAA | 74940 |
| ATACGTCAAA | ATAAACCTGG | TTTGCAGGCC | TCAACTCATT | ACCCTGGCAC | TTTTACCACA | 75000 |
| GTGGAGCATC | TGGCTCTCAA | CTTTACAGGT | ACAGAAACCA | AGCTTTGTGA | ACACTTAGAA | 75060 |
| AACAGGATCA | CTCCAGATTG | AAATTCATAC | TACTCTAGCT | CATGAAGCTG | ATGAAAGAAA | 75120 |
| TATACTTTAT | TTATTTATTT | ATTTTTAAAT | TATTACTATT | TTTTGAGATG | GAGTCTTGCT | 75180 |
| GGAGTGTAGT | GGTGCGATCT | CAGCTCACTG | CAATGTCCAC | CTCCCGGGTT | CAAGCAATTC | 75240 |
| CCCTGCCTCA | GCCTCTTGAG | TAGCTGGGAT | TACAGGCATG | TGCTACCATG | CCTGGCTAAT | 75300 |
| TTTTTGTATT | TTAGTAGAGA | CGGGGTTTCA | CCATGTTGGC | CAGGATGGTC | TTGATCTCCT | 75360 |
| GACCTCGTGA | TTCACCCACC | TCAGCCTCCC | AAAGTGCTGG | GATTACAGGC | GTGAGCCACT | 75420 |
| GCACCCGGCC | TATACTTGAT | TTATAAGTAC | ATCACAAGTA | ATGCAACAAC | CTACACACTT | 75480 |
| GCAACTACAA | ACTTTCAGAT | TATTTCCGTG | GCTGACTAAC | CTCCACATTA | TCAGAGCCAC | 75540 |
| ATTCTTTTAT | GGAAATATTT | AGGTTTGTGC | AAAAGTAATT | GCGGTCTTTG | CCATTAAAGT | 75600 |
| AAAGGCAAAA | ACCACAATTA | CTTTTGCACC | AATCTTTATA | TTTATATAAT | TCACTAGCTT | 75660 |
| GCAGTAAAAT | CCCACAAGCT | GATTACCAAT | TTTCTCTCTT | TCAGGAGTCC | TCTCTAACCT | 75720 |
| CTACCCTGAT | CTTTGTTTGT | GGATGTTGCT | CTTGAGCTCC | TGAGTACACT | CTTACTTCCC | 75780 |
| CCATTTCTAG | GATCTTGGGC | AATGGGGAAG | ACCTTGATTG | TAACTAACAT | ATATGAAAAC | 75840 |
| CCGTCTATAC | AAGAGTTAAA | GCTGCACCTG | TCTCCTACAC | AAAAATTCCA | CCTCATCCTA | 75900 |
| AGTCAAAGAC | CCTTCTTCTA | TATCATAGTC | ATCAAAACAC | TGTATGAATT | TATTTTTATT | 75960 |
| TTTTAATTTT | TATTTTTTTA | AGATAAGTAG | AGAGTTTATT | TGGGCCAAGT | TTGAAGACTG | 76020 |
| CAATCCAAGA | ACATAGATTC | AAATTGCCCT | GAATACACAC | TCCCACTGCA | TTAATTTAGA | 76080 |
| CAGCACTAAT | GGAAATTGCA | ACTTTACATC | TCCTCAGATG | AGAGTTTCAC | TTGATTTCTG | 76140 |
| TCAGTCTTAC | ACATAGGAAT | GCTTAAGATG | ACCCTAGGGT | AGTAGAACAG | TATTTCTCAG | 76200 |
| TTAACCATAA | TAAATGCCTG | TCACACTCAA | AGCTCCCCCT | GCCAAGAATT | ATGGACCCTC | 76260 |
| TTACCAGCCT | GGTTGTCTTA | AAATCCAGTC | TGGGTGATGT | TCATTATAAG | CTTTTACTTC | 76320 |
| AAGAAAATCG | CTCCAACTCA | GAAATCTAAC | TTCTTAAATC | ATAAGTAAAA | ACCTCTTTTT | 76380 |
| ATCCTTGTAA | CTGATAAAGT | GTTTGAACTT | GGCCCTAGTT | TCACAATTAA | ATTATCTAGC | 76440 |
| ACTCCTAACC | CAGCTTTCTC | CTGTGTCTTG | GCTGAAGAAC | AAGAAAATTA | ATTGGGTGAC | 76500 |
| TATAAGGAAT | CTGAGGCAAC | CTCTTCCACA | TCTGAGTGCC | TGCCTCCCAC | ACATGACTCT | 76560 |
| GCAGCAGGAA | ACTGGGACA | TTCTTCCAGC | TTCAGTGACT | CATGAGAAAA | TAATGTCCCA | 76620 |
| GTGGCTGATT | GTGTGTGTGT | GTGTGTTTGT | GTGAAAATAT | ATATAACACT | TAAGCATTTA | 76680 |

-continued

| | | | | | | |
|---|---|---|---|---|---|---|
| ACCACTTTTA | AGTATATAGT | TCAGTAGAAT | TAAGTGCTTT | TACATTGTTA | CATTGTTGTG | 76740 |
| CAACCATCAC | CATTCCCATC | TCCAAACTGC | AACTCAGTTT | CATCTTTCAT | CTTCTAAACT | 76800 |
| GAAACTCACT | ACCCATTAAA | CAATAACTGT | CCATTTTCTG | GTCTTGCCAA | CACCTTGTAA | 76860 |
| CCACTATTTT | ACTTTCTGTC | TCTATGAACT | TAACTACTCC | AGATGCCTTG | TATAAGCAAA | 76920 |
| GTCTTACAAT | ATTTGCCCTT | TTGTTTCTGG | CTTATTTTGC | TTGAATGTCT | TCAAGGCTTG | 76980 |
| TCATGTAGTA | GCGTGTGTCA | GACTTTCATT | CTTGTTTATC | CATTCATCCA | TAGATGGACA | 77040 |
| TTTGGTTTAC | TTCCACCTTT | TGACCATACT | TTCTTGACTC | CAGGAGAAGG | TACAGATTCA | 77100 |
| GAGACAAAAA | ATCCGGTCTG | ACTTTAAGAA | TCTCCAGTGT | TTCCTACATG | AGGAAGAGAA | 77160 |
| GTCTTATCTC | TGGAGGCTGG | AGAAAGAAGA | ACAACAGACT | CTGAGTAGAC | TGAGGGACTA | 77220 |
| TGAGGCTGGT | CTGGGGCTGA | AGAGCAATGA | ACTCAAGAGC | CACATCCTGG | AACTGGAGGA | 77280 |
| AAAATGTCAG | GGCTCAGCCC | AGAAATTGCT | GCAGGTGAGG | CTGTGTACTT | GGAGTAGGGA | 77340 |
| AAAAAGGTAT | GTTATAGTGC | TATTAAAGGA | GAATGGTAAG | GAAGCATGGG | AAGATAAAGT | 77400 |
| AATGTTTCTT | TTAGATGTAC | ATCAGTGCCA | TCAGGCTGGC | CTTCACTAAT | TTATAGGGTA | 77460 |
| CCTTTATGTC | AATTAGAAAA | ATAAACTTCT | GAGGGAACAC | AGCTTGGCCA | AATGAAACCA | 77520 |
| CGGGATAACA | TTTACCACTG | TTTGCCTCCT | TGGCCCATGT | GCAGAGAACC | CTGGTTGTTG | 77580 |
| ACTCTCTCCT | GAAATACTCC | ACTAGGTGAC | TGATGGGTGA | TGAAGTGGGG | CAGCCAAAAT | 77640 |
| GAGTGATAAC | CTTTTCCCTG | ATTTGCTTGT | AGAACCCTTG | CTCCAGAGCT | GTTATGGTAC | 77700 |
| AATCTACAGC | TTTATCTGTA | GGAAGATAAA | CATCTGGAGC | CATTAATTCT | GGTTCTAACT | 77760 |
| AACAGGATTG | GTGACTATAC | TGTAAGGCTG | AGTGTATAGC | ATGATTGCTT | TACCACTGTG | 77820 |
| TGATACCTGC | TACCACCATC | TTAGTGGCAG | TGGCCCAGTC | TCAGGGCTGT | GCACAGATTC | 77880 |
| ACCACTAAGG | ACCTTTATGA | TAAGTGTTCT | CTAATCTGGG | CTCACTGTGA | AGGAAATCCG | 77940 |
| ATCACCAAAA | GCTAGTCCTT | ACAGAGGGAG | CATGGACAAA | GCTCCTGGCC | CTCAGACTTC | 78000 |
| AGCAAGGATG | AGAATAGATG | CAAATGTTGA | TAAACATCCT | GCCATGCTGA | ATCTCCCAGA | 78060 |
| AGCTGGTAGG | AATTATTCCA | TCTGGGTATC | CATCAATACC | TAAGACTGGT | GGGAATTACT | 78120 |
| TTGTTTGAGT | ATCCATCAAT | ATCTAAGACT | AAGACTAGGG | TAACTCTCTT | TACTTCTTCG | 78180 |
| GGTAAAGCAA | AGAAGAATAG | CCCTGCATGA | CAAGCCCCAT | GAAATACCGA | TGTTCCCATG | 78240 |
| CTCACCTTTT | CTTTTTGTTT | CTTTATAGAA | TGTGAATGAC | ACTTTGAGCA | GGTAAGTCCT | 78300 |
| GTTTGAATGC | AGGAGGGGAG | GGGTGTGCGT | ATATAGAAAT | GAATGGAATG | CACCTCTGAA | 78360 |
| GAAATCTCTC | GCCTCTGCTT | ATTCTAGGAG | TTGGGCTGTG | AAGCTGGAAA | CATCAGAGGC | 78420 |
| TGTCTCCTTG | GAACTTCATA | CTATGTGCAA | TGTTTCCAAG | CTTTACTTCG | ATGTGAAGAA | 78480 |
| AATGTTAAGG | AGTCATCAAG | GTATGTTCAC | TAAAGAATTC | CTGAATACTG | TGGATAGAAG | 78540 |
| GGGCCTTATG | CAGTAACCAA | GTTACCACC | TGTCCCTTGG | CAGGCTCACA | GCCAGAGAGG | 78600 |
| TTGTTTAGTT | AATTTCAGTA | GAGCTTTCAT | ACTTTCTCTA | GTTAGTATGA | TTCACTGCTC | 78660 |
| AGTGAATGTG | ATGAGCATTG | CATTCTGGTT | ATCTGTGCAA | ACCTTTCAAA | TTCTTATTCT | 78720 |
| TTCACTTATT | AGCCATGTTA | CTCCAAGTGA | CTTGGTTTCC | CCCTCTGAAA | AATGAAAATA | 78780 |
| TTAACAGCTC | CTACTTCATT | GAGTTATCAT | CAAAATTAAA | TGCATCAACA | TGTACAAAGT | 78840 |
| GCTTAGCCCT | GTGACTGACA | CATGATCATA | ATAGCACATC | ATGGTATTAG | ATCTGATCAT | 78900 |
| AGTGTTTATT | ATCAATAGCT | CAGCCAACTC | TTAGAGCAAT | GCAAGAAAAG | TAGGTGAGTA | 78960 |
| TGATAACCTA | TCATTCACAT | ATTTTAGGAA | CTTGACTTAG | ATAACACAGA | TGACAAATGT | 79020 |
| TACAACCAAT | TTACAGATTC | CAAAATGTTA | GAACCATTTA | CTGAGTTTCC | TGCTCCCTTG | 79080 |

-continued

| | | | | | | |
|---|---|---|---|---|---|---|
| ATTTTTTAAA | TCAGTGCTGA | CTATACTTTC | ACAAATTTGT | ATCCGTAAGT | ACAAAATCAA | 79140 |
| AAAAACCCCT | GAAAATGGAA | AGTTTTATCA | TGATTCATTT | GGCTACAAAA | ATCTGGCCTA | 79200 |
| ACCTGAAATG | ATTTGGTGGT | TATATTAGTT | ATCTATTAGT | ACAAACAAAT | TACCATAATT | 79260 |
| TAGAACCTTA | ATACAACACT | GATATGTTAT | CTCAATTTTT | GTGGTTCAGG | AATCTGGGCA | 79320 |
| CAGCTTAGTT | GGGCCTGCTG | CTTAGGGTCT | GATAAGGCTG | CAGTTAAGGT | GTTGGTCAGG | 79380 |
| CTGTGTTCTT | ATCTGGAGGC | TAGGCTAAGG | AAGAATCCAC | TTCCAAGCTC | ACTGAGGTAG | 79440 |
| CAGGCAGAAT | TTCTTTCCTG | ATGGTTGCAG | GACTTTGGCC | CTGGTTATTT | CTGGCTGTTG | 79500 |
| GCTGGAGGTT | GCCCACAGCT | TCTACAGGCC | ACCCCTCAGC | TCTTTGCACA | TGGGCTTCTA | 79560 |
| ACATGGCCAG | TTATTTCTTC | AGAGAGAGCT | CAGGAGACAG | ACTCTTTAGA | GAAAATCTGC | 79620 |
| CAGCAAGATG | GAGTCTTACA | TAATGAAACG | TAATCATAGA | AATTATATCC | CATCATCTTT | 79680 |
| GCCATATCCT | ATTGGTCAGA | AGCAATTCAT | AAGCCCTGCT | CACACTCAAA | GACAAGGAAT | 79740 |
| TTACGAGGG | TGTGAACACC | AAGAGGCAGG | AATCATAGAA | GGCCACCCTT | GAGTCTGTCT | 79800 |
| TCCACAGTGG | CCAACCCTGA | ACGGCACTGA | GATGAGACTA | TTTAAAAGTC | TTTATTTATC | 79860 |
| CCACTTAATT | TGAATAAATG | TTTTGCTGCA | GATATATTGA | TGAATTTGAT | TACAGGGCTC | 79920 |
| TGCCTTAGGC | CATGATGGGG | TTGAACTTTA | GAGTATATGC | ATTTTTTGC | CTTTATAACT | 79980 |
| TCTAAACTAA | TTTGAATGGC | AAAGCCCATT | TTGTTCCAGG | GATTTCAGAA | AAGGAATTAT | 80040 |
| AGACCTGTGT | TCCCCTCAAA | TACACAACAA | CAAACAACAA | CAAAACCCAA | AAGCACTCTG | 80100 |
| TATTTCATCC | TATACAGATG | ACAGGAAGGA | AGAACAAGAC | TTTGTGTAAG | TTTTGCTGGG | 80160 |
| ATTTCACTGA | GTCAATTTGC | CTACTCTCAT | CTTTTACAGA | AGGAATCATA | ATATGGTTCA | 80220 |
| AGTGAAACTA | TTTCTTTCTT | TCTTTCTTTC | TTTTTTTTTT | TTTTGAGAC | AGAGTCTCGC | 80280 |
| TCTGTCGCCC | AGGCTGGAGT | GCAGTGGTGC | GATCTCGGCT | CACTGCAAGC | TCCGCCTTCC | 80340 |
| GGGTCAAGTG | AAACTATTTC | TTAAATGGGC | TTATCTTTTA | ACTAAATATT | TCTCCCCTCT | 80400 |
| TAAACACTGT | TTATTAAAAT | TTTTCTTTTT | TCAAATTTTT | TTTTGAGATG | GAGTCTCGCT | 80460 |
| GTTACCCAGG | CTGGCTTGCA | GTGCCGCAAT | CTCAGCTCAC | TGCAGCCTCT | GCCTCCTGGG | 80520 |
| TTCCAGCGCC | TCAGCCTCCC | GGGTAGCGTG | GGATTACAGG | TACGCACCAC | TATGCCTGGC | 80580 |
| TGATTTTTGT | ATTTTTAGTA | GAGATGGGGT | TTCACAATGT | TGGCCAGGCT | GGTCTCAAAC | 80640 |
| CCCTGACCTC | AGGTGATCTG | CCTGTCTCTG | CCTCCCAAAG | TGCTAGGATT | ACAAGTGTTA | 80700 |
| GTCACTGTGC | CCAGCTTTAT | TACAAAAGTG | ATAGGAATAA | ATTTTATTTT | TATTTTTAAA | 80760 |
| TGTATGTTTA | TTTTATTTTA | CATTGCCTTC | AAGCAGATGC | AACAAATACA | TTTTAATCAG | 80820 |
| TCAAACAATA | TAAAGGATAT | AAGGAGAAAG | TTCAAGGTTT | TTCCCACCCG | TCTCCAATCT | 80880 |
| GACTTCTCTA | GGTAGGGTGA | TCTATATCTT | TCCCTAAGTT | TGTACAAACG | TAACATATAT | 80940 |
| ACACTGTCTC | TTCTATGTTA | CTCGTTACTT | TTTATGTCTA | ATATTCCATA | AGAATATAAT | 81000 |
| AAATATATGT | AACCATATCC | CTACTGATGG | AGCTTCAGGC | TGTTTTAGA | ACTTAGTTAT | 81060 |
| TACAATGTTG | CTACAATAAC | TTTCTAGTCC | ATGCATCCTT | ATATCCTGGT | GCTTTCATTT | 81120 |
| CTTTTGGGAA | CATACCCCAA | ACTGGGATTG | CCGAGGTTGT | TGTTAATCTT | AATATATGGT | 81180 |
| ACCATATTAC | TTGACTCAAA | GTTGTAACAT | ACACTCCTAC | CAGCACCAGG | AATAATGACT | 81240 |
| CACATATACT | GAGCACTCTT | TAGTCTGTGA | CAGATTAGAA | AAGCTTTACT | TTTCTTGGTT | 81300 |
| CTTGTTTTAT | ATCACAGTCC | TCTCTATATG | GGGCATTTTT | GCTTTATAGA | GGAGGAAATA | 81360 |
| TGACACAGAG | AGGTTAGGTG | AGTGTTGTAG | GATCTCATAA | CTAGAAGGTA | GTCATAGAAA | 81420 |
| GAGTCTAGAG | TCTAGAAACC | ACTCTCTCAC | CATTTTGCAA | TGTGGCAGAA | AATGCAAAGT | 81480 |

| | | | | | | |
|---|---|---|---|---|---|---|
| TGTTATTTAC | TTATCTCTTT | TAGACAGGGT | CTCACTCTGT | CACCCAGGCT | GGAGTGCAAT | 81540 |
| GGCCCCATCA | TGGCTCCCTG | CAGCCTTAAA | TTCCTGGGCT | TAAGCAATCC | TCCCACGTCA | 81600 |
| GCTTCCCCAG | TAGCTGGGAC | CACAGGCAAG | CACTGCCACG | TCTGGCTAAT | TTTTTAAAAA | 81660 |
| TTTTTTGTAG | AAACACTATC | TCTTTATTTT | GTTCAGGCTG | GTCTTGAACT | CCTGGGCTCA | 81720 |
| AGCAGTCCTC | TCGCCTCGGC | CTTCTAAAGT | GTTGGGATTA | CAGGCATGAA | CCACCATCTC | 81780 |
| CGGCCTGAAG | TTTATTTAAT | CCATTGCCTT | GTGGACTGGG | CATTGAAGTT | GTGTGTAGTT | 81840 |
| GGGTTTTTTT | GTTGTTGTTG | CTGTTGCAGA | CAATACTACT | GTGAACATTC | TTATCCATGC | 81900 |
| TTCCTTGTGT | CCCGTAAATG | TTCCCTCCAG | GGAGATACCT | TGGAGTGACA | TGCTGGTGTG | 81960 |
| AGGGATGCAT | ATCATAATTT | TACCAGATAC | TACAGATCTT | GAAATTGTTC | CAATTCTACC | 82020 |
| CCACAAGCAA | TATAAGAGCT | CTCACTCCTC | CAAAACTCCC | TGAGTCTTTA | CTTATATAAT | 82080 |
| TTATGATTTT | GACAGTCTTA | CAGATTTAAA | ATGGTACCTA | ATTGTGTACT | TAATTTGTGC | 82140 |
| TTTTCTGATT | TCACTAGTGA | GATTGAGATT | CTTTTGTAT | GTCCATTAGC | CCTTCAGGCC | 82200 |
| TCTGTGATTT | ACCCATGATT | TACTGTGGTT | TAATAATTTT | TATTGGGTTC | TTTTCCTTAT | 82260 |
| TGATTTATGG | GAACTTATTA | TAGCTGATAT | CTTCTGGCAT | GTGGATGGCA | TTTTGCATTT | 82320 |
| TCATCCTGTT | TTTTGATAAA | TAGGGTTTCA | AAATTAAGTA | GACACATTTT | CCTTCAAGGT | 82380 |
| CTGTGTCTTT | TATGTCCAAA | GAGCTTAGTC | ATCAGTGGGC | AGTGAATTTT | ATCACCTAAT | 82440 |
| TAATTTTATT | AGCCCCGTGT | GCTATGCCTG | TAGTTCCAGC | TACTGGGGAG | ACTAGGGCAG | 82500 |
| GAGGATCTCC | TGAGCCCAGG | AGTTCGAGGC | TGCAGTAAGC | TATGATCACG | CCACTGTACC | 82560 |
| CAGCCTGGGC | AACAGAGCTA | GACCCTGTCT | ATTAAAGGAG | GAGGCCGGGT | ACAGTGGCTT | 82620 |
| ACGCCTGTAA | TCCCAGCACA | TTGGGAGGCC | GAGGCAGGAG | GATCACTTGA | GGGCAGGAGT | 82680 |
| TTGAGACCAG | CCTGGCCAGC | ATTGTGAAAC | CCTATCTCTA | CTAAAAATAC | AAAAATTAGC | 82740 |
| CAGGTGTGGT | GGTGTGCACT | TGCAGTCCTA | GCTACTCTGG | AGGCTTAGGC | AGAATTGCTT | 82800 |
| GAACCCAGAA | GGCAGAGGTT | GCAGTGAGCT | GAGATTGTGC | CACTGCACTC | CAGCTTGAGC | 82860 |
| GACAGAGTAA | GACTCCATCT | CAAAAAAAAA | AAGAAGAGAG | ATGAAGGAGG | AGGAGGAAGA | 82920 |
| GAAAGAGGTG | GGGGAGGGGA | AGGAAGAGAA | AGAAGAAGAA | AGGGACAAAA | AAATTTAGCT | 82980 |
| GTCATCTTTG | CTCTGATAGC | ATTATAATGA | TGATGAAGAC | AATTGCTAGG | TTGGTGAGAG | 83040 |
| AAGGCTATAT | ACACACCAGA | ACTCTCCACG | TATATGGCAA | GTTCATATAT | TTTGTTAAGT | 83100 |
| ATGTCTCATT | GGAGACCTTC | TTTTCCCGTA | ACTATGACCA | GTGCTCTGCC | AGCTCAGTCA | 83160 |
| ACAACAACAT | TGCATGTTGG | CTCCATACCT | GGACTCTTGG | TCCAATTGGT | AATGAAACCA | 83220 |
| TCCCACCAGT | GTCTTCATAA | TATATATATA | CACACACACA | TATATATATA | GTATTCTCTC | 83280 |
| CCAGTGTCTT | CATAATATAT | ATATATACAC | ATACACACAT | ATATTATATT | CTCTCTATAC | 83340 |
| ATATTTATTT | ATATATCTAT | ATCTATATCC | TTCCACCTCA | GGTCTCCCTC | TGTCTCCCAG | 83400 |
| GCTGAGTGGT | GCAGTAGTGC | GATTATGGCT | CAACCAATGA | GAGGATCAAT | GGCAATCCTC | 83460 |
| TCATTTCAGC | CTCCCCAGTA | GCTGGGACTA | CAGGCATGGG | CCACCACATC | TGGCTGATGT | 83520 |
| TTAAATTTTT | TTGAGACAGC | ATCTCTATAT | GCTATAGATA | TATATAGTAT | CCTCTCTCTA | 83580 |
| ATATGGATAG | AGGATACTAT | GTCTATATCT | GTATCTATCT | ATCTATGGAG | AAGGAATACT | 83640 |
| ATATATCTAA | TAAGATGTAA | TCTATATTAT | ATATAAAAGT | GAAGCATTGA | TTGGTACATA | 83700 |
| TAATATATAT | ATTGATTACT | GTGTGTATAT | ATTTGTTTTT | TCGAGACAGG | CTCTCACTCT | 83760 |
| GTTGCCCAAG | CCGAGTGGTA | CAGTGGTGCG | ATCATGGCTC | CACCACCTGA | GCTAAAGTGA | 83820 |
| TCTTCTCACC | TCAGCCTCCC | CAGTTGCTGG | GACTACAGGA | ACAGGCCACC | ATACCTGGCT | 83880 |

| | | | | | | |
|---|---|---|---|---|---|---|
| AATTTTTTAA | TTTTTTTTTG | AGACAGGGTC | TCCCTTTGCC | ACCCAGGCTG | GAGTGCACTG | 83940 |
| GCGCAATCTC | GACTCACTGC | AATCTCCACC | TCCCAGGCTC | AAGTGATCCT | CTCACCTCAG | 84000 |
| CTTCCCGAGT | AGCTGGGACT | ATTGGTGTGC | ACCACAATGC | CTGGATAATT | TTTCATATTT | 84060 |
| TTTGTAGAGA | TGGAATTTGG | CCATATTGAC | CAGGCTGGTC | TCAAACTCTT | GGACTCAAGT | 84120 |
| GATTGACCCG | CCTCAGCCTC | CCAACGTGCT | GGGATTACAG | GCATGAGTCA | CTGTGCCTGG | 84180 |
| CCTGATTATT | GTACACATTT | TTGATGTAAT | GTATTATATA | TGTCATATAT | GACAATCTAG | 84240 |
| ATGAATATAT | TAAAGATTGG | GTTTTCATTT | ATATATTGTA | AAATACATAC | ACTATACATA | 84300 |
| TATAATATGT | AGAACATATG | CTATACATAT | TATATATGTA | TATGTTAACA | TATATAATAC | 84360 |
| ATACACATAT | AATATGTATA | GTTGCAAATA | TAAAATTTGG | TTTGTTATTT | ATATTATTTT | 84420 |
| GTGCAGGAGT | TCTATATCTA | TGTCTATAAG | CGGGAGCCAT | AATTTCTAT | TCTTTGTAGG | 84480 |
| ATTTGGTATG | AGATTGGCAT | TACTCATGCC | TTGACTTCTA | AATTTCCTAT | AAAACTGACA | 84540 |
| AGTTCCATTT | TTGCTTGATA | AAGATGCACG | TTTTATTATC | TGTCGGTAAA | ATTAAAGTA | 84600 |
| GTGATTTCAT | TTCTTTAATG | TTAGGTCTGC | CCATGCTTTA | TTTGTTTTTT | GAGTGAGTTT | 84660 |
| TACTCAGAAA | TATTTTTTCT | AGGAAGTAAT | AATTTATCA | GTACTTTCAA | TTTTATTAGT | 84720 |
| AGCATAAGAT | TTATTATAAA | GTTCTGTAAT | ATTTAAAAAG | TTTCTGTATT | CATTCCATTT | 84780 |
| GTGCCTTCTG | TCTTACTTTG | ATAAATCTCA | TTGGAGGTAT | GTCTATTTA | TTAAATTTCT | 84840 |
| TTTAAAAGAA | GCTACCTTTT | TTTTTGTTTG | TTTTTCCTCT | TTATTGCATT | CTTGTTTTCT | 84900 |
| TTAACTTCAC | TGTTATATTG | TTTAATATCT | ATTTTTTCTT | TTTAAAAAAT | TATATTTGGC | 84960 |
| TTTCTATGTT | CTTTTTAAAA | TTTAAATTAG | ATGCTTGGCT | CATTAATGTT | CAGCTTTTTA | 85020 |
| ATTTTTCTAA | GATAAGCATT | TAAAGCCTAC | AAATTTTCCT | TAAAATTCTG | CTTTAGCTTC | 85080 |
| ATTGTATATT | TTTATAAATA | ACTTTTTATT | ATTGTTCCAT | TCTATACATC | TTCTAATGAC | 85140 |
| TTATTAGTAG | TTTACATTTC | CTAATATTTA | GAATCTTTTT | AGTCATCTTT | TTATTATTGG | 85200 |
| TTTATAATCT | TATATTGAGG | CTAGAGAAAA | TGATCTGTGT | AATACAGATT | TATTGAAACT | 85260 |
| TGTTCAGACT | GTTTTCTGCC | TAGTATTTAC | TCAGTTAGTG | CATGTTCCAT | CTATACCTGA | 85320 |
| GAAAACTGCA | TATTCTCTGC | TTACTATTAT | TAAACAATTG | CTGAGCTTTA | TGTATTGACT | 85380 |
| ATGAGATTGC | GCTTCTTAGA | TTGTTCAGAC | CTTCCGTATC | TTCCCTTATT | TCTTTCTTTT | 85440 |
| GGTCTGCCTG | ATCTATCAAT | TATGGAAAGA | AGAATGTTAA | AACATCCCAT | GATGATTGTA | 85500 |
| GATTTGTCCA | TTTCTCCTAT | AATTCTACAA | TTTTTGCTTT | GTATATTAAC | ACAATTCTAA | 85560 |
| ACATGAATTC | ACTAATAATG | TAGTACATTT | ATGTTTAAAA | TTGTGTTATC | TTTTTTAGGT | 85620 |
| GACTCCTTTC | ATTCTTTCTT | TTTTTTTTTT | TTTGAGACAG | AATCTCTCTC | TGTCACCCAG | 85680 |
| GCTGTAGTGT | AGTGGCGAAA | TCTCAGCTCA | CTGCAACCTC | TGCCTCCCCG | GTTCAAGTGA | 85740 |
| TTCTTGTGCT | TCAGCCTCCC | AAGTAGCTGG | GATTACAGGC | ATGTGCCACA | ATGCCCAGCT | 85800 |
| AATTGTTGTA | TTTTTGGTAG | AGCCAGGGTT | TTGCCATGTT | GGGCAGGCTG | GTCTTGAACT | 85860 |
| CCTGGCTTCA | AGTGATCCGC | CTGCCTTGGC | CTCCCAAAGT | GCTGGGATTA | CAGGCATGAG | 85920 |
| CCACCACACC | TGGCCCTTCT | TCCATTCTTA | ATAATGCTCT | GACTTAATAT | CTTTTGATAT | 85980 |
| AATACTATAA | CAGTATATGA | CTATATTATC | TATCTTTTAG | CTTCCAATCT | TTCTATATGT | 86040 |
| TTTTGTTGAT | GTGTCACACC | AATAGATAGG | TGGAATTTTA | AAAATCCAAT | TGATATTTTT | 86100 |
| TCTCTTAAGT | GGTATTACCA | CCCCGTAAAC | ATTTTAATTT | CTCAACATGG | GTTTTCCTGG | 86160 |
| GTCATTCAGG | TAATATGAAT | TGAAACCCCA | AACTTCTGTG | AGTCAGGCTG | ATAAAAGCTA | 86220 |
| ACTGAATAGA | GTTTGAAAAA | GGAGGGTATT | TACAAAGGTG | AGGAGTTGGG | AAATCCACAA | 86280 |

| | | | | | | |
|---|---|---|---|---|---|---|
| GGAACAGGAA | GCACCCAGAA | CTAGGAACAG | TTAGAGAGCC | ATCACCTCCT | CTGGGCCTCA | 86340 |
| AGTGGCAGGT | GTAGGGAGCT | GTAACTATAC | TAGAGTGTGC | CCAGAGGCAG | AGGAATGCAG | 86400 |
| ACCCTCCAAA | TCATAGCGTG | GGACTGGGGT | ACTGAATACT | CCCAAGGCTG | CTTCTTTGTG | 86460 |
| CCCTATGGTC | TCCTCTGGTG | CTTCCCATTG | GCTGAACCAA | GCCAGAGGGC | GGAAAGCCTG | 86520 |
| GTTAATCTGT | CCATGTCAGC | CTTCCTGGGC | ACAGAGCAAG | ACAGGGAAAA | GTGAGGGATT | 86580 |
| ATTTGGAAGA | ACAAACAGAG | AGCATCCAGC | ACAGGAAGTG | TTTCTGAATA | CTTGAATTCC | 86640 |
| TTAATTGTCA | CAGACCAACT | GATCAACATT | TAACTCAGTA | GCACAGTGGT | TTCCTTAACT | 86700 |
| CTCTTGTTAG | AACATCCTAT | TACCATTTTT | TATTTTAAA | ACTGCATACT | GTTCCAGTAT | 86760 |
| CTCACTTTAG | TTATCAGATC | TTTTTCTGTC | TTGTTTGATT | CTAGTCTGAT | ATTTTTCCAT | 86820 |
| GTTATATTGG | TCCTCCAGTG | TATTATTATC | TCATACTAAT | GCTTATGGAA | CATTATCTGA | 86880 |
| GGGGAAAGAG | AAGAGCTTAC | AATTAAAAGT | CATGGGACTA | GGCATGTGTC | ATGAGACCTG | 86940 |
| GGTCTTCCAA | TAACAAGCTA | AGACATTAGC | TGAGTCATTT | TCCCTCTCTG | ATTCTCAATG | 87000 |
| TTGGTGGTTA | TTCAGTAGAG | AAGGGAAAAG | GTATCTTTCT | GCTCAACTGT | CTCATGATTC | 87060 |
| CTGGAAGTCC | TGCATGGGAG | AAGAACTTTG | GACAGGATGG | TAACCATATT | AACAGGTTAG | 87120 |
| TTCTGTACCT | TGGCATCCTT | GAATAATTAA | GACGAAGATG | ATGTTGATGA | TATCATTATT | 87180 |
| ACTACATGTT | GTTAGAAGAG | CTGAAGCAGG | ACTGGCTTGT | CTGTCATAAT | GTAAAAGAGT | 87240 |
| CTTGGAAGAT | GTCCGGGGTC | CAGGGTCCAA | AACCCCTCGT | GGCCTTTGGA | ACACCAAGCT | 87300 |
| CTGTGCCAAA | TGGTGGAAGG | CTGCCCTGCC | GCACCACAAA | TCTAAGCCTA | GGGCATAAAA | 87360 |
| CCCCTTGTGG | CTTGGATGGA | ACCCAGGGCT | CAGGGCATAA | AACCCCTCAT | AGCCTCTGGA | 87420 |
| AAGTGCACAG | ACTTGTTGGT | TCCTTGCTTT | TCACTCATAA | ACGTGTCCTC | TACTATCTCA | 87480 |
| AGCAGCAGAG | TATATTCTAC | ATGTGTCAAA | GAAAATGCTA | AACTGTCACA | GCTACGCTTA | 87540 |
| ATGCACCACT | ACCTTTCTAC | CCCCATGTCC | TCATGCCCTC | ACCTGTTTAC | CCTCACGTCC | 87600 |
| TCACCACCTG | CTTCTTTGTT | TGATCACCAA | TAAATAGTGT | GGGCTCCCAG | AGCTTAGGGC | 87660 |
| CTTTGCAGCC | TCCAATCTAG | TGCTGGCACC | CTGGACCCAC | TTTATGCACT | CTTAACTTGT | 87720 |
| CTTTTCTCAT | TCCTTTGACC | CCGCCGGACT | TTGTAGCCCC | CACGGCCTGG | TGTTGGGCCT | 87780 |
| GATCACCCCA | ACAACTACCA | CTTATTAGTG | GTTACCATGT | ACCAGGAAAT | TTACCAAGC | 87840 |
| ATTAAGCAAA | CATAAGCTTA | TTCAATCCTA | CCCACCATTC | TCTGCAACAA | ATACGGTAAT | 87900 |
| TTCCACTTTA | TAGTTAACAA | ACTGAGGCTC | AGAAAGTTAA | ATGATTTGCC | TAAGCTCACC | 87960 |
| CAGTTTATAA | GAAACAATAG | TTGGGTTTGA | ACACAGGCTG | GTTTTATTGA | AAATAACTTG | 88020 |
| TGGCTGGGCA | TGGTGGCTCA | CACCTGTGTA | ATCCAGCACT | TTGGGAGGCC | GAGGTGGGTG | 88080 |
| GAACACTTCA | GGTCAGGAGT | TTGAGACCAG | CCTGGCCAAC | ATGGCGAAAC | CCCATCTCTA | 88140 |
| CAGAAAATTT | AAAAAAATTA | GCCACTTGTG | GTGGTGCGCA | CCTGTAGTCG | CAGTTACTCC | 88200 |
| GGAGGCTGAG | GCAGGAGAAT | TGCCTGAATC | CAGGAGGTGG | AGGTTGCAGT | GAGTTGAGAT | 88260 |
| AGTGCCAGTG | CACTCCAGCC | TGGGTGACAG | CAACACTCCA | TCTCAAAATA | AATAAAATA | 88320 |
| AAATAACCTG | TGTTCTTCAC | AGCAACAAAA | TTATTTTTGT | TTGTTTTGTT | TTGTTTTGCA | 88380 |
| GTTAGTGTGA | CTCTGGATCC | AGATACAGCT | CATCACGAAC | TAATTCTCTC | TGAGGATCGG | 88440 |
| AGACAAGTGA | CTCGTGGATA | CACCCAGGAG | AATCAGGACA | CATCTTCCAG | GAGATTTACT | 88500 |
| GCCTTCCCCT | GTGTCTTGGG | TTGTGAAGGC | TTCACCTCAG | GAAGACGTTA | CTTTGAAGTG | 88560 |
| GATGTTGGCG | AAGGAACCGG | ATGGGATTTA | GGAGTTTGTA | TGGAAAATGT | GCAGAGGGC | 88620 |
| ACTGGCATGA | AGCAAGAGCC | TCAGTCTGGA | TTCTGGACCC | TCAGGCTGTG | CAAAAAGAAA | 88680 |

| | | | | | | |
|---|---|---|---|---|---|---|
| GGCTATGTAG | CACTTACTTC | TCCCCCAACT | TCCCTTCATC | TGCATGAGCA | GCCCCTGCTT | 88740 |
| GTGGGAATTT | TTCTGGACTA | TGAGGCCGGA | GTTGTATCCT | TTTATAACGG | GAATACTGGC | 88800 |
| TGCCACATCT | TTACTTTCCC | GAAGGCTTCC | TTCTCTGATA | CTCTCCGGCC | CTATTTCCAG | 88860 |
| GTTTATCAAT | ATTCTCCTTT | GTTTCTGCCT | CCCCCAGGTG | ACTAAGGAAA | AGAGCAGAAG | 88920 |
| CTCCTTGGTT | TAACCAGCAC | AGAGAAAATA | ATATAAATCC | CATAAGGGCA | GACGTTTGGT | 88980 |
| CTGTTTTCTT | CGCTGTCATT | TCCTTAGTAG | TTAGACTAGT | GCTGAGATTT | TAGTGGATAT | 89040 |
| ATAATTGATT | TATGTTGAAT | ATATGGACTT | AGCAACTAAA | AATACCACAG | ATGGTTAACC | 89100 |
| TGGACTGGGG | CAAAGCAAGA | TAATAGTGAT | GATCGTATGT | TGCTGTCTCC | ATCCGTCTTT | 89160 |
| AATGGGTCAG | GGCTTTGATT | TCCAAGGGTC | TTCAGGTGAT | GAGTAGGGGT | ACCCACAAGT | 89220 |
| CAGAAGGTCT | GCGTTCTCCT | AGTTTGTTTG | CTGCCATTTG | AACTCATGTA | GGGAATGAAA | 89280 |
| GAAAGCTGCA | ATTATCCGCC | AACTGCATTT | AAAACAAAAC | AAAACAGAAA | AATCAAAATA | 89340 |
| ACATTGACTC | TTCCAACCAC | TGACATGTTG | TTTAATAATC | TAAGCGGCAG | TCCTGGAGGC | 89400 |
| TACCAGACTT | ACTGAGTTCT | ACCTGAGAAA | CAGCCAAGCA | AAGTGTGAGA | GAAGGGTTAA | 89460 |
| GACTGGCTTA | CAATGAGATG | CTTCAAATGA | AAAGGGAATT | ATGAGTAAAA | TTGAACTTTG | 89520 |
| ATGGGGGATT | CAGTTCTGGA | AAAGAATTTG | GTATTTTCCA | GTCTGCTAGG | ACCAATTACC | 89580 |
| TTGAAATATT | TTAAAATCTC | AGTAAATAGT | TATTGCTGAA | ATGGCTGTTG | GCAGTTCTTA | 89640 |
| TTATGATTCA | GAGAAGAGCA | AATAGACCTT | AACTTCATTT | TGAAAAGAC | CAAATTACCA | 89700 |
| TACCCGAGTG | AGTAATGACA | GGACTACAAC | TAAAACATAA | ACAACATTAA | TGATGACCAT | 89760 |
| AAAAAGTCAC | AAAATTGCTA | AATGTTATAA | TTTAGAGTTG | ACATAAAAAT | TGATGGCCAG | 89820 |
| GCATGGTGGC | TCACGCCTGT | AATCCCAGAA | CTATGTGAGG | CTGAGGCAGG | TGGATCACTT | 89880 |
| GAGGTCAGGA | GTTCAACACC | AGCCTGGCCA | ACATGGTGAA | ACCCTGTCTC | TACTAAAAAT | 89940 |
| ACAAAAATTA | GCCGGGCATG | GTGGTAGGGG | CCTGTAACCC | AGCTACTCGT | GAGGCCAAGG | 90000 |
| CAGGAGAATT | GCTTGAGCCT | GCAGCAGCTG | CAGTAAGCCA | AGATCATGCT | GTGCCTCAAG | 90060 |
| GAAAAAAAAA | ATTAATGTTT | ACTGATATTT | GTTGAAGTCC | TACAACATCA | CCTCTGAGAA | 90120 |
| TAGGAGAAAT | GAAGCAACAG | TTGTGTCTAG | ATGTCAGAGG | CATGGCTGGG | CCTCCATCTC | 90180 |
| TGCCTAAGGG | AGATATAAAA | GAGTTCAAAC | TATTGCCCAT | GTTCCCAGG | GTCAGAAGTT | 90240 |
| CTAATTATGA | TGATAGAGGC | TGGGTTGTAA | GTAGTAAGTG | AAGGGTAGCA | GAATATGCCA | 90300 |
| TCTTTGGCAT | AAGAAGTATT | TTGAGTTGAA | GACAATTGAG | AAAAAAAATA | GATTAAAAAC | 90360 |
| AAACAAACAC | CTCTGCCCTC | TCCCTATTTG | CCTAAAAGCA | GGATATGAAA | TTGTGAAGGT | 90420 |
| GTCTTCTTAC | TCGGGGAAGA | ACAAAAGTTA | GTCACCAGAG | ACTTAGACT | CTTATCAGCC | 90480 |
| TGGACATAGC | ACCAGAGAAG | TCTTTTTTTT | TAAAAAAAAA | AAAAAAAAA | GGGAAAGAAA | 90540 |
| AAGTTGCCTT | CCCACAATTT | ACTGCACTAG | AAACTCAAAG | TCCTTTTCGT | CTTCCTTGTC | 90600 |
| ACTTAAAAAA | TGTATTCTTT | TCTTAAAATG | CTATATAAGC | CCAAGTTCTA | AATCCTCTTT | 90660 |
| TGAGTATTCA | TCTCAGTACT | CCCCTGTGTT | TGTACAATGC | ACATGCTTTG | TTTCTGTCTT | 90720 |
| GTCAATCTGT | CTTTTGTTAG | TCTACTTGAT | AGGGCCACAG | ATGGAGAACC | TAAGATGAAT | 90780 |
| AGAAAAAAAA | GATTTTCTC | CCCAACAGAA | GGATTATCGC | CAGTTGCACT | TGTTCTATAT | 90840 |
| ACCCGTAGTC | TCGGTATGCT | GACCCAGACT | TGGGTAATAG | GACCCAGTGG | GTAACCGAGG | 90900 |
| AACCCCACCT | TTGTGCAGGA | TCAGTGAAGA | TGTAATCTGG | ATATTCATAA | GCTCTTCTCT | 90960 |
| ACCTCTTGGC | ATCCCACAGT | CCTGTGTTAA | TGTAAGTGTG | GTCTTCCCCA | GAAAGGGGAG | 91020 |
| GCCTCCCTAA | CATTGTTAAA | GCCTAGCATA | TGCTGCTTAG | AGGAAATTCT | ATATCCCTAA | 91080 |

-continued

| | | | | | | |
|---|---|---|---|---|---|---|
| GCACTTAGAT | TGCTGAATAA | GAAAGAATGA | TAATAAAATA | AACAATTAAA | TAAAAGTTTT | 91140 |
| AAAAAATGAA | TAAAATAAAC | CTGTGGAAAC | TATAAGGAAG | GCCAGAAGAA | ATATAAAATT | 91200 |
| GGAGATTAAT | TGGGGTGCAG | GAAAGTTATG | GAAAGAATAT | AAGTCCTGCT | AGATAAATCA | 91260 |
| TTAGCTATTT | TAATAAAGAA | TACAGAAGAA | AATAGGAACA | AAGAATATA | TACTGGAATA | 91320 |
| ATTTTGAGAG | TAATTTGAAG | AATTAGATGC | AAATAAATTT | GAAACCTTT | AAAAAGAAAC | 91380 |
| CAATGGCCTA | ACTGACCCAA | GAAGGAAAGA | AAATCTAAAC | AGACTGATAA | ATACAAAATG | 91440 |
| AAATTCAGAC | ACTTACAGAG | CAGCCAGGCA | TGGTGGCTCA | CACCTGTAAT | CCTGTCACTT | 91500 |
| TGGGAGGCTG | AGATGGGAGG | ATCACTTGAG | GCTAGGAGTT | TGAGACTAGC | CTGGGCAAGC | 91560 |
| TCCCATCTCT | AAAAGAAAAG | AAATTAGCTG | GGCATGGTGG | CATGTGCCTT | AGTTTCAGTA | 91620 |
| CTCAGGAGGC | TGAGACGAGG | ATTGCTTGAG | CCTAGGAGGG | CAAGGCTGCA | GTGAGCCATG | 91680 |
| GTCATGCCAC | TGAATTCCAG | CCTAAGTGAC | AGAGCAAGAC | CTTGTCTCAA | AAAAAAAAA | 91740 |
| AAAAAAGTT | ACAGAGCTCC | AACTAAATAA | TGTGGGGAAC | AAAAGAAAAA | AGAAGATGAT | 91800 |
| TTTATGGCTG | ATTTTTTTTT | TAAGGAAAAG | CAATTCATGT | ACCCTTGAAG | ATTAGATTAA | 91860 |
| GTTCTATAAA | ATAGCCCAAA | ATGACAGTGG | CTGAAACAAG | TTTATTTATC | TCCCATTTAA | 91920 |
| AGCAAGTCTA | GATGTGGAAG | TCTGGGAAGC | CCAGAAAATC | CAGGTCTTGT | TTGTGTATGG | 91980 |
| AAACTCCAGA | AAATCACAGA | TTCCTTCCAG | CCACCCCTCA | ATTACCCTG | GGATCCAAGA | 92040 |
| GAGCCACTAA | AGTTCCAGCC | ATCATACTCA | CAACCCAAGT | TGTAGGATGG | AAAAAAGGAC | 92100 |
| ACAAAGTAG | GGTGAAGAGC | ATGTGTGCAA | CAGCTCTCTT | TTACTCTAGT | GTCCTAAAAC | 92160 |
| CTATCATAAA | ACCTTTGGCT | TGCCTTGCAT | TAGCCAGAAT | TTAGTACATG | GCCACACTTA | 92220 |
| AGAAGTCAGA | AAGATTAGCT | TTTTTTCCAG | GGTAGTTGGC | TGAAAATCAG | GAGTTCTCAT | 92280 |
| ATTAAAAAAC | AGAGAAGGGA | CATCGAATAG | ATGACCAACA | ATCTCCTTCA | CACTCATACT | 92340 |
| ATTTAAACTG | TCCTAGTCAA | TGACCAAAAA | AGAAAAGCCT | ACAAACTCAT | TGATATAAAA | 92400 |
| GCTTAACAAA | GGTACTCCCC | GCCCCCCGCC | CGCCACACAC | CATCCCCAAA | AGGAAATTTC | 92460 |
| TAATCCAATT | AACAGTCTTA | GGTTGGGCTG | CTGAAACAAA | ATACCACAGC | CTGAGTGACT | 92520 |
| TAAACAACGA | CAATTTATCT | CTCACTGTTC | TGAGGTCTGA | GTTGATTCTT | TGTGAAGGCC | 92580 |
| CTTTCCTAGC | TTGCAGATGG | CTACCTTCCT | GCTATGTCTT | CACATGGCAA | AGAGAGAGCT | 92640 |
| AGCTTTCTGG | TCTTTTCTTA | TAAGGGACCA | GTCCCATCAT | GCCCATCATG | AAGACTCGAT | 92700 |
| CTGCTAGGAT | CTCAACTAAA | CCTAACTATC | ACCCAAAGAG | CCCACCTCCA | AAGACCATCA | 92760 |
| CATTGAATGT | GAGAGTTTCT | ACATATGCAT | TGTGGGAAAC | ACAAACATTT | ACTTCAACTG | 92820 |
| TAACTATTGA | AGCAAAAATG | TCCCCCCACC | ATAGACATCC | AGCACCACAG | TAGTACATTT | 92880 |
| ATTACAATTG | AACTTACATT | GACACGTCAT | TATCAACGAA | AGTCTGTAAT | TTACATTAGG | 92940 |
| GTTTATTCTT | GGTGTTGTGC | TTTCTATGGG | TTTTGACAAA | TGTATAATGT | CATGTATTCA | 93000 |
| CCATTATAGT | ATCACAGAAG | TTTCACTGCC | CTAAAAATCC | TGTGTTCTGC | CTTTTCAACA | 93060 |
| CTTCCTGTCA | CCCAATTTCT | ATCAACTAAT | CTTTTGACTG | TGTCCATAGT | TACTGTCTTT | 93120 |
| TCTAGAGTGT | CATACAGTTG | TGAAGCAGGA | AGCAGGAGTG | AACTCCGGAG | GCAGGGACTT | 93180 |
| TACTCCGGAC | CAGATTGAAG | ACTAGCCGAA | ACAGGGACGA | GGTTAAAGCA | CCTCTCCATA | 93240 |
| AGACACGCCC | ACCAGCGCCA | TGTCAGTTTT | TCGTTGCCAT | GGCAACAACA | GGACATTATC | 93300 |
| GACTTCTTTC | CTCTGTACCT | ACTCCGAAGT | TACCACTCTT | TTTCTAGAAA | TTTCTGCATA | 93360 |
| ATCCCCCTTA | ACATGCACTT | AACTAAAAGC | AGGTATATTA | CTGCAGAACT | GCCCCTGAGC | 93420 |
| TGCTACTCTG | GGCACATTAC | TTATGGGTTA | GCCCTGCTCA | GCAAGGAGCA | GTACCTGTTC | 93480 |

```
TGCTGTTGTA CACTGCTGCT TCAGTAAAAG TTGCTAACAC CACCACTTCA CCCTTGAATT   93540
CTTCCCGGGC TAAGCCCTAA TTTTTGGCTT GCTTGCCCTG CATCAGTTGG AGTCATATAG   93600
TATGCAGTCT TTTCAGGTTG GCTTTTTAGT AACATACATT TAAGTTTCCT TCATGTGTTT   93660
TCATGGCTTG ATCGTTTCTT TTCTTTTTCT TTTTCTTTTT TCTTTTCTTT CTTTTTTTTT   93720
TTTTTTTTGA GACAGAGGAG TCTTGCTCTG TTGCCCAGGC TGAAGTGCAG TGGCACTGGC   93780
TCACTGCAAC CTCCATCTCC CAGGTTCAAA CGATTCTCAT ATCTCAGCCT CCCGAGTAGC   93840
TGGGATTACA GGCTCACGCC ACTATGCCCG GCTAATTGGG GTTTTCCCAT GTTGACCAGG   93900
CTGGTCTCAA ACTCCTGGCC TCAAGCAATC CACCCACTTC GGCCTCCCAA AGTGAATGCA   93960
TTTCTTTTTA ACTCTAAATA ACATTCCATT ATTCAGAAGT ACCACAGTTA TCCACTTACC   94020
TACTGAAAGA CATCTTGTTT CCAAGTTTTG GATAAATTAT GAATAAAGCT GCTATAAACA   94080
TCTATGTGCA GGTTTTTGTG TGGAGATAAG TTTTCAATTC CTTTGGATAA ATACTAAGGA   94140
GTGTGATTGG TGAATCTTAT GGTAAAAGTA TGGTTACTTT TGTAAGAAAC CACCAAACTG   94200
TCTTCCAAAG TGATTGCACA TTTTGCATTC TCACCAGTAA TGAACAAGTT ACTATTGCTA   94260
CATATCTTTG CAACCTTTGG TGCTGACAGT GTTCTAAATT TTGGTCATTC TACTAGGTAT   94320
GCAGTGGTAT CTACTTGTTT TAATTTGCAG TTCCCTAATG ACATGATGTC AAGCATCTTT   94380
TCATATGCAT ACTTGCATCT GTGTATCTTC TTTGGTGAAC AGATGTTCAG GTCATTGGCC   94440
TGCTTTAAAT CAGGTTATTT TCTTACTGTT GAGTTTTAAG TATTCTTTGT ATATTCTAAA   94500
AATATTGTTC TTCATCAGAT CTGTCTTTTG CAAACATTAC CTGCCAATGT GTGGCTTTTC   94560
TTCAACACTT CTTTGTAAAT TTGCAAGTCC TTTGAGAAAA GAAATGCACC CAAAGTATTA   94620
ATTTGGCAAT CTCATATCAC GAGAGTACTC TAAAGCTAAA TAAATTACAG TTTTTCAAAT   94680
TTTGAATTAA TTGATCTTTG CTATTGTTAG CAAGGTCTTG TATTCTTTTT TTTTTTTTTT   94740
TTTTTTTTTA ATAGAGACGG GTCTTGCTAC AGTGCCCAGG CTGGTCTCGA ACTCCAGGCC   94800
TAAAATGATC CTCCTGCCTT GGCCTTCCAA AGTACTGGGA TTACAGGCAT AAGTCACCAC   94860
GCTCAGCCAT CTGGTATTCT TTAGCAACTG TTTGGTAACT TAATCTTTCA CTTTTTGAAA   94920
ACAAAAAATA GTTTTTTTCT CATAGTTTTC TAACAAAATC TTCATAACTG AAATAATTTC   94980
TCTTTATCAC CTCTTCTTAT AAATATGGTT TTCTTTTTTT AAATAAAAAT TTAAGACATT   95040
TTATAACTGG CCAAATTTAC TAGCTTAGAT ACTATTAGAT AGTCAATATT TTTTGTTGGA   95100
TATTTGATTT TTATTTCAGG CAACTAATAT CTATTCATTT TTGCACTGTT GGAAGAAAAT   95160
TACTGATCAA ATTCACTATG TATTTGCAGA AAATGGCTTT CAATATTGTC TACTTTATCA   95220
TCCTTTTTTT TTTTTTCTTT CTTCCTTTTT AGATACAGGG TCTCACTATG TTGCCCAGGC   95280
TGGTCTCCAA CTTCTGGGCT CAAACAATCC TCCCTCCTTG GCCTTCCAAA GGGTTGGATA   95340
TGTTTTATCT ACAGTTTTGT TGTTTTGTTC TGCTACAGGA TATTTGCAAT TGCCATTTAT   95400
CATGAAATTC ATGACATACC TTCTTCCACT CTCCTTTTTA TCTTTATTGT TCTGGTTATA   95460
GGACTAGCTT TGCATCTCTA CTCAATTCTG TATCAGTAGT ATGCTTTCAT TTTAAATTTT   95520
AAGTTTGTCC ATATGTATAT TGACACAGGG TCTTGCTCTG TTGCCCAGAC TGGAGTGCAG   95580
TGGCAAGATC AGGGCTCACT GCAGCCTTGA CTGCCTAGGC TCAAGTCATC CTCCCACCTC   95640
AGCCTCCAGA ATGGCTGGGA CTACAGGCAC GCACCACCAC ACATGGCTCA TTTTTTTGTA   95700
TTGAGACAGG GTTTCTCCAT GTTGCCCAGG CTGGTCTTGA ACTACTGGGC TCAAGCAATC   95760
CTCCCACCTT AGCCTCCCAA AGTGTTGGGA TTACAGGCTT GAGCCACCAT GCCTCGCTTC   95820
TACACTTATT TTTAATTCTA AAATAATTTA TAATAATAAA TATTAACAAT TAGATTTAAT   95880
```

| | | | | | | |
|---|---|---|---|---|---|---|
| TACTGATAAA | TATTAAATGT | TAAATAGGTT | TTATTAAATA | ATTAAATAAA | AATGAAAATA | 95940 |
| ATCAGTATTT | CAATTTAATT | ACTAATTATA | ATTCACAGTT | ATCCTTGTAA | CTCCTAATGT | 96000 |
| CTATATAAAA | GATTTTTATA | TTTTTTAATT | CTTAAAATTT | TATTATTTAT | TTCACACCAG | 96060 |
| GCCATCACTG | TGATACATTT | TTTAAAACAC | ATTAAATTAT | CACCAGAAAA | GTGCTGTGAT | 96120 |
| GGAAAATATA | AATTGAAATA | CCTTTTCTGG | TTAGGAGAGT | AATTCTGTTT | TTCTGATAGA | 96180 |
| GAATAGAAGA | GTCCTTCAGG | CCCCTCCAAA | CTGTCATATT | CCGGGCATCG | GGTGTCCCCA | 96240 |
| TCCTCACTTC | AGTCCACAGG | CAGGGTCCTC | AGTCTTCAGC | GCTCCTTCTC | TTTCCCCTTT | 96300 |
| GTCTTGTGTC | TCCTTGGGTC | TCTTTTCTCC | AAGACCTAAA | CTCCCTGAGG | ACAGGACTAT | 96360 |
| TTTTTACATC | TTGATGTCAC | TCCTGAGCAC | TTGCTTTAAT | GTGTTGGACA | CTGGGTCCAT | 96420 |
| TAAAGATTGT | ATGTGAAATT | ATAAAGAAA | CGTTTTCACC | TTTCTGTGGT | ACAGCTATAA | 96480 |
| TTTCTGGTTT | CATTTACCAA | CTGGGTGAAA | GTGGACCAGT | GACACCATTT | GTCTGGGCCT | 96540 |
| TCCTTTCCTG | AAATATAATA | TTGGGGCAAT | AGTCCCTGGT | TCTTGTAAGG | TGTTCAGGCA | 96600 |
| CAAAACGCTA | GGCATGTAAC | ATACTAAATG | AGGTTTTCCC | AGTTAATTTA | TATGATTGCA | 96660 |
| AAGGACGTTC | ATATACACGG | TCTGCTAAAG | AATTCTGGGG | CCAATTAATC | TCTGTGGCAT | 96720 |
| GATGGGTAAG | TCGATCCCTT | CTCTGGGCGT | CTATTACTTC | AGAAAGGCA | TGAACTCAAT | 96780 |
| TTTAGGGACC | ACACAAAAAA | ATTTATTCAC | TATCGTGTAG | GACTTGGTCA | TTAGAGAGCT | 96840 |
| TTTGTTTCTT | TTTTTTAAAA | TTTTTTTTAA | TTTTTATTTT | CGTGTATGTG | AATTTAATGG | 96900 |
| AGAGCTTTTA | AATAACCAGA | TATTTAAATA | ACCAGATAAT | ACAGATGCCC | GGCCTGCTCC | 96960 |
| AGACAAATTA | GAAAAGTATG | TAGGTGAGGA | GGGACCAGCC | AGAAGGCGGT | TTCAGCTCTG | 97020 |
| GAGTGACACT | GAACGTACTT | CTCTTCCAGG | GATGTCACGA | GGTGTCAATT | TCTCTGGCCT | 97080 |
| TACCCAGGTC | CATGCCCGCC | CCCAGGGGCC | CCAAGAATGA | CTTCAGCACC | CCACCCCCAC | 97140 |
| CTCCCTCTCC | AGATGTGGGT | CCTGGGAGCG | TTCAAGGCCC | GTCAGTCACT | CGAGCCACCC | 97200 |
| CTTGGCGGCT | GGACCAAATC | TTGGGCTGCC | GCCTGGATCT | GCAGCTGGAA | AGCGCCGTGA | 97260 |
| CCACCGGTGT | CCCCAGCTGG | AGCAGGGCGG | GCTGCACGAC | TCGCGAGGAC | GCCCTGAACC | 97320 |
| GCGGCTTCCT | CTTTCATAGC | CGCAGGACTC | GTGGTCAGAA | GGCCGACTCC | AAGCCTCAGC | 97380 |
| GGATCCACGA | AATGGCCTCT | TTGAGGCTGT | GGTGAAATTT | AAGATACCCT | TTCCCTGCCA | 97440 |
| TTGTTACTGA | CGTACTTCAG | CAAACAGGTT | AAAGTTCTGA | AAGGACGTGG | TCACGACTTT | 97500 |
| ATATTTCTTA | CAGATTTGTG | TCTCATGTTT | TGTGCGTAAA | AACCATTCGT | CCTCATTTGA | 97560 |
| GATTCTCATA | TCCGTAATTC | AGTTATACAT | AAAACTGAAT | TCAGTTATAT | CATAAAATGT | 97620 |
| TCCCATGCGG | GGAATGATTC | GTTGGGGTCT | CAGCCTGAGG | CCAGACGCAG | CAGAGAGATC | 97680 |
| GGGAGTTGGG | GGATGGCGGG | CGGGGAGCGG | AGAGGAGGCC | GCCCGCCGCC | AGACTCAGGG | 97740 |
| TCCAGCAGAG | CAGCAAATGC | TCCCCGGCTC | CCAGCCAGGG | CGCAGCTGCT | GGCCTGGGGC | 97800 |
| CGCCCCTCAC | GCCGCAGGAG | CCCCGCCCGC | AGCGCCGGCC | CTGCCCCTGG | CCTGTGAGGG | 97860 |
| CGCCAGCGCC | CCCTACAGCT | TGCAGTCGCC | CTGCGCGCCT | CCCCGCGAGG | CTTGTTTTCT | 97920 |
| AGCGCCTCTG | GTGGGCCGCC | TCCCGCAGGC | CTGGTGTGAG | CCTGGGGTCC | GTTCTCACAG | 97980 |
| CTGGATCTGG | GGTCTGAATG | CCGCGCCCTC | TGGAGAGCCA | CAGATGGGTC | TCCGCTGATG | 98040 |
| CTTCTCTCAA | TTTCCTCTAA | GAGCGAGAGC | TCCGGGAAAG | GAGCCGATCC | TGGTGGAAGA | 98100 |
| CTACAGGTCT | GAGTCCACTG | GACGAAAAAC | GAGGTGCGTT | AAGAGACCGC | GGGAGTGGGG | 98160 |
| AAATGGGGAA | GTGAGGGTGG | GGACTGGGCA | ATGGGGGCGG | GACGAGAGGT | CTGGGGCTGG | 98220 |
| CGGGGACAGG | GCTTAAGAGA | GAGCCACCCC | TCCTAGCCTT | GAAGCTGTAC | CGAGCTTCCC | 98280 |

| | | | | | | |
|---|---|---|---|---|---|---|
| TGTGATATTT | TAAAATGCAA | AAGTACAAAA | ATTGAAGTAA | TGGAACTATG | CGTACGCACC | 98340 |
| TCCTAGATTT | TTAAAGGTTA | ACGTGTGACT | GTGTTTACTT | CAGATGTTCC | TGAAATAAAT | 98400 |
| GAAAATGACC | AGTTAAAATG | AAGGAAGAAC | GCGCTTGCGT | CCCTCCTAGA | GGTCAAACAC | 98460 |
| TCTTCTGAGG | ATAGGTTGTA | TGCTCTCAGC | GCCTCTTTTT | ATTAAAAGTA | TTAAGAAGTA | 98520 |
| CTTTTCCAAA | TATTAGATGT | AGTGTGTCAT | ATCATTTAAA | CGATTTTTTT | TGTTTAAAAT | 98580 |
| AGTCTTTTAA | AAATAATCTT | TTTATTTTTA | GATTTTTTTG | AGACAGAGTC | TCGCTGTGTT | 98640 |
| GCTCAGGCTG | GAGTGCAGTG | GCGCCATCTC | CCCTCACTGC | AACCTCTGCC | TCCCAGGTTC | 98700 |
| AAGTGATTCT | CCTGCCTCAG | ACTCCCAAGT | AGCTGGGATT | AAAAGCGTGA | GCCACCACAC | 98760 |
| CCTACCAATT | TTTGTATTTT | AGTAGAGATG | GGGTTTCACT | ATGTTGTCCA | GGCTGGTCTC | 98820 |
| GAAATCATGA | CCTCCACTAA | TCCACCTACC | TCGGCCTCCC | AGAGTGCTGA | GATTACAGGC | 98880 |
| ATAAGCCACC | GTGCCTGGCC | ACTTTAATCA | TTTTTGTTTT | TGCATCTAGT | CTAAGAAATT | 98940 |
| CTGCACTAAA | ATTCTGCACT | ATTTCTTCT | AAAATTTTAA | AACATTTTCT | ATCTGTGTCT | 99000 |
| TTGTTAGATG | TAGAAACTTT | TGTGTATGAT | ATGGGGTATA | GCTATAATTT | TATTTTATT | 99060 |
| CCATATGAAA | GCCAGTTTCT | CAGCCCAGGT | AATTGAATAG | ACCATCCTTT | CTCCACCAAC | 99120 |
| TCTTAAGGCT | ACTTCTGCTC | TATTGTGTTC | ATAGTAGTTT | CTAGGCTTTC | TGTTTTGTTG | 99180 |
| TACTGATTTC | TTCACCTATT | TTTGCATCAA | GGCTCTCCTC | TTGGGGAAAT | AAAACAATCC | 99240 |
| TGCCAACCAA | AGACCCCTCT | GGATCCTCAA | ACACGCCATC | AGCATGGAAG | GCCGCTATGG | 99300 |
| CATAGCGAGA | GATAAATAGG | ATTCAGGCAG | TGCTGTCCTT | ACATCGCAAT | CATTCAGGTA | 99360 |
| GTTAGCAGGA | GCATCAATCA | GTACAGATAT | CCAGAGCTGA | TGGTCTTATT | TGTATGAATG | 99420 |
| CCCAGTGCAT | ATGGGATTGG | AGGGGAGGGC | TTGGAGTGGG | ATGAGGGGCT | AGTGGGATCC | 99480 |
| AGAAAGGGGC | TAGTCTTCAG | GTCTTCCCTG | GAGAGTATGT | AATCTCTTAT | AACTAAGTGT | 99540 |
| TGATTTTGT | TTTGTTGTA | CCTTCTTTAG | ATATTGAAGT | ATTCGCTAAG | GCTTAACATG | 99600 |
| TAATATATTT | AAATCTTCAT | ATGAATACGT | TTATCTGATA | GATTTTGGTG | AGACATAAAC | 99660 |
| TATGAAACAA | ACAGAAAGAT | GGAACATGAG | AAAGGGTCAA | GGGTGGCCTT | GGTTAGGGAT | 99720 |
| GGCAGCTTTT | ACAACTATGA | GCTAAGATAA | AATTTAGAAG | GTTTTCTTTT | TATTTAATT | 99780 |
| AATCATACCA | CTATTTTCT | CCTTTAATTT | CCATATATAA | TGAGTTGATT | GTAGTATTTT | 99840 |
| TATTGTGCTT | AACTATTTTA | AGATAATAGT | TGTCTCTCCT | CATTTTAGCA | AATAATATAT | 99900 |
| TTAATGAAAA | ATCAACTTTA | TTGAGGAATA | ATTTATACAC | AGTAAAATAC | ACCTGTATTA | 99960 |
| ATTATACAAT | TTGATGCGTT | TTATATACCC | AAACAGTTAC | TACTGTAATC | AAGTTACAGA | 100020 |
| ACACTTCCGT | CAACCTAGAT | AGTTTCCATT | TGTAGTATCA | CCTGTGCCGC | CTCTTCCATC | 100080 |
| CTCTTGGCCC | CAGGCAGCCA | CTGATGTACT | TTCCATAATT | ACAGCTTAGT | TTTCCCATTC | 100140 |
| CTAAAATTTC | ATATGAATGG | AATTTATATC | ATATGTATTT | TTTATTTTCC | TTCACATTTT | 100200 |
| TGAGATTCAT | CCATTTTGTG | TATATATCAG | TAGTTTATTC | CCTTTTATTG | CTTTATAATA | 100260 |
| TTCCAAGATA | TAGATATATT | GCAATTTTTT | TTTTTTTGA | GATGGAGTTT | CCATCTTGTT | 100320 |
| GCCCAGGCTG | AAGTGCAATG | GCATGGTCTT | GGCTCACTGC | AACCTCCGCC | TCTTCGGTTC | 100380 |
| AAGTGATTCT | CTTGCCTCAG | CCTTCCGAGT | AGCTGGGATT | ACAGGCGCCC | GTGACCATGC | 100440 |
| CCAGCTAATT | TTTTAGTAGA | GATGGGGTTT | CACCATGTTG | GATGGGCTGG | TCTCAAACTC | 100500 |
| CTGATCTCAG | GTGATCCGTA | CATCTTGGCC | TCCCAAAGTT | CTGGGATTAC | AGGCATGAAC | 100560 |
| CACTGCGTCT | GGCCGATATA | TTACAATTTA | TTTACCCATT | CACCTGTTGA | TGGACACGTG | 100620 |
| GGTTGTTTCC | AGTTTATAGC | ATTGTGAAAC | AAAGCCAGTA | TGAACATTTG | TACATGTCAT | 100680 |

| | | | | | | |
|---|---|---|---|---|---|---|
| AGTATGGACA | TGTGTTCATT | TATCTGGGAG | AAATGACCCA | GAAATATTGC | TGGGCTGTAT | 100740 |
| AAGTGTTTAA | TTTTATGTTA | GAAACAGCCA | AACTTTTTC | AAAGTAGTTG | TAACATTGTC | 100800 |
| CTCTTACATT | CACAATATAT | GAGAGTAGTT | TCCTCCACAC | CCTTGCTCAC | CCTGGGGATT | 100860 |
| GTCAGTCCTT | TTAACATTAG | CTATTCTGTT | GAATGTGAAG | TATCTCATTG | TGGTTTTGAC | 100920 |
| TTGCATTTCC | CTAGTAACTA | ATGATGTTTA | AAATCTTTTC | ATGTGCATAC | TGGCCATTTG | 100980 |
| TATGTTTTCT | TTTGTGAAAT | GTCTGTTGAA | AACTTTTACT | CTTTGTTTTG | GCTTGTCATC | 101040 |
| TTACTAAGTT | ATAAGGTTCC | TTATATTTTC | CAGGTGCGAG | TCCTTTGTCA | GATACATGTA | 101100 |
| TTATAAATAT | TTTCTCTCAG | CCTGTGATTT | TTCTTTTTCT | TTTCTATTTA | TTTATTTATT | 101160 |
| TATTTATTTT | TTAGGAAGAG | TCTCACTTTG | TCACCCAGGC | TGGAGTGCAG | TGGCACCATC | 101220 |
| TTGGCTCACT | GCAACCTGTA | GCTCCCGGGT | TCCAGTGATT | CTCATGCCTC | AGCCTCCTGC | 101280 |
| TTTTCATTTT | ATAATGTTTT | TTGAAAAGCA | AATTTTCACT | TTTGATGAAA | TTTATCATTT | 101340 |
| TGTTATTTAT | GTTTTATAAA | CTATAAACCT | GTTGTTTTGT | TTTAAAGAAA | TCTTTGCTAA | 101400 |
| TCCTAGGGTG | TTGATGATTT | TCTCCTATTT | TTTAAAGAAG | TTTTATAATT | TTAGCTTTTA | 101460 |
| CATTTAAGTC | TATGGTCTAT | TTTGAGTTAA | TTTTTGCATA | AAGTTTGAGG | TAAGGCTCCT | 101520 |
| GCTCCTCTCC | CCCACACCGG | ATGTCTACTT | GTTCAAGAAA | CATTACTGA | AAAGACGATT | 101580 |
| TTTTTACTTA | TTAAATAGCC | TTGACACCTT | TGTCAAAACC | AGTTGTCCAT | AGATGTGTGA | 101640 |
| ATCTATTTCT | GGGTTCTCTG | TTTTGTTTCA | CTGATCTTTG | TGTCTAACCT | TATACCAATT | 101700 |
| CATTCTGAAA | TACTTTCCAG | ATTACTATAG | CATTTAATA | AAATTTGAT | TGAATAGTTT | 101760 |
| AAGCCCTCGG | ACTTTTTCC | TTTTAAGTAT | ATCAACTTGG | AGAGGATTGA | TTCATATTTG | 101820 |
| TGTTTCATTT | TTTCATTTTT | CAAAATTATG | TTTCAAATTG | ACATAATAAT | TATATGTATA | 101880 |
| TATGGGGTGC | ATAGTGATGT | TCTTTTTTA | AAAAATATTT | ATTTATGTAT | TTATTTATTT | 101940 |
| TTGAAACAGA | GCCTTGCTCT | GTTACCCAGG | CTGGAGTGCA | GTGGCGCGAT | TTCGGCTCAC | 102000 |
| TGCAACCTCC | GCCTCCTGGG | TTCAAGCAAT | TCTCTTGCCT | CAGCCTCCTG | AGTAGCTGGG | 102060 |
| ATTACAGGCA | CATGCCACCA | CGCCTGGCTG | ATTTTGTAT | TTTTAGTAGG | GATGGAGTTT | 102120 |
| CACTATGTTG | GCCAGACTGG | TCTCTAACTC | CTGACCTCAA | GTGATCTGCT | TACCTTGGCC | 102180 |
| TCCCAAAGTG | CTGGGATTAC | AGGTGTGAGC | CACTGCGCCC | AGCCCATAGT | GTTATTTTA | 102240 |
| TACATACTGT | GTATAGTGAT | CAGATCAGGG | TAATTAATTA | GAATATCCAT | TATTTCAAGC | 102300 |
| ATTTCTCATT | TCTTTGTGTT | GGAAACATTC | AATGTCCTCT | TTTCTAGCTC | TTTGAAATTA | 102360 |
| TTTATTACTG | TTAACTATTG | CCATTCTGTA | GTACAAATAG | AACACTAGAA | CTGATTGCTC | 102420 |
| TTATCTAGCT | GTAACTTATT | TTAACGAATC | TCTCTTTATC | ATCTCTTTCC | CCTACCATTC | 102480 |
| CCAGCCTCTA | GTAATCTCTG | TTGTACTTTT | TACTTCAATG | AGATAAACTT | ATTTACTTAG | 102540 |
| TTAGCTAGCT | TCTGCATATA | AGTGAGAACA | TGTGGTGTTT | AACTTTCTGT | TTCTGGCTTA | 102600 |
| TTTCACTTAA | TGTAGTATCC | TGCAATTCCA | TCCATGTTGC | TACAAATGAC | AGGATTTCAT | 102660 |
| CCTGTCATGA | ACAAACAAAA | ATTTGCCAAA | ACAAAAATTA | CCTTAGTTAT | CACATTTCTT | 102720 |
| TTATTGACAT | AATTCATAAT | CATCAGAATC | ATCTGACTTG | TACATCATTG | TATCAGTTGG | 102780 |
| TTTTATGCTC | AAGATGTTGT | ATTGGTTCAT | TATTGTCTTA | ATATCCCAAC | CAACCCAATC | 102840 |
| TAGACATAAA | TGCTGGCCCC | TGTGACATGG | CAGGAAAGGG | AGACAGGCCT | GGGCCAAGCA | 102900 |
| TAGTGATAGC | AATGCACCTG | TGTTTGAAGC | TGTTAAATAT | TTGCTACAGT | CGTATTCCTA | 102960 |
| GACTCAAAAT | TAGATTCTTG | TTAAGTCCTA | CTTGTCAGTG | TCTATGGCTG | TGTGAGTTCT | 103020 |
| GGTTAGTAGA | AGGTGGGCAA | AAGTGATGTG | TATTCTTCCA | TAACTGGTCC | ATAACCACCT | 103080 |

-continued

| | | | | | | |
|---|---|---|---|---|---|---|
| ACCACTCACA | ATACTCCATG | CCTTTTTTTC | TCTTCAGGCT | CCTTGGATTA | GAGACCATCC | 103140 |
| TGAGGACATC | CTTGGGAGCC | ATGTGCTGAA | GATGGCCAAG | CCACAGGATG | AAAGGAGCTG | 103200 |
| CATCTTTGAG | TCACCACTGG | AGAAAGGTCT | CTCTAAATGG | ATTTGCAGAG | ACGTCTTCTC | 103260 |
| GAATACTCCC | CTTCTAAGTT | CCACTTGTAA | TCCACTTCTT | CTATTCTCCC | AGCAATCAAT | 103320 |
| GTGGTTTGGG | GAAATTCCAG | AATCTCATAA | TACCTTGGTC | ATGGGTAAAT | AAGGAAAGGA | 103380 |
| CCTTTACATA | CATGTGATGC | AAAGCAGATC | AAAACAAGCA | GAGCAGCCTA | AGAGCAGCAA | 103440 |
| GACCCCAAAG | GATAAGGGAA | GTCCTGCAGA | AGAGCAGAGC | GGTGCTGCAA | AGGCAGGCAG | 103500 |
| GTAAGGTAAG | CAGACAGGGC | CATCAGGATG | GATCCTTTGG | GCATGCCAGC | ATCCACCAGG | 103560 |
| GACTGGTAGA | GCTATTTAGA | GAAACTGATA | AAAAGCTCTG | CCAACTACAG | TCACAAAAGA | 103620 |
| TGGAGCTCAG | AATGATGAGT | AGATGCCTAA | AACATCTCCA | TTTTGTTGAT | GAAGAAAGTA | 103680 |
| AAGTTTATAG | AGCTTAGATT | ATTTGCTTTT | GTACCTAGCA | CAGTACTTAG | TTTATAGTAG | 103740 |
| ATGCACAATA | AGTATTTGTT | TAATGAGTGA | ATGAGTCACT | AGCCTAAGAC | CTTTAATATA | 103800 |
| ACATGCTTAA | ACCTGCTACC | AGGGATTGGG | AACTCACCTA | TTTAGTAGTG | AGTAGAGGGG | 103860 |
| TGTGGTACTG | GTACTTAAGA | CAGATGCATT | GTGGTTGGGT | ATGGTGTGTT | TTTGTTTTTG | 103920 |
| TTTTGAGACA | GGTTCTCCCT | CTGTTGCCCA | GGCTGAGATG | CAGTGGCATT | ATCATGGCTC | 103980 |
| ACTGCAGCCT | TAACCTCCCG | GGGCTCAAGC | GATCCTCCCA | CCTCAGCCTC | TGAGTAGCTG | 104040 |
| GGACCACAGG | TACGCATCAC | CGTGCCTGGC | TAATTTTGTT | TTTTGTTTGT | TTGTTTTGTA | 104100 |
| GGGACGGGAT | TTTGCCATGT | TGCCCAGGTT | GGTCTCGAAC | TCCTGGGCTC | AAGCTACACC | 104160 |
| CGCCCGCCTC | GGCCTCCCAA | AGTTGTAGGA | TTAAGGTGTG | AGCCACTGTG | TCCAGCAGAT | 104220 |
| ATAATGTTTT | TAAAAGTTTG | AGAGTTAATA | TGCTCTCTGG | TGTGCCCTAG | GTCCCACTAC | 104280 |
| TCCTATTGCC | TTAAAACTCA | CGCAGTACAC | ATTTGTCTTC | CATGGGCTTC | AGTTGTAAGA | 104340 |
| GAACCCTTTC | TACTCTTTGC | TGTTCACAAG | TCTCCTTTTA | AACAGAGCTT | GTTCCAATG | 104400 |
| CTGTTTTGTT | TTGCCCTCTG | CCATGTTCTT | CCGGCCATCA | CCTCCTGTGG | GGAAAAGAGA | 104460 |
| GAGAGATCAC | ATTGTTACTG | TGTCTGTGTA | GAAAGAAGTA | GACATAGGAG | ACTCCATTTT | 104520 |
| GTTCTGTACT | AAGAAAAATT | CTTCTGCCTT | GAGATGCTGT | TAATCTAACC | CTAGCCCCAA | 104580 |
| CCCTGTGCTC | CCTGAGACAT | ATGCTGTGTC | AACTCAGGGT | TAAATGGATT | AAGGGCTGTG | 104640 |
| CAAGATGTGC | TTTGTTAAAG | AAATGCTTGA | AGGCAGCATG | CTCGTTAAGA | GTCATCTCCA | 104700 |
| CTCCCTAATC | TCAAGTACTC | AGGGACACAA | AACACTGAGG | AAGGCCACAG | GGACCTCTGC | 104760 |
| CTAGGAAAGC | CAGGTATTGT | CCAAGGTTTC | TCCCCATGTG | ATAGTCTGAA | ATGTGGCCTC | 104820 |
| GTGGGAAGGG | AAAGACCTGA | CCGTCCCCCA | GCCCGACACC | CGTAAAGGGT | CTGTGCTGAG | 104880 |
| GAGGATTAGT | AAAAGAGGAA | GGAACGCCTC | TTTGCAGTTG | AGACAAGAGG | AAGGCATCTG | 104940 |
| TCTCCTGCTC | GTCCCTGGGC | AATGGAATGT | CTCAGTGTAA | AACCCGATTG | TATATTCCAT | 105000 |
| CTACTGAGAT | AGGGGAAAAC | TGCCTTAGGG | CTGGAGGTGG | GACATGCTGG | CAGCAATACT | 105060 |
| GCTCTTCAAG | TCATTGAGAT | GTTTATGTGT | ATGCATATCT | AAAGCACAGC | ACTTAATTCT | 105120 |
| TTACCTTGTT | TATGATGCAG | AGACCTTTGT | TCACGTGTTT | ACCTGCTGAC | CTTCTCTCCA | 105180 |
| CTATTATCCT | TTGACCCTGC | CACATCCCCC | TCTCCGAGAA | ACACCCAATA | ATGATCAATA | 105240 |
| AATACTAAGG | GAACTCAGAG | GCCGGTGGGA | TCCTCCGTAT | GCTGAACACC | GGTCCCCTGG | 105300 |
| ACCCCTTTTT | TTCTTTCTCT | ATACTTTGTC | TCTGTGTCTC | TTTCTTTTCC | AAGTCTCTCA | 105360 |
| TTCCACCTAA | CGAGAAACAA | CCACAGGTGT | GGAGGGGCAG | CCCAACCCTT | CAACCTACCT | 105420 |
| ATCTTATCTC | TTCCATTATC | TATCCACATA | TGTCCTCTGT | ATTTTTTTGA | GTAACATTTA | 105480 |

-continued

| | | | | | | |
|---|---|---|---|---|---|---|
| TAAGCATAAG | TCCTTAGGTA | GCTATGCCAC | TTACATAATG | AACTAGAAAA | GGTAACCAAA | 105540 |
| CAGAATAGGG | TTGTACTCAG | ATATACCTTC | TACAAGTTTG | TGTTACACAT | ATTTACACAT | 105600 |
| ATTTAAAAAT | ATATACATAT | TATTATTGTG | CTGTGTGGTT | ATTAGGCAAA | CTCAATAAGC | 105660 |
| AGTTCTTATA | AAGTATACTC | AATGTAACTT | TTATAAACTT | ACCATATTTT | ATAGTTATTC | 105720 |
| TGTTTTTATT | AGCTGCTATA | AACTACCTGG | GTGTCTTGCA | TGAGTCATTT | TATTGTAATG | 105780 |
| TTTTTGTATC | TGTTGAATGA | GGAGTTAGAA | GGCATCATCT | TTAAGGAGCT | TTACAGGTAC | 105840 |
| ATGTCCAGGG | CTCAATAATT | TTATTATTAT | TTCCTGGACA | GATAAAACCT | AAGCAGGTGA | 105900 |
| AGGGGAAAGA | ATAAAAGTGC | AGGGTGGAAG | TTGCTTGAAT | GCTAACTGGG | TCAACGATCT | 105960 |
| CCCAGAAAAC | CCCTGTAAAA | GAAACCTAAG | AACCTACATC | ACCAGGAGAC | CATTGGGACC | 106020 |
| AGTTCCTCTG | GAATCCCTGA | GGCCAGATAA | TCAGCTGAAG | CTTTACATTC | TGTCCCTTTC | 106080 |
| TGGTCATGAC | TTTCTCCACA | GTCTGCTTGG | TGCCTCCTCC | TCTGTGACTC | TAAATTCTTA | 106140 |
| GGATCAACCC | CTCTTGCATA | TGCACATCCG | CAGTGCCTGT | GGGATACGGT | GTGGTGTGGG | 106200 |
| GAGGAAACTC | TCTTCTGCCT | TAATATTTTC | CTGTGTGCCC | CAGGCCTTGA | CGGAATCCTG | 106260 |
| TCTCTCCATA | ATGTTGCTTT | TCGAGGAGAC | TGATTGATTG | AGATGGCGTC | TCACTTTGTC | 106320 |
| GCCCAGGCTG | GAATGCAGTG | GCGTGATCTC | GGCTCACCAA | CCTCCACCTC | CAAGGCTCGA | 106380 |
| GTGATTCTCC | CACTTAAGTC | TCTTGAGTAG | CTGGGACTAC | AGGTGCATGC | CACCACGCCT | 106440 |
| GACAAATTTT | TTTATTTTTT | GTAGAGATGA | GGTTTCGCCA | TGTTGACCAG | GCTGGTCTCA | 106500 |
| AACTCCTGGA | CTCAAGTGAT | CTGCCCACCT | CGGCCTCCCA | AAGTACTGGG | ATTACAGGCA | 106560 |
| TGAGCCAATG | TGCCCGTCCT | GAGGAGTTTT | CTTCTGGAAT | TCCTGCTGGG | TTTTGTAGT | 106620 |
| CAGTCCTCTC | CCCATTTCCC | ACATTGGCTC | TTGCAGACCT | TCCTTTTCCC | CATTTCTATT | 106680 |
| TGCTACCATG | TCAGACATGA | CTTTTGCCAT | AGGATCTCTA | TTCTACTATA | GAGGAAACCA | 106740 |
| AAGCCATCAG | TAGAAATTTC | ACTAACATGG | AATCAGATTT | ATAGAAGAAA | GGGGGAGGAA | 106800 |
| AGTTTTGCCT | TAACACCTGG | AAGGGTTTCG | TTTCTTTTAG | TAGCTGGGAG | ACAGAAACAT | 106860 |
| AAGAAAGTAG | CTTAGTAAGC | TTTCTGCTGT | TCAACTGATG | ATGTGTGAGC | TGTCAGTAGT | 106920 |
| TCAAACTAGT | CATTATCTTT | ATGAATTAAT | TATGTAATAA | CTTAAACAAT | GTCATAAACC | 106980 |
| TTCAAATCAG | TTTAAGTCTA | AATGTGTCAT | ATTTAATAAC | AAGAGCAAGA | AACATACGTT | 107040 |
| ATGATGAAGA | GCTCTTATAT | TTTCTTTGGA | TAAAAGTCAG | TAGGCGGGGC | GCGGTGGCTC | 107100 |
| ATGCCTGTGA | TCCTAGCACT | TTGGGAGGCT | GAGGTGGGCA | GATCATGAGG | TCAGGAGATC | 107160 |
| GAGACCATCC | CGGCTAACAC | GGTGAAACCC | TGTCTCTACT | AAAAATACAA | AAAATTAGCT | 107220 |
| GGGCGTGGTG | GCGGGCGCCT | GTGGTCCAG | CTACTCGGGA | GGTTGAGGCA | GGAGAATGGC | 107280 |
| GTGAATCCGG | GAGGCGGAGG | TTGCAGTGAG | CCGAGATTGT | GCCACTGCAT | TCCAGCCTGG | 107340 |
| GCGACAGAGC | AAGACTCCGT | CTCAGAAAAA | GAAAAAAAA | AAAGTCAGT | AAAATTTAAG | 107400 |
| AGAAAAATGC | ATTTGCTTTG | GGACTTTTAA | TATTTAGTCT | ACAAATCTAG | CCACCATAGA | 107460 |
| AATCTGCTGA | TTAAATACGG | GTTCTGTTAA | AATGGAAACA | TGCATTTTGG | GGGAAAAAG | 107520 |
| AGGGAGTGTT | TTAGTGATTT | TGTTTTTTAC | ACTTGTTTAT | AATAAATTT | TAAGCAATCT | 107580 |
| TGAGGGGAAC | ATTTTATTTC | TACTTGTAAC | TGCATAAAGT | TATGAGATAA | AGTTACAAGC | 107640 |
| TATATCACAT | ACAGTTTGTA | GCTTTATAAA | TTATGAAATT | CTAACAGAAT | AAATATGCTA | 107700 |
| ATATGATGAA | AATGTCATAA | ATTACATTAG | AATATATTTT | AATAAACCAA | TTCAGAAGGA | 107760 |
| GCCAATACCC | AATTTCAAAA | TCATATTAAT | TGTAAAATTA | ATTAGGGCAG | CCAAAATATT | 107820 |
| CTGGAATTCT | TTCTAATAAA | ACAAATGAGT | GTAAATACAG | TCGTACTGAC | AAATCTGAAG | 107880 |

| | | | | | | |
|---|---|---|---|---|---|---|
| AATTATGCAG | CATAAAAAGT | GATTATCCCA | GCACTTTGGG | AGGCCAAGGT | GGGCAGATCA | 107940 |
| TGAGGTCAGG | AGTTGGAGAC | CAGCCTGACC | AACATGGTGA | AACCCCGTCT | TTACTAAAAA | 108000 |
| TACAAAAATT | AGCCGGGCTT | GGTGGTGCAC | ACCTGTAATC | CCAGCTGCTC | AGGAGGCTAA | 108060 |
| GGCAGGAGAA | CTGCTTGAAT | CCAGGAGGTG | GAAGTTGCAG | TAAGCCAAGA | TCACGCCACT | 108120 |
| GCACTCCAGC | CTGGGCGACA | GAGTGTGACT | CTGACTCAAA | AAAAAAATAA | ATAAATAAAA | 108180 |
| ATAAAGTTT | TAAAAAGTG | ATTATTATGA | ACACAGAGTA | ATCTAGTAAA | AATGGTTAAG | 108240 |
| TGAAAACAGC | AAAATACAAA | ATTGAATATG | TACTATAACA | ATATATGCAA | AATATACTCA | 108300 |
| GATTTATAAA | AATTAGAATG | TAGAAAAGTA | AATATAGCTC | TTCATAATTT | TGTTCTGAAG | 108360 |
| TTTAAAAATA | TATATATTTT | TGAATGGATA | ACTTTCTTTT | TCTAAATGCT | TACAGTAGAG | 108420 |
| CCCACGATGG | TTGTTAAAAG | CCCCCAGGTT | CAGCCTTCTT | TAATTGTGTG | GTCAGCCTGC | 108480 |
| CATCAACCCG | AGGCCTCCCT | CTGCTGGGCA | AATTTGGGAA | CACATTGAGA | AATCCTTACA | 108540 |
| CGTAATTCCT | TCTCTTCATG | TTCCTGGTGA | GCATTTTCC | CATTGGGTTT | CCATACTCTG | 108600 |
| CCCTCTTGAA | GTCCTGCACC | CTGACATTGC | AGTGTCATTC | CTCTTCTACT | GAAGTCTACA | 108660 |
| ACTATTAGCT | TATTGTCTCT | AGCAAGTCTC | CCTTTAGCTA | CAAATATCAT | TCAGAGTTTT | 108720 |
| ACCTTTCAGA | AACTTTCTCC | ATGAGCATTC | TGGAGTAGAC | TCTAGGTGCA | CTAGGTGCAG | 108780 |
| TTAGAAAAAG | TTCTGATTTG | TTGGTGGAGC | TATAGGAGGA | GAGACAATGG | TGGGCTGGAG | 108840 |
| AAGGGTGTCT | ACATGCAGAG | AAACTGACTG | GAAACTCAGA | GAGATGATGG | GGATTAAAAT | 108900 |
| AATCCTATTG | AATCTGCACA | AAAGTGTTTT | ATTATAATTG | ATCCTGAACT | ATGTAAAGGT | 108960 |
| AAGCTCCAGT | GAGTAGTTAC | AGTCTGTCCC | TAAGATGGAC | TCTTTCTTTT | TGCTTTTATT | 109020 |
| TTTATTGTAT | TTATTTTATT | GTATTTTTT | TTTCTAAAGA | CAGGGTCTTG | CTATGTTACC | 109080 |
| CAGGGTGGTC | TCAAGTGGTC | CTCCTGGCAT | CAAATGATCC | TCCCACCTCA | GCCTCCCAAA | 109140 |
| GCGCTAGGAT | TACAGGTGTG | AGCTACCACA | CCCAAATGAT | TCTTTCTTTT | CAAATACAGA | 109200 |
| GTTCAGCAGC | AATTTTAAAG | AAGTACTGAA | CTCTACTGCC | TGGAAGATGG | AATGGCCCTC | 109260 |
| ACAATTCTTC | CAGGCAAGCT | CTGCACTCAG | TGGTATGGAC | CACAAGGCAA | GCCCATTAAG | 109320 |
| GGGTTAAATT | ACTGACAAAC | AATAATTTCT | AAATATGAAC | ATTTCAGGAG | GAACTAAGAT | 109380 |
| GGCTCCTTCT | TGGAGAATAA | GTTGGCCGGC | TTCTCTAGTT | ATCAGACTAT | CAGATGGGA | 109440 |
| GGAAAGAGCC | CCTCTGTCCC | GGTGAGACAG | GACCCGCCAG | CGCCCAAGCT | CTAAGGCTTT | 109500 |
| CTGATGAGCA | AATGGGGTTT | CCATCTTTCT | AGCTTCAGGA | CTCGTAACTA | CTCAGATTAT | 109560 |
| TTCCTTCAAT | CTGGATATTC | AAGACAAGAA | CAGTTCATGG | TGTTGCGAAG | GCCCAGATTT | 109620 |
| AAATCACATA | TGCAAAGATA | CTGACATTCA | GTGGAGGGTC | ACTTAGATTA | TAGCCAGATG | 109680 |
| ACTTTCCCTA | AATTGATAGC | TCAAATGGTA | GTTGTGGATA | TTTTTGCTCT | TAGTTACTTG | 109740 |
| CATAGTCACT | TGCCAGAGGT | AATAAAGTTT | TAGTGTGGTT | GTGGAAAATA | ATGGCCATAT | 109800 |
| ATTTAGGAAC | AAAATTTTAA | TGATGATTGA | AAACTGAATT | AGCTTTAACA | TGTGAATATG | 109860 |
| CTCAGGGGAC | ATAGGACCAC | AGATCTCTGT | TCCTTCCTAT | TGCCACTTCT | TTCCTTTCCC | 109920 |
| TGGTAGCATG | CTTCCATTAC | CCATTACTTC | AAACACTGTT | TCTGTGTCTC | CAACTCCCTT | 109980 |
| GCATCATGGT | CTTTTCATTA | TTCAGACACA | GACACAGCTC | GATTATGGGT | AAACTTTTTT | 110040 |
| CTGTGGCTAC | AGAAGAGTTG | AGCATGGCTG | AAGCATCGTT | GAGCATGACT | GAAGAAAAAC | 110100 |
| ACCTAACCTT | GAATTTTTTG | ATCAATATAA | ATTTATATCC | ACAGATTTTA | CCTGACTGAT | 110160 |
| CTTCATTGCC | CACCAGTCCT | ACAAAGTTTG | CCAGATTGGT | TCTGTTTCCA | CTTTACATAC | 110220 |
| TCAGCAAATA | CTTATTAAGC | ACACACTTTG | TGTTAGGCTT | AAGTGTAGAT | ATTGAAGAGG | 110280 |

-continued

| | | | | | |
|---|---|---|---|---|---|
|CACTGGTGAA|TGAGCAGAGG|CTCTGCCCCC|ATGGGACCTG|CATGCTATTT|GGCAGCTCTT 110340|
|TCAGACATTC|TCCTCTCTCA|AAGCTTTGAG|CCCCTCTATA|CCCCTATAAG|CACCTACTTT 110400|
|CAGCTGCTCC|CTCACTCCCC|CCTTCATGGG|GGAAATAACA|GCCATCGTGG|TAAAACCTCC 110460|
|ACTGCCTGAC|AGAGCTATAT|TTACCATCTT|TTCTTTAATT|TTTATTTTTA|ATGGACACAG 110520|
|TTGTATATAT|TTATGGGGTA|CTATGTGATA|TTTTGATACA|TGTATAGATT|GTGTAATGAT 110580|
|CAAATCAGGA|ATTAGATCAG|TTTTTTGTCT|TTTTTTTGGT|AAAAGATAAT|CTTTTATACT 110640|
|CTTTTGGTCC|TGAAAAATGG|AGGAGTGCCA|TATTAGGATT|CCAACAGAAA|AAGTTAAACC 110700|
|AAAAGAATAT|ATGAAGGGCA|TATAATGAAG|GGATATCTAC|AAAGTTGTGA|CAGGGCTAAT 110760|
|GGGAAGAACA|GGGGATATGA|GGCAGCCCAA|GATCAGCAAC|AGTAGTGATC|CAGTGTCACC 110820|
|CTGTGCTGGT|TATGAAGATT|TAGTCTCTTC|TATCTTTTCC|AATACCGCTT|TGCTAGCCAC 110880|
|CTCCCCAAAC|CCTACCAATA|GAAAGCACTG|GAGGAAGACT|AGAGGGCTGG|AAGGATGTGA 110940|
|AAAGATTTCC|CACTTTGTTT|GTTGACATCC|TCACAGAATG|GGTTCTTCAA|CCTGGCAGTG 111000|
|GCAGTTGAAT|CCAGTAACAG|CAGTTGGCTT|CAGTTTGGAG|ATCTTCCATG|CTCCTAAAAT 111060|
|CAGCCTCATC|ATGCCTCTAT|CTACAGACAT|ATCATCATCA|GTGGTCCAGC|ATACACTCCT 111120|
|CAGAGGTCCC|AGTTCTGGGG|ATCTCTTCAA|AGAATCTTTT|CCTTGTTCTC|CTAAACCTGG 111180|
|AGGTGGTAGT|TGCTTTCTGT|CATTACTATC|TCTGATACGT|TTGTCCACTT|TTCCATTTTC 111240|
|AGTCCTCTTA|TAACTAGTTA|ACAACCATTC|CCATAAAATT|CTTTGTTCAA|TTTCAGTGCA 111300|
|ATTTCTAGCT|CCCAGTTATA|CCCTGACAGA|CACACCTTTA|AATCTGAAGA|GGCAATGGGA 111360|
|GGGAACCTGT|AACCAGAGCT|AGGCCAGAGC|TGGGACTGTG|GAGGAAGAGC|TGCCCACCAA 111420|
|GCAGGGGGT|GATGCAGGGA|ATAAGTACAC|TAACCTCTCT|CTCCTTTGCC|ATCTACATTC 111480|
|CTGCTGGGCT|GATCACTGGC|CAAATCCAGC|TGTTGCAAGA|GGGCAGGGCT|GCCCAGCTAA 111540|
|TGCTATCTGT|AGAAGCTGGG|CTTCTGGGGC|ACAGAGCAAG|TCAGAGACAG|GCAGAACAGG 111600|
|GATGTGGGTT|TGGACCAAAC|ACTGAATAAA|CCAGATCAAG|GATTCTTCTA|TCAAGACAAG 111660|
|TTTATATACT|TGCAGCTTGA|TCCCATTGTT|TCCCTTAGAT|AACTGTGCAC|TTGTTTTTGT 111720|
|CTGCCCTCTT|TCCTGTGTCT|ACACTCTTCC|TGTCTTATTC|TATTTACACA|TAGCTCAGTC 111780|
|TTTTCCAATT|AAAAAAAAAA|AAAAAAGCT|TTCCCTCTCC|CAAATCTCCA|TGCAGCTGCT 111840|
|GACTTCTCTC|TTCCAAAGCC|ACACTGTGGG|AGAGTCAGTT|ACACCTCCTG|ACCTCTGACA 111900|
|GGTGCAACAC|ACTATAGTGA|GGCTTCTGCC|CTTGGTATTC|CTCTGGCTCC|ATTATTTACA 111960|
|AGGTCACTAA|TGACTTCCTA|TTTCTAAATC|CAGAGTGCCT|TTTTAGTTAT|CTTCCTTGCC 112020|
|TTCTTGGCAT|CTCTAGATAA|CAATACTTGT|CTCATTCTAA|CTTTTGTCTC|TCCTTACAGC 112080|
|TCTTTCATTC|ATAATTCATT|GTTATTCAGT|TGGAGCCTTG|ATGGTGTTAG|GGAGAAGCAG 112140|
|CATTCTGTAG|TCAAAGTGTT|AAGCCTCAGT|TTATTAGCAT|GCCTATATCT|TGGGGCTGGG 112200|
|ACCGTCACAA|GTGTTTATAA|TGATACAACT|CCTCCTCCTC|CTCCTTCTCC|TCCTCCTCTT 112260|
|CCTCAAGTGT|TTATAATGAT|ACAACTCCTC|CTCCTCCTTC|TCCTCCTCCT|CTTCCTCAAG 112320|
|TGTTTATAAT|GATACAACTC|CTCCTCCTCC|TCCTTCTCCT|CCTCTTCCTC|AAGTATTTAT 112380|
|AATGATACAA|CTCCTCTTCC|TCCTTCTCCT|CCTCCTCAGA|CCTTTGCTCC|TTTCCTGGCT 112440|
|GCACCATTTC|CAATTTATTT|TCATGAAGCT|CTGATCCCTG|TTGACTAATT|TTCTTCCCTT 112500|
|AAGTGAGACA|GAAAGCCTAG|ATGAGGCTGC|AGTGGGAAGA|ATTACCTTCT|CCCAGCTGGG 112560|
|ATAAGACTCT|GGCAAAATGT|TTTCCCCTTG|AGAGTAGGCC|TTTGTTTTGA|AGAAGGTTCT 112620|
|GGGGTGTATT|TCATAATAAT|TCTTCTCTCC|CTGCCAAAGC|CACAAGAGGA|TCCTTCTCAG 112680|

-continued

| | | | | | |
|---|---|---|---|---|---|
| ATCTTCACTG | CAGGAACCTG | GTGGGCTTTC | TGATGCCCAC | AAAAGTGTGG | GAGCTTCTCA 112740 |
| CTCTCATGGG | CATTCACAGT | TGGCCTCCAG | CTTTTTGTCA | GAGTTACCAA | TTTAAATGTT 112800 |
| CTCAAATGTG | ATACTGTCTC | AACTTCCAGG | ACATCACACA | CTCATGATTT | TCTACTATCC 112860 |
| TGACATTTGC | AGTCTTTTTA | GCAGATCTCC | CTCCCTCTCC | CTGCACCATG | GGTATTGGTC 112920 |
| ATCTCAGGAT | CTGTCCCAGG | CTTTCTACTC | TTCATGCCCT | TGAGACAAC | ACATGATCTG 112980 |
| ACCTGCCCTT | TCAGGAAGAA | ATGTTCTGTC | TACCTACTTG | CTCCAGTTAA | AAACCCTAGT 113040 |
| GTCATCTTTG | ACCCTTCTCA | TCCCTACATC | TAATCTGTTG | ATTCTACCTC | CTAATTTTCT 113100 |
| CTCAAACGCA | TCTATTTTTC | TTCAATTTCA | GTGCTACTCT | CTTGCTCTAA | TTGTACATCA 113160 |
| TCTTTTTTAG | AATTACTGTG | ACATTTTCTT | GCCTCCAGTT | CTGCCTCAGT | CCATCCACTT 113220 |
| CACAGCTAAA | TTTTGGATGT | ACACTTTTGA | ACTATTACTG | TAGCAAAAGT | AATATGTAAT 113280 |
| AACTGTAATG | CAGAAATATA | AATATGCAA | TATAAAGAA | ATACATGCAT | AAATGATCCC 113340 |
| AACACTAAGG | AAACAATATT | GATCAATAAT | TAAATAATTG | GTGGATAGTG | AATGACAACA 113400 |
| TAGAGCAAAG | TGTTCAGTAG | GTTTTAAAAG | CTGTGGGTTC | AATAAATGCT | CATGAAGCTT 113460 |
| GTTCAGGGGC | TTGCAAAATA | TGTAATTTGA | ATTTTTAAAG | AAAAGGAATT | TCAGATAAGA 113520 |
| AAAAACATAC | ATAACATGAA | ACAATACTTG | TGGTGGTTTC | AGGGAGGTCA | TGTTCTCACA 113580 |
| TTCAGGTGCC | AAGGCCACCG | TACATCCGGA | CACTGAGGCC | ACGGACTTGG | TCTGCAACCT 113640 |
| CCATGACAGC | CTTGTAGATT | TGAAACCGAA | CTCCAAGGAG | CAGTTGTGCT | GTGAGTTCCA 113700 |
| GAGTTTGGGG | ACAGAGGAAA | CACCATTCTT | TGGAAGTCTA | ACTTCCTTAA | GAGGTGTCCC 113760 |
| TTAGACATCT | AGTGTCCGGT | GTTATGGAGG | TCCTTGTGCT | CTGAGGAAGG | AGCCCCTTGT 113820 |
| TGATTGATGG | AGCAAAATTT | TTTTAAACAA | GGAACTGTAC | CCGTATCTGG | GCATGAAGCC 113880 |
| AGAGAAATCC | CTGAGGGCAG | GGCCAAGGCT | CTCAAAGATT | TCAGGGAGA | TTCCCAGCCT 113940 |
| TTTTAAGTCT | CGCCTATTCT | TTTTTTTTC | TCTAACTGGC | CATTTTGTAT | ATATGGAGGT 114000 |
| TATTGATTTT | TTTGCTTTTA | TATCCTGATA | TTTTAATAAC | TGTTCATTTT | TTAGTTATTT 114060 |
| GAATTATCTA | CATTGATTAT | TTGAATGTTC | TTTTTTTGT | TTTTTGAGA | CGAAGTCTCG 114120 |
| CTCTGTCGCC | CAGGGTGGGG | TGCAGTGACA | GGAACTTGGC | TCACTGCAAC | CTCTGCCTCC 114180 |
| TGGGTTCAAG | CGATTCTCCT | GCCTCAGTCT | CCTGATTAGC | TGGGATTACA | GGTGCCCGCC 114240 |
| ACCACACCCA | GCTAATTTTT | GTATTTTTAC | TAGAGATGAG | GTTTCACCAT | GTTGGCCAGT 114300 |
| CTGGTCTCAA | ACTCCTGACC | TCAGGTGATC | CACCCACATC | GGCCTCCCAA | AGTGCTGGTA 114360 |
| TTACAGACAT | GAGCTATTGC | ACTTGGGCTT | TGAATTTTCT | ACGTATCTGA | CTTCTACGAA 114420 |
| GAAAACTATA | ATGTATTACT | CAGATAAATT | AAACAGGAAA | ACTAAATAAT | GGAGGAGTAT 114480 |
| ATTTACAGTT | GAAGCGGTCA | ATATTTTAAA | GGTATTAATT | GTCCCCAAAC | TGATCTACAA 114540 |
| AACCATTGTA | ATCCTAATCA | GATTCCCAAT | AAGCTTTATT | ATAGAAATTG | ACAAACAGGG 114600 |
| TTCAAATTTA | ATACACAAAT | CCAAGGGCCC | AAAATAAACA | AATCTGTTGC | TTTATTAAAT 114660 |
| ATCAAAACTG | ATAAAATGAC | AATAATCAGG | GCAGTGTTGT | CCAAAAATAG | ACAAACGAAT 114720 |
| GGAACAGGCT | CAAACAAATA | TGGACATTGA | TTTACATCTA | AAGTGGCACC | ATACAACAAT 114780 |
| GGTGAAAGGA | CTCTTGTAAA | TAAATGGCAT | GGGACAATTG | TATAGCCTTT | TAAACAGAAA 114840 |
| AAGAACAAAA | AGGAAAAAAA | AAGAAACTTG | ACCCCTACT | TCACACTATA | CACAAAAAAC 114900 |
| AATTCCAGGG | GAACTAACAT | GAAAAGCAAA | ATAAAGTTAA | ACATGAAAAG | CAAAATAAAG 114960 |
| TATATGGTAA | AAAATTTATC | TTACCCAAAA | AGAGGTCTAG | CCTTTGCCCT | CAGCTACTGG 115020 |
| GAGATGAATT | TTAGACCCTT | GAAATGTTCT | CACTGATAAG | TGTGTCTTTG | TTTACCTGGA 115080 |

```
GGTTTTGACC  ACCACACAGT  CAACAATGTG  ATTTATAATA  GGAACTTTGA  GCCACACAGT  115140
ATCAGCTCTA  CCTGTGGAGG  TAGACTAAAA  GATCGGCCAT  GTGAGCAGTC  AACCATGGCA  115200
GGCCATTAAA  ACTGCACACT  GAGGCTCGGG  TGAAATACAG  TTCTCTTGTA  TACGGTTTCT  115260
ACATGGTTTT  AGTTCCTGTG  GTCTACTGCA  GTCCAAAAAT  AATAAACGGT  AAATTTCAGA  115320
AATAAACATT  CACCTAACTT  TTATACAGTA  TATTCTTAAC  AATTATTCTA  ATTTATTGTT  115380
ATTAATCTCT  TACTGTGCCT  AATTTATAAA  TTAAGCCTTA  TCATAGCTGT  GTCTGTATAG  115440
GAAAAACAG   CTATATAGAG  TTCAGTACTA  TCCATGGTTT  CAGACATCCA  CTGGAGGTCC  115500
TGGAACATAT  GTTTTGTGCA  TAAGTGGGGA  CTGCTCTGTA  CGTCATGTGT  ATTGTCACAC  115560
ATTAATGCTG  GGAAAGTAAT  ACTGTTCATA  TTACTGGGAG  AGGACAACTG  GAAGCTCATA  115620
TTTGGAACTT  GCCTGGATTG  TGCCTATATT  AGTTTCCTAG  GGCTGCTGTA  ACAAAGAGCT  115680
AGAAGCTAGG  GTGGCTTAAA  ACAACAAATA  TATTCTCTTG  TAGTTCTGGA  AGCTAGAAAT  115740
CTGACATGAA  GGTATCATTA  GATCTATGCT  TCCACTGAAG  CCTGTAGGAA  AATCCTTCCT  115800
TGACTCTTCC  TAGCTTCTCG  TACTTGCTGG  CAACCTTTGA  CATTCCTTGA  CCTGCAGCTG  115860
CATAACCTCA  GTCTCTGCCT  GTGTGTGTCT  GTCTTCACGT  GACCACCTTA  GAAGAATACT  115920
AGTTCTATTA  AAAAATATAT  ATATACTACT  TCTTCTAAGT  CACCAGCCCA  TCATACTGTA  115980
CTATAACCTC  ATCTTAACTA  ATTATATCTG  CAACTATCCT  ATTTCCAAAT  AAGGCCACAA  116040
TTCTGAGGTA  CTGGGAGTTG  GGACTTTAAA  CATATCTTCT  GGGGGCAAGG  GAGATCTGCA  116100
TACAATTCGA  TCCATAATAC  TGCCTTGTGT  GTTTCTTTTC  TCAGCTGATT  TTAATCTTTA  116160
TTCCTTGAGT  TGTTTCCCCT  TTTCAACTAT  TACAAACAAT  GAATTTGCT   GTGTATGTGT  116220
CTTGGTATAT  ATGTGCACAC  ATATCTGCTG  TTTGTATACC  TCAGAGTGAA  ATTGTTGGGT  116280
CAAATGCTAA  AATCTTTTTA  AAAGTAGTTG  TATAATTTTA  CATTGCATTG  GAATGACATA  116340
ATAAGCTATA  TATCCTATAA  TAAATTGTAA  CCATGAGGCT  AACAGCTTCA  GCAAGTTCTG  116400
TGAGTCCTTT  TAGCAAATTA  CTAACCTAAG  GTTGATTGGG  AACCACAGAC  CTCCCAACTT  116460
ATAATTGGTG  TTAGAAGTGA  GGGTAGTCTT  GAGAACTAAT  TTCACAAGAA  GGTATTATAA  116520
AATAAGATCT  TCATGACCTT  GAAATAGAAA  ATGATTTTTT  AAATAAGATA  CAAAAAAGGT  116580
TGTGCATAAA  AGGGCAGTGT  GCTTAATTTG  AGTACACTAA  ATTAATGACT  TTAATGCATC  116640
ATGAGATATC  ATTGGCTGGG  TGCAGTGGTG  GCTCACACCT  CTAGTCCCAA  CACTTTGGGA  116700
GGCCAAGGTT  GATGGATTGC  TTGAGCTCAG  GAGTTTGAGA  CCAACTTGGG  CAACAGCACC  116760
ATCTCTACAA  AAAAATACAA  AGATTAGCTG  GGCATGGTGG  CCTGCACATG  TAGTCCCACC  116820
TACTAAGGAG  GATAAGATGG  GAGGATCGCT  TGATCCTGGG  AGGTGGAGGC  TGCAGTGAGC  116880
TGTGATTGTG  CCACTGCACT  CCAGCCTCTG  ACAGAGTGAA  GACAAGTTAC  AGAGGAAATA  116940
CCTGCAACAC  ATAAAATGGA  TAAAGGGTTC  GTGAGCAAAA  TTTAAAAACT  TAAAACAGAA  117000
AAGACAGGCC  AGGTTTGGTG  GCTCACACCT  GTAATCTCAG  CATTTGGGA   GGCCGAGGCA  117060
GGTGGATCAC  CTGAGGTCAG  GAGTTTGAGA  CCAGCCTGGC  CAACATGGTG  AAACCCCGTC  117120
TCTATCAAAA  ATACAAAAAT  TAGCAGGGCG  CGGTGGTATG  CACCTGTAGT  CCCAGCTACT  117180
TGGGAGGAGG  AGAATTTCTT  GAACCCAGGA  GGTGGAGGTT  GCAGTGAGCT  GAGACAGCGC  117240
CACTGCACTC  CAACCCGGGT  GACACAGCAA  GAGTCCACCT  CAAAAAAAA   GAAAGGACAA  117300
AAAGGACAAA  AAGACAGCTA  TCTTAAACCA  ACAAGAAAAA  ACACAATCTT  TTTGGCCTAA  117360
ATTGTGTTCC  CCCAAAATTG  ATGTTGAAAC  TCTAACACCC  AATGTGCCTA  TATTTGGAGA  117420
TAGGGATTTT  GGGACTTTAT  GGAGATATTT  AAGGTTAAAT  GAGGTCATAA  GAGTAGGCCA  117480
```

| | | | | | | |
|---|---|---|---|---|---|---|
| GTAGTCTGAT | AGATCTGGTG | TCCTTATAAG | AAAAGGAAGA | GACATGAGGT | CATTTTATGG | 117540 |
| GCATATGAAG | AGGCCACATG | AGGACACAAA | AGGCGACTGC | TGTGGTTTGA | ATATGAGATG | 117600 |
| ACATCTCACA | TCTGCCATAA | CAGTAAGAAG | GCCCTTGCCA | GAGGTGGGCC | CCTCGACCAT | 117660 |
| AGGCTTTATA | GCCACCAGAA | TTGTAAGAAA | TAAATCTGTA | TTCTTTATAA | ATTATTTGGT | 117720 |
| CTCTGGTATT | CTGTTCAGCA | CCAAACAATC | TAAGACAGCA | ACTATCTTCA | GGTCAATAAG | 117780 |
| AGAGCCCTCA | CTAGAAACTG | AATCTCTTGG | CACCTCAATT | TAGGATTTCT | GGCCTGGCCT | 117840 |
| TTAGAACTGT | GAGGTAATAA | ACTCCTTTTG | TTCAAGCTAC | CTAGTCTAGT | ATTTTTGTTA | 117900 |
| TGGCAGCCCA | AGTCGACTGA | TATACAATCC | AATTAAGAAA | AAATGGGCAA | AGATGTAAA | 117960 |
| ATAAAACCAT | AATGAGATAA | TACTGCACAT | CTGCCACAAT | GGATAACATC | TTCAAAAGAT | 118020 |
| TAACAATTTT | AATTGGAAAA | AAATATTGGG | AAGTATATGG | AAGAACAGGA | ATTCCCAGCT | 118080 |
| AGATTCCATC | AACATTAGGT | TTGTGAGGTT | CATCCATGCT | GTTTATAACT | GTGGTTTTAA | 118140 |
| TTTTCATTTC | ATCGCATGTA | AACCTAATAT | CACCACTTTC | AAAAGAGTT | TAGCATTTGA | 118200 |
| CCCAACAATT | CCTCTCCTAG | GTATACAAAC | AAAATATGTA | TTCCTATATA | TACCAAGACA | 118260 |
| CATACACAGG | AATATTCACG | GTATTGTTTA | TATTAGCTGA | AAAAGGGAAG | CAAATATGCA | 118320 |
| TCAACAGTAG | ACACCTAAAT | TGTTGCACTC | ATAACATGGA | ATATTACATA | ACAATAAAAA | 118380 |
| TGAATTAAAG | TTATACACAG | CAACACAGAT | GAATCTATTC | AAACCTAATG | TTCTGGAGTG | 118440 |
| AAATATGTCA | GGTACATAGG | ATTACATTTG | TTTTATTTCC | ATTTTATATG | TTTCAAAAAC | 118500 |
| AGGCATACTA | AATTACAGCA | TTGGAAATCA | AAATAGGGGT | TATGTTTAGG | GCAGATGGAG | 118560 |
| TGATAATGTG | ACTGGAAGCA | AGCATCAGGC | GGCTCTGGGA | GGGTTGGCTG | ATTTCTGTT | 118620 |
| TTTTTACTTG | TGTGGCAATT | ATTATGGTGT | TCACTTTGTG | TTCATTTATT | GAGCTTTGCA | 118680 |
| TTTTTGTTTT | GCTGTGGTTT | TCTGTTTATA | TGTTATGCTT | CTCAGTTTAA | AGAATGTTGA | 118740 |
| AATCTTCTAA | TACGAAATTT | TTTTTCAATG | AGAAGGATTT | TAAGCATCCA | GAATCAATTT | 118800 |
| TAAAATCTCC | AATTTGCTTT | ATATGTAGGT | TTATGGACTG | CTTAACTGCT | ACTCATTTTT | 118860 |
| TCCTTCATTT | ATCAATAGTG | AAATATGAAA | TTAAATAAT | GACTATTTGT | GGCAAAATTA | 118920 |
| GGGACTATGT | AGCATATTAA | CAACTTTATA | AATAAAGAA | TAAATCAACT | CACCTGGGAG | 118980 |
| TTGTTACTGT | CATTGACCTA | ATGCTATTTC | CCATGGTACT | CCTTGTCCCC | ATTGAGAGAC | 119040 |
| ATGAGATACT | GCAGATTTAT | GGGTCACTTT | CAACATGTCT | CCTCCAGGCC | TCATTTAGA | 119100 |
| GAAGCATAAC | ATCATGAGGT | TCTATACAGG | CAAGATCTAG | GCTTGTGTCC | TTGAACCTTG | 119160 |
| CATTCCCTCT | CAAGAGCCAA | CCAATAATTG | AATGATCCTA | TAAAAAACAC | AGAAACACAG | 119220 |
| AGAATGGTAG | CAGAAAGCGG | ATGCTTACCA | AACCTATTTT | CTCTTTTCT | AAGCAAGGAA | 119280 |
| TAAGAATAAC | TTACCTTCCT | CCCTTGGAGT | TAGGAGTTCT | TATGTAGAAA | GGGAGGCAGA | 119340 |
| GTGACCTTCA | AGAGAGTTTG | GAAGGGGGAG | TGATAAATCA | GTTTAAAGAG | AGCACCCACT | 119400 |
| GATTCTTAGA | TAACTTATTC | TACTTTCCTT | CTCACTCTTT | TGCATTGACC | ATGGCTTAGA | 119460 |
| ATATATTTGA | GGAAAAGCAT | ACTGTCCATA | AGGTATTATT | GCCCTTTAAA | GCTGTTGGGG | 119520 |
| GGTACTATGG | GATGGTATTC | AGTGAGAGCA | GGACAGAGTC | TCTACAGAAT | TTTCTCTGAC | 119580 |
| AAAACAAAAA | CTAAATGACT | TCCAAGGCTT | CTCTAGCTCT | AAGCATTCCA | CAATTCTTTG | 119640 |
| GAAAGCTGGA | ATCTAAAATT | GCCTTAAAAT | TAAAAATAA | GAACAGTTAG | GGTGTACAGT | 119700 |
| CTTTACCATA | TTTATATAGA | ATCATCAGTC | TTCAGTGTGA | TACTGTGCTT | GAACCAACAG | 119760 |
| AAGGACTGAT | GAAACAGAAG | ACAAAGTCCA | GGTCTGGCGC | CATGGCTCAC | ACCTGTAATC | 119820 |
| CCAGCACTTC | GGGAGGCCGA | GGTGGCCAGA | TCACTTGAGG | CCAGGAGTTT | GAGACCAGTC | 119880 |

-continued

| | | | | | | |
|---|---|---|---|---|---|---|
| TGGCCAACAT | GGTGAAACCC | CATCTCTCCT | AAAAATACAA | AAATTAGCCA | GGCCTGGTGG | 119940 |
| CAGGTGCCTG | TAATCCCAGC | TACTCGGGAG | ACCAGAGGCA | TGAGAATCGC | TTGAACTCAG | 120000 |
| GAGGCAAAGG | TTGCAACTGA | GGTCATGGCA | CTGTACTCCA | CCATGGGTGA | CAGAGTAAGA | 120060 |
| CTCTGTCTAA | ATAAATAAAT | AAATAAATAA | AATAATAAAA | TACAACCTAA | AACCTAGCAA | 120120 |
| TCTCAGCCCT | GGAATTCTAT | TCAATTGCAC | CATGTTCAGC | AGTGGTAACT | GGAAACATCA | 120180 |
| ATGCTTATCA | ATAAGAAATG | GATGAATAAC | TTATGCTATT | CCATGTGAAG | GATTTCTTTT | 120240 |
| TTCATGACAG | GGTTTTAGAA | AAGTTTGGTT | AAGAGAAAAG | CAACATGCAG | AAGTGTATAT | 120300 |
| AACATCGTTG | TAAAAAATTT | TTATTATTTT | TGTTTTGAGA | CTGGGTCTCA | TTCTGTCACC | 120360 |
| TAGGCTTGAG | TGCAGTGGCA | CGATCTCTGC | TCACTGCAGC | CTCTACCTCC | CAGGTTCCAG | 120420 |
| TCATCTTCCC | ACCCCAGCCT | CCCAAGTAGC | TGGGACTATA | AGTGCGTGCC | ACTGGGCCTT | 120480 |
| GCTAATTTTT | TGTATTTTTT | GTCAAGATGG | GATTTCACCA | TGTTGCCCAG | GCTGGTCTTG | 120540 |
| AACTCCTGAG | CTCAAGTAAT | CTGCCCATCT | GGCTTCCTAA | AGTGCTGGGA | TTACAGATGT | 120600 |
| GAGCCACTGC | GTCCAGGCTT | TGTTTTTTAA | ATTAATAACC | CTAATCAAAA | GACAAACAA | 120660 |
| TTATGCATAC | AAGGCCAGGC | ACAGTGACCG | TAATCCCAAC | ACTTTGGGAG | GTCGATGATC | 120720 |
| ACTTGAGGCC | ATTTCTAGAC | CAGCTTGGAC | AACATGGTGT | GACTGTCTCC | ACAAAAATA | 120780 |
| AAAACAAAAA | GCCCGGCTTG | GTGGTGCGTG | CATGCAATCC | CAGCTACTCC | GGATGCTGAG | 120840 |
| GCTGCAGGAT | AGCCTGAGCC | CAGGAGTTGG | AGTTGGAGGT | TACAGTGTGC | TGTGATTATG | 120900 |
| CCACTGCAGT | CCAGTCTGGG | CAACAGACTG | AGACCCAGTC | TCAAAAGATA | ACGTGTTTTT | 120960 |
| TTTTTTTTT | TTTTAAAAAA | ACAAAACCAC | AAGTATGCAT | GTATATAGAT | AGGTGTATGT | 121020 |
| AAAATACTTA | GTTCAAAGAA | AAACATGTAT | ATTTCTCACA | AAAATAGGTG | AGAATTTTTG | 121080 |
| TTTTAAAGGA | TAAACCTAGG | TAGCTACATA | TTAGTTTGAG | GAAGGGGGAA | CAGGGATGTG | 121140 |
| ATGTGCCTGT | ATCCCTGACT | TTAGACGATG | GAAGGAGCTA | AGCAAAACAA | TTGAAAAAAG | 121200 |
| ACCGTTTGAA | AAATACAACT | GATTATTAAC | TCATATGCAC | ACACGCAAAA | ATAAACTTTT | 121260 |
| AGAATTGAAC | TGCACTAAGT | AAAAGTGAGT | AAACTTGGCT | CATCATATAC | TCTTGTCAGA | 121320 |
| TGTAAACAAA | AAAGTCCAAT | TATTAAAATC | TGACCCCCAG | AATTAAAATT | GCAAAAGCTT | 121380 |
| AAAGGGGCAG | TTCTGAGAAA | AGGATCTTCA | GTTTTGAATG | TGTGGGCTCC | ACCAGGGTTG | 121440 |
| AAAATCCTGC | ACGACTGATG | AAACACGATC | CAGTTAAGCA | CAGTAATTTT | CAAATATCCA | 121500 |
| ATCAGGGCGC | TTCCGTTTCT | AAAAACAGAG | AAACCGAGCA | AGGGATTTTG | GGTTGCAGCT | 121560 |
| CTAAAACTCC | AACAAACTAA | GCTCCTTTGT | CCTGACAAGG | GCCTAAACCA | AGTCGACAGC | 121620 |
| CCGTAAGTGC | ACCCATGGTA | AGGCGCTGCA | CAAAGAAAGC | ATTTTGCGTT | TCAAAGCTTT | 121680 |
| GTCATGATGG | CGCTGCAGAA | AGCAAGCGAG | CTAGGCCTAC | CTGGCGGGGC | TTTCAGAGGA | 121740 |
| CGCCAACGTG | GGCGCCAGCC | ACGCCAGCAG | GGTCACCGTC | CTTCCCAAGG | ACAGACAGCT | 121800 |
| CGCTAGCCAC | TCCTGTGGAG | AGGGCGTGGT | TAAGCCATAT | ATTTTGCCAA | CTATCCCAGA | 121860 |
| AGCATTTCTT | AGGACCACCC | AATTTCGGAA | AATGCTACTT | TAGCAATATT | GACCCCAAAA | 121920 |
| CGCAATATCC | CCACTTTAAC | CTTGTATAAT | AAAAAGCCTC | AAGCCTGGGA | CTGGGCTTCA | 121980 |
| ACCTTGGTTC | AATACGGTTA | TGACTAATTA | GCTTGGAGTC | GTGAGACGCG | GGACTTCCGG | 122040 |
| CTACCGAAAC | CCAGGTGACT | TTAAAACTCG | ATTTTAACTC | GGTGCATTTG | AATTCACCTT | 122100 |
| GCTATCTTTG | ATAGATTGAG | TAGTAAATTC | TTACTAGATG | AGGCTATGTT | AAAGTTCTAT | 122160 |
| CGACTCTCCA | AGTGATTCTA | ATATAATTGA | GGGCGTGTTG | CATTTGCTTG | GGGGATTTCA | 122220 |
| TCTGTGTACT | ACAGCTCTTT | TCCTGAAATG | CGTAGGTGGC | TCTTAAAAGA | GCCGTTGGGT | 122280 |

| | | | | | | |
|---|---|---|---|---|---|---|
| TACTAGAAGA | AACTTCTAAC | TGAATTTACT | TTTTCTTGGG | TGCCGCTTTC | TTGGGTTTGG | 122340 |
| CAGTCTTTGG | CTTCGTCACC | CTAGCCTTGG | CCGCCTTGGG | TTTTACAGCC | TTAGCTTTAG | 122400 |
| CAGGGCTTTT | AGCTACTTTC | TTGGGCTTTA | CAGTTTTGGG | TTTTTTTGGA | TTCTTGGAGG | 122460 |
| ATTTCCTTGT | TGCCGCAGGC | TTTTTAGCCT | TTTTCGGAGT | CTTGACGCTC | TTTTTGCTAG | 122520 |
| CCCCCGTGGC | CTTTTTGAGC | TTTTTAGATG | CACCCGTTGC | CTTAGTTTTT | GTAGCCACCT | 122580 |
| TTGAGGCGCC | GGGCTTGGTT | TCCACGGAGG | ACGCCTTCTT | GTTGAGCTTG | AAGGAACCCG | 122640 |
| AGGCTCCGGT | ACCCTTTGTC | TGCACCAACG | TTCCCTTGCT | TACCAGGCTC | TTAATGCCCA | 122700 |
| GCTTAATGCG | GCTGTTGTTC | TTCTCCACGT | CGTAGCCTGC | GGCCGCCAGC | GCCTTTTTAA | 122760 |
| GAGCTGCCAA | CGACACACCA | CCACGCTCCT | TAGAGGAGGA | AGCAGCCTGC | ACGATCAGCT | 122820 |
| CTGACACGGA | AGGGCCAGCG | GGTTTTTTCT | TGGAGGCTGC | TGCAGCCTTA | GCAGGTTTCT | 122880 |
| TTGCCTTCTT | GCCAGCTAAA | GGTTTCTCAG | GAGCAGCAGA | AGCGGCGGGG | GCGGGAGGCA | 122940 |
| CTGTTTCAGA | CATGGTGACT | AACACAGCAC | ACCAAATAAA | GTGGTATAAA | CCTGACGAAG | 123000 |
| CAGGATGCGA | AAAAAAGGCC | CCAACGCAGC | CTATTTATAG | GGTGGGACTG | CGCCGTGATT | 123060 |
| GGTGCCCGTC | AGTGCCGCC | CCTCGCGCCC | TAGCGCCCCC | TGCGCGCTGC | CGAGGGTTTC | 123120 |
| GCCCAGTCTC | AGAAGGCAGC | TGGGGGCCTC | TAGGGCCTAT | GGTCCTGCTC | CCCTCAACGC | 123180 |
| AAGCAAACAC | ACAGAAAAG | CCGCTCTGGT | TGCCTCATTG | TGAAGGAAAT | TGTAGGCAGA | 123240 |
| CTGCCGCCCA | GTAACATCAG | AGGGTACCGC | TTCTCTCTCA | AAAAGCAGCT | CTTTTTTAGG | 123300 |
| GAGTAGGTTG | AGAGGGGGCG | GTTTACAAAT | GCAGTGCCAC | AAGCATCCGA | GGAGTTTTAT | 123360 |
| TAGAAATTTT | TAGAGGTCCG | TTGCCAGAGA | TGTTAGTTTT | TAATTTGCAA | GAAATGTAAA | 123420 |
| ATACAGTGTT | TTGAATAGTT | GCGGAGGGAG | AGAAAAGTGC | GAGTTTTAGG | CCGTGTTAGG | 123480 |
| GCCAGTTGTC | ATCAACTCTA | TTACATTTTC | TGGCAATGTT | TTAGAGCGAT | GTGTCTCGCG | 123540 |
| AATACCTTTC | ACGTCAAACA | AGAATGAATC | GTAGACAACA | CCAGAATTCA | CAAACGCTGC | 123600 |
| AATTAATACT | CAAACTGCAA | GTGTGGAAAC | GTTTCTGCAC | TTGCAACTTA | TTTCCACAGT | 123660 |
| CCAATGTGGG | ATGCACTTCA | GGAATTTCCA | ATGCCTTTT | CATCCATACA | ACATGCCCCA | 123720 |
| AATTGGTATT | AAGGTTTACA | ACCTGTGTTC | CATGTCAGCA | CACGCAATCA | GCGCACCATG | 123780 |
| ACATGGTCAA | CTCATTCTTT | TATTCAACAA | ATATTTATGG | GCCTCACAAG | CCTGCGAAAG | 123840 |
| GCGTTAAATG | CTGGGTCCAC | GAAACCGGTT | CCCTGACAGG | CATTCTGCTG | GGGAGTTAAG | 123900 |
| TCCACTTAGT | GTGAAAGCAA | ACACGGGTGA | TAAATGCAAG | CACACCCTGG | GGATAAGATT | 123960 |
| TTATGGTAAC | AACCCTTTAA | CTTGTTTGTG | GCTGTTAAGT | GCATTTCAAA | GTATCAATAA | 124020 |
| GCTAAAACGA | TCTCACATTG | CCAATCAGAG | ACTCAGCTAA | TGGGAGAATA | AAAAACTATT | 124080 |
| AAATCGACAT | CCACTTCTAC | AATCCTATTC | TGGATAACCC | CCTAGCACAG | CACAGCAGAG | 124140 |
| AGTGAGGTAA | TGCGGTCTTA | TTTCCGCTCC | TGCTGTGGTA | GTTTTCAAAT | AAGTCCGAAC | 124200 |
| CATGCTAAGT | AACCTGAGCT | TTTCCCCTTT | TTGTTCAAAC | AACGTGCCAA | CCAAATAATG | 124260 |
| GAGTGGTCCC | AGATAAGTAT | TGTACCCATC | TTCTGCACCA | GTGCTTCCTA | CGTCCCATTT | 124320 |
| TATTGAGAAG | GCATGCATTC | AAATATTTCA | CGTAATTTCT | AAAAATTTGG | AAAATAACGG | 124380 |
| TTGGAAACTC | TACATCTTGG | TTTGACGGCT | AGTCAGTTAT | GAAACACAGG | TATACAAAAT | 124440 |
| TGGAAGATTT | TTGTAAGTAA | ACCCTTTGTG | AAAGATATAA | ACCTTTCTTA | GTGTAATAAG | 124500 |
| CGAGGTATCT | GAAAAAACGC | AACTTTTGAA | AAGGAAATAC | TCCTAATTAT | CTGATTCAGG | 124560 |
| AGTTTCCACT | TTAAATAATG | GGTTCTGCCT | CCCTTTTTTC | TATTGGGTTA | AACTGGTTTC | 124620 |
| AAATAAAATG | GGAACGCTCC | ATGCAAATGA | AGGATGATAG | ATCTGCTTTC | TAAATGGCTG | 124680 |

-continued

```
TTCAAGAAAA TAGCCTAAAC CAATCAAAAG ATAGAATGTG GCCTGTCTCT TGTGAATTTA 124740
AAAAGGTCAC AATCCACTTT TCAGTGTTTT GAGATTTTCA AAATGATTGC ATTAGCTCTT 124800
GGCAATGCTA AATTATGTTC CTTGCGAACC ACTATCCAGT TTCTCTTGGG CCAAGTCCAC 124860
CTCCTGCTCC GCAAGAGGAA CAACTCCCAG CTGGTGGTAC CTGGCGGCAG TGCTGGAGAA 124920
ACGCCATTTT GTGACTGGCA GAGTACACCT AGGCTTTAGA AAACAAAAGC TGCAGAACGC 124980
TGCAAGTTTA GGATTCAAAG AGCATAATCA AGAGAAAGAC GTCTCATAGA AAATGTTTCT 125040
GAGTAATAGT GTAATCCTAC TATGTTTGAG ATGCTTTGTA GATTTCAATA ACACTCCTAA 125100
GTCAATTAAA GCATTACAAA GGAATCCAAT TCTTGTGAAA GGTTTCAGAA ATTCCCGTAA 125160
AGGGTACATT TCCGGAGAGG AGGTGAGCAG TATTCCCTCT TTTTTTTTT TTTTTTTTT 125220
TTCCTAAAGA GCTGAAGGTT ATACGGAATT GGGGAATTAT AATACCTTTG GAATCAATGC 125280
CTTGTTTTAT GGAAAATAAA CACAGCCTTC AGGTTATGAA AACCAGATGT AGAAGAGGAC 125340
AAGTTTAAAA AATTAAAGTC CAAGCCGGCG CAGTGGGGCT CCCCTGTAAT CCCAGCTACT 125400
CTGGATGCTG AGGCGGGAAG ATCCTTTGAG CCCAAGTTTA AGACCAGCTT GGGGAACAAA 125460
GCAAAAGTAA AATAAAATAA TAGTAGTAAT AAAATACCAC TTAAATAATC ATCTGTAGAG 125520
TTGGAATAGA ATATAGTAGC CGGTGAAACT GCACGATTGT TGCTGGCTTA AAGATAGACC 125580
AATCAGAGTG TGTAACGTCA TATTTAGCGT CTTCTATCAT CCAATCACTG CACTTTACAC 125640
ACTATAAATA GAGCAGCTCA TGGGCGTATT TGCGCTAGTG TTGGGTGTTC CGCTGTGCTG 125700
TTTTTCCGTC ATGGCTCGCA CTAAGCAAAC TGCTCGGAAG TCTACTGGTG GCAAGGCGCC 125760
ACGCAAACAG TTGGCCACTA AGGCAGCCCG CAAAAGCGCT CCGGCCACCG GCGGCGTGAA 125820
AAAGCCCCAC CGCTACCGGC CGGGCACCGT GGCTCTGCGC GAGATCCGCC GTTATCAGAA 125880
GTCCACTGAA CTGCTTATTC GTAAACTACC TTTCCAGCGC CTGGTGCGCG AGATTGCGCA 125940
GGACTTTAAA ACAGACCTGC GTTTCCAGAG CTCCGCTGTG ATGGCTCTGC AGGAGGCGTG 126000
CGAGGCCTAC TTGGTAGGGC TATTTGAGGA CACTAACCTG TGCGCCATCC ACGCCAAGCG 126060
CGTCACTATC ATGCCCAAGG ACATCCAGCT CGCCCGCCGC ATCCGCGGAG AGAGGGCGTG 126120
ATTACTGTGG TCTCTCTGAC GGTCCAAGCA AAGGCTCTTT TCAGAGCCAC CACCTTTTCA 126180
AGTAAAGTAG CTGTAAGAAA CCAATTTAAG ACAAAAGGGA ATGCATTGGG AGCACTTTTC 126240
GTTTTAATGC TACTGAAGGC TTCAAAACCA ATCGATTTCG GCCGGTCGCG GTGACTCACG 126300
CCTGTAATTC AAGCACTTTG AGAGGCTGAG GCGGGCGGAT TACCAGAAAT CAGGAGTTCG 126360
GGATCAGCCT GGCCAACATG GCCGAATCCC GTCTCTACGA AAAATACAAA AACACGCCGG 126420
GCGCGACGGC GAGCGCTTGT AATCCCAGCT ACACTCTGAA GGCTGAGGCA GGAGAAACAC 126480
TTGAACCTGA GAGGCAGAGG TTTCAGTGAA TCGAGATGGC TCTAATGTAC TCCAGTCTGG 126540
GCGACAGAGA GATTCGGTTA AAAAAAAAGT TCGACTTAAA ATAATTCTGG AGTCAGAATG 126600
GGTTTACATT TAATTCTTAA CCCAGTTCCT CAAAGCCTGT AGCTCTGTTA AGAAAATAAA 126660
GGCCATTGGT CAAGCCTGCT TGGTCCCACC CTCATCTCCC CACCCTCCCC CAATCGCTGC 126720
TCCCGCCATT TCCTGGGGCT TGGAGGAGGG GTTAAAGGAG CGGACTGTAG GCGTCACATT 126780
TCCCGCCTGC GCGCTTTTCA GTCTCAGTGT CCGCTGGAGG TGGGGGCAGG GGTAACGTAG 126840
ATATATAAAG ATCGGTTTCC TATTCTCTCA CTTGCTCTTG GTTCACTTCT TGGGAAGTCA 126900
TGTCTGGACG TGGTAAGGGC GGGAAGGGTT TGGGTAAGGG GGGTGCCAAG CGCCACCGCA 126960
AGGTGTTGCG TGACAACATC CAGGGCATCA CCAAGCCGGC CATCCGGCGT CTGGCCCGGC 127020
GTGGCGGTGT GAAGCGGATC TCTGGTCTGA TCTACGAGGA GACTCGCGGG GTGCTCAAGG 127080
```

```
TGTTTTTGGA GAACGTGATC CGTGACGCTG TCACCTATAC GGAGCACGCC AAGCGCAAGA  127140
CAGTCACTGC CATGGACGTG GTCTACGCGC TTAAGCGCCA GGGACGCACC CTTTATGGCT  127200
TTGGCGGTTA AGGTTGCTGA TTTCTCCACA GCTTGCATTT CTGAACCAAA GGCCCTTTTC  127260
AGGGCCGCCC AACTAAACAA AAGAAGAGCT GTATCCATTA AGTCAAGAAG CTCAATGTGT  127320
AATTAAGATG AATGATACTG AGCTGACATC CTAAAAGGA AAGATTAGGG GAACTCCAAG  127380
TTTGCCCTCC ACTCACTACA TATGGGTAGG GGAGCAACGA TATTCCAACT CTGAAGAAAG  127440
AGTGGAAAAA AAGTAGTGTT AAAAATTTGT ATTAGTTTCC AAGGGACAAA GAAGCGCTGC  127500
CCAATCAATG AGGGCCATTC GTAGCTGTCA ACCAATCAGA ACTGATGAGC TAATATTTCC  127560
TGAGGCAAGC CAGGGAGCCG GAGGGGAAGC TAAGAAGCTT ATTGAGAAAA AACAAAAACC  127620
CTGTTTTAGG AAAAAAAAAA ACCATCTTTT AGCGATTATG AAATAAAATC ACAGAGACAT  127680
TTAAGTATCC CTCAATCATG TACTGAGAGC AATACTAAAT TTATCGCCAC CAATACAGTT  127740
TTACTCTATT AAAAGACCC TGAAAATTGA AACCCTATTC AGACTCCTGG AATACCCAGG  127800
ACACTAAATT CAGGGGAGAT TAAAATCTGT TTTAGAGAGA AAAGGCACCT TTTTCAGTGT  127860
TACCGCGGCC TTCAGCAGTT AACCTTTTTT TTTCCCCCTT TACGCAGAAA TGGAAATTTG  127920
GGTGATAGAA ATATTCCGAA ATTAAATTGT GATGATGGTT GTACAACTAA GAAAACACGG  127980
TAAAATTCAT TGAACTGTAC CTAAAGTGGG CAAATTTTGT GGTACATTAA ATATCAATAA  128040
AGCTGATTAT ATACATACAC ATATATTTTT ATATATGCAG AGAGAGAAAT GATGCAAGCA  128100
GGGTGGTAGG ACATGAGGTT GGTAGCATAG GCAATGTTGG TCTGTGAAGG GCCACCTGTG  128160
CTAAACCTGG AAGCCTGGGG TTTGTCCAGT CAAGCCATGG TAGCCATAGT TTTAAAGGAT  128220
GTTCCTGATG CAGTTATGTG TTCCAGTTAA GTACATCTAG CTTCAGAACT CAGCTGGAAA  128280
AGGGATGTGA ACTTCAGGTT AGCTGATAGG GAAATATCTT ACTCTCATCT GAGTAAATAT  128340
TCACAAATGC CTCTCATTGT GCTCTTTTG GTACCATTGT TATAGGACTG ATTTCAGCCT  128400
CACGATGTTA GCTTCAGTGA TGGATGTCTC TTTATTTTGA GGTCCTGTTT TCCACCTGAC  128460
AGTTTTCATC CAGGATTTCT TGAGGAATTA CACAAGTACC CAGCTTGGCT TAATTTAAAA  128520
CTGACAATGG AGAGAATTCA TAGCTGCATT CTGGATAGTT TCAGGAATCA GAGGAGCAAA  128580
AATGAGCCTG GTATGGAGGG TGGGTCATTT TATGTCTTTC TTAGTTGGTA TTTTAAAGAT  128640
ATTTATTGAT CTCATATGCC AGATATTGTT GAAATCATTG GGGTACATAA GTTAGAAAAT  128700
TTTAATTCCC TTTCCTGAAT TCCAGAGTCA ATGTAGAGGG GTGTGTGGAT ATCGATTACC  128760
CATATGGGAG GTATAGTCGT TGTAACAATA AGCCACGACT AGCTCCTGTT ACGTTTTGCC  128820
TGGCCTTTCA TAGCATTGCT ATGTTCATAG CATTGCTGAT ATGTCATACT CATCTTAGGC  128880
ATACCCACCA CCACCTTGGG CCTTCTTCAG TCCTAACACT CATGCAGTCC TTGTTCAGAA  128940
CAAAGATAAT GTTGCTTAAT TTGCAACCCC TAGACTATCC CCCAGATTTT CTAAAGAGAA  129000
ACTGCACGCT GATTGCTTCA GGCAGTGGCA GGTCAAGGAA TGAGATGGGG AATTGATTGT  129060
GTTAGCATTC TGGTGGGCTT AGTGGAGAGC CTGGAGACTT ACATAGAAAA TTCACACATC  129120
CTTTCATTCA ACAAACCTCC ATAAACTACC TGTTAAACGT CAGCCCTGTT CAAGGTGCTA  129180
GGGATACTTC TGGGACAAAA CAAAGTCCCT ACCTTCAAAA AATATATTCC AGTTGGGGGA  129240
GAGAGAACAA ACACAAAATA AAATATATCT AGTTATATGT ATTTTTTGTT AAATATATTA  129300
TTACATATAT AATTCTAGGT GGGGAAATGT TATATATATA TGCTATTGAG GATAGTCAAC  129360
TATATATATA TATGCTAAAT GAGCAGAAAA GCTTATTTTA CAAGGGATGA TTATGGGAGG  129420
TCTCTTTCGT AAGGTTGGTA TTTGAGGAGA GGCTTGAATG AAATGAGATC TAGAGCCATT  129480
```

-continued

| | | | | | | |
|---|---|---|---|---|---|---|
| CAGATATCCA | GGACAAGACC | CTTCTAGGGA | GAAAGAATAG | ATATAAAGGT | GCTGATGCTG | 129540 |
| GAAATGCTTG | GTCCATTCCA | GAAACAGCAA | GGTCAGTGAA | GAGAAAGAAC | TGCGAAGAGA | 129600 |
| ATGAGGTCAG | AGGGTAGCCA | GAGTACAGAT | CTAGTAGGTT | GAGCAGCTCA | TCCTAGTTTG | 129660 |
| CTTGGAACTT | TCTAAGTTTC | AGCACTGTAA | GTCTTACACC | CTGAGAAACC | CCTGAGAGTC | 129720 |
| AGGCAAACTG | TAATGGTTGG | TCATCTTACT | TGTAGGCTAT | GATAAGGATG | CTGGTTTTTA | 129780 |
| TTATGAAGGT | GATGGAAAGC | CAGTGGAATC | TTTTCAGCAG | ACAGTGGACA | TAATACCTTC | 129840 |
| AAAAGGATC | ACTGTTGATG | CTGGATAGAG | AAAAAACTGT | ATGACAGGGG | GATTAAAAGT | 129900 |
| GAAAACAAAG | ACCAGTTTGG | GGTCACTGTG | GTCATTCAGA | CAAACCGCCA | TGGCAGCTTG | 129960 |
| CTCCTAGAGA | AGCAGCAAAG | AAAACAATGA | AAGGTATTCT | GATTGATTTT | CAACAGAGCT | 130020 |
| GACTGCATTG | GGTGAAAGTT | GTAAGAAGCT | CAGGACAAAC | AATATTGCAC | AATTCCTGGC | 130080 |
| CCAAGCTGCT | TGAAGAATGG | AGTTCTATTG | ATTGACATGA | CAAATATCAG | AGGAAGAACA | 130140 |
| GACTTGGTGT | TTACGTATAA | ACATATTTTG | GACAAGTTCG | AGATGCCCAT | TATTCAATTA | 130200 |
| GATACATCAA | ATATGCAGTT | GTATATGAGT | CTAGAGATTT | AAGGTCAGGG | AGATGGTTTA | 130260 |
| TAATTGCAAA | CACTTATTTA | GAGACACAGT | TTCACTCTTG | TCTCCCAGGC | CTAAGTGTAA | 130320 |
| TAGCGCGATC | TCAACTCACT | GCAACTTCTG | CCTCCCGAGT | TCAAGCTATT | CTCCTGTCTC | 130380 |
| ACCCTCCCGA | GTAGCTTGGA | TTACAGTCGC | CCGCAACCAT | GCCCAGCTAA | TTTTTTTTT | 130440 |
| TTTTTTAGTA | GAGACGGGGT | TTCACAATAT | TGGCCAGGCT | GGTCTCGAAC | CCCTGACCCC | 130500 |
| AGGTGATCCA | CCAGGCTCAG | CTTTCCAAAG | TGCCGGGATT | ACAGGCGTGA | GCCACCTTGC | 130560 |
| CGGGCCTATA | TTTCTTAAGC | TCTATGTTTC | GTTCTGAAGC | TTGAAGTGGG | TGGAAGCAAA | 130620 |
| CTGATAGAAT | TTGGAGAGGT | GGTTAGGCAT | CCCGGGAATG | AGAAACAGCC | CGAAGCTGCC | 130680 |
| ACTATCACAG | GCTTTGGCAT | TGCTAGAAGT | TAACGTGGCA | CTTACAGCTA | GGCCGTGGTG | 130740 |
| TTCTGTTGAA | CAAACTATTT | GACAGAGCAC | AGAGCATGTA | AGTGGTGAGG | CCAGTTGAGT | 130800 |
| TAGCCAAGAA | AAGAGGAGTC | CAAGAACTGA | GCCAGAGTAC | ACCAGAGTAT | GTAGTGGAGT | 130860 |
| ACAGCTTTCT | CATTCTTTAG | TAGGGCTGTG | TAGAGAAATA | CTCTATTTTA | TGGATGTATA | 130920 |
| GATCACTCTA | GTCCTTTCTG | ATGAAAACTT | TACAGTTGCC | ACTCATTTAC | TATTACAAAC | 130980 |
| AATGCTGCAC | TACATTATGT | TTCAGTTTTT | AGCCATCTCA | TCTGGTCTCA | GCATTTATTT | 131040 |
| ATCTGCTGAT | GACTCACACA | TTTTTATCTC | CAGCTCAGAC | CTCTCACCCG | AACTCACTTA | 131100 |
| TTCAACTGCC | TATTCACTAT | ATCCTCCTGT | CAGGAGAAGC | TTGTTAGCAA | AGTAACCAGA | 131160 |
| AAACAAAGTT | GATTTTTTTT | GCTGAAGTAG | CCATCAATAT | ATTTGTTACT | AAATCAAAGA | 131220 |
| TGCTGAATAT | TTGGCTGACT | TCTAAAAATC | TGGTCACCTA | ACTTTGACAC | TTCCTAGGTC | 131280 |
| GTACAGTTTG | AAACTTTCAC | AATTAAATCA | GTTTTGGAAT | TTACAATTTA | AGGCAGGAAT | 131340 |
| AGAAGACTAT | TGGGTTGACA | GGTACAGTGA | AGATGCAAGT | CATCTGAGAA | TCTTACATCA | 131400 |
| GAGGGGGCTT | CCATCTTATA | GCTGCTGCCA | CGGACCTCGG | AGTCAGAAGA | AATTTGAGTC | 131460 |
| CTTATTTATA | AAACAGACTC | CCTTAGTCTA | CTAAGTGGGA | ATTTACGAAC | TGCGTAGGCA | 131520 |
| GCCTGCTTAG | GGGAGCCTCC | AGCCTGAGGA | CTGAAAATAG | CAAAGCAGCT | TAACCGCCA | 131580 |
| GTCCTACTCC | AGAGAAGGGG | GAGGTGACGT | CACTCAGCAG | GACGCCAAGC | TCAACTAGAA | 131640 |
| ATGGAAGTAA | AGGCTTCTGG | CGCTACCGGC | AGGGGCGGT | TAAGGACGGC | AGGTGTTACC | 131700 |
| AGGGAAGCTA | AAAGTACAGC | TTTTGCTGAC | GTTAAGTCAG | ATACGCCTGG | GAAAACAGAC | 131760 |
| CTGACACCCA | TTTTAATCCA | CCTACTCAGT | TCCAGGCAGC | TAGCATCTTA | GGCTCTCGTA | 131820 |
| CAAATAACGC | ACAACTCGTT | TTTAAAACTA | AAAAGCTGAG | CTACTCATTT | ATCGGACTCG | 131880 |

-continued

| | | | | | | |
|---|---|---|---|---|---|---|
| CGCTGCACGT | TAAGTTGCTT | GACATGTCAA | AACTATAGCA | TTGAAGTTTA | TAGCTCACTT | 131940 |
| ATCTCGGAGA | CCTCGTTTAC | TTAGCTGATT | TCTGCTTTAG | CAGCCACTCA | GACCAAACAA | 132000 |
| CCTGGTCTCT | CCCAACTGGT | TTATAATAGT | TCTACATACT | AGGCAGAATA | GCCGAGTAAA | 132060 |
| GCCATTGAGA | TGTTACCATC | CGAAAGAATA | CAATCACAGC | TCTTTCTGAG | AGGGAGTGGG | 132120 |
| CGGCCCTGAA | AAGGGCCATT | GGAAGAAAAC | TGACGAAAAG | ATTAACCGCC | GAAGCCGTAC | 132180 |
| AGAGTGCGTC | CTTGACGCTT | GAGCGCGTAA | ACCACATCCA | TGGCAGTGAC | AGTCTTGCGC | 132240 |
| TTGGCGTGCT | CCGTGTAGGT | CACGGCGTCC | CGGATCACGT | TCTCCAGAAA | CACCTTGAGA | 132300 |
| ACGCCACGAG | TCTCCTCATA | AATCAAACCG | GAAATTCGCT | TAACCCCACC | ACGCCTAGCA | 132360 |
| AGGCGCCGAA | TGGCCGGTTT | GGTGATGCCT | TGGATGTTAT | CCCGCAGCAC | TTTTCGGTGA | 132420 |
| CGCTTGGCAC | CTCCCTTACC | CAAACCTTTA | CCGCCTTTGC | CGCGACCAGA | CATGTCTAAC | 132480 |
| CAGCTGACAA | CAAAAACCAG | GTACGCGAAA | AGAAAGCAAG | CCACGAGCAT | TTATACACGA | 132540 |
| ACATCGGACC | TTATTGAGAA | CTGAAAGCGG | GAGCGAGGAT | AAGGAGGCGT | TGCTGCCTCA | 132600 |
| CTTTTTGCTC | CGCCCCTCGA | GGGGCAGTGA | CCTAAGGACT | GCGAGGGAGA | ACACAATAGT | 132660 |
| TTCACTTTTT | AATCCCTTTA | GTTTTCCCT | CCCGTTTACG | ACACTACTAT | TTGAATCTGA | 132720 |
| ATTTATACCC | TCGACTGAGA | ATTTTAATAA | GGGCTTATAT | TAAGGGCTTT | CACTAATATG | 132780 |
| CCGGAGTGGT | AAACTTTTTA | AGTCTTTCAA | GTGCTTGAAG | ACATATTGAC | TATTCAAAGG | 132840 |
| TACTTAAAAG | AGCAGGCGTG | AAAAGATCAC | TCTGGCCTTA | TGTTTTCTTG | AAAGCTGACC | 132900 |
| TGTTTCTTAG | AAGCAGTAGG | TGAAATTCTC | ATATGAAAGA | TGTTCTCACT | GTAGTTTAAA | 132960 |
| AAAAGCAACA | TTCTTCTCAA | GGATAGGAGG | CTGAGGCCAA | GAGAATTCTG | TACAAACCTT | 133020 |
| GCACTAGCCC | TTGCTGGGCG | CTTCTCTACA | CAGTTATATA | TTCTAGCCTA | AATCCCTTTG | 133080 |
| CTTTAGCGCA | TTTTTACATT | TTACTAATTG | TCCAATTCAT | TATATAAGTA | GCTAACTGCT | 133140 |
| TTTTTGGGC | TTTCATTACC | TTATGAGAGC | ACCTGTGTCA | CGTAAAACCT | GTGTTAAATA | 133200 |
| AATGCATATA | CCTTTCTCCT | GTTAATCCAT | TTACATTAA | TTTAATTTGC | TGGTCCAGCC | 133260 |
| AGAGCCCTAA | GAGGATGGGA | GTGGAGTTTT | GCTATCCTTC | ACACTGTACT | GTCTCATTCA | 133320 |
| GAAGAGGGTG | ATAGCTCATT | GCAACCGTGC | CTTCATCTGT | AAATCGGGTT | ATGATGATAC | 133380 |
| TCAGGGACT | TTTAATTAGC | TAATGTGAAC | GAGGCATGAG | AAGAGACTGT | GGAAAAGAAA | 133440 |
| TAAATATTAC | ATAATATGGT | TTAATTTTAG | ATGTTACTAC | TTAAAAAAAT | CTGCTCAGAG | 133500 |
| TTGGGATATT | GTCCTGAACT | CTCATTTCG | TGTTTTACT | CCCAACACTA | TATTGCTAGC | 133560 |
| AGCAACTATG | TATGTATTAG | TAAGGATTGT | TTTTTAAAA | TCACAGCCTG | TAATAACGTA | 133620 |
| CAAGGTGTTG | ACAGATTCCG | TTTAGCTTTT | CATATGTGAC | ATGTTAAAAT | TGTCCGAAAA | 133680 |
| TATTCCTTTG | TTCTCTTTTC | CAAGGTGCAA | TACAATAGCA | GCATTCGTGC | TTTCCTATAG | 133740 |
| CCAAGTCTGG | AGTGTAGTTC | AACTCTCCAT | ACACGCTTCT | CACTGTTGTT | TTAAATTTCC | 133800 |
| TGAAAACATT | CTTAAATCAC | TTCTATTGGA | AAAACTGCAA | GGGCTACTGC | TAAATTTTTA | 133860 |
| AGTCTGAAAA | ATGCACCCCA | AACTTGACTT | CTTTCTCTGA | GAATCTTAGC | CATCTCACCC | 133920 |
| AAATCTAACA | AACCAAAACT | GATTTTAGAC | TTCAACAGCA | TTAGCTGTAA | ACTTCAGCCT | 133980 |
| GCAGCATAAC | ATCACTTTGT | TGTGACTGGG | CAGGAAAAAC | CCTGTTAAAC | TGTTTCAGGC | 134040 |
| GCGTCCGTGT | GAAGAGACCA | TCAAACAGGG | TTTGTGTGAG | CAACAAGGCT | GTTTATTCTA | 134100 |
| CCTGGGTGCA | GGCGGGCTGA | GTCCGAAAAG | AGTCAGCGAA | GGGAGATGGG | GTGGGTCCGT | 134160 |
| TTTATAAGAT | TTGGGTAGAT | AGTGGAAAAT | TACAGTCAAA | GGGGGTTGTT | CTCTGGCTGG | 134220 |
| CAGGGGTGGG | GGTCACAAGG | TGCTCAGTGG | GGGAGCTTTT | GAGTCAGGAT | GAGCCAGGAG | 134280 |

| | | | | | | |
|---|---|---|---|---|---|---|
| AAGGAATTTC | ACAAGGTAAT | GTCATCAGTT | AAGGCAGGAA | CAGGGCATTT | TCACTTCTTT | 134340 |
| TGTGTTTCTT | CAGTTACTTC | AGGCCATCTA | GAGGCATACG | TGCAGTTCAC | AGGGGATATG | 134400 |
| ATGGCTTAGC | TTCGGCTCAG | AGGCCTGACA | AACTGAACAA | CTGGGAACAA | ACAACATTTA | 134460 |
| ATGCACACAA | TCTCTATCTT | GTAGGGAGGC | AAAATTTTAC | CTCTACTCTG | TTAGGGTCTC | 134520 |
| CAGCTGGACC | TGATAATTCA | TTTGCCATAA | AACAGATTAG | CAGAATGAAA | GCATACAAAT | 134580 |
| GTATTTAATG | TAAATTTTAT | GGGACAGGAG | AACCCTCATA | AAAAAGTGAA | GCCCCAAAGA | 134640 |
| AATGGCAAAA | GCTAAATGCT | TTCACATTAA | GTTAAAGAGA | GGCAATTGTG | GGAAAGTAAA | 134700 |
| CCATATGAGG | AGATTAAAGG | AATATATGAT | TATTTTAACA | AGGTTTGTTT | GTGTATAGAA | 134760 |
| GTCTCTCGGC | TATGACTCCC | TGCTGTGTTT | GTGCAGAATT | ATCTCATCTA | TGCCTCTGGG | 134820 |
| CTGAAGAATA | TGTCTTTTCA | CCTGGTACAA | GCAGAGCATT | TTTCACATTG | GAACTTTTAT | 134880 |
| CTCCTGTTTT | CAGAAAGAAA | AGTTTAGAAG | AATTCCCTTC | TTGAATGCTG | TTTTTGAAGT | 134940 |
| GCCTTTAGCT | CAAAAGAATC | CTGATCCCAC | AGTGGTCTAT | TTTTGGATGG | TATATTCTGC | 135000 |
| AAACAACACC | CCCTTTTTGT | CTCCAATCTC | TCCTTAATTA | CTCCTCTAAT | ACAAAACAAT | 135060 |
| AGATTCTTAA | TATAATATTA | AAATGTTTGC | ACTACTCACA | AATACAAAAT | GCTCAATAAA | 135120 |
| TTTTCTTTCA | CAAATGAGAA | TTTCATCCAT | TCGTTAATTT | TTAAATATCA | ACTGTCAATG | 135180 |
| AAGAGTTACA | GCAGAATCCT | TGTTCTGTTG | AGGAGGGGGC | AAAGAATGTA | AGTGAGGGAG | 135240 |
| TGGAAAATAG | CTGGACTGAG | CTACCACCCC | CTGTCCATCT | GATCCTCAGA | CAGTAATGTA | 135300 |
| ACTTTATTCT | TTTATGCTAT | TCGTCAGACC | CAGTACCTCC | AACACATTTG | TTTCCTACAG | 135360 |
| ATAAAGAAAA | TATAAAAAGT | CAAGCGCTAT | ACATCAGATC | CAGCACATCT | ATAACTGGAA | 135420 |
| AAAAAATACT | TGACCTTCAG | CTGGGCCCAG | AGCTTGTGAG | TAGTCACCTT | GGCATAGACC | 135480 |
| AAGTCCATTG | GCATCTCTAA | CATATCTATA | CTGTCTGTGG | ATAACAAATG | TCTATGCCAG | 135540 |
| TTAGAGTCGC | TTGTATAAGA | GTCAAGAAAA | ACGAATCATA | AACAAACTG | ACATATTCAT | 135600 |
| TTTCATAATT | TTTAAAATGC | AAATATTACT | TTATAAACCA | AAAACTGCCT | TATTAAAAGC | 135660 |
| TGGAACACAA | ATGAATTTAA | GTAAACGATG | CAATTCAAAT | TTAATCTTTT | GTGTGTGTGA | 135720 |
| TTTGTTGTTG | TTGACAGTTG | GTCAGGCGAT | TTTAGTATGG | TACATCAGTT | TACATTCTAG | 135780 |
| ATGTAGGCCA | AGAAAGAATG | TTAGGTGTAA | AAAATATTTA | TTGTAAAAAA | GAATGTGAGG | 135840 |
| CAAGGTCTTT | GGAATTAGTA | GTTTTAATGT | TGGACATTCT | GTGGTTGTTC | TAAAGTTAGT | 135900 |
| CTGTAAAATG | TGATGTAAAA | GCTATATGAT | AAAAAAATAC | AAAATATAAA | AATTTTAAAG | 135960 |
| TAAATATTAC | TTTTGTTTGC | GTACAGTATT | CCCATCCCTC | TAAATTTTCT | TCCAGTACTC | 136020 |
| AATCCCCAAC | CTCCAAAACC | GAAAAGCAAG | ATCAACAGAA | AGAAATGGT | TAAAACTTGT | 136080 |
| AAATTCTAGA | TTTTAATAAC | TACAGGCAAG | AAGTACTGAA | AAAAAGAATG | TGGCATGTCA | 136140 |
| TGGTGCATAG | TCCTAGAGGA | GACAAAGCAA | TGCAACCAGA | TAGACTATTT | ACAAGCAAAG | 136200 |
| CCACACATAT | AAAAATTCAT | ATATAAGGGA | TTAAATTATG | CTTGGTCGAC | AGACTGACAG | 136260 |
| ATTAAAGTG | GGTAGCTAGC | TATGGATAAA | ATGAGAGCCA | GTTAGATCCC | TGCCTCACAT | 136320 |
| TTTGCACCAG | AATAAATTTC | AGGTTAATGT | TAACAGCCAA | ATGAATTTAA | CAGTATATAT | 136380 |
| ATATATATAT | ATATATATAA | TATATGAGAA | AACCTAGGGG | ACTATGTATT | GAGCTGAGAA | 136440 |
| AATCTTCCTA | AGCATTTTGA | GGAAGACACT | GGAACTCGCA | AGACACAATT | TTCTAATCTT | 136500 |
| TTCAAAGCTT | TGCAAAAATG | CCTAGTAAGC | GCCAGTTAAC | TACTTACCAG | ATTTTTCCCT | 136560 |
| TACTCTTACA | AAGTTGTTTA | AACAAATGCT | AATCATAGCA | AGCTAGAGGC | CTGAATGATA | 136620 |
| GTGGACTTAC | ACAGCTTCTC | TCCAAATAGC | ACCTTAATAA | GGTCAGAAAT | AACCTACACT | 136680 |

| | | | | | |
|---|---|---|---|---|---|
| GCAAGACTGA | CCAAACCGTT | ATTTCTGTTA | ATCAACTTTA | AGACCATAGT | CTAATGCTTT 136740 |
| CCGGGGGGGT | CCTTAGAAAT | TTGTTCTGTT | AAGACAACAA | AAAATTATCA | CAGCTACTTT 136800 |
| CGTTGGAATA | AGTGGGTGGC | TCTGAAAAGA | GCCTTTGGGT | TTTAAGACTG | ATGAAAAAGT 136860 |
| GACTTTACAT | TTACGCTCTT | TCTCCGCGAA | TGCGGCGAGC | GAGCTGGATG | TCTTTGGGCA 136920 |
| TAATAGTCAC | TCGCTTAGCA | TGGATGGCGC | AAAGGTTTGT | GTCCTCAAAG | AGCCCTACCA 136980 |
| AGTAGGCCTC | ACAAGCCTCC | TGCAGCGCCA | TCACCGCAGA | GCTCTGGAAG | CGAAGATCGG 137040 |
| TCTTGAAGTC | TTGGGCGATT | TCTCGCACCA | GGCGCTGGAA | CGGCAGCTTC | CGAATCAGCA 137100 |
| ACTCGGTCGA | CTTTTGGTAG | CGGCGGATCT | CGCGCAGAGC | CACAGTGCCC | GGGCGGTAAC 137160 |
| GGTGAGGCTT | TTTCACGCCG | CCGGTAGCCG | GCGCGCTCTT | GCGAGCAGCC | TTGGTAGCCA 137220 |
| GCTGCTTGCG | TGGCGCTTTA | CCGCCGGTGG | ATTTCCGAGC | TGTCTGTTTA | GTACGAGCCA 137280 |
| TGGCAAAACC | ACAGAAAAGC | TTGCCTGCAG | AGACGTCTGT | GGAGGAAAGG | AAAGAGCTAC 137340 |
| TCTTCTTTTA | TAGAGTCAGA | CCACCAACTA | TTGGACCCAA | GAAAATTCAA | AAATCCCCGC 137400 |
| GCCCTTCTTG | GATTGGTCCA | TCTCTGTGCC | TGGTTGCAGA | TTAAGAGAGG | CTCCTGCCCA 137460 |
| TTACCGTAGC | TACTCTGACG | TCATTTTGTT | AACCCCTTAG | CTGCTATATC | CACTGTGGAC 137520 |
| AAGTCTTGTA | CTGGAAAAGT | TTCCTGAAGT | CTTAAAATTT | ACAACCACAC | AAAGCAACGC 137580 |
| GGAAACCTCC | AATTGTTTCT | AGTTAAAATA | TAAAAAGAA | ATCAGAGAAT | ATTGGAGACG 137640 |
| ATTAGGGAAA | TTTGCATATG | CGCTTTATTT | AAAATTGTAT | TTTTCTGGGT | GTCGCATAAG 137700 |
| AAGTGTGGGC | AATTAGAAAA | ATGCTCTTAG | CCGGGCGTGG | CGGCTCTCGC | CTGTAATCCC 137760 |
| AGCTACTCAG | AAGGCTGTCA | AGAGGATCGC | TTGAGCCCGA | GTTCGAGGTT | ACAGTGAGCT 137820 |
| GTTATCACGC | CGCTGCACTG | CAGCTTGGGC | GAGAGGGAGA | CTCCACCCCA | AAACAAAGCA 137880 |
| AAACATCCCC | AAACTGGAAA | AAAGCTCATT | TTGGGAAATA | CATACTCAAA | TGTTCAGTGG 137940 |
| TAATGTGTGT | GCTCTCAATT | GTGTATGCCA | TTAATTGCTA | CAGCAAATGG | TATGACATAT 138000 |
| TCAAACTTGT | GTGGGGCATG | CGGGTTTTAA | CACTTCCATT | CAAGATAGTT | AGGAATGCAC 138060 |
| TCATGGGTAT | AATTTCCTTC | CTCTAAAATG | TAGTAACTGC | TGTGTGTGAA | ACTTAACGCG 138120 |
| AATCACCCCT | GTAAACATGT | TTTGTGCTGC | ATGGCACTTC | TCCCACATAC | CTAGAATTCC 138180 |
| TGAGGTTTCT | ATGGATCTAA | TTTCTGCAGG | ACAAATTACT | AAAAGTGCCA | CACTCAAAGC 138240 |
| CATTAAAAAC | ACCTCAAAAA | CATCTTTATG | GGCGGCATAA | TCCAAAGCAC | AACAGCTCAT 138300 |
| TTAATGGAAG | TCGTAGGTGG | CTCTGAAAAG | AGCCTTTGCT | GTTAGGCTGA | TTTTGTCTGC 138360 |
| TGACAGAAAA | ACAGCAGTGC | ATGAAGCGTT | AACTCTTCAC | TTTCCCTTGG | CCTTATGATG 138420 |
| GCTCTCAGTT | TTCTTAGGCA | GCAGCACCGC | CTGAATATTA | GGCAAAACGC | CACCCTGCGC 138480 |
| GATGGTCACA | CGCCCCAAGA | GTTTATTAAG | CTCCTCGTCA | TTGCGGATGG | CCAATTGCAG 138540 |
| GTGGCGCGGG | ATGATGCGGG | TCTTCTTGTT | GTCGCGGGCC | GCATTGCCCG | CCAGCTCCAG 138600 |
| GATCTCGGCG | GTCAGGTACT | CAAGCACCGC | CGCGAGATAC | ACCGGCGCGC | CAGCCCCGAC 138660 |
| GCGCTCGGAG | TAGTTGCCTT | TGCGGAGCAG | GCGGTGCACT | CGGCCCACAG | GAAACTGCAA 138720 |
| ACCTGCACGA | GAAGACCGAG | TCTTAGCCTT | GGCGCGAGCT | TTACCGCCTT | GTTTGCCGCG 138780 |
| ACCAGACATA | ACTACTTCTG | ATAAGGGAAA | ATCGCCACAA | GAAAATGTAA | TGAAACTACA 138840 |
| TTAGAACGCA | AGGCAGAGAA | GTATTTATAC | TGACTGGAGG | TAGGCTGTGA | GGAATTCTCC 138900 |
| CATTGGCTAA | TGTCAAATAC | CCAATGGGAA | ATCAGAATCT | GCATCCTTCA | TTTGCATGTA 138960 |
| ATCCTTCCGT | CTGGTGTAAG | GTTTATGTTT | GACCCAATCC | CCAGTCTGGC | TTGACGAGCC 139020 |
| TTCGACTTGA | ATACTAATAA | TAATTGGCCG | AATTAGGATT | TTGTCAAAAT | ACCTTTTTTA 139080 |

| | | | | | |
|---|---|---|---|---|---|
| AGCATGAGTG | GAGGTTTTGT | TCTGGTTATT | TTGACTTTCA | GCCGCTCGTG | CTTTTCCCGG 139140 |
| ATTGTGACTC | ATGTTTTTGG | AAAGGAGTGG | ACTCCGACCA | ATTTCTAAAT | AGATATTTAA 139200 |
| GAGGTCCTTC | AAATCGGGCG | CAGTGGCTCA | TGCCCGTAAT | ACCAGCACTT | TGGGAGGCCG 139260 |
| AGGACGGCGG | GTCAGGCGTT | CGAGACCAGC | GTGGACAACA | TGGAGAAACC | CTGTCTCCAG 139320 |
| TAAAATAACC | AAAAAGAAA | CGGGGGAGAA | AAAGAAAAAA | AAAGCCGGG | CTTGGTAGTG 139380 |
| CACGCCTGTA | GTTCCAGTTA | CTCGAGAAGC | TGAGGTGGGA | GGATCGCTTG | AACCCGAGAG 139440 |
| GAGGAGGTTG | CAGTGAGTTC | ACATAGAGCC | ACCACACTCC | AGCGTGGGCG | ACAGAGCCAG 139500 |
| AAGACTGTGT | CTCAAAGACA | AAAAAGGGG | AGGGGAGTG | GGAGGGAAGA | AAAGCGAATA 139560 |
| CCCCAAATCC | CAGTGAACTG | TAGAAGCTTA | TAAGCTCTCT | TGATTCATAA | GGGAGAAAGA 139620 |
| AGGGGGATGT | AGGCAACTTA | GGGGAGAGTA | TATGATTTTG | GAGAAAATA | AATGGGTGTT 139680 |
| TCAAAGAATA | GGTGACAGCT | GTGACAAAGT | CTGTTTAGAT | GGTGTTAACC | ACCAGTCTCC 139740 |
| TCTCCTGTGA | TACAGTTAAT | CTTCTCTGGT | TGATGAGATT | CCCCAGGGAA | GTGAATCTTA 139800 |
| ACAACTAAAT | TCCTTTTTGA | ATTTTTTTT | AATTTTCAAA | TTTTTGATTA | GAGTTCAGCG 139860 |
| AAAGCCCTTC | CTTGAATTTA | CTGTTTCCTA | GGTGCCCTCA | GTTCAAAGAA | ATCAGCGTAA 139920 |
| CAAAGTGGCA | CATTTTTGAG | TTGCATTTCC | TGAACTTTTT | CACAACACTG | AATGAGGAGT 139980 |
| CTCTGGAATC | TTTCAGGAAA | TGAGAGAACA | AACATTCCAT | AACACAGAAA | TACTCAAAAT 140040 |
| GGGATTATGA | TTATAAAAGT | GTTTCACTGA | CCACCTTCTG | CCTTCCTGTC | TGTAAGTCCC 140100 |
| ATTCTCCCCA | AAGTCTAGCC | ATAGAAACCA | GAATTCCTCC | TCAAGGTAGG | CCATACAAAC 140160 |
| CAGAACTCCT | TTTCCCTAGA | ACCAGCCATA | AAACCTAAAA | GTATTACTCT | AACCTACCTT 140220 |
| GTTTGCCTGT | AGGTCATAAG | ACCCCCCATT | CTAAAAGAGA | GTCTTGTCCT | ATAACCAGAA 140280 |
| GGAAGAAATG | CTGCACTGAG | AGGTCAAGAA | GAATCTTGAC | AGACAAGCCT | TGCGGGCTT 140340 |
| CCCCACTCAG | TCTGTTAGCA | TTAGATCGTA | CCCTATACAG | CTGTTTATCT | TGTTGAACCT 140400 |
| AAGCATAAAA | ATGGGCAATT | TCCCCTGTAT | CTTTCAGTCT | TAATTCTAAA | ATCTCCTGTA 140460 |
| AAATTGTGAT | GAAATAAATA | TATATGCCTT | TTCTCCAGTT | AATCTGTGTT | TTGCCAGTAA 140520 |
| TTTTCCATAA | ACCTTGGGAG | GGCAAGGGG | AAGTTTTCC | TTGGCCGGGA | CAATATTATT 140580 |
| ACAGCCATTG | TCTGGCTCTC | CTGTTGAGGA | ACCTAAAATC | AAGACAGATT | GCCTAGGGAA 140640 |
| ATCTTGGTGT | TTTTCCTTTT | ATATTCCATG | AGATAGGAGC | AGATGGAGTA | CAGATGAACG 140700 |
| TGGATTAATT | ATTCCAGGAA | TTTCTGAGGT | ATCTACTACT | TCTATCTGTG | GTCTGCTTAT 140760 |
| ACTGAAACAG | GATGACAGAA | GGAAAAAGAA | ACATGAGTGT | AAAAAAATCT | GCTCCTGGCT 140820 |
| GGGCACGGTG | GCTGATGCCT | GTAATCCCAA | CACTTTGGGA | GGCCAAGGCG | GGCAGATCAC 140880 |
| TTGAGAACAG | GAGTTCGTAA | CCAGCCTGGC | CAACATGGTG | AAACCCCAGT | CTTCACTAAA 140940 |
| AATACAAAAA | ATTAGCTGGG | CGTGGTTGTG | GGAGCCTGTA | ATCCAGCTA | CTCCATAGGC 141000 |
| TGAAGCAGGA | GAATCGCTTG | AACCCTGGAG | ACAGAGGTTG | CAGTGAGCCG | AGATCGTGCC 141060 |
| ACTGCACTCC | AGCCTGGGCA | AGAGCGAAAC | TCCATTTCAA | AAAAAAAAA | AAAAAAATC 141120 |
| TGCTTCTAAG | CCAACGCTGT | CACAGAACTA | TGGATTTGAT | TCAGAGAAAC | TGTCAGGAGA 141180 |
| CTAAAGTGC | TCATTTTTAG | TTTGTTTTTT | GCCTTCTCCC | AAGTCTTCTG | ACTCTAGTGT 141240 |
| TATCTTTCCC | TTCACAATAT | TCAACTTCCC | TTTTCAAAAT | TATAATGATC | TTCACCCTCA 141300 |
| ACAATAGCCG | TAAACATCAG | TAATCACTGG | CTCATTTTCT | TTGAAAAGGT | ACAAGATTCA 141360 |
| TGATGGAGAT | GTTAAAAAGT | TATCTCAGAT | AGTGCCCTGA | AGAGATTATA | CTCAGAGAAG 141420 |
| GGAGGACTTA | CGTACATGAA | GATTAAATAG | CAGTGCACGT | TCTGCATATA | AAATAAAGAT 141480 |

-continued

| | | | | | | |
|---|---|---|---|---|---|---|
| TTTGAGCAAT | AAATCATACA | AAAGCACATG | GAAAAGAAGA | TTGATCAATG | TAAATTAGAA | 141540 |
| GGATTTAGAG | AGTTCATGAG | GGAGATGTAT | ATCCAGCATT | ATTAGTTCAG | CATATATTTA | 141600 |
| CTGAAAACCT | GCTAAGTGCC | AGAGAGTGTT | CTAGGTGCAG | GGAGCATAGC | AGTGAAAAAG | 141660 |
| CAGACAACCT | GTTTCCTTAC | GGTGCTACTT | GTCTTGTAGT | GGGAGGTGCA | CAATAAGGTA | 141720 |
| AATACATAAT | GAAAATGTAG | AGATAAGTGA | TGAGTGCTGT | GGAGAAAAAT | AAAGAAGGG | 141780 |
| GATAAGAAAA | AAGAATAGAA | ATAAGGATGG | AAAGTTTCAT | CAGGAGAATG | TCATTTGAAT | 141840 |
| TCAGACCTGA | AGGCAAGGAA | GAAGCCAGCC | AAGTAGGAAG | GATAAATACT | TCGATAAAAT | 141900 |
| GCTGGATGTG | TTTGAAGTCC | AGAAAATGTC | AGGAACCGTG | GTTCAGAAAG | TACAGCTATT | 141960 |
| CTAACTTCCT | AAACAAATCG | TAGACCATTT | TGGAAAGAGC | CTTGGATATG | TACAGGGCTA | 142020 |
| GATAAAATTG | AAACCAAGAT | TAAGGGTAGC | TTCAAAAACT | CAGACTAGAA | AGCAGGAGTA | 142080 |
| CATCCAGTCA | CAATATCAGT | AATCTATACT | CCACTGAGCC | ATGGATGAGA | AAAACTCTTC | 142140 |
| TTCTCATCCA | AGTTACCTTG | AATTAAGCAA | ACCAACAAGC | GCCTGGCATG | TACTATTAGC | 142200 |
| AAAACAACTT | GATGGCAATC | CTTTCAGTAA | GTGCTTCAAA | AACAGTAAAT | TCTAGGCACT | 142260 |
| TGCCTTCAAA | AAACATACAA | AAGGCAGATA | TTGGGGAGGG | AAATATTGGG | GGTTATTTAT | 142320 |
| TCCATATAAA | TATAAGAGGA | AAATAAGTTG | TTTCCCAATA | ACAACTCCAA | CACCAGGAGC | 142380 |
| AGAGAAAGTA | AGACAATCTA | TGCCTCGTGG | TTTGCGAAAA | CAATAAAAAA | AATCTGTTAA | 142440 |
| TTGCATAATA | CAATTCACCC | TTGAACACGC | TCCAAATCAG | TGCCCACTAG | CTACAAGTAG | 142500 |
| CTACTGTGAA | GTTGAAAAAG | GGTACTTCAG | ATTGAGCTAT | TCTGTAAATA | TGAAATAGAC | 142560 |
| TTAGTGTGTT | AGTTCGTTCT | TGCATTACTA | TAAGGGAATC | CCTGAAACTG | ACTAATTTAT | 142620 |
| AAAGAAAAGT | AATTTTTTTT | GGCTCACGGT | TGTGCAGGCT | GTACAGGAGG | TGTGGTGCAG | 142680 |
| GCATCTGCTA | CTGGCAAGTC | CTCAGGAAAC | TTCCAATCAT | GGTGGAAGGT | GAAGAGGGAG | 142740 |
| TAGGCATATC | ATATGGTGAG | AGCTGAGCGA | GAGAGATGGG | GGAGGTGTCA | CACTCTTTTA | 142800 |
| AAGAACCAGA | TCTCTTGTGA | ACTCAAAGTG | AGAACCCATT | GATTACCCTG | AAGAGTGCGC | 142860 |
| TTCATGAGGG | GTTCACCCTC | ACGATCCAAA | AACCTTTCAC | CAGGCTTCAC | TTCCAACATT | 142920 |
| GGAGATTACA | TTTCAACATG | AGATTTAGAG | GGACAAATA | TCCAAACCAT | ATCACTTAGT | 142980 |
| ATGAAGAAAG | AATGTAAAAC | ATCTGACTAA | TAATTATGCA | TATTGAATAC | ATGTTATAAT | 143040 |
| GACATTTTGA | CTACAAAAGT | TAACGAAAAT | ATACTATTGA | AGATACTCAA | AAATTTAAAA | 143100 |
| ATACATATAT | AATTTGTAGT | ACATTTGTAC | TGGGCAGAGG | AACCTCTAAC | AATGTTCCAA | 143160 |
| ATGTGGCCTG | TGTATGTGTA | TGATGTAGGA | GGGATCAGTC | ATGTAAGATG | ATCATAATAT | 143220 |
| AGTTACTTAG | TCCATTTTGT | GATACTATAA | CAGAATACCA | CAGACTGGCT | AACTTTTAAA | 143280 |
| GAAAAGAAAT | TTATTTCCTA | CTGTTCTAGA | ACCTGGGAAG | CTAAGGGCAT | GGAATTAGTA | 143340 |
| TCTGGTGAGG | GCCTTCTTAC | TGCATCATAA | CATGTTGAGA | GAGCAAGGGT | ATGTGTGTCA | 143400 |
| GCTCAGGTGT | CTCTTCCTTT | TCTTATAAGG | CCACCAGTCT | AAAGGAAATC | AAAATATTTT | 143460 |
| ACCCCAAAAT | ATATTTCTTT | GACATATTTT | GAAATGGCTG | CTGCTTGGCC | AGCAGGCAGA | 143520 |
| AATGGGCTTG | CAAAGCTGCC | TTAAATGGGA | AAAATTTTAC | ATCTGTAGAG | AATCTCCATT | 143580 |
| AATGCAGCCA | TGCCTCCTCA | CCTTTCTATA | CCTTTCCCCA | GATCCAGGAG | AGACTGAGAG | 143640 |
| TCTGACACTT | AAAAATCATA | AAAGAAACAT | TTACCATCTG | TTCTTTCTGA | GGGAGGCTTC | 143700 |
| ACCTACCTAA | CAAGGCCACC | TTTGCAAGCC | AAACCTCTTT | TGCCTCCCAT | AACCTGTTTT | 143760 |
| ACCAGAATCT | AAGCCCCAAT | TCTTTCTGTG | ATCTAAAAAT | GGTATATAAG | CATCTATAAC | 143820 |
| TCATTGGGAA | GTTAGGTAAT | TAATTCTGAA | TGCTCCCACA | TAGACACGTT | AAACAATAGG | 143880 |

```
TAAAATGCCT TTTCACCTAT TAATCAATCT GCCTTGTCAG TGATTTCTGG CAAACATTTA    143940
GTGGGCCAAG AGACTATGGT TCCCACACTA CCCTTCATGA ACTTAAGCCC TAAGATATCA    144000
ATAATTGCAT TAAATGTGTG TGGTATAAAT ACACCCATAA AAAAACAGTT TGGCTGGGCG    144060
CGAGGTCTCA CACCTGTAAT CCCAGCACTT TGGTAGGCCG AGGCTGGCGG ATCACTTGAG    144120
GTCAGGAGTT CGAGACCAGC CTGGGCAACA TGGTGAATCC TGTCTCTACT AAAAATACAA    144180
AAATTAGCCG GGTGTGGTGG CGCATGGCTG CAATCCCAGC TGCTCAAGAG GCTGAGGCAG    144240
GAGAATCCCT TGAACCCAGG AGGCGGAGGT TGCAGTGAGC TGAGACTGTG CCACTGCACC    144300
CCAGCCTGGA CAACAAGAGT GAAATTCCAT CTCAAAAAAA AAAAAACAAC AACTGTACAC    144360
TGTCTGCAAG AATCTCACTT CAAATATAAA CATAACGCAG GTTGAAATTA AAGGCTGCAA    144420
AAAAGATAAG CCATATAAAC ATCAGCCCAA AACTGCAAGA GTATCTGTAT TAATAATATC    144480
TGGGATCTGA AAGACCAAAA TAGATGCCCC TATACCAACT AAGACAGACT CTAAGATTAA    144540
GCAAACAAAG TTACCTACTG GTAGAGCATT CATGGCTTGG CTGGCATGGC AAATTCCTAA    144600
ATTCCAAAGA CTACCAAAAA ACTCACACTT GCTAAATTCC TTAACTATAG GAGCTATCAG    144660
AAGCCCTCCT AACTCTGATT TACAGTCCAG TCCACTACAA CTCTGATTGG ACAGAGGACC    144720
GCCTTGACAC ACATTCTATT CTTACACGTA ATTGTAGACC TTAAGCCATT TTCAGCCAGC    144780
TGCTAGAGGC AGCACGTAAA CTTTGTTCCT ATAGTTCACC TTGTGATGTA AAGACCTAAA    144840
TTCTACCTCA TTTTAACCAA AATTTAACCT CGAAGTGAAC ATGGGAGGTA TATTACACGT    144900
GTTTATCCAT TGTGAATGCA CTTGGCACCC CTCATAATAT ATATAGCTGT CCCCCCAAAC    144960
GTGCTAAATA TGTATGACTC TATTGTGTAA TATATAGCCT ATGAGGCATA AAAATAACCA    145020
ACCTGCTCCT TCTCCCCAAA GAGAGAGTAA TTTTGGCAGG TTCTGGGACC ATCTCTTCCT    145080
GGCTTGCAAA TTAGTATTGC CAGTAAATCT CTCCTTTCTA CTCTTTAGCC ATCCTGGTGG    145140
TCTTTTGGAT GATATATCAG ATAAGTATAT TTCAGAGCAA AGAAAATTAC TAGGAACAGA    145200
CAGGGATATT ACATAATGAT AACAGGGTCA ATCCAATACG AAAACAAGC AATTCTAAAT    145260
GTATATGCAC CAAATAACAG AACTGCAAAA TATGTGTAGC AAAACCTGAT AGAACCGAAA    145320
GGAGAAATAG ACACATACAT GATTTAAAGG TAGAGATTTC AACACCCCTT CCCCAATAAT    145380
TGATAGAACA ACGAAACAAA AAAATTACCA GGTGTATAGA ACTCAGTAAG TGACTGTATT    145440
ACTTGTTTTG ATCTGTAAAA CAATGATAAT AATAGTACTC ACACTTCATT GAGTTTTGGT    145500
GAAGATTGAA TGAATTTATA CTTATAAAGA ATTTAGAAAT GTGGCCGGGC CCAGTGGCTC    145560
ATACCTGTAA TCCCAGCACT TGGGAGGCC GAGGCGGGTG GATCACCTGA GGTCGGCAGT    145620
TCGAGACCAG TCTGACCAAC ATGGAGAAAC CTCATCTCTA ATAAAAATAC AAAATTAGCC    145680
AGGCGTGGTG GCGCTTGCCA GTAGTCCCAA TTACTGGGGA GGCTGAGGCA GGAGAATTGC    145740
TTGAACCCTG GAGGCGGAGG TTGCGGTGAG CCGAGATCGC ACCATTGCAC TCCAGCCTGG    145800
GCAACAAGTG TGAAACTCCG TCTCAAAAAA AAAAAAAAAA AAAATCTTAG AAATGTAACT    145860
GACATATCAT AAGCCCTCAA ACTTAATAAT CTTTTAATAC ATGGAGCTAT CTATTTAAAA    145920
TAATGTACAT AAGGCAACAT CCCAAAAGAA AATGGGCAAG AATCATGAGT AATCAAACCA    145980
TAATAGAAGA AATGTTATTA TCAAAATGTG CAGTCTCAAA CAATAATTGT CTTAAAAATA    146040
AAAACAACAA TGAGATTTAA TTGTTCATGT CGGCAATTTG AACAGACTAA CACACCCACT    146100
GTTCAAGAGC ATTTGTGGAA GTCAGGAAAA ACACCCTGT TGGTGAGAGT GTAAACAGAC    146160
CTTCAGGAGG CAACTTGGTA ACATGTATTA AAAATCAAAA TATGTATATC AATGGATGCA    146220
TGATTCCTAT CTCTATTTTT GCCCTTACAG CAATCTTGTG TGTAGAGAAA TACTGAAAAG    146280
```

-continued

| | | | | | | |
|---|---|---|---|---|---|---|
| CATTTTCATG | GTAACATGGT | TTAAATTTTT | AAAAAGCGAA | GGTCAGTGAA | TAAAGGGCAA | 146340 |
| TTATCTACTT | CCCTACAATG | AAATGCAGTA | ATGAAAATAA | TCATTAGAAT | CTCTTTTATT | 146400 |
| AATTTAAAAG | GATACTAGAA | AAGTGAAATA | CAATCTCACT | TATAGAAGAT | TTACATATTG | 146460 |
| GTTTGCATAG | ACTTGCACAA | GATAAAATTT | CTGTAAGATT | GGTCACCAAA | ATGTCCTGAA | 146520 |
| TGATAACATT | ACAATTAATG | TTTATATTGT | AGGGGAAAAG | AAAATTCTGT | TTTTCTCACC | 146580 |
| CATCAGTAAG | TTCATGCTTG | AGGCCCTCT | ACAAAAGAC | AGATTGGTCG | GGTGCAGTGG | 146640 |
| CTCACGTCTG | TAATCCGAGC | ACTTTGGCAG | GACGAGGCGG | GCGGATCACG | AGGTAAGGAG | 146700 |
| ATTGAGAACA | TCCTGGCCAA | CACGGTGAAA | CCCTGTCTCT | ACTAAAAATA | CAAAAATTAG | 146760 |
| CGGGGCATGG | TGGCACGTAT | CTGTGGTCCC | AGCTACTCGG | GAGGGCGAGG | CAGTAGAATC | 146820 |
| GCTTGAACCT | GGGAAGCGGA | GGTTGCAGTG | AGCCGAGATC | GCGCCATTGC | ACTCCAGCCT | 146880 |
| GGGTGACAGA | GCAAGGCTCA | GTCTCAAAAA | ACAAAAAAAA | AGATTAGCAA | GAGAAAGCA | 146940 |
| TACAAATGTA | TTTAATATAA | GTTTTATATT | ACATGGGACC | CTTCGGAAAT | GAAAACTCGA | 147000 |
| GGGAAGCGGG | AAACCTGTGA | ATTTTTATGG | CAAGTTTTGT | GAAATGCATA | GTTGTGGATT | 147060 |
| AATATGATTG | ACAGTAGGCA | TATGATCTAA | TGGTAATAAA | CTGAGGGGA | CATAGCAAGG | 147120 |
| CTTGTTTGTT | AATTACCTAT | TAACGATCAG | CCGAGTATCA | GCAGAGACAG | CAAAACATCC | 147180 |
| TAGTTTTGAG | TTAGAAGACC | TAGGTTTTTG | TTTTGGCTTA | TCAATTATGG | GTATTGTTTT | 147240 |
| AGATGAAACA | TCAAGTATTC | TTGATTTCTT | ATTTCAAAAA | TAAAAATAA | AAAATAAAGG | 147300 |
| AAGGAAAAAA | GAAGAAAAAA | AGAGAAGAAA | AGTGTCAGAG | TTACTTGAAC | CAGAGTAACT | 147360 |
| CCATTTGAG | TGAGGGCTAG | GAAAATGAGG | CTGAGACTTT | CTGGGCTGCA | TTCCCAGAAA | 147420 |
| GTCAGTCATT | CCTAGCTTCT | AGATGTTTAC | GGTTAAGGGA | ACAAATAAAT | AATGTTTACT | 147480 |
| AAACAGACTC | AGACTTAGGA | GTGTCCAGAT | ATCCCTATAT | CTGGAGAACA | AAGGCATTCT | 147540 |
| TAATTTTGTT | TAAAGATAAT | AATGTTGATT | CTTGCAAAAT | ATAGTAACTA | AGAAAATTAA | 147600 |
| TCCTTTATCA | CAAACTTGTA | GCAGAGCACA | TCTCCCATA | TATACAAGTA | TTGTACCTAG | 147660 |
| GGTGGATGCC | TTCCTCCTCT | TACTTCGGG | AATGTCCTGC | TCCGTCTATG | GAGTAGTTGT | 147720 |
| CGTTTCACCA | CTTTACTTTC | TTAGTAAACT | TGCATTTACT | TTGCACTGCG | GACTCACCCT | 147780 |
| GAACTCTTTC | TTGCGCGGGA | TCCAAGAACC | CTCTCTTGGG | GTCTGGATGG | GGACCTCTTT | 147840 |
| CCTGTAACAT | ATTTCTGGCC | ACCACAGAAG | GGACTATAGT | ACAGAAACCC | TGACCCAACA | 147900 |
| GCTACCTTTG | GGTAAGTGTT | GGAGTTCTGT | AACAAAGGAA | GAAGGCAGGC | AGGCAAAAAA | 147960 |
| TTTATGAAAG | AACATACGAC | AAAATAATTT | CTGCTTCAAA | ACTTCATATT | TTTTAATTT | 148020 |
| TTTTTTTTTT | TTTTTTTGA | GACGGAGTCT | CGCTCTGTCA | CCCAGGCTGG | AGTGCCATGG | 148080 |
| CGCGATCTCG | GCTCACTGCA | AGCTCCGCCT | CCCGCGTTCA | CGCCATTCTC | CTGCCTCAGC | 148140 |
| CTCCCGAGTA | GCTGGGACTA | CAGGCGCCCA | CCATCACGCC | CAGCTAATTA | TTTTGTATTT | 148200 |
| TTAGTAGAGA | CGGGGTTTCA | TCGTGTTAAG | CAGGATGGTC | TCCATCTCCT | GACCTCGTGA | 148260 |
| TCCGCCCGCC | TCGGCCTCCC | AAATTGCCGG | GATTAAAGGC | AAGAGGCACC | GCGCACGGCC | 148320 |
| CCGTCCAAGT | TAACCTTGGC | TCTAAAACTT | GTCTTCGCTA | ACATTCCAGT | TGATCCTCTA | 148380 |
| GAACTGAAAC | AGAATAGCAG | CAGCACCACC | TTAAGAAATT | GTGGTTATAG | CTCTCCTTGT | 148440 |
| GACAAAGTAG | GTGGCTCTGA | AAAGAGCCTT | TGGGTTTGGA | AGTGCTTACA | TAAGCACTTA | 148500 |
| TTTAGAGCTA | GTGTACTTGG | TAACTGCCTT | AGTGCCCTCG | GACACAGCAT | GCTTAGCCAG | 148560 |
| CTCCCCAGGC | AGCAGCAGGC | GCACAGCCGT | CTGAATCTCC | CTGGAGGTGA | TGGTCGAGCG | 148620 |
| CTTATTGTAG | TGAGCCAGGC | GAGAAGCCTC | GCCCGCGATG | CGCTCGAAGA | TGTCGTTGAC | 148680 |

```
GAAGGAATTC ATGATCCCCA TGGCCTTGGA TGAGATGCCG GTGTCGGGGT GGACCTGCTT  148740
CAGAACCTTG TACACATAGA TAGAATAGCT CTCCTTGCGG CTGCGCTTAC GCTTCTTACC  148800
ATCCTTCTTC TGCGCCTTAG TGATAGCCTT CTTAGAACCC TTTTTAGGGG CTGGAGCAGA  148860
CTTAGAGGGT TCAGGCATTG CTATTCCTAA ACAGAATAGA AAAGCTACTA ACACTCTCCA  148920
CTACAGAGTA GTACAGAGAA CAGTTCAGAG CCCATGTATT TATAGTCCTG AGATTCAAAT  148980
GACGGTTTAA GATTCCTCAC TTCTGATTGG ACAAAAGAAA CACGGTTTCA CTGAGGGGTG  149040
GGGTTTATGC AAATATGGAA TTTATGTTAT CTTTTTCTAT TGGATAAAGC ACCAAACATA  149100
ATTGACCAAT AGGATAGCTT CCTATTGCAG CCTTGCAGTT TGTATAAAAG GATTTGTTCA  149160
GGCGCCATTC CAGCTTGCTT GTCTTTCACA GTTTTCCGCT GCTTTCATAG GTCGCTATTT  149220
GCGGACGTGG AAAATGGAGC TAAAGCAAAA ACTTGTTCGT CGCTACCGGG CTTGCAGTTC  149280
CCAATAGGGC AGAGTCCGTC ATCTTTTCG AAAGGGCAAT TATTTGAGC CGGTCGGAGC   149340
CGGTGCGCCA GTGTACTTAC AATACCTGGC CGCCGAGATC TTAGAACTGG TGGGCAGCGC  149400
CATACGTGAC AAGACCCGCA GCATCATCCC CCGCCACCTG CAGCTGGCCA TCCGAAACGA  149460
CGAGGAGGTC AACAAGCAGC TGGGCAACGT CACTATTGCT CAGGGAGGCG TCCTGTCCAA  149520
TATTCAGGCC GTCCTGTTGC CAAAATAACA GAGCCACGAT AAGGCCAAGG TCAAGTAAAC  149580
ACTCAAATCA GAAAACGTAG CTTACACTTG AAACGGCATT TTTCAGAGCC GTCCATAGTT  149640
ACACAAGAAA GGATGATAAC TTGCTTCTGT TAGGGTATTT TTTGCTTTTC GTTTGGATTG  149700
GTTTGTTTTG AGACAGTCTA GTTCTGTCAC CCAGGCTGGA GTGCAGCGGC GCGATATCGG  149760
CTTACTGCAA CCTCCACCCC GCCGCTTCAC GCGGTTCTCA TGCCTCAGCC TCCTGTGTAC  149820
TTGGGATTAC AGGCGTCTGC TACCGCGCCC AGCTAGTTTT TGTATTTTA TGCGAGACGG   149880
GGTTTCACCA TTTTAGCCAG GGTTGTCTTG AACTCCTGGC CTCTAGTGAT CGTCCCATCT  149940
CGCCCTCCCA AAATGCTGGG ATTACAGGCG TGAGCCACCG CCCCCCTAGC CTAATGGTGT  150000
TAAAAAGTTA AGTTTCGAGA AAATAACACC TTCCTTTAGA AAGTACATTT TAGAGTATAC  150060
AAAGTGAAAC TTAAGGCCAA CCAAAATAAG ACATTTTGAG AACAGGCAGG GTGGGAATGT  150120
GACTTGGACT TAGAAAACAA AGGGCAAGGA AACTTGCTGT TCGCCAGTAA CAAAATAGCA  150180
TGGAATCTCA TTCTCTGAAT ATAAGCGTTA TTTCCCGACA TGAGTCTGAA CGTTTCTGGT  150240
GGTTTAGTGA GTGTTCACCA GCATTGATAA CTTGCGAGAC TGTCAGGAAT GCAGAATTTC  150300
AAGTCCCACT CAAACTTACT GAATCGGAAT TTACATTTTA AAAATCCTTA GATACCTTGT  150360
TATACACTCT GTTCTTTGGG ACTGGATGAA CTAGAATTTT AGACAATTTG TCGCTGCAGA  150420
TAACTGAAAC GAAAAGGACA GGATGGGCGG TGGGGCAACT CATCCAATAA GATTGTCTAG  150480
TAATGAACCA ATCAGTCTGG TCACTCTTCA GCCAATGATT TTATCGCGCG GGACTTTTGA  150540
AATATTACAG GACCAATCAG AATGTTTCTC ACTATATTTA AAGGCCACTT GCTCTCAGTT  150600
CACTACACTT TTGTGTGTGC TCTCATTGCA AATGGCTCGT ACGAAGCAAA CAGCTCGCAA  150660
GTCTACCGGC GGCAAAGCTC CGCGCAAGCA GCTTGCTACT AAAGCAGCCC GTAAGAGCGC  150720
TCCGGCCACC GGTGGCGTGA AGAAACCTCA TCGCTACCGC CCGGGCACCG TGGCCTTGCG  150780
CGAAATCCGT CGCTACCAGA AGTCCACCGA GCTGCTGATC CGGAAGCTGC CGTTCCAGCG  150840
CCTGGTGCGA GAAATCGCCC AGGACTTCAA AACCGACCTG CGTTTCCAGA GCTCTGCGGT  150900
GATGGCGCTG CAGGAGGCTT GTGAGGCCTA CCTGGTGGGA CTCTTCGAAG ACACCAATCT  150960
GTGCGCTATT CACGCTAAAC GCGTCACCAT CATGCCCAAA GATATCCAGC TGGCACGTCG  151020
CATCCGTGGG GAAAGGGCAT AAGTCTGCCC GTTCTTCCT CATTGAAAAG GCTCTTTTCA   151080
```

| | | | | | | |
|---|---|---|---|---|---|---|
| GAGCCACTCA | CAATTTCACT | TAAAAACAGT | TGTAACCCAT | TCGGTTGTCT | ATGTTAGTTT | 151140 |
| CCAGGAGATA | TAAAGGTGAT | AACTACACAC | AAGTTTTGTA | ACTGCAGACA | AGTCTATCAG | 151200 |
| GCCTTTTCAA | CCGGTTTTAC | TGCGAGAAAA | CAAGCTGAGT | TACTGTTTTG | CCCTTGTTAA | 151260 |
| AAAATTCCTA | GGGGTCTTTT | TAGCATGTAT | ATGTGTAAAT | ACTTACATAT | TGAAAGGCTC | 151320 |
| CTGGGGACAC | CACCGTCACT | CCTTTTAATC | CACGTGACAA | TTTTAGTTCT | GATGGCAGTA | 151380 |
| TTATTAAAGC | TATCATAAAG | ACAATGTGTG | TGTAGTTACC | TAAGTCCACA | AAAACAATAG | 151440 |
| CTGACCCCAA | AATTCAGTAT | TGGTTTTGGG | CTGCTGGAGG | TGGAGTCAGA | GCTCAGGTGG | 151500 |
| AAGAAACTGG | CCTCAGTACA | CACTGCCAAA | AGTCCACTAA | ATAGATTTAT | GTAACAAGTA | 151560 |
| CACAAGACTT | GCGTATGACC | ATCCAAAGAT | TATGCGGTCA | TCCTTATCCA | GGGAATTTGA | 151620 |
| GAATGAAGGG | TGGCAACTGC | AAAGCTCTTT | TACCCATGTC | CTCTTTTAAT | AAATATTTAA | 151680 |
| AAATATTCAA | ATGCTGATTT | CATCCATTTT | CTAAATATAT | TAGTATACTT | AACTGATGGG | 151740 |
| GTAGATCAAG | GTTTTCTGGG | GATCAAACCT | TTTACAACTT | GTTAACTATT | AAAAACTATA | 151800 |
| ATGTAAAATT | AAAAATGCAA | AAGTACTGCA | GACTGTAAAT | ATAAATTTAT | AATGGGAAAA | 151860 |
| TAAAATCAAA | TTCCAATTTT | ATAAAAGCTG | ACAAACAAC | AGCCATCACA | AAATTCAGAA | 151920 |
| AATAGCATAT | TTTATTAACT | TCTGAATATG | ACACTACCAA | GTATATTTTC | CTGTAGTTTT | 151980 |
| GACTGAATAC | TCTGATTCCA | TCTTCAGATC | GAAATTATTT | TGTAATGTTG | TCTATAGGTA | 152040 |
| ATGGAAATAG | AATTCAATCT | TTCCTCCAGG | GTGGCTGATG | ATAATATGTT | TTCTTCATAA | 152100 |
| CTTAGAAGTA | TTTCAGTTTC | AAAACACATT | ATTGGTAATG | TCAAGTAAGT | TTTTAGGATT | 152160 |
| GTTTTCAAAT | TTGGAAAATC | CTCTGTTAAG | CTCCTTTCAC | ATGTAAGTTG | TAAACTTTGT | 152220 |
| AAGAATTCTT | TCCAGACTAG | CTTCTGGCTC | TATACGTTTC | TACTCTCCAC | TAGACACTCA | 152280 |
| CTCTCAGTGC | TGGGAATGTG | TTTTGAATAC | TTAGATGTCA | TAACATTTTA | TCTAGACCTG | 152340 |
| CATCTTGCCA | GGAATTTAGG | TGAGTTATTC | CAGTGAGCAG | TAGGAACATT | CCTTGAAGCC | 152400 |
| ATTCTTTTTT | TTTTTTTTT | GAGACGGAGT | CTCGCTGTGT | CTCCCAGGTT | GGAGTGCAGT | 152460 |
| GGCGCAATCT | CGGCTCACTG | CAAGCTCCGC | CTCCCAGGTT | CATGCCATTC | TCCTGCCTCA | 152520 |
| GCCTCCCAAG | TAGCTGGGAC | TACAGGCGCC | CGCCAACACG | CCCGGCTAAT | TTTTTGTATT | 152580 |
| TTTAGTAGAA | ACGGGGTTTC | ACCGTGTTAG | CCAAGATGGT | CTCGATCTCC | TGACCTCGTG | 152640 |
| ATCCGCCCGT | CTCGGCCTCC | CAAAGTGCTA | GGATTACAGG | CGTGAGCCAC | CGCGCCCGGC | 152700 |
| CTCCTTGAAG | CCATTCTTAC | GTCAGATTGG | CTGGCAACGA | ATGAAGTACA | CATGATCACA | 152760 |
| TATGCAAATC | ACGTAACTTA | TTATCCCCAT | ACTAGATACA | TCTTCAACTA | AACTTTCTCT | 152820 |
| TACTCAAATT | CCAAATATTT | TCATCAGGAT | TCTAACATAA | TCAGACAATG | GTGATTTTAA | 152880 |
| TAAAAAGGAG | GATTGAGTGA | AAATAGCAGC | CTGAACCATC | CGTGATTAAA | GTACCTTAAT | 152940 |
| ACTGCAAATT | TTAAAATCAG | AGAGAGAGAG | AGAGACAAAC | TAACACATTT | GTAGGGCCCC | 153000 |
| TCTCTGCACC | TTGGAAGTAC | AGGCCCTTAC | ACTTGTGTTT | CATTAGCTTC | AGGATAAATC | 153060 |
| TGCCCCAGAT | CACTGGCCAA | ATTTTACGTG | GCCTTCTTCA | GCATCCTACC | ACTCTATTCA | 153120 |
| AATACATCTC | TGCAGGAGCA | CCCTGTGAGT | TGAGAATTAC | TGGTCTGGGA | TGACCACTGT | 153180 |
| TTGCATGATG | CTTTGGATGG | TGGTGCTGTT | CTCAGAAGAA | ATACCAGAAG | GAGAAAGGTT | 153240 |
| AGTCAGGAGA | ATATAAAGTC | AACCTTAAGC | AATTTGAACA | CTTCAGTGGT | TAAGTGAGTT | 153300 |
| CCCTGGGACA | ACTCTGCAAG | CTGTTTTAAC | TTTATTTGTA | TTGAATATTA | CCTTCTTTTA | 153360 |
| GAGAGGCCAA | CGTGTAGAAG | GAAATAACAA | TGAAACAAAG | GATTCATTAA | TAGTATAAAC | 153420 |
| TATAAACTAA | CTGTCATTGA | TAGTCTTCCA | CGGGCCAAGT | ACCACATGAA | GTGGTTGGTC | 153480 |

| | | | | | | |
|---|---|---|---|---|---|---|
| TGAATTATTG | TGTAAAATTC | TTACTTCAGC | ATTGTAAGGC | AAATTATCTC | ACTGTCTCCA | 153540 |
| TTTTACAGAA | GTGGAGGTTC | AGCCTCAGGA | ATTTCACTAA | ATTCGCCAAA | TTCTTACTAC | 153600 |
| CAGCAGATAT | CATTGCCAGG | CAGTGTCACA | CTTAATATC | TTCTAATCAA | TAAGATAACC | 153660 |
| CTAAAATTGA | TTATCATATA | TAATTTCCTT | CTCATATATA | GTTTCATACT | ATCATATATA | 153720 |
| GTTTCCTTTG | TTTCAGAAAT | TGGACTCCCT | CAGGGTGGAT | AAGGAGACAT | GGTGGTGTCC | 153780 |
| TGGCCTAAGT | ATTGTTGGAA | TCCTCTAGTC | AGAGGCCTGA | TGTGAGGTGA | AGTGGACAGT | 153840 |
| GAAACTGCCT | TTGCAAAAAT | CATAACTGAG | AAAATTATTA | CAGTGAAAGA | GATCTTACCT | 153900 |
| AACCGACTCC | ATCTAACGTC | TAAACTCCAA | GCTGTCCTTT | TCATTCCTGA | GTTTGGGATT | 153960 |
| AACTAACTTT | GGGAGGAGCT | TAGTTTATAC | TTTTGCTTTT | AAACAAAAAC | AATAACAGCC | 154020 |
| CTTTCAGAAA | CAAACCCCTT | TCCTGCCTGG | GGACCAGACT | GCTTTTGCAG | GACTAACAAA | 154080 |
| TTAGCCACAA | GATTATAAAT | TATGGTTTAG | GAGTCATGCA | GCTGGAAGCT | ACAAGATTCT | 154140 |
| AAACCTCAAA | TTGCTCCTGG | GGATAAAATC | ACTATTTTAA | AACCTAAGAT | CAATGCTTGA | 154200 |
| GCTATTTTGC | AGACCCTGAA | CACAATGGAT | TAGCTGGCAC | CACCCATATA | GATAAACTGG | 154260 |
| ATTATCTGGT | CTTGAGTCCC | CCACCCCACC | ACTCCCAGGA | ACTGATTTAG | CACAAGAGGA | 154320 |
| CAGCTTAGGC | TCCCTATAAT | TTCATCTCTG | ACCCAACCAA | GCAGCACTCC | CGACTCACTG | 154380 |
| GTCCCCTACA | ATCAAATTAT | CCTTAAAAAC | TTTGGTCCCC | AAATTCTCAA | GGAGACTGAT | 154440 |
| TTGAGTAATA | ATAAAACTCT | AGTCTCCTGT | AGCGCTGGCT | CCTTATTGCA | ATTCCCTGT | 154500 |
| CTTGATAAAT | CAGCTCTGTC | TAGGAAGTGG | ACAAGGAGAG | CCCGTTGGGT | GGTTACAATA | 154560 |
| GGACAAACCA | ATAAAATATA | AAGTATTAGA | GACACTACCT | GGGTTTCAGG | AACAGGTCAG | 154620 |
| AAAAAGTGTT | TTCTTGGAAA | ACATCTGGAT | TCTGCTGCAG | AGCAAGTATT | TGCTTGTGTC | 154680 |
| TTCCCAGAGT | ATAAAAGCTG | TCCTGTCCAA | GATAGTTGCC | ACTAACCATA | TGTGAGTATT | 154740 |
| AAGCATTGGA | AATGTGGCTA | CTCCAAACTG | TGATGTGCTT | TAAGTGTAAA | ATACACACCA | 154800 |
| GATTTCAAAG | AACTAGTAAA | ATAACAAAGT | AAAAACTCAA | TATTTTAATA | TTAGATACCT | 154860 |
| TGTTGAAACA | ATTTTTGGTT | ACACTGGATT | CAAATCATTA | AAATAGATTT | CTTTTTTCAC | 154920 |
| TTTTTAAAAT | GTGCCTATTA | AAAAATTTAA | AATTACATAT | GTGGACCCTA | TGTTTCTGAG | 154980 |
| GAACAGTGCC | AGGACATAGA | GGATAGTTAT | ATTCACTCAC | AGATCAAAAA | CTAGCAAAAC | 155040 |
| TATGAAATAC | CTAATAATTT | AATTTTTCAC | CTTAACTTTT | GGCATATTCC | ACAGATCTGT | 155100 |
| AGTATATTTG | AGTGTGATAG | CTTAGGAATA | AATATGATTG | GAACTCATTC | ATGTTTAGAG | 155160 |
| AGAAAGGGTG | TCAAATTGAG | AACCAGGCAG | ATACACCTAA | TCTTAAAATG | ACCCCAAAGT | 155220 |
| AAAGTGGTTG | AAGAAATTAA | ATCCCAAAGA | TTTTTGGTGA | AGAATGTTGT | AGTTTTCATC | 155280 |
| AGTATGTGTA | TGTTCAAATG | GAGATTAAAG | AAGGCAAAAT | AAGGCCGGGT | GCAGTGGCTC | 155340 |
| ACACCTGTAA | TCCCAGCACT | TTGAGAGGCC | AAGGCAGGCG | GATCATGAGG | TCAGGAGTTT | 155400 |
| GAGATCAGCC | TGGCCAACAT | AGTGAAACCC | TGTCTCTAAT | AAAAATACAA | AAATTAGCCG | 155460 |
| AGCACGATGG | CATGCGCCTG | TGGTCCCAGC | TACTAAGGAG | GCTGAGGCAG | GAGAATCACT | 155520 |
| TGAACCCGGG | AGGCAGAGGT | TGCAGCGAGC | CGAGATCACG | CCACTGCCCA | GCAGCCTGGG | 155580 |
| TGACAGTGAG | AGACTCCGTC | TCAAAAAAAA | AAAAAAAAA | AAGTCAAAAT | AAAAGAACTG | 155640 |
| TGGGCTGACA | ACTGTGGATT | AAGCATCAGT | TCTATTAAGA | AGGGCTAACT | TGAAGATGAA | 155700 |
| TCTTTTGAAG | ATACATTTTG | ACTCCAGCTC | TTTAGAGGAA | CAAAGTTTAC | CTTGATGTGA | 155760 |
| AATTCTTCAA | ATAAAAATTT | ATTGACTTTA | AATTTAAAAA | AAAATGCACA | CACACACACA | 155820 |
| CACACACACA | CAGCTAACTA | GCTACATCCT | TAATGACACC | AAGCTTTAGT | CCTTCACCCT | 155880 |

```
GAAGTGGGAA TGACAATGGC ACTTACTTCA AAGTGCTGTG ACAAGAATGT GTTTGAAAAT 155940
AAATATAGAG TAATCAGCAA CAGTGCTTGG CATATTGTAA ATAAGTGCTC AAAAAATGCT 156000
AGTTCCCAAA ACTGTTGTTG CCACTGTACC CTAAATCCCT ATTCTCTTCT GATATCCTTT 156060
AGTGATGTAA TTCTGTCTTG CACTGGGCCT GTTCATCTCT GGTATGAATT TCAACCACAA 156120
TGTCCTTACT ACATTTCCCT CAGGCTTATA TAGCCAAAAT ATCCAGAGCT TTGCCTAGGA 156180
GTGTATAATA TGATACTTCA ATTTGTAGCC ATGATAGCAC TGTGTATGAA AGTTTGGAAT 156240
AATGCGCCGG GCATGGTGGC TCACGCCTGT AATCCTAGCA CTTTGGGAGG CCGAGGTAGG 156300
TGGATCACTG AGGTCAGGAG TTCGAGACTA GCCTGGCAAA CATGGCGAAA CCCCGTCTCT 156360
ACTAAAAATA CAAAAAATT AGCCGGGTTT GGTGTCAGGT GCCTGTAATC CCAGTTACTC 156420
AGGAGGCTGA GGCAGGAGAA TTGCTTGAAC CGGGGAAGTG GAGGCTGCAG TGAACCAAGA 156480
TCACGCCATT GCACTCCAAC CTGGGTGACA GAGAGAGACT ATGTCTCAAA ATAAATAAAT 156540
AAATAAATAA AAAACAGAAA GTTTGGAATA ATGCATTACA AGTAGCCTCT AGTTTTTATG 156600
TTACTCATAG TTTTATCACA CAAGAACAAT GTCATAAATT TTCATGGTTG AATTATCAGT 156660
TGTTTATGCA ATATTCATTG ATGTTTTGG CTTATCAGCA GTGTTTCTGG AATTATTTGA 156720
ATATTATTAC CGTTTTTCAA AATTATTTTA TAAAACTAAT TTAAAAATCA AAATGATAT 156780
AATTACTAAT GTGAAATTAA ATATAAGTTT TGAAGAATAT CAGGATGTCA CCCCCAAATT 156840
ATTCTACTTT GGCATAAAAG TTATTTTCAG CTGAAGGCAA TTGAAAATCA ACAGGTGTAG 156900
GAAGAGGTCT CTGTCTTCTC TTTACCCAAA TTTCCCTTTG TGAAGGTGAC AGAAATTTCC 156960
CTTGTAAAAG TGTCCCCAAC TGCTATACCA GGAAAAAGAG AGCAATTCTT ATCACTAGAT 157020
ATGGAAGGTT GGCACTGAGA TGACTCTGCA AAAACAAACC TTACTACAAT TATTTCTATC 157080
TTTCATTTTA TCTTCCATGG TTTTTATTGC CCATGTATTT ATTTCCTTGT CACATTCCCA 157140
AATTCGTCAT CCCATGAAGT GCAAACTCCC TTTCCTTTGT TGGAATGGTG TATAAGTCTG 157200
TGAGTCTAAC CGCGTTTTTA AGGTTTCAAT TTTTTTTTCT TTGGGAACTC TGTGCATGTA 157260
ATATACTAAT AAAATTGCAT GCTCTTTTTT TCGCATGTTA ATCTGTCCTT TGTCAGTTAA 157320
ATTTGCAAGA CACTACTTAG TGAATCTAAG AGTACAGAAA AACATGTGTC CTCATTGACA 157380
GTTTCAAAAA CTAAGTAAAA TTGAGGCAAG AATCTTTTTC ATCTTAAAAT GGCCAATTTT 157440
AATTTCCAAA TGAATGGTTC ATTAGACCTA AGCCAGTAAG CTATGTGAAC AATTGTGATG 157500
GAATAAAACA AAACTAAAGA GCATGAACAA AATTGAGAAA ACATATGCAA GACTGAATCT 157560
AAAGGCCAAA TAGAATTGAA AATTTTTCTA ATTTTTAACT CTATAAATTA AAGGAATGTG 157620
TTTCATTTGA CGAGTTTCAT CTGTGGAAAC ATGTTTGCAG AAGACATTCG AGGTTAGGAT 157680
TAATTGAAAG TACATAAATC AAATGGATTA AGACCCCAAA GGGCATTGAA GGAAAATTAG 157740
AAAATCAGCT ATTTTGCTT GGGTTGATTC CTCTCCTGAC TAACTCTTGG AGATGATAAG 157800
AACATCAATT AAATGGGTAG CCATGAAAGT ATCTAAGGGA GAAAGGAACA CAGAAGTTCA 157860
ATGTACCATA ACTTTATTTT TATTTATTTA GTTTTTTGAG AGAGAGTCTG GCTCTGTCGC 157920
CCAGATGGAG TGCAGTGGCG TCATCTTAAC TCACTGCAAC CTCTGCCTCC TGGGTTCAAG 157980
TGATTCTCCT GTCTCAGCCT CCCGAGTAGC TAGGATTACA GGTGTGTGAC ACCACGCCCA 158040
GCTAATTTAT TGTGTGTTTT CATGGCCAGG CTGTATTTTC ATGGCCAGGC TGGTCCTGAA 158100
CTCCTGACCT CAGGTAATCT GCCTGACTCA GCCTCCCAAA GTGCTGGAAT TACAGGCGTG 158160
AGCCACTGCT TCCGGCTTTT TTTTTTTATG ACGGAGTCTC GCTGTGTCAC CCAGGCTGGA 158220
GTGCAAGGTC TCGCCTCACT GCAACCTCCG CCTCCCAGGT TCAAGCAATT CTCTGCCTCA 158280
```

-continued

| | | | | | | |
|---|---|---|---|---|---|---|
| GCCTCCCGAG | TAGCCGGGAT | TACAGGCGCC | TGCCACCATG | GTTGGCTAAT | TTTTATACTT | 158340 |
| TTAGTAGAGA | CGGGATTTCA | CCATCTTGGC | GAGGCTGGTC | TTGAACTCCT | GACCTCGTGA | 158400 |
| TCCACCCGCC | TAGGCCTCCC | AAAGAGCTGG | GATTATAGGC | GTGAGCCACC | GCGCCCAGCC | 158460 |
| TTTTTTTTTT | TTTTAATTGT | TTGATGTTGA | GATGGAGAAA | CAGGAGGAGG | TGGAAGAGAT | 158520 |
| CTTAATATAC | ATATGGAAAA | ATAAAAATG | GAATAACCAG | GAAAATTCTG | AAAAAGAAGA | 158580 |
| GTAATGAGAG | AAAATTAGCT | CTATCTGCTA | TTAAAGTCAC | GTTACAACAT | CTCAGTTAAT | 158640 |
| TAGTCTCCCA | AAGGGGAGAC | TAATGTAAAT | GCATGTTTAA | TAAACTGCAC | CCCCAGTGGA | 158700 |
| TGCCTGAAAC | CACAGATAGT | ACTGAACCGT | ATATACACTG | TTTTTTTCTA | TATACACATG | 158760 |
| GCAATGATGA | ATTTAATTTA | TAAATCAGGC | ACTGTAAGAG | ATTAGCAATA | ACTGATAATA | 158820 |
| AAACAACAAT | TATAACAATA | TACTGTAATA | AAAATGATTT | GAGTCTGTGA | ACGGTGGTTC | 158880 |
| ACGCCTGTAA | TCTAAGCACT | TTGGCAGGAT | GAGGTGGGCG | GATAACCTGA | GGTCAGGAGT | 158940 |
| TCGAGACCAG | CCTGGCCAAC | TTAGTGAAAC | CCCGTCTCTA | CTAAAAATAC | AAAAATTAGC | 159000 |
| CGGGCATGGT | GGCAGGCCCC | TGTAATCTCA | GCTACTCGGG | AGGCGGAGGC | AGGAGAATCG | 159060 |
| CTTGAACCCG | TGAGGCGGAG | GTTGCAGTGA | GCCGAGAACG | TGCCACAGCA | CTCCAGCCTG | 159120 |
| GGTGACAGAG | GGAAACTCCG | TCTCATAAAT | AAATAAATAA | ATATAAATAT | AAATTATATG | 159180 |
| ACTGTGATCT | CTCTCAAAAT | AGCTTACCGT | TTTACTTGTG | ATGATGTGAG | ATGACAGAAT | 159240 |
| GCCAGTAATG | AGATAAAGTG | AGGTGAATGG | AGTAGGCATT | GTGAAGTAGC | ATTAGGCTTG | 159300 |
| ATAAGATACT | ACAGATTTAG | GTATTAGTTG | AACACTTGCC | ATTTGTCACA | TAATCATCTC | 159360 |
| AGCATTGAGG | ATAGCACACA | ACACAATGTT | TAAAACAATA | CAATTCTACC | TTAAGAATTG | 159420 |
| TGGGAATGAC | TAAAGGAACA | AAATAGAAAC | CTGAGAAACC | TAAGACAGTC | CAACTGTCCA | 159480 |
| TGAAATTATA | GCGTATTAGC | CTATGACAAA | ACAGCCAAAA | TTGATAGGAG | CGTGGAGGGT | 159540 |
| GGCACGGGAG | GAAGAAGGGG | GAAGCAGAAA | TGAAAGTTCA | TAAATGGTCT | TGGGAAAAAT | 159600 |
| ATGTCCATAT | GTTAAACCTT | ACACCAAAAT | AGAGGGTTCA | CCATGTTAAA | CCGTGTTGTA | 159660 |
| ATGTAAAATT | AACAACACAA | AATTACTTAA | ACCATGGGAG | AATGTTTCT | CCTTCTTCCC | 159720 |
| TGCCTCTGTC | TTCCTGTCTC | TCTGCTTGCC | TCCCTCCCCT | TTCTCTTTCT | TGGGATGAAT | 159780 |
| CCGTGGTCAC | TATCACTAAC | AAATCAACTC | ACTATATTAA | TCATTGTGGA | GATGGTAGAA | 159840 |
| TAATTGAGCA | GCTTATCTCC | AGAAGCCCCA | GTCCCATAA | TTTAGGTCTC | ACCAAAATGT | 159900 |
| GCCCACCAGA | TTTTAAAAGA | AGCGAATATA | AGACGCTAGG | CTTTCTGTAT | TCAGAAGCAC | 159960 |
| CATGGATGTC | AAACAGAGGG | AACCATTAAC | GAAGGCCTTT | ATTAGAAATG | TCTCCCATTT | 160020 |
| ATCCATACAC | TCTTCATAGT | TAATAGTACA | AATACTGTTT | TCTGCATAGA | AACATTTGGA | 160080 |
| CTGCCAAACA | AAATACGTTT | AAAGGAACTT | CGATTTTTAA | ATGTTGCTGT | CTGTCTAAAC | 160140 |
| AGGATAAGCA | ACCGTAGTCA | TGCGAGGACA | AAATGGCTGG | CTAAAAGTTG | TGCTTTCGAT | 160200 |
| ACGCTCAAAA | TCGATACGCT | CAAACCTGTC | AGTTTAGCGG | AAGGCTACAT | GTTATGTGGC | 160260 |
| ACAAAAAACT | CCCTAGGTCC | ACGATTGCCT | TGGGTGGAGG | AAGGGCTATT | GCCGCTGTTG | 160320 |
| TGGCTGTTTT | TTAAATGCAT | TCCTTCGTTG | CCACAGGAAT | GAGAAATTAA | CAGCAGAGGA | 160380 |
| ATGTAGGACA | AAGGTACCTG | CACGCACTCT | CCTCCCAGGG | CTGGATGTTG | CCACTACCTC | 160440 |
| CAGGAGACAT | CAACTTGACT | ACCAACAACA | TGGAAAGCGT | CCGAAATCCC | AGACATTAAT | 160500 |
| ATAAAGAGAA | AAGAGGCAAA | ACTTTTAAGT | CACAGTAAAG | CAAAAAACAC | AGAATAAGCA | 160560 |
| ACGTCTTCCA | CCATCCAATT | AAATACAGAA | TGAAAGTCAT | GTACTAGAAG | AACGGACCAA | 160620 |
| CCCGGGAGCA | GGGCGGGACT | TTTGAAAATT | TTTTAGTCCA | ATCCGGACAT | CCCTTTAGAC | 160680 |

-continued

| | | | | | |
|---|---|---|---|---|---|
| TAAGAAACTG | GCTCTTGTTT | TGCGGTCTTT | TCTGCCGTTC | ACAGGCCTGG | GGCGGGACTG 160740 |
| CCATCCCAAA | ACCATCCGCC | AGCGAGAAAA | GCCTCCGGTC | AGGGACCTAG | AAGCCGCAAT 160800 |
| AAAGGTTTAA | ATGCTGTAAC | CTCACCACGG | CCACTCTCCA | ACCCCGTCAC | CCAATTCGTC 160860 |
| TGATACCTCA | GTAACTCCCA | TACGACTAAC | CTTAAGTAAC | AGGGCAGAAC | AAGAAAAGGC 160920 |
| AGATAGTAAA | GAAATTATCC | AGCTCTTTTA | TTGAGATCAG | TGGTGGCTCT | GAAAAGAGCC 160980 |
| TTTTGGGTTT | TAGAAGTAGG | CGTTCGCCTA | TTTCTTCTTG | GGCGCCGCCT | TCTTAGGCTT 161040 |
| GACAACCTTG | GGCTTAGCGG | CCTTGGGCTT | CACAGCCTTA | GCAGCACTTT | TGGCAGCTTT 161100 |
| CTTGGGCTTC | GCAACCTTGG | CCTTCTTTGG | GCTCTTAGCC | ACTTTCTTGG | TTACAGTGGC 161160 |
| CGCGGCCGGC | TTCTTCGCTT | TCTTCGGTGT | TTTCTTAGCG | CTCTTCTTCG | GAGTTGCGCC 161220 |
| GCCAGCCGCC | TTCTTGGGCT | TCTTGGCTGC | CCCAACTGGC | TTCTTAGGTT | TGGTTCCGCC 161280 |
| CGCCTTTTTA | ACCTTGGGCT | TGGCTTCCCC | GGAGGCTGCC | TTCTTGTTGA | GTTAAAGGA 161340 |
| GCCAGAAGCA | CCGGTGCCTT | TCGTTTGCAC | CAGAGTGCCC | TTGCTCACCA | GGCTCTTGAG 161400 |
| ACCAAGTTTG | ATACGGCTGT | TGTTTTTCTC | CACATCATAG | CCGGCGGCAG | CCAACGCTTT 161460 |
| TTTCAGAGCA | GCCAGAGAAA | CTCCGCTACG | CTCTTTAGAG | GCGGCCACAG | CCTTGGTGAT 161520 |
| GAGCTCTGAC | ACCGGGGGAC | CAGACGCCTT | ACGAGGCGTA | CCCCCAGCCT | TTTTGGCCGC 161580 |
| CTTCTTCTTT | ACAGGGCCT | TCTCCGCAGG | AGGCGCGGCA | GCGGGAGCGG | CAGGAGCAGT 161640 |
| CTCGGACATG | TTGAGAATCA | AAAACTCGGG | TACAAGTGGC | AAAGCGCCGA | TGAAGCAGCG 161700 |
| CCTGGGCAGG | GCCGCTGTAT | ATATAGAGCG | CAGGCGCGCT | CTGATTGGTG | CTCTGGTCGC 161760 |
| CCGCCTGGCT | GGCAGGCTCT | GAGCCGCTGC | GCTGCTCCCA | AGTTGTGTTT | GTTCCACCTC 161820 |
| ACAAAAGGGG | AAAAATATTA | AAATTCCCCG | CACCAAATCA | CTTGGGTTTG | GTCAGGAAAG 161880 |
| GATCTCAGAA | GCCTCGGGCT | TCATGCTCTT | CATTTATTTT | TTCCACAAAC | ACAAAAACAA 161940 |
| CGCGTCCAGG | CGTCCCCAAT | TCCCCCAACT | CCGAAGGAAG | TCTGGGGCAG | TCAGAGACCA 162000 |
| CTTTCTGTTT | TTCTTATAAA | TTACCTGTTC | GCTCCTTTGC | CCCTGAAGGT | TCTTTTTCCC 162060 |
| AGGGGTGGTT | GGGCACATGC | TTCCCTTATT | TTTGAAGAAA | AAAGCGAAAT | GGTTTCCACC 162120 |
| TAAATTTTCA | TGATAATTCT | GTTTCTTCAC | AAGGGAAGTA | ACACAGGTCC | TCTGTGAATT 162180 |
| CTTCGTGCAG | TCGCACAGGA | ACTGTGGACT | GGGACAAGGA | TTCCACGGCC | AGTCCAAAGC 162240 |
| AATTAGGGCG | GGATGGGAGG | GGGTTCATGA | GCCTTGCTAG | GGTCCGGGGT | GGTGGGGGC 162300 |
| TACAGACTTA | AATCTTTGAT | TTGAAGACAT | TGAAACTATC | AAATCCCTCT | TTTCATAGAT 162360 |
| GGGGGTGGGG | CATCCTTTTC | ACTTCTCTAC | AGGCGAGAAA | TTGGGCTCTT | TTTAAAGAGC 162420 |
| TCTGAGGTCC | CCCTCTGAGT | TGTGTAAGGC | AGGAGGTCTG | GCCCTCAAGA | TAGAGATCAT 162480 |
| AAAGGAACAA | GGGAGAGCCC | TTAAGCCTGC | AAAAAAGCCA | ATAGATTTGG | CAGTTAGAGG 162540 |
| CACTGAGATA | ATATGTTTTC | AAAGAAAACA | AGCATTTTTT | ATTTATTTAT | TTTTGTACGC 162600 |
| TGCAATATAG | AAATGAATTT | CAGCCCATGA | AAATTGTAGG | TTACTTTCAG | TAACCATACC 162660 |
| TTACGCAAGT | TACCATATAG | GACAATCTCC | AGTTGGGAAC | TCAAATATAT | CTTTTGAGTT 162720 |
| GCAAATAAAG | CAACTGACTT | TAATAAAACA | CACTCTTGAC | TTTTAAGATG | AACAATGTAT 162780 |
| TTGAAATTTA | TTTTTTTAAA | TAGCAAAATT | TAACACAGAA | AGACAAGAAA | AGTACCAGAA 162840 |
| CATGTAATTT | ATTATAAGAT | CTGTTGTTGA | TGAGCTGAAA | AATCACCTCT | TCTCATCCCC 162900 |
| TCTGAAACTA | TTCTGTTCTA | AAGTTTGCTA | CTTTAAGGTT | CACTACTTCT | TATTTACTC 162960 |
| TCCGACCCCA | AGTAATTGCT | ATTTTTTTCT | TGAGATTAAA | GGCAAAGTAA | ATTGTCTGCC 163020 |
| CATATATTTG | ATATAATTAT | AGATTCATAT | TTAGGGACAA | AGGTAATATT | ACAACTCCCC 163080 |

| | | | | | | |
|---|---|---|---|---|---|---|
| AACAATTTCT | GCTCAAATAT | ATGTTTTCAT | GAAAATATGT | GTTAAAGAGA | ACAGCCTTAG | 163140 |
| ATTGTGGGAA | AGTCAAAAGG | GAACCTACAA | ATAAGAGTTC | AATGACAAAT | GAAAAGTGAA | 163200 |
| ACATCTTTTA | GACTAAGGGT | GACCCCATTG | TTTTATTAAA | TAACATTTGT | CCAACATTTG | 163260 |
| TAAACATTGT | CTGCTTGTGT | GCTTATGTCC | TCTGGGAATT | AACAGTCTAA | TGAGATTAGT | 163320 |
| GATGGATGAA | TTAGCAGTGG | TGGAAAAACA | CTTAGACCGG | CTATTCCTCA | GAGTGACAGG | 163380 |
| GTATAAGAAT | TATACAAAAT | TATGGAAAGT | GTATAAACAA | TTGAAGCACC | TGCATCATAC | 163440 |
| TAATATATTG | TAGTAAAAGA | AATAATATAA | GGCTGGGCCC | CGTGGCCCAC | GCCTGTAATC | 163500 |
| CTAGCACTTT | GGGAGACTCG | GGGGCGGATC | ACCTGAGGCC | AGGAGTTTGA | GATCAGCCTA | 163560 |
| GCCGACATGG | TGAAACACCA | TCTCTACTAA | AAGTACAAAA | ATTAGCTGGG | GGTGGTGGCA | 163620 |
| CTCAGGAGGC | TGAGGCAAGG | GAATCGCTTG | AACCCGGGAA | GCAGAGGTTG | CAATGAGCCG | 163680 |
| AAATGACGCC | ACTGCACTCC | AGCCTGTGCA | ACAGGGTGAG | ACTCAGTCGA | AAAAAAAAGA | 163740 |
| AAGAAAGGAA | CAATATAAGA | ACATGTCACT | TAGGCCAGGC | TTGGTGGCTC | ACGCCTGTAA | 163800 |
| TCCTAGCACT | TTGGGAGGCT | GAGGCGGGCA | GATCGCCTGA | GGTCAGGAGT | TCGAGACCAG | 163860 |
| CCTGGCCAGC | ATGGTGAAAC | CCCATCTCTA | CTAAAAAAAA | TACAAAAATT | AGCCTGGCGT | 163920 |
| GGTGGCAGGC | AACTCTAATC | CCAGCTACTC | AGGAAACTGA | GGCAGGAGAA | TCATTTGAAC | 163980 |
| CCGGGAGGTG | GAGGTTGCAG | TGAGCCGAGA | TTGCCTCGTT | GCACTCCAGA | AGCCGAGATT | 164040 |
| GCCTCATTGC | ACTCCAGAAG | CCGAGATTGC | CTCATTGCAC | TCCAGCCTGG | GCAACAGAGC | 164100 |
| AAGACTCCAT | GTCAAAAAAA | AAAAAATAAA | ATAAACATTT | CACTTAGATC | TTATTCTATG | 164160 |
| TGCAATGAAC | CCCCTTCTCA | TTTAAAACTC | AGCTAAGTAT | ATCCATCATG | AAAATAGCTA | 164220 |
| TGAAACGTCT | TGATTACCAG | GTAACTGGAC | CTTCTTTCAC | TATAAATTGG | TGTCCTGGTT | 164280 |
| TATAAATCGA | CATGTAAATT | TAATCGCTGT | GATTCAGTTC | TCTAATATGA | TTTTTCTAGT | 164340 |
| CGACTCAATC | TAATCACATC | TCTTTATATG | CAAATCTCAA | GTCCAGACCT | CAAGCCATTA | 164400 |
| GGACATCCAG | CCACCCAGAA | TCTTGTCCCC | AACCTCCTGG | CAACATGGTG | GAGGCCAGAA | 164460 |
| GACAGAGAAA | CATGTAACCA | ACCCTTTTCT | AGATCCTTTA | TAAAGTGTGT | TGAAAAAGTT | 164520 |
| ATGCAAAACT | TAAAAGCAAC | GCAAAAATAT | TTCTCCATAT | CCTTCCAAGC | TATATTAGAG | 164580 |
| AATTATCTAA | AAAGCCTACT | TATGGGGTAC | CTGATGATGT | AAGGCAATAC | TAGACAGTAA | 164640 |
| AATAGAATGT | GAATCACATA | AATACTTTCC | AGATTTCTAG | TGGTCACATT | GAAAGAATGA | 164700 |
| AAAGAAACAA | GTAAAATTAA | TTTTAAGATA | TTTTATTTAA | CTTAATATAT | CTAAACTATT | 164760 |
| ATCACTTCAA | CATATAATAA | ATAAGCTAAA | AAAAAAGACA | GTTGACATTC | TTTTTTAAAT | 164820 |
| GATAAATCTT | CAGAACCTGG | TGTGTATTTT | ACACTTTTAG | AACATTTTAA | ATCAGTCTAG | 164880 |
| CTATAGTCCA | AATGGTCAAT | GATCACGTGT | AGCTAGTGGT | ACCTTATTGG | ACAACACTGT | 164940 |
| CCTACGTGAA | AGTAACTCTG | ACTTAATGTT | TACATTTTAT | TGGGTCCAGA | CTATCTAAAA | 165000 |
| GTAAACATTC | ACTTGTAGAA | GTTTAATAAA | TTAATAAGGA | TTTTGTCATA | GAGATGGAAA | 165060 |
| TGAATTCTTA | ATATAGAAAA | AATGACCCTA | AAAGTTATTA | TTGTATTGCC | TAATAAGTCA | 165120 |
| TTAAACAACT | TTATATCTGA | TTTTCCCTTC | CTCTTCCAGT | ATACATCCTT | TCCCTGACCA | 165180 |
| AATACATATT | TTATTCTCCC | GTATCTTCCT | TTGACCTAAT | TGTGATTCTG | CTTCCTCCTT | 165240 |
| CATTAATGAA | TTAAATCATT | CATTGACACA | TACACAAGCT | CACTATATAT | AGTACATATA | 165300 |
| TGTCAGTCAT | GTTTTTAACT | TCCTGAATGT | TGTACTTTGA | CACTTGGTTG | TTCAATTTCG | 165360 |
| CCTAAGAGCT | CTGAATCAGA | ACCTTTAGAA | GCCATTCTGA | AAAACTGGAA | GATACAAAGC | 165420 |
| TTTTGACTAT | CAACTCCATA | GCAACCTGAT | ATCTGGTTGG | TGTTCCATGG | AAACTGTATT | 165480 |

| | | | | | | |
|---|---|---|---|---|---|---|
| TCTCAAATTT | TGAAATAAGA | TTGAACAAGC | CTGTGAGCAA | CAACAAAAAA | AAAGTCTATT | 165540 |
| AGAATGACCT | CTGGCCGGGC | GGGGTGGCTC | ACGCCTGTAA | TCCCAGCACT | TTAGGAGGCT | 165600 |
| GAGGTGGGCA | GATCATGAGG | TCAGGAGTTT | AAGACCAGCC | TGACCAACAT | GGTGAAATTC | 165660 |
| CGTCTCTTCT | AAAAATACAA | AAATTAGCTC | GGCATGGTGG | CGTGCATCTG | TAATCCCAGC | 165720 |
| TACTTGGAAG | GCTGAGGCAG | GAGAATCACT | TGAACCCAGG | AGGCGGACGT | TGCAGTGAGC | 165780 |
| TGAGATTGCG | CCACTGCACT | CCAGCCTGGG | TGACAGAGCG | AGACTCTATT | TCAAAAAAA | 165840 |
| AAGAATGACC | TCCAAGGGAA | AGTTCAGATT | AAGGATGTGG | TCGTCCCACC | CAAAACTGAT | 165900 |
| GTCCTCAAGA | AAGCCACAAA | CAAATTGAGG | ACACAGTTAA | AATATTGTAA | TGCAATATAT | 165960 |
| TGTGTATTCT | TTTATTTACA | CACACATCAT | AAATATTATA | GGTTGACTAG | TTTTGTTTCA | 166020 |
| TGCCACACTC | TTCAGGGTCT | GGAAACCCTG | GTAGAAAAGT | TAAAAATGCA | GAGCAAAATG | 166080 |
| TCAAGTCCAA | ACAGCAGTAA | TGGGGCTAGA | GAGAGACTCA | AACAGCCAAG | ATATATTCAA | 166140 |
| AGGATAGTGA | GAGGAGTTGT | TAGGACAGGT | GTAAGGAATG | AGGGTGACAG | CTGGTTTTTC | 166200 |
| TTTCACTTTT | TCCTTCTACT | ATGCCAATTA | GAGTTCTTTG | TTTTTGATAG | AGACAGGGGT | 166260 |
| CTCACTATGT | TGCTCAGGCT | GGTCTCAAAC | TCTTGGCACC | AAGTGATCCT | CCTGCCTCAG | 166320 |
| CCTCCCAAAG | TTTTGAGATT | ATAGGTGTGA | ACCACCAAGC | CCAGCCTTAG | AGTAGGGTTC | 166380 |
| TGTCATCTTT | TGGATGTAGC | TAACCTAATA | TTACTAAATC | CTGTATAGGC | CAGAACTTTG | 166440 |
| AATGATTTAA | AGCTGTTTTT | TCCTGACTCA | CCAATTAATG | AAGCTAATAA | TAACAGCCAC | 166500 |
| CCCACTGGCA | GTGCCTGCCT | CAAAGAGTAA | GTGTTAGTGT | TGCTATCTGC | TTGAGACCAA | 166560 |
| CAATACAGGG | ACTCCAGGAT | ATTTTCAGCC | TAAATAAGAT | TGTAGGGGCT | CTTGTCTGTT | 166620 |
| GCCTGGCTTC | AGCCCCATAA | ACTTTTTTT | AACATATAAC | CCAGAGCCAC | AGTTTTGCTC | 166680 |
| ATATTTCAAT | CTTTGAAGGC | AAATGGCCAA | CAATTAGATT | AAACCTGAGG | CTAAATATTT | 166740 |
| CCTCACCTCA | AGGGCTGAGA | CGAAAGTTAC | TGCATCTGTA | TTCCCTAACA | CGCCCTCAAA | 166800 |
| ATGGGTTGCA | GAAAACAACA | GAAAATATAC | TAAAGCACAC | AGTAGGAGCA | TAATAAATAG | 166860 |
| TGATTAGCTG | GGTGCAGTGG | CATGCGCCTG | TAGTTCCCGC | TACTCTACTC | ATGAGGCTGA | 166920 |
| GGCAGGAGGA | TCACTTTTGC | CAAGCAGTTT | GAAGTTGCAG | AGAGCTATGA | TCACAACACT | 166980 |
| TCACTCTAAC | CTGGGCAACA | GAGCAAGACT | CTGTCCAGAA | AAATAAATAC | ATAAATATAA | 167040 |
| AATTTAAAAA | TATAAATAAA | TACATAGAGA | GTATTACAAA | AGGAACAATA | TATTGCAAAA | 167100 |
| TATATTTACC | TAACATTTTG | AAATTGCCAT | TATAATTGTA | TAAGTGACAT | AGGAAACTGG | 167160 |
| GTCATTAACA | GCTATCTTAT | TCTTCAAGCT | TCTTTCAAAT | GATGTCAAAG | CATTTCAGAA | 167220 |
| AGTCAAACCT | ACCCTCAAAG | GATAAGAATT | TGTCAATTGT | GAGGATATGC | ACATTTTTAC | 167280 |
| ACCTTCTCAA | TCTGTGTCTA | TATGAAGGCA | GTTATAAAGC | ACAAGATGCA | AACGTATATT | 167340 |
| AGGCAATAGT | CTTCATCAGA | ATAAGTACAT | AACCTGACAC | AATGACTATA | TTGGAAGAAA | 167400 |
| CATGGAAATG | CAAATTTCAA | TAGATTGGTT | GACATTATTT | TTTAATGTCT | AGTTTTTTAC | 167460 |
| TGTGCTGTGT | TTTTACACAC | TTAATGAGCA | CTTGTTAAGC | ACAGGACACC | AGGAGAAATA | 167520 |
| ATAAAAACTA | AGATCAGCCT | AGCAGTGTGT | CCTCTCAAGA | ACTTATACCT | GGTGGGACAG | 167580 |
| ATACAGACAA | ATATAACCAT | CATACAGTGT | GAGAAATCGA | TAGAAAAGAC | ACAGCCACTG | 167640 |
| AGAGCACAAA | AGAATAAAAA | CATAAAATGT | TAATGTGCTG | GCTAAACGTT | TGCCTTCAAG | 167700 |
| TATTTACCAG | TCTAGCTGGG | AAAATAAGAC | AGAAGACAAC | AGCCTAAAAT | AGTGGTTCTT | 167760 |
| AAACATTTAG | ATATCAGGAC | TTCTTTACAC | TCCTAAAAAC | TATCAGGCCT | CCAAAAAATA | 167820 |
| TTTTGCTAAA | TATAGGCATT | TATCACTTTG | GAAAACAAAG | CTGAGTATTA | ATTATTTAAT | 167880 |

```
TATTTATATT  AATATTTATT  TGATAACCTT  TAAAATATTA  TAAAATTAAT  ATTTATTTAT  167940
AATGCATATA  TGTGATTATA  TAGTTCATAT  GTAGCCATAT  ATTTATCATA  TATACCATAG  168000
ATTTATGTTA  TATATTACAT  ATGTATGAAG  AAAAAATGGA  AAGTAAACCC  AAAAGTTCCC  168060
CATTCCCTAA  CCCATTCAAA  ACCCTGGAAG  TCCCAGGCTA  ATCTGAAACT  TGTAAAACTG  168120
CCTGCATGTA  GAGAGCACAG  CTGAGCTGGT  AGTGTGGAAG  AGCAGAAAGA  CAGCAGTTCT  168180
GGAGCAAGGA  AGCTTTATAT  TTAATCCCAG  TTTCTCCATT  CATGAGCTTG  GTTACCCTGC  168240
CAAGTTCCTT  CTCTGTAAAA  TGGGAATAAT  ACTCCCAGAA  ATACAGTGAG  GATTAAATTA  168300
GATAATGTGC  ATACAGTTCC  TGGGATTGGG  ATCAGCACAC  AGTAGCCTCT  CATTTGAGGC  168360
ATATTTGCAT  TAGATCCTTG  CTGTATGATA  TCCTTCTGTT  TCTTTCTTTT  TTTTTTTTT   168420
CCTTTGGTGA  CCCTAAGAAA  GATGGTACTC  TCCTTAACTT  GGAGGGCTGG  ATGCGAAGAG  168480
ACCAAATCCA  ACAAGCTGGT  TCATTCTTTC  TAATTATGTG  TGCTTCCCTT  AGCTGCCTCT  168540
GAAAGGATAC  AGGCCCTAGG  TACTAGCCCC  AAGAAGCCTA  ATGATAAGAG  ATAGAGCTGG  168600
ACCACCAGAG  AAGAGATGAG  TGTGTATGTG  TGTGTGTGCA  AGCAATTATA  TGTGTGCATT  168660
TAGGAGTGGT  AGGTGTGTAA  ACAGTCTAGA  ACACTCATTC  TCACTGTGAT  GTGAGGATGT  168720
ATCCCCACAT  CACTGTTCTG  GGAGCTCACT  CCTTGTCCAT  CATCCAAGCT  TATGATGGAC  168780
AATTCTTTCC  CAAGTGGGAA  AGAATTCTGA  TGACACTCAC  ATAACTACCC  AGTCCCAACT  168840
TTCTGTATCC  AAGGTGTGTG  CATACCTTTG  ATAGCAGGCA  GGTGTGCCTA  GCCAATATAT  168900
TAGGAGCATG  GTATTCCAGC  ACTCTGCACT  TTTTTACTAT  AGAATTCATC  TCAACCTGCT  168960
TACATTACAT  GAAAGTTTTG  ATTGATATCA  AATTTTTATT  ATGTTTGCTT  ATCAAAGGAT  169020
TTGTAATTAT  GCTTCAGTTG  ATACATAGAT  TGTTTATATT  TTTCATGGTT  ACTTGAAGCA  169080
CTTATATTTT  CCTCATACTT  TTACAAAGTA  ATCAAGGAAA  AATACAGAGG  CAGCTTAGTA  169140
TATTAGTCAA  AAGAATAATT  AGACTGTCTT  GGAACCTGGA  ATGTCTGAGT  TCAAATTCAA  169200
TTTTGCCGTT  TTACCAGCTG  TGTGACTTTG  GGTGAGTTAA  TAAACCTTTT  CGTGTCTCAG  169260
TGTTCTCACA  TGTAAAGAGA  CAATAATAAG  CCTACCTGTT  TCATGGGTCA  TTATGAGGAT  169320
TAAGGAGTTA  ACATTTAAAT  AGTTCTTAGA  ACAACCTCTG  ACATATTTTA  AGTACAAAAA  169380
TATATACATA  TATTAAATAA  TAACTTTTCT  AAAACATCCT  ACCTACAATC  TTGTGTGCAA  169440
ATTGGTGGCT  CAATTCTGCA  ACTGTTGTTG  GTGGTGTTGT  TGTTAAGCTT  TTGTTTGTCA  169500
TGACTGTTAT  CAGTAATATT  AATACAGACA  GTTAACTGAA  CCCTTCCTCT  GCACCAGGCA  169560
TTATATGGAC  TATTTTCATT  CTGACTCCCT  GCATTCTATG  AGACAACCAC  CATTGTAATC  169620
ATTCTCACGT  TGCCAATAAG  GAAATGGAGA  ATGAGAATTC  AGACTTCTCC  AAGAAGTGCT  169680
GCAGACTGAT  TATAAATCAT  GCATCCTAAA  CACACACATA  TTAAAGTATC  AACTAAATCA  169740
AACAGAATAA  AACTTTTGTT  TTTCTATCTA  CAAAATGCAT  GAATTAAAAT  ATGCCCCAAC  169800
TACTTAACTA  ATATATTTAG  TAAGTAGAGG  GATGGAAGCG  TTTTCACTCC  TTCAATACAT  169860
TCTTCATCAA  CCTCTCTCAC  CTTACCCCTC  TGTCACAGGC  ATTTCCTATG  TCATGCGGTT  169920
TTTCTGATGT  ACGCTAGGTG  GCAGTCAAAA  CCACGAACTC  TTGAAAGAGA  GTATATTCCT  169980
ATTTTTCTGC  AGCCTCAACC  TCCAGGGCTC  AAACGATCCT  CCTGCCTCAG  CCTCCTGAGT  170040
AGCTGGGGCC  ACAGGTGCGA  GCCACCACAC  CTGGCTAACT  TTTACATTTT  TGATAGAGAC  170100
GGGGTCGCCA  TGTTAGCCAG  CCTGGTATCG  AATTCCTGAC  CTCAGGTGAT  CTGCCCGCCT  170160
CAGCCTCCCA  AAATGTTGGA  ATAACAGGAG  TGAGCCACAG  TACCTGGCCG  GTAATTTTTA  170220
ACTTCTAGCT  ATACACTTAG  TTTTTTGTCC  TTTTCAGTGG  ACAGAAATTA  TAATGCCTGT  170280
```

| | | | | | | |
|---|---|---|---|---|---|---|
| TTGACAGGGG | ATAATTCTGA | GGCACTGGGA | AGCCATGAGA | CTGCATGGAT | TGCACAGGCA | 170340 |
| GGCAAGAACA | TGGGAAGGAA | CAAGTGTCTT | AGACACTTGT | CTCAGTGGTC | TAGAAAAATC | 170400 |
| ATGCTAGCTG | ATTCATTCAC | TCCACAAACA | ACTGATCAAC | ATCTTCAAGA | AGCCTAACAA | 170460 |
| TGTACTGAGT | TCAGGGGACA | AGAAAATAAT | TCAGACAGGC | TCTACCTTCA | TGGTGGTGTT | 170520 |
| TGAAGAATAG | GGATCTAGAA | AACGGTAGGT | AATAGTGGCT | GTGCAAAAGA | TATCAGAGAT | 170580 |
| GATATGAAAA | GGAGGGACTA | GACCATTTTA | CCCAGGAGTG | GAGGTTAAAC | ATAGGGTCTT | 170640 |
| TAAGGGAAAC | GTAAAAATAT | TAATTCTTTT | CATTTTGAA | GTAAAATGAC | CATCGCTTCT | 170700 |
| CGGCCGTTTG | GCTAAGAACA | AGTGAAGTAA | AATGACTGAG | GATGACAGAC | ATAAATACTG | 170760 |
| CTATACAAAC | ATGGTAGCAC | TGAAATTGGC | TCTTGCCTGA | CAGGAAGCAA | AATTATAAAA | 170820 |
| TTCATTATTT | AGATATATCA | ATAATGATGG | TGATCAGGCT | GTAATAATAA | TGTTATTAAT | 170880 |
| CATTATGTAT | CAATAAGAAT | ACAGGTGTGT | GACTTTACAA | TGTGCCTAAG | AGCAACCCAA | 170940 |
| TATTTGATT | GTAAACCACA | TTCCCTTAAA | CACACACACA | CCTCAAACAA | GACCCCATAA | 171000 |
| AGCAGACTGC | ACTAAAGTGG | AGGTTATGTA | AAAGTCCAAC | AGAATAAGAA | CCCTCCCCCA | 171060 |
| TTGTGTATTA | ATCTGTGAAC | TAAAAAAAAA | TTTCATTAAA | TTGAAAATAT | CTAATTGTCA | 171120 |
| ACTAGCAATT | TTAAAGAGTT | TAGGCAGAAA | ATGAAATATA | AAGCTTTTTT | TTAACTTTTA | 171180 |
| GATTTTTCAA | AGCTAGCAGA | ACTGCTGAAG | AATAACAATT | CAAAACATAG | GTTTGCTTTG | 171240 |
| GTTTCAATCT | CTGTAGCCAA | AGGCATTTAC | AATGTAGGAT | GTTGTTTGTG | CTTTCAGACA | 171300 |
| CTAGATGACG | CTCCAAATCA | AAATGCCGGT | AGTTGGACAG | CCCCTGATCA | AGCCGCCCGG | 171360 |
| CAAATCATTA | ACTGGGTTGA | CACTGTATTA | CTCAGCAGAT | TTCAAAACTC | ATTCACATAC | 171420 |
| AGAGTCTTTT | GGTGGACAAA | AATAATTATT | ACCCACAATT | GACAGTGACA | GTACTGAGAA | 171480 |
| GCTGGGAAAC | TGAAGTAGGA | CCCTGGAGCA | GCCAAGTACA | GAGACTGGCT | CCCAGGACCT | 171540 |
| TAGGAGTTAA | TACTATTCCT | AAAGAGAATA | AATTGTCAAA | TAGACAAGAA | ATTCATGTGG | 171600 |
| GTTGATGCAT | TCACTTCCCC | AAAACAATTA | TTAAGCAGTA | GAAATGATAA | CTACGCTGGT | 171660 |
| AGTGGAAATA | GTTTACAGTA | AAAGGGAGAA | GACATGCAAA | AACCAAAAAA | AAAAACGGGG | 171720 |
| CCGGGCGCAG | TGGCTCACTC | CTGTAATCCC | AGCACTTTGG | GAGGCTGAGG | CGGGCCGATC | 171780 |
| ACGAGGTCAG | GAGATCGAGA | CCATCCTGGT | TAACAAAGTG | AAACCCCGTA | TCTACTAAAA | 171840 |
| ATACAAAAAT | TAGCCGGGCT | TGGTGGTGGG | TGCCTGTAGT | CCCAGCTGCT | CAGGAGGCTG | 171900 |
| AGGCAGGAGA | ATGGCGTGAA | TCCGGGAGGC | GGAGCTTGCA | GTGAGCGGAG | ATCACACCAC | 171960 |
| TGCACTCCAG | CCTGGGCAAC | AGAGCAAGAC | TCCGTCTCCA | AACAACAACA | ACAAAAAAAC | 172020 |
| AGGCAGTGAT | GTTTTATGTG | GGTCAGTGTG | AAGTAGAGAT | CAAAGGAGAA | AACGGCCAAT | 172080 |
| CTTACCAAAT | AATGGATGCA | GAAATAATCT | TCATGGAGAA | GCCACTTTAA | TTATGTCTTA | 172140 |
| AATGAGAGTA | ACAAATTAAA | CATAAGAACC | TGTAGGGGCT | AAGGGAAAAC | TTACTCTTTG | 172200 |
| GCCTCTGAAG | AGTCGCTGAA | AACCACCGAC | AAGAGGAAGA | TTAATAGGAT | AAAATGCATC | 172260 |
| CAATTTATTA | TTATTATTAT | TATTATTATT | ATTATTATTA | TTATTATTAT | TTTTAGACGG | 172320 |
| AGTCTCACTC | TGTCACCAGG | CTGGAGTGCA | GTGGCGCAAT | CTCGGCTCGC | TGCAACCTCC | 172380 |
| GCCTCCCGAG | TTCAAGCAAT | TCTCCTGCCT | CAGCCTCCCC | AGTAGCTGGG | ACTACAGGCA | 172440 |
| TGTGCCACCA | CGCCCAGCTA | ACTTTTGTAT | TTTTAATAGA | GACGGGGTTT | CACCATTTCG | 172500 |
| GCTAGGGTGG | TCTTGACCTC | GTGGTCTGCC | CGCCTCAGCT | CCCAAAGTGC | TGGGATTACA | 172560 |
| GGCGTGAGCC | ATTGCACCCG | GCTGCATCCA | ATTTATTAAT | GTGTATATTA | ATAAATTATC | 172620 |
| CAATTTATAT | CCAATTTATT | AATGTGTATT | AACATGTACA | GGGGAAATTG | TCCATTTTTA | 172680 |

| | | | | | |
|---|---|---|---|---|---|
| TTTTTTAGAT | TCAACAAAGT | ATGGGCCGCC | GTGTAGAAAT | AGGATTGCTA | ATAAACAGAG 172740 |
| TAGGGAAACC | CAGCAAGGCC | TGTCTGTCTA | GATTCTTCTT | CGCCTCTCTG | TGCAGCATTC 172800 |
| CTTCCTTCTG | GATCCTCTCT | GGAATGCGGT | CTGGTGATCT | ATGATCAAAT | AAGGTAGTTC 172860 |
| AGATAATTTC | TTTATGGCCA | GTTTTTACAC | AGAAAAACAG | AGGGAAAGTT | AGAGTAATAT 172920 |
| TTTTAGGTTT | TATGGCTGGG | CTCTGGGGAA | AAGGTGTTTT | GATTTCTATG | ACCTAACTTG 172980 |
| AGGAAGAGGA | ATTCTCATTT | CTATGGCTAG | ACTCCGGGGA | GAATGGGACT | CAGAGACAGG 173040 |
| AGGGCAGGAG | AAGATCAGAG | AAAAACTTTG | GCTTCTGCGG | TCTTTATTTT | GGGGTATTGT 173100 |
| TTTCTGAGTT | CCAACAAACC | CCAAGGACCT | ACAAAGACTG | CATACTTTTT | TTTTCCTTTT 173160 |
| TATTAATTGT | GAGATAACCA | CAGCATAGGC | AATTTGTTTT | TTGTTTTTGT | TTTTGAGACA 173220 |
| GGATTTTGCA | TTGTTGCCCA | GGCTGGAGTG | CAGTGGCATA | ATCATAGCTC | ACTGCGTCCC 173280 |
| CAAACTTCTA | GGCTCAAGAG | ATCCTCCCAG | CTTAGCCACA | ACTGAGAGGT | GCTACTAGCA 173340 |
| TTTAGTGAGT | AGAGAACAGA | TATGACTAGA | GGTTCATTAA | GTGTTTTGAG | CCTTTACAGC 173400 |
| TTCAAAATTG | TCTTTGCTAA | CCCCTAACTT | TTGGATGCTA | CAGAGGGCCC | CTGGAGTATC 173460 |
| CAAAGGAGAG | GTAAACAGGA | TCATTTGACA | CGTTTAGTTA | TATAGGATTG | TTGAAATAAG 173520 |
| GTGATATTTG | ATCTTCAGGT | CATATTTCAG | TGAAAACTGT | GAATGTGTGT | TCCAAAATTA 173580 |
| TAGGGGATTT | CTAGAGTTCT | GATATCTGAG | TTTGTGTCAT | CAGTTATAAT | TAGAGTTATT 173640 |
| GTGTTAGGCT | ATTGTAAATC | ACAGAGGTGA | CTAAATTTCT | TTGTCAATTG | TGTTTTTGAC 173700 |
| TGTGACTACC | CTAGGACATT | TTAACATTCA | TAGACAAATG | TTGTCTTGTT | TTGAAACTCT 173760 |
| GCAAAGAATG | GATTATAACC | CTCAATTGCA | GGTTTCTGAT | AACTTTGAAG | ATTGTGAACA 173820 |
| GGAGTTAACT | AGGTGAGCTG | AACTATTGGA | AAACTAATCT | TCTTGACTCT | TGCCTCTGTA 173880 |
| CCTAATTCTT | CCTGGATGCA | GGACAAGAAC | TCAGGCAAAG | GTGCTGCAGC | ATAAAGTCTG 173940 |
| GCCAGAGAAA | CTGACACTCC | AGAGGTTTTG | TAACAATATT | TTATGTTAAA | TAATTTATAC 174000 |
| GTATTTCCTA | TTCTAAGCAT | TTCAAGTGAT | TGTAAAAACT | CAACTCATGA | AAACTTATAG 174060 |
| CTGAGATGAT | GTATCCTGTG | ATTTTAACT | CAACTTTATA | CCAATCTAAG | TTGATTAGCA 174120 |
| TTCTTACAAA | GTTAAGAAG | TTAAGATTTG | CCATATTAAG | TATTGTCTTA | AGATTTTAA 174180 |
| GAATTGAAAA | ATTTGGAGCA | GTTTTGTTCA | TTAGTCAATT | GGATACTTTA | AAAGTCCAGT 174240 |
| ATGTCAGATT | TAAAAATTGC | AATTTATAAG | TTTTCTTCTT | AAAGTTCGTC | AAATTGCAAA 174300 |
| AGCCTTGCCA | AAAATGAATG | TTAAAAATTT | GGTAGATTAT | TTGTTCTATG | GGTTCTATGG 174360 |
| GAAAAAATTG | GTAGATTAAT | AAATGCCAAT | AGTAAGCATT | GTAAATTGAA | TTTAAAAGTT 174420 |
| TAAGGAAGAG | CTATTAATTT | AATTTGTCA | TAATAATGAA | TTGAATGTTG | TTTTTAAGT 174480 |
| ACCATAGTAC | TTGCTGAATG | ATCTTTCTGT | ATGGAAAAGG | ACATAAAAAT | GCACATTGGT 174540 |
| AACATCAACT | CTATTTCAGC | GGCGGGATTG | TGGGGTGAGC | TTATCTCCAG | GTTTGGGAAG 174600 |
| GATGTGTTGT | ATCATCTGCC | TCTTGTGTGT | GTACTACCTG | CCATTGCTGC | TTGGCCACCA 174660 |
| GCATCCATCT | TGGTGAGTCC | TGTCTCCCTC | TAAAAGACTC | GAGCTGTGCT | GTTCAATCCA 174720 |
| GTAGCCCCTA | GCTACATGTA | GCTATTGTAA | TGAATTAAAA | TTAAGTAAAA | TTAAACATTC 174780 |
| TGCTCCTCAG | ACACCAGTCA | CATTTCAAGT | GCACAATAGT | CACAAGTGGC | CAGTAGCTAG 174840 |
| TTTTGAACAG | TGTGGAAAGA | TTTCTGTCAT | CACAGAGCAT | TCTATTATCA | CGTTGTAAAG 174900 |
| CATTCTCTAG | CTCTTGCAAA | CTTGTCAGAT | CCCTTAAAAG | TTCTTAAAAA | TAATTCATCA 174960 |
| TTCGAATTTT | GCTCAGACTA | ATTTTAGGG | AAGTCTTTTT | CTGGAGGCGT | GGACTTGTGA 175020 |
| TCTCCATAAT | TCATCCCTTC | TACTATGTTA | GTTACCTTGA | GCTGCTGTAA | TAAAATACTA 175080 |

-continued

| | | | | | |
|---|---|---|---|---|---|
| TAGACTTAGT | CGCTAAAAAA | AAAATAACTT | TCTCACAGTT | CTGGAAGCTC | AGAAGTCCAA 175140 |
| GATCCAGGTG | CTGGCCAATT | CAGTTTCTAG | GTGAACGCTC | TCTTCCTGAC | TTGTTGGTGG 175200 |
| CAGCAGCATT | CTCACTATGT | GCTCATGTGG | TGTCCTTTTT | GTGCTTGTAG | GGCTTAGGCA 175260 |
| GTGGAGAGAA | GGAGGAGAGA | AAAGAGTTTC | ACTGTTTTCT | CCTTTTCCCG | AGACAGTTTT 175320 |
| TGTGTAGCCC | AGGTGGACAG | CAATGGCTCA | CTGCAGCTTC | TTCCTGGGGT | CAAGCAATCT 175380 |
| TCCCACTTCA | GCTTCCAGAG | TAGCTGGAGC | TTCAGATGTG | TACCACCACA | CCCAGTTCAT 175440 |
| TTTTTAAATT | TTTAGAAGTT | GGGGGTCTCA | CTATTTTGTC | CAAGCTGGTC | TTGAACTCCT 175500 |
| GGGCTAAAGC | GAGCCTCCTG | CTTCAGCCTC | TCATAGTGTT | GGAATTACAG | GCATCAGCTG 175560 |
| CAGCACCTGG | CTCTATTGTC | TTTTTTTTTT | TTTTTTTGA | GATGGAGTCT | CTATCACCCA 175620 |
| GGCTAGAGTA | CAGTGGTGTG | ATCTCACTGC | AACTTCCACC | TCCTGGTTTC | AAGGGATTCT 175680 |
| CCTGCCTCAG | CCTCCCAGGT | AGCTGGGAGT | ACAAGCGTGC | ACCACCACAC | CTGGCCAATT 175740 |
| TTTGTATTTT | TAGTAGACAT | GGGGTTTTAC | CATGTTGGCC | AGGCTGGTCT | CAAACTCCCA 175800 |
| ACCTCAGGTG | ATCCATCCAC | CTCAGCCTCC | CAAAGTGCTG | GGATTACAGG | CATGAGCCAC 175860 |
| TGCACCTGGC | CTGTTGTCTC | TTTTAATAAG | GGCATGAATT | TCATCATGAG | AGACACATCC 175920 |
| TGATGAGTTT | GTCTAAATAT | AATGACTTCC | CAAACGCCCC | AGCTCCAAGT | ACCATCACAC 175980 |
| TGGGGGTTAG | GGTTTCAACA | TATGAATTTT | GCGACGGGGA | GTCAATTCAG | TCCATAGTAC 176040 |
| CTACTGTATT | AGTTTTCTGG | GGCTGCAGTA | ACAAAGTACC | TCAAACTCGT | TGGCTTAACA 176100 |
| ACAGATATTT | ATCGTCACAC | AGTCCTGGAA | GCTGGAAGTC | TGAAATCAAA | GTATCATCAG 176160 |
| GTTTGATTCC | TTCTGAAGGC | AATGAGGGAT | AATCTGTTCC | AGGTTTCTCT | CCCAGCTTCT 176220 |
| GGTATCCCCA | GACTCATTGC | TTGACTTGAA | TGGTGATTCT | CCCTGTGTCT | ACTCACCACA 176280 |
| TTTTCTCTCT | ATAGGTGTCA | GTCTCTGTGT | ATGACATTTC | TCCTTTTTAT | AAGGACACCC 176340 |
| TTTATGTTGG | GTTAGAGCCC | ACTCTTATCT | TAACTGATGA | AGTGCAAAGA | CCCTATTTCC 176400 |
| AAATAAGGCC | ACATTCACAG | GTCCTGATAC | AGGAGGGGA | AAGTGCTGGG | AAGGGAAGGG 176460 |
| CATGGTCCCT | TTAAATGATA | TGGAAGTGGG | GAAGGGAAGG | GCGTGGTCCC | CGGCTAGGGC 176520 |
| TCCACCCCCA | GGCCTGTGCC | CAGGGACCAC | GGTGAGGACA | GGCATTTTTG | TTTTCCTGCC 176580 |
| CAAATGTTGC | ATTTCCCAAG | ACCTCCCCTG | GCCTGCCACA | AGACACGAAT | AGCTGGACGT 176640 |
| CCAGGGGAGC | ACACTGGCAG | AAGAGCACAC | AACAAACGTT | TGCCTGGCAA | AATGAGGCGG 176700 |
| AATTTGACTG | GGGTGGTTGG | AGGAGAGCCT | GGGCCACTGA | GTGGCTGACT | CCAAGGGAAA 176760 |
| ACTTTCCCAC | TCCATCCACT | TTTGGCTTTG | CCCAACTGCT | GAGAGCTACC | TCCACTTAAT 176820 |
| AAAACCTTGC | ACTCTTTCTC | TAAGCCCAGG | TGTGGTCTGA | TTTATTCCGG | TACACCAAGG 176880 |
| CAAGAACCTG | GGATACAGAA | AGCCTTCTTC | TGTCCTTGGG | ACAAGGTAGA | CGGTCTAATT 176940 |
| GAGTTGGTTA | ACACCAGCTG | CCTATAAATG | GCAAAACTAA | AAGAGCACCC | TGTAACACAC 177000 |
| ACCCACTGTG | GCTTCAGGAG | CTGTAAACAT | TCAACCCTAG | ACACTGTGGT | GGGGTCATGG 177060 |
| GGTTGGAGAC | CCACAACCTG | CCCGTCTTAA | TGTTCCCCTA | GAGGTTTGAG | CAGCCAGGCA 177120 |
| CTGAAGAAAT | TAGCCACACT | CCTATCACAT | GCCATGCGAG | CGGGACAAGG | GAACTTTTCC 177180 |
| CATTTCAGTA | CTGGTGGTTA | GGACTTCAAC | AACTTTATTT | TTGTGGGAAT | GCATACTTCA 177240 |
| ACCCATATTA | TGAGGGTTCC | TAGAATGTGG | ACTGCTGAGG | CTGAAGCACT | ACCTAAGTGC 177300 |
| CTGAGGCCAG | CCTGCAGTTG | GTTTCTGGCT | CTCATGAGTT | AGCTAACATC | TCGGGAGAGA 177360 |
| GGAAGACAGG | CCTAGGAAGA | GCAGAGCCCA | CGATTCATTC | TTCATTCCAC | CTCTGCTCTT 177420 |
| CAGAATCTCC | TTCAGTCTAT | GTGATGAGCC | ATCAGACCTC | TTGGTGGGAA | ATGGTGCTGC 177480 |

| | | | | | | |
|---|---|---|---|---|---|---|
| CGTGCCTAGC | CCTTTTCGAT | TGTGCTACCA | TGCTGAGATT | ACTGAGGGAC | CAGGAAGGCC | 177540 |
| TGGACTCAGA | CCATATAGGG | TGCCACCCTA | GTGGGAATGG | AACCTGTCAG | TGCTGGGTGA | 177600 |
| ATGTGACCGT | CCCATGAGGA | GAAGACAGAT | ACTCTTGCCA | AGCTGAGCAT | GGAGACCTGA | 177660 |
| TGGGACACTC | ATTATCATGA | GGGGATGAAG | ATCCAGGCTT | CCAAAGTTGG | TACCACAGGG | 177720 |
| TGGCTATGGC | ATGAACAGGG | GGTTAGGATG | AAGGACCCAG | AATCTAACAT | GCTGGAGAGG | 177780 |
| TAGGGAAAGG | AGTCAGAAAT | TCAGTCTTGT | TGAACCCTAA | ATATTGCATC | TCTCTCTCTC | 177840 |
| TTTATTTTTT | TTTTCTGGAG | ATGGGGGTCT | GGCTCTATCA | TCCAGGCTGG | GGTGTAGTGG | 177900 |
| CATGATCTCT | GCTCACTGCA | GTCTCCGCCT | TCTGGGTTCA | AGAGATCCTC | CCACCTCAGC | 177960 |
| TTCCTGAGTA | GCTGGGACTA | CAGGTGCGCG | CCACCACTCC | CAGCTCATTT | TTGTACGTTT | 178020 |
| TTGTAGAGAC | ACGGTCTCAC | CATGTTGTCC | AGACTGGTCT | CGATCTCCTG | AGCTTAAGCG | 178080 |
| ATCTGTCGCC | TCGGCCTCCC | AAGAAGGATT | GGGATTACAG | GCCTGAGCC | ACTGTGACCA | 178140 |
| GCCAACATTG | CATCTAATTT | TAGGGTATTC | ATCTGACTTT | CCTGAACACT | GCTTCTTGGG | 178200 |
| TGCTCATTTT | AGCAGGCATT | TGGCCATAGG | TAGATTTAAA | GTTTGGTGG | GTTTGTTGT | 178260 |
| TGTTGTTGAG | ACAAAGTGTC | ACTCTGTTGC | CCAGGCTGGA | GTGCAGTGGC | AAGATCTCAG | 178320 |
| CTAACTTCAA | CCTCCATCAC | TGTGCTTCAA | GTGAGTCTCC | TGCCTCAGGC | TCCCGAGTAG | 178380 |
| CTGGGATGAC | AGGTGTGTGC | CACCATGCCC | TGCTAATTTT | TTATATTTTT | AGTAGAGATG | 178440 |
| GGGTTTCGCC | ATGTTGGCCA | GGCTGGTCTG | GAACTTCTGA | CCTCAGATGA | TCTGCCCGCC | 178500 |
| TCAGCCTCCC | AAAGTGCTGG | GATTACAGGT | GTGAGCCACA | ACCCCTGGCC | AACGTTTTCT | 178560 |
| GAAAAAGCTA | TTCTAATCAG | GTAGGAAAGA | TGGGAAGCGG | GGTGGCGGGG | TGTACTTTTT | 178620 |
| TCTGCATATT | CAGTTGCAGG | GTCCCAGACC | AGGGAACAAT | CTTCAATCTC | TTACCTTCAA | 178680 |
| TCTCCCTTCA | TGGAAGTCAG | TGCTCAGCCT | GGCCATTTAC | TGTGTGCAGT | AGGTGTGATG | 178740 |
| TAGAAAGCCT | CTAAACCTCC | ATGCCTACCT | GCCAGGAACA | ATATACACAA | AGGTGTGTGT | 178800 |
| GTGTGTGTGT | GTGTGTGTGT | ATCTTACGGA | TTCTTCCACG | TAACTATGTG | GACATCTAAT | 178860 |
| CCATTGCTTC | CAACTCTATA | TTGTGCAGTG | ACTTCATTTT | ACCTCCACCT | CTCTCAGTGA | 178920 |
| AGGATATCAG | TCAGCCCACA | CTTTCCTGTC | ACCTTTATGG | GATATGTTTG | AGATGATATT | 178980 |
| TGGAAAATAT | TCCCAGGGAG | TGGGCACTCC | CATCAGCAGT | GTATGAGGAT | TCCTGAGTCT | 179040 |
| CCATATCCAC | ACCAATACTG | AGCATTATTC | AGCTCTCTAA | TTTGTTAATG | CTCTCTTTTA | 179100 |
| AATGCAAAAG | GACACATCAC | TTTACCTTTC | TTTCATTACC | AAGTGCTTTG | GATTTCCTG | 179160 |
| TATCTAAATT | TCTTGTTCAT | TTATTTCATA | TATATATATA | TATATATATA | TATATATATA | 179220 |
| TATATATATA | ATTTTTTTTT | TTTTGAGAC | AGAGTCTCAC | ACTGTCACCC | AGGCTGGAGT | 179280 |
| GCAATGGTGT | GATCTCAGCT | CACTGCAACC | TCTGCCTCCT | GAGTTTAAGT | GATTCTCCTG | 179340 |
| CCTCAGCCTC | CCAAGTAGCT | GGGATTATAG | GCACCCACCA | CCACGCCCGG | CTAATTTTTT | 179400 |
| GTATTTTTTG | TAGAGATGGG | GTTTCACAAT | GTTGGCCAGC | CTGGTCTCAA | ACTCCTGATC | 179460 |
| GGCCCGCCCT | GGCCTCCCAA | AGCGCTGGGA | TTACTGGCAT | GAGCCACCGC | GCCCGGCCTC | 179520 |
| ATACATTTTT | TATGTGGAGT | TTCTGTTTTG | TTCTTCTTGG | CCTTGTGCAT | TCTAATTACT | 179580 |
| CATCCTTTCG | TCTGATTCAG | ACATTTAATT | CTCTACCATC | CTTACAGCAG | TGTCTTAACT | 179640 |
| TTATCCATGG | GATCCTTCAT | TGAACCGGAA | TTCTTAATTT | TGACACAAAC | AAATTTATCA | 179700 |
| ATTTCTTTTT | TGTGTGTGTT | TTTTTTTTCT | GTGTGTGGTT | TTTGTTTTTC | ACATTTCTGA | 179760 |
| GTATGACCTA | GATTTATCCT | TTGATAACTT | CTTCTCTCTT | CCCCATTTTC | CTCCACTGGA | 179820 |
| GGTCAGCTAT | ATGTGTGTGA | GAGGGTTAGG | TATATGTGGA | TATATAGAGA | AAGTTTAGGT | 179880 |

| | | | | | | |
|---|---|---|---|---|---|---|
| ATACATATGT | GGAGAGGTCA | GATAAATATG | TATATATGGG | AGAGATATTG | GGTATATATT | 179940 |
| TTGGGGAGGG | GAGGTCAGGT | ATATGTGGAC | ATATGGGGAG | GGGAGACCAC | AGCTCTCCTG | 180000 |
| GAGTCACCCT | CTTCCTCTTC | CCTTCTGGGC | AGGTAACGGT | GGGGAGTGAG | AGGGTGTTCC | 180060 |
| TCCCTTCTTA | TTATTAGCCC | CTGGGTACTT | TAGGGTCTCT | AGTGGTTATT | TTTCACAGAA | 180120 |
| TTTTAACTGA | TAACTAATGA | ACAAATGTTT | TCCCCACAGA | AATATCTTTA | CGCCTTTTAC | 180180 |
| AATCATTTTT | ATTTTCTATG | CCATAACTTT | ATTAATATTT | GCCAATTTAC | TTGGGGTAGG | 180240 |
| ACTTTGAAAA | TTTTGTTTAA | ATTAAGGGAG | GAGACCACCC | CTCATATTGT | CTTATGCCCA | 180300 |
| ATTTCTGCCT | CCAAAGAAAG | AAAAAGTAAA | AATTAAAAGG | GAGAAATGAA | ATCCACAGGC | 180360 |
| AAACAGCCCG | GCACCGCACC | CTGGGTCTGG | TTAAAGATCG | ACCTTTGACC | TAACAGGTTA | 180420 |
| TGTTATCTAT | AGATTCCAGA | CATTGTATGG | AAAAGCATTG | TGAAAATCCC | TGTGCTGTTC | 180480 |
| TGTTCTGTTC | TGATTACTGA | TGCATGCAGC | CCCAGTCACG | TACCCGCTGC | TTGCTCAATC | 180540 |
| AATCACGACC | CTCTCATGCA | GACCCCCTTA | GAGTTGTAAG | CCCTTAAAAG | GGACAGGAAT | 180600 |
| TGCTCACTCA | GGGAGCTGGT | TTTTGGAGAC | AGAGGTGATT | AACGGACGGT | CAAGGCAGCC | 180660 |
| CCTTAGGCGA | CTTAGGCCTG | CCCTGTGGAG | CATCCCTACG | GGGAACTCCA | GCCAGTTTGA | 180720 |
| GCGACACAGA | TCTGGAGAGC | GCTCCCAGGT | AGGCAATTGC | CCCGGTGGAA | CGCCTCACCA | 180780 |
| GAGCAGCACG | TGGCAGGCCC | TCGTGGAGGA | TCAACGCAGT | GGCTGAACAC | CGGGAAGGAA | 180840 |
| CTGGCACTTT | GTTGTCAGGG | CATATTCCAA | AAGCATTAAG | GCCTTCCTAT | CAAAAATCCT | 180900 |
| TAACCCAGTA | ACCCGCGGAT | GGCCCAAATG | CATTCAATCT | GTAGCGGCAA | CTGCTTTGCT | 180960 |
| AACAGAAGAA | AGTAAAAAAA | TAACTTTTAC | AGGAAACCTC | ATTGTGAGCA | CACCTCACCG | 181020 |
| GTTCAGAAGT | ATCCTAAGGA | AAAAAGAAAA | AAGAAGATGA | TTTAACATTA | ACCACTGAAA | 181080 |
| ATTCTCTTAA | CCCGGCAGGT | TTCCTAACAG | GGGATCTAAA | TCTTAATTAC | CATACAAAGC | 181140 |
| TCTGACCAGA | CCTAGGGGAT | TCCCTTCAGG | ACAGGAGGAT | AGATGGTTCT | TCCCAGGTAA | 181200 |
| TTAAAAAAAA | AAAAAAGCCA | TCTATACCAA | TTCTAAGTTA | ATTTGGACTA | AATAAGGTCT | 181260 |
| TATTAATAGC | AAAGGATAAT | TGAAATCCCA | AACTTACAAG | GTTTTCAACA | AAAGTAAAGT | 181320 |
| TTGCTAAAAG | TTAACAGTGT | AACATGTATT | ATAGTAACTT | CTAATCTTGT | GGCCTTAGAC | 181380 |
| AGTCTAGTCC | ACAGACATAA | AAGAAGTTCG | CTTTGGAAAA | GAATGGTTAT | CATCCTCGGA | 181440 |
| AAAAAAAAAA | AGGAAATAAA | GAGGAGGCAG | AATTTATATA | AAAAGAATG | TTGTATGGAA | 181500 |
| AATCCTTGTC | CTGAGATAAA | TTAACTAGTT | GTTAAAGAA | AGGGATGTTT | GCAATAAGTC | 181560 |
| AGAAAGTTGA | GGCATGTCGA | AGAATTGTCT | GTGAAAGTCA | TGAAAAAAT | GTGTGTTAGA | 181620 |
| AAAATAAATT | TATGTAAGAA | ATGTTGTATA | ATTTAAAAGT | AATTAGGCCT | CCTTCTAAAT | 181680 |
| GTAAAACTAT | TGAATAAACA | GTTTATGTGC | AAGGTATGTA | AGGAAAGTAA | AATATACCTT | 181740 |
| TGGTAAAAGG | ATTATGAGGA | TGCATAAGAA | TGTGGATTTT | TACCTACATT | AAAAGGTTAC | 181800 |
| AAAAATTGTT | TTGAAGGTTT | AAGCAAGTTT | TGAAACCTTA | ATTGTAAAGA | AAATTCTGTG | 181860 |
| TCTAAACATA | TTGGCTAAAG | TTAAGGGTA | TCATACAGTT | TTTCTGTGAA | CTGAACATTA | 181920 |
| AAATAAAAAC | ACAACGGGTT | TTTCTTAAAG | CACTAACCTG | TTCTTTAACA | AAAATTATAA | 181980 |
| AAGGTTAAAG | AAAAGTCTAT | AAAAATCTTA | CCTTATGGTC | AGACATTAAA | AATCAAATAA | 182040 |
| ATATGTCTAC | AGAGTTTTAT | TAAAACTAAG | TTTAACATTA | ATAACACACC | AATATAAAGG | 182100 |
| TGAAATCTAG | CTTATCTGGT | ATAAACATAC | AAGAAGCGTT | GTCAAATATA | AAATGGCATT | 182160 |
| TGACTTTCTT | TGGTCTAAAA | ACTAATAAAA | ATAGGTGCTA | AAGGAAATTT | CTCAGTAAGA | 182220 |
| AGGCACCAAG | GACTATAAAG | TCCACTGCTG | ATGTCCCCAC | ATTTAAAACA | AAAGGTCAAC | 182280 |

-continued

| | | | | | |
|---|---|---|---|---|---|
| TTCTTAAAAG | TTATATACTT | GGTTTATCTT | CCACTTTCCT | TTCCCTCAAA | ACTAAAAGTC 182340 |
| TTTTAGCACA | TGTACCACCC | CTAGAATTTT | CTGTAAACCA | GCACCAGCCT | GAAGATCATG 182400 |
| TTCTCATCAA | AGGGTGGAAA | GAAGGAAAAC | TTGAGCCAGC | CTAGGAAGGA | CCCTACCTTG 182460 |
| TGCTGCTAAC | CACCGAGACT | GTTGTTCATA | CGGTGAAAAA | GGGATGGACT | CATCACACCC 182520 |
| GAGTCAAGAA | AGTGCCACCC | CCTCCAGAGT | CATGGGCCAT | AGTCCCAGGG | GAAAACCCTA 182580 |
| CCAAACTAAA | GCTAAGAAAA | ATTAACTCC | TTCATCTATT | CTATTACTCT | TTCTTCTTCC 182640 |
| CTCACTCTAT | TTCTGACCAT | CTAGTTATTA | ACATAACCAA | GTCAATTTTG | CCTCAAACTA 182700 |
| TTGAATTTAA | TGCTTGCCTT | GTTATACCCT | GTGGGGACTT | GCCAAGTCGA | AGACATCTCT 182760 |
| GTACTTCAGA | AAAGTACCTC | TGTCCCTCCT | GACTCTCCTC | AGACTGAGCC | TTAGTAAACT 182820 |
| GAGACCATTT | ATTCCAGAGA | GATTTCAATA | AAGACCCCAG | TGTCAACGAG | GAGTCTTGCC 182880 |
| CCCCGATGTA | GAGCTTTTAT | GCCATAGTTG | GTCGAATGTT | GTGTGGACCA | CTAAAGAGCA 182940 |
| AGGATGGACT | GCCCCAACCG | GTTTTTGTAA | TTTCCTAAAA | TCATACATTC | ATTTACTAG 183000 |
| AGGGTCATAG | AAGTTAAAGA | CTTAAAACAA | ACTTTGATAA | TTAAGCAGGA | TACCAAGATG 183060 |
| CAAATGCCCA | GTTGGAATGG | ATCAAATATT | CTGTCCACAC | ATTAAACAAA | ACCAATTGTT 183120 |
| ATGCTTGTGC | ACATGGCAGG | CCAGAGGGCC | AGATTATCCC | CTTTCCACTA | AGGTGGTCCT 183180 |
| CCTGTTGACC | AGGCATGGGC | TGCATGGTAA | CTGTTTTCCA | GGATTCTACA | GCCTGGAGTA 183240 |
| ATAAGTCGTG | CCAAGCTCTC | TCTGCTATAT | CCCAAAGTCC | AGCACCCTGC | AGGTCAACCC 183300 |
| CTGAGGGCCA | TCCAGCTTCC | ATCTCCCAAA | ACTAAGTTCA | CTTCTTGTCT | CTCATGACAG 183360 |
| GGAGGAAACT | TAGCATTCCT | TGGAGACCTG | AAGGGATGCA | GTGAGCTTAA | GAATTTTCAG 183420 |
| GAGCTTCTCA | ATCAGTCAGC | CTTTGTTCAT | CCCCAAGCGG | ATGTGTGGTG | GTATTGTGGT 183480 |
| GGACCTTTAC | TGGGCACTCT | GCCAAATAAC | TGGAGCGGCA | CTTGTACTTT | AGTCCAATTG 183540 |
| GCTATCCCTT | TCACCCTAGC | ATTTCATCAA | CCAGAGGGAG | GAAAATAAG | ACATCGTAAA 183600 |
| GCAAGAGAAG | ACCCTTATGT | GTCTTTCAAC | TCTCACATCT | ATTTAGATGC | AATTGGAGTC 183660 |
| CCACAGGGAA | TAGCAGATCA | ATTTAAATCC | CAAAATCAAA | TAGCTGCAGG | ATTTGAGTCA 183720 |
| ATATTTGGT | GGGTGACAGT | TAATAAAAAT | GTAGATTGGA | TAAACTACAT | CTATTACAAC 183780 |
| CAACAGCAAT | GAGTTTTCA | TGAGTTAAAA | GAAAAACTCA | TGTCGGCCCC | AGCCCTGGGG 183840 |
| CTACCTGACC | TGACAAAACC | CTTTACACTC | TATGTGTCAG | AAAGAGAAAA | AATGGCGGTT 183900 |
| GGAGTTTTGA | CCCAGACTGT | GGGGCCCTGG | CCGAGGCTGG | GCCTCCAAAC | AACTAGATGG 183960 |
| AGTTTCTAAG | GGTTGGCCTC | CATGCTTAAG | AGCCTTGGCA | GCAACAGCCC | TGCTAGCACA 184020 |
| AGAGGCAGAT | AAGCTAACTC | TTGGACAAAA | CCTAAACTTA | AAGGCCCTCC | ATGCTGTGGT 184080 |
| GACTTTAATA | AATACATCAT | TGGCTAACAA | ATGCTAGATT | AACCAAGTAC | CAAAGTTTGC 184140 |
| TATGTGAAAA | TCCCTGCATA | ACCATTGAAA | TTTGCAACAC | CCTAAAACCT | GCCACCTTGC 184200 |
| TCCTGGTATC | AGAAAGCCCA | GTTGAAAGTG | ACTGAGTAGA | GGTATTGGAC | TCAGTTAATT 184260 |
| CTAGTGGGCC | CAACTTCCAA | GACCATCCTT | GAACATCAGT | AGACTGTGAG | CTGTACGTGG 184320 |
| CAGCTTCGCC | AACGCCTGCA | AAGTGACTGA | AGAAGACAAC | AAGCCCTGCT | CCAGTCACAC 184380 |
| CCGGAAGCTG | ACTGGTCCAT | GCATGGCCGA | AACATGAGAA | AACTCATCAA | GGGACTCATT 184440 |
| TTCCTTAAAA | TTTGGACTTG | CACAGTAAAG | ACTTCAACTA | ACCTTCCTCA | GACTGAGGGC 184500 |
| TGTTCCCAGT | GTATACATCA | AGTCACTGAG | GTAGGACAAA | AAGTTGCTAC | AGTCTTATTA 184560 |
| TTTTATGGTT | ATTATAAGTG | TACAAAGACT | CTAAAAATAA | CTTGTTTGTA | TAATGCTATT 184620 |
| CTATACAAGG | TAGGTAGCCC | AAGAAATGAC | CAACCTGATG | TGTGTTATGA | CCCATCTGAG 184680 |

| | | | | | | |
|---|---|---|---|---|---|---|
| CCTCCCACGA | CCACAGTTTT | TGAAATAAGA | TTGAGGACTG | AGGACTGGTG | GGGGTTCATA | 184740 |
| AACGATACGA | GTAAAGTGTT | AGCCAAAACA | GAAGAAAAAG | GAATGCCCAA | ACAAGTCACC | 184800 |
| TTGAAATTTG | ATGCCTGTGC | TGTCATTAAT | AGTAATAAGT | TAGAAATAGG | ATGTGGTTCT | 184860 |
| GTTCATTAGG | AAAGAGGCTA | TATGGCAGAA | AATAAGTACG | CTTGTCATGA | ATTAAGACTG | 184920 |
| CGTGGAAATA | AATGTAGATA | CTGGTCTTGT | GTCATTTAGG | CAACTTGGTT | AAAAAATAAA | 184980 |
| AAGAATCCTG | TCCACCTTCA | GAAAGGGAAA | AGTGGCCCTT | CCTGTACCAG | TGGTCAGTGT | 185040 |
| AACCCCTTAG | AACTAGTAAT | AACCAACCCC | CTTGATTCTC | ACTGGAAAAA | AGGGGATCGT | 185100 |
| GTAACCTTAG | AAATAGTTGG | GGCTGGACTG | GATCCTTGAG | TAAATATGGT | GGTTTGAGGA | 185160 |
| GAAGTTTATA | AATGCTCCCC | TGAGCCAGTA | TTTCAAACCT | TCTTATGATG | AACTGAATGT | 185220 |
| GCCAGTACTA | GAAATTCCAG | GAAAAACAAG | AAATTTGTTT | TTGCAATTAG | CTGAGCATGT | 185280 |
| AGCCCAGTCT | CTCAATGTCA | CTTCATGTTA | TGTATGTATG | TGGAGGAACT | GTAATGGGAG | 185340 |
| ATCAATGGCC | ATGGGAAGCA | CGAGAATTAG | TACCTACAGA | CCCAGTTCCT | GATAAATTCC | 185400 |
| CAGCTCAAAA | GACTCACCCT | GATAACTTCT | GGGTCCTAAA | AGCCTCAATC | ATTAGACAAT | 185460 |
| ACTGTATAGC | AAAAGTGGGG | AAGGACTTCA | CCCTTCCTGT | GGGAAGACTC | AGCTGCCTTG | 185520 |
| GGCAAAAACT | GTATAATAGT | ACTATAAAAA | CAGCCACCTA | GTGGAGTTCA | AACCACACTA | 185580 |
| AGAAAAATCT | ATTTAGTAAA | TTCCCAAAGT | TGCAAACTGT | GTGGACCCAC | CCAGAGTCCC | 185640 |
| ACCGGGACTG | GACAGCCCCC | ACTGGATTAT | ACTGGATATG | TGGGCATACA | GCTTATGCCA | 185700 |
| AATTACCTGA | CCAGTGGGCA | GGTAGTTGTG | TTATTGACAC | TACTAAACCA | TCTTTCTTCC | 185760 |
| TACTGCCCAT | AAAGACAGGC | AAACTCCTGG | GCTTCCCCTG | TATATGCTTC | CCGCAAAAAA | 185820 |
| AAAAAAAAAA | AAAAAAAAAA | AAAAAAAAAA | AGCATAGCTA | TAGAAAATTG | GAAAAATAAT | 185880 |
| GAATGGCCCC | CTGAGAGAAT | CATACAATAT | TATGGGCCTG | CTACTTGGGC | ACAAGACGGC | 185940 |
| TTGTGGGGAT | ATGGGACCCC | CATTTACATG | CTCAACTGAA | TCATACGGTT | ACAAGCTGTC | 186000 |
| TTAGAAATAA | TTACTAATAA | GACCAGCAGA | GCCCTGACTA | CTGTGGCCTG | GCAAGAAACT | 186060 |
| CAGATGCAAA | ATGCTATCTA | TCCAAAATGG | ATTGGCTCTC | GACTACTTGC | TAGCAACTGA | 186120 |
| AGGAGGGGTC | TGTAGGAAAT | TTAACCTTAC | TAATTGCTGT | CTACACATAG | ATGATTAAGG | 186180 |
| GCAAGTAGTT | GAAGACATAG | TTAGAAATAT | GACAAAAGTG | GCACATGTGC | CCATGTAGGT | 186240 |
| GTGGTATGGA | TTTGTTTCTG | GGGCCATGTT | TGAAAAATGG | TTCCGAGTGC | TAAGAAGATT | 186300 |
| TAAAACTCTT | ATAATAGGAG | TTATAATATT | AATAGAAACC | TGCTTACTGC | TTCCTTGTTT | 186360 |
| GCTACCTGTA | CTTCTCCAAA | TGATAAAAAG | CTTCATCACT | ACCTTAGCTC | ACCAAAATGC | 186420 |
| TTCAGCACAA | GTGTACTATA | TGAATCATTA | TCAATCTGTC | TTTCAAGAAG | ACATAGGTAG | 186480 |
| TGAGAATAAA | AGTGAGAACT | CCCACTAATG | AGTGAGATTC | TCAAAGGGGG | TGAATAAGTG | 186540 |
| AGGCGACCAC | CCCTCATATT | GTCTTATGCC | CAATTTCTGC | CTCCAAAGAA | AGAAAAGTA | 186600 |
| AAAGCTAAAA | GGCAGAAATG | AAATCCACAG | GCAGACAGCC | TGGTGTTGCA | CCCTGGGTCT | 186660 |
| GGTTAAAGAT | TGACCCCCGA | CCTAACCGGT | TATGTTATCT | ATAGATTCCA | GACATTGTGT | 186720 |
| GGAAAAACAC | TGTGAAAATC | CCTGTTCTGT | TCTGATTACT | GGTGCATGCA | GCTGCCAGTC | 186780 |
| ACATACCCCC | ACTTGCTCAG | TCGATCATGA | CCCTCTCACA | CAGACCCCCT | TAGAGTTGCA | 186840 |
| AGCCCTTAAA | AGGGACAGGA | ATTGCTCACT | CAGGGAGCTC | GGTTTTTGGA | GATGTGAGTC | 186900 |
| TTGCCAAAGC | TCCCAGCTGA | ATAAAGCCCT | TCCTTCTTTA | ACTCAGTGTC | TGAGGGGTTT | 186960 |
| TGTCTGTAGC | TTGTCCTGCT | ACAAAAATAA | GTGTTAAACA | TGAGTTTTAT | ATTACCTCAT | 187020 |
| AGGTGGAAGA | AGACAGGCCA | AAAAAGCTGT | TTTAACAACA | ACAAAATGCA | CAAATATTTA | 187080 |

-continued

| | | | | | | |
|---|---|---|---|---|---|---|
| TACTAACAAG | ACAGATATCC | ATTGCAGTAT | GACACGAGAA | ACAAATAAAT | GAGACAAGCA | 187140 |
| GTCAATTCAG | ACATTTTAGG | AAGTGATTTT | TACAGAACAT | AGTGACAATT | GCTGAGATCT | 187200 |
| GGTAGCCTTG | CAAGATTCCT | TTGTTATAAT | AAAAATAACA | TTGGCAAAGA | CCATTTTATG | 187260 |
| ATGCAGACTT | CTGCTTTTTT | AAAGTTTGGG | GGGAAGGGGA | AACATTTTTA | TTCTATAATG | 187320 |
| CTGAAATTTC | ATTTTCTTT | TCTCTTTTTT | AAGACCAAGT | CTTGCTCTCT | CACCAAGGCT | 187380 |
| AGAGTGCAGT | GGCGTGATCT | CAGTTCACTG | CAACCTCCAC | CTCCCGGGTT | CAAGCAATTC | 187440 |
| TCCTGCCTCA | GCCTCCTGAG | TAGCTGGGAC | TACAGGCACC | ATGCCCGGCT | AGGATAACAT | 187500 |
| TTTTTGTTTT | TAGTAGAGAT | GGGGTTTCAC | CATGTTGGCC | AGAGTAGTCT | AGAACTCCTG | 187560 |
| ACCTCAAGTG | ATCTGCCCGC | CTCATCCTCC | CGAAGTGCTG | AGATTACAGG | TGTGAGGTAC | 187620 |
| AGCATCTGGC | CTCATGCTGA | GATTTCTTTC | ATTACCAGTT | CAAACACCTT | TCACTTTTCA | 187680 |
| AGGCACAAGG | AGAGGAATTC | CATGTGTTGA | CACTGGGAGG | AAGGGTACAG | ACCTACTTAA | 187740 |
| AAGATTCAAA | ACTTCTATGA | CAGTAAAAGA | AATGTATATC | AAGTTCCTTA | GGGCTGCCGT | 187800 |
| AACAAAGTAC | TATCAACTGG | GTGGCTTAGA | ACAAAGAAA | TTATTCTCT | CACAGTTACG | 187860 |
| TAGGCCAGTT | GAGATCAAGG | TATTATCAGG | GCCAAGATCC | CTCTGTAGCC | TCTGGGGAAG | 187920 |
| GATTCTTTCT | TGCCTGTTTC | CACTTCTAGC | AGCTTCCTGT | GTTTGGTTTG | TGGCAGCATA | 187980 |
| ACTCCAATCT | CTGCCTCCAT | CTCTACCTGG | CCATCATCCC | TCTGTGTCTG | TGAGGACCCC | 188040 |
| AGTCATTGGT | TGGAGGACTC | ACCCTATTCC | ACTATAATCT | CTTCTTAACC | AGTGAACTCA | 188100 |
| CCGTATTCCA | GATAAGGTCA | GGTTCACAGC | TACTGAGGGT | TAGGACAGAG | TATCTTTTGG | 188160 |
| GGAGATGCAA | TTCATCCCAT | AAGTGGGTGG | AAAAGGATGA | TTAACAAGTG | GTATGTGGGG | 188220 |
| ATGTATTGTT | TTGCATCTAC | GTAGCTCTCA | CCCCATTTCT | TTCCACAACA | CACATTTGTC | 188280 |
| ACTCTATTCT | TTATTAGGTT | TACAGAGAAA | AGTAGATCTT | CAACCACTTT | CCTGGGATGT | 188340 |
| GGATACAGCT | CTTTTTTTGG | AGACAGGGTC | TCATTCTGTC | ACCTAGACTG | GTGTGCAGTA | 188400 |
| GCACTATCAT | GGCTGACTAC | AGCCTCAATG | TCCCAGGCTT | AAGTGATCTT | CCCAACCTCC | 188460 |
| TGAGTGGCTG | GGACCACAAG | TGTGTGCCAC | CACACCTGAC | TAATTTATT | TTTTAATTGT | 188520 |
| TTTGTGAAGA | CAGCATCTCC | CTATGTTTCC | CAGGCTGGTC | TTGAATTCCT | GGGCTCAAGC | 188580 |
| CATCCTCCTG | CCTCGGCCTC | CCAAAGTGCT | GGGATTACAG | GCAAGAGCCT | CCATGCCTGG | 188640 |
| CCTTCAACTC | TTGACCTTAT | GAACACAGCC | CTATACCAGT | TCCCTTCATG | CATGTGCCTA | 188700 |
| TAAGCTAAAC | CCTTCCCAAG | TGTACATGAA | AATCTGAAAC | CCCAACAAAT | ATGGCCTAAT | 188760 |
| TCTAAATCTG | ACTTTCCCAG | GAGTAATTTT | TGTCATTTCC | AGCTTACCAG | CCTTTGTGAG | 188820 |
| TGTTGAATTT | CAGCATTTCT | GTTTGCTTGC | AGCAGAAGGT | GGAGCCAGGA | TAGGGTGGCT | 188880 |
| CAAGATTAGA | GTTTCTTCCT | TAACAGTTCA | GTCAACTTTT | TAATCTTGGA | TTTATAGCTT | 188940 |
| CCTACCTGCT | CTCTTAAAGG | TGAAATGATC | TATTCACCTT | CAGACCATTT | GCCCTCGGGG | 189000 |
| TCTCACTGAG | CAATCTATGG | CTTAAGTCTT | CTAAGTCTCT | TAATGGCCAA | ATACAATGGA | 189060 |
| CAATTTTCAG | GTATATCTGA | CACCATTTCT | CTGCAGCCTT | TGGCACCTAT | AACCACTCCA | 189120 |
| TGGCTTCCAC | AATGTGATTG | GTCATTTCTT | TTTTGTTTAT | ATGACAAGTT | TTTATTCTTC | 189180 |
| TTCTGCCTGT | TAAATGCGCC | TGACCCCCAG | TGTTCTGATT | TCACTATTT | TTCTTAAAAA | 189240 |
| AAAAAGTTTA | AATGAAAAAA | GTTTCTTATG | AAAATATTAA | AACATATACA | AAAATAGAAT | 189300 |
| AGACATTGAT | AATAGATCCT | AAAATTCCTA | GGGAAATTCA | GCAGACTGAG | AATAGCTAAT | 189360 |
| ATAGTCTTCC | AAAAAAAGAT | CAAATTTGAA | GTTGAGAAAC | TTCTTGAATT | CAATTTACTA | 189420 |
| AAAAGCTATA | GTAATCAAGA | CAGTGTAGTC | CTGACATAAA | GATAGGATTA | TAGTCTGGGT | 189480 |

```
GTGGTGGCTC  ATGCCTGTAA  TCCCAGCACT  TTGGGAGGCT  GAGGTGGGCA  GATCACCTGA  189540
GGTCAGGAGT  TCCAGACCAG  CCTGACCAAC  ATGGTGAAAC  CCCGTCTCTA  CTAAAAATAC  189600
AAAAATTAAC  CAGGCATGGT  GGCAGGTACC  TGTAATCCCA  GCTGCTTGGG  AGGCTGAGGC  189660
AGGAGAATTG  CTTGAACCTG  GGAGGAGGAG  CCAGTGGCCG  GGATTGGGCC  ACTGCACTCC  189720
AACCTGGGCA  ATAGAGTGAG  GCTCTGTCAA  AAAAAAAAA   AGATAGGATT  ATAGATTATA  189780
GCATAATGGG  ATAAAATTGA  GACTCCAGAA  ATAAACTCTC  ACATTTATGG  TAGATTGATT  189840
TTTGATAAGG  GTGCCAAAAC  ACTTCAATGA  AAAAGAGTC   TTCTCAACAA  GTGATGGTGG  189900
AACAACTGAA  TAACCACATT  TTTGTTCTAT  CTGGGGCCCT  GATTCAAAAA  CCCAGGCAAA  189960
GATGGAGAGA  AATCAGAACT  CTCATACACT  GCTGATAGGA  GGATAAAATG  CTTACTTTGG  190020
AAAAGAATGT  GGCAATTCCT  CAAAAGGTTA  AACAGTGTTA  CCATATGACC  CAGCAAACCC  190080
ACTTCTAGAT  ATATAACCAA  AAGAAATCAA  AACATAAGTC  TACAAAAAAA  CTTGTACATA  190140
AATGTTTATA  ACAGCACTAT  TCCCAATAGC  CATAAAGTAG  AAACAAACCA  ATGTCCATCG  190200
GCTGATGAAT  GAATAAATAA  ATATGTTGT   GGTATGTCCT  TATAATAGAT  ATTATTGGTC  190260
CATGAAAAAC  ATACATAAAA  ACATTATGCT  AAATGAAAGA  AGCCAGTCAC  GGCAAAGCAA  190320
TATATTATAT  GCCTCTATGT  ATACTAAATG  TTCCAAATAG  AAAGAAAGTA  GATTAAAGAT  190380
TGTCTAGGGC  TGGGAGGGGA  GGAGGAGGAG  AATGGAGGAA  TCTGGGAGGC  GATGAATTAA  190440
GGGTACTGAA  TTAGGGGAAC  ATGGTTTCTT  TTTGGGGAGA  TAGAAATGTA  AAATTTTGGT  190500
AATGGTTGCA  CATCTCTGTA  AATATACTAA  AATCCATTAA  TTTTTGCATT  TTATTTTATT  190560
TATTTTATTT  TTGAGACGGA  GTTTCGCTCT  TGTTGCCCAG  GCTGGAGTGC  AATGGCATGA  190620
TCTCGGCTCA  CCACAACCTC  CGCCTCCCAG  GTTCAAGCGA  TTCTCCTGTC  TCAGCTTCCC  190680
GAGTAGCTGG  AATTACAGGT  GCATGCCACC  ACACCCAGCT  AATTTTTTTT  TTTTGAGATG  190740
AAGTCTTGCT  CTTGTCTCCC  ATGCTGGAGT  GTGATGGCAC  GATCTTAGCT  CACTGCAACC  190800
TACGCCTCCC  GGGTTCAAGC  GATTCTCCTG  CCTCAGCCTC  TAATGTAGCT  GGGATTACAG  190860
TTGCCTGCTA  TCACGCCCGG  CTAATTTTTG  TATTTTTAGT  AAAGACGGGG  TTTCACCATG  190920
TTGGCCAGGC  TGGTCTCGAA  CCCCTGATCT  CAGGTGATCT  GCCTTCCTCG  GCCGCCCAAA  190980
GTGCTGGGAT  TACAAGCGTG  AGCCACTGAG  CCGGGCCAAT  TTTTGCATTT  TACATAGATG  191040
AATTATATGG  TATGCTAATT  ATATCTTACC  AAAAATTGAA  AAAAGGAAT   AGTACTATCA  191100
GCCCCAATGT  GCCCATCATC  AATATTCTAC  ATGTTTCCAA  TGTTATTGTA  TCTGTTTGCC  191160
TACAGTCGAG  GCCCTGATAT  CCTGTTTGAT  TTTCTTGAAT  TGCCAAAATT  TGCATACATG  191220
CTTACAAAAA  TAATGCCTGT  TGAATTTGCT  AGATATGTAA  AGGTTTGGAG  CAAATCAGGT  191280
GTATTAAATT  TATTAATATT  GTTTGAAATG  TCTAAGGCAA  TAATTCCCAA  ACTTCGTTGA  191340
GGGAGAAGGA  AAGCTTTTAA  AATCCCATTG  CCCAGGTGGC  ATCCCATACT  GTTACTGGGA  191400
ATTATGCATT  GGGATGGATC  CTTTAACCGA  GGAGATTATT  ATAGCCGGAG  CTCTGAACCA  191460
GCAATCTCAG  TTCTTGTGAT  AGTGAGCAAA  GAACTACAAA  CTAACACCAA  AATGCAAGCT  191520
TAAAGCAAAG  TTTATTGAAG  CACAATAATA  CACTCTGAGG  GACAGCGGGC  TTATTCTGC   191580
GAAGTGAACT  CAGCACTTCT  TTACAGAGCT  CAAGGTGCTT  TTATGGGGTT  TGTGGGGAGG  191640
AGTTGAGGTT  TGGGCTGTAT  CTGAGTGACA  GGATGATGTT  ATTTGATTGA  AGTGTATAGC  191700
TATACAATCT  AAAATTAAAC  TGTGCATGGT  CTTACCTATA  ATTTGTTAAG  AAAAGCCTCC  191760
CAGGGATGGG  GGGGCAAAAC  TGTATGTAAA  TTCTATTATA  ATGATGGCAT  GATGAACTTG  191820
GGGTGAACTT  GAAGACAGGC  TTTTGTGTTG  TTGGGCATGT  GCCACCTTAG  GGAATTTCCA  191880
```

-continued

| | | | | | | |
|---|---|---|---|---|---|---|
| CCTGTACCCT | CCTTTCTCTT | TCTCCAGGAT | ATTTTGGCCA | CAGACTTTAT | CATAAACTCC | 191940 |
| ATCCCTTAGG | GTGGCATTAG | GGTAGTCTTG | GGCCTGAATT | TAGGTGGGCC | AGTGGCTGTC | 192000 |
| TTAGTGACAG | CCTTTCCGCT | CTCTTCTGTC | ATCCCTCCC | AACTGCTAAT | GTCTAACTAC | 192060 |
| CTAACAATTA | CCCATTAAAT | CAGTGTGTCT | GGGGTTAGGA | GCAGGCCTCA | ATATGTTTAA | 192120 |
| TCATTCTCCA | GATAATCCCA | ATACTGTAAA | GTTTGTGAAA | CACTTGTCAG | ATAATTCAAT | 192180 |
| TATGAAGGCT | GTGGAAGGTG | TTTCAGTAGG | ATCTAATTGG | TTAATGTTAT | GACTTAATTA | 192240 |
| ATTTGAATCA | AAAAACAAAA | TGAAAAGCT | TTATATTTCT | AAGTCAAATA | AGACATAAGT | 192300 |
| TGGTCTAAGG | TTGAGATAAA | ATTTTTAAAT | GTATGATTGA | ATTTTGAAAA | TCATAAATAT | 192360 |
| TTAAATATCT | AAAGTTCAGA | TCAGAACATT | GCGAAGCTAC | TTTCCCCAAT | CAACAACACC | 192420 |
| CCTTCAGGAT | TTAAAAACCA | AGGGGGACAC | TGGATCACCT | AGTGTTTCAC | AAGCAGGTAC | 192480 |
| CTTCTGCTGT | AGGAGAGAGA | GAACTAAAGT | TCTGAAAGAC | CTGTTGCTTT | TCACCAGGAA | 192540 |
| GTTTTACTGG | GCATCTCCTG | AGCCTAGGCA | ATAGCTGTAG | GGTGACTTCT | GGAGCCATCC | 192600 |
| CCGTTTCCCC | GCCCCCCAAA | AGAAGCGGAG | ATTTAACGGG | GACGTGCGGC | CAGAGCTGGG | 192660 |
| GAAATGGGCC | CGCGAGCCAG | GCCGGCGCTT | CTCCTCCTGA | TGCTTTTGCA | GACCGCGGTC | 192720 |
| CTGCAGGGGC | GCTTGCTGCG | TGAGTCCGAG | GGCTGCGGGC | GAACTAGGGG | CGCGGCGGGG | 192780 |
| GTGGAAAAAT | CGAAACTAGC | TTTTTCTTTG | CGCTTGGGAG | TTTGCTAACT | TTGGAGGACC | 192840 |
| TGCTCAACCC | TATCCGCAAG | CCCCTCTCCC | TACTTTCTGC | GTCCAGACCC | CGTGAGGGAG | 192900 |
| TGCCTACCAC | TGAACTGCAG | ATAGGGGTCC | CTCGCCCCAG | GACCTGCCCC | CTCCCCCGGC | 192960 |
| TGTCCCGGCT | CTGCGGAGTG | ACTTTTGGAA | CCGCCCACTC | CCTTCCCCCA | ACTAGAATGC | 193020 |
| TTTTAAATAA | ATCTCGTAGT | TCCTCACTTG | AGCTGAGCTA | AGCCTGGGGC | TCCTTGAACC | 193080 |
| TGGAACTCGG | GTTTATTTCC | AATGTCAGCT | GTGCAGTTTT | TTCCCCAGTC | ATCTCCAAAC | 193140 |
| AGGAAGTTCT | TCCCTGAGTG | CTTGCCGAGA | AGGCTGAGCA | AACCCACAGC | AGGATCCGCA | 193200 |
| CGGGGTTTCC | ACCTCAGAAC | GAATGCGTTG | GGCGGTGGGG | GCGCGAAAGA | GTGGCGTTGG | 193260 |
| GGATCTGAAT | TCTTCACCAT | TCCACCCACT | TTTGGTGAGA | CCTGGGGTGG | AGGTCTCTAG | 193320 |
| GGTGGGAGGC | TCCTGAGAGA | GGCCTACCTC | GGGCCTTTCC | CCACTCTTGG | CAATTGTTCT | 193380 |
| TTTGCCTGGA | AAATTAAGTA | TATGTTAGTT | TTGAACGTTT | GAACTGAACA | ATTCTCTTTT | 193440 |
| CGGCTAGGCT | TTATTGATTT | GCAATGTGCT | GTGTAATTAA | GAGGCCTCTC | TACAAAGTAC | 193500 |
| TGATAATGAA | CATGTAAGCA | ATGCACTCAC | TTCTAAGTTA | CATTCATATC | TGATCTTATT | 193560 |
| TGATTTTCAC | TAGGCATAGG | GAGGTAGGAG | CTAATAATAC | GTTTATTTTA | CTAGAAGTTA | 193620 |
| ACTGGAATTC | AGATTATATA | ACTCTTTTCA | GGTTACAAAG | AACATAAATA | ATCTGGTTTT | 193680 |
| CTGATGTTAT | TTCAAGTACT | ACAGCTGCTT | CTAATCTTAG | TTGACAGTGA | TTTTGCCCTG | 193740 |
| TAGTGTAGCA | CAGTGTTCTG | TGGGTCACAC | GCCGGCCTCA | GCACAGCACT | TGAGTTTTG | 193800 |
| GTACTACGTG | TATCCACATT | TTACACATGA | CAAGAATGAG | GCATGGCACG | GCCTGCTTCC | 193860 |
| TGGCAAATTT | ATTCAATGGT | ACACTGGGCT | TTGGTGGCAG | AGCTCATGTC | TCCACTTCAT | 193920 |
| AGCTATGATT | CTTAAACATC | ACACTGCATT | AGAGGTTGAA | TAATAAAATT | TCATGTTGAG | 193980 |
| CAGAAATATT | CATTGTTTAC | AAGTGTAAAT | GAGTCCCAGC | CATGTGTTGC | ACTGTTCAAG | 194040 |
| CCCCAAGGGA | GAGAGCAGGG | AAACAAGTCT | TTACCCTTTG | ATATTTGCA | TTCTAGTGGG | 194100 |
| AGAGATGACA | ATAAGCAAAT | GAGCAGAAAG | ATATACAACA | TCAGGAAATC | ATGGGTGTTG | 194160 |
| TGAGAAGCAG | AGAAGTCAGG | GCAAGTCACT | CTGGGGCTGA | CACTTGAGCA | GAGACATGAA | 194220 |
| GGAAATAAGA | ATGATATTGA | CTGGGAGCAG | TATTTCCCAG | GCAAACTGAG | TGGGCCTGGC | 194280 |

| | | | | | | |
|---|---|---|---|---|---|---|
| AAGTTGGATT | AAAAAGCGGG | TTTTCTCAGC | ACTACTCATG | TGTGTGTGTG | TGGGGGGGGG | 194340 |
| GGGCGGCGTG | GGGGTGGGAA | GGGGGACTAC | CATCTGCATG | TAGGATGTCT | AGCAGTATCC | 194400 |
| TGTCCTCCCT | ACTCACTAGG | TGCTAGGAGC | ACTCCCCAG | TCTTGACAAC | CAAAAATGTC | 194460 |
| TCTAAACTTT | GCCACATGTC | ACCTAGTAGA | CAAACTCCTG | GTTAAGAAGC | TCGGGTTGAA | 194520 |
| AAAAATAAAC | AAGTAGTGCT | GGGGAGTAGA | GGCCAAGAAG | TAGGTAATGG | GCTCAGAAGA | 194580 |
| GGAGCCACAA | ACAAGGTTGT | GCAGGCGCCT | GTAGGCTGTG | GTGTGAATTC | TAGCCAAGGA | 194640 |
| GTAACAGTGA | TCTGTCACAG | GCTTTTAAAA | GATTGCTCTG | GCTGCTATGT | GGAAAGCAGA | 194700 |
| ATGAAGGGAG | CAACAGTAAA | AGCAGGGAGC | CCAGCCAGGA | AGCTGTTACA | CAGTCCAGGC | 194760 |
| AAGAGGTAGT | GGAGTGGGCT | GGGTGGGAAC | AGAAAGGGA | GTGACAAACC | ATTGTCTCCT | 194820 |
| GAATATATTC | TGAAGGAAGT | TGCTGAAGGA | TTCTATGTTG | TGTGAGAGAA | AGAGAAGAAT | 194880 |
| TGGCTGGGTG | TAGTAGCTCA | TGCCAAGGAG | GAGGCCAAGG | AGAGCAGATT | CCTGAGCTCA | 194940 |
| GGAGTTCAAG | ACCAGCCTGG | GCAACACAGC | AAAACCCCTT | CTCTACAAAA | AATACAAAAA | 195000 |
| TTAGCTGGGT | GTGGTGGCAT | GCACCTGTGA | TCCTAGCTAC | TCGGGAGGCT | GAGGTGGAGG | 195060 |
| GTATTGCTTG | AGCCCAGGAA | GTTGAGGCTG | CAGTGAGCCA | TGACTGTGCC | ACTGTACTTC | 195120 |
| AGCCTAGGTG | ACAGAGCAAG | ACCCTGTCTC | CCCTGACCCC | CTGAAAAAGA | GAAGAGTTAA | 195180 |
| AGTTGACTTT | GTTCTTTATT | TTAATTTTAT | TGGCCTGAGC | AGTGGGGTAA | TTGGCAATGC | 195240 |
| CATTTCTGAG | ATGGTGAAGG | CAGAGGAAAG | AGCAGTTTGG | GGTAAATCAA | GGATCTGCAT | 195300 |
| TTGGGACATG | TTAAGTTTGA | GATTCCAGTC | AGGCTTCCAA | GTGGTGAGGC | CACATAGGCA | 195360 |
| GTTCAGTGTA | AGAATTCAGG | ACCAAGGCTG | GGCACGGTGG | CTCACTTCTG | TAATCCCAGC | 195420 |
| ACTTTGGTGG | CTGAGGCAGG | TAGATCATTT | GAGGTCAGGA | GTTTGAGACA | AGCTTGGCCA | 195480 |
| ACATGGTGAA | ACCCCATGTC | TACTAAAAAT | ACAAAAATTA | GCCTGGTGTG | GTGGCGCACG | 195540 |
| CCTATAGTCC | CAGGTTTTCA | GGAGGCTTAG | GTAGGAGAAT | CCCTTGAACC | CAGGAGGTGC | 195600 |
| AGGTTGCAGT | GAGCTGAGAT | TGTGCCACTG | CACTCCAGCC | TGGGTGATAG | AGTGAGACTC | 195660 |
| TGTCTCAAAA | AAAAAAAAAA | AAAAAAAAAA | AAAACTGAA | GGAATTATTC | CTCAGGATTT | 195720 |
| GGGTCTAATT | TGCCCTGAGC | ACCAACTCCT | GAGTTCAACT | ACCATGGCTA | GACACACCTT | 195780 |
| AACATTTTCT | AGAATCCACC | AGCTTTAGTG | GAGTCTGTCT | AATCATGAGT | ATTGGAATAG | 195840 |
| GATCTGGGGG | CAGTGAGGGG | GTGGCAGCCA | CGTGTGGCAG | AGAAAAGCAC | ACAAGGAAAG | 195900 |
| AGCACCCAGG | ACTGTCATAT | GGAAGAAAGA | CAGGACTGCA | ACTCACCCTT | CACAAAATGA | 195960 |
| GGACCAGACA | CAGCTGATGG | TATGAGTTGA | TGCAGGTGTG | TGGAGCCTCA | ACATCCTGCT | 196020 |
| CCCCTCCTAC | TACACATGGT | TAAGGCCTGT | TGCTCTGTCT | CCAGGTTCAC | ACTCTCTGCA | 196080 |
| CTACCTCTTC | ATGGGTGCCT | CAGAGCAGGA | CCTTGGTCTT | TCCTTGTTTG | AAGCTTTGGG | 196140 |
| CTACGTGGAT | GACCAGCTGT | TCGTGTTCTA | TGATCATGAG | AGTCGCCGTG | TGGAGCCCCG | 196200 |
| AACTCCATGG | GTTTCCAGTA | GAATTTCAAG | CCAGATGTGG | CTGCAGCTGA | GTCAGAGTCT | 196260 |
| GAAAGGGTGG | GATCACATGT | TCACTGTTGA | CTTCTGGACT | ATTATGGAAA | ATCACAACCA | 196320 |
| CAGCAAGGGT | ATGTGGAGAG | GGGGCCTCAC | CTTCCTGAGG | TTGTCAGAGC | TTTTCATCTT | 196380 |
| TTCATGCATC | TTGAAGGAAA | CAGCTGGAAG | TCTGAGGTCT | TGTGGGAGCA | GGGAAGAGGG | 196440 |
| AAGGAATTTG | CTTCCTGAGA | TCATTTGGTC | CTTGGGGATG | GTGGAAATAG | GGACCTATTC | 196500 |
| CTTTGGTTGC | AGTTAACAAG | GCTGGGGATT | TTTCCAGAGT | CCCACACCCT | GCAGGTCATC | 196560 |
| CTGGGCTGTG | AAATGCAAGA | AGACAACAGT | ACCGAGGGCT | ACTGGAAGTA | CGGGTATGAT | 196620 |
| GGGCAGGACC | ACCTTGAATT | CTGCCCTGAC | ACACTGGATT | GGAGAGCAGC | AGAACCCAGG | 196680 |

-continued

| | | | | | | |
|---|---|---|---|---|---|---|
| GCCTGGCCCA | CCAAGCTGGA | GTGGGAAAGG | CACAAGATTC | GGGCCAGGCA | GAACAGGGCC | 196740 |
| TACCTGGAGA | GGGACTGCCC | TGCACAGCTG | CAGCAGTTGC | TGGAGCTGGG | GAGAGGTGTT | 196800 |
| TTGGACCAAC | AAGGTATGGT | GGAAACACAC | TTCTGCCCCT | ATACTCTAGT | GGCAGAGTGG | 196860 |
| AGGAGGTTGC | AGGGCACGGA | ATCCCTGGTT | GGAGTTTCAG | AGGTGGCTGA | GGCTGTGTGC | 196920 |
| CTCTCCAAAT | TCTGGGAAGG | GACTTTCTCA | ATCCTAGAGT | CTCTACCTTA | TAATTGAGAT | 196980 |
| GTATGAGACA | GCCACAAGTC | ATGGGTTTAA | TTTCTTTTCT | CCATGCATAT | GGCTCAAAGG | 197040 |
| GAAGTGTCTA | TGGCCCTTGC | TTTTTATTTA | ACCAATAATC | TTTTGTATAT | TTATACCTGT | 197100 |
| TAAAAATTCA | GAAATGTCAA | GGCCGGGCAC | GGTGGCTCAC | CCCTGTAATC | CCAGCACTTT | 197160 |
| GGGAGGCCGA | GGCGGGTGGT | CACAAGGTCA | GGAGTTTGAG | ACCAGCCTGA | CCAACATGGT | 197220 |
| GAAACCCGTC | TCTAAAAAAA | TACAAAAATT | AGCTGGTCAC | AGTCATGCGC | ACCTGTAGTC | 197280 |
| CCAGCTAATT | GGAAGGCTGA | GGCAGGAGCA | TCGCTTGAAC | CTGGGAAGCG | GAAGTTGCAC | 197340 |
| TGAGCCAAGA | TCGCGCCACT | GCACTCCAGC | CTAGGCAGCA | GAGTGAGACT | CCATCTTAAA | 197400 |
| AAAAAAAAAA | AAAAAAAAAA | GAGAATTCAG | AGATCTCAGC | TATCATATGA | ATACCAGGAC | 197460 |
| AAAATATCAA | GTGAGGCCAC | TTATCAGAGT | AGAAGAATCC | TTTAGGTTAA | AAGTTTCTTT | 197520 |
| CATAGAACAT | AGCAATAATC | ACTGAAGCTA | CCTATCTTAC | AAGTCCGCTT | CTTATAACAA | 197580 |
| TGCCTCCTAG | GTTGACCCAG | GTGAAACTGA | CCATCTGTAT | TCAATCATTT | TCAATGCACA | 197640 |
| TAAAGGGCAA | TTTTATCTAT | CAGAACAAAG | AACATGGGTA | ACAGATATGT | ATATTTACAT | 197700 |
| GTGAGGAGAA | CAAGCTGATC | TGACTGCTCT | CCAAGTGACA | CTGTGTTAGA | GTCCAATCTT | 197760 |
| AGGACACAAA | ATGGTGTCTC | TCCTGTAGCT | TGTTTTTTC | TGAAAAGGGT | ATTTCCTTCC | 197820 |
| TCCAACCTAT | AGAAGGAAGT | GAAAGTTCCA | GTCTTCCTGG | CAAGGGTAAA | CAGATCCCCT | 197880 |
| CTCCTCATCC | TTCCTCTTTC | CTGTCAAGTG | CCTCCTTTGG | TGAAGGTGAC | ACATCATGTG | 197940 |
| ACCTCTTCAG | TGACCACTCT | ACGGTGTCGG | GCCTTGAACT | ACTACCCCA | GAACATCACC | 198000 |
| ATGAAGTGGC | TGAAGGATAA | GCAGCCAATG | GATGCCAAGG | AGTTCGAACC | TAAAGACGTA | 198060 |
| TTGCCCAATG | GGGATGGGAC | CTACCAGGGC | TGGATAACCT | TGGCTGTACC | CCCTGGGGAA | 198120 |
| GAGCAGAGAT | ATACGTGCCA | GGTGGAGCAC | CCAGGCCTGG | ATCAGCCCCT | CATTGTGATC | 198180 |
| TGGGGTATGT | GACTGATGAG | AGCCAGGAGC | TGAGAAAATC | TATTGGGGGT | TGAGAGGAGT | 198240 |
| GCCTGAGGAG | GTAATTATGG | CAGTGAGATG | AGGATCTGCT | CTTTGTTAGG | GGGTGGGCTG | 198300 |
| AGGGTGGCAA | TCAAAGGCTT | TAACTTGCTT | TTTCTGTTTT | AGAGCCCTCA | CCGTCTGGCA | 198360 |
| CCCTAGTCAT | TGGAGTCATC | AGTGGAATTG | CTGTTTTTGT | CGTCATCTTG | TTCATTGGAA | 198420 |
| TTTTGTTCAT | AATATTAAGG | AAGAGGCAGG | GTTCAAGTGA | GTAGGAACAA | GGGGAAGTC | 198480 |
| TCTTAGTACC | TCTGCCCCAG | GGCACAGTGG | GAAGAGGGGC | AGAGGGATC | TGGCATCCAT | 198540 |
| GGGAAGCATT | TTTCTCATTT | ATATTCTTTG | GGGACACCAG | CAGCTCCCTG | GGAGACAGAA | 198600 |
| AATAATGGTT | CTCCCCAGAA | TGAAAGTCTC | TAATTCAACA | AACATCTTCA | GAGCACCTAC | 198660 |
| TATTTTGCAA | GAGCTGTTTA | AGGTAGTACA | GGGGCTTTGA | GGTTGAGAAG | TCACTGTGGC | 198720 |
| TATTCTCAGA | ACCCAAATCT | GGTAGGGAAT | GAAATTGATA | GCAAGTAAAT | GTAGTTAAAG | 198780 |
| AAGACCCCAT | GAGGTCCTAA | AGCAGGCAGG | AAGCAAATGC | TTAGGGTGTC | AAAGGAAAGA | 198840 |
| ATGATCACAT | TCAGCTGGGG | ATCAAGATAG | CCTTCTGGAT | CTTGAAGGAG | AAGCTGGATT | 198900 |
| CCATTAGGTG | AGGTTGAAGA | TGATGGGAGG | TCTACACAGA | CGGAGCAACC | ATGCCAAGTA | 198960 |
| GGAGAGTATA | AGGCATACTG | GGAGATTAGA | AATAATTACT | GTACCTTAAC | CCTGAGTTTG | 199020 |
| CGTAGCTATC | ACTCACCAAT | TATGCATTTC | TACCCCCTGA | ACATCTGTGG | TGTAGGGAAA | 199080 |

| | | | | | | |
|---|---|---|---|---|---|---|
| AGAGAATCAG | AAAGAAGCCA | GCTCATACAG | AGTCCAAGGG | TCTTTTGGGA | TATTGGGTTA | 199140 |
| TGATCACTGG | GGTGTCATTG | AAGGATCCTA | AGAAAGGAGG | ACCACGATCT | CCCTTATATG | 199200 |
| GTGAATGTGT | TGTTAAGAAG | TTAGATGAGA | GGTGAGGAGA | CCAGTTAGAA | AGCCAATAAG | 199260 |
| CATTTCCAGA | TGAGAGATAA | TGGTTCTTGA | AATCCAATAG | TGCCCAGGTC | TAAATTGAGA | 199320 |
| TGGGTGAATG | AGGAAAATAA | GGAAGAGAGA | AGAGGCAAGA | TGGTGCCTAG | GTTTGTGATG | 199380 |
| CCTCTTTCCT | GGGTCTCTTG | TCTCCACAGG | AGGAGCCATG | GGGCACTACG | TCTTAGCTGA | 199440 |
| ACGTGAGTGA | CACGCAGCCT | GCAGACTCAC | TGTGGGAAGG | AGACAAAACT | AGAGACTCAA | 199500 |
| AGAGGGAGTG | CATTTATGAG | CTCTTCATGT | TTCAGGAGAG | AGTTGAACCT | AAACATAGAA | 199560 |
| ATTGCCTGAC | GAACTCCTTG | ATTTTAGCCT | TCTCTGTTCA | TTTCCTCAAA | AAGATTTCCC | 199620 |
| CATTTAGGTT | TCTGAGTTCC | TGCATGCCGG | TGATCCCTAG | CTGTGACCTC | TCCCCTGGAA | 199680 |
| CTGTCTCTCA | TGAACCTCAA | GCTGCATCTA | GAGGCTTCCT | TCATTTCCTC | CGTCACCTCA | 199740 |
| GAGACATACA | CCTATGTCAT | TTCATTTCCT | ATTTTGGAA | GAGGACTCCT | TAAATTTGGG | 199800 |
| GGACTTACAT | GATTCATTTT | AACATCTGAG | AAAAGCTTTG | AACCCTGGGA | CGTGGCTAGT | 199860 |
| CATAACCTTA | CCAGATTTTT | ACACATGTAT | CTATGCATTT | TCTGGACCCG | TTCAACTTTT | 199920 |
| CCTTTGAATC | CTCTCTCTGT | GTTACCCAGT | AACTCATCTG | TCACCAAGCC | TTGGGGATTC | 199980 |
| TTCCATCTGA | TTGTGATGTG | AGTTGCACAG | CTATGAAGGC | TGTACACTGC | ACGAATGGAA | 200040 |
| GAGGCACCTG | TCCCAGAAAA | AGCATCATGG | CTATCTGTGG | GTAGTATGAT | GGGTGTTTTT | 200100 |
| AGCAGGTAGG | AGGCAAATAT | CTTGAAAGGG | GTTGTGAAGA | GGTGTTTTTT | CTAATTGGCA | 200160 |
| TGAAGGTGTC | ATACAGATTT | GCAAAGTTTA | ATGGTGCCTT | CATTTGGGAT | GCTACTCTAG | 200220 |
| TATTCCAGAC | CTGAAGAATC | ACAATAATTT | TCTACCTGGT | CTCTCCTTGT | TCTGATAATG | 200280 |
| AAAATTATGA | TAAGGATGAT | AAAAGCACTT | ACTTCGTGTC | CGACTCTTCT | GAGCACCTAC | 200340 |
| TTACATGCAT | TACTGCATGC | ACTTCTTACA | ATAATTCTAT | GAGATAGGTA | CTATTATCCC | 200400 |
| CATTTCTTTT | TTAAATGAAG | AAAGTGAAGT | AGGCCGGGCA | CGGTGGCTCA | CGCCTGTAAT | 200460 |
| CCCAGCACTT | TGGGAGGCCA | AAGCGGGTGG | ATCACGAGGT | CAGGAGATCG | AGACCATCCT | 200520 |
| GGCTAACATG | GTGAAACCCC | ATCTCTAATA | AAAATACAAA | AAATTAGCTG | GGCGTGGTGG | 200580 |
| CAGACGCCTG | TAGTCCCAGC | TACTCGGAAG | GCTGAGGCAG | GAGAATGGCA | TGAACCCAGG | 200640 |
| AGGCAGAGCT | TGCAGTGAGC | CGAGTTTGCG | CCACTGCACT | CCAGCCTAGG | TGACAGAGTG | 200700 |
| AGACTCCATC | TCAAAAAAAT | AAAAATAAAA | ATAAAAAAAT | GAAAAAAAAA | AGAAAGTGAA | 200760 |
| GTATAGAGTA | TCTCATAGTT | TGTCAGTGAT | AGAAACAGGT | TTCAAACTCA | GTCAATCTGA | 200820 |
| CCGTTTGATA | CATCTCAGAC | ACCACTACAT | TCAGTAGTTT | AGATGCCTAG | AATAAATAGA | 200880 |
| GAAGGAAGGA | GATGGCTCTT | CTCTTGTCTC | ATTGTGTTTC | TTCTGAGTGA | GCTTGAATCA | 200940 |
| CATGAAGGGG | AACAGCAGAA | AACAACCAAC | TGATCCTCAG | CTGTCATGTT | TCCTTTAAAA | 201000 |
| GTCCCTGAAG | GAAGGTCCTG | GAATGTGACT | CCCTTGCTCC | TCTGTTGCTC | TCTTTGGCAT | 201060 |
| TCATTTCTTT | GGACCCTACG | CAAGGACTGT | AATTGGTGGG | ACAGCTAGT | GGCCCTGCTG | 201120 |
| GGCTTCACAC | ACGGTGTCCT | CCCTAGGCCA | GTGCCTCTGG | AGTCAGAACT | CTGGTGGTAT | 201180 |
| TTCCCTCAAT | GAAGTGGAGT | AAGCTCTCTC | ATTTTGAGAT | GGTATAATGG | AAGCCACCAA | 201240 |
| GTGGCTTAGA | GGATGCCCAG | GTCCTTCCAT | GGAGCCACTG | GGGTTCCGGT | GCACATTAAA | 201300 |
| AAAAAAATCT | AACCAGGACA | TTCAGGAATT | GCTAGATTCT | GGGAAATCAG | TTCACCATGT | 201360 |
| TCAAAAGAGT | CTTTTTTTTT | TTTTGAGAC | TCTATTGCCC | AGGCTGGAGT | GCAATGGCAT | 201420 |
| GATCTCGGCT | CACTGTAACC | TCTGCCTCCC | AGGTTCAAGC | GATTCTCCTG | TCTCAGCCTC | 201480 |

```
CCAAGTAGCT  GGGATTACAG  GCGTGCACCA  CCATGCCCGG  CTAATTTTTG  TATTTTTAGT  201540
AGAGACAGGG  TTTCACCATG  TTGGCCAGGC  TGGTCTCGAA  CTCTCCTGAC  CTCGTGATCC  201600
GCCTGCCTCG  GCCTCCCAAA  GTGCTGAGAT  TACAGGTGTG  AGCCACCCTG  CCCAGCCGTC  201660
AAAAGAGTCT  TAATATATAT  ATCCAGATGG  CATGTGTTTA  CTTTATGTTA  CTACATGCAC  201720
TTGGCTGCAT  AAATGTGGTA  CAAGCATTCT  GTCTTGAAGG  GCAGGTGCTT  CAGGATACCA  201780
TATACAGCTC  AGAAGTTTCT  TCTTTAGGCA  TTAAATTTTA  GCAAAGATAT  CTCATCTCTT  201840
CTTTTAAACC  ATTTTCTTTT  TTTGTGGTTA  GAAAAGTTAT  GTAGAAAAAA  GTAAATGTGA  201900
TTTACGCTCA  TTGTAGAAAA  GCTATAAAAT  GAATACAATT  AAAGCTGTTA  TTTAATTAGC  201960
CAGTGAAAAA  CTATTAACAA  CTTGTCTATT  ACCTGTTAGT  ATTATTGTTG  CATTAAAAAT  202020
GCATATACTT  TAATAAATGT  ATATTGTATT  GTATACTGCA  TGATTTTATT  GAAGTTCTTG  202080
TTCATCTTGT  GTATATACTT  AATCGCTTTG  TCATTTGGA   GACATTATT   TTGCTTCTAA  202140
TTTCTTTACA  TTTTGTCTTA  CGGAATATTT  TCATTCAACT  GTGGTAGCCG  AATTAATCGT  202200
GTTCTTCAC   TCTAGGGACA  TTGTCGTCTA  AGTTGTAAGA  CATTGGTTAT  TTACCAGCA   202260
AACCATTCTG  AAAGCATATG  ACAAATTATT  TCTCTCTTAA  TATCTTACTA  TACTGAAAGC  202320
AGACTGCTAT  AAGGCTTCAC  TTACTCTTCT  ACCTCATAAG  GAATATGTTA  CAATTAATTT  202380
ATTAGGTAAG  CATTTGTTTT  ATATTGGTTT  TATTTCACCT  GGGCTGAGAT  TCAAGAAAC   202440
ACCCCAGTCT  TCACAGTAAC  ACATTTCACT  AACACATTTA  CTAAACATCA  GCAACTGTGG  202500
CCTGTTAATT  TTTTTAATAG  AAATTTTAAG  TCCTCATTTT  CTTTCGGTGT  TTTTTAAGCT  202560
TAATTTTTCT  GGCTTTATTC  ATAAATTCTT  AAGGTCAACT  ACATTTGAAA  AATCAAAGAC  202620
CTGCATTTTA  AATTCTTATT  CACCTCTGGC  AAAACCATTC  ACAAACCATG  GTAGTAAAGA  202680
GAAGGGTGAC  ACCTGGTGGC  CATAGGTAAA  TGTACCACGG  TGGTCCGGTG  ACCAGAGATG  202740
CAGCGCTGAG  GGTTTTCCTG  AAGGTAAAGG  AATAAAGAAT  GGGTGGAGGG  GCGTGCACTG  202800
GAAATCACTT  GTAGAGAAAA  GCCCCTGAAA  ATTTGAGAAA  ACAAACAAGA  AACTACTTAC  202860
CAGCTATTTG  AATTGCTGGA  ATCACAGGCC  ATTGCTGAGC  TGCCTGAACT  GGGAACACAA  202920
CAGAAGGAAA  ACAAACCACT  CTGATAATCA  TTGAGTCAAG  TACAGCAGGT  GATTGAGGAC  202980
TGCTGAGAGG  TACAGGCCAA  AATTCTTATG  TTGTATTATA  ATAATGTCAT  CTTATAATAC  203040
TGTCAGTATT  TTATAAAACA  TTCTTCACAA  ACTCACACAC  ATTTAAAAAC  AAAACACTGT  203100
CTCTAAAATC  CCCAAATTTT  TCATAAACTC  AGTTTAAAC   TAACTTTTTT  TCAAACCACA  203160
ATCTGATTTA  ACAATGACTA  TCATTTAAAT  ATTTCTGACT  TTCAAATTAA  AGATTTTCAC  203220
ATGCAGGCTG  ATATTTGTAA  TTGTGATTCT  CTCTGTAGGC  TTTGGGTATA  ATGTGTTCTT  203280
TTCCTTTTTT  GCATCAGCGA  TTAACTTCTA  CACTCTAACA  TGTAGAATGT  TACTACAATA  203340
TTAAAGTATT  TTGTATGACA  ATTTTATTTG  AAAGCCTAGG  ATGCGTTGAC  ATCCTGCATG  203400
CATTTATTAC  TTGATATGCA  TGCATTCTGG  TATCTCAAGC  ATTCTATTTC  TGAGTAATTG  203460
TTTAAGGTGT  AGAAGAGATA  GATATGGTGG  ATTTGGAGTT  GATACTTATA  TATTTTCTAT  203520
TTCTTGGATG  GATGAATTTG  TACATTAAAA  GTTTTCCATG  GCAGAAATCT  TTTCAAAAAC  203580
TTTTTTTTTC  CGGGATGGAT  TGAAGGCCCT  GATTTCACCA  CAATGCAATA  TATTAATGTA  203640
GCAAAATTGT  ACTTGTACCC  CATGAATATA  TATAATCTTA  AGAAAATTTT  TTTAGCCAAT  203700
TATTATTACT  TACTAGATAT  TAGGCTGTGT  TCTGAATCTT  AATTTAATTC  CTCCAAAGAA  203760
TCTTATGAGG  TAGGTAGGAG  CTATTGCTGC  TATTCTGTTA  TGCTTATGTT  GCTGTTATGA  203820
AACCAAGGCA  CAGAGAGGTT  AGTTAACTTG  CTGAAGAAAA  TGATGTGCTG  GATTTTTATT  203880
```

```
CTAGCTATTC  TGGAATAACA  ACTACACAAC  CTTATGTCTG  AGCCAAGGAA  ACATACGGTG  203940
TGGCAACAGT  TACCATGTTT  TTAGGAACAG  CAGCACTCCT  AATGTTTGCT  GCAGGGAAAA  204000
AGGAATCTCA  GAATTTGCCT  GATCCCTATA  ATTTTTTTCC  TAAATATTTT  GAAATATCTT  204060
TCAGATGTAT  TTTAAAATTT  AAGGATATTT  TGTTCAGTTC  ATACAGAATT  TTTTTTTTTT  204120
TCTCGAGATG  GAGTCTCACT  CTATCACCCA  GGCTGGAATG  CAGTGGCATG  ATCTCGGCTC  204180
ACTGCAACCT  CTGCCTCCTG  GGTTCAAGCA  ATTTTCCTGC  CTCAGCCTCC  CAAGTGGCTG  204240
AGACTACAGG  CGCATGCCAC  CATGCACGGC  TAATTTTTTT  TGTATTTTTA  GTAGAGATGG  204300
AGTTTCACCA  TGTTGGCCAG  GCTGGTCTCG  AACTCCTGAC  CTCAAATGAT  CCGCCCTTTT  204360
TGGCCTCCCA  AAGTGCTGGG  ATTACAGGCG  TGAGCTACCG  CGCCCAGCCA  AATTTCTAAC  204420
TTGTTTTGTT  GTTGTTGAGA  CAGGGTCTCA  GTCTGACACC  AAGGCTGGTG  TGCAGTACTG  204480
CGATCACGGC  TCACTGCAGT  CTCGACCTCC  TGAGCTCAAG  TGATCCTCCC  ACCTCAGCCT  204540
ACTGAGTAGC  TGGGACCACC  ACGCCTGGCT  CATTTTTTTC  TATTATTTAT  TGAAACGGGT  204600
TCTGGCTATG  TTGCCCAGGT  TGGTCTTGAA  CTCCGGAGCT  CATGCGATCC  ACCCACCTCA  204660
GCGTCCGAAA  GGATTATCAG  GAGTGAGCCA  CCGTGCCCGG  CCAAATTTCT  AACTTTGAA   204720
TTGACATATT  CATTTATTCT  CTTTATCATT  CAGGGAGAAA  TTTGGGGATG  GATAGCCTTG  204780
AAGCATCATC  CACCAAGTTA  TTTTATACAC  CAGATTTAGA  TACAAAGTAT  TTTTTTATTA  204840
TTTAAAAAAA  TCAAATTCTA  GCTTTTACTC  TGAAGATTCT  AAAAAGAATT  TTGGAGTCTT  204900
TAATTCATAC  TTCAGGGGCA  GGGGAATAAG  TACCAATATT  CGTATAACTT  TCAGTGCAAG  204960
TCACGTTAGC  TAACTGTAGT  CTATTGAGTT  AAATATCCTT  GATTTATTCC  TTAAAACTGA  205020
GTCACTATGA  CGGCACTTTT  TTGTTTTTTT  TTTTCGAGAC  GGAGCTCGCC  CTGTCTCCCA  205080
GGCTGGAGTG  CGGTGGTGCG  ATCTCGGCTC  ACTGCAATCT  CCGCCTCCCA  GGTTCAAGCG  205140
ATTCTCCTGC  CCCAGCCTCC  TGAGTAGCTG  GGACTACAGG  CACACACCAC  CACGCCCAGC  205200
TAATGTTTGT  ATTTTTAGTA  GAGACAGGGT  TTCATCATTT  TGGTCAGGCT  GGTCTTGAAC  205260
TCCTGACCTC  GTGATCAGCC  TGCCTCGACC  TCCCAAAGTG  CTGGGATTAC  AGTCATGAGC  205320
CACTGCACCC  GGCTGAATGG  CACTTTCATA  AACAGTAAA   TAACCAACTT  CACTACTGCC  205380
CCCAAGAGTT  TTACTATGTA  TATGAGGGCA  TCTGTTTTAA  GTATGGGTAT  AATGTTACGG  205440
GTTTTTCTTT  GTGTAAGTTT  GGGTTCACAA  TTTCATCATT  AAAACAAATG  TAAAATACTT  205500
TGTGCTTTCT  GTGTGCTATT  AAGAAAGTAT  TCAAGGGAAT  TTTGAAAATC  AAATTTAATT  205560
ACTCTCATGT  TTGTAAAATT  TTTGAAACAA  ATGTTTAAGA  GAGGATAATG  TTAGAAATTA  205620
TCTTTCCAGC  CAGACCTGGT  GGCTCACGCC  AGTAATCCTA  GCATTTGGG   AGGACAAGGT  205680
GGGCAGATCA  CTTAAGCCCA  GGAATTCAAG  ACCAGCCTGG  ACAACACAGG  GAAAGCCCAT  205740
CTCTACAAAA  TATACAAAAT  TAGTGGCCGA  GCGTGGTGGC  TCACGCCTGT  AATCCCAGCA  205800
CTTTGGGAGG  CCGAGGCGGG  CAGATCACCT  GAGGTCAGGA  GTTCCAGACC  AGCCTCAACA  205860
TGGAGAAACC  CCGTCTCTAC  TAAAAATACA  AAATTAGCTG  GGCGTGGTGA  TGCATGCCTG  205920
TAATCCCAGC  TACTCGGGAG  GCTGAGGCAG  GAGAATTGCT  TGAACCTGGG  AGGTAGAGGT  205980
TGCGGTGAGC  CGAGATCCCG  CCATTGCACT  CCAGCCTGGG  CAACAAGAGC  GAAACTCCAT  206040
CTCAAAAAAC  AAAACAAACA  AATAAACAAA  ATTAGTCAGG  TGTGGTTGTG  CACACCTGTA  206100
GTCCAGCTA   CTTGGGAGGC  TGAGGTGGGA  GGATCACTTG  AGCCCGGGGA  AGTGTAGGCT  206160
ACCATGAGCC  ATCATGGTGC  CACTGTACTC  CAGTCTAGGA  AAAAAATAAA  CATTAAAAAT  206220
TTTAAAATCT  TAAAAAAAGA  AAAGAAATTT  TCTGTCCAGA  TATCTTTATT  TTAACAAAT   206280
```

-continued

| | | | | | | |
|---|---|---|---|---|---|---|
| CGAAGTGTAT | TAATAGTGTT | TATGGGAGCG | TGCCCACACA | AGGACAGCAA | GCCTAGGAAG | 206340 |
| TGCAAGTCAA | GAAAACTTTT | TGTGAAATAA | TTTAAACTGA | AAAGAAAAG | CAGAGATTTT | 206400 |
| TTTCTAGAAA | AGTAAGGAGT | GGAGGTAAAA | AAAAAACACA | GCAGAGACAC | AGGTATGCTA | 206460 |
| CGGAACCAAA | GGTGTGCCAA | TGGTACTGAC | AGTTTAATTC | AGAAAAAAAT | GAATCAGAAA | 206520 |
| ATGGATATTT | TTAAATAAGT | TAGGTTGCTG | AAAAAGAGAA | ATGCAGTGAA | GCCTTAGATG | 206580 |
| GGAGTGAGAT | AAATCAGCCA | TTGGCTAGAG | GAGTTTCTTG | CCCAAGACCA | GTGGTGATGT | 206640 |
| CCCCAAATGC | CTGGAAACAA | CTGTTGTGAC | ATTATAAAGC | CCCCATAGTC | TAAGTTGGGT | 206700 |
| GAGACTATAC | TTATGCATTT | TCTCACCTGT | AATATAGCTT | AAAAGTATTT | CTACTCTGGG | 206760 |
| ATTTCTTTAC | ATTTTACTAA | AGCGCAATTA | TATACTTAAA | ACTGATAGTG | TATGCTGGGC | 206820 |
| TGCTAGTCAT | TCTCAACCCT | GGCCAATTAT | CAGAATTGTT | TGTTGAATAT | ATAGGTGCCA | 206880 |
| TATATAGGTG | CATACACACA | CACACACACA | CACATACACA | CACACACACA | CACACACACA | 206940 |
| CCATATTTCA | TTCCTCATAT | CGAATATTCT | GAGAGAGTTA | GTTTGTGGAG | GGTAGTTCTG | 207000 |
| GACAATTTAT | ATTTTCATAA | CACCTCTGGT | TATTTTTTT | TAAGTAGAGA | TGAAGACTTG | 207060 |
| CTATGTTGCC | CAAAATGGTC | TTGAACTCCT | GAGCTCAAGC | GATTCTCCCA | ACTCAGCCTC | 207120 |
| CTGAAGTGCT | GGGATTACAG | CCGTGAGCCA | CTGCATTAAC | CTCTGATTAA | TATCATAGAT | 207180 |
| TAACCTCTGA | TTAATATCAT | AGATTTATTT | GTTGAATGC | TTCATGTATC | CTCTCAACCA | 207240 |
| CAACTTGTTT | GCAGAGTTTT | AATCTGAAGG | GCTTAGGTCT | CTTGTTCAAT | GAATGAGTTT | 207300 |
| GATCTGATGG | GTGAGAGGAA | GGTGAAATGG | AAAGCGAACG | AGAAGCCATA | CAGATTAGGC | 207360 |
| GAGTGAGCCT | AATCTCTCCC | TAACCATAAG | ATTGAGTATG | CCTGAATTCT | TCGCAGAGTG | 207420 |
| GAAGAATCCA | TTTTAAATAT | ATATATCTAC | ATGTACAGAT | CCTTTAAATA | TTTGTTCTGA | 207480 |
| CATTCATTGT | TTTTGAGTCA | CTGTCATTGA | GAAAAGTTTA | GAAAGGAGAT | ATTAGGAGCA | 207540 |
| GGAAATAGAA | AGTAAATAAA | ATATCAAAAT | AAAAATGGGG | TTTTATAAAT | GATATAATAG | 207600 |
| GCAAAATAAA | GGAAAGGCAT | CCTAGACCTC | TGGTTAAAAT | GAAGATGGCA | CTTGGCGAGA | 207660 |
| TGTGTTCCAG | GGTAGTTCAC | ATGATGTATG | TTTTCAGAGA | ATTGTCATAT | TGCATATGCT | 207720 |
| GCTATATTTT | TTATTTTCAT | GAATTAAAAG | GCATGTTGAG | ATTTCAGAGT | TTTACTTATG | 207780 |
| ATCTCAGACT | CTGCATTTTT | TCTCTGTAAT | GTTTGACATT | TCTTCCTAGC | TAAGTCTCTA | 207840 |
| GTTATAAGGT | CTGTGTTGTG | GCATGTGGAC | AGTGAGTGGA | AGAACCTAAG | AACTCAATTT | 207900 |
| GGGGCAGAAG | AATGTAATCA | ATTATTTCAG | AAGTGATACA | AACAATATGA | CATGTAGAGC | 207960 |
| ATTCTGGCCT | TTCCTGGGTC | TTTTTTCTCC | ATTCCTGGAT | TTCTTCTCTT | CATGTGAGCA | 208020 |
| AGTCTGAGGT | TACTATATAA | TGTCTCTCAC | AGGCCACAGC | CCCATTCTAA | ATATTCCAA | 208080 |
| TAGAAATTCA | TTTATTAACC | AGAGAGTGGT | GGGTGGGGTT | GTTTTTGTTT | TTAAACAAA | 208140 |
| AGTGGATCTT | ATGGGCATTC | TGGAAAGCTC | CCGCAGGAAG | CTAAGAATAA | AATTTTGAAT | 208200 |
| TGAGAAGTCC | CTTTCTTCAA | ACCACATTCA | GACCCAATTC | TGCTATTCTA | TTTATTTTTC | 208260 |
| AAGGGGATTA | GCCTTATTTT | AACACCAATA | ATCTTATCAC | AAAAACCTCC | CAGAGGAAGA | 208320 |
| CCCTGTAGAT | TTTGTAATGA | CCTTAATCAA | GTATTAGCCC | TACACTTCAA | TTAATCCCCA | 208380 |
| ACTGTACAAA | ACGAATGTTC | TTTTCTCTAA | AGCTGTAGCA | AGTTGAAAGG | GGATTAAAAA | 208440 |
| CGGAGGGAAG | GGAAGAGTGT | TTGGAATTTC | AGGCACAGCA | AACAGGCACA | GCAGACCAGG | 208500 |
| AAGAGCGTCC | CGGGAAAACA | TATTATCCAG | ACTTAAGTTT | ATATTCCCTG | TCTCTCTCAG | 208560 |
| ACTTTTGCAG | AAAAATGAGT | CATTCAACAA | ATATTTGAAT | CGAGATAGGG | AAAGTGACGA | 208620 |
| GGAAGAAGTT | TGCACTTATG | AGGTTTTAAT | TTGCAATTAT | TTGGCTACCT | TTTTGCCTTC | 208680 |

| | | | | | | |
|---|---|---|---|---|---|---|
| CCAAAACATA | GGGTCTTTAG | GAGTGAAACT | TCATAGCCAA | ACTTATACCT | TGTCCAGCAC | 208740 |
| AGAGAAGGCC | ATCAAAATGC | CTGGTTTAAA | TAAAATATT | AAAATGATTG | GGAGGGTAAA | 208800 |
| TCCCTTGACC | TATAAATCTG | ACCTCCTTTA | AACATTATTT | GTATGTTCCC | CAATAAACTA | 208860 |
| TTCCGTAATT | TATTAGTTAG | CAAGTGGAAA | TAAAAGAAA | TGTGGAATGG | GGCTATGCTT | 208920 |
| AGCGTCATTA | AGCTGACAGG | AATACAGCGC | ATTCAACTTG | CAAACACCCT | TCCACTCCCA | 208980 |
| CAAAGAGCAA | GCTGTCACTG | GCCAATCAAA | ACAATGAACC | ATAATGAAAC | AGTTTTCTT | 209040 |
| GCTCCACCCA | CTTGGTGACC | AAATTTGAAA | AAAAAAAAA | ACCGCGCCAA | CTCATGTTGT | 209100 |
| TTTCAATCAG | GTCCGCCAAG | TTTGTATTTA | AGGAACTGTT | TCAGTTCATA | CCTTCCACTG | 209160 |
| CGATAGGAAT | CATGTCTGGT | CGCGGCAAAG | GCGGAAAAGG | CTTGGGAAG | GGTGGTGCTA | 209220 |
| AGCGCCATCG | TAAGGTGCTC | CGGGATAACA | TCCAGGGCAT | TACAAAACCG | GCTATTCGCC | 209280 |
| GTTTGGCTCG | GCGCGGTGGC | GTCAAGCGCA | TTTCCGGTCT | TATCTATGAG | GAGACTCGAG | 209340 |
| GTGTGCTTAA | GGTTTTCTTA | GAGAACGTTA | TTCGAGACGC | CGTCACCTAT | ACGGAGCACG | 209400 |
| CCAAGCGCAA | AACTGTCACA | GCCATGGATG | TAGTATATGC | CCTAAAACGT | CAGGGGCGCA | 209460 |
| CTCTGTATGG | CTTCGGCGGC | TGAATCTAAG | AATACGCGGT | CTCCTGAGAA | CTTCAAAAAA | 209520 |
| CAAAAACAAA | AAACCCAAA | GGCCCTTTTC | AGGGCCGCTC | ACAAAGTCGT | TTAAAGAGCT | 209580 |
| GAAATGCGTT | GCGAGAATGA | GTTTGGATGA | CAGAAATAAC | CGTGACATCC | TGCATAAGAA | 209640 |
| TGAATTGTGT | TTGCCATGAC | CGGCCACACT | GTGACAAAAT | TTCAAAGCAT | AAAGTAGGCA | 209700 |
| TAGAGAGGTA | AGCGCTAATA | AAGTGATTGG | CTCCACAAAA | AGCATTTTGC | TGGGCGCAGT | 209760 |
| GGCTCACGAC | TGTAATCCCA | GCACTTTGGG | AGGCCAAAGC | TAGTGTATCA | CTTGAGATCA | 209820 |
| AGAATCCGAG | ACCAGCCTGG | CCAAAATGGT | GAAACCCCCT | CTACCAAAAA | AATACAAAA | 209880 |
| CTTAGCCGGG | CGTGGTGGTC | TGCACCTGTA | GGCCCAGCTA | GCCCGGAAGC | AGAGATTGCA | 209940 |
| GTGAGCCGAG | ATCGCGCCAC | TCCCCTCCAG | CCTGGGAGAC | AGAGAGAGAC | TCCTCAAAAA | 210000 |
| AAAAAAAAAA | AAAAAAAAAA | AAAATTATGT | ATTTTAGAGC | ATTCTAAGAA | TGGTACTTTG | 210060 |
| GACTTAACCG | AAGGGCTGGA | GGCGCGTGTT | GAACAAAGGT | TATCACCTTT | TGGCTCATGC | 210120 |
| GGCACACAGC | TATGTAAATA | AAGCATCTTT | AGGGACAAGC | TCTCATTTGC | GGAGGGTTCT | 210180 |
| ATGGCTGTTG | TCCTATTGGC | CAAAACAAAG | TGGTCTAAGT | CCGGGCGCGG | TGGCTCACGC | 210240 |
| CTGTATTCCC | AGCAGTTTGG | TAGGCCAAGG | TGGGTGGATC | ACGAGGTCTG | GCGTTCAAGA | 210300 |
| CCAGCCTGGC | CAAGATGGTG | AAACCCCGTC | TACTAAAAAT | ACAAAAATTA | GCCGGGCGTG | 210360 |
| GTGGCGGGCA | CCTGTAATCC | CAGCTACGTG | GGAGGCTGAG | CCAGAGAACT | GCTTGAACCC | 210420 |
| AGGAGGCAGA | GGTTGCAGTG | AACCGAGATT | GTGCCACTGC | ACTCTAGCCT | GGGTGACAGA | 210480 |
| GCGAGGCTCC | ATCCAAAACA | AAACAAAACA | AAAAGTGGT | CTAATAATCC | CCAGAACTGG | 210540 |
| AGGAAGAACC | ATAACTTATT | GATTTGTTT | TTAACCTTAT | GTATGCCAGG | CATGCTAGCC | 210600 |
| TTGTATACAT | ACAAGGCTAG | AGGAGCAAAG | GTGCAGGAAG | CCATCTTGAG | GGAGTCCCAT | 210660 |
| ATTATTGAGA | GACCGGCCAG | CTGCTGGGAG | AGGCTAGTTG | TTCATCCTCA | CTGTATGTGA | 210720 |
| TGAGAATCTG | GTGACAGTCC | ATTGCTGGGC | ACAGCATTTA | GGCAAAATGG | CTCTCTGCTA | 210780 |
| TGTCAGGCAA | GTGAGGCATA | TTTTTGCACA | ATCCTAGTAA | TTCCGAACTC | ATTGGGAAAC | 210840 |
| AATGGCAATT | ACATCCAAGC | AAGGAAAGGT | CTGTGGTTGA | TTTTATCTAT | ACAAATTTAA | 210900 |
| AACATAATGT | TTACAACCTT | TCATTATAGG | ACACAATTTT | TAAAAGATG | CCAAACTATA | 210960 |
| CAAATAAGTT | CAGAAAAGTG | AGGTACTATT | GAACCGTCTG | GAAAACATAA | ATGTATGTGA | 211020 |
| AATAATGCAA | TGCATAGTTT | TGCAGGGGAC | TTTGTTCAAA | GTTTCTCGAA | ATACCATGGT | 211080 |

| | | | | | |
|---|---|---|---|---|---|
| CCAAAGTAGA | CTAACATTAG | CATTGGTTAT | TTATGATGAT | CAGTAAGAAT | ACTAAATCAA 211140 |
| AAATCAAAGG | AAAATTAAAC | TATGTCTGTT | TAAAGAGAAA | CGTAGTTTAC | CTCAGACTGA 211200 |
| GAGTTAAAAC | AAGTTTGTGA | TTCAGGAAGG | TGGAATTCAG | AACCTAATTG | GGCAGCCTCC 211260 |
| AACATTTCCA | TTAAGGTTTG | GATTCTTAAA | ATTTTTCAGT | CTTCGGTATG | CTCTGGTAGT 211320 |
| CTGATGAAAC | TTACAGATTC | TTTTCATAAA | TAAGATACTT | AAAGTAATTC | ATAGGGTTAC 211380 |
| AATTGTATTA | GACCAATAAT | ATTAAAATAA | TTATCAAACC | ACTTGACCGT | AATATGTGTG 211440 |
| TTTTTGTTGA | TATACCTAAT | AGTACTTCGG | AAATAAGCAA | GCACGATTTC | CAGATTCTTG 211500 |
| CAACAACTAT | AACCTACAAA | TTTGTTATTT | CTATCAGTCA | CACACAATGG | AAGAAAATTC 211560 |
| TAAATTTCAG | CTACAGGATA | ATGAATAGAT | GAAAACAAC | AACAACAACA | ACAACAAAAA 211620 |
| AACTCCCCTA | ATCCATATTC | TGGGACACCT | TGATTCCTAT | TTATTGATCC | CTTGAAGTCA 211680 |
| GTGGATAGCA | TATTAAGAAA | CAATAGTTAC | AATGACACCA | CAGAAAGACT | AGAATGTAGT 211740 |
| ACTTGTGTTA | AAAAAAAAA | AAGTATCAGC | AAGTTATGTT | TGGATGCCAA | ATTGCTCTCC 211800 |
| ACTTCCCTTC | CCTGACACTG | GCATTTCCAG | AACTTAGATG | CTCTTACATG | TAAAAGCCTC 211860 |
| CTCTAGTGCA | CCATCGAGCT | TTTCAGGATT | GGACATCAGA | CTTTTTAGTT | CCTGGACCTC 211920 |
| TAGATATACG | GCAGTCTCTG | ACAAGAAGCC | CTTTTCTGT | TTTAACTTTT | TTTTTTTTA 211980 |
| AGTTTTGAGA | CAACGTCTGA | CTCGCTGTCA | CCCAGGCTGG | AGTGAGGTAG | CACCATCATA 212040 |
| GCTCACTGTA | TCCTTAAACG | CCTGGGTGCA | GGGACTAAGG | GAGCGTGCCA | ACCATGCTTG 212100 |
| ACTAATTTAC | TTTTTGTAA | AACCAGTAGT | CTCCAACCTT | TTTGACACAA | GAGACCGTTT 212160 |
| TGTGTAAGAC | AATTATACCA | CGGACCAGGG | GGTGCAGGGG | CTGGGAGCAA | TGATTTCCGG 212220 |
| ACTAAAACTG | CTCCAACCTC | AGATCATCAG | GCATTAGATT | GTCACAAGGA | GCCTGAAACC 212280 |
| TAGATCCCTT | GCATGTGCCA | TTCACAATAC | AGTTTGAGCT | TATGAGAATC | TATCTAATGC 212340 |
| TGCAGCTAAC | CTGACAGGCG | GTGGAGCTCA | GTTGGTTAAT | GTTCGCTCAC | CCCTCAGCTG 212400 |
| TGCGGCTCAA | TTCATAACGT | GCCATGGACA | GGGACCGGTT | ACCGGTCGGT | GGCCGGGGAA 212460 |
| ATGAGGACCC | CTGGTATAGA | TGGTAGTCTG | GCTATGTTGC | CCAGGATGGT | CTTGAAGCCT 212520 |
| GGCCTGAATT | AATTCTCCAA | TCTCAAGCCT | TTTCAACTCA | GCTGCATCAC | AACTTAAACC 212580 |
| TATAGATAAC | TGTCACAGAA | ACTTGTTTCC | AGTGTTACGC | CATCTTAAAA | TAATGTGGGT 212640 |
| GGCTCTTAAA | AGAGCCTTTG | GGTTCTTTCC | AAATTGGCCT | CCCGGAAAGC | TCTTTACTTC 212700 |
| TTAGATGTGG | CCTTTCTAAC | ATTAACTTCA | TGATGTTGGG | TCAATTTTGA | CTTCGAAGCC 212760 |
| CTTGCCTTCA | CTGGGCTCTT | CTGCTGTTGC | TTACCCTTGG | CTCCTTTAGC | CTTTCTCCCG 212820 |
| CTCCTAACAG | TTTTAGGAGT | TGTCGCTCTC | GGCTTCTTGG | CTCTCTTATT | GGTTTTAGCA 212880 |
| GTCTTTGGTG | ACTTGGAGTC | CCTGGATAAA | ACCAGCTTCT | TGGTCTTGGC | AGAAACTGAC 212940 |
| TTTTTAGCCT | TGCTTCTGGT | AGATTAGGA | ATCACCTTCT | TACTAAGCTT | AAAGGAACCG 213000 |
| GAAGCACCAG | TACCCCTGGT | TTGCACCAGG | ATTCCCTTGT | TCACTAAGCT | CTTGAGGGAC 213060 |
| AGTTTGATGC | GGCTGTTATT | CTTCTCTACG | TCGTAGCCAG | CAGCGGCCAA | TGCCTTCTTG 213120 |
| AGCGCAACCA | AAGACATACC | TACTCGTTCC | TGTGACACTG | AAAGGGCCTC | GGTGATCAAC 213180 |
| TTGGACACAG | AGAGGTTCGG | CACTTTGCGA | CTTGCACTTA | TCAAGCCAGC | CGGCTTCCTC 213240 |
| CCTCGCTTCT | TGGTTGGAAG | TTTCTCCATA | GCGGCTACAC | CAGCACTGGC | AGAAGCTGCA 213300 |
| GGCACGGTTT | CAGACATAAC | AACAGAGAAA | CGCAAGATGT | AATAACCAGC | GAAAAGCATG 213360 |
| AAACACCCGG | GCGGCCTCGG | GGCCTTATAT | AGGGTAGGGC | GCGCTGTGAT | TGGTGCATCA 213420 |
| CCTAGGCACC | GCCCCCGCCC | CTTGGAGGAG | GAGTATTTGT | GTTTGTTTTA | CCCGGAAAAG 213480 |

-continued

| | | | | | |
|---|---|---|---|---|---|
|TTGAGTATAA|CAAAACCCCT|CTTTACAGAA|TCTCCCAGGG|TCTAGTGCTG|AATAATCTGC 213540|
|GGAAATTCAT|ATTTGACATG|ACTTTTCTCT|TTTTAATGAA|AAATGACCCT|GGATGCCAAA 213600|
|ACTATTCGAG|AAAGCCCTCG|ATTTTCAATC|AAATTCACGG|AGAGGAACAA|AACTTCCCCT 213660|
|TTTCCTTGTA|AATTAATAAG|TAATCTTTGG|CAGAAGACTT|ATTTCATCTC|TTCAGAGTGG 213720|
|TCTTCCAAAT|GGATAGCTTC|AAATCGGTAG|AGGAAAGAAA|TTATTCACGC|CATGATTTTT 213780|
|ATTTAAAATT|ATTTATATAT|GTGAGGGAAG|TAACACAGAT|CTCTTAGCTG|TCTAATTGCG 213840|
|GAGTCAGAAG|ATGCTTATAG|AATTGTCAAA|AGACTGCAGA|GGATGTCTTT|ATTTAGGCAT 213900|
|GTGCAATCTA|ATAAATCATA|ATCCACAGGA|ACATGGGTTG|TCTGTAATTA|AAGGTGCTCC 213960|
|CAAGTCCCTG|TAGCTTTATA|GAGGACTCTC|AAGGATGGGG|TAATATCAAG|ATCTCACACA 214020|
|TTATGTAAGA|TTGGCCATAA|TCAGGCCACT|CTCATGACCG|GTGTCCTCAA|CTGAGTTTTG 214080|
|CTTCTGGTTT|CATTAATTGA|AGTCCCTCT|ATCCCCTGC|CCACCCCTAC|ATCCCAGAT 214140|
|AAACAGACAC|AGTCCCTCCC|CTAAATTAAC|TATAAACAT|GAGGTAGGAA|CCCTAGACTC 214200|
|AAGAACCTAC|TAGAAACTAC|AGACCCCATG|TCTAACAAGA|CTGGGCGGGT|TGGCTGGGCG 214260|
|CAGTGATTCA|TGCCTGTAAT|TACAGCACTT|CGGAAGGCTG|GAGGCCAGGA|GTTCAAGACT 214320|
|AGGTTGGCCT|GGTCCCTACT|GAAAAAAAAA|AAAATTAGCT|GGGTGTGGTG|GCACATGCCT 214380|
|GCAGTCCCAG|CTTCTGGGTA|GACTGAAGAG|GATCACTTAG|AGCCCAGGAG|CTTGAGGTCG 214440|
|CAGCTACTGC|ACTCCAGCCT|GGGCAGACCC|TCATCTCTGA|ATTGCTTAAT|TAATTAACTG 214500|
|AGCTGGCAGA|TTTGGCTGCA|TAGCTGTGGG|GAAAGGGTTG|TTGGAATAAT|GTCCAGTGTG 214560|
|CTCCCCTGAG|CTTCTACTGG|AACAGGTCTT|TGTGAGAGGC|CTGGAGATAA|GAGCTTGCTC 214620|
|ACAAAGGCTG|AGGCCTTTCT|GGGATGCTGA|ATGAGTTTAG|TGTGGCCAGA|GCATAGGGTC 214680|
|TCAGCAAAGG|AAAACTCCAT|AAGGGCCATT|TGTGAAGATC|CCCAAATACT|TGTGTGAAAC 214740|
|ATTTGGTAGA|TATTAGAAGT|TTTGTTTTGG|TTTGGTTTGA|GACAGAGTTT|TGCTCTTGTT 214800|
|GCCCAGGCTG|GAGTGCAATG|GTGTGATCTT|GGCTCAGTGC|AACCTCCACC|TCCCAGGTTC 214860|
|AGGCAATTCT|CCTGCCTCAG|CCTCCCAATT|AGCTGGGATT|ATAGGCGCCC|ACCACCATGC 214920|
|CTGGCTAATT|TTTTGTATTT|TTAGTAGAGA|TGGGGTTTCA|TCATGTTGGC|CAGGCTAGTC 214980|
|TCGAACTCCC|CACCTCAAGT|GATCTGCCCG|CCTCTGCCTC|CAAAGTGCTG|GGAATACATG 215040|
|CGTGAGCCGC|CGCGCCCGGC|AGACATTGGA|AGTTTTAAG|CAGAGAATTT|GTTGTATTGT 215100|
|TGTAGTTGTC|TTGGGTTTAG|ATTTATTGCA|TAAACAATCA|TTTTTGAGAA|GGGCCCACAG 215160|
|TCAGAAGTTG|GGAGTCTGTT|GCAATAGTCT|CAGAAGAATG|GCAAAGACCT|TGCCTAAGGG 215220|
|GACAGTGTGG|TAAAGGAGAG|AGTCTACATT|TGAAATATTT|CTGAAACAAA|AGCCAAAAGA 215280|
|TAAGACTTCA|AACTTCTGAT|TGCAAAGTGA|GATAGAAAAG|TTTCTTTCTC|TCTGTCTCTC 215340|
|TGTTATACCC|ATACACACAC|ACATATGCAC|AAACACCTGA|AAGAAAAAAA|AATTCAGGGA 215400|
|ACAGGCCAGG|TAGGGTGGCT|CATGCCTATA|ATCCCATAAA|TTTGGGAGGC|TGAGGCTAGT 215460|
|GGATCACTAG|AGCCCAGGAG|TTCACAAGGC|CAGCCTAAGC|ACATAGCAAG|ACCCTGTCTC 215520|
|TACAATTAAA|AAATTACCCG|GGTGTGGTGG|CACGTACCTG|TGGTCCAGT|TACTCAAAAG 215580|
|GCTGAGGTGG|GAGAATCACT|TGGGCCCAGG|AGGTCAAGGC|TGCAGTGAGC|ATGATTGTGC 215640|
|CACTGCACTT|CAGCCTGGGC|AAGAGCGAGA|CCCTGTCTCA|AAAAAAAAA|ATTTTTTTT 215700|
|TTTTTCCAGA|AAACAATACT|ATCTTAAGCA|CCAGCACTTT|AGTATATTCT|ACTGTGGACT 215760|
|AGTTCATTTT|TAAAAGAACA|CTAGGTTGGA|AATCATGAGA|TTGATTCCAC|AACTCACTAA 215820|
|AGCACCGTGT|CACTCAGTTT|GGAAAATATT|TCTCCTTAGA|GAGATTACAG|GTGCATCTTT 215880|

| | | | | | | |
|---|---|---|---|---|---|---|
| CTGAGCACCT | GTATGTTTTT | ACATTTGTTT | GGCTTCTCTG | ACCTTTGATA | ATTTCTGAGT | 215940 |
| GTTGTACTAT | TAAATATTAG | TGGCTAGGGG | TCAAATTGTG | GATCAGGTTG | ATCCTTATAT | 216000 |
| TTACAAGTTG | ACAGATACGT | TACTCCATTG | CTTTAAAACT | AACACAGAAT | TAGAGAATTT | 216060 |
| AGAAAATTCT | TACATTCCAT | AATTTAAGAC | CCAGAAAAAA | AAGATTCATA | TTTTGCATTA | 216120 |
| GATAGCTAAA | ATGGTACCAT | AAAAACAAAT | GATATCCACA | TATATATAGT | ATATAGTGCT | 216180 |
| TCTTCTGTGC | CAGTCACTAT | CCTAAGTTTT | TCTCTCCCTT | CCCCAAAAAT | GTAGGAATTA | 216240 |
| ACTTTATAGA | TGAAGAAACT | GAGGCACAGG | AATGTCACAT | GACTTGCCCA | AAGGAAATTC | 216300 |
| AGTCTTCCTT | TTTCAATTCT | TTTTTCTTTT | TACTTTGCTG | CAGGGTCTCG | CTGTGTTGCC | 216360 |
| CAGGATGCTC | TTGAACTCCC | GGACTCAAGC | GATCCTCCTT | CTTCAGCCTC | TCAAAGTGCT | 216420 |
| GGGATTACAG | GCATGAGCCA | CTGCGCCCAG | TCAGGAAATT | CAGTCTTCTA | AACATTCATT | 216480 |
| ATTGAAATAA | TATTTCCATA | AACATTTCT | TAGATAAACT | TTGGCATCTC | TAACTTCTAA | 216540 |
| GTAGCAAAGT | CATGGAAACA | GTCACAGAGA | AAATAACTTT | ATTTAAAAA | TAATAAATTC | 216600 |
| TTATCTCCGG | TGATAAGAAA | AGTATACAGC | CCATTTTTA | AAGTATTAAT | TTTACATTCT | 216660 |
| AATTTGGTTT | TTTTAATGTT | TACCATATAT | TTCTCTTTCT | ACATATGTGT | GTGAGTGAAT | 216720 |
| AAAATAAAGG | CATCTACAGA | TTTTTACATG | TTCAGTGAGA | TTAGCAGGGT | TTCACTTGAC | 216780 |
| AGCACTCTTA | CCATACTCAC | TTCTTGGCTT | TTCCTGATAT | CTAACATTTT | TAAAATGAGT | 216840 |
| AGTCCCTTTT | CATATGATTC | TTCCTTTTTC | AAGCACTATT | TTTGAACTTT | ATATTTGATT | 216900 |
| GGCAATAATT | TTTACAGACA | TTATTTTACG | ATTAACTTTA | ACTCTGTTCA | AATGATTTCT | 216960 |
| TCATTTTCAA | GTATTTTATT | TGAACTGCTT | TTTTTGGTTC | AACTACTGAG | TATTTAATTT | 217020 |
| GTCTGTTTTG | TAGAAAGGGT | ATGTAGATAA | TTCCATGTTT | TGTAAAAGTT | GTCTCTAAAA | 217080 |
| ATCTAACAAG | TGTAAGTACG | ATGCTATTAC | AGGGCTGAGA | GACACAGAAA | AAACACACAC | 217140 |
| ACACACACAA | AATTTTTTTT | TAAGTATTAC | TTGGTCTCTA | AACTAAAGAA | TTTACCATCT | 217200 |
| ATTTTGGGAG | ATGAAATCCA | AACATAAGCA | ATGACAACAA | TTATTATGTG | CTTAAATCAA | 217260 |
| TGTCCAAGAC | AATAATTGAC | CCCAAGGCAG | GGAAATCACT | GAGAGAGTAT | AGCAGAGAAG | 217320 |
| GTGTCCTCTC | TGTTCAGATG | AGCCTGAATA | ATTTGTTCAG | TAGGTTTCTG | CTACTCATTT | 217380 |
| ATAAACTGCA | CATCTTCTGT | AGTCCTGGAA | AATGTCTAAG | AGGAGAGAGG | AACTAAGATC | 217440 |
| AGGGCCACCA | TTTAATTAGG | AAGTTCTGGG | AGTACCTGAC | CCAGAAGAAA | GATCAGCATA | 217500 |
| GCTGAAAATC | ACCCATAGGA | GAAACATCTA | GGTAATCTTA | TTTCTGTTCC | ACCTGACATT | 217560 |
| TCAACCTCTC | TTTTCAGCTA | TAAGTATATA | AGTACTTATA | TGTAAGTAAA | GAAATTTACC | 217620 |
| CACATCATGT | TGTTTTTTAT | TCAATGCTTA | ACATGTATAA | TGCTAACAAC | ACAGACTTGA | 217680 |
| TGTCCAAAAC | ATTTCTATGA | ACAGCTCATT | ACTGGATGAC | TGAAATAATT | TTTCCAAGCC | 217740 |
| ACGTGGAGGT | TAATGAGTCA | GTTTTGAAA | GCAAGGAGAG | AAAAACATTA | GAATTTAAGG | 217800 |
| TGACGTTTCT | GTTGCGTTGT | AATCCAGAAT | ACAGAATAGT | CAGAGAAAAG | CAGAAAGTCT | 217860 |
| TTCTTCTTAA | ATTTTCTGAA | AACCAAGGTG | TGCATTAAAA | TGGTACATGC | CTACTTCCCT | 217920 |
| TTCCCTTTAC | CCTTTTTTCC | TGCATGGAAC | ATAGATATGA | CCCCTAGACA | TGCTGCAGAT | 217980 |
| GACCATGAGG | TTGAAAGATA | CATGGAAGAT | GGTTAACACA | GGATGATAGA | AGAGACCTGC | 218040 |
| ATACTTGGGC | AGCCTAGACA | GCTCCTGCCA | GCCCCAACA | AAACAGCCTA | GCCTTCTTGC | 218100 |
| CAATCAAGAA | AAAAAATCCC | TTCTGGTAAC | CCACTGTAAG | TGAATTTCTG | TAAATGTGGC | 218160 |
| CCAATGTATC | CATAATTGAT | ATACAAATAT | TAGTTTAGTG | GGTAGCACCT | CTCCATGAGC | 218220 |
| ATGTCGACTT | CATGAGACTG | AGATTTTTGA | CTGTCATGTG | CAGTTGTCCC | ATTACAGTGC | 218280 |

| | | | | | | |
|---|---|---|---|---|---|---|
|CTGGTGCATG|GGAACAGCTC|AACTGTGCAT|ACCCATTGAA|GAAATAGATG|CATGGTCAAT|218340|
|CGAATTTCCA|GGTATATCAT|ATGTTTCCAT|AAAAAAAGTA|AACATACAGC|ATATCTCCTT|218400|
|CCAGTTTATT|TATTTTTCTC|TCTAGGACCA|ATTTACAGTC|TATCAGCAGT|GCGTGAGCAC|218460|
|CTGTTTCACC|ACATATACAA|ACCCCTCCAA|GACTATAAGG|ATATCATTAA|GCTTTTTATC|218520|
|ACTGTCAGTT|AAGTGGTAAA|CATAGTTTTC|TACATACTTT|GCATTTTGT|TTCTCATGAG|218580|
|ATTCAATGTT|TTACATGGGT|AAGTTGTTAG|ATCATATTTA|TTCAAGATGA|GGCATTTGTC|218640|
|TCCTGGTAAG|ACATCTTGGT|CTAATGCTGA|CTCTGGGGTG|TGGACATTTG|GCTGTTGACT|218700|
|GTGAGGTGGC|TATCTACATG|TGGAGTGGAG|GAGTCCTGGC|CTTGGATTGA|GGAGAACAAG|218760|
|GTCAACTTCT|CACCTCACTT|GTTTCTGGCT|TTTGTGACCT|TGGACAAGTT|TAACTTTCT|218820|
|CTCTCCTAGT|CTTAGTTTTC|TTGTCTGTAA|GTGACAGCAA|TGATGCTGTC|TTTGTTGGGG|218880|
|TGGGCTGCCA|TAAAAAAATA|CCATAGATTG|TGTGGTTTAA|ACAACAAAT|TTTATCACAG|218940|
|TTCTGGAGGC|TGGAAGTCTC|AGAGCAGGGT|ATAGCATGGC|TGGATTCTGT|GGAGAGGGCT|219000|
|CTCTTGCTGG|CTTGTAGAGT|GCTACCTTCT|CACTGTGAGA|GCTCACATAG|CCTTTCCTCA|219060|
|GTATATGTGC|AGAGCTCCCT|CTCTTCCTCT|TTTTTTTTT|TCTTTAAAT|AAATTATTTA|219120|
|ATTTGGAAGA|CCAAGTGCAG|AATCTTCCTC|TTCTTATAAG|GCCACCAATC|CTATCCAGTT|219180|
|AGGAACCCAT|CCTAATGACC|TCATTTAACC|TTAATTACCT|CTTATAAGTC|CTGTCTAGGA|219240|
|ATAGAGTCAT|ATTGGGGTTT|ATGGCTTCAA|TATATGAATT|TGGGGGGATG|GGGAGACAAT|219300|
|TCAGTCCATA|GTAAACACTT|CCTCAAAGAG|TAGTTATAAT|GTTTATAAGA|GACAATGTAG|219360|
|GTAAAAGTAG|TTTCAGTTGC|ATGCAGCTAA|ATGCAGTTTA|GTATCCCTTC|AGAGTCCTCC|219420|
|GCAGAAAAGG|CACCTGATAA|ATATTTATGT|GGCCTTAACC|TAAGGTATTA|TTCTTTATAT|219480|
|AGTGCCTTCC|CATGTAATGA|TTGATGTCAT|GTTTATCATT|TGCAGTGCAG|TTTATTTCTT|219540|
|ATAGGTCATG|GCTACAGAAA|CATGGGAGAA|TGACCATCAT|TAATAGGTCA|TTAGAATATG|219600|
|TAATTTCAAT|TTTTTTTTCT|TTTGAAGGAC|TATTAGGTTA|ACAATGATTT|TTAAAATTTA|219660|
|TAGTAGATAT|GAGTGCTATA|AAACAGGAAT|TTCCATATTA|TTTTGGGATT|ATAAATTGGT|219720|
|ATGATCCTGA|ATAGCAATTT|GGCAATGTAT|ATGTTAAGAA|CCTTAGAAAA|TGTTTTTCAC|219780|
|TTTTGATTTA|GTATTTCCAC|TTCATGAAGT|CTATCCTTAG|GAAATAATAT|TTGAACAAAG|219840|
|ATTTATGTAC|AAAGATGTGT|GAGCTATATA|ATCTATAATA|TAATGCATAA|AAATGGGAAT|219900|
|CAATTGAAGT|AGTCAATAAC|AAATACATAA|TTATCAATAT|ATCCATAAAT|TATACATCCA|219960|
|TAAAAAAGTT|TCTAAGTATA|TTTATCTAAA|TATATATCAT|GACACCTAAA|TTTATTTTAT|220020|
|ATATGATACA|TGATGTGAGA|TATATGTATA|TATGAATATG|AGTATATATA|ATATACATAT|220080|
|AAAAGAATA|GGAGATACTA|GGAGTTATTT|TAATTTTGTC|TTTATGTTTC|CTGTGTCATA|220140|
|AATTTCTATG|AAGAATATTT|TAATAGTTTT|ATGCATAGAA|AAAAGAGCTA|ATTTTCTCA|220200|
|GCCAGGTGTT|CATTTGTCCT|TCTTTGATTG|TTCAAAATAC|CTCCATTTAT|CTTCTTCTAG|220260|
|GATCACTCAT|TTTCATTGGT|TTATTTGCAA|GATGAAACAG|TGTCCAGCAG|TGACGACTGT|220320|
|TGGAAAAGAT|ATGTCTAAAA|GCTGTTGTCT|CCCCCTGGAG|AAAAGAGAGA|GAGTGATTGA|220380|
|TTCACTTCTG|TAATTTATCA|GATATGAGAT|ATTGTATTTG|ACTCTGAGAA|CAATGATAAT|220440|
|GATGATGGCT|AAAGTTCACT|GGATGTTTGC|TCTGTGCCAG|GCAGTGTTTT|AAGCACTTTA|220500|
|CACAATAGAT|ACCAATGCAT|TTAGTTGTTC|CAACAACCTT|ATGAGATACC|TACTGTCATT|220560|
|CTCCCTGCGT|TATAGATGAG|GAAATTAAGG|CACAGAGAGG|TTAAGTTTCC|CAGGTAGCAC|220620|
|AGCTGTTGGA|TAATGAGCCT|GTGCAGTAAA|CCCACATCCT|CTAGCCCTTG|AATGTCTGTA|220680|

| | | | | | | |
|---|---|---|---|---|---|---|
| CGCTCTTAAA | AGATGAATGT | AACCTAGTCA | GTGTCCTAAA | GTTCCATTTG | ATCTAAACTT | 220740 |
| GAAGGATAAA | AATTTATCCA | GTGAGGAAAA | AGACTTAGTG | TTTTTCATAA | AGAAGATACA | 220800 |
| GCGACGAAGG | CCAGGCCGTG | GGGACTGTCT | GATTTTTAGA | GCCTAGAACC | CTGAGCACAC | 220860 |
| TCTCTAAACC | CTCCAACATG | CTCTTACTCT | GTTGCCTGCT | GAGCATCTTT | GATCCACTCT | 220920 |
| TGAGGCTAGC | AGTTTTCCTT | CCATTCAAGA | TCTCACAACG | TGTATTGTTC | TCTGCAGATT | 220980 |
| TTTTAAACAT | GCAATTTTAT | TTTTTAATTG | TTAAAAATAT | ATTTATTTCA | GTGCACTGAA | 221040 |
| GCTCAAATGT | GTGTGTTTTA | AAATCTAGTG | TCCAAGGTTC | ATTACCCCAA | TTGTTTAAGC | 221100 |
| AAGTCTAACA | ACAAAAGGGG | CACATTTTAA | TTTTCAATTT | TTTTTGTTC | TAGCCTACAG | 221160 |
| TTGAGTTTGG | GCAAATAATA | GTAGACAAAA | AAGTGAAAAG | AAAACTAAGG | ACAAGAAAAT | 221220 |
| AAAGGAAGGG | AGAATGGGGG | GAGAGGAGGG | AGAAAAGTGA | AAACAAAAGT | TTATTCATAT | 221280 |
| TTCTCTTGAA | TCCAATTCTT | TTACCATTTG | AAAACTTGAT | ATGGTCAGAG | AATAAGCCTA | 221340 |
| GAATTTTAAG | TGATGAGGAT | AAGGTTTTAC | CACAGGTAGC | CTCCTCTACA | TAGGTCTATT | 221400 |
| TCCTCATAGA | ATGAGAGAAG | CCCCATCATT | TCTGCTCTTT | TACCCTTCTG | AGCCAGCAGC | 221460 |
| AAGGAGATCT | ACTATCAAGG | CATGAGCAAC | TGTAGAAACA | TGAGACCAGA | TGTCTCTATT | 221520 |
| AATTATTCTA | CAAATTGCGC | ATTGGATGAT | AAGGTTACAT | GAATCTTTAA | ATCAGCAAAC | 221580 |
| CAAAGTCCCA | TTATTATTAC | ATATTTTTC | CTCCTCAGAA | CTGAAGTGGG | GCGGGGTACA | 221640 |
| GTGACTCACA | CTAGTAATCC | CAACAATTTG | GGAGGCTGAG | GCAGGAGGAT | CACTTAAGCC | 221700 |
| CAGGAGTTTG | AGACCAGCCT | GGGCAACATA | GTAAGACCCC | ATCTCTACAA | AAAACTTTTT | 221760 |
| AAAAAATTAG | CTTGGCATGG | TGGTGTGCAC | CTGCTGTGGT | TCCAGATACT | CAGGATGCTG | 221820 |
| AGGCAGGAGG | ATGGCTTCAG | CCCAGAAGGT | GGAGGTTACA | ATGAGATGCG | ATTGCGCCAC | 221880 |
| TACACTCCAG | CCTGGCAGCC | TGGGCAACAA | AGTGAGACCC | TGTCTCTGAA | AAAAAGAACT | 221940 |
| GAGGTCAAGG | AGTAGTAAGA | AAGTGGCTCA | TTCTCCAGAT | TTACTCTCTT | TTTCTTAATT | 222000 |
| ATAATGAACT | CATGATACTT | GAGGATATGT | CAAACTGATC | TTCAGACCCC | AAAGAAATTA | 222060 |
| CTCAGAGCCT | AGAATACCTT | TCAGGAAATG | TTACAGTGGT | ATACTCTACT | CAATTTAATT | 222120 |
| TTATGCTTGG | TCATCCAGGA | TTACACAGGC | TAAAGGTAGG | AAAAGTTTCA | CTAATTTTTA | 222180 |
| ATGTCTTTTA | ATTTAGGACT | ACTGGGATTG | TCTGTCAATG | TGCTGAATAT | ATATATCCTT | 222240 |
| CCAAATCTGG | AAGATTTAAG | AGAAATGATA | GTTATCATTC | TTTAAGTCCT | TAGGAATATG | 222300 |
| CCTAGAGAGC | TAATTTCATA | TGTTCAGGGA | AAAAAAGTGT | ATTTTTTCTC | AACCTGTTGG | 222360 |
| ACCCCGGTAA | ACATACTATG | ATCAACTGGC | ATTTTCATAT | CAAATAATTT | ATGAAATTCT | 222420 |
| TATAATTTAT | AGAAGGCCAA | CTCCTACCAA | AGTCTTCAGT | CATAAGCTGC | TTCAAGTCCT | 222480 |
| TTTAGGAGCG | TAAAGATGGT | TATAAATAAA | ATTTGTCAAA | CAGCAGTAAA | CACAGTGGTT | 222540 |
| TATATGCATT | AAGGATCTTT | AATCTTCACA | TACTTCTAGA | AGGTAGGTGC | TATTACCATC | 222600 |
| ACTGTAAAGG | TATAGAGAAG | GATACTAATG | CACAGAGAGA | TTAAATGACC | TGCCTCAGAG | 222660 |
| TCCCACATCT | TATATGTGGT | GATCTGGGAG | TCAAACTTGG | AGTCTGTCTC | CAGAAGCTTC | 222720 |
| ACTTTTTGTC | ATCATTGAGC | AGTGCTGTGC | AGCCATTTTA | CTAGCATGAT | ACCACGTCTG | 222780 |
| GAACTAGTGT | TCTATAGGTG | CTATTTCATT | TAATCTTCAC | CCCATCTTTA | TGAGTAGGGC | 222840 |
| AATTATTACC | ACTCTATAGG | CTCAGGGTAG | TTGAGTTTGT | CAAACTGTGA | CTGAAAGACA | 222900 |
| TTTAATTTTT | GGCATACTAT | TTACTTGTGC | TCAAGGTATA | TCAAGCAATG | GACTGATTTC | 222960 |
| ACTCAACAAA | GTATTTTAAA | AAGATGATTT | ATAAAATAGA | AATGGGAGAA | AAAAACTACA | 223020 |
| AACTGTCTAG | GAATAGGATG | TTATGTTTGC | ACATTATTTT | CAGTAGAAAA | GAGTTTAGTA | 223080 |

```
TGGATACTCT CTTCTTGTAT AAACCAAGAA TGTTAAAAGA AAACAATTAG TGATTCTCTA    223140
GAAACAATTA GTGATTCTCT AGAAACACTT AAGATTGGCT GTGCAGCACT ATGGCTATCT    223200
CTGTGTAGTA TTTTCCACTG ACAACCAACA TTTCCATGTT AGGTAGGCCA TGTCTTCACG    223260
ATTTCTGGCA CCAGAGTTTT TCAACTCCTC CATTTTTGGT AAAAATATCT CATAAAGGAG    223320
CAAGTCTAAC CATGTGAGTT TGTTTAGTTT TTTGTTTTTT GTTTTTTGA CAATGGCTTT    223380
GTAACAACAT TTAATAATCT GCATATTAGA GAAGCACAGA AGTAGGGCAA AAAAAAAGT    223440
TATGAGGGTA ATTACAAATA TTATAAGAAT TCCTTAAAGT ACAAATTGTC TCCAAGAATT    223500
TAATTGGCTT GTCTTAGATG AATAGGTCTC AAAGATCAGT TTGGTCAAAG ATCAGTTTGG    223560
TCAACTTTAG TTAAACAAGT TCATTTTCC TAATTGATTA TTTTGACTCA AATGTGGGCC    223620
ACAGGCAGAA ATAAATTTTC TAGTAAATAT TCTTATTTAG GAACTTTTAG TCAAGTTATA    223680
AAGGTCCTTG TTACAAACCT GCAAAAGTT AGCATGCCAA TATCTTAGTA AAATATAACT    223740
GAGATTTGTT TATTTGCTTG TTTTTTAATA CTTGGGAGGG CCAGATCAAA ATTTCATCAC    223800
TGGAAAGACA GATAATGGAG AAAAGGACAA AACAGAATAA TACCACAGGT AAAAGAAGGA    223860
AGAAGCTGTC TATTTCAGAC CTCATCTTCC TCTGTAGACT TGAAGAGGA AACTTCCTAC    223920
TTCCAGAATT CTGGAGGTCT TTTAATGAAT CTCAGAACTG TATTTTAGT GATAGTGTAT    223980
TTCTCAGTGA GATTCCAAAT GTGTTTACAC TGGGAAGCAC ATATCCATCT GCTCTGAAGT    224040
ATAAAGCAG TATTTGTTGT TTGAAGTACT GAAAATGGAG GTTCCAGCAT TGTTATAATG    224100
TTGTCAGAGA AGATTGGTTA TTACATTAAG ATATGAATAT AAATCATGGC TATATAAAAA    224160
TAAGAAAAAG ATTGAAGTCT TATTTTAGAG TGACAATCCA TAGTAAATTG AATGTACCAC    224220
ATTAACAAAC AGTAACAACT TTTTAAATAA GTAAAGGCTC AAGGTAGTCA TTATCTCGAA    224280
TGCTTACTTG TGTTTCTCTG TAGCTATAGT ACTTGATAGA GTCAGAGCTG TTTGGATTAA    224340
CCATAGCCCT TAAACAAAGC AGGCAATTGT GTTCCGCAT AGGCATGACG AAAACAGAGG    224400
CAGTCATCCA AAACCTGCAT GGTCCTCTAC GCCCACACGT ATACAGTACG TGATTTACAA    224460
ATCTAAAGTG GCGAAAGCAA CAGTATCTAT TCTAAGGCAA TCATATGTTC TCTTATCTGT    224520
TTATCAATGG TTATTCTAAA CTGTGTAAAA ATGTTATTTG CATAAAACTA CACTGTTTCT    224580
TGTGATTTGT ATTTGTACC CTCCAATTTA GAAATTGTCC AGGTATCCAA AGATTGAGAA    224640
TTAATTTACT CAATTTAATA ATATTCACCT AAATTCTTAA AGTTATCATA CACTGTGAAC    224700
TCAGTACTTA AGCTCACACA TTGAATCCTT ATAATTAGTA ACATAAAATT TAATTCCATT    224760
TTTAAAAATG ACATTATCTA TTATCATTTA ATTTGGTTCA ATGAATAATT TACAATTTTA    224820
GAATAATAAA TAAAGTGATG TTAACTCATG TAACCAGTAC AACTAGTGGA AGAAATTTAG    224880
TAAATGCAAG TTAAATTAGC TTTTGTTTTT GTTTTTAGA ATATGAACCC TAAACTTGTG    224940
TATACTATAA TATTCTGCTA ATATTATTTT TACAGTATAA GAATAAAGAA GCCATTTTA    225000
AAATGAAATT ATTAAGCCAA TTTGTCCAAA AAAAATCTTG ATTAGATGTA TTATATATTT    225060
TCCTTATTAA AAAAACCTAA TAAAAGAGGT ATTAATATTT TAAGTTATT TAAAAATTGT    225120
GAAGTATTTT TTTTACAAAA TACTTTAAGC TGTTAACTAA GACCACTAAT GAAACTCACA    225180
GTTAAACTTT TTTTCTCTTA ATTAGAACTT AAAGAGGTAG CACATTTAAA GCACAAGGAA    225240
AATTTTTGAT TTTTTTTTAG ACAAATGAGT TTTTATTTAA ATTGATGTAT TTTAAGTCTT    225300
TATGTAAGCC AACTAAAATT TAAGATTACA TTATAATTTA TTAATTCCCT TAAGTGGATA    225360
ATTTCACAAT TATTTAAATT CATAAAATAA GATAGTCTTT TCTGGGCACG GTGGCTCACG    225420
CCTGTAATCT CATCACTTTG GGAGGCCGAG GTGGATCACC TGAGTTCGAG ACCAGTTTGG    225480
```

| | | | | | | |
|---|---|---|---|---|---|---|
| CCAACATGGC | GAAACCCCAT | CTCTACTAAA | AATGCACAAA | TTAGCCAGGC | GTGGTGGTGC | 225540 |
| ACCTGTAATC | CCAGCTACTG | GGGAGGCTGA | GGCAGGAAAA | TTGCTAGAAC | CCTGGAGGCA | 225600 |
| GAGGTTGCAG | TGAGCCGAGA | TTGTGCCACT | GCACCCCAGC | CTGGGCCACA | GAGCAAAATT | 225660 |
| CTGTCTCAAA | AAAAAAAAAA | AGATAGTCTC | AATCTTATTG | CCAATTAGGA | AAGCTAACCG | 225720 |
| TGCTAATAGA | ACAGAATTTA | AAGTGGGTAA | AAACAGAGCC | ATAGGTTATC | TATTTAGCAT | 225780 |
| GTTGATCAGT | TAAAGAAATA | AAAGTATGTA | ATTAAGATCA | GAAGTCCCTC | AGGTGGCACC | 225840 |
| ACTGCTGAGA | ATATGAATAA | TTCTGATTCT | CAGTTTAGAA | GAAAATTCTA | GTTTCCTAGT | 225900 |
| TTCCAGCATC | ACATCCCTTA | CAATAAACTC | GTTAAGGTTT | AGAAAATATT | AAATCTTTGT | 225960 |
| TTTATTCAGA | TATTGAAAGC | ACTCTTTTTT | TTCCCTGACT | CAATAGTCCA | ATTTGTAACA | 226020 |
| ACATTATGTT | TCTTCTGTCC | TCTAACCTTA | CTTAAAGAAC | GTGAAGGGGC | AATAATGTGA | 226080 |
| AATTACTAAA | ATTAATAATA | AGCTGTAGAG | CCTCTGCCAT | AGCAGTTATT | GAGACCAGAC | 226140 |
| ATTCGGTTTC | CTTGATTTCC | TTTTTGTCTC | CTGTTAGTCC | TAACACTTTC | TTAAAGTCAA | 226200 |
| AAGTTATAAC | AGGGCAGCCA | TTTTATATTC | ATATCATCTT | AACACAGGAA | TACTGGTTTT | 226260 |
| GCAGATATCG | ACAACTATTT | GGACTCAAAA | AAGACAAGTT | TTGGAAGGTG | GAAAGAGGCA | 226320 |
| TACAAGCACA | AAACATCAAA | TCCCATGTAA | AGTCAGAAAG | AAAAACACCA | ACTCTAACCC | 226380 |
| TGTGTCCTCA | CAGAGAATAT | CAACATCTTC | AAACAAAAAC | ACCCCAAAAA | AAGGTTAATA | 226440 |
| AATAAACCAG | ATTTCCTGTC | CTCTCCACTG | ACTAATCACT | TAATGATGTG | ACCAGAAAAC | 226500 |
| CAGAATTCAA | ATTCTACTAC | TGCCACCAAT | ATGCAACCAA | TCAGCCAAGT | CCAATTAGAA | 226560 |
| TAACCAAAAC | AAACAAACGC | GGACGATAAA | CTTTTAGCAT | GCAAAAGCCA | AAGGAAAGTG | 226620 |
| AACAGAAAAC | TCAAAGGGTC | CAGGGATAGA | CAACCTGTTT | CCAAGCACACA | CATTTCTGTT | 226680 |
| GGTTCTTATT | GTATGACTCA | CATAAACACT | GTCTTGGTGG | AAAATTCAGA | AATAAATGAC | 226740 |
| CAAGAAGTTA | ATAATTTGCT | TACTGGGTAC | TTGTACAGAA | GAGAGAACAA | GCAATAGAAT | 226800 |
| TATTTCATCT | AACACAGGCA | AAAACATAAT | CTATGTAAGA | GAAAGGGGAA | AAGGCGGGGG | 226860 |
| AAACAATACT | GAATTTGTT | TGCAGATTTT | GGTTACACTG | ATTAGTTAGT | TGGCAGGTAA | 226920 |
| GAAAACGGTC | AGTCTGAATG | GGAATAAGTG | ACCAGGTCCA | TTACAGGCAT | AGAAAAAAAA | 226980 |
| AAAACCATTT | AGGCCCGGCG | CGGTGGCTCA | AGCCTGTAAT | CCAGGACTTT | GGGAGGCCAA | 227040 |
| GGCGGGCAAA | TCACCTGATG | TCCGGAGTTC | GAGACCAGCC | TGACCGACAT | GGAGAAACCT | 227100 |
| CGTCTCTACT | AAAAATACAA | AATTAGCCAG | GGTGTCGTGG | CGCATGCCTG | TAATCCCAGC | 227160 |
| TACTCCGGAG | GCTGAGGCAG | GAGAATGGCT | TGAACCCGGG | AGGCGGAGGT | TGCTGTGAGC | 227220 |
| CAAGATCGCG | CCATTGCACT | CCAGCCTGGG | AAACAAGAGA | GAAACTTCGT | CTCTAAAAAA | 227280 |
| AAAAAAAAAA | AGAAAAAAAA | ATTTACTTGT | GAGGGACTCT | GGAAATTTCA | TTTCTCATCA | 227340 |
| GAATTTCTCA | GATAAGTTAT | CTAGGCAAGG | CAGCCTGTGA | TTGCACAGCA | GTGTTCAAGT | 227400 |
| ATAAGGCCTT | GTCTGGCACC | AAAGACAGGC | CTTAGTTTAT | TTCCCAGGTG | TGAAAGAAAT | 227460 |
| TGCAGATTTA | AGATCACACA | GTCCTTATGT | TAAATAACTG | TAACCTAAAT | TACATGGTAT | 227520 |
| TTAAGTTTGT | AAAAATCTGC | TTTAACACTA | ATTTTATTTA | TTGTATATTC | CCGGTTTTTA | 227580 |
| ATGGAGAAAG | CAAACTTCTA | GGTGCTAAAA | ACGTGTTCTA | GACTTGAATA | AAAAGATAGG | 227640 |
| TAGACTACGT | CTAACCCTTC | ATCTTAAAAT | CTTTACCTGG | AAAAGACCAT | GAGTAAAATA | 227700 |
| CTTAAGGGAA | TGTGGAATTT | CCCAGGCCAC | AAAGCGGCCT | GCAGTTGTCT | AGGAAGGGAG | 227760 |
| AGTCCTCTAG | GAGATACAGT | GTATGTGCTA | AGTTTAATGA | CGTCTCCTCT | TCATTCTCCC | 227820 |
| CCACCCAGCG | CCTAGTCCTT | ACTGGCCTTC | AGTTCAGTGT | TCGAAGGCTT | GTCAATTTAC | 227880 |

| | | | | | | |
|---|---|---|---|---|---|---|
| CCAGCAGTTA | AGAGTTGGCT | TCTCCTAAAG | CAACTTTCAA | ACTTGTCTGC | ATGTTACAAG | 227940 |
| CCCCCTACGG | AGATTTTAAG | TTTCAATCAG | GCAACACACC | ATTTATGGCT | GACTGAGCAC | 228000 |
| TGGGATTCAA | GCAAAATTTG | ATTTGATTTG | AATCTTGAAT | AAACCAGTTG | AATAGAATAA | 228060 |
| GATGTATGAA | GCAACATCTG | GCGCAGTGCT | TACATCTTTA | GTTCTGTACT | GCCTTAGTGT | 228120 |
| TGTTATCAAA | ACTGACGCAT | ATTAGTTAAA | AGACTATTAC | CGGGGCAGTT | GGAAACCCAG | 228180 |
| GAGACACACC | TTCAGTATAC | TACGAAGGTG | TGCGCCACGA | AAACAGAGGG | GGAGTCCTTC | 228240 |
| CTTAGGCAGT | TACTGCCCAG | GTTCCCACTC | CGGTCCGCTA | TGTAAATCAG | AGTCTCAAAA | 228300 |
| CAGCTTTCCC | TCGATTGGTT | AATATTTAAA | ATGACAGGAC | AGCCTATTGG | CTAGAAGCTG | 228360 |
| GTGGCGAAAT | TATGACATTA | CGGCAACCGT | TGATCCTGGC | GACGTAGACA | GGGACAGACA | 228420 |
| GCTGGGTCTG | AAACCTAAGC | GAGCCTGCGG | TTTCTTCCGG | GAACGCCGAG | TTAGCAAAAT | 228480 |
| GGCCGCTTGT | CTCCATTTTA | AATTTAAGCA | CAACGAATTG | ACCCAAAGC | CATTTTTAAT | 228540 |
| GGCTGGCTTC | TTTCGGGTTC | AGGACCCTTT | GTCCCTCTCT | AAGCTGCAAC | ACTTGTCCCC | 228600 |
| ACCCCTCTCC | AGTTCCTATA | TTCTAATACC | CCTCCGCCGC | CAAATAAAAT | TTGGCGTCTG | 228660 |
| GCCACAGCTC | TTTTAGTGGG | TATCTGGGTG | GCTCTTAAAA | GAGCCTTTGG | GGTTAGGTGT | 228720 |
| TAAGACGCTT | ACTTGGAATG | TTTACTTGGA | GCTGGTGTAC | TTGGTGACGG | CCTTGGTGCC | 228780 |
| CTCCGACACG | GCGTGCTTGG | CCAGCTCTCC | GGGAAGCAGC | AGGCGCACGG | CCGTCTGGAT | 228840 |
| CTCCCTGGAG | GTGATGGTCG | AGCGCTTGTT | GTAATGCGCC | AGGCGGGAAG | CCTCGCCCGC | 228900 |
| GATGCGCTCA | AATATGTCGT | TAACGAAAGA | ATTCATGATG | CCCATGGCCT | TGGAAGAGAT | 228960 |
| GCCAGTGTCG | GGATGGACCT | GTTTCAGCAC | CTTGTACACG | TACACAGAGT | AACTCTCCTT | 229020 |
| GCGGCTGCGC | TTGCGCTTCT | TGCCATCTTT | CTTCTGCGCT | TTGGTCACTG | CCTTCTTGGA | 229080 |
| GCCCTTCTTC | GGGGCGGGAG | CAGACTTGGC | TGGCTCAGGC | ATCTTAAAAC | ACCAGAAATG | 229140 |
| TGTCGAAAGT | AAAGAGCGGA | TTTCTGCTAC | TTATAGGGCT | TTTATGCTAA | TGAGGGATGG | 229200 |
| AGAGTACCTC | TTAGTTAATT | GGAAGACAAA | CTGCACAGTT | GTCATCCGTG | GGCAGAGCTA | 229260 |
| TGCAAATGAG | GTATGAAAGT | ACAGCTTTTC | TATTGGCTAT | CTGACTAGCA | TTTGCTACCG | 229320 |
| ACCAATCAAA | AAGTCGGATT | TACTCCCCAG | GAACTACCTA | TAAAAGCGGC | CATGTTTTAC | 229380 |
| ATATTTCTTG | ATTTGTTTG | TTTTCTCGTG | AGCTTAGGCC | GCTGGTTTTG | GTGATTTTTG | 229440 |
| TCTGATTGCA | ATGTCTGGAC | GTGGTAAGCA | AGGAGGCAAA | GCTCGCGCCA | AAGCGAAATC | 229500 |
| CCGCTCTTCT | CGCGCTGGTC | TCCAGTTCCC | GGTGGGCCGA | GTGCACCGCC | TGCTCCGTAA | 229560 |
| AGGCAACTAC | GCAGAGCGGG | TTGGGGCAGG | CGCGCCGGTG | TACCTGGCGG | CGGTGTTAGA | 229620 |
| GTACCTGACC | GCCGAGATCC | TGGAGCTGGC | CGGCAACGCG | GCTCGCGACA | ACAAGAAGAC | 229680 |
| TCGCATCATC | CCGCGCCACT | TGCAGCTGGC | CATCCGCAAC | GACGAGGAGC | TCAACAAACT | 229740 |
| GCTAGGCCGG | GTGACCATTG | CTCAGGGCGG | CGTCCTTCCT | AACATCCAGG | CCGTGCTTCT | 229800 |
| GCCTAAGAAG | ACCGAGAGTC | ACCACAAGGC | CAAGGGCAAG | TGATTTGACA | GGTATCTGAG | 229860 |
| CTCCCGGAAA | CGCTATCAAA | CCCAAAGGCT | CTTTTCAGAG | CCCCCCTACC | GTTTCAAAGG | 229920 |
| AAGAGCTAAC | CTCACTGCTT | GTAGGTAGAA | GGAAAAAAGG | CACTAAGGTA | AGTTAATTTT | 229980 |
| ATGCCAACCT | TGAGCAAAGC | GTATTACTGC | TTTTCGGTTT | TGGGGAGCG | CTGTTACTAA | 230040 |
| AGGTTGGTCT | GTTTGTATGT | AATAGTAGGT | CAGTTACGTA | CTATCATACT | CTAAAGAAAT | 230100 |
| ATTCTAGTTA | ATGCTTTGTA | AGATCGACCA | TAGTTAGTGC | CTAACAGTTT | ACATGCAGGG | 230160 |
| ATGCCTCGTG | ATCTAAACAC | TTCGTTGTGA | TTACTTTAAA | AATGTAAATT | GAAGGCAAAA | 230220 |
| CTCTAACGTG | TTGGTAACCT | TGTTTGGTCC | TCCGACTAGT | CCCCCGTCTA | TTTTTTTCTC | 230280 |

| | | | | | | |
|---|---|---|---|---|---|---|
| AATTTAGGCT | GTAGGCAGCC | TCACTTTCCT | AATTCTGTGA | GAGTTATAGG | TCCCATTCCT | 230340 |
| GCTAAAGTGC | AGAGTATATT | ACCTAAAAGT | TAACCAGGGA | GTTGAAAGGT | GTCTGTAAAA | 230400 |
| CAGACTAATG | TCCCTAATGT | AGAACGGTGC | CTGACATGCA | ACTTACTCTT | GTATTTTAAG | 230460 |
| AAGCTCAAGC | GTCTAGGTTG | CCATTACAGG | CAGAAAAGGA | AATAGAGTGG | GGCCTGTGGC | 230520 |
| CACTCAAAAA | CCTTTGCTTT | CTGCTCACCC | CTCTAATCCT | ACCACTTTGG | GAGGCCGAGG | 230580 |
| GGGCTGATCA | CCTGAGGTCA | CGACTTCGAC | ACTAACCTGG | CCAACATGGT | GAAACACCTC | 230640 |
| TCTACTAAAT | AAAAATAATA | AATAAAAAAA | TAAGTTGGGC | GTGGTGGCAC | ATACCTTGTA | 230700 |
| ATCCCAGCTA | CTCTTGAAGC | TGACGCAGGA | GAGTCGCTTG | AGCCTGGGAG | GCGGAGGTTG | 230760 |
| TAGTAAGCCG | AGATCGTGCC | ACTGCCCTCC | AGCCTGGGCA | ACAGTGAGAC | ACGGTCCCC | 230820 |
| AAAAAAACCT | TTGCTTCTAG | GGATCTGGTA | ACAGCTGCCC | CACCCACAAG | AAATGGAGAT | 230880 |
| CTGGGACCAT | GGACAAATTT | CTAGAGACCT | ATTTTCCTGG | ATTCTGTGAA | TCTCGCCGAG | 230940 |
| GTTTTCTTCC | GGATCTCGGT | TTCTGCATTT | TTTTGTTTGT | TTGCTTGCTT | TTTTGAAACG | 231000 |
| GAGTTTTGCT | CCTGTTGCCC | AAGCTGGAAT | GCAGTGGCGC | GATCTCGGCT | CACTGCATAC | 231060 |
| AAACTCCGCC | TCCCGGGTTC | AGACGACTCT | CCGGCCTCAG | CCTCCCTAGT | AGATGGGATT | 231120 |
| ACAAGCGCCC | GCCACCAGTA | GAAACGGAGT | TTCACCAGGT | TAGCCGGGCT | GGTCTCGAAC | 231180 |
| TCCTGACCTC | AGGTGATCCG | CCAGCCTCTG | CCTACCAAAG | TGCTGGGATT | ACAGGCGTGA | 231240 |
| GCCACCGCGC | CCGGCCGGTT | TCTGCTTTGA | TCGGAATTAA | GTGGGCAGAA | AAGTCTAGGC | 231300 |
| GGGCTAAGTC | TTGCCTATGC | ATCTGCGCCC | AGCTGCTCAG | ACTGGCCAAA | CAGACCCAGT | 231360 |
| CGTTTAGTCT | AACGCTTCTG | GAACTCCACT | GAAGCGTTTT | GCATTGTTTC | GTTTGGAGCC | 231420 |
| TTCAAATCCG | AGTGTGTGGC | AGGAGATAAT | AATCCTAGCA | GAAGCTGTTT | ACTGCTGACG | 231480 |
| CGCCTCCCAC | TTCCCAGATA | CTGACACCGG | CTCAGGGCGG | ATCCAGCCTT | TTCCGCTCTT | 231540 |
| CCCTCCCTCC | ACCCCTCCT | TTCCCTACAA | CTACTCTCAA | AGGAAAAGGG | TTGGATGTCC | 231600 |
| CATTTGGGTG | AAAACAAAGT | GGCATAAAAG | CAAATGATCA | CCTTTGATAG | CCACATATTA | 231660 |
| GAATTTTCCG | AGGGTATTTT | TAAATTACAA | CGATTCTAAT | GGGCAGCTGG | GCTGAGAATC | 231720 |
| ATCAGATTTG | AAGGTCTGGT | TTCACATGGC | TCTTGGGCTG | AGAAGACCGG | ATTTTCCCCC | 231780 |
| CCCAGCATTT | CCTGTATGTC | CGAGAATTTC | GATCCTAAGG | TTAGAATTGC | CTTATGGGCC | 231840 |
| TTGGAATCCT | TTTTATTCAC | TGACCAAATT | GCCTTTGATT | CCAGCTCCCA | ATCGGTGTGT | 231900 |
| GACCTTGGCC | TAGGGCTTAA | TCTCTTCCTA | CCTCCATCTC | TTCCTTGTAT | GCTTTTGCTC | 231960 |
| ACCTTGAAAT | GAAAAGAACC | TGGCTCAGCA | AGTGTAGATT | CTGAAATCAG | AAAACAGGCT | 232020 |
| GAATAAGAGA | GATGGTTTAT | TAGGCACTAC | TGTGTGCCAG | GCACATTTCA | TGAGCTTCCA | 232080 |
| GTATGTTAAT | TCATTTAATC | CAACAATCTA | AGAGATAGGT | TTTATCCTTA | TTCCGAATTT | 232140 |
| TGAGATGAGC | AAACTAAGAA | ACAGCTTAAA | GAACTTAAGT | TGTAAGGCCA | GGAAAACAGT | 232200 |
| ACTTATAACA | GCTGACTATT | CTATAACCAC | ACCTCCTTAA | GAGATTATTG | TCAGAAAAAT | 232260 |
| AGAAAGAGTA | AAACATCCAT | ACATAATGGG | TAAACTTTGT | CCACATACCA | GAATGTTACT | 232320 |
| AATGGCTTTC | TAACCTCTGA | AGAATTTAAG | GGAAGGAGGA | AAGGTAATTT | TCCCAGGGA | 232380 |
| ATCTACACGA | AGAGGTAAAT | CTTGACAATG | TATTAATACT | GTAAACCCAG | GGAAAAAAG | 232440 |
| CCAGTACAAT | TTTTATTTAG | GGTGTGGCAA | ATAAACAAA | GGGACACGTG | AAAACATGGC | 232500 |
| TCAGTAAAGA | GCTACAAGAC | TTGGTGCAAC | TGACTTATTG | TGGTGAGTGA | GAAAAGGAGA | 232560 |
| GAGAGAAAAC | TTGAATTTCA | ATTCTTCTCT | CTGGGCTCCA | ATAACAAGAT | TTTGTATTCG | 232620 |
| GTCTATTTAG | TAGTGAATGA | TACATTGTGT | TAAGTTTGTT | AACCTAGAGG | CTTTCATCTT | 232680 |

-continued

| | | | | | |
|---|---|---|---|---|---|
| AAGCAGTACT | TAAGATGTAG | ACCCCCTCTT | ATTCAAATAC | TGATAATCAG | CATAGAACTT 232740 |
| GGCATACAAG | AGACACTTGG | CTGTTGGGCA | TTGAGAAAAT | GTTGAACTGA | ATGAATCAAT 232800 |
| GACTTAGGCA | GCCAGGAAGC | ACTTTGTTGT | AGAGAGTTGG | TTTATTACTA | AGGAAGACAT 232860 |
| TAAGTATTAA | ATATTAGACT | AATAGGTTGC | TAATAGTGTT | TTCTCTTTCC | AATAGAAAAT 232920 |
| GTCTTCTGAG | GCTGATCTGG | TGTCTCACAT | CTGTAATCCC | AGCACTTGGG | GAGGCTGAGG 232980 |
| TGGGTAGATC | ACCTGAGGTC | AGGAGTTTGA | GACCAGCCTG | GCCAACATGG | CGAAACCCCA 233040 |
| TCTCTAATAA | AACTACACAA | ATTAGTCAGG | TGTGGCGGTG | TTCACCTGTA | GGCGCCTGTA 233100 |
| GTCCAGCTA | CTCAGGAGAC | TGAGGCAGAA | GAATCACTTG | AACCCCGGGA | GGTGGAGGTT 233160 |
| GTAGTGAGCC | AAGATCGTGC | CACTGCACTC | CAGCCTGGGC | GACAAAGTGA | AACTCCGTCT 233220 |
| CAAAAAAAAA | CCAACCCCAT | CTCTACTAAA | AAATACAAAA | ATTAGCTGGG | CATGCTAGTG 233280 |
| CACGCCTGTA | GTCCCAGCTA | CTCGGGAGGC | TGAGGCAAGA | GAATCACTTG | AATATAGGAG 233340 |
| GGGGAGGTTG | CAGTGAGAGT | GAGACTCTCA | AAAAAAAACA | ACAAAACAAA | AAGTAACAAG 233400 |
| AAAAAGAAA | CTATATTCCA | AAAATCCAAA | TTTCACTGGC | AGTTGTTCT | GGGAGCTTCA 233460 |
| GACACATAGA | AGGTGTCAGT | TAACCAGTTC | TTACCTAAGA | GGTACTGCTA | AGAGCCAGT 233520 |
| CCCTAAGCAA | AGGGAGCTTC | AGAGAAACAC | AGAAGGTGCC | AGTTAACCAG | TTCTTACCTA 233580 |
| AGAGGTACTG | CTAAGAGCCT | AGTCCCTAAG | CAAAGGACAT | TCCTCGTAGC | TCTGTCCTGT 233640 |
| CTCCTCATCT | CCAAAATACT | TTACCTTCTA | CTTGAAATG | CCCACTATTA | TATTCAAAAG 233700 |
| CCCTAGTTAC | TTCCAGGGAA | AATTATCTAT | TGAGCAATGA | ATTTCGGTAG | CTTCAGTTGG 233760 |
| ATTCCAACTC | TTGAGCAAGT | TTTCATCTCC | CTTGCCTGAA | TGGCCCTGGG | GAGGACTATT 233820 |
| TAAATTGGGG | CGAGTGGATG | AGGATGCTAA | ACCTAGAGGT | CTCCCAATTA | CCAAAGGCAC 233880 |
| CTGGGCACCA | GGGACTAAAG | TTTGTCTCAG | GAATTTACTG | AGATATGAGG | CTGAGATAAA 233940 |
| ATCATTTTT | GGTACATAAG | GTATCTTGAA | CAAAGCAGAT | CAGTTTAACA | CAAAATCAAC 234000 |
| AATCGTAATT | TCCCTTTTA | AATTTCCAAA | TCTATGTAGC | AATATCCTTT | CCTTTAATTC 234060 |
| ATTCATCATC | TCTATTCACT | TTTTGTATTC | TGTAAATCAT | TTGAACTTTT | ATAAGAATTA 234120 |
| TATTTTCCCC | TTGAGGTCAC | AAAAAAGAAA | GTATTAGAAA | TTTTATAACC | AATTTTTAAA 234180 |
| AAATTATATT | TTAAGGTTAA | ATACAAACCT | TCTAAAGGTT | TGTCATCTGT | TGATCCTAAA 234240 |
| TTATAATTAT | AAATTTATAT | ATTCCTGTTG | AATATAATGC | ATGTGTGTTA | CAAGATTATT 234300 |
| AGCAATTTGA | GAATTTCCCG | TGCATATTGG | AGATGAGCAA | ATGGAATAAG | TGCTCATGTG 234360 |
| TAGCGACAGG | ATTCTCTATT | TTATTTCAAT | ACTTAATATT | GTACCAAACC | AAGTAAGAGG 234420 |
| AGCATCATGA | GAAAATGTAC | TAAAGGACAG | TCATTACCTA | TATTTACACC | TAGAAAGAA 234480 |
| AACTATATTA | TTGATAAACT | GATAAATCTA | TTTTATGTAT | TTATTTATTA | TTTTGCTCTG 234540 |
| TCATCCAGGC | TGGAGTGTAC | TGGTGCGATT | TCCACTCATT | GCAACCTCCT | GCTCCCAGGT 234600 |
| TCAAGCAATT | CTACCTCAGC | CTCCCTAGTA | ACTGGGACTA | CAGGCATGCA | CCACCACACC 234660 |
| CAGCTAATTT | TTATATTTAT | AGTAGAGACA | GGGTTTCACC | ATGTTGGCCA | GCCTGGTCTC 234720 |
| AAACTCCTGA | CCTCAGGTGA | TATGCCCACC | TCAGCCTCTC | AAATGCTAGG | ATTACAGGTA 234780 |
| TGAGCCACCG | CGCCCAGTCT | GATAAATCTA | TATTAAAAG | AATAAATATA | ACCATTGCAT 234840 |
| CTTCAACAGA | AATTGGAATA | TGGCATGTAG | ATTTCAAAAT | AAAATGAATT | CTCTGGCATT 234900 |
| GAATTACTGT | ACTCATGTTG | AAGAAATGTC | AGAACTTCAT | TGGATGTTAT | TATATTACAG 234960 |
| TTGTTTGTTT | GAGTTGTAGT | TTGGGCAGAG | TAAAGGAGCC | AACATGTCTT | AGGATTTAGA 235020 |
| ACTTGTGCAC | ATTGCCTACA | GTTGAAAGAA | GAAAGCATGC | TAAATTCCAG | CCTCTTTGGT 235080 |

```
ATGTGGTTGG GACGTAAAGT TTTACCACAT CCTTCATTGT CTTAGCCTAC TCAGGCTGCC    235140
ATAACAAAAT ACCAGAGACT GGATGGCTTA AACAACAGAA TCTTTTTTTC CATATCTAAG    235200
AGGCTTGGAA CAGAAATTCA TTTTCTCACA GTTTTGGAGC CTGGAAGTTT AAGATCAAGG    235260
TGCCAACATA GTTTATGGTG AGAATCTGTT CCTGGCTAAC AGATGGCTGC CATCTCACTG    235320
TGTGTTTGTA TGGTGTTTCC TTGGTGCCTG CGTGGAGAGA GAGCTCTAAG TGTCTCATCT    235380
TCTGTAAGGA CACCAGCCCC AATGGGATTA GGGCCCTATC CTGTGATCTT TAGTTTTATG    235440
TACCCCCTAA AGGCTCTATG TCCAAATGCA GTCACACTGG GGTTTAGGGT TTTAATAAAT    235500
GAATTTTGGG GGACACAGTT TAGTCCATAA CATTCTGTCC TTGACCTGCC AAAATGTATG    235560
TCCTTCTCCC ATACAAGATA AATTTATTCC ATCCAGCCG GGCATGGTGG CTCACACGTG    235620
TAATCCCAGC ACTTTGGGAA GCCAAGGCAG GCGGATCAGA AGGTCAAGAG ATCGAGACCA    235680
TTCTGGCTAA CACGGTGAAA CCCCATCTCT ACTAAAATAA AAAAAAATT AGCCAGGCGT    235740
GGTGGCGGGC GCCTGTAGTC CCAGCTACTC TGGAGGCTGA GACATGAGAA TGGCATAAAC    235800
CCGGGAGGCA GAGCTTGCAG TGAGCCAAGA TGGTGCCACT GCACTCCAGC CTGGGCGACA    235860
GAGCTAGACT CCGTCTCAAA AAAAAAAAAA AAATTATTCC ATCCAACAG CCCCCTGAAA    235920
GTCTTAACTC ATTCTAGCAT CAATTCTAAA GTTCAAAGTG TCATCTAAAA AATCATCTAA    235980
ATCAGGTTAC GGGTGAGGCT CAATGTGTGA TTCATCCAGA GACAAAATTC CTTTCCAGCT    236040
TTGAACGTGT GAAACCAGAA ATGTTACATG CTTCTAAGGT ACAATGGTGA ACAGGCATA    236100
ATAGACATTC CCATTAGAAA ATGGAGAAAT AGGAAAGAAG GAAGGTGTAA TGTGTCCTAA    236160
TCAAGTCCAA AACCTGGCAA GGCAAATTCT GTTAGGTCTT AAGAAAAACC CTCTTTGGCT    236220
TGATGCCCTG ATTTCCAGGC CCAGTGGTGT CTCAGTGTCA CCTCTGGCTC TGTAGTTGGC    236280
CTACTCCATC TGCCCTGCCT GAAGTCTCGG TCTTTCAGTT TGGTGGGGTC CCACCCAGGC    236340
AGCCATCTGT GAGAGACTCC CACACAGTTC TGCAGGGCAT CTTTGAAACA GGTAGAGTCA    236400
GCCTTGACTA CATGTTCCCA CCCCCACCCT ATCCCATCTG TACTCTCTGA GTCTGACATC    236460
AAAGTGGCAG CCCTGGCGGC TCCTGCCTGT AATCCCAGCA CTTTGGGAGG CCAATGAGAA    236520
TGGATCACTG GAGGTCAGGA GTTCCAAACT AGCCTGGCCA ACATAGTGAA ACCCCATCTC    236580
TACTAAAAAT ACAAAAATTA GCTGGGCAAG TGGTGGCAGG AGCGCTACTC GGGAGGGTAC    236640
AGATTTAGAG CCTGTAATCC CAGCTACTTG GGAGTCTAAG GCAAGAGAAT CCCTTGAACC    236700
TGGGAGGTGG AGATTGCAGT GAGCTGAGAT CACACCATTG CCCTACAGCC TGGGTGACAG    236760
TGAGACTGCC TCAAGAAAAA ACAAAAGAGT CAGCCCTAGT GATCTTGTAA GTTGCCTTTG    236820
GTGGGTCAGT CTTTCCTTTT CTTAAAGAAT AGTACACATT GACAGCCAGG TAGCTCTATG    236880
ATCCTGTTCT ATAGAATTCA AAAAGTCGAC AACCTTCCTT TGTTCCTTTC TGTTTTCTCT    236940
GCCTACGTTA GTTTAAATTG GCAGTGTCTC TGCTGGAATA ATCCCATCTC TCTTCCTGGC    237000
TTCTGCTGAG ATGGCTGATT AAATCCTTGG GTCACACCCA TTATCTCTTT ATCAAATGGT    237060
TGTTCAGGCT AGGCTCAGTG TTTCACGCCT GTAATCCCAA CACTTTGGGA GACTGAGGAG    237120
GGCAGATCAC TTGAGCTCAG GAGTTAGAGA CCAGCCTAGG CAACATGTCA AAACCCCATC    237180
TCTATAAACA ACAACAAAAA ATTAGCCAGG GTGTGGTGGT GCATACATGT AGTCCAGCT    237240
ACTTAGGAGG CTGAGGTGGG AGGATTGCTT GAGCCTGAAG GCAAAGGTTG CACTGAACTG    237300
AGATTGTGCC ACTGCACTCC AGCCTGGATG ACATAGCCAG ACCCTGTCTC AAAAAACATA    237360
AAAATAAAAA TAAAACCAAG AAAAAAAAAG AAAAGAAAA CATTGTTCAA CCATACCTCT    237420
TCAAGAAAAA CTTTCTCAAT TTTTACAATA TAGATTGAGA AATCTATCCC AAATCTCCAA    237480
```

| | | | | | |
|---|---|---|---|---|---|
| GTTCTGATTG | TGTTTTGCTT | AAAAATTCCT | TCTTTATTTC | GGCTCTTTCC | TCTCACATTT 237540 |
| CACTTTAAGC | AGTAAGGAGG | ACCTAAATCA | CACCTTCAAT | ACTTTGCTTA | GACATCTCTT 237600 |
| CTGGTAAATA | TCCAGTTTTA | CTGCTTATAA | GTTCTTTCCA | GTAAACACTA | CAGCGTAATT 237660 |
| CAGCCAAGTT | CTTGACACAT | TGTAACAAGA | ACAGTGATTT | CTACAGTTTC | CAATAACCTG 237720 |
| TCCCTCATTT | TCATCTGAGA | CCTCACAAGA | GTTGACTTTA | ATGTCCATAT | ATATATATTT 237780 |
| TTTGTGTGTG | TGTGGCGGGG | GGAGTGGAGT | CCTGCTCTGT | ATCCCAGGCT | GGAGTGCAGT 237840 |
| GGTGTGATCT | TGGGTCACTG | CAACCTCCAC | CCCCGGGTT | TAAGCGATTC | TTCAGCCTCA 237900 |
| GCCTCCCGAG | TAGCTGGGAC | CACAGAAGCA | CATCACCATG | CCCAGCTAAT | TTTTGTATTT 237960 |
| TTAGTAGAGA | CAGGGTTTCG | CCATATTGGC | CAGGCTGGTC | TCAAACTCCC | GACCTCGTGA 238020 |
| TCTGTGCCCT | CAGCCTCCCA | AAGTGCTGAG | ATTACAGGCG | TGAGCCACCA | CGCCTGGCCT 238080 |
| AAAGTCCATA | TTTTAACCAG | CATATTTAAT | ATTCTATCCA | TGATCGTTAT | AAATCTAAGT 238140 |
| TTCTATGAAA | ATGGAAGCTT | TCTGTCCAGC | TCTCTTCCTT | TCTGAGCCTT | TGCCAGAATT 238200 |
| GCCTTTAATG | TCCATATTTC | TTTCAATAGT | CCCTTCACAA | TTGGCTTTTT | CTAGTATGAA 238260 |
| CCTCAAACTC | TTCCAGCCTT | TACCCATCAC | CAATTTCCAA | AGCCACTTCC | CCATGTTTAG 238320 |
| GTATTTGTTG | TTGCAGCATC | CCACGCCTGG | GTACCAAAAC | TTAGTCAGCT | TGGACTGCCA 238380 |
| TAACAAAATA | CTACAGACTG | GTGGCTTAAA | CGATAGACAT | TTATTTCTA | ACAATTCTGC 238440 |
| AGGCTGGAAA | TCTAAGATCC | AAGTTGCCAG | CATAGTCAGT | TTCTGGTGAG | GATCTCTTCC 238500 |
| TGGCTTAAAT | TATTTCACAG | ACACCAGGCA | GATAACCATA | TCCATTCTTT | CCTGTATTCG 238560 |
| TTAATAGTCA | GAGCTAAAAG | TGTAGGGCTC | TAAATTTACA | CTTCAACAAA | TTGTTCTGTT 238620 |
| ATTAAGTATT | CACCTCAAAA | TGACCAGACT | ATACTATCCT | CTAAATTTTA | GAAACTTGGA 238680 |
| GCTTGGCTCT | GGTCCCTAGT | CTTTGTTCTG | TCTCATTAAT | GGCTTCATCA | ATACTACGGT 238740 |
| TCCAAAGACT | ATCTATATGC | AGTAAACTTC | CAATTTTACA | TCTCCAGCCT | GACCTTTTTT 238800 |
| CTGAAATGCA | AATGTGTGTA | GCCACATTTT | CACTTGACAT | CTCCATTTAG | AACTCTAATA 238860 |
| GGTCTTTCAC | CCTAAACACT | TCCAAGACAC | AGGAATAAAC | GTGCTCCTTA | AGCCTGTTAT 238920 |
| CCCTTCCAGT | TCTCCCCAGT | TCAATAACTG | ACACTACCAT | TTACTCAAAT | CAACATTCTA 238980 |
| AGAGTGTCAC | TTGCTACATT | TCCTTCATCT | CTACAAATCC | AAAGTATCTG | TGAGTCACGT 239040 |
| CACCTACATA | TTCAATACAT | GCAATAATTC | ATTCTCCATA | CTCCTTACCA | TGACTTAAGG 239100 |
| GCCCACTCAG | TGACCATCTC | TGGCCTCTGT | TCACCTCTTC | TGCTGTTCTC | CTTTGCTGTT 239160 |
| CCAGCCACGC | TGGTCTCTTT | TCACATCAAG | CAGCTAAGCT | CTGCCCATTT | AAGACATTTA 239220 |
| ACTTCTTGGC | CTCAATCTCT | GAAATGCCTG | TTTGATTTTT | CTTCTGGTGA | GCTCATTTTC 239280 |
| ACTCATCAGG | TCCCAGCTCT | GTTTCAGACA | AGGCTATCTA | AAATAGACCT | ACCTAAATGG 239340 |
| ATTAAAAATC | TGAGAATATG | AAATAACAAA | TATCAGATGA | CATTTTAGGA | GACCCTTTAT 239400 |
| ATACCTCATT | TGTGTGTGTG | TGTGTGTGTG | TGTGTGTGTG | TGTGTGTTTG | GAAATGGTGA 239460 |
| TGGAGGGTGT | CATTGCTAAG | TGAGGAGGAA | ACACAAAGC | CATCTAGGAA | AGGACACAGA 239520 |
| CTAGATAGGT | CCAAAAGTGG | TTTAAGACAG | AATATATGTA | AAGAGAGTTA | TAGAAAGAGC 239580 |
| AATAAGTTGG | GATAAAGGAT | TTCCAAAACA | TATACGGGGT | TAGTAACCTC | AATTTACAGG 239640 |
| GACAAACTGC | AAAACGTTAG | TGAAAAGGCA | AACAACATAA | TATAAAAGAT | GATTAAACGG 239700 |
| TATTTTATAT | CATGTATTAA | ATTCATATGG | CCAATACATA | TGAAAAACAA | GAAACAAAAA 239760 |
| ACCTTCCTAG | TAATTCAAAA | TTATGCATAT | TAATACAACA | AAGGGATACC | ACTTCTTTTT 239820 |
| TTTTTTTTTT | TTTGAGACAG | AGTCTTGCTC | AGGTACCCAG | GCTGGAGTGT | AGTGGCATGA 239880 |

```
TCTCAACTCA CTGCAACTTC CACCCCCTGG GTTCAAGCGA TTCTCCTGCC TCAGCCTCCC 239940
GAGTAGCTGG GACTACAGGC GCCTGCTACC ACGCTCAGCT AACTTTTGTA TTTTTATTAG 240000
AGATGGGGTT TTACCATGTT GGTTGGCCAG GATGGTCTCG GTCTCTTGAC CTCGTGATCT 240060
GACGGCCTCA GCCTCCCAAA GTGCTGTGAT TACAGGCGTG AACCACTGCA CCTGGCCTAA 240120
TTTTTGTATT ATTAGTAGAG ATGGGGTTTC ACCATATTGG CCAGGCTGGT GTCGAACTCC 240180
TCCTGACCTC AGATGATCCA CCCACTTCAG GCTCCCAAAG TGCTGGGATT ACAGGCATGA 240240
GCCACTGTGC CCAGCCTGGG ATACCATTTC TTACCTATGA ATAGACAACC ACTAAAGCCA 240300
GTATACTCAG GACTGCAAAG GATGAGGAAG AATTGCCATT GTCATATAGT TTTTCATAAC 240360
TTTTCCTGAC AATGTCTATT AAATTGTATT AATAGACATT TGGAAAGGGA GAGTGTCAAC 240420
AATCTAGAAT AAAGGCCCCA CTAGGTAAGG TTACATATGT AAGGACTCTT TCAAAACTGT 240480
CACAAGAATT CAGGTACGGT GGCTCATGCC TGTAATCCTA GCATTTGGG AGGCTGAGGC 240540
GGGTGGATCA CTTGAGGTCA GGGGTTTGAG ACCCGCCTGG CCAACATGGT TAAAACCTAT 240600
CTCTACTAAA AATACAACGA TTAGCCATGC ATGGTGGCAC ATGCCTGTAA TCCCAGCTAC 240660
TCGGTAGCCT GAGGCAGGAG AATAGCTTGA ACCCAAGAGG CAGAGGTTAC AGTGAGCCGA 240720
GATCGCACCA CTCCAGCCTG GGCAACAGAG TGAGACTCCA TCTCAAAACA AACAAAAAA 240780
ACTACTCAAA ACTGTAATAA GAAAAAAAAA AACCTAATTA TACATGTAAA ACATTTAAAT 240840
AACTAAAATA AGAATACTGT TGACATAGTG AGACATCCAT TTATACTATG GAATGTTATG 240900
CAGCTACCTG AAACAATAAT CCGGTGAAAC AAAATCACAC ACACAACTGA TGAGAGTAAA 240960
TAGAGAACCG TATGGAAGAA AACATACCAC AGTAATTATC TCAGATAGCT GAAACTAAGT 241020
TGGTGCAAAA GTAATTGTGG TTCTTACCAT TACTTTCACT GGCAAAAGCT GCAATTACTT 241080
TTGTACCAAC CTAATAGAAT GGGGTGAGGA GAGGTAAACC TTTATAAACA TCTCTGTGTG 241140
AACTGTTAAA ATGAGCAAGT ATATTTTTT TAAAGTATAA AGAGAGAAAA AAGTAAACTT 241200
TCTCCATTTC CCACCTCAAA TTATGTTCTG TCACTCATCC TGTTTAGATT CTTTCAAATG 241260
CAGTTTGAAG TTTTATTTAT GAGATTCCTT GTTGTTTGCC TCTTTCCATT AAACCTAGCT 241320
CCACAAAGTA GGGACCTGAT GTATTCATTC ACTGTTATAT CCCAGCATCT AGCAGAGGGC 241380
CTGACACTTA GTGGGAACGC AAGTATCTGG TATATAAACC AGAGAATAGA TATTTTTTA 241440
GCCCAGAAAG CTGTTTCACT GCACAGAGTG TAATTATCTG AATTTCTATA AAAATGTCTA 241500
TCTATAAATC ATTGTCAATA CATTACCTAC TCACCTTACC CAGCTACCAG GAACACTATG 241560
AAGTTTTGAA TTACACCCCA TTTGTTTTCC ACACTCTTAC CATTTTCCCA GTTTCTGCAC 241620
TGACCTCTCC AGACATCATG TGTACTGATA ATTCTAAGTT GTCTAGATTG TTAATTCTTT 241680
TAAGGGCCTG TTCTCTGCTA GCTGGCATCA TGCATAAAAT AATTCTCTTT AATATGCTCT 241740
GGGTCTAGGG TTAATAGATG TTTGCTTAAA ATCATGGAAA GAAATGGTC ACACAGCTGG 241800
TATGTGTGAT CAAATTTGTG CTGTTTCATC CACTTAATGT TTACTTTGTG GTAATGGAAC 241860
CTCCAGCTT TTATTTTCCT TCCTTCCTTC CTTCCTTCCT TCCTTCCTTC CTTCCTTCCT 241920
TCCTCCCTCC CTCCCTCCCT CCCTCCCTTC CTTTCTTTCT TCACAGAGTC TAGCTCTGTT 241980
GCCCAGGCTG GAATGCAGTG GTGCGATCTC AGCTCACTGC AACCTCTGCC TCCCGGGTTC 242040
AAGCGATTCT CCTGCCTCAG CCTCCCAAGT ATCTAGGATT ACAGGTGCAT GCTGCCACAC 242100
CTGGCTAGTT TTTGTATTTT TAGTAAAGAT GGAGTTTCAG ATGTTGGCCA GGCTGGTCTC 242160
CAACACCAGG CCTCAAGTGA TCCGCCTGCC TTGGCCTCCC AAATTGCTGG GATTAACAGG 242220
CCTCAGCCAC TGTGCCCGAC CCCAGCTTTT ATATTCTAAT GCTGAGATTA TTCAGTTAAC 242280
```

```
ACTCTTACCT  GCTAGGATAA  GTTTGTTGGA  GAATTTTACC  TTACCTTGTA  CCCTTTACCT  242340

TCACATCTAC  CTGTACCCTG  GCCCTTCACA  TCCTTTCCAT  ATAATATATC  TTCAGTAAAT  242400

ACAGGGAAAA  AAACCCAGAA  TGATTATGTT  GACAGCAAAA  CATGTTTGTG  CAGAAACGGA  242460

GTAGTCACTA  TCTAAGCCAC  AGAGACTTAG  GAGTGTATTC  CTGAGTTATG  TATCATTTTA  242520

ACCATCACTG  GATCTTAAAT  CCCAGTTGCT  AAATTGAAGG  GAGATACATG  ACTCTTTTA   242580

GGGCTTTGCT  CTCTGATACA  GTAGCCATTA  GCCACATGTG  ATATTTAAA   TTTAAATAAT  242640

TAAGTCAAAA  ATTCAGTTTC  CTCAGTCTCA  CCACATTTCA  GGTTGCTGGT  GTCTACTGTA  242700

TTGGATACAC  AGACATAGAA  CATGTCTATC  ATCACAGAAA  ATTCTATTGC  ATTGCACTGG  242760

GATAGGTACT  TTTTGTGCCC  TTGGGCTGAT  AAGTTCAAGT  GCACTTAACT  AGCTTCCTCC  242820

AAGTGGAATC  AGAGGATAAA  TTTACCATAC  AAAATACAGG  ATACCCAATT  ATATTTGAAT  242880

TTCAAACAGG  CAACAAATAA  TTGCTTAAGT  ATGCCCCTCA  CTGCACACCC  AAATATTACA  242940

TGAGACATTC  TATACATATA  TATATATATA  TATATATATA  TATATATATA  TATATATATA  243000

TATATATATT  TGAAATTCAG  ATTTAACTGG  ACATTTGGTA  TTTTTAATGT  GCCAAATCTA  243060

GCAACCCTAT  CTGAAGAGCA  AAACTGGAGT  GTCTAGTCTG  GATAGGTCCT  TTTACACCAC  243120

AGGGAGTTAT  TTGAGGAATT  GAGAAGGGCT  GTGGTACCTG  TAAAGAACTA  ACTCATTATG  243180

AAGAAAGGA   TCTGTAAGTT  TTTCTGTATG  TGTAAGGAAG  GCCAAGAAGG  TGGTTTCCAG  243240

ATATATTTAC  TTTTTCTTCT  CTCTCTCTTA  GGTTGCAAAA  GCTTCTCATT  TCAGAGAGAT  243300

GCCAGGATCC  TAAGTGCCTG  CCAAACTTAC  CAATTCTAAG  GAATAAGTGG  ATGGATGGCA  243360

TTACTGATTC  CTACATTACT  GATTGATTCT  GCATCCGCAA  ATTGTTTTAT  TAAAAACATT  243420

CTACATCATG  TGTGGGGAGA  TAAGGAGGAT  AAAATGAAGA  GAAAGAATAT  TATTGAGGGG  243480

AAGTTCTTCT  GAATACAAAA  TGTGTTTAAT  TTTTTAAATA  AGTATTACAT  TCACAGGGTT  243540

CAAACTATTT  GAAGTAAAGA  GATTATATAT  AAAGAATCCA  TCCCTCAACT  TACCCAGGTG  243600

GTCACTTTTC  TTTTTCTTGT  GTATCTGCCC  AGTATTCATT  CCTGCTGATA  TCAGTCAATA  243660

ATGAATGATA  CGTGTTTTCT  TCACTTTTTT  CATTCTTGTC  AGGTAGCAGA  CTGTGTAGAC  243720

TTTTCTGCAC  TTGCCCTTTT  CATAACAATC  TATCTTGGAG  AACTTTCCCT  ATGAGAACAT  243780

ACAGAGCTTC  CTGTACACAG  TTGCATGTAC  TGCATTATGC  AAATGCATTA  TATTTTATGT  243840

AACCTGTCCA  CTGTTGGTAG  GCACTTGAGT  TGTTTTAGTC  TTTTGCTATC  AAACAGTTCT  243900

GGGATGATTA  ACCCTGATTT  ACTGCAAAAT  TGAAATTGCT  CTGCTATTCT  GCTGGAATGG  243960

TGGTAAGTGA  ACTGAAAATT  CCAGTCACTC  TTGGGCTAGA  CTCAACGTTC  TTAAAAACTA  244020

TGTGGCCATC  ACCAAATTAG  TTATTTTGAA  CCTTAATTTC  TTCACCTCTA  AAATGGAGGT  244080

AATACTTACC  TTAAGTGGCT  ATGAGAATGA  AGATCATGTG  TATGAATTGT  TGGTGCTCTA  244140

AAGAACAGCA  CAAATAAAAT  TATTTTCAAA  TTTAATTTTA  ATTGAACTAT  GTGTAATTTC  244200

TTAATTTTGA  AATAATTTTA  TTTGTAATGT  GCATAATCTT  ATTTAATGTA  TAATGTATAC  244260

ATTGTAATAG  AAACAGATTT  CCCAAATTCC  AGCCTGGCAT  GAGGTAATAA  AAGGTAATGC  244320

AAAGGGAGAG  GAAAGCATGT  GTCATTAATT  TTCTGCCTAG  GACACCTCCC  TGGTTAAATT  244380

GCCATTTCCT  TTCTTCCTTG  CATAATGATT  AGGAAACACA  TCCTCCTGAC  CTGCCTGCCC  244440

TCTTTTGCCT  ACTTTTTCAT  CTGCAGTCAA  GGTCTGGTTT  TAAGACTGAC  TGTTACTTTT  244500

ACAAATCTGT  GTGTATTGGT  GGCTAAGGGC  CTGTATGGTC  CACTGCTGTA  TTCCCAGGTC  244560

CCAGCATGGT  GCCTGACGCT  GCCTGGCAAA  TAGTAGTCAC  CCGAGAAATG  GCTGATGAAT  244620

TCATGAGGCC  TACTCTGTAT  GGAAATTTCA  ATTCTGGCCC  CGAATTTTCA  GGAGCTGGCA  244680
```

-continued

| | | | | | |
|---|---|---|---|---|---|
| AGAGAGCCAC | CTTAATATCA | TAGGCTGAGT | TGGAAGAAGG | GAACACCCAA | TTTATTCTTA 244740 |
| AGAAGTACTT | TGCCCAGGTA | CTGTGGCTTA | GGCCAGTAAT | CCTAGCATTT | GGGGAAGCCA 244800 |
| AGTTGGGCAG | ATGGCTTGAA | CCCAGGATTT | CGAGATCAGC | CTGGACAACA | TGGAGAAACC 244860 |
| CCATCTCTAC | AAAATATGTA | AAATTTAACT | GCTTGGTGGG | CCTGCACTTC | TGGTCCCAGC 244920 |
| TACTCCAGGG | CTAGGGTGGG | AGGATTGTTT | GATCCCTGGA | GGTCAAGGCT | GCAGTGAGCC 244980 |
| ATGATCACAG | CAATGCGCTC | CAGCTCTGGG | CAACAGAGCG | AGACCCTGTC | TCAAAAAAA 245040 |
| CAAAATGCC | TATACAATAA | ATCTATAAAA | AGTGGGTTTT | GTGTGTCTAT | ACACACACAC 245100 |
| ACACACACAC | ACCTGCATAG | ACACTCAGGT | GTTCTGGAAA | GACACAGGAA | TCTGAAGCCA 245160 |
| AAATACTTGT | GATTTTTTTT | CAGCTCTGCC | ACTCACCAAA | TGTCTGATGG | GATTAGTTAC 245220 |
| CTGCCATCTC | AGAATTTCTC | TTCTGTAAAA | TAAGGTAATA | GTACCTCCCA | GAGTTATGAA 245280 |
| AAACTATCAA | ATGAGATGGC | AGATGAGAAA | ACACTATATT | CCTTGTAAAA | CCTGACAAAT 245340 |
| ATGTGCAAGA | TTATATAAAG | ACTGTCTTCT | GTCCATTTTC | AAATGTGGAA | AAGTGAAAGC 245400 |
| AGGACAGGAT | GTTGGGATTT | CTGTCAGAGA | TTTGCTGGCT | TCCACCTGCA | GAAATTGAAG 245460 |
| TAATTGGGGT | TCTTACACCT | AAGTACTAAC | TGAGTCTGGT | TGCAGTTTGC | CCCCATGGCT 245520 |
| ACATGAAGCT | TTTAGAAGAG | TCAGCATGGT | AGACATGGAA | TGTTGAATGG | TGGTGGAGTG 245580 |
| TACCCACACA | CCTCCCACCA | AGTCAGCTCC | AGGTTCAGAA | GCAGCAGCCC | CAGTGGAAGG 245640 |
| CATGCGTGTT | TGTAACTCAG | CTGAGCCACC | TTTCAAGAAG | CAGAAGCTTT | CCAAACAGGG 245700 |
| ATGCCCCTG | CTTTTGGTTC | AACTTGACTT | CCTACCTTCA | GTGAGGACAT | GGAGAATTCA 245760 |
| TCTAGACTGG | GTACCTGAGC | AAACTTGGCA | GAGCAAAGAG | AAATGTGGAA | GGCCCTAGGT 245820 |
| AGACAGGCCC | TGTGGAAGGA | AAGAATGAAA | GAGGACAGAA | AGAAACTCCC | ATTTTCTTTA 245880 |
| GCACAGTCCC | TTCAGATTAA | GGATGAAGAG | GCTGGGGTTC | TGAATTGGTT | GGCCTTAGGT 245940 |
| AATGGTCACA | AAAACAAGTC | AATGGCTTTT | CCACATCCGT | ACATTGAGAT | ATATTTCTGC 246000 |
| CCTTGGTATT | CATTTTCTCT | GACCTCCAAT | TAAAGATCTA | TGCGTCATTT | TAAAGCCTTC 246060 |
| CTTCCTTTCT | ACTCTGTGGT | CAGCGTAACA | TTGGTGGTTT | GAAACTGGCC | ATAATAGCAG 246120 |
| CATTTACATC | ATGGGAACTA | GCATATGTTA | CATCAGGGTT | TTTTGTTTT | GTTTCTGGAG 246180 |
| AGCCAGTAAA | CATACATCGT | CACACCACTT | AAATATTCTC | TGCTTAAATA | TTCTCTGCTC 246240 |

(2) INFORMATION FOR SEQ ID NO:22:

(i) SEQUENCE CHARACTERISTICS:
        (A) LENGTH: 246240 base pairs
        (B) TYPE: nucleic acid
        (C) STRANDEDNESS: Not Relevant
        (D) TOPOLOGY: Not Relevant (ii) MOLECULE TYPE: cDNA (ix) FEATURE:
        (A) NAME/KEY: misc_feature
        (B) LOCATION: 1..246240
        (D) OTHER INFORMATION: /note= "HLA-H.CONTIG"

(xi) SEQUENCE DESCRIPTION: SEQ ID NO:22:

| | | | | | |
|---|---|---|---|---|---|
| TTTGTAAGTA | TTCTATTTTA | TTTATATGTG | TTTGTGTTTC | TGAGTATGTC | CTGAGTTGCA 60 |
| CGATAATACT | ATATTTCTTA | TTGGGTAACA | TTGTCAGAAA | AGTTTCTAAA | AACTTTCTCT 120 |
| GCTGCACTTA | TTTTATACAT | TTTATTTATG | TTAATAATCT | CACATTTAAC | ACACTTATGA 180 |
| TTTATTCTCA | ACAGAAAAAG | GTGGTATTTC | TTTCATTTAG | TCTTTTAAAA | AGCTCACATT 240 |
| ATCAAATGAT | TGCTCAATCA | TTTAATCTCT | TTGCTTCTCT | TATATGCATT | GATTTAATAA 300 |

-continued

| | | | | | | |
|---|---|---|---|---|---|---|
| ATATGTATAC | TAGTTTCTCC | ATCGATTCTT | TAGATTTGAA | ACTTATTTTC | CTTTTATTCT | 360 |
| TACAAAACTG | ACTTGTCTAT | AGGCCCACTT | CTACTTCCTT | TATTCTATCA | TCTTCCTCAA | 420 |
| CTTATTCTGT | GGTCAAAGAA | TGGAGAAATA | ATATTAATAA | TATGTTTTC | TCATCAATGA | 480 |
| CTTCCACCTG | TTCTCTGAGA | AATTCAGCTT | CAAGAACTTT | AGTTTGATAT | GACTGCAAAG | 540 |
| ATAATACACA | GTCTAAATCA | TAAAAATGTC | TCAAAGGTTT | TTTTTTATT | TGTTTCTTTG | 600 |
| AAATATCCAT | GAACAGGCAT | GTTTCTCCCC | CTGTAGTGCA | ATTTGTGTGA | AATTCTGGCA | 660 |
| TGCACTTAAG | AGGATGTCCT | AAAATACCAA | TATTTAATTG | ATTCTAAGTC | ATGTATTGTA | 720 |
| TCACATTTTT | GCCCATGGAT | TGTTGAAATC | CATGGACAAA | ACTGATAGCA | TTTTAGAACT | 780 |
| TCCTTTGTCT | AGTGGCAGTC | TTGATATATT | CACACTATCT | ATTGACAAAA | AATCTAAAGC | 840 |
| ACCAGGCTCA | AAGCTTGTAG | AGTAGGTGTC | AGTGATTTGG | AGGACATCTC | TAGGGCAATA | 900 |
| GTAGAGGCAT | TTTTAACCCC | TAACAACTAA | ATGATCATCA | GAAGTGAGTG | ATATCCTCAC | 960 |
| TCATGACCCC | AACTGCTCTA | ATTTCTATTG | TTTTCTTGCA | GAAATGAGAG | CAGGTGGGGT | 1020 |
| CATGGGTGAG | GAATGAGGTG | TTGAAAGTGA | ATGGGGTGTT | GAAAGCAAGG | TGTTTAGCAG | 1080 |
| TGTTCTGAAA | GCATACATTT | AAGTAGGCTA | TCCGGGCACT | GTCAATAGCT | AAGTGTCAAG | 1140 |
| CTAAGTACTC | TATTTTATTC | TAAGAACTAT | TTTAGAAAT | GCTGAATCAA | CAAATCTCAG | 1200 |
| ATGGCACAGA | GGTTGTCATT | TTTGAATAAT | ATGAATATCA | GTAATTTTAG | TTGGAAAAGA | 1260 |
| AGATTTTCAA | AGAGCCATCT | AAGTTTCCAA | AATAAGTGTT | GCAGTCATAT | TAACTATTAT | 1320 |
| ATTTTCCTGC | CTGTTGATCT | ACTGCCTGTG | AATTGCTTAT | CAAACCAACA | ACCAACTGGA | 1380 |
| ATACATAGAC | TGCATGTCTT | GTTCATTTCC | TGCATTCTCA | AGTAATGGTT | TAACAAACTC | 1440 |
| ATGAGCTTAC | TCTTTAATCT | GAACCATGCT | TAACTTCAAT | TATGTTGATT | TAGTCTAAGG | 1500 |
| ATGCAGAATT | TATTTTATAG | TTATGTAGGA | ACTGGAATCC | AAAATGTAAT | ATGCCTCCAA | 1560 |
| GCTTTTCTTT | GTTGGCCTCT | GAAGGAGCAT | CACCTCTACA | ACTTCAACGT | TGTTATGAAT | 1620 |
| ACCTCTGGGG | AGGTGTTCAC | CTCAGGACCC | AAATTTGGAA | AAAGGGAAGT | GCCACTTTGG | 1680 |
| AGGAGTGCTC | TGAGCAGCTG | ATCCATTAAA | TGTCCCGATC | ACATGCACGT | GGAAGTGTCA | 1740 |
| TTGCAATATC | TGCACTAACA | GAAGCTCAGT | GACTTGAGAA | GTGAGTCTGG | AATTCTAAGA | 1800 |
| AAAAGGCAAG | GCATCTCTCT | TGCCACTTGT | TATTTTTCCA | GTCAAGCAAC | TGTGATAAGA | 1860 |
| GGGCATGGAG | AGCAGGAAGA | AGTGAAAAAT | CCCAGGAAAG | TCTGGAGTGG | AATCATTAAA | 1920 |
| CCAATTCTGC | TCCCTCTCTA | GGCCAACTTG | GGCCTATTAT | GAATAAGGAG | GTCTCTTATA | 1980 |
| ATCCATCTAA | CTCCACTCAG | GAACAATTTG | GGGATCTGAG | ACTGTGAACT | CAGTGGGCAA | 2040 |
| AAAAATATTT | CTTGGCCTAT | CATTATTCTC | TGTAGGATGT | TAAGGACAGG | TTTCTGTATG | 2100 |
| TGGAGTCCTC | AGTTTTTGCC | TTCTCTCCTT | GAGATATTTT | TATGCTATTT | AGTAATTGAT | 2160 |
| GGCCACAGTT | GATCGACCAC | ATTTCTGGGC | AACTCTAATA | ATCCTTGTTA | TATTAATCAT | 2220 |
| TGGACCAATC | TTGATTGTGT | ATGACCATCA | TCTTGTAGCT | ACCACCTCTA | TGTGGATGCT | 2280 |
| CTCCTCACCC | TGCTTAAGTG | CCAATGTCTG | TGCTATGGGC | CTACCTGTCA | CATGGATAAT | 2340 |
| CTCTTCACTC | CAGTCAGGCT | CCAACATTAA | CACAGGGCTG | TTCTCTTGTC | CCCCTTTGAA | 2400 |
| GACAGCTTCA | TCACCCTATT | CAAGTTGCAG | TACTCTCACT | GGGCCTCCAC | TGTTGCCTCT | 2460 |
| CTCTCACTCT | GCTTAGGTTT | CTTCACTCCA | CTCCAGGCAA | CTGTCACTAA | ACATCCTTTC | 2520 |
| CCCCATATAT | AACACAGACA | TCTACCTTGC | TTGGCCAAAC | CCACTGGATT | TCAGACTCAC | 2580 |
| TCATTCAGAG | AGTAAGACAG | AGAGGGGTTC | ATTTTTTATT | TTATTTTATT | TTTATTTTT | 2640 |
| TGAGACGTTG | TCTCACCCTG | TCGCCCAGGC | TGGAGTGCAG | TGGTGCAGTC | TTGGCTCACT | 2700 |

```
GCAATCCCCA CGTCCCAGGT TCAAACGATT CTCCTGCCTC AGTCTCCCAA GCAGCTGGGA    2760
TTACAGGTGC CTGCCACCAT GCCCAGCTAA TTTTTGTATT TTTAGTAGAG ACAGGGTTTC    2820
GCCGTGTTGG CCAGGCTGGT CTCGAACTCC TGACCTCAAG TGATCTACCC GCCTCGGCCT    2880
CCCAAAGTGC TGGGATTACA GGTGTGAGCC ACTGCGCCCA GCCGGGGTTC ATCCTTAATA    2940
CATACATTAG AGATATAGAT TCTGTTTTTA TCTAAAAAGT CTTTATAAGG CCGGGCGCGG    3000
TGGCTCACGC CTGTAATCCC AGCACTTTGG GAGGCCGAGG CGGGCGGATC ACGAGGTCAG    3060
GAGATCGAGA CCATCCCGGC TAAAACGGTG AAACCCCGTC TCTACTAAAA ATACAAAAAA    3120
TTAGCCGGGC GTAGTGGCGG GCGCCTGTAG TCCCAGCTAC TTGGGAGGCT GAGGCAGGAG    3180
AATGGCGTGA ACCCGGGAGG CGGAGCTTGC AGTGAGCCGA GATCCCGCCA CTGCACTCCA    3240
GCCTGGGCGA CAGAGCAAGA CTCCGTCTCA AAAAAAAAAA AAAAAAAAA AAAAAAAGT    3300
CTTTATAAAA ATCTGATTGA ATGGTTGAAT GCTGTGCTAA AATCTGCATA ATATCTTACA    3360
ACACTTCTGT GAATCACGAG ACAGTTTTGA ATGCTAAATG TCAGTTAACA GATCTAAAGG    3420
GACCAACATC TGCTTTCCCA AATTATATGA AAGAAGATCC TGATCCCTCA TCAGGTGAAA    3480
CTCACATCAG ACAACAGTGT CTGCATTTCT CCAAAACCCG CCTCAGCCCC ATGGCCACTT    3540
TCCAGGGTTA TCCTGCCTAC CAAGCACTCT CTTTCCTCAG AAAAACTTGG GGGAAAATGT    3600
AGAATAATAA TTTTTTGAAG TTCTGACCAA CTTCTTGAAT CACTCAGCAT GTTTTGACT    3660
GCAGGTACAG AAAACGCTGA CTCAACAAAT TTAAACACTA TATAAATTTC TTATCTCCCC    3720
AAACAGGACA TCAAAGGCAG AAAGGTTCCA GAGCAGGGTG ATCAGAGCTC TGGCTCCACT    3780
GCCCTCAGTC TTCTTGCCTC TGCTCTCCTT CACAGCAGGC TTTACCCCCC ATGCTGGTCA    3840
CAGTTTCAAG TGTCCATGCA GACACAAGTT AAAGGCAGGA AGAAACAGTG CGTTTCTCTT    3900
GGAGATCAAG GAATGCCTTT CCAGAAAACT CCCCCTTATG TCTCATTTGC CAAAACTTGG    3960
CCTAGTCTCA GGTGCTGCCT GAGCTAATCA GCTACAGAAG AAGGGACCAC ATGACTGGTG    4020
TGGACCAGTC AGAATTCACC ACATGAAGCT AGTAATGTGG CTCACACTTC CCAGGGGAT    4080
ATGGCCAGGT AGCAGACAGT GGATCGCTGA ACAGAATACT GATAGATTTC AGCACCAAGG    4140
TTAGAATGGC TACCACACCT AATCCCACCC TATCCCGTT TCCTTCTTTA ATTTTTTCCA    4200
TAGCACTTAT CAGTAGCTGA CAAACTGTAT ATGTTTTAC TTTTTTATTG TCTGTAGCTC    4260
CCAAGTAGAA TACAAACATC TGAAACTCAC TGTATCCATC CTGAGTAATG TTCTTTTCAG    4320
CTCAGTCACA ATCATTTTTT GATAGCCTAT CCTATAAGCT TAACTTATAG TGTTAATCAG    4380
TATTAATACA TCTTAGTGGG AAAGAAGGAA AAAATAAACG ATCACACACA CACACACACA    4440
CACACACACA CACATACATT TACGTAACAG AGCAAGTGTG AAAATACCTA AAGGCTTTAT    4500
AGCTCCTTTT GTCAATGGAT ACATGACAGC ATTTTTGGCA TTCTTTACTA CTCTTATTCT    4560
ATGCTCCATT TGTCTTCAGT CAGCACCTCA GCTGCCCTTA TGTTTTACTT GGTAAGGCAA    4620
ATTCCTAAAT GAGCCTGGTA ATTAGTCATC CAGCTTATAG GAAGGTACTA TAGTTTTTCA    4680
TTAACTTTTT CACTGGGCTT GAGAGTAGTA AGGACTCCCA GAGAATTCCT TGTGTTCCAA    4740
AAGTACTTCT CCTTGACATC TTGGTATAGG ATTAATAACT GTTACCTTT GATAATCAGG    4800
AAGAATGACT CCAGCTAGTA CAGTTACGTG ATGCCTATAC ATTCCTTTTT TTCTGGGAAA    4860
AATGTAATGT GAAATTAAGT GCAAAAACCA TGCCTTGTTT ATGTATGTAT CAAACACTTC    4920
TAGAGCTTTC CCAATACAGT TCTCTTCTCA GCAAACAAGA GGACTATACC CTCATCCCCA    4980
CCCCTGCACT TAGGTGTAGC CAATGTGTTG TAACTTAAAG AGGAGAGGGC ACTGGATGAA    5040
GGGAAATCTG TCTAACAAGC TTCTTTATTT CACCTAGTGG AAAAAAGCCT TAATCTGCAG    5100
```

| | | | | | | |
|---|---|---|---|---|---|---|
| TGGGGCAGTT | TTCAAGGACA | TAGACTGAAT | TGGCTCATGC | ATTTATGGAA | GATGAGGAGT | 5160 |
| CCCATGATCT | GTAATCTGCA | AGCTGGAGAC | CCAGGAAAGC | TGGTGGTATG | ATTCAGTCTG | 5220 |
| AATCTGAAGG | CCTGAGAACC | AGAGGAACTG | ATGATGTAAA | TCCCAGTTCA | AGAGCAGGAG | 5280 |
| ACCAGATGAG | ATGTCCCAGC | TCAAGCAGTG | AGGCAGAAAA | AAAGGCCCAA | ATTCCCCCTT | 5340 |
| CCTCTGCCTT | TTCTTCTATT | CAGACCCTGA | ATATCAGGTG | GCATAATGCC | ATCCACACTG | 5400 |
| GGAAAGACAG | TTTACTTTAC | TAGGATCACC | TATTCAAAGG | CTAATCTCAT | CCAGAAACAC | 5460 |
| GCTCACAAAC | ACAGCCAGAA | ATAATGTTTA | ACCAGATAGC | TGGTTATCCC | CTGACTCAGT | 5520 |
| CAAGTTGACA | CAAAAAATGA | ACTATTTCAA | AGCTTACTGT | AATCAACAGT | TTTGTCAAAA | 5580 |
| AGATAGACAC | AAATCAGTGG | AATGAGATAA | ACAGTCTAGA | AATAAACCAA | CAAAAATATT | 5640 |
| GCCAACTAAG | GCAAAGGTAA | TCAATGGAAA | AAAGATAGTC | TTAGCAACAA | ATAGTACTGG | 5700 |
| AACACCACAA | TGTGTTAATA | AAGTGAAACT | GGAGACATCT | CTCACACCTT | ATACAAAAGT | 5760 |
| AACTAAAAAT | AAATCAAAGG | ACTAGATGTA | ATGTATCAAA | CATTACATCT | TTTAGAATGT | 5820 |
| ATCAAACATT | ACAAGCTTTT | AGAATAAAAT | ATAGAAGAAA | ATTTACATGA | TCTAAGATTT | 5880 |
| GGCCCCAATG | AAGTTTTAGC | TATAATAACA | AAAGTATTAG | TCATGGAAGA | AAACAAAATT | 5940 |
| GATAAGTTCA | GGTGGGCTAA | ATTAAGGGAA | AAAAATCACT | TTGCAGTAGA | GAAACCTGAA | 6000 |
| ACATTACCTA | AACCACATGA | TGAAGGTTAA | TATCAGTGAT | GTCATGTGGA | TATCATGTTC | 6060 |
| TCCCTAAAAT | GATGTGACAA | GAAGGGCCCT | TGCCCTTGT | GGTATTATTT | CAAAAAATCT | 6120 |
| ATAACTCCGG | TGTAATTATG | AAAAAAAAGC | AAATGATCTT | CAGGACTGTT | AAGGTCATGA | 6180 |
| AAAGCAAGAA | AAGACTGAGA | CATTGTCACA | GACAAAAAAA | GACTAGGGAG | ATATGACAAG | 6240 |
| AAAATGCAGT | GTGGTATTCC | AGATTGGACC | TTGGAACAGA | AAGAAACAT | TAGTGGAAAC | 6300 |
| AGTGGTGAAA | TCCACATAAA | GTCTAGGGTT | TGGTTAATAG | AGTTTCATGT | ATCAATGTGA | 6360 |
| GTTGCTTATA | TTTGACAAAT | GTATCATAAT | AATGTAAAAT | CCTAACAATG | GGGGAAAGCT | 6420 |
| AGGTGAAAGA | TATATGGGAA | CTCTCCTGTA | CTGTCTTTGT | ACTATCTTTG | CAACTTTCCT | 6480 |
| GAAAATCCAA | ATTATTCTAA | AACAGAAAAG | TTCATGCTAT | TAGAAGTGAG | GATAGAGGTT | 6540 |
| ACCTTGAAGA | AGCTGAGGTC | TAGAAGAGAC | CATGAAGGGT | CTAATTAGCT | AACACACGTT | 6600 |
| GAGTATCCCT | TATGCTTAGA | ACCAGAAGTA | TTTCAGATTT | TTTCAGATTT | GGAATGTTTG | 6660 |
| CATTATACTG | AGTATCTCAA | ATCCAAAAAT | CCAAAATCTG | AAATATTCCA | TGAGCACTCC | 6720 |
| TTTGAGAATC | ATGTTAGCAT | TCAAAAGTT | GCCGATTTTG | GAGCATTTTG | AATTTCCAAT | 6780 |
| TTTTAGATTA | GGAATACTCA | ACCTGAGTAG | AGGCTGCCTG | CTAATTACCT | GGGAGCTAAT | 6840 |
| TACATGGATA | TGTCATTTTG | AGAAAGTTTA | GCTTGCTGAT | ATGGATGATT | TTCTGGATAA | 6900 |
| AAATTATACT | TTGATAACAA | TTCTTTTAAA | GGAGACAATA | ATTATTAACT | TTAAGTACT | 6960 |
| TTTAGCTCT | ACAATTCAGA | ATTCTTTAGT | GCTAAATATT | ACATATTTTG | AAACAAAAGT | 7020 |
| TTTGTTTATA | TTTATTTATT | TGTTTCCCCC | CCCCTTTTTT | TTTTTTGAG | ACAAGTTCTC | 7080 |
| ACCTTATTGC | CCATGCTATA | GTGCAGTGGG | TGATTATAGC | TCACTGCAGC | CTCAAACTCC | 7140 |
| TGGACTCAAA | GGATCCTCCT | GCCTCAACCT | CCCAAGTAGC | TAGGAGTACA | AGCATGCACC | 7200 |
| ACCATATCCA | GCTAATTTTT | GTTTATTTCT | ACAGAGGCAG | GGTCTCACTA | TGTTGCCCAG | 7260 |
| GCTGATCTCA | AATTCCTGGC | CTCAAGTATC | CTCCCACCTC | TGCTTCCCAA | AGCGCTGGGA | 7320 |
| TTACAGGTGT | AAGTCATTGC | ACCCAGCCAA | AAGTTTTATT | TTAAACTTAT | TATTATGAGC | 7380 |
| ATGTAACAGA | TTTATGTGGT | TTGAAATTCA | AACCTACAAA | AGAAATAAT | AAAAAGCTAA | 7440 |
| CAGATAGACA | AACAAAAACA | AAAGCAAAAC | CCCACTTGGC | CATGCTCTCT | AGTTCCTCAT | 7500 |

-continued

| | | | | | |
|---|---|---|---|---|---|
| TTCTCTCTTG | GAAGAAACCA | GAGCAATGTT | CCCTGTGTAT | CCTTCCAGAG | ATAATTTTTT | 7560 |
| AAAATACTTT | TTTCTTTTTA | ACAGAAGAGA | TGGTAGACTA | CTTCTTTTAA | ATTAAATTAA | 7620 |
| TATACATTTA | CTTGTTTCTT | TTTATTGCTA | TAGAAAATGA | AGTTGGGGAA | ACAGGAAAAA | 7680 |
| TGACCTAGTA | TTATCATACT | AACATACCAA | AATTTTTCAG | TTATATGTAT | TTCCTGTTTC | 7740 |
| AGTTTTTACC | CCACCTGTTT | TTTATTTGGT | TTGAAATCAT | AGTACAGATA | AAAACTTGAG | 7800 |
| GCAGGTATTT | TAGACTTGTT | TTTCTTTTGT | AACATAAAAC | TTTGAGAGCA | CCAGGAAATC | 7860 |
| TGGAAATATT | CATTTAGTTA | TTCATAATTC | AAAATATTGT | TATATCCACT | TTGTGTCAGA | 7920 |
| CTATTTGTTA | AGAACTAAAC | TAAAAGAAAA | AGATGGGGCT | GGACATGGTG | GCTCACACCT | 7980 |
| GTAATCCCAG | CACTTTGGGA | GGCTGAGGCG | GGTGGATCAC | CTGAGTTTGG | GAGTTCGAGG | 8040 |
| AAAGCCTTGC | CAACACGGTG | AAACCCTGTC | TCTACTAAAA | ATACAAAAAT | TAGCCAGGTG | 8100 |
| TGGTGACACA | CGTCTGTAAT | CCCAGCTACT | CAGGAGGCTG | AGGCAGGAGA | ATCACTTGAA | 8160 |
| CCCAGGAGGT | GGAGGTTGCT | GTGAGCCGAG | ATCATGCCAC | TGCACTCCAG | CCTGGGCAGC | 8220 |
| AAAGCAAGAT | TCCATCTCAA | AAAAAAGAT | GATAACACCC | TCTGGGAGAT | TACATTCAGA | 8280 |
| TAGAACAAAT | AAAGGTGTAG | AACCTAAGAT | GTGACAAGGA | CACTGTTGGG | TGACTGATTC | 8340 |
| TTCCTGGGAA | CATTTATAAA | GGCTTCCTAG | GGGAGGGCGT | GTTTGTGTAA | GAGCTTTCCA | 8400 |
| GGTCAGAAAG | TATGTACAGT | GGAAAATGTA | TATGAAAAGA | CCGTGTTTGG | GAATCAGGGA | 8460 |
| TTATATATTG | TGATTAGAGG | AAAGAGTCCT | AGGGTTTGAT | ACCTACAAAG | AATTAGAGTT | 8520 |
| TCTAGGTGCT | TCTGGACATG | TGGATTGATG | ACAGCAATAC | TAAAAATACA | AAAATTAGTG | 8580 |
| GGGCATAGTG | GTGAGCGCCT | GTAGTCCCAG | CTACTTGGGA | GGCTGAGGCA | GGAGAATAGC | 8640 |
| TTGAACCCGG | GAGGCGGAGG | TTGCAGTGAG | CCGAGATTGT | GCCACTGCAC | TCCAGCCTGG | 8700 |
| GTGACAGAAC | GAGACTCCGT | CTCAAAAAAA | AAAAAGAAA | AAAAGCAGGA | GTTAGCAGAA | 8760 |
| AACCAACAAG | ACATGGGAAG | GAGAGAGAGA | GCTGCAACAC | CCAAGAGAAA | AAATAGCAAT | 8820 |
| GCTGAAATCA | AAGTATAATG | AAGGAGAGAG | GATGCTGGAA | GCTATGAAAT | TCTTTCTGTG | 8880 |
| AGGCAATGGG | GCAATGACCC | TAGAACTGCT | GAGTTAGCAG | CAGTGACAGA | CTCAGTGCCA | 8940 |
| AATCATATAT | TAGAAAAAAA | AATCAGATAG | AGGTAAAGTC | CAGATCCAAA | GAAGAGGGTT | 9000 |
| TTTAGCAGTA | AAGCAGACAG | TAGAACCCAC | CCAGCTTTCT | AGGGTGCAGG | GGGCCTCCCT | 9060 |
| TTCAGGCATC | ATGAACAGTG | GGGGACCATA | ACTAGGCATG | ATGGCTTCAG | ATACAGGGCT | 9120 |
| TGTTCATCTC | TTGTTGTGGT | CAGGCACTGC | CTAATGAGAG | CAACCCCTTC | CAAATGCTAC | 9180 |
| TGCTGTGTTT | AACTAGGGCT | CTTGATAATC | TGACCAGCTT | CTGTCTTACT | GATTTTAGGA | 9240 |
| GAAAATGGA | GCAACCTGCA | AGATGAGTGG | GATTAGCTTC | GTGCTGTCTC | CCATGCACAC | 9300 |
| CACTCATGCA | CACTTGGCGA | GCATGGCAGT | TCCATTTATT | TTGCACCCAG | TTGTGATTTA | 9360 |
| AAAACTTTTA | ATTAATTAGT | CTTATTAGTC | TTCAGTTGGA | TTTAAATGCC | AAATAATAAC | 9420 |
| CTTCTACCTT | GTAAGAGGAG | CCCTTTTACC | TAAAGCAAGG | CTTAAGTTTG | GATAAATTTT | 9480 |
| GTCCTATTTA | TTATTCATCC | ACAAGCTCTC | TTAAAACACT | GAATACACAC | TAAGAAGGCT | 9540 |
| CTCAGCACTC | CGAATAGTGT | GATAAATCAA | AAGCCAGTAA | CTTCTCAAAG | TCATTGTGTA | 9600 |
| TTAGTCAGGG | CTCTCCAGAA | AAATAAAACC | AATAGAACAT | ATATACATGG | GCTTTTACCC | 9660 |
| AAATGTCATC | TTTTCAATGA | GTCCTCTTGC | CTGCTTAATT | TTTCTTTTTA | GCATTTGCCA | 9720 |
| CCTCCATATA | ACATGCACTT | TACTTATTTA | TTGTCTTATT | CTCTTTCACA | TGGGCAGGGG | 9780 |
| TTGCATTTGT | CTGTTTACTG | CTGTATCCCT | AGCACCTAGA | GTGGTGCCTG | GCATACGGCT | 9840 |
| GGTGTGTGAT | ACATATATTT | GGAGTGGAGG | TAAAAGTCAC | CACTTAGGCT | ATCCACTTTT | 9900 |

-continued

| | | | | | | |
|---|---|---|---|---|---|---|
| GTGACAGGGA | CAACACACGT | ATCACTTGTC | ATTGTACCTA | TAGCATCTCA | CCCAGAGCCA | 9960 |
| CAAAAAAGT | GGCTCAAAGT | ATATATTAAC | AAAGAACAAA | ATGGAATAAT | CCCATCTGAA | 10020 |
| GGCGAGGATA | TAATAAAAGC | AACATACCTT | TTTTTGGAAG | GACATGGAGA | GCATCAACCT | 10080 |
| TAAGACTAAA | GACTAAACTT | GAGAAGCAAT | TATTACATTT | CTATTAAAAA | TTACCAAATA | 10140 |
| CAAATAGTTA | ACTTTGAAGA | AATATATGAA | TAATGATGGT | ATCTGCAAAA | GAGGAAAAGA | 10200 |
| CTTACTCAAT | TTCATTGTAC | CTTAGTTGTA | AATAGTATTC | AGGCCACCAT | TTGGAACCTA | 10260 |
| TGTGACACAG | TTTAGTTCCT | GTCTATGTTC | ATAAGAGAGG | GCAAAGGCCC | GTTTACATCC | 10320 |
| AACCTCTGTA | TGCCAGCAGC | CACGTATGCC | ACACTCTAAA | ATGGCTAAAC | AGTCATTCAT | 10380 |
| CAGAATCGGT | TCCAAGAACT | CCAACAAAAA | TTAGAGCTCA | TGGTGCCAGA | TTGGCCTGGA | 10440 |
| TTTTCATGCT | CCTGGGTGAT | TACAAAGTTG | TAAATAATGA | TGCTGTCCAC | TGATTTTCAT | 10500 |
| CATGCGGGGC | TCTCTGCTTC | ACTGTGCCTT | CCTCTTATGT | CCATGGCACC | AATTTCTCTG | 10560 |
| ATAGTTCCCC | CAGGGGATAG | GGTTAGATGT | GGGTTCATAA | GCGCTGGACC | ACTGAGGGTA | 10620 |
| ATTCACTCTT | AAGACTAGCG | AGCACTTTCT | GAATCTGAGG | AGTCACATAT | TAAAGAGGC | 10680 |
| AGAATCATCT | TCTGATTTCA | AAAAGCAAC | TACATGACCA | CCCTGAAAGT | GATTTCAAAA | 10740 |
| CAGTTGAAAG | CTAGCTGTTC | AAGTTGATAA | AAGCCACTGC | AGTTCCCTGC | AGGGAATGCT | 10800 |
| GATGGGCTCC | GTTCCCTCTG | CACATTAGAG | CCATTTAAAT | GAAATAATTG | ATCATATTAA | 10860 |
| CTGAAATCAC | CTGGCTTATA | GCTCAGGTCC | TAAGAATTGT | TAGTGGCACT | TGGAGCTACA | 10920 |
| AAGAGGAGTC | CCCAAAAGAA | ACGATTCTCA | CTTTATTTTG | GCAAATGGGT | GGCTTAAGTA | 10980 |
| GAACTGGTCC | TATTCCATAA | CAATAAAAAA | GGAAAAAATA | AATTTTATAT | AAACTTATTT | 11040 |
| CCAAGATTTC | TTACCCCTTC | TTGTCAGCAT | TTCAACTTTA | TTTGGTGGAA | CTATCTTTTC | 11100 |
| TCAATTATGT | GTGATGTATT | GTGGTCGTGA | ATCATGGTGT | CCTGAACTCC | CTTTGGAAGC | 11160 |
| TAAAACGGTC | TGTTGAGGCT | CTGCCTACCA | GCTCTCTAGG | GTTTGTTAAA | GCAAAAGAGT | 11220 |
| GAGCACTTTA | CTTAAATTTC | ACCAATTATA | TTATCTTCTG | AGACCTTAAA | TGTTGAGTAG | 11280 |
| AGGGAAAATA | CAAGTTCAAG | CCTATTTATT | TCAACAATGG | AGCAAGTTGC | TACAGCTAAG | 11340 |
| ACCTTTTGAG | GCTGCCTGTT | TCTTCAGGTT | TTCCTTTGAT | TCTCAGAGTA | ACCCCACCTC | 11400 |
| AATTTATTTG | AATACATGTA | CTTATGGCTT | AACCAACACA | CAGGTGGTTT | CTTTAACTAC | 11460 |
| AGTGCAAAAA | TCTTCACACA | TACAAACTTT | TTAAAAAACA | ATTCTCAATA | TGAAAAGAG | 11520 |
| AAATCAATAT | AATTGGCTAC | AAATTATTGG | CATCTTTTCA | GAGATTTTCT | CAAGAAAGTA | 11580 |
| ACTGAATTCC | TAAAATTCTT | ATGACTTTGT | TAAAGGACTC | AAAATGAACA | TATATTCTGG | 11640 |
| CTGGGCAGGT | GGCTCATGCT | TGTAATCATA | GCACTTTGGG | AGGCCAAGGA | TTGTGGATCA | 11700 |
| CTTGAGGTCA | GGAGTTCGAG | ACCAGCCTGG | CCAACATGGT | GAAACCCCGT | CTCTACCAGA | 11760 |
| AATACAAAAA | TTAGCCAGGC | GTGGTAGTGG | GTGCCTGTAA | TCCCAGCTAC | TTGGAAGGCT | 11820 |
| GAGGCAGGAG | AATTGCTTGA | ACCCAGGAGG | CAGAGGTTGC | AGTGAGCCAA | GATTGCGCCA | 11880 |
| TTGCACTCCA | GCACGGGCAA | CAGAGGGAGA | CTGCATCTCC | AAAAAAAAAA | AAAACAAAA | 11940 |
| ACCTCATATG | TCCTACAAAG | CAAGTGATAA | AAATCAAAAT | ATGACAATGG | GCTGAGAGGA | 12000 |
| AAGGGAAACT | AGTAGTATTA | AAGAAAGTTT | TTAATGAACA | AATAATGTTA | AGGCGGATTT | 12060 |
| TTTTGTTTGT | TTATTTGTTT | TTGGCCTTTT | TTTTTTTTTT | TTTTTTTTTT | TTTTGAGACA | 12120 |
| GAGTCTCACT | CTGTCGCCGA | GGCTGGAGGG | CAGTGGCACT | GTGTTGGCTC | ACTGCAACCT | 12180 |
| CCGTCTCCTG | GGTTCAAGCA | ATTCTCCTGT | GCTAAGGCAA | ATTTTAAGG | ATTATAAATA | 12240 |
| GTAAATATTA | GAAGGGATAC | TGCTTAAAAA | TAAACAATTT | GGATAGCTAA | ATGGTCTTCA | 12300 |

| | | | | | | |
|---|---|---|---|---|---|---|
| GACTCTTTTG | ATTGTACAAC | ATGTAAAAGA | ATTTTGAAAA | CTTTAGGCAT | TCCTTTGAAT | 12360 |
| ATTTTTAACT | TGATTTCTAA | AACTTTTCAT | CAAAAAATAA | ATTGTTTTGT | AAATAAAAGA | 12420 |
| AAACATTAAA | CATGTTATAA | GATGAAATAA | GATGAAGAGT | GACTATAATT | AGAATAAGTA | 12480 |
| TTTCATGACA | TAAGTTTATT | TTAATAAAAG | TTCTAACCAC | TTTATTGTAT | CATTCATATC | 12540 |
| AAGTTTTTTA | AATATATATT | GAAATTTGGT | GCTCTGGGAA | AATATGCCAG | CTTCATTTGA | 12600 |
| AAGAATGAGT | TCCTATCCTG | TACTGCTTCA | GTTATTCTGA | ATTCAGAACA | TTCCCACTCT | 12660 |
| GGCCAGTCCT | CTCTTATAAT | AAAACATACA | ATACTGTGCA | TATTCTCAGT | GATTAAAAAA | 12720 |
| AATACACACA | GCAGATAAAA | GAAGAGGGAG | CAGGCAAACC | AAGAGCCAAG | GTGAATGTGT | 12780 |
| TAATCATTAG | CAGGTTATCC | CCAAACCAAT | ATTTGGAAGT | ACTCCTTTGT | TGACAACCAG | 12840 |
| GAAGTGTTTA | CACTTCAGGC | ATTGCACCTA | AATAAAGTGT | GGATGCCTTT | CCTTTCTAAA | 12900 |
| GTGGAAGGAG | GGATATTGTG | GACATAGGCA | CATTCTGAGG | CAATTTTAGG | AAATAAGTTG | 12960 |
| AAATTGATGG | AAATTGAGAA | AGACTTTGGA | AAGTGTTTGC | CTGCCTCCAC | TACCAAAAAG | 13020 |
| TCCATGGAGA | AAGCAAAGTA | AAAGGTCCAA | AAATGAAAGT | CAGCAGAAAC | CAGAAAGATG | 13080 |
| GGCAACAAGG | TTTTACCATA | CAGATAAATA | GAAGAGAGAT | TCTTAGTAAA | GAAAACAAAT | 13140 |
| TGAGGACAAT | CACTAAATAA | AACAAAATCG | AAGGAAACTC | TAAGACCACC | AGCCAAAAAG | 13200 |
| CAAGAGAAAA | TGATTAACAC | CTTGGCACAT | CTTGGTGAAG | GAATTCCAGG | ATAAAGAGAA | 13260 |
| TCCTATAGCA | CCTAGCCTAA | ACATAGCTCT | CCTACAAAAA | GTAGCTGGCT | AACTAGACTT | 13320 |
| CCTCATATTG | GACATCAGAA | GAGACTAGCA | GGAAGTCAAT | ACTGTTTTGA | ATAAGACAAA | 13380 |
| TTGTGGAACA | AAATTTCTGT | TCCCAGCTAA | GTTAATATTA | CAATGTTTTA | AGGCTCCACA | 13440 |
| GTGATCATAA | AGAGTACTAT | GAAATAAATT | CTCAGCTACT | GTGGGACTCA | GAGGCTCATC | 13500 |
| CAAGTACTGC | TCCAAAAAAA | TACTCCATTG | AAATGTTTTG | AGATGAAGAA | GGATAAAGGA | 13560 |
| TGGACATGAA | AAAACAAAAC | AAAAAACACT | TCATTGTCCA | GGGGTATGCT | AAGTGAGCAA | 13620 |
| GAAGTGTCCA | GCACTCAAAA | TTAAGGAGGC | ACTCACTCTC | ATGTGCCAAT | TCTGTTCTTG | 13680 |
| CATGAGCCTA | AGAAAGGATG | CCTCCTTAAA | TATTGCTTCT | TGGGCACCTC | ACTTGCCTCA | 13740 |
| TCTTGGTTTC | AGCCCTCAAA | TTATGTTCAA | ATAACAGTGA | AAAGTATAAT | ACCCAACAGA | 13800 |
| ATGCAAATGG | TATAATTCTT | CTATGGAAAC | TACTCAATGC | AAAATTAATA | CATTAACTGC | 13860 |
| AAAAGGTCAG | AGCAAAACTT | CCAGAGAACA | GTAGTGAAAC | CAAGAGTGAG | ATGATAGGAT | 13920 |
| GCCTCAGTGT | GTCTGTTTTC | TTATTATATA | TAAGGAGAGA | GACATGGCTA | GGCATGGTGT | 13980 |
| CTCATGTCTG | TCATCCCAGC | ATTTTGTGAG | ACCAAGGCAG | GAGGATCCCT | TGAAGCCAGC | 14040 |
| AGTTTCAGAC | CAGCCTGAGC | AACACAGCAA | GATCCCTGTA | TCTACAAAAA | AAAAAAAAAA | 14100 |
| AAAAAAAAGC | TGAGAGTCAA | CAGCCACTTT | TTTACTATAT | AGGTTATTAA | CTTGAGAAAT | 14160 |
| AAAGCATTAA | AAGAACAATG | AATTTGGGAG | CACAACACAG | CAAAATGTAA | TCTGCCCACA | 14220 |
| AAATTGGACT | TAGAGGAGCA | ATTTTCCTCT | AAGCTTTAAC | CTGTTTCATA | ATTAAATGAA | 14280 |
| AAATAAATAA | ACTATCCAAA | ACAAAATTTA | TATGAAGTAA | AGCAAAGGGA | AATAGGACAT | 14340 |
| AAGCTTGATA | AAAGATAAAG | CTAATCAAAT | ATAAATAAA | AAGACAAGCA | GGGCTGGGCG | 14400 |
| CAGTGGCTCA | TGCCTGTAAT | CCCAGCACTT | TGGGAGGCCA | AGGTGGGTAG | ATCATCTAAG | 14460 |
| GTCAGGAGTT | TGAGACCAGC | TTGGCCAACA | TAGCAAAACC | CCATCTCTAT | TAAAAATACA | 14520 |
| GAAATTAGCC | AGACATGGTG | GTGCATGACT | GTAATCCCAG | CTACTCGGGA | GTCTGAGGCA | 14580 |
| GGAGAATCAC | TTGAACCCGG | GAGGCGGAGG | TTGCAGTGAG | CCGAGATCGC | GCCACTGCAC | 14640 |
| TCCAGCCTGG | GTGACAGAGT | GAGACTCCGT | CTCAAAAATA | AATAAGTAAA | TAAATAAAAG | 14700 |

| ACAAGCTATT | CTTAAAATTA | GTAAATGACT | AAGTAGTCTA | ATGAAGGAGA | AAGAAAGCAC | 14760 |
| ACATGCAATT | GGGTCAGAAG | TACAAGAAG | CTAAAACCTC | AGATATAGAT | AAAATGATAT | 14820 |
| ATTATTAAAA | AGATAGCCTG | ATAAAACAGT | TGAATTTTTG | CAAATATACT | TTAAATAGTG | 14880 |
| TGTAAAATAG | ATGATCCTCC | AGATAACATA | AATGGTCCAA | ATTGATCAAA | GAAAATATA | 14940 |
| AAACCCCTTA | AAAGACCAGT | AACTGAAGGA | AATTGAGAAA | GTTATCAAAG | TCTCCTCAAA | 15000 |
| ATGGCTTTCA | GCCTGCATGA | TTTTTACAAA | CCAATGCTTT | CAAGCTTTCA | AATAACAACA | 15060 |
| GCAATTATAA | AAATTCCATT | CTAGTCAATC | TTTTTCAGAG | TAATGGGGAA | AAAGGAAAGT | 15120 |
| TCTCCTTTCT | TGTTTTTGAA | ATCAGCATAA | GCTCCATATC | CAGACACAAA | AAAGATACAC | 15180 |
| AAAACACATG | TATGCATACA | GAGCCAATCT | CATATATCAG | TACATCAGCC | AAAGTCCTAA | 15240 |
| ATAAACTATT | AGTGAATCAA | ATTCTGTCGT | ACATCAAAAG | AATATTCAAG | GGAAAGCTCA | 15300 |
| ACATTAAGAA | ATACATTAAT | ATAATTCATA | ATATTTAACA | GTCAAGGAGA | AAAAGTAAGT | 15360 |
| CATCTCATCA | TTAGGTAGAT | GACAATAAAC | TATTTGAGAA | AAGTGAATTA | ATTTTCATGA | 15420 |
| CTATTGTTAG | AAACAATCCT | TTAGGGATGG | GGAGGGGAGA | TGAATTAGAA | ATGTTTCCTA | 15480 |
| TCAGTTCACA | ATTGCATCTA | TTCTGAAGCC | ATTAGGAATG | TGAATGGTAA | CTCTTCCTCA | 15540 |
| AACCATCACA | TAAGGAAAGA | TACCCTGAAA | GTCTGACACA | CCGAAGTCAT | CTGTCAGGAA | 15600 |
| TCAATCAGAG | AAGCTGCTGG | GAAAACCTCA | GAGAAGCTGC | TGGGAAAACC | TAGGCATTCT | 15660 |
| GAGTCATCAT | TGTTCTTATC | ACCCGTGGCA | ACTGATGCAA | TTGGAAGCAA | CTGATGCTTT | 15720 |
| CAGGGTCATG | GTTTCTTCAA | AGCCTGAGCT | CATTAATTTT | GCTGTTGAG | AACTTGCAGT | 15780 |
| TTGATCCAAA | AGCTGACAGC | ATCGATTGAC | CCATTGCCTT | CCTTCCTGCT | CTGATACTGG | 15840 |
| AAGTTCCAAC | AAAAGAGGAG | GAGGAACAGG | ACCAAGAAGA | ACATGAAAGC | AGAGGACCAG | 15900 |
| GGGCCGGGCG | CGGTGGCTCA | CACCTGTAAT | CCCAGCACTT | TGGGAGGCTC | AGGTGGGCGG | 15960 |
| ATCACGAGGT | CAGGAGATCG | AGACCATCCT | GGCTAACATG | GTGAAACCCC | GTCTCTACTA | 16020 |
| AAAAATACAA | AAAATTAGCC | GGGCATGGTG | GCAGGTGCCT | GTAGTCCCAG | CTACTGGGGA | 16080 |
| GGCTGAGGCA | GGAGAATGGC | ATGAACCCGG | GAGGCAAAGC | TTTCAGTGAG | CTAAGATCGA | 16140 |
| GCCACTGCAC | TCCAGCCCGG | GCGACAGAGT | AAGACTCTGT | CTAAAAAAAA | AAAAAAAAA | 16200 |
| AAAAAAGCA | AAGGACCGAA | GGACCAAGAC | CCCTTCCCAA | CTGCTCCATT | GGTCAAAACG | 16260 |
| AAGTCAGAGC | AGAAGCTCTC | AAAAGGATGA | TACTTTGAAT | TTGCTTTCTG | TTTTATTTTC | 16320 |
| TACATTCATA | AACGTGCACA | AATCATAAAT | GTACAATATT | CACAAAGTAA | ACACACATCC | 16380 |
| AAGTCAAGAA | ATAAAATATT | TCTAGTACCC | CAGGAGCACT | TCTTAAGTAC | CATCCATCCA | 16440 |
| GCCACAACCC | CCATCCCTGC | ACAAGGGAAA | TCGCTCACTG | ATTTTAACA | GGACAGATTG | 16500 |
| GTTGTAGCTG | TTTTTAAAAA | GTATTTTATA | AACCTTTAAA | AGAATGTGCG | TTTTGTCTTC | 16560 |
| CTTTAATCAA | TATTGTGCTT | ATGAGACCCA | TTCATCTATT | ATATATTGGG | GTCTGTTAAT | 16620 |
| TCTCATTGCT | ATACAAATAG | ACCGTGGTTT | ATTTACTCAT | TCTTTTTTTA | ACAGACAACT | 16680 |
| TCCTGTTCAG | GCTATTACAG | ATAGTGCTCC | TATGAACATT | GTTGTACATG | TTTTATGGAT | 16740 |
| GTATATGTGC | ATTTCTAAGT | AAAATGTTTG | AGTCACTGGA | ATTGTACATT | TAGCTTTAGG | 16800 |
| AGATATTGCC | GAGCAGCTTT | CCAAAGTTCA | CATTCGTAAC | GTATGAAAGT | TCCAGTTGCT | 16860 |
| CCACATGTCT | GGCAACATTT | TGTTTTCCAT | CTCCTTTCAT | TTTATCCATT | AGTTAATTTT | 16920 |
| ATAGTGGTAT | TTCATTGTAG | TTTTGATTTT | CATTTCTGTA | ATGACTAATG | AAGTTGAACA | 16980 |
| TCTTTTTATA | TGTTAAGGAG | CCACTTACAT | TTTCTCTTTT | ATGAAGTCCC | TGTTCAAGTC | 17040 |
| ATTGGCCCAT | TTTTTAGTTG | GGTTGTCTGT | CCCCCACCCT | TTTTGTTTT | TTTTTCTCT | 17100 |

| | | | | | | |
|---|---|---|---|---|---|---|
| TTTTTCTGTA | CATAATTTGA | CTACCTATTA | TACTATGTCT | TTCTTTTTTC | TTCTACTTCT | 17160 |
| TCTTTTAGTT | TTCTGCAAAC | CCCCTTTCCT | CTTTGTGTTG | TCAATATCAT | GAAGGCAAAA | 17220 |
| TCAATGTTCT | CATCTTAGTA | CCACCCTCAG | GGCCTGACAC | TCTGTTTTTC | TGAAAACTT | 17280 |
| GCTCAAAAAT | ACCCATTGAT | TTGCATTAGG | AGATTCTCTT | CATCTGCTGA | ATTAACCCAA | 17340 |
| GGTTCTTGTC | CAAGCAGTTT | TTTAATAGGA | TTTAAAATAT | GGTGGGAACT | TCTTCTCTAG | 17400 |
| ACATGTTGTG | GCAAAACCAG | AATCAGTTCT | GTGTGAGGAG | ACAAACTAAA | GGATATGTCT | 17460 |
| TAAGTGTTAG | GAGCCAAATT | AATTCCTGTT | AGAGTTGACG | CTGCCTATCT | GAGTATCTTG | 17520 |
| GGAAAGTAAG | AAAAATATGA | AGAAGGTTAA | ATTATCTTTT | TCTACGCTCA | AAAGGAACTT | 17580 |
| CTCTTGTATG | TGATACACTT | CTATGCCTTG | TATGTGATAC | ATTTCTATGC | CTTTTCTCAT | 17640 |
| CTTGTTATGT | CTTCAATATT | TTTCTCCCCC | ATATAAATTG | TCATTTCACT | TGAAAGTGTC | 17700 |
| TCTGTCATCT | CTCTCCAATT | TTCATTATAT | GGTCTAAACT | ATATTGCTAT | CCCTTCTGGA | 17760 |
| AGTGTCTACA | TTGCCTTCCT | TCACATTCAT | TCTTCTCACA | ATACAAGCCT | TCCAGTTCTA | 17820 |
| TCTTCTCTGT | CCTTGATTTC | TAAGTTAACC | TCATTTATTT | AATCTTGTAT | TGGTCATTTT | 17880 |
| CTCATCATTA | ATCTCTTGCA | ATTGGGCTAG | GATAAATAAA | TATCTGTTTA | ATCTGATGGA | 17940 |
| AATATCTGGA | TCTAAATAAT | TTGAAAATGG | TCTATTTTAT | TTTAGCATGT | AAATTTTAAT | 18000 |
| AGAATTTAAT | CACATAAATA | AACGTCTATG | TTTTACAATG | TATAAAAAAT | AATAAAAACT | 18060 |
| TTAATTCTGG | GGATTATAGC | TTTACAGTTC | CGATCGGTGC | TGAGATCTGT | AACATATGGC | 18120 |
| TACAATTCCG | AGCAGATCTT | CTCTGCATCC | AATAACCTGC | CCCACCATGA | AGATATTTAT | 18180 |
| CAGTGATCAT | TTTCACATGA | ATTTTTATTT | ATTAGTACT | TTCCAATGAG | GAAAATTCAA | 18240 |
| AGGCCACATG | AATTGACTTT | TCAAGTTTGT | CCAGCTGTTG | TCAACCCCGG | GCGCATGCTA | 18300 |
| GAAACCTCTA | AGGAGTATCT | AAAAATTAGT | AGTATCTGGG | TTCCACCCCA | GACCAATTCA | 18360 |
| TTCAGAATCT | CTGGAGTGGG | TCCCAAGTAT | CAGTGTCTTA | TAAAGGCTCC | CCAGGGAAGA | 18420 |
| CTAACACACA | GCCAGAGTTA | AGAACTGCTG | AGTCTATGGT | CAGGAATATG | GAGAGAAGTA | 18480 |
| AAAAATGTTT | AAAAAGTTCA | TGCTCAGTAC | CACATTTAAG | TTTGTAACTT | TATGTCCTCA | 18540 |
| GAGGCGGGTA | AGGGTCCTCT | CTTTGGCCCA | GTCTTGAAGT | TCTGCTTGTC | CAAACGTGAG | 18600 |
| GTAAAGACC | AGGCCAAACA | TGTTGACTGC | AGCAGACAGG | AAAAAGACAT | TCCTCCAACC | 18660 |
| AGACTCAAAA | TCCTAGATGT | AAAAAACAGA | GAAAATGATC | AATCTCACAA | GTTCCTTCTA | 18720 |
| CACCAGTTCT | AGTAGCCCTC | CCAGTTGTGT | ATTGCAATGT | TGATCACAAG | GAATATAAGG | 18780 |
| AACAATGTGC | AGTAGTTACT | TAAGAAAGTT | TATGAAACTA | TTGGAAACAA | AATGGCCAAA | 18840 |
| ATGCACATGG | GGTTCTGAGT | TGAGATGGTT | ATTTCTTTAA | ACAAAAATAA | AATACACTAA | 18900 |
| TGTTTTTCTG | AAAATTTGGA | TTTCAACATA | TAATATTACT | CATTTAAAAT | TATGCCTAAA | 18960 |
| ATGGCATTGT | GGCATTGTGT | TTGTGTCTTC | TCTGTTTTTT | TTTGTTGTTG | TTGTTGCTGT | 19020 |
| TTGTTTTGTT | TTTTTTTGTT | TCTGTATTGG | CTGTTGACAA | CTATCACTAC | AACCCATCTC | 19080 |
| AATTCAACAT | GAGTTCTCTT | TGGTCTTCTG | TGTGACCCTC | CTCAGAAAGC | CTACTAAGT | 19140 |
| CATTTCCAGC | ATTATAGTCA | CAGTGGATTC | CTAGCAGTTT | AGTCAAATAT | TAACCTGGGA | 19200 |
| ACTTGATCAC | ATAGAAATGT | AGTAAAAACA | AAACTTCTCT | TTGTAAGTTG | GTTCTCGTCA | 19260 |
| GTCCTTCCAT | CCCTGCCTGG | GTCTGTCTTT | TCATCTTCCT | CATGAGCCTG | CATTTCCAAA | 19320 |
| CACCGAGCAA | GCCTCCTTGC | AATGTCTCAC | AGCCGATCTG | TTTCCAGACA | TTAAATTATC | 19380 |
| TTTAAACTGG | CCTAGGACAC | TTTGTTTCCC | TTTTGTGATT | TTTTAAAAAT | TGGATTAGTC | 19440 |
| TGAACATATT | CTTCATGATC | TTCTTTTGCC | CCTCTGTCTT | CGTCTCTTGC | TATTCCTTGA | 19500 |

```
CATGTGTCTT TCATTCTGGT CATAACTAAG AACTGTTTCA TGCTCATGTA CCTCTAGGAA    19560
GTCACACGTG CTGTCTTCTG CACCGGAACA GCTCATTTTA ATCAATCTAA CATCTATTCA    19620
TCTTGAGAAA ATAAGCTTAT ATTTTCTTC  CTCTGGGAAA TCTGACCTAC CAGAGTCTGA    19680
TTTAGAGGCT CATGTAAATA GAGTAATTGT GTTGCCATCC AGATCTTTAG AGCACCGTGT    19740
GTATCTCCAA CACCTAAAAC AATACCTGCC ACTTGAAGAT GTTCAATAAA CTGGCCCAAC    19800
CTGACTGATG AGGAATCCAG TGGCAGTGGA AGAGATGATT CCTGCGATGA GCCCAAATCC    19860
CCTTGAGATT CCCATGAGGA AACTTGCATA TCTGTGGGAA GATGATTTTA TAAATGATTT    19920
TATATAGAAA GCCACCTACA GCTTCTGCAG CAACTCAACT TTAATGCAAT TCAGCTCTAA    19980
TGGCAAAGTC ATTTGCTTA  ATGCAGTTTT TCATTCACCT AAAGACATTC AGGGCAATGT    20040
CTATTTGCCA AACCTGAAAT TACCAATCTA CCAAGTCAAT AACCAGGGAG CAATGCAGTC    20100
TCTCTGGGAA CCACGTTTCT TTACCCCGGC TGCTCAGTGG AGAAGCCAGT TTGTGCAACG    20160
GGCAGGACAC AGACTCCAAA GCCAGACTCC CCCAGTCCAA ATCCTGGCTC TGCCTTTATG    20220
TGACCATAGT CACACCATTT AACCTCCTTG TGCCTCAGCC TTCTCCCTTA TAAAATGGGG    20280
ATAACAATAG GGCCTACCTA ATATAACTGT GAGGATTAGA TGTGTTGATA TATGGCAAGT    20340
CTTGGCACAG GAGCTGGCTT ATTGTGACTG TATATATATA TATATATATA TATATATATA    20400
TATGGTAGCT AATATGAACA ACACCATGGA AACTTTTCCA AATCACCTGT GTGTGGGCCT    20460
TTTCCCAGCA TACACAGTTC AATCTCTGTT AGGGAAGCTT GGGAAGGTTT TTGTCAAAAT    20520
GATTACTGGC CAAGATTGGA AATTGTTGTT CTAAAAATGC CACATTTGTT GTTCTAAAAA    20580
TGGCCACAGA CAGATATTTG TAGTTATTTG TCATTCTGCC ATTAGTGCAA TGTCAGTAAC    20640
ATTAAAGAGT TTCACGGCGA CCACTGAGGT CTAACACCTC TGGAGGGGTC TGGAGGAGGG    20700
GAAAAAACAG GTAGAGCTCT TACCTGGGGG CGATATCTAA GGTGTTGATG ATAAACCCTG    20760
AGTCACATAG GTTACTGGTC CCAGGAATAA GTATCAGCAA AATAATGGTT ATCACGTAAC    20820
TGGAGGCCAC AAAGGGCAGG GCCACAGCAC ATATTGATGG AAGGAGGAGC CCTGGGCAAT    20880
GAGGACATGC TGTCAGGGAA CCCTCTGAGA CCATGTGCAG AAAAGGGATT GGTTAAATGG    20940
GCCCACACGC TTATCCTTAC CAAGAGATGA AAAGAGCTTT CGCACAGTGA TCAATCTGAG    21000
AAGATTCCTG GACAAAAGGA AATCTGCCAG CTGACCTCCT AAAATTGTAC AGCTTGCAGC    21060
AGCAATAAAA GGCAGGGAGG ACAGAACTCC ACTCTGAAGG AAGGAAGTTT ATACAGAGTA    21120
GTTATAGAGA TACGTTAGCA CCAAAATTTG TCAGTTACAC AGACCAGCCA TTAACTTACC    21180
CCCATGATAC TGTGGGTTGT TGGGGGAAA  ATTAGCATCC TTTTTCACAC TAAAAGAACA    21240
CTGTCTCAGA TAAGAGGGCC AGAAGCTGCA TCACTCTGGG CTCCAGATAA AAGCAATATT    21300
AATTTCTTGG GTTTTTTGTT TTTGAAACGG AGTCTTACTC TGTCGCCCAG GCTGGAGTGC    21360
AGTGGCATGA TCTTGGCTCA ATGCAACCTC CACCTCCTGG GTTCAAGCGA TTCTCCTGTC    21420
TCAGCCTCCT GAATAGCTGG GATTACAGGT GCCTGCCACC ACACCTGGCT AATTTTTGTA    21480
TTTTTAGTAG ATGATATTTA GTAAACCATA TTGGTCAGGC TGGTCTTGCA TTCCTGACCT    21540
CATGATCTGC CTGCCTCGGC CTCCCAAAGT GCTGGAATTA CAGGCATGAC CACCATGCCT    21600
GGCCCAGCAA TATTATTTCT AAAAGAAGCT TTGGAATCAG CTGGTGTGGT AGTATAGCAT    21660
AGTGGTTAAG AATATGGATG CTGCAGCAGC TCTATCACTT AGTATTGTGC AACCTGGGC    21720
AAGTTATCTC ACCTCTAAGT GTCCTGTTTC CACATCTGTG AAAAGGGAAT TATAACAATG    21780
CCTCTCTCAA GGTCATTGTG AAGGTTAAAT TAATGGTTAT ATGTAAAGCC AGAATGTAAT    21840
AGGTAACACA GAACTGTTTC TCCTTATTAC CATTATCATT TTCGTAGAAG TATAGGAAGT    21900
```

| | | | | | | |
|---|---|---|---|---|---|---|
| AAACTCACAT | CTCTGATGTT | AACATGGAGC | AGAGTACTGA | TATACGTTGG | TAGGTATGTT | 21960 |
| AGGATGATGG | TGCACAACCA | GAAATGGCTG | AAAAAACCCA | GGAAAATGGC | CCAAAGTGGT | 22020 |
| AGGCATGTGA | CCATCGCCTT | TATGGGGACA | GCTCGTCCAG | GAGAACTGGG | CTGAAAAGAA | 22080 |
| AGATCTAATC | AGCATGAGTA | TTAGAGCAGC | CAAGATGGTG | CCTCTCAGAG | GAGATCCACA | 22140 |
| CCCTGCCCTA | GAGACCTCTG | CATGGGCCAC | AGGTACAAGG | TGTGCACTGT | ACCTGTTGAG | 22200 |
| CCAGTGAGGA | CAGGATGTGC | TCCTTTTCCC | TAACACTTAT | GCACGGGTGA | TGCATGGGGT | 22260 |
| CATCATAAAT | CACTGTGAAC | CATAGGAGAC | AGCAGACACA | GCCAGTGCTA | CCTGGGAAGA | 22320 |
| AGGGATAAAA | TTAGTTTTTA | GGTAGATTTG | TTTACTGGGG | GAAGGAAGTT | TCCTCTGAAG | 22380 |
| TGGCATGCCT | CTCCCTTCTA | CACACTAATC | AATTAATGCT | TATTCTACCA | TAAGGACCTA | 22440 |
| AATGTTCCCA | TTCTTTCTTT | CAATCCTTCT | ACAAACCTGT | TAAAGCTTTT | TAGATATTAC | 22500 |
| GTCTCAAATA | GAAAGCCACC | ATTTGTCAAT | GTCAGAGCCC | TCTGGAGATA | ACAGGAGCGT | 22560 |
| GGCATTGCAT | AGCTGATTAA | TTACTTTAAA | GTCTCCAATG | ATTACAGTGT | TATGTATTTT | 22620 |
| AGGCAGCAAC | TTCTTAATGC | ACACATAAGT | TGTCTTGTTG | CGGAAGATCT | GAATAGTCAG | 22680 |
| GTTTGCAGTC | ATACATACAC | GAAACAACCT | TCCATGAAAT | CATGTGGCAG | GGAAAAATTT | 22740 |
| CCAATGCACT | TACAAGAGAC | AGTATTATTT | GTATTCAAGC | CATACATCCA | TTATGGATTC | 22800 |
| CCAAAAGAAA | TATTTTTGTA | CAATACCTGG | TTAACATGTA | CAAACCAAAA | TAATTAGCAT | 22860 |
| CATTAATGAG | AAAGCCATTC | AGGCCAGGAC | TATATTTAAT | GACACCATTT | GGCTATAAAA | 22920 |
| ACAAATCAAG | TGTAGAAAAT | TGTCTTATTA | TTGGAATTCC | TTATTTGAAG | AACATTCTAT | 22980 |
| GTTAAAAGAT | TCTGAGGACT | AGTTTTCTTT | AAATCCCCTC | TAATTACTGG | ATTCACTGAT | 23040 |
| TCTTTTATTT | TAAAGCTAAA | AATCAGGCAC | CATGATGACA | CCCAAGTGAT | GAAAACATAG | 23100 |
| AATGGATTCC | TTGCCTCAAG | CATTTCACAG | TCTAGTGGAA | AGAAAGGAG | AAATAAATAA | 23160 |
| TTACACACCA | ACATAACCTA | GAGAGGAAAT | ATCATAAAGG | AGAGAATGCC | AGAATCTGAT | 23220 |
| AGGGTAAGCC | CTGGAAGGGC | CCATGGGGAA | GGGAACATTT | GAATTGAACT | TTGCAAGATT | 23280 |
| AACTTGGTAG | AGAACAGGTG | AAAGGCATCT | TGGACAGAAA | TAATAATTAT | AATGAAATAT | 23340 |
| GAAGACACAT | TGAAAATGTA | CTTCACTATC | TTTGACATCT | TAACTGCATA | TAGCAGGCAC | 23400 |
| TTCAGATGTG | GTGGTAGAGA | TTCTGCAGAA | GGTGCTTGAT | ATGGAAGGAC | AAGACTGCAT | 23460 |
| CACAAGTCGG | TGGGTGCCAT | GTGAATAGTC | AACTCCTCTA | CCTTGTGCGT | GTGGCTTCCC | 23520 |
| AGAACCACCA | GGAAGGTGTT | AATCAGGTTG | TGTGACTAGA | TTAAAAATGA | TACCAACCGT | 23580 |
| TGACATTTTT | TATCATCTTC | CATTTGATAA | AGGACATTTT | CTTTCATATA | GGAAGAATGT | 23640 |
| GGGTGGTGTA | GGTGCCAAAA | TGGATGCTCA | GGAAATGGAG | GCGTTAGGAT | TTAAGAGAAA | 23700 |
| GTGACTCACC | AAAGATGTAC | AAGATAAAAG | GCCAGCTCAA | GGCCTGTGAG | ATTAGTCCCC | 23760 |
| CCACACAGAG | GATGATGAAG | GATCCAAATG | CTGACCCTAA | AGGAAAAAGG | GAGAAAAACA | 23820 |
| CTTATGAAAA | TATCAAAGGC | TGAGACTTCG | TGGCCTCCCT | AAACAATGTC | CCAACAGTGA | 23880 |
| GGTGGCAGAC | TTAGAATTAT | TGGGCAATGA | GAGTATTTAT | TTCTAAAATA | GCTCACAGAT | 23940 |
| TTTCCCCAGT | AAAGTAATAT | GATATAATTA | AAATTAACAA | ATAATAGTAA | CACACTCTCT | 24000 |
| GATTCTTCAA | TGGCTCCTCA | ACACCAATGT | GACCAAATCT | AAATCCCTTA | GTTTGTCACA | 24060 |
| GTAACTCTCT | GCTATCACAG | CCCATTAGCA | TTTTCTTGTG | ATTACAGTTG | CATTCTTGCA | 24120 |
| TGATCTAATA | TGAGGCTAGG | GGCAGGAAAT | GAAAGACTTA | CAAAAATCGG | TAAGATACAG | 24180 |
| CCCCTGCCCT | CAAAGAGCTT | CTGGTCCAAT | TGGAGAGAAA | AATGTGAATA | AAATTGATTG | 24240 |
| TCACTAGTGA | AATGCCATGT | AGGCTTTGGA | AGTCTACATT | AAAAAACAAC | AAGACACATA | 24300 |

-continued

| | | | | | | |
|---|---|---|---|---|---|---|
|TTTCACAGAG|ACCTATAGTA|AGAAATGCAT|TTTACAGGGT|AACATAACAC|ACACACCAAT|24360|
|ATGCATAAAC|ACTTGTACAT|ACAACCACAC|ACATATGCCT|CAAACGATGG|TTTCATGAAT|24420|
|CGATATTTAA|CTTTACCATG|TCCAATGCAC|TCCAACAATT|TCTATTCTAT|TCTATTCATT|24480|
|TTTTAAAATA|ATGATTTTAA|CCCGCTCAAT|GGATTTTATG|ACTCACTAAT|GGGTCCCAAA|24540|
|CTGAAATTTG|AAAAAAAGA|TGTAAAATAT|AAATATAATA|AAACTACAAT|GTACGTGGAA|24600|
|GTATATCTGA|GGATAAATTG|ATAATAATTA|TAAGATTTAG|GAAGTTTTGG|CCGGGCGCGG|24660|
|TGGCTCACGC|CTGTAATCCC|AGCACTTTGG|GAGGCCGAGG|CGGGCGGATC|ACGAGGTCAG|24720|
|GAGATTGAGA|CCATCCTGGC|TTGAAACCCC|GTCTCTACTA|AAAATACAAA|AAATTAGCCG|24780|
|GTCATGGTGG|CAGGCGCCTG|TAGTCCCAGC|TACTCGGGAG|GCTGAGGCAG|GAAAATGGCG|24840|
|TGAACCCGGG|AGGCGGAGCT|TGCAGTGAGC|CGAGATAGCG|CTACTGCAGT|CCGGCCTGGG|24900|
|CGAAAGAGTG|AGACACCGTC|TCAAAAAAAA|AAAAAAAAA|AAAAAAAAA|GGTTTAGGAA|24960|
|GTTTTTACAT|AAGCTATGCA|ATAGGATAGA|TGGAATTTTG|GCACAAGGAA|CAGGGGCAAA|25020|
|GAACTTTCCA|GGCATATAAA|CTAACGGGAG|CAGAGCCAGA|GGGAAGTGCA|GTGCAGATCT|25080|
|ATGTGGAGAG|CAGCCAATGT|CCAGTGCCAC|TGGAGCCATG|CTTGCACAGG|GGAGTTGAGT|25140|
|GGAACAAGGT|TGGGGCCAGA|TGGCTAAGAA|CTTTTGTATT|CATGCAATAA|AGAGGTCAGG|25200|
|CTTTACTCTG|TAAGCATGAA|GGAACACATT|GAAAATTCTC|AAGCGGGTGA|GTAAAAATGT|25260|
|GCCATCTTTA|TTTTAGCAAG|CTAACTTGGT|TTTGGTGGGA|AGAAGGTTGA|AAGAAACCAG|25320|
|TCTAGAAGAG|AGAGATCAGC|AGATAGTATT|TGCAAATAGA|GGAGATGGTT|ACAACTATGA|25380|
|TGGAAGGAAG|CAAGAACGCA|GGAGGGTTGC|TTGAGGTAAA|AGTCTGCAGG|ATGCAGCTGT|25440|
|GTAGTGGACC|TAGGAGTGAG|AAGCTGGATG|GAATTTTAGT|TCTGCTCTTC|GAGTATATAC|25500|
|TCTCAGCACG|ACAGGCTGGG|GAGAACAGCA|ATGATAAAGC|TGTAGAGGCC|TGAGTAGGAT|25560|
|CACATACCAT|GGAAAGGCAG|TCTAGCATAG|TGATTGAGAA|TGTCTGCTCT|GGGGCTAAAA|25620|
|TCTGCATGGG|CTTAAATCTC|AGACCTACCA|CCTGCTGGCT|ATTTGTATTT|GGGCAATTTT|25680|
|CTTAATCTCC|ACCTTCCTTA|ACTCCCTTCT|CTGTAAAATA|AGAATTTAAA|ATGGTACTTA|25740|
|TATGAGAGGG|TTGTTGTGAG|AATTAATGAG|CTCATAATAG|AATAGTAAAG|AGCTTAGAAT|25800|
|AATACAGAAA|CTTCAAACTC|TTCCAGCCTG|ATTTCTCTCC|TTACCACCTG|GAGCTGTGGT|25860|
|AGCCTTAATT|CTCACTTCAA|AATCATTGCT|AAGATGGTGT|ATATATAGCT|TACTTGATCT|25920|
|TTTTCCATGT|GTGCAATTCT|TAAAGGTTTA|AACTTTTTCC|GACAAGGCTT|TTCTGACTAC|25980|
|TAAGGCTTTT|CTGACTACTA|AGGCTTTTCT|GAGCTGAAAC|CTAGCTCACA|ATGGTTTTTT|26040|
|CTACTTCTAA|GCTTCAATGT|CTTTACTGCA|CAGATGCATC|TTTCCTATTT|GTGATGCAAG|26100|
|TGTCTTATAT|TGTTGAATTT|TTCAGCAGTA|CTTTTTCTCT|CTCTTCCCCA|AACCATTTGA|26160|
|TTCATAGAAG|ATAAGACACA|GTGGGATGGA|ACAGATGACA|AAGCTATGAC|CCATCTGTGC|26220|
|ACACTTACCT|GATCCTGCAA|TGGTGGTGAG|CTTGCTTCGT|TCAAGTGGAG|GAGCCCACTT|26280|
|TGCCCAAATA|GTAAACTGAC|CTGTCCATGC|CATTCCCTGA|AATGAAAATC|ATTAAGACCT|26340|
|TTGATATTTT|GTAGAATTCA|GAAATCTGGA|TCCCACCAAG|AATGAGAAAG|TATCTGGATA|26400|
|CCTGGGCCAA|GCCCTGGACT|GTCCGAACCA|TGATGACCAA|AATCACTCCG|AAGTCAGCAG|26460|
|CCAGTGGTGT|AAAGAGGGTG|AGAAGGGAAG|AGATCAGCAA|ACCAGCACCA|AGCATTTTTT|26520|
|TTGCTCCAAA|TATCCCTGCT|AAATATCCAC|TTGGGATCAG|AGTCAGTATT|ATCCCATAGT|26580|
|TGATGGAGCT|AAAGATGATA|CCCTGAGTTT|CTGGGCTCCA|TTGATACACA|GAGGCCTGGG|26640|
|GGAAAAATAG|GAAAACTCTT|TGTCAAGAAG|TCCTATTATG|AAAATCTACT|TTACAGTCAG|26700|

-continued

| | | | | | | |
|---|---|---|---|---|---|---|
| AGTTGCTTGA | GGTTAGTGAG | ACCCTAGTAT | AAAATATTGA | TTTTTGTTTC | TCTCTATATT | 26760 |
| CTTCCTACCT | TCCCAAATAA | CCAATTATAC | CCCTAATTTG | CTTGTCTTAG | TAGAAGGAGA | 26820 |
| GAAAACAGA | AGAAATGAAG | AAAAGAGGTA | AAGAAAATGA | TTATATAGAT | GAATAATAGG | 26880 |
| AAGAAGTAAA | TGGAAGAAAA | CATTGAGAGA | TATTTCATCT | GTGAAAGCAC | TTCCTCTATT | 26940 |
| TTGCTTCTAG | TAAAAGTTGA | GTAACATCTT | GACTCTTATA | TCAAAGAATT | TTTTAAAACA | 27000 |
| CACACACAAA | ACTTTACTGA | ACTCTTAACC | AAAATCAGTG | CCTAATTAAA | AAGAAAAGTC | 27060 |
| AAGTTTGGGA | ATCATGGTCT | GCCCTGGCTG | AACTGAGTTC | CTAAAACACA | TATTACAAAT | 27120 |
| GAATAAGATC | ACATTCTTCT | GATATAACTC | AATAAATAAT | TTGAATTATT | TTAAAATAAC | 27180 |
| TACCTAAAAT | TCCTAAATAA | TTACATAAAT | TATATTACCT | GAATATTTAC | CTAAAAATAA | 27240 |
| ATAGATTTTA | AAATAAATAA | ATAAAAAATA | AAATAGATTT | TAAATAAAA | TAAAAAATAA | 27300 |
| ATGCAATAAG | GCCCCTAAAT | ATCTGGCATC | ATGCTATAAA | GTAGAGAGCC | AAAGAATATA | 27360 |
| AAATATGAAA | TATTTTACCC | ACTCAAAAAA | ACTATAAATA | ATACAAGGTA | TATGATTCAT | 27420 |
| GTGAGAATCA | AGATTTGAGG | ATGAACATAA | ATAAACAGA | GACTTTGAGA | GGAGAAAATA | 27480 |
| ATAATTTGGG | AAGGTCCCAG | AAAGGAAGCA | ATACTTGAAC | TATCCCTTGA | AAAATGACTA | 27540 |
| TGATTTGTAG | AAAGTCAAAA | AGGAAAATTT | TATCTCATCG | GAAAAAATAG | CAAAAGTGAA | 27600 |
| CTTGTAGCAT | TTGGAAGAAA | CTAACAGGGA | CTCTGGCTTG | CTCAGGGCAA | AAACTTTCCA | 27660 |
| TGGGTCATTG | ATAGCAGATG | TGAGTGTGCT | GAGAAGCAGG | CCCAAATTCT | GAAGGAACAC | 27720 |
| AGCATGTCCA | GTGAACACTG | CATGTTTGGC | AACTTGAAGG | TGTCCAAGAT | TCCTGAGTAG | 27780 |
| TGAATCTACT | CAGTGTGGAT | ATGTAGACGG | GATAATGGAG | GAAAGACTGG | AGACAATAAA | 27840 |
| TTTATGTACT | CATTGTAAAT | AAGCTAGGTC | CAATGTAATA | AAATCATTAA | TCATGAATTA | 27900 |
| TAGGGATGAC | ATGGGAAATG | TACAGTACAA | GATAATTTAA | AGGATAATTT | TTTTAATTGG | 27960 |
| GTAAATTCAT | GGTTTTCATA | TAAATGTAAA | ATAAACATAC | AACAAAGATT | TTATTTAACT | 28020 |
| CATTGATTAA | TGGAGGAAGT | AAGTAAGATG | TTATAACTGG | TTCAAAGGAA | AACTCAAAGA | 28080 |
| ATCACGCATA | ACACAAGCAG | GAAGCAATGC | TGAAATAGAC | TTTAAATATA | CAGCAGAGCC | 28140 |
| TGGCACAGTG | GCTCACACCT | GTAATCCCAA | CACTTTGGGA | GGCCGAGGCG | GGTGGATCAC | 28200 |
| CTGAGGTCAG | GAGTTCGAGA | CCAGCCTAGT | GAAACCCTGT | CTTTACTAAA | AATACAAAAA | 28260 |
| TTAGCCAGCC | GCGGTGGCAT | GCCCCCTTAC | TCCAGCTAC | TTGGGAGGCC | GAGACAGGAA | 28320 |
| AATCTCTTGA | ACCCGGGAGG | CGGAGGCTGC | AGTGAGCTGA | GATCATGCCA | CTGCACTCCA | 28380 |
| GCCTGAATGA | CAGAGGAAGA | CTCTATCTCA | AAAACAAAC | AAACAAACAA | ACAGCAAAAT | 28440 |
| TGGCTAATTC | AACTGGGAGG | TGAGTGGAGA | AAAGTTTTAA | CTGATTTTTC | TCTTGGCAAA | 28500 |
| ATTTATTTGC | AAAGCTATGG | ACAAGAATCG | TTTGCATTTC | TATTGGTTAT | ATAGAATTTA | 28560 |
| CAGGGATATA | AAATTGCTCA | GAAACAATAA | AACAGGCAGA | GAACTGAATA | GGATTGAGTA | 28620 |
| ACCTATAAGA | ATGTGCCCAG | GTAATACCTA | GTTTTTCATT | GAAGACATCA | CATAAACTGT | 28680 |
| TCCATTTTTA | AATTTTTCAC | ATTTAACTCT | ACAGTTCCCC | CACCTTATAA | TCATAATAAC | 28740 |
| CTCAATGAAA | TCTTATTTTT | ATTATTGAAG | TAAGCAATGT | CTCAAAGAAA | AATAGTTCCA | 28800 |
| GTCAGTTTTA | ATTTGTCATT | GGAAATGTAT | ACTTCCATAC | TCCACAGAAT | CAAGATCTAT | 28860 |
| GCCTTCCTTT | CAAAGTTTTT | TCTCTCAACA | AAGAGCCCTA | TTTTCCATCA | TACTTACCTT | 28920 |
| TGTATCAAAT | TCCTTGATGG | ATATGCTGGA | GTTATTGAAG | GCATCTGCAA | CAGGCCCCTC | 28980 |
| AGTGGAGGCA | TTAGATAGAC | CTTGCTGCTG | AGTGGTGTTC | ACCATGGCGA | TGATCGCAAT | 29040 |
| GCTCAGACTC | ACACGCTGCG | TTATCATGGT | GAAGTTTGAG | AAGTGCATGA | TAAGAGCCAG | 29100 |

| | | | | | | |
|---|---|---|---|---|---|---|
| CCCATAGCGT | AATGAACAGA | AATCTGGACC | TAGACAACAA | CACAGATGTA | TGTAGTGAGC | 29160 |
| ATCCTGACTG | AGACCCCTTT | CTTTTCCTTT | CTCTCACAGC | TCGATCTGAT | AGAACTTTGG | 29220 |
| ATGACACATG | AAGTCTCATT | GTCTTTTTTT | CACCAAAATA | GCCAGCACTA | CAAACCCACT | 29280 |
| TTGTCAAATT | ATTTGGTTGG | CTTCAAGACA | GCGAATATGG | GATCTTATAA | CCAAGTAAAG | 29340 |
| CAAATATGGC | CATCTTTCAA | GGGGATAGGA | AACACATGAT | AAATAGAGAA | AACCCACATG | 29400 |
| TAAGGCATTT | ATGTCATATT | GCTCCAAAAT | GAAGTGAATG | GGGATGACAG | TGGCAGAGCC | 29460 |
| AGTCACATAA | CCTTCTCAGC | GTCAATAAAA | TTCCCTGGGC | TGTAAGTGAA | TAGTCCCATC | 29520 |
| TGTTATGCAC | ATTTGTTTAT | CACAAAGCTT | GAGAGTTTAT | ACATAACGAG | CTGCCTTTGA | 29580 |
| ATTAAGGTAT | TGCACATCCA | AGGATTCTCT | TTTAATACAT | TTGAGAGATG | GTACTTTAAA | 29640 |
| TGAGCACTTC | GACTAATTCC | CTAGTGTAAT | GTCTACTTGG | AAATGTTATT | GCTATGTGTC | 29700 |
| ACTAGGTCCT | GCCTTCACAT | ATGTTCAACT | TAAAAAAAAA | AAAAAACTAC | GTGGGGTGCA | 29760 |
| GTGGCTCACG | CCTGTAGTCC | CAGCATTTTG | GGAGGCTAAG | GCAGGTGGAT | CACTTGAGGT | 29820 |
| CAGGAGTTTG | AGACCAGCCT | GGTCAACATG | GTGAAACCCC | ATCTCTACTA | AAAATACAAA | 29880 |
| AATTACCCAG | GCATGGTGAT | GCATGCCTGT | AATCCCAGCT | ACTCGGGAGG | CTGAGTCAGG | 29940 |
| AGAATCACTT | GAACCCAGGA | GGCAGAGGTT | GCAATGAGCC | AAGATCATGT | CACTGTACTC | 30000 |
| CAGCCTGGGT | GACAGAATGA | GACTCAATCT | CAAAAAAAAA | AAAAAATTA | ATATGTAGAA | 30060 |
| CTATTTTTAC | AAAGCTTGCA | GGTGATGTGG | TGCTGGAAGA | TATTCAATAT | ATTGAAAGGA | 30120 |
| CAAATTTTTT | CTTTAAAAGC | ATCCCCATAA | AATGGAACAA | CCACAGACCA | ATATTGAAAG | 30180 |
| GGTTCCCATG | TGCATGATAG | ATTGGATTTT | TCCTGCTTAT | TTGAAGAAAA | GCACTAAAGT | 30240 |
| GAAAGAAAGA | GAAAACCTGT | GAAGACACAG | ATAAAAATAT | AATGGAAGAA | ATAATTTTA | 30300 |
| ATGGCCAAAA | AAGCTCACAG | ATAAGAGTGG | TGGTCTGGGA | AATAATTATT | TCCATTTTAC | 30360 |
| TGGAGGTTTC | CAAGCTCAGG | AGAAAGAGCC | AGCCGCTTGG | TGAGAATATT | ATAGTAGGGA | 30420 |
| TTCATACATA | GGTTGGTTTA | AAATGACTTT | CCCGGGCCAG | GCGTGGTGGC | CCATGCCTGT | 30480 |
| AATCCCAGCA | CTTTGGGAGG | CCGAGGCCGG | TGGATCACGA | GGTCAGGAGA | TCGAGACCAT | 30540 |
| CCTGGCTAAC | ACGGCGAAAC | TCCATCTCTA | CTAAAAATAC | AAAAATTCAT | CTGGGCATGG | 30600 |
| TGGTGTGTGC | CTGTAGTCCA | AGCTACTCGG | GAGGCTGAGG | CAGGAGAATC | ACTTGAACCC | 30660 |
| GGGAGGCAGA | GGTTGCAGTG | AGCCGAGATC | GCACCACTGC | ACTCCAGCCT | GTGAGACAGA | 30720 |
| GCAAGACTCA | GTCAAAAAAA | AAAAAAAAA | AGACTTTCCC | AAAACTATT | CCACTCCCTA | 30780 |
| GATCCCAGGA | TTTATTGCTT | ATTTGGCTTA | ATTTCTCACA | GATGATTTCA | TGGGGCTAAG | 30840 |
| GAAAAGCAA | CAGGATCAGG | GGCTGGAGCT | GGCTCCAATG | TTACACTGGG | AGTATCTTTA | 30900 |
| CGAAGGGTCA | GTGTGATGCA | GAGATGTGTA | AATGTGTCGG | AATAAGCTTC | AGCTTATTAA | 30960 |
| CATAGCCTGC | AAACAAGAGC | AGTGGCTTTA | CCTTTCCTGG | TGGCAGGCTT | CCCGTCCATT | 31020 |
| TAGCTTCTGT | GGGAAATGGT | ACCACGCTTT | GTGGTGGAGT | TTCCCTGTGC | CCTGAATCTC | 31080 |
| TTTTACTACG | ACAGTCTTTT | ATCTATGGAG | AGAACATAAT | CCAAAACATA | ATACACAAAT | 31140 |
| AATTTCCCCT | TGTTAATGTT | GCCTCCTCTT | AGCATCAGTA | AAAGTTTTGA | CCCAACACAG | 31200 |
| CTCTATAACT | TACATTTTAT | GGGGCACTAC | TGGTATGCTT | TTGGTTACAG | GATTGTTAAA | 31260 |
| AGGAAATCTG | GCTGTAAGTT | CCAGCTGTGT | GACCTAGAGC | TAGTCATTTA | AATTCTCTAA | 31320 |
| TCATTCATTT | CCTCATCTGT | TCAATAAAGA | TAAGGCTCCT | TTCTTAGTGC | AGCTGGAAGA | 31380 |
| ATTAAATGAA | AAATTGCATG | TACTTTATCA | AACCACAGAG | AAGCATGCGA | AGGTGAAGAG | 31440 |
| TGGTATTGCT | TGTAGCAGAC | CATAAGACAG | GACAATTAAA | CTAAGCTCAA | GAGCTAAGGA | 31500 |

| | | | | | |
|---|---|---|---|---|---|
| GGAAGGTTCC | AGAGCGGTCT | TTCCTTTCAT | TCTGATGGTG | TTTCTCTCCC | CTCTGTACCA | 31560 |
| CCAGAACAAT | GTTCCATGTG | CCTTCGAACA | TGAAGGATGA | CATTACATAA | CACTAATATG | 31620 |
| TATTACATTT | AAAAGTTTAA | AATGTTTATT | CTCATGTTTG | CTACACACAA | TGTGGACACT | 31680 |
| TGCTTGGACT | GACAAAGTCT | TCATATCACC | TAGAAAATTA | TAATGAACAG | GGACTAATTA | 31740 |
| CTACAATTGT | GAATAAATCC | AGCTATTGTG | ACAGGCAAAG | AGAATTCATG | GCTCTAAATA | 31800 |
| TGGACATGTT | TAATTTAATA | TTTGTATACT | AATCAAATTA | TCTTTGGGGA | TGCATACATT | 31860 |
| TGTTTCTTTT | AGGAAAAATC | CATATCCTAA | GAATATCATC | AATTTTCCAT | TCATTCCTAA | 31920 |
| ATTGAAGCTT | CTATGACTTT | ATTTTTTAAA | TTGCTTAAAA | TCCTTCAAGA | CATCTGAAAT | 31980 |
| TTCTGTGACT | TTAAAAACAC | ATGTATCGGC | CGGGTGCAGT | GGCTCACACC | TGTAATCCCA | 32040 |
| GCACTTTGGG | AGACTGAGGT | GGGTGGATCA | CTTGAGGTCA | GGTGTTCGAG | ATCATCCTGG | 32100 |
| CCAACATGGT | GAAACCCCAT | CTCTACTAAA | AATACAAAAA | CAGCCGGGTG | TGGTGGCACA | 32160 |
| TGCCTGTAGA | CCCTGCTACT | AAGGAGGCTG | AGGCAGGATA | ATTGCTTGAA | CCCAAGAGGC | 32220 |
| AAAGGTTGCA | GTGAGCCAAG | ATCGTGCCAC | TGCACTACAG | CTTGGGGGAC | AGAGCAGGAA | 32280 |
| TCCGTCTCAA | AACAAACAAA | CAAAAAAACA | CATATATCAA | ACCTCTATTT | TATCATTCAA | 32340 |
| GGCTTTGCAC | TGTTTTTGCA | CACAAAATTT | AAAAGACTTG | TCCGTACTTT | AAAGATATTC | 32400 |
| ATAATCTGTG | ACCTTAGGAT | GAAGGATTAT | AAAGAAAGGC | ATAGATGAAA | AATTGTGTCC | 32460 |
| AAAAATATCC | TTTGTAGTAT | TACTCATGAC | TGCATAATGT | TAGAGATAAA | TTAACCTAAT | 32520 |
| AATGAGAGTC | TGGCAAGTCA | ATTTGATAGA | TTATTGTGAT | GGAAGCTATT | TTAAAATGTT | 32580 |
| TTCGACAATA | TTGAATTACA | TTAGAAAAAT | GCTAGTACTC | TAGTGTACAA | AGCAGGATAC | 32640 |
| GCTGTGCACA | TCCACATACA | GGAATAGAAA | CTGATTCACA | CAAGTGCCAG | TAATGACTAT | 32700 |
| TTCTGGGTTA | CAAAACAGGA | TGATCACTTC | ATTCTTTGTG | ACTTTCTATA | TTTACCAAGT | 32760 |
| GATTTTGTAA | ATAATTAGTA | GATACTCATT | TTATATTCAG | AAGTAGCTAA | ATGTATTTAA | 32820 |
| AAGAGCAATA | ATTGGACTTC | ATCAGCATGG | CAAGTATAGT | TTTCTGCTTT | CCAAATATCT | 32880 |
| CTAGAATTCT | GGGAATAGTA | TCTCTCCATC | TAAATTTTGA | ATTTGGGTG | TTTGGAGATT | 32940 |
| TTATTGTTGT | TGTTGTTGTT | GTTTTGTACA | ATGGACCCAA | ATGGAGGCCC | AATTGCTAGT | 33000 |
| AAGATCAGGT | CAGCACCAGG | ACAGATACTG | GTTGTTGCTC | TGCCTTAGAA | GGCCTCCAAG | 33060 |
| TCTTGCTAAC | ATCTGGATAT | CAGGAGTTCA | GCTCATTGCT | CTACACTCAG | ATCCTAGCTG | 33120 |
| AAGTCATCTG | TGGTCAAACC | CAGAGTTTGG | ACCATTTCT | ATTTGATTTC | ACTTTTTATG | 33180 |
| CAAGATCCCG | TGGCTTGGCT | GAAGGCAACT | CTTTAACTGT | ACATGCAGCT | GCAATTACTT | 33240 |
| ACACTCCACT | TAAAGCTTTC | CCACCAACTT | CTCCAATCTT | ATAAACACTG | AAAGCTGAAA | 33300 |
| GAGACTCAGA | GATCCTCTGG | CCCAACTGTT | TATTTATTG | ATAAGAAAAT | TTGCGTAGAA | 33360 |
| AATTTGAAAA | GTTGCCTGAA | ACCACATGAT | GCACAGAGCC | AGCACCAGAT | CCCCTAATGC | 33420 |
| CTAGACTACT | GCTTGTTCTA | CCTATTACAA | CTTCCCCTTT | GTTTTCGTAA | TATTTAATC | 33480 |
| ACAAGCTTAA | AACTCAATGG | GGTAGCTCCA | TTTTGAGGTA | TTATAAAGGA | GAATTTGTAT | 33540 |
| ATTTTAAATC | AAGTTTTAAT | CATTTATTCT | AGAAGGAAGT | TTGATAATGA | AAAATACTTT | 33600 |
| TAGGTTGAGC | TTTGAATATT | AAACATAAAC | ACAACAAAAC | TACTTCTCCT | TGCTCTTTAT | 33660 |
| GTTACTGGAA | TTGTATCACA | AACCCATCAC | TTTAGTTTTT | CTTCCCATTC | TCTGTTGCTG | 33720 |
| TCTAACGAGA | AAGGATGAAA | AGCCCTACTT | AAGTTTTATG | GTTTCAAATG | CTACTTTGAT | 33780 |
| TTTGTATCAA | TAGGTAATTT | CAGTTCTTCG | TTTCCTATTT | TCCTTTGCAT | GAGACGAATG | 33840 |
| CAGAAATCAG | GCTAACATAC | CAAACCATCC | TAAACTGAGG | TCTTTCATGG | TAATGGGAAA | 33900 |

-continued

| | | | | | | |
|---|---|---|---|---|---|---|
| TGTTTTTCCA | AAATAAGCAC | AGAAGCTAAT | AAAATTATGG | AGGCTGAACA | CTGGCATGGT | 33960 |
| TGATATGTAC | TTAGAGACAC | TGGAATAATT | ATTAACCTAT | TTGCAAACAA | TTGAGAACAT | 34020 |
| GTAACAGTGT | CAGAACCCTT | CCCTTTAAGG | AGATATACCT | CTAAAAAAAA | ATTGTGAATT | 34080 |
| CTAGTGCCAA | AGTTGTAAGT | AGACACAGAA | AAATGAATTG | AAATTAAGTT | AAAGGAAAAT | 34140 |
| GTTATATTAA | AAAAAATTAC | TTGACACAGT | ATAGGTTGAA | TTTGAGAAAA | AAATAAATAA | 34200 |
| TGTAAATATT | ATGGTATACG | CATAAGCAAA | AAAACAGGTT | TTTCCCTTTT | TTTAAGTCTA | 34260 |
| GAACTCATGA | TTTTATTATA | ATGGTCGTTA | GATTGCTCTT | AGATTCTCCT | AATATCCAGC | 34320 |
| CTGTCTTGCT | TCATCTCTGT | TAGCCCAGAG | TCCTAGTTTA | CTCAGAGTAA | ATGTTACACC | 34380 |
| TAGATCAAAG | AGCATGAACC | TGCAGTGGGA | GGATATTCAA | GGACTGAATT | CTGCTCTGCC | 34440 |
| ATTCCCAAAT | TGAGTAAACC | AGGTAAAGTT | TCAAAAACTC | TTAGGGCTTT | CACTGTTTCA | 34500 |
| TAGGAAGAAT | TGGGATAATG | TTACTTCACT | GGGCAGTTTG | GAGTGAAAAC | AAAAGTATGA | 34560 |
| GACATGCCTC | GTAAATTGCA | AAGTGTTATA | TGTTGTATAA | TATTCTAGAT | ACTAGCAACA | 34620 |
| GCAATAATAA | TAAACAGTCA | CAATATTGGC | AGTCTAGCCC | TCTCAGATCC | ATAAATACAG | 34680 |
| GCCTACAGCA | AATGAAATGT | ATTTCTATAA | AAGTGCCTTT | GATTGGTTGT | TAAATTGGTT | 34740 |
| TTAAATGTTT | CTTTTTTAAA | GTGGATTCTT | CTGGCCTGGA | ATCCTCAAGA | TGAGTGGGGA | 34800 |
| GGAGTTCACC | AGAAAACATA | GAAGCAATTC | CTTCAGTGTT | AGAAAACTG | AGGGCCCTCT | 34860 |
| CATCATCTGC | CTATCTTTCT | GAGAAATTGG | TGCTGACCAC | AATGTCCCTG | GGTGCCTTTT | 34920 |
| CTTAGCTGTA | CAATGAGGGC | AACAAGCTAG | GTGATCTCTA | CAAGCGTACA | ATTTCTTGC | 34980 |
| CTTCAGTCTT | ATTCATAACT | TTGGTCATGT | TCTCCTTTTC | TTTTATTATT | ATTATTTTT | 35040 |
| TGAGACAGAG | TCTTACTCTG | TCACCTAGGC | TGGAGTGCAG | TGGTATGATC | TCAACTACTG | 35100 |
| CAACCTCTAC | GTCCTGGGTT | CAAGCAATTC | TCCTGCCTCA | GCCTTCTGAA | TAGCTGGCAC | 35160 |
| GCGCACTATG | CATGCGCATA | GGTGCACGCG | CCGCTACGCC | CTGCTAATTT | TTGTATTTTT | 35220 |
| AGTGGAGACA | GGGTTTCACC | ATGTTGGCCA | GGCTGGTCTC | AAACTCCTGA | CCTCAAGTGA | 35280 |
| TCTGCCCGCC | TCAGCCTGCC | AAAGTGCTGG | GATTACAGGC | GTGAGCCACC | AGGCCCGGCC | 35340 |
| ATGTTCTCCT | TTTCCTGAGA | GACCATTTCA | AATTCATATA | GAAGTCTGAA | AAGACTCGTT | 35400 |
| AGCCACAGTC | CCAAACACAA | ATCTTGTCAG | TTCTGATCAG | TATTTCATTC | CACAGCCAAT | 35460 |
| CCCAGTCTGA | CTAATCACAG | CATCACAGTT | AATACTCACA | GCGTCCTTGG | AGAAATGACC | 35520 |
| ATTGTCCACA | GTGTCCATTG | GTACCAGTGG | CTTCTCAAGC | CTTGCCCTAG | GGTCTTCATT | 35580 |
| GAATCAGTTA | TCTTTTTCAG | AGAGTCTCTT | CATTTTGGAA | TTAGGCAATA | TTACCAGATG | 35640 |
| GAGATCCTTA | TGTTGCTGTT | AATGTCTTTT | CTCTGACTTC | TCCTAAAACT | GTTCCCTCCC | 35700 |
| CTTAATGGAC | CTTTGGTAAG | TTAGTAATAA | TCCTTCTACC | CAAAAGAAG | AAAAGCACTT | 35760 |
| ACCTTCACCA | TTAAACCAGT | ATTTTAAGCC | CTAGACTATA | AGGCTAACTT | GGAAAAGGAG | 35820 |
| GGAGTTTTCT | GTCCCTTCTT | CCCTTTCAAA | TACTTTTGCA | GATTTTTACA | GGGATAAATA | 35880 |
| GTGAGCCACG | TGGCAGTCAG | ACGGCAACAG | GTTGGCCCC | ACTTCTCAG | AAAGCCTCGG | 35940 |
| CTTGGTTTTG | CCGCTTAATT | TTTAACTTCA | TTTTCAAGTT | CTCACTGTTA | GAGTATCTCA | 36000 |
| AAAGATGTCA | TCGTGTGTTT | CTGCTTTGAA | CTGTGCATAC | AACCATTCAG | TCAACAAGCC | 36060 |
| TTTTTTTCTG | AAAGCAAGGG | GGCATGGTGT | GGAGGAAAGG | GCAGGGCTCC | TGAAATCAGT | 36120 |
| GATGGAGTCA | GACCCATATT | CACTTCCTAG | TGTTTTCCCT | GAGCTTGGAC | AAGTCACTGA | 36180 |
| ACCTCTTTGA | ATTGGCTTCC | GCTTTAGTAA | AGCAAGGATT | GTGTTACTGT | ACTCATGGGG | 36240 |
| TTATTGAACA | AATGAAATAC | ATATTCTAAT | TGGTAGTAGC | TCCTCAATAA | ATGAGGTGTT | 36300 |

| | | | | | | |
|---|---|---|---|---|---|---|
| CATTCCTCTT | CAGGAGTTCA | GTTAAGTCAG | CTAGATTTTC | CATATGCATT | TGGTGCCCAC | 36360 |
| AGCCTAATGA | ATGTGAACTG | TGACTGCCCT | GGCAACTTCC | CAGGAAGCTG | CCTTGTACCC | 36420 |
| CTCCTTCCTG | TTTCATATCA | TCCATGTCTT | CCCTAATCCA | TTTTCTGCTT | GGCTCCCGAC | 36480 |
| TCTTGGAATT | GTGTCCTATT | TGTAATCATT | AATTTTGAGA | CTGTGGTTGC | TATTGGATCT | 36540 |
| TCCTAGTGTG | ACGCAACCCT | TATAAAATGA | AATGAGAGCC | TTCCCTCTCT | GGCTTATCAG | 36600 |
| CTTCAGACTT | CCTTAATTGA | GTTCCGCCAT | CCTAGTGAGT | CTCACCATAC | TCCCGAAATA | 36660 |
| ACCTGCTGGA | GTAGGCTTAT | CCTACTCAAC | TCCTCAGATC | TCTGTATTTA | ATTCTATTTT | 36720 |
| ATTGCTGTTG | TAGTAAATTA | CCACAACTGT | GATGGCTTGA | AACAACACAA | AATTATTTAT | 36780 |
| TTATTTACAA | TTCTAAAGGT | CAGAAGTCCA | AAATGGGTTT | CACTGAGCCA | AAATCAAGGT | 36840 |
| ATTGGCAAGG | TTGTGCCCCC | TCCAGAGGCT | TTAGGGGAAA | ATCCATTTCT | TTTTCTTTTC | 36900 |
| AGCTTGTAGT | GACCACTGCA | TTTTTGGCT | CTTGGCCTTT | CCTCCACCTT | AAAGCCAGCA | 36960 |
| GTGTAACATC | TTGAAGTATT | TTTCTCTTAT | TCTGACTCTT | CTGCCTGTCT | CTTATAAGGA | 37020 |
| CCCTTGTGAT | TACACTAGGG | CCCATCTGCA | AAATTCAGGA | AAATCTGCCC | ATCTCAAAAT | 37080 |
| TCTTAACTTA | TTAAACATGT | AAAGTCCCTT | TTGTCATATA | AGGTAATATA | TTTACAGGTT | 37140 |
| CTGGGGATTA | GGACATGGAT | ATCTTTGGAG | GACAACATTC | AGCCTACCCT | TTGAGGGAT | 37200 |
| AGAGGGGTAG | CAGGAAGAGT | TGAAACAATT | CCTTCCTTTC | TTTATTTAAA | AATTCTGGTT | 37260 |
| ATTGATTTAT | TATAGTTATC | ATGTGCCTGA | TAAGCCAATG | AAAATAGTTA | TAATGGCCAG | 37320 |
| GGGCAGTGGC | TCATGCCTGT | AATCCCAGGA | CTTTGGGAGG | CTGAGGCAGG | AGAATCGCAT | 37380 |
| AAGCCCAGGA | ATCCAAGACC | AGCCTTAGCA | ACATAGGGAG | ATCCGTCTC | CACAAAAAAA | 37440 |
| TGCAAAAATT | AGCTTGATGT | TGTGGCACAT | GCCTATAGTC | CCAGCTACTC | AGGAGGATTG | 37500 |
| CTTGAGCCCT | GGAGTTCAAG | GCTGCAGTGA | GCTGAGATTG | CACCACTGCA | CTCCAGCCTA | 37560 |
| GGCAATAGAG | CAAGACCCTG | TCAGAAAGAA | AAAGAAAGAA | AGAAAGAAAG | AAAGAAAGAA | 37620 |
| AGAAAGAAAG | AAAGAGAGAG | AGAGAAAGAA | AGAAAGAGAA | AGAGAGAAAG | AAAGAAAGAG | 37680 |
| AGAAAGAGAA | GAAAGGAGAA | CTTTCTTGGC | TTAATTTACC | CAAAAGGTAT | GATATTTTCT | 37740 |
| TAATTTGCAT | AAGGCAGAGC | ATGAGCTGAT | ACCAGTTCTG | GTAGAAAAAG | TAGGTGAGAC | 37800 |
| TGGATCCCCC | AAACAAGAGT | AAATATTTAA | TATAATAAGG | AAAGAGTGGC | CGAAAGTATT | 37860 |
| CAATGCCACA | AGTAAGATTC | AGAGTAGATT | TTTCAAACTG | CATAATTTGT | TTAAAAAGCA | 37920 |
| TAATTTTATA | GCTGGATTTT | GCAAGCTCTC | TGAGGGGATC | TTGTTCATTT | TGAGAATCAC | 37980 |
| TATATCCACA | ATTCTTGGCA | CAGTGTCTGT | CCTATGGTGT | GTGCTATGAT | CCAAATGTCT | 38040 |
| GTATCCTCTC | AAAACTCATG | TTGAAATCCT | AACCCACAAA | GTGATAATAT | TAGAAGGAGG | 38100 |
| GGTCTTTGGG | CAGTAGTTAT | ACCATGAGGG | CAGAAACCTC | ATCACTAGGA | TTAGTGTCCT | 38160 |
| TATAAAAGAA | ACCCAAGGAA | GTTTATTCAA | CCCTTCTGCC | ATGTTAGGAC | TCAGCAAAAA | 38220 |
| GATGGCTACC | TGTCCTCACC | AGACACTAAA | TTTGCCAGGG | CCTTAATCTT | AGACTTCCCA | 38280 |
| CCTCCAGAAC | TGTAAGAAAT | AAATTTTTTG | TTGTTTATAA | GTCACCCAGT | TTATGATATT | 38340 |
| TTGTTACAGC | AGTCTGAACA | GACTAAGACA | GTACACGCTT | AATAAACATT | AGTTTACTGA | 38400 |
| ATGAATGAAT | TCTTGCATTG | CTTCACCACC | AACAATCAAG | ATCTCTGTAG | CTGGTTTAAC | 38460 |
| CCCCTCACTC | CCAATCATGA | TTTTCATATA | ACAAAGTTAA | CTCAGTTAAA | TCAACTCAAT | 38520 |
| AAGGTATACA | TTAAATGAAA | TTAAGAAGT | TGTAACATTT | ATAAACATCA | AGAGTAATGT | 38580 |
| AGAAGAAAAG | TCCAGAGATC | CTTAAAAATT | TAAGCCTCTC | TGGCCTGACA | TTAACAGCTA | 38640 |
| AGGCAGGAAC | AGAAAACCAA | ACACCTCATG | TTCTCACTTA | TGAGTGGGAG | CTGAACAATG | 38700 |

| | | | | | | |
|---|---|---|---|---|---|---|
| AGAACATGTG | GACACAGGGA | GGGGAACAAC | ACTCACTGGG | GCCTGTTGGG | GGAGGATGGG | 38760 |
| GTGGGGGTGT | GGGAGAACAT | TAGGTAAAAG | AGCTAATGCA | TGCTGTACTT | AATACCTAGG | 38820 |
| TGATGGGTTG | ATAGGTGCAG | CAAATCACCA | TGGCACACGT | TTACCTATGT | AACAAACCTG | 38880 |
| CACATCCTGT | ACTTGTACCC | AGGAACTTAA | AAAATAATAA | TTTTTAAAA | AACAGCTATT | 38940 |
| TCCAATCAGA | GCAGTTCAAT | TCCATACAAT | TATTATTATT | ATTATTATTA | TTATTATTAT | 39000 |
| TATTATTTTG | AGATGGAGTC | TCACTGTCGC | CCAGGCTGGA | GTGCAGTGGC | ATGATCTCAG | 39060 |
| CTCATTGCAA | TCTCTGCCTC | CCAGGTTCAA | GTGATCCTCC | CGCTTCAGCC | TCCTGAGTAG | 39120 |
| CTGGGATTAC | AGGTGGGCAC | CACCACGCCT | GGCTACTTTT | TGTATTTTTA | GTAGAGATGA | 39180 |
| GGTTTCACCA | TTTTGGCCAG | GCTGGTCTTG | AATTTCTGAC | CTCATGTGAT | CCTCCTGCCT | 39240 |
| CGGCCTCCCA | AAGTGCTGGG | ATTACGGGCT | TGATCCACTG | CGCCCAGCCA | ACATACTATA | 39300 |
| TTTTTTTTG | ATAAATTTTC | TGTATTCTAG | ACATGACATT | AGCTTCCGAC | AATATTAATT | 39360 |
| TATTAAGATC | TGACCCATGA | CATGACTTCA | TAAGAGTTCA | GAGTCCACTG | AATGAGACCA | 39420 |
| CACACAGAGA | CAGACAACTA | GAATGAAGGA | TGATAAACAT | GAACAATACA | AACTTGCACA | 39480 |
| GGTGACTAGA | AAAGAACAAA | TGAAGACTCC | TGCCAACTGG | GGGTATCAGG | GGAAGGCTTC | 39540 |
| CCAGGCAGAA | CAGGGCTGCG | CCAGTCTCCA | TGTGTGGTAT | GAATAAGTCA | GTAATACAGG | 39600 |
| GGAAGCACCT | TCCAGAAAGA | GCAAACCCGT | TGAGGCTTGG | TGTGAGGAAT | AAGAAGTGTC | 39660 |
| CAACATGACT | GGGGATTAAA | GTACAAAGGT | ATAAAGGAAA | TGTGGTGAAC | TGACTGGAAA | 39720 |
| GATAAGAATT | TTTTTTAACA | GTTACTTTTC | CAATAGTAG | AATTAACTAG | ACAGGAATAG | 39780 |
| AAATGGAAGA | AGTTTTTATG | TTCCCTTAGA | ATGAAAACTA | TACATTTTTT | AAGAATTATA | 39840 |
| TGAACAAGGA | AAATGTGACT | CAAAGGCAGA | AAATGATAGA | ATTTATTAT | AGGGCAGAAA | 39900 |
| ACAGGATCTG | GCTAAATTAA | ACTAAGTACT | CTACTATACT | ATACCATATG | CTATATTCTT | 39960 |
| GAATGGGAGA | AGTAATACCA | TAAAAACTAT | TGATTCTTCC | TAAATTAGTA | AACACATTGA | 40020 |
| GTGAAAATCC | AAGAGGAAGA | AAGAAAAATG | GAAGACAAAC | TGGAAATAGC | CCAAATTTTC | 40080 |
| ATCAGTGGAA | GACTGAGTAC | TTTGTGATAC | ATAGTCATTG | CAGAAAAATA | ACACAGTTAA | 40140 |
| AAAGAATGAA | TCACATCTAT | AACATTTGAC | CTGAATACTT | TCATATAATG | TAATACATTT | 40200 |
| TTAAATGAGT | AAAGCAGATA | CTAAGGACGT | ATAAAGGGAC | TCCATTTTTT | TCTGAATATT | 40260 |
| AATCAAGAAA | ATTCTATATA | TCTGTATCTT | TGTTTACATA | AGATTGTGTG | AGCCATAATA | 40320 |
| GCTGTTGACT | TGGGTTATCA | GGTTTGGGTA | AACAGTTTAG | TGGTAAAAAA | AAGATGTGTA | 40380 |
| AGACTTGGCC | GGGTGCAGTG | GCTCACATCT | GTAATCCCAG | AACTTTGGGA | ATCTGAGGCA | 40440 |
| GGCAGATCAC | TTGAGGTCAG | GAGTTCCAGA | CCAGCTTGGC | CAACATGGTG | AAACCTCGTC | 40500 |
| TCTATAAAAA | AACTACAAAA | ATTAGCCAGG | CATGGTGGCG | CACACCTGTA | GTACCAGCTA | 40560 |
| CTCAGGAGGC | TAAGGCAGGA | GAACCGCTTG | AACCCGGGAG | GTCGAGGTTG | CAGTGAGGTG | 40620 |
| AGATCGCGCT | ACTGCACTAA | GCCTGGGCAA | TGACAACAAA | ACTCCGTCTC | AAAAAAAAA | 40680 |
| AAAAAAGTG | TAAGACTTAG | CAAAAGGTG | ACCAAAAAA | AGCAACATTT | ATAAACTATG | 40740 |
| GATGTAAAAC | TCTATGTATG | TGTGAGTGTG | TATACATGTG | TGAATATACA | TAGGATACAT | 40800 |
| TTTTGTCTGT | ATGTGTATAT | GTACATACAT | GCATGTATGT | GTATGTGTGT | GTATATATAC | 40860 |
| AAGCTTTTTT | AAAATGTTTT | CAACAATATT | GAATTACATT | AGAAAAATGC | TAGTACTGTA | 40920 |
| GTGTACAAAG | CAGGATGCGT | TGTGCACATC | CACATACAGG | AATAGAAACA | GATATATACA | 40980 |
| TACACACACA | CTACACACAC | CCCTATACCT | ACACCAAATA | TACATTGAGA | GAGAGAGATA | 41040 |
| GAGAAAATAG | TAACTAAGGT | AGTTAATTCT | GGCCACAAGG | ATTTTTAGAT | GAATCTGACT | 41100 |

-continued

```
TTCTTCCTTA GGTTTTTTTT GTATTGTTTA AAGTTTCACA CAAATAGCAT TTATTTACTG   41160
TATAATCATA AAAGGCAAAA ACCTATTTTG ATTTTAGGAA AACACAAAGC ATCCAAACCA   41220
AAAATCTCAA CTTAGGAAAT AGCGGGAAAT CTAGGGAAGT CAACAGGACC AGGTCATGAC   41280
GGTCTTTTAT GCAATGTCCA GGAGCTTGAA CTTTATCTTG TCGTTCCTAT ATTTCCTCAA   41340
AACAAATGTG TGTGGACGCA GAAATGGAAA TGCACAGCAG TGCACTGAGG TCACAGGAAA   41400
AATACAAAAC AGTTTTTCTG AAGTACTAAC TTCACTCAAA ACTTCGGGAA ACATTTTAAA   41460
AATGGTTTTA AACAAATTTG ACTAAATTTG ACAAATTTAG TCAAATGCAA AATTTTCATT   41520
TTTAAAAGGA AATAAATTTT AGAGGAAAAA ACAGATGTGA AAAAGAATAC ATGAAATAGT   41580
ACATGAAGGA ATACATGCAC GTGGCATACA CTTGAATCCA TGTATATGCC AGGTTTTCTT   41640
GTGTTGCACA CAAGACCAAC TCTGAAGTTA AAGATAACCC AGTAGAAAAA ATTAAATGAT   41700
GGGGAGTAAT TAAAATGTTT TCAGCAGGAG TAGGACATGA TTTTTATATT TAGACTGTTT   41760
AGTCGGCTAG TTATGTCTGA CGGATAGAAG TGAGGACACT CCTAATTGAA AAGTAAGTGC   41820
TACTAAGAAA CTAACGTGGG GGTCATAGA ATGAAGCCAG ACTTTTGTTC CCAAGCAGGA    41880
GACAGATGCA GATAAGAGGG AATGAAGATG AAGTAAGGGC TGAACCACAG AAGCTTCGCA   41940
TCATAAGTCA TTGTATTTCT CTGAGTGAAC ATCATAGAAC TTATTTACTA TCTGGTCACA   42000
AAATGCCACT GACATGAAAA GAAATCGGGT TGAAATGGCT CTAGACCAAG ATTCCCAAGA   42060
CATCAAGAAA TCACCAAAAG TTGCCTCAGG TTCACAAAAA AAGATATTCC AAGGGAGTTC   42120
TCCAAGTAAG TAAACACTCA TTATTTCTAT AAGGCTTAGG CCACAAGACC TTGGCTGAGA   42180
CCCCTGTCTC TGTGATCTGG TCTGTACCAC ATTGGAAGGG CCATGACTGA TTTCTACCTA   42240
GACATTTAAG GCTGAACGGA GGCTGAAGAA CCTCTTGCTT GCTTTCCCAT AGACTCACAT   42300
CTGATAACAG CCCTCATCTT AGGCCCCAGA GGGCAAGAAG AGGTTAAGAA GGATCAACCA   42360
AAGGTAAAGT ACACCAAGAA AAGAGCAGCT CTTTGGTTAG AATTTTAAGA TAAAGAGAGA   42420
CACATAAAAG CTACTGTTGA AAAATAACAG AAGGAACAAC GTTTTATCTA ATCAATAGAT   42480
GGAACAAGAC AATAGAGGAC CATCTCAACA ATAACCTAGA ATACCATGGA AGACAGACAT   42540
AAATCATCTG TATTTGTCCT GCTCAAGACT TGCCATATGC CAGGTATGGT GGCTTATACC   42600
TATAATCCCA GAACTTTTAG GCTAAGGCAG GAGAATTGCT TGAGCGCAGG AGTTCCAGAC   42660
CAGCTTGTCT CTACAAAGTT CTCTGGGGGT TTTTTTTCGT TTGTTTGTTT TTTAGGCAGG   42720
TGTGATGGCA CACACTTGTG GTCCCAGCTA CTCAGGATGC TGAGGTGGGA GAACAGATTG   42780
ATTCTGGGAG GTCAAGGCTG CAGTGAGCTA TGATTGCTCC ACTGCACTCC ACCCTGGGTG   42840
ACAGGAACTG CAGACAGCCT CTAGAAGTTG AATCAGCCTC TACCAAGAAG CTTCTACCGG   42900
TGCAAAGAAC TGAATTTTTC AACAAACCTG AGGGAGCTTG GAAGTGGAAA TTTCCACAAT   42960
CAAGCCTCTG ATGAGAATTC AGACTCAGCC AACACCTGGA TTGCAGCCAC ATGAGGCTTG   43020
AAGCAGGGAA CCCAGTTAAG CCATGTCAGA ACTTCTATCC ACAGACCTTA GGTAATAATA   43080
AATGTGTGTT GCTTTAAGCC ACTAAGTTTT TGCTAATTTG TTTTGTAACA ATTATATATA   43140
ACTAGTACAC ATGAATAGTA GAATCTAATA TCAGCCATTG ACTTCAATGA AGGAAAAAAC   43200
AGATGTGAAA AAGAATACAT GAAATAGTAC ATGAAAGAAT ACCTGCACAT GGCATACACT   43260
TGAATCCATG TATATGCCAG GCTTTCTTGT GTTGCACACC CAGACCAACC CTGTAGTTAA   43320
AGATAACACA GTAGAAAAAC TGAAGAGTTA CTGAGAGTAA TTAAAATGTC TTAAGCAGGA   43380
GTGGGGCATG ATTTTTATTT TTAGACCGTT TAGTCTGCTA GTTATATCTG ATGGTTAGAA   43440
GTGAGCCTAT CTCTGGTCCC ATGTTCTTAG AGAGAGTACT TTTATCTCTT TATCCATCTA   43500
```

| | | | | | | |
|---|---|---|---|---|---|---|
| ACATCTCTAA | TTTATGTAAC | ATCCCAAGTC | CTCATTAATC | CTGTGTTATT | GCTGTTGGAA | 43560 |
| GTCCATCTAT | CCCCTCAAGA | ACAGAGCCTG | AAATTCCTCT | TTGAAAAATT | TCCATTCATC | 43620 |
| ATAATCTCAA | ATTTCTCCAA | TGTCATTTTC | CACCTAAATT | TCATGTGTGA | CTTGAATCTC | 43680 |
| AAGACTATTC | ATCTGCCCCA | GGTATCTGTT | TGATGCCTGG | ATATGTCTGA | ATTATTATTA | 43740 |
| TTGTTATTAT | TATTATTTTT | TTTTAAATG | GAGTCTTGCT | CTGTCACCCA | GGCTGGAGTG | 43800 |
| CAGTGGTGCG | ATCTCAGCTC | ACTACAACCT | CTGCCTCCTG | AGTTCAAGTG | ATTGTCCTCC | 43860 |
| CTCAGCCTCC | CCAGTAGCTG | GGATTACAGG | TGCCTGGCAC | CTCGCCCAGC | TAATTTTTT | 43920 |
| GTATTCTTAG | TAGAGATGGG | TTTTCACCAT | GTTGGCCAGG | CTGGTTTTGA | ACTCCTGACC | 43980 |
| TCAAGTGATC | CACCCACCTC | AGTCTCCCAA | AGTGCTGGGA | TTACAGGTAT | GAGCCGCCAC | 44040 |
| ACCCAACCTT | AGACCTCATC | CTACCCAGCT | CACGTGTCTT | TTAATCCTTT | AGCTGAGGTT | 44100 |
| GTAGTTTTAA | CTTATTGCTG | CTTGAACCTA | TTTCAATGCA | AAAGTTCTAA | AAGAACTCAG | 44160 |
| CCACCAAAAT | TCCCTTGATT | TGCTGCACTG | TACCAAATAT | TAGTCTTAAT | GAAATACAAG | 44220 |
| ATTTGTTTCA | GGATCTCAAG | CCCAATATTT | TCAACTGTAG | GCTTCCCAGT | ATCCAAGGTT | 44280 |
| TACGCAGGAG | ATTGGCAGTG | GGTACATTCC | CAGGGTCAGT | GGTTTTATC | CAGGAAGGAA | 44340 |
| CCTCAGAATC | ACCTGGGGAA | TTTTAGCAAC | ATACACACCA | GTGTTCTCAG | GAGTGAGGCT | 44400 |
| CAGGTATGTG | GATGGCAACA | ATACTTCCCT | TATCAAAAG | CTGCCACCAC | ACCAGACAAA | 44460 |
| TGAAAACTGC | TCTTTAATTA | TACAGCTTGG | CCTTACCTAA | TGGTTCTCAA | TTTTGGATGG | 44520 |
| ACATTCAAAT | CACAAGGGTA | GTTGGTTTTT | TTGTTTTGT | TTTGTTGAGA | CAGACTCTCA | 44580 |
| CTCTGTCGCC | CAGGTTGGAG | TGCAGTGGCG | CCATCTCGGC | TCACTGCAAC | CTCCACCTCA | 44640 |
| TGAACGTAGT | TTTAAACAGC | ACTAGTGCCT | AAACCAGACT | CCAGAGATCA | TGATCCCTAA | 44700 |
| TCCTATCCCT | ACCCTGCGGT | ACTCATTCTG | AGATATGCCC | TGGGTAATAA | GAATTTTAGA | 44760 |
| AGGTACTCAG | GTGATTCTAA | TGTTCAACCA | GTCTGAGAAC | CATTCGCAGA | CTTCATATAG | 44820 |
| ATACTTTATT | CCAAACAGCT | GAGCTGGACC | ATAGCTAGAA | GAAGGAATAG | AGATGAATGA | 44880 |
| GAGTTCATAT | TTTCCATAGA | AAGCCGCTGC | CCTCTTCTAA | ATGTGAATGG | AAGTTCTGGA | 44940 |
| GACCCCTATC | CTAAGGTAGA | CAGATGACAG | ATACACTGGA | GAATGCTGAA | GGAAGCAGAT | 45000 |
| AGGAGTCTAG | GCTTTAGACC | ACACCTTCCA | AGACGTACTA | CTCATGCCTG | ATGAAGTATT | 45060 |
| ACCAAACATA | CCCCTGGGCC | AATAAACAAA | GCAGGAGCAA | ATGTGTTTGT | GTGTGTATAA | 45120 |
| CTTTCTACAC | AAAATACAGA | AAAAAGTGAT | TCAATGTTCA | GCATAAATAA | AATTTTGTGT | 45180 |
| TTAGTATTG | TTTTATTTCA | AAGTACATCT | TGGTGAGAAT | GCATTATTTT | GAACTGGATA | 45240 |
| AAAGCCCCCC | ACTACTGAAT | CCCAGGTCTC | TCTATGAAGC | CTGAATAGAG | GCACTGTAAC | 45300 |
| TCTAATGGCC | AAAGGGCTGG | CCTGGAAATT | CTCCCTTCAG | CTGCAAAAAG | AGAAAAGAA | 45360 |
| TAATCCAAGC | AAACAAACAA | AACAAAGAAA | TGAGCAAACC | ACTACAACAC | AAAACCCTTG | 45420 |
| GGATGAGATG | AGTACTAGAC | TGGGAAAGTG | ATAGCTCTGG | TATTCATGTG | TGTGTGTGTG | 45480 |
| TGTGTGTGTG | TGTGTGTGAG | AGAGAGAGAG | AGAGAGAGAG | CACATGAGAG | CACACACAAG | 45540 |
| ACCCTATAGA | GGAACCAAGT | AGCTTATCTT | CTTCCTTGGA | TTCCTCTATC | TCATAGCCTA | 45600 |
| GAAGACATGG | GGTGATCCTA | GCCCCTGGTA | GTGTAGGACA | AGGTAGAGTG | GGACTGTGGT | 45660 |
| TTTAAAATAC | TTTTTAGACC | GGGTGTGGTG | GCTCATCAAC | ACTTTCGGAG | GCGGAGGTGG | 45720 |
| GTGGATCACC | TGAGGTCAGG | AGTTTGAGAC | AAGCTTGACC | AACATGCTGA | AACCCCGTCT | 45780 |
| CTACTAAAAA | TATAAAAATT | AGCTGGGCAT | GGTGGCAGGC | ACCTGTAATC | TCAGCTACTC | 45840 |
| AGGAGTCTGA | GGCAAGAGAA | TCGCTTAAAC | ACAGGAGGCA | GAGTTTGCAG | TGAGCCAACA | 45900 |

-continued

| | | | | | | |
|---|---|---|---|---|---|---|
| TCATGCCATT | GCACTCCAGC | CTGGGTGACA | AGGGTGAAAC | TCTGACTCAA | AGTTAATTAG | 45960 |
| TTAATTAAAA | TAAAATACTT | TTTTATTTGG | GGCTGGGTGC | AGTGGCTCAT | GCCTATAATT | 46020 |
| CTAGCACTTT | GGGAGGCCAA | AGTGGGAGGA | TCACTTGGGG | CAGGAGTTT | GAGACTAGCC | 46080 |
| TGGGTGACAT | AGCAACATGC | CATCTCTACA | AAAATTTAAA | AATAAAAAT | TAGCTGAGTG | 46140 |
| CAGTGGTGCA | CACCTGAAGT | ACCAGCTACT | CATGAGCCTG | AGGTAGGGGG | AATTACTGGA | 46200 |
| GCCCAGGAAG | TTGAGGCTGC | AGTGAGCAAT | GATTGGGCCA | CTGAGCTACA | GCCTGGTGAC | 46260 |
| AGAATAAGAT | GCTGTCTCTA | AAAACAAAAA | ACAAACAAAA | AAAACCCAAA | AACCTTCTTA | 46320 |
| TTTTAAAATG | ATTTCAAACA | TATAGAAAAA | TCAGAAAAAC | AGTACAAAGA | ACACTCATAT | 46380 |
| ACTTTTTACC | TAGATTGTTA | ATATTATACA | TTTGCTTTTT | CTCTACCTAT | CCATTTATTT | 46440 |
| ATATGTCTTT | ATATCTCTTT | ATATATATAT | ATACTTACTG | AAACATTTGA | AAGTTGCAGA | 46500 |
| TAATCATCTT | CCTATATTAC | TCAATACTTT | ATCTTTAAAT | TCAAATTCAA | ATTTTACCAG | 46560 |
| CTGTCCCAAT | CATGTCTCTG | ACAACACTTT | TTCCCCTCAA | TCCAGGATCA | CAAATTGCAT | 46620 |
| TTGGTTGCTA | TCTCTTTAGT | CTCTATTAAC | CTGGAACAGT | TTCCTGGCCT | TTCTTTATCT | 46680 |
| TTCATGATAT | GAAATGACAA | TGAATTTTTA | AAGGTTAGGT | GTTTTGTAGA | TTAGTTCAGT | 46740 |
| TTTAAAACTT | CACAACAAAG | TGCCAAAGAT | GTCTTGGCAG | CAGTGCTCAA | AACAGGTTGG | 46800 |
| AGATGCATAG | GAGCCACAGA | GAAGGGTCTG | GTTCAAAGGC | CAGTGGTCGT | CTCATTACAG | 46860 |
| CACTGCTCCA | TCAGGTCTAG | GTCTGGAGAC | TTGGTAGCAC | GTCTATGGCC | CCAAAGTGTG | 46920 |
| TAGAGAATGT | TGAGAATTGC | CTAGGGTGGC | AGACTTAGAG | GAAGAAAGGT | TGGTATGAGG | 46980 |
| CCTGTCTAAA | ATTGAATTTG | GCTATAGAGT | TATGGAAGGG | TTTTAGGCCA | TGTCTGGGTG | 47040 |
| GAATCAGATT | CAGTCAGCAA | GTAAGGGGTC | TTTGGGAGGT | GAGCTTAGGC | TGTCTGGGCC | 47100 |
| CCTTCGAGGA | GGGCAGATTT | TATGGGGAAG | GGCTCTCCTA | GAAGAACCTA | GTTAGGATG | 47160 |
| AGCAAATCAC | GCAGGTTCAT | TCTCCACTTT | ACCCTAGCAC | TTCCTAGGCT | CAGTGGTGGT | 47220 |
| TTTGAACTTT | TCCCATCCCT | GCAATTACTC | CATAAAGGGA | ATGTGCAAGG | AAGAGGGGAG | 47280 |
| GAAAGAGATG | TGAGTTCTGC | CAGAGGCTTC | ACTGTTTCAT | TCCCAGATTT | ATTTGAAACC | 47340 |
| AACCCTCCTC | CTGTACTTCA | TGCTCTCCAA | GCTCATGGTC | CTGGAACTTC | ACATTTACAT | 47400 |
| AATACGGAAT | TTTTTTTATT | ACCCTTGATC | TTTATGCATG | CAATCTTTCT | GAACACCCTG | 47460 |
| GACCCCCTCC | TTCTCTTGGT | GACCTTTTCC | TTCTCCAAAA | CATGGTTCAC | CAGTTATTAC | 47520 |
| CTCTGCAGCA | GTGGTCCTTC | CAGGAGTTGC | TTGCTGCTTT | GTTCTTCTCT | CAGCCTCAAC | 47580 |
| ACTTTTTCTT | ATCTTGTTAC | AGCATTAGA | ATGTAATGTT | TTGTTTTGTT | TTTAAAACAC | 47640 |
| ATCTTGGCTT | TCTGGAAACT | TATATAGAAA | ATAATTTTTT | TTCCCTCAAT | AGATATATGG | 47700 |
| CTAGGGTCCA | GCCTAATGTC | TGCCATAGAG | AAGCCTAATG | TCCAGCCTAA | TGTCAATAAA | 47760 |
| TGTTTATTGT | GGGCATAAAG | GAATACATTT | TAAAATAATG | GAGTGTTTAG | GTAAAATTAG | 47820 |
| GATTATTAGC | TTGAGTCATT | TAAAATCATC | CACAAGAACC | AGATCAAATG | TACATGTCTT | 47880 |
| TAATACTGGT | GAAAGAAGTA | GTTACGCTGT | CTTAAAGGCA | AAACGATATG | GACATAGCCA | 47940 |
| CCAGAAATAC | AAGAGTGCCA | TCTCTTGGTA | AACCTGTTAG | CAGACAGAGA | AGACACTGAG | 48000 |
| AAGCCATGTA | AAATATACTT | GATAATGTGT | CTCTTATGTA | GGTTATGTAA | AATGTGGAAG | 48060 |
| AAAGATGGAA | ACAAATTGA | GAGACGTGGT | TATGGCATTT | TCCAGGAAAA | TTGGAAAATA | 48120 |
| TTTTCTCCTA | ATAATTCATG | CAAAATGTAA | TGATATTTTT | TAATGCAGAA | GAAACAGTG | 48180 |
| TAACAAAAAG | CATTATAATT | ATGGCAAATT | GTTGAATGCT | TTCTCCACCC | CTGCCCTTTC | 48240 |
| CACTCAGAGT | AGGAATGAAA | TAAGGATGTC | AGTTATCACA | CTTTATGTTC | AATATTATAT | 48300 |

| | | | | | | |
|---|---|---|---|---|---|---|
| GGGAGATGCT | AGCCAGTGTA | CTGTGGAAAG | AAAAATAAAT | GTTAATGTTA | GATGTTAATG | 48360 |
| GTGTAAATAT | TTCAATTGAA | AGGCAAAGAT | TGTTAGAATC | GACTTAAAAA | TGCAAGAACC | 48420 |
| AAACACGTTG | GCTAGAAGAG | AAACATCTTA | AATATAAAAA | CACAGATAAC | TTGAGAATAA | 48480 |
| ACATATTAAA | ATATATACAC | TATGCAAACA | GAAAGCATAA | AAAGACTAAA | ATGGCTATAA | 48540 |
| TAATAACAGC | TAAAATAGAG | TTTAAGACAG | AGAGTGTTAC | CAGAGACAGA | GTGATATTTT | 48600 |
| GTATTGTTAA | AGGAGTCAGT | TGCCAGCCTG | GCCAACATAG | AAAAACCCCA | TCTCTACTAA | 48660 |
| AAATACAAAA | ATTAGCCAGT | CATGGTGGTA | TGTGCCTGTA | ATCCCAGCTA | CTCGGGAGGC | 48720 |
| TGAGGCATGG | GAATTGCTTG | AACCCAGGAG | GCGGAGGTTG | CAGTGAGCCA | AGATCACACC | 48780 |
| ACCGCATTCT | ACCCTGGGTG | ACAGAGTGAG | ACTCTGTCTC | AAAAAAATAA | AATAAAATAA | 48840 |
| AAATGCCGAG | GTGGGCGGAT | CACCTGAGGT | CAGAGGTTCG | AGACCAGCCT | GGCCAACGTG | 48900 |
| GTGAAACTCT | GTCTCTAATA | AAAATACAAA | ATTAGTTTGG | CATGCTGGCA | CATGCCTGTA | 48960 |
| ATCCCAGCTA | CTTGGAGGCT | GAGTCAGGAG | ACTCGCTTGA | ACCCAGGAGG | TGGAGGTTGC | 49020 |
| AGTGAACCAA | GATTGTGCCA | CTGTACTCCA | GCCTGGGCAA | CAGAGTGAGA | CTCCATTTCA | 49080 |
| GAAAAAACAA | AAACAATGAC | AATAGAAAAG | TGTCATTTCA | TCAAGAAAAC | ATAATAATCA | 49140 |
| TAAATGTATG | ATTCTAACAA | CAGAGTTTCA | AAATACATAA | CGAAGTTTTA | AAATACATAG | 49200 |
| CAAAATGTCA | TAACAGAGTT | TCAAAATACA | TAAAGTAAAA | ATGGAAAAGA | AAAGACAAAA | 49260 |
| TAGACAATTC | TACAATCACA | TTTGGAGAGT | TTAACACCCT | TTTTTTGGTA | ATGATGCAAT | 49320 |
| AACTAGACAA | AATATCAGTA | AAGACACAGA | AGATCTGAAC | AATCCTATCT | ATTATCTTGA | 49380 |
| GCTAATTGAT | TTATAGAACA | TTATACACAA | TATCTGCATG | CACATTTTGC | TCAAGTACAC | 49440 |
| ATGATATATA | CATCATGATA | GATCATATTC | TTTTTTTCTT | TTATTTTTAG | TTGACATATA | 49500 |
| ATAACTGTAC | ATATATACGG | GATAAAGAGT | GATATTTTTA | TATGTGTACA | CAATGTGTAA | 49560 |
| TAATCAAATC | AGAGTAATTA | GTATATCCAT | CACCTTAAAC | ATTTATCATT | TATTTTGTTG | 49620 |
| TGAGTATTCA | AAATTCTTTT | CTAGCTTTTT | GAAAATATAC | AATAAATGAG | AGTTAACCAT | 49680 |
| ATGCACCCTA | CAATGGTGCA | GAACACCGGA | ACTCATTTCT | ACAATCTAGC | TGTAATTTTG | 49740 |
| TCACCATTAA | CCAACCTCTC | CCTATCCTCC | CCTCCTTGCT | ACCCTTCCCA | GCTTCCGGTA | 49800 |
| CCCACAGTTC | TGTTCTCTAA | ATCCATGAGC | TAAAAATTTT | TCTCTACTTT | CACATATGAG | 49860 |
| TGATAACATG | TAGTATTTAT | CTTTCCAATC | CTAGCTTATC | TTACTTAACA | TAATGTTCTC | 49920 |
| CAGTTTCATC | TACGTTGCCA | CAAATGACAA | GATTGCATTC | TTCTCATGGC | CAAATAGTAT | 49980 |
| TTCATTGTGT | ATATATGCCA | CATTTTCTAT | CCATTTGTCT | GTTAATGAAC | ATTTAGGGTT | 50040 |
| GACTCTATAT | ATCAGCTCTT | GTGAAGAGTG | ACGCAATAAA | CATGGGGATG | TAGGTGTCTC | 50100 |
| TTTGTATACT | GATTTCCTTC | CCTTTGGATA | AATAGCCAGT | AGCAGATTTT | CAGCCTCATC | 50160 |
| TGGTAGATCT | ATTTTTAGGT | TTCTGAGAAA | CCTCTGTTGT | CAGTAGGCTG | GTTCAGATTC | 50220 |
| TTGAATTCCC | TGCACAAAAG | AATTTGAAAG | CCAGTCCAAA | GTAAAAGTAG | GCAAAGGAGT | 50280 |
| TTATTGCAAG | GTGAAAGTAC | ACGCTGATAG | CAGAGTCAGG | GTCGGCTACT | TCAGCACCAA | 50340 |
| TTGACACTGA | AGAAACTCCC | GTTATGGGAG | TCCTACGTGA | TTATCCATGA | GGGGGTGGGA | 50400 |
| ATGGGCATTG | TTGTTAAATA | TGTTTTGGGT | GGTCTCTTGA | ATGTGCATGC | AATATTGCCA | 50460 |
| TACACGCTAG | TACATACATC | ACATGTATTA | TTAGCATTTT | AATTCTCTAC | CCAAGGGTGT | 50520 |
| GTTTCTTACT | ATTAAAATGA | GTATATGTCA | ACCTGAGAAC | ACAGCTTGTG | GGTTTCTGCA | 50580 |
| CTTGCACGAA | CTTAGGGATT | TTCCCTCCTG | CTCTTCTACC | TCCTTGACTG | AGGATATTCT | 50640 |
| AACCACTAGC | CCCAGATGCA | GTTTGTGTAA | TGTCAAGAGA | TTTGTTCTCT | CCATCAATTT | 50700 |

| | | | | | | |
|---|---|---|---|---|---|---|
| GACAAGTTTC | TTGTTTCCTT | TCAAGGGAGG | CTGTGACCAC | CCTATGTAAC | CTACCTCACT | 50760 |
| TCCATACTAT | TTTGCATAAT | GGCTATGCTA | ATTGACATTT | CCACCAGTGG | GACATAAGAG | 50820 |
| TCCCCTCTTC | TGTACATCCT | CACCAGCATT | TGTTATTTTT | TGTTTTTTTG | ACAATAGCCA | 50880 |
| TTCTAACTGG | GGTGAGATGA | TACCTTATTG | TGGTTTTGAT | TTGCATTTCC | CTGATGATTA | 50940 |
| GTTATTTATA | TGGTTTGGCT | GTGTCCCTAC | CCAAATCTCA | TCTTGAATTG | TAACTCCCAC | 51000 |
| AATTCCCATG | TGTCCTGGGA | GGAACCCAGT | GGGAGGTGAC | TGAATTATGG | GCCGGGTCTT | 51060 |
| TCCTATGCTG | TTCTTATGAT | AGTGAATGAG | TCTCACGAGA | TCTGATGGTT | TTAAAACGG | 51120 |
| GAGTTTCCCT | GCACAAGCTC | TCTCTTTGCC | TGCTGCCATC | CATGTAAGAT | GTGACTTGCT | 51180 |
| CCTCCTTGCC | TTCCACCATG | ATTGTGAGAT | CTCTCCAGCC | ATGTGGAACT | GTAAGTCCAT | 51240 |
| TAAACCTCTT | TCTCTTGTAA | ATTCCCAGT | CTCAGGTTAA | GTCTTTATTA | GCAGCATGAA | 51300 |
| AACAGACTAA | TACAGTGATG | TTGAGCATTC | TTTCATATAT | TTGTTGGCCA | ATTGTATGCC | 51360 |
| TTCTTTTGAG | AAATGTCTGT | TCAGTTCACT | TGCCCACTTT | TAAATGAAT | TGTTGGTTGT | 51420 |
| GCACGGGTGG | CTCGTGCCTA | TAATCCCAGC | ACTTTGGGTG | GCTGAGGCAG | GAGAACTGCT | 51480 |
| TGGGACTAGG | AGTTTGGGAC | AAACCTGGGC | AACACAGAAA | GGCCCTGTCT | CTAAAAAAT | 51540 |
| GAAAATAATA | AAAATAAATG | AATTATTAAA | TCTGACTACA | GTAGAAATAA | ATTTGAAATC | 51600 |
| AATAAAAATA | AGAAATGTAG | AAAAAAACAC | ACATATTTGG | AAATTAAACA | TCATTCTAAT | 51660 |
| TAATCAATCT | CTCCAAACAA | ATCACAAAAA | ATTACAAAAT | ACATTGTACT | ATATAATAAT | 51720 |
| GACAATAAAG | CACATCAAAA | TTCATGGGAT | GCAACTTAAA | CAGTGTGTAG | AGAGATCTGT | 51780 |
| AACTTAAATT | GCTTATAGTA | GAAAACAAAT | AAAGTCTAAA | ATGAAAGTCC | AGATTCTACA | 51840 |
| AAGGTGGTAT | GTCTAATAAG | AGATACTTGT | GTTCTCCCAG | TAATACTGCG | ATCCCAAAGG | 51900 |
| ATGATAAAAG | TAAACTAGAA | GTAATCCCAT | CCTACTCTCT | GGAAACTGCT | AGAATGTTTG | 51960 |
| CTCTGCTTCT | CAGCAGAGCA | AGGGATGTGA | GAGAGGTGGG | GAGAGACAGA | GAGAGAGAGA | 52020 |
| GAGAGAGAGA | GAGATCATCA | ATCCTGATAA | GTTGTAACCA | CAAGCCAACT | TTTATACACA | 52080 |
| TTTAGGCTAA | AAAATAAAAA | GTCTTGGCTA | GCCACAGAGG | CTCATGCCTG | TAACCCCAGC | 52140 |
| ACTTTGGGAG | ACCAAGGTGG | GAGGATCACT | TGAGCCCAGG | AGCTCGAGAC | TGGCCTGGGC | 52200 |
| AACAAAGTGA | GCCCCATCTC | TAAAAAAAAT | ATTTAAAAAA | TTAGTCAGGC | ATGGTGGCAC | 52260 |
| ACACCTGTAG | TCCTAGCTAT | ACAGAATGGT | GAGGCAGAAG | GATTGCTTGA | GCTCAGTAGG | 52320 |
| TTGAGGCTGC | AGTGAGCCAT | GTTCACACCG | CTGCACTCCA | GCCTGGGTGA | CAGAGTAGGA | 52380 |
| CTCTGCGTAA | AAAAAAAAAA | AAAAAAAAA | GTCTCAATTC | ATGAATTGAG | TTTAAAGTAA | 52440 |
| TACTTGACTG | GTGGTACCCC | AGCTTCCTGG | CAAAAGCAGA | CACAAACCCC | CTCTAGAAGA | 52500 |
| AAGAACATCC | CAGTCCTCAG | TGACCCATAA | GTAATTTTAC | CAGAAAAATA | AAGAAGTTAC | 52560 |
| TGGCAAAATC | ATCAAATGCA | CAAAATGGAT | TGGAGGAAGC | GTAGCAAGAA | TAAATGAAGA | 52620 |
| GGAGCTGGGT | GCTGTGGCTC | ACGCCTGTAA | TCCCAGCACT | TGGGAGGCT | GAGGTCAGGC | 52680 |
| GTTTGAGACC | AACCTGGCCA | ACATGGCAAA | ACCCCGTCTC | TACTAAAAAT | ATAATAATTA | 52740 |
| GCTGGGCATG | GTGGCATGTG | CCTATAGTCC | CAGCTACTTG | GGAGGCCTGA | GGCAGGAGAA | 52800 |
| TCGCTTGAAC | CCGAGAGGTA | GAGGCTGCAG | TGAGCCTAGA | TGGTGCCACT | GCACTCCAGC | 52860 |
| CTGGGCAACA | GAGTCAGACT | CTGTCTCAAA | AATAAATAAA | TAAATAAATA | AATAAATAAA | 52920 |
| TAAATAAATA | AATAAATAGG | GATCAGGAGG | TTTGAGTAAA | TAAGGTTAAA | AGTGATGGTG | 52980 |
| TTCTAGACTA | TTTGTGTCTT | TATATTAAAG | TGAATTTTTT | GTAGGCAGCA | TGTTGTGGCT | 53040 |
| CTTTTTTTGC | TTTTTTTTGT | TGTTGTCTGT | TTTTTAATT | CAATCTGACA | ACCTCTGCTT | 53100 |

-continued

| | | | | | | |
|---|---|---|---|---|---|---|
| TTGTATTAGA | GTATTTAGAT | CATTTACCTT | AAGTGTGATA | ATCTATATGG | GTAGAGTTAA | 53160 |
| GTCTATCATC | TTGCTATTAC | TTTCCCATTT | GTCCCATCTG | TTCTTTGTTC | TCTTTTTCCT | 53220 |
| CTTTTTTTTC | CCATCTGTTG | AACAACTTAA | ATATTTTTC  | TCATTCTATT | TTATTTCTTT | 53280 |
| TTGTGGCTTG | TTAGCCATAA | TTCTTCGTTT | CATTATTTCA | GTGGTTGCCT | TAGAGTTTAT | 53340 |
| AGTATACATC | ATTAATTTAT | CGTAGTTCAT | CTAAAAGTAT | ACCACTTATA | TAAAATAACA | 53400 |
| TTATTTTCAT | TTCCACTTCT | TTTGCACTGT | TGTTGTCATA | CACTTTTCTT | TTGTGTGTGT | 53460 |
| GTGTGTGTGT | GACAGAGTCT | AGCTCTGTTG | CCTAGGCTGG | AGCACAGTGG | TATAATTTTG | 53520 |
| CCTCACTGCA | ACTTCCACCT | CCTGGATTCA | AGTGATTCTT | GTGCCTCAGC | CTCCAGAGTA | 53580 |
| GCTGGGATTA | CAGGCGTGCA | CCACCACGCC | TGGTTAATTT | TTGTATTTTT | AGTAGAGATG | 53640 |
| GGGTTTTGCC | ATGTTAGCCA | GGCTGGTCTT | GAACTCCTGT | CCTCAAGTGA | TCTGCACGCC | 53700 |
| TCGGCCTCCA | AAAGTGCTGG | GATTACAGGC | ACGAACCTTT | GTGCCCGGCC | TGTTTTACTT | 53760 |
| TTAAATGCTA | TAAATCACAC | ATTACATTGT | TAACTATTTT | TGTGAAAATA | GTCAACCACA | 53820 |
| TTTTATGGAG | AAAAAATATT | ATCTGTTTAC | TCACATAGTT | ACAATTTTCT | AGTACTGTTT | 53880 |
| ATTCCTTTGT | ATAAATAGGA | ATTTCAATAT | GCCTAAGGGA | CTTTTATCAT | TCTGCCTAAA | 53940 |
| GGACTTTTAA | AAAATATTTT | TTATTGTTCT | AGTCTGCTGA | TTAGATGTTT | ATTGCCTTTA | 54000 |
| GGCAGGGAGA | TAAAAAAATA | CTACAATATT | TTAGTTAATG | ACTGTGTCAA | TCAAAAGAA  | 54060 |
| GCAAGACAAT | CTACCATTTA | ATTGCACGGT | TGATTTTTTA | AATGAAATAG | AAAACATCCA | 54120 |
| CATATACAGT | ACAAAATGTA | TCATAAAACT | CTCACATATG | ACTAGATAAA | TTCCTTCCTC | 54180 |
| TTTTCTCTGT | ATTAAATTGT | CTTATTTCAC | CCTCATTTGG | GGGGAGTTTT | TTTGCTTGGT | 54240 |
| ACAGAATTGT | AGGTCTTTCA | TTAATCTAAA | AAATTTTGCT | CCACTGTCTT | TTTGCTTATA | 54300 |
| TTGTGTCTAT | GAGAAATATG | TGATCTATAC | ACTTGTTCTT | CTGTACATAA | TGTGCCTTTT | 54360 |
| GTTCTTGGCT | GCTTGAAAT  | TTTTCATTTT | CCTCTTGCTT | GCTTGGGTT  | TGATTTGTTC | 54420 |
| TTATTTTTCT | AGTTTCTTTT | TTTTTTTTAA | TTTGAGACG  | GAGTCTCGCT | CTGTCTCCCA | 54480 |
| GGCTGGAATG | CAGTGGCGCG | ATCTCAGCTC | ACTGCAATCT | CTGCCTCCTG | GGTTCAAGTG | 54540 |
| ATTCTCCTGC | CTCAGTGTCC | CGAGTAGCTG | GGACTACAGG | CAGATGCCAC | CAGGCCTGGC | 54600 |
| TAATTTTTGT | ATTTGTTAG  | TAGAGACAGG | GTTTCACCAT | GTTGGTCAGG | CTGGTCTCAA | 54660 |
| ACTCCTGACC | TCGTGATCTG | TCCGCCTTGG | CCTCCCAAAG | TGCTGGGATT | ACAGGCGTGA | 54720 |
| GCCATCACGC | CCAGCCTAGT | TATTGATTTC | TATCTTCATT | CCACTTTGGT | CAGAGAATAT | 54780 |
| ATACTCTATT | ATTATAGTCC | TTTTACATTT | ATTGAGACTT | ATTTCATGAA | GTAATATACA | 54840 |
| GTCTATCCTG | AAAAATGTTT | CATGTGAGCT | TCAGAAGGAT | GTTTATTCTG | CTGTTTTGGG | 54900 |
| GTGTAGTGAC | CTATAGATTT | ATGTTAGGGT | CAGGTTAGGT | GTTTTCAAGT | GTTAAGTCTT | 54960 |
| CTATTTTTT  | GTTGATCTTG | TCTAACTAGT | GAGGTATTGA | TGTCTCCAAC | TATTATTGTC | 55020 |
| GAATTTTCTA | TTTCTCCCTT | CAATTCTGTC | AGTTTTGTTT | CATGAATATT | AGGGCTCTGT | 55080 |
| TGTTAGGTGC | ATGTATGTTT | ATAATGTTAT | GTTTTCTTGA | TGAATTGACA | CTTTTATCAT | 55140 |
| TACAAAATAC | CTTTCTTTAT | TTATTATAAC | AATGCTTATC | TTAAAGTTTA | TTTTGTCTGA | 55200 |
| TATTAGTATA | CCTACTCCAG | ACATCTTTTG | AGTACTATTT | GTATGTGATG | AATTGTTCCT | 55260 |
| TTCTTTCTGC | TCTCAAGATT | CATCTTCTTC | ATCTTTTGAT | AATCTGATTA | TGATGTGTCT | 55320 |
| AGGTATGGAT | CTCTTTGAGT | GTATCCTACT | TGGAATTCAT | TGAGCTCCTA | AAATATGTAT | 55380 |
| GCAAGTTAAT | GCTTTTTTGC | CAAACATGGG | AAGCTTTGAG | AAATTATTTC | TCCAAACATT | 55440 |
| CTCTCTCCCT | GTCCTCTCAC | TTTTCTCCTT | CTAGGAGTCC | CATTATGCAT | ATATTAGTAT | 55500 |

-continued

| | | | | | |
|---|---|---|---|---|---|
| GCTTGATGGT | ATCCCCTGTC | TCTAAGGCTC | TATTTCTTTT | TCTTCATTCT | GTCTTCTTTC | 55560 |
| TGTTTTTCAG | AGTAGATCAT | TTCAATTGAC | CTATCTTTGA | GTTCACTGAT | TACTTCTTTT | 55620 |
| TGCTGCTCAA | ATTTGCTGTT | AAAGCCCTCT | AGTAATTTTT | TTTTCTTACA | GATGAGATAT | 55680 |
| CATGCTGTCG | TTCAGGCTGG | AGTGACCATG | ATCCTCTTAC | TGGGATCACA | GATCACGCAT | 55740 |
| GCTCCAGTCT | GAGCAGCAGC | ATGAGCTCCA | GCTTGCTCCA | GCCTGAACAG | CAGCAATACA | 55800 |
| TTCTTTCACA | CACAAAAGGG | TTATTGGATC | TCACACAAGA | AGGAATTTGG | GGCTAGTCCA | 55860 |
| TACAGTAAAG | TGAAAACAAG | TTTATTAAGA | AAGTAAAGAA | GGGCCGAGCG | CAGTGATTTA | 55920 |
| TGCCTGTAAT | CACAGCACTT | TGGGAGGCTG | AGGCAGGCAG | ACCACTTGAG | GTTAGGAGTT | 55980 |
| CGAGACAAGC | CTGACAAACA | TGGCAAGACA | CTGTCTCTAC | TAAAAATACA | AAATTAGCTG | 56040 |
| GGTGTAGTGG | CACATGTCTG | TAGTCCCAGC | TCCTCAGGAG | ACTGAGGCAG | AAGAATCGCT | 56100 |
| TGAACCCAGG | AGGCAGAGGT | TGCAGTGAAC | CAAGATCGCA | CCACTGCACT | CCAGCCTCTA | 56160 |
| GCCTGGGTGA | CAGAGTGAGA | CTCTGTCTCA | AAAAAACAAA | AAAAAGTTAA | GAAATAAAAG | 56220 |
| AATGGGTCAT | GCATAGTGGG | TAATGCCTGT | AATCCTAGCA | CTTTGGGAGG | CCAAGGCAAG | 56280 |
| TGGATCGCTT | GAGGCCAGGA | GTTCGAGACC | AGCCTGGCCA | ACATGGCGAA | ACCCATCTC | 56340 |
| TACTAATAAT | ACAAAAATTA | GCCAGGCATG | GTGGCACCCA | CCTGTGGTCC | CAGCTAGTTG | 56400 |
| GGAGGCTGAG | GCAGGAGAAT | TGCTTGAACC | CGGGAGGTGA | AGGTTGCAGT | GAGCCAAAAC | 56460 |
| ACGTCACTGC | ACTCCAGACT | CCAGCCTGAG | TGACAGAGCG | AGTCTTTATC | TAAAAAATAA | 56520 |
| AAATAAAAGA | AAAGAATGGC | TACTCCATAG | GCAGAGCAGC | AGTATGGACT | GCTCAAATAA | 56580 |
| GCAGACGTAT | AGTTATTTCT | GGATTATGTG | CTAAACTAAT | GGATTATTCA | AGAATTTTTC | 56640 |
| AGGAAAGAGG | TGGACAATTC | CCAGAACTAA | GGGTTCTTCC | CCGTTTAGA | CCATATAAGG | 56700 |
| TAACGTCCAG | ATGTTGTCAT | GGTATTTGTA | AACTGTCGTG | GCACTGGTGG | GAGTGTCTTG | 56760 |
| TAGCATGCTA | ATGCAGTATA | ATTAGTGTAT | ATGAGCAGTG | AGGATGACAA | GAGGTCACTT | 56820 |
| TTGTGGCCAT | GTTGGTTTTG | GTGGGCTTTA | GCTGGCTTCT | TTACCGTTAC | CTATTTTATC | 56880 |
| AGCAAGGTCT | TTGTGACGGG | TACCTTGTGC | AACCTTCTAT | CTCATCCTGT | GACTAAACTC | 56940 |
| CTGGTTAGAA | TGCCTAACCT | AACCCAGCAG | GCCTCAGCCT | TATTTTACCC | AGCCCCTATT | 57000 |
| CAAGATGGAG | TCACTCTGAT | TCAAATGCCT | CTGACATATT | TTCCCACTCC | CTTTTACCAG | 57060 |
| GGAACCCTTA | ATCCTAAGGA | TTGCAGTGGG | ATAAAGATCC | GTCTTCTATA | ACTTCTTCAG | 57120 |
| ACTAAATAGG | GGCAATGATA | TTCCTGTCTA | ATTATTAGGG | TCTCTTGTGT | CCAGGGTAGA | 57180 |
| GAGGAGCTCA | GTCACAAAGT | GTCAGTATGG | TGAGACATTC | ATAACTCTGA | GGCTTCCCAA | 57240 |
| AGTGTTGAGA | TTACAGGCGT | GAGCCACTGT | GCCTGGCCAG | GGTCCCATTT | TTATACCAGA | 57300 |
| TCCTGGATCC | CAAAAGAGGG | AATCAGCCCT | CTTTTGGGGG | ATCAGCCATC | TCCCCTGGGA | 57360 |
| ATCTTATCTC | TCGGTGGGGA | TGGAGACATT | TCCATACCTT | CTAGGTAGTC | AAGAGAATGC | 57420 |
| TTCTTGTGAT | CCAAAAGTGC | AAATAGCCAA | GTATTCACCT | ATATTGCCT | TTAGCTATCC | 57480 |
| CCAGAAGTAT | ATTTCCTACC | TGGTTATTAC | ACACCAGATC | TCCCTCATAA | TGCAAAGTAA | 57540 |
| TTTCTGATAC | CCCCAAAAGT | CAAAAACATC | AGATAACATA | ATGCAAAGCC | AAACAGAGCC | 57600 |
| TTAGATTTTG | CGAAGGATCT | ATCCACTTCC | AGTTCCTGGG | GTTTCATGAG | GAAAACAGAG | 57660 |
| GTTTTCCCAA | AATGGGTCT | GTGGTGCCTC | CTCTGCTTTT | CCCAAGGAGT | CCCAGGCTTT | 57720 |
| TAGAGATTGA | ATATCCACTT | TTAATTAAGC | TTTTAACCAT | AAACCATAGC | ACTCTAAAGC | 57780 |
| AAAAAAAAAA | GGAGTCCTTT | TAAGTTTCTT | ATTACTCAAC | TTTAGCCATC | CCACACGGCC | 57840 |
| ATTATTTCTG | GCTTTTGAAC | TTTACCAAAG | ATAATCTCCC | AGGTTCTCAG | AGAGAGGAAA | 57900 |

| | | | | | | |
|---|---|---|---|---|---|---|
| ACTCAAGACA | GTGTGTGGAG | GGGAAGAGAA | CAGAATCAAC | AAATGGTAAA | GGTCACACAG | 57960 |
| ATATCAATCA | GAAAGTACTC | ATTCCCTAAG | CCAGGATTGA | ACCTTGGCCG | CCATTATAAA | 58020 |
| ATGACAAATC | CTTAGCTGCT | GAGCTACAAC | ACTGGTTAGT | TTCCATTGCC | CTTCCCAGAA | 58080 |
| GGGGTCCAGA | GCAGCCAATT | TTGAGCTTGC | AATGGCTTGA | GATAATTTTT | AGAGTTAACT | 58140 |
| ATTACATAAA | CCCCAAAATT | CCTGTTCCCT | GGATGGCAGA | GACCAAGAGA | AAGTACCGCC | 58200 |
| ACGTGGTTAC | AAGGTGAAGC | TCCAAAGGAC | ATAAACAAG | ATGAGAAGGA | AACTTCATCC | 58260 |
| AGTTTTTATT | TTTTTTTTT | TCCAGGGACC | TGTAATAAAC | TTTGCAACGG | ACCAGTTTAC | 58320 |
| TGGGCTGGCT | TGAACAGCAG | GCTTATGGAG | TCCTGAGCCC | ATGTTCTATC | CTACCATATT | 58380 |
| CCTCTTTATG | ACAGAGTAAT | ACAGAAAGAC | AAATTGATAT | CACAAAGTAT | ACCAGATTCA | 58440 |
| TTACAGCTTA | AGACTAGCCC | CACAAATCCT | TGTTCCCATT | AATCAAAACT | TTACAGAGGT | 58500 |
| GATAAACAGT | GATTTTTACC | ATTCATTCAG | TTTTCACTAA | GAGAGAGAGG | CCAGAAGCCT | 58560 |
| GACTGGTAAG | AAATCTTTAC | CCTTTTGCTG | GCATGCCAGG | TTTCTGGGTT | CTCTTTCACT | 58620 |
| GAGCAGCACT | AGCAACCTTG | CTCACTGCAA | AGCCCTTGGG | TCCAAGCTAC | GACACAAAAG | 58680 |
| AAAACCAACT | TTTTTCTGTT | TCATGGAACC | ACAGGCAAAT | AAATGTCTCT | CACTTTTGTA | 58740 |
| AGATGCTGCC | CAATGGCCAC | ATAAAGTAAC | CAAATTAACG | TTTTCCATTT | CAGCCAGAGC | 58800 |
| AATATACATG | TGACAAAACA | TAGACATTGG | CCACTCCACT | TAGCACCCAA | TATCTAACTG | 58860 |
| GGAAGGCTCA | AACTTGCCCC | CAGATAGGCC | CTTTCATCTT | TAATCAAACT | TCTGACCAGG | 58920 |
| AGTTTCAACA | TATGGTCTCT | GGGCAAGATG | GTTGTCTCAA | GTAACAGAAA | AGACAGAAAA | 58980 |
| GAGAAAAGAG | AGAAAGGGAG | AAAAGCATTG | CCTGTGGTGA | GATGGGGAAG | GTGAGGAGTT | 59040 |
| CACAGAGGCC | AGAGAAAGAC | CCACCCATTG | CAGCAACACT | GAATCAAAAG | TTCAGGCGGC | 59100 |
| TGCTTGTCAT | AGCAAAGGGA | TCTTTTCCAA | CAGTCCTATC | AGCTGTCAAG | CTTCCCCTTT | 59160 |
| TGGAGAGAAG | AAAAGTTCCC | AATGTCCCGT | GATCCTGTAC | ATGCCTAATC | CTGTCACCCA | 59220 |
| TAGCTGTCAG | CAAAGAGCAC | AGGGAAGATT | AATACAAACA | GAATAGCAGT | TAACATCCCC | 59280 |
| TAATGCTAAA | TCCGTTTTTA | ACCAAGAGAG | ACTTTACTGA | GAGGGCCTC | TAACCCCTTA | 59340 |
| AATCTTAAGG | ACTGTAGCCT | TCCTAAGTTG | GGTCTCAAAC | CCAAGTTCGG | TCAAGCATTC | 59400 |
| TTGCCCTTTA | TTAAGAGCGG | ACTGAAACCC | TCTCTGTCTT | AGGAGAGACC | CTATCTCCCC | 59460 |
| TAAGTTGCAC | CTCTAACCCA | ATCCTATCCT | TTACCCGGGG | ACTCCACCAC | TTACCCAAAG | 59520 |
| TCAGCCAGTT | GGTGCTGTAG | TCTGTTTCCT | TTGGCTTCAG | AGTCTCCTCA | GTATTGTCCC | 59580 |
| TTCGTGGTCA | CAGAAAGATT | TACCAGAAAN | GGGTCTTGAT | CCAGACCCCA | AGAGAGGGTT | 59640 |
| CTTGGATCTC | ACACAAGAAA | GAATTTAGGG | CAAGTCCATA | CAGTAAAGTG | AAAGCAGGTT | 59700 |
| TATTAAGAAA | GTAAGGAAAT | AAAAGAATGG | CTACTCTGTA | GGCAGAACAG | CAGCGTGGTC | 59760 |
| TGCTCAAATA | AGCATACTTA | TAGTTATTTC | TGGATTATGT | GCTAAACAAG | GGTGGATTA | 59820 |
| TTCATGAGCA | TTCCAAAAAA | GGGGTGGACA | ATTCCCAAAA | TTGAGGGTTC | CTCCACCTTT | 59880 |
| TAGACCATAT | AAGGTAAAGT | CCAGATATTG | CCGCAGTATT | TGTAAGCTGT | CATGATGCTG | 59940 |
| GTAGGAGTGT | CTTTTAGCAT | GTTAATACAT | TATAATTAAC | ATATAATGAG | CAGTGAAGAC | 60000 |
| AACCAGAGGT | CCCTTTGGTG | GCCATGTTGG | TTTTGATGGG | TTTTGGCCAA | CTTCTTTACC | 60060 |
| ACAACCTATT | TTATCAGCAA | GGTCTTTGTG | ATGTGTACCT | TGTGCTGACT | TCCTATCTCA | 60120 |
| TCCTGTGACT | AAGAATGCCT | AACATACTGG | AAATGCAGCC | TAGCAGGTGT | CAGCCTTATT | 60180 |
| TTATCCAGCG | CCTATTCAAG | ATAGAGTCAT | TCTGGTTCAA | ATGCCTCTGA | CAATGCAGCC | 60240 |
| TTGAATTCCT | GGGCTGAAGC | CATCTTCCCA | CTTCAGCCTC | CTGAGTAGCA | GGGACTACAG | 60300 |

| | | | | | |
|---|---|---|---|---|---|
| GCACACACCA | TCATGCCTGG | CTAATTTTTT | TGTATTTTTT | TTTTTAGAGA | TGGGGTCTCA | 60360 |
| CTGTGTTGCC | CAGGCTGGTC | TTGAGCTCCT | AGGCTAAAGC | AATCCTCCTG | TGTCATCCTC | 60420 |
| CCAAAGTGTT | GGGCTTGTCA | GAGGTATTTG | AACAAGAAAG | ACTCCATCTT | GAATAGGAGC | 60480 |
| TGGGTGAAAT | AAGGCTGAGT | CCTGCTGGGC | TGCATTCCCT | GTAAGTTAGG | CATTGTAAGC | 60540 |
| CACAGGATGA | GGCAGGCAGT | GGGCACAAAA | TACAGGTCAT | AAAGACCTTG | CTGATAAAAC | 60600 |
| AGGTTGCAGT | AAAGAAGCCG | GCTAGGCCAG | GTGGGGTGGC | TCACACCTAT | AAGCCCAGCA | 60660 |
| CTTTGGGAGG | CTAAGGTGGC | TGGATGGCTT | GAGCGCAGGA | GTTGGAGATC | AGCGTAGGCA | 60720 |
| ACATGGCGAA | ACCCGGTCTC | TATTAAAAAT | ATAAAAATT | AGCTGGGTGT | GGTGGCACAT | 60780 |
| GCCTGTAATC | CCAGCTACTT | GGGAGGCTGA | GGCACGAGAA | TCGCTTGAAC | TCAGAAATTG | 60840 |
| GAGGTTTCAG | TGAGCTGAGA | TCGTGCCACT | GCACTCCAGC | CTGGGCAAAA | AAAAAAAGA | 60900 |
| AAAAGTAAA | GAAGCTGGCT | AAACCCCACC | AAATCCAAGA | TGGCGATGAG | AGTGACCTCT | 60960 |
| GGTCATCCTC | ACTGCTCCCC | ACCAAATCCA | AGATGGCGAT | GAGAGTGACC | TCTGGTCGTC | 61020 |
| CTCACTGCTA | TGCTCATACC | AGCGCCACGA | CAGTTTACGA | ATGCCATGGC | AACGTCAGGA | 61080 |
| AGTTACTTTA | TATGGTCTAA | AAAATGGAGG | CATGAATTAT | CCACCCCTTG | TTTAGCACAT | 61140 |
| AATCAAGAAA | TAACCATAAA | AATGAGCGAC | CAGCAGCCCT | CAGAGCTGCT | CTGCCTATGG | 61200 |
| AGTAGCCGTT | CTTTTATTCC | TCTACTTTCT | TAATAAACTT | GCTTTCACTT | TACAGACTCG | 61260 |
| CCCGAATTCT | TTCTTGTGTG | AGATCCAAGA | ACCCTCTCTT | GGGGTCTGGA | TCTGGACGGA | 61320 |
| CCCCTTTCCG | GTAACAGGAT | TACAGGTGTG | AGTGAGCCAC | CATCCCCAGC | CTTAGTAAAT | 61380 |
| TTTTATTTCA | GTTATTATAT | ATTTTTATTT | ATTTTCTGTT | TTTCAGTTAT | TATATTTGAA | 61440 |
| ACTCCAGAAT | TTTTATTTAG | AATGTATTAA | CAAATCAGGA | GTACTGGCAT | AAGCCTGGCA | 61500 |
| CAAAGCAAAT | GTTGACATAG | GTCTGGCACA | AAACAAGTGT | TCAATGCATT | TTAGCTACCT | 61560 |
| TTAAGTGTAT | TATTACTAGC | TGCTTCTGGG | GCTATCCGGG | GAAAATTATC | CTTGCAAAAC | 61620 |
| CCCCACTCAC | TTCCAGAGCA | GGCTTCAGTG | AAGCAGTCAT | CTGTGTCATG | ACAAGAGCCA | 61680 |
| AACTCTGTAA | AACATTTGAA | GAGATTTATT | CTGAGCCAAA | TTTGAGTGAC | CATGGCCCAT | 61740 |
| GACACAGCCC | TCAGGAGGTC | CTGAGAACAA | GCGCTCAAGG | TGGTTGGGAT | GCACCTTGGC | 61800 |
| TTTATACATT | TTAGGGAGGC | ATGGGACATC | AATCAAATAC | GTTTAAGAAA | TGTACACTGG | 61860 |
| TTTGGTCCAG | AGAGGCGGGA | CAACTGGAAG | CAGCGGAGGA | GTGGGGTGGA | GGTGATGACA | 61920 |
| ATTGGTTGAG | TTTGTATAAA | GATTTGGGAT | TAATAGAAAG | GAGCACTAGG | TTGTGATAAC | 61980 |
| AGGTTGTGAA | GACCAAAGTT | GTACTATGGG | ATGAAGTTTT | TAGCTAGCAG | GCTTCAGAGA | 62040 |
| GAATAGGTTG | TAAAATGTTC | TTATCAGACT | TAAAAGCTGT | GTTGATGTTA | ATGCCAGAGA | 62100 |
| GGAATAATGA | GGCATGTTCA | ACCCCCACTT | CCCTTAATGG | CCTGAGCCAG | TCTTTCAGGT | 62160 |
| TACATTTTAA | GAAGCCTGAC | TGAAGAGAAA | GTCTATTCAG | ATGGTTGGGG | GCTTTAGAAT | 62220 |
| TTTATTTTTG | TTTTATACCT | TTGCCCTTGG | AAGTTTTGCT | GAAAAATGAA | CACAAAAAAA | 62280 |
| GGCAGATTCA | TAAGATAAAA | GGCTTTACAA | TTTAATTACT | CTGTGGTTCT | CCTCATGCAC | 62340 |
| ATAGTACCAA | TATCCCAGTG | GAATTTAGAA | GCTTATATGC | CACCTTGAAG | TTGAAGAAAT | 62400 |
| AACAGGGGCT | TGATCCTTGC | AAAATAGGTT | ATGGGAAACA | GAAGAAGAGG | AATTCTGTTG | 62460 |
| AGGGGCAATA | TGTAACTACC | AGGAGAGACT | AATTGGATCA | AGAACAGAT | AAATTTGTAA | 62520 |
| ATAGTTCTCC | TTGGAATTTA | AATGATGCTT | AGAGACTGAT | TATCTTATAA | AAGGGTCTGT | 62580 |
| TCAGGTGTGG | TTACATTCTT | GGTCTTTCCT | ATAATGCACA | ATGAGATAAC | AGAGAGGGAG | 62640 |
| AAAAGAACAA | TTGTTCTCGC | TGGTGGGGCC | ATCCTATTTT | TATGTACCTA | GGGAAAAGTC | 62700 |

| | | | | | | |
|---|---|---|---|---|---|---|
| TCTTTAGTGT | CTGTTGATCT | CTAAGAGTTT | TTCATTCAAA | ATACTCATTA | TATCAGGAAG | 62760 |
| CCACATTTTG | GGGTGAAATT | CACTACTCCC | TTTTAGAGAT | ACGGGTACAA | ACTGTTTGTA | 62820 |
| AAGAATGCTA | AGACTTTGCC | GGGTGCAGTG | ACTCACGCCT | GTAATCCCAG | CACTATGGAG | 62880 |
| GGGCCAAGGT | GGGCAGATCA | CTTGAGGTCA | GGAGTTCAAG | ACCTGCCTGG | TTAACATGGC | 62940 |
| AAAACCCCAT | CTCTATTAAA | AAAACAAAA | ATTAGCCAGG | CGTGGTGGTG | GGCATCTGTA | 63000 |
| ATCCCAGCTA | CTTGGGAGGC | TGAAGGCAGG | GAGAATTGCT | TGAGCCTGGG | AGGCAGCTGT | 63060 |
| TGCAGTGAGC | CGAGATCACG | CCACTGAACT | TCAGCCTGGG | CAACACAGCG | AGACTGTCTC | 63120 |
| AAAAAAAAAA | AAAAAATGCT | AAGACTTACT | TTGGGACATC | CTTTGTCAGG | GTCCATGATT | 63180 |
| CTGATTAGCT | CAAGGCAGGT | ATTTTTTTTT | TTTAATAGAG | ACAGCATCTT | GCTATGTTGG | 63240 |
| CCAGGCTCGT | CTCGAACTCC | TGGCCTCCAG | TGACTCCCCC | CACCTCAGCC | TCCCAAGTG | 63300 |
| CTGTGATTAC | AGGTGTGAGC | CACCACACCG | GTCTGGTTTT | TTTGGTGGT | TGTTGTTTTA | 63360 |
| ATCCTATAAT | CCTGTGTCCT | TTCTTCCTAC | CTCTGAGTAG | TGCTTACTCT | CTCCCCTTTA | 63420 |
| GTCATTTGAA | AAGTTTATCA | GAAAGTGGGT | GCAGTTTCAG | GCTGGGTACC | GTGGCTCATG | 63480 |
| CCTGTAATCC | CAACACTTTG | AAATGCTTAG | ATGGGAGGAT | CATTTGAACC | CAGTTCAAGA | 63540 |
| TTACAGTGAG | CTGTGATCGT | ACCATTGTAC | TTCAGCCAGG | GTGACAGTGC | AAGAGCCTGT | 63600 |
| CTCTAAAAAC | AAACAAAAAA | TTGCTTTCAC | ACTGTGATGC | TATCACATCT | CTCCTAAGCT | 63660 |
| CTTGTTGGGG | CTCAGAAATT | GATACCCTAA | TATATGGCCC | TTGGTCATAT | TGAACTGAAG | 63720 |
| AAGCCTCAAA | GTCTCTCTGA | CATCCCTGCC | ACCAACTATC | CCTACCAAAA | CACATCGTGG | 63780 |
| AATTAAAGTT | TCTTTATCTA | CCTAAGATCC | AGACCCACCA | AAAGAGCAA | TTATTTTTAT | 63840 |
| TTACCCTTCC | TGTAAGACCA | AGAATGTAAC | CATGCCCGAA | CGGACTTTCA | CAAGATAATG | 63900 |
| TTCAAGTTAA | TCTCTGTTCC | CTGATCTACT | TACTCTCCCT | AGTAATGAAA | GGAGTTGGCC | 63960 |
| AGCTTGCTTT | AGGCAGACAG | TAAGGGAATG | GTACCCAGAG | AACCTCTGAC | CTGCCCCACA | 64020 |
| AGTGCTTACA | CCGGATGTTT | TGTGCAGATA | AGGGAACTTG | CACAGGGGGC | TTGCCTAAAC | 64080 |
| ATGCCTGCAG | TGGATGATTC | CTTTCCTTAA | CACATGCACA | GTTCAGGAAA | TTAATCAATA | 64140 |
| TGGAGTAGCT | CAGTCTAAAG | GCCTGCATGC | ACTGGTAGGA | CAGGGTGGAG | TTGTCAGGAA | 64200 |
| TTTGAGTCTT | AAGCCCTAGT | ATTCAACTGT | GAAGAGCAAA | CCAGAAATCT | GCTTTCAGGA | 64260 |
| CCCTTGTCTT | TGCTGAGAGC | TTTCCTTTCA | CTTAATAAAT | TCTACTCCAC | TCATTCTTTG | 64320 |
| ATGGCTGCAT | GCCTAATTCT | TCCTGGCTGT | GAGACAAAAA | CCCGGACCTA | GCTGAGCGAA | 64380 |
| GGAGCAAAAA | TCCGCAACAG | TAATCCCATC | AACAGAGTTT | CTCTTCTTCC | CCTCCCATAA | 64440 |
| TCTGTTTTGC | CAGGATAATA | TATAAGCTTT | TAAGCCCTCT | TGGGAAGTGG | ATAATCATTC | 64500 |
| TATGGTTCTC | CCTGTGTACA | TGTTAATAAA | TTTGTGAGTT | GATTTTTCAG | CAAAGTTTCC | 64560 |
| CCAGAAGCCA | AAGGGGAAAT | TTCCCTTGGC | CCCTCCACTC | TCTTTTCCCA | GCTCTTCTTT | 64620 |
| TACTTTCGTT | TTTATTTCCT | CAGCCCAGTA | GGTCACAGCC | TTCTTTTTAT | TTCTTCTCTG | 64680 |
| TCCAAACCAT | CAGTATATCC | TACAGGTGGG | AGAGAAGCAG | CTCTCTGGGA | AACCAGTAAG | 64740 |
| CACCATGAGT | TCTGATACTT | TCTAGTACCA | TTTGACATAT | TAACATCCCC | GCCACCCCTA | 64800 |
| ATATGTATGG | ACACGCACAC | ACATACCACA | TCACATGCAT | CACACTAACA | CAAACTATGT | 64860 |
| ATCACATACC | ACACACAGCA | CACACAGTAC | CACATACCCC | ACACAACACC | CACACCACAC | 64920 |
| TACGTGCATC | ATGCACATAT | GTGCACACAC | CTCTTGTGAT | GTGTGTTTAG | TGCAATTCAG | 64980 |
| AAAGTTACTC | TTTGATTTAA | TGCACATCAC | TATGCTTAGA | AATATTCTAG | TTACTGGGAT | 65040 |
| TCATCAGTGA | ACAATATTGA | AAAAAATCCA | TCCCTTTGCA | TTCTCATGAG | GGAAGCAAAC | 65100 |

-continued

| | | | | | | |
|---|---|---|---|---|---|---|
| ACTAAACAAA | ATAAATTAGT | AAAATATTCA | GTGATAAGTG | CCATGGGAAC | AAAATAGATT | 65160 |
| TGAAAATGTT | TGGGAGGGAG | AGAGGGGTAC | ACTTGCTAAC | AAGTGGTCAG | GATAGGGTTA | 65220 |
| GTTGAGAGGC | AAAATCTGAA | GGAGTTGAGG | AAAGGCATTC | TAGGAATAGC | TGAGTGCTGA | 65280 |
| CTCTTGCCCA | CAGTGGGAAC | ACACAGTACA | GAGCTTCTGA | AGGAGACTCT | AGTGACCTAC | 65340 |
| TTCCCATTGT | GAGTCTTTGG | ACTCCTATAT | CCCATAATCA | CAGGATCAAG | CCTAACTTTA | 65400 |
| CATATTAGAG | ATAATGCATT | CCTCCTTGGG | GATAGTTCAG | GTTGATTTCT | CCCTAGGCCT | 65460 |
| GCCTTTGTCA | ACATATTCCT | GAAGTCTCAT | CTGCACCCCA | TCTCTGCTTC | TAATATTGGC | 65520 |
| CACTCTGTGC | ATGAACCAGC | CCCTCCTTCC | TGCAATGGGA | AACAGGTGTG | AGATGGGACA | 65580 |
| GCTGTCACAA | TCCGTTTTGC | TTTTGTCTTG | CTGTTATTAT | TGGTAATGGT | AGTTTGTTTC | 65640 |
| CTTTTTAGCA | TTCACTAGCT | TCCTTTTCCT | GATCCTTTGA | TAGTGTTACC | AGAAAGGGGG | 65700 |
| TCCCAACCCA | GACCCTAAGA | GAAGTTCTTA | GATCTCGTGT | GAGAAAGAAT | TTGGGGCAAG | 65760 |
| TCTACACAGT | AAAGTGAAAG | CAAGAAAGTA | AAGGAATAAA | AGAACGGCTA | CTCTACAGGC | 65820 |
| AGAGCATCAG | CTTCTGGACT | AAGGATACTG | ATATGGTTTG | GCTGTGTCCC | CACCTAACTC | 65880 |
| TCATCTTAAA | TTCCCACATA | TTGTGGGAGG | GACCTGGTGG | GAGGTAATTG | AATCATGGGG | 65940 |
| GCAGGTCTTT | CCCTGAGTAA | TTTATACTGC | TGTTCTCATG | ATAGTCAATA | AGTTTCATGA | 66000 |
| GACCTGATGG | TTTTATAGAA | AGGAATTTCC | CTGCACAAGC | TCTTTGCCTG | CTGCCATCCA | 66060 |
| TGTAAGACCT | GACTTGCTCC | TCCTTGCCTT | CTGCTGTGGT | TGTGAGGTCT | CCCCAGACAC | 66120 |
| GTGGGACTGT | AAGAGCATGA | AACATTTTTT | CCTGGTATAA | ATTACTCAGT | CTCAGGTATG | 66180 |
| TCTGGATCAG | CAGTGTGAAA | ATGGACTAAT | ACAGATACTT | ACAGTTATTT | CTTGATTATG | 66240 |
| TACTAAACAA | GGAGTGGATT | ATTCATATGT | TTTCTGGGAA | AGATGTGGGC | AATTCCCAGA | 66300 |
| ACCAAGCGTT | CCTCCCCTTT | TTAGACTATA | TAGGGTAGCT | TCCTGACATC | GCCATGGTAT | 66360 |
| TTATAAACCA | CTATGGAGCT | GGTGGGAATG | CCTTCTAACT | TGCTAACACA | TTATAATTCG | 66420 |
| TGTATAATGA | GCAATGAGAA | TGACTAGAGG | CCACTCTTGT | TGCCATCTTG | ATTTTGGTGG | 66480 |
| GTTTTGGTCA | GCTTCTTTAC | TGCAACCTGT | TTTATCAGCA | AGATCTTTAT | GACCTGTGTC | 66540 |
| TTGTGCCAAC | TGCCTATTTC | ATCCTGTGAC | TTACAATGCC | TAACTTCCTG | GGAATGCAGC | 66600 |
| CCAGTAGGTC | TCAGCCTTAT | TTTACCTAGC | CCCCATTCAA | AATGGAGTCA | TTCTGGTTTG | 66660 |
| AACACCTCTG | ACAATAGGAC | AGATCTGGAA | TGAGCCATGC | CTGGGTACAG | AGTCACATCC | 66720 |
| ACAACAATGA | AAGTTGTAGA | TATCTGCAAG | GACTCATCGT | GGGACCAAGG | ATTCAGGGGC | 66780 |
| TCATTCTTTC | TCCTCTCTCT | GTGTGCTGGT | TGCCTCAGGA | GTAGAATGTC | CCATGCTATG | 66840 |
| CATGGGGTCT | GCAACCATCA | TGCCAGGGCA | TGATGAATCG | TAGGTGGCAA | AACAACAGAA | 66900 |
| GGCTCTGTGA | GCACCCAGGA | GGGTGCAGTG | CTGAAGAGTC | TTCTGCTTGG | TATAGGAAGA | 66960 |
| AAGGAACGTG | TTTCCCAATC | TTGCCTTTAT | TTTGAGTAGT | TGGACCAGAG | GGATTGCAGC | 67020 |
| TGGGCCAAAC | TCCATGTTCC | ATTGGCTATC | AGGGTCAGCA | GGCAGGCCAG | GGGCCCAGAC | 67080 |
| AGGCCAGTGG | CTCCCAGAAT | TCAAGTTTAA | TTTCTCCTCC | CACCTGTGTC | CTGAGCTCCC | 67140 |
| CTTACTGGTT | CCCTTGGACC | ACTGCATCTA | CTTAAGCCAG | CATTTATTAT | GTTGTTATCA | 67200 |
| TAAATGCCTC | TTACACCTGA | GACTTATAAA | TGTGACAAGC | TCTTATTGTG | AGATAGTAAT | 67260 |
| CCATCTTTTT | TCCCCATGAA | ATAATAATTC | TAACGGGTGG | TGATAGTACT | TTTCCTTTCA | 67320 |
| TTTTGAAGTG | GAGAAGCTGG | AGCTAAGTCA | TTAAGGACTT | GACCCTGGAC | CCCACAGCCT | 67380 |
| TTTCTCCACA | AAGCACAAAG | CAGAGTGATG | GTCCCAGGGA | TCCCACACAG | CTCTAAGCTG | 67440 |
| GGGGCACTCA | CTGCTGGGCC | ACTAGTGACT | CCCATTTTCT | ATCCTGGCTG | ACCCTCGCTA | 67500 |

| | | | | | | |
|---|---|---|---|---|---|---|
| TTGAAGAAGA | TCTGAGTCCT | GCAGAAGGAC | AGCAAGGAGA | AAAACAAGAC | ACAGAACGGG | 67560 |
| ACAGAGAAGA | ATAGAAAGCT | GACTCAGATG | AATTTTGTGA | TGCCAATGAG | TCCTACTGCT | 67620 |
| GTTACCACCC | CTTTTTCCAC | CACACCCTTC | AGAGCAGTTA | TAGAACCACA | AGCAACCCAT | 67680 |
| AAATAGCAAA | AGAAGTAACA | TCAGCTAGGA | AGGCTTAAGG | ACTCCCAAGG | GAGTTGGTGG | 67740 |
| CAAAAGTAGA | AAGATCTCAA | ATCAGAGTCT | GTGAACTGAA | CCTCTGCAGG | CTTCCTGTTT | 67800 |
| TTAGATACTC | TGTGTTGGGG | TCACATGATA | GTTACAGGG | TTATTAATTG | GTTCCTTCTT | 67860 |
| TTTATTGCTG | TAAAAGAAGG | ATATTTCTT | CCTACGTTTC | CCCCTCCTTT | ACCGGAGAGG | 67920 |
| CGGAGTGCAA | ATGATATGAA | CAACGTCACT | AGTTTTCTCC | TAAATCTTAT | GAGCCCCGCC | 67980 |
| TCCCACAGTA | GTTTCACTTC | TCAGTTTAAT | CCGGTCTGAG | TTAACTTCCT | GACCCAGGAA | 68040 |
| GTGGCAGCAA | CAGAGGGGAC | TAGCAGCGAA | TATGTAAGTG | TCTGAGCAGT | GAAGGTTACG | 68100 |
| GAAAGGTCC | AGGCTAAGGT | TTTCTCAGTG | GATATGTGAG | TGTGTACTGA | TGGCAAGTGG | 68160 |
| GGTGGGGAAT | ATATTTCGTG | ACAGCAGGGC | CCCTCCAACT | CTGAAAATGG | TCAGGACTTT | 68220 |
| CTTTGTTTTA | CAGCTCTCAC | CTCTTTCCTG | CTCTTTCTTT | CACCAGACTT | TACACCAAAT | 68280 |
| CTCAGAAGAT | TCAGAACTTA | GATGAGTGGG | GCCCAGGACA | GGAACCCTGG | AGCCTTGGAA | 68340 |
| GGAGGGGAGC | CCCATCTCCC | CAGAAGAGCA | GTGACCCCAG | CAGAGAGGGG | CCTGGTGTAT | 68400 |
| CACTGGAGGA | AATAGCCTGC | CAAGGAATAC | ACGTCTTCAG | AAGAAATTCT | GTGTGGCTTC | 68460 |
| AAGAGACTGA | TCAAATTGTG | AGAGGAAAAC | AGCCTACCCG | GTAATTGTAG | TTAAATTACT | 68520 |
| GTTTTTATT | CTAGGCACTC | TTCAAACTTC | CTCCTGACTC | TGCCCCTGTC | CTAGAGGAGC | 68580 |
| TCCCAGGAGT | AGGGGTGTGG | GGGCGGGCGG | GGGGAGGGA | TCGGGGTAC | AGGGAGAGCC | 68640 |
| CAGCTAGGTT | CTCAGAAGAG | GCAGGCTTTT | TCGCTCCTGG | TCACTCCTCT | GTTGCCTATC | 68700 |
| CCTGGCCTCC | CCCATCTTCT | TTCTGCCTTC | CCTACCTCCT | TGGGTCTGCA | AACTCTTTAT | 68760 |
| GTTGCAATCA | CTCTGAACAT | GTCTCTTGAG | ATAGGTCCTG | TCCTGGAGAA | GAGATAGTAA | 68820 |
| AAGTAAACTC | CCCAGTTCTG | CAGGAGCTCT | GATCCCATAG | AAATAACTGC | TCCTCAGGAG | 68880 |
| CAAACCCTCT | GCTCTGCAGC | CTTCTTTCCA | ATTCTTATTC | CCTCAGTTTA | GGGAGAGGGC | 68940 |
| ACAAAAGGA | TAAACCGGTT | CTTCTGGTTG | TTCTGGTTGC | CTTGATTGCT | TCCATTATCC | 69000 |
| TCCTGGTTGG | GTCTCTAGCA | AGACGTTATT | AGCCAGGGAA | GTCCACTTA | GGCACCCCTC | 69060 |
| TCTGCAGAAG | AGGTATTCAC | TATTCTCCTT | TCTCTTTCTT | TTGCCTATTA | TACCTCTGCT | 69120 |
| CCTGAAAGCA | AAAACAACAA | CAACAAAAC | ACAAACAAAA | AACAACCGAC | CTTATTAACC | 69180 |
| AGTGTTGGTT | GTTGTTCTTT | GTGGGGATG | GGGGGGTCG | AGGTGGAGTC | AAATTTTATT | 69240 |
| GTCATGATGG | TGTAGGAGCC | AAGGGAACAC | TTCCCCTTTG | CCTTCTGAAG | TTCACTGAAA | 69300 |
| AATCGACTCA | CAAAAGGCAG | GCTAATTGGA | GAAAAGGCAT | ACAAATTTAT | TAACAAGTAC | 69360 |
| ATGGGCTAGA | ATCACAGAGT | GATTACCCCC | TCTGCCAATG | GGGGTAGATA | CTTATATAGC | 69420 |
| CTTATTTATA | AATACTTATG | TATAAATACA | TAAATATAAA | TATGTATGCA | TATGTATGTA | 69480 |
| TGTATAAATA | TGTATGTATA | CTGTATAAAT | ATGTATGTAT | AACGTTTATA | CATGTATACA | 69540 |
| TATTTATTTC | AGAGGGGAAG | GGTGATATCA | GGAGAATATA | GGTAATTCTT | TGAGGGCAG | 69600 |
| TAAATGATTA | CTAGGGAGAA | TAAATGAATA | TTTGGGAGGA | TGAATGAATG | GAGGAACAGA | 69660 |
| GTTAACTTG | TAAATGTTCT | CTTTGGAAAA | TGAATGAGCC | TGAGAGACAG | ACATTATTTT | 69720 |
| GTGAAAGTGT | CTGATTAGGT | CTGGTAACAT | TCTTAGTCCT | CTTTTCTTCA | GTACAAAATG | 69780 |
| AGATAATAGG | GGTTGGAAGG | AAAAACAATT | GTTCTTCTTG | TCTAGTGTGA | CTGGTCTTTA | 69840 |
| TGTAGATAGG | GGAAAAGTCT | CTTCCAGCAT | CTGCTGATCT | CTAAGGGCCT | TTAATTCAAA | 69900 |

| | | | | | | |
|---|---|---|---|---|---|---|
| ATACTCATTA | TACCAGGGAG | TCATATATTG | GGGTGAAGCT | CCCCATACTC | CTTCAATGGA | 69960 |
| ATCTGTCACA | GATCACCCAA | TTGCATAAGT | GTTACTACTA | ATTACAAAGA | GTAATTCTGG | 70020 |
| TACCAATTAT | TCTTTTTTTT | TTTTTAAGA | CAGATTCTCG | CTCTTTCACC | CAGGCTGGAG | 70080 |
| TGCAGTGGTG | TAATCTGGGC | TCACTGCAAC | CTCCCCCTCC | GGAGCTCAAG | TCATTCTCCT | 70140 |
| TCCTCAGCCT | CCTGAGCAGC | TGGGATTACA | GGTGTGCACC | ACCACATCTA | GCTAACTTTT | 70200 |
| TGTATTTTTA | GTAGAGATGA | GGTTTTGCCA | TGTTGGTCAG | GCTGGTCTCA | AACTCCTGAC | 70260 |
| CTCAGGTGAT | CTGCCCGCCT | CGGCTTCCCA | AAGTGCTAGG | ATTACAGGCG | TGAGCCACCG | 70320 |
| TGCTGGCCTG | GTAACAATTA | TTCTTGAAGT | TAACTAGAAT | AGGAAAGAGT | TTCACACTCC | 70380 |
| CTGAGTTCTC | TCTTTTACAG | CTTTTGTGAG | GAAGCCTGCA | TTGCTTCTCC | CAGCACTTGG | 70440 |
| TCCAAGGTAA | CTTTCTGTGA | TAACAGAATG | TTGTATATTG | AGGCTGTTAT | GTAGCCACTA | 70500 |
| GTCACATGCA | ACTATTAAGC | AATCAAAATG | TGGCAACTGG | AACAGAAAAA | CTGAATTTTT | 70560 |
| TCATTTTAAT | TTTTATTAAG | TTAAATTTAA | ATTCCTACTC | ATGATAGTGG | CTACTGTATT | 70620 |
| AGCTATACAG | CTAGATGTTT | GTGTATCCTC | TAAATTCCAA | TGCATTTCTT | CTTTCTGGAG | 70680 |
| AGAAGACTTT | AGCTGGACAT | GGTGGCACAT | ACCTGTAGTC | CCAGCCACTC | TGCCAGGGTG | 70740 |
| AGGCAGGAGG | ATTGCTTAAA | CCCAGGAGGT | CGAGGCTGCA | GTGAGCTGTG | GTCATGCCAC | 70800 |
| TGCCCTCCAC | TACAGCCTGG | GCAAGAGAGC | GAGAACTTGT | CTTATAAGAA | AAGAAAAAGA | 70860 |
| GGCTGGGCAC | GGTGGCTCAT | GCCTGTAATC | CTGGCACTTT | GGGAGGCTGA | GGCGGGTGGA | 70920 |
| TCACAAGGTC | AAGAGATCGA | GCCAACCAAC | ATGGTGAAAC | CCCATCTCTA | CTAAAAATAC | 70980 |
| AAAAATTAGC | TGGGCGTAGT | GGTGCACACC | TGTAGACCCA | GCTACTACTC | GGGAGGCTGA | 71040 |
| GGCAGGAGAA | TCGCTTGAAC | CCGGGAGGCG | GAGGTGCAGT | GAGCCGAGAT | AGCGTCACTG | 71100 |
| CACTCCAGCC | TGGGTGACAG | AGTGAGACTC | CGTCTCATTA | AAAAAAAAA | AAAAAGTTAG | 71160 |
| AAGACTGAGA | AAAGAAAAAT | AATGAAATAA | TTTAGAGCAG | TCTGAGCTAT | GTGAGGTATG | 71220 |
| CAAAATTTAT | CAGGACAAGT | GAGGCAGGAG | TATAGGTCTT | CCAGTTAAGA | CCCCATGTTT | 71280 |
| TAAAAGCATT | TTGTTCCTGA | CTGGCTGCCT | CATCTATTAC | CTACATATTC | CCGAGATTTG | 71340 |
| TTAATACAAA | GAAACAATGT | TATAGCCAGT | CCAAAAGCTT | ATGCTATTTT | AATGTTAAAT | 71400 |
| CCTTGGCAAA | CAACTTTAAA | ACTGCTTTAA | ACTGCTTTTT | TCCTCTAACA | CACTTGTACT | 71460 |
| GCTTGCTAAT | GAGGCACTTG | AACTCTGCAC | TTGGTTGCAG | TTTCTCAAAG | TGCCCCAAAC | 71520 |
| AACCTTCACT | CAATTTCTTC | CTTTTAGTTC | CTCTTTTCTT | CAATACAAAA | TGAGATAATA | 71580 |
| GGGGTTGGAA | GGAAAACTTT | CAAGACCTAT | GGAAGTCAGT | TGCAGCCAGC | TCATCACATA | 71640 |
| GAGGTGCAGG | TGAGGTGTAT | TTTCATCACG | GTGGAAAATT | CTGGCTGCTT | CATCTCCATC | 71700 |
| TCTAGAGCCA | ATATTGGAGC | TTTTCAATAA | AAGCTATGGC | CTCAACCACC | AGCACCAAGA | 71760 |
| AGATGATGGA | GGAAGCCACC | TGCTCCATCT | GCCTGAGCCT | GATGACGAAC | CCAGTAAGCA | 71820 |
| TCAACTGTGG | ACACAGCTAC | TGCCACTTGT | GTATAACAGA | CTTCTTTAAA | AACCCAAGCC | 71880 |
| AAAAGCAACT | GAGGCAGGAG | ACATTCTGCT | GTCCCCAGTG | TCGGGCTCCA | TTTCATATGG | 71940 |
| ATAGCCTCCG | ACCCAACAAG | CAGCTGGGAA | GCCTCATTGA | AGCCCTCAAA | GAGACGGATC | 72000 |
| AAGAAATGTC | ATGTGAGGAA | CACGGAGAGC | AGTTCCACCT | GTTCTGCGAA | GACGAGGGGC | 72060 |
| AGCTCATCTG | CTGGCGCTGT | GAGCGGGCAC | CACAGCACAA | AGGGCACACC | ACAGCTCTTG | 72120 |
| TTGAAGACGT | ATGCCAGGGC | TACAAGGTGA | GTGTGTGGGC | CCGGGAGCTT | TGGTAAGTAC | 72180 |
| CAAGTCTTAT | CCTGCTCCCC | AGGAGCTGAG | ATGATTTAAC | TTGAAACCTA | ACATTATGAC | 72240 |
| TTGGAAATAC | AGCTTTCATC | ATGTCATTCT | TCTGAAAAAT | AGTTTATGAT | GATTTCTTGC | 72300 |

-continued

| | | | | | |
|---|---|---|---|---|---|
| TCAATTATCT | AGACTGTCCA | TCCTGACCTT | CAATGGGATG | GTTGGACTCT | TATCTCTATC | 72360 |
| CATTTGTGTT | ATGATGAATT | TCTTTTTGCT | TTAGAACAGG | TTGTTCTCAA | ACCAAACACC | 72420 |
| CGCATTTTTT | CTTGTTTCAC | ACCATGAATA | TCATTTGAAA | AACCACAATA | TGTAAAGCCA | 72480 |
| TGCAGTAGGG | CCTGAAAACA | GGGAAGAAAG | ACCCATCACC | TTTTAGGTAT | CTACAGTCTA | 72540 |
| GTAAAGAAAA | CAAACCATCA | AAAATGTCTG | CCTGGAGGTC | CCTGGTTTTG | GTGGTGGGGA | 72600 |
| GGGACATTTA | GGGTAGAGAG | TGGTTCATCT | TAGAAGTAAC | TCCTGAAGGA | CACGTAAAAA | 72660 |
| TTGAACACCT | ATTGGGGGAT | TTTCATTTGG | GGAATGAAGG | GTCAGTGACA | TTGAAAATAT | 72720 |
| CACTCTGGTA | CCTCTACTTT | TTTTTTTTTT | TTTTTTTTTT | TTTCCTGAGG | TAGGGTCTTG | 72780 |
| CTCTGTATCC | CAGGTTGGAG | TACAATGGTG | CAATCTCGGC | TCACTGCAGC | CTCAACCTTC | 72840 |
| TGGGGCTCAA | GCAATCCTCC | CACCTCAGCC | TCCCAAGTAG | CTAGGACTAC | AGGGATGCCC | 72900 |
| CACCATACCT | GGATAATTTT | TTTATTTTTT | GTAGAGACAT | GGTCTGCCTT | TCTTGCTTAT | 72960 |
| ACTGGCCTCA | AACCCCTGGT | CTCCCTCCCA | TCTCAGCCTC | CCAAAATGCT | GGGATTAGAG | 73020 |
| GCATGAACCA | CTGTGCCCAG | CTACTGTGGC | ATGTCTATGA | TAAAAGGAAT | ATCAAGGAGT | 73080 |
| AAAATTCAAA | CTATCCGTAT | AAGAAAGGGA | GGAGAGGGCA | GATTTTAAGC | ACGATTCAGG | 73140 |
| AAGAAGAGTC | AAAGATTTGG | AAATGCTTGG | TTGTGGAAGG | TGAAGCAGAG | GGAGAGGTTT | 73200 |
| TGTGTACCAT | CCAGATTTCT | TGCCAGAAAG | CATATTAAGG | AAGGTGGGAC | TTTGCTGTTG | 73260 |
| GCAGCATGGA | GGAATGGGCA | TAGTCCTGAT | GTCCTTTTC | CTTCTCTGTC | CTGCCTAAAT | 73320 |
| TTGAGGAAAA | TGTTGTCTCC | AGTGTCAGGC | TCCTTATTCT | GTCCTCCATG | AGGCAGAGGT | 73380 |
| GGTCTTGTAT | GAAGGCTCTA | AGTCCTTCTA | AGGACATGTC | AATCATGACC | ACCACTCAGC | 73440 |
| TCATGGCAGC | TCTTCCTTAA | ACTCCATGGA | GCAGCTAATA | ACTGCGATGA | TCATATTCCC | 73500 |
| ATTTGAATTA | CTTTTCCACC | AAGTAGTAAG | AAAAGGAACC | AGCTTATGTT | GAAATTGAGT | 73560 |
| TTTGTCACTT | ACTAGATGGG | CAATTTTGGG | CACGTTACTT | AATGTCTTCA | CACCTTGGTT | 73620 |
| TCTCCATCTG | TAAATGGGGA | TAATAGCAGT | GTCCTCCCTC | CCTAAAACAC | ATACACAGGA | 73680 |
| GGTGGTTATA | AGCTTTGAGG | ACATTAAAAT | ATAGAATGCA | TAGAATAGCA | CTTGGCATAT | 73740 |
| AGTAAGGACA | ATGTCATCTT | TTGCTAAAAC | AGTTACATAG | AACCTTTTCC | TGAGAACACT | 73800 |
| CGAGAATGAA | TGAGTATACT | TGTTGGGTTT | ACAGAGGACA | GGAGACAATT | CTTTCAGCAT | 73860 |
| TGACTACAAT | TAGCAATTTG | GGTCAGCTTC | AAATCACTTT | CAATAGAAAT | ATGAGAAACT | 73920 |
| GTTTTGAAGA | ATAAGCTAAA | AGCTTGACAT | GAATACTAAA | TCATTTAAA | TTGGATTCAT | 73980 |
| GATACCATTG | TTCAAAAGAT | ACCAGAATTC | CCCTCTTCCA | TGAACTGTTT | CTAATAACCA | 74040 |
| GCTGGCATCC | TGATTTTCC | TGACTCATAA | GACACAAAAT | TTCATGTTGT | TGCCAAACAC | 74100 |
| TGGTATTGGT | TTTGCTTGGT | TCAGCATGTT | GTTTACAAA | ATCTTTTAGA | TGATGATTAC | 74160 |
| CTTGTTCTAT | ATCCAACTTT | TTCCTGGCAG | GACTCTAGTG | GTGGACATAG | CTCAGGCTCT | 74220 |
| GGGTCAGCAG | ATGAGATTGC | AATTGTTGCT | CCACCACCTG | GCAGTCATAG | CCCTTTGGGC | 74280 |
| AAGTTATTTT | ACCCCTTTCT | TAGTCTCATT | TTCTACAGCA | CAGAAATGAA | GTTTAAAATC | 74340 |
| CTACCAACTA | TTCAGGGTTG | CCAAGGGGAT | CAGTATGTTC | CTGCACATAT | AGCCTTTAGC | 74400 |
| ATGCTCTCTA | GCAAAAAACA | ATGAGGACTC | TATAAATATT | CACTATTATT | CAAATATATC | 74460 |
| TTAGAAGATT | GGGATTCCCC | CTAGGTCCCT | AATGAAGAGT | CAAATTGAAT | AGGCTTCACT | 74520 |
| TATCAAATTT | TTCCTTCAGG | AAAAGCTCCA | GAAAGCTGTG | ACAAAACTGA | AGCAACTTGA | 74580 |
| AGACAGATGT | ACGGAGCAGA | AGCTGTCCAC | AGCAATGCGA | ATAACTAAAT | GGAAAGTAAG | 74640 |
| AATCTGACTT | CATTGATCTC | AAGCTATTTT | CCATTCTAGA | GCTTAGGCAT | AGGGGATGAT | 74700 |

| | | | | | | |
|---|---|---|---|---|---|---|
| TGAGGAAAAG | CACAATGAGG | ATTTATTCTC | ACTAAACCAG | ATTGAAAAAA | TGAAACCCAA | 74760 |
| GGAAGAAACC | ATTATTTGTA | CTTATGCCCC | TGGTTCCAGG | TTTACATCCA | TGAGTATTTA | 74820 |
| GCACCAATCT | TTCCATCTTT | AAACTGTAGT | TGGCTGGGAT | TCCTGATACT | TCAGTCAGAA | 74880 |
| GAAGCAGAAT | TAGTATGACT | ATTTACCTAG | AAAAAGCATC | GAGTGGGTCT | CAAACTTTAA | 74940 |
| ATACGTCAAA | ATAAACCTGG | TTTGCAGGCC | TCAACTCATT | ACCCTGGCAC | TTTTACCACA | 75000 |
| GTGGAGCATC | TGGCTCTCAA | CTTTACAGGT | ACAGAAACCA | AGCTTTGTGA | ACACTTAGAA | 75060 |
| AACAGGATCA | CTCCAGATTG | AAATTCATAC | TACTCTAGCT | CATGAAGCTG | ATGAAAGAAA | 75120 |
| TATACTTTAT | TTATTTATTT | ATTTTTAAAT | TATTACTATT | TTTGAGATG | GAGTCTTGCT | 75180 |
| GGAGTGTAGT | GGTGCGATCT | CAGCTCACTG | CAATGTCCAC | CTCCGGGTT | CAAGCAATTC | 75240 |
| CCCTGCCTCA | GCCTCTTGAG | TAGCTGGGAT | TACAGGCATG | TGCTACCATG | CCTGGCTAAT | 75300 |
| TTTTTGTATT | TTAGTAGAGA | CGGGGTTTCA | CCATGTTGGC | CAGGATGGTC | TTGATCTCCT | 75360 |
| GACCTCGTGA | TTCACCCACC | TCAGCCTCCC | AAAGTGCTGG | GATTACAGGC | GTGAGCCACT | 75420 |
| GCACCCGGCC | TATACTTGAT | TTATAAGTAC | ATCACAAGTA | ATGCAACAAC | CTACACACTT | 75480 |
| GCAACTACAA | ACTTTCAGAT | TATTTCCGTG | GCTGACTAAC | CTCCACATTA | TCAGAGCCAC | 75540 |
| ATTCTTTTAT | GGAAATATTT | AGGTTTGTGC | AAAAGTAATT | GCGGTCTTTG | CCATTAAAGT | 75600 |
| AAAGGCAAAA | ACCACAATTA | CTTTTGCACC | AATCTTTATA | TTTATATAAT | TCACTAGCTT | 75660 |
| GCAGTAAAAT | CCCACAAGCT | GATTACCAAT | TTTCTCTCTT | TCAGGAGTCC | TCTCTAACCT | 75720 |
| CTACCCTGAT | CTTTGTTTGT | GGATGTTGCT | CTTGAGCTCC | TGAGTACACT | CTTACTTCCC | 75780 |
| CCATTTCTAG | GATCTTGGGC | AATGGGGAAG | ACCTTGATTG | TAACTAACAT | ATATGAAAAC | 75840 |
| CCGTCTATAC | AAGAGTTAAA | GCTGCACCTG | TCTCCTACAC | AAAAATTCCA | CCTCATCCTA | 75900 |
| AGTCAAAGAC | CCTTCTTCTA | TATCATAGTC | ATCAAAACAC | TGTATGAATT | TATTTTTATT | 75960 |
| TTTTAATTTT | TATTTTTTTA | AGATAAGTAG | AGAGTTTATT | TGGGCCAAGT | TTGAAGACTG | 76020 |
| CAATCCAAGA | ACATAGATTC | AAATTGCCCT | GAATACACAC | TCCCACTGCA | TTAATTTAGA | 76080 |
| CAGCACTAAT | GGAAATTGCA | ACTTTACATC | TCCTCAGATG | AGAGTTTCAC | TTGATTTCTG | 76140 |
| TCAGTCTTAC | ACATAGGAAT | GCTTAAGATG | ACCCTAGGGT | AGTAGAACAG | TATTTCTCAG | 76200 |
| TTAACCATAA | TAAATGCCTG | TCACACTCAA | AGCTCCCCCT | GCCAAGAATT | ATGGACCCTC | 76260 |
| TTACCAGCCT | GGTTGTCTTA | AAATCCAGTC | TGGGTGATGT | TCATTATAAG | CTTTTACTTC | 76320 |
| AAGAAAATCG | CTCCAACTCA | GAAATCTAAC | TTCTTAAATC | ATAAGTAAAA | ACCTCTTTTT | 76380 |
| ATCCTTGTAA | CTGATAAAGT | GTTTGAACTT | GGCCCTAGTT | TCACAATTAA | ATTATCTAGC | 76440 |
| ACTCCTAACC | CAGCTTTCTC | CTGTGTCTTG | GCTGAAGAAC | AAGAAAATTA | ATTGGGTGAC | 76500 |
| TATAAGGAAT | CTGAGGCAAC | CTCTTCCACA | TCTGAGTGCC | TGCCTCCCAC | ACATGACTCT | 76560 |
| GCAGCAGGAA | ACTGGGGACA | TTCTTCCAGC | TTCAGTGACT | CATGAGAAAA | TAATGTCCCA | 76620 |
| GTGGCTGATT | GTGTGTGTGT | GTGTGTTTGT | GTGAAAATAT | ATATAACACT | TAAGCATTTA | 76680 |
| ACCACTTTTA | AGTATATAGT | TCAGTAGAAT | TAAGTGCTTT | TACATTGTTA | CATTGTTGTG | 76740 |
| CAACCATCAC | CATTCCCATC | TCCAAACTGC | AACTCAGTTT | CATCTTTCAT | CTTCTAAACT | 76800 |
| GAAACTCACT | ACCCATTAAA | CAATAACTGT | CCATTTTCTG | GTCTTGCCAA | CACCTTGTAA | 76860 |
| CCACTATTTT | ACTTTCTGTC | TCTATGAACT | TAACTACTCC | AGATGCCTTG | TATAAGCAAA | 76920 |
| GTCTTACAAT | ATTTGCCCTT | TTGTTTCTGG | CTTATTTTGC | TTGAATGTCT | TCAAGGCTTG | 76980 |
| TCATGTAGTA | GCGTGTGTCA | GACTTTCATT | CTTGTTTATC | CATTCATCCA | TAGATGGACA | 77040 |
| TTTGGTTTAC | TTCCACCTTT | TGACCATACT | TTCTTGACTC | CAGGAGAAGG | TACAGATTCA | 77100 |

| | | | | | | |
|---|---|---|---|---|---|---|
| GAGACAAAAA | ATCCGGTCTG | ACTTTAAGAA | TCTCCAGTGT | TTCCTACATG | AGGAAGAGAA | 77160 |
| GTCTTATCTC | TGGAGGCTGG | AGAAAGAAGA | ACAACAGACT | CTGAGTAGAC | TGAGGGACTA | 77220 |
| TGAGGCTGGT | CTGGGGCTGA | AGAGCAATGA | ACTCAAGAGC | CACATCCTGG | AACTGGAGGA | 77280 |
| AAAATGTCAG | GGCTCAGCCC | AGAAATTGCT | GCAGGTGAGG | CTGTGTACTT | GGAGTAGGGA | 77340 |
| AAAAGGTAT | GTTATAGTGC | TATTAAAGGA | GAATGGTAAG | GAAGCATGGG | AAGATAAAGT | 77400 |
| AATGTTTCTT | TTAGATGTAC | ATCAGTGCCA | TCAGGCTGGC | CTTCACTAAT | TTATAGGGTA | 77460 |
| CCTTTATGTC | AATTAGAAAA | ATAAACTTCT | GAGGGAACAC | AGCTTGGCCA | AATGAAACCA | 77520 |
| CGGGATAACA | TTTACCACTG | TTTGCCTCCT | TGGCCCATGT | GCAGAGAACC | CTGGTTGTTG | 77580 |
| ACTCTCTCCT | GAAATACTCC | ACTAGGTGAC | TGATGGGTGA | TGAAGTGGGG | CAGCCAAAAT | 77640 |
| GAGTGATAAC | CTTTTCCCTG | ATTTGCTTGT | AGAACCCTTG | CTCCAGAGCT | GTTATGGTAC | 77700 |
| AATCTACAGC | TTTATCTGTA | GGAAGATAAA | CATCTGGAGC | CATTAATTCT | GGTTCTAACT | 77760 |
| AACAGGATTG | GTGACTATAC | TGTAAGGCTG | AGTGTATAGC | ATGATTGCTT | TACCACTGTG | 77820 |
| TGATACCTGC | TACCACCATC | TTAGTGGCAG | TGGCCCAGTC | TCAGGGCTGT | GCACAGATTC | 77880 |
| ACCACTAAGG | ACCTTTATGA | TAAGTGTTCT | CTAATCTGGG | CTCACTGTGA | AGGAAATCCG | 77940 |
| ATCACCAAAA | GCTAGTCCTT | ACAGAGGGAG | CATGGACAAA | GCTCCTGGCC | CTCAGACTTC | 78000 |
| AGCAAGGATG | AGAATAGATG | CAAATGTTGA | TAAACATCCT | GCCATGCTGA | ATCTCCCAGA | 78060 |
| AGCTGGTAGG | AATTATTCCA | TCTGGGTATC | CATCAATACC | TAAGACTGGT | GGGAATTACT | 78120 |
| TTGTTTGAGT | ATCCATCAAT | ATCTAAGACT | AAGACTAGGG | TAACTCTCTT | TACTTCTTCG | 78180 |
| GGTAAAGCAA | AGAAGAATAG | CCCTGCATGA | CAAGCCCCAT | GAAATACCGA | TGTTCCCATG | 78240 |
| CTCACCTTTT | CTTTTTGTTT | CTTTATGAA | TGTGAATGAC | ACTTTGAGCA | GGTAAGTCCT | 78300 |
| GTTTGAATGC | AGGAGGGGAG | GGGTGTGCGT | ATATAGAAAT | GAATGGAATG | CACCTCTGAA | 78360 |
| GAAATCTCTC | GCCTCTGCTT | ATTCTAGGAG | TTGGGCTGTG | AAGCTGGAAA | CATCAGAGGC | 78420 |
| TGTCTCCTTG | GAACTTCATA | CTATGTGCAA | TGTTTCCAAG | CTTTACTTCG | ATGTGAAGAA | 78480 |
| AATGTTAAGG | AGTCATCAAG | GTATGTTCAC | TAAAGAATTC | CTGAATACTG | TGGATAGAAG | 78540 |
| GGGCCTTATG | CAGTAACCAA | GTTTACCACC | TGTCCCTTGG | CAGGCTCACA | GCCAGAGAGG | 78600 |
| TTGTTTAGTT | AATTTCAGTA | GAGCTTTCAT | ACTTTCTCTA | GTTAGTATGA | TTCACTGCTC | 78660 |
| AGTGAATGTG | ATGAGCATTG | CATTCTGGTT | ATCTGTGCAA | ACCTTTCAAA | TTCTTATTCT | 78720 |
| TTCACTTATT | AGCCATGTTA | CTCCAAGTGA | CTTGGTTTCC | CCCTCTGAAA | AATGAAAATA | 78780 |
| TTAACAGCTC | CTACTTCATT | GAGTTATCAT | CAAAATTAAA | TGCATCAACA | TGTACAAAGT | 78840 |
| GCTTAGCCCT | GTGACTGACA | CATGATCATA | ATAGCACATC | ATGGTATTAG | ATCTGATCAT | 78900 |
| AGTGTTTATT | ATCAATAGCT | CAGCCAACTC | TTAGAGCAAT | GCAAGAAAAG | TAGGTGAGTA | 78960 |
| TGATAACCTA | TCATTCACAT | ATTTTAGGAA | CTTGACTTAG | ATAACACAGA | TGACAAATGT | 79020 |
| TACAACCAAT | TTACAGATTC | CAAAATGTTA | GAACCATTTA | CTGAGTTTCC | TGCTCCCTTG | 79080 |
| ATTTTTTAAA | TCAGTGCTGA | CTATACTTTC | ACAAATTGT | ATCCGTAAGT | ACAAAATCAA | 79140 |
| AAAACCCCT | GAAAATGGAA | AGTTTTATCA | TGATTCATTT | GGCTACAAAA | ATCTGGCTA | 79200 |
| ACCTGAAATG | ATTTGGTGGT | TATATTAGTT | ATCTATTAGT | ACAAACAAAT | TACCATAATT | 79260 |
| TAGAACCTTA | ATACAACACT | GATATGTTAT | CTCAATTTTT | GTGGTTCAGG | AATCTGGGCA | 79320 |
| CAGCTTAGTT | GGGCCTGCTG | CTTAGGGTCT | GATAAGGCTG | CAGTTAAGGT | GTTGGTCAGG | 79380 |
| CTGTGTTCTT | ATCTGGAGGC | TAGGCTAAGG | AAGAATCCAC | TTCCAAGCTC | ACTGAGGTAG | 79440 |
| CAGGCAGAAT | TTCTTTCCTG | ATGGTTGCAG | GACTTTGGCC | CTGGTTATTT | CTGGCTGTTG | 79500 |

| | | | | | | |
|---|---|---|---|---|---|---|
| GCTGGAGGTT | GCCCACAGCT | TCTACAGGCC | ACCCCTCAGC | TCTTTGCACA | TGGGCTTCTA | 79560 |
| ACATGGCCAG | TTATTTCTTC | AGAGAGAGCT | CAGGAGACAG | ACTCTTTAGA | GAAAATCTGC | 79620 |
| CAGCAAGATG | GAGTCTTACA | TAATGAAACG | TAATCATAGA | AATTATATCC | CATCATCTTT | 79680 |
| GCCATATCCT | ATTGGTCAGA | AGCAATTCAT | AAGCCCTGCT | CACACTCAAA | GACAAGGAAT | 79740 |
| TTTACGAGGG | TGTGAACACC | AAGAGGCAGG | AATCATAGAA | GGCCACCCTT | GAGTCTGTCT | 79800 |
| TCCACAGTGG | CCAACCCTGA | ACGGCACTGA | GATGAGACTA | TTTAAAGTC | TTTATTTATC | 79860 |
| CCACTTAATT | TGAATAAATG | TTTTGCTGCA | GATATATTGA | TGAATTTGAT | TACAGGGCTC | 79920 |
| TGCCTTAGGC | CATGATGGGG | TTGAACTTTA | GAGTATATGC | ATTTTTTGC | CTTTATAACT | 79980 |
| TCTAAACTAA | TTTGAATGGC | AAAGCCCATT | TTGTTCCAGG | GATTTCAGAA | AAGGAATTAT | 80040 |
| AGACCTGTGT | TCCCCTCAAA | TACACAACAA | CAAACAACAA | CAAAACCCAA | AAGCACTCTG | 80100 |
| TATTTCATCC | TATACAGATG | ACAGGAAGGA | AGAACAAGAC | TTTGTGTAAG | TTTTGCTGGG | 80160 |
| ATTTCACTGA | GTCAATTTGC | CTACTCTCAT | CTTTTACAGA | AGGAATCATA | ATATGGTTCA | 80220 |
| AGTGAAACTA | TTTCTTTCTT | TCTTTCTTTC | TTTTTTTTT | TTTTGAGAC | AGAGTCTCGC | 80280 |
| TCTGTCGCCC | AGGCTGGAGT | GCAGTGGTGC | GATCTCGGCT | CACTGCAAGC | TCCGCCTTCC | 80340 |
| GGGTCAAGTG | AAACTATTTC | TTAAATGGGC | TTATCTTTTA | ACTAAATATT | TCTCCCCTCT | 80400 |
| TAAACACTGT | TTATTAAAAT | TTTTCTTTTT | TCAAATTTTT | TTTTGAGATG | GAGTCTCGCT | 80460 |
| GTTACCCAGG | CTGGCTTGCA | GTGCCGCAAT | CTCAGCTCAC | TGCAGCCTCT | GCCTCCTGGG | 80520 |
| TTCCAGCGCC | TCAGCCTCCC | GGGTAGCGTG | GGATTACAGG | TACGCACCAC | TATGCCTGGC | 80580 |
| TGATTTTTGT | ATTTTAGTA | GAGATGGGGT | TTCACAATGT | TGGCCAGGCT | GGTCTCAAAC | 80640 |
| CCCTGACCTC | AGGTGATCTG | CCTGTCTCTG | CCTCCCAAAG | TGCTAGGATT | ACAAGTGTTA | 80700 |
| GTCACTGTGC | CCAGCTTTAT | TACAAAAGTG | ATAGGAATAA | ATTTTATTTT | TATTTTTAAA | 80760 |
| TGTATGTTTA | TTTTATTTTA | CATTGCCTTC | AAGCAGATGC | AACAAATACA | TTTTAATCAG | 80820 |
| TCAAACAATA | TAAAGGATAT | AAGGAGAAAG | TTCAAGGTTT | TTCCCACCCG | TCTCCAATCT | 80880 |
| GACTTCTCTA | GGTAGGGTGA | TCTATATCTT | TCCCTAAGTT | TGTACAAACG | TAACATATAT | 80940 |
| ACACTGTCTC | TTCTATGTTA | CTCGTTACTT | TTTATGTCTA | ATATTCCATA | AGAATATAAT | 81000 |
| AAATATATGT | AACCATATCC | CTACTGATGG | AGCTTCAGGC | TGTTTTAGA | ACTTAGTTAT | 81060 |
| TACAATGTTG | CTACAATAAC | TTTCTAGTCC | ATGCATCCTT | ATATCCTGGT | GCTTTCATTT | 81120 |
| CTTTTGGGAA | CATACCCCAA | ACTGGGATTG | CCGAGGTTGT | TGTTAATCTT | AATATATGGT | 81180 |
| ACCATATTAC | TTGACTCAAA | GTTGTAACAT | ACACTCCTAC | CAGCACCAGG | AATAATGACT | 81240 |
| CACATATACT | GAGCACTCTT | TAGTCTGTGA | CAGATTAGAA | AAGCTTACT | TTTCTTGGTT | 81300 |
| CTTGTTTTAT | ATCACAGTCC | TCTCTATATG | GGGCATTTTT | GCTTTATAGA | GGAGGAAATA | 81360 |
| TGACACAGAG | AGGTTAGGTG | AGTGTTGTAG | GATCTCATAA | CTAGAAGGTA | GTCATAGAAA | 81420 |
| GAGTCTAGAG | TCTAGAAACC | ACTCTCTCAC | CATTTTGCAA | TGTGGCAGAA | AATGCAAAGT | 81480 |
| TGTTATTTAC | TTATCTCTTT | TAGACAGGGT | CTCACTCTGT | CACCCAGGCT | GGAGTGCAAT | 81540 |
| GGCCCCATCA | TGGCTCCCTG | CAGCCTTAAA | TTCCTGGGCT | TAAGCAATCC | TCCCACGTCA | 81600 |
| GCTTCCCCAG | TAGCTGGGAC | CACAGGCAAG | CACTGCCACG | TCTGGCTAAT | TTTTAAAAA | 81660 |
| TTTTTGTAG | AAACACTATC | TCTTTATTTT | GTTCAGGCTG | GTCTTGAACT | CCTGGGCTCA | 81720 |
| AGCAGTCCTC | TCGCCTCGGC | CTTCTAAAGT | GTTGGGATTA | CAGGCATGAA | CCACCATCTC | 81780 |
| CGGCCTGAAG | TTTATTTAAT | CCATTGCCTT | GTGGACTGGG | CATTGAAGTT | GTGTGTAGTT | 81840 |
| GGGTTTTTTT | GTTGTTGTTG | CTGTTGCAGA | CAATACTACT | GTGAACATTC | TTATCCATGC | 81900 |

```
TTCCTTGTGT CCCGTAAATG TTCCCTCCAG GGAGATACCT TGGAGTGACA TGCTGGTGTG    81960
AGGGATGCAT ATCATAATTT TACCAGATAC TACAGATCTT GAAATTGTTC CAATTCTACC    82020
CCACAAGCAA TATAAGAGCT CTCACTCCTC CAAAACTCCC TGAGTCTTTA CTTATATAAT    82080
TTATGATTTT GACAGTCTTA CAGATTTAAA ATGGTACCTA ATTGTGTACT TAATTTGTGC    82140
TTTTCTGATT TCACTAGTGA GATTGAGATT CTTTTTGTAT GTCCATTAGC CCTTCAGGCC    82200
TCTGTGATTT ACCCATGATT TACTGTGGTT TAATAATTTT TATTGGGTTC TTTTCCTTAT    82260
TGATTTATGG GAACTTATTA TAGCTGATAT CTTCTGGCAT GTGGATGGCA TTTTGCATTT    82320
TCATCCTGTT TTTTGATAAA TAGGGTTTCA AAATTAAGTA GACACATTTT CCTTCAAGGT    82380
CTGTGTCTTT TATGTCCAAA GAGCTTAGTC ATCAGTGGGC AGTGAATTTT ATCACCTAAT    82440
TAATTTTATT AGCCCCGTGT GCTATGCCTG TAGTTCCAGC TACTGGGGAG ACTAGGGCAG    82500
GAGGATCTCC TGAGCCCAGG AGTTCGAGGC TGCAGTAAGC TATGATCACG CCACTGTACC    82560
CAGCCTGGGC AACAGAGCTA GACCCTGTCT ATTAAAGGAG GAGGCCGGGT ACAGTGGCTT    82620
ACGCCTGTAA TCCCAGCACA TTGGGAGGCC GAGGCAGGAG GATCACTTGA GGGCAGGAGT    82680
TTGAGACCAG CCTGGCCAGC ATTGTGAAAC CCTATCTCTA CTAAAAATAC AAAAATTAGC    82740
CAGGTGTGGT GGTGTGCACT TGCAGTCCTA GCTACTCTGG AGGCTTAGGC AGAATTGCTT    82800
GAACCCAGAA GGCAGAGGTT GCAGTGAGCT GAGATTGTGC CACTGCACTC CAGCTTGAGC    82860
GACAGAGTAA GACTCCATCT CAAAAAAAAA AAGAAGAGAG ATGAAGGAGG AGGAGGAAGA    82920
GAAAGAGGTG GGGGAGGGGA AGGAAGAGAA AGAAGAAGAA AGGGACAAAA AAATTTAGCT    82980
GTCATCTTTG CTCTGATAGC ATTATAATGA TGATGAAGAC AATTGCTAGG TTGGTGAGAG    83040
AAGGCTATAT ACACACCAGA ACTCTCCACG TATATGGCAA GTTCATATAT TTTGTTAAGT    83100
ATGTCTCATT GGAGACCTTC TTTTCCCGTA ACTATGACCA GTGCTCTGCC AGCTCAGTCA    83160
ACAACAACAT TGCATGTTGG CTCCATACCT GGACTCTTGG TCCAATTGGT AATGAAACCA    83220
TCCCACCAGT GTCTTCATAA TATATATATA CACACACACA TATATATATA GTATTCTCTC    83280
CCAGTGTCTT CATAATATAT ATATATACAC ATACACACAT ATATTATATT CTCTCTATAC    83340
ATATTTATTT ATATATCTAT ATCTATATCC TTCCACCTCA GGTCTCCCTC TGTCTCCCAG    83400
GCTGAGTGGT GCAGTAGTGC GATTATGGCT CAACCAATGA GAGGATCAAT GGCAATCCTC    83460
TCATTTCAGC CTCCCCAGTA GCTGGGACTA CAGGCATGGG CCACCACATC TGGCTGATGT    83520
TTAAATTTTT TTGAGACAGC ATCTCTATAT GCTATAGATA TATATAGTAT CCTCTCTCTA    83580
ATATGGATAG AGGATACTAT GTCTATATCT GTATCTATCT ATCTATGGAG AAGGAATACT    83640
ATATATCTAA TAAGATGTAA TCTATATTAT ATATAAAAGT GAAGCATTGA TTGGTACATA    83700
TAATATATAT ATTGATTACT GTGTGTATAT ATTTGTTTTT TCGAGACAGG CTCTCACTCT    83760
GTTGCCCAAG CCGAGTGGTA CAGTGGTGCG ATCATGGCTC CACCACCTGA GCTAAAGTGA    83820
TCTTCTCACC TCAGCCTCCC CAGTTGCTGG GACTACAGGA ACAGGCCACC ATACCTGGCT    83880
AATTTTTTAA TTTTTTTTTG AGACAGGGTC TCCCTTTGCC ACCCAGGCTG GAGTGCACTG    83940
GCGCAATCTC GACTCACTGC AATCTCCACC TCCCAGGCTC AAGTGATCCT CTCACCTCAG    84000
CTTCCCGAGT AGCTGGGACT ATTGGTGTGC ACCACAATGC CTGGATAATT TTTCATATTT    84060
TTTGTAGAGA TGGAATTTGG CCATATTGAC CAGGCTGGTC TCAAACTCTT GGACTCAAGT    84120
GATTGACCCG CCTCAGCCTC CCAACGTGCT GGGATTACAG GCATGAGTCA CTGTGCCTGG    84180
CCTGATTATT GTACACATTT TTGATGTAAT GTATTATATA TGTCATATAT GACAATCTAG    84240
ATGAATATAT TAAAGATTGG GTTTTCATTT ATATATTGTA AAATACATAC ACTATACATA    84300
```

-continued

| | | | | | | |
|---|---|---|---|---|---|---|
| TATAATATGT | AGAACATATG | CTATACATAT | TATATATGTA | TATGTTAACA | TATATAATAC | 84360 |
| ATACACATAT | AATATGTATA | GTTGCAAATA | TAAAATTTGG | TTTGTTATTT | ATATTATTTT | 84420 |
| GTGCAGGAGT | TCTATATCTA | TGTCTATAAG | CGGGAGCCAT | AATTTCTAT | TCTTTGTAGG | 84480 |
| ATTTGGTATG | AGATTGGCAT | TACTCATGCC | TTGACTTCTA | AATTTCCTAT | AAAACTGACA | 84540 |
| AGTTCCATTT | TTGCTTGATA | AAGATGCACG | TTTTATTATC | TGTCGGTAAA | ATTTAAAGTA | 84600 |
| GTGATTTCAT | TTCTTTAATG | TTAGGTCTGC | CCATGCTTTA | TTTGTTTTTT | GAGTGAGTTT | 84660 |
| TACTCAGAAA | TATTTTTTCT | AGGAAGTAAT | AATTTTATCA | GTACTTTCAA | TTTTATTAGT | 84720 |
| AGCATAAGAT | TTATTATAAA | GTTCTGTAAT | ATTTAAAAAG | TTTCTGTATT | CATTCCATTT | 84780 |
| GTGCCTTCTG | TCTTACTTTG | ATAAATCTCA | TTGGAGGTAT | GTCTATTTTA | TTAAATTTCT | 84840 |
| TTTAAAAGAA | GCTACCTTTT | TTTTTGTTTG | TTTTTCCTCT | TTATTGCATT | CTTGTTTTCT | 84900 |
| TTAACTTCAC | TGTTATATTG | TTTAATATCT | ATTTTTTCTT | TTTAAAAAAT | TATATTTGGC | 84960 |
| TTTCTATGTT | CTTTTTAAAA | TTTAAATTAG | ATGCTTGGCT | CATTAATGTT | CAGCTTTTTA | 85020 |
| ATTTTTCTAA | GATAAGCATT | TAAAGCCTAC | AAATTTTCCT | TAAAATTCTG | CTTTAGCTTC | 85080 |
| ATTGTATATT | TTTATAAATA | ACTTTTTATT | ATTGTTCCAT | TCTATACATC | TTCTAATGAC | 85140 |
| TTATTAGTAG | TTTACATTTC | CTAATATTTA | GAATCTTTTT | AGTCATCTTT | TTATTATTGG | 85200 |
| TTTATAATCT | TATATTGAGG | CTAGAGAAAA | TGATCTGTGT | AATACAGATT | TATTGAAACT | 85260 |
| TGTTCAGACT | GTTTTCTGCC | TAGTATTTAC | TCAGTTAGTG | CATGTTCCAT | CTATACCTGA | 85320 |
| GAAAACTGCA | TATTCTCTGC | TTACTATTAT | TAAACAATTG | CTGAGCTTTA | TGTATTGACT | 85380 |
| ATGAGATTGC | GCTTCTTAGA | TTGTTCAGAC | CTTCCGTATC | TTCCCTTATT | TCTTTCTTTT | 85440 |
| GGTCTGCCTG | ATCTATCAAT | TATGGAAAGA | AGAATGTTAA | AACATCCCAT | GATGATTGTA | 85500 |
| GATTTGTCCA | TTTCTCCTAT | AATTCTACAA | TTTTTGCTTT | GTATATTAAC | ACAATTCTAA | 85560 |
| ACATGAATTC | ACTAATAATG | TAGTACATTT | ATGTTAAAA | TTGTGTTATC | TTTTTAGGT | 85620 |
| GACTCCTTTC | ATTCTTTCTT | TTTTTTTTTT | TTTGAGACAG | AATCTCTCTC | TGTCACCCAG | 85680 |
| GCTGTAGTGT | AGTGGCGAAA | TCTCAGCTCA | CTGCAACCTC | TGCCTCCCCG | GTTCAAGTGA | 85740 |
| TTCTTGTGCT | TCAGCCTCCC | AAGTAGCTGG | GATTACAGGC | ATGTGCCACA | ATGCCCAGCT | 85800 |
| AATTGTTGTA | TTTTTGGTAG | AGCCAGGGTT | TTGCCATGTT | GGGCAGGCTG | GTCTTGAACT | 85860 |
| CCTGGCTTCA | AGTGATCCGC | CTGCCTTGGC | CTCCCAAAGT | GCTGGGATTA | CAGGCATGAG | 85920 |
| CCACCACACC | TGGCCCTTCT | TCCATTCTTA | ATAATGCTCT | GACTTAATAT | CTTTTGATAT | 85980 |
| AATACTATAA | CAGTATATGA | CTATATTATC | TATCTTTTAG | CTTCCAATCT | TTCTATATGT | 86040 |
| TTTTGTTGAT | GTGTCACACC | AATAGATAGG | TGGAATTTTA | AAAATCCAAT | TGATATTTTT | 86100 |
| TCTCTTAAGT | GGTATTACCA | CCCCGTAAAC | ATTTTAATTT | CTCAACATGG | GTTTTCCTGG | 86160 |
| GTCATTCAGG | TAATATGAAT | TGAAACCCCA | AACTTCTGTG | AGTCAGGCTG | ATAAAAGCTA | 86220 |
| ACTGAATAGA | GTTTGAAAAA | GGAGGGTATT | TACAAAGGTG | AGGAGTTGGG | AAATCCACAA | 86280 |
| GGAACAGGAA | GCACCCAGAA | CTAGGAACAG | TTAGAGAGCC | ATCACCTCCT | CTGGGCCTCA | 86340 |
| AGTGGCAGGT | GTAGGGAGCT | GTAACTATAC | TAGAGTGTGC | CCAGAGGCAG | AGGAATGCAG | 86400 |
| ACCCTCCAAA | TCATAGCGTG | GGACTGGGGT | ACTGAATACT | CCCAAGGCTG | CTTCTTTGTG | 86460 |
| CCCTATGGTC | TCCTCTGGTG | CTTCCCATTG | GCTGAACCAA | GCCAGAGGGC | GGAAAGCCTG | 86520 |
| GTTAATCTGT | CCATGTCAGC | CTTCCTGGGC | ACAGAGCAAG | ACAGGGAAAA | GTGAGGGATT | 86580 |
| ATTTGGAAGA | ACAAACAGAG | AGCATCCAGC | ACAGGAAGTG | TTTCTGAATA | CTTGAATTCC | 86640 |
| TTAATTGTCA | CAGACCAACT | GATCAACATT | TAACTCAGTA | GCACAGTGGT | TTCCTTAACT | 86700 |

| | | | | | | |
|---|---|---|---|---|---|---|
| CTCTTGTTAG | AACATCCTAT | TACCATTTTT | TATTTTTAAA | ACTGCATACT | GTTCCAGTAT | 86760 |
| CTCACTTTAG | TTATCAGATC | TTTTTCTGTC | TTGTTTGATT | CTAGTCTGAT | ATTTTTCCAT | 86820 |
| GTTATATTGG | TCCTCCAGTG | TATTATTATC | TCATACTAAT | GCTTATGGAA | CATTATCTGA | 86880 |
| GGGGAAAGAG | AAGAGCTTAC | AATTAAAAGT | CATGGGACTA | GGCATGTGTC | ATGAGACCTG | 86940 |
| GGTCTTCCAA | TAACAAGCTA | AGACATTAGC | TGAGTCATTT | TCCCTCTCTG | ATTCTCAATG | 87000 |
| TTGGTGGTTA | TTCAGTAGAG | AAGGGAAAAG | GTATCTTTCT | GCTCAACTGT | CTCATGATTC | 87060 |
| CTGGAAGTCC | TGCATGGGAG | AAGAACTTTG | GACAGGATGG | TAACCATATT | AACAGGTTAG | 87120 |
| TTCTGTACCT | TGGCATCCTT | GAATAATTAA | GACGAAGATG | ATGTTGATGA | TATCATTATT | 87180 |
| ACTACATGTT | GTTAGAAGAG | CTGAAGCAGG | ACTGGCTTGT | CTGTCATAAT | GTAAAAGAGT | 87240 |
| CTTGGAAGAT | GTCCGGGGTC | CAGGGTCCAA | AACCCCTCGT | GGCCTTTGGA | ACACCAAGCT | 87300 |
| CTGTGCCAAA | TGGTGGAAGG | CTGCCCTGCC | GCACCACAAA | TCTAAGCCTA | GGGCATAAAA | 87360 |
| CCCCTTGTGG | CTTGGATGGA | ACCCAGGGCT | CAGGGCATAA | AACCCCTCAT | AGCCTCTGGA | 87420 |
| AAGTGCACAG | ACTTGTTGGT | TCCTTGCTTT | TCACTCATAA | ACGTGTCCTC | TACTATCTCA | 87480 |
| AGCAGCAGAG | TATATTCTAC | ATGTGTCAAA | GAAAATGCTA | AACTGTCACA | GCTACGCTTA | 87540 |
| ATGCACCACT | ACCTTTCTAC | CCCCATGTCC | TCATGCCCTC | ACCTGTTTAC | CCTCACGTCC | 87600 |
| TCACCACCTG | CTTCTTTGTT | TGATCACCAA | TAAATAGTGT | GGGCTCCCAG | AGCTTAGGGC | 87660 |
| CTTTGCAGCC | TCCAATCTAG | TGCTGGCACC | CTGGACCCAC | TTTATGCACT | CTTAACTTGT | 87720 |
| CTTTTCTCAT | TCCTTTGACC | CCGCCGGACT | TTGTAGCCCC | CACGGCCTGG | TGTTGGGCCT | 87780 |
| GATCACCCCA | ACAACTACCA | CTTATTAGTG | GTTACCATGT | ACCAGGAAAT | TTTACCAAGC | 87840 |
| ATTAAGCAAA | CATAAGCTTA | TTCAATCCTA | CCCACCATTC | TCTGCAACAA | ATACGGTAAT | 87900 |
| TTCCACTTTA | TAGTTAACAA | ACTGAGGCTC | AGAAAGTTAA | ATGATTTGCC | TAAGCTCACC | 87960 |
| CAGTTTATAA | GAAACAATAG | TTGGGTTTGA | ACACAGGCTG | GTTTATTGA | AATAACTTG | 88020 |
| TGGCTGGGCA | TGGTGGCTCA | CACCTGTGTA | ATCCAGCACT | TTGGGAGGCC | GAGGTGGGTG | 88080 |
| GAACACTTCA | GGTCAGGAGT | TTGAGACCAG | CCTGGCCAAC | ATGGCGAAAC | CCCATCTCTA | 88140 |
| CAGAAAATTT | AAAAAAATTA | GCCACTTGTG | GTGGTGCGCA | CCTGTAGTCG | CAGTTACTCC | 88200 |
| GGAGGCTGAG | GCAGGAGAAT | TGCCTGAATC | CAGGAGGTGG | AGGTTGCAGT | GAGTTGAGAT | 88260 |
| AGTGCCAGTG | CACTCCAGCC | TGGGTGACAG | CAACACTCCA | TCTCAAAATA | AATAAAATA | 88320 |
| AAATAACCTG | TGTTCTTCAC | AGCAACAAAA | TTATTTTTGT | TTGTTTGTT | TTGTTTTGCA | 88380 |
| GTTAGTGTGA | CTCTGGATCC | AGATACAGCT | CATCACGAAC | TAATTCTCTC | TGAGGATCGG | 88440 |
| AGACAAGTGA | CTCGTGGATA | CACCCAGGAG | AATCAGGACA | CATCTTCCAG | GAGATTTACT | 88500 |
| GCCTTCCCCT | GTGTCTTGGG | TTGTGAAGGC | TTCACCTCAG | GAAGACGTTA | CTTTGAAGTG | 88560 |
| GATGTTGGCG | AAGGAACCGG | ATGGGATTTA | GGAGTTTGTA | TGGAAAATGT | GCAGAGGGGC | 88620 |
| ACTGGCATGA | AGCAAGAGCC | TCAGTCTGGA | TTCTGGACCC | TCAGGCTGTG | CAAAAAGAAA | 88680 |
| GGCTATGTAG | CACTTACTTC | TCCCCCAACT | TCCCTTCATC | TGCATGAGCA | GCCCTGCTT | 88740 |
| GTGGGAATTT | TTCTGGACTA | TGAGGCCGGA | GTTGTATCCT | TTTATAACGG | GAATACTGGC | 88800 |
| TGCCACATCT | TTACTTTCCC | GAAGGCTTCC | TTCTCTGATA | CTCTCCGGCC | CTATTTCCAG | 88860 |
| GTTTATCAAT | ATTCTCCTTT | GTTTCTGCCT | CCCCCAGGTG | ACTAAGGAAA | AGAGCAGAAG | 88920 |
| CTCCTTGGTT | TAACCAGCAC | AGAGAAAATA | ATATAAATCC | CATAAGGGCA | GACGTTTGGT | 88980 |
| CTGTTTTCTT | CGCTGTCATT | TCCTTAGTAG | TTAGACTAGT | GCTGAGATTT | TAGTGGATAT | 89040 |
| ATAATTGATT | TATGTTGAAT | ATATGGACTT | AGCAACTAAA | AATACCACAG | ATGGTTAACC | 89100 |

-continued

| | | | | | |
|---|---|---|---|---|---|
| TGGACTGGGG | CAAAGCAAGA | TAATAGTGAT | GATCGTATGT | TGCTGTCTCC | ATCCGTCTTT | 89160 |
| AATGGGTCAG | GGCTTTGATT | TCCAAGGGTC | TTCAGGTGAT | GAGTAGGGGT | ACCCACAAGT | 89220 |
| CAGAAGGTCT | GCGTTCTCCT | AGTTTGTTTG | CTGCCATTTG | AACTCATGTA | GGGAATGAAA | 89280 |
| GAAAGCTGCA | ATTATCCGCC | AACTGCATTT | AAAACAAAAC | AAAACAGAAA | AATCAAAATA | 89340 |
| ACATTGACTC | TTCCAACCAC | TGACATGTTG | TTTAATAATC | TAAGCGGCAG | TCCTGGAGGC | 89400 |
| TACCAGACTT | ACTGAGTTCT | ACCTGAGAAA | CAGCCAAGCA | AAGTGTGAGA | GAAGGGTTAA | 89460 |
| GACTGGCTTA | CAATGAGATG | CTTCAAATGA | AAAGGGAATT | ATGAGTAAAA | TTGAACTTTG | 89520 |
| ATGGGGATT | CAGTTCTGGA | AAAGAATTTG | GTATTTTCCA | GTCTGCTAGG | ACCAATTACC | 89580 |
| TTGAAATATT | TTAAAATCTC | AGTAAATAGT | TATTGCTGAA | ATGGCTGTTG | GCAGTTCTTA | 89640 |
| TTATGATTCA | GAGAAGAGCA | AATAGACCTT | AACTTCATTT | TGAAAAGAC | CAAATTACCA | 89700 |
| TACCCGAGTG | AGTAATGACA | GGACTACAAC | TAAAACATAA | ACAACATTAA | TGATGACCAT | 89760 |
| AAAAAGTCAC | AAAATTGCTA | AATGTTATAA | TTTAGAGTTG | ACATAAAAAT | TGATGGCCAG | 89820 |
| GCATGGTGGC | TCACGCCTGT | AATCCCAGAA | CTATGTGAGG | CTGAGGCAGG | TGGATCACTT | 89880 |
| GAGGTCAGGA | GTTCAACACC | AGCCTGGCCA | ACATGGTGAA | ACCCTGTCTC | TACTAAAAAT | 89940 |
| ACAAAATTA | GCCGGGCATG | GTGGTAGGGG | CCTGTAACCC | AGCTACTCGT | GAGGCCAAGG | 90000 |
| CAGGAGAATT | GCTTGAGCCT | GCAGCAGCTG | CAGTAAGCCA | AGATCATGCT | GTGCCTCAAG | 90060 |
| GAAAAAAAA | ATTAATGTTT | ACTGATATTT | GTTGAAGTCC | TACAACATCA | CCTCTGAGAA | 90120 |
| TAGGAGAAAT | GAAGCAACAG | TTGTGTCTAG | ATGTCAGAGG | CATGGCTGGG | CCTCCATCTC | 90180 |
| TGCCTAAGGG | AGATATAAAA | GAGTTCAAAC | TATTGCCCAT | GTTCCCAGG | GTCAGAAGTT | 90240 |
| CTAATTATGA | TGATAGAGGC | TGGGTTGTAA | GTAGTAAGTG | AAGGGTAGCA | GAATATGCCA | 90300 |
| TCTTTGGCAT | AAGAAGTATT | TTGAGTTGAA | GACAATTGAG | AAAAAAATA | GATTAAAAAC | 90360 |
| AAACAAACAC | CTCTGCCCTC | TCCCTATTTG | CCTAAAAGCA | GGATATGAAA | TTGTGAAGGT | 90420 |
| GTCTTCTTAC | TCGGGAAGA | ACAAAGTTA | GTCACCAGAG | ACTTTAGACT | CTTATCAGCC | 90480 |
| TGGACATAGC | ACCAGAGAAG | TCTTTTTTTT | TAAAAAAAAA | AAAAAAAAA | GGGAAAGAAA | 90540 |
| AAGTTGCCTT | CCCACAATTT | ACTGCACTAG | AAACTCAAAG | TCCTTTTCGT | CTTCCTTGTC | 90600 |
| ACTTAAAAAA | TGTATTCTTT | TCTTAAAATG | CTATATAAGC | CCAAGTTCTA | AATCCTCTTT | 90660 |
| TGAGTATTCA | TCTCAGTACT | CCCCTGTGTT | TGTACAATGC | ACATGCTTTG | TTTCTGTCTT | 90720 |
| GTCAATCTGT | CTTTTGTTAG | TCTACTTGAT | AGGGCCACAG | ATGGAGAACC | TAAGATGAAT | 90780 |
| AGAAAAAAAA | GATTTTTCTC | CCCAACAGAA | GGATTATCGC | CAGTTGCACT | TGTTCTATAT | 90840 |
| ACCCGTAGTC | TCGGTATGCT | GACCCAGACT | TGGGTAATAG | GACCCAGTGG | GTAACCGAGG | 90900 |
| AACCCCACCT | TTGTGCAGGA | TCAGTGAAGA | TGTAATCTGG | ATATTCATAA | GCTCTTCTCT | 90960 |
| ACCTCTTGGC | ATCCCACAGT | CCTGTGTTAA | TGTAAGTGTG | GTCTTCCCCA | GAAAGGGGAG | 91020 |
| GCCTCCCTAA | CATTGTTAAA | GCCTAGCATA | TGCTGCTTAG | AGGAAATTCT | ATATCCCTAA | 91080 |
| GCACTTAGAT | TGCTGAATAA | GAAAGAATGA | TAATAAAATA | AACAATTAAA | TAAAGTTTT | 91140 |
| AAAAAATGAA | TAAAATAAAC | CTGTGGAAAC | TATAAGGAAG | GCCAGAAGAA | ATATAAAATT | 91200 |
| GGAGATTAAT | TGGGGTGCAG | GAAAGTTATG | GAAAGAATAT | AAGTCCTGCT | AGATAAATCA | 91260 |
| TTAGCTATTT | TAATAAAGAA | TACAGAAGAA | AATAGGAACA | AAGAATATA | TACTGGAATA | 91320 |
| ATTTTGAGAG | TAATTTGAAG | AATTAGATGC | AAATAAATTT | GAAACCTTT | AAAAGAAAC | 91380 |
| CAATGGCCTA | ACTGACCCAA | GAAGGAAAGA | AAATCTAAAC | AGACTGATAA | ATACAAAATG | 91440 |
| AAATTCAGAC | ACTTACAGAG | CAGCCAGGCA | TGGTGGCTCA | CACCTGTAAT | CCTGTCACTT | 91500 |

| | | | | | | |
|---|---|---|---|---|---|---|
| TGGGAGGCTG | AGATGGGAGG | ATCACTTGAG | GCTAGGAGTT | TGAGACTAGC | CTGGGCAAGC | 91560 |
| TCCCATCTCT | AAAAGAAAAG | AAATTAGCTG | GGCATGGTGG | CATGTGCCTT | AGTTTCAGTA | 91620 |
| CTCAGGAGGC | TGAGACGAGG | ATTGCTTGAG | CCTAGGAGGG | CAAGGCTGCA | GTGAGCCATG | 91680 |
| GTCATGCCAC | TGAATTCCAG | CCTAAGTGAC | AGAGCAAGAC | CTTGTCTCAA | AAAAAAAAA | 91740 |
| AAAAAAGTT | ACAGAGCTCC | AACTAAATAA | TGTGGGGAAC | AAAAGAAAAA | AGAAGATGAT | 91800 |
| TTTATGGCTG | ATTTTTTTTT | TAAGGAAAAG | CAATTCATGT | ACCCTTGAAG | ATTAGATTAA | 91860 |
| GTTCTATAAA | ATAGCCCAAA | ATGACAGTGG | CTGAAACAAG | TTTATTTATC | TCCCATTTAA | 91920 |
| AGCAAGTCTA | GATGTGGAAG | TCTGGGAAGC | CCAGAAAATC | CAGGTCTTGT | TTGTGTATGG | 91980 |
| AAACTCCAGA | AAATCACAGA | TTCCTTCCAG | CCACCCCTCA | ATTACCCCTG | GGATCCAAGA | 92040 |
| GAGCCACTAA | AGTTCCAGCC | ATCATACTCA | CAACCCAAGT | TGTAGGATGG | AAAAAAGGAC | 92100 |
| ACAAAGTAG | GGTGAAGAGC | ATGTGTGCAA | CAGCTCTCTT | TTACTCTAGT | GTCCTAAAAC | 92160 |
| CTATCATAAA | ACCTTTGGCT | TGCCTTGCAT | TAGCCAGAAT | TTAGTACATG | GCCACACTTA | 92220 |
| AGAAGTCAGA | AAGATTAGCT | TTTTTTCCAG | GGTAGTTGGC | TGAAAATCAG | GAGTTCTCAT | 92280 |
| ATTAAAAAAC | AGAGAAGGGA | CATCGAATAG | ATGACCAACA | ATCTCCTTCA | CACTCATACT | 92340 |
| ATTTAAACTG | TCCTAGTCAA | TGACCAAAAA | AGAAAAGCCT | ACAAACTCAT | TGATATAAAA | 92400 |
| GCTTAACAAA | GGTACTCCCC | GCCCCCCGCC | CGCCACACAC | CATCCCCAAA | AGGAAATTTC | 92460 |
| TAATCCAATT | AACAGTCTTA | GGTTGGGCTG | CTGAAACAAA | ATACCACAGC | CTGAGTGACT | 92520 |
| TAAACAACGA | CAATTTATCT | CTCACTGTTC | TGAGGTCTGA | GTTGATTCTT | TGTGAAGGCC | 92580 |
| CTTTCCTAGC | TTGCAGATGG | CTACCTTCCT | GCTATGTCTT | CACATGGCAA | AGAGAGAGCT | 92640 |
| AGCTTTCTGG | TCTTTTCTTA | TAAGGGACCA | GTCCATCAT | GCCCATCATG | AAGACTCGAT | 92700 |
| CTGCTAGGAT | CTCAACTAAA | CCTAACTATC | ACCCAAAGAG | CCCACCTCCA | AAGACCATCA | 92760 |
| CATTGAATGT | GAGAGTTTCT | ACATATGCAT | TGTGGGAAAC | ACAAACATTT | ACTTCAACTG | 92820 |
| TAACTATTGA | AGCAAAAATG | TCCCCCCACC | ATAGACATCC | AGCACCACAG | TAGTACATTT | 92880 |
| ATTACAATTG | AACTTACATT | GACACGTCAT | TATCAACGAA | AGTCTGTAAT | TTACATTAGG | 92940 |
| GTTTATTCTT | GGTGTTGTGC | TTTCTATGGG | TTTTGACAAA | TGTATAATGT | CATGTATTCA | 93000 |
| CCATTATAGT | ATCACAGAAG | TTTCACTGCC | CTAAAAATCC | TGTGTTCTGC | CTTTTCAACA | 93060 |
| CTTCCTGTCA | CCCAATTTCT | ATCAACTAAT | CTTTTGACTG | TGTCCATAGT | TACTGTCTTT | 93120 |
| TCTAGAGTGT | CATACAGTTG | TGAAGCAGGA | AGCAGGAGTG | AACTCCGGAG | GCAGGGACTT | 93180 |
| TACTCCGGAC | CAGATTGAAG | ACTAGCCGAA | ACAGGGACGA | GGTTAAAGCA | CCTCTCCATA | 93240 |
| AGACACGCCC | ACCAGCGCCA | TGTCAGTTTT | TCGTTGCCAT | GGCAACAACA | GGACATTATC | 93300 |
| GACTTCTTTC | CTCTGTACCT | ACTCCGAAGT | TACCACTCTT | TTTCTAGAAA | TTTCTGCATA | 93360 |
| ATCCCCCTTA | ACATGCACTT | AACTAAAAGC | AGGTATATTA | CTGCAGAACT | GCCCCTGAGC | 93420 |
| TGCTACTCTG | GGCACATTAC | TTATGGGTTA | GCCCTGCTCA | GCAAGGAGCA | GTACCTGTTC | 93480 |
| TGCTGTTGTA | CACTGCTGCT | TCAGTAAAAG | TTGCTAACAC | CACCACTTCA | CCCTTGAATT | 93540 |
| CTTCCCGGGC | TAAGCCCTAA | TTTTTGGCTT | GCTTGCCCTG | CATCAGTTGG | AGTCATATAG | 93600 |
| TATGCAGTCT | TTTCAGGTTG | GCTTTTTAGT | AACATACATT | TAAGTTTCCT | TCATGTGTTT | 93660 |
| TCATGGCTTG | ATCGTTTCTT | TTCTTTTTCT | TTTTCTTTTT | TCTTTTCTTT | CTTTTTTTTT | 93720 |
| TTTTTTTTGA | GACAGAGGAG | TCTTGCTCTG | TTGCCCAGGC | TGAAGTGCAG | TGGCACTGGC | 93780 |
| TCACTGCAAC | CTCCATCTCC | CAGGTTCAAA | CGATTCTCAT | ATCTCAGCCT | CCCGAGTAGC | 93840 |
| TGGGATTACA | GGCTCACGCC | ACTATGCCCG | GCTAATTGGG | GTTTTCCCAT | GTTGACCAGG | 93900 |

-continued

| | | | | | | |
|---|---|---|---|---|---|---|
| CTGGTCTCAA | ACTCCTGGCC | TCAAGCAATC | CACCCACTTC | GGCCTCCCAA | AGTGAATGCA | 93960 |
| TTTCTTTTTA | ACTCTAAATA | ACATTCCATT | ATTCAGAAGT | ACCACAGTTA | TCCACTTACC | 94020 |
| TACTGAAAGA | CATCTTGTTT | CCAAGTTTTG | GATAAATTAT | GAATAAAGCT | GCTATAAACA | 94080 |
| TCTATGTGCA | GGTTTTTGTG | TGGAGATAAG | TTTTCAATTC | CTTTGGATAA | ATACTAAGGA | 94140 |
| GTGTGATTGG | TGAATCTTAT | GGTAAAAGTA | TGGTTACTTT | TGTAAGAAAC | CACCAAACTG | 94200 |
| TCTTCCAAAG | TGATTGCACA | TTTTGCATTC | TCACCAGTAA | TGAACAAGTT | ACTATTGCTA | 94260 |
| CATATCTTTG | CAACCTTTGG | TGCTGACAGT | GTTCTAAATT | TTGGTCATTC | TACTAGGTAT | 94320 |
| GCAGTGGTAT | CTACTTGTTT | TAATTTGCAG | TTCCCTAATG | ACATGATGTC | AAGCATCTTT | 94380 |
| TCATATGCAT | ACTTGCATCT | GTGTATCTTC | TTTGGTGAAC | AGATGTTCAG | GTCATTGGCC | 94440 |
| TGCTTTAAAT | CAGGTTATTT | TCTTACTGTT | GAGTTTTAAG | TATTCTTTGT | ATATTCTAAA | 94500 |
| AATATTGTTC | TTCATCAGAT | CTGTCTTTTG | CAAACATTAC | CTGCCAATGT | GTGGCTTTTC | 94560 |
| TTCAACACTT | CTTTGTAAAT | TTGCAAGTCC | TTTGAGAAAA | GAAATGCACC | CAAAGTATTA | 94620 |
| ATTTGGCAAT | CTCATATCAC | GAGAGTACTC | TAAAGCTAAA | TAAATTACAG | TTTTTCAAAT | 94680 |
| TTTGAATTAA | TTGATCTTTG | CTATTGTTAG | CAAGGTCTTG | TATTCTTTTT | TTTTTTTTTT | 94740 |
| TTTTTTTTTA | ATAGAGACGG | GTCTTGCTAC | AGTGCCCAGG | CTGGTCTCGA | ACTCCAGGCC | 94800 |
| TAAAATGATC | CTCCTGCCTT | GGCCTTCCAA | AGTACTGGGA | TTACAGGCAT | AAGTCACCAC | 94860 |
| GCTCAGCCAT | CTGGTATTCT | TTAGCAACTG | TTTGGTAACT | TAATCTTTCA | CTTTTTGAAA | 94920 |
| ACAAAAAATA | GTTTTTTTCT | CATAGTTTTC | TAACAAAATC | TTCATAACTG | AAATAAATTC | 94980 |
| TCTTTATCAC | CTCTTCTTAT | AAATATGGTT | TTCTTTTTTT | AAATAAAAAT | TTAAGACATT | 95040 |
| TTATAACTGG | CCAAATTTAC | TAGCTTAGAT | ACTATTAGAT | AGTCAATATT | TTTTGTTGGA | 95100 |
| TATTTGATTT | TTATTTCAGG | CAACTAATAT | CTATTCATTT | TTGCACTGTT | GGAAGAAAAT | 95160 |
| TACTGATCAA | ATTCACTATG | TATTTGCAGA | AAATGGCTTT | CAATATTGTC | TACTTTATCA | 95220 |
| TCCTTTTTTT | TTTTTTCTTT | CTTCCTTTTT | AGATACAGGG | TCTCACTATG | TTGCCCAGGC | 95280 |
| TGGTCTCCAA | CTTCTGGGCT | CAAACAATCC | TCCCTCCTTG | GCCTTCCAAA | GGGTTGGATA | 95340 |
| TGTTTTATCT | ACAGTTTTGT | TGTTTTGTTC | TGCTACAGGA | TATTTGCAAT | TGCCATTTAT | 95400 |
| CATGAAATTC | ATGACATACC | TTCTTCCACT | CTCCTTTTTA | TCTTTATTGT | TCTGGTTATA | 95460 |
| GGACTAGCTT | TGCATCTCTA | CTCAATTCTG | TATCAGTAGT | ATGCTTTCAT | TTTAAATTTT | 95520 |
| AAGTTTGTCC | ATATGTATAT | TGACACAGGG | TCTTGCTCTG | TTGCCCAGAC | TGGAGTGCAG | 95580 |
| TGGCAAGATC | AGGGCTCACT | GCAGCCTTGA | CTGCCTAGGC | TCAAGTCATC | CTCCCACCTC | 95640 |
| AGCCTCCAGA | ATGGCTGGGA | CTACAGGCAC | GCACCACCAC | ACATGGCTCA | TTTTTTTGTA | 95700 |
| TTGAGACAGG | GTTTCTCCAT | GTTGCCCAGG | CTGGTCTTGA | ACTACTGGGC | TCAAGCAATC | 95760 |
| CTCCCACCTT | AGCCTCCCAA | AGTGTTGGGA | TTACAGGCTT | GAGCCACCAT | GCCTCGCTTC | 95820 |
| TACACTTATT | TTTAATTCTA | AAATAATTTA | TAATAATAAA | TATTAACAAT | TAGATTTAAT | 95880 |
| TACTGATAAA | TATTAAATGT | TAAATAGGTT | TTATTAAATA | ATTAAATAAA | AATGAAAATA | 95940 |
| ATCAGTATTT | CAATTTAATT | ACTAATTATA | ATTCACAGTT | ATCCTTGTAA | CTCCTAATGT | 96000 |
| CTATATAAAA | GATTTTTATA | TTTTTTAATT | CTTAAAATTT | TATTATTTAT | TTCACACCAG | 96060 |
| GCCATCACTG | TGATACATTT | TTTAAAACAC | ATTAAATTAT | CACCAGAAAA | GTGCTGTGAT | 96120 |
| GGAAAATATA | AATTGAAATA | CCTTTTCTGG | TTAGGAGAGT | AATTCTGTTT | TTCTGATAGA | 96180 |
| GAATAGAAGA | GTCCTTCAGG | CCCCTCCAAA | CTGTCATATT | CCGGGCATCG | GGTGTCCCCA | 96240 |
| TCCTCACTTC | AGTCCACAGG | CAGGGTCCTC | AGTCTTCAGC | GCTCCTTCTC | TTTCCCCTTT | 96300 |

| | | | | | | |
|---|---|---|---|---|---|---|
| GTCTTGTGTC | TCCTTGGGTC | TCTTTTCTCC | AAGACCTAAA | CTCCCTGAGG | ACAGGACTAT | 96360 |
| TTTTTACATC | TTGATGTCAC | TCCTGAGCAC | TTGCTTTAAT | GTGTTGGACA | CTGGGTCCAT | 96420 |
| TAAAGATTGT | ATGTGAAATT | ATAAAGAAA | CGTTTTCACC | TTTCTGTGGT | ACAGCTATAA | 96480 |
| TTTCTGGTTT | CATTTACCAA | CTGGGTGAAA | GTGGACCAGT | GACACCATTT | GTCTGGGCCT | 96540 |
| TCCTTTCCTG | AAATATAATA | TTGGGGCAAT | AGTCCCTGGT | TCTTGTAAGG | TGTTCAGGCA | 96600 |
| CAAAACGCTA | GGCATGTAAC | ATACTAAATG | AGGTTTTCCC | AGTTAATTTA | TATGATTGCA | 96660 |
| AAGGACGTTC | ATATACACGG | TCTGCTAAAG | AATTCTGGGG | CCAATTAATC | TCTGTGGCAT | 96720 |
| GATGGGTAAG | TCGATCCCTT | CTCTGGGCGT | CTATTACTTC | AGAAAAGGCA | TGAACTCAAT | 96780 |
| TTTAGGGACC | ACACAAAAAA | ATTTATTCAC | TATCGTGTAG | GACTTGGTCA | TTAGAGAGCT | 96840 |
| TTTGTTTCTT | TTTTTAAAA | TTTTTTTAA | TTTTTATTTT | CGTGTATGTG | AATTTAATGG | 96900 |
| AGAGCTTTTA | AATAACCAGA | TATTTAAATA | ACCAGATAAT | ACAGATGCCC | GGCCTGCTCC | 96960 |
| AGACAAATTA | GAAAAGTATG | TAGGTGAGGA | GGGACCAGCC | AGAAGGCGGT | TTCAGCTCTG | 97020 |
| GAGTGACACT | GAACGTACTT | CTCTTCCAGG | GATGTCACGA | GGTGTCAATT | TCTCTGGCCT | 97080 |
| TACCCAGGTC | CATGCCCGCC | CCCAGGGGCC | CCAAGAATGA | CTTCAGCACC | CCACCCCCAC | 97140 |
| CTCCCTCTCC | AGATGTGGGT | CCTGGGAGCG | TTCAAGGCCC | GTCAGTCACT | CGAGCCACCC | 97200 |
| CTTGGCGGCT | GGACCAAATC | TTGGGCTGCC | GCCTGGATCT | GCAGCTGGAA | AGCGCCGTGA | 97260 |
| CCACCGGTGT | CCCCAGCTGG | AGCAGGGCGG | GCTGCACGAC | TCGCGAGGAC | GCCCTGAACC | 97320 |
| GCGGCTTCCT | CTTTCATAGC | CGCAGGACTC | GTGGTCAGAA | GGCCGACTCC | AAGCCTCAGC | 97380 |
| GGATCCACGA | AATGGCCTCT | TTGAGGCTGT | GGTGAAATTT | AAGATACCCT | TTCCCTGCCA | 97440 |
| TTGTTACTGA | CGTACTTCAG | CAAACAGGTT | AAAGTTCTGA | AAGGACGTGG | TCACGACTTT | 97500 |
| ATATTTCTTA | CAGATTTGTG | TCTCATGTTT | TGTGCGTAAA | AACCATTCGT | CCTCATTTGA | 97560 |
| GATTCTCATA | TCCGTAATTC | AGTTATACAT | AAAACTGAAT | TCAGTTATAT | CATAAAATGT | 97620 |
| TCCCATGCGG | GGAATGATTC | GTTGGGGTCT | CAGCCTGAGG | CCAGACGCAG | CAGAGAGATC | 97680 |
| GGGAGTTGGG | GGATGGCGGG | CGGGGAGCGG | AGAGGAGGCC | GCCCGCCGCC | AGACTCAGGG | 97740 |
| TCCAGCAGAG | CAGCAAATGC | TCCCCGGCTC | CCAGCCAGGG | CGCAGCTGCT | GGCCTGGGGC | 97800 |
| CGCCCCTCAC | GCCGCAGGAG | CCCCGCCCGC | AGCGCCGGCC | CTGCCCCTGG | CCTGTGAGGG | 97860 |
| CGCCAGCGCC | CCCTACAGCT | TGCAGTCGCC | CTGCGCGCCT | CCCCGCGAGG | CTTGTTTTCT | 97920 |
| AGCGCCTCTG | GTGGGCCGCC | TCCCGCAGGC | CTGGTGTGAG | CCTGGGGTCC | GTTCTCACAG | 97980 |
| CTGGATCTGG | GGTCTGAATG | CCGCGCCCTC | TGGAGAGCCA | CAGATGGGTC | TCCGCTGATG | 98040 |
| CTTCTCTCAA | TTTCCTCTAA | GAGCGAGAGC | TCCGGGAAAG | GAGCCGATCC | TGGTGGAAGA | 98100 |
| CTACAGGTCT | GAGTCCACTG | GACGAAAAAC | GAGGTGCGTT | AAGAGACCGC | GGGAGTGGGG | 98160 |
| AAATGGGGAA | GTGAGGGTGG | GGACTGGGCA | ATGGGGCGG | GACGAGAGGT | CTGGGGCTGG | 98220 |
| CGGGGACAGG | GCTTAAGAGA | GAGCCACCCC | TCCTAGCCTT | GAAGCTGTAC | CGAGCTTCCC | 98280 |
| TGTGATATTT | TAAAATGCAA | AAGTACAAAA | ATTGAAGTAA | TGGAACTATG | CGTACGCACC | 98340 |
| TCCTAGATTT | TTAAAGGTTA | ACGTGTGACT | GTGTTTACTT | CAGATGTTCC | TGAAATAAAT | 98400 |
| GAAAATGACC | AGTTAAAATG | AAGGAAGAAC | GCGCTTGCGT | CCCTCCTAGA | GGTCAAACAC | 98460 |
| TCTTCTGAGG | ATAGGTTGTA | TGCTCTCAGC | GCCTCTTTTT | ATTAAAGTA | TTAAGAAGTA | 98520 |
| CTTTTCCAAA | TATTAGATGT | AGTGTGTCAT | ATCATTTAAA | CGATTTTTTT | TGTTTAAAAT | 98580 |
| AGTCTTTTAA | AAATAATCTT | TTTATTTTTA | GATTTTTTTG | AGACAGAGTC | TCGCTGTGTT | 98640 |
| GCTCAGGCTG | GAGTGCAGTG | GCGCCATCTC | CCCTCACTGC | AACCTCTGCC | TCCCAGGTTC | 98700 |

-continued

| | | | | | | |
|---|---|---|---|---|---|---|
| AAGTGATTCT | CCTGCCTCAG | ACTCCCAAGT | AGCTGGGATT | AAAAGCGTGA | GCCACCACAC | 98760 |
| CCTACCAATT | TTTGTATTTT | AGTAGAGATG | GGGTTTCACT | ATGTTGTCCA | GGCTGGTCTC | 98820 |
| GAAATCATGA | CCTCCACTAA | TCCACCTACC | TCGGCCTCCC | AGAGTGCTGA | GATTACAGGC | 98880 |
| ATAAGCCACC | GTGCCTGGCC | ACTTTAATCA | TTTTTGTTTT | TGCATCTAGT | CTAAGAAATT | 98940 |
| CTGCACTAAA | ATTCTGCACT | ATTTTCTTCT | AAAATTTTAA | AACATTTTCT | ATCTGTGTCT | 99000 |
| TTGTTAGATG | TAGAAACTTT | TGTGTATGAT | ATGGGGTATA | GCTATAATTT | TATTTTATT | 99060 |
| CCATATGAAA | GCCAGTTTCT | CAGCCCAGGT | AATTGAATAG | ACCATCCTTT | CTCCACCAAC | 99120 |
| TCTTAAGGCT | ACTTCTGCTC | TATTGTGTTC | ATAGTAGTTT | CTAGGCTTTC | TGTTTTGTTG | 99180 |
| TACTGATTTC | TTCACCTATT | TTTGCATCAA | GGCTCTCCTC | TTGGGGAAAT | AAAACAATCC | 99240 |
| TGCCAACCAA | AGACCCTCT | GGATCCTCAA | ACACGCCATC | AGCATGGAAG | GCCGCTATGG | 99300 |
| CATAGCGAGA | GATAAATAGG | ATTCAGGCAG | TGCTGTCCTT | ACATCGCAAT | CATTCAGGTA | 99360 |
| GTTAGCAGGA | GCATCAATCA | GTACAGATAT | CCAGAGCTGA | TGGTCTTATT | TGTATGAATG | 99420 |
| CCCAGTGCAT | ATGGGATTGG | AGGGGAGGGC | TTGGAGTGGG | ATGAGGGGCT | AGTGGGATCC | 99480 |
| AGAAGGGGC | TAGTCTTCAG | GTCTTCCCTG | GAGAGTATGT | AATCTCTTAT | AACTAAGTGT | 99540 |
| TGATTTTTGT | TTTGTTTGTA | CCTTCTTTAG | ATATTGAAGT | ATTCGCTAAG | GCTTAACATG | 99600 |
| TAATATATTT | AAATCTTCAT | ATGAATACGT | TTATCTGATA | GATTTTGGTG | AGACATAAAC | 99660 |
| TATGAAACAA | ACAGAAAGAT | GGAACATGAG | AAAGGGTCAA | GGGTGGCCTT | GGTTAGGGAT | 99720 |
| GGCAGCTTTT | ACAACTATGA | GCTAAGATAA | AATTTAGAAG | GTTTTCTTTT | TATTTTAATT | 99780 |
| AATCATACCA | CTATTTTTCT | CCTTTAATTT | CCATATATAA | TGAGTTGATT | GTAGTATTTT | 99840 |
| TATTGTGCTT | AACTATTTTA | AGATAATAGT | TGTCTCTCCT | CATTTTAGCA | AATAATATAT | 99900 |
| TTAATGAAAA | ATCAACTTTA | TTGAGGAATA | ATTTATACAC | AGTAAAATAC | ACCTGTATTA | 99960 |
| ATTATACAAT | TTGATGCGTT | TTATATACCC | AAACAGTTAC | TACTGTAATC | AAGTTACAGA | 100020 |
| ACACTTCCGT | CAACCTAGAT | AGTTTCCATT | TGTAGTATCA | CCTGTGCCGC | CTCTTCCATC | 100080 |
| CTCTTGGCCC | CAGGCAGCCA | CTGATGTACT | TTCCATAATT | ACAGCTTAGT | TTTCCCATTC | 100140 |
| CTAAAATTTC | ATATGAATGG | AATTTATATC | ATATGTATTT | TTTATTTTCC | TTCACATTTT | 100200 |
| TGAGATTCAT | CCATTTGTG | TATATATCAG | TAGTTTATTC | CCTTTTATTG | CTTTATAATA | 100260 |
| TTCCAAGATA | TAGATATATT | GCAATTTTTT | TTTTTTTGA | GATGGAGTTT | CCATCTTGTT | 100320 |
| GCCCAGGCTG | AAGTGCAATG | GCATGGTCTT | GGCTCACTGC | AACCTCCGCC | TCTTCGGTTC | 100380 |
| AAGTGATTCT | CTTGCCTCAG | CCTTCCGAGT | AGCTGGGATT | ACAGGCGCCC | GTGACCATGC | 100440 |
| CCAGCTAATT | TTTTAGTAGA | GATGGGGTTT | CACCATGTTG | GATGGGCTGG | TCTCAAACTC | 100500 |
| CTGATCTCAG | GTGATCCGTA | CATCTTGGCC | TCCCAAAGTT | CTGGGATTAC | AGGCATGAAC | 100560 |
| CACTGCGTCT | GGCCGATATA | TTACAATTTA | TTTACCCATT | CACCTGTTGA | TGGACACGTG | 100620 |
| GGTTGTTTCC | AGTTTATAGC | ATTGTGAAAC | AAAGCCAGTA | TGAACATTTG | TACATGTCAT | 100680 |
| AGTATGGACA | TGTGTTCATT | TATCTGGGAG | AAATGACCCA | GAAATATTGC | TGGGCTGTAT | 100740 |
| AAGTGTTTAA | TTTTATGTTA | GAAACAGCCA | AACTTTTTTC | AAAGTAGTTG | TAACATTGTC | 100800 |
| CTCTTACATT | CACAATATAT | GAGAGTAGTT | TCCTCCACAC | CCTTGCTCAC | CCTGGGGATT | 100860 |
| GTCAGTCCTT | TTAACATTAG | CTATTCTGTT | GAATGTGAAG | TATCTCATTG | TGGTTTTGAC | 100920 |
| TTGCATTTCC | CTAGTAACTA | ATGATGTTTA | AAATCTTTTC | ATGTGCATAC | TGGCCATTTG | 100980 |
| TATGTTTTCT | TTTGTGAAAT | GTCTGTTGAA | AACTTTTACT | CTTTGTTTTG | GCTTGTCATC | 101040 |
| TTACTAAGTT | ATAAGGTTCC | TTATATTTTC | CAGGTGCGAG | TCCTTTGTCA | GATACATGTA | 101100 |

| | | | | | | |
|---|---|---|---|---|---|---|
| TTATAAATAT | TTTCTCTCAG | CCTGTGATTT | TTCTTTTTCT | TTTCTATTTA | TTTATTTATT | 101160 |
| TATTTATTTT | TTAGGAAGAG | TCTCACTTTG | TCACCCAGGC | TGGAGTGCAG | TGGCACCATC | 101220 |
| TTGGCTCACT | GCAACCTGTA | GCTCCGGGT | TCCAGTGATT | CTCATGCCTC | AGCCTCCTGC | 101280 |
| TTTTCATTTT | ATAATGTTTT | TTGAAAAGCA | AATTTTCACT | TTTGATGAAA | TTTATCATTT | 101340 |
| TGTTATTTAT | GTTTTATAAA | CTATAAACCT | GTTGTTTTGT | TTTAAAGAAA | TCTTTGCTAA | 101400 |
| TCCTAGGGTG | TTGATGATTT | TCTCCTATTT | TTTAAAGAAG | TTTTATAATT | TTAGCTTTTA | 101460 |
| CATTTAAGTC | TATGGTCTAT | TTGAGTTAA | TTTTTGCATA | AAGTTTGAGG | TAAGGCTCCT | 101520 |
| GCTCCTCTCC | CCCACACCGG | ATGTCTACTT | GTTCAAGAAA | CATTACTGA | AAAGACGATT | 101580 |
| TTTTTACTTA | TTAAATAGCC | TTGACACCTT | TGTCAAAACC | AGTTGTCCAT | AGATGTGTGA | 101640 |
| ATCTATTTCT | GGGTTCTCTG | TTTTGTTTCA | CTGATCTTTG | TGTCTAACCT | TATACCAATT | 101700 |
| CATTCTGAAA | TACTTTCCAG | ATTACTATAG | CATTTTAATA | AAATTTTGAT | TGAATAGTTT | 101760 |
| AAGCCCTCGG | ACTTTTTTCC | TTTTAAGTAT | ATCAACTTGG | AGAGGATTGA | TTCATATTTG | 101820 |
| TGTTTCATTT | TTTCATTTTT | CAAAATTATG | TTTCAAATTG | ACATAATAAT | TATATGTATA | 101880 |
| TATGGGGTGC | ATAGTGATGT | TCTTTTTTTA | AAAAATATTT | ATTTATGTAT | TTATTTATTT | 101940 |
| TTGAAACAGA | GCCTTGCTCT | GTTACCCAGG | CTGGAGTGCA | GTGGCGCGAT | TTCGGCTCAC | 102000 |
| TGCAACCTCC | GCCTCCTGGG | TTCAAGCAAT | TCTCTTGCCT | CAGCCTCCTG | AGTAGCTGGG | 102060 |
| ATTACAGGCA | CATGCCACCA | CGCCTGGCTG | ATTTTTGTAT | TTTTAGTAGG | GATGGAGTTT | 102120 |
| CACTATGTTG | GCCAGACTGG | TCTCTAACTC | CTGACCTCAA | GTGATCTGCT | TACCTTGGCC | 102180 |
| TCCCAAAGTG | CTGGGATTAC | AGGTGTGAGC | CACTGCGCCC | AGCCCATAGT | GTTATTTTA | 102240 |
| TACATACTGT | GTATAGTGAT | CAGATCAGGG | TAATTAATTA | GAATATCCAT | TATTTCAAGC | 102300 |
| ATTTCTCATT | TCTTTGTGTT | GGAAACATTC | AATGTCCTCT | TTTCTAGCTC | TTTGAAATTA | 102360 |
| TTTATTACTG | TTAACTATTG | CCATTCTGTA | GTACAAATAG | AACACTAGAA | CTGATTGCTC | 102420 |
| TTATCTAGCT | GTAACTTATT | TTAACGAATC | TCTCTTTATC | ATCTCTTTCC | CCTACCATTC | 102480 |
| CCAGCCTCTA | GTAATCTCTG | TTGTACTTTT | TACTTCAATG | AGATAAACTT | ATTTACTTAG | 102540 |
| TTAGCTAGCT | TCTGCATATA | AGTGAGAACA | TGTGGTGTTT | AACTTTCTGT | TTCTGGCTTA | 102600 |
| TTTCACTTAA | TGTAGTATCC | TGCAATTCCA | TCCATGTTGC | TACAAATGAC | AGGATTTCAT | 102660 |
| CCTGTCATGA | ACAAACAAAA | ATTTGCCAAA | ACAAAAATTA | CCTTAGTTAT | CACATTTCTT | 102720 |
| TTATTGACAT | AATTCATAAT | CATCAGAATC | ATCTGACTTG | TACATCATTG | TATCAGTTGG | 102780 |
| TTTTATGCTC | AAGATGTTGT | ATTGGTTCAT | TATTGTCTTA | ATATCCCAAC | CAACCCAATC | 102840 |
| TAGACATAAA | TGCTGGCCCC | TGTGACATGG | CAGGAAAGGG | AGACAGGCCT | GGGCCAAGCA | 102900 |
| TAGTGATAGC | AATGCACCTG | TGTTTGAAGC | TGTTAAATAT | TTGCTACAGT | CGTATTCCTA | 102960 |
| GACTCAAAAT | TAGATTCTTG | TTAAGTCCTA | CTTGTCAGTG | TCTATGGCTG | TGTGAGTTCT | 103020 |
| GGTTAGTAGA | AGGTGGGCAA | AAGTGATGTG | TATTCTTCCA | TAACTGGTCC | ATAACCACCT | 103080 |
| ACCACTCACA | ATACTCCATG | CCTTTTTTTC | TCTTCAGGCT | CCTTGGATTA | GAGACCATCC | 103140 |
| TGAGGACATC | CTTGGGAGCC | ATGTGCTGAA | GATGGCCAAG | CCACAGGATG | AAAGGAGCTG | 103200 |
| CATCTTTGAG | TCACCACTGG | AGAAAGGTCT | CTCTAAATGG | ATTTGCAGAG | ACGTCTTCTC | 103260 |
| GAATACTCCC | CTTCTAAGTT | CCACTTGTAA | TCCACTTCTT | CTATTCTCCC | AGCAATCAAT | 103320 |
| GTGGTTTGGG | GAAATTCCAG | AATCTCATAA | TACCTTGGTC | ATGGGTAAAT | AAGGAAAGGA | 103380 |
| CCTTTACATA | CATGTGATGC | AAAGCAGATC | AAAACAAGCA | GAGCAGCCTA | AGAGCAGCAA | 103440 |
| GACCCCAAAG | GATAAGGGAA | GTCCTGCAGA | AGAGCAGAGC | GGTGCTGCAA | AGGCAGGCAG | 103500 |

| | | | | | | |
|---|---|---|---|---|---|---|
| GTAAGGTAAG | CAGACAGGGC | CATCAGGATG | GATCCTTTGG | GCATGCCAGC | ATCCACCAGG | 103560 |
| GACTGGTAGA | GCTATTTAGA | GAAACTGATA | AAAAGCTCTG | CCAACTACAG | TCACAAAAGA | 103620 |
| TGGAGCTCAG | AATGATGAGT | AGATGCCTAA | AACATCTCCA | TTTTGTTGAT | GAAGAAAGTA | 103680 |
| AAGTTTATAG | AGCTTAGATT | ATTTGCTTTT | GTACCTAGCA | CAGTACTTAG | TTTATAGTAG | 103740 |
| ATGCACAATA | AGTATTTGTT | TAATGAGTGA | ATGAGTCACT | AGCCTAAGAC | CTTTAATATA | 103800 |
| ACATGCTTAA | ACCTGCTACC | AGGGATTGGG | AACTCACCTA | TTTAGTAGTG | AGTAGAGGGG | 103860 |
| TGTGGTACTG | GTACTTAAGA | CAGATGCATT | GTGGTTGGGT | ATGGTGTGTT | TTTGTTTTTG | 103920 |
| TTTTGAGACA | GGTTCTCCCT | CTGTTGCCCA | GGCTGAGATG | CAGTGGCATT | ATCATGGCTC | 103980 |
| ACTGCAGCCT | TAACCTCCCG | GGCTCAAGC | GATCCTCCCA | CCTCAGCCTC | TGAGTAGCTG | 104040 |
| GGACCACAGG | TACGCATCAC | CGTGCCTGGC | TAATTTTGTT | TTTTGTTTGT | TTGTTTTGTA | 104100 |
| GGGACGGGAT | TTTGCCATGT | TGCCCAGGTT | GGTCTCGAAC | TCCTGGGCTC | AAGCTACACC | 104160 |
| CGCCCGCCTC | GGCCTCCCAA | AGTTGTAGGA | TTAAGGTGTG | AGCCACTGTG | TCCAGCAGAT | 104220 |
| ATAATGTTTT | TAAAAGTTTG | AGAGTTAATA | TGCTCTCTGG | TGTGCCCTAG | GTCCCACTAC | 104280 |
| TCCTATTGCC | TTAAAACTCA | CGCAGTACAC | ATTTGTCTTC | CATGGGCTTC | AGTTGTAAGA | 104340 |
| GAACCCTTTC | TACTCTTTGC | TGTTCACAAG | TCTCCTTTTA | AACAGAGCTT | GTTCCCAATG | 104400 |
| CTGTTTTGTT | TTGCCCTCTG | CCATGTTCTT | CCGGCCATCA | CCTCCTGTGG | GGAAAAGAGA | 104460 |
| GAGAGATCAC | ATTGTTACTG | TGTCTGTGTA | GAAAGAAGTA | GACATAGGAG | ACTCCATTTT | 104520 |
| GTTCTGTACT | AAGAAAAATT | CTTCTGCCTT | GAGATGCTGT | TAATCTAACC | CTAGCCCCAA | 104580 |
| CCCTGTGCTC | CCTGAGACAT | ATGCTGTGTC | AACTCAGGGT | TAAATGGATT | AAGGGCTGTG | 104640 |
| CAAGATGTGC | TTTGTTAAAG | AAATGCTTGA | AGGCAGCATG | CTCGTTAAGA | GTCATCTCCA | 104700 |
| CTCCCTAATC | TCAAGTACTC | AGGGACACAA | AACACTGAGG | AAGGCCACAG | GGACCTCTGC | 104760 |
| CTAGGAAAGC | CAGGTATTGT | CCAAGGTTTC | TCCCCATGTG | ATAGTCTGAA | ATGTGGCCTC | 104820 |
| GTGGGAAGGG | AAAGACCTGA | CCGTCCCCCA | GCCCGACACC | CGTAAAGGGT | CTGTGCTGAG | 104880 |
| GAGGATTAGT | AAAAGAGGAA | GGAACGCCTC | TTTGCAGTTG | AGACAAGAGG | AAGGCATCTG | 104940 |
| TCTCCTGCTC | GTCCCTGGGC | AATGGAATGT | CTCAGTGTAA | AACCCGATTG | TATATTCCAT | 105000 |
| CTACTGAGAT | AGGGAAAAC | TGCCTTAGGG | CTGGAGGTGG | GACATGCTGG | CAGCAATACT | 105060 |
| GCTCTTCAAG | TCATTGAGAT | GTTTATGTGT | ATGCATATCT | AAAGCACAGC | ACTTAATTCT | 105120 |
| TTACCTTGTT | TATGATGCAG | AGACCTTTGT | TCACGTGTTT | ACCTGCTGAC | CTTCTCTCCA | 105180 |
| CTATTATCCT | TTGACCCTGC | CACATCCCCC | TCTCCGAGAA | ACACCCAATA | ATGATCAATA | 105240 |
| AATACTAAGG | GAACTCAGAG | GCCGGTGGGA | TCCTCCGTAT | GCTGAACACC | GGTCCCTGG | 105300 |
| ACCCCTTTTT | TTCTTTCTCT | ATACTTTGTC | TCTGTGTCTC | TTTCTTTTCC | AAGTCTCTCA | 105360 |
| TTCCACCTAA | CGAGAAACAA | CCACAGGTGT | GGAGGGGCAG | CCCAACCCTT | CAACCTACCT | 105420 |
| ATCTTATCTC | TTCCATTATC | TATCCACATA | TGTCCTCTGT | ATTTTTTTGA | GTAACATTTA | 105480 |
| TAAGCATAAG | TCCTTAGGTA | GCTATGCCAC | TTACATAATG | AACTAGAAAA | GGTAACCAAA | 105540 |
| CAGAATAGGG | TTGTACTCAG | ATATACCTTC | TACAAGTTTG | TGTTACACAT | ATTTACACAT | 105600 |
| ATTTAAAAAT | ATATACATAT | TATTATTGTG | CTGTGTGGTT | ATTAGGCAAA | CTCAATAAGC | 105660 |
| AGTTCTTATA | AAGTATACTC | AATGTAACTT | TTATAAACTT | ACCATATTTT | ATAGTTATTC | 105720 |
| TGTTTTTATT | AGCTGCTATA | AACTACCTGG | GTGTCTTGCA | TGAGTCATTT | TATTGTAATG | 105780 |
| TTTTTGTATC | TGTTGAATGA | GGAGTTAGAA | GGCATCATCT | TTAAGGAGCT | TTACAGGTAC | 105840 |
| ATGTCCAGGG | CTCAATAATT | TTATTATTAT | TTCCTGGACA | GATAAAACCT | AAGCAGGTGA | 105900 |

| | | | | | | |
|---|---|---|---|---|---|---|
| AGGGGAAAGA | ATAAAAGTGC | AGGGTGGAAG | TTGCTTGAAT | GCTAACTGGG | TCAACGATCT | 105960 |
| CCCAGAAAAC | CCCTGTAAAA | GAAACCTAAG | AACCTACATC | ACCAGGAGAC | CATTGGGACC | 106020 |
| AGTTCCTCTG | GAATCCCTGA | GGCCAGATAA | TCAGCTGAAG | CTTTACATTC | TGTCCCTTTC | 106080 |
| TGGTCATGAC | TTTCTCCACA | GTCTGCTTGG | TGCCTCCTCC | TCTGTGACTC | TAAATTCTTA | 106140 |
| GGATCAACCC | CTCTTGCATA | TGCACATCCG | CAGTGCCTGT | GGGATACGGT | GTGGTGTGGG | 106200 |
| GAGGAAACTC | TCTTCTGCCT | TAATATTTTC | CTGTGTGCCC | CAGGCCTTGA | CGGAATCCTG | 106260 |
| TCTCTCCATA | ATGTTGCTTT | TCGAGGAGAC | TGATTGATTG | AGATGGCGTC | TCACTTTGTC | 106320 |
| GCCCAGGCTG | GAATGCAGTG | GCGTGATCTC | GGCTCACCAA | CCTCCACCTC | CAAGGCTCGA | 106380 |
| GTGATTCTCC | CACTTAAGTC | TCTTGAGTAG | CTGGGACTAC | AGGTGCATGC | CACCACGCCT | 106440 |
| GACAAATTTT | TTTATTTTTT | GTAGAGATGA | GGTTTCGCCA | TGTTGACCAG | GCTGGTCTCA | 106500 |
| AACTCCTGGA | CTCAAGTGAT | CTGCCCACCT | CGGCCTCCCA | AAGTACTGGG | ATTACAGGCA | 106560 |
| TGAGCCAATG | TGCCCGTCCT | GAGGAGTTTT | CTTCTGGAAT | TCCTGCTGGG | TTTTTGTAGT | 106620 |
| CAGTCCTCTC | CCCATTTCCC | ACATTGGCTC | TTGCAGACCT | TCCTTTTCCC | CATTTCTATT | 106680 |
| TGCTACCATG | TCAGACATGA | CTTTTGCCAT | AGGATCTCTA | TTCTACTATA | GAGGAAACCA | 106740 |
| AAGCCATCAG | TAGAAATTTC | ACTAACATGG | AATCAGATTT | ATAGAAGAAA | GGGGGAGGAA | 106800 |
| AGTTTTGCCT | TAACACCTGG | AAGGGTTTCG | TTTCTTTTAG | TAGCTGGGAG | ACAGAAACAT | 106860 |
| AAGAAAGTAG | CTTAGTAAGC | TTTCTGCTGT | TCAACTGATG | ATGTGTGAGC | TGTCAGTAGT | 106920 |
| TCAAACTAGT | CATTATCTTT | ATGAATTAAT | TATGTAATAA | CTTAAACAAT | GTCATAAACC | 106980 |
| TTCAAATCAG | TTTAAGTCTA | AATGTGTCAT | ATTTAATAAC | AAGAGCAAGA | AACATACGTT | 107040 |
| ATGATGAAGA | GCTCTTATAT | TTTCTTTGGA | TAAAAGTCAG | TAGGCGGGGC | GCGGTGGCTC | 107100 |
| ATGCCTGTGA | TCCTAGCACT | TTGGGAGGCT | GAGGTGGGCA | GATCATGAGG | TCAGGAGATC | 107160 |
| GAGACCATCC | CGGCTAACAC | GGTGAAACCC | TGTCTCTACT | AAAAATACAA | AAAATTAGCT | 107220 |
| GGGCGTGGTG | GCGGGCGCCT | GTGGTCCCAG | CTACTCGGGA | GGTTGAGGCA | GGAGAATGGC | 107280 |
| GTGAATCCGG | GAGGCGGAGG | TTGCAGTGAG | CCGAGATTGT | GCCACTGCAT | TCCAGCCTGG | 107340 |
| GCGACAGAGC | AAGACTCCGT | CTCAGAAAAA | GAAAAAAAAA | AAAGTCAGT | AAAATTTAAG | 107400 |
| AGAAAAATGC | ATTTGCTTTG | GGACTTTTAA | TATTTAGTCT | ACAAATCTAG | CCACCATAGA | 107460 |
| AATCTGCTGA | TTAAATACGG | GTTCTGTTAA | AATGGAAACA | TGCATTTTGG | GGGAAAAAG | 107520 |
| AGGGAGTGTT | TTAGTGATTT | TGTTTTTTAC | ACTTGTTTAT | AATAAAATTT | TAAGCAATCT | 107580 |
| TGAGGGGAAC | ATTTTATTTC | TACTTGTAAC | TGCATAAAGT | TATGAGATAA | AGTTACAAGC | 107640 |
| TATATCACAT | ACAGTTTGTA | GCTTTATAAA | TTATGAAATT | CTAACAGAAT | AAATATGCTA | 107700 |
| ATATGATGAA | AATGTCATAA | ATTACATTAG | AATATATTTT | AATAAACCAA | TTCAGAAGGA | 107760 |
| GCCAATACCC | AATTTCAAAA | TCATATTAAT | TGTAAAATTA | ATTAGGGCAG | CCAAAATATT | 107820 |
| CTGGAATTCT | TTCTAATAAA | ACAAATGAGT | GTAAATACAG | TCGTACTGAC | AAATCTGAAG | 107880 |
| AATTATGCAG | CATAAAAAGT | GATTATCCCA | GCACTTTGGG | AGGCCAAGGT | GGGCAGATCA | 107940 |
| TGAGGTCAGG | AGTTGGAGAC | CAGCCTGACC | AACATGGTGA | AACCCCGTCT | TTACTAAAAA | 108000 |
| TACAAAAATT | AGCCGGGCTT | GGTGGTGCAC | ACCTGTAATC | CCAGCTGCTC | AGGAGGCTAA | 108060 |
| GGCAGGAGAA | CTGCTTGAAT | CCAGGAGGTG | GAAGTTGCAG | TAAGCCAAGA | TCACGCCACT | 108120 |
| GCACTCCAGC | CTGGGCGACA | GAGTGTGACT | CTGACTCAAA | AAAAAAATAA | ATAAATAAAA | 108180 |
| ATAAAAGTTT | TAAAAAAGTG | ATTATTATGA | ACACAGAGTA | ATCTAGTAAA | AATGGTTAAG | 108240 |
| TGAAAACAGC | AAAATACAAA | ATTGAATATG | TACTATAACA | ATATATGCAA | AATATACTCA | 108300 |

-continued

| | | | | | | |
|---|---|---|---|---|---|---|
| GATTTATAAA | AATTAGAATG | TAGAAAAGTA | AATATAGCTC | TTCATAATTT | TGTTCTGAAG | 108360 |
| TTTAAAAATA | TATATATTTT | TGAATGGATA | ACTTTCTTTT | TCTAAATGCT | TACAGTAGAG | 108420 |
| CCCACGATGG | TTGTTAAAAG | CCCCCAGGTT | CAGCCTTCTT | TAATTGTGTG | GTCAGCCTGC | 108480 |
| CATCAACCCG | AGGCCTCCCT | CTGCTGGGCA | AATTTGGGAA | CACATTGAGA | AATCCTTACA | 108540 |
| CGTAATTCCT | TCTCTTCATG | TTCCTGGTGA | GCATTTTCC | CATTGGGTTT | CCATACTCTG | 108600 |
| CCCTCTTGAA | GTCCTGCACC | CTGACATTGC | AGTGTCATTC | CTCTTCTACT | GAAGTCTACA | 108660 |
| ACTATTAGCT | TATTGTCTCT | AGCAAGTCTC | CCTTTAGCTA | CAAATATCAT | TCAGAGTTTT | 108720 |
| ACCTTTCAGA | AACTTTCTCC | ATGAGCATTC | TGGAGTAGAC | TCTAGGTGCA | CTAGGTGCAG | 108780 |
| TTAGAAAAAG | TTCTGATTTG | TTGGTGGAGC | TATAGGAGGA | GAGACAATGG | TGGGCTGGAG | 108840 |
| AAGGGTGTCT | ACATGCAGAG | AAACTGACTG | GAAACTCAGA | GAGATGATGG | GGATTAAAAT | 108900 |
| AATCCTATTG | AATCTGCACA | AAAGTGTTTT | ATTATAATTG | ATCCTGAACT | ATGTAAAGGT | 108960 |
| AAGCTCCAGT | GAGTAGTTAC | AGTCTGTCCC | TAAGATGGAC | TCTTTCTTTT | TGCTTTTATT | 109020 |
| TTTATTGTAT | TTATTTTATT | GTATTTTTTT | TTTCTAAAGA | CAGGGTCTTG | CTATGTTACC | 109080 |
| CAGGGTGGTC | TCAAGTGGTC | CTCCTGGCAT | CAAATGATCC | TCCCACCTCA | GCCTCCCAAA | 109140 |
| GCGCTAGGAT | TACAGGTGTG | AGCTACCACA | CCCAAATGAT | TCTTTCTTTT | CAAATACAGA | 109200 |
| GTTCAGCAGC | AATTTAAAG | AAGTACTGAA | CTCTACTGCC | TGGAAGATGG | AATGGCCCTC | 109260 |
| ACAATTCTTC | CAGGCAAGCT | CTGCACTCAG | TGGTATGGAC | CACAAGGCAA | GCCCATTAAG | 109320 |
| GGGTTAAATT | ACTGACAAAC | AATAATTTCT | AAATATGAAC | ATTTCAGGAG | GAACTAAGAT | 109380 |
| GGCTCCTTCT | TGGAGAATAA | GTTGGCCGGC | TTCTCTAGTT | ATCAGACTAT | CAGATGGGGA | 109440 |
| GGAAAGAGCC | CCTCTGTCCC | GGTGAGACAG | GACCCGCCAG | CGCCCAAGCT | CTAAGGCTTT | 109500 |
| CTGATGAGCA | AATGGGGTTT | CCATCTTTCT | AGCTTCAGGA | CTCGTAACTA | CTCAGATTAT | 109560 |
| TTCCTTCAAT | CTGGATATTC | AAGACAAGAA | CAGTTCATGG | TGTTGCGAAG | GCCCAGATTT | 109620 |
| AAATCACATA | TGCAAAGATA | CTGACATTCA | GTGGAGGGTC | ACTTAGATTA | TAGCCAGATG | 109680 |
| ACTTTCCCTA | AATTGATAGC | TCAAATGGTA | GTTGTGGATA | TTTTTGCTCT | TAGTTACTTG | 109740 |
| CATAGTCACT | TGCCAGAGGT | AATAAAGTTT | TAGTGTGGTT | GTGGAAAATA | ATGGCCATAT | 109800 |
| ATTAGGAAC | AAAATTTAA | TGATGATTGA | AAACTGAATT | AGCTTTAACA | TGTGAATATG | 109860 |
| CTCAGGGGAC | ATAGGACCAC | AGATCTCTGT | TCCTTCCTAT | TGCCACTTCT | TTCCTTTCCC | 109920 |
| TGGTAGCATG | CTTCCATTAC | CCATTACTTC | AAACACTGTT | TCTGTGTCTC | CAACTCCCTT | 109980 |
| GCATCATGGT | CTTTTCATTA | TTCAGACACA | GACACAGCTC | GATTATGGGT | AAACTTTTTT | 110040 |
| CTGTGGCTAC | AGAAGAGTTG | AGCATGGCTG | AAGCATCGTT | GAGCATGACT | GAAGAAAAAC | 110100 |
| ACCTAACCTT | GAATTTTTTG | ATCAATATAA | ATTTATATCC | ACAGATTTTA | CCTGACTGAT | 110160 |
| CTTCATTGCC | CACCAGTCCT | ACAAAGTTTG | CCAGATTGGT | TCTGTTTCCA | CTTTACATAC | 110220 |
| TCAGCAAATA | CTTATTAAGC | ACACACTTTG | TGTTAGGCTT | AAGTGTAGAT | ATTGAAGAGG | 110280 |
| CACTGGTGAA | TGAGCAGAGG | CTCTGCCCCC | ATGGGACCTG | CATGCTATTT | GGCAGCTCTT | 110340 |
| TCAGACATTC | TCCTCTCTCA | AAGCTTTGAG | CCCCTCTATA | CCCCTATAAG | CACCTACTTT | 110400 |
| CAGCTGCTCC | CTCACTCCCC | CCTTCATGGG | GGAAATAACA | GCCATCGTGG | TAAAACCTCC | 110460 |
| ACTGCCTGAC | AGAGCTATAT | TTACCATCTT | TTCTTTAATT | TTTATTTTA | ATGGACACAG | 110520 |
| TTGTATATAT | TTATGGGGTA | CTATGTGATA | TTTGATACA | TGTATAGATT | GTGTAATGAT | 110580 |
| CAAATCAGGA | ATTAGATCAG | TTTTTTGTCT | TTTTTTTGGT | AAAAGATAAT | CTTTTATACT | 110640 |
| CTTTTGGTCC | TGAAAAATGG | AGGAGTGCCA | TATTAGGATT | CCAACAGAAA | AAGTTAAACC | 110700 |

-continued

| | | | | | | |
|---|---|---|---|---|---|---|
| AAAAGAATAT | ATGAAGGGCA | TATAATGAAG | GGATATCTAC | AAAGTTGTGA | CAGGGCTAAT | 110760 |
| GGGAAGAACA | GGGGATATGA | GGCAGCCCAA | GATCAGCAAC | AGTAGTGATC | CAGTGTCACC | 110820 |
| CTGTGCTGGT | TATGAAGATT | TAGTCTCTTC | TATCTTTTCC | AATACCGCTT | TGCTAGCCAC | 110880 |
| CTCCCCAAAC | CCTACCAATA | GAAAGCACTG | GAGGAAGACT | AGAGGGCTGG | AAGGATGTGA | 110940 |
| AAAGATTTCC | CACTTTGTTT | GTTGACATCC | TCACAGAATG | GGTTCTTCAA | CCTGGCAGTG | 111000 |
| GCAGTTGAAT | CCAGTAACAG | CAGTTGGCTT | CAGTTTGGAG | ATCTTCCATG | CTCCTAAAAT | 111060 |
| CAGCCTCATC | ATGCCTCTAT | CTACAGACAT | ATCATCATCA | GTGGTCCAGC | ATACACTCCT | 111120 |
| CAGAGGTCCC | AGTTCTGGGG | ATCTCTTCAA | AGAATCTTTT | CCTTGTTCTC | CTAAACCTGG | 111180 |
| AGGTGGTAGT | TGCTTTCTGT | CATTACTATC | TCTGATACGT | TTGTCCACTT | TTCCATTTTC | 111240 |
| AGTCCTCTTA | TAACTAGTTA | ACAACCATTC | CCATAAAATT | CTTTGTTCAA | TTTCAGTGCA | 111300 |
| ATTTCTAGCT | CCCAGTTATA | CCCTGACAGA | CACACCTTTA | AATCTGAAGA | GGCAATGGGA | 111360 |
| GGGAACCTGT | AACCAGAGCT | AGGCCAGAGC | TGGGACTGTG | GAGGAAGAGC | TGCCCACCAA | 111420 |
| GCAGGGGGT | GATGCAGGGA | ATAAGTACAC | TAACCTCTCT | CTCCTTTGCC | ATCTACATTC | 111480 |
| CTGCTGGGCT | GATCACTGGC | CAAATCCAGC | TGTTGCAAGA | GGGCAGGGCT | GCCCAGCTAA | 111540 |
| TGCTATCTGT | AGAAGCTGGG | CTTCTGGGGC | ACAGAGCAAG | TCAGAGACAG | GCAGAACAGG | 111600 |
| GATGTGGGTT | TGGACCAAAC | ACTGAATAAA | CCAGATCAAG | GATTCTTCTA | TCAAGACAAG | 111660 |
| TTTATATACT | TGCAGCTTGA | TCCCATTGTT | TCCCTTAGAT | AACTGTGCAC | TTGTTTTTGT | 111720 |
| CTGCCCTCTT | TCCTGTGTCT | ACACTCTTCC | TGTCTTATTC | TATTTACACA | TAGCTCAGTC | 111780 |
| TTTTCCAATT | AAAAAAAAAA | AAAAAAGCT | TTCCCTCTCC | CAAATCTCCA | TGCAGCTGCT | 111840 |
| GACTTCTCTC | TTCCAAAGCC | ACACTGTGGG | AGAGTCAGTT | ACACCTCCTG | ACCTCTGACA | 111900 |
| GGTGCAACAC | ACTATAGTGA | GGCTTCTGCC | CTTGGTATTC | CTCTGGCTCC | ATTATTTACA | 111960 |
| AGGTCACTAA | TGACTTCCTA | TTTCTAAATC | CAGAGTGCCT | TTTTAGTTAT | CTTCCTTGCC | 112020 |
| TTCTTGGCAT | CTCTAGATAA | CAATACTTGT | CTCATTCTAA | CTTTTGTCTC | TCCTTACAGC | 112080 |
| TCTTTCATTC | ATAATTCATT | GTTATTCAGT | TGGAGCCTTG | ATGGTGTTAG | GGAGAAGCAG | 112140 |
| CATTCTGTAG | TCAAAGTGTT | AAGCCTCAGT | TTATTAGCAT | GCCTATATCT | TGGGGCTGGG | 112200 |
| ACCGTCACAA | GTGTTTATAA | TGATACAACT | CCTCCTCCTC | CTCCTTCTCC | TCCTCCTCTT | 112260 |
| CCTCAAGTGT | TTATAATGAT | ACAACTCCTC | CTCCTCCTTC | TCCTCCTCCT | CTTCCTCAAG | 112320 |
| TGTTTATAAT | GATACAACTC | CTCCTCCTCC | TCCTTCTCCT | CCTCTTCCTC | AAGTATTTAT | 112380 |
| AATGATACAA | CTCCTCTTCC | TCCTTCTCCT | CCTCCTCAGA | CCTTTGCTCC | TTTCCTGGCT | 112440 |
| GCACCATTTC | CAATTTATTT | TCATGAAGCT | CTGATCCCTG | TTGACTAATT | TTCTTCCCTT | 112500 |
| AAGTGAGACA | GAAAGCCTAG | ATGAGGCTGC | AGTGGGAAGA | ATTACCTTCT | CCCAGCTGGG | 112560 |
| ATAAGACTCT | GGCAAAATGT | TTTCCCCTTG | AGAGTAGGCC | TTTGTTTTGA | AGAAGGTTCT | 112620 |
| GGGGTGTATT | TCATAATAAT | TCTTCTCTCC | CTGCCAAAGC | CACAAGAGGA | TCCTTCTCAG | 112680 |
| ATCTTCACTG | CAGGAACCTG | GTGGGCTTTC | TGATGCCCAC | AAAAGTGTGG | GAGCTTCTCA | 112740 |
| CTCTCATGGG | CATTCACAGT | TGGCCTCCAG | CTTTTTGTCA | GAGTTACCAA | TTTAAATGTT | 112800 |
| CTCAAATGTG | ATACTGTCTC | AACTTCCAGG | ACATCACACA | CTCATGATTT | TCTACTATCC | 112860 |
| TGACATTTGC | AGTCTTTTTA | GCAGATCTCC | CTCCCTCTCC | CTGCACCATG | GGTATTGGTC | 112920 |
| ATCTCAGGAT | CTGTCCCAGG | CTTTCTACTC | TTCATGCCCT | TTGAGACAAC | ACATGATCTG | 112980 |
| ACCTGCCCTT | TCAGGAAGAA | ATGTTCTGTC | TACCTACTTG | CTCCAGTTAA | AAACCCTAGT | 113040 |
| GTCATCTTTG | ACCCTTCTCA | TCCCTACATC | TAATCTGTTG | ATTCTACCTC | CTAATTTTCT | 113100 |

| | | | | | | |
|---|---|---|---|---|---|---|
| CTCAAACGCA | TCTATTTTTC | TTCAATTTCA | GTGCTACTCT | CTTGCTCTAA | TTGTACATCA | 113160 |
| TCTTTTTTAG | AATTACTGTG | ACATTTTCTT | GCCTCCAGTT | CTGCCTCAGT | CCATCCACTT | 113220 |
| CACAGCTAAA | TTTTGGATGT | ACACTTTTGA | ACTATTACTG | TAGCAAAAGT | AATATGTAAT | 113280 |
| AACTGTAATG | CAGAAATATA | AAATATGCAA | TATAAAAGAA | ATACATGCAT | AAATGATCCC | 113340 |
| AACACTAAGG | AAACAATATT | GATCAATAAT | TAAATAATTG | GTGGATAGTG | AATGACAACA | 113400 |
| TAGAGCAAAG | TGTTCAGTAG | GTTTTAAAAG | CTGTGGGTTC | AATAAATGCT | CATGAAGCTT | 113460 |
| GTTCAGGGGC | TTGCAAAATA | TGTAATTTGA | ATTTTTAAAG | AAAGGAATT | TCAGATAAGA | 113520 |
| AAAAACATAC | ATAACATGAA | ACAATACTTG | TGGTGGTTTC | AGGGAGGTCA | TGTTCTCACA | 113580 |
| TTCAGGTGCC | AAGGCCACCG | TACATCCGGA | CACTGAGGCC | ACGGACTTGG | TCTGCAACCT | 113640 |
| CCATGACAGC | CTTGTAGATT | TGAAACCGAA | CTCCAAGGAG | CAGTTGTGCT | GTGAGTTCCA | 113700 |
| GAGTTTGGGG | ACAGAGGAAA | CACCATTCTT | TGGAAGTCTA | ACTTCCTTAA | GAGGTGTCCC | 113760 |
| TTAGACATCT | AGTGTCCGGT | GTTATGGAGG | TCCTTGTGCT | CTGAGGAAGG | AGCCCCTTGT | 113820 |
| TGATTGATGG | AGCAAAATTT | TTTTAAACAA | GGAACTGTAC | CCGTATCTGG | GCATGAAGCC | 113880 |
| AGAGAAATCC | CTGAGGGCAG | GGCCAAGGCT | CTCAAAGATT | TTCAGGGAGA | TTCCCAGCCT | 113940 |
| TTTTAAGTCT | CGCCTATTCT | TTTTTTTTC | TCTAACTGGC | CATTTTGTAT | ATATGGAGGT | 114000 |
| TATTGATTTT | TTTGCTTTTA | TATCCTGATA | TTTTAATAAC | TGTTCATTTT | TTAGTTATTT | 114060 |
| GAATTATCTA | CATTGATTAT | TTGAATGTTC | TTTTTTTGT | TTTTTGAGA | CGAAGTCTCG | 114120 |
| CTCTGTCGCC | CAGGGTGGGG | TGCAGTGACA | GGAACTTGGC | TCACTGCAAC | CTCTGCCTCC | 114180 |
| TGGGTTCAAG | CGATTCTCCT | GCCTCAGTCT | CCTGATTAGC | TGGGATTACA | GGTGCCCGCC | 114240 |
| ACCACACCCA | GCTAATTTTT | GTATTTTAC | TAGAGATGAG | GTTTCACCAT | GTTGGCCAGT | 114300 |
| CTGGTCTCAA | ACTCCTGACC | TCAGGTGATC | CACCCACATC | GGCCTCCCAA | AGTGCTGGTA | 114360 |
| TTACAGACAT | GAGCTATTGC | ACTTGGGCTT | TGAATTTTCT | ACGTATCTGA | CTTCTACGAA | 114420 |
| GAAAACTATA | ATGTATTACT | CAGATAAATT | AAACAGGAAA | ACTAAATAAT | GGAGGAGTAT | 114480 |
| ATTTACAGTT | GAAGCGGTCA | ATATTTTAAA | GGTATTAATT | GTCCCCAAAC | TGATCTACAA | 114540 |
| AACCATTGTA | ATCCTAATCA | GATTCCCAAT | AAGCTTTATT | ATAGAAATTG | ACAAACAGGG | 114600 |
| TTCAAATTTA | ATACACAAAT | CCAAGGGCCC | AAAATAAACA | AATCTGTTGC | TTTATTAAAT | 114660 |
| ATCAAAACTG | ATAAAATGAC | AATAATCAGG | GCAGTGTTGT | CCAAAAATAG | ACAAACGAAT | 114720 |
| GGAACAGGCT | CAAACAAATA | TGGACATTGA | TTTACATCTA | AAGTGGCACC | ATACAACAAT | 114780 |
| GGTGAAAGGA | CTCTTGTAAA | TAAATGGCAT | GGGACAATTG | TATAGCCTTT | TAAACAGAAA | 114840 |
| AAGAACAAAA | AGGAAAAAAA | AAGAAACTTG | ACCCCTACT | TCACACTATA | CACAAAAAAC | 114900 |
| AATTCCAGGG | GAACTAACAT | GAAAAGCAAA | ATAAAGTTAA | ACATGAAAAG | CAAAATAAAG | 114960 |
| TATATGGTAA | AAAATTTATC | TTACCCAAAA | AGAGGTCTAG | CCTTTGCCCT | CAGCTACTGG | 115020 |
| GAGATGAATT | TTAGACCCTT | GAAATGTTCT | CACTGATAAG | TGTGTCTTTG | TTTACCTGGA | 115080 |
| GGTTTTGACC | ACCACACAGT | CAACAATGTG | ATTTATAATA | GGAACTTTGA | GCCACACAGT | 115140 |
| ATCAGCTCTA | CCTGTGGAGG | TAGACTAAAA | GATCGGCCAT | GTGAGCAGTC | AACCATGGCA | 115200 |
| GGCCATTAAA | ACTGCACACT | GAGGCTCGGG | TGAAATACAG | TTCTCTTGTA | TACGGTTTCT | 115260 |
| ACATGGTTTT | AGTTCCTGTG | GTCTACTGCA | GTCCAAAAAT | AATAAACGGT | AAATTTCAGA | 115320 |
| AATAAACATT | CACCTAACTT | TTATACAGTA | TATTCTTAAC | AATTATTCTA | ATTTATTGTT | 115380 |
| ATTAATCTCT | TACTGTGCCT | AATTTATAAA | TTAAGCCTTA | TCATAGCTGT | GTCTGTATAG | 115440 |
| GAAAAAACAG | CTATATAGAG | TTCAGTACTA | TCCATGGTTT | CAGACATCCA | CTGGAGGTCC | 115500 |

-continued

| | | | | | |
|---|---|---|---|---|---|
|TGGAACATAT|GTTTTGTGCA|TAAGTGGGGA|CTGCTCTGTA|CGTCATGTGT|ATTGTCACAC 115560|
|ATTAATGCTG|GGAAAGTAAT|ACTGTTCATA|TTACTGGGAG|AGGACAACTG|GAAGCTCATA 115620|
|TTTGGAACTT|GCCTGGATTG|TGCCTATATT|AGTTTCCTAG|GGCTGCTGTA|ACAAAGAGCT 115680|
|AGAAGCTAGG|GTGGCTTAAA|ACAACAAATA|TATTCTCTTG|TAGTTCTGGA|AGCTAGAAAT 115740|
|CTGACATGAA|GGTATCATTA|GATCTATGCT|TCCACTGAAG|CCTGTAGGAA|AATCCTTCCT 115800|
|TGACTCTTCC|TAGCTTCTCG|TACTTGCTGG|CAACCTTTGA|CATTCCTTGA|CCTGCAGCTG 115860|
|CATAACCTCA|GTCTCTGCCT|GTGTGTGTCT|GTCTTCACGT|GACCACCTTA|GAAGAATACT 115920|
|AGTTCTATTA|AAAAATATAT|ATATACTACT|TCTTCTAAGT|CACCAGCCCA|TCATACTGTA 115980|
|CTATAACCTC|ATCTTAACTA|ATTATATCTG|CAACTATCCT|ATTTCCAAAT|AAGGCCACAA 116040|
|TTCTGAGGTA|CTGGGAGTTG|GGACTTTAAA|CATATCTTCT|GGGGGCAAGG|GAGATCTGCA 116100|
|TACAATTCGA|TCCATAATAC|TGCCTTGTGT|GTTTCTTTTC|TCAGCTGATT|TTAATCTTTA 116160|
|TTCCTTGAGT|TGTTTCCCCT|TTTCAACTAT|TACAAACAAT|GAATTTTGCT|GTGTATGTGT 116220|
|CTTGGTATAT|ATGTGCACAC|ATATCTGCTG|TTTGTATACC|TCAGAGTGAA|ATTGTTGGGT 116280|
|CAAATGCTAA|AATCTTTTTA|AAAGTAGTTG|TATAATTTTA|CATTGCATTG|GAATGACATA 116340|
|ATAAGCTATA|TATCCTATAA|TAAATTGTAA|CCATGAGGCT|AACAGCTTCA|GCAAGTTCTG 116400|
|TGAGTCCTTT|TAGCAAATTA|CTAACCTAAG|GTTGATTGGG|AACCACAGAC|CTCCCAACTT 116460|
|ATAATTGGTG|TTAGAAGTGA|GGGTAGTCTT|GAGAACTAAT|TTCACAAGAA|GGTATTATAA 116520|
|AATAAGATCT|TCATGACCTT|GAAATAGAAA|ATGATTTTTT|AAATAAGATA|CAAAAAAGGT 116580|
|TGTGCATAAA|AGGGCAGTGT|GCTTAATTTG|AGTACACTAA|ATTAATGACT|TTAATGCATC 116640|
|ATGAGATATC|ATTGGCTGGG|TGCAGTGGTG|GCTCACACCT|CTAGTCCCAA|CACTTTGGGA 116700|
|GGCCAAGGTT|GATGGATTGC|TTGAGCTCAG|GAGTTTGAGA|CCAACTTGGG|CAACAGCACC 116760|
|ATCTCTACAA|AAAAATACAA|AGATTAGCTG|GGCATGGTGG|CCTGCACATG|TAGTCCCACC 116820|
|TACTAAGGAG|GATAAGATGG|GAGGATCGCT|TGATCCTGGG|AGGTGGAGGC|TGCAGTGAGC 116880|
|TGTGATTGTG|CCACTGCACT|CCAGCCTCTG|ACAGAGTGAA|GACAAGTTAC|AGAGGAAATA 116940|
|CCTGCAACAC|ATAAAATGGA|TAAAGGGTTC|GTGAGCAAAA|TTTAAAAACT|TAAAACAGAA 117000|
|AAGACAGGCC|AGGTTTGGTG|GCTCACACCT|GTAATCTCAG|CATTTTGGGA|GGCCGAGGCA 117060|
|GGTGGATCAC|CTGAGGTCAG|GAGTTTGAGA|CCAGCCTGGC|CAACATGGTG|AAACCCCGTC 117120|
|TCTATCAAAA|ATACAAAAAT|TAGCAGGGCG|CGGTGGTATG|CACCTGTAGT|CCCAGCTACT 117180|
|TGGGAGGAGG|AGAATTTCTT|GAACCCAGGA|GGTGGAGGTT|GCAGTGAGCT|GAGACAGCGC 117240|
|CACTGCACTC|CAACCCGGGT|GACACAGCAA|GAGTCCACCT|CAAAAAAAAA|GAAAGGACAA 117300|
|AAAGGACAAA|AAGACAGCTA|TCTTAAACCA|ACAAGAAAAA|ACACAATCTT|TTTGGCCTAA 117360|
|ATTGTGTTCC|CCCAAAATTG|ATGTTGAAAC|TCTAACACCC|AATGTGCCTA|TATTTGGAGA 117420|
|TAGGGATTTT|GGGACTTTAT|GGAGATATTT|AAGGTTAAAT|GAGGTCATAA|GAGTAGGCCA 117480|
|GTAGTCTGAT|AGATCTGGTG|TCCTTATAAG|AAAAGGAAGA|GACATGAGGT|CATTTATGG 117540|
|GCATATGAAG|AGGCCACATG|AGGACACAAA|AGGCGACTGC|TGTGGTTTGA|ATATGAGATG 117600|
|ACATCTCACA|TCTGCCATAA|CAGTAAGAAG|GCCCTTGCCA|GAGGTGGGCC|CCTCGACCAT 117660|
|AGGCTTTATA|GCCACCAGAA|TTGTAAGAAA|TAAATCTGTA|TTCTTTATAA|ATTATTTGGT 117720|
|CTCTGGTATT|CTGTTCAGCA|CCAAACAATC|TAAGACAGCA|ACTATCTTCA|GGTCAATAAG 117780|
|AGAGCCCTCA|CTAGAAACTG|AATCTCTTGG|CACCTCAATT|TAGGATTTCT|GGCCTGGCCT 117840|
|TTAGAACTGT|GAGGTAATAA|ACTCCTTTTG|TTCAAGCTAC|CTAGTCTAGT|ATTTTGTTA 117900|

| | | | | | | |
|---|---|---|---|---|---|---|
| TGGCAGCCCA | AGTCGACTGA | TATACAATCC | AATTAAGAAA | AAATGGGCAA | AAGATGTAAA | 117960 |
| ATAAAACCAT | AATGAGATAA | TACTGCACAT | CTGCCACAAT | GGATAACATC | TTCAAAAGAT | 118020 |
| TAACAATTTT | AATTGGAAAA | AAATATTGGG | AAGTATATGG | AAGAACAGGA | ATTCCAGCT  | 118080 |
| AGATTCCATC | AACATTAGGT | TTGTGAGGTT | CATCCATGCT | GTTTATAACT | GTGGTTTTAA | 118140 |
| TTTTCATTTC | ATCGCATGTA | AACCTAATAT | CACCACTTTC | AAAAGAGTT  | TAGCATTTGA | 118200 |
| CCCAACAATT | CCTCTCCTAG | GTATACAAAC | AAAATATGTA | TTCCTATATA | TACCAAGACA | 118260 |
| CATACACAGG | AATATTCACG | GTATTGTTTA | TATTAGCTGA | AAAAGGGAAG | CAAATATGCA | 118320 |
| TCAACAGTAG | ACACCTAAAT | TGTTGCACTC | ATAACATGGA | ATATTACATA | ACAATAAAAA | 118380 |
| TGAATTAAAG | TTATACACAG | CAACACAGAT | GAATCTATTC | AAACCTAATG | TTCTGGAGTG | 118440 |
| AAATATGTCA | GGTACATAGG | ATTACATTTG | TTTTATTTCC | ATTTTATATG | TTTCAAAAAC | 118500 |
| AGGCATACTA | AATTACAGCA | TTGGAAATCA | AATAGGGGT  | TATGTTTAGG | GCAGATGGAG | 118560 |
| TGATAATGTG | ACTGGAAGCA | AGCATCAGGC | GGCTCTGGGA | GGGTTGGCTG | ATTTCTGTT  | 118620 |
| TTTTTACTTG | TGTGGCAATT | ATTATGGTGT | TCACTTTGTG | TTCATTTATT | GAGCTTTGCA | 118680 |
| TTTTTGTTTT | GCTGTGGTTT | TCTGTTTATA | TGTTATGCTT | CTCAGTTTAA | AGAATGTTGA | 118740 |
| AATCTTCTAA | TACGAAATTT | TTTTTCAATG | AGAAGGATTT | TAAGCATCCA | GAATCAATTT | 118800 |
| TAAAATCTCC | AATTTGCTTT | ATATGTAGGT | TTATGGACTG | CTTAACTGCT | ACTCATTTTT | 118860 |
| TCCTTCATTT | ATCAATAGTG | AAATATGAAA | TTAAATAAT  | GACTATTTGT | GGCAAAATTA | 118920 |
| GGGACTATGT | AGCATATTAA | CAACTTTATA | AATAAAAGAA | TAAATCAACT | CACCTGGGAG | 118980 |
| TTGTTACTGT | CATTGACCTA | ATGCTATTTC | CCATGGTACT | CCTTGTCCCC | ATTGAGAGAC | 119040 |
| ATGAGATACT | GCAGATTTAT | GGGTCACTTT | CAACATGTCT | CCTCCAGGCC | TCATTTTAGA | 119100 |
| GAAGCATAAC | ATCATGAGGT | TCTATACAGG | CAAGATCTAG | GCTTGTGTCC | TTGAACCTTG | 119160 |
| CATTCCCTCT | CAAGAGCCAA | CCAATAATTG | AATGATCCTA | TAAAAAACAC | AGAAACACAG | 119220 |
| AGAATGGTAG | CAGAAAGCGG | ATGCTTACCA | AACCTATTTT | CTCTTTTCT  | AAGCAAGGAA | 119280 |
| TAAGAATAAC | TTACCTTCCT | CCCTTGGAGT | TAGGAGTTCT | TATGTAGAAA | GGGAGGCAGA | 119340 |
| GTGACCTTCA | AGAGAGTTTG | GAAGGGGGAG | TGATAAATCA | GTTAAAGAG  | AGCACCCACT | 119400 |
| GATTCTTAGA | TAACTTATTC | TACTTTCCTT | CTCACTCTTT | TGCATTGACC | ATGGCTTAGA | 119460 |
| ATATATTTGA | GGAAAAGCAT | ACTGTCCATA | AGGTATTATT | GCCCTTTAAA | GCTGTTGGGG | 119520 |
| GGTACTATGG | GATGGTATTC | AGTGAGAGCA | GGACAGAGTC | TCTACAGAAT | TTTCTCTGAC | 119580 |
| AAAACAAAAA | CTAAATGACT | TCCAAGGCTT | CTCTAGCTCT | AAGCATTCCA | CAATTCTTTG | 119640 |
| GAAAGCTGGA | ATCTAAAATT | GCCTTAAAAT | TAAAAATAA  | GAACAGTTAG | GGTGTACAGT | 119700 |
| CTTTACCATA | TTTATATAGA | ATCATCAGTC | TTCAGTGTGA | TACTGTGCTT | GAACCAACAG | 119760 |
| AAGGACTGAT | GAAACAGAAG | ACAAAGTCCA | GGTCTGGCGC | CATGGCTCAC | ACCTGTAATC | 119820 |
| CCAGCACTTC | GGGAGGCCGA | GGTGGCCAGA | TCACTTGAGG | CCAGGAGTTT | GAGACCAGTC | 119880 |
| TGGCCAACAT | GGTGAAACCC | CATCTCTCCT | AAAAATACAA | AAATTAGCCA | GGCCTGGTGG | 119940 |
| CAGGTGCCTG | TAATCCCAGC | TACTCGGGAG | ACCAGAGGCA | TGAGAATCGC | TTGAACTCAG | 120000 |
| GAGGCAAAGG | TTGCAACTGA | GGTCATGGCA | CTGTACTCCA | CCATGGGTGA | CAGAGTAAGA | 120060 |
| CTCTGTCTAA | ATAAATAAAT | AAATAAATAA | AATAATAAAA | TACAACCTAA | AACCTAGCAA | 120120 |
| TCTCAGCCCT | GGAATTCTAT | TCAATTGCAC | CATGTTCAGC | AGTGGTAACT | GGAAACATCA | 120180 |
| ATGCTTATCA | ATAAGAAATG | GATGAATAAC | TTATGCTATT | CCATGTGAAG | GATTTCTTTT | 120240 |
| TTCATGACAG | GGTTTTAGAA | AAGTTTGGTT | AAGAGAAAAG | CAACATGCAG | AAGTGTATAT | 120300 |

-continued

| | | | | | |
|---|---|---|---|---|---|
| AACATCGTTG | TAAAAAATTT | TTATTATTTT | TGTTTTGAGA | CTGGGTCTCA | TTCTGTCACC 120360 |
| TAGGCTTGAG | TGCAGTGGCA | CGATCTCTGC | TCACTGCAGC | CTCTACCTCC | CAGGTTCCAG 120420 |
| TCATCTTCCC | ACCCCAGCCT | CCCAAGTAGC | TGGGACTATA | AGTGCGTGCC | ACTGGGCCTT 120480 |
| GCTAATTTTT | TGTATTTTTT | GTCAAGATGG | GATTTCACCA | TGTTGCCCAG | GCTGGTCTTG 120540 |
| AACTCCTGAG | CTCAAGTAAT | CTGCCCATCT | GGCTTCCTAA | AGTGCTGGGA | TTACAGATGT 120600 |
| GAGCCACTGC | GTCCAGGCTT | TGTTTTTTAA | ATTAATAACC | CTAATCAAAA | GACAAACAA 120660 |
| TTATGCATAC | AAGGCCAGGC | ACAGTGACCG | TAATCCCAAC | ACTTTGGGAG | GTCGATGATC 120720 |
| ACTTGAGGCC | ATTTCTAGAC | CAGCTTGGAC | AACATGGTGT | GACTGTCTCC | ACAAAAATA 120780 |
| AAAACAAAAA | GCCCGGCTTG | GTGGTGCGTG | CATGCAATCC | CAGCTACTCC | GGATGCTGAG 120840 |
| GCTGCAGGAT | AGCCTGAGCC | CAGGAGTTGG | AGTTGGAGGT | TACAGTGTGC | TGTGATTATG 120900 |
| CCACTGCAGT | CCAGTCTGGG | CAACAGACTG | AGACCCAGTC | TCAAAAGATA | ACGTGTTTTT 120960 |
| TTTTTTTTTT | TTTTAAAAAA | ACAAAACCAC | AAGTATGCAT | GTATATAGAT | AGGTGTATGT 121020 |
| AAAATACTTA | GTTCAAAGAA | AAACATGTAT | ATTTCTCACA | AAAATAGGTG | AGAATTTTTG 121080 |
| TTTTAAAGGA | TAAACCTAGG | TAGCTACATA | TTAGTTTGAG | GAAGGGGGAA | CAGGGATGTG 121140 |
| ATGTGCCTGT | ATCCCTGACT | TTAGACGATG | GAAGGAGCTA | AGCAAAACAA | TTGAAAAAG 121200 |
| ACCGTTTGAA | AAATACAACT | GATTATTAAC | TCATATGCAC | ACACGCAAAA | ATAAACTTTT 121260 |
| AGAATTGAAC | TGCACTAAGT | AAAAGTGAGT | AAACTTGGCT | CATCATATAC | TCTTGTCAGA 121320 |
| TGTAAACAAA | AAAGTCCAAT | TATTAAAATC | TGACCCCAG | AATTAAAATT | GCAAAAGCTT 121380 |
| AAAGGGGCAG | TTCTGAGAAA | AGGATCTTCA | GTTTTGAATG | TGTGGGCTCC | ACCAGGGTTG 121440 |
| AAAATCCTGC | ACGACTGATG | AAACACGATC | CAGTTAAGCA | CAGTAATTTT | CAAATATCCA 121500 |
| ATCAGGGCGC | TTCCGTTTCT | AAAAACAGAG | AAACCGAGCA | AGGGATTTTG | GGTTGCAGCT 121560 |
| CTAAAACTCC | AACAAACTAA | GCTCCTTTGT | CCTGACAAGG | GCCTAAACCA | AGTCGACAGC 121620 |
| CCGTAAGTGC | ACCCATGGTA | AGGCGCTGCA | CAAAGAAAGC | ATTTTGCGTT | TCAAAGCTTT 121680 |
| GTCATGATGG | CGCTGCAGAA | AGCAAGCGAG | CTAGGCCTAC | CTGGCGGGGC | TTTCAGAGGA 121740 |
| CGCCAACGTG | GGCGCCAGCC | ACGCCAGCAG | GGTCACCGTC | CTTCCCAAGG | ACAGACAGCT 121800 |
| CGCTAGCCAC | TCCTGTGGAG | AGGGCGTGGT | TAAGCCATAT | ATTTTGCCAA | CTATCCCAGA 121860 |
| AGCATTTCTT | AGGACCACCC | AATTTCGGAA | AATGCTACTT | TAGCAATATT | GACCCCAAAA 121920 |
| CGCAATATCC | CCACTTTAAC | CTTGTATAAT | AAAAAGCCTC | AAGCCTGGGA | CTGGGCTTCA 121980 |
| ACCTTGGTTC | AATACGGTTA | TGACTAATTA | GCTTGGAGTC | GTGAGACGCG | GGACTTCCGG 122040 |
| CTACCGAAAC | CCAGGTGACT | TTAAAACTCG | ATTTTAACTC | GGTGCATTTG | AATTCACCTT 122100 |
| GCTATCTTTG | ATAGATTGAG | TAGTAAATTC | TTACTAGATG | AGGCTATGTT | AAAGTTCTAT 122160 |
| CGACTCTCCA | AGTGATTCTA | ATATAATTGA | GGGCGTGTTG | CATTTGCTTG | GGGGATTTCA 122220 |
| TCTGTGTACT | ACAGCTCTTT | TCCTGAAATG | CGTAGGTGGC | TCTTAAAAGA | GCCGTTGGGT 122280 |
| TACTAGAAGA | AACTTCTAAC | TGAATTTACT | TTTTCTTGGG | TGCCGCTTTC | TTGGGTTTGG 122340 |
| CAGTCTTTGG | CTTCGTCACC | CTAGCCTTGG | CCGCCTTGGG | TTTTACAGCC | TTAGCTTTAG 122400 |
| CAGGGCTTTT | AGCTACTTTC | TTGGGCTTTA | CAGTTTTGGG | TTTTTTGGA | TTCTTGGAGG 122460 |
| ATTTCCTTGT | TGCCGCAGGC | TTTTTAGCCT | TTTTCGGAGT | CTTGACGCTC | TTTTTGCTAG 122520 |
| CCCCCGTGGC | CTTTTTGAGC | TTTTTAGATG | CACCCGTTGC | CTTAGTTTTT | GTAGCCACCT 122580 |
| TTGAGGCGCC | GGGCTTGGTT | CCACGGAGG | ACGCCTTCTT | GTTGAGCTTG | AAGGAACCCG 122640 |
| AGGCTCCGGT | ACCCTTTGTC | TGCACCAACG | TTCCCTTGCT | TACCAGGCTC | TTAATGCCCA 122700 |

-continued

| | | | | | | |
|---|---|---|---|---|---|---|
| GCTTAATGCG | GCTGTTGTTC | TTCTCCACGT | CGTAGCCTGC | GGCCGCCAGC | GCCTTTTTAA | 122760 |
| GAGCTGCCAA | CGACACACCA | CCACGCTCCT | TAGAGGAGGA | AGCAGCCTGC | ACGATCAGCT | 122820 |
| CTGACACGGA | AGGGCCAGCG | GGTTTTTTCT | TGGAGGCTGC | TGCAGCCTTA | GCAGGTTTCT | 122880 |
| TTGCCTTCTT | GCCAGCTAAA | GGTTTCTCAG | GAGCAGCAGA | AGCGGCGGGG | GCGGGAGGCA | 122940 |
| CTGTTTCAGA | CATGGTGACT | AACACAGCAC | ACCAAATAAA | GTGGTATAAA | CCTGACGAAG | 123000 |
| CAGGATGCGA | AAAAAAGGCC | CCAACGCAGC | CTATTTATAG | GGTGGGACTG | CGCCGTGATT | 123060 |
| GGTGCCCGTC | AGTGCCCGCC | CCTCGCGCCC | TAGCGCCCCC | TGCGCGCTGC | CGAGGGTTTC | 123120 |
| GCCCAGTCTC | AGAAGGCAGC | TGGGGGCCTC | TAGGGCCTAT | GGTCCTGCTC | CCCTCAACGC | 123180 |
| AAGCAAACAC | ACAGAAAAAG | CCGCTCTGGT | TGCCTCATTG | TGAAGGAAAT | TGTAGGCAGA | 123240 |
| CTGCCGCCCA | GTAACATCAG | AGGGTACCGC | TTCTCTCTCA | AAAAGCAGCT | CTTTTTTAGG | 123300 |
| GAGTAGGTTG | AGAGGGGGCG | GTTACAAAT | GCAGTGCCAC | AAGCATCCGA | GGAGTTTTAT | 123360 |
| TAGAAATTTT | TAGAGGTCCG | TTGCCAGAGA | TGTTAGTTTT | TAATTTGCAA | GAAATGTAAA | 123420 |
| ATACAGTGTT | TTGAATAGTT | GCGGAGGGAG | AGAAAAGTGC | GAGTTTTAGG | CCGTGTTAGG | 123480 |
| GCCAGTTGTC | ATCAACTCTA | TTACATTTTC | TGGCAATGTT | TTAGAGCGAT | GTGTCTCGCG | 123540 |
| AATACCTTTC | ACGTCAAACA | AGAATGAATC | GTAGACAACA | CCAGAATTCA | CAAACGCTGC | 123600 |
| AATTAATACT | CAAACTGCAA | GTGTGGAAAC | GTTTCTGCAC | TTGCAACTTA | TTTCCACGT | 123660 |
| CCAATGTGGG | ATGCACTTCA | GGAATTTCCA | ATGCCCTTTT | CATCCATACA | ACATGCCCCA | 123720 |
| AATTGGTATT | AAGGTTTACA | ACCTGTGTTC | CATGTCAGCA | CACGCAATCA | GCGCACCATG | 123780 |
| ACATGGTCAA | CTCATTCTTT | TATTCAACAA | ATATTTATGG | GCCTCACAAG | CCTGCGAAAG | 123840 |
| GCGTTAAATG | CTGGGTCCAC | GAAACCGGTT | CCCTGACAGG | CATTCTGCTG | GGGAGTTAAG | 123900 |
| TCCACTTAGT | GTGAAAGCAA | ACACGGGTGA | TAAATGCAAG | CACACCCTGG | GGATAAGATT | 123960 |
| TTATGGTAAC | AACCCTTTAA | CTTGTTTGTG | GCTGTTAAGT | GCATTTCAAA | GTATCAATAA | 124020 |
| GCTAAAACGA | TCTCACATTG | CCAATCAGAG | ACTCAGCTAA | TGGGAGAATA | AAAAACTATT | 124080 |
| AAATCGACAT | CCACTTCTAC | AATCCTATTC | TGGATAACCC | CCTAGCACAG | CACAGCAGAG | 124140 |
| AGTGAGGTAA | TGCGGTCTTA | TTTCCGCTCC | TGCTGTGGTA | GTTTTCAAAT | AAGTCCGAAC | 124200 |
| CATGCTAAGT | AACCTGAGCT | TTTCCCCTTT | TTGTTCAAAC | AACGTGCCAA | CCAAATAATG | 124260 |
| GAGTGGTCCC | AGATAAGTAT | TGTACCCATC | TTCTGCACCA | GTGCTTCCTA | CGTCCCATTT | 124320 |
| TATTGAGAAG | GCATGCATTC | AAATATTTCA | CGTAATTTCT | AAAAATTTGG | AAAATAACGG | 124380 |
| TTGGAAACTC | TACATCTTGG | TTTGACGGCT | AGTCAGTTAT | GAAACACAGG | TATACAAAAT | 124440 |
| TGGAAGATTT | TTGTAAGTAA | ACCCTTTGTG | AAAGATATAA | ACCTTTCTTA | GTGTAATAAG | 124500 |
| CGAGGTATCT | GAAAAAACGC | AACTTTTGAA | AAGGAAATAC | TCCTAATTAT | CTGATTCAGG | 124560 |
| AGTTTCCACT | TTAAATAATG | GGTTCTGCCT | CCCTTTTTTC | TATTGGGTTA | AACTGGTTTC | 124620 |
| AAATAAAATG | GGAACGCTCC | ATGCAAATGA | AGGATGATAG | ATCTGCTTTC | TAAATGGCTG | 124680 |
| TTCAAGAAAA | TAGCCTAAAC | CAATCAAAAG | ATAGAATGTG | GCCTGTCTCT | TGTGAATTTA | 124740 |
| AAAAGGTCAC | AATCCACTTT | TCAGTGTTTT | GAGATTTTCA | AAATGATTGC | ATTAGCTCTT | 124800 |
| GGCAATGCTA | AATTATGTTC | CTTGCGAACC | ACTATCCAGT | TTCTCTTGGG | CCAAGTCCAC | 124860 |
| CTCCTGCTCC | GCAAGAGGAA | CAACTCCCAG | CTGGTGGTAC | CTGGCGGCAG | TGCTGGAGAA | 124920 |
| ACGCCATTTT | GTGACTGGCA | GAGTACACCT | AGGCTTTAGA | AAACAAAAGC | TGCAGAACGC | 124980 |
| TGCAAGTTTA | GGATTCAAAG | AGCATAATCA | AGAGAAAGAC | GTCTCATAGA | AAATGTTTCT | 125040 |
| GAGTAATAGT | GTAATCCTAC | TATGTTTGAG | ATGCTTTGTA | GATTTCAATA | ACACTCCTAA | 125100 |

-continued

| | | | | | | |
|---|---|---|---|---|---|---|
| GTCAATTAAA | GCATTACAAA | GGAATCCAAT | TCTTGTGAAA | GGTTTCAGAA | ATTCCCGTAA | 125160 |
| AGGGTACATT | TCCGGAGAGG | AGGTGAGCAG | TATTCCCTCT | TTTTTTTTTT | TTTTTTTTTT | 125220 |
| TTCCTAAAGA | GCTGAAGGTT | ATACGGAATT | GGGGAATTAT | AATACCTTTG | GAATCAATGC | 125280 |
| CTTGTTTTAT | GGAAAATAAA | CACAGCCTTC | AGGTTATGAA | AACCAGATGT | AGAAGAGGAC | 125340 |
| AAGTTTAAAA | AATTAAAGTC | CAAGCCGGCG | CAGTGGGGCT | CCCCTGTAAT | CCCAGCTACT | 125400 |
| CTGGATGCTG | AGGCGGGAAG | ATCCTTTGAG | CCCAAGTTTA | AGACCAGCTT | GGGGAACAAA | 125460 |
| GCAAAAGTAA | AATAAAATAA | TAGTAGTAAT | AAAATACCAC | TTAAATAATC | ATCTGTAGAG | 125520 |
| TTGGAATAGA | ATATAGTAGC | CGGTGAAACT | GCACGATTGT | TGCTGGCTTA | AAGATAGACC | 125580 |
| AATCAGAGTG | TGTAACGTCA | TATTTAGCGT | CTTCTATCAT | CCAATCACTG | CACTTTACAC | 125640 |
| ACTATAAATA | GAGCAGCTCA | TGGGCGTATT | TGCGCTAGTG | TTGGGTGTTC | CGCTGTGCTG | 125700 |
| TTTTTCCGTC | ATGGCTCGCA | CTAAGCAAAC | TGCTCGGAAG | TCTACTGGTG | GCAAGGCGCC | 125760 |
| ACGCAAACAG | TTGGCCACTA | AGGCAGCCCG | CAAAAGCGCT | CCGGCCACCG | GCGGCGTGAA | 125820 |
| AAAGCCCCAC | CGCTACCGGC | CGGGCACCGT | GGCTCTGCGC | GAGATCCGCC | GTTATCAGAA | 125880 |
| GTCCACTGAA | CTGCTTATTC | GTAAACTACC | TTTCCAGCGC | CTGGTGCGCG | AGATTGCGCA | 125940 |
| GGACTTTAAA | ACAGACCTGC | GTTTCCAGAG | CTCCGCTGTG | ATGGCTCTGC | AGGAGGCGTG | 126000 |
| CGAGGCCTAC | TTGGTAGGGC | TATTTGAGGA | CACTAACCTG | TGCGCCATCC | ACGCCAAGCG | 126060 |
| CGTCACTATC | ATGCCCAAGG | ACATCCAGCT | CGCCCGCCGC | ATCCGCGGAG | AGGGGCGTG  | 126120 |
| ATTACTGTGG | TCTCTCTGAC | GGTCCAAGCA | AAGGCTCTTT | TCAGAGCCAC | CACCTTTTCA | 126180 |
| AGTAAAGTAG | CTGTAAGAAA | CCAATTTAAG | ACAAAAGGGA | ATGCATTGGG | AGCACTTTTC | 126240 |
| GTTTTAATGC | TACTGAAGGC | TTCAAAACCA | ATCGATTTCG | GCCGGTCGCG | GTGACTCACG | 126300 |
| CCTGTAATTC | AAGCACTTTG | AGAGGCTGAG | GCGGGCGGAT | TACCAGAAAT | CAGGAGTTCG | 126360 |
| GGATCAGCCT | GGCCAACATG | GCCGAATCCC | GTCTCTACGA | AAAATACAAA | AACACGCCGG | 126420 |
| GCGCGACGGC | GAGCGCTTGT | AATCCCAGCT | ACACTCTGAA | GGCTGAGGCA | GGAGAAACAC | 126480 |
| TTGAACCTGA | GAGGCAGAGG | TTTCAGTGAA | TCGAGATGGC | TCTAATGTAC | TCCAGTCTGG | 126540 |
| GCGACAGAGA | GATTCGGTTA | AAAAAAAAGT | TCGACTTAAA | ATAATTCTGG | AGTCAGAATG | 126600 |
| GGTTTACATT | TAATTCTTAA | CCCAGTTCCT | CAAAGCCTGT | AGCTCTGTTA | AGAAAATAAA | 126660 |
| GGCCATTGGT | CAAGCCTGCT | TGGTCCCACC | CTCATCTCCC | CACCCTCCCC | CAATCGCTGC | 126720 |
| TCCCGCCATT | TCCTGGGGCT | TGGAGGAGGG | GTTAAAGGAG | CGGACTGTAG | GCGTCACATT | 126780 |
| TCCCGCCTGC | GCGCTTTTCA | GTCTCAGTGT | CCGCTGGAGG | TGGGGGCAGG | GGTAACGTAG | 126840 |
| ATATATAAAG | ATCGGTTTCC | TATTCTCTCA | CTTGCTCTTG | GTTCACTTCT | TGGGAAGTCA | 126900 |
| TGTCTGGACG | TGGTAAGGGC | GGGAAGGGTT | TGGGTAAGGG | GGGTGCCAAG | CGCCACCGCA | 126960 |
| AGGTGTTGCG | TGACAACATC | CAGGGCATCA | CCAAGCCGGC | CATCCGGCGT | CTGGCCCGGC | 127020 |
| GTGGCGGTGT | GAAGCGGATC | TCTGGTCTGA | TCTACGAGGA | GACTCGCGGG | GTGCTCAAGG | 127080 |
| TGTTTTTGGA | GAACGTGATC | CGTGACGCTG | TCACCTATAC | GGAGCACGCC | AAGCGCAAGA | 127140 |
| CAGTCACTGC | CATGGACGTG | GTCTACGCGC | TTAAGCGCCA | GGGACGCACC | CTTTATGGCT | 127200 |
| TTGGCGGTTA | AGGTTGCTGA | TTTCTCCACA | GCTTGCATTT | CTGAACCAAA | GGCCCTTTTC | 127260 |
| AGGGCCGCCC | AACTAAACAA | AGAAGAGCT  | GTATCCATTA | AGTCAAGAAG | CTCAATGTGT | 127320 |
| AATTAAGATG | AATGATACTG | AGCTGACATC | CTAAAAGGA  | AAGATTAGGG | GAACTCCAAG | 127380 |
| TTTGCCCTCC | ACTCACTACA | TATGGGTAGG | GGAGCAACGA | TATTCCAACT | CTGAAGAAAG | 127440 |
| AGTGGAAAAA | AAGTAGTGTT | AAAAATTTGT | ATTAGTTTCC | AAGGGACAAA | GAAGCGCTGC | 127500 |

-continued

| | | | | | | |
|---|---|---|---|---|---|---|
| CCAATCAATG | AGGGCCATTC | GTAGCTGTCA | ACCAATCAGA | ACTGATGAGC | TAATATTTCC | 127560 |
| TGAGGCAAGC | CAGGGAGCCG | GAGGGGAAGC | TAAGAAGCTT | ATTGAGAAAA | AACAAAAACC | 127620 |
| CTGTTTTAGG | AAAAAAAAAA | ACCATCTTTT | AGCGATTATG | AAATAAAATC | ACAGAGACAT | 127680 |
| TTAAGTATCC | CTCAATCATG | TACTGAGAGC | AATACTAAAT | TTATCGCCAC | CAATACAGTT | 127740 |
| TTACTCTATT | AAAAAGACCC | TGAAAATTGA | AACCCTATTC | AGACTCCTGG | AATACCCAGG | 127800 |
| ACACTAAATT | CAGGGGAGAT | TAAAATCTGT | TTTAGAGAGA | AAAGGCACCT | TTTTCAGTGT | 127860 |
| TACCGCGGCC | TTCAGCAGTT | AACCTTTTTT | TTTCCCCCTT | TACGCAGAAA | TGGAAATTTG | 127920 |
| GGTGATAGAA | ATATTCCGAA | ATTAAATTGT | GATGATGGTT | GTACAACTAA | GAAAACACGG | 127980 |
| TAAAATTCAT | TGAACTGTAC | CTAAAGTGGG | CAAATTTTGT | GGTACATTAA | ATATCAATAA | 128040 |
| AGCTGATTAT | ATACATACAC | ATATATTTTT | ATATATGCAG | AGAGAGAAAT | GATGCAAGCA | 128100 |
| GGGTGGTAGG | ACATGAGGTT | GGTAGCATAG | GCAATGTTGG | TCTGTGAAGG | GCCACCTGTG | 128160 |
| CTAAACCTGG | AAGCCTGGGG | TTTGTCCAGT | CAAGCCATGG | TAGCCATAGT | TTTAAAGGAT | 128220 |
| GTTCCTGATG | CAGTTATGTG | TTCCAGTTAA | GTACATCTAG | CTTCAGAACT | CAGCTGGAAA | 128280 |
| AGGGATGTGA | ACTTCAGGTT | AGCTGATAGG | GAAATATCTT | ACTCTCATCT | GAGTAAATAT | 128340 |
| TCACAAATGC | CTCTCATTGT | GCTCTTTTTG | GTACCATTGT | TATAGGACTG | ATTTCAGCCT | 128400 |
| CACGATGTTA | GCTTCAGTGA | TGGATGTCTC | TTTATTTTGA | GGTCCTGTTT | TCCACCTGAC | 128460 |
| AGTTTTCATC | CAGGATTTCT | TGAGGAATTA | CACAAGTACC | CAGCTTGGCT | TAATTTAAAA | 128520 |
| CTGACAATGG | AGAGAATTCA | TAGCTGCATT | CTGGATAGTT | TCAGGAATCA | GAGGAGCAAA | 128580 |
| AATGAGCCTG | GTATGGAGGG | TGGGTCATTT | TATGTCTTTC | TTAGTTGGTA | TTTTAAAGAT | 128640 |
| ATTTATTGAT | CTCATATGCC | AGATATTGTT | GAAATCATTG | GGGTACATAA | GTTAGAAAAT | 128700 |
| TTTAATTCCC | TTTCCTGAAT | TCCAGAGTCA | ATGTAGAGGG | GTGTGTGGAT | ATCGATTACC | 128760 |
| CATATGGGAG | GTATAGTCGT | TGTAACAATA | AGCCACGACT | AGCTCCTGTT | ACGTTTTGCC | 128820 |
| TGGCCTTTCA | TAGCATTGCT | ATGTTCATAG | CATTGCTGAT | ATGTCATACT | CATCTTAGGC | 128880 |
| ATACCCACCA | CCACCTTGGG | CCTTCTTCAG | TCCTAACACT | CATGCAGTCC | TTGTTCAGAA | 128940 |
| CAAAGATAAT | GTTGCTTAAT | TTGCAACCCC | TAGACTATCC | CCCAGATTTT | CTAAAGAGAA | 129000 |
| ACTGCACGCT | GATTGCTTCA | GGCAGTGGCA | GGTCAAGGAA | TGAGATGGGG | AATTGATTGT | 129060 |
| GTTAGCATTC | TGGTGGGCTT | AGTGGAGAGC | CTGGAGACTT | ACATAGAAAA | TTCACACATC | 129120 |
| CTTTCATTCA | ACAAACCTCC | ATAAACTACC | TGTTAAACGT | CAGCCCTGTT | CAAGGTGCTA | 129180 |
| GGGATACTTC | TGGGACAAAA | CAAAGTCCCT | ACCTTCAAAA | AATATATTCC | AGTTGGGGA | 129240 |
| GAGAGAACAA | ACACAAAATA | AAATATATCT | AGTTATATGT | ATTTTTTGTT | AAATATATTA | 129300 |
| TTACATATAT | AATTCTAGGT | GGGGAAATGT | TATATATATA | TGCTATTGAG | GATAGTCAAC | 129360 |
| TATATATATA | TATGCTAAAT | GAGCAGAAAA | GCTTATTTTA | CAAGGGATGA | TTATGGGAGG | 129420 |
| TCTCTTTCGT | AAGGTTGGTA | TTTGAGGAGA | GGCTTGAATG | AAATGAGATC | TAGAGCCATT | 129480 |
| CAGATATCCA | GGACAAGACC | CTTCTAGGGA | GAAAGAATAG | ATATAAAGGT | GCTGATGCTG | 129540 |
| GAAATGCTTG | GTCCATTCCA | GAAACAGCAA | GGTCAGTGAA | GAGAAAGAAC | TGCGAAGAGA | 129600 |
| ATGAGGTCAG | AGGGTAGCCA | GAGTACAGAT | CTAGTAGGTT | GAGCAGCTCA | TCCTAGTTTG | 129660 |
| CTTGGAACTT | TCTAAGTTTC | AGCACTGTAA | GTCTTACACC | CTGAGAAACC | CCTGAGAGTC | 129720 |
| AGGCAAACTG | TAATGGTTGG | TCATCTTACT | TGTAGGCTAT | GATAAGGATG | CTGGTTTTTA | 129780 |
| TTATGAAGGT | GATGGAAAGC | CAGTGGAATC | TTTTCAGCAG | ACAGTGGACA | TAATACCTTC | 129840 |
| AAAAAGGATC | ACTGTTGATG | CTGGATAGAG | AAAAAACTGT | ATGACAGGGG | GATTAAAAGT | 129900 |

| | | | | | | |
|---|---|---|---|---|---|---|
| GAAAACAAAG | ACCAGTTTGG | GGTCACTGTG | GTCATTCAGA | CAAACCGCCA | TGGCAGCTTG | 129960 |
| CTCCTAGAGA | AGCAGCAAAG | AAAACAATGA | AAGGTATTCT | GATTGATTTT | CAACAGAGCT | 130020 |
| GACTGCATTG | GGTGAAAGTT | GTAAGAAGCT | CAGGACAAAC | AATATTGCAC | AATTCCTGGC | 130080 |
| CCAAGCTGCT | TGAAGAATGG | AGTTCTATTG | ATTGACATGA | CAAATATCAG | AGGAAGAACA | 130140 |
| GACTTGGTGT | TTACGTATAA | ACATATTTTG | GACAAGTTCG | AGATGCCCAT | TATTCAATTA | 130200 |
| GATACATCAA | ATATGCAGTT | GTATATGAGT | CTAGAGATTT | AAGGTCAGGG | AGATGGTTTA | 130260 |
| TAATTGCAAA | CACTTATTTA | GAGACACAGT | TTCACTCTTG | TCTCCCAGGC | CTAAGTGTAA | 130320 |
| TAGCGCGATC | TCAACTCACT | GCAACTTCTG | CCTCCCGAGT | TCAAGCTATT | CTCCTGTCTC | 130380 |
| ACCCTCCCGA | GTAGCTTGGA | TTACAGTCGC | CCGCAACCAT | GCCCAGCTAA | TTTTTTTTTT | 130440 |
| TTTTTTAGTA | GAGACGGGGT | TTCACAATAT | TGGCCAGGCT | GGTCTCGAAC | CCCTGACCCC | 130500 |
| AGGTGATCCA | CCAGGCTCAG | CTTTCCAAAG | TGCCGGGATT | ACAGGCGTGA | GCCACCTTGC | 130560 |
| CGGGCCTATA | TTTCTTAAGC | TCTATGTTTC | GTTCTGAAGC | TTGAAGTGGG | TGGAAGCAAA | 130620 |
| CTGATAGAAT | TTGGAGAGGT | GGTTAGGCAT | CCCGGGAATG | AGAAACAGCC | CGAAGCTGCC | 130680 |
| ACTATCACAG | GCTTTGGCAT | TGCTAGAAGT | TAACGTGGCA | CTTACAGCTA | GGCCGTGGTG | 130740 |
| TTCTGTTGAA | CAAACTATTT | GACAGAGCAC | AGAGCATGTA | AGTGGTGAGG | CCAGTTGAGT | 130800 |
| TAGCCAAGAA | AAGAGGAGTC | CAAGAACTGA | GCCAGAGTAC | ACCAGAGTAT | GTAGTGGAGT | 130860 |
| ACAGCTTTCT | CATTCTTTAG | TAGGGCTGTG | TAGAGAAATA | CTCTATTTTA | TGGATGTATA | 130920 |
| GATCACTCTA | GTCCTTTCTG | ATGAAAACTT | TACAGTTGCC | ACTCATTTAC | TATTACAAAC | 130980 |
| AATGCTGCAC | TACATTATGT | TTCAGTTTTT | AGCCATCTCA | TCTGGTCTCA | GCATTTATTT | 131040 |
| ATCTGCTGAT | GACTCACACA | TTTTTATCTC | CAGCTCAGAC | CTCTCACCCG | AACTCACTTA | 131100 |
| TTCAACTGCC | TATTCACTAT | ATCCTCCTGT | CAGGAGAAGC | TTGTTAGCAA | AGTAACCAGA | 131160 |
| AAACAAAGTT | GATTTTTTTT | GCTGAAGTAG | CCATCAATAT | ATTTGTTACT | AAATCAAAGA | 131220 |
| TGCTGAATAT | TTGGCTGACT | TCTAAAAATC | TGGTCACCTA | ACTTTGACAC | TTCCTAGGTC | 131280 |
| GTACAGTTTG | AAACTTTCAC | AATTAAATCA | GTTTTGGAAT | TTACAATTTA | AGGCAGGAAT | 131340 |
| AGAAGACTAT | TGGGTTGACA | GGTACAGTGA | AGATGCAAGT | CATCTGAGAA | TCTTACATCA | 131400 |
| GAGGGGGCTT | CCATCTTATA | GCTGCTGCCA | CGGACCTCGG | AGTCAGAAGA | AATTTGAGTC | 131460 |
| CTTATTTATA | AAACAGACTC | CCTTAGTCTA | CTAAGTGGGA | ATTTACGAAC | TGCGTAGGCA | 131520 |
| GCCTGCTTAG | GGGAGCCTCC | AGCCTGAGGA | CTGAAAATAG | CAAAGCAGCT | TTAACCGCCA | 131580 |
| GTCCTACTCC | AGAGAAGGGG | GAGGTGACGT | CACTCAGCAG | GACGCCAAGC | TCAACTAGAA | 131640 |
| ATGGAAGTAA | AGGCTTCTGG | CGCTACCGGC | AGGGGCGGT | TAAGGACGGC | AGGTGTTACC | 131700 |
| AGGGAAGCTA | AAAGTACAGC | TTTTGCTGAC | GTTAAGTCAG | ATACGCCTGG | GAAAACAGAC | 131760 |
| CTGACACCCA | TTTTAATCCA | CCTACTCAGT | TCCAGGCAGC | TAGCATCTTA | GGCTCTCGTA | 131820 |
| CAAATAACGC | ACAACTCGTT | TTTAAAACTA | AAAAGCTGAG | CTACTCATTT | ATCGGACTCG | 131880 |
| CGCTGCACGT | TAAGTTGCTT | GACATGTCAA | AACTATAGCA | TTGAAGTTTA | TAGCTCACTT | 131940 |
| ATCTCGGAGA | CCTCGTTTAC | TTAGCTGATT | TCTGCTTTAG | CAGCCACTCA | GACCAAACAA | 132000 |
| CCTGGTCTCT | CCCAACTGGT | TTATAATAGT | TCTACATACT | AGGCAGAATA | GCCGAGTAAA | 132060 |
| GCCATTGAGA | TGTTACCATC | CGAAAGAATA | CAATCACAGC | TCTTTCTGAG | AGGGAGTGGG | 132120 |
| CGGCCCTGAA | AAGGGCCATT | GGAAGAAAAC | TGACGAAAAG | ATTAACCGCC | GAAGCCGTAC | 132180 |
| AGAGTGCGTC | CTTGACGCTT | GAGCGCGTAA | ACCACATCCA | TGGCAGTGAC | AGTCTTGCGC | 132240 |
| TTGGCGTGCT | CCGTGTAGGT | CACGGCGTCC | CGGATCACGT | TCTCCAGAAA | CACCTTGAGA | 132300 |

| | | | | | | |
|---|---|---|---|---|---|---|
| ACGCCACGAG | TCTCCTCATA | AATCAAACCG | GAAATTCGCT | TAACCCCACC | ACGCCTAGCA | 132360 |
| AGGCGCCGAA | TGGCCGGTTT | GGTGATGCCT | TGGATGTTAT | CCCGCAGCAC | TTTTCGGTGA | 132420 |
| CGCTTGGCAC | CTCCCTTACC | CAAACCTTTA | CCGCCTTTGC | CGCGACCAGA | CATGTCTAAC | 132480 |
| CAGCTGACAA | CAAAAACCAG | GTACGCGAAA | AGAAAGCAAG | CCACGAGCAT | TTATACACGA | 132540 |
| ACATCGGACC | TTATTGAGAA | CTGAAAGCGG | GAGCGAGGAT | AAGGAGGCGT | TGCTGCCTCA | 132600 |
| CTTTTTGCTC | CGCCCCTCGA | GGGGCAGTGA | CCTAAGGACT | GCGAGGGAGA | ACACAATAGT | 132660 |
| TTCACTTTTT | AATCCCTTTA | GTTTTCCCT | CCCGTTACG | ACACTACTAT | TTGAATCTGA | 132720 |
| ATTTATACCC | TCGACTGAGA | ATTTTAATAA | GGGCTTATAT | TAAGGGCTTT | CACTAATATG | 132780 |
| CCGGAGTGGT | AAACTTTTA | AGTCTTTCAA | GTGCTTGAAG | ACATATTGAC | TATTCAAAGG | 132840 |
| TACTTAAAAG | AGCAGGCGTG | AAAAGATCAC | TCTGGCCTTA | TGTTTCTTG | AAAGCTGACC | 132900 |
| TGTTTCTTAG | AAGCAGTAGG | TGAAATTCTC | ATATGAAAGA | TGTTCTCACT | GTAGTTTAAA | 132960 |
| AAAAGCAACA | TTCTTCTCAA | GGATAGGAGG | CTGAGGCCAA | GAGAATTCTG | TACAAACCTT | 133020 |
| GCACTAGCCC | TTGCTGGGCG | CTTCTCTACA | CAGTTATATA | TTCTAGCCTA | AATCCCTTTG | 133080 |
| CTTTAGCGCA | TTTTTACATT | TTACTAATTG | TCCAATTCAT | TATATAAGTA | GCTAACTGCT | 133140 |
| TTTTTGGGC | TTTCATTACC | TTATGAGAGC | ACCTGTGTCA | CGTAAAACCT | GTGTTAAATA | 133200 |
| AATGCATATA | CCTTTCTCCT | GTTAATCCAT | TTTACATTAA | TTTAATTTGC | TGGTCCAGCC | 133260 |
| AGAGCCCTAA | GAGGATGGGA | GTGGAGTTTT | GCTATCCTTC | ACACTGTACT | GTCTCATTCA | 133320 |
| GAAGAGGGTG | ATAGCTCATT | GCAACCGTGC | CTTCATCTGT | AAATCGGGTT | ATGATGATAC | 133380 |
| TCAGGGACT | TTTAATTAGC | TAATGTGAAC | GAGGCATGAG | AAGAGACTGT | GGAAAAGAAA | 133440 |
| TAAATATTAC | ATAATATGGT | TTAATTTAG | ATGTTACTAC | TTAAAAAAAT | CTGCTCAGAG | 133500 |
| TTGGGATATT | GTCCTGAACT | CTCATTTTCG | TGTTTTACT | CCCAACACTA | TATTGCTAGC | 133560 |
| AGCAACTATG | TATGTATTAG | TAAGGATTGT | TTTTTAAAA | TCACAGCCTG | TAATAACGTA | 133620 |
| CAAGGTGTTG | ACAGATTCCG | TTTAGCTTTT | CATATGTGAC | ATGTTAAAAT | TGTCCGAAAA | 133680 |
| TATTCCTTTG | TTCTCTTTTC | CAAGGTGCAA | TACAATAGCA | GCATTCGTGC | TTTCCTATAG | 133740 |
| CCAAGTCTGG | AGTGTAGTTC | AACTCTCCAT | ACACGCTTCT | CACTGTTGTT | TTAAATTTCC | 133800 |
| TGAAAACATT | CTTAAATCAC | TTCTATTGGA | AAAACTGCAA | GGGCTACTGC | TAAATTTTTA | 133860 |
| AGTCTGAAAA | ATGCACCCCA | AACTTGACTT | CTTTCTCTGA | GAATCTTAGC | CATCTCACCC | 133920 |
| AAATCTAACA | AACCAAAACT | GATTTAGAC | TTCAACAGCA | TTAGCTGTAA | ACTTCAGCCT | 133980 |
| GCAGCATAAC | ATCACTTTGT | TGTGACTGGG | CAGGAAAAAC | CCTGTTAAAC | TGTTTCAGGC | 134040 |
| GCGTCCGTGT | GAAGAGACCA | TCAAACAGGG | TTTGTGTGAG | CAACAAGGCT | GTTTATTCTA | 134100 |
| CCTGGGTGCA | GGCGGGCTGA | GTCCGAAAAG | AGTCAGCGAA | GGGAGATGGG | GTGGGTCCGT | 134160 |
| TTTATAAGAT | TTGGGTAGAT | AGTGGAAAAT | TACAGTCAAA | GGGGGTTGTT | CTCTGGCTGG | 134220 |
| CAGGGGTGGG | GGTCACAAGG | TGCTCAGTGG | GGGAGCTTTT | GAGTCAGGAT | GAGCCAGGAG | 134280 |
| AAGGAATTTC | ACAAGGTAAT | GTCATCAGTT | AAGGCAGGAA | CAGGGCATTT | TCACTTCTTT | 134340 |
| TGTGTTTCTT | CAGTTACTTC | AGGCCATCTA | GAGGCATACG | TGCAGTTCAC | AGGGGATATG | 134400 |
| ATGGCTTAGC | TTCGGCTCAG | AGGCCTGACA | AACTGAACAA | CTGGGAACAA | ACAACATTTA | 134460 |
| ATGCACACAA | TCTCTATCTT | GTAGGGAGGC | AAAATTTTAC | CTCTACTCTG | TTAGGGTCTC | 134520 |
| CAGCTGGACC | TGATAATTCA | TTTGCCATAA | AACAGATTAG | CAGAATGAAA | GCATACAAAT | 134580 |
| GTATTTAATG | TAAATTTTAT | GGGACAGGAG | AACCCTCATA | AAAAAGTGAA | GCCCCAAAGA | 134640 |
| AATGGCAAAA | GCTAAATGCT | TTCACATTAA | GTTAAAGAGA | GGCAATTGTG | GGAAAGTAAA | 134700 |

| | | | | | | |
|---|---|---|---|---|---|---|
| CCATATGAGG | AGATTAAAGG | AATATATGAT | TATTTTAACA | AGGTTTGTTT | GTGTATAGAA | 134760 |
| GTCTCTCGGC | TATGACTCCC | TGCTGTGTTT | GTGCAGAATT | ATCTCATCTA | TGCCTCTGGG | 134820 |
| CTGAAGAATA | TGTCTTTTCA | CCTGGTACAA | GCAGAGCATT | TTTCACATTG | GAACTTTTAT | 134880 |
| CTCCTGTTTT | CAGAAAGAAA | AGTTTAGAAG | AATTCCCTTC | TTGAATGCTG | TTTTTGAAGT | 134940 |
| GCCTTTAGCT | CAAAAGAATC | CTGATCCCAC | AGTGGTCTAT | TTTTGGATGG | TATATTCTGC | 135000 |
| AAACAACACC | CCCTTTTTGT | CTCCAATCTC | TCCTTAATTA | CTCCTCTAAT | ACAAACAAT | 135060 |
| AGATTCTTAA | TATAATATTA | AAATGTTTGC | ACTACTCACA | AATACAAAAT | GCTCAATAAA | 135120 |
| TTTTCTTTCA | CAAATGAGAA | TTTCATCCAT | TCGTTAATTT | TTAAATATCA | ACTGTCAATG | 135180 |
| AAGAGTTACA | GCAGAATCCT | TGTTCTGTTG | AGGAGGGGGC | AAAGAATGTA | AGTGAGGGAG | 135240 |
| TGGAAAATAG | CTGGACTGAG | CTACCACCCC | CTGTCCATCT | GATCCTCAGA | CAGTAATGTA | 135300 |
| ACTTTATTCT | TTTATGCTAT | TCGTCAGACC | CAGTACCTCC | AACACATTTG | TTTCCTACAG | 135360 |
| ATAAAGAAAA | TATAAAAAGT | CAAGCGCTAT | ACATCAGATC | CAGCACATCT | ATAACTGGAA | 135420 |
| AAAAAATACT | TGACCTTCAG | CTGGGCCCAG | AGCTTGTGAG | TAGTCACCTT | GGCATAGACC | 135480 |
| AAGTCCATTG | GCATCTCTAA | CATATCTATA | CTGTCTGTGG | ATAACAAATG | TCTATGCCAG | 135540 |
| TTAGAGTCGC | TTGTATAAGA | GTCAAGAAAA | ACGAATCATA | AAACAAACTG | ACATATTCAT | 135600 |
| TTTCATAATT | TTTAAAATGC | AAATATTACT | TTATAAACCA | AAAACTGCCT | TATTAAAAGC | 135660 |
| TGGAACACAA | ATGAATTTAA | GTAAACGATG | CAATTCAAAT | TTAATCTTTT | GTGTGTGTGA | 135720 |
| TTTGTTGTTG | TTGACAGTTG | GTCAGGCGAT | TTTAGTATGG | TACATCAGTT | TACATTCTAG | 135780 |
| ATGTAGGCCA | AGAAAGAATG | TTAGGTGTAA | AAAATATTTA | TTGTAAAAAA | GAATGTGAGG | 135840 |
| CAAGGTCTTT | GGAATTAGTA | GTTTTAATGT | TGGACATTCT | GTGGTTGTTC | TAAAGTTAGT | 135900 |
| CTGTAAAATG | TGATGTAAAA | GCTATATGAT | AAAAAAATAC | AAAATATAAA | AATTTTAAAG | 135960 |
| TAAATATTAC | TTTTGTTTGC | GTACAGTATT | CCCATCCCTC | TAAATTTTCT | TCCAGTACTC | 136020 |
| AATCCCCAAC | CTCCAAAACC | GAAAAGCAAG | ATCAACAGAA | AGAAAATGGT | TAAAACTTGT | 136080 |
| AAATTCTAGA | TTTTAATAAC | TACAGGCAAG | AAGTACTGAA | AAAAAGAATG | TGGCATGTCA | 136140 |
| TGGTGCATAG | TCCTAGAGGA | GACAAAGCAA | TGCAACCAGA | TAGACTATTT | ACAAGCAAAG | 136200 |
| CCACACATAT | AAAAATTCAT | ATATAAGGGA | TTAAATTATG | CTTGGTCGAC | AGACTGACAG | 136260 |
| ATTTAAAGTG | GGTAGCTAGC | TATGGATAAA | ATGAGAGCCA | GTTAGATCCC | TGCCTCACAT | 136320 |
| TTTGCACCAG | AATAAATTTC | AGGTTAATGT | TAACAGCCAA | ATGAATTTAA | CAGTATATAT | 136380 |
| ATATATATAT | ATATATATAA | TATATGAGAA | AACCTAGGGG | ACTATGTATT | GAGCTGAGAA | 136440 |
| AATCTTCCTA | AGCATTTTGA | GGAAGACACT | GGAACTCGCA | AGACACAATT | TTCTAATCTT | 136500 |
| TTCAAAGCTT | TGCAAAAATG | CCTAGTAAGC | GCCAGTTAAC | TACTTACCAG | ATTTTTCCCT | 136560 |
| TACTCTTACA | AAGTTGTTTA | AACAAATGCT | AATCATAGCA | AGCTAGAGGC | CTGAATGATA | 136620 |
| GTGGACTTAC | ACAGCTTCTC | TCCAAATAGC | ACCTTAATAA | GGTCAGAAAT | AACCTACACT | 136680 |
| GCAAGACTGA | CCAAACCGTT | ATTTCTGTTA | ATCAACTTTA | AGACCATAGT | CTAATGCTTT | 136740 |
| CCGGGGGGT | CCTTAGAAAT | TTGTTCTGTT | AAGACAACAA | AAAATTATCA | CAGCTACTTT | 136800 |
| CGTTGGAATA | AGTGGGTGGC | TCTGAAAAGA | GCCTTTGGGT | TTTAAGACTG | ATGAAAAAGT | 136860 |
| GACTTTACAT | TTACGCTCTT | TCTCCGCGAA | TGCGGCGAGC | GAGCTGGATG | TCTTTGGGCA | 136920 |
| TAATAGTCAC | TCGCTTAGCA | TGGATGGCGC | AAAGGTTTGT | GTCCTCAAAG | AGCCCTACCA | 136980 |
| AGTAGGCCTC | ACAAGCCTCC | TGCAGCGCCA | TCACCGCAGA | GCTCTGGAAG | CGAAGATCGG | 137040 |
| TCTTGAAGTC | TTGGGCGATT | TCTCGCACCA | GGCGCTGGAA | CGGCAGCTTC | CGAATCAGCA | 137100 |

```
ACTCGGTCGA CTTTTGGTAG CGGCGGATCT CGCGCAGAGC CACAGTGCCC GGGCGGTAAC 137160
GGTGAGGCTT TTTCACGCCG CCGGTAGCCG GCGCGCTCTT GCGAGCAGCC TTGGTAGCCA 137220
GCTGCTTGCG TGGCGCTTTA CCGCCGGTGG ATTTCCGAGC TGTCTGTTTA GTACGAGCCA 137280
TGGCAAAACC ACAGAAAAGC TTGCCTGCAG AGACGTCTGT GGAGGAAAGG AAAGAGCTAC 137340
TCTTCTTTTA TAGAGTCAGA CCACCAACTA TTGGACCCAA GAAAATTCAA AAATCCCCGC 137400
GCCCTTCTTG GATTGGTCCA TCTCTGTGCC TGGTTGCAGA TTAAGAGAGG CTCCTGCCCA 137460
TTACCGTAGC TACTCTGACG TCATTTGTT AACCCCTTAG CTGCTATATC CACTGTGGAC 137520
AAGTCTTGTA CTGGAAAAGT TTCCTGAAGT CTTAAAATTT ACAACCACAC AAAGCAACGC 137580
GGAAACCTCC AATTGTTTCT AGTTAAAATA TAAAAAGAA ATCAGAGAAT ATTGGAGACG 137640
ATTAGGGAAA TTTGCATATG CGCTTTATTT AAAATTGTAT TTTTCTGGGT GTCGCATAAG 137700
AAGTGTGGGC AATTAGAAAA ATGCTCTTAG CCGGGCGTGG CGGCTCTCGC CTGTAATCCC 137760
AGCTACTCAG AAGGCTGTCA AGAGGATCGC TTGAGCCCGA GTTCGAGGTT ACAGTGAGCT 137820
GTTATCACGC CGCTGCACTG CAGCTTGGGC GAGAGGGAGA CTCCACCCCA AAACAAAGCA 137880
AAACATCCCC AAACTGGAAA AAAGCTCATT TTGGGAAATA CATACTCAAA TGTTCAGTGG 137940
TAATGTGTGT GCTCTCAATT GTGTATGCCA TTAATTGCTA CAGCAAATGG TATGACATAT 138000
TCAAACTTGT GTGGGGCATG CGGGTTTTAA CACTTCCATT CAAGATAGTT AGGAATGCAC 138060
TCATGGGTAT AATTTCCTTC CTCTAAAATG TAGTAACTGC TGTGTGTGAA ACTTAACGCG 138120
AATCACCCCT GTAAACATGT TTTGTGCTGC ATGGCACTTC TCCCACATAC CTAGAATTCC 138180
TGAGGTTTCT ATGGATCTAA TTTCTGCAGG ACAAATTACT AAAAGTGCCA CACTCAAAGC 138240
CATTAAAAAC ACCTCAAAAA CATCTTTATG GGCGGCATAA TCCAAAGCAC AACAGCTCAT 138300
TTAATGGAAG TCGTAGGTGG CTCTGAAAAG AGCCTTTGCT GTTAGGCTGA TTTTGTCTGC 138360
TGACAGAAAA ACAGCAGTGC ATGAAGCGTT AACTCTTCAC TTTCCCTTGG CCTTATGATG 138420
GCTCTCAGTT TTCTTAGGCA GCAGCACCGC CTGAATATTA GGCAAAACGC CACCCTGCGC 138480
GATGGTCACA CGCCCCAAGA GTTTATTAAG CTCCTCGTCA TTGCGGATGG CCAATTGCAG 138540
GTGGCGCGGG ATGATGCGGG TCTTCTTGTT GTCGCGGGCC GCATTGCCCG CCAGCTCCAG 138600
GATCTCGGCG GTCAGGTACT CAAGCACCGC CGCGAGATAC ACCGGCGCGC CAGCCCCGAC 138660
GCGCTCGGAG TAGTTGCCTT TGCGGAGCAG GCGGTGCACT CGGCCCACAG GAAACTGCAA 138720
ACCTGCACGA GAAGACCGAG TCTTAGCCTT GGCGCGAGCT TTACCGCCTT GTTTGCCGCG 138780
ACCAGACATA ACTACTTCTG ATAAGGGAAA ATCGCCACAA GAAAATGTAA TGAAACTACA 138840
TTAGAACGCA AGGCAGAGAA GTATTTATAC TGACTGGAGG TAGGCTGTGA GGAATTCTCC 138900
CATTGGCTAA TGTCAAATAC CCAATGGGAA ATCAGAATCT GCATCCTTCA TTTGCATGTA 138960
ATCCTTCCGT CTGGTGTAAG GTTTATGTTT GACCCAATCC CCAGTCTGGC TTGACGAGCC 139020
TTCGACTTGA ATACTAATAA TAATTGGCCG AATTAGGATT TTGTCAAAAT ACCTTTTTTA 139080
AGCATGAGTG GAGGTTTTGT TCTGGTTATT TTGACTTTCA GCCGCTCGTG CTTTTCCGG 139140
ATTGTGACTC ATGTTTTTGG AAAGGAGTGG ACTCCGACCA ATTTCTAAAT AGATATTTAA 139200
GAGGTCCTTC AAATCGGGCG CAGTGGCTCA TGCCCGTAAT ACCAGCACTT TGGGAGGCCG 139260
AGGACGGCGG GTCAGGCGTT CGAGACCAGC GTGGACAACA TGGAGAAACC CTGTCTCCAG 139320
TAAAATAACC AAAAAAGAAA CGGGGGAGAA AAAGAAAAAA AAAGCCGGG CTTGGTAGTG 139380
CACGCCTGTA GTTCCAGTTA CTCGAGAAGC TGAGGTGGGA GGATCGCTTG AACCCGAGAG 139440
GAGGAGGTTG CAGTGAGTTC ACATAGAGCC ACCACACTCC AGCGTGGGCG ACAGAGCCAG 139500
```

```
AAGACTGTGT  CTCAAAGACA  AAAAAAGGGG  AGGGGGAGTG  GGAGGGAAGA  AAAGCGAATA  139560
CCCCAAATCC  CAGTGAACTG  TAGAAGCTTA  TAAGCTCTCT  TGATTCATAA  GGGAGAAAGA  139620
AGGGGGATGT  AGGCAACTTA  GGGGAGAGTA  TATGATTTTG  GAGAAAAATA  AATGGGTGTT  139680
TCAAAGAATA  GGTGACAGCT  GTGACAAAGT  CTGTTAGAT   GGTGTTAACC  ACCAGTCTCC  139740
TCTCCTGTGA  TACAGTTAAT  CTTCTCTGGT  TGATGAGATT  CCCCAGGGAA  GTGAATCTTA  139800
ACAACTAAAT  TCCTTTTTGA  ATTTTTTTT   AATTTCAAA   TTTTTGATTA  GAGTTCAGCG  139860
AAAGCCCTTC  CTTGAATTTA  CTGTTCCTA   GGTGCCCTCA  GTTCAAAGAA  ATCAGCGTAA  139920
CAAAGTGGCA  CATTTTTGAG  TTGCATTTCC  TGAACTTTTT  CACAACACTG  AATGAGGAGT  139980
CTCTGGAATC  TTTCAGGAAA  TGAGAGAACA  AACATTCCAT  AACACAGAAA  TACTCAAAAT  140040
GGGATTATGA  TTATAAAAGT  GTTTCACTGA  CCACCTTCTG  CCTTCCTGTC  TGTAAGTCCC  140100
ATTCTCCCCA  AAGTCTAGCC  ATAGAAACCA  GAATTCCTCC  TCAAGGTAGG  CCATACAAAC  140160
CAGAACTCCT  TTTCCCTAGA  ACCAGCCATA  AAACCTAAAA  GTATTACTCT  AACCTACCTT  140220
GTTTGCCTGT  AGGTCATAAG  ACCCCCCATT  CTAAAGAGA   GTCTTGTCCT  ATAACCAGAA  140280
GGAAGAAATG  CTGCACTGAG  AGGTCAAGAA  GAATCTTGAC  AGACAAGCCT  TGCGGGGCTT  140340
CCCCACTCAG  TCTGTTAGCA  TTAGATCGTA  CCCTATACAG  CTGTTTATCT  TGTTGAACCT  140400
AAGCATAAAA  ATGGGCAATT  TCCCCTGTAT  CTTTCAGTCT  TAATTCTAAA  ATCTCCTGTA  140460
AAATTGTGAT  GAAATAAATA  TATATGCCTT  TTCTCCAGTT  AATCTGTGTT  TTGCCAGTAA  140520
TTTTCCATAA  ACCTTGGGAG  GGCAAGGGG   AAGTTTTCC   TTGGCCGGGA  CAATATTATT  140580
ACAGCCATTG  TCTGGCTCTC  CTGTTGAGGA  ACCTAAAATC  AAGACAGATT  GCCTAGGGAA  140640
ATCTTGGTGT  TTTTCCTTTT  ATATTCCATG  AGATAGGAGC  AGATGGAGTA  CAGATGAACG  140700
TGGATTAATT  ATTCCAGGAA  TTTCTGAGGT  ATCTACTACT  TCTATCTGTG  GTCTGCTTAT  140760
ACTGAAACAG  GATGACAGAA  GGAAAAGAA   ACATGAGTGT  AAAAAAATCT  GCTCCTGGCT  140820
GGGCACGGTG  GCTGATGCCT  GTAATCCCAA  CACTTTGGGA  GGCCAAGGCG  GCAGATCAC   140880
TTGAGAACAG  GAGTTCGTAA  CCAGCCTGGC  CAACATGGTG  AAACCCCAGT  CTTCACTAAA  140940
AATACAAAAA  ATTAGCTGGG  CGTGGTTGTG  GGAGCCTGTA  ATCCCAGCTA  CTCCATAGGC  141000
TGAAGCAGGA  GAATCGCTTG  AACCCTGGAG  ACAGAGGTTG  CAGTGAGCCG  AGATCGTGCC  141060
ACTGCACTCC  AGCCTGGGCA  AGAGCGAAAC  TCCATTTCAA  AAAAAAAAA   AAAAAAAATC  141120
TGCTTCTAAG  CCAACGCTGT  CACAGAACTA  TGGATTTGAT  TCAGAGAAAC  TGTCAGGAGA  141180
CTAAAAGTGC  TCATTTTTAG  TTTGTTTTTT  GCCTTCTCCC  AAGTCTTCTG  ACTCTAGTGT  141240
TATCTTTCCC  TTCACAATAT  TCAACTTCCC  TTTTCAAAAT  TATAATGATC  TTCACCCTCA  141300
ACAATAGCCG  TAAACATCAG  TAATCACTGG  CTCATTTTCT  TTGAAAAGGT  ACAAGATTCA  141360
TGATGGAGAT  GTTAAAAAGT  TATCTCAGAT  AGTGCCCTGA  AGAGATTATA  CTCAGAGAAG  141420
GGAGGACTTA  CGTACATGAA  GATTAAATAG  CAGTGCACGT  TCTGCATATA  AAATAAAGAT  141480
TTTGAGCAAT  AAATCATACA  AAAGCACATG  GAAAAGAAGA  TTGATCAATG  TAAATTAGAA  141540
GGATTTAGAG  AGTTCATGAG  GGAGATGTAT  ATCCAGCATT  ATTAGTTCAG  CATATATTTA  141600
CTGAAAACCT  GCTAAGTGCC  AGAGAGTGTT  CTAGGTGCAG  GGAGCATAGC  AGTGAAAAAG  141660
CAGACAACCT  GTTTCCTTAC  GGTGCTACTT  GTCTTGTAGT  GGGAGGTGCA  CAATAAGGTA  141720
AATACATAAT  GAAAATGTAG  AGATAAGTGA  TGAGTGCTGT  GGAGAAAAAT  AAAGAAGGG   141780
GATAAGAAAA  AAGAATAGAA  ATAAGGATGG  AAAGTTTCAT  CAGGAGAATG  TCATTTGAAT  141840
TCAGACCTGA  AGGCAAGGAA  GAAGCCAGCC  AAGTAGGAAG  GATAAATACT  TCGATAAAAT  141900
```

| | | | | | |
|---|---|---|---|---|---|
| GCTGGATGTG | TTTGAAGTCC | AGAAAATGTC | AGGAACCGTG | GTTCAGAAAG | TACAGCTATT 141960 |
| CTAACTTCCT | AAACAAATCG | TAGACCATTT | TGGAAAGAGC | CTTGGATATG | TACAGGGCTA 142020 |
| GATAAAATTG | AAACCAAGAT | TAAGGGTAGC | TTCAAAAACT | CAGACTAGAA | AGCAGGAGTA 142080 |
| CATCCAGTCA | CAATATCAGT | AATCTATACT | CCACTGAGCC | ATGGATGAGA | AAAACTCTTC 142140 |
| TTCTCATCCA | AGTTACCTTG | AATTAAGCAA | ACCAACAAGC | GCCTGGCATG | TACTATTAGC 142200 |
| AAAACAACTT | GATGGCAATC | CTTTCAGTAA | GTGCTTCAAA | AACAGTAAAT | TCTAGGCACT 142260 |
| TGCCTTCAAA | AAACATACAA | AAGGCAGATA | TTGGGGAGGG | AAATATTGGG | GGTTATTTAT 142320 |
| TCCATATAAA | TATAAGAGGA | AAATAAGTTG | TTTCCCAATA | ACAACTCCAA | CACCAGGAGC 142380 |
| AGAGAAAGTA | AGACAATCTA | TGCCTCGTGG | TTTGCGAAAA | CAATAAAAAA | AATCTGTTAA 142440 |
| TTGCATAATA | CAATTCACCC | TTGAACACGC | TCCAAATCAG | TGCCCACTAG | CTACAAGTAG 142500 |
| CTACTGTGAA | GTTGAAAAAG | GGTACTTCAG | ATTGAGCTAT | TCTGTAAATA | TGAAATAGAC 142560 |
| TTAGTGTGTT | AGTTCGTTCT | TGCATTACTA | TAAGGGAATC | CCTGAAACTG | ACTAATTTAT 142620 |
| AAAGAAAAGT | AATTTTTTTT | GGCTCACGGT | TGTGCAGGCT | GTACAGGAGG | TGTGGTGCAG 142680 |
| GCATCTGCTA | CTGGCAAGTC | CTCAGGAAAC | TTCCAATCAT | GGTGGAAGGT | GAAGAGGGAG 142740 |
| TAGGCATATC | ATATGGTGAG | AGCTGAGCGA | GAGAGATGGG | GGAGGTGTCA | CACTCTTTTA 142800 |
| AAGAACCAGA | TCTCTTGTGA | ACTCAAAGTG | AGAACCCATT | GATTACCCTG | AAGAGTGCGC 142860 |
| TTCATGAGGG | GTTCACCCTC | ACGATCCAAA | AACCTTTCAC | CAGGCTTCAC | TTCCAACATT 142920 |
| GGAGATTACA | TTTCAACATG | AGATTTAGAG | GGGACAAATA | TCCAAACCAT | ATCACTTAGT 142980 |
| ATGAAGAAAG | AATGTAAAAC | ATCTGACTAA | TAATTATGCA | TATTGAATAC | ATGTTATAAT 143040 |
| GACATTTTGA | CTACAAAAGT | TAACGAAAAT | ATACTATTGA | AGATACTCAA | AAATTTAAAA 143100 |
| ATACATATAT | AATTTGTAGT | ACATTTGTAC | TGGGCAGAGG | AACCTCTAAC | AATGTTCCAA 143160 |
| ATGTGGCCTG | TGTATGTGTA | TGATGTAGGA | GGGATCAGTC | ATGTAAGATG | ATCATAATAT 143220 |
| AGTTACTTAG | TCCATTTTGT | GATACTATAA | CAGAATACCA | CAGACTGGCT | AACTTTTAAA 143280 |
| GAAAAGAAAT | TTATTTCCTA | CTGTTCTAGA | ACCTGGGAAG | CTAAGGGCAT | GGAATTAGTA 143340 |
| TCTGGTGAGG | GCCTTCTTAC | TGCATCATAA | CATGTTGAGA | GAGCAAGGGT | ATGTGTGTCA 143400 |
| GCTCAGGTGT | CTCTTCCTTT | TCTTATAAGG | CCACCAGTCT | AAAGGAAATC | AAAATATTTT 143460 |
| ACCCCAAAAT | ATATTTCTTT | GACATATTTT | GAAATGGCTG | CTGCTTGGCC | AGCAGGCAGA 143520 |
| AATGGGCTTG | CAAAGCTGCC | TTAAATGGGA | AAAATTTTAC | ATCTGTAGAG | AATCTCCATT 143580 |
| AATGCAGCCA | TGCCTCCTCA | CCTTTCTATA | CCTTTCCCCA | GATCCAGGAG | AGACTGAGAG 143640 |
| TCTGACACTT | AAAAATCATA | AAAGAAACAT | TTACCATCTG | TTCTTTCTGA | GGGAGGCTTC 143700 |
| ACCTACCTAA | CAAGGCCACC | TTTGCAAGCC | AAACCTCTTT | TGCCTCCCAT | AACCTGTTTT 143760 |
| ACCAGAATCT | AAGCCCCAAT | TCTTTCTGTG | ATCTAAAAAT | GGTATATAAG | CATCTATAAC 143820 |
| TCATTGGGAA | GTTAGGTAAT | TAATTCTGAA | TGCTCCCACA | TAGACACGTT | AAACAATAGG 143880 |
| TAAAATGCCT | TTTCACCTAT | TAATCAATCT | GCCTTGTCAG | TGATTTCTGG | CAAACATTTA 143940 |
| GTGGGCCAAG | AGACTATGGT | TCCCACACTA | CCCTTCATGA | ACTTAAGCCC | TAAGATATCA 144000 |
| ATAATTGCAT | TAAATGTGTG | TGGTATAAAT | ACACCCATAA | AAAAACAGTT | TGGCTGGGCG 144060 |
| CGAGGTCTCA | CACCTGTAAT | CCCAGCACTT | TGGTAGGCCG | AGGCTGGCGG | ATCACTTGAG 144120 |
| GTCAGGAGTT | CGAGACCAGC | CTGGGCAACA | TGGTGAATCC | TGTCTCTACT | AAAAATACAA 144180 |
| AAATTAGCCG | GGTGTGGTGG | CGCATGGCTG | CAATCCCAGC | TGCTCAAGAG | GCTGAGGCAG 144240 |
| GAGAATCCCT | TGAACCCAGG | AGGCGGAGGT | TGCAGTGAGC | TGAGACTGTG | CCACTGCACC 144300 |

| | | | | | | |
|---|---|---|---|---|---|---|
| CCAGCCTGGA | CAACAAGAGT | GAAATTCCAT | CTCAAAAAAA | AAAAAACAAC | AACTGTACAC | 144360 |
| TGTCTGCAAG | AATCTCACTT | CAAATATAAA | CATAACGCAG | GTTGAAATTA | AAGGCTGCAA | 144420 |
| AAAAGATAAG | CCATATAAAC | ATCAGCCCAA | AACTGCAAGA | GTATCTGTAT | TAATAATATC | 144480 |
| TGGGATCTGA | AAGACCAAAA | TAGATGCCCC | TATACCAACT | AAGACAGACT | CTAAGATTAA | 144540 |
| GCAAACAAAG | TTACCTACTG | GTAGAGCATT | CATGGCTTGG | CTGGCATGGC | AAATTCCTAA | 144600 |
| ATTCCAAAGA | CTACCAAAAA | ACTCACACTT | GCTAAATTCC | TTAACTATAG | GAGCTATCAG | 144660 |
| AAGCCCTCCT | AACTCTGATT | TACAGTCCAG | TCCACTACAA | CTCTGATTGG | ACAGAGGACC | 144720 |
| GCCTTGACAC | ACATTCTATT | CTTACACGTA | ATTGTAGACC | TTAAGCCATT | TTCAGCCAGC | 144780 |
| TGCTAGAGGC | AGCACGTAAA | CTTTGTTCCT | ATAGTTCACC | TTGTGATGTA | AAGACCTAAA | 144840 |
| TTCTACCTCA | TTTTAACCAA | AATTTAACCT | CGAAGTGAAC | ATGGGAGGTA | TATTACACGT | 144900 |
| GTTTATCCAT | TGTGAATGCA | CTTGGCACCC | CTCATAATAT | ATATAGCTGT | CCCCCCAAAC | 144960 |
| GTGCTAAATA | TGTATGACTC | TATTGTGTAA | TATATAGCCT | ATGAGGCATA | AAAATAACCA | 145020 |
| ACCTGCTCCT | TCTCCCCAAA | GAGAGAGTAA | TTTTGGCAGG | TTCTGGGACC | ATCTCTTCCT | 145080 |
| GGCTTGCAAA | TTAGTATTGC | CAGTAAATCT | CTCCTTTCTA | CTCTTTAGCC | ATCCTGGTGG | 145140 |
| TCTTTTGGAT | GATATATCAG | ATAAGTATAT | TTCAGAGCAA | AGAAAATTAC | TAGGAACAGA | 145200 |
| CAGGGATATT | ACATAATGAT | AACAGGGTCA | ATCCAATACG | AAAAACAAGC | AATTCTAAAT | 145260 |
| GTATATGCAC | CAAATAACAG | AACTGCAAAA | TATGTGTAGC | AAAACCTGAT | AGAACCGAAA | 145320 |
| GGAGAAATAG | ACACATACAT | GATTTAAAGG | TAGAGATTTC | AACACCCCTT | CCCCAATAAT | 145380 |
| TGATAGAACA | ACGAAACAAA | AAAATTACCA | GGTGTATAGA | ACTCAGTAAG | TGACTGTATT | 145440 |
| ACTTGTTTTG | ATCTGTAAAA | CAATGATAAT | AATAGTACTC | ACACTTCATT | GAGTTTTGGT | 145500 |
| GAAGATTGAA | TGAATTTATA | CTTATAAAGA | ATTTAGAAAT | GTGGCCGGGC | CAGTGGCTC | 145560 |
| ATACCTGTAA | TCCCAGCACT | TTGGGAGGCC | GAGGCGGGTG | GATCACCTGA | GGTCGGCAGT | 145620 |
| TCGAGACCAG | TCTGACCAAC | ATGGAGAAAC | CTCATCTCTA | ATAAAAATAC | AAAATTAGCC | 145680 |
| AGGCGTGGTG | GCGCTTGCCA | GTAGTCCCAA | TTACTGGGGA | GGCTGAGGCA | GGAGAATTGC | 145740 |
| TTGAACCCTG | GAGGCGGAGG | TTGCGGTGAG | CCGAGATCGC | ACCATTGCAC | TCCAGCCTGG | 145800 |
| GCAACAAGTG | TGAAACTCCG | TCTCAAAAAA | AAAAAAAAA | AAAATCTTAG | AAATGTAACT | 145860 |
| GACATATCAT | AAGCCCTCAA | ACTTAATAAT | CTTTTAATAC | ATGGAGCTAT | CTATTTAAAA | 145920 |
| TAATGTACAT | AAGGCAACAT | CCCAAAAGAA | AATGGGCAAG | AATCATGAGT | AATCAAACCA | 145980 |
| TAATAGAAGA | AATGTTATTA | TCAAAATGTG | CAGTCTCAAA | CAATAATTGT | CTTAAAAATA | 146040 |
| AAAACAACAA | TGAGATTTAA | TTGTTCATGT | CGGCAATTTG | AACAGACTAA | CACACCCACT | 146100 |
| GTTCAAGAGC | ATTTGTGGAA | GTCAGGAAAA | AACACCCTGT | TGGTGAGAGT | GTAAACAGAC | 146160 |
| CTTCAGGAGG | CAACTTGGTA | ACATGTATTA | AAAATCAAAA | TATGTATATC | AATGGATGCA | 146220 |
| TGATTCCTAT | CTCTATTTTT | GCCCTTACAG | CAATCTTGTG | TGTAGAGAAA | TACTGAAAAG | 146280 |
| CATTTTCATG | GTAACATGGT | TTAAATTTTT | AAAAGCGAA | GGTCAGTGAA | TAAAGGGCAA | 146340 |
| TTATCTACTT | CCCTACAATG | AAATGCAGTA | ATGAAATAA | TCATTAGAAT | CTCTTTTATT | 146400 |
| AATTTAAAAG | GATACTAGAA | AAGTGAAATA | CAATCTCACT | TATAGAAGAT | TTACATATTG | 146460 |
| GTTTGCATAG | ACTTGCACAA | GATAAAATTT | CTGTAAGATT | GGTCACCAAA | ATGTCCTGAA | 146520 |
| TGATAACATT | ACAATTAATG | TTTATATTGT | AGGGGAAAAG | AAAATTCTGT | TTTTCTCACC | 146580 |
| CATCAGTAAG | TTCATGCTTG | AGGCCCCTCT | ACAAAAGAC | AGATTGGTCG | GGTGCAGTGG | 146640 |
| CTCACGTCTG | TAATCCGAGC | ACTTTGGCAG | GACGAGGCGG | GCGGATCACG | AGGTAAGGAG | 146700 |

-continued

| | | | | | | |
|---|---|---|---|---|---|---|
| ATTGAGAACA | TCCTGGCCAA | CACGGTGAAA | CCCTGTCTCT | ACTAAAAATA | CAAAAATTAG | 146760 |
| CGGGGCATGG | TGGCACGTAT | CTGTGGTCCC | AGCTACTCGG | GAGGGCGAGG | CAGTAGAATC | 146820 |
| GCTTGAACCT | GGGAAGCGGA | GGTTGCAGTG | AGCCGAGATC | GCGCCATTGC | ACTCCAGCCT | 146880 |
| GGGTGACAGA | GCAAGGCTCA | GTCTCAAAAA | ACAAAAAAAA | AGATTAGCAA | GAGAAAGCA | 146940 |
| TACAAATGTA | TTTAATATAA | GTTTTATATT | ACATGGGACC | CTTCGGAAAT | GAAAACTCGA | 147000 |
| GGGAAGCGGG | AAACCTGTGA | ATTTTTATGG | CAAGTTTTGT | GAAATGCATA | GTTGTGGATT | 147060 |
| AATATGATTG | ACAGTAGGCA | TATGATCTAA | TGGTAATAAA | CTGAGGGGA | CATAGCAAGG | 147120 |
| CTTGTTTGTT | AATTACCTAT | TAACGATCAG | CCGAGTATCA | GCAGAGACAG | CAAAACATCC | 147180 |
| TAGTTTTGAG | TTAGAAGACC | TAGGTTTTTG | TTTTGGCTTA | TCAATTATGG | GTATTGTTTT | 147240 |
| AGATGAAACA | TCAAGTATTC | TTGATTTCTT | ATTTCAAAAA | TAAAAAATAA | AAAATAAAGG | 147300 |
| AAGGAAAAAA | GAAGAAAAAA | AGAGAAGAAA | AGTGTCAGAG | TTACTTGAAC | CAGAGTAACT | 147360 |
| CCATTTTGAG | TGAGGGCTAG | GAAAATGAGG | CTGAGACTTT | CTGGGCTGCA | TTCCCAGAAA | 147420 |
| GTCAGTCATT | CCTAGCTTCT | AGATGTTTAC | GGTTAAGGGA | ACAAATAAAT | AATGTTTACT | 147480 |
| AAACAGACTC | AGACTTAGGA | GTGTCCAGAT | ATCCCTATAT | CTGGAGAACA | AAGGCATTCT | 147540 |
| TAATTTTGTT | TAAAGATAAT | AATGTTGATT | CTTGCAAAAT | ATAGTAACTA | AGAAAATTAA | 147600 |
| TCCTTTATCA | CAAACTTGTA | GCAGAGCACA | TCTCCCCATA | TATACAAGTA | TTGTACCTAG | 147660 |
| GGTGGATGCC | TTCCTCCTCT | TACTTTCGGG | AATGTCCTGC | TCCGTCTATG | GAGTAGTTGT | 147720 |
| CGTTTCACCA | CTTTACTTTC | TTAGTAAACT | TGCATTTACT | TTGCACTGCG | GACTCACCCT | 147780 |
| GAACTCTTTC | TTGCGCGGGA | TCCAAGAACC | CTCTCTTGGG | GTCTGGATGG | GGACCTCTTT | 147840 |
| CCTGTAACAT | ATTTCTGGCC | ACCACAGAAG | GGACTATAGT | ACAGAAACCC | TGACCCAACA | 147900 |
| GCTACCTTTG | GGTAAGTGTT | GGAGTTCTGT | AACAAAGGAA | GAAGGCAGGC | AGGCAAAAAA | 147960 |
| TTTATGAAAG | AACATACGAC | AAAATAATTT | CTGCTTCAAA | ACTTCATATT | TTTTTAATTT | 148020 |
| TTTTTTTTTT | TTTTTTTGA | GACGGAGTCT | CGCTCTGTCA | CCCAGGCTGG | AGTGCCATGG | 148080 |
| CGCGATCTCG | GCTCACTGCA | AGCTCCGCCT | CCCGCGTTCA | CGCCATTCTC | CTGCCTCAGC | 148140 |
| CTCCCGAGTA | GCTGGGACTA | CAGGCGCCCA | CCATCACGCC | CAGCTAATTA | TTTTGTATTT | 148200 |
| TTAGTAGAGA | CGGGGTTTCA | TCGTGTTAAG | CAGGATGGTC | TCCATCTCCT | GACCTCGTGA | 148260 |
| TCCGCCCGCC | TCGGCCTCCC | AAATTGCCGG | GATTAAAGGC | AAGAGGCACC | GCGCACGGCC | 148320 |
| CCGTCCAAGT | TAACCTTGGC | TCTAAAACTT | GTCTTCGCTA | ACATTCCAGT | TGATCCTCTA | 148380 |
| GAACTGAAAC | AGAATAGCAG | CAGCACCACC | TTAAGAAATT | GTGGTTATAG | CTCTCCTTGT | 148440 |
| GACAAAGTAG | GTGGCTCTGA | AAAGAGCCTT | TGGGTTTGGA | AGTGCTTACA | TAAGCACTTA | 148500 |
| TTTAGAGCTA | GTGTACTTGG | TAACTGCCTT | AGTGCCCTCG | GACACAGCAT | GCTTAGCCAG | 148560 |
| CTCCCCAGGC | AGCAGCAGGC | GCACAGCCGT | CTGAATCTCC | CTGGAGGTGA | TGGTCGAGCG | 148620 |
| CTTATTGTAG | TGAGCCAGGC | GAGAAGCCTC | GCCCGCGATG | CGCTCGAAGA | TGTCGTTGAC | 148680 |
| GAAGGAATTC | ATGATCCCCA | TGGCCTTGGA | TGAGATGCCG | GTGTCGGGGT | GGACCTGCTT | 148740 |
| CAGAACCTTG | TACACATAGA | TAGAATAGCT | CTCCTTGCGG | CTGCGCTTAC | GCTTCTTACC | 148800 |
| ATCCTTCTTC | TGCGCCTTAG | TGATAGCCTT | CTTAGAACCC | TTTTAGGGG | CTGGAGCAGA | 148860 |
| CTTAGAGGGT | TCAGGCATTG | CTATTCCTAA | ACAGAATAGA | AAAGCTACTA | ACACTCTCCA | 148920 |
| CTACAGAGTA | GTACAGAGAA | CAGTTCAGAG | CCCATGTATT | TATAGTCCTG | AGATTCAAAT | 148980 |
| GACGGTTTAA | GATTCCTCAC | TTCTGATTGG | ACAAAAGAAA | CACGGTTTCA | CTGAGGGGTG | 149040 |
| GGGTTTATGC | AAATATGGAA | TTTATGTTAT | CTTTTCTAT | TGGATAAAGC | ACCAAACATA | 149100 |

| | | | | | |
|---|---|---|---|---|---|
| ATTGACCAAT | AGGATAGCTT | CCTATTGCAG | CCTTGCAGTT | TGTATAAAAG | GATTTGTTCA 149160 |
| GGCGCCATTC | CAGCTTGCTT | GTCTTTCACA | GTTTTCCGCT | GCTTTCATAG | GTCGCTATTT 149220 |
| GCGGACGTGG | AAAATGGAGC | TAAAGCAAAA | ACTTGTTCGT | CGCTACCGGG | CTTGCAGTTC 149280 |
| CCAATAGGGC | AGAGTCCGTC | ATCTTTTTCG | AAAGGGCAAT | TATTTTGAGC | CGGTCGGAGC 149340 |
| CGGTGCGCCA | GTGTACTTAC | AATACCTGGC | CGCCGAGATC | TTAGAACTGG | TGGGCAGCGC 149400 |
| CATACGTGAC | AAGACCCGCA | GCATCATCCC | CCGCCACCTG | CAGCTGGCCA | TCCGAAACGA 149460 |
| CGAGGAGGTC | AACAAGCAGC | TGGGCAACGT | CACTATTGCT | CAGGGAGGCG | TCCTGTCCAA 149520 |
| TATTCAGGCC | GTCCTGTTGC | CAAAATAACA | GAGCCACGAT | AAGGCCAAGG | TCAAGTAAAC 149580 |
| ACTCAAATCA | GAAAACGTAG | CTTACACTTG | AAACGGCATT | TTTCAGAGCC | GTCCATAGTT 149640 |
| ACACAAGAAA | GGATGATAAC | TTGCTTCTGT | TAGGGTATTT | TTTGCTTTTC | GTTTGGATTG 149700 |
| GTTTGTTTTG | AGACAGTCTA | GTTCTGTCAC | CCAGGCTGGA | GTGCAGCGGC | GCGATATCGG 149760 |
| CTTACTGCAA | CCTCCACCCC | GCCGCTTCAC | GCGGTTCTCA | TGCCTCAGCC | TCCTGTGTAC 149820 |
| TTGGGATTAC | AGGCGTCTGC | TACCGCGCCC | AGCTAGTTTT | TGTATTTTTA | TGCGAGACGG 149880 |
| GGTTTCACCA | TTTTAGCCAG | GGTTGTCTTG | AACTCCTGGC | CTCTAGTGAT | CGTCCATCT 149940 |
| CGCCCTCCCA | AAATGCTGGG | ATTACAGGCG | TGAGCCACCG | CCCCCCTAGC | CTAATGGTGT 150000 |
| TAAAAGTTA | AGTTTCGAGA | AAATAACACC | TTCCTTTAGA | AAGTACATTT | TAGAGTATAC 150060 |
| AAAGTGAAAC | TTAAGGCCAA | CCAAAATAAG | ACATTTTGAG | AACAGGCAGG | GTGGGAATGT 150120 |
| GACTTGGACT | TAGAAAACAA | AGGGCAAGGA | AACTTGCTGT | TCGCCAGTAA | CAAAATAGCA 150180 |
| TGGAATCTCA | TTCTCTGAAT | ATAAGCGTTA | TTTCCCGACA | TGAGTCTGAA | CGTTTCTGGT 150240 |
| GGTTTAGTGA | GTGTTCACCA | GCATTGATAA | CTTGCGAGAC | TGTCAGGAAT | GCAGAATTTC 150300 |
| AAGTCCCACT | CAAACTTACT | GAATCGGAAT | TTACATTTTA | AAAATCCTTA | GATACCTTGT 150360 |
| TATACACTCT | GTTCTTTGGG | ACTGGATGAA | CTAGAATTTT | AGACAATTTG | TCGCTGCAGA 150420 |
| TAACTGAAAC | GAAAAGGACA | GGATGGGCGG | TGGGGCAACT | CATCCAATAA | GATTGTCTAG 150480 |
| TAATGAACCA | ATCAGTCTGG | TCACTCTTCA | GCCAATGATT | TTATCGCGCG | GGACTTTTGA 150540 |
| AATATTACAG | GACCAATCAG | AATGTTTCTC | ACTATATTTA | AAGGCCACTT | GCTCTCAGTT 150600 |
| CACTACACTT | TTGTGTGTGC | TCTCATTGCA | AATGGCTCGT | ACGAAGCAAA | CAGCTCGCAA 150660 |
| GTCTACCGGC | GGCAAAGCTC | CGCGCAAGCA | GCTTGCTACT | AAAGCAGCCC | GTAAGAGCGC 150720 |
| TCCGGCCACC | GGTGGCGTGA | AGAAACCTCA | TCGCTACCGC | CCGGGCACCG | TGGCCTTGCG 150780 |
| CGAAATCCGT | CGCTACCAGA | AGTCCACCGA | GCTGCTGATC | CGGAAGCTGC | CGTTCCAGCG 150840 |
| CCTGGTGCGA | GAAATCGCCC | AGGACTTCAA | AACCGACCTG | CGTTTCCAGA | GCTCTGCGGT 150900 |
| GATGGCGCTG | CAGGAGGCTT | GTGAGGCCTA | CCTGGTGGGA | CTCTTCGAAG | ACACCAATCT 150960 |
| GTGCGCTATT | CACGCTAAAC | GCGTCACCAT | CATGCCCAAA | GATATCCAGC | TGGCACGTCG 151020 |
| CATCCGTGGG | GAAAGGGCAT | AAGTCTGCCC | GTTTCTTCCT | CATTGAAAAG | GCTCTTTTCA 151080 |
| GAGCCACTCA | CAATTTCACT | TAAAAACAGT | TGTAACCCAT | TCGGTTGTCT | ATGTTAGTTT 151140 |
| CCAGGAGATA | TAAAGGTGAT | AACTACACAC | AAGTTTTGTA | ACTGCAGACA | AGTCTATCAG 151200 |
| GCCTTTTCAA | CCGGTTTTAC | TGCGAGAAAA | CAAGCTGAGT | TACTGTTTTG | CCCTTGTTAA 151260 |
| AAAATTCCTA | GGGGTCTTTT | TAGCATGTAT | ATGTGTAAAT | ACTTACATAT | TGAAAGGCTC 151320 |
| CTGGGGACAC | CACCGTCACT | CCTTTTAATC | CACGTGACAA | TTTTAGTTCT | GATGGCAGTA 151380 |
| TTATTAAAGC | TATCATAAAG | ACAATGTGTG | TGTAGTTACC | TAAGTCCACA | AAAACAATAG 151440 |
| CTGACCCCAA | AATTCAGTAT | TGGTTTTGGG | CTGCTGGAGG | TGGAGTCAGA | GCTCAGGTGG 151500 |

| | | | | | | |
|---|---|---|---|---|---|---|
| AAGAAACTGG | CCTCAGTACA | CACTGCCAAA | AGTCCACTAA | ATAGATTTAT | GTAACAAGTA | 151560 |
| CACAAGACTT | GCGTATGACC | ATCCAAAGAT | TATGCGGTCA | TCCTTATCCA | GGGAATTTGA | 151620 |
| GAATGAAGGG | TGGCAACTGC | AAAGCTCTTT | TACCCATGTC | CTCTTTTAAT | AAATATTTAA | 151680 |
| AAATATTCAA | ATGCTGATTT | CATCCATTTT | CTAAATATAT | TAGTATACTT | AACTGATGGG | 151740 |
| GTAGATCAAG | GTTTTCTGGG | GATCAAACCT | TTTACAACTT | GTTAACTATT | AAAAACTATA | 151800 |
| ATGTAAAATT | AAAAATGCAA | AAGTACTGCA | GACTGTAAAT | ATAAATTTAT | AATGGGAAAA | 151860 |
| TAAAATCAAA | TTCCAATTTT | ATAAAAGCTG | ACAAACAAC | AGCCATCACA | AAATTCAGAA | 151920 |
| AATAGCATAT | TTTATTAACT | TCTGAATATG | ACACTACCAA | GTATATTTTC | CTGTAGTTTT | 151980 |
| GACTGAATAC | TCTGATTCCA | TCTTCAGATC | GAAATTATTT | TGTAATGTTG | TCTATAGGTA | 152040 |
| ATGGAAATAG | AATTCAATCT | TTCCTCCAGG | GTGGCTGATG | ATAATATGTT | TTCTTCATAA | 152100 |
| CTTAGAAGTA | TTTCAGTTTC | AAAACACATT | ATTGGTAATG | TCAAGTAAGT | TTTAGGATT | 152160 |
| GTTTTCAAAT | TTGGAAAATC | CTCTGTTAAG | CTCCTTTCAC | ATGTAAGTTG | TAAACTTTGT | 152220 |
| AAGAATTCTT | TCCAGACTAG | CTTCTGGCTC | TATACGTTTC | TACTCTCCAC | TAGACACTCA | 152280 |
| CTCTCAGTGC | TGGGAATGTG | TTTTGAATAC | TTAGATGTCA | TAACATTTTA | TCTAGACCTG | 152340 |
| CATCTTGCCA | GGAATTTAGG | TGAGTTATTC | CAGTGAGCAG | TAGGAACATT | CCTTGAAGCC | 152400 |
| ATTCTTTTTT | TTTTTTTTT | GAGACGGAGT | CTCGCTGTGT | CTCCAGGTT | GGAGTGCAGT | 152460 |
| GGCGCAATCT | CGGCTCACTG | CAAGCTCCGC | CTCCCAGGTT | CATGCCATTC | TCCTGCCTCA | 152520 |
| GCCTCCCAAG | TAGCTGGGAC | TACAGGCGCC | CGCCAACACG | CCCGGCTAAT | TTTTTGTATT | 152580 |
| TTTAGTAGAA | ACGGGGTTTC | ACCGTGTTAG | CCAAGATGGT | CTCGATCTCC | TGACCTCGTG | 152640 |
| ATCCGCCCGT | CTCGGCCTCC | CAAAGTGCTA | GGATTACAGG | CGTGAGCCAC | CGCGCCCGGC | 152700 |
| CTCCTTGAAG | CCATTCTTAC | GTCAGATTGG | CTGGCAACGA | ATGAAGTACA | CATGATCACA | 152760 |
| TATGCAAATC | ACGTAACTTA | TTATCCCCAT | ACTAGATACA | TCTTCAACTA | AACTTTCTCT | 152820 |
| TACTCAAATT | CCAAATATTT | TCATCAGGAT | TCTAACATAA | TCAGACAATG | GTGATTTTAA | 152880 |
| TAAAAGGAG | GATTGAGTGA | AAATAGCAGC | CTGAACCATC | CGTGATTAAA | GTACCTTAAT | 152940 |
| ACTGCAAATT | TTAAAATCAG | AGAGAGAGAG | AGAGACAAAC | TAACACATTT | GTAGGGCCCC | 153000 |
| TCTCTGCACC | TTGGAAGTAC | AGGCCCTTAC | ACTTGTGTTT | CATTAGCTTC | AGGATAAATC | 153060 |
| TGCCCCAGAT | CACTGGCCAA | ATTTTACGTG | GCCTTCTTCA | GCATCCTACC | ACTCTATTCA | 153120 |
| AATACATCTC | TGCAGGAGCA | CCCTGTGAGT | TGAGAATTAC | TGGTCTGGGA | TGACCACTGT | 153180 |
| TTGCATGATG | CTTTGGATGG | TGGTGCTGTT | CTCAGAAGAA | ATACCAGAAG | GAGAAAGGTT | 153240 |
| AGTCAGGAGA | ATATAAAGTC | AACCTTAAGC | AATTTGAACA | CTTCAGTGGT | TAAGTGAGTT | 153300 |
| CCCTGGGACA | ACTCTGCAAG | CTGTTTTAAC | TTTATTTGTA | TTGAATATTA | CCTTCTTTTA | 153360 |
| GAGAGGCCAA | CGTGTAGAAG | GAAATAACAA | TGAAACAAAG | GATTCATTAA | TAGTATAAAC | 153420 |
| TATAAACTAA | CTGTCATTGA | TAGTCTTCCA | CGGGCCAAGT | ACCACATGAA | GTGGTTGGTC | 153480 |
| TGAATTATTG | TGTAAAATTC | TTACTTCAGC | ATTGTAAGGC | AAATTATCTC | ACTGTCTCCA | 153540 |
| TTTTACAGAA | GTGGAGGTTC | AGCCTCAGGA | ATTTCACTAA | ATTCGCCAAA | TTCTTACTAC | 153600 |
| CAGCAGATAT | CATTGCCAGG | CAGTGTCACA | CTTAATATC | TTCTAATCAA | TAAGATAACC | 153660 |
| CTAAAATTGA | TTATCATATA | TAATTTCCTT | CTCATATATA | GTTTCATACT | ATCATATATA | 153720 |
| GTTTCCTTTG | TTTCAGAAAT | TGGACTCCCT | CAGGGTGGAT | AAGGAGACAT | GGTGGTGTCC | 153780 |
| TGGCCTAAGT | ATTGTTGGAA | TCCTCTAGTC | AGAGGCCTGA | TGTGAGGTGA | AGTGGACAGT | 153840 |
| GAAACTGCCT | TTGCAAAAAT | CATAACTGAG | AAAATTATTA | CAGTGAAAGA | GATCTTACCT | 153900 |

| | | | | | | |
|---|---|---|---|---|---|---|
| AACCGACTCC | ATCTAACGTC | TAAACTCCAA | GCTGTCCTTT | TCATTCCTGA | GTTTGGGATT | 153960 |
| AACTAACTTT | GGGAGGAGCT | TAGTTTATAC | TTTTGCTTTT | AAACAAAAAC | AATAACAGCC | 154020 |
| CTTTCAGAAA | CAAACCCCTT | TCCTGCCTGG | GGACCAGACT | GCTTTTGCAG | GACTAACAAA | 154080 |
| TTAGCCACAA | GATTATAAAT | TATGGTTTAG | GAGTCATGCA | GCTGGAAGCT | ACAAGATTCT | 154140 |
| AAACCTCAAA | TTGCTCCTGG | GGATAAAATC | ACTATTTTAA | AACCTAAGAT | CAATGCTTGA | 154200 |
| GCTATTTTGC | AGACCCTGAA | CACAATGGAT | TAGCTGGCAC | CACCCATATA | GATAAACTGG | 154260 |
| ATTATCTGGT | CTTGAGTCCC | CCACCCCACC | ACTCCCAGGA | ACTGATTTAG | CACAAGAGGA | 154320 |
| CAGCTTAGGC | TCCCTATAAT | TTCATCTCTG | ACCCAACCAA | GCAGCACTCC | CGACTCACTG | 154380 |
| GTCCCCTACA | ATCAAATTAT | CCTTAAAAAC | TTTGGTCCCC | AAATTCTCAA | GGAGACTGAT | 154440 |
| TTGAGTAATA | ATAAAACTCT | AGTCTCCTGT | AGCGCTGGCT | CCTTATTGCA | ATTCCCTGT | 154500 |
| CTTGATAAAT | CAGCTCTGTC | TAGGAAGTGG | ACAAGGAGAG | CCCGTTGGGT | GGTTACAATA | 154560 |
| GGACAAACCA | ATAAAATATA | AAGTATTAGA | GACACTACCT | GGGTTTCAGG | AACAGGTCAG | 154620 |
| AAAAAGTGTT | TTCTTGGAAA | ACATCTGGAT | TCTGCTGCAG | AGCAAGTATT | TGCTTGTGTC | 154680 |
| TTCCCAGAGT | ATAAAAGCTG | TCCTGTCCAA | GATAGTTGCC | ACTAACCATA | TGTGAGTATT | 154740 |
| AAGCATTGGA | AATGTGGCTA | CTCCAAACTG | TGATGTGCTT | TAAGTGTAAA | ATACACACCA | 154800 |
| GATTTCAAAG | AACTAGTAAA | ATAACAAAGT | AAAAACTCAA | TATTTTAATA | TTAGATACCT | 154860 |
| TGTTGAAACA | ATTTTTGGTT | ACACTGGATT | CAAATCATTA | AAATAGATTT | CTTTTTTCAC | 154920 |
| TTTTTAAAAT | GTGCCTATTA | AAAAATTTAA | AATTACATAT | GTGGACCCTA | TGTTTCTGAG | 154980 |
| GAACAGTGCC | AGGACATAGA | GGATAGTTAT | ATTCACTCAC | AGATCAAAAA | CTAGCAAAAC | 155040 |
| TATGAAATAC | CTAATAATTT | AATTTTTCAC | CTTAACTTTT | GGCATATTCC | ACAGATCTGT | 155100 |
| AGTATATTTG | AGTGTGATAG | CTTAGGAATA | AATATGATTG | GAACTCATTC | ATGTTTAGAG | 155160 |
| AGAAAGGGTG | TCAAATTGAG | AACCAGGCAG | ATACACCTAA | TCTTAAAATG | ACCCCAAAGT | 155220 |
| AAAGTGGTTG | AAGAAATTAA | ATCCCAAAGA | TTTTTGGTGA | AGAATGTTGT | AGTTTTCATC | 155280 |
| AGTATGTGTA | TGTTCAAATG | GAGATTAAAG | AAGGCAAAAT | AAGGCCGGGT | GCAGTGGCTC | 155340 |
| ACACCTGTAA | TCCCAGCACT | TTGAGAGGCC | AAGGCAGGCG | GATCATGAGG | TCAGGAGTTT | 155400 |
| GAGATCAGCC | TGGCCAACAT | AGTGAAACCC | TGTCTCTAAT | AAAAATACAA | AAATTAGCCG | 155460 |
| AGCACGATGG | CATGCGCCTG | TGGTCCCAGC | TACTAAGGAG | GCTGAGGCAG | GAGAATCACT | 155520 |
| TGAACCCGGG | AGGCAGAGGT | TGCAGCGAGC | CGAGATCACG | CCACTGCCCA | GCAGCCTGGG | 155580 |
| TGACAGTGAG | AGACTCCGTC | TCAAAAAAAA | AAAAAAAAA | AAGTCAAAAT | AAAAGAACTG | 155640 |
| TGGGCTGACA | ACTGTGGATT | AAGCATCAGT | TCTATTAAGA | AGGGCTAACT | TGAAGATGAA | 155700 |
| TCTTTTGAAG | ATACATTTTG | ACTCCAGCTC | TTTAGAGGAA | CAAAGTTTAC | CTTGATGTGA | 155760 |
| AATTCTTCAA | ATAAAAATTT | ATTGACTTTA | AATTTAAAAA | AAAATGCACA | CACACACACA | 155820 |
| CACACACACA | CAGCTAACTA | GCTACATCCT | TAATGACACC | AAGCTTTAGT | CCTTCACCCT | 155880 |
| GAAGTGGGAA | TGACAATGGC | ACTTACTTCA | AAGTGCTGTG | ACAAGAATGT | GTTTGAAAAT | 155940 |
| AAATATAGAG | TAATCAGCAA | CAGTGCTTGG | CATATTGTAA | ATAAGTGCTC | AAAAAATGCT | 156000 |
| AGTTCCCAAA | ACTGTTGTTG | CCACTGTACC | CTAAATCCCT | ATTCTCTTCT | GATATCCTTT | 156060 |
| AGTGATGTAA | TTCTGTCTTG | CACTGGGCCT | GTTCATCTCT | GGTATGAATT | TCAACCACAA | 156120 |
| TGTCCTTACT | ACATTTCCCT | CAGGCTTATA | TAGCCAAAAT | ATCCAGAGCT | TGCCTAGGA | 156180 |
| GTGTATAATA | TGATACTTCA | ATTTGTAGCC | ATGATAGCAC | TGTGTATGAA | AGTTTGGAAT | 156240 |
| AATGCGCCGG | GCATGGTGGC | TCACGCCTGT | AATCCTAGCA | CTTTGGGAGG | CCGAGGTAGG | 156300 |

-continued

| | | | | | |
|---|---|---|---|---|---|
| TGGATCACTG | AGGTCAGGAG | TTCGAGACTA | GCCTGGCAAA | CATGGCGAAA | CCCCGTCTCT 156360 |
| ACTAAAAATA | CAAAAAAATT | AGCCGGGTTT | GGTGTCAGGT | GCCTGTAATC | CCAGTTACTC 156420 |
| AGGAGGCTGA | GGCAGGAGAA | TTGCTTGAAC | CGGGGAAGTG | GAGGCTGCAG | TGAACCAAGA 156480 |
| TCACGCCATT | GCACTCCAAC | CTGGGTGACA | GAGAGAGACT | ATGTCTCAAA | ATAAATAAAT 156540 |
| AAATAAATAA | AAAACAGAAA | GTTTGGAATA | ATGCATTACA | AGTAGCCTCT | AGTTTTTATG 156600 |
| TTACTCATAG | TTTTATCACA | CAAGAACAAT | GTCATAAATT | TTCATGGTTG | AATTATCAGT 156660 |
| TGTTTATGCA | ATATTCATTG | ATGTTTTGG | CTTATCAGCA | GTGTTTCTGG | AATTATTGA 156720 |
| ATATTATTAC | CGTTTTTCAA | AATTATTTTA | TAAAACTAAT | TTAAAAATCA | AAAATGATAT 156780 |
| AATTACTAAT | GTGAAATTAA | ATATAAGTTT | TGAAGAATAT | CAGGATGTCA | CCCCCAAATT 156840 |
| ATTCTACTTT | GGCATAAAAG | TTATTTTCAG | CTGAAGGCAA | TTGAAAATCA | ACAGGTGTAG 156900 |
| GAAGAGGTCT | CTGTCTTCTC | TTTACCCAAA | TTTCCCTTTG | TGAAGGTGAC | AGAAATTTCC 156960 |
| CTTGTAAAAG | TGTCCCCAAC | TGCTATACCA | GGAAAAAGAG | AGCAATTCTT | ATCACTAGAT 157020 |
| ATGGAAGGTT | GGCACTGAGA | TGACTCTGCA | AAAACAAACC | TTACTACAAT | TATTTCTATC 157080 |
| TTTCATTTTA | TCTTCCATGG | TTTTTATTGC | CCATGTATTT | ATTTCCTTGT | CACATTCCCA 157140 |
| AATTCGTCAT | CCCATGAAGT | GCAAACTCCC | TTTCCTTTGT | TGGAATGGTG | TATAAGTCTG 157200 |
| TGAGTCTAAC | CGCGTTTTTA | AGGTTTCAAT | TTTTTTTTCT | TGGGAACTC | TGTGCATGTA 157260 |
| ATATACTAAT | AAAATTGCAT | GCTCTTTTTT | TCGCATGTTA | ATCTGTCCTT | TGTCAGTTAA 157320 |
| ATTTGCAAGA | CACTACTTAG | TGAATCTAAG | AGTACAGAAA | AACATGTGTC | CTCATTGACA 157380 |
| GTTTCAAAAA | CTAAGTAAAA | TTGAGGCAAG | AATCTTTTTC | ATCTTAAAAT | GGCCAATTTT 157440 |
| AATTTCCAAA | TGAATGGTTC | ATTAGACCTA | AGCCAGTAAG | CTATGTGAAC | AATTGTGATG 157500 |
| GAATAAAACA | AAACTAAAGA | GCATGAACAA | AATTGAGAAA | ACATATGCAA | GACTGAATCT 157560 |
| AAAGGCCAAA | TAGAATTGAA | AATTTTTCTA | ATTTTTAACT | CTATAAATTA | AAGGAATGTG 157620 |
| TTTCATTTGA | CGAGTTTCAT | CTGTGGAAAC | ATGTTTGCAG | AAGACATTCG | AGGTTAGGAT 157680 |
| TAATTGAAAG | TACATAAATC | AAATGGATTA | AGACCCCAAA | GGGCATTGAA | GGAAAATTAG 157740 |
| AAAATCAGCT | ATTTTTGCTT | GGGTTGATTC | CTCTCCTGAC | TAACTCTTGG | AGATGATAAG 157800 |
| AACATCAATT | AAATGGGTAG | CCATGAAAGT | ATCTAAGGGA | GAAAGGAACA | CAGAAGTTCA 157860 |
| ATGTACCATA | ACTTTATTTT | TATTTATTTA | GTTTTTTGAG | AGAGAGTCTG | GCTCTGTCGC 157920 |
| CCAGATGGAG | TGCAGTGGCG | TCATCTTAAC | TCACTGCAAC | CTCTGCCTCC | TGGGTTCAAG 157980 |
| TGATTCTCCT | GTCTCAGCCT | CCCGAGTAGC | TAGGATTACA | GGTGTGTGAC | ACCACGCCCA 158040 |
| GCTAATTTAT | TGTGTGTTTT | CATGGCCAGG | CTGTATTTTC | ATGGCCAGGC | TGGTCCTGAA 158100 |
| CTCCTGACCT | CAGGTAATCT | GCCTGACTCA | GCCTCCCAAA | GTGCTGGAAT | TACAGGCGTG 158160 |
| AGCCACTGCT | TCCGGCTTTT | TTTTTTTATG | ACGGAGTCTC | GCTGTGTCAC | CCAGGCTGGA 158220 |
| GTGCAAGGTC | TCGCCTCACT | GCAACCTCCG | CCTCCCAGGT | TCAAGCAATT | CTCTGCCTCA 158280 |
| GCCTCCCGAG | TAGCCGGGAT | TACAGGCGCC | TGCCACCATG | GTTGGCTAAT | TTTTATACTT 158340 |
| TTAGTAGAGA | CGGGATTTCA | CCATCTTGGC | GAGGCTGGTC | TTGAACTCCT | GACCTCGTGA 158400 |
| TCCACCCGCC | TAGGCCTCCC | AAAGAGCTGG | GATTATAGGC | GTGAGCCACC | GCGCCCAGCC 158460 |
| TTTTTTTTTT | TTTTAATTGT | TTGATGTTGA | GATGGAGAAA | CAGGAGGAGG | TGGAAGAGAT 158520 |
| CTTAATATAC | ATATGGAAAA | ATAAAAAATG | GAATAACCAG | GAAAATTCTG | AAAAAGAAGA 158580 |
| GTAATGAGAG | AAAATTAGCT | CTATCTGCTA | TTAAAGTCAC | GTTACAACAT | CTCAGTTAAT 158640 |
| TAGTCTCCCA | AAGGGGAGAC | TAATGTAAAT | GCATGTTTAA | TAAACTGCAC | CCCCAGTGGA 158700 |

-continued

| | | | | | | |
|---|---|---|---|---|---|---|
| TGCCTGAAAC | CACAGATAGT | ACTGAACCGT | ATATACACTG | TTTTTTTCTA | TATACACATG | 158760 |
| GCAATGATGA | ATTTAATTTA | TAAATCAGGC | ACTGTAAGAG | ATTAGCAATA | ACTGATAATA | 158820 |
| AAACAACAAT | TATAACAATA | TACTGTAATA | AAAATGATTT | GAGTCTGTGA | ACGGTGGTTC | 158880 |
| ACGCCTGTAA | TCTAAGCACT | TTGGCAGGAT | GAGGTGGGCG | GATAACCTGA | GGTCAGGAGT | 158940 |
| TCGAGACCAG | CCTGGCCAAC | TTAGTGAAAC | CCCGTCTCTA | CTAAAAATAC | AAAAATTAGC | 159000 |
| CGGGCATGGT | GGCAGGCCCC | TGTAATCTCA | GCTACTCGGG | AGGCGGAGGC | AGGAGAATCG | 159060 |
| CTTGAACCCG | TGAGGCGGAG | GTTGCAGTGA | GCCGAGAACG | TGCCACAGCA | CTCCAGCCTG | 159120 |
| GGTGACAGAG | GGAAACTCCG | TCTCATAAAT | AAATAAATAA | ATATAAATAT | AAATTATATG | 159180 |
| ACTGTGATCT | CTCTCAAAAT | AGCTTACCGT | TTTACTTGTG | ATGATGTGAG | ATGACAGAAT | 159240 |
| GCCAGTAATG | AGATAAAGTG | AGGTGAATGG | AGTAGGCATT | GTGAAGTAGC | ATTAGGCTTG | 159300 |
| ATAAGATACT | ACAGATTTAG | GTATTAGTTG | AACACTTGCC | ATTTGTCACA | TAATCATCTC | 159360 |
| AGCATTGAGG | ATAGCACACA | ACACAATGTT | TAAAACAATA | CAATTCTACC | TTAAGAATTG | 159420 |
| TGGGAATGAC | TAAAGGAACA | AAATAGAAAC | CTGAGAAACC | TAAGACAGTC | CAACTGTCCA | 159480 |
| TGAAATTATA | GCGTATTAGC | CTATGACAAA | ACAGCCAAAA | TTGATAGGAG | CGTGGAGGGT | 159540 |
| GGCACGGGAG | GAAGAAGGGG | GAAGCAGAAA | TGAAAGTTCA | TAAATGGTCT | TGGGAAAAAT | 159600 |
| ATGTCCATAT | GTTAAACCTT | ACACCAAAAT | AGAGGGTTCA | CCATGTTAAA | CCGTGTTGTA | 159660 |
| ATGTAAAATT | AACAACACAA | AATTACTTAA | ACCATGGGAG | AATGTTTCT | CCTTCTTCCC | 159720 |
| TGCCTCTGTC | TTCCTGTCTC | TCTGCTTGCC | TCCCTCCCCT | TTCTCTTTCT | TGGGATGAAT | 159780 |
| CCGTGGTCAC | TATCACTAAC | AAATCAACTC | ACTATATTAA | TCATTGTGGA | GATGGTAGAA | 159840 |
| TAATTGAGCA | GCTTATCTCC | AGAAGCCCCA | GTCCCCATAA | TTTAGGTCTC | ACCAAAATGT | 159900 |
| GCCCACCAGA | TTTTAAAAGA | AGCGAATATA | AGACGCTAGG | CTTTCTGTAT | TCAGAAGCAC | 159960 |
| CATGGATGTC | AAACAGAGGG | AACCATTAAC | GAAGGCCTTT | ATTAGAAATG | TCTCCCATTT | 160020 |
| ATCCATACAC | TCTTCATAGT | TAATAGTACA | AATACTGTTT | TCTGCATAGA | AACATTTGGA | 160080 |
| CTGCCAAACA | AAATACGTTT | AAAGGAACTT | CGATTTTTAA | ATGTTGCTGT | CTGTCTAAAC | 160140 |
| AGGATAAGCA | ACCGTAGTCA | TGCGAGGACA | AAATGGCTGG | CTAAAAGTTG | TGCTTTCGAT | 160200 |
| ACGCTCAAAA | TCGATACGCT | CAAACCTGTC | AGTTTAGCGG | AAGGCTACAT | GTTATGTGGC | 160260 |
| ACAAAAAACT | CCCTAGGTCC | ACGATTGCCT | TGGGTGGAGG | AAGGGCTATT | GCCGCTGTTG | 160320 |
| TGGCTGTTTT | TTAAATGCAT | TCCTTCGTTG | CCACAGGAAT | GAGAAATTAA | CAGCAGAGGA | 160380 |
| ATGTAGGACA | AAGGTACCTG | CACGCACTCT | CCTCCCAGGG | CTGGATGTTG | CCACTACCTC | 160440 |
| CAGGAGACAT | CAACTTGACT | ACCAACAACA | TGGAAAGCGT | CCGAAATCCC | AGACATTAAT | 160500 |
| ATAAAGAGAA | AAGAGGCAAA | ACTTTTAAGT | CACAGTAAAG | CAAAAAACAC | AGAATAAGCA | 160560 |
| ACGTCTTCCA | CCATCCAATT | AAATACAGAA | TGAAAGTCAT | GTACTAGAAG | AACGGACCAA | 160620 |
| CCCGGGAGCA | GGGCGGGACT | TTTGAAAATT | TTTTAGTCCA | ATCCGGACAT | CCCTTTAGAC | 160680 |
| TAAGAAACTG | GCTCTTGTTT | TGCGGTCTTT | TCTGCCGTTC | ACAGGCCTGG | GGCGGGACTG | 160740 |
| CCATCCCAAA | ACCATCCGCC | AGCGAGAAAA | GCCTCCGGTC | AGGGACCTAG | AAGCCGCAAT | 160800 |
| AAAGGTTTAA | ATGCTGTAAC | CTCACCACGG | CCACTCTCCA | ACCCCGTCAC | CCAATTCGTC | 160860 |
| TGATACCTCA | GTAACTCCCA | TACGACTAAC | CTTAAGTAAC | AGGGCAGAAC | AAGAAAAGGC | 160920 |
| AGATAGTAAA | GAAATTATCC | AGCTCTTTTA | TTGAGATCAG | TGGTGGCTCT | GAAAAGAGCC | 160980 |
| TTTTGGGTTT | TAGAAGTAGG | CGTTCGCCTA | TTTCTTCTTG | GGCGCCGCCT | TCTTAGGCTT | 161040 |
| GACAACCTTG | GGCTTAGCGG | CCTTGGGCTT | CACAGCCTTA | GCAGCACTTT | TGGCAGCTTT | 161100 |

| | | | | | | |
|---|---|---|---|---|---|---|
| CTTGGGCTTC | GCAACCTTGG | CCTTCTTTGG | GCTCTTAGCC | ACTTTCTTGG | TTACAGTGGC | 161160 |
| CGCGGCCGGC | TTCTTCGCTT | TCTTCGGTGT | TTTCTTAGCG | CTCTTCTTCG | GAGTTGCGCC | 161220 |
| GCCAGCCGCC | TTCTTGGGCT | TCTTGGCTGC | CCCAACTGGC | TTCTTAGGTT | TGGTTCCGCC | 161280 |
| CGCCTTTTTA | ACCTTGGGCT | TGGCTTCCCC | GGAGGCTGCC | TTCTTGTTGA | GTTTAAAGGA | 161340 |
| GCCAGAAGCA | CCGGTGCCTT | TCGTTTGCAC | CAGAGTGCCC | TTGCTCACCA | GGCTCTTGAG | 161400 |
| ACCAAGTTTG | ATACGGCTGT | TGTTTTTCTC | CACATCATAG | CCGGCGGCAG | CCAACGCTTT | 161460 |
| TTTCAGAGCA | GCCAGAGAAA | CTCCGCTACG | CTCTTTAGAG | GCGGCCACAG | CCTTGGTGAT | 161520 |
| GAGCTCTGAC | ACCGGGGGAC | CAGACGCCTT | ACGAGGCGTA | CCCCCAGCCT | TTTTGGCCGC | 161580 |
| CTTCTTCTTT | ACAGGGCCT | TCTCCGCAGG | AGGCGCGGCA | GCGGGAGCGG | CAGGAGCAGT | 161640 |
| CTCGGACATG | TTGAGAATCA | AAAACTCGGG | TACAAGTGGC | AAAGCGCCGA | TGAAGCAGCG | 161700 |
| CCTGGGCAGG | GCCGCTGTAT | ATATAGAGCG | CAGGCGCGCT | CTGATTGGTG | CTCTGGTCGC | 161760 |
| CCGCCTGGCT | GGCAGGCTCT | GAGCCGCTGC | GCTGCTCCCA | AGTTGTGTTT | GTTCCACCTC | 161820 |
| ACAAAGGGG | AAAAATATTA | AAATTCCCCG | CACCAAATCA | CTTGGGTTTG | GTCAGGAAAG | 161880 |
| GATCTCAGAA | GCCTCGGGCT | TCATGCTCTT | CATTTATTTT | TTCCACAAAC | ACAAAAACAA | 161940 |
| CGCGTCCAGG | CGTCCCCAAT | TCCCCCAACT | CCGAAGGAAG | TCTGGGGCAG | TCAGAGACCA | 162000 |
| CTTTCTGTTT | TTCTTATAAA | TTACCTGTTC | GCTCCTTTGC | CCCTGAAGGT | TCTTTTTCCC | 162060 |
| AGGGGTGGTT | GGGCACATGC | TTCCCTTATT | TTTGAAGAAA | AAAGCGAAAT | GGTTTCCACC | 162120 |
| TAAATTTTCA | TGATAATTCT | GTTTCTTCAC | AAGGGAAGTA | ACACAGGTCC | TCTGTGAATT | 162180 |
| CTTCGTGCAG | TCGCACAGGA | ACTGTGGACT | GGGACAAGGA | TTCCACGGCC | AGTCCAAAGC | 162240 |
| AATTAGGGCG | GGATGGGAGG | GGGTTCATGA | GCCTTGCTAG | GGTCCGGGGT | GGTGGGGGC | 162300 |
| TACAGACTTA | AATCTTTGAT | TTGAAGACAT | TGAAACTATC | AAATCCCTCT | TTTCATAGAT | 162360 |
| GGGGGTGGGG | CATCCTTTTC | ACTTCTCTAC | AGGCGAGAAA | TTGGGCTCTT | TTTAAAGAGC | 162420 |
| TCTGAGGTCC | CCCTCTGAGT | TGTGTAAGGC | AGGAGGTCTG | GCCCTCAAGA | TAGAGATCAT | 162480 |
| AAAGGAACAA | GGGAGAGCCC | TTAAGCCTGC | AAAAAAGCCA | ATAGATTTGG | CAGTTAGAGG | 162540 |
| CACTGAGATA | ATATGTTTTC | AAAGAAAACA | AGCATTTTTT | ATTTATTTAT | TTTTGTACGC | 162600 |
| TGCAATATAG | AAATGAATTT | CAGCCCATGA | AAATTGTAGG | TTACTTTCAG | TAACCATACC | 162660 |
| TTACGCAAGT | TACCATATAG | GACAATCTCC | AGTTGGGAAC | TCAAATATAT | CTTTTGAGTT | 162720 |
| GCAAATAAAG | CAACTGACTT | TAATAAAACA | CACTCTTGAC | TTTTAAGATG | AACAATGTAT | 162780 |
| TTGAAATTTA | TTTTTTTAAA | TAGCAAAATT | TAACACAGAA | AGACAAGAAA | AGTACCAGAA | 162840 |
| CATGTAATTT | ATTATAAGAT | CTGTTGTTGA | TGAGCTGAAA | AATCACCTCT | TCTCATCCCC | 162900 |
| TCTGAAACTA | TTCTGTTCTA | AAGTTTGCTA | CTTTAAGGTT | CACTACTTCT | TATTTTACTC | 162960 |
| TCCGACCCCA | AGTAATTGCT | ATTTTTTTCT | TGAGATTAAA | GGCAAAGTAA | ATTGTCTGCC | 163020 |
| CATATATTTG | ATATAATTAT | AGATTCATAT | TTAGGGACAA | AGGTAATATT | ACAACTCCCC | 163080 |
| AACAATTTCT | GCTCAAATAT | ATGTTTTCAT | GAAAATATGT | GTTAAAGAGA | ACAGCCTTAG | 163140 |
| ATTGTGGGAA | AGTCAAAAGG | GAACCTACAA | ATAAGAGTTC | AATGACAAAT | GAAAAGTGAA | 163200 |
| ACATCTTTTA | GACTAAGGGT | GACCCCATTG | TTTTATTAAA | TAACATTTGT | CCAACATTTG | 163260 |
| TAAACATTGT | CTGCTTGTGT | GCTTATGTCC | TCTGGGAATT | AACAGTCTAA | TGAGATTAGT | 163320 |
| GATGGATGAA | TTAGCAGTGG | TGGAAAAACA | CTTAGACCGG | CTATTCCTCA | GAGTGACAGG | 163380 |
| GTATAAGAAT | TATACAAAAT | TATGGAAAGT | GTATAAACAA | TTGAAGCACC | TGCATCATAC | 163440 |
| TAATATATTG | TAGTAAAAGA | AATAATATAA | GGCTGGGCCC | CGTGGCCCAC | GCCTGTAATC | 163500 |

```
CTAGCACTTT GGGAGACTCG GGGGCGGATC ACCTGAGGCC AGGAGTTTGA GATCAGCCTA  163560
GCCGACATGG TGAAACACCA TCTCTACTAA AAGTACAAAA ATTAGCTGGG GGTGGTGGCA  163620
CTCAGGAGGC TGAGGCAAGG GAATCGCTTG AACCCGGGAA GCAGAGGTTG CAATGAGCCG  163680
AAATGACGCC ACTGCACTCC AGCCTGTGCA ACAGGGTGAG ACTCAGTCGA AAAAAAAGA   163740
AAGAAAGGAA CAATATAAGA ACATGTCACT TAGGCCAGGC TTGGTGGCTC ACGCCTGTAA  163800
TCCTAGCACT TTGGGAGGCT GAGGCGGGCA GATCGCCTGA GGTCAGGAGT TCGAGACCAG  163860
CCTGGCCAGC ATGGTGAAAC CCCATCTCTA CTAAAAAAAA TACAAAAATT AGCCTGGCGT  163920
GGTGGCAGGC AACTCTAATC CCAGCTACTC AGGAAACTGA GGCAGGAGAA TCATTTGAAC  163980
CCGGGAGGTG GAGGTTGCAG TGAGCCGAGA TTGCCTCGTT GCACTCCAGA AGCCGAGATT  164040
GCCTCATTGC ACTCCAGAAG CCGAGATTGC CTCATTGCAC TCCAGCCTGG CAACAGAGC   164100
AAGACTCCAT GTCAAAAAAA AAAAAATAAA ATAAACATTT CACTTAGATC TTATTCTATG  164160
TGCAATGAAC CCCCTTCTCA TTTAAAACTC AGCTAAGTAT ATCCATCATG AAAATAGCTA  164220
TGAAACGTCT TGATTACCAG GTAACTGGAC CTTCTTTCAC TATAAATTGG TGTCCTGGTT  164280
TATAAATCGA CATGTAAATT TAATCGCTGT GATTCAGTTC TCTAATATGA TTTTCTAGT   164340
CGACTCAATC TAATCACATC TCTTTATATG CAAATCTCAA GTCCAGACCT CAAGCCATTA  164400
GGACATCCAG CCACCCAGAA TCTTGTCCCC AACCTCCTGG CAACATGGTG GAGGCCAGAA  164460
GACAGAGAAA CATGTAACCA ACCCTTTTCT AGATCCTTTA TAAAGTGTGT TGAAAAGTT   164520
ATGCAAAACT TAAAAGCAAC GCAAAATAT  TTCTCCATAT CCTTCCAAGC TATATTAGAG  164580
AATTATCTAA AAAGCCTACT TATGGGGTAC CTGATGATGT AAGGCAATAC TAGACAGTAA  164640
AATAGAATGT GAATCACATA AATACTTTCC AGATTCTAG  TGGTCACATT GAAAGAATGA  164700
AAAGAAACAA GTAAAATTAA TTTTAAGATA TTTTATTTAA CTTAATATAT CTAAACTATT  164760
ATCACTTCAA CATATAATAA ATAAGCTAAA AAAAAAGACA GTTGACATTC TTTTTTAAAT  164820
GATAAATCTT CAGAACCTGG TGTGTATTTT ACACTTTTAG AACATTTTAA ATCAGTCTAG  164880
CTATAGTCCA AATGGTCAAT GATCACGTGT AGCTAGTGGT ACCTTATTGG ACAACACTGT  164940
CCTACGTGAA AGTAACTCTG ACTTAATGTT TACATTTTAT TGGGTCCAGA CTATCTAAAA  165000
GTAAACATTC ACTTGTAGAA GTTTAATAAA TTAATAAGGA TTTTGTCATA GAGATGGAAA  165060
TGAATTCTTA ATATAGAAAA AATGACCCTA AAAGTTATTA TTGTATTGCC TAATAAGTCA  165120
TTAAACAACT TTATATCTGA TTTTCCCTTC CTCTTCCAGT ATACATCCTT TCCCTGACCA  165180
AATACATATT TTATTCTCCC GTATCTTCCT TTGACCTAAT TGTGATTCTG CTTCCTCCTT  165240
CATTAATGAA TTAAATCATT CATTGACACA TACACAAGCT CACTATATAT AGTACATATA  165300
TGTCAGTCAT GTTTTTAACT TCCTGAATGT TGTACTTTGA CACTTGGTTG TTCAATTTCG  165360
CCTAAGAGCT CTGAATCAGA ACCTTTAGAA GCCATTCTGA AAAACTGGAA GATACAAAGC  165420
TTTTGACTAT CAACTCCATA GCAACCTGAT ATCTGGTTGG TGTTCCATGG AAACTGTATT  165480
TCTCAAATTT TGAAATAAGA TTGAACAAGC CTGTGAGCAA CAACAAAAAA AAAGTCTATT  165540
AGAATGACCT CTGGCCGGGC GGGGTGGCTC ACGCCTGTAA TCCCAGCACT TTAGGAGGCT  165600
GAGGTGGGCA GATCATGAGG TCAGGAGTTT AAGACCAGCC TGACCAACAT GGTGAAATTC  165660
CGTCTCTTCT AAAAATACAA AAATTAGCTC GGCATGGTGG CGTGCATCTG TAATCCCAGC  165720
TACTTGGAAG GCTGAGGCAG GAGAATCACT TGAACCCAGG AGGCGGACGT TGCAGTGAGC  165780
TGAGATTGCG CCACTGCACT CCAGCCTGGG TGACAGAGCG AGACTCTATT TCAAAAAAAA  165840
AAGAATGACC TCCAAGGGAA AGTTCAGATT AAGGATGTGG TCGTCCCACC CAAAACTGAT  165900
```

| | | | | | | |
|---|---|---|---|---|---|---|
| GTCCTCAAGA | AAGCCACAAA | CAAATTGAGG | ACACAGTTAA | AATATTGTAA | TGCAATATAT | 165960 |
| TGTGTATTCT | TTTATTTACA | CACACATCAT | AAATATTATA | GGTTGACTAG | TTTTGTTTCA | 166020 |
| TGCCACACTC | TTCAGGGTCT | GGAAACCCTG | GTAGAAAAGT | TAAAAATGCA | GAGCAAAATG | 166080 |
| TCAAGTCCAA | ACAGCAGTAA | TGGGGCTAGA | GAGAGACTCA | AACAGCCAAG | ATATATTCAA | 166140 |
| AGGATAGTGA | GAGGAGTTGT | TAGGACAGGT | GTAAGGAATG | AGGGTGACAG | CTGGTTTTTC | 166200 |
| TTTCACTTTT | TCCTTCTACT | ATGCCAATTA | GAGTTCTTTG | TTTTGATAG | AGACAGGGGT | 166260 |
| CTCACTATGT | TGCTCAGGCT | GGTCTCAAAC | TCTTGGCACC | AAGTGATCCT | CCTGCCTCAG | 166320 |
| CCTCCCAAAG | TTTTGAGATT | ATAGGTGTGA | ACCACCAAGC | CCAGCCTTAG | AGTAGGGTTC | 166380 |
| TGTCATCTTT | TGGATGTAGC | TAACCTAATA | TTACTAAATC | CTGTATAGGC | CAGAACTTTG | 166440 |
| AATGATTTAA | AGCTGTTTTT | TCCTGACTCA | CCAATTAATG | AAGCTAATAA | TAACAGCCAC | 166500 |
| CCCACTGGCA | GTGCCTGCCT | CAAAGAGTAA | GTGTTAGTGT | TGCTATCTGC | TTGAGACCAA | 166560 |
| CAATACAGGG | ACTCCAGGAT | ATTTTCAGCC | TAAATAAGAT | TGTAGGGGCT | CTTGTCTGTT | 166620 |
| GCCTGGCTTC | AGCCCCATAA | ACTTTTTTTT | AACATATAAC | CCAGAGCCAC | AGTTTGCTC | 166680 |
| ATATTTCAAT | CTTTGAAGGC | AAATGGCCAA | CAATTAGATT | AAACCTGAGG | CTAAATATTT | 166740 |
| CCTCACCTCA | AGGGCTGAGA | CGAAAGTTAC | TGCATCTGTA | TTCCCTAACA | CGCCCTCAAA | 166800 |
| ATGGGTTGCA | GAAAACAACA | GAAAATATAC | TAAAGCACAC | AGTAGGAGCA | TAATAAATAG | 166860 |
| TGATTAGCTG | GGTGCAGTGG | CATGCGCCTG | TAGTTCCCGC | TACTCTACTC | ATGAGGCTGA | 166920 |
| GGCAGGAGGA | TCACTTTTGC | CAAGCAGTTT | GAAGTTGCAG | AGAGCTATGA | TCACAACACT | 166980 |
| TCACTCTAAC | CTGGGCAACA | GAGCAAGACT | CTGTCCAGAA | AAATAAATAC | ATAAATATAA | 167040 |
| AATTTAAAAA | TATAAATAAA | TACATAGAGA | GTATTACAAA | AGGAACAATA | TATTGCAAAA | 167100 |
| TATATTTACC | TAACATTTTG | AAATTGCCAT | TATAATTGTA | TAAGTGACAT | AGGAAACTGG | 167160 |
| GTCATTAACA | GCTATCTTAT | TCTTCAAGCT | TCTTTCAAAT | GATGTCAAAG | CATTTCAGAA | 167220 |
| AGTCAAACCT | ACCCTCAAAG | GATAAGAATT | TGTCAATTGT | GAGGATATGC | ACATTTTTAC | 167280 |
| ACCTTCTCAA | TCTGTGTCTA | TATGAAGGCA | GTTATAAAGC | ACAAGATGCA | AACGTATATT | 167340 |
| AGGCAATAGT | CTTCATCAGA | ATAAGTACAT | AACCTGACAC | AATGACTATA | TTGGAAGAAA | 167400 |
| CATGGAAATG | CAAATTTCAA | TAGATTGGTT | GACATTATTT | TTTAATGTCT | AGTTTTTAC | 167460 |
| TGTGCTGTGT | TTTTACACAC | TTAATGAGCA | CTTGTTAAGC | ACAGGACACC | AGGAGAAATA | 167520 |
| ATAAAAACTA | AGATCAGCCT | AGCAGTGTGT | CCTCTCAAGA | ACTTATACCT | GGTGGGACAG | 167580 |
| ATACAGACAA | ATATAACCAT | CATACAGTGT | GAGAAATCGA | TAGAAAAGAC | ACAGCCACTG | 167640 |
| AGAGCACAAA | AGAATAAAAA | CATAAAATGT | TAATGTGCTG | GCTAAACGTT | TGCCTTCAAG | 167700 |
| TATTTACCAG | TCTAGCTGGG | AAAATAAGAC | AGAAGACAAC | AGCCTAAAAT | AGTGGTTCTT | 167760 |
| AAACATTTAG | ATATCAGGAC | TTCTTTACAC | TCCTAAAAAC | TATCAGGCCT | CCAAAAAATA | 167820 |
| TTTTGCTAAA | TATAGGCATT | TATCACTTTG | GAAAACAAAG | CTGAGTATTA | ATTATTTAAT | 167880 |
| TATTTATATT | AATATTTATT | TGATAACCTT | TAAAATATTA | TAAAATTAAT | ATTTATTTAT | 167940 |
| AATGCATATA | TGTGATTATA | TAGTTCATAT | GTAGCCATAT | ATTTATCATA | TATACCATAG | 168000 |
| ATTTATGTTA | TATATTACAT | ATGTATGAAG | AAAAAATGGA | AAGTAAACCC | AAAAGTTCCC | 168060 |
| CATTCCCTAA | CCCATTCAAA | ACCCTGGAAG | TCCAGGCTA | ATCTGAAACT | TGTAAAACTG | 168120 |
| CCTGCATGTA | GAGAGCACAG | CTGAGCTGGT | AGTGTGGAAG | AGCAGAAAGA | CAGCAGTTCT | 168180 |
| GGAGCAAGGA | AGCTTTATAT | TTAATCCCAG | TTTCTCCATT | CATGAGCTTG | GTTACCCTGC | 168240 |
| CAAGTTCCTT | CTCTGTAAAA | TGGGAATAAT | ACTCCCAGAA | ATACAGTGAG | GATTAAATTA | 168300 |

| | | | | | | |
|---|---|---|---|---|---|---|
| GATAATGTGC | ATACAGTTCC | TGGGATTGGG | ATCAGCACAC | AGTAGCCTCT | CATTTGAGGC | 168360 |
| ATATTTGCAT | TAGATCCTTG | CTGTATGATA | TCCTTCTGTT | TCTTTCTTTT | TTTTTTTTTT | 168420 |
| CCTTTGGTGA | CCCTAAGAAA | GATGGTACTC | TCCTTAACTT | GGAGGGCTGG | ATGCGAAGAG | 168480 |
| ACCAAATCCA | ACAAGCTGGT | TCATTCTTTC | TAATTATGTG | TGCTTCCCTT | AGCTGCCTCT | 168540 |
| GAAAGGATAC | AGGCCCTAGG | TACTAGCCCC | AAGAAGCCTA | ATGATAAGAG | ATAGAGCTGG | 168600 |
| ACCACCAGAG | AAGAGATGAG | TGTGTATGTG | TGTGTGTGCA | AGCAATTATA | TGTGTGCATT | 168660 |
| TAGGAGTGGT | AGGTGTGTAA | ACAGTCTAGA | ACACTCATTC | TCACTGTGAT | GTGAGGATGT | 168720 |
| ATCCCCACAT | CACTGTTCTG | GGAGCTCACT | CCTTGTCCAT | CATCCAAGCT | TATGATGGAC | 168780 |
| AATTCTTTCC | CAAGTGGGAA | AGAATTCTGA | TGACACTCAC | ATAACTACCC | AGTCCCAACT | 168840 |
| TTCTGTATCC | AAGGTGTGTG | CATACCTTTG | ATAGCAGGCA | GGTGTGCCTA | GCCAATATAT | 168900 |
| TAGGAGCATG | GTATTCCAGC | ACTCTGCACT | TTTTTACTAT | AGAATTCATC | TCAACCTGCT | 168960 |
| TACATTACAT | GAAAGTTTTG | ATTGATATCA | AATTTTTATT | ATGTTTGCTT | ATCAAAGGAT | 169020 |
| TTGTAATTAT | GCTTCAGTTG | ATACATAGAT | TGTTTATATT | TTTCATGGTT | ACTTGAAGCA | 169080 |
| CTTATATTTT | CCTCATACTT | TTACAAAGTA | ATCAAGGAAA | AATACAGAGG | CAGCTTAGTA | 169140 |
| TATTAGTCAA | AAGAATAATT | AGACTGTCTT | GGAACCTGGA | ATGTCTGAGT | TCAAATTCAA | 169200 |
| TTTTGCCGTT | TTACCAGCTG | TGTGACTTTG | GGTGAGTTAA | TAAACCTTTT | CGTGTCTCAG | 169260 |
| TGTTCTCACA | TGTAAAGAGA | CAATAATAAG | CCTACCTGTT | TCATGGGTCA | TTATGAGGAT | 169320 |
| TAAGGAGTTA | ACATTTAAAT | AGTTCTTAGA | ACAACCTCTG | ACATATTTA | AGTACAAAAA | 169380 |
| TATATACATA | TATTAAATAA | TAACTTTTCT | AAAACATCCT | ACCTACAATC | TTGTGTGCAA | 169440 |
| ATTGGTGGCT | CAATTCTGCA | ACTGTTGTTG | GTGGTGTTGT | TGTTAAGCTT | TTGTTTGTCA | 169500 |
| TGACTGTTAT | CAGTAATATT | AATACAGACA | GTTAACTGAA | CCCTTCCTCT | GCACCAGGCA | 169560 |
| TTATATGGAC | TATTTTCATT | CTGACTCCCT | GCATTCTATG | AGACAACCAC | CATTGTAATC | 169620 |
| ATTCTCACGT | TGCCAATAAG | GAAATGGAGA | ATGAGAATTC | AGACTTCTCC | AAGAAGTGCT | 169680 |
| GCAGACTGAT | TATAAATCAT | GCATCCTAAA | CACACACATA | TTAAAGTATC | AACTAAATCA | 169740 |
| AACAGAATAA | AACTTTTGTT | TTTCTATCTA | CAAAATGCAT | GAATTAAAAT | ATGCCCCAAC | 169800 |
| TACTTAACTA | ATATATTTAG | TAAGTAGAGG | GATGGAAGCG | TTTTCACTCC | TTCAATACAT | 169860 |
| TCTTCATCAA | CCTCTCTCAC | CTTACCCCTC | TGTCACAGGC | ATTTCCTATG | TCATGCGGTT | 169920 |
| TTTCTGATGT | ACGCTAGGTG | GCAGTCAAAA | CCACGAACTC | TTGAAAGAGA | GTATATTCCT | 169980 |
| ATTTTTCTGC | AGCCTCAACC | TCCAGGGCTC | AAACGATCCT | CCTGCCTCAG | CCTCCTGAGT | 170040 |
| AGCTGGGGCC | ACAGGTGCGA | GCCACCACAC | CTGGCTAACT | TTTACATTTT | TGATAGAGAC | 170100 |
| GGGGTCGCCA | TGTTAGCCAG | CCTGGTATCG | AATTCCTGAC | CTCAGGTGAT | CTGCCCGCCT | 170160 |
| CAGCCTCCCA | AAATGTTGGA | ATAACAGGAG | TGAGCCACAG | TACCTGGCCG | GTAATTTTTA | 170220 |
| ACTTCTAGCT | ATACACTTAG | TTTTTTGTCC | TTTTCAGTGG | ACAGAAATTA | TAATGCCTGT | 170280 |
| TTGACAGGGG | ATAATTCTGA | GGCACTGGGA | AGCCATGAGA | CTGCATGGAT | TGCACAGGCA | 170340 |
| GGCAAGAACA | TGGAAGGAA | CAAGTGTCTT | AGACACTTGT | CTCAGTGGTC | TAGAAAAATC | 170400 |
| ATGCTAGCTG | ATTCATTCAC | TCCACAAACA | ACTGATCAAC | ATCTTCAAGA | AGCCTAACAA | 170460 |
| TGTACTGAGT | TCAGGGACA | AGAAAATAAT | TCAGACAGGC | TCTACCTTCA | TGGTGGTGTT | 170520 |
| TGAAGAATAG | GGATCTAGAA | AACGGTAGGT | AATAGTGGCT | GTGCAAAAGA | TATCAGAGAT | 170580 |
| GATATGAAAA | GGAGGGACTA | GACCATTTTA | CCCAGGAGTG | GAGGTTAAAC | ATAGGGTCTT | 170640 |
| TAAGGGAAAC | GTAAAAATAT | TAATTCTTTT | CATTTTTGAA | GTAAAATGAC | CATCGCTTCT | 170700 |

-continued

| | | | | | |
|---|---|---|---|---|---|
| CGGCCGTTTG | GCTAAGAACA | AGTGAAGTAA | AATGACTGAG | GATGACAGAC | ATAAATACTG 170760 |
| CTATACAAAC | ATGGTAGCAC | TGAAATTGGC | TCTTGCCTGA | CAGGAAGCAA | AATTATAAAA 170820 |
| TTCATTATTT | AGATATATCA | ATAATGATGG | TGATCAGGCT | GTAATAATAA | TGTTATTAAT 170880 |
| CATTATGTAT | CAATAAGAAT | ACAGGTGTGT | GACTTTACAA | TGTGCCTAAG | AGCAACCCAA 170940 |
| TATTTTGATT | GTAAACCACA | TTCCCTTAAA | CACACACACA | CCTCAAACAA | GACCCCATAA 171000 |
| AGCAGACTGC | ACTAAAGTGG | AGGTTATGTA | AAAGTCCAAC | AGAATAAGAA | CCCTCCCCCA 171060 |
| TTGTGTATTA | ATCTGTGAAC | TAAAAAAAAA | TTTCATTAAA | TTGAAAATAT | CTAATTGTCA 171120 |
| ACTAGCAATT | TTAAAGAGTT | TAGGCAGAAA | ATGAAATATA | AAGCTTTTTT | TTAACTTTTA 171180 |
| GATTTTTCAA | AGCTAGCAGA | ACTGCTGAAG | AATAACAATT | CAAAACATAG | GTTTGCTTTG 171240 |
| GTTTCAATCT | CTGTAGCCAA | AGGCATTTAC | AATGTAGGAT | GTTGTTTGTG | CTTTCAGACA 171300 |
| CTAGATGACG | CTCCAAATCA | AAATGCCGGT | AGTTGGACAG | CCCCTGATCA | AGCCGCCCGG 171360 |
| CAAATCATTA | ACTGGGTTGA | CACTGTATTA | CTCAGCAGAT | TTCAAAACTC | ATTCACATAC 171420 |
| AGAGTCTTTT | GGTGGACAAA | AATAATTATT | ACCCACAATT | GACAGTGACA | GTACTGAGAA 171480 |
| GCTGGGAAAC | TGAAGTAGGA | CCCTGGAGCA | GCCAAGTACA | GAGACTGGCT | CCCAGGACCT 171540 |
| TAGGAGTTAA | TACTATTCCT | AAAGAGAATA | AATTGTCAAA | TAGACAAGAA | ATTCATGTGG 171600 |
| GTTGATGCAT | TCACTTCCCC | AAAACAATTA | TTAAGCAGTA | GAAATGATAA | CTACGCTGGT 171660 |
| AGTGGAAATA | GTTTACAGTA | AAAGGGAGAA | GACATGCAAA | AACCAAAAAA | AAAAACGGGG 171720 |
| CCGGGCGCAG | TGGCTCACTC | CTGTAATCCC | AGCACTTTGG | GAGGCTGAGG | CGGGCCGATC 171780 |
| ACGAGGTCAG | GAGATCGAGA | CCATCCTGGT | TAACAAAGTG | AAACCCCGTA | TCTACTAAAA 171840 |
| ATACAAAAAT | TAGCCGGGCT | TGGTGGTGGG | TGCCTGTAGT | CCCAGCTGCT | CAGGAGGCTG 171900 |
| AGGCAGGAGA | ATGGCGTGAA | TCCGGGAGGC | GGAGCTTGCA | GTGAGCGGAG | ATCACACCAC 171960 |
| TGCACTCCAG | CCTGGGCAAC | AGAGCAAGAC | TCCGTCTCCA | AACAACAACA | ACAAAAAAAC 172020 |
| AGGCAGTGAT | GTTTTATGTG | GGTCAGTGTG | AAGTAGAGAT | CAAAGGAGAA | AACGGCCAAT 172080 |
| CTTACCAAAT | AATGGATGCA | GAAATAATCT | TCATGGAGAA | GCCACTTTAA | TTATGTCTTA 172140 |
| AATGAGAGTA | ACAAATTAAA | CATAAGAACC | TGTAGGGGCT | AAGGGAAAAC | TTACTCTTTG 172200 |
| GCCTCTGAAG | AGTCGCTGAA | AACCACCGAC | AAGAGGAAGA | TTAATAGGAT | AAAATGCATC 172260 |
| CAATTTATTA | TTATTATTAT | TATTATTATT | ATTATTATTA | TTATTATTAT | TTTTAGACGG 172320 |
| AGTCTCACTC | TGTCACCAGG | CTGGAGTGCA | GTGGCGCAAT | CTCGGCTCGC | TGCAACCTCC 172380 |
| GCCTCCCGAG | TTCAAGCAAT | TCTCCTGCCT | CAGCCTCCCC | AGTAGCTGGG | ACTACAGGCA 172440 |
| TGTGCCACCA | CGCCCAGCTA | ACTTTTGTAT | TTTTAATAGA | GACGGGGTTT | CACCATTTCG 172500 |
| GCTAGGGTGG | TCTTGACCTC | GTGGTCTGCC | CGCCTCAGCT | CCCAAAGTGC | TGGGATTACA 172560 |
| GGCGTGAGCC | ATTGCACCCG | GCTGCATCCA | ATTTATTAAT | GTGTATATTA | ATAAATTATC 172620 |
| CAATTTATAT | CCAATTTATT | AATGTGTATT | AACATGTACA | GGGGAAATTG | TCCATTTTTA 172680 |
| TTTTTTAGAT | TCAACAAAGT | ATGGGCCGCC | GTGTAGAAAT | AGGATTGCTA | ATAAACAGAG 172740 |
| TAGGGAAACC | CAGCAAGGCC | TGTCTGTCTA | GATTCTTCTT | CGCCTCTCTG | TGCAGCATTC 172800 |
| CTTCCTTCTG | GATCCTCTCT | GGAATGCGGT | CTGGTGATCT | ATGATCAAAT | AAGGTAGTTC 172860 |
| AGATAATTTC | TTTATGGCCA | GTTTTACAC | AGAAAACAG | AGGGAAAGTT | AGAGTAATAT 172920 |
| TTTTAGGTTT | TATGGCTGGG | CTCTGGGGAA | AAGGTGTTTT | GATTTCTATG | ACCTAACTTG 172980 |
| AGGAAGAGGA | ATTCTCATTT | CTATGGCTAG | ACTCCGGGGA | GAATGGGACT | CAGAGACAGG 173040 |
| AGGGCAGGAG | AAGATCAGAG | AAAAACTTTG | GCTTCTGCGG | TCTTTATTTT | GGGGTATTGT 173100 |

| | | | | | | |
|---|---|---|---|---|---|---|
|TTTCTGAGTT|CCAACAAACC|CCAAGGACCT|ACAAAGACTG|CATACTTTTT|TTTTCCTTTT|173160|
|TATTAATTGT|GAGATAACCA|CAGCATAGGC|AATTTGTTTT|TTGTTTTTGT|TTTTGAGACA|173220|
|GGATTTTGCA|TTGTTGCCCA|GGCTGGAGTG|CAGTGGCATA|ATCATAGCTC|ACTGCGTCCC|173280|
|CAAACTTCTA|GGCTCAAGAG|ATCCTCCCAG|CTTAGCCACA|ACTGAGAGGT|GCTACTAGCA|173340|
|TTTAGTGAGT|AGAGAACAGA|TATGACTAGA|GGTTCATTAA|GTGTTTGAG|CCTTTACAGC|173400|
|TTCAAAATTG|TCTTTGCTAA|CCCCTAACTT|TTGGATGCTA|CAGAGGGCCC|CTGGAGTATC|173460|
|CAAAGGAGAG|GTAAACAGGA|TCATTGACA|CGTTTAGTTA|TATAGGATTG|TTGAAATAAG|173520|
|GTGATATTTG|ATCTTCAGGT|CATATTTCAG|TGAAAACTGT|GAATGTGTGT|TCCAAAATTA|173580|
|TAGGGGATTT|CTAGAGTTCT|GATATCTGAG|TTTGTGTCAT|CAGTTATAAT|TAGAGTTATT|173640|
|GTGTTAGGCT|ATTGTAAATC|ACAGAGGTGA|CTAAATTTCT|TTGTCAATTG|TGTTTTTGAC|173700|
|TGTGACTACC|CTAGGACATT|TTAACATTCA|TAGACAAATG|TTGTCTTGTT|TTGAAACTCT|173760|
|GCAAAGAATG|GATTATAACC|CTCAATTGCA|GGTTTCTGAT|AACTTTGAAG|ATTGTGAACA|173820|
|GGAGTTAACT|AGGTGAGCTG|AACTATTGGA|AAACTAATCT|TCTTGACTCT|TGCCTCTGTA|173880|
|CCTAATTCTT|CCTGGATGCA|GGACAAGAAC|TCAGGCAAAG|GTGCTGCAGC|ATAAAGTCTG|173940|
|GCCAGAGAAA|CTGACACTCC|AGAGGTTTTG|TAACAATATT|TTATGTTAAA|TAATTTATAC|174000|
|GTATTTCCTA|TTCTAAGCAT|TTCAAGTGAT|TGTAAAAACT|CAACTCATGA|AAACTTATAG|174060|
|CTGAGATGAT|GTATCCTGTG|ATTTTTAACT|CAACTTTATA|CCAATCTAAG|TTGATTAGCA|174120|
|TTCTTACAAA|GTTTAAGAAG|TTAAGATTTG|CCATATTAAG|TATTGTCTTA|AGATTTTAA|174180|
|GAATTGAAAA|ATTTGGAGCA|GTTTTGTTCA|TTAGTCAATT|GGATACTTTA|AAAGTCCAGT|174240|
|ATGTCAGATT|TAAAAATTGC|AATTTATAAG|TTTTCTTCTT|AAAGTTCGTC|AAATTGCAAA|174300|
|AGCCTTGCCA|AAAATGAATG|TTAAAAATTT|GGTAGATTAT|TTGTTCTATG|GGTTCTATGG|174360|
|GAAAAAATTG|GTAGATTAAT|AAATGCCAAT|AGTAAGCATT|GTAAATTGAA|TTTAAAGTT|174420|
|TAAGGAAGAG|CTATTAATTT|AATTTTGTCA|TAATAATGAA|TTGAATGTTG|TTTTTTAAGT|174480|
|ACCATAGTAC|TTGCTGAATG|ATCTTTCTGT|ATGGAAAAGG|ACATAAAAAT|GCACATTGGT|174540|
|AACATCAACT|CTATTTCAGC|GGCGGGATTG|TGGGGTGAGC|TTATCTCCAG|GTTTGGGAAG|174600|
|GATGTGTTGT|ATCATCTGCC|TCTTGTGTGT|GTACTACCTG|CCATTGCTGC|TTGGCCACCA|174660|
|GCATCCATCT|TGGTGAGTCC|TGTCTCCCTC|TAAAAGACTC|GAGCTGTGCT|GTTCAATCCA|174720|
|GTAGCCCCTA|GCTACATGTA|GCTATTGTAA|TGAATTAAAA|TTAAGTAAAA|TTAAACATTC|174780|
|TGCTCCTCAG|ACACCAGTCA|CATTTCAAGT|GCACAATAGT|CACAAGTGGC|CAGTAGCTAG|174840|
|TTTTGAACAG|TGTGGAAAGA|TTTCTGTCAT|CACAGAGCAT|TCTATTATCA|CGTTGTAAAG|174900|
|CATTCTCTAG|CTCTTGCAAA|CTTGTCAGAT|CCCTTAAAAG|TTCTTAAAAA|TAATTCATCA|174960|
|TTCGAATTTT|GCTCAGACTA|ATTTTAGGG|AAGTCTTTTT|CTGGAGGCGT|GGACTTGTGA|175020|
|TCTCCATAAT|TCATCCCTTC|TACTATGTTA|GTTACCTTGA|GCTGCTGTAA|TAAAATACTA|175080|
|TAGACTTAGT|CGCTAAAAAA|AAAATAACTT|TCTCACAGTT|CTGGAAGCTC|AGAAGTCCAA|175140|
|GATCCAGGTG|CTGGCCAATT|CAGTTTCTAG|GTGAACGCTC|TCTTCCTGAC|TTGTTGGTGG|175200|
|CAGCAGCATT|CTCACTATGT|GCTCATGTGG|TGTCCTTTTT|GTGCTTGTAG|GGCTTAGGCA|175260|
|GTGGAGAGAA|GGAGGAGAGA|AAAGAGTTTC|ACTGTTTTCT|CCTTTTCCCG|AGACAGTTTT|175320|
|TGTGTAGCCC|AGGTGGACAG|CAATGGCTCA|CTGCAGCTTC|TTCCTGGGGT|CAAGCAATCT|175380|
|TCCCACTTCA|GCTTCCAGAG|TAGCTGGAGC|TTCAGATGTG|TACCACCACA|CCCAGTTCAT|175440|
|TTTTTAAATT|TTTAGAAGTT|GGGGGTCTCA|CTATTTTGTC|CAAGCTGGTC|TTGAACTCCT|175500|

| | | | | | | |
|---|---|---|---|---|---|---|
| GGGCTAAAGC | GAGCCTCCTG | CTTCAGCCTC | TCATAGTGTT | GGAATTACAG | GCATCAGCTG | 175560 |
| CAGCACCTGG | CTCTATTGTC | TTTTTTTTTT | TTTTTTTGA | GATGGAGTCT | CTATCACCCA | 175620 |
| GGCTAGAGTA | CAGTGGTGTG | ATCTCACTGC | AACTTCCACC | TCCTGGTTTC | AAGGGATTCT | 175680 |
| CCTGCCTCAG | CCTCCCAGGT | AGCTGGGAGT | ACAAGCGTGC | ACCACCACAC | CTGGCCAATT | 175740 |
| TTTGTATTTT | TAGTAGACAT | GGGGTTTTAC | CATGTTGGCC | AGGCTGGTCT | CAAACTCCCA | 175800 |
| ACCTCAGGTG | ATCCATCCAC | CTCAGCCTCC | CAAAGTGCTG | GGATTACAGG | CATGAGCCAC | 175860 |
| TGCACCTGGC | CTGTTGTCTC | TTTTAATAAG | GGCATGAATT | TCATCATGAG | AGACACATCC | 175920 |
| TGATGAGTTT | GTCTAAATAT | AATGACTTCC | CAAACGCCCC | AGCTCCAAGT | ACCATCACAC | 175980 |
| TGGGGGTTAG | GGTTTCAACA | TATGAATTTT | GCGACGGGGA | GTCAATTCAG | TCCATAGTAC | 176040 |
| CTACTGTATT | AGTTTTCTGG | GGCTGCAGTA | ACAAAGTACC | TCAAACTCGT | TGGCTTAACA | 176100 |
| ACAGATATTT | ATCGTCACAC | AGTCCTGGAA | GCTGGAAGTC | TGAAATCAAA | GTATCATCAG | 176160 |
| GTTGATTCC | TTCTGAAGGC | AATGAGGGAT | AATCTGTTCC | AGGTTTCTCT | CCCAGCTTCT | 176220 |
| GGTATCCCCA | GACTCATTGC | TTGACTTGAA | TGGTGATTCT | CCCTGTGTCT | ACTCACCACA | 176280 |
| TTTTCTCTCT | ATAGGTGTCA | GTCTCTGTGT | ATGACATTTC | TCCTTTTTAT | AAGGACACCC | 176340 |
| TTTATGTTGG | GTTAGAGCCC | ACTCTTATCT | TAACTGATGA | AGTGCAAAGA | CCCTATTTCC | 176400 |
| AAATAAGGCC | ACATTCACAG | GTCCTGATAC | AGGAGGGGA | AAGTGCTGGG | AAGGGAAGGG | 176460 |
| CATGGTCCCT | TTAAATGATA | TGGAAGTGGG | GAAGGGAAGG | GCGTGGTCCC | CGGCTAGGGC | 176520 |
| TCCACCCCCA | GGCCTGTGCC | CAGGGACCAC | GGTGAGGACA | GGCATTTTG | TTTTCCTGCC | 176580 |
| CAAATGTTGC | ATTTCCCAAG | ACCTCCCCTG | GCCTGCCACA | AGACACGAAT | AGCTGGACGT | 176640 |
| CCAGGGGAGC | ACACTGGCAG | AAGAGCACAC | AACAAACGTT | TGCCTGGCAA | AATGAGGCGG | 176700 |
| AATTTGACTG | GGGTGGTTGG | AGGAGAGCCT | GGGCCACTGA | GTGGCTGACT | CCAAGGGAAA | 176760 |
| ACTTTCCCAC | TCCATCCACT | TTTGGCTTTG | CCCAACTGCT | GAGAGCTACC | TCCACTTAAT | 176820 |
| AAAACCTTGC | ACTCTTTCTC | TAAGCCCAGG | TGTGGTCTGA | TTTATTCCGG | TACACCAAGG | 176880 |
| CAAGAACCTG | GGATACAGAA | AGCCTTCTTC | TGTCCTTGGG | ACAAGGTAGA | CGGTCTAATT | 176940 |
| GAGTTGGTTA | ACACCAGCTG | CCTATAAATG | GCAAAACTAA | AAGAGCACCC | TGTAACACAC | 177000 |
| ACCCACTGTG | GCTTCAGGAG | CTGTAAACAT | TCAACCCTAG | ACACTGTGGT | GGGGTCATGG | 177060 |
| GGTTGGAGAC | CCACAACCTG | CCCGTCTTAA | TGTTCCCCTA | GAGGTTTGAG | CAGCCAGGCA | 177120 |
| CTGAAGAAAT | TAGCCACACT | CCTATCACAT | GCCATGCGAG | CGGGACAAGG | GAACTTTTCC | 177180 |
| CATTTCAGTA | CTGGTGGTTA | GGACTTCAAC | AACTTTATTT | TTGTGGGAAT | GCATACTTCA | 177240 |
| ACCCATATTA | TGAGGGTTCC | TAGAATGTGG | ACTGCTGAGG | CTGAAGCACT | ACCTAAGTGC | 177300 |
| CTGAGGCCAG | CCTGCAGTTG | GTTTCTGGCT | CTCATGAGTT | AGCTAACATC | TCGGGAGAGA | 177360 |
| GGAAGACAGG | CCTAGGAAGA | GCAGAGCCCA | CGATTCATTC | TTCATTCCAC | CTCTGCTCTT | 177420 |
| CAGAATCTCC | TTCAGTCTAT | GTGATGAGCC | ATCAGACCTC | TTGGTGGGAA | ATGGTGCTGC | 177480 |
| CGTGCCTAGC | CCTTTTCGAT | TGTGCTACCA | TGCTGAGATT | ACTGAGGGAC | CAGGAAGGCC | 177540 |
| TGGACTCAGA | CCATATAGGG | TGCCACCCTA | GTGGGAATGG | AACCTGTCAG | TGCTGGGTGA | 177600 |
| ATGTGACCGT | CCCATGAGGA | GAAGACAGAT | ACTCTTGCCA | AGCTGAGCAT | GGAGACCTGA | 177660 |
| TGGGACACTC | ATTATCATGA | GGGGATGAAG | ATCCAGGCTT | CCAAAGTTGG | TACCACAGGG | 177720 |
| TGGCTATGGC | ATGAACAGGG | GGTTAGGATG | AAGGACCCAG | AATCTAACAT | GCTGGAGAGG | 177780 |
| TAGGGAAAGG | AGTCAGAAAT | TCAGTCTTGT | TGAACCCTAA | ATATTGCATC | TCTCTCTCTC | 177840 |
| TTTATTTTTT | TTTTCTGGAG | ATGGGGGTCT | GGCTCTATCA | TCCAGGCTGG | GGTGTAGTGG | 177900 |

| | | | | | | |
|---|---|---|---|---|---|---|
| CATGATCTCT | GCTCACTGCA | GTCTCCGCCT | TCTGGGTTCA | AGAGATCCTC | CCACCTCAGC | 177960 |
| TTCCTGAGTA | GCTGGGACTA | CAGGTGCGCG | CCACCACTCC | CAGCTCATTT | TTGTACGTTT | 178020 |
| TTGTAGAGAC | ACGGTCTCAC | CATGTTGTCC | AGACTGGTCT | CGATCTCCTG | AGCTTAAGCG | 178080 |
| ATCTGTCGCC | TCGGCCTCCC | AAGAAGGATT | GGGATTACAG | GGCCTGAGCC | ACTGTGACCA | 178140 |
| GCCAACATTG | CATCTAATTT | TAGGGTATTC | ATCTGACTTT | CCTGAACACT | GCTTCTTGGG | 178200 |
| TGCTCATTTT | AGCAGGCATT | TGGCCATAGG | TAGATTTAAA | GTTTTGGTGG | GTTTTGTTGT | 178260 |
| TGTTGTTGAG | ACAAAGTGTC | ACTCTGTTGC | CCAGGCTGGA | GTGCAGTGGC | AAGATCTCAG | 178320 |
| CTAACTTCAA | CCTCCATCAC | TGTGCTTCAA | GTGAGTCTCC | TGCCTCAGGC | TCCCGAGTAG | 178380 |
| CTGGGATGAC | AGGTGTGTGC | CACCATGCCC | TGCTAATTTT | TTATATTTTT | AGTAGAGATG | 178440 |
| GGGTTTCGCC | ATGTTGGCCA | GGCTGGTCTG | GAACTTCTGA | CCTCAGATGA | TCTGCCCGCC | 178500 |
| TCAGCCTCCC | AAAGTGCTGG | GATTACAGGT | GTGAGCCACA | ACCCTGGCC | AACGTTTCT | 178560 |
| GAAAAGCTA | TTCTAATCAG | GTAGGAAAGA | TGGGAAGCGG | GGTGGCGGGG | TGTACTTTTT | 178620 |
| TCTGCATATT | CAGTTGCAGG | GTCCCAGACC | AGGGAACAAT | CTTCAATCTC | TTACCTTCAA | 178680 |
| TCTCCCTTCA | TGGAAGTCAG | TGCTCAGCCT | GGCCATTTAC | TGTGTGCAGT | AGGTGTGATG | 178740 |
| TAGAAAGCCT | CTAAACCTCC | ATGCCTACCT | GCCAGGAACA | ATATACACAA | AGGTGTGTGT | 178800 |
| GTGTGTGTGT | GTGTGTGTGT | ATCTTACGGA | TTCTTCCACG | TAACTATGTG | GACATCTAAT | 178860 |
| CCATTGCTTC | CAACTCTATA | TTGTGCAGTG | ACTTCATTTT | ACCTCCACCT | CTCTCAGTGA | 178920 |
| AGGATATCAG | TCAGCCCACA | CTTTCCTGTC | ACCTTTATGG | GATATGTTTG | AGATGATATT | 178980 |
| TGGAAAATAT | TCCCAGGGAG | TGGGCACTCC | CATCAGCAGT | GTATGAGGAT | TCCTGAGTCT | 179040 |
| CCATATCCAC | ACCAATACTG | AGCATTATTC | AGCTCTCTAA | TTTGTTAATG | CTCTCTTTTA | 179100 |
| AATGCAAAAG | GACACATCAC | TTTACCTTTC | TTTCATTACC | AAGTGCTTTG | GATTTTCCTG | 179160 |
| TATCTAAATT | TCTTGTTCAT | TTATTTCATA | TATATATATA | TATATATATA | TATATATATA | 179220 |
| TATATATATA | ATTTTTTTTT | TTTTGAGAC | AGAGTCTCAC | ACTGTCACCC | AGGCTGGAGT | 179280 |
| GCAATGGTGT | GATCTCAGCT | CACTGCAACC | TCTGCCTCCT | GAGTTTAAGT | GATTCTCCTG | 179340 |
| CCTCAGCCTC | CCAAGTAGCT | GGGATTATAG | GCACCCACCA | CCACGCCCGG | CTAATTTTTT | 179400 |
| GTATTTTTG | TAGAGATGGG | GTTTCACAAT | GTTGGCCAGC | CTGGTCTCAA | ACTCCTGATC | 179460 |
| GGCCCGCCCT | GGCCTCCCAA | AGCGCTGGGA | TTACTGGCAT | GAGCCACCGC | GCCCGGCCTC | 179520 |
| ATACATTTTT | TATGTGGAGT | TTCTGTTTTG | TTCTTCTTGG | CCTTGTGCAT | TCTAATTACT | 179580 |
| CATCCTTTCG | TCTGATTCAG | ACATTTAATT | CTCTACCATC | CTTACAGCAG | TGTCTTAACT | 179640 |
| TTATCCATGG | GATCCTTCAT | TGAACCGGAA | TTCTTAATTT | TGACACAAAC | AAATTTATCA | 179700 |
| ATTTCTTTTT | TGTGTGTGTT | TTTTTTTCT | GTGTGTGGTT | TTTGTTTTTC | ACATTTCTGA | 179760 |
| GTATGACCTA | GATTTATCCT | TTGATAACTT | CTTCTCTCTT | CCCCATTTTC | CTCCACTGGA | 179820 |
| GGTCAGCTAT | ATGTGTGTGA | GAGGGTTAGG | TATATGTGGA | TATATAGAGA | AAGTTTAGGT | 179880 |
| ATACATATGT | GGAGAGGTCA | GATAAATATG | TATATATGGG | AGAGATATTG | GGTATATATT | 179940 |
| TTGGGGAGGG | GAGGTCAGGT | ATATGTGGAC | ATATGGGGAG | GGGAGACCAC | AGCTCTCCTG | 180000 |
| GAGTCACCCT | CTTCCTCTTC | CCTTCTGGGC | AGGTAACGGT | GGGGAGTGAG | AGGGTGTTCC | 180060 |
| TCCCTTCTTA | TTATTAGCCC | CTGGGTACTT | TAGGGTCTCT | AGTGGTTATT | TTTCACAGAA | 180120 |
| TTTTAACTGA | TAACTAATGA | ACAAATGTTT | TCCCCACAGA | AATATCTTTA | CGCCTTTTAC | 180180 |
| AATCATTTTT | ATTTTCTATG | CCATAACTTT | ATTAATATTT | GCCAATTTAC | TTGGGGTAGG | 180240 |
| ACTTTGAAAA | TTTTGTTTAA | ATTAAGGGAG | GAGACCACCC | CTCATATTGT | CTTATGCCCA | 180300 |

| | | | | | | |
|---|---|---|---|---|---|---|
| ATTTCTGCCT | CCAAAGAAAG | AAAAAGTAAA | AATTAAAAGG | GAGAAATGAA | ATCCACAGGC | 180360 |
| AAACAGCCCG | GCACCGCACC | CTGGGTCTGG | TTAAAGATCG | ACCTTTGACC | TAACAGGTTA | 180420 |
| TGTTATCTAT | AGATTCCAGA | CATTGTATGG | AAAAGCATTG | TGAAAATCCC | TGTGCTGTTC | 180480 |
| TGTTCTGTTC | TGATTACTGA | TGCATGCAGC | CCCAGTCACG | TACCCGCTGC | TTGCTCAATC | 180540 |
| AATCACGACC | CTCTCATGCA | GACCCCCTTA | GAGTTGTAAG | CCCTTAAAAG | GACAGGAAT | 180600 |
| TGCTCACTCA | GGGAGCTGGT | TTTTGGAGAC | AGAGGTGATT | AACGGACGGT | CAAGGCAGCC | 180660 |
| CCTTAGGCGA | CTTAGGCCTG | CCCTGTGGAG | CATCCCTACG | GGGAACTCCA | GCCAGTTTGA | 180720 |
| GCGACACAGA | TCTGGAGAGC | GCTCCCAGGT | AGGCAATTGC | CCCGGTGGAA | CGCCTCACCA | 180780 |
| GAGCAGCACG | TGGCAGGCCC | TCGTGGAGGA | TCAACGCAGT | GGCTGAACAC | CGGGAAGGAA | 180840 |
| CTGGCACTTT | GTTGTCAGGG | CATATTCCAA | AAGCATTAAG | GCCTTCCTAT | CAAAAATCCT | 180900 |
| TAACCCAGTA | ACCCGCGGAT | GGCCCAAATG | CATTCAATCT | GTAGCGGCAA | CTGCTTTGCT | 180960 |
| AACAGAAGAA | AGTAAAAAAA | TAACTTTTAC | AGGAAACCTC | ATTGTGAGCA | CACCTCACCG | 181020 |
| GTTCAGAAGT | ATCCTAAGGA | AAAAGAAAA | AAGAAGATGA | TTTAACATTA | ACCACTGAAA | 181080 |
| ATTCTCTTAA | CCCGGCAGGT | TTCCTAACAG | GGGATCTAAA | TCTTAATTAC | CATACAAAGC | 181140 |
| TCTGACCAGA | CCTAGGGGAT | TCCCTTCAGG | ACAGGAGGAT | AGATGGTTCT | TCCCAGGTAA | 181200 |
| TTAAAAAAAA | AAAAAGCCA | TCTATACCAA | TTCTAAGTTA | ATTTGGACTA | AATAAGGTCT | 181260 |
| TATTAATAGC | AAAGGATAAT | TGAAATCCCA | AACTTACAAG | GTTTTCAACA | AAAGTAAAGT | 181320 |
| TTGCTAAAAG | TTAACAGTGT | AACATGTATT | ATAGTAACTT | CTAATCTTGT | GGCCTTAGAC | 181380 |
| AGTCTAGTCC | ACAGACATAA | AAGAAGTTCG | CTTTGGAAAA | GAATGGTTAT | CATCCTCGGA | 181440 |
| AAAAAAAAA | AGGAAATAAA | GAGGAGGCAG | AATTTATATA | AAAAGAATG | TTGTATGGAA | 181500 |
| AATCCTTGTC | CTGAGATAAA | TTAACTAGTT | GTTAAAGAA | AGGGATGTTT | GCAATAAGTC | 181560 |
| AGAAAGTTGA | GGCATGTCGA | AGAATTGTCT | GTGAAAGTCA | TGAAAAAAAT | GTGTGTTAGA | 181620 |
| AAAATAAATT | TATGTAAGAA | ATGTTGTATA | ATTTAAAAGT | AATTAGGCCT | CCTTCTAAAT | 181680 |
| GTAAAACTAT | TGAATAAACA | GTTTATGTGC | AAGGTATGTA | AGGAAAGTAA | AATATACCTT | 181740 |
| TGGTAAAAGG | ATTATGAGGA | TGCATAAGAA | TGTGGATTTT | TACCTACATT | AAAAGGTTAC | 181800 |
| AAAAATTGTT | TTGAAGGTTT | AAGCAAGTTT | TGAAACCTTA | ATTGTAAAGA | AATTCTGTG | 181860 |
| TCTAAACATA | TTGGCTAAAG | TTAAGGGGTA | TCATACAGTT | TTTCTGTGAA | CTGAACATTA | 181920 |
| AAATAAAAAC | ACAACGGGTT | TTTCTTAAAG | CACTAACCTG | TTCTTTAACA | AAAATTATAA | 181980 |
| AAGGTTAAAG | AAAAGTCTAT | AAAAATCTTA | CCTTATGGTC | AGACATTAAA | AATCAAATAA | 182040 |
| ATATGTCTAC | AGAGTTTTAT | TAAAACTAAG | TTTAACATTA | ATAACACACC | AATATAAAGG | 182100 |
| TGAAATCTAG | CTTATCTGGT | ATAAACATAC | AAGAAGCGTT | GTCAAATATA | AAATGGCATT | 182160 |
| TGACTTTCTT | TGGTCTAAAA | ACTAATAAAA | ATAGGTGCTA | AAGGAAATTT | CTCAGTAAGA | 182220 |
| AGGCACCAAG | GACTATAAAG | TCCACTGCTG | ATGTCCCAC | ATTTAAAACA | AAAGGTCAAC | 182280 |
| TTCTTAAAAG | TTATATACTT | GGTTTATCTT | CCACTTTCCT | TTCCCTCAAA | ACTAAAGTC | 182340 |
| TTTTAGCACA | TGTACCACCC | CTAGAATTTT | CTGTAAACCA | GCACCAGCCT | GAAGATCATG | 182400 |
| TTCTCATCAA | AGGGTGGAAA | GAAGGAAAAC | TTGAGCCAGC | CTAGGAAGGA | CCCTACCTTG | 182460 |
| TGCTGCTAAC | CACCGAGACT | GTTGTTCATA | CGGTGAAAAA | GGGATGGACT | CATCACACCC | 182520 |
| GAGTCAAGAA | AGTGCCACCC | CCTCCAGAGT | CATGGGCCAT | AGTCCCAGGG | GAAAACCCTA | 182580 |
| CCAAACTAAA | GCTAAGAAAA | ATTTAACTCC | TTCATCTATT | CTATTACTCT | TTCTTCTTCC | 182640 |
| CTCACTCTAT | TTCTGACCAT | CTAGTTATTA | ACATAACCAA | GTCAATTTTG | CCTCAAACTA | 182700 |

-continued

| | | | | | |
|---|---|---|---|---|---|
| TTGAATTTAA | TGCTTGCCTT | GTTATACCCT | GTGGGGACTT | GCCAAGTCGA | AGACATCTCT 182760 |
| GTACTTCAGA | AAAGTACCTC | TGTCCCTCCT | GACTCTCCTC | AGACTGAGCC | TTAGTAAACT 182820 |
| GAGACCATTT | ATTCCAGAGA | GATTTCAATA | AAGACCCCAG | TGTCAACGAG | GAGTCTTGCC 182880 |
| CCCCGATGTA | GAGCTTTTAT | GCCATAGTTG | GTCGAATGTT | GTGTGGACCA | CTAAAGAGCA 182940 |
| AGGATGGACT | GCCCCAACCG | GTTTTTGTAA | TTTCCTAAAA | TCATACATTC | ATTTTACTAG 183000 |
| AGGGTCATAG | AAGTTAAAGA | CTTAAAACAA | ACTTTGATAA | TTAAGCAGGA | TACCAAGATG 183060 |
| CAAATGCCCA | GTTGGAATGG | ATCAAATATT | CTGTCCACAC | ATTAAACAAA | ACCAATTGTT 183120 |
| ATGCTTGTGC | ACATGGCAGG | CCAGAGGGCC | AGATTATCCC | CTTTCCACTA | AGGTGGTCCT 183180 |
| CCTGTTGACC | AGGCATGGGC | TGCATGGTAA | CTGTTTTCCA | GGATTCTACA | GCCTGGAGTA 183240 |
| ATAAGTCGTG | CCAAGCTCTC | TCTGCTATAT | CCCAAAGTCC | AGCACCCTGC | AGGTCAACCC 183300 |
| CTGAGGGCCA | TCCAGCTTCC | ATCTCCCAAA | ACTAAGTTCA | CTTCTTGTCT | CTCATGACAG 183360 |
| GGAGGAAACT | TAGCATTCCT | TGGAGACCTG | AAGGGATGCA | GTGAGCTTAA | GAATTTTCAG 183420 |
| GAGCTTCTCA | ATCAGTCAGC | CTTTGTTCAT | CCCCAAGCGG | ATGTGTGGTG | GTATTGTGGT 183480 |
| GGACCTTTAC | TGGGCACTCT | GCCAAATAAC | TGGAGCGGCA | CTTGTACTTT | AGTCCAATTG 183540 |
| GCTATCCCTT | TCACCCTAGC | ATTTCATCAA | CCAGAGGGAG | GAAAAATAAG | ACATCGTAAA 183600 |
| GCAAGAGAAG | ACCCTTATGT | GTCTTTCAAC | TCTCACATCT | ATTTAGATGC | AATTGGAGTC 183660 |
| CCACAGGGAA | TAGCAGATCA | ATTTAAATCC | CAAAATCAAA | TAGCTGCAGG | ATTTGAGTCA 183720 |
| ATATTTGGT | GGGTGACAGT | TAATAAAAAT | GTAGATTGGA | TAAACTACAT | CTATTACAAC 183780 |
| CAACAGCAAT | GAGTTTTTCA | TGAGTTAAAA | GAAAAACTCA | TGTCGGCCCC | AGCCCTGGGG 183840 |
| CTACCTGACC | TGACAAAACC | CTTTACACTC | TATGTGTCAG | AAAGAGAAAA | AATGGCGGTT 183900 |
| GGAGTTTTGA | CCCAGACTGT | GGGGCCCTGG | CCGAGGCTGG | GCCTCCAAAC | AACTAGATGG 183960 |
| AGTTTCTAAG | GGTTGGCCTC | CATGCTTAAG | AGCCTTGGCA | GCAACAGCCC | TGCTAGCACA 184020 |
| AGAGGCAGAT | AAGCTAACTC | TTGGACAAAA | CCTAAACTTA | AAGGCCCTCC | ATGCTGTGGT 184080 |
| GACTTTAATA | AATACATCAT | TGGCTAACAA | ATGCTAGATT | AACCAAGTAC | CAAAGTTTGC 184140 |
| TATGTGAAAA | TCCCTGCATA | ACCATTGAAA | TTTGCAACAC | CCTAAAACCT | GCCACCTTGC 184200 |
| TCCTGGTATC | AGAAAGCCCA | GTTGAAAGTG | ACTGAGTAGA | GGTATTGGAC | TCAGTTAATT 184260 |
| CTAGTGGGCC | CAACTTCCAA | GACCATCCTT | GAACATCAGT | AGACTGTGAG | CTGTACGTGG 184320 |
| CAGCTTCGCC | AACGCCTGCA | AAGTGACTGA | AGAAGACAAC | AAGCCCTGCT | CCAGTCACAC 184380 |
| CCGGAAGCTG | ACTGGTCCAT | GCATGGCCGA | AACATGAGAA | AACTCATCAA | GGGACTCATT 184440 |
| TTCCTTAAAA | TTTGGACTTG | CACAGTAAAG | ACTTCAACTA | ACCTTCCTCA | GACTGAGGGC 184500 |
| TGTTCCCAGT | GTATACATCA | AGTCACTGAG | GTAGGACAAA | AAGTTGCTAC | AGTCTTATTA 184560 |
| TTTTATGGTT | ATTATAAGTG | TACAAAGACT | CTAAAAATAA | CTTGTTTGTA | TAATGCTATT 184620 |
| CTATACAAGG | TAGGTAGCCC | AAGAAATGAC | CAACCTGATG | TGTGTTATGA | CCCATCTGAG 184680 |
| CCTCCCACGA | CCACAGTTTT | TGAAATAAGA | TTGAGGACTG | AGGACTGGTG | GGGGTTCATA 184740 |
| AACGATACGA | GTAAAGTGTT | AGCCAAAACA | GAAGAAAAG | GAATGCCCAA | ACAAGTCACC 184800 |
| TTGAAATTTG | ATGCCTGTGC | TGTCATTAAT | AGTAATAAGT | TAGAAATAGG | ATGTGGTTCT 184860 |
| GTTCATTAGG | AAAGAGGCTA | TATGGCAGAA | AATAAGTACG | CTTGTCATGA | ATTAAGACTG 184920 |
| CGTGGAAATA | AATGTAGATA | CTGGTCTTGT | GTCATTTAGG | CAACTTGGTT | AAAAAATAAA 184980 |
| AAGAATCCTG | TCCACCTTCA | GAAAGGGAAA | AGTGGCCCTT | CCTGTACCAG | TGGTCAGTGT 185040 |
| AACCCCTTAG | AACTAGTAAT | AACCAACCCC | CTTGATTCTC | ACTGGAAAAA | AGGGGATCGT 185100 |

| | | | | | | |
|---|---|---|---|---|---|---|
| GTAACCTTAG | AAATAGTTGG | GGCTGGACTG | GATCCTTGAG | TAAATATGGT | GGTTTGAGGA | 185160 |
| GAAGTTTATA | AATGCTCCCC | TGAGCCAGTA | TTTCAAACCT | TCTTATGATG | AACTGAATGT | 185220 |
| GCCAGTACTA | GAAATTCCAG | GAAAAACAAG | AAATTTGTTT | TTGCAATTAG | CTGAGCATGT | 185280 |
| AGCCCAGTCT | CTCAATGTCA | CTTCATGTTA | TGTATGTATG | TGGAGGAACT | GTAATGGGAG | 185340 |
| ATCAATGGCC | ATGGGAAGCA | CGAGAATTAG | TACCTACAGA | CCCAGTTCCT | GATAAATTCC | 185400 |
| CAGCTCAAAA | GACTCACCCT | GATAACTTCT | GGGTCCTAAA | AGCCTCAATC | ATTAGACAAT | 185460 |
| ACTGTATAGC | AAAAGTGGGG | AAGGACTTCA | CCCTTCCTGT | GGGAAGACTC | AGCTGCCTTG | 185520 |
| GGCAAAAACT | GTATAATAGT | ACTATAAAAA | CAGCCACCTA | GTGGAGTTCA | AACCACACTA | 185580 |
| AGAAAAATCT | ATTTAGTAAA | TTCCCAAAGT | TGCAAACTGT | GTGGACCCAC | CCAGAGTCCC | 185640 |
| ACCGGGACTG | GACAGCCCCC | ACTGGATTAT | ACTGGATATG | TGGGCATACA | GCTTATGCCA | 185700 |
| AATTACCTGA | CCAGTGGGCA | GGTAGTTGTG | TTATTGACAC | TACTAAACCA | TCTTTCTTCC | 185760 |
| TACTGCCCAT | AAAGACAGGC | AAACTCCTGG | GCTTCCCCTG | TATATGCTTC | CCGCAAAAAA | 185820 |
| AAAAAAAAAA | AAAAAAAAAA | AAAAAAAAAA | AGCATAGCTA | TAGAAAATTG | GAAAAATAAT | 185880 |
| GAATGGCCCC | CTGAGAGAAT | CATACAATAT | TATGGGCCTG | CTACTTGGGC | ACAAGACGGC | 185940 |
| TTGTGGGGAT | ATGGGACCCC | CATTTACATG | CTCAACTGAA | TCATACGGTT | ACAAGCTGTC | 186000 |
| TTAGAAATAA | TTACTAATAA | GACCAGCAGA | GCCCTGACTA | CTGTGGCCTG | GCAAGAAACT | 186060 |
| CAGATGCAAA | ATGCTATCTA | TCCAAAATGG | ATTGGCTCTC | GACTACTTGC | TAGCAACTGA | 186120 |
| AGGAGGGGTC | TGTAGGAAAT | TTAACCTTAC | TAATTGCTGT | CTACACATAG | ATGATTAAGG | 186180 |
| GCAAGTAGTT | GAAGACATAG | TTAGAAATAT | GACAAAGTG | GCACATGTGC | CCATGTAGGT | 186240 |
| GTGGTATGGA | TTTGTTTCTG | GGGCCATGTT | TGAAAAATGG | TTCCGAGTGC | TAAGAAGATT | 186300 |
| TAAAACTCTT | ATAATAGGAG | TTATAATATT | AATAGAAACC | TGCTTACTGC | TTCCTTGTTT | 186360 |
| GCTACCTGTA | CTTCTCCAAA | TGATAAAAAG | CTTCATCACT | ACCTTAGCTC | ACCAAAATGC | 186420 |
| TTCAGCACAA | GTGTACTATA | TGAATCATTA | TCAATCTGTC | TTTCAAGAAG | ACATAGGTAG | 186480 |
| TGAGAATAAA | AGTGAGAACT | CCCACTAATG | AGTGAGATTC | TCAAAGGGGG | TGAATAAGTG | 186540 |
| AGGCGACCAC | CCCTCATATT | GTCTTATGCC | CAATTTCTGC | CTCCAAAGAA | AGAAAAAGTA | 186600 |
| AAAGCTAAAA | GGCAGAAATG | AAATCCACAG | GCAGACAGCC | TGGTGTTGCA | CCCTGGGTCT | 186660 |
| GGTTAAAGAT | TGACCCCCGA | CCTAACCGGT | TATGTTATCT | ATAGATTCCA | GACATTGTGT | 186720 |
| GGAAAAACAC | TGTGAAAATC | CCTGTTCTGT | TCTGATTACT | GGTGCATGCA | GCTGCCAGTC | 186780 |
| ACATACCCCC | ACTTGCTCAG | TCGATCATGA | CCCTCTCACA | CAGACCCCCT | TAGAGTTGCA | 186840 |
| AGCCCTTAAA | AGGGACAGGA | ATTGCTCACT | CAGGGAGCTC | GGTTTTTGGA | GATGTGAGTC | 186900 |
| TTGCCAAAGC | TCCCAGCTGA | ATAAAGCCCT | TCCTTCTTTA | ACTCAGTGTC | TGAGGGGTTT | 186960 |
| TGTCTGTAGC | TTGTCCTGCT | ACAAAATAA | GTGTTAAACA | TGAGTTTTAT | ATTACCTCAT | 187020 |
| AGGTGGAAGA | AGACAGGCCA | AAAAAGCTGT | TTTAACAACA | ACAAAATGCA | CAAATATTTA | 187080 |
| TACTAACAAG | ACAGATATCC | ATTGCAGTAT | GACACGAGAA | ACAAATAAAT | GAGACAAGCA | 187140 |
| GTCAATTCAG | ACATTTTAGG | AAGTGATTTT | TACAGAACAT | AGTGACAATT | GCTGAGATCT | 187200 |
| GGTAGCCTTG | CAAGATTCCT | TTGTTATAAT | AAAAATAACA | TTGGCAAAGA | CCATTTTATG | 187260 |
| ATGCAGACTT | CTGCTTTTTT | AAAGTTTGGG | GGGAAGGGGA | AACATTTTTA | TTCTATAATG | 187320 |
| CTGAAATTTC | ATTTTTCTTT | TCTCTTTTTT | AAGACCAAGT | CTTGCTCTCT | CACCAAGGCT | 187380 |
| AGAGTGCAGT | GGCGTGATCT | CAGTTCACTG | CAACCTCCAC | CTCCGGGTT | CAAGCAATTC | 187440 |
| TCCTGCCTCA | GCCTCCTGAG | TAGCTGGGAC | TACAGGCACC | ATGCCCGGCT | AGGATAACAT | 187500 |

```
TTTTTGTTTT  TAGTAGAGAT  GGGGTTTCAC  CATGTTGGCC  AGAGTAGTCT  AGAACTCCTG  187560
ACCTCAAGTG  ATCTGCCCGC  CTCATCCTCC  CGAAGTGCTG  AGATTACAGG  TGTGAGGTAC  187620
AGCATCTGGC  CTCATGCTGA  GATTTCTTTC  ATTACCAGTT  CAAACACCTT  TCACTTTTCA  187680
AGGCACAAGG  AGAGGAATTC  CATGTGTTGA  CACTGGGAGG  AAGGGTACAG  ACCTACTTAA  187740
AAGATTCAAA  ACTTCTATGA  CAGTAAAAGA  AATGTATATC  AAGTTCCTTA  GGGCTGCCGT  187800
AACAAAGTAC  TATCAACTGG  GTGGCTTAGA  ACAAAGAAA   TTTATTCTCT  CACAGTTACG  187860
TAGGCCAGTT  GAGATCAAGG  TATTATCAGG  GCCAAGATCC  CTCTGTAGCC  TCTGGGGAAG  187920
GATTCTTTCT  TGCCTGTTTC  CACTTCTAGC  AGCTTCCTGT  GTTTGGTTTG  TGGCAGCATA  187980
ACTCCAATCT  CTGCCTCCAT  CTCTACCTGG  CCATCATCCC  TCTGTGTCTG  TGAGGACCCC  188040
AGTCATTGGT  TGGAGGACTC  ACCCTATTCC  ACTATAATCT  CTTCTTAACC  AGTGAACTCA  188100
CCGTATTCCA  GATAAGGTCA  GGTTCACAGC  TACTGAGGGT  TAGGACAGAG  TATCTTTTGG  188160
GGAGATGCAA  TTCATCCCAT  AAGTGGGTGG  AAAAGGATGA  TTAACAAGTG  GTATGTGGGG  188220
ATGTATTGTT  TTGCATCTAC  GTAGCTCTCA  CCCCATTTCT  TTCCACAACA  CACATTTGTC  188280
ACTCTATTCT  TTATTAGGTT  TACAGAGAAA  AGTAGATCTT  CAACCACTTT  CCTGGGATGT  188340
GGATACAGCT  CTTTTTTTGG  AGACAGGGTC  TCATTCTGTC  ACCTAGACTG  GTGTGCAGTA  188400
GCACTATCAT  GGCTGACTAC  AGCCTCAATG  TCCCAGGCTT  AAGTGATCTT  CCCAACCTCC  188460
TGAGTGGCTG  GGACCACAAG  TGTGTGCCAC  CACACCTGAC  TAATTTTATT  TTTTAATTGT  188520
TTTGTGAAGA  CAGCATCTCC  CTATGTTTCC  CAGGCTGGTC  TTGAATTCCT  GGGCTCAAGC  188580
CATCCTCCTG  CCTCGGCCTC  CCAAAGTGCT  GGGATTACAG  GCAAGAGCCT  CCATGCCTGG  188640
CCTTCAACTC  TTGACCTTAT  GAACACAGCC  CTATACCAGT  TCCCTTCATG  CATGTGCCTA  188700
TAAGCTAAAC  CCTTCCCAAG  TGTACATGAA  AATCTGAAAC  CCCAACAAAT  ATGGCCTAAT  188760
TCTAAATCTG  ACTTTCCCAG  GAGTAATTTT  TGTCATTTCC  AGCTTACCAG  CCTTTGTGAG  188820
TGTTGAATTT  CAGCATTTCT  GTTTGCTTGC  AGCAGAAGGT  GGAGCCAGGA  TAGGGTGGCT  188880
CAAGATTAGA  GTTTCTTCCT  TAACAGTTCA  GTCAACTTTT  TAATCTTGGA  TTTATAGCTT  188940
CCTACCTGCT  CTCTTAAAGG  TGAAATGATC  TATTCACCTT  CAGACCATTT  GCCCTCGGGG  189000
TCTCACTGAG  CAATCTATGG  CTTAAGTCTT  CTAAGTCTCT  TAATGGCCAA  ATACAATGGA  189060
CAATTTTCAG  GTATATCTGA  CACCATTTCT  CTGCAGCCTT  TGGCACCTAT  AACCACTCCA  189120
TGGCTTCCAC  AATGTGATTG  GTCATTTCTT  TTTTGTTTAT  ATGACAAGTT  TTTATTCTTC  189180
TTCTGCCTGT  TAAATGCGCC  TGACCCCAG   TGTTCTGATT  TTCACTATTT  TTCTTAAAAA  189240
AAAAAGTTTA  AATGAAAAAA  GTTTCTTATG  AAAATATTAA  AACATATACA  AAAATAGAAT  189300
AGACATTGAT  AATAGATCCT  AAAATTCCTA  GGGAAATTCA  GCAGACTGAG  AATAGCTAAT  189360
ATAGTCTTCC  AAAAAAAGAT  CAAATTTGAA  GTTGAGAAAC  TTCTTGAATT  CAATTTACTA  189420
AAAAGCTATA  GTAATCAAGA  CAGTGTAGTC  CTGACATAAA  GATAGGATTA  TAGTCTGGGT  189480
GTGGTGGCTC  ATGCCTGTAA  TCCCAGCACT  TTGGGAGGCT  GAGGTGGGCA  GATCACCTGA  189540
GGTCAGGAGT  TCCAGACCAG  CCTGACCAAC  ATGGTGAAAC  CCCGTCTCTA  CTAAAAATAC  189600
AAAAATTAAC  CAGGCATGGT  GGCAGGTACC  TGTAATCCCA  GCTGCTTGGG  AGGCTGAGGC  189660
AGGAGAATTG  CTTGAACCTG  GGAGGAGGAG  CCAGTGGCCG  GGATTGGGCC  ACTGCACTCC  189720
AACCTGGGCA  ATAGAGTGAG  GCTCTGTCAA  AAAAAAAAA   AGATAGGATT  ATAGATTATA  189780
GCATAATGGG  ATAAAATTGA  GACTCCAGAA  ATAAACTCTC  ACATTTATGG  TAGATTGATT  189840
TTTGATAAGG  GTGCCAAAAC  ACTTCAATGA  AAAAGAGTC   TTCTCAACAA  GTGATGGTGG  189900
```

| | | | | | | |
|---|---|---|---|---|---|---|
|AACAACTGAA|TAACCACATT|TTTGTTCTAT|CTGGGGCCCT|GATTCAAAAA|CCCAGGCAAA|189960|
|GATGGAGAGA|AATCAGAACT|CTCATACACT|GCTGATAGGA|GGATAAAATG|CTTACTTTGG|190020|
|AAAAGAATGT|GGCAATTCCT|CAAAAGGTTA|AACAGTGTTA|CCATATGACC|CAGCAAACCC|190080|
|ACTTCTAGAT|ATATAACCAA|AAGAAATCAA|AACATAAGTC|TACAAAAAAA|CTTGTACATA|190140|
|AATGTTTATA|ACAGCACTAT|TCCCAATAGC|CATAAAGTAG|AAACAAACCA|ATGTCCATCG|190200|
|GCTGATGAAT|GAATAAATAA|AATATGTTGT|GGTATGTCCT|TATAATAGAT|ATTATTGGTC|190260|
|CATGAAAAAC|ATACATAAAA|ACATTATGCT|AAATGAAAGA|AGCCAGTCAC|GGCAAAGCAA|190320|
|TATATTATAT|GCCTCTATGT|ATACTAAATG|TTCCAAATAG|AAAGAAAGTA|GATTAAAGAT|190380|
|TGTCTAGGGC|TGGGAGGGGA|GGAGGAGGAG|AATGGAGGAA|TCTGGGAGGC|GATGAATTAA|190440|
|GGGTACTGAA|TTAGGGGAAC|ATGGTTTCTT|TTTGGGGAGA|TAGAAATGTA|AAATTTTGGT|190500|
|AATGGTTGCA|CATCTCTGTA|AATATACTAA|AATCCATTAA|TTTTTGCATT|TTATTTTATT|190560|
|TATTTTATTT|TTGAGACGGA|GTTTCGCTCT|TGTTGCCCAG|GCTGGAGTGC|AATGGCATGA|190620|
|TCTCGGCTCA|CCACAACCTC|CGCCTCCCAG|GTTCAAGCGA|TTCTCCTGTC|TCAGCTTCCC|190680|
|GAGTAGCTGG|AATTACAGGT|GCATGCCACC|ACACCCAGCT|AATTTTTTTT|TTTGAGATG|190740|
|AAGTCTTGCT|CTTGTCTCCC|ATGCTGGAGT|GTGATGGCAC|GATCTTAGCT|CACTGCAACC|190800|
|TACGCCTCCC|GGGTTCAAGC|GATTCTCCTG|CCTCAGCCTC|TAATGTAGCT|GGGATTACAG|190860|
|TTGCCTGCTA|TCACGCCCGG|CTAATTTTTG|TATTTTTAGT|AAAGACGGGG|TTTCACCATG|190920|
|TTGGCCAGGC|TGGTCTCGAA|CCCCTGATCT|CAGGTGATCT|GCCTTCCTCG|GCCGCCCAAA|190980|
|GTGCTGGGAT|TACAAGCGTG|AGCCACTGAG|CCGGGCCAAT|TTTTGCATTT|TACATAGATG|191040|
|AATTATATGG|TATGCTAATT|ATATCTTACC|AAAAATTGAA|AAAAGGAAT|AGTACTATCA|191100|
|GCCCCAATGT|GCCCATCATC|AATATTCTAC|ATGTTTCCAA|TGTTATTGTA|TCTGTTTGCC|191160|
|TACAGTCGAG|GCCCTGATAT|CCTGTTTGAT|TTTCTTGAAT|TGCCAAAATT|TGCATACATG|191220|
|CTTACAAAAA|TAATGCCTGT|TGAATTTGCT|AGATATGTAA|AGGTTTGGAG|CAAATCAGGT|191280|
|GTATTAAATT|TATTAATATT|GTTTGAAATG|TCTAAGGCAA|TAATTCCCAA|ACTTCGTTGA|191340|
|GGGAGAAGGA|AAGCTTTTAA|AATCCCATTG|CCCAGGTGGC|ATCCATACT|GTTACTGGGA|191400|
|ATTATGCATT|GGGATGGATC|CTTTAACCGA|GGAGATTATT|ATAGCCGGAG|CTCTGAACCA|191460|
|GCAATCTCAG|TTCTTGTGAT|AGTGAGCAAA|GAACTACAAA|CTAACACCAA|AATGCAAGCT|191520|
|TAAAGCAAAG|TTTATTGAAG|CACAATAATA|CACTCTGAGG|GACAGCGGGC|TTATTCTGC|191580|
|GAAGTGAACT|CAGCACTTCT|TTACAGAGCT|CAAGGTGCTT|TTATGGGGTT|TGTGGGGAGG|191640|
|AGTTGAGGTT|TGGGCTGTAT|CTGAGTGACA|GGATGATGTT|ATTTGATTGA|AGTGTATAGC|191700|
|TATACAATCT|AAAATTAAAC|TGTGCATGGT|CTTACCTATA|ATTTGTTAAG|AAAAGCCTCC|191760|
|CAGGGATGGG|GGGGCAAAAC|TGTATGTAAA|TTCTATTATA|ATGATGGCAT|GATGAACTTG|191820|
|GGGTGAACTT|GAAGACAGGC|TTTTGTGTTG|TTGGGCATGT|GCCACCTTAG|GGAATTTCCA|191880|
|CCTGTACCCT|CCTTTCTCTT|TCTCCAGGAT|ATTTTGGCCA|CAGACTTTAT|CATAAACTCC|191940|
|ATCCCTTAGG|GTGGCATTAG|GGTAGTCTTG|GGCCTGAATT|TAGGTGGGCC|AGTGGCTGTC|192000|
|TTAGTGACAG|CCTTTCCGCT|CTCTTCTGTC|ATCCCTCCC|AACTGCTAAT|GTCTAACTAC|192060|
|CTAACAATTA|CCCATTAAAT|CAGTGTGTCT|GGGGTTAGGA|GCAGGCCTCA|ATATGTTTAA|192120|
|TCATTCTCCA|GATAATCCCA|ATACTGTAAA|GTTTGTGAAA|CACTTGTCAG|ATAATTCAAT|192180|
|TATGAAGGCT|GTGGAAGGTG|TTTCAGTAGG|ATCTAATTGG|TTAATGTTAT|GACTTAATTA|192240|
|ATTTGAATCA|AAAAACAAAA|TGAAAAAGCT|TTATATTTCT|AAGTCAAATA|AGACATAAGT|192300|

| | | | | | | |
|---|---|---|---|---|---|---|
| TGGTCTAAGG | TTGAGATAAA | ATTTTTAAAT | GTATGATTGA | ATTTTGAAAA | TCATAAATAT | 192360 |
| TTAAATATCT | AAAGTTCAGA | TCAGAACATT | GCGAAGCTAC | TTTCCCCAAT | CAACAACACC | 192420 |
| CCTTCAGGAT | TTAAAAACCA | AGGGGGACAC | TGGATCACCT | AGTGTTTCAC | AAGCAGGTAC | 192480 |
| CTTCTGCTGT | AGGAGAGAGA | GAACTAAAGT | TCTGAAAGAC | CTGTTGCTTT | TCACCAGGAA | 192540 |
| GTTTTACTGG | GCATCCCTG | AGCCTAGGCA | ATAGCTGTAG | GGTGACTTCT | GGAGCCATCC | 192600 |
| CCGTTTCCCC | GCCCCCCAAA | AGAAGCGGAG | ATTTAACGGG | GACGTGCGGC | CAGAGCTGGG | 192660 |
| GAAATGGGCC | CGCGAGCCAG | GCCGGCGCTT | CTCCTCCTGA | TGCTTTTGCA | GACCGCGGTC | 192720 |
| CTGCAGGGGC | GCTTGCTGCG | TGAGTCCGAG | GGCTGCGGGC | GAACTAGGGG | CGCGGCGGGG | 192780 |
| GTGGAAAAAT | CGAAACTAGC | TTTTTCTTTG | CGCTTGGGAG | TTTGCTAACT | TTGGAGGACC | 192840 |
| TGCTCAACCC | TATCCGCAAG | CCCCTCTCCC | TACTTCTGC | GTCCAGACCC | CGTGAGGGAG | 192900 |
| TGCCTACCAC | TGAACTGCAG | ATAGGGGTCC | CTCGCCCCAG | GACCTGCCCC | CTCCCCGGC | 192960 |
| TGTCCCGGCT | CTGCGGAGTG | ACTTTTGGAA | CCGCCCACTC | CCTTCCCCCA | ACTAGAATGC | 193020 |
| TTTTAAATAA | ATCTCGTAGT | TCCTCACTTG | AGCTGAGCTA | AGCCTGGGGC | TCCTTGAACC | 193080 |
| TGGAACTCGG | GTTTATTTCC | AATGTCAGCT | GTGCAGTTTT | TTCCCCAGTC | ATCTCCAAAC | 193140 |
| AGGAAGTTCT | TCCCTGAGTG | CTTGCCGAGA | AGGCTGAGCA | AACCCACAGC | AGGATCCGCA | 193200 |
| CGGGGTTTCC | ACCTCAGAAC | GAATGCGTTG | GGCGGTGGGG | GCGCGAAAGA | GTGGCGTTGG | 193260 |
| GGATCTGAAT | TCTTCACCAT | TCCACCCACT | TTTGGTGAGA | CCTGGGGTGG | AGGTCTCTAG | 193320 |
| GGTGGGAGGC | TCCTGAGAGA | GGCCTACCTC | GGGCCTTTCC | CCACTCTTGG | CAATTGTTCT | 193380 |
| TTTGCCTGGA | AAATTAAGTA | TATGTTAGTT | TTGAACGTTT | GAACTGAACA | ATTCTCTTTT | 193440 |
| CGGCTAGGCT | TTATTGATTT | GCAATGTGCT | GTGTAATTAA | GAGGCCTCTC | TACAAAGTAC | 193500 |
| TGATAATGAA | CATGTAAGCA | ATGCACTCAC | TTCTAAGTTA | CATTCATATC | TGATCTTATT | 193560 |
| TGATTTTCAC | TAGGCATAGG | GAGGTAGGAG | CTAATAATAC | GTTTATTTTA | CTAGAAGTTA | 193620 |
| ACTGGAATTC | AGATTATATA | ACTCTTTTCA | GGTTACAAAG | AACATAAATA | ATCTGGTTTT | 193680 |
| CTGATGTTAT | TTCAAGTACT | ACAGCTGCTT | CTAATCTTAG | TTGACAGTGA | TTTTGCCCTG | 193740 |
| TAGTGTAGCA | CAGTGTTCTG | TGGGTCACAC | GCCGGCCTCA | GCACAGCACT | TTGAGTTTTG | 193800 |
| GTACTACGTG | TATCCACATT | TTACACATGA | CAAGAATGAG | GCATGGCACG | GCCTGCTTCC | 193860 |
| TGGCAAATTT | ATTCAATGGT | ACACTGGGCT | TTGGTGGCAG | AGCTCATGTC | TCCACTTCAT | 193920 |
| AGCTATGATT | CTTAAACATC | ACACTGCATT | AGAGGTTGAA | TAATAAAATT | TCATGTTGAG | 193980 |
| CAGAAATATT | CATTGTTTAC | AAGTGTAAAT | GAGTCCCAGC | CATGTGTTGC | ACTGTTCAAG | 194040 |
| CCCCAAGGGA | GAGAGCAGGG | AAACAAGTCT | TTACCCTTTG | ATATTTGCA | TTCTAGTGGG | 194100 |
| AGAGATGACA | ATAAGCAAAT | GAGCAGAAAG | ATATACAACA | TCAGGAAATC | ATGGGTGTTG | 194160 |
| TGAGAAGCAG | AGAAGTCAGG | GCAAGTCACT | CTGGGGCTGA | CACTTGAGCA | GAGACATGAA | 194220 |
| GGAAATAAGA | ATGATATTGA | CTGGGAGCAG | TATTTCCCAG | GCAAACTGAG | TGGGCCTGGC | 194280 |
| AAGTTGGATT | AAAAAGCGGG | TTTTCTCAGC | ACTACTCATG | TGTGTGTGTG | TGGGGGGGGG | 194340 |
| GGGCGGCGTG | GGGGTGGGAA | GGGGGACTAC | CATCTGCATG | TAGGATGTCT | AGCAGTATCC | 194400 |
| TGTCCTCCCT | ACTCACTAGG | TGCTAGGAGC | ACTCCCCAG | TCTTGACAAC | CAAAAATGTC | 194460 |
| TCTAAACTTT | GCCACATGTC | ACCTAGTAGA | CAAACTCCTG | GTTAAGAAGC | TCGGGTTGAA | 194520 |
| AAAAATAAAC | AAGTAGTGCT | GGGGAGTAGA | GGCCAAGAAG | TAGGTAATGG | GCTCAGAAGA | 194580 |
| GGAGCCACAA | ACAAGGTTGT | GCAGGCGCCT | GTAGGCTGTG | GTGTGAATTC | TAGCCAAGGA | 194640 |
| GTAACAGTGA | TCTGTCACAG | GCTTTTAAAA | GATTGCTCTG | GCTGCTATGT | GGAAAGCAGA | 194700 |

| | | | | | | |
|---|---|---|---|---|---|---|
| ATGAAGGGAG | CAACAGTAAA | AGCAGGGAGC | CCAGCCAGGA | AGCTGTTACA | CAGTCCAGGC | 194760 |
| AAGAGGTAGT | GGAGTGGGCT | GGGTGGGAAC | AGAAAAGGGA | GTGACAAACC | ATTGTCTCCT | 194820 |
| GAATATATTC | TGAAGGAAGT | TGCTGAAGGA | TTCTATGTTG | TGTGAGAGAA | AGAGAAGAAT | 194880 |
| TGGCTGGGTG | TAGTAGCTCA | TGCCAAGGAG | GAGGCCAAGG | AGAGCAGATT | CCTGAGCTCA | 194940 |
| GGAGTTCAAG | ACCAGCCTGG | GCAACACAGC | AAAACCCCTT | CTCTACAAAA | AATACAAAAA | 195000 |
| TTAGCTGGGT | GTGGTGGCAT | GCACCTGTGA | TCCTAGCTAC | TCGGGAGGCT | GAGGTGGAGG | 195060 |
| GTATTGCTTG | AGCCCAGGAA | GTTGAGGCTG | CAGTGAGCCA | TGACTGTGCC | ACTGTACTTC | 195120 |
| AGCCTAGGTG | ACAGAGCAAG | ACCCTGTCTC | CCCTGACCCC | CTGAAAAAGA | GAAGAGTTAA | 195180 |
| AGTTGACTTT | GTTCTTTATT | TTAATTTTAT | TGGCCTGAGC | AGTGGGGTAA | TTGGCAATGC | 195240 |
| CATTTCTGAG | ATGGTGAAGG | CAGAGGAAAG | AGCAGTTTGG | GGTAAATCAA | GGATCTGCAT | 195300 |
| TTGGGACATG | TTAAGTTTGA | GATTCCAGTC | AGGCTTCCAA | GTGGTGAGGC | CACATAGGCA | 195360 |
| GTTCAGTGTA | AGAATTCAGG | ACCAAGGCTG | GCACGGTGG | CTCACTTCTG | TAATCCCAGC | 195420 |
| ACTTTGGTGG | CTGAGGCAGG | TAGATCATTT | GAGGTCAGGA | GTTTGAGACA | AGCTTGGCCA | 195480 |
| ACATGGTGAA | ACCCCATGTC | TACTAAAAAT | ACAAAAATTA | GCCTGGTGTG | GTGGCGCACG | 195540 |
| CCTATAGTCC | CAGGTTTTCA | GGAGGCTTAG | GTAGGAGAAT | CCCTTGAACC | CAGGAGGTGC | 195600 |
| AGGTTGCAGT | GAGCTGAGAT | TGTGCCACTG | CACTCCAGCC | TGGGTGATAG | AGTGAGACTC | 195660 |
| TGTCTCAAAA | AAAAAAAAAA | AAAAAAAAAA | AAAAACTGAA | GGAATTATTC | CTCAGGATTT | 195720 |
| GGGTCTAATT | TGCCCTGAGC | ACCAACTCCT | GAGTTCAACT | ACCATGGCTA | GACACACCTT | 195780 |
| AACATTTTCT | AGAATCCACC | AGCTTTAGTG | GAGTCTGTCT | AATCATGAGT | ATTGGAATAG | 195840 |
| GATCTGGGGG | CAGTGAGGGG | GTGGCAGCCA | CGTGTGGCAG | AGAAAAGCAC | ACAAGGAAAG | 195900 |
| AGCACCCAGG | ACTGTCATAT | GGAAGAAAGA | CAGGACTGCA | ACTCACCCTT | CACAAAATGA | 195960 |
| GGACCAGACA | CAGCTGATGG | TATGAGTTGA | TGCAGGTGTG | TGGAGCCTCA | ACATCCTGCT | 196020 |
| CCCCTCCTAC | TACACATGGT | TAAGGCCTGT | TGCTCTGTCT | CCAGGTTCAC | ACTCTCTGCA | 196080 |
| CTACCTCTTC | ATGGGTGCCT | CAGAGCAGGA | CCTTGGTCTT | TCCTTGTTTG | AAGCTTTGGG | 196140 |
| CTACGTGGAT | GACCAGCTGT | TCGTGTTCTA | TGATCATGAG | AGTCGCCGTG | TGGAGCCCCG | 196200 |
| AACTCCATGG | GTTTCCAGTA | GAATTTCAAG | CCAGATGTGG | CTGCAGCTGA | GTCAGAGTCT | 196260 |
| GAAAGGGTGG | GATCACATGT | TCACTGTTGA | CTTCTGGACT | ATTATGGAAA | ATCACAACCA | 196320 |
| CAGCAAGGGT | ATGTGGAGAG | GGGGCCTCAC | CTTCCTGAGG | TTGTCAGAGC | TTTTCATCTT | 196380 |
| TTCATGCATC | TTGAAGGAAA | CAGCTGGAAG | TCTGAGGTCT | TGTGGGAGCA | GGGAAGAGGG | 196440 |
| AAGGAATTTG | CTTCCTGAGA | TCATTTGGTC | CTTGGGGATG | GTGGAAATAG | GGACCTATTC | 196500 |
| CTTTGGTTGC | AGTTAACAAG | GCTGGGGATT | TTTCCAGAGT | CCCACACCCT | GCAGGTCATC | 196560 |
| CTGGGCTGTG | AAATGCAAGA | AGACAACAGT | ACCGAGGGCT | ACTGGAAGTA | CGGGTATGAT | 196620 |
| GGGCAGGACC | ACCTTGAATT | CTGCCCTGAC | ACACTGGATT | GGAGAGCAGC | AGAACCCAGG | 196680 |
| GCCTGGCCCA | CCAAGCTGGA | GTGGGAAAGG | CACAAGATTC | GGGCCAGGCA | GAACAGGGCC | 196740 |
| TACCTGGAGA | GGGACTGCCC | TGCACAGCTG | CAGCAGTTGC | TGGAGCTGGG | GAGAGGTGTT | 196800 |
| TTGGACCAAC | AAGGTATGGT | GGAAACACAC | TTCTGCCCCT | ATACTCTAGT | GGCAGAGTGG | 196860 |
| AGGAGGTTGC | AGGGCACGGA | ATCCCTGGTT | GGAGTTTCAG | AGGTGGCTGA | GGCTGTGTGC | 196920 |
| CTCTCCAAAT | TCTGGGAAGG | GACTTTCTCA | ATCCTAGAGT | CTCTACCTTA | TAATTGAGAT | 196980 |
| GTATGAGACA | GCCACAAGTC | ATGGGTTTAA | TTTCTTTTCT | CCATGCATAT | GGCTCAAAGG | 197040 |
| GAAGTGTCTA | TGGCCCTTGC | TTTTTATTTA | ACCAATAATC | TTTTGTATAT | TTATACCTGT | 197100 |

-continued

| | | | | | | |
|---|---|---|---|---|---|---|
| TAAAAATTCA | GAAATGTCAA | GGCCGGGCAC | GGTGGCTCAC | CCCTGTAATC | CCAGCACTTT | 197160 |
| GGGAGGCCGA | GGCGGGTGGT | CACAAGGTCA | GGAGTTTGAG | ACCAGCCTGA | CCAACATGGT | 197220 |
| GAAACCCGTC | TCTAAAAAAA | TACAAAAATT | AGCTGGTCAC | AGTCATGCGC | ACCTGTAGTC | 197280 |
| CCAGCTAATT | GGAAGGCTGA | GGCAGGAGCA | TCGCTTGAAC | CTGGGAAGCG | GAAGTTGCAC | 197340 |
| TGAGCCAAGA | TCGCGCCACT | GCACTCCAGC | CTAGGCAGCA | GAGTGAGACT | CCATCTTAAA | 197400 |
| AAAAAAAAAA | AAAAAAAAAA | GAGAATTCAG | AGATCTCAGC | TATCATATGA | ATACCAGGAC | 197460 |
| AAAATATCAA | GTGAGGCCAC | TTATCAGAGT | AGAAGAATCC | TTTAGGTTAA | AAGTTTCTTT | 197520 |
| CATAGAACAT | AGCAATAATC | ACTGAAGCTA | CCTATCTTAC | AAGTCCGCTT | CTTATAACAA | 197580 |
| TGCCTCCTAG | GTTGACCCAG | GTGAAACTGA | CCATCTGTAT | TCAATCATTT | TCAATGCACA | 197640 |
| TAAAGGGCAA | TTTTATCTAT | CAGAACAAAG | AACATGGGTA | ACAGATATGT | ATATTTACAT | 197700 |
| GTGAGGAGAA | CAAGCTGATC | TGACTGCTCT | CCAAGTGACA | CTGTGTTAGA | GTCCAATCTT | 197760 |
| AGGACACAAA | ATGGTGTCTC | TCCTGTAGCT | TGTTTTTTTC | TGAAAGGGT | ATTTCCTTCC | 197820 |
| TCCAACCTAT | AGAAGGAAGT | GAAAGTTCCA | GTCTTCCTGG | CAAGGGTAAA | CAGATCCCCT | 197880 |
| CTCCTCATCC | TTCCTCTTTC | CTGTCAAGTG | CCTCCTTTGG | TGAAGGTGAC | ACATCATGTG | 197940 |
| ACCTCTTCAG | TGACCACTCT | ACGGTGTCGG | GCCTTGAACT | ACTACCCCA | GAACATCACC | 198000 |
| ATGAAGTGGC | TGAAGGATAA | GCAGCCAATG | GATGCCAAGG | AGTTCGAACC | TAAAGACGTA | 198060 |
| TTGCCCAATG | GGGATGGGAC | CTACCAGGGC | TGGATAACCT | TGGCTGTACC | CCCTGGGGAA | 198120 |
| GAGCAGAGAT | ATACGTGCCA | GGTGGAGCAC | CCAGGCCTGG | ATCAGCCCCT | CATTGTGATC | 198180 |
| TGGGGTATGT | GACTGATGAG | AGCCAGGAGC | TGAGAAAATC | TATTGGGGGT | TGAGAGGAGT | 198240 |
| GCCTGAGGAG | GTAATTATGG | CAGTGAGATG | AGGATCTGCT | CTTTGTTAGG | GGGTGGGCTG | 198300 |
| AGGGTGGCAA | TCAAAGGCTT | TAACTTGCTT | TTTCTGTTTT | AGAGCCCTCA | CCGTCTGGCA | 198360 |
| CCCTAGTCAT | TGGAGTCATC | AGTGGAATTG | CTGTTTTGT | CGTCATCTTG | TTCATTGGAA | 198420 |
| TTTTGTTCAT | AATATTAAGG | AAGAGGCAGG | GTTCAAGTGA | GTAGGAACAA | GGGGGAAGTC | 198480 |
| TCTTAGTACC | TCTGCCCCAG | GGCACAGTGG | GAAGAGGGGC | AGAGGGATC | TGGCATCCAT | 198540 |
| GGGAAGCATT | TTTCTCATTT | ATATTCTTTG | GGACACCAG | CAGCTCCCTG | GGAGACAGAA | 198600 |
| AATAATGGTT | CTCCCCAGAA | TGAAAGTCTC | TAATTCAACA | AACATCTTCA | GAGCACCTAC | 198660 |
| TATTTTGCAA | GAGCTGTTTA | AGGTAGTACA | GGGGCTTTGA | GGTTGAGAAG | TCACTGTGGC | 198720 |
| TATTCTCAGA | ACCCAAATCT | GGTAGGGAAT | GAAATTGATA | GCAAGTAAAT | GTAGTTAAAG | 198780 |
| AAGACCCCAT | GAGGTCCTAA | AGCAGGCAGG | AAGCAAATGC | TTAGGGTGTC | AAAGGAAAGA | 198840 |
| ATGATCACAT | TCAGCTGGGG | ATCAAGATAG | CCTTCTGGAT | CTTGAAGGAG | AAGCTGGATT | 198900 |
| CCATTAGGTG | AGGTTGAAGA | TGATGGGAGG | TCTACACAGA | CGGAGCAACC | ATGCCAAGTA | 198960 |
| GGAGAGTATA | AGGCATACTG | GGAGATTAGA | AATAATTACT | GTACCTTAAC | CCTGAGTTTG | 199020 |
| CGTAGCTATC | ACTCACCAAT | TATGCATTTC | TACCCCCTGA | ACATCTGTGG | TGTAGGGAAA | 199080 |
| AGAGAATCAG | AAAGAAGCCA | GCTCATACAG | AGTCCAAGGG | TCTTTTGGGA | TATTGGGTTA | 199140 |
| TGATCACTGG | GGTGTCATTG | AAGGATCCTA | AGAAAGGAGG | ACCACGATCT | CCCTTATATG | 199200 |
| GTGAATGTGT | TGTTAAGAAG | TTAGATGAGA | GGTGAGGAGA | CCAGTTAGAA | AGCCAATAAG | 199260 |
| CATTTCCAGA | TGAGAGATAA | TGGTTCTTGA | AATCCAATAG | TGCCCAGGTC | TAAATTGAGA | 199320 |
| TGGGTGAATG | AGGAAAATAA | GGAAGAGAGA | AGAGGCAAGA | TGGTGCCTAG | GTTTGTGATG | 199380 |
| CCTCTTTCCT | GGGTCTCTTG | TCTCCACAGG | AGGAGCCATG | GGGCACTACG | TCTTAGCTGA | 199440 |
| ACGTGAGTGA | CACGCAGCCT | GCAGACTCAC | TGTGGGAAGG | AGACAAAACT | AGAGACTCAA | 199500 |

| | | | | | | |
|---|---|---|---|---|---|---|
| AGAGGGAGTG | CATTTATGAG | CTCTTCATGT | TTCAGGAGAG | AGTTGAACCT | AAACATAGAA | 199560 |
| ATTGCCTGAC | GAACTCCTTG | ATTTTAGCCT | TCTCTGTTCA | TTTCCTCAAA | AAGATTTCCC | 199620 |
| CATTTAGGTT | TCTGAGTTCC | TGCATGCCGG | TGATCCCTAG | CTGTGACCTC | TCCCTGGAA | 199680 |
| CTGTCTCTCA | TGAACCTCAA | GCTGCATCTA | GAGGCTTCCT | TCATTTCCTC | CGTCACCTCA | 199740 |
| GAGACATACA | CCTATGTCAT | TTCATTTCCT | ATTTTTGGAA | GAGGACTCCT | TAAATTTGGG | 199800 |
| GGACTTACAT | GATTCATTTT | AACATCTGAG | AAAAGCTTTG | AACCCTGGGA | CGTGGCTAGT | 199860 |
| CATAACCTTA | CCAGATTTTT | ACACATGTAT | CTATGCATTT | TCTGGACCCG | TTCAACTTTT | 199920 |
| CCTTTGAATC | CTCTCTCTGT | GTTACCCAGT | AACTCATCTG | TCACCAAGCC | TTGGGGATTC | 199980 |
| TTCCATCTGA | TTGTGATGTG | AGTTGCACAG | CTATGAAGGC | TGTACACTGC | ACGAATGGAA | 200040 |
| GAGGCACCTG | TCCCAGAAAA | AGCATCATGG | CTATCTGTGG | GTAGTATGAT | GGGTGTTTTT | 200100 |
| AGCAGGTAGG | AGGCAAATAT | CTTGAAAGGG | GTTGTGAAGA | GGTGTTTTTT | CTAATTGGCA | 200160 |
| TGAAGGTGTC | ATACAGATTT | GCAAAGTTTA | ATGGTGCCTT | CATTTGGGAT | GCTACTCTAG | 200220 |
| TATTCCAGAC | CTGAAGAATC | ACAATAATTT | TCTACCTGGT | CTCTCCTTGT | TCTGATAATG | 200280 |
| AAAATTATGA | TAAGGATGAT | AAAAGCACTT | ACTTCGTGTC | CGACTCTTCT | GAGCACCTAC | 200340 |
| TTACATGCAT | TACTGCATGC | ACTTCTTACA | ATAATTCTAT | GAGATAGGTA | CTATTATCCC | 200400 |
| CATTTCTTTT | TTAAATGAAG | AAAGTGAAGT | AGGCCGGGCA | CGGTGGCTCA | CGCCTGTAAT | 200460 |
| CCCAGCACTT | TGGGAGGCCA | AAGCGGGTGG | ATCACGAGGT | CAGGAGATCG | AGACCATCCT | 200520 |
| GGCTAACATG | GTGAAACCCC | ATCTCTAATA | AAAATACAAA | AAATTAGCTG | GGCGTGGTGG | 200580 |
| CAGACGCCTG | TAGTCCCAGC | TACTCGGAAG | GCTGAGGCAG | GAGAATGGCA | TGAACCCAGG | 200640 |
| AGGCAGAGCT | TGCAGTGAGC | CGAGTTTGCG | CCACTGCACT | CCAGCCTAGG | TGACAGAGTG | 200700 |
| AGACTCCATC | TCAAAAAAAT | AAAAATAAAA | ATAAAAAAAT | GAAAAAAAAA | AGAAAGTGAA | 200760 |
| GTATAGAGTA | TCTCATAGTT | TGTCAGTGAT | AGAAACAGGT | TTCAAACTCA | GTCAATCTGA | 200820 |
| CCGTTTGATA | CATCTCAGAC | ACCACTACAT | TCAGTAGTTT | AGATGCCTAG | AATAAATAGA | 200880 |
| GAAGGAAGGA | GATGGCTCTT | CTCTTGTCTC | ATTGTGTTTC | TTCTGAGTGA | GCTTGAATCA | 200940 |
| CATGAAGGGG | AACAGCAGAA | AACAACCAAC | TGATCCTCAG | CTGTCATGTT | TCCTTTAAAA | 201000 |
| GTCCCTGAAG | GAAGGTCCTG | GAATGTGACT | CCCTTGCTCC | TCTGTTGCTC | TCTTTGGCAT | 201060 |
| TCATTTCTTT | GGACCCTACG | CAAGGACTGT | AATTGGTGGG | GACAGCTAGT | GGCCCTGCTG | 201120 |
| GGCTTCACAC | ACGGTGTCCT | CCCTAGGCCA | GTGCCTCTGG | AGTCAGAACT | CTGGTGGTAT | 201180 |
| TTCCCTCAAT | GAAGTGGAGT | AAGCTCTCTC | ATTTTGAGAT | GGTATAATGG | AAGCCACCAA | 201240 |
| GTGGCTTAGA | GGATGCCCAG | GTCCTTCCAT | GGAGCCACTG | GGGTTCCGGT | GCACATTAAA | 201300 |
| AAAAAAATCT | AACCAGGACA | TTCAGGAATT | GCTAGATTCT | GGGAAATCAG | TTCACCATGT | 201360 |
| TCAAAGAGT | CTTTTTTTT | TTTTGAGAC | TCTATTGCCC | AGGCTGGAGT | GCAATGGCAT | 201420 |
| GATCTCGGCT | CACTGTAACC | TCTGCCTCCC | AGGTTCAAGC | GATTCTCCTG | TCTCAGCCTC | 201480 |
| CCAAGTAGCT | GGGATTACAG | GCGTGCACCA | CCATGCCCGG | CTAATTTTG | TATTTTTAGT | 201540 |
| AGAGACAGGG | TTTCACCATG | TTGGCCAGGC | TGGTCTCGAA | CTCCTGAC | CTCGTGATCC | 201600 |
| GCCTGCCTCG | GCCTCCCAAA | GTGCTGAGAT | TACAGGTGTG | AGCCACCCTG | CCCAGCCGTC | 201660 |
| AAAAGAGTCT | TAATATATAT | ATCCAGATGG | CATGTGTTTA | CTTTATGTTA | CTACATGCAC | 201720 |
| TTGGCTGCAT | AAATGTGGTA | CAAGCATTCT | GTCTTGAAGG | GCAGGTGCTT | CAGGATACCA | 201780 |
| TATACAGCTC | AGAAGTTTCT | TCTTTAGGCA | TTAAATTTTA | GCAAAGATAT | CTCATCTCTT | 201840 |
| CTTTTAAACC | ATTTTCTTTT | TTTGTGGTTA | GAAAAGTTAT | GTAGAAAAAA | GTAAATGTGA | 201900 |

-continued

| | | | | | | |
|---|---|---|---|---|---|---|
| TTTACGCTCA | TTGTAGAAAA | GCTATAAAAT | GAATACAATT | AAAGCTGTTA | TTTAATTAGC | 201960 |
| CAGTGAAAAA | CTATTAACAA | CTTGTCTATT | ACCTGTTAGT | ATTATTGTTG | CATTAAAAAT | 202020 |
| GCATATACTT | TAATAAATGT | ATATTGTATT | GTATACTGCA | TGATTTATT | GAAGTTCTTG | 202080 |
| TTCATCTTGT | GTATATACTT | AATCGCTTTG | TCATTTTGGA | GACATTTATT | TTGCTTCTAA | 202140 |
| TTTCTTTACA | TTTTGTCTTA | CGGAATATTT | TCATTCAACT | GTGGTAGCCG | AATTAATCGT | 202200 |
| GTTTCTTCAC | TCTAGGGACA | TTGTCGTCTA | AGTTGTAAGA | CATTGGTTAT | TTTACCAGCA | 202260 |
| AACCATTCTG | AAAGCATATG | ACAAATTATT | TCTCTCTTAA | TATCTTACTA | TACTGAAAGC | 202320 |
| AGACTGCTAT | AAGGCTTCAC | TTACTCTTCT | ACCTCATAAG | GAATATGTTA | CAATTAATTT | 202380 |
| ATTAGGTAAG | CATTTGTTTT | ATATTGGTTT | TATTTCACCT | GGGCTGAGAT | TTCAAGAAAC | 202440 |
| ACCCCAGTCT | TCACAGTAAC | ACATTTCACT | AACACATTTA | CTAAACATCA | GCAACTGTGG | 202500 |
| CCTGTTAATT | TTTTAATAG | AAATTTTAAG | TCCTCATTTT | CTTTCGGTGT | TTTTAAGCT | 202560 |
| TAATTTTTCT | GGCTTTATTC | ATAAATTCTT | AAGGTCAACT | ACATTTGAAA | AATCAAAGAC | 202620 |
| CTGCATTTTA | AATTCTTATT | CACCTCTGGC | AAAACCATTC | ACAAACCATG | GTAGTAAAGA | 202680 |
| GAAGGGTGAC | ACCTGGTGGC | CATAGGTAAA | TGTACCACGG | TGGTCCGGTG | ACCAGAGATG | 202740 |
| CAGCGCTGAG | GGTTTTCCTG | AAGGTAAAGG | AATAAAGAAT | GGGTGGAGGG | GCGTGCACTG | 202800 |
| GAAATCACTT | GTAGAGAAAA | GCCCCTGAAA | ATTTGAGAAA | ACAAACAAGA | AACTACTTAC | 202860 |
| CAGCTATTTG | AATTGCTGGA | ATCACAGGCC | ATTGCTGAGC | TGCCTGAACT | GGGAACACAA | 202920 |
| CAGAAGGAAA | ACAAACCACT | CTGATAATCA | TTGAGTCAAG | TACAGCAGGT | GATTGAGGAC | 202980 |
| TGCTGAGAGG | TACAGGCCAA | AATTCTTATG | TTGTATTATA | ATAATGTCAT | CTTATAATAC | 203040 |
| TGTCAGTATT | TTATAAAACA | TTCTTCACAA | ACTCACACAC | ATTTAAAAAC | AAAACACTGT | 203100 |
| CTCTAAAATC | CCCAAATTTT | TCATAAACTC | AGTTTTAAAC | TAACTTTTTT | TCAAACCACA | 203160 |
| ATCTGATTTA | ACAATGACTA | TCATTTAAAT | ATTTCTGACT | TTCAAATTAA | AGATTTTCAC | 203220 |
| ATGCAGGCTG | ATATTTGTAA | TTGTGATTCT | CTCTGTAGGC | TTTGGGTATA | ATGTGTTCTT | 203280 |
| TTCCTTTTTT | GCATCAGCGA | TTAACTTCTA | CACTCTAACA | TGTAGAATGT | TACTACAATA | 203340 |
| TTAAAGTATT | TTGTATGACA | ATTTTATTTG | AAAGCCTAGG | ATGCGTTGAC | ATCCTGCATG | 203400 |
| CATTTATTAC | TTGATATGCA | TGCATTCTGG | TATCTCAAGC | ATTCTATTTC | TGAGTAATTG | 203460 |
| TTTAAGGTGT | AGAAGAGATA | GATATGGTGG | ATTTGGAGTT | GATACTTATA | TATTTCTAT | 203520 |
| TTCTTGGATG | GATGAATTTG | TACATTAAAA | GTTTTCCATG | GCAGAAATCT | TTTCAAAAAC | 203580 |
| TTTTTTTTTC | CGGGATGGAT | TGAAGGCCCT | GATTTCACCA | CAATGCAATA | TATTAATGTA | 203640 |
| GCAAAATTGT | ACTTGTACCC | CATGAATATA | TATAATCTTA | AGAAAATTTT | TTTAGCCAAT | 203700 |
| TATTATTACT | TACTAGATAT | TAGGCTGTGT | TCTGAATCTT | AATTTAATTC | CTCCAAAGAA | 203760 |
| TCTTATGAGG | TAGGTAGGAG | CTATTGCTGC | TATTCTGTTA | TGCTTATGTT | GCTGTTATGA | 203820 |
| AACCAAGGCA | CAGAGAGGTT | AGTTAACTTG | CTGAAGAAAA | TGATGTGCTG | GATTTTTATT | 203880 |
| CTAGCTATTC | TGGAATAACA | ACTACACAAC | CTTATGTCTG | AGCCAAGGAA | ACATACGGTG | 203940 |
| TGGCAACAGT | TACCATGTTT | TTAGGAACAG | CAGCACTCCT | AATGTTTGCT | GCAGGGAAAA | 204000 |
| AGGAATCTCA | GAATTTGCCT | GATCCCTATA | ATTTTTTTCC | TAAATATTTT | GAAATATCTT | 204060 |
| TCAGATGTAT | TTTAAAATTT | AAGGATATTT | TGTTCAGTTC | ATACAGAATT | TTTTTTTTTT | 204120 |
| TCTCGAGATG | GAGTCTCACT | CTATCACCCA | GGCTGGAATG | CAGTGGCATG | ATCTCGGCTC | 204180 |
| ACTGCAACCT | CTGCCTCCTG | GGTTCAAGCA | ATTTTCCTGC | CTCAGCCTCC | CAAGTGGCTG | 204240 |
| AGACTACAGG | CGCATGCCAC | CATGCACGGC | TAATTTTTTT | TGTATTTTTA | GTAGAGATGG | 204300 |

| | | | | | |
|---|---|---|---|---|---|
| AGTTTCACCA | TGTTGGCCAG | GCTGGTCTCG | AACTCCTGAC | CTCAAATGAT | CCGCCCTTTT 204360 |
| TGGCCTCCCA | AAGTGCTGGG | ATTACAGGCG | TGAGCTACCG | CGCCCAGCCA | AATTTCTAAC 204420 |
| TTGTTTTGTT | GTTGTTGAGA | CAGGGTCTCA | GTCTGACACC | AAGGCTGGTG | TGCAGTACTG 204480 |
| CGATCACGGC | TCACTGCAGT | CTCGACCTCC | TGAGCTCAAG | TGATCCTCCC | ACCTCAGCCT 204540 |
| ACTGAGTAGC | TGGGACCACC | ACGCCTGGCT | CATTTTTTC | TATTATTTAT | TGAAACGGGT 204600 |
| TCTGGCTATG | TTGCCCAGGT | TGGTCTTGAA | CTCCGGAGCT | CATGCGATCC | ACCCACCTCA 204660 |
| GCGTCCGAAA | GGATTATCAG | GAGTGAGCCA | CCGTGCCCGG | CCAAATTTCT | AACTTTTGAA 204720 |
| TTGACATATT | CATTTATTCT | CTTTATCATT | CAGGGAGAAA | TTTGGGGATG | GATAGCCTTG 204780 |
| AAGCATCATC | CACCAAGTTA | TTTTATACAC | CAGATTTAGA | TACAAAGTAT | TTTTTTATTA 204840 |
| TTTAAAAAAA | TCAAATTCTA | GCTTTTACTC | TGAAGATTCT | AAAAAGAATT | TTGGAGTCTT 204900 |
| TAATTCATAC | TTCAGGGGCA | GGGGAATAAG | TACCAATATT | CGTATAACTT | TCAGTGCAAG 204960 |
| TCACGTTAGC | TAACTGTAGT | CTATTGAGTT | AAATATCCTT | GATTTATTCC | TTAAAACTGA 205020 |
| GTCACTATGA | CGGCACTTTT | TTGTTTTTTT | TTTTCGAGAC | GGAGCTCGCC | CTGTCTCCCA 205080 |
| GGCTGGAGTG | CGGTGGTGCG | ATCTCGGCTC | ACTGCAATCT | CCGCCTCCCA | GGTTCAAGCG 205140 |
| ATTCTCCTGC | CCCAGCCTCC | TGAGTAGCTG | GGACTACAGG | CACACACCAC | CACGCCCAGC 205200 |
| TAATGTTTGT | ATTTTAGTA | GAGACAGGGT | TTCATCATTT | TGGTCAGGCT | GGTCTTGAAC 205260 |
| TCCTGACCTC | GTGATCAGCC | TGCCTCGACC | TCCCAAAGTG | CTGGGATTAC | AGTCATGAGC 205320 |
| CACTGCACCC | GGCTGAATGG | CACTTTCATA | AAACAGTAAA | TAACCAACTT | CACTACTGCC 205380 |
| CCCAAGAGTT | TTACTATGTA | TATGAGGGCA | TCTGTTTTAA | GTATGGGTAT | AATGTTACGG 205440 |
| GTTTTTCTTT | GTGTAAGTTT | GGGTTCACAA | TTTCATCATT | AAAACAAATG | TAAAATACTT 205500 |
| TGTGCTTTCT | GTGTGCTATT | AAGAAAGTAT | TCAAGGGAAT | TTTGAAAATC | AAATTTAATT 205560 |
| ACTCTCATGT | TTGTAAAATT | TTTGAAACAA | ATGTTTAAGA | GAGGATAATG | TTAGAAATTA 205620 |
| TCTTTCCAGC | CAGACCTGGT | GGCTCACGCC | AGTAATCCTA | GCATTTGGG | AGGACAAGGT 205680 |
| GGGCAGATCA | CTTAAGCCCA | GGAATTCAAG | ACCAGCCTGG | ACAACACAGG | GAAAGCCCAT 205740 |
| CTCTACAAAA | TATACAAAAT | TAGTGGCCGA | GCGTGGTGGC | TCACGCCTGT | AATCCCAGCA 205800 |
| CTTTGGGAGG | CCGAGGCGGG | CAGATCACCT | GAGGTCAGGA | GTTCCAGACC | AGCCTCAACA 205860 |
| TGGAGAAACC | CCGTCTCTAC | TAAAAATACA | AAATTAGCTG | GGCGTGGTGA | TGCATGCCTG 205920 |
| TAATCCCAGC | TACTCGGGAG | GCTGAGGCAG | GAGAATTGCT | TGAACCTGGG | AGGTAGAGGT 205980 |
| TGCGGTGAGC | CGAGATCCCG | CCATTGCACT | CCAGCCTGGG | CAACAAGAGC | GAAACTCCAT 206040 |
| CTCAAAAAAC | AAAACAAACA | AATAAACAAA | ATTAGTCAGG | TGTGGTTGTG | CACACCTGTA 206100 |
| GTCCCAGCTA | CTTGGGAGGC | TGAGGTGGGA | GGATCACTTG | AGCCCGGGGA | AGTGTAGGCT 206160 |
| ACCATGAGCC | ATCATGGTGC | CACTGTACTC | CAGTCTAGGA | AAAAATAAA | CATTAAAAAT 206220 |
| TTTAAAATCT | TAAAAAAGA | AAAGAAATTT | TCTGTCCAGA | TATCTTTATT | TTAACAAAT 206280 |
| CGAAGTGTAT | TAATAGTGTT | TATGGGAGCG | TGCCCACACA | AGGACAGCAA | GCCTAGGAAG 206340 |
| TGCAAGTCAA | GAAAACTTTT | TGTGAAATAA | TTTAAACTGA | AAGAAAAAG | CAGAGATTTT 206400 |
| TTTCTAGAAA | AGTAAGGAGT | GGAGGTAAAA | AAAAACACA | GCAGAGACAC | AGGTATGCTA 206460 |
| CGGAACCAAA | GGTGTGCCAA | TGGTACTGAC | AGTTTAATTC | AGAAAAAAT | GAATCAGAAA 206520 |
| ATGGATATTT | TTAAATAAGT | TAGGTTGCTG | AAAAAGAGAA | ATGCAGTGAA | GCCTTAGATG 206580 |
| GGAGTGAGAT | AAATCAGCCA | TTGGCTAGAG | GAGTTTCTTG | CCCAAGACCA | GTGGTGATGT 206640 |
| CCCCAAATGC | CTGGAAACAA | CTGTTGTGAC | ATTATAAAGC | CCCCATAGTC | TAAGTTGGGT 206700 |

-continued

| | | | | | | |
|---|---|---|---|---|---|---|
| GAGACTATAC | TTATGCATTT | TCTCACCTGT | AATATAGCTT | AAAAGTATTT | CTACTCTGGG | 206760 |
| ATTTCTTTAC | ATTTTACTAA | AGCGCAATTA | TATACTTAAA | ACTGATAGTG | TATGCTGGGC | 206820 |
| TGCTAGTCAT | TCTCAACCCT | GGCCAATTAT | CAGAATTGTT | TGTTGAATAT | ATAGGTGCCA | 206880 |
| TATATAGGTG | CATACACACA | CACACACACA | CACATACACA | CACACACACA | CACACACACA | 206940 |
| CCATATTTCA | TTCCTCATAT | CGAATATTCT | GAGAGAGTTA | GTTTGTGGAG | GGTAGTTCTG | 207000 |
| GACAATTTAT | ATTTTCATAA | CACCTCTGGT | TATTTTTTTT | TAAGTAGAGA | TGAAGACTTG | 207060 |
| CTATGTTGCC | CAAAATGGTC | TTGAACTCCT | GAGCTCAAGC | GATTCTCCCA | ACTCAGCCTC | 207120 |
| CTGAAGTGCT | GGGATTACAG | CCGTGAGCCA | CTGCATTAAC | CTCTGATTAA | TATCATAGAT | 207180 |
| TAACCTCTGA | TTAATATCAT | AGATTTATTT | GTTGAATGC | TTCATGTATC | CTCTCAACCA | 207240 |
| CAACTTGTTT | GCAGAGTTTT | AATCTGAAGG | GCTTAGGTCT | CTTGTTCAAT | GAATGAGTTT | 207300 |
| GATCTGATGG | GTGAGAGGAA | GGTGAAATGG | AAAGCGAACG | AGAAGCCATA | CAGATTAGGC | 207360 |
| GAGTGAGCCT | AATCTCTCCC | TAACCATAAG | ATTGAGTATG | CCTGAATTCT | TCGCAGAGTG | 207420 |
| GAAGAATCCA | TTTTAAATAT | ATATATCTAC | ATGTACAGAT | CCTTTAAATA | TTTGTTCTGA | 207480 |
| CATTCATTGT | TTTTGAGTCA | CTGTCATTGA | GAAAAGTTTA | GAAAGGAGAT | ATTAGGAGCA | 207540 |
| GGAAATAGAA | AGTAAATAAA | ATATCAAAAT | AAAAATGGGG | TTTTATAAAT | GATATAATAG | 207600 |
| GCAAAATAAA | GGAAAGGCAT | CCTAGACCTC | TGGTTAAAAT | GAAGATGGCA | CTTGGCGAGA | 207660 |
| TGTGTTCCAG | GGTAGTTCAC | ATGATGTATG | TTTTCAGAGA | ATTGTCATAT | TGCATATGCT | 207720 |
| GCTATATTTT | TTATTTTCAT | GAATTAAAAG | GCATGTTGAG | ATTTCAGAGT | TTTACTTATG | 207780 |
| ATCTCAGACT | CTGCATTTTT | TCTCTGTAAT | GTTTGACATT | TCTTCCTAGC | TAAGTCTCTA | 207840 |
| GTTATAAGGT | CTGTGTTGTG | GCATGTGGAC | AGTGAGTGGA | AGAACCTAAG | AACTCAATTT | 207900 |
| GGGGCAGAAG | AATGTAATCA | ATTATTTCAG | AAGTGATACA | AACAATATGA | CATGTAGAGC | 207960 |
| ATTCTGGCCT | TTCCTGGGTC | TTTTTTCTCC | ATTCCTGGAT | TTCTTCTCTT | CATGTGAGCA | 208020 |
| AGTCTGAGGT | TACTATATAA | TGTCTCTCAC | AGGCCACAGC | CCCATTCTAA | ATATTCCCAA | 208080 |
| TAGAAATTCA | TTTATTAACC | AGAGAGTGG | GGGTGGGGTT | GTTTTGTTT | TTTAAACAAA | 208140 |
| AGTGGATCTT | ATGGGCATTC | TGGAAAGCTC | CCGCAGGAAG | CTAAGAATAA | AATTTTGAAT | 208200 |
| TGAGAAGTCC | CTTTCTTCAA | ACCACATTCA | GACCCAATTC | TGCTATTCTA | TTTATTTTTC | 208260 |
| AAGGGGATTA | GCCTTATTTT | AACACCAATA | ATCTTATCAC | AAAAACCTCC | CAGAGGAAGA | 208320 |
| CCCTGTAGAT | TTTGTAATGA | CCTTAATCAA | GTATTAGCCC | TACACTTCAA | TTAATCCCCA | 208380 |
| ACTGTACAAA | ACGAATGTTC | TTTTCTCTAA | AGCTGTAGCA | AGTTGAAAGG | GGATTAAAAA | 208440 |
| CGGAGGGAAG | GGAAGAGTGT | TTGGAATTTC | AGGCACAGCA | AACAGGCACA | GCAGACCAGG | 208500 |
| AAGAGCGTCC | CGGGAAAACA | TATTATCCAG | ACTTAAGTTT | ATATTCCCTG | TCTCTCTCAG | 208560 |
| ACTTTTGCAG | AAAAATGAGT | CATTCAACAA | ATATTTGAAT | CGAGATAGGG | AAAGTGACGA | 208620 |
| GGAAGAAGTT | TGCACTTATG | AGGTTTTAAT | TTGCAATTAT | TTGGCTACCT | TTTTGCCTTC | 208680 |
| CCAAAACATA | GGGTCTTTAG | GAGTGAAACT | TCATAGCCAA | ACTTATACCT | TGTCCAGCAC | 208740 |
| AGAGAAGGCC | ATCAAAATGC | CTGGTTTAAA | TAAAAATATT | AAAATGATTG | GGAGGGTAAA | 208800 |
| TCCCTTGACC | TATAAATCTG | ACCTCCTTTA | AACATTATTT | GTATGTTCCC | CAATAAACTA | 208860 |
| TTCCGTAATT | TATTAGTTAG | CAAGTGGAAA | TAAAAGAAA | TGTGGAATGG | GGCTATGCTT | 208920 |
| AGCGTCATTA | AGCTGACAGG | AATACAGCGC | ATTCAACTTG | CAAACACCCT | TCCACTCCCA | 208980 |
| CAAAGAGCAA | GCTGTCACTG | GCCAATCAAA | ACAATGAACC | ATAATGAAAC | AGTTTTCTT | 209040 |
| GCTCCACCCA | CTTGGTGACC | AAATTTGAAA | AAAAAAAAAA | ACCGCGCCAA | CTCATGTTGT | 209100 |

| | | | | | |
|---|---|---|---|---|---|
| TTTCAATCAG | GTCCGCCAAG | TTTGTATTTA | AGGAACTGTT | TCAGTTCATA | CCTTCCACTG 209160 |
| CGATAGGAAT | CATGTCTGGT | CGCGGCAAAG | GCGGAAAAGG | CTTGGGGAAG | GGTGGTGCTA 209220 |
| AGCGCCATCG | TAAGGTGCTC | CGGGATAACA | TCCAGGGCAT | TACAAAACCG | GCTATTCGCC 209280 |
| GTTTGGCTCG | GCGCGGTGGC | GTCAAGCGCA | TTTCCGGTCT | TATCTATGAG | GAGACTCGAG 209340 |
| GTGTGCTTAA | GGTTTTCTTA | GAGAACGTTA | TTCGAGACGC | CGTCACCTAT | ACGGAGCACG 209400 |
| CCAAGCGCAA | AACTGTCACA | GCCATGGATG | TAGTATATGC | CCTAAAACGT | CAGGGGCGCA 209460 |
| CTCTGTATGG | CTTCGGCGGC | TGAATCTAAG | AATACGCGGT | CTCCTGAGAA | CTTCAAAAAA 209520 |
| CAAAAACAAA | AAAACCCAAA | GGCCCTTTTC | AGGGCCGCTC | ACAAAGTCGT | TTAAAGAGCT 209580 |
| GAAATGCGTT | GCGAGAATGA | GTTTGGATGA | CAGAAATAAC | CGTGACATCC | TGCATAAGAA 209640 |
| TGAATTGTGT | TTGCCATGAC | CGGCCACACT | GTGACAAAAT | TTCAAAGCAT | AAAGTAGGCA 209700 |
| TAGAGAGGTA | AGCGCTAATA | AAGTGATTGG | CTCCACAAAA | AGCATTTTGC | TGGGCGCAGT 209760 |
| GGCTCACGAC | TGTAATCCCA | GCACTTTGGG | AGGCCAAAGC | TAGTGTATCA | CTTGAGATCA 209820 |
| AGAATCCGAG | ACCAGCCTGG | CCAAAATGGT | GAAACCCCCT | CTACCAAAAA | AATACAAAA 209880 |
| CTTAGCCGGG | CGTGGTGGTC | TGCACCTGTA | GGCCCAGCTA | GCCCGGAAGC | AGAGATTGCA 209940 |
| GTGAGCCGAG | ATCGCGCCAC | TCCCCTCCAG | CCTGGGAGAC | AGAGAGAGAC | TCCTCAAAAA 210000 |
| AAAAAAAAAA | AAAAAAAAAA | AAAATTATGT | ATTTTAGAGC | ATTCTAAGAA | TGGTACTTTG 210060 |
| GACTTAACCG | AAGGGCTGGA | GGCGCGTGTT | GAACAAAGGT | TATCACCTTT | TGGCTCATGC 210120 |
| GGCACACAGC | TATGTAAATA | AAGCATCTTT | AGGGACAAGC | TCTCATTTGC | GGAGGGTTCT 210180 |
| ATGGCTGTTG | TCCTATTGGC | CAAAACAAAG | TGGTCTAAGT | CCGGGCGCGG | TGGCTCACGC 210240 |
| CTGTATTCCC | AGCAGTTTGG | TAGGCCAAGG | TGGGTGGATC | ACGAGGTCTG | GCGTTCAAGA 210300 |
| CCAGCCTGGC | CAAGATGGTG | AAACCCCGTC | TACTAAAAAT | ACAAAATTA | GCCGGGCGTG 210360 |
| GTGGCGGGCA | CCTGTAATCC | CAGCTACGTG | GGAGGCTGAG | CCAGAGAACT | GCTTGAACCC 210420 |
| AGGAGGCAGA | GGTTGCAGTG | AACCGAGATT | GTGCCACTGC | ACTCTAGCCT | GGGTGACAGA 210480 |
| GCGAGGCTCC | ATCCAAAACA | AAACAAAACA | AAAAGTGGT | CTAATAATCC | CCAGAACTGG 210540 |
| AGGAAGAACC | ATAACTTATT | GATTTGTTT | TTAACCTTAT | GTATGCCAGG | CATGCTAGCC 210600 |
| TTGTATACAT | ACAAGGCTAG | AGGAGCAAAG | GTGCAGGAAG | CCATCTTGAG | GGAGTCCCAT 210660 |
| ATTATTGAGA | GACCGGCCAG | CTGCTGGGAG | AGGCTAGTTG | TTCATCCTCA | CTGTATGTGA 210720 |
| TGAGAATCTG | GTGACAGTCC | ATTGCTGGGC | ACAGCATTTA | GGCAAATGG | CTCTCTGCTA 210780 |
| TGTCAGGCAA | GTGAGGCATA | TTTTTGCACA | ATCCTAGTAA | TTCCGAACTC | ATTGGGAAAC 210840 |
| AATGGCAATT | ACATCCAAGC | AAGGAAAGGT | CTGTGGTTGA | TTTTATCTAT | ACAAATTTAA 210900 |
| AACATAATGT | TTACAACCTT | TCATTATAGG | ACACAATTTT | TAAAAAGATG | CCAAACTATA 210960 |
| CAAATAAGTT | CAGAAAAGTG | AGGTACTATT | GAACCGTCTG | GAAAACATAA | ATGTATGTGA 211020 |
| AATAATGCAA | TGCATAGTTT | TGCAGGGGAC | TTTGTTCAAA | GTTTCTCGAA | ATACCATGGT 211080 |
| CCAAAGTAGA | CTAACATTAG | CATTGGTTAT | TTATGATGAT | CAGTAAGAAT | ACTAAATCAA 211140 |
| AAATCAAAGG | AAAATTAAAC | TATGTCTGTT | TAAAGAGAAA | CGTAGTTTAC | CTCAGACTGA 211200 |
| GAGTTAAAAC | AAGTTTGTGA | TTCAGGAAGG | TGGAATTCAG | AACCTAATTG | GGCAGCCTCC 211260 |
| AACATTTCCA | TTAAGGTTTG | GATTCTTAAA | ATTTTTCAGT | CTTCGGTATG | CTCTGGTAGT 211320 |
| CTGATGAAAC | TTACAGATTC | TTTTCATAAA | TAAGATACTT | AAAGTAATTC | ATAGGGTTAC 211380 |
| AATTGTATTA | GACCAATAAT | ATTAAAATAA | TTATCAAACC | ACTTGACCGT | AATATGTGTG 211440 |
| TTTTTGTTGA | TATACCTAAT | AGTACTTCGG | AAATAAGCAA | GCACGATTTC | CAGATTCTTG 211500 |

| | | | | | | |
|---|---|---|---|---|---|---|
| CAACAACTAT | AACCTACAAA | TTTGTTATTT | CTATCAGTCA | CACACAATGG | AAGAAAATTC | 211560 |
| TAAATTTCAG | CTACAGGATA | ATGAATAGAT | GAAAACAAC | AACAACAACA | ACAACAAAAA | 211620 |
| AACTCCCCTA | ATCCATATTC | TGGGACACCT | TGATTCCTAT | TTATTGATCC | CTTGAAGTCA | 211680 |
| GTGGATAGCA | TATTAAGAAA | CAATAGTTAC | AATGACACCA | CAGAAAGACT | AGAATGTAGT | 211740 |
| ACTTGTGTTA | AAAAAAAAA | AAGTATCAGC | AAGTTATGTT | TGGATGCCAA | ATTGCTCTCC | 211800 |
| ACTTCCCTTC | CCTGACACTG | GCATTTCCAG | AACTTAGATG | CTCTTACATG | TAAAAGCCTC | 211860 |
| CTCTAGTGCA | CCATCGAGCT | TTTCAGGATT | GGACATCAGA | CTTTTTAGTT | CCTGGACCTC | 211920 |
| TAGATATACG | GCAGTCTCTG | ACAAGAAGCC | CTTTTTCTGT | TTTAACTTTT | TTTTTTTTA | 211980 |
| AGTTTTGAGA | CAACGTCTGA | CTCGCTGTCA | CCCAGGCTGG | AGTGAGGTAG | CACCATCATA | 212040 |
| GCTCACTGTA | TCCTTAAACG | CCTGGGTGCA | GGGACTAAGG | GAGCGTGCCA | ACCATGCTTG | 212100 |
| ACTAATTTAC | TTTTTTGTAA | AACCAGTAGT | CTCCAACCTT | TTTGACACAA | GAGACCGTTT | 212160 |
| TGTGTAAGAC | AATTATACCA | CGGACCAGGG | GGTGCAGGGG | CTGGGAGCAA | TGATTTCCGG | 212220 |
| ACTAAAACTG | CTCCAACCTC | AGATCATCAG | GCATTAGATT | GTCACAAGGA | GCCTGAAACC | 212280 |
| TAGATCCCTT | GCATGTGCCA | TTCACAATAC | AGTTTGAGCT | TATGAGAATC | TATCTAATGC | 212340 |
| TGCAGCTAAC | CTGACAGGCG | GTGGAGCTCA | GTTGGTTAAT | GTTCGCTCAC | CCCTCAGCTG | 212400 |
| TGCGGCTCAA | TTCATAACGT | GCCATGGACA | GGGACCGGTT | ACCGGTCGGT | GGCCGGGGAA | 212460 |
| ATGAGGACCC | CTGGTATAGA | TGGTAGTCTG | GCTATGTTGC | CCAGGATGGT | CTTGAAGCCT | 212520 |
| GGCCTGAATT | AATTCTCCAA | TCTCAAGCCT | TTTCAACTCA | GCTGCATCAC | AACTTAAACC | 212580 |
| TATAGATAAC | TGTCACAGAA | ACTTGTTTCC | AGTGTTACGC | CATCTTAAAA | TAATGTGGGT | 212640 |
| GGCTCTTAAA | AGAGCCTTTG | GGTTCTTTCC | AAATTGGCCT | CCCGGAAAGC | TCTTTACTTC | 212700 |
| TTAGATGTGG | CCTTTCTAAC | ATTAACTTCA | TGATGTTGGG | TCAATTTTGA | CTTCGAAGCC | 212760 |
| CTTGCCTTCA | CTGGGCTCTT | CTGCTGTTGC | TTACCCTTGG | CTCCTTAGC | CTTTCTCCG | 212820 |
| CTCCTAACAG | TTTTAGGAGT | TGTCGCTCTC | GGCTTCTTGG | CTCTCTTATT | GGTTTTAGCA | 212880 |
| GTCTTTGGTG | ACTTGGAGTC | CCTGGATAAA | ACCAGCTTCT | TGGTCTTGGC | AGAAACTGAC | 212940 |
| TTTTTAGCCT | TGCTTCTGGT | AGATTTAGGA | ATCACCTTCT | TACTAAGCTT | AAAGGAACCG | 213000 |
| GAAGCACCAG | TACCCCTGGT | TTGCACCAGG | ATTCCCTTGT | TCACTAAGCT | CTTGAGGGAC | 213060 |
| AGTTTGATGC | GGCTGTTATT | CTTCTCTACG | TCGTAGCCAG | CAGCGGCCAA | TGCCTTCTTG | 213120 |
| AGCGCAACCA | AAGACATACC | TACTCGTTCC | TGTGACACTG | AAAGGGCCTC | GGTGATCAAC | 213180 |
| TTGGACACAG | AGAGGTTCGG | CACTTTGCGA | CTTGCACTTA | TCAAGCCAGC | CGGCTTCCTC | 213240 |
| CCTCGCTTCT | TGGTTGGAAG | TTTCTCCATA | GCGGCTACAC | CAGCACTGGC | AGAAGCTGCA | 213300 |
| GGCACGGTTT | CAGACATAAC | AACAGAGAAA | CGCAAGATGT | AATAACCAGC | GAAAAGCATG | 213360 |
| AAACACCCGG | GCGGCCTCGG | GGCCTTATAT | AGGGTAGGGC | GCGCTGTGAT | TGGTGCATCA | 213420 |
| CCTAGGCACC | GCCCCCGCCC | CTTGGAGGAG | GAGTATTTGT | GTTTGTTTTA | CCCGGAAAAG | 213480 |
| TTGAGTATAA | CAAAACCCCT | CTTTACAGAA | TCTCCCAGGG | TCTAGTGCTG | AATAATCTGC | 213540 |
| GGAAATTCAT | ATTTGACATG | ACTTTTCTCT | TTTTAATGAA | AAATGACCCT | GGATGCCAAA | 213600 |
| ACTATTCGAG | AAAGCCCTCG | ATTTTCAATC | AAATTCACGG | AGAGGAACAA | AACTTCCCCT | 213660 |
| TTTCCTTGTA | AATTAATAAG | TAATCTTTGG | CAGAAGACTT | ATTTCATCTC | TTCAGAGTGG | 213720 |
| TCTTCCAAAT | GGATAGCTTC | AAATCGGTAG | AGGAAAGAAA | TTATTCACGC | CATGATTTTT | 213780 |
| ATTTAAAATT | ATTTATATAT | GTGAGGGAAG | TAACACAGAT | CTCTTAGCTG | TCTAATTGCG | 213840 |
| GAGTCAGAAG | ATGCTTATAG | AATTGTCAAA | AGACTGCAGA | GGATGTCTTT | ATTTAGGCAT | 213900 |

```
GTGCAATCTA  ATAAATCATA  ATCCACAGGA  ACATGGGTTG  TCTGTAATTA  AAGGTGCTCC  213960
CAAGTCCCTG  TAGCTTTATA  GAGGACTCTC  AAGGATGGGG  TAATATCAAG  ATCTCACACA  214020
TTATGTAAGA  TTGGCCATAA  TCAGGCCACT  CTCATGACCG  GTGTCCTCAA  CTGAGTTTTG  214080
CTTCTGGTTT  CATTAATTGA  AGTCCCTCT   ATCCCCTGC   CCACCCCTAC  ATCCCAGAT   214140
AAACAGACAC  AGTCCCTCCC  CTAAATTAAC  TATAAAACAT  GAGGTAGGAA  CCCTAGACTC  214200
AAGAACCTAC  TAGAAACTAC  AGACCCCATG  TCTAACAAGA  CTGGGCGGGT  TGGCTGGGCG  214260
CAGTGATTCA  TGCCTGTAAT  TACAGCACTT  CGGAAGGCTG  GAGGCCAGGA  GTTCAAGACT  214320
AGGTTGGCCT  GGTCCCTACT  GAAAAAAAA   AAAATTAGCT  GGGTGTGGTG  GCACATGCCT  214380
GCAGTCCCAG  CTTCTGGGTA  GACTGAAGAG  GATCACTTAG  AGCCCAGGAG  CTTGAGGTCG  214440
CAGCTACTGC  ACTCCAGCCT  GGGCAGACCC  TCATCTCTGA  ATTGCTTAAT  TAATTAACTG  214500
AGCTGGCAGA  TTTGGCTGCA  TAGCTGTGGG  GAAAGGGTTG  TTGGAATAAT  GTCCAGTGTG  214560
CTCCCCTGAG  CTTCTACTGG  AACAGGTCTT  TGTGAGAGGC  CTGGAGATAA  GAGCTTGCTC  214620
ACAAAGGCTG  AGGCCTTTCT  GGGATGCTGA  ATGAGTTTAG  TGTGGCCAGA  GCATAGGGTC  214680
TCAGCAAAGG  AAAACTCCAT  AAGGGCCATT  TGTGAAGATC  CCCAAATACT  TGTGTGAAAC  214740
ATTTGGTAGA  TATTAGAAGT  TTTGTTTTGG  TTTGGTTTGA  GACAGAGTTT  TGCTCTTGTT  214800
GCCCAGGCTG  GAGTGCAATG  GTGTGATCTT  GGCTCAGTGC  AACCTCCACC  TCCCAGGTTC  214860
AGGCAATTCT  CCTGCCTCAG  CCTCCCAATT  AGCTGGGATT  ATAGGCGCCC  ACCACCATGC  214920
CTGGCTAATT  TTTTGTATTT  TTAGTAGAGA  TGGGGTTTCA  TCATGTTGGC  CAGGCTAGTC  214980
TCGAACTCCC  CACCTCAAGT  GATCTGCCCG  CCTCTGCCTC  CAAAGTGCTG  GGAATACATG  215040
CGTGAGCCGC  CGCGCCCGGC  AGACATTGGA  AGTTTTAAG   CAGAGAATTT  GTTGTATTGT  215100
TGTAGTTGTC  TTGGGTTTAG  ATTTATTGCA  TAAACAATCA  TTTTTGAGAA  GGGCCCACAG  215160
TCAGAAGTTG  GGAGTCTGTT  GCAATAGTCT  CAGAAGAATG  GCAAAGACCT  TGCCTAAGGG  215220
GACAGTGTGG  TAAAGGAGAG  AGTCTACATT  TGAAATATTT  CTGAAACAAA  AGCCAAAAGA  215280
TAAGACTTCA  AACTTCTGAT  TGCAAAGTGA  GATAGAAAAG  TTTCTTCTC   TCTGTCTCTC  215340
TGTTATACCC  ATACACACAC  ACATATGCAC  AAACACCTGA  AGAAAAAAA   AATTCAGGGA  215400
ACAGGCCAGG  TAGGGTGGCT  CATGCCTATA  ATCCCATAAA  TTTGGGAGGC  TGAGGCTAGT  215460
GGATCACTAG  AGCCCAGGAG  TTCACAAGGC  CAGCCTAAGC  ACATAGCAAG  ACCCTGTCTC  215520
TACAATTAAA  AAATTACCCG  GGTGTGGTGG  CACGTACCTG  TGGTCCCAGT  TACTCAAAAG  215580
GCTGAGGTGG  GAGAATCACT  TGGGCCCAGG  AGGTCAAGGC  TGCAGTGAGC  ATGATTGTGC  215640
CACTGCACTT  CAGCCTGGGC  AAGAGCGAGA  CCCTGTCTCA  AAAAAAAAA   ATTTTTTTT   215700
TTTTTCCAGA  AAACAATACT  ATCTTAAGCA  CCAGCACTTT  AGTATATTCT  ACTGTGGACT  215760
AGTTCATTTT  TAAAAGAACA  CTAGGTTGGA  AATCATGAGA  TTGATTCCAC  AACTCACTAA  215820
AGCACCGTGT  CACTCAGTTT  GGAAAATATT  TCTCCTTAGA  GAGATTACAG  GTGCATCTTT  215880
CTGAGCACCT  GTATGTTTTT  ACATTTGTTT  GGCTTCTCTG  ACCTTTGATA  ATTTCTGAGT  215940
GTTGTACTAT  TAAATATTAG  TGGCTAGGGG  TCAAATTGTG  GATCAGGTTG  ATCCTTATAT  216000
TTACAAGTTG  ACAGATACGT  TACTCCATTG  CTTTAAAACT  AACACAGAAT  TAGAGAATTT  216060
AGAAAATTCT  TACATTCCAT  AATTTAAGAC  CCAGAAAAA   AAGATTCATA  TTTTGCATTA  216120
GATAGCTAAA  ATGGTACCAT  AAAAACAAAT  GATATCCACA  TATATATAGT  ATATAGTGCT  216180
TCTTCTGTGC  CAGTCACTAT  CCTAAGTTTT  TCTCTCCCTT  CCCCAAAAAT  GTAGGAATTA  216240
ACTTTATAGA  TGAAGAAACT  GAGGCACAGG  AATGTCACAT  GACTTGCCCA  AAGGAAATTC  216300
```

-continued

| | | | | | |
|---|---|---|---|---|---|
| AGTCTTCCTT | TTTCAATTCT | TTTTTCTTTT | TACTTTGCTG | CAGGGTCTCG | CTGTGTTGCC 216360 |
| CAGGATGCTC | TTGAACTCCC | GGACTCAAGC | GATCCTCCTT | CTTCAGCCTC | TCAAAGTGCT 216420 |
| GGGATTACAG | GCATGAGCCA | CTGCGCCCAG | TCAGGAAATT | CAGTCTTCTA | AACATTCATT 216480 |
| ATTGAAATAA | TATTTCCATA | AACATTTTCT | TAGATAAACT | TTGGCATCTC | TAACTTCTAA 216540 |
| GTAGCAAAGT | CATGGAAACA | GTCACAGAGA | AAATAACTTT | ATTTAAAAA | TAATAAATTC 216600 |
| TTATCTCCGG | TGATAAGAAA | AGTATACAGC | CCATTTTTA | AAGTATTAAT | TTTACATTCT 216660 |
| AATTTGGTTT | TTTTAATGTT | TACCATATAT | TTCTCTTTCT | ACATATGTGT | GTGAGTGAAT 216720 |
| AAAATAAAGG | CATCTACAGA | TTTTTACATG | TTCAGTGAGA | TTAGCAGGGT | TTCACTTGAC 216780 |
| AGCACTCTTA | CCATACTCAC | TTCTTGGCTT | TTCCTGATAT | CTAACATTTT | TAAAATGAGT 216840 |
| AGTCCCTTTT | CATATGATTC | TTCCTTTTTC | AAGCACTATT | TTTGAACTTT | ATATTTGATT 216900 |
| GGCAATAATT | TTTACAGACA | TTATTTTACG | ATTAACTTTA | ACTCTGTTCA | AATGATTTCT 216960 |
| TCATTTTCAA | GTATTTTATT | TGAACTGCTT | TTTTTGGTTC | AACTACTGAG | TATTTAATTT 217020 |
| GTCTGTTTTG | TAGAAAGGGT | ATGTAGATAA | TTCCATGTTT | TGTAAAAGTT | GTCTCTAAAA 217080 |
| ATCTAACAAG | TGTAAGTACG | ATGCTATTAC | AGGGCTGAGA | GACACAGAAA | AAACACACAC 217140 |
| ACACACACAA | AATTTTTTTT | TAAGTATTAC | TTGGTCTCTA | AACTAAAGAA | TTTACCATCT 217200 |
| ATTTTGGGAG | ATGAAATCCA | AACATAAGCA | ATGACAACAA | TTATTATGTG | CTTAAATCAA 217260 |
| TGTCCAAGAC | AATAATTGAC | CCCAAGGCAG | GGAAATCACT | GAGAGAGTAT | AGCAGAGAAG 217320 |
| GTGTCCTCTC | TGTTCAGATG | AGCCTGAATA | ATTTGTTCAG | TAGGTTTCTG | CTACTCATTT 217380 |
| ATAAACTGCA | CATCTTCTGT | AGTCCTGGAA | AATGTCTAAG | AGGAGAGAGG | AACTAAGATC 217440 |
| AGGGCCACCA | TTTAATTAGG | AAGTTCTGGG | AGTACCTGAC | CCAGAAGAAA | GATCAGCATA 217500 |
| GCTGAAAATC | ACCCATAGGA | GAAACATCTA | GGTAATCTTA | TTTCTGTTCC | ACCTGACATT 217560 |
| TCAACCTCTC | TTTTCAGCTA | TAAGTATATA | AGTACTTATA | TGTAAGTAAA | GAAATTTACC 217620 |
| CACATCATGT | TGTTTTTTAT | TCAATGCTTA | ACATGTATAA | TGCTAACAAC | ACAGACTTGA 217680 |
| TGTCCAAAAC | ATTTCTATGA | ACAGCTCATT | ACTGGATGAC | TGAAATAATT | TTTCCAAGCC 217740 |
| ACGTGGAGGT | TAATGAGTCA | GTTTTTGAAA | GCAAGGAGAG | AAAAACATTA | GAATTTAAGG 217800 |
| TGACGTTTCT | GTTGCGTTGT | AATCCAGAAT | ACAGAATAGT | CAGAGAAAAG | CAGAAAGTCT 217860 |
| TTCTTCTTAA | ATTTTCTGAA | AACCAAGGTG | TGCATTAAAA | TGGTACATGC | CTACTTCCCT 217920 |
| TTCCCTTTAC | CCTTTTTTCC | TGCATGGAAC | ATAGATATGA | CCCCTAGACA | TGCTGCAGAT 217980 |
| GACCATGAGG | TTGAAAGATA | CATGGAAGAT | GGTTAACACA | GGATGATAGA | AGAGACCTGC 218040 |
| ATACTTGGGC | AGCCTAGACA | GCTCCTGCCA | GCCCCCAACA | AAACAGCCTA | GCCTTCTTGC 218100 |
| CAATCAAGAA | AAAAAATCCC | TTCTGGTAAC | CCACTGTAAG | TGAATTTCTG | TAAATGTGGC 218160 |
| CCAATGTATC | CATAATTGAT | ATACAAATAT | TAGTTTAGTG | GGTAGCACCT | CTCCATGAGC 218220 |
| ATGTCGACTT | CATGAGACTG | AGATTTTTGA | CTGTCATGTG | CAGTTGTCCC | ATTACAGTGC 218280 |
| CTGGTGCATG | GGAACAGCTC | AACTGTGCAT | ACCCATTGAA | GAAATAGATG | CATGGTCAAT 218340 |
| CGAATTTCCA | GGTATATCAT | ATGTTTCCAT | AAAAAAAGTA | AACATACAGC | ATATCTCCTT 218400 |
| CCAGTTTATT | TATTTTTCTC | TCTAGGACCA | ATTTACAGTC | TATCAGCAGT | GCGTGAGCAC 218460 |
| CTGTTTCACC | ACATATACAA | ACCCCTCCAA | GACTATAAGG | ATATCATTAA | GCTTTTATC 218520 |
| ACTGTCAGTT | AAGTGGTAAA | CATAGTTTTC | TACATACTTT | GCATTTTGT | TTCTCATGAG 218580 |
| ATTCAATGTT | TTACATGGGT | AAGTTGTTAG | ATCATATTTA | TTCAAGATGA | GGCATTTGTC 218640 |
| TCCTGGTAAG | ACATCTTGGT | CTAATGCTGA | CTCTGGGGTG | TGGACATTTG | GCTGTTGACT 218700 |

| | | | | | | |
|---|---|---|---|---|---|---|
| GTGAGGTGGC | TATCTACATG | TGGAGTGGAG | GAGTCCTGGC | CTTGGATTGA | GGAGAACAAG | 218760 |
| GTCAACTTCT | CACCTCACTT | GTTTCTGGCT | TTTGTGACCT | TGGACAAGTT | TAACTTTTCT | 218820 |
| CTCTCCTAGT | CTTAGTTTTC | TTGTCTGTAA | GTGACAGCAA | TGATGCTGTC | TTTGTTGGGG | 218880 |
| TGGGCTGCCA | TAAAAAAATA | CCATAGATTG | TGTGGTTTAA | ACAACAAAAT | TTTATCACAG | 218940 |
| TTCTGGAGGC | TGGAAGTCTC | AGAGCAGGGT | ATAGCATGGC | TGGATTCTGT | GGAGAGGGCT | 219000 |
| CTCTTGCTGG | CTTGTAGAGT | GCTACCTTCT | CACTGTGAGA | GCTCACATAG | CCTTTCCTCA | 219060 |
| GTATATGTGC | AGAGCTCCCT | CTCTTCCTCT | TTTTTTTTT | TCTTTTAAAT | AAATTATTTA | 219120 |
| ATTTGGAAGA | CCAAGTGCAG | AATCTTCCTC | TTCTTATAAG | GCCACCAATC | CTATCCAGTT | 219180 |
| AGGAACCCAT | CCTAATGACC | TCATTTAACC | TTAATTACCT | CTTATAAGTC | CTGTCTAGGA | 219240 |
| ATAGAGTCAT | ATTGGGGTTT | ATGGCTTCAA | TATATGAATT | TGGGGGGATG | GGGAGACAAT | 219300 |
| TCAGTCCATA | GTAAACACTT | CCTCAAAGAG | TAGTTATAAT | GTTTATAAGA | GACAATGTAG | 219360 |
| GTAAAAGTAG | TTTCAGTTGC | ATGCAGCTAA | ATGCAGTTTA | GTATCCCTTC | AGAGTCCTCC | 219420 |
| GCAGAAAAGG | CACCTGATAA | ATATTTATGT | GGCCTTAACC | TAAGGTATTA | TTCTTTATAT | 219480 |
| AGTGCCTTCC | CATGTAATGA | TTGATGTCAT | GTTTATCATT | TGCAGTGCAG | TTTATTTCTT | 219540 |
| ATAGGTCATG | GCTACAGAAA | CATGGGAGAA | TGACCATCAT | TAATAGGTCA | TTAGAATATG | 219600 |
| TAATTTCAAT | TTTTTTTTCT | TTTGAAGGAC | TATTAGGTTA | ACAATGATTT | TTAAAATTTA | 219660 |
| TAGTAGATAT | GAGTGCTATA | AAACAGGAAT | TTCCATATTA | TTTTGGGATT | ATAAATTGGT | 219720 |
| ATGATCCTGA | ATAGCAATTT | GGCAATGTAT | ATGTTAAGAA | CCTTAGAAAA | TGTTTTTCAC | 219780 |
| TTTTGATTTA | GTATTTCCAC | TTCATGAAGT | CTATCCTTAG | GAAATAATAT | TTGAACAAAG | 219840 |
| ATTTATGTAC | AAAGATGTGT | GAGCTATATA | ATCTATAATA | TAATGCATAA | AAATGGGAAT | 219900 |
| CAATTGAAGT | AGTCAATAAC | AAATACATAA | TTATCAATAT | ATCCATAAAT | TATACATCCA | 219960 |
| TAAAAAAGTT | TCTAAGTATA | TTTATCTAAA | TATATATCAT | GACACCTAAA | TTTATTTTAT | 220020 |
| ATATGATACA | TGATGTGAGA | TATATGTATA | TATGAATATG | AGTATATATA | ATATACATAT | 220080 |
| AAAAAGAATA | GGAGATACTA | GGAGTTATTT | TAATTTTGTC | TTTATGTTTC | CTGTGTCATA | 220140 |
| AATTTCTATG | AAGAATATTT | TAATAGTTTT | ATGCATAGAA | AAAAGAGCTA | ATTTTTCTCA | 220200 |
| GCCAGGTGTT | CATTTGTCCT | TCTTTGATTG | TTCAAAATAC | CTCCATTTAT | CTTCTTCTAG | 220260 |
| GATCACTCAT | TTTCATTGGT | TTATTTGCAA | GATGAAACAG | TGTCCAGCAG | TGACGACTGT | 220320 |
| TGGAAAAGAT | ATGTCTAAAA | GCTGTTGTCT | CCCCCTGGAG | AAAAGAGAGA | GAGTGATTGA | 220380 |
| TTCACTTCTG | TAATTTATCA | GATATGAGAT | ATTGTATTTG | ACTCTGAGAA | CAATGATAAT | 220440 |
| GATGATGGCT | AAAGTTCACT | GGATGTTTGC | TCTGTGCCAG | GCAGTGTTTT | AAGCACTTTA | 220500 |
| CACAATAGAT | ACCAATGCAT | TTAGTTGTTC | CAACAACCTT | ATGAGATACC | TACTGTCATT | 220560 |
| CTCCCTGCGT | TATAGATGAG | GAAATTAAGG | CACAGAGAGG | TTAAGTTTCC | CAGGTAGCAC | 220620 |
| AGCTGTTGGA | TAATGAGCCT | GTGCAGTAAA | CCCACATCCT | CTAGCCCTTG | AATGTCTGTA | 220680 |
| CGCTCTTAAA | AGATGAATGT | AACCTAGTCA | GTGTCCTAAA | GTTCCATTTG | ATCTAAACTT | 220740 |
| GAAGGATAAA | AATTTATCCA | GTGAGGAAAA | AGACTTAGTG | TTTTTCATAA | AGAAGATACA | 220800 |
| GCGACGAAGG | CCAGGCCGTG | GGGACTGTCT | GATTTTTAGA | GCCTAGAACC | CTGAGCACAC | 220860 |
| TCTCTAAACC | CTCCAACATG | CTCTTACTCT | GTTGCCTGCT | GAGCATCTTT | GATCCACTCT | 220920 |
| TGAGGCTAGC | AGTTTTCCTT | CCATTCAAGA | TCTCACAACG | TGTATTGTTC | TCTGCAGATT | 220980 |
| TTTTAAACAT | GCAATTTTAT | TTTTTAATTG | TTAAAAATAT | ATTTATTTCA | GTGCACTGAA | 221040 |
| GCTCAAATGT | GTGTGTTTTA | AAATCTAGTG | TCCAAGGTTC | ATTACCCCAA | TTGTTTAAGC | 221100 |

| | | | | | | |
|---|---|---|---|---|---|---|
| AAGTCTAACA | ACAAAAGGGG | CACATTTTAA | TTTTCAATTT | TTTTTTGTTC | TAGCCTACAG | 221160 |
| TTGAGTTTGG | GCAAATAATA | GTAGACAAAA | AAGTGAAAAG | AAAACTAAGG | ACAAGAAAAT | 221220 |
| AAAGGAAGGG | AGAATGGGGG | GAGAGGAGGG | AGAAAAGTGA | AAACAAAAGT | TTATTCATAT | 221280 |
| TTCTCTTGAA | TCCAATTCTT | TTACCATTTG | AAAACTTGAT | ATGGTCAGAG | AATAAGCCTA | 221340 |
| GAATTTAAG | TGATGAGGAT | AAGGTTTTAC | CACAGGTAGC | CTCCTCTACA | TAGGTCTATT | 221400 |
| TCCTCATAGA | ATGAGAGAAG | CCCCATCATT | TCTGCTCTTT | TACCCTTCTG | AGCCAGCAGC | 221460 |
| AAGGAGATCT | ACTATCAAGG | CATGAGCAAC | TGTAGAAACA | TGAGACCAGA | TGTCTCTATT | 221520 |
| AATTATTCTA | CAAATTGCGC | ATTGGATGAT | AAGGTTACAT | GAATCTTTAA | ATCAGCAAAC | 221580 |
| CAAAGTCCCA | TTATTATTAC | ATATTTTTC | CTCCTCAGAA | CTGAAGTGGG | GCGGGGTACA | 221640 |
| GTGACTCACA | CTAGTAATCC | CAACAATTTG | GGAGGCTGAG | GCAGGAGGAT | CACTTAAGCC | 221700 |
| CAGGAGTTTG | AGACCAGCCT | GGGCAACATA | GTAAGACCCC | ATCTCTACAA | AAACTTTTT | 221760 |
| AAAAAATTAG | CTTGGCATGG | TGGTGTGCAC | CTGCTGTGGT | TCCAGATACT | CAGGATGCTG | 221820 |
| AGGCAGGAGG | ATGGCTTCAG | CCCAGAAGGT | GGAGGTTACA | ATGAGATGCG | ATTGCGCCAC | 221880 |
| TACACTCCAG | CCTGGCAGCC | TGGGCAACAA | AGTGAGACCC | TGTCTCTGAA | AAAAAGAACT | 221940 |
| GAGGTCAAGG | AGTAGTAAGA | AAGTGGCTCA | TTCTCCAGAT | TTACTCTCTT | TTTCTTAATT | 222000 |
| ATAATGAACT | CATGATACTT | GAGGATATGT | CAAACTGATC | TTCAGACCCC | AAAGAAATTA | 222060 |
| CTCAGAGCCT | AGAATACCTT | TCAGGAAATG | TTACAGTGGT | ATACTCTACT | CAATTTAATT | 222120 |
| TTATGCTTGG | TCATCCAGGA | TTACACAGGC | TAAAGGTAGG | AAAAGTTTCA | CTAATTTTA | 222180 |
| ATGTCTTTTA | ATTTAGGACT | ACTGGGATTG | TCTGTCAATG | TGCTGAATAT | ATATATCCTT | 222240 |
| CCAAATCTGG | AAGATTTAAG | AGAAATGATA | GTTATCATTC | TTTAAGTCCT | TAGGAATATG | 222300 |
| CCTAGAGAGC | TAATTTCATA | TGTTCAGGGA | AAAAAAGTGT | ATTTTTTCTC | AACCTGTTGG | 222360 |
| ACCCCGGTAA | ACATACTATG | ATCAACTGGC | ATTTTCATAT | CAAATAATTT | ATGAAATTCT | 222420 |
| TATAATTTAT | AGAAGGCCAA | CTCCTACCAA | AGTCTTCAGT | CATAAGCTGC | TTCAAGTCCT | 222480 |
| TTTAGGAGCG | TAAAGATGGT | TATAAATAAA | ATTTGTCAAA | CAGCAGTAAA | CACAGTGGTT | 222540 |
| TATATGCATT | AAGGATCTTT | AATCTTCACA | TACTTCTAGA | AGGTAGGTGC | TATTACCATC | 222600 |
| ACTGTAAAGG | TATAGAGAAG | GATACTAATG | CACAGAGAGA | TTAAATGACC | TGCCTCAGAG | 222660 |
| TCCCACATCT | TATATGTGGT | GATCTGGGAG | TCAAACTTGG | AGTCTGTCTC | CAGAAGCTTC | 222720 |
| ACTTTTTGTC | ATCATTGAGC | AGTGCTGTGC | AGCCATTTTA | CTAGCATGAT | ACCACGTCTG | 222780 |
| GAACTAGTGT | TCTATAGGTG | CTATTTCATT | TAATCTTCAC | CCCATCTTTA | TGAGTAGGGC | 222840 |
| AATTATTACC | ACTCTATAGG | CTCAGGGTAG | TTGAGTTTGT | CAAACTGTGA | CTGAAAGACA | 222900 |
| TTTAATTTTT | GGCATACTAT | TTACTTGTGC | TCAAGGTATA | TCAAGCAATG | GACTGATTTC | 222960 |
| ACTCAACAAA | GTATTTTAAA | AAGATGATTT | ATAAATAGA | AATGGGAGAA | AAAAACTACA | 223020 |
| AACTGTCTAG | GAATAGGATG | TTATGTTTGC | ACATTATTTT | CAGTAGAAAA | GAGTTTAGTA | 223080 |
| TGGATACTCT | CTTCTTGTAT | AAACCAAGAA | TGTTAAAAGA | AACAATTAG | TGATTCTCTA | 223140 |
| GAAACAATTA | GTGATTCTCT | AGAAACACTT | AAGATTGGCT | GTGCAGCACT | ATGGCTATCT | 223200 |
| CTGTGTAGTA | TTTTCCACTG | ACAACCAACA | TTTCCATGTT | AGGTAGGCCA | TGTCTTCACG | 223260 |
| ATTTCTGGCA | CCAGAGTTTT | TCAACTCCTC | CATTTTTGGT | AAAAATATCT | CATAAAGGAG | 223320 |
| CAAGTCTAAC | CATGTGAGTT | TGTTTAGTTT | TTTGTTTTTT | GTTTTTTTGA | CAATGGCTTT | 223380 |
| GTAACAACAT | TTAATAATCT | GCATATTAGA | GAAGCACAGA | AGTAGGGCAA | AAAAAAAGT | 223440 |
| TATGAGGGTA | ATTACAAATA | TTATAAGAAT | TCCTTAAAGT | ACAAATTGTC | TCCAAGAATT | 223500 |

```
TAATTGGCTT GTCTTAGATG AATAGGTCTC AAAGATCAGT TTGGTCAAAG ATCAGTTTGG    223560
TCAACTTTAG TTAAACAAGT TCATTTTCC  TAATTGATTA TTTTGACTCA AATGTGGGCC    223620
ACAGGCAGAA ATAAATTTTC TAGTAAATAT TCTTATTTAG GAACTTTTAG TCAAGTTATA    223680
AAGGTCCTTG TTACAAACCT GCAAAAAGTT AGCATGCCAA TATCTTAGTA AAATATAACT    223740
GAGATTTGTT TATTTGCTTG TTTTTTAATA CTTGGGAGGG CCAGATCAAA ATTTCATCAC    223800
TGGAAAGACA GATAATGGAG AAAAGGACAA AACAGAATAA TACCACAGGT AAAAGAAGGA    223860
AGAAGCTGTC TATTTCAGAC CTCATCTTCC TCTGTAGACT TTGAAGAGGA AACTTCCTAC    223920
TTCCAGAATT CTGGAGGTCT TTTAATGAAT CTCAGAACTG TATTTTAGT  GATAGTGTAT    223980
TTCTCAGTGA GATTCCAAAT GTGTTACAC  TGGGAAGCAC ATATCCATCT GCTCTGAAGT    224040
ATAAAGCAG  TATTTGTTGT TTGAAGTACT GAAAATGGAG GTTCCAGCAT TGTTATAATG    224100
TTGTCAGAGA AGATTGGTTA TTACATTAAG ATATGAATAT AAATCATGGC TATATAAAA     224160
TAAGAAAAAG ATTGAAGTCT TATTTAGAG  TGACAATCCA TAGTAAATTG AATGTACCAC    224220
ATTAACAAAC AGTAACAACT TTTTAAATAA GTAAAGGCTC AAGGTAGTCA TTATCTCGAA    224280
TGCTTACTTG TGTTTCTCTG TAGCTATAGT ACTTGATAGA GTCAGAGCTG TTTGGATTAA    224340
CCATAGCCCT TAAACAAAGC AGGCAATTGT GTTCCCGCAT AGGCATGACG AAAACAGAGG    224400
CAGTCATCCA AAACCTGCAT GGTCCTCTAC GCCCACACGT ATACAGTACG TGATTTACAA    224460
ATCTAAAGTG GCGAAAGCAA CAGTATCTAT TCTAAGGCAA TCATATGTTC TCTTATCTGT    224520
TTATCAATGG TTATTCTAAA CTGTGTAAAA ATGTTATTTG CATAAAACTA CACTGTTTCT    224580
TGTGATTTGT ATTTTGTACC CTCCAATTTA GAAATTGTCC AGGTATCCAA AGATTGAGAA    224640
TTAATTTACT CAATTTAATA ATATTCACCT AAATTCTTAA AGTTATCATA CACTGTGAAC    224700
TCAGTACTTA AGCTCACACA TTGAATCCTT ATAATTAGTA ACATAAAATT TAATTCCATT    224760
TTTAAAAATG ACATTATCTA TTATCATTTA ATTTGGTTCA ATGAATAATT TACAATTTTA    224820
GAATAATAAA TAAAGTGATG TTAACTCATG TAACCAGTAC AACTAGTGGA AGAAATTTAG    224880
TAAATGCAAG TTAAATTAGC TTTTGTTTTT GTTTTTAGA  ATATGAACCC TAAACTTGTG    224940
TATACTATAA TATTCTGCTA ATATTATTTT TACAGTATAA GAATAAAGAA GCCATTTTA     225000
AAATGAAATT ATTAAGCCAA TTTGTCCAAA AAAAATCTTG ATTAGATGTA TTATATATTT    225060
TCCTTATTAA AAAAACCTAA TAAAAGAGGT ATTAATATTT TTAAGTTATT TAAAAATTGT    225120
GAAGTATTTT TTTTACAAAA TACTTTAAGC TGTTAACTAA GACCACTAAT GAAACTCACA    225180
GTTAAACTTT TTTTCTCTTA ATTAGAACTT AAAGAGGTAG CACATTTAAA GCACAAGGAA    225240
AATTTTTGAT TTTTTTTTAG ACAAATGAGT TTTTATTTAA ATTGATGTAT TTAAGTCTT     225300
TATGTAAGCC AACTAAAATT TAAGATTACA TTATAATTTA TTAATTCCCT TAAGTGGATA    225360
ATTTCACAAT TATTTAAATT CATAAAATAA GATAGTCTTT TCTGGGCACG GTGGCTCACG    225420
CCTGTAATCT CATCACTTTG GGAGGCCGAG GTGGATCACC TGAGTTCGAG ACCAGTTTGG    225480
CCAACATGGC GAAACCCCAT CTCTACTAAA AATGCACAAA TTAGCCAGGC GTGGTGGTGC    225540
ACCTGTAATC CCAGCTACTG GGGAGGCTGA GGCAGGAAAA TTGCTAGAAC CCTGGAGGCA    225600
GAGGTTGCAG TGAGCCGAGA TTGTGCCACT GCACCCCAGC CTGGGCCACA GAGCAAAATT    225660
CTGTCTCAAA AAAAAAAAA  AGATAGTCTC AATCTTATTG CCAATTAGGA AAGCTAACCG    225720
TGCTAATAGA ACAGAATTTA AAGTGGGTAA AAACAGAGCC ATAGGTTATC TATTTAGCAT    225780
GTTGATCAGT TAAAGAAATA AAAGTATGTA ATTAAGATCA GAAGTCCCTC AGGTGGCACC    225840
ACTGCTGAGA ATATGAATAA TTCTGATTCT CAGTTTAGAA GAAAATTCTA GTTTCCTAGT    225900
```

| | | | | | |
|---|---|---|---|---|---|
| TTCCAGCATC | ACATCCCTTA | CAATAAACTC | GTTAAGGTTT | AGAAAATATT | AAATCTTTGT 225960 |
| TTTATTCAGA | TATTGAAAGC | ACTCTTTTTT | TTCCCTGACT | CAATAGTCCA | ATTTGTAACA 226020 |
| ACATTATGTT | TCTTCTGTCC | TCTAACCTTA | CTTAAAGAAC | GTGAAGGGGC | AATAATGTGA 226080 |
| AATTACTAAA | ATTAATAATA | AGCTGTAGAG | CCTCTGCCAT | AGCAGTTATT | GAGACCAGAC 226140 |
| ATTCGGTTTC | CTTGATTTCC | TTTTGTCTC | CTGTTAGTCC | TAACACTTTC | TTAAAGTCAA 226200 |
| AAGTTATAAC | AGGGCAGCCA | TTTTATATTC | ATATCATCTT | AACACAGGAA | TACTGGTTTT 226260 |
| GCAGATATCG | ACAACTATTT | GGACTCAAAA | AAGACAAGTT | TTGGAAGGTG | GAAAGAGGCA 226320 |
| TACAAGCACA | AAACATCAAA | TCCCATGTAA | AGTCAGAAAG | AAAAACACCA | ACTCTAACCC 226380 |
| TGTGTCCTCA | CAGAGAATAT | CAACATCTTC | AAACAAAAAC | ACCCCAAAAA | AAGGTTAATA 226440 |
| AATAAACCAG | ATTTCCTGTC | CTCTCCACTG | ACTAATCACT | TAATGATGTG | ACCAGAAAAC 226500 |
| CAGAATTCAA | ATTCTACTAC | TGCCACCAAT | ATGCAACCAA | TCAGCCAAGT | CCAATTAGAA 226560 |
| TAACCAAAAC | AAACAAACGC | GGACGATAAA | CTTTTAGCAT | GCAAAAGCCA | AAGGAAAGTG 226620 |
| AACAGAAAAC | TCAAAGGGTC | CAGGGATAGA | CAACCTGTTT | CCAAGCACA | CATTTCTGTT 226680 |
| GGTTCTTATT | GTATGACTCA | CATAAACACT | GTCTTGGTGG | AAAATTCAGA | AATAAATGAC 226740 |
| CAAGAAGTTA | ATAATTTGCT | TACTGGGTAC | TTGTACAGAA | GAGAGAACAA | GCAATAGAAT 226800 |
| TATTTCATCT | AACACAGGCA | AAAACATAAT | CTATGTAAGA | GAAAGGGGAA | AAGGCGGGGG 226860 |
| AAACAATACT | GAATTTGTT | TGCAGATTTT | GGTTACACTG | ATTAGTTAGT | TGGCAGGTAA 226920 |
| GAAAACGGTC | AGTCTGAATG | GGAATAAGTG | ACCAGGTCCA | TTACAGGCAT | AGAAAAAAAA 226980 |
| AAAACCATTT | AGGCCCGGCG | CGGTGGCTCA | AGCCTGTAAT | CCAGGACTTT | GGGAGGCCAA 227040 |
| GGCGGGCAAA | TCACCTGATG | TCCGGAGTTC | GAGACCAGCC | TGACCGACAT | GGAGAAACCT 227100 |
| CGTCTCTACT | AAAAATACAA | AATTAGCCAG | GGTGTCGTGG | CGCATGCCTG | TAATCCCAGC 227160 |
| TACTCCGGAG | GCTGAGGCAG | GAGAATGGCT | TGAACCCGGG | AGGCGGAGGT | TGCTGTGAGC 227220 |
| CAAGATCGCG | CCATTGCACT | CCAGCCTGGG | AAACAAGAGA | GAAACTTCGT | CTCTAAAAAA 227280 |
| AAAAAAAAAA | AGAAAAAAAA | ATTTACTTGT | GAGGGACTCT | GGAAATTTCA | TTTCTCATCA 227340 |
| GAATTTCTCA | GATAAGTTAT | CTAGGCAAGG | CAGCCTGTGA | TTGCACAGCA | GTGTTCAAGT 227400 |
| ATAAGGCCTT | GTCTGGCACC | AAAGACAGGC | CTTAGTTTAT | TTCCAGGTG | TGAAAGAAAT 227460 |
| TGCAGATTTA | AGATCACACA | GTCCTTATGT | TAAATAACTG | TAACCTAAAT | TACATGGTAT 227520 |
| TTAAGTTTGT | AAAAATCTGC | TTTAACACTA | ATTTTATTTA | TTGTATATTC | CCGGTTTTA 227580 |
| ATGGAGAAAG | CAAACTTCTA | GGTGCTAAAA | ACGTGTTCTA | GACTTGAATA | AAAAGATAGG 227640 |
| TAGACTACGT | CTAACCCTTC | ATCTTAAAAT | CTTTACCTGG | AAAAGACCAT | GAGTAAAATA 227700 |
| CTTAAGGGAA | TGTGGAATTT | CCCAGGCCAC | AAAGCGGCCT | GCAGTTGTCT | AGGAAGGGAG 227760 |
| AGTCCTCTAG | GAGATACAGT | GTATGTGCTA | AGTTTAATGA | CGTCTCCTCT | TCATTCTCCC 227820 |
| CCACCCAGCG | CCTAGTCCTT | ACTGGCCTTC | AGTTCAGTGT | TCGAAGGCTT | GTCAATTTAC 227880 |
| CCAGCAGTTA | AGAGTTGGCT | TCTCCTAAAG | CAACTTTCAA | ACTTGTCTGC | ATGTTACAAG 227940 |
| CCCCCTACGG | AGATTTTAAG | TTTCAATCAG | GCAACACACC | ATTTATGGCT | GACTGAGCAC 228000 |
| TGGGATTCAA | GCAAATTTG | ATTTGATTTG | AATCTTGAAT | AAACCAGTTG | AATAGAATAA 228060 |
| GATGTATGAA | GCAACATCTG | GCGCAGTGCT | TACATCTTTA | GTTCTGTACT | GCCTTAGTGT 228120 |
| TGTTATCAAA | ACTGACGCAT | ATTAGTTAAA | AGACTATTAC | CGGGGCAGTT | GGAAACCCAG 228180 |
| GAGACACACC | TTCAGTATAC | TACGAAGGTG | TGCGCCACGA | AAACAGAGGG | GGAGTCCTTC 228240 |
| CTTAGGCAGT | TACTGCCCAG | GTTCCCACTC | CGGTCCGCTA | TGTAAATCAG | AGTCTCAAAA 228300 |

-continued

```
CAGCTTTCCC  TCGATTGGTT  AATATTTAAA  ATGACAGGAC  AGCCTATTGG  CTAGAAGCTG  228360
GTGGCGAAAT  TATGACATTA  CGGCAACCGT  TGATCCTGGC  GACGTAGACA  GGGACAGACA  228420
GCTGGGTCTG  AAACCTAAGC  GAGCCTGCGG  TTTCTTCCGG  GAACGCCGAG  TTAGCAAAAT  228480
GGCCGCTTGT  CTCCATTTTA  AATTTAAGCA  CAACGAATTG  ACCCCAAAGC  CATTTTTAAT  228540
GGCTGGCTTC  TTTCGGGTTC  AGGACCCTTT  GTCCTCTCT   AAGCTGCAAC  ACTTGTCCCC  228600
ACCCCTCTCC  AGTTCCTATA  TTCTAATACC  CCTCCGCCGC  CAAATAAAAT  TTGGCGTCTG  228660
GCCACAGCTC  TTTTAGTGGG  TATCTGGGTG  GCTCTTAAAA  GAGCCTTTGG  GGTTAGGTGT  228720
TAAGACGCTT  ACTTGGAATG  TTTACTTGGA  GCTGGTGTAC  TTGGTGACGG  CCTTGGTGCC  228780
CTCCGACACG  GCGTGCTTGG  CCAGCTCTCC  GGGAAGCAGC  AGGCGCACGG  CCGTCTGGAT  228840
CTCCCTGGAG  GTGATGGTCG  AGCGCTTGTT  GTAATGCGCC  AGGCGGGAAG  CCTCGCCCGC  228900
GATGCGCTCA  AATATGTCGT  TAACGAAAGA  ATTCATGATG  CCCATGGCCT  TGAAGAGAT   228960
GCCAGTGTCG  GGATGGACCT  GTTTCAGCAC  CTTGTACACG  TACACAGAGT  AACTCTCCTT  229020
GCGGCTGCGC  TTGCGCTTCT  TGCCATCTTT  CTTCTGCGCT  TTGGTCACTG  CCTTCTTGGA  229080
GCCCTTCTTC  GGGGCGGGAG  CAGACTTGGC  TGGCTCAGGC  ATCTTAAAAC  ACCAGAAATG  229140
TGTCGAAAGT  AAAGAGCGGA  TTTCTGCTAC  TTATAGGGCT  TTTATGCTAA  TGAGGGATGG  229200
AGAGTACCTC  TTAGTTAATT  GGAAGACAAA  CTGCACAGTT  GTCATCCGTG  GGCAGAGCTA  229260
TGCAAATGAG  GTATGAAAGT  ACAGCTTTTC  TATTGGCTAT  CTGACTAGCA  TTTGCTACCG  229320
ACCAATCAAA  AAGTCGGATT  TACTCCCCAG  GAACTACCTA  TAAAAGCGGC  CATGTTTTAC  229380
ATATTTCTTG  ATTTTGTTTG  TTTTCTCGTG  AGCTTAGGCC  GCTGGTTTTG  GTGATTTTTG  229440
TCTGATTGCA  ATGTCTGGAC  GTGGTAAGCA  AGGAGGCAAA  GCTCGCGCCA  AAGCGAAATC  229500
CCGCTCTTCT  CGCGCTGGTC  TCCAGTTCCC  GGTGGGCCGA  GTGCACCGCC  TGCTCCGTAA  229560
AGGCAACTAC  GCAGAGCGGG  TTGGGGCAGG  CGCGCCGGTG  TACCTGGCGG  CGGTGTTAGA  229620
GTACCTGACC  GCCGAGATCC  TGGAGCTGGC  CGGCAACGCG  GCTCGCGACA  ACAAGAAGAC  229680
TCGCATCATC  CCGCGCCACT  TGCAGCTGGC  CATCCGCAAC  GACGAGGAGC  TCAACAAACT  229740
GCTAGGCCGG  GTGACCATTG  CTCAGGGCGG  CGTCCTTCCT  AACATCCAGG  CCGTGCTTCT  229800
GCCTAAGAAG  ACCGAGAGTC  ACCACAAGGC  CAAGGGCAAG  TGATTTGACA  GGTATCTGAG  229860
CTCCCGGAAA  CGCTATCAAA  CCCAAAGGCT  CTTTTCAGAG  CCCCCCTACC  GTTTCAAAGG  229920
AAGAGCTAAC  CTCACTGCTT  GTAGGTAGAA  GGAAAAAAGG  CACTAAGGTA  AGTTAATTTT  229980
ATGCCAACCT  TGAGCAAAGC  GTATTACTGC  TTTTCGGTTT  TTGGGGAGCG  CTGTTACTAA  230040
AGGTTGGTCT  GTTTGTATGT  AATAGTAGGT  CAGTTACGTA  CTATCATACT  CTAAAGAAAT  230100
ATTCTAGTTA  ATGCTTTGTA  AGATCGACCA  TAGTTAGTGC  CTAACAGTTT  ACATGCAGGG  230160
ATGCCTCGTG  ATCTAAACAC  TTCGTTGTGA  TTACTTTAAA  AATGTAAATT  GAAGGCAAAA  230220
CTCTAACGTG  TTGGTAACCT  TGTTTGGTCC  TCCGACTAGT  CCCCCGTCTA  TTTTTTTCTC  230280
AATTTAGGCT  GTAGGCAGCC  TCACTTTCCT  AATTCTGTGA  GAGTTATAGG  TCCCATTCCT  230340
GCTAAAGTGC  AGAGTATATT  ACCTAAAAGT  TAACCAGGGA  GTTGAAGGT   GTCTGTAAAA  230400
CAGACTAATG  TCCCTAATGT  AGAACGGTGC  CTGACATGCA  ACTTACTCTT  GTATTTTAAG  230460
AAGCTCAAGC  GTCTAGGTTG  CCATTACAGG  CAGAAAAGGA  AATAGAGTGG  GGCCTGTGGC  230520
CACTCAAAAA  CCTTTGCTTT  CTGCTCACCC  CTCTAATCCT  ACCACTTTGG  GAGGCCGAGG  230580
GGGCTGATCA  CCTGAGGTCA  CGACTTCGAC  ACTAACCTGG  CCAACATGGT  GAAACACCTC  230640
TCTACTAAAT  AAAAATAATA  AATAAAAAAA  TAAGTTGGGC  GTGGTGGCAC  ATACCTTGTA  230700
```

| | | | | | | |
|---|---|---|---|---|---|---|
| ATCCCAGCTA | CTCTTGAAGC | TGACGCAGGA | GAGTCGCTTG | AGCCTGGGAG | GCGGAGGTTG | 230760 |
| TAGTAAGCCG | AGATCGTGCC | ACTGCCCTCC | AGCCTGGGCA | ACAGTGAGAC | ACGGTCCCCC | 230820 |
| AAAAAAACCT | TTGCTTCTAG | GGATCTGGTA | ACAGCTGCCC | CACCCACAAG | AAATGGAGAT | 230880 |
| CTGGGACCAT | GGACAAATTT | CTAGAGACCT | ATTTTCCTGG | ATTCTGTGAA | TCTCGCCGAG | 230940 |
| GTTTTCTTCC | GGATCTCGGT | TTCTGCATTT | TTTTGTTTGT | TTGCTTGCTT | TTTTGAAACG | 231000 |
| GAGTTTTGCT | CCTGTTGCCC | AAGCTGGAAT | GCAGTGGCGC | GATCTCGGCT | CACTGCATAC | 231060 |
| AAACTCCGCC | TCCCGGGTTC | AGACGACTCT | CCGGCCTCAG | CCTCCCTAGT | AGATGGGATT | 231120 |
| ACAAGCGCCC | GCCACCAGTA | GAAACGGAGT | TTCACCAGGT | TAGCCGGGCT | GGTCTCGAAC | 231180 |
| TCCTGACCTC | AGGTGATCCG | CCAGCCTCTG | CCTACCAAAG | TGCTGGGATT | ACAGGCGTGA | 231240 |
| GCCACCGCGC | CCGGCCGGTT | TCTGCTTTGA | TCGGAATTAA | GTGGGCAGAA | AAGTCTAGGC | 231300 |
| GGGCTAAGTC | TTGCCTATGC | ATCTGCGCCC | AGCTGCTCAG | ACTGGCCAAA | CAGACCCAGT | 231360 |
| CGTTTAGTCT | AACGCTTCTG | GAACTCCACT | GAAGCGTTTT | GCATTGTTTC | GTTTGGAGCC | 231420 |
| TTCAAATCCG | AGTGTGTGGC | AGGAGATAAT | AATCCTAGCA | GAAGCTGTTT | ACTGCTGACG | 231480 |
| CGCCTCCCAC | TTCCCAGATA | CTGACACCGG | CTCAGGGCGG | ATCCAGCCTT | TTCCGCTCTT | 231540 |
| CCCTCCCTCC | ACCCCCTCCT | TTCCCTACAA | CTACTCTCAA | AGGAAAAGGG | TTGGATGTCC | 231600 |
| CATTTGGGTG | AAAACAAAGT | GGCATAAAAG | CAAATGATCA | CCTTTGATAG | CCACATATTA | 231660 |
| GAATTTTCCG | AGGGTATTTT | TAAATTACAA | CGATTCTAAT | GGGCAGCTGG | GCTGAGAATC | 231720 |
| ATCAGATTTG | AAGGTCTGGT | TTCACATGGC | TCTTGGGCTG | AGAAGACCGG | ATTTTCCCCC | 231780 |
| CCCAGCATTT | CCTGTATGTC | CGAGAATTTC | GATCCTAAGG | TTAGAATTGC | CTTATGGGCC | 231840 |
| TTGGAATCCT | TTTTATTCAC | TGACCAAATT | GCCTTGATT | CCAGCTCCCA | ATCGGTGTGT | 231900 |
| GACCTTGGCC | TAGGGCTTAA | TCTCTTCCTA | CCTCCATCTC | TTCCTTGTAT | GCTTTTGCTC | 231960 |
| ACCTTGAAAT | GAAAAGAACC | TGGCTCAGCA | AGTGTAGATT | CTGAAATCAG | AAAACAGGCT | 232020 |
| GAATAAGAGA | GATGGTTTAT | TAGGCACTAC | TGTGTGCCAG | GCACATTTCA | TGAGCTTCCA | 232080 |
| GTATGTTAAT | TCATTTAATC | CAACAATCTA | AGAGATAGGT | TTTATCCTTA | TTCCGAATTT | 232140 |
| TGAGATGAGC | AAACTAAGAA | ACAGCTTAAA | GAACTTAAGT | TGTAAGGCCA | GGAAAACAGT | 232200 |
| ACTTATAACA | GCTGACTATT | CTATAACCAC | ACCTCCTTAA | GAGATTATTG | TCAGAAAAAT | 232260 |
| AGAAAGAGTA | AAACATCCAT | ACATAATGGG | TAAACTTTGT | CCACATACCA | GAATGTTACT | 232320 |
| AATGGCTTTC | TAACCTCTGA | AGAATTTAAG | GGAAGGAGGA | AAGGTAATTT | TCCCCAGGGA | 232380 |
| ATCTACACGA | AGAGGTAAAT | CTTGACAATG | TATTAATACT | GTAAACCCAG | GGAAAAAAAG | 232440 |
| CCAGTACAAT | TTTTATTTAG | GGTGTGGCAA | ATAAACAAA | GGGACACGTG | AAAACATGGC | 232500 |
| TCAGTAAAGA | GCTACAAGAC | TTGGTGCAAC | TGACTTATTG | TGGTGAGTGA | GAAAAGGAGA | 232560 |
| GAGAGAAAAC | TTGAATTTCA | ATTCTTCTCT | CTGGGCTCCA | ATAACAAGAT | TTTGTATTCG | 232620 |
| GTCTATTTAG | TAGTGAATGA | TACATTGTGT | TAAGTTTGTT | AACCTAGAGG | CTTTCATCTT | 232680 |
| AAGCAGTACT | TAAGATGTAG | ACCCCTCTT | ATTCAAATAC | TGATAATCAG | CATAGAACTT | 232740 |
| GGCATACAAG | AGACACTTGG | CTGTTGGGCA | TTGAGAAAAT | GTTGAACTGA | ATGAATCAAT | 232800 |
| GACTTAGGCA | GCCAGGAAGC | ACTTTGTTGT | AGAGAGTTGG | TTTATTACTA | AGGAAGACAT | 232860 |
| TAAGTATTAA | ATATTAGACT | AATAGGTTGC | TAATAGTGTT | TTCTCTTTCC | AATAGAAAAT | 232920 |
| GTCTTCTGAG | GCTGATCTGG | TGTCTCACAT | CTGTAATCCC | AGCACTTGGG | GAGGCTGAGG | 232980 |
| TGGGTAGATC | ACCTGAGGTC | AGGAGTTTGA | GACCAGCCTG | GCCAACATGG | CGAAACCCCA | 233040 |
| TCTCTAATAA | AACTACACAA | ATTAGTCAGG | TGTGGCGGTG | TTCACCTGTA | GGCGCCTGTA | 233100 |

| | | | | | | |
|---|---|---|---|---|---|---|
| GTCCCAGCTA | CTCAGGAGAC | TGAGGCAGAA | GAATCACTTG | AACCCCGGGA | GGTGGAGGTT | 233160 |
| GTAGTGAGCC | AAGATCGTGC | CACTGCACTC | CAGCCTGGGC | GACAAAGTGA | AACTCCGTCT | 233220 |
| CAAAAAAAAA | CCAACCCCAT | CTCTACTAAA | AAATACAAAA | ATTAGCTGGG | CATGCTAGTG | 233280 |
| CACGCCTGTA | GTCCCAGCTA | CTCGGGAGGC | TGAGGCAAGA | GAATCACTTG | AATATAGGAG | 233340 |
| GGGGAGGTTG | CAGTGAGAGT | GAGACTCTCA | AAAAAAAACA | ACAAAACAAA | AAGTAACAAG | 233400 |
| AAAAAGAAA | CTATATTCCA | AAAATCCAAA | TTTCACTGGC | AGTTGTTCT | GGGAGCTTCA | 233460 |
| GACACATAGA | AGGTGTCAGT | TAACCAGTTC | TTACCTAAGA | GGTACTGCTA | AGAGCCTAGT | 233520 |
| CCCTAAGCAA | AGGGAGCTTC | AGAGAAACAC | AGAAGGTGCC | AGTTAACCAG | TTCTTACCTA | 233580 |
| AGAGGTACTG | CTAAGAGCCT | AGTCCCTAAG | CAAAGGACAT | TCCTCGTAGC | TCTGTCCTGT | 233640 |
| CTCCTCATCT | CCAAAATACT | TTACCTTCTA | CTTTGAAATG | CCCACTATTA | TATTCAAAAG | 233700 |
| CCCTAGTTAC | TTCCAGGGAA | AATTATCTAT | TGAGCAATGA | ATTTCGGTAG | CTTCAGTTGG | 233760 |
| ATTCCAACTC | TTGAGCAAGT | TTTCATCTCC | CTTGCCTGAA | TGGCCCTGGG | GAGGACTATT | 233820 |
| TAAATTGGGG | CGAGTGGATG | AGGATGCTAA | ACCTAGAGGT | CTCCCAATTA | CCAAAGGCAC | 233880 |
| CTGGGCACCA | GGGACTAAAG | TTTGTCTCAG | GAATTTACTG | AGATATGAGG | CTGAGATAAA | 233940 |
| ATCATTTTTT | GGTACATAAG | GTATCTTGAA | CAAAGCAGAT | CAGTTTAACA | CAAAATCAAC | 234000 |
| AATCGTAATT | TCCCTTTTTA | AATTTCCAAA | TCTATGTAGC | AATATCCTTT | CCTTTAATTC | 234060 |
| ATTCATCATC | TCTATTCACT | TTTTGTATTC | TGTAAATCAT | TTGAACTTTT | ATAAGAATTA | 234120 |
| TATTTTCCCC | TTGAGGTCAC | AAAAAAGAAA | GTATTAGAAA | TTTTATAACC | AATTTTTAAA | 234180 |
| AAATTATATT | TTAAGGTTAA | ATACAAACCT | TCTAAAGGTT | TGTCATCTGT | TGATCCTAAA | 234240 |
| TTATAATTAT | AAATTTATAT | ATTCCTGTTG | AATATAATGC | ATGTGTGTTA | CAAGATTATT | 234300 |
| AGCAATTTGA | GAATTTCCCG | TGCATATTGG | AGATGAGCAA | ATGGAATAAG | TGCTCATGTG | 234360 |
| TAGCGACAGG | ATTCTCTATT | TTATTTCAAT | ACTTAATATT | GTACCAAACC | AAGTAAGAGG | 234420 |
| AGCATCATGA | GAAAATGTAC | TAAAGGACAG | TCATTACCTA | TATTTACACC | TAGAAAAGAA | 234480 |
| AACTATATTA | TTGATAAACT | GATAAATCTA | TTTTATGTAT | TTATTTATTA | TTTTGCTCTG | 234540 |
| TCATCCAGGC | TGGAGTGTAC | TGGTGCGATT | TCCACTCATT | GCAACCTCCT | GCTCCCAGGT | 234600 |
| TCAAGCAATT | CTACCTCAGC | CTCCCTAGTA | ACTGGGACTA | CAGGCATGCA | CCACCACACC | 234660 |
| CAGCTAATTT | TTATATTTAT | AGTAGAGACA | GGGTTTCACC | ATGTTGGCCA | GCCTGGTCTC | 234720 |
| AAACTCCTGA | CCTCAGGTGA | TATGCCCACC | TCAGCCTCTC | AAATGCTAGG | ATTACAGGTA | 234780 |
| TGAGCCACCG | CGCCCAGTCT | GATAAATCTA | TATTAAAAAG | AATAAATATA | ACCATTGCAT | 234840 |
| CTTCAACAGA | AATTGGAATA | TGGCATGTAG | ATTTCAAAAT | AAAATGAATT | CTCTGGCATT | 234900 |
| GAATTACTGT | ACTCATGTTG | AAGAAATGTC | AGAACTTCAT | TGGATGTTAT | TATATTACAG | 234960 |
| TTGTTTGTTT | GAGTTGTAGT | TTGGGCAGAG | TAAAGGAGCC | AACATGTCTT | AGGATTTAGA | 235020 |
| ACTTGTGCAC | ATTGCCTACA | GTTGAAAGAA | GAAAGCATGC | TAAATTCCAG | CCTCTTTGGT | 235080 |
| ATGTGGTTGG | GACGTAAAGT | TTTACCACAT | CCTTCATTGT | CTTAGCCTAC | TCAGGCTGCC | 235140 |
| ATAACAAAAT | ACCAGAGACT | GGATGGCTTA | AACAACAGAA | TCTTTTTTTC | CATATCTAAG | 235200 |
| AGGCTTGGAA | CAGAAATTCA | TTTTCTCACA | GTTTTGGAGC | CTGGAAGTTT | AAGATCAAGG | 235260 |
| TGCCAACATA | GTTTATGGTG | AGAATCTGTT | CCTGGCTAAC | AGATGGCTGC | CATCTCACTG | 235320 |
| TGTGTTTGTA | TGGTGTTTCC | TTGGTGCCTG | CGTGGAGAGA | GAGCTCTAAG | TGTCTCATCT | 235380 |
| TCTGTAAGGA | CACCAGCCCC | AATGGGATTA | GGGCCCTATC | CTGTGATCTT | TAGTTTTATG | 235440 |
| TACCCCCTAA | AGGCTCTATG | TCCAAATGCA | GTCACACTGG | GGTTTAGGGT | TTTAATAAAT | 235500 |

-continued

| | | | | | |
|---|---|---|---|---|---|
| GAATTTTGGG | GGACACAGTT | TAGTCCATAA | CATTCTGTCC | TTGACCTGCC | AAAATGTATG 235560 |
| TCCTTCTCCC | ATACAAGATA | AATTTATTCC | ATCCAGCCG | GGCATGGTGG | CTCACACGTG 235620 |
| TAATCCCAGC | ACTTTGGGAA | GCCAAGGCAG | GCGGATCAGA | AGGTCAAGAG | ATCGAGACCA 235680 |
| TTCTGGCTAA | CACGGTGAAA | CCCCATCTCT | ACTAAAATAA | AAAAAAAATT | AGCCAGGCGT 235740 |
| GGTGGCGGGC | GCCTGTAGTC | CCAGCTACTC | TGGAGGCTGA | GACATGAGAA | TGGCATAAAC 235800 |
| CCGGGAGGCA | GAGCTTGCAG | TGAGCCAAGA | TGGTGCCACT | GCACTCCAGC | CTGGGCGACA 235860 |
| GAGCTAGACT | CCGTCTCAAA | AAAAAAAAA | AAATTATTCC | ATCCAACAG | CCCCCTGAAA 235920 |
| GTCTTAACTC | ATTCTAGCAT | CAATTCTAAA | GTTCAAAGTG | TCATCTAAAA | AATCATCTAA 235980 |
| ATCAGGTTAC | GGGTGAGGCT | CAATGTGTGA | TTCATCCAGA | GACAAAATTC | CTTTCCAGCT 236040 |
| TTGAACGTGT | GAAACCAGAA | ATGTTACATG | CTTCTAAGGT | ACAATGGTGA | AACAGGCATA 236100 |
| ATAGACATTC | CCATTAGAAA | ATGGAGAAAT | AGGAAAGAAG | GAAGGTGTAA | TGTGTCCTAA 236160 |
| TCAAGTCCAA | AACCTGGCAA | GGCAAATTCT | GTTAGGTCTT | AAGAAAACC | CTCTTTGGCT 236220 |
| TGATGCCCTG | ATTTCCAGGC | CCAGTGGTGT | CTCAGTGTCA | CCTCTGGCTC | TGTAGTTGGC 236280 |
| CTACTCCATC | TGCCCTGCCT | GAAGTCTCGG | TCTTTCAGTT | TGGTGGGGTC | CCACCCAGGC 236340 |
| AGCCATCTGT | GAGAGACTCC | CACACAGTTC | TGCAGGGCAT | CTTTGAAACA | GGTAGAGTCA 236400 |
| GCCTTGACTA | CATGTTCCCA | CCCCCACCCT | ATCCCATCTG | TACTCTCTGA | GTCTGACATC 236460 |
| AAAGTGGCAG | CCCTGGCGGC | TCCTGCCTGT | AATCCCAGCA | CTTTGGGAGG | CCAATGAGAA 236520 |
| TGGATCACTG | GAGGTCAGGA | GTTCCAAACT | AGCCTGGCCA | ACATAGTGAA | ACCCCATCTC 236580 |
| TACTAAAAAT | ACAAAAATTA | GCTGGGCAAG | TGGTGGCAGG | AGCGCTACTC | GGGAGGGTAC 236640 |
| AGATTTAGAG | CCTGTAATCC | CAGCTACTTG | GGAGTCTAAG | GCAAGAGAAT | CCCTTGAACC 236700 |
| TGGGAGGTGG | AGATTGCAGT | GAGCTGAGAT | CACACCATTG | CCCTACAGCC | TGGGTGACAG 236760 |
| TGAGACTGCC | TCAAGAAAAA | ACAAAAGAGT | CAGCCCTAGT | GATCTTGTAA | GTTGCCTTTG 236820 |
| GTGGGTCAGT | CTTTCCTTTT | CTTAAAGAAT | AGTACACATT | GACAGCCAGG | TAGCTCTATG 236880 |
| ATCCTGTTCT | ATAGAATTCA | AAAAGTCGAC | AACCTTCCTT | TGTTCCTTTC | TGTTTTCTCT 236940 |
| GCCTACGTTA | GTTTAAATTG | GCAGTGTCTC | TGCTGGAATA | ATCCCATCTC | TCTTCCTGGC 237000 |
| TTCTGCTGAG | ATGGCTGATT | AAATCCTTGG | GTCACACCCA | TTATCTCTTT | ATCAAATGGT 237060 |
| TGTTCAGGCT | AGGCTCAGTG | TTTCACGCCT | GTAATCCCAA | CACTTTGGGA | GACTGAGGAG 237120 |
| GGCAGATCAC | TTGAGCTCAG | GAGTTAGAGA | CCAGCCTAGG | CAACATGTCA | AAACCCCATC 237180 |
| TCTATAAACA | ACAACAAAAA | ATTAGCCAGG | GTGTGGTGGT | GCATACATGT | AGTCCCAGCT 237240 |
| ACTTAGGAGG | CTGAGGTGGG | AGGATTGCTT | GAGCCTGAAG | GCAAAGGTTG | CACTGAACTG 237300 |
| AGATTGTGCC | ACTGCACTCC | AGCCTGGATG | ACATAGCCAG | ACCCTGTCTC | AAAAAACATA 237360 |
| AAAATAAAAA | TAAAACCAAG | AAAAAAAAG | AAAAGAAAA | CATTGTTCAA | CCATACCTCT 237420 |
| TCAAGAAAAA | CTTTCTCAAT | TTTTACAATA | TAGATTGAGA | AATCTATCCC | AAATCTCCAA 237480 |
| GTTCTGATTG | TGTTTTGCTT | AAAAATTCCT | TCTTTATTTC | GGCTCTTTCC | TCTCACATTT 237540 |
| CACTTTAAGC | AGTAAGGAGG | ACCTAAATCA | CACCTTCAAT | ACTTTGCTTA | GACATCTCTT 237600 |
| CTGGTAAATA | TCCAGTTTTA | CTGCTTATAA | GTTCTTTCCA | GTAAACACTA | CAGCGTAATT 237660 |
| CAGCCAAGTT | CTTGACACAT | TGTAACAAGA | ACAGTGATTT | CTACAGTTTC | CAATAACCTG 237720 |
| TCCCTCATTT | TCATCTGAGA | CCTCACAAGA | GTTGACTTTA | ATGTCCATAT | ATATATATTT 237780 |
| TTTGTGTGTG | TGTGGCGGGG | GGAGTGGAGT | CCTGCTCTGT | ATCCCAGGCT | GGAGTGCAGT 237840 |
| GGTGTGATCT | TGGGTCACTG | CAACCTCCAC | CCCCCGGGTT | TAAGCGATTC | TTCAGCCTCA 237900 |

| | | | | | |
|---|---|---|---|---|---|
| GCCTCCCGAG | TAGCTGGGAC | CACAGAAGCA | CATCACCATG | CCCAGCTAAT | TTTTGTATTT 237960 |
| TTAGTAGAGA | CAGGGTTTCG | CCATATTGGC | CAGGCTGGTC | TCAAACTCCC | GACCTCGTGA 238020 |
| TCTGTGCCCT | CAGCCTCCCA | AAGTGCTGAG | ATTACAGGCG | TGAGCCACCA | CGCCTGGCCT 238080 |
| AAAGTCCATA | TTTTAACCAG | CATATTTAAT | ATTCTATCCA | TGATCGTTAT | AAATCTAAGT 238140 |
| TTCTATGAAA | ATGGAAGCTT | TCTGTCCAGC | TCTCTTCCTT | TCTGAGCCTT | TGCCAGAATT 238200 |
| GCCTTTAATG | TCCATATTTC | TTTCAATAGT | CCCTTCACAA | TTGGCTTTTT | CTAGTATGAA 238260 |
| CCTCAAACTC | TTCCAGCCTT | TACCCATCAC | CAATTTCCAA | AGCCACTTCC | CCATGTTTAG 238320 |
| GTATTTGTTG | TTGCAGCATC | CCACGCCTGG | GTACCAAAAC | TTAGTCAGCT | TGGACTGCCA 238380 |
| TAACAAAATA | CTACAGACTG | GTGGCTTAAA | CGATAGACAT | TTATTTTCTA | ACAATTCTGC 238440 |
| AGGCTGGAAA | TCTAAGATCC | AAGTTGCCAG | CATAGTCAGT | TTCTGGTGAG | GATCTCTTCC 238500 |
| TGGCTTAAAT | TATTTCACAG | ACACCAGGCA | GATAACCATA | TCCATTCTTT | CCTGTATTCG 238560 |
| TTAATAGTCA | GAGCTAAAAG | TGTAGGGCTC | TAAATTTACA | CTTCAACAAA | TTGTTCTGTT 238620 |
| ATTAAGTATT | CACCTCAAAA | TGACCAGACT | ATACTATCCT | CTAAATTTTA | GAAACTTGGA 238680 |
| GCTTGGCTCT | GGTCCCTAGT | CTTTGTTCTG | TCTCATTAAT | GGCTTCATCA | ATACTACGGT 238740 |
| TCCAAAGACT | ATCTATATGC | AGTAAACTTC | CAATTTTACA | TCTCCAGCCT | GACCTTTTTT 238800 |
| CTGAAATGCA | AATGTGTGTA | GCCACATTTT | CACTTGACAT | CTCCATTTAG | AACTCTAATA 238860 |
| GGTCTTTCAC | CCTAAACACT | TCCAAGACAC | AGGAATAAAC | GTGCTCCTTA | AGCCTGTTAT 238920 |
| CCCTTCCAGT | TCTCCCCAGT | TCAATAACTG | ACACTACCAT | TTACTCAAAT | CAACATTCTA 238980 |
| AGAGTGTCAC | TTGCTACATT | TCCTTCATCT | CTACAAATCC | AAAGTATCTG | TGAGTCACGT 239040 |
| CACCTACATA | TTCAATACAT | GCAATAATTC | ATTCTCCATA | CTCCTTACCA | TGACTTAAGG 239100 |
| GCCCACTCAG | TGACCATCTC | TGGCCTCTGT | TCACCTCTTC | TGCTGTTCTC | CTTTGCTGTT 239160 |
| CCAGCCACGC | TGGTCTCTTT | TCACATCAAG | CAGCTAAGCT | CTGCCCATTT | AAGACATTTA 239220 |
| ACTTCTTGGC | CTCAATCTCT | GAAATGCCTG | TTTGATTTTT | CTTCTGGTGA | GCTCATTTTC 239280 |
| ACTCATCAGG | TCCCAGCTCT | GTTTCAGACA | AGGCTATCTA | AAATAGACCT | ACCTAAATGG 239340 |
| ATTAAAAATC | TGAGAATATG | AAATAACAAA | TATCAGATGA | CATTTTAGGA | GACCCTTTAT 239400 |
| ATACCTCATT | TGTGTGTGTG | TGTGTGTGTG | TGTGTGTGTG | TGTGTGTTTG | GAAATGGTGA 239460 |
| TGGAGGGTGT | CATTGCTAAG | TGAGGAGGAA | ACACAAAAGC | CATCTAGGAA | AGGACACAGA 239520 |
| CTAGATAGGT | CCAAAAGTGG | TTTAAGACAG | AATATATGTA | AAGAGAGTTA | TAGAAAGAGC 239580 |
| AATAAGTTGG | GATAAAGGAT | TTCCAAAACA | TATACGGGGT | TAGTAACCTC | AATTTACAGG 239640 |
| GACAAACTGC | AAAACGTTAG | TGAAAAGGCA | AACAACATAA | TATAAAAGAT | GATTAAACGG 239700 |
| TATTTTATAT | CATGTATTAA | ATTCATATGG | CCAATACATA | TGAAAAACAA | GAAACAAAAA 239760 |
| ACCTTCCTAG | TAATTCAAAA | TTATGCATAT | TAATACAACA | AAGGGATACC | ACTTCTTTTT 239820 |
| TTTTTTTTTT | TTTGAGACAG | AGTCTTGCTC | AGGTACCCAG | GCTGGAGTGT | AGTGGCATGA 239880 |
| TCTCAACTCA | CTGCAACTTC | CACCCCCTGG | GTTCAAGCGA | TTCTCCTGCC | TCAGCCTCCC 239940 |
| GAGTAGCTGG | GACTACAGGC | GCCTGCTACC | ACGCTCAGCT | AACTTTGTA | TTTTATTAG 240000 |
| AGATGGGGTT | TTACCATGTT | GGTTGGCCAG | GATGGTCTCG | GTCTCTTGAC | CTCGTGATCT 240060 |
| GACGGCCTCA | GCCTCCCAAA | GTGCTGTGAT | TACAGGCGTG | AACCACTGCA | CCTGGCCTAA 240120 |
| TTTTTGTATT | ATTAGTAGAG | ATGGGGTTTC | ACCATATTGG | CCAGGCTGGT | GTCGAACTCC 240180 |
| TCCTGACCTC | AGATGATCCA | CCCACTTCAG | GCTCCCAAAG | TGCTGGGATT | ACAGGCATGA 240240 |
| GCCACTGTGC | CCAGCCTGGG | ATACCATTTC | TTACCTATGA | ATAGACAACC | ACTAAAGCCA 240300 |

| | | | | | | |
|---|---|---|---|---|---|---|
| GTATACTCAG | GACTGCAAAG | GATGAGGAAG | AATTGCCATT | GTCATATAGT | TTTTCATAAC | 240360 |
| TTTTCCTGAC | AATGTCTATT | AAATTGTATT | AATAGACATT | TGGAAAGGGA | GAGTGTCAAC | 240420 |
| AATCTAGAAT | AAAGGCCCCA | CTAGGTAAGG | TTACATATGT | AAGGACTCTT | TCAAAACTGT | 240480 |
| CACAAGAATT | CAGGTACGGT | GGCTCATGCC | TGTAATCCTA | GCATTTGGG | AGGCTGAGGC | 240540 |
| GGGTGGATCA | CTTGAGGTCA | GGGGTTTGAG | ACCCGCCTGG | CCAACATGGT | TAAAACCTAT | 240600 |
| CTCTACTAAA | AATACAACGA | TTAGCCATGC | ATGGTGGCAC | ATGCCTGTAA | TCCCAGCTAC | 240660 |
| TCGGTAGCCT | GAGGCAGGAG | AATAGCTTGA | ACCCAAGAGG | CAGAGGTTAC | AGTGAGCCGA | 240720 |
| GATCGCACCA | CTCCAGCCTG | GGCAACAGAG | TGAGACTCCA | TCTCAAAACA | AAACAAAAAA | 240780 |
| ACTACTCAAA | ACTGTAATAA | GAAAAAAAAA | AACCTAATTA | TACATGTAAA | ACATTTAAAT | 240840 |
| AACTAAAATA | AGAATACTGT | TGACATAGTG | AGACATCCAT | TTATACTATG | GAATGTTATG | 240900 |
| CAGCTACCTG | AAACAATAAT | CCGGTGAAAC | AAAATCACAC | ACACAACTGA | TGAGAGTAAA | 240960 |
| TAGAGAACCG | TATGGAAGAA | AACATACCAC | AGTAATTATC | TCAGATAGCT | GAAACTAAGT | 241020 |
| TGGTGCAAAA | GTAATTGTGG | TTCTTACCAT | TACTTTCACT | GGCAAAAGCT | GCAATTACTT | 241080 |
| TTGTACCAAC | CTAATAGAAT | GGGGTGAGGA | GAGGTAAACC | TTTATAAACA | TCTCTGTGTG | 241140 |
| AACTGTTAAA | ATGAGCAAGT | ATATTTTTT | TAAAGTATAA | AGAGAGAAAA | AAGTAAACTT | 241200 |
| TCTCCATTTC | CCACCTCAAA | TTATGTTCTG | TCACTCATCC | TGTTTAGATT | CTTTCAAATG | 241260 |
| CAGTTTGAAG | TTTTATTTAT | GAGATTCCTT | GTTGTTTGCC | TCTTTCCATT | AAACCTAGCT | 241320 |
| CCACAAAGTA | GGGACCTGAT | GTATTCATTC | ACTGTTATAT | CCCAGCATCT | AGCAGAGGGC | 241380 |
| CTGACACTTA | GTGGGAACGC | AAGTATCTGG | TATATAAACC | AGAGAATAGA | TATTTTTTA | 241440 |
| GCCCAGAAAG | CTGTTTCACT | GCACAGAGTG | TAATTATCTG | AATTTCTATA | AAAATGTCTA | 241500 |
| TCTATAAATC | ATTGTCAATA | CATTACCTAC | TCACCTTACC | CAGCTACCAG | GAACACTATG | 241560 |
| AAGTTTTGAA | TTACACCCCA | TTTGTTTCC | ACACTCTTAC | CATTTTCCCA | GTTTCTGCAC | 241620 |
| TGACCTCTCC | AGACATCATG | TGTACTGATA | ATTCTAAGTT | GTCTAGATTG | TTAATTCTTT | 241680 |
| TAAGGGCCTG | TTCTCTGCTA | GCTGGCATCA | TGCATAAAAT | AATTCTCTTT | AATATGCTCT | 241740 |
| GGGTCTAGGG | TTAATAGATG | TTTGCTTAAA | ATCATGGAAA | GAAAATGGTC | ACACAGCTGG | 241800 |
| TATGTGTGAT | CAAATTTGTG | CTGTTTCATC | CACTTAATGT | TTACTTTGTG | GTAATGGAAC | 241860 |
| CTCCCAGCTT | TTATTTTCCT | TCCTTCCTTC | CTTCCTTCCT | TCCTTCCTTC | CTTCCTTCCT | 241920 |
| TCCTCCCTCC | CTCCCTCCCT | CCCTCCCTTC | CTTTCTTTCT | TCACAGAGTC | TAGCTCTGTT | 241980 |
| GCCCAGGCTG | GAATGCAGTG | GTGCGATCTC | AGCTCACTGC | AACCTCTGCC | TCCCGGGTTC | 242040 |
| AAGCGATTCT | CCTGCCTCAG | CCTCCCAAGT | ATCTAGGATT | ACAGGTGCAT | GCTGCCACAC | 242100 |
| CTGGCTAGTT | TTTGTATTTT | TAGTAAAGAT | GGAGTTTCAG | ATGTTGGCCA | GGCTGGTCTC | 242160 |
| CAACACCAGG | CCTCAAGTGA | TCCGCCTGCC | TTGGCCTCCC | AAATTGCTGG | GATTAACAGG | 242220 |
| CCTCAGCCAC | TGTGCCCGAC | CCCAGCTTTT | ATATTCTAAT | GCTGAGATTA | TTCAGTTAAC | 242280 |
| ACTCTTACCT | GCTAGGATAA | GTTTGTTGGA | GAATTTTACC | TTACCTTGTA | CCCTTTACCT | 242340 |
| TCACATCTAC | CTGTACCCTG | GCCCTTCACA | TCCTTTCCAT | ATAATATATC | TTCAGTAAAT | 242400 |
| ACAGGGAAAA | AAACCCAGAA | TGATTATGTT | GACAGCAAAA | CATGTTTGTG | CAGAAACGGA | 242460 |
| GTAGTCACTA | TCTAAGCCAC | AGAGACTTAG | GAGTGTATTC | CTGAGTTATG | TATCATTTTA | 242520 |
| ACCATCACTG | GATCTTAAAT | CCCAGTTGCT | AAATTGAAGG | GAGATACATG | ACTCTTTTTA | 242580 |
| GGGCTTTGCT | CTCTGATACA | GTAGCCATTA | GCCACATGTG | ATATTTAAA | TTTAAATAAT | 242640 |
| TAAGTCAAAA | ATTCAGTTTC | CTCAGTCTCA | CCACATTTCA | GGTTGCTGGT | GTCTACTGTA | 242700 |

| | | | | | | |
|---|---|---|---|---|---|---|
| TTGGATACAC | AGACATAGAA | CATGTCTATC | ATCACAGAAA | ATTCTATTGC | ATTGCACTGG | 242760 |
| GATAGGTACT | TTTTGTGCCC | TTGGGCTGAT | AAGTTCAAGT | GCACTTAACT | AGCTTCCTCC | 242820 |
| AAGTGGAATC | AGAGGATAAA | TTTACCATAC | AAAATACAGG | ATACCCAATT | ATATTTGAAT | 242880 |
| TTCAAACAGG | CAACAAATAA | TTGCTTAAGT | ATGCCCCTCA | CTGCACACCC | AAATATTACA | 242940 |
| TGAGACATTC | TATACATATA | TATATATATA | TATATATATA | TATATATATA | TATATATATA | 243000 |
| TATATATATT | TGAAATTCAG | ATTTAACTGG | ACATTTGGTA | TTTTTAATGT | GCCAAATCTA | 243060 |
| GCAACCCTAT | CTGAAGAGCA | AAACTGGAGT | GTCTAGTCTG | GATAGGTCCT | TTTACACCAC | 243120 |
| AGGGAGTTAT | TTGAGGAATT | GAGAAGGGCT | GTGGTACCTG | TAAAGAACTA | ACTCATTATG | 243180 |
| AAGAAAAGGA | TCTGTAAGTT | TTTCTGTATG | TGTAAGGAAG | GCCAAGAAGG | TGGTTTCCAG | 243240 |
| ATATATTTAC | TTTTTCTTCT | CTCTCTCTTA | GGTTGCAAAA | GCTTCTCATT | TCAGAGAGAT | 243300 |
| GCCAGGATCC | TAAGTGCCTG | CCAAACTTAC | CAATTCTAAG | GAATAAGTGG | ATGGATGGCA | 243360 |
| TTACTGATTC | CTACATTACT | GATTGATTCT | GCATCCGCAA | ATTGTTTTAT | TAAAAACATT | 243420 |
| CTACATCATG | TGTGGGGAGA | TAAGGAGGAT | AAAATGAAGA | GAAGAATAT | TATTGAGGGG | 243480 |
| AAGTTCTTCT | GAATACAAAA | TGTGTTTAAT | TTTTAAATA | AGTATTACAT | TCACAGGGTT | 243540 |
| CAAACTATTT | GAAGTAAAGA | GATTATATAT | AAAGAATCCA | TCCCTCAACT | TACCCAGGTG | 243600 |
| GTCACTTTTC | TTTTTCTTGT | GTATCTGCCC | AGTATTCATT | CCTGCTGATA | TCAGTCAATA | 243660 |
| ATGAATGATA | CGTGTTTTCT | TCACTTTTTT | CATTCTTGTC | AGGTAGCAGA | CTGTGTAGAC | 243720 |
| TTTTCTGCAC | TTGCCCTTTT | CATAACAATC | TATCTTGGAG | AACTTTCCCT | ATGAGAACAT | 243780 |
| ACAGAGCTTC | CTGTACACAG | TTGCATGTAC | TGCATTATGC | AAATGCATTA | TATTTATGT | 243840 |
| AACCTGTCCA | CTGTTGGTAG | GCACTTGAGT | TGTTTAGTC | TTTTGCTATC | AAACAGTTCT | 243900 |
| GGGATGATTA | ACCCTGATTT | ACTGCAAAAT | TGAAATTGCT | CTGCTATTCT | GCTGGAATGG | 243960 |
| TGGTAAGTGA | ACTGAAAATT | CCAGTCACTC | TTGGGCTAGA | CTCAACGTTC | TTAAAAACTA | 244020 |
| TGTGGCCATC | ACCAAATTAG | TTATTTTGAA | CCTTAATTTC | TTCACCTCTA | AAATGGAGGT | 244080 |
| AATACTTACC | TTAAGTGGCT | ATGAGAATGA | AGATCATGTG | TATGAATTGT | TGGTGCTCTA | 244140 |
| AAGAACAGCA | CAAATAAAAT | TATTTTCAAA | TTTAATTTTA | ATTGAACTAT | GTGTAATTTC | 244200 |
| TTAATTTTGA | AATAATTTTA | TTTGTAATGT | GCATAATCTT | ATTTAATGTA | TAATGTATAC | 244260 |
| ATTGTAATAG | AAACAGATTT | CCCAAATTCC | AGCCTGGCAT | GAGGTAATAA | AAGGTAATGC | 244320 |
| AAAGGGAGAG | GAAAGCATGT | GTCATTAATT | TTCTGCCTAG | GACACCTCCC | TGGTTAAATT | 244380 |
| GCCATTTCCT | TTCTTCCTTG | CATAATGATT | AGGAAACACA | TCCTCCTGAC | CTGCCTGCCC | 244440 |
| TCTTTTGCCT | ACTTTTTCAT | CTGCAGTCAA | GGTCTGGTTT | TAAGACTGAC | TGTTACTTTT | 244500 |
| ACAAATCTGT | GTGTATTGGT | GGCTAAGGGC | CTGTATGGTC | CACTGCTGTA | TTCCCAGGTC | 244560 |
| CCAGCATGGT | GCCTGACGCT | GCCTGGCAAA | TAGTAGTCAC | CCGAGAAATG | GCTGATGAAT | 244620 |
| TCATGAGGCC | TACTCTGTAT | GGAAATTTCA | ATTCTGGCCC | CGAATTTTCA | GGAGCTGGCA | 244680 |
| AGAGAGCCAC | CTTAATATCA | TAGGCTGAGT | TGGAAGAAGG | GAACACCCAA | TTTATTCTTA | 244740 |
| AGAAGTACTT | TGCCCAGGTA | CTGTGGCTTA | GGCCAGTAAT | CCTAGCATTT | GGGGAAGCCA | 244800 |
| AGTTGGGCAG | ATGGCTTGAA | CCCAGGATTT | CGAGATCAGC | CTGGACAACA | TGGAGAAACC | 244860 |
| CCATCTCTAC | AAAATATGTA | AAATTTAACT | GCTTGGTGGG | CCTGCACTTC | TGGTCCCAGC | 244920 |
| TACTCCAGGG | CTAGGGTGGG | AGGATTGTTT | GATCCCTGGA | GGTCAAGGCT | GCAGTGAGCC | 244980 |
| ATGATCACAG | CAATGCGCTC | CAGCTCTGGG | CAACAGAGCG | AGACCCTGTC | TCAAAAAAAA | 245040 |
| CAAAAATGCC | TATACAATAA | ATCTATAAAA | AGTGGGTTTT | GTGTGTCTAT | ACACACACAC | 245100 |

| | | | | | | |
|---|---|---|---|---|---|---|
| ACACACACAC | ACCTGCATAG | ACACTCAGGT | GTTCTGGAAA | GACACAGGAA | TCTGAAGCCA | 245160 |
| AAATACTTGT | GATTTTTTTT | CAGCTCTGCC | ACTCACCAAA | TGTCTGATGG | GATTAGTTAC | 245220 |
| CTGCCATCTC | AGAATTTCTC | TTCTGTAAAA | TAAGGTAATA | GTACCTCCCA | GAGTTATGAA | 245280 |
| AAACTATCAA | ATGAGATGGC | AGATGAGAAA | ACACTATATT | CCTTGTAAAA | CCTGACAAAT | 245340 |
| ATGTGCAAGA | TTATATAAAG | ACTGTCTTCT | GTCCATTTTC | AAATGTGGAA | AAGTGAAAGC | 245400 |
| AGGACAGGAT | GTTGGGATTT | CTGTCAGAGA | TTTGCTGGCT | TCCACCTGCA | GAAATTGAAG | 245460 |
| TAATTGGGGT | TCTTACACCT | AAGTACTAAC | TGAGTCTGGT | TGCAGTTTGC | CCCCATGGCT | 245520 |
| ACATGAAGCT | TTTAGAAGAG | TCAGCATGGT | AGACATGGAA | TGTTGAATGG | TGGTGGAGTG | 245580 |
| TACCCACACA | CCTCCCACCA | AGTCAGCTCC | AGGTTCAGAA | GCAGCAGCCC | CAGTGGAAGG | 245640 |
| CATGCGTGTT | TGTAACTCAG | CTGAGCCACC | TTTCAAGAAG | CAGAAGCTTT | CCAAACAGGG | 245700 |
| ATGCCCCTG | CTTTTGGTTC | AACTTGACTT | CCTACCTTCA | GTGAGGACAT | GGAGAATTCA | 245760 |
| TCTAGACTGG | GTACCTGAGC | AAACTTGGCA | GAGCAAAGAG | AAATGTGGAA | GGCCCTAGGT | 245820 |
| AGACAGGCCC | TGTGGAAGGA | AAGAATGAAA | GAGGACAGAA | AGAAACTCCC | ATTTTCTTTA | 245880 |
| GCACAGTCCC | TTCAGATTAA | GGATGAAGAG | GCTGGGGTTC | TGAATTGGTT | GGCCTTAGGT | 245940 |
| AATGGTCACA | AAAACAAGTC | AATGGCTTTT | CCACATCCGT | ACATTGAGAT | ATATTTCTGC | 246000 |
| CCTTGGTATT | CATTTTCTCT | GACCTCCAAT | TAAAGATCTA | TGCGTCATTT | TAAAGCCTTC | 246060 |
| CTTCCTTTCT | ACTCTGTGGT | CAGCGTAACA | TTGGTGGTTT | GAAACTGGCC | ATAATAGCAG | 246120 |
| CATTTACATC | ATGGGAACTA | GCATATGTTA | CATCAGGGTT | TTTTGTTTT | GTTTCTGGAG | 246180 |
| AGCCAGTAAA | CATACATCGT | CACACCACTT | AAATATTCTC | TGCTTAAATA | TTCTCTGCTC | 246240 |

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "Mbo I-S primer"

( x i ) SEQUENCE DESCRIPTION: SEQ ID NO:23:

CCTGATGCTC GAGTGAATTC                                    20

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note= "vector-vector splicing"

( x i ) SEQUENCE DESCRIPTION: SEQ ID NO:24:

CGACCCAGCA ACCTGGAGAT                                    20

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: Not Relevant ( i i ) MOLECULE TYPE: cDNA ( i x ) FEATURE:
    ( A ) NAME/KEY: misc_feature
    ( B ) LOCATION: 1..20
    ( D ) OTHER INFORMATION: /note= "cryptic donor-1021"

( x i ) SEQUENCE DESCRIPTION: SEQ ID NO:25:

AGCTCGAGCG GCCGCTGCAG     20

( 2 ) INFORMATION FOR SEQ ID NO:26:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: Not Relevant ( i i ) MOLECULE TYPE: cDNA ( i x ) FEATURE:
    ( A ) NAME/KEY: misc_feature
    ( B ) LOCATION: 1..20
    ( D ) OTHER INFORMATION: /note= "cryptic donor-1134"

( x i ) SEQUENCE DESCRIPTION: SEQ ID NO:26:

AGACCCCAAC CCACAAGAAG     20

( 2 ) INFORMATION FOR SEQ ID NO:27:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: Not Relevant ( i i ) MOLECULE TYPE: cDNA ( i x ) FEATURE:
    ( A ) NAME/KEY: misc_feature
    ( B ) LOCATION: 1..20
    ( D ) OTHER INFORMATION: /note= "MAP1"

( x i ) SEQUENCE DESCRIPTION: SEQ ID NO:27:

CGTTAGAACG CGGCTACAAT     20

( 2 ) INFORMATION FOR SEQ ID NO:28:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: Not Relevant ( i i ) MOLECULE TYPE: cDNA ( i x ) FEATURE:
    ( A ) NAME/KEY: misc_feature
    ( B ) LOCATION: 1..20
    ( D ) OTHER INFORMATION: /note= "MAP2"

( x i ) SEQUENCE DESCRIPTION: SEQ ID NO:28:

GCCGATTCAT TAATGCAGGT     20

( 2 ) INFORMATION FOR SEQ ID NO:29:

( i ) SEQUENCE CHARACTERISTICS:
  ( A ) LENGTH: 20 base pairs
  ( B ) TYPE: nucleic acid
  ( C ) STRANDEDNESS: Not Relevant
  ( D ) TOPOLOGY: Not Relevant ( i i ) MOLECULE TYPE: cDNA ( i x ) FEATURE:
  ( A ) NAME/KEY: misc_feature
  ( B ) LOCATION: 1..20
  ( D ) OTHER INFORMATION: /note= "-21"

( x i ) SEQUENCE DESCRIPTION: SEQ ID NO:29:

CTGTAAAACG ACGGCCAGTC  20

( 2 ) INFORMATION FOR SEQ ID NO:30:

( i ) SEQUENCE CHARACTERISTICS:
  ( A ) LENGTH: 19 base pairs
  ( B ) TYPE: nucleic acid
  ( C ) STRANDEDNESS: Not Relevant
  ( D ) TOPOLOGY: Not Relevant ( i i ) MOLECULE TYPE: cDNA ( i x ) FEATURE:
  ( A ) NAME/KEY: misc_feature
  ( B ) LOCATION: 1..19
  ( D ) OTHER INFORMATION: /note= "REV"

( x i ) SEQUENCE DESCRIPTION: SEQ ID NO:30:

GCAGGAAACA GCTATGACC  19

( 2 ) INFORMATION FOR SEQ ID NO:31:

( i ) SEQUENCE CHARACTERISTICS:
  ( A ) LENGTH: 20 amino acids
  ( B ) TYPE: amino acid
  ( C ) STRANDEDNESS: Not Relevant
  ( D ) TOPOLOGY: Not Relevant ( i i ) MOLECULE TYPE: peptide ( i x ) FEATURE:
  ( A ) NAME/KEY: Peptide
  ( B ) LOCATION: 3
  ( D ) OTHER INFORMATION: /note= "may be I or V"

( i x ) FEATURE:
  ( A ) NAME/KEY: Peptide
  ( B ) LOCATION: 5
  ( D ) OTHER INFORMATION: /note= "X is 11-30 peptides long"

( i x ) FEATURE:
  ( A ) NAME/KEY: Peptide
  ( B ) LOCATION: 10
  ( D ) OTHER INFORMATION: /note= "may be F, I or L"

( i x ) FEATURE:
  ( A ) NAME/KEY: Peptide
  ( B ) LOCATION: 15
  ( D ) OTHER INFORMATION: /note= "may be I, L or M"

( i x ) FEATURE:
  ( A ) NAME/KEY: Peptide
  ( B ) LOCATION: 16
  ( D ) OTHER INFORMATION: /note= "X is 10-18 peptides long"

-continued (x i) SEQUENCE DESCRIPTION: SEQ ID NO:31:

```
Cys Xaa Xaa Cys Xaa Cys Xaa His Xaa Xaa Cys Xaa Xaa Cys Xaa Xaa
1               5                   10                  15
Cys Pro Xaa Cys
            20
```